US012428406B2

(12) United States Patent
Vu et al.

(10) Patent No.: US 12,428,406 B2
(45) Date of Patent: Sep. 30, 2025

(54) METHODS AND COMPOUNDS FOR RESTORING MUTANT p53 FUNCTION

(71) Applicant: PMV Pharmaceuticals, Inc., Princeton, NJ (US)

(72) Inventors: Binh Vu, North Caldwell, NJ (US); Romyr Dominique, East Brunswick, NJ (US); Hongju Li, Edison, NJ (US); Bruce Fahr, East Windsor, NJ (US); Andrew Good, Wallingford, CT (US)

(73) Assignee: PMV PHARMACEUTICALS, INC., Princeton, NJ (US)

( * ) Notice: Subject to any disclaimer, the term of this patent is extended or adjusted under 35 U.S.C. 154(b) by 0 days.

(21) Appl. No.: 18/328,433

(22) Filed: Jun. 2, 2023

(65) Prior Publication Data

US 2023/0312539 A1    Oct. 5, 2023

Related U.S. Application Data

(63) Continuation of application No. 17/028,720, filed on Sep. 22, 2020, now Pat. No. 11,814,373.

(60) Provisional application No. 63/038,388, filed on Jun. 12, 2020, provisional application No. 62/904,369, filed on Sep. 23, 2019.

(51) Int. Cl.
| | |
|---|---|
| *C07D 405/14* | (2006.01) |
| *C07D 209/14* | (2006.01) |
| *C07D 401/12* | (2006.01) |
| *C07D 401/14* | (2006.01) |
| *C07D 403/06* | (2006.01) |
| *C07D 403/12* | (2006.01) |
| *C07D 405/12* | (2006.01) |
| *C07D 409/12* | (2006.01) |
| *C07D 409/14* | (2006.01) |
| *C07D 417/14* | (2006.01) |
| *C07D 471/04* | (2006.01) |
| *C07D 471/08* | (2006.01) |
| *C07D 491/107* | (2006.01) |
| *C07F 7/08* | (2006.01) |
| *C07H 15/26* | (2006.01) |

(52) U.S. Cl.
CPC ......... *C07D 405/14* (2013.01); *C07D 209/14* (2013.01); *C07D 401/12* (2013.01); *C07D 401/14* (2013.01); *C07D 403/06* (2013.01); *C07D 403/12* (2013.01); *C07D 405/12* (2013.01); *C07D 409/12* (2013.01); *C07D 409/14* (2013.01); *C07D 417/14* (2013.01); *C07D 471/04* (2013.01); *C07D 471/08* (2013.01); *C07D 491/107* (2013.01); *C07F 7/0812* (2013.01); *C07H 15/26* (2013.01)

(58) Field of Classification Search
CPC ..... A61P 35/00; C07F 7/0812; C07D 413/06; C07D 405/06
See application file for complete search history.

(56) References Cited

U.S. PATENT DOCUMENTS

| | | | |
|---|---|---|---|
| 7,601,714 B2 | 10/2009 | Barbosa et al. | |
| 8,822,689 B2 | 9/2014 | Soll et al. | |
| 8,859,780 B2 | 10/2014 | Ehring et al. | |
| 8,865,715 B2 | 10/2014 | Dorsch et al. | |
| 8,933,113 B2 | 1/2015 | Crespo et al. | |
| 9,090,661 B2 | 7/2015 | Coburn et al. | |
| 9,447,103 B2 | 9/2016 | Lu et al. | |
| 10,138,219 B2 * | 11/2018 | Vu | A61P 15/00 |
| 10,640,485 B2 | 5/2020 | Vu et al. | |
| 2002/0048271 A1 | 4/2002 | Rastinejad et al. | |
| 2010/0130731 A1 | 5/2010 | Fersht et al. | |
| 2012/0258920 A1 | 10/2012 | Sal et al. | |
| 2017/0240525 A1 * | 8/2017 | Vu | C07D 405/12 |
| 2019/0002460 A1 | 1/2019 | Whitehead et al. | |
| 2019/0119249 A1 | 4/2019 | Vu et al. | |
| 2021/0002252 A1 | 1/2021 | Vu et al. | |
| 2022/0213062 A1 | 7/2022 | Vu et al. | |

FOREIGN PATENT DOCUMENTS

| | | |
|---|---|---|
| CA | 3084777 A1 | 7/2019 |
| CN | 104119332 A | 10/2014 |
| CN | 104672241 | 6/2015 |
| WO | WO-0032175 A2 | 6/2000 |
| WO | WO-03032911 A3 | 7/2003 |
| WO | WO-2006136823 A1 | 12/2006 |
| WO | WO-2009136175 A1 | 11/2009 |
| WO | WO-2012135149 A2 | 10/2012 |
| WO | WO-2012175962 A1 | 12/2012 |

(Continued)

OTHER PUBLICATIONS

Ansel, Howard C, et al. Pharmaceutical Dosage Forms and Drug Delivery Systems. Philadelphia, PA: Lippincott-Williams & Wilkins, 1999. Print.
Bilbao, et al., Two-Dimensional Nanoporous Networks Formed by Liquid-to-Solid Transfer of Hydrogen-Bonded Macrocycles Built from DNA Bases, 2015.
Chinese Office Action issued in Chinese Patent Application No. 2017800134506 on Apr. 13, 2021.
Coburn et al., (Caplus abstract of WO2010111483 (Sep. 30, 2010)).

(Continued)

*Primary Examiner* — Pancham Bakshi
(74) *Attorney, Agent, or Firm* — WILSON SONSINI GOODRICH & ROSATI

(57) ABSTRACT

Mutations in oncogenes and tumor suppressors contribute to the development and progression of cancer. The present disclosure describes compounds and methods to recover wild-type function to p53 mutants. The compounds of the present invention can bind to mutant p53 and restore the ability of the p53 mutant to bind DNA and activate downstream effectors involved in tumor suppression. The disclosed compounds can be used to reduce the progression of cancers that contain a p53 mutation.

20 Claims, No Drawings
Specification includes a Sequence Listing.

(56) References Cited

FOREIGN PATENT DOCUMENTS

| WO | WO-2013036208 A1 | 3/2013 |
|---|---|---|
| WO | WO-2015178955 A1 | 11/2015 |
| WO | WO-2016004513 A1 | 1/2016 |
| WO | WO-2017143291 A1 | 8/2017 |
| WO | WO-2018075937 A1 | 4/2018 |
| WO | WO-2018191587 A1 | 10/2018 |

OTHER PUBLICATIONS

Dellacqua, et al., MediaChrom: Discovering a Class of Pyrimidoindolone-Based Polarity-Sensitive Dyes, 2015, Journal of Organic Chemistry, vol. 80 (21, pp. 10939-10954.
English Translation of JP Application No. 2018-544186 Office Action mailed Jan. 27, 2021.
English Translation of Second Office Action issued in Chinese Application No. 2017800134506 on Apr. 13, 2021.
European Application No. 17753995.4 Office Action dated Jan. 13, 2021.
European Serial No. 17753995.4 Extended Search Report dated Jun. 17, 2019.
Fiandanese, et al., A straightforward synthesis of indole and benzofuran derivatives, 2007, Tetrahedron, Elsevier Science Publishers, vol. 64 (1), pp. 53-60.
Gangjee, et al., Synthesis and Biological Activity of N4-phenylsubstituted-6-(2,4-dichloro phenylmethyl)-7H-pyrrolo[2,3-d]pyrimidine-2,4-diamines as Vascular Endothelial Growth Factor Receptor-2 Inhibitors and Antiangiogenic and Antitumor Agents, 2010, Bioorg Med Chem, vol. 18(10), pp. 1-33.
Gennaro, A.R., Remington: The science and practice of pharmacy. 19th edition. 1995. 12 Pages.
Gergely, et al., C2-Selective Direct Alkynylation of Indoles, 2012, Organic Letters, vol. 15(1), pp. 112-115.
Guo, et al., PIM inhibitors target CD25-positive AML cells through concomitant suppression of STAT5 activation and degradation of MYC oncogene, 2014, Blood, vol. 124 (11), pp. 1777-1789.
Hoover, J. et al., Remington's Pharmaceutical science. 1970.
International Search Report and written opinion dated Jun. 21, 2017 for International Application No. PCT/US2017/018511.
International Search Report and written opinion dated Dec. 22, 2020 for International Application No. PCT/US2020/051998.
Joerger, et al., Structure-function-rescue: the diverse nature of common p53 cancer mutants. Oncogene (2007) 26, 2226-2242.
Kubinyi. 3D QSAR in Drug Design: Ligand-Protein Interactions and Molecular Similarity. (vol. 2-3, Springer, 1998, 800 pages). pp. 243-244 provided.
Leblanc, et al., Homogeneous time-resolved fluorescence assay for identifying p53 interactions with its protein partners, directly in a cellular extract. Analytical Biochemistry 308 (2002) 247-254.
Liberman, H.A., Pharmaceutical Dosage Forms: Parenteral Medications. 1992. vol. 1. 4 pages.
Liu, et al., Small molecule induced reactivation of mutant p53 in cancer cells. Nucleic Acids Research, 2013, vol. 41, No. 12. 6034-6044.
Notice of Allowance issued in Israeli Patent Application No. 261175 issued Jun. 30, 2021.
Notice of Allowance issued in Japanese Patent Application No. 2018-544186 on Sep. 3, 2021.
Notice of Allowance issued in Mexican Patent Application No. MX/a/2018/009947 on Apr. 15, 2021.
Office Action issued in Brazilian Application No. BR112018016890-4 on Aug. 11, 2021.
Patent Certificate 371916 issued in Indian Application No. 201817032237 on Jul. 14, 2021.
Ribeiro, et al., Chemical Variations on the p53 reactivation theme. Pharmaceuticals, May 2016; 9(25):1-33.
Selivanova, et al., Reactivation of mutant p53: molecular mechanisms and therapeutic potential, Oncogene, Apr. 2, 2007; vol. 26: p. 2243-2254.
Shinohara, et al., Design of environmentally sensitive fluorescent 2-deoxyguanosine containing arylethynyl moieties: Distenction of thymine base by base-discriminating fluorescent (BDF) probe, 2010, Bioorganic & Medicinal Chemistry Letters, vol. 20, pp. 2817-2820.
U.S. Appl. No. 15/436,333 Notice of Allowance dated Aug. 27, 2018.
U.S. Appl. No. 15/436,333 Notice of Allowance dated Jul. 23, 2018.
U.S. Appl. No. 16/163,829 Notice of Allowance dated Dec. 20, 2019.
U.S. Appl. No. 16/163,829 Non-Final Office Action issued May 2, 2019.
U.S. Appl. No. 16/819,934 Non-Final Office Action issued May 25, 2021.
U.S. Appl. No. 15/436,333 Office Action dated Dec. 7, 2017.
Wermuth. The Practice of Medicinal Chemistry, 2d ed. 768 pages, chapters 9-10 provided (2003).
Wilcken, et al., Halogen-Enriched Fragment Libraries as Leads for Drug Rescue of Mutant p53. Journal of the American chemical society. 2012; 134:6810-6818.
Bauer, et al., Harnessing Fluorine-Sulfur Contacts and Multipolar Interactions for the Design of p53 Mutant Y220C Rescue Drugs, ACS Chem. Biol., 11:2265-2274, (2016).
Boeckler, et al., Targeted Rescue of a Destabilized Mutant of p53 by an in Silico Screened Drug, PNAS, 105:10360-10365, (2008).
Bohm, et al., Fluorine in Medicinal Chemistry. Chembiochem., 5:637-643, (2004).
Gillis, et al., Applications of Fluorine in Medicinal Chemistry, J. Med. Chem., 58:8315-8359, (2015).
Joerger, et al., Crystal Structure of a Superstable Mutant of Human p53 Core Domain. Insights into the Mechanism of Rescuing Oncogenic Mutations, J. Biol. Chem., 279:1291-1296, (2004).
Joerger, et al., Structural Basis for Understanding Oncogenic p53 Mutations and Designing Rescue Drugs, PNAS, 103:15056-15061, (2006).
Welsch, et al., Privileged Scaffolds for Library Design and Drug Discovery, Curr. Opin. Chem. Biol., 14:347-361, (2010).
Wilcken, et al., Halogen-Enriched Fragment Libraries as Leads for Drug Rescue of Mutant p53, J. Am. Chem. Soc., 134:6810-6818, (2012).

* cited by examiner

SEQUENCE LISTING

```
Sequence total quantity: 1
SEQ ID NO: 1           moltype = AA  length = 219
FEATURE                Location/Qualifiers
```

```
source          1..219
                mol_type = protein
                organism = synthetic construct
SEQUENCE: 1
SSSVPSQKTY QGSYGFRLGF LHSGTAKSVT CTYSPALNKM FCQLAKTCPV QLWVDSTPPP    60
GTRVRAMAIY KQSQHMTEVV RRCPHHERCS DSDGLAPPQH LIRVEGNLRV EYLDDRNTFR   120
HSVVVPCEPP EVGSDCTTIH YNYMCNSSCM GGMNRRPILT IITLEDSSGN LLGRNSFEVH   180
VCACPGRDRR TEEENLRKKG EPHHELPPGS TKRALSNNT                          219
```

METHODS AND COMPOUNDS FOR RESTORING MUTANT p53 FUNCTION

CROSS-REFERENCE

This application is a Continuation of U.S. application Ser. No. 17/028,720, filed Sep. 22, 2020, which claims the benefit of U.S. Provisional Application No. 63/038,388, filed Jun. 12, 2020; and U.S. Provisional Application No. 62/904,369, filed Sep. 23, 2019, each of which are incorporated herein by reference in their entirety.

SEQUENCE LISTING

The instant application contains a Sequence Listing, which has been submitted electronically in XML format and is hereby incorporated by reference in its entirety. Said XML copy, created on May 26, 2023, is named 44727-705_301_SL.xml and is 2111 bytes in size.

BACKGROUND

Cancer, an uncontrolled proliferation of cells, is a multifactorial disease characterized by tumor formation, growth, and in some instances, metastasis. Cells carrying an activated oncogene, damaged genome, or other cancer-promoting alterations can be prevented from replicating through an elaborate tumor suppression network. A central component of this tumor suppression network is p53, one of the most potent tumor suppressors in the cell. Both the wild type and mutant conformations of p53 are implicated in the progression of cancer.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, described herein is a compound, the compound comprising: a heterocyclyl group comprising a halo substituent, wherein the compound binds a mutant p53 protein and increases wild-type p53 activity of the mutant p53 protein.

In some embodiments, described herein is a compound of the formula:

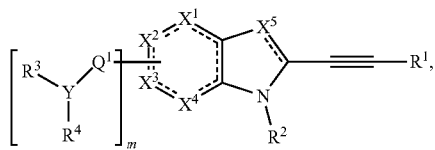

wherein:
each ══════ is independently a single bond or a double bond;
$X^1$ is $CR^5$, $CR^5R^6$, N, $NR^5$, O, S, C═O, C═S, or a carbon atom connected to $Q^1$;
$X^2$ is $CR^7$, $CR^7R^8$, N, $NR^7$, O, S, C═O, C═S, or a carbon atom connected to $Q^1$;
$X^3$ is $CR^9$, $CR^9R^{10}$, N, $NR^9$, O, S, C═O, C═S, or a carbon atom connected to $Q^1$;
$X^5$ is $CR^{13}$, N, or $NR^{13}$;

wherein at least one of $X^1$, $X^2$, $X^3$, and $X^4$ is a carbon atom connected to $Q^1$;
$Q^1$ is C═O, C═S, C═$CR^{14}R^{15}$, C═$NR^{14}$, alkylene, alkenylene, or alkynylene, each of which is independently substituted or unsubstituted, or a bond;
m is 1, 2, 3, or 4;
Y is N, O, or absent;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, C═O, C═S, —CN, —Si$R^{16}R^{17}R^{18}$, alkyl, alkenyl, alkynyl, aryl, heteroaryl, or heterocyclyl, each of which is independently substituted or unsubstituted, or hydrogen;
each $R^3$ and $R^4$ is independently, —C(O)$R^{19}$, —C(O)O$R^{19}$, —C(O)N$R^{19}R^{20}$, —SO$R^{19}$, —SO$_2R^{19}$, alkyl, alkylene, alkenyl, alkenylene, alkynyl, aryl, heteroaryl, or heterocyclyl, each of which is independently substituted or unsubstituted, or hydrogen, or $R^3$ and $R^4$ together with the Y atom to which $R^3$ and $R^4$ are bound form a ring, wherein the ring is substituted or unsubstituted, or $R^3$ is absent;
each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof, wherein the compound is not a compound of Table 1.

In some embodiments, described herein is a compound of the formula:

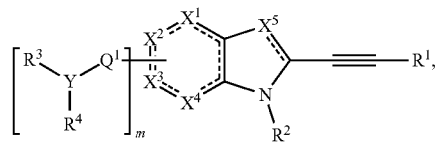

wherein:
each ══════ is independently a single bond or a double bond;
$X^1$ is $CR^5$, $CR^5R^6$, N, $NR^5$, O, S, C═O, C═S, or a carbon atom connected to $Q^1$;
$X^2$ is $CR^7$, $CR^7R^8$, N, $NR^7$, O, S, C═O, C═S, or a carbon atom connected to $Q^1$;
$X^3$ is $CR^9$, $CR^9R^{10}$, N, $NR^9$, O, S, C═O, C═S, or a carbon atom connected to $Q^1$;
$X^4$ is $CR^{11}$, $CR^{11}R^{12}$, N, $NR^{11}$, O, S, C═O, C═S, or a carbon atom connected to $Q^1$;
$X^5$ is $CR^{13}$, N, or $NR^{13}$;

wherein at least one of $X^1$, $X^2$, $X^3$, and $X^4$ is a carbon atom connected to $Q^1$;

$Q^1$ is C=O, C=S, C=CR$^{14}$R$^{15}$, C=NR$^{14}$, alkylene, alkenylene, or alkynylene, each of which is independently substituted or unsubstituted, or a bond;

m is 1, 2, 3, or 4;

Y is N, O, or absent;

$R^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, C=O, C=S, —CN, —SiR$^{16}$R$^{17}$R$^{18}$, alkyl, alkenyl, alkynyl, aryl, heteroaryl, or heterocyclyl, each of which is independently substituted or unsubstituted, or hydrogen;

each $R^3$ and $R^4$ is independently, —C(O)R$^{19}$, —C(O)OR$^{19}$, —C(O)NR$^{19}$R$^{20}$, —SOR$^{19}$, —SO$_2$R$^{19}$, alkyl, alkylene, alkenyl, alkenylene, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent, wherein at least one of $R^3$ and $R^4$ is alkyl, alkylene, alkenyl, alkenylene, alkynyl, aryl, heteroaryl, or heterocyclyl, each of which is substituted at least with halo-;

each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, described herein is a compound, the compound comprising: a heterocyclyl group comprising a halogenated substituent, wherein the compound binds a mutant p53 protein and increases wild-type p53 activity of the mutant p53.

In some embodiments, described herein is a method of treating a cancer, the method comprising administering to a subject in need thereof a compound of Formula (I):

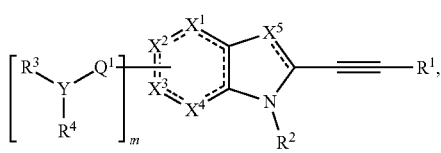

wherein:

each ------- is independently a single bond or a double bond;

$X^1$ is CR$^5$, CR$^5$R$^6$, N, NR$^5$, O, S, C=O, C=S, or a carbon atom connected to $Q^1$;

$X^2$ is CR$^7$, CR$^7$R$^8$, N, NR$^7$, O, S, C=O, C=S, or a carbon atom connected to $Q^1$;

$X^3$ is CR$^9$, CR$^9$R$^{10}$, N, NR$^9$, O, S, C=O, C=S, or a carbon atom connected to $Q^1$;

$X^4$ is CR$^{11}$, CR$^{11}$R$^{12}$, N, NR$^{11}$, O, S, C=O, C=S, or a carbon atom connected to $Q^1$;

$X^5$ is CR$^{13}$, N, or NR$^{13}$;

wherein at least one of $X^1$, $X^2$, $X^3$, and $X^4$ is a carbon atom connected to $Q^1$;

$Q^1$ is C=O, C=S, C=CR$^{14}$R$^{15}$, C=NR$^{14}$, alkylene, alkenylene, or alkynylene, each of which is independently substituted or unsubstituted, or a bond;

m is 1, 2, 3, or 4;

Y is N, O, or absent;

$R^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, C=O, C=S, —CN, —SiR$^{16}$R$^{17}$R$^{18}$, alkyl, alkenyl, alkynyl, aryl, heteroaryl, or heterocyclyl, each of which is independently substituted or unsubstituted, or hydrogen;

each $R^3$ and $R^4$ is independently, —C(O)R$^{19}$, —C(O)OR$^{19}$, —C(O)NR$^{19}$R$^{20}$, —SOR$^{19}$, —SO$_2$R$^{19}$, alkyl, alkylene, alkenyl, alkenylene, alkynyl, aryl, heteroaryl, or heterocyclyl, each of which is independently substituted or unsubstituted, or hydrogen, or $R^3$ and $R^4$ together with the Y atom to which $R^3$ and $R^4$ are bound form a ring, wherein the ring is substituted or unsubstituted, or $R^3$ is absent;

each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically acceptable salt thereof;

wherein the compound has an SC$_{150}$ value for p53 Y220C of less than 1 μM as measured by a homogeneous time-resolved fluorescence (HTRF) assay.

In some embodiments, described herein is a compound of the formula:

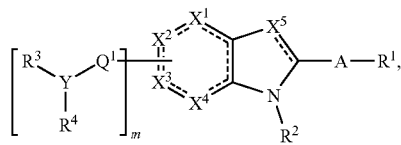

wherein:

each ------- is independently a single bond or a double bond;

$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
A is a linking group;
$Q^1$ is C=O, C=S, C=$CR^{14}R^{15}$, C=$NR^{14}$, alkylene, alkenylene, or alkynylene, each of which is independently substituted or unsubstituted, or a bond;
m is 1, 2, 3, or 4;
Y is N, O, or absent;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;
each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent; wherein at least one of $R^3$ and $R^4$ is alkyl, alkylene, alkenyl, alkenylene, alkynyl, alkynylene, aryl, heteroaryl, or heterocyclyl, each of which is substituted with at least halo;
each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is independently —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen,
or a pharmaceutically-acceptable salt thereof In some embodiments, described herein is a compound of the formula:

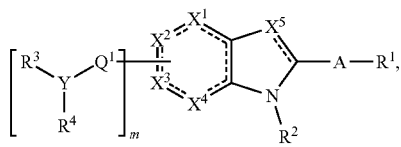

wherein:
each ------- is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
A is a linking group;
$Q^1$ is C=O, C=S, C=$CR^{14}R^{15}$, C=$NR^{14}$, alkylene, alkenylene, or alkynylene, each of which is independently substituted or unsubstituted, or a bond;
m is 1, 2, 3, or 4;
Y is N, O, or absent;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;
each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is independently —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen,
or a pharmaceutically-acceptable salt thereof, wherein the compound is not a compound of Table 1.

In some embodiments, described herein is a method of inducing apoptosis in a cell, the method comprising contacting the cell with a therapeutically-effective amount of a compound of the disclosure that binds a p53 mutant, wherein the compound increases the ability of the p53 mutant to bind DNA, wherein the cell expresses the p53 mutant.

In some embodiments, described herein is a method of treating a cancer, the method comprising administering to a subject in need thereof a therapeutically-effective amount of a compound of the disclosure.

DETAILED DESCRIPTION

The present invention provides compounds and methods for restoring wild-type function to mutant p53. The compounds of the present invention can bind to mutant p53 and restore the ability of the p53 mutant to bind DNA. The restoration of activity of the p53 mutant can allow for the activation of downstream effectors of p53 leading to inhibition of cancer progression. The invention further provides methods of treatment of a cancerous lesion or a tumor harboring a p53 mutation.

Cancer is a collection of related diseases characterized by uncontrolled proliferation of cells with the potential to metastasize throughout the body. Cancer can be classified into five broad categories including, for example: carcinomas, which can arise from cells that cover internal and external parts of the body such as the lung, breast, and colon; sarcomas, which can arise from cells that are located in bone, cartilage, fat, connective tissue, muscle, and other supportive tissues; lymphomas, which can arise in the lymph nodes and immune system tissues; leukemia, which can arise in the bone marrow and accumulate in the bloodstream; and adenomas, which can arise in the thyroid, the pituitary gland, the adrenal gland, and other glandular tissues.

Although different cancers can develop in virtually any of the body's tissues, and contain unique features, the basic processes that cause cancer can be similar in all forms of the disease. Cancer begins when a cell breaks free from the normal restraints on cell division and begins to grow and divide out of control. Genetic mutations in the cell can preclude the ability of the cell to repair damaged DNA or initiate apoptosis, and can result in uncontrolled growth and division of cells.

The ability of tumor cell populations to multiply is determined not only by the rate of cell proliferation but also by the rate of cell attrition. Programmed cell death, or apoptosis, represents a major mechanism of cellular attrition. Cancer cells can evade apoptosis through a variety of strategies, for example, through the suppression of p53 function, thereby suppressing expression of pro-apoptotic proteins.

Oncogenes and tumor suppressor genes can regulate the proliferation of cells. Genetic mutations can affect oncogenes and tumor suppressors, potentially activating or suppressing activity abnormally, further facilitating uncontrolled cell division. Whereas oncogenes assist in cellular growth, tumor suppressor genes slow cell division by repairing damaged DNA and activating apoptosis. Cellular oncogenes that can be mutated in cancer include, for example, Cdk1, Cdk2, Cdk3, Cdk4, Cdk6, EGFR, PDGFR, VEGF, HER2, Raf kinase, K-Ras, and myc. Tumor suppressor genes that can be mutated in cancer include, for example, BRCA1, BRCA2, cyclin-dependent kinase inhibitor 1C, Retinoblastoma protein (pRb), PTEN, p16, p27, p53, and p73.

Tumor Suppressor p53.

The tumor suppressor protein p53 is a 393 amino acid transcription factor that can regulate cell growth in response to cellular stresses including, for example, UV radiation, hypoxia, oncogene activation, and DNA damage. p53 has various mechanisms for inhibiting the progression of cancer including, for example, initiation of apoptosis, maintenance of genomic stability, cell cycle arrest, induction of senescence, and inhibition of angiogenesis. Due to the critical role of p53 in tumor suppression, p53 is inactivated in almost all cancers either by direct mutation or through perturbation of associated signaling pathways involved in tumor suppression. Homozygous loss of the p53 gene occurs in almost all types of cancer, including carcinomas of the breast, colon, and lung. The presence of certain p53 mutations in several types of human cancer can correlate with less favorable patient prognosis.

In the absence of stress signals, p53 levels are maintained at low levels via the interaction of p53 with Mdm2, an E3 ubiquitin ligase. In an unstressed cell, Mdm2 can target p53 for degradation by the proteasome. Under stress conditions, the interaction between Mdm2 and p53 is disrupted, and p53 accumulates. The critical event leading to the activation of p53 is phosphorylation of the N-terminal domain of p53 by protein kinases, thereby transducing upstream stress signals. The phosphorylation of p53 leads to a conformational change, which can promote DNA binding by p53 and allow transcription of downstream effectors. The activation of p53 can induce, for example, the intrinsic apoptotic pathway, the extrinsic apoptotic pathway, cell cycle arrest, senescence, and DNA repair. p53 can activate proteins involved in the above pathways including, for example, Fas/Apo 1, KILLER/DR5, Bax, Puma, Noxa, Bid, caspase-3, caspase-6, caspase-7, caspase-8, caspase-9, and p21 (WAF1). Additionally, p53 can repress the transcription of a variety of genes including, for example, c-MYC, Cyclin B, VEGF, RAD51, and hTERT.

Each chain of the p53 tetramer is composed of several functional domains including the transactivation domain (amino acids 1-100), the DNA-binding domain (amino acids 101-306), and the tetramerization domain (amino acids 307-355), which are highly mobile and largely unstructured. Most p53 cancer mutations are located in the DNA-binding core domain of the protein, which contains a central β-sandwich of anti-parallel β-sheets that serves as a basic scaffold for the DNA-binding surface. The DNA-binding surface is composed of two β-turn loops, L2 and L3, which are stabilized by a zinc ion, for example, at Arg175 and Arg248, and a loop-sheet-helix motif. Altogether, these structural elements form an extended DNA-binding surface that is rich in positively-charged amino acids and makes specific contact with various p53 response elements.

Due to the prevalence of p53 mutations in virtually every type of cancer, the reactivation of wild type p53 function in a cancerous cell can be an effective therapy. Mutations in p53 located in the DNA-binding domain of the protein or periphery of the DNA-binding surface result in aberrant protein folding required for DNA recognition and binding. Mutations in p53 can occur, for example, at amino acids Val143, His168, Arg175, Tyr220, Gly245, Arg248, Arg249, Phe270, Arg273, and Arg282. p53 mutations that can abrogate the activity of p53 include, for example, R175H, Y220C, G245S, R248Q, R248W, R273H, and R282H. These p53 mutations can either distort the structure of the DNA-binding site or thermodynamically destabilize the folded protein at body temperature. Wild-type function of p53 mutants can be recovered by binding of the p53 mutant to a compound that can shift the folding-unfolding equilibrium towards the folded state, thereby reducing the rate of unfolding and destabilization.

Non-limiting examples of amino acids include: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); and valine (V, Val).

Mechanism of Compounds of the Invention.

The compounds of the present invention can selectively bind to a p53 mutant and can recover wild-type activity of the p53 mutant including, for example, DNA binding function and activation of downstream targets involved in tumor suppression. In some embodiments, a compound of the invention selectively binds to the p53 Y220C mutant. The Y220C mutant is a temperature sensitive mutant, which binds to DNA at lower temperature and is denatured at body temperature. A compound of the invention can stabilize the Y220C mutant to reduce the likelihood of denaturation of the protein at body temperature.

Located in the periphery of the p53β-sandwich connecting β-strands S7 and S8, the aromatic ring of Y220 is an integral part of the hydrophobic core of the β-sandwich. The Y220C mutation can be highly destabilizing, due to the formation of an internal surface cavity. A compound of the invention can bind to and occupy this surface crevice to stabilize the β-sandwich, thereby restoring wild-type p53 DNA-binding activity.

To determine the ability of a compound of the invention to bind and stabilize mutant p53, assays can be employed to detect, for example, a conformational change in the p53 mutant or activation of wild-type p53 targets. Conformational changes in p53 can be measured by, for example, differential scanning fluorimetry (DSF), isothermal titration calorimetry (ITC), nuclear magnetic resonance spectrometry (NMR), or X-ray crystallography. Additionally, antibodies specific for the wild type of mutant conformation of p53 can be used to detect a conformational change via, for example, immunoprecipitation (IP), immunofluorescence (IF), or immunoblotting.

Methods used to detect the ability of the p53 mutant to bind DNA can include, for example, DNA affinity immunoblotting, modified enzyme-linked immunosorbent assay (ELISA), electrophoretic mobility shift assay (EMSA), fluorescence resonance energy transfer (FRET), homogeneous time-resolved fluorescence (HTRF), and a chromatin immunoprecipitation (ChIP) assay.

To determine whether a compound described herein is able to reactivate the transcriptional activity of p53, the activation of downstream targets in the p53 signaling cascade can be measured. Activation of p53 effector proteins can be detected by, for example, immunohistochemistry (IHC-P), reverse transcription polymerase chain reaction (RT-PCR), and western blotting. The activation of p53 can also be measured by the induction of apoptosis via the caspase cascade and using methods including, for example, Annexin V staining, TUNEL assays, pro-caspase and caspase levels, and cytochrome c levels. Another consequence of p53 activation is senescence, which can be measured using methods such as #i-galactosidase staining.

A p53 mutant that can be used to determine the effectiveness of a compound of the invention to increase the DNA binding ability of a p53 mutant is a p53 truncation mutant, which contains only amino acids 94-312, encompassing the DNA-binding domain of p53. For example, the sequence of the p53 Y220C mutant used for testing compound efficacy can be:

SSSVPSQ KTYQGSYGFR LGFLHSGTAK SVTCTYSPAL NKMFCQLAKT CPVQLWVDST PPPGTRVRAM AIYKQSQHMT EVVRRCPHHE RCSDSDGLAP PQHLIRVEGN LRVEYLDDRN TFRHSVVVPC EPPEVGSDCT TIHYNYMCNS SCMGGMNRRP ILTIITLEDS SGNLLGRNSF EVHVCACPGR DRRTEEENLR KKGEPHHELP PGSTKRALSN NT (SEQ ID NO. 1)

A compound of the invention can increase the ability of a p53 mutant to bind DNA by at least or up to about 0.1%, at least or up to about 0.2%, at least or up to about 0.3%, at least or up to about 0.4%, at least or up to about 0.5%, at least or up to about 0.6%, at least or up to about 0.7%, at least or up to about 0.8%, at least or up to about 0.9%, at least or up to about 1%, at least or up to about 2%, at least or up to about 3%, at least or up to about 4%, at least or up to about 5%, at least or up to about 6%, at least or up to about 7%, at least or up to about 8%, at least or up to about 9%, at least or up to about 10%, at least or up to about 11%, at least or up to about 12%, at least or up to about 13%, at least or up to about 14%, at least or up to about 15%, at least or up to about 16%, at least or up to about 17%, at least or up to about 18%, at least or up to about 19%, at least or up to about 20%, at least or up to about 21%, at least or up to about 22%, at least or up to about 23%, at least or up to about 24%, at least or up to about 25%, at least or up to about 26%, at least or up to about 27%, at least or up to about 28%, at least or up to about 29%, at least or up to about 30%, at least or up to about 31%, at least or up to about 32%, at least or up to about 33%, at least or up to about 34%, at least or up to about 35%, at least or up to about 36%, at least or up to about 37%, at least or up to about 38%, at least or up to about 39%, at least or up to about 40%, at least or up to about 41%, at least or up to about 42%, at least or up to about 43%, at least or up to about 44%, at least or up to about 45%, at least or up to about 46%, at least or up to about 47%, at least or up to about 48%, at least or up to about 49%, at least or up to about 50%, at least or up to about 51%, at least or up to about 52%, at least or up to about 53%, at least or up to about 54%, at least or up to about 55%, at least or up to about 56%, at least or up to about 57%, at least or up to about 58%, at least or up to about 59%, at least or up to about 60%, at least or up to about 610%, at least or up to about 62%, at least or up to about 63%, at least or up to about 64%, at least or up to about 65%, at least or up to about 66%, at least or up to about 67%, at least or up to about 68%, at least or up to about 69%, at least or up to about 70%, at least or up to about 71%, at least or up to about 72%, at least or up to about 73%, at least or up to about 74%, at least or up to about 75%, at least or up to about 76%, at least or up to about 77%, at least or up to about 78%, at least or up to about 79%, at least or up to about 80%, at least or up to about 81%, at least or up to about 82%, at least or up to about 83%, at least or up to about 84%, at least or up to about 85%, at least or up to about 86%, at least or up to about 87%, at least or up to about 88%, at least or up to about 89%, at least or up to about 90%, at least or up to about 910%, at least or up to about 92%, at least or up to about 93%, at least or up to about 94%, at least or up to about 95%, at least or up to about 96%, at least or up to about 97%, at least or up to about 98%, at least or up to about 99%, at least or up to about 100%, at least or up to about 125%, at least or up to about 150%, at least or up to about 175%, at least or up to about 200%, at least or up to about 225%, or at least or up to about 250% as compared to the ability of the p53 mutant to bind DNA in the absence of a compound of the invention.

A compound described herein can increase the activity of the p53 mutant that is, for example, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 11-fold, at least or up to about 12-fold, at least or up to about 13-fold, at least or up to about 14-fold, at least or up to about 15-fold, at least or up to about 16-fold, at least or up to about 17-fold, at least or up to about 18-fold, at least or up to about 19-fold, at least or up to about 20-fold, at least or up to about 25-fold, at least or up to about 30-fold, at least or up to about 35-fold, at least or up to about 40-fold, at least or up to about 45-fold, at least or up to about 50-fold, at least or up to about 55-fold, at least or up to about 60-fold, at least or up to about 65-fold, at least or up to about 70-fold, at least or up to about 75-fold, at least or up to about 80-fold, at least or up to about 85-fold, at least or up to about 90-fold, at least or up to about 95-fold, at least or up to about 100-fold, at least or up to about 110-fold, at least or up to about 120-fold, at least or up to about 130-fold, at least or up to about 140-fold, at least or up to about 150-fold, at least or up to about 160-fold, at least or up to about 170-fold, at least or up to about 180-fold, at least or up to about 190-fold, at least or up to about 200-fold, at least or up to about 250-fold, at least or up to about 300-fold, at least or up to about 350-fold, at least or up to about 400-fold, at least or up to about 450-fold, at least or up to about 500-fold, at least or up to about 550-fold, at least or up to about 600-fold, at least or up to about 650-fold, at least or up to about 700-fold, at least or up to about 750-fold, at least or up to about 800-fold, at least or up to about 850-fold, at least or up to about 900-fold, at least or up to about 950-fold, at least or up to about 1,000-fold, at least or up to about 1,500-fold, at least or up to about 2,000-fold, at least or up to about 3,000-fold, at least or up to about 4,000-fold, at least or up to about 5,000-fold, at least or up to about 6,000-fold, at least or up to about 7,000-fold, at least or up to about 8,000-fold, at least or up to about 9,000-fold, or at least or up to about 10,000-fold greater than the activity of the p53 mutant in the absence of the compound.

A compound of the invention can be used, for example, to induce apoptosis, cell cycle arrest, or senescence in a cell. In some embodiments, the cell is a cancer cell. In some embodiments, the cell carries a mutation in p53.

Compounds of the Invention.

In some embodiments, a compound of the disclosure comprises a heterocyclyl group comprising a halo substituent, wherein the compound binds a mutant p53 protein and increases wild-type p53 activity of the mutant protein. In some embodiments, the compound further comprises an indole group. In some embodiments, the indole group has a 1,1,1,-trifluoroethyl substituent at a 1-position of the indole group.

In some embodiments, the indole group has a propargyl substituent at a 2-position of the indole group. In some embodiments, the propargyl substituent is attached to the indole group via an sp carbon atom of the propargyl substituent. In some embodiments, the propargyl substituent is attached to a nitrogen atom of an aniline group via a methylene group of the propargyl substituent. In some embodiments, the indole group comprises an amino substituent at a 4-position of the indole group. In some embodiments, the amino substituent is attached to the heterocyclyl group. In some embodiments, the heterocyclyl group is a piperidine group. In some embodiments, the halo substituent is a fluoro group. In some embodiments, the halo substituent is a chloro group. In some embodiments, the compound has oral bioavailability that is at least about 50% greater than that of an analogous compound that lacks the halo substituent on the heterocyclyl group.

Non-limiting examples of compounds of the invention include compounds of any of the following formulae:

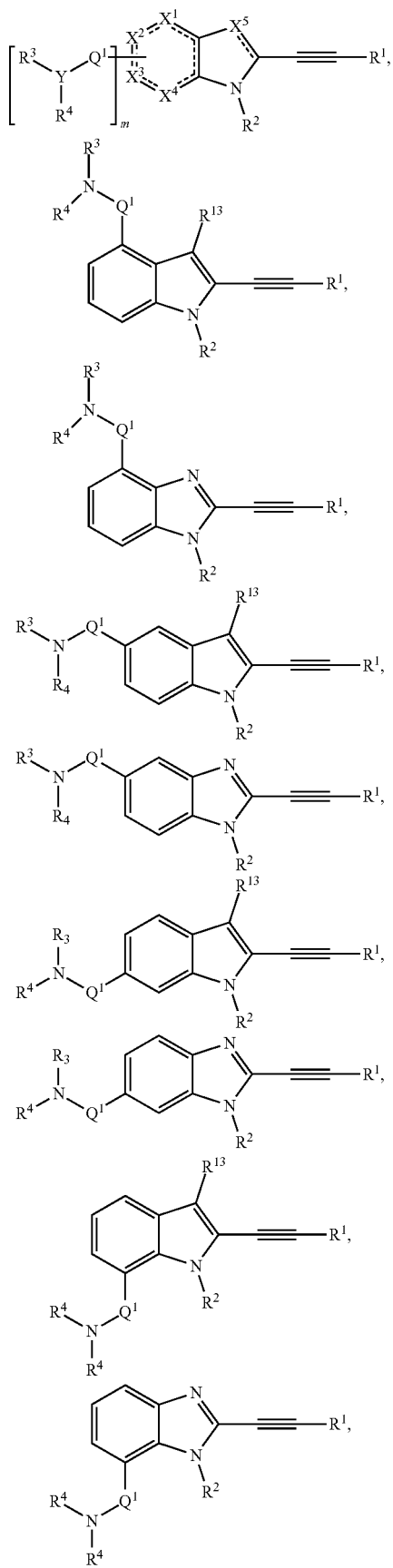

-continued
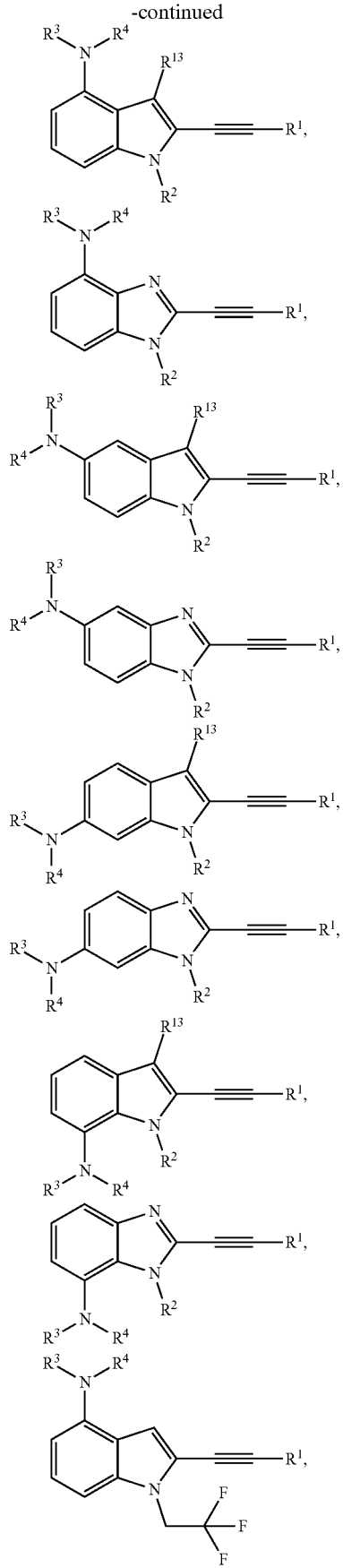
-continued
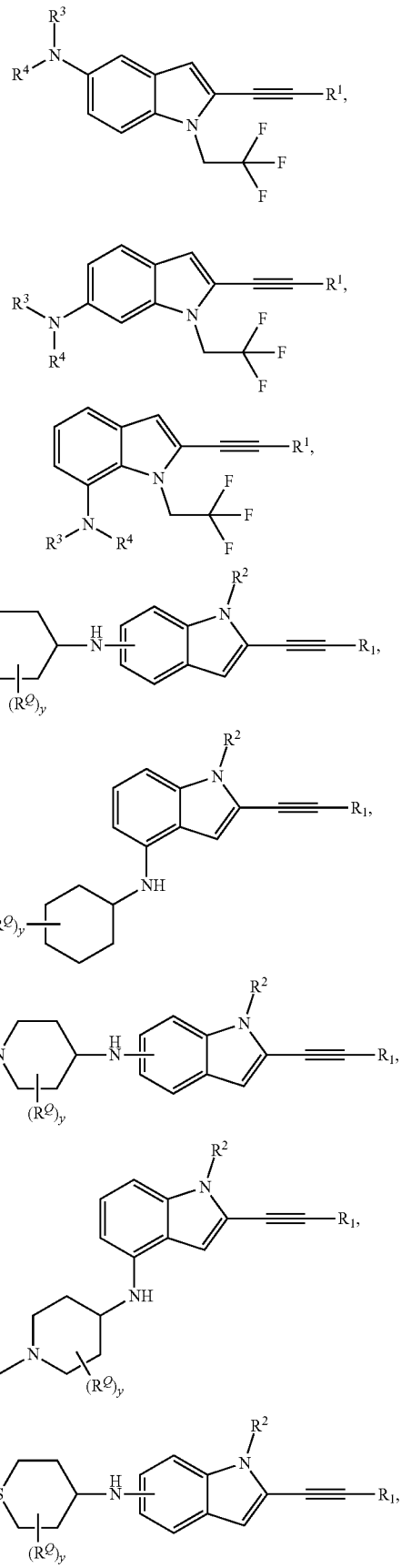

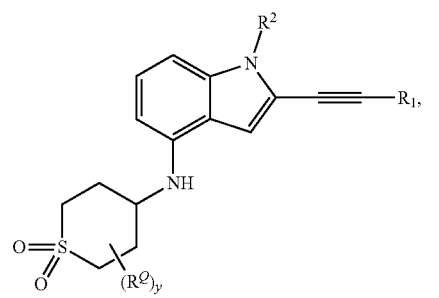
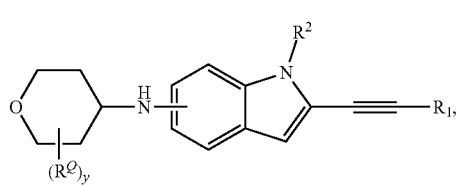
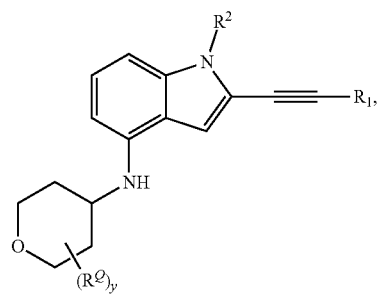
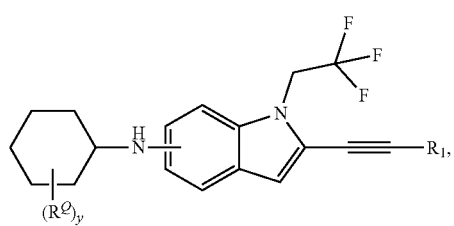
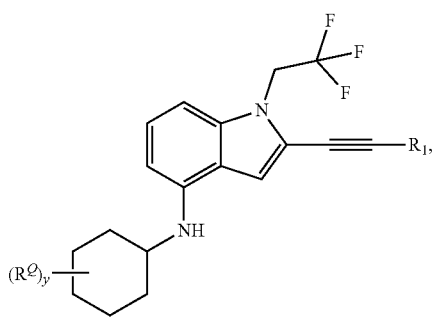
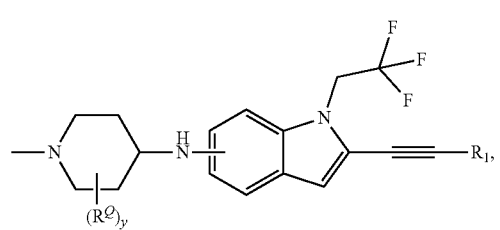
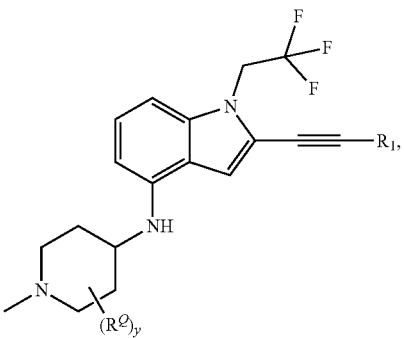
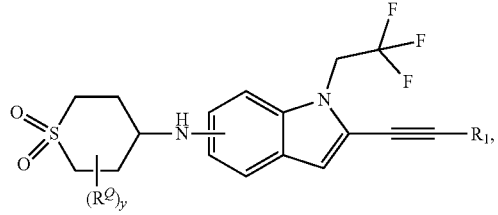
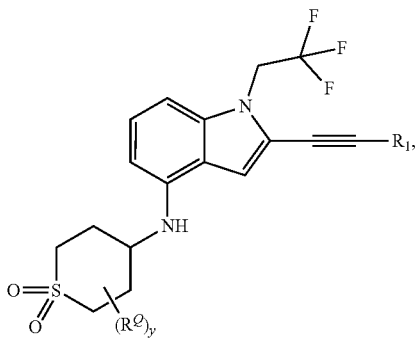
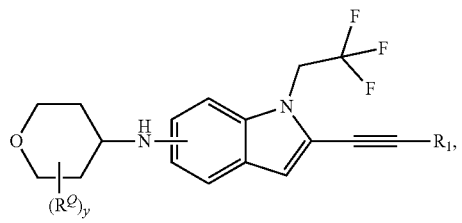
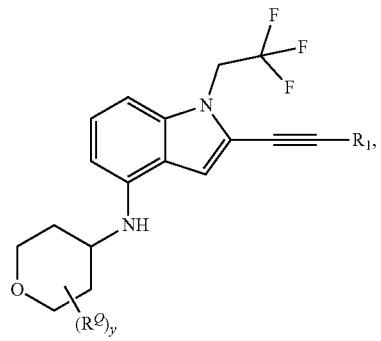
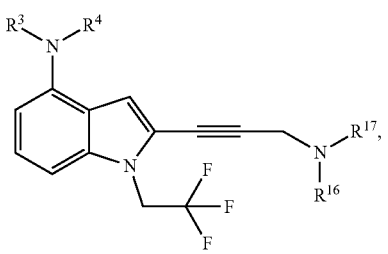

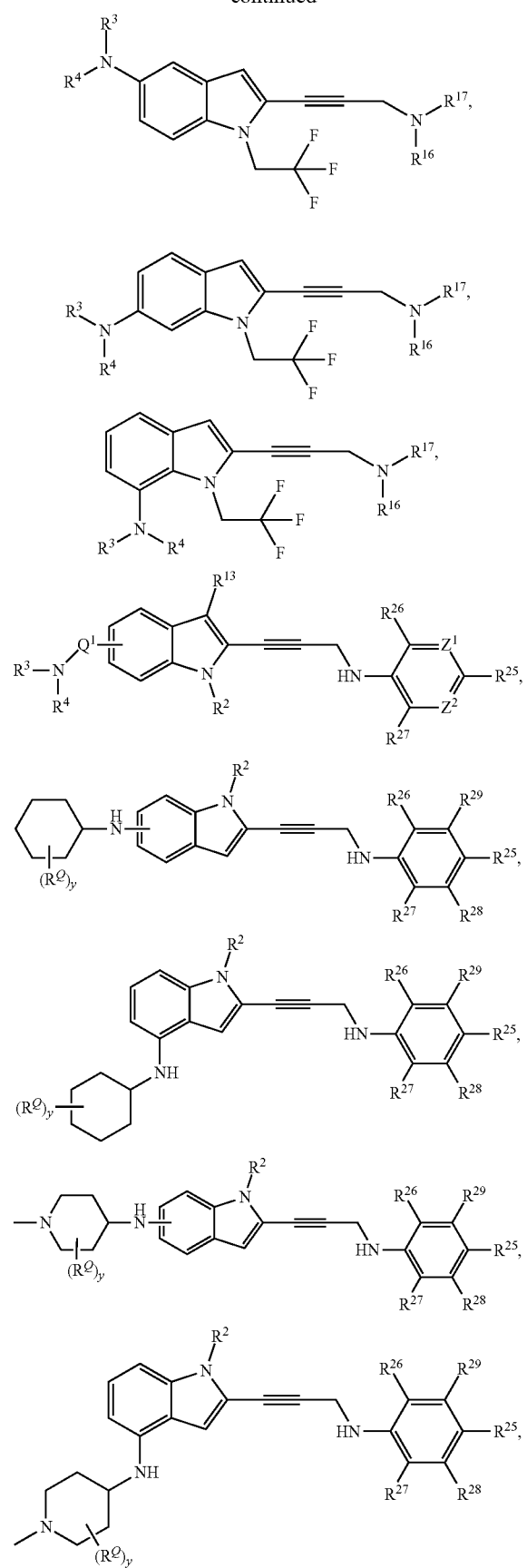
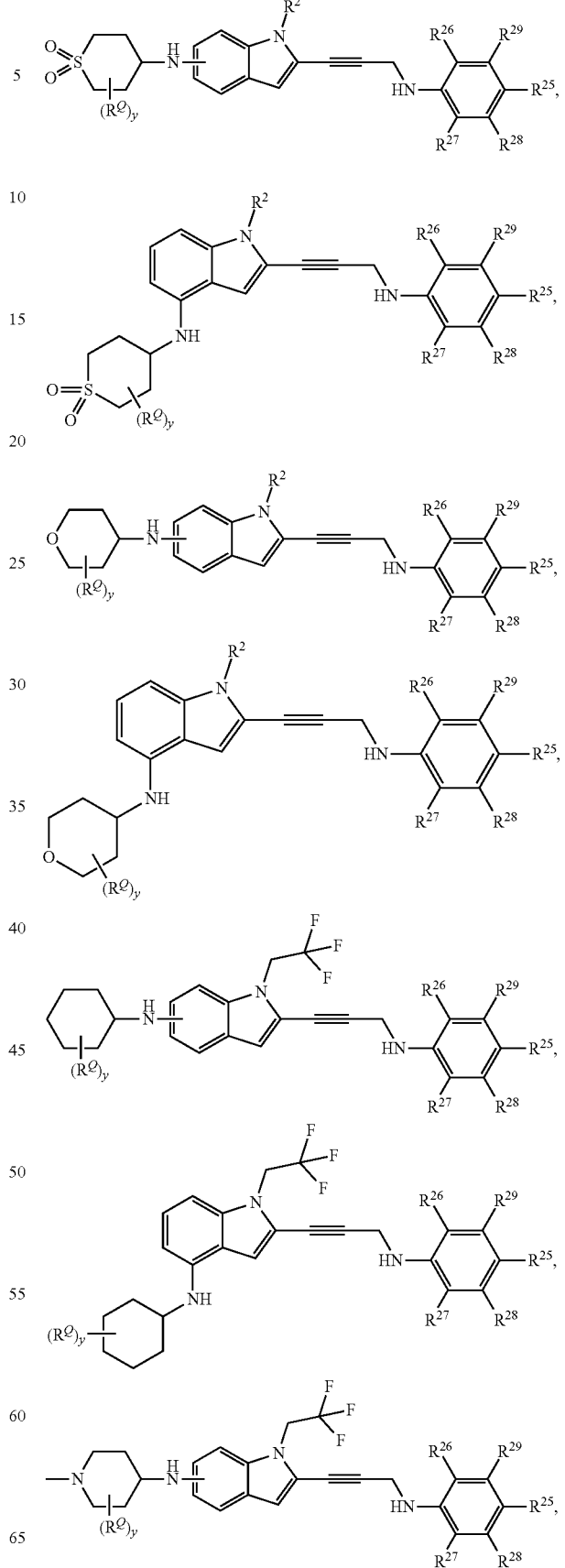

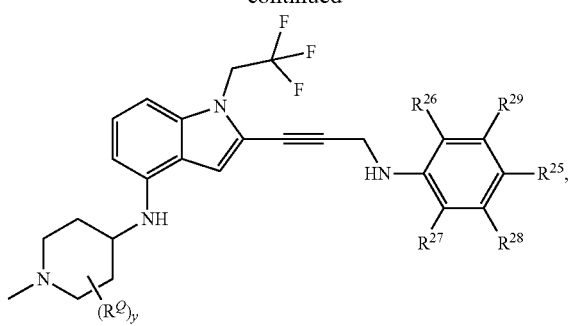
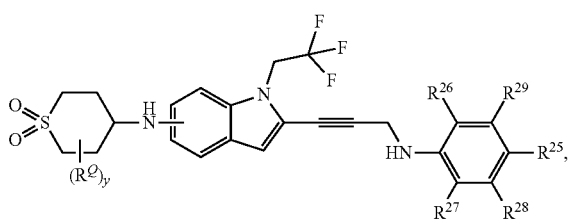
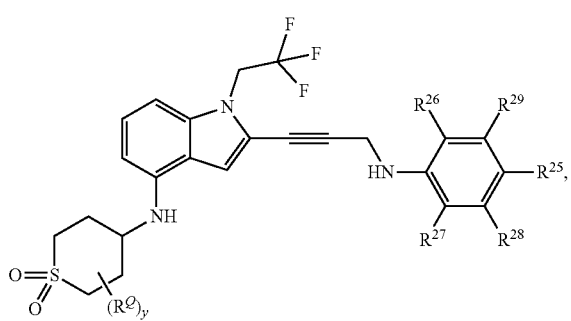
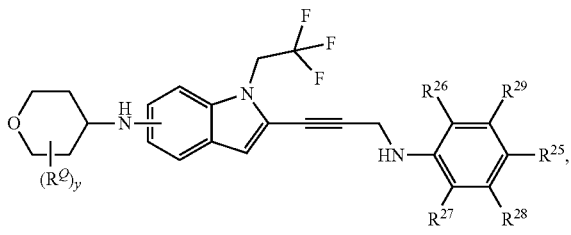
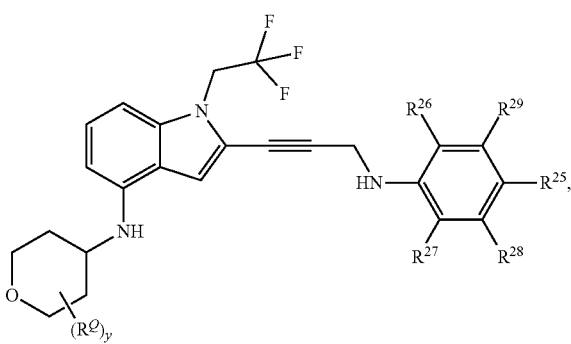
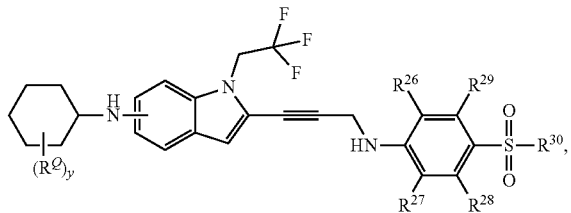
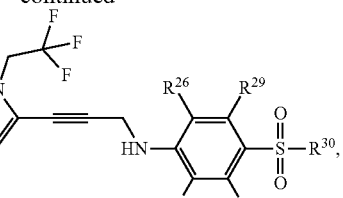
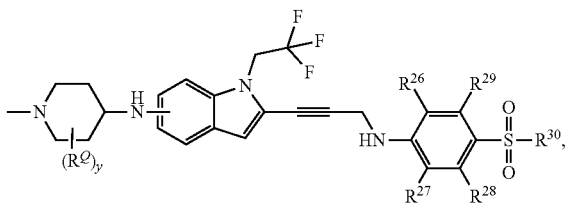
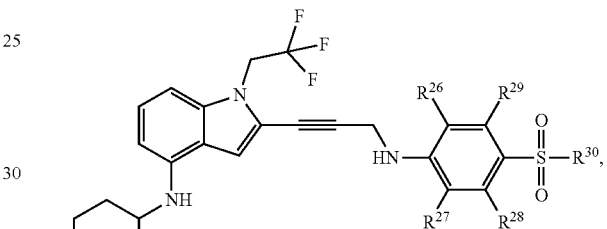
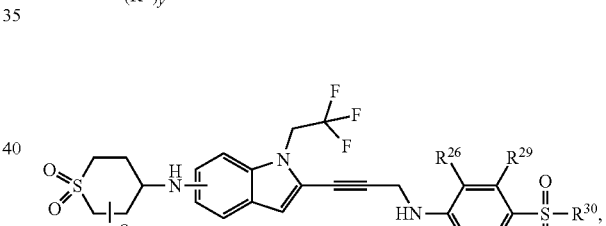
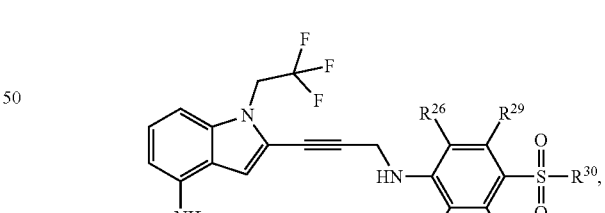
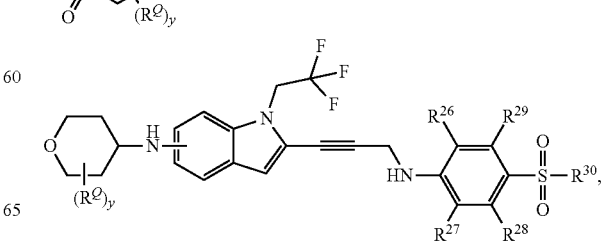

-continued

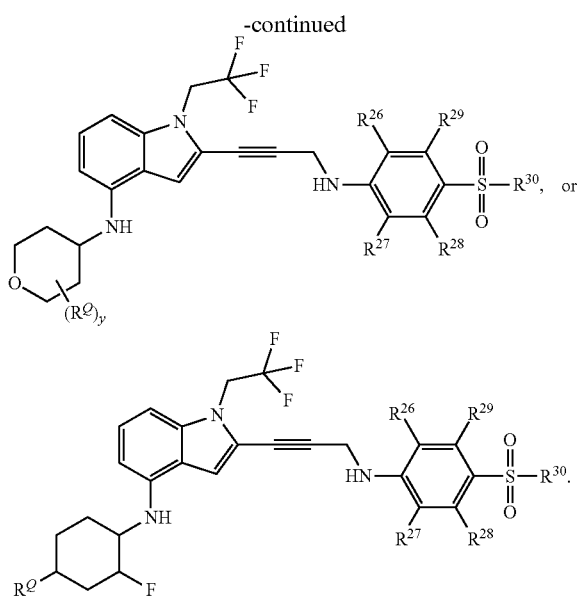

In some embodiments, the disclosure provides a compound of the formula:

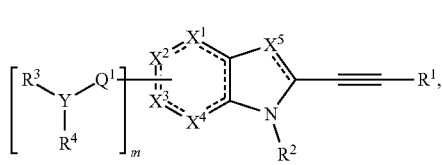

wherein:
each ≡≡≡ is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
$Q^1$ is C=O, C=S, C=$CR^{14}R^{15}$, C=$NR^{14}$, alkylene, alkenylene, or alkynylene, each of which is independently substituted or unsubstituted, or a bond;
m is 1, 2, 3, or 4;
Y is N, O, or absent;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, C=O, C=S, —CN, —Si$R^{16}R^{17}R^{18}$, alkyl, alkenyl, alkynyl, aryl, heteroaryl, or heterocyclyl, each of which is independently substituted or unsubstituted, or hydrogen;
each $R^3$ and $R^4$ is independently, —C(O)$R^{19}$, —C(O)O$R^{19}$, —C(O)N$R^{19}R^{20}$, —SO$R^{19}$, —SO$_2R^{19}$, alkyl, alkylene, alkenyl, alkenylene, alkynyl, aryl, heteroaryl, or heterocyclyl, each of which is independently substituted or unsubstituted, or hydrogen, or $R^3$ and $R^4$ together with the Y atom to which $R^3$ and $R^4$ are bound form a ring, wherein the ring is substituted or unsubstituted, or $R^3$ is absent;

each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen,
or a pharmaceutically-acceptable salt thereof, wherein the compound is not a compound of Table 1.

In some embodiments, disclosed herein is a compound of the formula:

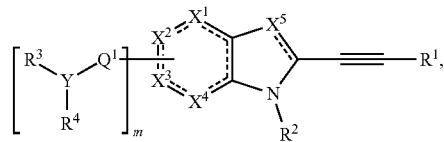

wherein:
each ≡≡≡ is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
$Q^1$ is C=O, C=S, C=$CR^{14}R^{15}$, C=$NR^{14}$, alkylene, alkenylene, or alkynylene, each of which is independently substituted or unsubstituted, or a bond;
m is 1, 2, 3, or 4;
Y is N, O, or absent;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, C=O, C=S, —CN, —Si$R^{16}R^{17}R^{18}$, alkyl, alkenyl, alkynyl, aryl, heteroaryl, or heterocyclyl, each of which is independently substituted or unsubstituted, or hydrogen;
each $R^3$ and $R^4$ is independently, —C(O)$R^{19}$, —C(O)O$R^{19}$, —C(O)N$R^{19}R^{20}$, —SO$R^{19}$, —SO$_2R^{19}$, alkyl, alkylene, alkenyl, alkenylene, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent, wherein at least one of $R^3$ and $R^4$ is alkyl, alkylene, alkenyl, alkenylene, alkynyl, aryl, heteroaryl, or heterocyclyl, each of which is substituted at least with halo-;

each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, the compound is of the formula:

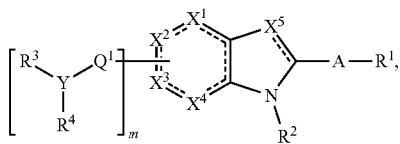

wherein:
each ------- is independently a single bond or a double bond;
$X^1$ is C$R^5$, C$R^5R^6$, N, N$R^5$, O, S, C=O, C=S, or a carbon atom connected to $Q^1$;
$X^2$ is C$R^7$, C$R^7R^8$, N, N$R^7$, O, S, C=O, C=S, or a carbon atom connected to $Q^1$;
$X^3$ is C$R^9$, C$R^9R^{10}$, N, N$R^9$, O, S, C=O, C=S, or a carbon atom connected to $Q^1$;
$X^4$ is C$R^{11}$, C$R^{11}R^{12}$, N, N$R^{11}$, O, S, C=O, C=S, or a carbon atom connected to $Q^1$;
$X^5$ is C$R^{13}$, N, or N$R^{13}$;
wherein at least one of $X^1$, $X^2$, $X^3$, and $X^4$ is a carbon atom connected to $Q^1$;
A is a linking group;
$Q^1$ is C=O, C=S, C=C$R^{14}R^{15}$, C=N$R^{14}$, alkylene, alkenylene, or alkynylene, each of which is independently substituted or unsubstituted, or a bond;
m is 1, 2, 3, or 4;
Y is N, O, or absent;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;
each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent; wherein at least one of $R^3$ and $R^4$ is alkyl, alkylene, alkenyl, alkenylene, alkynyl, alkynylene, aryl, heteroaryl, or heterocyclyl, each of which is substituted with at least halo;

each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is independently —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, the compound is of the formula:

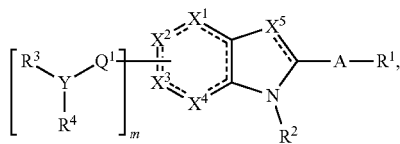

wherein:
each ------- is independently a single bond or a double bond;
$X^1$ is C$R^5$, C$R^5R^6$, N, N$R^5$, O, S, C=O, C=S, or a carbon atom connected to $Q^1$;
$X^2$ is C$R^7$, C$R^7R^8$, N, N$R^7$, O, S, C=O, C=S, or a carbon atom connected to $Q^1$;
$X^3$ is C$R^9$, C$R^9R^{10}$, N, N$R^9$, O, S, C=O, C=S, or a carbon atom connected to $Q^1$;
$X^4$ is C$R^{11}$, C$R^{11}R^{12}$, N, N$R^{11}$, O, S, C=O, C=S, or a carbon atom connected to $Q^1$;
$X^5$ is C$R^{13}$, N, or N$R^{13}$;
wherein at least one of $X^1$, $X^2$, $X^3$, and $X^4$ is a carbon atom connected to $Q^1$;
A is a linking group;
$Q^1$ is C=O, C=S, C=C$R^{14}R^{15}$, C=N$R^{14}$, alkylene, alkenylene, or alkynylene, each of which is independently substituted or unsubstituted, or a bond;
m is 1, 2, 3, or 4;
Y is N, O, or absent;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;
each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;

each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is independently —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof, wherein the compound is not a compound of Table 1.

In some embodiments, A is alkylene, alkenylene, or alkynylene, each of which is substituted or unsubstituted. In some embodiments, A is alkylene. In some embodiments, A is alkenylene. In some embodiments, A is alkynylene.

In some embodiments, the compound of the formula is:

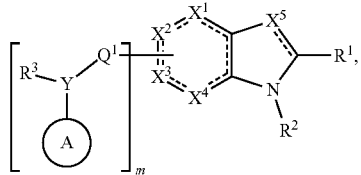

wherein:
each ====== is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
$Q^1$ is C=O, C=S, C=$CR^{14}R^{15}$, C=$NR^{14}$, alkylene, alkenylene, or alkynylene, each of which is independently substituted or unsubstituted, or a bond;
m is 1, 2, 3, or 4;
Y is N, O, or absent;
A is a cyclic group substituted with at least halo;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, C=O, C=S, —CN, —Si$R^{16}R^{17}R^{18}$, alkyl, alkenyl, alkynyl, aryl, heteroaryl, or heterocyclyl, each of which is independently substituted or unsubstituted, or hydrogen;

$R^3$ is —C(O)$R^{19}$, —C(O)O$R^{19}$, —C(O)N$R^{19}R^{20}$, —SO$R^{19}$, —SO$_2R^{19}$, alkyl, alkylene, alkenyl, alkenylene, alkynyl, aryl, heteroaryl, or heterocyclyl, each of which is independently substituted or unsubstituted, or hydrogen, or $R^3$ and A together with the nitrogen atom to which $R^3$ and A are bound form a ring, wherein the ring is substituted or unsubstituted, or $R^3$ is absent, each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, the compound is of the formula:

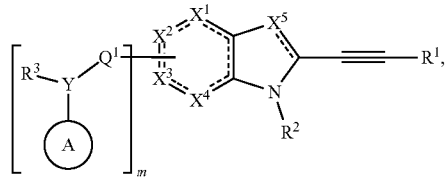

wherein:
each ====== is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
$Q^1$ is C=O, C=S, C=$CR^{14}R^{15}$, C=$NR^{14}$, alkylene, alkenylene, or alkynylene, each of which is independently substituted or unsubstituted, or a bond;
m is 1, 2, 3, or 4;
Y is N, O, or absent;
A is a cyclic group substituted with at least halo;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, C=O, C=S, —CN, —Si$R^{16}R^{17}R^{18}$, alkyl, alkenyl, alkynyl, aryl, heteroaryl, or heterocyclyl, each of which is independently substituted or unsubstituted, or hydrogen;

R³ is —C(O)R¹⁹, —C(O)OR¹⁹, —C(O)NR¹⁹R²⁰, —SOR¹⁹, —SO₂R¹⁹, alkyl, alkylene, alkenyl, alkenylene, alkynyl, aryl, heteroaryl, or heterocyclyl, each of which is independently substituted or unsubstituted, or hydrogen, or R³ and A together with the nitrogen atom to which R³ and A are bound form a ring, wherein the ring is substituted or unsubstituted, or R³ is absent, each R², R⁵, R⁶, R⁷, R⁸, R⁹, R¹⁰, R¹¹, R¹², R¹³, R¹⁴, R¹⁵, R¹⁶, R¹⁷, and R¹⁸ is independently —C(O)R²¹, —C(O)OR²¹, —C(O)NR²¹R²², —OR²¹, —SR²¹, —NR²¹R²², —NR²¹C(O)R²², —OC(O)R²¹, alkyl, alkenyl, alkynyl, aryl, heteroaryl, or heterocyclyl, each of which is independently substituted or unsubstituted, or hydrogen or halogen;

each R¹⁹ and R²⁰ is C(O)R²³, —C(O)OR²³, —C(O)NR²³R²⁴, —OR²³, —SR²³, —NR²³R²⁴, —NR²³C(O)R²⁴, —OC(O)R²³, alkyl, alkenyl, alkynyl, aryl, heteroaryl, or heterocyclyl, each of which is independently substituted or unsubstituted, or hydrogen or halogen;

each R²¹ and R²² is independently alkyl, alkenyl, alkynyl, aryl, heteroaryl, or heterocyclyl, each of which is independently substituted or unsubstituted, or hydrogen; and each R²³ and R²⁴ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, the pattern of dashed bonds is chosen to provide an aromatic system, for example, an indole, an indolene, a pyrrolopyridine, a pyrrolopyrimidine, or a pyrrolopyrazine.

In some embodiments, X¹ is CR⁵, CR⁵R⁶, or a carbon atom connected to Q¹. In some embodiments, X² is CR⁷, CR⁷R⁸, or a carbon atom connected to Q¹. In some embodiments, X³ is CR⁹, CR⁹R¹⁰, or a carbon atom connected to Q¹. In some embodiments, X⁴ is CR¹¹, CR¹¹R¹², or a carbon atom connected to Q¹. In some embodiments, X⁵ is CR¹³, N, or NR¹³. In some embodiments, X¹ is a carbon atom connected to Q¹. In some embodiments, X² is a carbon atom connected to Q¹. In some embodiments, X³ is a carbon atom connected to Q¹. In some embodiments, X⁴ is a carbon atom connected to Q¹. In some embodiments, X⁵ is N.

In some embodiments, Q¹ is a bond. In some embodiments, Q¹ is C₁-alkylene.

In some embodiments, m is 1. In some embodiments, m is 2. In some embodiments, m is 3. In some embodiments, m is 4.

In some embodiments, ring A is aryl, heteroaryl, or heterocyclyl, each of which is substituted or unsubstituted. In some embodiments, ring A is substituted aryl. In some embodiments, ring A is aryl substituted with fluoro-. In some embodiments, ring A is aryl substituted with chloro-. In some embodiments, ring A is substituted heteroaryl, In some embodiments, ring A is heteroaryl substituted with fluoro-. In some embodiments, ring A is heteroaryl substituted with chloro-. In some embodiments, ring A is substituted heterocyclyl. In some embodiments, ring A is heterocyclyl substituted with fluoro-. In some embodiments, ring A is heterocyclyl substituted with chloro-.

In some embodiments, R¹ is alkyl, alkenyl, —C(O)R¹⁶, —C(O)OR¹⁶, or —C(O)NR¹⁶R¹⁷, each of which is unsubstituted or substituted. In some embodiments, R¹ is substituted alkyl. In some embodiments, R¹ is alkyl substituted with NR¹⁶R¹⁷.

In some embodiments, each R¹⁶ and R¹⁷ is independently alkyl, alkenyl, aryl, heteroaryl, heterocyclyl, each of which is independently substituted or unsubstituted, or hydrogen. In some embodiments, R¹⁶ is hydrogen or alkyl. In some embodiments, R¹⁷ is aryl, heteroaryl, or heterocyclyl, each of which is independently substituted or unsubstituted. In some embodiments, R¹⁷ is substituted aryl. In some embodiments, R¹⁷ is substituted phenyl. In some embodiments, R¹⁷ is phenyl substituted with a sulfoxide group, carboxyl group, amide group, amino group, alkyl, alkoxy, hydroxy, halo, cyano, or heterocyclyl, each of which is independently substituted or unsubstituted. In some embodiments, R¹⁷ is phenyl substituted with methoxy. In some embodiments, R¹⁷ is phenyl substituted with a substituted sulfoxide group. In some embodiments, R¹⁷ is phenyl substituted with a carboxyl group. In some embodiments, R¹⁷ is phenyl substituted with a substituted amide group.

In some embodiments, the compound is of the formula:

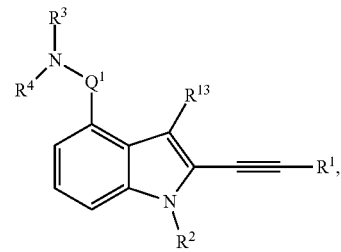

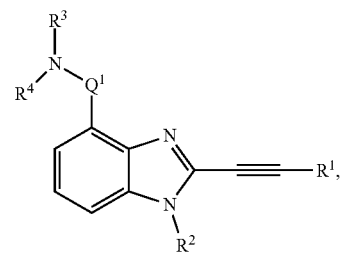

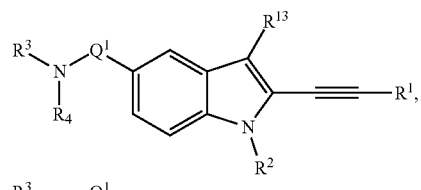

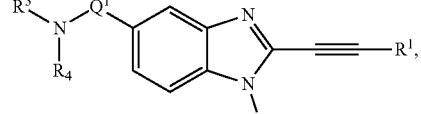

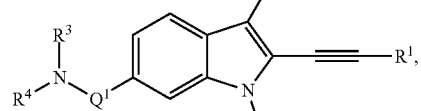

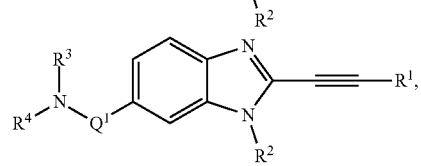

-continued

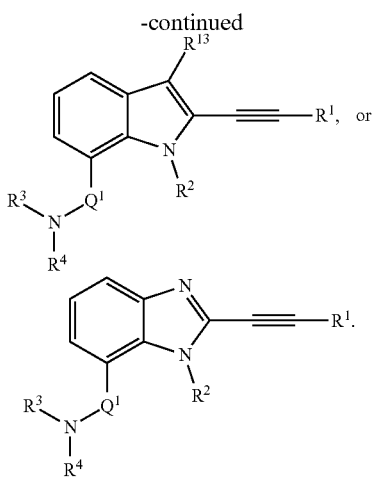

In some embodiments, $Q^1$ is C=O, C=S, C=$CR^{14}R^{15}$, C=$NR^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene or a bond. In some embodiments, $Q^1$ is $C_1$-alkylene. In some embodiments, $Q^1$ is a bond.

In some embodiments, Y is N. In some embodiments, Y is O. In some embodiments, Y is absent.

In some embodiments, $R^2$ is hydrogen or alkyl. In some embodiments, $R^2$ is alkyl. In some embodiments, $R^2$ is substituted $C_1$-$C_5$-alkyl. In some embodiments, $R^2$ is trifluoroethyl. In some embodiments, $R^2$ is cycloalkyl. In some embodiments, $R^2$ is cyclopropyl.

In some embodiments, $R^{13}$ is alkyl, alkenyl, hydrogen, or halogen. In some embodiments, $R^{13}$ is hydrogen.

In some embodiments, $R^2$ is $C_1$-$C_5$-alkyl, and $R^{13}$ is $C_1$-$C_5$-alkyl. In some embodiments, $R^2$ is $C_1$-$C_5$-alkyl, and $R^{13}$ is hydrogen. In some embodiments, $R^2$ is substituted $C_1$-$C_5$-alkylene. In some embodiments, $R^2$ is methyl, ethyl, propyl, iso-propyl, butyl, or tert-butyl, each of which is substituted or unsubstituted. In some embodiments, $R^{13}$ is methyl, ethyl, propyl, iso-propyl, butyl or tert-butyl. In some embodiments, $R^2$ is hydrogen, and $R^{13}$ is hydrogen. In some embodiments, $R^2$ is trifluoroethyl, and $R^{13}$ is hydrogen.

In some embodiments, the compound is of the formula:

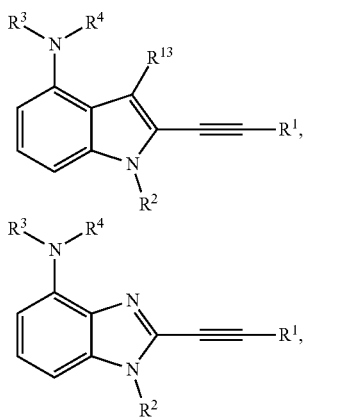

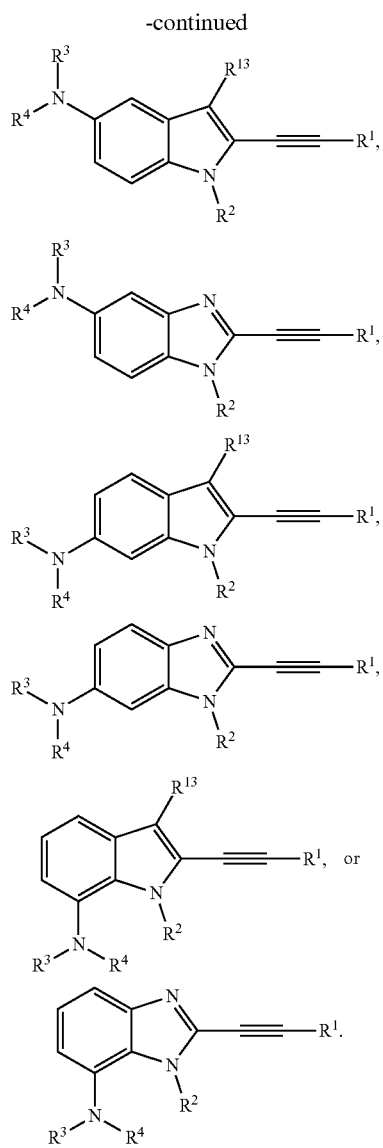

In some embodiments, the compound is of the formula:

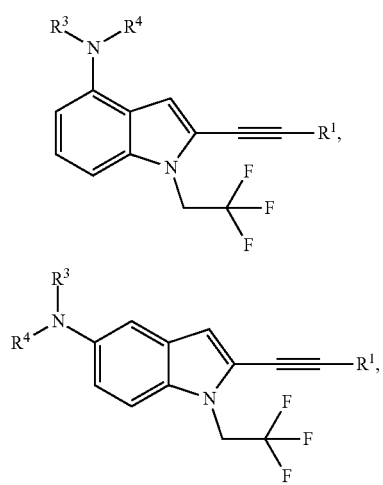

-continued

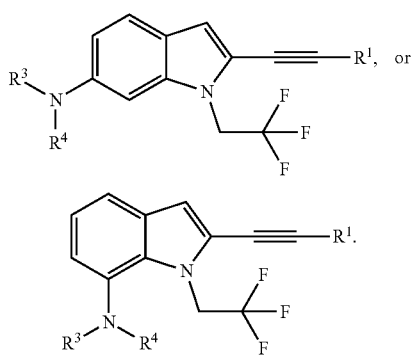

In some embodiments, $R^3$ is H, and $R^4$ is —C(O)$R^{19}$, —C(O)O$R^{19}$, —C(O)N$R^{19}R^{20}$, —SO$R^{19}$, —SO$_2R^{19}$, alkyl, alkylene, alkenyl, alkenylene, alkynyl, aryl, heteroaryl, or heterocyclyl, each of which is independently substituted or unsubstituted. In some embodiments, each $R^3$ and $R^4$ is independently substituted or unsubstituted $C_1$-$C_5$-alkylene. In some embodiments, $R^3$ is H, and $R^4$ is substituted or unsubstituted $C_1$-$C_4$ alkylene. In some embodiments, $R^3$ is H, and $R^4$ is substituted or unsubstituted heterocyclyl. In some embodiments, $R^3$ is H, and $R^4$ is substituted or unsubstituted piperidinyl. In some embodiments, $R^3$ is H, and $R^4$ is substituted or unsubstituted cycloalkyl. In some embodiments, $R^3$ is H, and $R^4$ is cycloalkyl substituted with an amino group. In some embodiments, $R^3$ is H, and $R^4$ is substituted or unsubstituted cyclobutyl. In some embodiments, $R^3$ is H, and $R^4$ is cyclobutyl substituted with an amino group. In some embodiments, $R^3$ is H, and $R^4$ is substituted or unsubstituted cyclohexyl. In some embodiments, $R^3$ is H, and $R^4$ is cyclohexyl substituted with an amino group.

In some embodiments, the compound is of the formula:

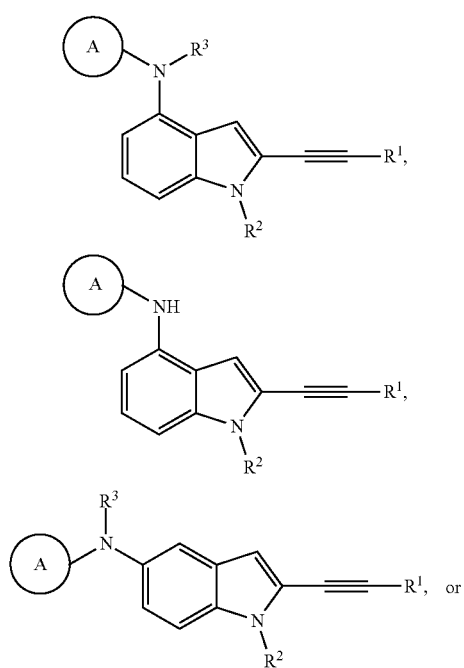

-continued

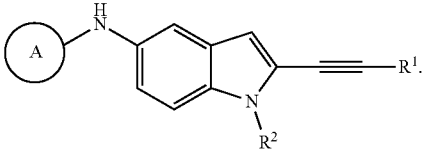

In some embodiments, the compound is of the formula:

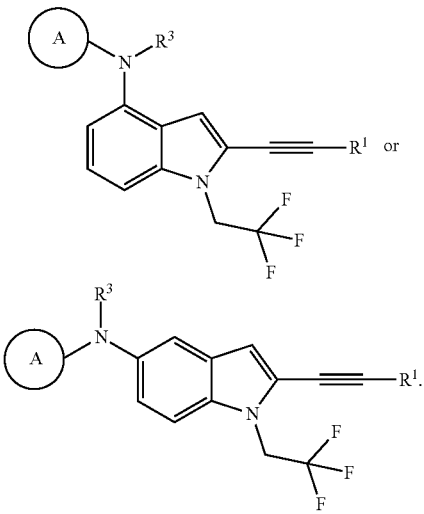

$R^1$ can be a group substituted with one or more substituents selected from a hydroxyl group, sulfhydryl group, halogens, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group. In some embodiments, $R^1$ is alkyl, alkenyl, —C(O)$R^{16}$, —C(O)O$R^{16}$, or —C(O)N$R^{16}R^{17}$. In some embodiments, $R^1$ is substituted or unsubstituted $C_1$-$C_3$ alkyl. In some embodiments, $R^1$ is $C_1$-$C_3$-alkyl substituted with an amine group. In some embodiments, $R^1$ is $C_1$-alkyl substituted with N$R^{16}R^{17}$. In some embodiments, each $R^{16}$ and $R^{17}$ is independently aryl, heteroaryl, or heterocyclyl, each of which is independently substituted or unsubstituted, or hydrogen. In some embodiments, $R^{16}$ is H, and $R^{17}$ is substituted aryl. In some embodiments, $R^{16}$ is H, and $R^{17}$ is substituted phenyl. In some embodiments, $R^{16}$ is H, and $R^{17}$ is phenyl substituted with alkyl, alkoxy, halo, sulfonamide, a sulfone, or a carboxy group. In some embodiments, $R^{16}$ is H, and $R^{17}$ is substituted heteroaryl. In some embodiments, $R^{16}$ is H, and $R^{17}$ is substituted heterocyclyl.

In some embodiments, $R^3$ is —C(O)$R^{19}$, —C(O)O$R^{19}$, alkyl, alkenyl, alkynyl, aryl, heteroaryl, or heterocyclyl, each of which is independently substituted or unsubstituted, or hydrogen, and $R^4$ is —C(O)$R^{19}$, —C(O)O$R^{19}$, alkyl, alkenyl, alkynyl, aryl, heteroaryl, or heterocyclyl, each of which is independently substituted or unsubstituted, or hydrogen. In some embodiments, $R^3$ is alkyl, alkenyl, alkynyl, aryl, heteroaryl, or heterocyclyl, each of which is independently substituted or unsubstituted, or hydrogen. In some embodiments, $R^3$ is substituted alkyl. In some embodiments, $R^3$ is H.

In some embodiments, $R^3$ is hydrogen and $R^4$ is a ring A. In some embodiments, $R^4$ or ring A is cycloalkyl, aryl, heteroaryl, or heterocyclyl, each of which is independently substituted or unsubstituted. In some embodiments, $R^4$ or ring A is substituted or unsubstituted aryl. In some embodiments, $R^4$ or ring A is substituted or unsubstituted phenyl. In some embodiments, $R^4$ or ring A is substituted or unsubstituted cycloalkyl. In some embodiments, $R^4$ or ring A is substituted or unsubstituted cyclopropyl. In some embodiments, $R^4$ or ring A is substituted cyclopropyl. In some embodiments, $R^4$ or ring A is substituted cyclohexyl. In some embodiments, $R^4$ or ring A is cyclohexyl substituted with an amino group.

In some embodiments, $R^3$ is H, and $R^4$ or ring A is unsubstituted or substituted heterocyclyl. In some embodiments, $R^4$ or ring A is heterocyclyl. In some embodiments, $R^4$ or ring A is piperidinyl, piperazinyl, tetahydropyranyl, morpholinyl, or pyrrolidinyl, each of which is independently substituted or unsubstituted. In some embodiments, $R^3$ is H, and $R^4$ or ring A is substituted piperidinyl. In some embodiments, $R^3$ is H, and $R^4$ or ring A is piperidine substituted with alkyl, carboxy, heterocyclyl, or an amide group. In some embodiments, $R^3$ is H, and $R^4$ or ring A is unsubstituted or substituted methyl piperidinyl. In some embodiments, $R^3$ is H, and $R^4$ or ring A is 3-fluoro-1-methylpiperidinyl. In some embodiments, $R^3$ is H, and $R^4$ or ring A is piperidinyl substituted with methoxypropanol. In some embodiments, $R^3$ is H, and $R^4$ or ring A is 3-fluoro-1-(2-hydroxy-3-methoxypropyl)piperidinyl. In some embodiments, $R^3$ is H, and $R^4$ or ring A is unsubstituted or substituted tetrahydropyranyl. In some embodiments, $R^3$ is H, and $R^4$ or ring A is unsubstituted tetrahydropyranyl. In some embodiments, $R^3$ is H, and $R^4$ or ring A is tetrahydropyranyl substituted with alkyl. In some embodiments, $R^3$ is H, and $R^4$ or ring A is tetrahydrothiopyran-1,1-dioxide.

In some embodiments, $R^4$ or ring A is cycloalkyl, aryl, heteroaryl, or heterocyclyl, each of which is substituted at least with halo-. In some embodiments, $R^4$ or ring A is $C_4$-$C_6$-cycloalkyl substituted with at least halo-. In some embodiments, $R^4$ or ring A is cyclohexyl substituted with at least halo-. In some embodiments, $R^4$ or ring A is aryl substituted with at least halo-. In some embodiments, $R^4$ or ring A is phenyl substituted with at least halo-. In some embodiments, $R^4$ or ring A is aryl substituted with fluoro-. In some embodiments, $R^4$ or ring A is phenyl substituted with fluoro-. In some embodiments, $R^4$ or ring A is aryl substituted with chloro-. In some embodiments, $R^4$ or ring A is phenyl substituted with chloro-. In some embodiments, $R^4$ or ring A is heteroaryl substituted with at least halo-. In some embodiments, $R^4$ or ring A is heteroaryl substituted with fluoro-. In some embodiments, $R^4$ or ring A is heteroaryl substituted with chloro-. In some embodiments, $R^4$ or ring A is $C_4$-$C_6$-heterocyclyl substituted with at least halo-. In some embodiments, $R^4$ or ring A is heterocyclyl substituted with fluoro-. In some embodiments, $R^4$ or ring A is heterocyclyl substituted with chloro-.

In some embodiments, $R^4$ or ring A is piperidinyl, piperazinyl, tetahydropyranyl, morpholinyl, or pyrrolidinyl, each of which is independently substituted with at least halo-. In some embodiments, $R^4$ or ring A is piperidinyl substituted with halo-. In some embodiments, $R^4$ or ring A is methylpiperidinyl substituted with halo-. In some embodiments, $R^4$ or ring A is 3-fluoro-1-methylpiperidinyl. In some embodiments, $R^4$ or ring A is 3-fluoro-1-(2-hydroxy-3-methoxypropyl)piperidinyl. In some embodiments, $R^4$ or ring A is tetrahydropyranyl substituted with at least halo-.

In some embodiments, $R^4$ or Ring A is a ring that is:

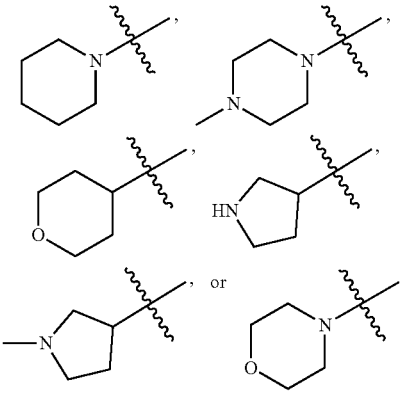

wherein the ring is substituted or unsubstituted. In some embodiments, the ring is substituted with halo-. In some embodiments, the ring is substituted with fluoro. In some embodiments, $R^3$ is H, and $R^4$ is a ring that is

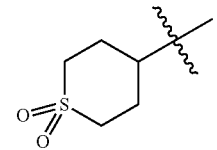

wherein the ring is substituted or unsubstituted. In some embodiments, the ring is substituted with halo-. In some embodiments, the ring is substituted with fluoro. In some embodiments, $R^3$ is H, and $R^4$ is a ring that is

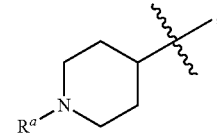

wherein the ring is substituted or unsubstituted. In some embodiments, $R^a$ is alkylene. In some embodiments, $R^a$ is methyl. In some embodiments, the ring is substituted with halo. In some embodiments, the ring is substituted with fluoro. In some embodiments, $R^3$ is H, and $R^4$ is a ring that is

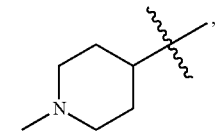

wherein the ring is substituted or unsubstituted. In some embodiments, the ring is substituted with halo. In some embodiments, the ring is substituted with fluoro. In some embodiments, $R^3$ is H, and $R^4$ is a ring that is

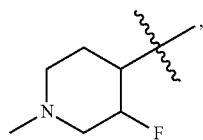 [SMILES: *C1CCN(C)CC1F]

wherein the ring is substituted or unsubstituted.

In some embodiments, the $R^4$ or ring A is substituted with one or more substituents selected from a hydroxyl group, sulfhydryl group, halogens, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group.

In some embodiments, $R^3$ and $R^4$ together with the nitrogen atom to which $R^3$ and $R^4$ are bound form a ring, wherein the ring is substituted or unsubstituted. In some embodiments, $R^3$ and $R^4$ together with the nitrogen atom to which $R^3$ and $R^4$ are bound form a substituted heterocycle. In some embodiments, $R^3$ and $R^4$ together with the nitrogen atom to which $R^3$ and $R^4$ are bound form a heterocycle substituted with a hydroxyl group, halogen, amino group, or alkyl group. In some embodiments, $R^3$ and $R^4$ together with the nitrogen atom to which $R^3$ and $R^4$ are bound form a heterocycle, wherein the heterocycle is substituted by a substituted or unsubstituted heterocycle.

In some embodiments, the compound is of the formula:

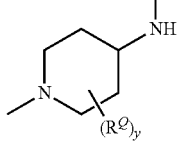

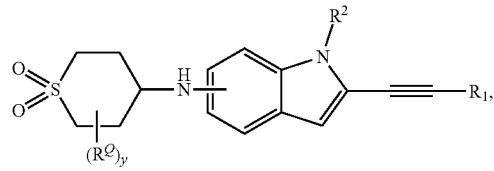

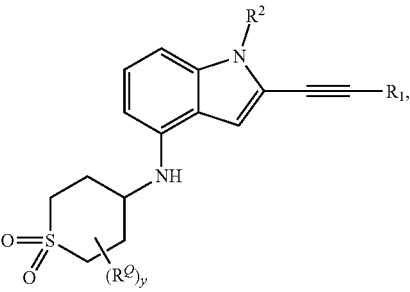

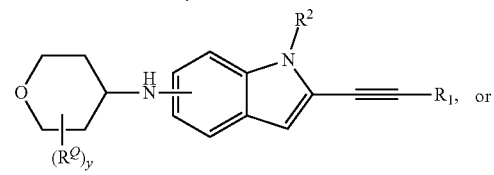

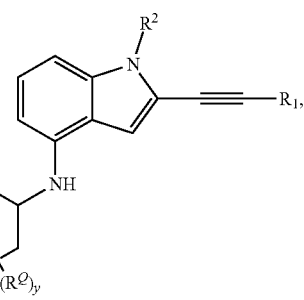

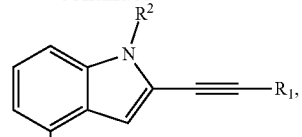

-continued wherein:
$R^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, C=O, C=S, —CN, —SiR$^{16}$R$^{17}$R$^{18}$, alkyl, alkenyl, alkynyl, aryl, heteroaryl, or heterocyclyl, each of which is independently substituted or unsubstituted, or hydrogen;

each $R^Q$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

y is 0, 1, 2, 3, or 4;

each $R^{16}$, $R^{17}$, and $R^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is $C(O)R^{23}$, —$C(O)OR^{23}$, —$C(O)NR^{23}R^{24}$, —$OR^{23}$, —$SR^{23}$, —$NR^{23}R^{24}$, —$NR^{23}C(O)R^{24}$, —$OC(O)R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, $R^1$ is —$C(O)R^{16}$, —$C(O)OR^{16}$, —$C(O)NR^{16}R^{17}$, —$OR^{16}$, —$SR^{16}$, —$NR^{16}R^{17}$, —$NR^{16}C(O)R^{16}$, —$OC(O)R^{16}$, —$SiR^{16}R^{17}R^{18}$, alkyl, alkenyl, alkynyl, alkoxy, aryl, heteroaryl, or heterocyclyl, each of which is independently substituted or unsubstituted, or hydrogen. In some embodiments, $R^1$ is alkyl, alkylene, alkoxy, —$NR^{21}R^{22}$, or aryl, each of which is independently substituted or unsubstituted; halo or hydrogen.

In some embodiments, $R^1$ is substituted $C_1$-$C_3$-alkyl. In some embodiments, $R^1$ is $C_1$-$C_3$-alkyl substituted with $NR^{16}R^{17}$. In some embodiments, $R^1$ is methyl substituted with $NR^{16}R^{17}$, wherein each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^1$ is methyl substituted with $NR^{16}R^{17}$, wherein $R^{16}$ is hydrogen, and $R^{17}$ is a substituted carboxyl group. In some embodiments, $R^1$ is methyl substituted with $NR^{16}R^{17}$, wherein $R^{16}$ is hydrogen, and $R^{17}$ is substituted aryl. In some embodiments, $R^1$ is methyl substituted with $NR^{16}R^{17}$, wherein $R^{16}$ is hydrogen, and $R^{17}$ is substituted phenyl. In some embodiments, $R^1$ is methyl substituted with $NR^{16}R^{17}$, wherein $R^{16}$ is hydrogen, and $R^{17}$ is phenyl. substituted with a sulfoxide group, carboxyl group, amide group, amino group, alkyl, alkoxy, hydroxy, halo, cyano, or heterocyclyl, each of which is independently substituted or unsubstituted. In some embodiments, $R^{17}$ is phenyl substituted with methoxy. In some embodiments, $R^{17}$ is phenyl substituted with a substituted sulfoxide group. In some embodiments, $R^{17}$ is phenyl substituted with a carboxyl group. In some embodiments, $R^{17}$ is a substituted amide group. In some embodiments, $R^{17}$ is substituted with methoxy and sulfonamide.

In some embodiments, $R^2$ is hydrogen or alkyl. In some embodiments, $R^2$ is substituted $C_1$-$C_5$-alkylene. In some embodiments, $R^2$ is trifluoroethyl.

In some embodiments, the compound is of the formula:

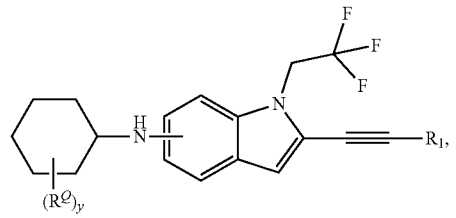

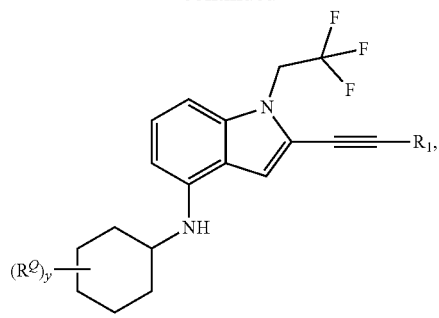

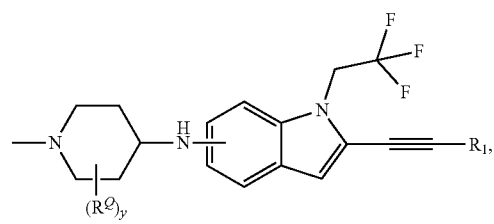

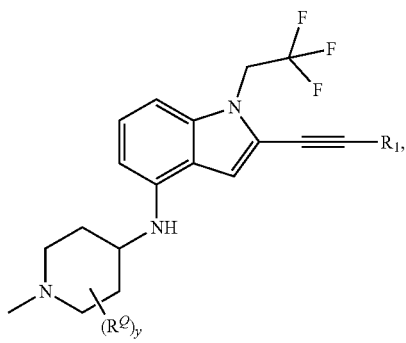

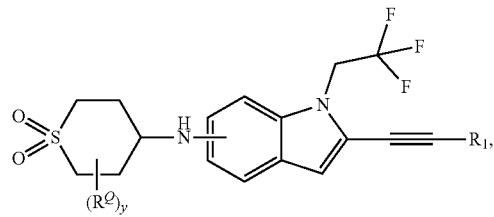

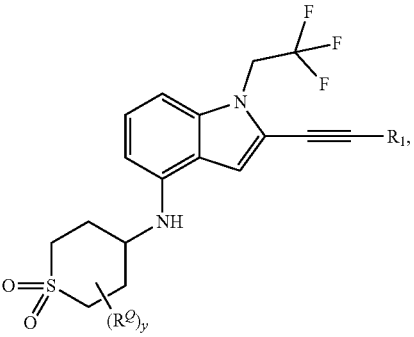

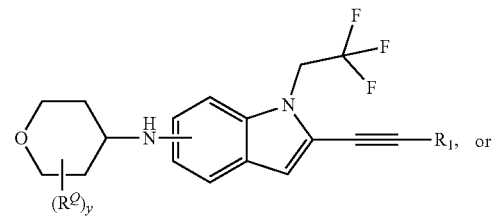

-continued

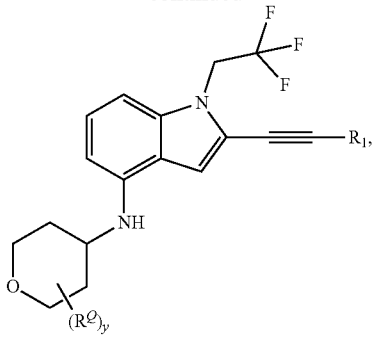

or a pharmaceutically-acceptable salt thereof, wherein the variables are as defined above.

In some embodiments, each $R^Q$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen. In some embodiments, each $R^Q$ is In some embodiments, y is 1. In some embodiments, y is 2. In some embodiments, y is 3. In some embodiments, y is 4.

In some embodiments, $R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, or heterocyclyl, each of which is independently substituted or unsubstituted, or hydrogen. In some embodiments, $R^1$ is alkyl, alkylene, alkoxy, —N$R^{21}R^{22}$, or aryl, each of which is independently substituted or unsubstituted; halo or hydrogen.

In some embodiments, $R^1$ is substituted alkyl. In some embodiments, $R^1$ is substituted $C_1$-$C_3$-alkyl. In some embodiments, $R^1$ is alkyl substituted with N$R^{16}R^{17}$. In some embodiments, $R^1$ is $C_1$-$C_3$-alkyl substituted with N$R^{16}R^{17}$. In some embodiments, $R^1$ is methyl substituted with N$R^{16}R^{17}$, wherein each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^1$ is methyl substituted with N$R^{16}R^{17}$, wherein $R^{16}$ is hydrogen, and $R^{17}$ is a substituted carboxyl group.

In some embodiments, $R^{16}$ is alkyl, alkenyl, aryl, heteroaryl, heterocyclyl, or hydrogen, and $R^{17}$ is aryl, heteroaryl, or heterocyclyl. In some embodiments, $R^{16}$ is hydrogen, and $R^{17}$ is phenyl, indolyl, piperidinyl, imidazolyl, thiazolyl, morpholinyl, pyrrolyl, or pyridinyl, each of which is substituted or unsubstituted.

In some embodiments, the compound is of the formula:

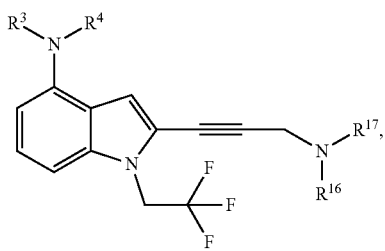

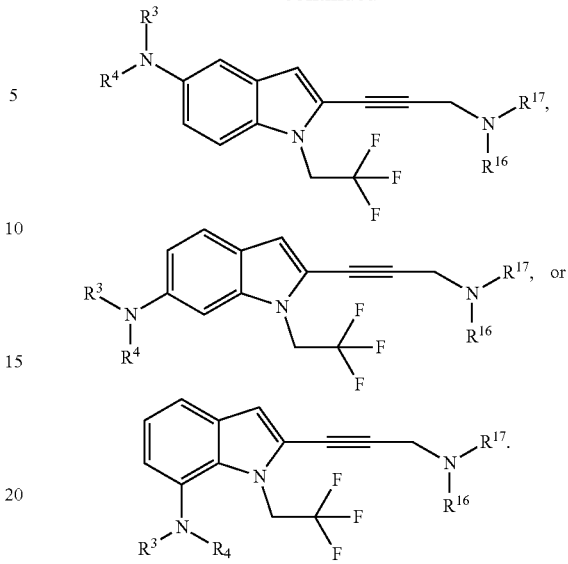

In some embodiments, each $R^{16}$ and $R^{17}$ is independently alkyl, alkenyl, aryl, heteroaryl, heterocyclyl, or hydrogen. In some embodiments, $R^{16}$ is aryl, and $R^{17}$ is alkyl. In some embodiments, $R^{16}$ is aryl, and $R^{17}$ is hydrogen. In some embodiments, $R^{16}$ is heteroaryl, and $R^{17}$ is alkyl. In some embodiments, $R^{16}$ is heteroaryl, and $R^{17}$ is hydrogen. In some embodiments, $R^{16}$ is substituted heteroaryl, and $R^{17}$ is hydrogen. In some embodiments, $R^{16}$ is substituted alkyl, and $R^{17}$ is hydrogen. In some embodiments, $R^{17}$ is aryl, heteroaryl, or heterocyclyl, each of which is independently substituted or unsubstituted with halogen, alkyl, or hydroxyl. In some embodiments, $R^{16}$ is hydrogen, and $R^{17}$ is aryl or heteroaryl, substituted or unsubstituted with halogen or alkyl. In some embodiments, $R^{16}$ is alkyl, and $R^{17}$ is heteroaryl substituted with halogen or alkyl. In some embodiments, $R^{16}$ is hydrogen. In some embodiments, $R^{17}$ is aryl, heteroaryl, or heterocyclyl, each of which is independently substituted or unsubstituted with alkyl. In some embodiments, $R^{17}$ is aryl or heteroaryl, each of which is independently substituted with alkyl, wherein the alkyl is optionally substituted with fluorine, chlorine, bromine, iodine, or cyano. In some embodiments, $R^{16}$ is alkyl, alkenyl, aryl, heteroaryl, heterocyclyl, or hydrogen, and $R^{17}$ is aryl, heteroaryl, or heterocyclyl. In some embodiments, $R^{16}$ is hydrogen, and $R^{17}$ is phenyl, indolyl, piperidinyl, imidazolyl, thiazolyl, morpholinyl, pyrrolyl, or pyridinyl, each of which is substituted or unsubstituted. In some embodiments, $R^{16}$ is hydrogen, and $R^{17}$ is substituted phenyl. In some embodiments, $R^{16}$ is hydrogen, and $R^{17}$ is phenyl substituted with a sulfoxide group, carboxyl group, amide group, amino group, alkyl, alkoxy, hydroxy, halo, cyano, or heterocyclyl, each of which is independently substituted or unsubstituted. In some embodiments, $R^{17}$ is phenyl substituted with methoxy. In some embodiments, $R^{17}$ is phenyl substituted with a substituted sulfoxide group. In some embodiments, $R^{17}$ is phenyl substituted with a carboxyl group. In some embodiments, $R^{17}$ is a substituted amide group. In some embodiments, $R^{17}$ is substituted with methoxy and sulfonamide.

In some embodiments, each $R^3$ and $R^4$ is independently unsubstituted or substituted alkyl. In some embodiments, $R^3$ is hydrogen and $R^4$ is —C(O)$R^{19}$, —C(O)O$R^{19}$, alkyl, alkenyl, alkynyl, aryl, heteroaryl, or heterocyclyl, each of which is independently substituted or unsubstituted. In some embodiments, $R^3$ is hydrogen, and $R^4$ is alkyl, aryl, heteroaryl, or heterocyclyl, each of which is independently substituted or unsubstituted. In some embodiments, $R^3$ is H, and $R^4$ is substituted heterocyclyl. In some embodiments, $R^3$ is H, and $R^4$ is substituted or unsubstituted $C_4$-$C_6$-heterocyclyl. In some embodiments, $R^3$ is H, and $R^4$ is substituted alkyl. In some embodiments, $R^3$ is H, and $R^4$ is substituted $C_1$-$C_5$-alkyl. In some embodiments, $R^3$ is H, and $R^4$ is substituted or unsubstituted cycloalkyl. In some embodiments, $R^3$ is H, and $R^4$ is substituted or unsubstituted $C_4$-$C_6$-cycloalkyl. In some embodiments, $R^3$ is H, and $R^4$ is $C_4$-$C_6$-cycloalkyl substituted with an amino group.

In some embodiments, the compound is of the formula:

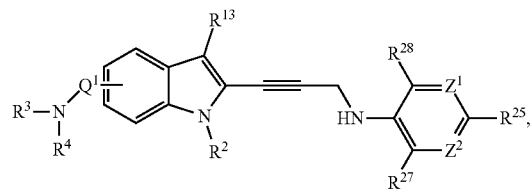

wherein:
- $Q^1$ is C=O, C=S, C=$CR^{14}R^{15}$, C=$NR^{14}$, alkylene, alkenylene, or alkynylene, each of which is independently substituted or unsubstituted, or a bond;
- $R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, C=O, C=S, —CN, —Si$R^{16}R^{17}R^{18}$, alkyl, alkenyl, alkynyl, aryl, heteroaryl, or heterocyclyl, each of which is independently substituted or unsubstituted, or hydrogen;
- each $R^3$ and $R^4$ is independently, —C(O)$R^{19}$, —C(O)O$R^{19}$, —C(O)N$R^{19}R^{20}$, —SO$R^{19}$, —SO$_2R^{19}$, alkyl, alkylene, alkenyl, alkenylene, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent, wherein at least one of $R^3$ and $R^4$ is alkyl, alkylene, alkenyl, alkenylene, alkynyl, aryl, heteroaryl, or heterocyclyl, each of which is substituted at least with halo-;
- each $Z^1$ and $Z^2$ is independently $CR^{28}$, $CR^{29}$, or N;
- each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
- each $R^{19}$ and $R^{20}$ is C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
- each $R^{21}$ and $R^{22}$ is independently alkyl, alkenyl, alkynyl, aryl, heteroaryl, or heterocyclyl, each of which is independently substituted or unsubstituted, or hydrogen;
- each $R^{23}$ and $R^{24}$ is independently alkyl, alkenyl, alkynyl, aryl, heteroaryl, or heterocyclyl, each of which is independently substituted or unsubstituted, or hydrogen; and
- each $R^{25}$, $R^{26}$, $R^{27}$, $R^{28}$, and $R^{29}$ is independently hydrogen or a substituent selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and ester group. or a pharmaceutically-acceptable salt thereof.

In some embodiments, $Z^1$ is N. In some embodiments, $Z^1$ and $Z^2$ are N. In some embodiments, each $R^{25}$ and $R^{26}$ is independently a halogen. In some embodiments, $R^{25}$ is

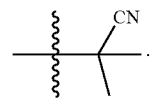

In some embodiments, $R^{25}$ is a substituted sulfone group. In some embodiments, $R^{25}$ is a sulfone group substituted with alkyl. In some embodiments, $R^{25}$ is a methanesulfonyl group. In some embodiments, $R^{25}$ is a sulfone group substituted with an amino group. In some embodiments, $R^{25}$ is a sulfonamide. In some embodiments, $R^{25}$ is a carboxy group. In some embodiments, $R^{25}$ is a methoxycarbonyl group.

In some embodiments, the compound is of the formula:

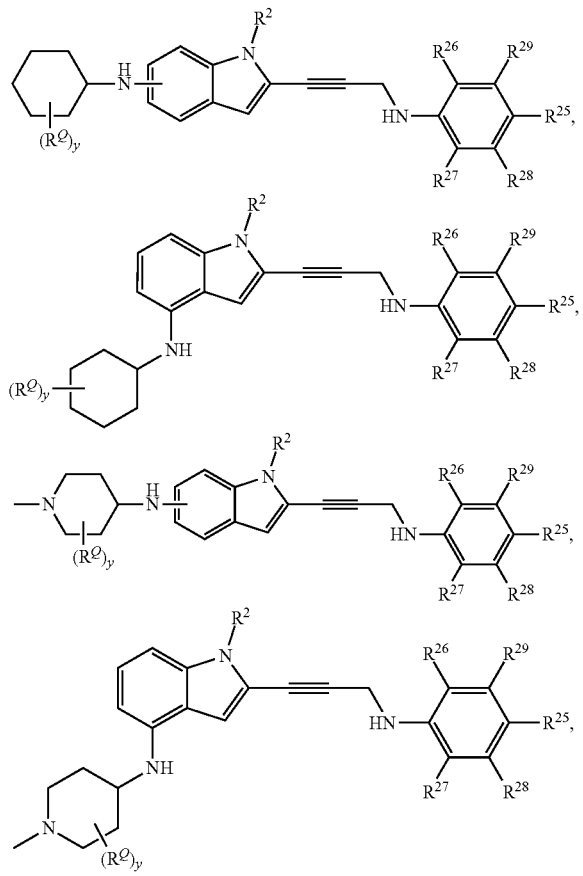

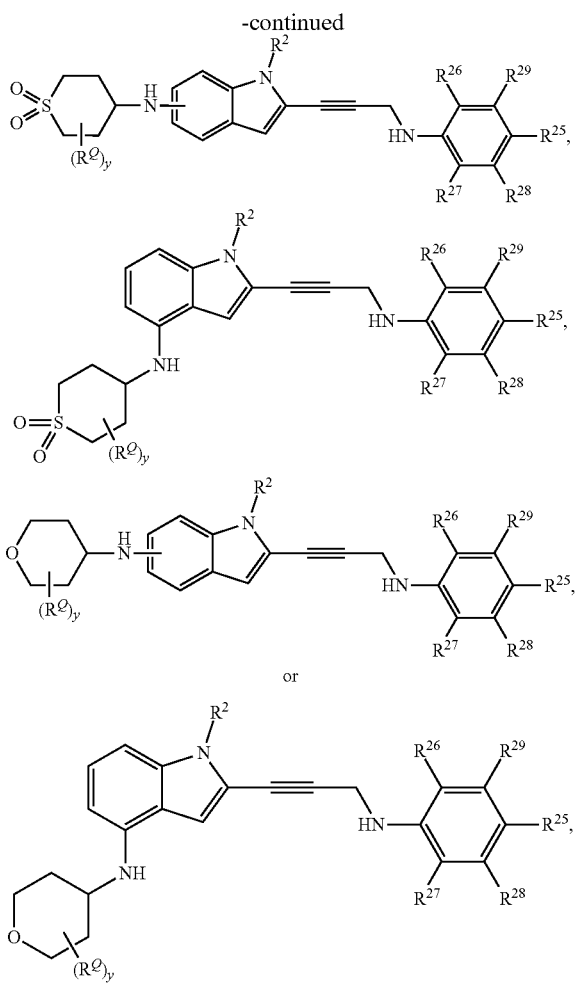

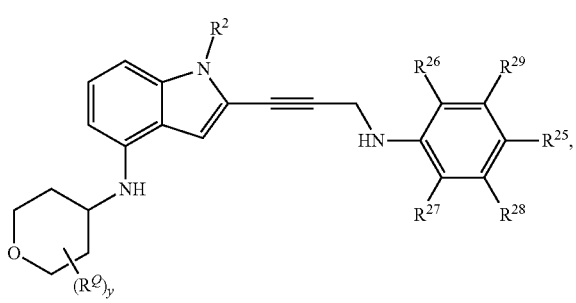

wherein:
R² is —C(O)R²¹, —C(O)OR²¹, —C(O)NR²¹R²², —OR²¹, —SR²¹, —NR²¹R²², —NR²¹C(O)R²², —OC(O)R²¹, alkyl, alkenyl, alkynyl, aryl, heteroaryl, or heterocyclyl, each of which is independently substituted or unsubstituted, or hydrogen or halogen;
each $R^Q$ is independently —C(O)R²¹, —C(O)OR²¹, —C(O)NR²¹R²², —OR²¹, —SR²¹, —NR²¹R²², —NR²¹C(O)R²², —OC(O)R²¹, alkyl, alkenyl, alkynyl, aryl, heteroaryl, or heterocyclyl, each of which is independently substituted or unsubstituted;
y is 0, 1, 2, 3, or 4;
each R²¹ and R²² is independently alkyl, alkenyl, alkynyl, aryl, heteroaryl, or heterocyclyl, each of which is independently substituted or unsubstituted, or hydrogen; and
each R²⁵, R²⁶, R²⁷, R²⁸, and R²⁹ is independently hydrogen or a substituent selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and ester group.
or a pharmaceutically-acceptable salt thereof.

In some embodiments, the compound is of the formula:

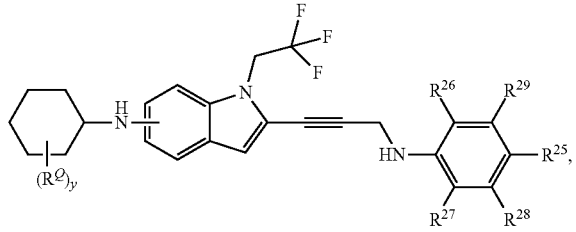

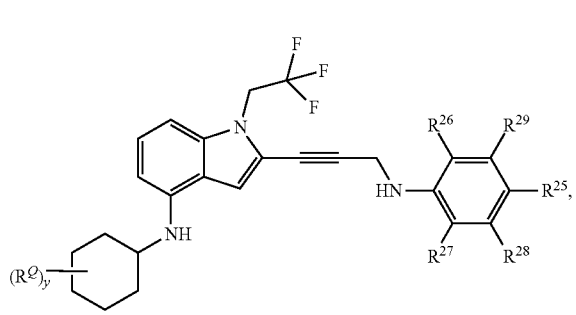

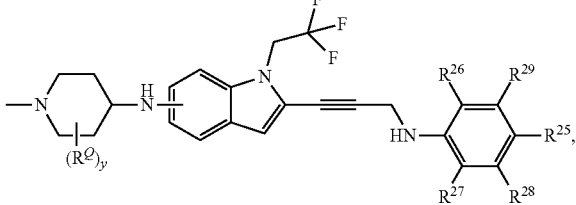

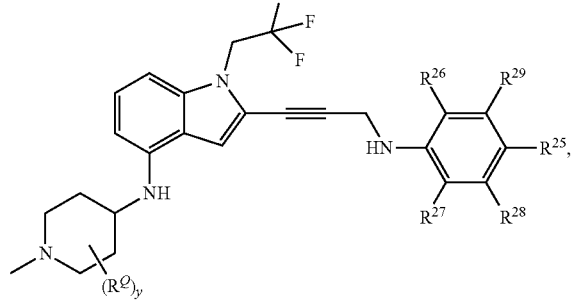

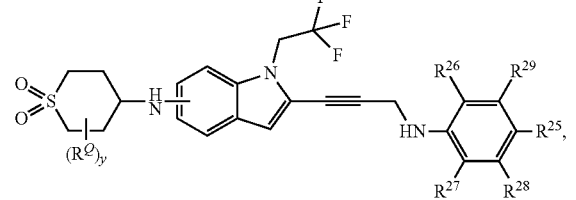

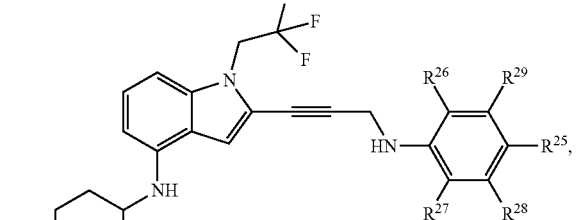

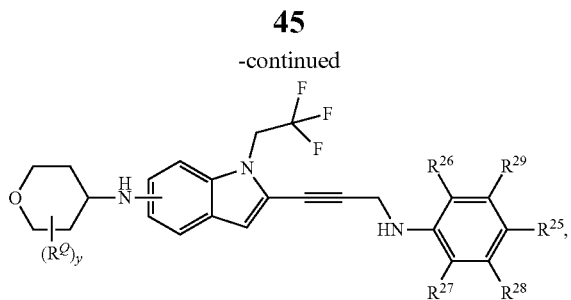

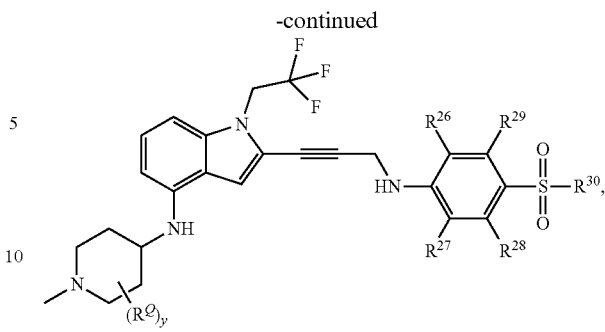

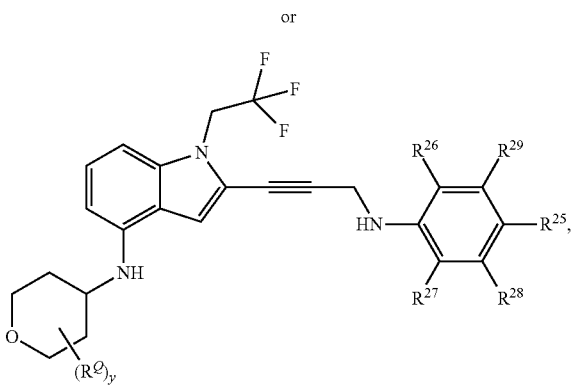

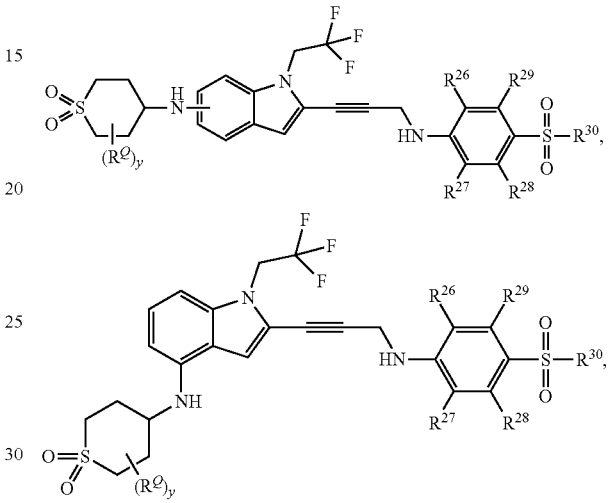

In some embodiments, R²⁵ is a substituted sulfone group. In some embodiments, R²⁵ is a sulfone group substituted with alkyl. In some embodiments, R²⁵ is a methanesulfonyl group. In some embodiments, R²⁵ is a sulfone group substituted with an amino group. In some embodiments, R²⁵ is a sulfonamide. In some embodiments, R²⁵ is a carboxy group. In some embodiments, R²⁵ is a methoxycarbonyl group.

In some embodiments, the compound is of the formula:

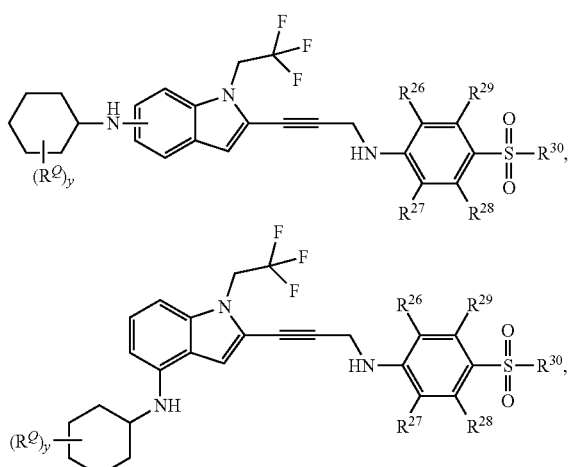

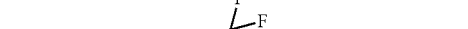

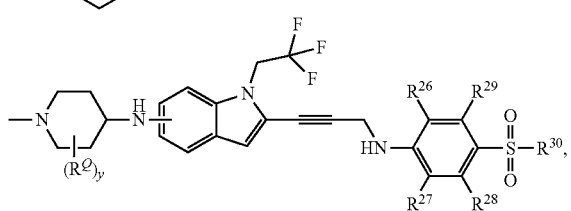

wherein:

each $R^Q$ is independently —C(O)R²¹, —C(O)OR²¹, —C(O)NR²¹R²², —OR²¹, —SR²¹, —NR²¹R²², —NR²¹C(O)R²², —OC(O)R²¹, alkyl, alkenyl, alkynyl, aryl, heteroaryl, or heterocyclyl, each of which is independently substituted or unsubstituted;

y is 0, 1, 2, 3, or 4;

each R²¹ and R²² is independently alkyl, alkenyl, alkynyl, aryl, heteroaryl, or heterocyclyl, each of which is independently substituted or unsubstituted, or hydrogen;

each $R^{26}$, $R^{27}$, $R^{28}$, and $R^{29}$ is independently hydrogen or a substituent selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, haloalkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and ester group; and $R^{30}$ is alkyl or an amino group, each of which is substituted or unsubstituted, or a pharmaceutically-acceptable salt thereof.

In some embodiments, $R^{30}$ is methyl. In some embodiments, $R^{30}$ is $NH_2$. In some embodiments, $R^{30}$ is NHMe. In some embodiments, $R^{30}$ is $NMe_2$.

In some embodiments, the compound is of the formula:

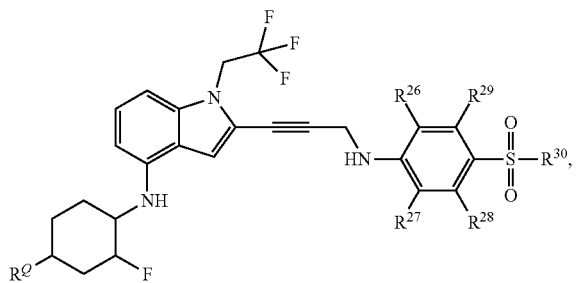

wherein $R^{30}$ is alkyl or an amino group, each of which is unsubstituted or substituted. In some embodiments, $R^{30}$ is methyl.

Non-limiting examples of compounds of the current disclosure include the following:

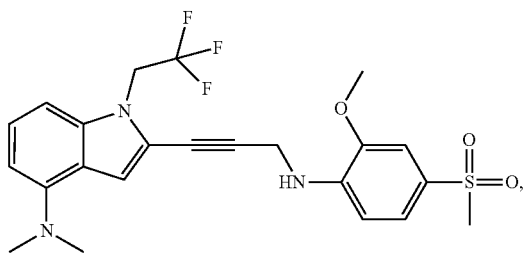

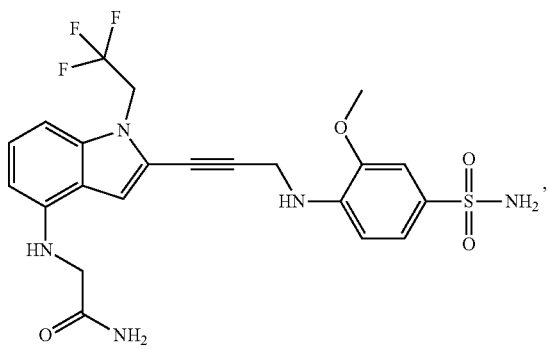

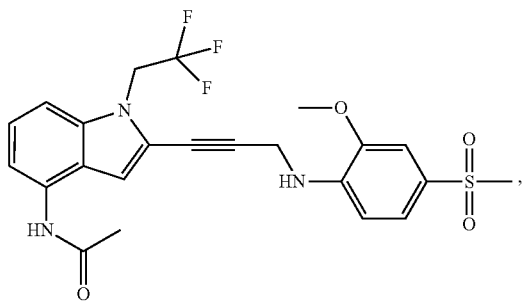

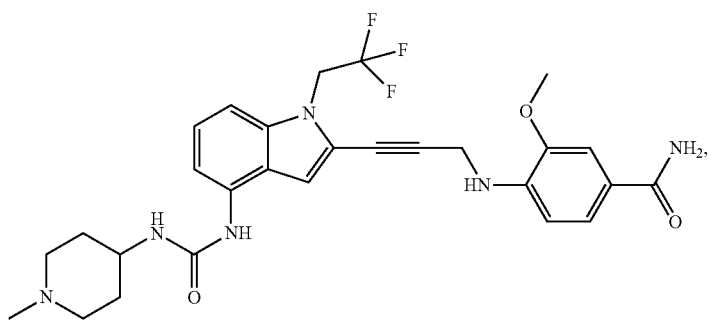

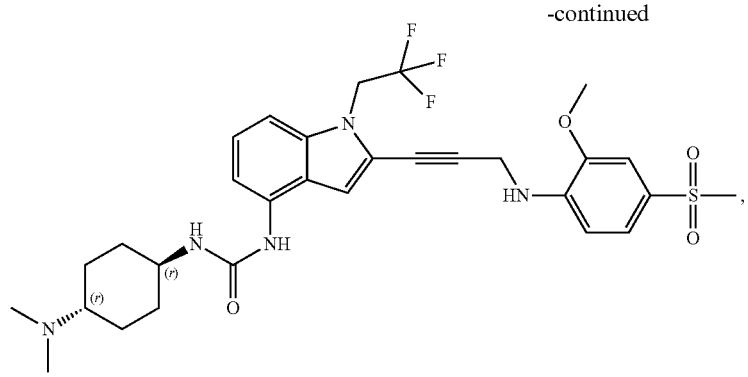
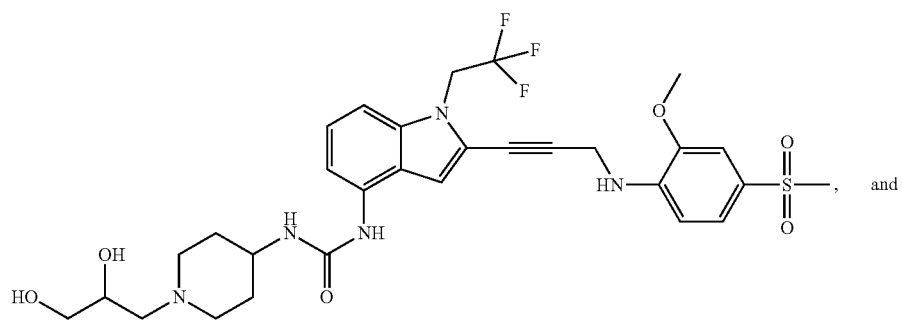
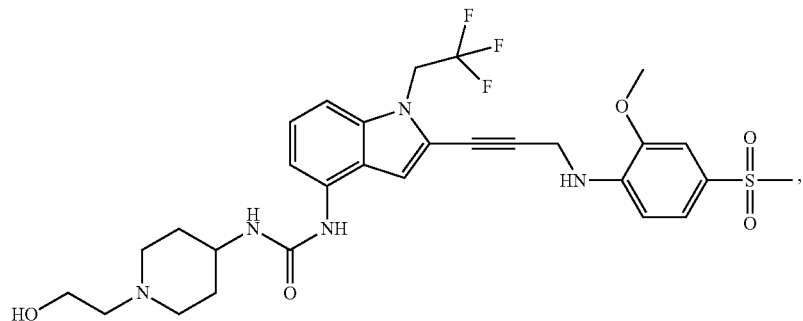
or a pharmaceutically-acceptable salt thereof.
Non-limiting examples of compounds of the current disclosure include the following:
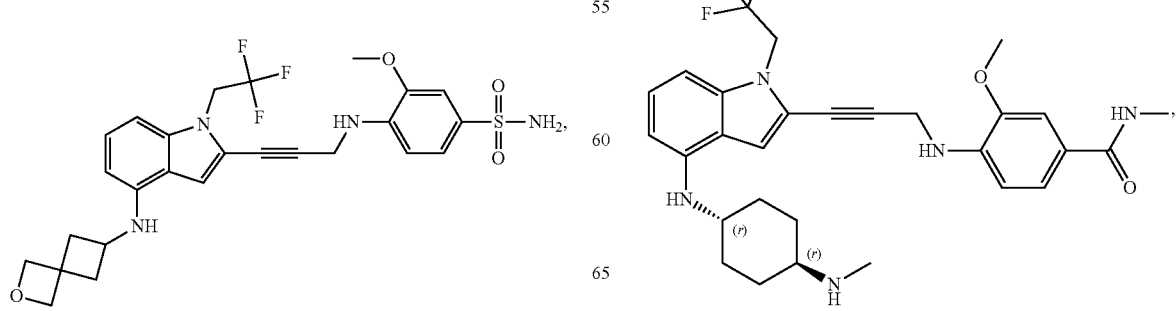

51
-continued
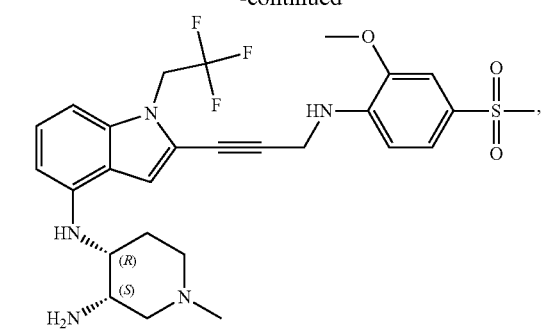
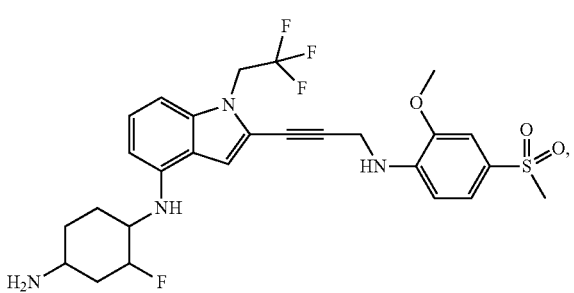
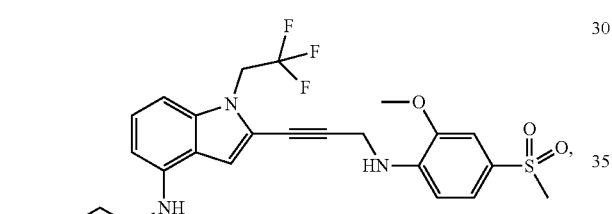
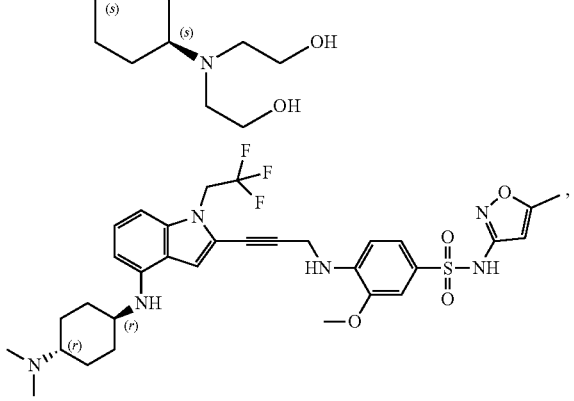
52
-continued
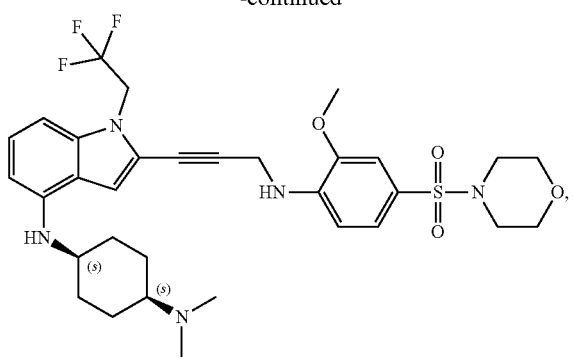
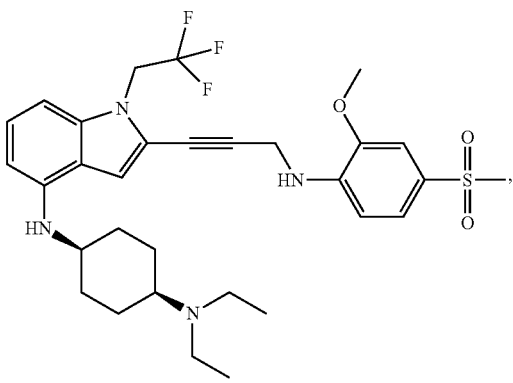
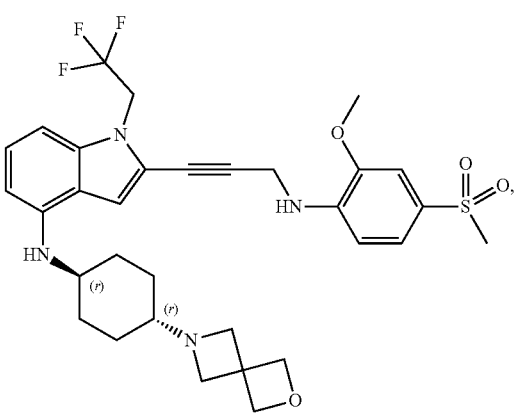
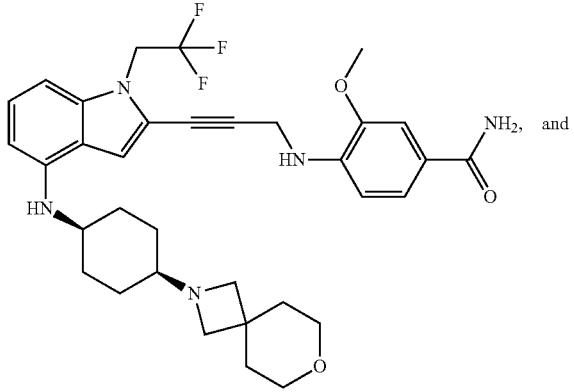
and

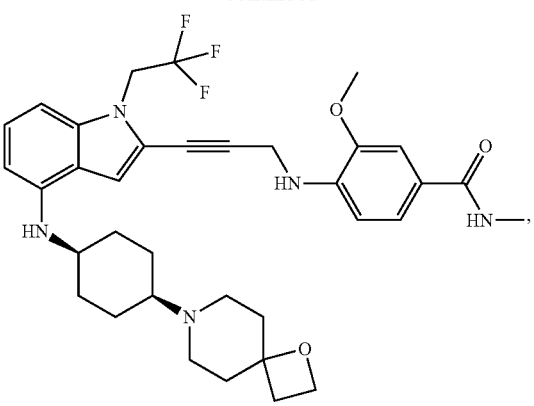
or a pharmaceutically-acceptable salt thereof.
Non-limiting examples of compounds of the current disclosure include the following:
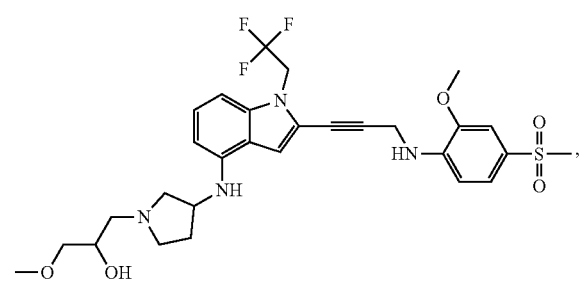
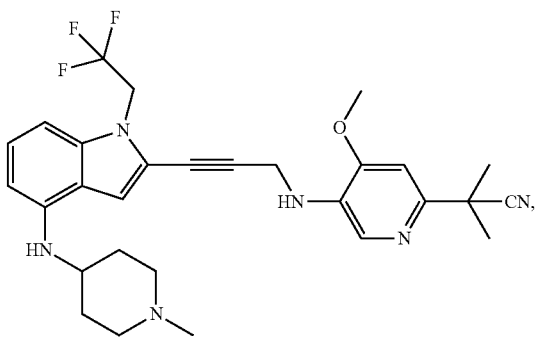
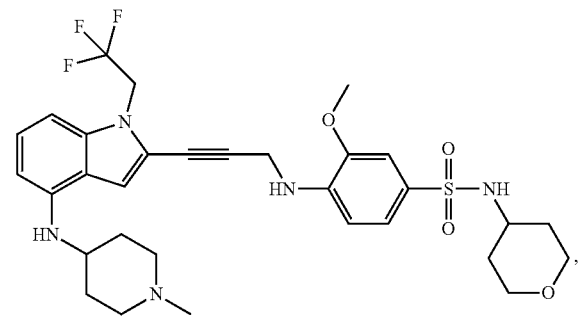
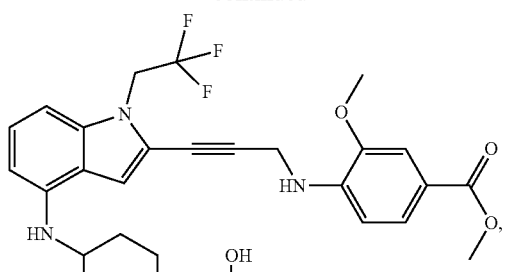
, and
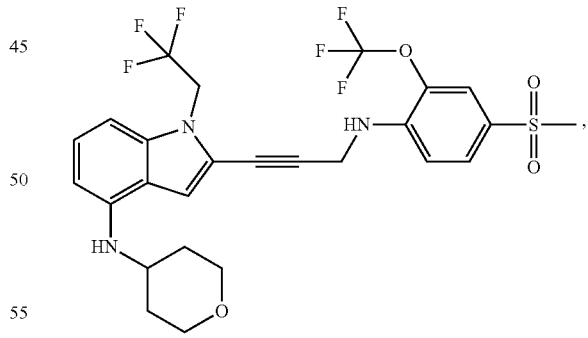
or a pharmaceutically-acceptable salt thereof.
Non-limiting examples of compounds of the current disclosure include the following:
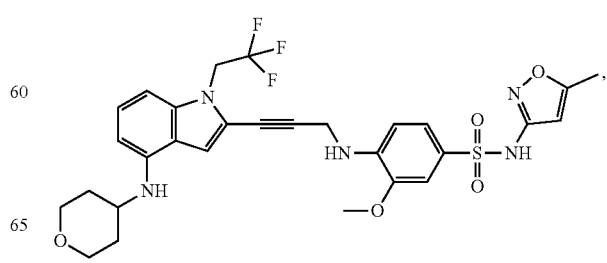

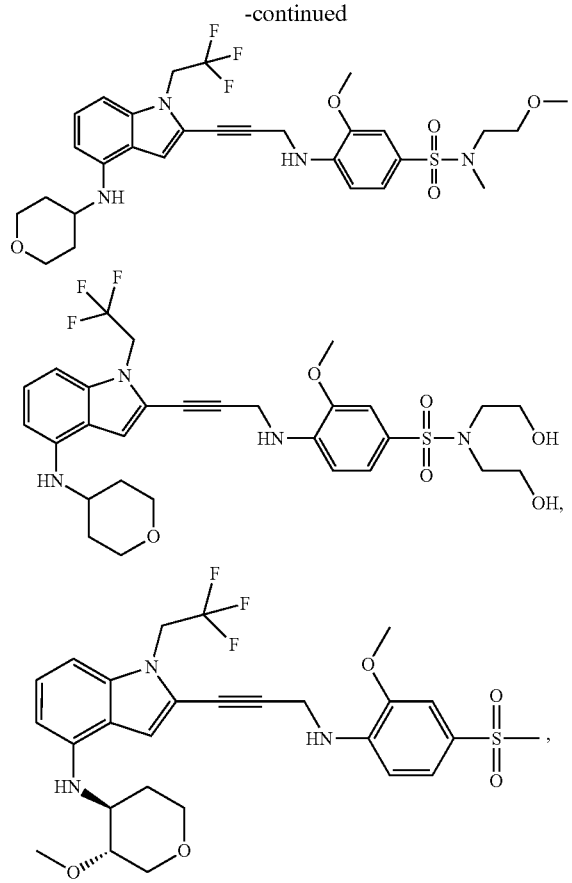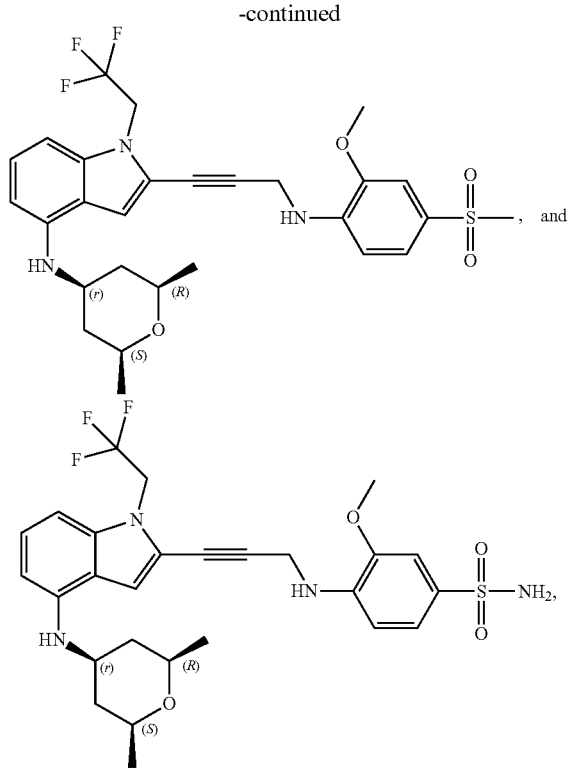
or a pharmaceutically-acceptable salt thereof.
Non-limiting examples of compounds of the current disclosure include the following:
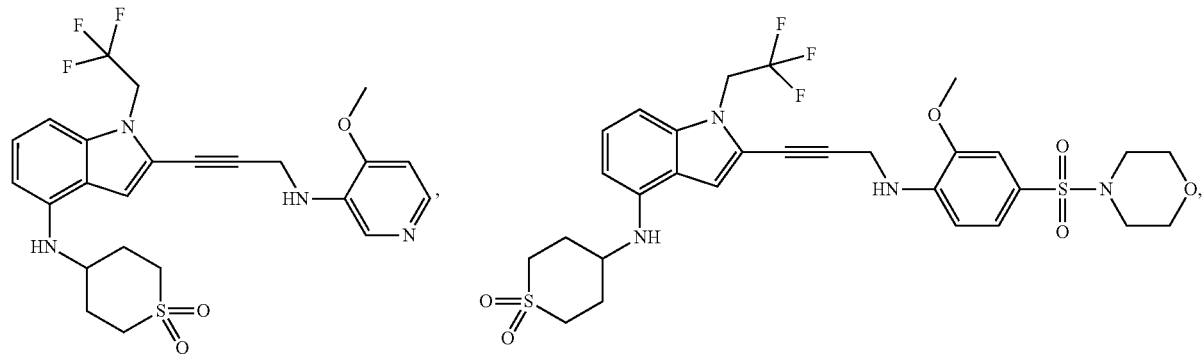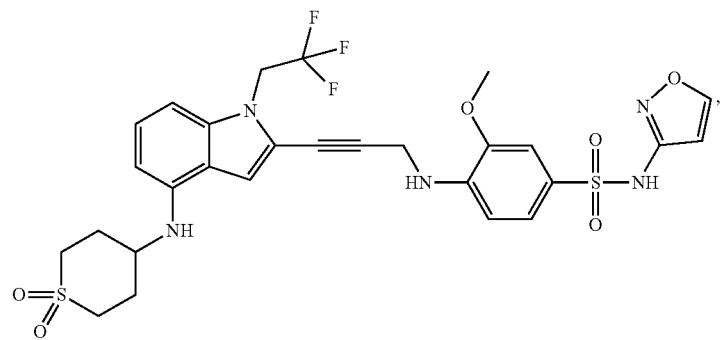

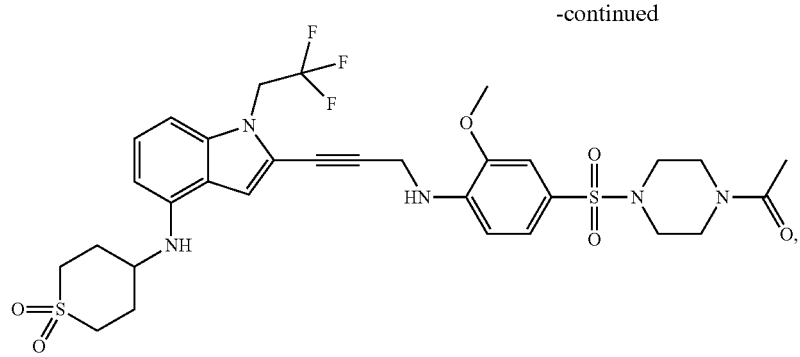
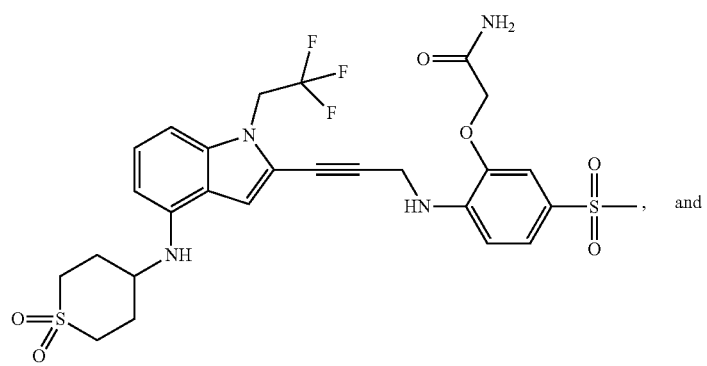
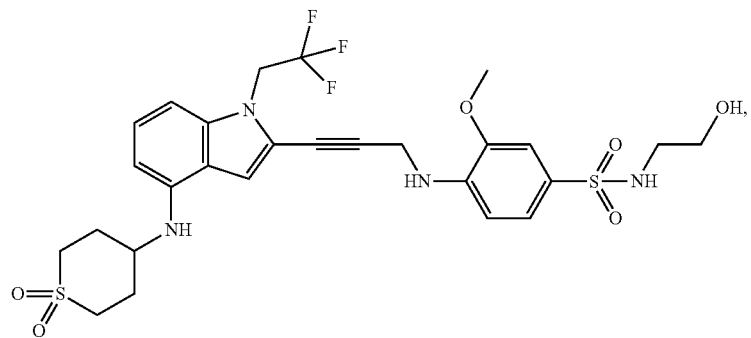
or a pharmaceutically-acceptable salt thereof.
Non-limiting examples of compounds of the current disclosure include the following:
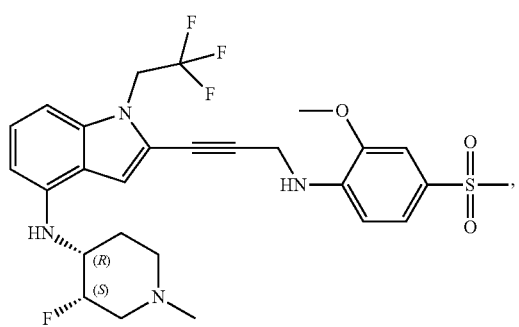
-continued
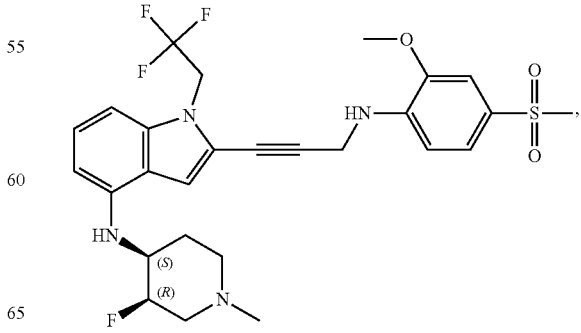

-continued
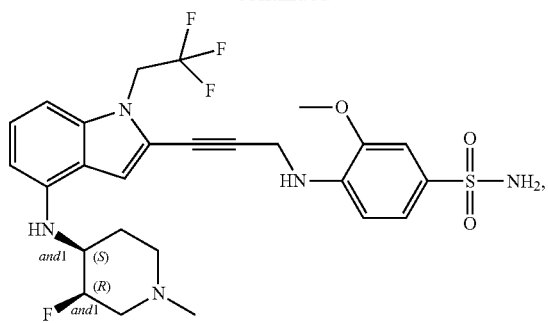
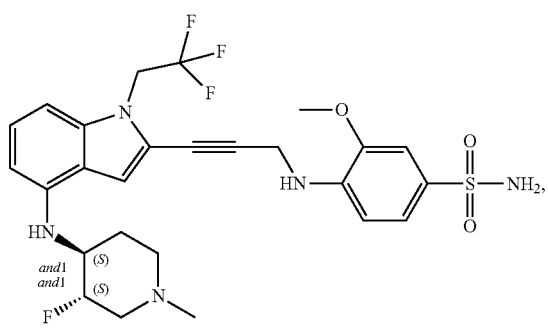
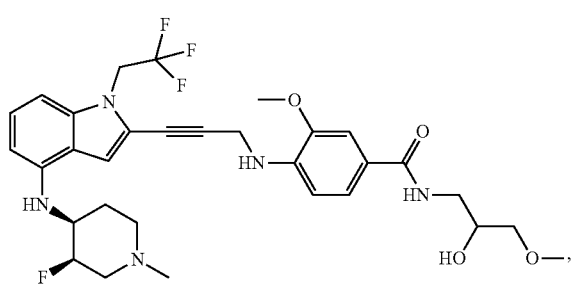
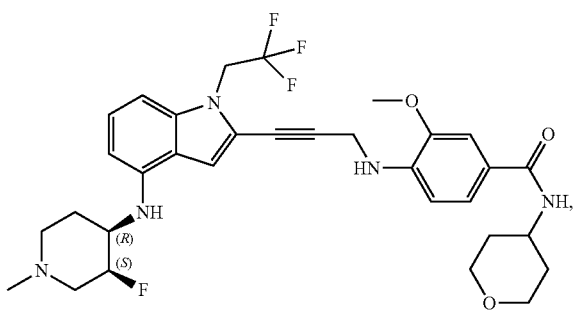
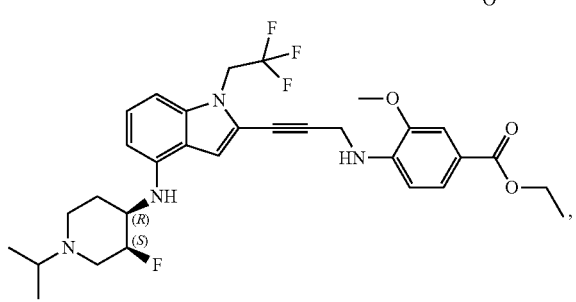
-continued
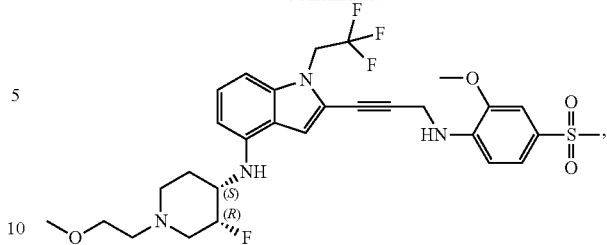
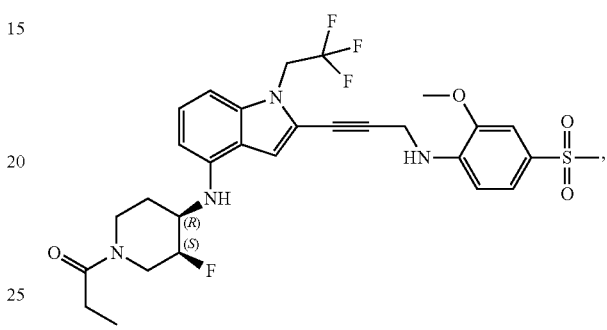
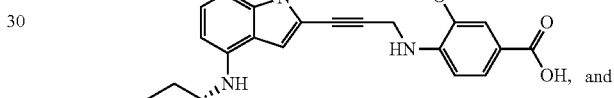
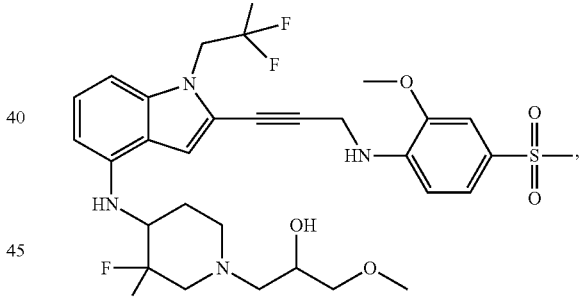
or a pharmaceutically-acceptable salt thereof.
Non-limiting examples of compounds of the current disclosure include the following:
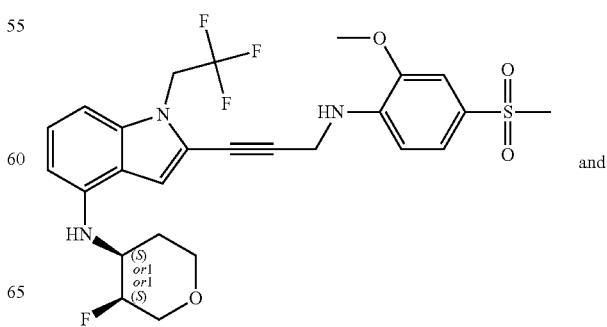

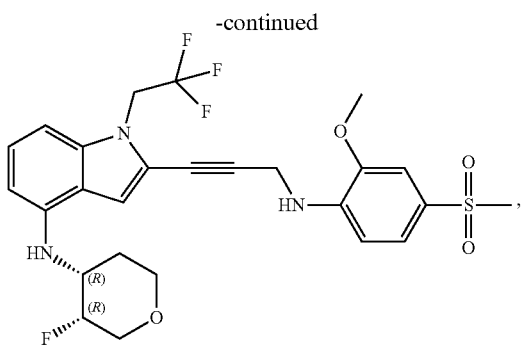

or a pharmaceutically-acceptable salt thereof.

Compounds herein can include all stereoisomers, enantiomers, diastereomers, mixtures, racemates, atropisomers, and tautomers thereof.

Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, ureido groups, epoxy groups, and ester groups.

Non-limiting examples of alkyl and alkylene groups include straight, branched, and cyclic alkyl and alkylene groups. An alkyl or alkylene group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of substituted alkyl groups includes hydroxymethyl, chloromethyl, trifluoromethyl, aminomethyl, 1-chloroethyl, 2-hydroxyethyl, 1,2-difluoroethyl, and 3-carboxypropyl.

Non-limiting examples of cyclic alkyl groups include cyclopropyl, cyclobutyl, cyclopentyl, cyclohexyl, cycloheptlyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups. Non-limiting examples of cyclic alkyl groups include cyclopropyl, 2-methyl-cycloprop-1-yl, cycloprop-2-en-1-yl, cyclobutyl, 2,3-dihydroxycyclobut-1-yl, cyclobut-2-en-1-yl, cyclopentyl, cyclopent-2-en-1-yl, cyclopenta-2,4-dien-1-yl, cyclohexyl, cyclohex-2-en-1-yl, cycloheptyl, cyclooctanyl, 2,5-dimethylcyclopent-1-yl, 3,5-dichlorocyclohex-1-yl, 4-hydroxycyclohex-1-yl, 3,3,5-trimethylcyclohex-1-yl, octahydropentalenyl, octahydro-1H-indenyl, 3a,4,5,6,7,7a-hexahydro-3H-inden-4-yl, decahydroazulenyl, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkenyl and alkenylene groups include ethenyl, prop-1-en-1-yl, isopropenyl, but-1-en-4-yl; 2-chloroethenyl, 4-hydroxybuten-1-yl, 7-hydroxy-7-methyloct-4-en-2-yl, and 7-hydroxy-7-methyloct-3,5-dien-2-yl.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkynyl or alkynylene groups include ethynyl, prop-2-yn-1-yl, prop-1-yn-1-yl, and 2-methyl-hex-4-yn-1-yl; 5-hydroxy-5-methylhex-3-yn-1-yl, 6-hydroxy-6-methylhept-3-yn-2-yl, and 5-hydroxy-5-ethylhept-3-yn-1-yl.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl. Non-limiting examples of substituted aryl groups include 3,4-dimethylphenyl, 4-tert-butylphenyl, 4-cyclopropylphenyl, 4-diethylaminophenyl, 4-(trifluoromethyl)phenyl, 4-(difluoromethoxy)-phenyl, 4-(trifluoromethoxy)phenyl, 3-chlorophenyl, 4-chlorophenyl, 3,4-dichlorophenyl, 2-fluorophenyl, 2-chlorophenyl, 2-iodophenyl, 3-iodophenyl, 4-iodophenyl, 2-methylphenyl, 3-fluorophenyl, 3-methylphenyl, 3-methoxyphenyl, 4-fluorophenyl, 4-methylphenyl, 4-methoxyphenyl, 2,3-difluorophenyl, 3,4-difluorophenyl, 3,5-difluorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, 3,5-dimethoxyphenyl, 2,4-difluorophenyl, 2,5-difluorophenyl, 2,6-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2,4-dichlorophenyl, 2,5-dichlorophenyl, 2,6-dichlorophenyl, 3,4-dichlorophenyl, 2,3,4-trichlorophenyl, 2,3,5-trichlorophenyl, 2,3,6-trichlorophenyl, 2,4,5-trichlorophenyl, 3,4,5-trichlorophenyl, 2,4,6-trichlorophenyl, 2,3-dimethylphenyl, 2,4-dimethylphenyl, 2,5-dimethylphenyl, 2,6-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 2,3,4-triethylphenyl, 2,3,5-triethylphenyl, 2,3,6-triethylphenyl, 2,4,5-triethylphenyl, 2,4,6-triethylphenyl, 2-isopropylphenyl, 3-isopropylphenyl, and 4-isopropylphenyl.

Non-limiting examples of substituted aryl groups include 2-aminophenyl, 2-(N-methylamino)phenyl, 2-(N,N-dimethylamino)phenyl, 2-(N-ethylamino)phenyl, 2-(N,N-diethylamino)phenyl, 3-aminophenyl, 3-(N-methylamino)phenyl, 3-(N,N-dimethylamino)phenyl, 3-(N-ethylamino)phenyl, 3-(N,N-diethylamino)phenyl, 4-aminophenyl, 4-(N-methylamino)phenyl, 4-(N,N-dimethylamino)phenyl, 4-(N-ethylamino)phenyl, and 4-(N,N-diethylamino)phenyl.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

Non-limiting examples of heterocycles include: heterocyclic units having a single ring containing one or more heteroatoms, non-limiting examples of which include, diazirinyl, aziridinyl, azetidinyl, pyrazolidinyl, imidazolidinyl, oxazolidinyl, isoxazolinyl, thiazolidinyl, isothiazolinyl, oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl, 2,3,4,5-tetrahydro-1H-azepinyl, 2,3-dihydro-1H-indole, and 1,2,3,4-tetrahydroquinoline; and ii) heterocyclic units having 2 or more rings one of which is a heterocyclic ring, non-limiting examples of which include hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, and decahydro-1H-cycloocta[b]pyrrolyl.

Non-limiting examples of heteroaryl include: i) heteroaryl rings containing a single ring, non-limiting examples of which include, 1,2,3,4-tetrazolyl, [1,2,3]triazolyl, [1,2,4]triazolyl, triazinyl, thiazolyl, 1H-imidazolyl, oxazolyl, isoxazolyl, isothiazolyl, furanyl, thiophenyl, pyrimidinyl, 2-phenylpyrimidinyl, pyridinyl, 3-methylpyridinyl, and 4-dimethylaminopyridinyl; and ii) heteroaryl rings containing 2 or more fused rings one of which is a heteroaryl ring, non-limiting examples of which include: 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 4,5,6,7-tetrahydro-1-H-indolyl, quinoxalinyl, quinazolinyl, quinolinyl, 8-hydroxy-quinolinyl, and isoquinolinyl.

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 510% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

In some embodiments, the compounds of the disclosure do not include compounds of Table 1, or a pharmaceutically-acceptable salt thereof.

TABLE 1

| | List of compounds | |
|---|---|---|
| # | Structure | IUPAC name |
| 1-P | | 1-Anilino-3-{1-ethyl-5-[(1-methyl-4-piperidylamino)methyl]-1H-indol-2-yl}-2-propyne |

TABLE 1-continued

List of compounds

| # | Structure IUPAC name |
|---|---|
| 2-P | 1-Anilino-3-{1-ethyl-5-[(methylamino)methyl]-1H-indol-2-yl}-2-propyne |
| 3-P | 1-Anilino-3-{1-ethyl-5-[(tetrahydro-2H-pyran-4-ylamino)methyl]-1H-indol-2-yl}-2-propyne |
| 4-P | 1-Anilino-3-[5-(benzylaminomethyl)-1-ethyl-1H-indol-2-yl]-2-propyne |
| 5-P | 3-{1-Ethyl-5-[(methylamino)methyl]-1H-indol-2-yl}-1-(p-fluorophenylamino)-2-propyne |

TABLE 1-continued

List of compounds

| # | Structure IUPAC name |
|---|---|
| 6-P | 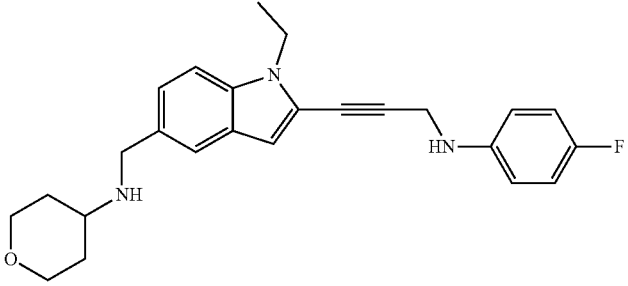 [SMILES: CCn1c(C#CCNc2ccc(F)cc2)cc2cc(CNC3CCOCC3)ccc21]<br>3-{1-Ethyl-5-[(tetrahydro-2H-pyran-4-ylamino)methyl]-1H-indol-2-yl}-1-(p-fluorophenylamino)-2-propyne |
| 7-P | 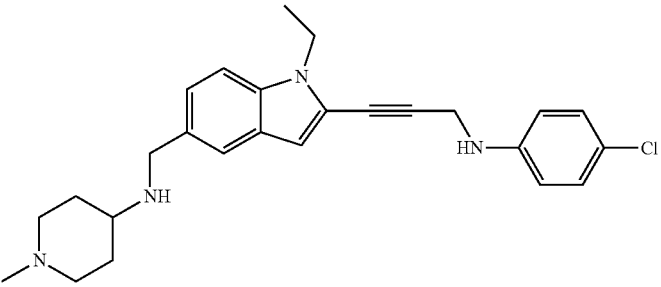 [SMILES: CCn1c(C#CCNc2ccc(Cl)cc2)cc2cc(CNC3CCN(C)CC3)ccc21]<br>1-(p-Chlorophenylamino)-3-{1-ethyl-5-[(1-methyl-4-piperidylamino)methyl]-1H-indol-2-yl}-2-propyne |
| 8-P | 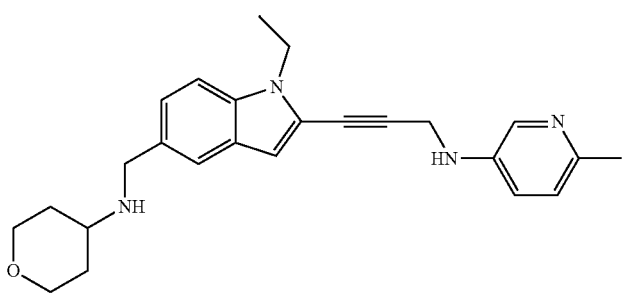 [SMILES: CCn1c(C#CCNc2ccc(C)nc2)cc2cc(CNC3CCOCC3)ccc21]<br>3-{1-Ethyl-5-[(tetrahydro-2H-pyran-4-ylamino)methyl]-1H-indol-2-yl}-1-(6-methyl-3-pyridylamino)-2-propyne |
| 9-P | 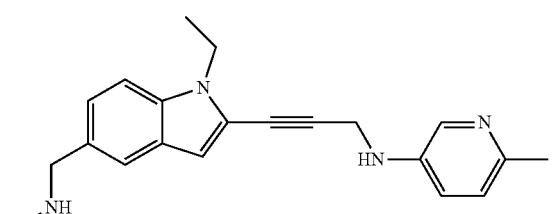<br>3-{1-Ethyl-5-[(methylamino)methyl]-1H-indol-2-yl}-1-(6-methyl-3-pyridylamino)-2-propyne |

TABLE 1-continued
List of compounds
| # | Structure IUPAC name |
|---|---|
| 10-P | 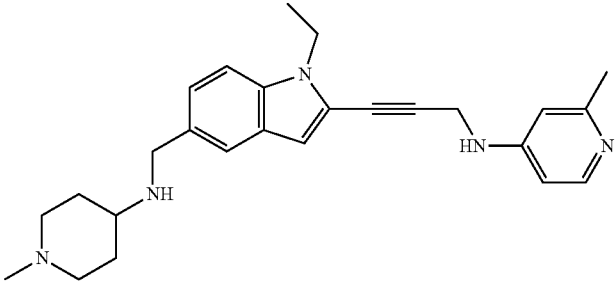 [SMILES: CCn1c(C#CCNc2ccnc(C)c2)cc2cc(CNC3CCN(C)CC3)ccc21]<br>3-{1-Ethyl-5-[(1-methyl-4-piperidylamino)methyl]-1H-indol-2-yl}-1-(2-methyl-4-pyridylamino)-2-propyne |
| 11-P | 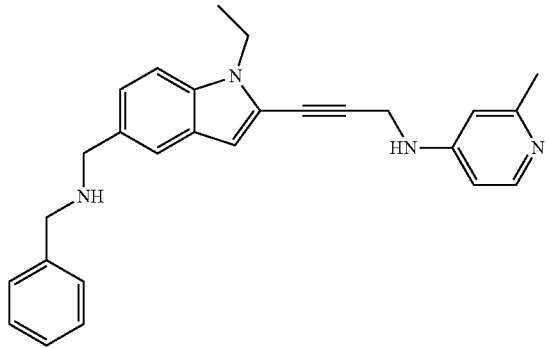 [SMILES: CCn1c(C#CCNc2ccnc(C)c2)cc2cc(CNCc3ccccc3)ccc21]<br>3-[5-(Benzylaminomethyl)-1-ethyl-1H-indol-2-yl]-1-(2-methyl-4-pyridylamino)-2-propyne |
| 12-P | 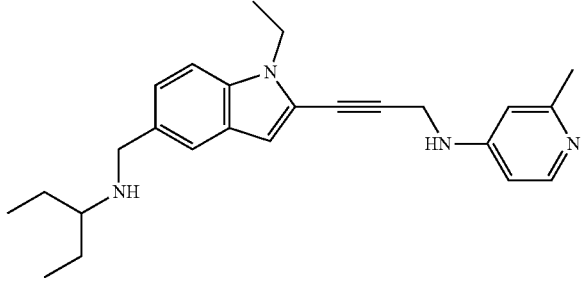 [SMILES: CCC(CC)NCc1ccc2c(c1)cc(C#CCNc1ccnc(C)c1)n2CC]<br>N-(3-{5-[(Diethylamino)methyl]-1-ethyl-1H-indol-2-yl}prop-2-yn-1-yl)aniline |
| 13-P | 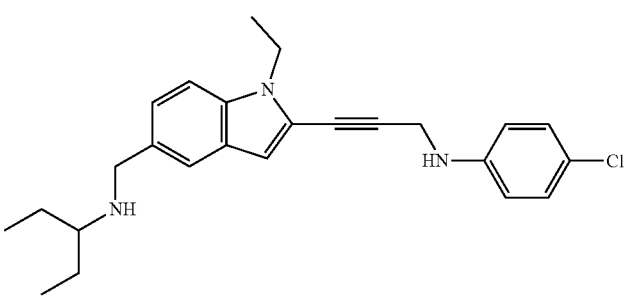 [SMILES: CCC(CC)NCc1ccc2c(c1)cc(C#CCNc1ccc(Cl)cc1)n2CC]<br>4-Chloro-N-(3-{5-[(diethylamino)methyl]-1-ethyl-1H-indol-2-yl}prop-2-yn-1-yl)aniline |

TABLE 1-continued
List of compounds
| # | Structure IUPAC name |
|---|---|
| 14-P | 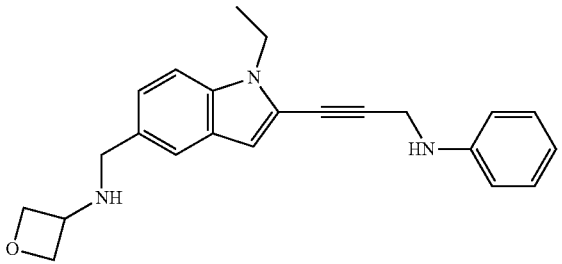 [SMILES: CCn1c(C#CCNc2ccccc2)cc2cc(CNC3COC3)ccc21] N-({1-Ethyl-2-[3-(phenylamino)pro-1-yn-1-yl]-1H-indol-5-yl}methyl)oxetan-3-amine |
| 15-P | 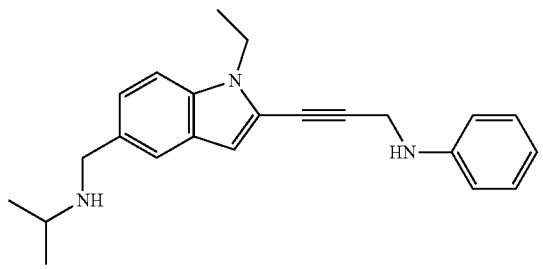 [SMILES: CCn1c(C#CCNc2ccccc2)cc2cc(CNC(C)C)ccc21] N-[3-(1-Ethyl-5-{[(2-methylpropyl)amino]methyl}-1H-indol-2-yl)prop-2-yn-1-yl]aniline |
| 16-P | 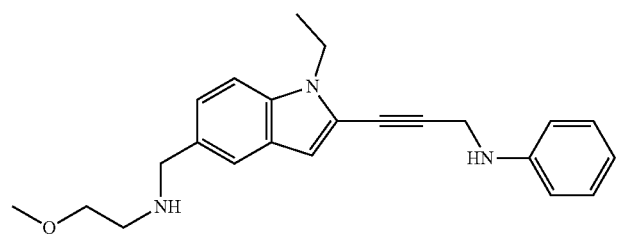 [SMILES: CCn1c(C#CCNc2ccccc2)cc2cc(CNCCOC)ccc21] N-[3-(1-Ethyl-5-{[(2-methylpropyl)amino]methyl}-1H-indol-2-yl)prop-2-yn-1-yl]aniline |
| 17-P | 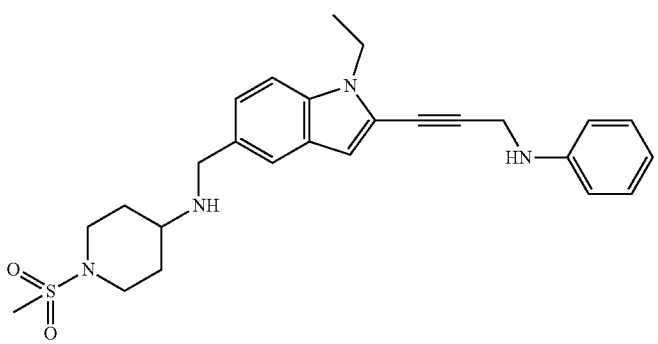 [SMILES: CCn1c(C#CCNc2ccccc2)cc2cc(CNC3CCN(S(C)(=O)=O)CC3)ccc21] N-({1-ethyl-2-[3-(phenylamino)prop-1-yn-1-yl]-1H-indol-5-yl}methyl)-1-methanesulfonylpiperidin-4-amine |

TABLE 1-continued

List of compounds

| # | Structure IUPAC name |
|---|---|
| 18-P | 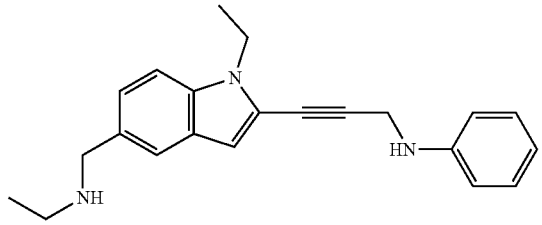 [SMILES: CCNCc1ccc2c(c1)cc(C#CCNc1ccccc1)n2CC]

N-(3-{1-Ethyl-5-[(ethylamino)methyl]-1H-indol-2-yl}prop-2-yn-1-yl)aniline |
| 19-P | 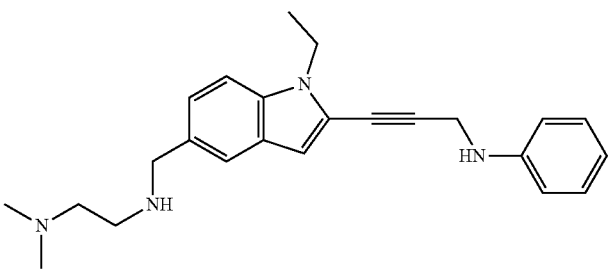 [SMILES: CCn1c(C#CCNc2ccccc2)cc2cc(CNCCN(C)C)ccc21]

N-{3-[5-({[2-(Dimethylamino)ethyl]amino}methyl)-1-ethyl-1H-indol-2-yl]prop-2-yn-1-yl}aniline |
| 20-P | 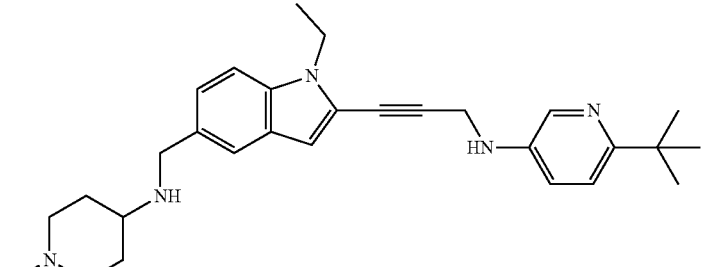

6-tert-Butyl-N-[3-(1-ethyl-5-{[(1-methylpiperidin-4-yl)amino]methyl}-1H-indol-2-yl)prop-2-yn-1-yl]pyridin-3-amine |
| 21-P | 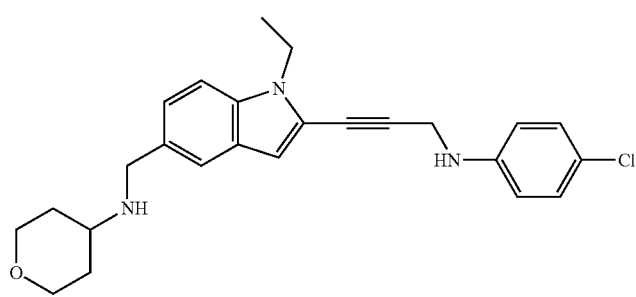 [SMILES: CCn1c(C#CCNc2ccc(Cl)cc2)cc2cc(CNC3CCOCC3)ccc21]

N-[(2-{3-[(4-Chlorophenyl)amino]prop-1-yn-1-yl}-1-ethyl-1H-indol-5-yl)methyl]oxan-4-amine |
| 22-P | 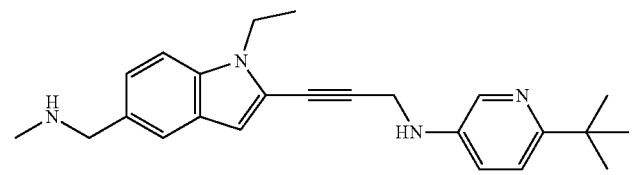 [SMILES: CCn1c(C#CCNc2ccc(C(C)(C)C)nc2)cc2cc(CNC)ccc21]

6-tert-Butyl-N-(3-{1-ethyl-5-[(methylamino)methyl]-1H-indol-2-yl}prop-2-yn-1-yl)pyridin-3-amine |

TABLE 1-continued

List of compounds

| # | Structure IUPAC name |
|---|---|
| 23-P | 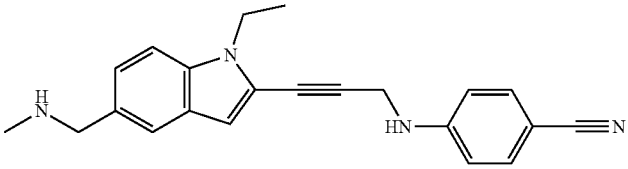 [SMILES: CCn1c(C#CCNc2ccc(C#N)cc2)cc2cc(CNC)ccc21]<br>4-[(3-{1-Ethyl-5-[(methylamino)methyl]-1H-indol-2-yl}prop-2-yn-1-yl)amino]benzonitrile |
| 24-P | 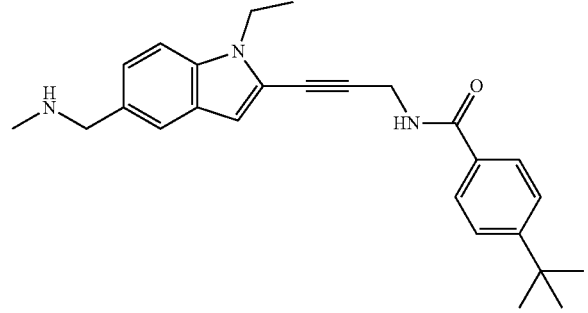 [SMILES: CCn1c(C#CCNC(=O)c2ccc(C(C)(C)C)cc2)cc2cc(CNC)ccc21]<br>4-tert-Butyl-N-(3-{1-ethyl-5-[(methylamino)methyl]-1H-indol-2-yl}prop-2-yn-1-yl)benzamide |
| 25-P | 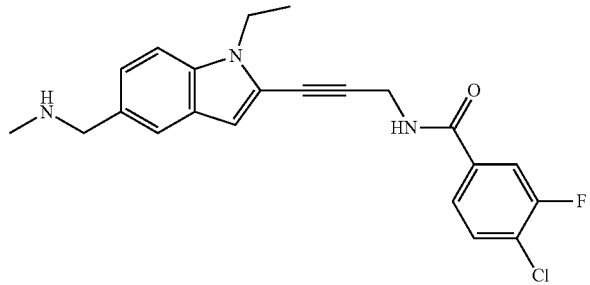 [SMILES: CCn1c(C#CCNC(=O)c2ccc(Cl)c(F)c2)cc2cc(CNC)ccc21]<br>4-Chloro-N-(3-{1-ethyl-5-[(methylamino)methyl]-1H-indol-2-yl}prop-2-yn-1-yl)-3-fluorobenzamide |
| 26-P | 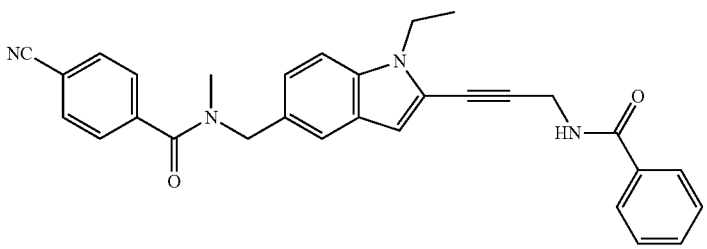 [SMILES: CCn1c(C#CCNC(=O)c2ccccc2)cc2cc(CN(C)C(=O)c3ccc(C#N)cc3)ccc21]<br>4-Cyano-N-({1-ethyl-2-[3-(phenylformamido)prop-1-yn-1-yl]-1H-indol-5-yl}methyl)-N-methylbenzamide |
| 27-P | 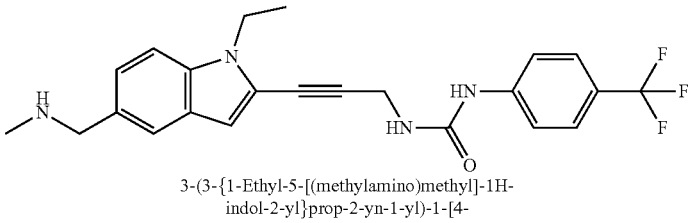<br>3-(3-{1-Ethyl-5-[(methylamino)methyl]-1H-indol-2-yl}prop-2-yn-1-yl)-1-[4-(trifluoromethyl)phenyl]urea |

TABLE 1-continued

List of compounds

| # | Structure IUPAC name |
|---|---|
| 28-P | 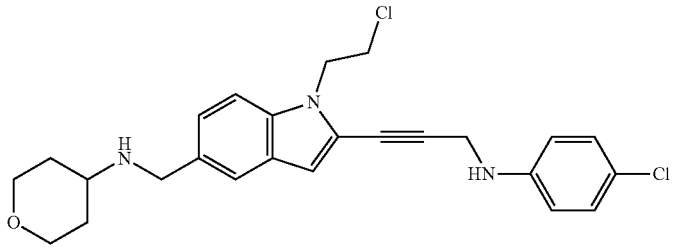 [SMILES: ClCCn1c(C#CCNc2ccc(Cl)cc2)cc2cc(CNC3CCOCC3)ccc21]<br>N-{[1-(2-Chloroethyl)-2-{3-[(4-chlorophenyl)amino]prop-1-yn-1-yl}-1H-indol-5-yl]methyl}oxan-4-amine |
| 29-P | 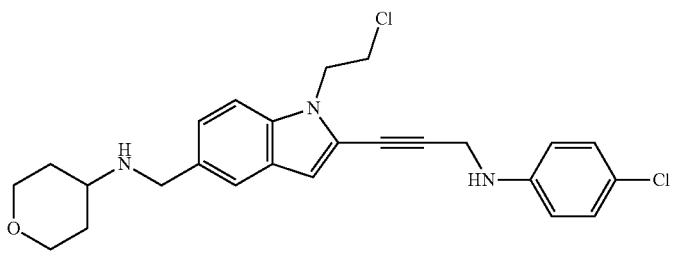 [SMILES: ClCCn1c(C#CCNc2ccc(Cl)cc2)cc2cc(CNC3CCOCC3)ccc21]<br>2-(4-{[3-(1-Ethyl-5-{[(1-methylpiperidin-4-yl)amino]methyl}-1H-indol-2-yl)prop-2-yn-1-yl]amino}phenyl)-2-methylpropanenitrile |
| 30-P | 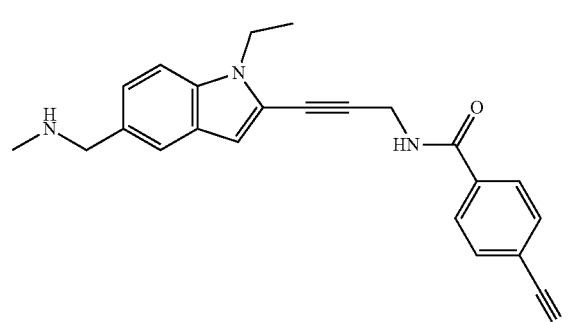<br>4-Cyano-N-(3-{1-ethyl-5-[(methylamino)methyl]-1H-indol-2-yl}prop-2-yn-1-yl)benzamide |
| 31-P | 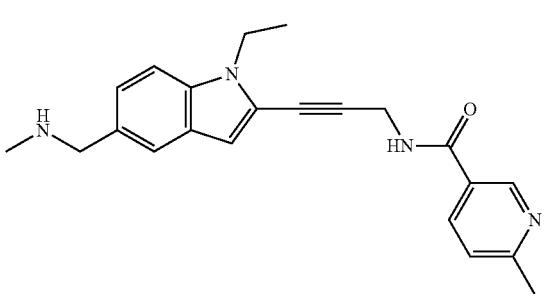<br>N-(3-{1-Ethyl-5-[(methylamino)methyl]-1H-indol-2-yl}prop-2-yn-1-yl)-6-methylpyridine-3-carboxamide |

TABLE 1-continued

List of compounds

| # | Structure IUPAC name |
|---|---|
| 32-P | 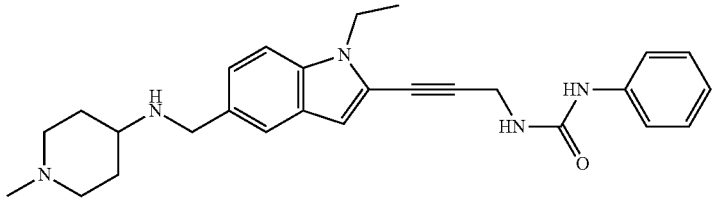 [SMILES: CCn1c(C#CCNC(=O)Nc2ccccc2)cc2cc(CNC3CCN(C)CC3)ccc21]<br>3-[3-(1-Ethyl-5-{[(1-methylpiperidin-4-yl)amino]methyl}-1H-indol-2-yl)prop-2-yn-1-yl]-1-phenylurea |
| 33-P | 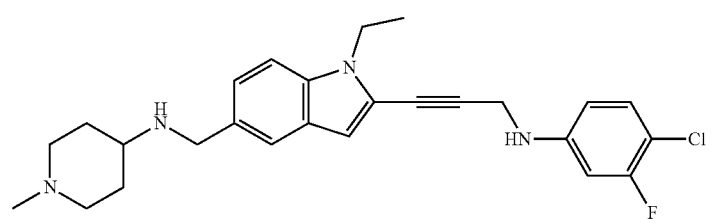 [SMILES: CCn1c(C#CCNc2ccc(Cl)c(F)c2)cc2cc(CNC3CCN(C)CC3)ccc21]<br>N-[(2-{3-[(4-Chloro-3-fluorophenyl)amino]prop-1-yn-1-yl}-1-ethyl-1H-indol-5-yl)methyl]-1-methylpiperidin-4-amine |
| 34-P | 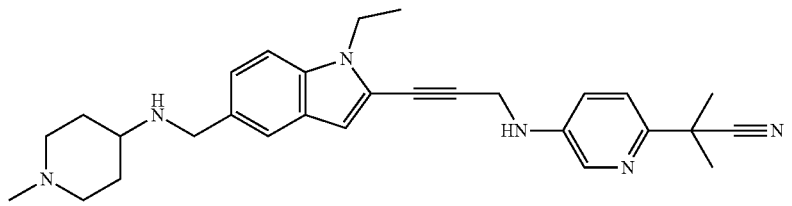 [SMILES: CCn1c(C#CCNc2ccc(C(C)(C)C#N)nc2)cc2cc(CNC3CCN(C)CC3)ccc21]<br>2-(5-{[3-(1-Ethyl-5-{[(1-methylpiperidin-4-yl)amino]methyl}-1H-indol-2-yl)prop-2-yn-1-yl]amino}pyridin-2-yl)-2-methylpropanenitrile |
| 35-P | 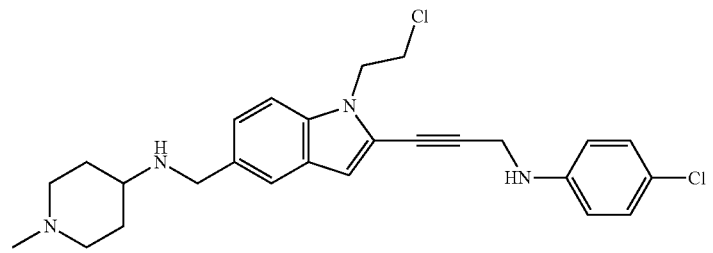 [SMILES: CN1CCC(NCc2ccc3c(c2)cc(C#CCNc2ccc(Cl)cc2)n3CCCl)CC1]<br>N-{1-(2-Chloroethyl)-2-{3-[(4-chlorophenyl)amino]prop-1-yn-1-yl}-1H-indol-5-yl]methyl}-1-methylpiperidin-4-amine |
| 36-P | 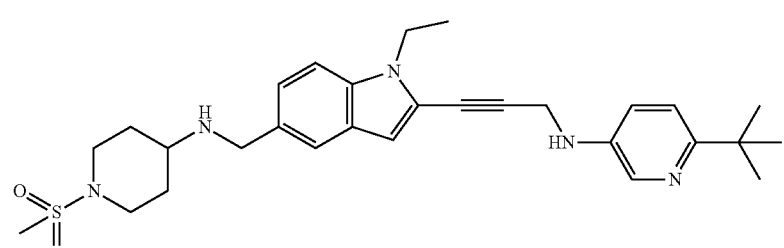<br>6-tert-Butyl-N-[3-(1-ethyl-5-{[(1-methanesulfonylpiperidin-4-yl)amino]methyl}-1H-indol-2-yl)prop-2-yn-1-yl]pyridin-3-amine |

TABLE 1-continued

List of compounds

| # | Structure IUPAC name |
|---|---|
| 37-P | 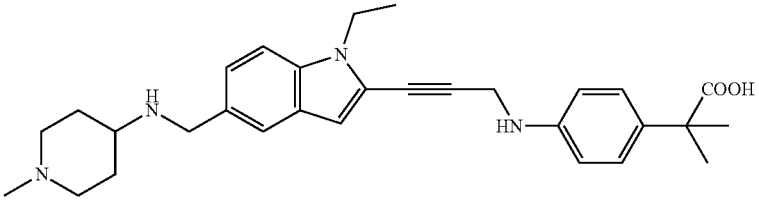 [SMILES: CCn1c(C#CCNc2ccc(C(C)(C)C(=O)O)cc2)cc2cc(CNC3CCN(C)CC3)ccc21]

2-(4-{[3-(1-Ethyl-5-{[(1-methylpiperidin-4-yl)amino]methyl}-1H-indol-2-yl)prop-2-yn-1-yl]amino}phenyl)-2-methylpropanoic acid |
| 38-P | 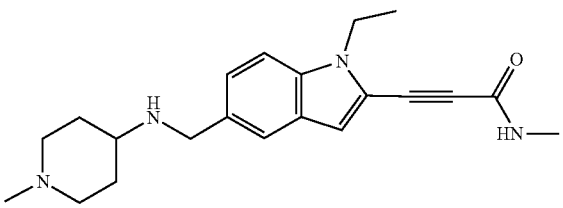

3-(1-Ethyl-5-{[(1-methylpiperidin-4-yl)amino]methyl}-1H-indol-2-yl)-N-methylprop-2-ynamide |
| 39-P | 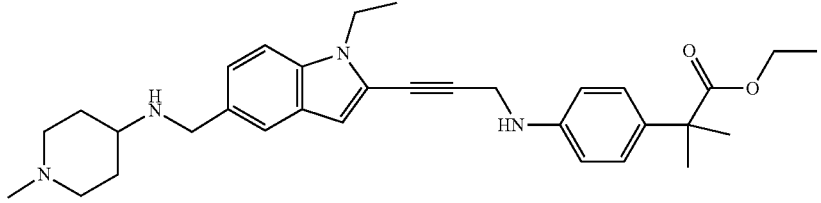 [SMILES: CCOC(=O)C(C)(C)c1ccc(NCC#Cc2cc3cc(CNC4CCN(C)CC4)ccc3n2CC)cc1]

Ethyl 2-(4-{[3-(1-ethyl-5-{[(1-methylpiperidin-4-yl)amino]methyl}-1H-indol-2-yl)prop-2-yn-1-yl]amino}phenyl)-2-methylpropanoate |
| 40-P | 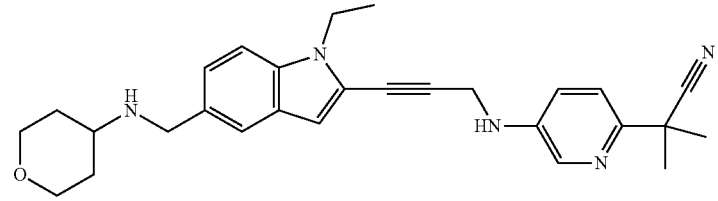 [SMILES: CCn1c(C#CCNc2ccc(C(C)(C)C#N)nc2)cc2cc(CNC3CCOCC3)ccc21]

2-(5-{[3-(1-Ethyl-5-{[(oxan-4-yl)amino]methyl}-1H-indol-2-yl)prop-2-yn-1-yl]amino}pyridin-2-yl)-2-methylpropanenitrile |
| 41-P | 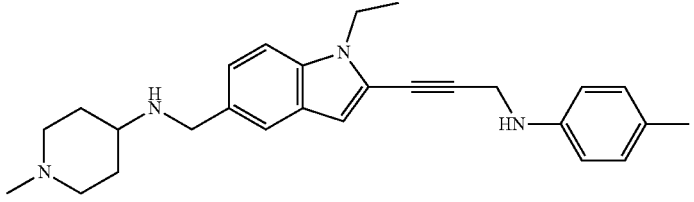

N-[(1-Ethyl-2-{3-[(4-methylphenyl)amino]prop-1-yn-1-yl}-1H-indol-5-yl)methyl]-1-methylpiperidin-4-amine |

TABLE 1-continued

List of compounds

| # | Structure IUPAC name |
|---|---|
| 42-P | 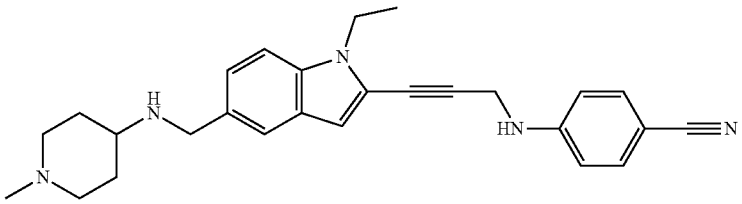 [SMILES: CCn1c(C#CCNc2ccc(C#N)cc2)cc2cc(CNC3CCN(C)CC3)ccc21]<br>4-{[3-(1-Ethyl-5-{[(1-methylpiperidin-4-yl)amino]methyl}-1H-indol-2-yl)prop-2-yn-1-yl]aminl}benzonitrile |
| 43-P | 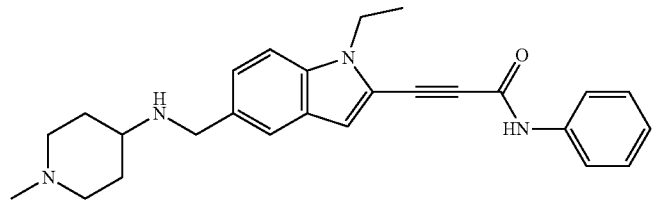 [SMILES: CCn1c(C#CC(=O)Nc2ccccc2)cc2cc(CNC3CCN(C)CC3)ccc21]<br>3-(1-Ethyl-5-{[(1-methylpiperidin-4-yl)amino]methyl}-1H-indol-2-yl)-N-phenylprop-2-ynamide |
| 44-P | 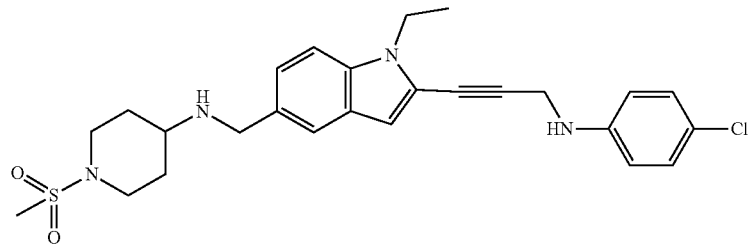 [SMILES: CCn1c(C#CCNc2ccc(Cl)cc2)cc2cc(CNC3CCN(S(C)(=O)=O)CC3)ccc21]<br>N-[(2-{3-[(4-Chlorophenyl)amino]prop-1-yn-1-yl}-1-ethyl-1H-indol-5-yl)methyl]-1-methanesulfonylpiperidin-4-amine |
| 45-P | 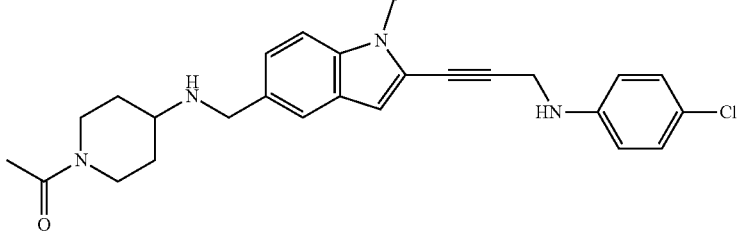<br>1-(4-{[(2-{3-[(4-Chlorophenyl)amino]prop-1-yn-1-yl}-1-ethyl-1H-indol-5-yl)methyl]amino}piperidin-1-yl)ethan-1-one |
| 46-P | 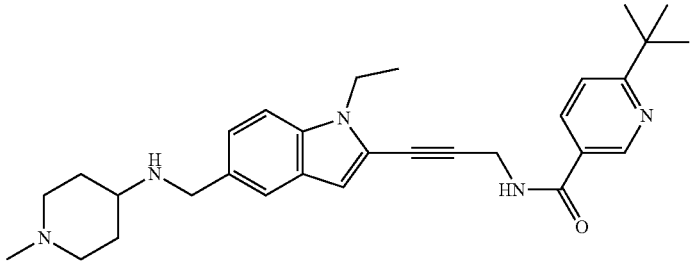 [SMILES: CCn1c(C#CCNC(=O)c2ccc(C(C)(C)C)nc2)cc2cc(CNC3CCN(C)CC3)ccc21]<br>6-tert-Butyl-N-[3-(1-ethyl-5-{[(1-methylpiperidin-4-yl)amino]methyl}-1H-indol-2-yl)prop-2-yn-1-yl]pyridine-3-carboxamide |

TABLE 1-continued
List of compounds
| # | Structure IUPAC name |
|---|---|
| 47-P | 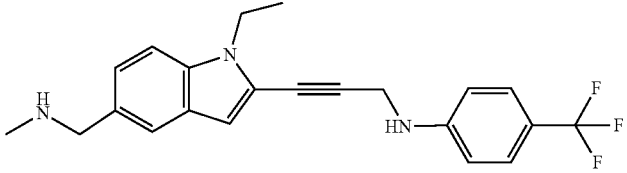 [SMILES: CCn1c(C#CCNc2ccc(C(F)(F)F)cc2)cc2cc(CNC)ccc21]<br>N-(3-{1-Ethyl-5-[(methylamino)methyl]-1H-indol-2-yl}prop-2-yn-1-yl)-4-(trifluoromethyl)aniline |
| 48-P | 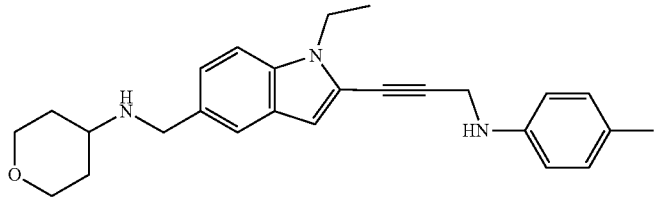 [SMILES: CCn1c(C#CCNc2ccc(C)cc2)cc2cc(CNC3CCOCC3)ccc21]<br>N-[(1-Ethyl-2-{3-[(4-methylphenyl)amino]prop-1-yn-1-yl}-1H-indol-5-yl)methyl]oxan-4-amine |
| 49-P | 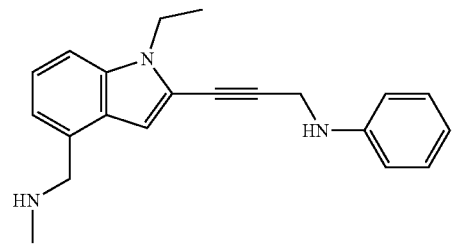 [SMILES: CCn1c(C#CCNc2ccccc2)cc2c(CNC)cccc21]<br>N-(3-{1-ethyl-4-[(methylamino)methyl]-1H-indol-2-yl}prop-2-yn-1-yl)aniline |
| 50-P | 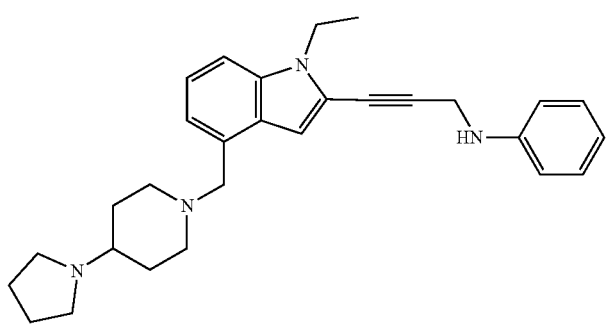 [SMILES: CCn1c(C#CCNc2ccccc2)cc2c(CN3CCC(N4CCCC4)CC3)cccc21]<br>N-[3-(1-ethyl-4-{[4-(pyrrolidin-1-yl)piperidin-1-yl]methyl}-1H-indol-2-yl)prop-2-yn-1-yl]aniline |

TABLE 1-continued

List of compounds

| # | Structure IUPAC name |
|---|---|
| 51-P | 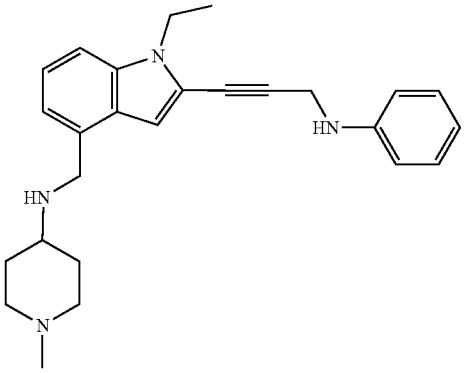 [SMILES: CCn1c(C#CCNc2ccccc2)cc2c(CNC3CCN(C)CC3)cccc21]<br>N-({1-ethyl-2-[3-(phenylamino)prop-1-yn-1-yl]-1H-indol-4-yl}methyl)-1-methylpiperidin-4-amine |
| 52-P | 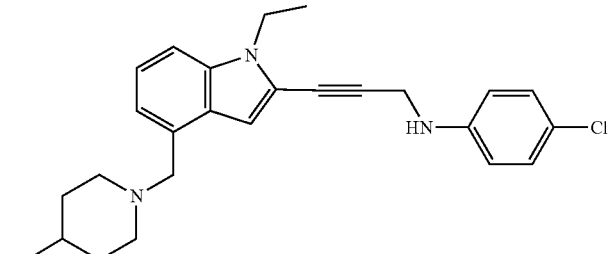<br>1-[(2-{3-[(4-Chlorophenyl)amino]prop-1-yn-1-yl}-1-ethyl-1H-indol-4-yl)methyl]piperidin-4-ol |
| 53-P | 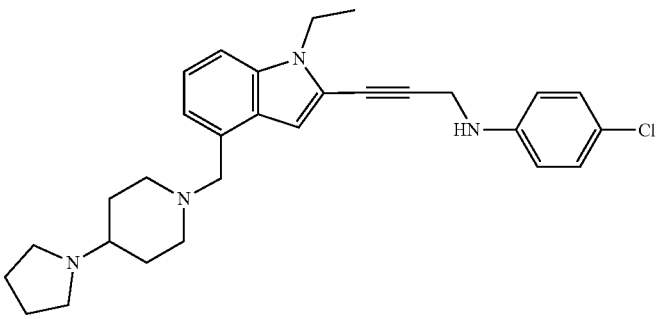 [SMILES: CCn1c(C#CCNc2ccc(Cl)cc2)cc2c(CN3CCC(N4CCCC4)CC3)cccc21]<br>4-Chloro-N-[3-(1-ethyl-4-{[4-(pyrrolidin-1-yl)piperidin-1-yl]methyl}-1H-indol-2-yl)prop-2-yn-1-yl]aniline |
| 54-P | 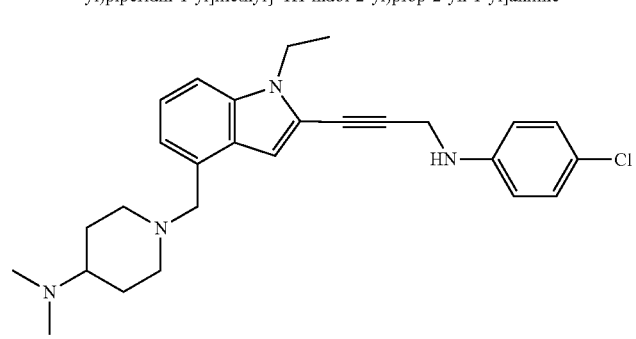<br>1-[(2-{3-[(4-chlorophenyl)amino]prop-1-yn-1-yl}-1-ethyl-1H-indol-4-yl)methyl]-N,N-dimethylpiperidin-4-amine |

TABLE 1-continued

List of compounds

| # | Structure | IUPAC name |
|---|---|---|
| 55-P | 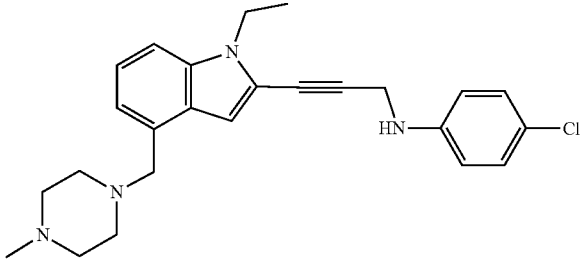 [SMILES: CCn1c(C#CCNc2ccc(Cl)cc2)cc2c(CN3CCN(C)CC3)cccc21] | 4-Chloro-N-(3-{1-ethyl-4-[(4-methylpiperazin-1-yl)methyl]-1H-indol-2-yl}prop-2-yn-1-yl)aniline |
| 56-P | 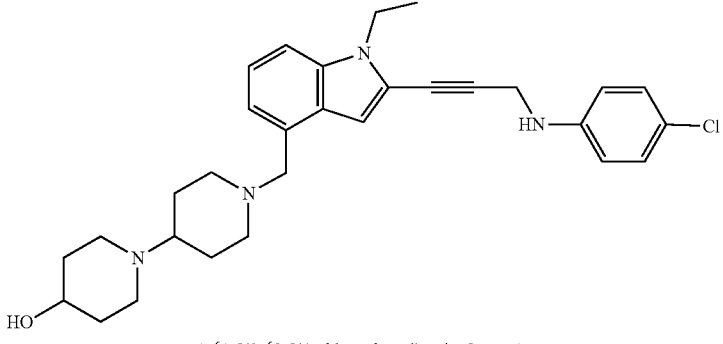 | 1-{1-[(2-{3-[(4-chlorophenyl)amino]prop-1-yn-1-yl}-1-ethyl-1H-indol-4-yl)methyl]piperidin-4-yl}piperidin-4-ol |
| 57-P | 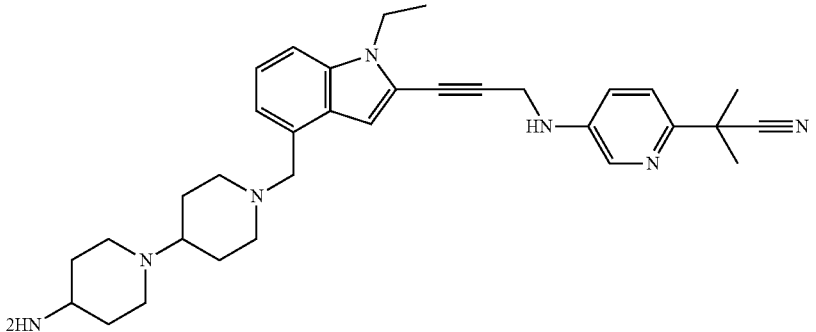 | 2-(5-{[3-(4-{[4-(4-Aminopiperidin-1-yl)piperidin-1-yl]methyl}-1-ethyl-1H-indol-2-yl)prop-2-yn-1-yl]amino}pyridin-2-yl)-2-methylpropanenitrile |
| 58-P | 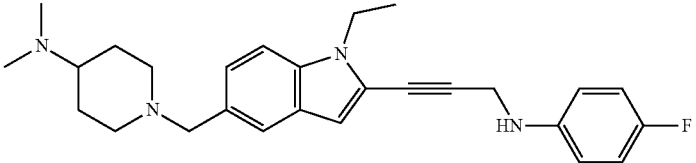 [SMILES: CCn1c(C#CCNc2ccc(F)cc2)cc2cc(CN3CCC(N(C)C)CC3)ccc21] | 1-[(1-ethyl-2-{3-{(4-fluorophenyl)amino]prop-1-yn-1-yl}-1H-indol-5-yl)methyl]-N,N-dimethylpiperidin-4-amine |

TABLE 1-continued

List of compounds

| # | Structure IUPAC name |
|---|---|
| 59-P | 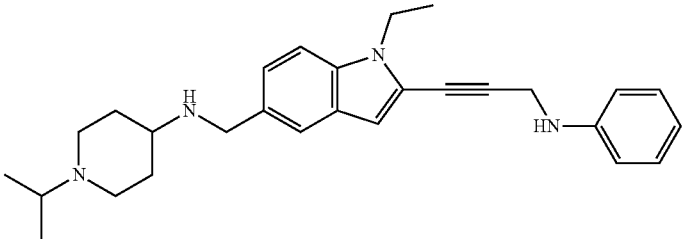 [SMILES: CCn1c(C#CCNc2ccccc2)cc2cc(CNC3CCN(C(C)C)CC3)ccc21]
4-N-({1-ethyl-2-[3-(phenylamino)prop-1-yn-1-yl]-1H-indol-5-yl}methyl)-1-N,1-N-dimethylcyclohexane-1,4-diamine |
| 60-P | 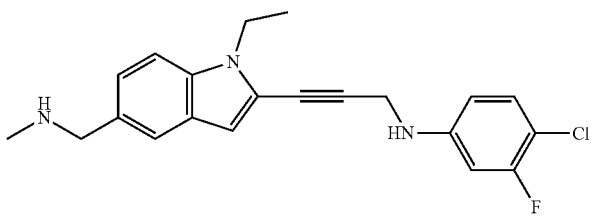 [SMILES: CCn1c(C#CCNc2ccc(Cl)c(F)c2)cc2cc(CNC)ccc21]
4-chloro-N-(3-{1-ethyl-5-[(methylamino)methyl]-1H-indol-2-yl}prop-2-yn-1-yl)-3-fluoroaniline |
| 61-P | 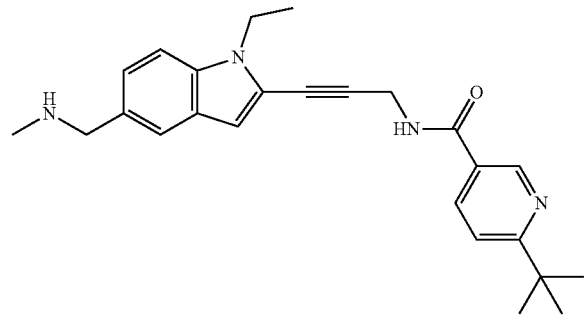 [SMILES: CCn1c(C#CCNC(=O)c2ccc(C(C)(C)C)nc2)cc2cc(CNC)ccc21]
6-tert-butyl-N-(3-{1-ethyl-5-[(methylamino)methyl]-1H-indol-2-yl}prop-2-yn-1-yl)pyridine-3-carboxamide |
| 62-P | 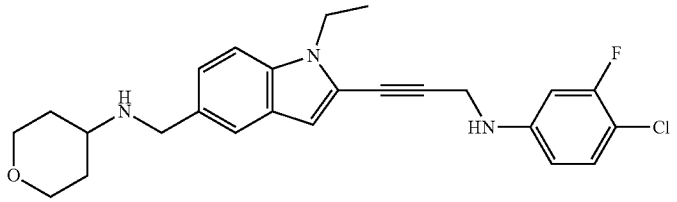 [SMILES: CCn1c(C#CCNc2ccc(Cl)c(F)c2)cc2cc(CNC3CCOCC3)ccc21]
N-(3-{1-ethyl-5-[(methylamino)methyl]-1H-indol-2-yl}prop-2-yn-1-yl)benzamide |
| 63-P | 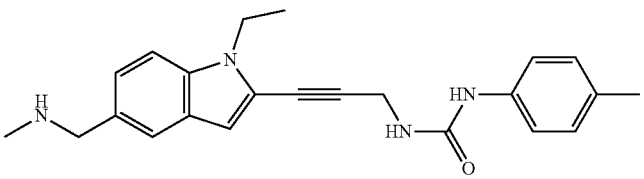
3-(3-{1-ethyl-5-[(methylamino)methyl]-1H-indol-2-yl}prop-2-yn-1-yl)-1-(4-methylphenyl)urea |

TABLE 1-continued

List of compounds

| # | Structure IUPAC name |
|---|---|
| 64-P | 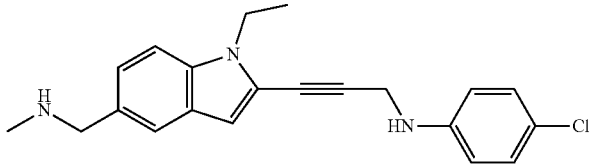 [SMILES: CCn1c(C#CCNc2ccc(Cl)cc2)cc2cc(CNC)ccc21]<br>4-chloro-N-(3-{1-ethyl-5-[(methylamino)methyl]-1H-indol-2-yl}prop-2-yn-1-yl)aniline |
| 65-P | 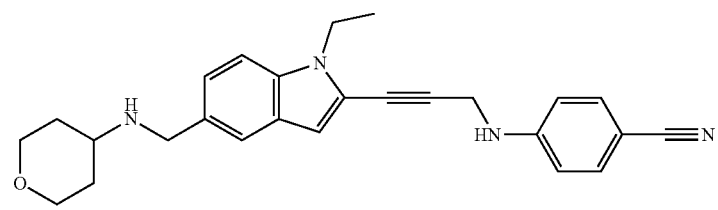 [SMILES: CCn1c(C#CCNc2ccc(C#N)cc2)cc2cc(CNC3CCOCC3)ccc21]<br>4-{[3-(1-ethyl-5-{[(oxan-4-yl)amino]methyl}-1H-indol-2-yl)prop-2-yn-1-yl]amino}benzonitrile |
| 66-P | 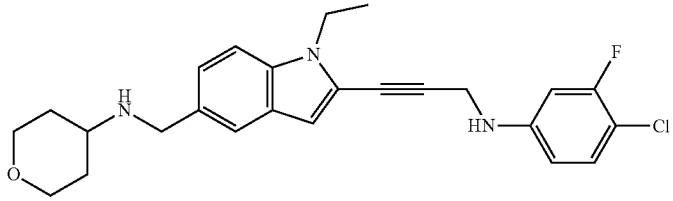 [SMILES: CCn1c(C#CCNc2ccc(Cl)c(F)c2)cc2cc(CNC3CCOCC3)ccc21]<br>N-[(2-{3-[(4-chloro-3-fluorophenyl)amino]prop-1-yn-1-yl}-1-ethyl-1H-indol-5-yl)methyl]oxan-4-amine |
| 67-P | 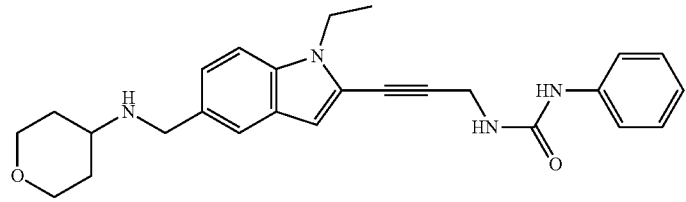 [SMILES: CCn1c(C#CCNC(=O)Nc2ccccc2)cc2cc(CNC3CCOCC3)ccc21]<br>3-[3-(1-ethyl-5-{[(oxan-4-yl)amino]methyl}-1H-indol-2-yl)prop-2-yn-1-yl]-1-phenylurea |
| 68-P | 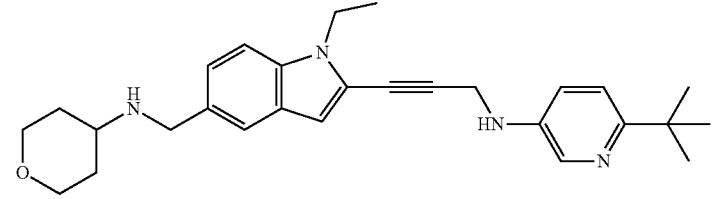 [SMILES: CCn1c(C#CCNc2ccc(C(C)(C)C)nc2)cc2cc(CNC3CCOCC3)ccc21]<br>6-tert-butyl-N-[3-(1-ethyl-5-{[(oxan-4-yl)amino]methyl}-1H-indol-2-yl)prop-2-yn-1-yl]pyridin-3-amine |

TABLE 1-continued

List of compounds

| # | Structure IUPAC name |
|---|---|
| 69-P | 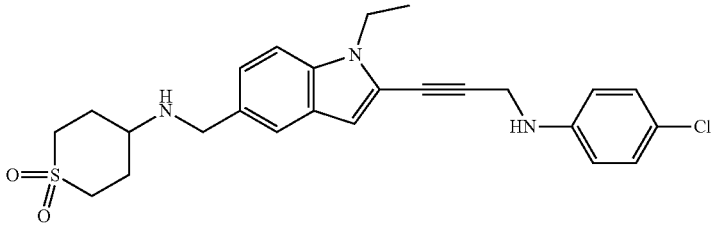 [SMILES: CCn1c(C#CCNc2ccc(Cl)cc2)cc2cc(CNC3CCS(=O)(=O)CC3)ccc21]<br>4-{[(2-{3-[(4-chlorophenyl)amino]prop-1-yn-1-yl}-1-ethyl-1H-indol-5-yl)methyl]amino}-1$\lambda^6$-thiane-1,1-dione |
| 70-P | 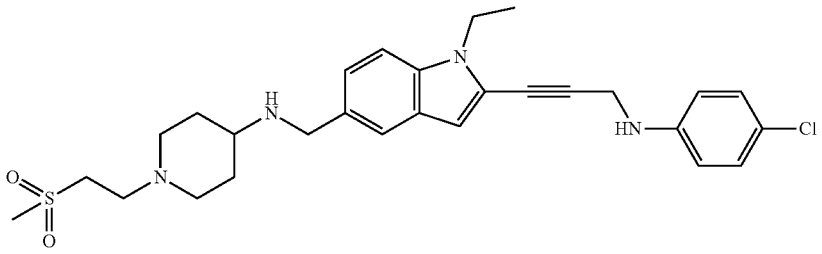 [SMILES: CCn1c(C#CCNc2ccc(Cl)cc2)cc2cc(CNC3CCN(CCS(C)(=O)=O)CC3)ccc21]<br>N-[(2-{3-[(4-chlorophenyl)amino]prop-1-yn-1-yl}-1-ethyl-1H-indol-5-yl)methyl]-1-(2-methanesulfonylethyl)piperidin-4-amine |
| 71-P | 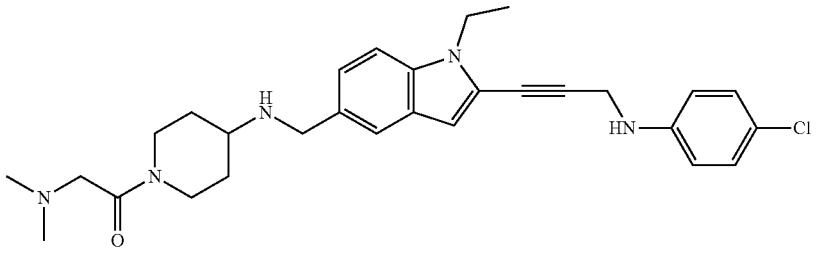 [SMILES: CCn1c(C#CCNc2ccc(Cl)cc2)cc2cc(CNC3CCN(C(=O)CN(C)C)CC3)ccc21]<br>1-(4-{[(2-{3-[(4-chlorophenyl)amino]prop-1-yn-1-yl}-1-ethyl-1H-indol-5-yl)methyl]amino}piperidin-1-yl)-2-(dimethylamino)ethan-1-one |
| 72-P | 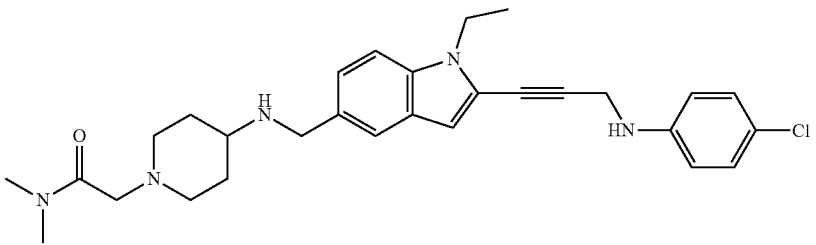 [SMILES: CCn1c(C#CCNc2ccc(Cl)cc2)cc2cc(CNC3CCN(CC(=O)N(C)C)CC3)ccc21]<br>2-(4-{[(2-{3-[(4-chlorophenyl)amino]prop-1-yn-1-yl}-1-ethyl-1H-indol-5-yl)methyl]amino}piperidin-1-yl)-N,N-dimethylacetamide |
| 73-P | 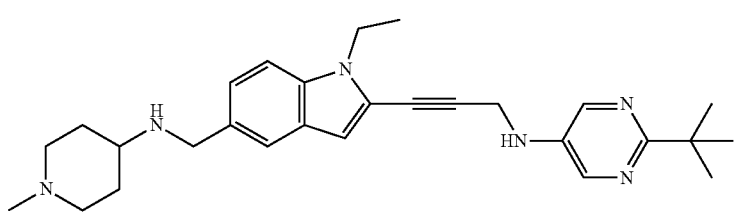 [SMILES: CCn1c(C#CCNc2cnc(C(C)(C)C)nc2)cc2cc(CNC3CCN(C)CC3)ccc21]<br>2-tert-butyl-N-[3-(1-ethyl-5-{[(1-methylpiperidin-4-yl)amino]methyl}-1H-indol-2-yl)prop-2-yn-1-yl]pyrimidin-5-amine |

TABLE 1-continued

List of compounds

| # | Structure | IUPAC name |
|---|---|---|
| 74-P | 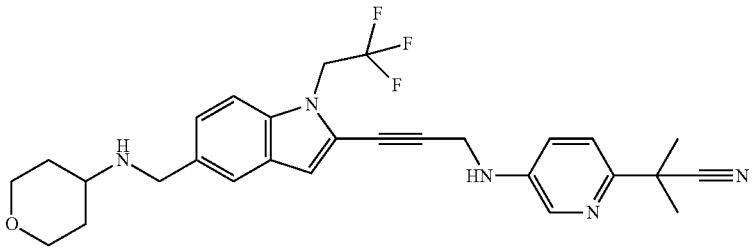 [SMILES: CC(C)(C#N)c1ccc(NCC#Cc2cc3cc(CNC4CCOCC4)ccc3n2CC(F)(F)F)cn1] | 2-methyl-2-(5-{[3-(5-{[(oxan-4-yl)amino]methyl]-1-(2,2,2-trifluoroethyl)-1H-indol-2-yl)prop-2-yn-1-yl]amino}pyridin-2-yl)propanenitrile |
| 75-P | 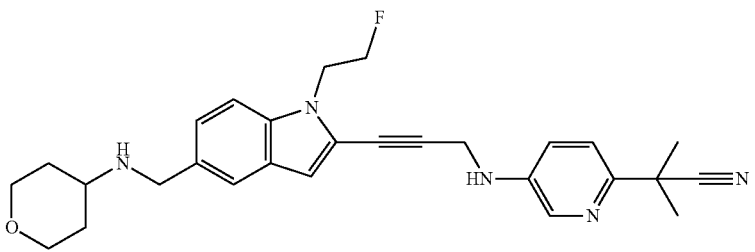 | 2-[5-({3-[1-(2-fluoroethyl)-5-{[(oxan-4-yl)amino]methyl}-1H-indol-2-yl]prop-2-yn-1-yl}amino)pyridin-2-yl]-2-methylpropanenitrile |
| 76-P | 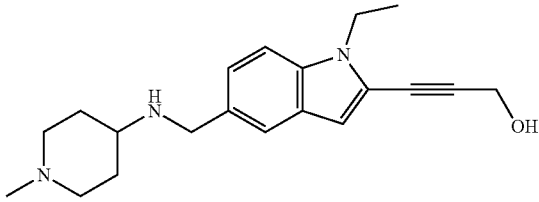 [SMILES: CCn1c(C#CCO)cc2cc(CNC3CCN(C)CC3)ccc21] | 3-(1-ethyl-5-{[(1-methylpiperidin-4-yl)amino]methyl}-1H-indol-2-yl)prop-2-yn-1-ol |
| 77-P | 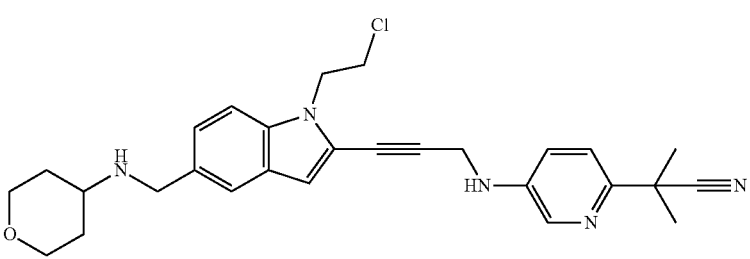 [SMILES: CC(C)(C#N)c1ccc(NCC#Cc2cc3cc(CNC4CCOCC4)ccc3n2CCCl)cn1] | 2-[5-({3-[1-(2-chloroethyl)-5-{[(oxan-4-yl)amino]methyl}-1H-indol-2-yl]prop-2-yn-1-yl}amino)pyridin-2-yl]-2-methylpropanenitrile |
| 78-P | 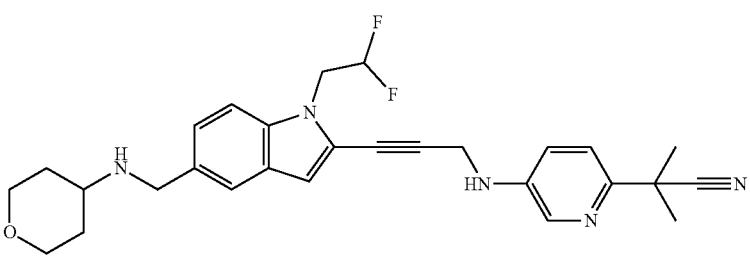 | 2-[5-({3-[1-(2,2-difluoroethyl)-5-{[(oxan-4-yl)amino]methyl}-1H-indol-2-yl]prop-2-yn-1-yl}amino)pyridin-2-yl]-2-methylpropanenitrile |

TABLE 1-continued

List of compounds

| # | Structure IUPAC name |
|---|---|
| 79-P | 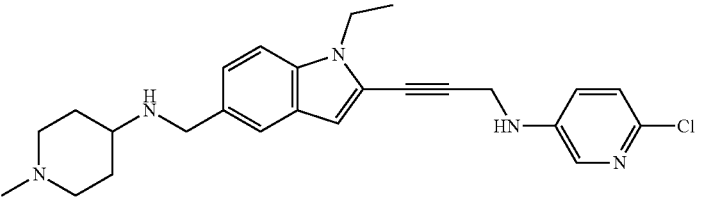 [SMILES: CCn1c(C#CCNc2ccc(Cl)nc2)cc2cc(CNC3CCN(C)CC3)ccc21]<br>6-chloro-N-[3-(1-ethyl-5-{[(1-methylpiperidin-4-yl)amino]methyl}-1H-indol-2-yl)prop-2-yn-1-yl]pyridin-3-amine |
| 80-P | 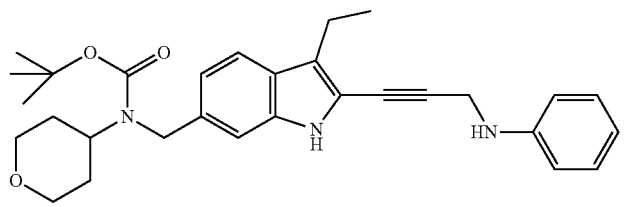 [SMILES: CCc1c(C#CCNc2ccccc2)[nH]c2cc(CN(C(=O)OC(C)(C)C)C3CCOCC3)ccc12]<br>tert-butyl N-({3-ethyl-2-{3-(phenylamino)prop-1-yn-1-yl]-1H-indol-6-yl}methyl)-N-(oxan-4-yl)carbamate |
| 81-P | 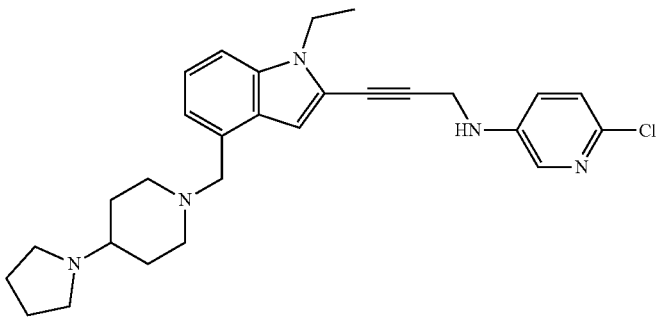 [SMILES: CCn1c(C#CCNc2ccc(Cl)nc2)cc2c(CN3CCC(N4CCCC4)CC3)cccc21]<br>6-Chloro-N-[3-(1-ethyl-4-{[4-(pyrrolidin-1-yl)piperidin-1-yl]methyl}-1H-indol-2-yl)prop-2-yn-1-yl]pyridin-3-amine |
| 82-P | 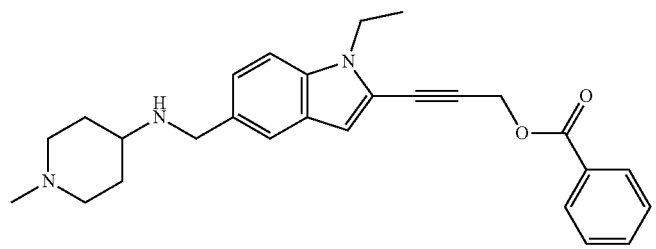 [SMILES: CCn1c(C#CCOC(=O)c2ccccc2)cc2cc(CNC3CCN(C)CC3)ccc21]<br>3-(1-ethyl-5-{[(1-methylpiperidin-4-yl)amino]methyl}-1H-indol-2-yl)prop-2-yn-1-yl benzoate |
| 83-P | 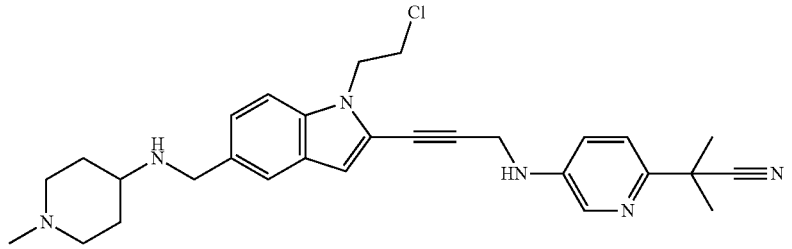 [SMILES: CN1CCC(NCc2ccc3c(c2)cc(C#CCNc2ccc(C(C)(C)C#N)nc2)n3CCCl)CC1]<br>2-[5-({3-[1-(2-chloroethyl)-5-{[(1-methylpiperidin-4-yl)amino]methyl}-1H-indol-2-yl]prop-2-yn-1-yl}amino)pyridin-2-yl]-2-methylpropanenitrile |

TABLE 1-continued

List of compounds

| # | Structure IUPAC name |
|---|---|
| 84-P | 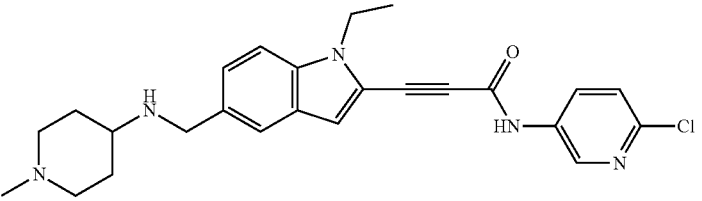 [SMILES: CCn1c(C#CC(=O)Nc2ccc(Cl)nc2)cc2cc(CNC3CCN(C)CC3)ccc21]<br>N-(6-chloropyridin-3-yl)-3-(1-ethyl-5-{[(1-methylpiperidin-4-yl)amino]methyl}-1H-indol-2-yl)prop-2-ynamide |
| 85-P | 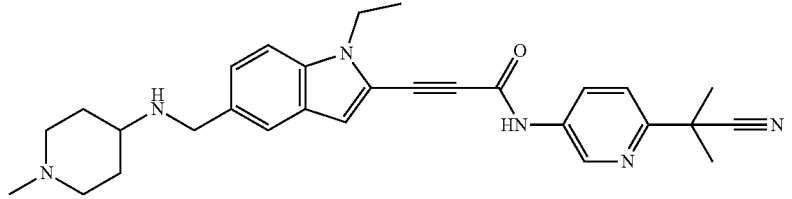<br>N-[6-(1-cyano-1-methylethyl)pyridin-3-yl]-3-(1-ethyl-5-{[(1-methylpiperidin-4-yl)amino]methyl}-1H-indol-2-yl)prop-2-ynamide |
| 86-P | 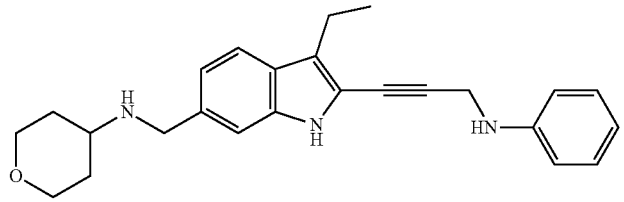 [SMILES: CCc1c(C#CCNc2ccccc2)[nH]c2cc(CNC3CCOCC3)ccc12]<br>N-({3-ethyl-2-{3-(phenylamino)prop-1-yn-1-yl]-1H-indol-6-yl}methyl)oxan-4-amine |
| 87-P | 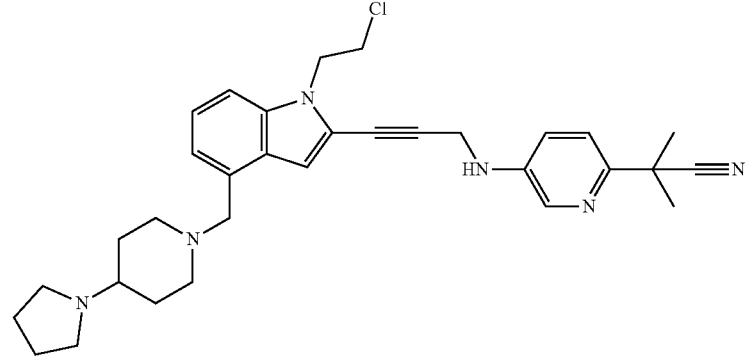 [SMILES: CC(C)(C#N)c1ccc(NCC#Cc2cc3c(CN4CCC(N5CCCC5)CC4)cccc3n2CCCl)cn1]<br>2-[5-({3-[1-(2-chloroethyl)-4-{[4-(pyrrolidin-1-yl)piperidin-1-yl]methyl}-1H-indol-2-yl]prop-2-yn-1-yl}amino)pyridin-2-yl]-2-methylpropanenitrile |

TABLE 1-continued

List of compounds

| # | Structure IUPAC name |
|---|---|
| 88-P | 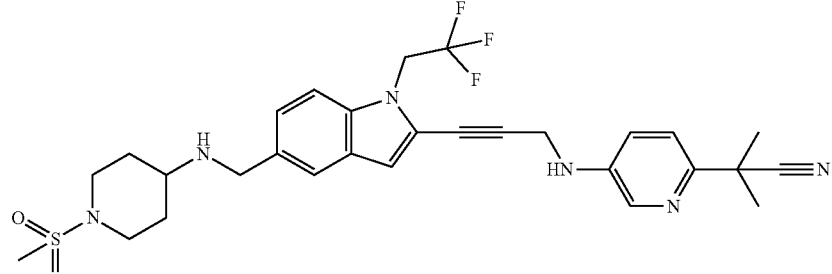<br>2-(5-{[3-(5-{[(1-methanesulfonylpiperidin-4-yl)amino]methyl}-1-(2,2,2-trifluoroethyl)-1H-indol-2-yl)prop-2-yn-1-yl]amino}pyridin-2-yl)-2-methylpropanenitrile |
| 89-P | 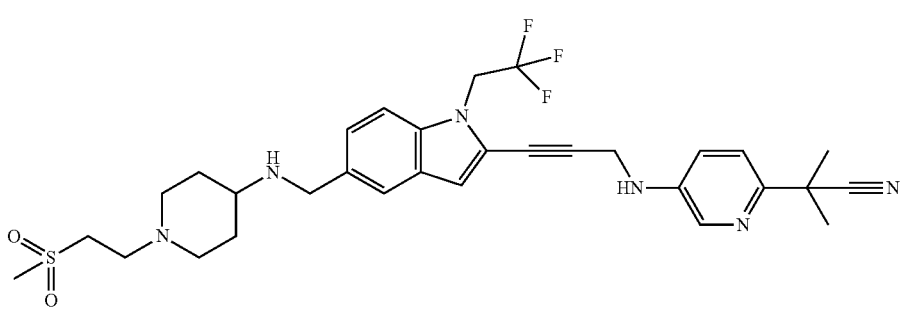 [SMILES: CC(C)(C#N)c1ccc(NCC#Cc2cc3cc(CNC4CCN(CCS(C)(=O)=O)CC4)ccc3n2CC(F)(F)F)cn1]<br>2-[5-({3-[5-({[1-(2-methanesulfonylethyl)piperidin-4-yl]amino}methyl)-1-(2,2,2-trifluoroethyl)-1H-indol-2-yl]prop-2-yn-1-yl}amino)pyridin-2-yl]-2-methylpropanenitrile |
| 90-P | 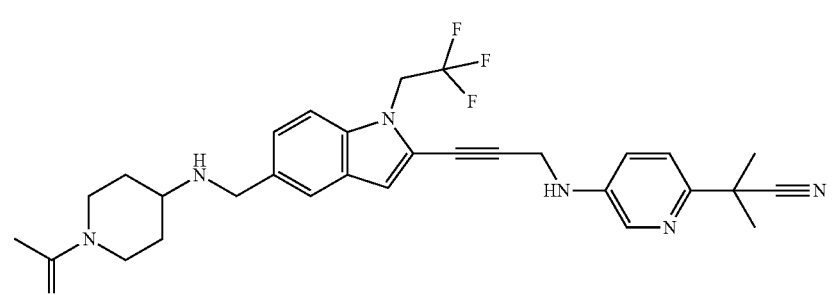<br>2-(5-{[3-(5-{[3-(5-{[(1-acetylpiperidin-4-yl)amino]methyl}-1-(2,2,2-trifluoroethyl)-1H-indol-2-yl)prop-2-yn-1-yl]amino}pyridin-2-yl)-2-methylpropanenitrile |

TABLE 1-continued

List of compounds

| # | Structure IUPAC name |
|---|---|
| 91-P | 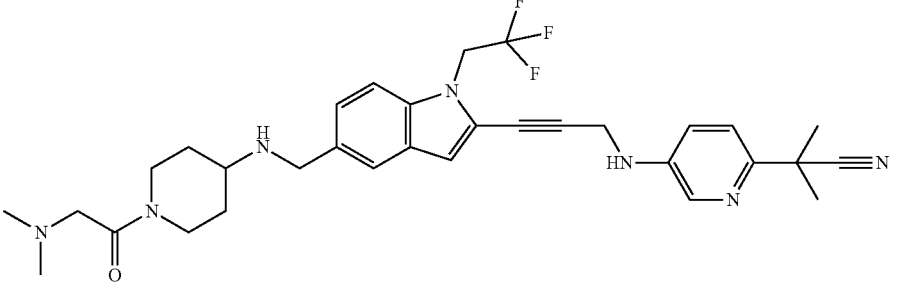<br>2-{5-[(3-{5-[({1-[2-(dimethylamino)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 92-P | 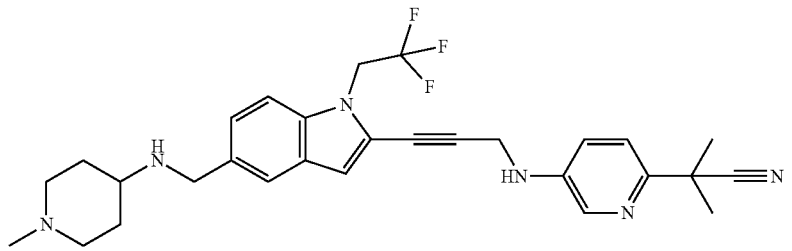 [SMILES: CN1CCC(NCc2ccc3c(c2)cc(C#CCNc2ccc(C(C)(C)C#N)nc2)n3CC(F)(F)F)CC1]<br>2-methyl-2-(5-{[3-(5-{[(1-methylpiperidin-4-yl)amino]methyl}-1-(2,2,2-trifluoroethyl)-1H-indol-2-yl)prop-2-yn-1-yl]amino}pyridin-2-yl)propanenitrile |
| 93-P | 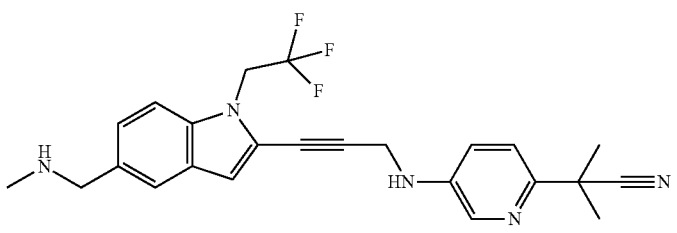 [SMILES: CNCc1ccc2c(c1)cc(C#CCNc1ccc(C(C)(C)C#N)nc1)n2CC(F)(F)F]<br>2-methyl-2-{5-[(3-{5-[(methylamino)methyl]-1-(2,2,2-trifluoroethyl)-1H-indol-2-yl}prop-2-yn-1-yl)amino]pyridin-2-yl}propanenitrile |
| 94-P | 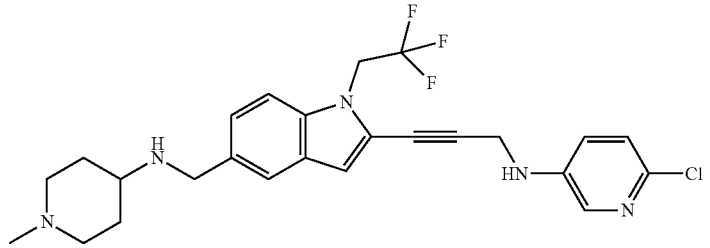 [SMILES: CN1CCC(NCc2ccc3c(c2)cc(C#CCNc2ccc(Cl)nc2)n3CC(F)(F)F)CC1]<br>6-Chloro-N-[3-(5-{[(1-methylpiperidin-4-yl)amino]methyl}-1-(2,2,2-trifluoroethyl)-1H-indol-2-yl)prop-2-yn-1-yl]pyridin-3-amine |

TABLE 1-continued

List of compounds

| # | Structure IUPAC name |
|---|---|
| 95-P | 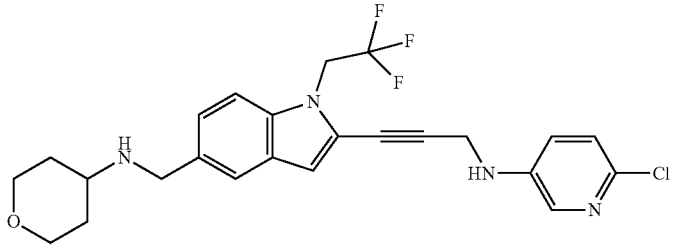6-chloro-N-[3-(5-{[(oxan-4-yl)amino]methyl}-1-(2,2,2-trifluoroethyl)-1H-indol-2-yl)prop-2-yn-1-yl]pyridin-3-amine |
| 96-P | 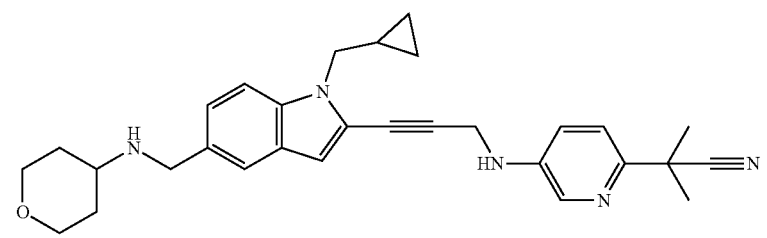2-[5-({3-[1-(cyclopropylmethyl)-5-{[(oxan-4-yl)amino]methyl}-1H-indol-2-yl]prop-2-yn-1-yl}amino)pyridin-2-yl]-2-methylpropanenitrile |
| 97-P | 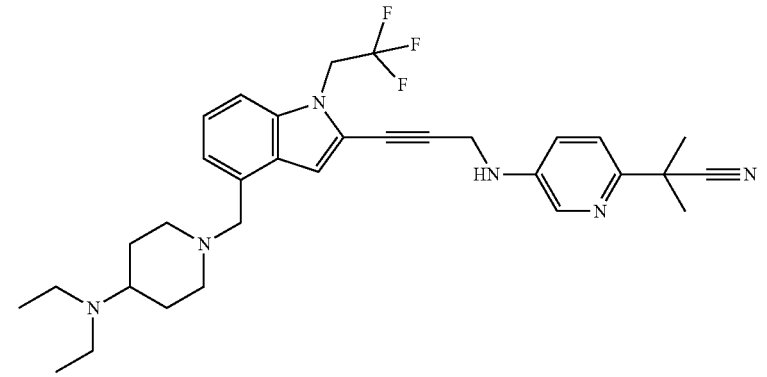 [SMILES: CCN(CC)C1CCN(Cc2cccc3c2cc(C#CCNc2ccc(C(C)(C)C#N)nc2)n3CC(F)(F)F)CC1]2-(5-{[3-(4-{[4-(4-hydroxypiperidin-1-yl]methyl}-1-(2,2,2-trifluoroethyl)-1H-indol-2-yl)prop-2-yn-1-yl]amino}pyridin-2-yl)-2-methylpropanenitrile |
| 98-P | 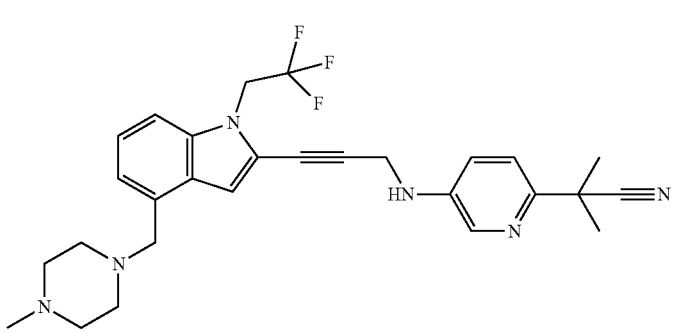 [SMILES: CN1CCN(Cc2cccc3c2cc(C#CCNc2ccc(C(C)(C)C#N)nc2)n3CC(F)(F)F)CC1]2-methyl-2-{5-[(3-{4-[(4-methylpiperazin-1-yl)methyl]-1-(2,2,2-trifluoroethyl)-1H-indol-2-yl}prop-2-yn-1-yl)amino]pyridin-2-yl}propanenitrile |

TABLE 1-continued

List of compounds

| # | Structure IUPAC name |
|---|---|
| 99-P | 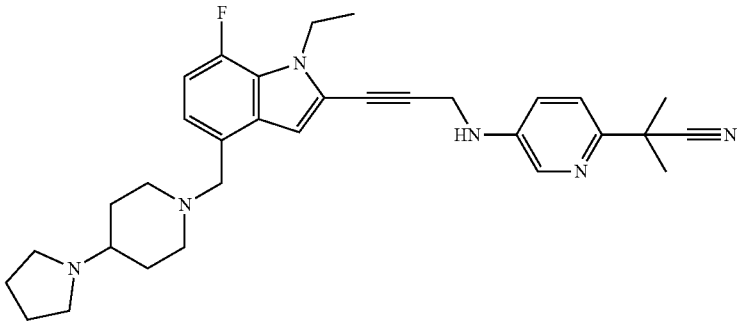 [SMILES: CCn1c(C#CCNc2ccc(C(C)(C)C#N)nc2)cc2c(CN3CCC(N4CCCC4)CC3)ccc(F)c21]<br>2-(5-{[3-(1-ethyl-7-fluoro-4-{[4-(pyrrolidin-1-yl)piperidin-1-yl]methyl}-1H-indol-2-yl)prop-2-yn-1-yl]amino}pyridin-2-yl)-2-methylpropanenitrile |
| 100-P | 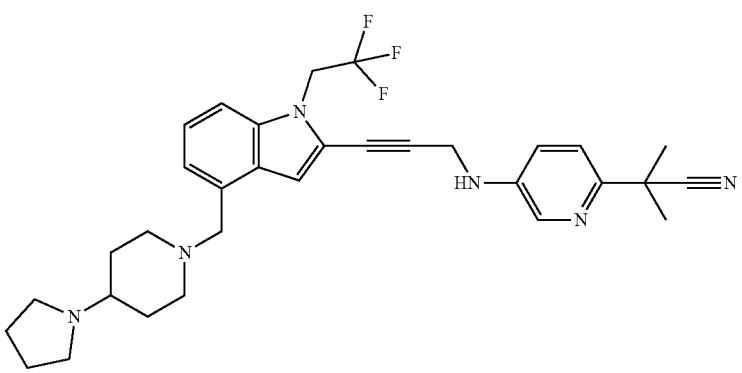 [SMILES: CC(C)(C#N)c1ccc(NCC#Cc2cc3c(CN4CCC(N5CCCC5)CC4)cccc3n2CC(F)(F)F)cn1]<br>2-methyl-2-(5-{[3-(4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)propanenitrile |
| 101-P | 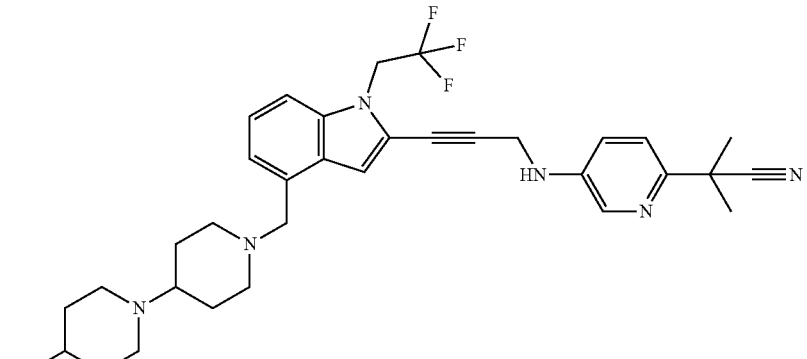<br>2-(5-{[3-(4-{[4-(4-hydroxypiperidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |

TABLE 1-continued

List of compounds

| # | Structure IUPAC name |
|---|---|
| 102-P | 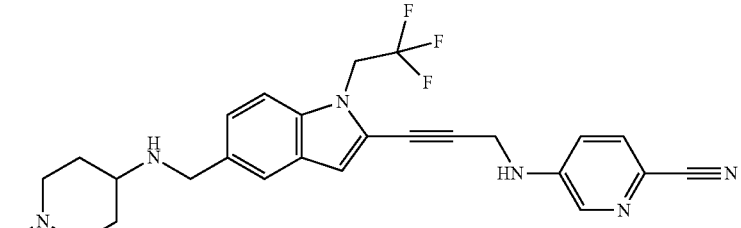<br>N-(6-cyanopyridin-3-yl)-3-(1-ethyl-5-{[(1-methylpiperidin-4-yl)amino]methyl}-1H-indol-2-yl)prop-2-ynamide |
| 103-P | 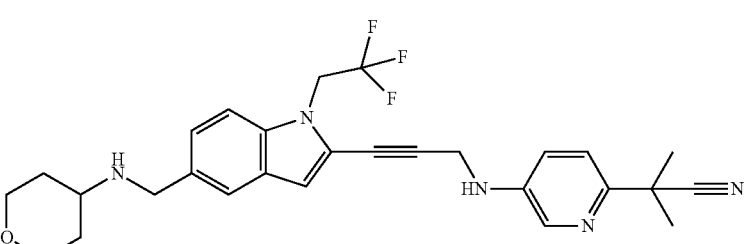<br>N-[6-(1-cyano-1-methylethyl)pyridin-3-yl]-3-(5-{[(oxan-4-yl)amino]methyl}-1-(2,2,2-trifluoroethyl)-1H-indol-2-yl)prop-2-ynamide |
| 104-P | 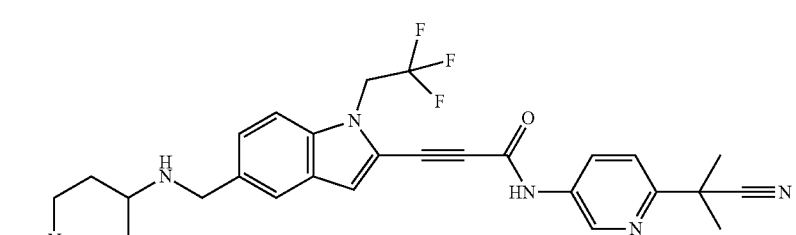<br>N-[6-(1-cyano-1-methylethyl)pyridin-3-yl]-3-(5-{[(1-methylpiperidin-4-yl)amino]methyl}-1-(2,2,2-trifluoroethyl)-1H-indol-2-yl)prop-2-ynamide |
| 105-P | 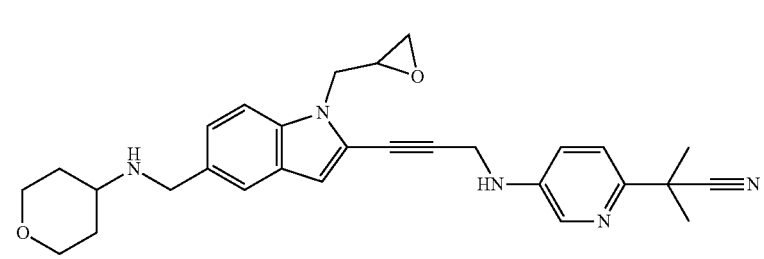 [SMILES: CC(C)(C#N)c1ccc(NCC#Cc2cc3cc(CNC4CCOCC4)ccc3n2CC2CO2)cn1]<br>2-methyl-2-(5-{[3-(5-{[(oxan-4-yl)amino]methyl}-1-(oxiran-2-ylmethyl)-1H-indol-2-yl)prop-2-yn-1-yl]amino}pyridin-2-yl)propanenitrile |

TABLE 1-continued

List of compounds

| # | Structure IUPAC name |
|---|---|
| 106-P | 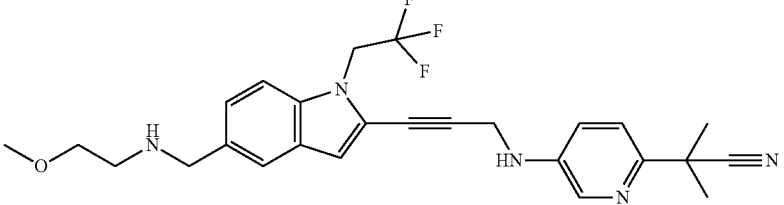<br>2-(5-{[3-(5-{[(2-methoxyethyl)amino]methyl}-1-(2,2,2-trifluoroethyl)-1H-indol-2-yl)prop-2-yn-1-yl]amino}pyridin-2-yl)-2-methylpropanenitrile |
| 107-P | 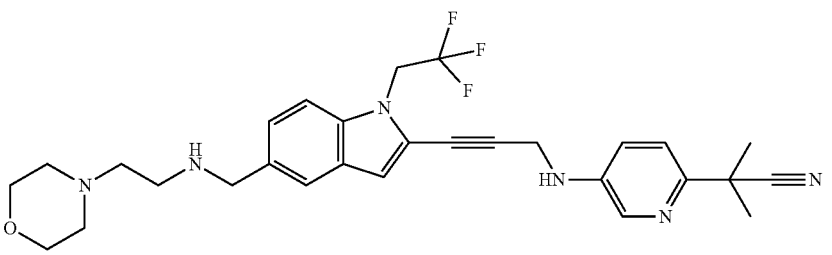 [SMILES: CC(C)(C#N)c1ccc(NCC#Cc2cc3cc(CNCCN4CCOCC4)ccc3n2CC(F)(F)F)cn1]<br>2-methyl-2-[5-({3-[5-({[2-(morpholin-4-yl)ethyl]amino}methyl)-1-(2,2,2-trifluoroethyl)-1H-indol-2-yl]prop-2-yn-1-yl}amino)pyridin-2-yl]propanenitrile |
| 108-P | 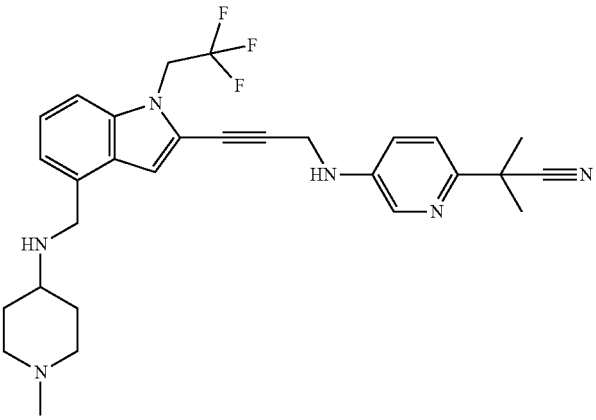 [SMILES: CN1CCC(NCc2cccc3c2cc(C#CCNc2ccc(C(C)(C)C#N)nc2)n3CC(F)(F)F)CC1]<br>2-methyl-2-(5-{[3-(4-{[(1-methylpiperidin-4-yl)amino]methyl}-1-(2,2,2-trifluoroethyl)-1H-indol-2-yl)prop-2-yn-1-yl]amino}pyridin-2-yl)propanenitrile |

TABLE 1-continued

List of compounds

| # | Structure IUPAC name |
|---|---|
| 109-P | 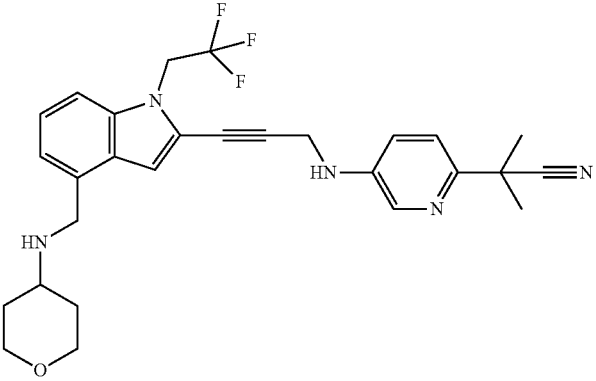 [SMILES: CC(C)(C#N)c1ccc(NCC#Cc2cc3c(CNC4CCOCC4)cccc3n2CC(F)(F)F)cn1]<br>2-methyl-2-(5-{[3-(4-{[(oxan-4-yl)amino]methyl}-1-(2,2,2-trifluoroethyl)-1H-indol-2-yl)prop-2-yn-1-yl]amino}pyridin-2-yl)propanenitrile |
| 110-P | 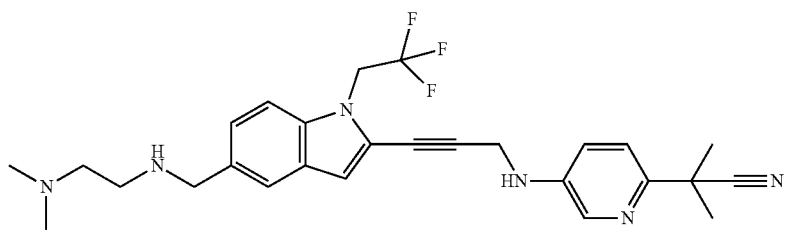 [SMILES: CN(C)CCNCc1ccc2c(c1)cc(C#CCNc1ccc(C(C)(C)C#N)nc1)n2CC(F)(F)F]<br>2-(5-({3-[5-({[2-(dimethylamino)ethyl]amino}methyl)-1-(2,2,2-trifluoroethyl)-1H-indol-2-yl]prop-2-yn-1-yl}amino)pyridin-2-yl]-2-methylpropanenitrile |
| 111-P | 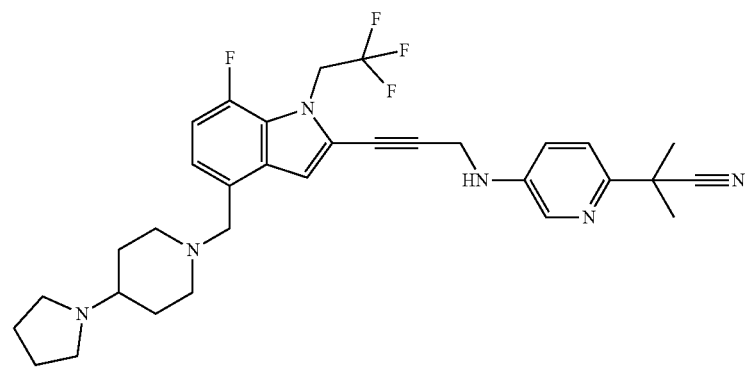 [SMILES: CC(C)(C#N)c1ccc(NCC#Cc2cc3c(CN4CCC(N5CCCC5)CC4)ccc(F)c3n2CC(F)(F)F)cn1]<br>2-(5-{[3-(7-fluoro-4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 112-P | 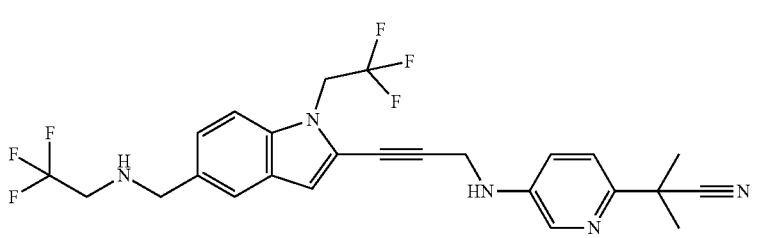 [SMILES: CC(C)(C#N)c1ccc(NCC#Cc2cc3cc(CNCC(F)(F)F)ccc3n2CC(F)(F)F)cn1]<br>2-methyl-2-[5-({3-[1-(2,2,2-trifluoroethyl)-5-{[(2,2,2-trifluoroethyl)amino]methyl}-1H-indol-2-yl]prop-2-yn-1-yl}amino)pyridin-2-yl]propanenitrile |

TABLE 1-continued

List of compounds

| # | Structure IUPAC name |
|---|---|
| 113-P | 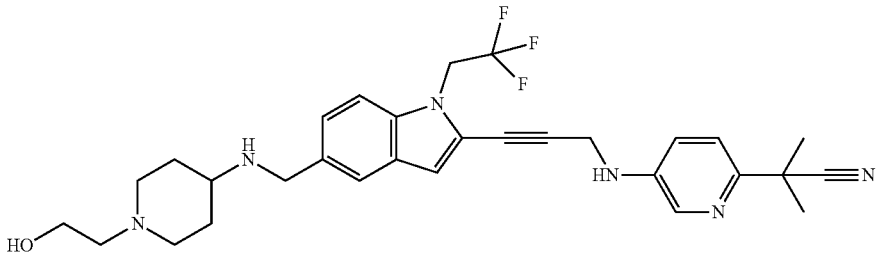 [SMILES: CC(C)(C#N)c1ccc(NCC#Cc2cc3cc(CNC4CCN(CCO)CC4)ccc3n2CC(F)(F)F)cn1]<br>2-[5-({3-[5-({[1-(2-hydroxyethyl)piperidin-4-yl]amino}methyl)-1-(2,2,2-trifluoroethyl)-1H-indol-2-yl]prop-2-yn-1-yl}amino)pyridin-2-yl]-2-methylpropanenitrile |
| 114-P | 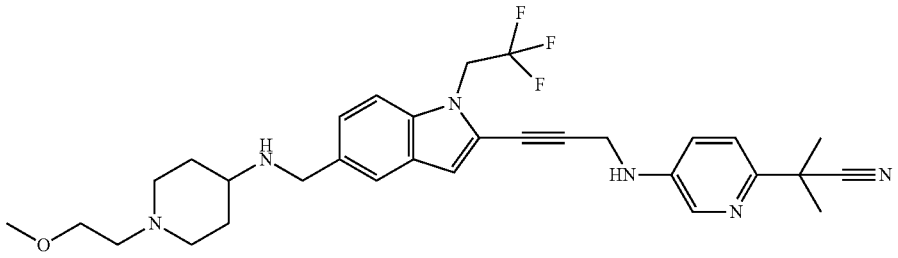 [SMILES: COCCN1CCC(NCc2ccc3c(c2)cc(C#CCNc2ccc(C(C)(C)C#N)nc2)n3CC(F)(F)F)CC1]<br>2-[5-({3-[5-({[1-(2-methoxyethyl)piperidin-4-yl]amino}methyl)-1(2,2,2-trifluoroethyl)-1H-indol-2-yl]prop-2-yn-1-yl}amino)pyridin-2-yl]-2-methylpropanenitrile |
| 115-P | 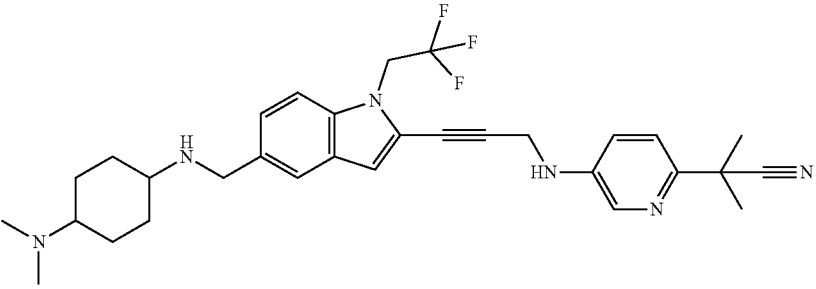 [SMILES: CN(C)C1CCC(NCc2ccc3c(c2)cc(C#CCNc2ccc(C(C)(C)C#N)nc2)n3CC(F)(F)F)CC1]<br>2-[5-({3-[5-({[4-(dimethylamino)cyclohexyl]amino}methyl)-1-(2,2,2-trifluoroethyl)-1H-indol-2-yl]prop-2-yn-1-yl}amino)pyridin-2-yl]-2-methylpropanenitrile |
| 116-P | 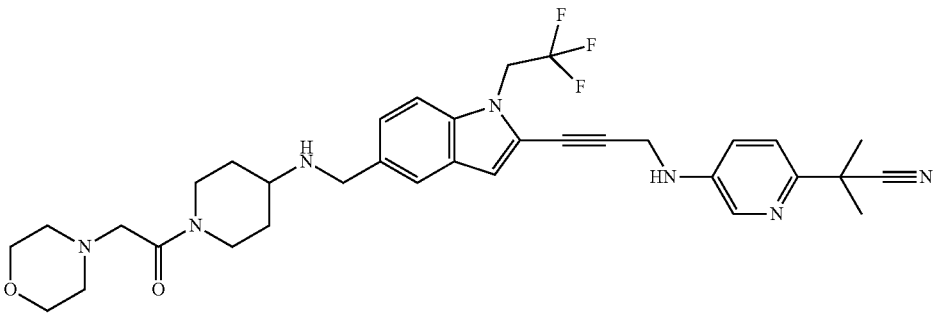 [SMILES: CC(C)(C#N)c1ccc(NCC#Cc2cc3cc(CNC4CCN(C(=O)CN5CCOCC5)CC4)ccc3n2CC(F)(F)F)cn1]<br>2-methyl-2-{5-[(3-{5-[({1-[2-(morpholin-4-yl)acetyl]piperidin-4-yl}amino)methyl]-1-(2,2,2-trifluoroethyl)-1H-indol-2-yl}prop-2-yn-1-yl)amino]pyridin-2-yl}propanenitrile |

TABLE 1-continued

List of compounds

| # | Structure | IUPAC name |
|---|---|---|
| 117-P | 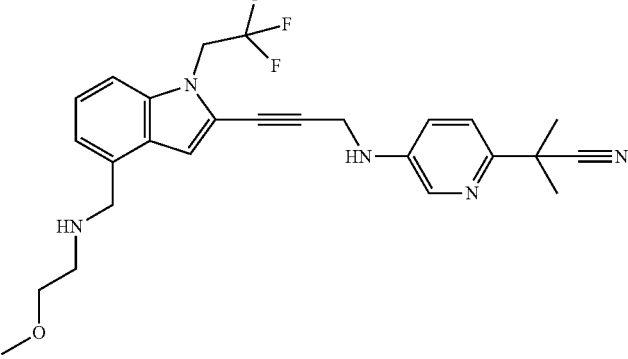 | 2-(5-{[3-(4-{[(2-methoxyethyl)amino]methyl}-1-(2,2,2-trifluoroethyl)-1H-indol-2-yl)prop-2-yn-1-yl]amino}pyridin-2-yl)-2-methylpropanenitrile |
| 118-P | 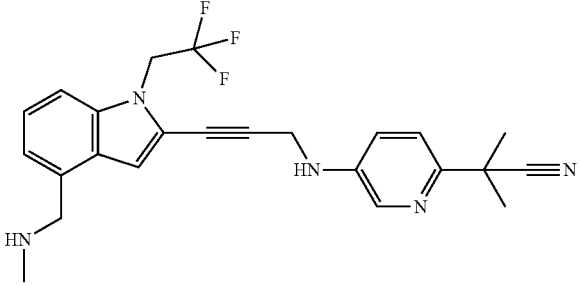 [SMILES: CNCc1cccc2c1cc(C#CCNc1ccc(C(C)(C)C#N)nc1)n2CC(F)(F)F] | 2-methyl-2-{5-[(3-{4-[(methylamino)methyl]-1-(2,2,2-trifluoroethyl)-1H-indol-2-yl}prop-2-yn-1-yl)amino]pyridin-2-yl}propanenitrile |
| 119-P | 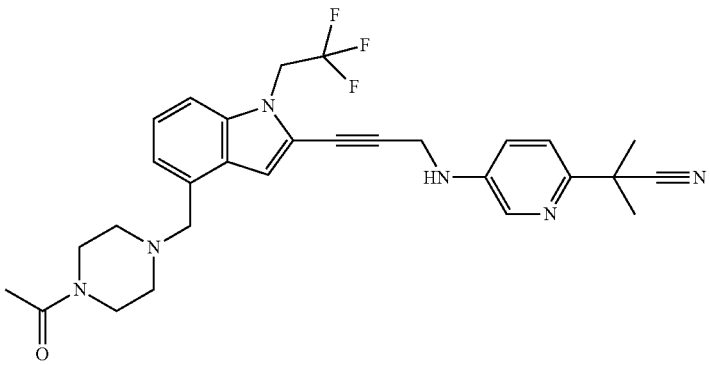 [SMILES: CC(=O)N1CCN(Cc2cccc3c2cc(C#CCNc2ccc(C(C)(C)C#N)nc2)n3CC(F)(F)F)CC1] | 2-{5-[(3-{4-[(4-acetylpiperazin-1-yl)methyl]-1-(2,2,2-trifluoroethyl)-1H-indol-2-yl}prop-2-yn-1-yl)amino]pyridin-2-yl}-2-methylpropanenitrile |

TABLE 1-continued

List of compounds

| # | Structure IUPAC name |
|---|---|
| 120-P | 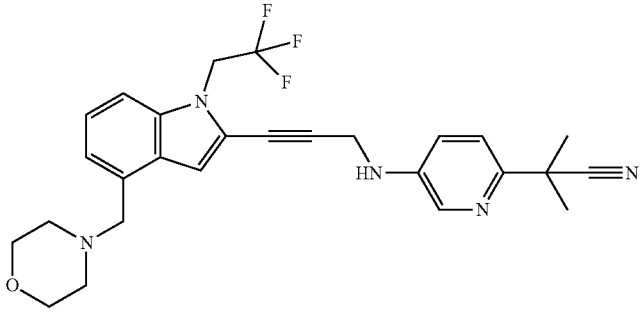 [SMILES: CC(C)(C#N)c1ccc(NCC#Cc2cc3c(CN4CCOCC4)cccc3n2CC(F)(F)F)cn1]
2-methyl-2-[5-({3-[4-(morpholin-4-ylmethyl)-1-(2,2,2-trifluoroethyl)-1H-indol-2-yl]prop-2-yn-1-yl}amino)pyridin-2-yl]propanenitrile |
| 121-P | 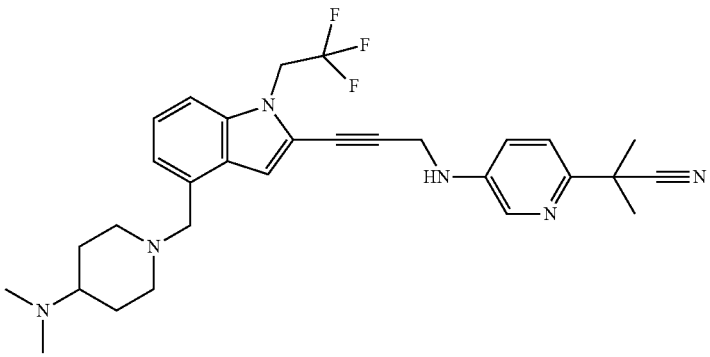 [SMILES: CN(C)C1CCN(Cc2cccc3c2cc(C#CCNc2ccc(C(C)(C)C#N)nc2)n3CC(F)(F)F)CC1]
2-(5-{[3-(4-{[4-(dimethylamino)piperidin-1-yl]methyl}-1-(2,2,2-trifluoroethyl)-1H-indol-2-yl)prop-2-yn-1-yl]amino}pyridin-2-yl)-2-methylpropanenitrile |
| 122-P | 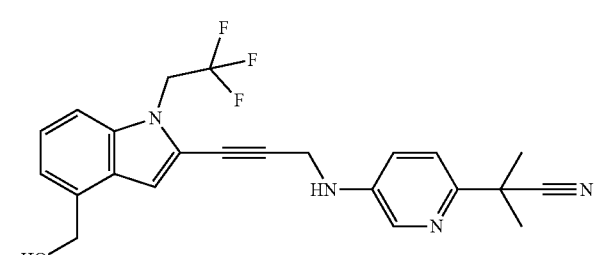
2-[5-({3-[4-(hydroxymethyl)-1-(2,2,2-trifluoroethyl)-1H-indol-2-yl]prop-2-yn-1-yl}amino)pyridin-2-yl]-2-methylpropanenitrile |

TABLE 1-continued

List of compounds

| # | Structure IUPAC name |
|---|---|
| 123-P | 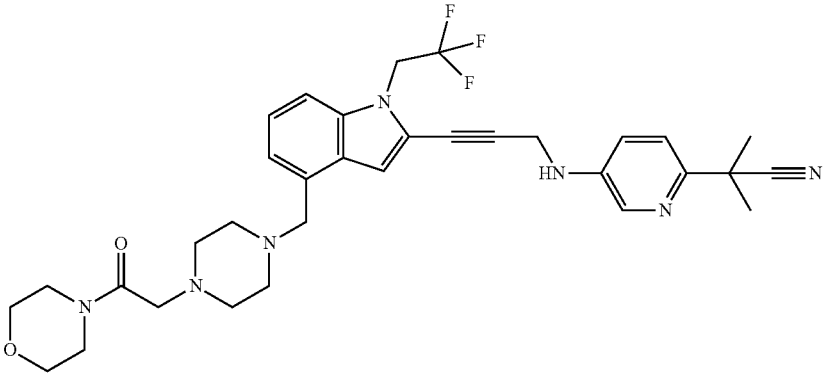
2-methyl-2-[5-({3-[4-({4-[2-(morpholin-4-yl)-2-oxoethyl]piperazin-1-yl}methyl)-1-(2,2,2-trifluoroethyl)-1H-indol-2-yl]prop-2-yn-1-yl}amino)pyridin-2-yl]propanenitrile |
| 124-P | 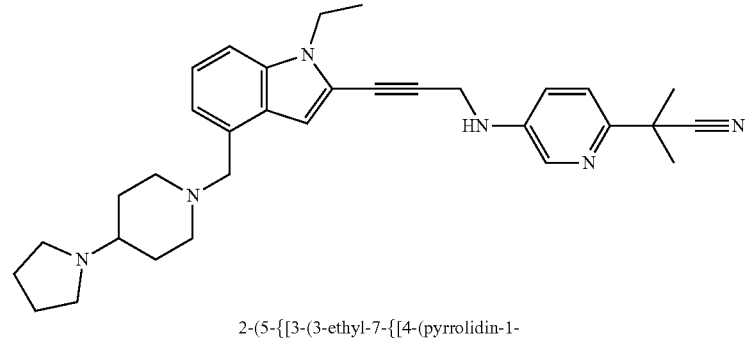
2-(5-{[3-(3-ethyl-7-{[4-(pyrrolidin-1-yl)piperidin-1-yl]methyl}-1H-indol-2-yl)prop-2-yn-1-yl]amino}pyridin-2-yl)-2-methylpropanenitrile |
| 125-P | 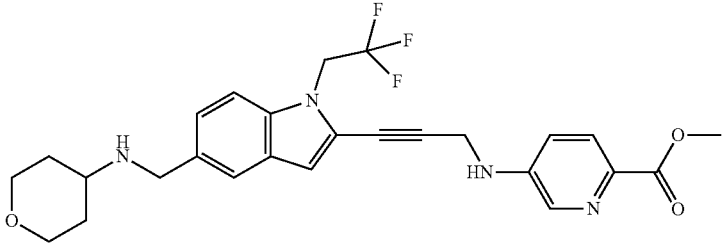 [SMILES: COC(=O)c1ccc(NCC#Cc2cc3cc(CNC4CCOCC4)ccc3n2CC(F)(F)F)cn1]
methyl 5-{[3-(5-{[(oxan-4-yl)amino]methyl}-1-(2,2,2-trifluoroethyl)-1H-indol-2-yl)prop-2-yn-1-yl]amino}pyridine-2-carboxylate |
| 126-P | 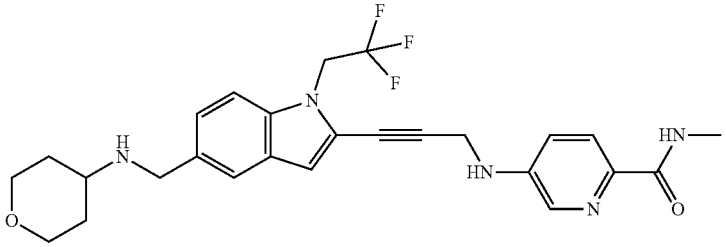
N-methyl-5-{[3-(5-{[(oxan-4-yl)amino]methyl}-1-(2,2,2-trifluoroethyl)-1H-indol-2-yl)prop-2-yn-1-yl]amino}pyridine-2-carboxamide |

TABLE 1-continued

List of compounds

| # | Structure IUPAC name |
|---|---|
| 127-P | 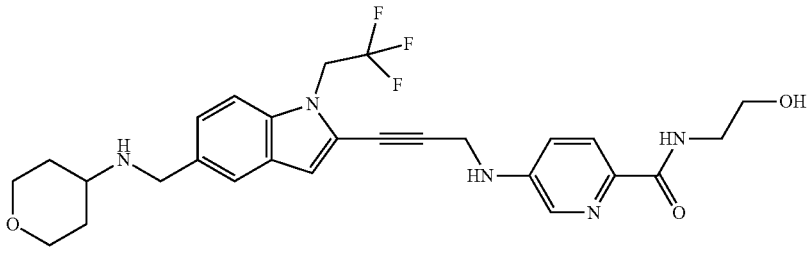 [SMILES: O=C(NCCO)c1ccc(NCC#Cc2cc3cc(CNC4CCOCC4)ccc3n2CC(F)(F)F)cn1] N-(2-hydroxyethyl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 128-P | 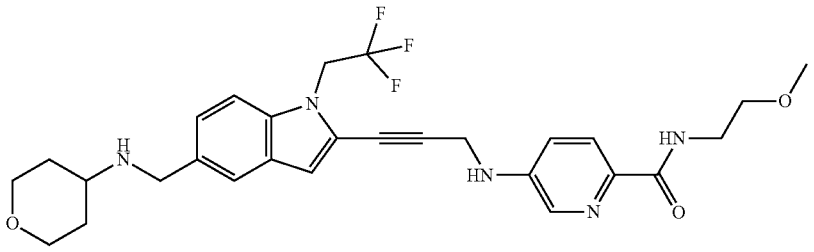 [SMILES: COCCNC(=O)c1ccc(NCC#Cc2cc3cc(CNC4CCOCC4)ccc3n2CC(F)(F)F)cn1] N-(2-methoxyethyl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 129-P | 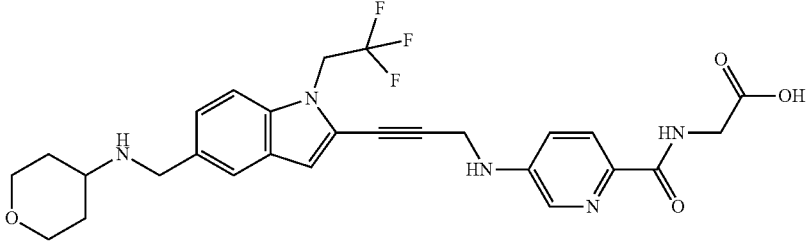 [SMILES: O=C(O)CNC(=O)c1ccc(NCC#Cc2cc3cc(CNC4CCOCC4)ccc3n2CC(F)(F)F)cn1] 2-[(5-{[3-(5-{[(oxan-4-yl)amino]methyl}-1-(2,2,2-trifluoroethyl)-1H-indol-2-yl)prop-2-yn-1-yl]amino}pyridin-2-yl)formamido]acetic acid |
| 130-P | 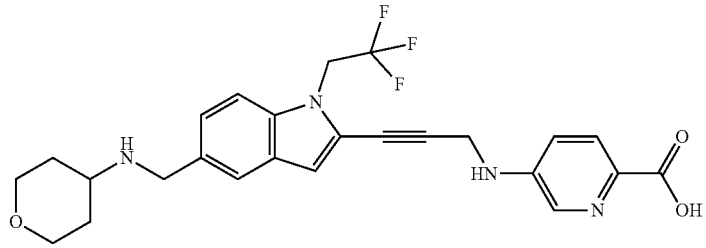 [SMILES: O=C(O)c1ccc(NCC#Cc2cc3cc(CNC4CCOCC4)ccc3n2CC(F)(F)F)cn1] 5-{[3-(5-{[(oxan-4-yl)amino]methyl}-1-(2,2,2-trifluoroethyl)-1H-indol-2-yl)prop-2-yn-1-yl]amino}pyridine-2-carboxylic acid |

TABLE 1-continued

List of compounds

| # | Structure | IUPAC name |
|---|---|---|
| 131-P | 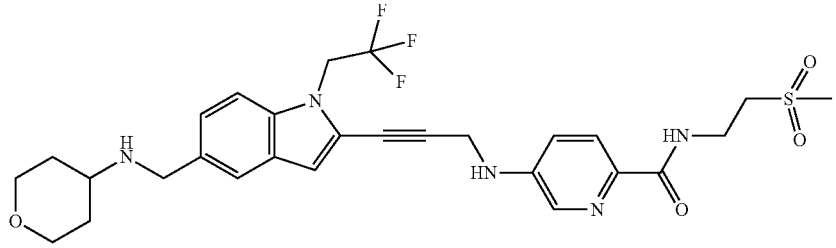 [SMILES: CS(=O)(=O)CCNC(=O)c1ccc(NCC#Cc2cc3cc(CNC4CCOCC4)ccc3n2CC(F)(F)F)cn1] | N-(2-methanesulfonylethyl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 132-P | 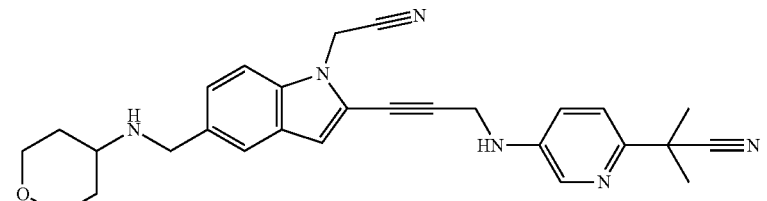 | 2-[5-({3-[1-(cyanomethyl)-5-{[(oxan-4-yl)amino]methyl}-1H-indol-2-yl]prop-2-yn-1-yl}amino)pyridin-2-yl]-2-methylpropanenitrile |
| 133-P | 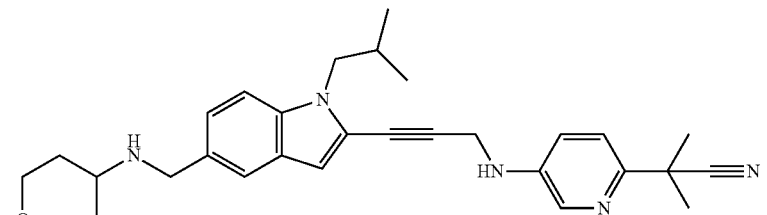 | 2-methyl-2-[5-({3-[1-(2-methylpropyl)-5-{[(oxan-4-yl)amino]methyl}-1H-indol-2-yl]prop-2-yn-1-yl}amino)pyridin-2-yl]propanenitrile |
| 134-P | 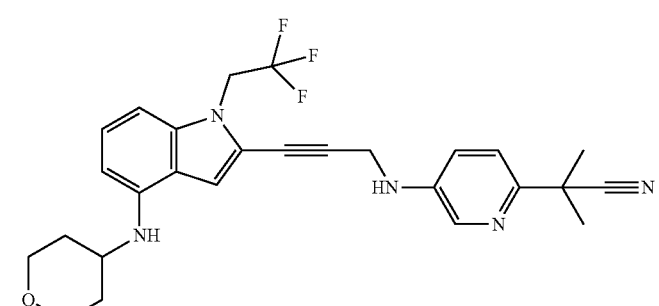 | 2-methyl-2-{5-[(3-{4-[(oxan-4-yl)amino]-1-(2,2,2-trifluoroethyl)-1H-indol-2-yl}prop-2-yn-1-yl)amino]pyridin-2-yl}propanenitrile |

TABLE 1-continued

List of compounds

| # | Structure IUPAC name |
|---|---|
| 135-P | 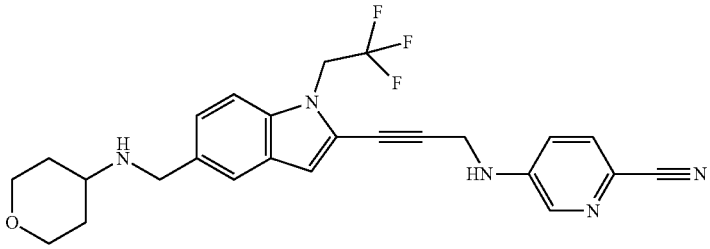 [SMILES: N#Cc1ccc(NCC#Cc2cc3cc(CNC4CCOCC4)ccc3n2CC(F)(F)F)cn1]  5-{[3-(5-{[(oxan-4-yl)amino]methyl}-1-(2,2,2-trifluoroethyl)-1H-indol-2-yl)prop-2-yn-1-yl]amino}pyridine-2-carbonitrile |
| 136-P | 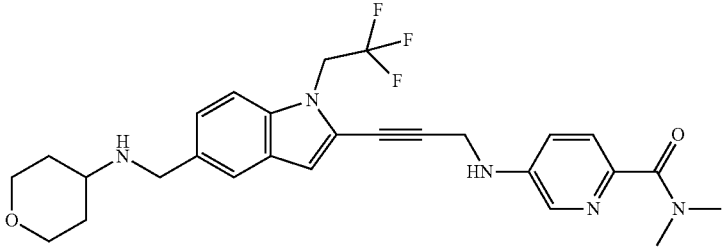 [SMILES: CN(C)C(=O)c1ccc(NCC#Cc2cc3cc(CNC4CCOCC4)ccc3n2CC(F)(F)F)cn1]  N,N-dimethyl-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 137-P | 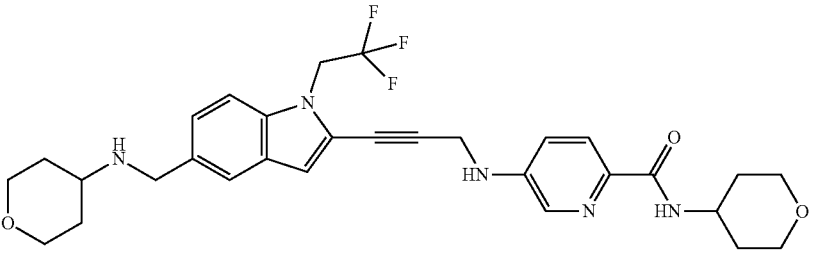 [SMILES: O=C(NC1CCOCC1)c1ccc(NCC#Cc2cc3cc(CNC4CCOCC4)ccc3n2CC(F)(F)F)cn1]  N-(oxan-4-yl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 138-P | 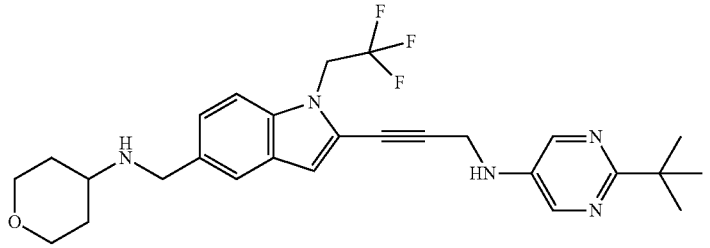 [SMILES: CC(C)(C)c1ncc(NCC#Cc2cc3cc(CNC4CCOCC4)ccc3n2CC(F)(F)F)cn1]  2-tert-butyl-N-[3-(5-{[(oxan-4-yl)amino]methyl}-1-(2,2,2-trifluoroethyl)-1H-indol-2-yl)prop-2-yn-1-yl]pyrimidin-5-amine |

TABLE 1-continued

List of compounds

| # | Structure | IUPAC name |
|---|---|---|
| 139-P | 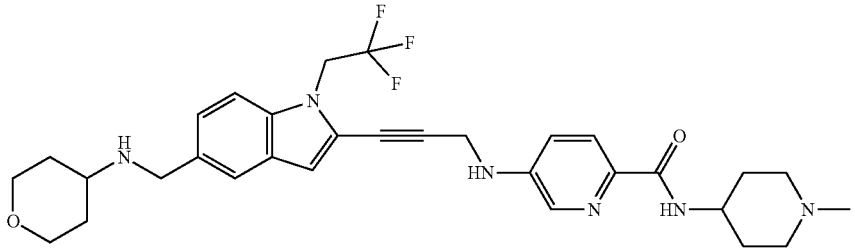 [SMILES: CN1CCC(NC(=O)c2ccc(NCC#Cc3cc4cc(CNC5CCOCC5)ccc4n3CC(F)(F)F)cn2)CC1] | N-(1-methylpiperidin-4-yl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 140-P | 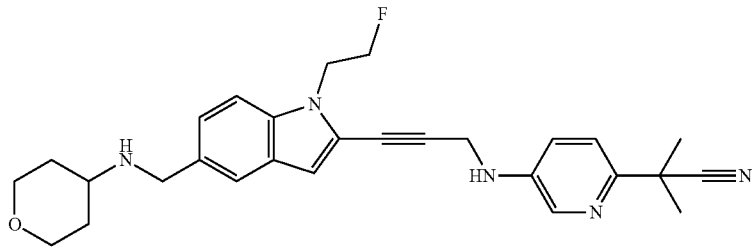 | N-[6-(1-cyano-1-methylethyl)pyridin-3-yl]-3-[1-(2-fluoroethyl)-5-{[(oxan-4-yl)amino]methyl}-1H-indol-2-yl]prop-2-ynamide |
| 141-P | 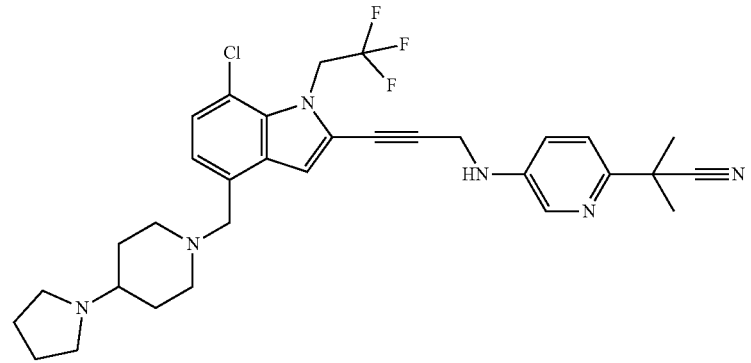 | 2-(5-{[3-(7-chloro-4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 142-P | 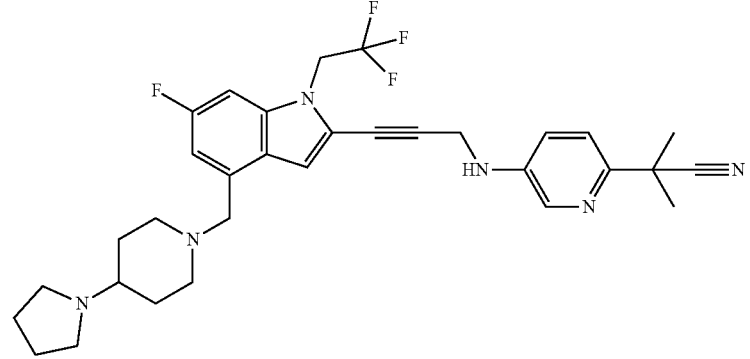 | 2-(5-{[3-(6-fluoro-4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |

TABLE 1-continued

List of compounds

| # | Structure IUPAC name |
|---|---|
| 143-P | 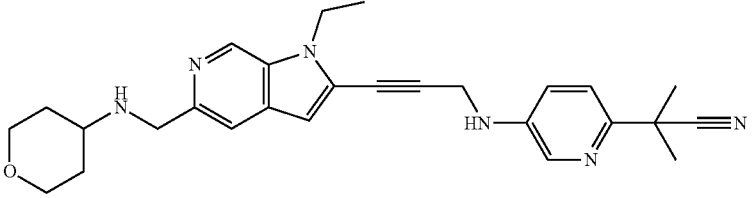 [SMILES: CCn1c(C#CCNc2ccc(C(C)(C)C#N)nc2)cc2cc(CNC3CCOCC3)ncc21]

2-(5-{[3-(1-ethyl-5-{[(oxan-4-yl)amino]methyl}-1H-pyrrolo[2,3-c]pyridin-2-yl)prop-2-yn-1-yl]amino}pyridin-2-yl)-2-methylpropanenitrile |
| 144-P | 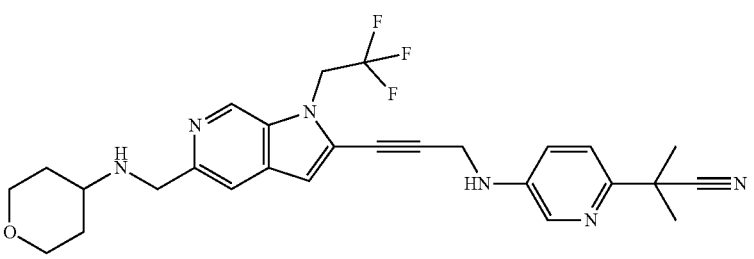

2-methyl-2-(5-{[3-(5-{[(oxan-4-yl)amino]methyl}-1-(2,2,2-trifluoroethyl)-1H-pyrrolo[2,3-c]pyridin-2-yl)prop-2-yn-1-yl]amino}pyridin-2-yl)propanenitrile |
| 145-P | 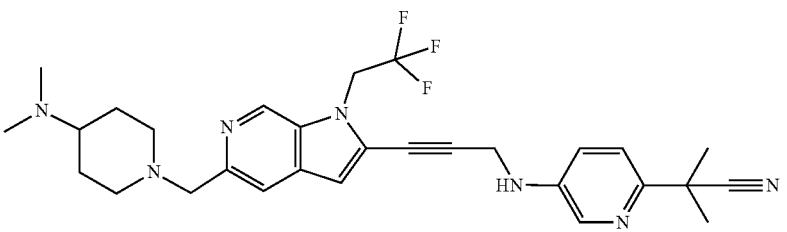 [SMILES: CN(C)C1CCN(Cc2cc3cc(C#CCNc4ccc(C(C)(C)C#N)nc4)n(CC(F)(F)F)c3cn2)CC1]

2-(5-{[3-(5-{[4-(dimethylamino)piperidin-1-yl]methyl}-1-(2,2,2-trifluoroethyl)-1H-pyrrolo[2,3-c]pyridin-2-yl)prop-2-yn-1-yl]amino}pyridin-2-yl)-2-methylpropanenitrile |
| 146-P | 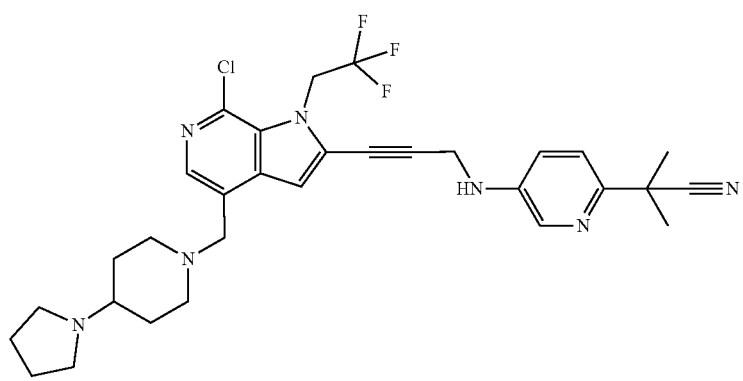 [SMILES: CC(C)(C#N)c1ccc(NCC#Cc2cc3c(CN4CCC(N5CCCC5)CC4)cnc(Cl)c3n2CC(F)(F)F)cn1]

2-(5-{[3-(7-chloro-4-{[4-(pyrrolidin-1-yl)piperidin-1-yl]methyl}-1-(2,2,2-trifluoroethyl)-1H-pyrrolo[2,3-c]pyridin-2-yl)prop-2-yn-1-yl]amino}pyridin-2-yl)-2-methylpropanenitrile |

TABLE 1-continued

List of compounds

| # | Structure IUPAC name |
|---|---|
| 147-P | 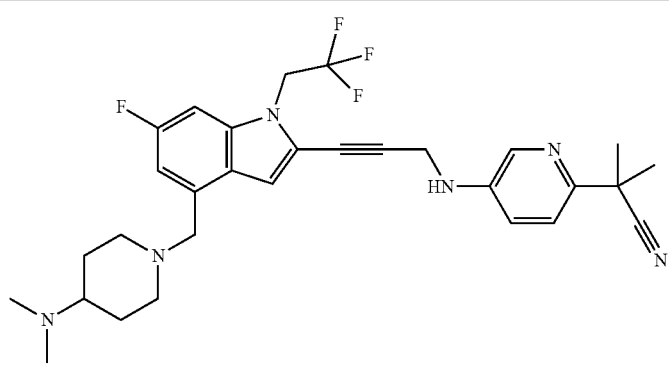 [SMILES: CN(C)C1CCN(Cc2cc(F)cc3c2cc(C#CCNc2ccc(C(C)(C)C#N)nc2)n3CC(F)(F)F)CC1]

2-(5-{[3-(4-{[4-(diethylamino)piperidin-1-yl]methyl}-6-fluoro-1-(2,2,2-trifluoroethyl)-1H-indol-2-yl)prop-2-yn-1-yl]amino}pyridin-2-yl)-2-methylpropanenitrile |
| 148-P | 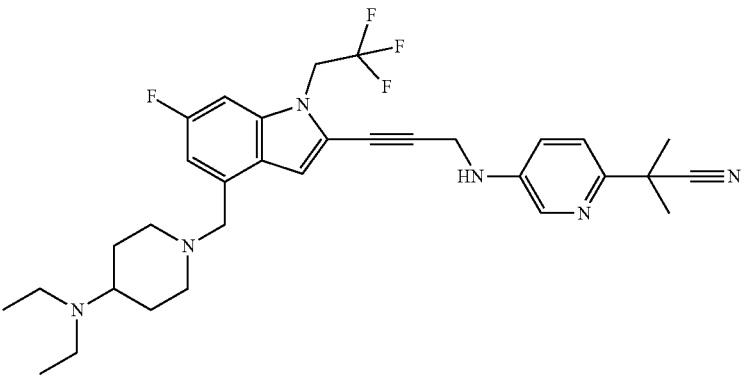 [SMILES: CCN(CC)C1CCN(Cc2cc(F)cc3c2cc(C#CCNc2ccc(C(C)(C)C#N)nc2)n3CC(F)(F)F)CC1]

2-(5-{[3-(4-{[4-(dimethylamino)-piperidin-1-yl]methyl}-6-fluoro-1-(2,2,2-trifluoroethyl)-1H-indol-2-yl)prop-2-yn-1-yl]amino}pyridin-2-yl)-2-methylpropanenitrile |
| 149-P | 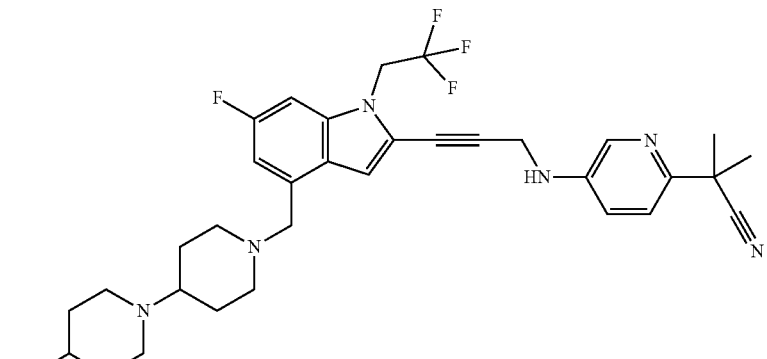

2-(5-{[3-(6-fluoro-4-{[4-(4-hydroxypiperidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |

TABLE 1-continued

List of compounds

| # | Structure IUPAC name |
|---|---|
| 150-P | 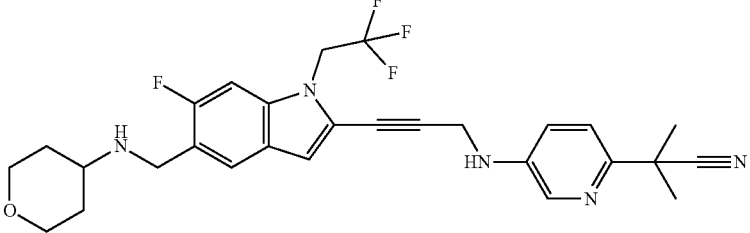 2-(5-{[3-(6-fluoro-5-{[(oxan-4-yl)amino]methyl}-1-(2,2,2-trifluoroethyl)-1H-indol-2-yl)prop-2-yn-1-yl]amino}pyridin-2-yl)-2-methylpropanenitrile |
| 151-P | 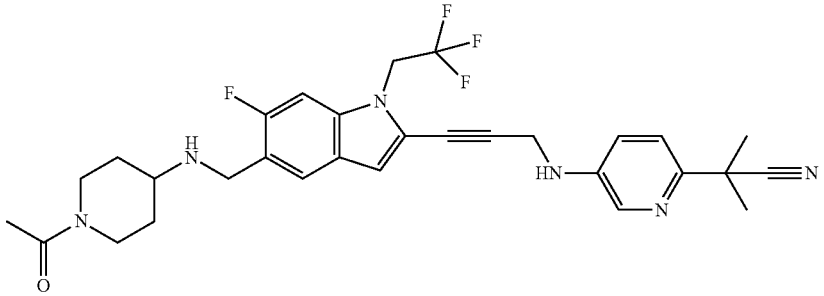 [SMILES: CC(=O)N1CCC(NCc2cc3cc(C#CCNc4ccc(C(C)(C)C#N)nc4)n(CC(F)(F)F)c3cc2F)CC1] 2-(5-{[3-(5-{[(1-acetylpiperidin-4-yl)amino]methyl}-6-fluoro-1-(2,2,2-trifluoroethyl)-1H-indol-2-yl)prop-2-yn-1-yl]amino}pyridin-2-yl)-2-methylpropanenitrile |
| 152-P | 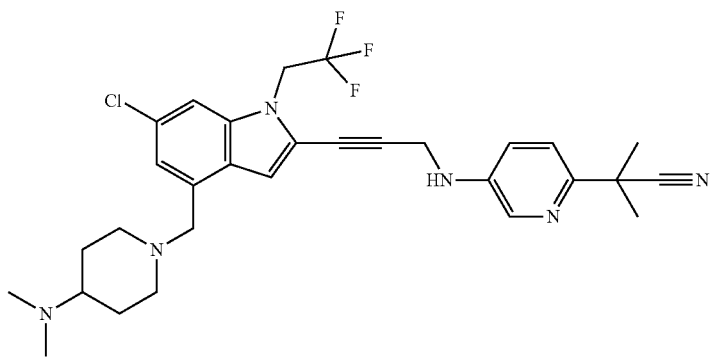 [SMILES: CN(C)C1CCN(Cc2cc(Cl)cc3c2cc(C#CCNc2ccc(C(C)(C)C#N)nc2)n3CC(F)(F)F)CC1] 2-(5-{[3-(6-chloro-4-{[4-(dimethylamino)piperidin-1-yl]methyl}-1-(2,2,2-trifluoroethyl)-1H-indol-2-yl)prop-2-yn-1-yl]amino}pyridin-2-yl)-2-methylpropanenitrile |

TABLE 1-continued

List of compounds

| # | Structure IUPAC name |
|---|---|
| 153-P | 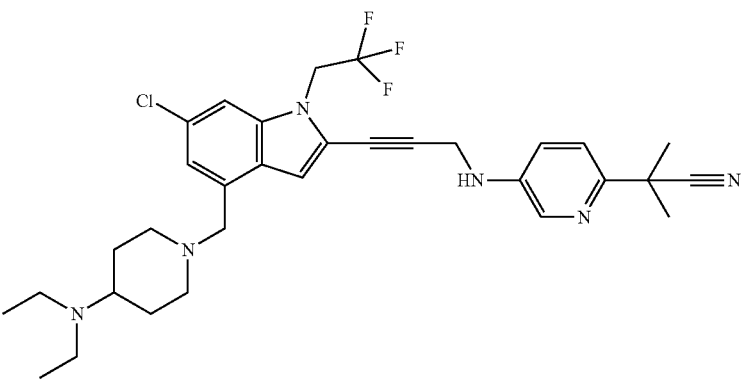 [SMILES: CCN(CC)C1CCN(Cc2cc(Cl)cc3c2cc(C#CCNc2ccc(C(C)(C)C#N)nc2)n3CC(F)(F)F)CC1] 2-(5-{[3-(6-chloro-4-{[4-(diethylamino)piperidin-1-yl]methyl}-1-(2,2,2-trifluoroethyl)-1H-indol-2-yl)prop-2-yn-1-yl]amino}pyridin-2-yl)-2-methylpropanenitrile |
| 154-P | 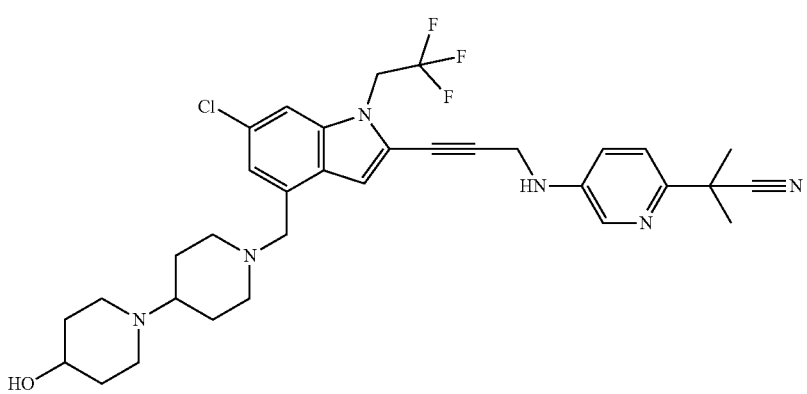 [SMILES: CC(C)(C#N)c1ccc(NCC#Cc2cc3c(CN4CCC(N5CCC(O)CC5)CC4)cc(Cl)cc3n2CC(F)(F)F)cn1] 2-(5-{[3-(6-chloro-4-{[4-(4-hydroxypiperidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 155-P | 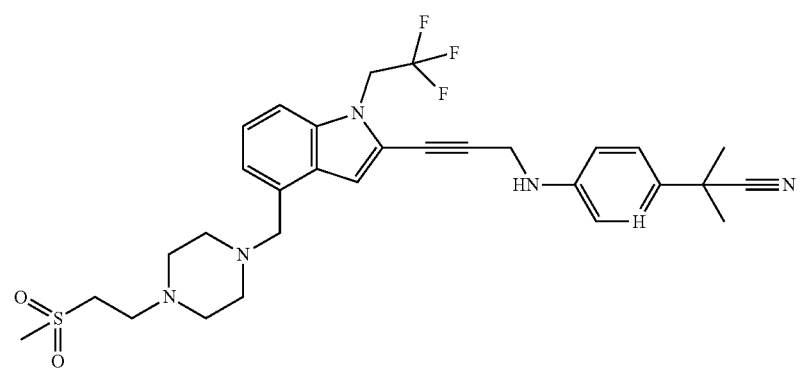 2-(5-{[3-(4-{[4-(2-methanesulfonyl-ethyl)piperazin-1-yl]methyl}-1-(2,2,2-trifluoroethyl)-1H-indol-2-yl)prop-2-yn-1-yl]amino}pyridin-2-yl)-2-methylpropanenitrile |

TABLE 1-continued

List of compounds

| # | Structure IUPAC name |
|---|---|
| 156-P | 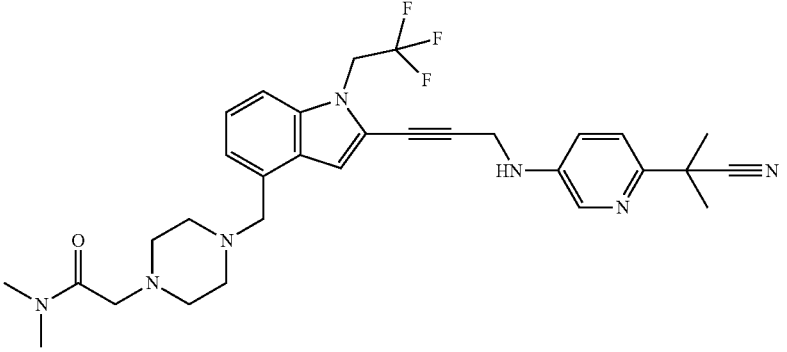 [SMILES: CN(C)C(=O)CN1CCN(Cc2cccc3c2cc(C#CCNc2ccc(C(C)(C)C#N)nc2)n3CC(F)(F)F)CC1] 2-(4-{[2-(3-{[6-(1-cyano-1-methylethyl)pyridin-3-yl]amino}prop-1-yn-1-yl)-1-(2,2,2-trifluoroethyl)-1H-indol-4-yl]methyl}piperazin-1-yl)-N,N-dimethylacetamide |
| 157-P | 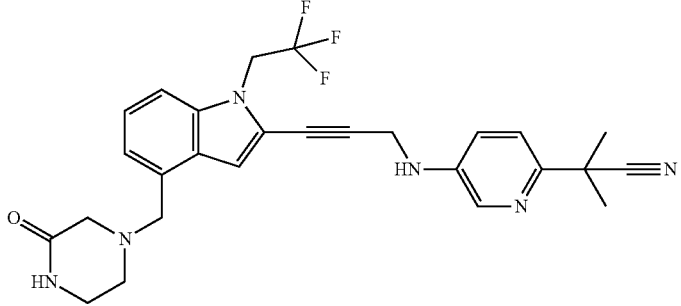 [SMILES: CC(C)(C#N)c1ccc(NCC#Cc2cc3c(CN4CCNC(=O)C4)cccc3n2CC(F)(F)F)cn1] 2-methyl-2-{5-[(3-{4-[(3-oxopiperazin-1-yl)methyl]-1-(2,2,2-trifluoroethyl)-1H-indol-2-yl}prop-2-yn-1-yl)amino]pyridin-2-yl}propanenitrile |
| 158-P | 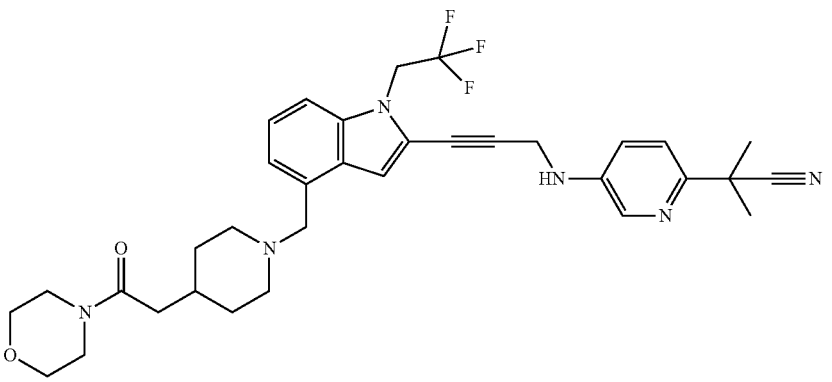 [SMILES: CC(C)(C#N)c1ccc(NCC#Cc2cc3c(CN4CCC(CC(=O)N5CCOCC5)CC4)cccc3n2CC(F)(F)F)cn1] 2-methyl-2-[5-({3-[4-({4-[2-(morpholin-4-yl)-2-oxoethyl]piperidin-1-yl}methyl)-1-(2,2,2-trifluoroethyl)-1H-indol-2-yl]prop-2-yn-1-yl}amino)pyridin-2-yl]propanenitrile |

TABLE 1-continued

List of compounds

| # | Structure IUPAC name |
|---|---|

159-P 2-(4-{[2-(3-{[6-(1-cyano-1-methylethyl)pyridin-3-yl]amino}prop-1-yn-1-yl)-1-(2,2,2-trifluoroethyl)-1H-indol-4-yl]methyl}piperazin-1-yl)acetamide

160-P

N-[6-(1-cyano-1-methylethyl)pyridin-3-yl]-3-(4-{[4-(pyrrolidin-1-yl)piperidin-1-yl]methyl}-1-(2,2,2-trifluoroethyl)-1H-indol-2-yl)prop-2-ynamide

161-P 2-(1-{[2-(3-{[6-(1-cyano-1-methylethyl)pyridin-3-yl]amino}prop-1-yn-1-yl)-1-(2,2,2-trifluoroethyl)-1H-indol-4-yl]methyl}piperidin-4-yl)acetamide TABLE 1-continued List of compounds

| # | Structure IUPAC name |
|---|---|

162-P

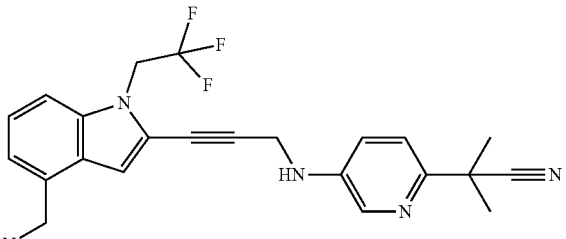

2-(5-{[3-(4-{[4-(2-aminoethyl)-piperazin-1-yl]methyl}-1-(2,2,2-trifluoroethyl)-1H-indol-2-yl)prop-2-yn-1-yl]amino}pyridin-2-yl)-2-methylpropanenitrile

163-P

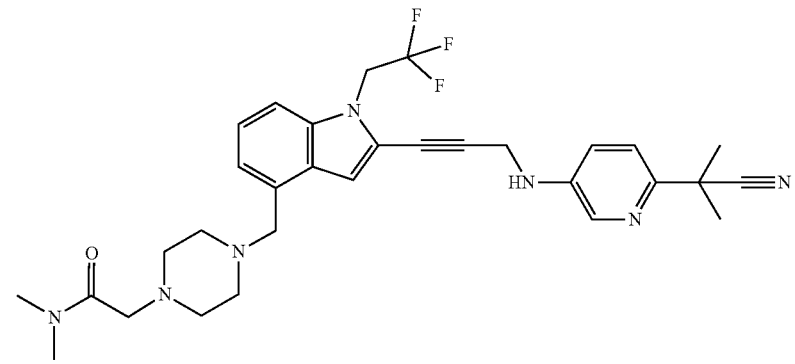 [SMILES: CN(C)C(=O)CN1CCN(Cc2cccc3c2cc(C#CCNc2ccc(C(C)(C)C#N)nc2)n3CC(F)(F)F)CC1]

2-(1-{[2-(3-{[6-(1-cyano-1-methylethyl)pyridin-3-yl]amino}prop-1-yn-1-yl)-1-(2,2,2-trifluoroethyl)-1H-indol-4-yl]methyl}piperidin-4-yl)-N,N-dimethylacetamide

164-P

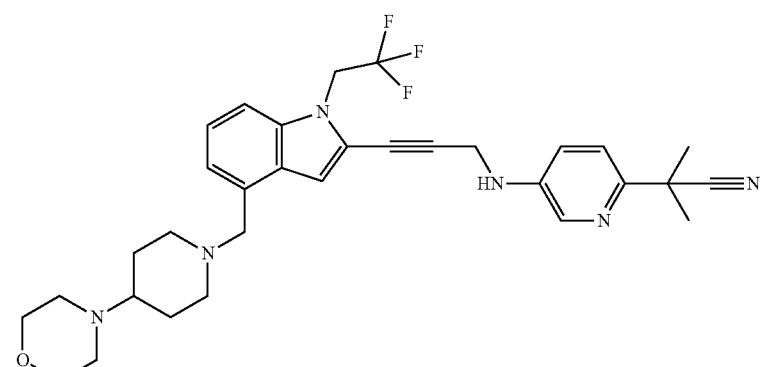

2-methyl-2-(5-{[3-(4-{[4-(morpholin-4-yl)piperidin-1-yl]methyl}-1-(2,2,2-trifluoroethyl)-1H-indol-2-yl)prop-2-yn-1-yl]amino}pyridin-2-yl)propanenitrile TABLE 1-continued List of compounds

| # | Structure IUPAC name |
|---|---|
| 165-P | 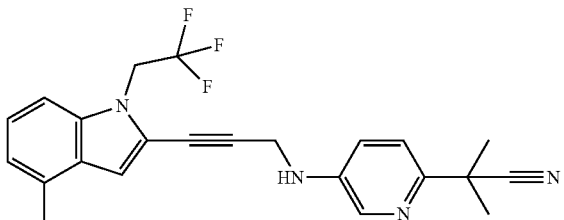<br>2-(5-{[3-(4-{[4-(4-aminopiperidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 166-P | 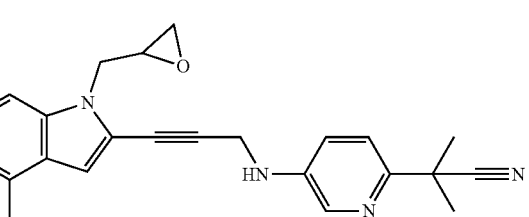<br>2-methyl-2-[5-({3-[1-(oxiran-2-ylmethyl)-4-{[4-(pyrrolidin-1-yl)piperidin-1-yl]methyl}-1H-indol-2-yl]prop-2-yn-1-yl}amino)pyridin-2-yl]propanenitrile |
| 167-P | 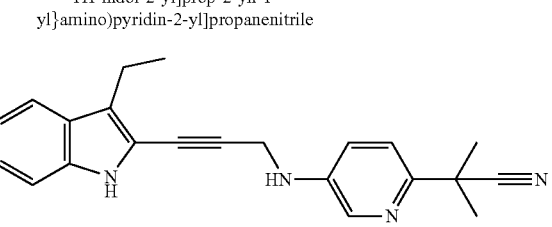<br>2-(5-{[3-(3-ethyl-6-{[(oxan-4-yl)amino]methyl}-1H-indol-2-yl)prop-2-yn-1-yl]amino}pyridin-2-yl)-2-methylpropanenitrile |
| 168-P | 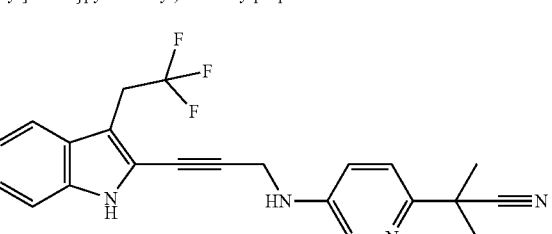<br>2-methyl-2-(5-{[3-(6-{[(oxan-4-yl)amino]methyl}-3-(2,2,2-trifluoroethyl)-1H-indol-2-yl)prop-2-yn-1-yl]amino}pyridin-2-yl)propanenitrile |

TABLE 1-continued

List of compounds

| # | Structure IUPAC name |
|---|---|
| 169-P | 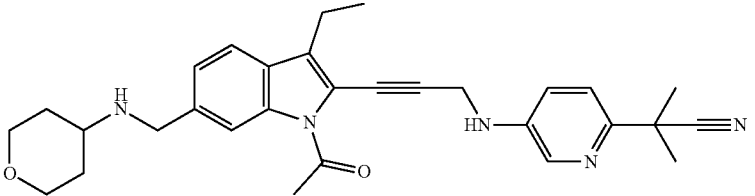 [SMILES: CCc1c(C#CCNc2ccc(C(C)(C)C#N)nc2)n(C(C)=O)c2cc(CNC3CCOCC3)ccc12] 2-(5-{[3-(1-acetyl-3-ethyl-6-{[(oxan-4-yl)amino]methyl}-1H-indol-2-yl)prop-2-yn-1-yl]amino}pyridin-2-yl)-2-methylpropanenitrile |
| 170-P | 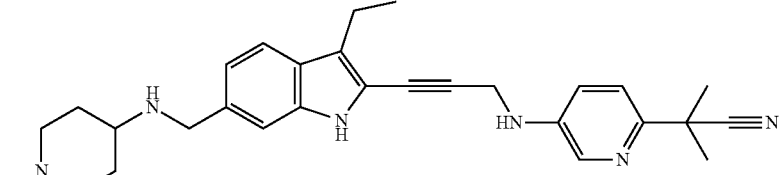 2-(5-{[3-(3-ethyl-6-{[(1-methylpiperidin-4-yl)amino]methyl}-1H-indol-2-yl)prop-2-yn-1-yl]amino}pyridin-2-yl)-2-methylpropanenitrile |
| 171-P | 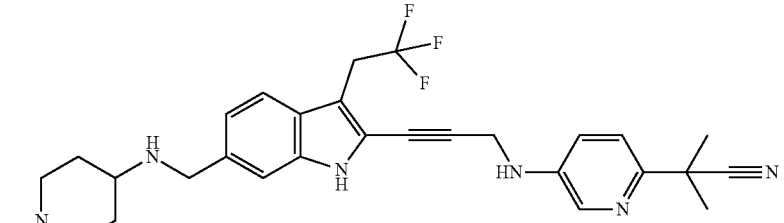 2-methyl-2-(5-{[3-(6-{[(1-methylpiperidin-4-yl)amino]methyl}-3-(2,2,2-trifluoroethyl)-1H-indol-2-yl)prop-2-yn-1-yl]amino}pyridin-2-yl)propanenitrile |
| 172-P | 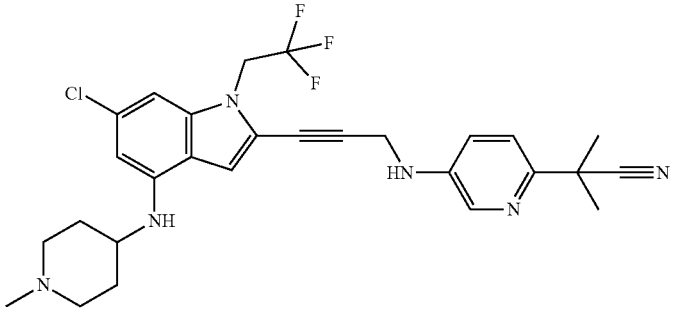 [SMILES: CN1CCC(Nc2cc(Cl)cc3c2cc(C#CCNc2ccc(C(C)(C)C#N)nc2)n3CC(F)(F)F)CC1] 2-{5-[(3-{6-chloro-4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile |

TABLE 1-continued

List of compounds

| # | Structure IUPAC name |
|---|---|
| 173-P | 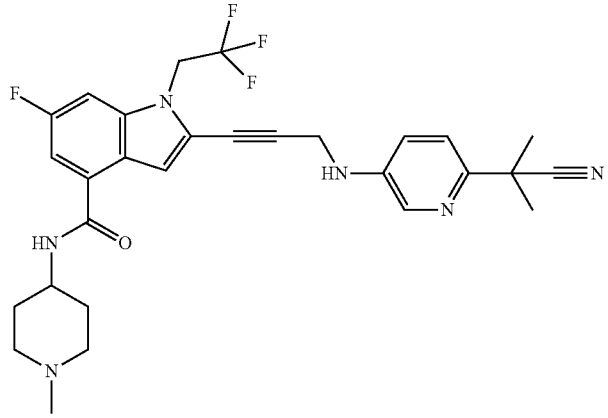 [SMILES: CN1CCC(NC(=O)c2cc(F)cc3c2cc(C#CCNc2ccc(C(C)(C)C#N)nc2)n3CC(F)(F)F)CC1]<br>2-(3-{[6-(1-cyano-1-methylethyl)pyridin-3-yl]amino}prop-1-yn-1-yl)-6-fluoro-N-(1-methylpiperidin-4-yl)-1-(2,2,2-trifluoroethyl)-1H-indole-4-carboxamide |
| 174-P | 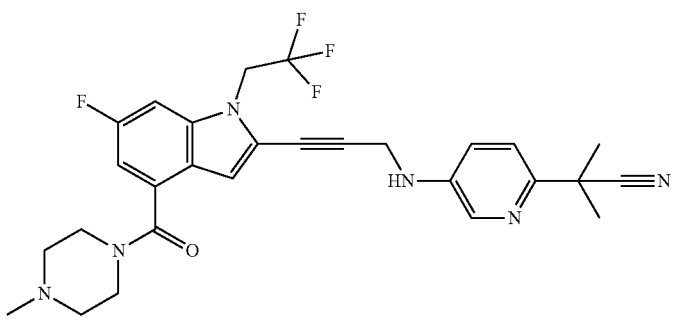 [SMILES: CN1CCN(C(=O)c2cc(F)cc3c2cc(C#CCNc2ccc(C(C)(C)C#N)nc2)n3CC(F)(F)F)CC1]<br>2-[5-({3-[6-fluoro-4-(4-methylpiperazine-1-carbonyl)-1-(2,2,2-trifluoroethyl)-1H-indol-2-yl]prop-2-yn-1-yl}amino)pyridin-2-yl]-2-methylpropanenitrile |
| 175-P | 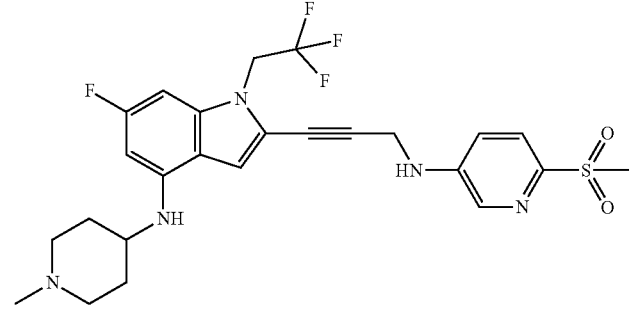<br>6-fluoro-2-{3-[(6-methanesulfonylpyridin-3-yl)amino]prop-1-yn-1-yl}-N-(1-methylpiperidin-4-yl)-1-(2,2,2-trifluoroethyl)-1H-indol-4-amine |

TABLE 1-continued

List of compounds

| # | Structure | IUPAC name |
|---|---|---|
| 176-P | 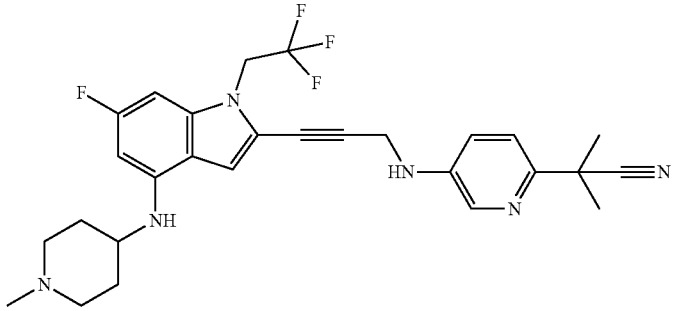 | 2-{5-[(3-{6-fluoro-4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile |
| 177-P | 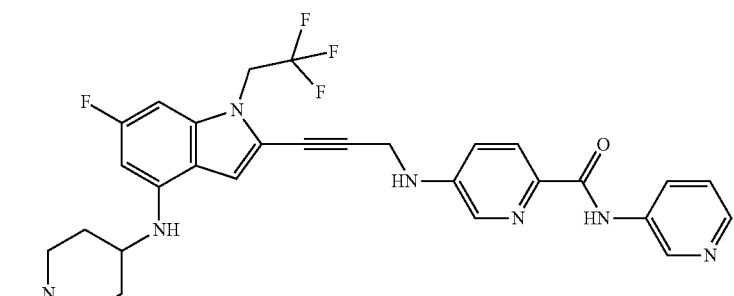 | 5-[(3-{6-fluoro-4-[(1-methylpiperidin-4-yl)amino]-1-(2,2,2-trifluoroethyl)-1H-indol-2-yl}prop-2-yn-1-yl)amino]-N-(pyridin-3-yl)pyridine-2-carboxamide |
| 178-P | 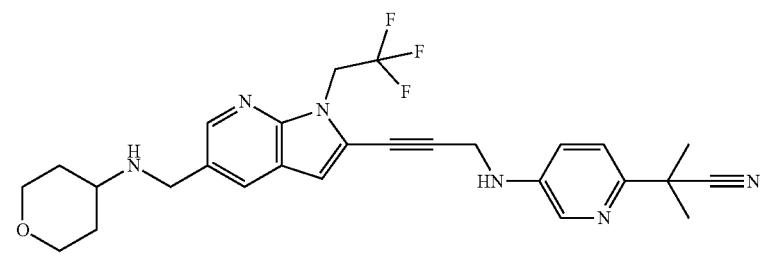 | 2-methyl-2-(5-{[3-(5-{[(oxan-4-yl)amino]methyl}-1-(2,2,2-trifluoroethyl)-1H-pyrrolo[2,3-b]pyridin-2-yl)prop-2-yn-1-yl]amino}pyridin-2-yl)propanenitrile |
| 179-P | 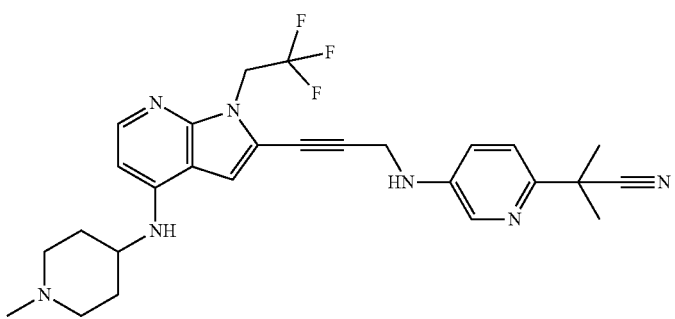 | 2-methyl-2-{5-[(3-{4-[(1-methylpiperidin-4-yl)amino]-1-(2,2,2-trifluoroethyl)-1H-pyrrolo[2,3-b]pyridin-2-yl}prop-2-yn-1-yl)amino]pyridin-2-yl}propanenitrile |

TABLE 1-continued

List of compounds

| # | Structure IUPAC name |
|---|---|
| 180-P | 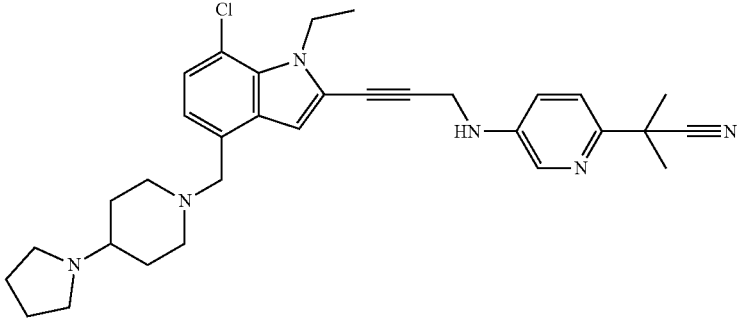2-(5-{[3-(7-chloro-1-ethyl-4-{[4-(pyrrolidin-1-yl)piperidin-1-yl]methyl}-1H-indol-2-yl)prop-2-yn-1-yl]amino}pyridin-2-yl)-2-methylpropanenitrile |
| 181-P | 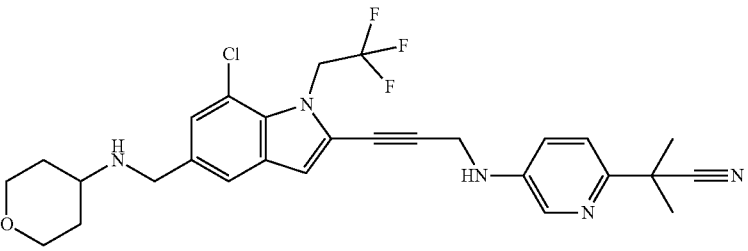 [SMILES: CC(C)(C#N)c1ccc(NCC#Cc2cc3cc(CNC4CCOCC4)cnc3n2CC(F)(F)F)cn1]2-(5-{[3-(7-chloro-5-{[(oxan-4-yl)amino]methyl}-1-(2,2,2-trifluoroethyl)-1H-indol-2-yl)prop-2-yn-1-yl]amino}pyridin-2-yl)-2-methylpropanenitrile |
| 182-P | 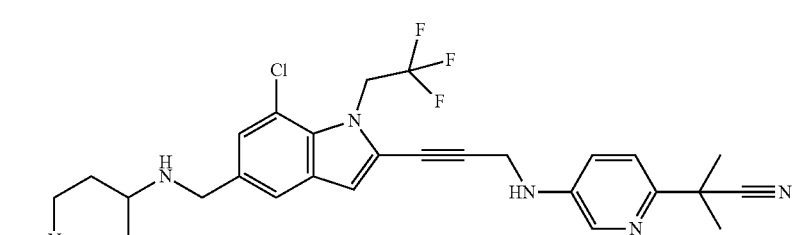2-(5-{[3-(7-chloro-5-{[(1-methylpiperidin-4-yl)amino]methyl}-1-(2,2,2-trifluoroethyl)-1H-indol-2-yl)prop-2-yn-1-yl]amino}pyridin-2-yl)-2-methylpropanenitrile |
| 183-P | 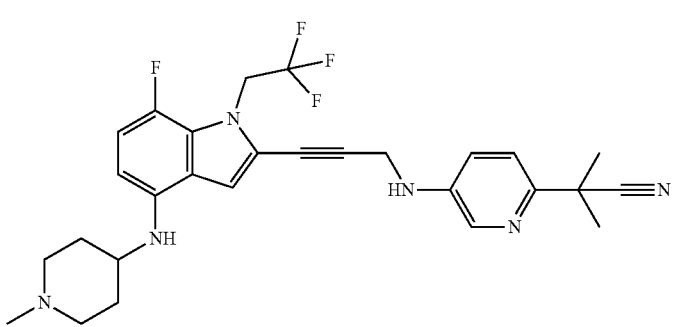 [SMILES: CN1CCC(Nc2ccc(F)c3c2cc(C#CCNc2ccc(C(C)(C)C#N)nc2)n3CC(F)(F)F)CC1]2-{5-[(3-{7-fluoro-4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile |

TABLE 1-continued

List of compounds

| # | Structure IUPAC name |
|---|---|
| 184-P | 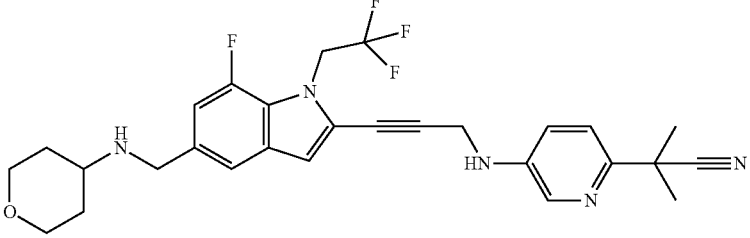<br>2-(5-{[3-(7-fluoro-5-{[(oxan-4-yl)amino]methyl}-1-(2,2,2-trifluoroethyl)-1H-indol-2-yl)prop-2-yn-1-yl]amino}pyridin-2-yl)-2-methylpropanenitrile |
| 185-P | 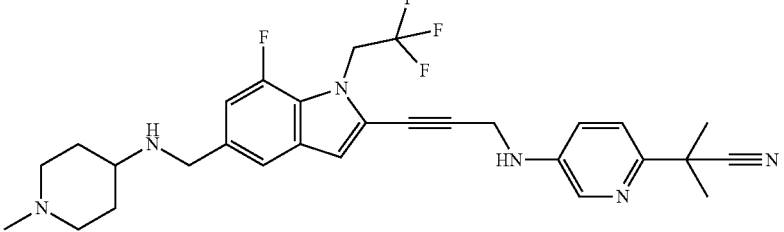<br>2-(5-{[3-(7-fluoro-5-{[(1-methylpiperidin-4-yl)amino]methyl}-1-(2,2,2-trifluoroethyl)-1H-indol-2-yl)prop-2-yn-1-yl]amino}pyridin-2-yl)-2-methylpropanenitrile |
| 186-P | 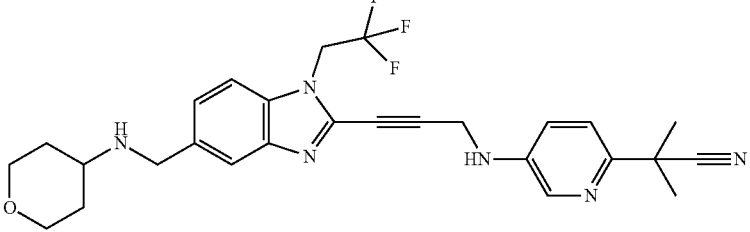<br>2-methyl-2-(5-{[3-(5-{[(oxan-4-yl)amino]methyl}-1-(2,2,2-trifluoroethyl)-1H-1,3-benzodiazol-2-yl)prop-2-yn-1-yl]amino}pyridin-2-yl)propanenitrile |
| 187-P | 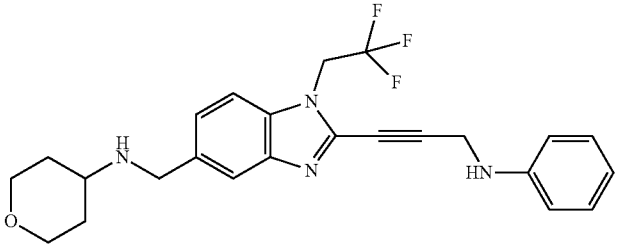<br>N-{[2-(2-phenylethynyl)-1-(2,2,2-trifluoroethyl)-1H-1,3-benzodiazol-5-yl]methyl}oxan-4-amine |

TABLE 1-continued

List of compounds

| # | Structure IUPAC name |
|---|---|
| 188-P | 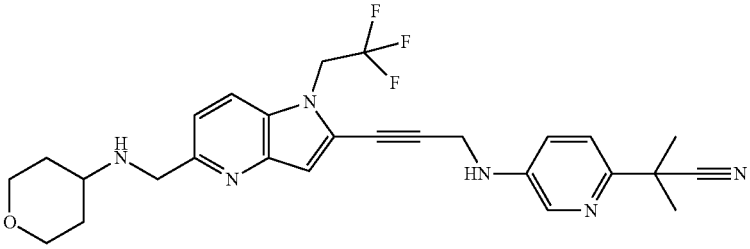 [SMILES: CC(C)(C#N)c1ccc(NCC#Cc2nc3cc(CNC4CCOCC4)ccc3n2CC(F)(F)F)cn1]
2-methyl-2-(5-{[3-(5-{[(oxan-4-yl)amino]methyl}-1-(2,2,2-trifluoroethyl)-1H-pyrrolo[3,2-b]pyridin-2-yl)prop-2-yn-1-yl]amino}pyridin-2-yl)propanenitrile |
| 189-P | 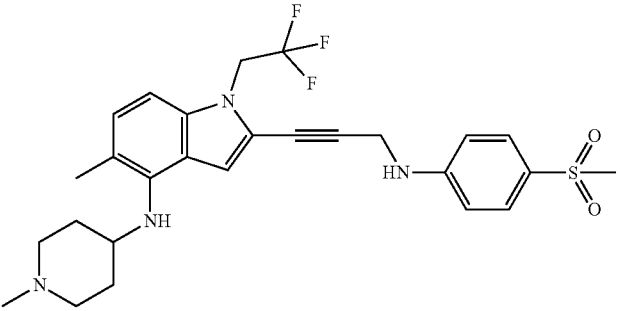
2-{3-[(4-methanesulfonylphenyl)amino]prop-1-yn-1-yl}-5-methyl-N-(1-methylpiperidin-4-yl)-1-(2,2,2-trifluoroethyl)-1H-indol-4-amine |
| 190-P | 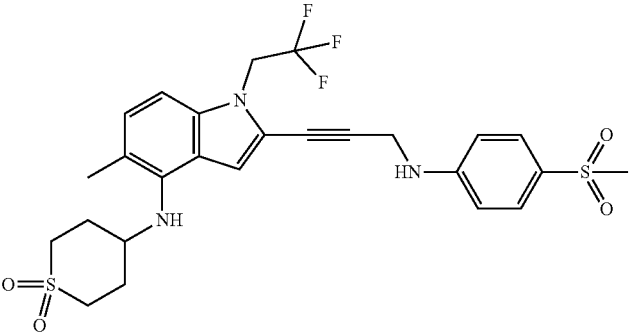 [SMILES: Cc1ccc2c(cc(C#CCNc3ccc(S(C)(=O)=O)cc3)n2CC(F)(F)F)c1NC1CCS(=O)(=O)CC1]
4-[(2-{3-[(4-methanesulfonylphenyl)amino]prop-1-yn-1-yl}-5-methyl-1-(2,2,2-trifluoroethyl)-1H-indol-4-yl)amino]-1λ⁶-thiane-1,1-dione |
| 191-P | 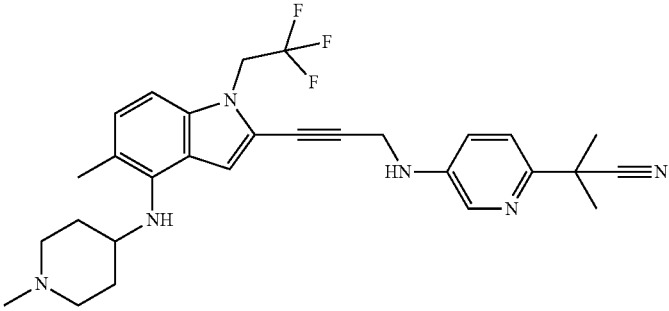 [SMILES: Cc1ccc2c(cc(C#CCNc3ccc(C(C)(C)C#N)nc3)n2CC(F)(F)F)c1NC1CCN(C)CC1]
2-methyl-2-{5-[(3-{5-methyl-4-[(1-methylpiperidin-4-yl)amino]-1-(2,2,2-trifluoroethyl)-1H-indol-2-yl}prop-2-yn-1-yl)amino]pyridin-2-yl}propanenitrile |

TABLE 1-continued

List of compounds

| # | Structure IUPAC name |
|---|---|
| 192-P | 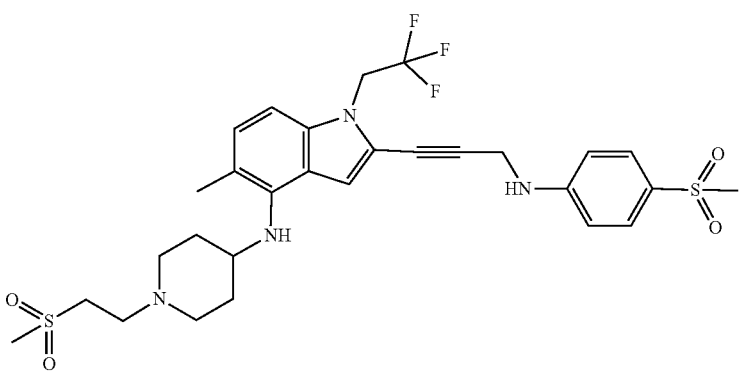 [SMILES: Cc1ccc2c(cc(C#CCNc3ccc(S(C)(=O)=O)cc3)n2CC(F)(F)F)c1NC1CCN(CCS(C)(=O)=O)CC1]<br>N-[1-(2-methanesulfonylethyl)piperidin-4-yl]-2-{3-[(4-methanesulfonylphenyl)amino]prop-1-yn-1-yl}-5-methyl-1-(2,2,2-trifluoroethyl)-1H-indol-4-amine |
| 193-P | 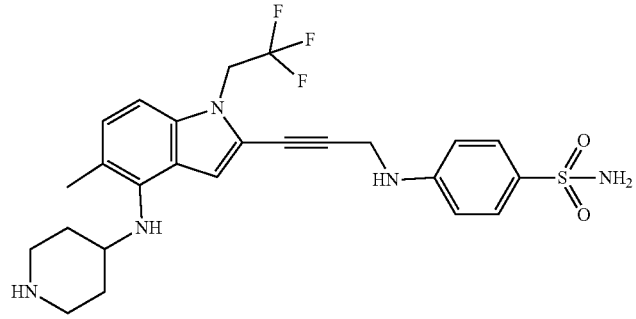 [SMILES: Cc1ccc2c(cc(C#CCNc3ccc(S(N)(=O)=O)cc3)n2CC(F)(F)F)c1NC1CCNCC1]<br>4-[(3-{5-methyl-4-[(piperidin-4-yl)amino]-1-(2,2,2-trifluoroethyl)-1H-indol-2-yl}prop-2-yn-1-yl)amino]benzene-1-sulfonamide |
| 194-P | 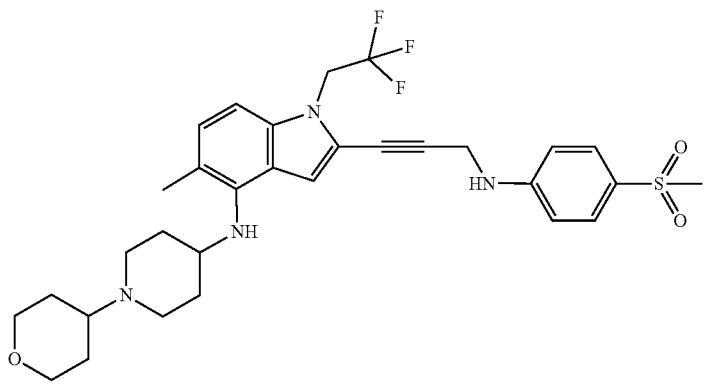 [SMILES: Cc1ccc2c(cc(C#CCNc3ccc(S(C)(=O)=O)cc3)n2CC(F)(F)F)c1NC1CCN(C2CCOCC2)CC1]<br>2-{3-[(4-methanesulfonylphenyl)amino]prop-1-yn-1-yl}-5-methyl-N-[1-(oxan-4-yl)piperidin-4-yl]-1-(2,2,2-trifluoroethyl)-1H-indol-4-amine |

TABLE 1-continued

List of compounds

| # | Structure IUPAC name |
|---|---|
| 195-P | 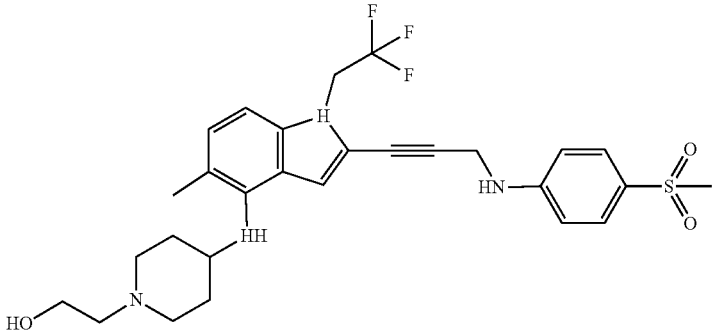

2-{4-[(2-{3-[(4-methanesulfonylphenyl)amino]prop-1-yn-1-yl}-5-methyl-1-(2,2,2-trifluoroethyl)-1H-indol-4-yl)amino]piperidin-1-yl}ethan-1-ol |
| 196-P | 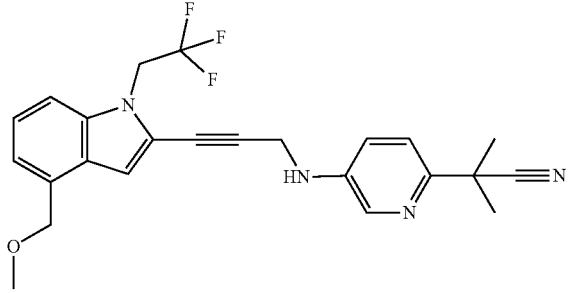 [SMILES: COCc1cccc2c1cc(C#CCNc1ccc(C(C)(C)C#N)nc1)n2CC(F)(F)F]

2-[5-({3-[4-(methoxymethyl)-1-(2,2,2-trifluoroethyl)-1H-indol-2-yl]prop-2-yn-1-yl}amino)pyridin-2-yl]-2-methylpropanenitrile |
| 197-P | 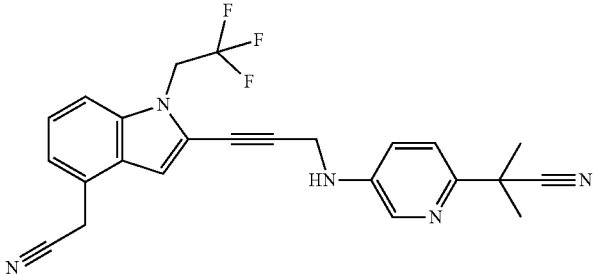 [SMILES: CC(C)(C#N)c1ccc(NCC#Cc2cc3c(CC#N)cccc3n2CC(F)(F)F)cn1]

2-[5-({3-[4-(cyanomethyl)-1-(2,2,2-trifluoroethyl)-1H-indol-2-yl]prop-2-yn-1-yl}amino)pyridin-2-yl]-2-methylpropanenitrile |
| 198-P | 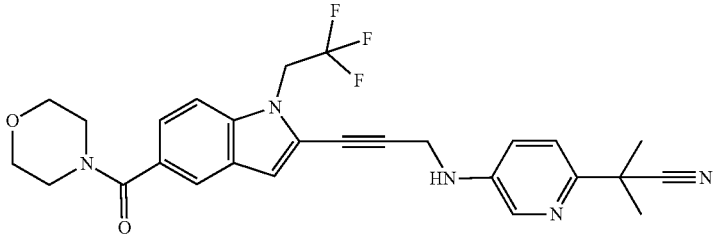 [SMILES: CC(C)(C#N)c1ccc(NCC#Cc2cc3cc(C(=O)N4CCOCC4)ccc3n2CC(F)(F)F)cn1]

2-methyl-2-[5-({3-[5-(morpholine-4-carbonyl)-1-(2,2,2-trifluoroethyl)-1H-indol-2-yl]prop-2-yn-1-yl}amino)pyridin-2-yl]propanenitrile |

TABLE 1-continued

List of compounds

| # | Structure IUPAC name |
|---|---|
| 199-P | 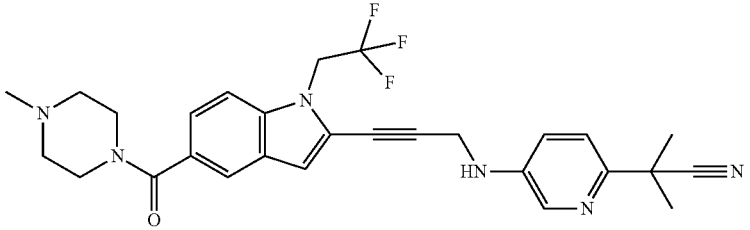 [SMILES: CN1CCN(C(=O)c2ccc3c(c2)cc(C#CCNc2ccc(C(C)(C)C#N)nc2)n3CC(F)(F)F)CC1]<br>2-methyl-2-[5-({3-[5-(4-methylpiperazine-1-carbonyl)-1-(2,2,2-trifluoroethyl)-1H-indol-2-yl]prop-2-yn-1-yl}amino)pyridin-2-yl]propanenitrile |
| 200-P | 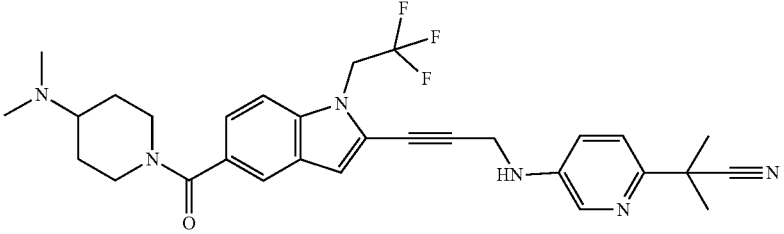 [SMILES: CN(C)C1CCN(C(=O)c2ccc3c(c2)cc(C#CCNc2ccc(C(C)(C)C#N)nc2)n3CC(F)(F)F)CC1]<br>2-{5-[(3-{5-[4-(dimethylamino)piperidine-1-carbonyl]-1-(2,2,2-trifluoroethyl)-1H-indol-2-yl}prop-2-yn-1-yl)amino]pyridin-2-yl}-2-methylpropanenitrile |
| 201-P | 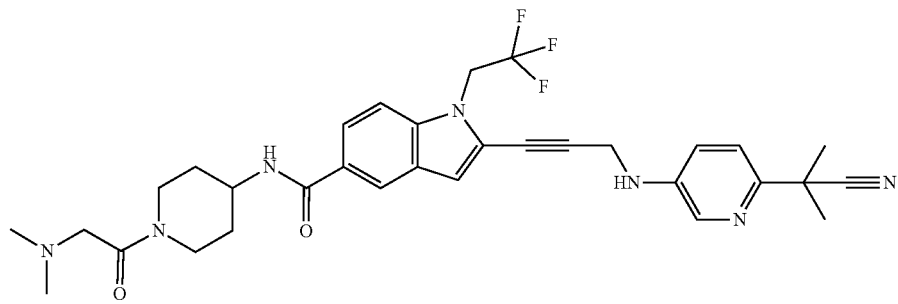 [SMILES: CN(C)CC(=O)N1CCC(NC(=O)c2ccc3c(c2)cc(C#CCNc2ccc(C(C)(C)C#N)nc2)n3CC(F)(F)F)CC1]<br>2-(3-{[6-(1-cyano-1-methylethyl)pyridin-3-yl]amino}prop-1-yn-1-yl)-N-{1-[2-(dimethylamino)acetyl]piperidin-4-yl}-1-(2,2,2-trifluoroethyl)-1H-indole-5-carboxamide |
| 202-P | 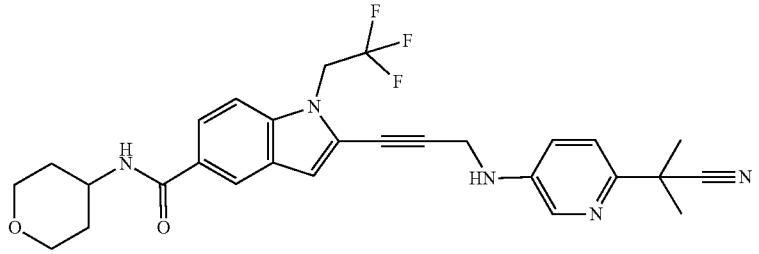 [SMILES: CC(C)(C#N)c1ccc(NCC#Cc2cc3cc(C(=O)NC4CCOCC4)ccc3n2CC(F)(F)F)cn1]<br>2-(3-{[6-(1-cyano-1-methylethyl)pyridin-3-yl]amino}prop-1-yn-1-yl)-N-(oxan-4-yl)-1-(2,2,2-trifluoroethyl)-1H-indole-5-carboxamide |

TABLE 1-continued

List of compounds

| # | Structure IUPAC name |
|---|---|
| 203-P | 2-methyl-2-(5-{[3-(5-{1-[(oxan-4-yl)amino]ethyl}-1-(2,2,2-trifluoroethyl)-1H-indol-2-yl)prop-2-yn-1-yl]amino}pyridin-2-yl)propanenitrile |
| 204-P | 2-methyl-2-{5-[3-{4-[(1-methylpiperidin-4-yl)amino]-1-(2,2,2-trifluoroethyl)-1H-pyrrolo[3,2-c]pyridin-2-yl}prop-2-yn-1-yl)amino]pyridin-2-yl}propanenitrile |
| 205-P | 2-methyl-2-[5-({3-[5-(morpholin-4-ylmethyl)-1-(2,2,2-trifluoroethyl)-1H-indol-2-yl]prop-2-yn-1-yl}amino)pyridin-2-yl]propanenitrile |
| 206-P | 2-[5-({3-[5-({[1-(2-cyanoethyl)-piperidin-4-yl]amino}methyl)-1-(2,2,2-trifluoroethyl)-1H-indol-2-yl]prop-2-yn-1-yl}amino)pyridin-2-yl]-2-methylpropanenitrile |

TABLE 1-continued

List of compounds

| # | Structure IUPAC name |
|---|---|
| 207-P | 2-methyl-2-(5-{[3-(5-{[(1-methylazetidin-3-yl)amino]methyl}-1-(2,2,2-trifluoroethyl)-1H-indol-2-yl)prop-2-yn-1-yl]amino}pyridin-2-yl)propanenitrile |
| 208-P | 2-methyl-2-(5-{[3-(5-{[(oxetan-3-yl)amino]methyl}-1-(2,2,2-trifluoroethyl)-1H-indol-2-yl)prop-2-yn-1-yl]amino}pyridin-2-yl)propanenitrile |
| 209-P | 2-(5-{[3-(5-{[4-(dimethylamino)-piperidin-1-yl]methyl}-1-(2,2,2-trifluoroethyl)-1H-indol-2-yl)prop-2-yn-1-yl]amino}pyridin-2-yl)-2-methylpropanenitrile |
| 210-P | 2-methyl-2-{5-[(3-{5-[({1-[2-(4-methylpiperazin-1-yl)acetyl]piperidin-4-yl}amino)methyl]-1-(2,2,2-trifluoroethyl)-1H-indol-2-yl}prop-2-yn-1-yl)amino]pyridin-2-yl}propanenitrile |

TABLE 1-continued

List of compounds

| # | Structure IUPAC name |
|---|---|
| 211-P | 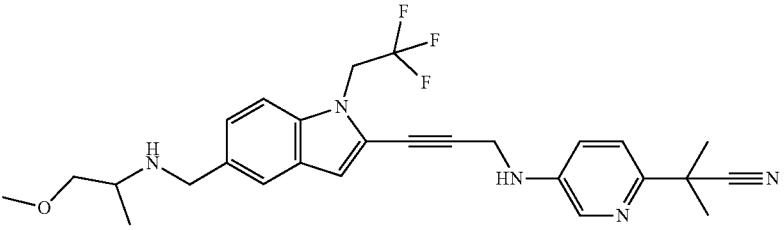 [SMILES: COCC(C)NCc1ccc2c(c1)cc(C#CCNc1ccc(C(C)(C)C#N)nc1)n2CC(F)(F)F]<br>2-(5-{[3-(5-{[(1-methoxypropan-2-yl)amino]methyl}-1-(2,2,2-trifluoroethyl)-1H-indol-2-yl)prop-2-yn-1-yl]amino}pyridin-2-yl)-2-methylpropanenitrile |
| 212-P | 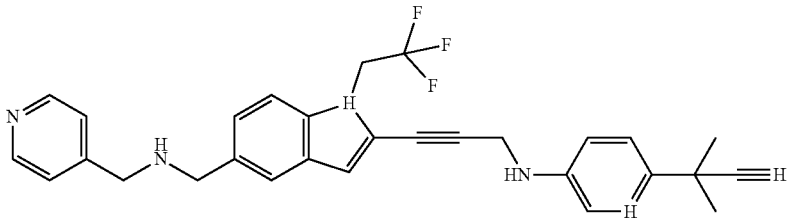<br>2-methyl-2-(5-{[3-(5-{[(pyridin-4-ylmethyl)amino]methyl]-1-(2,2,2-trifluoroethyl)-1H-indol-2-yl)prop-2-yn-1-yl]amino}pyridin-2-yl)propanenitrile |
| 213-P | 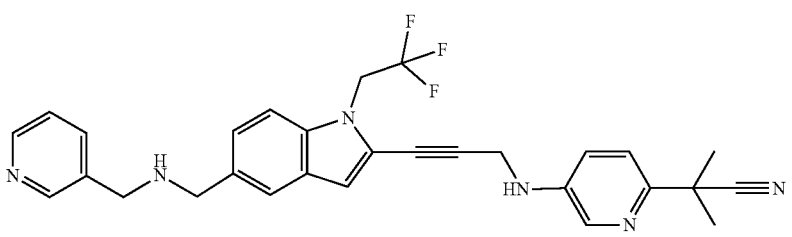 [SMILES: CC(C)(C#N)c1ccc(NCC#Cc2cc3cc(CNCc4cccnc4)ccc3n2CC(F)(F)F)cn1]<br>2-methyl-2-(5-{[3-(5-{[(pyridin-3-ylmethyl)amino]methyl}-1-(2,2,2-trifluoroethyl)-1H-indol-2-yl)prop-2-yn-1-yl]amino}pyridin-2-yl)propanenitrile |
| 214-P | 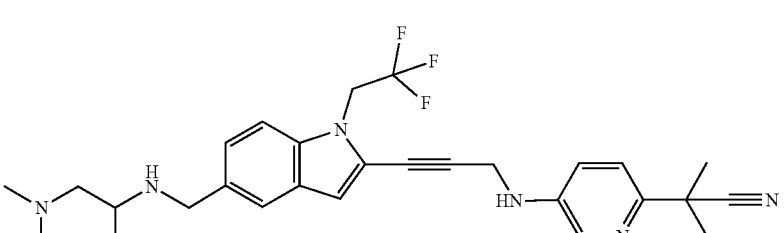<br>2-[5-({3-[5-({[1-(dimethylamino)-propan-2-yl]amino}methyl)-1-(2,2,2-trifluoroethyl)-1H-indol-2-yl]prop-2-yn-1-yl}amino)pyridin-2-yl]-2-methylpropanenitrile |

TABLE 1-continued

List of compounds

| # | Structure IUPAC name |
|---|---|

215-P

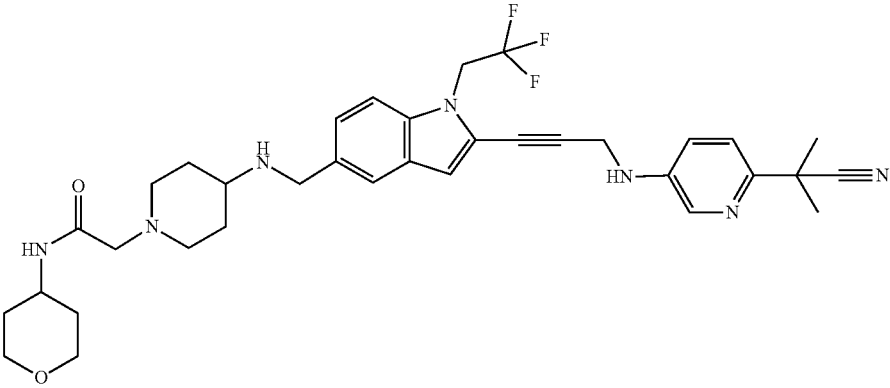 [SMILES: CC(C)(C#N)c1ccc(NCC#Cc2cc3cc(CNC4CCN(CC(=O)NC5CCOCC5)CC4)ccc3n2CC(F)(F)F)cn1]

2-[4-({[2-(3-{[6-(1-cyano-1-
methylethyl)pyridin-3-yl]amino}prop-1-yn-
1-yl)-1-(2,2,2-trifluoroethyl)-1H-indol-5-
yl]methyl}amino)piperidin-1-yl]-N-(oxan-4-yl)acetamide

216-P

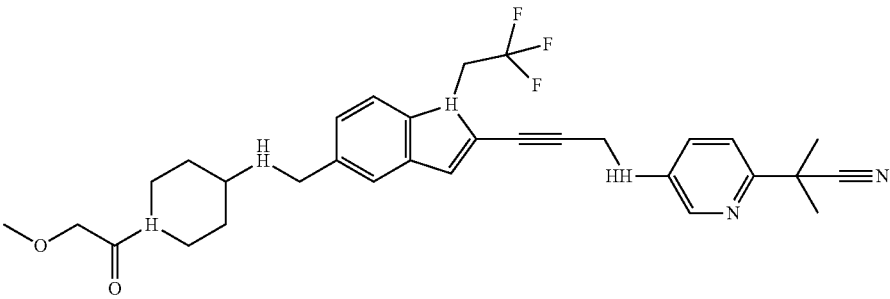

2-[5-({3-[5-({[1-(2-methoxyacetyl)-
piperidin-4-yl]amino}methyl)-1-(2,2,2-
trifluoroethyl)-1H-indol-2-yl]prop-2-yn-1-
yl}amino)pyridin-2-yl]-2-
methylpropanenitrile

217-P

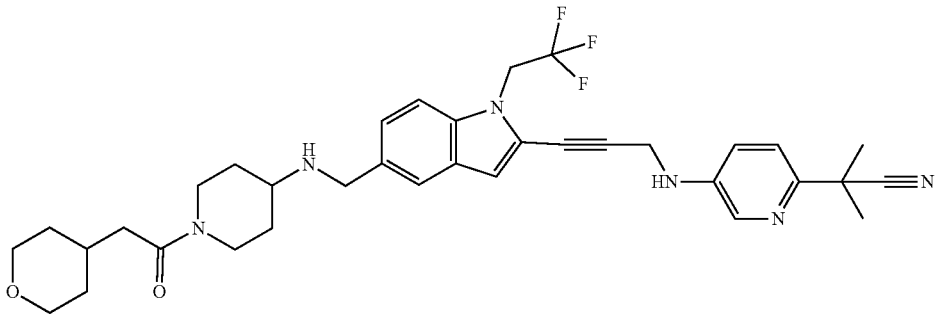 [SMILES: CC(C)(C#N)c1ccc(NCC#Cc2cc3cc(CNC4CCN(C(=O)CC5CCOCC5)CC4)ccc3n2CC(F)(F)F)cn1]

2-methyl-2-{5-[(3-{5-[({1-[2-(oxan-4-
yl)acetyl]piperidin-4-yl}amino)-methyl]-1-
(2,2,2-trifluoroethyl)-1H-indol-2-yl}prop-2-
yn-1-yl)amino]-pyridin-2-yl}propanenitrile TABLE 1-continued List of compounds

| # | Structure IUPAC name |
|---|---|
| 218-P | 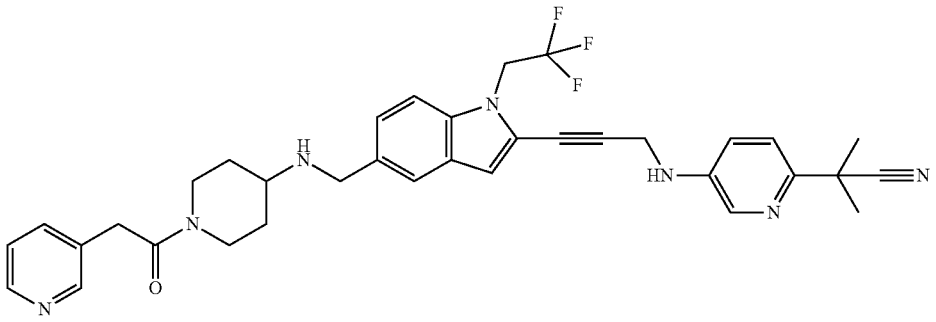 [SMILES: CC(C)(C#N)c1ccc(NCC#Cc2cc3cc(CNC4CCN(C(=O)Cc5cccnc5)CC4)ccc3n2CC(F)(F)F)cn1]<br>2-methyl-2-{5-[(3-{5-[({1-[2-(pyridin-3-yl)acetyl]piperidin-4-yl}amino)-methyl]-1-(2,2,2-trifluoroethyl)-1H-indol-2-yl}prop-2-yn-1-yl)amino]-pyridin-2-yl}propanenitrile |
| 219-P | 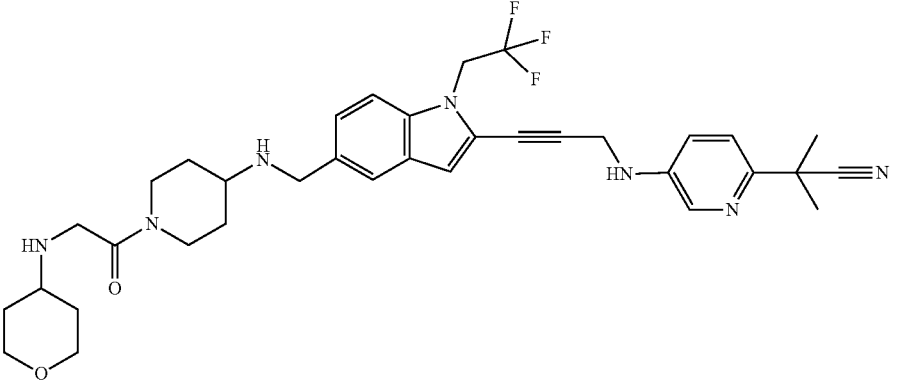 [SMILES: CC(C)(C#N)c1ccc(NCC#Cc2cc3cc(CNC4CCN(C(=O)CNC5CCOCC5)CC4)ccc3n2CC(F)(F)F)cn1]<br>2-methyl-2-(5-{[3-(5-{[(1-{2-[(oxan-4-yl)amino]acetyl}piperidin-4-yl)amino]methyl}-1-(2,2,2-trifluoroethyl)-1H-indol-2-yl)prop-2-yn-1-yl]amino}pyridin-2-yl)-propanenitrile |
| 220-P | 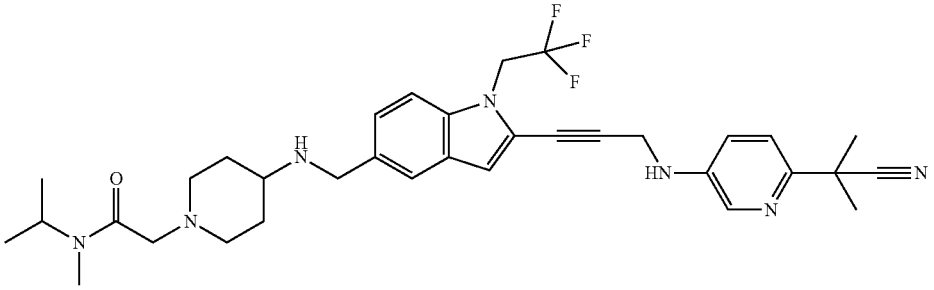 [SMILES: CC(C)N(C)C(=O)CN1CCC(NCc2ccc3c(c2)cc(C#CCNc2ccc(C(C)(C)C#N)nc2)n3CC(F)(F)F)CC1]<br>2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-methyl-N-(propan-2-yl)acetamide |

TABLE 1-continued

List of compounds

| # | Structure IUPAC name |
|---|---|
| 221-P | 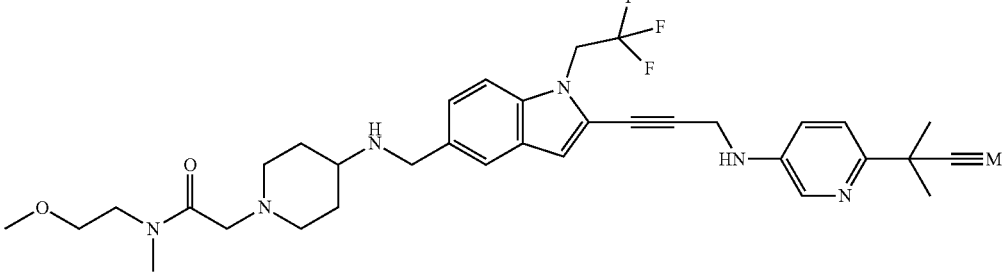<br>2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(2-methoxyethyl)-N-methylacetamide |
| 222-P | 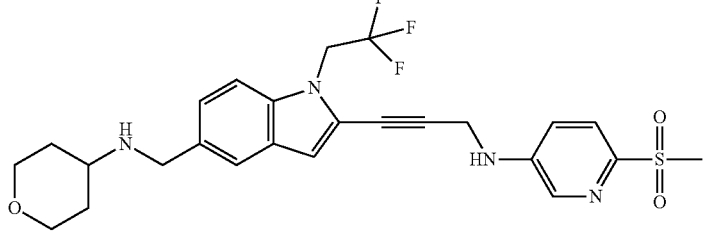<br>6-methanesulfonyl-N-[3-(5-{[(oxan-4-yl)amino]methyl}-1-(2,2,2-trifluoroethyl)-1H-indol-2-yl)prop-2-yn-1-yl]pyridin-3-amine |
| 223-P | 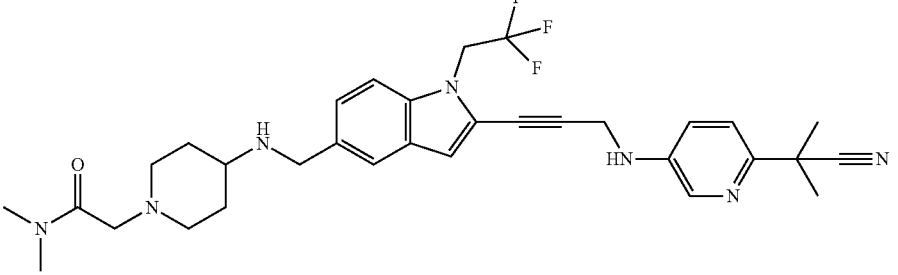<br>2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N,N-dimethylacetamide |
| 224-P | 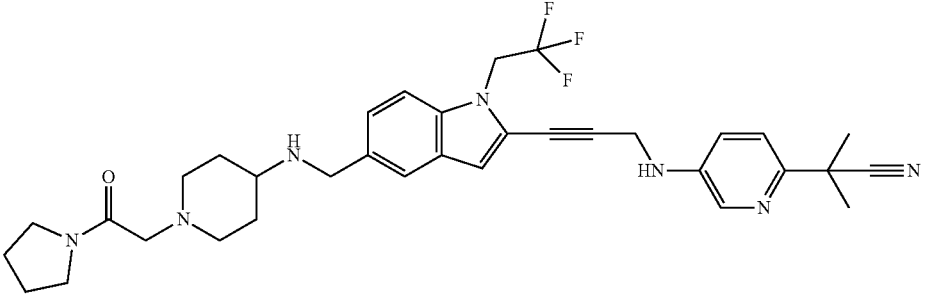 [SMILES: CC(C)(C#N)c1ccc(NCC#Cc2cc3cc(CNC4CCN(CC(=O)N5CCCC5)CC4)ccc3n2CC(F)(F)F)cn1]<br>2-methyl-2-{5-[(3-{5-[({1-[2-oxo-2-(pyrrolidin-1-yl)ethyl]piperidin-4-yl}amino)methyl]-1-(2,2,2-trifluoroethyl)-1H-indol-2-yl}prop-2-yn-1-yl)amino]pyridin-2-yl}propanenitrile |

TABLE 1-continued

List of compounds

| # | Structure IUPAC name |
|---|---|
| 225-P | 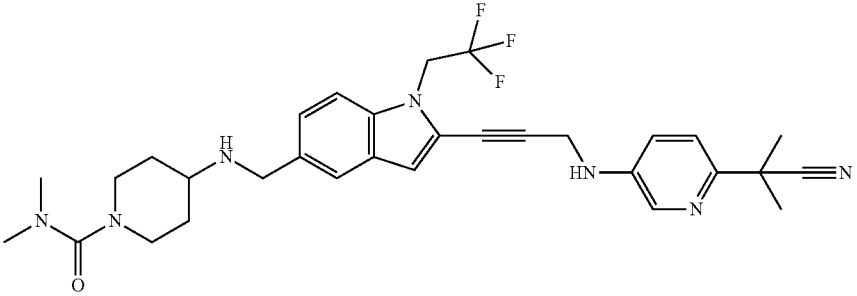 [SMILES: CN(C)C(=O)N1CCC(NCc2ccc3c(c2)cc(C#CCNc2ccc(C(C)(C)C#N)nc2)n3CC(F)(F)F)CC1]

4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)-N,N-dimethylpiperidine-1-carboxamide |
| 226-P | 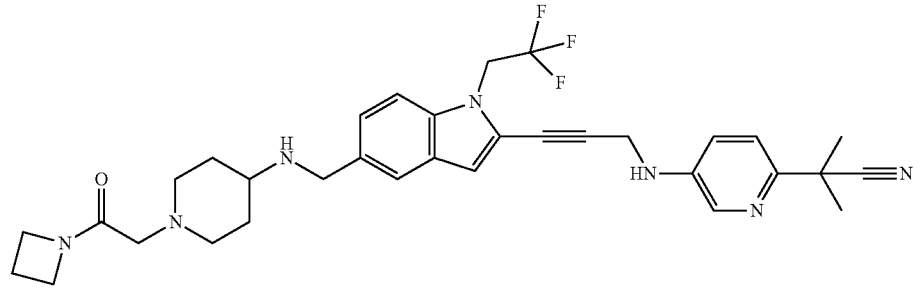 [SMILES: CC(C)(C#N)c1ccc(NCC#Cc2cc3cc(CNC4CCN(CC(=O)N5CCC5)CC4)ccc3n2CC(F)(F)F)cn1]

2-{5-[(3-{5-[({1-[2-(azetidin-1-yl)-2-oxoethyl]piperidin-4-yl}amino)-methyl]-1-(2,2,2-trifluoroethyl)-1H-indol-2-yl}prop-2-yn-1-yl)amino]-pyridin-2-yl}-2-methylpropanenitrile |
| 227-P | 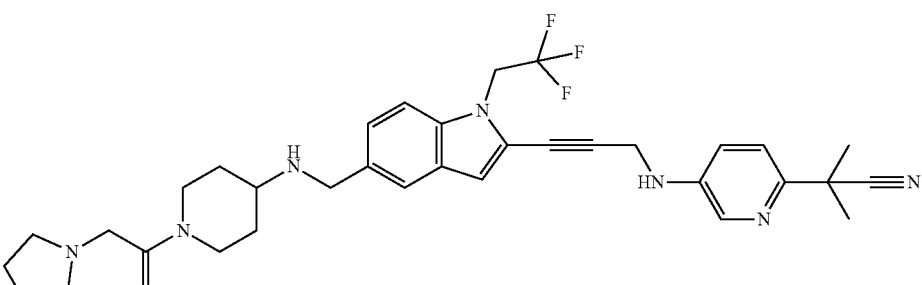

2-methyl-2-{5-[(3-{5-[({1-[2-(pyrrolidin-1-yl)acetyl]piperidin-4-yl}amino)methyl]-1-(2,2,2-trifluoroethyl)-1H-indol-2-yl}prop-2-yn-1-yl)amino]pyridin-2-yl}-propanenitrile |

TABLE 1-continued

List of compounds

| # | Structure IUPAC name |
|---|---|

228-P

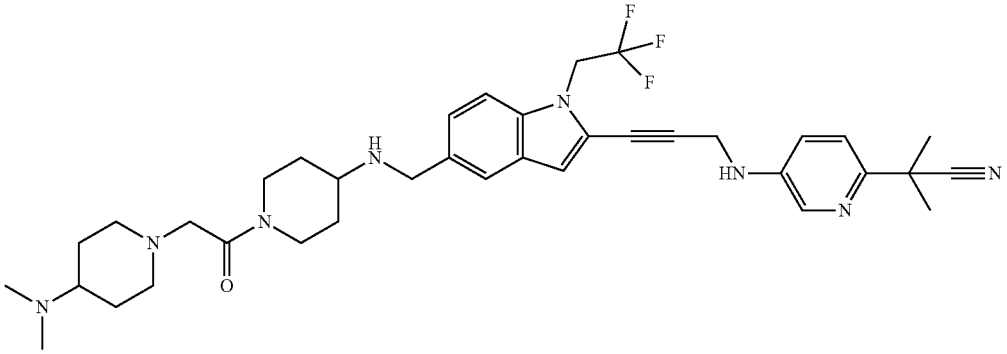 [SMILES: CN(C)C1CCN(CC(=O)N2CCC(NCc3ccc4c(c3)cc(C#CCNc3ccc(C(C)(C)C#N)nc3)n4CC(F)(F)F)CC2)CC1]

2-(5-{[3-(5-{[(1-{2-[4-
(dimethylamino)piperidin-1-
yl]acetyl}piperidin-4-yl)amino]-methyl}-1-
(2,2,2-trifluoroethyl)-1H-indol-2-yl)prop-2-
yn-1-yl]amino}pyridin-2-yl)-2-methylpropanenitrile

229-P

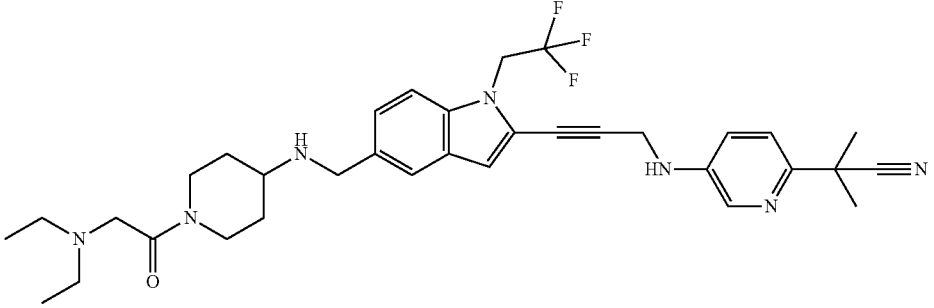 [SMILES: CCN(CC)CC(=O)N1CCC(NCc2ccc3c(c2)cc(C#CCNc2ccc(C(C)(C)C#N)nc2)n3CC(F)(F)F)CC1]

2-{5-[(3-{5-[({1-[2-
(diethylamino)acetyl]piperidin-4-
yl}amino)methyl]-1-(2,2,2-trifluoroethyl)-
1H-indol-2-yl}prop-2-yn-1-
yl)amino]pyridin-2-yl}-2-methylpropanenitrile

230-P

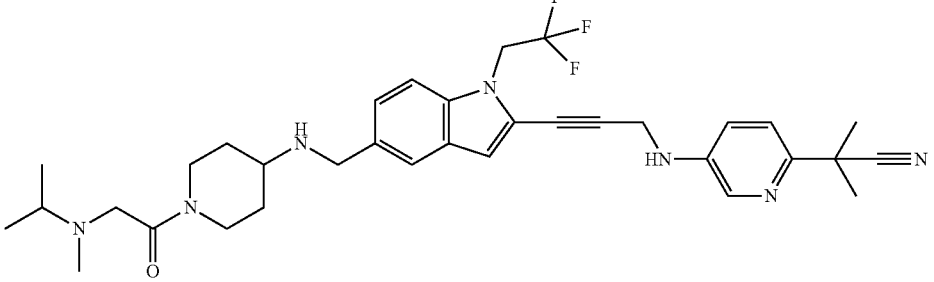

2-methyl-2-(5-{[3-(5-{[(1-{2-
[methyl(propan-2-yl)amino]acetyl}piperidin-
4-yl)amino]methyl}-1-(2,2,2-trifluoroethyl)-
1H-indol-2-yl)prop-2-yn-1-
yl]amino}pyridin-2-yl)propanenitrile TABLE 1-continued List of compounds

| # | Structure IUPAC name |
|---|---|
| 231-P | 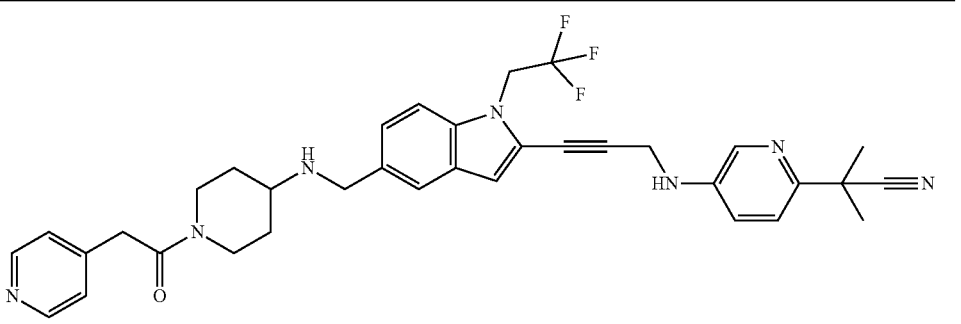<br>2-methyl-2-{5-[(3-{5-[({1-[2-(pyridin-4-yl)acetyl]piperidin-4-yl]amino)methyl]-1-(2,2,2-trifluoroethyl)-1H-indol-2-yl}prop-2-yn-1-yl)amino]pyridin-2-yl}propanenitrile |
| 232-P | 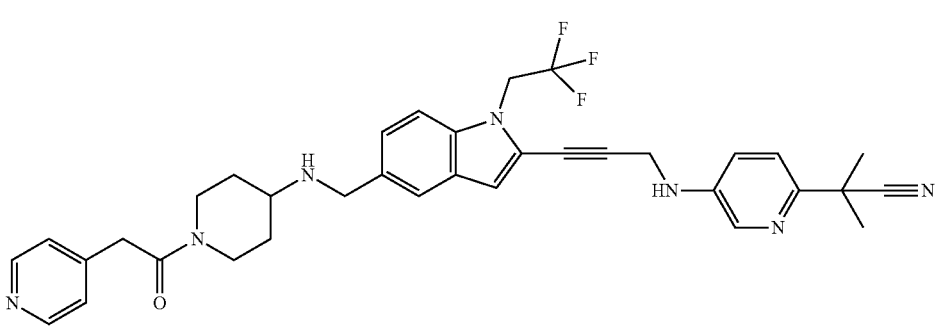<br>2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(pyridin-4-yl)acetamide |
| 233-P | 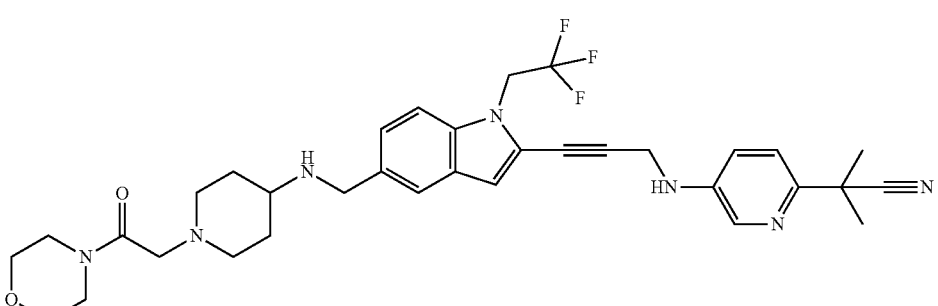 [SMILES: CC(C)N(C)CC(=O)N1CCC(NCc2ccc3c(c2)cc(C#CCNc2ccc(C(C)(C)C#N)nc2)n3CC(F)(F)F)CC1]<br>2-methyl-2-{5-[(3-{5-[({1-[2-(morpholin-4-yl)-2-oxoethyl]piperidin-4-yl}amino)methyl]-1-(2,2,2-trifluoroethyl)-1H-indol-2-yl}prop-2-yn-1-yl)amino]pyridin-2-yl}propanenitrile |

TABLE 1-continued

List of compounds

| # | Structure IUPAC name |
|---|---|
| 234-P | 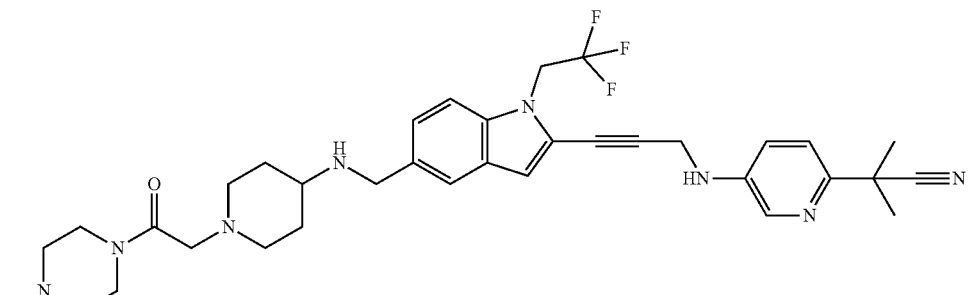

2-methyl-2-{5-[(3-{5-[({1-[2-(4-methylpiperazin-1-yl)-2-oxoethyl]piperidin-4-yl}amino)methyl]-1-(2,2,2-trifluoroethyl)-1H-indol-2-yl}prop-2-yn-1-yl)amino]pyridin-2-yl}propanenitrile |
| 235-P | 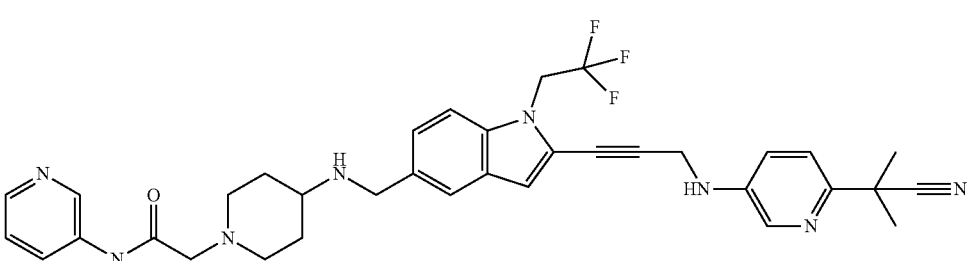

2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(pyridin-3-yl)acetamide |
| 236-P | 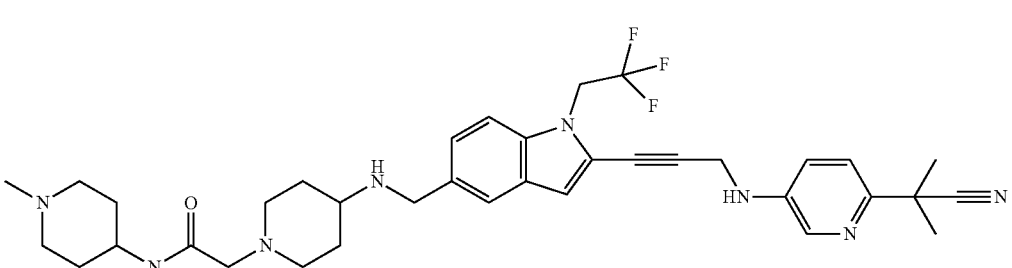

2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(1-methylpiperidin-4-yl)acetamide |

TABLE 1-continued

List of compounds

| # | Structure IUPAC name |

237-P
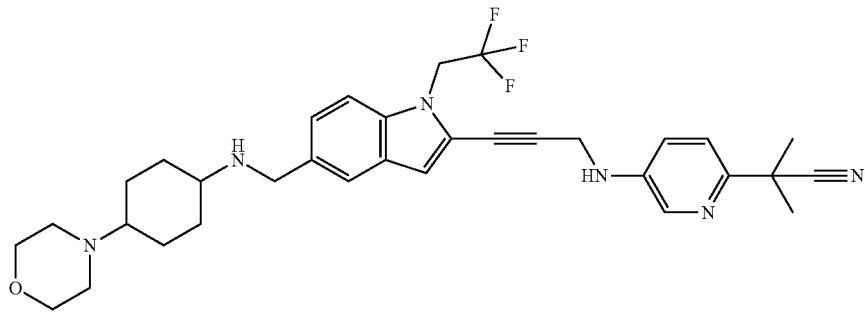 [SMILES: CC(C)(C#N)c1ccc(NCC#Cc2cc3cc(CNC4CCC(N5CCOCC5)CC4)ccc3n2CC(F)(F)F)cn1]

2-methyl-2-{5-({3-[5-({[4-(morpholin-4-yl)cyclohexyl]amino}methyl)-1-(2,2,2-trifluoroethyl)-1H-indol-2-yl]prop-2-yn-1-yl}amino)pyridin-2-yl]propanenitrile 238-P
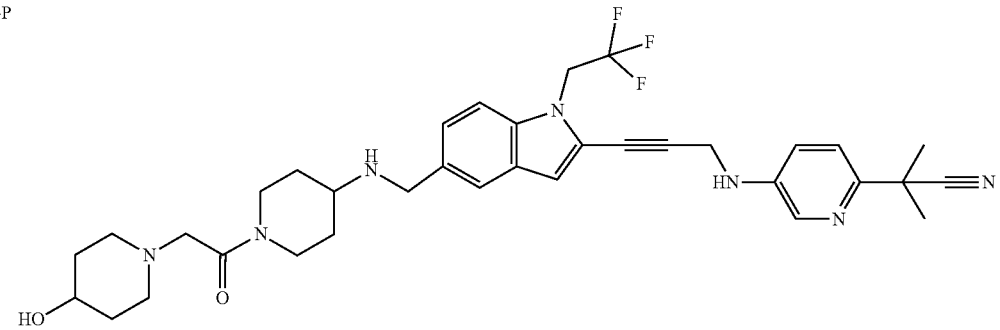

2-{5-[(3-{5-[({1-[2-(4-hydroxypiperidin-1-yl)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile 239-P
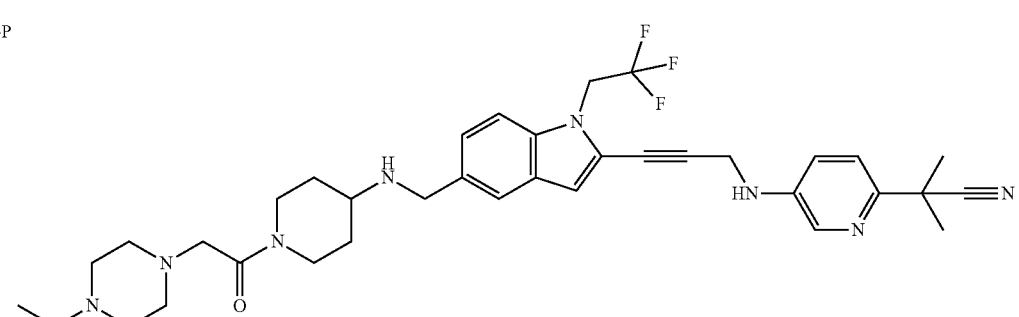

2-{5-[(3-{5-[({1-[2-(4-acetylpiperazin-1-yl)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile TABLE 1-continued

| # | Structure IUPAC name |
|---|---|
| 240-P | 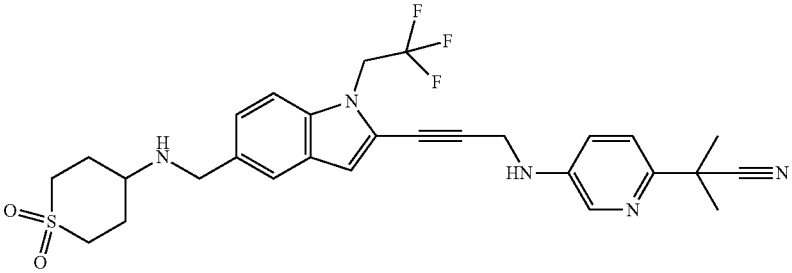 [SMILES: CC(C)(C#N)c1ccc(NCC#Cc2cc3cc(CNC4CCS(=O)(=O)CC4)ccc3n2CC(F)(F)F)cn1]
2-(5-{[3-(5-{[(1,1-dioxo-1λ⁶-thian-4-yl)amino]methyl}-1-(2,2,2-trifluoroethyl)-1H-indol-2-yl)prop-2-yn-1-yl]amino}pyridin-2-yl)-2-methylpropanenitrile |
| 241-P | 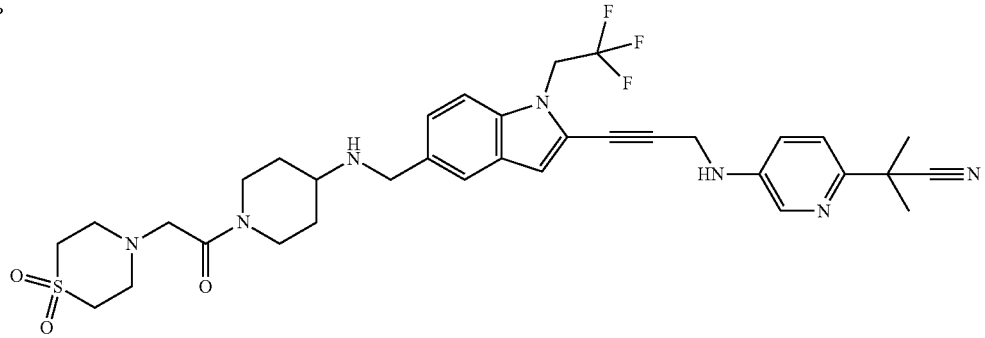
2-{5-[(3-{5-[({1-[2-(1,1-dioxo-1λ⁶,4-thiomorpholin-4-yl)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 242-P | 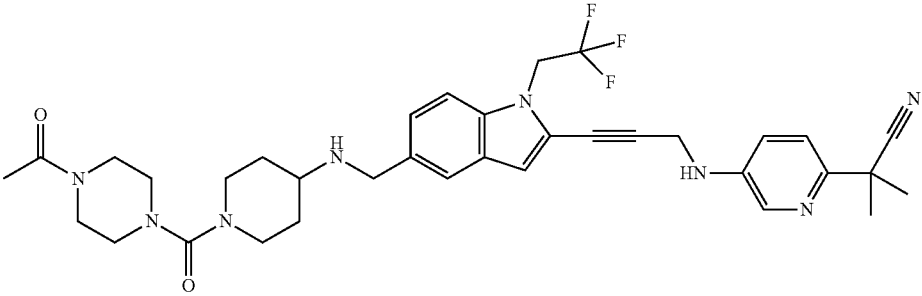 [SMILES: CC(=O)N1CCN(C(=O)N2CCC(NCc3ccc4c(c3)cc(C#CCNc3ccc(C(C)(C)C#N)nc3)n4CC(F)(F)F)CC2)CC1]
2-[5-({3-[5-({[1-(4-acetylpiperazine-1-carbonyl)piperidin-4-yl]amino}methyl)-1-(2,2,2-trifluoroethyl)-1H-indol-2-yl]prop-2-yn-1-yl}amino)pyridin-2-yl]-2-methylpropanenitrile |

TABLE 1-continued

List of compounds

| # | Structure IUPAC name |
|---|---|
| 243-P | 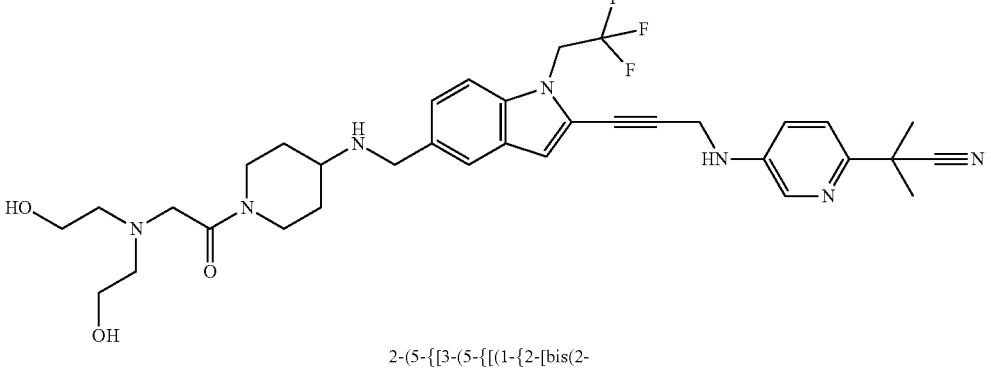
2-(5-{[3-(5-{[(1-{2-[bis(2-hydroxyethyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |
| 244-P | 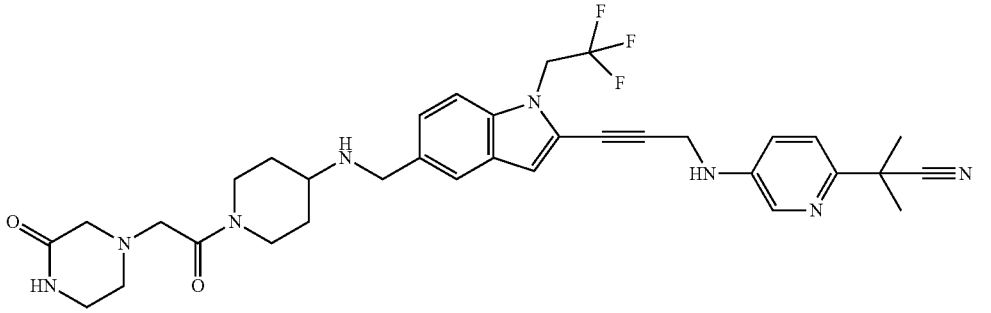 [SMILES: CC(C)(C#N)c1ccc(NCC#Cc2cc3cc(CNC4CCN(C(=O)CN5CCNC(=O)C5)CC4)ccc3n2CC(F)(F)F)cn1]
2-methyl-2-{5-[(3-{5-[({1-[2-(3-oxopiperazin-1-yl)acetyl]piperidin-4-yl}amino)methyl]-1-(2,2,2-trifluoroethyl)-1H-indol-2-yl}prop-2-yn-1-yl)amino]pyridin-2-yl}propanenitrile |
| 245-P | 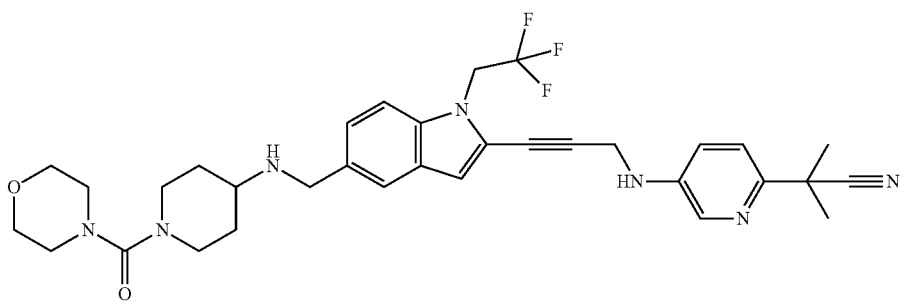 [SMILES: CC(C)(C#N)c1ccc(NCC#Cc2cc3cc(CNC4CCN(C(=O)N5CCOCC5)CC4)ccc3n2CC(F)(F)F)cn1]
2-methyl-2-[5-({3-[5-({[1-(morpholine-4-carbonyl)piperidin-4-yl]amino}-methyl)-1-(2,2,2-trifluoroethyl)-1H-indol-2-yl]prop-2-yn-1-yl}amino)pyridin-2-yl]propanenitrile |

TABLE 1-continued

List of compounds

| # | Structure IUPAC name |
|---|---|
| 246-P | 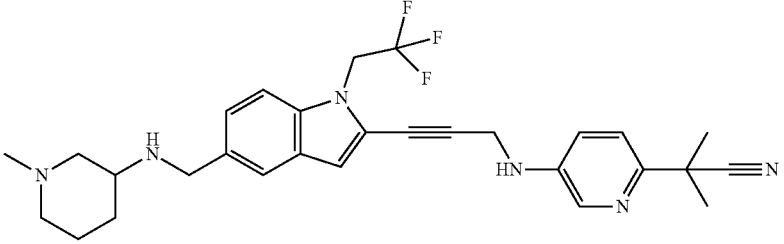 [SMILES: CN1CCCC(NCc2ccc3c(c2)cc(C#CCNc2ccc(C(C)(C)C#N)nc2)n3CC(F)(F)F)C1]
2-methyl-2-(5-{[3-(5-{[(1-methylpiperidin-3-yl)amino]methyl}-1-(2,2,2-trifluoroethyl)-1H-indol-2-yl)prop-2-yn-1-yl]amino}pyridin-2-yl)propanenitrile |
| 247-P | 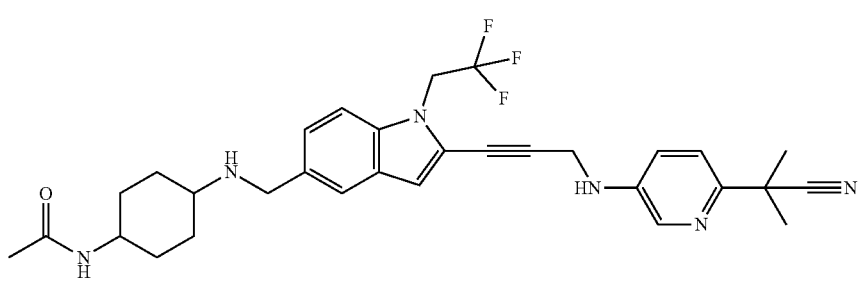 [SMILES: CC(=O)NC1CCC(NCc2ccc3c(c2)cc(C#CCNc2ccc(C(C)(C)C#N)nc2)n3CC(F)(F)F)CC1]
N-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)-cyclohexyl]acetamide |
| 248-P | 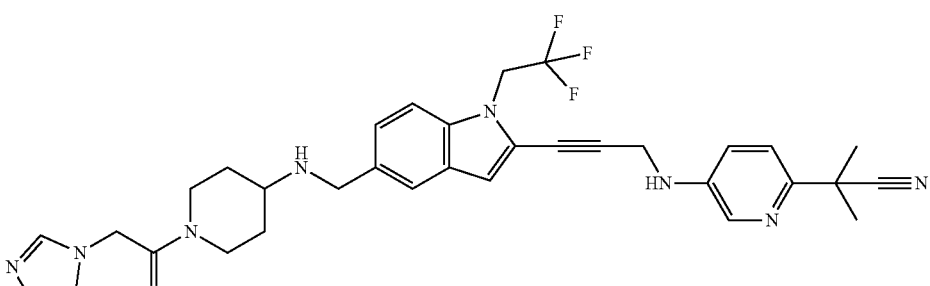
2-{5-[(3-{5-[({1-[2-(1H-imidazol-1-yl)acetyl]piperidin-4-yl}amino)-methyl]-1-(2,2,2-trifluoroethyl)-1H-indol-2-yl}prop-2-yn-1-yl)amino]pyridin-2-yl}-2-methylpropanenitrile |
| 249-P | 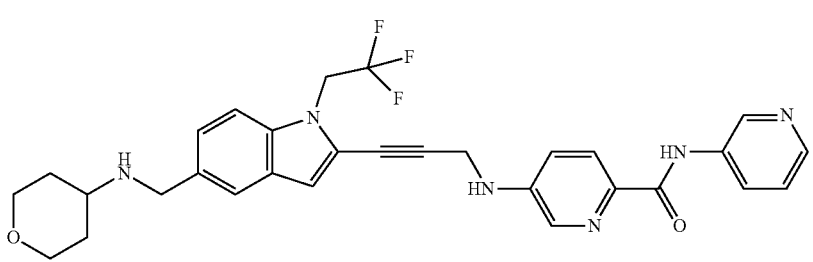 [SMILES: O=C(Nc1cccnc1)c1ccc(NCC#Cc2cc3cc(CNC4CCOCC4)ccc3n2CC(F)(F)F)cn1]
2-(5-{[3-(5-{[(1-{2-[(2-methoxyethyl)(methyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |

TABLE 1-continued

List of compounds

| # | Structure IUPAC name |
|---|---|
| 250-P | 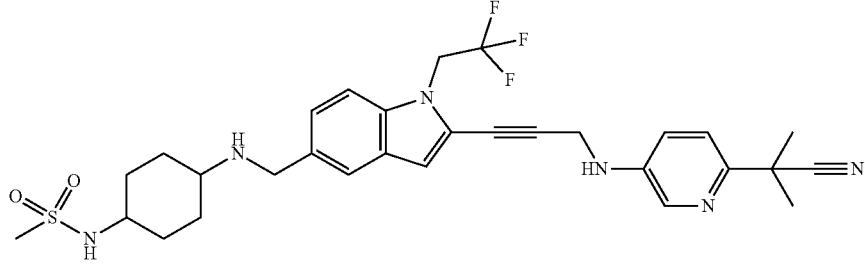 [SMILES: CC(C)(C#N)c1ccc(NCC#Cc2cc3cc(CNC4CCC(NS(C)(=O)=O)CC4)ccc3n2CC(F)(F)F)cn1]  N-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)-cyclohexyl]methanesulfonamide |
| 251-P | 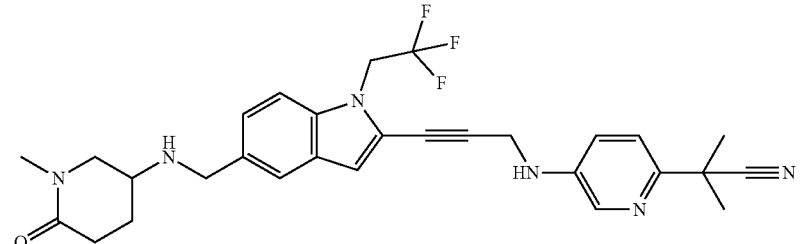  2-methyl-2-(5-{[3-(5-{[(1-methyl-6-oxopiperidin-3-yl)amino]methyl}-1-(2,2,2-trifluoroethyl)-1H-indol-2-yl)prop-2-yn-1-yl]amino}pyridin-2-yl)propanenitrile |
| 252-P | 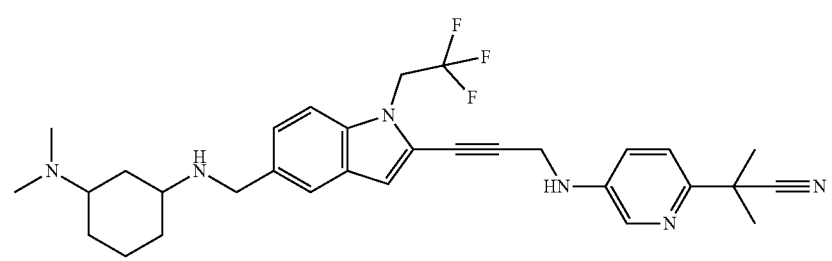 [SMILES: CN(C)C1CCCC(NCc2ccc3c(c2)cc(C#CCNc2ccc(C(C)(C)C#N)nc2)n3CC(F)(F)F)C1]  2-[5-({3-[5-({[3-(dimethylamino)cyclohexyl]amino}methyl)-1-(2,2,2-trifluoroethyl)-1H-indol-2-yl]prop-2-yn-1-yl}amino)pyridin-2-yl]-2-methylpropanenitrile |
| 253-P | 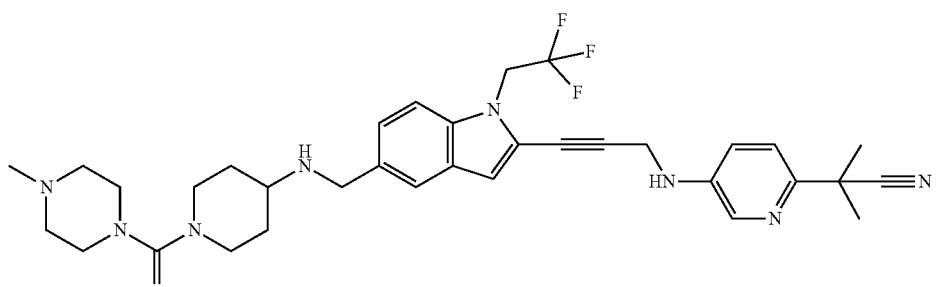  2-methyl-2-[5-({3-[5-({[1-(4-methylpiperazine-1-carbonyl)piperidin-4-yl]amino}methyl)-1-(2,2,2-trifluoroethyl)-1H-indol-2-yl]prop-2-yn-1-yl}amino)pyridin-2-yl]propanenitrile |

TABLE 1-continued

List of compounds

| # | Structure IUPAC name |
|---|---|
| 254-P | 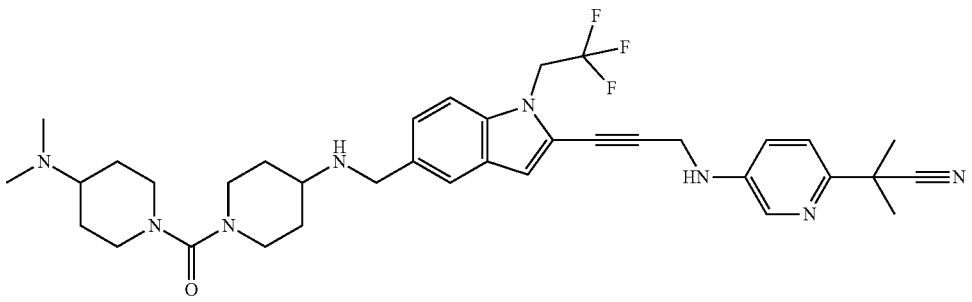 [SMILES: CN(C)C1CCN(C(=O)N2CCC(NCc3ccc4c(c3)cc(C#CCNc3ccc(C(C)(C)C#N)nc3)n4CC(F)(F)F)CC2)CC1]<br>2-{5-[(3-{5-[({1-[4-(dimethylamino)piperidine-1-carbonyl]piperidin-4-yl}amino)-methyl]-1-(2,2,2-trifluoroethyl)-1H-indol-2-yl}prop-2-yn-1-yl)amino]pyridin-2-yl}-2-methylpropanenitrile |
| 255-P | 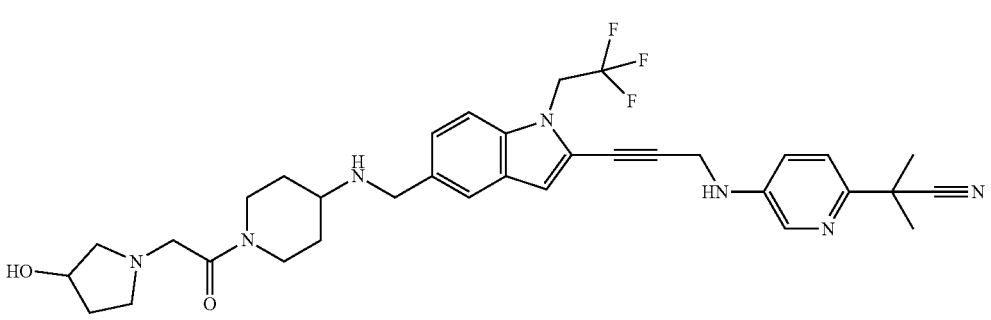 [SMILES: CC(C)(C#N)c1ccc(NCC#Cc2cc3cc(CNC4CCN(C(=O)CN5CCC(O)C5)CC4)ccc3n2CC(F)(F)F)cn1]<br>2-{5-[(3-{5-[({1-[2-(3-hydroxypyrrolidin-1-yl)acetyl]-piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 256-P | 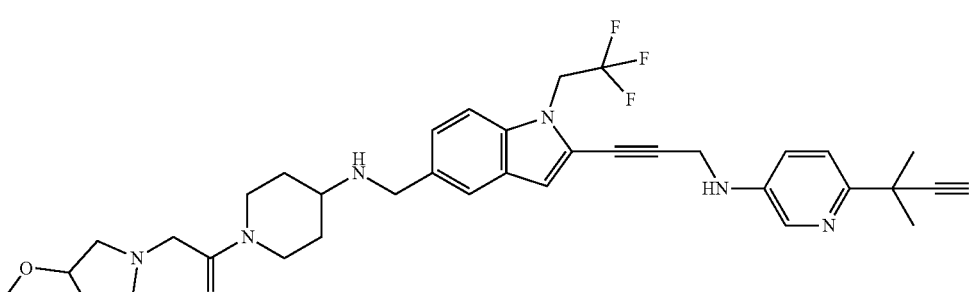<br>2-{5-[(3-{5-[({1-[2-(3-methoxypyrrolidin-1-yl)acetyl]-piperidin-4-yl}amino)methyl]-1-(2,2,2-trifluoroethyl)-1H-indol-2-yl}prop-2-yn-1-yl)amino]pyridin-2-yl}-2-methylpropanenitrile |

TABLE 1-continued

List of compounds

| # | Structure IUPAC name |
|---|---|
| 257-P | 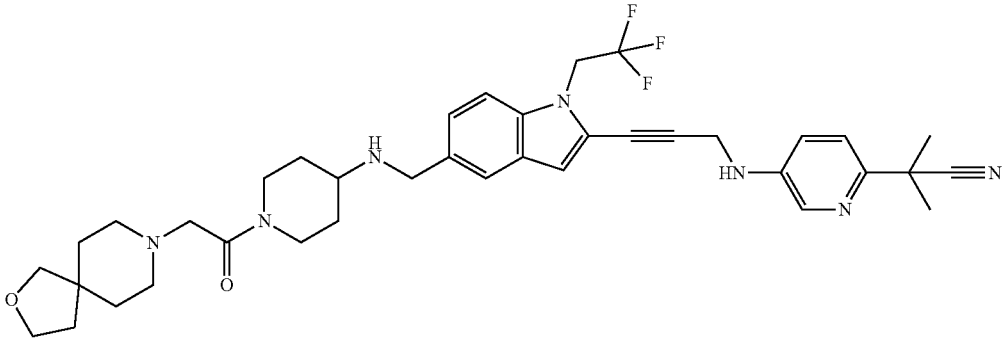 [SMILES: CC(C)(C#N)c1ccc(NCC#Cc2cc3cc(CNC4CCN(C(=O)CN5CCC6(CCOC6)CC5)CC4)ccc3n2CC(F)(F)F)cn1]  2-methyl-2-[5-({3-[5-({[1-(2-{2-oxa-8-azaspiro[4.5]decan-8-yl}acetyl)-piperidin-4-yl]amino}methyl)-1-(2,2,2-trifluoroethyl)-1H-indol-2-yl]prop-2-yn-1-yl}amino)pyridin-2-yl]propanenitrile |
| 258-P | 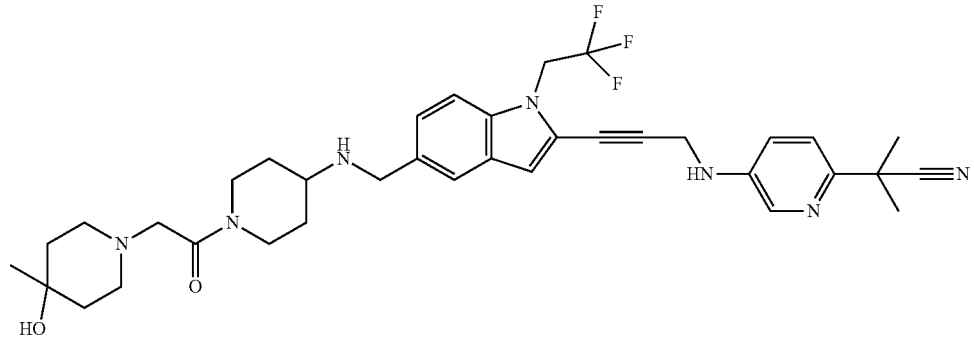 [SMILES: CC1(O)CCN(CC(=O)N2CCC(NCc3ccc4c(c3)cc(C#CCNc3ccc(C(C)(C)C#N)nc3)n4CC(F)(F)F)CC2)CC1]  2-{5-[(3-{5-[({1-[2-(4-hydroxy-4-methylpiperidin-1-yl)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 259-P | 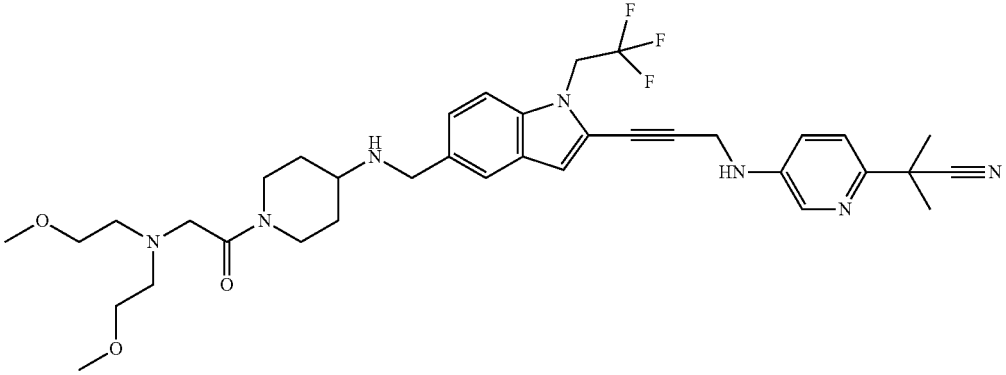 [SMILES: COCCN(CCOC)CC(=O)N1CCC(NCc2ccc3c(c2)cc(C#CCNc2ccc(C(C)(C)C#N)nc2)n3CC(F)(F)F)CC1]  2-(5-{[3-(5-{[(1-{2-[bis(2-methoxyethyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |

TABLE 1-continued

List of compounds

| # | Structure IUPAC name |
|---|---|
| 260-P | 2-(5-{[3-(5-{[(1-{2-[methoxy(methyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |
| 261-P | 2-(5-{[3-(5-{[(1-{2-[(2,3-dihydroxypropyl)(methyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |
| 262-P | 2-methyl-2-(5-{[3-(5-{[(1-methyl-2-oxopiperidin-4-yl)amino]methyl}-1-(2,2,2-trifluoroethyl)-1H-indol-2-yl)prop-2-yn-1-yl]amino}pyridin-2-yl)propanenitrile |
| 263-P | 2-methyl-2-(5-{[3-(5-{[(1-{2-[methyl(1-methylpiperidin-4-yl)amino]acetyl}piperidin-4-yl)amino]methyl}-1-(2,2,2-trifluoroethyl)-1H-indol-2-yl)prop-2-yn-1-yl]amino}pyridin-2-yl)-2-yl)propanenitrile |

TABLE 1-continued

List of compounds

| # | Structure IUPAC name |
|---|---|
| 264-P | 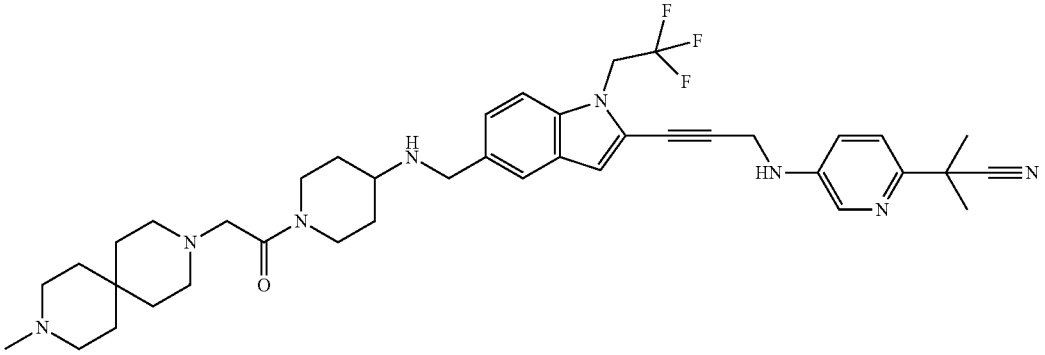 [SMILES: CN1CCC2(CC1)CCN(CC(=O)N1CCC(NCc3ccc4c(c3)cc(C#CCNc3ccc(C(C)(C)C#N)nc3)n4CC(F)(F)F)CC1)CC2]<br>2-methyl-2-[5-({3-[5-({[1-(2-{9-methyl-3,9-diazaspiro[5.5]undecan-3-yl}acetyl)piperidin-4-yl]amino}methyl)-1-(2,2,2-trifluoroethyl)-1H-indol-2-yl]prop-2-yn-1-yl}amino)pyridin-2-yl]propanenitrile |
| 265-P | 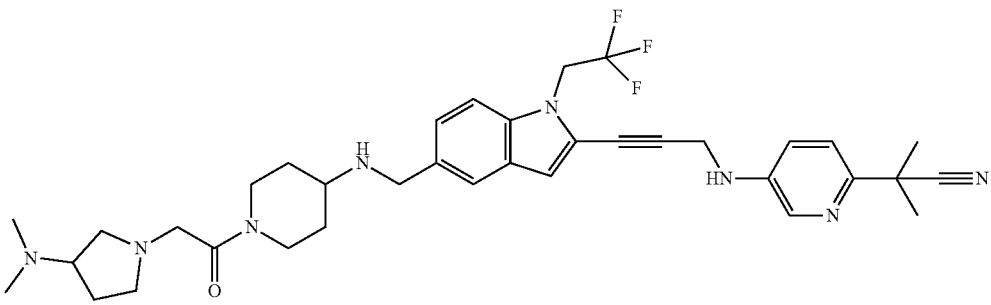 [SMILES: CN(C)C1CCN(CC(=O)N2CCC(NCc3ccc4c(c3)cc(C#CCNc3ccc(C(C)(C)C#N)nc3)n4CC(F)(F)F)CC2)C1]<br>2-(5-{[3-(5-{[(1-{2-[3-(dimethyl-amino)pyrrolidin-1-yl]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |
| 266-P | 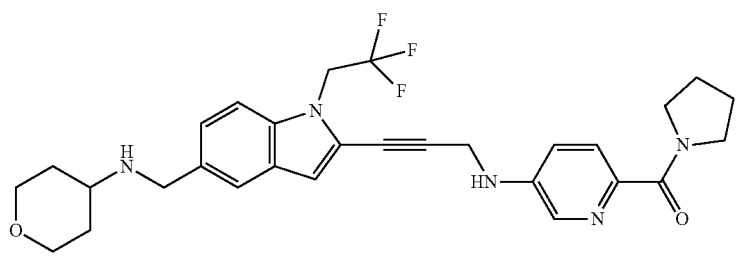 [SMILES: O=C(c1ccc(NCC#Cc2cc3cc(CNC4CCOCC4)ccc3n2CC(F)(F)F)cn1)N1CCCC1]<br>N-[3-(5-{[(oxan-4-yl)amino]methyl}-1-(2,2,2-trifluoroethyl)-1H-indol-2-yl)prop-2-yn-1-yl]-6-(pyrrolidine-1-carbonyl)pyridin-3-amine |
| 267-P | 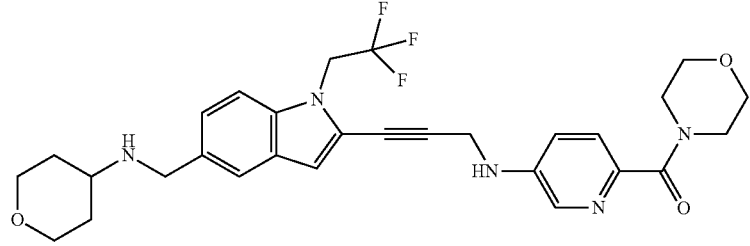 [SMILES: O=C(c1ccc(NCC#Cc2cc3cc(CNC4CCOCC4)ccc3n2CC(F)(F)F)cn1)N1CCOCC1]<br>6-(morpholine-4-carbonyl)-N-[3-(5-{[(oxan-4-yl)amino]methyl}-1-(2,2,2-trifluoroethyl)-1H-indol-2-yl)prop-2-yn-1-yl]pyridin-3-amine |

TABLE 1-continued

List of compounds

| # | Structure IUPAC name |
|---|---|
| 268-P | 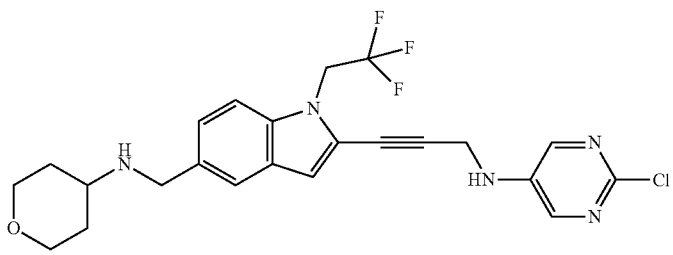 [SMILES: FC(F)(F)Cn1c(C#CCNc2cnc(Cl)nc2)cc2cc(CNC3CCOCC3)ccc21]<br>2-chloro-N-[3-(5-{[(oxan-4-yl)amino]-methyl}-1-(2,2,2-trifluoroethyl)-1H-indol-2-yl)prop-2-yn-1-yl]pyrimidin-5-amine |
| 269-P | 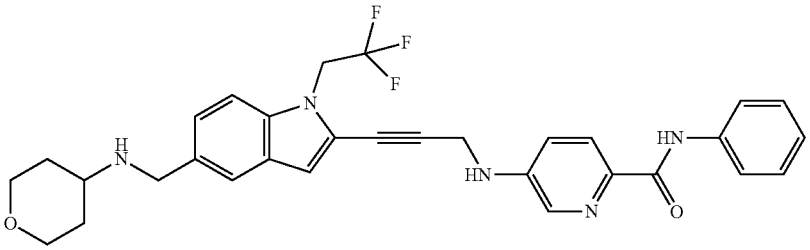<br>5-{[3-(5-{[(oxan-4-yl)amino]methyl}-1-(2,2,2-trifluoroethyl)-1H-indol-2-yl)prop-2-yn-1-yl]amino}-N-phenylpyridine-2-carboxamide |
| 270-P | 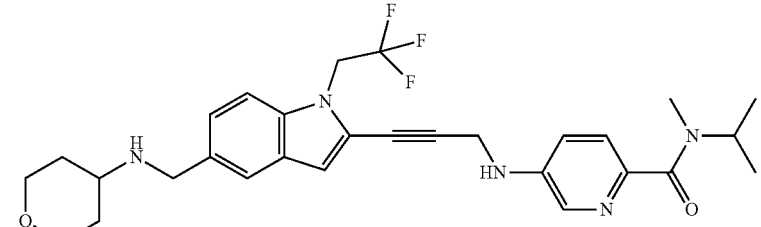<br>N-methyl-5-{[3-(5-{[(oxan-4-yl)amino]methyl}-1-(2,2,2-trifluoroethyl)-1H-indol-2-yl)prop-2-yn-1-yl]amino}-N-(propan-2-yl)pyridine-2-carboxamide |
| 271-P | 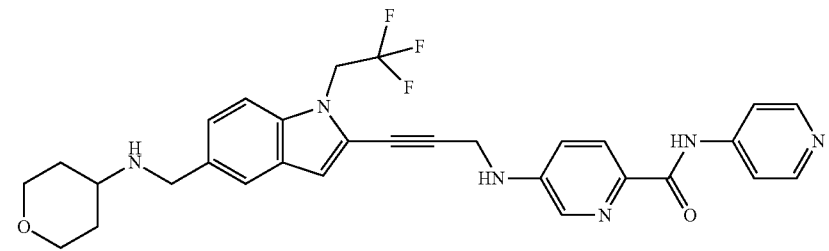 [SMILES: O=C(Nc1ccncc1)c1ccc(NCC#Cc2cc3cc(CNC4CCOCC4)ccc3n2CC(F)(F)F)cn1]<br>5-{[3-(5-{[(oxan-4-yl)amino]methyl}-1-(2,2,2-trifluoroethyl)-1H-indol-2-yl)prop-2-yn-1-yl]amino}-N-(pyridin-4-yl)pyridine-2-carboxamide |

TABLE 1-continued

List of compounds

| # | Structure IUPAC name |
|---|---|
| 272-P | 5-{[3-(5-{[(oxan-4-yl)amino]methyl}-1-(2,2,2-trifluoroethyl)-1H-indol-2-yl)prop-2-yn-1-yl]amino}-N-(pyridin-3-yl)pyridine-2-carboxamide |
| 273-P | N-(1-methylazetidin-3-yl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 274-P | N,N-diethyl-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 275-P | 5-{[3-(5-{[(oxan-4-yl)amino]methyl}-1-(2,2,2-trifluoroethyl)-1H-indol-2-yl)prop-2-yn-1-yl]amino}-N-(oxetan-3-yl)pyridine-2-carboxamide |

TABLE 1-continued

List of compounds

| # | Structure IUPAC name |
|---|---|
| 276-P | 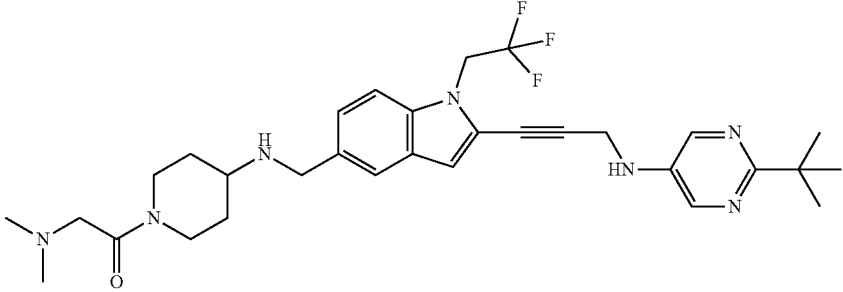 [SMILES: CN(C)CC(=O)N1CCC(NCc2ccc3c(c2)cc(C#CCNc2cnc(C(C)(C)C)nc2)n3CC(F)(F)F)CC1]<br>1-(4-{[(2-{3-[(2-tert-butylpyrimidin-5-yl)amino]prop-1-yn-1-yl}-1-(2,2,2-trifluoroethyl)-1H-indol-5-yl)methyl]amino}piperidin-1-yl)-2-(dimethylamino)ethan-1-one |
| 277-P | 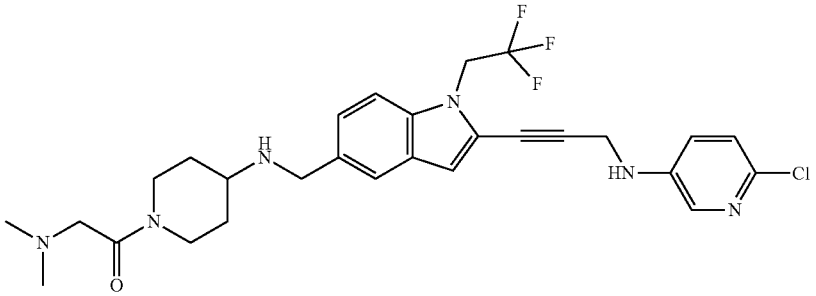 [SMILES: CN(C)CC(=O)N1CCC(NCc2ccc3c(c2)cc(C#CCNc2ccc(Cl)nc2)n3CC(F)(F)F)CC1]<br>1-(4-{[(2-{3-[(6-chloropyridin-3-yl)amino]prop-1-yn-1-yl}-1-(2,2,2-trifluoroethyl)-1H-indol-5-yl)methyl]amino}piperidin-1-yl)-2-(dimethylamino)ethan-1-one |
| 278-P | 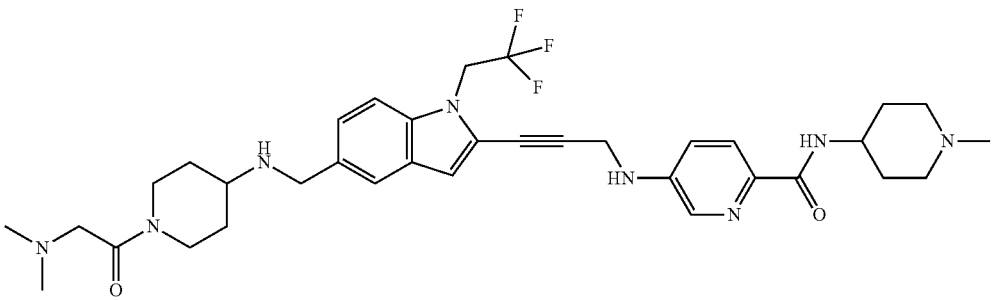<br>5-[(3-{5-[({1-[2-(dimethylamino)-acetyl]piperidin-4-yl}amino)methyl]-1-(2,2,2-trifluoroethyl)-1H-indol-2-yl}prop-2-yn-1-yl)amino]-N-(1-methylpiperidin-4-yl)pyridine-2-carboxamide |

TABLE 1-continued

List of compounds

| # | Structure IUPAC name |
|---|---|
| 279-P | 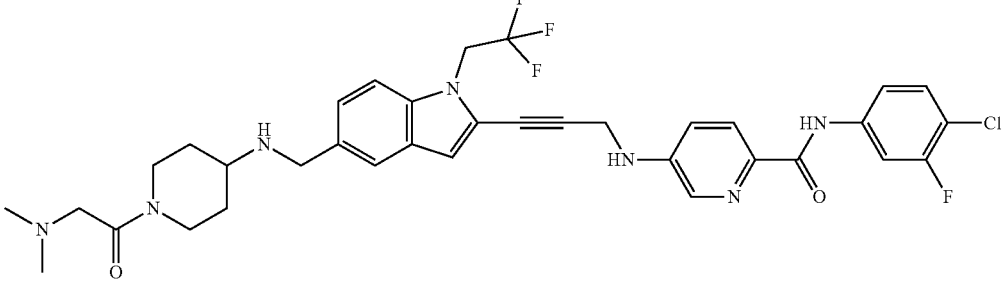<br>1-(4-{[(2-{3-[(4-chloro-3-fluorophenyl)amino]prop-1-yn-1-yl}-1-(2,2,2-trifluoroethyl)-1H-indol-5-yl)methyl]amino}piperidin-1-yl)-2-(dimethylamino)ethan-1-one |
| 280-P | 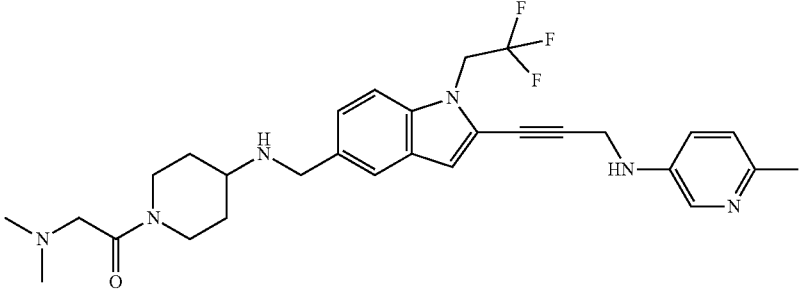<br>2-(dimethylamino)-1-(4-{[(2-{3-[(6-methylpyridin-3-yl)amino]prop-1-yn-1-yl}-1-(2,2,2-trifluoroethyl)-1H-indol-5-yl)methyl]amino}piperidin-1-yl)ethan-1-one |
| 281-P | 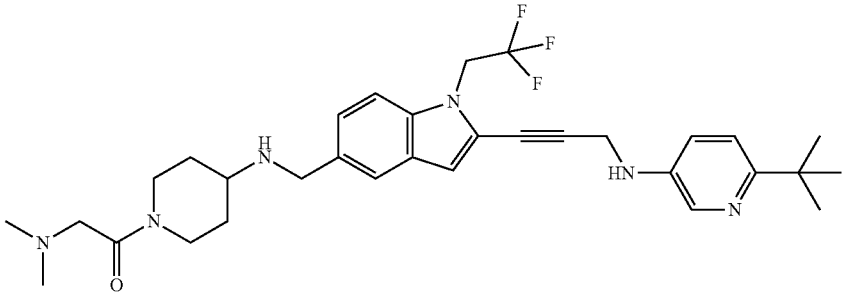<br>1-(4-{[(2-{3-[(6-tert-butylpyridin-3-yl)amino]prop-1-yn-1-yl}-1-(2,2,2-trifluoroethyl)-1H-indol-5-yl)methyl]amino}piperidin-1-yl)-2-(dimethylamino)ethan-1-one |
| 282-P | 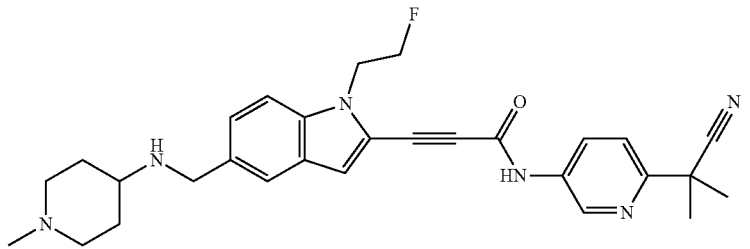 [SMILES: CN1CCC(NCc2ccc3c(c2)cc(C#CC(=O)Nc2ccc(C(C)(C)C#N)nc2)n3CCF)CC1]<br>N-[6-(1-cyano-1-methylethyl)pyridin-3-yl]-3-[1-(2-fluoroethyl)-5-{[(1-methylpiperidin-4-yl)amino]methyl}-1H-indol-2-yl]prop-2-ynamide |

TABLE 1-continued

List of compounds

| # | Structure IUPAC name |
|---|---|
| 283-P | 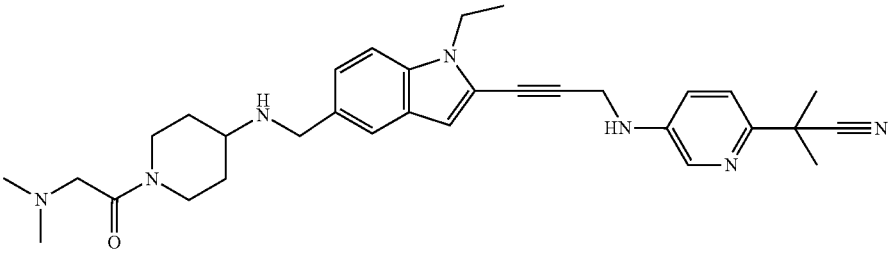 [SMILES: CCn1c(C#CCNc2ccc(C(C)(C)C#N)nc2)cc2cc(CNC3CCN(C(=O)CN(C)C)CC3)ccc21]
2-{5-[(3-{5-[({1-[2-(dimethylamino)acetyl]piperidin-4-yl}amino)methyl]-1-ethyl-1H-indol-2-yl}prop-2-yn-1-yl)amino]pyridin-2-yl}-2-methylpropanenitrile |
| 284-P | 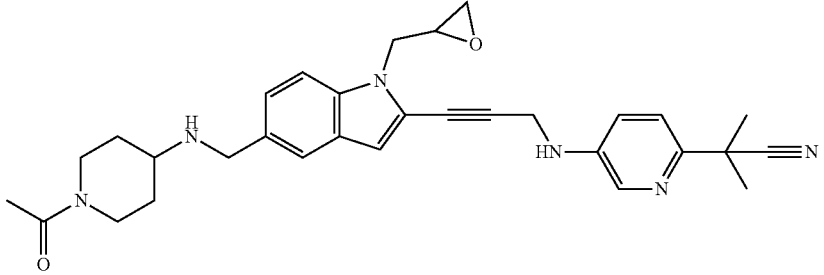 [SMILES: CC(=O)N1CCC(NCc2ccc3c(c2)cc(C#CCNc2ccc(C(C)(C)C#N)nc2)n3CC2CO2)CC1]
2-[5-({3-[1-(2,2-difluoroethyl)-5-[({1-[2-(dimethylamino)acetyl]piperidin-4-yl}amino)methyl]-1H-indol-2-yl]prop-2-yn-1-yl}amino)pyridin-2-yl]-2-methylpropanenitrile |
| 285-P | 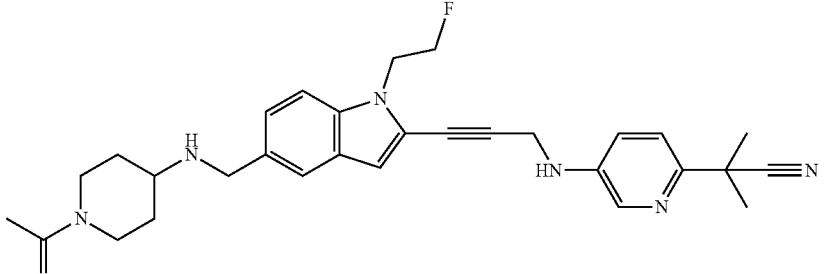
2-{5-[(3-{5-[({1-[2-(dimethylamino)acetyl]piperidin-4-yl}amino)methyl]-1-(2-fluoroethyl)-1H-indol-2-yl}prop-2-yn-1-yl)amino]pyridin-2-yl}-2-methylpropanenitrile |
| 286-P | 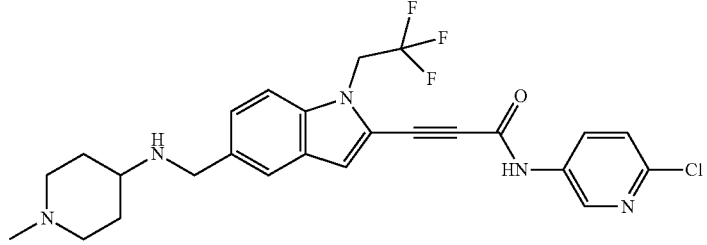 [SMILES: CN1CCC(NCc2ccc3c(c2)cc(C#CC(=O)Nc2ccc(Cl)nc2)n3CC(F)(F)F)CC1]
N-(6-chloropyridin-3-yl)-3-(5-{[(1-methylpiperidin-4-yl)amino]methyl}-1-(2,2,2-trifluoroethyl)-1H-indol-2-yl)prop-2-ynamide |

TABLE 1-continued

List of compounds

| # | Structure IUPAC name |
|---|---|
| 287-P | 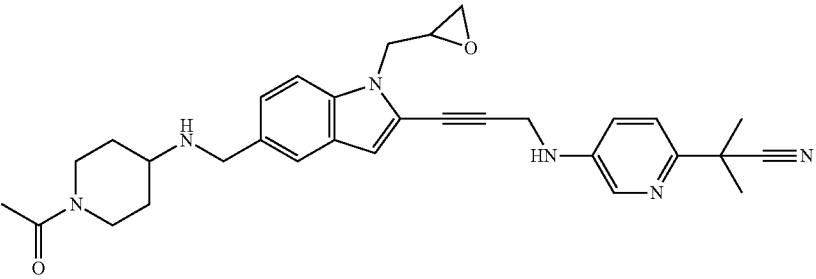 [SMILES: CC(=O)N1CCC(NCc2ccc3c(c2)cc(C#CCNc2ccc(C(C)(C)C#N)nc2)n3CC2CO2)CC1]<br>2-(5-{[3-(5-{[(1-acetylpiperidin-4-yl)amino]methyl}-1-(oxiran-2-ylmethyl)-1H-indol-2-yl)prop-2-yn-1-yl]amino}pyridin-2-yl)-2-methylpropanenitrile |
| 288-P | 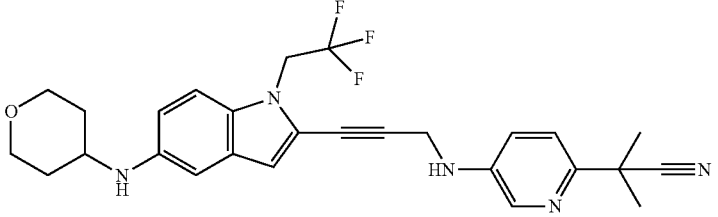 [SMILES: CC(C)(C#N)c1ccc(NCC#Cc2cc3cc(NC4CCOCC4)ccc3n2CC(F)(F)F)cn1]<br>2-methyl-2-{5-[(3-{5-[(oxan-4-yl)amino]-1-(2,2,2-trifluoroethyl)-1H-indol-2-yl}prop-2-yn-1-yl)amino]pyridin-2-yl}propanenitrile |
| 289-P | 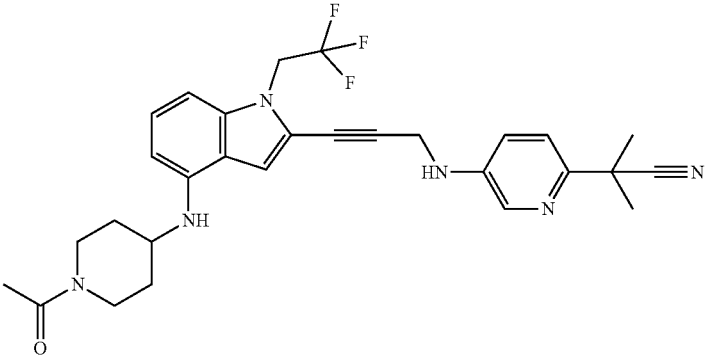 [SMILES: CC(=O)N1CCC(Nc2cccc3c2cc(C#CCNc2ccc(C(C)(C)C#N)nc2)n3CC(F)(F)F)CC1]<br>2-{5-[(3-{4-[(1-acetylpiperidin-4-yl)amino]-1-(2,2,2-trifluoroethyl)-1H-indol-2-yl}prop-2-yn-1-yl)amino]pyridin-2-yl}-2-methylpropanenitrile |
| 290-P | 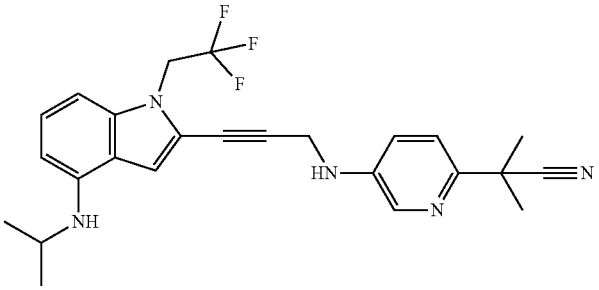 [SMILES: CC(C)Nc1cccc2c1cc(C#CCNc1ccc(C(C)(C)C#N)nc1)n2CC(F)(F)F]<br>2-methyl-2-{5-[(3-{4-[(propan-2-yl)amino]-1-(2,2,2-trifluoroethyl)-1H-indol-2-yl}prop-2-yn-1-yl)amino]pyridin-2-yl}propanenitrile |

TABLE 1-continued

List of compounds

| # | Structure IUPAC name |
|---|---|
| 291-P | 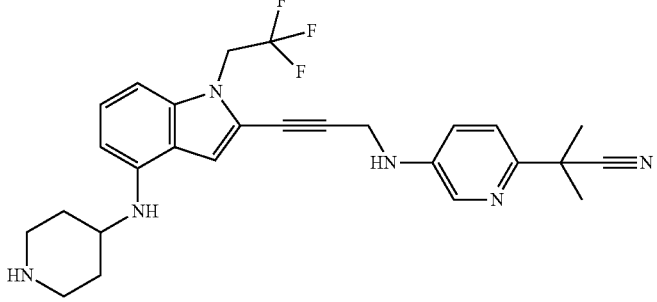
2-methyl-2-{5-[(3-{4-[(piperidin-4-yl)amino]-1-(2,2,2-trifluoroethyl)-1H-indol-2-yl}prop-2-yn-1-yl)amino]pyridin-2-yl}propanenitrile |
| 292-P | 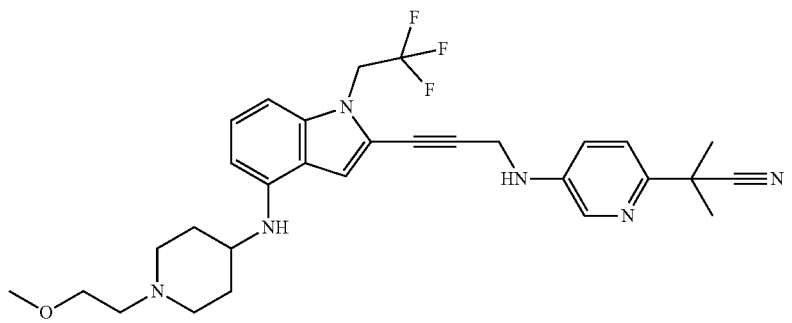 [SMILES: COCCN1CCC(Nc2cccc3c2cc(C#CCNc2ccc(C(C)(C)C#N)nc2)n3CC(F)(F)F)CC1]
2-(5-{[3-(4-{[1-(2-methoxyethyl)-piperidin-4-yl]amino}-1-(2,2,2-trifluoroethyl)-1H-indol-2-yl)prop-2-yn-1-yl]amino}pyridin-2-yl)-2-methylpropanenitrile |
| 293-P | 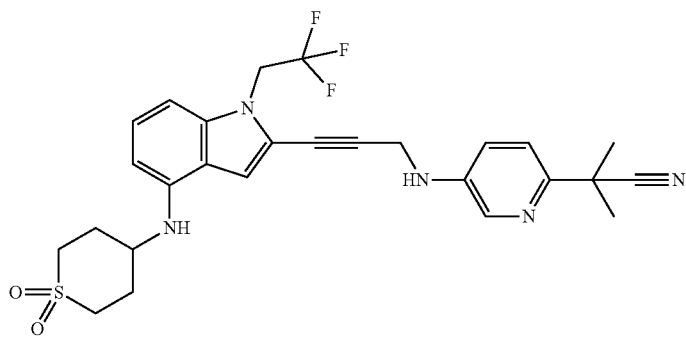
2-{5-[(3-{4-[(1,1-dioxo-1$\lambda^6$-thian-4-yl)amino]-1-(2,2,2-trifluoroethyl)-1H-indol-2-yl}prop-2-yn-1-yl)amino]pyridin-2-yl}-2-methylpropanenitrile |

TABLE 1-continued

List of compounds

| # | Structure IUPAC name |
|---|---|
| 294-P | 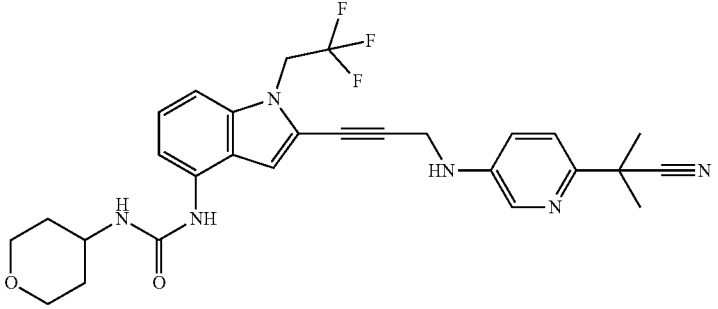 [SMILES: CC(C)(C#N)c1ccc(NCC#Cc2cc3c(NC(=O)NC4CCOCC4)cccc3n2CC(F)(F)F)cn1]<br>3-[2-(3-{[6-(1-cyano-1-methylethyl)-pyridin-3-yl]amino}prop-1-yn-1-yl)-1-(2,2,2-trifluoroethyl)-1H-indol-4-yl]-1-(oxan-4-yl)urea |
| 295-P | 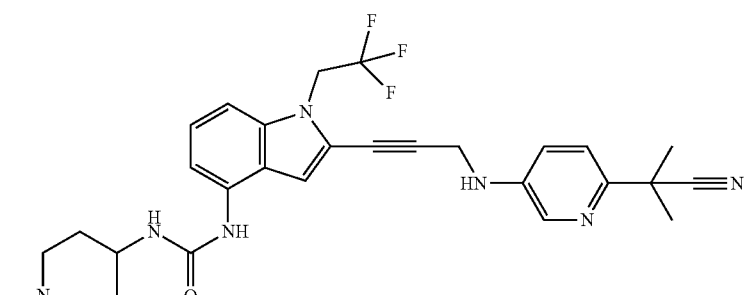<br>3-[2-(3-{[6-(1-cyano-1-methylethyl)-pyridin-3-yl]amino}prop-1-yn-1-yl)-1-(2,2,2-trifluoroethyl)-1H-indol-4-yl]-1-(1-methylpiperidin-4-yl)urea |
| 296-P | 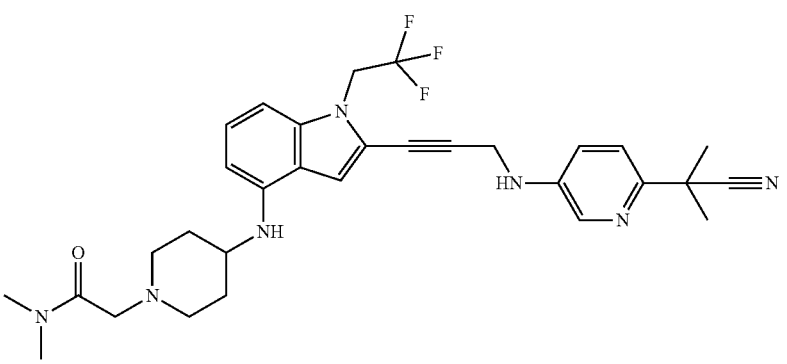 [SMILES: CN(C)C(=O)CN1CCC(Nc2cccc3c2cc(C#CCNc2ccc(C(C)(C)C#N)nc2)n3CC(F)(F)F)CC1]<br>2-(4-{[2-(3-{[6-(1-cyano-1-methylethyl)-pyridin-3-yl]amino}prop-1-yn-1-yl)-1-(2,2,2-trifluoroethyl)-1H-indol-4-yl]amino}piperidin-1-yl)-N,N-dimethylacetamide |

TABLE 1-continued

List of compounds

| # | Structure IUPAC name |
|---|---|
| 297-P | 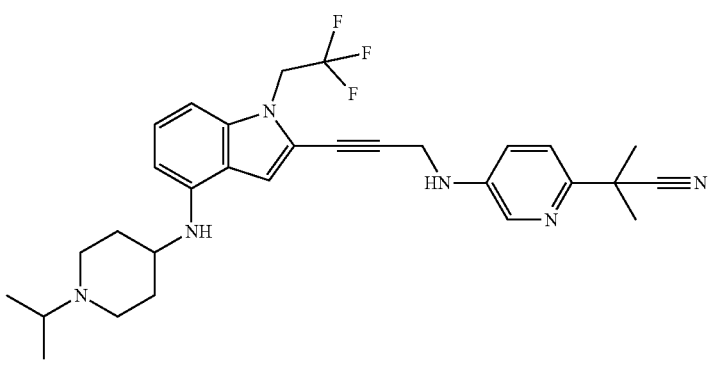 [SMILES: CC(C)N1CCC(Nc2cccc3c2cc(C#CCNc2ccc(C(C)(C)C#N)nc2)n3CC(F)(F)F)CC1]<br>2-methyl-2-(5-{[3-(4-{[1-(propan-2-yl)piperidin-4-yl]amino}-1-(2,2,2-trifluoroethyl)-1H-indol-2-yl)prop-2-yn-1-yl]amino}pyridin-2-yl)propanenitrile |
| 298-P | 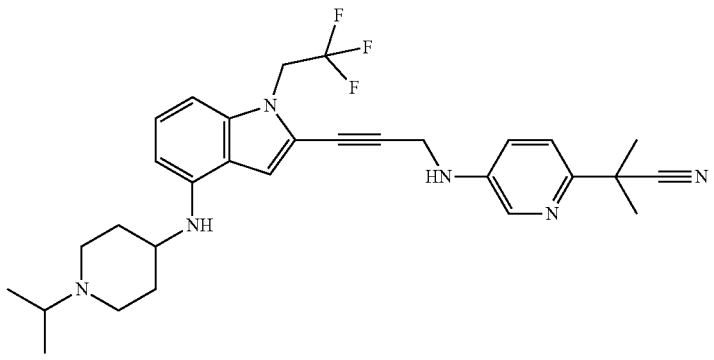 [SMILES: CC(C)N1CCC(Nc2cccc3c2cc(C#CCNc2ccc(C(C)(C)C#N)nc2)n3CC(F)(F)F)CC1]<br>2-methyl-2-(5-{[3-(4-{[1-(1-methylpiperidin-4-yl)piperidin-4-yl]amino}-1-(2,2,2-trifluoroethyl)-1H-indol-2-yl)prop-2-yn-1-yl]amino}pyridin-2-yl)propanenitrile |
| 299-P | 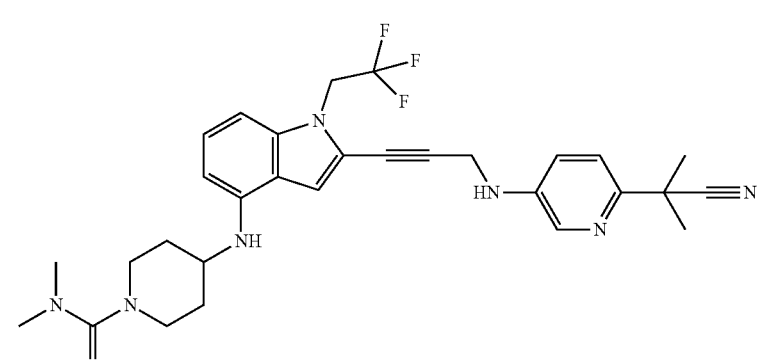<br>4-{[2-(3-{[6-(1-cyano-1-methylethyl)-pyridin-3-yl]amino}prop-1-yn-1-yl)-1-(2,2,2-trifluoroethyl)-1H-indol-4-yl]amino}-N,N-dimethylpiperidine-1-carboxamide |

TABLE 1-continued

List of compounds

| # | Structure IUPAC name |
|---|---|
| 300-P | 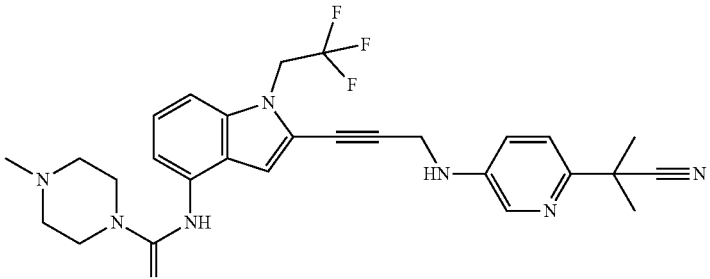<br>N-[2-(3-{[6-(1-cyano-1-methylethyl)-pyridin-3-yl]amino}prop-1-yn-1-yl)-1-(2,2,2-trifluoroethyl)-1H-indol-4-yl]-4-methylpiperazine-1-carboxamide |
| 301-P | 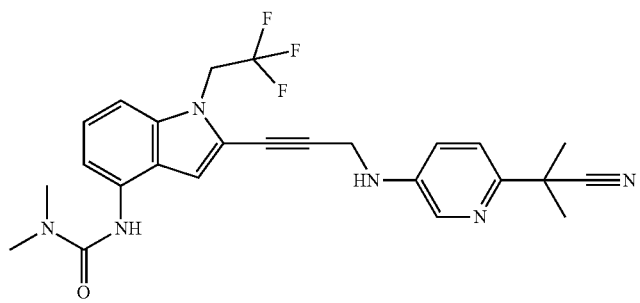 [SMILES: CN(C)C(=O)Nc1cccc2c1cc(C#CCNc1ccc(C(C)(C)C#N)nc1)n2CC(F)(F)F]<br>1-[2-(3-{[6-(1-cyano-1-methylethyl)pyridin-3-yl]amino}prop-1-yn-1-yl)-1-(2,2,2-trifluoroethyl)-1H-indol-4-yl]-3,3-dimethylurea |
| 302-P | 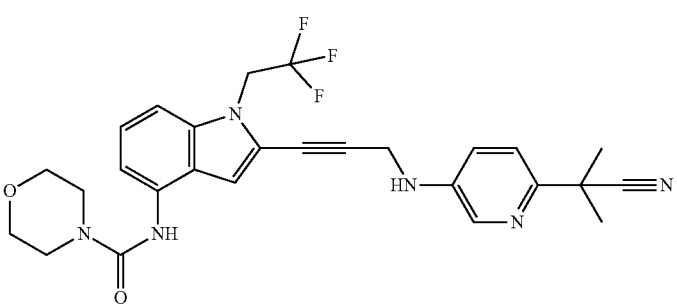 [SMILES: CC(C)(C#N)c1ccc(NCC#Cc2cc3c(NC(=O)N4CCOCC4)cccc3n2CC(F)(F)F)cn1]<br>N-[2-(3-{[6-(1-cyano-1-methylethyl)-pyridin-3-yl]amino}prop-1-yn-1-yl)-1-(2,2,2-trifluoroethyl)-1H-indol-4-yl]morpholine-4-carboxamide |
| 303-P | 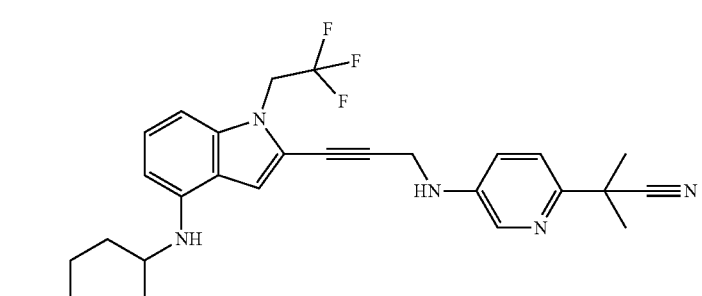<br>2-{5-[(3-{4-[(4-hydroxycyclohexyl)-amino]-1-(2,2,2-trifluoroethyl)-1H-indol-2-yl}prop-2-yn-1-yl)amino]pyridin-2-yl}-2-methylpropanenitrile |

TABLE 1-continued

List of compounds

| # | Structure IUPAC name |
|---|---|
| 304-P | 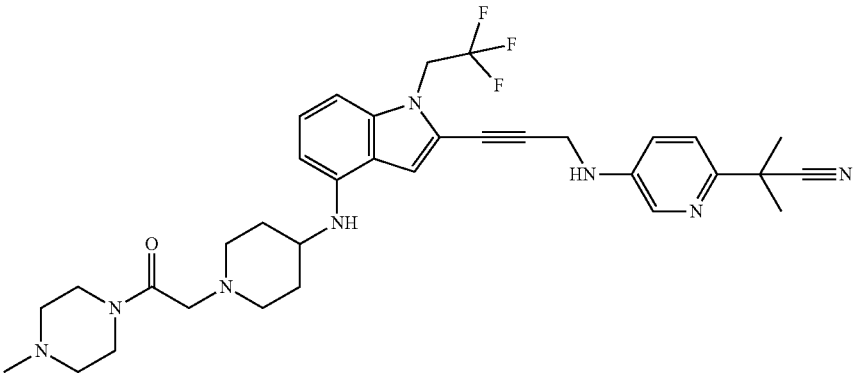 [SMILES: CN1CCN(C(=O)CN2CCC(Nc3cccc4c3cc(C#CCNc3ccc(C(C)(C)C#N)nc3)n4CC(F)(F)F)CC2)CC1]<br>2-methyl-2-[5-({3-[4-({1-[2-(4-methylpiperazin-1-yl)-2-oxoethyl]-piperidin-4-yl}amino)-1-(2,2,2-trifluoroethyl)-1H-indol-2-yl]prop-2-yn-1-yl}amino)pyridin-2-yl]propanenitrile |
| 305-P | 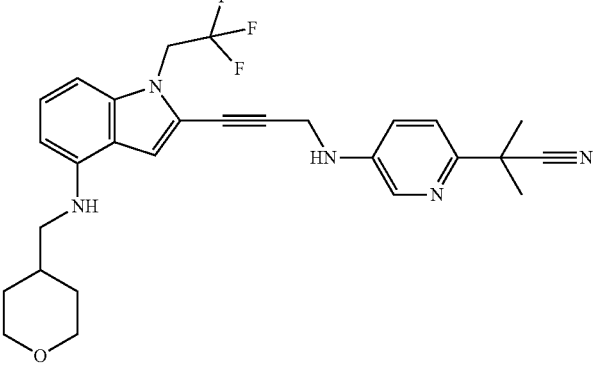<br>2-methyl-2-{5-[(3-{4-[(oxan-4-ylmethyl)amino]-1-(2,2,2-trifluoroethyl)-1H-indol-2-yl}prop-2-yn-1-yl)amino]pyridin-2-yl}propanenitrile |
| 306-P | 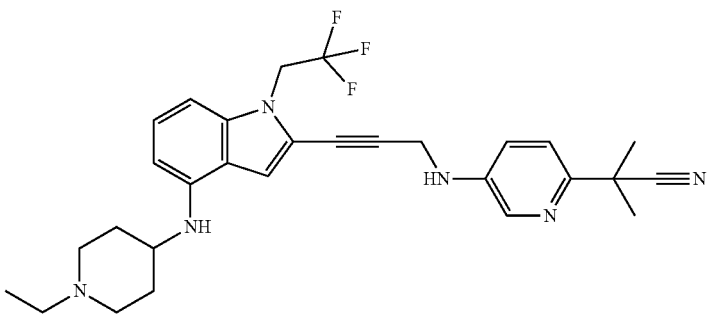 [SMILES: CCN1CCC(Nc2cccc3c2cc(C#CCNc2ccc(C(C)(C)C#N)nc2)n3CC(F)(F)F)CC1]<br>2-{5-[(3-{4-[(1-ethylpiperidin-4-yl)amino]-1-(2,2,2-trifluoroethyl)-1H-indol-2-yl}prop-2-yn-1-yl)amino]pyridin-2-yl}-2-methylpropanenitrile |

TABLE 1-continued

List of compounds

| # | Structure IUPAC name |
|---|---|
| 307-P | 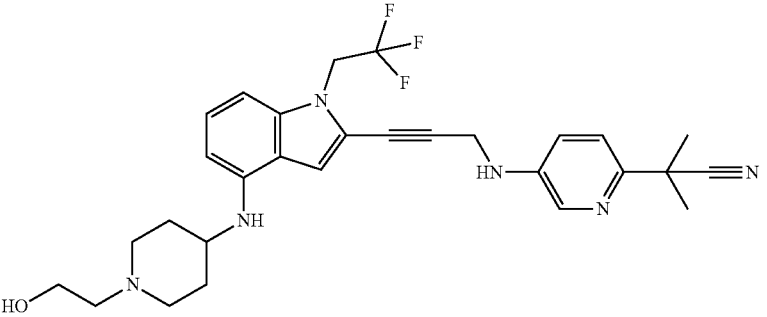 [SMILES: CC(C)(C#N)c1ccc(NCC#Cc2cc3c(NC4CCN(CCO)CC4)cccc3n2CC(F)(F)F)cn1]  2-(5-{[3-(4-{[1-(2-hydroxyethyl)piperidin-4-yl]amino}-1-(2,2,2-trifluoroethyl)-1H-indol-2-yl)prop-2-yn-1-yl]amino}pyridin-2-yl)-2-methylpropanenitrile |
| 308-P | 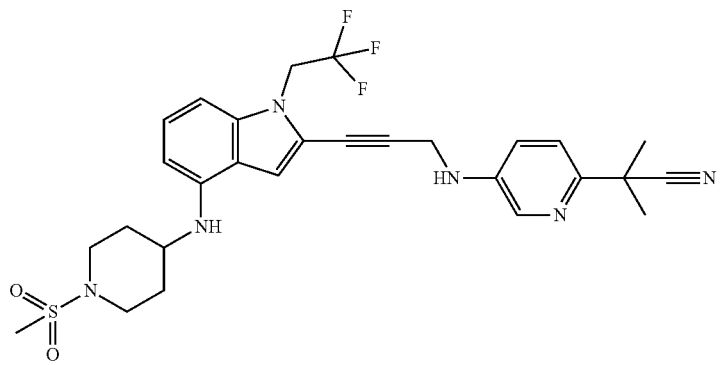 [SMILES: CC(C)(C#N)c1ccc(NCC#Cc2cc3c(NC4CCN(S(C)(=O)=O)CC4)cccc3n2CC(F)(F)F)cn1]  2-{5-(3-{4-[(1-methanesulfonylpiperidin-4-yl)amino]-1-(2,2,2-trifluoroethyl)-1H-indol-2-yl}prop-2-yn-1-yl)amino]pyridin-2-yl}-2-methylpropanenitrile |
| 309-P | 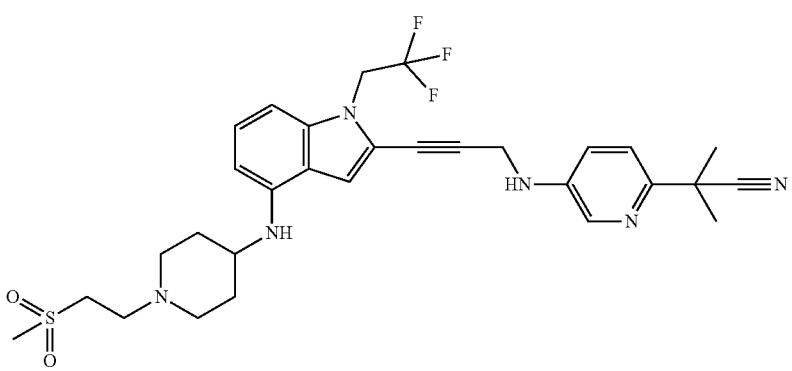 [SMILES: CC(C)(C#N)c1ccc(NCC#Cc2cc3c(NC4CCN(CCS(C)(=O)=O)CC4)cccc3n2CC(F)(F)F)cn1]  2-(5-{[3-(4-{[1-(2-methanesulfonyl-ethyl)piperidin-4-yl]amino}-1-(2,2,2-trifluoroethyl)-1H-indol-2-yl)prop-2-yn-1-yl]amino}pyridin-2-yl)-2-methylpropanenitrile |

TABLE 1-continued

List of compounds

| # | Structure IUPAC name |
|---|---|
| 310-P | 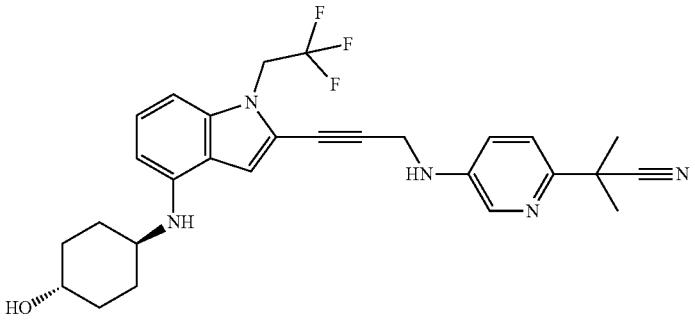 [SMILES: CC(C)(C#N)c1ccc(NCC#Cc2cc3c(N[C@H]4CC[C@H](O)CC4)cccc3n2CC(F)(F)F)cn1] 2-methyl-2-(5-{[3-(4-{[(1R,4R)-4-hydroxycyclohexyl]amino}-1-(2,2,2-trifluoroethyl)-1H-indol-2-yl)prop-2-yn-1-yl]amino}pyridin-2-yl)propanenitrile |
| 311-P | 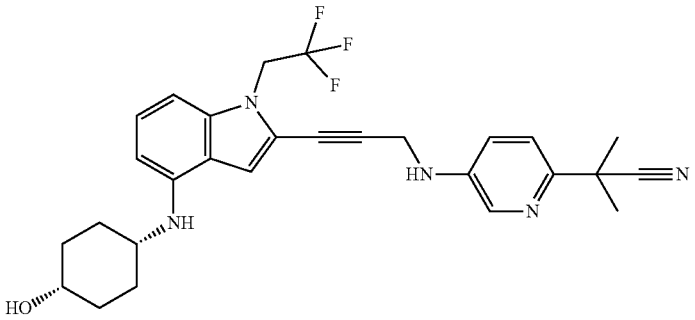 2-methyl-2-(5-{[3-(4-{[(1S,4S)-4-hydroxycyclohexyl]amino}-1-(2,2,2-trifluoroethyl)-1H-indol-2-yl)prop-2-yn-1-yl]amino}pyridin-2-yl)propanenitrile |
| 312-P | 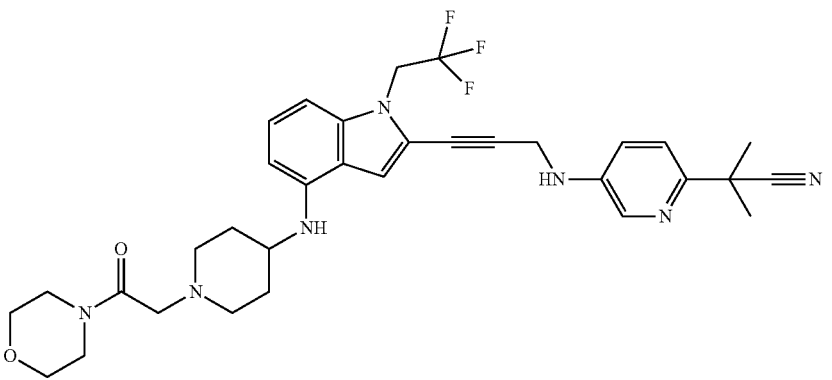 [SMILES: CC(C)(C#N)c1ccc(NCC#Cc2cc3c(NC4CCN(CC(=O)N5CCOCC5)CC4)cccc3n2CC(F)(F)F)cn1] 2-methyl-2-[5-({3-[4-({1-[2-(morpholin-4-yl)-2-oxoethyl]piperidin-4-yl}amino)-1-(2,2,2-trifluoroethyl)-1H-indol-2-yl]prop-2-yn-1-yl}amino)pyridin-2-yl]propanenitrile |

TABLE 1-continued

List of compounds

| # | Structure IUPAC name |
|---|---|

313-P

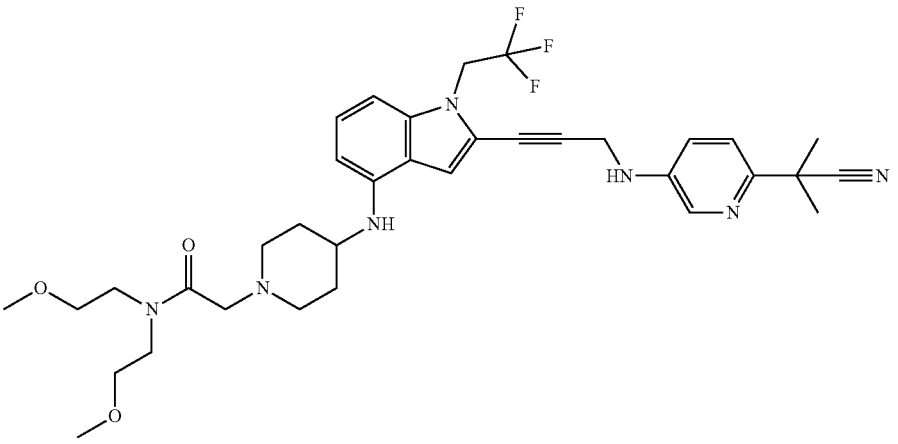 [SMILES: COCCN(CCOC)C(=O)CN1CCC(Nc2cccc3c2cc(C#CCNc2ccc(C(C)(C)C#N)nc2)n3CC(F)(F)F)CC1]

2-(4-{[2-(3-{[6-(1-cyano-1-
methylethyl)pyridin-3-yl]amino}prop-1-yn-
1-yl)-1-(2,2,2-trifluoroethyl)-1H-indol-4-
yl]amino}piperidin-1-yl)-N,N-bis(2-
methoxyethyl)acetamide

314-P

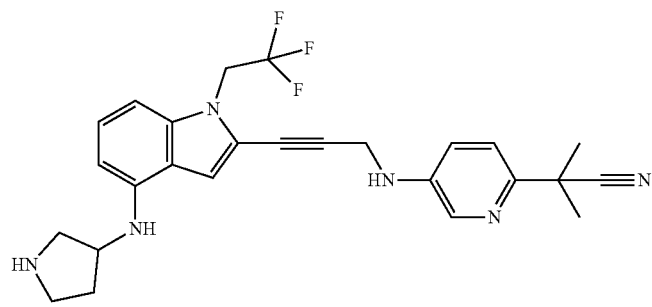 [SMILES: CC(C)(C#N)c1ccc(NCC#Cc2cc3c(NC4CCNC4)cccc3n2CC(F)(F)F)cn1]

2-methyl-2-{5-[(3-{4-[(pyrrolidin-3-
yl)amino]-1-(2,2,2-trifluoroethyl)-1H-indol-
2-yl}prop-2-yn-1-yl)amino]pyridin-2-yl}propanenitrile

315-P

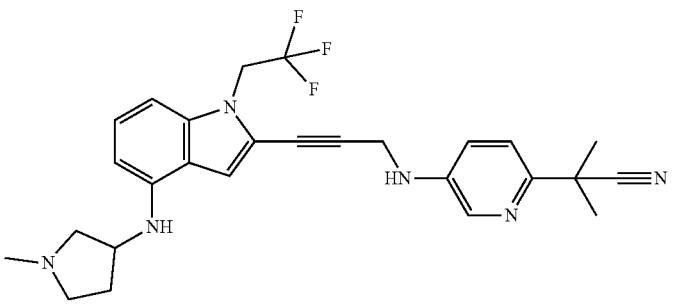 [SMILES: CN1CCC(Nc2cccc3c2cc(C#CCNc2ccc(C(C)(C)C#N)nc2)n3CC(F)(F)F)C1]

2-methyl-2-{5-[(3-{4-[(1-methylpyrrolidin-3-
yl)amino]-1-(2,2,2-trifluoroethyl)-1H-indol-
2-yl}prop-2-yn-1-yl)amino]pyridin-2-yl}propanenitrile TABLE 1-continued List of compounds

| # | Structure IUPAC name |
|---|---|
| 316-P | 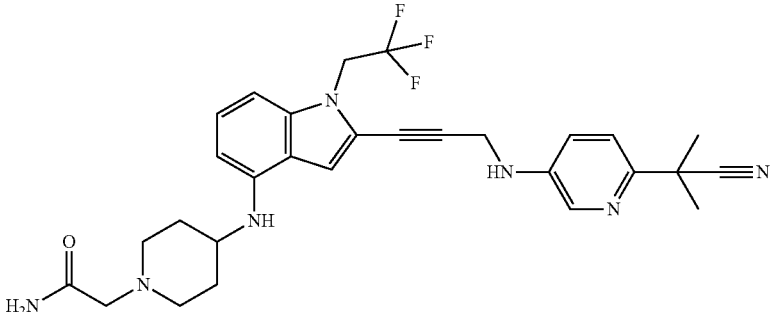<br>2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)acetamide |
| 317-P | 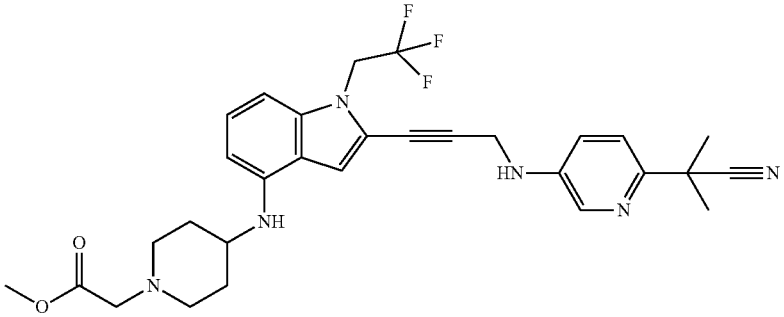 [SMILES: COC(=O)CN1CCC(Nc2cccc3c2cc(C#CCNc2ccc(C(C)(C)C#N)nc2)n3CC(F)(F)F)CC1]<br>methyl 2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)acetate |
| 318-P | 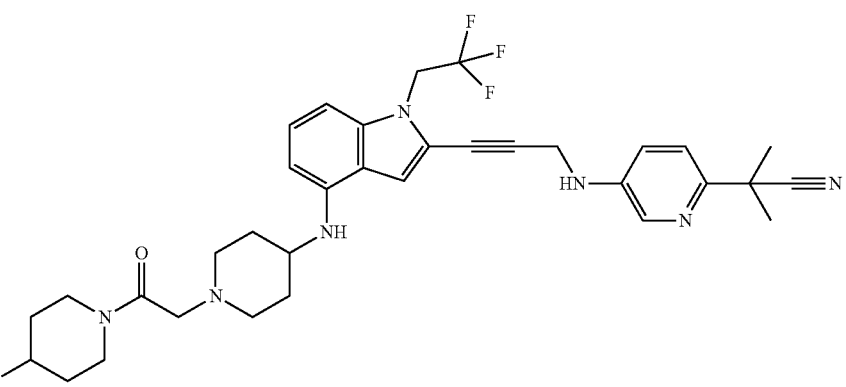<br>2-[5-({3-[4-({1-[2-(4-hydroxypiperidin-1-yl)-2-oxoethyl]piperidin-4-yl}amino)-1-(2,2,2-trifluoroethyl)-1H-indol-2-yl]prop-2-yn-1-yl}amino)pyridin-2-yl]-2-methylpropanenitrile |

TABLE 1-continued

List of compounds

| # | Structure IUPAC name |
|---|---|
| 319-P | 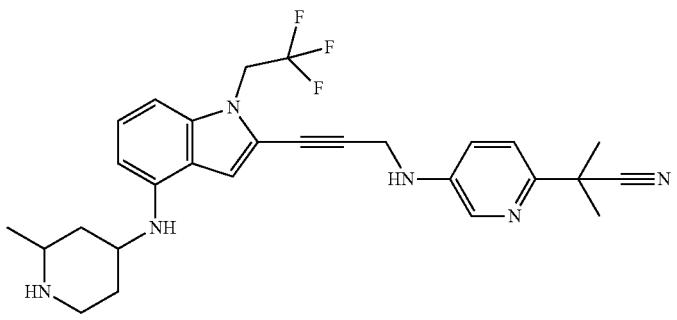 [SMILES: CC1CC(Nc2cccc3c2cc(C#CCNc2ccc(C(C)(C)C#N)nc2)n3CC(F)(F)F)CCN1]<br>2-methyl-2-{5-[(3-{4-[(2-methylpiperidin-4-yl)amino]-1-(2,2,2-trifluoroethyl)-1H-indol-2-yl}prop-2-yn-1-yl)amino]pyridin-2-yl}propanenitrile |
| 320-P | 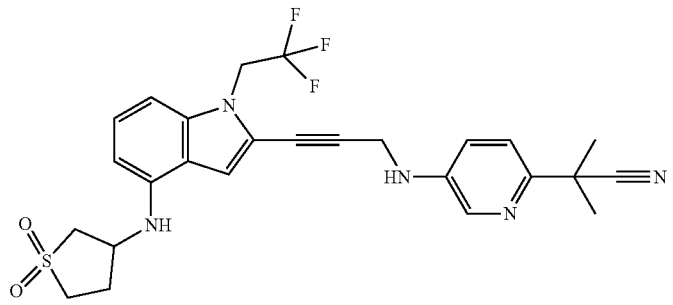 [SMILES: CC(C)(C#N)c1ccc(NCC#Cc2cc3c(NC4CCS(=O)(=O)C4)cccc3n2CC(F)(F)F)cn1]<br>2-{5-[(3-{4-[(1,1-dioxo-1λ⁶-thiolan-3-yl)amino]-1-(2,2,2-trifluoroethyl)-1H-indol-2-yl}prop-2-yn-1-yl)amino]pyridin-2-yl}-2-methylpropanenitrile |
| 321-P | 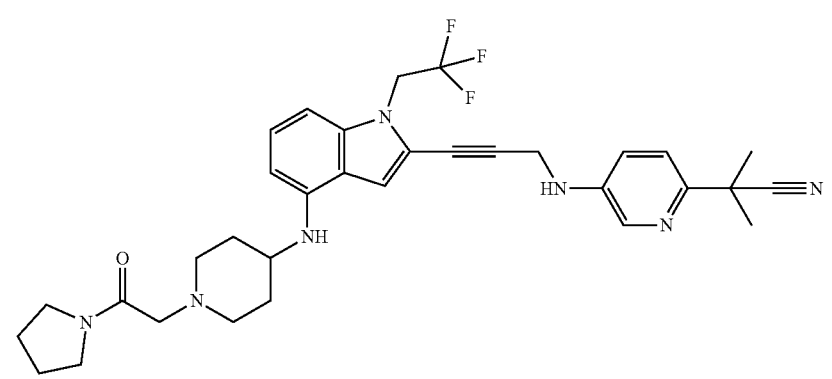 [SMILES: CC(C)(C#N)c1ccc(NCC#Cc2cc3c(NC4CCN(CC(=O)N5CCCC5)CC4)cccc3n2CC(F)(F)F)cn1]<br>2-methyl-2-[5-({3-[4-({1-[2-oxo-2-(pyrrolidin-1-yl)ethyl]piperidin-4-yl}amino)-1-(2,2,2-trifluoroethyl)-1H-indol-2-yl]prop-2-yn-1-yl}amino)pyridin-2-yl]propanenitrile |

TABLE 1-continued

List of compounds

| # | Structure IUPAC name |
|---|---|
| 322-P | 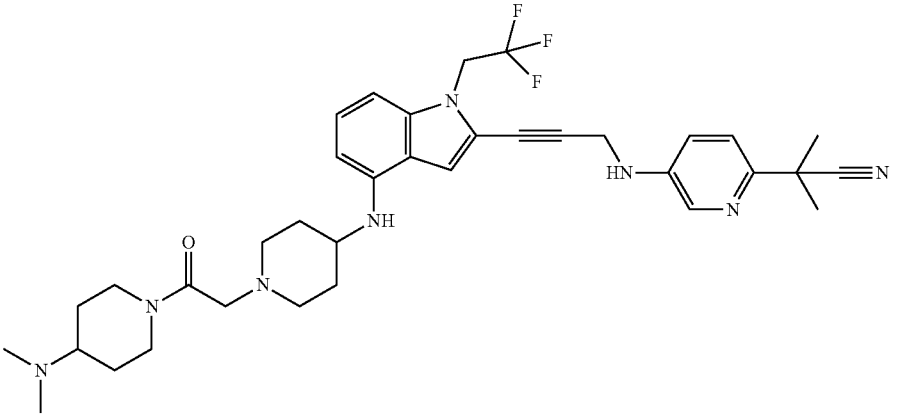 [SMILES: CN(C)C1CCN(C(=O)CN2CCC(Nc3cccc4c3cc(C#CCNc3ccc(C(C)(C)C#N)nc3)n4CC(F)(F)F)CC2)CC1]<br>2-{5-[(3-{4-[(1-{2-[4-(dimethylamino)piperidin-1-yl]-2-oxoethyl}piperidin-4-yl)amino]-1-(2,2,2-trifluoroethyl)-1H-indol-2-yl}prop-2-yn-1-yl)amino]pyridin-2-yl}-2-methylpropanenitrile |
| 323-P | 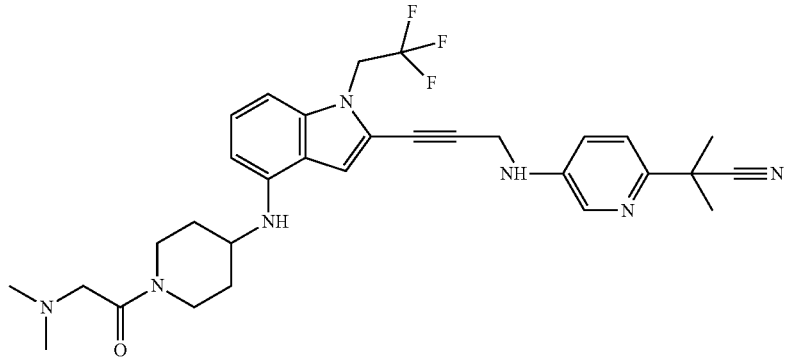 [SMILES: CN(C)CC(=O)N1CCC(Nc2cccc3c2cc(C#CCNc2ccc(C(C)(C)C#N)nc2)n3CC(F)(F)F)CC1]<br>2-[5-({3-[4-({1-[2-(dimethylamino)acetyl]piperidin-4-yl}amino)-1-(2,2,2-trifluoroethyl)-1H-indol-2-yl]prop-2-yn-1-yl}amino)pyridin-2-yl]-2-methylpropanenitrile |
| 324-P | 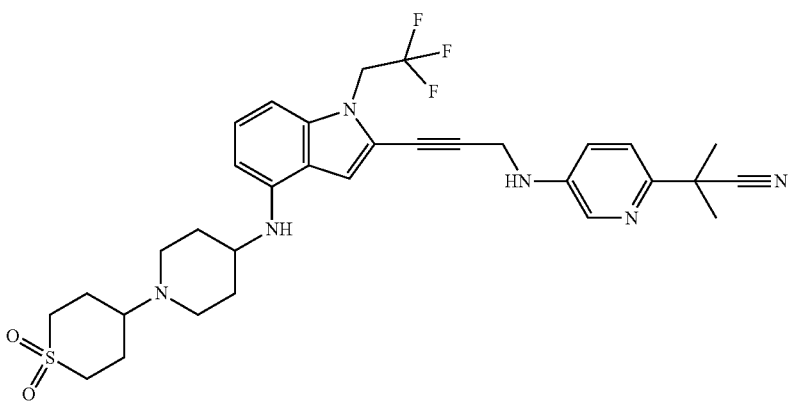 [SMILES: CC(C)(C#N)c1ccc(NCC#Cc2cc3c(NC4CCN(C5CCS(=O)(=O)CC5)CC4)cccc3n2CC(F)(F)F)cn1]<br>2-(5-{[3-(4-{[1-(1,1-dioxo-1λ⁶-thian-4-yl)piperidin-4-yl]amino}-1-(2,2,2-trifluoroethyl)-1H-indol-2-yl)prop-2-yn-1-yl]amino}pyridin-2-yl)-2-methylpropanenitrile |

TABLE 1-continued

List of compounds

| # | Structure IUPAC name |
|---|---|
| 325-P | 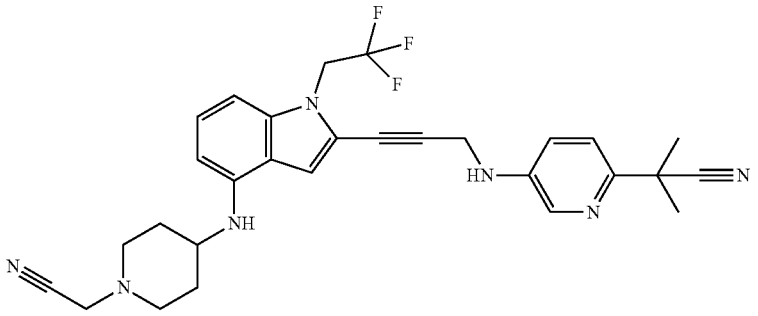 [SMILES: CC(C)(C#N)c1ccc(NCC#Cc2cc3c(NC4CCN(CC#N)CC4)cccc3n2CC(F)(F)F)cn1]

2-(5-{[3-(4-{[1-(cyanomethyl)piperidin-4-yl]amino}-1-(2,2,2-trifluoroethyl)-1H-indol-2-yl)prop-2-yn-1-yl]amino}pyridin-2-yl)-2-methylpropanenitrile |
| 326-P | 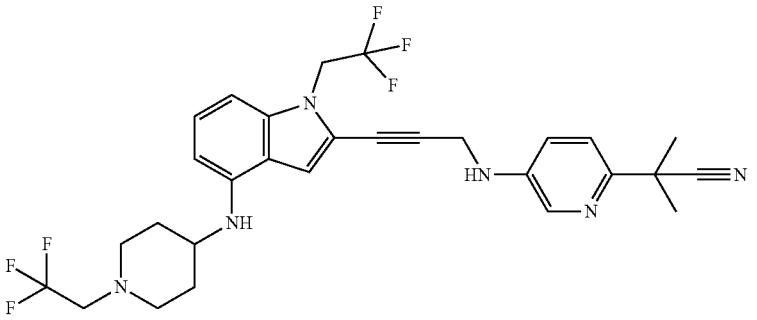 [SMILES: CC(C)(C#N)c1ccc(NCC#Cc2cc3c(NC4CCN(CC(F)(F)F)CC4)cccc3n2CC(F)(F)F)cn1]

2-methyl-2-[5-({3-[1-(2,2,2-trifluoroethyl)-4-{[1-(2,2,2-trifluoroethyl)piperidin-4-yl]amino}-1H-indol-2-yl]prop-2-yn-1-yl}amino)pyridin-2-yl]propanenitrile |
| 327-P | 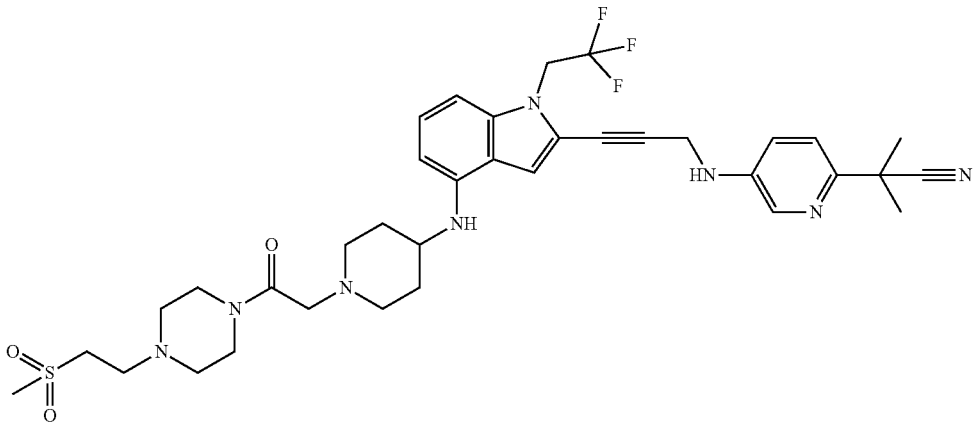 [SMILES: CC(C)(C#N)c1ccc(NCC#Cc2cc3c(NC4CCN(CC(=O)N5CCN(CCS(C)(=O)=O)CC5)CC4)cccc3n2CC(F)(F)F)cn1]

2-{5-[(3-{4-[(1-{2-[4-(2-methanesulfonylethyl)piperazin-1-yl]-2-oxoethyl}piperidin-4-yl)amino]-1-(2,2,2-trifluoroethyl)-1H-indol-2-yl}prop-2-yn-1-yl)amino]pyridin-2-yl}-2-methylpropanenitrile |

TABLE 1-continued

List of compounds

| # | Structure IUPAC name |
|---|---|
| 328-P | 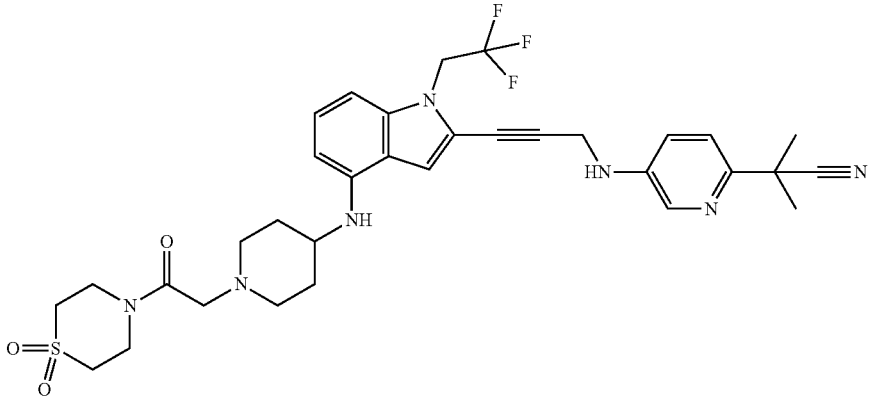 [SMILES: CC(C)(C#N)c1ccc(NCC#Cc2cc3c(NC4CCN(CC(=O)N5CCS(=O)(=O)CC5)CC4)cccc3n2CC(F)(F)F)cn1]<br>2-[5-({3-[4-({1-[2-(1,1-dioxo-1λ⁶,4-thiomorpholin-4-yl)-2-oxoethyl]piperidin-4-yl}amino)-1-(2,2,2-trifluoroethyl)-1H-indol-2-yl]prop-2-yn-1-yl}amino)pyridin-2-yl]-2-methylpropanenitrile |
| 329-P | 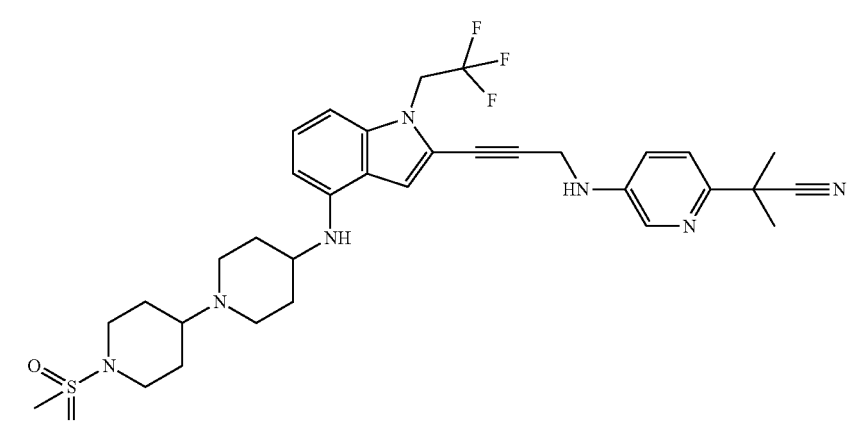<br>2-(5-{[3-(4-{[1-(1-methanesulfonylpiperazin-4-yl)piperidin-4-yl]amino}-1-(2,2,2-trifluoroethyl)-1H-indol-2-yl)prop-2-yn-1-yl]amino}pyridin-2-yl)-2-methylpropanenitrile |
| 330-P | 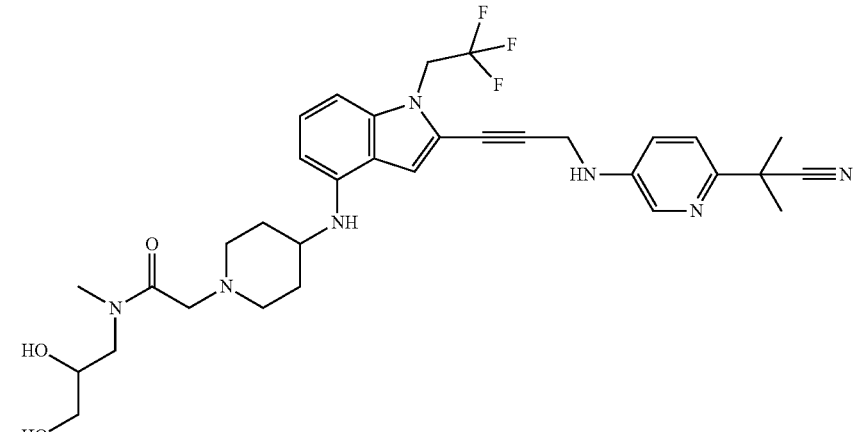<br>2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)-N-(2,3-dihydroxypropyl)-N-methylacetamide |

TABLE 1-continued
List of compounds
| # | Structure IUPAC name |
|---|---|
331-P
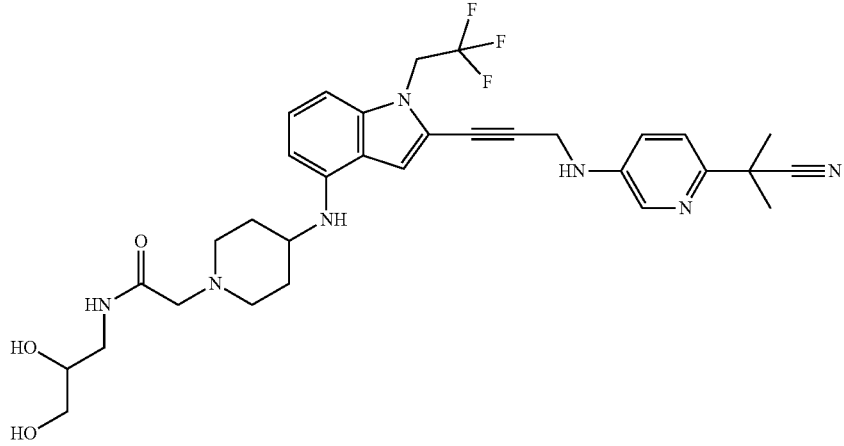 [SMILES: CC(C)(C#N)c1ccc(NCC#Cc2cc3c(NC4CCN(CC(=O)NCC(O)CO)CC4)cccc3n2CC(F)(F)F)cn1]
2-(4-{[2-(3-{[6-(1-cyano-1-
methylethyl)pyridin-3-yl]amino}prop-1-yn-
1-yl)-1-(2,2,2-trifluoroethyl)-1H-indol-4-
yl]amino}piperidin-1-yl)-N-(2,3-
dihydroxypropyl)acetamide
332-P
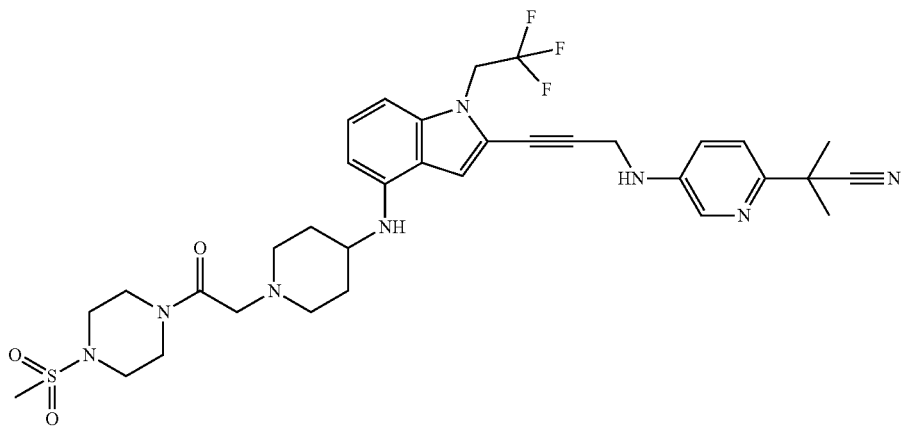 [SMILES: CC(C)(C#N)c1ccc(NCC#Cc2cc3c(NC4CCN(CC(=O)N5CCN(S(C)(=O)=O)CC5)CC4)cccc3n2CC(F)(F)F)cn1]
2-[5-({3-[4-({1-[2-(4-
methanesulfonylpiperidin-1-yl)-2-
oxoethyl]piperidin-4-yl}amino]-1-(2,2,2-
trifluoroethyl)-1H-indol-2-yl]prop-2-yn-1-
yl}amino)pyridin-2-yl]-2-
methylpropanenitrile

| # | Structure | IUPAC name |
|---|---|---|
| 333-P | 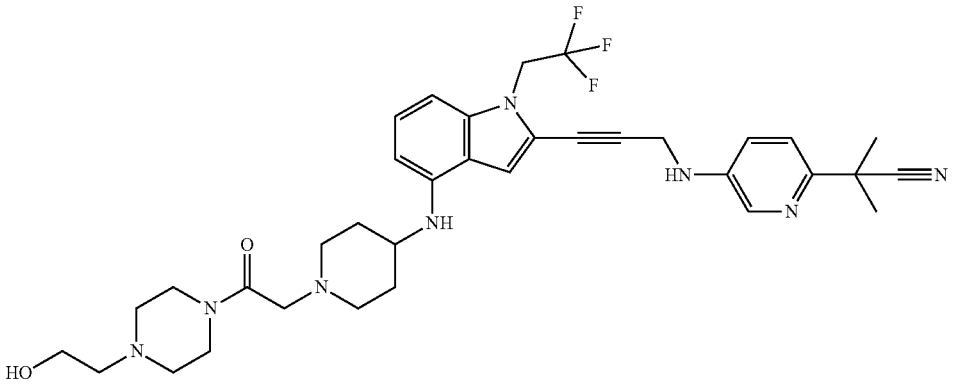 [SMILES: CC(C)(C#N)c1ccc(NCC#Cc2cc3c(NC4CCN(CC(=O)N5CCN(CCO)CC5)CC4)cccc3n2CC(F)(F)F)cn1] | 2-{5-[(3-{4-[(1-{2-[4-(2-hydroxyethyl)piperazin-1-yl]-2-oxoethyl}piperidin-4-yl)amino]-1-(2,2,2-trifluoroethyl)-1H-indol-2-yl}prop-2-yn-1-yl)amino]pyridin-2-yl}-2-methylpropanenitrile |
| 334-P | 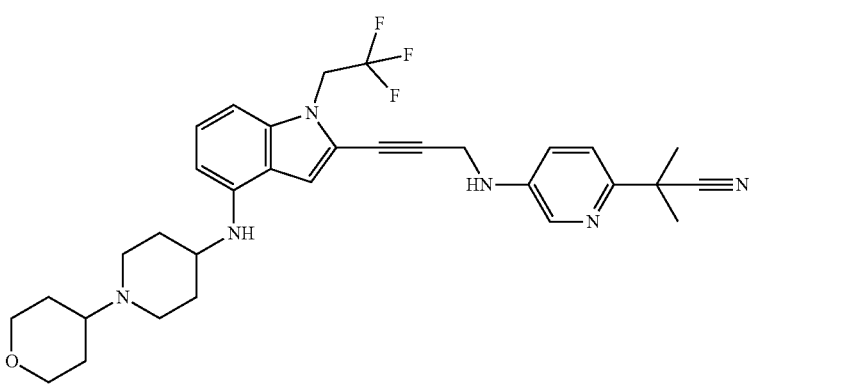 [SMILES: CC(C)(C#N)c1ccc(NCC#Cc2cc3c(NC4CCN(C5CCOCC5)CC4)cccc3n2CC(F)(F)F)cn1] | 2-methyl-2-(5-{[3-(4-{[1-(oxan-4-yl)piperidin-4-yl]amino}-1-(2,2,2-trifluoroethyl)-1H-indol-2-yl)prop-2-yn-1-yl]amino}pyridin-2-yl)propanenitrile |
| 335-P | 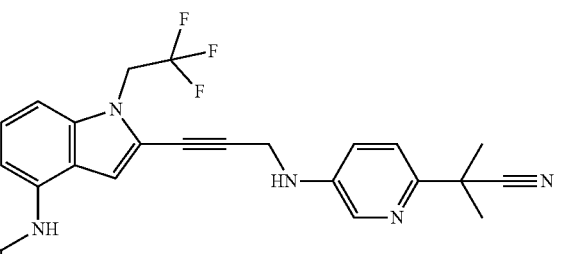 | 2-[5-({3-[4-({1-[1-(2-methanesulfonylethyl)piperidine-4-yl]piperidin-4-yl}amino)-1-(2,2,2-trifluoroethyl)-1H-indol-2-yl]prop-2-yn-1-yl}amino)pyridin-2-yl]-2-methylpropanenitrile |

TABLE 1-continued

List of compounds

| # | Structure IUPAC name |
|---|---|
| 336-P | 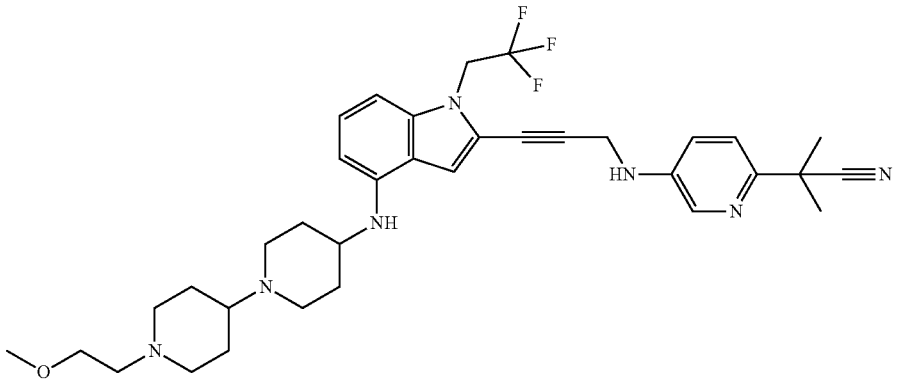 [SMILES: COCCN1CCC(N2CCC(Nc3cccc4c3cc(C#CCNc3ccc(C(C)(C)C#N)nc3)n4CC(F)(F)F)CC2)CC1]<br>2-[5-({3-[4-({1-[1-(2-methoxyethyl)piperidin-4-yl]piperidin-4-yl}amino)-1-(2,2,2-trifluoroethyl)-1H-indol-2-yl]prop-2-yn-1-yl}amino)pyridin-2-yl]-2-methylpropanenitrile |
| 337-P | 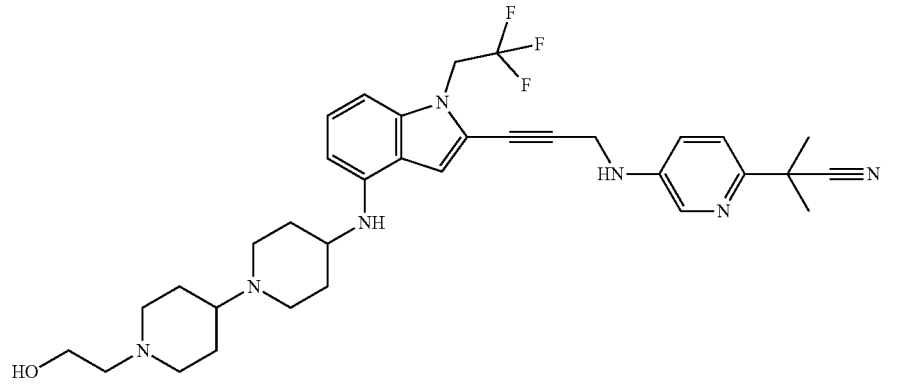 [SMILES: CC(C)(C#N)c1ccc(NCC#Cc2cc3c(NC4CCN(C5CCN(CCO)CC5)CC4)cccc3n2CC(F)(F)F)cn1]<br>2-[5-({3-[4-({1-[1-(2-hydroxyethyl)piperidin-4-yl]piperidin-4-yl}amino)-1-(2,2,2-trifluoroethyl)-1H-indol-2-yl]prop-2-yn-1-yl}amino)pyridin-2-yl]-2-methylpropanenitrile |
| 338-P | 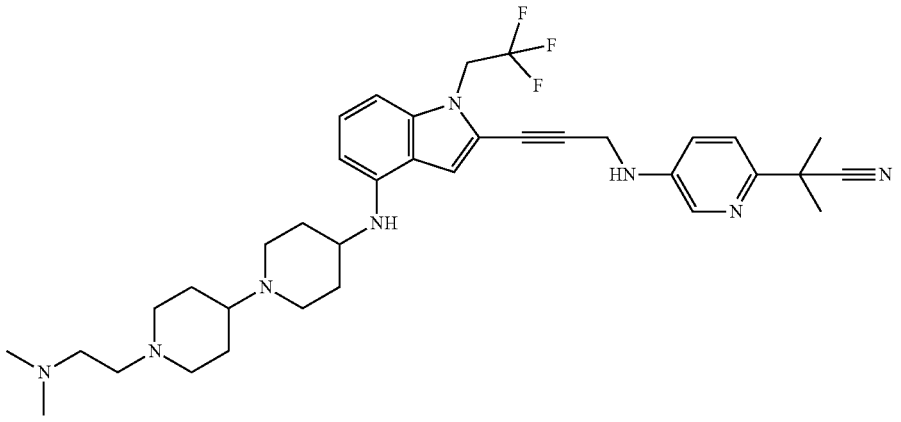 [SMILES: CN(C)CCN1CCC(N2CCC(Nc3cccc4c3cc(C#CCNc3ccc(C(C)(C)C#N)nc3)n4CC(F)(F)F)CC2)CC1]<br>2-[5-({3-[4-({1-[2-(dimethylamino)ethyl]piperidin-4-yl}amino)-1-(2,2,2-trifluoroethyl)-1H-indol-2-yl]prop-2-yn-1-yl}amino)pyridin-2-yl]-2-methylpropanenitrile |

TABLE 1-continued

List of compounds

| # | Structure IUPAC name |
|---|---|
| 339-P | 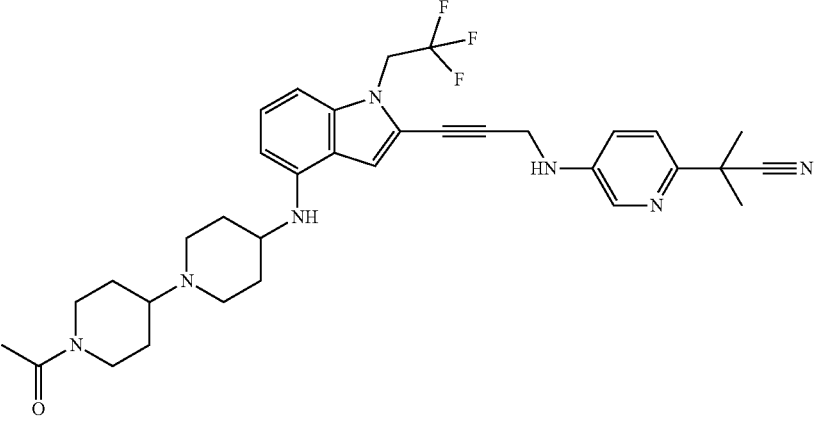 [SMILES: CC(=O)N1CCC(N2CCC(Nc3cccc4c3cc(C#CCNc3ccc(C(C)(C)C#N)nc3)n4CC(F)(F)F)CC2)CC1]<br>2-(5-{[3-(4-{[1-(1-acetylpiperidin-4-yl)piperidin-4-yl]amino}-1-(2,2,2-trifluoroethyl)-1H-indol-2-yl)prop-2-yn-1-yl]amino}pyridin-2-yl)-2-methylpropanenitrile |
| 340-P | 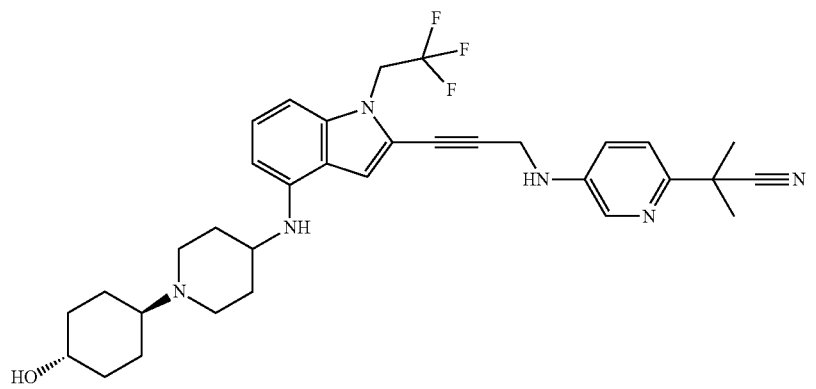 [SMILES: CC(C)(C#N)c1ccc(NCC#Cc2cc3c(NC4CCN([C@H]5CC[C@H](O)CC5)CC4)cccc3n2CC(F)(F)F)cn1]<br>2-methyl-2-[5-({3-[4-({1-[(1R,4R)-4-hydroxycyclohexyl]piperidin-4-yl}amino)-1-(2,2,2-trifluoroethyl)-1H-indol-2-yl]prop-2-yn-1-yl}amino)pyridin-2-yl]propanenitrile |
| 341-P | 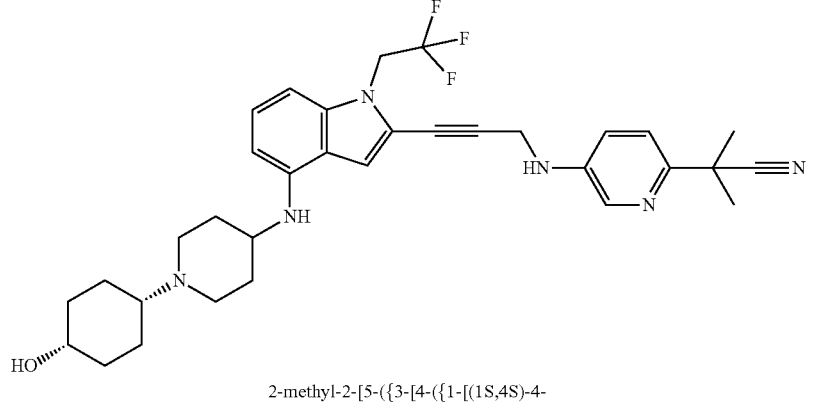<br>2-methyl-2-[5-({3-[4-({1-[(1S,4S)-4-hydroxycyclohexyl]piperidin-4-yl}amino)-1-(2,2,2-trifluoroethyl)-1H-indol-2-yl]prop-2-yn-1-yl}amino)pyridin-2-yl]propanenitrile |

TABLE 1-continued

List of compounds

| # | Structure IUPAC name |
|---|---|
| 342-P | 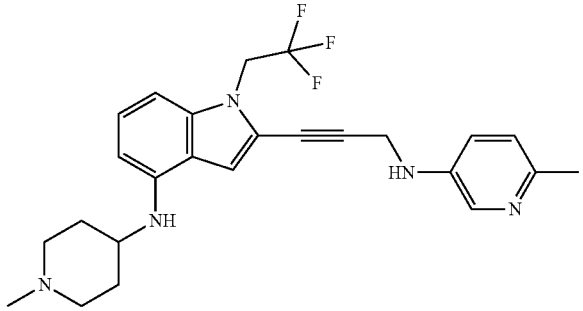<br>N-(1-methylpiperidin-4-yl)-2-{3-[(6-methylpyridin-3-yl)amino]prop-1-yn-1-yl}-1-(2,2,2-trifluoroethyl)-1H-indol-4-amine |
| 343-P | 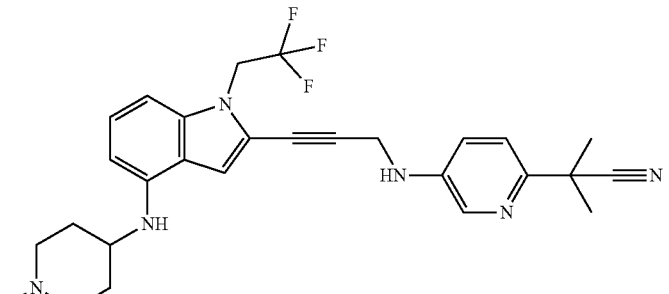<br>2-methyl-2-{5-[(3-{4-[(1-methylpiperidin-4-yl)amino]-1-(2,2,2-trifluoroethyl)-1H-indol-2-yl}prop-2-yn-1-yl)amino]pyridin-2-yl}propanenitrile |
| 344-P | 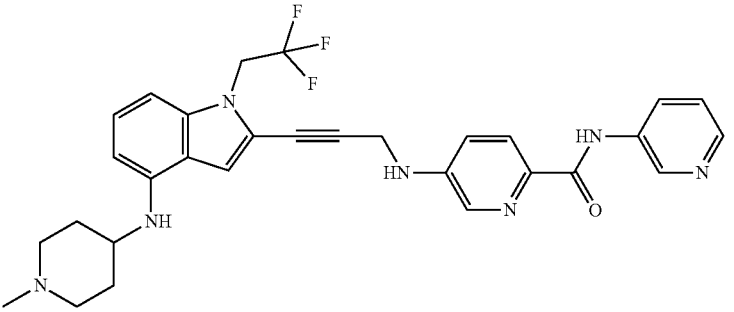 [SMILES: CN1CCC(Nc2cccc3c2cc(C#CCNc2ccc(C(=O)Nc4cccnc4)nc2)n3CC(F)(F)F)CC1]<br>5-[(3-{4-[(1-methylpiperidin-4-yl)amino]-1-(2,2,2-trifluoroethyl)-1H-indol-2-yl}prop-2-yn-1-yl)amino]-N-(pyridin-3-yl)pyridine-2-carboxamide |
| 345-P | 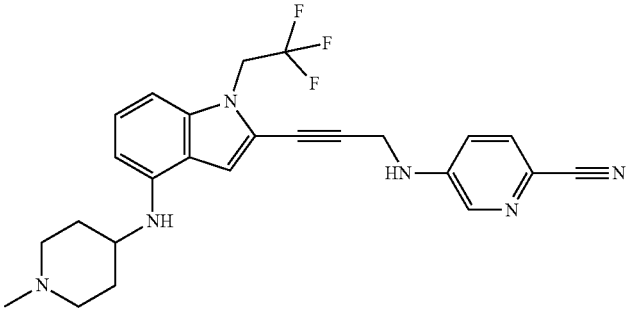 [SMILES: CN1CCC(Nc2cccc3c2cc(C#CCNc2ccc(C#N)nc2)n3CC(F)(F)F)CC1]<br>5-[(3-{4-[(1-methylpiperidin-4-yl)amino]-1-(2,2,2-trifluoroethyl)-1H-indol-2-yl}prop-2-yn-1-yl)amino]pyridine-2-carbonitrile |

TABLE 1-continued

List of compounds

| # | Structure IUPAC name |
|---|---|
| 346-P | 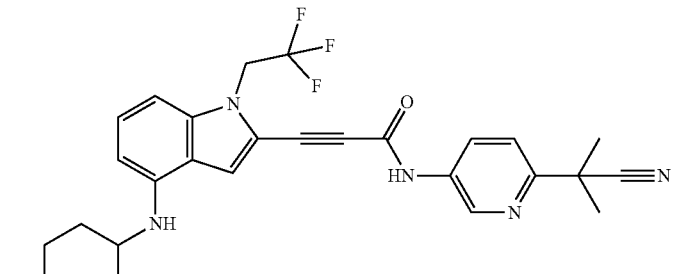<br>N-[6-(1-cyano-1-methylethyl)pyridin-3-yl]-<br>3-{4-[(1-methylpiperidin-4-yl)amino]-1-<br>(2,2,2-trifluoroethyl)-1H-indol-2-yl}prop-2-ynamide |
| 347-P | 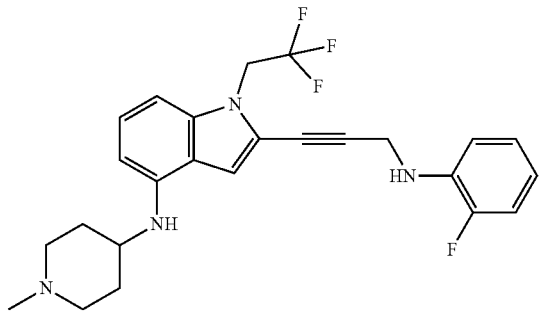<br>2-{3-[(2-fluorophenyl)amino]prop-1-yn-1-<br>yl}-N-(1-methylpiperidin-4-yl)-1-(2,2,2-<br>trifluoroethyl)-1H-indol-4-amine |
| 348-P | 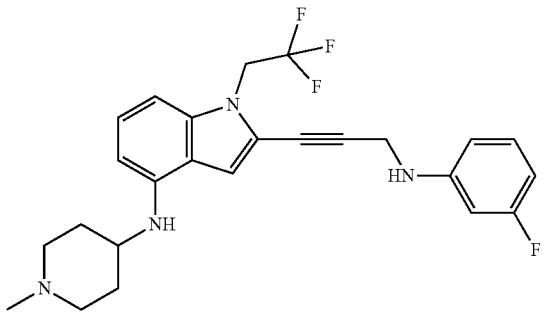 [SMILES: CN1CCC(Nc2cccc3c2cc(C#CCNc2cccc(F)c2)n3CC(F)(F)F)CC1]<br>2-{3-[(3-fluorophenyl)amino]prop-1-yn-1-<br>yl}-N-(1-methylpiperidin-4-yl)-1-(2,2,2-<br>trifluoroethyl)-1H-indol-4-amine |
| 349-P | 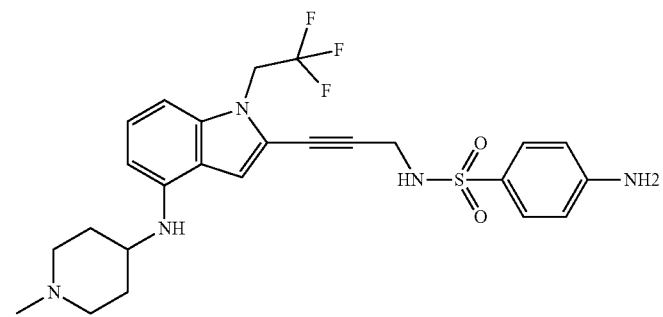 [SMILES: CN1CCC(Nc2cccc3c2cc(C#CCNS(=O)(=O)c2ccc(N)cc2)n3CC(F)(F)F)CC1]<br>4-amino-N-(3-{4-[(1-methylpiperidin-4-<br>yl)amino]-1-(2,2,2-trifluoroethyl)-1H-indol-<br>2-yl}prop-2-yn-1-yl)benzene-1-sulfonamide |

TABLE 1-continued

List of compounds

| # | Structure IUPAC name |
|---|---|
| 350-P | 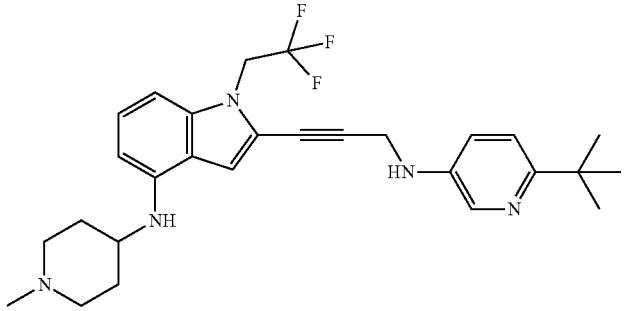 [SMILES: CN1CCC(Nc2cccc3c2cc(C#CCNc2ccc(C(C)(C)C)nc2)n3CC(F)(F)F)CC1]
2-{3-[(6-tert-butylpyridin-3-yl)amino]prop-1-yn-1-yl}-N-(1-methylpiperidin-4-yl)-1-(2,2,2-trifluoroethyl)-1H-indol-4-amine |
| 351-P | 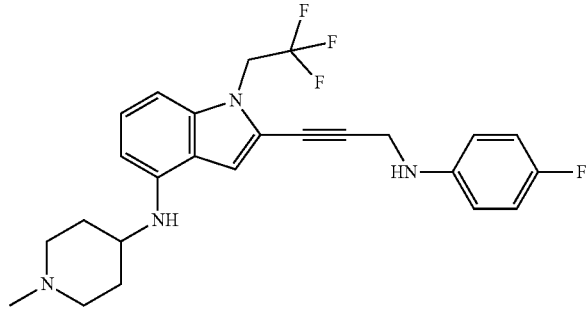 [SMILES: CN1CCC(Nc2cccc3c2cc(C#CCNc2ccc(F)cc2)n3CC(F)(F)F)CC1]
2-{3-[(4-fluorophenyl)amino]prop-1-yn-1-yl}-N-(1-methylpiperidin-4-yl)-1-(2,2,2-trifluoroethyl)-1H-indol-4-amine |
| 352-P | 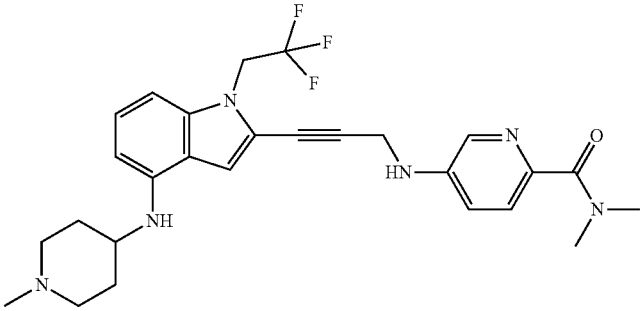
N,N-dimethyl-5-[(3-{4-[(1-methylpiperidin-4-yl)amino]-1-(2,2,2-trifluoroethyl)-1H-indol-2-yl}prop-2-yn-1-yl)amino]pyridine-2-carboxamide |
| 353-P | 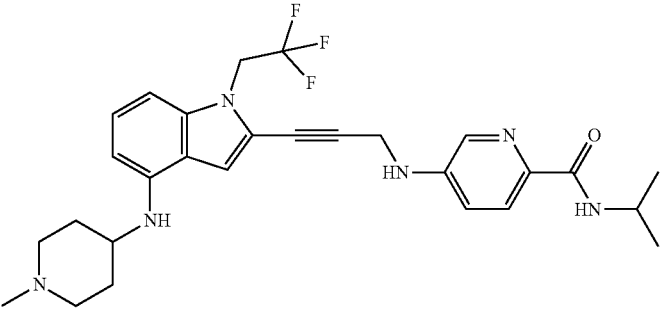 [SMILES: CC(C)NC(=O)c1ccc(NCC#Cc2cc3c(NC4CCN(C)CC4)cccc3n2CC(F)(F)F)cn1]
5-[(3-{4-[(1-methylpiperidin-4-yl)amino]-1-(2,2,2-trifluoroethyl)-1H-indol-2-yl}prop-2-yn-1-yl)amino]-N-(propan-2-yl)pyridine-2-carboxamide |

TABLE 1-continued

List of compounds

| # | Structure IUPAC name |
|---|---|
| 354-P | N-(pyridin-3-yl)-5-{[3-(4-{[(1R,4R)-4-(dimethylamino)cyclohexyl]amino}-1-(2,2,2-trifluoroethyl)-1H-indol-2-yl)prop-2-yn-1-yl]amino}pyridine-2-carboxamide |
| 355-P | N-(pyridin-3-yl)-5-{[3-(4-{[(1S,4S)-4-(dimethylamino)cyclohexyl]amino}-1-(2,2,2-trifluoroethyl)-1H-indol-2-yl)prop-2-yn-1-yl]amino}pyridine-2-carboxamide |
| 356-P | 2-{3-[(6-methanesulfonylpyridin-3-yl)amino]prop-1-yn-1-yl}-N-(1-methylpiperidin-4-yl)-1-(2,2,2-trifluoroethyl)-1H-indol-4-amine |

TABLE 1-continued

List of compounds

| # | Structure IUPAC name |
|---|---|
| 357-P | 
6-tert-butyl-N-(3-{4-[(1-methylpiperidin-4-yl)amino]-1-(2,2,2-trifluoroethyl)-1H-indol-2-yl}prop-2-yn-1-yl)pyridine-3-carboxamide |
| 358-P | 
2-{3-{(6-chloropyridin-3-yl)amino]prop-1-yn-1-yl}-N-(1-methylpiperidin-4-yl)-1-(2,2,2-trifluoroethyl)-1H-indol-4-amine |
| 359-P | 
2-{4-[(3-{4-[(1-methylpiperidin-4-yl)amino]-1-(2,2,2-trifluoroethyl)-1H-indol-2-yl}prop-2-yn-1-yl)amino]phenyl}propan-2-ol |
| 360-P | 
6-methyl-N-(3-{4-[(1-methylpiperidin-4-yl)amino]-1-(2,2,2-trifluoroethyl)-1H-indol-2-yl}prop-2-yn-1-yl)pyridine-3-carboxamide |

TABLE 1-continued
List of compounds
| # | Structure IUPAC name |
|---|---|
| 361-P | 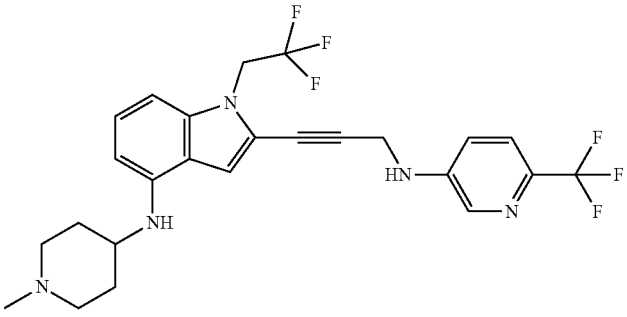 [SMILES: CN1CCC(Nc2cccc3c2cc(C#CCNc2ccc(C(F)(F)F)nc2)n3CC(F)(F)F)CC1]<br>N-(1-methylpiperidin-4-yl)-1-(2,2,2-trifluoroethyl)-2-(3-{[6-(trifluoromethyl)pyridin-3-yl]amino}prop-1-yn-1-yl)-1H-indol-4-amine |
| 362-P | 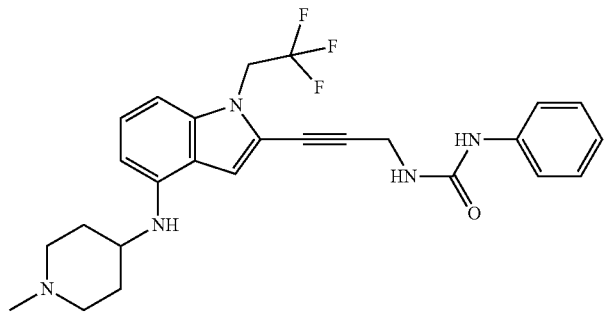 [SMILES: CN1CCC(Nc2cccc3c2cc(C#CCNC(=O)Nc2ccccc2)n3CC(F)(F)F)CC1]<br>3-(3-{4-[(1-methylpiperidin-4-yl)amino]-1-(2,2,2-trifluoroethyl)-1H-indol-2-yl}prop-2-yn-1-yl)-1-phenylurea |
| 363-P | 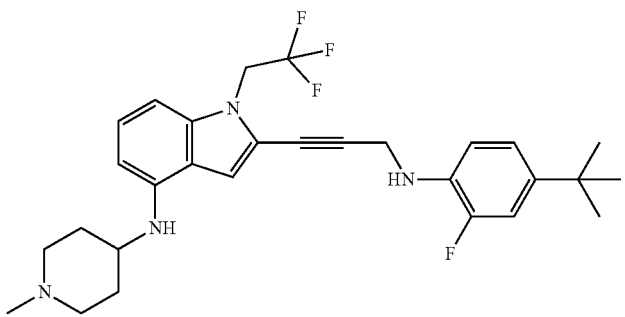<br>2-{3-[(4-tert-butyl-2-fluorophenyl)-amino]prop-1-yn-1-yl}-N-(1-methylpiperidin-4-yl)-1-(2,2,2-trifluoroethyl)-1H-indol-4-amine |

TABLE 1-continued

List of compounds

| # | Structure IUPAC name |
|---|---|
| 364-P | 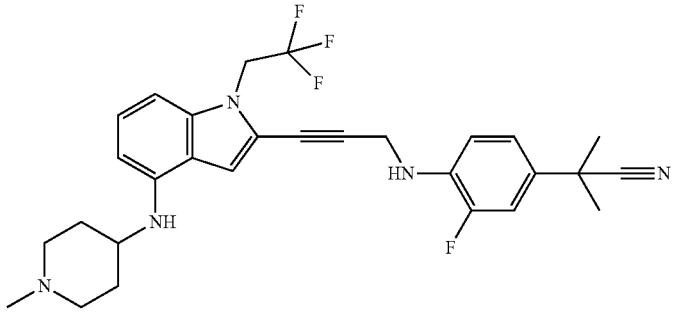 [SMILES: CN1CCC(Nc2cccc3c2cc(C#CCNc2ccc(C(C)(C)C#N)cc2F)n3CC(F)(F)F)CC1]<br>2-{3-fluoro-4-[(3-{4-[(1-methylpiperidin-4-yl)amino]-1-(2,2,2-trifluoroethyl)-1H-indol-2-yl}prop-2-yn-1-yl)amino]phenyl}-2-methylpropanenitrile |
| 365-P | 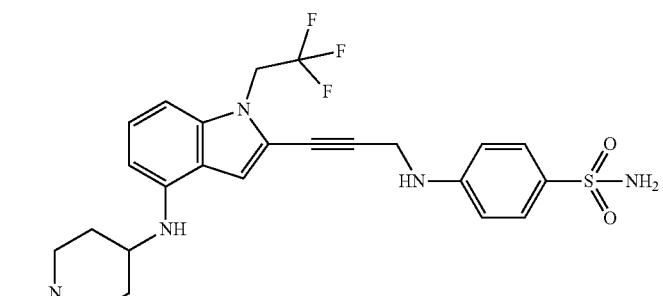<br>4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 366-P | 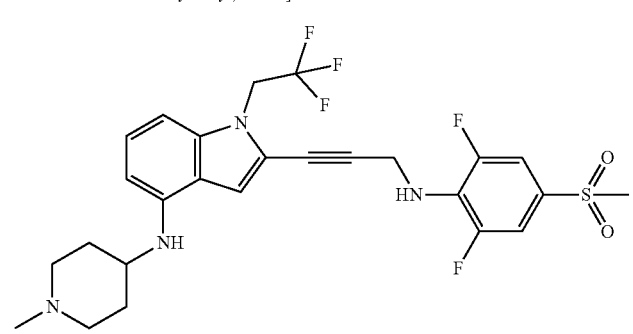<br>2-{3-[(2,6-difluoro-4-methane-sulfonylphenyl)amino]prop-1-yn-1-yl}-N-(1-methylpiperidin-4-yl)-1-(2,2,2-trifluoroethyl)-1H-indol-4-amine |
| 367-P | 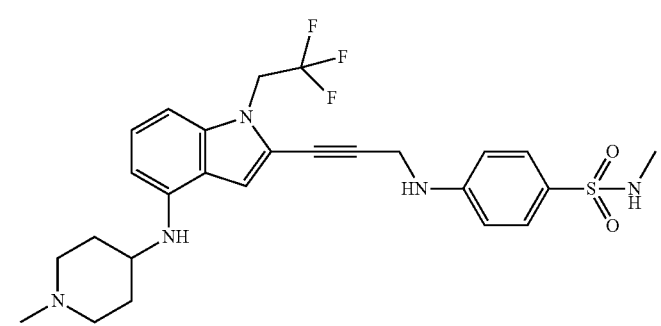<br>N-methyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |

TABLE 1-continued

List of compounds

| # | Structure IUPAC name |
|---|---|
| 368-P | 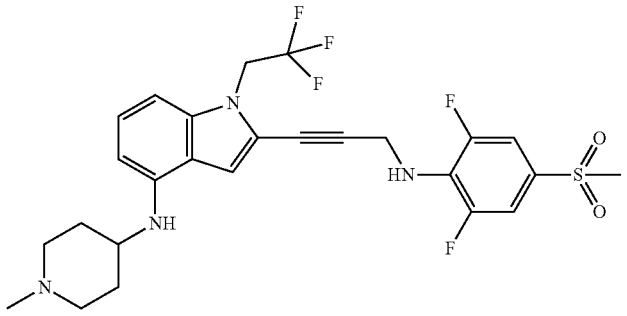<br>2-{3-[(4-methanesulfonyl-3-methoxyphenyl)amino]prop-1-yn-1-yl}-N-(1-methylpiperidin-4-yl)-1-(2,2,2-trifluoroethyl)-1H-indol-4-amine |
| 369-P | 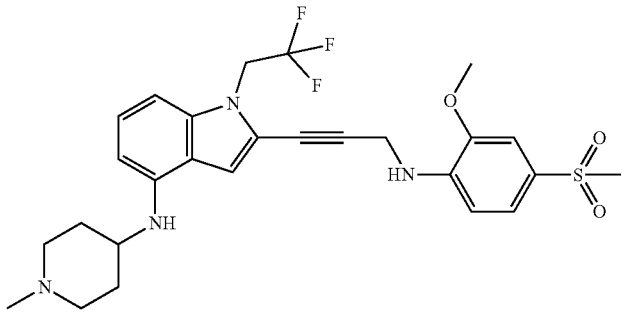<br>2-{3-[(4-methanesulfonyl-2-methoxyphenyl)amino]prop-1-yn-1-yl}-N-(1-methylpiperidin-4-yl)-1-(2,2,2-trifluoroethyl)-1H-indol-4-amine |
| 370-P | 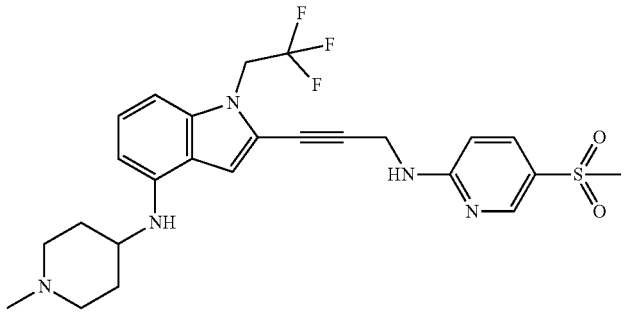<br>2-{3-[(5-methanesulfonylpyridin-2-yl)amino]prop-1-yn-1-yl}-N-(1-methylpiperidin-4-yl)-1-(2,2,2-trifluoroethyl)-1H-indol-4-amine |

TABLE 1-continued

List of compounds

| # | Structure | IUPAC name |
|---|---|---|
| 371-P | 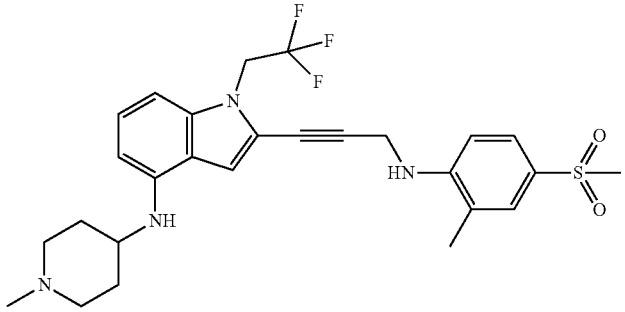 | 2-{3-[(4-methanesulfonyl-2-methylphenyl)amino]prop-1-yn-1-yl}-N-(1-methylpiperidin-4-yl)-1-(2,2,2-trifluoroethyl)-1H-indol-4-amine |
| 372-P | 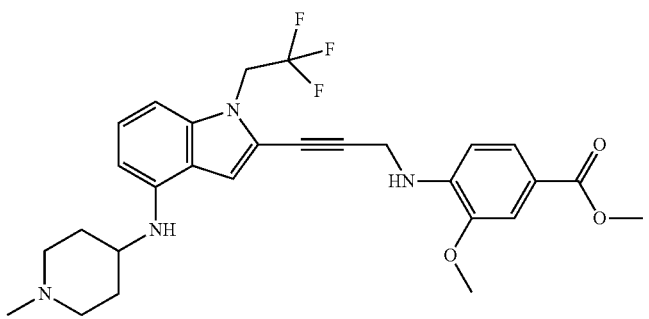 | methyl 3-methoxy-4-[(3-{4-[(1-methylpiperidin-4-yl)amino]-1-(2,2,2-trifluoroethyl)-1H-indol-2-yl}prop-2-yn-1-yl)amino]benzoate |
| 373-P | 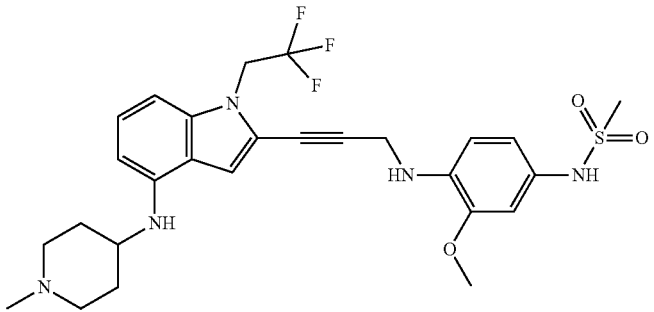 [SMILES: COc1cc(NS(C)(=O)=O)ccc1NCC#Cc1cc2c(NC3CCN(C)CC3)cccc2n1CC(F)(F)F] | N-{3-methoxy-4-[(3-{4-[(1-methylpiperidin-4-yl)amino]-1-(2,2,2-trifluoroethyl)-1H-indol-2-yl}prop-2-yn-1-yl)amino]phenyl}methanesulfonamide |
| 374-P | 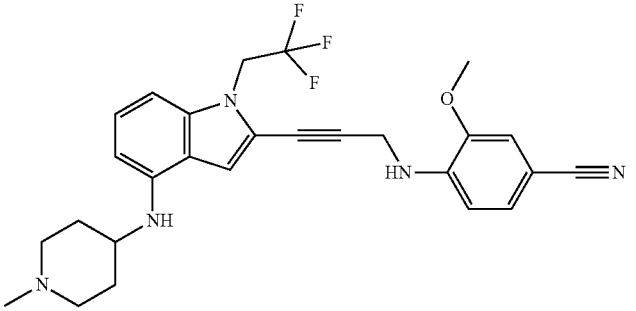 [SMILES: COc1cc(C#N)ccc1NCC#Cc1cc2c(NC3CCN(C)CC3)cccc2n1CC(F)(F)F] | 3-methoxy-4-[(3-{4-[(1-methylpiperidin-4-yl)amino]-1-(2,2,2-trifluoroethyl)-1H-indol-2-yl}prop-2-yn-1-yl)amino]benzonitrile |

TABLE 1-continued

List of compounds

| # | Structure IUPAC name |
|---|---|
| 375-P | 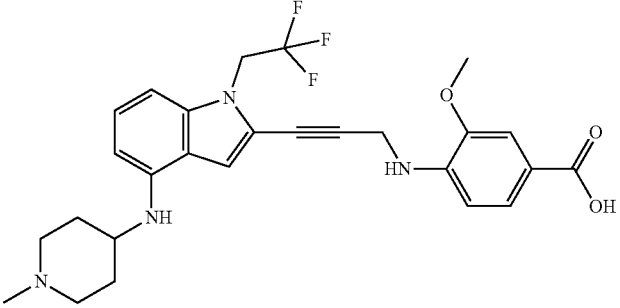 [SMILES: COc1cc(C(=O)O)ccc1NCC#Cc1cc2c(NC3CCN(C)CC3)cccc2n1CC(F)(F)F]<br>3-methoxy-4-[(3-{4-[(1-methylpiperidin-4-yl)amino]-1-(2,2,2-trifluoroethyl)-1H-indol-2-yl}prop-2-yn-1-yl)amino]benzoic acid |
| 376-P | 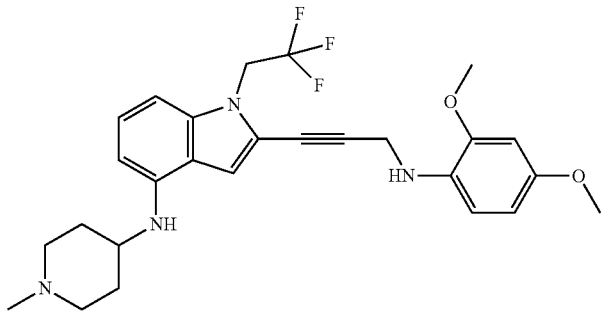<br>2-{3-[(2,4-dimethoxyphenyl)amino]prop-1-yn-1-yl}-N-(1-methylpiperidin-4-yl)-1-(2,2,2-trifluoroethyl)-1H-indol-4-amine |
| 377-P | 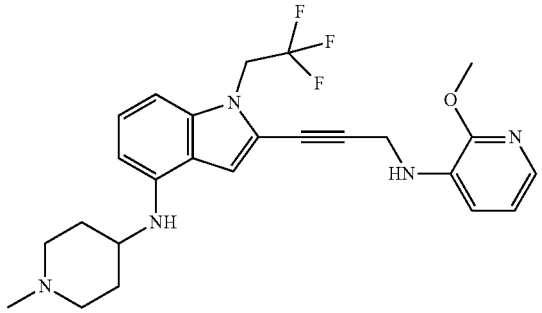<br>2-{3-[(2-methoxypyridin-3-yl)amino]prop-1-yn-1-yl}-N-(1-methylpiperidin-4-yl)-1-(2,2,2-trifluoroethyl)-1H-indol-4-amine |
| 378-P | 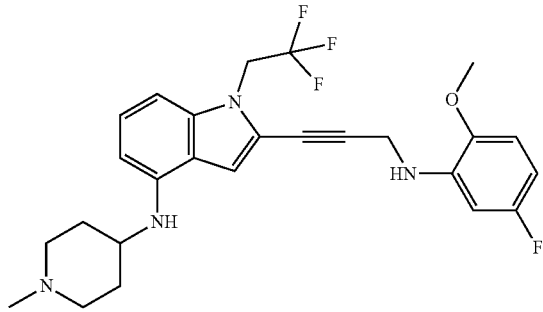 [SMILES: COc1ccc(F)cc1NCC#Cc1cc2c(NC3CCN(C)CC3)cccc2n1CC(F)(F)F]<br>2-{3-[(5-fluoro-2-methoxyphenyl)-amino]prop-1-yn-1-yl}-N-(1-methylpiperidin-4-yl)-1-(2,2,2-trifluoroethyl)-1H-indol-4-amine |

TABLE 1-continued
List of compounds
| # | Structure IUPAC name |
|---|---|
379-P
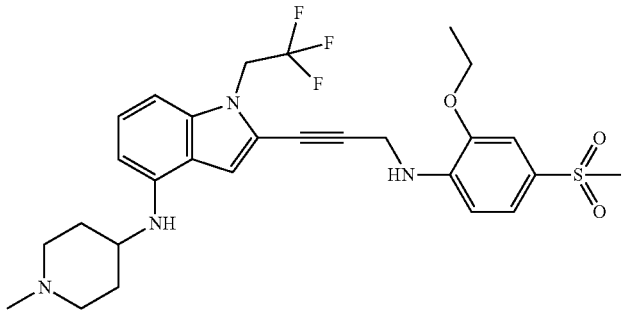
2-{3-[(2-ethoxy-4-methane-
sulfonylphenyl)amino]prop-1-yn-1-yl}-N-(1-
methylpiperidin-4-yl)-1-(2,2,2-
trifluoroethyl)-1H-indol-4-amine
380-P
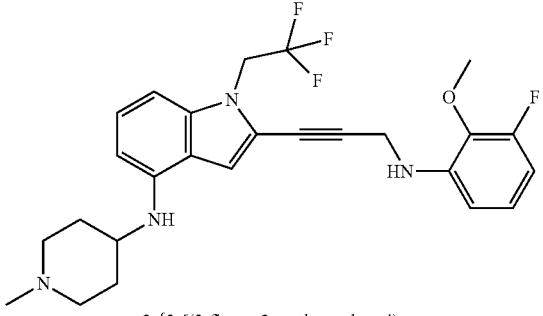
2-{3-[(3-fluoro-2-methoxyphenyl)-
amino]prop-1-yn-1-yl}-N-(1-
methylpiperidin-4-yl)-1-(2,2,2-
trifluoroethyl)-1H-indol-4-amine
381-P
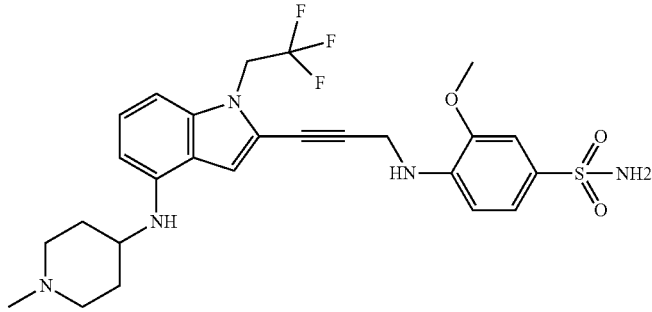 [SMILES: COc1cc(S(N)(=O)=O)ccc1NCC#Cc1cc2c(NC3CCN(C)CC3)cccc2n1CC(F)(F)F]
3-methoxy-4-[(3-{4-[(1-methylpiperidin-4-
yl)amino]-1-(2,2,2-trifluoroethyl)-1H-indol-
2-yl}prop-2-yn-1-yl)amino]benzene-1-sulfonamide TABLE 1-continued
List of compounds
| # | Structure IUPAC name |
|---|---|
| 382-P | 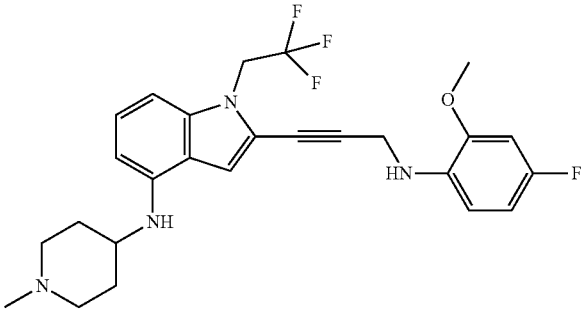 [SMILES: COc1cc(F)ccc1NCC#Cc1cc2c(NC3CCN(C)CC3)cccc2n1CC(F)(F)F]<br>2-{3-[(4-fluoro-2-methoxyphenyl)-amino]prop-1-yn-1-yl}-N-(1-methylpiperidin-4-yl)-1-(2,2,2-trifluoroethyl)-1H-indol-4-amine |
| 383-P | 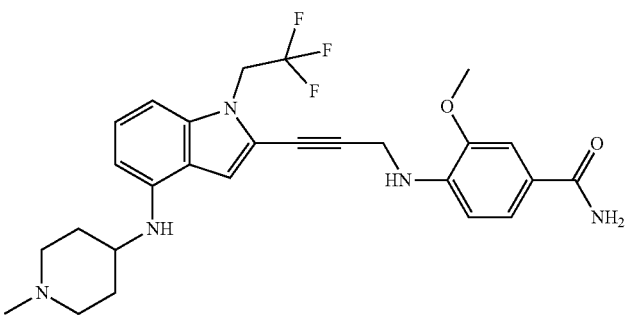 [SMILES: COc1cc(C(N)=O)ccc1NCC#Cc1cc2c(NC3CCN(C)CC3)cccc2n1CC(F)(F)F]<br>3-methoxy-4-[(3-{4-[(1-methylpiperidin-4-yl)amino]-1-(2,2,2-trifluoroethyl)-1H-indol-2-yl}prop-2-yn-1-yl)amino]-benzamide |
| 384-P | 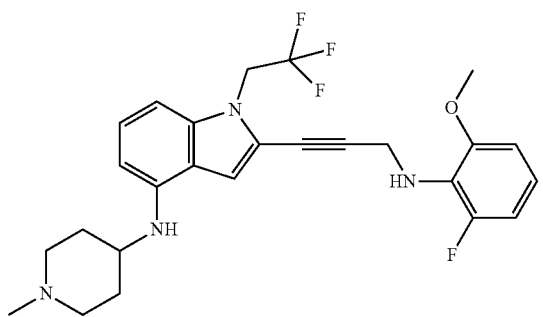<br>2-{3-[(2-fluoro-6-methoxyphenyl)-amino]prop-1-yn-1-yl}-N-(1-methylpiperidin-4-yl)-1-(2,2,2-trifluoroethyl)-1H-indol-4-amine |

TABLE 1-continued

List of compounds

| # | Structure | IUPAC name |
|---|---|---|
| 385-P | 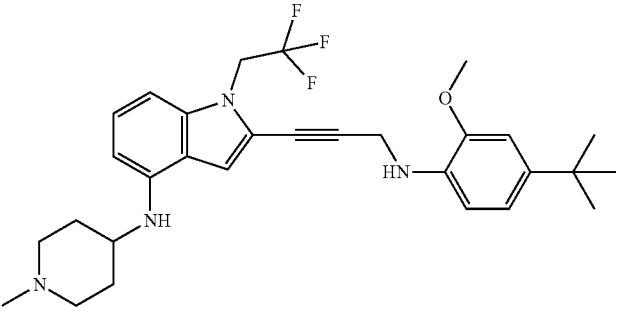 [SMILES: COc1cc(C(C)(C)C)ccc1NCC#Cc1cc2c(NC3CCN(C)CC3)cccc2n1CC(F)(F)F] | 2-{3-[(4-tert-butyl-2-methoxyphenyl)-amino]prop-1-yn-1-yl}-N-(1-methylpiperidin-4-yl)-1-(2,2,2-trifluoroethyl)-1H-indol-4-amine |
| 386-P | 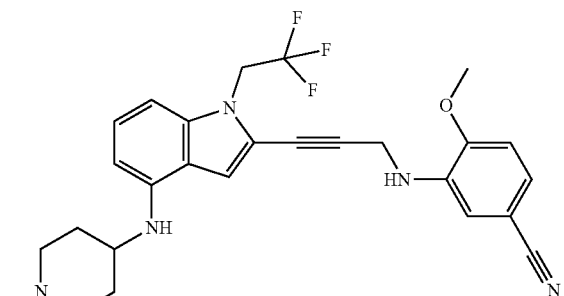 | 4-methoxy-3-[(3-{4-[(1-methylpiperidin-4-yl)amino]-1-(2,2,2-trifluoroethyl)-1H-indol-2-yl}prop-2-yn-1-yl)amino]-benzonitrile |
| 387-P | 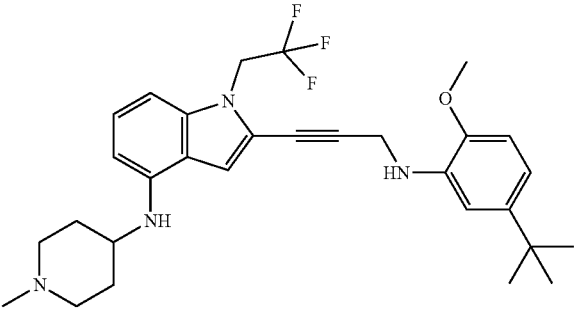 [SMILES: COc1ccc(C(C)(C)C)cc1NCC#Cc1cc2c(NC3CCN(C)CC3)cccc2n1CC(F)(F)F] | 2-{3-[(5-tert-butyl-2-methoxyphenyl)-amino]prop-1-yn-1-yl}-N-(1-methylpiperidin-4-yl)-1-(2,2,2-trifluoroethyl)-1H-indol-4-amine |
| 388-P | 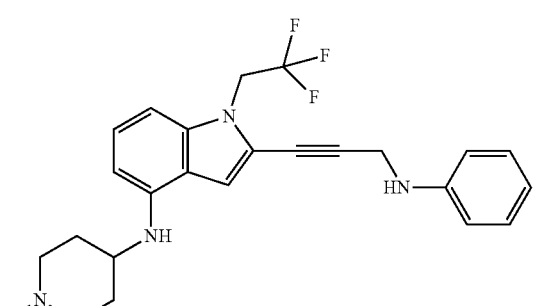 | N-(1-methylpiperidin-4-yl)-2-[3-(phenylamino)prop-1-yn-1-yl]-1-(2,2,2-trifluoroethyl)-1H-indol-4-amine |

TABLE 1-continued
List of compounds
| # | Structure | IUPAC name |
|---|---|---|
| 389-P | 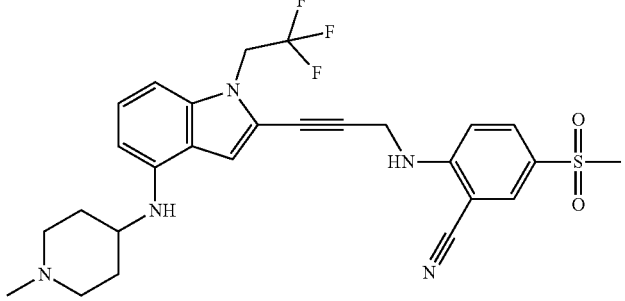 | 5-methanesulfonyl-2-[(3-{4-[(1-methylpiperidin-4-yl)amino]-1-(2,2,2-trifluoroethyl)-1H-indol-2-yl}prop-2-yn-1-yl)amino]benzonitrile |
| 390-P | 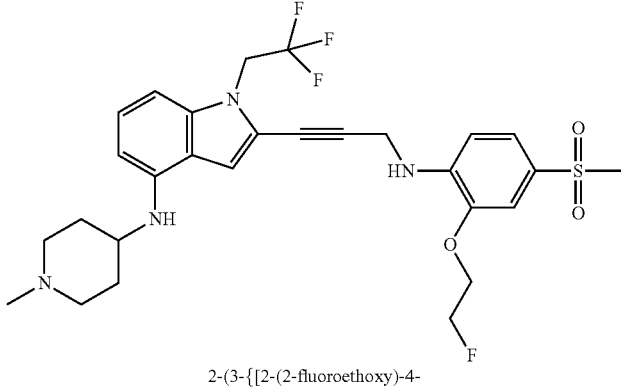 | 2-(3-{[2-(2-fluoroethoxy)-4-methanesulfonylphenyl]amino}prop-1-yn-1-yl)-N-(1-methylpiperidin-4-yl)-1-(2,2,2-trifluoroethyl)-1H-indol-4-amine |
| 391-P | 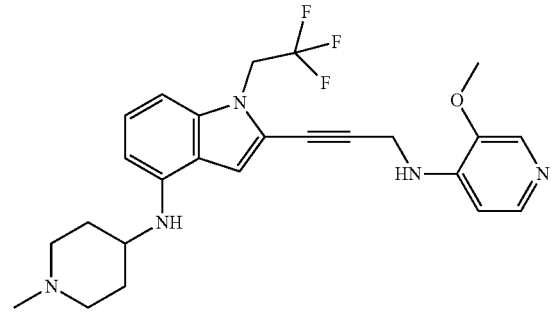 [SMILES: COc1cnccc1NCC#Cc1cc2c(NC3CCN(C)CC3)cccc2n1CC(F)(F)F] | 2-{3-[(3-methoxypyridin-4-yl)amino]prop-1-yn-1-yl}-N-(1-methylpiperidin-4-yl)-1-(2,2,2-trifluoroethyl)-1H-indol-4-amine |

TABLE 1-continued

List of compounds

| # | Structure IUPAC name |
|---|---|
| 392-P | 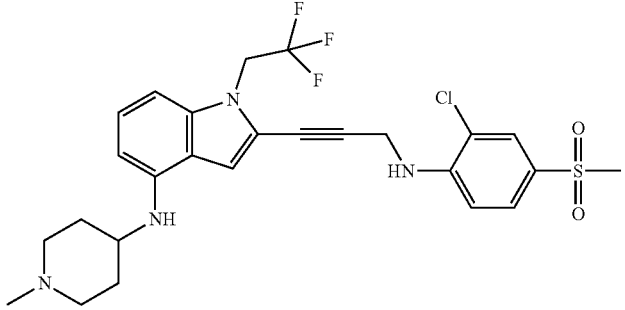<br>2-{3-[(2-chloro-4-methanesulfonyl-phenyl)amino]prop-1-yn-1-yl}-N-(1-methylpiperidin-4-yl)-1-(2,2,2-trifluoroethyl)-1H-indol-4-amine |
| 393-P | 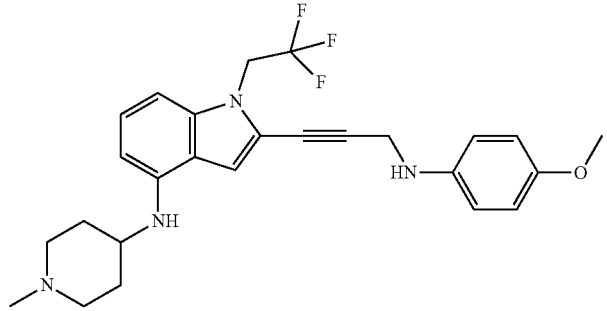<br>2-{3-[(4-methoxyphenyl)amino]prop-1-yn-1-yl}-N-(1-methylpiperidin-4-yl)-1-(2,2,2-trifluoroethyl)-1H-indol-4-amine |
| 394-P | 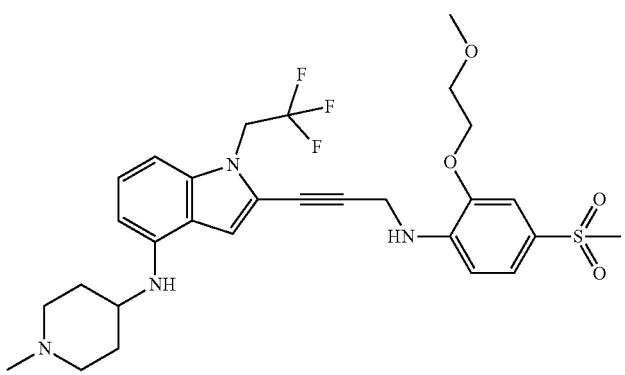<br>2-(3-{[4-methanesulfonyl-2-(2-methoxyethoxy)phenyl]amino}prop-1-yn-1-yl)-N-(1-methylpiperidin-4-yl)-1-(2,2,2-trifluoroethyl)-1H-indol-4-amine |

TABLE 1-continued
List of compounds
| # | Structure IUPAC name |
|---|---|
| 395-P | 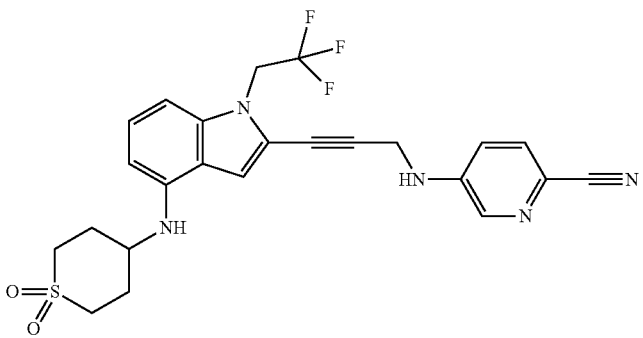 [SMILES: N#Cc1ccc(NCC#Cc2cc3c(NC4CCS(=O)(=O)CC4)cccc3n2CC(F)(F)F)cn1]<br>5-[(3-{4-[(1,1-dioxo-1λ⁶-thian-4-yl)amino]-1-(2,2,2-trifluoroethyl)-1H-indol-2-yl}prop-2-yn-1-yl)amino]pyridine-2-carbonitrile |
| 396-P | 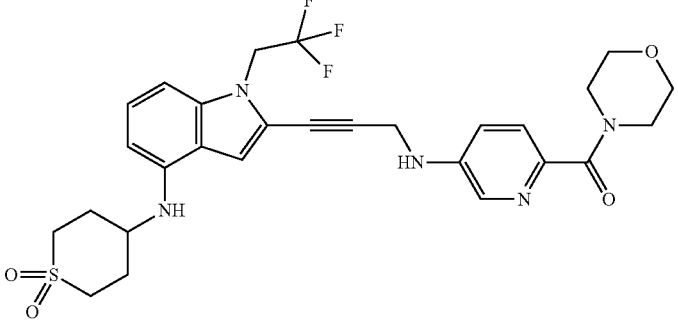<br>4-{[2-(3-{[6-(morpholine-4-carbonyl)pyridin-3-yl]amino}prop-1-yn-1-yl)-1-(2,2,2-trifluoroethyl)-1H-indol-4-yl]amino}-1λ⁶-thiane-1,1-dione |
| 397-P | 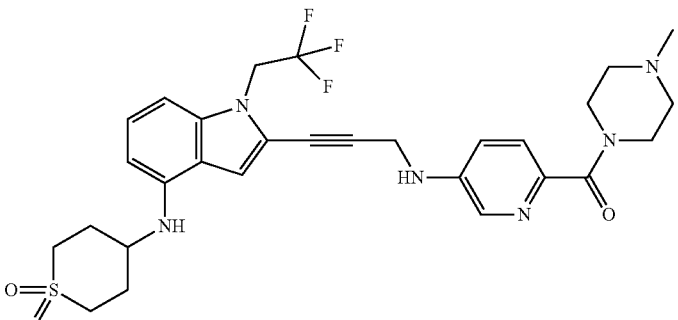<br>4-{[2-(3-{[6-(4-methylpiperazine-1-carbonyl)pyridin-3-yl]amino}prop-1-yn-1-yl)-1-(2,2,2-trifluoroethyl)-1H-indol-4-yl]amino}-1λ⁶-thiane-1,1-dione |

TABLE 1-continued
List of compounds
| # | Structure IUPAC name |
|---|---|
| 398-P | 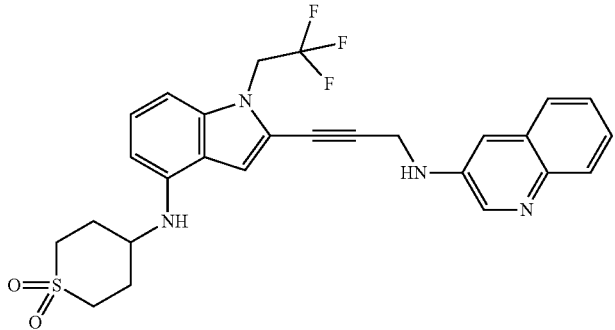 [SMILES: O=S1(=O)CCC(Nc2cccc3c2cc(C#CCNc2cnc4ccccc4c2)n3CC(F)(F)F)CC1]  4-[(2-{3-[(quinolin-3-yl)amino]prop-1-yn-1-yl}-1-(2,2,2-trifluoroethyl)-1H-indol-4-yl)amino]-1λ⁶-thiane-1,1-dione |
| 399-P | 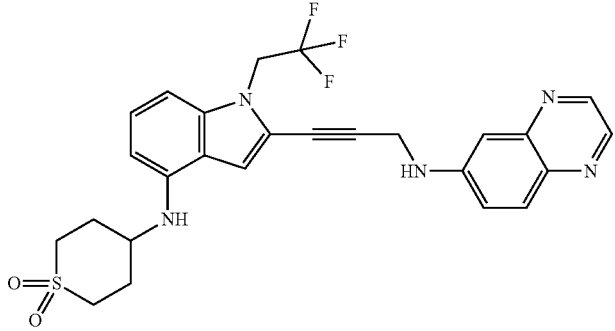 [SMILES: O=S1(=O)CCC(Nc2cccc3c2cc(C#CCNc2ccc4nccnc4c2)n3CC(F)(F)F)CC1]  4-[(2-{3-[(quinoxalin-6-yl)amino]prop-1-yn-1-yl}-1-(2,2,2-trifluoroethyl)-1H-indol-4-yl)amino]-1λ⁶-thiane-1,1-dione |
| 400-P | 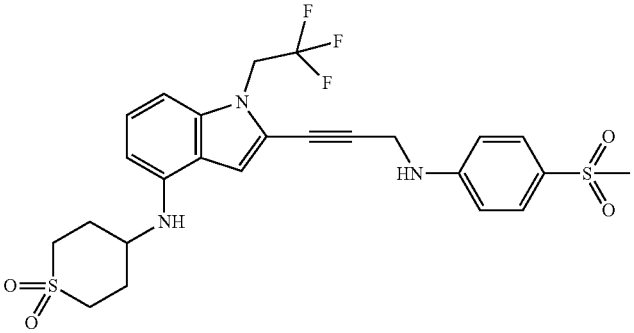  4-[(2-{3-[(4-methanesulfonylphenyl)amino]prop-1-yn-1-yl}-1-(2,2,2-trifluoroethyl)-1H-indol-4-yl)amino]-1λ⁶-thiane-1,1-dione |

TABLE 1-continued
List of compounds
| # | Structure IUPAC name |
|---|---|
| 401-P | 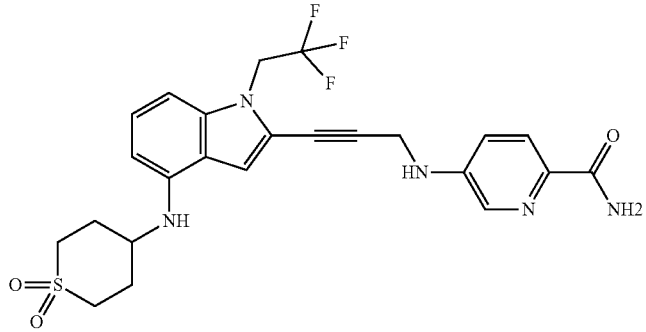 [SMILES: NC(=O)c1ccc(NCC#Cc2cc3c(NC4CCS(=O)(=O)CC4)cccc3n2CC(F)(F)F)cn1]\n\n5-[(3-{4-[(1,1-dioxo-1λ⁶-thian-4-yl)amino]-1-(2,2,2-trifluoroethyl)-1H-indol-2-yl}prop-2-yn-1-yl)amino]pyridine-2-carboxamide |
| 402-P | 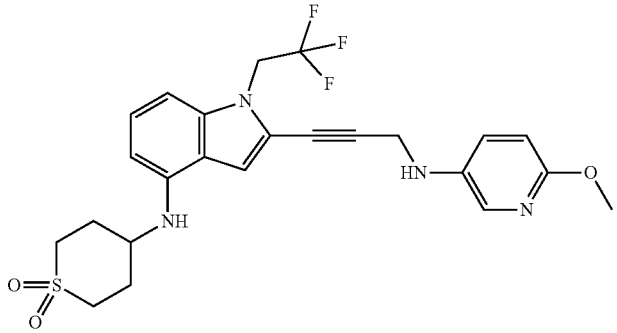 [SMILES: COc1ccc(NCC#Cc2cc3c(NC4CCS(=O)(=O)CC4)cccc3n2CC(F)(F)F)cn1]\n\n4-[(2-{3-[(6-methoxypyridin-3-yl)amino]prop-1-yn-1-yl}-1-(2,2,2-trifluoroethyl)-1H-indol-4-yl)amino]-1λ⁶-thiane-1,1-dione |
| 403-P | 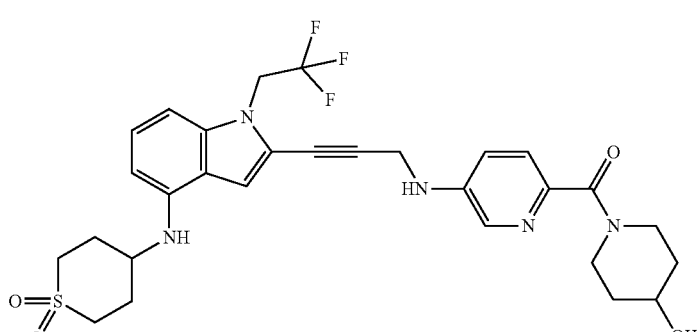\n\n4-{[2-(3-{[6-(4-hydroxypiperidine-1-carbonyl)pyridin-3-yl]amino}prop-1-yn-1-yl)-1-(2,2,2-trifluoroethyl)-1H-indol-4-yl]amino}-1λ⁶-thiane-1,1-dione |

TABLE 1-continued
List of compounds
| # | Structure IUPAC name |
|---|---|
| 404-P | 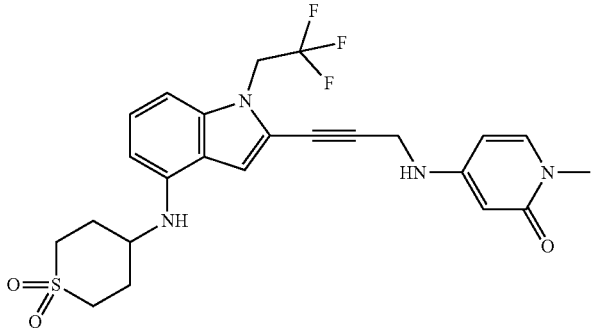 [SMILES: Cn1ccc(NCC#Cc2cc3c(NC4CCS(=O)(=O)CC4)cccc3n2CC(F)(F)F)cc1=O]
4-[(2-{3-[(1-methyl-2-oxo-1,2-dihydropyridin-4-yl)amino]prop-1-yn-1-yl}-1-(2,2,2-trifluoroethyl)-1H-indol-4-yl)amino]-1λ⁶-thiane-1,1-dione |
| 405-P | 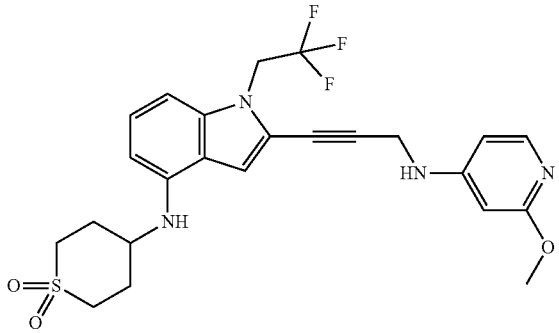 [SMILES: COc1cc(NCC#Cc2cc3c(NC4CCS(=O)(=O)CC4)cccc3n2CC(F)(F)F)ccn1]
4-[(2-{3-[(2-methoxypyridin-4-yl)amino]prop-1-yn-1-yl}-1-(2,2,2-trifluoroethyl)-1H-indol-4-yl)amino]-1λ⁶-thiane-1,1-dione |
| 406-P | 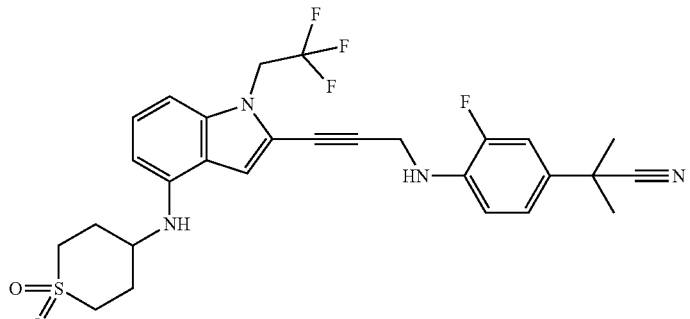
2-{4-[(3-{4-[(1,1-dioxo-1λ⁶-thian-4-yl)amino]-1-(2,2,2-trifluoroethyl)-1H-indol-2-yl}prop-2-yn-1-yl)amino]-3-fluorophenyl}-2-methylpropanenitrile |

TABLE 1-continued

List of compounds

| # | Structure IUPAC name |
|---|---|
| 407-P | 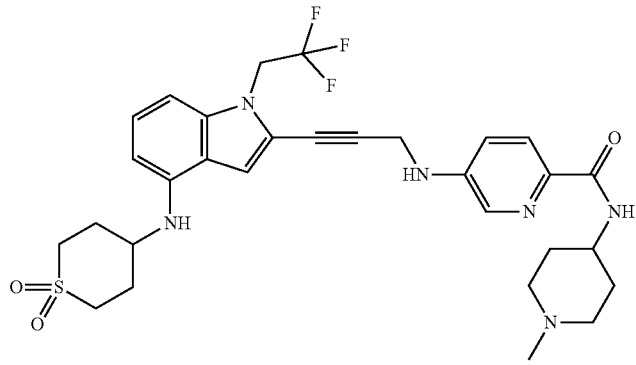 [SMILES: CN1CCC(NC(=O)c2ccc(NCC#Cc3cc4c(NC5CCS(=O)(=O)CC5)cccc4n3CC(F)(F)F)cn2)CC1]<br>5-[(3-{4-[(1,1-dioxo-1λ⁶-thian-4-yl)amino]-1-(2,2,2-trifluoroethyl)-1H-indol-2-yl}prop-2-yn-1-yl)amino]-N-(1-methylpiperidin-4-yl)pyridine-2-carboxamide |
| 408-P | 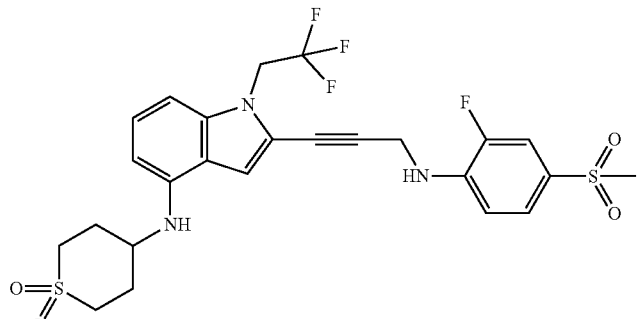<br>4-[(2-{3-[(2-fluoro-4-methanesulfonyl-phenyl)amino]prop-1-yn-1-yl}-1-(2,2,2-trifluoroethyl)-1H-indol-4-yl)amino]-1λ⁶-thiane-1,1-dione |
| 409-P | 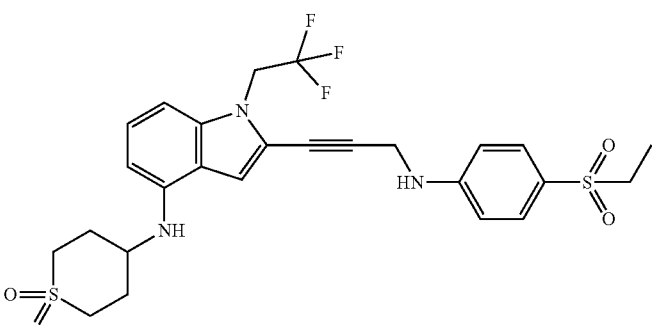<br>4-{[(2-(3-{[4-(ethanesulfonyl)-phenyl]amino}prop-1-yn-1-yl)-1-(2,2,2-trifluoroethyl)-1H-indol-4-yl]amino}-1λ⁶-thiane-1,1-dione |

TABLE 1-continued
List of compounds
| # | Structure IUPAC name |
|---|---|
| 410-P | 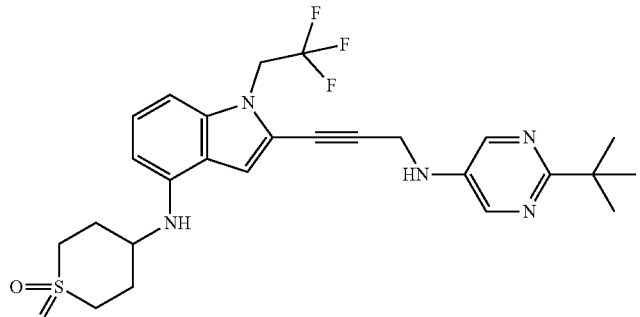<br>4-[(2-{3-[(2-tert-butylpyrimidin-5-yl)amino]prop-1-yn-1-yl}-1-(2,2,2-trifluoroethyl)-1H-indol-4-yl)amino]-1λ⁶-thiane-1,1-dione |
| 411-P | 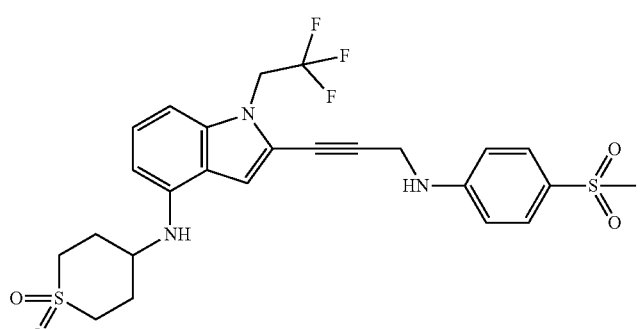<br>3-{4-[(1,1-dioxo-1λ⁶-thian-4-yl)amino]-1-(2,2,2-trifluoroethyl)-1H-indol-2-yl}-N-(4-methanesulfonyl-phenyl)-prop-2-ynamide |
| 412-P | 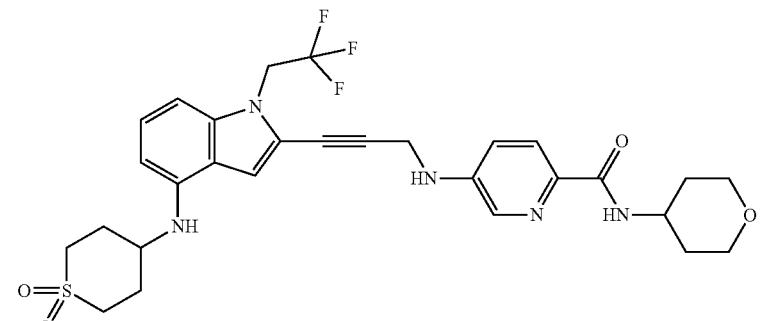<br>5-[(3-{4-[(1,1-dioxo-1λ⁶-thian-4-yl)amino]-1-(2,2,2-trifluoroethyl)-1H-indol-2-yl}prop-2-yn-1-yl)amino]-N-(oxan-4-yl)pyridine-2-carboamide |

| # | Structure IUPAC name |
|---|---|
| 413-P | 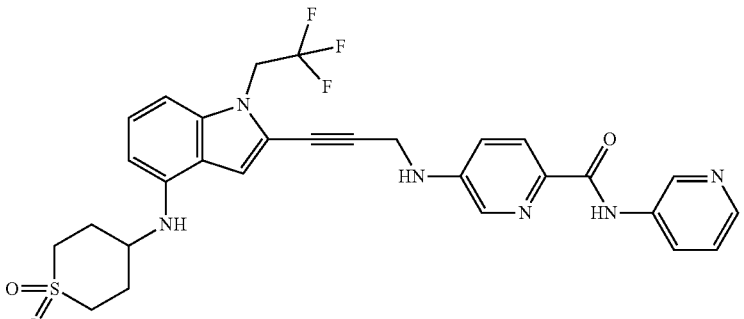 5-[(3-{4-[(1,1-dioxo-1λ⁶-thian-4-yl)amino]-1-(2,2,2-trifluoroethyl)-1H-indol-2-yl}prop-2-yn-1-yl)amino]-N-(pyridin-3-yl)pyridine-2-carboxamide |
| 414-P | 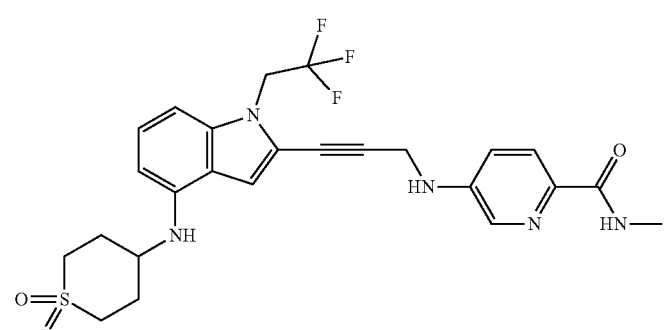 5-[(3-{4-[(1,1-dioxo-1λ⁶-thian-4-yl)amino]-1-(2,2,2-trifluoroethyl)-1H-indol-2-yl}prop-2-yn-1-yl)amino]-N-methylpyridine-2-carboxamide |
| 415-P | 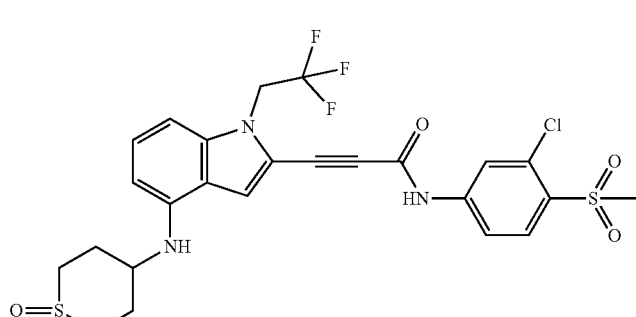 4-[(2-{3-[(3-chloro-4-methanesulfonylphenyl)amino]prop-1-yn-1-yl}-1-(2,2,2-trifluoroethyl)-1H-indol-4-yl)amino]-1λ⁶-thiane-1,1-dione |

TABLE 1-continued

List of compounds

| # | Structure | IUPAC name |
|---|---|---|
| 416-P | 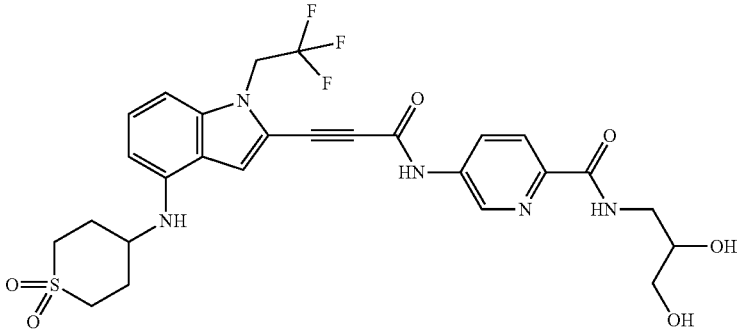 [SMILES: O=C(C#Cc1cc2c(NC3CCS(=O)(=O)CC3)cccc2n1CC(F)(F)F)Nc1ccc(C(=O)NCC(O)CO)nc1] | N-(2,3-dihydroxypropyl)-5-[(3-{4-[(1,1-dioxo-1λ⁶-thian-4-yl)amino]-1-(2,2,2-trifluoroethyl)-1H-indol-2-yl}prop-2-yn-1-yl)amino]pyridine-2-carboxamide |
| 417-P | 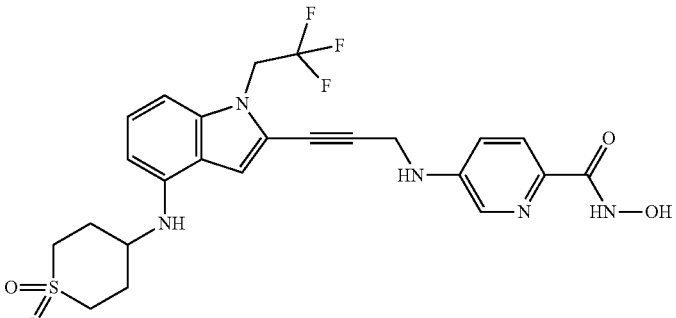 | 5-[(3-{4-[(1,1-dioxo-1λ⁶-thian-4-yl)amino]-1-(2,2,2-trifluoroethyl)-1H-indol-2-yl}prop-2-yn-1-yl)amino]-N-hydroxypyridine-2-carboxamide |
| 418-P | 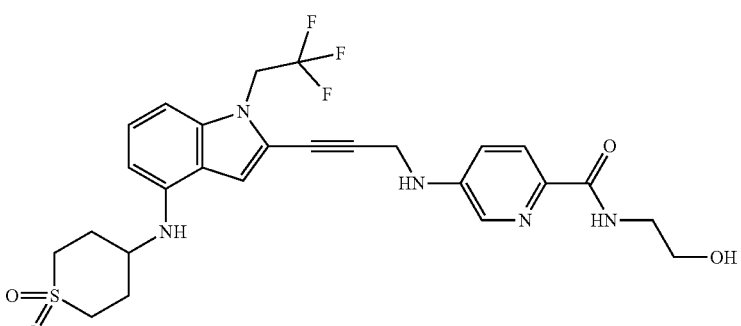 | 5-[(3-{4-[(1,1-dioxo-1λ⁶-thian-4-yl)amino]-1-(2,2,2-trifluoroethyl)-1H-indol-2-yl}prop-2-yn-1-yl)amino]-N-(2-hydroxyethyl)pyridine-2-carboxamide |

TABLE 1-continued
List of compounds
| # | Structure IUPAC name |
|---|---|
419-P
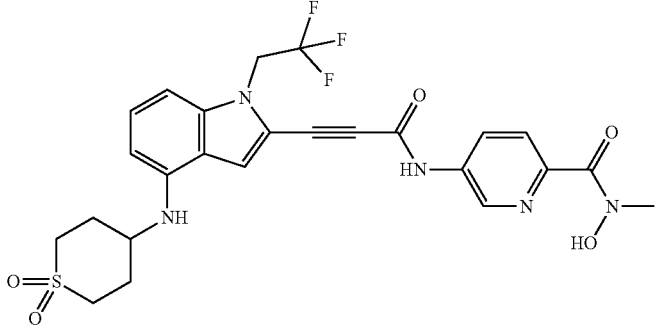 [SMILES: CN(O)C(=O)c1ccc(NC(=O)C#Cc2cc3c(NC4CCS(=O)(=O)CC4)cccc3n2CC(F)(F)F)cn1]
5-[(3-{4-[(1,1-dioxo-1λ⁶-thian-4-yl)amino]-1-(2,2,2-trifluoroethyl)-1H-indol-2-yl}prop-2-yn-1-yl)amino]-N-hydroxy-N-methylpyridine-2-carboxamide
420-P
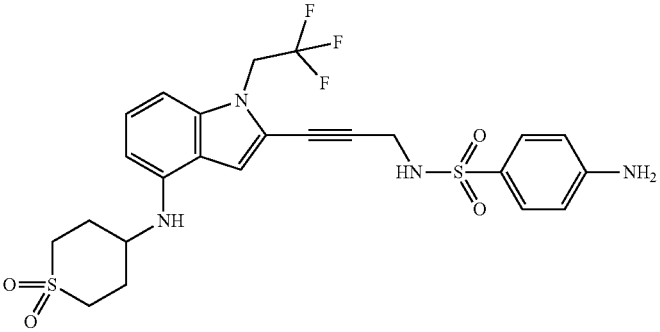 [SMILES: Nc1ccc(S(=O)(=O)NCC#Cc2cc3c(NC4CCS(=O)(=O)CC4)cccc3n2CC(F)(F)F)cc1]
4-amino-N-(3-{4-[(1,1-dioxo-1λ⁶-thian-4-yl)amino]-1-(2,2,2-trifluoroethyl)-1H-indol-2-yl}prop-2-yn-1-yl)benzene-1-sulfonamide
421-P
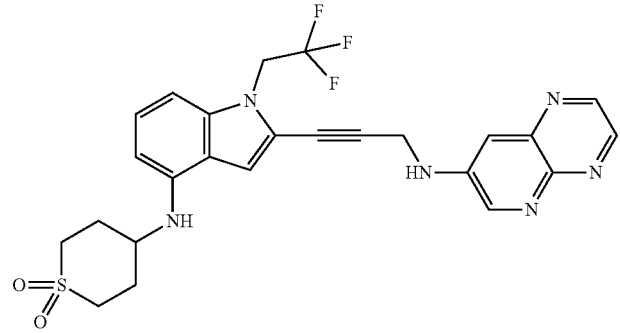 [SMILES: O=S1(=O)CCC(Nc2cccc3c2cc(C#CCNc2cnc4nccnc4c2)n3CC(F)(F)F)CC1]
4-({2-[3-({pyrido[2,3-b]pyrazin-7-yl}amino)prop-1-yn-1-yl]-1-(2,2,2-trifluoroethyl)-1H-indol-4-yl}amino)-1λ⁶-thiane-1,1-dione TABLE 1-continued
List of compounds
| # | Structure IUPAC name |
|---|---|
| 422-P | 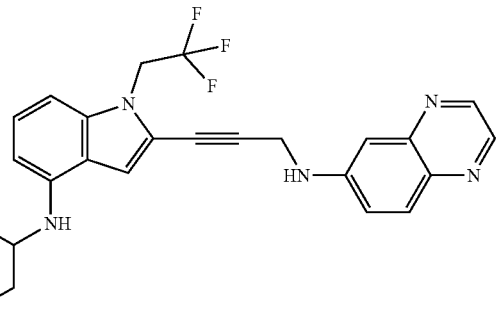<br>4-[(3-{4-[(1,1-dioxo-1λ⁶-thian-4-yl)amino]-1-(2,2,2-trifluoroethyl)-1H-indol-2-yl}prop-2-yn-1-yl)amino]-benzamide |
| 423-P | 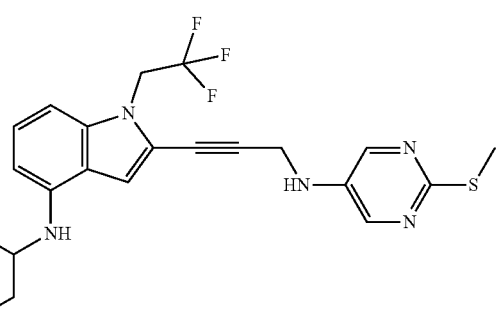<br>4-{[2-(3-{[2-(methylsulfanyl)pyrimidin-5-yl]amino}prop-1-yn-1-yl)-1-(2,2,2-trifluoroethyl)-1H-indol-4-yl]amino}-1λ⁶-thiane-1,1-dione |
| 424-P | 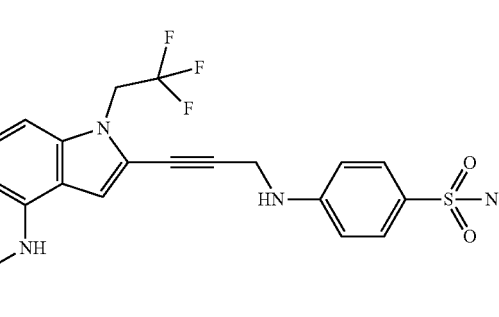<br>4-[(3-{4-[(1,1-dioxo-1λ⁶-thian-4-yl)amino]-1-(2,2,2-trifluoroethyl)-1H-indol-2-yl}prop-2-yn-1-yl)amino]benzene-1-sulfonamide |

TABLE 1-continued
List of compounds
| # | Structure IUPAC name |
|---|---|
| 425-P | 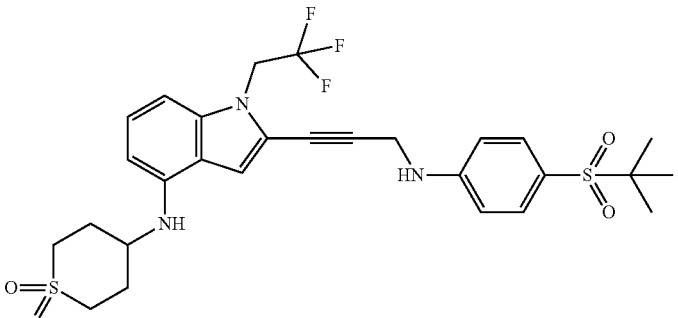  4-{[2-(3-{[4-(2-methylpropane-2-sulfonyl)phenyl]amino}prop-1-yn-1-yl)-1-(2,2,2-trifluoroethyl)-1H-indol-4-yl]amino}-1$\lambda^6$-thiane-1,1-dione |
| 426-P | 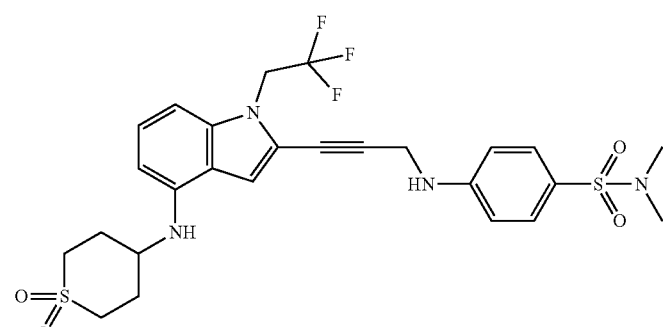  4-[(3-{4-[(1,1-dioxo-1$\lambda^6$-thian-4-yl)amino]-1-(2,2,2-trifluoroethyl)-1H-indol-2-yl}prop-2-yn-1-yl)amino]-N,N-dimethylbenzene-1-sulfonamide |
| 427-P | 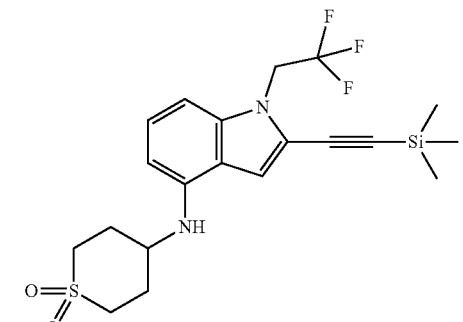  4-{[1-(2,2,2-trifluoroethyl)-2-[2-(trimethylsilyl)ethynyl]-1H-indol-4-yl]amino}-1$\lambda^6$-thiane-1,1-dione |

TABLE 1-continued

List of compounds

| # | Structure IUPAC name |
|---|---|
| 428-P | 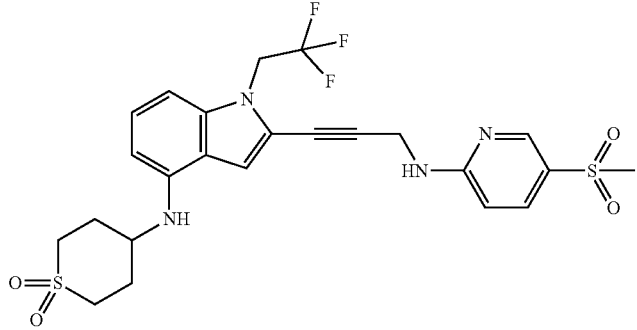<br>4-[(2-{3-[(5-methanesulfonylpyridin-2-yl)amino]prop-1-yn-1-yl}-1-(2,2,2-trifluoroethyl)-1H-indol-4-yl)amino]-1$\lambda^6$-thiane-1,1-dione |
| 429-P | 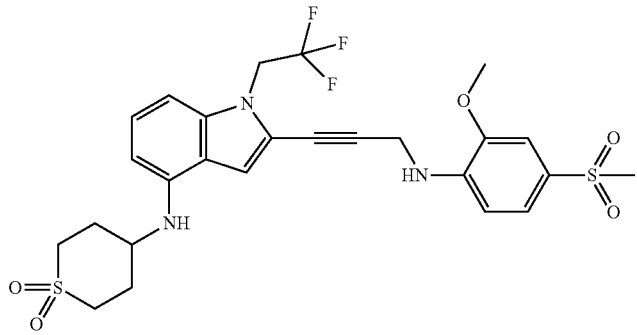 [SMILES: COc1cc(S(C)(=O)=O)ccc1NCC#Cc1cc2c(NC3CCS(=O)(=O)CC3)cccc2n1CC(F)(F)F]<br>4-[(2-{3-[(4-methanesulfonyl-2-methoxyphenyl)amino]prop-1-yn-1-yl}-1-(2,2,2-trifluoroethyl)-1H-indol-4-yl)amino]-1$\lambda^6$-thiane-1,1-dione |
| 430-P | 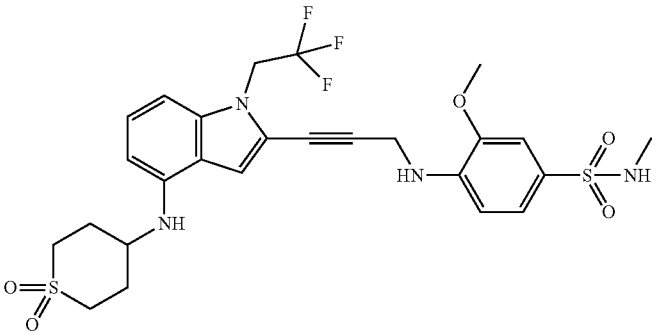 [SMILES: CNS(=O)(=O)c1ccc(NCC#Cc2cc3c(NC4CCS(=O)(=O)CC4)cccc3n2CC(F)(F)F)c(OC)c1]<br>4-[(3-{4-[(1,1-dioxo-1$\lambda^6$-thian-4-yl)amino]-1-(2,2,2-trifluoroethyl)-1H-indol-2-yl}prop-2-yn-1-yl)amino]-N-methylbenzene-1-sulfonamide |

TABLE 1-continued
List of compounds
| # | Structure IUPAC name |
|---|---|
| 431-P | 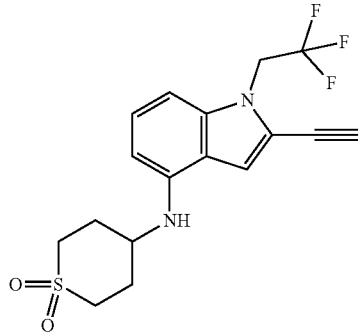 [SMILES: C#Cc1cc2c(NC3CCS(=O)(=O)CC3)cccc2n1CC(F)(F)F]<br>4-{[2-ethynyl-1-(2,2,2-trifluoroethyl)-1H-indol-4-yl]amino}-1λ⁶-thiane-1,1-dione |
| 432-P | 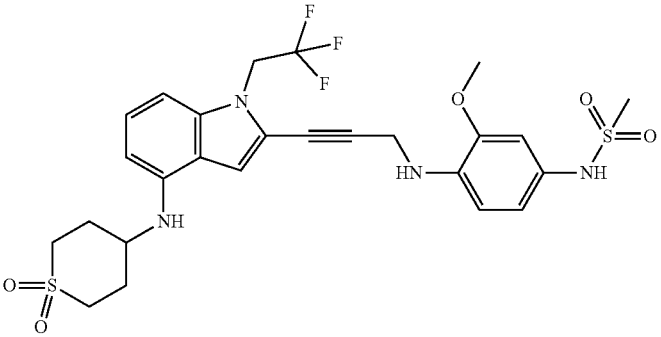 [SMILES: COc1cc(NS(C)(=O)=O)ccc1NCC#Cc1cc2c(NC3CCS(=O)(=O)CC3)cccc2n1CC(F)(F)F]<br>N-{4-[(3-{4-[(1,1-dioxo-1λ⁶-thian-4-yl)amino]-1-(2,2,2-trifluoroethyl)-1H-indol-2-yl}prop-2-yn-1-yl)amino]-3-methoxyphenyl}methanesulfonamide |
| 433-P | 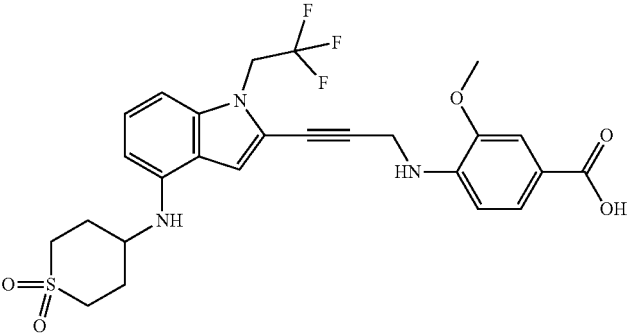 [SMILES: COc1cc(C(=O)O)ccc1NCC#Cc1cc2c(NC3CCS(=O)(=O)CC3)cccc2n1CC(F)(F)F]<br>4-[(3-{4-[(1,1-dioxo-1λ⁶-thian-4-yl)amino]-1-(2,2,2-trifluoroethyl)-1H-indol-2-yl}prop-2-yn-1-yl)amino]-3-methoxybenzoic acid |

TABLE 1-continued
List of compounds
| # | Structure IUPAC name |
|---|---|
| 434-P | 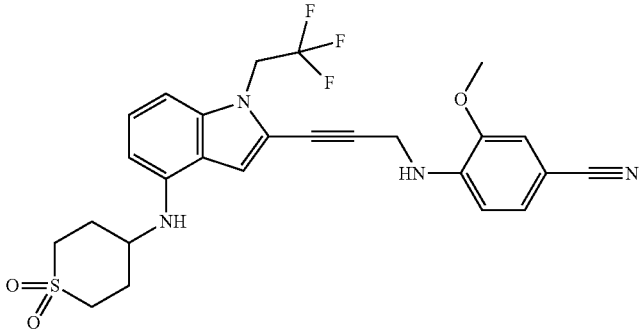 [SMILES: COc1cc(C#N)ccc1NCC#Cc1cc2c(NC3CCS(=O)(=O)CC3)cccc2n1CC(F)(F)F]<br>4-[(3-{4-[(1,1-dioxo-1λ⁶-thian-4-yl)amino]-1-(2,2,2-trifluoroethyl)-1H-indol-2-yl}prop-2-yn-1-yl)amino]-3-methoxybenzonitrile |
| 435-P | 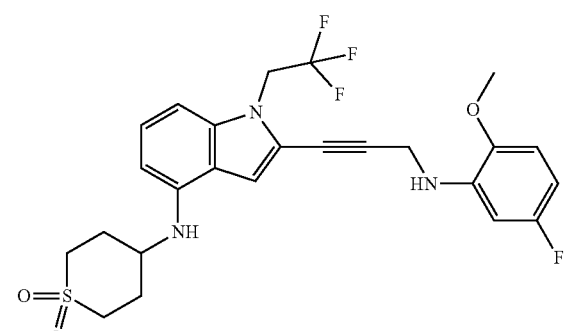<br>4-[(2-{3-[(5-fluoro-2-methoxyphenyl)amino]prop-1-yn-1-yl}-1-(2,2,2-trifluoroethyl)-1H-indol-4-yl)amino]-1λ⁶-thiane-1,1-dione |
| 436-P | 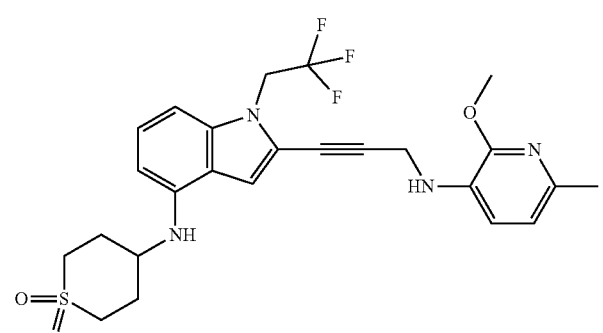<br>4-[(2-{3-[(2-methoxy-6-methylpyridin-3-yl)amino]prop-1-yn-1-yl}-1-(2,2,2-trifluoroethyl)-1H-indol-4-yl)amino]-1λ⁶-thiane-1,1-dione |

TABLE 1-continued
List of compounds
| # | Structure IUPAC name |
|---|---|
| 437-P | 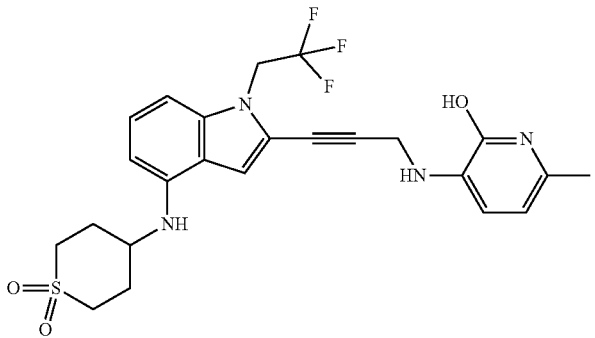 [SMILES: Cc1ccc(NCC#Cc2cc3c(NC4CCS(=O)(=O)CC4)cccc3n2CC(F)(F)F)c(O)n1]<br>4-[(2-{3-[(2-hydroxy-6-methylpyridin-3-yl)amino]prop-1-yn-1-yl}-1-(2,2,2-trifluoroethyl)-1H-indol-4-yl)amino]-1λ⁶-thiane-1,1-dione |
| 438-P | 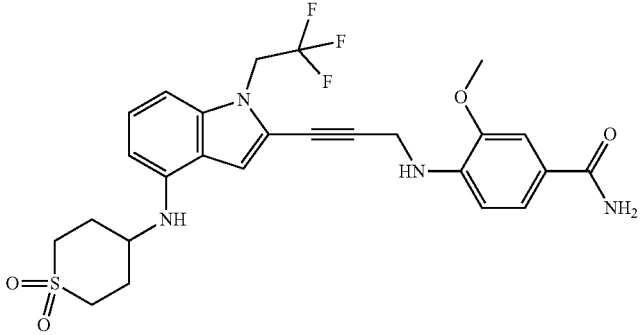 [SMILES: COc1cc(C(N)=O)ccc1NCC#Cc1cc2c(NC3CCS(=O)(=O)CC3)cccc2n1CC(F)(F)F]<br>4-[(3-{4-[(1,1-dioxo-1λ⁶-thian-4-yl)amino]-1-(2,2,2-trifluoroethyl)-1H-indol-2-yl}prop-2-yn-1-yl)amino]-3-methoxybenzamide |
| 439-P | 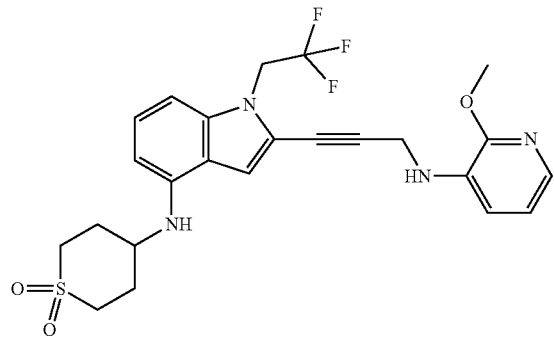 [SMILES: COc1ncccc1NCC#Cc1cc2c(NC3CCS(=O)(=O)CC3)cccc2n1CC(F)(F)F]<br>4-[(2-{3-[(2-methoxypyridin-3-yl)amino]prop-1-yn-1-yl}-1-(2,2,2-trifluoroethyl)-1H-indol-4-yl)amino]-1λ⁶-thiane-1,1-dione |

| # | Structure IUPAC name |
|---|---|
| 440-P | 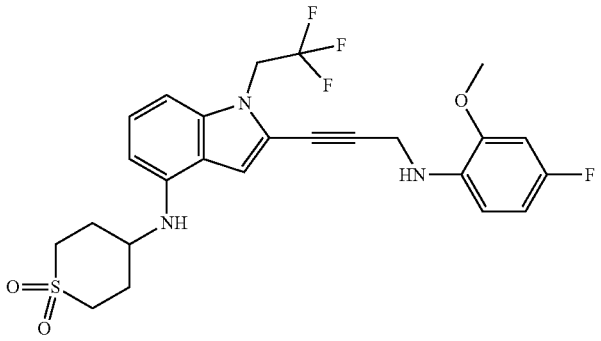 [SMILES: COc1cc(F)ccc1NCC#Cc1cc2c(NC3CCS(=O)(=O)CC3)cccc2n1CC(F)(F)F]
4-[(2-{3-[(4-fluoro-2-methoxyphenyl)amino]prop-1-yn-1-yl}-1-(2,2,2-trifluoroethyl)-1H-indol-4-yl)amino]-1λ⁶-thiane-1,1-dione |
| 441-P | 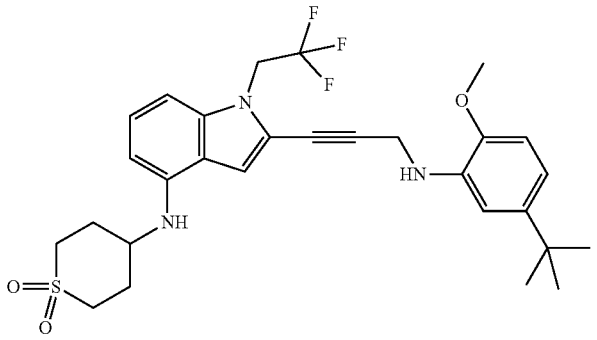 [SMILES: COc1ccc(C(C)(C)C)cc1NCC#Cc1cc2c(NC3CCS(=O)(=O)CC3)cccc2n1CC(F)(F)F]
4-[(2-{3-[(5-tert-butyl-2-methoxyphenyl)amino]prop-1-yn-1-yl}-1-(2,2,2-trifluoroethyl)-1H-indol-4-yl)amino]-1λ⁶-thiane-1,1-dione |
| 442-P | 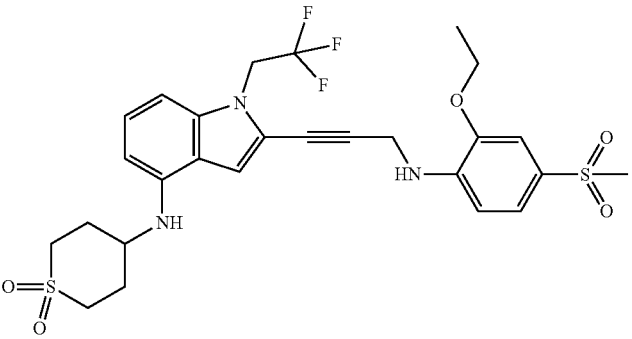 [SMILES: CCOc1cc(S(C)(=O)=O)ccc1NCC#Cc1cc2c(NC3CCS(=O)(=O)CC3)cccc2n1CC(F)(F)F]
4-[(2-{3-[(2-ethoxy-4-methanesulfonylphenyl)amino]prop-1-yn-1-yl}-1-(2,2,2-trifluoroethyl)-1H-indol-4-yl)amino]-1λ⁶-thiane-1,1-dione |

TABLE 1-continued
List of compounds
| # | Structure IUPAC name |
|---|---|
| 443-P | 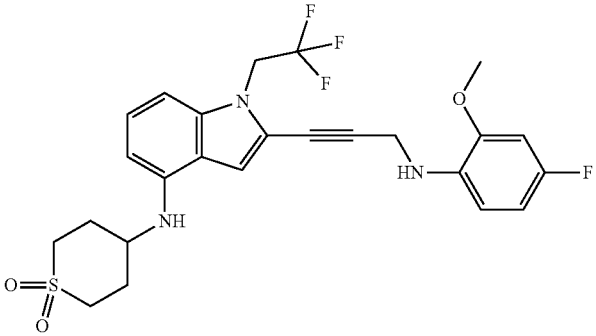 [SMILES: COc1cc(F)ccc1NCC#Cc1cc2c(NC3CCS(=O)(=O)CC3)cccc2n1CC(F)(F)F]<br>4-[(2-{3-[(3-fluoro-2-methoxyphenyl)-amino]prop-1-yn-1-yl}-1-(2,2,2-trifluoroethyl)-1H-indol-4-yl)amino]-1$\lambda^6$-thiane-1,1-dione |
| 444-P | 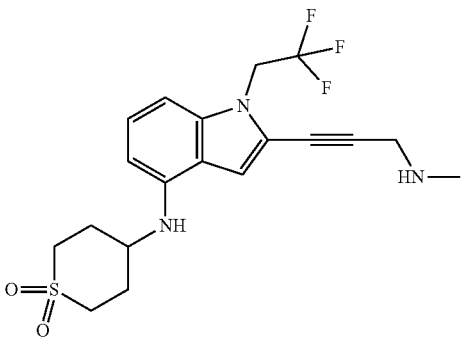 [SMILES: CNCC#Cc1cc2c(NC3CCS(=O)(=O)CC3)cccc2n1CC(F)(F)F]<br>4-({2-[3-(methylamino)prop-1-yn-1-yl]-1-(2,2,2-trifluoroethyl)-1H-indol-4-yl}amino)-1$\lambda^6$-thiane-1,1-dione |
| 445-P | 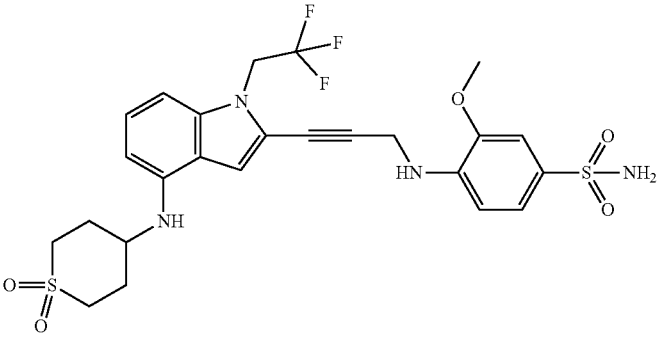 [SMILES: COc1cc(S(N)(=O)=O)ccc1NCC#Cc1cc2c(NC3CCS(=O)(=O)CC3)cccc2n1CC(F)(F)F]<br>4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxybenzene-1-sulfonamide |

TABLE 1-continued
List of compounds
| # | Structure IUPAC name |
|---|---|
| 446-P | 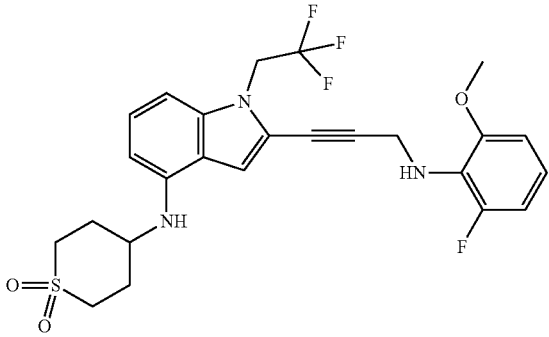 [SMILES: COc1cccc(F)c1NCC#Cc1cc2c(NC3CCS(=O)(=O)CC3)cccc2n1CC(F)(F)F]
4-[(2-{3-[(2-fluoro-6-methoxyphenyl)-amino]prop-1-yn-1-yl}-1-(2,2,2-trifluoroethyl)-1H-indol-4-yl)amino]-1$\lambda^6$-thiane-1,1-dione |
| 447-P | 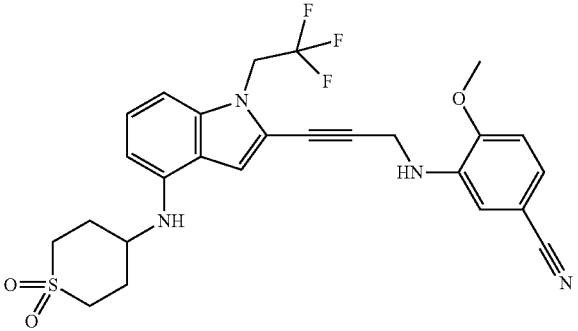 [SMILES: COc1ccc(C#N)cc1NCC#Cc1cc2c(NC3CCS(=O)(=O)CC3)cccc2n1CC(F)(F)F]
3-[(3-{4-[(1,1-dioxo-1$\lambda^6$-thian-4-yl)amino]-1-(2,2,2-trifluoroethyl)-1H-indol-2-yl}prop-2-yn-1-yl)amino]-4-methoxybenzonitrile |
| 448-P | 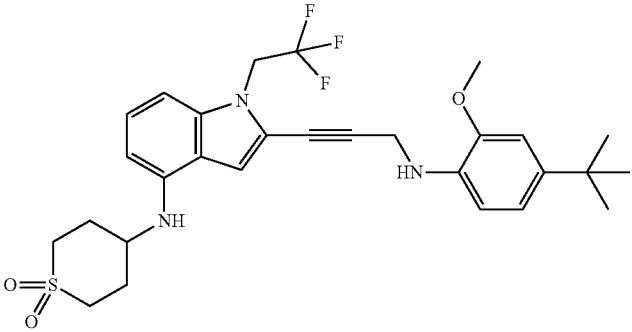
4-[(2-{3-[(4-tert-butyl-2-methoxy-phenyl)amino]prop-1-yn-1-yl}-1-(2,2,2-trifluoroethyl)-1H-indol-4-yl)amino]-1$\lambda^6$-thiane-1,1-dione |

TABLE 1-continued

List of compounds

| # | Structure IUPAC name |
|---|---|
| 449-P | 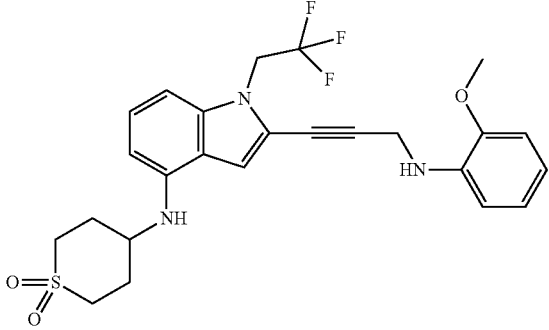 [SMILES: COc1ccccc1NCC#Cc1cc2c(NC3CCS(=O)(=O)CC3)cccc2n1CC(F)(F)F]<br>4-({2-[3-(phenylamino)prop-1-yn-1-yl]-1-(2,2,2-trifluoroethyl)-1H-indol-4-yl}amino)-1$\lambda^6$-thiane-1,1-dione |
| 450-P | 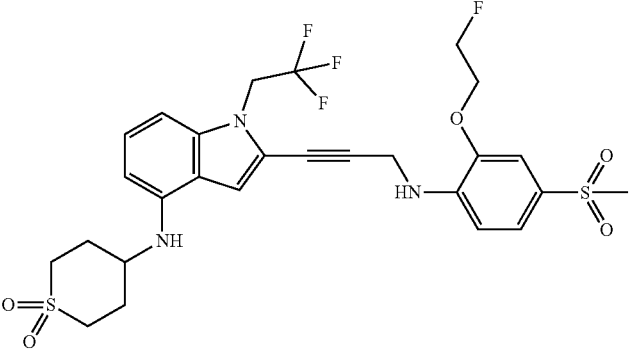 [SMILES: CS(=O)(=O)c1ccc(NCC#Cc2cc3c(NC4CCS(=O)(=O)CC4)cccc3n2CC(F)(F)F)c(OCCF)c1]<br>4-{[2-(3-{[2-(2-fluoroethoxy)-4-methanesulfonylphenyl]amino}prop-1-yn-1-yl)-1-(2,2,2-trifluoroethyl)-1H-indol-4-yl]amino]-1$\lambda^6$-thiane-1,1-dione |
| 451-P | 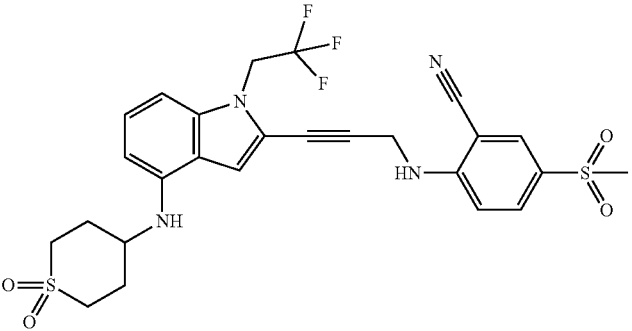 [SMILES: CS(=O)(=O)c1ccc(NCC#Cc2cc3c(NC4CCS(=O)(=O)CC4)cccc3n2CC(F)(F)F)c(C#N)c1]<br>2-[(3-{4-[(1,1-dioxo-1$\lambda^6$-thian-4-yl)amino]-1-(2,2,2-trifluoroethyl)-1H-indol-2-yl}prop-2-yn-1-yl)amino]-5-methanesulfonylbenzonitrile |

TABLE 1-continued
List of compounds
| # | Structure IUPAC name |
|---|---|
| 452-P | 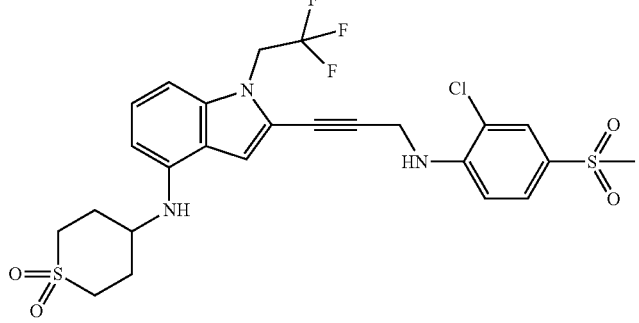 4-[(2-{3-[(2-chloro-4-methanesulfonyl-phenyl)amino]prop-1-yn-1-yl}-1-(2,2,2-trifluoroethyl)-1H-indol-4-yl)amino]-1λ⁶-thiane-1,1-dione |
| 453-P | 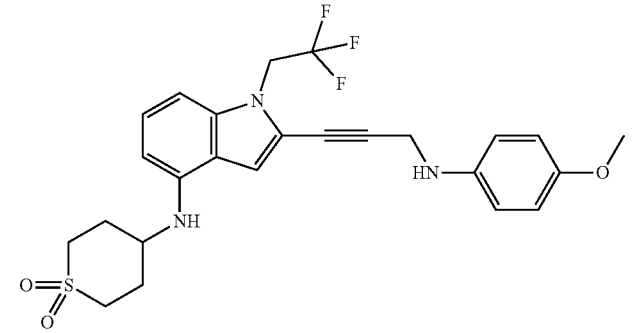 [SMILES: COc1ccc(NCC#Cc2cc3c(NC4CCS(=O)(=O)CC4)cccc3n2CC(F)(F)F)cc1] 4-[(2-{3-[(4-methoxyphenyl)amino]prop-1-yn-1-yl}-1-(2,2,2-trifluoroethyl)-1H-indol-4-yl)amino]-1λ⁶-thiane-1,1-dione |
| 454-P | 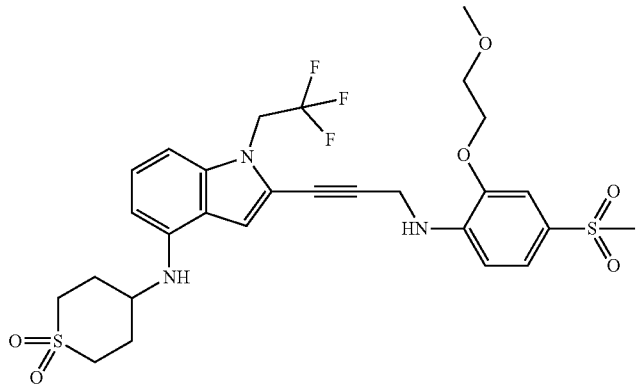 [SMILES: COCCOc1cc(S(C)(=O)=O)ccc1NCC#Cc1cc2c(NC3CCS(=O)(=O)CC3)cccc2n1CC(F)(F)F] 4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}-1λ⁶-thiane-1,1-dione |

TABLE 1-continued

List of compounds

| # | Structure IUPAC name |
|---|---|
| 455-P | 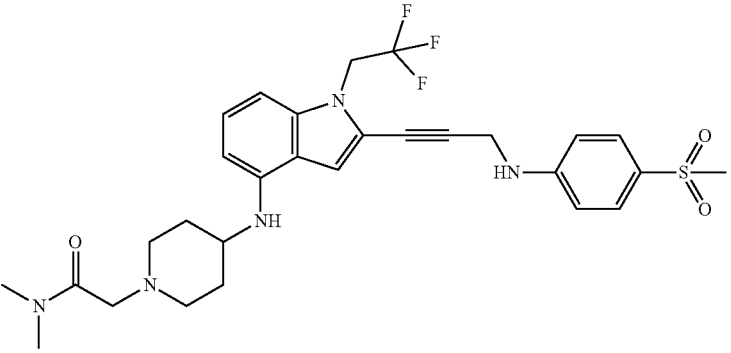<br>2-{4-[(2-{3-[(4-methanesulfonylphenyl)amino]prop-1-yn-1-yl}-1-(2,2,2-trifluoroethyl)-1H-indol-4-yl)amino]piperidin-1-yl}-N,N-dimethylacetamide |
| 456-P | 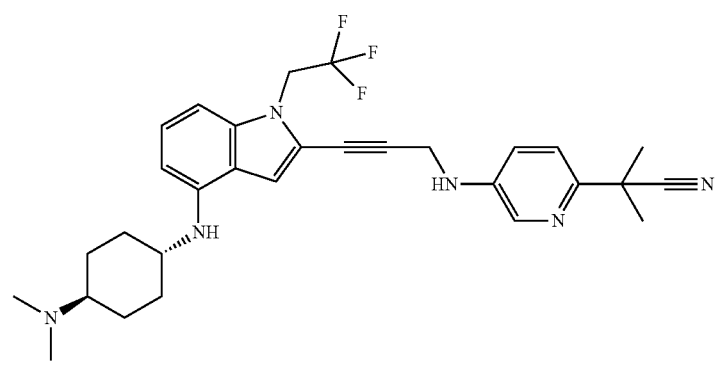 [SMILES: CN(C)[C@H]1CC[C@H](Nc2cccc3c2cc(C#CCNc2ccc(C(C)(C)C#N)nc2)n3CC(F)(F)F)CC1]<br>2-methyl-2-(5-{[3-(4-{[(1R,4R)-4-(dimethylamino)cyclohexyl]amino}-1-(2,2,2-trifluoroethyl)-1H-indol-2-yl)prop-2-yn-1-yl]amino}pyridin-2-yl)propanenitrile |
| 457-P | 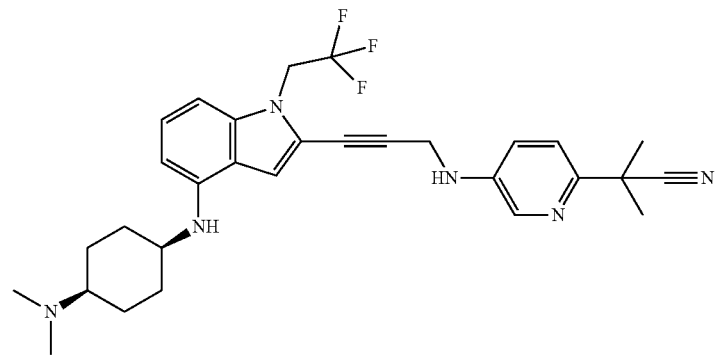 [SMILES: CN(C)[C@H]1CC[C@@H](Nc2cccc3c2cc(C#CCNc2ccc(C(C)(C)C#N)nc2)n3CC(F)(F)F)CC1]<br>2-(5-((3-(4-(((1S,4S)-4-(dimethylamino)-cyclohexyl)amino)-1-(2,2,2-trifluoroethyl)-1H-indol-2-yl)prop-2-yn-1-yl)amino)pyridin-2-yl)-2-methylpropanenitrile |

TABLE 1-continued

List of compounds

| # | Structure IUPAC name |
|---|---|

458-P

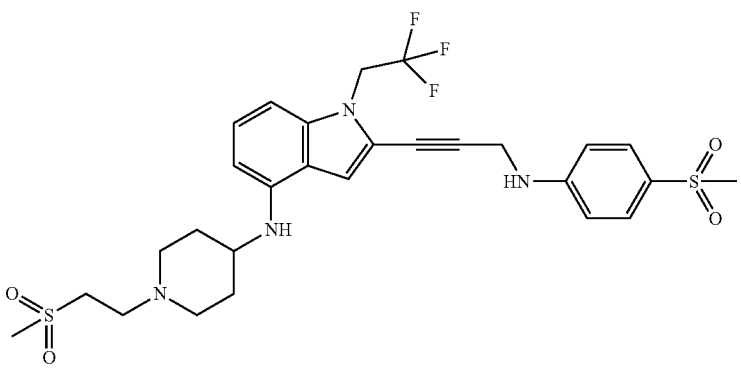 [SMILES: CS(=O)(=O)CCN1CCC(Nc2cccc3c2cc(C#CCNc2ccc(S(C)(=O)=O)cc2)n3CC(F)(F)F)CC1]

N-[1-(2-methanesulfonylethyl)piperidin-4-
yl]-2-{3-[(4-methanesulfonylphenyl)-
amino]prop-1-yn-1-yl}-1-(2,2,2-
trifluoroethyl)-1H-indol-4-amine

459-P

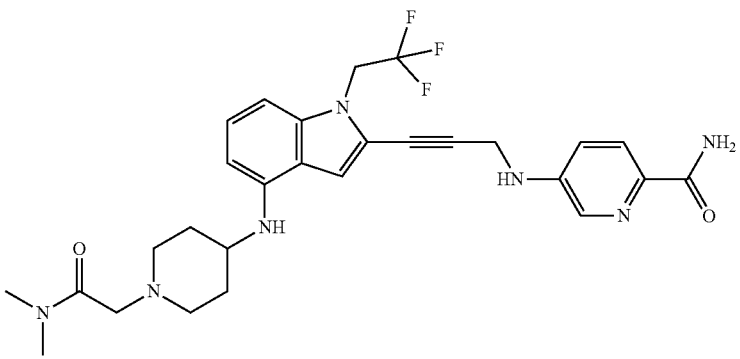 [SMILES: CN(C)C(=O)CN1CCC(Nc2cccc3c2cc(C#CCNc2ccc(C(N)=O)nc2)n3CC(F)(F)F)CC1]

5-({3-[4-({1-
[(dimethylcarbamoyl)methyl]piperidin-4-
yl}amino)-1-(2,2,2-trifluoroethyl)-1H-indol-
2-yl]prop-2-yn-1-yl}amino)pyridine-2-carboxamide

460-P

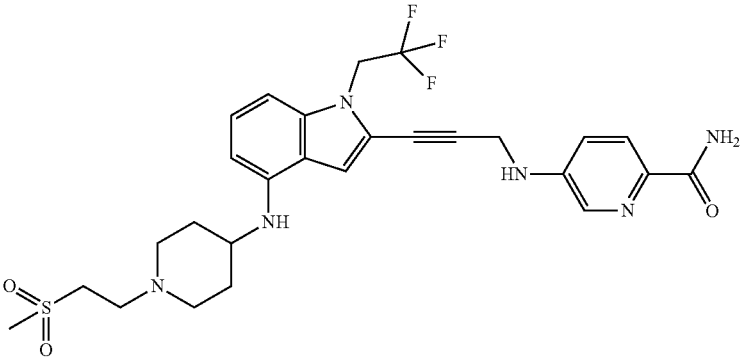 [SMILES: CS(=O)(=O)CCN1CCC(Nc2cccc3c2cc(C#CCNc2ccc(C(N)=O)nc2)n3CC(F)(F)F)CC1]

5-{[3-(4-{[1-(2-
methanesulfonylethyl)piperidin-4-yl]amino}-
1-(2,2,2-trifluoroethyl)-1H-indol-2-yl)prop-
2-yn-1-yl]amino}pyridine-2-carboxamide TABLE 1-continued
List of compounds
| # | Structure IUPAC name |
|---|---|
| 461-P | 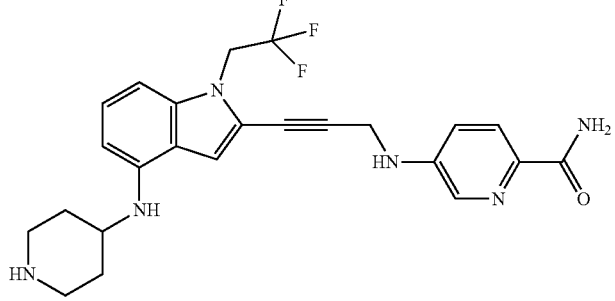
5-[(3-{4-[(piperidin-4-yl)amino]-1-(2,2,2-trifluoroethyl)-1H-indol-2-yl}prop-2-yn-1-yl)amino]pyridine-2-carboxamide |
| 462-P | 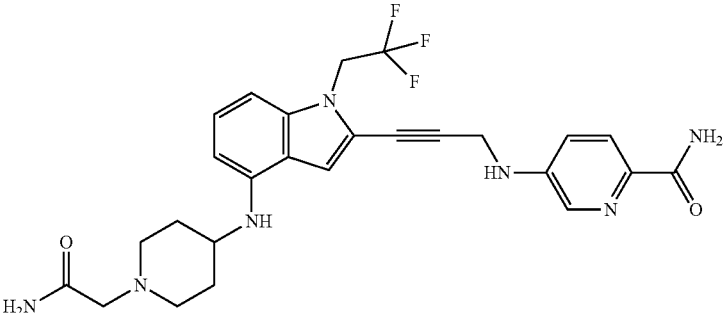
5-{[3-(4-{[1-(carbamoylmethyl)piperidin-4-yl]amino}-1-(2,2,2-trifluoroethyl)-1H-indol-2-yl)prop-2-yn-1-yl]amino}pyridine-2-carboxamide |
| 463-P | 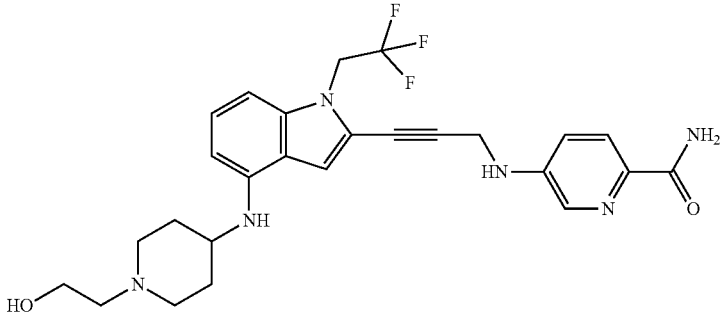 [SMILES: NC(=O)c1ccc(NCC#Cc2cc3c(NC4CCN(CCO)CC4)cccc3n2CC(F)(F)F)cn1]
5-{[3-(4-{[1-(2-hydroxyethyl)piperidin-4-yl]amino}-1-(2,2,2-trifluoroethyl)-1H-indol-2-yl)prop-2-yn-1-yl]amino}pyridine-2-carboxamide |

TABLE 1-continued
List of compounds
| # | Structure IUPAC name |
|---|---|
| 464-P | 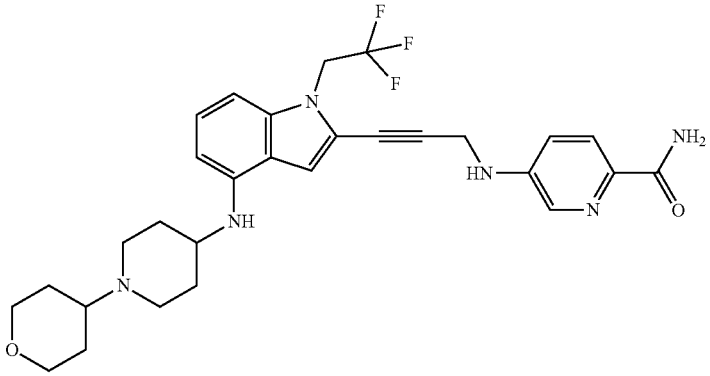 [SMILES: NC(=O)c1ccc(NCC#Cc2cc3c(NC4CCN(C5CCOCC5)CC4)cccc3n2CC(F)(F)F)cn1]
5-{[3-(4-{[1-(oxan-4-yl)piperidin-4-yl]amino}-1-(2,2,2-trifluoroethyl)-1H-indol-2-yl)prop-2-yn-1-yl]amino}pyridine-2-carboxamide |
| 465-P | 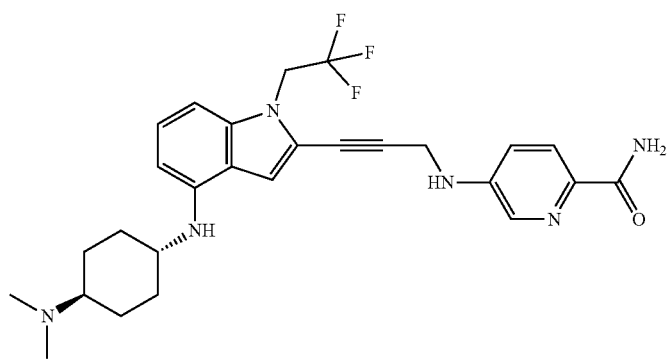 [SMILES: CN(C)[C@H]1CC[C@H](Nc2cccc3c2cc(C#CCNc2ccc(C(N)=O)nc2)n3CC(F)(F)F)CC1]
5-{[3-(4-{[(1R,4R)-4-(dimethylamino)-cyclohexyl]amino}-1-(2,2,2-trifluoroethyl)-1H-indol-2-yl)prop-2-yn-1-yl]amino}pyridine-2-carboxamide |
| 466-P | 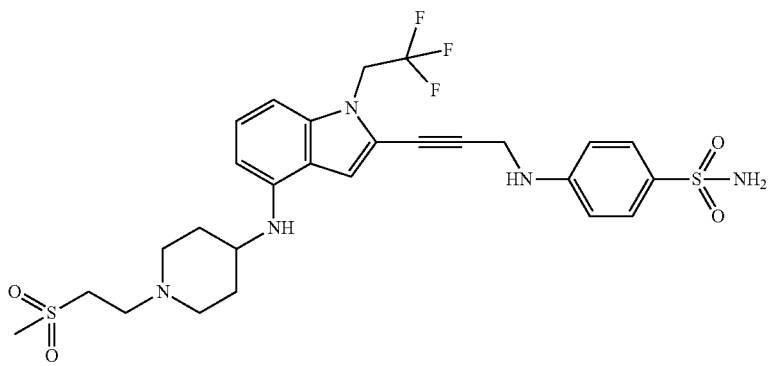 [SMILES: CS(=O)(=O)CCN1CCC(Nc2cccc3c2cc(C#CCNc2ccc(S(N)(=O)=O)cc2)n3CC(F)(F)F)CC1]
4-{[3-(4-{[1-(2-methanesulfonyl-ethyl)piperidin-4-yl]amino}-1-(2,2,2-trifluoroethyl)-1H-indol-2-yl)prop-2-yn-1-yl]amino}benzene-1-sulfonamide |

TABLE 1-continued

List of compounds

| # | Structure IUPAC name |
|---|---|
| 467-P | 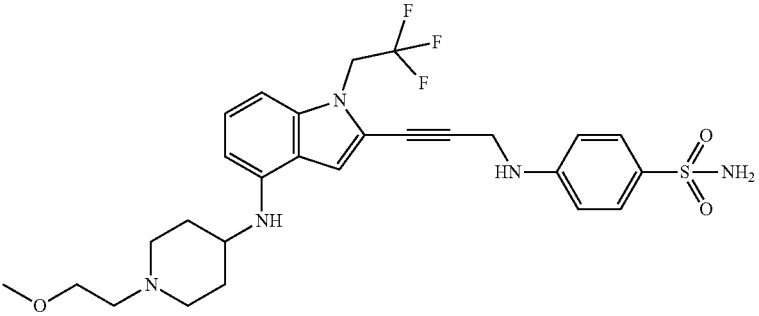 [SMILES: COCCN1CCC(Nc2cccc3c2cc(C#CCNc2ccc(S(N)(=O)=O)cc2)n3CC(F)(F)F)CC1]<br>4-{[3-(4-{[1-(2-methoxyethyl)piperidin-4-yl]amino}-1-(2,2,2-trifluoroethyl)-1H-indol-2-yl)prop-2-yn-1-yl]aminl}benzene-1-sulfonamide |
| 468-P | 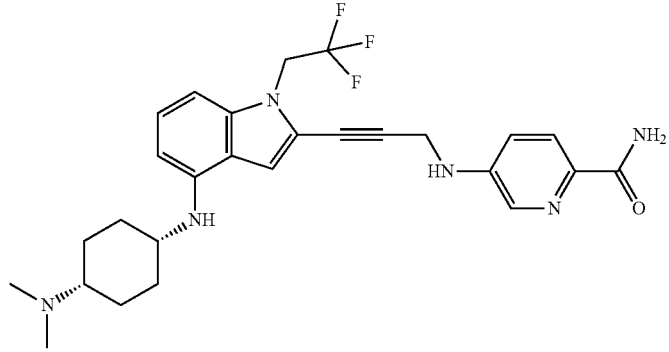 [SMILES: CN(C)[C@H]1CC[C@@H](Nc2cccc3c2cc(C#CCNc2ccc(C(N)=O)nc2)n3CC(F)(F)F)CC1]<br>5-{[3-(4-{[(1S,4S)-4-(dimethylamino)-cyclohexyl]amino}-1-(2,2,2-trifluoroethyl)-1H-indol-2-yl)prop-2-yn-1-yl]amino}pyridine-2-carboxamide |
| 469-P | 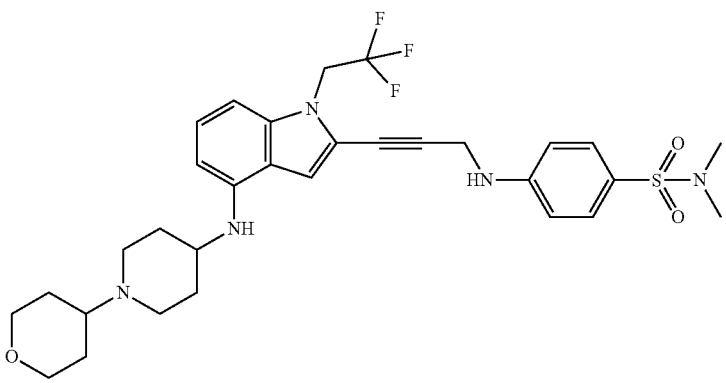 [SMILES: CN(C)S(=O)(=O)c1ccc(NCC#Cc2cc3c(NC4CCN(C5CCOCC5)CC4)cccc3n2CC(F)(F)F)cc1]<br>N,N-dimethyl-4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide |

TABLE 1-continued

List of compounds

| # | Structure IUPAC name |
|---|---|
| 470-P | 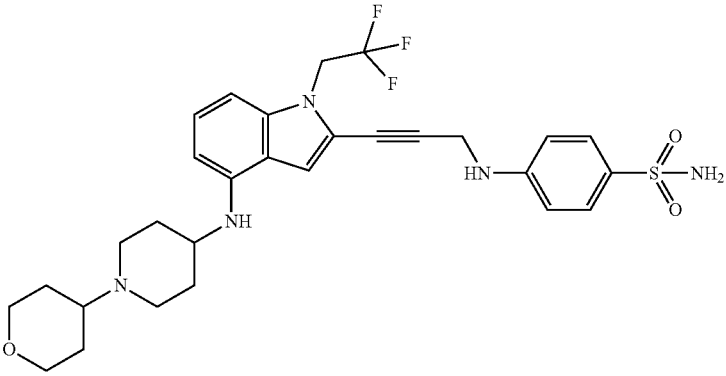 [SMILES: NS(=O)(=O)c1ccc(NCC#Cc2cc3c(NC4CCN(C5CCOCC5)CC4)cccc3n2CC(F)(F)F)cc1]<br>4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide |
| 471-P | 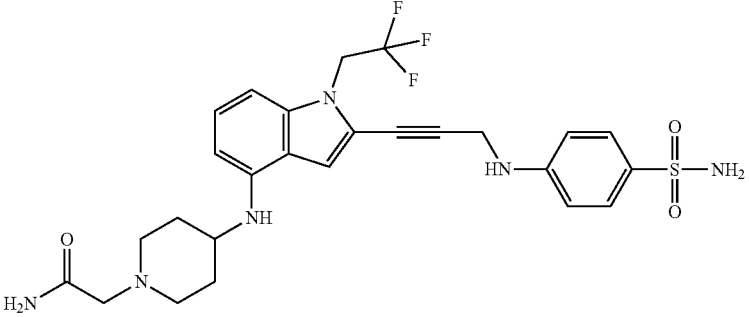 [SMILES: NC(=O)CN1CCC(Nc2cccc3c2cc(C#CCNc2ccc(S(N)(=O)=O)cc2)n3CC(F)(F)F)CC1]<br>2-{4-[(2-{3-[(4-sulfamoylphenyl)-amino]prop-1-yn-1-yl}-1-(2,2,2-trifluoroethyl)-1H-indol-4-yl)amino]-piperidin-1-yl}acetamide |
| 472-P | 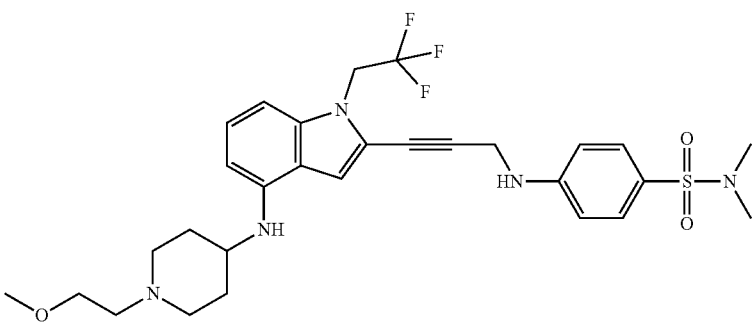<br>4-{[(3-(4-{[1-(2-methoxyethyl)piperidin-4-yl]amino}-1-(2,2,2-trifluoroethyl)-1H-indol-2-yl)prop-2-yn-1-yl]amino}-N,N-dimethylbenzene-1-sulfonamide |

TABLE 1-continued
List of compounds
| # | Structure IUPAC name |
|---|---|
| 473-P | 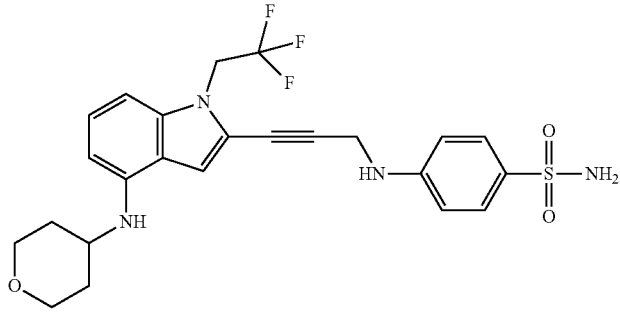 [SMILES: NS(=O)(=O)c1ccc(NCC#Cc2cc3c(NC4CCOCC4)cccc3n2CC(F)(F)F)cc1]<br>4-[(3-{4-[(oxan-4-yl)amino]-1-(2,2,2-trifluoroethyl)-1H-indol-2-yl}prop-2-yn-1-yl)amino]benzene-1-sulfonamide |
| 474-P | 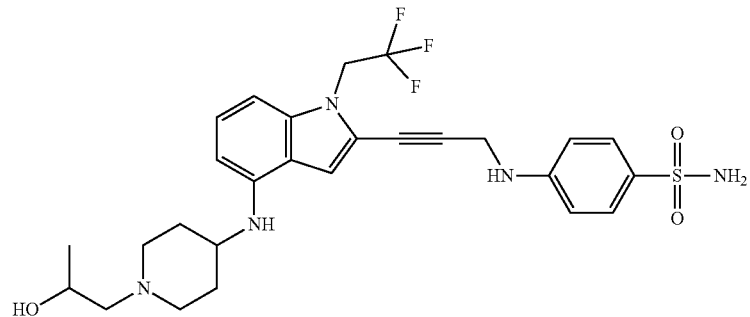 [SMILES: CC(O)CN1CCC(Nc2cccc3c2cc(C#CCNc2ccc(S(N)(=O)=O)cc2)n3CC(F)(F)F)CC1]<br>4-{[3-(4-{[1-(2-hydroxyethyl)piperidin-4-yl]amino}-1-(2,2,2-trifluoroethyl)-1H-indol-2-yl)prop-2-yn-1-yl]amino}benzene-1-sulfonamide |
| 475-P | 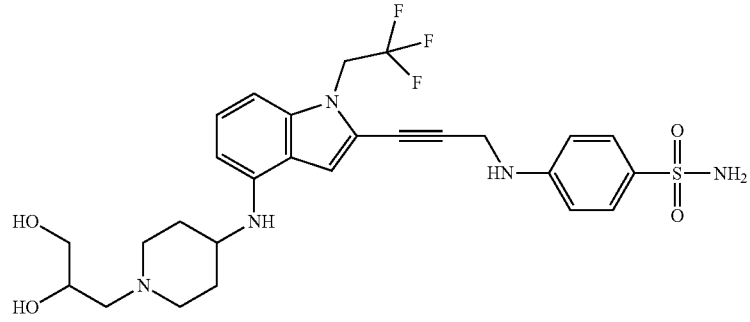 [SMILES: NS(=O)(=O)c1ccc(NCC#Cc2cc3c(NC4CCN(CC(O)CO)CC4)cccc3n2CC(F)(F)F)cc1]<br>4-{[3-(4-{[1-(2,3-dihydroxypropyl)piperidin-4-yl]amino}-1-(2,2,2-trifluoroethyl)-1H-indol-2-yl)prop-2-yn-1-yl]amino}benzene-1-sulfonamide |

TABLE 1-continued

List of compounds

| # | Structure IUPAC name |
|---|---|
| 476-P | 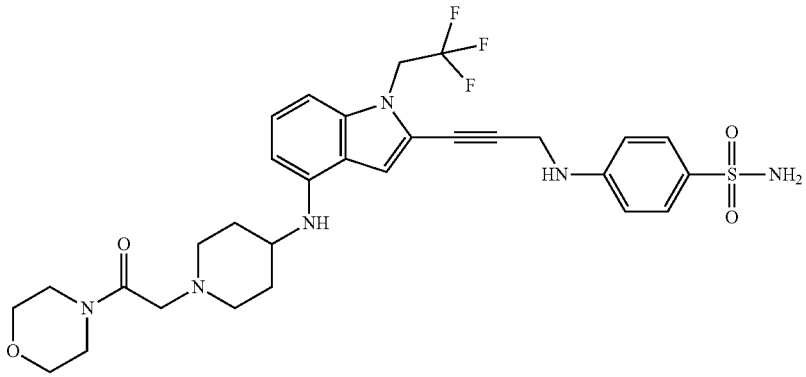 [SMILES: NS(=O)(=O)c1ccc(NCC#Cc2cc3c(NC4CCN(CC(=O)N5CCOCC5)CC4)cccc3n2CC(F)(F)F)cc1]<br>4-({3-[4-({1-[2-(morpholin-4-yl)-2-oxoethyl]piperidin-4-yl}amino)-1-(2,2,2-trifluoroethyl)-1H-indol-2-yl]prop-2-yn-1-yl}amino)benzene-1-sulfonamide |
| 477-P | 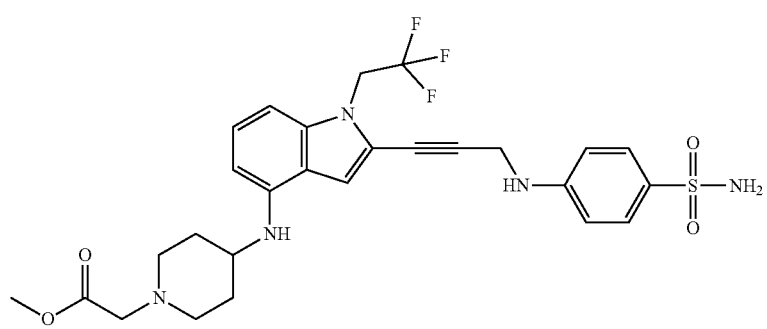 [SMILES: COC(=O)CN1CCC(Nc2cccc3c2cc(C#CCNc2ccc(S(N)(=O)=O)cc2)n3CC(F)(F)F)CC1]<br>methyl 2-{4-[(2-{3-[(4-sulfamoylphenyl)-amino]prop-1-yn-1-yl}-1-(2,2,2-trifluoro-ethyl)-1H-indol-4-yl)amino]piperidin-1-yl}acetate |
| 478-P | 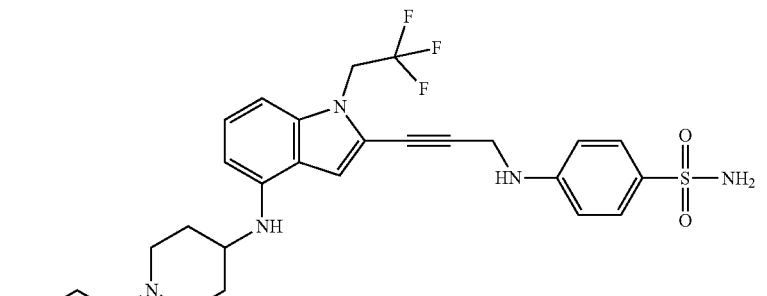<br>4-{[3-(4-{[1-(2-hydroxyethyl)piperidin-4-yl]amino}-1-(2,2,2-trifluoroethyl)-1H-indol-2-yl)prop-2-yn-1-yl]amino}benzene-1-sulfonamide |

TABLE 1-continued

List of compounds

| # | Structure IUPAC name |
|---|---|
| 479-P | 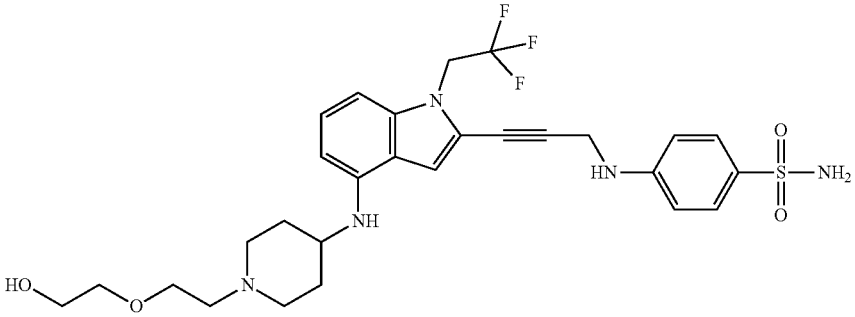 [SMILES: NS(=O)(=O)c1ccc(NCC#Cc2cc3c(NC4CCN(CCOCCO)CC4)cccc3n2CC(F)(F)F)cc1]<br>4-({3-[4-({1-[2-(2-hydroxyethoxy)ethyl]piperidin-4-yl}amino)-1-(2,2,2-trifluoroethyl)-1H-indol-2-yl]prop-2-yn-1-yl}amino)benzene-1-sulfonamide |
| 480-P | 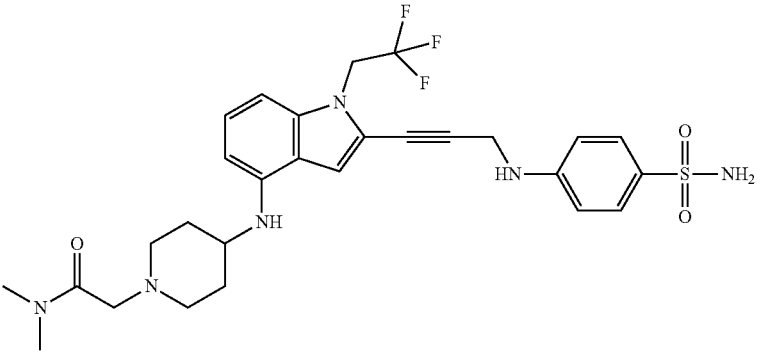 [SMILES: CN(C)C(=O)CN1CCC(Nc2cccc3c2cc(C#CCNc2ccc(S(N)(=O)=O)cc2)n3CC(F)(F)F)CC1]<br>N,N-dimethyl-2-{4-[(2-{3-[(4-sulfamoylphenyl)amino]prop-1-yn-1-yl}-1-(2,2,2-trifluoroethyl)-1H-indol-4-yl)amino]piperidin-1-yl}acetamide |
| 481-P | 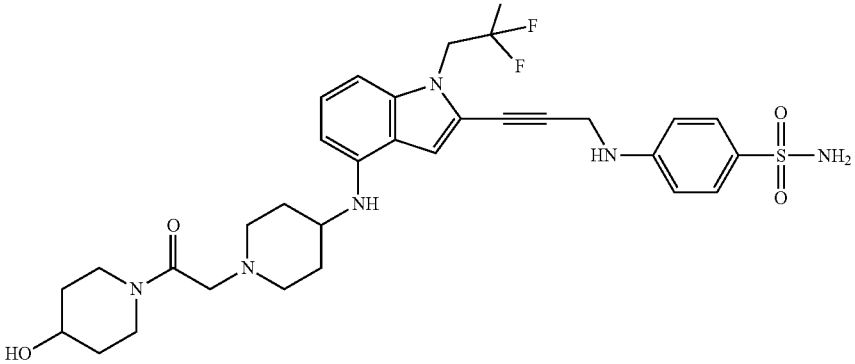<br>4-({3-[4-({1-[2-(4-hydroxypiperidin-1-yl)-2-oxoethyl]piperidin-4-yl}amino)-1-(2,2,2-trifluoroethyl)-1H-indol-2-yl]prop-2-yn-1-yl}amino)benzene-1-sulfonamide |

TABLE 1-continued

List of compounds

| # | Structure IUPAC name |
|---|---|
| 482-P | 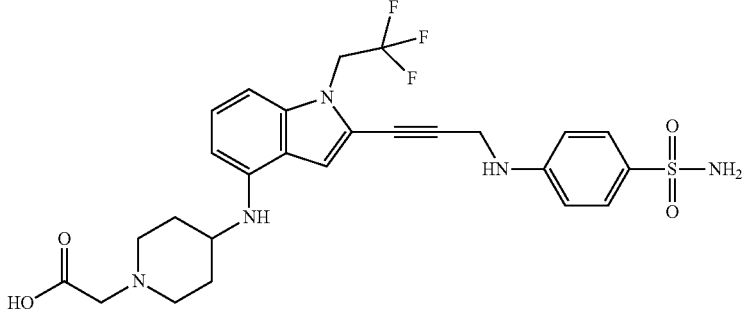 [SMILES: NS(=O)(=O)c1ccc(NCC#Cc2cc3c(NC4CCN(CC(=O)O)CC4)cccc3n2CC(F)(F)F)cc1]<br>2-{4-[(2-{3-[(4-sulfamoylphenyl)amino]prop-1-yn-1-yl}-1-(2,2,2-trifluoroethyl)-1H-indol-4-yl)amino]piperidin-1-yl}acetic acid |
| 483-P | 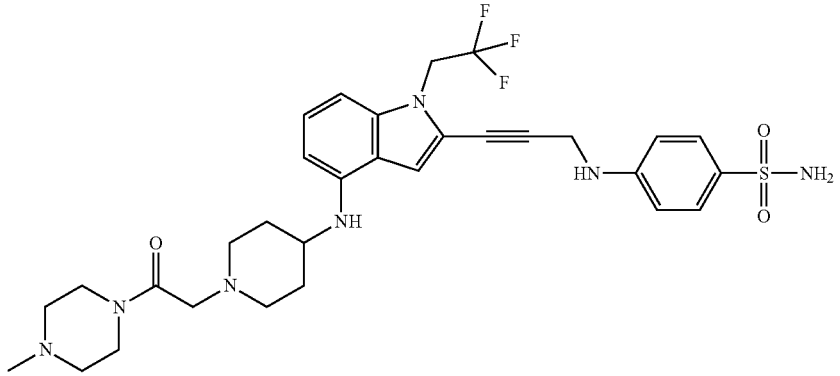 [SMILES: CN1CCN(C(=O)CN2CCC(Nc3cccc4c3cc(C#CCNc3ccc(S(N)(=O)=O)cc3)n4CC(F)(F)F)CC2)CC1]<br>4-({3-[4-({1-[2-(4-methylpiperazin-1-yl)-2-oxoethyl]piperidin-4-yl}amino)-1-(2,2,2-trifluoroethyl)-1H-indol-2-yl]prop-2-yn-1-yl}amino)benzene-1-sulfonamide |
| 484-P | 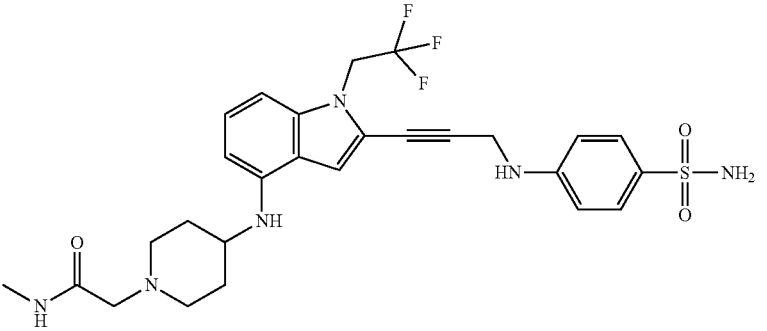 [SMILES: CNC(=O)CN1CCC(Nc2cccc3c2cc(C#CCNc2ccc(S(N)(=O)=O)cc2)n3CC(F)(F)F)CC1]<br>N-methyl-2-{4-[(2-{3-[(4-sulfamoylphenyl)amino]prop-1-yn-1-yl}-1-(2,2,2-trifluoroethyl)-1H-indol-4-yl)amino]piperidin-1-yl}acetamide |

| # | Structure | IUPAC name |
|---|---|---|
| 485-P | 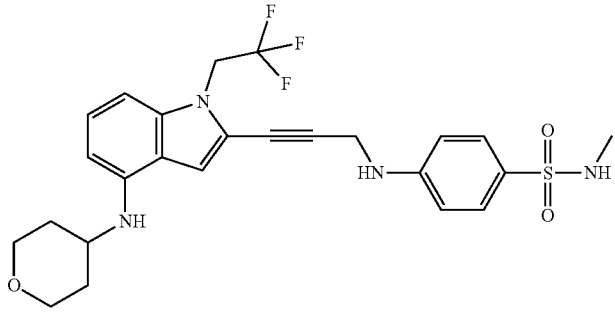 [SMILES: CNS(=O)(=O)c1ccc(NCC#Cc2cc3c(NC4CCOCC4)cccc3n2CC(F)(F)F)cc1] | N-methyl-4-[(3-{4-[(oxan-4-yl)amino]-1-(2,2,2-trifluoroethyl)-1H-indol-2-yl}prop-2-yn-1-yl)amino]benzene-1-sulfonamide |
| 486-P | 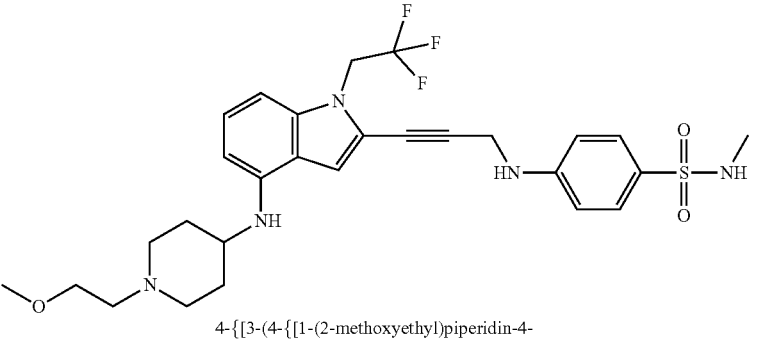 | 4-{[3-(4-{[1-(2-methoxyethyl)piperidin-4-yl]amino}-1-(2,2,2-trifluoroethyl)-1H-indol-2-yl)prop-2-yn-1-yl]amino}-N-methylbenzene-1-sulfonamide |
| 487-P | 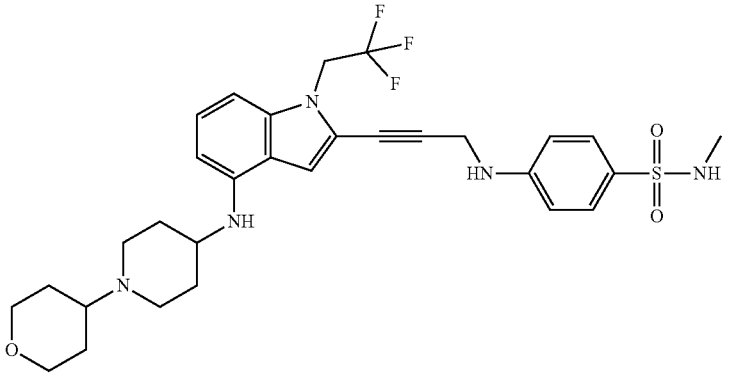 | N-methyl-4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide |

TABLE 1-continued
List of compounds
| # | Structure IUPAC name |
|---|---|
| 488-P | 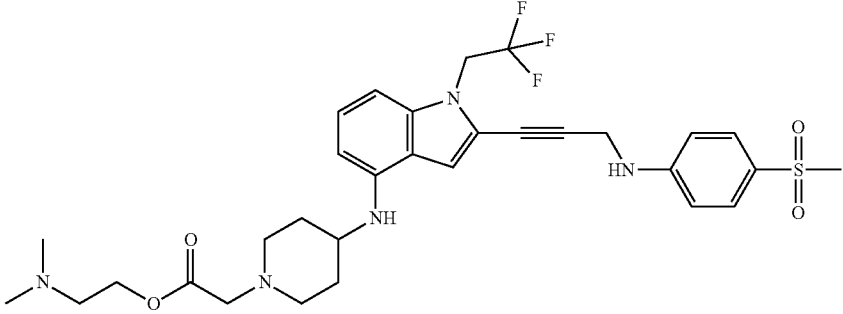<br>2-(dimethylamino)ethyl 2-{4-[(2-{3-[(4-methanesulfonylphenyl)-amino]prop-1-yn-1-yl}-1-(2,2,2-trifluoroethyl)-1H-indol-4-yl)amino]piperidin-1-yl}acetate |
| 489-P | 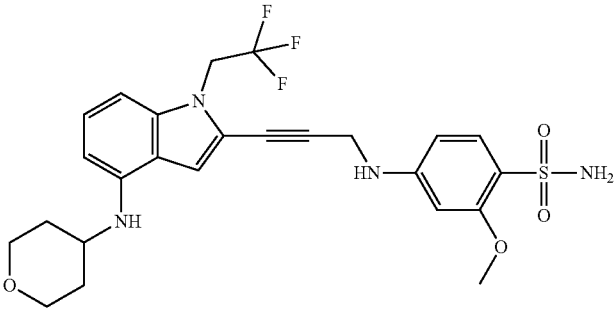 [SMILES: COc1cc(NCC#Cc2cc3c(NC4CCOCC4)cccc3n2CC(F)(F)F)ccc1S(N)(=O)=O]<br>2-methoxy-4-[(3-{4-{[(oxan-4-yl)amino]-1-(2,2,2-trifluoroethyl)-1H-indol-2-yl}prop-2-yn-1-yl)amino]benzene-1-sulfonamide |
| 490-P | 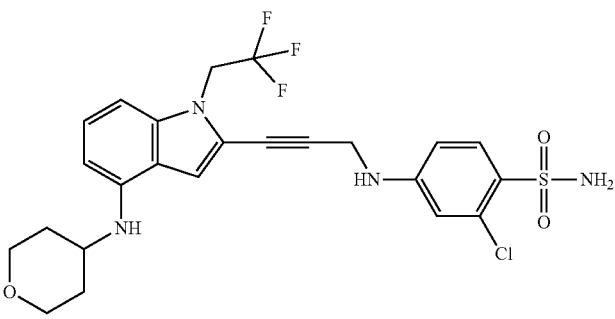 [SMILES: NS(=O)(=O)c1ccc(NCC#Cc2cc3c(NC4CCOCC4)cccc3n2CC(F)(F)F)cc1Cl]<br>2-chloro-4-[(3-{4-[(oxan-4-yl)amino]-1-(2,2,2-trifluoroethyl)-1H-indol-2-yl}prop-2-yn-1-yl)amino]benzene-1-sulfonamide |

TABLE 1-continued
List of compounds
| # | Structure | IUPAC name |
|---|---|---|
| 491-P | 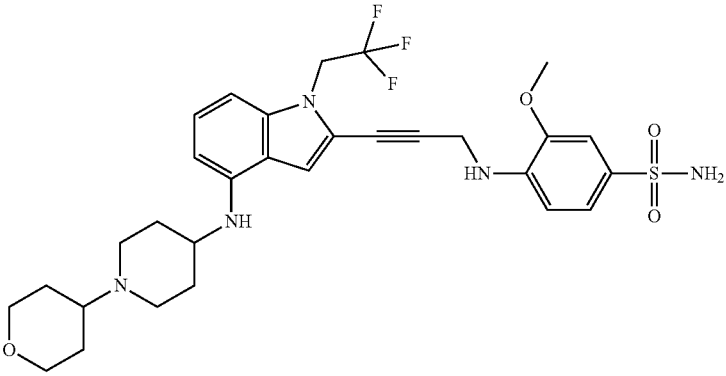 [SMILES: COc1cc(S(N)(=O)=O)ccc1NCC#Cc1cc2c(NC3CCN(C4CCOCC4)CC3)cccc2n1CC(F)(F)F] | 3-methoxy-4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide |
| 492-P | 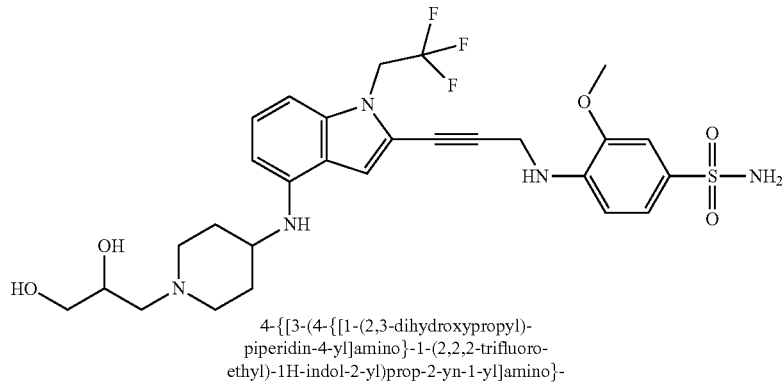 | 4-{[3-(4-{[1-(2,3-dihydroxypropyl)-piperidin-4-yl]amino}-1-(2,2,2-trifluoro-ethyl)-1H-indol-2-yl)prop-2-yn-1-yl]amino}-3-methoxybenzene-1-sulfonamide |
| 493-P | 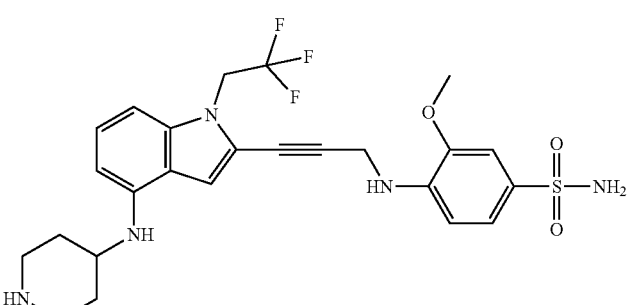 | 3-methoxy-4-[(3-{4-[(piperidin-4-yl)amino]-1-(2,2,2-trifluoroethyl)-1H-indol-2-yl}prop-2-yn-1-yl)amino]benzene-1-sulfonamide |

TABLE 1-continued

List of compounds

| # | Structure IUPAC name |
|---|---|
| 494-P | 3-methoxy-4-[(3-{4-[(oxan-4-yl)amino]-1-(2,2,2-trifluoroethyl)-1H-indol-2-yl}prop-2-yn-1-yl)amino]benzene-1-sulfonamide |
| 495-P | 3-methoxy-4-[(3-{4-[(oxan-4-yl)amino]-1-(2,2,2-trifluoroethyl)-1H-indol-2-yl}prop-2-yn-1-yl)amino]benzamide |
| 496-P | 3-methoxy-4-{[3-(4-{[1-(oxan-4-yl)piperidin-4-yl]amino}-1-(2,2,2-trifluoroethyl)-1H-indol-2-yl)prop-2-yn-1-yl]amino}benzamide |

TABLE 1-continued

List of compounds

| # | Structure IUPAC name |
|---|---|
| 497-P | 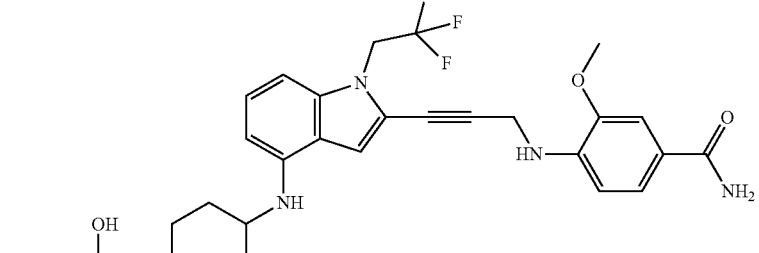<br>4-{[3-(4-{[1-(2,3-dihydroxypropyl)-piperidin-4-yl]amino}-1-(2,2,2-trifluoroethyl)-1H-indol-2-yl)prop-2-yn-1-yl]amino}-3-methoxybenzamide |
| 498-P | 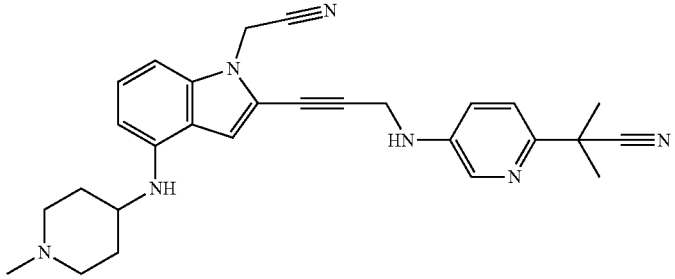 [SMILES: CN1CCC(Nc2cccc3c2cc(C#CCNc2ccc(C(C)(C)C#N)nc2)n3CC#N)CC1]<br>2-[5-({3-[1-(cyanomethyl)-4-[(1-methylpiperidin-4-yl)amino]-1H-indol-2-yl]prop-2-yn-1-yl}amino)pyridin-2-yl]-2-methylpropanenitrile |
| 499-P | 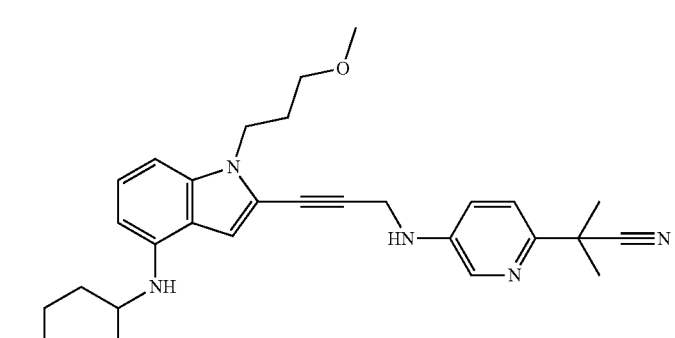<br>2-[5-({3-[1-(3-methoxypropyl)-4-[(1-methylpiperidin-4-yl)amino]-1H-indol-2-yl]prop-2-yn-1-yl}amino)pyridin-2-yl]-2-methylpropanenitrile |

TABLE 1-continued

List of compounds

| # | Structure IUPAC name |
|---|---|
| 500-P | 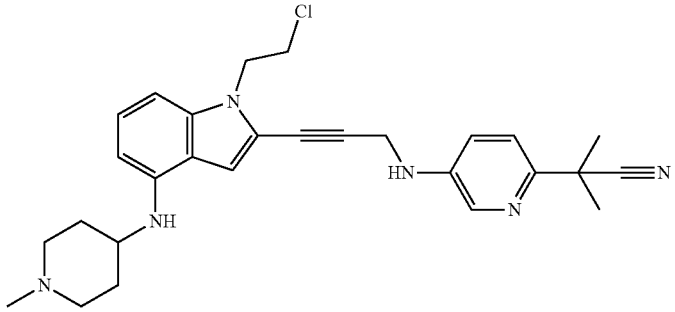 [SMILES: CN1CCC(Nc2cccc3c2cc(C#CCNc2ccc(C(C)(C)C#N)nc2)n3CCCl)CC1] 2-[5-({3-[1-(2-chloroethyl)-4-[(1-methylpiperidin-4-yl)amino]-1H-indol-2-yl]prop-2-yn-1-yl}amino)pyridin-2-yl]-2-methylpropanenitrile |
| 501-P | 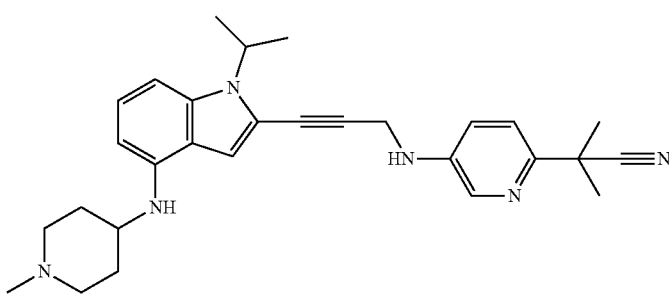 [SMILES: CC(C)n1c(C#CCNc2ccc(C(C)(C)C#N)nc2)cc2c(NC3CCN(C)CC3)cccc21] 2-methyl-2-{5-[(3-{4-[(1-methylpiperidin-4-yl)amino]-1-(propan-2-yl)-1H-indol-2-yl}prop-2-yn-1-yl)amino]pyridin-2-yl}propanenitrile |
| 502-P | 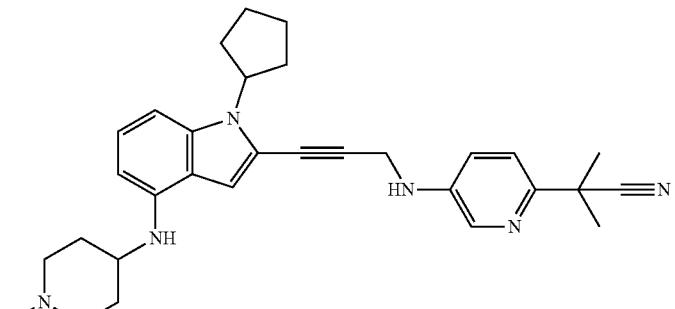 2-{5-[(3-{1-cyclopentyl-4-[(1-methylpiperidin-4-yl)amino]-1H-indol-2-yl}prop-2-yn-1-yl)amino]pyridin-2-yl}-2-methylpropanenitrile |
| 503-P | 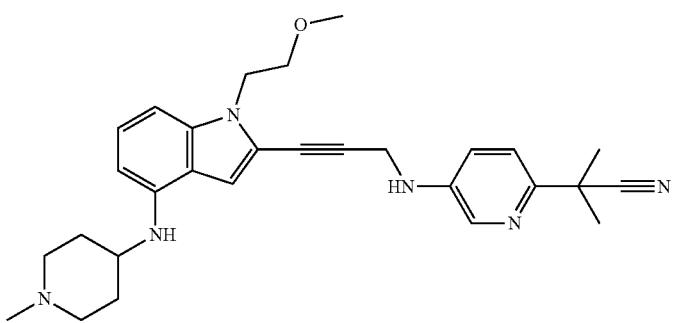 [SMILES: COCCn1c(C#CCNc2ccc(C(C)(C)C#N)nc2)cc2c(NC3CCN(C)CC3)cccc21] 2-methyl-2-{5-[(3-{4-[(1-methylpiperidin-4-yl)amino]-1-(3,3,3-trifluoropropyl)-1H-indol-2-yl}prop-2-yn-1-yl)amino]pyridin-2-yl}propanenitrile |

TABLE 1-continued

List of compounds

| # | Structure IUPAC name |
|---|---|
| 504-P | 1-(2-chloroethyl)-N-(1-methylpiperidin-4-yl)-2-{3-[(6-methylpyridin-3-yl)amino]-prop-1-yn-1-yl}-1H-indol-4-amine |
| 505-P | 1-(2-chloroethyl)-N-(1-methylpiperidin-4-yl)-2-{3-[(6-methylpyridin-3-yl)amino]-prop-1-yn-1-yl}-1H-indol-4-amine |
| 506-P | 1-(2-chloroethyl)-2-{3-[(4-chlorophenyl)-amino]prop-1-yn-1-yl}-N-(1-methylpiperidin-4-yl)-1H-indol-4-amine |

TABLE 1-continued

List of compounds

| # | Structure IUPAC name |
|---|---|
| 507-P | 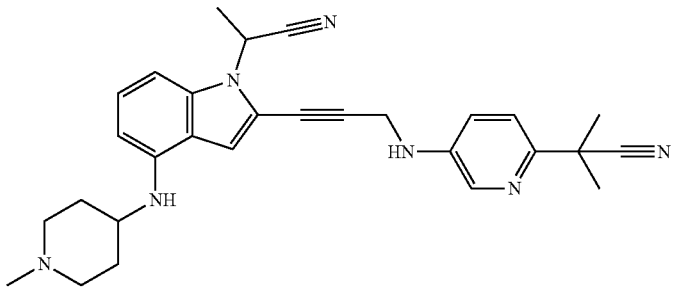<br>2-[5-({3-[1-(1-cyanoethyl)-4-[(1-methylpiperidin-4-yl)amino]-1H-indol-2-yl]prop-2-yn-1-yl}amino)pyridin-2-yl]-2-methylpropanenitrile<br>2-[5-({3-[1-(1-cyanoethyl)-4-[(1-methylpiperidin-4-yl)amino]-1H-indol-2-yl]prop-2-yn-1-yl}amino)pyridin-2-yl]-2-methylpropanenitrile |
| 508-P | 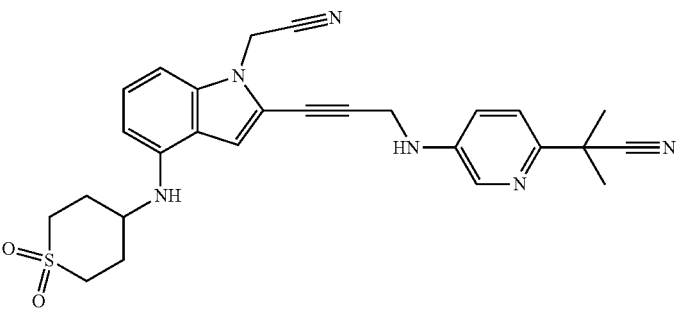<br>2-[5-({3-[1-(cyanomethyl)-4-[(1,1-dioxo-1λ⁶-thian-4-yl)amino]-1H-indol-2-yl]prop-2-yn-1-yl}amino)pyridin-2-yl]-2-methylpropanenitrile<br>2-[5-({3-[1-(cyanomethyl)-4-[(1,1-dioxo-1λ⁶-thian-4-yl)amino]-1H-indol-2-yl]prop-2-yn-1-yl}amino)pyridin-2-yl]-2-methylpropanenitrile |
| 509-P | 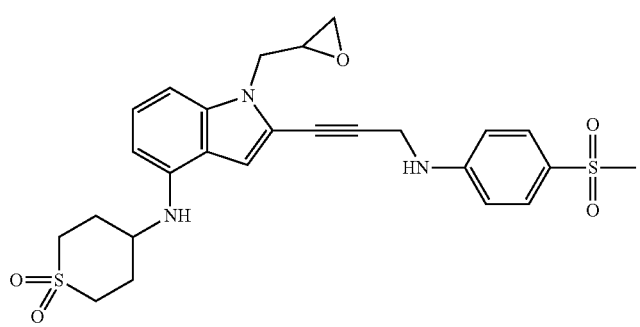<br>4-[(2-{3-[(4-methanesulfonylphenyl)amino]prop-1-yn-1-yl}-1-(oxiran-2-ylmethyl)-1H-indol-4-yl)amino]-1λ⁶-thiane-1,1-dione<br>4-[(2-{3-{(4-methanesulfonylphenyl)amino]prop-1-yn-1-yl}-1-(oxiran-2-ylmethyl)-1H-indol-4-yl)amino]-1λ⁶-thiane-1,1-dione |

TABLE 1-continued

List of compounds

| # | Structure IUPAC name |
|---|---|
| 510-P | 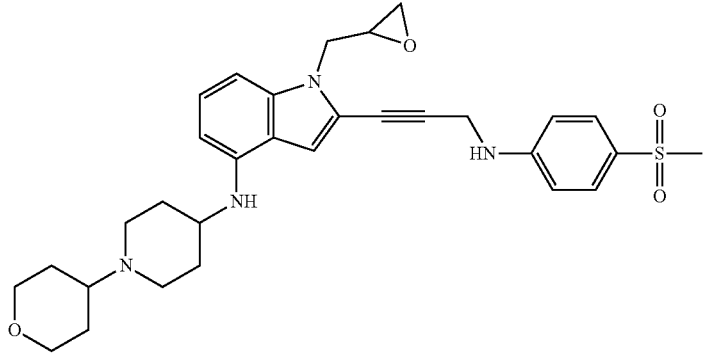<br>2-{3-[(4-methanesulfonylphenyl)-amino]prop-1-yn-1-yl}-N-[1-(oxan-4-yl)piperidin-4-yl]-1-(oxiran-2-ylmethyl)-1H-indol-4-amine<br>2-{3-[(4-methanesulfonylphenyl)-amino]prop-1-yn-1-yl}-N-[1-(oxan-4-yl)piperidin-4-yl]-1-(oxiran-2-ylmethyl)-1H-indol-4-amine |
| 511-P | 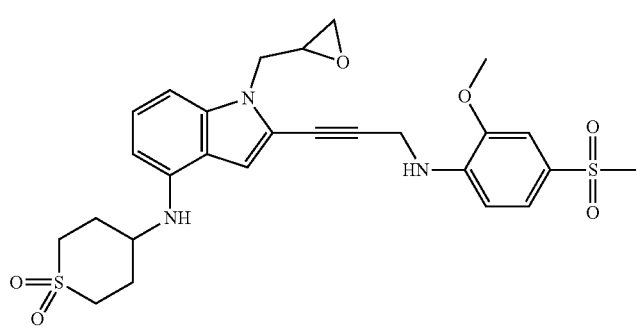<br>4-[(2-{3-[(4-methanesulfonyl-2-methoxyphenyl)amino]prop-1-yn-1-yl}-1-(oxiran-2-ylmethyl)-1H-indol-4-yl)aminno]-1λ⁶-thiane-1,1-dione<br>4-[(2-{3-[(4-methanesulfonyl-2-methoxyphenyl)amino]prop-1-yn-1-yl}-1-(oxiran-2-ylmethyl)-1H-indol-4-yl)amino]-1λ⁶-thiane-1,1-dione |
| 512-P | 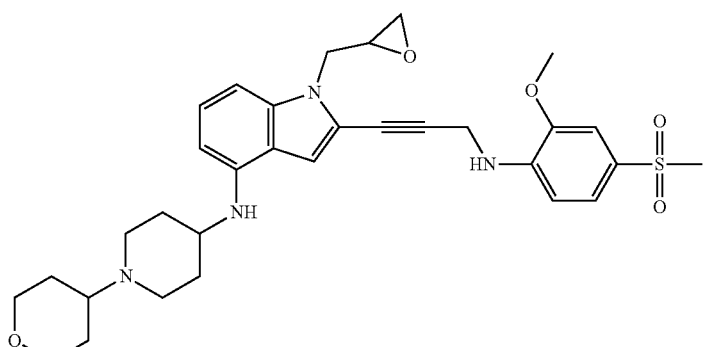<br>2-{3-[(4-methanesulfonyl-2-methoxy-phenyl)amino]prop-1-yn-1-yl}-N-[1-(oxan-4-yl)piperidin-4-yl]-1-(oxiran-2-ylmethyl)-1H-indol-4-amine<br>2-{3-[(4-methanesulfonyl-2-methoxy-phenyl)amino]prop-1-yn-1-yl}-N-[1-(oxan-4-yl)piperidin-4-yl]-1-(oxiran-2-ylmethyl)-1H-indol-4-amine |

TABLE 1-continued

List of compounds

| # | Structure IUPAC name |
|---|---|

513-P

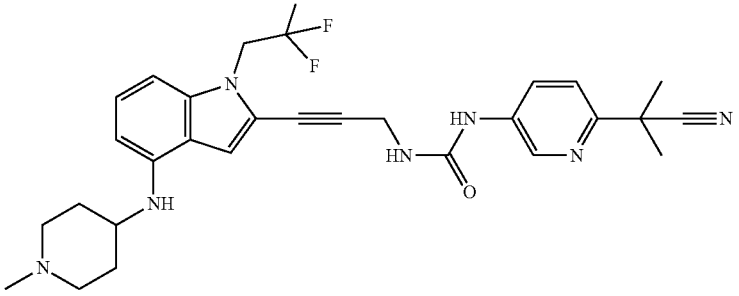

1-[6-(1-cyano-1-methylethyl)pyridin-3-yl]-3-(3-{4-[(1-methylpiperidin-4-yl)
amino]-1-(2,2,2-trifluoroethyl)-1H-indol-2-yl}prop-2-yn-1-yl)urea 1-[6-(1-cyano-1-methylethyl)pyridin-3-yl]-3-
(3-{4-[(1-methylpiperidin-4-yl)amino]-1-
(2,2,2-trifluoroethyl)-1H-indol-2-yl}prop-2-yn-1-yl)urea

514-P

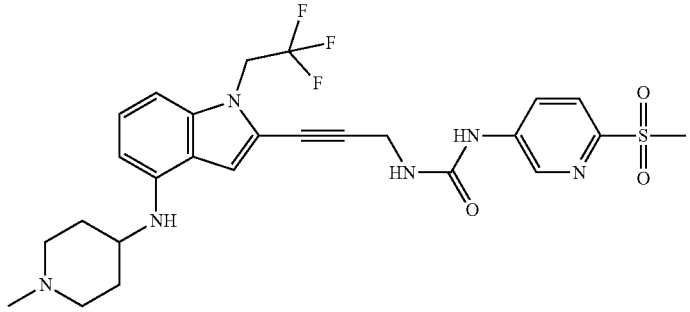

1-(6-methanesulfonylpyridin-3-yl)-3-(3-{4-[(1-methylpiperidin-4-yl)amino]
-1-(2,2,2-trifluoroethyl)-1H-indol-2-yl}prop-2-yn-1-yl)urea 1-(6-methanesulfonylpyridin-3-yl)-3-(3-{4-
[(1-methylpiperidin-4-yl)amino]-1-(2,2,2-
trifluoroethyl)-1H-indol-2-yl}prop-2-yn-1-yl)urea

515-P

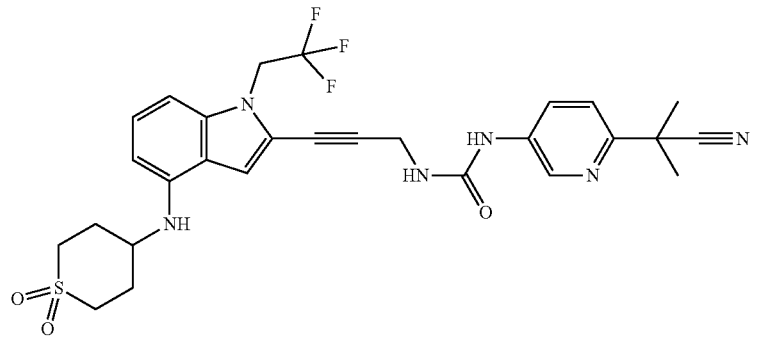

1-[6-(1-cyano-1-methylethyl)pyridin-3-yl]-3-(3-{4-[(1,1-dioxo-1λ⁶-thian-4-yl)amino]
-1-(2,2,2-trifluoroethyl)-1H-indol-2-yl}prop-2-yn-1-yl)urea 1-[6-(1-cyano-1-methylethyl)pyridin-3-yl]-3-
(3-{4-[(1,1-dioxo-1λ⁶-thian-4-yl)amino]-1-
(2,2,2-trifluoroethyl)-1H-indol-2-yl}prop-2-yn-1-yl)urea TABLE 1-continued List of compounds

| # | Structure IUPAC name |
|---|---|
| 516-P | 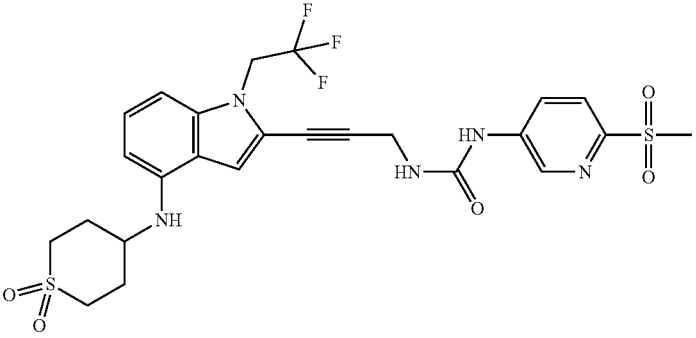<br>3-(3-{4-[(1,1-dioxo-1λ⁶-thian-4-yl)amino]-1-(2,2,2-trifluoroethyl)-1H-indol-2-yl}prop-2-yn-1-yl)-1-(6-methanesulfonylpyridin-3-yl)urea<br>3-(3-{4-[(1,1-dioxo-1λ⁶-thian-4-yl)amino]-1-(2,2,2-trifluoroethyl)-1H-indol-2-yl}prop-2-yn-1-yl)-1-(6-methanesulfonylpyridin-3-yl)urea |
| 517-P | 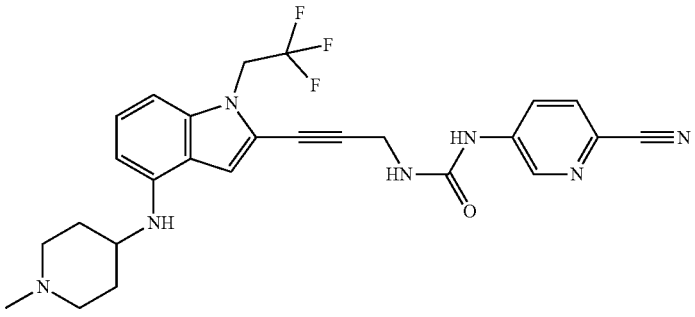<br>1-(6-cyanopyridin-3-yl)-3-(3-{4-[(1-methylpiperidin-4-yl)amino]-1-(2,2,2-trifluoroethyl)-1H-indol-2-yl}prop-2-yn-1-yl)urea<br>1-(6-cyanopyridin-3-yl)-3-(3-{4-[(1-methylpiperidin-4-yl)amino]-1-(2,2,2-trifluoroethyl)-1H-indol-2-yl}prop-2-yn-1-yl)urea |
| 518-P | 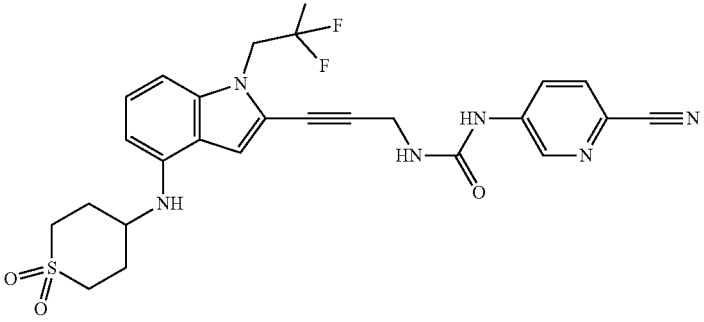<br>1-(6-cyanopyridin-3-yl)-3-(3-{4-[(1,1-dioxo-1λ⁶-thian-4-yl)amino]-1-(2,2,2-trifluoroethyl)-1H-indol-2-yl}prop-2-yn-1-yl)urea<br>1-(6-cyanopyridin-3-yl)-3-(3-{4-[(1,1-dioxo-1λ⁶-thian-4-yl)amino]-1-(2,2,2-trifluoroethyl)-1H-indol-2-yl}prop-2-yn-1-yl)urea |

TABLE 1-continued

List of compounds

| # | Structure IUPAC name |
|---|---|
| 519-P | 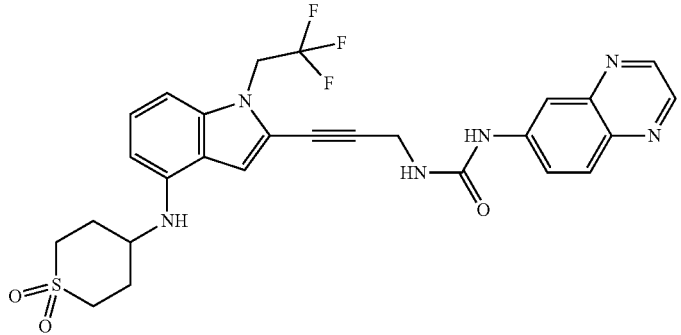 [SMILES: O=C(NCC#Cc1cc2c(NC3CCS(=O)(=O)CC3)cccc2n1CC(F)(F)F)Nc1ccc2nccnc2c1]<br>3-(3-{4-[(1,1-dioxo-1λ⁶-thian-4-yl)amino]-1-(2,2,2-trifluoroethyl)-1H-indol-2-yl}prop-2-yn-1-yl)-1-(quinoxalin-6-yl)urea |
| 520-P | 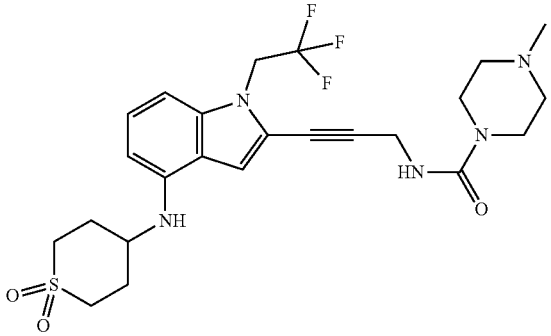<br>N-(3-{4-[(1,1-dioxo-1λ⁶-thian-4-yl)amino]-1-(2,2,2-trifluoroethyl)-1H-indol-2-yl}prop-2-yn-1-yl)-4-methylpiperazine-1-carboxamide<br>N-(3-{4-[(1,1-dioxo-1λ⁶-thian-4-yl)amino]-1-(2,2,2-trifluoroethyl)-1H-indol-2-yl}prop-2-yn-1-yl)-4-methylpiperazine-1-carboxamide |
| 521-P | 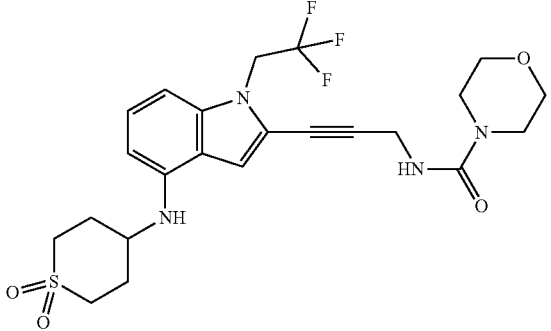<br>N-(3-{4-[(1,1-dioxo-1λ⁶-thian-4-yl)amino]-1-(2,2,2-trifluoroethyl)-1H-indol-2-yl}prop-2-yn-1-yl)morpholine-4-carboxamide<br>N-(3-{4-[(1,1-dioxo-1λ⁶-thian-4-yl)amino]-1-(2,2,2-trifluoroethyl)-1H-indol-2-yl}prop-2-yn-1-yl)morpholine-4-carboxamide |

TABLE 1-continued

List of compounds

| # | Structure IUPAC name |
|---|---|
| 522-P | 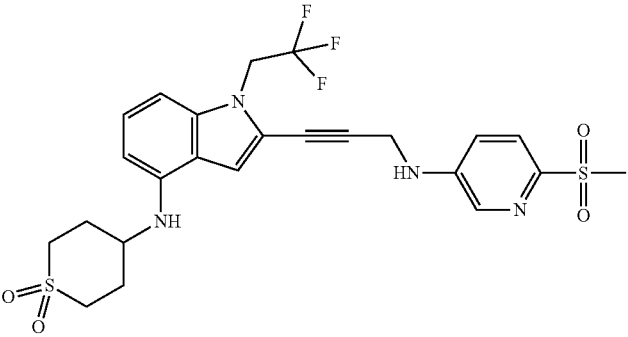  4-[(2-{3-[(6-methanesulfonylpyridin-3-yl)amino]prop-1-yn-1-yl}-1-(2,2,2-trifluoroethyl)-1H-indol-4-yl)amino]-1λ⁶-thiane-1,1-dione |
| 523-P | 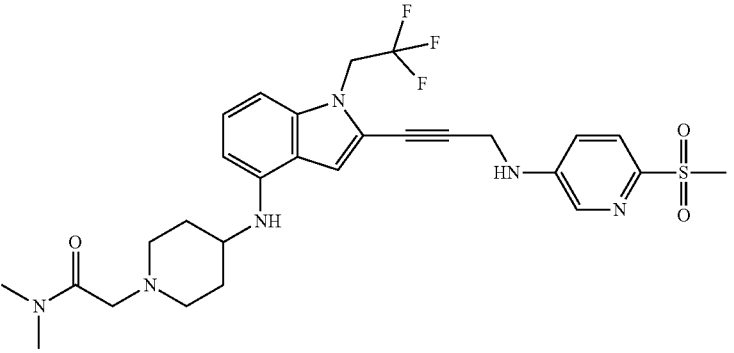  2-{4-[(2-{3-[(6-methanesulfonylpyridin-3-yl)amino]prop-1-yn-1-yl}-1-(2,2,2-trifluoroethyl)-1H-indol-4-yl)amino]piperidin-1-yl}-N,N-dimethylacetamide |
| 524-P | 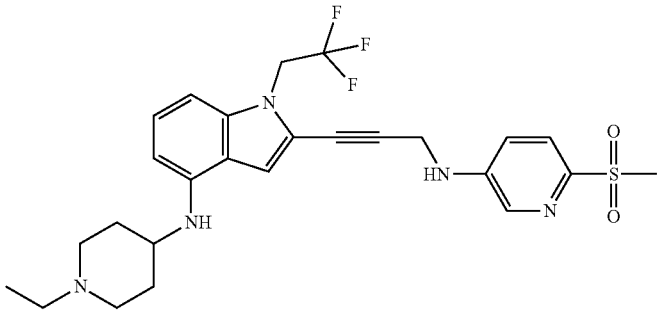 [SMILES: CCN1CCC(Nc2cccc3c2cc(C#CCNc2ccc(S(C)(=O)=O)nc2)n3CC(F)(F)F)CC1]  N-(1-ethylpiperidin-4-yl)-2-{3-[(6-methanesulfonylpyridin-3-yl)amino]prop-1-yn-1-yl}-1-(2,2,2-trifluoroethyl)-1H-indol-4-amine |

TABLE 1-continued

List of compounds

| # | Structure IUPAC name |
|---|---|
| 525-P | 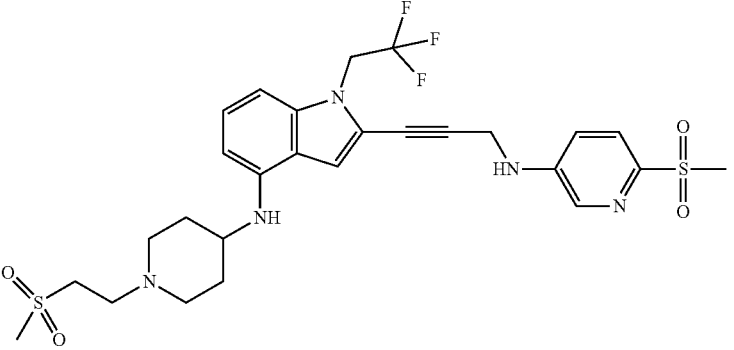 [SMILES: CS(=O)(=O)CCN1CCC(Nc2cccc3c2cc(C#CCNc2ccc(S(C)(=O)=O)nc2)n3CC(F)(F)F)CC1]<br>N-[1-(2-methanesulfonylethyl)piperidin-4-yl]-2-{3-[(6-methanesulfonylpyridin-3-yl)amino]prop-1-yn-1-yl}-1-(2,2,2-trifluoroethyl)-1H-indol-4-amine |
| 526-P | 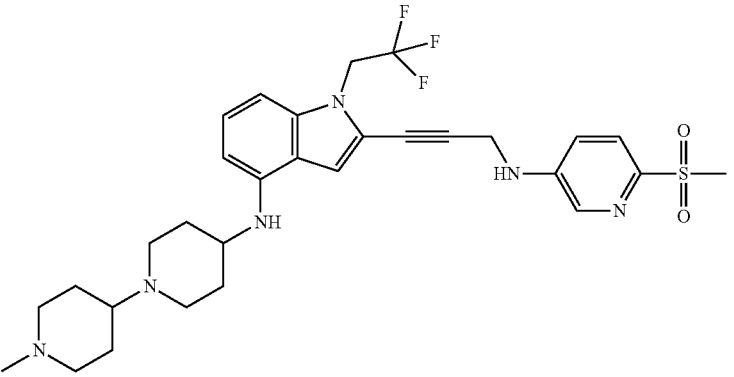<br>2-{3-[(6-methanesulfonylpyridin-3-yl)amino]prop-1-yn-1-yl}-N-[1-(1-methylpiperidin-4-yl)piperidin-4-yl]-1-(2,2,2-trifluoroethyl)-1H-indol-4-amine |
| 527-P | 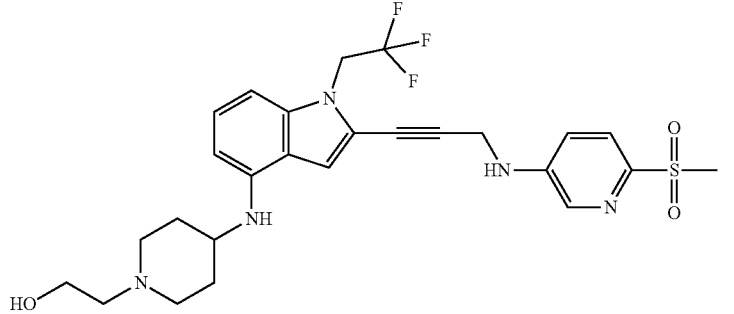<br>2-{4-[(2-{3-[(6-methanesulfonylpyridin-3-yl)amino]prop-1-yn-1-yl}-1-(2,2,2-trifluoroethyl)-1H-indol-4-yl)amino]piperidin-1-yl]ethan-1-ol |

TABLE 1-continued

List of compounds

| # | Structure IUPAC name |
|---|---|
| 528-P | 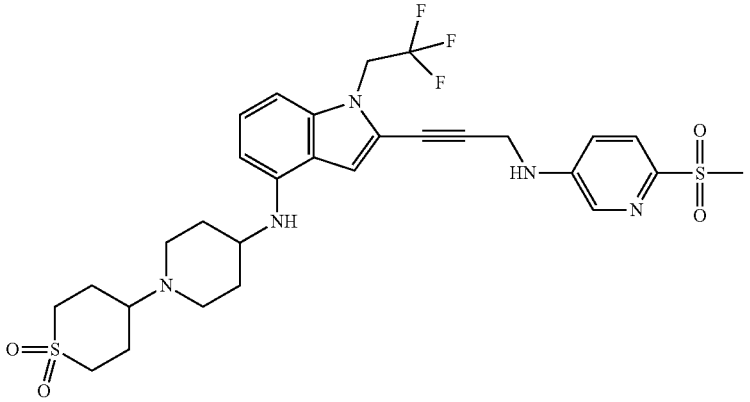 [SMILES: CS(=O)(=O)c1ccc(NCC#Cc2cc3c(NC4CCN(C5CCS(=O)(=O)CC5)CC4)cccc3n2CC(F)(F)F)cn1]<br>4-{4-[(2-{3-{[(6-methanesulfonylpyridin-3-yl)amino]prop-1-yn-1-yl}-1-(2,2,2-trifluoroethyl)-1H-indol-4-yl)amino]piperidin-1-yl}-1$\lambda^6$-thiane-1,1-dione |
| 529-P | 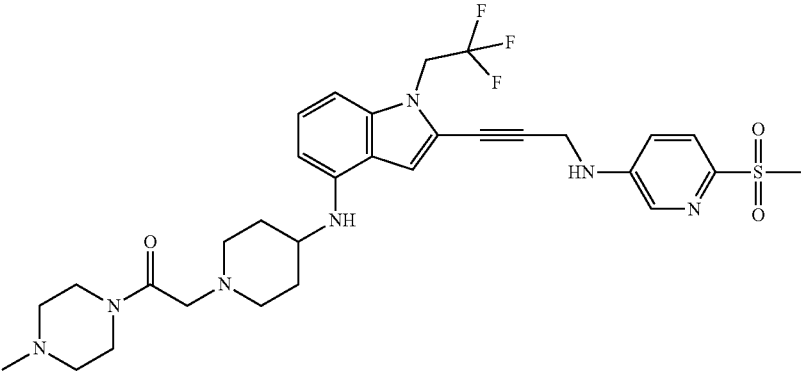<br>2-{4-[(2-{3-[(6-methanesulfonylpyridin-3-yl)amino]prop-1-yn-1-yl}-1-(2,2,2-trifluoroethyl)-1H-indol-4-yl)amino]piperidin-1-yl}-1-(4-methylpiperazin-1-yl)ethan-1-one |
| 530-P | 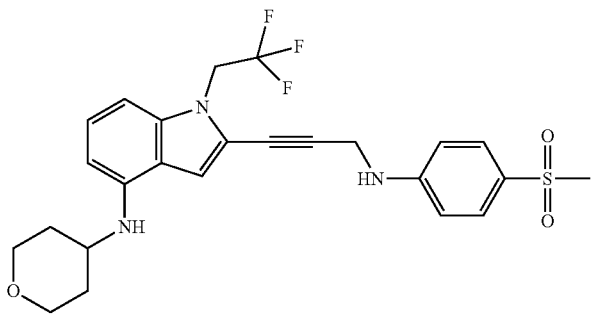 [SMILES: CS(=O)(=O)c1ccc(NCC#Cc2cc3c(NC4CCOCC4)cccc3n2CC(F)(F)F)cc1]<br>2-{3-[(4-methanesulfonylphenyl)amino]prop-1-yn-1-yl}-N-(oxan-4-yl)-1-(2,2,2-trifluoroethyl)-1H-indol-4-amine |

TABLE 1-continued

List of compounds

| # | Structure IUPAC name |
|---|---|

531-P

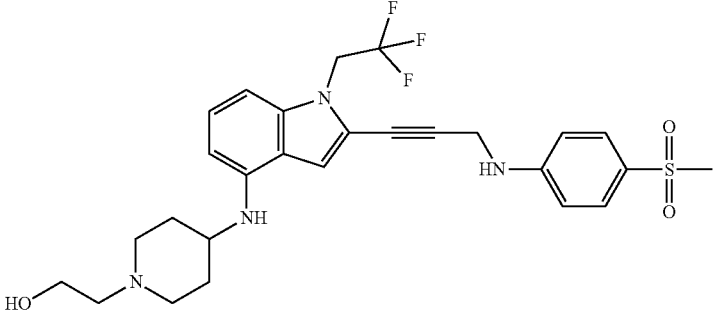

2-{4-[(2-{3-[(4-methanesulfonylphenyl)amino]prop-1-yn-1-yl}-1-(2,2,2-trifluoroethyl)-1H-indol-4-yl)amino]piperidin-1-yl}ethan-1-ol

532-P

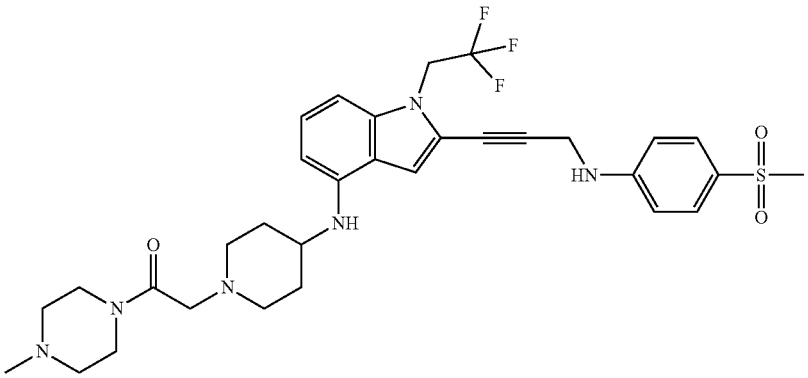

2-{4-[(2-{3-[(4-methanesulfonylphenyl)amino]prop-1-yn-1-yl}-1-(2,2,2-trifluoroethyl)-1H-indol-4-yl)amino]piperidin-1-yl}-1-(4-methylpiperazin-1-yl)ethan-1-one

533-P

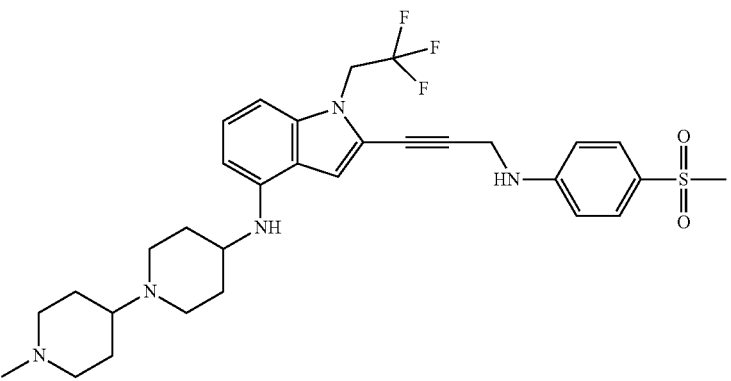

2-{3-[(4-methanesulfonylphenyl)amino]prop-1-yn-1-yl}-N-[1-(1-methylpiperidin-4-yl)piperidin-4-yl]-1-(2,2,2-trifluoroethyl)-1H-indol-4-amine TABLE 1-continued List of compounds

| # | Structure IUPAC name |
|---|---|
| 534-P | 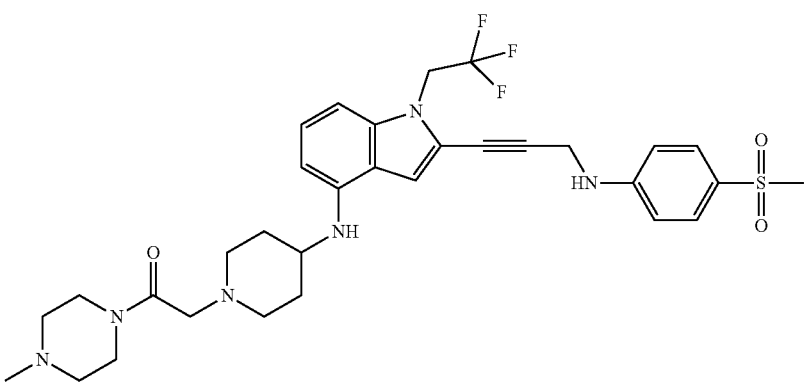<br>N-(2,3-dihydroxypropyl)-2-{4-[(2-{3-[(4-methanesulfonylphenyl)-amino]prop-1-yn-1-yl}-1-(2,2,2-trifluoroethyl)-1H-indol-4-yl)amino]piperidin-1-yl}-N-methylacetamide |
| 535-P | 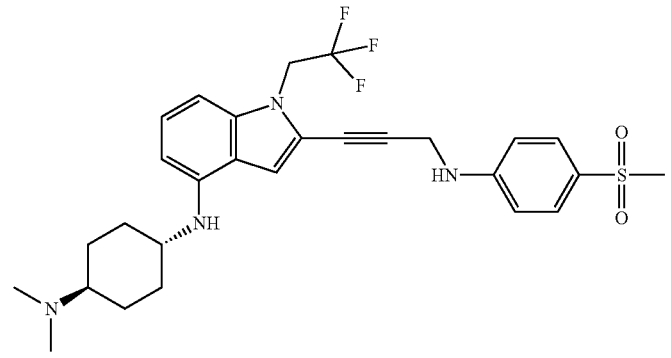<br>4-N-(2-{3-[(4-methanesulfonylphenyl)-amino]prop-1-yn-1-yl}-1-(2,2,2-trifluoroethyl)-1H-indol-4-yl)-1-N,1-N-dimethylcyclohexane-1,4-diamine |
| 536-P | 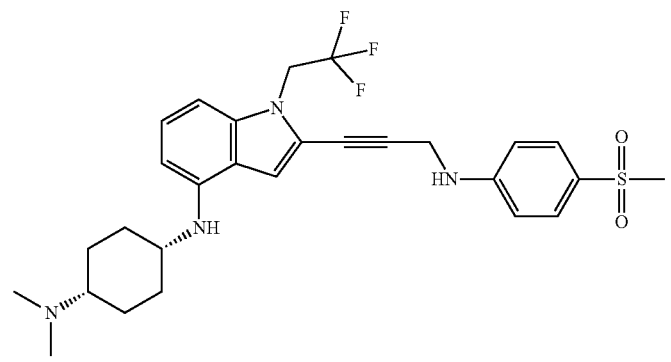<br>(1S,4S)-4-N-(2-{3-[(4-methanesulfonyl-phenyl)amino]prop-1-yn-1-yl}-1-(2,2,2-trifluoroethyl)-1H-indol-4-yl)-1-N,1-N-dimethylcyclohexane-1,4-diamine |

TABLE 1-continued

List of compounds

| # | Structure | IUPAC name |
|---|---|---|
| 537-P | 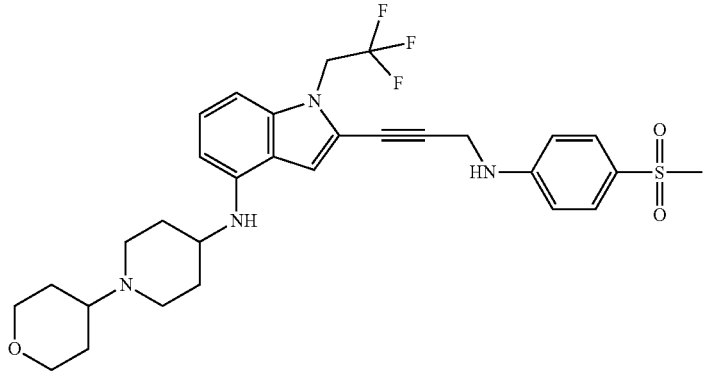 [SMILES: CS(=O)(=O)c1ccc(NCC#Cc2cc3c(NC4CCN(C5CCOCC5)CC4)cccc3n2CC(F)(F)F)cc1] | 2-{3-[(4-methanesulfonylphenyl)-amino]prop-1-yn-1-yl}-N-[1-(oxan-4-yl)piperidin-4-yl]-1-(2,2,2-trifluoroethyl)-1H-indol-4-amine |
| 538-P | 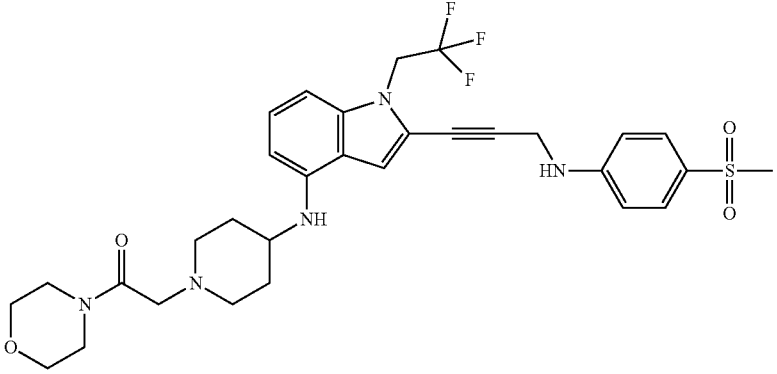 [SMILES: CS(=O)(=O)c1ccc(NCC#Cc2cc3c(NC4CCN(CC(=O)N5CCOCC5)CC4)cccc3n2CC(F)(F)F)cc1] | 2-{4-[(2-{3-[(4-methanesulfonylphenyl)amino]prop-1-yn-1-yl}-1-(2,2,2-trifluoroethyl)-1H-indol-4-yl)amino]piperidin-1-yl}-1-(morpholin-4-yl)ethan-1-one |
| 539-P | 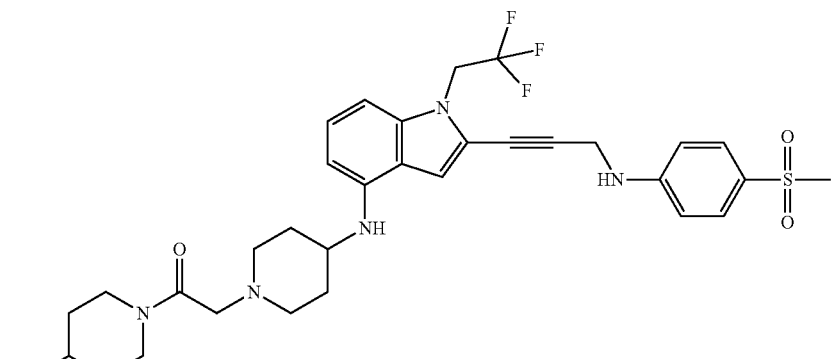 | 1-(4-hydroxypiperidin-1-yl)-2-{4-[(2-{3-[(4-methanesulfonylphenyl)-amino]prop-1-yn-1-yl}-1-(2,2,2-trifluoroethyl)-1H-indol-4-yl)amino]piperidin-1-yl}ethan-1-one |

TABLE 1-continued

List of compounds

| # | Structure IUPAC name |
|---|---|
| 540-P | 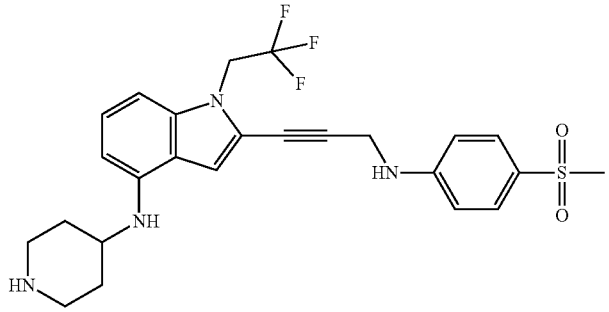 [SMILES: CS(=O)(=O)c1ccc(NCC#Cc2cc3c(NC4CCNCC4)cccc3n2CC(F)(F)F)cc1]<br>2-{3-[(4-methanesulfonylphenyl)-amino]prop-1-yn-1-yl}-N-(piperidin-4-yl)-1-(2,2,2-trifluoroethyl)-1H-indol-4-amine |
| 541-P | 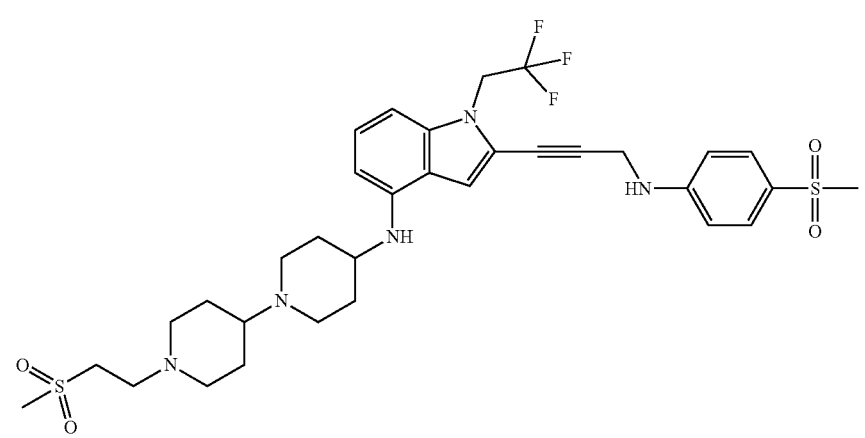 [SMILES: CS(=O)(=O)CCN1CCC(N2CCC(Nc3cccc4c3cc(C#CCNc3ccc(S(C)(=O)=O)cc3)n4CC(F)(F)F)CC2)CC1]<br>N-{1-[1-(2-methanesulfonylethyl)piperidin-4-yl]piperidin-4-yl}-2-{3-[(4-methanesulfonylphenyl)amino]prop-1-yn-1-yl}-1-(2,2,2-trifluoroethyl)-1H-indol-4-amine |
| 542-P | 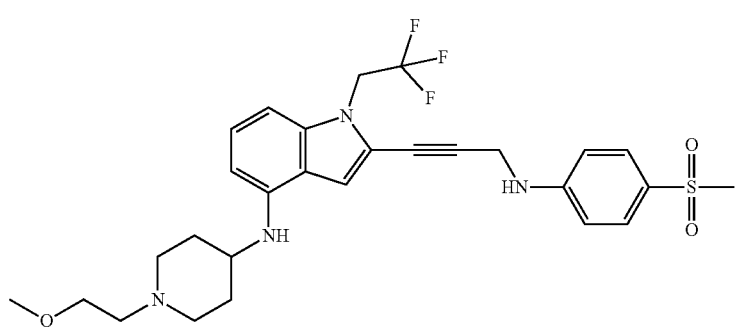<br>2-{3-[(4-methanesulfonylphenyl)-amino]prop-1-yn-1-yl}-N-[1-(2-methoxyethyl)piperidin-4-yl]-1-(2,2,2-trifluoroethyl)-1H-indol-4-amine |

TABLE 1-continued

List of compounds

| # | Structure IUPAC name |
|---|---|
| 543-P | 3-{4-[(2-{3-[(4-methane-sulfonylphenyl)-amino]prop-1-yn-1-yl}-1-(2,2,2-trifluoroethyl)-1H-indol-4-yl)amino]piperidin-1-yl}propanenitrile |
| 544-P | 2-{3-[(4-methanesulfonylphenyl)-amino]prop-1-yn-1-yl}-N-(1-methylpiperidin-4-yl)-1-(2,2,2-trifluoroethyl)-1H-indol-4-amine |
| 545-P | 2-{4-[(2-{3-[(4-methane-sulfonylphenyl)-amino]prop-1-yn-1-yl}-1-(2,2,2-trifluoroethyl)-1H-indol-4-yl)amino]piperidin-1-yl}acetamide |

TABLE 1-continued

List of compounds

| # | Structure IUPAC name |
|---|---|
| 546-P | 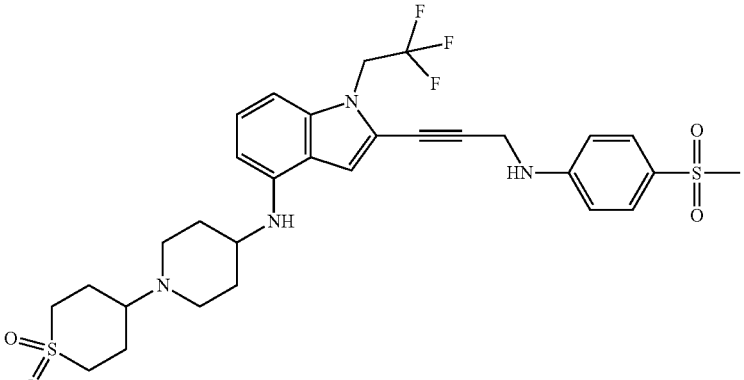<br>4-{4-[(2-{3-[(4-methane-sulfonylphenyl)-amino]prop-1-yn-1-yl}-1-(2,2,2-trifluoroethyl)-1H-indol-4-yl)amino]piperidin-1-yl}-1λ⁶-thiane-1,1-dione |
| 547-P | 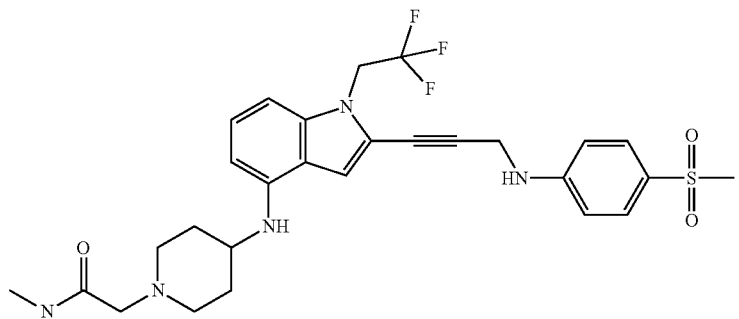<br>2-{4-[(2-{3-[(4-methane-sulfonylphenyl)amino]prop-1-yn-1-yl}-1-(2,2,2-trifluoroethyl)-1H-indol-4-yl)amino]piperidin-1-yl}-N-methylacetamide |
| 548-P | 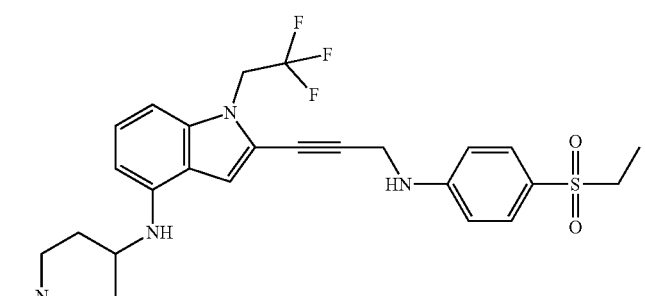<br>2-(3-{[4-(ethanesulfonyl)phenyl]amino}prop-1-yn-1-yl)-N-(1-methylpiperidin-4-yl)-1-(2,2,2-trifluoroethyl)-1H-indol-4-amine |

TABLE 1-continued

List of compounds

| # | Structure IUPAC name |
|---|---|
| 549-P | 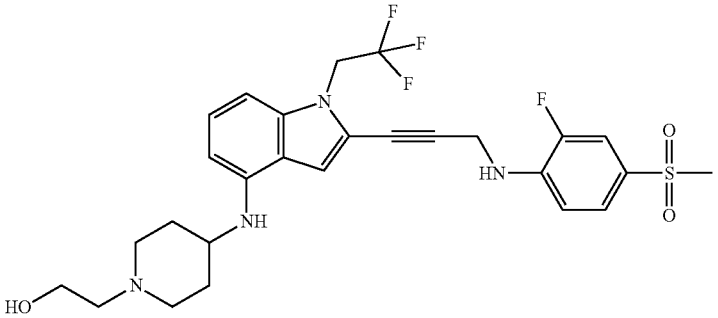 [SMILES: CS(=O)(=O)c1ccc(NCC#Cc2cc3c(NC4CCN(CCO)CC4)cccc3n2CC(F)(F)F)c(F)c1]<br>2-{4-[(2-{3-[(2-fluoro-4-methanesulfonylphenyl)amino]prop-1-yn-1-yl}-1-(2,2,2-trifluoroethyl)-1H-indol-4-yl)amino]piperidin-1-yl}ethan-1-ol |
| 550-P | 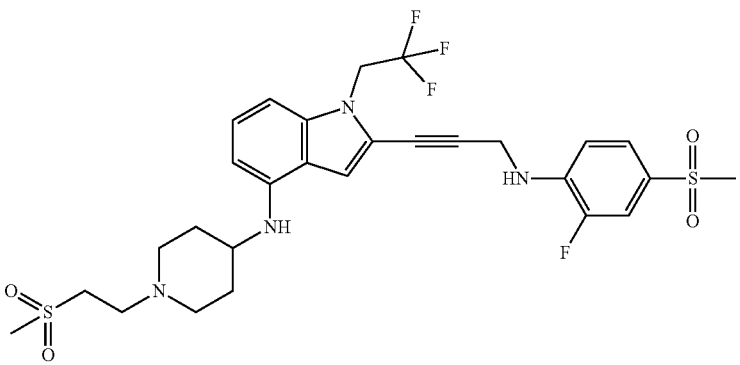 [SMILES: CS(=O)(=O)CCN1CCC(Nc2cccc3c2cc(C#CCNc2ccc(S(C)(=O)=O)cc2F)n3CC(F)(F)F)CC1]<br>2-{3-[(2-fluoro-4-methane-sulfonylphenyl)-amino]prop-1-yn-1-yl}-N-[1-(2-methanesulfonylethyl)-piperidin-4-yl]-1-(2,2,2-trifluoroethyl)-1H-indol-4-amine |
| 551-P | 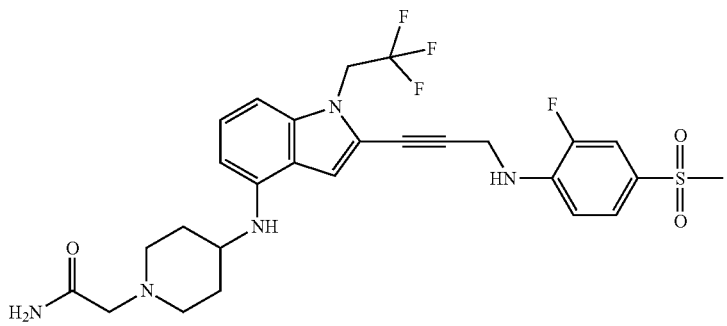 [SMILES: CS(=O)(=O)c1ccc(NCC#Cc2cc3c(NC4CCN(CC(N)=O)CC4)cccc3n2CC(F)(F)F)c(F)c1]<br>2-{4-[(2-{3-[(2-fluoro-4-methanesulfonylphenyl)amino]prop-1-yn-1-yl}-1-(2,2,2-trifluoroethyl)-1H-indol-4-yl)amino]piperidin-1-yl}acetamide |

TABLE 1-continued
List of compounds
| # | Structure IUPAC name |
|---|---|
552-P
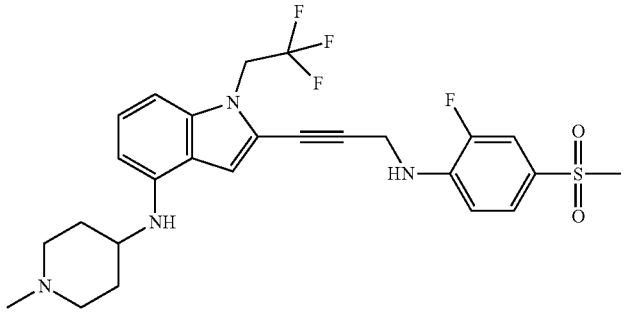
2-{3-[(2-fluoro-4-methane-sulfonylphenyl)-
amino]prop-1-yn-1-yl}-N-(1-
methylpiperidin-4-yl)-1-(2,2,2-
trifluoroethyl)-1H-indol-4-amine
553-P
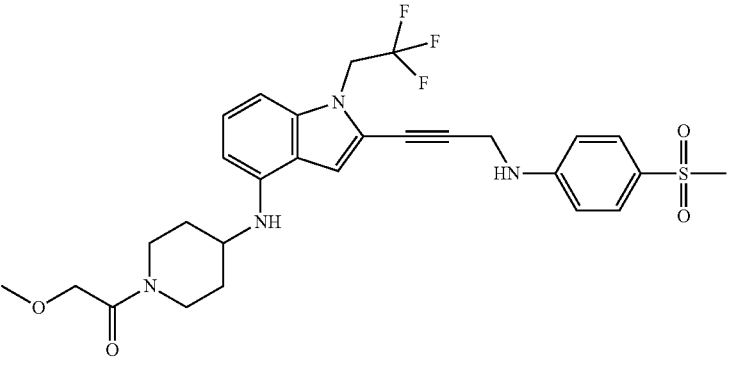
1-{4-[(2-{3-[(4-methanesulfonyl-
phenyl)amino]prop-1-yn-1-yl}-1-(2,2,2-
trifluoroethyl)-1H-indol-4-yl)
amino]piperidin-1-yl}-2-methoxyethan-1-one
554-P
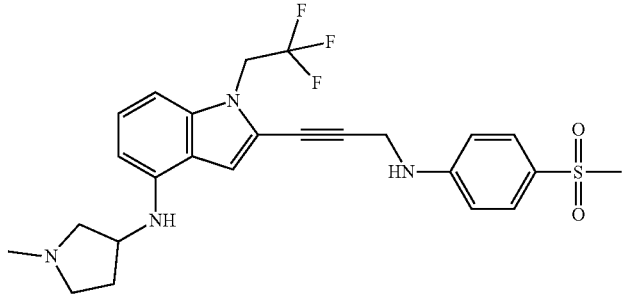
2-{3-[(4-methanesulfonyl-
phenyl)amino]prop-1-yn-1-yl}-N-(1-
methylpyrrolidin-3-yl)-1-(2,2,2-
trifluoroethyl)-1H-indol-4-amine TABLE 1-continued List of compounds

| # | Structure IUPAC name |
|---|---|

555-P

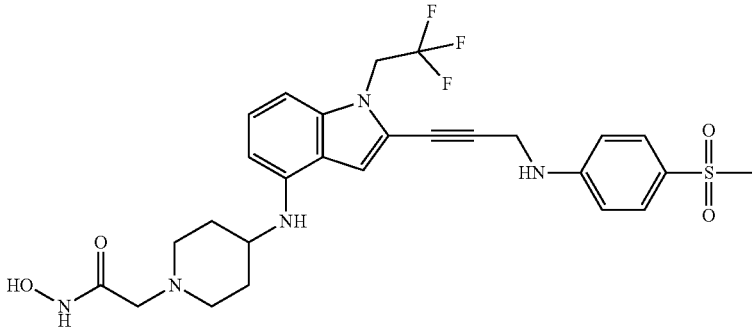 [SMILES: CS(=O)(=O)c1ccc(NCC#Cc2cc3c(NC4CCN(CC(=O)NO)CC4)cccc3n2CC(F)(F)F)cc1]

N-hydroxy-2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetamide

556-P

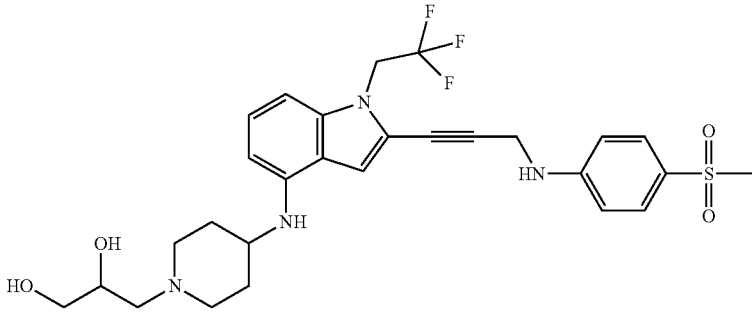 [SMILES: CS(=O)(=O)c1ccc(NCC#Cc2cc3c(NC4CCN(CC(O)CO)CC4)cccc3n2CC(F)(F)F)cc1]

3-{4-[(2-{3-[(4-methanesulfonyl-phenyl)amino]prop-1-yn-1-yl}-1-(2,2,2-trifluoroethyl)-1H-indol-4-yl)amino]piperidin-1-yl}propane-1,2-diol

557-P

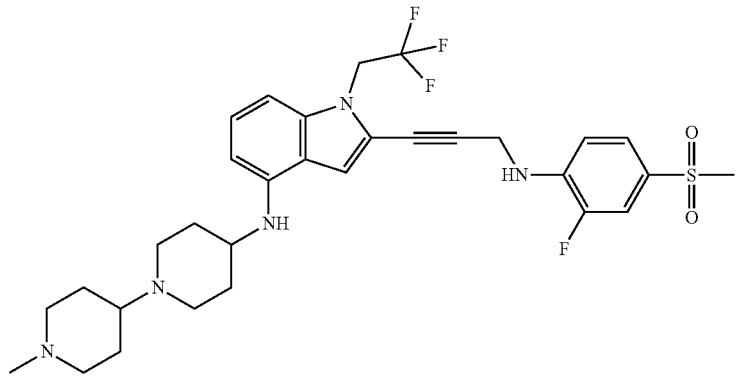

2-{3-[(2-fluoro-4-methanesulfonyl-phenyl)amino]prop-1-yn-1-yl}-N-[1-(1-methylpiperidin-4-yl)piperidin-4-yl]-1-(2,2,2-trifluoroethyl)-1H-indol-4-amine

TABLE 1-continued

List of compounds

| # | Structure IUPAC name |
|---|---|
| 558-P | 2-(3-{[4-(ethanesulfonyl)phenyl]amino}prop-1-yn-1-yl)-N-[1-(1-methylpiperidin-4-yl)piperidin-4-yl]-1-(2,2,2-trifluoroethyl)-1H-indol-4-amine |
| 559-P | 2-{3-[(2-fluoro-4-methanesulfonyl-phenyl)amino]prop-1-yn-1-yl}-N-(oxan-4-yl)-1-(2,2,2-trifluoroethyl)-1H-indol-4-amine |
| 560-P | 2-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)ethan-1-ol |

TABLE 1-continued

List of compounds

| # | Structure IUPAC name |
|---|---|
| 561-P | 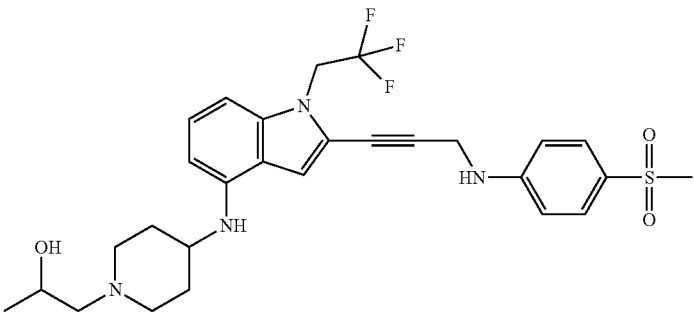 [SMILES: CC(O)CN1CCC(Nc2cccc3c2cc(C#CCNc2ccc(S(C)(=O)=O)cc2)n3CC(F)(F)F)CC1] 1-{4-[(2-{3-[(4-methanesulfonyl-phenyl)amino]prop-1-yn-1-yl}-1-(2,2,2-trifluoroethyl)-1H-indol-4-yl)amino]piperidin-1-yl}propan-2-ol |
| 562-P | 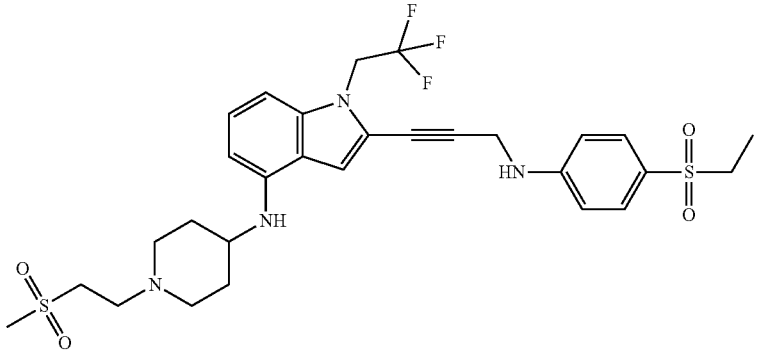 [SMILES: CCS(=O)(=O)c1ccc(NCC#Cc2cc3c(NC4CCN(CCS(C)(=O)=O)CC4)cccc3n2CC(F)(F)F)cc1] 2-(3-{[4-(ethanesulfonyl)-phenyl]amino}prop-1-yn-1-yl)-N-[1-(2-methanesulfonylethyl)piperidin-4-yl]-1-(2,2,2-trifluoroethyl)-1H-indol-4-amine |
| 563-P | 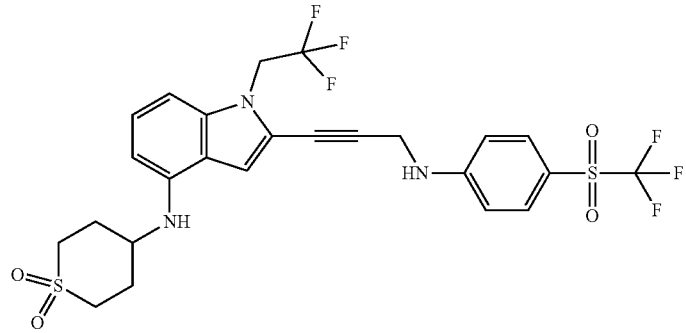 [SMILES: O=S1(=O)CCC(Nc2cccc3c2cc(C#CCNc2ccc(S(=O)(=O)C(F)(F)F)cc2)n3CC(F)(F)F)CC1] 4-{[1-(2,2,2-trifluoroethyl)-2-{3-[(4-trifluoromethanesulfonylphenyl)amino]prop-1-yn-1-yl}-1H-indol-4-yl]amino}-1$\lambda^6$-thiane-1,1-dione |

TABLE 1-continued

List of compounds

| # | Structure IUPAC name |
|---|---|
| 564-P | 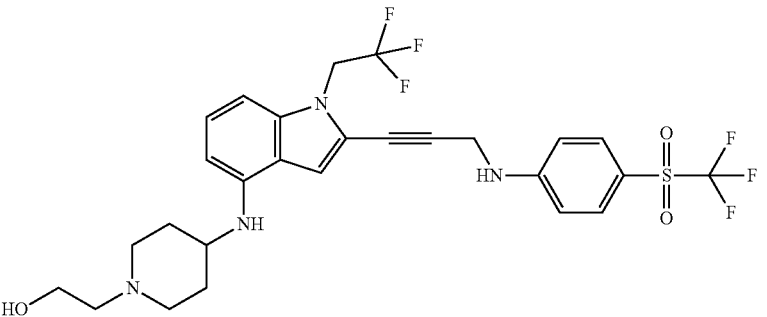 [SMILES: O=S(=O)(c1ccc(NCC#Cc2cc3c(NC4CCN(CCO)CC4)cccc3n2CC(F)(F)F)cc1)C(F)(F)F]<br>2-(4-{[1-(2,2,2-trifluoroethyl)-2-{3-[(4-trifluoromethanesulfonylphenyl)amino]prop-1-yn-1-yl}-1H-indol-4-yl]amino}piperidin-1-yl)ethan-1-ol |
| 565-P | 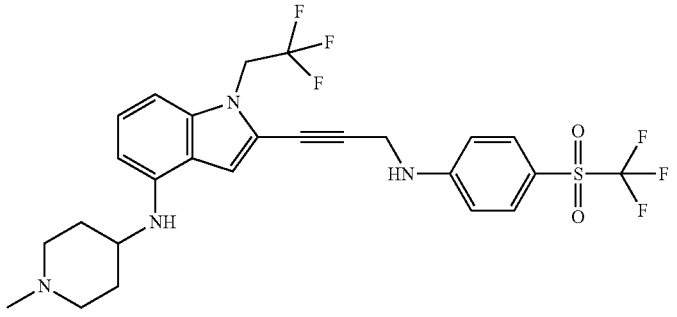 [SMILES: CN1CCC(Nc2cccc3c2cc(C#CCNc2ccc(S(=O)(=O)C(F)(F)F)cc2)n3CC(F)(F)F)CC1]<br>N-(1-methylpiperidin-4-yl)-1-(2,2,2-trifluoroethyl)-2-{3-[(4-trifluoromethanesulfonylphenyl)amino]prop-1-yn-1-yl}-1H-indol-4-amine |
| 566-P | 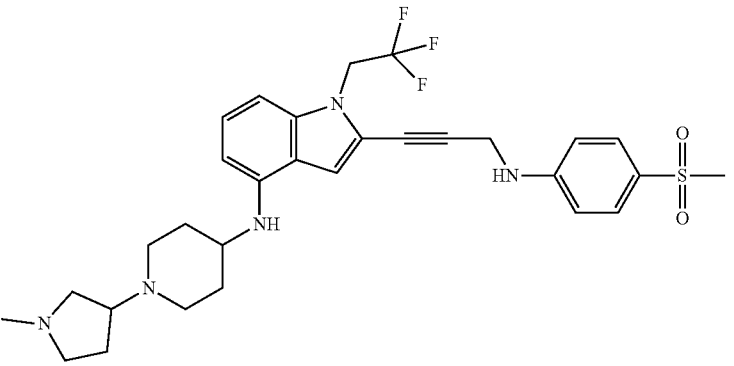<br>2-{3-[(4-methanesulfonyl-phenyl)amino]prop-1-yn-1-yl}-N-[1-(1-methylpyrrolidin-3-yl)piperidin-4-yl]-1-(2,2,2-trifluoroethyl)-1H-indol-4-amine |

TABLE 1-continued

List of compounds

| # | Structure IUPAC name |
|---|---|
| 567-P | 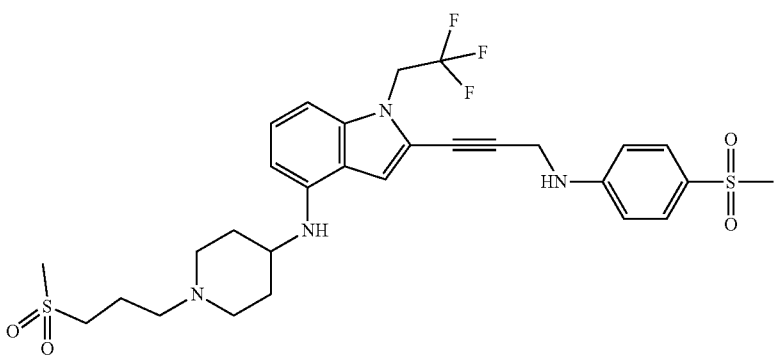 [SMILES: CS(=O)(=O)CCCN1CCC(Nc2cccc3c2cc(C#CCNc2ccc(S(C)(=O)=O)cc2)n3CC(F)(F)F)CC1]<br>2-{3-[(4-methanesulfonyl-phenyl)amino]prop-1-yn-1-yl}-N-[1-(3-methanesulfonylpropyl)piperidin-4-yl]-1-(2,2,2-trifluoroethyl)-1H-indol-4-amine |
| 568-P | 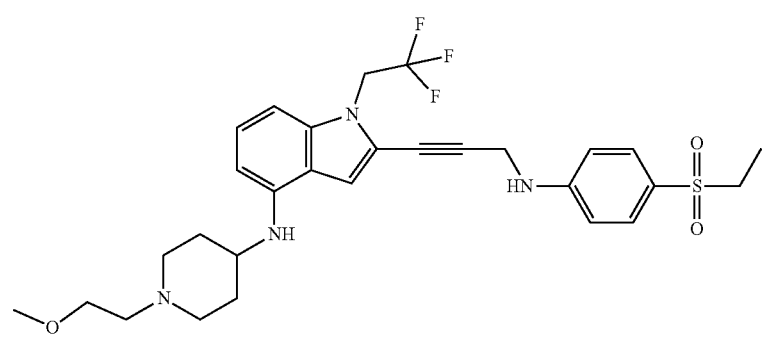 [SMILES: CCS(=O)(=O)c1ccc(NCC#Cc2cc3c(NC4CCN(CCOC)CC4)cccc3n2CC(F)(F)F)cc1]<br>2-(3-{[4-(ethanesulfonyl)-phenyl]amino}prop-1-yn-1-yl)-N-[1-(2-methoxyethyl)piperidin-4-yl]-1-(2,2,2-trifluoroethyl)-1H-indol-4-amine |
| 569-P | 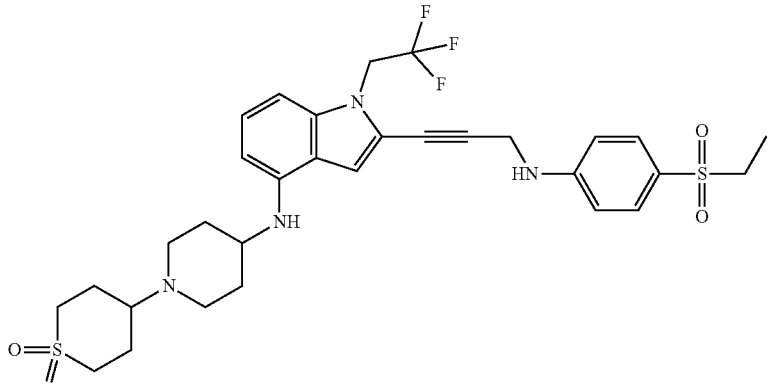<br>4-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)-1$\lambda^6$-thiane-1,1-dione |

TABLE 1-continued

List of compounds

| # | Structure IUPAC name |
|---|---|
| 570-P | 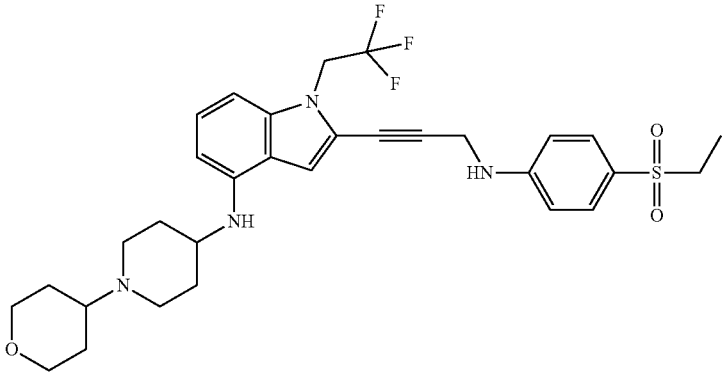 [SMILES: CCS(=O)(=O)c1ccc(NCC#Cc2cc3c(NC4CCN(C5CCOCC5)CC4)cccc3n2CC(F)(F)F)cc1]<br>2-(3-{[4-(ethanesulfonyl)-phenyl]amino}prop-1-yn-1-yl)-N-[1-(oxan-4-yl)piperidin-4-yl]-1-(2,2,2-trifluoroethyl)-1H-indol-4-amine |
| 571-P | 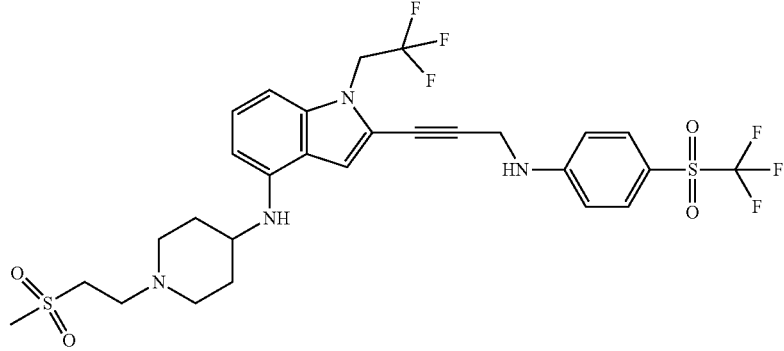 [SMILES: CS(=O)(=O)CCN1CCC(Nc2cccc3c2cc(C#CCNc2ccc(S(=O)(=O)C(F)(F)F)cc2)n3CC(F)(F)F)CC1]<br>N-[1-(2-methanesulfonylethyl)-piperidin-4-yl]-1-(2,2,2-trifluoroethyl)-2-{3-[(4-trifluoromethane-sulfonylphenyl)amino]prop-1-yn-1-yl}-1H-indol-4-amine |
| 572-P | 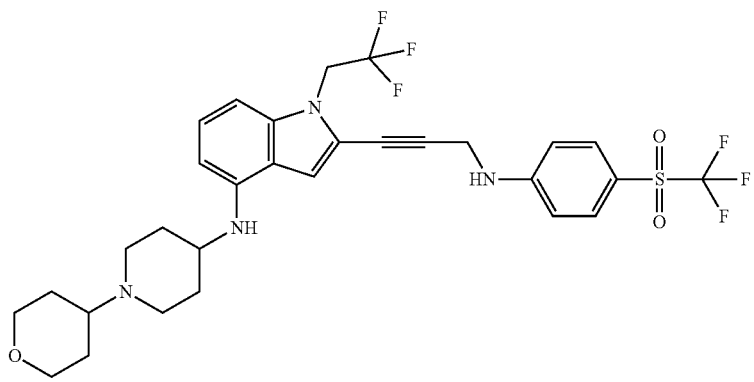 [SMILES: O=S(=O)(c1ccc(NCC#Cc2cc3c(NC4CCN(C5CCOCC5)CC4)cccc3n2CC(F)(F)F)cc1)C(F)(F)F]<br>N-[1-(oxan-4-yl)piperidin-4-yl]-1-(2,2,2-trifluoroethyl)-2-{3-[(4-trifluoromethanesulfonylphenyl)amino]prop-1-yn-1-yl}-1H-indol-4-amine |

TABLE 1-continued

List of compounds

| # | Structure IUPAC name |
|---|---|
| 573-P | 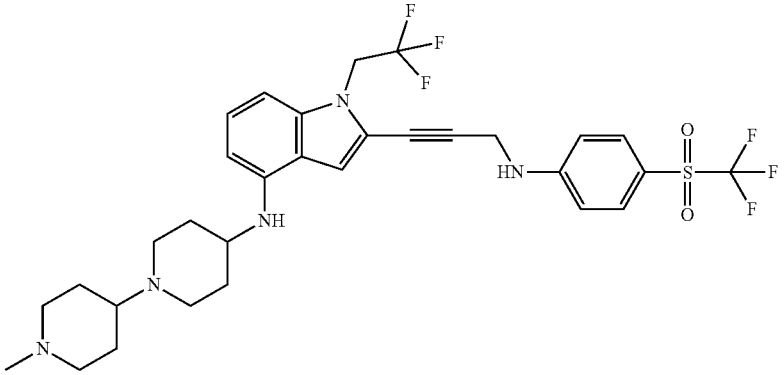 [SMILES: CN1CCC(N2CCC(Nc3cccc4c3cc(C#CCNc3ccc(S(=O)(=O)C(F)(F)F)cc3)n4CC(F)(F)F)CC2)CC1]<br>N-[1-(1-methylpiperidin-4-yl)piperidin-4-yl]-1-(2,2,2-trifluoroethyl)-2-{3-[(4-trifluoromethanesulfonylphenyl)amino]prop-1-yn-1-yl}-1H-indol-4-amine |
| 574-P | 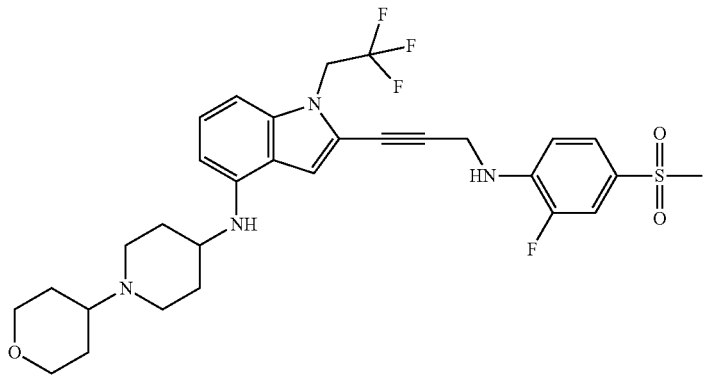 [SMILES: CS(=O)(=O)c1ccc(NCC#Cc2cc3c(NC4CCN(C5CCOCC5)CC4)cccc3n2CC(F)(F)F)c(F)c1]<br>2-{3-[(2-fluoro-4-methanesulfonyl-phenyl)amino]prop-1-yn-1-yl}-N-[1-(oxan-4-yl)piperidin-4-yl]-1-(2,2,2-trifluoroethyl)-1H-indol-4-amine |
| 575-P | 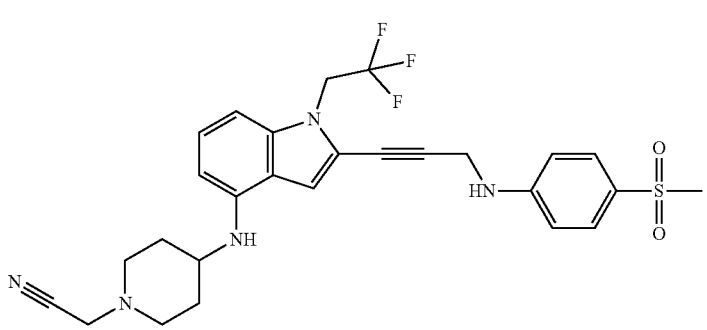 [SMILES: CS(=O)(=O)c1ccc(NCC#Cc2cc3c(NC4CCN(CC#N)CC4)cccc3n2CC(F)(F)F)cc1]<br>2-{4-[(2-{3-[(4-methanesulfonyl-phenyl)amino]prop-1-yn-1-yl}-1-(2,2,2-trifluoroethyl)-1H-indol-4-yl)amino]piperidin-1-yl}acetonitrile |

TABLE 1-continued

List of compounds

| # | Structure IUPAC name |
|---|---|
| 576-P | 2-{3-[(2-fluoro-4-methanesulfonylphenyl)amino]prop-1-yn-1-yl}-N-[1-(2-methoxyethyl)piperidin-4-yl]-1-(2,2,2-trifluoroethyl)-1H-indol-4-amine |
| 577-P | 2-{3-[(3-chloro-4-methanesulfonylphenyl)amino]prop-1-yn-1-yl}-N-[1-(oxan-4-yl)piperidin-4-yl]-1-(2,2,2-trifluoroethyl)-1H-indol-4-amine |
| 578-P | 2-{3-[(2,6-difluoro-4-methanesulfonyl-phenyl)amino]prop-1-yn-1-yl}-N-[1-(oxan-4-yl)piperidin-4-yl]-1-(2,2,2-trifluoroethyl)-1H-indol-4-amine |

TABLE 1-continued

List of compounds

| # | Structure IUPAC name |
|---|---|
| 579-P | 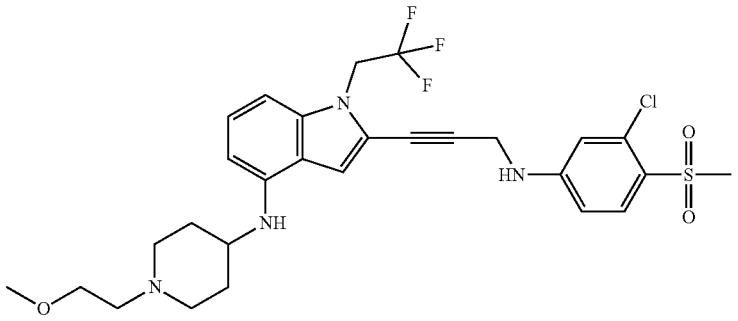 2-{3-[(3-chloro-4-methanesulfonyl-phenyl)amino]prop-1-yn-1-yl}-N-[1-(2-methoxyethyl)piperidin-4-yl]-1-(2,2,2-trifluoroethyl)-1H-indol-4-amine |
| 580-P | 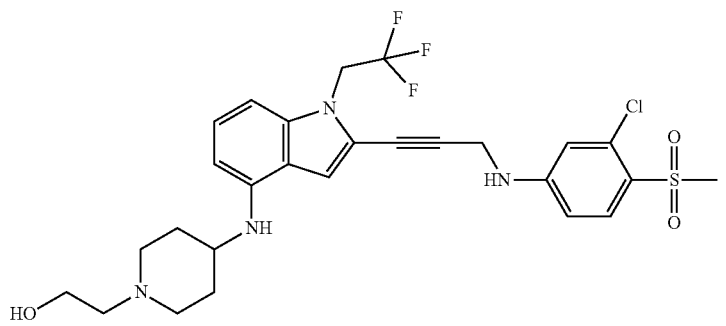 [SMILES: CS(=O)(=O)c1ccc(NCC#Cc2cc3c(NC4CCN(CCO)CC4)cccc3n2CC(F)(F)F)cc1Cl] 2-{4-[(2-{3-[(3-chloro-4-methanesulfonylphenyl)amino]prop-1-yn-1-yl}-1-(2,2,2-trifluoroethyl)-1H-indol-4-yl)amino]piperidin-1-yl}ethan-1-ol |
| 581-P | 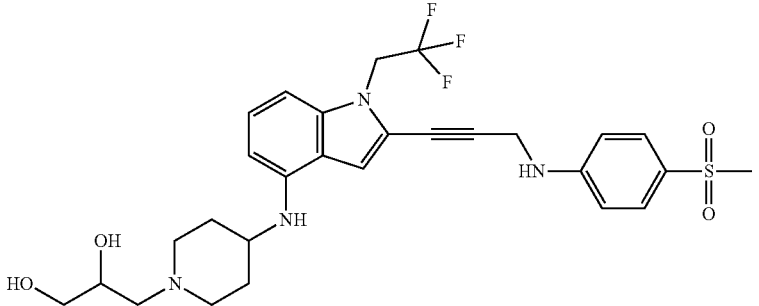 [SMILES: CS(=O)(=O)c1ccc(NCC#Cc2cc3c(NC4CCN(CC(O)CO)CC4)cccc3n2CC(F)(F)F)cc1] (2S)-3-{4-[(2-{3-[(4-methanesulfonyl-phenyl)amino]prop-1-yn-1-yl}-1-(2,2,2-trifluoroethyl)-1H-indol-4-yl)amino]piperidin-1-yl}propane-1,2-diol |

TABLE 1-continued
List of compounds
| # | Structure IUPAC name |
|---|---|
| 582-P | 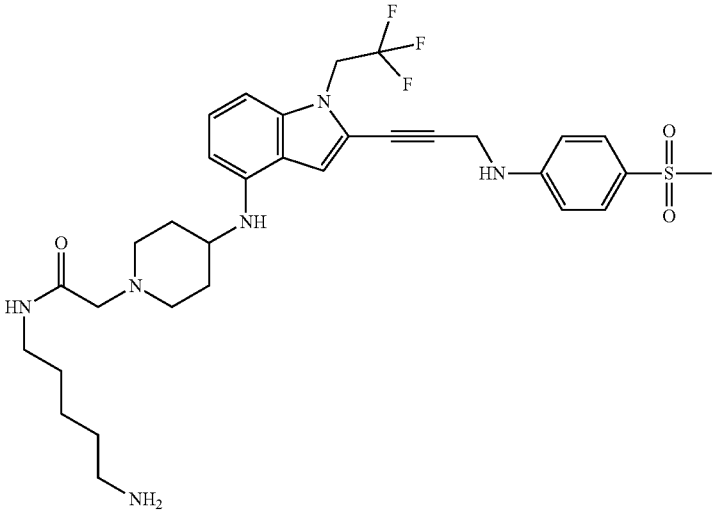 [SMILES: CS(=O)(=O)c1ccc(NCC#Cc2cc3c(NC4CCN(CC(=O)NCCCCCN)CC4)cccc3n2CC(F)(F)F)cc1] N-(5-aminopentyl)-2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetamide |
| 583-P | 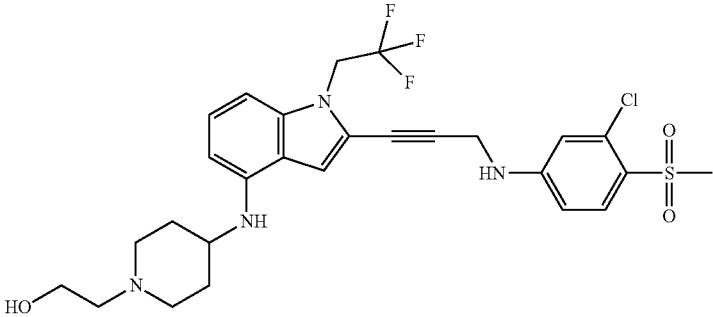 [SMILES: CS(=O)(=O)c1ccc(NCC#Cc2cc3c(NC4CCN(CCO)CC4)cccc3n2CC(F)(F)F)cc1Cl] 2-{3-[(2,6-difluoro-4-methanesulfonyl-phenyl)amino]prop-1-yn-1-yl}-N-[1-(2-methoxyethyl)piperidin-4-yl]-1-(2,2,2-trifluoroethyl)-1H-indol-4-amine |
| 584-P | 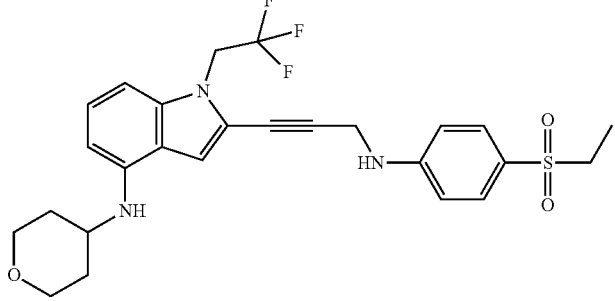 2-(3-{[4-(ethanesulfonyl)phenyl]-amino}prop-1-yn-1-yl)-N-(oxan-4-yl)-1-(2,2,2-trifluoroethyl)-1H-indol-4-amine |

TABLE 1-continued

List of compounds

| # | Structure IUPAC name |
|---|---|
| 585-P | 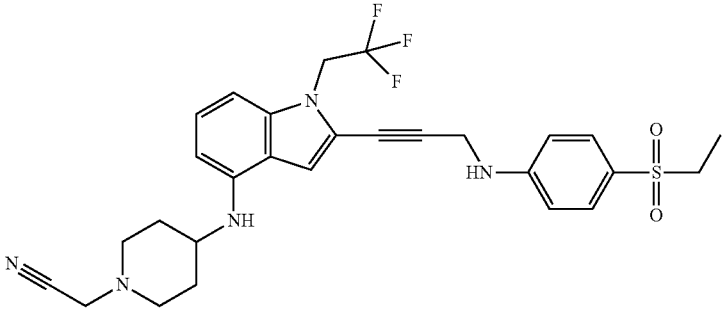 [SMILES: CCS(=O)(=O)c1ccc(NCC#Cc2cc3c(NC4CCN(CC#N)CC4)cccc3n2CC(F)(F)F)cc1]
2-(4-{[2-(3-{[4-(ethanesulfonyl)phenyl]amino}prop-1-yn-1-yl)-1-(2,2,2-trifluoroethyl)-1H-indol-4-yl]amino}piperidin-1-yl)acetonitrile |
| 586-P | 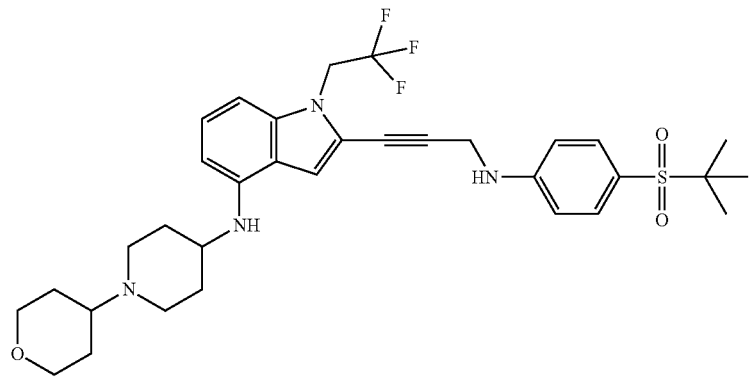 [SMILES: CC(C)(C)S(=O)(=O)c1ccc(NCC#Cc2cc3c(NC4CCN(C5CCOCC5)CC4)cccc3n2CC(F)(F)F)cc1]
2-(3-{[4-(2-methylpropane-2-sulfonyl)phenyl]amino}prop-1-yn-1-yl)-N-[1-(oxan-4-yl)piperidin-4-yl]-1-(2,2,2-trifluoroethyl)-1H-indol-4-amine |
| 587-P | 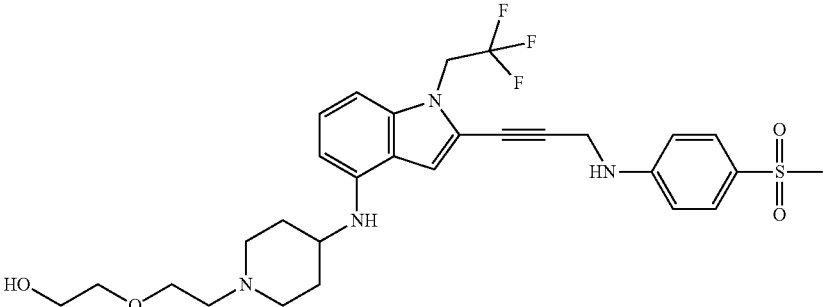
2-(2-{4-[(2-{3-[(4-methanesulfonyl-phenyl)amino]prop-1-yn-1-yl}-1-(2,2,2-trifluoroethyl)-1H-indol-4-yl)amino]piperidin-1-yl}ethoxy)ethan-1-ol |

TABLE 1-continued

List of compounds

| # | Structure IUPAC name |
|---|---|
| 588-P | 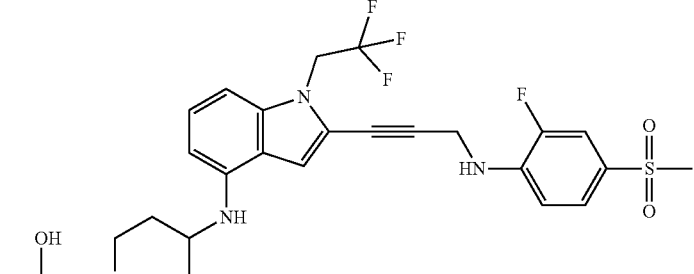<br>1-{4-[(2-{3-[(2-fluoro-4-methane-sulfonylphenyl)amino]prop-1-yn-1-yl}-1-(2,2,2-trifluoroethyl)-1H-indol-4-yl)amino]piperidin-1-yl}propan-2-ol |
| 589-P | 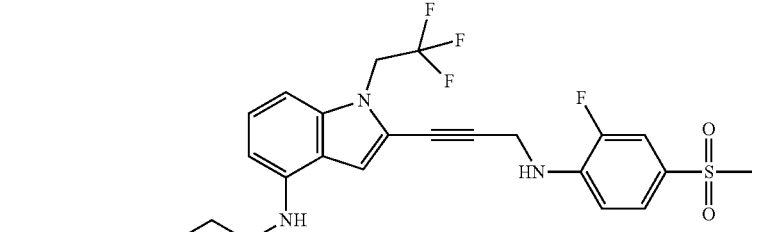<br>3-{4-[(2-{3-[(2-fluoro-4-methanesulfonylphenyl)amino]prop-1-yn-1-yl}-1-(2,2,2-trifluoroethyl)-1H-indol-4-yl)amino]piperidin-1-yl}propane-1,2-diol |
| 590-P | 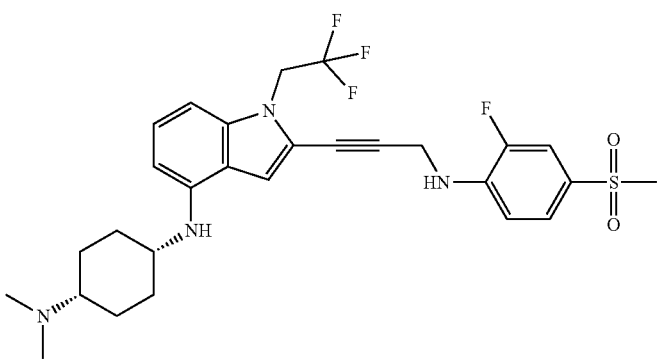<br>(1S,4S)-4-N-(2-{3-[(2-fluoro-4-methanesulfonylphenyl)amino]prop-1-yn-1-yl}-1-(2,2,2-trifluoroethyl)-1H-indol-4-yl)-1-N,1-N-dimethylcyclohexane-1,4-diamine |

TABLE 1-continued

List of compounds

| # | Structure IUPAC name |
|---|---|
| 591-P | 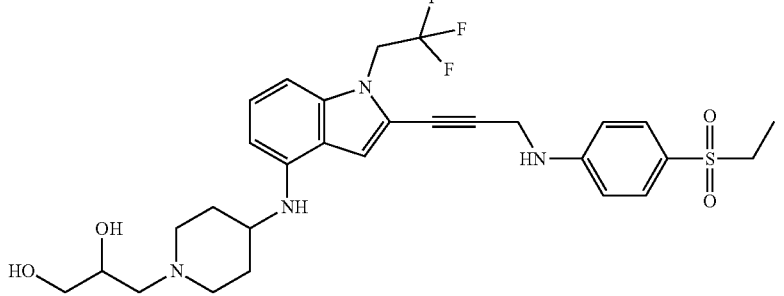<br>3-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)propane-1,2-diol |
| 592-P | 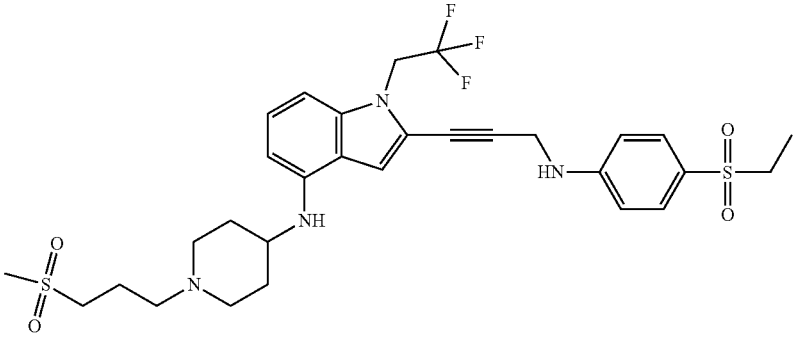 [SMILES: CCS(=O)(=O)c1ccc(NCC#Cc2cc3c(NC4CCN(CCCS(C)(=O)=O)CC4)cccc3n2CC(F)(F)F)cc1]<br>2-(3-{[4-(ethanesulfonyl)-phenyl]amino}prop-1-yn-1-yl)-N-[1-(3-methanesulfonylpropyl)-piperidin-4-yl]-1-(2,2,2-trifluoroethyl)-1H-indol-4-amine |
| 593-P | 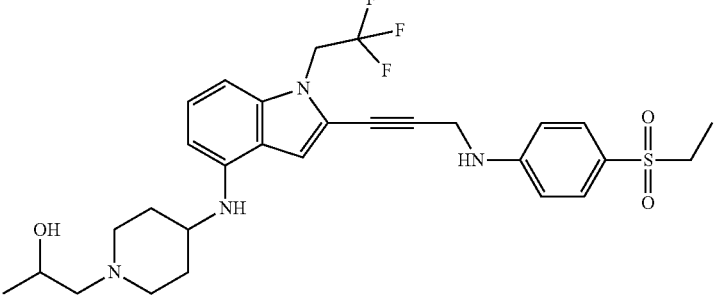<br>1-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)propan-2-ol |

TABLE 1-continued

List of compounds

| # | Structure IUPAC name |
|---|---|
| 594-P | 2-[2-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)ethoxy]ethan-1-ol |
| 595-P | (1R,4R)-4-N-(2-{3-[(2-fluoro-4-methanesulfonylphenyl)amino]prop-1-yn-1-yl}-1-(2,2,2-trifluoroethyl)-1H-indol-4-yl)-1-N,1-N-dimethyl-cyclohexane-1,4-diamine |
| 596-P | 2-{3-[(2,6-difluoro-4-methanesulfonylphenyl)amino]prop-1-yn-1-yl}-N-[1-(2-methanesulfonylethyl)piperidin-4-yl]-1-(2,2,2-trifluoroethyl)-1H-indol-4-amine |

TABLE 1-continued

List of compounds

| # | Structure IUPAC name |
|---|---|

597-P

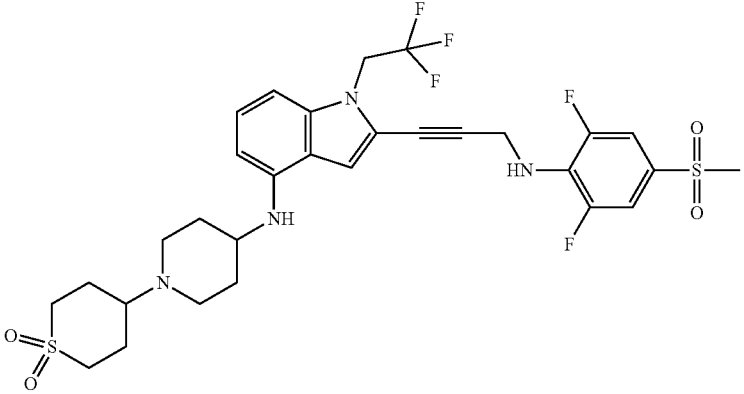 [SMILES: CS(=O)(=O)c1cc(F)c(NCC#Cc2cc3c(NC4CCN(C5CCS(=O)(=O)CC5)CC4)cccc3n2CC(F)(F)F)c(F)c1]

4-{4-[(2-{3-[(2,6-difluoro-4-
methanesulfonylphenyl)amino]prop-1-yn-1-
yl}-1-(2,2,2-trifluoroethyl)-1H-indol-4-
yl)amino]piperidin-1-yl}-1λ⁶-thiane-1,1-dione

598-P

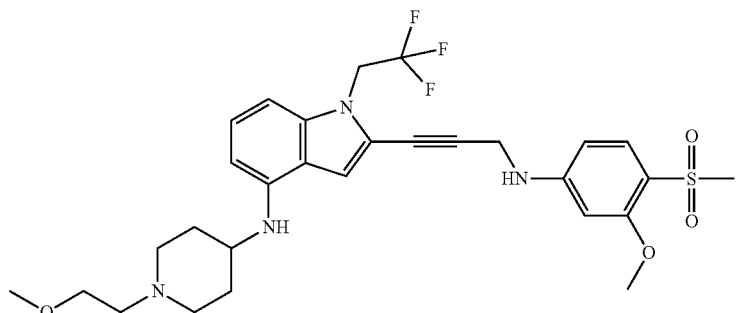

2-{3-[(4-methanesulfonyl-3-
methoxyphenyl)amino]prop-1-yn-1-yl}-N-
[1-(oxan-4-yl)piperidin-4-yl]-1-(2,2,2-
trifluoroethyl)-1H-indol-4-amine

599-P

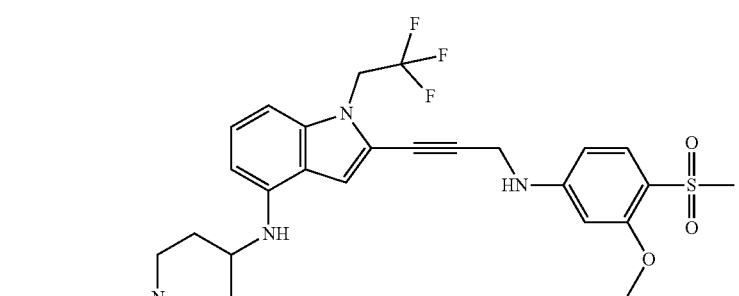

2-{3-[(4-methanesulfonyl-3-
methoxyphenyl)amino]prop-1-yn-1-yl}-N-
[1-(2-methoxyethyl)piperidin-4-yl]-1-(2,2,2-
trifluoroethyl)-1H-indol-4-amine TABLE 1-continued List of compounds

| # | Structure | IUPAC name |
|---|---|---|
| 600-P | 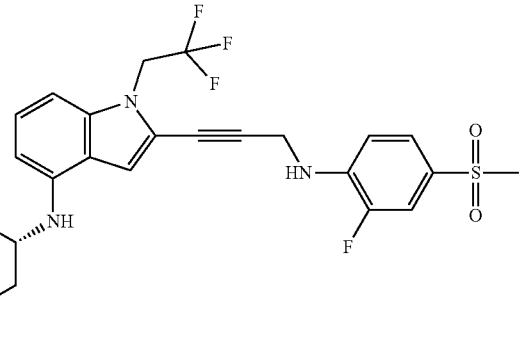 | 4-N-(2-{3-[(2-fluoro-4-methanesulfonylphenyl)amino]prop-1-yn-1-yl}-1-(2,2,2-trifluoroethyl)-1H-indol-4-yl)-1-N,1-N-dimethylcyclohexane-1,4-diamine |
| 601-P | 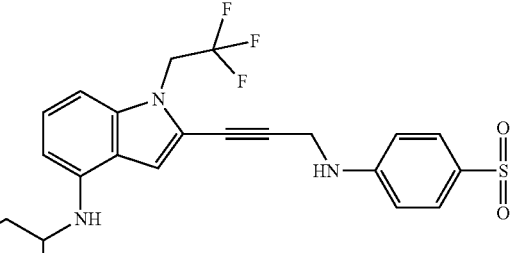 | 2-{4-[(2-{3-[(4-methanesulfonyl-phenyl)amino]prop-1-yn-1-yl}-1-(2,2,2-trifluoroethyl)-1H-indol-4-yl)amino]piperidin-1-yl}acetic acid |
| 602-P | 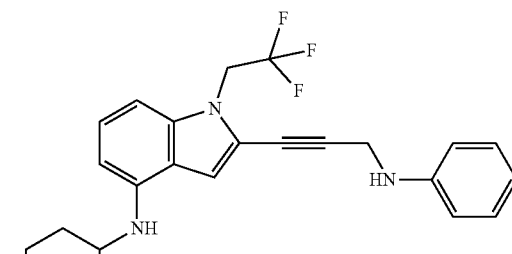 | 2-hydroxyethyl 2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetate |

TABLE 1-continued

List of compounds

| # | Structure IUPAC name |
|---|---|

603-P

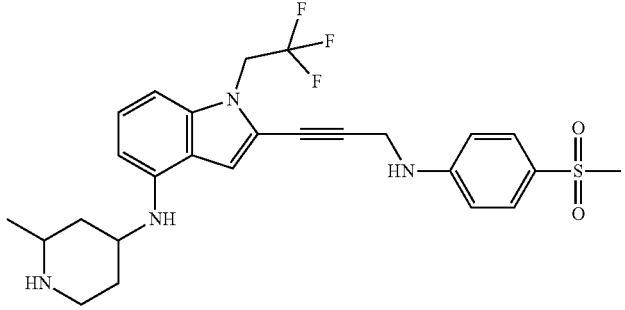

2-{3-[(4-methanesulfonylphenyl)-
amino]prop-1-yn-1-yl}-N-(2-
methylpiperidin-4-yl)-1-(2,2,2-
trifluoroethyl)-1H-indol-4-amine

604-P

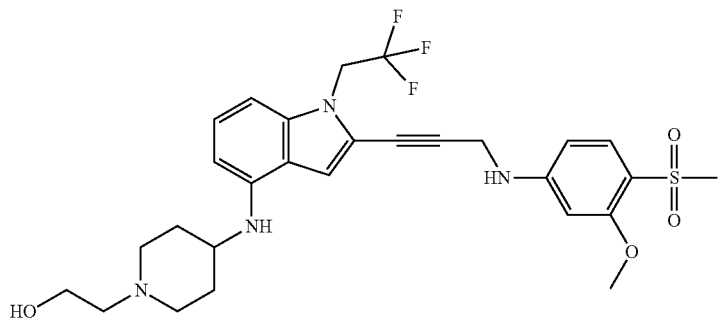 [SMILES: COc1cc(NCC#Cc2cc3c(NC4CCN(CCO)CC4)cccc3n2CC(F)(F)F)ccc1S(C)(=O)=O]

2-{4-[(2-{3-[(4-methanesulfonyl-3-
methoxyphenyl)amino]prop-1-yn-1-yl}-1-
(2,2,2-trifluoroethyl)-1H-indol-4-
yl)amino]piperidin-1-yl}ethan-1-ol

605-P

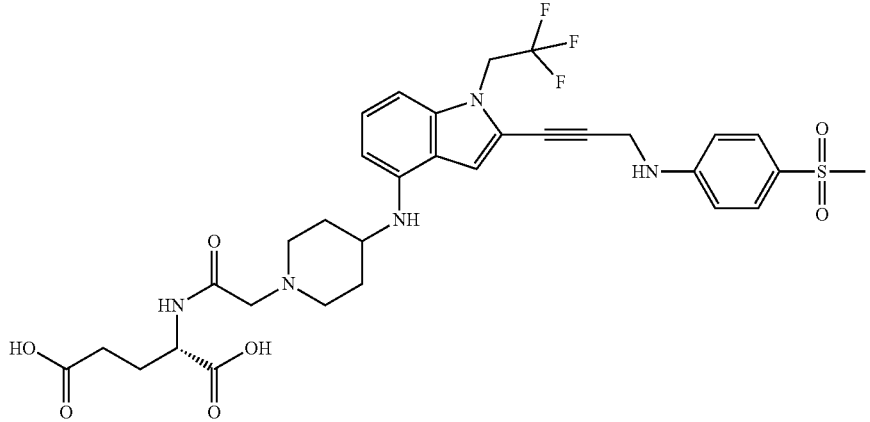 [SMILES: CS(=O)(=O)c1ccc(NCC#Cc2cc3c(NC4CCN(CC(=O)N[C@@H](CCC(=O)O)C(=O)O)CC4)cccc3n2CC(F)(F)F)cc1]

(2S)-2-(2-{4-[(2-{3-[(4-methane-
sulfonylphenyl)amino]prop-1-yn-1-yl}-1-
(2,2,2-trifluoroethyl)-1H-indol-4-
yl)amino]piperidin-1-
yl}acetamido)pentanedioic acid TABLE 1-continued List of compounds

| # | Structure IUPAC name |
|---|---|
| 606-P | 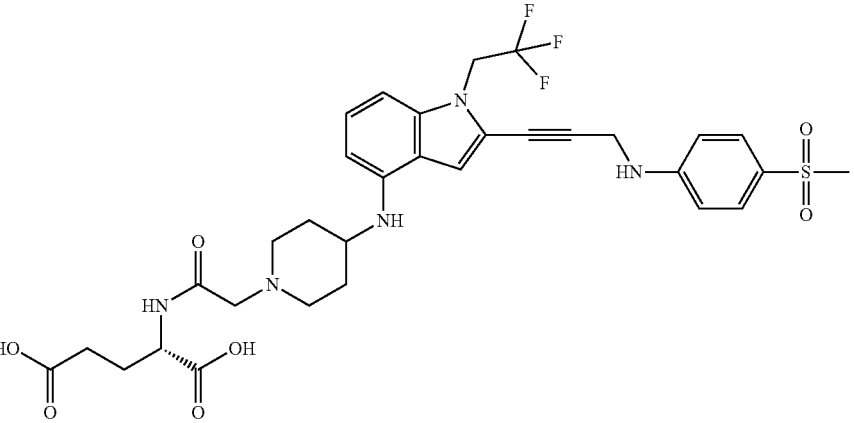<br>1,5-dimethyl (2S)-2-(2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetamido)pentanedioate |
| 607-P | 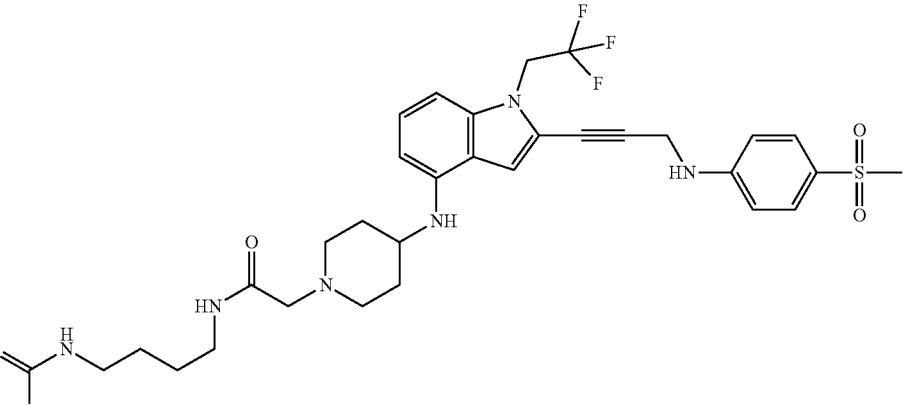<br>N-(4-carbamimidamidobutyl)-2-{4-[(2-{3-[(4-methanesulfonylphenyl)-amino]prop-1-yn-1-yl}-1-(2,2,2-trifluoroethyl)-1H-indol-4-yl)amino]piperidin-1-yl}acetamide |
| 608-P | 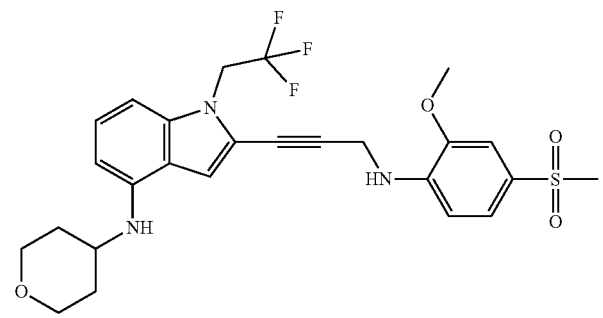 [SMILES: COc1cc(S(C)(=O)=O)ccc1NCC#Cc1cc2c(NC3CCOCC3)cccc2n1CC(F)(F)F]<br>2-{3-[(4-methanesulfonyl-2-methoxyphenyl)amino]prop-1-yn-1-yl}-N-(oxan-4-yl)-1-(2,2,2-trifluoroethyl)-1H-indol-4-amine |

TABLE 1-continued

List of compounds

| # | Structure IUPAC name |
|---|---|
| 609-P | 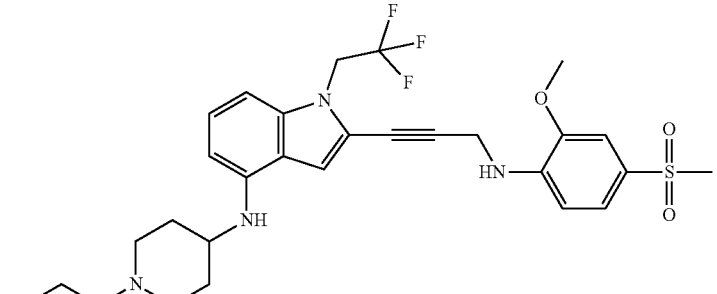<br>2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethan-1-ol |
| 610-P | 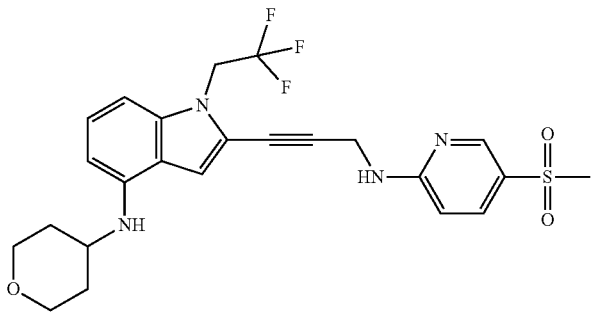 [SMILES: CS(=O)(=O)c1ccc(NCC#Cc2cc3c(NC4CCOCC4)cccc3n2CC(F)(F)F)nc1]<br>2-{3-[(5-methanesulfonylpyridin-2-yl)amino]prop-1-yn-1-yl}-N-(oxan-4-yl)-1-(2,2,2-trifluoroethyl)-1H-indol-4-amine |
| 611-P | 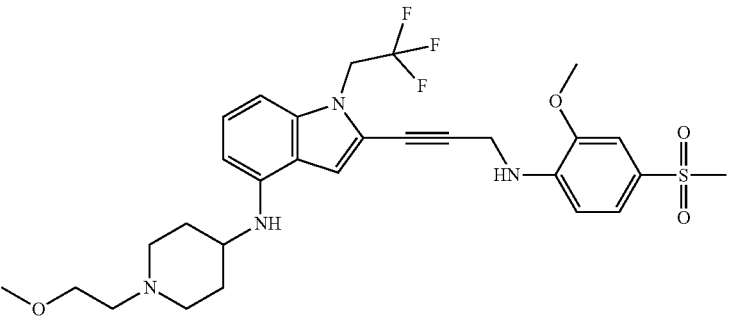<br>3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propane-1,2-diol |

TABLE 1-continued

List of compounds

| # | Structure | IUPAC name |
|---|---|---|
| 612-P | 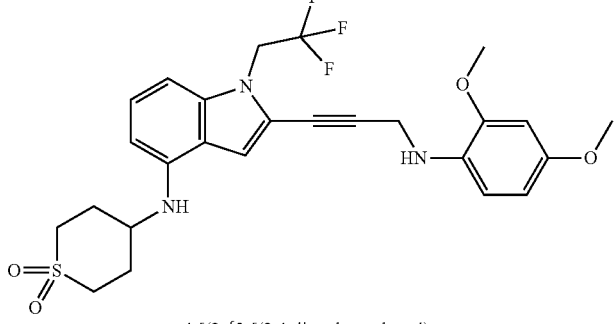 | 4-[(2-{3-[(2,4-dimethoxyphenyl)-amino]prop-1-yn-1-yl}-1-(2,2,2-trifluoroethyl)-1H-indol-4-yl)amino]-1$\lambda^6$-thiane-1,1-dione |
| 613-P | 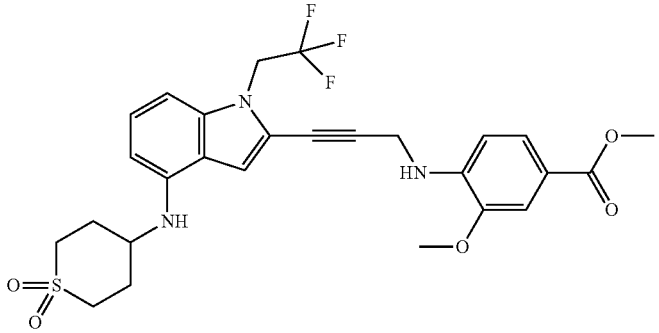 [SMILES: COC(=O)c1ccc(NCC#Cc2cc3c(NC4CCS(=O)(=O)CC4)cccc3n2CC(F)(F)F)c(OC)c1] | methyl 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxybenzoate |
| 614-P | 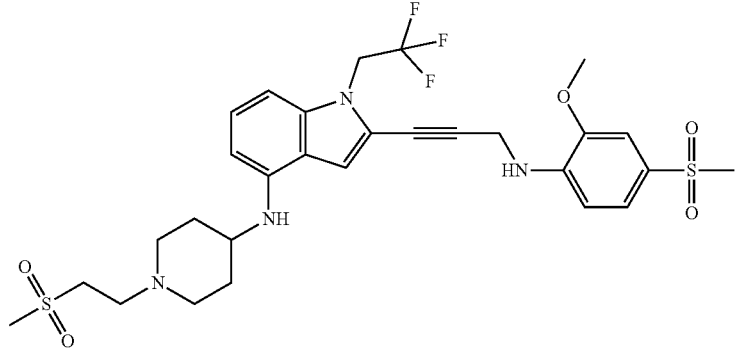 | 2-{3-[(4-methanesulfonyl-2-methoxyphenyl)amino]prop-1-yn-1-yl}-N-[1-(2-methanesulfonylethyl)-piperidin-4-yl]-1-(2,2,2-trifluoroethyl)-1H-indol-4-amine |

TABLE 1-continued

List of compounds

| # | Structure IUPAC name |
|---|---|
| 615-P | 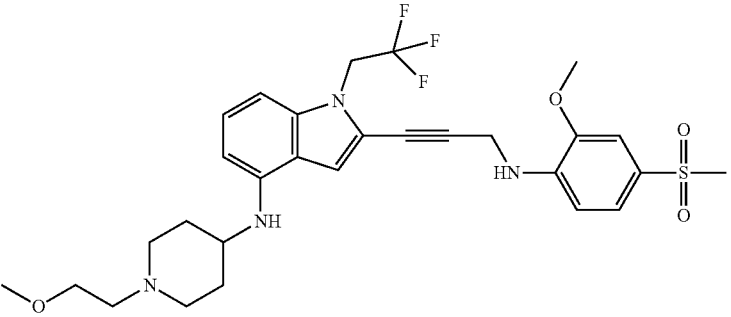<br>2-{3-[(4-methanesulfonyl-2-methoxyphenyl)amino]prop-1-yn-1-yl}-N-[1-(2-methoxyethyl)piperidin-4-yl]-1-(2,2,2-trifluoroethyl)-1H-indol-4-amine |
| 616-P | 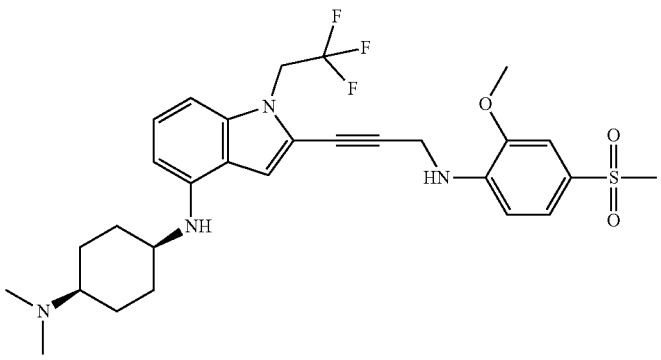<br>(1S,4S)-4-N-(2-{3-[(4-methanesulfonyl-2-methoxyphenyl)amino]prop-1-yn-1-yl}-1-(2,2,2-trifluoroethyl)-1H-indol-4-yl)-1-N,1-N-dimethylcyclohexane-1,4-diamine |
| 617-P | 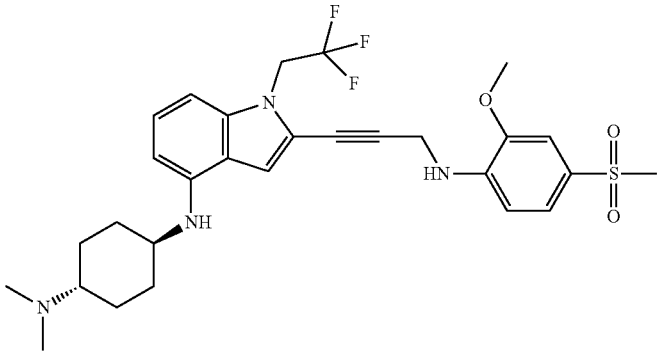<br>(1R,4R)-4-N-(2-{3-[(4-methanesulfonyl-2-methoxyphenyl)amino]prop-1-yn-1-yl}-1-(2,2,2-trifluoroethyl)-1H-indol-4-yl)-1-N,1-N-dimethylcyclohexane-1,4-diamine |

TABLE 1-continued

List of compounds

| # | Structure IUPAC name |
|---|---|
| 618-P | 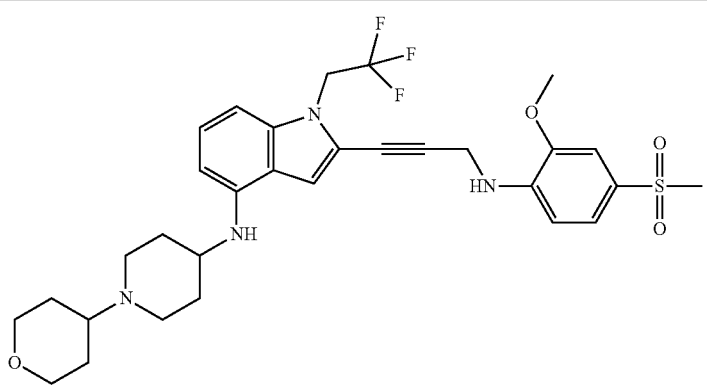 [SMILES: COc1cc(S(C)(=O)=O)ccc1NCC#Cc1cc2c(NC3CCN(C4CCOCC4)CC3)cccc2n1CC(F)(F)F] 2-{3-[(4-methanesulfonyl-2-methoxyphenyl)amino]prop-1-yn-1-yl}-N-[1-(oxan-4-yl)piperidin-4-yl]-1-(2,2,2-trifluoroethyl)-1H-indol-4-amine |
| 619-P | 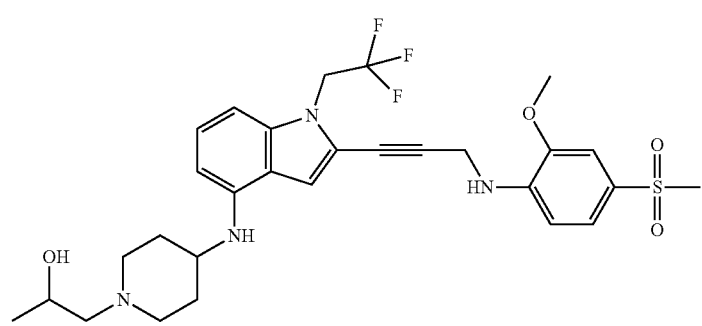 [SMILES: COc1cc(S(C)(=O)=O)ccc1NCC#Cc1cc2c(NC3CCN(CC(C)O)CC3)cccc2n1CC(F)(F)F] 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-o |
| 620-P | 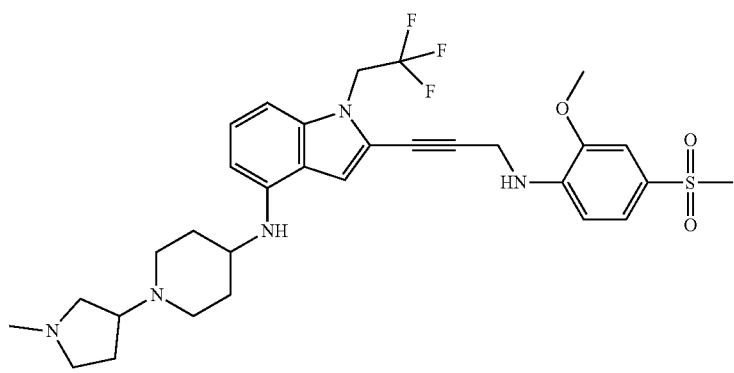 2-{3-[(4-methanesulfonyl-2-methoxyphenyl)amino]prop-1-yn-1-yl}-N-[1-(1-methylpyrrolidin-3-yl)piperidin-4-yl]-1-(2,2,2-trifluoroethyl)-1H-indol-4-amine |

TABLE 1-continued

List of compounds

| # | Structure IUPAC name |
|---|---|
| 621-P | 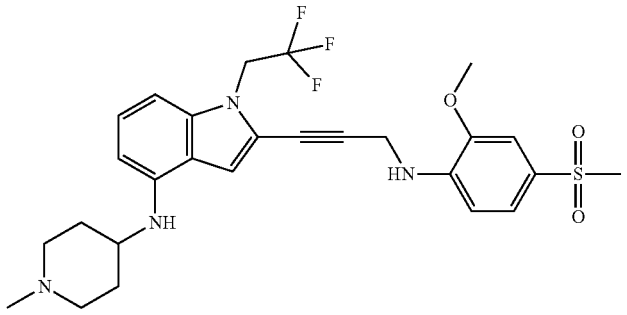<br>2-{3-[(4-methanesulfonyl-2-methoxyphenyl)amino]prop-1-yn-1-yl}-N-(2-methylpiperidin-4-yl)-1-(2,2,2-trifluoroethyl)-1H-indol-4-amine |
| 622-P | 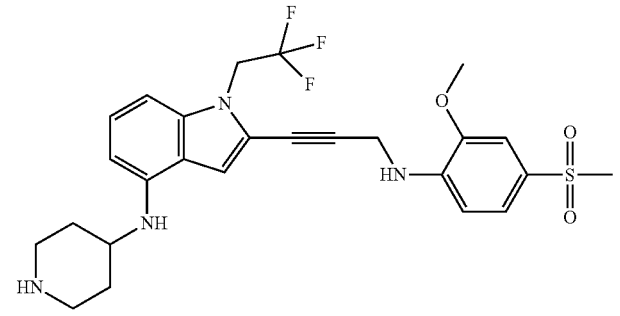 [SMILES: COc1cc(S(C)(=O)=O)ccc1NCC#Cc1cc2c(NC3CCNCC3)cccc2n1CC(F)(F)F]<br>2-{3-[(4-methanesulfonyl-2-methoxyphenyl)amino]prop-1-yn-1-yl}-N-(piperidin-4-yl)-1-(2,2,2-trifluoroethyl)-1H-indol-4-amine |
| 623-P | 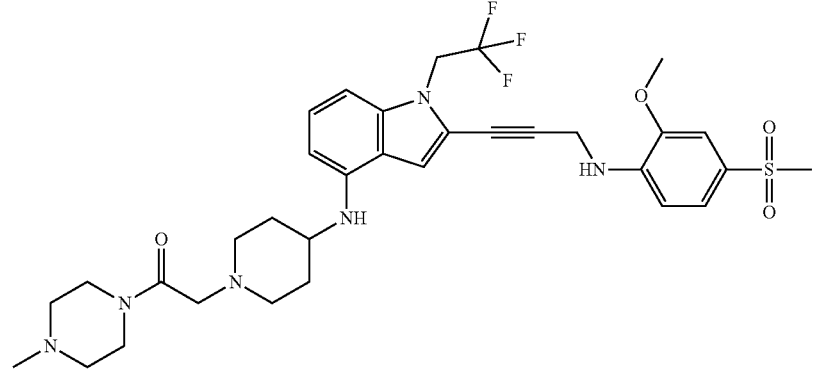<br>2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-1-(4-methylpiperazin-1-yl)ethan-1-one |

TABLE 1-continued

List of compounds

| # | Structure IUPAC name |
|---|---|
| 624-P | 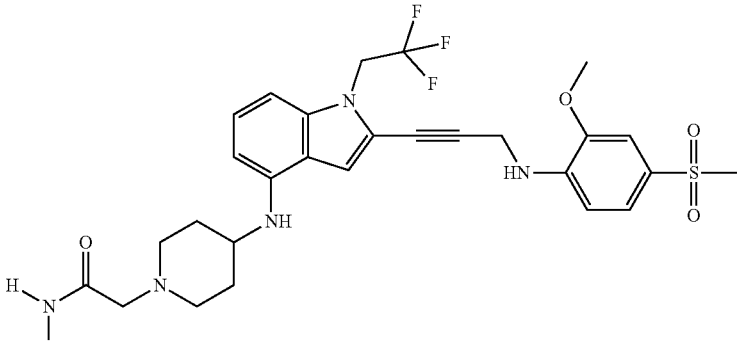<br>2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}acetamide |
| 625-P | 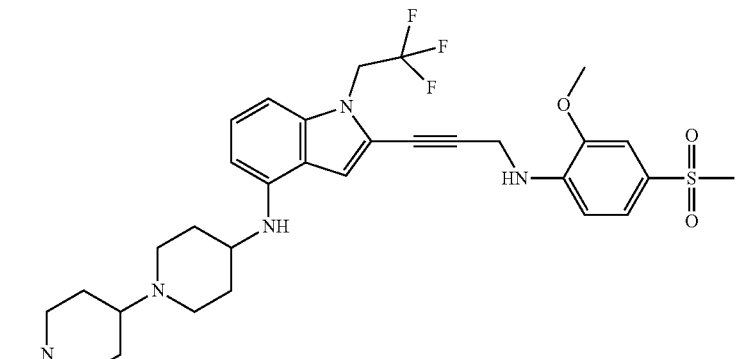<br>2-{3-[(4-methanesulfonyl-2-methoxyphenyl)amino]prop-1-yn-1-yl}-N-[1-(1-methylpiperidin-4-yl)piperidin-4-yl]-1-(2,2,2-trifluoroethyl)-1H-indol-4-amine |
| 626-P | 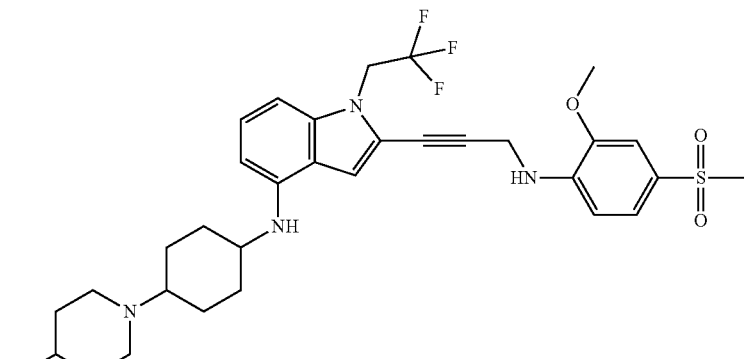<br>1-{4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl}piperidin-4-ol |

TABLE 1-continued

List of compounds

| # | Structure IUPAC name |
|---|---|
| 627-P | 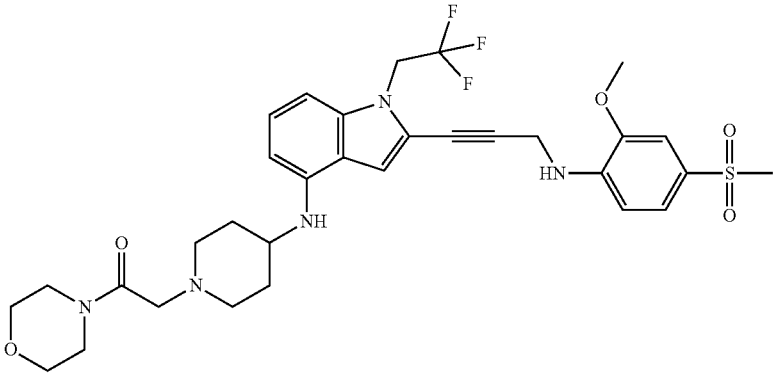 [SMILES: COc1cc(S(C)(=O)=O)ccc1NCC#Cc1cc2c(NC3CCN(CC(=O)N4CCOCC4)CC3)cccc2n1CC(F)(F)F] 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-1-(morpholin-4-yl)ethan-1-one |
| 628-P | 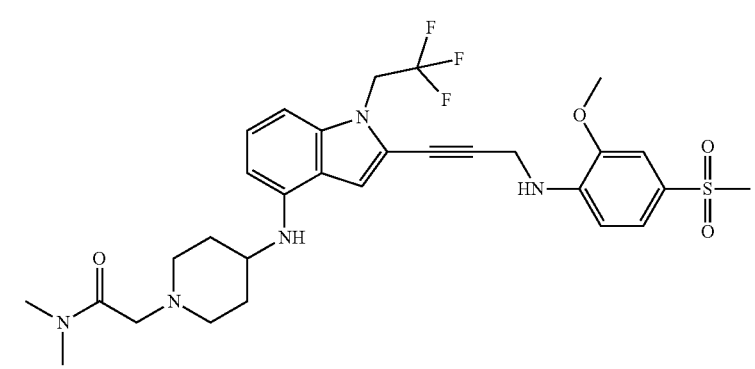 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-N,N-dimethylacetamide |
| 629-P | 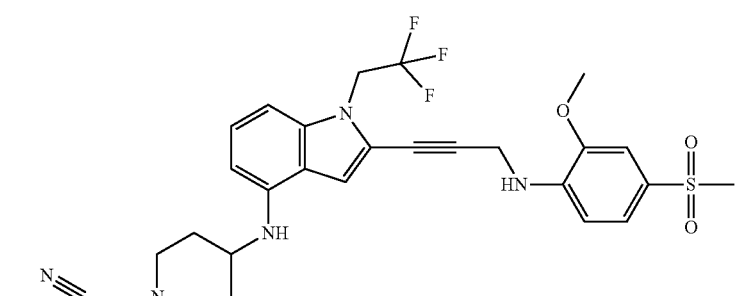 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}acetonitrile |

TABLE 1-continued

List of compounds

| # | Structure IUPAC name |
|---|---|
| 630-P | 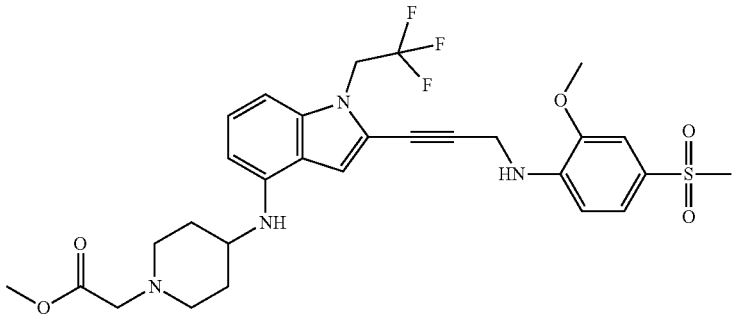<br>methyl 2-{4-[(2-{3-[(4-methane-sulfonyl-2-methoxyphenyl)amino]prop-1-yn-1-yl}-1-(2,2,2-trifluoroethyl)-1H-indol-4-yl)amino]piperidin-1-yl}acetate |
| 631-P | 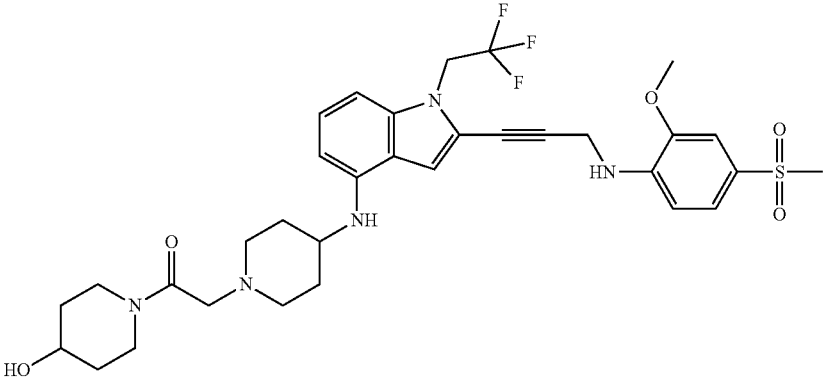 [SMILES: COc1cc(S(C)(=O)=O)ccc1NCC#Cc1cc2c(NC3CCN(CC(=O)N4CCC(O)CC4)CC3)cccc2n1CC(F)(F)F]<br>1-(4-hydroxypiperidin-1-yl)-2-{4-[(2-{3-[(4-methanesulfonyl-2-methoxy-phenyl)amino]prop-1-yn-1-yl}-1-(2,2,2-trifluoroethyl)-1H-indol-4-yl)amino]piperidin-1-yl}ethan-1-one |
| 632-P | 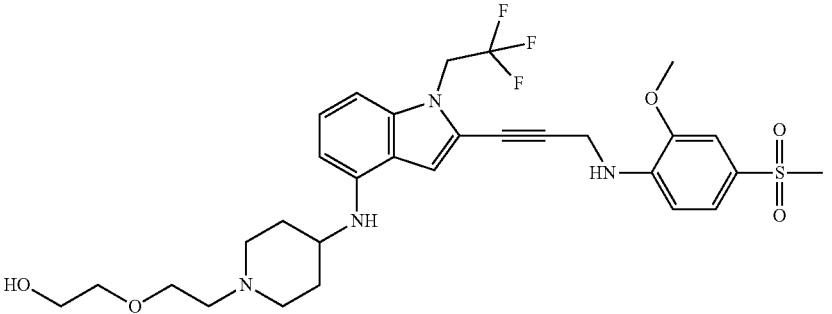 [SMILES: COc1cc(S(C)(=O)=O)ccc1NCC#Cc1cc2c(NC3CCN(CCOCCO)CC3)cccc2n1CC(F)(F)F]<br>2-(2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethoxy)ethan-1-ol |

TABLE 1-continued

List of compounds

| # | Structure IUPAC name |
|---|---|
| 633-P | 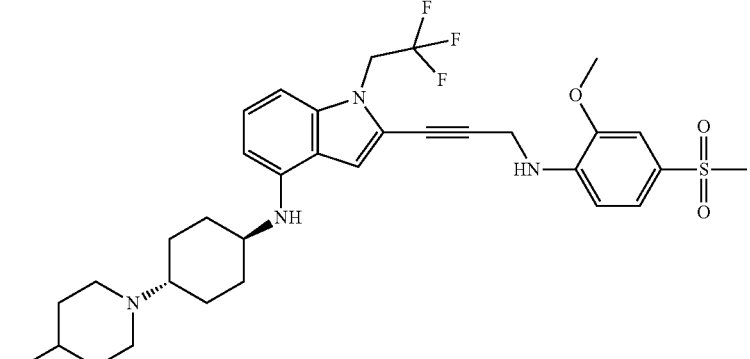<br>-[(1R,4R)-4-[(2-{3-[(4-methane-sulfonyl-2-methoxyphenyl)amino]prop-1-yn-1-yl}-1-(2,2,2-trifluoroethyl)-1H-indol-4-yl)amino]cyclohexyl]piperidin-4-ol |
| 634-P | 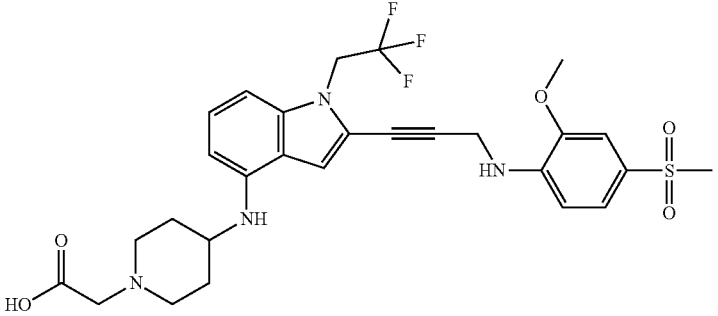 [SMILES: COc1cc(S(C)(=O)=O)ccc1NCC#Cc1cc2c(NC3CCN(CC(=O)O)CC3)cccc2n1CC(F)(F)F]<br>2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}acetic acid |
| 635-P | 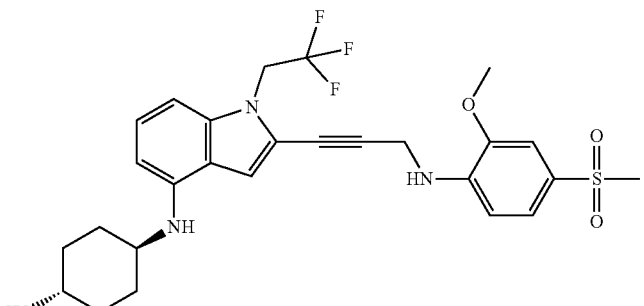<br>(1R,4R)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol |

TABLE 1-continued

List of compounds

| # | Structure IUPAC name |
|---|---|
| 636-P | 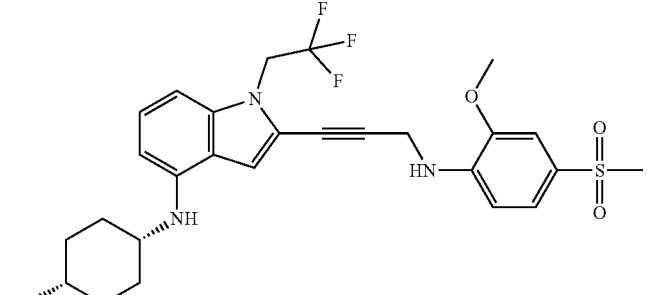<br>(1S,4S)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol |
| 637-P | 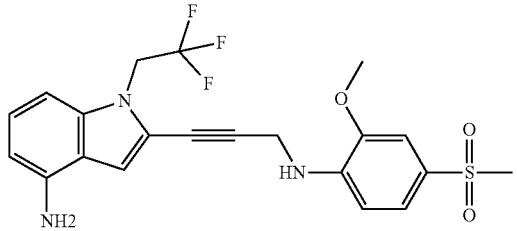 [SMILES: COc1cc(S(C)(=O)=O)ccc1NCC#Cc1cc2c(N)cccc2n1CC(F)(F)F]<br>2-{3-[(4-methanesulfonyl-2-methoxyphenyl)amino]prop-1-yn-1-yl}-1-(2,2,2-trifluoroethyl)-1H-indol-4-amine |
| 638-P | 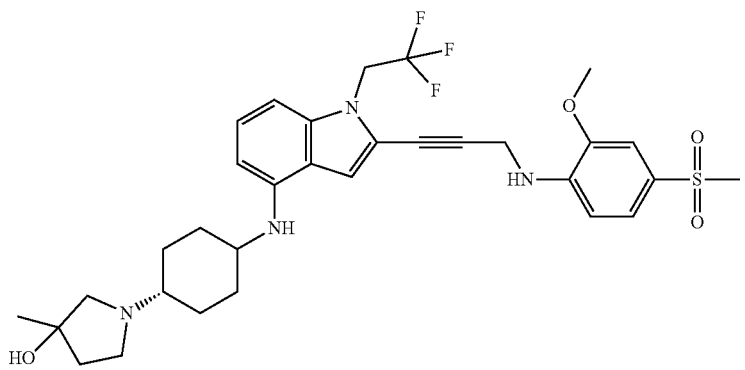<br>1-{4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl}-3-methylpyrrolidin-3-ol |

TABLE 1-continued

List of compounds

| # | Structure IUPAC name |
|---|---|
| 639-P | 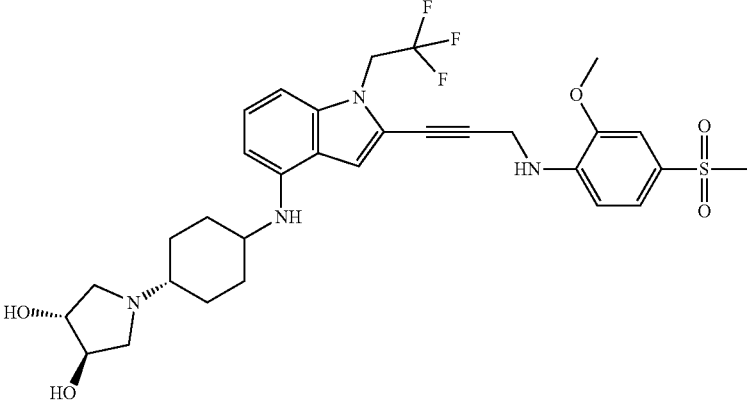<br>(3R,4R)-1-{4-[(2-{3-[(4-methane-sulfonyl-2-methoxyphenyl)amino]prop-1-yn-1-yl}-1-(2,2,2-trifluoroethyl)-1H-indol-4-yl)amino]cyclohexyl}-pyrrolidine-3,4-diol |
| 640-P | 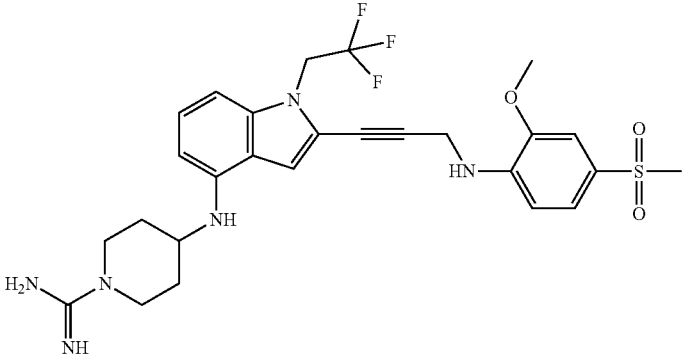<br>4-[(2-{3-[(4-methanesulfonyl-2-methoxyphenyl)amino]prop-1-yn-1-yl}-1-(2,2,2-trifluoroethyl)-1H-indol-4-yl)amino]piperidine-1-carboximidamide |
| 641-P | 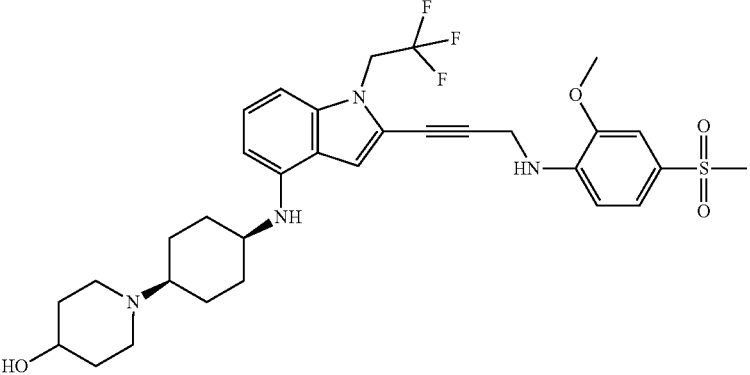 [SMILES: COc1cc(S(C)(=O)=O)ccc1NCC#Cc1cc2c(N[C@H]3CC[C@@H](N4CCC(O)CC4)CC3)cccc2n1CC(F)(F)F]<br>1-[(1S,4S)-4-[(2-{3-[(4-methane-sulfonyl-2-methoxyphenyl)amino]prop-1-yn-1-yl}-1-(2,2,2-trifluoroethyl)-1H-indol-4-yl)amino]cyclohexyl]piperidin-4-ol |

TABLE 1-continued

List of compounds

| # | Structure IUPAC name |
|---|---|
| 642-P | 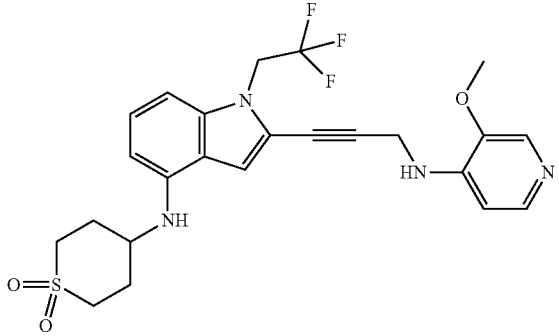 [SMILES: COc1cnccc1NCC#Cc1cc2c(NC3CCS(=O)(=O)CC3)cccc2n1CC(F)(F)F]<br>4-[(2-{3-[(3-methoxypyridin-4-yl)amino]prop-1-yn-1-yl}-1-(2,2,2-trifluoroethyl)-1H-indol-4-yl)amino]-1λ⁶-thiane-1,1-dione |
| 643-P | 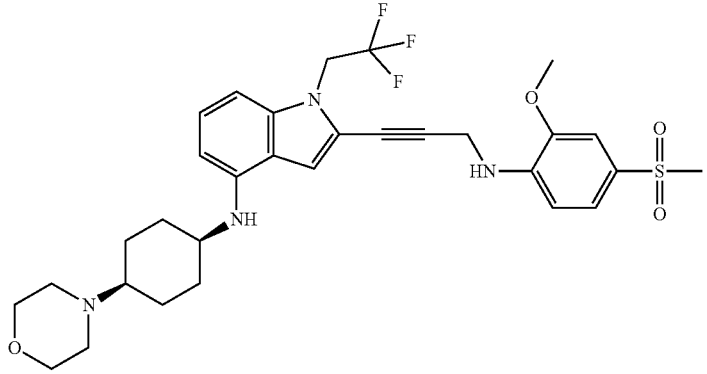 [SMILES: COc1cc(S(C)(=O)=O)ccc1NCC#Cc1cc2c(N[C@H]3CC[C@@H](N4CCOCC4)CC3)cccc2n1CC(F)(F)F]<br>2-{3-[(4-methanesulfonyl-2-methoxyphenyl)amino]prop-1-yn-1-yl}-N-[(1S,4S)-4-(morpholin-4-yl)cyclohexyl]-1-(2,2,2-trifluoroethyl)-1H-indol-4-amine |
| 644-P | 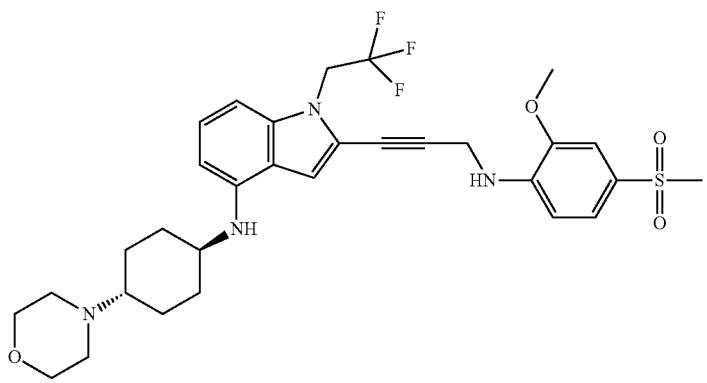 [SMILES: COc1cc(S(C)(=O)=O)ccc1NCC#Cc1cc2c(N[C@H]3CC[C@H](N4CCOCC4)CC3)cccc2n1CC(F)(F)F]<br>2-{3-[(4-methanesulfonyl-2-methoxyphenyl)amino]prop-1-yn-1-yl}-N-[(1R,4R)-4-(morpholin-4-yl)cyclohexyl]-1-(2,2,2-trifluoroethyl)-1H-indol-4-amine |

TABLE 1-continued

| # | Structure IUPAC name |
|---|---|
| 645-P | 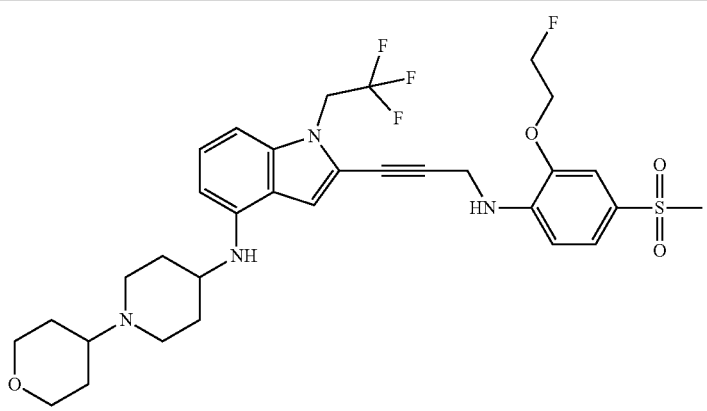 [SMILES: CS(=O)(=O)c1ccc(NCC#Cc2cc3c(NC4CCN(C5CCOCC5)CC4)cccc3n2CC(F)(F)F)c(OCCF)c1]<br>2-(3-{[2-(2-fluoroethoxy)-4-methanesulfonylphenyl]amino}prop-1-yn-1-yl)-N-[1-(oxan-4-yl)piperidin-4-yl]-1-(2,2,2-trifluoroethyl)-1H-indol-4-amine |
| 646-P | 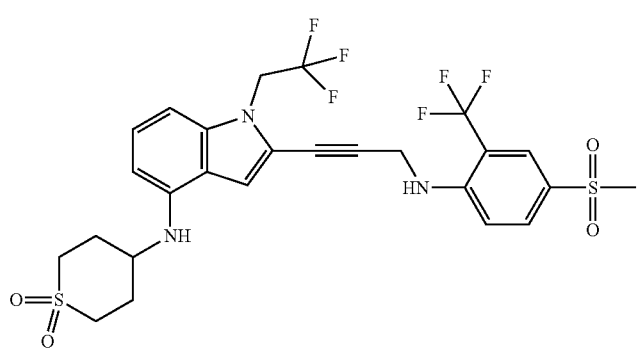 [SMILES: CS(=O)(=O)c1ccc(NCC#Cc2cc3c(NC4CCS(=O)(=O)CC4)cccc3n2CC(F)(F)F)c(C(F)(F)F)c1]<br>4-{[2-(3-{[4-methanesulfonyl-2-(trifluoromethyl)phenyl]amino}prop-1-yn-1-yl)-1-(2,2,2-trifluoroethyl)-1H-indol-4-yl]amino}-1λ⁶-thiane-1,1-dione |
| 647-P | 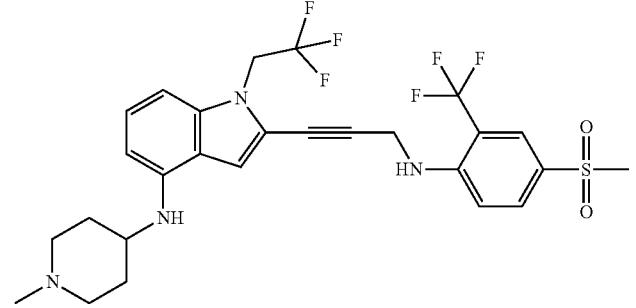<br>2-(3-{[4-methanesulfonyl-2-(trifluoromethyl)phenyl]amino}prop-1-yn-1-yl)-N-(1-methylpiperidin-4-yl)-1-(2,2,2-trifluoroethyl)-1H-indol-4-amine |

TABLE 1-continued

List of compounds

| # | Structure IUPAC name |
|---|---|
| 648-P | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethan-1-one |
| 649-P | 3-methoxy-4-{[3-(4-{[1-(1-methylpiperidin-4-yl)piperidin-4-yl]amino}-1-(2,2,2-trifluoroethyl)-1H-indol-2-yl)prop-2-yn-1-yl]amino}benzene-1-sulfonamide |
| 650-P | 3-methoxy-4-[(3-{4-[(piperidin-4-yl)amino]-1-(2,2,2-trifluoroethyl)-1H-indol-2-yl}prop-2-yn-1-yl)amino]-benzamide |

TABLE 1-continued

List of compounds

| # | Structure IUPAC name |
|---|---|
| 651-P | 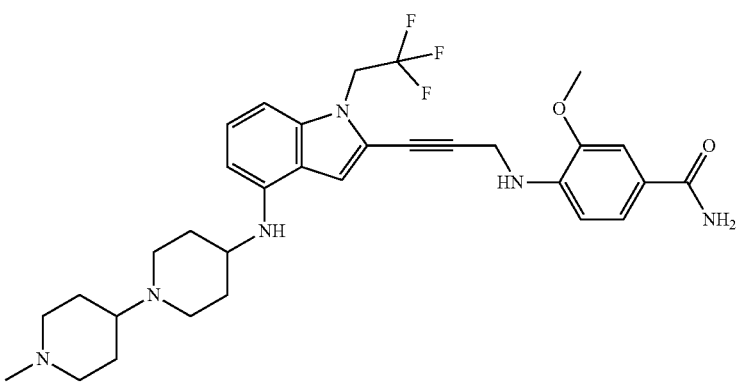 [SMILES: COc1cc(C(N)=O)ccc1NCC#Cc1cc2c(NC3CCN(C4CCN(C)CC4)CC3)cccc2n1CC(F)(F)F]<br>3-methoxy-4-{[3-(4-{[1-(1-methylpiperidin-4-yl)piperidin-4-yl]amino}-1-(2,2,2-trifluoroethyl)-1H-indol-2-yl)prop-2-yn-1-yl]amino}benzamide |
| 652-P | 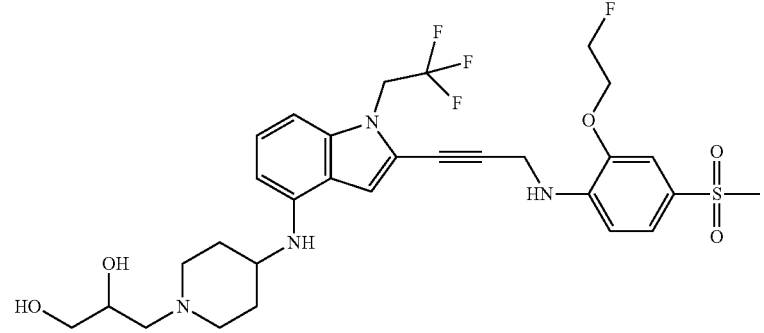 [SMILES: CS(=O)(=O)c1ccc(NCC#Cc2cc3c(NC4CCN(CC(O)CO)CC4)cccc3n2CC(F)(F)F)c(OCCF)c1]<br>3-(4-{[2-(3-{[2-(2-fluoroethoxy)-4-methanesulfonylphenyl]amino}prop-1-yn-1-yl)-1-(2,2,2-trifluoroethyl)-1H-indol-4-yl]amino}piperidin-1-yl)propane-1,2-diol |
| 653-P | 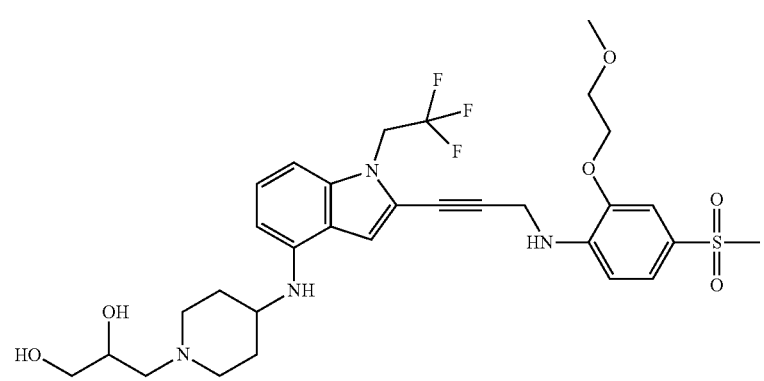 [SMILES: COCCOc1cc(S(C)(=O)=O)ccc1NCC#Cc1cc2c(NC3CCN(CC(O)CO)CC3)cccc2n1CC(F)(F)F]<br>3-(4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}piperidin-1-yl)propane-1,2-diol |

TABLE 1-continued

List of compounds

| # | Structure IUPAC name |
|---|---|

654-P

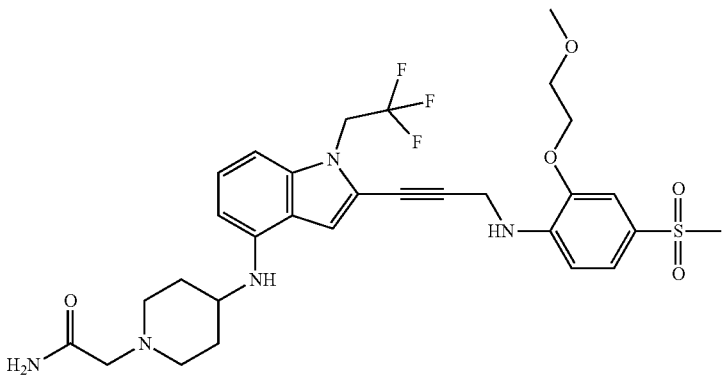 [SMILES: COCCOc1cc(S(C)(=O)=O)ccc1NCC#Cc1cc2c(NC3CCN(CC(N)=O)CC3)cccc2n1CC(F)(F)F]

2-(4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}piperidin-1-yl)acetamide

655-P

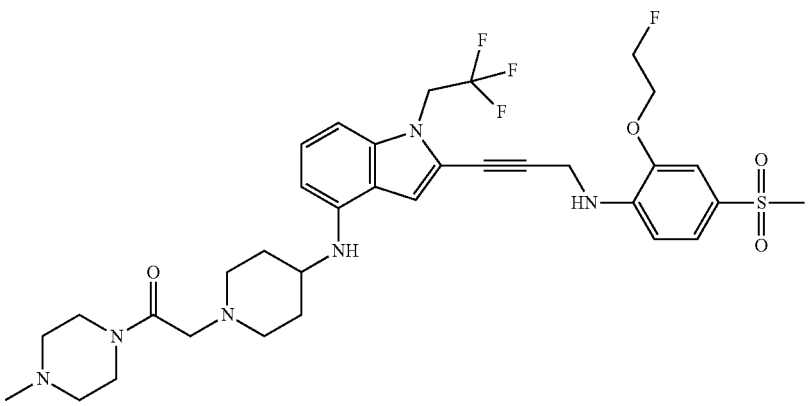

2-(4-{[2-(3-{[2-(2-fluoroethoxy)-4-methanesulfonylphenyl]amino}prop-1-yn-1-yl)-1-(2,2,2-trifluoroethyl)-1H-indol-4-yl]amino}piperidin-1-yl)-1-(4-methylpiperazin-1-yl)ethan-1-one

656-P

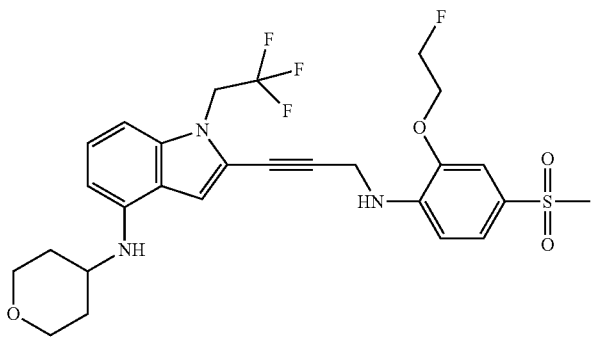 [SMILES: CS(=O)(=O)c1ccc(NCC#Cc2cc3c(NC4CCOCC4)cccc3n2CC(F)(F)F)c(OCCF)c1]

2-(3-{[2-(2-fluoroethoxy)-4-methanesulfonylphenyl]amino}prop-1-yn-1-yl)-N-(oxan-4-yl)-1-(2,2,2-trifluoroethyl)-1H-indol-4-amine TABLE 1-continued

| # | Structure IUPAC name |
|---|---|
| 657-P | 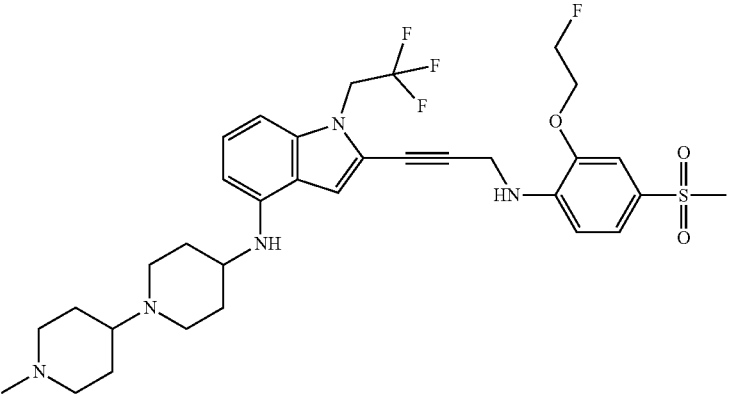
2-(3-{[2-(2-fluoroethoxy)-4-methanesulfonylphenyl]amino}prop-1-yn-1-yl)-N-[1-(1-methylpiperidin-4-yl)piperidin-4-yl]-1-(2,2,2-trifluoroethyl)-1H-indol-4-amine |
| 658-P | 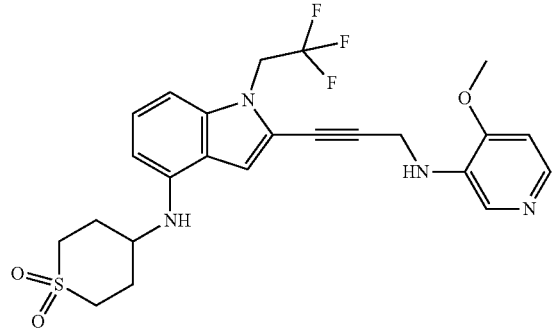 [SMILES: COc1ccncc1NCC#Cc1cc2c(NC3CCS(=O)(=O)CC3)cccc2n1CC(F)(F)F]
4-[(2-{3-[(4-methoxypyridin-3-yl)amino]prop-1-yn-1-yl}-1-(2,2,2-trifluoroethyl)-1H-indol-4-yl)amino]-1$\lambda^6$-thiane-1,1-dione |
| 659-P | 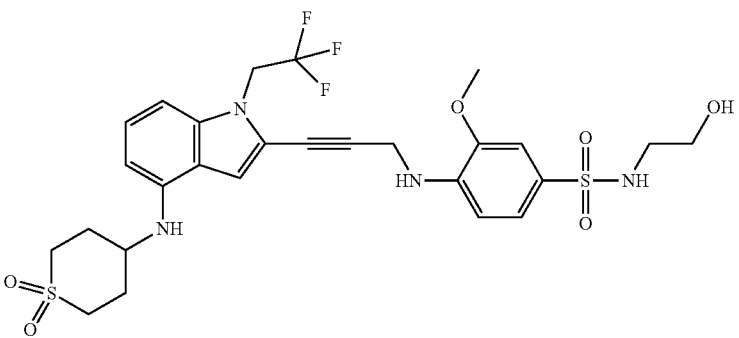 [SMILES: COc1cc(S(=O)(=O)NCCO)ccc1NCC#Cc1cc2c(NC3CCS(=O)(=O)CC3)cccc2n1CC(F)(F)F]
S-{4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxyphenyl}-2-hydroxyethane-1-sulfonamido |

TABLE 1-continued

List of compounds

| # | Structure IUPAC name |
|---|---|

660-P

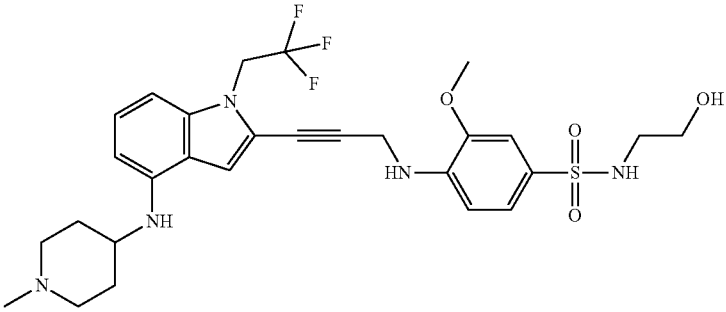 [SMILES: COc1cc(S(=O)(=O)NCCO)ccc1NCC#Cc1cc2c(NC3CCN(C)CC3)cccc2n1CC(F)(F)F]

2-hydroxy-S-{3-methoxy-4-[(3-{4-[(1-methylpiperidin-4-yl)amino]-1-(2,2,2-trifluoroethyl)-1H-indol-2-yl}prop-2-yn-1-yl)amino]phenyl}ethane-1-sulfonamido

661-P

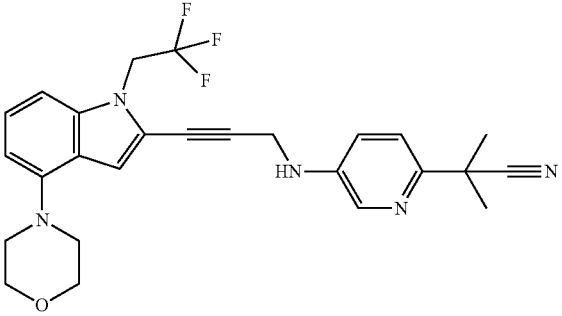 [SMILES: CC(C)(C#N)c1ccc(NCC#Cc2cc3c(N4CCOCC4)cccc3n2CC(F)(F)F)cn1]

2-methyl-2-[5-({3-[4-(morpholin-4-yl)-1-(2,2,2-trifluoroethyl)-1H-indol-2-yl]prop-2-yn-1-yl}amino)pyridin-2-yl]propanenitrile

662-P

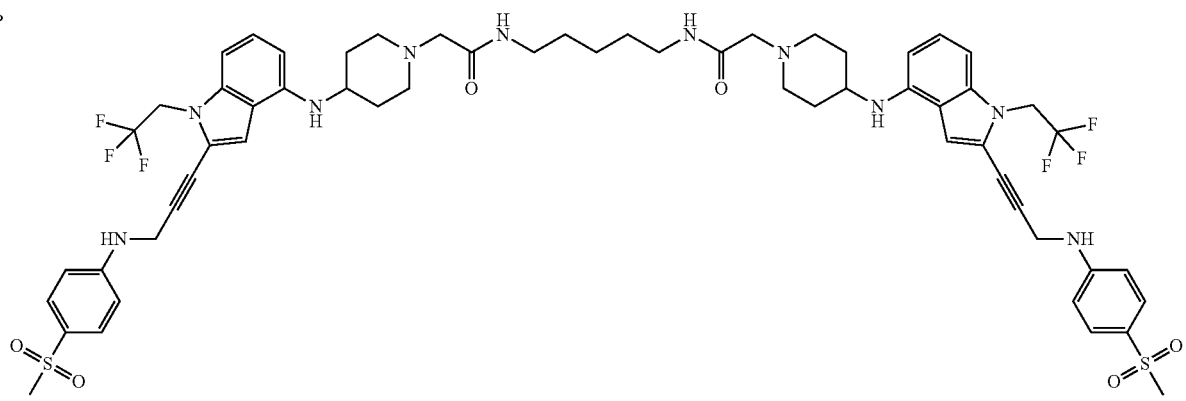 [SMILES: CS(=O)(=O)c1ccc(NCC#Cc2cc3c(NC4CCN(CC(=O)NCCCCCNC(=O)CN5CCC(Nc6cccc7c6cc(C#CCNc6ccc(S(C)(=O)=O)cc6)n7CC(F)(F)F)CC5)CC4)cccc3n2CC(F)(F)F)cc1]

-{4-[(2-{3-[(4-methanesulfonylphenyl)amino]prop-1-yn-1-yl}-1-(2,2,2-trifluoroethyl)-1H-indol-4-yl)amino]piperidin-1-yl}-N-[5-(2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetamido)pentyl]acetamide

| # | Structure IUPAC name |
|---|---|
| 663-P | 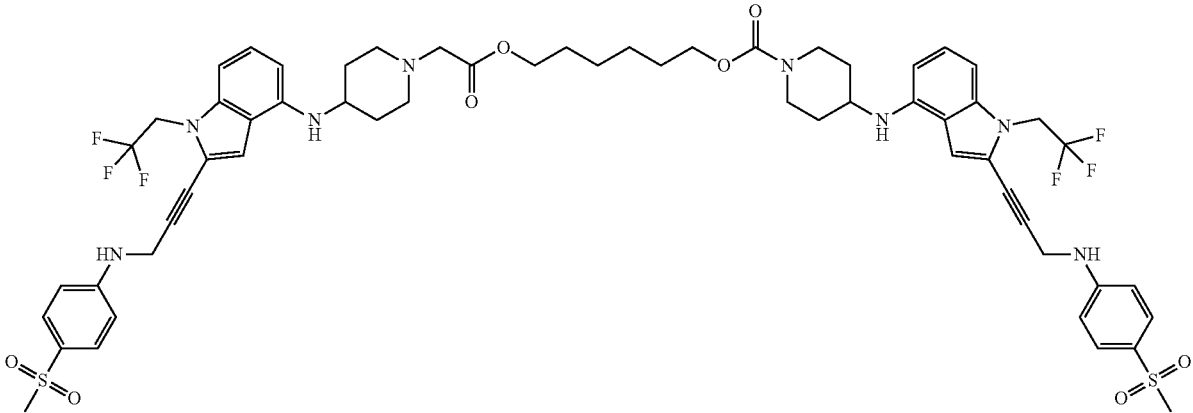 [SMILES: CS(=O)(=O)c1ccc(NCC#Cc2cc3c(NC4CCN(CC(=O)OCCCCCCOC(=O)N5CCC(Nc6cccc7c6cc(C#CCNc6ccc(S(C)(=O)=O)cc6)n7CC(F)(F)F)CC5)CC4)cccc3n2CC(F)(F)F)cc1]

6-[(2-{4-[(2-{3-[(4-
methanesulfonylphenyl)amino]prop-1-yn-1-
yl}-1-(2,2,2-trifluoroethyl)-1H-indol-4-
yl)amino]piperidin-1-yl}acetyl)oxy]hexyl 2-
{4-[(2-{3-[(4-
methanesulfonylphenyl)amino]prop-1-yn-1-
yl}-1-(2,2,2-trifluoroethyl)-1H-indol-4-
yl)amino]piperidin-1-yl}acetate |
| 664-P | 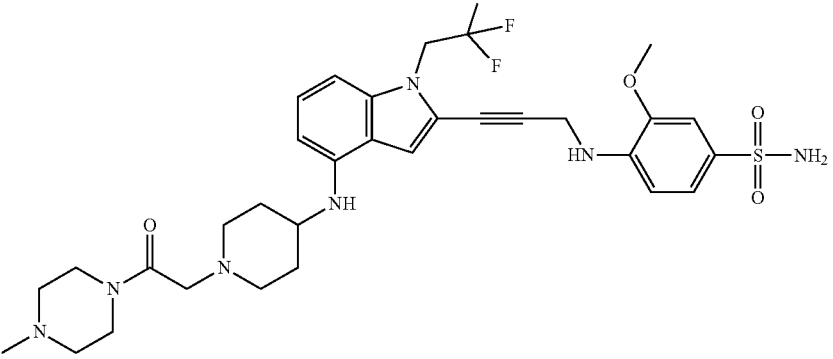

3-methoxy-4-({3-[4-({1-[2-(4-
methylpiperazin-1-yl)-2-oxoethyl]piperidin-
4-yl}amino)-1-(2,2,2-trifluoroethyl)-1H-
indol-2-yl]prop-2-yn-1-yl}amino)benzene-1-sulfonamide |
| 665-P | 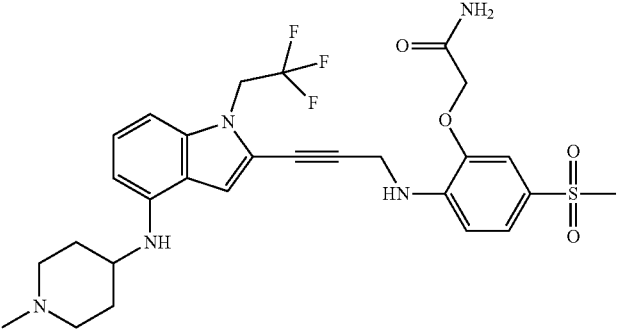

2-{5-methanesulfonyl-2-[(3-{4-[(1-
methylpiperidin-4-yl)amino]-1-(2,2,2-
trifluoroethyl)-1H-indol-2-yl}prop-2-yn-1-
yl)amino]phenoxy}acetamide |

TABLE 1-continued
List of compounds
| # | Structure | IUPAC name |
|---|---|---|
| 666-P | 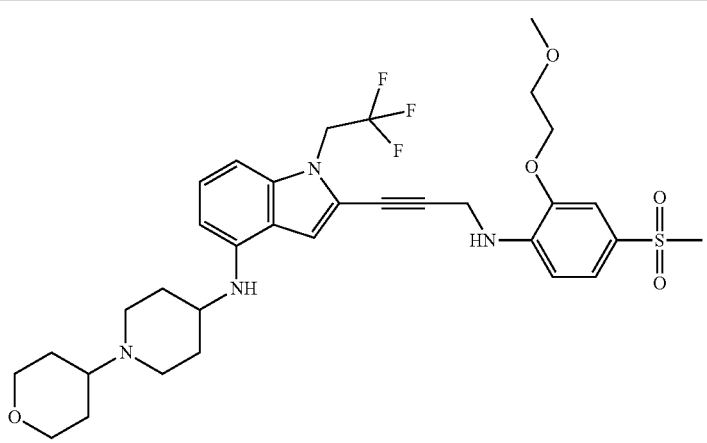 [SMILES: COCCOc1cc(S(C)(=O)=O)ccc1NCC#Cc1cc2c(NC3CCN(C4CCOCC4)CC3)cccc2n1CC(F)(F)F] | 2-(3-{[4-methanesulfonyl-2-(2-methoxyethoxy)phenyl]amino}prop-1-yn-1-yl)-N-[1-(oxan-4-yl)piperidin-4-yl]-1-(2,2,2-trifluoroethyl)-1H-indol-4-amine |
| 667-P | 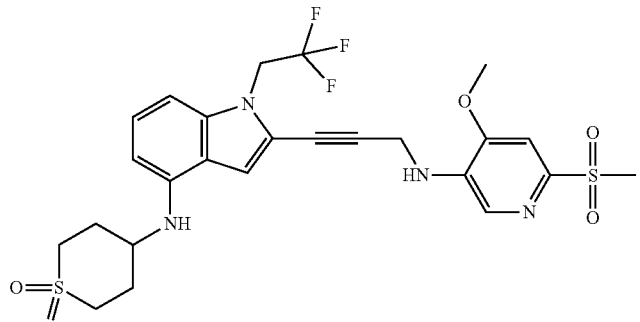 | 2-(4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}piperidin-1-yl)ethan-1-ol |
| 668-P | 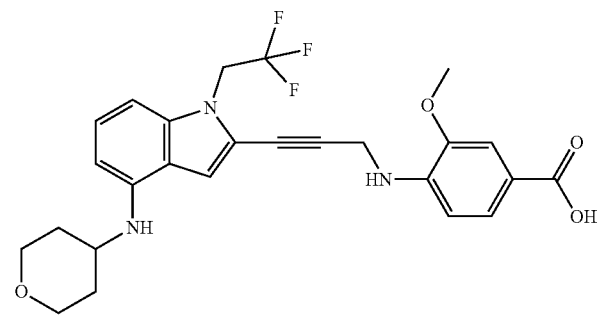 [SMILES: COc1cc(C(=O)O)ccc1NCC#Cc1cc2c(NC3CCOCC3)cccc2n1CC(F)(F)F] | 3-methoxy-4-[(3-{4-[(oxan-4-yl)amino]-1-(2,2,2-trifluoroethyl)-1H-indol-2-yl}prop-2-yn-1-yl)amino]benzoic acid |

TABLE 1-continued

List of compounds

| # | Structure IUPAC name |
|---|---|
| 669-P | 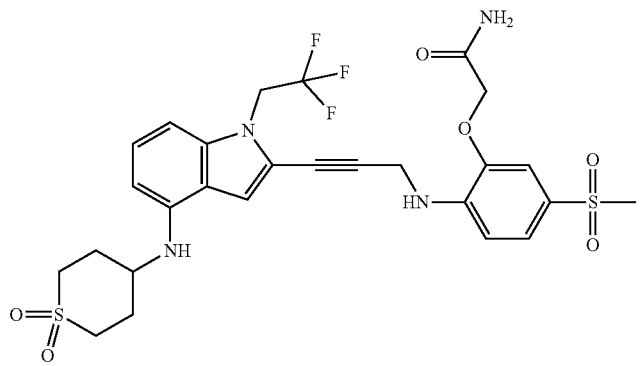 [SMILES: CS(=O)(=O)c1ccc(NCC#Cc2cc3c(NC4CCS(=O)(=O)CC4)cccc3n2CC(F)(F)F)c(OCC(N)=O)c1]<br>2-{2-[(3-{4-[(1,1-dioxo-1λ⁶-thian-4-yl)amino]-1-(2,2,2-trifluoroethyl)-1H-indol-2-yl}prop-2-yn-1-yl)amino]-5-methanesulfonylphenoxy}acetamide |
| 670-P | 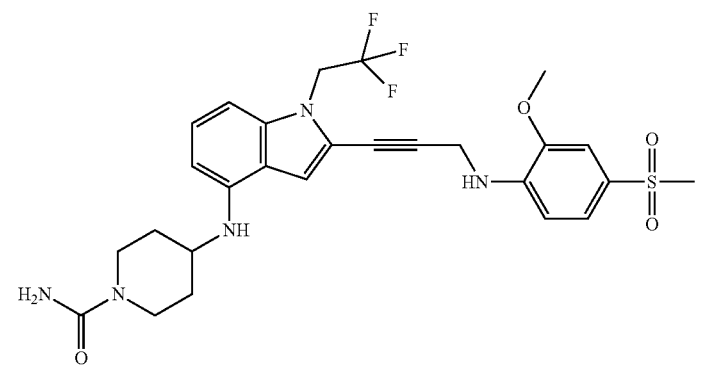 [SMILES: COc1cc(S(C)(=O)=O)ccc1NCC#Cc1cc2c(NC3CCN(C(N)=O)CC3)cccc2n1CC(F)(F)F]<br>4-[(2-{3-[(4-methanesulfonyl-2-methoxyphenyl)amino]prop-1-yn-1-yl}-1-(2,2,2-trifluoroethyl)-1H-indol-4-yl)amino]piperidine-1-carboxamide |
| 671-P | 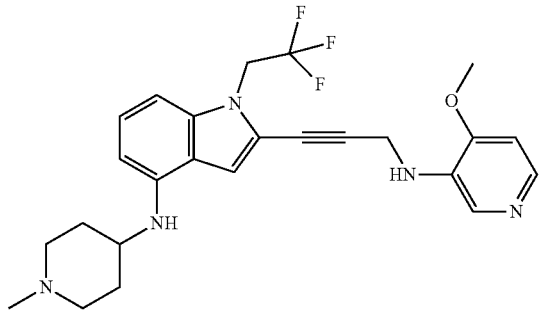 [SMILES: COc1ccncc1NCC#Cc1cc2c(NC3CCN(C)CC3)cccc2n1CC(F)(F)F]<br>2-{3-[(4-methoxypyridin-3-yl)amino]prop-1-yn-1-yl}-N-(1-methylpiperidin-4-yl)-1-(2,2,2-trifluoroethyl)-1H-indol-4-amine |

TABLE 1-continued

List of compounds

| # | Structure | IUPAC name |
|---|-----------|------------|
| 672-P | 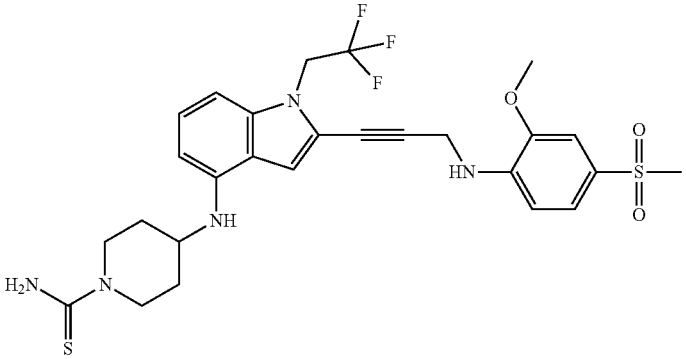 [SMILES: COc1cc(S(C)(=O)=O)ccc1NCC#Cc1cc2c(NC3CCN(C(N)=S)CC3)cccc2n1CC(F)(F)F] | 4-[(2-{3-[(4-methanesulfonyl-2-methoxyphenyl)amino]prop-1-yn-1-yl}-1-(2,2,2-trifluoroethyl)-1H-indol-4-yl)amino]piperidine-1-carbothioamide |
| 673-P | 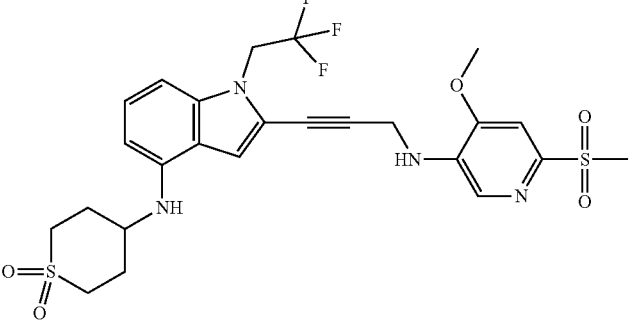 | 4-[(2-{3-[(6-methanesulfonyl-4-methoxypyridin-3-yl)amino]prop-1-yn-1-yl}-1-(2,2,2-trifluoroethyl)-1H-indol-4-yl)amino]-1λ⁶-thiane-1,1-dione |
| 674-P | 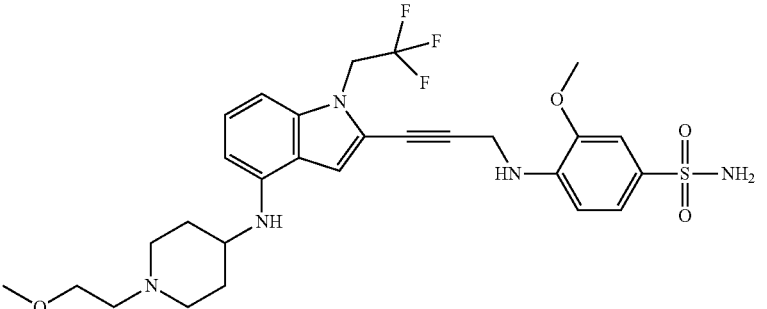 | 3-methoxy-4-{[3-(4-{[1-(2-methoxyethyl)piperidin-4-yl]amino}-1-(2,2,2-trifluoroethyl)-1H-indol-2-yl)prop-2-yn-1-yl]amino}benzene-1-sulfonamide |

TABLE 1-continued

List of compounds

| # | Structure IUPAC name |
|---|---|
| 675-P | 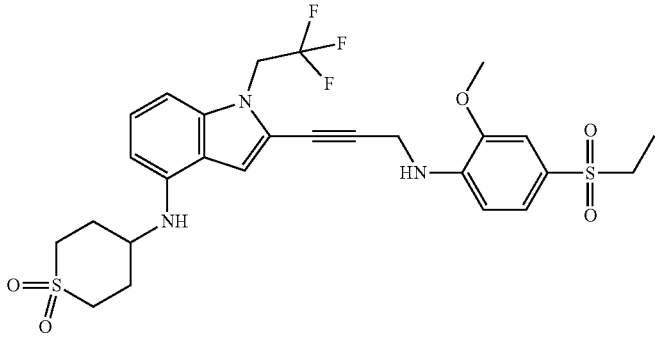 [SMILES: CCS(=O)(=O)c1ccc(NCC#Cc2cc3c(NC4CCS(=O)(=O)CC4)cccc3n2CC(F)(F)F)c(OC)c1]<br>4-{[2-(3-{[4-(ethanesulfonyl)-2-methoxyphenyl]amino}prop-1-yn-1-yl)-1-(2,2,2-trifluoroethyl)-1H-indol-4-yl]amino}-1$\lambda^6$-thiane-1,1-dione |
| 676-P | 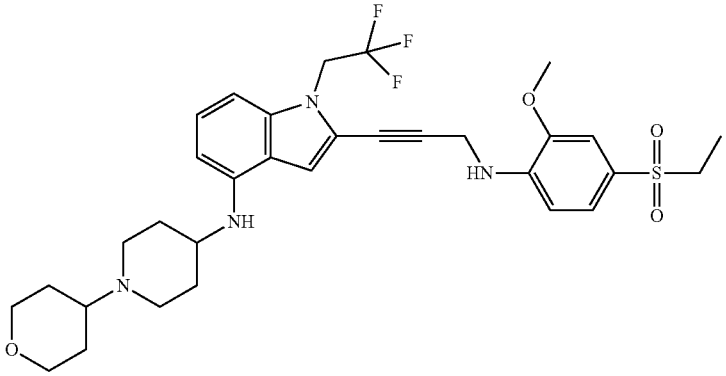 [SMILES: CCS(=O)(=O)c1ccc(NCC#Cc2cc3c(NC4CCN(C5CCOCC5)CC4)cccc3n2CC(F)(F)F)c(OC)c1]<br>2-(3-{[4-(ethanesulfonyl)-2-methoxyphenyl]amino}prop-1-yn-1-yl)-N-[1-(oxan-4-yl)piperidin-4-yl]-1-(2,2,2-trifluoroethyl)-1H-indol-4-amine |
| 677-P | 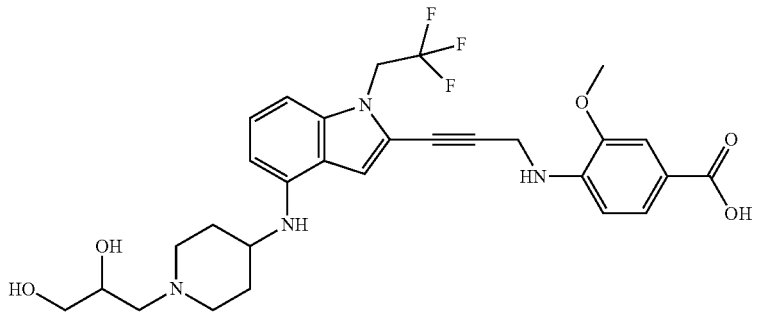 [SMILES: COc1cc(C(=O)O)ccc1NCC#Cc1cc2c(NC3CCN(CC(O)CO)CC3)cccc2n1CC(F)(F)F]<br>4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxybenzoic acid |

| # | Structure IUPAC name |
|---|---|
| 678-P | 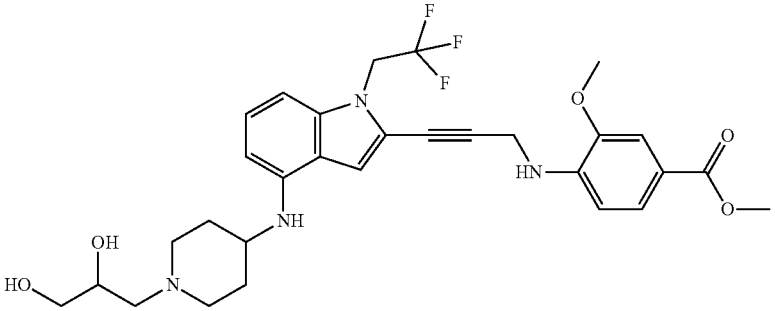 [SMILES: COC(=O)c1ccc(NCC#Cc2cc3c(NC4CCN(CC(O)CO)CC4)cccc3n2CC(F)(F)F)c(OC)c1]
methyl 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxybenzoate |
| 679-P | 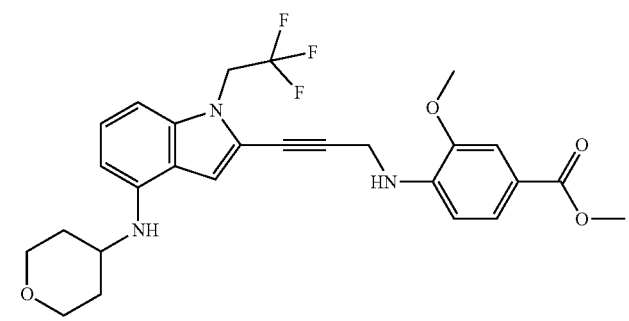 [SMILES: COC(=O)c1ccc(NCC#Cc2cc3c(NC4CCOCC4)cccc3n2CC(F)(F)F)c(OC)c1]
methyl 3-methoxy-4-[(3-{4-[(oxan-4-yl)amino]-1-(2,2,2-trifluoroethyl)-1H-indol-2-yl}prop-2-yn-1-yl)amino]benzoate |
| 680-P | 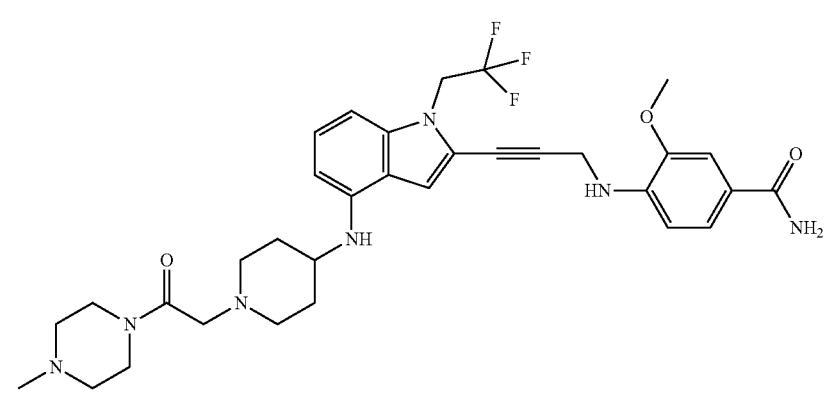 [SMILES: COc1cc(C(N)=O)ccc1NCC#Cc1cc2c(NC3CCN(CC(=O)N4CCN(C)CC4)CC3)cccc2n1CC(F)(F)F]
3-methoxy-4-({3-[4-({1-[2-(4-methylpiperazin-1-yl)-2-oxoethyl]piperidin-4-yl}amino)-1-(2,2,2-trifluoroethyl)-1H-indol-2-yl]prop-2-yn-1-yl}amino)benzamide |

TABLE 1-continued

List of compounds

| # | Structure IUPAC name |
|---|---|
| 681-P | 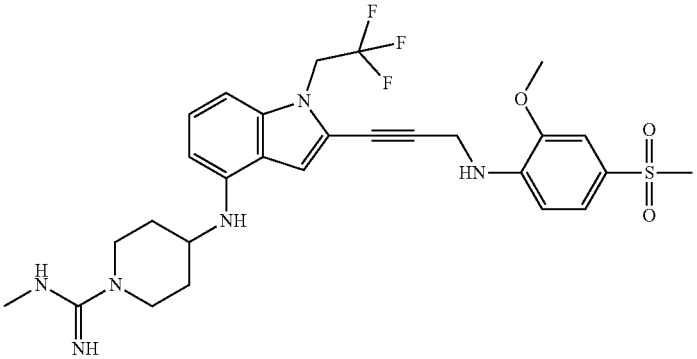<br>4-[(2-{3-[(4-methanesulfonyl-2-methoxyphenyl)amino]prop-1-yn-1-yl}-1-(2,2,2-trifluoroethyl)-1H-indol-4-yl)amino]-N-methylpiperidine-1-carboximidamide |
| 682-P | 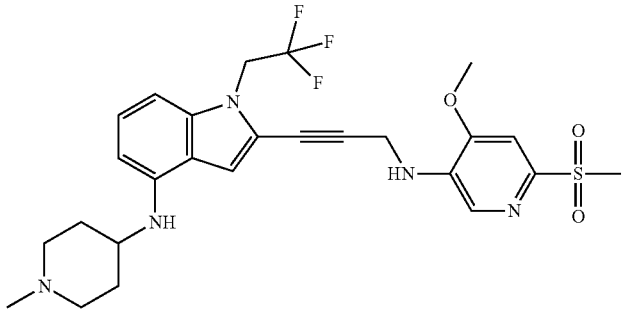<br>2-{3-[(6-methanesulfonyl-4-methoxypyridin-3-yl)amino]prop-1-yn-1-yl}-N-(1-methylpiperidin-4-yl)-1-(2,2,2-trifluoroethyl)-1H-indol-4-amine |
| 683-P | 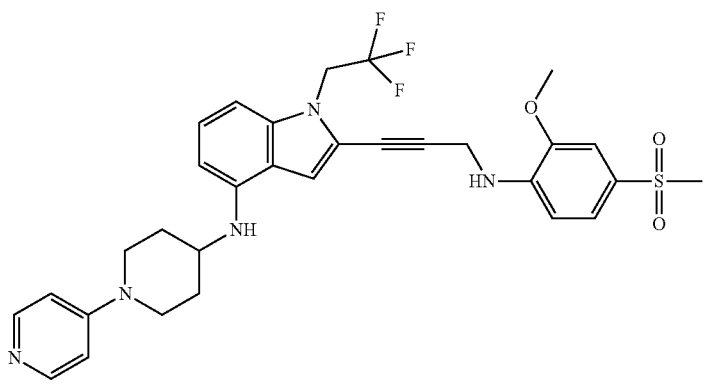 [SMILES: COc1cc(S(C)(=O)=O)ccc1NCC#Cc1cc2c(NC3CCN(c4ccncc4)CC3)cccc2n1CC(F)(F)F]<br>2-{3-[(4-methanesulfonyl-2-methoxyphenyl)amino]prop-1-yn-1-yl}-N-[1-(pyridin-4-yl)piperidin-4-yl]-1-(2,2,2-trifluoroethyl)-1H-indol-4-amine |

TABLE 1-continued

List of compounds

| # | Structure IUPAC name |
|---|---|
| 684-P | 3-(4-{[2-(3-{[4-(ethanesulfonyl)-2-methoxyphenyl]amino}prop-1-yn-1-yl)-1-(2,2,2-trifluoroethyl)-1H-indol-4-yl]amino}piperidin-1-yl)propane-1,2-diol |
| 685-P | 2-(3-{[4-(ethanesulfonyl)-2-methoxyphenyl]amino}prop-1-yn-1-yl)-N-(1-methylpiperidin-4-yl)-1-(2,2,2-trifluoroethyl)-1H-indol-4-amine |
| 686-P | 2-hydroxy-S-{3-methoxy-4-[(3-{4-[(oxan-4-yl)amino]-1-(2,2,2-trifluoroethyl)-1H-indol-2-yl}prop-2-yn-1-yl)amino]phenyl}ethane-1-sulfonamido |

TABLE 1-continued

List of compounds

| # | Structure IUPAC name |
|---|---|
| 687-P | 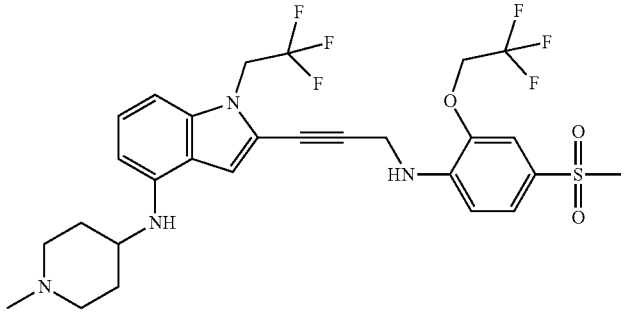 2-(3-{[4-methanesulfonyl-2-(2,2,2-trifluoroethoxy)phenyl]amino}prop-1-yn-1-yl)-N-(1-methylpiperidin-4-yl)-1-(2,2,2-trifluoroethyl)-1H-indol-4-amine |
| 688-P | 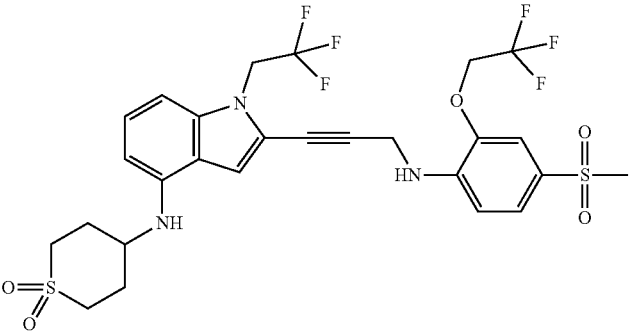 [SMILES: CS(=O)(=O)c1ccc(NCC#Cc2cc3c(NC4CCS(=O)(=O)CC4)cccc3n2CC(F)(F)F)c(OCC(F)(F)F)c1] 4-{[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]amino}-1$\lambda^6$-thiane-1,1-dione |
| 689-P | 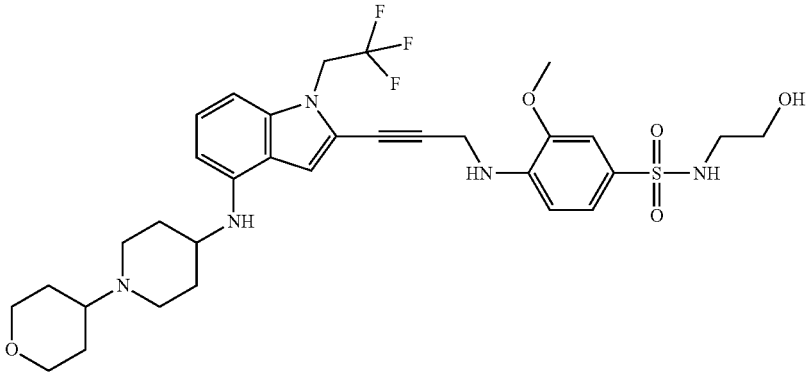 [SMILES: COc1cc(S(=O)(=O)NCCO)ccc1NCC#Cc1cc2c(NC3CCN(C4CCOCC4)CC3)cccc2n1CC(F)(F)F] 2-hydroxy-S-(3-methoxy-4-{[3-(4-{[1-(oxan-4-yl)piperidin-4-yl]amino}-1-(2,2,2-trifluoroethyl)-1H-indol-2-yl)prop-2-yn-1-yl]amino}phenyl)ethane-1-sulfonamido |

TABLE 1-continued

List of compounds

| # | Structure IUPAC name |
|---|---|
| 690-P | S-(4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxyphenyl)-2-hydroxyethane-1-sulfonamido |
| 691-P | 2-{3-methoxy-4-[(3-{4-[(1-methylpiperidin-4-yl)amino]-1-(2,2,2-trifluoroethyl)-1H-indol-2-yl}prop-2-yn-1-yl)amino]phenyl}-2-methylpropanenitrile |
| 692-P | 3-methoxy-4-{[3-(4-{[(1S,4S)-4-[(3R,4R)-3,4-dihydroxypyrrolidin-1-yl]cyclohexyl]amino}-1-(2,2,2-trifluoroethyl)-1H-indol-2-yl)prop-2-yn-1-yl]amino}benzene-1-sulfonamide |

TABLE 1-continued

List of compounds

| # | Structure IUPAC name |
|---|---|
| 693-P | 3-methoxy-4-{[3-(4-{[(1R,4R)-4-[(3R,4R)-3,4-dihydroxypyrrolidin-1-yl]cyclohexyl]amino}-1-(2,2,2-trifluoroethyl)-1H-indol-2-yl)prop-2-yn-1-yl]amino}benzene-1-sulfonamide |
| 694-P | 3-methoxy-4-{[3-(4-{[(1S,4S)-4-(4-hydroxypiperidin-1-yl)cyclohexyl]amino}-1-(2,2,2-trifluoroethyl)-1H-indol-2-yl)prop-2-yn-1-yl]amino}benzene-1-sulfonamide |
| 695-P | 3-methoxy-4-{[3-(4-{[(1R,4R)-4-(4-hydroxypiperidin-1-yl)cyclohexyl]amino}-1-(2,2,2-trifluoroethyl)-1H-indol-2-yl)prop-2-yn-1-yl]amino}benzene-1-sulfonamide |

TABLE 1-continued

| List of compounds | |
|---|---|
| # | Structure IUPAC name |

696-P

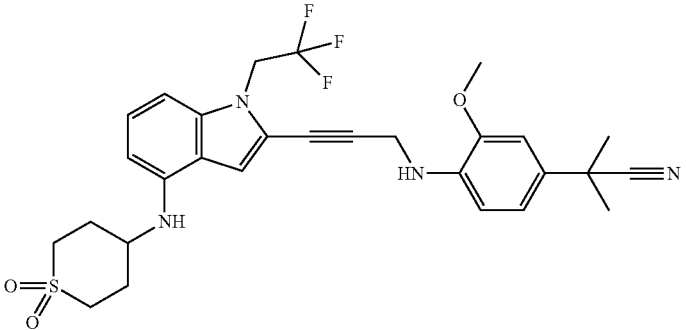 [SMILES: COc1cc(C(C)(C)C#N)ccc1NCC#Cc1cc2c(NC3CCS(=O)(=O)CC3)cccc2n1CC(F)(F)F]

2-{4-[(3-{4-[(1,1-dioxo-1λ⁶-thian-4-yl)amino]-1-(2,2,2-trifluoroethyl)-1H-indol-2-yl}prop-2-yn-1-yl)amino]-3-methoxyphenyl}-2-methylpropanenitrile

697-P

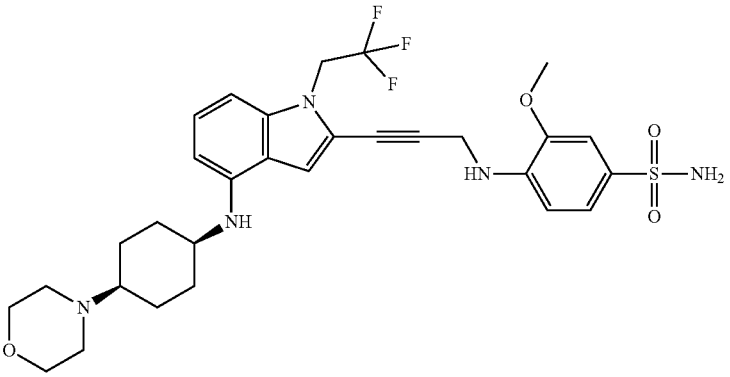 [SMILES: COc1cc(S(N)(=O)=O)ccc1NCC#Cc1cc2c(N[C@H]3CC[C@@H](N4CCOCC4)CC3)cccc2n1CC(F)(F)F]

3-methoxy-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzene-1-sulfonamide

698-P

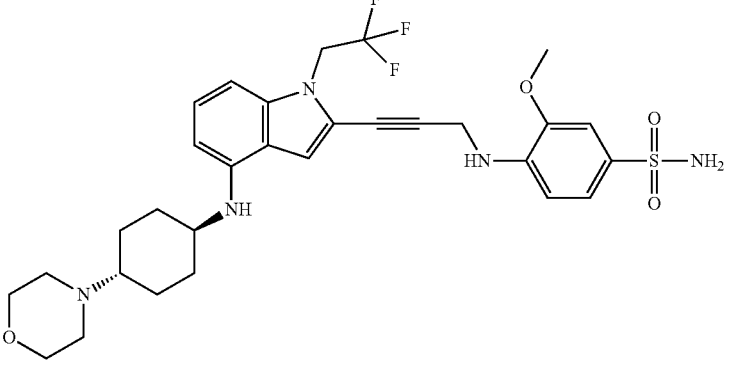

3-methoxy-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide TABLE 1-continued List of compounds

| # | Structure IUPAC name |
|---|---|
| 699-P | 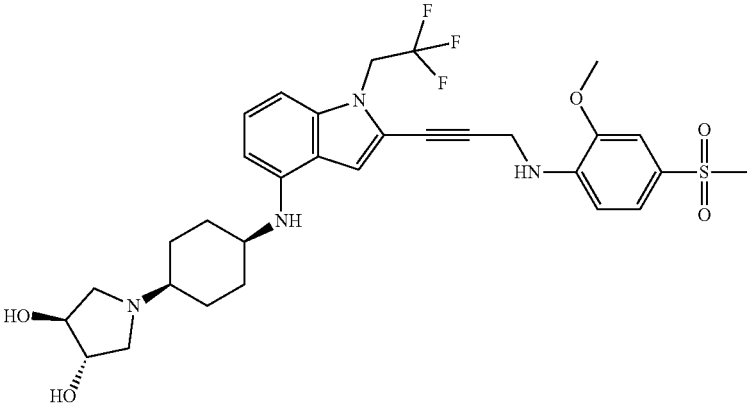 [SMILES: COc1cc(S(C)(=O)=O)ccc1NCC#Cc1cc2c(N[C@H]3CC[C@@H](N4C[C@H](O)[C@@H](O)C4)CC3)cccc2n1CC(F)(F)F]<br>(3S,4S)-1-[(1S,4S)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]pyrrolidine-3,4-diol |
| 700-P | 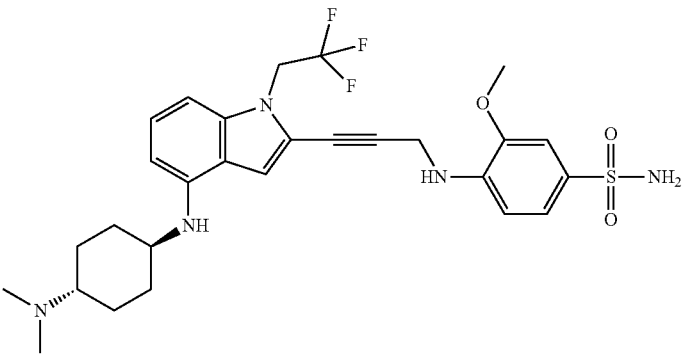 [SMILES: COc1cc(S(N)(=O)=O)ccc1NCC#Cc1cc2c(N[C@H]3CC[C@H](N(C)C)CC3)cccc2n1CC(F)(F)F]<br>3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 701-P | 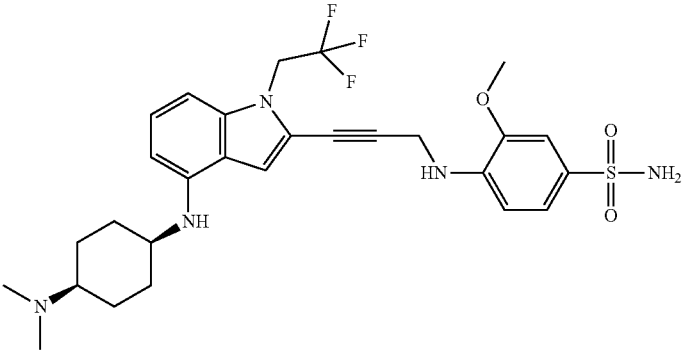 [SMILES: COc1cc(S(N)(=O)=O)ccc1NCC#Cc1cc2c(N[C@H]3CC[C@@H](N(C)C)CC3)cccc2n1CC(F)(F)F]<br>3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |

In some embodiments, disclosed herein is a method of treating a cancer, the method comprising administering to a subject in need thereof a therapeutically-effective amount of a compound of the disclosure. A compound of the invention can, for example, slow the proliferation of cancer cell lines, or kill cancer cells. Non-limiting examples of cancer that can be treated by a compound of the invention include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenstrom macroglobulinemia, and Wilms tumor.

In some embodiments, the compounds of the invention show non-lethal toxicity.

In some embodiments, disclosed herein is a method of treating cancer comprising administering to a subject in need thereof a compound of Formula (I):

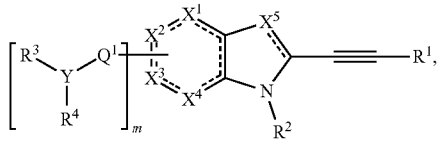

wherein:
each ------- is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
$Q^1$ is C=O, C=S, C=CR$^{14}$R$^{15}$, C=NR$^{14}$, alkylene, alkenylene, or alkynylene, each of which is independently substituted or unsubstituted, or a bond;
m is 1, 2, 3, or 4;
Y is N, O, or absent;
$R^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, C=O, C=S, —CN, —SiR$^{16}$R$^{17}$R$^{18}$, alkyl, alkenyl, alkynyl, aryl, heteroaryl, or heterocyclyl, each of which is independently substituted or unsubstituted, or hydrogen;
each $R^3$ and $R^4$ is independently, —C(O)R$^{19}$, —C(O)OR$^{19}$, —C(O)NR$^{19}$R$^{20}$, —SOR$^{19}$, —SO$_2$R$^{19}$, alkyl, alkylene, alkenyl, alkenylene, alkynyl, aryl, heteroaryl, or heterocyclyl, each of which is independently substituted or unsubstituted, or hydrogen, or $R^3$ and $R^4$ together with the Y atom to which $R^3$ and $R^4$ are bound form a ring, wherein the ring is substituted or unsubstituted, or $R^3$ is absent;
each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen,
or a pharmaceutically acceptable salt thereof;
wherein the compound has an SC$_{150}$ value for p53 Y220C of less than 1 µM as measured by a homogeneous time-resolved fluorescence (HTRF) assay In some embodiments, disclosed herein is a method of inducing apoptosis in a cell, the method comprising contacting the cell with a therapeutically-effective amount of a compound that binds a p53 mutant, wherein the compound is a compound disclosed herein. In some embodiments, the compound increases the ability of the p53 mutant to bind DNA. In some embodiments, the cell expresses the p53. In some embodiments, the p53 mutant has a mutation at amino acid 220. In some embodiments, the p53 mutant is p53 Y220C. In some embodiments, the compound induces a conformational change in the p53 mutant. In some embodiments, the compound selectively binds the p53 mutant as compared to a wild type p53. In some embodiments, the therapeutically effective amount is from about 50 mg to about 3000 mg. In some embodiments, the compound increases a stability of a biologically active conformation of the p53 mutant relative to a stability of the biologically active conformation of the p53 mutant in an absence of the compound.

Pharmaceutically-Acceptable Salts.

The invention provides the use of pharmaceutically-acceptable salts of any therapeutic compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Pharmaceutical Compositions of the Invention.

A pharmaceutical composition of the invention can be used, for example, before, during, or after treatment of a subject with, for example, another pharmaceutical agent.

Subjects can be, for example, elderly adults, adults, adolescents, pre-adolescents, children, toddlers, infants, neonates, and non-human animals. In some embodiments, a subject is a patient.

A pharmaceutical composition of the invention can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration.

A pharmaceutical composition can be administered in a local manner, for example, via injection of the compound directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining the active compounds with pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N, N'-bis(2-ethanesulfonic acid) buffer (PIPES), and saline sodium citrate buffer (SSC). Non-limiting examples of co-solvents used in an oral dissolvable formulation can include sucrose, urea, cremaphor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

The compounds of the invention can be applied topically to the skin, or a body cavity, for example, oral, vaginal, bladder, cranial, spinal, thoracic, or pelvic cavity of a subject. The compounds of the invention can be applied to an accessible body cavity.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, and PEG. In suppository forms of the compositions, a low-melting wax such as a mixture of fatty acid glycerides, optionally in combination with cocoa butter, can be melted.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulations can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include liquid, powder, gel, nanosuspension, nanoparticle, microgel, aqueous or oily suspensions, emulsion, and any combination thereof.

Non-limiting examples of pharmaceutically-acceptable excipients suitable for use in the invention include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 h.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 h.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Multiple therapeutic agents can be administered in any order or simultaneously. In some embodiments, a compound of the invention is administered in combination with, before, or after treatment with another therapeutic agent. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneously, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 h of the onset of the symptoms, within the first 24 h of the onset of the symptoms, within the first 6 h of the onset of the symptoms, or within 3 h of the onset of the symptoms. The initial administration can be via any route practical, such as by any route described herein using any formulation described herein.

A compound can be administered as soon as is practical after the onset of a disease or condition is detected or suspected, and for a length of time necessary for the treatment of the disease, such as, for example, from about 1 month to about 3 months. In some embodiments, the length of time a compound can be administered can be about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months about 23 months, about 2 years, about 2.5 years, about 3 years, about 3.5 years, about 4 years, about 4.5 years, about 5 years, about 6 years, about 7 years, about 8 years, about 9 years, or about 10 years. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of pharmaceutically active agents suitable for combination with compositions of the disclosure include anti-infectives, i.e., aminoglycosides, antiviral agents, antimicrobials, anticholinergics/antispasmotics, antidiabetic agents, antihypertensive agents, antineoplastics, cardiovascular agents, central nervous system agents, coagulation modifiers, hormones, immunologic agents, immunosuppressive agents, and ophthalmic preparations.

Compounds can be delivered via liposomal technology. The use of liposomes as drug carriers can increase the therapeutic index of the compounds. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compositions of the invention can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Dosing.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A dose can be expressed in terms of an amount of the drug divided by the mass of the subject, for example, milligrams of drug per kilograms of subject body mass. A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

In some embodiments, a compound is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg. In some embodiments, a compound described herein can be present in a composition in a range of from about 20 mg/kg to about 400 mg/kg. In some embodiments, a compound described herein can be present in a composition in a range of from about 20 mg/kg to about 240 mg/kg. In some embodiments, a compound described herein can be present in a composition in a range of from about 75 mg/kg to about 150 mg/kg. In some embodiments, a compound described herein can be present in a composition in a range of from about 75 mg/kg to about 150 mg/kg. In some embodiments, a compound described herein can be present in a composition in a range of from about 100 mg/kg to about 150 mg/kg.

In some embodiments, a compound described herein can be present in a composition in an amount of about 75 mg/kg. In some embodiments, a compound described herein can be present in a composition in an amount of about 100 mg/kg. In some embodiments, a compound described herein can be present in a composition in an amount of about 150 mg/kg. In some embodiments, a compound described herein can be present in a composition in an amount of about 200 mg/kg. In some embodiments, a compound described herein can be present in a composition in an amount of about 250 mg/kg. In some embodiments, a compound described herein can be present in a composition in an amount of about 400 mg/kg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a compound described herein can be present in a composition in an amount of about 100 mg, about 120 mg, about 140 mg, about 160 mg, about 180 mg, about 200 mg, about 220 mg, about 240 mg, about 260 mg, about 280 mg, or about 300 mg. In some embodiments, a compound described herein can be present in a composition in an amount of about 150 mg. In some embodiments, a compound described herein can be present in a composition in an amount of about 170 mg. In some embodiments, a compound described herein can be present in a composition in an amount of about 280 mg. In some embodiments, a compound described herein can be present in a composition in an amount of about 300 mg.

EXAMPLES

A. Synthesis of Alkynyl Reagents

Example A1: Synthesis of 3-(fluoromethoxy)-N-methyl-4-(prop-2-yn-1-ylamino)benzamide

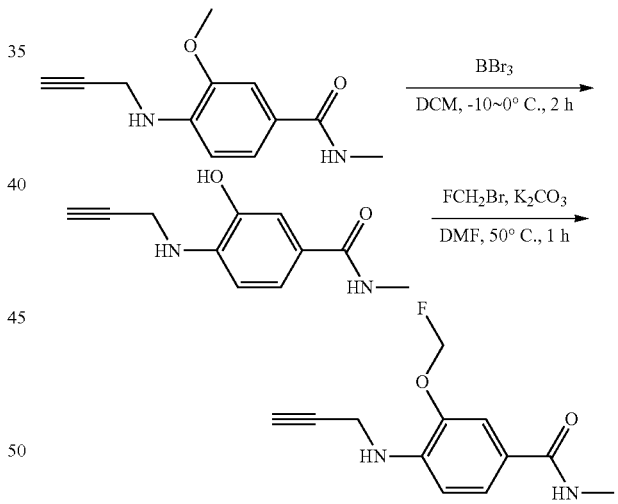

Step 1. To a solution of 3-methoxy-N-methyl-4-(prop-2-yn-1-ylamino)benzamide (947.37 mg, 4.12 mmol, 1 eq.) in DCM (50 mL) was added dropwise BBr$_3$ (3.62 g, 14.43 mmol, 1.39 mL, 3.5 eq.) at −10° C. The mixture was stirred at 0° C. for 2 h. TLC analysis (DCM:MeOH=20:1, R$_f$=0.4) indicated that ~10% of the starting material remained, and one new spot with polarity lower than that of the starting material was detected. Saturated solution of NaOH was added until the pH of the mixture was greater than 11. The mixture was extracted with DCM (50 mL×3), and the organic layer was discarded. 12M HCl was added into the aqueous phase until the pH was 8. The aqueous phase was extracted with EtOAc (150 mL×3), and the combined organic layers were washed with brine (150 mL×3), dried over anhydrous sodium sulfate, filtered, and concentrated under reduced pressure. The resulting residue was stirred in PE (50 mL) at 25° C. for 12 h. The mixture then was filtered to afford 3-hydroxy-N-methyl-4-(prop-2-yn-1-ylamino)benzamide (0.7 g, 3.08 mmol, 74.81% yield) as a yellow solid.

Step 2. To a solution of 3-hydroxy-N-methyl-4-(prop-2-yn-1-ylamino)benzamide (0.3 g, 1.32 mmol, 1 eq.) and bromofluoromethane (298.60 mg, 2.64 mmol, 251.45 µL, 2 eq.) in DMF (10 mL) was added $K_2CO_3$ (365.45 mg, 2.64 mmol, 2 eq.). The mixture was stirred at 50° C. for 1 h, after which time TLC analysis (DCM:MeOH=20:1, $R_f$=0.5) indicated that the starting phenol was completely consumed, and one new spot was observed. The mixture was poured into water (20 mL) and extracted with EtOAc (20 mL×3). The combined organic layers were washed with brine (20 mL×3), dried over anhydrous sodium sulfate, filtered, and concentrated. The resulting residue was purified by prep-TLC (DCM:MeOH=20:1, $R_f$=0.5) to afford 3-(fluoromethoxy)-N-methyl-4-(prop-2-yn-1-ylamino)benzamide (0.3 g, 1.08 mmol, 81.64% yield) as a yellow solid.

Example A2: Synthesis of 3-(2-cyanoethoxy)-N-methyl-4-(prop-2-yn-1-ylamino)benzamide

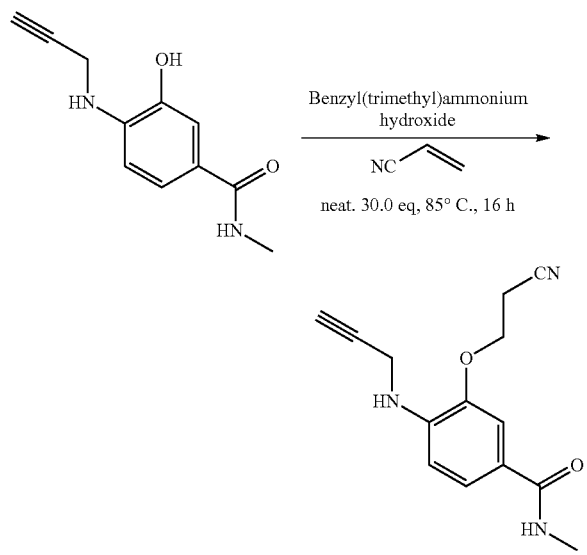

A mixture of 3-hydroxy-N-methyl-4-(prop-2-yn-1-ylamino)benzamide (200 mg, 685.52 µmol, 1 eq.) and benzyl(trimethyl)ammonium hydroxide (3.82 mg, 6.86 µmol, 4.15 µL, 30% purity, 0.01 eq.) was stirred in acrylonitrile (1.09 g, 20.57 mmol, 1.36 mL, 30 eq.) at 85° C. for 16 h under $N_2$. TLC analysis indicated that ~50% of the starting phenol remained, and one new spot with polarity lower than that of the starting material was observed. The mixture was concentrated under reduced pressure to provide a residue, which was purified by prep-TLC (DCM:MeOH=20:1, $R_f$=0.5) to afford 3-(2-cyanoethoxy)-N-methyl-4-(prop-2-yn-1-ylamino)benzamide (100 mg, 349.80 µmol, 39.69% yield) as a yellow solid.

Example A3: Synthesis of 3-(cyanomethoxy)-4-(prop-2-yn-1-ylamino)benzenesulfonamide

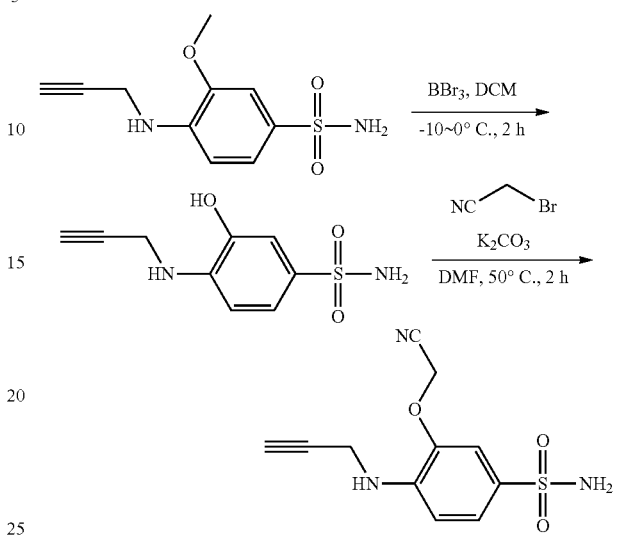

Step 1. To a solution of 3-methoxy-4-(prop-2-yn-1-ylamino)benzenesulfonamide (0.4 g, 1.42 mmol, 1 eq.) in DCM (10 mL) was added dropwise $BBr_3$ (1.24 g, 4.95 mmol, 477.20 µL, 3.5 eq.) at −10° C. The mixture was stirred at 0° C. for 2 h, after which time TLC analysis (DCM:MeOH=10:1, $R_f$=0.4) indicated that ~10% of the starting methyl ether remained, and two new spots with polarity greater than that of the starting material were observed. 1N NaOH was added until the pH of the mixture was greater than 11. The mixture was extracted with DCM (50 mL×3), and the organic layer was discarded. 12M HCl was added into the aqueous phase until the pH was equal to 8, and the aqueous phase was extracted with EtOAc (150 mL×3). The combined organic layers were washed with brine (150 mL×3), dried over anhydrous sodium sulfate, filtered, and concentrated under reduced pressure. The resulting residue was purified by prep-TLC (DCM:MeOH=10:1, $R_f$=0.4) to afford 3-hydroxy-4-(prop-2-yn-1-ylamino)benzenesulfonamide (0.25 g, 983.42 µmol, 69.50% yield) as a yellow solid.

Step 2. To a solution of 3-hydroxy-4-(prop-2-yn-1-ylamino)benzenesulfonamide (0.25 g, 983.42 µmol, 1 eq.) and bromoacrylonitrile (235.92 mg, 1.97 mmol, 131.07 µL, 2 eq.) in DMF (10 mL) was added $K_2CO_3$ (271.84 mg, 1.97 mmol, 2 eq.). The mixture was stirred at 50° C. for 2 h. TLC analysis (DCM:MeOH=10:1, $R_f$=0.5) indicated that the starting phenol was completely consumed, and one new spot was observed. The mixture was poured into water (30 mL) and extracted with EtOAc (30 mL×3). The combined organic layers were washed with brine (30 mL×3), dried over anhydrous sodium sulfate, filtered, and concentrated under reduced pressure. The resulting residue was purified by prep-TLC (DCM:MeOH=10:1, $R_f$=0.5) to afford 3-(cyanomethoxy)-4-(prop-2-yn-1-ylamino)benzenesulfonamide (0.2 g, 716.20 µmol, 72.83% yield) as a yellow solid.

Example A4: General Procedure for Preparation of 2-(fluoromethoxy)-4-(methylsulfonyl)-N-(prop-2-yn-1-yl)aniline, and 2-(5-(methylsulfonyl)-2-(prop-2-yn-1-ylamino)phenoxy)acetonitrile

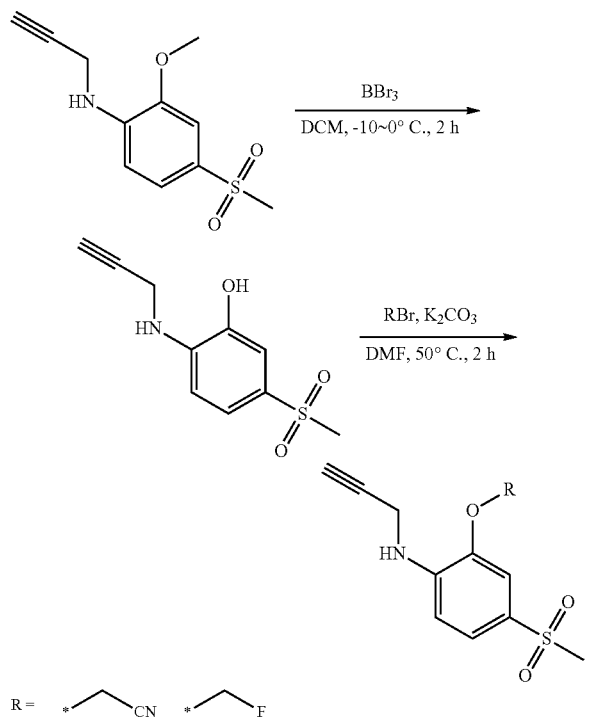

Synthesis of 5-(methylsulfonyl)-2-(prop-2-yn-1-ylamino)phenol: To a solution of 2-methoxy-4-(methylsulfonyl)-N-(prop-2-yn-1-yl)aniline (5 g, 19.85 mmol, 1 eq.) in DCM (50 mL) was added dropwise BBr₃ (12.43 g, 49.63 mmol, 4.78 mL, 2.5 eq.) at −10° C. The mixture was stirred at 0° C. for 2 h. TLC analysis (PE:EtOAc=1:1, R$_f$=0.4) indicated that ~10% of the starting methyl ether remained, and one major new spot with polarity greater than that of the starting material was observed. 1N NaOH was added until the pH of the mixture was greater than 11. The mixture was extracted with DCM (50 mL×3), and the organic layer was discarded. 12M HCl was added into the aqueous phase until the pH was equal to 8, and the aqueous phase was extracted with EtOAc (150 mL×3). The combined organic layers were washed with brine (150 mL×3), dried over anhydrous sodium sulfate, filtered, and concentrated under reduced pressure. The resulting residue was stirred in PE (50 mL) at 25° C. for 12 h. The mixture was then filtered and dried to afford 5-(methylsulfonyl)-2-(prop-2-yn-1-ylamino)phenol (8 g, 30.19 mmol, 76.04% yield) as a yellow solid.

Synthesis of 2-(fluoromethoxy)-4-(methylsulfonyl)-N-(prop-2-yn-1-yl)aniline, and 2-(5-(methylsulfonyl)-2-(prop-2-yn-1-ylamino)phenoxy)acetonitrile: To a solution of 5-(methylsulfonyl)-2-(prop-2-yn-1-ylamino)phenol (0.5 g, 2.22 mmol, 1 eq.) and 2-bromoacetonitrile (450 mg, 3.77 mmol, 2 eq.) or bromofluoromethane: 422 mg, 3.77 mmol, 2 eq.) in DMF (10 mL) was added K₂CO₃ (521.5 mg, 3.77 mmol, 2 eq.). The mixture was stirred at 50° C. for 2 h, and the mixture was poured into water (50 mL). The mixture was extracted with EtOAc (30 mL×3), and the combined organic layers were washed with brine (40 mL×3), dried over anhydrous sodium sulfate, filtered and concentrated under reduced pressure. The resulting residue was purified by column chromatography to afford 2-(fluoromethoxy)-4-(methylsulfonyl)-N-(prop-2-yn-1-yl)aniline (700 mg, crude) or 2-(5-(methylsulfonyl)-2-(prop-2-yn-1-ylamino)phenoxy)acetonitrile as a yellow gum.

Example A5: General Procedure for Preparation of N-((3-methoxy-4-(prop-2-yn-1-ylamino)phenyl)sulfonyl)acetamide and N-((3-methoxy-4-(prop-2-yn-1-ylamino)phenyl)sulfonyl)propionamide

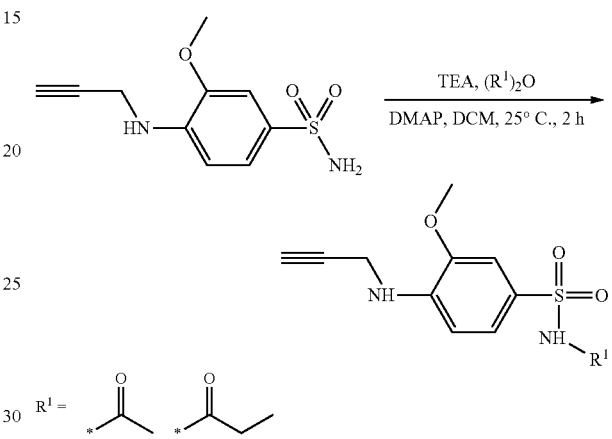

To a mixture of 3-methoxy-4-(prop-2-yn-1-ylamino)benzenesulfonamide (1 eq.), DMAP (0.1 eq.), and TEA (1 eq.) in THF (4 mL) was added (R¹)₂O (2 eq.) under N₂ at 25° C. The mixture was stirred at 25° C. for 2 h, and TLC analysis indicated that the reaction was complete. The reaction mixture was diluted with water (20 mL) and extracted with EtOAc (20 mL×3). The combined organic layers were washed with brine (20 mL), dried over anhydrous sodium sulfate, filtered, and concentrated under reduced pressure. The residue was purified by prep-TLC to provide the desired product as a yellow oil.

Example A6: Preparation of N-((3-methoxy-4-(prop-2-yn-1-ylamino)phenyl)sulfonyl)-N-methyl-propionamide

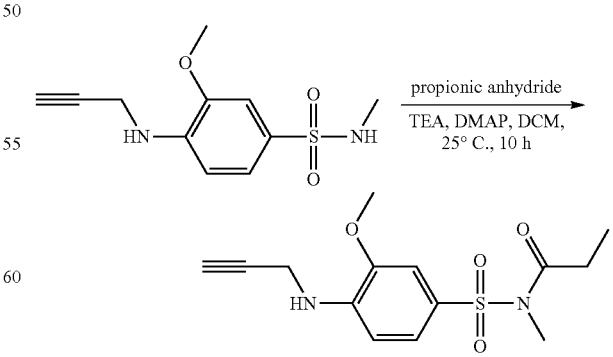

To a solution of 3-methoxy-N-methyl-4-(prop-2-yn-1-ylamino)benzenesulfonamide (0.06 g, 235.94 μmol, 1 eq.) in THF (2 mL) were added DMAP (2.88 mg, 23.59 μmol, 0.1 eq.), TEA (23.87 mg, 235.94 μmol, 32.84 μL, 1 eq.), and propionic anhydride (61.41 mg, 471.87 μmol, 60.80 μL, 2 eq.). The reaction mixture was stirred at 25° C. for 10 h. LC-MS analysis detected the desired mass. The reaction mixture was concentrated under reduced pressure, and the resulting residue was purified by prep-TLC (SiO$_2$, PE:EtOAc=1:1, R$_f$=0.43) to provide N-((3-methoxy-4-(prop-2-yn-1-ylamino)phenyl)sulfonyl)-N-methylpropionamide (0.04 g, 90.22 μmol, 38.24% yield) as a yellow solid.

Example A7: Preparation of N-methyl-5-(methylsulfonyl)-2-(prop-2-yn-1-yloxy)aniline, N,N-dimethyl-5-(methylsulfonyl)-2-(prop-2-yn-1-yloxy)aniline, and N-(5-(methylsulfonyl)-2-(prop-2-yn-1-yloxy)phenyl)acetamide Synthesis of N-(5-(methylsulfonyl)-2-(prop-2-yn-1-yloxy)phenyl)acetamide: A mixture of 5-(methylsulfonyl)-2-(prop-2-yn-1-yloxy)aniline (100 mg, 399.53 μmol, 1 eq.), acetic anhydride (203.94 mg, 2 mmol, 187.10 μL, 5 eq.), and TEA (80.86 mg, 799.06 μmol, 111.22 μL, 2 eq.) in DCM (3 mL) was stirred at 50° C. for 2 h. TLC analysis (EtOAc, R$_f$=0.24) indicated that the reaction was complete. The reaction mixture was concentrated under reduced pressure to remove solvent. The residue was purified by prep-TLC to provide N-(5-(methylsulfonyl)-2-(prop-2-yn-1-yloxy)phenyl)acetamide (100 mg, 374.11 μmol, 93.64% yield) as a light yellow solid.

Synthesis of N-methyl-5-(methylsulfonyl)-2-(prop-2-yn-1-yloxy)aniline: To a solution of 5-(methylsulfonyl)-2-(prop-2-yn-1-yloxy)aniline (0.5 g, 2.2 mmol, 1 eq.) in MeOH (5 mL) were added AcOH (53.3 mg, 887.8 μmol,

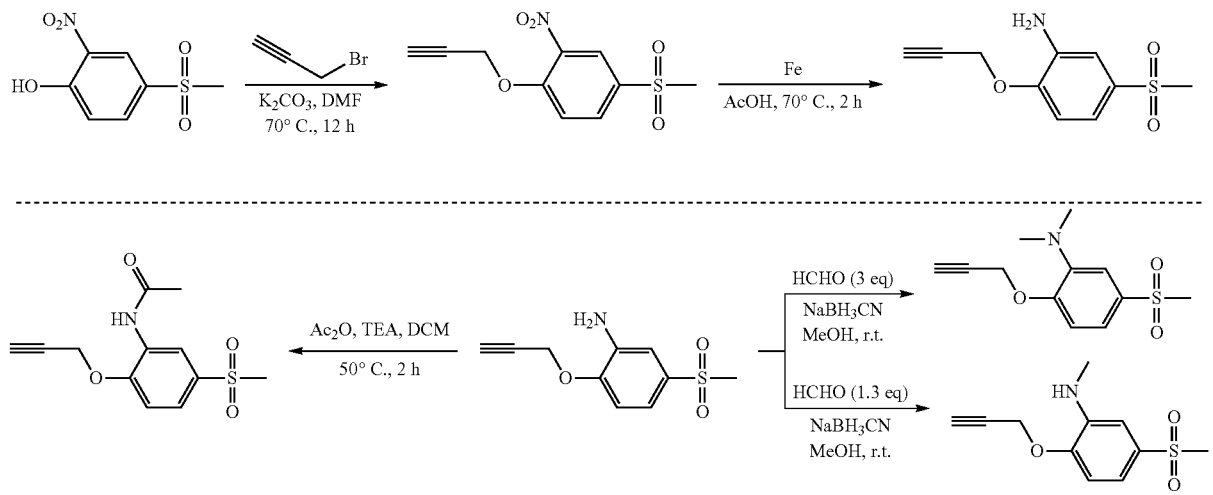

50.8 μL, 0.4 eq.) and NaBH$_3$CN (418.5 mg, 6.66 mmol, 3 eq.). The mixture was stirred at 25° C. for 0.5 h, then formaldehyde (234.2 mg, 2.9 mmol, 214.8 μL, 1.3 eq.) was added. The mixture was stirred further at 25° C. for 9.5 h, after which time LC-MS analysis indicated that the reaction was complete. The reaction mixture was partitioned by adding a saturated solution of NaHCO$_3$ (30 mL) and EtOAc (10 mL), and extracted with EtOAc (5 mL×3). The combined organic layers were washed with brine (10 mL×3), dried over anhydrous sodium sulfate, filtered, and concentrated under reduced pressure. The residue was first purified by prep-TLC (PE:EtOAc=2:1, R$_f$=0.6) and further purified by prep-HPLC to provide N-methyl-5-(methylsulfonyl)-2-(prop-2-yn-1-yloxy)aniline (100 mg, 376.11 μmol, 16.94% yield) as a colorless oil.

Synthesis of N,N-dimethyl-5-(methylsulfonyl)-2-(prop-2-yn-1-yloxy)aniline: To a solution of 5-(methylsulfonyl)-2-(prop-2-yn-1-yloxy)aniline (0.2 g, 887.8 μmol, 1 eq.) in MeOH (5 mL) were added AcOH (21.3 mg, 355.1 μmol, 20.3 μL, 0.4 eq.) and NaBH$_3$CN (167.4 mg, 2.66 mmol, 3 eq.). The mixture was stirred at 25° C. for 0.5 h, then formaldehyde (216.2 mg, 2.7 mmol, 198.3 μL, 3 eq.) was added. The mixture was stirred further at 25° C. for 9.5 h, after which time LC-MS analysis indicated that the reaction was complete. The reaction mixture was partitioned by adding a saturated solution of NaHCO$_3$ (30 mL) and EtOAc (10 mL), and extracted with EtOAc (5 mL×3). The combined organic layers were washed with brine (10 mL×3), Synthesis of 4-(methylsulfonyl)-2-nitro-1-(prop-2-yn-1-yloxy)benzene: To a mixture of propargyl bromide (2.74 g, 23 mmol, 1.98 mL, 5 eq.) and 4-(methylsulfonyl)-2-nitrophenol (1 g, 4.60 mmol, 1 eq.) in DMF (10 mL) was added K$_2$CO$_3$ (1.91 g, 13.80 mmol, 3 eq.). The mixture was stirred at 50° C. for 2 h, after which time TLC (EtOAc, Rf=0.43) indicated that the reaction was complete. The reaction mixture was quenched with water (150 mL) and extracted with EtOAc (50 mL×3). The combined organic layers were dried over anhydrous sodium sulfate, filtered, and concentrated under reduced pressure to provide crude 4-(methylsulfonyl)-2-nitro-1-(prop-2-yn-1-yloxy)benzene as a light yellow solid.

Synthesis of 5-(methylsulfonyl)-2-(prop-2-yn-1-yloxy)aniline: To a solution of 4-(methylsulfonyl)-2-nitro-1-(prop-2-yn-1-yloxy)benzene (1.2 g, 4.70 mmol, 1 eq.) in AcOH (10 mL) was added Fe (1.31 g, 23.51 mmol, 5 eq.). The mixture was stirred at 70° C. for 2 h, after which time TLC analysis (PE:EtOAc=1:1, R$_f$=0.43) indicated that the reaction was complete. The reaction mixture was concentrated under reduced pressure to remove solvent and diluted with EtOAc (50 mL). The reaction mixture was quenched by adding a saturated solution of NaHCO$_3$ (200 mL) at 25° C. and extracted with EtOAc (50 mL×3). The combined organic layers were dried over anhydrous sodium sulfate, filtered, and concentrated under reduced pressure. The residue was purified by column chromatography (SiO$_2$, PE:EtOAc=1:1) to provide 5-(methylsulfonyl)-2-(prop-2-yn-1-yloxy)aniline (0.86 g, 3.44 mmol, 73.09% yield) as a light yellow solid.

dried over anhydrous sodium sulfate, and concentrated under reduced pressure. The residue was first purified by prep-TLC (PE:EtOAc=2:1, R$_f$=0.6) to provide N,N-dimethyl-5-(methylsulfonyl)-2-(prop-2-yn-1-yloxy)aniline (0.1 g, 355.29 μmol, 40% yield) as a colorless oil.

Example A8: Preparation of 4-(methylsulfonyl)-N-(prop-2-yn-1-yl)-2-(trifluoromethyl)aniline

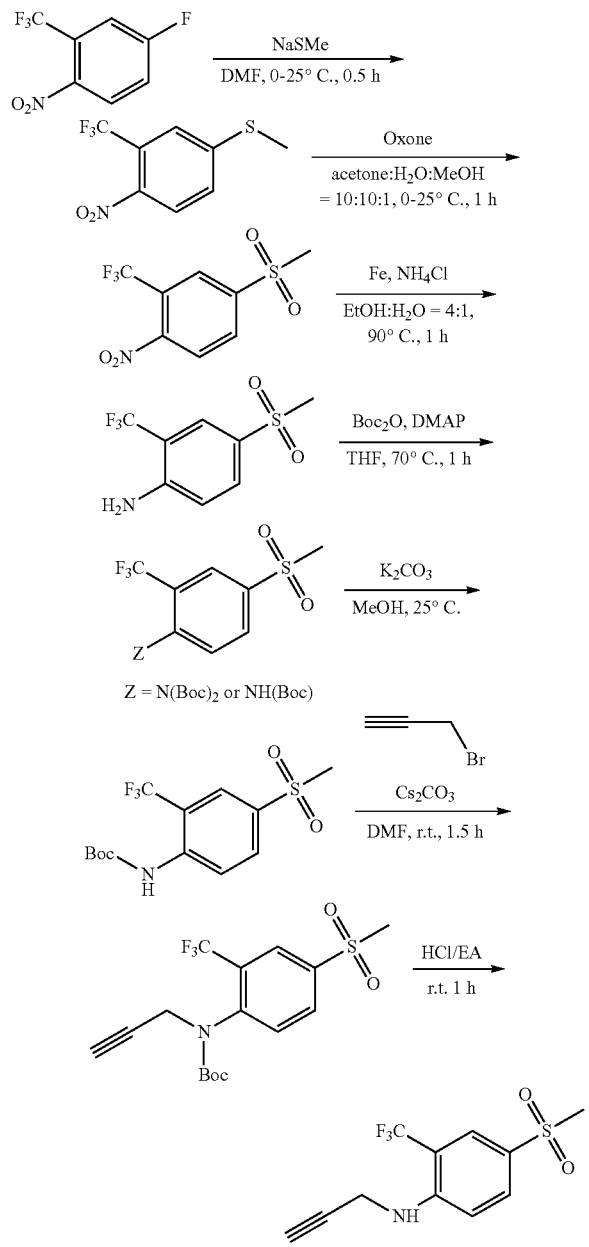

Synthesis of methyl(4-nitro-3-(trifluoromethyl)phenyl) sulfane: To a solution of 4-fluoro-1-nitro-2-(trifluoromethyl)benzene (10 g, 47.82 mmol, 1 eq.) in DMF (100 mL) was added NaSMe (33.52 g, 95.65 mmol, 30.47 mL, 20% purity, 2 eq.) in one portion at 0° C. under N$_2$. The mixture was stirred at 25° C. for 60 min, after which time TLC analysis indicated that the reaction was complete. The reaction was diluted with water (100 mL) and extracted with EtOAc (100 mL×3). The organic layer was then washed with half-saturated brine (100 mL×5), dried over anhydrous sodium sulfate, filtered, and concentrated to give 4-methylsulfanyl-1-nitro-2-(trifluoromethyl)benzene (11.4 g, crude) as a brown liquid, which was used in the next step without purification.

Synthesis of 4-(methylsulfonyl)-1-nitro-2-(trifluoromethyl)benzene: To a solution of 4-methylsulfanyl-1-nitro-2-(trifluoromethyl)benzene (10 g, 42.16 mmol, 1 eq.) in acetone (100 mL), water (100 mL), and MeOH (10 mL) was added potassium peroxymonosulfate (51.84 g, 84.32 mmol, 2 eq.) in one portion at 0° C. under N$_2$. The mixture was stirred at 25° C. for 60 min, after which time TLC and LC-MS analysis indicated that the reaction was complete. The reaction was quenched by adding a saturated solution of Na$_2$S$_2$O$_3$. The reaction mixture was slowly added to saturated NaHCO$_3$ (15 mL), then added saturated Na$_2$S$_2$O$_3$ (20 mL) was added. Completion of the reaction was monitored by KI starch test paper. Then the mixture was extracted with EtOAc (50 mL×3), and the organic phase was washed with brine (40 mL×3). The organic phase was dried over anhydrous sodium sulfate, filtered and concentrated in vacuo to afford crude 4-methylsulfonyl-1-nitro-2-(trifluoromethyl)benzene (9.8 g, 36.40 mmol, 86.35% yield) as a white solid.

Synthesis of 4-(methylsulfonyl)-2-(trifluoromethyl)aniline: A solution of 4-methylsulfonyl-1-nitro-2-(trifluoromethyl)benzene (9.5 g, 35.29 mmol, 1 eq.) in EtOH (200 mL) and NH$_4$Cl (aq) (50 mL) was heated to 90° C., and Fe (9.85 g, 176.45 mmol, 5 eq.) was then added in one portion at 90° C. The reaction mixture was stirred at 90° C. for 1 h, after which time TLC analysis indicated that the reaction was complete. The reaction was filtered while the reaction mixture was still hot. The filtrate was diluted with water (100 mL) and extracted with EtOAc (200 mL×4). The combined organic layers were washed with brine (200 mL×2), dried over anhydrous sodium sulfate, filtered, and concentrated to provide crude 4-methylsulfonyl-2-(trifluoromethyl)aniline (7.2 g) as a yellow solid. The crude product was purified by column chromatography (SiO$_2$, PE:EtOAc=2:1 to 1:1) to provide 4-methylsulfonyl-2-(trifluoromethyl)aniline (6.8 g, 28.43 mmol, 97.14% yield) as a yellow solid.

Synthesis of tert-butyl (4-(methylsulfonyl)-2-(trifluoromethyl)phenyl)carbamate and tert-butyl (tert-butoxycarbonyl)(4-(methylsulfonyl)-2-(trifluoromethyl)phenyl)carbamate:
To a solution of 4-methylsulfonyl-2-(trifluoromethyl)aniline (4 g, 16.72 mmol, 1 eq.) in THF (25 mL) were added Boc$_2$O (4.38 g, 20.07 mmol, 4.61 mL, 1.2 eq.) and DMAP (2.45 g, 20.07 mmol, 1.2 eq.). The reaction mixture was stirred at 70° C. for 1 h, after which time TLC analysis indicated that the reaction was complete. The reaction was diluted with water (30 mL) and extracted with EtOAc (30 mL×3). The combined organic layers were washed with water (30 mL×3) and brine (30 mL×3), dried over anhydrous sodium sulfate, filtered, and concentrated in vacuo. The residue was purified by column chromatography (SiO$_2$, PE:EtOAc=6:1 to 4:1) to provide a mixture of tert-butyl N-[4-methylsulfonyl-2-(trifluoromethyl)phenyl]carbamate and tert-butyl N-tert-butoxycarbonyl-N-[4-methylsulfonyl-2-(trifluoromethyl)phenyl]carbamate as a yellow gum.

Synthesis of tert-butyl (4-(methylsulfonyl)-2-(trifluoromethyl)phenyl)carbamate: To the mixture of the previous step (2.5 g, 5.69 mmol, 1 eq.) dissolved in MeOH (40 mL) was added K$_2$CO$_3$ (2.36 g, 17.07 mmol, 3 eq.) in one portion. The mixture was stirred at 25° C. for 6 h, after which time LC-MS analysis indicated that the reaction was complete. The reaction was filtered and concentrated to afford tert-butyl N-[4-methylsulfonyl-2-(trifluoromethyl)phenyl]carbamate (2.0 g, crude) as a red solid.

Synthesis of tert-butyl (4-(methylsulfonyl)-2-(trifluoromethyl)phenyl)(prop-2-yn-1-yl)carbamate: To a solution of tert-butyl N-[4-methylsulfonyl-2-(trifluoromethyl)phenyl] carbamate (2 g, 5.89 mmol, 1 eq.) in DMF (12 mL) were added Cs$_2$CO$_3$ (5.76 g, 17.68 mmol, 3 eq.) and propargyl bromide (2.10 g, 17.68 mmol, 1.52 mL, 3 eq.). The reaction mixture was stirred for 1.5 h at 25° C., after which time TLC analysis (PE:EtOAc=1:1, R$_{f(starting\ material)}$=0.68, product R$_{f(product)}$=0.50) indicated that the reaction was complete. The reaction was diluted with water (30 mL) and extracted with EtOAc (30 mL×3). The combined organic layers were washed with water (30 mL×3) and brine (30 mL×3), dried over anhydrous sodium sulfate, filtered, and concentrated. The residue was purified by column chromatography (SiO$_2$, PE:EtOAc=4:1 to 2:1) to provide tert-butyl N-[4-methylsulfonyl-2-(trifluoromethyl)phenyl]-N-prop-2-ynyl-carbamate (1.7 g, 4.50 mmol, 76.43% yield) as a colorless gum.

Synthesis of 4-(methylsulfonyl)-N-(prop-2-yn-1-yl)-2-(trifluoromethyl)aniline: A solution of tert-butyl N-[4-methylsulfonyl-2-(trifluoromethyl)phenyl]-N-prop-2-ynyl-carbamate (1.7 g, 4.50 mmol, 1 eq.) in HCl/EtOAc (4 M, 34 mL, 30.19 eq.) was stirred at 25° C. for 1 h, after which time TLC analysis (PE:EtOAc=1:1, R$_{f(starting\ material)}$=0.49, R$_{f(product)}$=0.27) indicated that the reaction was complete. The reaction was concentrated directly to provide 4-methylsulfonyl-N-prop-2-ynyl-2-(trifluoromethyl)aniline (1.1 g, 3.97 mmol, 88.07% yield) as a white solid.

Example A9: Preparation of 2-chloro-4-(methylsulfonyl)-N-(prop-2-yn-1-yl)aniline

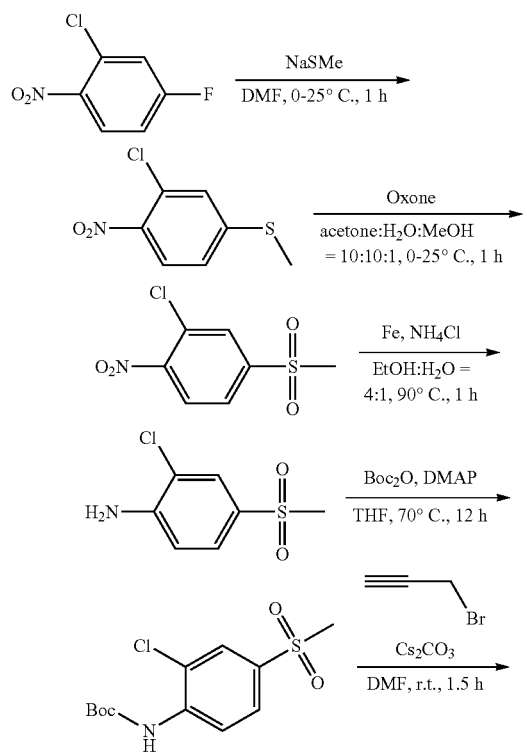

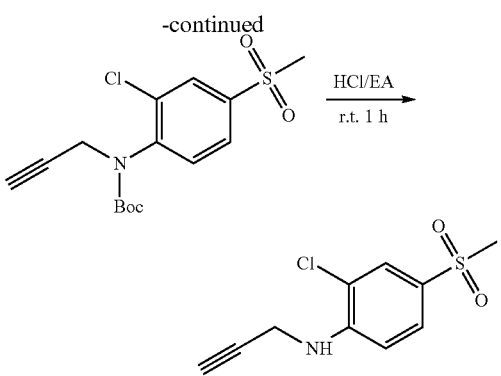

Synthesis of (3-chloro-4-nitrophenyl)(methyl)sulfane: To a mixture of 2-chloro-4-fluoro-1-nitro-benzene (10 g, 56.97 mmol, 1 eq.) in DMF (120 mL) was added NaSMe (39.93 g, 113.93 mmol, 36.30 mL, 20% purity, 2 eq.) in one portion at 0° C. under N$_2$. The mixture was stirred at 25° C. for 60 min, after which time TLC analysis (PE:EtOAc=10:1, R$_{f1}$=0.66, R$_{f2}$=0.55) indicated that the reaction was complete. The reaction was diluted with water (100 mL) and extracted with EtOAc (100 mL×3). The combined organic layers were washed with half-saturated brine (100 mL×5), dried over anhydrous sodium sulfate, filtered, and concentrated. The residue was purified by column chromatography (SiO$_2$, PE:EtOAc=5:1) to provide 2-chloro-4-methylsulfanyl-1-nitro-benzene (4.3 g, 21.12 mmol, 37.07% yield) as a yellow solid.

Synthesis of 2-chloro-4-(methylsulfonyl)-1-nitrobenzene: To a mixture of 2-chloro-4-methylsulfanyl-1-nitro-benzene (4.3 g, 21.12 mmol, 1 eq.) in toluene (25 mL), MeOH (2.5 mL), and water (25 mL) was added potassium peroxymonosulfate (25.96 g, 42.23 mmol, 2 eq.) in one portion at 0° C. under N$_2$. The mixture was stirred at 25° C. for 60 min, after which time TLC (PE:EtOAc=1:1, R$_{f(sm)}$=0.63, R$_{f(pdt)}$=0.51) indicated that the reaction was complete. The reaction was quenched with saturated Na$_2$S$_2$O$_3$ (200 mL) and extracted with EtOAc (100 mL×3). The combined organic layers were washed with brine (100 mL×2), dried over anhydrous sodium sulfate, filtered, and concentrated to provide crude 2-chloro-4-methylsulfonyl-1-nitro-benzene (5.0 g, crude) as a yellow solid.

Synthesis of 2-chloro-4-(methylsulfonyl)aniline: A mixture of 2-chloro-4-methylsulfonyl-1-nitro-benzene (4.5 g, 19.10 mmol, 1 eq.) in EtOH (40 mL) and a saturated NH$_4$Cl solution (10 mL) was heated to 90° C., and then Fe (3.20 g, 57.29 mmol, 3 eq.) was added in one portion. The reaction mixture was stirred at 90° C. for 1 h, after which time TLC analysis (PE:EtOAc=1:1, R$_{f(starting\ material)}$=0.7, R$_{f(product)}$=0.31) indicated that the reaction was complete. The reaction was diluted with water (50 mL) and extracted with EtOAc (100 mL×3). The combined organic layers were washed with water (50 mL×3) and brine (50 mL×2), dried over anhydrous sodium sulfate, filtered, and concentrated under reduced pressure. The residue was purified by column chromatography (SiO$_2$, PE:EtOAc=4:1 to 2:1) to provide 2-chloro-4-methylsulfonyl-aniline (3.7 g, 17.99 mmol, 94.21% yield) as an off-white solid.

Synthesis of tert-butyl (2-chloro-4-(methylsulfonyl)phenyl)carbamate: To a mixture of 2-chloro-4-methylsulfonyl-aniline (3.7 g, 17.99 mmol, 1 eq.) and (Boc)$_2$O (4.71 g, 21.59 mmol, 4.96 mL, 1.2 eq.) in THF (50 mL) was added DMAP (2.20 g, 17.99 mmol, 1 eq.) in one portion. The mixture was stirred at 70° C. for 12 h, after which time TLC (PE:EtOAc=1:1, $R_{f(sm)}$=0.45, $R_{f(pdt)}$=0.66) indicated that some starting primary amine remained in the mixture. The reaction was diluted with water (30 mL) and extracted with EtOAc (30 mL×3). The combined organic layers were washed with water (30 mL×3) and brine (30 mL×2), dried over anhydrous sodium sulfate, filtered, and concentrated. The residue was purified by column chromatography (SiO$_2$, PE:EtOAc=4:1 to 2:1) to provide tert-butyl N-(2-chloro-4-methylsulfonyl-phenyl)carbamate (2.7 g, 8.83 mmol, 49.08% yield) as a white solid.

Synthesis of tert-butyl (2-chloro-4-(methylsulfonyl)phenyl)(prop-2-yn-1-yl)carbamate: To a mixture of tert-butyl N-(2-chloro-4-methylsulfonyl-phenyl)carbamate (2.4 g, 7.85 mmol, 1 eq.) in DMF (24 mL) were added Cs$_2$CO$_3$ (7.67 g, 23.55 mmol, 3 eq.) and propargyl bromide (2.80 g, 23.55 mmol, 2.03 mL, 3 eq.). The reaction mixture was stirred for 1.5 h at 25° C., after which time TLC analysis (PE:EtOAc=1:1, $R_{f(starting\ material)}$=0.68, $R_{f(product)}$=0.60) indicated that the reaction was complete. The reaction was diluted with water (30 mL) and extracted with EtOAc (30 mL×3). The combined organic layers were washed with water (30 mL×3) and brine (30 mL×2), dried over anhydrous sodium sulfate, filtered, and concentrated. The residue was purified by column chromatography (SiO$_2$, PE:EtOAc=4:1 to 3:1) to provide tert-butyl N-(2-chloro-4-methylsulfonyl-phenyl)-N-prop-2-ynyl-carbamate (1.7 g, 4.94 mmol, 62.99% yield) as a colorless gum.

Synthesis of 2-chloro-4-(methylsulfonyl)-N-(prop-2-yn-1-yl)aniline: A solution of tert-butyl N-(2-chloro-4-methylsulfonyl-phenyl)-N-prop-2-ynyl-carbamate (300 mg, 872.54 mmol, 1 eq.) in HCl/EtOAc (4 M, 6.59 μL, 30.19 eq.) was stirred at 25° C. for 1 h, after which time LC-MS analysis indicated that the reaction was complete. The reaction mixture was directly concentrated to provide crude 2-chloro-4-methylsulfonyl-N-prop-2-ynyl-aniline (180 mg, crude) as a brown solid.

Example A10: Preparation of 3-methoxy-N-methyl-4-(prop-2-yn-1-ylamino)benzamide

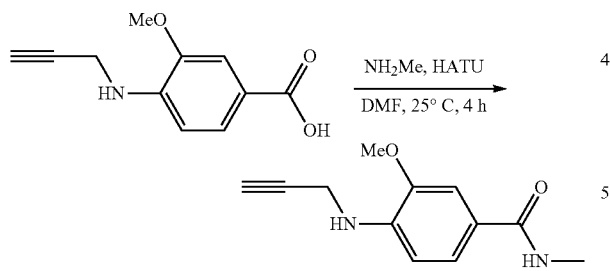

A mixture of 3-methoxy-4-(prop-2-yn-1-ylamino)benzoic acid (50 mg, 207.11 μmol, 1 eq.), HATU (94.50 mg, 248.53 μmol, 1.2 eq.), and DIPEA (53.53 mg, 414.21 μmol, 72.15 μL, 2 eq.) in DMF (3 mL) was stirred at 25° C. for 15 min, and NH$_2$Me (20.97 mg, 310.66 μmol, 1.5 eq.) was added. The mixture was stirred for 3.75 h, after which time LC-MS analysis indicated that the reaction was complete. The reaction mixture was quenched by adding water (40 mL), and the resulting mixture was extracted with EtOAc (10 mL×4). The combined organic layers were dried over anhydrous sodium sulfate, filtered, and concentrated under reduced pressure. The residue was purified by prep-TLC (SiO$_2$, EtOAc:PE=2:1, $R_f$=0.25) to provide 3-methoxy-N-methyl-4-(prop-2-yn-1-ylamino)benzamide (45 mg, 185.57 μmol, 89.60% yield) as a light yellow oil.

Example A11: Preparation of N,N-bis(2-hydroxyethyl)-3-methoxy-4-(prop-2-yn-1-ylamino)benzenesulfonamide

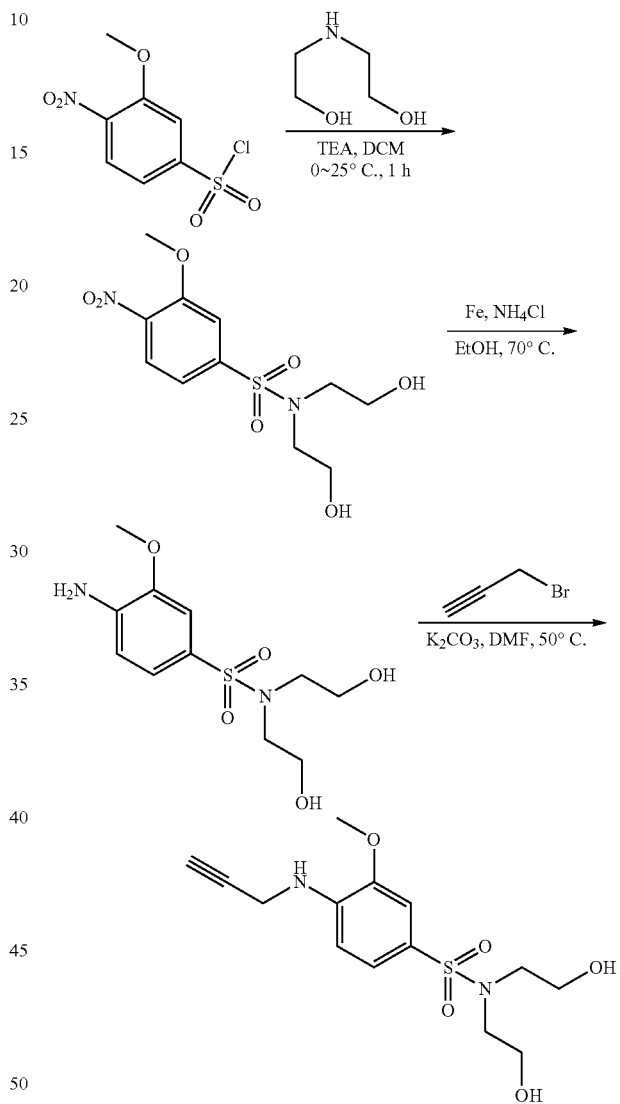

Synthesis of N,N-bis(2-hydroxyethyl)-3-methoxy-4-nitrobenzenesulfonamide: To a mixture of diethanolamine (835.59 mg, 7.95 mmol, 766.59 μL, 2 eq.) and TEA (804.23 mg, 7.95 mmol, 1.11 mL, 2 eq.) in DCM (10 mL) was added a solution of 3-methoxy-4-nitrobenzenesulfonyl chloride (1 g, 3.97 mmol, 1 eq.) in DCM (5 mL) at 0° C. The reaction was warmed to 25° C. over 1 h with stirring, after which time TLC analysis (PE:EtOAc=1:2, $R_f$=0.3) indicated that the reaction was complete. The reaction mixture was diluted with water (20 mL) and extracted with EtOAc (20 mL×3). The combined organic layers were washed with brine (20 mL), dried over anhydrous sodium sulfate, filtered, and concentrated under reduced pressure. The resulting residue was purified by column chromatography (SiO$_2$, PE:EtOAc=1:2, $R_f$=0.3) to afford N,N-bis(2-hydroxyethyl)-

3-methoxy-4-nitrobenzenesulfonamide (1.2 g, 3.0 mmol, 75.42% yield) as a yellow solid.

Synthesis of 4-amino-N,N-bis(2-hydroxyethyl)-3-methoxybenzenesulfonamide: To a mixture of N,N-bis(2-hydroxyethyl)-3-methoxy-4-nitrobenzenesulfonamide (1.2 g, 3 mmol, 1 eq.) and NH₄Cl (801.55 mg, 15 mmol, 523.89 µL, 5 eq.) in EtOH (20 mL) and water (4 mL) at 70° C. was added Fe (836.92 mg, 15 mmol, 5 eq.). The mixture was stirred at 70° C. for 1 h, after which time LC-MS analysis indicated that the reaction was complete. The reaction mixture was diluted with water (20 mL) and extracted with EtOAc (20 mL×3). The combined organic layers were washed with brine (20 mL), dried over anhydrous sodium sulfate, filtered, and concentrated under reduced pressure. The resulting residue was purified by column chromatography (SiO₂, EtOAc, $R_f$=0.28) to provide 4-amino-N,N-bis(2-hydroxyethyl)-3-methoxybenzenesulfonamide (0.8 g, 2.20 mmol, 73.55% yield) as a yellow oil.

Synthesis of N,N-bis(2-hydroxyethyl)-3-methoxy-4-(prop-2-yn-1-ylamino)benzenesulfonamide: A mixture of 4-amino-N,N-bis(2-hydroxyethyl)-3-methoxybenzenesulfonamide (0.1 g, 275.54 µmol, 1 eq.), propargyl bromide (49.17 mg, 413.32 µmol, 35.63 µL, 1.5 eq.), and K₂CO₃ (38.08 mg, 275.54 µmol, 1 eq.) in DMF (2 mL) was stirred at 50° C. for 12 h, after which time LC-MS analysis indicated that the desired product was present in the mixture. The reaction mixture was diluted with water (20 mL) and extracted with EtOAc (20 mL×3). The combined organic layers were washed with brine (20 mL), dried over anhydrous sodium sulfate, filtered, and concentrated under reduced pressure. The residue was purified by prep-TLC (SiO₂, EtOAc:PE=1:1, $R_f$=0.31) to afford N,N-bis(2-hydroxyethyl)-3-methoxy-4-(prop-2-yn-1-ylamino)benzenesulfonamide (0.05 g, 121.81 µmol, 44.210% yield) as a yellow oil.

Example A12: Preparation of 2-methoxy-4-((4-methylpiperazin-1-yl)sulfonyl)-N-(prop-2-yn-1-yl)aniline

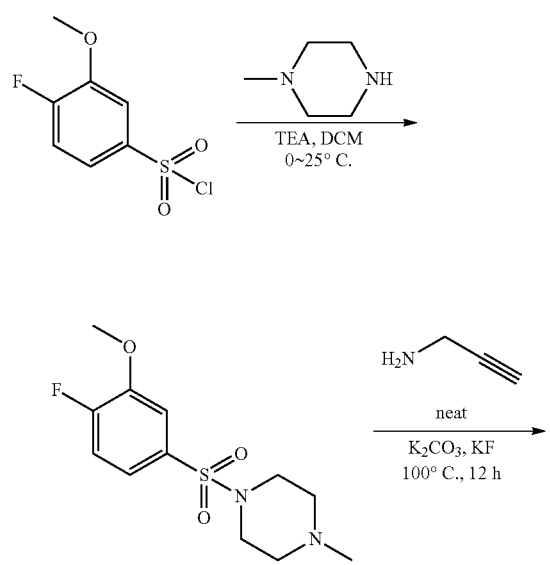

-continued

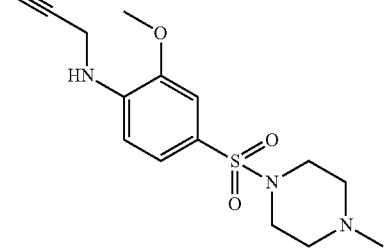

Synthesis of 1-((4-fluoro-3-methoxyphenyl)sulfonyl)-4-methylpiperazine: To a solution of N-methylpiperazine (312.12 mg, 3.12 mmol, 345.65 µL, 2 eq.) in DCM (2 mL) was added TEA (315.32 mg, 3.12 mmol, 433.73 µL, 2 eq.). The resulting solution was then added into a solution of 4-fluoro-3-methoxybenzenesulfonyl chloride (350 mg, 1.56 mmol, 1 eq.) in DCM (4 mL) dropwise. The reaction mixture was warmed to 25° C. over 2 h with stirring, after which time TLC analysis (PE:EtOAc=1:1, $R_f$=0.40) indicated that the reaction was complete. The reaction mixture was quenched by adding water (60 mL) at 25° C. and extracted with EtOAc (20 mL×4). The combined organic layers were dried over anhydrous sodium sulfate, filtered, and concentrated under reduced pressure. The resulting residue was purified by column chromatography (SiO₂, PE:EtOAc=1:0 to 1:1) to provide 1-((4-fluoro-3-methoxyphenyl)sulfonyl)-4-methylpiperazine (410 mg, 1.35 mmol, 86.70% yield) as a light yellow solid. MS (ES⁺, m/z): 288.9.

Synthesis of 2-methoxy-4-((4-methylpiperazin-1-yl)sulfonyl)-N-(prop-2-yn-1-yl)aniline: A mixture of 1-((4-fluoro-3-methoxyphenyl)sulfonyl)-4-methylpiperazine (100 mg, 329.47 µmol, 1 eq.), propargylamine (1.72 g, 31.23 mmol, 2 mL, 94.78 eq.), K₂CO₃ (91.07 mg, 658.95 µmol, 2 eq.), and KF (38.28 mg, 658.95 µmol, 15.44 µL, 2 eq.) was stirred at 100° C. for 12 h in a sealed tube, after which time TLC analysis (PE:EtOAc=1:1, $R_f$=0.23) detected a new compound. The reaction mixture was quenched by adding water (40 mL) and extracted with EtOAc (10 mL×3). The combined organic layers were dried over anhydrous sodium sulfate, filtered, and concentrated under reduced pressure. The residue was purified by prep-TLC (SiO₂, PE:EtOAc=1:1) over two runs to provide 2-methoxy-4-((4-methylpiperazin-1-yl)sulfonyl)-N-(prop-2-yn-1-yl)aniline (25 mg, 69.57 µmol, 21.12% yield) as a light yellow solid.

Example A13: Preparation of 2-(5-(methylsulfonyl)-2-(prop-2-yn-1-ylamino)phenoxy)acetamide

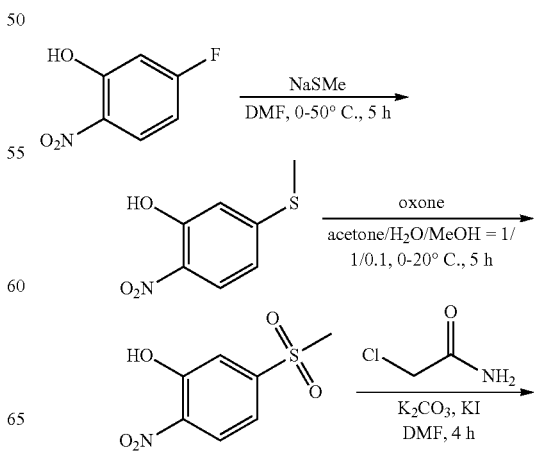

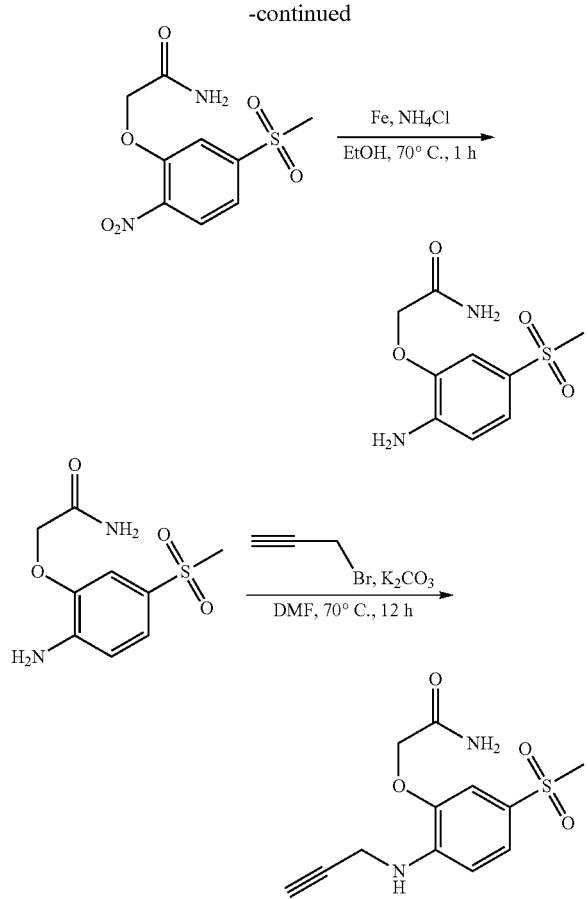

Synthesis of 5-(methylthio)-2-nitrophenol: To a solution of 5-fluoro-2-nitrophenol (5 g, 31.83 mmol, 1 eq.) in DMF (50 mL) was added NaSMe (66.93 g, 190.98 mmol, 60.85 mL, 6 eq.) at 0° C. The mixture was heated to 50° C. for 5 h, after which time HPLC and LC-MS analysis indicated that the reaction was complete. The residue was poured into a saturated aqueous solution of NH$_4$Cl (300 mL), and the aqueous phase was extracted with EtOAc (200 mL×3). The combined organic layers were washed with brine (200 mL×3), dried over anhydrous sodium sulfate, filtered, and concentrated in vacuo to afford 5-(methylthio)-2-nitrophenol (5.20 g, crude) as a yellow solid.

Synthesis of 5-(methylsulfonyl)-2-nitrophenol: To a solution of 5-(methylthio)-2-nitrophenol (1 g, 5.40 mmol, 1 eq.) in acetone (10 mL), water (10 mL), and MeOH (1 mL) was added potassium peroxymonosulfate (8.30 g, 13.50 mmol, 2.50 eq.) at 0° C. The mixture warmed to 20° C. and stirred for 5 r h, after which time LC-MS analysis indicated that the reaction was complete. The residue was poured into a saturated aqueous solution of Na$_2$SO$_3$ (50 mL), and 12N HCl (20 mL) was added to adjust the pH of the solution to <7. The aqueous phase was extracted with EtOAc (50 mL×3). The organic phase was dried over anhydrous sodium sulfate, filtered, and concentrated in vacuo to afford 5-(methylsulfonyl)-2-nitrophenol (1.10 g, crude) as a yellow solid.

Synthesis of 2-(5-(methylsulfonyl)-2-nitrophenoxy)acetamide: To a mixture of 5-(methylsulfonyl)-2-nitrophenol (500 mg, 2.30 mmol, 1 eq.) in DMF (10 mL) were added K$_2$CO$_3$ (953.65 mg, 6.90 mmol, 3 eq.), 2-chloroacetamide (537.68 mg, 5.75 mmol, 2.50 eq.), and KI (382.14 mg, 2.30 mmol, 1 eq.). The mixture was stirred at 50° C. for 2 h, after which time HPLC analysis indicated a reactant to product ratio of 1:1. Second portions of 2-chloroacetamide (215.07 mg, 2.30 mmol, 1 eq.), K$_2$CO$_3$ (476.82 mg, 3.45 mmol, 1.50 eq.), and KI (190.90 mg, 1.15 mmol, 0.50 eq.) was added to the reaction, and the resulting mixture was stirred further at 50° C. for 2 h. HPLC analysis indicated a reactant to product ratio of 1:5. The residue was poured into water (30 mL), and the aqueous phase was extracted with EtOAc (30 mL×3). The combined organic layers were washed with brine (30 mL×3), dried over anhydrous sodium sulfate, filtered, and concentrated in vacuo to afford 2-(5-(methylsulfonyl)-2-nitrophenoxy)acetamide (380 mg, crude) as a yellow solid.

Synthesis of 2-(2-amino-5-(methylsulfonyl)phenoxy)acetamide: To a solution of 2-(5-(methylsulfonyl)-2-nitrophenoxy)acetamide (380 mg, 1.39 mmol, 1 eq.) in EtOH (3 mL) was added NH$_4$Cl (74.12 mg, 1.39 mmol, 48.44 µL, 1 eq.). The mixture was heated to 70° C., and Fe (773.86 mg, 13.86 mmol, 10 eq.) was added. The reaction mixture was stirred at 70° C. for 1 h, after which time HPLC analysis indicated that the reaction was complete. The mixture was poured into water (50 mL), filtered with diatomite, and extracted with EtOAc (50 mL×3). The combined organic layers were washed with brine (50 mL×3), dried over anhydrous sodium sulfate, filtered, and concentrated in vacuo to afford 2-(2-amino-5-(methylsulfonyl)phenoxy)acetamide (270 mg, crude) as a black brown solid.

Synthesis of 2-(5-(methylsulfonyl)-2-(prop-2-yn-1-ylamino)phenoxy)acetamide: To a solution of 2-(2-amino-5-(methylsulfonyl)phenoxy)acetamide (240 mg, 982.52 µmol, 1 eq.) in DMF (8 mL) were added K$_2$CO$_3$ (407.38 mg, 2.95 mmol, 3 eq.) and 3-bromoprop-1-yne (584.40 mg, 4.91 mmol, 423.48 µL, 5 eq.). The mixture was stirred at 70° C. for 3 h, after which time HPLC analysis indicated that 29.5% of the starting primary amine remained and 25.5% of desired compound was detected, with the percent values referring to the peak area. The reaction mixture was poured into water (20 mL) and extracted with EtOAc (20 mL×3). The combined organic layers were washed with brine (10 mL×3), dried over anhydrous sodium sulfate, filtered, and concentrated under reduced pressure. The residue was purified by prep-TLC (DCM:MeOH=10:1, R$_f$=0.40) to provide 2-(5-(methylsulfonyl)-2-(prop-2-yn-1-ylamino)phenoxy)acetamide (80 mg, 276.68 µmol, 28.16% yield) as a light red solid. MS (ES$^+$, m/z): 283.0.

Example A14: Preparation of N-(isoxazol-3-yl)-3-methoxy-4-(prop-2-yn-1-ylamino)benzenesulfonamide

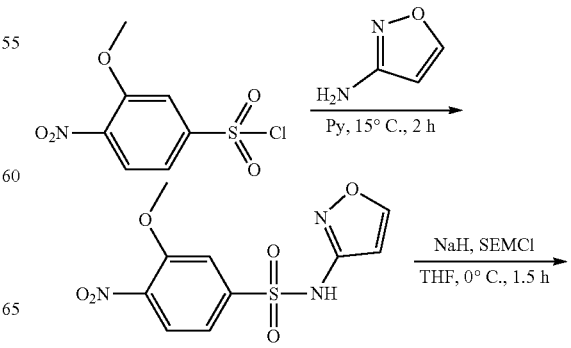

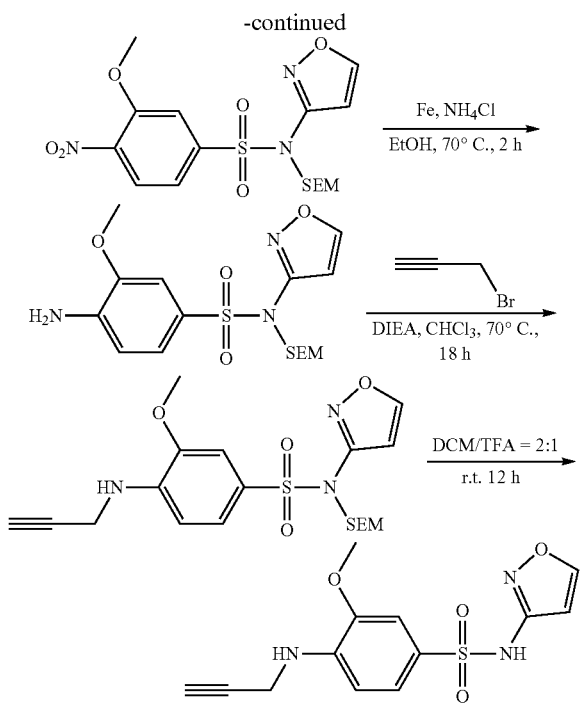

Synthesis of N-(isoxazol-3-yl)-3-methoxy-4-nitrobenzenesulfonamide: To a solution of 3-methoxy-4-nitrobenzenesulfonyl chloride (2 g, 7.95 mmol, 1 eq.) in pyridine (10 mL) was added isoxazol-3-amine (801.86 mg, 9.54 mmol, 703.39 µL, 1.2 eq.). The mixture was stirred at 20° C. for 2 h, after which time TLC analysis (EtOAc:DCM:PE:TEA=1:1:3:0.5, $R_{f(starting\ material)}$=0.40, $R_{f(product)}$=0.04) indicated that the starting material was consumed. The mixture was poured into water (20 mL) and extracted with EtOAc (20 mL×2, 10 mL×1). The combined organic layers were dried over anhydrous sodium sulfate, filtered, and concentrated under reduced pressure. The residue was purified by column chromatography to provide N-(isoxazol-3-yl)-3-methoxy-4-nitrobenzenesulfonamide (6.5 g, 21.72 mmol, 91.10% yield) as a black brown oil. MS (ES+, m/z): 300.0.

Synthesis of N-(isoxazol-3-yl)-3-methoxy-4-nitro-N-((2-(trimethylsilyl)ethoxy)methyl)benzene sulfonamide: To a solution of N-(isoxazol-3-yl)-3-methoxy-4-nitrobenzenesulfonamide (2 g, 6.68 mmol, 1 eq.) in THF (20 mL) was added NaH (534.60 mg, 13.37 mmol, 60% in mineral oil, 2 eq.) at 0° C. under $N_2$. The mixture was stirred at 0° C. for 30 mins, and (2-(chloromethoxy)ethyl)trimethylsilane (SEMCl) (1.67 g, 10.02 mmol, 1.77 mL, 1.5 eq.) was added. The resulting mixture was stirred at 0° C. for 1 h, after which time TLC analysis (PE:EtOAc=3:1, $R_{f(starting\ material)}$=0.60, $R_{f(product)}$=0.35) indicated that the reaction was complete. The residue was poured into water (100 mL), and the aqueous phase was extracted with EtOAc (40 mL×3). The combined organic layers were dried over anhydrous sodium sulfate, filtered, and concentrated in vacuo. The residue was purified by silica gel chromatography (PE:EtOAc=1:0 to 10:1 to afford N-(isoxazol-3-yl)-3-methoxy-4-nitro-N-((2-(trimethylsilyl)ethoxy)methyl)benzenesulfonamide (1.8 g, 3.98 mmol, 59.57% yield) as a black brown oil.

Synthesis of 4-amino-N-(isoxazol-3-yl)-3-methoxy-N-((2-(trimethylsilyl)ethoxy)methyl)benzenesulfonamide: To a solution of N-(isoxazol-3-yl)-3-methoxy-4-nitro-N-((2-(trimethylsilyl)ethoxy)methyl)benzenesulfonamide (1.8 g, 3.98 mmol, 1 eq.) in EtOH (10 mL) was added saturated solution of $NH_4Cl$ (0.5 mL). The mixture was heated to 70° C., Fe (2.22 g, 39.81 mmol, 10 eq.) was added, and the mixture was stirred further at 70° C. for 2 h. TLC analysis (PE:EtOAc=3:1, $R_f$=0.35) indicated that the reaction was complete. The mixture was poured into a saturated aqueous solution of $NaHCO_3$ (100 mL), filtered with diatomite, and extracted with EtOAc (60 mL×3). The combined organic layers were dried over anhydrous sodium sulfate, filtered, and concentrated in vacuo. The residue was purified by silica gel chromatography (PE:EtOAc=1:0 to 3:1) to afford 4-amino-N-(isoxazol-3-yl)-3-methoxy-N-((2-(trimethylsilyl)ethoxy)methyl)benzenesulfonamide (1 g, 2.25 mmol, 56.58% yield) as a black brown oil.

Synthesis of N-(isoxazol-3-yl)-3-methoxy-4-(prop-2-yn-1-ylamino)-N-((2-(trimethylsilyl)ethoxy)methyl)benzenesulfonamide: To a mixture of 4-amino-N-(isoxazol-3-yl)-3-methoxy-N-((2-(trimethylsilyl)ethoxy)methyl)benzenesulfonamide (450 mg, 1.01 mmol, 1 eq.) in $CHCl_3$ (10 mL) was added DIEA (655.04 mg, 5.07 mmol, 882.80 µL, 5 eq.). The mixture was heated to 70° C., propargyl bromide (241.17 mg, 2.03 mmol, 174.76 µL, 2 eq.) was added, and the mixture was stirred further for 12 h. LC-MS and HPLC analysis indicated that ~58% of the starting primary amine remained and 11% of the product was detected, with the percent values referring to the peak area. An additional portion of propargyl bromide (602.93 mg, 5.07 mmol, 436.91 µL, 5 eq.) was added, and the mixture was stirred further at 70° C. for 6 h. LC-MS and HPLC analysis indicated that ~15% of the starting primary amine remained and 45% of the desired product was detected, with the percent values referring to the peak area. The mixture was poured into water (30 mL) and extracted with EtOAc (20 mL×3). The combined organic layers were dried over anhydrous sodium sulfate, filtered, and concentrated in vacuo. The residue was purified by silica gel chromatography (PE:EtOAc=1:0 to 10:1 to afford N-(isoxazol-3-yl)-3-methoxy-4-(prop-2-yn-1-ylamino)-N-((2-(trimethylsilyl)ethoxy)methyl)benzenesulfonamide (340 mg, 568.29 µmol, 56% yield) as a yellow oil.

Synthesis of N-(isoxazol-3-yl)-3-methoxy-4-(prop-2-yn-1-ylamino)benzenesulfonamide: To a solution of N-(isoxazol-3-yl)-3-methoxy-4-(prop-2-yn-1-ylamino)-N-((2-(trimethylsilyl)ethoxy)methyl)benzenesulfonamide (280 mg, 468.01 µmol, 1 eq.) in DCM (4 mL) was added TFA (1 mL). The mixture was stirred at 20° C. for 12 h, after which time LC-MS and HPLC analysis indicated that the reaction was complete. The mixture was poured into a saturated aqueous solution of $NaHCO_3$ (40 mL) and extracted with EtOAc (25 mL×3). The combined organic layers were dried over anhydrous sodium sulfate, filtered, and concentrated in vacuo. The residue was purified by silica gel chromatography (PE:EtOAc=1:0 to 3:1) to afford N-(isoxazol-3-yl)-3-methoxy-4-(prop-2-yn-1-ylamino)benzenesulfonamide (150 mg, 379.50 µmol, 81% yield) as a yellow solid.

Example A15: Preparation of N-(2-hydroxyethyl)-3-methoxy-N-methyl-4-(prop-2-yn-1-ylamino)benzenesulfonamide

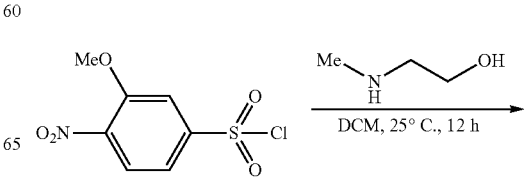

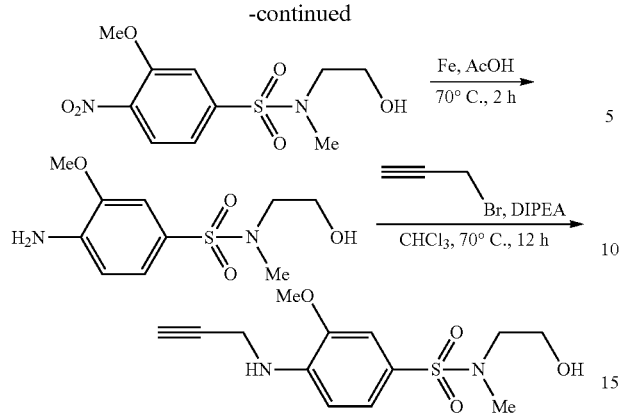

Synthesis of N-(2-hydroxyethyl)-3-methoxy-N-methyl-4-nitrobenzenesulfonamide. To a mixture of 3-methoxy-4-nitrobenzenesulfonyl chloride (2.5 g, 9.93 mmol, 1 eq.) and 2-(methylamino)ethan-1-ol (969.59 mg, 12.91 mmol, 1.04 mL, 1.3 eq.) in DCM (25 mL) was added TEA (5.03 g, 49.65 mmol, 6.91 mL, 5 eq.) at 25° C. The mixture was stirred at 25° C. for 12 h, after which time LC-MS analysis indicated that the reaction was complete. The mixture was poured into water (100 mL) and extracted with DCM (80 mL×3). The combined organic layers were dried over anhydrous sodium sulfate, filtered, and concentrated in vacuo to afford N-(2-hydroxyethyl)-3-methoxy-N-methyl-4-nitrobenzenesulfonamide (2.1 g, crude) as a black brown oil. MS (ES+, m/z): 291.1.

Synthesis of 4-amino-N-(2-hydroxyethyl)-3-methoxy-N-methylbenzenesulfonamide: N-(2-hydroxyethyl)-3-methoxy-N-methyl-4-nitrobenzenesulfonamide (2.1 g, 7.23 mmol, 1 eq.) dissolved in AcOH (20 mL), and the mixture was heated to 70° C. Fe (4.04 g, 72.34 mmol, 10 eq.) was then added, and the mixture was stirred further at 70° C. for 2 h, after which time LC-MS analysis indicated that the reaction was complete. The residue was poured into a saturated aqueous solution of NaHCO3 (500 mL), filtered with diatomite, and extracted with EtOAc (300 mL×3). The combined organic layers were dried over anhydrous sodium sulfate, filtered, and concentrated in vacuo. The residue was purified by silica gel chromatography to afford 4-amino-N-(2-hydroxyethyl)-3-methoxy-N-methylbenzenesulfonamide (1.8 g, 6.22 mmol, 86% yield) as a black brown solid. MS (ES+, m/z): 261.2.

Synthesis of N-(2-hydroxyethyl)-3-methoxy-N-methyl-4-(prop-2-yn-1-ylamino)benzenesulfonamide. To a mixture of 4-amino-N-(2-hydroxyethyl)-3-methoxy-N-methylbenzenesulfonamide (500 mg, 1.73 mmol, 1 eq.) in CHCl3 (5 mL) was added DIPEA (1.12 g, 8.64 mmol, 1.51 mL, 5 eq.). The mixture was heated to 70° C., and propargyl bromide (1.03 g, 8.64 mmol, 745.10 µL, 5 eq.) was added. The mixture was stirred at 70° C. for 12 h, after which time HPLC and LC-MS analysis indicated that 12.6% of the starting material remained, 68.1% of the product was detected, and 7.7% of a byproduct were detected (percent values refer to peak areas). The mixture was poured into water (60 mL) and extracted with EtOAc (60 mL×3). The combined organic layers were dried over anhydrous sodium sulfate, filtered, and concentrated in vacuo. The residue was purified by silica gel chromatography, (column height: 250 mm, diameter: 100 mm, 100-200 mesh silica gel) concentrated, dissolved in PE:EtOAc=1:1 (20 mL), and heated to 70° C. Additional EtOAc (5 mL) was added to dissolve any remaining solids, and the mixture was stirred further for 1 h. The mixture was cooled to 25° C., and the resulting solid precipitate was filtered. The mother liquor was subjected to two rounds of prep-HPLC, then combine two parts to afford N-(2-hydroxyethyl)-3-methoxy-N-methyl-4-(prop-2-yn-1-ylamino)benzenesulfonamide (0.28 g, 50.0% yield) as a yellow solid. MS (ES+, m/z): 299.1.

Example A16: Preparation of 3-methoxy-N-(5-methylisoxazol-3-yl)-4-(prop-2-yn-1-ylamino)benzenesulfonamide

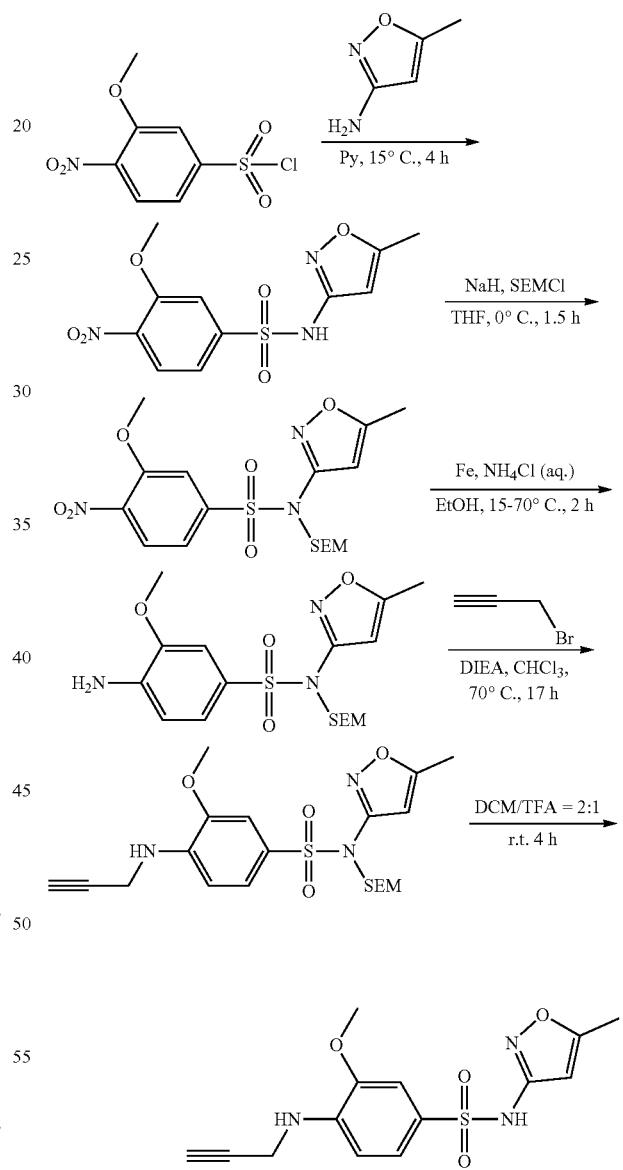

3-methoxy-N-(5-methylisoxazol-3-yl)-4-(prop-2-yn-1-ylamino)benzenesulfonamide was prepared via a procedure analogous to the synthesis of N-(isoxazol-3-yl)-3-methoxy-4-(prop-2-yn-1-ylamino)benzenesulfonamide according to EXAMPLE A14, using 5-methylisoxazol-3-amine in place of isoxazol-3-amine.

Example A17: Preparation of 2-(2-(dimethylamino)ethoxy)-4-(methylsulfonyl)-N-(prop-2-yn-1-yl)aniline hydrochloride

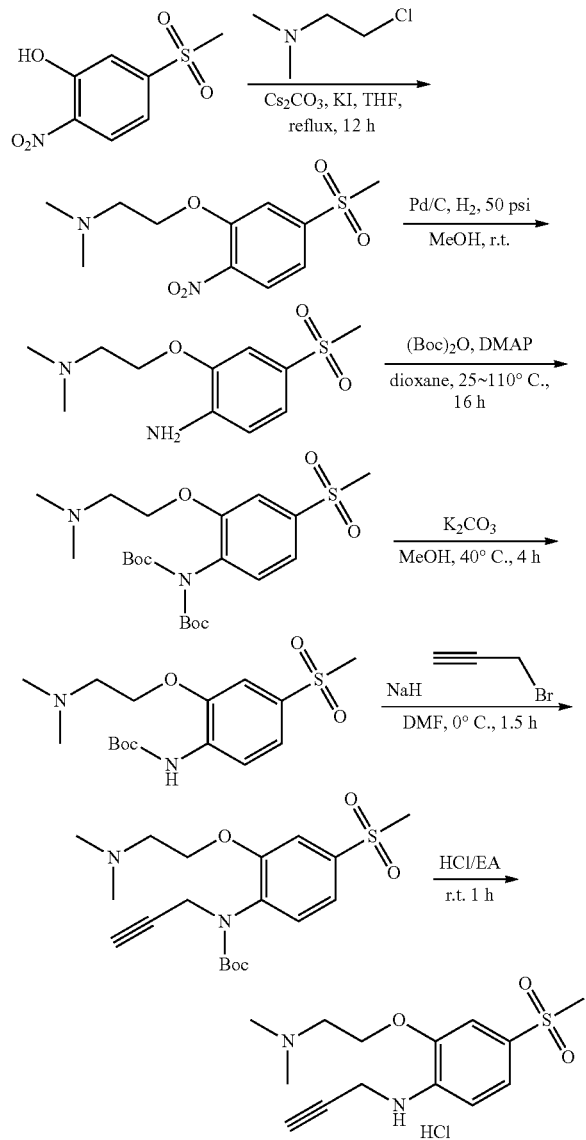

Synthesis of N,N-dimethyl-2-(5-(methylsulfonyl)-2-nitrophenoxy)ethan-1-amine: To a mixture of 5-(methylsulfonyl)-2-nitrophenol (prepared according to the first two steps of Example A13) (200 mg, 920.81 μmol, 1 eq.) in THF (10 mL) were added KI (29.96 mg, 180.48 μmol, 0.196 eq.), 2-chloro-N,N-dimethyl-ethanamine (213.54 mg, 1.48 mmol, 1.61 eq., HCl), and $Cs_2CO_3$ (738.05 mg, 2.27 mmol, 2.46 eq.). The mixture was stirred at 70° C. for 16 h, after which time HPLC analysis indicated a reactant:product ratio of 4:1. The mixture was poured into water (40 mL) and extracted with EtOAc (20 mL×3). The combined organic layers were washed with brine (20 mL×3), dried over anhydrous sodium sulfate, filtered, and concentrated under reduced pressure to provide N,N-dimethyl-2-(5-(methylsulfonyl)-2-nitrophenoxy)ethan-1-amine (300 mg, crude) as a yellow oil. MS ($ES^+$, m/z): 288.9.

Synthesis of 2-(2-(dimethylamino)ethoxy)-4-(methylsulfonyl)aniline: To a solution of N,N-dimethyl-2-(5-(methylsulfonyl)-2-nitrophenoxy)ethan-1-amine (0.5 g, 1.73 mmol, 1 eq.) in MeOH (50 mL) was added Pd/C (50 mg, 227.18 mmol, 15% purity, 131 eq.). The mixture was degassed and purged with $H_2$ (349.59 ug, 173.42 μmol, 2.33e-2 μL) and stirred under $H_2$ (50 psi) at 20° C. for 12 h, after which time LC-MS analysis indicated that the reaction was complete. The mixture was poured into MeOH (100 mL), filtered with diatomite, and concentrated to provide 2-(2-(dimethylamino)ethoxy)-4-(methylsulfonyl)aniline (450 mg, crude) as a black brown oil. MS ($ES^+$, m/z): 259.1.

Synthesis of tert-butyl (tert-butoxycarbonyl)(2-(2-(dimethylamino)ethoxy)-4-(methylsulfonyl)phenyl)carbamate: To a solution of 2-(2-(dimethylamino)-sulfonyl)aniline (200 mg, 774.18 μmol, 1 eq.) in dioxane (7 mL) were added $Boc_2O$ (1.01 g, 4.65 mmol, 1.07 mL, 6 eq.) and DMAP (94.58 mg, 774.18 μmol, 1 eq.). The reaction was then stirred at 110° C. for 16 h, after which time LC-MS analysis indicated that the reaction was complete. The mixture was poured into water (50 mL) and extracted with EtOAc (30 mL×3). The combined organic layers were washed with brine (30 mL×3), dried over anhydrous sodium sulfate, filtered, and concentrated under reduced pressure to provide tert-butyl (tert-butoxycarbonyl)(2-(2-(dimethylamino)ethoxy)-4-(methylsulfonyl)phenyl)carbamate (550 mg, crude) as a black brown oil. MS ($ES^+$, m/z): 459.1.

Synthesis of tert-butyl (2-(2-(dimethylamino)ethoxy)-4-(methylsulfonyl)phenyl)carbamate: To a solution of tert-butyl (tert-butoxycarbonyl)(2-(2-(dimethylamino)ethoxy)-4-(methylsulfonyl)phenyl)carbamate (550 mg, 1.20 mmol, 1 eq.) in MeOH (10 mL) was added $K_2CO_3$ (497.29 mg, 3.60 mmol, 3 eq.). The resulting mixture was stirred at 40° C. for 4 h, after which time LC-MS analysis indicated that the reaction was complete. The mixture was concentrated in vacuo, diluted with EtOAc (30 mL) and water (30 mL), and extracted with EtOAc (30 mL×3). The combined organic layers were washed with brine (30 mL×3), dried over anhydrous sodium sulfate, filtered, and concentrated in vacuo. The residue was purified by column chromatography ($SiO_2$, DCM to DCM:MeOH=10:1) to provide tert-butyl (2-(2-(dimethylamino)ethoxy)-4-(methylsulfonyl)phenyl)carbamate (210 mg, 535.18 μmol, 44.6% yield) as a yellow oil. MS ($ES^+$, m/z): 359.1.

Synthesis of tert-butyl (2-(2-(dimethylamino)ethoxy)-4-(methylsulfonyl)phenyl)(prop-2-yn-1-yl)carbamate: To a mixture of tert-butyl (2-(2-(dimethylamino)ethoxy)-4-(methylsulfonyl)phenyl)carbamate (50 mg, 127.42 μmol, 1 eq.) in DMF (1.5 mL) was added NaH (10.19 mg, 254.85 μmol, 60% in mineral oil, 2 eq.) at 0° C. The mixture was stirred at 0° C. for 0.5 h, and a solution of propargyl bromide (22.74 mg, 191.13 μmol, 16.48 μL, 1.5 eq.) in DMF (0.5 mL) was then added dropwise. The mixture was stirred for a further 1 h at 0° C., after which time a new spot was observed upon TLC analysis (DCM:MeOH=20:1, $R_{f(starting\ material)}$=0.23, $R_{f(product)}$=0.17). The mixture was poured into a saturated aqueous solution of $NH_4Cl$ (10 mL), EtOAc (10 mL) was added, and the resulting mixture was extracted with EtOAc (10 mL×3). The combined organic layers were washed with brine (10 mL×3), dried over anhydrous sodium sulfate, filtered, and concentrated in vacuo. The residue was purified by prep-TLC to provide tert-butyl (2-(2-(dimethylamino)ethoxy)-4-(methylsulfonyl)phenyl)(prop-2-yn-1-yl)carbamate (35 mg, 80.26 μmol, 31.5% yield) as a yellow oil. MS ($ES^+$, m/z): 397.4.

Synthesis of 2-(2-(dimethylamino)ethoxy)-4-(methylsulfonyl)-N-(prop-2-yn-1-yl)aniline hydrochloride: A solution of tert-butyl (2-(2-(dimethylamino)ethoxy)-4-(methyl-sulfonyl)phenyl)(prop-2-yn-1-yl)carbamate (35 mg, 80.26 µmol, 1 eq.) in HCl/EtOAc (4 M, 20.06 µL) was stirred at 15° C. for 1 h, after which time HPLC and LC-MS analysis indicated that the reaction was complete. The mixture was concentrated in vacuo to provide 2-(2-(dimethylamino) ethoxy)-4-(methylsulfonyl)-N-(prop-2-yn-1-yl)aniline hydrochloride (30 mg, crude) as a yellow oil. MS (ES+, m/z): 296.9.

Example A18: Preparation of 2-methoxy-4-(morpholinosulfonyl)-N-(prop-2-yn-1-yl)aniline

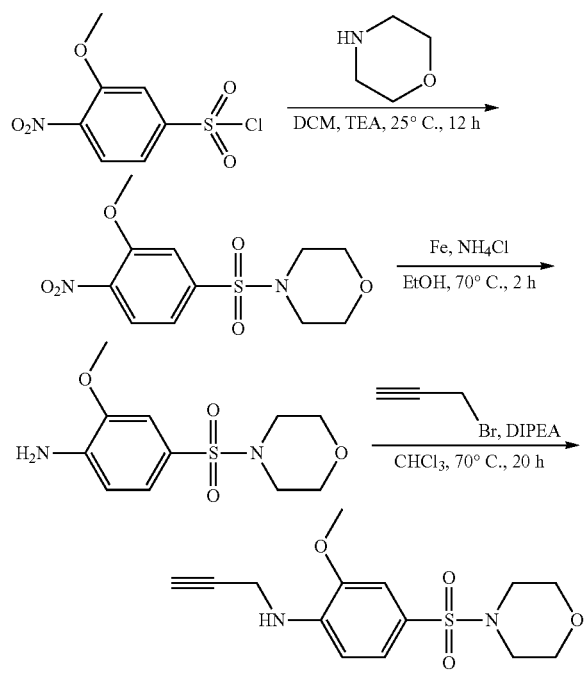

2-Methoxy-4-(morpholinosulfonyl)-N-(prop-2-yn-1-yl) aniline was prepared via a procedure analogous to the synthesis of N-(2-hydroxyethyl)-3-methoxy-N-methyl-4-(prop-2-yn-1-ylamino)benzenesulfonamide according to EXAMPLE A15, using morpholine in place of 2-(methylamino)ethan-1-ol. MS (ES+, m/z): 311.1.

Example A19: Preparation of 1-(4-((3-methoxy-4-(prop-2-yn-1-ylamino)phenyl) sulfonyl)piperazin-1-yl)ethan-1-one

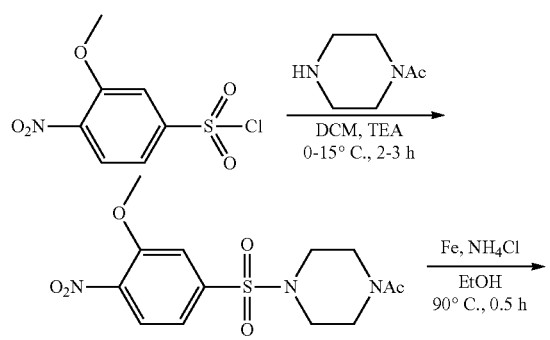

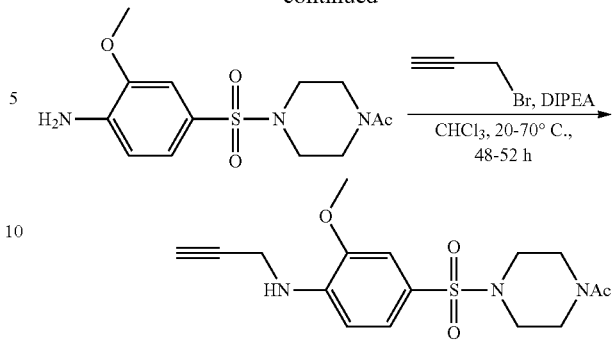

1-(4-((3-methoxy-4-(prop-2-yn-1-ylamino)phenyl)sulfonyl)piperazin-1-yl)ethan-1-one was prepared via a procedure analogous to the synthesis of N-(2-hydroxyethyl)-3-methoxy-N-methyl-4-(prop-2-yn-1-ylamino) benzenesulfonamide according to EXAMPLE A15, using N-acetylpiperazine in place of 2-(methylamino)ethan-1-ol.

Example A20: Preparation of N-(2,3-dihydroxypropyl)-3-methoxy-4-(prop-2-yn-1-ylamino)benzenesulfonamide

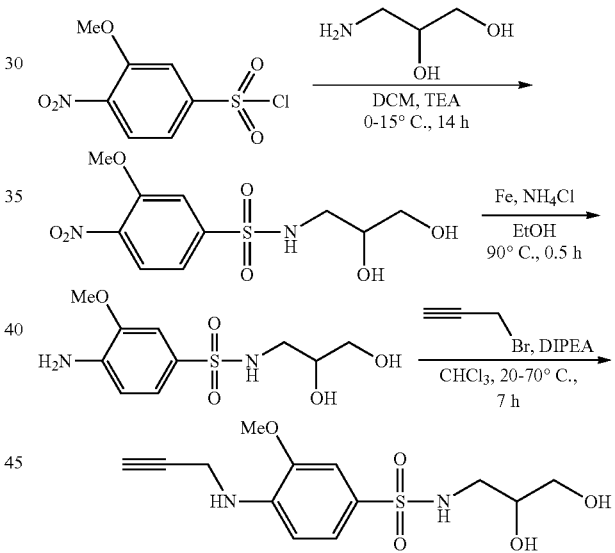

N-(2,3-dihydroxypropyl)-3-methoxy-4-(prop-2-yn-1-ylamino)benzenesulfonamide was prepared via a procedure analogous to the synthesis of N-(2-hydroxyethyl)-3-methoxy-N-methyl-4-(prop-2-yn-1-ylamino)benzenesulfonamide according to EXAMPLE A15, using (rac)-3-aminopropane-1,2-diol in place of 2-(methylamino)ethan-1-ol.

Example A21: Preparation of 2-(fluoromethoxy)-4-(methylsulfonyl)-N-(prop-2-yn-1-yl)aniline

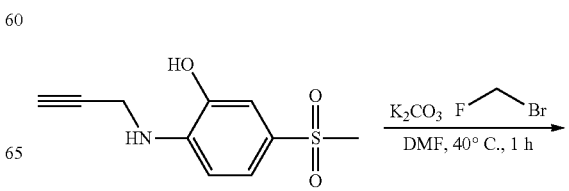

-continued

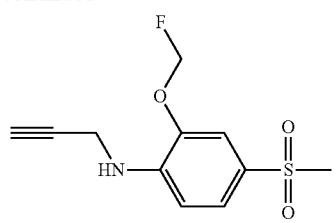

To a solution of 5-(methylsulfonyl)-2-(prop-2-yn-1-ylamino)phenol (400 mg, 1.60 mmol, 1 eq.) in DMF (8 mL) were added $K_2CO_3$ (662.61 mg, 4.79 mmol, 3 eq.) and bromo(fluoro)methane (360.95 mg, 3.20 mmol, 2 eq.) in one portion under $N_2$. The mixture was stirred at 40° C. for 60 min. TLC and LC-MS analysis showed that the reaction was complete. The reaction was diluted with water (30 mL) and extracted with EtOAc (30 mL×3). The combined organic layers were washed with water (30 mL×3) and brine (30 mL×2), dried over anhydrous sodium sulfate, filtered, and concentrated in vacuo. The crude residue was purified by column chromatography ($SiO_2$, PE:EtOAc=1.5:1 to 1:1) to afford the desired product (320 mg, 1.24 mmol, 77.83% yield) as a pink solid. MS ($ES^+$, m/z): 258.0.

Example A22: Preparation of methyl 2-(5-(methylsulfonyl)-2-(prop-2-yn-1-ylamino)phenoxy)acetate

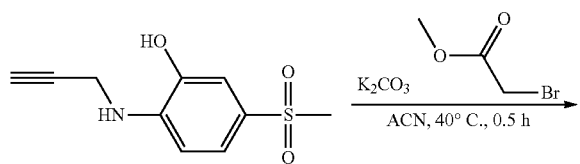

To a solution of 5-(methylsulfonyl)-2-(prop-2-yn-1-ylamino) phenol (0.3 g, 1.3 mmol, 1 eq.) in acetonitrile (5 mL) were added $K_2CO_3$ (552.18 mg, 4 mmol, 3 eq.) and methyl 2-bromoacetate (1.5 eq.). Then the mixture was stirred for 0.5 h at 40° C. under $N_2$. TLC analysis showed that the reaction was complete. The reaction was quenched with water (20 mL) and extracted with EtOAc (20 mL×3). The combined organic layers were washed with saturate brine (20 mL×3), dried over anhydrous sodium sulfate, filtered, and concentrated in vacuo. The residue was purified by prep-TLC ($SiO_2$, DCM:MeOH=1:0) to afford the desired product as a yellow solid. 75.8% yield, MS ($ES^+$, m/z): 298.1.

Example A23: Preparation of 6-(methylsulfonyl)-3-(prop-2-yn-1-yl)benzo[d]oxazol-2 (3H)-one

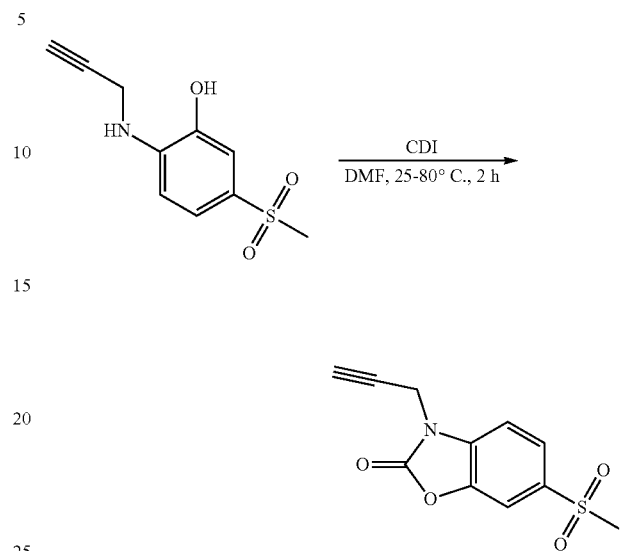

To a solution of 5-(methylsulfonyl)-2-(prop-2-yn-1-ylamino)phenol (0.9 g, 4 mmol, 1 eq.) in DMF (9 mL) was added CDI (777.40 mg, 4.79 mmol, 1.2 eq.) at 25° C. The mixture was stirred at 25° C. for 1 h and then at 80° C. for 1 h. LC-MS analysis showed that the starting material was consumed completely, and one main peak with the mass of the desired product was detected. The mixture was poured into water (50 mL), and the resulting mixture was extracted with DCM (20 mL×3). The combined organic layers were washed with water (20 mL×3), dried over anhydrous sodium sulfate, filtered, and concentrated under reduced pressure to give a residue. The crude residue was lyophilized to afford the desired product (1 g, crude) as a yellow solid. MS ($ES^+$, m/z): 252.0.

Example A24: Synthesis of (3R,4R)-3-methoxy-N-(prop-2-yn-1-yl)tetrahydro-2H-pyran-4-amine

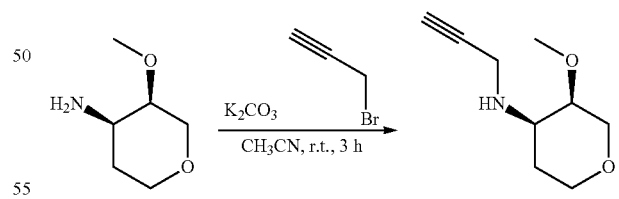

To a solution of (3R)-3-methoxytetrahydropyran-4-amine (0.1 g, 596.54 μmol, 1 eq., HCl) in $CH_3CN$ (2 mL) were added $K_2CO_3$ (0.5 g, 3.62 mmol, 6 eq.) and 3-bromoprop-1-yne (56.77 mg, 477.23 μmol, 41.14 μL, 0.8 eq.). The mixture was stirred at 25° C. for 1 h. LC-MS analysis showed that the reaction was complete. The reaction was concentrated under reduced pressure and purified by prep-TLC ($SiO_2$, DCM:MeOH=20:1) to afford the desired product (0.029 g, 145.67 μmol, 24.4% yield) as a yellow oil. MS ($ES^+$, m/z): 170.2.

Example A25: Synthesis of 2-fluoro-5-methoxy-4-(prop-2-yn-1-ylamino)benzoic acid

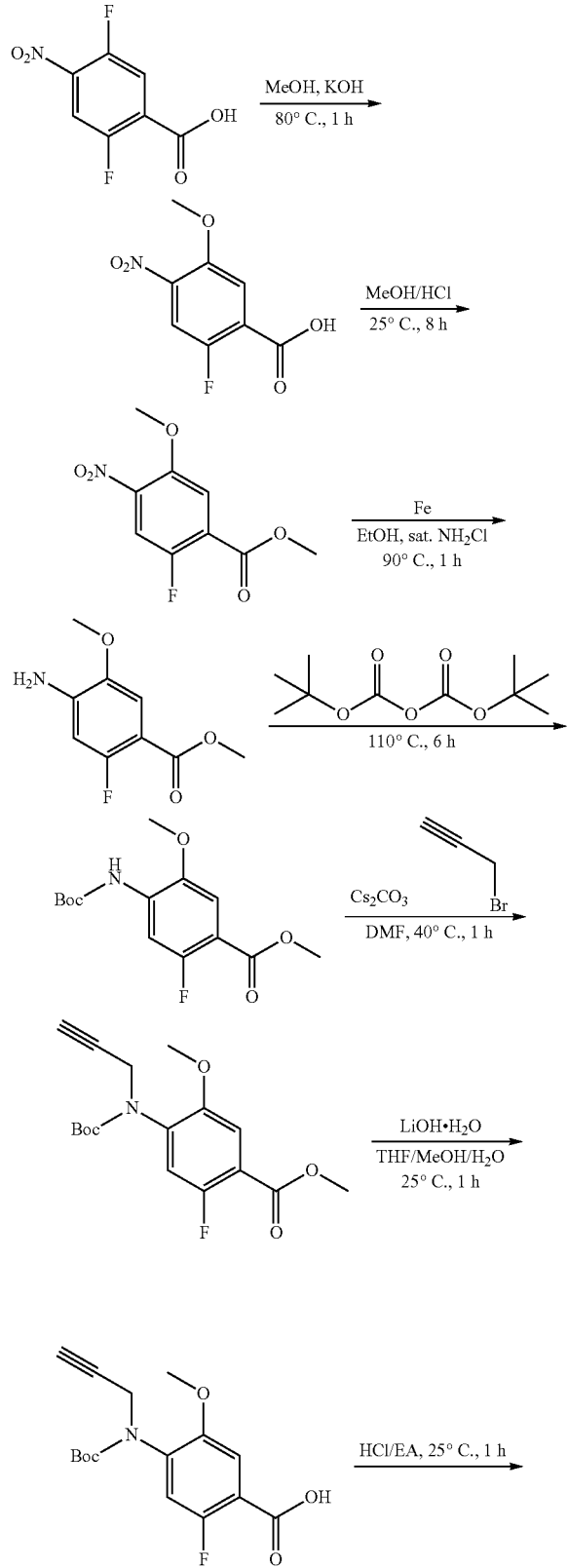

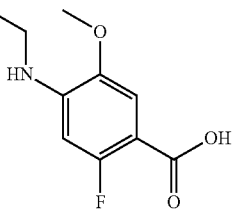

Preparation of 2-fluoro-5-methoxy-4-nitrobenzoic acid: To a solution of 2,5-difluoro-4-nitro-benzoic acid (5 g, 24.62 mmol, 1 eq.) in MeOH (60 mL) was added a solution of KOH (4.14 g, 73.86 mmol, 3 eq.) in MeOH (20 mL) dropwise. The mixture was heated at reflux for 2 h (oil bath temperature: 80° C.). The resulting mixture was stirred at 80° C. for 2 h. LC-MS analysis showed that the reaction was complete. 2 N HCl was added to the reaction mixture at 20° C. to adjust the pH of the mixture to 2. The mixture was then concentrated to remove MeOH. The residue was extracted with water (100 mL) and EtOAc (100 mL×3). The organic layer was washed with brine (100 mL), dried over anhydrous sodium sulfate, filtered, and concentrated to afford the crude product (5.2 g, crude) as a yellow solid.

Preparation of methyl 2-fluoro-5-methoxy-4-nitrobenzoate: A solution of 2-fluoro-5-methoxy-4-nitrobenzoic acid (0.3 g, 1.39 mmol, 1 eq.) in HCl/MeOH (10 mL) was stirred at 25° C. for 3 h until a yellow solid formed. LC-MS analysis showed that the reaction was complete. The reaction was concentrated under reduced pressure to afford the desired product (0.3 g, 1.24 mmol, 89.2% yield) as a yellow solid.

Preparation of methyl 4-amino-2-fluoro-5-methoxybenzoate: To a mixture of methyl 2-fluoro-5-methoxy-4-nitrobenzoate (0.3 g, 1.24 mmol, 1 eq.) in EtOH (3 mL) and saturated aqueous $NH_4Cl$ (1 mL) at 90° C. was added Fe (347.26 mg, 6.22 mmol, 5 eq.). The mixture was stirred at 90° C. for 1 h. TLC analysis showed that the reaction was complete. The mixture was extracted with EtOAc (20 mL×3). The organic layer was washed with brine (20 mL×2), dried over anhydrous sodium sulfate, filtered, and concentrated under reduced pressure. The residue was purified by prep-TLC ($SiO_2$, PE:EtOAc=3:1) to afford the desired product (0.22 g, 994.08 μmol, 79.93% yield) as an orange solid.

Preparation of methyl 4-((tert-butoxycarbonyl)amino)-2-fluoro-5-methoxybenzoate: To a solution of methyl 4-amino-2-fluoro-5-methoxy-benzoate (200 mg, 903.71 μmol, 1 eq.) in di-tert-butyl-dicarbonate (4.75 g, 21.76 mmol, 5 mL, 24.08 eq.) was stirred at 110° C. for 6 h. LC-MS analysis showed that some starting material remained. The reaction mixture was concentrated under reduced pressure and purified by prep-TLC ($SiO_2$, PE:EtOAc=4:1) to afford the desired product (0.23 g, 691.63 μmol, 76.53% yield) as a white solid. MS ($ES^+$, m/z): 300.2.

Preparation of methyl 4-((tert-butoxycarbonyl)(prop-2-yn-1-yl)amino)-2-fluoro-5-methoxybenzoate: To a solution of methyl 4-((tert-butoxycarbonyl)amino)-2-fluoro-5-methoxybenzoate (0.2 g, 601.42 μmol, 1 eq.) in DMF (4 mL) were added $Cs_2CO_3$ (587.86 mg, 1.80 mmol, 3 eq.) and 3-bromoprop-1-yne (143.09 mg, 1.20 mmol, 103.69 μL, 2 eq.). The reaction mixture was stirred at 40° C. for 1 h. LC-MS analysis showed that the reaction was complete. The reaction mixture was poured into EtOAc (15 mL) and extracted with EtOAc (15 mL×3). The combined organic layers were washed with brine (15 mL×3), dried over anhydrous sodium sulfate, filtered, and concentrated under reduced pressure. The residue was purified by prep-TLC (SiO$_2$, PE:EtOAc=5:1) to afford the desired product (0.18 g, 480.22 μmol, 79.85% yield) as a white oil.

Preparation of 4-((tert-butoxycarbonyl)(prop-2-yn-1-yl) amino)-2-fluoro-5-methoxybenzoic acid: To a solution of methyl 4-((tert-butoxycarbonyl)(prop-2-yn-1-yl)amino)-2-fluoro-5-methoxybenzoate (0.16 g, 426.87 μmol, 1 eq.) in THF (1 mL), MeOH (1 mL), and water (1 mL) was added lithium hydroxide hydrate (53.74 mg, 1.28 mmol, 3 eq.). The mixture was stirred at 25° C. for 1 h. TLC analysis showed that the reaction was complete. 1M HCl was added to adjust the pH of the reaction mixture to 2. The mixture was extracted with EtOAc (20 mL×3). The organic layer was washed with brine (20 mL×3), dried over anhydrous sodium sulfate, filtered, and concentrated under reduced pressure to obtain the crude product (0.14 g, crude) as a white solid. The crude product was used without purification.

Preparation of 2-fluoro-5-methoxy-4-(prop-2-yn-1-ylamino)benzoic acid: A solution of 4-((tert-butoxycarbonyl)(prop-2-yn-1-yl)amino)-2-fluoro-5-methoxybenzoic acid (0.15 g, 463.94 μmol, 1 eq.) in 4N HCl/EtOAc (6 mL, 51.73 eq.) was stirred at 25° C. for 1 h. LC-MS analysis showed that the reaction was complete. The reaction was concentrated under reduced pressure to obtain the crude product (0.1 g, crude, HCl) as a yellow solid. The crude product was used without purification. MS (ES$^+$, m/z): 222.0.

Example A26: Preparation of (3S)-3-methoxy-N-(prop-2-yn-1-yl)tetrahydro-2H-pyran-4-amine

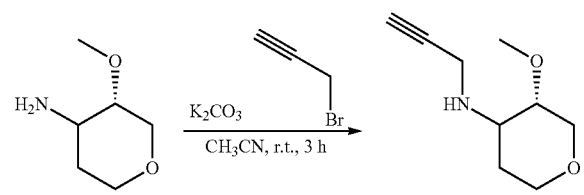

To a solution of (3S)-3-methoxytetrahydro-2H-pyran-4-amine (0.5 g, 3.81 mmol, 1 eq.) in CH$_3$CN (8 mL) was added K$_2$CO$_3$ (1.58 g, 11.44 mmol, 3 eq.). The mixture was stirred at 25° C., and 3-bromoprop-1-yne (362.76 mg, 3.05 mmol, 262.87 μL, 0.8 eq.) was added to the solution. The resulting reaction mixture was stirred at 25° C. for 3 h. TLC analysis showed that the reaction was complete, and some starting material remained. The reaction was filtered and concentrated under reduced pressure. The residue was purified by column chromatography (SiO$_2$, PE:EtOAc=10:1 to 5:1) to afford the desired product (0.33 g, 1.76 mmol, 46.04% yield) as a yellow oil. MS (ES$^+$, m/z): 170.1.

Example A27: Synthesis of 2-(COOR)-4-(methylsulfonyl)-N-(prop-2-yn-1-yl)aniline

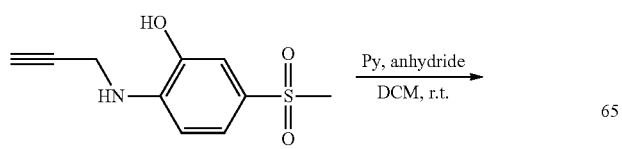

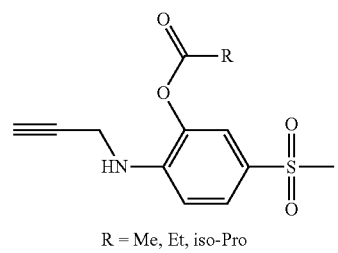

R = Me, Et, iso-Pro

To a solution of 5-(methylsulfonyl)-2-(prop-2-yn-1-ylamino)phenol (1 eq.) in DCM (5 mL) were added pyridine (1 eq.) and R-anhydride (1 eq.). The mixture was stirred at 25° C. for 2 h. LC-MS analysis showed the desired product. The reaction mixture was quenched by adding water (100 mL) at 0° C. and extracted with EtOAc (30 mL×3). The combined organic layers were washed with brine (30 mL), dried over anhydrous sodium sulfate, filtered, and concentrated under reduced pressure. The residue was purified by prep-TLC (SiO$_2$, PE:EtOAc=PE:EtOAc=1:1, R$_f$=0.5) to afford the desired product.

Example A28: Synthesis of 4-(methylsulfonyl)-N-(prop-2-yn-1-yl)-2-(trifluoromethoxy)aniline

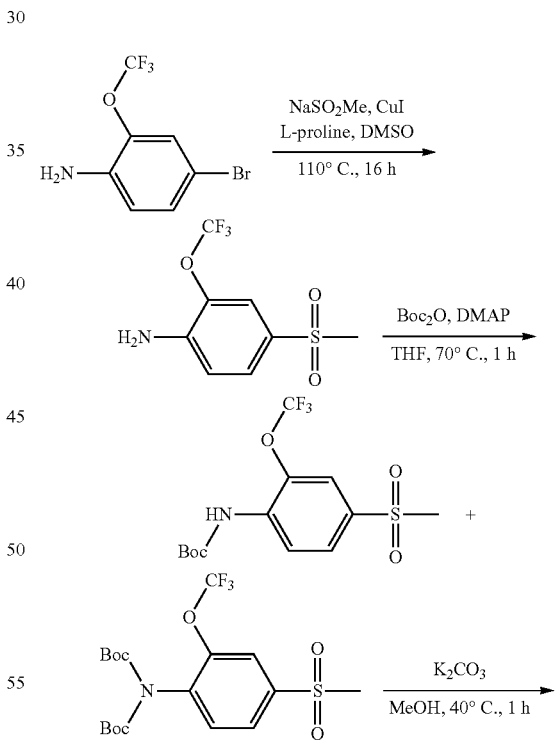

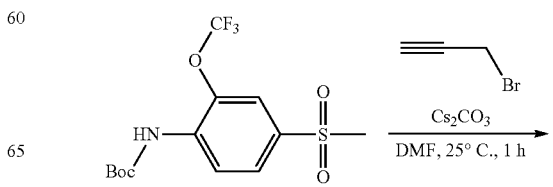

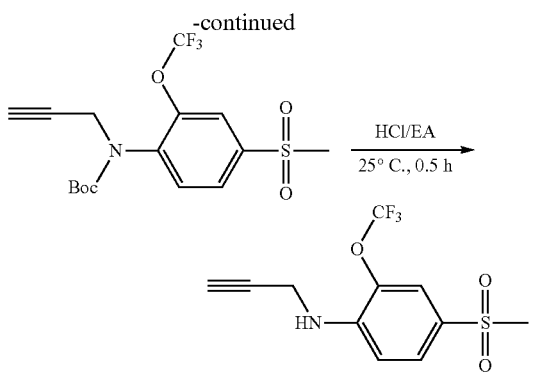

Preparation of 4-(methylsulfonyl)-2-(trifluoromethoxy)aniline: To a mixture of 4-bromo-2-(trifluoromethoxy)aniline (5 g, 19.53 mmol, 2.96 mL, 1 eq.) and sodium methyl sulfate (5.98 g, 58.59 mmol, 3 eq.) in DMSO (50 mL) were added L-proline (1.12 g, 9.76 mmol, 0.5 eq.) and CuI (1.49 g, 7.81 mmol, 0.4 eq.). The reaction mixture was stirred at 100° C. for 16 h under $N_2$. TLC analysis showed that some of the starting material remained. The mixture was stirred at 20° C. for 1 h and was extracted with EtOAc (50 mL×3). The combined organic layers were washed with brine (50 mL×3), dried over anhydrous sodium sulfate, filtered, and concentrated under reduced pressure. The residue was purified by column chromatography ($SiO_2$, PE:EtOAc=10:1 to 1:1) to afford the desired product (2.6 g, 10.19 mmol, 52.16% yield) as a white solid.

Preparation of tert-butyl (4-(methylsulfonyl)-2-(trifluoromethoxy)phenyl) carbamate: To a solution of tert-butyl (4-(methylsulfonyl)-2-(trifluoromethoxy)phenyl) carbamate (500 mg, 1.76 mmol, 1 eq.) in THF (10 mL) were added $Boc_2O$ (461.78 mg, 2.12 mmol, 486.09 µL, 1.2 eq.) and DMAP (258.49 mg, 2.12 mmol, 1.2 eq.). The reaction mixture was stirred at 70° C. for 1 h. TLC and LC-MS analysis showed that the reaction was complete. The reaction was diluted with water (20 mL) and extracted with EtOAc (20 mL×3). The combined organic layers were washed with brine (20 mL×3), dried over anhydrous sodium sulfate, filtered, and concentrated under reduced pressure. The crude residue was purified by column chromatography ($SiO_2$, PE:EtOAc=10:1 to 1:1) to afford tert-butyl (4-(methylsulfonyl)-2-(trifluoromethoxy)phenyl)carbamate (900 mg, 1.98 mmol, 112.07% yield) and N,N-di(tert-butoxycarbonyl)-4-(methylsulfonyl)-2-(trifluoromethoxy)aniline (900 mg, 2.53 mmol, 143.65% yield) as a white solid.

A mixture of tert-butyl (4-(methylsulfonyl)-2-(trifluoromethoxy)phenyl)carbamate (700 mg, 1.54 mmol, 1 eq.), N,N-di(tert-butoxycarbonyl)-4-(methylsulfonyl)-2-(trifluoromethoxy)aniline (700 mg, 1.97 mmol, 1.28 eq.), and $K_2CO_3$ (637.25 mg, 4.61 mmol, 3 eq.) in MeOH (18 mL) was stirred at 40° C. for 2 h. LC-MS analysis showed that the reaction was complete. The reaction mixture was filtered and concentrated under reduced pressure to give the crude product (1 g) as a light yellow solid.

Preparation of tert-butyl (4-(methylsulfonyl)-2-(trifluoromethoxy)phenyl)(prop-2-yn-1-yl)carbamate: To the solution of tert-butyl (4-(methylsulfonyl)-2-(trifluoromethoxy) phenyl) carbamate (0.8 g, 2.25 mmol, 1 eq.) in DMF (20 mL) were added $Cs_2CO_3$ (2.20 g, 6.75 mmol, 3 eq.) and 3-bromoprop-1-yne (803.49 mg, 6.75 mmol, 582.24 µL, 3 eq.) at 25° C. The mixture was stirred for 1 h. TLC and LC-MS showed that the reaction was complete. The reaction was diluted with water (20 mL) and extracted with EtOAc (10 mL×3). The combined organic layers were washed with brine (10 mL×3), dried over anhydrous sodium sulfate, filtered, and concentrated in vacuo. The crude residue was purified by column chromatography ($SiO_2$, DCM:MeOH=10:1) to afford the desired product (0.65 g, 1.49 mmol, 66.05% yield) as a yellow solid.

Preparation of 4-(methylsulfonyl)-N-(prop-2-yn-1-yl)-2-(trifluoromethoxy)aniline: A solution of tert-butyl (4-(methylsulfonyl)-2-(trifluoromethoxy)phenyl)(prop-2-yn-1-yl) carbamate (650 mg, 1.49 mmol, 1 eq.) in HCl/EtOAc (4 M, 13.50 mL, 36.31 eq.) was stirred at 25° C. for 0.5 h. LC-MS analysis showed that the reaction was complete. The reaction was diluted with EtOAc (10 mL) and concentrated in vacuo. The desired product (340 mg, crude, HCl) was obtained as a yellow solid. MS ($ES^+$, m/z): 291.9.

Example A29: Synthesis of 2-methyl-4-(methylsulfonyl)-N-(prop-2-yn-1-yl)aniline

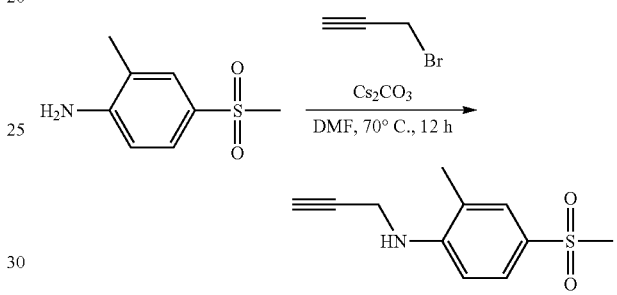

To a solution of 2-methyl-4-(methylsulfonyl)aniline (1 g, 5.40 mmol, 1 eq.) in DMF (10 mL) were added $K_2CO_3$ (2.24 g, 16.19 mmol, 3 eq.) and 3-bromoprop-1-yne (642.18 mg, 5.40 mmol, 465.35 µL, 1 eq.) at 70° C. The mixture was stirred at 70° C. for 12 h. TLC analysis showed that some of the starting material remained. The reaction was poured into water (20 mL) and extracted with EtOAc (20 mL×3). The combined organic layers were washed with brine (20 mL×3), dried over anhydrous sodium sulfate, filtered, and concentrated in vacuo. The residue was purified by column chromatography ($SiO_2$, PE:EtOAc=10:1 to 1:1) to afford the desired product (0.5 g, 2.02 mmol, 37.33% yield) as a yellow solid. MS ($ES^+$, m/z): 224.1.

Example A30: Synthesis of 2-fluoro-5-methoxy-N-methyl-4-(prop-2-yn-1-ylamino)benzamide

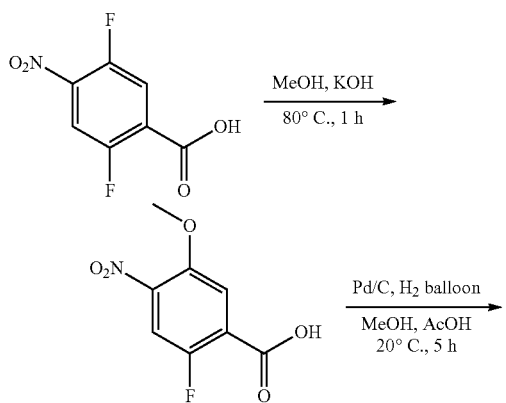

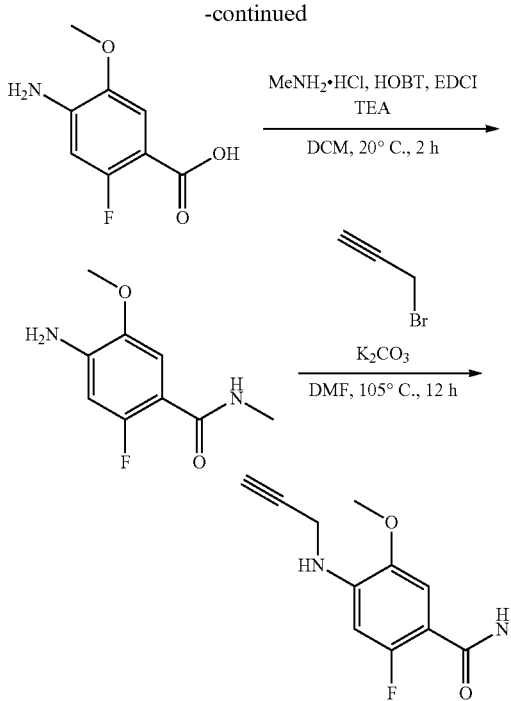

Preparation of 2-fluoro-5-methoxy-4-nitrobenzoic acid: To a solution of 2,5-difluoro-4-nitro-benzoic acid (4 g, 19.69 mmol, 1 eq.) in MeOH (64 mL) was added a solution of KOH (3.31 g, 59.08 mmol, 3 eq.; dropwise addition) in MeOH (16 mL) at 80° C. The resulting mixture was stirred at 80° C. for 2 h. HPLC analysis showed that the reaction was complete. To the solution was added 2 N HCl at 20° C. to adjust the pH of the mixture to 2. The mixture was concentrated to remove MeOH, and the residue was extracted with water (30 mL) and EtOAc (40 mL×3). The organic layer was washed with brine (30 mL), dried over anhydrous sodium sulfate, filtered, and concentrated. The crude product (4 g, 18.59 mmol, 94.41% yield) was obtained as a yellow solid and used without purification.

Preparation of 4-amino-2-fluoro-5-methoxybenzoic acid: A mixture of 2-fluoro-5-methoxy-4-nitrobenzoic acid (4 g, 18.59 mmol, 1 eq.) and Pd/C (2 g, 1.88 mmol, 10% purity, 1.01e-1 eq.) in MeOH (50 mL) was degassed and purged with $N_2$ three times and stirred at 20° C. for 5 h under $H_2$ (15 Psi). LC-MS and HPLC analysis showed that the reaction was complete. The mixture was filtered through silica gel, and the filtrate was concentrated. The crude residue (3.5 g, 17.01 mmol, 91.50% yield) was obtained as a yellow solid and used without purification. MS ($ES^+$, m/z): 184.2.

Preparation of 4-amino-2-fluoro-5-methoxy-N-methylbenzamide: A mixture of 4-amino-2-fluoro-5-methoxybenzoic acid (2 g, 10.80 mmol, 1 eq.), methanamine hydrochloride (1.46 g, 21.60 mmol, 2 eq.), HOBt (2.19 g, 16.20 mmol, 1.5 eq.), EDCI (3.11 g, 16.20 mmol, 1.5 eq.), and TEA (4.37 g, 43.21 mmol, 6 mL, 4 eq.) in DCM (30 mL) was degassed and purged with $N_2$ three times. The mixture was stirred at 20° C. for 2 h under $N_2$. LC-MS analysis showed that the reaction was complete. The mixture was extracted with water (30 mL) and DCM (50 mL×5). The organic layer was washed with brine (40 mL), dried over anhydrous sodium sulfate, filtered, and concentrated. The residue was purified by column chromatography (SiO₂, PE:EtOAc=3:1) to obtain the desired product (1.1 g, 5 mmol, 46.24% yield) as a white solid. MS ($ES^+$, m/z): 199.1.

Preparation of 2-fluoro-5-methoxy-N-methyl-4-(prop-2-yn-1-ylamino)benzamide: A mixture of 4-amino-2-fluoro-5-methoxy-N-methylbenzamide (0.7 g, 3.18 mmol, 1 eq.), 3-bromoprop-1-yne (2.27 g, 19.07 mmol, 1.64 mL, 6 eq.), and $K_2CO_3$ (1.32 g, 9.54 mmol, 3 eq.) in DMF (10 mL) was degassed and purged with $N_2$ three times, and the mixture was stirred at 105° C. for 12 h under $N_2$. TLC analysis showed that the starting material was consumed. The reaction mixture was extracted with water (60 mL) and EtOAc (40 mL×3). The organic layer was washed with brine (15 mL×3), dried over anhydrous sodium sulfate, filtered, and concentrated in vacuo. The residue was purified by column chromatography (SiO₂, PE:EtOAc=5:1 to 3:1) to obtain the desired product (0.6 g, 1.78 mmol, 55.93% yield) as a yellow solid.

Example A31: Synthesis of 2-amino-N-((3-methoxy-4-(prop-2-yn-1-ylamino)phenyl)sulfonyl)acetamide

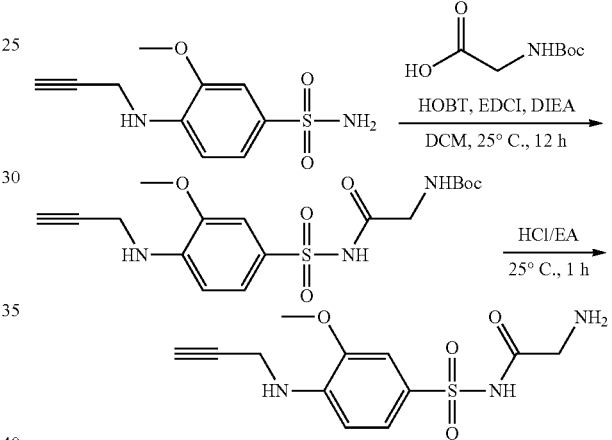

Preparation of tert-butyl (2-((3-methoxy-4-(prop-2-yn-1-ylamino)phenyl)sulfonamido)-2-oxoethyl)carbamate: To a solution of (tert-butoxycarbonyl)glycine (437.45 mg, 2.50 mmol, 70.16 μL, 2 eq.) in DCM (6 mL) were added HATU (949.47 mg, 2.50 mmol, 2 eq.) and TEA (252.68 mg, 2.50 mmol, 347.57 μL, 2 eq.). The mixture was stirred at 25° C. for 0.5 h. 3-Methoxy-4-(prop-2-yn-1-ylamino)benzenesulfonamide (300 mg, 1.25 mmol, 1 eq.) was then added to the reaction, and the mixture was stirred at 25° C. for 2 h. TLC analysis showed that 40% of the starting material remained. Second portions of 3-methoxy-4-(prop-2-yn-1-ylamino)benzenesulfonamide (437.45 mg, 2.50 mmol, 2 eq.), HATU (949.47 mg, 2.50 mmol, 2 eq.), and TEA (252.68 mg, 2.50 mmol, 347.57 μL, 2 eq.) were added to the reaction, and the mixture was stirred further at 25° C. for 10 h. TLC analysis showed that the starting material was consumed. The mixture was poured into water (10 mL), and the aqueous phase was extracted with DCM (10 mL×3). The combined organic layers were washed with brine (10 mL×3), dried over anhydrous sodium sulfate, filtered, and concentrated in vacuo. The residue was purified by silica gel chromatography (PE:EtOAc=1:1 to 1:2) to afford the desired product (560 mg, 845.40 μmol, 67.71% yield) as a colorless oil.

Preparation of 2-amino-N-((3-methoxy-4-(prop-2-yn-1-ylamino)phenyl)sulfonyl)acetamide: tert-Butyl (2-((3- methoxy-4-(prop-2-yn-1-ylamino)phenyl)sulfonamido)-2-oxoethyl)carbamate (490 mg, 739.72 μmol, 1 eq.) was dissolved in 4N HCl in EtOAc (5 mL) and the solution was stirred at 25° C. for 1 h. LC-MS analysis showed that the reaction was complete. The residue was concentrated in vacuo to afford the crude product (350 mg, crude) as a white solid. MS (ES+, m/z): 298.1.

Example A32: Synthesis of 4-methoxy-N-prop-2-ynyl-pyridin-3-amine

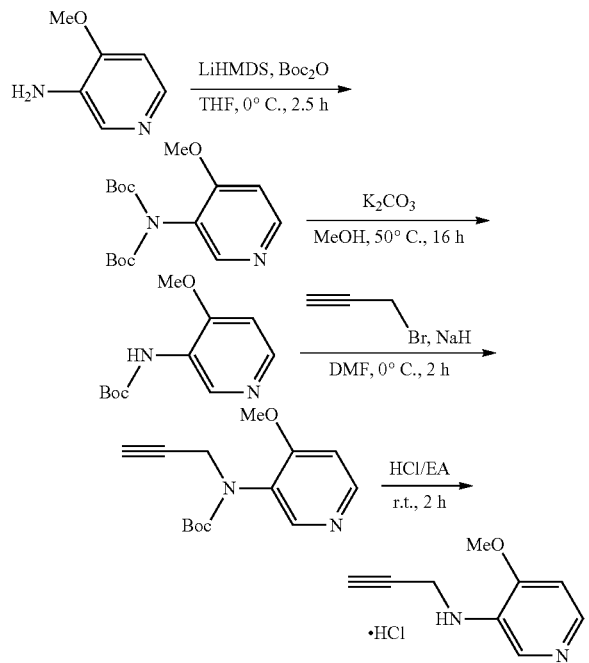

Preparation of tert-butyl N-tert-butoxycarbonyl-N-(4-methoxy-3-pyridyl)carbamate: To a solution of 4-methoxy-pyridin-3-amine (810 mg, 6.52 mmol, 1 eq.) in THF (25 mL) was added LiHMDS (1 M, 399.55 μL, 2.48 eq.). The solution was purged with N₂ three times, and the mixture was stirred at 0° C. for 30 mins under N₂. Then, Boc₂O (2.85 g, 13.04 mmol, 3 mL, 2 eq.) was added to the reaction, and the mixture was stirred at 0° C. for 2 h under N₂. TLC analysis showed that the starting material was partially consumed, and one spot for the desired product was detected. The reaction mixture was poured into a saturated NH₄Cl solution (100 mL) and was extracted with EtOAc (50 mL×1, then 25 mL×2). The combined organic layers were dried over anhydrous sodium sulfate, filtered, and concentrated under reduced pressure to afford tert-butyl N-tert-butoxycarbonyl-N-(4-methoxy-3-pyridyl)carbamate (1.5 g, crude) as a yellow oil.

Preparation of tert-butyl N-(4-methoxy-3-pyridyl)carbamate: A mixture of tert-butyl N-tert-butoxycarbonyl-N-(4-methoxy-3-pyridyl)carbamate (1.50 g, 4.62 mmol, 1 eq.) and K₂CO₃ (639.13 mg, 4.62 mmol, 1 eq.) in MeOH (2 mL) was degassed and purged with N₂ three times. The mixture was stirred at 50° C. for 16 h under N₂. TLC analysis showed that the starting material was consumed, and one spot for the desired product was observed. The mixture was poured into water (100 mL) and extracted with EtOAc (50 mL×1, then 25 mL×2). The combined organic layers were dried over anhydrous sodium sulfate, filtered, and concentrated under reduced pressure. The crude product was purified by column chromatography to afford tert-butyl N-(4-methoxy-3-pyridyl)carbamate (1 g, 4.01 mmol, 86.87% yield) as a yellow oil.

Preparation of tert-butyl N-(4-methoxy-3-pyridyl)-N-prop-2-ynyl-carbamate: A mixture of tert-butyl N-(4-methoxy-3-pyridyl)carbamate (500 mg, 2.23 mmol, 1 eq.) and NaH (160.56 mg, 6.69 mmol, 3 eq., 60% in mineral oil) in THF (25 mL) was stirred at 0° C. for 1 h under N₂. Then, 3-bromoprop-1-yne (530.46 mg, 4.46 mmol, 384.39 μL, 2 eq.) was added, and the resulting mixture was stirred at 0° C. for 1 h under N₂. TLC analysis showed that the starting material was consumed, and one new spot for the desired product was observed. The mixture was poured into water (100 mL) and extracted with EtOAc (50 mL×1, then 25 mL×2). The combined organic layers were dried over anhydrous sodium sulfate, filtered, and concentrated under reduced pressure. The crude product was purified by column chromatography (PE:EtOAc=2:1) to afford tert-butyl N-(4-methoxy-3-pyridyl)-N-prop-2-ynyl-carbamate (200 mg, 762.49 μmol, 34.19% yield) as a yellow oil.

Preparation of 4-methoxy-N-prop-2-ynyl-pyridin-3-amine: To a solution of tert-butyl N-(4-methoxy-3-pyridyl)-N-prop-2-ynyl-carbamate (200 mg, 762.49 μmol, 1 eq.) in EtOH (10 mL) was added HCl/EtOAc (4 M, 190.62 μL, 1 eq.). The solution was purged with N₂ three times and stirred at 25° C. for 2 h under N₂. TLC analysis showed that the starting material was consumed, and one spot for the desired product was observed. The mixture was concentrated under reduced pressure to afford 4-methoxy-N-prop-2-ynyl-pyridin-3-amine (150 mg, 755.10 μmol, 99.03% yield, HCl) as a yellow solid. The desired product was used without further purification.

Example A33: Synthesis of 2-methoxy-N-prop-2-ynyl-4-(trifluoromethyl)aniline

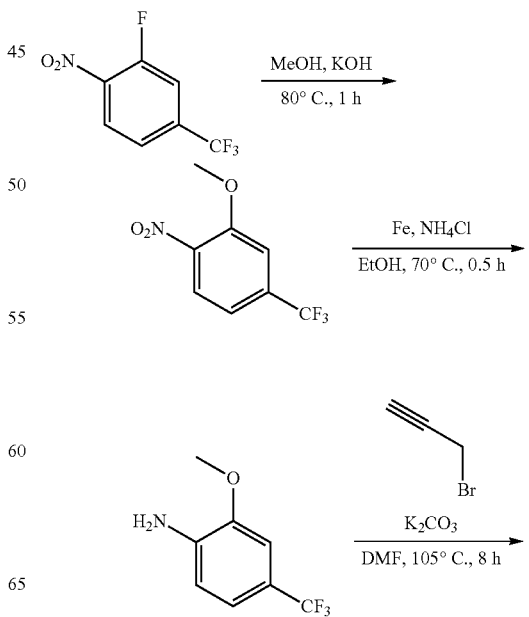

-continued

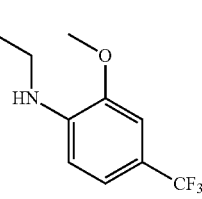

Synthesis of 2-methoxy-1-nitro-4-(trifluoromethyl)benzene: To a solution of 2-fluoro-1-nitro-4-(trifluoromethyl)benzene (23 g, 110 mmol, 1 eq.) in MeOH (350 mL) was added a solution of KOH (18.51 g, 329.99 mmol, 3 eq.) in MeOH (100 mL) at 80° C. The resulting mixture was stirred at 80° C. for 2 h. TLC analysis ($R_{f(product)}$=0.6, PE:EtOAc=5:1) showed that the starting material was consumed, and that a new spot had formed. 2 N HCl was added to the reaction mixture to adjust the pH of the mixture to 2. The solution was then concentrated. The crude residue was washed with water (150 mL) and extracted with EtOAc (300 mL×2). The organic layer was washed with brine (15 mL), dried over anhydrous sodium sulfate, filtered, and concentrated in vacuo to afford 2-methoxy-1-nitro-4-(trifluoromethyl)benzene (22.5 g, 91.57 mmol, 83.25% yield) as a yellow solid. The crude residue was used directly without any purification.

Synthesis of 2-methoxy-4-(trifluoromethyl)aniline: To a solution of 2-methoxy-1-nitro-4-(trifluoromethyl)benzene (23.8 g, 96.86 mmol, 1 eq.) in EtOH (300 mL) and saturated NH$_4$Cl (100 mL) was added Fe (27.05 g, 484.32 mmol, 5 eq.) in several portions at 70° C. over 10 min. The resulting mixture was stirred at 70° C. for 0.5 h. TLC analysis ($R_{f(product)}$=0.50, PE:EtOAc=5:1) showed that the reaction was complete. The reaction mixture was poured into EtOAc (1500 mL), and the resulting mixture was washed with water (500 mL) and extracted with EtOAc (300 mL×2). The organic layer was washed with brine (200 mL×2), dried over anhydrous sodium sulfate, filtered, and concentrated in vacuo to afford 2-methoxy-4-(trifluoromethyl)aniline (19 g, 89.46 mmol, 92.35% yield) as a yellow oil. The residue was used directly without any purification.

Synthesis of 2-methoxy-N-prop-2-ynyl-4-(trifluoromethyl)aniline: A mixture of 2-methoxy-4-(trifluoromethyl)aniline (1 g, 5.23 mmol, 1 eq.), 3-bromoprop-1-yne (3.11 g, 26.16 mmol, 2.25 mL, 5 eq.), K$_2$CO$_3$ (2.17 g, 15.69 mmol, 3 eq.) was prepared in DMF (10 mL). The mixture was degassed and purged with N$_2$ three times, and the mixture was stirred at 105° C. for 8 h under a N$_2$ atmosphere. TLC analysis showed that the starting material was consumed (PE:EtOAc=5:1). The mixture was washed with water (60 mL) and extracted with EtOAc (40 mL×3). The combined organic layers were washed with brine (15 mL×3), dried over anhydrous sodium sulfate, filtered, and concentrated in vacuo. The residue was purified by column chromatography (SiO$_2$, PE:EtOAc=25:1 to 15:1) to afford 2-methoxy-N-prop-2-ynyl-4-(trifluoromethyl)aniline (0.8 g, 2.44 mmol, 46.70% yield) as a yellow oil.

Example A34: Synthesis of ((4-((tert-butoxycarbonyl)(prop-2-yn-1-yl)amino)-3-methoxyphenyl)sulfonyl)methyl acetate

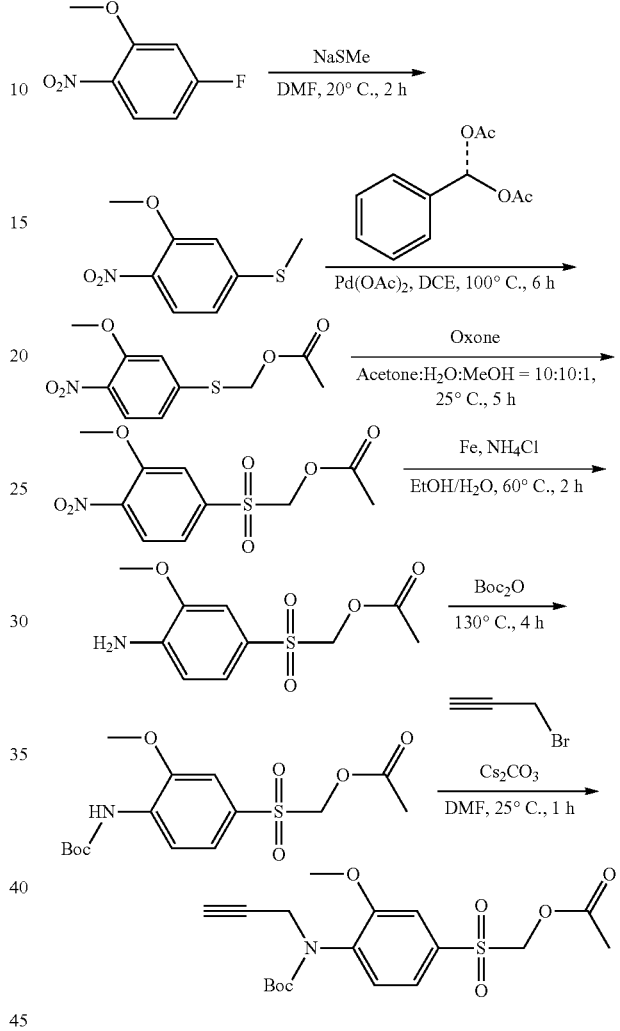

Preparation of (3-methoxy-4-nitrophenyl)(methyl)sulfane: To a solution of 4-fluoro-2-methoxy-1-nitrobenzene (2 g, 11.69 mmol, 1 eq.) in DMF (20 mL) was added sodium methanethiolate (5.32 g, 15.19 mmol, 4.84 mL, 20% purity, 1.3 eq.). The mixture was stirred at 20° C. for 2 h. TLC analysis showed that the reaction was complete. The reaction mixture was diluted by adding a saturated NH$_4$Cl solution (100 mL). The mixture was filtered and concentrated under reduced pressure to give (3-methoxy-4-nitrophenyl)(methyl)sulfane (2.4 g, crude) as a yellow solid.

Preparation of ((3-methoxy-4-nitrophenyl)thio)methyl acetate: To a solution of (3-methoxy-4-nitrophenyl)(methyl) sulfane (1.4 g, 7.03 mmol, 1 eq.) in DCE (15 mL) were added phenyl-λ$^3$-iodanediyl diacetate (3.40 g, 10.54 mmol, 1.5 eq.) and Pd(OAc)$_2$ (473.30 mg, 2.11 mmol, 0.3 eq.). The mixture was stirred at 100° C. for 6 h under N$_2$. TLC analysis showed that the reaction was complete. The reaction mixture was quenched with water (300 mL) and extracted with EtOAc (100 mL×3). The combined organic layers were washed with brine (100 mL×2), dried over anhydrous sodium sulfate, filtered, and concentrated under reduced pressure. The residue was purified by column chromatography (SiO$_2$, PE:EtOAc=8:1 to 3:1) to afford ((3-methoxy-4-nitrophenyl)thio)methyl acetate (1 g, 3.89 mmol, 55.31% yield) as a yellow solid.

Preparation of ((3-methoxy-4-nitrophenyl)sulfonyl) methyl acetate: To a solution of ((3-methoxy-4-nitrophenyl)thio)methyl acetate (0.9 g, 3.50 mmol, 1 eq.) in a mixture of acetone (4 mL), water (0.4 mL), and MeOH (4 mL) was added oxone (6.45 g, 10.50 mmol, 3 eq.). The mixture was stirred at 25° C. for 5 h. LC-MS analysis showed that the reaction was complete. The reaction mixture was diluted with saturated Na$_2$S$_2$O$_3$ solution (200 mL) and extracted with EtOAc (50 mL×3). The combined organic layers were washed with brine (50 mL×2), dried over anhydrous sodium sulfate, filtered, and concentrated under reduced pressure to afford ((3-methoxy-4-nitrophenyl)sulfonyl)methyl acetate (1 g, crude) as a yellow solid. The crude product was used in the next step without purification. MS (ES$^+$, m/z): 311.9.

Preparation of ((4-amino-3-methoxyphenyl)sulfonyl) methyl acetate: To a solution of ((3-methoxy-4-nitrophenyl)sulfonyl)methyl acetate (0.9 g, 3.11 mmol, 1 eq.) in EtOH (8 mL) were added saturated NH$_4$Cl solution (166.43 mg, 3.11 mmol, 2 mL, 1 eq.) and Fe (521.26 mg, 9.33 mmol, 3 eq.). The mixture was stirred at 60° C. for 2 h. TLC analysis showed that the reaction was complete. The reaction mixture was filtered, diluted with water (100 mL), extracted with EtOAc (50 mL×3). The combined organic layers were washed with brine (50 mL×2), dried over anhydrous sodium sulfate, filtered, and concentrated under reduced pressure. The crude residue was purified by column chromatography (SiO$_2$, PE:EtOAc=10:1 to 4:1) to afford ((4-amino-3-methoxyphenyl)sulfonyl)methyl acetate (580 mg, 2.24 mmol, 71.90% yield) as a yellow solid.

Preparation of ((4-((tert-butoxycarbonyl)amino)-3-methoxyphenyl)sulfonyl)methyl acetate: To a solution of ((4-amino-3-methoxyphenyl)sulfonyl)methyl acetate (0.49 g, 1.89 mmol, 1 eq.) in tert-butoxycarbonyl tert-butyl carbonate (20.62 g, 94.49 mmol, 21.71 mL, 50 eq.) was stirred at 130° C. for 4 h. LC-MS analysis showed that the reaction was complete. The reaction mixture was filtered, diluted with water (100 mL) and extracted with EtOAc (50 mL×3). The combined organic layers were washed with brine (50 mL×2), dried over anhydrous sodium sulfate, filtered, and concentrated under reduced pressure. The crude residue was purified by column chromatography (SiO$_2$, PE:EtOAc=10:1 to 4:1) to afford ((4-((tert-butoxycarbonyl)amino)-3-methoxyphenyl)sulfonyl)methyl acetate (0.45 g, 1.25 mmol, 66.25% yield) as a white oil.

Preparation of ((4-((tert-butoxycarbonyl)(prop-2-yn-1-yl)amino)-3-methoxyphenyl)sulfonyl)methyl acetate: To a solution of ((4-((tert-butoxycarbonyl)amino)-3-methoxyphenyl)sulfonyl)methyl acetate (0.35 g, 973.86 μmol, 1 eq.) in DMF (4 mL) were added 3-bromoprop-1-yne (217.22 mg, 1.46 mmol, 157.41 μL, 1.5 eq.) and Cs$_2$CO$_3$ (634.61 mg, 1.95 mmol, 2 eq.). The mixture was stirred at 25° C. for 1 h under N$_2$ LC-MS analysis showed that the reaction was complete. The reaction mixture was diluted with water (100 mL) and extracted with EtOAc (50 mL×2). The combined organic layers were washed with water (50 mL×2) and brine (50 mL×2), dried over anhydrous sodium sulfate, filtered, and concentrated under reduced pressure. The crude residue was purified by prep-TLC (SiO$_2$, PE:EtOAc=1:1) to afford ((4-((tert-butoxycarbonyl)(prop-2-yn-1-yl)amino)-3-methoxyphenyl)sulfonyl)methyl acetate (0.3 g, 754.83 μmol, 77.51% yield) as a yellow oil. MS (ES$^+$, m/z): 342.0.

Example A35: Synthesis of tert-butyl (5-fluoro-2-methoxy-4-(methylcarbamoyl)phenyl)(prop-2-yn-1-yl)carbamate

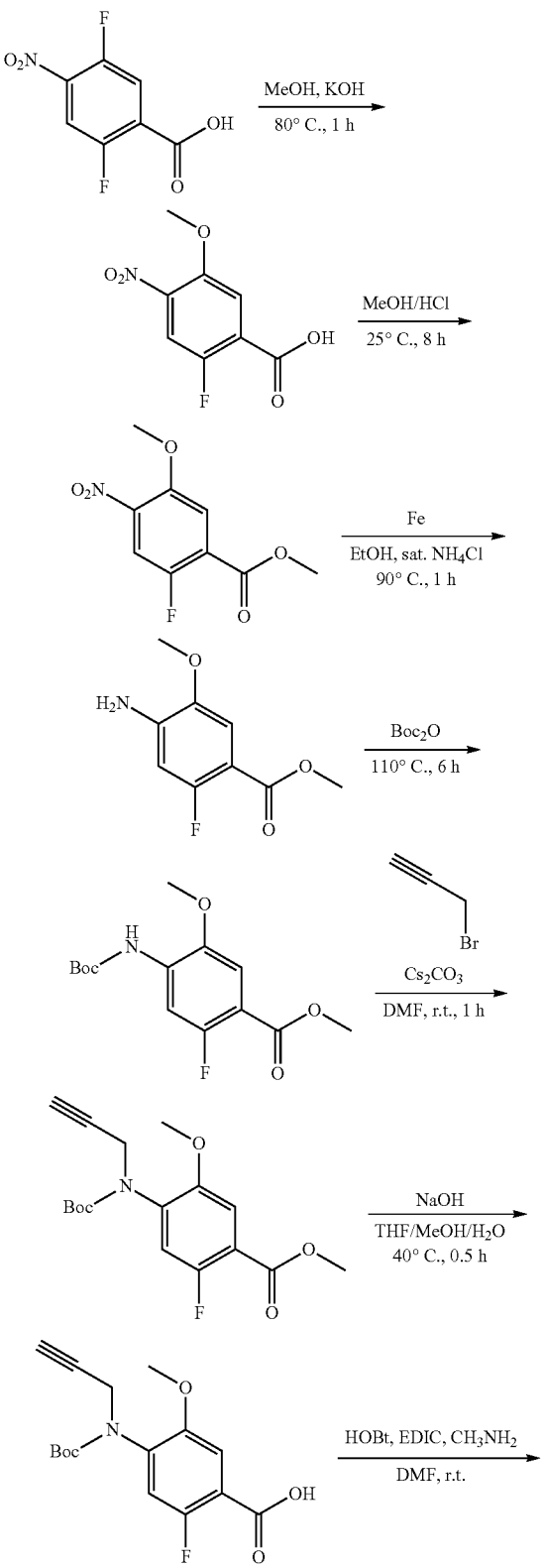

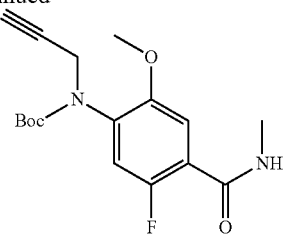

Preparation of 2-fluoro-5-methoxy-4-nitro-benzoic acid: A mixture of 2,5-difluoro-4-nitro-benzoic acid (20 g, 98.47 mmol, 1 eq.) in MeOH (200 mL) was added dropwise KOH (16.57 g, 295.42 mmol, 3 eq.) in MeOH (50 mL) at 80° C. The mixture was stirred at 80° C. for 1 h. TLC analysis (SiO$_2$, DCM:MeOH:AcOH=400:20:1, R$_f$=0.6) indicated that the starting material was consumed completely. 6M HCl was added dropwise into the mixture to adjust the pH of the solution to pH<2. The mixture was then concentrated under reduced pressure to remove MeOH. The mixture was diluted with water (200 mL) and EtOAc (200 mL) and extracted with EtOAc (200 mL×3). The combined organic layers were washed with brine (200 mL×3), dried over anhydrous sodium sulfate, filtered, and concentrated under reduced pressure to give a crude product. The crude product was used directly in the next step without purification. $^1$H NMR (400 MHz, DMSO-d$_6$) δ 8.02-7.99 (d, J=9.6 Hz, 1H), 7.67-7.66 (d, J=5.6 Hz, 1H), 3.956 (s, 3H).

Preparation of methyl 2-fluoro-5-methoxy-4-nitro-benzoate: A mixture of 2-fluoro-5-methoxy-4-nitro-benzoic acid (19.5 g, 90.64 mmol, 1 eq.) in HCl/MeOH (4 M, 195 mL, 8.61 eq.) was stirred at 25° C. for 8 h. TLC (SiO$_2$, PE:EtOAc=2:1, R$_f$=0.5) indicated the starting material was consumed completely. The reaction mixture was concentrated under reduced pressure to remove solvent to give a residue. The crude product (19 g) was obtained as a yellow solid and used in the next step without purification. $^1$H NMR (400 MHz, DMSO-d$_6$) δ 8.21-8.20 (d, J=4.0 Hz, 1H), 7.50-7.48 (d, J=8.0 Hz, 1H), 4.01 (s, 3H), 3.71 (s, 3H).

Preparation of methyl 4-amino-2-fluoro-5-methoxy-benzoate: To a solution of methyl 2-fluoro-5-methoxy-4-nitro-benzoate (19 g, 82.91 mmol, 1 eq.) and NH$_4$Cl (26.61 g, 497.46 mmol, 6 eq.) in EtOH (200 mL) and water (40 mL) was added Fe (13.89 g, 248.73 mmol, 3 eq.) at 90° C., and the resulting mixture was stirred for 1 h. LC-MS analysis showed that 23% of the nitro starting material remained, several new peaks were observed, and 22% of desired compound was detected. Fe (9.26 g, 165.82 mmol, 2 eq.) was added into the mixture, and the mixture was stirred further at 90° C. for 2 h. TLC analysis indicated that the starting material was consumed completely. The mixture was diluted with EtOH (200 mL) and filtered through a pad of diatomaceous earth. The filtrate was concentrated under reduced pressure to give the crude product, which was purified by column chromatography (SiO$_2$, PE:EtOAc=30:1 to PE:EtOAc:DCM=30:2:3, R$_f$=0.5). Methyl 4-amino-2-fluoro-5-methoxy-benzoate (17 g, 80.23 mmol, 53.27% yield) was obtained as light yellow solid. $^1$H NMR (400 MHz, DMSO-d$_6$) δ 7.16-7.15 (d, J=2.0 Hz, 1H), 6.02-6.01 (d, J=6.4 Hz, 1H), 3.74 (s, 3H), 3.41 (s, 3H). MS (ES$^+$, m/z): 199.1.

Preparation of Methyl 4-(tert-butoxycarbonylamino)-2-fluoro-5-methoxy-benzoate: A mixture of methyl 4-amino-2-fluoro-5-methoxy-benzoate (16 g, 80.33 mmol, 1 eq.) and Boc$_2$O (152 g, 696.46 mmol, 160 mL, 8.67 eq.) was stirred at 110° C. for 6 h. TLC analysis (SiO$_2$, PE:EtOAc=4:1, R$_f$=0.6) indicated that 10% of the starting material was remained, and one major new spot with polarity lower than that of the starting material was detected. The reaction mixture was concentrated under reduced pressure to remove solvent to give a residue. The residue was purified by column chromatography (SiO$_2$, PE:EtOAc=60:1 to 50:1, R$_f$=0.6). Methyl 4-(tert-butoxycarbonylamino)-2-fluoro-5-methoxy-benzoate (17 g, 51.12 mmol, 63.64% yield) was obtained as a light yellow solid. $^1$H NMR (400 MHz, DMSO-d$_6$) δ 8.45 (s, 1H), 7.62 (d, J=6.0 Hz, 1H), 7.45 (d, J=5.6 Hz, 1H), 3.90 (s, 3H), 3.80 (s, 3H), 1.48 (s, 6H).

Preparation of methyl 4-((tert-butoxycarbonyl)(prop-2-yn-1-yl)amino)-2-fluoro-5-methoxybenzoate: A mixture of methyl 4-(tert-butoxycarbonylamino)-2-fluoro-5-methoxy-benzoate (15 g, 45.11 mmol, 1 eq.) and Cs$_2$CO$_3$ (29.39 g, 90.21 mmol, 2 eq.) in DMF (110 mL) was added propargyl bromide (10.73 g, 90.21 mmol, 7.78 mL, 2 eq.). The mixture was stirred at 25° C. for 1 h. TLC (SiO$_2$, PE:EtOAc=8:1, Rf=0.5) indicated the starting material was consumed completely. The mixture was diluted with water (500 mL). The mixture was extracted with EtOAc (200 mL×3). The combined organic layers were washed with saturated brine (200 mL×3), dried over anhydrous sodium sulfate, filtered, and concentrated under reduced pressure to give a crude product. The residue was purified by column chromatography (SiO$_2$, PE:EtOAc=0:1) to give methyl 4-((tert-butoxycarbonyl)(prop-2-yn-1-yl)amino)-2-fluoro-5-methoxybenzoate. 1H NMR (400 MHz, DMSO-d6) δ 7.45 (d, J=2.4 Hz, 1H), 7.30 (d, J=5.6 Hz, 1H), 7.35 (s, 2H), 3.90 (s, 3H), 3.80 (s, 3H), 3.20 (s, 1H), 1.35 (s, 6H).

Preparation of 4-((tert-butoxycarbonyl)(prop-2-yn-1-yl)amino)-2-fluoro-5-methoxybenzoic acid: To a solution of methyl 4-((tert-butoxycarbonyl)(prop-2-yn-1-yl)amino)-2-fluoro-5-methoxybenzoate (2 g, 5.93 mmol, 1 eq.) in THF (5 mL), MeOH (5 mL), and water (5 mL) was added NaOH (474.26 mg, 11.86 mmol, 2 eq.). The mixture was stirred for 0.5 h at 40° C. TLC analysis showed that the reaction was complete. The reaction was quenched with water (50 mL), and the pH of the mixture was adjusted to 3 using 1N HCl. The resulting mixture was filtered and concentrated to afford 4-((tert-butoxycarbonyl)(prop-2-yn-1-yl)amino)-2-fluoro-5-methoxybenzoic acid as a light-yellow solid.

Preparation of tert-butyl (5-fluoro-2-methoxy-4-(methylcarbamoyl)phenyl)(prop-2-yn-1-yl)carbamate: To a solution of 4-((tert-butoxycarbonyl)(prop-2-yn-1-yl)amino)-2-fluoro-5-methoxybenzoic acid (1.7 g, 5.26 mmol, 1 eq.) in DMF (15 mL) were added HOBt (1.42 g, 10.52 mmol, 2 eq.), EDIC (2.02 g, 10.52 mmol, 2 eq.), DIPEA (2.04 g, 15.77 mmol, 2.75 mL, 3 eq.) and methanamine (1.07 g, 15.77 mmol, 3 eq., HCl salt). The mixture was stirred for 1 h at 25° C. under N$_2$. TLC analysis showed that the reaction was complete. The reaction was quenched with water (50 mL) and extracted with EtOAc (30 mL). The combined organic layers were washed with brine (30 mL×3), dried over anhydrous sodium sulfate, filtered, and concentrated in vacuo. The crude residue was purified by column chromatography (SiO$_2$, PE:EtOAc=4:1 to 2:1) to afford tert-butyl (5-fluoro-2-methoxy-4-(methylcarbamoyl)phenyl)(prop-2-yn-1-yl)carbamate (1.6 g, 4.76 mmol, 90.47% yield) as a yellow oil.

Example A36: Synthesis of 3-methoxy-N,N-dimethyl-4-(prop-2-yn-1-ylamino)benzenesulfonamide

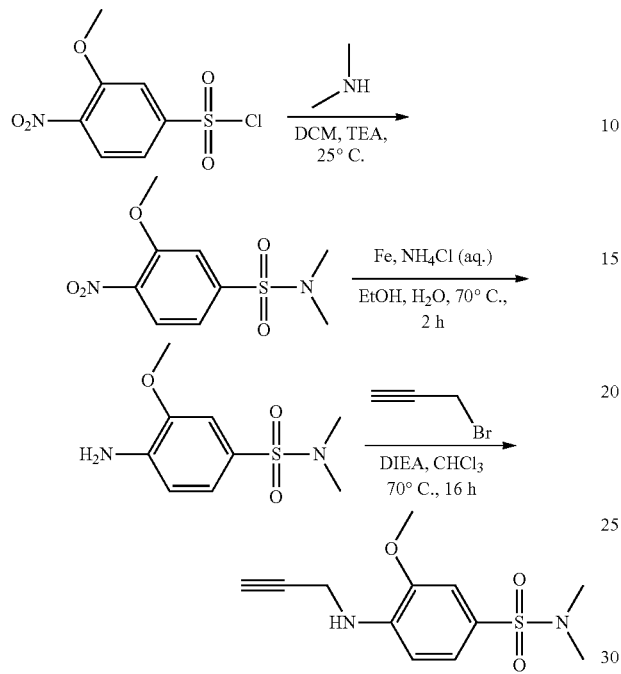

Preparation of 3-methoxy-N,N-dimethyl-4-nitrobenzenesulfonamide: A solution of dimethylamine (145.82 mg, 1.79 mmol, 1.5 eq.) in DCM (1 mL) was added into TEA (241.27 mg, 2.38 mmol, 331.87 µL, 2 eq.). The resulting mixture was then added dropwise to a solution of 3-methoxy-4-nitrobenzenesulfonyl chloride (300 mg, 1.19 mmol, 1 eq.) in DCM and stirred at 25° C. for 2 h. TLC analysis (PE:EtOAc=3:1, $R_f$=0.40) indicated that the reaction was complete. The mixture was quenched with water (40 mL) and extracted with EtOAc (20 mL×3). The combined organic layers were dried over anhydrous sodium sulfate, filtered, and concentrated under reduced pressure. The crude residue was purified by prep-TLC (SiO$_2$, PE:EtOAc=3:1) to afford 3-methoxy-N,N-dimethyl-4-nitrobenzenesulfonamide (270 mg, 933.66 µmol, 78.32% yield) as a light-yellow solid.

Preparation of 4-amino-3-methoxy-N,N-dimethylbenzenesulfonamide: To a solution of 3-methoxy-N,N-dimethyl-4-nitrobenzenesulfonamide (250 mg, 864.50 µmol, 1 eq.) and solid NH$_4$Cl (231.22 mg, 4.32 mmol, 5 eq.) in EtOH (5 mL) and water (1 mL) was added Fe (482.78 mg, 8.64 mmol, 10 eq.) at 70° C. The mixture was stirred for 2 h. TLC analysis (PE:EtOAc=1:1, $R_f$=0.24) indicated that the reaction was complete. The mixture was quenched with water (60 mL) and extracted with EtOAc (20 mL×3). The combined organic layers were dried over anhydrous sodium sulfate, filtered, and concentrated under reduced pressure to afford 4-amino-3-methoxy-N,N-dimethylbenzenesulfonamide (210 mg, crude) as a light-yellow solid.

Preparation of 3-methoxy-N,N-dimethyl-4-(prop-2-yn-1-ylamino)benzenesulfonamide: A solution of 4-amino-3-methoxy-N,N-dimethylbenzenesulfonamide (330 mg, 1.43 µmol, 1 eq.) in CHCl$_3$ (10 mL) was added into a mixture of 3-bromoprop-1-yne (340.94 mg, 2.87 µmol, 247.06 µL, 2 eq.) and DIPEA (926.02 mg, 7.17 mmol, 1.25 mL, 5 eq.) in CHCl$_3$ (3 mL). The mixture was stirred at 70° C. for 16 h. TLC analysis (PE:EtOAc=1:1, $R_f$=0.43) indicated that the reaction was complete. The mixture was quenched with water (40 mL) and extracted with EtOAc (20 mL×3). The combined organic layers were dried over anhydrous sodium sulfate, filtered, and concentrated under reduced pressure. The residue was purified by prep-TLC (SiO$_2$, PE:EtOAc=1:1) to afford 3-methoxy-N,N-dimethyl-4-(prop-2-yn-1-ylamino)benzenesulfonamide (210 mg, 47.5% yield) as a light-yellow solid. MS (ES$^+$, m/z): 269.2.

Example A37: Synthesis of tert-butyl (2-fluoro-6-methoxy-4-(methylsulfonyl)phenyl)(prop-2-yn-1-yl)carbamate

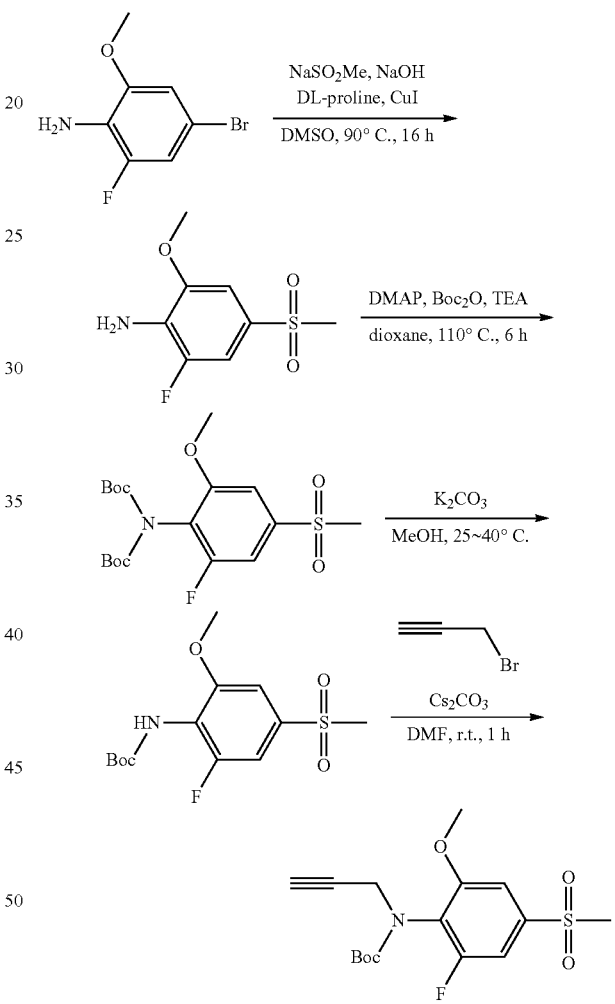

Preparation of 2-fluoro-6-methoxy-4-(methylsulfonyl)aniline: To a solution of 4-bromo-2-fluoro-6-methoxyaniline (626.34 mg, 6.14 mmol, 3 eq.) in DMSO (15 mL) were added DL-proline (117.73 mg, 1.02 mmol, 0.5 eq.), CuI (389.49 mg, 2.05 mmol, 1 eq.), and NaOH (81.80 mg, 2.05 mmol, 1 eq.). The reaction mixture was stirred at 90° C. for 16 h under N$_2$. TLC analysis (PE:EtOAc=2:1, $R_f$=0.5) indicated that the starting material was consumed completely, and one major new spot with lower polarity than that of the starting material was detected. The mixture was diluted with a saturated EDTA solution (100 mL) and extracted with EtOAc (30 mL×3). The combined organic layers were washed with brine (30 mL×3), dried over anhydrous sodium sulfate, filtered, and concentrated under reduced pressure. The crude residue was purified by column chromatography (SiO₂, PE:EtOAc=10:1 to 2:1) to afford the desired product (1.2 g, 5.47 mmol, 89.22% yield) as a white solid.

Preparation of 2-fluoro-6-methoxy-N,N-di(tert-butyloxycarbonyl)-4-(methylsulfonyl)aniline: To a mixture of 2-fluoro-6-methoxy-4-(methylsulfonyl)aniline (1.2 g, 4.93 mmol, 1 eq.) and Boc₂O (4.30 g, 19.71 mmol, 4.53 mL, 4 eq.) in 1,4-dioxane (12 mL) were added DMAP (60.18 mg, 492.63 µmol, 0.1 eq.) and TEA (1.99 g, 19.71 mmol, 2.74 mL, 4 eq.). The reaction mixture was stirred at 110° C. for 6 h. TLC analysis (PE:EtOAc=2:1, $R_f$=0.5) indicated that the starting material was consumed completely, and one major new spot with lower polarity than that of the starting material was detected. The mixture was diluted with water (100 mL) and extracted with EtOAc (30 mL×3). The combined organic layers were washed with brine (30 mL×3), dried over anhydrous sodium sulfate, filtered, and concentrated under reduced pressure. The residue was purified by column chromatography (SiO₂, PE:EtOAc=20:1 to 2:1) to afford the desired product (1.9 g, 4.08 mmol, 82.75% yield) as a yellow oil.

Preparation of tert-butyl (2-fluoro-6-methoxy-4-(methylsulfonyl)phenyl)carbamate: A mixture of 2-fluoro-6-methoxy-N,N-di(tert-butyloxycarbonyl)-4-(methylsulfonyl)aniline (900 mg, 1.93 mmol, 1 eq.) and K₂CO₃ (1.33 g, 9.66 mmol, 5 eq.) in MeOH (10 mL) was stirred at 25° C. for 2 h. The mixture was then heated to 40° C. and stirred further for 2 h. TLC analysis (PE:EtOAc=2:1, $R_f$=0.4) indicated that the starting material was consumed completely, and one major new spot with polarity greater than that of the starting material was detected. The reaction mixture was concentrated under reduced pressure. The crude residue was diluted with water (200 mL) and extracted with EtOAc (70 mL×3). The combined organic layers were washed with brine (30 mL×3), dried over anhydrous sodium sulfate, filtered, and concentrated under reduced pressure. The crude residue (1.6 g, crude) was obtained as a light-yellow solid and used directly in the next step.

Preparation of tert-butyl (2-fluoro-6-methoxy-4-(methylsulfonyl)phenyl)(prop-2-yn-1-yl)carbamate: A mixture of tert-butyl (2-fluoro-6-methoxy-4-(methylsulfonyl)phenyl)carbamate (1.5 g, 4.23 mmol, 1 eq.) and Cs₂CO₃ (2.75 g, 8.45 mmol, 2 eq.) in DMF (16 mL) was stirred at 25° C. for 1 h. TLC analysis (PE:EtOAc=2:1, $R_f$=0.4) indicated that the starting material was consumed completely, and one major new spot with polarity lower than that of the starting material was detected. The mixture was diluted with water (100 mL) and extracted with EtOAc (30 mL×3). The combined organic layers were washed with brine (30 mL×3), dried over anhydrous sodium sulfate, filtered, and concentrated under reduced pressure. The crude residue was purified by column chromatography (SiO₂, PE:EtOAc=20:1 to 4:1) to afford tert-butyl (2-fluoro-6-methoxy-4-(methylsulfonyl)phenyl)(prop-2-yn-1-yl)carbamate (1.9 g, 3.99 mmol, 94.32% yield) as a light-yellow oil.

Example A38: Synthesis of 3-methoxy-N,N-dimethyl-4-(prop-2-yn-1-ylamino)benzenesulfonamide

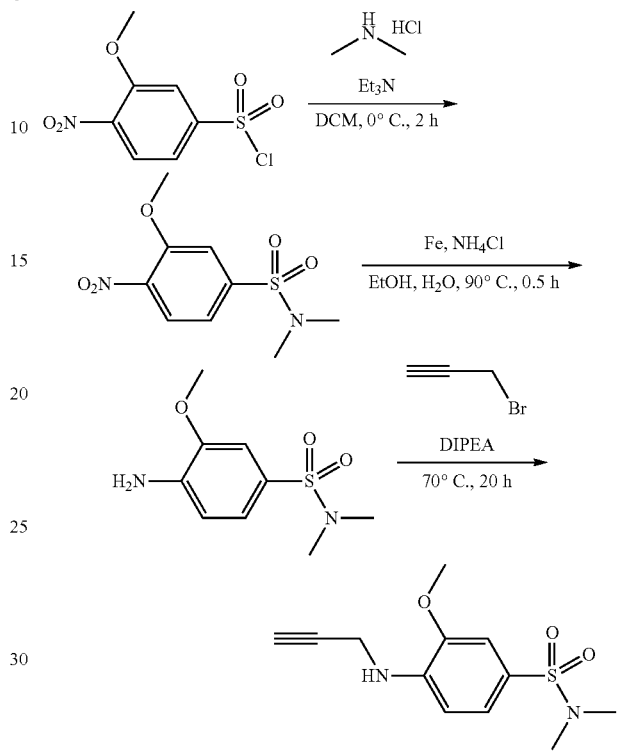

Preparation of 3-methoxy-N,N-dimethyl-4-nitrobenzenesulfonamide: A solution of N-methylmethanamine (194.43 mg, 2.38 mmol, 218.46 µL, 1.2 eq., HCl) in DCM (15 mL) and Et₃N (1.01 g, 9.93 mmol, 1.38 mL, 5 eq.) was prepared under N₂ at 0° C. A solution of 3-methoxy-4-nitrobenzenesulfonyl chloride (500 mg, 1.99 mmol, 1 eq.) in DCM (5 mL) was added dropwise to the mixture, and the mixture was stirred at 20° C. for 2 h. TLC analysis (PE:EtOAc=1:1, $R_f$=0.42) showed that the reaction was complete. The mixture was concentrated in vacuo and purified by column chromatography (SiO₂, PE:EtOAc=20:1 to 0:1, $R_f$=0.42) to afford the desired product (500 mg, 1.86 mmol, 93.69% yield) as a yellow solid. MS (ES⁺, m/z): 261.1.

Preparation of 4-amino-3-methoxy-N,N-dimethylbenzenesulfonamide: To a solution of 3-methoxy-N,N-dimethyl-4-nitrobenzenesulfonamide (450 mg, 1.68 mmol, 1 eq.) in EtOH (15 mL) and water (5 mL) was added NH₄Cl (448.09 mg, 8.38 mmol, 292.87 µL, 5 eq.) under N₂. Fe (467.85 mg, 8.38 mmol, 5 eq.) was added to the mixture at 90° C., and the resulting mixture was stirred at 90° C. for 0.5 h. TLC analysis (PE:EtOAc=1:1, $R_f$=0.39) showed that the reaction was complete. The reaction mixture was subjected to heat filtration, filtered and concentrated in vacuo. The crude residue was purified by column chromatography (SiO₂, PE:EtOAc=10:1 to 0:1, $R_f$=0.39) to afford the desired product (380 mg, 1.54 mmol, 91.99% yield) as a light yellow solid. MS (ES⁺, m/z): 231.0.

Preparation of 3-methoxy-N,N-dimethyl-4-(prop-2-yn-1-ylamino)benzenesulfonamide: To a mixture of 4-amino-3-methoxy-N,N-dimethylbenzenesulfonamide in CHCl₃ (10 mL) were added DIPEA (865.91 mg, 6.70 mmol, 1.17 mL, 5 eq.) and 3-bromoprop-1-yne (797.03 mg, 6.70 mmol, 577.56 µL, 5 eq.). The mixture was degassed and purged with $N_2$ three times at 20° C., and the mixture was stirred at 70° C. for 10 h. Then, DIPEA (346.37 mg, 2.68 mmol, 466.81 µL, 2 eq.) and 3-bromoprop-1-yne (318.81 mg, 2.68 mmol, 231.02 µL, 2 eq.) were added to the mixture, and the resulting mixture was stirred further at 70° C. for 10 h. LC-MS and TLC analysis (PE:EtOAc=1:1, $R_f$=0.50) indicated that 20% of the starting material remained, and one major new spot was detected. The mixture was concentrated in vacuo and purified by column chromatography ($SiO_2$, PE:EtOAc=10:1 to 0:1, $R_f$=0.5) to afford the desired product (120 mg, 290.69 µmol, 21.69% yield) as a light-yellow solid. MS ($ES^+$, m/z): 268.9.

Example A41: Synthesis of 4-methoxy-6-(methylsulfonyl)-N-(prop-2-yn-1-yl)pyridin-3-amine

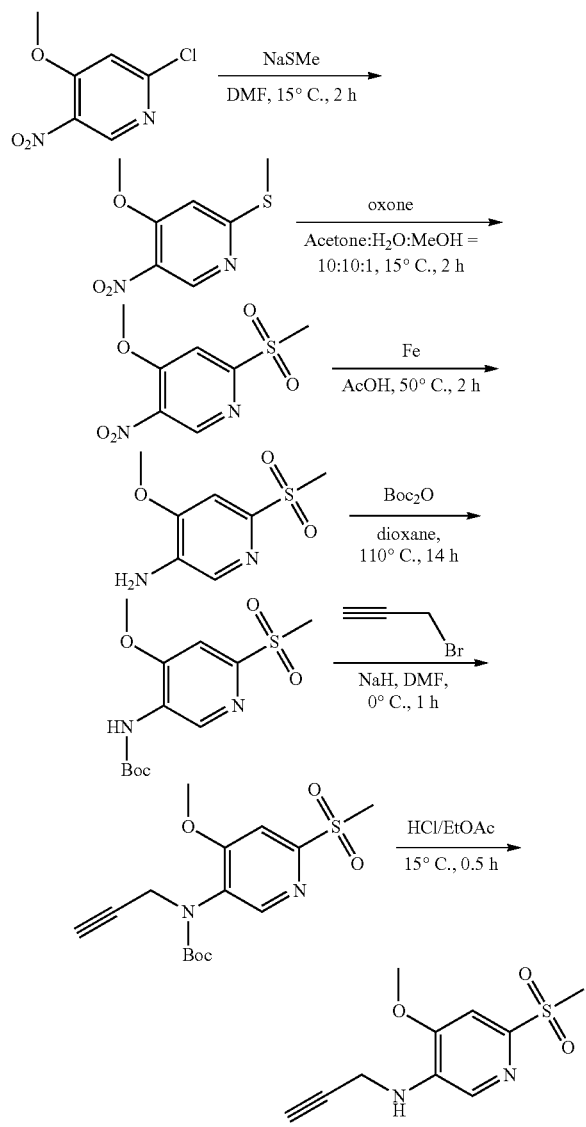

Preparation of 4-methoxy-2-(methylthio)-5-nitropyridine: To a solution of 2-chloro-4-methoxy-5-nitro-pyridine (1.50 g, 7.95 mmol, 1 eq.) in DMF (20 mL) was added NaSMe (3.34 g, 47.70 mmol, 3.04 mL, 6 eq.). The mixture was stirred at 15° C. for 2 h. LC-MS analysis showed that the starting material was consumed completely, and one main peak with the mass of the desired product was detected. The reaction mixture was partitioned by adding water (50 mL) and EtOAc (50 mL). The organic phase was separated, washed with brine (10 mL×3), dried over anhydrous sodium sulfate, filtered, and concentrated under reduced pressure to afford the desired product (1.30 g, 6.49 mmol, 81.68% yield) as a brown solid. MS ($ES^+$, m/z): 200.8.

Preparation of 4-methoxy-2-(methylsulfonyl)-5-nitropyridine: To a solution of 4-methoxy-2-(methylthio)-5-nitropyridine (1.30 g, 6.49 mmol, 1 eq.) in acetone (20 mL), MeOH (2 mL) and water (20 mL) was added oxone (11.98 g, 19.48 mmol, 3 eq.). The mixture was stirred at 0~15° C. for 2 h. LC-MS analysis showed that the starting material was consumed completely, and one main peak with the desired mass was detected. The reaction mixture was partitioned using a saturated $Na_2S_2O_4$ solution (100 mL) and EtOAc (100 mL). The organic phase was separated, washed with brine (30 mL×3), dried over anhydrous sodium sulfate, filtered, and concentrated under reduced pressure to afford the desired product (1.45 g, 5.68 mmol, 87.56% yield) as a yellow solid. MS ($ES^+$, m/z): 233.1.

Preparation of 4-methoxy-6-(methylsulfonyl)pyridin-3-amine: To a solution of 4-methoxy-2-methylsulfonyl-5-nitro-pyridine (1 g, 4.31 mmol, 1 eq.) in AcOH (20 mL) was added Fe (2.41 g, 43.10 mmol, 10 eq.). The mixture was stirred at 50° C. for 2 h. LC-MS analysis showed that the starting material was consumed completely, and one main peak with the desired mass was detected. The reaction mixture was partitioned by adding water (100 mL) and EtOAc (100 mL). The organic phase was separated, washed with brine (30 mL×3), dried over anhydrous sodium sulfate, filtered, and concentrated under reduced pressure to give a residue. The residue was purified by column chromatography ($SiO_2$, PE:EtOAc=10:1 to 1:1) to afford the desired product (510 mg, 2.52 mmol, 58.51% yield) as a brown solid. MS ($ES^+$, m/z): 202.8.

Preparation of tert-butyl (4-methoxy-6-(methylsulfonyl)pyridin-3-yl)carbamate: To a solution of 4-methoxy-6-(methylsulfonyl)pyridin-3-amine (650 mg, 3.21 mmol, 1 eq.) in dioxane (10 mL) was added $Boc_2O$ (4.20 g, 19.26 mmol, 4.42 mL, 6 eq.). The mixture was stirred at 110° C. for 14 h. LC-MS analysis showed that the starting material was consumed completely, and one main peak with the desired mass was detected. The reaction mixture was concentrated under reduced pressure to give a residue. The residue was purified by column chromatography ($SiO_2$, PE:EtOAc=10:1 to 1:1) to afford the desired product (0.65 g, 2.15 mmol, 66.97% yield) as a yellow oil. MS ($ES^+$, m/z): 302.9.

Preparation of tert-butyl (4-methoxy-6-(methylsulfonyl)pyridin-3-yl)(prop-2-yn-1-yl)carbamate: To a mixture of NaH (529.20 mg, 13.23 mmol, 60% in mineral oil, 10 eq.) in DMF (4 mL) was added tert-butyl (4-methoxy-6-(methylsulfonyl)pyridin-3-yl)carbamate (400 mg, 1.32 mmol, 1 eq.). The mixture was stirred at 0° C. for 30 min, and 3-bromoprop-1-yne (236.07 mg, 1.98 mmol, 171.07 µL, 1.50 eq.) was added to the mixture. LC-MS analysis showed that the starting material was consumed completely, and one main peak with the desired mas was detected. The reaction mixture was partitioned by adding water (40 mL) and EtOAc (40 mL). The organic phase was separated, washed with brine (10 mL×3), dried over anhydrous sodium sulfate, filtered, and concentrated under reduced pressure to give a residue. The residue was purified by column chromatography (SiO$_2$, PE:EtOAc=10:1 to 1:1) to afford the desired product (250 mg, 734.44 μmol, 55.51% yield) as a yellow oil. MS (ES$^+$, m/z): 341.2.

Preparation of 4-methoxy-6-(methylsulfonyl)-N-(prop-2-yn-1-yl)pyridin-3-amine: To a solution of tert-butyl (4-methoxy-6-(methylsulfonyl)pyridin-3-yl)(prop-2-yn-1-yl)carbamate (170 mg, 499.42 μmol, 1 eq.) was added HCl/EtOAc (4 M, 2.02 mL, 16.17 eq.). The mixture was stirred at 15° C. for 1 h. LC-MS analysis showed that the starting material was consumed completely, and one main peak with the desired mass was detected. The reaction mixture was concentrated under reduced pressure to afford the desired product (100 mg, 361.35 μmol, 72.35% yield, HCl) was obtained as a brown solid. MS (ES$^+$, m/z): 241.1.

Example A42: Synthesis of 2-(4-methoxy-5-(prop-2-yn-1-ylamino)pyridin-2-yl)-2-methylpropanenitrile Route 1:

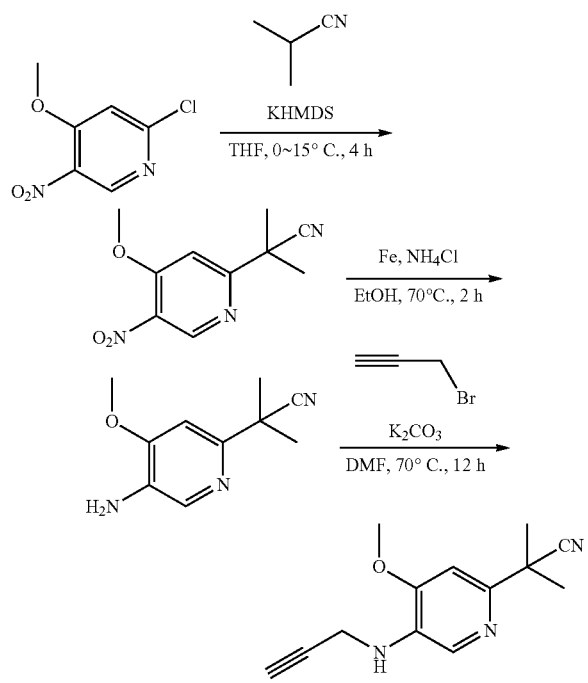

Preparation of 2-(4-methoxy-5-nitropyridin-2-yl)-2-methylpropanenitrile: To a solution of 2-chloro-4-methoxy-5-nitropyridine (2 g, 10.61 mmol, 1 eq.) in THF (5 mL) was added KHMDS (1 M, 53.03 mL, 5 eq.) drop-wise at 0° C. under N$_2$. Then, isobutyronitrile (2.20 g, 31.82 mmol, 3 eq.) was added, and the resulting mixture was stirred at 0° C. for 2 h. TLC analysis (PE:EtOAc=1:1) showed that the starting material was consumed completely. The reaction was quenched by adding ice slowly, and the mixture was extracted with EtOAc (10 mL×2). The combined organic layers were washed with brine (10 mL), dried over anhydrous sodium sulfate, filtered, and concentrated in vacuo. The residue was purified by column chromatography (SiO$_2$, PE:EtOAc=10:1 to 1:1) to afford 2-(4-methoxy-5-nitropyridin-2-yl)-2-methylpropanenitrile (0.66 g, 2.98 mmol, 28.13% yield) as a yellow solid.

Preparation of 2-(5-amino-4-methoxypyridin-2-yl)-2-methylpropanenitrile: To a solution of 2-(4-methoxy-5-nitropyridin-2-yl)-2-methylpropanenitrile (0.35 g, 1.58 mmol, 1 eq.) in EtOH (5 mL) and water (1 mL) were added NH$_4$Cl (423.16 mg, 7.91 mmol, 276.57 μL, 5 eq.), and Fe (441.83 mg, 7.91 mmol, 5 eq.) in order at 90° C. under N$_2$. The mixture was heated to 90° C. and stirred for 1 h. TLC analysis showed that the reaction was complete. The mixture was filtered and concentrated under reduced pressure. The residue was poured into a mixture of DCM and water (w/w=1:1) (20 mL) and stirred for 30 min. The aqueous phase was extracted with DCM (5 mL×2). The combined organic layers were washed with brine (5 mL), dried over anhydrous sodium sulfate, filtered, and concentrated in vacuo. The residue was purified by prep-TLC (SiO$_2$, PE:EtOAc=1:1) to afford the desired product (0.22 g, 1.15 mmol, 72.71% yield) as a yellow solid.

Preparation of 2-(4-methoxy-5-(prop-2-yn-1-ylamino)pyridin-2-yl)-2-methylpropanenitrile: To a mixture of 2-(5-amino-4-methoxypyridin-2-yl)-2-methylpropanenitrile (0.24 g, 1.26 mmol, 1 eq.) and 3-bromoprop-1-yne (746.50 mg, 6.28 mmol, 540.94 μL, 5 eq.) in DMF (5 mL) was added K$_2$CO$_3$ (520.36 mg, 3.77 mmol, 3 eq.) in one portion at 25° C. under N$_2$. The mixture was stirred at 70° C. for 12 h. LC-MS and TLC analysis (PE:EtOAc=1:1, R$_f$=0.45) showed that the reaction was complete. The mixture was poured into water (50 mL) and stirred for 2 min. The aqueous phase was extracted with EtOAc (20 mL×3). The combined organic layers were washed with brine (20 mL), dried over anhydrous sodium sulfate, filtered, and concentrated in vacuo. The crude residue was purified by silica gel chromatography (PE:EtOAc=10:1 to 0:1) to afford the desired product (0.255 g, 889.75 μmol, 70.89% yield) as a yellow solid. MS (ES$^+$, m/z): 230.0.

Route 2:

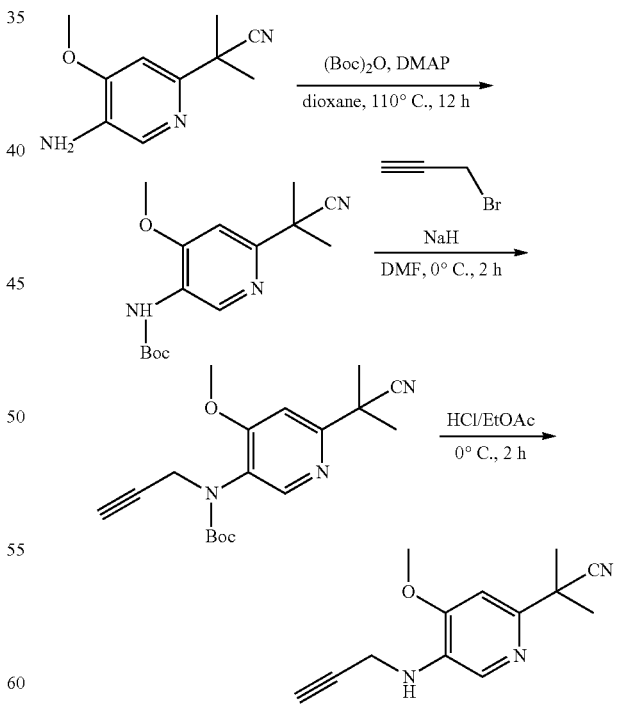

Preparation of tert-butyl (6-(2-cyanopropan-2-yl)-4-methoxypyridin-3-yl)carbamate: To a solution of 2-(5-amino-4-methoxypyridin-2-yl)-2-methylpropanenitrile (0.15 g, 784.40 μmol, 1 eq.) in dioxane (5 mL) were added (Boc)$_2$O (855.96 mg, 3.92 mmol, 901.01 μL, 5 eq.) and DMAP (191.66 mg, 1.57 mmol, 2 eq.) in one portion at 25° C. under N₂. The mixture was stirred at 110° C. for 12 h. LC-MS analysis showed that the reaction was complete, and a di-Boc byproduct was detected. The mixture was cooled to 25° C. and concentrated under reduced pressure at 50° C. The residue was added to solution of 500 mg solid Na₂CO₃ in MeOH (10 mL) to convert the di-Boc byproduct to the desired mono-Boc-protected product. The mixture was stirred at 40° C. for 2 h. The mixture was cooled to 25° C. and concentrated under reduced pressure at 40° C. The crude residue was purified by silica gel chromatography (PE: EtOAc=30:1 to 3:1) to afford the desired product (0.18 g, 586.93 μmol, 74.83% yield) as a colorless oil. MS (ES⁺, m/z): 291.9.=

Preparation of tert-butyl (6-(2-cyanopropan-2-yl)-4-methoxypyridin-3-yl)(prop-2-yn-1-yl)carbamate: To a mixture of tert-butyl (6-(2-cyanopropan-2-yl)-4-methoxypyridin-3-yl)carbamate (0.18 g, 617.82 μmol, 1 eq.) in DMF (2 mL) was added NaH (37.07 mg, 926.74 μmol, 60% in mineral oil, 1.5 eq.) in one portion at 0° C. under N₂. The mixture was stirred at 0° C. for 30 min, then 3-bromoprop-1-yne (88.20 mg, 741.39 μmol, 63.91 μL, 1.2 eq.) was added in one portion at 0° C. under N₂. The mixture was stirred at 0° C. for 1.5 h. LC-MS analysis showed that the reaction was complete. The mixture was poured into water (20 mL) and stirred for 2 min. The aqueous phase was extracted with EtOAc (10 mL×2). The combined organic layers were washed with brine (10 mL), dried over anhydrous sodium sulfate, filtered, and concentrated in vacuo. The crude residue was purified by silica gel chromatography (PE: EtOAc=30:1 to 3:1) to afford the desired product (0.15 g, 432.61 μmol, 70.02% yield) as a colorless oil. MS (ES⁺, m/z): 329.9.

Preparation of 2-(4-methoxy-5-(prop-2-yn-1-ylamino) pyridin-2-yl)-2-methylpropanenitrile: A solution of tert-butyl (6-(2-cyanopropan-2-yl)-4-methoxypyridin-3-yl) (prop-2-yn-1-yl)carbamate (120 mg, 364.31 μmol, 1 eq.) in HCl/EtOAc (5 mL) was prepared at 0° C. under N₂ and stirred at 0° C. for 2 h. TLC analysis (PE:EtOAc=3:1, R𝒻=0) showed that the reaction was complete. The mixture was poured into a saturated Na₂CO₃ solution (50 mL) and stirred for 2 min. The aqueous phase was extracted with EtOAc (10 mL×3). The combined organic layers were washed with brine (10 mL), dried over anhydrous sodium sulfate, filtered and concentrated in vacuo. The crude residue was purified by prep-TLC (PE:EtOAc=3:1, R𝒻=0.4) to afford the desired product (100 mg, 417.88 μmol) as a white solid. MS (ES⁺, m/z): 230.3.

Example A43: Synthesis of 3-methoxy-4-(prop-2-yn-1-ylamino)benzoic acid

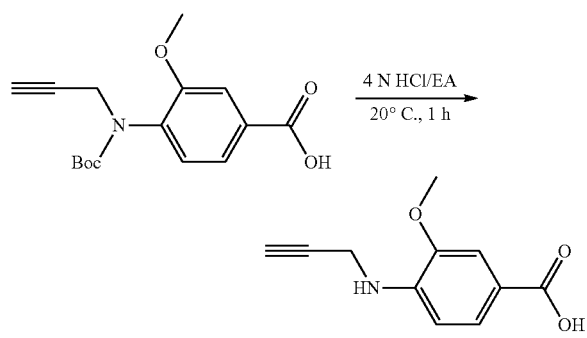

A solution of 4-[tert-butoxycarbonyl(prop-2-ynyl)amino]-3-methoxy-benzoic acid (1.1 g, 3.60 mmol, 1 eq.) in 4 N HCl/EtOAc (50 mL) was stirred at 20° C. for 2 h. TLC analysis (PE:EtOAc=1:1, R𝒻=0.5) showed that the starting material was consumed. The mixture was concentrated to afford the crude product (0.8 g, 3.51 mmol, 97.39% yield) as a yellow solid. The crude product was used without purification.

Example A44: Synthesis of methyl 3-methoxy-4-(prop-2-yn-1-ylamino)benzoate

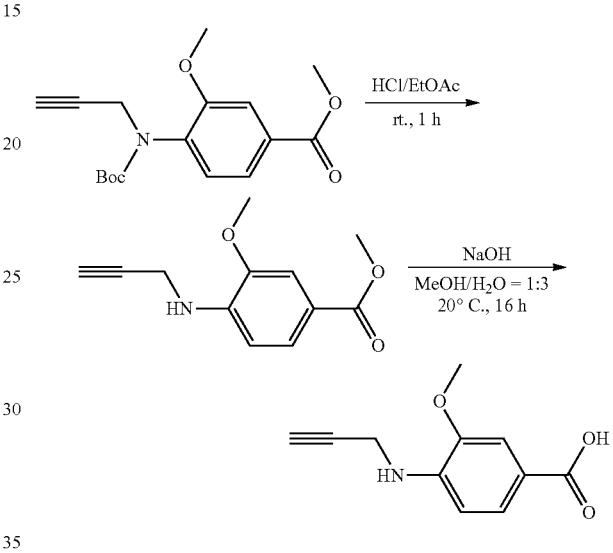

Preparation of methyl 3-methoxy-4-(prop-2-yn-1-ylamino)benzoate: A solution of methyl 4-((tert-butoxycarbonyl)(prop-2-yn-1-yl)amino)-3-methoxybenzoate in 4N HCl in EtOAc (20 mL) was degassed and purged with N₂ three times. The mixture was then stirred at 20° C. for 1 h under N₂. TLC analysis (PE:EtOAc=3:1, R𝒻=0.55) indicated that the starting material was consumed, and one new spot had formed. The reaction mixture was quenched by adding a saturated NaHCO₃ solution (30 mL) and was extracted with EtOAc (40 mL×3). The combined organic layers were washed with brine (25 mL×3), dried over anhydrous sodium sulfate, filtered, and concentrated under reduced pressure. The crude product (0.58 g, 2.12 mmol, 67.59% yield) was obtained as a yellow solid and used without purification.

Preparation of 3-methoxy-4-(prop-2-yn-1-ylamino)benzoic acid: A solution of methyl 3-methoxy-4-(prop-2-yn-1-ylamino)benzoate in MeOH and water (10 mL, MeOH: water=1:3) was degassed and purged with N₂ three times. The solution was stirred at 20° C. for 1 h under N₂. TLC analysis (PE:EtOAc=3:1, R𝒻=0) indicated that the starting material remained, and one major new spot was detected. The reaction mixture was extracted with EtOAc (50 mL×2), and the pH of the mixture was adjusted to 3~4 by adding 2M HCl. The organic layer was washed with brine (50 mL×3), dried over anhydrous sodium sulfate, filtered, and concentrated under reduced pressure to afford the desired product (0.6 g, 2.34 mmol, 42.73% yield) as a yellow solid.

Example A45: Synthesis of 3-methoxy-4-(prop-2-yn-1-ylamino)benzamide

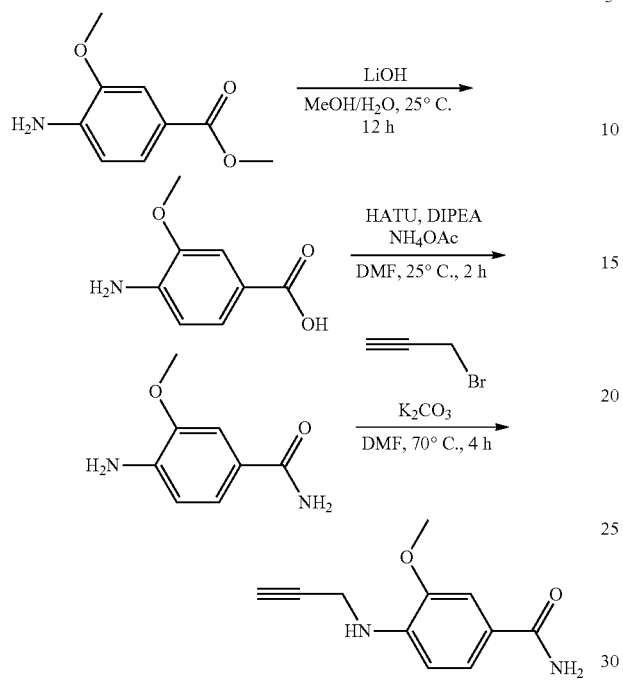

Preparation of 4-amino-3-methoxybenzoic acid: To a solution of methyl 4-amino-3-methoxybenzoate (4.5 g, 23.59 mmol, 1 eq.) in MeOH (45 mL), water (15 mL), and THF (15 mL) was added LiOH (4.95 g, 117.97 mmol, 5 eq.) in one portion at 25° C. under $N_2$. The mixture was stirred at 25° C. for 12 h. TLC analysis (PE:EtOAc=3:1, $R_f$=0) showed that the reaction was complete. The mixture was concentrated under reduced pressure at 40° C. The residue was poured into water (50 mL) and stirred for 1 min. The aqueous phase was extracted with EtOAc (30 mL×3). 2 N HCl was added to the aqueous phase to adjust the pH of the solution to 2. The aqueous phase was filtered and concentrated in vacuo to afford the desired product (4 g, 22.73 mmol, 96.35% yield) as a light yellow solid.

Preparation of 4-amino-3-methoxybenzamide: To a solution of 4-amino-3-methoxybenzoic acid (4 g, 22.73 mmol, 1 eq., 95% purity) in DMF (50 mL) were added $NH_4OAc$ (8.76 g, 113.66 mmol, 5 eq.), DIPEA (29.38 g, 227.32 mmol, 39.60 mL, 10 eq.), and HATU (17.29 g, 45.46 mmol, 2 eq.) in one portion at 25° C. under $N_2$. The mixture was stirred at 25° C. for 2 h. TLC analysis (PE:EtOAc=0:1, $R_f$=0.30) showed that the reaction was complete. The mixture was poured into water (800 mL) and stirred for 2 min. The aqueous phase was extracted with EtOAc (300 mL×3). The combined organic layers were washed with brine (300 mL×1), dried over anhydrous sodium sulfate, filtered, and concentrated in vacuo. The residue was purified by silica gel chromatography ($SiO_2$, PE:EtOAc=100:1 to 0:1) to afford the desired product (5 g, 18.05 mmol, 79.42% yield) as a yellow oil.

Preparation of 3-methoxy-4-(prop-2-yn-1-ylamino)benzamide: To a mixture of 4-amino-3-methoxybenzamide (5 g, 18.05 mmol, 1 eq., 60% purity) and 3-bromoprop-1-yne (4.52 g, 36.11 mmol, 3.28 mL, 2 eq., 95% purity) in DMF (50 mL) was added $K_2CO_3$ (7.49 g, 54.16 mmol, 3 eq.) in one portion at 25° C. under $N_2$. The mixture was stirred at 70° C. for 4 h. TLC analysis (PE:EtOAc=0:1, $R_f$=0.40) showed that the reaction was complete. The mixture was cooled to 25° C., and the residue was poured into water (500 mL) and stirred for 2 min. The aqueous phase was extracted with EtOAc (200 mL×3). The combined organic layers were washed with brine (300 mL×1), dried over anhydrous sodium sulfate, filtered, and concentrated in vacuo. The residue was purified by silica gel chromatography ($SiO_2$, PE:EtOAc=100:1 to 0:1) to afford the desired product (3.32 g, 12.19 mmol, 67.54% yield) as a yellow solid.

Example A46: Synthesis of 2-((3-methoxy-4-(prop-2-yn-1-ylamino)phenyl)sulfonyl)ethan-1-ol

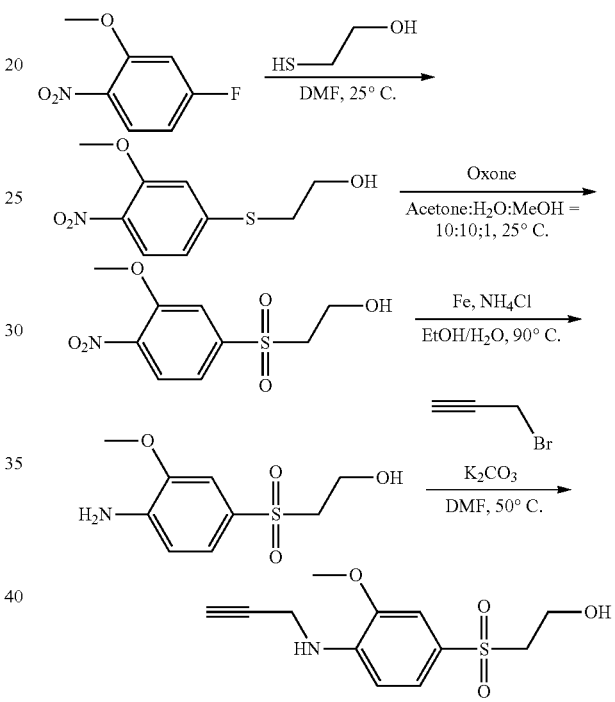

Preparation of 2-((3-methoxy-4-nitrophenyl)thio)ethan-1-ol: A solution of 4-fluoro-2-methoxy-1-nitrobenzene (1.24 g, 11.69 mmol, 1 eq.) and 2-mercaptoethan-1-ol (1.83 g, 23.37 mmol, 1.63 mL, 2 eq.) was degassed and purged with $N_2$ three times. The mixture was stirred at 25° C. for 19 h under $N_2$. TLC analysis (PE:EtOAc=5:1, $R_f$=0.05; DCM:MeOH=10:1, $R_f$=0.45) showed that the reaction was complete. The residue was poured into water (200 mL) and was stirred for 30 min. The mixture was filtered and concentrated in vacuo. The residue was poured into water (200 mL) and extracting the mixture with EtOAc (100 mL×3). The combined organic layers were washed with brine (80 mL×3), filtered and concentrated in vacuo. The crude product (2.8 g, crude) was obtained as a yellow solid and used without purification.

Preparation of 2-((3-methoxy-4-nitrophenyl)sulfonyl)ethan-1-ol: To a solution of 2-((3-methoxy-4-nitrophenyl)thio)ethan-1-ol (2.8 g, 12.21 mmol, 1 eq.) in acetone (40 mL), water (40 mL), and MeOH (4 mL) was added oxone (15.02 g, 24.43 mmol, 2 eq.). The mixture was stirred at 25° C. for 2 h. TLC analysis (DCM:MeOH=10:1, $R_f$=0.4) indicated that the starting material was consumed completely, and one new spot was detected. The residue was poured into a saturated solution of Na₂SO₃ (300 mL) and stirred for 30 min. The mixture was filtered and concentrated in vacuo. The residue was poured into a saturated Na₂SO₃ solution (300 mL) and stirred for 30 min and extracting the mixture with EtOAc (100 mL×3). The combined organic layers were washed with brine (80 mL×3), filtered and concentrated in vacuo. The crude product (3 g, crude) was obtained as a white solid and used without purification.

Preparation of 2-((4-amino-3-methoxyphenyl)sulfonyl)ethan-1-ol: A solution of 2-((3-methoxy-4-nitrophenyl)sulfonyl)ethan-1-ol (3 g, 11.48 mmol, 1 eq.) in EtOH (20 mL) and water (4 mL) were added NH₄Cl (3.69 g, 68.90 mmol, 6 eq.) and Fe (1.92 g, 34.45 mmol, 3 eq.) at 90° C. The mixture was stirred at 90° C. for 0.5 h. TLC analysis (DCM:MeOH=10:1, $R_f$=0.5) indicated that 50% of the starting material remained, and two major new spots with polarity greater than that of the starting material were detected. An additional portion of Fe (1.28 g, 22.97 mmol, 2 eq.) was added into the mixture, and the mixture was stirred at 90° C. for 1 h. TLC analysis (DCM:MeOH=10:1, $R_f$=0.5) indicated that the starting material was consumed completely, and one major new spot with polarity greater than that of the starting material was detected. The residue was diluted with EtOAc (400 mL). The mixture was diluted with water (400 mL) and extracted with EtOAc (200 mL×3). The combined organic layers were washed with brine (200 mL×3), dried over anhydrous sodium sulfate, filtered, and concentrated under reduced pressure. The crude product (2.8 g, crude) was obtained as a white oil. MS (ES⁺, m/z): 232.0. 1H NMR (400 MHz, DMSO-d6) δ ppm 3.27-3.35 (m, 2H) 3.60-3.68 (m, 2H) 3.80-3.88 (m, 3H) 4.78-4.87 (m, 1H) 5.67-5.81 (m, 2H) 6.69-6.77 (m, 1H) 7.13-7.18 (m, 1H) 7.18-7.24 (m, 1H).

Preparation of 2-((3-methoxy-4-(prop-2-yn-1-ylamino)phenyl)sulfonyl)ethan-1-ol: To a solution of 2-((4-amino-3-methoxyphenyl)sulfonyl)ethan-1-ol (0.15 g, 648.6 µmol, 1 eq.) in DMF (1 mL) were added K₂CO₃ (179.3 mg, 1.30 mmol, 2 eq.) and 3-bromoprop-1-yne (67.51 mg, 454.02 µmol, 48.92 µL, 0.7 eq.). The mixture was degassed and purged with N₂ three times, and the mixture was stirred at 50° C. for 19 h under N₂. TLC analysis (PE:EtOAc=1:2, $R_f$=0.5) indicated that 10% of the starting material remained, and one major new spot with polarity lower than that of the starting material was detected. The residue was diluted with water (50 mL) and extracted with EtOAc (30 mL×3). The combined organic layers were washed with brine (30 mL×3), dried over anhydrous sodium sulfate, filtered, and concentrated under reduced pressure. The residue was purified by prep-TLC (SiO₂, PE:EtOAc=0:1) to afford the desired product (0.053 g, 177.12 µmol, 27.31% yield) as a yellow oil. 1H NMR (400 MHz, DMSO-d6) δ ppm 3.09 (s, 1H) 3.33-3.37 (m, 2H) 3.63 (q, J=6.44 Hz, 2H) 3.87 (s, 3H) 4.00 (br d, J=4.16 Hz, 2H) 4.84 (t, J=5.56 Hz, 1H) 6.26-6.38 (m, 1H) 6.69-6.80 (m, 1H) 7.11-7.24 (m, 1H) 7.35 (br d, J=8.19 Hz, 1H).

Example A47: Synthesis of 3-methoxy-N-methyl-4-(prop-2-yn-1-ylamino)benzenesulfonamide and 3-methoxy-N,N-dimethyl-4-(prop-2-yn-1-ylamino)benzenesulfonamide

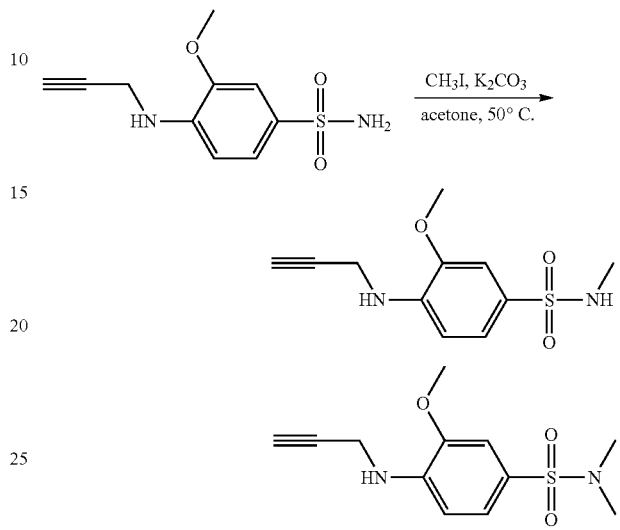

To a solution of 3-methoxy-4-(prop-2-yn-1-ylamino)benzenesulfonamide (1 g, 4.16 mmol, 1 eq.) in acetone (10 mL) were added K₂CO₃ (1.15 g, 8.32 mmol, 2 eq.) and CH₃I (708.87 mg, 4.99 mmol, 310.91 µL, 1.2 eq.). The mixture was stirred at 50° C. for 6 h. LC-MS analysis showed that 27% of the starting material remained, and the desired compound was detected. The reaction mixture was diluted with water (300 mL) and extracted with EtOAc (100 mL×2). The combined organic layers were washed with water (200 mL×2) and brine (200 mL×2), dried over anhydrous sodium sulfate, filtered, and concentrated under reduced pressure. The residue was purified by prep-TLC (SiO₂, PE:EtOAc=1:1) to afford the desired products as yellow oils. 3-methoxy-N-methyl-4-(prop-2-yn-1-ylamino)benzenesulfonamide (0.7 g, 2.75 mmol), 66.08% yield, MS (ES⁺, m/z): 255.1; 3-methoxy-N,N-dimethyl-4-(prop-2-yn-1-ylamino)benzenesulfonamide (0.2 g, 745.35 µmol), 17.91% yield, MS (ES⁺, m/z): 269.1.

Example A48: Synthesis of 5-((tert-butoxycarbonyl)(prop-2-yn-1-yl)amino)thiophene-2-carboxylic acid

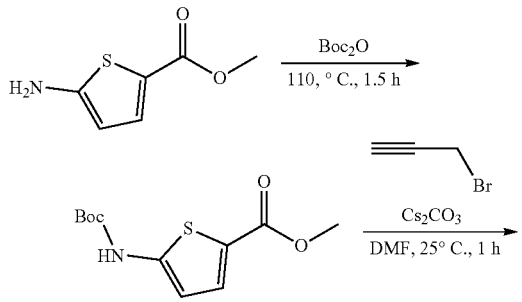

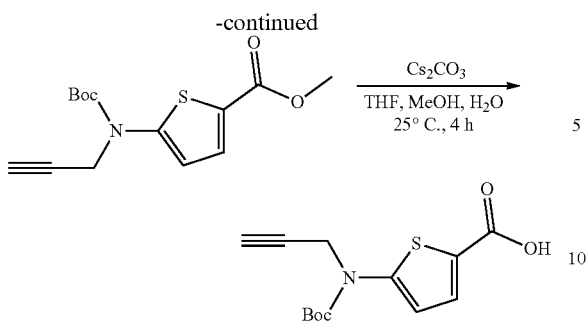

Preparation of methyl 5-((tert-butoxycarbonyl)amino)thiophene-2-carboxylate: A mixture of methyl 5-aminothiophene-2-carboxylate (1 g, 6.36 mmol, 1 eq.) and Boc$_2$O (4.17 g, 19.09 mmol, 4.38 mL, 3 eq.) was degassed and purged with N$_2$ three times, and the mixture was stirred at 110° C. for 1.5 h under N$_2$. TLC analysis (PE:EtOAc=3:1, R$_f$=0.50) indicated that the starting material remained, and one major new spot was detected. The reaction mixture was quenched by adding PE (200 mL) and stirring the mixture for 1 h. The mixture was filtered and concentrated under reduced pressure to give a residue. The crude product (1.6 g, 5.60 mmol, 87.97% yield) was obtained as a yellow solid and used without further purification. MS (ES$^+$, m/z): 258.1.

Preparation of methyl 5-((tert-butoxycarbonyl)(prop-2-yn-1-yl)amino)thiophene-2-carboxylate: A mixture of methyl 5-(tert-butoxycarbonylamino)thiophene-2-carboxylate (1.5 g, 5.25 mmol, 1 eq.), 3-bromoprop-1-yne (686.56 mg, 5.77 mmol, 497.51 µL, 1.1 eq.), and Cs$_2$CO$_3$ (5.13 g, 15.74 mmol, 3 eq.) in DMF (20 mL) was degassed and purged with N$_2$ three times, The mixture was then stirred at 25° C. for 4 h under N$_2$. TLC analysis (PE:EtOAc=3:1, R$_f$=0.60) indicated that the starting material remained, and one major new spot was detected. The reaction mixture was quenched by adding water (200 mL) and extracting the mixture with EtOAc (100 mL×3). The combined organic layers were washed with brine (30 mL×4), filtered, and concentrated under reduced pressure to give a residue. The residue was purified by column chromatography (SiO$_2$, PE:EtOAc=1:0 to 40:1) to afford the desired product (1.1 g, 3.35 mmol, 63.89% yield) as a yellow solid.

Preparation of 5-((tert-butoxycarbonyl)(prop-2-yn-1-yl)amino)thiophene-2-carboxylic acid: A mixture of methyl 5-((tert-butoxycarbonyl)(prop-2-yn-1-yl)amino)thiophene-2-carboxylate (0.5 g, 1.69 mmol, 1 eq.) and Cs$_2$CO$_3$ (5.52 g, 16.93 mmol, 10 eq.) in MeOH (5 mL), water (5 mL), and THF (5 mL) was degassed and purged with N$_2$ three times. The mixture was then stirred at 25° C. for 4 h under N$_2$ atmosphere. TLC analysis (EtOAc=1, R$_f$=0.3) indicated that the starting material remained, and one major new spot was detected. The reaction mixture was concentrated under reduced pressure to remove THF and MeOH. The residue was diluted with water (10 mL), and 2N HCl was added to adjust the pH of the mixture to 5. The mixture was then extracted with EtOAc (30 mL×3). The combined organic layers were washed with brine (20 mL×3), dried over anhydrous sodium sulfate, filtered, and concentrated under reduced pressure. The crude product (0.43 g, 1.36 mmol, 80.36% yield) was obtained as a yellow solid and used without purification. MS (ES$^+$, m/z): 282.0.

Example A49: Synthesis of ethyl 3-methoxy-4-(prop-2-yn-1-ylamino)benzoate

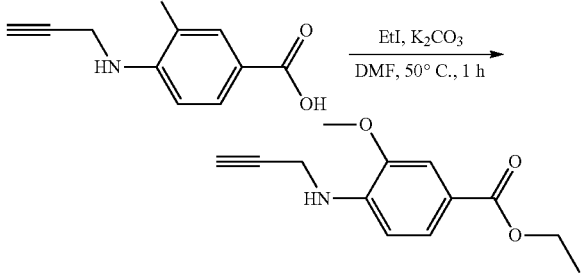

Preparation of ethyl 3-methoxy-4-(prop-2-yn-1-ylamino)benzoate: To a solution of 3-methoxy-4-(prop-2-yn-1-ylamino)benzoic acid (500 mg, 2.44 mmol, 1 eq.) in DMF (6 mL) were added iodoethane (570.02 mg, 3.65 mmol, 292.32 µL, 1.5 eq.) and K$_2$CO$_3$ (1.01 g, 7.31 mmol, 3 eq.). The mixture was stirred at 50° C. for 1 h. TLC analysis showed that the reaction was complete. The reaction mixture was quenched by adding water (80 mL) and extracted with EtOAc (30 mL×3). The combined organic layers were washed with brine (50 mL×3), dried over anhydrous sodium sulfate, filtered, and concentrated under reduced pressure. The desired product (540 mg, crude) was obtained as a yellow solid and used without purification.

Example A50: Synthesis of 3-hydroxy-4-(prop-2-yn-1-ylamino)benzenesulfonamide

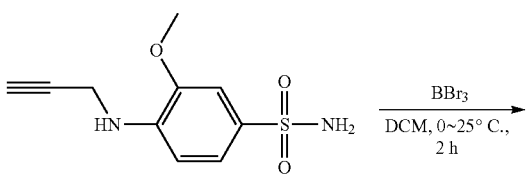

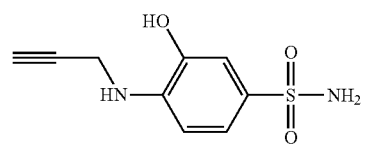

To a solution of 3-methoxy-4-(prop-2-yn-1-ylamino)benzenesulfonamide (0.2 g, 707.51 µmol, 1 eq.) in DCM (2 mL) at 0° C. was added boron tribromide (886.24 mg, 3.54 mmol, 340.86 µL, 5 eq.) under N$_2$. The mixture was stirred at 0~25° C. for 1 h. TLC analysis showed that the reaction was complete. The reaction mixture was quenched by adding water (100 mL) at 0° C. and extracted with EtOAc (30 mL×3). The combined organic layers were washed with brine (30 mL), dried over anhydrous sodium sulfate, filtered, and concentrated under reduced pressure. The crude residue was purified by prep-TLC (SiO$_2$, PE:EtOAc=1:3) to afford the desired product (0.12 g, 424.31 µmol, 59.97% yield) as a yellow oil.

B. Compounds with 2-ethynyl-N-(alkyl)-1H-indole-4-amine Core
Example B1: Synthesis of Compounds 6A, 7A, 8A, and 9A
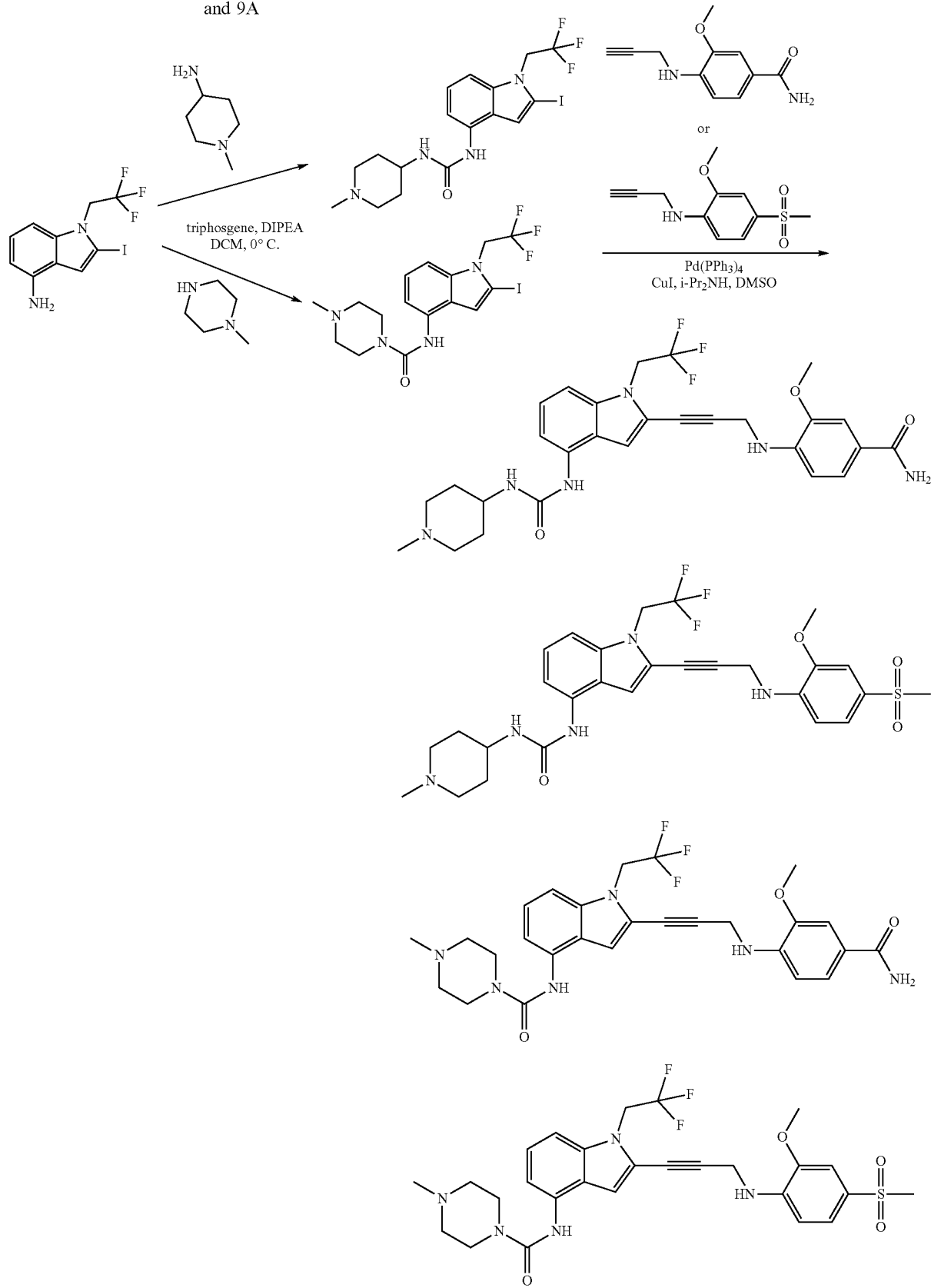

Preparation of 1-(2-iodo-1-(2,2,2-trifluoroethyl)-1H-indol-4-yl)-3-(1-methylpiperidin-4-yl)urea and N-(2-iodo-1-(2,2,2-trifluoroethyl)-1H-indol-4-yl)-4-methylpiperazine-1-carboxamide: To a solution of 2-iodo-1-(2,2,2-trifluoroethyl)-1H-indol-4-amine (1 eq.) and DIPEA (12 eq.) in DCM (6 mL) was added triphosgene (441.07 mol, 1 eq.). The mixture was stirred at 0° C. for 0.5 h. 1-Methylpiperazine or 1-methylpiperidin-4-amine (1.2 eq.) was then added into the mixture, and the resulting mixture was stirred further at 0° C. for 0.5 h. The reaction mixture was poured into a saturated aqueous solution of $Na_2CO_3$ (20 mL) and extracted with DCM (20 mL×3). The combined organic layers were concentrated under reduced pressure to give a residue. The crude residue was dissolved in toluene and concentrated (10 mL×2) to obtain the desired product.

Preparation of N-[2-iodo-1-(2,2,2-trifluoroethyl)indol-4-yl]-4-methyl-piperazine-1-carboxamide: To a solution of 2-iodo-1-(2,2,2-trifluoroethyl)indol-4-amine (150 mg, 441.07 μmol, 1 eq.) and DIPEA (684 mg, 5.29 mmol, 921.92 μL, 12 eq.) in DCM (2 mL) was added triphosgene (131 mg, 441.07 μmol, 1 eq.). The mixture was stirred at 0° C. for 0.5 h. 1-Methylpiperazine (53 mg, 529.28 μmol, 59 μL, 1.2 eq.) was added into the mixture, and the mixture was stirred at 0° C. for 0.5 h. TLC analysis (DCM:MeOH=20:1, $R_f$=0.2) indicated that the starting material was consumed completely, and one new spot was detected. The reaction mixture was poured into a saturated aqueous $Na_2CO_3$ solution (20 mL) and extracted with DCM (20 mL×3). The combined organic layers were concentrated under reduced pressure to give a residue. The residue was diluted with toluene (10 mL), and the mixture was concentrated under reduced pressure to give a residue. After repeating the toluene dilution step twice, the residue was diluted with toluene (10 mL) and filtered to obtain the desired product. N-[2-iodo-1-(2,2,2-trifluoroethyl)indol-4-yl]-4-methyl-piperazine-1-carboxamide (150 mg, 294.06 μmol, 66.67% yield). LC-MS (ES$^+$, m/z): 467.0 [(M+H)$^+$].

Preparation of final products: To a mixture of 3-methoxy-4-(prop-2-yn-1-ylamino)benzamide or 2-methoxy-4-(methylsulfonyl)-N-(prop-2-yn-1-yl)aniline (1-2 eq.) in DMSO (2 mL) were added i-Pr$_2$NH (10~30 eq.), CuI (1~2 eq.), 1-(2-iodo-1-(2,2,2-trifluoroethyl)-1H-indol-4-yl)-3-(1-methylpiperidin-4-yl)urea or N-(2-iodo-1-(2,2,2-trifluoroethyl)-1H-indol-4-yl)-4-methylpiperazine-1-carboxamide (1 eq.), and Pd(PPh$_3$)$_4$ (0.20~0.50 eq.). The mixture was stirred at 20~40° C. for 1~3 h under N$_2$. LC-MS or TLC analysis detected that the reaction was complete. The mixture was poured into saturated EDTA solution (20 mL) and stirred for 1 h, and the aqueous phase was extracted with EtOAc (20 mL×3). The combined organic layers were washed with saturated brine (20 mL×3), dried over anhydrous sodium sulfate, filtered, and concentrated in vacuo. The residue was purified by TLC, prep-TLC or prep-HPLC to afford the desired product.

3-Methoxy-4-{[3-(4-{[(1-methylpiperidin-4-yl)carbamoyl]amino}-1-(2,2,2-trifluoroethyl)-1H-indol-2-yl)prop-2-yn-1-yl]amino}benzamide, MS (ES$^+$, m/z): 557.1; 3-(2-{3-[(4-methanesulfonyl-2-methoxyphenyl)amino]prop-1-yn-1-yl}-1-(2,2,2-trifluoroethyl)-1H-indol-4-yl)-1-(1-methylpiperidin-4-yl)urea, MS (ES$^+$, m/z): 592.1; N-(2-{3-[(4-carbamoyl-2-methoxyphenyl)amino]prop-1-yn-1-yl}-1-(2,2,2-trifluoroethyl)-1H-indol-4-yl)-4-methylpiperazine-1-carboxamide, MS (ES$^+$, m/z): 543.1; and N-(2-{3-[(4-methanesulfonyl-2-methoxyphenyl)amino]prop-1-yn-1-yl}-1-(2,2,2-trifluoroethyl)-1H-indol-4-yl)-4-methylpiperazine-1-carboxamide, MS (ES$^+$, m/z): 578.3.

Example B2: Synthesis of Compounds 13A, 15A, 16A, and 17A

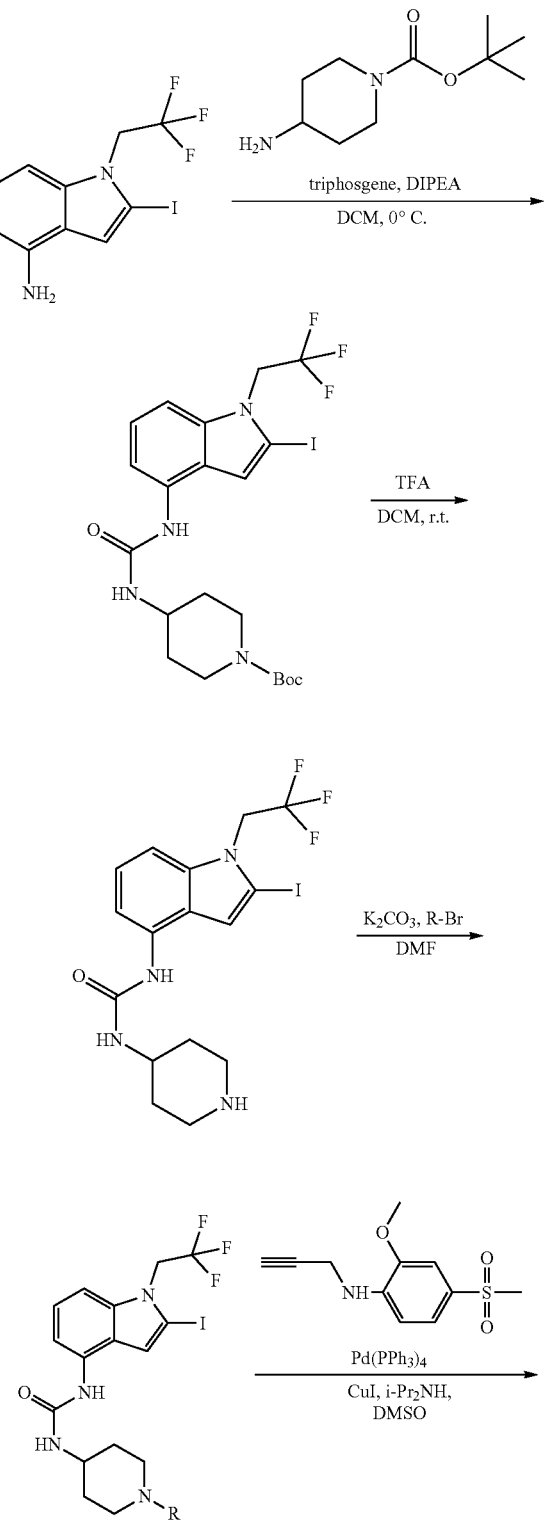

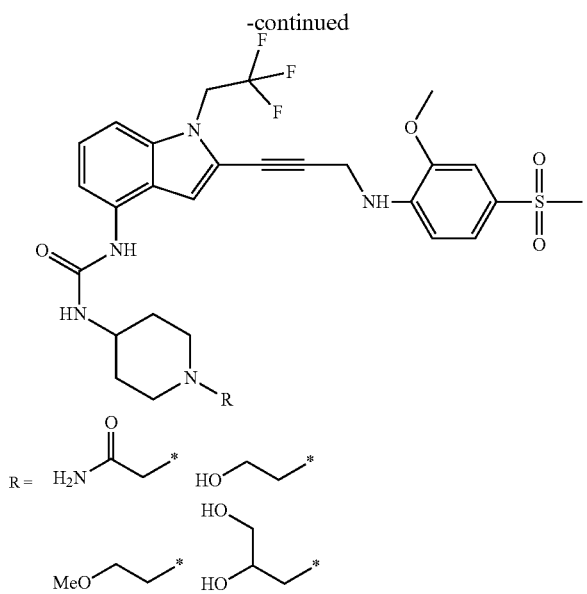

Preparation of tert-butyl 4-(3-(2-iodo-1-(2,2,2-trifluoroethyl)-1H-indol-4-yl)ureido)piperidine-1-carboxylate 1-(2-iodo-1-(2,2,2-trifluoroethyl)-1H-indol-4-yl)-3-(piperidin-4-yl)urea: To a solution of 2-iodo-1-(2,2,2-trifluoroethyl)-1H-indol-4-amine (800 mg, 2.35 mmol) and DIPEA (3.65 g, 28.23 mmol, 4.92 mL, 12 eq.) in DCM (10 mL) was added triphosgene (698.07 mg, 2.35 mmol, 1 eq.). The mixture was stirred at 0° C. for 0.5 h. tert-Butyl 4-aminopiperidine-1-carboxylate (565.35 mg, 2.82 mmol, 1.2 eq.) was then added into the mixture, and the resulting mixture was stirred at 0° C. for 0.5 h. TLC analysis (PE:EtOAc=1:1, $R_f$=0.16) showed that the starting material was consumed completely. Saturated solution of $NaHCO_3$ (30 mL) was added to the reaction mixture, and the aqueous phase was extracted with EtOAc (20 mL×3). The combined organic layers were concentrated in vacuo to obtain the crude product. MS ($ES^+$, m/z): 566.8.

Preparation of 1-(2-iodo-1-(2,2,2-trifluoroethyl)-1H-indol-4-yl)-3-(piperidin-4-yl)urea: To a solution of tert-butyl 4-(3-(2-iodo-1-(2,2,2-trifluoroethyl)-1H-indol-4-yl)ureido)piperidine-1-carboxylate-1-(2-iodo-1-(2,2,2-trifluoroethyl)-1H-indol-4-yl)-3-(piperidin-4-yl)urea (0.8 g, 1.34 mmol, 1 eq.) in DCM (3 mL) was added TFA (4.59 g, 40.26 mmol, 2.98 mL, 30 eq.). The reaction mixture was stirred at 25° C. for 0.5 h. LC-MS analysis showed that the starting material was consumed completely. The reaction mixture was washed with a saturated solution of $NaHCO_3$ (30 mL) and extracted with EtOAc (5 mL×3). The combined organic layers were washed with brine (80 mL), dried over anhydrous sodium sulfate, filtered, and concentrated under reduced pressure to give the crude product as a brown solid (350 mg, 55.9% yield). MS ($ES^+$, m/z): 467.0.

Preparation of 2-iodo-N—C(O)R-1-(2,2,2-trifluoroethyl)-1H-indol-4-amine: To a mixture of 1-(2-iodo-1-(2,2,2-trifluoroethyl)-1H-indol-4-yl)-3-(piperidin-4-yl) urea (100 mg, 214.48 µmol, 1 eq.) and R—Br (428.96 µmol, 2 eq.) in DMF (3 mL) was added $K_2CO_3$ (59.29 mg, 428.96 µmol, 2 eq.). The mixture was stirred at 25° C. for 4 h. LC-MS or TLC analysis showed that the reaction was complete. The reaction mixture was quenched by adding water (40 mL) and extracting the mixture with EtOAc (50 mL×3). The combined organic layers were dried over anhydrous sodium sulfate, filtered, and concentrated under reduced pressure. The residue was purified by prep-TLC to afford the desired products as brown oils.

2-(4-(3-(2-iodo-1-(2,2,2-trifluoroethyl)-1H-indol-4-yl)ureido)piperidin-1-yl)acetamide, 36% yield, MS ($ES^+$, m/z): 524.0; 1-(1-(2-hydroxyethyl)piperidin-4-yl)-3-(2-iodo-1-(2,2,2-trifluoroethyl)-1H-indol-4-yl)urea, 34% yield, MS ($ES^+$, m/z): 511.0; 1-(2-iodo-1-(2,2,2-trifluoroethyl)-1H-indol-4-yl)-3-(1-(2-methoxyethyl)piperidin-4-yl)urea, MS ($ES^+$, m/z): 525.0; 1-(1-(2,3-dihydroxypropyl)piperidin-4-yl)-3-(2-iodo-1-(2,2,2-trifluoroethyl)-1H-indol-4-yl)urea, 37% yield, MS ($ES^+$, m/z): 541.0.

Preparation of 2-(3-((2-methoxy-4-(methylsulfonyl)phenyl)amino)prop-1-yn-1-yl)-N—C(O)R-1-(2,2,2-trifluoroethyl)-1H-indol-4-amine: To a solution of 2-methoxy-4-(methylsulfonyl)-N-(prop-2-yn-1-yl)aniline (26.90 mg, 112.44 µmol, 1.5 eq.) in DMSO (3 mL) were added 2-iodo-N—C(O)R-1-(2,2,2-trifluoroethyl)-1H-indol-4-amine (45 mg, 74.96 µmol, 1 eq.), CuI (1 eq.), N-isopropylpropan-2-amine (1 eq.), and $Pd(PPh_3)_4$ (0.02 eq.). The mixture was stirred at 45° C. for 1 h. LC-MS or TLC analysis indicated that the reaction was complete. The reaction mixture was quenched by adding a saturated EDTA solution (40 mL) at 25° C. and extracting the mixture with EtOAc (20 mL×3). The combined organic layers were dried over anhydrous sodium sulfate, filtered, and concentrated under reduced pressure to give a residue. The residue was purified by prep-TLC ($SiO_2$, DCM:MeOH=10:1, $R_f$=0.24) and prep-HPLC to afford the desired products as light yellow solids.

2-(4-{[(2-{3-[(4-methanesulfonyl-2-methoxyphenyl)amino]prop-1-yn-1-yl}-1-(2,2,2-trifluoroethyl)-1H-indol-4-yl)carbamoyl]amino}piperidin-1-yl)acetamide, MS ($ES^+$, m/z): 635.5; 1-[1-(2-hydroxyethyl)piperidin-4-yl]-3-(2-{3-[(4-methanesulfonyl-2-methoxyphenyl)amino]prop-1-yn-1-yl}-1-(2,2,2-trifluoroethyl)-1H-indol-4-yl)urea, MS ($ES^+$, m/z): 622.3; 3-(2-{3-[(4-methanesulfonyl-2-methoxyphenyl)amino]prop-1-yn-1-yl}-1-(2,2,2-trifluoroethyl)-1H-indol-4-yl)-1-[1-(2-methoxyethyl)piperidin-4-yl]urea, MS ($ES^+$, m/z): 636.1; and 1-[1-(2,3-dihydroxypropyl)piperidin-4-yl]-3-(2-{3-[(4-methanesulfonyl-2-methoxyphenyl)amino]prop-1-yn-1-yl}-1-(2,2,2-trifluoroethyl)-1H-indol-4-yl)urea, MS ($ES^+$, m/z): 652.2.

Example B3: Synthesis of 3-(2-{3-[(4-methanesulfonyl-2-methoxyphenyl)amino]prop-1-yn-1-yl}-1-(2,2,2-trifluoroethyl)-1H-indol-4-yl)-1-[1-(oxan-4-yl)piperidin-4-yl]urea (Compound 14A)

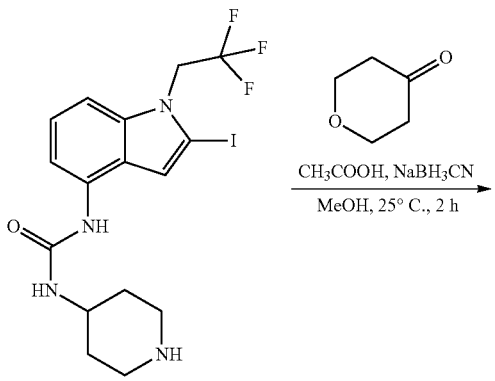

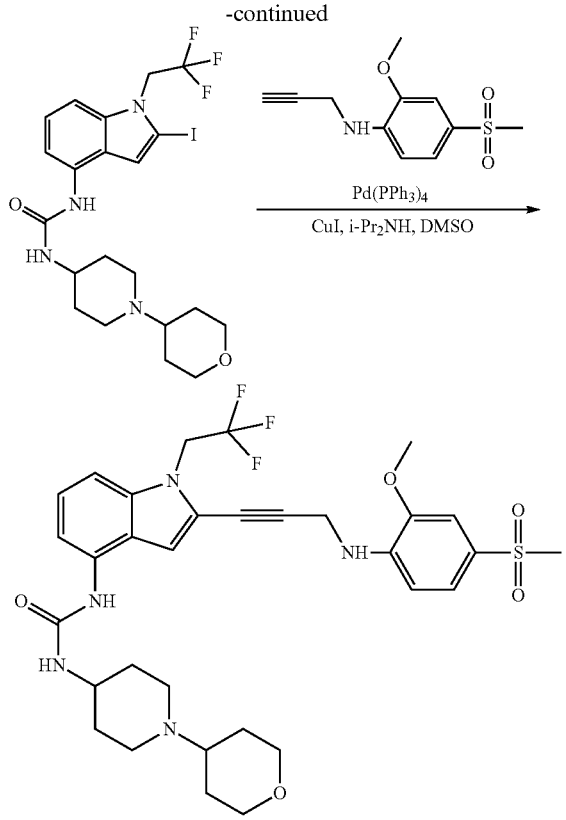

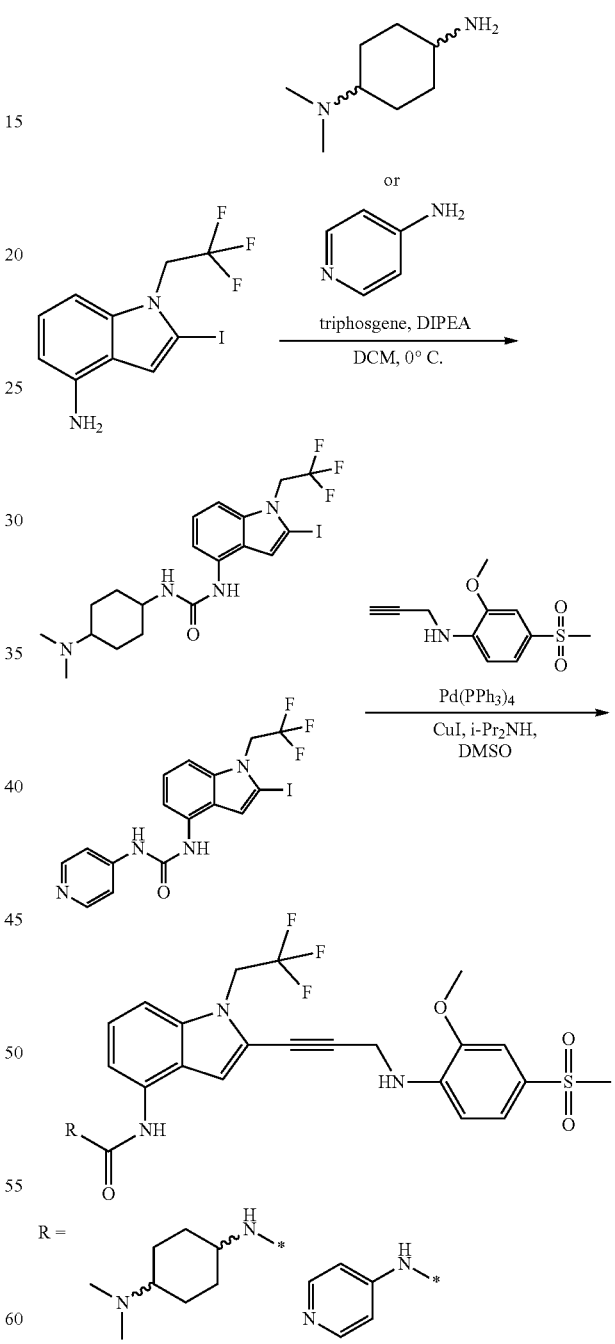

Preparation of 1-(2-iodo-1-(2,2,2-trifluoroethyl)-1H-indol-4-yl)-3-(1-(tetrahydro-2H-pyran-4-yl)piperidin-4-yl)urea: A mixture of 1-(2-iodo-1-(2,2,2-trifluoroethyl)-1H-indol-4-yl)-3-(piperidin-4-yl)urea (107.37 mg, 1.07 mmol, 98.50 μL, 5 eq.), tetrahydro-4H-pyran-4-one (100 mg, 214.48 μmol, 1 eq.), AcOH (12.88 g, 2.14e-1 μmol, 1.23e-2 μL, 0.001 eq.), and NaBH$_3$CN (26.96 mg, 428.96 μmol, 2 eq.) in MeOH (2 mL) was stirred at 25° C. for 2 h. LC-MS analysis confirmed that the reaction was complete. The reaction mixture was quenched by adding a saturated solution of NH$_4$HCO$_3$ (40 mL) and extracting the mixture with EtOAc (50 mL×3). The combined organic layers were dried over anhydrous sodium sulfate, filtered, and concentrated under reduced pressure to give a residue. The crude residue was purified by prep-TLC (SiO$_2$, DCM:MeOH=10:1, R$_f$=0.24) to afford the desired product as a brown solid. 29% yield, MS (ES$^+$, m/z): 551.0.

Preparation of 3-(2-{3-[(4-methanesulfonyl-2-methoxyphenyl)amino]prop-1-yn-1-yl}-1-(2,2,2-trifluoroethyl)-1H-indol-4-yl)-1-[1-(oxan-4-yl)piperidin-4-yl]urea: To a solution of 2-methoxy-4-(methylsulfonyl)-N-(prop-2-yn-1-yl)aniline (22.17 mg, 92.67 μmol, 1.5 eq.) in DMSO (3 mL) were added 1-(2-iodo-1-(2,2,2-trifluoroethyl)-1H-indol-4-yl)-3-(1-(tetrahydro-2H-pyran-4-yl)piperidin-4-yl)urea (40 mg, 61.78 μmol, 1 eq.), CuI (11.77 mg, 61.78 μmol, 1 eq.), N-isopropylpropan-2-amine (6.25 mg, 61.78 μmol, 8.73 μL, 1 eq.), and Pd(PPh$_3$)$_4$ (1.43 mg, 1.24 μmol, 0.02 eq.). The mixture was stirred at 45° C. for 1 h. LC-MS analysis indicated that the reaction was complete. The reaction mixture was quenched by adding a saturated EDTA solution (40 mL) at 25° C., and the mixture was extracted with EtOAc (20 mL×3). The combined organic layers were dried over anhydrous sodium sulfate, filtered, and concentrated under reduced pressure to give a residue. The residue was purified by prep-HPLC to obtain the desired product (17.2 mg, 25.89 μmol, 41.91% yield) as a light yellow solid. 3-(2-{3-[(4-methanesulfonyl-2-methoxyphenyl)amino]prop-1-yn-1-yl}-1-(2,2,2-trifluoroethyl)-1H-indol-4-yl)-1-[1-(oxan-4-yl)piperidin-4-yl]urea, MS (ES$^+$, m/z): 662.3.

Example B4: Synthesis of Compounds 10A, 11A, and 12A

General procedure for the preparation of 1-(4-(dimethylamino)cyclohexyl)-3-(2-iodo-1-(2,2,2-trifluoroethyl)-1H-indol-4-yl)urea and 1-(2-iodo-1-(2,2,2-trifluoroethyl)-1H-indol-4-yl)-3-(pyridin-4-yl)urea: To a solution of 2-iodo-1-(2,2,2-trifluoroethyl)-1H-indol-4-amine (1 eq.) and DIPEA (12 eq.) in DCM was added triphosgene (1 eq.). The mixture was stirred at 0° C. for 0.5 h, and N¹,N¹-dimethylcyclohexane-1,4-diamine or pyridine-4-amine (1.2 eq.) was added to the reaction. The resulting reaction mixture was stirred further at 0° C. for 0.5 h. TLC analysis showed that the staring material was consumed completely. The reaction mixture was quenched by adding a saturated solution of $Na_2CO_3$. The reaction mixture was partitioned by adding EtOAc, and the aqueous phase was extracted with EtOAc (×3). The organic phase was washed with brine (×3), dried over anhydrous sodium sulfate, filtered, and concentrated in vacuo to give the crude product. The residue was purified by prep-TLC to give the desired products as brown solids.

Preparation of 1-(4-(dimethylamino)cyclohexyl)-3-(2-iodo-1-(2,2,2-trifluoroethyl)-1H-indol-4-yl)urea and 1-(2-iodo-1-(2,2,2-trifluoroethyl)-1H-indol-4-yl)-3-(pyridin-4-yl)urea: To a solution of 2-methoxy-4-(methylsulfonyl)-N-(prop-2-yn-1-yl)aniline (1.2 eq.) in DMSO were added i-$Pr_2$NH (10 eq.), CuI (1 eq.), 1-(4-(dimethylamino)cyclohexyl)-3-(2-iodo-1-(2,2,2-trifluoroethyl)-1H-indol-4-yl)urea or 1-(2-iodo-1-(2,2,2-trifluoroethyl)-1H-indol-4-yl)-3-(pyridin-4-yl)urea (1 eq.), and Pd(PPh$_3$)$_4$ (0.2 eq.) at 25° C. The mixture was stirred at 25° C. for 1-2 h under N$_2$. LC-MS and TLC analysis showed that the reaction was complete. The reaction mixture was quenched by adding a saturated EDTA solution and stirring the mixture at 25° C. for 2 h. The reaction mixture was partitioned by adding EtOAc, and the aqueous phase was extracted with EtOAc. The organic phase was washed with brine, dried over anhydrous sodium sulfate, filtered, and concentrated in vacuo. The residue was purified by prep-TLC prep-HPLC to give solutions of the desired products. The solutions were lyophilized to give the desired products as yellow solids.

3-(2-{3-[(4-methanesulfonyl-2-methoxyphenyl)amino]prop-1-yn-1-yl}-1-(2,2,2-trifluoroethyl)-1H-indol-4-yl)-1-[(1R,4R)-4-(dimethylamino)cyclohexyl]urea, MS (ES⁺, m/z): 620.3; 3-(2-{3-[(4-methanesulfonyl-2-methoxyphenyl)amino]prop-1-yn-1-yl}-1-(2,2,2-trifluoroethyl)-1H-indol-4-yl)-1-[(1S,4S)-4-(dimethylamino)cyclohexyl]urea, MS (ES⁺, m/z): 620.3; and 1-(2-(3-((2-methoxy-4-(methylsulfonyl)phenyl)amino)prop-1-yn-1-yl)-1-(2,2,2-trifluoroethyl)-1H-indol-4-yl)-3-(pyridin-4-yl)urea, MS (ES⁺, m/z): 572.3.

Example B5: Preparation of Compound 2-{3-[(4-methanesulfonyl-2-methoxyphenyl)amino]prop-1-yn-1-yl}-N,N-dimethyl-1-(2,2,2-trifluoroethyl)-1H-indol-4-amine (Compound 1A)

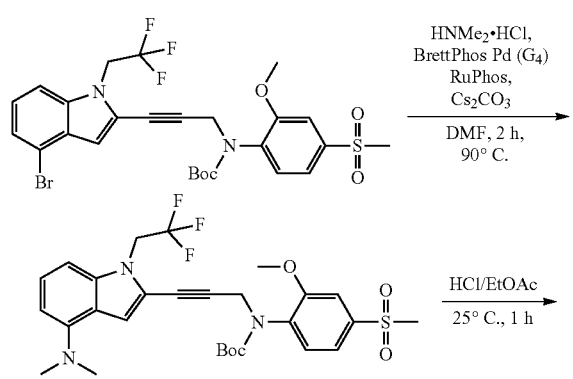

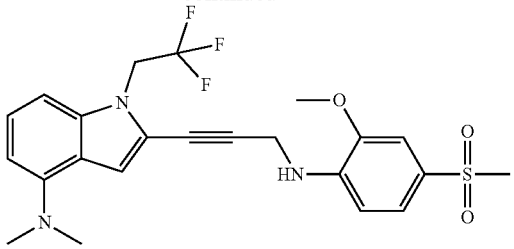

Preparation of tert-butyl (3-(4-(dimethylamino)-1-(2,2,2-trifluoroethyl)-1H-indol-2-yl)prop-2-yn-1-yl)(2-methoxy-4-(methylsulfonyl)phenyl)carbamate: To a mixture of tert-butyl (3-(4-bromo-1-(2,2,2-trifluoroethyl)-1H-indol-2-yl)prop-2-yn-1-yl)(2-methoxy-4-(methylsulfonyl)phenyl)carbamate (150 mg, 238.8 μmol, 1 eq.) and dimethylamine hydrochloride (31 mg, 262.73 μmol, 1.1 eq.) in DMF (2 mL) were added Brettphos Pd (G$_4$) (15 mg, 16.72 μmol, 0.07 eq.), Cs$_2$CO$_3$ (233 mg, 716.54 μmol, 3 eq.) and RuPhos (15 mg, 33.44 μmol, 0.14 eq.). The reaction mixture was degassed and purged with N$_2$. The mixture was heated to 90° C. and stirred for 2 h, after which time TLC (PE:EtOAc=1:1, R$_f$=0.45) and LC-MS analysis indicated that the reaction was complete. The mixture was poured into saturated EDTA solution (10 mL) and stirred for 1 h. The mixture was extracted with EtOAc (20 mL×3), and the combined organic layers were washed with brine (10 mL), dried over anhydrous sodium sulfate, and concentrated. The crude residue was purified by column chromatography (SiO$_2$, PE:EtOAc=8:1 to 3:1) to provide tert-butyl (3-(4-(dimethylamino)-1-(2,2,2-trifluoroethyl)-1H-indol-2-yl)prop-2-yn-1-yl)(2-methoxy-4-(methylsulfonyl)phenyl)carbamate (100 mg, 141.47 μmol, 72% yield).

Preparation of final product: To a solution of tert-butyl (3-(4-(dimethylamino)-1-(2,2,2-trifluoroethyl)-1H-indol-2-yl)prop-2-yn-1-yl)(2-methoxy-4-(methylsulfonyl)phenyl)carbamate (0.1 g, 172.52 μmol, 1 eq.) in EtOAc (2 mL) was added HCl/EtOAc (4 M, 10 mL, 231.85 eq.). The mixture was stirred at 25° C. for 1 h, after which time TLC analysis (PE:EtOAc=1:1, R$_f$=0.3) indicated that the reaction was complete. The reaction mixture was filtered and concentrated in vacuo. The residue was purified by prep-HPLC to provide 2-{3-[(4-methanesulfonyl-2-methoxyphenyl)amino]prop-1-yn-1-yl}-N,N-dimethyl-1-(2,2,2-trifluoroethyl)-1H-indol-4-amine (27.6 mg, 57.56 μmol, 33.36% yield) as a light yellow solid.

Example B6: Preparation of Compound 4-[(3-{4-[(1,5-dihydroxypentan-3-yl)amino]-1-(2,2,2-trifluoroethyl)-1H-indol-2-yl}prop-2-yn-1-yl)amino]-3-methoxybenzene-1-sulfonamide (Compound 4A)

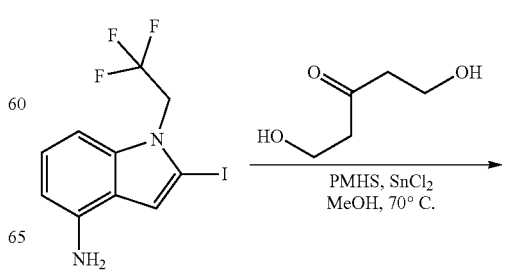

-continued

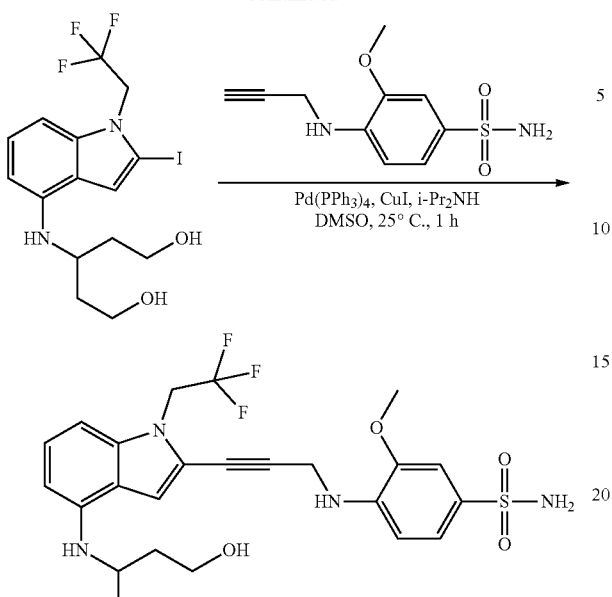

Synthesis of 3-((2-iodo-1-(2,2,2-trifluoroethyl)-1H-indol-4-yl)amino)pentane-1,5-diol: To a mixture of 2-iodo-1-(2,2,2-trifluoroethyl)-1H-indol-4-amine (0.1 g, 294.05 μmol, 1 eq.) in MeOH (5 mL) were added 1,5-dihydroxypentan-3-one (69.47 mg, 588.09 μmol, 40.50 μL, 2 eq.) and SnCl$_2$·2H$_2$O (13.27 mg, 58.81 μmol, 4.90 μL, 0.20 eq.), followed by PMHS (70.57 mg, 1.18 mmol, 4 eq.). The resulting mixture was stirred for 3 h at 70° C., after which time LC-MS analysis indicated that a species with the desired mass had formed. The mixture was concentrated under reduced pressure to provide a crude residue that was purified by prep-TLC (SiO$_2$, EtOAc:PE=2:1, R$_f$=0.16. 3-((2-iodo-1-(2,2,2-trifluoroethyl)-1H-indol-4-yl)amino)pentane-1,5-diol (0.05 g, 96.11 μmol, 32.68% yield) was obtained as a yellow oil. MS (ES$^+$, m/z): 443.1.

Synthesis of final product: To a mixture of 3-methoxy-4-(prop-2-yn-1-ylamino)benzenesulfonamide (40.75 mg, 144.16 μmol, 1.5 eq.) and 3-((2-iodo-1-(2,2,2-trifluoroethyl)-1H-indol-4-yl)amino)pentane-1,5-diol (0.05 g, 96.11 μmol, 1 eq.) in DMSO (2 mL) were added CuI (18.30 mg, 96.11 μmol, 1 eq.), followed by Pd(PPh$_3$)$_4$ (11.11 mg, 9.61 μmol, 0.10 eq.) and N-isopropylpropan-2-amine (9.73 mg, 96.11 μmol, 13.58 μL, 1 eq.). The reaction mixture was stirred at 30° C. for 1 h under N$_2$, after which time TLC analysis (PE:EtOAc=1:2, R$_f$=0.30) indicated that the reaction was complete The reaction mixture was quenched by adding a saturated EDTA solution (30 mL). EtOAc (10 mL) was added, the resulting mixture was stirred at 25° C. for 1 h, and the mixture was extracted with EtOAc (20 mL×3). The combined organic layers were washed with brine (30 mL), dried over anhydrous sodium sulfate, filtered, and concentrated under reduced pressure. The resulting residue was purified by prep-TLC (SiO$_2$, PE:EtOAc=1:2, R$_f$=0.30) and further purified by prep-HPLC to afford 4-[(3-{4-[(1,5-dihydroxypentan-3-yl)amino]-1-(2,2,2-trifluoroethyl)-1H-indol-2-yl}prop-2-yn-1-yl)amino]-3-methoxybenzene-1-sulfonamide (0.007 g, 12.47 μmol, 12.98% yield) as white solid. MS (ES$^+$, m/z): 555.2.

Example B7: Synthesis of 2-[(2-{3-[(2-methoxy-4-sulfamoylphenyl)amino]prop-1-yn-1-yl}-1-(2,2,2-trifluoroethyl)-1H-indol-4-yl)amino]acetamide (Compound 3A)

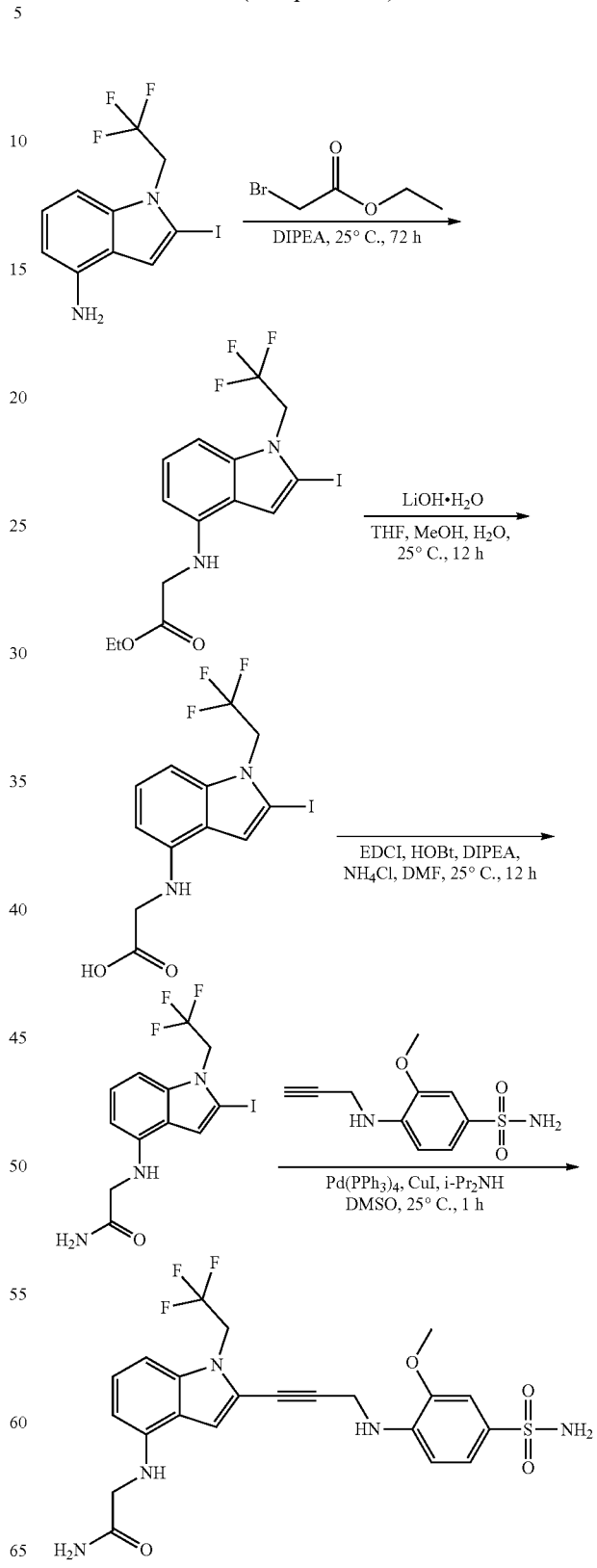

Synthesis of ethyl (2-iodo-1-(2,2,2-trifluoroethyl)-1H-indol-4-yl)glycinate: To a mixture of 2-iodo-1-(2,2,2-trifluoroethyl)-1H-indol-4-amine (0.5 g, 1.47 mmol, 1 eq.) and ethyl 2-bromoacetate (2.46 g, 14.70 mmol, 1.63 mL, 10 eq.) in THF (5 mL) was added DIPEA (1.28 mL, 4.41 mmol, 3 eq.) in one portion at 25° C. under $N_2$. The mixture was stirred at 25° C. for 96 h, after which time TLC analysis (PE:EtOAc=5:1, $R_f$=0.4) indicated that the reaction was complete. The mixture was concentrated in vacuo at 45° C., and the residue was purified by silica gel chromatography ($SiO_2$, PE:EtOAc=100:1 to 5:1) to afford ethyl (2-iodo-1-(2,2,2-trifluoroethyl)-1H-indol-4-yl)glycinate (400 mg, 844.73 μmol, 57.46% yield) as a yellow solid.

Synthesis of (2-iodo-1-(2,2,2-trifluoroethyl)-1H-indol-4-yl)glycine: To a mixture of ethyl (2-iodo-1-(2,2,2-trifluoroethyl)-1H-indol-4-yl)glycinate (400 mg, 938.59 μmol, 1 eq.) in MeOH (3 mL), THF (9 mL), and water (3 mL) was added $LiOH \cdot H_2O$ (196.93 mg, 4.69 mmol, 5 eq.) in one portion at 25° C. under $N_2$. The mixture was stirred at 25° C. for 12 h, after which time LC-MS analysis indicated that the reaction was complete. The mixture was concentrated under reduced pressure at 40° C., and the residue was poured into water (10 mL) and stirred for 1 min. The aqueous phase was extracted with EtOAc (10 mL×2), adjusted to pH 2 by adding 2N HCl, and extracting the mixture again with EtOAc (10 mL×2). The combined organic layers were washed with brine (10 mL), dried over anhydrous sodium sulfate, filtered, and concentrated in vacuo to afford (2-iodo-1-(2,2,2-trifluoroethyl)-1H-indol-4-yl)glycine (280 mg, 668.14 μmol, 71.19% yield) as a yellow solid.

Synthesis of 2-((2-iodo-1-(2,2,2-trifluoroethyl)-1H-indol-4-yl)amino)acetamide: To a mixture of (2-iodo-1-(2,2,2-trifluoroethyl)-1H-indol-4-yl)glycine (120 mg, 301.42 μmol, 1 eq.) in DMF (5 mL) were added 1-(3-Dimethylaminopropyl)-3-ethylcarbodiimide (EDCI) (115.56 mg, 602.84 μmol, 2 eq.), HOBt (81.46 mg, 602.84 μmol, 2 eq.), DIPEA (155.82 mg, 1.21 mmol, 210.01 μL, 4 eq.) and $NH_4Cl$ (32.25 mg, 602.84 μmol, 21.08 μL, 2 eq.) under $N_2$. The mixture was stirred at 25° C. for 12 h, after which time LC-MS analysis indicated that the reaction was complete. The mixture was poured into water (30 mL) and stirred for 2 min, and the aqueous phase was extracted with EtOAc (20 mL×5). The combined organic layers were washed with brine (10 mL), dried over anhydrous sodium sulfate, filtered, and concentrated in vacuo. The residue was washed with DCM (10 mL×3), filtered, and concentrated in vacuo to afford 2-((2-iodo-1-(2,2,2-trifluoroethyl)-1H-indol-4-yl)amino)acetamide (70 mg, 96.66 μmol, 32.07% yield) as light yellow solid.

Preparation of final product: To a mixture of 3-methoxy-4-(prop-2-yn-1-ylamino)benzenesulfonamide (36.30 mg, 151.08 μmol, 1.2 eq.) in DMSO (2 mL) were added i-$Pr_2NH$ (127.40 mg, 1.26 mmol, 177.93 μL, 10 eq.), CuI (23.98 mg, 125.90 μmol, 1 eq.), 2-((2-iodo-1-(2,2,2-trifluoroethyl)-1H-indol-4-yl)amino)acetamide (50 mg, 125.90 μmol, 1 eq.), and $Pd(PPh_3)_4$ (29.10 mg, 25.18 μmol, 0.2 eq.) under $N_2$. The mixture was stirred at 45° C. for 1 h, after which time LC-MS and TLC analysis (PE:EtOAc=0:1, $R_f$=0.32) indicated that the reaction was complete. EtOAc (10 mL) was added, and the mixture was poured into a saturated EDTA solution (40 mL) and stirred for 15 min. The aqueous phase was extracted with EtOAc (40 mL×2), and the organic layer was poured again into a saturated EDTA solution (40 mL) and stirred for 1 h. The aqueous phase was extracted again with EtOAc (40 mL×3). The combined organic layers were washed with brine (40 mL×3), dried over anhydrous sodium sulfate, treated with activated carbon, filtered, and concentrated in vacuo. The residue was purified by prep-TLC (PE:EtOAc=0:1, $R_f$=0.32) and further purified by prep-HPLC to afford 2-[(2-{3-[(2-methoxy-4-sulfamoylphenyl)amino]prop-1-yn-1-yl}-1-(2,2,2-trifluoroethyl)-1H-indol-4-yl)amino]acetamide (5.1 mg, 9.04 μmol, 7.18% yield) as light yellow solid. MS ($ES^+$, m/z): 510.1.

TABLE 2 shows compounds with a 2-ethynyl-N-(alkyl)-1H-indole-4-amine core.

TABLE 2

| Compound No. | Structure | IUPAC | LC-MS ($ES^+$, m/z) |
|---|---|---|---|
| 1A | 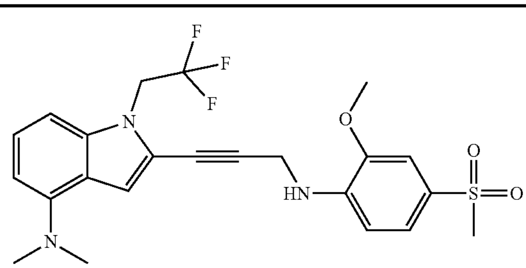 | 2-{3-[(4-methanesulfonyl-2-methoxyphenyl)amino]prop-1-yn-1-yl}-N,N-dimethyl-1-(2,2,2-trifluoroethyl)-1H-indol-4-amine | 480.0 |
| 2A | 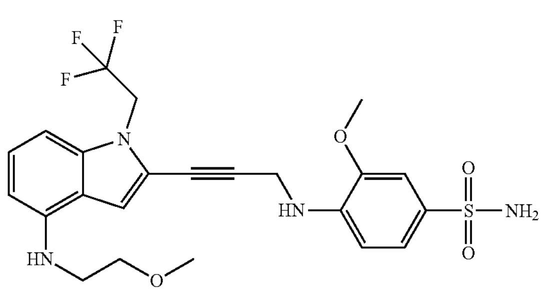 [SMILES: COCCNc1cccc2c1cc(C#CCNc1ccc(S(N)(=O)=O)cc1OC)n2CC(F)(F)F] | 3-methoxy-4-[(3-{4-[(2-methoxyethyl)amino]-1-(2,2,2-trifluoroethyl)-1H-indol-2-yl}prop-2-yn-1-yl)amino]benzene-1-sulfonamide | 511.1 |

TABLE 2-continued

| Compound No. | Structure | IUPAC | LC-MS (ES+, m/z) |
|---|---|---|---|
| 3A | 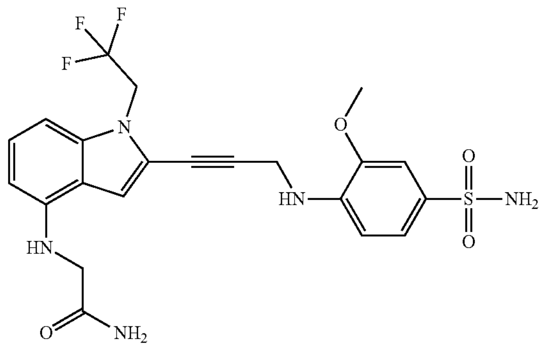 [SMILES: COc1cc(S(N)(=O)=O)ccc1NCC#Cc1cc2c(NCC(N)=O)cccc2n1CC(F)(F)F] | 2-[(2-{3-[(2-methoxy-4-sulfamoylphenyl)amino]prop-1-yn-1-yl}-1-(2,2,2-trifluoroethyl)-1H-indol-4-yl)amino]acetamide | 510.1 |
| 4A | 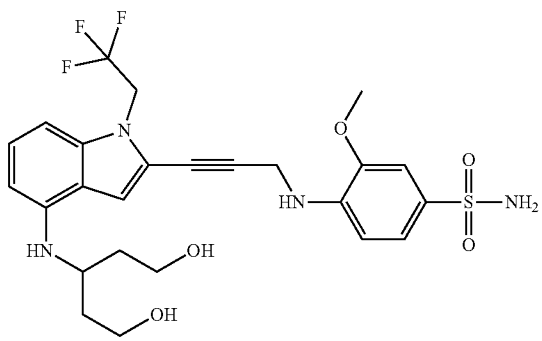 [SMILES: COc1cc(S(N)(=O)=O)ccc1NCC#Cc1cc2c(NC(CCO)CCO)cccc2n1CC(F)(F)F] | 4-[(3-{4-[(1,5-dihydroxypentan-3-yl)amino]-1-(2,2,2-trifluoroethyl)-1H-indol-2-yl}prop-2-yn-1-yl)amino]-3-methoxybenzene-1-sulfonamide | 555.2 |
| 5A | 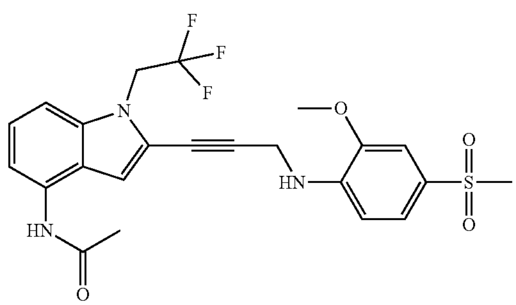 [SMILES: COc1cc(S(C)(=O)=O)ccc1NCC#Cc1cc2c(NC(C)=O)cccc2n1CC(F)(F)F] | N-(2-{3-[(4-methanesulfonyl-2-methoxyphenyl)amino]prop-1-yn-1-yl}-1-(2,2,2-trifluoroethyl)-1H-indol-4-yl)acetamide | 494.2 |
| 6A | 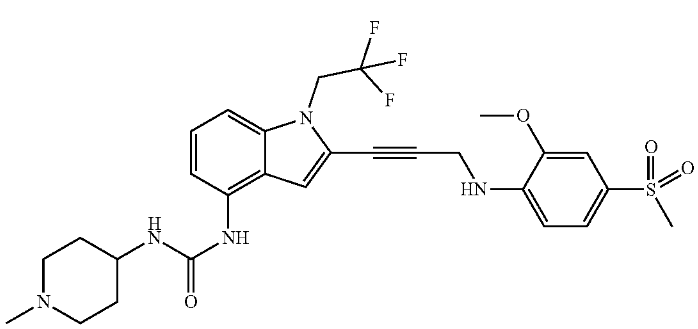 [SMILES: COc1cc(S(C)(=O)=O)ccc1NCC#Cc1cc2c(NC(=O)NC3CCN(C)CC3)cccc2n1CC(F)(F)F] | 3-(2-{3-[(4-methanesulfonyl-2-methoxyphenyl)amino]prop-1-yn-1-yl}-1-(2,2,2-trifluoroethyl)-1H-indol-4-yl)-1-(1-methylpiperidin-4-yl)urea | 592.1 |

TABLE 2-continued

| Compound No. | Structure | IUPAC | LC-MS (ES+, m/z) |
|---|---|---|---|
| 7A | 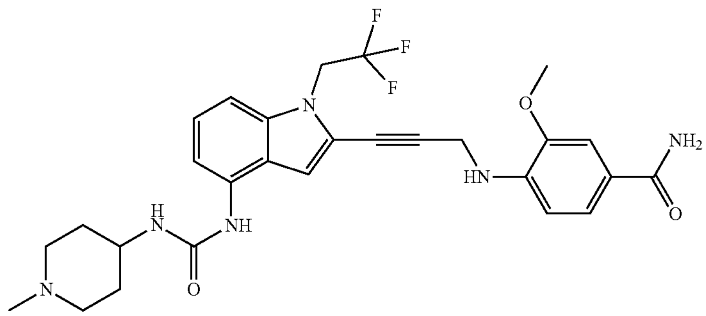 [SMILES: COc1cc(C(N)=O)ccc1NCC#Cc1cc2c(NC(=O)NC3CCN(C)CC3)cccc2n1CC(F)(F)F] | 3-methoxy-4-{[3-(4-{[(1-methylpiperidin-4-yl)carbamoyl]amino}-1-(2,2,2-trifluoroethyl)-1H-indol-2-yl)prop-2-yn-1-yl]amino}benzamide | 557.1 |
| 8A | 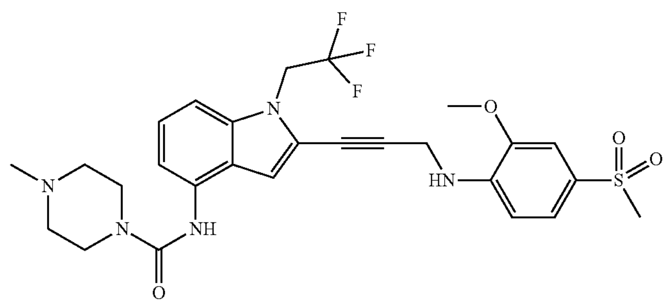 [SMILES: COc1cc(S(C)(=O)=O)ccc1NCC#Cc1cc2c(NC(=O)N3CCN(C)CC3)cccc2n1CC(F)(F)F] | N-(2-{3-[(4-methanesulfonyl-2-methoxyphenyl)amino]prop-1-yn-1-yl}-1-(2,2,2-trifluoroethyl)-1H-indol-4-yl)-4-methylpiperazine-1-carboxamide | 578.3 |
| 9A | 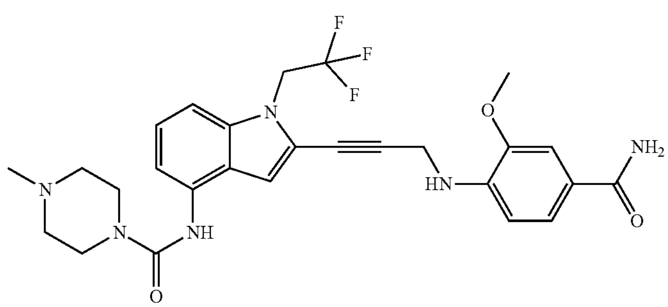 [SMILES: COc1cc(C(N)=O)ccc1NCC#Cc1cc2c(NC(=O)N3CCN(C)CC3)cccc2n1CC(F)(F)F] | N-(2-{3-[(4-carbamoyl-2-methoxyphenyl)amino]prop-1-yn-1-yl}-1-(2,2,2-trifluoroethyl)-1H-indol-4-yl)-4-methylpiperazine-1-carboxamide | 543.1 |
| 10A | 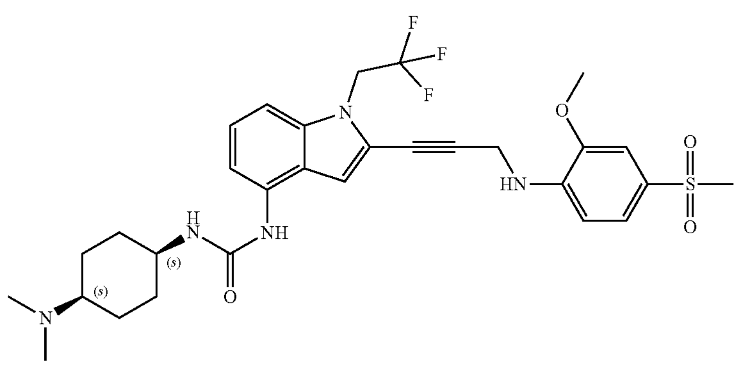 | 3-(2-{3-[(4-methanesulfonyl-2-methoxyphenyl)amino]prop-1-yn-1-yl}-1-(2,2,2-trifluoroethyl)-1H-indol-4-yl)-1-[(1S,4S)-4-(dimethylamino)cyclohexyl]urea | 620.3 |

TABLE 2-continued

| Compound No. | Structure | IUPAC | LC-MS (ES+, m/z) |
|---|---|---|---|
| 11A | 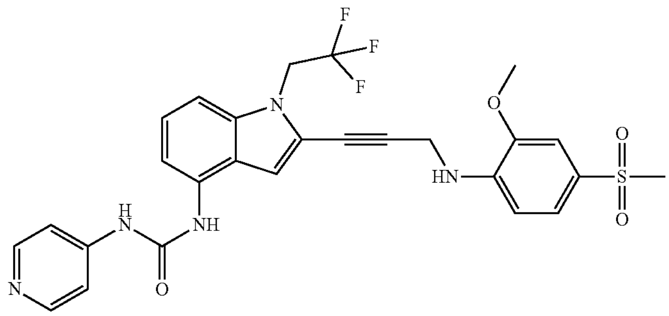 [SMILES: COc1cc(S(C)(=O)=O)ccc1NCC#Cc1cc2c(NC(=O)Nc3ccncc3)cccc2n1CC(F)(F)F] | 1-(2-(3-((2-methoxy-4-(methylsulfonyl)phenyl)amino)prop-1-yn-1-yl)-1-(2,2,2-trifluoroethyl)-1H-indol-4-yl)-3-(pyridin-4-yl)urea | 572.3 |
| 12A | 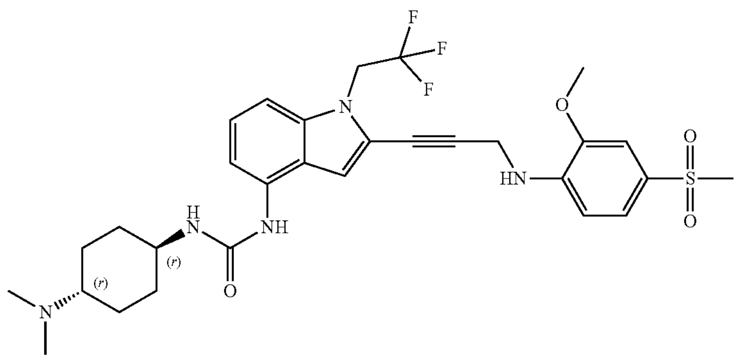 | 3-(2-{3-[(4-methanesulfonyl-2-methoxyphenyl)amino]prop-1-yn-1-yl}-1-(2,2,2-trifluoroethyl)-1H-indol-4-yl)-1-[(1R,4R)-4-(dimethylamino)cyclohexyl]urea | 620.3 |
| 13A | 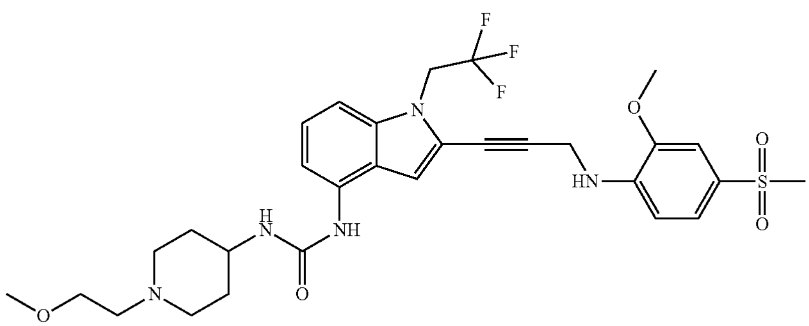 | 3-(2-{3-[(4-methanesulfonyl-2-methoxyphenyl)amino]prop-1-yn-1-yl}-1-(2,2,2-trifluoroethyl)-1H-indol-4-yl)-1-[1-(2-methoxyethyl)piperidin-4-yl]urea | 636.1 |
| 14A | 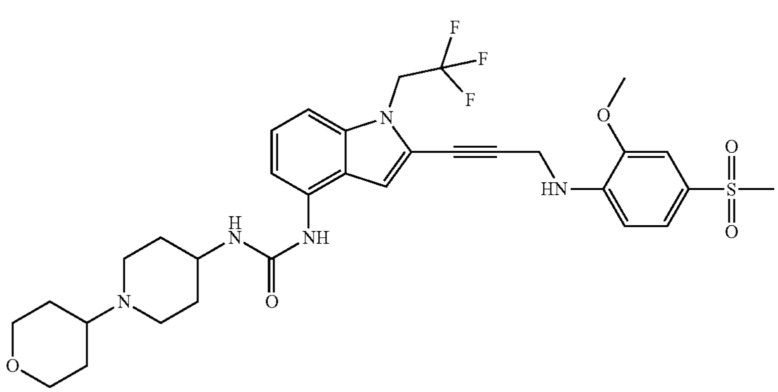 [SMILES: COc1cc(S(C)(=O)=O)ccc1NCC#Cc1cc2c(NC(=O)NC3CCN(C4CCOCC4)CC3)cccc2n1CC(F)(F)F] | 3-(2-{3-[(4-methanesulfonyl-2-methoxyphenyl)amino]prop-1-yn-1-yl}-1-(2,2,2-trifluoroethyl)-1H-indol-4-yl)-1-[1-(oxan-4-yl)piperidin-4-yl]urea | 662.3 |

TABLE 2-continued

| Compound No. | Structure | IUPAC | LC-MS (ES+, m/z) |
|---|---|---|---|
| 15A | 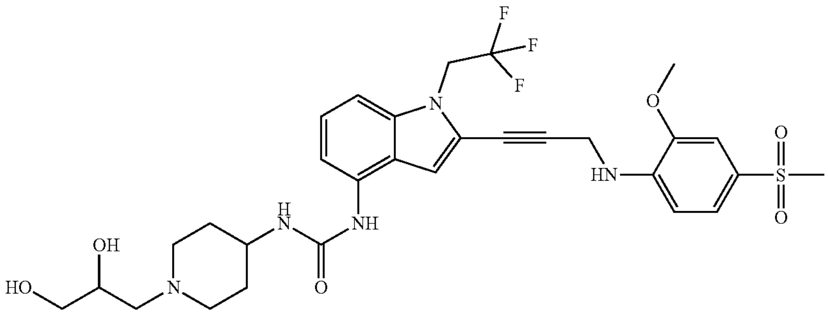 [SMILES: COc1cc(S(C)(=O)=O)ccc1NCC#Cc1cc2c(NC(=O)NC3CCN(CC(O)CO)CC3)cccc2n1CC(F)(F)F] | 1-[1-(2,3-dihydroxypropyl)piperidin-4-yl]-3-(2-{3-[(4-methanesulfonyl-2-methoxyphenyl)amino]prop-1-yn-1-yl}-1-(2,2,2-trifluoroethyl)-1H-indol-4-yl)urea | 652.2 |
| 16A | 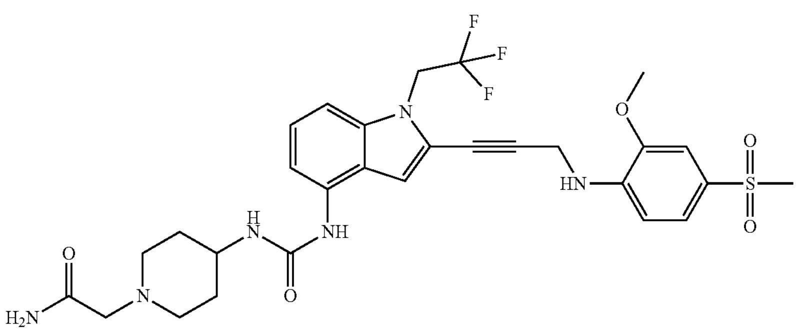 [SMILES: COc1cc(S(C)(=O)=O)ccc1NCC#Cc1cc2c(NC(=O)NC3CCN(CC(N)=O)CC3)cccc2n1CC(F)(F)F] | 2-(4-{[(2-{3-[(4-methanesulfonyl-2-methoxyphenyl)amino]prop-1-yn-1-yl}-1-(2,2,2-trifluoroethyl)-1H-indol-4-yl)carbamoyl]amino}piperidin-1-yl)acetamide | 635.2 |
| 17A | 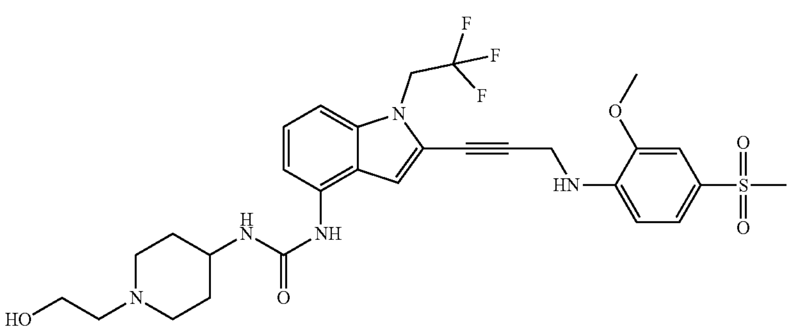 [SMILES: COc1cc(S(C)(=O)=O)ccc1NCC#Cc1cc2c(NC(=O)NC3CCN(CCO)CC3)cccc2n1CC(F)(F)F] | 1-[1-(2-hydroxyethyl)piperidin-4-yl]-3-(2-{3-[(4-methanesulfonyl-2-methoxyphenyl)amino]prop-1-yn-1-yl}-1-(2,2,2-trifluoroethyl)-1H-indol-4-yl)urea | 622.3 |

C. Compounds with 2-ethynyl-N-(cycloalkyl)-1H-indole-4-amine Core

Example C1: Synthesis of Compounds 31A, 32A, 33A, 34A, and 35A

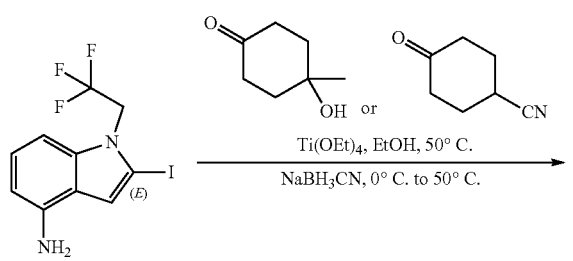

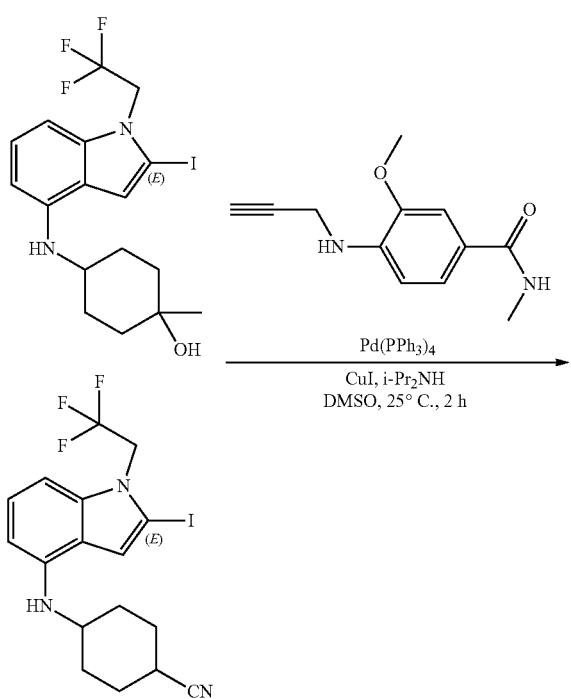

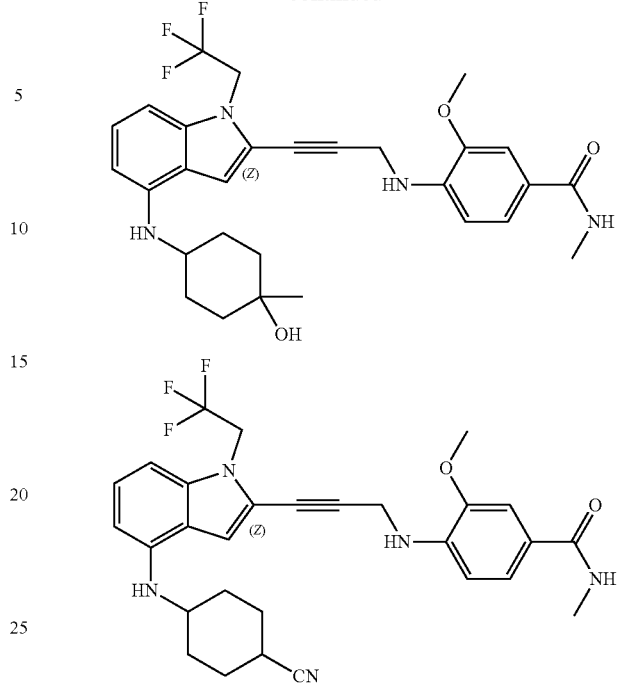

General procedure for the preparation of 4-((2-iodo-1-(2,2,2-trifluoroethyl)-1H-indol-4-yl)amino)-1-methylcyclohexan-1-ol and 4-((2-iodo-1-(2,2,2-trifluoroethyl)-1H-indol-4-yl)amino)cyclohexane-1-carbonitrile: To a solution of 2-iodo-1-(2,2,2-trifluoroethyl)-1H-indol-4-amine (1 eq.) in EtOH were added 4-hydroxy-4-methylcyclohexan-1-one or 4-oxocyclohexane-1-carbonitrile (5 eq.) and Ti(OEt)$_4$ (5 eq.). The reaction mixture was stirred at 50° C. for 3~5 h. Then, NaBH$_3$CN (5 eq.) was added to the reaction under N$_2$ at 0° C., and the mixture was stirred for 5 min. The reaction mixture was warmed to 50° C. and stirred further for 1 h. TLC analysis showed that the starting material was consumed completely. The solution was dried in vacuo to give the crude residue, which was purified by column chromatography or prep-TLC to afford 4-((2-iodo-1-(2,2,2-trifluoroethyl)-1H-indol-4-yl)amino)-1-methylcyclohexan-1-ol and 4-((2-iodo-1-(2,2,2-trifluoroethyl)-1H-indol-4-yl)amino)cyclohexane-1-carbonitrile as a yellow or brown oil.

Preparation of final products: To a mixture of 3-methoxy-N-methyl-4-(prop-2-yn-1-ylamino)benzamide (1.2 eq.) in DMSO were added i-Pr$_2$NH (10 eq.), CuI (1 eq.), 4-((2-iodo-1-(2,2,2-trifluoroethyl)-1H-indol-4-yl)amino)-1-methylcyclohexan-1-ol or 4-((2-iodo-1-(2,2,2-trifluoroethyl)-1H-indol-4-yl)amino)cyclohexane-1-carbonitrile (1 eq.), and Pd(PPh$_3$)$_4$ (0.2 eq.) at 25° C. The mixture was stirred for 1-2 h under N$_2$. LC-MS and TLC analysis showed that the reaction was complete. The reaction mixture was quenched by adding a saturated EDTA solution at 25° C. and stirring the mixture for 2 h. The reaction mixture was partitioned by adding EtOAc, and the aqueous phase was extracted with EtOAc. The organic phase was washed with brine, dried over anhydrous sodium sulfate, filtered, and concentrated in vacuo. The crude residue was purified by column chromatography or prep-TLC, then purified further by prep-HPLC to give a solution of the desired product. The solution was lyophilized to afford the desired product as a yellow solid.

3-methoxy-N-methyl-4-{[3-(4-{[(1R,4R)-4-hydroxy-4-methylcyclohexyl]amino}-1-(2,2,2-trifluoroethyl)-1H-indol-2-yl)prop-2-yn-1-yl]amino}benzamide, MS (ES+, m/z): 543.2; 3-methoxy-N-methyl-4-{[3-(4-{[(1S,4S)-4-hydroxy-4-methylcyclohexyl]amino}-1-(2,2,2-trifluoroethyl)-1H-indol-2-yl)prop-2-yn-1-yl]amino}benzamide, MS (ES+, m/z): 543.2; 4-[(3-{4-[(4-cyanocyclohexyl)amino]-1-(2,2,2-trifluoroethyl)-1H-indol-2-yl}prop-2-yn-1-yl)amino]-3-methoxy-N-methylbenzamide, MS (ES+, m/z): 538.2; 3-methoxy-N-methyl-4-{[3-(4-{[(1R,4R)-4-cyanocyclohexyl]amino}-1-(2,2,2-trifluoroethyl)-1H-indol-2-yl)prop-2-yn-1-yl]amino}benzamide, MS (ES+, m/z): 538.2; and 3-methoxy-N-methyl-4-{[3-(4-{[(1S,4S)-4-cyanocyclohexyl]amino}-1-(2,2,2-trifluoroethyl)-1H-indol-2-yl)prop-2-yn-1-yl]amino}benzamide, MS (ES+, m/z): 538.2.

Example C2: Synthesis of Compounds 279A and 280A

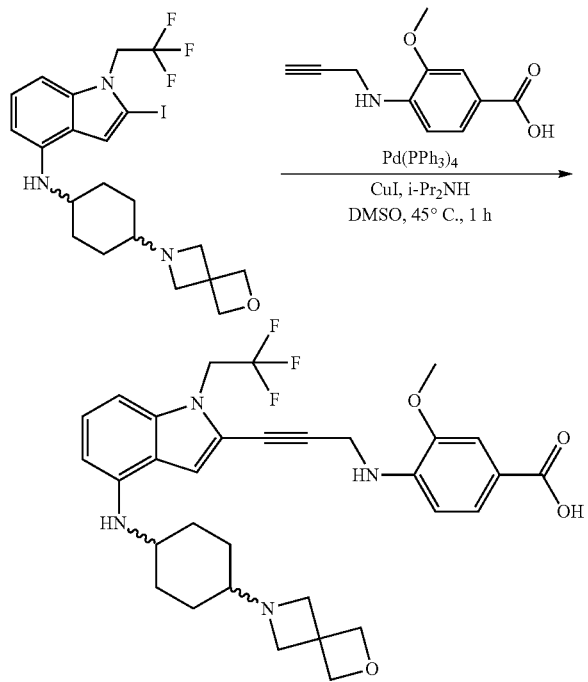

To a solution of 3-methoxy-4-(prop-2-yn-1-ylamino)benzoic acid (52.68 mg, 231.06 µmol, 1.5 eq.) in DMSO (3 mL) were added N-(4-(2-oxa-6-azaspiro[3.3]heptan-6-yl)cyclohexyl)-2-iodo-1-(2,2,2-trifluoroethyl)-1H-indol-4-amine (100 mg, 154.04 µmol, 1 eq.), CuI (29.34 mg, 154.04 µmol, 1 eq.), N-isopropylpropan-2-amine (15.59 mg, 154.04 µmol, 21.77 µL, 1 eq.), and Pd(PPh₃)₄ (3.56 mg, 3.08 µmol, 0.02 eq.). The resulting mixture was stirred at 45° C. for 1 h. TLC analysis (DCM:MeOH=10:1, $R_f$=0.24) indicated that the reaction was complete. The reaction mixture was quenched with saturated EDTA solution (40 mL) at 25° C. and extracted with EtOAc (20 mL×3). The combined organic layers were dried over anhydrous sodium sulfate, filtered, and concentrated under reduced pressure. The crude residue was purified by prep-TLC (SiO₂, DCM:MeOH=10:1) and by prep-HPLC to afford the desired products as yellow solids.

4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxybenzoic acid (26.6 mg, 44.27 µmol, 28.74% yield), MS (ES+, m/z): 597.2; and 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxybenzoic acid (26.3 mg, 40.51 µmol, 26.30% yield), MS (ES+, m/z): 597.2.

Example C3: Synthesis of 3-methoxy-N-methyl-4-{[3-(4-{[(1S,4S)-4-aminocyclohexyl]amino}-1-(2,2,2-trifluoroethyl)-1H-indol-2-yl)prop-2-yn-1-yl]amino}benzamide (Compound 25A)

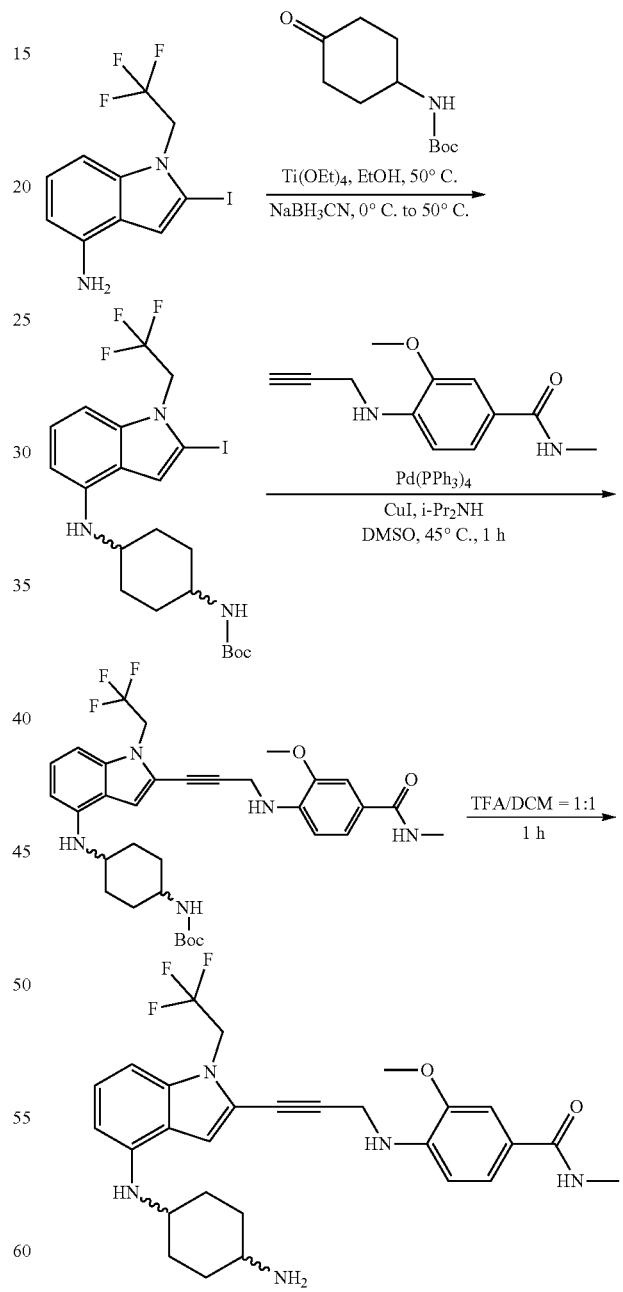

Preparation of tert-butyl (4-((2-iodo-1-(2,2,2-trifluoroethyl)-1H-indol-4-yl)amino)cyclohexyl)carbamate: To a solution of 2-iodo-1-(2,2,2-trifluoroethyl)-1H-indol-4-amine (300 mg, 882.14 µmol, 1 eq.) in EtOH (3 mL) were added tert-butyl (4-oxocyclohexyl)carbamate (940.68 mg, 4.41 mmol, 940.68 μL, 5 eq.) and Ti(OEt)₄ (1.01 g, 4.41 mmol, 914.66 μL, 5 eq.). The reaction mixture was stirred at 50° C. for 3 h. Then, NaBH₃CN (184.78 mg, 2.94 mmol, 5 eq.) was added to the reaction under N₂ at 0° C., and the reaction mixture was stirred further for 5 min. The reaction mixture was warmed to 50° C. and stirred further for 1 h. TLC analysis showed that the starting material was consumed completely. The solution was dried in vacuo, and the crude residue was purified by column chromatography or prep-TLC to give the desired product (300 mg, crude) as a yellow oil or solid. MS (ES⁺, m/z): 552.1.

Preparation of tert-butyl (4-((2-(3-((2-methoxy-4-(methylcarbamoyl)phenyl)amino)prop-1-yn-1-yl)-1-(2,2,2-trifluoroethyl)-1H-indol-4-yl)amino)cyclohexyl)carbamate: To a mixture of 3-methoxy-N-methyl-4-(prop-2-yn-1-ylamino)benzamide (73.11 mg, 334.97 μmol, 2 eq.) and tert-butyl (4-((2-iodo-1-(2,2,2-trifluoroethyl)-1H-indol-4-yl)amino)cyclohexyl)carbamate (100 mg, 167.49 μmol, 1 eq.) in DMSO (3 mL) were added i-Pr₂NH (16.95 mg, 167.49 μmol, 23.67 μL, 1 eq.), Pd(PPh₃)₄ (3.87 mg, 3.35 μmol, 0.02 eq.), and CuI (31.90 mg, 167.49 μmol, 1 eq.) under N₂. The reaction mixture was stirred for 1 h at 45° C. TLC analysis indicated that the reaction was complete. The reaction mixture was quenched by adding a saturated EDTA solution (40 mL) at 25° C., and extracting the mixture was extracted with EtOAc (20 mL×3). The combined organic layers were dried over anhydrous sodium sulfate, filtered, and concentrated under reduced pressure to give a residue. The crude residue was purified by prep-TLC to afford tert-butyl (4-((2-(3-((2-methoxy-4-(methylcarbamoyl)phenyl)amino)prop-1-yn-1-yl)-1-(2,2,2-trifluoroethyl)-1H-indol-4-yl)amino)cyclohexyl)carbamate (70% yield) as a light-yellow solid.

Preparation of 3-methoxy-N-methyl-4-{[3-(4-{[(1S,4S)-4-aminocyclohexyl]amino}-1-(2,2,2-trifluoroethyl)-1H-indol-2-yl)prop-2-yn-1-yl]amino}benzamide: A solution of tert-butyl (4-((2-(3-((2-methoxy-4-(methylcarbamoyl)phenyl)amino)prop-1-yn-1-yl)-1-(2,2,2-trifluoroethyl)-1H-indol-4-yl)amino)cyclohexyl)carbamate (80 mg, 114.71 μmol, 1 eq.) in a 1:1 mixture of DCM (0.5 mL) and TFA (0.5 mL) was stirred at 25° C. for 1 h. TLC analysis indicated that reaction was complete. The reaction mixture was concentrated under reduced pressure and purified by prep-TLC and prep-HPLC to afford the desired product (13.4 mg, 24.51 μmol, 21.37% yield) as a light-yellow solid. MS (ES⁺, m/z): 528.2.

Example C4: Synthesis of Compounds 269A, 270A, 396A, and 397A

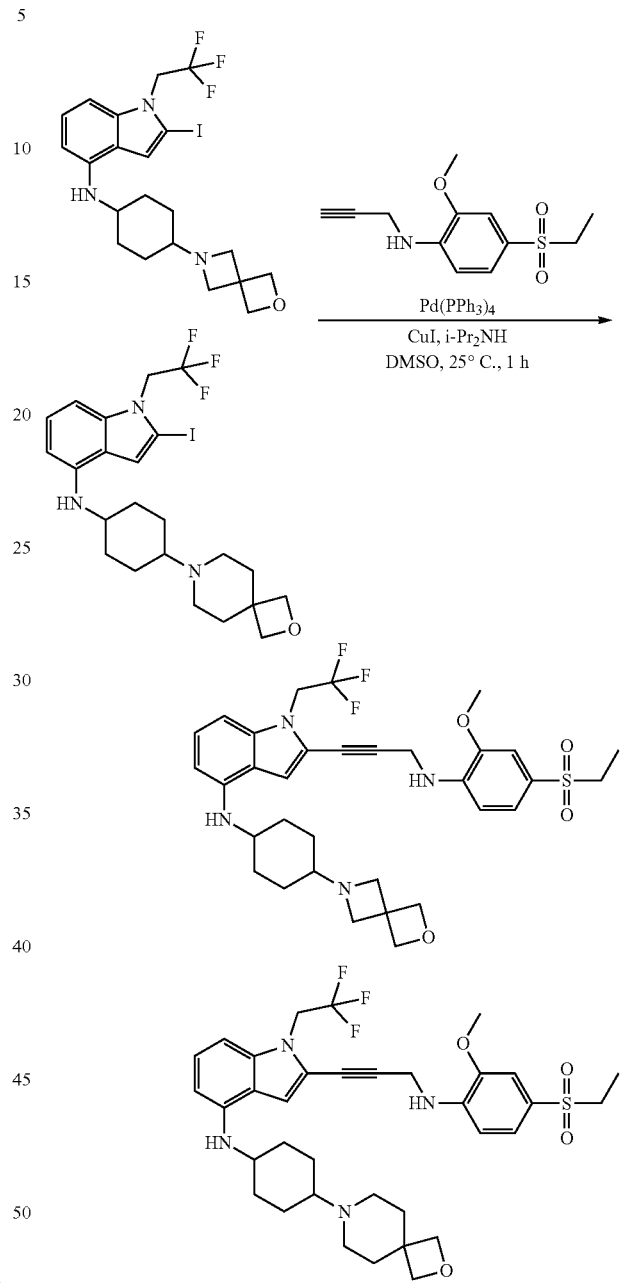

General Procedure: To a mixture of 4-(ethylsulfonyl)-2-methoxy-N-(prop-2-yn-1-yl)aniline (1.3 eq.) in DMSO were added i-Pr₂NH (10 eq.), CuI (0.5 eq.), N-(4-(2-oxa-6-azaspiro[3.3]heptan-6-yl)cyclohexyl)-2-iodo-1-(2,2,2-trifluoroethyl)-1H-indol-4-amine or N-(4-(2-oxa-7-azaspiro[3.5]nonan-7-yl)cyclohexyl)-2-iodo-1-(2,2,2-trifluoroethyl)-1H-indol-4-amine (1 eq.), and Pd(PPh₃)₄ (0.20 eq.) at 25° C. The mixture was stirred for 1 h. LC-MS analysis showed that the reaction was complete. EtOAc was poured into the reaction, and the resulting mixture was then poured into a saturated EDTA solution and stirred for 1 h. The aqueous phase was extracted with EtOAc (3×). The combined organic layers were washed with brine (3×), dried over anhydrous sodium sulfate, mixed with activated carbon to remove color, and concentrated in vacuo. The crude residue was purified by prep-TLC and prep-HPLC to obtain the desired product as a light-yellow solid.

N-((1R,4R)-4-(2-oxa-6-azaspiro[3.3]heptan-6-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine, MS (ES$^+$, m/z): 645.2; N-((1S,4S)-4-(2-oxa-6-azaspiro[3.3]heptan-6-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine, MS (ES$^+$, m/z): 645.2; N-((1R,4R)-4-(2-oxa-7-azaspiro[3.5]nonan-7-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine, MS (ES$^+$, m/z): 673.2; and N-((1S,4S)-4-(2-oxa-7-azaspiro[3.5]nonan-7-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine, MS (ES$^+$, m/z): 673.2.

Example C5: Synthesis of 3-methoxy-4-{[3-(4-{[(1R,4R)-4-(pyrrolidin-1-yl)cyclohexyl]amino}-1-(2,2,2-trifluoroethyl)-1H-indol-2-yl)prop-2-yn-1-yl]amino}benzene-1-sulfonamide (Compound 422A)

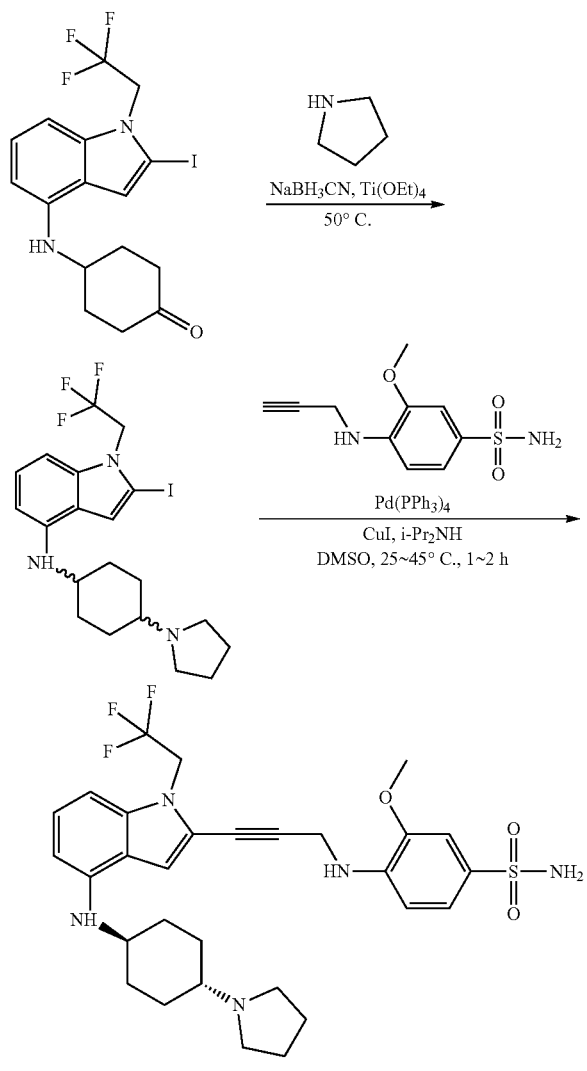

General procedure for the preparation of 2-iodo-N-(4-(pyrrolidin-1-yl)cyclohexyl)-1-(2,2,2-trifluoroethyl)-1H-indol-4-amine: To a solution of 4-((2-iodo-1-(2,2,2-trifluoroethyl)-1H-indol-4-yl)amino)cyclohexan-1-one (1 eq.) in EtOH were added pyrrolidine (5 eq.) and Ti(OEt)$_4$ (5 eq.). The reaction mixture was stirred at 50° C. for 3 h. Then, NaBH$_3$CN (5 eq.) was added to the reaction under N$_2$ at 0° C., and the resulting mixture was stirred for 5 min. The reaction mixture was warmed to 50° C. and stirred for 1 h. TLC and LC-MS analysis showed that the starting material was consumed completely. The solution was dried in vacuo, and the crude residue was purified by column chromatography (SiO$_2$) to afford 2-iodo-N-(4-(pyrrolidin-1-yl)cyclohexyl)-1-(2,2,2-trifluoroethyl)-1H-indol-4-amine.

General procedure for the preparation of 3-methoxy-4-((3-(4-(((1R,4R)-4-(pyrrolidin-1-yl)cyclohexyl)amino)-1-(2,2,2-trifluoroethyl)-1H-indol-2-yl)prop-2-yn-1-yl)amino)benzenesulfonamide: To a mixture of 3-methoxy-4-(prop-2-yn-1-ylamino)benzenesulfonamide (1.2 eq.) in DMSO were added i-Pr$_2$NH (10 eq.), CuI (1 eq.), 2-iodo-N-(4-(pyrrolidin-1-yl)cyclohexyl)-1-(2,2,2-trifluoroethyl)-1H-indol-4-amine (1 eq.), and Pd(PPh$_3$)$_4$ (0.2 eq.) at 25-45° C. The mixture was stirred for 1 h under N$_2$. LC-MS and TLC analysis showed that the reaction was complete. The reaction mixture was quenched by adding a saturated solution of EDTA and stirring the resulting mixture at 25° C. for 2 h. EtOAc was added to the reaction mixture, and the aqueous phase was extracted with EtOAc. The organic phase was washed with brine, dried over anhydrous sodium sulfate, filtered, and concentrated in vacuo to give the crude product. The crude residue was purified by prep-TLC and prep-HPLC to give the solution of the desired product. The solution was lyophilized to afford 3-methoxy-4-{[3-(4-{[(1R,4R)-4-(pyrrolidin-1-yl)cyclohexyl]amino}-1-(2,2,2-trifluoroethyl)-1H-indol-2-yl)prop-2-yn-1-yl]amino}benzene-1-sulfonamide. MS (ES$^+$, m/z): 604.2.

Example C6: Synthesis of Compounds 331A, 332A, 333A, and 334A

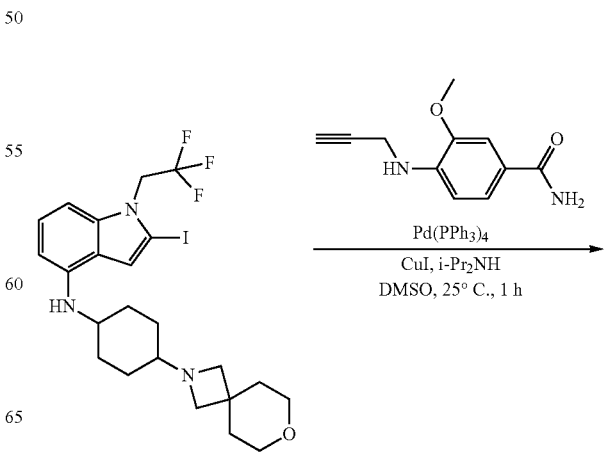

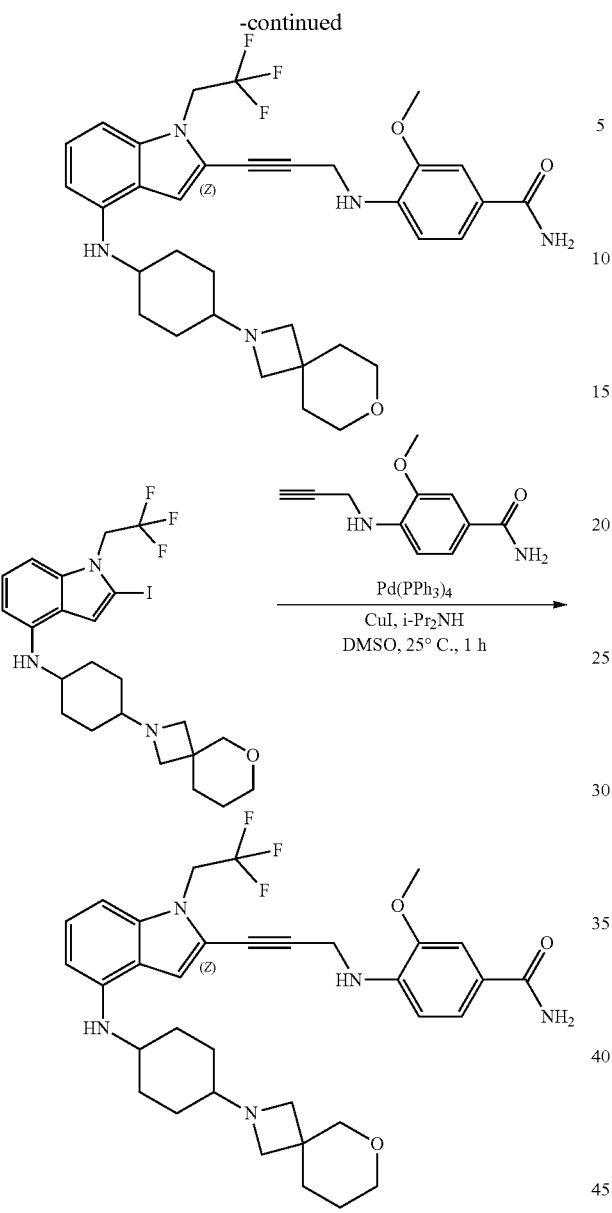

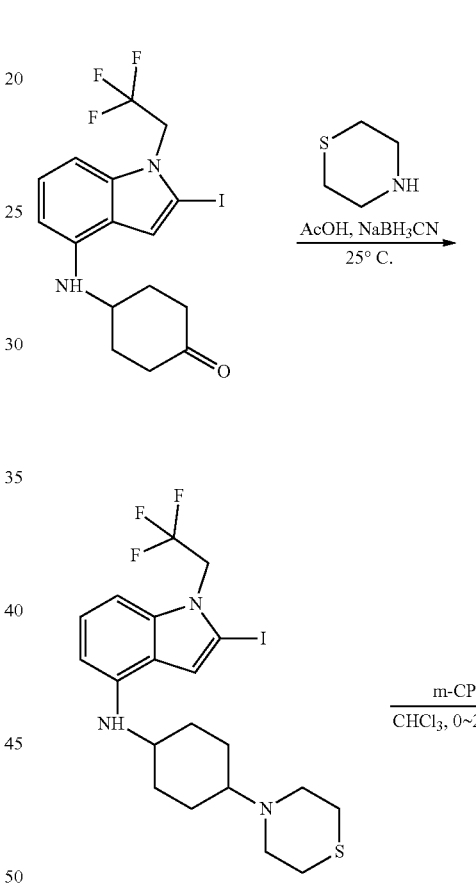

To a solution of 3-methoxy-4-(prop-2-yn-1-ylamino)benzamide (35.88 mg, 147.97 μmol, 1.5 eq.) in DMSO (3 mL) were added i-Pr₂NH (9.98 mg, 98.65 μmol, 13.94 μL, 1 eq.), CuI (626.26 mg, 3.29 mmol, 2 eq.), N-(4-(7-oxa-2-azaspiro[3.5]nonan-2-yl)cyclohexyl)-2-iodo-1-(2,2,2-trifluoroethyl)-1H-indol-4-amine or N-(4-(6-oxa-2-azaspiro[3.5]nonan-2-yl)cyclohexyl)-2-iodo-1-(2,2,2-trifluoroethyl)-1H-indol-4-amine (60 mg, 98.65 μmol, 1 eq.), and Pd(PPh₃)₄ (2.28 mg, 1.97 μmol, 0.02 eq.) at 25° C. The mixture was stirred at 25° C. for 1 h under N₂. The mixture was poured into a saturated EDTA solution (20 mL), stirred at 25° C. for 1 h, and extracted with EtOAc (20 mL×3). The combined organic layers were concentrated under reduced pressure to give a residue, which was purified by prep-TLC and prep-HPLC to afford the desired product.

3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide, MS (ES⁺, m/z): 624.3; 4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzamide, MS (ES⁺, m/z): 624.3; 3-methoxy-4-{[3-(4-{[(1R,4R)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzamide, MS (ES⁺, m/z): 624.3; 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzamide. MS (ES⁺, m/z): 624.3.

Example C7: Synthesis of 3-methoxy-4-{[3-(4-{[(1R,4R)-4-(1,1-dioxo-1λ⁶-thiomorpholin-4-yl)cyclohexyl]amino}-1-(2,2,2-trifluoroethyl)-1H-indol-2-yl)prop-2-yn-1-yl]amino}benzene-1-sulfonamide (Compound 372A)

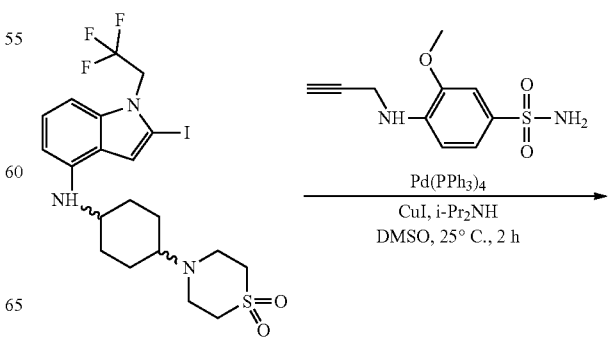

-continued

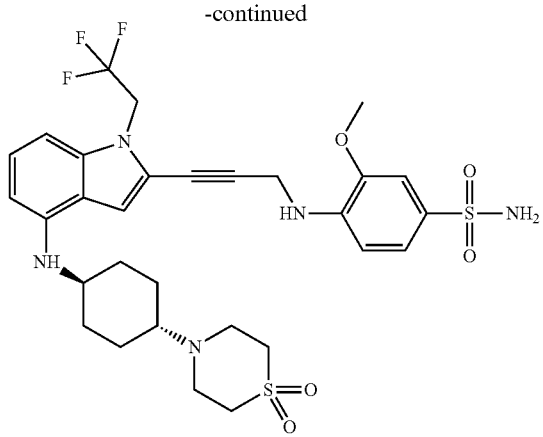

Preparation of 2-iodo-N-(4-thiomorpholinocyclohexyl)-1-(2,2,2-trifluoroethyl)-1H-indol-4-amine: To a solution of 4-((2-iodo-1-(2,2,2-trifluoroethyl)-1H-indol-4-yl)amino)cyclohexan-1-one (1 eq.) in thiomorpholine (10.90 g, 105.63 mmol, 10 mL, 51.20 eq.) was added AcOH (1 eq.). The reaction mixture was stirred at 25° C. for 2 h. Then, NaBH$_3$CN (5 eq.) was added to the reaction mixture under N$_2$ at 0° C., and the mixture was stirred for 5 min. The reaction mixture was warmed to 50° C. and stirred further for 3 h. TLC and LC-MS analysis showed that the starting material was consumed completely. The reaction was partitioned by adding water (100 mL) and EtOAc (20 mL). The residue was purified by column chromatography (SiO$_2$, PE:EtOAc=10:1 to 0:1) to afford 2-iodo-N-(4-thiomorpholinocyclohexyl)-1-(2,2,2-trifluoroethyl)-1H-indol-4-amine.

Preparation of 4-(4-((2-iodo-1-(2,2,2-trifluoroethyl)-1H-indol-4-yl)amino)cyclohexyl)thiomorpholine 1,1-dioxide: A mixture of 2-iodo-N-(4-thiomorpholinocyclohexyl)-1-(2,2,2-trifluoroethyl)-1H-indol-4-amine (1 eq.) in CHCl$_3$ (20 mL) was added m-CPBA (5 eq.) at 0° C. The mixture was stirred at 0~25° C. for 5 h. TLC and LC-MS analysis showed that the reaction was complete. The reaction was partitioned by adding a saturated solution of Na$_2$CO$_3$ (200 mL) and EtOAc (50 mL). The residue was purified by column chromatography (SiO$_2$) to afford 4-(4-((2-iodo-1-(2,2,2-trifluoroethyl)-1H-indol-4-yl)amino)cyclohexyl)thiomorpholine 1,1-dioxide.

Preparation of 3-methoxy-4-{[3-(4-{[(1R,4R)-4-(1,1-dioxo-1λ$^6$-thiomorpholin-4-yl)cyclohexyl]amino}-1-(2,2,2-trifluoroethyl)-1H-indol-2-yl)prop-2-yn-1-yl]amino}benzene-1-sulfonamide: To a solution of 3-methoxy-4-(prop-2-yn-1-ylamino)benzenesulfonamide (1.2 eq.) in DMSO (1 mL) were added i-Pr$_2$NH (10 eq.), CuI (1 eq.), 4-(4-((2-iodo-1-(2,2,2-trifluoroethyl)-1H-indol-4-yl)amino)cyclohexyl)thiomorpholine 1,1-dioxide (1 eq.), and Pd(PPh$_3$)$_4$ (0.2 eq.) at 25° C. The mixture was stirred for 1 h under N$_2$. LC-MS and TLC analysis showed that the reaction was complete. The reaction mixture was quenched by adding a saturated EDTA solution (30 mL) at 25° C. and stirring the mixture for 2 h. The resulting mixture was partitioned by adding EtOAc (10 mL), and the aqueous phase was extracted with EtOAc (10 mL×3). The organic phase was washed with brine (10 mL×3), dried over anhydrous sodium sulfate, filtered, and concentrated in vacuo to give the crude product. The crude residue was purified by prep-TLC and prep-HPLC to give a solution of the desired product. The solution was lyophilized to afford 3-methoxy-4-{[3-(4-{[(1R,4R)-4-(1,1-dioxo-1λ$^6$-thiomorpholin-4-yl)cyclohexyl]amino}-1-(2,2,2-trifluoroethyl)-1H-indol-2-yl)prop-2-yn-1-yl]amino}benzene-1-sulfonamide. MS (ES$^+$, m/z): 668.2.

Example C8: Synthesis of Compounds 77A and 78A

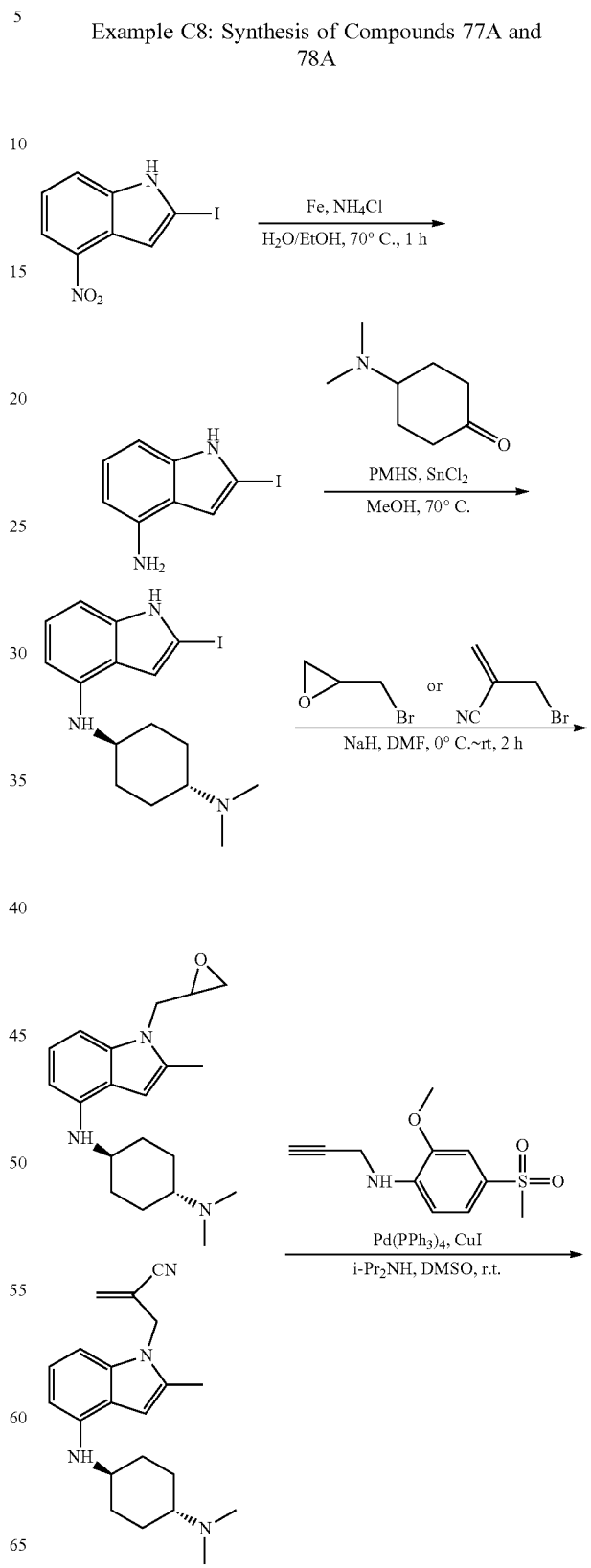

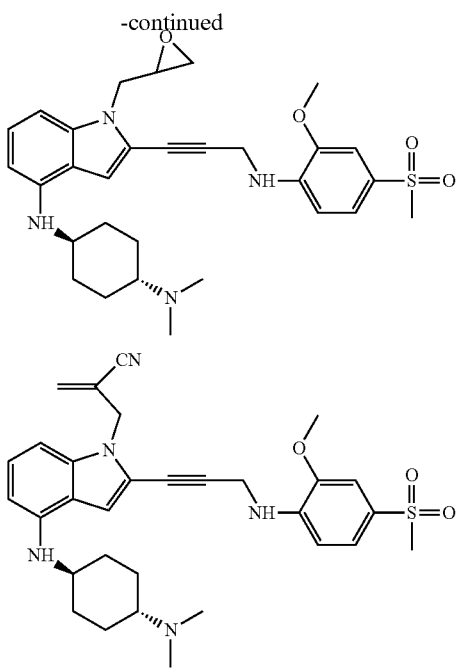

Preparation of 2-iodo-1H-indol-4-amine: To a solution of 2-iodo-4-nitro-1H-indole (3 g, 10.4 mmol, 1 eq.) in EtOH (30 mL) was added saturated solution of NH$_4$Cl (5 mL) at 25° C. The mixture was heated to 70° C., and Fe (2.9 g, 52.1 mmol, 5 eq.) was added. The resulting mixture was stirred at 70° C. for 1 h. TLC analysis (PE:EtOAc=3:1, R$_f$=0.5) showed that the reaction was complete. The reaction mixture was dried, and the residue was dissolved in EtOAc (15 mL) and washed with water (50 mL). The organic layer was then concentrated, and the crude product was purified by column chromatography (PE:EtOAc=2:1) to afford 2-iodo-1H-indol-4-amine (2.5 g, 9.7 mmol, 93% yield) as a black brown solid.

Preparation of (1R,4R)—N$^1$-(2-iodo-1H-indol-4-yl)-N$^4$,N$^4$-dimethylcyclohexane-1,4-diamine: To a solution of 2-iodo-1H-indol-4-amine (0.5 g, 1.9 mmol, 1 eq.) in MeOH (5 mL) were added 4-(dimethylamino)cyclohexanone (1.37 g, 9.7 mmol, 5 eq.), polymethyldrosiloxane (PMHS) (581.26 mg, 9.69 mmol, 5 eq.), and SnCl$_2$·2H$_2$O (437.20 mg, 1.94 mmol, 1 eq.). The mixture was stirred at 70° C. for 3 h. LC-MS analysis showed that the reaction was complete. 2 g of sodium sulfate was added to the reaction, and the mixture was filtered. The filtered solution was concentrated in vacuo, and the crude product was purified by prep-TLC (MeOH, R$_f$=0.3) to afford (1R,4R)—N$^1$-(2-iodo-1H-indol-4-yl)-N$^4$,N$^4$-dimethylcyclohexane-1,4-diamine (260 mg, 474.9 μmol, 24.5% yield) as a gray solid. MS (ES$^+$, m/z): 382.0.

Preparation of (1R,4R)—N$^1$-(2-iodo-1-(oxiran-2-ylmethyl)-1H-indol-4-yl)-N$^4$,N$^4$-dimethylcyclohexane-1,4-diamine and 2-((4-(((1R,4R)-4-(dimethylamino)cyclohexyl)amino)-2-iodo-1H-indol-1-yl)methyl)acrylonitrile: To a solution of (1R,4R)—N$^1$-(2-iodo-1H-indol-4-yl)-N$^4$,N$^4$-dimethylcyclohexane-1,4-diamine (1 eq.) in DMF (10 mL) was added NaH (2 eq.). The reaction mixture was stirred at 0° C. for 20 min, and 2-(bromomethyl)oxirane or 2-(bromomethyl)acrylonitrile (1.2 eq.) was added. The reaction mixture was stirred further at 0~25° C. for 40 min. LC-MS analysis showed that the reaction was complete. The reaction mixture was quenched with water (10 mL) and extracted with EtOAc (10 mL). The combined organic layers were dried over sodium sulfate, filtered, and concentrated in vacuo. The crude product was purified by prep-TLC to afford the desired products as brown solids. (1R,4R)—N$^1$-(2-iodo-1-(oxiran-2-ylmethyl)-1H-indol-4-yl)-N$^4$,N$^4$-dimethylcyclohexane-1,4-diamine, MS (ES$^+$, m/z): 440.2; and 2-((4-(((1R,4R)-4-(dimethylamino)cyclohexyl)amino)-2-iodo-1H-indol-1-yl)methyl)acrylonitrile, MS (ES$^+$, m/z): 449.0.

General procedure for the preparation of (1R,4R)—N$^4$-(2-{3-[(4-methanesulfonyl-2-methoxyphenyl)amino]prop-1-yn-1-yl}-1-[(oxiran-2-yl)methyl]-1H-indol-4-yl)-N$^1$,N$^1$-dimethylcyclohexane-1,4-diamine and 2-[(2-{3-[(4-methanesulfonyl-2-methoxyphenyl)amino]prop-1-yn-1-yl}-4-{[(1R,4R)-4-(dimethylamino)cyclohexyl]amino}-1H-indol-1-yl)methyl]prop-2-enenitrile: To a mixture of 2-methoxy-4-(methylsulfonyl)-N-(prop-2-yn-1-yl)aniline (1.3 eq.) in DMSO were added i-Pr$_2$NH (10 eq.), CuI (1 eq.), (1R,4R)—N$^1$-(2-iodo-1-(oxiran-2-ylmethyl)-1H-indol-4-yl)-N$^4$,N$^4$-dimethylcyclohexane-1,4-diamine or 2-((4-(((1R,4R)-4-(dimethylamino)cyclohexyl)amino)-2-iodo-1H-indol-1-yl)methyl)acrylonitrile (1 eq.), and Pd(PPh$_3$)$_4$ (0.2 eq.) at 25° C. The mixture was stirred for 1 h under N$_2$. LC-MS or TLC analysis showed that the reaction was complete. The reaction mixture was quenched by adding a saturated EDTA solution, and the resulting mixture was stirred at 25° C. for 2 h. The reaction mixture was partitioned by adding EtOAc. The layers were separated, and the aqueous phase was extracted with EtOAc. The organic phase was washed with brine, dried over anhydrous sodium sulfate, filtered, and concentrated in vacuo. The crude residue was purified by prep-TLC and prep-HPLC to give a solution of the desired product. The solution was lyophilized to afford the desired product as a light-yellow solid. (1R,4R)—N$^4$-(2-{3-[(4-methanesulfonyl-2-methoxyphenyl)amino]prop-1-yn-1-yl}-1-[(oxiran-2-yl)methyl]-1H-indol-4-yl)-N$^1$,N$^1$-dimethylcyclohexane-1,4-diamine, MS (ES$^+$, m/z): 551.2; and 2-[(2-{3-[(4-methanesulfonyl-2-methoxyphenyl)amino]prop-1-yn-1-yl}-4-{[(1R,4R)-4-(dimethylamino)cyclohexyl]amino}-1H-indol-1-yl)methyl]prop-2-enenitrile, MS (ES$^+$, m/z): 560.3.

Example C9: Synthesis of Compounds 119A, 120A, 314A, and 315A

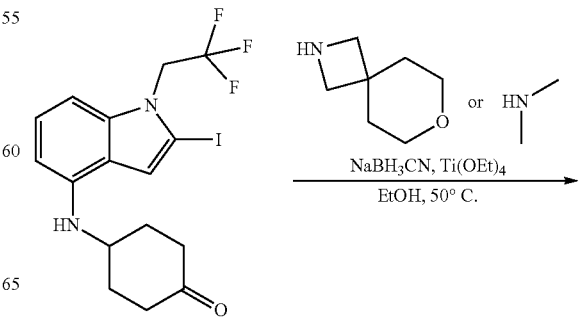

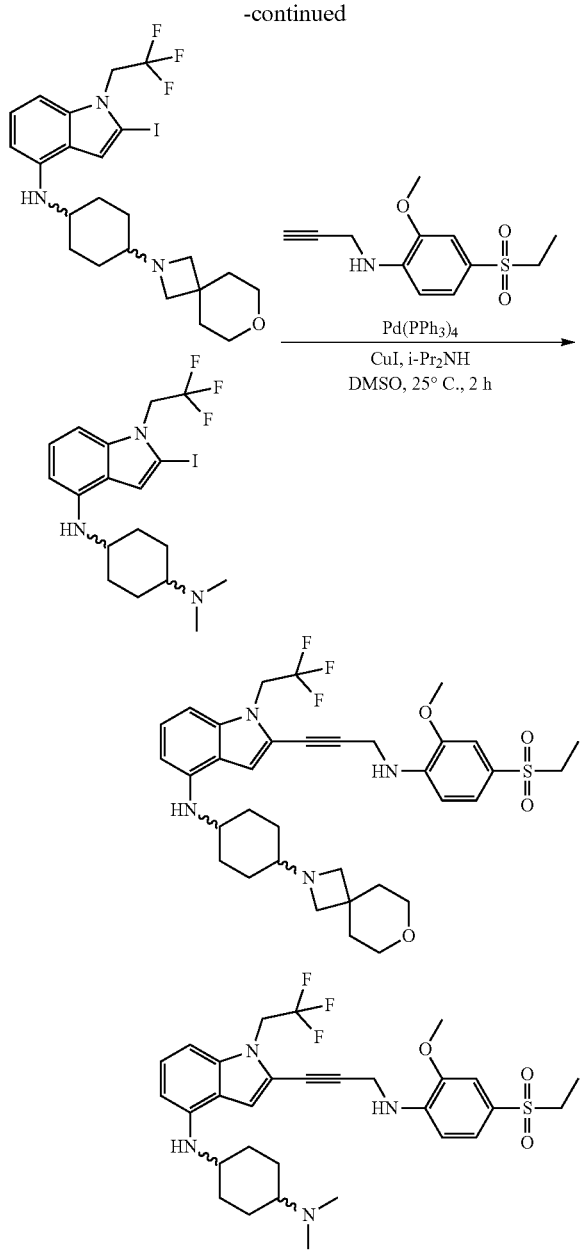

General Procedure for the preparation of N-(4-(7-oxa-2-azaspiro[3.5]nonan-2-yl)cyclohexyl)-2-iodo-1-(2,2,2-trifluoroethyl)-1H-indol-4-amine and N¹-(2-iodo-1-(2,2,2-trifluoroethyl)-1H-indol-4-yl)-N⁴,N⁴-dimethylcyclohexane-1,4-diamine: To a solution of 4-((2-iodo-1-(2,2,2-trifluoroethyl)-1H-indol-4-yl)amino)cyclohexan-1-one (1 eq.) in EtOH were added 7-oxa-2-azaspiro[3.5]nonane or dimethylamine (5 eq.), Ti(OEt)₄ (5 eq.), and i-Pr₂NH (1 eq.). The reaction mixture was stirred at 50° C. for 3 h. Then, NaBH₃CN (5 eq.) was added to the reaction mixture under N₂ at 0° C., and the mixture was stirred further for 5 min, warmed to 50° C., and stirred for 1 h. TLC and LC-MS analysis showed that the starting material was consumed completely. The solution was concentrated under reduced pressure to give the crude product. The crude residue was purified by column chromatography (SiO₂) to afford the desired products.

Preparation of final products: To a solution of 4-(ethylsulfonyl)-2-methoxy-N-(prop-2-yn-1-yl)aniline (1.2 eq.) in DMSO were added i-Pr₂NH (10 eq.), CuI (1 eq.), N-(4-(7-oxa-2-azaspiro[3.5]nonan-2-yl)cyclohexyl)-2-iodo-1-(2,2,2-trifluoroethyl)-1H-indol-4-amine or N¹-(2-iodo-1-(2,2,2-trifluoroethyl)-1H-indol-4-yl)-N⁴,N⁴-dimethylcyclohexane-1,4-diamine (1 eq.), and Pd(PPh₃)₄ (0.2 eq.) at 25° C. The mixture was stirred at 25° C. for 1 h under N₂. LC-MS and TLC analysis showed that the reaction was complete. The reaction mixture was quenched by adding a saturated EDTA solution at 25° C. and stirring the mixture for 2 h. EtOAc was added to the mixture, and the aqueous phase was extracted with EtOAc, The organic phase was washed with brine, dried over anhydrous sodium sulfate, filtered, and concentrated in vacuo to give the crude product. The crude residue was purified by prep-TLC and prep-HPLC to give solutions of the desired products. The solutions were lyophilized to afford the desired products.

2-(3-{[4-(ethanesulfonyl)-2-methoxyphenyl]amino}prop-1-yn-1-yl)-N-[(1R,4R)-4-{7-oxa-2-azaspiro[3.5]nonan-2-yl}cyclohexyl]-1-(2,2,2-trifluoroethyl)-1H-indol-4-amine, MS (ES⁺, m/z): 673.4; 2-(3-{[4-(ethanesulfonyl)-2-methoxyphenyl]amino}prop-1-yn-1-yl)-N-[(1S,4S)-4-{7-oxa-2-azaspiro[3.5]nonan-2-yl}cyclohexyl]-1-(2,2,2-trifluoroethyl)-1H-indol-4-amine, MS (ES⁺, m/z): 673.3; (1R,4R)—N⁴-[2-(3-{[4-(ethanesulfonyl)-2-methoxyphenyl]amino}prop-1-yn-1-yl)-1-(2,2,2-trifluoroethyl)-1H-indol-4-yl]-N¹,N¹-dimethylcyclohexane-1,4-diamine, MS (ES⁺, m/z): 591.4; and (1S,4S)—N⁴-[2-(3-{[4-(ethanesulfonyl)-2-methoxyphenyl]amino}prop-1-yn-1-yl)-1-(2,2,2-trifluoroethyl)-1H-indol-4-yl]-N¹,N¹-dimethylcyclohexane-1,4-diamine, MS (ES⁺, m/z): 591.3.

Example C10: Synthesis of Compounds 153A and 154A

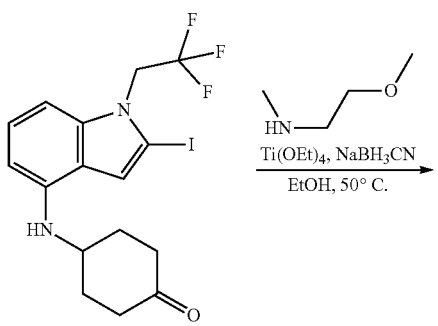

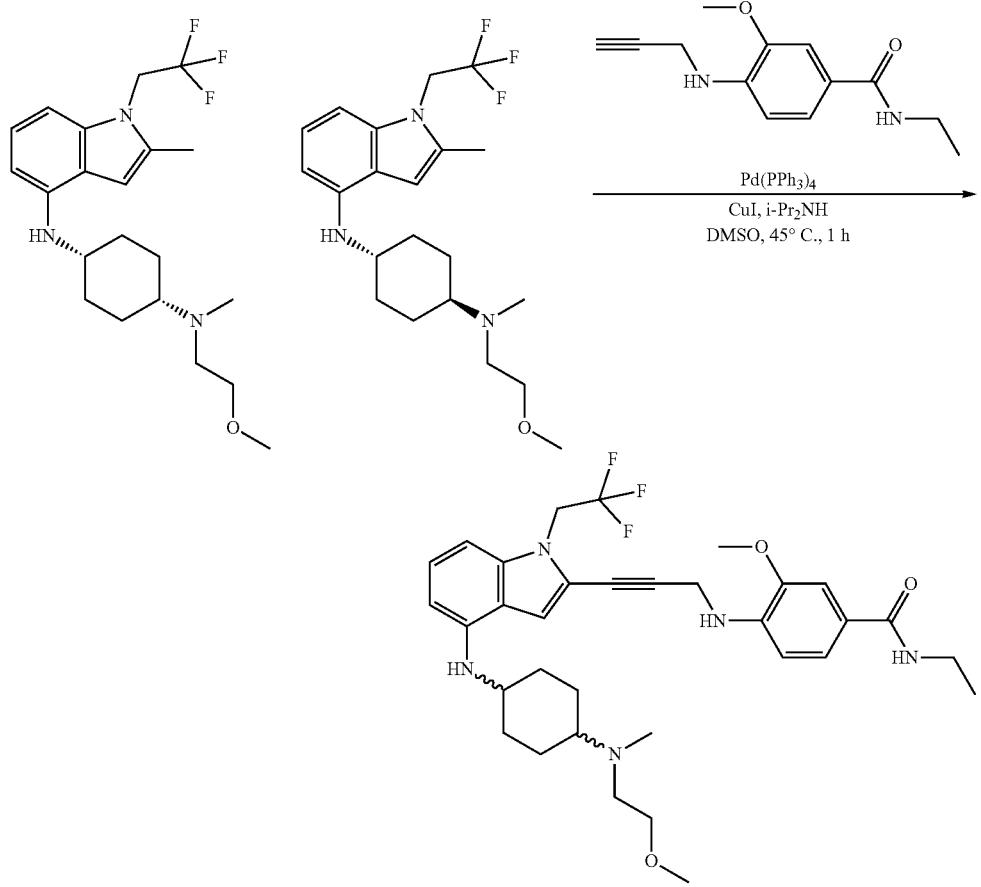

Preparation of (1R,4R)—N$^1$-(2-iodo-1-(2,2,2-trifluoroethyl)-1H-indol-4-yl)-N$^4$-(2-methoxyethyl)-N$^4$-methylcyclohexane-1,4-diamine and (1S,4S)—N$^1$-(2-iodo-1-(2,2,2-trifluoroethyl)-1H-indol-4-yl)-N$^4$-(2-methoxyethyl)-N$^4$-methylcyclohexane-1,4-diamine: To a solution of 4-((2-iodo-1-(2,2,2-trifluoroethyl)-1H-indol-4-yl)amino)cyclohexan-1-one (1 g, 2.20 mmol, 1 eq.) and 2-methoxy-N-methyl-ethanamine (980.84 mg, 11 mmol, 1.18 mL, 5 eq.) in EtOH (10 mL) was added Ti(OEt)$_4$ (2.01 g, 8.80 mmol, 1.83 mL, 4 eq.). The mixture was stirred at 50° C. for 4 h, and NaBH$_3$CN (276.59 mg, 4.40 mmol, 2 eq.) was added. The resulting mixture was stirred at 50° C. for 1 h. LC-MS and TLC analysis (PE:EtOAc=3:1, R$_{f1}$=0.05, R$_{f2}$=0.10) showed that the reaction was complete. The reaction mixture was poured into a saturated aqueous solution of NaHCO$_3$ (60 mL) and filtered to give a filter liquor. The filter liquor was extracted with EtOAc (60 mL×3). The combined organic layers were washed with brine (40 mL), dried over anhydrous sodium sulfate, filtered, and concentrated in vacuo. The residue was purified by column chromatography (SiO$_2$, PE:EtOAc:TEA=20:20:1, R$_{f1}$=0.3, R$_{f2}$=0.4) to afford the desired product as a yellow oil.

(1R,4R)—N$^1$-(2-iodo-1-(2,2,2-trifluoroethyl)-1H-indol-4-yl)-N$^4$-(2-methoxyethyl)-N$^4$-methylcyclohexane-1,4-diamine (600 mg, 1.06 mmol, 48.17% yield); and (1S,4S)—N$^1$-(2-iodo-1-(2,2,2-trifluoroethyl)-1H-indol-4-yl)-N$^4$-(2-methoxyethyl)-N$^4$-methylcyclohexane-1,4-diamine (500 mg, 883.49 mol, 40.14% yield).

Preparation of N-ethyl-3-methoxy-4-((3-(4-((4-((2-methoxyethyl)(methyl)amino)cyclohexyl)-amino)-1-(2,2,2-trifluoroethyl)-1H-indol-2-yl)prop-2-yn-1-yl)amino)benzamide: To a mixture of N-ethyl-3-methoxy-4-(prop-2-yn-1-ylamino)benzamide (1~2 eq., HCl or free) in DMSO (1~10 mL) were added i-Pr$_2$NH (10~30 eq.), CuI (1~2 eq.), (1R,4R)—N$^1$-(2-iodo-1-(2,2,2-trifluoroethyl)-1H-indol-4-yl)-N$^4$-(2-methoxyethyl)-N$^4$-methylcyclohexane-1,4-diamine or (1S,4S)—N$^1$-(2-iodo-1-(2,2,2-trifluoroethyl)-1H-indol-4-yl)-N$^4$-(2-methoxyethyl)-N$^4$-methylcyclohexane-1,4-diamine (1 eq.), and Pd(PPh$_3$)$_4$ (0.20~0.50 eq.) at 20~45° C. The mixture was stirred at 20~45° C. for 1~4 h. EtOAc (10 mL) was poured into the reaction mixture, and the resulting mixture was then poured into 2N aqueous EDTA (40 mL) and stirred for 15 min. The aqueous phase was extracted with EtOAc (30 mL×3). The organic layer was poured again into saturated EDTA solution (30 mL) (saturation) and stirred further for 1 h. The aqueous phase was extracted with EtOAc (30 mL×3). The combined organic layers were washed with brine (30 mL×3), dried over anhydrous sodium sulfate, treated with activated carbon, filtered, and concentrated in vacuo. The crude residue was purified by prep-TLC or column chromatography, then purified once or twice prep-HPLC to afford N-ethyl-3-methoxy-4-((3-(4-((4-((2-methoxyethyl)(methyl)amino)cyclohexyl)amino)-1-(2,2,2-trifluoroethyl)-1H-indol-2-yl)prop-2-yn-1-yl)amino)benzamide.

Example C11: Synthesis of Compounds 117A, 118A, 155A, 156A, and 661A

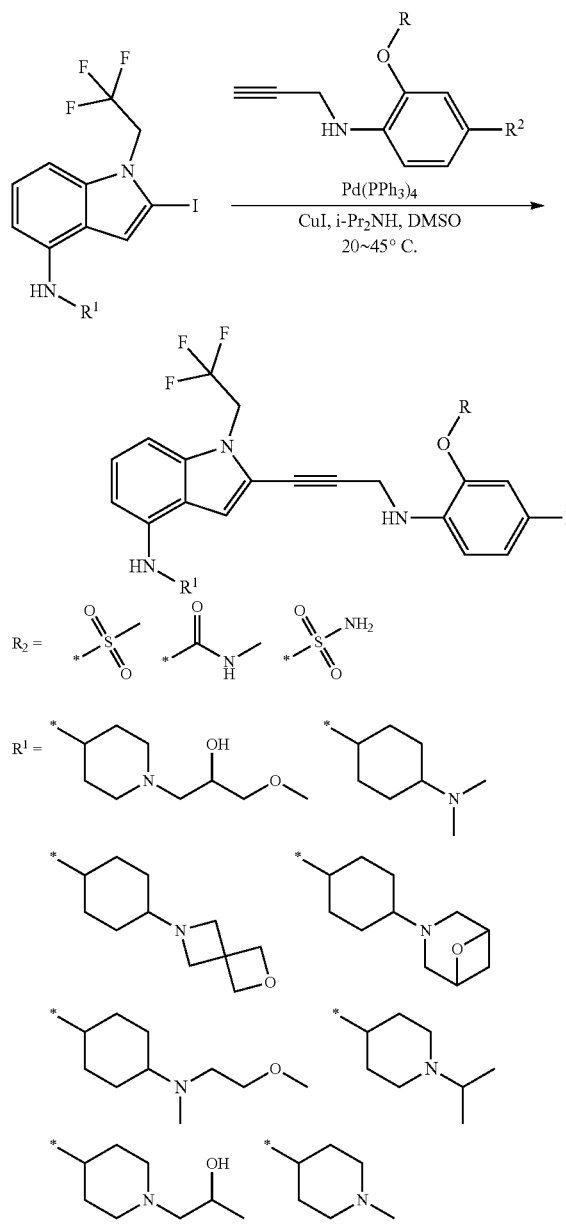

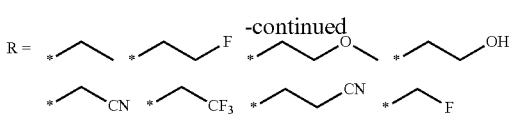

General Procedure: To a mixture of the R- and $R^2$-substituted alkyne compound above (1~2 eq.) in DMSO were added i-Pr$_2$NH (10~30 eq.), CuI (1~2 eq.), $R^1$-substituted 2-iodo-1-(2,2,2-trifluoroethyl)-1H-indol-4-amine (1 eq.), and Pd(PPh$_3$)$_4$ (0.20~0.50 eq.). The mixture was stirred at 20~45° C. for 1-3 h under N$_2$. The mixture was poured into a saturated aqueous solution of EDTA and stirred for 1 h, and the aqueous phase was extracted with EtOAc (3×) The combined organic layers were washed with brine (3×), dried over anhydrous sodium sulfate, filtered, and concentrated in vacuo. The residue was purified by TLC, prep-HPLC, or TLC and prep-HPLC to afford the desired product.

(1R,4R)—$N^1$-(2-(3-((2-(fluoromethoxy)-4-(methylsulfonyl)phenyl)amino)prop-1-yn-1-yl)-1-(2,2,2-trifluoroethyl)-1H-indol-4-yl)-$N^4$,$N^4$-dimethylcyclohexane-1,4-diamine, MS (ES$^+$, m/z): 595.2; (1S,4S)—$N^1$-(2-(3-((2-(fluoromethoxy)-4-(methylsulfonyl)phenyl)amino)prop-1-yn-1-yl)-1-(2,2,2-trifluoroethyl)-1H-indol-4-yl)-$N^4$,$N^4$-dimethylcyclohexane-1,4-diamine, MS (ES$^+$, m/z): 595.2; (1R,4R)—$N^1$-(2-(3-((2-(fluoromethoxy)-4-(methylsulfonyl)phenyl)amino)prop-1-yn-1-yl)-1-(2,2,2-trifluoroethyl)-1H-indol-4-yl)-$N^4$-(2-methoxyethyl)-$N^4$-methylcyclohexane-1,4-diamine, MS (ES$^+$, m/z): 639.3; (1S,4S)—$N^1$-(2-(3-((2-(fluoromethoxy)-4-(methylsulfonyl)phenyl)amino)prop-1-yn-1-yl)-1-(2,2,2-trifluoroethyl)-1H-indol-4-yl)-$N^4$-(2-methoxyethyl)-$N^4$-methylcyclohexane-1,4-diamine, MS (ES$^+$, m/z): 639.3; and 2-(2-{[3-(4-{[1-(2-hydroxypropyl)piperidin-4-yl]amino}-1-(2,2,2-trifluoroethyl)-1H-indol-2-yl)prop-2-yn-1-yl]amino}-5-methanesulfonylphenoxy)acetonitrile, MS (ES$^+$, m/z): 618.2.

Example C12: Synthesis of Compounds 183A and 184A

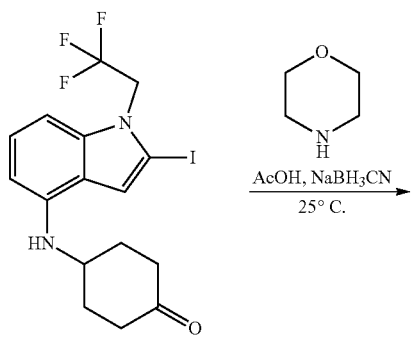

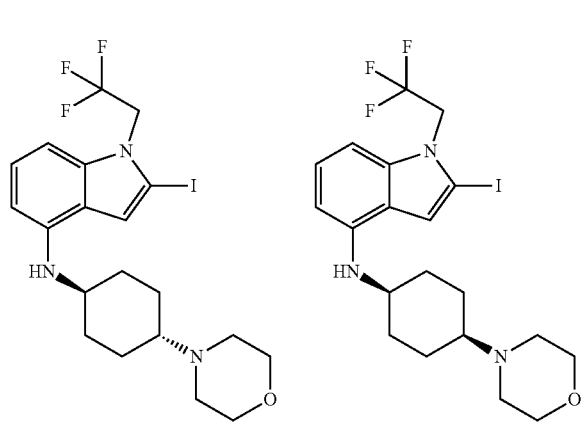
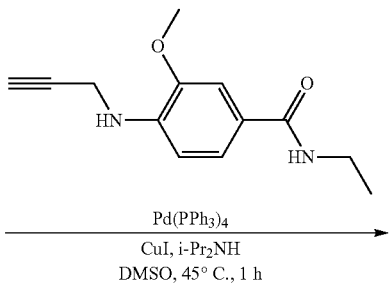

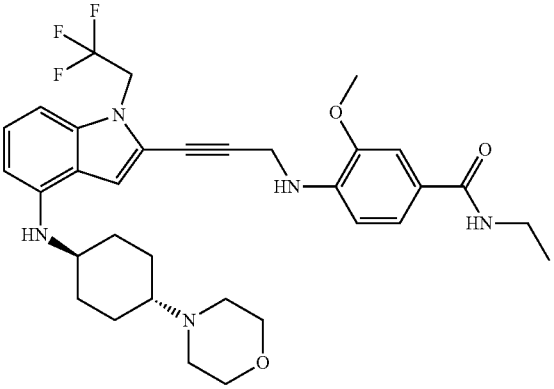

Preparation of 2-iodo-N-((1R,4R)-4-morpholinocyclohexyl)-1-(2,2,2-trifluoroethyl)-1H-indol-4-amine and 2-iodo-N-((1S,4S)-4-morpholinocyclohexyl)-1-(2,2,2-trifluoroethyl)-1H-indol-4-amine: To a mixture of 4-((2-iodo-1-(2,2,2-trifluoroethyl)-1H-indol-4-yl)amino)cyclohexan-1-one (1 g, 2.20 mmol, 1 eq.) and morpholine (9.59 g, 110.04 mmol, 9.68 mL, 50 eq.) was added AcOH (158.59 mg, 2.64 mmol, 151.04 μL, 1.2 eq.). The mixture was stirred at 25° C. for 4 h, and NaBH$_3$CN (276.60 mg, 4.40 mmol, 2 eq.) was added. The resulting mixture was stirred at 25° C. for 1 h. LC-MS and TLC analysis (PE:EtOAc=3:1, R$_{f1}$, =0.1, R$_{f2}$=0.15) showed that the reaction was complete. The reaction mixture was poured into a saturated aqueous solution of NaHCO$_3$ (60 mL) and filtered to give a filter liquor. It was then extracted with EtOAc (60 mL×3). The combined organic layers were washed with brine (40 mL), dried over anhydrous sodium sulfate, filtered, and concentrated in vacuo. The crude residue was purified by column chromatography (SiO$_2$, PE:EtOAc=2:1 to 0:1, R$_{f1}$=0.2, R$_{f2}$=0.3) to afford the desired products as light-yellow solids. 2-iodo-N-((1R,4R)-4-morpholinocyclohexyl)-1-(2,2,2-trifluoroethyl)-1H-indol-4-amine (550 mg, 975.70 μmol, 44.33% yield); and 2-iodo-N-((1S,4S)-4-morpholinocyclohexyl)-1-(2,2,2-trifluoroethyl)-1H-indol-4-amine (500 mg, 887 μmol, 40.30% yield).

Preparation of N-ethyl-3-methoxy-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide and N-ethyl-3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzamide: To a solution of N-ethyl-3-methoxy-4-(prop-2-yn-1-ylamino)benzamide (1~2 eq., HCl or free) in DMSO (1~10 mL) were added i-Pr$_2$NH (10~30 eq.), CuI (1~2 eq.), 2-iodo-N-((1R,4R)-4-morpholinocyclohexyl)-1-(2,2,2-trifluoroethyl)-1H-indol-4-amine or 2-iodo-N-((1S,4S)-4-morpholinocyclohexyl)-1-(2,2,2-trifluoroethyl)-1H-indol-4-amine (1 eq.), and Pd(PPh$_3$)$_4$ (0.20~0.50 eq.) at 20~45° C. The mixture was stirred at 20~45° C. for 1~4 h. EtOAc (10 mL) was poured into the mixture, and the resulting mixture was then poured into 2N aqueous EDTA (40 mL) and stirred for 15 min. The aqueous phase was extracted with EtOAc (3×). The combined organic layers were poured to 2N aqueous EDTA and stirred for 1 h. The aqueous phase was extracted again with EtOAc (3×). The combined organic layers were washed with brine (3×), dried over anhydrous sodium sulfate, treated with activated carbon, filtered, and concentrated in vacuo. The crude mixture was purified by prep-TLC or column chromatography, then purified once or twice using prep-HPLC to afford the desired products.

N-ethyl-3-methoxy-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide, MS (ES$^+$, m/z): 612.3; and N-ethyl-3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzamide, MS (ES$^+$, m/z): 612.3.

Example C13: Synthesis of Compounds 324A and 325A

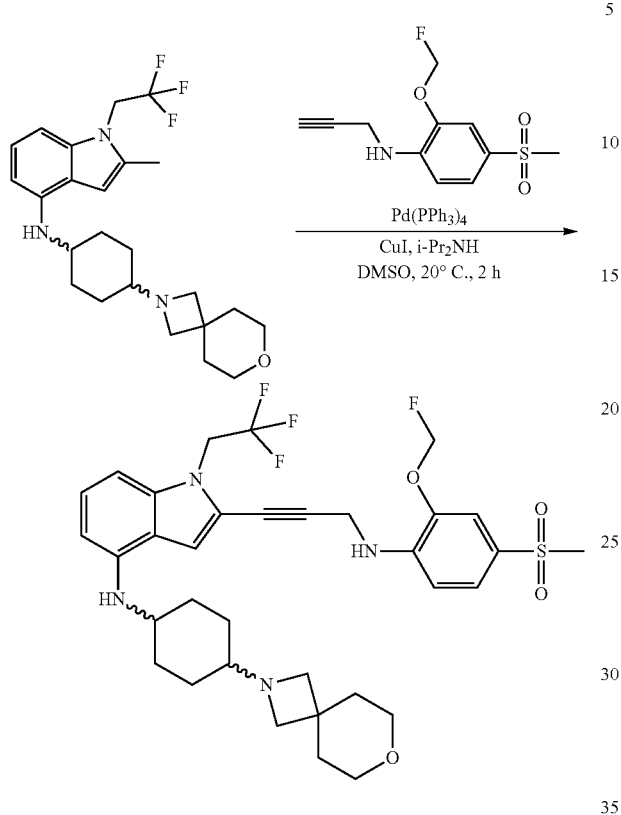

Preparation of N-((1R,4R)-4-(7-oxa-2-azaspiro[3.5]nonan-2-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine and N-((1S,4S)-4-(7-oxa-2-azaspiro[3.5]nonan-2-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine: To a mixture of N-(4-(7-oxa-2-azaspiro[3.5]nonan-2-yl)cyclohexyl)-2-iodo-1-(2,2,2-trifluoroethyl)-1H-indol-4-amine (1 eq.) and 2-(fluoromethoxy)-4-(methylsulfonyl)-N-(prop-2-yn-1-yl)aniline (1.2 eq.) in DMSO (3 mL) were added i-Pr$_2$NH (10 eq.), CuI (1 eq.), and Pd(PPh$_3$)$_4$ (0.2 eq.) in one portion under N$_2$. The mixture was stirred at 20° C. for 2 h. LC-MS analysis showed that the reaction was complete. The reaction mixture was diluted with EtOAc (20 mL), and the resulting mixture was poured into saturated EDTA solution (10 mL) and stirred for 0.5 h. The organic layer was poured into saturated EDTA solution (20 mL) and stirred further for 1 h. The resulting aqueous phase was extracted with EtOAc (20 mL×3). The combined organic layers were washed with water (25 mL×3) and brine (15 mL×2), dried over anhydrous sodium sulfate, filtered, and concentrated in vacuo. The crude residue was purified by prep-TLC and prep-HPLC to obtain the desired product as a white solid. N-((1R,4R)-4-(7-oxa-2-azaspiro[3.5]nonan-2-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine, MS (ES$^+$, m/z): 677.3; and N-((1S,4S)-4-(7-oxa-2-azaspiro[3.5]nonan-2-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine, MS (ES$^+$, m/z): 677.3.

Example C14: Synthesis of Compounds 83A, 84A, 85A, and 86A

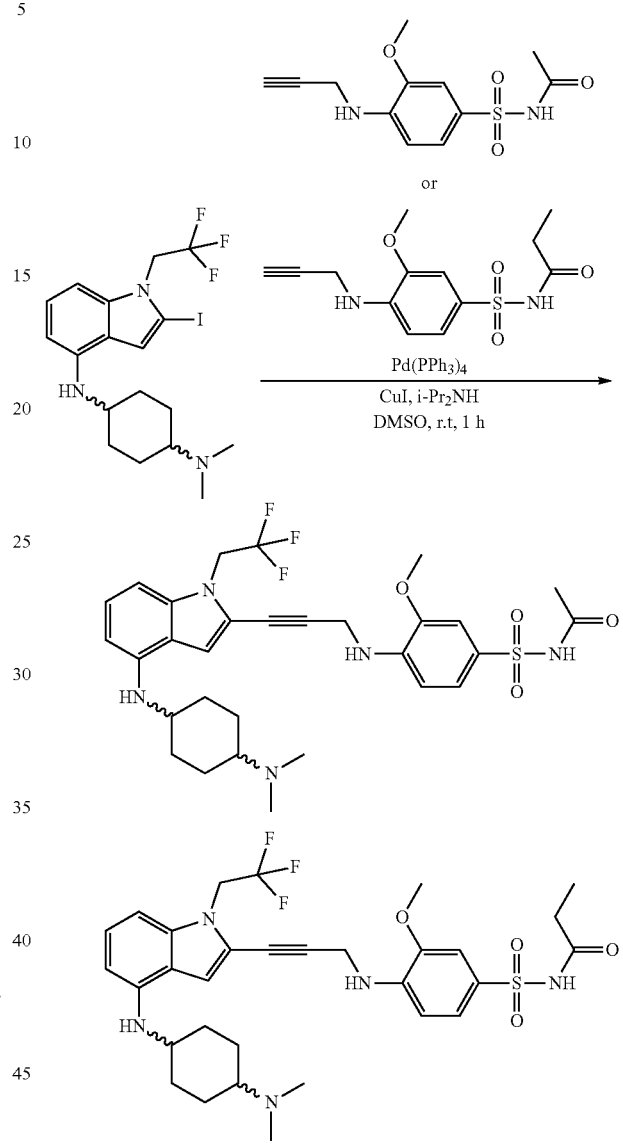

To a mixture of N-((3-methoxy-4-(prop-2-yn-1-ylamino)phenyl)sulfonyl)acetamide or N-((3-methoxy-4-(prop-2-yn-1-ylamino)phenyl)sulfonyl)propionamide (1.5 eq.) and N$^1$-(2-iodo-1-(2,2,2-trifluoroethyl)-1H-indol-4-yl)-N$^4$,N$^4$-dimethylcyclohexane-1,4-diamine (1 eq.) in DMSO (2 mL) were added CuI (1 eq.), Pd(PPh$_3$)$_4$ (0.10 eq.), and N-isopropylpropan-2-amine (1 eq.) at 30° C. The mixture was stirred for 1 h under N$_2$. TLC analysis showed that the reaction was complete. The reaction mixture was quenched by adding a saturated EDTA solution (30 mL) and EtOAc (10 mL) and stirring the mixture at 25° C. for 1 h. The aqueous phase was extracted with EtOAc (20 mL×3). The combined organic layers were washed with brine (30 mL), dried over anhydrous sodium sulfate, filtered, and concentrated under reduced pressure. The crude residue was purified by prep-TLC and prep-HPLC to afford the desired products.

N-(3-methoxy-4-{[3-(4-{[(1R,4R)-4-(dimethylamino)cyclohexyl]amino}-1-(2,2,2-trifluoroethyl)-1H-indol-2-yl)

prop-2-yn-1-yl]amino}benzenesulfonyl)acetamide, C-MS (ES+, m/z): 620.1; N-(3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzenesulfonyl)acetamide, C-MS (ES+, m/z): 620.3; N-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzenesulfonyl)propanamide, C-MS (ES+, m/z): 634.3; and N-(3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzenesulfonyl)propenamide, MS (ES+, m/z): 634.2.

Example C15: Synthesis of Compounds 95A, 234A, 329A, 330A, 346A, 347A, 393A, 394A, 518A

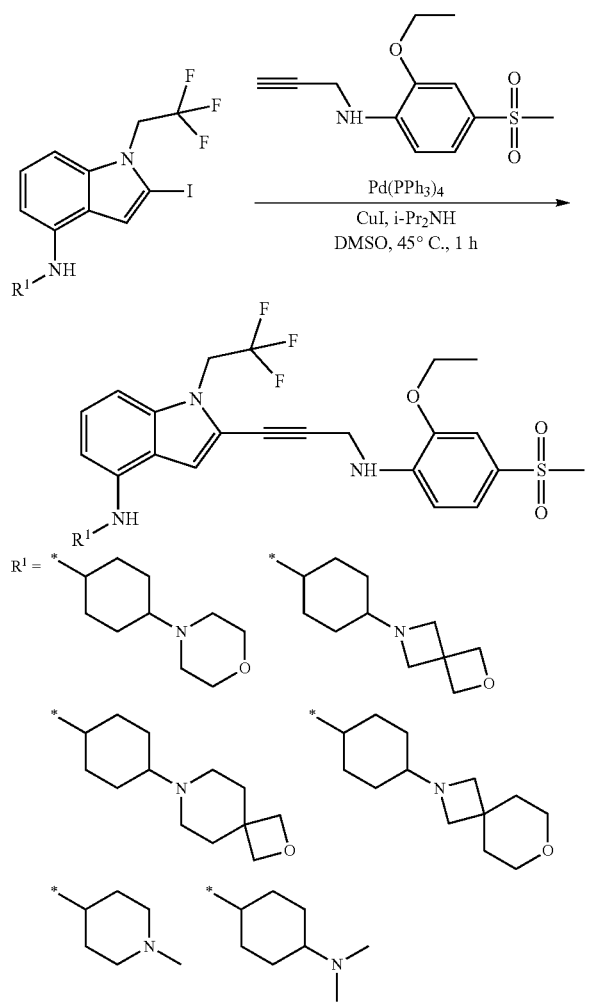

To a solution of 2-ethoxy-4-(methylsulfonyl)-N-(prop-2-yn-1-yl)aniline (1.5 eq.) in DMSO (25 mg/mL) were added 2-iodo-N—(R$^1$)-1-(2,2,2-trifluoroethyl)-1H-indol-4-amine (1 eq.), CuI (1 eq.), i-Pr$_2$NH (1 eq.), and Pd(PPh$_3$)$_4$ (0.02 eq.). The mixture was stirred at 45° C. for 1 h. TLC analysis (EtOAc:TEA=10:1, R$_f$=0.24) indicated that the reaction was complete. The reaction mixture was quenched by adding a saturated EDTA solution (40 mL) at 25° C. and extracting the mixture with EtOAc (20 mL×3). The combined organic layers were dried over anhydrous$_{sodium\ sulfate}$, filtered, and concentrated under reduced pressure. The crude residue was purified by prep-TLC and prep-HPLC to afford the desired products as yellow solids.

N-((1R,4R)-4-(2-oxa-7-azaspiro[3.5]nonan-7-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine, MS (ES+, m/z): 673.2; N-((1S,4S)-4-(2-oxa-7-azaspiro[3.5]nonan-7-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine, MS (ES+, m/z): 673.2; N-((1R,4R)-4-(7-oxa-2-azaspiro[3.5]nonan-2-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine, MS (ES+, m/z): 673.3; N-((1S,4S)-4-(7-oxa-2-azaspiro[3.5]nonan-2-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine, MS (ES+, m/z): 673.3; 2-(3-((2-ethoxy-4-(methylsulfonyl)phenyl)amino)prop-1-yn-1-yl)-N-(1-methylpiperidin-4-yl)-1-(2,2,2-trifluoroethyl)-1H-indol-4-amine, MS (ES+, m/z): 563.2; 2-(3-((2-ethoxy-4-(methylsulfonyl)phenyl)amino)prop-1-yn-1-yl)-N-((1R,4R)-4-morpholinocyclohexyl)-1-(2,2,2-trifluoroethyl)-1H-indol-4-amine, MS (ES+, m/z): 633.2; 2-(3-((2-ethoxy-4-(methylsulfonyl)phenyl)amino)prop-1-yn-1-yl)-N-((1S,4S)-4-morpholinocyclohexyl)-1-(2,2,2-trifluoroethyl)-1H-indol-4-amine, MS (ES+, m/z): 633.2; 2-{3-[(2-ethoxy-4-methanesulfonylphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine, MS (ES+, m/z): 645.2; and (1R,4R)—N$^4$-(2-{3-[(2-ethoxy-4-methanesulfonylphenyl)amino]prop-1-yn-1-yl}-1-(2,2,2-trifluoroethyl)-1H-indol-4-yl)-N$^1$,N$^1$-dimethylcyclohexane-1,4-diamine, MS (ES+, m/z): 591.2.

Example C16: Synthesis of Compounds 174A, 175A, 176A, 177A, 178A, 179A, and 180A

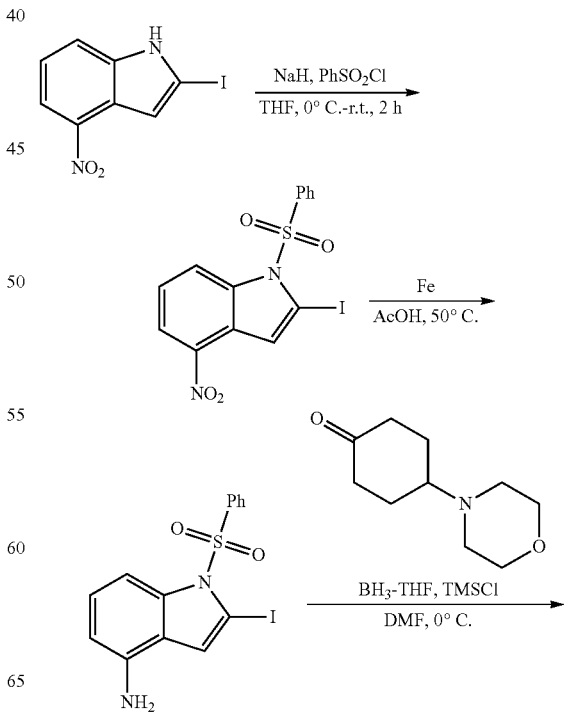

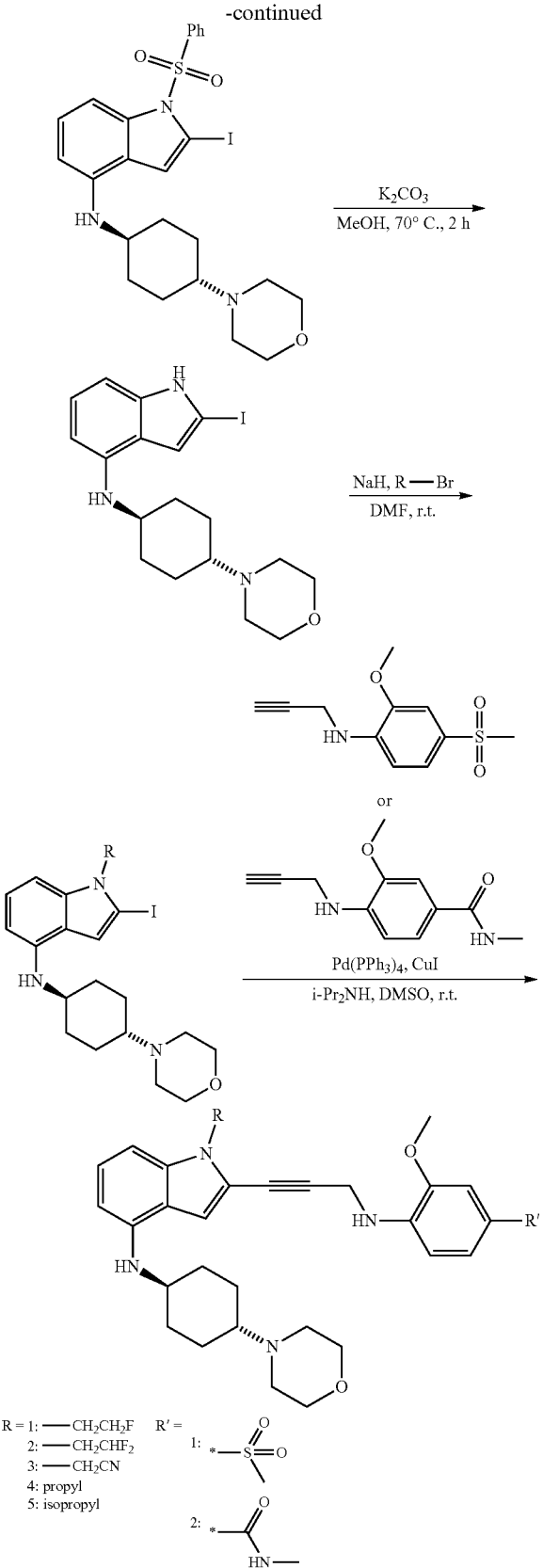

Preparation of 2-iodo-4-nitro-1-(phenylsulfonyl)-1H-indole: To a solution of 2-iodo-4-nitro-1H-indole (3 g, 10.4 mmol, 1 eq.) in THF (30 mL) was added NaH (1.3 g, 31.3 mmol, 60% in mineral oil, 3 eq.). The reaction mixture was stirred at 0° C. for 10 min, and benzenesulfonyl chloride (2.8 g, 15.7 mmol, 2 mL, 1.5 eq.) was then added to the solution. The reaction mixture was stirred at 25° C. for 50 min. TLC analysis (PE:EtOAc=5:1, $R_f$=0.5) showed that the reaction was complete. The reaction mixture was quenched by adding water (50 mL) and extracted with EtOAc (50 mL). The crude product was washed with PE (100 mL), and the resulting solution was filtered and concentrated to afford the desired product (4.15 g, 9.7 mmol, 93.1% yield) as a yellow solid.

Preparation of 2-iodo-1-(phenylsulfonyl)-1H-indol-4-amine: A solution of 2-iodo-4-nitro-1-(phenylsulfonyl)-1H-indole (1.3 g, 3 mmol, 1 eq.) in AcOH (15 mL) was heated to 70° C., and Fe (847.7 mg, 15.2 mmol, 5 eq.) was added. The resulting mixture was stirred further at 70° C. for 1 h. TLC analysis (PE:EtOAc=3:1, $R_f$=0.5) showed that the reaction was complete. The reaction mixture was concentrated, and the crude product was extracted with EtOAc (15 mL) and washed with water (50 mL). The crude residue was purified by silica gel chromatography (PE:EtOAc=2:1) and again by prep-HPLC to afford the desired product (1 g, 2.51 mmol, 82.71% yield) as a yellow oil. MS (ES+, m/z): 399.1.

Preparation of 2-iodo-N-((1R,4R)-4-morpholinocyclohexyl)-1-(phenylsulfonyl)-1H-indol-4-amine: To a mixture of 2-iodo-1-(phenylsulfonyl)-1H-indol-4-amine (1 g, 2.5 mmol, 1 eq.) and 4-morpholinocyclohexanone (920.3 mg, 5 mmol, 2 eq.) in DMF (10 mL) was added TMSCl (545.6 mg, 5 mmol, 637.4 μL, 2 eq.). The mixture was stirred at 0° C. for 1 h, and BH$_3$·THF (1M, 7.5 mL, 3 eq.) was added to the reaction mixture under N$_2$. The mixture was stirred further at 0° C. for 2 h. TLC analysis (PE:EtOAc=5:1, $R_f$=0.5) showed that the starting material was consumed completely. The reaction mixture was partitioned by adding water (100 mL) and EtOAc (100 mL). The organic phase was separated, dried over anhydrous Na$_2$SO$_4$, filtered, and concentrated under reduced pressure to give a filter liquor. The filter liquor was dried further by vacuum to give the crude product as a yellow oil. The yellow oil was purified by chromatography on silica gel column chromatography (PE:EtOAc=5:1) to give the desired product (0.55 g, crude) as a yellow oil.

Preparation of 2-iodo-N-((1R,4R)-4-morpholinocyclohexyl)-1H-indol-4-amine: To a solution of 2-iodo-N-((1R,4R)-4-morpholinocyclohexyl)-1-(phenylsulfonyl)-1H-indol-4-amine (0.3 g, 530.5 μmol, 1 eq.) in MeOH (10 mL) was added K$_2$CO$_3$ (586.6 mg, 4.2 mmol, 8 eq.) at 20° C. The mixture was heated to 80° C. and stirred for 2 h. LC-MS analysis showed that the reaction was complete. The reaction mixture was concentrated and purified using silica gel column chromatography (PE:EtOAc=1:1, added Et$_3$N, $R_f$=0.5) to afford the desired product (0.2 g, 470. μmol, 88.6% yield) as a yellow solid.

General Procedure for the preparation of R-substituted 2-iodo-1-R—N-((1R,4R)-4-morpholinocyclohexyl)-1H-indol-4-amine: To a solution of 2-iodo-N-((1R,4R)-4-morpholinocyclohexyl)-1H-indol-4-amine (1 eq.) in DMF (10 mL) was added NaH (2 eq.; 60% in mineral oil). The reaction mixture was stirred at 0° C. for 20 min, and R—Br was added (1~1.2 eq.). The resulting reaction mixture was stirred at 0~25° C. for 40 min. LC-MS analysis showed that the reaction was complete. The reaction mixture was quenched by adding water (10 mL) and extracted with EtOAc (10 mL). The organic phase was concentrated in vacuo and purified by prep-TLC to give the desired product as a brown solid.

General Procedure for the preparation of final products: To a mixture of 2-methoxy-4-(methylsulfonyl)-N-(prop-2-yn-1-yl)aniline or 3-methoxy-N-methyl-4-(prop-2-yn-1-ylamino)benzamide (1.3 eq.) in DMSO were added i-Pr₂NH (10 eq.), CuI (1 eq.), 2-iodo-1-(R-substituted)-N-((1R,4R)-4-morpholinocyclohexyl)-1H-indol-4-amine (1 eq.), and Pd(PPh₃)₄ (0.2 eq.) at 25° C. The mixture was stirred for 1 h under N₂. LC-MS or TLC analysis showed that the reaction was complete. The reaction mixture was quenched by adding a saturated EDTA solution at 25° C. and stirring the mixture for 2 h. The reaction mixture was partitioned between by adding EtOAc, and the aqueous phase was extracted with EtOAc. The organic phase was washed with brine, dried over anhydrous$_{Na2SO4}$, filtered, and concentrated in vacuo to give the crude product. The crude residue was purified by prep-TLC and prep-HPLC to give the solution of the desired product. The solution was lyophilized to afford the desired products as light yellow solids.

1-(2-fluoroethyl)-2-{3-[(4-methanesulfonyl-2-methoxyphenyl)amino]prop-1-yn-1-yl}-N-[(1R,4R)-4-(morpholin-4-yl)cyclohexyl]-1H-indol-4-amine, MS (ES⁺, m/z): 583.3; 1-(2,2-difluoroethyl)-2-{3-[(4-methanesulfonyl-2-methoxyphenyl)amino]prop-1-yn-1-yl}-N-[(1R,4R)-4-(morpholin-4-yl)cyclohexyl]-1H-indol-4-amine, MS (ES⁺, m/z): 601.3; 2-(2-{3-[(4-methanesulfonyl-2-methoxyphenyl)amino]prop-1-yn-1-yl}-4-{[(1R,4R)-4-(morpholin-4-yl)cyclohexyl]amino}-1H-indol-1-yl)acetonitrile, MS (ES⁺, m/z): 576.3; 4-({3-[1-(2-fluoroethyl)-4-{[(1R,4R)-4-(morpholin-4-yl)cyclohexyl]amino}-1H-indol-2-yl]prop-2-yn-1-yl}amino)-3-methoxy-N-methylbenzamide, MS (ES⁺, m/z): 562.3; 4-({3-[1-(cyanomethyl)-4-{[(1R,4R)-4-(morpholin-4-yl)cyclohexyl]amino}-1H-indol-2-yl]prop-2-yn-1-yl}amino)-3-methoxy-N-methylbenzamide, MS (ES⁺, m/z): 555.3; 2-{3-[(4-methanesulfonyl-2-methoxyphenyl)amino]prop-1-yn-1-yl}-1-propyl-N-[(1R,4R)-4-(morpholin-4-yl)cyclohexyl]-1H-indol-4-amine, MS (ES⁺, m/z): 579.3; and 2-{3-[(4-methanesulfonyl-2-methoxyphenyl)amino]prop-1-yn-1-yl}-1-(2-methylpropyl)-N-[(1R,4R)-4-(morpholin-4-yl)cyclohexyl]-1H-indol-4-amine, MS (ES⁺, m/z): 593.3.

Example C17: Synthesis of Compounds 309A, 310A, 311A, and 312A

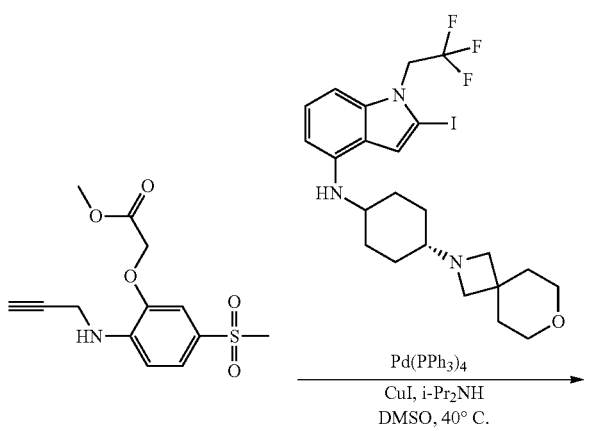

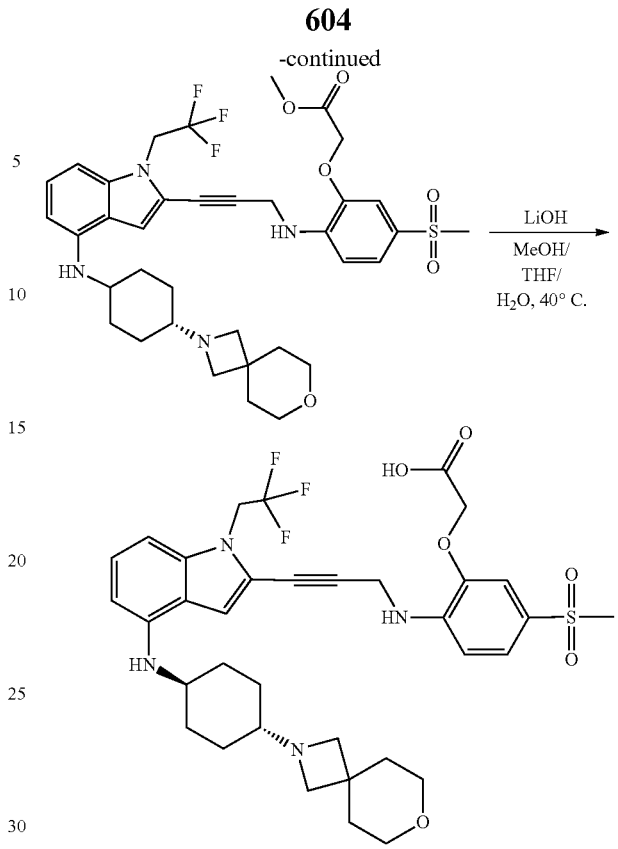

Preparation of methyl 2-(2-((3-(4-((4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetate: To a solution of methyl 2-(5-(methylsulfonyl)-2-(prop-2-yn-1-ylamino)phenoxy)acetate (19.55 mg, 65.77 μmol, 1.2 eq.) in DMSO (2 mL) were added i-Pr₂NH (16.64 mg, 164.42 μmol, 23.24 μL, 3 eq.), CuI (10.44 mg, 54.81 μmol, 1 eq.), N-(4-(7-oxa-2-azaspiro[3.5]nonan-2-yl)cyclohexyl)-2-iodo-1-(2,2,2-trifluoroethyl)-1H-indol-4-amine (0.03 g, 54.81 μmol, 1 eq.), and Pd(PPh₃)₄ (6.33 mg, 5.48 μmol, 0.1 eq.). The mixture was stirred for 10 min at 40° C. under N₂. LC-MS analysis showed that the reaction was complete. The reaction was diluted with EtOAc (20 mL) and saturated EDTA solution (20 mL) and stirred at 20° C. for 1 h. The mixture was then extracted with EtOAc (20 mL×3). The combined organic layers were washed with brine (50 mL), dried over anhydrous$_{sodium\ sulfate}$, filtered, and concentrated under reduced pressure. The crude residue was purified by prep-HPLC to afford the desired product (0.0103 g, 13.84 μmol, 25.25% yield) as a light yellow solid. MS (ES⁺, m/z): 717.2.

Preparation of 2-(2-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetic acid: To a solution of methyl 2-(2-((3-(4-((4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetate (0.08 g, 111.61 μmol, 1 eq.) in THF (1 mL) were added MeOH (1 mL), water (0.4 mL), and LiOH·H₂O (9.37 mg, 223.21 μmol, 2 eq.). The mixture was stirred for 0.5 h at 40° C. under N₂. LC-MS analysis showed that the reaction was complete. The pH of the reaction mixture was adjusted to 6 using 2M aqueous formic acid, and the resulting white solid was filtered, and concentrated. The crude residue was purified by prep-HPLC to afford the desired product (0.0085 g, 12.09 μmol, 10.84% yield) as a white solid. MS (ES+, m/z): 703.2.

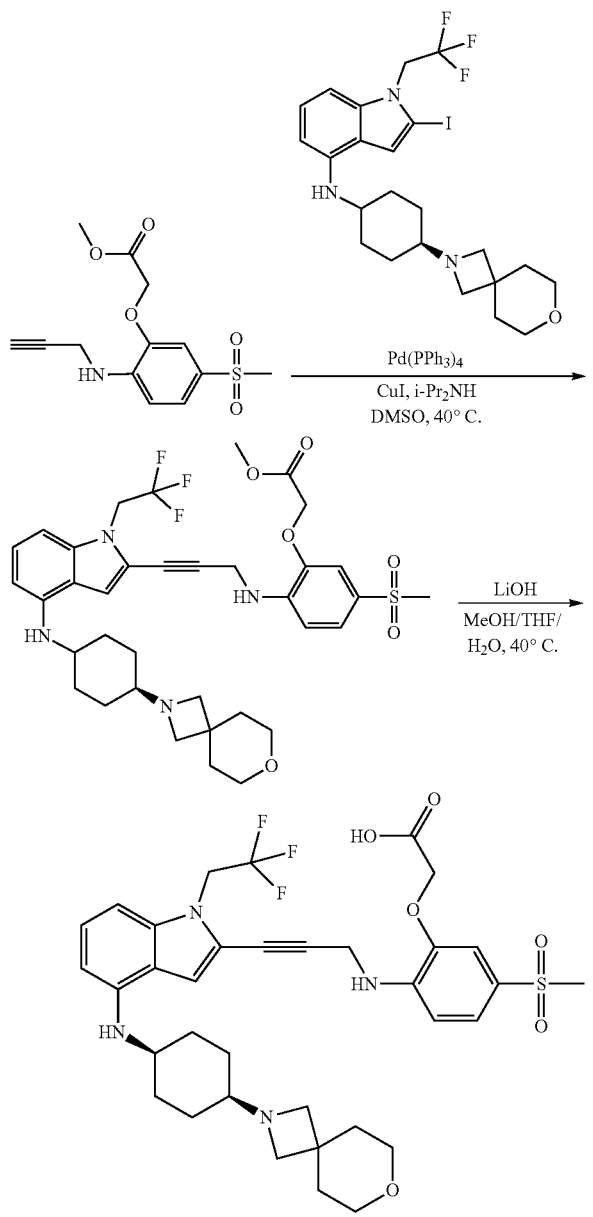

Preparation of methyl 2-(2-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetate: To a solution of 2-iodo-N-[4-(7-oxa-2-azaspiro[3.5]nonan-2-yl)cyclohexyl]-1-(2,2,2-trifluoroethyl)indol-4-amine (0.15 g, 274.03 μmol, 1 eq.) in DMSO (5 mL) were added i-Pr$_2$NH (83.19 mg, 822.08 μmol, 116.18 μL, 3 eq.), CuI (52.19 mg, 274.03 μmol, 1 eq.), methyl 2-(5-(methylsulfonyl)-2-(prop-2-yn-1-ylamino)phenoxy)acetate (122.21 mg, 411.04 μmol, 1.5 eq.), and Pd(PPh$_3$)$_4$ (31.67 mg, 27.40 μmol, 0.1 eq.). The mixture was stirred for 10 min at 40° C. under N$_2$. TLC analysis showed that the reaction was complete. The reaction was diluted with EtOAc (20 mL) and saturated EDTA solution and stirred further at 20° C. for 1 h. The reaction mixture was extracted with EtOAc (20 mL×3). The combined organic layers were washed with brine (50 mL), dried over anhydrous$_{sodium sulfate}$, filtered, and concentrated under reduced pressure. The crude residue was purified by prep-TLC (SiO$_2$, DCM:MeOH=20:1) and prep-HPLC to afford the desired product (0.0169 g, 23.46 μmol, 8.56% yield) as a light yellow solid. MS (ES+, m/z): 717.2.

Preparation of 2-(2-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetic acid: To a solution of methyl 2-(2-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetate (0.06 g, 83.70 μmol, 1 eq.) in MeOH (0.5 mL) were added THF (0.5 mL), water (0.2 mL), and LiOH·H$_2$O (7.02 mg, 167.41 μmol, 2 eq.). The mixture was stirred for 0.5 h at 40° C. under N$_2$. LC-MS analysis showed that the reaction was complete. The mixture was purified by prep-HPLC to afford the desired product (0.0162 g, 23.05 μmol, 27.54% yield) as a white solid. MS (ES+, m/z): 703.2.

Example C18: Synthesis of Compounds 130A, 131A, 265A, 266A, 512A, and 716A

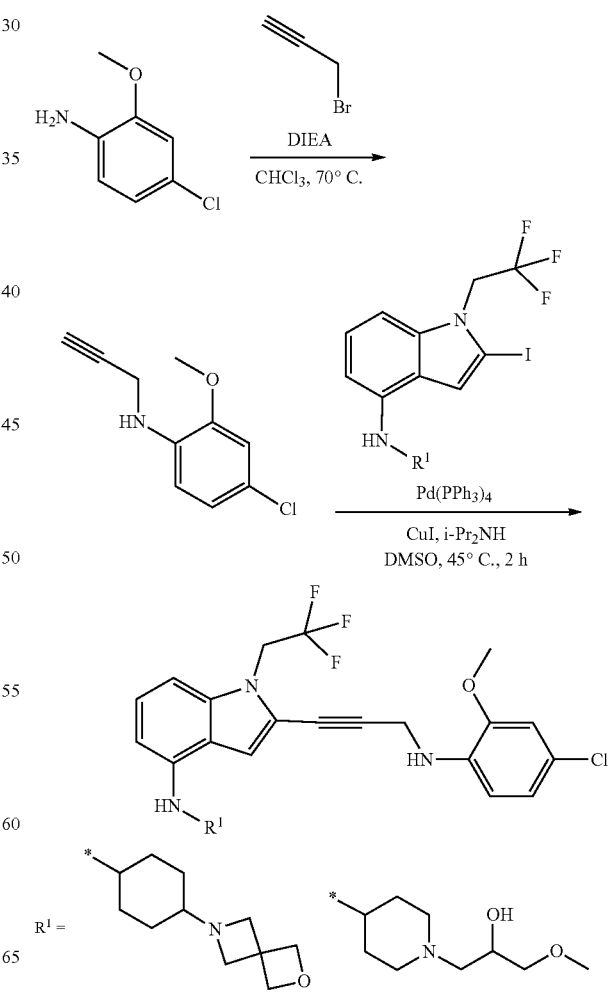

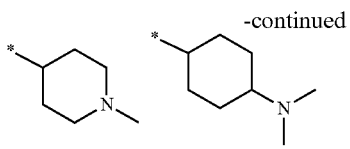

Preparation of 4-chloro-2-methoxy-N-(prop-2-yn-1-yl) aniline: To a mixture of 4-chloro-2-methoxyaniline (2 g, 1 eq.) and 3-bromoprop-1-yne (1.27 g, 0.8 eq.) in CHCl$_3$ (10 mL) and THF (10 mL) was added DIPEA (6.30 mL, 3 eq.). The mixture was stirred at 70° C. for 6 h. LC-MS or TLC analysis showed that the reaction was complete. The reaction mixture was concentrated in vacuo. The crude product was poured into water, and the aqueous phase was extracted with EtOAc (200 mL×3). The combined organic layers were washed with brine (80 mL), dried over anhydrous Na$_2$SO$_4$, filtered, and concentrated in vacuo. The crude residue was purified by column chromatography to afford the desired product (700 mg, 26.71% yield) as a yellow oil. MS (ES$^+$, m/z): 196.0.

General procedure for the preparation of 2-(3-((4-chloro-2-methoxyphenyl)amino)prop-1-yn-1-yl)-N—R$^1$-substituted-1-(2,2,2-trifluoroethyl)-1H-indol-4-amines: To a solution of 4-chloro-2-methoxy-N-(prop-2-yn-1-yl)aniline (2 eq.) in DMSO (3 mL) were added i-Pr$_2$NH (10 eq.), CuI (1 eq.), 2-iodo-N—R$^1$-substituted-1-(2,2,2-trifluoroethyl)-1H-indol-4-amine (1 eq.), and Pd(PPh$_3$)$_4$ (0.40 eq.). The mixture was stirred at 45° C. for 2~5 h under N$_2$. LC-MS or TLC analysis showed that the reaction was complete. The mixture was poured into a saturated EDTA solution and stirred for 1 h. The aqueous phase was extracted with EtOAc (3×). The combined organic layers were washed with brine (3×), dried over anhydrous sodium sulfate, filtered, and concentrated in vacuo. The residue was purified by TLC, prep-HPLC, or TLC and prep-HPLC to afford the desired products.

(1R,4R)—N$^4$-(2-{3-[(4-chloro-2-methoxyphenyl)amino] prop-1-yn-1-yl}-1-(2,2,2-trifluoroethyl)-1H-indol-4-yl)-N$^1$,N$^1$-dimethylcyclohexane-1,4-diamine, MS (ES$^+$, m/z): 533.2; (1S,4S)—N$^1$-(2-(3-((4-chloro-2-methoxyphenyl) amino)prop-1-yn-1-yl)-1-(2,2,2-trifluoroethyl)-1H-indol-4-yl)-N$^4$,N$^4$-dimethylcyclohexane-1,4-diamine, MS (ES$^+$, m/z): 533.2; N-((1R,4R)-4-(2-oxa-6-azaspiro[3.3]heptan-6-yl)cyclohexyl)-2-(3-((4-chloro-2-methoxyphenyl)amino) prop-1-yn-1-yl)-1-(2,2,2-trifluoroethyl)-1H-indol-4-amine, MS (ES$^+$, m/z): 587.2; N-((1S,4S)-4-(2-oxa-6-azaspiro[3.3] heptan-6-yl)cyclohexyl)-2-(3-((4-chloro-2-methoxyphenyl) amino)prop-1-yn-1-yl)-1-(2,2,2-trifluoroethyl)-1H-indol-4-amine, MS (ES$^+$, m/z): 587.2; 2-{3-[(4-chloro-2-methoxyphenyl)amino]prop-1-yn-1-yl}-N-(1-methylpiperidin-4-yl)-1-(2,2,2-trifluoroethyl)-1H-indol-4-amine, MS (ES$^+$, m/z): 505.1; and 1-{4-[(2-{3-[(4-chloro-2-methoxyphenyl)amino]prop-1-yn-1-yl}-1-(2,2,2-trifluoroethyl)-1H-indol-4-yl)amino]piperidin-1-yl}-3-methoxypropan-2-ol, MS (ES$^+$, m/z): 579.2.

Example C19: Synthesis of 4-(3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)-7-(methylsulfonyl)-2H-benzo[b][1,4]oxazin-3(4H)-one (Compound 326A)

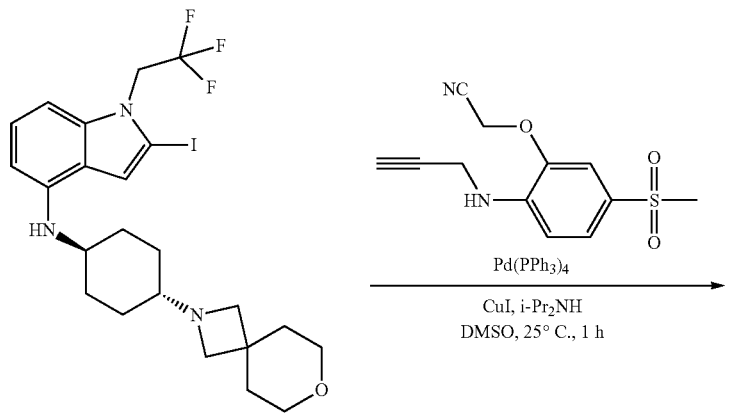

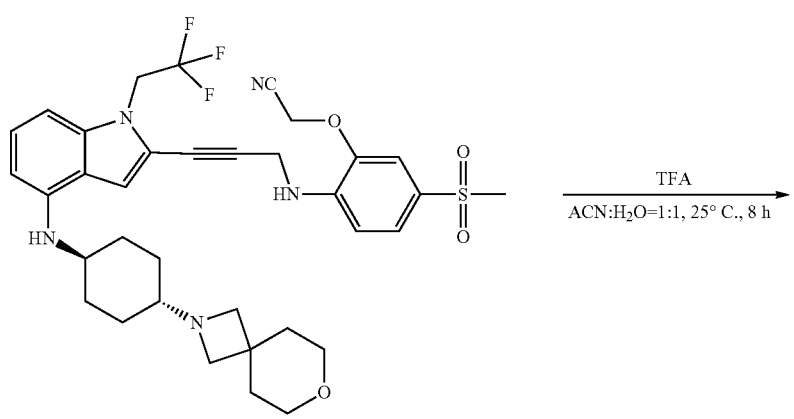

-continued

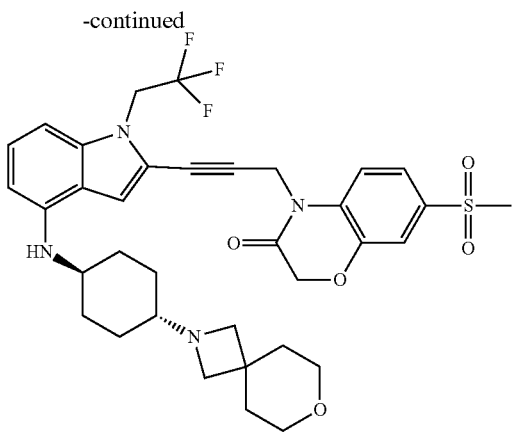

Preparation of 2-(2-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetonitrile: To a solution of 6-(methylsulfonyl)-3-(prop-2-yn-1-yl)benzo[d]oxazol-2(3H)-one (706.14 mg, 2.14 mmol, 1.3 eq.) in DMSO (10 mL) were added i-Pr$_2$NH (4.99 g, 49.32 mmol, 6.97 mL, 30 eq.), CuI (626.26 mg, 3.29 mmol, 2 eq.), N-((1R,4R)-4-(7-oxa-2-azaspiro[3.5]nonan-2-yl)cyclohexyl)-2-iodo-1-(2,2,2-trifluoroethyl)-1H-indol-4-amine (1 g, 1.64 mmol, 1 eq.), and Pd(PPh$_3$)$_4$ (474.98 mg, 411.04 µmol, 0.25 eq.) at 25° C. The mixture was stirred at 25° C. for 1 h under N$_2$. TLC analysis (DCM:TEA:MeOH=100:1:10, R$_f$=0.3) indicated that the starting material consumed completely. The mixture was poured into saturated EDTA solution (100 mL), stirred at 25° C. for 1 h, and extracted with EtOAc (50 mL×3). The combined organic layers were poured into a saturated EDTA solution (200 mL) and stirred at 25° C. for 1 h. The aqueous phase was extracted with EtOAc (100 mL×3). The combined organic layers were concentrated under reduced pressure to give a residue, which was purified by column chromatography (DCM:MeOH=50:1 to 5:1) to afford the desired product (1 g, 1.46 mmol, 88.95% yield). MS (ES$^+$, m/z): 684.3.

Preparation of 4-(3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)-7-(methylsulfonyl)-2H-benzo[b][1,4]oxazin-3(4H)-one: To a mixture of 2-(2-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetonitrile (0.5 g, 731.23 µmol, 1 eq.) in acetonitrile (10 mL) and water (10 mL) was added TFA (19.25 g, 168.83 mmol, 12.50 mL, 230.88 eq.) at 25° C. The mixture was stirred at 25° C. for 8 h. LC-MS analysis showed that the starting material was consumed completely. The mixture was poured into a saturated Na$_2$CO$_3$ solution (50 mL) and extracted with EtOAc (30 mL×3). The combined organic layers were washed with brine (30 mL×3), dried over anhydrous sodium sulfate, filtered, and concentrated under reduced pressure. The crude residue was purified by prep-TLC (DCM:MeOH=10:1, R$_f$=0.3) and further purified by prep-HPLC. The resulting solution was concentrated under reduced pressure to remove acetonitrile. A saturated Na$_2$CO$_3$ solution was added drop-wise into the mixture to adjust the pH of the solution to 8. The mixture was then extracted with EtOAc (30 mL×3). The combined organic layers were washed with brine (30 mL×3), dried over anhydrous sodium sulfate, filtered, and concentrated under reduced pressure to afford the desired product (154.4 mg, 220.52 µmol, 30.16% yield) as a yellow solid. MS (ES$^+$, m/z): 685.3.

Example C20: Synthesis of Compounds 125A, 126A, 291A, 292A, 493A, and 671A

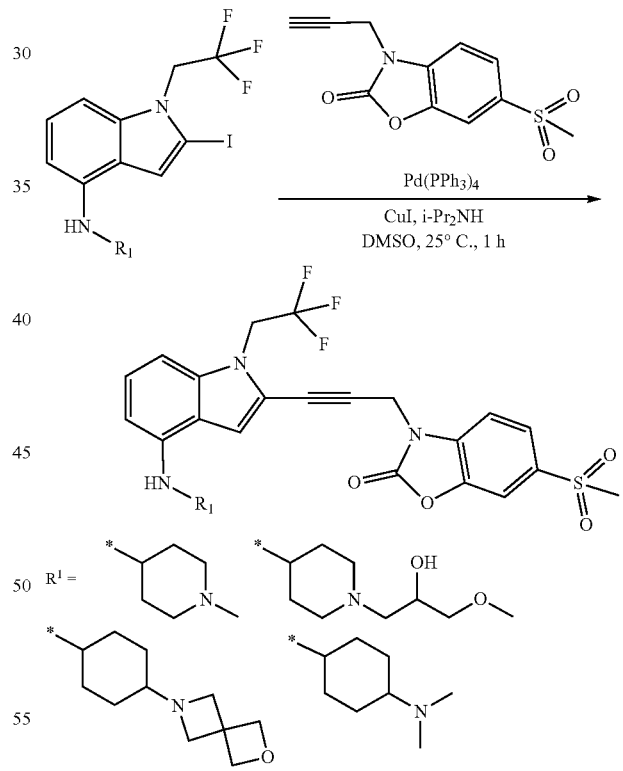

General Procedure: To a solution of 6-(methylsulfonyl)-3-(prop-2-yn-1-yl)benzo[d]oxazol-2(3H)-one (2 eq.) in DMSO (1 mL) were added i-Pr$_2$NH (30 eq.), CuI (1~2 eq.), 2-iodo-N—R$^1$-1-(2,2,2-trifluoroethyl)-1H-indol-4-amine (1 eq.), and Pd(PPh$_3$)$_4$ (0.15~0.50 eq.). The mixture was stirred at 25° C. for 1 h under N$_2$. LC-MS or TLC analysis showed that the reaction was complete. The mixture was poured into a saturated EDTA solution and stirred for 1 h. The aqueous phase was extracted with EtOAc (3×). The combined organic layers were washed with brine (3×), dried over anhydrous sodium sulfate, filtered, and concentrated in vacuo. The residue was purified by prep-TLC, prep-HPLC, or prep-TLC and prep-HPLC to afford the desired products.

3-(3-(4-(((1R,4R)-4-(2-oxa-6-azaspiro[3.3]heptan-6-yl) cyclohexyl)amino)-1-(2,2,2-trifluoroethyl)-1H-indol-2-yl) prop-2-yn-1-yl)-6-(methylsulfonyl)benzo[d]oxazol-2 (3H)-one, MS (ES+, m/z): 643.2; 3-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-6-(methylsulfonyl)benzo[d]oxazol-2 (3H)-one, MS (ES+, m/z): 643.2; 3-(3-(4-((1-(2-hydroxy-3-methoxypropyl)piperidin-4-yl)amino)-1-(2,2,2-trifluoroethyl)-1H-indol-2-yl) prop-2-yn-1-yl)-6-(methylsulfonyl)benzo[d]oxazol-2 (3H)-one, MS (ES+, m/z): 635.3; 3-(3-(4-((1-methylpiperidin-4-yl)amino)-1-(2,2,2-trifluoroethyl)-1H-indol-2-yl)prop-2-yn-1-yl)-6-(methylsulfonyl)benzo[d]oxazol-2 (3H)-one, MS (ES+, m/z): 561.2; 3-(3-(4-(((1R,4R)-4-(dimethylamino)cyclohexyl)amino)-1-(2,2,2-trifluoroethyl)-1H-indol-2-yl) prop-2-yn-1-yl)-6-(methylsulfonyl)benzo[d]oxazol-2 (3H)-one, MS (ES+, m/z): 589.2; 3-(3-(4-(((1S,4S)-4-(dimethylamino)cyclohexyl)amino)-1-(2,2,2-trifluoroethyl)-1H-indol-2-yl)prop-2-yn-1-yl)-6-(methylsulfonyl)benzo[d]oxazol-2 (3H)-one, MS (ES+, m/z): 589.2.

Example C21: Synthesis of Compounds 148A, 187A, and 395A mL) were added i-Pr$_2$NH (10 eq.) and CuI (1 eq.). Then, 2-iodo-4-R-1-(2,2,2-trifluoroethyl)-1H-indole (1 eq.) and Pd(PPh$_3$)$_4$ (0.2-0.4 eq.) were added, and the resulting mixture was stirred at 25° C. for 60 min under N$_2$. TLC and LC-MS analysis were used to monitor the reaction. The reaction mixture was diluted with EtOAc (15 mL), and poured into saturated EDTA solution (20 mL), and stirred for 1 h. The aqueous phase was then extracted with EtOAc (20 mL×3). The combined organic layers were washed with water (20 mL×2) and brine (20 mL×2), dried over anhydrous sodium sulfate, filtered, and concentrated to give a residue. The residue was purified by prep-TLC and prep-HPLC to afford the desired products.

3-methoxy-N-methyl-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide, MS (ES+, m/z): 674.2; 3-methoxy-N-methyl-4-{[3-(4-{[(1R,4R)-4-(morpholin-4-yl)cyclohexyl] amino}-1-(2,2,2-trifluoroethyl)-1H-indol-2-yl)prop-2-yn-1-yl]amino}benzene-1-sulfonamide, MS (ES+, m/z): 634.3; and 3-methoxy-N-methyl-4-{[3-(4-{[(1R,4R)-4-(diethylamino)cyclohexyl]amino}-1-(2,2,2-trifluoroethyl)-1H-indol-2-yl)prop-2-yn-1-yl]amino}benzene-1-sulfonamide, MS (ES+, m/z): 620.2.

Example C22: Synthesis of 3-methoxy-N,N-dimethyl-4-{[3-(4-{[(1R,4R)-4-(dimethylamino)cyclohexyl]amino}-1-(2,2,2-trifluoroethyl)-1H-indol-2-yl) prop-2-yn-1-yl]amino}benzene-1-sulfonamide (Compound 127A)

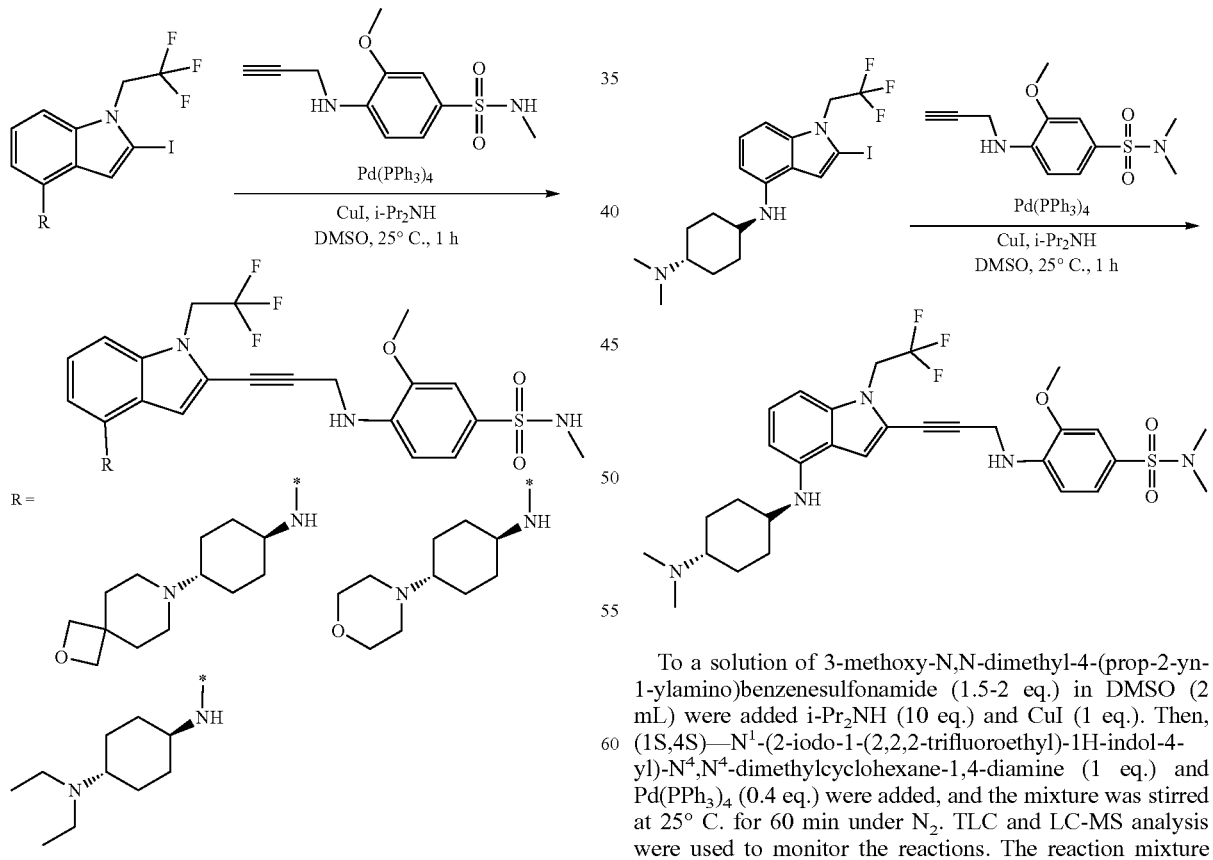

To a solution of 3-methoxy-N-methyl-4-(prop-2-yn-1-ylamino)benzenesulfonamide (2-2.2 eq.) in DMSO (2-4

To a solution of 3-methoxy-N,N-dimethyl-4-(prop-2-yn-1-ylamino)benzenesulfonamide (1.5-2 eq.) in DMSO (2 mL) were added i-Pr$_2$NH (10 eq.) and CuI (1 eq.). Then, (1S,4S)—N$^1$-(2-iodo-1-(2,2,2-trifluoroethyl)-1H-indol-4-yl)-N$^4$,N$^4$-dimethylcyclohexane-1,4-diamine (1 eq.) and Pd(PPh$_3$)$_4$ (0.4 eq.) were added, and the mixture was stirred at 25° C. for 60 min under N$_2$. TLC and LC-MS analysis were used to monitor the reactions. The reaction mixture was diluted with EtOAc (15 mL) and poured into saturated EDTA solution (20 mL) and stirred for 1 h. The aqueous phase was extracted with EtOAc (20 mL×3). The combined organic layers were washed with water (20 mL×2) and brine (20 mL×2), dried over anhydrous sodium sulfate, filtered, and concentrated to give a residue. The residue was purified by prep-TLC and prep-HPLC to obtain the desired product. MS (ES$^+$, m/z): 606.2.

Example C23: Synthesis of 2-fluoro-5-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide (Compound 136A)

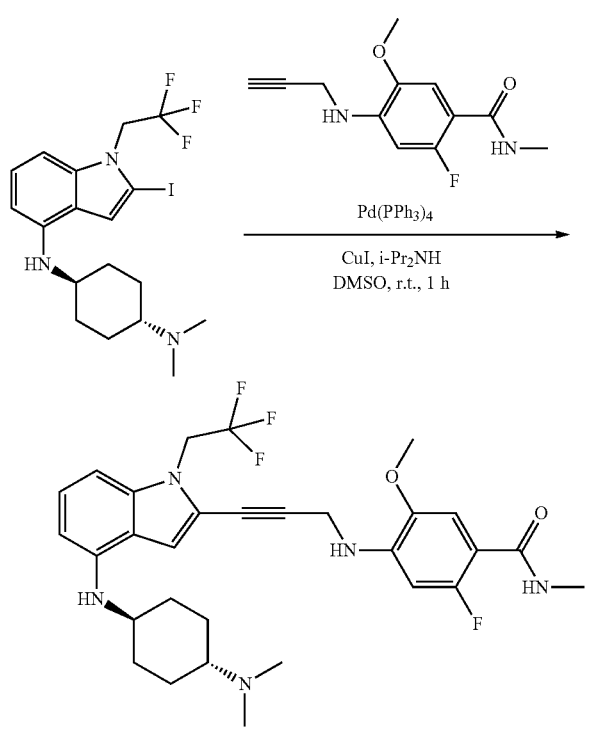

A mixture of (1R,4R)—N$^1$-(2-iodo-1-(2,2,2-trifluoroethyl)-1H-indol-4-yl)-N$^4$,N$^4$-dimethylcyclohexane-1,4-diamine (180 mg, 386.85 µmol), 2-fluoro-5-methoxy-N-methyl-4-(prop-2-ynylamino)benzamide (91.39 mg, 386.85 µmol, 1 eq.), CuI (73.68 mg, 386.85 µmol, 1 eq.), Pd(PPh$_3$)$_4$ (89.41 mg, 77.37 µmol, 0.2 eq.), and i-Pr$_2$NH (391.46 mg, 3.87 mmol, 546.73 µL, 10 eq.) in DMSO (3 mL) was degassed and purged with N$_2$ three times. The mixture was then stirred at 20° C. for 1 h under N$_2$. TLC analysis (EtOAc:TEA=10:1, R$_f$=0.5) indicated that the starting material remained, and one major new spot was detected. The mixture was added to saturated EDTA solution and stirred at 20° C. for 1 h under N$_2$. The reaction mixture was quenched by adding water (20 mL) and extracted with EtOAc (15 mL×3). The combined organic layers were washed with brine (10 mL×3), dried over anhydrous sodium sulfate, filtered, and concentrated under reduced pressure to give a residue. The residue was purified by prep-TLC (SiO$_2$, EtOAc:TEA=10:1) and prep-HPLC to afford the desired product (0.058 g, 100.61 µmol, 26.01% yield) as a yellow solid. MS (ES$^+$, m/z): 574.3.

Example C24: Synthesis of N-[(7S,8R)-7-fluoro-1,4-dioxaspiro[4.5]decan-8-yl]-2-{3-[(4-methanesulfonyl-2-methoxyphenyl)amino]prop-1-yn-1-yl}-1-(2,2,2-trifluoroethyl)-1H-indol-4-amine (Compound 870A)

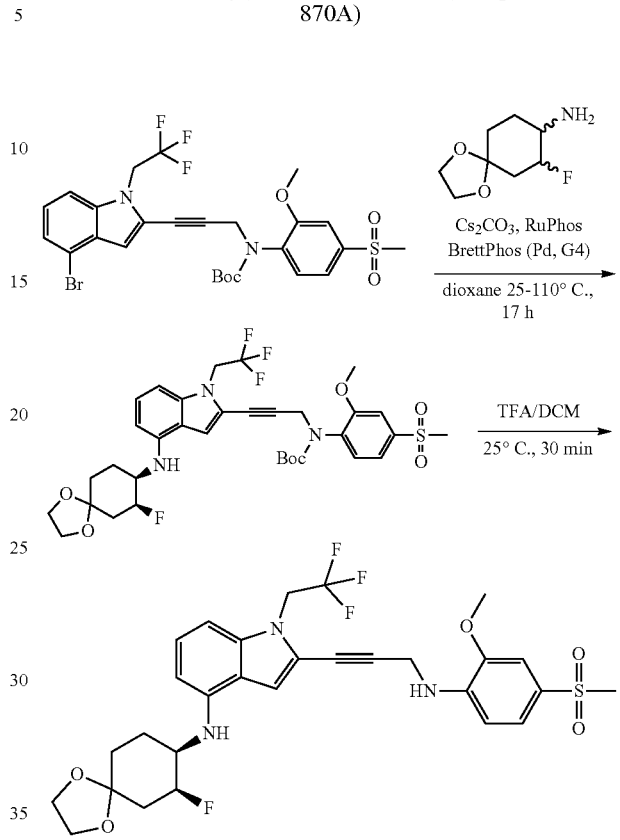

Preparation of tert-butyl (3-(4-(((7S,8R)-7-fluoro-1,4-dioxaspiro[4.5]decan-8-yl)amino)-1-(2,2,2-trifluoroethyl)-1H-indol-2-yl)prop-2-yn-1-yl)(2-methoxy-4-(methylsulfonyl)phenyl)carbamate: To a mixture of tert-butyl (3-(4-bromo-1-(2,2,2-trifluoroethyl)-1H-indol-2-yl)prop-2-yn-1-yl)(2-methoxy-4-(methylsulfonyl)phenyl)carbamate (500 mg, 812.40 µmol, 1 eq.) and 7-fluoro-1,4-dioxaspiro[4.5]decan-8-amine (189.15 mg, 893.64 µmol, 1.1 eq., HCl) in dioxane (5 mL) were added Cs$_2$CO$_3$ (794.09 mg, 2.44 mmol, 3 eq.), RuPhos (49.28 mg, 105.61 µmol, 0.13 eq.), and BrettPhos (Pd, G$_4$) (44.87 mg, 48.74 µmol, 0.06 eq.) under N$_2$. The mixture was stirred at 20° C. and slowly warmed to 110° C. under N$_2$. The mixture was then stirred at 110° C. for 17 h. TLC analysis (PE:EtOAc=1:1, R$_f$=0.5) indicated that 10% of the starting material remained, and one major new spot with polarity larger than that of the starting material was detected. The reaction mixture was quenched by adding a saturated EDTA solution (100 mL) and extracted with EtOAc (100 mL×3). The combined organic layers were washed with brine (50 mL×3), dried over anhydrous sodium sulfate, filtered, and concentrated under reduced pressure. The crude residue was purified by column chromatography (SiO$_2$, PE:EtOAc=5:1 to 1:1) and reversed-phase HPLC to afford the desired product (240 mg, 324.62 µmol, 38.40% yield) as a yellow solid. MS (ES$^+$, m/z): 710.3.

Preparation of N-[(7S,8R)-7-fluoro-1,4-dioxaspiro[4.5]decan-8-yl]-2-{3-[(4-methanesulfonyl-2-methoxyphenyl)amino]prop-1-yn-1-yl}-1-(2,2,2-trifluoroethyl)-1H-indol-4-amine: A solution of tert-butyl (3-(4-(((7S,8R)-7-fluoro-1,4-dioxaspiro[4.5]decan-8-yl)amino)-1-(2,2,2-trifluoroethyl)-1H-indol-2-yl)prop-2-yn-1-yl)(2-methoxy-4-(methylsulfonyl)phenyl)carbamate (30 mg, 40.58 μmol, 1 eq.) in TFA (770 mg, 6.75 mmol, 0.5 mL, 166.42 eq.) and DCM (1 mL) was degassed and purged with $N_2$ three times. The mixture was stirred at 25° C. for 30 min under $N_2$. TLC analysis (PE:EtOAc=1:1, $R_f$=0.4) indicated that 10% of the starting material remained, and one major new spot with polarity greater than that of the starting material was detected. The reaction mixture was concentrated under reduced pressure to remove solvent. The residue was diluted with a saturated $Na_2CO_3$ solution (5 mL) and extracted with EtOAc (20 mL×3). The combined organic layers were washed with brine (3 mL×3), dried over anhydrous sodium sulfate, filtered, and concentrated under reduced pressure. The crude product was purified by reversed-phase HPLC to give the desired product (11.4 mg, 18.59 μmol, 45.81% yield) as a white solid. MS (ES+, m/z): 610.2.

Example C25: Synthesis of Compounds 273A, 274A, 281A, 282A, 521A, and 696A

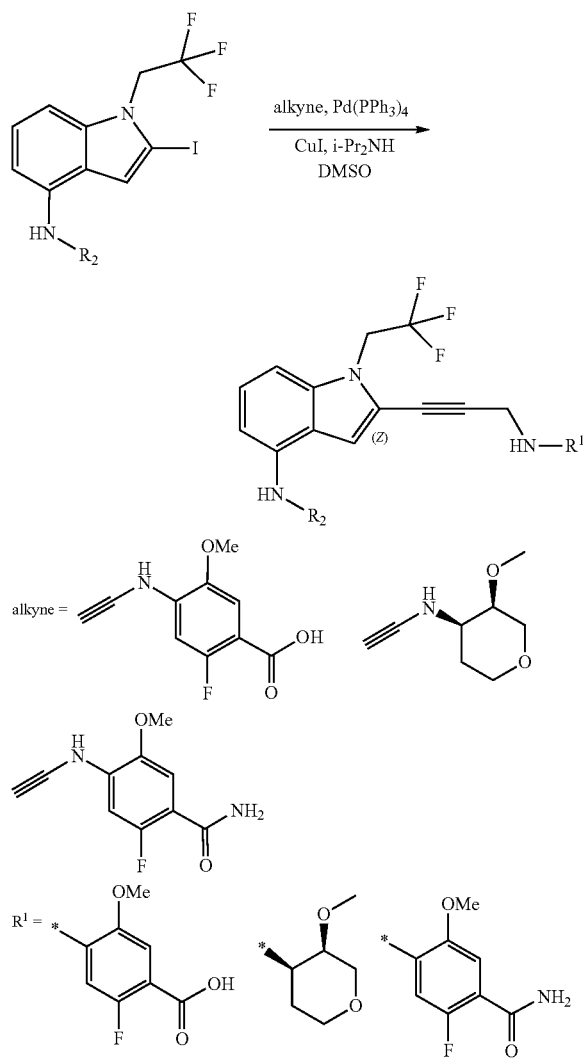

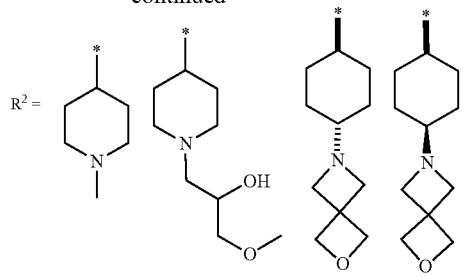

General Procedure: To a mixture of alkyne (1~2 eq.) in DMSO (2 mL) were added i-Pr$_2$NH (3~10 eq.), CuI (0.20~1 eq.), 2-iodo-N—(R²-substituted)-1-(2,2,2-trifluoroethyl)-1H-indol-4-amine (1 eq.), and Pd(PPh$_3$)$_4$ (0.20~0.50 eq.). The mixture was stirred at 20~40° C. for 1~3 h under $N_2$. LC-MS or TLC analysis detected the reaction was complete. The mixture was poured into saturated EDTA solution and stirred for 1 h. The aqueous phase was extracted with EtOAc (3×). The combined organic layers were washed with brine (3×), dried over anhydrous sodium sulfate, filtered, and concentrated in vacuo. The residue was purified by prep-TLC, then by prep-HPLC to afford the desired compound.

2-fluoro-5-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide), MS (ES+, m/z): 614.2; 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxybenzamide, MS (ES+, m/z): 614.2; 2-fluoro-5-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzoic acid, MS (ES+, m/z): 615.2; 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxybenzoic acid, MS (ES+, m/z): 615.2; 2-(3-(((3R,4R)-3-methoxytetrahydro-2H-pyran-4-yl)amino)prop-1-yn-1-yl)-N-(1-methylpiperidin-4-yl)-1-(2,2,2-trifluoroethyl)-1H-indol-4-amine, MS (ES+, m/z): 497.2; and 1-methoxy-3-(4-((2-(3-(((3R,4R)-3-methoxytetrahydro-2H-pyran-4-yl)amino)prop-1-yn-1-yl)-1-(2,2,2-trifluoroethyl)-1H-indol-4-yl)amino)piperidin-1-yl)propan-2-ol, MS (ES+, m/z): 553.2.

Example C26: Synthesis of Compounds 305A and 306A

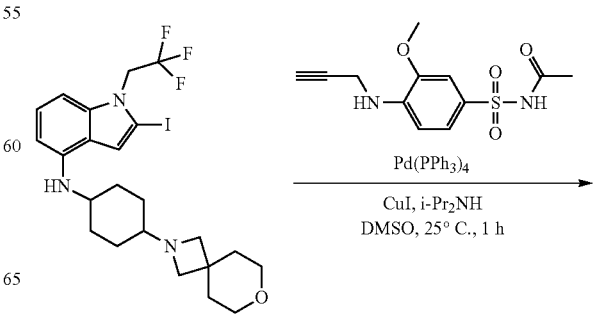

617

-continued

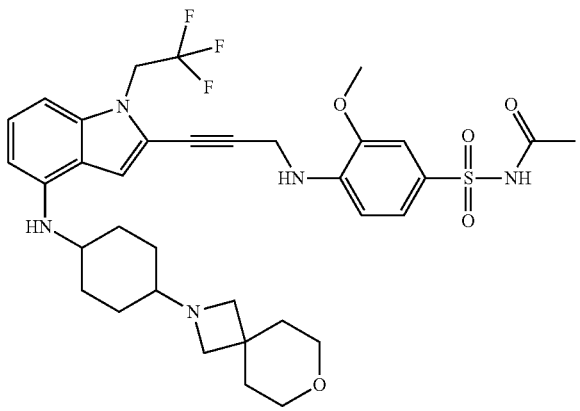

General Procedure: To a mixture of N-((3-methoxy-4-(prop-2-yn-1-ylamino)phenyl)sulfonyl)acetamide (1.3 eq.) in DMSO were added i-Pr$_2$NH (10 eq.), CuI (0.5 eq.), N-(4-(7-oxa-2-azaspiro[3.5]nonan-2-yl)cyclohexyl)-2-iodo-1-(2,2,2-trifluoroethyl)-1H-indol-4-amine (1 eq.), and Pd(PPh$_3$)$_4$ (0.20 eq.) at 25° C. The mixture was stirred at 25° C. for 1 h. LC-MS analysis showed that the reaction was complete. EtOAc (20 mL) was poured into the mixture, and the resulting mixture was poured into a saturated EDTA solution (30 mL) and stirred for 1 h. The aqueous phase was extracted with EtOAc (20 mL×3). The combined organic layers were washed with brine (30 mL×3), dried over anhydrous sodium sulfate, treated with activated carbon, filtered, and concentrated in vacuo. The residue was purified by prep-TLC and prep-HPLC to afford the desired products as white solids.

N-((4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)acetamide, MS (ES$^+$, m/z): 702.3; and N-((4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)acetamide, MS (ES$^+$, m/z): 702.3.

Example C27: Synthesis of Compounds 307A and 308A

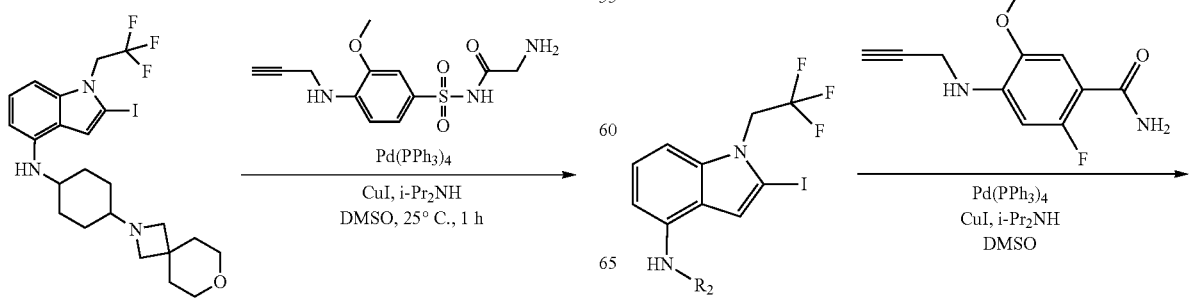

618

-continued

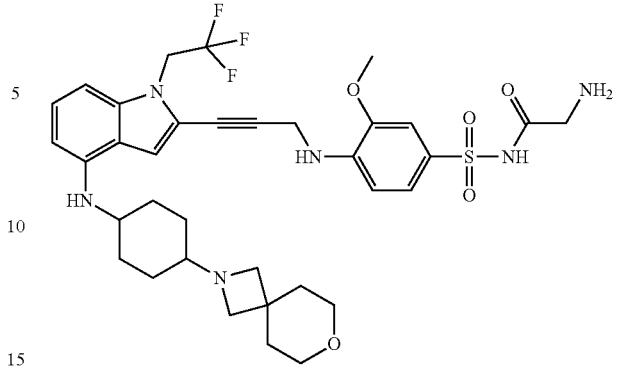

General Procedure: To a mixture of 2-amino-N-((3-methoxy-4-(prop-2-yn-1-ylamino)phenyl)sulfonyl)acetamide (1.2 eq.) in DMSO were added i-Pr$_2$NH (10 eq.), CuI (0.5 eq.), N-(4-(7-oxa-2-azaspiro[3.5]nonan-2-yl)cyclohexyl)-2-iodo-1-(2,2,2-trifluoroethyl)-1H-indol-4-amine (1 eq.), and Pd(PPh$_3$)$_4$ (0.20 eq.) at 25° C. The mixture was stirred at 25° C. for 1 h. LC-MS and HPLC analysis showed that the reaction was complete. EtOAc (10 mL) was poured into the mixture, and the resulting mixture was poured into a saturated EDTA solution (30 mL) and stirred for 15 min. The aqueous phase was extracted with EtOAc (30 mL×2). The organic layer was poured to a saturated EDTA solution (30 mL) and stirred further for 1 h. The aqueous phase was extracted with EtOAc (30 mL×3). The combined organic layers were washed with brine (30 mL×3), dried over anhydrous sodium sulfate, filtered, and concentrated in vacuo. The crude residue was purified by prep-HPLC to afford the desired products as light yellow solids.

N-((4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)-2-aminoacetamide, MS (ES$^+$, m/z): 717.3; and N-((4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)-2-aminoacetamide, MS (ES$^+$, m/z): 717.3.

Example C28: Synthesis of Compounds 514A, 513A, 683A, 684A, 132A, 133A, 128A, 129A, 271A, and 272A

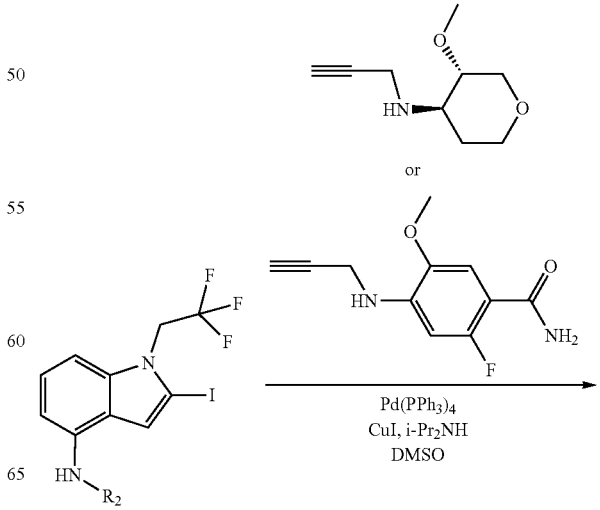

-continued

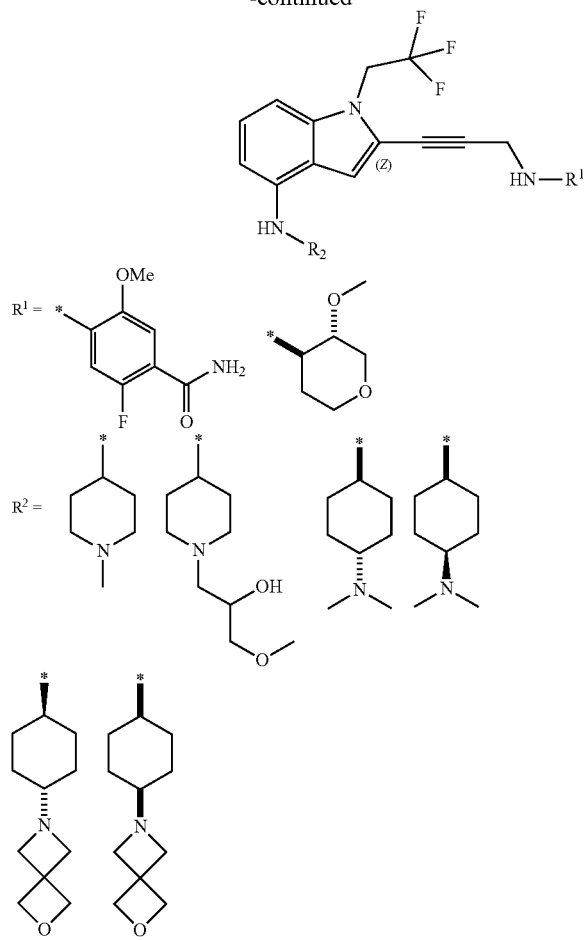

General Procedure: To a solution of (3S,4R)-3-methoxy-N-(prop-2-yn-1-yl)tetrahydro-2H-pyran-4-amine or 2-fluoro-5-methoxy-4-(prop-2-yn-1-ylamino)benzamide (1-2 eq.) in DMSO (2 mL) were added i-Pr$_2$NH (3~10 eq.), CuI (0.20~1 eq.), 2-iodo-N—(R$^2$-substituted)-1-(2,2,2-trifluoroethyl)-1H-indol-4-amine (1 eq.), and Pd(PPh$_3$)$_4$ (0.20~0.50 eq.). The mixture was stirred at 20~40° C. for 1-3 h under N$_2$. LC-MS or TLC analysis showed that the reaction was complete. The mixture was poured into saturated EDTA solution and stirred for 1 h. The aqueous phase was extracted with EtOAc (3×). The combined organic layers were washed with brine (3×), dried over anhydrous sodium sulfate, filtered, and concentrated in vacuo. The residue was purified by prep-TLC and prep-HPLC to afford the desired products.

2-fluoro-5-methoxy-4-[(3-{4-[(1-methylpiperidin-4-yl)amino]-1-(2,2,2-trifluoroethyl)-1H-indol-2-yl}prop-2-yn-1-yl)amino]benzamide, MS (ES$^+$, m/z): 532.2; 2-(3-(((3S,4R)-3-methoxytetrahydro-2H-pyran-4-yl)amino)prop-1-yn-1-yl)-N-(1-methylpiperidin-4-yl)-1-(2,2,2-trifluoroethyl)-1H-indol-4-amine, MS (ES$^+$, m/z): 479.2; 2-fluoro-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-5-methoxybenzamide, MS (ES$^+$, m/z): 606.2; 1-methoxy-3-(4-((2-(3-(((3S,4R)-3-methoxytetrahydro-2H-pyran-4-yl)amino)prop-1-yn-1-yl)-1-(2,2,2-trifluoroethyl)-1H-indol-4-yl)amino)piperidin-1-yl)propan-2-ol, MS (ES$^+$, m/z): 553.2; 4-((3-(4-(((1R,4R)-4-(dimethylamino)cyclohexyl)amino)-1-(2,2,2-trifluoroethyl)-1H-indol-2-yl)prop-2-yn-1-yl)amino)-2-fluoro-5-methoxybenzamide, MS (ES$^+$, m/z): 560.2; 4-((3-(4-(((1S,4S)-4-(dimethylamino)cyclohexyl)amino)-1-(2,2,2-trifluoroethyl)-1H-indol-2-yl)prop-2-yn-1-yl)amino)-2-fluoro-5-methoxybenzamide, MS (ES$^+$, m/z): 560.2; (1R,4R)—N$^1$-(2-(3-(((3S,4R)-3-methoxytetrahydro-2H-pyran-4-yl)amino)prop-1-yn-1-yl)-1-(2,2,2-trifluoroethyl)-1H-indol-4-yl)-N$^4$,N$^4$-dimethylcyclohexane-1,4-diamine, MS (ES$^+$, m/z): 507.3; (1S,4S)—N$^1$-(2-(3-(((3S,4R)-3-methoxytetrahydro-2H-pyran-4-yl)amino)prop-1-yn-1-yl)-1-(2,2,2-trifluoroethyl)-1H-indol-4-yl)-N$^4$,N$^4$-dimethylcyclohexane-1,4-diamine, MS (ES$^+$, m/z): 507.3; N-((1R,4R)-4-(2-oxa-6-azaspiro[3.3]heptan-6-yl)cyclohexyl)-2-(3-(((3S,4R)-3-methoxytetrahydro-2H-pyran-4-yl)amino)prop-1-yn-1-yl)-1-(2,2,2-trifluoroethyl)-1H-indol-4-amine, MS (ES$^+$, m/z): 561.3; and N-((1S,4S)-4-(2-oxa-6-azaspiro[3.3]heptan-6-yl)cyclohexyl)-2-(3-(((3S,4R)-3-methoxytetrahydro-2H-pyran-4-yl)amino)prop-1-yn-1-yl)-1-(2,2,2-trifluoroethyl)-1H-indol-4-amine, MS (ES$^+$, m/z): 561.3.

Example C29: Synthesis of (3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol (Compound 43A)

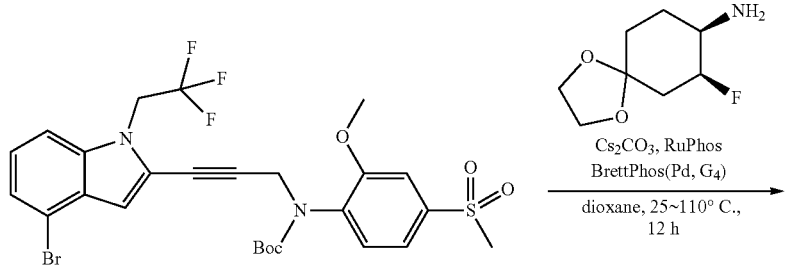

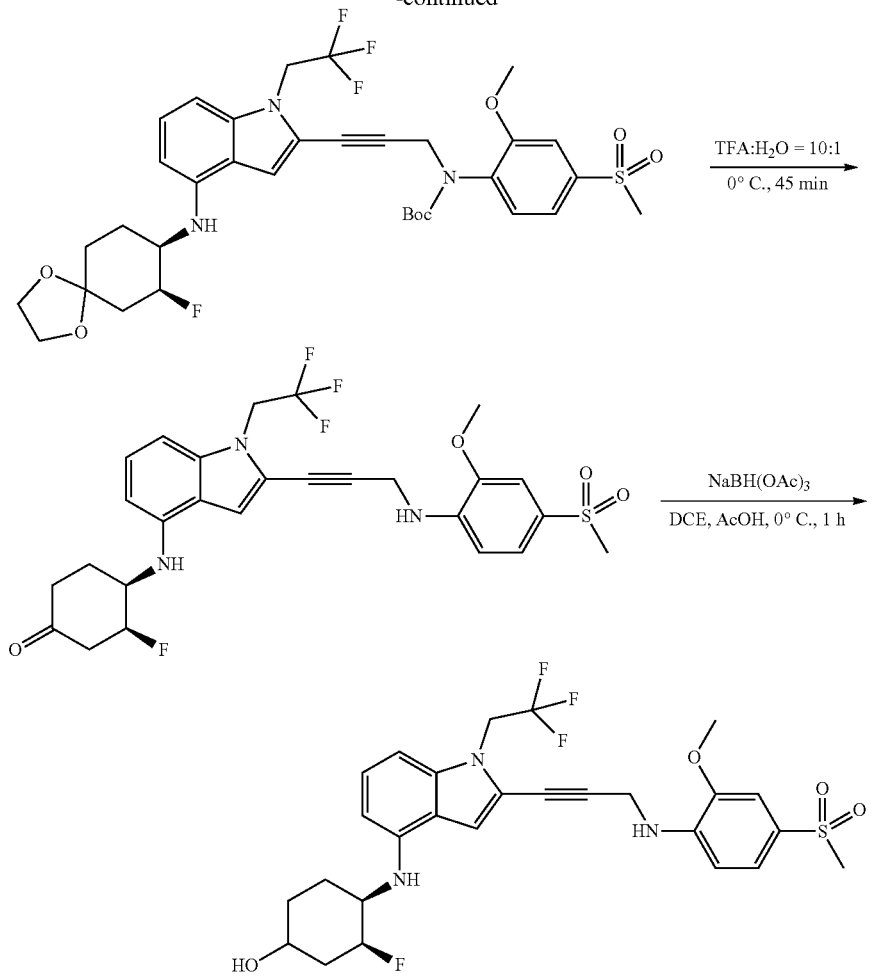

Preparation of tert-butyl (3-(4-(((7S,8R)-7-fluoro-1,4-dioxaspiro[4.5]decan-8-yl)amino)-1-(2,2,2-trifluoroethyl)-1H-indol-2-yl)prop-2-yn-1-yl)(2-methoxy-4-(methylsulfonyl)phenyl)carbamate: To a mixture of tert-butyl (3-(4-bromo-1-(2,2,2-trifluoroethyl)-1H-indol-2-yl)prop-2-yn-1-yl)(2-methoxy-4-(methylsulfonyl)phenyl)carbamate (0.5 g, 812.40 μmol, 1 eq.), Cs₂CO₃ (794.09 mg, 2.44 mmol, 3 eq.), RuPhos (49.28 mg, 105.61 μmol, 0.13 eq.), and (7R,8R)-7-fluoro-1,4-dioxaspiro[4.5]decan-8-amine (189.15 mg, 893.64 μmol, 1.1 eq., HCl) in dioxane (10 mL) was added BrettPhos (Pd, G4) (44.87 mg, 48.74 μmol, 0.06 eq.) at 25° C. under N₂. The mixture was de-gassed and heated to 110° C. and stirred for 12 h under N₂. TLC analysis (PE: EtOAc=1:1, R_f=0.2) indicated that 10% of the starting material remained, and one major new spot with polarity greater than that of the starting material was detected. The reaction mixture was concentrated under reduced pressure to remove dioxane. The residue was diluted with water (50 mL) and extracted with EtOAc (50 mL×3). The combined organic layers were washed with brine (50 mL×3), dried over anhydrous sodium sulfate, filtered, and concentrated under reduced pressure. The crude residue was purified by column chromatography (SiO₂, PE:EtOAc=10:1 to 1:2) to afford the desired product (0.6 g, 798.88 μmol, 56.70% yield) as a yellow solid.

Preparation of (3S,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)cyclohexan-1-one: To a solution of tert-butyl (3-(4-(((7S,8R)-7-fluoro-1,4-dioxaspiro[4.5]decan-8-yl)amino)-1-(2,2,2-trifluoroethyl)-1H-indol-2-yl)prop-2-yn-1-yl)(2-methoxy-4-(methylsulfonyl)phenyl)carbamate (100 mg, 140.90 μmol, 1 eq.) in water (0.3 mL) was added TFA (3 mL) at 0° C. The mixture was stirred for 45 min. TLC analysis (PE:EtOAc=1:1) showed that the starting material remained, and one new spot was detected. The mixture was poured into a saturated aqueous solution of Na₂CO₃ (50 mL) and extracted with EtOAc (20 mL×3). The combined organic layers were washed with brine (20 mL×3), dried over anhydrous sodium sulfate, filtered, and concentrated under reduced pressure to give the desired product (0.09 g, crude) as a yellow solid.

Preparation of (3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol: To a solution of (3S,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)cyclohexan-1-one (50 mg, 88.41 μmol, 1 eq.) in DCE (1 mL) were added AcOH (0.2 mL) and NaBH(OAc)₃ (37.47 mg, 176.81 μmol, 2 eq.). The mixture was stirred at 0° C. for 1 h. TLC analysis (PE:EtOAc=1:2, R_f=0.2) indicated that 30% of the starting material remained, and one major new spot with polarity greater than that of the starting material was detected. The mixture was poured into a saturated aqueous solution of Na$_2$CO$_3$ (40 mL) and extracted with EtOAc (30 mL×3). The combined organic layers were washed with brine (20 mL×3), dried over anhydrous sodium sulfate, filtered, and concentrated under reduced pressure. The crude residue was purified by prep-TLC (PE:EtOAc:DCM:MeOH=50:50:30:3) and prep-HPLC to afford the desired product (15 mg, 25.58 μmol, 28.94% yield) as a white solid. MS (ES$^+$, m/z): 568.2.

Example C30: Synthesis of Compounds 37A, 38A, 39A, 40A, 41A, and 42A

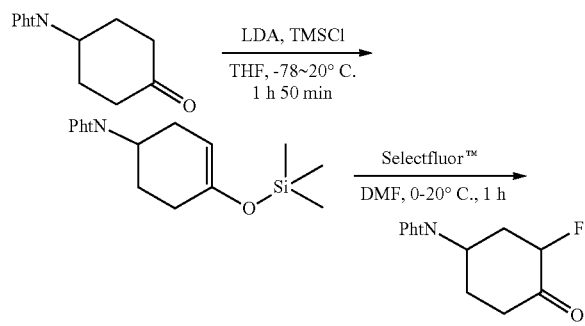

Preparation of 2-(((4-((trimethylsilyl)oxy)cyclohex-3-en-1-yl)-λ$^2$-azaneyl)carbonyl)benzoic acid: To a solution of 2-(((4-oxocyclohexyl)-λ$^2$-azaneyl)carbonyl)benzoic acid (10 g, 41.11 mmol, 1 eq.) in THF (150 mL) was added LDA (2 M, 30.83 mL, 1.5 eq.) at −78° C. The mixture was stirred at −78° C. for 10 min, then warmed up to 20° C. and stirred further at 20° C. for 10 min. The mixture was then cooled to −78° C., and TMSCl (4.91 g, 45.22 mmol, 5.74 mL, 1.1 eq.) was added into the reaction. The mixture was then stirred at −78° C. for 0.5 h, then warmed up to 20° C. for 1 h. TLC analysis (PE:EtOAc=3:1, R$_f$=0.4) indicated that 30% of the starting material remained, and one major new spot with polarity lower than that of the starting material was detected. The mixture was poured into saturated solution of NH$_4$Cl (100 mL) and extracted with EtOAc (100 mL×3). The combined organic layers were washed with brine (100 mL×3), dried over anhydrous sodium sulfate, filtered, and concentrated under reduced pressure. The crude residue was purified by column chromatography (SiO$_2$, PE:EtOAc=50:1 to 1:1) to afford the desired product (4 g, 11.41 mmol, 27.76% yield) as a light yellow solid.

Preparation of 2-(((3-fluoro-4-oxocyclohexyl)-λ$^2$-azaneyl)carbonyl)benzoic acid: To solution of 2-(((4-((trimethylsilyl)oxy)cyclohex-3-en-1-yl)-λ$^2$-azaneyl)carbonyl) benzoic acid (1.5 g, 4.76 mmol, 1 eq.) in DMF (16 mL) was added a solution of Selectfluor™ (1.85 g, 5.23 mmol, 1.1 eq.) in DMF (12 mL) at 0° C. The mixture was slowly was warmed to 20° C. and stirred for 1 h under N$_2$. TLC analysis (PE:EtOAc=3:1, R$_f$=0.1) indicated that the starting material was consumed completely, and one new spot was detected. The reaction mixture was diluted with saturated solution of NH$_4$Cl (100 mL) and extracted with EtOAc (40 mL×3). The combined organic layers were washed with brine (40 mL×3), dried over anhydrous sodium sulfate, filtered, and concentrated under reduced pressure to give the desired product (1 g, crude) as a light yellow solid.

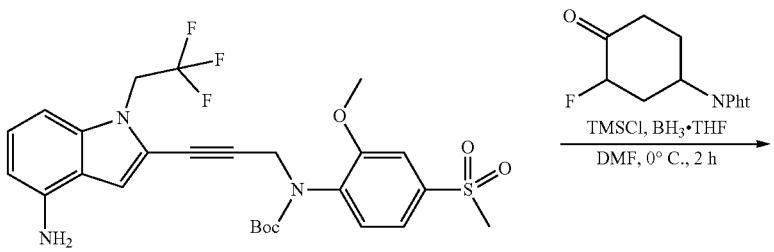

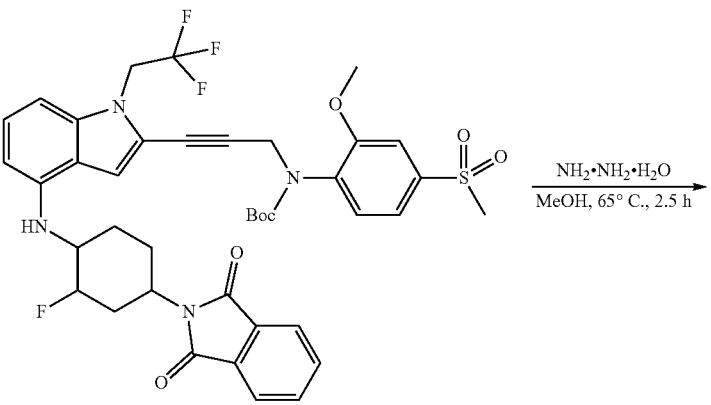

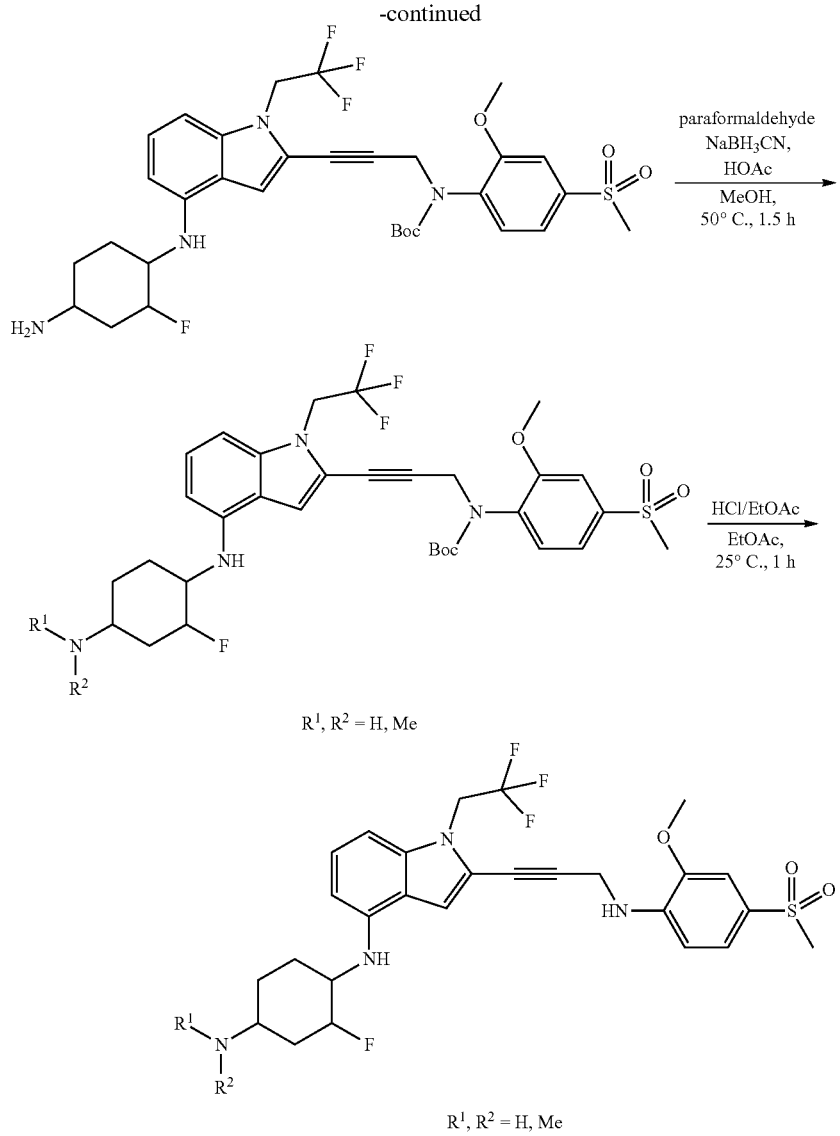

Preparation of tert-butyl (3-(4-((4-(1,3-dioxoisoindolin-2-yl)-2-fluorocyclohexyl)amino)-1-(2,2,2-trifluoroethyl)-1H-indol-2-yl)prop-2-yn-1-yl)(2-methoxy-4-(methylsulfonyl)phenyl)-carbamate: To a mixture of tert-butyl (3-(4-amino-1-(2,2,2-trifluoroethyl)-1H-indol-2-yl)prop-2-yn-1-yl)(2-methoxy-4-(methylsulfonyl)phenyl)carbamate (500 mg, 906.49 μmol, 1 eq.) and 2-(((3-fluoro-4-oxocyclohexyl)-λ²-azaneyl)carbonyl)benzoic acid (473.64 mg, 1.81 mmol, 2 eq.) in DMF (10 mL) was added TMSCl (246.21 mg, 2.27 mmol, 287.63 μL, 2.5 eq.) at 0° C. The mixture was stirred at 0° C. for 1 h, BH$_3$·THF (1 M, 2.72 mL, 3 eq.) was added into the mixture at 0° C., and the resulting mixture was stirred further at 0° C. for 1 h. HPLC analysis showed that 5% of the starting material remained, and 57.3% of the desired compound was detected. The mixture was poured into a saturated aqueous solution of Na$_2$CO$_3$ (20 mL) and extracted with EtOAc (20 mL×3). The combined organic layers were washed with brine (20 mL×3), dried over anhydrous sodium sulfate, filtered, and concentrated under reduced pressure. The crude residue was purified by prep-HPLC.

The solution obtained from peak 2 (retention time 3.6 min) was adjusted to pH>9 by adding a saturated solution of Na$_2$CO$_3$. The mixture was then extracted with EtOAc (20 mL×3). The combined organic layers were washed with brine (20 mL×3), dried over anhydrous sodium sulfate, filtered, and concentrated under reduced pressure to give tert-butyl N-[3-[4-[[4-(1,3-dioxoisoindolin-2-yl)-2-fluoro-cyclohexyl]amino]-1-(2,2,2-trifluoroethyl)indol-2-yl]prop-2-ynyl]-N-(2-methoxy-4-methylsulfonyl-phenyl)carbamate (0.2 g, 144.57 μmol, 15.95% yield) was obtained as a yellow solid.

Preparation of tert-butyl (3-(4-((4-amino-2-fluorocyclohexyl)amino)-1-(2,2,2-trifluoroethyl)-1H-indol-2-yl)prop-2-yn-1-yl)(2-methoxy-4-(methylsulfonyl)phenyl)carbamate: To a solution of tert-butyl (3-(4-((4-(1,3-dioxoisoindolin-2-yl)-2-fluorocyclohexyl)amino)-1-(2,2,2-trifluoroethyl)-1H-indol-2-yl)prop-2-yn-1-yl)(2-methoxy-4-(methylsulfonyl)phenyl)carbamate (0.18 g, 221.83 μmol, 1 eq.) in MeOH (3 mL) was added NH$_2$NH$_2$·H$_2$O (33.31 mg, 665.49 μmol, 32.34 μL, 3 eq.) at 65° C. The mixture was stirred for 2.5 h under N$_2$. LC-MS and HPLC analysis showed that the starting material was consumed completely, and one main peak with the desired mass was detected. The mixture was poured into saturated solution of Na$_2$CO$_3$ (30 mL) and extracted with EtOAc (20 mL×3). The combined organic layers were washed with brine (20 mL×3), dried over anhydrous sodium sulfate, filtered, and concentrated under reduced pressure to give the desired product (0.16 g, crude) as a yellow solid. MS (ES$^+$, m/z): 667.3.

Preparation of Boc-protected intermediates: To a solution of tert-butyl (3-(4-((4-amino-2-fluorocyclohexyl)amino)-1-(2,2,2-trifluoroethyl)-1H-indol-2-yl)prop-2-yn-1-yl)(2-methoxy-4-(methylsulfonyl)phenyl)carbamate (0.14 g, 209.98 μmol, 1 eq.) in MeOH (1 mL) were added AcOH (37.11 mg, 617.91 μmol, 35.34 μL, 2.94 eq.), paraformaldehyde (31.52 mg), and NaBH$_3$CN (65.98 mg, 1.05 mmol, 5 eq.) at 50° C. The mixture was stirred for 1.5 h under N$_2$. LC-MS analysis showed that the starting material remained, and several new peaks were observed. The reaction mixture was diluted with saturated solution of Na$_2$CO$_3$ (30 mL) and extracted with EtOAc (20 mL×3). The combined organic layers were washed with brine (20 mL×3), dried over anhydrous sodium sulfate, filtered, and concentrated under reduced pressure. The residue was purified by prep-TLC (PE:EtOAc:DCM:MeOH:TEA=50:50:100:10:30) to afford the desired products as yellow solids.

tert-Butyl (3-(4-((4-(dimethylamino)-2-fluorocyclohexyl) amino)-1-(2,2,2-trifluoroethyl)-1H-indol-2-yl)prop-2-yn-1-yl)(2-methoxy-4-(methylsulfonyl)phenyl)carbamate (15 mg, 21.59 μmol, 30% yield), MS (ES$^+$, m/z): 695.3; tert-butyl (3-(4-((2-fluoro-4-(methylamino)cyclohexyl)amino)-1-(2,2,2-trifluoroethyl)-1H-indol-2-yl)prop-2-yn-1-yl)(2-methoxy-4-(methylsulfonyl)phenyl)carbamate (15 mg, 22.03 μmol, 30.62% yield), MS (ES$^+$, m/z): 681.2; tert-butyl (3-(4-((4-amino-2-fluorocyclohexyl)amino)-1-(2,2,2-trifluoroethyl)-1H-indol-2-yl)prop-2-yn-1-yl)(2-methoxy-4-(methylsulfonyl)phenyl)carbamate (30 mg, 43.29 μmol, 60.15% yield), MS (ES$^+$, m/z): 667.2.

General procedure for the preparation of final products: To a solution of tert-butyl (3-(4-((4-(dimethylamino)-2-fluorocyclohexyl)amino)-1-(2,2,2-trifluoroethyl)-1H-indol-2-yl)prop-2-yn-1-yl)(2-methoxy-4-(methylsulfonyl)phenyl) carbamate; tert-butyl (3-(4-((2-fluoro-4-(methylamino) cyclohexyl)amino)-1-(2,2,2-trifluoroethyl)-1H-indol-2-yl) prop-2-yn-1-yl)(2-methoxy-4-(methylsulfonyl)phenyl) carbamate; or tert-butyl (3-(4-((4-amino-2-fluorocyclohexyl)amino)-1-(2,2,2-trifluoroethyl)-1H-indol-2-yl)prop-2-yn-1-yl)(2-methoxy-4-(methylsulfonyl)phenyl) carbamate (30 mg, 45 μmol, 1 eq.) in EtOAc (1 mL) was added HCl/EtOAc (4 M, 2.08 mL, 185 eq.) at 25° C. The mixture was stirred for 1 h. LC-MS analysis showed that the starting material was consumed completely, and one main peak with desired mass was detected. The mixture was poured into a saturated solution of Na$_2$CO$_3$ (20 mL) and extracted with EtOAc (20 mL×3). The combined organic layers were washed with brine (20 mL×3), dried over anhydrous sodium sulfate, filtered, and concentrated under reduced pressure. The crude residue as purified by prep-HPLC to afford the desired products.

(1R,2R,4S)-2-fluoro-N$^1$-(2-(3-((2-methoxy-4-(methylsulfonyl)phenyl)amino)prop-1-yn-1-yl)-1-(2,2,2-trifluoroethyl)-1H-indol-4-yl)-N$^4$,N$^4$-dimethylcyclohexane-1,4-diamine, MS (ES$^+$, m/z): 595.3; (1R,2R,4S)-2-fluoro-N$^1$-(2-(3-((2-methoxy-4-(methylsulfonyl)phenyl)amino)prop-1-yn-1-yl)-1-(2,2,2-trifluoroethyl)-1H-indol-4-yl)-N$^4$-methylcyclohexane-1,4-diamine, MS (ES$^+$, m/z): 581.3; and (1R,2R,4S)-2-fluoro-N$^1$-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine, MS (ES$^+$, m/z): 567.2; 2-fluoro-N$^1$-(2-(3-((2-methoxy-4-(methylsulfonyl) phenyl)amino)prop-1-yn-1-yl)-1-(2,2,2-trifluoroethyl)-1H-indol-4-yl)-N$^4$,N$^4$-dimethylcyclohexane-1,4-diamine, MS (ES$^+$, m/z): 595.3; 2-fluoro-N$^1$-(2-{3-[(4-methanesulfonyl-2-methoxyphenyl)amino]prop-1-yn-1-yl}-1-(2,2,2-trifluoroethyl)-1H-indol-4-yl)-N$^4$-methylcyclohexane-1,4-diamine, MS (ES$^+$, m/z): 581.3; 2-fluoro-N$^1$-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine, MS (ES$^+$, m/z): 567.2.

Example C31: Synthesis of Compounds 58A, 475A, 481A, 545A, 546A, 556A, 560A, 561A, 615A, 693A, 717A, 1004A, and 1005A

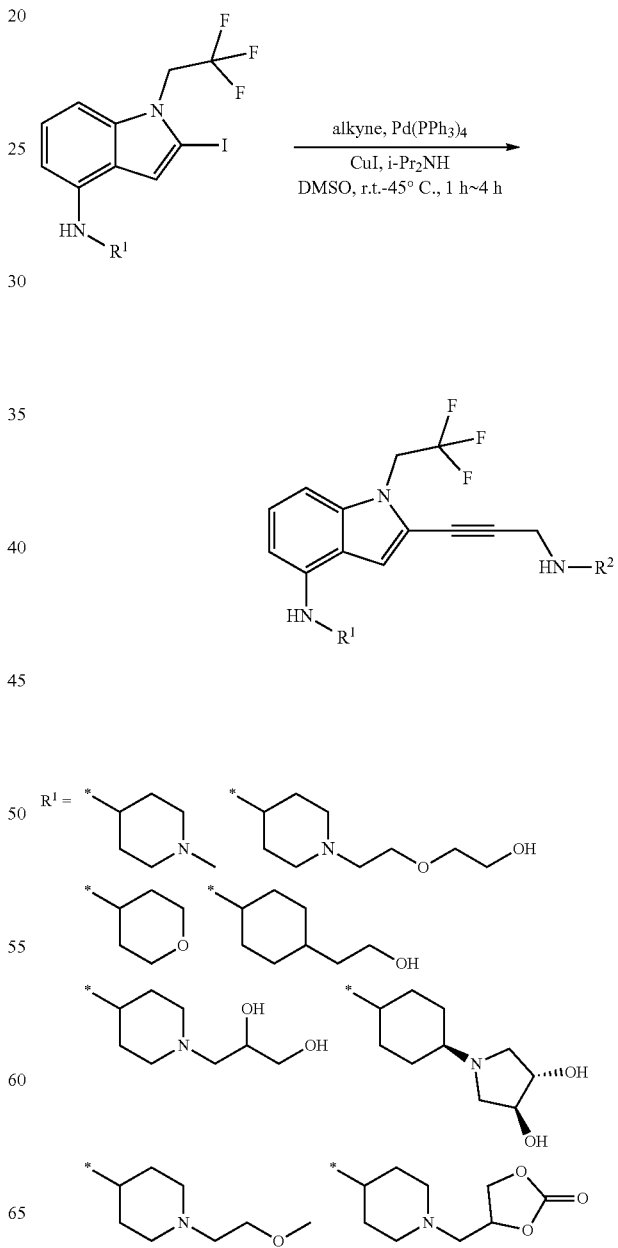

alkyne =

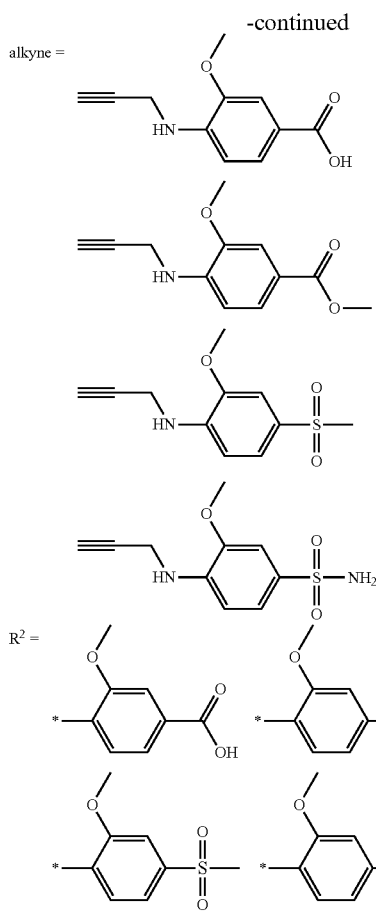

To a solution of alkyne (1~2 eq., HCl or free) in DMSO (1~10 mL) were added i-Pr₂NH (10~30 eq.), CuI (1~2 eq.), 1-(2,2-difluoroethyl)-2-iodo-N—(R¹-substituted)-1H-indol-4-amine (1 eq.), Pd(PPh₃)₄ (0.20~0.50 eq.) at 20~45° C. The mixture was stirred at for 1~4 h. TLC or LC-MS analysis detected that the reaction was complete. EtOAc (10 mL) was poured into the mixture, and the resulting mixture was poured into a saturated EDTA solution (40 mL) and stirred for 15 min. The aqueous phase was extracted with EtOAc (40 mL×2). The combined organic layers were poured to a saturated EDTA solution (40 mL) and stirred further for 1 h. The aqueous phase was extracted with EtOAc (40 mL×3). The combined organic layers were washed with brine (40 mL×3), dried over anhydrous sodium sulfate, treated with activated carbon, filtered, and concentrated in vacuo. The mixture was purified by prep-TLC or column chromatography, then purified once or twice by prep-HPLC to afford the desired products.

3-methoxy-4-{[3-(4-{[(1S,4S)-4-[(3S,4S)-3,4-dihydroxypyrrolidin-1-yl]cyclohexyl]amino}-1-(2,2,2-trifluoroethyl)-1H-indol-2-yl)prop-2-yn-1-yl]amino}benzene-1-sulfonamide, MS (ES⁺, m/z): 621.3; 3-methoxy-4-((3-(4-((1-methylpiperidin-4-yl)amino)-1-(2,2,2-trifluoroethyl)-1H-indol-2-yl)prop-2-yn-1-yl)amino)benzoic acid, MS (ES⁺, m/z): 515.1; 2-(2-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)ethoxy)ethan-1-ol, MS (ES⁺, m/z): 623.2; 3-methoxy-4-((3-(4-((tetrahydro-2H-pyran-4-yl)amino)-1-(2,2,2-trifluoroethyl)-1H-indol-2-yl)prop-2-yn-1-yl)amino)benzoic acid, MS (ES⁺, m/z): 502.2; 2-(4-((2-(3-((2-methoxy-4-(methylsulfonyl)phenyl) amino)prop-1-yn-1-yl)-1-(2,2,2-trifluoroethyl)-1H-indol-4-yl)amino)piperidin-1-yl)ethan-1-ol, MS (ES⁺, m/z): 579.2; 4-((3-(4-((1-(2,3-dihydroxypropyl)piperidin-4-yl)amino)-1-(2,2,2-trifluoroethyl)-1H-indol-2-yl)prop-2-yn-1-yl)amino)-3-methoxybenzoic acid, MS (ES⁺, m/z): 575.2; methyl 3-methoxy-4-((3-(4-((tetrahydro-2H-pyran-4-yl)amino)-1-(2,2,2-trifluoroethyl)-1H-indol-2-yl)prop-2-yn-1-yl)amino)benzoate, MS (ES⁺, m/z): 516.2; methyl 4-((3-(4-((1-(2,3-dihydroxypropyl)piperidin-4-yl)amino)-1-(2,2,2-trifluoroethyl)-1H-indol-2-yl)prop-2-yn-1-yl)amino)-3-methoxybenzoate, MS (ES⁺, m/z): 589.2; 2-(3-((2-methoxy-4-(methylsulfonyl)phenyl)amino)prop-1-yn-1-yl)-N-(1-(2-methoxyethyl)piperidin-4-yl)-1-(2,2,2-trifluoroethyl)-1H-indol-4-amine, MS (ES⁺, m/z): 593.2; 3-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)propane-1,2-diol, MS (ES⁺, m/z): 609.3; 3-methoxy-4-({3-[4-({1-[(2-oxo-1,3-dioxolan-4-yl)methyl]piperidin-4-yl}amino)-1-(2,2,2-trifluoroethyl)-1H-indol-2-yl]prop-2-yn-1-yl}amino)benzene-1-sulfonamide, MS (ES⁺, m/z): 636.2; 4-({4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}methyl)-1,3-dioxolan-2-one, MS (ES⁺, m/z): 635.2; and 6-fluoro-2-{3-[(4-methanesulfonyl-2-methoxyphenyl)amino]prop-1-yn-1-yl}-N-(1-methylpiperidin-4-yl)-1-(2,2,2-trifluoroethyl)-1H-indol-4-amine, MS (ES⁺, m/z): 567.2.

Example C32: Synthesis of Compounds 202A, 203A, 204A, 205A, 398A, 399A, 400A, 401A, and 1047A

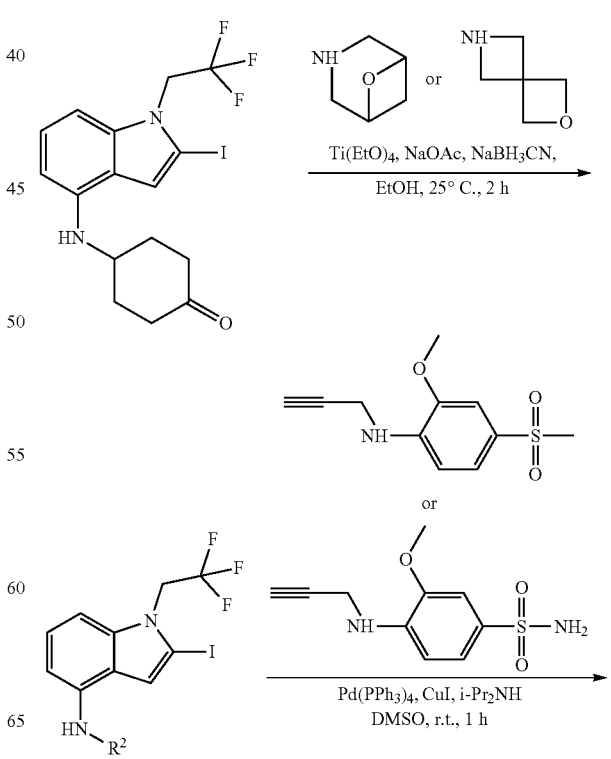

-continued

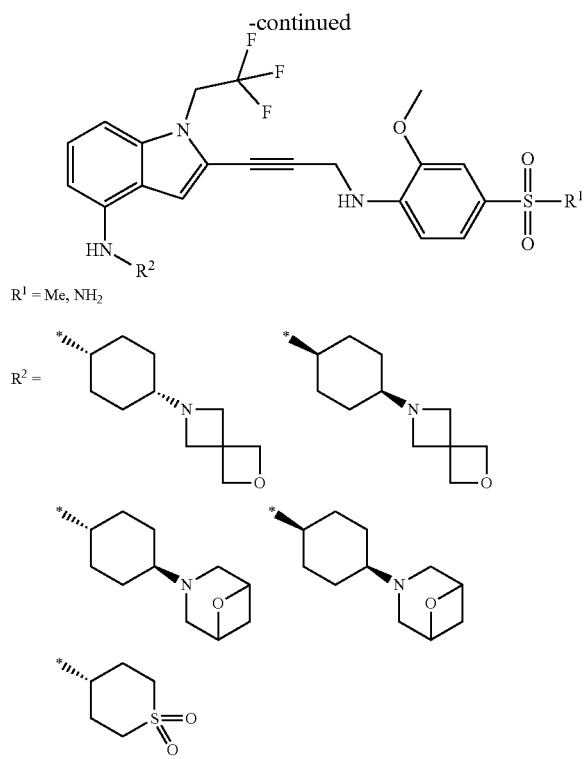

$R^1$ = Me, $NH_2$

General procedure for the preparation of 2-iodo-N—($R^2$-substituted)-1-(2,2,2-trifluoroethyl)-1H-indol-4-amine: A mixture of 6-oxa-3$\lambda^2$-azabicyclo[3.1.1]heptane or 2-oxa-6$\lambda^2$-azaspiro[3.3]heptane (1.5 eq.) 4-((2-iodo-1-(2,2,2-trifluoroethyl)-1H-indol-4-yl)amino)cyclohexan-1-one (1 eq.) with NaOAc (2 eq.) and Ti(OEt)$_4$ (2 eq.) in EtOH (10 mL) was stirred for 1~11 h at 25° C., and NaBH$_3$CN (2 eq.) was added. The reaction mixture was stirred at 25° C. for 1 h. TLC analysis showed that the starting material was consumed completely, and two new spots were detected. The reaction mixture was poured into a saturated aqueous solution of NaHCO$_3$ and filtered. The filtrate was extracted with EtOAc (2×). The combined organic layers were concentrated under reduced pressure to give a residue. The residue was purified by column chromatography (SiO$_2$, PE:EtOAc=2:1 to 1:1) to afford the desired products.

Preparation of final products: To a solution of 2-methoxy-4-(methylsulfonyl)-N-(prop-2-yn-1-yl)aniline or 3-methoxy-4-(prop-2-yn-1-ylamino)benzenesulfonamide (1.2 eq.) in DMSO were added CuI (1 eq.) and N-isopropylpropan-2-amine (10 eq.). The mixture was degassed with N$_2$ three times, and 2-iodo-N—($R^2$-substituted)-1-(2,2,2-trifluoroethyl)-1H-indol-4-amine (1 eq.) and Pd(PPh$_3$)$_4$ (0.2 eq.) were added. The mixture was stirred at 25° C. for 1 h. TLC analysis (DCM:MeOH=10:1, R$_f$=0.25) showed that the starting material was consumed completely, and one main peak with the desired mass was detected. The reaction mixture was diluted with EtOAc, and the resulting mixture was poured into saturated EDTA solution (30 mL), stirred for 2 h, and extracted with EtOAc (2×). The combined organic layers were washed with brine (10 mL), and the organic layer was then concentrated under reduced pressure to give a residue. The residue was purified by prep-TLC to give a residue, and the residue was further purified by prep-HPLC to afford the final products.

2-{3-[(4-methanesulfonyl-2-methoxyphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine, 27% yield, MS (ES$^+$, m/z): 631.2; 2-{3-[(4-methanesulfonyl-2-methoxyphenyl)amino]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine, 18% yield, MS (ES$^+$, m/z): 631.2; 3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide, 14.2% yield, MS (ES$^+$, m/z): 632.2; 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide, 13.7% yield, MS (ES$^+$, m/z): 632.2; 2-{3-[(4-methanesulfonyl-2-methoxyphenyl)amino]prop-1-yn-1-yl}-N-[(1R,4R)-4-{6-oxa-3-azabicyclo[3.1.1]heptan-3-yl}cyclohexyl]-1-(2,2,2-trifluoroethyl)-1H-indol-4-amine, 27.1% yield, MS (ES$^+$, m/z): 631.2; 2-{3-[(4-methanesulfonyl-2-methoxyphenyl)amino]prop-1-yn-1-yl}-N-[(1S,4S)-4-{6-oxa-3-azabicyclo[3.1.1]heptan-3-yl}cyclohexyl]-1-(2,2,2-trifluoroethyl)-1H-indol-4-amine, 21.5% yield, MS (ES$^+$, m/z): 631.2; 3-methoxy-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzene-1-sulfonamide, 23% yield, MS (ES$^+$, m/z): 632.2; 3-methoxy-4-{[3-(4-{[(1S,4S)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzene-1-sulfonamide, 13.1% yield, MS (ES$^+$, m/z): 632.2; and 4-[(2-{3-[(2-methoxy-4-{2-oxa-6-azaspiro[3.3]heptane-6-sulfonyl}phenyl)amino]prop-1-yn-1-yl}-1-(2,2,2-trifluoroethyl)-1H-indol-4-yl)amino]-1$\lambda^6$-thiane-1,1-dione, 12.5% yield, MS (ES$^+$, m/z): 667.1.

Example C33: Synthesis of 200A and 201A

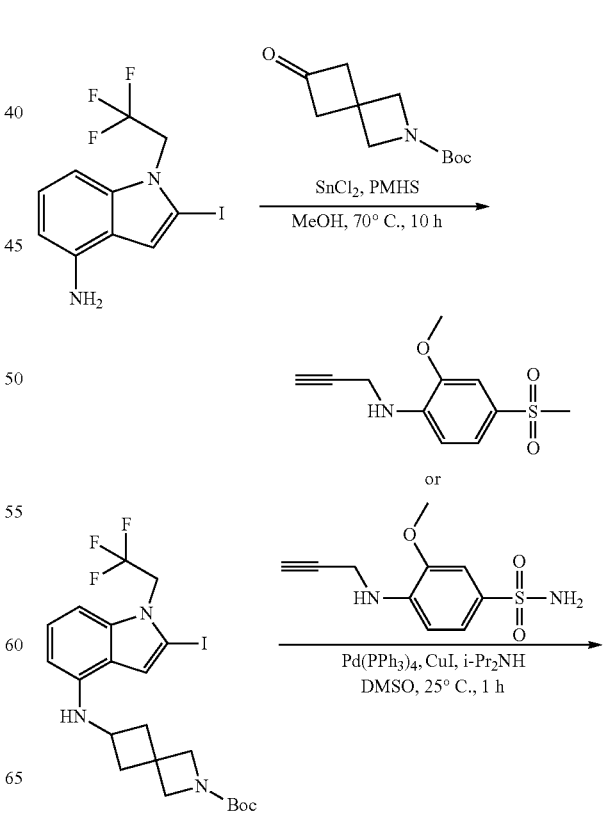

-continued

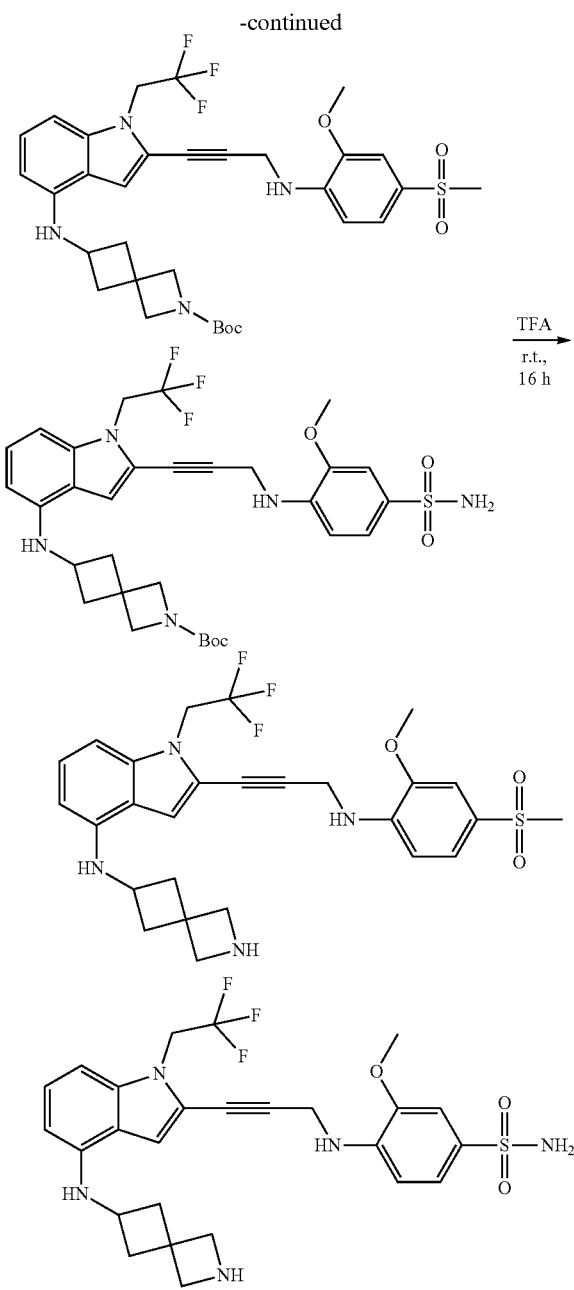

Preparation of tert-butyl 6-((2-iodo-1-(2,2,2-trifluoroethyl)-1H-indol-4-yl)amino)-2-azaspiro[3.3]heptane-2-carboxylate: To a solution of 2-iodo-1-(2,2,2-trifluoroethyl)-1H-indol-4-amine (0.5 g, 1.47 mmol, 1 eq.) in MeOH (5 mL) were added tert-butyl 6-oxo-2-azaspiro[3.3]heptane-2-carboxylate (776.49 mg, 3.68 mmol, 40.50 µL, 2.5 eq.) and SnCl$_2$·2H$_2$O (66.35 mg, 294.05 µmol, 24.48 µL, 0.20 eq.). tert-Butyl 6-oxo-2-azaspiro[3.3]heptane-2-carboxylate (352.86 mg, 5.88 mmol, 4 eq.) was then added to the mixture at 70° C., and the reaction mixture was stirred for 3 h. TLC analysis showed that the reaction was complete. The mixture was concentrated, and the crude residue was purified by column chromatography to afford the desired product as a white solid. MS (ES$^+$, m/z): 535.9.

General procedure for the preparation of tert-butyl 6-((2-(3-((2-methoxy-4-(methylsulfonyl)phenyl)amino)prop-1-yn-1-yl)-1-(2,2,2-trifluoroethyl)-1H-indol-4-yl)amino)-2-azaspiro[3.3]heptane-2-carboxylate and tert-butyl 6-((2-(3-((2-methoxy-4-sulfamoylphenyl)amino)-prop-1-yn-1-yl)-1-(2,2,2-trifluoroethyl)-1H-indol-4-yl)amino)-2-azaspiro[3.3] heptane-2-carboxylate: To a mixture 2-methoxy-4-(methylsulfonyl)-N-(prop-2-yn-1-yl)aniline or 3-methoxy-4-(prop-2-yn-1-ylamino)benzenesulfonamide (1.5 eq.) and tert-butyl 6-((2-iodo-1-(2,2,2-trifluoroethyl)-1H-indol-4-yl)amino)-2-azaspiro[3.3]heptane-2-carboxylate (1 eq.) in DMSO were added CuI (1 eq.), Pd(PPh$_3$)$_4$ (0.10 eq.), and N-isopropylpropan-2-amine (1 eq.). The mixture was stirred at 25° C. for 1 h under N$_2$. LC-MS analysis showed that the reaction was complete. The reaction was poured into saturated EDTA solution (50 mL) and extracted with EtOAc (20 mL×3). The combined organic layers were washed with saturated EDTA solution (20 mL) by stirring the mixture for 1 h. The organic layer was washed with brine (50 mL), dried over anhydrous sodium sulfate, filtered, and concentrated under reduced pressure. The crude product was purified by prep-TLC to afford the desired products as yellow solids.

General procedure for the preparation of 2-(3-((2-methoxy-4-(methylsulfonyl)phenyl)amino)prop-1-yn-1-yl)-N-(2-azaspiro[3.3]heptan-6-yl)-1-(2,2,2-trifluoroethyl)-1H-indol-4-amine and 4-((3-(4-((2-azaspiro[3.3]heptan-6-yl)amino)-1-(2,2,2-trifluoroethyl)-1H-indol-2-yl)prop-2-yn-1-yl)amino)-3-methoxybenzenesulfonamide: To a solution of tert-butyl 6-((2-(3-((2-methoxy-4-(methylsulfonyl)phenyl)amino)prop-1-yn-1-yl)-1-(2,2,2-trifluoroethyl)-1H-indol-4-yl)amino)-2-azaspiro[3.3]heptane-2-carboxylate or tert-butyl 6-((2-(3-((2-methoxy-4-sulfamoylphenyl)amino)prop-1-yn-1-yl)-1-(2,2,2-trifluoroethyl)-1H-indol-4-yl)amino)-2-azaspiro[3.3]heptane-2-carboxylate (1 eq.) in DCM was added 2,2,2-trifluoroacetic acid (175 eq.) at 20° C. The mixture was stirred for 16 h. LC-MS analysis indicated that the starting material was consumed, and one main peak with the desired mass was detected. The reaction mixture was concentrated under reduced pressure to remove solvent. The residue was purified by prep-HPLC to afford the desired products as yellow solids.

2-(3-((2-methoxy-4-(methylsulfonyl)phenyl)amino)prop-1-yn-1-yl)-N-(2-azaspiro[3.3]heptan-6-yl)-1-(2,2,2-trifluoroethyl)-1H-indol-4-amine, MS (ES$^+$, m/z): 547.2; and 4-((3-(4-((2-azaspiro[3.3]heptan-6-yl)amino)-1-(2,2,2-trifluoroethyl)-1H-indol-2-yl)prop-2-yn-1-yl)amino)-3-methoxybenzenesulfonamide, MS (ES$^+$, m/z): 548.2.

Example C34: Synthesis of Compounds 79A, 80A, 487A, 621A, 731A, and 1009A

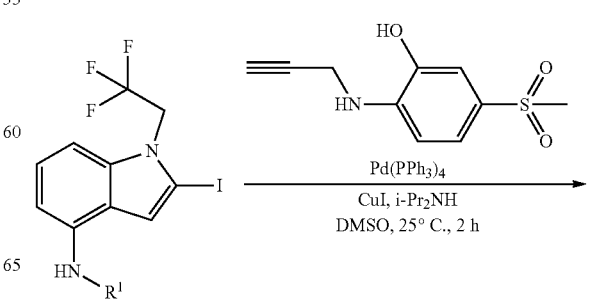

-continued

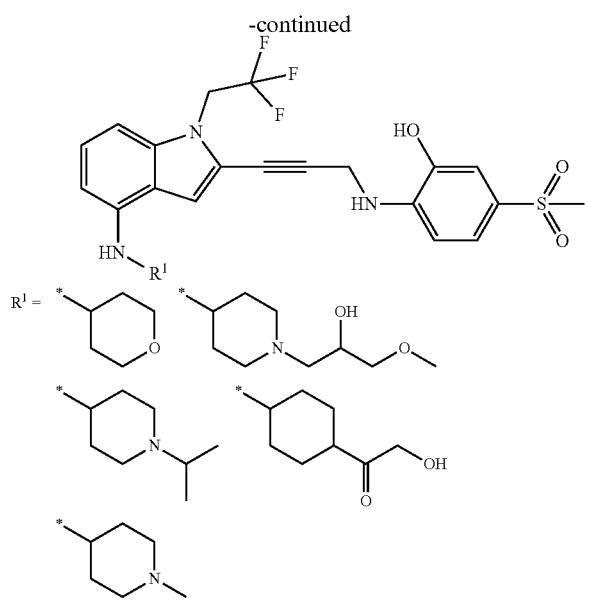

General Procedure: To a mixture of 5-(methylsulfonyl)-2-(prop-2-yn-1-ylamino)phenol (1.2 eq.) in DMSO were added i-Pr₂NH (10 eq.), CuI (1 eq.), 2-iodo-N—(R¹-substituted)-1-(2,2,2-trifluoroethyl)-1H-indol-4-amine (1 eq.), and Pd(PPh₃)₄ (0.20 eq.) at 25° C. The mixture was stirred for 2 h under N₂. LC-MS and TLC analysis showed that the reaction was complete. The reaction mixture was quenched by adding a saturated EDTA solution and stirring the resulting mixture at 25° C. for 2 h. The reaction mixture was partitioned by adding EtOAc, and the aqueous phase was extracted with EtOAc. The combined organic layers were washed with brine, dried over anhydrous sodium sulfate, filtered, and concentrated in vacuo. The residue was purified by prep-TLC and prep-HPLC to give a solution of the desired product. The solution was lyophilized to afford the desired product as a light yellow solid.

5-methanesulfonyl-2-[(3-{4-[(oxan-4-yl)amino]-1-(2,2,2-trifluoroethyl)-1H-indol-2-yl}prop-2-yn-1-yl)amino]phenol, MS (ES⁺, m/z): 522.1; 2-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-5-methanesulfonylphenol, MS (ES⁺, m/z): 609.2; 5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenol, MS (ES⁺, m/z): 563.2; 5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenol, MS (ES⁺, m/z): 563.1; 2-hydroxy-1-{4-[(2-{3-[(2-hydroxy-4-methanesulfonyl-phenyl)amino]prop-1-yn-1-yl}-1-(2,2,2-trifluoroethyl)-1H-indol-4-yl)amino]piperidin-1-yl}ethan-1-one, MS (ES⁺, m/z): 579.2; and 2-{3-[(4-methanesulfonyl-2-methoxyphenyl)amino]prop-1-yn-1-yl}-6-methoxy-N-(1-methylpiperidin-4-yl)-1-(2,2,2-trifluoroethyl)-1H-indol-4-amine, MS (ES⁺, m/z): 579.2.

Example C35: Synthesis of Compounds 52A, 53A, 90A, 91A, 216A, 217A, 218A, 219A, 224A, 636A, 640A, and 641A

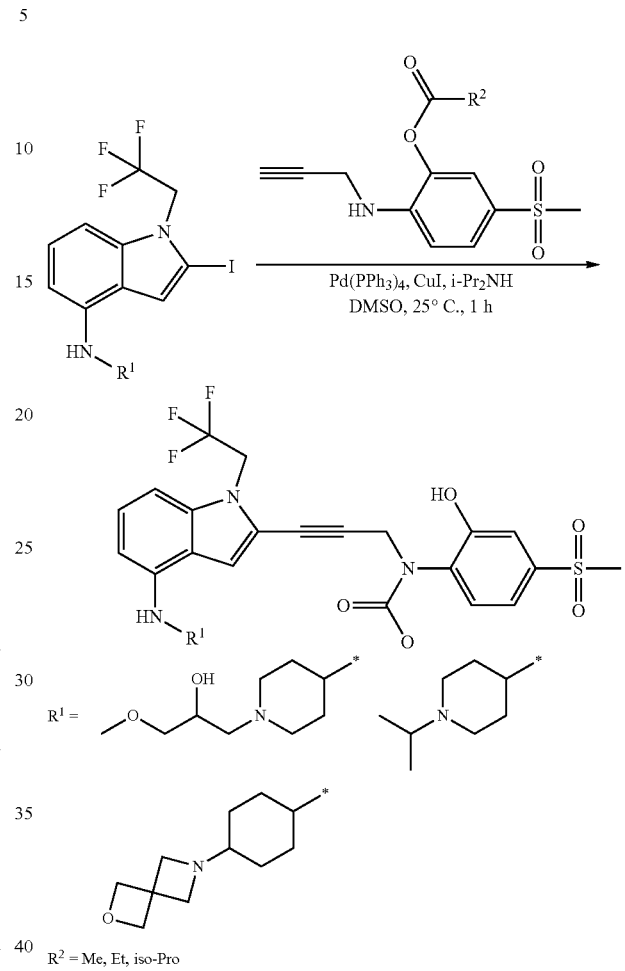

R² = Me, Et, iso-Pro

To a mixture of R²-substituted alkyne (1.2 eq.) and 2-iodo-N—(R¹-substituted)-1-(2,2,2-trifluoroethyl)-1H-indol-4-amine (1 eq.) in DMSO (2 mL) were added CuI (1 eq.), Pd(PPh₃)₄ (0.10 eq.), and N-isopropylpropan-2-amine (1 eq.). The mixture was stirred at 25~30° C. for 1 h under N₂. LC-MS analysis showed that the reaction was complete. The reaction mixture was quenched by adding a saturated EDTA solution (30 mL) and EtOAc (10 mL), and the resulting mixture was stirred at 25° C. for 1 h. The aqueous phase was extracted with EtOAc (20 mL×3). The combined organic layers were washed with brine (30 mL), dried over anhydrous sodium sulfate, filtered, and concentrated under reduced pressure to give a residue. The residue was purified by prep-TLC and prep-HPLC to afford the desired product.

N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)propionamide, MS (ES⁺, m/z): 673.1; N-(3-(4-((1-(2-hydroxy-3-methoxypropyl)piperidin-4-yl)amino)-1-(2,2,2-trifluoroethyl)-1H-indol-2-yl)prop-2-yn-1-yl)-N-(2-hydroxy-4-(N-propionylsulfamoyl)phenyl)propionamide MS (ES⁺, m/z): 722.3; N-(3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)propionamide, MS (ES⁺, m/z):

673.1; and N-(3-(4-(((1S,4S)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)propionamide. MS (ES+, m/z): 619.1.

Compounds 90A, 91A, 640A, 218A, 224A, 618A, and 641A were synthesized using the method described above.

N-(3-(4-((1-(2-hydroxy-3-methoxypropyl)piperidin-4-yl)amino)-1-(2,2,2-trifluoroethyl)-1H-indol-2-yl)prop-2-yn-1-yl)-N-(2-hydroxy-4-(methylsulfonyl)phenyl)propionamide, MS (ES+, m/z): 665.3; N-(3-(4-((1-(2-hydroxy-3-methoxypropyl)piperidin-4-yl)amino)-1-(2,2,2-trifluoroethyl)-1H-indol-2-yl)prop-2-yn-1-yl)-N-(2-hydroxy-4-(methylsulfonyl)phenyl)isobutyramide, MS (ES+, m/z): 679.3; N-(2-hydroxy-4-methanesulfonylphenyl)-2-methyl-N-[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]propanamide, MS (ES+, m/z): 687.2; N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide, MS (ES+, m/z): 687.2; 5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl 2-methylpropanoate, MS (ES+, m/z): 687.4; N-(3-(4-(((1R,4R)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide, MS (ES+, m/z): 633.3; and N-(3-(4-(((1S,4S)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide, MS (ES+, m/z): 633.3.

Example C36: Synthesis of Compounds 140A, 141A, 142A, 143A, 283A, 284A, 285A, 286A, 703A, and 710A

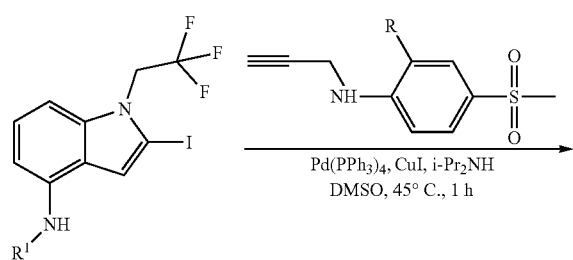

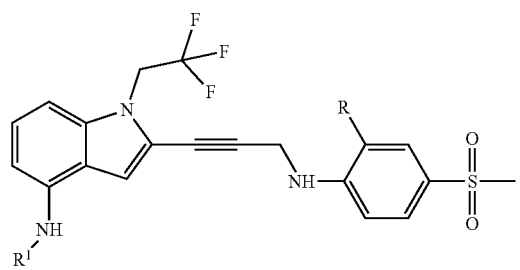

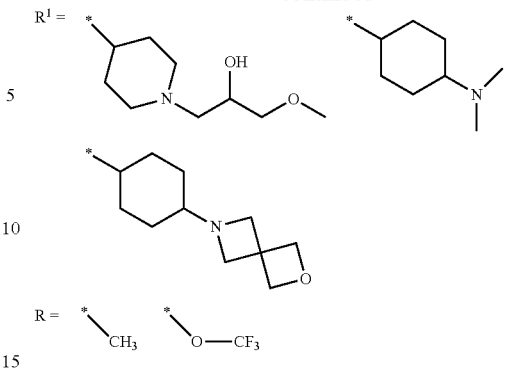

General Procedure: To a solution of 2-(R-substituted)-4-(methylsulfonyl)-N-(prop-2-yn-1-yl)aniline (1.5 eq.; Example A28 and A29) in DMSO were added 2-iodo-N—(R1-substituted)-1-(2,2,2-trifluoroethyl)-1H-indol-4-amine (1 eq.), CuI (1 eq.), i-Pr2NH (1 eq.), and Pd(PPh3)4 (0.02 eq.). The mixture was stirred at 45° C. for 1 h. TLC analysis (EtOAc:TEA=10:1, Rf=0.24) indicated that the reaction was complete. The reaction mixture was quenched by adding a saturated EDTA solution (40 mL) at 25° C. and extracting the resulting mixture with EtOAc (20 mL×3). The combined organic layers were dried over anhydrous sodium sulfate, filtered, and concentrated under reduced pressure. The residue was purified by prep-TLC and prep-HPLC to obtain the desired product as a light yellow solid.

1-{4-[(2-{3-[(4-methanesulfonyl-2-methylphenyl)amino]prop-1-yn-1-yl}-1-(2,2,2-trifluoroethyl)-1H-indol-4-yl)amino]piperidin-1-yl}-3-methoxypropan-2-ol, MS (ES+, m/z): 607.3; (1R,4R)—N4-[2-(3-{[4-methanesulfonyl-2-(trifluoromethoxy)phenyl]amino}prop-1-yn-1-yl)-1-(2,2,2-trifluoroethyl)-1H-indol-4-yl]-N1,N1-dimethylcyclohexane-1,4-diamine, MS (ES+, m/z): 631.1; (1S,4S)—N1,N1-dimethyl-N4-(2-(3-((4-(methylsulfonyl)-2-(trifluoromethoxy)phenyl)amino)prop-1-yn-1-yl)-1-(2,2,2-trifluoroethyl)-1H-indol-4-yl)cyclohexane-1,4-diamine, MS (ES+, m/z): 631.1; (1R,4R)—N4-(2-{3-[(4-methanesulfonyl-2-methylphenyl)amino]prop-1-yn-1-yl}-1-(2,2,2-trifluoroethyl)-1H-indol-4-yl)-N1,N1-dimethylcyclohexane-1,4-diamine, MS (ES+, m/z): 561.3; (1S,4S)—N1,N1-dimethyl-N4-(2-(3-((2-methyl-4-(methylsulfonyl)phenyl)amino)prop-1-yn-1-yl)-1-(2,2,2-trifluoroethyl)-1H-indol-4-yl)cyclohexane-1,4-diamine, MS (ES+, m/z): 561.3; 2-{3-[(4-methanesulfonyl-2-methylphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine, MS (ES+, m/z): 615.3; N-((1S,4S)-4-(2-oxa-6-azaspiro[3.3]heptan-6-yl)cyclohexyl)-2-(3-((2-methyl-4-(methylsulfonyl)phenyl)amino)prop-1-yn-1-yl)-1-(2,2,2-trifluoroethyl)-1H-indol-4-amine, MS (ES+, m/z): 615.3; 2-(3-{[4-methanesulfonyl-2-(trifluoromethoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine, MS (ES+, m/z): 685.2; N-((1S,4S)-4-(2-oxa-6-azaspiro[3.3]heptan-6-yl)cyclohexyl)-2-(3-((4-(methylsulfonyl)-2-(trifluoromethoxy)phenyl)amino)prop-1-yn-1-yl)-1-(2,2,2-trifluoroethyl)-1H-indol-4-amine, MS (ES+, m/z): 685.2; and 1-(4-{[2-(3-1{[4-methanesulfonyl-2-(trifluoromethoxy)phenyl]amino}prop-1-yn-1-yl)-1-(2,2,2-trifluoroethyl)-1H-indol-4-yl]amino}piperidin-1-yl)-3-methoxypropan-2-ol, MS (ES+, m/z): 677.1.

Example C37: Synthesis of Compounds 249A and 250A

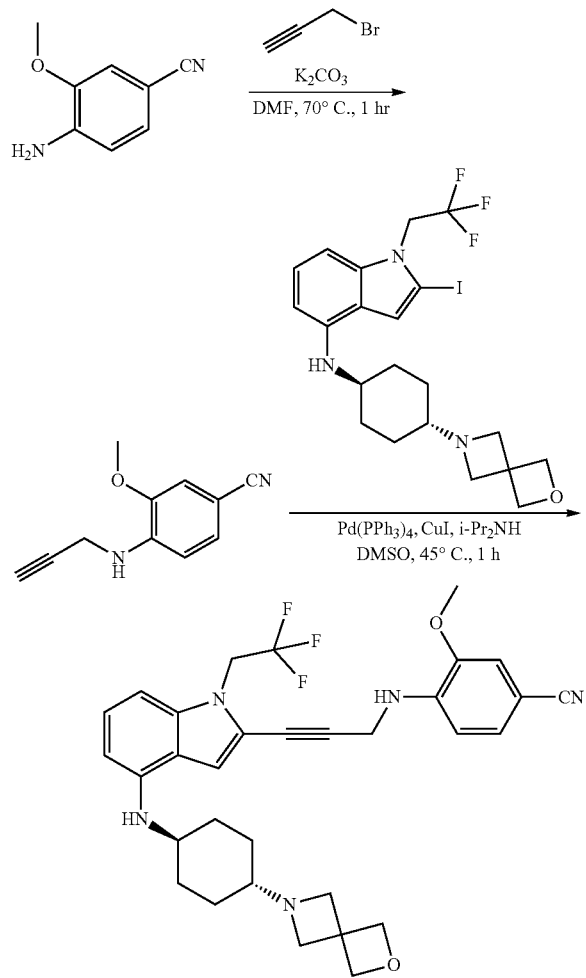

General procedure for the preparation of 3-methoxy-4-(prop-2-yn-1-ylamino)benzonitrile: To a solution of 4-amino-3-methoxybenzonitrile (1 eq.) in DMF were added K$_2$CO$_3$ (3 eq.) and 3-bromoprop-1-yne (3 eq.). The mixture was stirred at 70° C. for 1 h. TLC analysis (PE:EtOAc=3:1) indicated that 10% of the starting material remained, and one major new spot with polarity lower than that of the starting material was detected. The reaction mixture was diluted with water (10 mL) and extracted with EtOAc. The combined organic layers were washed with brine, dried over anhydrous sodium sulfate, filtered, and concentrated under reduced pressure to give a residue. The residue was purified by prep-TLC to afford the desired product as a brown solid.

General procedure for the preparation of final products: To a solution of 3-methoxy-4-(prop-2-yn-1-ylamino)benzonitrile (1.2 eq.) in DMSO were added i-Pr$_2$NH (10 eq.), CuI (1 eq.), N-((1R,4R)-4-(2-oxa-6-azaspiro[3.3]heptan-6-yl)cyclohexyl)-2-iodo-1-(2,2,2-trifluoroethyl)-1H-indol-4-amine (1 eq.), and Pd(PPh$_3$)$_4$ (0.2 eq.) at 45° C. The mixture was stirred at 45° C. for 1 h under N$_2$. LC-MS and TLC analysis showed that the reaction was complete. The reaction mixture was quenched by adding a saturated EDTA solution at 25° C. and stirring the resulting mixture for 2 h. The reaction mixture was partitioned by adding EtOAc, and the aqueous phase was extracted with EtOAc. The organic phase was washed with brine, dried over anhydrous sodium sulfate, filtered, and concentrated in vacuo to give the crude product. The residue was purified by prep-TLC and prep-HPLC to give a solution of the desired product. The solution was lyophilized to give the desired final product as a light yellow solid.

3-methoxy-4-[(3-{4-[(4-{2-oxa-6-azaspiro[3.3]heptan-6-yl}cyclohexyl)amino]-1-(2,2,2-trifluoroethyl)-1H-indol-2-yl}prop-2-yn-1-yl)amino]benzonitrile, MS (ES$^+$, m/z): 578.2; and 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzonitrile, MS (ES$^+$, m/z): 578.3.

Example C38: Synthesis of Compounds 121A, 122A, 251A, 252A, 301A, 302A, and 665A

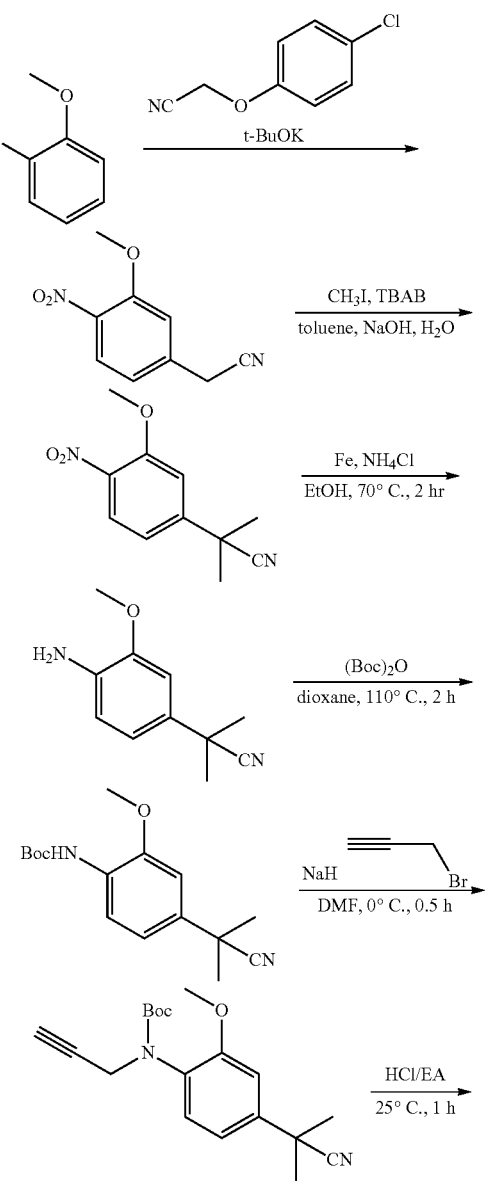

-continued

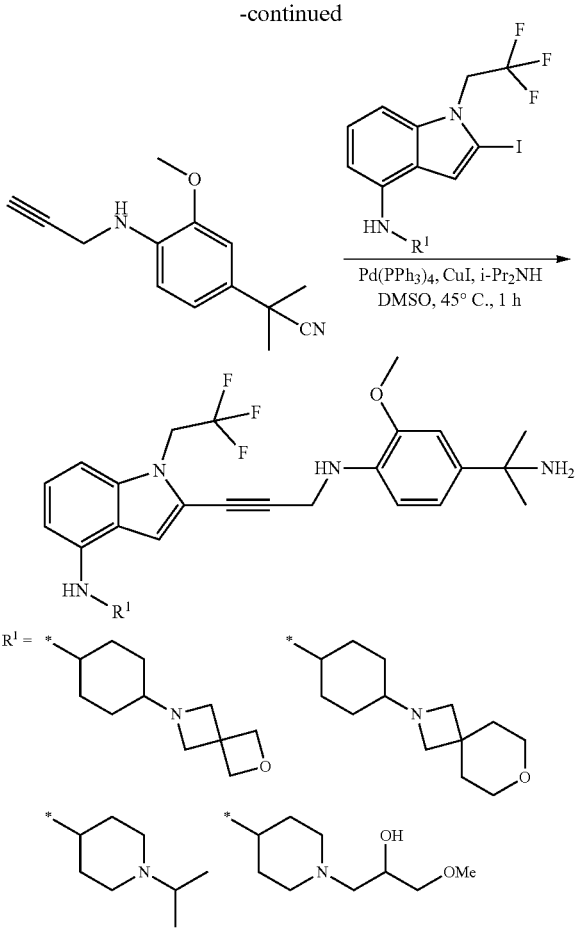

General procedure for the preparation of 2-(3-methoxy-4-nitrophenyl)acetonitrile: To a mixture of 1-methoxy-2-nitrobenzene (10 g, 65.30 mmol, 8 mL, 1 eq.) and 2-(4-chlorophenoxy)acetonitrile (1.3 eq.) (14.23 g, 84.89 mmol, 1.3 eq.) in DMF (1 mL) was added a solution of t-BuOK (2.2 eq.) in DMF (2 mL) at −20° C. The mixture was stirred at −20° C. for 30 min, poured into ice-cold 2M HCl, and stirred further for 1 h. TLC analysis (PE:EtOAc=3:1) indicated that 40% of the starting material remained, and two major new spots with polarity greater than that of the starting material were detected. The mixture was poured into ice-cold 2M HCl and stirred further for 1 h. The reaction mixture was then diluted with water and extracted with EtOAc (100 mL). The combined organic layers were washed with brine, dried over anhydrous sodium sulfate, filtered, and concentrated under reduced pressure. The crude residue was purified by column chromatography to obtain the desired product as a brown solid.

General procedure for the preparation of 2-(3-methoxy-4-nitrophenyl)-2-methylpropanenitrile: To a mixture of 2-(3-methoxy-4-nitrophenyl)acetonitrile (1 eq.) and tetrabutylammonium bromide (TBAB; 1.8 eq.) in toluene were added NaOH (1.67 g, 41.63 mmol, 10 eq.) and CH$_3$I (10 eq.). The mixture was stirred at 25° C. for 1 h. TLC analysis (PE:EtOAc=3:1) indicated that the starting material was consumed completely, and two new spots were detected. The reaction mixture was diluted with water (20 mL) and extracted with EtOAc (40 mL). The combined organic layers were washed with brine (20 mL), dried over anhydrous sodium sulfate, filtered, and concentrated under reduced pressure to give a residue. The residue was purified by prep-TLC (SiO$_2$, PE:EtOAc=3:1) to obtain the desired product as a yellow solid.

Preparation of 2-(4-amino-3-methoxyphenyl)-2-methylpropanenitrile: To a solution of 2-(3-methoxy-4-nitrophenyl)-2-methylpropanenitrile (1 eq.) in EtOH (2 mL) and water (0.5 mL) were added NH$_4$Cl (5 eq.) and Fe (5 eq.). The mixture was stirred at 70° C. for 2 h. LC-MS analysis showed that the starting material was consumed completely, and the desired mass was detected. The reaction mixture was diluted with water (10 mL) and extracted with EtOAc (20 mL). The combined organic layers were washed with saturated brine (20 mL), dried over anhydrous sodium sulfate, filtered, and concentrated under reduced pressure. The crude residue was purified by prep-TLC (SiO$_2$, PE:EtOAc=3:1) to obtain the desired product as a yellow oil.

Preparation of tert-butyl (4-(2-cyanopropan-2-yl)-2-methoxyphenyl)carbamate: To a solution of 2-(4-amino-3-methoxyphenyl)-2-methylpropanenitrile (1 eq.) in dioxane (4 mL) was added (Boc)$_2$O (2 eq.). The mixture was stirred at 110° C. for 2 h. TLC analysis (PE:EtOAc=3:1) showed that 10% of the starting material remained, and two new spots were detected. The reaction mixture was diluted with water (20 mL) and extracted with EtOAc (10 mL). The combined organic layers were washed with saturated brine (10 mL), dried over anhydrous sodium sulfate, filtered, and concentrated under reduced pressure to give a residue. The residue was purified by prep-TLC (SiO$_2$, PE:EtOAc=3:1) to obtain the desired product as a light-yellow oil.

Preparation of tert-butyl (4-(2-cyanopropan-2-yl)-2-methoxyphenyl)(prop-2-yn-1-yl)carbamate: To a solution of tert-butyl (4-(2-cyanopropan-2-yl)-2-methoxyphenyl)carbamate (0.3 g, 1.03 mmol, 1 eq.) in DMF (2 mL) was added NaH (3 eq., 60% in mineral oil) at 0° C. The mixture was stirred at 0° C. for 10 min, and 3-bromoprop-1-yne (368.73 mg, 3.10 mmol, 267.20 µL, 3 eq.) was added to the mixture at 0° C. The mixture was stirred further for 20 min. LC-MS analysis showed that the starting material was consumed completely, and the desired mass was detected. The reaction mixture was diluted with saturated solution of NH$_4$Cl (10 mL) and extracted with EtOAc (20 mL×3). The combined organic layers were washed with brine (10 mL), dried over anhydrous sodium sulfate, filtered, and concentrated under reduced pressure. The crude product was obtained as a light-yellow oil.

Preparation of 2-(3-methoxy-4-(prop-2-yn-1-ylamino)phenyl)-2-methylpropanenitrile: To a solution of tert-butyl (4-(2-cyanopropan-2-yl)-2-methoxyphenyl)(prop-2-yn-1-yl)carbamate (1 eq.) in EtOAc (1 mL) was added HCl/EtOAc (5 mL; 4 N). The mixture was stirred at 25° C. for 1 h. LC-MS analysis showed that the starting material was consumed completely, and the desired mass was detected. The reaction mixture was diluted with saturated solution of NaHCO$_3$ (10 mL) and extracted with EtOAc (10 mL). The combined organic layers were washed with saturated brine (10 mL), dried over anhydrous sodium sulfate, filtered, and concentrated under reduced pressure. The crude residue was purified by prep-TLC (SiO$_2$, PE:EtOAc=5:1) to afford the desired product as a yellow oil.

Preparation of final products: To a solution of 2-(3-methoxy-4-(prop-2-yn-1-ylamino)phenyl)-2-methylpropanenitrile (1.2 eq.) in DMSO (2 mL) were added i-Pr$_2$NH (10 eq.), CuI (1 eq.), 2-iodo-N—(R-substituted)-1-(2,2,2-trifluoroethyl)-1H-indol-4-amine (1 eq.), and Pd(PPh$_3$)$_4$ (0.2 eq.). The mixture was stirred at room temperature for 1 h under N$_2$. LC-MS and TLC analysis showed that the reaction was complete. The reaction mixture was quenched by adding a saturated EDTA solution (20 mL) at 45° C. and stirring the resulting mixture for 1 h. The reaction mixture was partitioned by adding EtOAc (10 mL), and the aqueous phase was extracted with EtOAc (10 mL×2). The organic phase was washed with brine (10 mL×3), dried over anhydrous sodium sulfate, filtered, and concentrated in vacuo. The crude residue was purified by prep-TLC and prep-HPLC to give a solution of the desired product. The solution was lyophilized to give the desired product as a light-yellow oil.

2-(3-methoxy-4-{[3-(4-{[(1R,4R)-4-{2-oxa-6-azaspiro [3.3]heptan-6-yl}cyclohexyl]amino}-1-(2,2,2-trifluoroethyl)-1H-indol-2-yl)prop-2-yn-1-yl]amino}phenyl)-2-methylpropanenitrile, MS (ES$^+$, m/z): 620.3; 2-(4-((3-(4-(((1S,4S)-4-(2-oxa-6-azaspiro[3.3]heptan-6-yl)cyclohexyl) amino)-1-(2,2,2-trifluoroethyl)-1H-indol-2-yl)prop-2-yn-1-yl)amino)-3-methoxyphenyl)-2-methylpropanenitrile, MS (ES$^+$, m/z): 620.3; 2-(3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl] amino}phenyl)-2-methylpropanenitrile, MS (ES$^+$, m/z): 648.4; 2-(4-((3-(4-(((1S,4S)-4-(7-oxa-2-azaspiro[3.5] nonan-2-yl)cyclohexyl)amino)-1-(2,2,2-trifluoroethyl)-1H-indol-2-yl)prop-2-yn-1-yl)amino)-3-methoxyphenyl)-2-methylpropanenitrile, MS (ES$^+$, m/z): 648.4; 2-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl] amino}phenyl)-2-methylpropanenitrile, MS (ES$^+$, m/z): 566.2; 2-(4-((3-(4-(((1S,4S)-4-(dimethylamino)cyclohexyl) amino)-1-(2,2,2-trifluoroethyl)-1H-indol-2-yl)prop-2-yn-1-yl)amino)-3-methoxyphenyl)-2-methylpropanenitrile, MS (ES$^+$, m/z): 566.2; and 2-(4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxyphenyl)-2-methylpropanenitrile, MS (ES$^+$, m/z): 612.3.

Example C39: Synthesis of Compounds 160A, 161A, 181A, 182A, 204A, 205A, 375A, 377A, and 378A

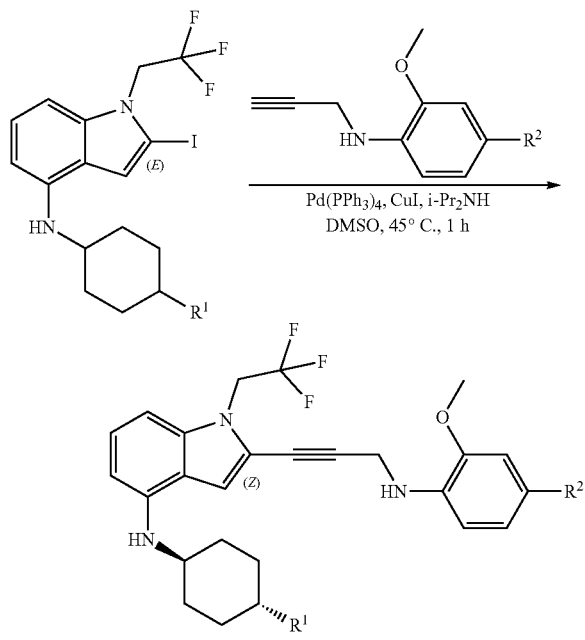

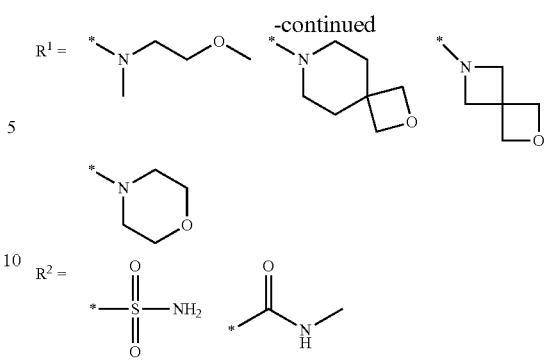

General Procedure: To a mixture of 2-methoxy-4-(R$^2$-substituted)-N-(prop-2-yn-1-yl)aniline (100 mg, 164.42 μmol, 1 eq.) in DMSO (3 mL) were added i-Pr$_2$NH (16.64 mg, 164.42 μmol, 23.24 μL, 1 eq.), CuI (31.31 mg, 164.42 μmol, 1 eq.), 2-iodo-N-(4-(R$^1$-substituted)cyclohexyl)-1-(2,2,2-trifluoroethyl)-1H-indol-4-amine (1 eq.), and Pd(PPh$_3$)$_4$ (0.2 eq.) at 45° C. The mixture was stirred at 45° C. for 1 h under N$_2$. LC-MS and TLC analysis showed that the reaction was complete. The reaction mixture was quenched by adding a saturated EDTA solution (40 mL) at 25° C. for 1 h. The reaction mixture was partitioned by adding EtOAc (20 mL), and the aqueous phase was extracted with EtOAc (20 mL×3). The organic phase was washed with brine (20 mL×3), dried over anhydrous sodium sulfate, filtered, and concentrated in vacuo. The crude residue was purified by prep-TLC (SiO$_2$, EtOAc:MeOH:TEA=10:1:1, R$_f$=0.43) and prep-HPLC to give a solution of the desired product. The solution was lyophilized to give the desired product as a light yellow solid.

3-methoxy-N-methyl-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzamide, MS (ES$^+$, m/z): 638.4; 3-methoxy-N-methyl-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzamide, MS (ES$^+$, m/z): 638.3; 3-methoxy-4-{[3-(4-{[(1R,4R)-4-[(2-methoxyethyl) (methyl)amino]cyclohexyl]amino}-1-(2,2,2-trifluoroethyl)-1H-indol-2-yl)prop-2-yn-1-yl]amino}benzene-1-sulfonamide, MS (ES$^+$, m/z): 622.2; 3-methoxy-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino) benzenesulfonamide, MS (ES$^+$, m/z): 622.2; 3-methoxy-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide, MS (ES$^+$, m/z): 660.2; 4-((3-(4-(((1S,4S)-4-(2-oxa-7-azaspiro [3.5]nonan-7-yl)cyclohexyl)amino)-1-(2,2,2-trifluoroethyl)-1H-indol-2-yl)prop-2-yn-1-yl)amino)-3-methoxybenzenesulfonamide, MS (ES$^+$, m/z): 660.2; 3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide, MS (ES$^+$, m/z): 632.2; 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide, MS (ES$^+$, m/z): 632.2; 3-methoxy-4-((3-(4-(((1R,4R)-4-morpholinocyclohexyl)amino)-1-(2,2,2-trifluoroethyl)-1H-indol-2-yl)prop-2-yn-1-yl)amino) benzenesulfonamide, MS (ES$^+$, m/z): 620.2; and 3-methoxy-4-((3-(4-(((1S,4S)-4-morpholinocyclohexyl)

amino)-1-(2,2,2-trifluoroethyl)-1H-indol-2-yl)prop-2-yn-1-yl)amino)benzenesulfonamide, MS (ES+, m/z): 620.2.

Example C40: Synthesis of Compounds 46A, 47A, 49A, 51A, 58A, 59A, 60A, 360A, 361A, 465A, 470A, 548A, 552A, 768A, 993A, and 1041A

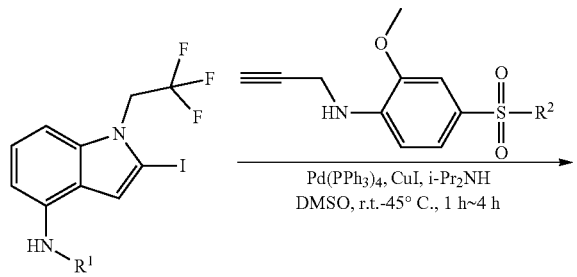

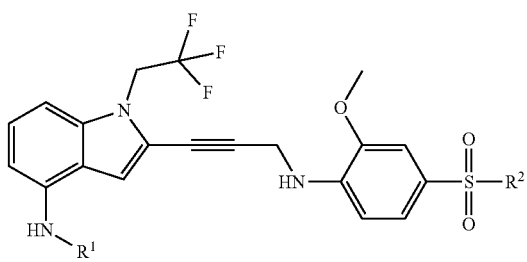

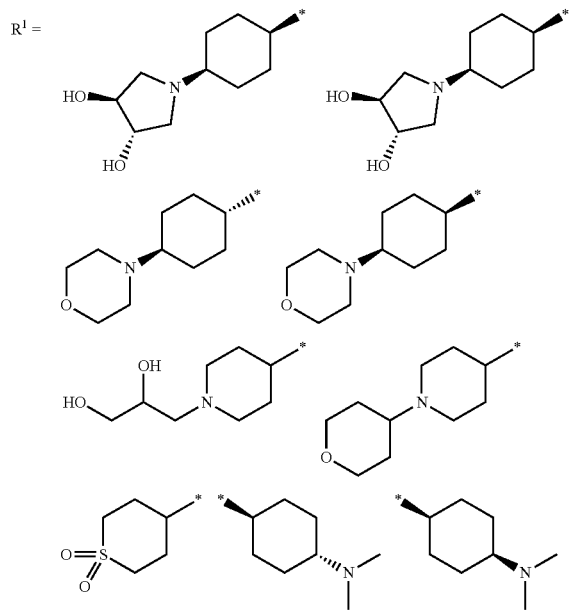

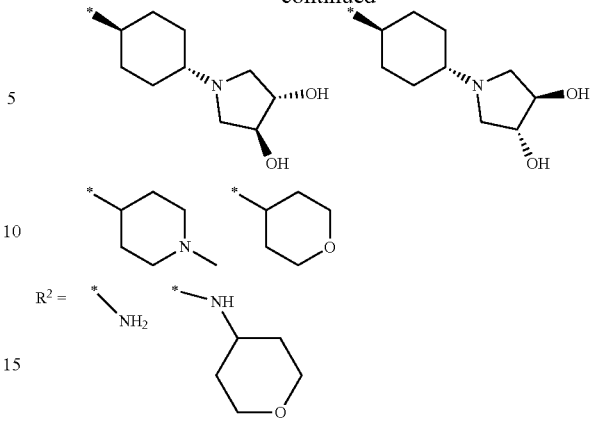

General Procedure: To a solution of $R^2$-substituted alkyne (1-2 eq., HCl or free) in DMSO (1~10 mL) were added i-Pr$_2$NH (10~30 eq.), CuI (1~2 eq.), 2-iodo-N—($R^1$-substituted)methyl-1-(2,2,2-trifluoroethyl)-1H-indol-4-amine (1 eq.), and Pd(PPh$_3$)$_4$ (0.20~0.50 eq.) at 20-45° C. The mixture was stirred for 1~4 h. TLC or LC-MS analysis detected that the reaction was complete. EtOAc (10 mL) was poured into the mixture, and the resulting mixture was poured into a 2N aqueous EDTA (40 mL) and stirred for 15 min. The aqueous phase was extracted with EtOAc (3×). The organic layer was poured to saturated EDTA solution and stirred for 1 h. The aqueous phase was extracted with EtOAc (3×). The combined organic layers were washed with brine (3×), dried over anhydrous sodium sulfate, mixed with activated carbon, filtered, and concentrated in vacuo. The mixture was purified by prep-TLC or column chromatography then purified further by prep-HPLC to afford the desired compounds.

3-Methoxy-4-{[3-(4-{[(1S,4S)-4-[(3S,4S)-3,4-dihydroxypyrrolidin-1-yl]cyclohexyl]amino}-1-(2,2,2-trifluoroethyl)-1H-indol-2-yl)prop-2-yn-1-yl]amino}benzene-1-sulfonamide, MS (ES+, m/z): 636.2; 4-((3-(4-(((1R,4S)-4-((3S,4S)-3,4-dihydroxypyrrolidin-1-yl)cyclohexyl)amino)-1-(2,2,2-trifluoroethyl)-1H-indol-2-yl)prop-2-yn-1-yl)amino)-3-methoxybenzenesulfonamide, MS (ES+, m/z): 636.2; 3-methoxy-4-((3-(4-(((1R,4R)-4-morpholinocyclohexyl)amino)-1-(2,2,2-trifluoroethyl)-1H-indol-2-yl)prop-2-yn-1-yl)amino)benzenesulfonamide, MS (ES+, m/z): 620.3; 3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzenesulfonamide, MS (ES+, m/z): 636.2; 4-((3-(4-(((1R,4R)-4-(dimethylamino)cyclohexyl)amino)-1-(2,2,2-trifluoroethyl)-1H-indol-2-yl)prop-2-yn-1-yl)amino)-3-methoxybenzenesulfonamide, MS (ES+, m/z): 578.2; 4-((3-(4-(((1S,4S)-4-(dimethylamino)cyclohexyl)amino)-1-(2,2,2-trifluoroethyl)-1H-indol-2-yl)prop-2-yn-1-yl)amino)-3-methoxybenzenesulfonamide, MS (ES+, m/z): 578.3; 3-methoxy-4-((3-(4-((1-methylpiperidin-4-yl)amino)-1-(2,2,2-trifluoroethyl)-1H-indol-2-yl)prop-2-yn-1-yl)amino)benzenesulfonamide, MS (ES+, m/z): 550.2; 4-((3-(4-(((1R,4R)-4-((3R,4R)-3,4-dihydroxypyrrolidin-1-yl)cyclohexyl)amino)-1-(2,2,2-trifluoroethyl)-1H-indol-2-yl)prop-2-yn-1-yl)amino)-3-methoxybenzenesulfonamide, MS (ES+, m/z): 636.2; 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-(oxan-4-yl)benzene-1-sulfonamide, MS (ES+, m/z): 694.3; 3-methoxy-N-(oxan-4-yl)-4-[(3-{4-[(oxan-4-yl)amino]-1-(2,2,2-trifluoroethyl)-1H-indol-2-yl}prop-2-yn-1-yl)amino]benzene-1- sulfonamide, MS (ES+, m/z): 621.3; 4-[(3-{4-[(1,1-dioxo-1λ6-thian-4-yl)amino]-1-(2,2,2-trifluoroethyl)-1H-indol-2-yl}prop-2-yn-1-yl)amino]-3-methoxy-N-(oxan-4-yl)benzene-1-sulfonamide, MS (ES+, m/z): 669.1; 3-methoxy-4-((3-(4-((1-(tetrahydro-2H-pyran-4-yl)piperidin-4-yl)amino)-1-(2,2,2-trifluoroethyl)-1H-indol-2-yl)prop-2-yn-1-yl)amino)benzenesulfonamide, MS (ES+, m/z): 620.2; 3-methoxy-N-(oxan-4-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide, MS (ES+, m/z): 662.2; 3-methoxy-4-[(3-{4-[(1-methylpiperidin-4-yl)amino]-1-(2,2,2-trifluoroethyl)-1H-indol-2-yl}prop-2-yn-1-yl)amino]-N-(oxan-4-yl)benzene-1-sulfonamide, MS (ES+, m/z): 634.2; and 3-methoxy-N-(oxan-4-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide, MS (ES+, m/z): 662.3.

Example C41: Synthesis of Compounds 44A and 45A

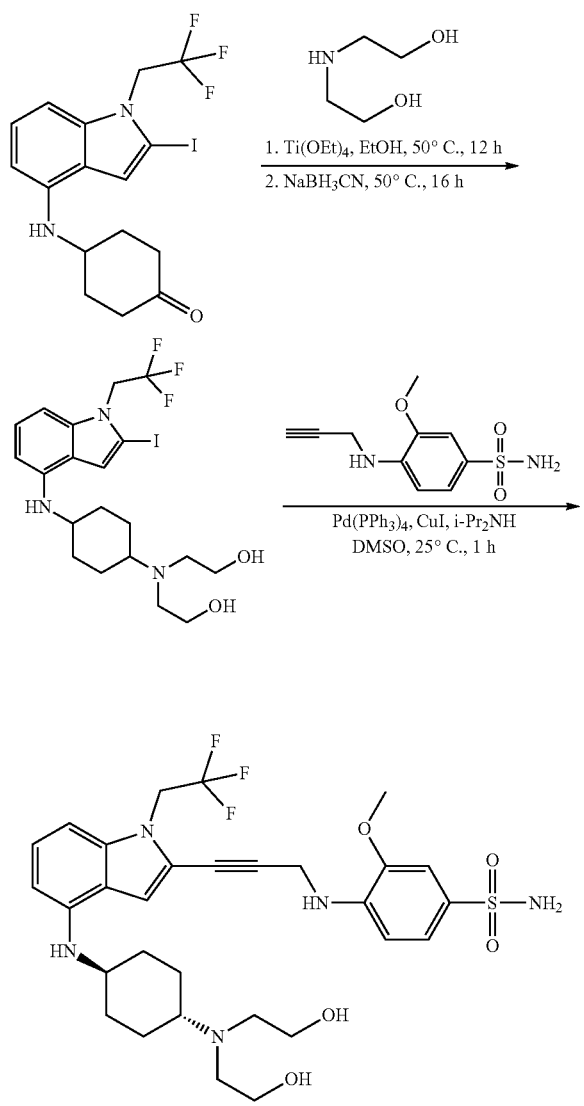

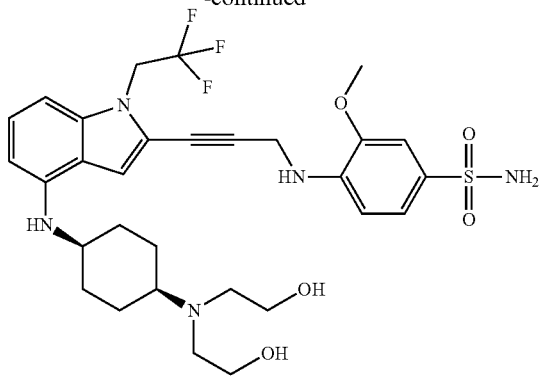

Preparation of 2,2'-((4-((2-iodo-1-(2,2,2-trifluoroethyl)-1H-indol-4-yl)amino)cyclohexyl)azanediyl)bis(ethan-1-ol): To a solution of 4-((2-iodo-1-(2,2,2-trifluoroethyl)-1H-indol-4-yl)amino)cyclohexan-1-one (80 mg, 179 μmol, 1 eq.) in EtOH (5 mL) were added 2,2'-azanediylbis(ethan-1-ol) (112.91 mg, 1.07 mmol, 103.59 μL, 6 eq.) and Ti(OEt)₄ (204.15 mg, 894.98 mol, 185.59 μL, 5 eq.). The mixture was stirred at 50° C. for 12 h. The mixture was then cooled to 20° C., and NaBH₃CN (56.24 mg, 894.98 μmol, 5 eq.) was added to the reaction. The resulting reaction mixture was stirred at 20° C. for 4 h. LC-MS analysis showed that 33% of the starting material remained. The mixture was stirred at 50° C. for 12 h. HPLC analysis showed that 13% of the starting material remained. The reaction mixture was poured into a saturated aqueous solution of NaHCO₃ (30 mL) and stirred for 30 min. The mixture was then filtered through diatomite and washed with EtOAc (30 mL). The aqueous layer was extracted with EtOAc (30 mL×3). The combined organic layers were washed with brine (30 mL×3), dried over anhydrous sodium sulfate, filtered, and concentrated in vacuo. The residue was purified by prep-TLC (SiO₂, EtOAc: TEA=10:1, $R_f$=0.24) to afford the desired product (30 mg) as a yellow solid. MS (ES+, m/z): 526.2.

Preparation of final products: To a solution of 3-methoxy-4-(prop-2-yn-1-ylamino)benzene sulfonamide (29.48 mg, 104.27 μmol, 2 eq.) in DMSO (1 mL) were added i-Pr₂NH (52.76 mg, 521.37 μmol, 73.68 μL, 10 eq.), CuI (9.93 mg, 52.14 μmol, 1 eq.), 2,2'-((4-((2-iodo-1-(2,2,2-trifluoroethyl)-1H-indol-4-yl)amino)cyclohexyl)azanediyl)bis(ethan-1-ol) (30 mg, 52.14 μmol, 1 eq.), and Pd(PPh₃)₄ (12.05 mg, 10.43 μmol, 0.20 eq.) at 25° C. The mixture was stirred at 25° C. for 1 h under N₂. LC-MS and TLC analysis showed that the reaction was complete. EtOAc (10 mL) was poured into the mixture, and the resulting mixture was poured into 2N aqueous EDTA (40 mL) and stirred for 15 min. The aqueous phase was extracted with EtOAc (40 mL×2). The organic layer was poured to 2N aqueous EDTA (40 mL) and stirred for 1 h, and the aqueous phase was extracted with EtOAc (40 mL×3). The combined organic layers were washed with brine (40 mL×3), dried over anhydrous sodium sulfate, treated with activated carbon, filtered, and concentrated in vacuo. The crude residue was purified by prep-TLC and prep-HPLC to afford the desired products as light yellow solids.

3-methoxy-4-{[3-(4-{[(1R,4R)-4-[bis(2-hydroxyethyl)amino]cyclohexyl]amino}-1-(2,2,2-trifluoroethyl)-1H-indol-2-yl)prop-2-yn-1-yl]amino}benzene-1-sulfonamide, MS (ES+, m/z): 638.3; and 3-methoxy-4-{[3-(4-{[(1S,4S)-4-[bis(2-hydroxyethyl)amino]cyclohexyl]amino}-1-(2,2,2- trifluoroethyl)-1H-indol-2-yl)prop-2-yn-1-yl]amino}benzene-1-sulfonamide, MS (ES+, m/z): 638.3.

Example C42: Synthesis of Compounds 134A, 135A, 277A, 278A, and 515A

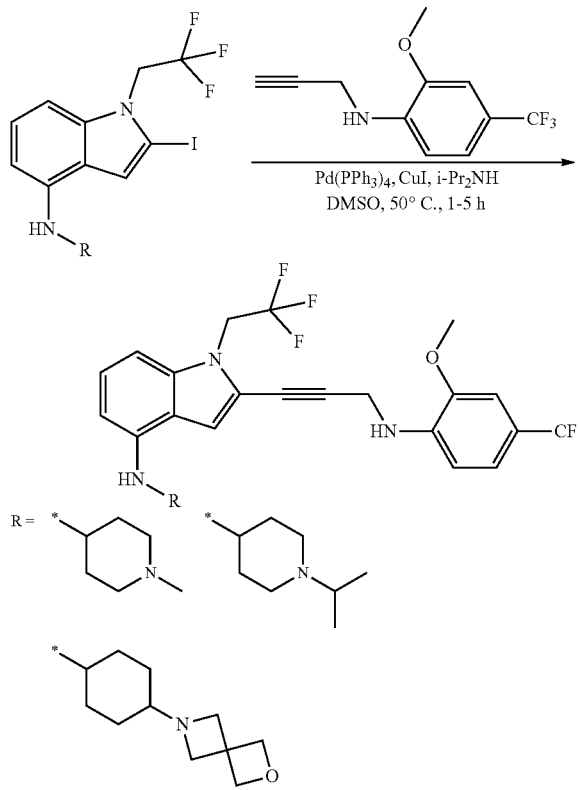

A mixture of 2-iodo-N—(R-substituted)-1-(2,2,2-trifluoroethyl)-1H-indol-4-amine (1 eq.), 2-methoxy-N-(prop-2-yn-1-yl)-4-(trifluoromethyl)aniline (1-3 eq.), CuI (21.78 mg, 114.35 μmol, 1 eq.), i-Pr₂NH (115.71 mg, 1.14 mmol, 161.61 μL, 10 eq.), and Pd(PPh₃)₄ (52.86 mg, 45.74 μmol, 0.4 eq.) in DMSO (1 mL) was degassed and purged with N₂ three times and was then stirred at 50° C. for 1~2 h under N₂. A saturated EDTA solution (15 mL) was added to the reaction, and the mixture was stirred further for 1.5 h. The resulting mixture was extracted with EtOAc (15 mL×3). The combined organic layers were washed with brine (10 mL), dried over anhydrous sodium sulfate, filtered, and concentrated. The crude residue was purified by prep-HPLC to obtain the desired compound.

2-(3-{[2-methoxy-4-(trifluoromethyl)phenyl]amino}prop-1-yn-1-yl)-N-(1-methylpiperidin-4-yl)-1-(2,2,2-trifluoroethyl)-1H-indol-4-amine, MS (ES+, m/z): 539.2; 2-(3-{[2-methoxy-4-(trifluoromethyl)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine, MS (ES+, m/z): 621.2; N-((1S,4S)-4-(2-oxa-6-azaspiro[3.3]heptan-6-yl)cyclohexyl)-2-(3-((2-methoxy-4-(trifluoromethyl)phenyl)amino)prop-1-yn-1-yl)-1-(2,2,2-trifluoroethyl)-1H-indol-4-amine, MS (ES+, m/z): 621.2; (1R,4R)—N⁴-[2-(3-{[2-methoxy-4-(trifluoromethyl)phenyl]amino}prop-1-yn-1-yl)-1-(2,2,2-trifluoroethyl)-1H-indol-4-yl]-N¹,N¹-dimethylcyclohexane-1,4-diamine, MS (ES+, m/z): 567.2; and (1S,4S)—N¹-(2-(3-((2-methoxy-4-(trifluoromethyl)phenyl)amino)prop-1-yn-1-yl)-1-(2,2,2-trifluoroethyl)-1H-indol-4-yl)-N⁴,N⁴-dimethylcyclohexane-1,4-diamine, MS (ES+, m/z): 567.2.

Example C43: Synthesis of Compounds 136A, 137A, 275A, 276A, 335A, 516A, and 690A

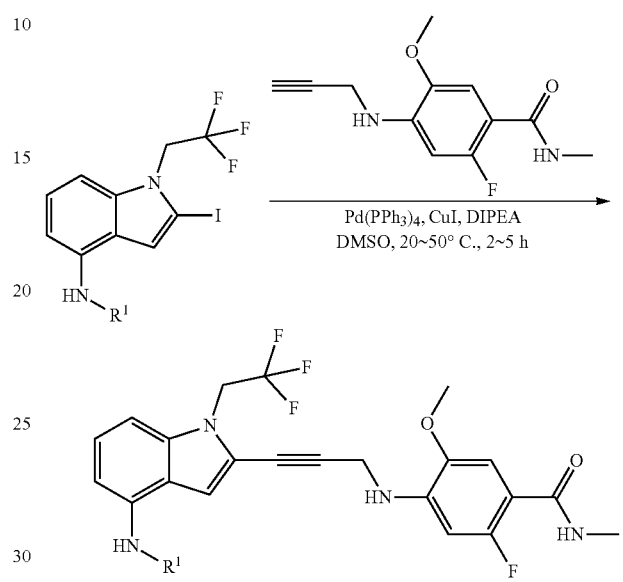

A mixture of 2-iodo-N—(R-substituted)-1-(2,2,2-trifluoroethyl)-1H-indol-4-amine (1 eq.), 2-fluoro-5-methoxy-N-methyl-4-(prop-2-yn-1-ylamino)benzamide (51.98 mg, 220.02 μmol, 5 eq.), DIPEA (189.57 mg, 1.47 mmol, 255.49 μL, 10 eq.), CuI (27.94 mg, 146.68 μmol, 1 eq.), and Pd(PPh₃)₄ (33.90 mg, 29.34 μmol, 0.2 eq.) in DMSO (5 mL) was degassed and purged with N₂ three times, and the mixture was stirred at 20° C. for 1 h under N₂. To the mixture was added a saturated EDTA solution (25 mL), and the mixture was stirred further for 1.5 h. The mixture was then extracted with EtOAc (20 mL×3). The organic layer was washed with brine (10 mL), dried over anhydrous sodium sulfate, filtered, and concentrated under reduced pressure. The residue was purified by prep-TLC (SiO₂, EtOAc:TEA=50:1, $R_f$=0.5) and prep-HPLC to obtain the desired products.

2-fluoro-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-5-methoxy-N-methylbenzamide, MS (ES+, m/z): 620.3; 2-fluoro-5-methoxy-N-methyl-4-[(3-{4-[(1-methylpiperidin-4-yl)amino]-1-(2,2,2-trifluoroethyl)-1H-indol-2-yl}prop-2-yn-1-yl)amino]benzamide, MS (ES+, m/z): 546.2; 2-fluoro-5-methoxy-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide, MS (ES+, m/z): 628.2; 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxy-N-methylbenzamide, MS (ES+, m/z): 628.2; 2-fluoro-5-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide, MS (ES+, m/z): 574.3; 4-((3-(4-(((1S,4S)-4-(dimethylamino)cyclohexyl)amino)-1-(2,2,2- trifluoroethyl)-1H-indol-2-yl)prop-2-yn-1-yl)amino)-2-fluoro-5-methoxy-N-methylbenzamide, MS (ES+, m/z): 574.2; and 2-fluoro-5-methoxy-N-methyl-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide, MS (ES+, m/z): 656.3.

Example C44: Preparation of Compounds 71A, 72A, 74A, 75A, 170A, 171A, 482A, 484A, 596A, 601A, 609A, 620A, 1003A, and 1008A

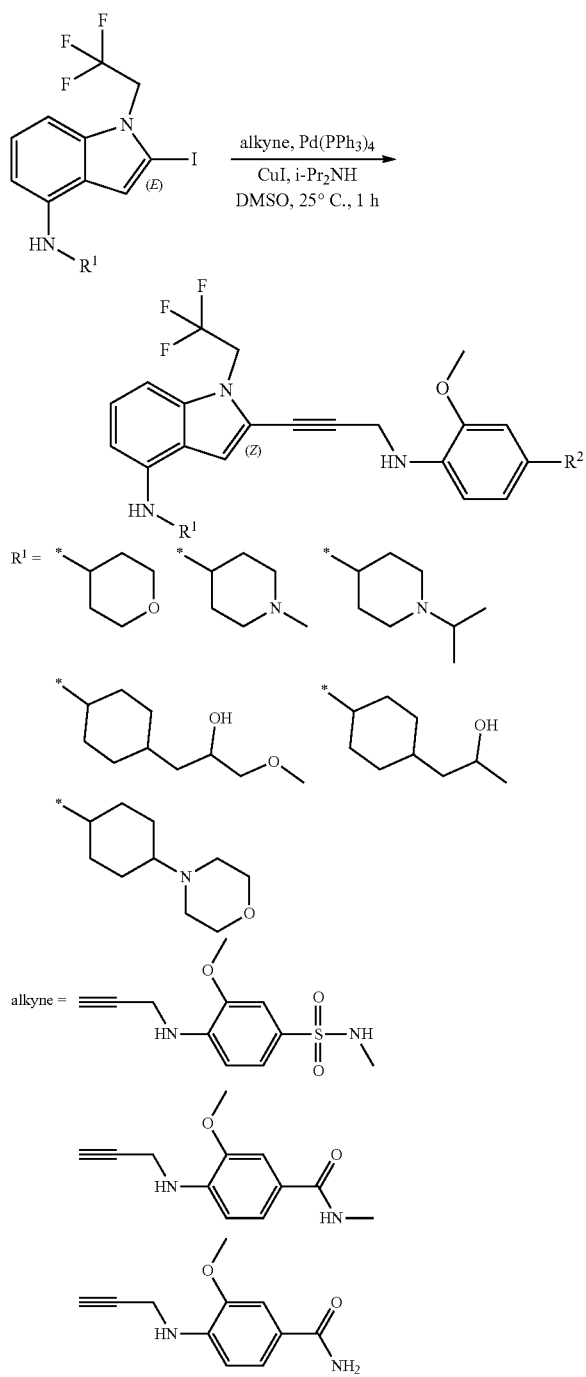

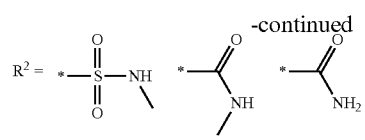

General procedure: To a mixture of alkyne (1.2 eq.) in DMSO were added i-Pr$_2$NH (10 eq.), CuI (1 eq.), 2-iodo-N—(R$^1$-substituted)-1-(2,2,2-trifluoroethyl)-1H-indol-4-amine (1 eq.), and Pd(PPh$_3$)$_4$ (0.2 eq.) at 25° C. The mixture was stirred at 25° C. for 1 h under N$_2$. LC-MS and TLC analysis showed that the reaction was complete. The reaction mixture was quenched by adding a saturated solution of EDTA and stirring the resulting mixture at 25° C. for 2 h. The reaction mixture was partitioned by adding EtOAc, and the aqueous phase was extracted with EtOAc. The organic phase was washed with brine, dried over anhydrous sodium sulfate, filtered, and concentrated in vacuo. The crude residue was purified by prep-TLC and prep-HPLC to give a solution of the desired product. The solution was lyophilized to give the desired product as a yellow solid.

3-methoxy-N-methyl-4-[(3-{4-[(oxan-4-yl)amino]-1-(2,2,2-trifluoroethyl)-1H-indol-2-yl}prop-2-yn-1-yl)amino]benzene-1-sulfonamide, MS (ES+, m/z): 551.2; 3-methoxy-N-methyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide, MS (ES+, m/z): 564.2; 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxy-N-methylbenzene-1-sulfonamide, MS (ES+, m/z): 638.2; 3-methoxy-N-methyl-4-[(3-{4-[(oxan-4-yl)amino]-1-(2,2,2-trifluoroethyl)-1H-indol-2-yl}prop-2-yn-1-yl)amino]benzamide, MS (ES+, m/z): 515.2; 3-methoxy-N-methyl-4-[(3-{4-[(1-methylpiperidin-4-yl)amino]-1-(2,2,2-trifluoroethyl)-1H-indol-2-yl}prop-2-yn-1-yl)amino]benzamide, MS (ES+, m/z): 528.2; 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxy-N-methylbenzamide, MS (ES+, m/z): 602.4; 4-{[3-(4-{[1-(2-hydroxypropyl)piperidin-4-yl]amino}-1-(2,2,2-trifluoroethyl)-1H-indol-2-yl)prop-2-yn-1-yl]amino}-3-methoxy-N-methylbenzamide, MS (ES+, m/z): 572.3; 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzamide, MS (ES+, m/z): 588.3; 3-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide, MS (ES+, m/z): 592.2; 3-methoxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide, MS (ES+, m/z): 592.3; 3-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide, MS (ES+, m/z): 556.3; 3-methoxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide, MS (ES+, m/z): 556.3; 3-methoxy-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide, MS (ES+, m/z): 584.2; and 3-methoxy-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzamide, MS (ES+, m/z): 584.2.

Example C45: General Procedure for Preparation of Compounds 123A, 124A, 149A, 150A, 157A, 158A, 185A, 186A, 303A, 304A, 407A, 408A, 489A, 663A, and 664A

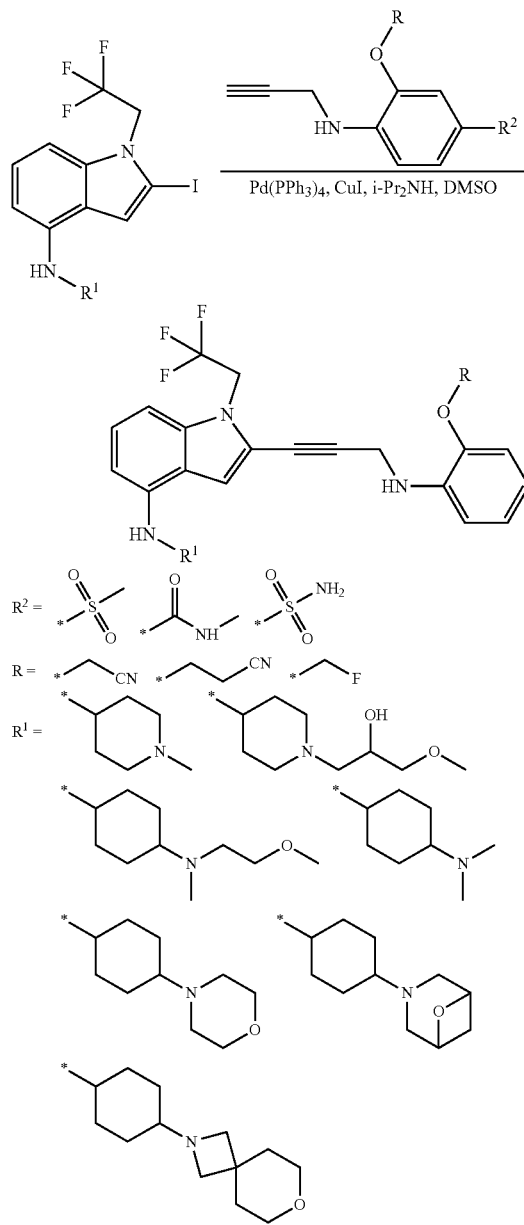

To a mixture of R-substituted alkyne (1~2 eq.) in DMSO (2 mL) was added i-Pr$_2$NH (10~30 eq.). CuI (1~2 eq.), R$^1$-substituted indole (1 eq.), and Pd(PPh$_3$)$_4$ (0.20~0.50 eq.) were then added to the mixture, and the mixture was stirred at 20~40° C. for 1~3 h under N$_2$. The progress of the reaction was monitored by LC-MS or TLC analysis. The mixture was poured into a saturated EDTA solution (15 mL) and stirred for 1 h. The aqueous phase was extracted with EtOAc (20 mL×3), and the combined organic layers were washed with brine (20 mL×3), dried over anhydrous sodium sulfate, filtered, and concentrated in vacuo. The residue was purified by prep-TLC, prep-HPLC, or prep-TLC followed by prep-HPLC to afford the desired compounds.

2-{5-methanesulfonyl-2-[(3-{4-[(1-methylpiperidin-4-yl)amino]-1-(2,2,2-trifluoroethyl)-1H-indol-2-yl}prop-2-yn-1-yl)amino]phenoxy}acetonitrile, MS (ES$^+$, m/z): 574.3; 1-(4-{[2-(3-{[2-(fluoromethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol, MS (ES$^+$, m/z): 641.6; 3-(fluoromethoxy)-N-methyl-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide, MS (ES$^+$, m/z): 618.3; 3-(fluoromethoxy)-N-methyl-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzamide, MS (ES$^+$, m/z): 618.3; 3-(fluoromethoxy)-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-N-methylbenzamide, MS (ES$^+$, m/z): 620.2; 3-(cyanomethoxy)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide, MS (ES$^+$, m/z): 603.4; 3-(cyanomethoxy)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide, MS (ES$^+$, m/z): 603.3; 2-(5-methanesulfonyl-2-{[3-(4-{[(1R,4R)-4-(morpholin-4-yl)cyclohexyl]amino}-1-(2,2,2-trifluoroethyl)-1H-indol-2-yl)prop-2-yn-1-yl]amino}phenoxy)acetonitrile, MS (ES$^+$, m/z): 644.2; 2-(5-methanesulfonyl-2-{[3-(4-{[(1S,4S)-4-(morpholin-4-yl)cyclohexyl]amino}-1-(2,2,2-trifluoroethyl)-1H-indol-2-yl)prop-2-yn-1-yl]amino}phenoxy)acetonitrile, MS (ES$^+$, m/z): 644.2; 2-(5-methanesulfonyl-2-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}phenoxy)acetonitrile, MS (ES$^+$, m/z): 646.2; 2-(5-methanesulfonyl-2-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}phenoxy)acetonitrile, MS (ES$^+$, m/z): 646.2; 2-(5-methanesulfonyl-2-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}phenoxy)acetonitrile, MS (ES$^+$, m/z): 656.2; 2-(5-methanesulfonyl-2-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}phenoxy)acetonitrile, MS (ES$^+$, m/z): 656.2; 2-(5-methanesulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetonitrile, MS (ES$^+$, m/z): 684.3; and 2-(5-methanesulfonyl-2-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetonitrile, MS (ES$^+$, m/z): 684.3.

Example C46: General Procedure for Preparation of Compounds 253A, 254A, 255A, 256A, 257A, 258A, 259A and 260A

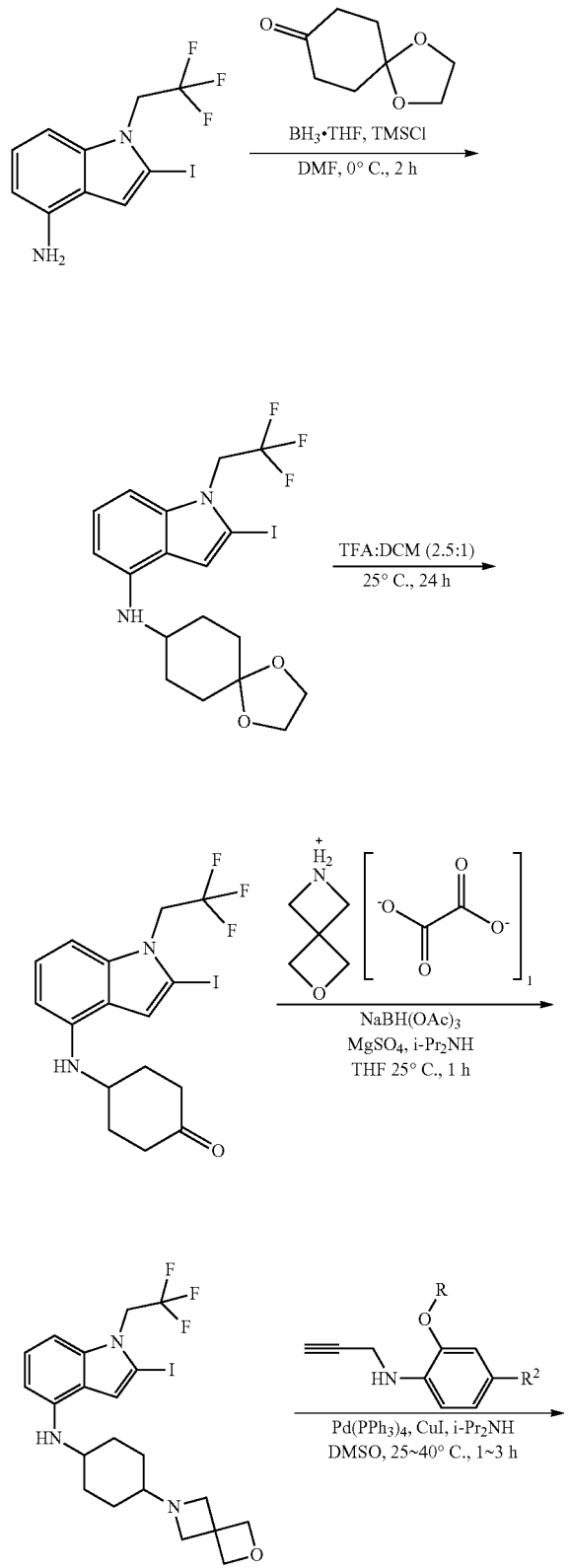

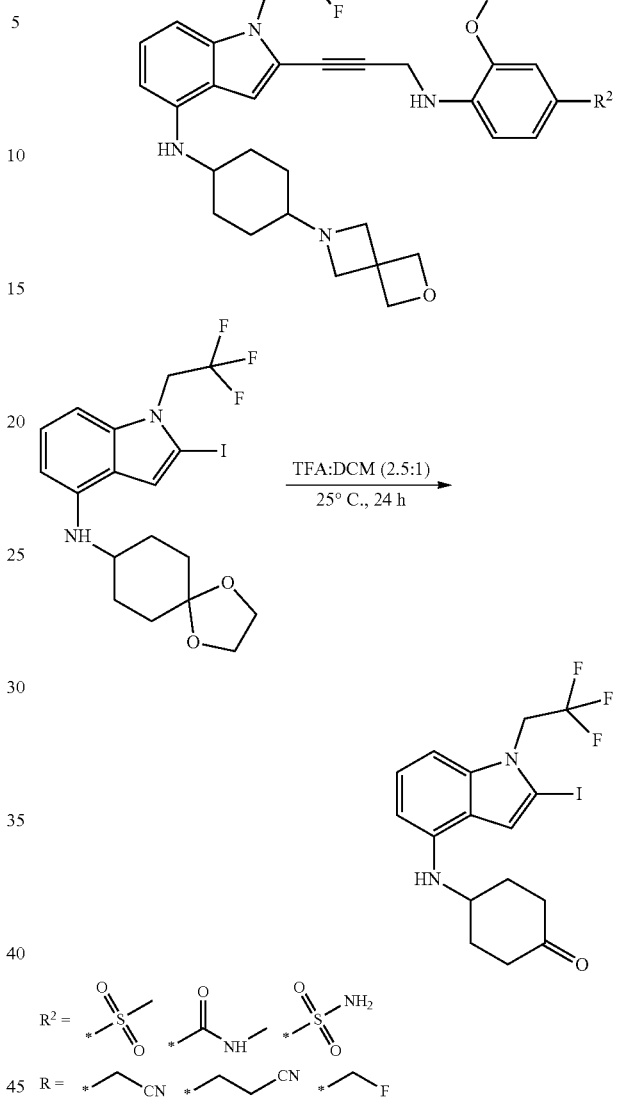

Synthesis of 2-iodo-N-(1,4-dioxaspiro[4.5]decan-8-yl)-1-(2,2,2-trifluoroethyl)-1H-indol-4-amine: To a solution of 2-iodo-1-(2,2,2-trifluoroethyl)-1H-indol-4-amine (10 g, 29.40 mmol, 1 eq.) and 1,4-dioxaspiro[4.5]decan-8-one (11.48 g, 73.51 mmol, 2.5 eq.) in DMF (100 mL) was added $BH_3 \cdot THF$ (1 M, 88.21 mL, 3 eq.). The mixture was stirred at 0° C. for 1 h, TMSCl (7.99 g, 73.51 mmol, 9.33 mL, 2.5 eq.) was added to the reaction, and the mixture was stirred at 0° C. for 1 h. LC-MS and TLC analysis showed that the reaction was completed. The reaction mixture was poured into ice-water (1000 mL), and the aqueous phase was extracted with EtOAc (300 mL×3). The combined organic layers were washed with brine (100 mL×2), dried over anhydrous sodium sulfate, filtered and concentrated in vacuo to give a residue. The residue was washed with PE (20 mL) at 25° C. for 10 h and filtered to obtained desired compound 2-iodo-N-(1,4-dioxaspiro[4.5]decan-8-yl)-1-(2,2,2-trifluoroethyl)-1H-indol-4-amine (30 g, 61.84 mmol, 70.10% yield) as a light yellow solid.

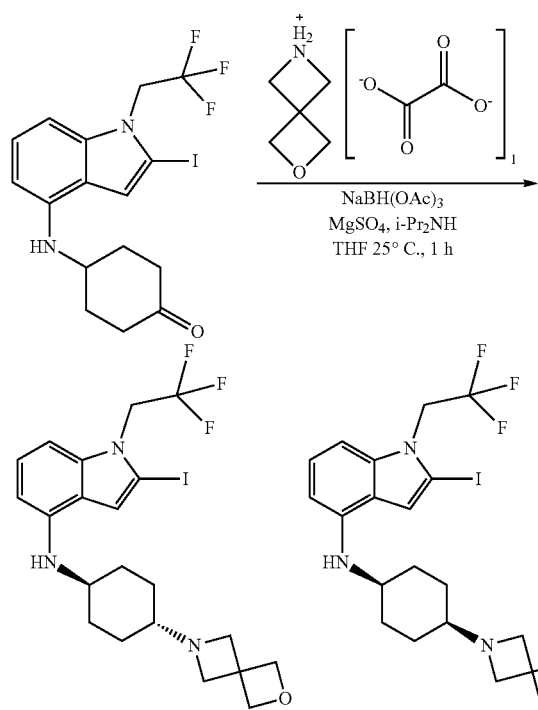

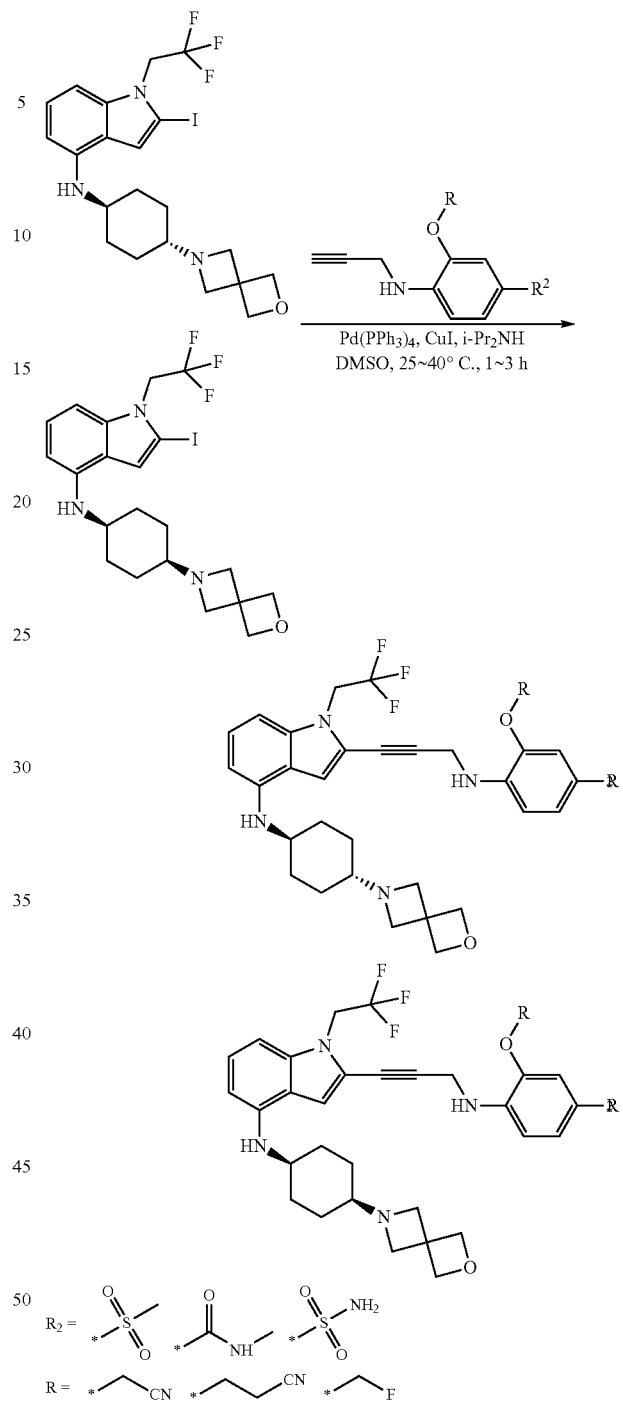

Synthesis of N-((1R,4R)-4-(2-oxa-6-azaspiro[3.3]heptan-6-yl)cyclohexyl)-2-iodo-1-(2,2,2-trifluoroethyl)-1H-indol-4-amine and N-((1S,4S)-4-(2-oxa-6-azaspiro[3.3]heptan-6-yl)cyclohexyl)-2-iodo-1-(2,2,2-trifluoroethyl)-1H-indol-4-amine: To a solution of 2-iodo-N-(1,4-dioxaspiro[4.5]decan-8-yl)-1-(2,2,2-trifluoroethyl)-1H-indol-4-amine (5.5 g, 10.72 mmol, 1 eq.) and 2-oxa-6-azaspiro[3.3]heptan-6-ium oxalate (2.43 g, 12.86 mmol, 1.2 eq.) in THF (100 mL) were added $MgSO_4$ (6.45 g, 53.59 mmol, 5 eq.) and i-$Pr_2NH$ (5.42 g, 53.59 mmol, 7.57 mL, 5 eq.). The mixture was stirred at 25° C. for 0.5 h. $NaBH(OAc)_3$ (4.54 g, 21.43 mmol, 2 eq.) was added into the reaction, and the resulting mixture was stirred at 25° C. for 1 h, after which time TLC analysis indicated that the ketone starting material was completely consumed. The reaction mixture was then poured into water (200 mL), and the residue was extracted with EtOAc (100 mL×3). The combined organic layers were washed with brine (100 mL×3), dried over anhydrous sodium sulfate, filtered, and concentrated under reduced pressure to give a residue that was purified by column chromatography ($SiO_2$, PE:EtOAc=2:1 to EtOAc to DCM:MeOH=10:1) to afford desired diastereomers N-((1R,4R)-4-(2-oxa-6-azaspiro[3.3]heptan-6-yl)cyclohexyl)-2-iodo-1-(2,2,2-trifluoroethyl)-1H-indol-4-amine (3 g, 4.91 mmol, 91.63% yield) as yellow solid and N-((1S,4S)-4-(2-oxa-6-azaspiro[3.3]heptan-6-yl)cyclohexyl)-2-iodo-1-(2,2,2-trifluoroethyl)-1H-indol-4-amine (1.7 g, 2.78 mmol, 51.92% yield) as yellow solids.

Representative Procedure: To a solution of 2-[5-methylsulfonyl-2-(prop2 ynylamino)phenoxy]acetonitrile (81.4 mg, 231 μmol, 1.5 eq.) in DMSO (2 mL) were added i-$Pr_2NH$ (4.62 mmol, 650 μL, 30 eq.), Cu (58.7 mg, 308 μmol, 2 eq.), 2-iodo-N-[4-(2-oxa-6-azaspiro[3.3]heptan-6-yl)cyclohexyl]-1-(2,2,2-trifluoroethyl)indol-4-amine (100 mg, 154 μmol, 1 eq.), and $Pd(PPh_3)_4$ (44.5 mg, 38.5 μmol, 0.25 eq.). The mixture was stirred at 25° C. for 1 h under $N_2$. TLC analysis (DCM:MeOH=20:1, $R_f$=0.21) indicated that the iodide was consumed completely, and one new spot was detected. The mixture was poured into a saturated aqueous EDTA solution (20 mL) and stirred at 25° C. for 1 h. The mixture was extracted with EtOAc (20 mL×3). The combined organic layers were washed with brine (20 mL×3), dried over anhydrous sodium sulfate, filtered, and concentrated under reduced pressure to give a residue, which was purified by prep-TLC (DCM:MeOH:TEA=150:10:0.5), then further purified by prep-HPLC to afford 2-[5-methylsulfonyl-2-[3-[4-[[4-(2-oxa-6-azaspiro[3.3]heptan-6-yl)cyclohexyl]amino]-1-(2,2,2-trifluoroethyl)indol-2-yl]prop-2-ynylamino]phenoxy]acetonitrile (10.1 mg, 13.9 μmol, 9.0% yield, FA salt) as a light yellow solid. The other analogs in the series were prepared using the same method.

3-(2-cyanoethoxy)-N-methyl-4-{[3-(4-{[1 (1R,4R)-4-{2-oxa-6-azaspiro[13.3]heptan-6-yl}cyclohexyl]amino}-1-(2,2,2-trifluoroethyl)-1H-indol-2-yl)prop-2-yn-1-yl]amino}benzamide, MS (ES+, m/z): 649.3; 3-(2-cyanoethoxy)-N-methyl-4-{[3-(4-{[1 (1S,4S)-4-{2-oxa-6-azaspiro[13.3]heptan-6-yl}cyclohexyl]amino}-1-(2,2,2-trifluoroethyl)-1H-indol-2-yl)prop-2-yn-1-yl]amino}benzamide, MS (ES+, m/z): 649.3; 2-(3-{[2-(fluoromethoxy)-4-methanesulfonylphenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine, (ES+, m/z): 649.3; 2-(3-{[2-(fluoromethoxy)-4-methanesulfonylphenyl]amino}prop-1-yn-1-yl)-N-[(1S,4S)-4-{2-oxa-6-azaspiro[3.3]heptan-6-yl}cyclohexyl]-1-(2,2,2-trifluoroethyl)-1H-indol-4-amine, (ES+, m/z): 649.3; 3-(fluoromethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide, (ES+, m/z): 628.3; 3-(fluoromethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide, (ES+, m/z): 628.3; 3-(cyanomethoxy)-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide, (ES+, m/z): 657.4; and 3-(cyanomethoxy)-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide, (ES+, m/z): 657.4.

Example C47: General Procedure for Preparation of Compounds 389A and 390A

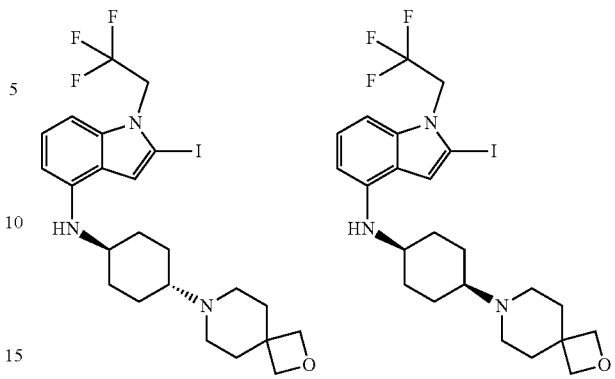

Synthesis of N-((1R,4R)-4-(2-oxa-7-azaspiro[3.5]nonan-7-yl)cyclohexyl)-2-iodo-1-(2,2,2-trifluoroethyl)-1H-indol-4-amine and N-((1S,4S)-4-(2-oxa-7-azaspiro[3.5]nonan-7-yl)cyclohexyl)-2-iodo-1-(2,2,2-trifluoroethyl)-1H-indol-4-amine: To a solution of 4-((2-iodo-1-(2,2,2-trifluoroethyl)-1H-indol-4-yl)amino)cyclohexan-1-one and 2-oxa-7-azaspiro[3.5]nonan-7-ium oxalate (1.15 g, 5.31 mmol, 5 eq.) in DCE (4 mL) were added MgSO4 (640 mg, 5.31 mmol, 5 eq.), molecular sieve powder (400 mg) and i-Pr2NH (10.6 mmol, 1.50 mL, 10 eq.). The mixture was heated and stirred at 50° C. for 0.5 h, and NaBH(OAc)3 (450.4 mg, 2.13 mmol, 2 eq.) was then added. The mixture was heated and stirred at 70° C.~100° C. for 1 h, after which time LC-MS analysis indicated that the starting ketone was consumed completely, and one main peak pertaining to the desired product mass was detected. The reaction mixture was diluted with DCM (20 mL), filtered, and concentrated under reduced pressure to provide a residue that was purified by prep-HPLC to afford desired diastereomers N-((1R,4R)-4-(2-oxa-7-azaspiro[3.5]nonan-7-yl)cyclohexyl)-2-iodo-1-(2,2,2-trifluoroethyl)-1H-indol-4-amine (0.1 g, 176 μmol, 8.0% yield) and N-((1S,4S)-4-(2-oxa-7-azaspiro[3.5]nonan-7-yl)cyclohexyl)-2-iodo-1-(2,2,2-trifluoroethyl)-1H-indol-4-amine (0.1 g, 179 μmol, 8.2% yield) as yellow solids.

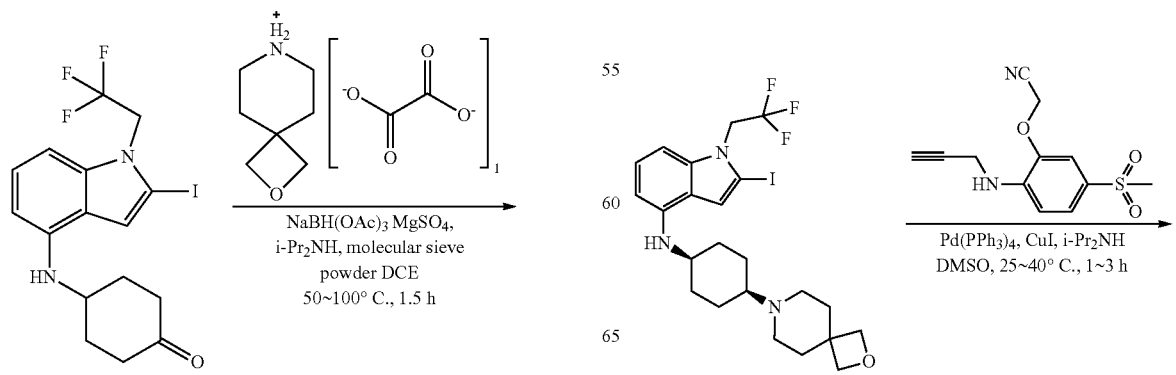

-continued

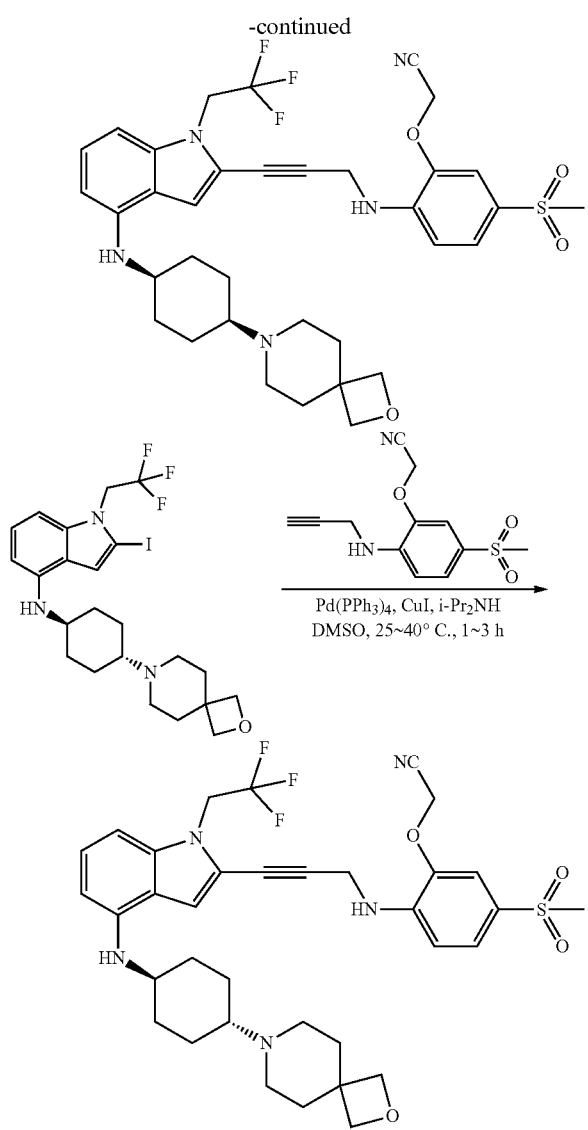

Representative procedure for trans isomer: To a solution of 2-[5-methylsulfonyl-2-(prop-2-ynylamino)phenoxy]acetonitrile (44.6 mg, 143 μmol, 2 eq.) in DMSO (1 mL) were added i-Pr₂NH (2.15 mmol, 303 μL, 30 eq.), CuI (27.3 mg, 143 μmol, 2 eq.), 2-iodo-N-[4-(2-oxa-7-azaspiro[3.5]nonan-7-yl)cyclohexyl]-1-(2,2,2-trifluoroethyl)indol-4-amine (40 mg, 71.7 μmol, 1 eq.), and Pd(PPh₃)₄ (20.7 mg, 17.9 μmol, 0.25 eq.) at 25° C. The mixture was stirred at 25° C. for 1 h under N₂. TLC analysis (DCM:MeOH=10:1, R$_f$=0.25) indicated that the iodide starting material was consumed completely, and one new spot was detected. The mixture was poured into saturated aqueous EDTA (20 mL) and stirred at 25° C. for 1 h. The mixture was then extracted with EtOAc (3×20 mL). The combined organic layers were washed with brine (3×20 mL), dried over anhydrous sodium sulfate, filtered, and concentrated under reduced pressure to give a residue that was purified by prep-TLC (DCM:MeOH=10:1, R$_f$=0.25), then further purified by prep-HPLC to afford 2-[5-methylsulfonyl-2-[3-[4-[[4-(2-oxa-7-azaspiro[3.5]nonan-7-yl)cyclohexyl]amino]-1-(2,2,2-trifluoroethyl)indol-2-yl]prop-2-ynylamino]phenoxy]acetonitrile (18.0 mg, 24.4 μmol, 34.1% yield, FA salt) as a yellow solid.

The corresponding cis-isomer was synthesized using the method described above. MS (ES⁺, m/z): 538.2, 89.6% yield 2-(5-methanesulfonyl-2-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}phenoxy)acetonitrile, MS (ES⁺, m/z): 684.2; and 2-(5-methanesulfonyl-2-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}phenoxy)acetonitrile, MS (ES⁺, m/z): 684.2.

Example C48: General Procedure for Preparation of Compounds 162A, 163A, 322A, 323A, 350A, 351A, 424A, 425A, 436A, 437A, 442A, and 443A

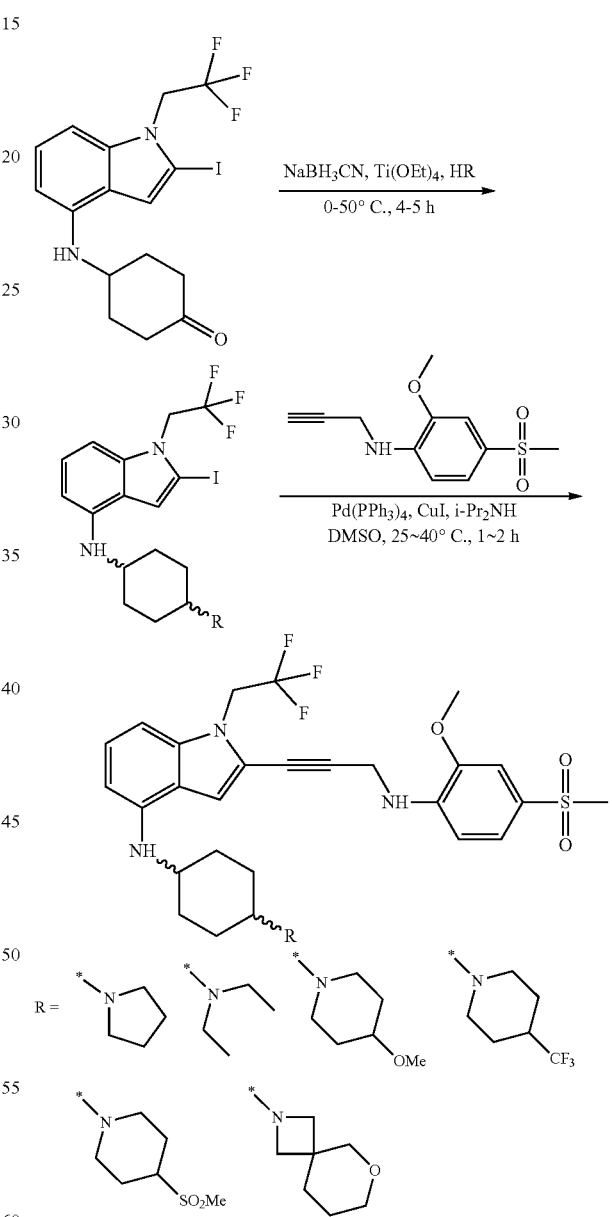

Representative procedure for reductive amination: To a solution of 4-[[2-iodo-1-(2,2,2-trifluoroethyl)indol-4-yl]amino]cyclohexanone (600 mg, 1.24 mmol, 1 eq.) in EtOH (3 mL) was added 4-methoxypiperidine (6.19 mmol, 59 μL, 5 eq.) and Ti(OEt)₄ (6.19 mmol, 1.28 mL, 5 eq.). The reaction mixture was heated and stirred at 50° C. for 4 h.

Then to the reaction mixture was added NaBH₃CN (389 mg, 6.19 mmol, 5 eq.) under N₂. The reaction mixture was warmed stirred at 50° C. for 1 h. TLC analysis (DCM:MeOH=10:1, $R_{f1}$=0.3, $R_{f2}$=0.25) showed that the starting material was consumed. The solution was dried under vacuum to give the crude product. The residue was purified by column chromatography (SiO₂, PE:EtOAc=5:1 to 0:1) to afford the intermediate product 2-iodo-N-[4-(4-methoxy-1-piperidyl)cyclohexyl]-1-(2,2,2-trifluoroethyl)indol-4-amine (550 mg, 1.03 mmol, 83.0% yield) as a brown oil.

Step 2: The above specified R-substituted iodoindoles were coupled to 2-methoxy-4-(methylsulfonyl)-N-(prop-2-yn-1-yl)aniline according to the general procedure specified in EXAMPLE C47. In each case, TLC/LC-MS analysis indicated that the starting material was completely consumed after heating at 45° C. for 2 h.

2-{3-[(4-methanesulfonyl-2-methoxyphenyl)amino]prop-1-yn-1-yl}-N-[(1R,4R)-4-(pyrrolidin-1-yl)cyclohexyl]-1-(2,2,2-trifluoroethyl)-1H-indol-4-amine, MS (ES⁺, m/z): 603.2; 2-{3-[(4-methanesulfonyl-2-methoxyphenyl)amino]prop-1-yn-1-yl}-N-[(1S,4S)-4-(pyrrolidin-1-yl)cyclohexyl]-1-(2,2,2-trifluoroethyl)-1H-indol-4-amine, MS (ES⁺, m/z): 603.2; (1R,4R)—N¹,N¹-diethyl-N⁴-(2-{3-[(4-methanesulfonyl-2-methoxyphenyl)amino]prop-1-yn-1-yl}-1-(2,2,2-trifluoroethyl)-1H-indol-4-yl)cyclohexane-1,4-diamine, MS (ES⁺, m/z): 605.4; (1S,4S)—N¹,N¹-diethyl-N⁴-(2-{3-[(4-methanesulfonyl-2-methoxyphenyl)amino]prop-1-yn-1-yl}-1-(2,2,2-trifluoroethyl)-1H-indol-4-yl)cyclohexane-1,4-diamine, MS (ES⁺, m/z): 605.2; 2-{3-[(4-methanesulfonyl-2-methoxyphenyl)amino]prop-1-yn-1-yl}-N-[(1R,4R)-4-(4-methoxypiperidin-1-yl)cyclohexyl]-1-(2,2,2-trifluoroethyl)-1H-indol-4-amine, MS (ES⁺, m/z): 647.3; 2-{3-[(4-methanesulfonyl-2-methoxyphenyl)amino]prop-1-yn-1-yl}-N-[(1S,4S)-4-(4-methoxypiperidin-1-yl)cyclohexyl]-1-(2,2,2-trifluoroethyl)-1H-indol-4-amine, MS (ES⁺, m/z): 647.2; 2-{3-[(4-methanesulfonyl-2-methoxyphenyl)amino]prop-1-yn-1-yl}-N-[(1R,4R)-4-[4-(trifluoromethyl)piperidin-1-yl]cyclohexyl]-1-(2,2,2-trifluoroethyl)-1H-indol-4-amine, MS (ES⁺, m/z): 685.2; 2-{3-[(4-methanesulfonyl-2-methoxyphenyl)amino]prop-1-yn-1-yl}-N-[(1S,4S)-4-[4-(trifluoromethyl)piperidin-1-yl]cyclohexyl]-1-(2,2,2-trifluoroethyl)-1H-indol-4-amine, MS (ES⁺, m/z): 685.2; 2-{3-[(4-methanesulfonyl-2-methoxyphenyl)amino]prop-1-yn-1-yl}-N-[(1R,4R)-4-(4-methanesulfonylpiperidin-1-yl)cyclohexyl]-1-(2,2,2-trifluoroethyl)-1H-indol-4-amine, MS (ES⁺, m/z): 695.2; 2-{3-[(4-methanesulfonyl-2-methoxyphenyl)amino]prop-1-yn-1-yl}-N-[(1S,4S)-4-(4-methanesulfonylpiperidin-1-yl)cyclohexyl]-1-(2,2,2-trifluoroethyl)-1H-indol-4-amine, MS (ES⁺, m/z): 695.2; 2-{3-[(4-methanesulfonyl-2-methoxyphenyl)amino]prop-1-yn-1-yl}-N-[(1R,4R)-4-{6-oxa-2-azaspiro[3.5]nonan-2-yl}cyclohexyl]-1-(2,2,2-trifluoroethyl)-1H-indol-4-amine, MS (ES⁺, m/z): 659.2; and 2-{3-[(4-methanesulfonyl-2-methoxyphenyl)amino]prop-1-yn-1-yl}-N-[(1S,4S)-4-{6-oxa-2-azaspiro[3.5]nonan-2-yl}cyclohexyl]-1-(2,2,2-trifluoroethyl)-1H-indol-4-amine, MS (ES⁺, m/z): 659.2.

Example C49: General Procedure for Preparation of Compounds 144A, 145A, 318A, 319A, 352A, 353A, 420A, 421A, 438A, 439A, 444A, and 445A

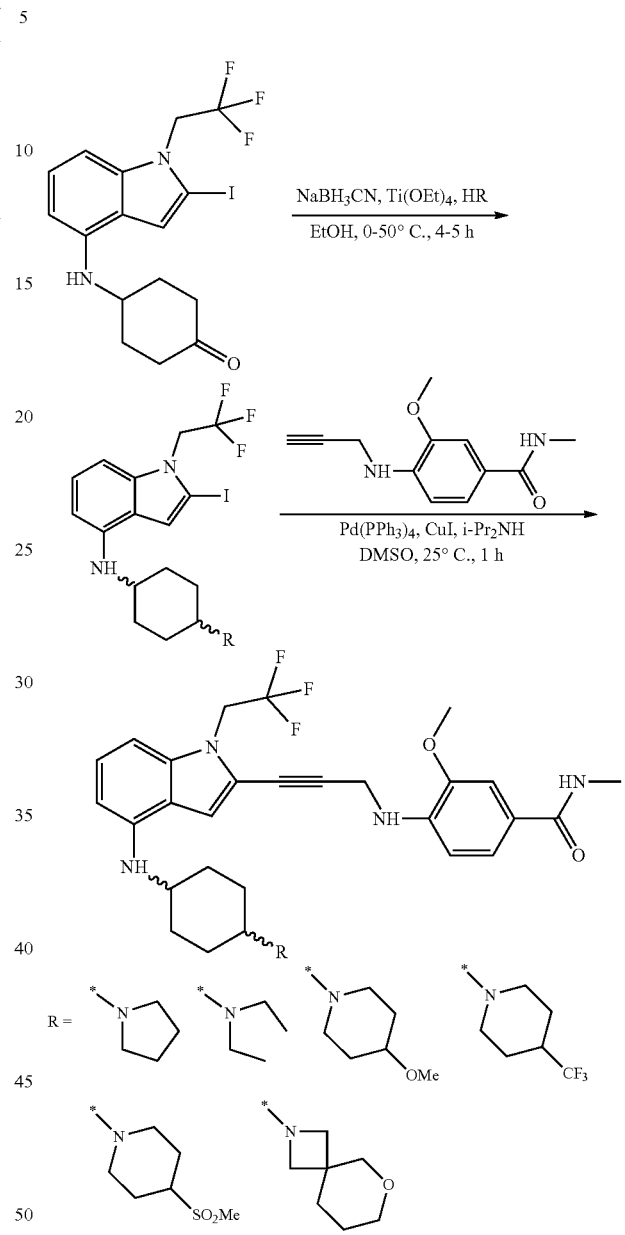

Compounds 144A, 145A, 318A, 319A, 352A, 353A, 420A, 421A, 438A, 439A, 444A, and 445A were prepared via a procedure analogous to the synthesis of the compounds described in EXAMPLE C32, using 3-methoxy-N-methyl-4-(prop-2-yn-1-ylamino)benzamide in place of 2-methoxy-4-(methylsulfonyl)-N-(prop-2-yn-1-yl)aniline.

3-methoxy-N-methyl-4-{[3-(4-{[(1R,4R)-4-(pyrrolidin-1-yl)cyclohexyl]amino}-1-(2,2,2-trifluoroethyl)-1H-indol-2-yl)prop-2-yn-1-yl]amino}benzamide, MS (ES⁺, m/z): 582.3; 3-methoxy-N-methyl-4-{[3-(4-{[(1S,4S)-4-(pyrrolidin-1-yl)cyclohexyl]amino}-1-(2,2,2-trifluoroethyl)-1H-indol-2-yl)prop-2-yn-1-yl]amino}benzamide, MS (ES⁺, m/z): 582.3; 3-methoxy-N-methyl-4-{[3-(4-{[(1R,4R)-4-(diethylamino)cyclohexyl]amino}-1-(2,2,2-trifluoroethyl)-1H-indol-2-yl)prop-2-yn-1-yl]amino}benzamide, MS (ES⁺, m/z):

584.3; 3-methoxy-N-methyl-4-{[3-(4-{[(1S,4S)-4-(diethylamino)cyclohexyl]amino}-1-(2,2,2-trifluoroethyl)-1H-indol-2-yl)prop-2-yn-1-yl]amino}benzamide, MS (ES+, m/z): 584.3; 3-methoxy-N-methyl-4-{[3-(4-{[(1R,4R)-4-(4-methoxypiperidin-1-yl)cyclohexyl]amino}-1-(2,2,2-trifluoroethyl)-1H-indol-2-yl)prop-2-yn-1-yl]amino}benzamide, MS (ES+, m/z): 626.3; 3-methoxy-N-methyl-4-{[3-(4-{[(1S,4S)-4-(4-methoxypiperidin-1-yl)cyclohexyl]amino}-1-(2,2,2-trifluoroethyl)-1H-indol-2-yl)prop-2-yn-1-yl]amino}benzamide, MS (ES+, m/z): 626.3; 3-methoxy-N-methyl-4-{[3-(4-{[(1R,4R)-4-(4-(trifluoromethyl)piperidin-1-yl]cyclohexyl]amino}-1-(2,2,2-trifluoroethyl)-1H-indol-2-yl)prop-2-yn-1-yl]amino}benzamide, MS (ES+, m/z): 664.3; 3-methoxy-N-methyl-4-{[3-(4-{[(1S,4S)-4-[4-(trifluoromethyl)piperidin-1-yl]cyclohexyl]amino}-1-(2,2,2-trifluoroethyl)-1H-indol-2-yl)prop-2-yn-1-yl]amino}benzamide, MS (ES+, m/z): 664.2; 3-methoxy-N-methyl-4-{[3-(4-{[(1R,4R)-4-(4-methanesulfonylpiperidin-1-yl)cyclohexyl]amino}-1-(2,2,2-trifluoroethyl)-1H-indol-2-yl)prop-2-yn-1-yl]amino}benzamide, MS (ES+, m/z): 674.3; 3-methoxy-N-methyl-4-{[3-(4-{[(1S,4S)-4-(4-methanesulfonylpiperidin-1-yl)cyclohexyl]amino}-1-(2,2,2-trifluoroethyl)-1H-indol-2-yl)prop-2-yn-1-yl]amino}benzamide, MS (ES+, m/z): 674.3; 3-methoxy-N-methyl-4-{[3-(4-{[(1R,4R)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzamide, MS (ES+, m/z): 638.3; and 3-methoxy-N-methyl-4-{[3-(4-{[(1S,4S)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzamide, MS (ES+, m/z): 638.3.

Example C50: General Procedure for Preparation of Compounds 146A, 147A, 320A, 321A, 354A, 355A, 422A, 423A, 440A, 441A, 446A, and 447A

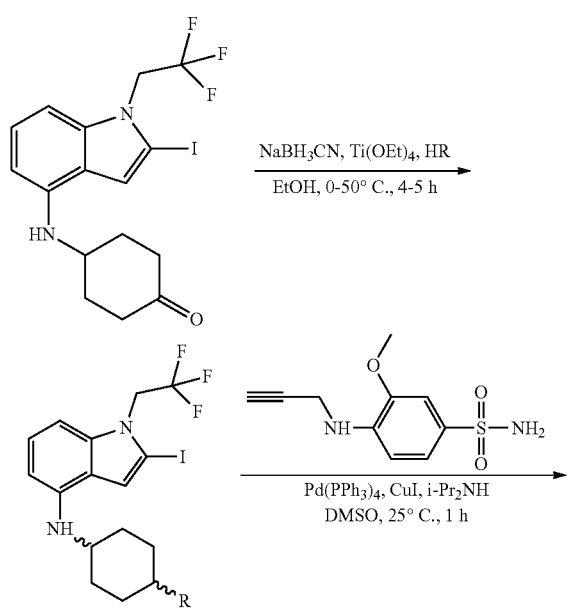

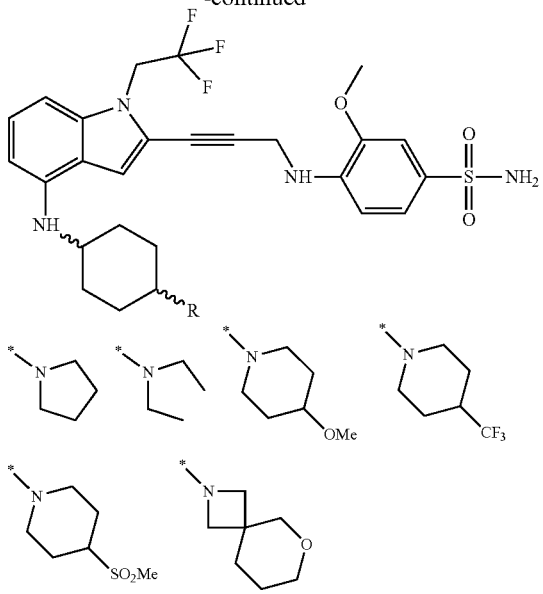

Compounds 146A, 147A, 320A, 321A, 354A, 355A, 422A, 423A, 440A, 441A, 446A, and 447A were prepared via a procedure analogous to the synthesis of the compounds described in EXAMPLE C32, using 3-methoxy-4-(prop-2-yn-1-ylamino)benzenesulfonamide in place of 2-methoxy-4-(methylsulfonyl)-N-(prop-2-yn-1-yl)aniline.

3-methoxy-4-{[3-(4-{[(1R,4R)-4-(pyrrolidin-1-yl)cyclohexyl]amino}-1-(2,2,2-trifluoroethyl)-1H-indol-2-yl)prop-2-yn-1-yl]amino}benzene-1-sulfonamide, MS (ES+, m/z): 604.3; 3-methoxy-4-{[3-(4-{[(1S,4S)-4-(pyrrolidin-1-yl)cyclohexyl]amino}-1-(2,2,2-trifluoroethyl)-1H-indol-2-yl)prop-2-yn-1-yl]amino}benzene-1-sulfonamide, MS (ES+, m/z): 604.2; 3-methoxy-4-{[3-(4-{[(1R,4R)-4-(diethylamino)cyclohexyl]amino}-1-(2,2,2-trifluoroethyl)-1H-indol-2-yl)prop-2-yn-1-yl]amino}benzene-1-sulfonamide, MS (ES+, m/z): 606.2; 3-methoxy-4-{[3-(4-{[(1S,4S)-4-(diethylamino)cyclohexyl]amino}-1-(2,2,2-trifluoroethyl)-1H-indol-2-yl)prop-2-yn-1-yl]amino}benzene-1-sulfonamide, MS (ES+, m/z): 606.2; 3-methoxy-4-{[3-(4-{[(1R,4R)-4-(4-methoxypiperidin-1-yl)cyclohexyl]amino}-1-(2,2,2-trifluoroethyl)-1H-indol-2-yl)prop-2-yn-1-yl]amino}benzene-1-sulfonamide, MS (ES+, m/z): 648.3; 3-methoxy-4-{[3-(4-{[(1S,4S)-4-(4-methoxypiperidin-1-yl)cyclohexyl]amino}-1-(2,2,2-trifluoroethyl)-1H-indol-2-yl)prop-2-yn-1-yl]amino}benzene-1-sulfonamide, MS (ES+, m/z): 648.3; 3-methoxy-4-{[3-(4-{[(1R,4R)-4-[4-(trifluoromethyl)piperidin-1-yl]cyclohexyl]amino}-1-(2,2,2-trifluoroethyl)-1H-indol-2-yl)prop-2-yn-1-yl]amino}benzene-1-sulfonamide, MS (ES+, m/z): 686.2; 3-methoxy-4-{[3-(4-{[(1S,4S)-4-[4-(trifluoromethyl)piperidin-1-yl]cyclohexyl]amino}-1-(2,2,2-trifluoroethyl)-1H-indol-2-yl)prop-2-yn-1-yl]amino}benzene-1-sulfonamide, MS (ES+, m/z): 686.2; 3-methoxy-4-{[3-(4-{[(1R,4R)-4-(4-methanesulfonylpiperidin-1-yl)cyclohexyl]amino}-1-(2,2,2-trifluoroethyl)-1H-indol-2-yl)prop-2-yn-1-yl]amino}benzene-1-sulfonamide, MS (ES+, m/z): 696.2; 3-methoxy-4-{[3-(4-{[(1S,4S)-4-(4-methanesulfonylpiperidin-1-yl)cyclohexyl]amino}-1-(2,2,2-trifluoroethyl)-1H-indol-2-yl)prop-2-yn-1-yl]amino}benzene-1-sulfonamide, MS (ES+, m/z): 696.2; 3-methoxy-4-{[3-(4-{[(1R,4R)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide, MS (ES+, m/z): 660.3;

and 3-methoxy-4-{[3-(4-{[(1S,4S)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide, MS (ES+, m/z): 660.3.

Example C51: Preparation of Compounds 194A and 195A

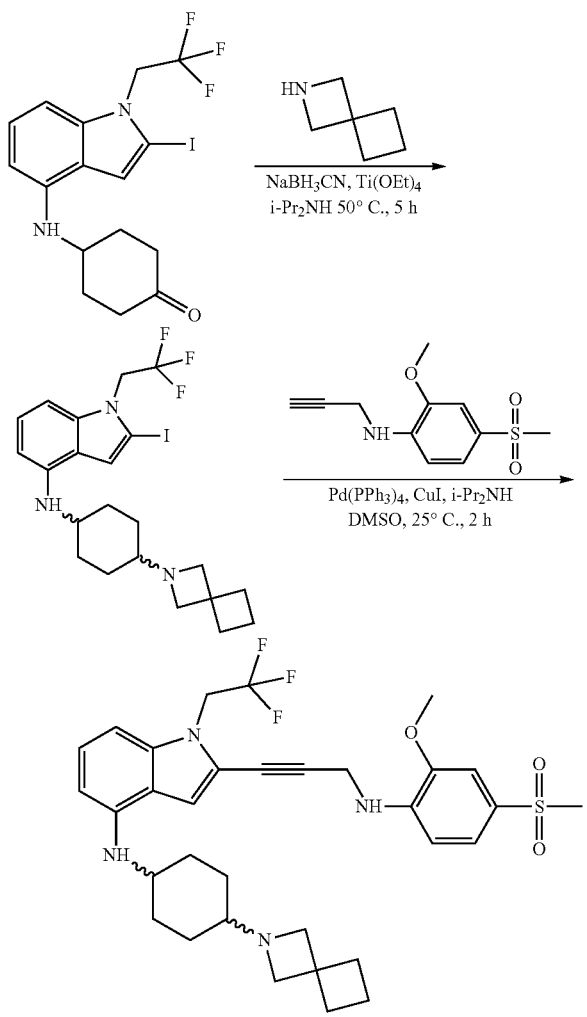

Synthesis of N-((1R,4R)-4-(2-azaspiro[3.3]heptan-2-yl)cyclohexyl)-2-iodo-1-(2,2,2-trifluoroethyl)-1H-indol-4-amine and N-((1S,4S)-4-(2-azaspiro[3.3]heptan-2-yl)cyclohexyl)-2-iodo-1-(2,2,2-trifluoroethyl)-1H-indol-4-amine Step 1: To a solution of 4-[[2-iodo-1-(2,2,2-trifluoroethyl)indol-4-yl]amino]cyclohexanone (600 mg, 1.24 mmol, 1 eq.) in EtOH (1 mL) were added 2-azaspiro[3.3]heptane oxalic acid salt (1.76 g, 6.20 mmol, 5 eq.), Ti(OEt)$_4$ (6.20 mmol, 1.29 mL, 5 eq.), and i-Pr$_2$NH (1.24 mmol, 175 μL, 1 eq.). The reaction mixture was stirred at 50° C. for 3 h. Then the reaction mixture was cooled, and NaBH$_3$CN (389.6 mg, 6.20 mmol, 5 eq.) was added to the reaction under N$_2$ at 0° C. The reaction mixture was stirred for 5 min, then warmed to 50° C. for 1 h. TLC analysis (EtOAc:TEA=20:1, R$_{f1}$=0.6, R$_{f2}$=0.55) showed that the starting material was completely consumed. The solution was dried under vacuum to give the crude product. The residue was purified by column chromatography (SiO$_2$, PE:EtOAc=5:1 to 0:1) to provide the N-[4-(2-azaspiro[3.3]heptan-2-yl)cyclohexyl]-2-iodo-1-(2,2,2-trifluoroethyl)indol-4-amine (600 mg, 1.16 mmol, 93.5% yield) as a brown oil.

Step 2: To a solution of 2-methoxy-4-methylsulfonyl-N-prop-2-ynyl-aniline (92.5 mg, 348 μmol, 1.2 eq.) in DMSO (3 mL) were added i-Pr$_2$NH (2.90 mmol, 410 μL, 10 eq.), Pd(PPh$_3$)$_4$ (67.0 mg, 58 μmol, 0.2 eq.), N-[4-(2-azaspiro[3.3]heptan-2-yl)cyclohexyl]-2-iodo-1-(2,2,2-trifluoroethyl)indol-4-amine (150 mg, 290 μmol, 1 eq.), and CuI (55.2 mg, 290 μmol, 1 eq.). The mixture was stirred at 25° C. for 2 h under N$_2$. TLC analysis (EtOAc:TEA=20:1, R$_f$=0.3, R$_f$=0.2) showed that the starting material was completely consumed. The reaction mixture was quenched by addition of saturated aqueous EDTA (30 mL) and stirring the mixture at 25° C. for 2 h. The reaction mixture was partitioned with EtOAc, and the aqueous phase was extracted with EtOAc (3×10 mL). The organic phase was washed with brine (10 mL×3), dried over anhydrous sodium sulfate, filtered and concentrated in vacuo to give the crude product. The residue was purified by prep-TLC (EtOAc:TEA=20:1, R$_f$=0.3, R$_f$=0.2), then further purified by prep-HPLC to give cis-N-[4-(2-azaspiro[3.3]heptan-2-yl)cyclohexyl]-2-[3-(2-methoxy-4-methylsulfonyl-anilino)prop-1-ynyl]-1-(2,2,2-trifluoroethyl)indol-4-amine (45.2 mg, 71.9 μmol, 24.8% yield) MS (ES+, m/z): 629.2, and trans-N-[4-(2-azaspiro[3.3]heptan-2-yl)cyclohexyl]-2-[3-(2-methoxy-4-methylsulfonyl-anilino)prop-1-ynyl]-1-(2,2,2-trifluoroethyl)indol-4-amine (46.5 mg, 74.0 μmol, 25.5% yield) MS (ES+, m/z): 629.2 as a yellow solid.

Example C52: Preparation of Compounds 196A and 197A

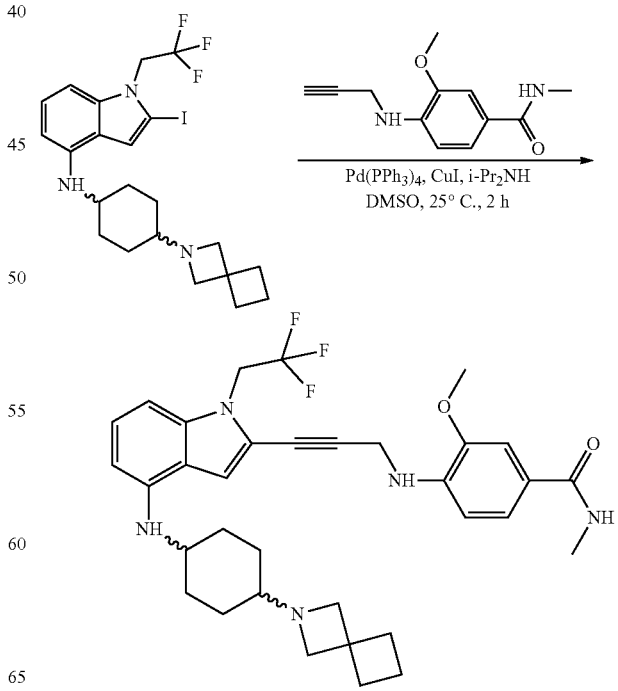

The desired products were prepared via a procedure analogous to EXAMPLE C51, using 3-methoxy-N-methyl-4-(prop-2-yn-1-ylamino)benzamide in place of 2-methoxy-4-(methylsulfonyl)-N-(prop-2-yn-1-yl)aniline.

3-methoxy-N-methyl-4-{[3-(4-{[(1R,4R)-4-{2-azaspiro[3.3]heptan-2-yl}cyclohexyl]amino}-1-(2,2,2-trifluoroethyl)-1H-indol-2-yl)prop-2-yn-1-yl]amino}benzamide, MS (ES+, m/z): 608.3; 3-methoxy-N-methyl-4-{[3-(4-{[(1S,4S)-4-{2-azaspiro[3.3]heptan-2-yl}cyclohexyl]amino}-1-(2,2,2-trifluoroethyl)-1H-indol-2-yl)prop-2-yn-1-yl]amino}benzamide, MS (ES+, m/z): 608.3.

Example C53: Preparation of Compounds 198A and 199A

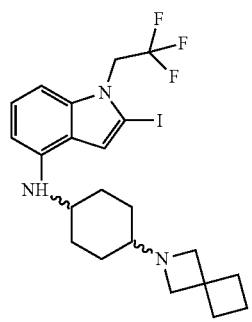
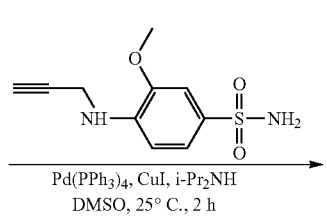

The desired products were prepared via a procedure analogous to EXAMPLE C51, using 3-methoxy-4-(prop-2-yn-1-ylamino)benzenesulfonamide in place of 2-methoxy-4-(methylsulfonyl)-N-(prop-2-yn-1-yl)aniline.

3-methoxy-4-{[3-(4-{[(1R,4R)-4-{2-azaspiro[3.3]heptan-2-yl}cyclohexyl]amino}-1-(2,2,2-trifluoroethyl)-1H-indol-2-yl)prop-2-yn-1-yl]amino}benzene-1-sulfonamide, MS (ES+, m/z): 630.3; and 3-methoxy-4-{[3-(4-{[(1S,4S)-4-{2-azaspiro[3.3]heptan-2-yl}cyclohexyl]amino}-1-(2,2,2-trifluoroethyl)-1H-indol-2-yl)prop-2-yn-1-yl]amino}benzene-1-sulfonamide, MS (ES+, m/z): 630.3.

Example C54: Preparation of Compounds 362A, 363A, 364A, and 365A

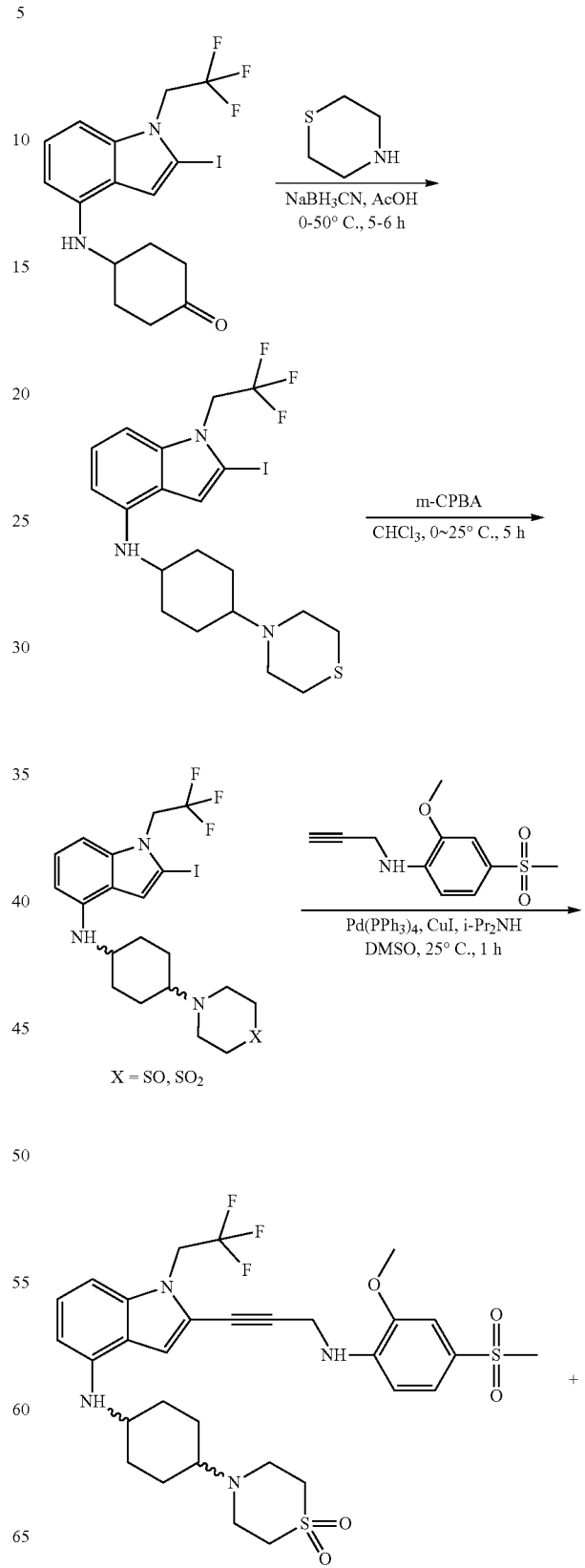

X = SO, SO₂

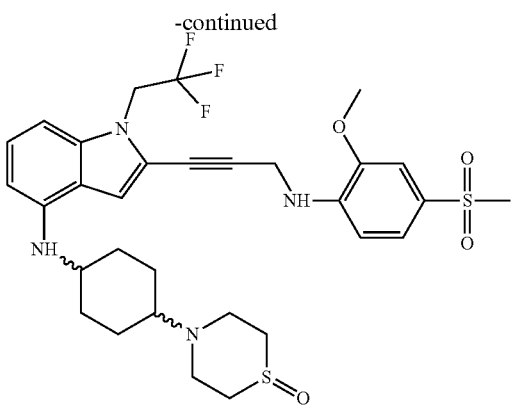

Synthesis of 1-(((difluoro-13-methyl)-12-fluoraneyl)methyl)-2-iodo-N-(4-thiomorpholinocyclohexyl)-1H-indol-4-amine: To a solution of 4-((2-iodo-1-(2,2,2-trifluoroethyl)-1H-indol-4-yl)amino)cyclohexan-1-one (1 g, 2.06 mmol, 1 eq.) in thiomorpholine (105.6 mmol, 10 mL, 51 eq.) was added AcOH (2.06 mmol, 118 µL, 1 eq.). The reaction mixture was stirred at 25° C. for 2 h, and NaBH$_3$CN (5 eq.) was added under N$_2$ at 0° C. The mixture was stirred further for 5 min, and then heated to 50° C. and stirred for 3 h, after which time TLC and LC-MS analysis indicated that the ketone starting material was completely consumed. The reaction was partitioned by adding water (100 mL) and EtOAc (20 mL). The residue was purified by column chromatography (SiO$_2$) (PE:EtOAc=10:1 to 0:1) to afford 1-(((difluoro-λ$^3$-methyl)-λ$^2$-fluoraneyl)methyl)-2-iodo-N-(4-thiomorpholinocyclohexyl)-1H-indol-4-amine (1.1 g, crude) (ES$^+$, m/z): 523.8.

Synthesis of 4-(4-((1-(((difluoro-λ$^3$-methyl)-λ$^2$-fluoraneyl)methyl)-2-iodo-1H-indol-4-yl)amino)cyclohexyl)thiomorpholine 1,1-dioxide: To a solution of 1-(((difluoro-λ$^3$-methyl)-λ$^2$-fluoraneyl)methyl)-2-iodo-N-(4-thiomorpholinocyclohexyl)-1H-indol-4-amine (1 g, 1.91 mmol, 1 eq.) in CHCl$_3$ (20 mL) was added m-CPBA (2.06 g, 9.55 mmol, 80% purity, 5 eq.) at 0° C. The mixture was stirred at 0~25° C. for 5 h, after which time TLC and LC-MS analysis indicated that the reaction was complete. The reaction was partitioned by adding a saturated aqueous solution of Na$_2$CO$_3$ (200 mL) and EtOAc (50 mL). The residue was purified by column chromatography (SiO$_2$) (PE:EtOAc=5:1 to 0:1, DCM:MeOH=10:1) to afford 4-(4-((1-(((difluoro-13-methyl)-12-fluoraneyl)methyl)-2-iodo-1H-indol-4-yl)amino)cyclohexyl)thiomorpholine 1,1-dioxide (0.8 g, 1.44 mmol, 75.4% yield). MS (ES$^+$, m/z): 555.7.

Preparation of final products: 4-(4-((1-(((difluoro-X$^3$-methyl)-X$^2$-fluoraneyl)methyl)-2-iodo-1H-indol-4-yl)amino)cyclohexyl)thiomorpholine 1,1-dioxide was coupled to 2-methoxy-4-(methylsulfonyl)-N-(prop-2-yn-1-yl)aniline according to the general procedure specified in EXAMPLE C51. In each case, TLC and LC-MS analysis indicated that the starting material was completely consumed after stirring the reaction mixture at 25° C. for 1 h. The resulting products were purified by prep-HPLC to afford the desired pure compounds.

4-[(1R,4R)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1λ$^6$-thiomorpholine-1,1-dione, MS (ES$^+$, m/z): 667.2; 4-[(1S,4S)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1λ$^6$-thiomorpholine-1,1-dione, MS (ES$^+$, m/z): 667.2; 4-[(1R,4R)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1λ$^4$-thiomorpholin-1-one, MS (ES$^+$, m/z): 651.2; 4-[(1S,4S)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1λ$^4$-thiomorpholin-1-one, MS (ES$^+$, m/z): 651.2.

Example C55: Preparation of Compounds 366A, 367A, 368A, and 369A

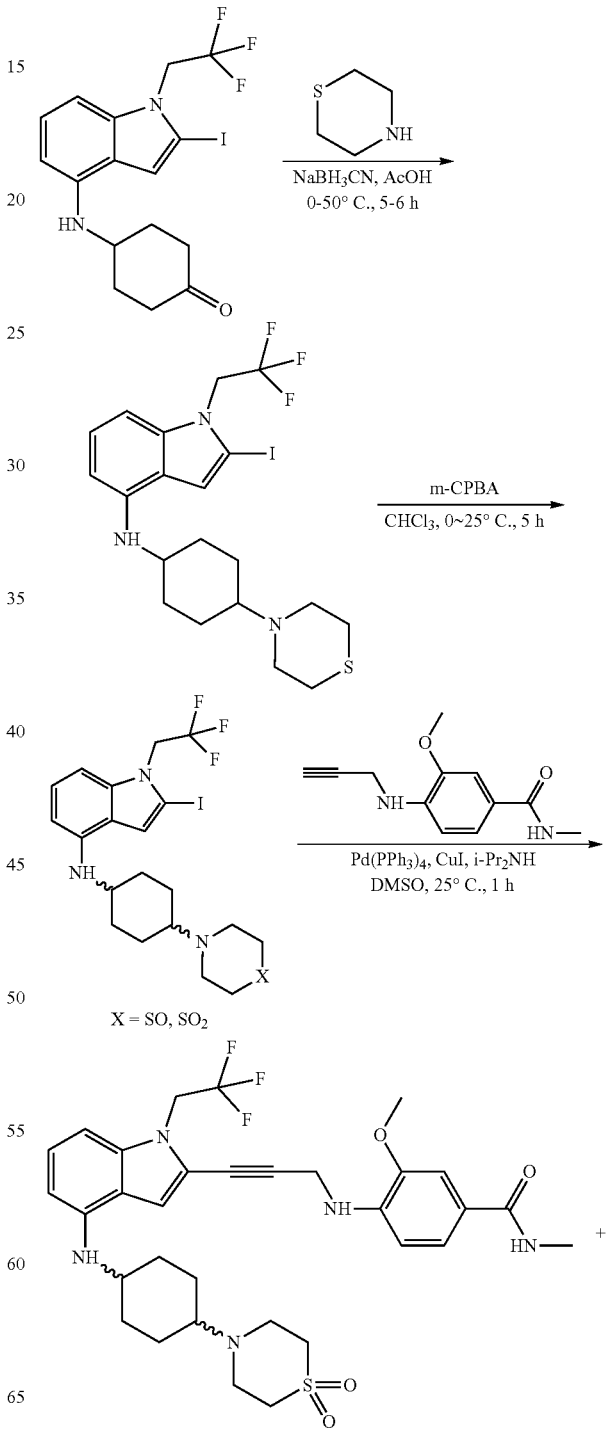

673

-continued

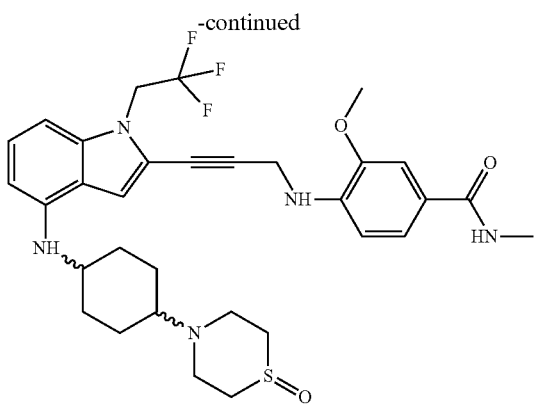

Compounds 366A, 367A, 368A, and 369A were prepared via a procedure analogous to EXAMPLE C54, using 3-methoxy-N-methyl-4-(prop-2-yn-1-ylamino)benzamide in place of 2-methoxy-4-(methylsulfonyl)-N-(prop-2-yn-1-yl)aniline.

4-((3-(4-(((1S,4S)-4-(1,1-dioxidothiomorpholino)cyclohexyl)amino)-1-(2,2,2-trifluoroethyl)-1H-indol-2-yl)prop-2-yn-1-yl)amino)-3-methoxy-N-methylbenzamide, MS (ES$^+$, m/z): 646.2; 3-methoxy-N-methyl-4-{[3-(4-{[(1R,4R)-4-(1-oxo-1λ$^4$-thiomorpholin-4-yl)cyclohexyl]amino}-1-(2,2,2-trifluoroethyl)-1H-indol-2-yl)prop-2-yn-1-yl]amino}benzamide, MS (ES$^+$, m/z): 630.6; and 3-methoxy-N-methyl-4-{[3-(4-{[(1S,4S)-4-(1-oxo-1λ$^4$-thiomorpholin-4-yl)cyclohexyl]amino}-1-(2,2,2-trifluoroethyl)-1H-indol-2-yl)prop-2-yn-1-yl]amino}benzamide, MS (ES$^+$, m/z): 630.2.

Example C56: Preparation of Compounds 370A, 371A, 372A, and 373A

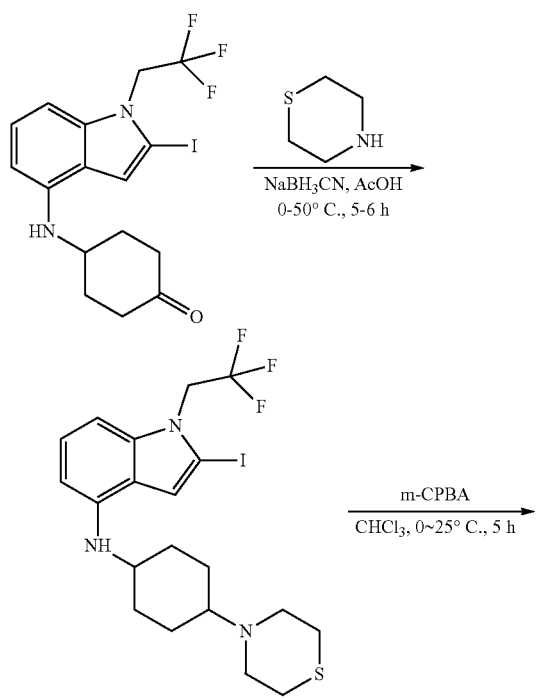

674

-continued

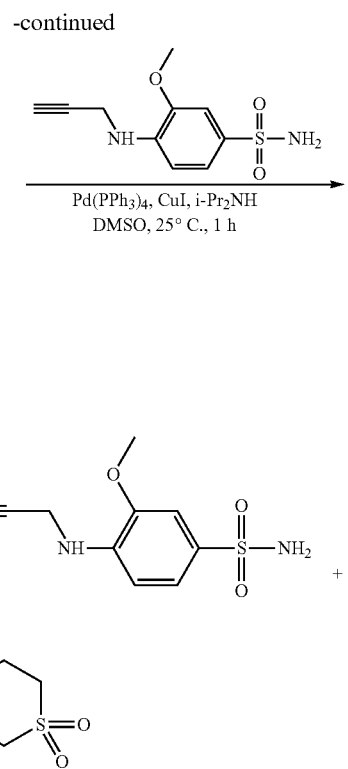

X = SO, SO$_2$

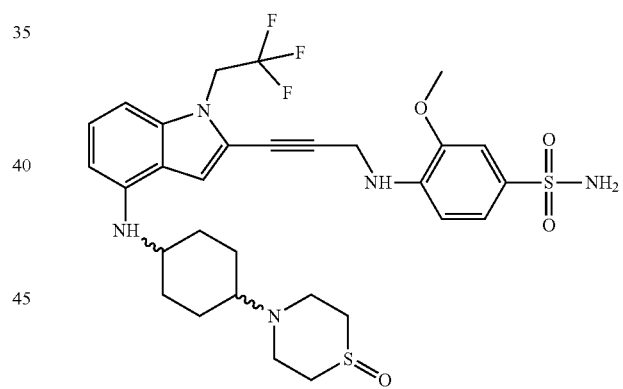

Compounds 370A, 371A, 372A, and 373A were prepared via a procedure analogous to EXAMPLE C54, using 3-methoxy-4-(prop-2-yn-1-ylamino)benzenesulfonamide in place of 2-methoxy-4-(methylsulfonyl)-N-(prop-2-yn-1-yl)aniline.

3-methoxy-4-{[3-(4-{[(1S,4S)-4-(1,1-dioxo-1,-thiomorpholin-4-yl)cyclohexyl]amino}-1-(2,2,2-trifluoroethyl)-1H-indol-2-yl)prop-2-yn-1-yl]amino}benzene-1-sulfonamide, MS (ES$^+$, m/z): 668.1; 3-methoxy-4-{[3-(4-{[(1R,4R)-4-(1-oxo-1λ$^4$-thiomorpholin-4-yl)cyclohexyl]amino}-1-(2,2,2-trifluoroethyl)-1H-indol-2-yl)prop-2-yn-1-yl]amino}benzene-1-sulfonamide, MS (ES$^+$, m/z): 652.2; and 3-methoxy-4-{[3-(4-{[(1S,4S)-4-(1-oxo-1λ$^4$-thiomorpholin-4-yl)cyclohexyl]amino}-1-(2,2,2-trifluoroethyl)-1H-indol-2-yl)prop-2-yn-1-yl]amino}benzene-1-sulfonamide, MS (ES$^+$, m/z): 652.1.

Example C57: General Procedure for Preparation of Compounds 348A, 349A, 414A, and 415A

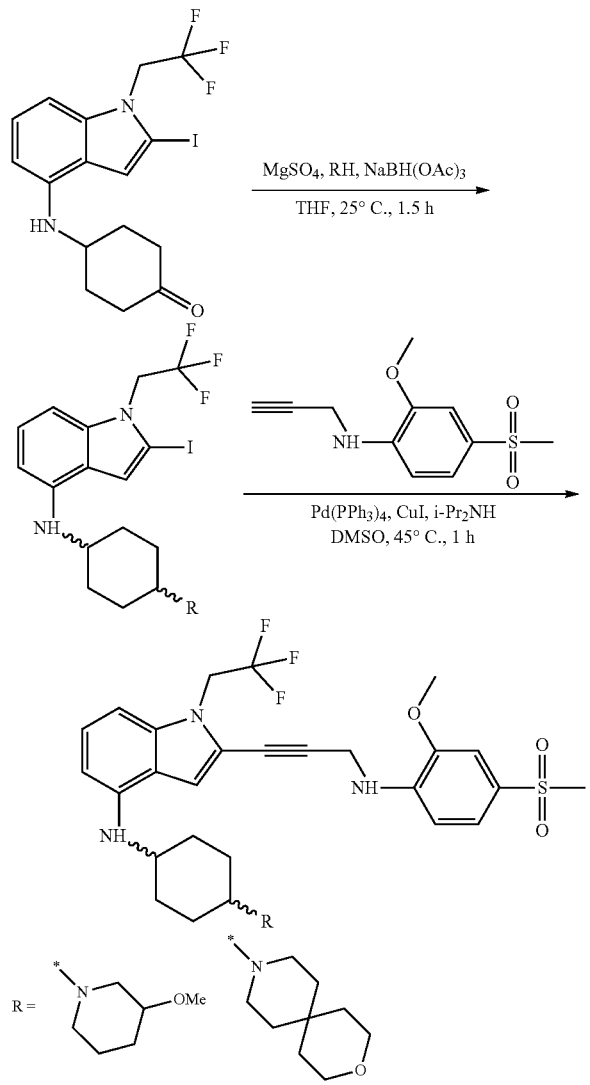

Step 1: To a solution of 4-((2-iodo-1-(2,2,2-trifluoroethyl)-1H-indol-4-yl)amino)cyclohexan-1-one (1 eq.) and amine RH (2 eq.) in THF (2 mL) was added MgSO$_4$ (5 eq.). The mixture was stirred at 25° C. for 0.5 h, and NaBH(OAc)$_3$ (2 eq.) was added. The mixture was stirred at 25° C. for 1 h, after which time TLC/LC-MS analysis indicated that the starting material was completely consumed. The reaction mixture was diluted with water (10 mL) and extracted with EtOAc (2 mL×2). The combined organic layers were washed with brine (10 mL), dried over anhydrous sodium sulfate, filtered, and concentrated under reduced pressure. The residue was purified by column chromatography (SiO$_2$, PE:EtOAc=3:1 to DCM:MeOH=10:1) to afford 2-iodo-N-[4-(3-methoxy-1-piperidyl)cyclohexyl]-1-(2,2,2-trifluoroethyl)indol-4-amine (600 mg, crude) was obtained as yellow solid.

Step 2: The above specified R-substituted iodoindoles were coupled to 2-methoxy-4-(methylsulfonyl)-N-(prop-2-yn-1-yl)aniline according to the general procedure specified in EXAMPLE C51. In each case, TLC/LC-MS analysis indicated that the starting material was completely consumed after heating at 45° C. for 1 h.

2-{3-[(4-methanesulfonyl-2-methoxyphenyl)amino]prop-1-yn-1-yl}-N-[(1R,4R)-4-(3-methoxypiperidin-1-yl)cyclohexyl]-1-(2,2,2-trifluoroethyl)-1H-indol-4-amine, MS (ES$^+$, m/z): 647.2; 2-{3-[(4-methanesulfonyl-2-methoxyphenyl)amino]prop-1-yn-1-yl}-N-[(1S,4S)-4-(3-methoxypiperidin-1-yl)cyclohexyl]-1-(2,2,2-trifluoroethyl)-1H-indol-4-amine, MS (ES$^+$, m/z): 647.2; 2-{3-[(4-methanesulfonyl-2-methoxyphenyl)amino]prop-1-yn-1-yl}-N-[(1R,4R)-4-{3-oxa-9-azaspiro[5.5]undecan-9-yl}cyclohexyl]-1-(2,2,2-trifluoroethyl)-1H-indol-4-amine, MS (ES$^+$, m/z): 687.3; and 2-{3-[(4-methanesulfonyl-2-methoxyphenyl)amino]prop-1-yn-1-yl}-N-[(1S,4S)-4-{3-oxa-9-azaspiro[5.5]undecan-9-yl}cyclohexyl]-1-(2,2,2-trifluoroethyl)-1H-indol-4-amine, MS (ES$^+$, m/z): 687.3.

Example C58: General Procedure for Preparation of Compounds 356A, 357A, 416A, and 417A

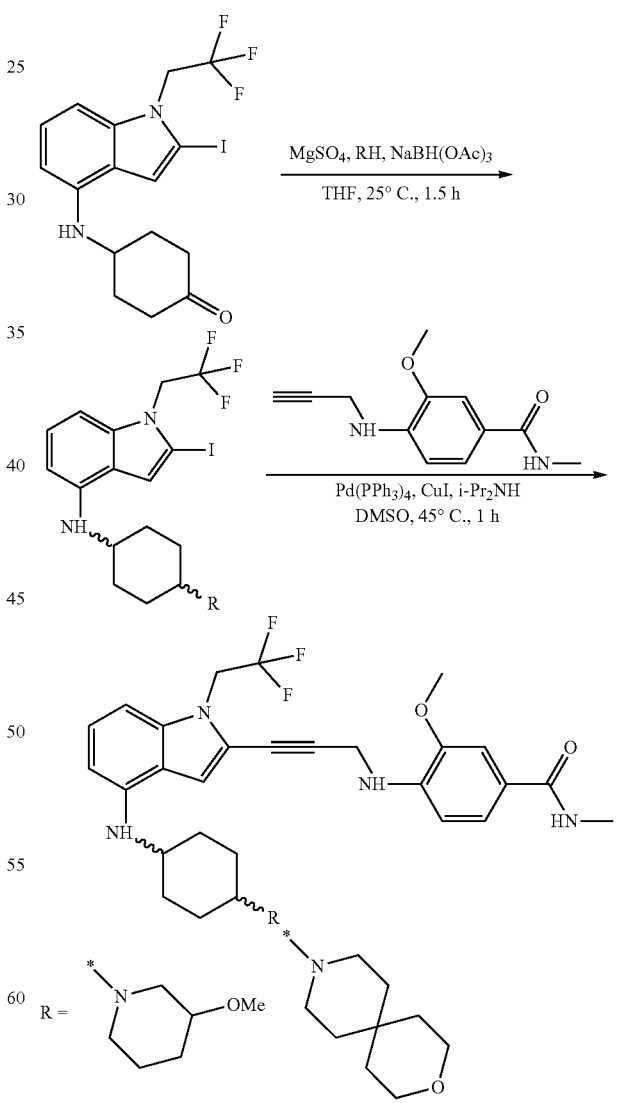

Compounds 356A, 357A, 416A, and 417A were prepared via a procedure analogous to EXAMPLE C51, using 3-methoxy-N-methyl-4-(prop-2-yn-1-ylamino)benzamide in place of 2-methoxy-4-(methylsulfonyl)-N-(prop-2-yn-1-yl)aniline.

3-methoxy-N-methyl-4-{[3-(4-{[(1R,4R)-4-(3-methoxypiperidin-1-yl)cyclohexyl]amino}-1-(2,2,2-trifluoroethyl)-1H-indol-2-yl)prop-2-yn-1-yl]amino}benzamide, MS (ES+, m/z): 626.3; 3-methoxy-N-methyl-4-{[3-(4-{[(1S,4S)-4-(3-methoxypiperidin-1-yl)cyclohexyl]amino}-1-(2,2,2-trifluoroethyl)-1H-indol-2-yl)prop-2-yn-1-yl]amino}benzamide, MS (ES+, m/z): 626.3; 3-methoxy-N-methyl-4-{[3-(4-{[(1R,4R)-4-{3-oxa-9-azaspiro[5.5]undecan-9-yl}cyclohexyl]amino}-1-(2,2,2-trifluoroethyl)-1H-indol-2-yl)prop-2-yn-1-yl]amino}benzamide, MS (ES+, m/z): 666.4; and 3-methoxy-N-methyl-4-{[3-(4-{[(1S,4S)-4-{3-oxa-9-azaspiro[5.5]undecan-9-yl}cyclohexyl]amino}-1-(2,2,2-trifluoroethyl)-1H-indol-2-yl)prop-2-yn-1-yl]amino}benzamide, MS (ES+, m/z): 666.3.

Example C59: General Procedure for Preparation of Compounds 358A, 359A, 418A, and 419A 3-methoxy-4-(prop-2-yn-1-ylamino)benzenesulfonamide in place of 2-methoxy-4-(methylsulfonyl)-N-(prop-2-yn-1-yl)aniline.

3-methoxy-4-{[3-(4-{[(1R,4R)-4-(3-methoxypiperidin-1-yl)cyclohexyl]amino}-1-(2,2,2-trifluoroethyl)-1H-indol-2-yl)prop-2-yn-1-yl]amino}benzene-1-sulfonamide, MS (ES+, m/z): 648.3; 3-methoxy-4-{[3-(4-{[(1S,4S)-4-(3-methoxypiperidin-1-yl)cyclohexyl]amino}-1-(2,2,2-trifluoroethyl)-1H-indol-2-yl)prop-2-yn-1-yl]amino}benzene-1-sulfonamide, MS (ES+, m/z): 648.3; 3-methoxy-4-{[3-(4-{[(1R,4R)-4-{3-oxa-9-azaspiro[5.5]undecan-9-yl}cyclohexyl]amino}-1-(2,2,2-trifluoroethyl)-1H-indol-2-yl)prop-2-yn-1-yl]amino}benzene-1-sulfonamide, MS (ES+, m/z): 688.3; and 3-methoxy-4-{[3-(4-{[(1S,4S)-4-{3-oxa-9-azaspiro[5.5]undecan-9-yl}cyclohexyl]amino}-1-(2,2,2-trifluoroethyl)-1H-indol-2-yl)prop-2-yn-1-yl]amino}benzene-1-sulfonamide, MS (ES+, m/z): 688.3.

Example: General Procedure for Preparation of Compounds 188A, 189A, 336A, 337A, 383A, 384A, 432A, 433A, 451A, and 452A

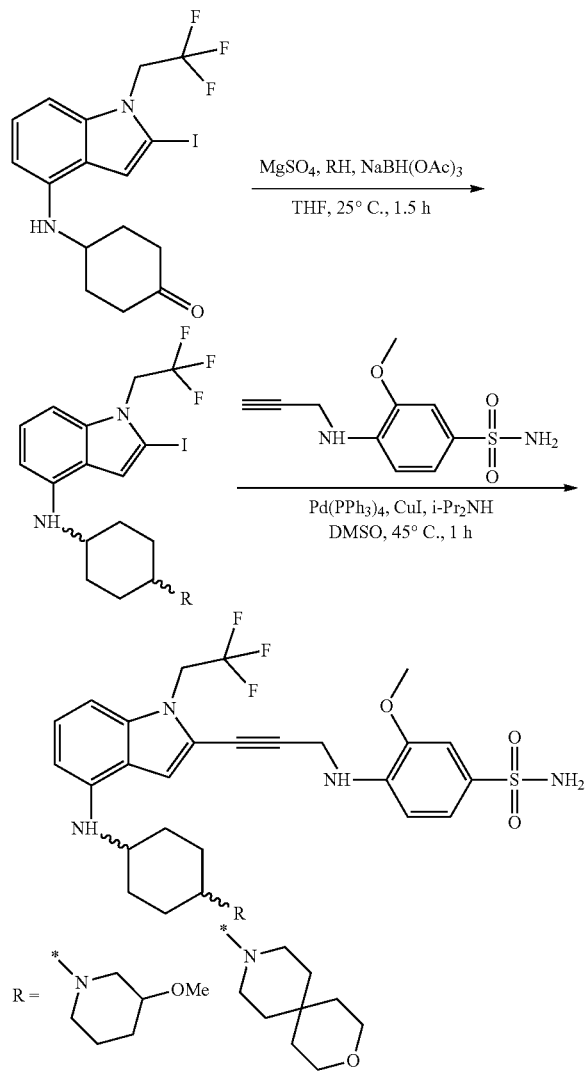

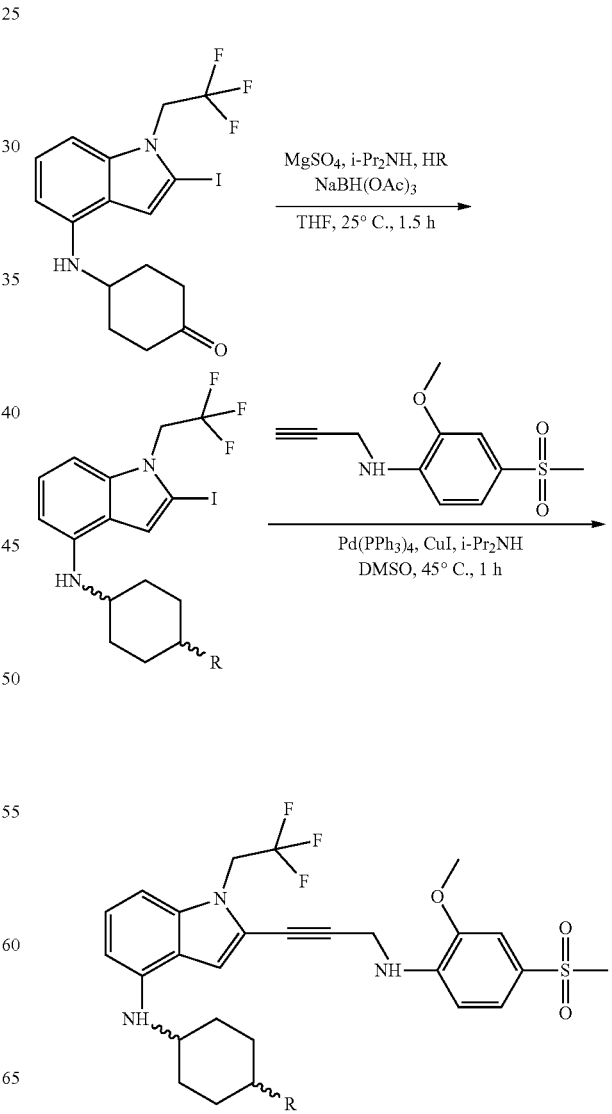

Compounds 358A, 359A, 418A, and 419A were prepared via a procedure analogous to EXAMPLE C51, using

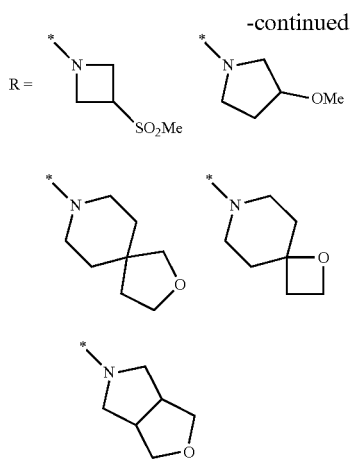

Representative Procedure:

Step 1: To a solution of 4-[[2-iodo-1-(2,2,2-trifluoroethyl)indol-4-yl]amino]cyclohexanone (600 mg, 1.31 mmol, 1 eq.) and 3-methoxypiperidine (301 mg, 2.61 mmol, 2 eq.) in THF (5 mL) was added MgSO$_4$ (786.4 mg, 6.53 mmol, 5 eq.). The mixture was stirred at 25° C. for 0.5 h. NaBH(OAc)$_3$ (553.9 mg, 2.61 mmol, 2 eq.) was added into the mixture and the mixture was stirred at 25° C. for 1 h. TLC analysis (DCM:MeOH=10:1) indicated that the ketone was completely consumed, and two major new spots with polarity greater than that of the starting material were detected. The reaction mixture was diluted with water (10 mL) and extracted with EtOAc (10 mL×2). The combined organic layers were washed with brine (10 mL), dried over anhydrous sodium sulfate, filtered, and concentrated under reduced pressure to give a residue. The residue was purified by column chromatography (SiO$_2$, PE:EtOAc=3:1 to DCM:MeOH=10:1) to afford 2-iodo-N-[4-(3-methoxy-1-piperidyl)cyclohexyl]-1-(2,2,2-trifluoroethyl)indol-4-amine (600 mg, crude) as yellow solid.

Step 2: The above specified R-substituted iodoindoles were coupled to 2-methoxy-4-(methylsulfonyl)-N-(prop-2-yn-1-yl)aniline according to the general procedure specified in EXAMPLE C51. In each case, TLC/LC-MS analysis indicated that the starting material was completely consumed after heating at 45° C. for 1 h.

2-{3-[(4-methanesulfonyl-2-methoxyphenyl)amino]prop-1-yn-1-yl}-N-[(1R,4R)-4-(3-methanesulfonylazetidin-1-yl)cyclohexyl]-1-(2,2,2-trifluoroethyl)-1H-indol-4-amine, MS (ES$^+$, m/z): 667.2; 2-{3-[(4-methanesulfonyl-2-methoxyphenyl)amino]prop-1-yn-1-yl}-N-[(1S,4S)-4-(3-methanesulfonylazetidin-1-yl)cyclohexyl]-1-(2,2,2-trifluoroethyl)-1H-indol-4-amine, MS (ES$^+$, m/z): 667.2; 2-(3-((2-methoxy-4-(methyl-(methylene)sulfinyl)phenyl)amino)prop-1-yn-1-yl)-N-((1R,4R)-4-(3-methoxypyrrolidin-1-yl)cyclohexyl)-1-(2,2,2-trifluoroethyl)-1H-indol-4-amine, MS (ES$^+$, m/z): 633.2; 2-(3-((2-methoxy-4-(methyl-(methylene)sulfinyl)phenyl)amino)prop-1-yn-1-yl)-N-((1S,4S)-4-(3-methoxypyrrolidin-1-yl)cyclohexyl)-1-(2,2,2-trifluoroethyl)-1H-indol-4-amine, MS (ES$^+$, m/z): 633.2; N-((1R,4R)-4-(2-oxa-8-azaspiro[4.5]decan-8-yl)cyclohexyl)-2-(3-((2-methoxy-4-(methylsulfonyl)phenyl)amino)prop-1-yn-1-yl)-1-(2,2,2-trifluoroethyl)-1H-benzo[d]imidazol-4-amine, MS (ES$^+$, m/z): 673.3; N-((1S,4S)-4-(2-oxa-8-azaspiro[4.5]decan-8-yl)cyclohexyl)-2-(3-((2-methoxy-4-(methylsulfonyl)phenyl)amino)prop-1-yn-1-yl)-1-(2,2,2-trifluoroethyl)-1H-benzo[d]imidazol-4-amine, MS (ES$^+$, m/z): 673.3; 2-{3-[(4-methanesulfonyl-2-methoxyphenyl)amino]prop-1-yn-1-yl}-N-[(1R,4R)-4-{1-oxa-7-azaspiro[3.5]nonan-7-yl}cyclohexyl]-1-(2,2,2-trifluoroethyl)-1H-indol-4-amine, MS (ES$^+$, m/z): 659.3; 2-{3-[(4-methanesulfonyl-2-methoxyphenyl)amino]prop-1-yn-1-yl}-N-[(1S,4S)-4-{1-oxa-7-azaspiro[3.5]nonan-7-yl}cyclohexyl]-1-(2,2,2-trifluoroethyl)-1H-indol-4-amine, MS (ES$^+$, m/z): 659.3; 2-{3-[(4-methanesulfonyl-2-methoxyphenyl)amino]prop-1-yn-1-yl}-N-[(1R,4R)-4-{hexahydro-1H-furo[3,4-c]pyrrol-5-yl}cyclohexyl]-1-(2,2,2-trifluoroethyl)-1H-indol-4-amine, MS (ES$^+$, m/z): 645.2; and 2-{3-[(4-methanesulfonyl-2-methoxyphenyl)amino]prop-1-yn-1-yl}-N-[(1S,4S)-4-{hexahydro-1H-furo[3,4-c]pyrrol-5-yl}cyclohexyl]-1-(2,2,2-trifluoroethyl)-1H-indol-4-amine, MS (ES$^+$, m/z): 645.2.

Example C60: General Procedure for Preparation of Compounds 192A, 193A, 385A, 386A, 428A, 429A, 434A, 435A, 453A, and 454A

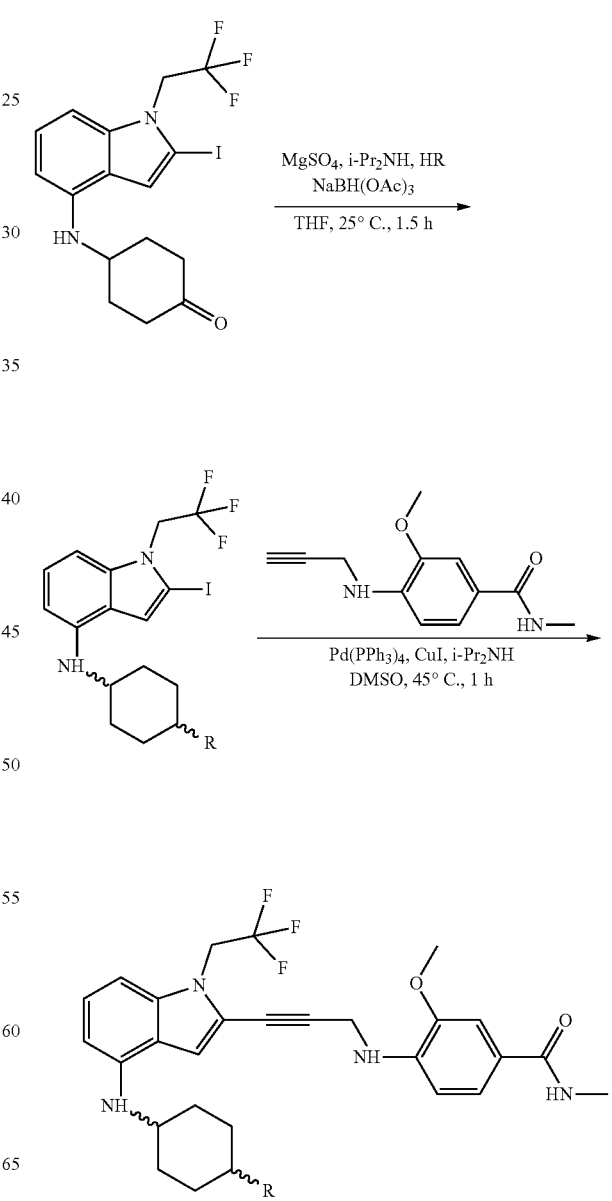

R = 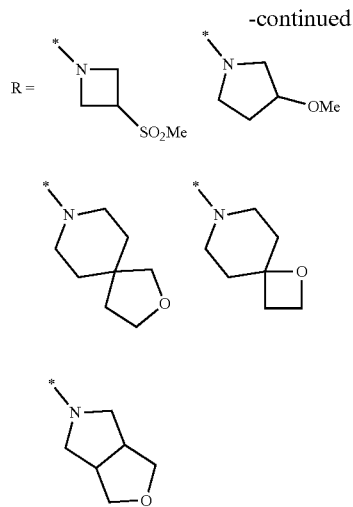

Compounds 192A, 193A, 385A, 386A, 428A, 429A, 434A, 435A, 453A, and 454A were prepared via a procedure analogous to the synthesis of the compounds described by EXAMPLE C51, using 3-methoxy-N-methyl-4-(prop-2-yn-1-ylamino)benzamide in place of 2-methoxy-4-(methylsulfonyl)-N-(prop-2-yn-1-yl)aniline.

3-methoxy-N-methyl-4-{[3-(4-{[(1R,4R)-4-(3-methanesulfonylazetidin-1-yl)cyclohexyl]amino}-1-(2,2,2-trifluoroethyl)-1H-indol-2-yl)prop-2-yn-1-yl]amino}benzamide, MS (ES+, m/z): 646.2; 3-methoxy-N-methyl-4-{[3-(4-{[(1S,4S)-4-(3-methanesulfonylazetidin-1-yl)cyclohexyl]amino}-1-(2,2,2-trifluoroethyl)-1H-indol-2-yl)prop-2-yn-1-yl]amino}benzamide, MS (ES+, m/z): 646.2; 3-methoxy-N-methyl-4-{[3-(4-{[(1R,4R)-4-(3-methoxypyrrolidin-1-yl)cyclohexyl]amino}-1-(2,2,2-trifluoroethyl)-1H-indol-2-yl)prop-2-yn-1-yl]amino}benzamide, MS (ES+, m/z): 612.3; 3-methoxy-N-methyl-4-{[3-(4-{[(1S,4S)-4-(3-methoxypyrrolidin-1-yl)cyclohexyl]amino}-1-(2,2,2-trifluoroethyl)-1H-indol-2-yl)prop-2-yn-1-yl]amino}benzamide, MS (ES+, m/z): 612.3; 4-((3-(4-(((1R,4R)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxy-N-methylbenzamide, MS (ES+, m/z): 652.3; 4-((3-(4-(((1S,4S)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxy-N-methylbenzamide, MS (ES+, m/z): 652.3; 3-methoxy-N-methyl-4-{[3-(4-{[(1R,4R)-4-{1-oxa-7-azaspiro[3.5]nonan-7-yl}cyclohexyl]amino}-1-(2,2,2-trifluoroethyl)-1H-indol-2-yl)prop-2-yn-1-yl]amino}benzamide, MS (ES+, m/z): 638.3; 3-methoxy-N-methyl-4-{[3-(4-{[(1S,4S)-4-{1-oxa-7-azaspiro[3.5]nonan-7-yl}cyclohexyl]amino}-1-(2,2,2-trifluoroethyl)-1H-indol-2-yl)prop-2-yn-1-yl]amino}benzamide, MS (ES+, m/z): 638.3; 3-methoxy-N-methyl-4-{[3-(4-{[(1R,4R)-4-{hexahydro-1H-furo[3,4-c]pyrrol-5-yl}cyclohexyl]amino}-1-(2,2,2-trifluoroethyl)-1H-indol-2-yl)prop-2-yn-1-yl]amino}benzamide, MS (ES+, m/z): 624.3; and 3-methoxy-N-methyl-4-{[3-(4-{[(1S,4S)-4-{hexahydro-1H-furo[3,4-c]pyrrol-5-yl}cyclohexyl]amino}-1-(2,2,2-trifluoroethyl)-1H-indol-2-yl)prop-2-yn-1-yl]amino}benzamide, MS (ES+, m/z): 624.3.

Example C61: General Procedure for Preparation of Compounds 190A, 191A, 338A, 339A, 387A, 388A, 412A, 413A, 430A, and 431A Compounds 190A, 191A, 338A, 339A, 387A, 388A, 412A, 413A, 430A, and 431A were prepared via a procedure analogous to EXAMPLE C51, using 3-methoxy-4-(prop-2-yn-1-ylamino)benzenesulfonamide in place of 2-methoxy-4-(methylsulfonyl)-N-(prop-2-yn-1-yl)aniline.

3-methoxy-4-{[3-(4-{[(1R,4R)-4-(3-methanesulfonylazetidin-1-yl)cyclohexyl]amino}-1-(2,2,2-trifluoroethyl)-1H-indol-2-yl)prop-2-yn-1-yl]amino}benzene-1-sulfonamide, MS (ES+, m/z): 668.2; 3-methoxy-4-{[3-(4-{[(1S,4S)-4-(3-methanesulfonylazetidin-1-yl)cyclohexyl]amino}-1-(2,2,2-trifluoroethyl)-1H-indol-2-yl)prop-2-yn-1-yl]amino}benzene-1-sulfonamide, MS (ES+, m/z): 668.2; 3-methoxy-4-((3-(4-(((1R,4R)-4-(3-methoxypyrrolidin-1-yl)cyclohexyl)amino)-1-(2,2,2-trifluoroethyl)-1H-indol-2-yl)prop-2-yn-1-yl)amino)benzenesulfonamide, MS (ES+, m/z): 634.3; 3-methoxy-4-((3-(4-(((1S,4S)-4-(3-methoxypyrrolidin-1-yl)cyclohexyl)amino)-1-(2,2,2-trifluoroethyl)-1H-indol-2-yl)prop-2-yn-1-yl)amino)benzenesulfonamide, MS (ES+, m/z): 634.3; 4-((3-(4-(((1R,4R)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxybenzenesulfonamide, MS (ES+, m/z): 674.3; 4-((3-(4-(((1S,4S)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxybenzenesulfonamide, MS (ES+, m/z): 674.3; 3-methoxy-4-{[3-(4-{[(1R,4R)-4-{1-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide, MS (ES+, m/z): 660.3; 3-methoxy-4-{[3-(4-{[(1S,4S)-4-{1-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide, MS (ES+, m/z): 660.3; 3-methoxy-4-{[3-(4-{[(1R,4R)-4-{hexahydro-1H-furo[3,4-c]pyrrol-5-yl}cyclohexyl]amino}-1-(2,2,2-trifluoroethyl)-1H-indol-2-yl)prop-2-yn-1-yl]amino}benzene-1-sulfonamide, MS (ES+, m/z): 646.3; and 3-methoxy-4-{[3-(4-{[(1S,4S)-4-{hexahydro-1H-furo[3,4-c]pyrrol-5-yl}cyclohexyl]amino}-1-(2,2,2-trifluoroethyl)-1H-indol-2-yl)prop-2-yn-1-yl]amino}benzene-1-sulfonamide, MS (ES+, m/z): 646.3.

Example C62: General Procedure for Preparation of Compounds 206A, 207A, 208A, 209A, 606A, 607A, 624A, 627A, 628A, 761A, and 760A

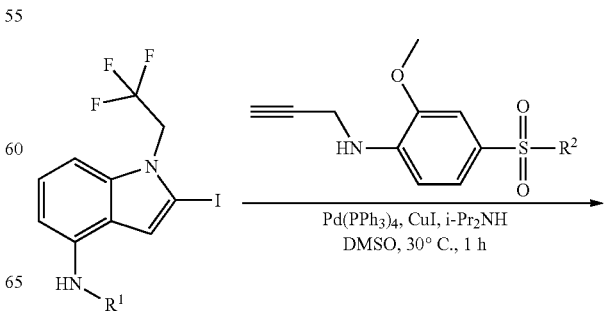

-continued

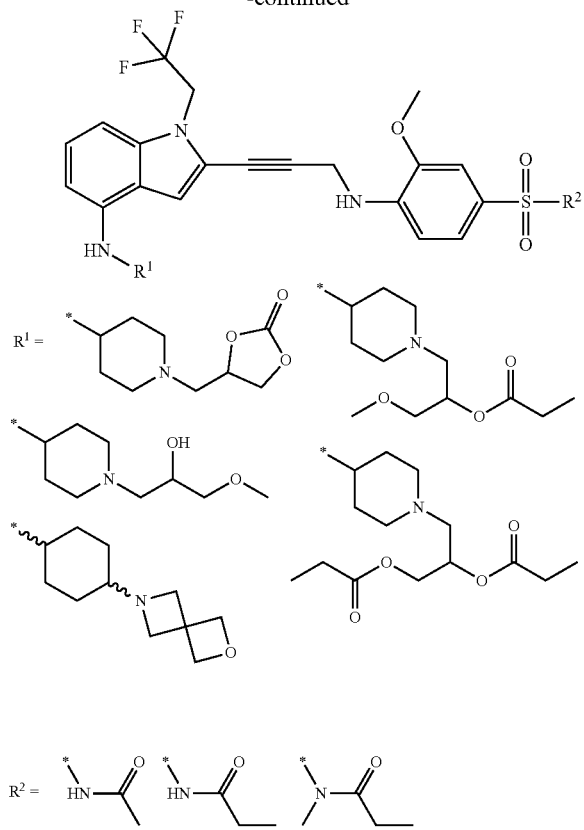

The R² -substituted alkynes were coupled to the R¹ -substituted iodoindoles specified above according to the general procedure specified in EXAMPLE C51. In each case, the reactions were deemed complete after stirring for 1 h at 30° C.

N-[3-methoxy-4-({3-[4-({1-[(2-oxo-1,3-dioxolan-4-yl) methyl]piperidin-4-yl}amino)-1-(2,2,2-trifluoroethyl)-1H-indol-2-yl]prop-2-yn-1-yl}amino)benzenesulfonyl]acetamide, MS (ES⁺, m/z): 678.2. N-((3-methoxy-4-((3-(4-((1-((2-oxo-1,3-dioxolan-4-yl)methyl)piperidin-4-yl)amino)-1-(2,2,2-trifluoroethyl)-1H-indol-2-yl)prop-2-yn-1-yl)amino) phenyl)sulfonyl)propionamide, MS (ES⁺, m/z): 692.2; N-(4-{[3-(4-{[1-(2-hydroxy-3-methoxypropyl)piperidin-4-yl] amino}-1-(2,2,2-trifluoroethyl)-1H-indol-2-yl)prop-2-yn-1-yl]amino}-3-methoxybenzenesulfonyl)-N-methylpropanamide, MS (ES⁺, m/z): 694.3; N-(3-methoxy-4-{[3-(4-{[(1R,4R)-4-{2-oxa-6-azaspiro[3.3]heptan-6-yl}cyclohexyl] amino}-1-(2,2,2-trifluoroethyl)-1H-indol-2-yl)prop-2-yn-1-yl]amino}benzenesulfonyl)acetamide, MS (ES⁺, m/z): 674.3; N-(3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)acetamide, MS (ES⁺, m/z): 674.3; N-(3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)propanamide, MS (ES⁺, m/z): 688.4; and N-(3-methoxy-4-{[3-(4-{[(1S,4S)-4-{2-oxa-6-azaspiro[3.3]heptan-6-yl}cyclohexyl] amino}-1-(2,2,2-trifluoroethyl)-1H-indol-2-yl)prop-2-yn-1-yl]amino}benzenesulfonyl)propanamide, MS (ES⁺, m/z): 688.4; N-(4-{[3-(4-{[1-(2-hydroxy-3-methoxypropyl)piperidin-4-yl]amino}-1-(2,2,2-trifluoroethyl)-1H-indol-2-yl) prop-2-yn-1-yl]amino}-3-methoxybenzenesulfonyl)acetamide, MS (ES⁺, m/z): 666.2; 1-methoxy-3-(4-{[2-(3-{[2-methoxy-4-(propanamidosulfonyl)phenyl]amino}prop-1-yn-1-yl)-1-(2,2,2-trifluoroethyl)-1H-indol-4-yl]amino} piperidin-1-yl)propan-2-yl propanoate, MS (ES⁺, m/z): 736.3; 1-(4-{[2-(3-{[2-methoxy-4-(propanamidosulfonyl) phenyl]amino}prop-1-yn-1-yl)-1-(2,2,2-trifluoroethyl)-1H-indol-4-yl]amino}piperidin-1-yl)-3-(propanoyloxy)propan-2-yl propanoate, MS (ES⁺, m/z): 778.1; and N-(4-{[3-(4-{[1-(2-hydroxy-3-methoxypropyl)piperidin-4-yl]amino}-1-(2,2,2-trifluoroethyl)-1H-indol-2-yl)prop-2-yn-1-yl] amino}-3-methoxybenzenesulfonyl)propanamide, MS (ES⁺, m/z): 680.3.

Example C63: General Procedure for Preparation of Compounds 94A, 100A, 109A, 112A, 115A, 116A, 233A, 245A, 246A, 488A, and 651A

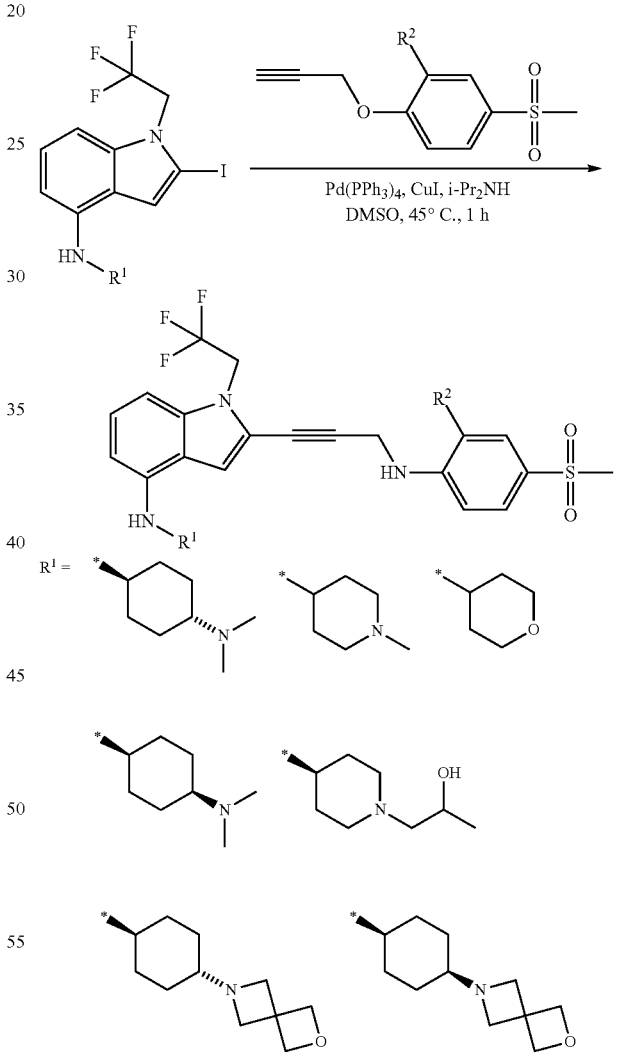

The R¹-substituted iodoindoles specified above were coupled to the R²-substituted alkynes according to the general procedure specified in EXAMPLE C51. In each case, the reactions were deemed complete after stirring for 1 h at 45° C., and the crude compounds were first purified by prep-TLC and further purified by prep-HPLC.

(1R,4R)—$N^4$-{2-[3-(2-amino-4-methanesulfonylphenoxy)prop-1-yn-1-yl]-1-(2,2,2-trifluoroethyl)-1H-indol-4-yl}-$N^1$,$N^1$-dimethylcyclohexane-1,4-diamine, MS (ES$^+$, m/z): 563.2; (1S,4S)—$N^4$-{2-[3-(2-amino-4-methanesulfonylphenoxy)prop-1-yn-1-yl]-1-(2,2,2-trifluoroethyl)-1H-indol-4-yl}-$N^1$,$N^1$-dimethylcyclohexane-1,4-diamine, MS (ES$^+$, m/z): 563.1; N-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]oxy}phenyl)acetamide, MS (ES$^+$, m/z): 605.2; N-(5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]oxy}phenyl)acetamide, MS (ES$^+$, m/z): 605.2; 1-{4-[(2-{3-[4-methanesulfonyl-2-(methylamino)phenoxy]prop-1-yn-1-yl}-1-(2,2,2-trifluoroethyl)-1H-indol-4-yl)amino]piperidin-1-yl}-3-methoxypropan-2-ol, MS (ES$^+$, m/z): 623.4; (1R,4R)—$N^4$-(2-{3-[4-methanesulfonyl-2-(methylamino)phenoxy]prop-1-yn-1-yl}-1-(2,2,2-trifluoroethyl)-1H-indol-4-yl)-$N^1$,$N^1$-dimethylcyclohexane-1,4-diamine, MS (ES$^+$, m/z): 577.3; 2-{3-[4-methanesulfonyl-2-(methylamino)phenoxy]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine, MS (ES$^+$, m/z): 631.2; 2-[3-(2-amino-4-methanesulfonylphenoxy)prop-1-yn-1-yl]-N-[(1R,4R)-4-{2-oxa-6-azaspiro[3.3]heptan-6-yl}cyclohexyl]-1-(2,2,2-trifluoroethyl)-1H-indol-4-amine, MS (ES$^+$, m/z): 617.2; 2-[3-(2-amino-4-methanesulfonylphenoxy)prop-1-yn-1-yl]-N-[(1S,4S)-4-{2-oxa-6-azaspiro[3.3]heptan-6-yl}cyclohexyl]-1-(2,2,2-trifluoroethyl)-1H-indol-4-amine, MS (ES$^+$, m/z): 617.1; (1R,4R)—$N^4$-(2-{3-[2-(dimethylamino)-4-methanesulfonylphenoxy]prop-1-yn-1-yl}-1-(2,2,2-trifluoroethyl)-1H-indol-4-yl)-$N^1$,$N^1$-dimethylcyclohexane-1,4-diamine, MS (ES$^+$, m/z): 591.2; and 2-{3-[2-(dimethylamino)-4-methanesulfonylphenoxy]prop-1-yn-1-yl}-N-(1-methylpiperidin-4-yl)-1-(2,2,2-trifluoroethyl)-1H-indol-4-amine, MS (ES$^+$, m/z): 563.2.

Example C64: General Procedure for Preparation of Compounds 164A, 165A, 166A, 167A, 168A, 169A, 261A, 262A, 299A, 300A, 316A, 317A, 340A, 341A, 342A, 343A, 344A, 345A, 379A, 380A, 381A, 382A, 391A, 392A, 490A, 666A, 667A, and 668A

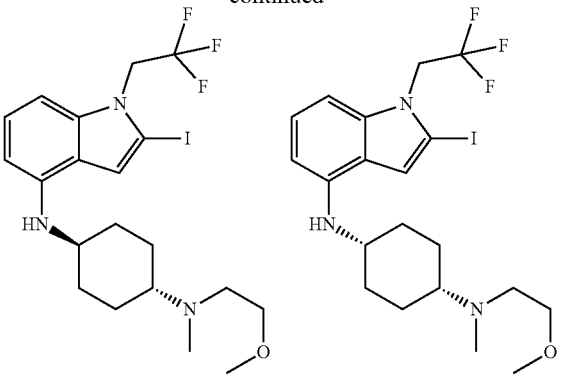

Preparation of (1R,4R)—$N^1$-(2-iodo-1-(2,2,2-trifluoroethyl)-1H-indol-4-yl)-$N^4$-(2-methoxyethyl)-$N^4$-methylcyclohexane-1,4-diamine and (1S,4S)—$N^1$-(2-iodo-1-(2,2,2-trifluoroethyl)-1H-indol-4-yl)-$N^4$-(2-methoxyethyl)-$N^4$-methylcyclohexane-1,4-diamine: A mixture of 4-((2-iodo-1-(2,2,2-trifluoroethyl)-1H-indol-4-yl)amino)cyclohexan-1-one (300 mg, 0.675 mmol, 1 eq.), 2-methoxy-N-methylethanamine (2.70 mmol, 290 µL, 4 eq.), and Ti(OEt)$_4$ (2.70 mmol, 560 µL, 4 eq.) in EtOH (3 mL) was stirred at 50° C. for 11 h. NaBH$_3$CN (84.7 mg, 1.35 mmol, 2 eq.) was then added, and the mixture was stirred for an additional 1 h at 50° C. TLC analysis (PE:EtOAc=3:1, R$_f$=0.01) indicated that the reaction was complete. The reaction mixture was quenched by adding a saturated solution of NaHCO$_3$ (60 mL) at 25° C., diluted with water (20 mL), and extracted with EtOAc (30 mL×3). The combined organic layers were dried over anhydrous sodium sulfate, filtered, and concentrated under reduced pressure. The resulting residue was purified by prep-TLC (PE:EtOAc:TEA=5:5:1, R$_{f1}$=0.24, R$_{f2}$=0.43). (1R,4R)—$N^1$-(2-iodo-1-(2,2,2-trifluoroethyl)-1H-indol-4-yl)-$N^4$-(2-methoxyethyl)-$N^4$-methylcyclohexane-1,4-diamine (90 mg, 159 µmol, 23.6% yield) and (1S,4S)—$N^1$-(2-iodo-1-(2,2,2-trifluoroethyl)-1H-indol-4-yl)-$N^4$-(2-methoxyethyl)-$N^4$-methylcyclohexane-1,4-diamine (130 mg, 231 µmol, 34.2% yield) were obtained as light yellow solids.

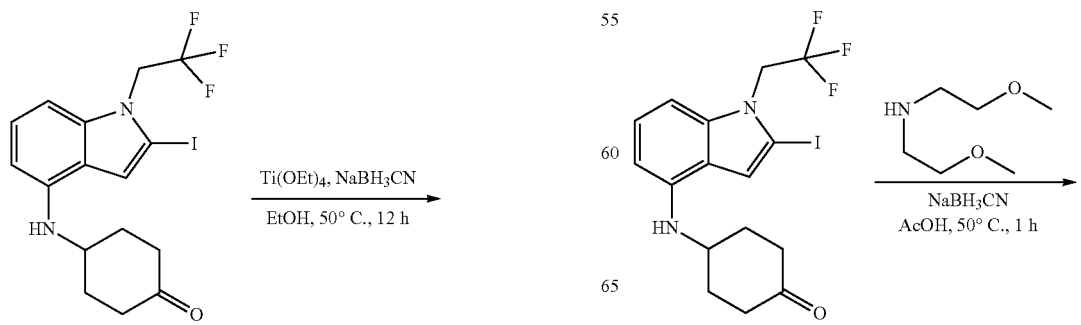

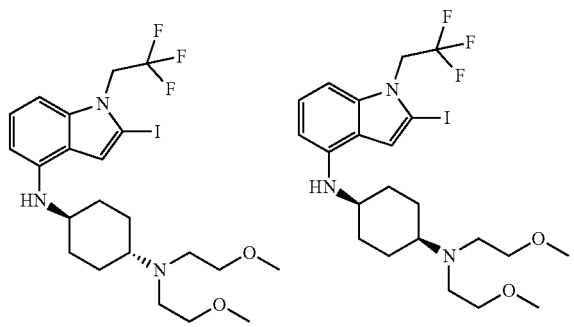

Preparation of (1R,4R)—N$^1$-(2-iodo-1-(2,2,2-trifluoroethyl)-1H-indol-4-yl)-N$^4$,N$^4$-bis(2-methoxyethyl)cyclohexane-1,4-diamine and (1S,4S)—N$^1$-(2-iodo-1-(2,2,2-trifluoroethyl)-1H-indol-4-yl)-N$^4$,N$^4$-bis(2-methoxyethyl)cyclohexane-1,4-diamine: To a mixture of 4-((2-iodo-1-(2,2,2-trifluoroethyl)-1H-indol-4-yl)amino)cyclohexan-1-one (250 mg, 573 μmol, 1 eq.) and AcOH (1.15 mmol, 65.6 μL, 2 eq.) in neat bis(2-methoxyethyl)amine (16.93 mmol, 2.50 mL, 29.5 eq.) was added NaBH$_3$CN (72.0 mg, 1.15 mmol, 2 eq.). The mixture was stirred at 50° C. for 1 h, after which time TLC analysis (PE:EtOAc=3:1, R$_{f1}$=0.18, R$_{f2}$=0.24) indicated that the reaction was complete. The reaction mixture was quenched with water (40 mL) and extracted with EtOAc (20 mL×3). The combined organic layers were dried over anhydrous sodium sulfate, filtered, and concentrated under reduced pressure to provide a residue that was purified by prep-TLC (SiO$_2$, PE:EtOAc=3:1). (1R,4R)—N$^1$-(2-iodo-1-(2,2,2-trifluoroethyl)-1H-indol-4-yl)-N$^4$, N$^4$-bis(2-methoxyethyl)cyclohexane-1,4-diamine (120 mg, 184 μmol, 32.2% yield) and (1S,4S)—N$^1$-(2-iodo-1-(2,2,2-trifluoroethyl)-1H-indol-4-yl)-N$^4$, N$^4$-bis(2-methoxyethyl)cyclohexane-1,4-diamine (110 mg, 179 μmol, 31.2% yield) were obtained as light yellow solids.

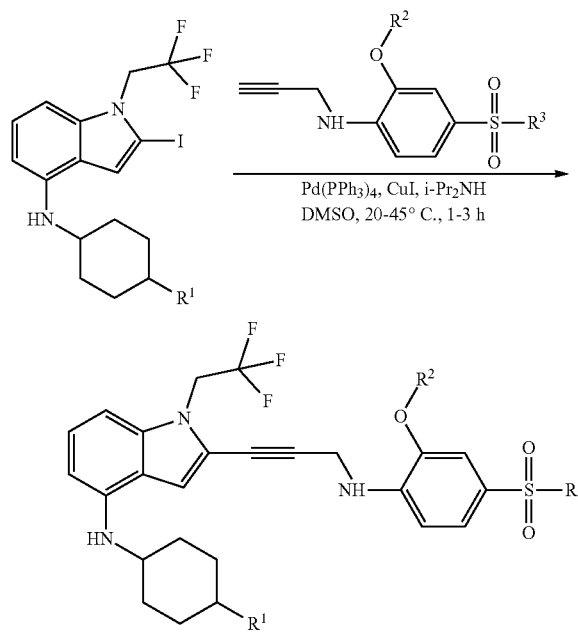

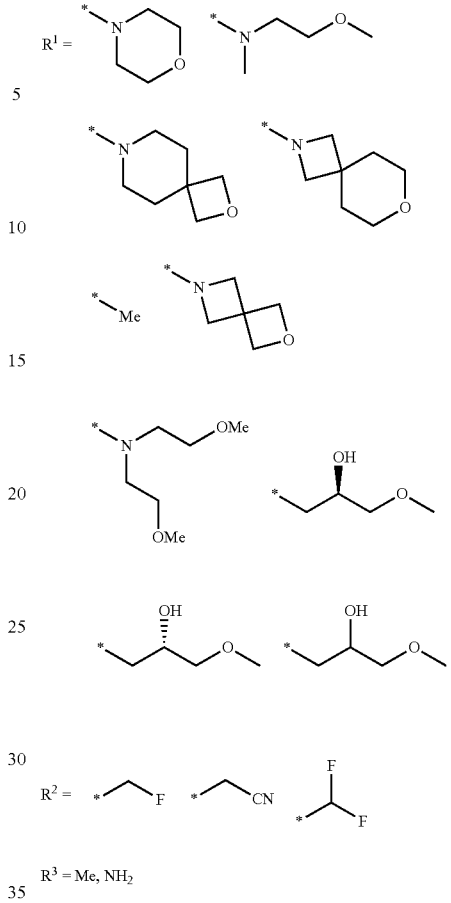

Preparation of final products: To a mixture of R$^2$ and R$^3$ substituted alkyne (1~2 eq.) in DMSO (5 mL) was added i-Pr$_2$NH (10~30 eq.). Then, CuI (1~2 eq.), R$^1$-substituted iodoindole (1 eq.), and Pd(PPh$_3$)$_4$ (0.20~0.50 eq.) were added into the mixture. The mixture was stirred at 20~45° C. for 1~3 h under N$_2$. LC-MS or TLC analysis detected completion of the reaction. The mixture was poured into saturated EDTA solution 30 mL and stirred for 1 h. The aqueous phase was extracted with EtOAc (10 mL×3). The combined organic layers were washed with brine (10 mL×3), dried over anhydrous sodium sulfate, filtered, and concentrated in vacuo. The residue was purified by TLC, prep-HPLC, or TLC and prep-HPLC to afford the desired compound.

3-(cyanomethoxy)-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide, MS (ES$^+$, m/z): 645.2; 3-(cyanomethoxy)-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzene-1-sulfonamide, MS (ES$^+$, m/z): 645.2; 3-(cyanomethoxy)-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide, MS (ES$^+$, m/z): 647.2; 3-(cyanomethoxy)-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide, MS (ES$^+$, m/z): 647.2; 3-(cyanomethoxy)-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide, MS (ES+, m/z): 685.2; 3-(cyanomethoxy)-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide, MS (ES+, m/z): 685.2; 3-(cyanomethoxy)-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide, MS (ES+, m/z): 685.2; 3-(cyanomethoxy)-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide, MS (ES+, m/z): 685.2; 3-(fluoromethoxy)-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide, MS (ES+, m/z): 638.2; 3-(fluoromethoxy)-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzene-1-sulfonamide, MS (ES+, m/z): 3-(fluoromethoxy)-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide, MS (ES+, m/z): 640.2; 3-(fluoromethoxy)-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide, MS (ES+, m/z): 640.2; 3-(fluoromethoxy)-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide, MS (ES+, m/z): 650.2; 3-(fluoromethoxy)-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide, MS (ES+, m/z): 650.2; 3-(fluoromethoxy)-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide, MS (ES+, m/z): 678.2; 3-(fluoromethoxy)-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide, MS (ES+, m/z): 678.2; 3-(fluoromethoxy)-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide, MS (ES+, m/z): 678.2; 3-(fluoromethoxy)-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide, MS (ES+, m/z): 678.2; 3-(fluoromethoxy)-4-{[3-(4-{[(1R,4R)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide, MS (ES+, m/z): 684.2; 3-(fluoromethoxy)-4-{[3-(4-{[(1S,4S)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide, MS (ES+, m/z): 684.2; (2R)-1-(4-{[2-(3-{[2-(fluoromethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol, MS (ES+, m/z): 641.2; (2S)-1-(4-{[2-(3-{[2-(fluoromethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol, MS (ES+, m/z): 641.2; 2-(3-{[2-(fluoromethoxy)-4-methanesulfonylphenyl]amino}prop-1-yn-1-yl)-N-(1-methylpiperidin-4-yl)-1-(2,2,2-trifluoroethyl)-1H-indol-4-amine, MS (ES+, m/z): 641.2; 2-(3-{[2-(fluoromethoxy)-4-methanesulfonylphenyl]amino}prop-1-yn-1-yl)-N-[(1R,4R)-4-{2-oxa-7-azaspiro[3.5]nonan-7-yl}cyclohexyl]-1-(2,2,2-trifluoroethyl)-1H-indol-4-amine, MS (ES+, m/z): 677.3; 2-(3-{[2-(fluoromethoxy)-4-methanesulfonylphenyl]amino}prop-1-yn-1-yl)-N-[(1S,4S)-4-{2-oxa-7-azaspiro[3.5]nonan-7-yl}cyclohexyl]-1-(2,2,2-trifluoroethyl)-1H-indol-4-amine, MS (ES+, m/z): 677.3; 2-(3-{[2-(fluoromethoxy)-4-methanesulfonylphenyl]amino}prop-1-yn-1-yl)-N-[(1R,4R)-4-(morpholin-4-yl)cyclohexyl]-1-(2,2,2-trifluoroethyl)-1H-indol-4-amine, MS (ES+, m/z): 637.2; 2-(3-1{[2-(fluoromethoxy)-4-methanesulfonylphenyl]amino}prop-1-yn-1-yl)-N-[(1S,4S)-4-(morpholin-4-yl)cyclohexyl]-1-(2,2,2-trifluoroethyl)-1H-indol-4-amine, MS (ES+, m/z): 637.2; and 1-(4-{[2-(3-{[2-(difluoromethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol, MS (ES+, m/z): 659.2.

Example C65: General Procedure for Preparation of Compounds 139A, 138A, 287A, 288A, 289A, 290A, 708A, and 713A

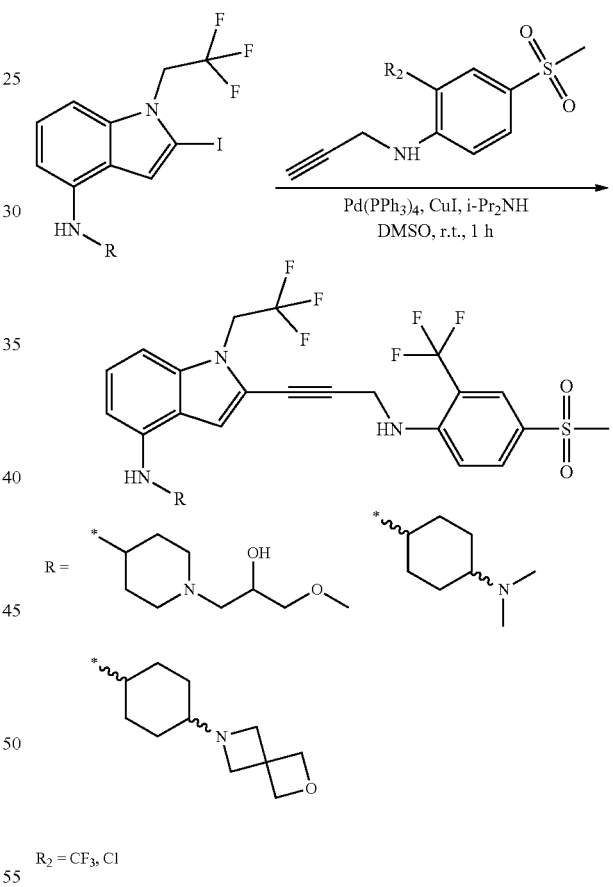

To a mixture of 4-methylsulfonyl-N-prop-2-ynyl-2-(trifluoromethyl)aniline (1-2.5 eq.) or 2-chloro-4-(methylsulfonyl)-N-(prop-2-yn-1-yl)aniline (1-2.5 eq.) in DMSO (2 mL) were added i-PrNH$_2$ (10 eq.), CuI (1 eq.), R-substituted iodoindole (0.1 g, 195.57 μmol, 1 eq), and Pd(PPh$_3$)$_4$ (74.51 mg, 64.48 μmol, 0.3 eq.) in one portion under N$_2$. The mixture was stirred at 25° C. for 60 min, after which time TLC analysis indicated that the reaction was complete. The reaction was diluted with EtOAc (20 mL) and then poured into aqueous 2M EDTA (20 mL) and stirred for 1 h. The mixture was extracted with EtOAc (20 mL×3), and the combined organic layers were washed with water (20 mL×2) and brine (20 mL×2), dried over anhydrous sodium sulfate, filtered, and concentrated. The residue was purified by column chromatography (SiO$_2$, EtOAc:TEA=100:2), and then further purified by prep-HPLC to obtain the desired products as white solids.

1-(4-{[2-(3-{[4-methanesulfonyl-2-(trifluoromethyl)phenyl]amino}prop-1-yn-1-yl)-1-(2,2,2-trifluoroethyl)-1H-indol-4-yl]amino}piperidin-1-yl)-3-methoxypropan-2-ol, MS (ES$^+$, m/z): 661.3; (1R,4R)—N$^4$-[2-(3-{[4-methanesulfonyl-2-(trifluoromethyl)phenyl]amino}prop-1-yn-1-yl)-1-(2,2,2-trifluoroethyl)-1H-indol-4-yl]-N$^1$,N$^1$-dimethylcyclohexane-1,4-diamine, MS (ES$^+$, m/z): 615.3; (1S,4S)—N$^4$-[2-(3-1{[4-methanesulfonyl-2-(trifluoromethyl)phenyl]amino}prop-1-yn-1-yl)-1-(2,2,2-trifluoroethyl)-1H-indol-4-yl]-N$^1$,N$^1$-dimethylcyclohexane-1,4-diamine, MS (ES$^+$, m/z): 615.3; 2-(3-{[4-methanesulfonyl-2-(trifluoromethyl)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine, MS (ES$^+$, m/z): 669.2; 2-(3-{[4-methanesulfonyl-2-(trifluoromethyl)phenyl]amino}prop-1-yn-1-yl)-N-[(1S,4S)-4-{2-oxa-6-azaspiro[3.3]heptan-6-yl}cyclohexyl]-1-(2,2,2-trifluoroethyl)-1H-indol-4-amine, MS (ES$^+$, m/z): 669.2; 1-{4-[(2-{3-[(2-chloro-4-methanesulfonylphenyl)amino]prop-1-yn-1-yl}-1-(2,2,2-trifluoroethyl)-1H-indol-4-yl)amino]piperidin-1-yl}-3-methoxypropan-2-ol, MS (ES$^+$, m/z): 627.4; 2-{3-[(2-chloro-4-methanesulfonylphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine, MS (ES$^+$, m/z): 635.3; and 2-{3-[(2-chloro-4-methanesulfonylphenyl)amino]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine, MS (ES$^+$, m/z): 635.2.

Example C66: General Procedure for Preparation of Compounds 67A, 68A, 480A, 582A, and 1002A

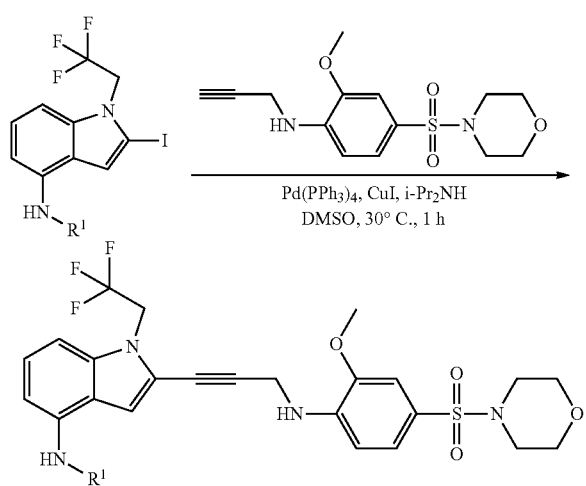

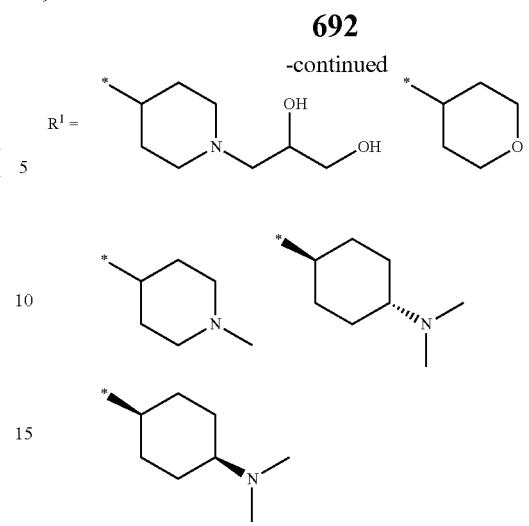

2-Methoxy-4-(morpholinosulfonyl)-N-(prop-2-yn-1-yl) aniline was coupled to the R$^1$-substituted iodoindoles specified above according to the general procedure specified in EXAMPLE C51. In each case, the reactions were deemed complete after stirring for 1 h at 30° C., and the crude compounds were purified by prep-TLC and further purified by prep-HPLC.

3-(4-{[2-(3-{[2-methoxy-4-(morpholine-4-sulfonyl)phenyl]amino}prop-1-yn-1-yl)-1-(2,2,2-trifluoroethyl)-1H-indol-4-yl]amino}piperidin-1-yl)propane-1,2-diol, MS (ES$^+$, m/z): 680.2; 2-(3-{[2-methoxy-4-(morpholine-4-sulfonyl)phenyl]amino}prop-1-yn-1-yl)-N-(oxan-4-yl)-1-(2,2,2-trifluoroethyl)-1H-indol-4-amine, MS (ES$^+$, m/z): 607.2; 2-(3-{[2-methoxy-4-(morpholine-4-sulfonyl)phenyl]amino}prop-1-yn-1-yl)-N-(1-methylpiperidin-4-yl)-1-(2,2,2-trifluoroethyl)-1H-indol-4-amine, MS (ES$^+$, m/z): 620.2; (1R,4R)—N$^4$-[2-(3-{[2-methoxy-4-(morpholine-4-sulfonyl)phenyl]amino}prop-1-yn-1-yl)-1-(2,2,2-trifluoroethyl)-1H-indol-4-yl]-N$^1$,N$^1$-dimethylcyclohexane-1,4-diamine, MS (ES$^+$, m/z): 648.2; and (1S,4S)—N$^4$-[2-(3-{[2-methoxy-4-(morpholine-4-sulfonyl)phenyl]amino}prop-1-yn-1-yl)-1-(2,2,2-trifluoroethyl)-1H-indol-4-yl]-N$^1$,N$^1$-dimethylcyclohexane-1,4-diamine, MS (ES$^+$, m/z): 648.3.

Example C67: General Procedure for Preparation of Compounds 69A, 70A, 483A, 595A, and 1007A

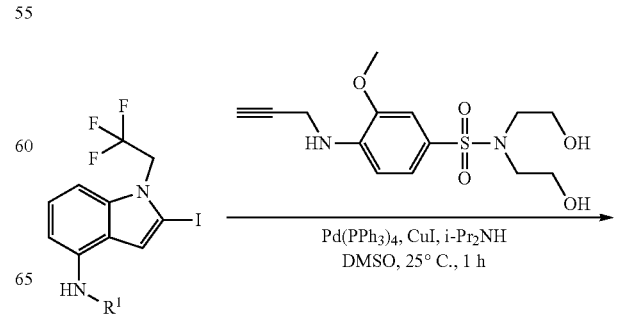

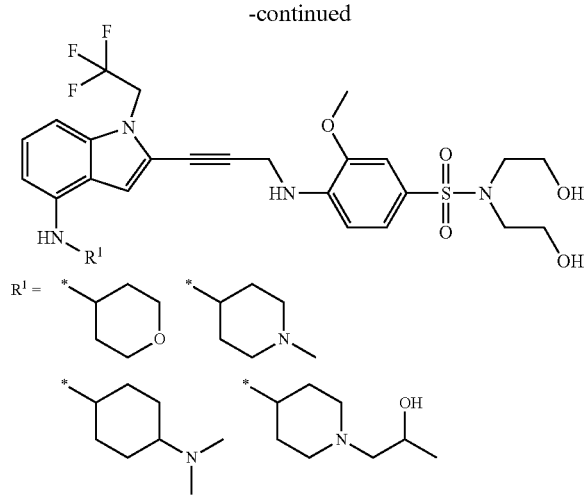

N,N-bis(2-hydroxyethyl)-3-methoxy-4-(prop-2-yn-1-ylamino)benzenesulfonamide was coupled to the $R^1$-substituted iodoindoles specified above according to the general procedure specified in EXAMPLE C51. In each case, the reactions were deemed complete after stirring for 1 h at 30° C., and the crude compounds were first purified by prep-TLC and further purified by prep-HPLC.

N,N-bis(2-hydroxyethyl)-3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide, MS (ES+, m/z): 666.2; N,N-bis(2-hydroxyethyl)-3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide, MS (ES+, m/z): 666.3; N,N-bis(2-hydroxyethyl)-4-{[3-(4-{[1-(2-hydroxypropyl)piperidin-4-yl]amino}-1-(2,2,2-trifluoroethyl)-1H-indol-2-yl)prop-2-yn-1-yl]amino}-3-methoxybenzene-1-sulfonamide, MS (ES+, m/z): 682.2; N,N-bis(2-hydroxyethyl)-3-methoxy-4-[(3-{4-[(oxan-4-yl)amino]-1-(2,2,2-trifluoroethyl)-1H-indol-2-yl}prop-2-yn-1-yl)amino]benzene-1-sulfonamide, MS (ES+, m/z): 625.2; and N,N-bis(2-hydroxyethyl)-3-methoxy-4-[(3-{4-[(1-methylpiperidin-4-yl)amino]-1-(2,2,2-trifluoroethyl)-1H-indol-2-yl}prop-2-yn-1-yl)amino]benzene-1-sulfonamide, MS (ES+, m/z): 638.2.

Example C68: General Procedure for Preparation of Compounds 76A, 485A, 559A, 1048A, and 1011A

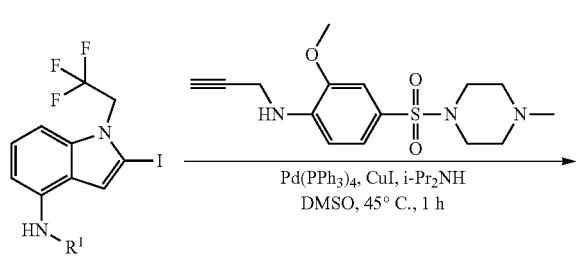

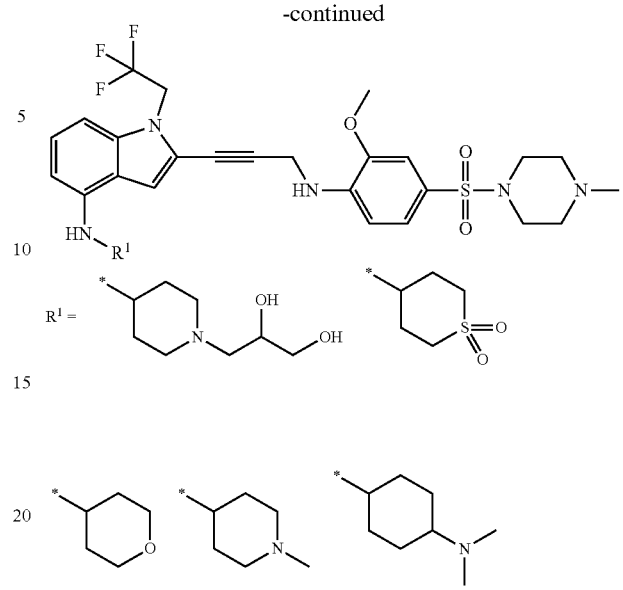

2-methoxy-4-((4-methylpiperazin-1-yl)sulfonyl)-N-(prop-2-yn-1-yl)aniline was coupled to the $R^1$-substituted iodoindoles specified above according to the general procedure specified in EXAMPLE C51. In each case, the reactions were deemed complete after stirring for 1 h at 45° C., and the crude compounds were first purified by prep-TLC and further purified by prep-HPLC.

3-[4-({2-[3-({2-methoxy-4-[(4-methylpiperazin-1-yl)sulfonyl]phenyl}amino)prop-1-yn-1-yl]-1-(2,2,2-trifluoroethyl)-1H-indol-4-yl}amino)piperidin-1-yl]propane-1,2-diol, MS (ES+, m/z): 693.3; 4-({2-[3-({2-methoxy-4-[(4-methylpiperazin-1-yl)sulfonyl]phenyl}amino)prop-1-yn-1-yl]-1-(2,2,2-trifluoroethyl)-1H-indol-4-yl}amino)-$\lambda^6$-thiane-1,1-dione, MS (ES+, m/z): 668.2; 2-[3-({2-methoxy-4-[(4-methylpiperazin-1-yl)sulfonyl]phenyl}amino)prop-1-yn-1-yl]-N-(oxan-4-yl)-1-(2,2,2-trifluoroethyl)-1H-indol-4-amine, MS (ES+, m/z): 620.4; 2-[3-({2-methoxy-4-[(4-methylpiperazin-1-yl)sulfonyl]phenyl}amino)prop-1-yn-1-yl]-N-(1-methylpiperidin-4-yl)-1-(2,2,2-trifluoroethyl)-1H-indol-4-amine, MS (ES+, m/z): 633.3; and (1R,4R)—$N^4$-{2-[3-({2-methoxy-4-[(4-methylpiperazin-1-yl)sulfonyl]phenyl}amino)prop-1-yn-1-yl]-1-(2,2,2-trifluoroethyl)-1H-indol-4-yl}-$N^1,N^1$-dimethylcyclohexane-1,4-diamine, MS (ES+, m/z): 661.4.

Example C69: General Procedure for Preparation of Compounds 63A and 64A

-continued

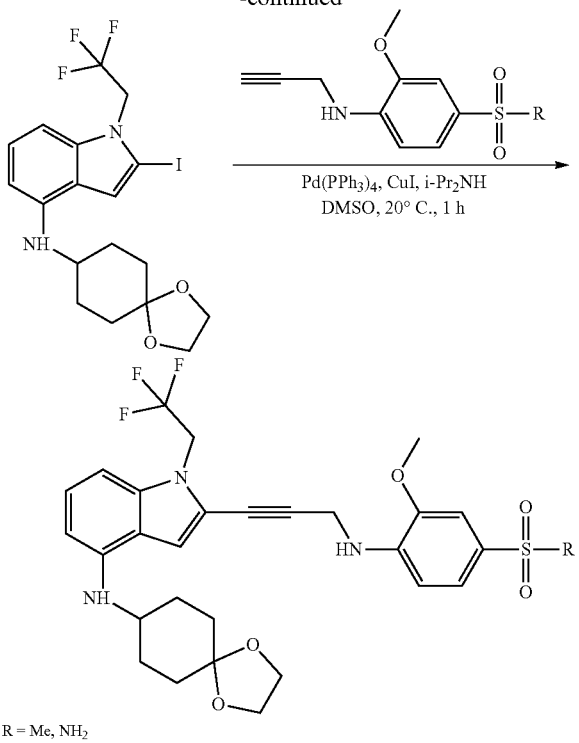

R = Me, NH₂

Synthesis of 2-iodo-N-(1,4-dioxaspiro[4.5]decan-8-yl)-1-(2,2,2-trifluoroethyl)-1H-indol-4-amine: To a solution of 2-iodo-1-(2,2,2-trifluoroethyl)-1H-indol-4-amine (500 mg, 1.47 mmol, 1 eq.) in MeOH (5 mL) were added 1,4-dioxaspiro[4.5]decan-8-one (1.15 g, 7.35 mmol, 5 eq.), and SnCl₂·2H₂O (66.4 mg, 294 μmol, 0.2 eq.). Polymethylhydrosiloxane (PMHS) (197.2 mg, 2.94 mmol, 2 eq.) was then added in one portion, and the resulting mixture was heated and stirred for 1 h at 70° C., after which time LC-MS analysis indicated that reaction was complete. The mixture was dried over anhydrous sodium sulfate, filtered with diatomite, and concentrated in vacuo. The residue was purified by silica gel chromatography (SiO₂, PE:EtOAc=50:1 to 5:1) to afford 2-iodo-N-(1,4-dioxaspiro[4.5]decan-8-yl)-1-(2,2,2-trifluoroethyl)-1H-indol-4-amine (800 mg, 1.33 mmol, 90.6% yield) as a yellow oil.

Preparation of final products: To a mixture of R-substituted alkyne (1.2 eq.) in DMSO (2 mL) were added diisopropylamine (3.12 mmol, 441 μL, 10 eq.), CuI (59.5 mg, 312 μmol, 1 eq.), 2-iodo-N-(1,4-dioxaspiro[4.5]decan-8-yl)-1-(2,2,2-trifluoroethyl)-1H-indol-4-amine (150 mg, 312 μmol, 1 eq.), and Pd(PPh₃)₄ (72.2 mg, 62.5 μmol, 0.2 eq.) under N₂. The mixture was stirred at 25° C. for 1 h, after which time LC-MS and TLC analysis indicated that the reaction was complete. 10 mL of EtOAc was then added, and the mixture was poured into a saturated EDTA solution (40 mL) and stirred for 15 min. The aqueous phase was extracted with EtOAc (40 mL×2), and the organic phase was poured into a saturated EDTA solution (40 mL) and stirred for 1 h. The aqueous phase was again extracted with EtOAc (40 mL×3), and the combined organic layers were washed with brine (40 mL×3), dried over anhydrous sodium sulfate, treated with activated carbon, filtered, and concentrated in vacuo. The residue was purified by prep-TLC, and then further purified by prep-HPLC to afford the desired compounds.

4-({3-[4-({1,4-dioxaspiro[4.5]decan-8-yl}amino)-1-(2,2,2-trifluoroethyl)-1H-indol-2-yl]prop-2-yn-1-yl}amino)-3-methoxybenzene-1-sulfonamide, MS (ES⁺, m/z): 593.2; and N-{1,4-dioxaspiro[4.5]decan-8-yl}-2-{3-[(4-methanesulfonyl-2-methoxyphenyl)amino]prop-1-yn-1-yl}-1-(2,2,2-trifluoroethyl)-1H-indol-4-amine, MS (ES⁺, m/z): 592.2.

Example C70: General Procedure for Preparation of Compounds 56A, 57A, 202A, 203A, 204A, 205A, 212A, 213A, 293A, 294A, 313A, 374A, 398A, 399A, 400A, 401A, and 1047A

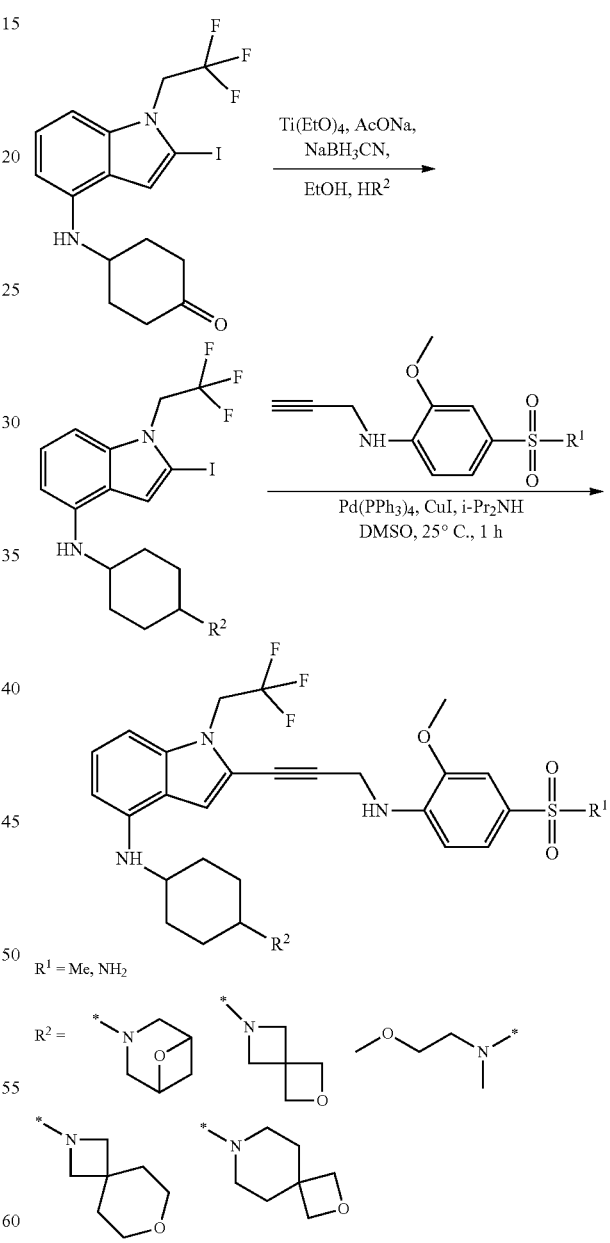

R¹ = Me, NH₂

Representative procedure for reductive amination reaction: A solution of 4-[[2-iodo-1-(2,2,2-trifluoroethyl)indol-4-yl]amino]cyclohexanone (380 mg, 854 μmol, 1 eq.), 6-oxa-3-azabicyclo[3.1.1]heptane (308 mg, 1.28 mmol, 1.5 eq.), NaOAc (140 mg, 1.71 mmol, 2 eq.), and tetraethoxytitanium (1.71 mmol, 354 µL, 2 eq.) in EtOH (10 mL) was stirred for 1 h at 25° C. NaBH₃CN (107.3 mg, 1.71 mmol, 2 eq.) was then added to the reaction, and the resulting reaction mixture was stirred at 25° C. for 1 h. TLC analysis showed that the ketone was consumed completely, and two new spot were detected. The reaction mixture was poured into a saturated NaHCO₃ (20 mL) and filtered, and the filtrate was extracted with EtOAc (20 mL×2). The organic layers were concentrated under reduced pressure to give a residue. The residue was purified by column chromatography (SiO₂, PE:EtOAc=2:1 to 1:1).

Representative procedure for Sonogashira coupling reaction: To a mixture of 2-methoxy-4-methylsulfonyl-N-prop-2-ynyl-aniline (874.9 mg, 3.33 mmol, 1.2 eq.) and 2-iodo-N-[4-(6-oxa-3-azabicyclo[3.1.1]heptan-3-yl)cyclohexyl]-1-(2,2,2-trifluoroethyl)indol-4-amine (1.8 g, 2.77 mmol, 1 eq.) in DMSO (30 mL) were added CuI (528 mg, 2.77 mmol, 1 eq.) and N-isopropylpropan-2-amine (27.7 mmol, 3.92 mL, 10 eq.), and Pd(PPh₃)₄ (640.8 mg, 555 µmol, 0.2 eq.) under N₂. The reaction mixture was stirred for 1 h at 25° C. LC-MS analysis indicated that the reaction was complete. The reaction mixture was quenched by adding saturated aqueous EDTA (50 mL) and stirred at 25° C. for 1 h, then extracted with EtOAc (50 mL×3). The combined organic layers were dried over anhydrous sodium sulfate, filtered, and concentrated under reduced pressure to give a residue. The residue was purified by column chromatography (SiO₂, PE:EtOAc=2:1 to 1:1) and further purified by prep-HPLC to afford the desired product as a yellow solid.

2-{3-[(4-methanesulfonyl-2-methoxyphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine, MS (ES⁺, m/z): 631.2; 2-{3-[(4-methanesulfonyl-2-methoxyphenyl)amino]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine, MS (ES⁺, m/z): 631.2; 3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide, MS (ES⁺, m/z): 632.2; 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide, MS (ES⁺, m/z): 632.2; 2-{3-[(4-methanesulfonyl-2-methoxyphenyl)amino]prop-1-yn-1-yl}-N-[(1R,4R)-4-{6-oxa-3-azabicyclo[3.1.1]heptan-3-yl}cyclohexyl]-1-(2,2,2-trifluoroethyl)-1H-indol-4-amine, MS (ES⁺, m/z): 631.2; 2-{3-[(4-methanesulfonyl-2-methoxyphenyl)amino]prop-1-yn-1-yl}-N-[(1S,4S)-4-{6-oxa-3-azabicyclo[3.1.1]heptan-3-yl}cyclohexyl]-1-(2,2,2-trifluoroethyl)-1H-indol-4-amine, MS (ES⁺, m/z): 631.2; 3-methoxy-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzene-1-sulfonamide, MS (ES⁺, m/z): 632.2; 3-methoxy-4-{[3-(4-{[(1S,4S)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzene-1-sulfonamide, MS (ES⁺, m/z): 632.2; 4-[(2-{3-[(2-methoxy-4-{2-oxa-6-azaspiro[3.3]heptane-6-sulfonyl}phenyl)amino]prop-1-yn-1-yl}-1-(2,2,2-trifluoroethyl)-1H-indol-4-yl)amino]-1λ⁶-thiane-1,1-dione, MS (ES⁺, m/z): 667.1; 3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide, MS (ES⁺, m/z): 596.1; 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide, MS (ES⁺, m/z): 596.1; 2-{3-[(4-methanesulfonyl-2-methoxyphenyl)amino]prop-1-yn-1-yl}-N-[(1R,4R)-4-{7-oxa-2-azaspiro[3.5]nonan-2-yl}cyclohexyl]-1-(2,2,2-trifluoroethyl)-1H-indol-4-amine, MS (ES⁺, m/z): 659.3; 2-{3-[(4-methanesulfonyl-2-methoxyphenyl)amino]prop-1-yn-1-yl}-N-[(1S,4S)-4-{7-oxa-2-azaspiro[3.5]nonan-2-yl}cyclohexyl]-1-(2,2,2-trifluoroethyl)-1H-indol-4-amine, MS (ES⁺, m/z): 659.4; 2-{3-[(4-methanesulfonyl-2-methoxyphenyl)amino]prop-1-yn-1-yl}-N-[(1R,4R)-4-{2-oxa-7-azaspiro[3.5]nonan-7-yl}cyclohexyl]-1-(2,2,2-trifluoroethyl)-1H-indol-4-amine, MS (ES⁺, m/z): 659.2; 2-{3-[(4-methanesulfonyl-2-methoxyphenyl)amino]prop-1-yn-1-yl}-N-[(1S,4S)-4-{2-oxa-7-azaspiro[3.5]nonan-7-yl}cyclohexyl]-1-(2,2,2-trifluoroethyl)-1H-indol-4-amine, MS (ES⁺, m/z): 659.3; (1R,4R)—N⁴-(2-{3-[(4-methanesulfonyl-2-methoxyphenyl)amino]prop-1-yn-1-yl}-1-(2,2,2-trifluoroethyl)-1H-indol-4-yl)-N¹-(2-methoxyethyl)-N¹-methylcyclohexane-1,4-diamine, MS (ES⁺, m/z): 621.3; and (1S,4S)—N⁴-(2-{3-[(4-methanesulfonyl-2-methoxyphenyl)amino]prop-1-yn-1-yl}-1-(2,2,2-trifluoroethyl)-1H-indol-4-yl)-N¹-(2-methoxyethyl)-N¹-methylcyclohexane-1,4-diamine, MS (ES⁺, m/z): 621.3.

Example C71: General Procedure for Preparation of Compounds 21A and 22A

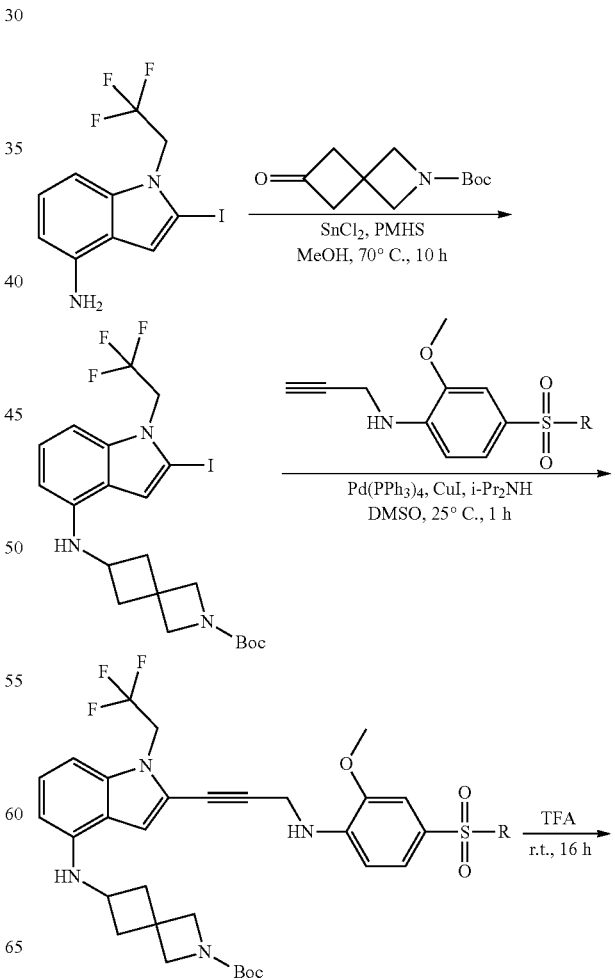

-continued

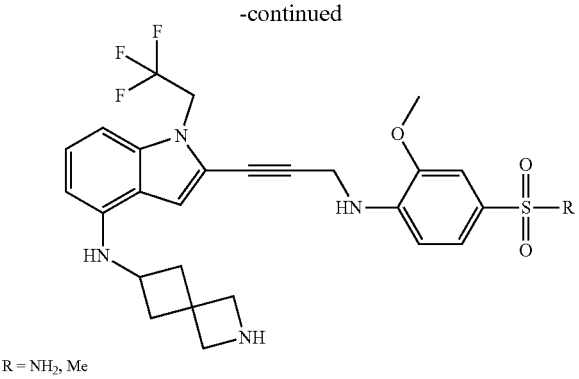

R = NH₂, Me

Synthesis of tert-butyl 6-((2-iodo-1-(2,2,2-trifluoroethyl)-1H-indol-4-yl)amino)-2-azaspiro[3.3]heptane-2-carboxylate: To a solution of 2-iodo-1-(2,2,2-trifluoroethyl)-1H-indol-4-amine (0.5 g, 1.47 mmol, 1 eq.) in MeOH (5 mL) were added tert-butyl 6-oxo-2-azaspiro[3.3]heptane-2-carboxylate (776.5 mg, 3.68 mmol, 2.5 eq.) and $SnCl_2 \cdot 2H_2O$ (66.4 mg, 294 μmol, 0.20 eq.). Polymethylhydrosiloxane (PMHS) (352.9 mg, 5.88 mmol, 4 eq.) was then added, and the mixture was stirred at 70° C. for 3 h, after which time TLC analysis indicated that the reaction was complete. The mixture was evaporated to afford the crude product, which was then purified by column chromatography to afford tert-butyl 6-((2-iodo-1-(2,2,2-trifluoroethyl)-1H-indol-4-yl)amino)-2-azaspiro[3.3]heptane-2-carboxylate as white solid.

Synthesis of tert-butyl 6-((2-(3-((2-methoxy-4-sulfamoylphenyl)amino)prop-1-yn-1-yl)-1-(2,2,2-trifluoroethyl)-1H-indol-4-yl)amino)-2-azaspiro[3.3]heptane-2-carboxylate and tert-butyl 6-((2-(3-((2-methoxy-4-(methylsulfonyl)phenyl)amino)prop-1-yn-1-yl)-1-(2,2,2-trifluoroethyl)-1H-indol-4-yl)amino)-2-azaspiro[3.3]heptane-2-carboxylate: To a mixture of 2-iodo-N-[4-(2-oxa-6-azaspiro[3.3]heptan-6-yl)cyclohexyl]-1-(2,2,2-trifluoroethyl)indol-4-amine (50 mg, 86.7 μmol, 1 eq.) and 2-methoxy-4-methylsulfonyl-N-prop-2-ynyl-aniline (27.3 mg, 104 μmol, 1.2 eq.) in DMSO (3 mL) were added CuI (16.5 mg, 86.7 μmol, 1 eq.), N-isopropylpropan-2-amine (86.7 μmol, 12.2 μL, 1 eq.), and Pd(PPh₃)₄ (2.0 mg, 1.73 μmol, 0.02 eq.) under N₂. The reaction mixture was stirred for 1 h at 25° C. LC-MS analysis indicated that all of the iodide was consumed. The reaction mixture was quenched by adding a saturated aqueous EDTA solution (60 mL) at 25° C. and stirring the mixture for 1 h, followed by extraction with EtOAc (20 mL×4). The combined organic layers were dried over anhydrous sodium sulfate, filtered, and concentrated under reduced pressure to give a residue. The residue was purified by prep-TLC (SiO₂, DCM:MeOH=10:1, $R_{f1}$, =0.43, $R_{f2}$=0.37) and purified further by prep-HPLC to obtain the desired product as a yellow solid.

General procedure for preparation of final products: A solution of the Boc-protected amine (1 eq.) in DCM was added into 2,2,2-trifluoroacetic acid (174.7 eq.) at 20° C. and stirred for 16 h. LC-MS analysis indicated that the starting material was consumed, and one main mass with desired compound was observed. The reaction mixture was concentrated under reduced pressure, and the residue was purified by prep-HPLC to afford the compounds as yellow solids.

N-{2-azaspiro[3.3]heptan-6-yl}-2-{3-[(4-methanesulfonyl-2-methoxyphenyl)amino]prop-1-yn-1-yl}-1-(2,2,2-trifluoroethyl)-1H-indol-4-amine, MS (ES⁺, m/z): 547.2; and 4-({3-[4-({2-azaspiro[3.3]heptan-6-yl}amino)-1-(2,2,2-trifluoroethyl)-1H-indol-2-yl]prop-2-yn-1-yl}amino)-3-methoxybenzene-1-sulfonamide, MS (ES⁺, m/z): 548.2.

Example C72: General Procedure for Preparation of Compounds 151A, 152A, 295A, 296A, 375A, and 376A

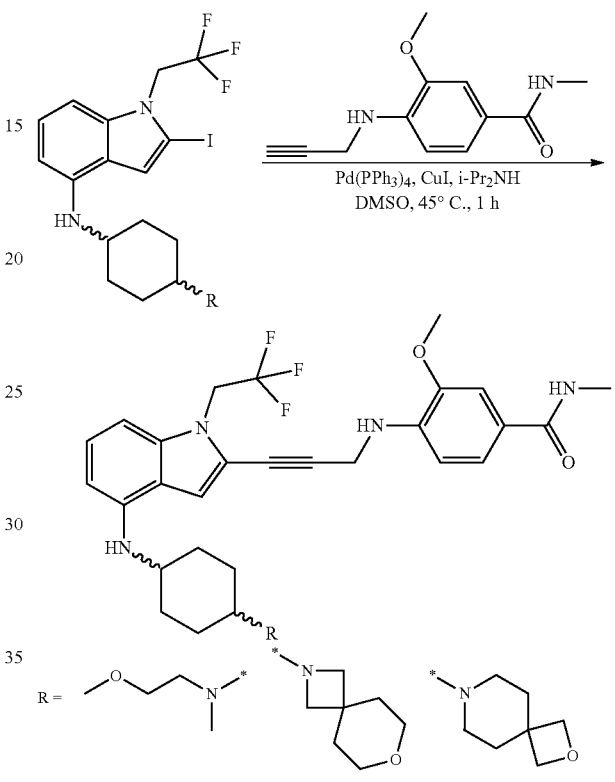

Representative procedure: To a mixture of 3-methoxy-N-methyl-4-(prop-2-ynylamino)benzamide (38.6 mg, 159 μmol, 1.5 eq.) and N¹-[2-iodo-1-(2,2,2-trifluoroethyl)indol-4-yl]-N⁴-(2-methoxyethyl)-N⁴-methyl-cyclohexane-1,4-diamine (60.0 mg, 106.0 μmol, 1 eq.) in DMSO (3 mL) were added N-isopropylpropan-2-amine (106 μmol, 15 μL, 1 eq.) and Pd(PPh₃)₄ (2.5 mg, 2.1 μmol, 0.02 eq.), followed by CuI (20.2 mg, 106 μmol, 1 eq.) under N₂. The reaction mixture was stirred for 1 h at 45° C. and monitored by TLC analysis (DCM:MeOH=10:1). The reaction mixture was quenched by adding a saturated EDTA solution (40 mL), and extracted with EtOAc (20 mL×3). The combined organic layers were dried over anhydrous sodium sulfate, filtered, and concentrated under reduced pressure. The resulting residue was purified by prep-TLC (SiO₂, DCM:MeOH=10:1), and further purified by prep-HPLC to give 3-methoxy-4-[3-[4-[[4-[2-methoxyethyl(methyl)amino]cyclohexyl]amino]-1-(2,2,2-trifluoroethyl)indol-2-yl]prop-2-ynylamino]-N-methyl-benzamide (17.0 mg, 27.5 μmol, 26.0% yield) as light yellow solid.

3-methoxy-N-methyl-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide, MS (ES⁺, m/z): 600.3; 3-methoxy-N-methyl-4-{[3-(4-{[(1S,4S)-4-[(2-methoxyethyl)(methyl)amino]cyclohexyl]amino}-1-(2,2,2-trifluoroethyl)-1H-indol-2-yl)prop- 2-yn-1-yl]amino}benzamide, MS (ES+, m/z): 600.3; 3-methoxy-N-methyl-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide, MS (ES+, m/z): 638.4; 3-methoxy-N-methyl-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide, MS (ES+, m/z): 638.4; 3-methoxy-N-methyl-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzamide, MS (ES+, m/z): 638.4; and 3-methoxy-N-methyl-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzamide, MS (ES+, m/z): 638.3.

Example C73: General Procedure for Preparation of Compounds 297A, 298A, 400A, and 401A

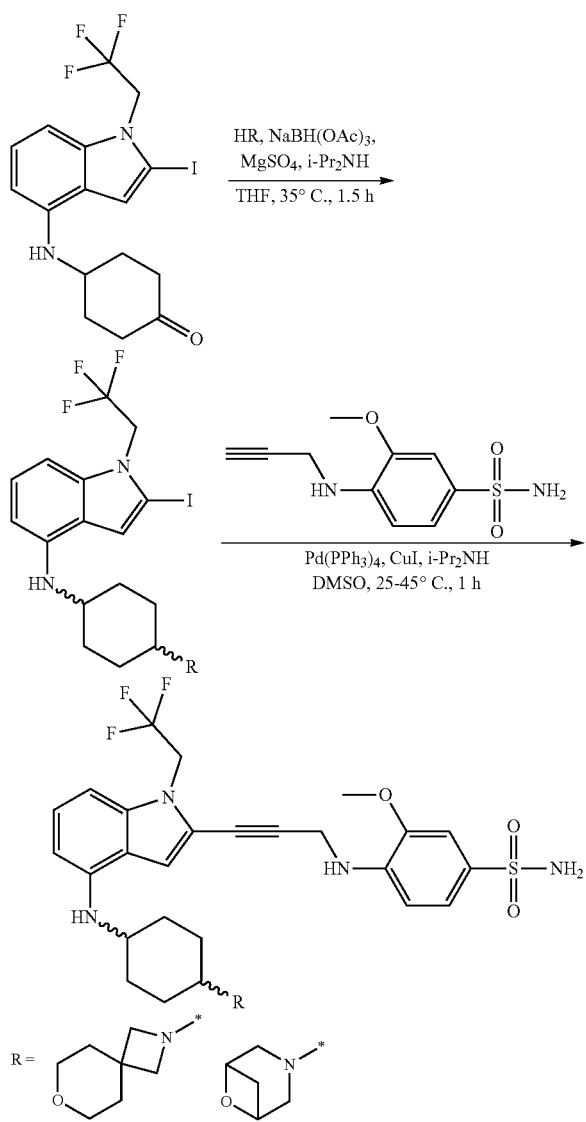

Representative procedure for reductive amination: To a solution of 4-[[2-iodo-1-(2,2,2-trifluoroethyl)indol-4-yl]amino]cyclohexanone (5 g, 11.1 mmol, 1 eq) and 7-oxa-2-azaspiro[3.5]nonane oxalic acid (4.60 g, 13.3 mmol, 1.2 eq.) in THF (100 mL) were added i-Pr$_2$NH (55.6 mmol, 7.86 mL, 5 eq.) and MgSO$_4$ (6.69 g, 55.6 mmol, 5 eq.). The mixture was heated and stirred at 35° C. for 0.5 h, and NaBH(OAc)$_3$ (4.71 g, 22.2 mmol, 2 eq) was added to the reaction. The resulting mixture was stirred further at 35° C. for 1 h. TLC analysis (PE:EtOAc=3:1) showed that the reaction was complete. The reaction mixture was poured into water (100 mL), and the aqueous phase was extracted with EtOAc (40 mL×3). The combined organic layers were washed with brine (40 mL), dried over anhydrous sodium sulfate, filtered, and concentrated in vacuo. The residue was purified by column chromatography (SiO$_2$, PE:EtOAc=3:1 to 0:1) to give the desired product 2-iodo-N-[4-(7-oxa-2-azaspiro[3.5]nonan-2-yl)cyclohexyl]-1-(2,2,2-trifluoroethyl)indol-4-amine (10 g, 16.4 mmol, 49.3% yield) as light yellow solid.

Representative Procedure for Sonogashira coupling: To a solution of 3-methoxy-4-(prop-2-ynylamino)benzenesulfonamide (1.58 g, 5.92 mmol, 1.2 eq.) in DMSO (30 mL) were added i-Pr$_2$NH (49.3 mmol, 6.97 mL, 10 eq.) and CuI (939 mg, 4.93 mmol, 1 eq) at 45° C. under N$_2$. Then, 2-iodo-N-[4-(7-oxa-2-azaspiro[3.5]nonan-2-yl)cyclohexyl]-1-(2,2,2-trifluoroethyl)indol-4-amine (3 g, 4.93 mmol, 1 eq) and Pd(PPh$_3$)$_4$ (1.14 g, 986 μmol, 0.2 eq) were added to the reaction. The resulting mixture was stirred at 45° C. for 1 h. TLC analysis (DCM:MeOH=10:1) showed that the reaction was complete. The mixture was poured into a saturated aqueous EDTA solution (100 mL) and stirred for 1 h. The aqueous phase was extracted with EtOAc (200 mL×3). The combined organic layers were washed with brine (60 mL), dried over anhydrous sodium sulfate, filtered, and concentrated in vacuo. The resulting residue was purified by prep-TLC and prep-HPLC to give the desired product 3-methoxy-4-[3-[4-[[4-(7-oxa-2-azaspiro[3.5]nonan-2-yl)cyclohexyl]amino]-1-(2,2,2-trifluoroethyl)indol-2-yl]prop-2-ynylamino]benzenesulfonamide (6 g, 8.64 mmol, 58.4% yield).

3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide, MS (ES+, m/z): 660.3; 3-methoxy-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide, MS (ES+, m/z): 660.3; 3-methoxy-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzene-1-sulfonamide, MS (ES+, m/z): 632.2; and 3-methoxy-4-{[3-(4-{[(1S,4S)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzene-1-sulfonamide, MS (ES+, m/z): 632.2.

Example C74: Preparation of Compounds 210A and 211A

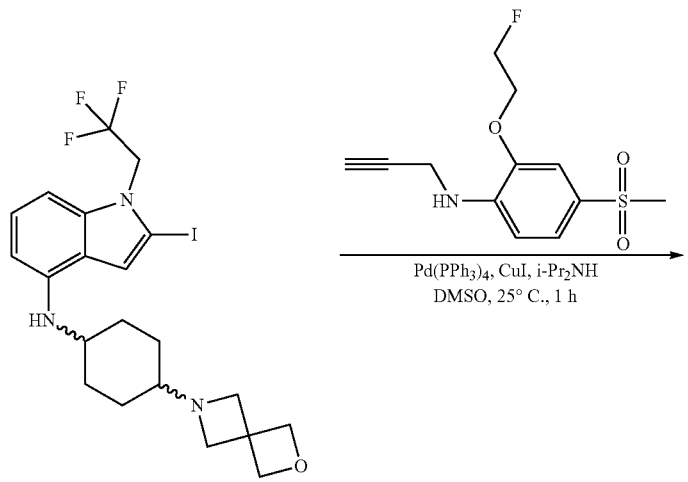

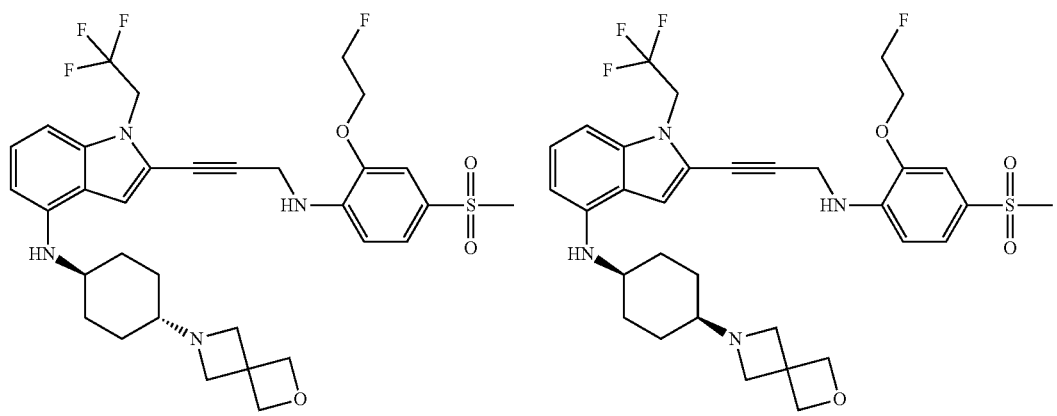

Compounds 210A and 211A were prepared via a procedure analogous to the synthesis of Compounds 389A and 390A according to EXAMPLE C47, starting from N-(4-(2-oxa-6-azaspiro[3.3]heptan-6-yl)cyclohexyl)-2-iodo-1-(2,2,2-trifluoroethyl)-1H-indol-4-amine and 2-(2-fluoroethoxy)-4-(methylsulfonyl)-N-(prop-2-yn-1-yl)aniline. (2-(3-{[2-(2-fluoroethoxy)-4-methanesulfonylphenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine) was purified by column chromatography (SiO$_2$, PE:EtOAc=2:1 to EtOAc to DCM:MeOH=10:1, R$_f$=0.3) and further purified by prep-HPLC to obtain the desired product in 50.8% yield (830.2 mg, 1.25 mmol, MS (ES$^+$, m/z): 663.2) as a yellow solid. (2-(3-{[2-(2-fluoroethoxy)-4-methanesulfonylphenyl]amino}prop-1-yn-1-yl)-N-[(1S,4S)-4-{2-oxa-6-azaspiro[3.3]heptan-6-yl}cyclohexyl]-1-(2,2,2-trifluoroethyl)-1H-indol-4-amine) was purified by prep-TLC (DCM:MeOH=20:1) and further purified by prep-HPLC to obtain the desired product in 17.4% yield (10.3 mg, 14.26 μmol, MS (ES$^+$, m/z): 663.2) as a yellow solid.

Example C75: General Procedure for Preparation of Compounds 48A, 50A, 54A, 55A, 469A, 471A, 472A, 473A, 477A, 479A, 528A, 529A, 544A, 547A, 551A, 553A, 555A, 564A, 572A, 577A, 718A, 726A, 992A, 994A, 996A, 999A, 1000A, 1001A, 1015A, 1036A, 1037A, 1038A, 1039A, 1040A, 1042A, 1043A, 1044A, 1045A, 1046A, 1052A, and 1053A

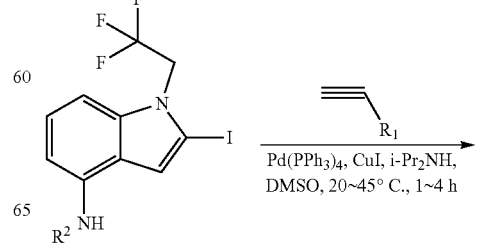

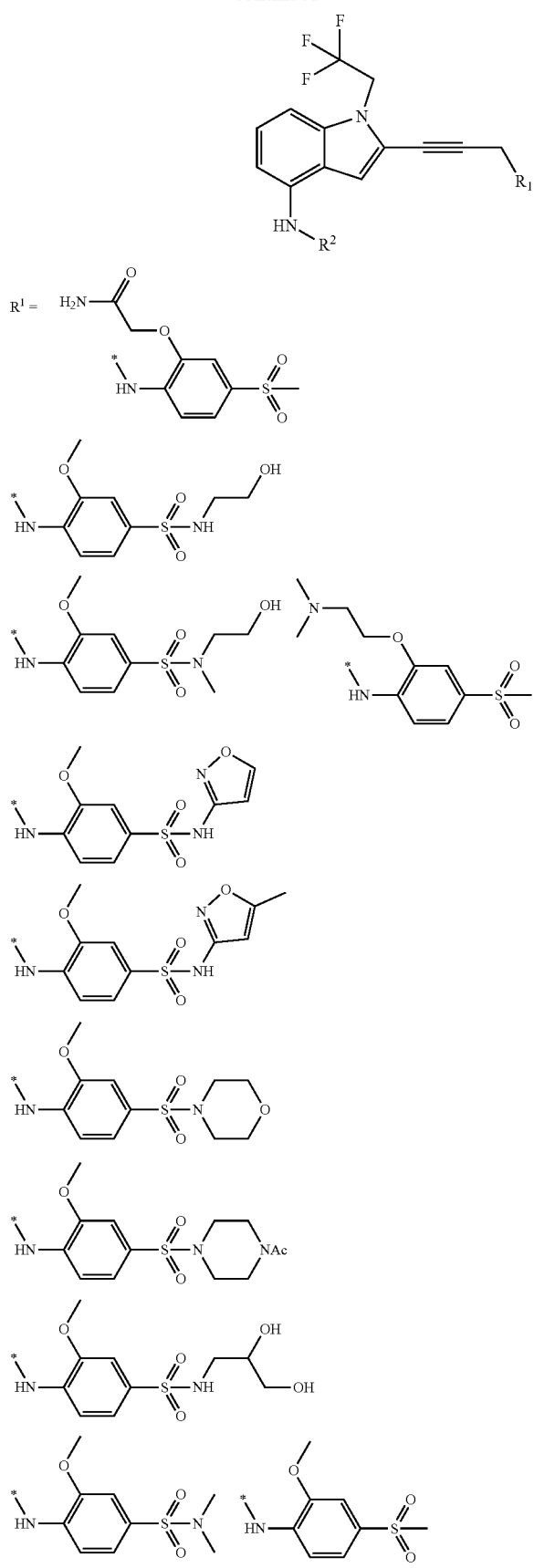
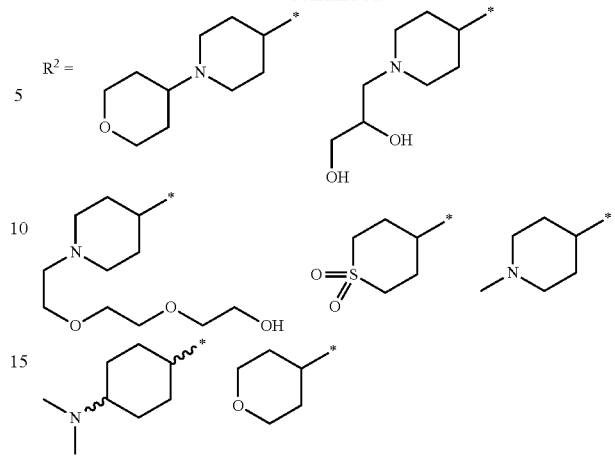

Representative Procedure: To a mixture of 2-methoxy-4-methylsulfonyl-N-prop-2-ynyl-aniline (18.4 mg, 66.9 μmol, 0.87 eq., HCl) in DMSO (2 mL) were added i-Pr$_2$NH (769 μmol, 108 μL, 10 eq), CuI (14.6 mg, 76.9 μmol, 1 eq), 2-iodo-N-(1-tetrahydropyran-4-yl-4-piperidyl)-1-(2,2,2-trifluoroethyl)indol-4-amine (50.0 mg, 76.9 μmol, 1 eq.), and Pd(PPh$_3$)$_4$ (88.8 mg, 76.9 μmol, 1 eq.) at 25° C. The mixture was stirred at 25° C. for 1 h. TLC and LC-MS analysis showed that the reaction was complete. EtOAc (10 mL) was poured into the mixture, and the mixture was poured into saturated aqueous EDTA (30 mL) and stirred for 15 min. The aqueous phase was extracted with EtOAc (30 mL×2). The organic layer was poured into saturated aqueous EDTA (30 mL) and stirred for 1 h. The aqueous phase was extracted with EtOAc (30 mL×3). The combined organic layers were washed with brine (30 mL×3), dried over anhydrous sodium sulfate, treated with activated carbon, filtered and concentrated in vacuo. The residue was purified by prep-TLC and prep-HPLC to afford 2-[3-(2-methoxy-4-methylsulfonyl-anilino)prop-1-ynyl]-N-(1-tetrahydropyran-4-yl-4-piperidyl)-1-(2,2,2-trifluoroethyl)indol-4-amine (13.3 mg, 20.2 μmol, 26.3% yield) as light yellow solid. The other compounds were prepared using the same procedure.

2-(2-((3-(4-((1,1-dioxidotetrahydro-2H-thiopyran-4-yl)amino)-1-(2,2,2-trifluoroethyl)-1H-indol-2-yl)prop-2-yn-1-yl)amino)-5-(methylsulfonyl)phenoxy)acetamide, MS (ES$^+$, m/z): 627.2; 2-(2-((3-(4-((1-methylpiperidin-4-yl)amino)-1-(2,2,2-trifluoroethyl)-1H-indol-2-yl)prop-2-yn-1-yl)amino)-5-(methylsulfonyl)phenoxy)acetamide, MS (ES$^+$, m/z): 592.2; 4-((3-(4-((1,1-dioxidotetrahydro-2H-thiopyran-4-yl)amino)-1-(2,2,2-trifluoroethyl)-1H-indol-2-yl)prop-2-yn-1-yl)amino)-N-(2-hydroxyethyl)-3-methoxybenzenesulfonamide, MS (ES$^+$, m/z): 629.2; N-(2-hydroxyethyl)-3-methoxy-4-((3-(4-((tetrahydro-2H-pyran-4-yl)amino)-1-(2,2,2-trifluoroethyl)-1H-indol-2-yl)prop-2-yn-1-yl)amino)benzenesulfonamide, MS (ES$^+$, m/z): 581.2; N-(2-hydroxyethyl)-3-methoxy-4-((3-(4-((1-(tetrahydro-2H-pyran-4-yl)piperidin-4-yl)amino)-1-(2,2,2-trifluoroethyl)-1H-indol-2-yl)prop-2-yn-1-yl)amino)benzenesulfonamide, MS (ES$^+$, m/z): 664.3; 4-((3-(4-((1-(2,3-dihydroxypropyl)piperidin-4-yl)amino)-1-(2,2,2-trifluoroethyl)-1H-indol-2-yl)prop-2-yn-1-yl)amino)-N-(2-hydroxyethyl)-3-methoxybenzenesulfonamide, MS (ES$^+$, m/z): 654.2; 2-[2-(2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethoxy)ethoxy]ethan-1-ol, MS (ES$^+$, m/z): 667.2; N-(2-hydroxyethyl)-3-methoxy-4-((3-(4-((1-methylpiperidin-4-yl)amino)-1-(2,2,2-trifluoroethyl)-1H-indol-2-yl)prop-2-yn-1-yl)amino)benzenesulfonamide, MS (ES$^+$, m/z): 594.2; 3-methoxy-4-[(3-{4-[(oxan-4-yl)amino]-1-(2,2,2-trifluoroethyl)-1H-indol-2-yl}prop-2-yn-1-yl)amino]-N-(1,2-oxazol-3-yl)benzene-1-sulfonamide, MS (ES$^+$, m/z): 604.2; 4-[(3-{4-[(1,1-dioxo-1λ$^6$-thian-4-yl)amino]-1-(2,2,2-trifluoroethyl)-1H-indol-2-yl}prop-2-yn-1-yl)amino]-N-(2-hydroxyethyl)-3-methoxy-N-methylbenzene-1-sulfonamide, MS (ES$^+$, m/z): 643.1; 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-(1,2-oxazol-3-yl)benzene-1-sulfonamide, MS (ES$^+$, m/z): 604.2; 3-methoxy-N-(1,2-oxazol-3-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide, MS (ES$^+$, m/z): 645.3; 3-methoxy-N-(1,2-oxazol-3-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide, MS (ES$^+$, m/z): 645.2; 3-methoxy-N-(5-methyl-1,2-oxazol-3-yl)-4-[(3-{4-[(1-methylpiperidin-4-yl)amino]-1-(2,2,2-trifluoroethyl)-1H-indol-2-yl}prop-2-yn-1-yl)amino]benzene-1-sulfonamide, MS (ES$^+$, m/z): 631.2; 3-methoxy-N-(5-methyl-1,2-oxazol-3-yl)-4-[(3-{4-[(oxan-4-yl)amino]-1-(2,2,2-trifluoroethyl)-1H-indol-2-yl}prop-2-yn-1-yl)amino]benzene-1-sulfonamide, MS (ES$^+$, m/z): 618.2; 4-({2-[3-({2-[2-(dimethylamino)ethoxy]-4-methanesulfonylphenyl}amino)prop-1-yn-1-yl]-1-(2,2,2-trifluoroethyl)-1H-indol-4-yl}amino)-1λ$^6$-thiane-1,1-dione, MS (ES$^+$, m/z): 641.2; 4-[(3-{4-[(1,1-dioxo-1λ$^6$-thian-4-yl)amino]-1-(2,2,2-trifluoroethyl)-1H-indol-2-yl}prop-2-yn-1-yl)amino]-3-methoxy-N-(5-methyl-1,2-oxazol-3-yl)benzene-1-sulfonamide, MS (ES$^+$, m/z): 666.2; 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-(5-methyl-1,2-oxazol-3-yl)benzene-1-sulfonamide, MS (ES$^+$, m/z): 691.2; 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-N-(2-hydroxyethyl)-3-methoxy-N-methylbenzene-1-sulfonamide, MS (ES$^+$, m/z): 668.2; 4-{[2-(3-{[2-methoxy-4-(morpholine-4-sulfonyl)phenyl]amino}prop-1-yn-1-yl)-1-(2,2,2-trifluoroethyl)-1H-indol-4-yl]amino}-1λ$^6$-thiane-1,1-dione, MS (ES$^+$, m/z): 655.3; 4-[(3-{4-[(1,1-dioxo-1λ$^6$-thian-4-yl)amino]-1-(2,2,2-trifluoroethyl)-1H-indol-2-yl}prop-2-yn-1-yl)amino]-3-methoxy-N-(1,2-oxazol-3-yl)benzene-1-sulfonamide, MS (ES$^+$, m/z): 652.1; 3-methoxy-4-[(3-{4-[(1-methylpiperidin-4-yl)amino]-1-(2,2,2-trifluoroethyl)-1H-indol-2-yl}prop-2-yn-1-yl)amino]-N-(1,2-oxazol-3-yl)benzene-1-sulfonamide, MS (ES$^+$, m/z): 617.2; N-[2-(dimethylamino)ethyl]-4-[(3-{4-[(1,1-dioxo-1λ$^6$-thian-4-yl)amino]-1-(2,2,2-trifluoroethyl)-1H-indol-2-yl}prop-2-yn-1-yl)amino]-3-methoxy-N-methylbenzene-1-sulfonamide, MS (ES$^+$, m/z): 670.2; 3-methoxy-N-(2-methoxyethyl)-N-methyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide, MS (ES$^+$, m/z): 622.2; N-(2,3-dihydroxypropyl)-4-[(3-{4-[(1,1-dioxo-1λ$^6$-thian-4-yl)amino]-1-(2,2,2-trifluoroethyl)-1H-indol-2-yl}prop-2-yn-1-yl)amino]-3-methoxybenzene-1-sulfonamide, MS (ES$^+$, m/z): 659.1; 3-methoxy-N-(5-methyl-1,2-oxazol-3-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide, MS (ES$^+$, m/z): 659.3; 3-methoxy-N-(5-methyl-1,2-oxazol-3-yl)-4-{1[3-(4-{[(1S,4S)-4-(dimethylamino)cyclohexyl]amino}-1-(2,2,2-trifluoroethyl)-1H-indol-2-yl)prop-2-yn-1-yl] amino}benzene-1-sulfonamide, MS (ES$^+$, m/z): 659.2; N-(2-hydroxyethyl)-3-methoxy-N-methyl-4-[(3-{4-[(oxan-4-yl)amino]-1-(2,2,2-trifluoroethyl)-1H-indol-2-yl}prop-2-yn-1-yl)amino]benzene-1-sulfonamide, MS (ES$^+$, m/z): 595.2; N-(2-hydroxyethyl)-3-methoxy-N-methyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide, MS (ES$^+$, m/z): 608.2; N-(2-hydroxyethyl)-3-methoxy-N-methyl-4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide, MS (ES$^+$, m/z): 678.3; 3-methoxy-N,N-dimethyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide, MS (ES$^+$, m/z): 578.2; 4-[(3-{4-[(1,1-dioxo-1λ-thian-4-yl)amino]-1-(2,2,2-trifluoroethyl)-1H-indol-2-yl}prop-2-yn-1-yl)amino]-3-methoxy-N,N-dimethylbenzene-1-sulfonamide, MS (ES$^+$, m/z): 613.1; 3-methoxy-N,N-dimethyl-4-[(3-{4-[(oxan-4-yl)amino]-1-(2,2,2-trifluoroethyl)-1H-indol-2-yl}prop-2-yn-1-yl)amino]benzene-1-sulfonamide, MS (ES$^+$, m/z): 565.2; 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N,N-dimethylbenzene-1-sulfonamide, MS (ES$^+$, m/z): 638.3; 1-(4-{3-methoxy-4-[(3-{4-[(1-methylpiperidin-4-yl)amino]-1-(2,2,2-trifluoroethyl)-1H-indol-2-yl}prop-2-yn-1-yl)amino]benzenesulfonyl}piperazin-1-yl)ethan-1-one, MS (ES$^+$, m/z): 661.3; 4-({2-[3-({4-[(4-acetylpiperazin-1-yl)sulfonyl]-2-methoxyphenyl}amino)prop-1-yn-1-yl]-1-(2,2,2-trifluoroethyl)-1H-indol-4-yl}amino)-1λ$^6$-thiane-1,1-dione, MS (ES$^+$, m/z): 696.2; 1-(4-{3-methoxy-4-[(3-{4-[(oxan-4-yl)amino]-1-(2,2,2-trifluoroethyl)-1H-indol-2-yl}prop-2-yn-1-yl)amino]benzenesulfonyl}piperazin-1-yl)ethan-1-one, MS (ES$^+$, m/z): 648.2; 1-[4-(4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxybenzenesulfonyl)piperazin-1-yl]ethan-1-one, MS (ES$^+$, m/z): 721.3; 4-[(3-{4-[(1,1-dioxo-1λ$^6$-thian-4-yl)amino]-1-(2,2,2-trifluoroethyl)-1H-indol-2-yl}prop-2-yn-1-yl)amino]-3-methoxy-N-(2-methoxyethyl)-N-methylbenzene-1-sulfonamide, MS (ES$^+$, m/z): 657.2; 3-methoxy-N-(2-methoxyethyl)-N-methyl-4-[(3-{4-[(oxan-4-yl)amino]-1-(2,2,2-trifluoroethyl)-1H-indol-2-yl}prop-2-yn-1-yl)amino]benzene-1-sulfonamide, MS (ES$^+$, m/z): 609.2; and 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-(2-methoxyethyl)-N-methylbenzene-1-sulfonamide, MS (ES$^+$, m/z): 682.2.

Example C76: Synthesis of Compounds 263A, 264A, 327A, 328A, and 617A

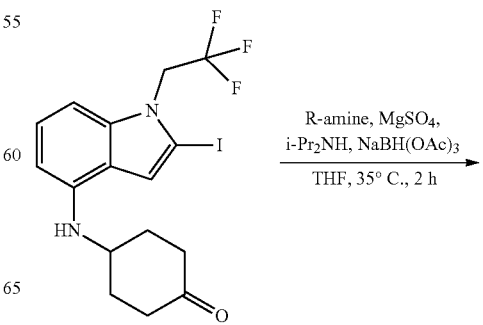

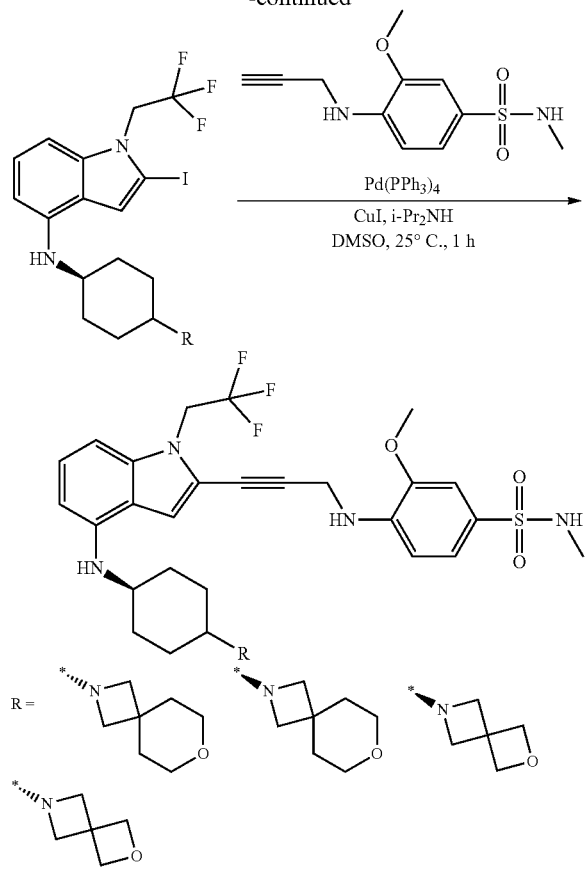

Representative Procedure for Reductive Amination: Preparation of 2-iodo-4-(R-substituted)-1-(2,2,2-trifluoroethyl)-1H-indole: A mixture of 4-[[2-iodo-1-(2,2,2-trifluoroethyl)indol-4-yl]amino]cyclohexanone (2.5 g, 5.73 mmol, 1 eq.), 7-oxa-2-azaspiro[3.5]nonane oxalic acid salt (1.97 g, 5.73 mmol, 1 eq.), and NaBH(OAc)$_3$ (2.43 g, 11.5 mmol, 2 eq.) and MgSO$_4$ (3.45 g, 28.7 mmol, 5 eq.) in THF (10 mL) was stirred 1 h at 25° C. Then, i-Pr$_2$NH (28.7 mmol, 4.05 mL, 5 eq.) was added to the reaction and stirred for an additional 1 h. LC-MS analysis showed that the reaction was complete. The reaction mixture was quenched by adding a saturated aqueous NaHCO$_3$ solution (40 mL) at 25° C. The mixture was diluted with water (100 mL) and extracted with EtOAc (100 mL×2). The combined organic layers were dried over anhydrous sodium sulfate, filtered, and concentrated under reduced pressure to give a residue. The residue was purified by chromatography over silica gel (SiO$_2$, DCM:MeOH=10:1, R$_{f1}$=0.28, R$_{f2}$=0.24) to give 2-iodo-N-[4-(7-oxa-2-azaspiro[3.5]nonan-2-yl)cyclohexyl]-1-(2,2,2-trifluoroethyl)indol-4-amine (3 g, 5.48 mmol, 47.8% yield) as a light yellow solid. $^1$H NMR (400 MHz, DMSO) δ=7.24 (s, 1H), 6.90-6.86 (m, 1H), 6.75-6.73 (d, 2H), 6.13-6.11 (d, 1H), 5.57-5.35 (d, 1H), 5-4.94 (m, 2H), 3.50-3.48 (m, 4H), 3.39 (s, 1H), 3.17-3.16 (d, 2H), 2.89 (m, 4H), 2.39 (m, 1H), 2.16 (m, 1H), 1.67-1.59 (m, 10H), 1.57-1.41 (m, 1H).

Representative Procedure (Sonogashira Coupling): To a mixture of N-[3-methoxy-4-(prop-2-ynylamino)phenyl]sulfonylacetamide (43.0 mg, 137 μmol, 1.5 eq.) in DMSO (2 mL) were added i-Pr$_2$NH (913 μmol, 129 μL, 10 eq.), CuI (8.7 mg, 46 μmol, 0.5 eq.), 2-iodo-N-[4-(7-oxa-2-azaspiro[3.5]nonan-2-yl)cyclohexyl]-1-(2,2,2-trifluoroethyl)indol-4-amine (50 mg, 91.3 μmol, 1 eq.), and Pd(PPh$_3$)$_4$ (21.1 mg, 18.3 μmol, 0.2 eq.) at 25° C. The mixture was stirred for 1 h. TLC analysis (DCM:MeOH=10:1, R$_f$=0.6) showed that the reaction was complete. EtOAc (10 mL) was poured into the reaction, and the mixture was poured into a saturated aqueous EDTA solution (30 mL) and stirred for 15 min. The aqueous phase was extracted with EtOAc (30 mL×2). The organic layer was poured into a saturated aqueous EDTA solution (30 mL) and stirred for 1 h. The aqueous phase was extracted with EtOAc (30 mL×3). The combined organic layers were washed with brine (30 mL×3), dried over anhydrous sodium sulfate, and concentrated in vacuo. The mixture was purified by prep-TLC (DCM:MeOH=10:1, R$_f$=0.5) followed by prep-HPLC to afford the desired products as a white solid (18.5 mg, 24.2 μmol, formic acid salt).

3-methoxy-4-{[3-(4-{[1-(2-methoxyethyl)piperidin-4-yl]amino}-1-(2,2,2-trifluoroethyl)-1H-indol-2-yl)prop-2-yn-1-yl]amino}-N-methylbenzene-1-sulfonamide, MS (ES$^+$, m/z): 608.2; 4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzenesulfonamide, MS (ES$^+$, m/z): 674.3; 4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzenesulfonamide, MS (ES$^+$, m/z): 674.3; 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N-methylbenzenesulfonamide, and MS (ES$^+$, m/z): 646.2; 4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N-methylbenzenesulfonamide, MS (ES$^+$, m/z): 646.3.

Example C77: Synthesis of Compounds 267A and 268A

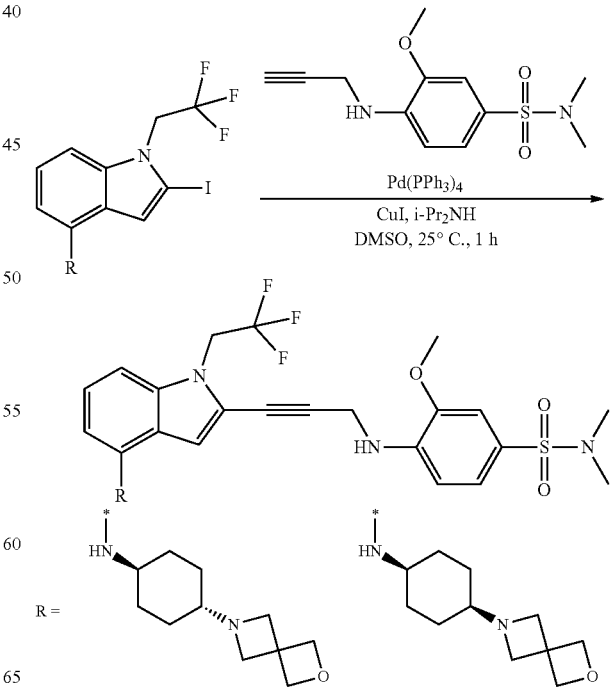

To a mixture of 3-methoxy-N,N-dimethyl-4-(prop-2-ynylamino)benzenesulfonamide (31.0 mg, 115.5 µmol, 1.2 eq.) in DMSO (3 mL) were added i-Pr₂NH (963 µmol, 136 µL, 10 eq), CuI (3.7 mg, 19.6 mol, 0.2 eq.), followed by 2-iodo-N-[4-(2-oxa-6-azaspiro[3.3]heptan-6-yl)cyclohexyl]-1-(2,2,2-trifluoroethyl)indol-4-amine (50 mg, mol, 1 eq) and Pd(PPh₃)₄ (11.1 mg, 9.63 µmol, 0.1 eq.). The mixture was stirred at 25° C. for 1 h under N₂. LC-MS analysis showed that the reaction was complete. The reaction mixture was stirred with a saturated aqueous EDTA solution (50 mL) and EtOAc (25 mL) at 25° C. for 1 h, then extracted with EtOAc (25 mL×2). The organic layers were washed with water (100 mL×2) and brine (100 mL×2), dried over anhydrous sodium sulfate, stirred with activated carbon, filtered, and concentrated under reduced pressure to give a residue. The residue was purified by prep-TLC (SiO₂, PE:EtOAc:TEA=1:1:0.2) and further purified by prep-HPLC to give the product 3-methoxy-N,N-dimethyl-4-[3-[4-[[4-(2-oxa-6-azaspiro[3.3]heptan-6-yl)cyclohexyl]amino]-1-(2,2,2-trifluoroethyl)indol-2-yl]prop-2-ynylamino]benzenesulfonamide (17.2 mg, 26.1 µmol, 27.1% yield).

4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N,N-dimethylbenzenesulfonamide, MS (ES⁺, m/z): 660.2; 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N,N-dimethylbenzenesulfonamide, MS (ES⁺, m/z): 660.2.

TABLE 3 shows compounds with a 2-ethynyl-N-(cycloalkyl)-1H-indole-4-amine core.

TABLE 3

| Compound No. | Structure | IUPAC | LC-MS (ES⁺, m/z) |
|---|---|---|---|
| 18A | 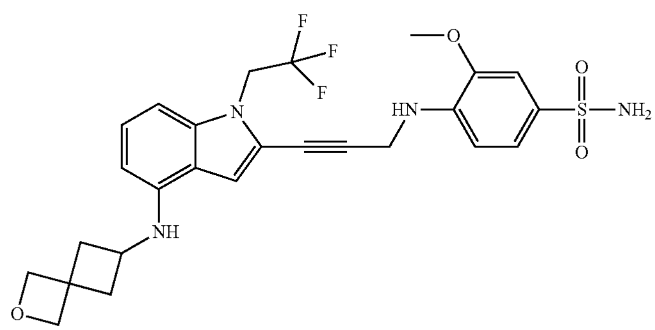 [SMILES: COc1cc(S(N)(=O)=O)ccc1NCC#Cc1cc2c(NC3CC4(COC4)C3)cccc2n1CC(F)(F)F] | 3-methoxy-4-{3-[4-({2-oxaspiro[3.3]heptan-6-yl}amino)-1-(2,2,2-trifluoroethyl)-1H-indol-2-yl]prop-2-yn-1-yl}amino)benzene-1-sulfonamide | 549.2 |
| 19A | 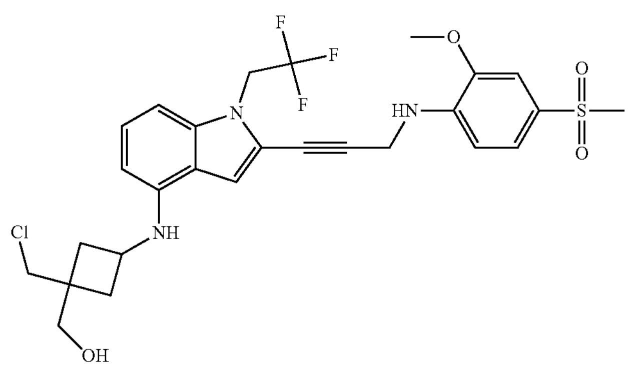 [SMILES: COc1cc(S(C)(=O)=O)ccc1NCC#Cc1cc2c(NC3CC(CO)(CCl)C3)cccc2n1CC(F)(F)F] | [1-(chloromethyl)-3-[(2-{3-[(4-methanesulfonyl-2-methoxyphenyl)amino]prop-1-yn-1-yl}-1-(2,2,2-trifluoroethyl)-1H-indol-4-yl)amino]cyclobutyl]methanol | 584.2 |
| 20A | 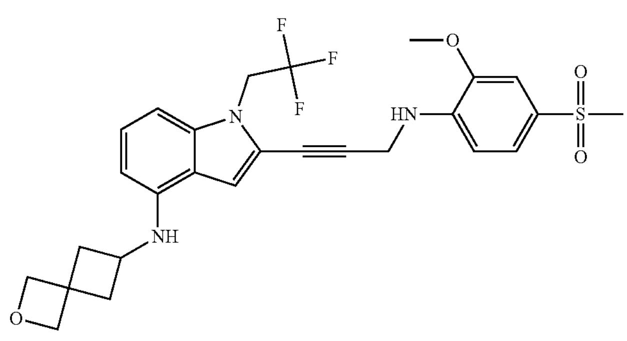 [SMILES: COc1cc(S(C)(=O)=O)ccc1NCC#Cc1cc2c(NC3CC4(COC4)C3)cccc2n1CC(F)(F)F] | 2-{3-[(4-methanesulfonyl-2-methoxyphenyl)amino]prop-1-yn-1-yl}-N-{2-oxaspiro[3.3]heptan-6-yl}-1-(2,2,2-trifluoroethyl)-1H-indol-4-amine | 548.2 |

TABLE 3-continued

| Compound No. | Structure | IUPAC | LC-MS (ES+, m/z) |
|---|---|---|---|
| 21A | 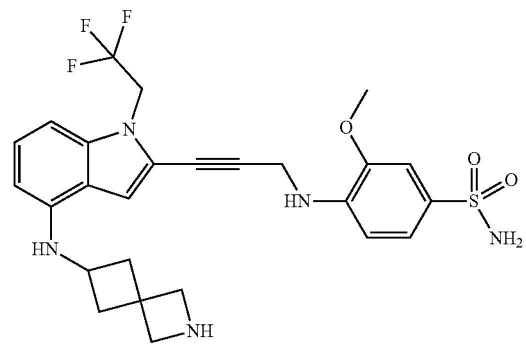 [SMILES: COc1cc(S(N)(=O)=O)ccc1NCC#Cc1cc2c(NC3CC4(CNC4)C3)cccc2n1CC(F)(F)F] | 4-({3-[4-({2-azaspiro[3.3]heptan-6-yl}amino)-1-(2,2,2-trifluoroethyl)-1H-indol-2-yl]prop-2-yn-1-yl}amino)-3-methoxybenzene-1-sulfonamide | 548.2 |
| 22A | 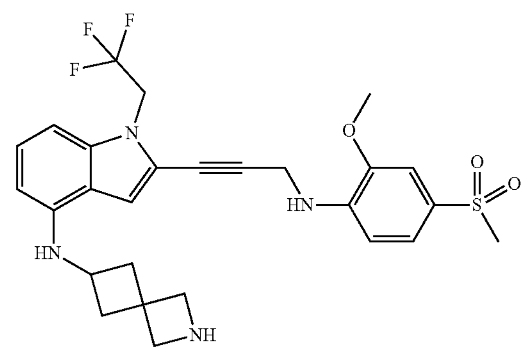 [SMILES: COc1cc(S(C)(=O)=O)ccc1NCC#Cc1cc2c(NC3CC4(CNC4)C3)cccc2n1CC(F)(F)F] | N-{2-azaspiro[3.3]heptan-6-yl}-2-{3-[(4-methanesulfonyl-2-methoxyphenyl)amino]prop-1-yn-1-yl}-1-(2,2,2-trifluoroethyl)-1H-indol-4-amine | 547.2 |
| 23A | 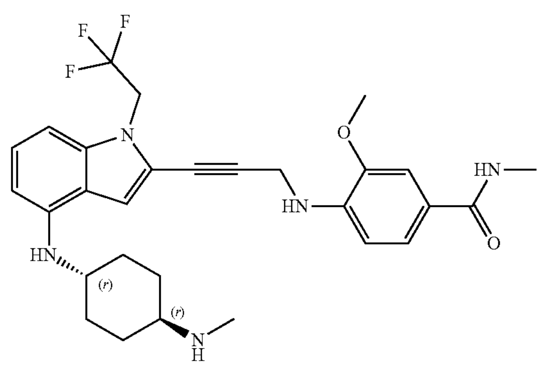 [SMILES: CNC(=O)c1ccc(NCC#Cc2cc3c(N[C@H]4CC[C@H](NC)CC4)cccc3n2CC(F)(F)F)c(OC)c1] | 3-methoxy-N-methyl-4-{[3-(4-{[(1R,4R)-4-(methylamino)cyclohexyl]amino}-1-(2,2,2-trifluoroethyl)-1H-indol-2-yl)prop-2-yn-1-yl]amino}benzamide | 542.2 |
| 24A | 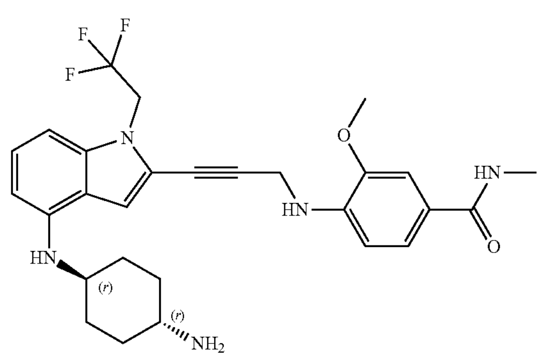 [SMILES: CNC(=O)c1ccc(NCC#Cc2cc3c(N[C@H]4CC[C@H](N)CC4)cccc3n2CC(F)(F)F)c(OC)c1] | 3-methoxy-N-methyl-4-{[3-(4-{[(1R,4R)-4-aminocyclohexyl]amino}-1-(2,2,2-trifluoroethyl)-1H-indol-2-yl)prop-2-yn-1-yl]amino}benzamide | 528.2 |

TABLE 3-continued

| Compound No. | Structure | IUPAC | LC-MS (ES+, m/z) |
|---|---|---|---|
| 25A | 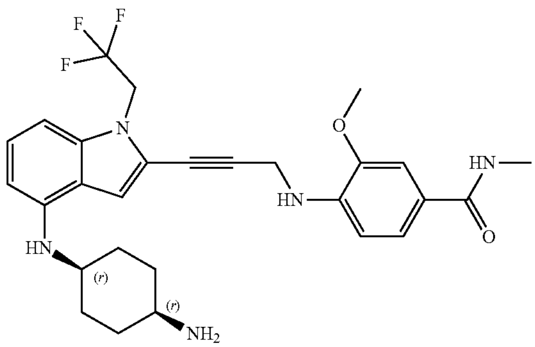 [SMILES: CNC(=O)c1ccc(NCC#Cc2cc3c(N[C@H]4CC[C@@H](N)CC4)cccc3n2CC(F)(F)F)c(OC)c1] | 3-methoxy-N-methyl-4-{[3-(4-{[(1S,4S-4-aminocyclohexyl]amino}-1-(2,2,2-trifluoroethyl)-1H-indol-2-yl)prop-2-yn-1-yl]amino}benzamide | 528.2 |
| 26A | 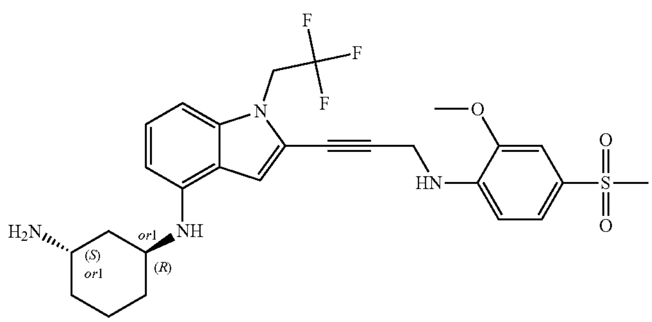 | rel-(1R,3R)-N$^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,3-diamine | 548.9 |
| 27A | 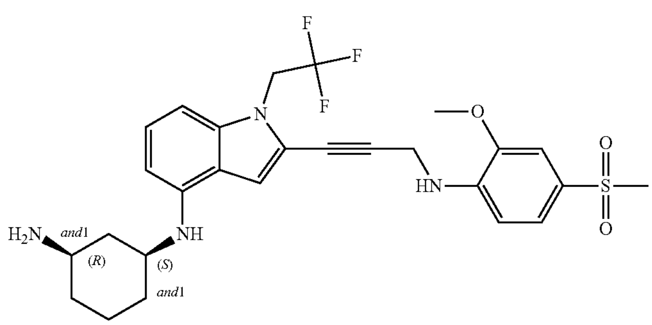 | rac-(1R,3S)-N$^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,3-diamine | 548.9 |
| 28A | 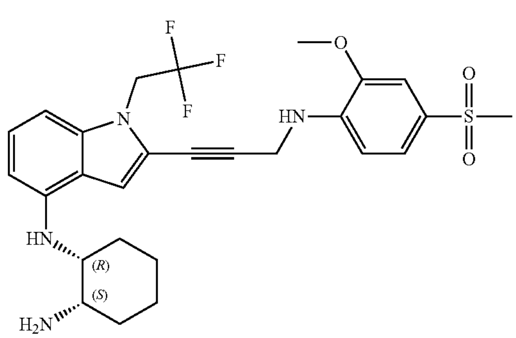 | (1R,2S)-N$^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,2-diamine | 548.9 |

TABLE 3-continued

| Compound No. | Structure | IUPAC | LC-MS (ES+, m/z) |
|---|---|---|---|
| 29A | 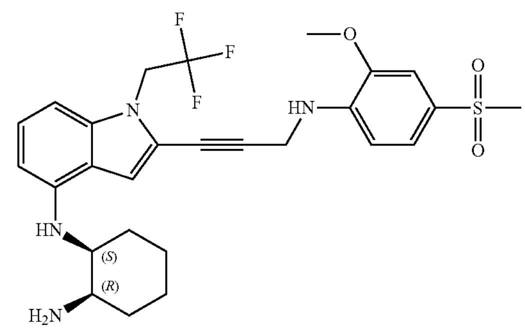 | rac-(1R,2S)-N¹-(2-{3-[(4-methanesulfonyl-2-methoxyphenyl)amino]prop-1-yn-1-yl}-1-(2,2,2-trifluoroethyl)-1H-indol-4-yl)cyclohexane-1,2-diamine | 548.9 |
| 30A | 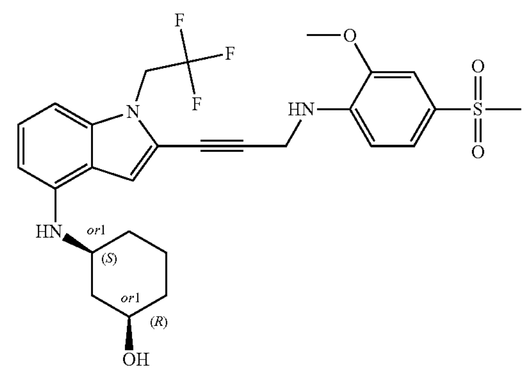 | rel-(1R,3S)-3-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol | 549.9 |
| 31A | 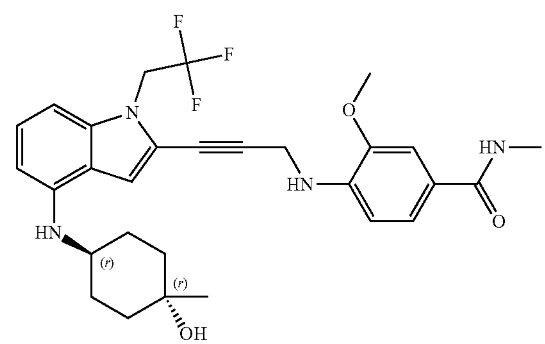 [SMILES: CNC(=O)c1ccc(NCC#Cc2cc3c(N[C@H]4CC[C@](C)(O)CC4)cccc3n2CC(F)(F)F)c(OC)c1] | 3-methoxy-N-methyl-4-{[3-(4-{[(1R,4R)-4-hydroxy-4-methyl-cyclohexyl]amino}-1-(2,2,2-trifluoroethyl)-1H-indol-2-yl)prop-2-yn-1-yl]amino}benzamide | 543.2 |
| 32A | 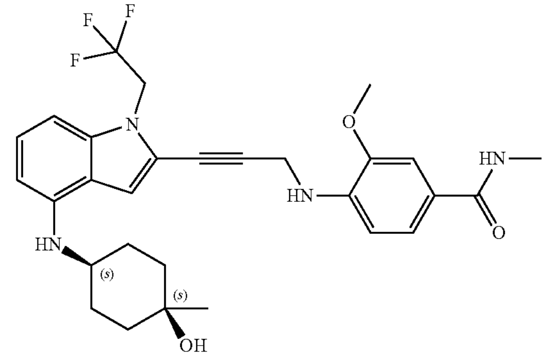 [SMILES: CNC(=O)c1ccc(NCC#Cc2cc3c(N[C@H]4CC[C@@](C)(O)CC4)cccc3n2CC(F)(F)F)c(OC)c1] | 3-methoxy-N-methyl-4-{[3-(4-{[(1S,4S)-4-hydroxy-4-methyl-cyclohexyl]amino}-1-(2,2,2-trifluoroethyl)-1H-indol-2-yl)prop-2-yn-1-yl]amino}benzamide | 543.2 |

TABLE 3-continued

| Compound No. | Structure | IUPAC | LC-MS (ES+, m/z) |
|---|---|---|---|
| 33A | 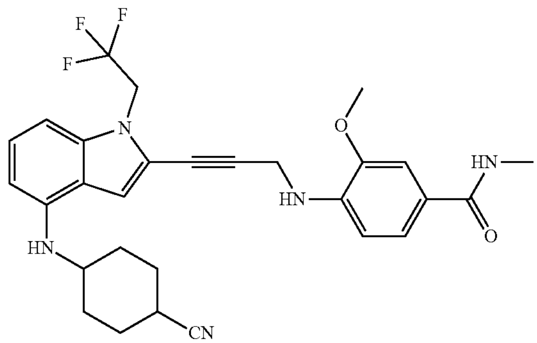 [SMILES: CNC(=O)c1ccc(NCC#Cc2cc3c(NC4CCC(C#N)CC4)cccc3n2CC(F)(F)F)c(OC)c1] | 4-[(3-{4-[(4-cyano-cyclohexyl)amino]-1-(2,2,2-trifluoroethyl)-1H-indol-2-yl}prop-2-yn-1-yl)amino]-3-methoxy-N-methylbenzamide | 538.2 |
| 34A | 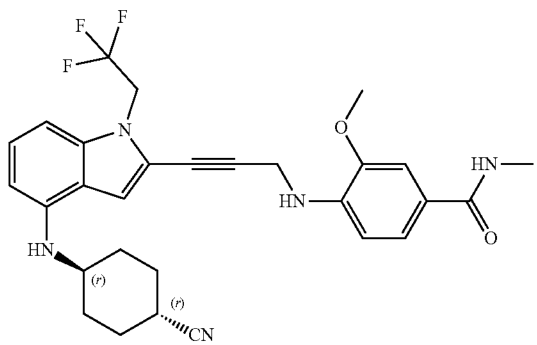 [SMILES: CNC(=O)c1ccc(NCC#Cc2cc3c(N[C@H]4CC[C@H](C#N)CC4)cccc3n2CC(F)(F)F)c(OC)c1] | 3-methoxy-N-methyl-4-{[3-(4-{[(1R,4R)-4-cyanocyclohexyl]amino}-1-(2,2,2-trifluoroethyl)-1H-indol-2-yl)prop-2-yn-1-yl]amino}benzamide | 538.2 |
| 35A | 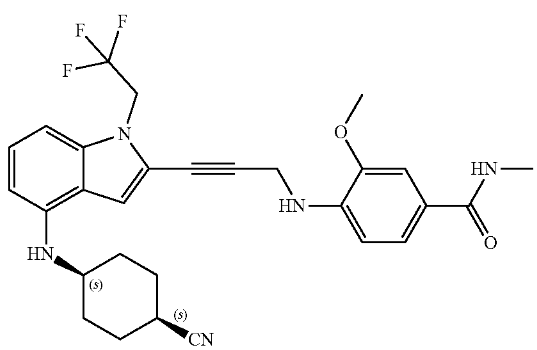 | 3-methoxy-N-methyl-4-{[3-(4-{[(1S,4S)-4-cyanocyclohexyl]amino}-1-(2,2,2-trifluoro-ethyl)-1H-indol-2-yl)prop-2-yn-1-yl]amino}benzamide | 538.2 |
| 36A | 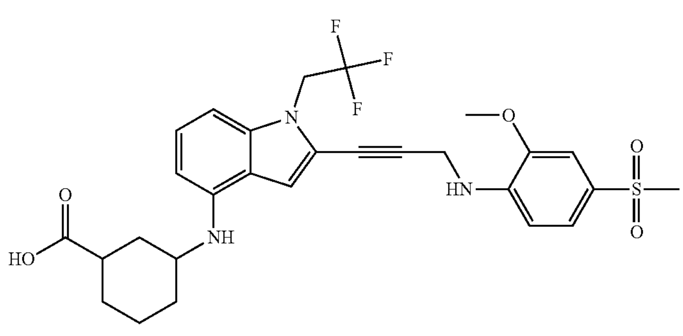 [SMILES: COc1cc(S(C)(=O)=O)ccc1NCC#Cc1cc2c(NC3CCCC(C(=O)O)C3)cccc2n1CC(F)(F)F] | 3-[(2-{3-[(4-methane-sulfonyl-2-methoxy-phenyl)amino]prop-1-yn-1-yl}-1-(2,2,2-trifluoroethyl)-1H-indol-4-yl)amino]cyclohexane-1-carboxylic acid | 577.9 |

TABLE 3-continued

| Compound No. | Structure | IUPAC | LC-MS (ES+, m/z) |
|---|---|---|---|
| 37A | 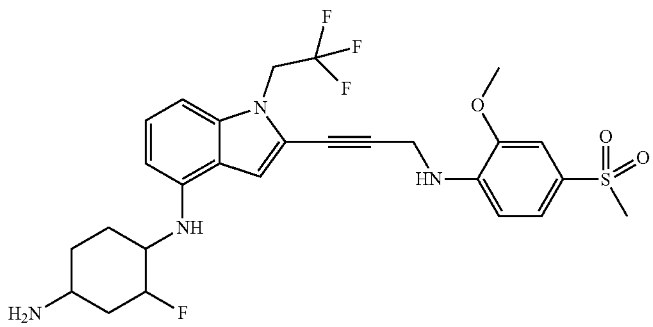 [SMILES: COc1cc(S(C)(=O)=O)ccc1NCC#Cc1cc2c(NC3CCC(N)CC3F)cccc2n1CC(F)(F)F] | 2-fluoro-N¹-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine | 567.2 |
| 38A | 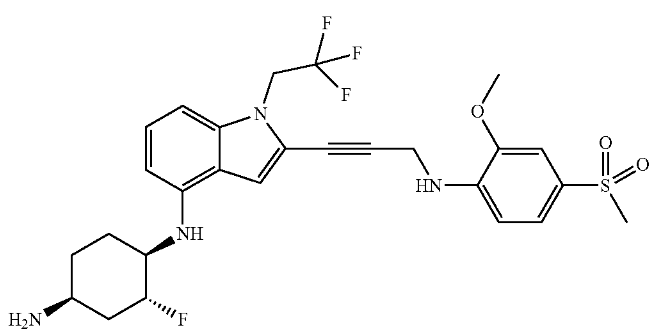 [SMILES: COc1cc(S(C)(=O)=O)ccc1NCC#Cc1cc2c(N[C@@H]3CC[C@H](N)C[C@H]3F)cccc2n1CC(F)(F)F] | (1R,2R,4S)-2-fluoro-N¹-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine | 567.2 |
| 39A | 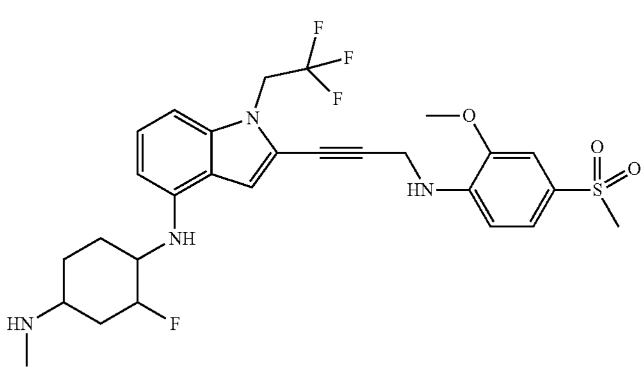 [SMILES: CNC1CCC(Nc2cccc3c2cc(C#CCNc2ccc(S(C)(=O)=O)cc2OC)n3CC(F)(F)F)C(F)C1] | 2-fluoro-N¹-(2-{3-[(4-methanesulfonyl-2-methoxyphenyl)amino]prop-1-yn-1-yl}-1-(2,2,2-trifluoroethyl)-1H-indol-4-yl)-N⁴-methyl-cyclohexane-1,4-diamine | 581.3 |

TABLE 3-continued

| Compound No. | Structure | IUPAC | LC-MS (ES+, m/z) |
|---|---|---|---|
| 40A | 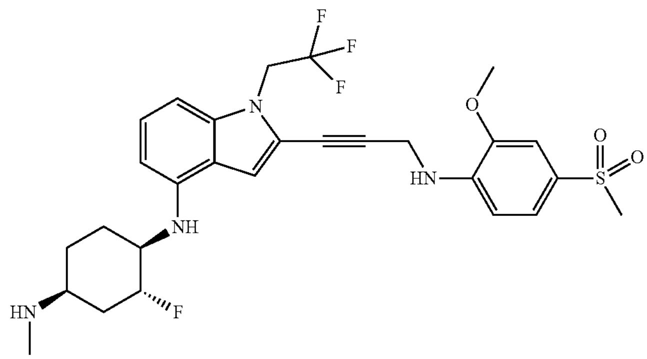 [SMILES: CN[C@H]1CC[C@@H](Nc2cccc3c2cc(C#CCNc2ccc(S(C)(=O)=O)cc2OC)n3CC(F)(F)F)[C@H](F)C1] | (1R,2R,4S)-2-fluoro-N¹-(2-(3-((2-methoxy-4-(methylsulfonyl)phenyl)amino)prop-1-yn-1-yl)-1-(2,2,2-trifluoroethyl)-1H-indol-4-yl)-N⁴-methylcyclohexane-1,4-diamine | 581.3 |
| 41A | 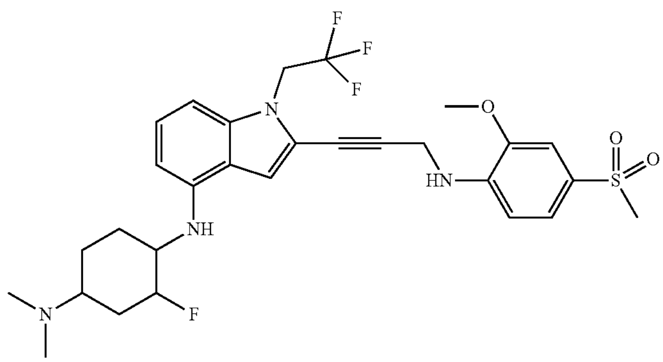 [SMILES: COc1cc(S(C)(=O)=O)ccc1NCC#Cc1cc2c(NC3CCC(N(C)C)CC3F)cccc2n1CC(F)(F)F] | 2-fluoro-N¹-(2-(3-((2-methoxy-4-(methylsulfonyl)phenyl)amino)prop-1-yn-1-yl)-1-(2,2,2-trifluoroethyl)-1H-indol-4-yl)-N⁴,N⁴-dimethylcyclohexane-1,4-diamine | 595.3 |
| 42A | 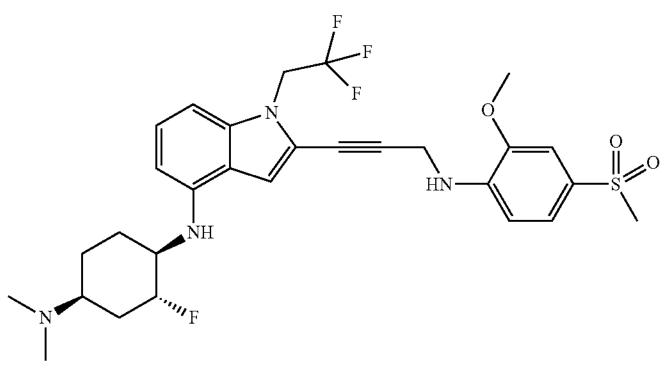 [SMILES: COc1cc(S(C)(=O)=O)ccc1NCC#Cc1cc2c(N[C@@H]3CC[C@H](N(C)C)C[C@H]3F)cccc2n1CC(F)(F)F] | (1R,2R,4S)-2-fluoro-N¹-(2-(3-((2-methoxy-4-(methylsulfonyl)phenyl)amino)prop-1-yn-1-yl)-1-(2,2,2-trifluoroethyl)-1H-indol-4-yl)-N⁴,N⁴-dimethylcyclohexane-1,4-diamine | 595.3 |
| 43A | 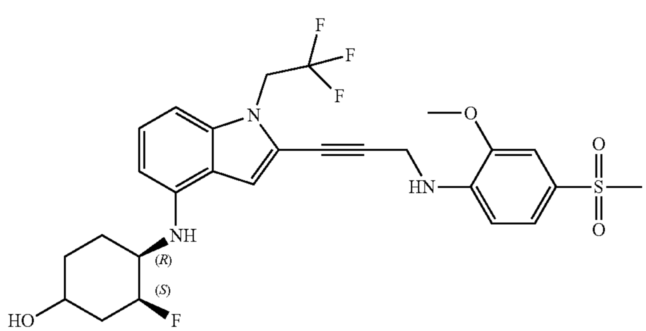 | (3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol | 568.2 |

TABLE 3-continued

| Compound No. | Structure | IUPAC | LC-MS (ES+, m/z) |
|---|---|---|---|
| 44A | 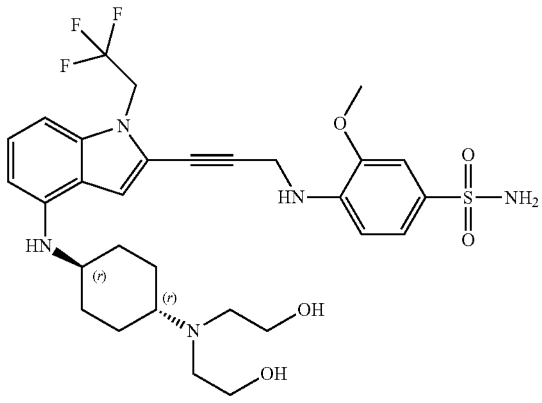 [SMILES: COc1cc(S(N)(=O)=O)ccc1NCC#Cc1cc2c(N[C@H]3CC[C@H](N(CCO)CCO)CC3)cccc2n1CC(F)(F)F] | 3-methoxy-4-{[3-(4-{[(1R,4R)-4-[bis(2-hydroxyethyl)amino]cyclohexyl]amino}-1-(2,2,2-trifluoroethyl)-1H-indol-2-yl)prop-2-yn-1-yl]amino}benzene-1-sulfonamide | 638.3 |
| 45A | 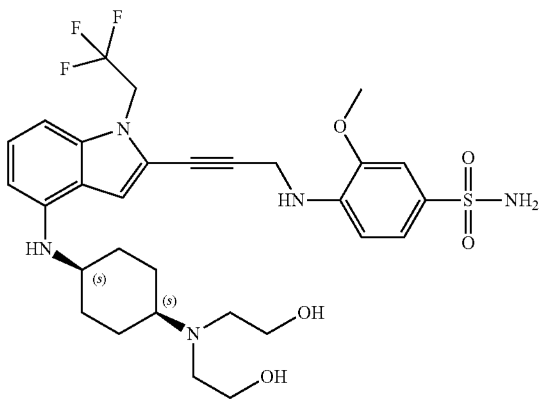 [SMILES: COc1cc(S(N)(=O)=O)ccc1NCC#Cc1cc2c(N[C@H]3CC[C@@H](N(CCO)CCO)CC3)cccc2n1CC(F)(F)F] | 3-methoxy-4-{[3-(4-{[(1S,4S)-4-[bis(2-hydroxyethyl)amino]cyclohexyl]amino}-1-(2,2,2-trifluoroethyl)-1H-indol-2-yl)prop-2-yn-1-yl]amino}benzene-1-sulfonamide | 638.3 |
| 46A | 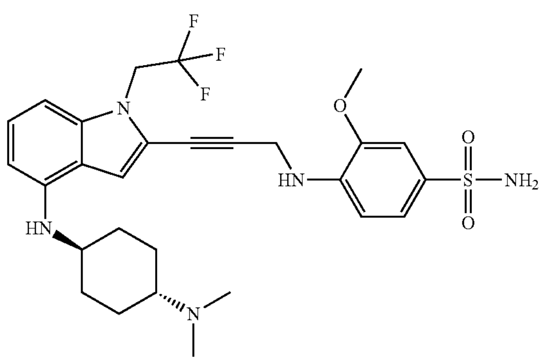 [SMILES: COc1cc(S(N)(=O)=O)ccc1NCC#Cc1cc2c(N[C@H]3CC[C@H](N(C)C)CC3)cccc2n1CC(F)(F)F] | 4-((3-(4-(((1R,4R)-4-(dimethylamino)cyclohexyl)amino)-1-(2,2,2-trifluoroethyl)-1H-indol-2-yl)prop-2-yn-1-yl)amino)-3-methoxybenzenesulfonamide | 578.2 |
| 47A | 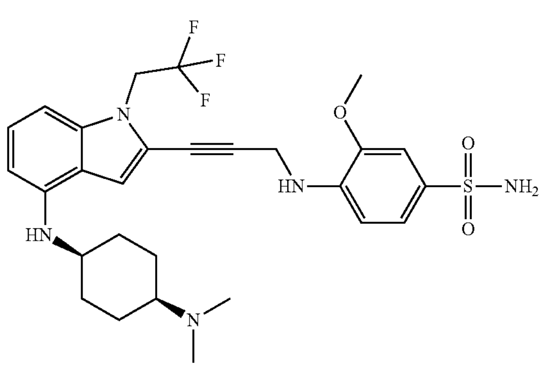 [SMILES: COc1cc(S(N)(=O)=O)ccc1NCC#Cc1cc2c(N[C@H]3CC[C@@H](N(C)C)CC3)cccc2n1CC(F)(F)F] | 4-((3-(4-(((1S,4S)-4-(dimethylamino)cyclohexyl)amino)-1-(2,2,2-trifluoroethyl)-1H-indol-2-yl)prop-2-yn-1-yl)amino)-3-methoxybenzenesulfonamide | 578.3 |

TABLE 3-continued

| Compound No. | Structure | IUPAC | LC-MS (ES+, m/z) |
|---|---|---|---|
| 48A | 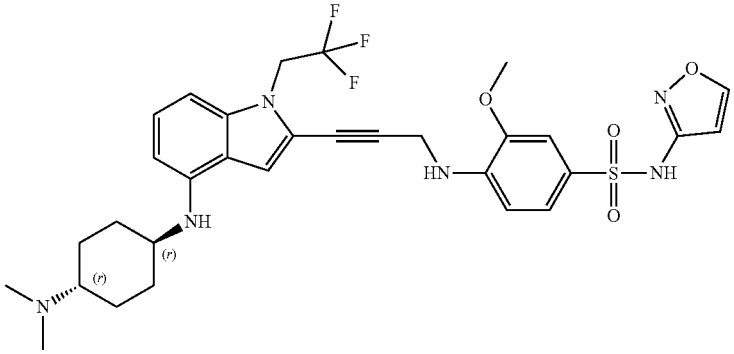 [SMILES: COc1cc(S(=O)(=O)Nc2ccon2)ccc1NCC#Cc1cc2c(N[C@H]3CC[C@H](N(C)C)CC3)cccc2n1CC(F)(F)F] | 3-methoxy-N-(1,2-oxazol-3-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide | 645.3 |
| 49A | 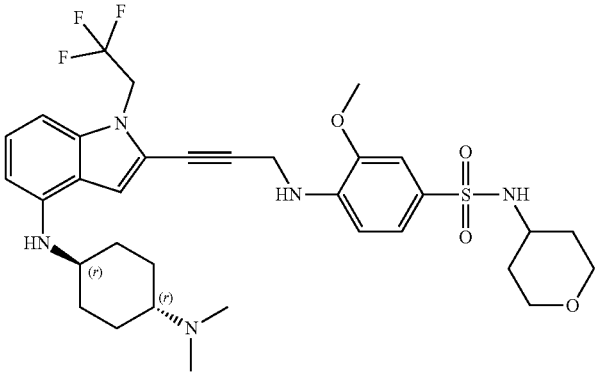 [SMILES: COc1cc(S(=O)(=O)NC2CCOCC2)ccc1NCC#Cc1cc2c(N[C@H]3CC[C@H](N(C)C)CC3)cccc2n1CC(F)(F)F] | 3-methoxy-N-(oxan-4-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide | 662.2 |
| 50A | 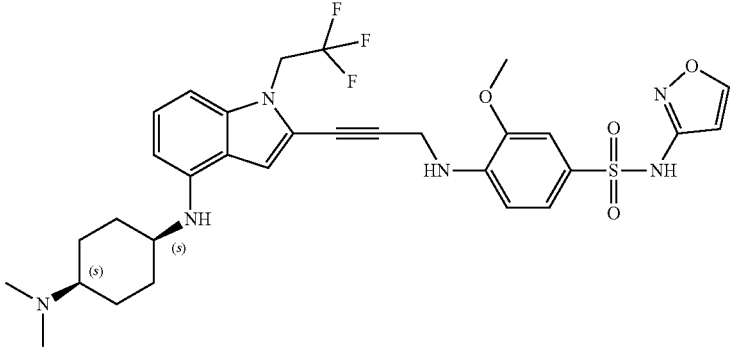 [SMILES: COc1cc(S(=O)(=O)Nc2ccon2)ccc1NCC#Cc1cc2c(N[C@H]3CC[C@@H](N(C)C)CC3)cccc2n1CC(F)(F)F] | 3-methoxy-N-(1,2-oxazol-3-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide | 645.2 |
| 51A | 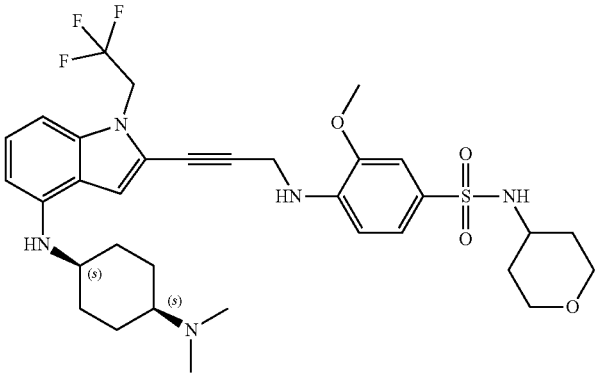 [SMILES: COc1cc(S(=O)(=O)NC2CCOCC2)ccc1NCC#Cc1cc2c(N[C@H]3CC[C@@H](N(C)C)CC3)cccc2n1CC(F)(F)F] | 3-methoxy-N-(oxan-4-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide | 662.3 |

TABLE 3-continued

| Compound No. | Structure | IUPAC | LC-MS (ES+, m/z) |
|---|---|---|---|
| 52A | 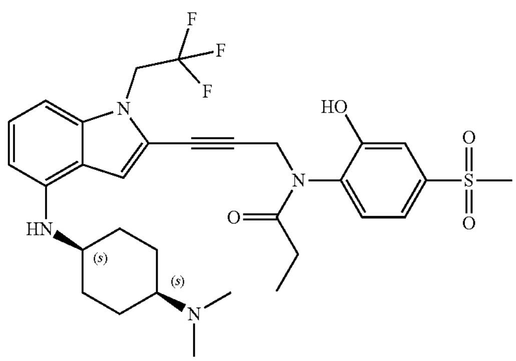 [SMILES: CCC(=O)N(CC#Cc1cc2c(N[C@H]3CC[C@@H](N(C)C)CC3)cccc2n1CC(F)(F)F)c1ccc(S(C)(=O)=O)cc1O] | N-(3-(4-(((1S,4S)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)propionamide | 619.1 |
| 53A | 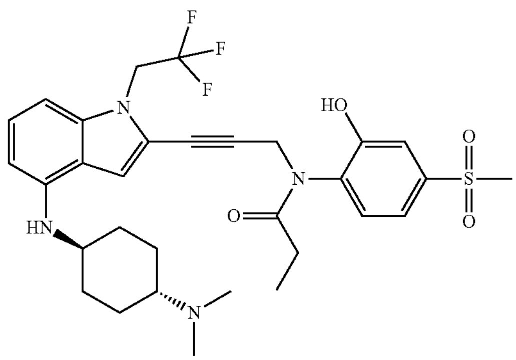 [SMILES: CCC(=O)N(CC#Cc1cc2c(N[C@H]3CC[C@H](N(C)C)CC3)cccc2n1CC(F)(F)F)c1ccc(S(C)(=O)=O)cc1O] | N-(3-(4-(((1R,4R)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)propionamide | |
| 54A | 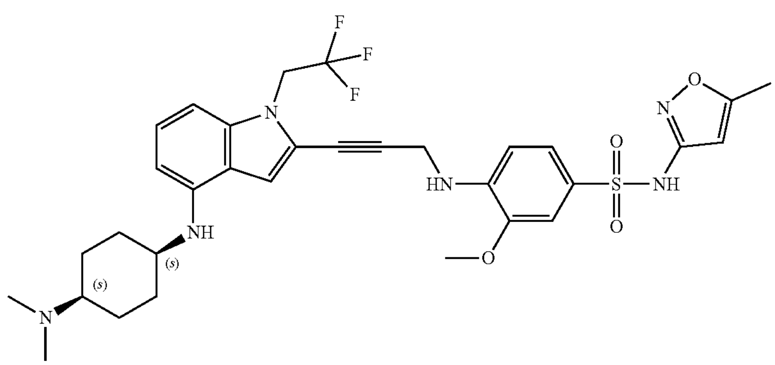 | 3-methoxy-N-(5-methyl-1,2-oxazol-3-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide | 659.2 |
| 55A | 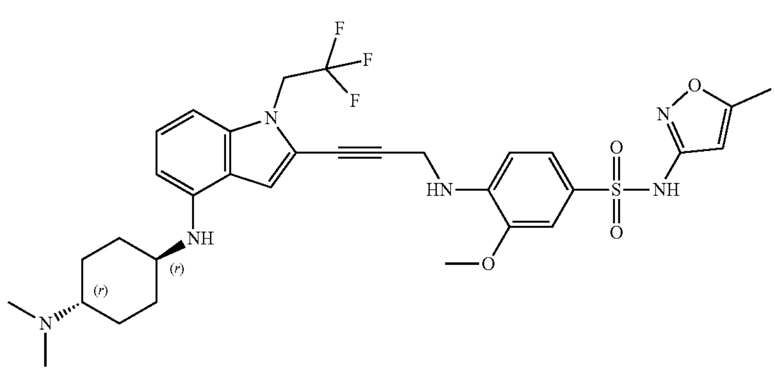 | 3-methoxy-N-(5-methyl-1,2-oxazol-3-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide | 659.3 |

TABLE 3-continued

| Compound No. | Structure | IUPAC | LC-MS (ES+, m/z) |
|---|---|---|---|
| 56A | 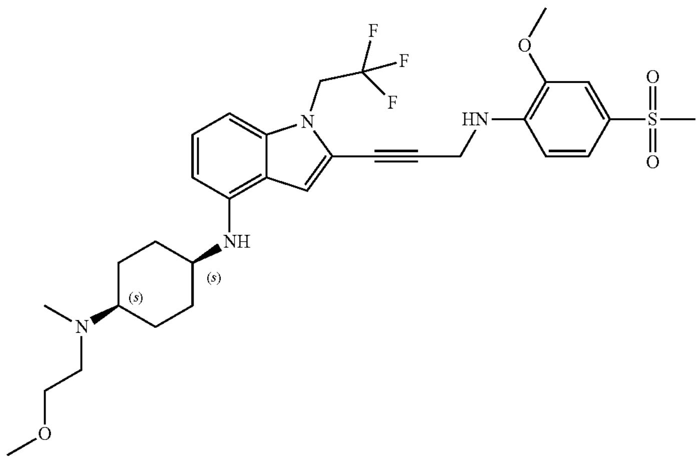 | (1S,4S)-N⁴-(2-{3-[(4-methanesulfonyl-2-methoxyphenyl)amino]prop-1-yn-1-yl}-1-(2,2,2-trifluoroethyl)-1H-indol-4-yl)-N¹-(2-methoxyethyl)-N¹-methylcyclohexane-1,4-diamine | 621.3 |
| 57A | 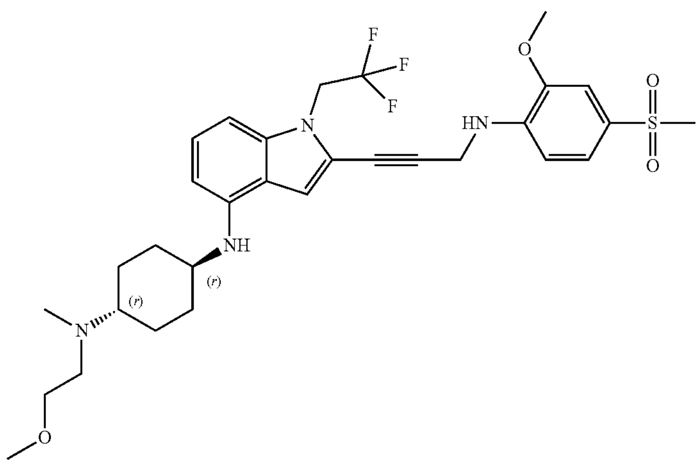 | (1R,4R)-N⁴-(2-{3-[(4-methanesulfonyl-2-methoxyphenyl)amino]prop-1-yn-1-yl}-1-(2,2,2-trifluoroethyl)-1H-indol-4-yl)-N¹-(2-methoxyethyl)-N¹-methylcyclohexane-1,4-diamine | 621.3 |
| 58A | 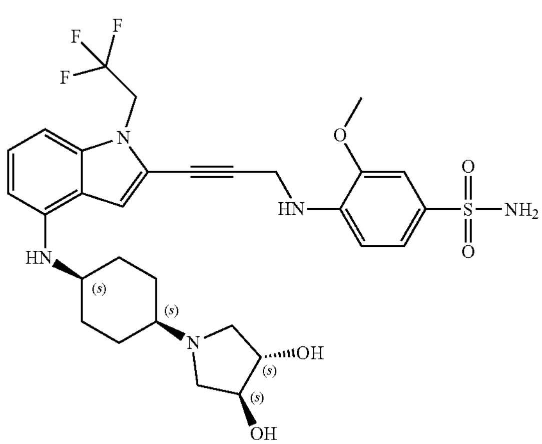 [SMILES: COc1cc(S(N)(=O)=O)ccc1NCC#Cc1cc2c(N[C@H]3CC[C@@H](N4C[C@H](O)[C@@H](O)C4)CC3)cccc2n1CC(F)(F)F] | 3-methoxy-4-{[3-(4-{[(1S,4S)-4-[(3S,4S)-3,4-dihydroxypyrrolidin-1-yl]cyclohexyl]amino}-1-(2,2,2-trifluoroethyl)-1H-indol-2-yl)prop-2-yn-1-yl]amino}benzene-1-sulfonamide | 636.2 |

TABLE 3-continued

| Compound No. | Structure | IUPAC | LC-MS (ES+, m/z) |
|---|---|---|---|
| 59A | 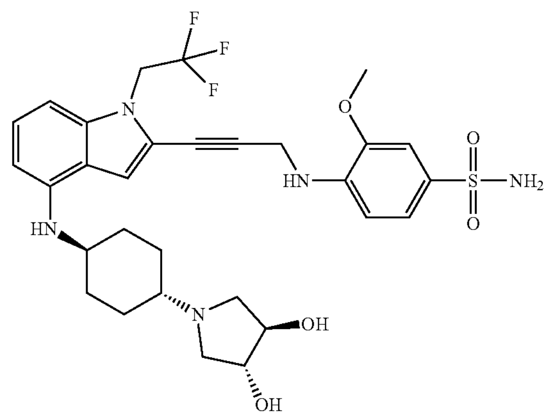 [SMILES: COc1cc(S(N)(=O)=O)ccc1NCC#Cc1cc2c(N[C@H]3CC[C@H](N4C[C@@H](O)[C@H](O)C4)CC3)cccc2n1CC(F)(F)F] | 4-((3-(4-(((1R,4R)-4-((3R,4R)-3,4-dihydroxypyrrolidin-1-yl)cyclohexyl)amino)-1-(2,2,2-trifluoroethyl)-1H-indol-2-yl)prop-2-yn-1-yl)amino)-3-methoxybenzenesulfonamide | 636.2 |
| 60A | 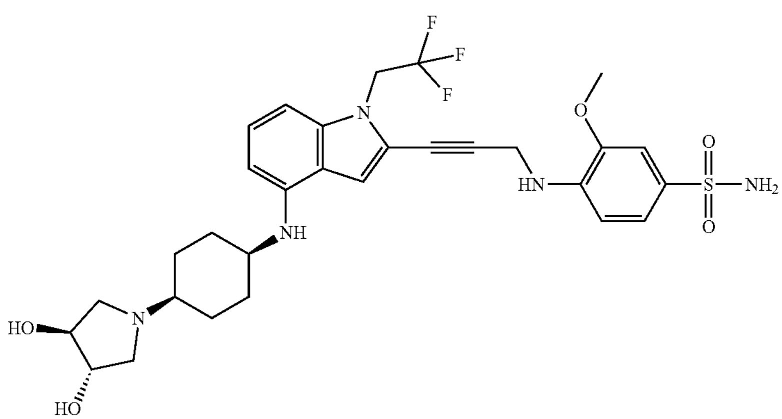 [SMILES: COc1cc(S(N)(=O)=O)ccc1NCC#Cc1cc2c(N[C@H]3CC[C@@H](N4C[C@H](O)[C@@H](O)C4)CC3)cccc2n1CC(F)(F)F] | 4-((3-(4-(((1R,4S)-4-((3S,4S)-3,4-dihydroxypyrrolidin-1-yl)cyclohexyl)amino)-1-(2,2,2-trifluoroethyl)-1H-indol-2-yl)prop-2-yn-1-yl)amino)-3-methoxybenzenesulfonamide | 636.2 |
| 61A | 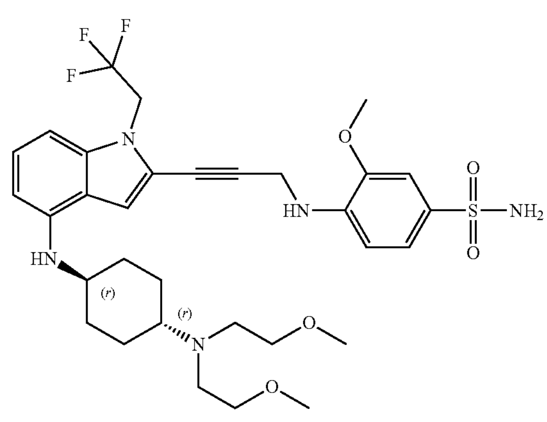 [SMILES: COCCN(CCOC)[C@H]1CC[C@H](Nc2cccc3c2cc(C#CCNc2ccc(S(N)(=O)=O)cc2OC)n3CC(F)(F)F)CC1] | 3-methoxy-4-{[3-(4-{[(1R,4R)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide | 666.3 |

TABLE 3-continued

| Compound No. | Structure | IUPAC | LC-MS (ES+, m/z) |
|---|---|---|---|
| 62A | 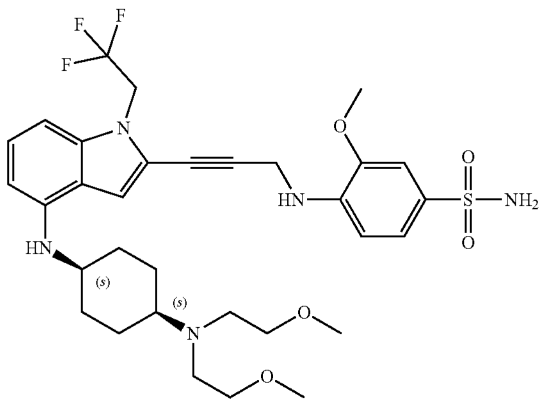 [SMILES: COCCN(CCOC)[C@H]1CC[C@@H](Nc2cccc3c2cc(C#CCNc2ccc(S(N)(=O)=O)cc2OC)n3CC(F)(F)F)CC1] | 3-methoxy-4-{[3-(4-{[(1S,4S)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide | 666.3 |
| 63A | 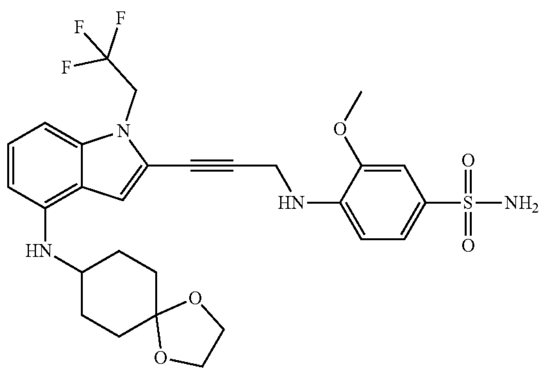 [SMILES: COc1cc(S(N)(=O)=O)ccc1NCC#Cc1cc2c(NC3CCC4(CC3)OCCO4)cccc2n1CC(F)(F)F] | 4-({3-[4-({1,4-dioxaspiro[4.5]decan-8-yl}amino)-1-(2,2,2-trifluoroethyl)-1H-indol-2-yl]prop-2-yn-1-yl}amino)-3-methoxybenzene-1-sulfonamide | 593.2 |
| 64A | 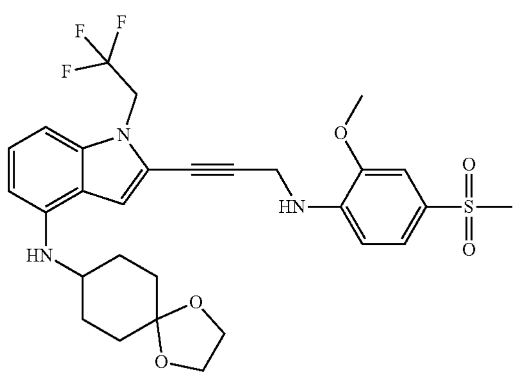 [SMILES: COc1cc(S(C)(=O)=O)ccc1NCC#Cc1cc2c(NC3CCC4(CC3)OCCO4)cccc2n1CC(F)(F)F] | N-{1,4-dioxaspiro[4.5]decan-8-yl}-2-{3-[(4-methanesulfonyl-2-methoxyphenyl)amino]prop-1-yn-1-yl}-1-(2,2,2-trifluoroethyl)-1H-indol-4-amine | 592.2 |
| 65A | 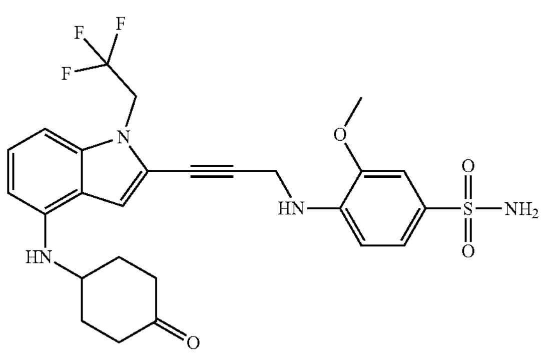 [SMILES: COc1cc(S(N)(=O)=O)ccc1NCC#Cc1cc2c(NC3CCC(=O)CC3)cccc2n1CC(F)(F)F] | 3-methoxy-4-[(3-{4-[(4-oxocyclohexyl)amino]-1-(2,2,2-trifluoroethyl)-1H-indol-2-yl}prop-2-yn-1-yl)amino]benzene-1-sulfonamide | 549.1 |

TABLE 3-continued

| Compound No. | Structure | IUPAC | LC-MS (ES+, m/z) |
|---|---|---|---|
| 66A | 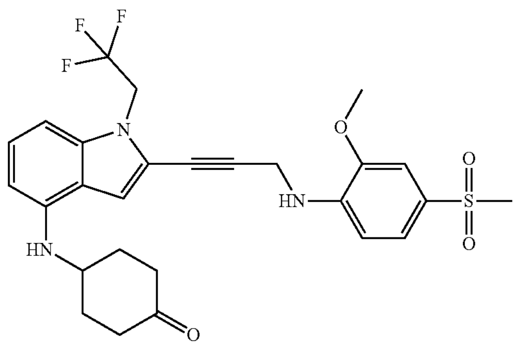 [SMILES: COc1cc(S(C)(=O)=O)ccc1NCC#Cc1cc2c(NC3CCC(=O)CC3)cccc2n1CC(F)(F)F] | 4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-one | 548.2 |
| 67A | 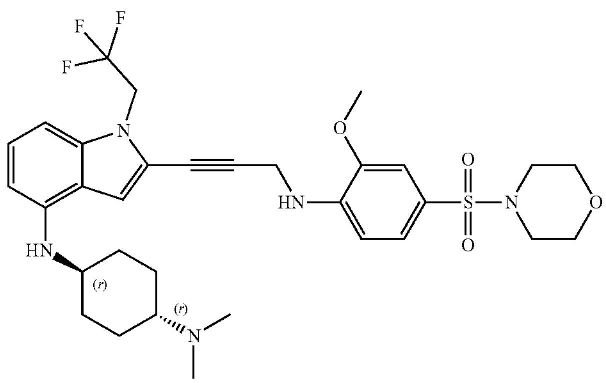 [SMILES: COc1cc(S(=O)(=O)N2CCOCC2)ccc1NCC#Cc1cc2c(N[C@H]3CC[C@H](N(C)C)CC3)cccc2n1CC(F)(F)F] | (1R,4R)-N⁴-[2-(3-{[2-methoxy-4-(morpholine-4-sulfonyl)phenyl]amino}prop-1-yn-1-yl)-1-(2,2,2-trifluoroethyl)-1H-indol-4-yl]-N¹,N¹-dimethylcyclohexane-1,4-diamine | 648.2 |
| 68A | 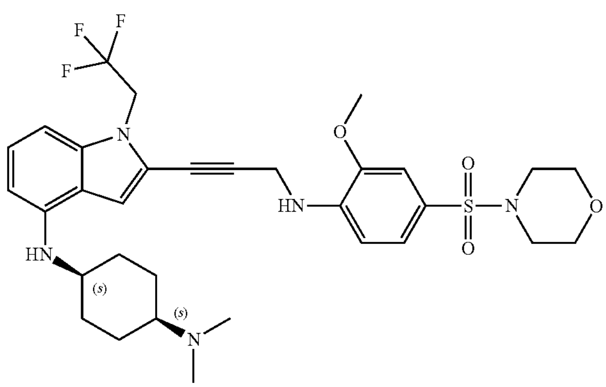 [SMILES: COc1cc(S(=O)(=O)N2CCOCC2)ccc1NCC#Cc1cc2c(N[C@H]3CC[C@@H](N(C)C)CC3)cccc2n1CC(F)(F)F] | (1S,4S)-N4-[2-(3-{[2-methoxy-4-(morpholine-4-sulfonyl)phenyl]amino}prop-1-yn-1-yl)-1-(2,2,2-trifluoroethyl)-1H-indol-4-yl]-N¹,N¹-dimethylcyclohexane-1,4-diamine | 648.3 |
| 69A | 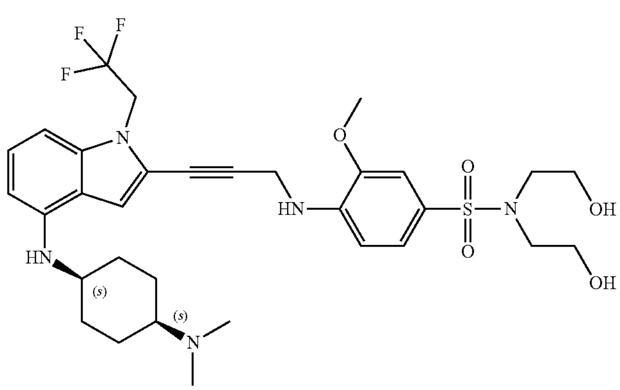 [SMILES: COc1cc(S(=O)(=O)N(CCO)CCO)ccc1NCC#Cc1cc2c(N[C@H]3CC[C@@H](N(C)C)CC3)cccc2n1CC(F)(F)F] | N,N-bis(2-hydroxyethyl)-3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide | 666.3 |

TABLE 3-continued

| Compound No. | Structure | IUPAC | LC-MS (ES+, m/z) |
|---|---|---|---|
| 70A | 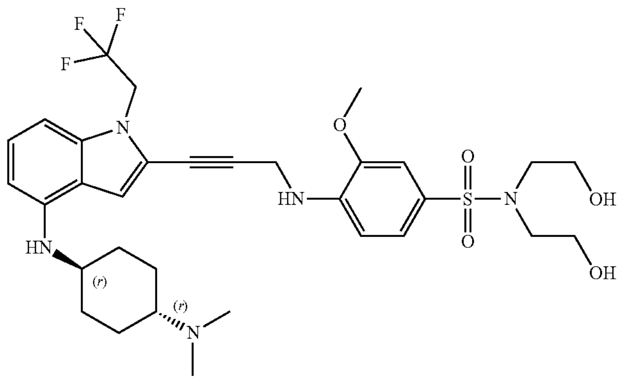 [SMILES: COc1cc(S(=O)(=O)N(CCO)CCO)ccc1NCC#Cc1cc2c(N[C@H]3CC[C@H](N(C)C)CC3)cccc2n1CC(F)(F)F] | N,N-bis(2-hydroxyethyl)-3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide | 666.2 |
| 71A | 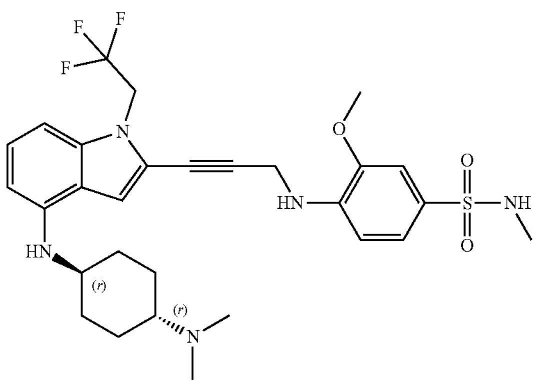 [SMILES: CNS(=O)(=O)c1ccc(NCC#Cc2cc3c(N[C@H]4CC[C@H](N(C)C)CC4)cccc3n2CC(F)(F)F)c(OC)c1] | 3-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide | 592.2 |
| 72A | 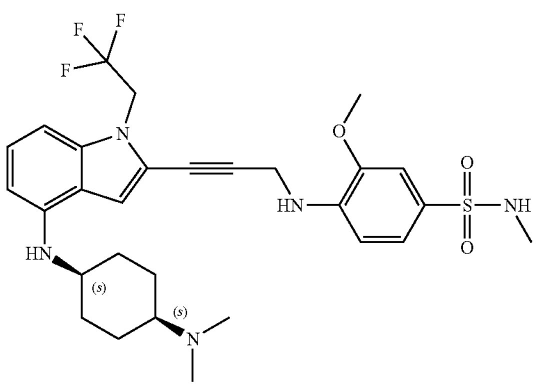 [SMILES: CNS(=O)(=O)c1ccc(NCC#Cc2cc3c(N[C@H]4CC[C@@H](N(C)C)CC4)cccc3n2CC(F)(F)F)c(OC)c1] | 3-methoxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide | 592.3 |
| 73A | 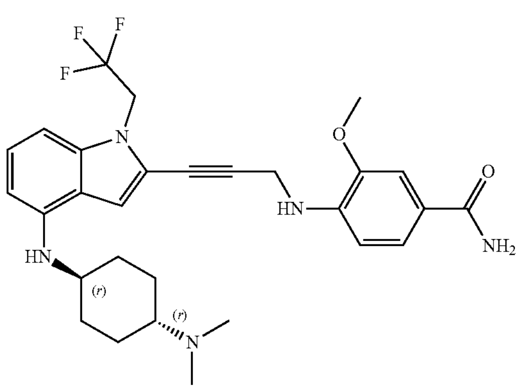 [SMILES: COc1cc(C(N)=O)ccc1NCC#Cc1cc2c(N[C@H]3CC[C@H](N(C)C)CC3)cccc2n1CC(F)(F)F] | 3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide | 542.2 |

TABLE 3-continued

| Compound No. | Structure | IUPAC | LC-MS (ES+, m/z) |
|---|---|---|---|
| 74A | 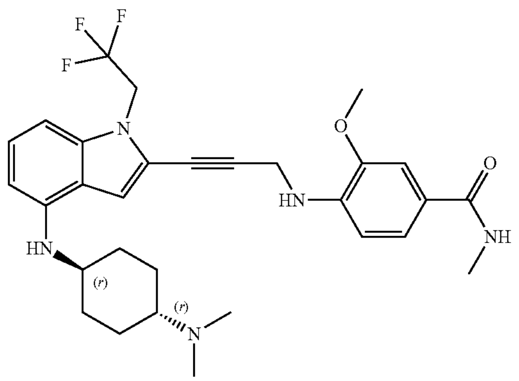 [SMILES: CNC(=O)c1ccc(NCC#Cc2cc3c(N[C@H]4CC[C@H](N(C)C)CC4)cccc3n2CC(F)(F)F)c(OC)c1] | 3-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide | 556.3 |
| 75A | 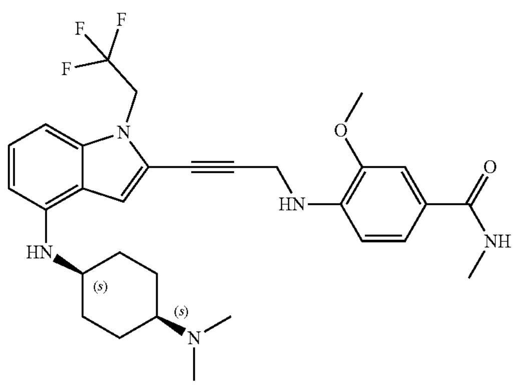 [SMILES: CNC(=O)c1ccc(NCC#Cc2cc3c(N[C@H]4CC[C@@H](N(C)C)CC4)cccc3n2CC(F)(F)F)c(OC)c1] | 3-methoxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide | 556.3 |
| 76A | 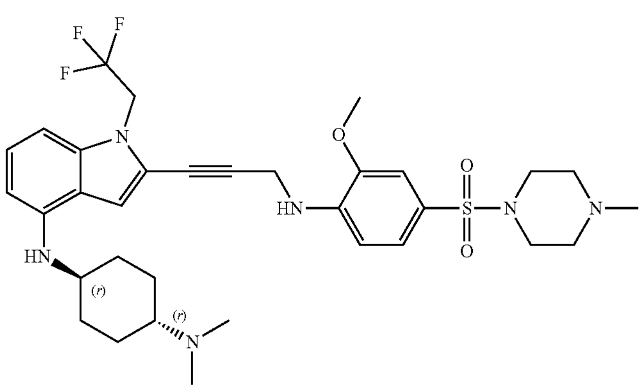 [SMILES: COc1cc(S(=O)(=O)N2CCN(C)CC2)ccc1NCC#Cc1cc2c(N[C@H]3CC[C@H](N(C)C)CC3)cccc2n1CC(F)(F)F] | (1R,4R)-N4-{2-[3-({2-methoxy-4-[(4-methylpiperazin-1-yl)sulfonyl]phenyl}amino)prop-1-yn-1-yl]-1-(2,2,2-trifluoroethyl)-1H-indol-4-yl}-N1,N1-dimethylcyclohexane-1,4-diamine | 661.4 |
| 77A | 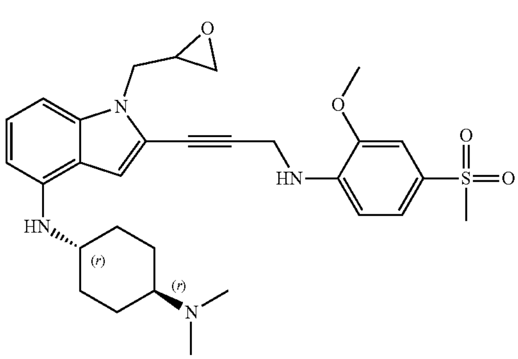 [SMILES: COc1cc(S(C)(=O)=O)ccc1NCC#Cc1cc2c(N[C@H]3CC[C@H](N(C)C)CC3)cccc2n1CC1CO1] | (1R,4R)-N4-(2-{3-[(4-methanesulfonyl-2-methoxyphenyl)amino]prop-1-yn-1-yl}-1-[(oxiran-2-yl)methyl]-1H-indol-4-yl)-N1,N1-dimethylcyclohexane-1,4-diamine | 551.1 |

TABLE 3-continued

| Compound No. | Structure | IUPAC | LC-MS (ES+, m/z) |
|---|---|---|---|
| 78A | 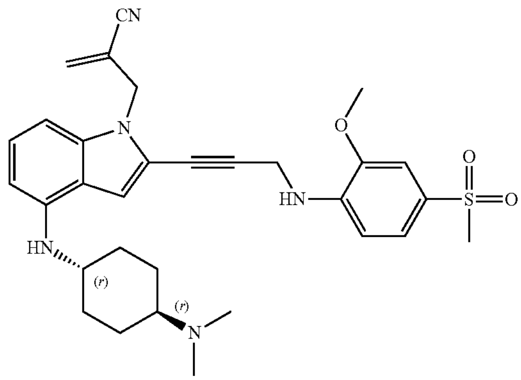 [SMILES: C=C(C#N)Cn1c(C#CCNc2ccc(S(C)(=O)=O)cc2OC)cc2c(N[C@H]3CC[C@H](N(C)C)CC3)cccc21] | 2-[(2-{3-[(4-methane-sulfonyl-2-methoxy-phenyl)amino]prop-1-yn-1-yl}-4-{[(1R,4R)-4-(dimethylamino)cyclohexyl]amino}-1H-indol-1-yl)methyl]prop-2-enenitrile | 560.4 |
| 79A | 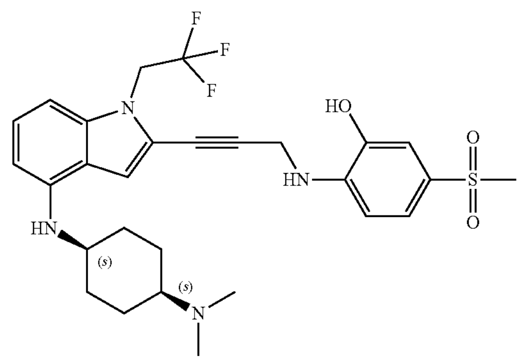 [SMILES: CN(C)[C@H]1CC[C@@H](Nc2cccc3c2cc(C#CCNc2ccc(S(C)(=O)=O)cc2O)n3CC(F)(F)F)CC1] | 5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenol | 563.1 |
| 80A | 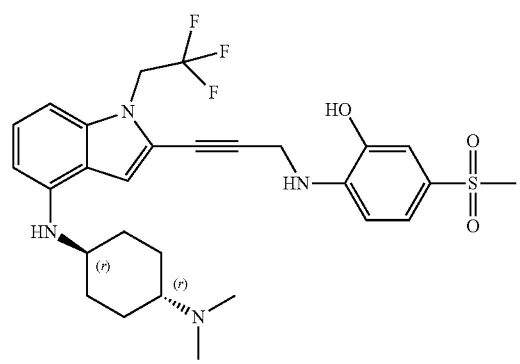 [SMILES: CN(C)[C@H]1CC[C@H](Nc2cccc3c2cc(C#CCNc2ccc(S(C)(=O)=O)cc2O)n3CC(F)(F)F)CC1] | 5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenol | 563.2 |
| 81A | 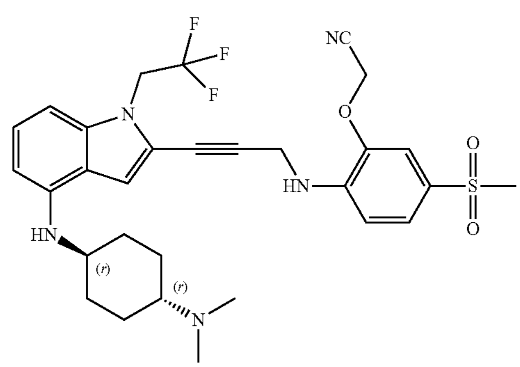 [SMILES: CN(C)[C@H]1CC[C@H](Nc2cccc3c2cc(C#CCNc2ccc(S(C)(=O)=O)cc2OCC#N)n3CC(F)(F)F)CC1] | 2-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenoxy)acetonitrile | 602.3 |

TABLE 3-continued

| Compound No. | Structure | IUPAC | LC-MS (ES+, m/z) |
|---|---|---|---|
| 82A | 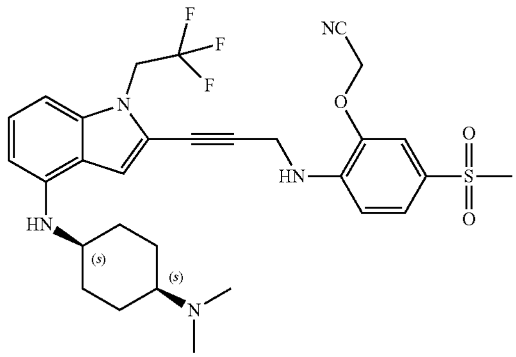 [SMILES: CN(C)[C@H]1CC[C@@H](Nc2cccc3c2cc(C#CCNc2ccc(S(C)(=O)=O)cc2OCC#N)n3CC(F)(F)F)CC1] | 2-(5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenoxy)acetonitrile | 602.2 |
| 83A | 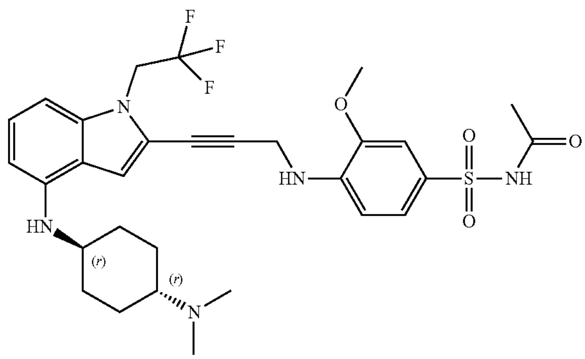 [SMILES: COc1cc(S(=O)(=O)NC(C)=O)ccc1NCC#Cc1cc2c(N[C@H]3CC[C@H](N(C)C)CC3)cccc2n1CC(F)(F)F] | N-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzenesulfonyl)acetamide | 620.1 |
| 84A | 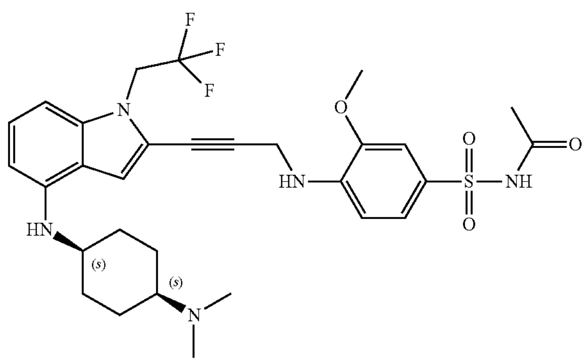 [SMILES: COc1cc(S(=O)(=O)NC(C)=O)ccc1NCC#Cc1cc2c(N[C@H]3CC[C@@H](N(C)C)CC3)cccc2n1CC(F)(F)F] | N-(3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzenesulfonyl)acetamide | 620.3 |
| 85A | 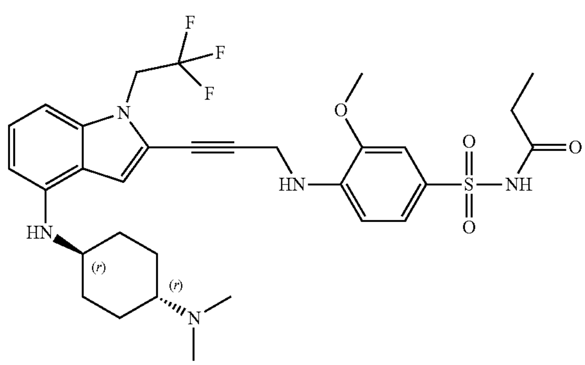 [SMILES: CCC(=O)NS(=O)(=O)c1ccc(NCC#Cc2cc3c(N[C@H]4CC[C@H](N(C)C)CC4)cccc3n2CC(F)(F)F)c(OC)c1] | N-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzenesulfonyl)propanamide | 634.3 |

TABLE 3-continued

| Compound No. | Structure | IUPAC | LC-MS (ES+, m/z) |
|---|---|---|---|
| 86A | 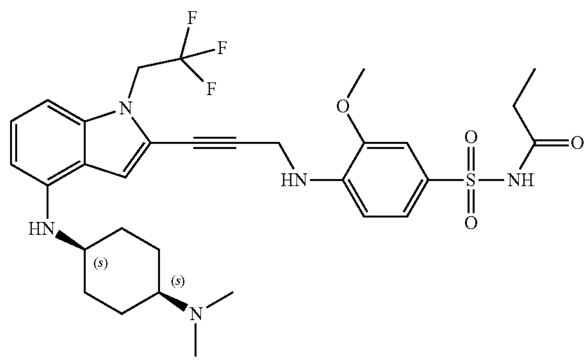 [SMILES: CCC(=O)NS(=O)(=O)c1ccc(NCC#Cc2cc3c(N[C@H]4CC[C@@H](N(C)C)CC4)cccc3n2CC(F)(F)F)c(OC)c1] | N-(3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzenesulfonyl)propanamide | 634.2 |
| 87A | 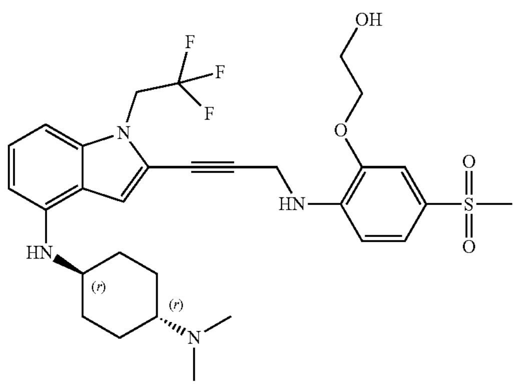 [SMILES: CN(C)[C@H]1CC[C@H](Nc2cccc3c2cc(C#CCNc2ccc(S(C)(=O)=O)cc2OCCO)n3CC(F)(F)F)CC1] | 2-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenoxy)ethan-1-ol | 607.1 |
| 88A | 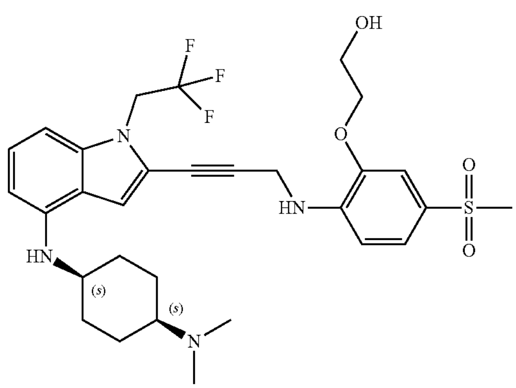 [SMILES: CN(C)[C@H]1CC[C@@H](Nc2cccc3c2cc(C#CCNc2ccc(S(C)(=O)=O)cc2OCCO)n3CC(F)(F)F)CC1] | 2-(5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenoxy)ethan-1-ol | 607.4 |
| 89A | 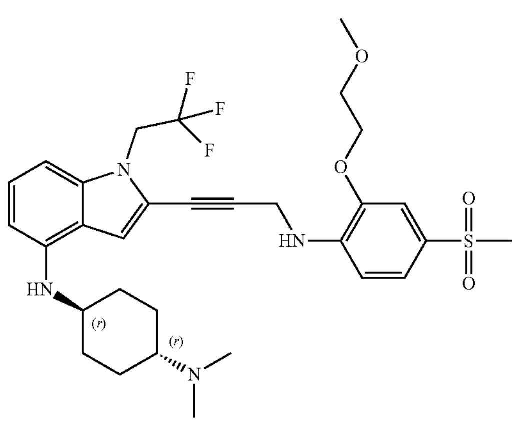 [SMILES: COCCOc1cc(S(C)(=O)=O)ccc1NCC#Cc1cc2c(N[C@H]3CC[C@H](N(C)C)CC3)cccc2n1CC(F)(F)F] | (1R,4R)-N4-[2-(3-{[4-methanesulfonyl-2-(2-methoxyethoxy)phenyl]amino}prop-1-yn-1-yl)-1-(2,2,2-trifluoroethyl)-1H-indol-4-yl]-N1,N1-dimethylcyclohexane-1,4-diamine | 621.4 |

TABLE 3-continued

| Compound No. | Structure | IUPAC | LC-MS (ES+, m/z) |
|---|---|---|---|
| 90A | 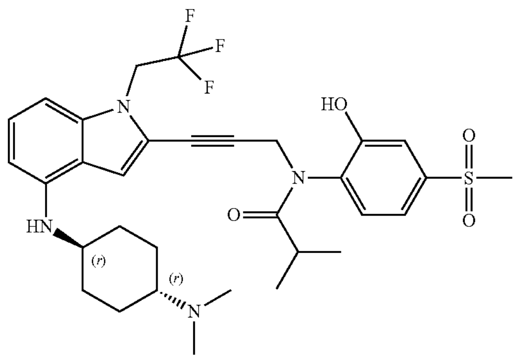 [SMILES: CC(C)C(=O)N(CC#Cc1cc2c(N[C@H]3CC[C@H](N(C)C)CC3)cccc2n1CC(F)(F)F)c1ccc(S(C)(=O)=O)cc1O] | N-(3-(4-(((1R,4R)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide | 633.3 |
| 91A | 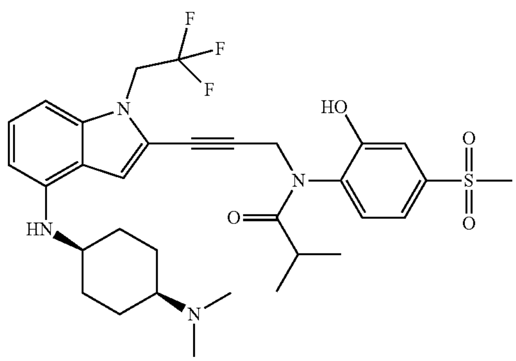 [SMILES: CC(C)C(=O)N(CC#Cc1cc2c(N[C@H]3CC[C@@H](N(C)C)CC3)cccc2n1CC(F)(F)F)c1ccc(S(C)(=O)=O)cc1O] | N-(3-(4-(((1S,4S)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide | 633.3 |
| 92A | 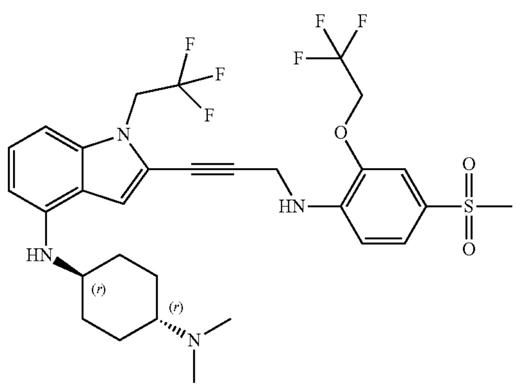 [SMILES: CN(C)[C@H]1CC[C@H](Nc2cccc3c2cc(C#CCNc2ccc(S(C)(=O)=O)cc2OCC(F)(F)F)n3CC(F)(F)F)CC1] | (1R,4R)-N$^4$-[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]-N$^1$,N$^1$-dimethylcyclohexane-1,4-diamine | 645.3 |
| 93A | 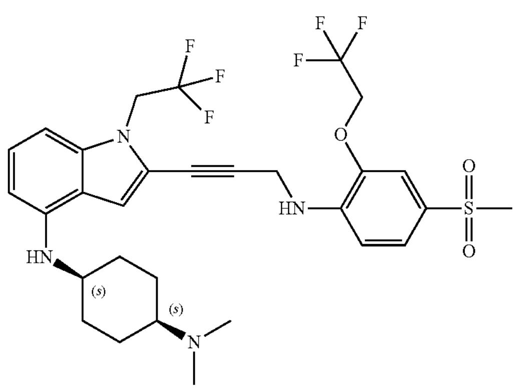 [SMILES: CN(C)[C@H]1CC[C@@H](Nc2cccc3c2cc(C#CCNc2ccc(S(C)(=O)=O)cc2OCC(F)(F)F)n3CC(F)(F)F)CC1] | (1S,4S)-N$^4$-[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]-N$^1$,N$^1$-dimethylcyclohexane-1,4-diamine | 645.3 |

TABLE 3-continued

| Compound No. | Structure | IUPAC | LC-MS (ES+, m/z) |
|---|---|---|---|
| 94A | 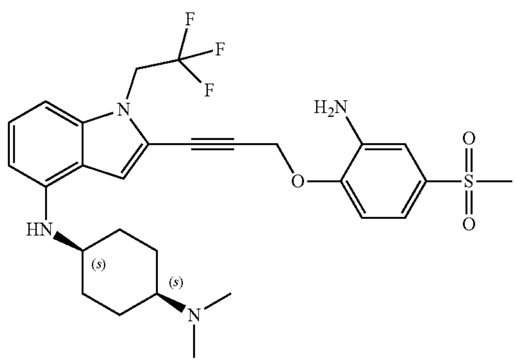 [SMILES: CN(C)[C@H]1CC[C@@H](Nc2cccc3c2cc(C#CCOc2ccc(S(C)(=O)=O)cc2N)n3CC(F)(F)F)CC1] | (1S,4S)- N4-{2-[3-(2-amino-4-methane-sulfonylphenoxy)prop-1-yn-1-yl]-1-(2,2,2-trifluoroethyl)-1H-indol-4-yl}-N¹,N¹-dimethylcyclohexane-1,4-diamine | 563.1 |
| 95A | 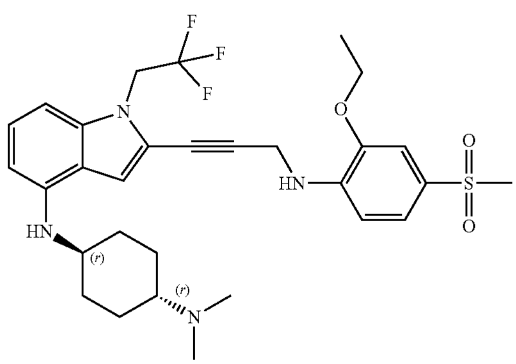 [SMILES: CCOc1cc(S(C)(=O)=O)ccc1NCC#Cc1cc2c(N[C@H]3CC[C@H](N(C)C)CC3)cccc2n1CC(F)(F)F] | (1R,4R)-N⁴-(2-{3-[(2-ethoxy-4-methane-sulfonylphenyl)amino]prop-1-yn-1-yl}-1-(2,2,2-trifluoroethyl)-1H-indol-4-yl)-N¹,N¹-dimethylcyclohexane-1,4-diamine | 591.2 |
| 96A | 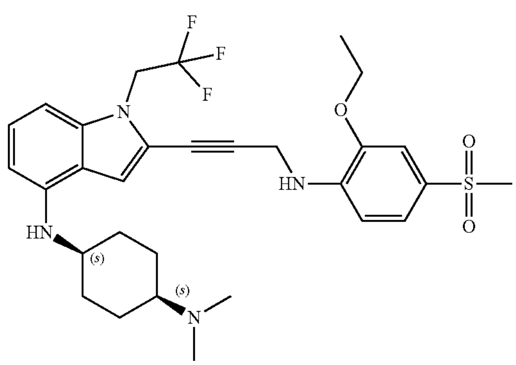 | (1S,4S)-N⁴-(2-{3-[(2-ethoxy-4-methane-sulfonylphenyl)amino]prop-1-yn-1-yl}-1-(2,2,2-trifluoroethyl)-1H-indol-4-yl)-N¹,N¹-dimethylcyclohexane-1,4-diamine | 591.2 |
| 97A | 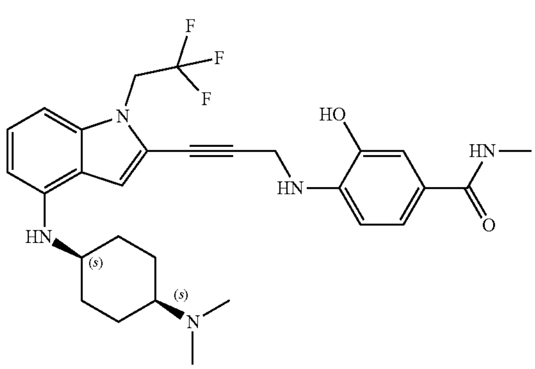 | 3-hydroxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide | 542.2 |

TABLE 3-continued

| Compound No. | Structure | IUPAC | LC-MS (ES+, m/z) |
|---|---|---|---|
| 98A | 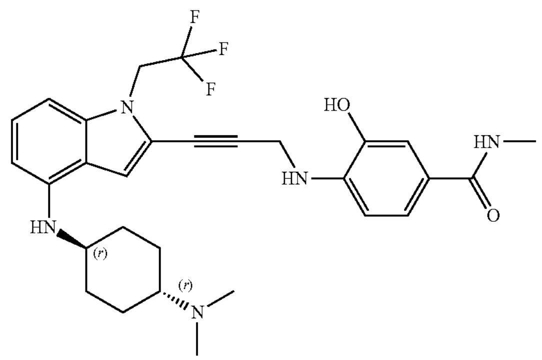 [SMILES: CNC(=O)c1ccc(NCC#Cc2cc3c(N[C@H]4CC[C@H](N(C)C)CC4)cccc3n2CC(F)(F)F)c(O)c1] | 3-hydroxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide | 542.2 |
| 99A | 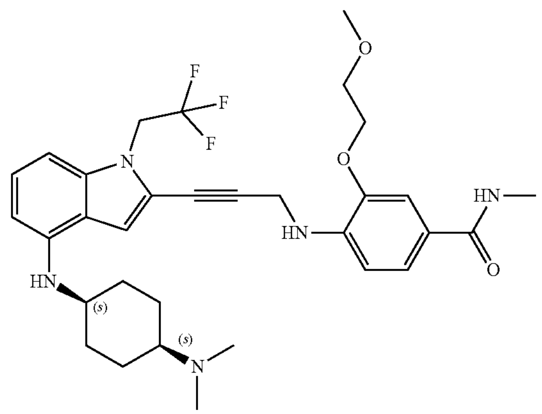 [SMILES: CNC(=O)c1ccc(NCC#Cc2cc3c(N[C@H]4CC[C@@H](N(C)C)CC4)cccc3n2CC(F)(F)F)c(OCCOC)c1] | 3-(2-methoxyethoxy)-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide | 600.3 |
| 100A | 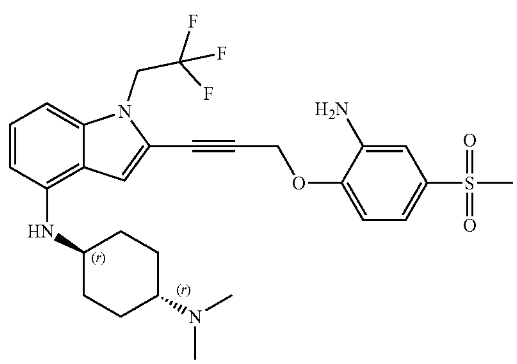 [SMILES: CN(C)[C@H]1CC[C@H](Nc2cccc3c2cc(C#CCOc2ccc(S(C)(=O)=O)cc2N)n3CC(F)(F)F)CC1] | (1R,4R)-N4-{2-[3-(2-amino-4-methanesulfonylphenoxy)prop-1-yn-1-yl]-1-(2,2,2-trifluoroethyl)-1H-indol-4-yl}-N1,N1-dimethylcyclohexane-1,4-diamine | 563.2 |
| 101A | 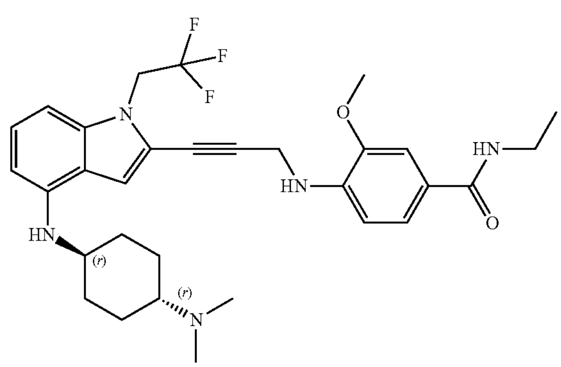 | N-ethyl-3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide | 570.3 |

TABLE 3-continued

| Compound No. | Structure | IUPAC | LC-MS (ES+, m/z) |
|---|---|---|---|
| 102A | 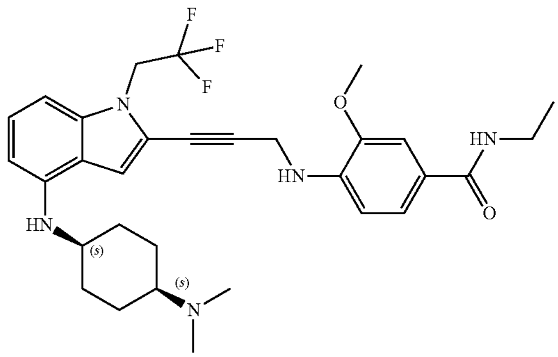 [SMILES: CCNC(=O)c1ccc(NCC#Cc2cc3c(N[C@H]4CC[C@@H](N(C)C)CC4)cccc3n2CC(F)(F)F)c(OC)c1] | N-ethyl-3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide | 570.3 |
| 103A | 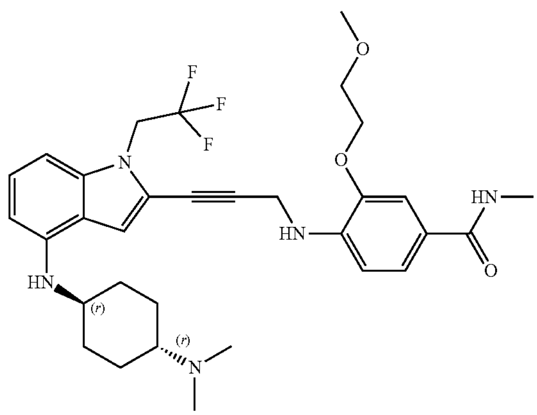 [SMILES: CNC(=O)c1ccc(NCC#Cc2cc3c(N[C@H]4CC[C@H](N(C)C)CC4)cccc3n2CC(F)(F)F)c(OCCOC)c1] | 3-(2-methoxyethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide | 600.3 |
| 104A | 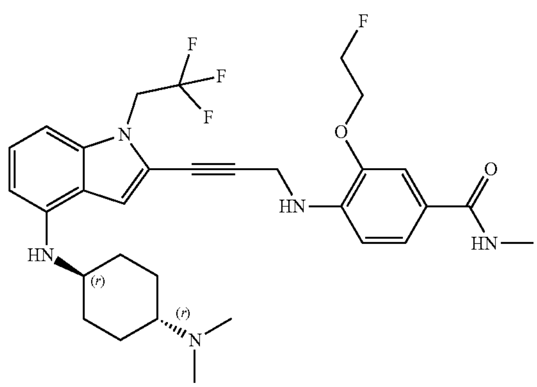 [SMILES: CNC(=O)c1ccc(NCC#Cc2cc3c(N[C@H]4CC[C@H](N(C)C)CC4)cccc3n2CC(F)(F)F)c(OCCF)c1] | 3-(2-fluoroethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide | 588.3 |
| 105A | 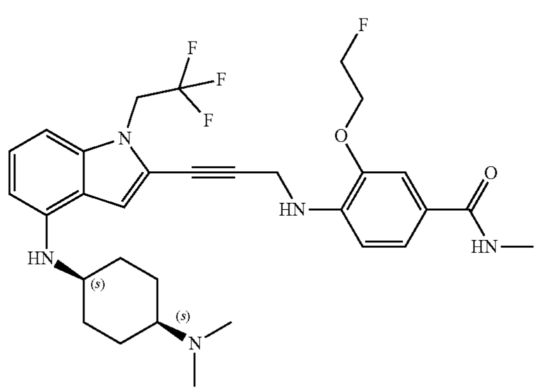 [SMILES: CNC(=O)c1ccc(NCC#Cc2cc3c(N[C@H]4CC[C@@H](N(C)C)CC4)cccc3n2CC(F)(F)F)c(OCCF)c1] | 3-(2-fluoroethoxy)-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide | 588.3 |

TABLE 3-continued

| Compound No. | Structure | IUPAC | LC-MS (ES+, m/z) |
|---|---|---|---|
| 106A | 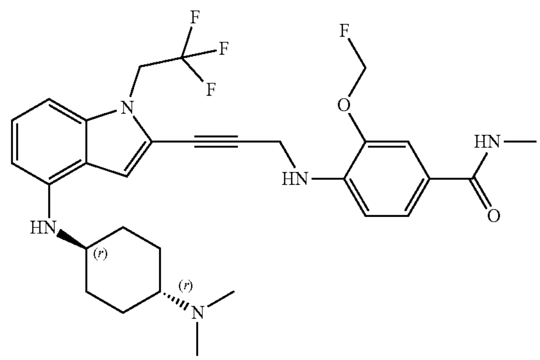 [SMILES: CNC(=O)c1ccc(NCC#Cc2cc3c(N[C@H]4CC[C@H](N(C)C)CC4)cccc3n2CC(F)(F)F)c(OCF)c1] | 3-(fluoromethoxy)-N-methyl-4-{[3-(4-{[(1R,4R)-4-(dimethyl-amino)cyclohexyl]amino}-1-(2,2,2-trifluoro-ethyl)-1H-indol-2-yl)prop-2-yn-1-yl]amino}benzamide | 574.3 |
| 107A | 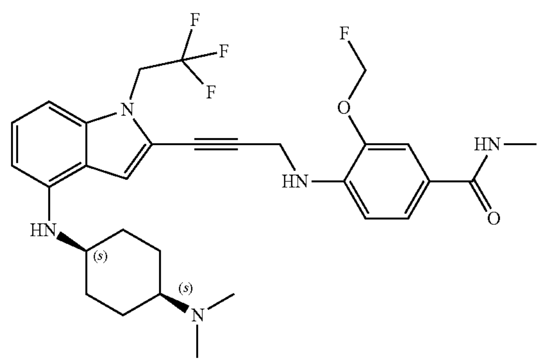 [SMILES: CNC(=O)c1ccc(NCC#Cc2cc3c(N[C@H]4CC[C@@H](N(C)C)CC4)cccc3n2CC(F)(F)F)c(OCF)c1] | 3-(fluoromethoxy)-N-methyl-4-{[3-(4-{[(1S,4S)-4-(dimethyl-amino)cyclohexyl]amino}-1-(2,2,2-trifluoro-ethyl)-1H-indol-2-yl)prop-2-yn-1-yl]amino}benzamide | 574.3 |
| 108A | 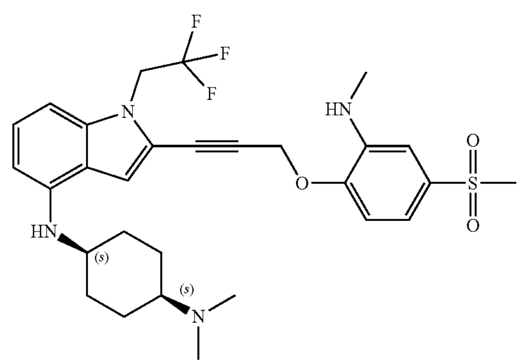 [SMILES: CNc1cc(S(C)(=O)=O)ccc1OCC#Cc1cc2c(N[C@H]3CC[C@@H](N(C)C)CC3)cccc2n1CC(F)(F)F] | (1S,4S)-N4-(2-{3-[4-methanesulfonyl-2-(methylamino)phenoxy]prop-1-yn-1-yl}-1-(2,2,2-trifluoroethyl)-1H-indol-4-yl)-N1,N1-dimethylcyclohexane-1,4-diamine | 577.3 |
| 109A | 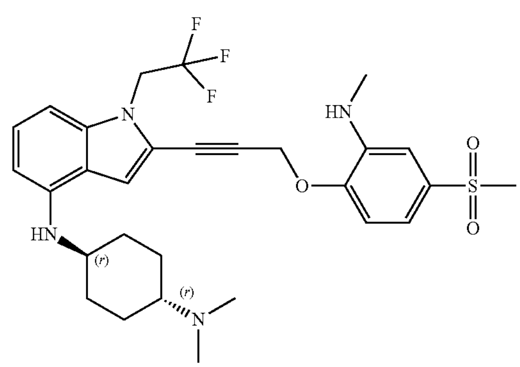 [SMILES: CNc1cc(S(C)(=O)=O)ccc1OCC#Cc1cc2c(N[C@H]3CC[C@H](N(C)C)CC3)cccc2n1CC(F)(F)F] | (1R,4R)-N4-(2-{3-[4-methanesulfonyl-2-(methylamino)phenoxy]prop-1-yn-1-yl}-1-(2,2,2-trifluoroethyl)-1H-indol-4-yl)-N1,N1-dimethylcyclohexane-1,4-diamine | 577.3 |

TABLE 3-continued

| Compound No. | Structure | IUPAC | LC-MS (ES+, m/z) |
|---|---|---|---|
| 110A | 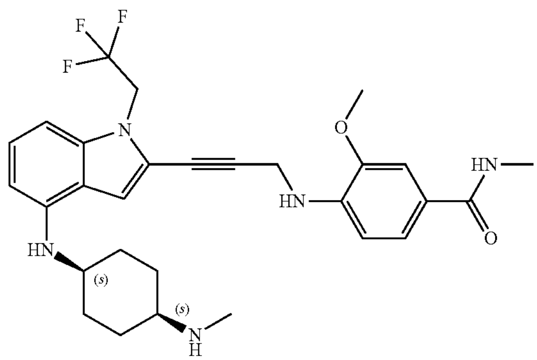 [SMILES: CNC(=O)c1ccc(NCC#Cc2cc3c(N[C@H]4CC[C@@H](NC)CC4)cccc3n2CC(F)(F)F)c(OC)c1] | 3-methoxy-N-methyl-4-{[3-(4-{[(1S,4S)-4-(methylamino)cyclohexyl]amino}-1-(2,2,2-trifluoroethyl)-1H-indol-2-yl)prop-2-yn-1-yl]amino}benzamide | 542.2 |
| 111A | 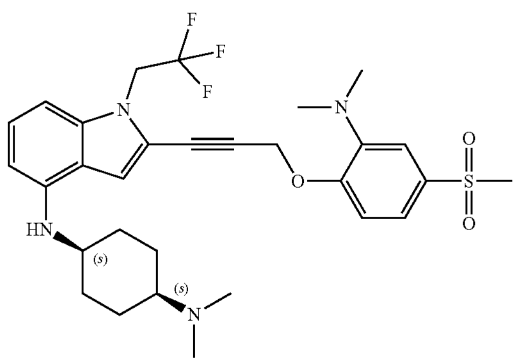 [SMILES: CN(C)c1cc(S(C)(=O)=O)ccc1OCC#Cc1cc2c(N[C@H]3CC[C@@H](N(C)C)CC3)cccc2n1CC(F)(F)F] | (1S,4S)-N⁴-(2-{3-[2-(dimethylamino)-4-methanesulfonylphenoxy]prop-1-yn-1-yl}-1-(2,2,2-trifluoroethyl)-1H-indol-4-yl)-N¹,N¹-dimethylcyclohexane-1,4-diamine | 591.2 |
| 112A | 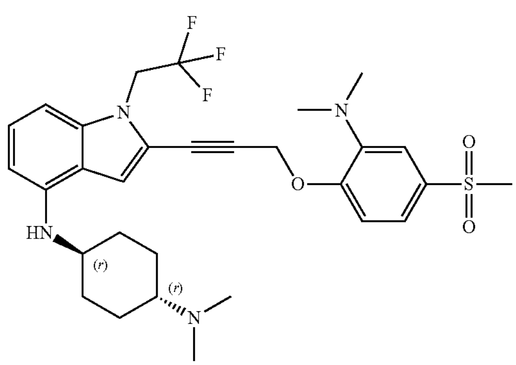 [SMILES: CN(C)c1cc(S(C)(=O)=O)ccc1OCC#Cc1cc2c(N[C@H]3CC[C@H](N(C)C)CC3)cccc2n1CC(F)(F)F] | (1R,4R)-N⁴-(2-{3-[2-(dimethylamino)-4-methanesulfonylphenoxy]prop-1-yn-1-yl}-1-(2,2,2-trifluoroethyl)-1H-indol-4-yl)-N¹,N¹-dimethylcyclohexane-1,4-diamine | 591.2 |
| 113A | 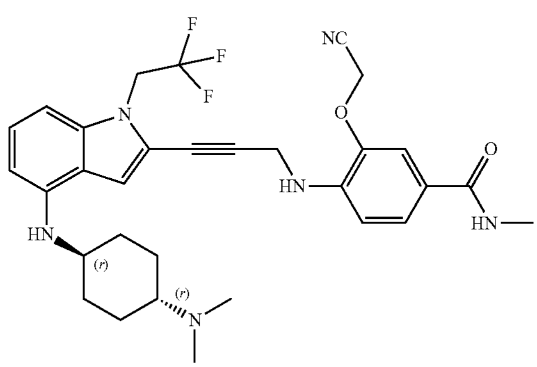 [SMILES: CNC(=O)c1ccc(NCC#Cc2cc3c(N[C@H]4CC[C@H](N(C)C)CC4)cccc3n2CC(F)(F)F)c(OCC#N)c1] | 3-(cyanomethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide | 581.3 |

TABLE 3-continued

| Compound No. | Structure | IUPAC | LC-MS (ES+, m/z) |
|---|---|---|---|
| 114A | 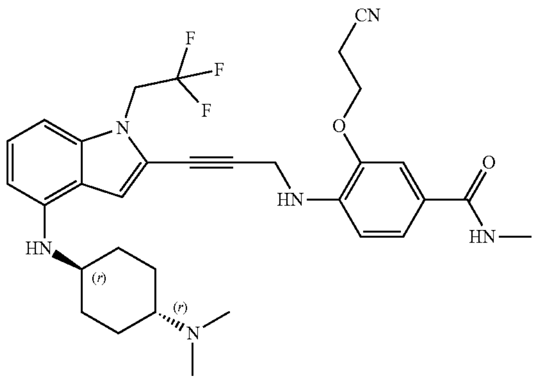 [SMILES: CNC(=O)c1ccc(NCC#Cc2cc3c(N[C@H]4CC[C@H](N(C)C)CC4)cccc3n2CC(F)(F)F)c(OCCC#N)c1] | 3-(2-cyanoethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide | 595.3 |
| 115A | 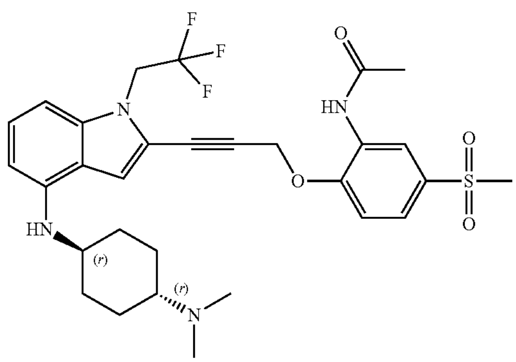 [SMILES: CC(=O)Nc1cc(S(C)(=O)=O)ccc1OCC#Cc1cc2c(N[C@H]3CC[C@H](N(C)C)CC3)cccc2n1CC(F)(F)F] | N-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]oxy}phenyl)acetamide | 605.2 |
| 116A | 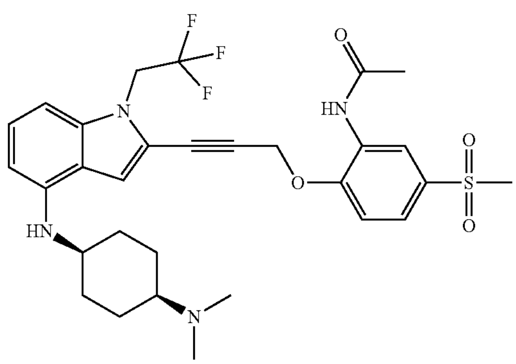 [SMILES: CC(=O)Nc1cc(S(C)(=O)=O)ccc1OCC#Cc1cc2c(N[C@H]3CC[C@@H](N(C)C)CC3)cccc2n1CC(F)(F)F] | N-(2-((3-(4-(((1S,4S)-4-(dimethylamino)cyclohexyl)amino)-1-(2,2,2-trifluoroethyl)-1H-indol-2-yl)prop-2-yn-1-yl)oxy)-5-(methylsulfonyl)phenyl)acetamide | 605.2 |
| 117A | 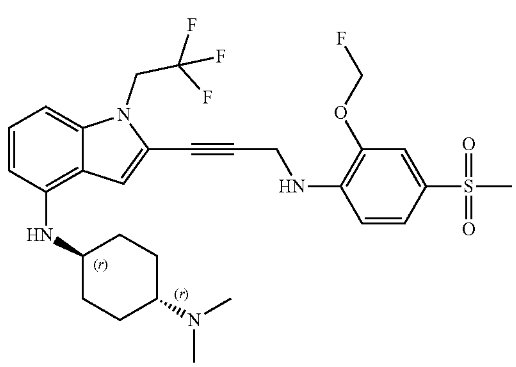 [SMILES: CN(C)[C@H]1CC[C@H](Nc2cccc3c2cc(C#CCNc2ccc(S(C)(=O)=O)cc2OCF)n3CC(F)(F)F)CC1] | (1R,4R)-N$^1$-(2-(3-((2-(fluoromethoxy)-4-(methylsulfonyl)phenyl)amino)prop-1-yn-1-yl)-1-(2,2,2-trifluoroethyl)-1H-indol-4-yl)-N$^4$,N$^4$-dimethylcyclohexane-1,4-diamine | 595.2 |

TABLE 3-continued

| Compound No. | Structure | IUPAC | LC-MS (ES+, m/z) |
|---|---|---|---|
| 118A | 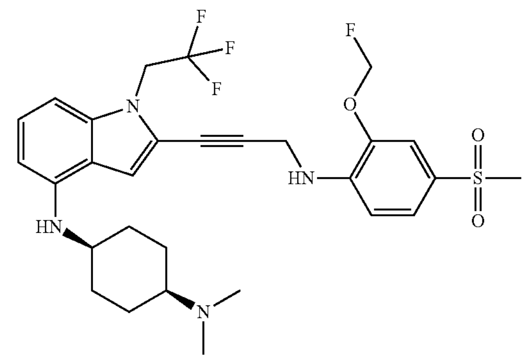 [SMILES: CN(C)[C@H]1CC[C@@H](Nc2cccc3c2cc(C#CCNc2ccc(S(C)(=O)=O)cc2OCF)n3CC(F)(F)F)CC1] | (1S,4S)-N¹-(2-(3-((2-(fluoromethoxy)-4-(methylsulfonyl)phenyl)amino)prop-1-yn-1-yl)-1-(2,2,2-trifluoroethyl)-1H-indol-4-yl)-N⁴,N⁴-dimethylcyclohexane-1,4-diamine | 595.2 |
| 119A | 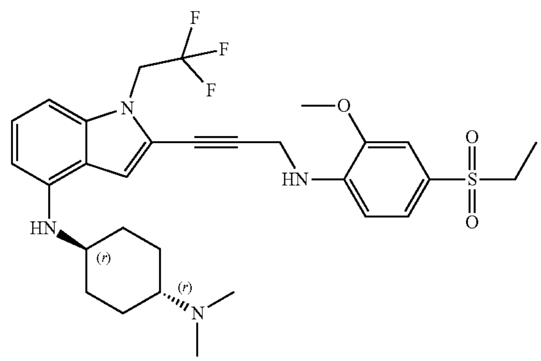 [SMILES: CCS(=O)(=O)c1ccc(NCC#Cc2cc3c(N[C@H]4CC[C@H](N(C)C)CC4)cccc3n2CC(F)(F)F)c(OC)c1] | (1R,4R)-N4-[2-(3-{[4-(ethanesulfonyl)-2-methoxyphenyl]amino}prop-1-yn-1-yl)-1-(2,2,2-trifluoroethyl)-1H-indol-4-yl]-N1,N1-dimethylcyclohexane-1,4-diamine | 591.4 |
| 120A | 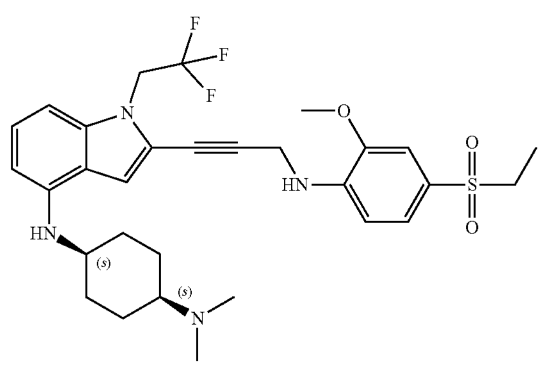 [SMILES: CCS(=O)(=O)c1ccc(NCC#Cc2cc3c(N[C@H]4CC[C@@H](N(C)C)CC4)cccc3n2CC(F)(F)F)c(OC)c1] | (1S,4S)-N⁴-[2-(3-{[4-(ethanesulfonyl)-2-methoxyphenyl]amino}prop-1-yn-1-yl)-1-(2,2,2-trifluoroethyl)-1H-indol-4-yl]-N¹,N¹-dimethylcyclohexane-1,4-diamine | 591.3 |
| 121A | 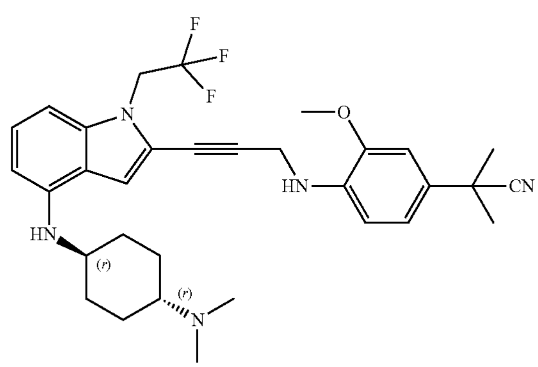 [SMILES: COc1cc(C(C)(C)C#N)ccc1NCC#Cc1cc2c(N[C@H]3CC[C@H](N(C)C)CC3)cccc2n1CC(F)(F)F] | 2-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}phenyl)-2-methylpropanenitrile | 566.2 |

TABLE 3-continued

| Compound No. | Structure | IUPAC | LC-MS (ES+, m/z) |
|---|---|---|---|
| 122A | 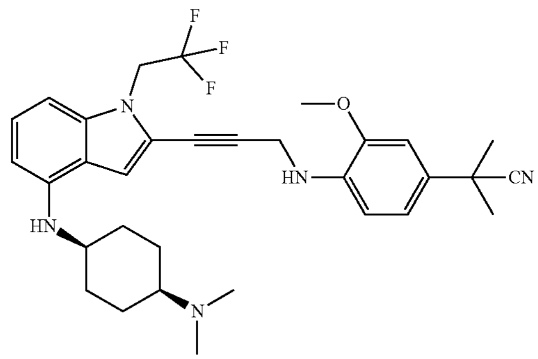 [SMILES: COc1cc(C(C)(C)C#N)ccc1NCC#Cc1cc2c(N[C@H]3CC[C@@H](N(C)C)CC3)cccc2n1CC(F)(F)F] | 2-(4-((3-(4-(((1S,4S)-4-(dimethylamino)cyclohexyl)amino)-1-(2,2,2-trifluoroethyl)-1H-indol-2-yl)prop-2-yn-1-yl)amino)-3-methoxyphenyl)-2-methylpropanenitrile | 566.2 |
| 123A | 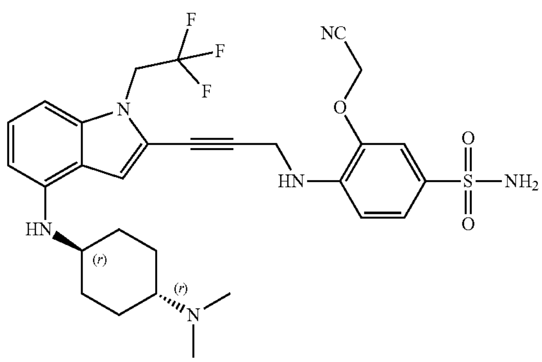 [SMILES: CN(C)[C@H]1CC[C@H](Nc2cccc3c2cc(C#CCNc2ccc(S(N)(=O)=O)cc2OCC#N)n3CC(F)(F)F)CC1] | 3-(cyanomethoxy)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide | 603.4 |
| 124A | 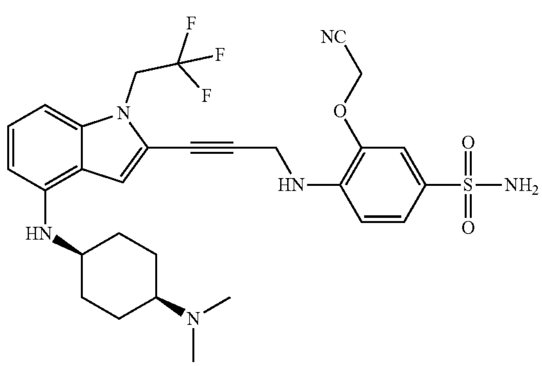 [SMILES: CN(C)[C@H]1CC[C@@H](Nc2cccc3c2cc(C#CCNc2ccc(S(N)(=O)=O)cc2OCC#N)n3CC(F)(F)F)CC1] | 3-(cyanomethoxy)-4-((3-(4-(((1S,4S)-4-(dimethylamino)cyclohexyl)amino)-1-(2,2,2-trifluoroethyl)-1H-indol-2-yl)prop-2-yn-1-yl)amino)benzenesulfonamide | 603.3 |
| 125A | 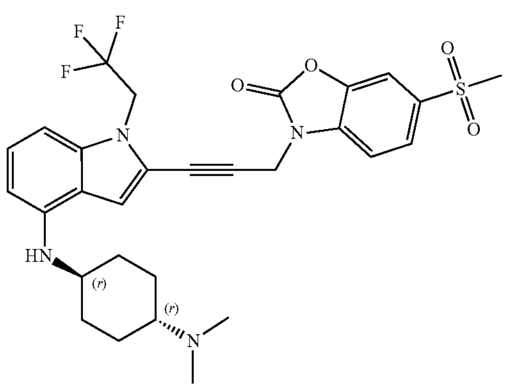 [SMILES: CN(C)[C@H]1CC[C@H](Nc2cccc3c2cc(C#CCn2c(=O)oc4cc(S(C)(=O)=O)ccc42)n3CC(F)(F)F)CC1] | 3-(3-(4-(((1R,4R)-4-(dimethylamino)cyclohexyl)amino)-1-(2,2,2-trifluoroethyl)-1H-indol-2-yl)prop-2-yn-1-yl)-6-(methylsulfonyl)benzo[d]oxazol-2(3H)-one | 589.2 |

TABLE 3-continued

| Compound No. | Structure | IUPAC | LC-MS (ES+, m/z) |
|---|---|---|---|
| 126A | 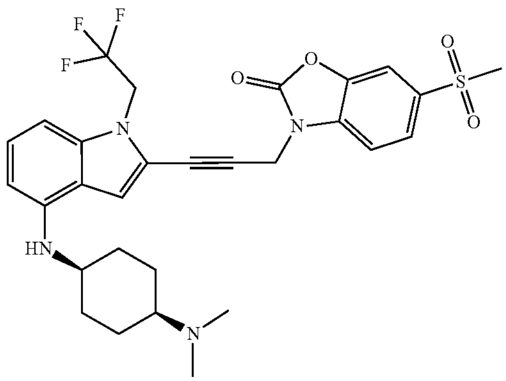 [SMILES: CN(C)[C@H]1CC[C@@H](Nc2cccc3c2cc(C#CCn2c(=O)oc4cc(S(C)(=O)=O)ccc42)n3CC(F)(F)F)CC1] | 3-(3-(4-(((1S,4S)-4-(dimethylamino)cyclohexyl)amino)-1-(2,2,2-trifluoroethyl)-1H-indol-2-yl)prop-2-yn-1-yl)-6-(methylsulfonyl)benzo[d]oxazol-2(3H)-one | 589.2 |
| 127A | 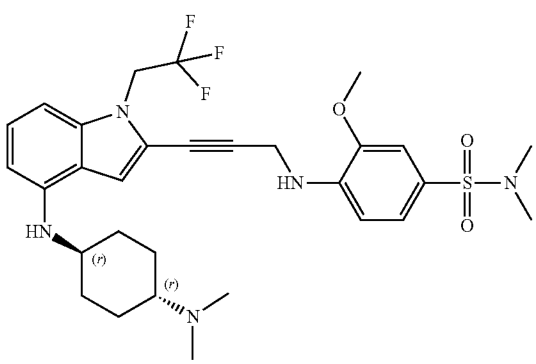 [SMILES: COc1cc(S(=O)(=O)N(C)C)ccc1NCC#Cc1cc2c(N[C@H]3CC[C@H](N(C)C)CC3)cccc2n1CC(F)(F)F] | 3-methoxy-N,N-dimethyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide | 606.2 |
| 128A | 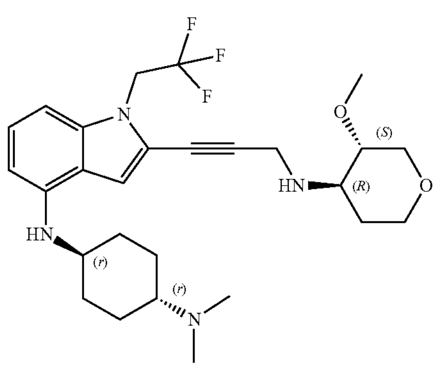 | (1R,4R)-N$^1$-(2-(3-(((3S,4R)-3-methoxytetrahydro-2H-pyran-4-yl)amino)prop-1-yn-1-yl)-1-(2,2,2-trifluoroethyl)-1H-indol-4-yl)-N$^4$,N$^4$-dimethylcyclohexane-1,4-diamine | 507.3 |
| 129A | 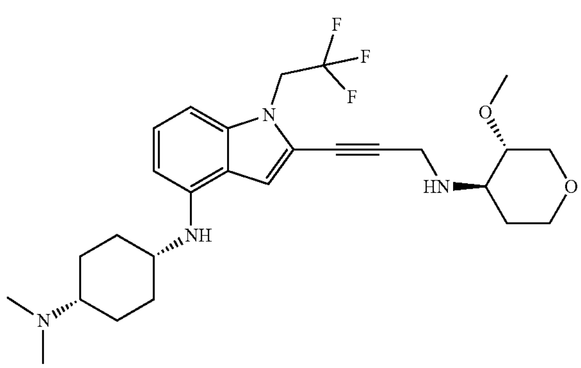 [SMILES: CO[C@@H]1COCC[C@H]1NCC#Cc1cc2c(N[C@H]3CC[C@@H](N(C)C)CC3)cccc2n1CC(F)(F)F] | (1S,4S)-N$^1$-(2-(3-(((3S,4R)-3-methoxytetrahydro-2H-pyran-4-yl)amino)prop-1-yn-1-yl)-1-(2,2,2-trifluoroethyl)-1H-indol-4-yl)-N$^4$,N$^4$-dimethylcyclohexane-1,4-diamine | 507.3 |

TABLE 3-continued

| Compound No. | Structure | IUPAC | LC-MS (ES+, m/z) |
|---|---|---|---|
| 130A | 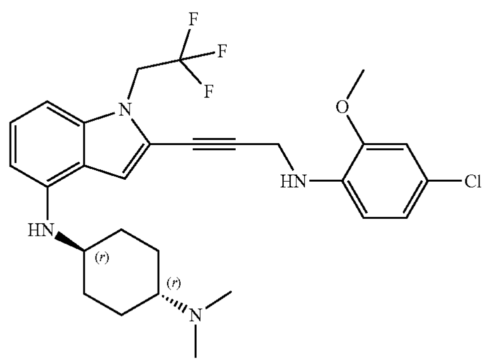 [SMILES: COc1cc(Cl)ccc1NCC#Cc1cc2c(N[C@H]3CC[C@H](N(C)C)CC3)cccc2n1CC(F)(F)F] | (1R,4R)-N⁴-(2-{3-[(4-chloro-2-methoxy-phenyl)amino]prop-1-yn-1-yl}-1-(2,2,2-trifluoro-ethyl)-1H-indol-4-yl)-N¹,N¹-dimethylcyclo-hexane-1,4-diamine | 533.2 |
| 131A | 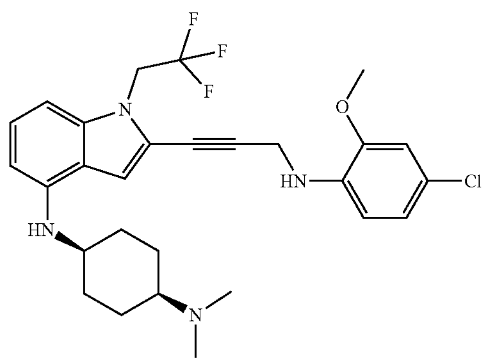 [SMILES: COc1cc(Cl)ccc1NCC#Cc1cc2c(N[C@H]3CC[C@@H](N(C)C)CC3)cccc2n1CC(F)(F)F] | (1S,4S)-N¹-(2-(3-((4-chloro-2-methoxy-phenyl)amino)prop-1-yn-1-yl)-1-(2,2,2-trifluoro-ethyl)-1H-indol-4-yl)-N⁴,N⁴-dimethylcyclo-hexane-1,4-diamine | 533.2 |
| 132A | 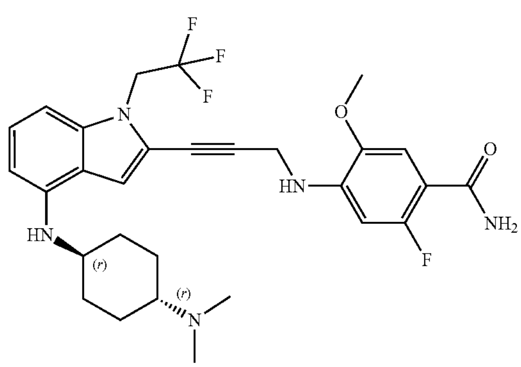 [SMILES: COc1cc(C(N)=O)c(F)cc1NCC#Cc1cc2c(N[C@H]3CC[C@H](N(C)C)CC3)cccc2n1CC(F)(F)F] | 4-((3-(4-(((1R,4R)-4-(dimethylamino)cyclo-hexyl)amino)-1-(2,2,2-trifluoroethyl)-1H-indol-2-yl)prop-2-yn-1-yl)amino)-2-fluoro-5-methoxy-benzamide | 560.2 |
| 133A | 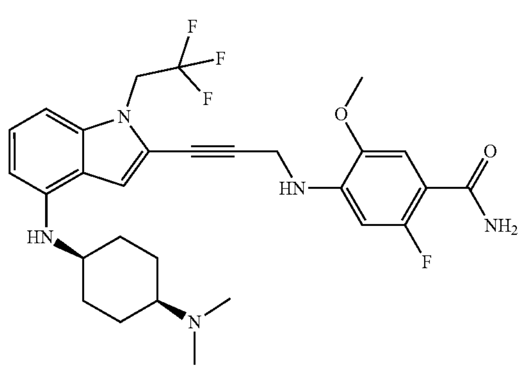 [SMILES: COc1cc(C(N)=O)c(F)cc1NCC#Cc1cc2c(N[C@H]3CC[C@@H](N(C)C)CC3)cccc2n1CC(F)(F)F] | 4-((3-(4-(((1S,4S)-4-(dimethylamino)cyclo-hexyl)amino)-1-(2,2,2-trifluoroethyl)-1H-indol-2-yl)prop-2-yn-1-yl)amino)-2-fluoro-5-methoxy-benzamide | 560.2 |

TABLE 3-continued

| Compound No. | Structure | IUPAC | LC-MS (ES+, m/z) |
|---|---|---|---|
| 134A | 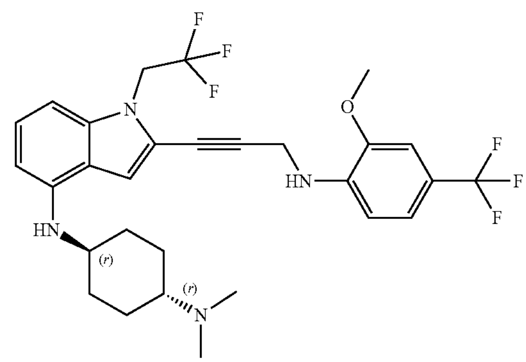 [SMILES: COc1cc(C(F)(F)F)ccc1NCC#Cc1cc2c(N[C@H]3CC[C@H](N(C)C)CC3)cccc2n1CC(F)(F)F] | (1R,4R)-N⁴-[2-(3-{[2-methoxy-4-(trifluoromethyl)phenyl]amino}prop-1-yn-1-yl)-1-(2,2,2-trifluoroethyl)-1H-indol-4-yl]-N¹,N¹-dimethylcyclohexane-1,4-diamine | 567.2 |
| 135A | 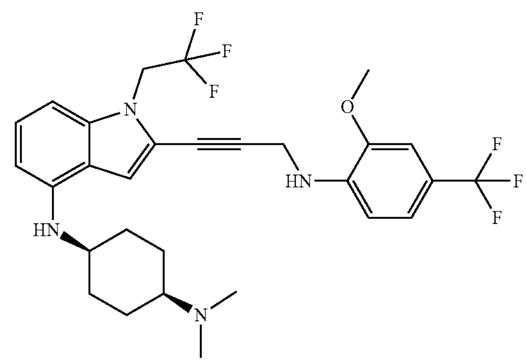 [SMILES: COc1cc(C(F)(F)F)ccc1NCC#Cc1cc2c(N[C@H]3CC[C@@H](N(C)C)CC3)cccc2n1CC(F)(F)F] | (1S,4S)-N¹-(2-(3-((2-methoxy-4-(trifluoromethyl)phenyl)amino)prop-1-yn-1-yl)-1-(2,2,2-trifluoroethyl)-1H-indol-4-yl)-N⁴,N⁴-dimethylcyclohexane-1,4-diamine | 567.2 |
| 136A | 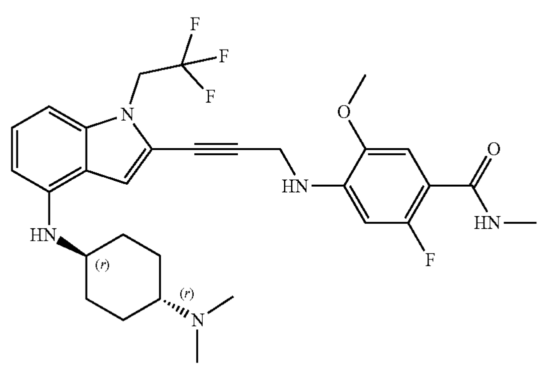 [SMILES: CNC(=O)c1cc(OC)c(NCC#Cc2cc3c(N[C@H]4CC[C@H](N(C)C)CC4)cccc3n2CC(F)(F)F)cc1F] | 2-fluoro-5-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide | 574.3 |
| 137A | 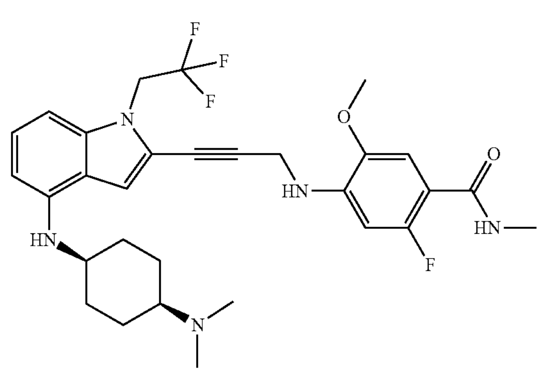 [SMILES: CNC(=O)c1cc(OC)c(NCC#Cc2cc3c(N[C@H]4CC[C@@H](N(C)C)CC4)cccc3n2CC(F)(F)F)cc1F] | 4-((3-(4-(((1S,4S)-4-(dimethylamino)cyclohexyl)amino)-1-(2,2,2-trifluoroethyl)-1H-indol-2-yl)prop-2-yn-1-yl)amino)-2-fluoro-5-methoxy-N-methylbenzamide | 574.2 |

TABLE 3-continued

| Compound No. | Structure | IUPAC | LC-MS (ES+, m/z) |
|---|---|---|---|
| 138A | 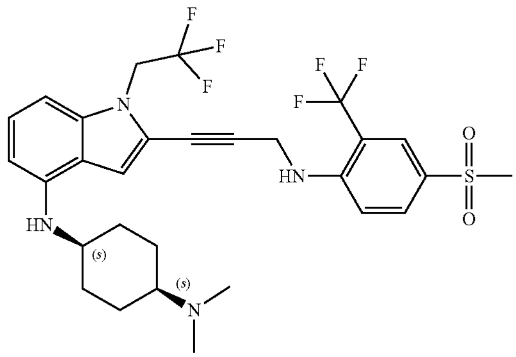 [SMILES: CN(C)[C@H]1CC[C@@H](Nc2cccc3c2cc(C#CCNc2ccc(S(C)(=O)=O)cc2C(F)(F)F)n3CC(F)(F)F)CC1] | (1S,4S)-N⁴-[2-(3-{[4-methanesulfonyl-2-(trifluoromethyl)phenyl]amino}prop-1-yn-1-yl)-1-(2,2,2-trifluoroethyl)-1H-indol-4-yl]-N¹,N¹-dimethylcyclohexane-1,4-diamine | 615.3 |
| 139A | 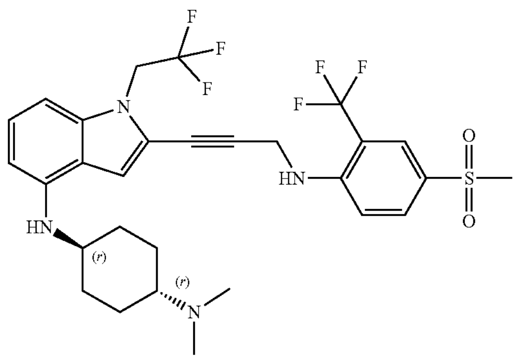 [SMILES: CN(C)[C@H]1CC[C@H](Nc2cccc3c2cc(C#CCNc2ccc(S(C)(=O)=O)cc2C(F)(F)F)n3CC(F)(F)F)CC1] | (1R,4R)-N⁴-[2-(3-{[4-methanesulfonyl-2-(trifluoromethyl)phenyl]amino}prop-1-yn-1-yl)-1-(2,2,2-trifluoroethyl)-1H-indol-4-yl]-N¹,N¹-dimethylcyclohexane-1,4-diamine | 615.3 |
| 140A | 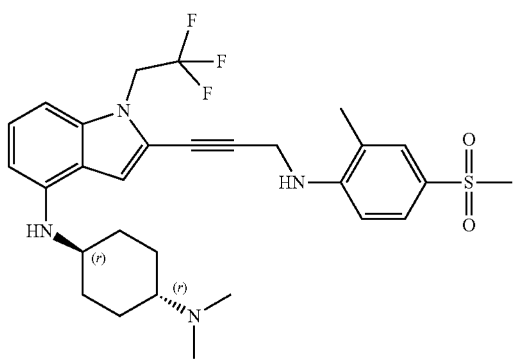 [SMILES: Cc1cc(S(C)(=O)=O)ccc1NCC#Cc1cc2c(N[C@H]3CC[C@H](N(C)C)CC3)cccc2n1CC(F)(F)F] | (1R,4R)-N⁴-(2-{3-[(4-methanesulfonyl-2-methylphenyl)amino]prop-1-yn-1-yl}-1-(2,2,2-trifluoroethyl)-1H-indol-4-yl)-N¹,N¹-dimethylcyclohexane-1,4-diamine | 561.3 |
| 141A | 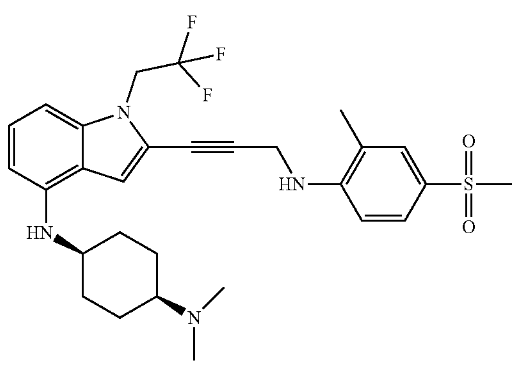 [SMILES: Cc1cc(S(C)(=O)=O)ccc1NCC#Cc1cc2c(N[C@H]3CC[C@@H](N(C)C)CC3)cccc2n1CC(F)(F)F] | (1S,4S)-N¹,N¹-dimethyl-N⁴-(2-(3-((2-methyl-4-(methylsulfonyl)phenyl)amino)prop-1-yn-1-yl)-1-(2,2,2-trifluoroethyl)-1H-indol-4-yl)cyclohexane-1,4-diamine | 561.3 |

TABLE 3-continued

| Compound No. | Structure | IUPAC | LC-MS (ES+, m/z) |
|---|---|---|---|
| 142A | 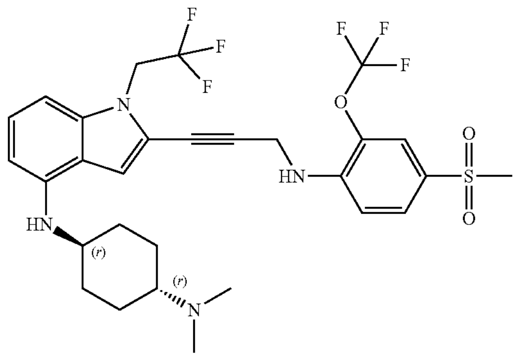 [SMILES: CN(C)[C@H]1CC[C@H](Nc2cccc3c2cc(C#CCNc2ccc(S(C)(=O)=O)cc2OC(F)(F)F)n3CC(F)(F)F)CC1] | (1R,4R)-N4-[2-(3-{[4-methanesulfonyl-2-(trifluoromethoxy)phenyl]amino}prop-1-yn-1-yl)-1-(2,2,2-trifluoroethyl)-1H-indol-4-yl]-N1,N1-dimethyl-cyclohexane-1,4-diamine | 631.1 |
| 143A | 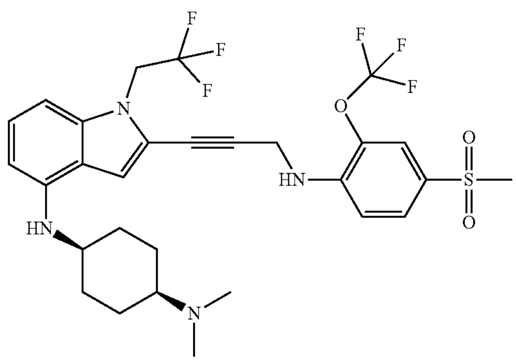 [SMILES: CN(C)[C@H]1CC[C@@H](Nc2cccc3c2cc(C#CCNc2ccc(S(C)(=O)=O)cc2OC(F)(F)F)n3CC(F)(F)F)CC1] | (1S,4S)-N1,N1-dimethyl-N4-(2-(3-((4-(methyl-sulfonyl)-2-(trifluoro-methoxy)phenyl)amino)prop-1-yn-1-yl)-1-(2,2,2-trifluoroethyl)-1H-indol-4-yl)cyclohexane-1,4-diamine | 631.1 |
| 144A | 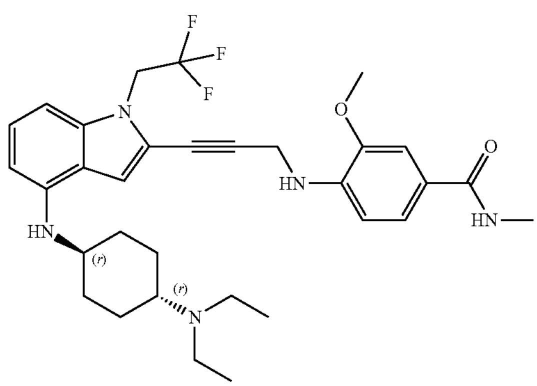 [SMILES: CCN(CC)[C@H]1CC[C@H](Nc2cccc3c2cc(C#CCNc2ccc(C(=O)NC)cc2OC)n3CC(F)(F)F)CC1] | 3-methoxy-N-methyl-4-{[3-(4-([(1R,4R)-4-(diethylamino)cyclohexyl]amino}-1-(2,2,2-trifluoro-ethyl)-1H-indol-2-yl)prop-2-yn-1-yl]amino}benzamide | 584.3 |
| 145A | 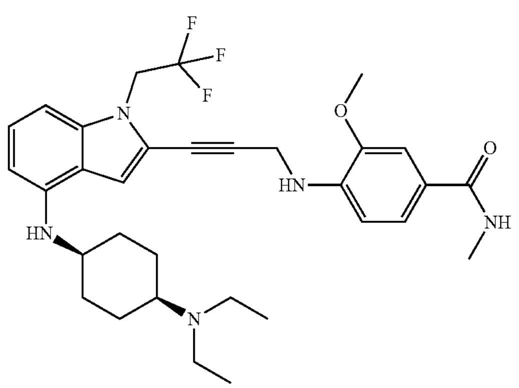 [SMILES: CCN(CC)[C@H]1CC[C@@H](Nc2cccc3c2cc(C#CCNc2ccc(C(=O)NC)cc2OC)n3CC(F)(F)F)CC1] | 4-((3-(4-(((1S,4S)-4-(diethylamino)cyclo-hexyl)amino)-1-(2,2,2-trifluoroethyl)-1H-indol-2-yl)prop-2-yn-1-yl)amino)-3-methoxy-N-methyl-benzamide | 584.3 |

TABLE 3-continued

| Compound No. | Structure | IUPAC | LC-MS (ES+, m/z) |
|---|---|---|---|
| 146A | 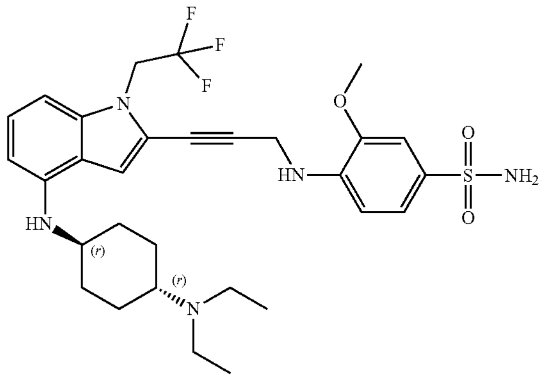 [SMILES: CCN(CC)[C@H]1CC[C@H](Nc2cccc3c2cc(C#CCNc2ccc(S(N)(=O)=O)cc2OC)n3CC(F)(F)F)CC1] | 3-methoxy-4-{[3-(4-{[(1R,4R)-4-(diethylamino)cyclohexyl]amino}-1-(2,2,2-trifluoroethyl)-1H-indol-2-yl)prop-2-yn-1-yl]amino}benzene-1-sulfonamide | 606.2 |
| 147A | 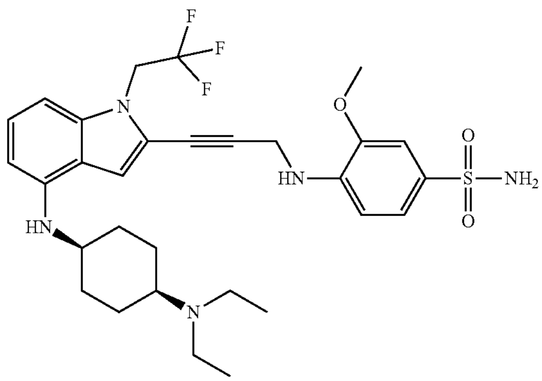 [SMILES: CCN(CC)[C@H]1CC[C@@H](Nc2cccc3c2cc(C#CCNc2ccc(S(N)(=O)=O)cc2OC)n3CC(F)(F)F)CC1] | 4-((3-(4-(((1S,4S)-4-(diethylamino)cyclohexyl)amino)-1-(2,2,2-trifluoroethyl)-1H-indol-2-yl)prop-2-yn-1-yl)amino)-3-methoxybenzenesulfonamide | 606.2 |
| 148A | 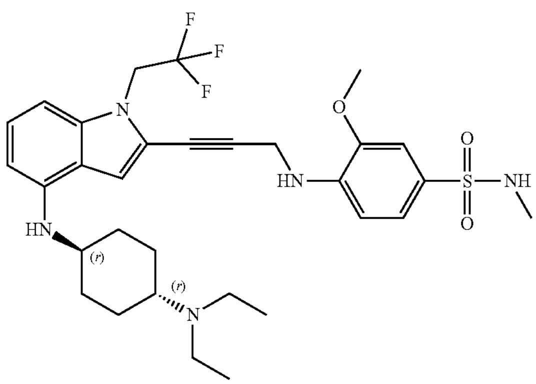 [SMILES: CCN(CC)[C@H]1CC[C@H](Nc2cccc3c2cc(C#CCNc2ccc(S(=O)(=O)NC)cc2OC)n3CC(F)(F)F)CC1] | 3-methoxy-N-methyl-4-{[3-(4-{[(1R,4R)-4-(diethylamino)cyclohexyl]amino}-1-(2,2,2-trifluoroethyl)-1H-indol-2-yl)prop-2-yn-1-yl]amino}benzene-1-sulfonamide | 620.2 |
| 149A | 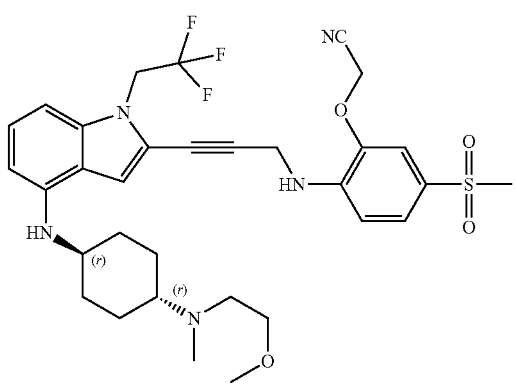 | 2-(5-methanesulfonyl-2-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}phenoxy)acetonitrile | 646.2 |

TABLE 3-continued

| Compound No. | Structure | IUPAC | LC-MS (ES+, m/z) |
|---|---|---|---|
| 150A | 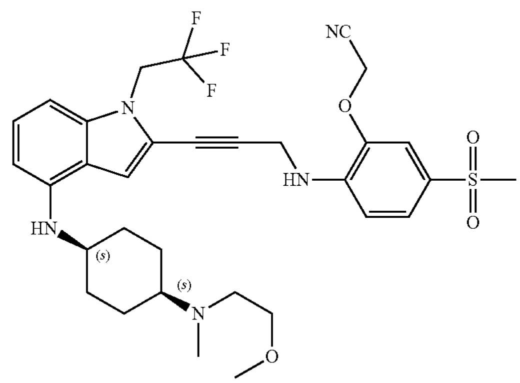 [SMILES: COCCN(C)[C@H]1CC[C@@H](Nc2cccc3c2cc(C#CCNc2ccc(S(C)(=O)=O)cc2OCC#N)n3CC(F)(F)F)CC1] | 2-(5-methanesulfonyl-2-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}phenoxy)acetonitrile | 646.2 |
| 151A | 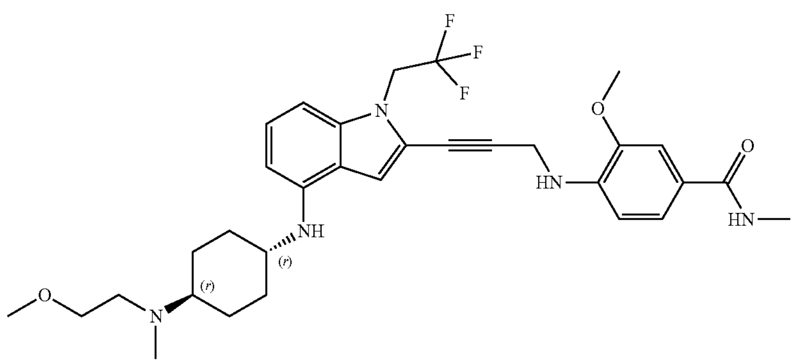 | 3-methoxy-N-methyl-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide | 600.3 |
| 152A | 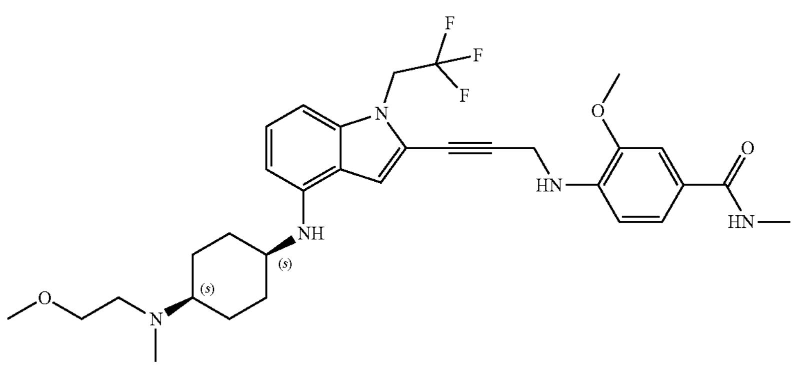 | 3-methoxy-N-methyl-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzamide | 600.3 |
| 153A | 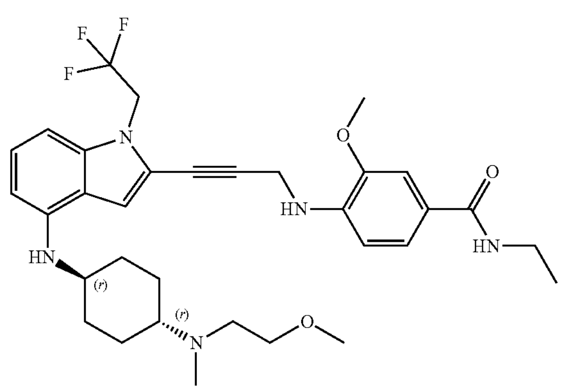 [SMILES: CCNC(=O)c1ccc(NCC#Cc2cc3c(N[C@H]4CC[C@H](N(C)CCOC)CC4)cccc3n2CC(F)(F)F)c(OC)c1] | N-ethyl-3-methoxy-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide | 614.4 |

TABLE 3-continued

| Compound No. | Structure | IUPAC | LC-MS (ES+, m/z) |
|---|---|---|---|
| 154A | 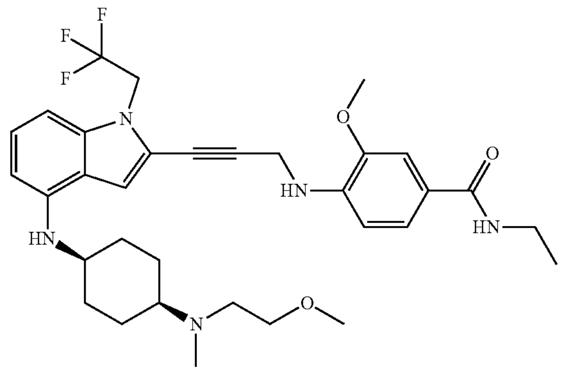 [SMILES: CCNC(=O)c1ccc(NCC#Cc2cc3c(N[C@H]4CC[C@@H](N(C)CCOC)CC4)cccc3n2CC(F)(F)F)c(OC)c1] | N-ethyl-3-methoxy-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino)benzamide | 614.4 |
| 155A | 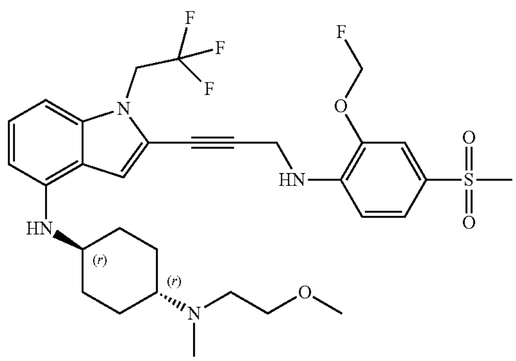 [SMILES: COCCN(C)[C@H]1CC[C@H](Nc2cccc3c2cc(C#CCNc2ccc(S(C)(=O)=O)cc2OCF)n3CC(F)(F)F)CC1] | (1R,4R)-N¹-(2-(3-((2-(fluoromethoxy)-4-(methylsulfonyl)phenyl)amino)prop-1-yn-1-yl)-1-(2,2,2-trifluoroethyl)-1H-indol-4-yl)-N⁴-(2-methoxyethyl)-N⁴-methylcyclohexane-1,4-diamine | 639.3 |
| 156A | 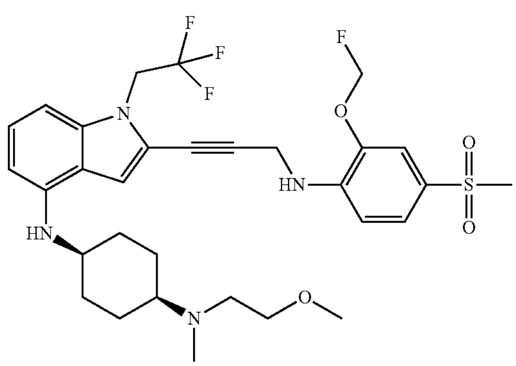 [SMILES: COCCN(C)[C@H]1CC[C@@H](Nc2cccc3c2cc(C#CCNc2ccc(S(C)(=O)=O)cc2OCF)n3CC(F)(F)F)CC1] | (1S,4S)-N¹-(2-(3-((2-(fluoromethoxy)-4-(methylsulfonyl)phenyl)amino)prop-1-yn-1-yl)-1-(2,2,2-trifluoroethyl)-1H-indol-4-yl)-N⁴-(2-methoxyethyl)-N⁴-methylcyclohexane-1,4-diamine | 639.3 |
| 157A | 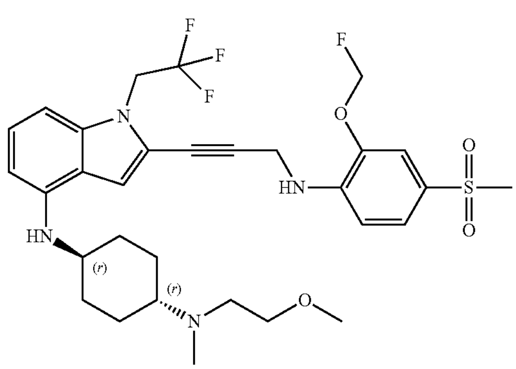 [SMILES: COCCN(C)[C@H]1CC[C@H](Nc2cccc3c2cc(C#CCNc2ccc(S(C)(=O)=O)cc2OCF)n3CC(F)(F)F)CC1] | 3-(fluoromethoxy)-N-methyl-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide | 618.3 |

TABLE 3-continued

| Compound No. | Structure | IUPAC | LC-MS (ES+, m/z) |
|---|---|---|---|
| 158A | 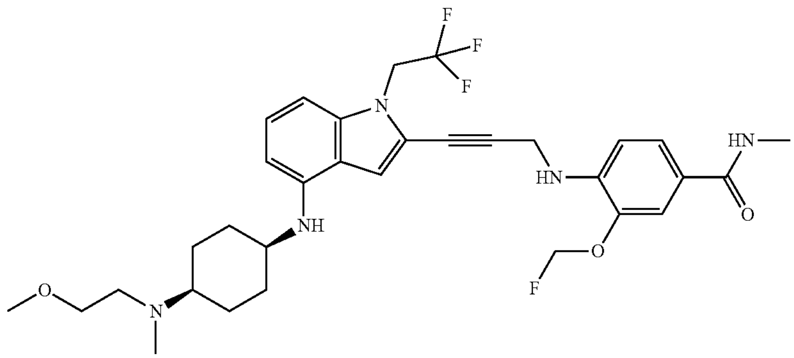 | 3-(fluoromethoxy)-N-methyl-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzamide | 618.3 |
| 159A | 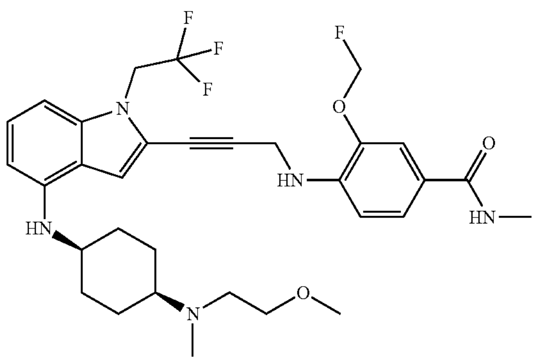 [SMILES: CNC(=O)c1ccc(NCC#Cc2cc3c(N[C@H]4CC[C@@H](N(C)CCOC)CC4)cccc3n2CC(F)(F)F)c(OCF)c1] | 3-(fluoromethoxy)-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino)-N-methylbenzamide | 618.3 |
| 160A | 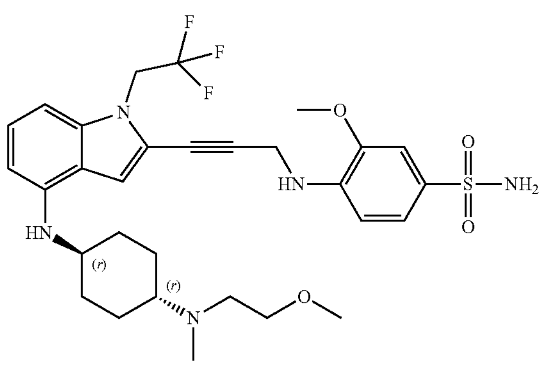 [SMILES: COCCN(C)[C@H]1CC[C@H](Nc2cccc3c2cc(C#CCNc2ccc(S(N)(=O)=O)cc2OC)n3CC(F)(F)F)CC1] | 3-methoxy-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide | 622.2 |
| 161A | 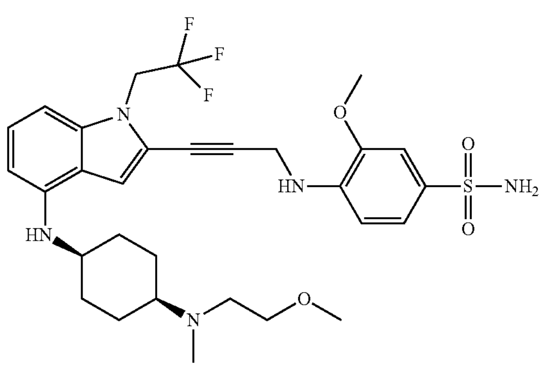 [SMILES: COCCN(C)[C@H]1CC[C@@H](Nc2cccc3c2cc(C#CCNc2ccc(S(N)(=O)=O)cc2OC)n3CC(F)(F)F)CC1] | 3-methoxy-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino)benzenesulfonamide | 622.2 |

TABLE 3-continued

| Compound No. | Structure | IUPAC | LC-MS (ES+, m/z) |
|---|---|---|---|
| 162A | 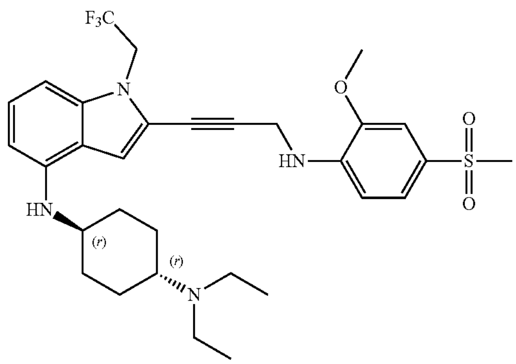 [SMILES: CCN(CC)[C@H]1CC[C@H](Nc2cccc3c2cc(C#CCNc2ccc(S(C)(=O)=O)cc2OC)n3CC(F)(F)F)CC1] | (1R,4R)-N¹,N¹-diethyl-N4-(2-{3-[(4-methanesulfonyl-2-methoxyphenyl)amino]prop-1-yn-1-yl}-1-(2,2,2-trifluoroethyl)-1H-indol-4-yl)cyclohexane-1,4-diamine | 605.4 |
| 163A | 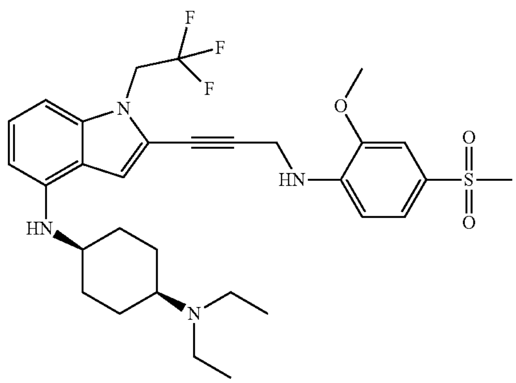 [SMILES: CCN(CC)[C@H]1CC[C@@H](Nc2cccc3c2cc(C#CCNc2ccc(S(C)(=O)=O)cc2OC)n3CC(F)(F)F)CC1] | (1S,4S)-N¹,N¹-diethyl-N⁴-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine | 605.2 |
| 164A | 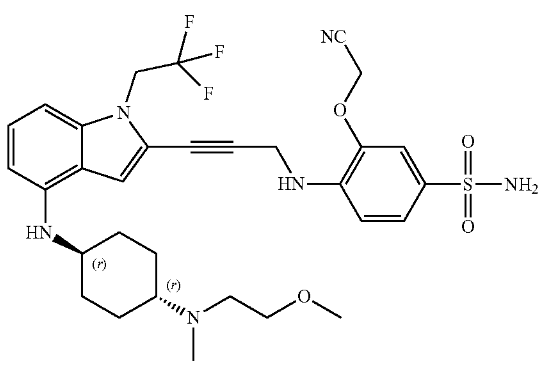 [SMILES: COCCN(C)[C@H]1CC[C@H](Nc2cccc3c2cc(C#CCNc2ccc(S(N)(=O)=O)cc2OCC#N)n3CC(F)(F)F)CC1] | 3-(cyanomethoxy)-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide | 647.2 |
| 165A | 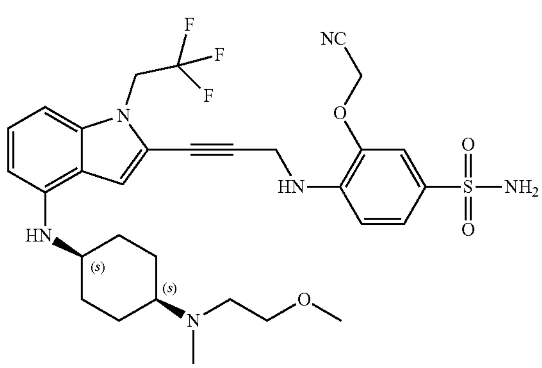 [SMILES: COCCN(C)[C@H]1CC[C@@H](Nc2cccc3c2cc(C#CCNc2ccc(S(N)(=O)=O)cc2OCC#N)n3CC(F)(F)F)CC1] | 3-(cyanomethoxy)-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide | 647.2 |

TABLE 3-continued

| Compound No. | Structure | IUPAC | LC-MS (ES+, m/z) |
|---|---|---|---|
| 166A | 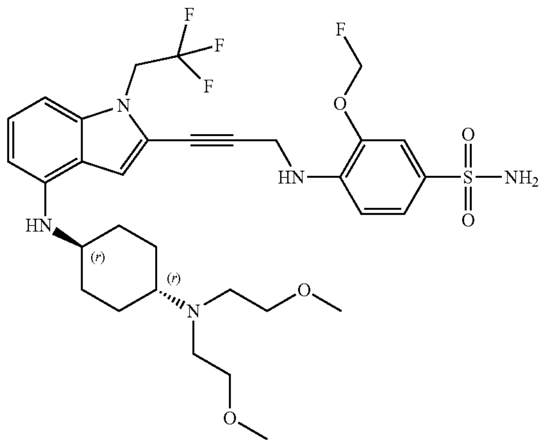 [SMILES: COCCN(CCOC)[C@H]1CC[C@H](Nc2cccc3c2cc(C#CCNc2ccc(S(N)(=O)=O)cc2OCF)n3CC(F)(F)F)CC1] | 3-(fluoromethoxy)-4-{[3-(4-{[(1R,4R)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide | 684.3 |
| 167A | 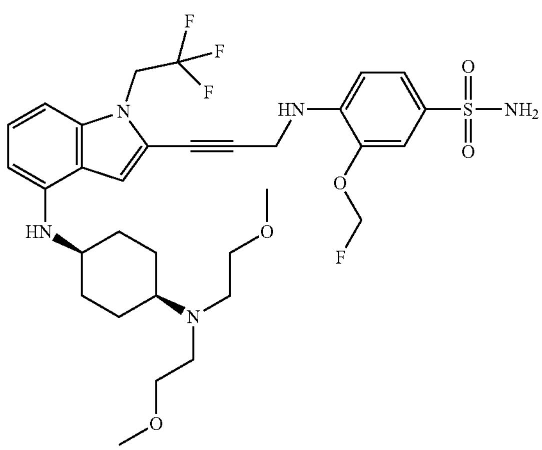 [SMILES: COCCN(CCOC)[C@H]1CC[C@@H](Nc2cccc3c2cc(C#CCNc2ccc(S(N)(=O)=O)cc2OCF)n3CC(F)(F)F)CC1] | 3-(fluoromethoxy)-4-{[3-(4-{[(1S,4S)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide | 684.2 |
| 168A | 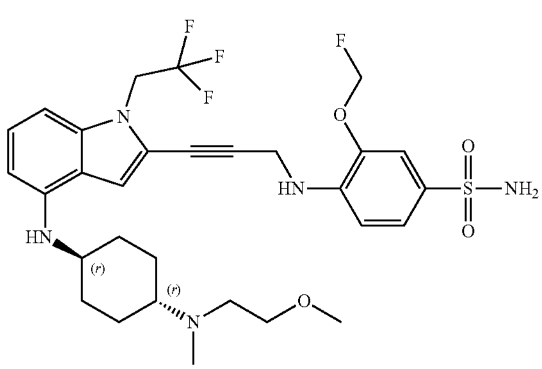 [SMILES: COCCN(C)[C@H]1CC[C@H](Nc2cccc3c2cc(C#CCNc2ccc(S(N)(=O)=O)cc2OCF)n3CC(F)(F)F)CC1] | 3-(fluoromethoxy)-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide | 640.2 |

TABLE 3-continued

| Compound No. | Structure | IUPAC | LC-MS (ES+, m/z) |
|---|---|---|---|
| 169A | 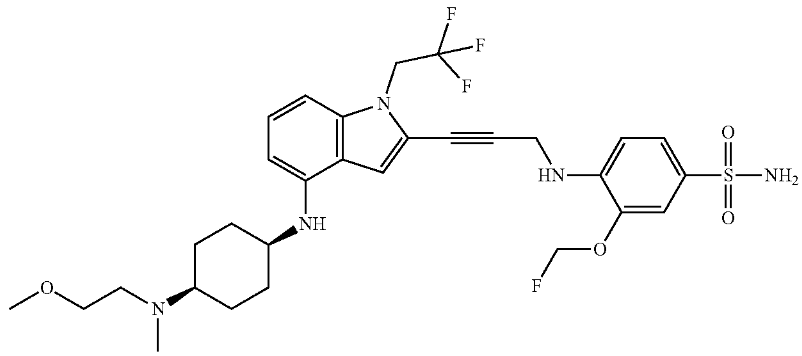 [SMILES: COCCN(C)[C@H]1CC[C@@H](Nc2cccc3c2cc(C#CCNc2ccc(S(N)(=O)=O)cc2OCF)n3CC(F)(F)F)CC1] | 3-(fluoromethoxy)-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide | 640.2 |
| 170A | 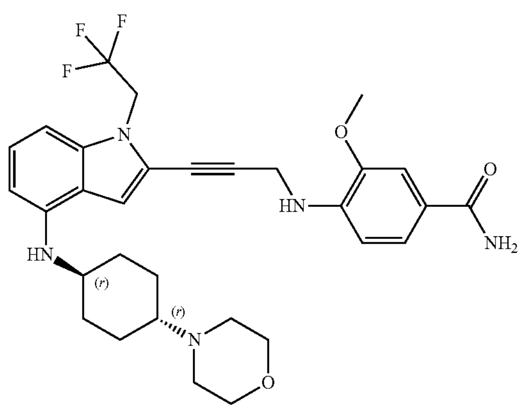 [SMILES: COc1cc(C(N)=O)ccc1NCC#Cc1cc2c(N[C@H]3CC[C@H](N4CCOCC4)CC3)cccc2n1CC(F)(F)F] | 3-methoxy-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide | 584.2 |
| 171A | 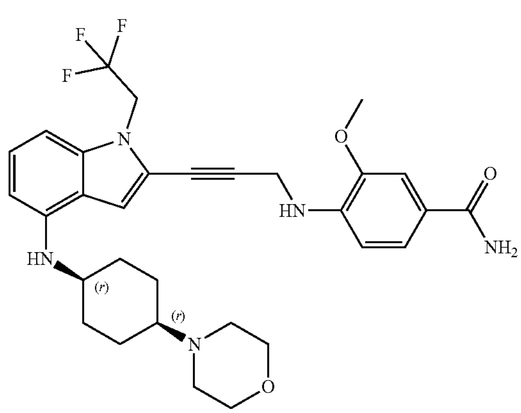 [SMILES: COc1cc(C(N)=O)ccc1NCC#Cc1cc2c(N[C@H]3CC[C@@H](N4CCOCC4)CC3)cccc2n1CC(F)(F)F] | 3-methoxy-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzamide | 584.2 |

TABLE 3-continued

| Compound No. | Structure | IUPAC | LC-MS (ES+, m/z) |
|---|---|---|---|
| 172A | 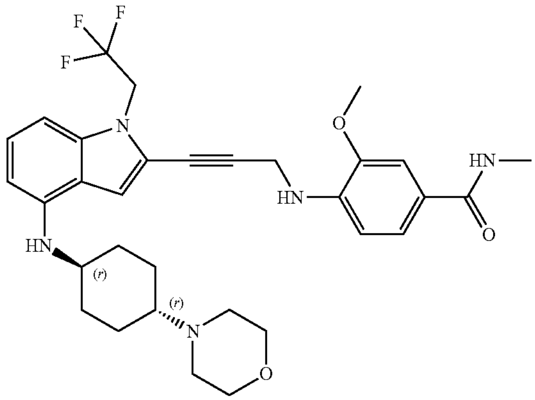 [SMILES: CNC(=O)c1ccc(NCC#Cc2cc3c(N[C@H]4CC[C@H](N5CCOCC5)CC4)cccc3n2CC(F)(F)F)c(OC)c1] | 3-methoxy-N-methyl-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide | 598.3 |
| 173A | 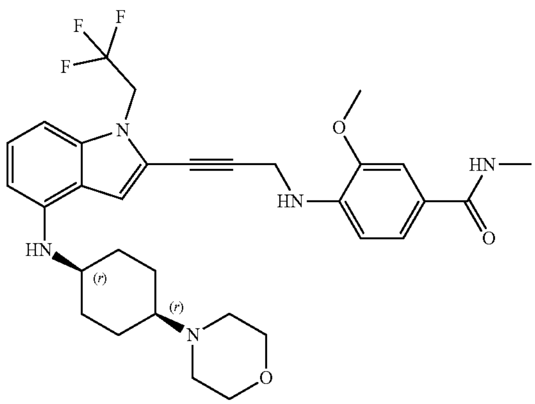 [SMILES: CNC(=O)c1ccc(NCC#Cc2cc3c(N[C@H]4CC[C@@H](N5CCOCC5)CC4)cccc3n2CC(F)(F)F)c(OC)c1] | 3-methoxy-N-methyl-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzamide | 598.3 |
| 174A | 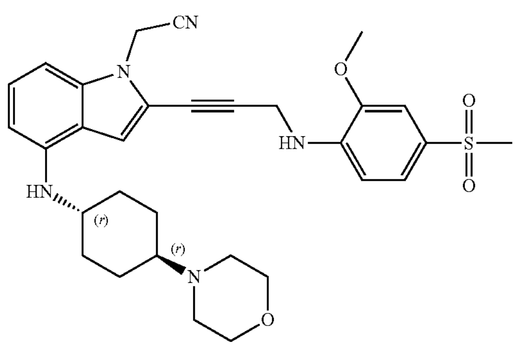 [SMILES: COc1cc(S(C)(=O)=O)ccc1NCC#Cc1cc2c(N[C@H]3CC[C@H](N4CCOCC4)CC3)cccc2n1CC#N] | 2-(2-{3-[(4-methanesulfonyl-2-methoxyphenyl)amino]prop-1-yn-1-yl}-4-{[(1R,4R)-4-(morpholin-4-yl)cyclohexyl]amino}-1H-indol-1-yl)acetonitrile | 576.3 |
| 175A | 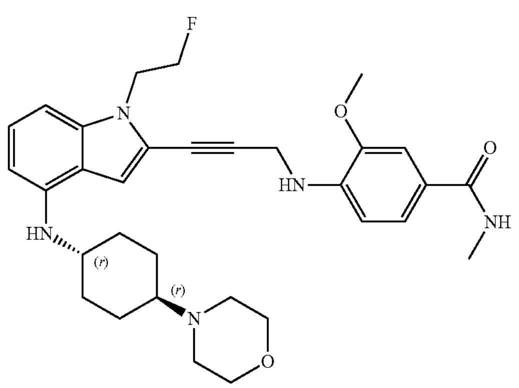 [SMILES: CNC(=O)c1ccc(NCC#Cc2cc3c(N[C@H]4CC[C@H](N5CCOCC5)CC4)cccc3n2CCF)c(OC)c1] | 4-({3-[1-(2-fluoroethyl)-4-{[(1R,4R)-4-(morpholin-4-yl)cyclohexyl]amino}-1H-indol-2-yl]prop-2-yn-1-yl}amino)-3-methoxy-N-methylbenzamide | 562.3 |

TABLE 3-continued

| Compound No. | Structure | IUPAC | LC-MS (ES+, m/z) |
|---|---|---|---|
| 176A | 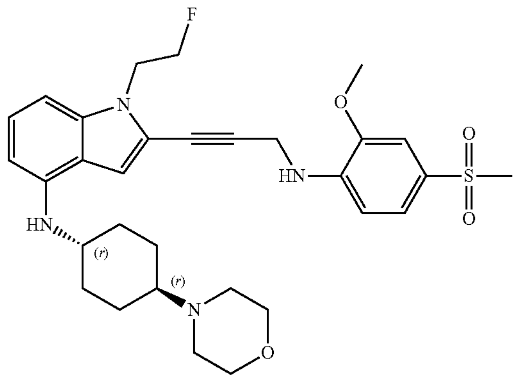 [SMILES: COc1cc(S(C)(=O)=O)ccc1NCC#Cc1cc2c(N[C@H]3CC[C@H](N4CCOCC4)CC3)cccc2n1CCF] | 1-(2-fluoroethyl)-2-{3-[(4-methane-sulfonyl-2-methoxy-phenyl)amino]prop-1-yn-1-yl}-N-[(1R,4R)-4-(morpholin-4-yl)cyclo-hexyl]-1H-indol-4-amine | 583.3 |
| 177A | 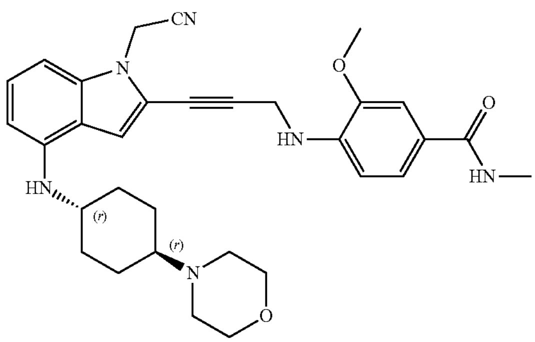 [SMILES: CNC(=O)c1ccc(NCC#Cc2cc3c(N[C@H]4CC[C@H](N5CCOCC5)CC4)cccc3n2CC#N)c(OC)c1] | 4-({3-[1-(cyanomethyl)-4-{[(1R,4R)-4-(morpholin-4-yl)cyclohexyl]amino}-1H-indol-2-yl]prop-2-yn-1-yl}amino)-3-methoxy-N-methyl-benzamide | 555.3 |
| 178A | 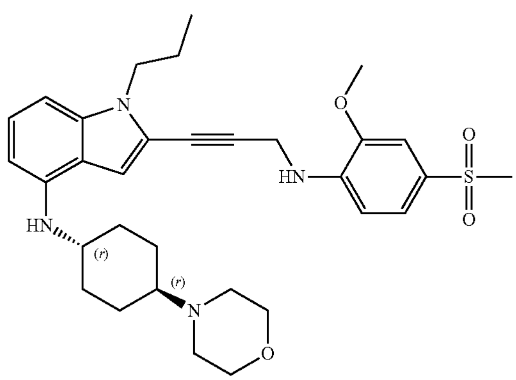 [SMILES: CCCn1c(C#CCNc2ccc(S(C)(=O)=O)cc2OC)cc2c(N[C@H]3CC[C@H](N4CCOCC4)CC3)cccc21] | 2-{3-[(4-methane-sulfonyl-2-methoxy-phenyl)amino]prop-1-yn-1-yl}-1-propyl-N-[(1R,4R)-4-(morpholin-4-yl)cyclohexyl]-1H-indol-4-amine | 579.3 |
| 179A | 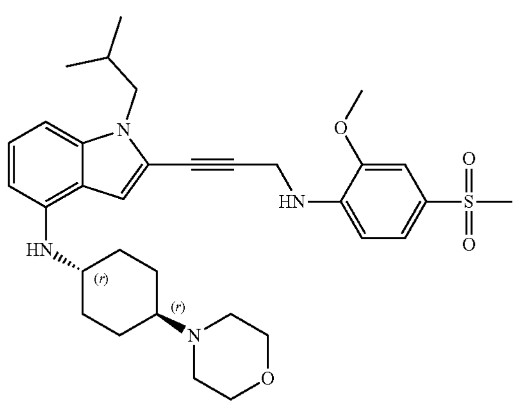 [SMILES: COc1cc(S(C)(=O)=O)ccc1NCC#Cc1cc2c(N[C@H]3CC[C@H](N4CCOCC4)CC3)cccc2n1CC(C)C] | 2-{3-[(4-methane-sulfonyl-2-methoxy-phenyl)amino]prop-1-yn-1-yl}-1-(2-methyl-propyl)-N-[(1R,4R)-4-(morpholin-4-yl)cyclohexyl]-1H-indol-4-amine | 593.3 |

TABLE 3-continued

| Compound No. | Structure | IUPAC | LC-MS (ES+, m/z) |
|---|---|---|---|
| 180A | 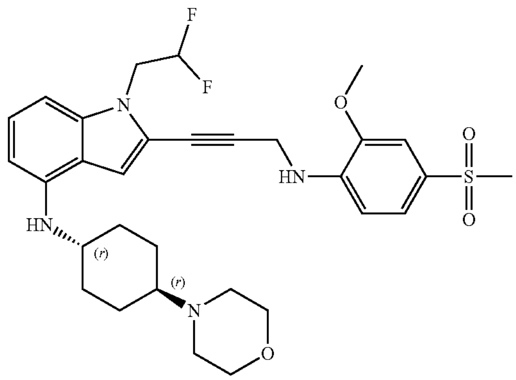 [SMILES: COc1cc(S(C)(=O)=O)ccc1NCC#Cc1cc2c(N[C@H]3CC[C@H](N4CCOCC4)CC3)cccc2n1CC(F)F] | 1-(2,2-difluoroethyl)-2-{3-[(4-methanesulfonyl-2-methoxyphenyl)amino]prop-1-yn-1-yl}-N-[(1R,4R)-4-(morpholin-4-yl)cyclohexyl]-1H-indol-4-amine | 601.3 |
| 181A | 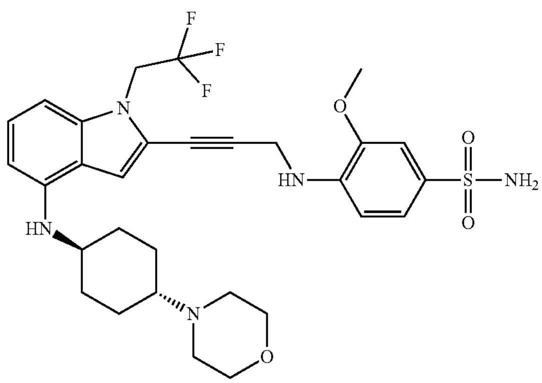 [SMILES: COc1cc(S(N)(=O)=O)ccc1NCC#Cc1cc2c(N[C@H]3CC[C@H](N4CCOCC4)CC3)cccc2n1CC(F)(F)F] | 3-methoxy-4-((3-(4-(((1R,4R)-4-morpholinocyclohexyl)amino)-1-(2,2,2-trifluoroethyl)-1H-indol-2-yl)prop-2-yn-1-yl)amino)benzenesulfonamide | 620.2 |
| 182A | 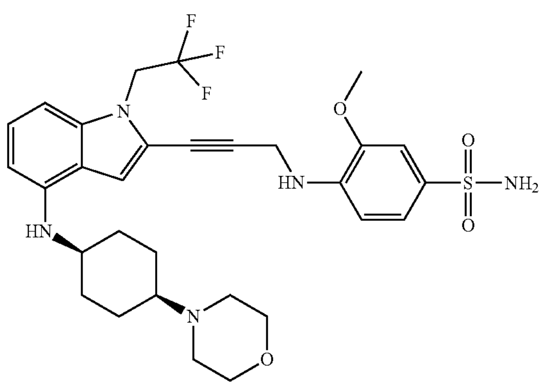 [SMILES: COc1cc(S(N)(=O)=O)ccc1NCC#Cc1cc2c(N[C@H]3CC[C@@H](N4CCOCC4)CC3)cccc2n1CC(F)(F)F] | 3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzenesulfonamide | 620.2 |
| 183A | 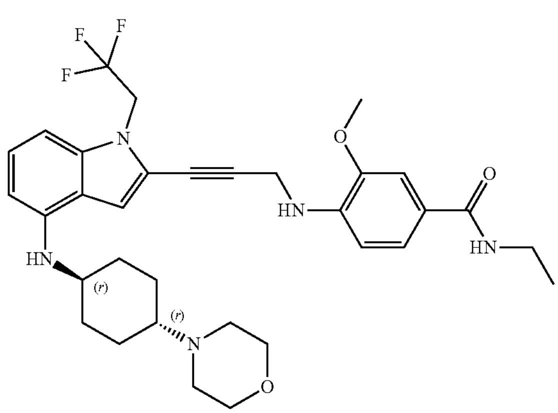 [SMILES: CCNC(=O)c1ccc(NCC#Cc2cc3c(N[C@H]4CC[C@H](N5CCOCC5)CC4)cccc3n2CC(F)(F)F)c(OC)c1] | N-ethyl-3-methoxy-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide | 612.3 |

TABLE 3-continued

| Compound No. | Structure | IUPAC | LC-MS (ES+, m/z) |
| --- | --- | --- | --- |
| 184A | 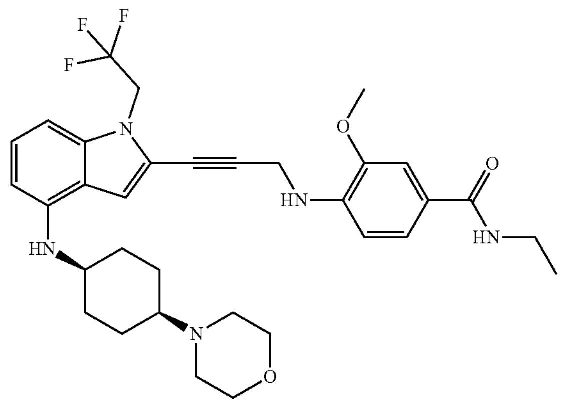 [SMILES: CCNC(=O)c1ccc(NCC#Cc2cc3c(N[C@H]4CC[C@@H](N5CCOCC5)CC4)cccc3n2CC(F)(F)F)c(OC)c1] | N-ethyl-3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzamide | 612.3 |
| 185A | 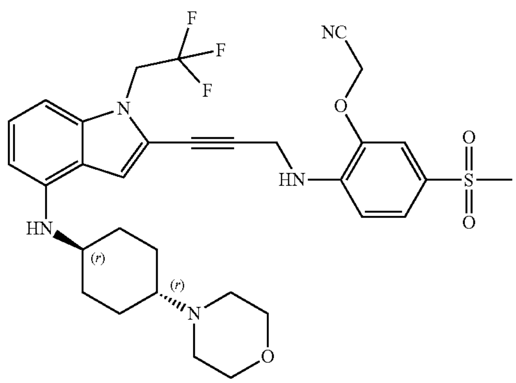 [SMILES: CS(=O)(=O)c1ccc(NCC#Cc2cc3c(N[C@H]4CC[C@H](N5CCOCC5)CC4)cccc3n2CC(F)(F)F)c(OCC#N)c1] | 2-(5-methanesulfonyl-2-{[3-(4-{[(1R,4R)-4-(morpholin-4-yl)cyclohexyl]amino}-1-(2,2,2-trifluoroethyl)-1H-indol-2-yl)prop-2-yn-1-yl]amino}phenoxy)acetonitrile | 644.2 |
| 186A | 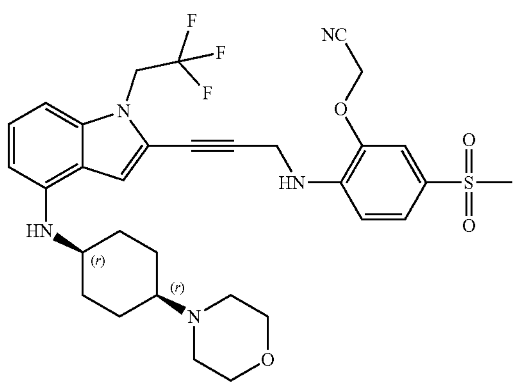 [SMILES: CS(=O)(=O)c1ccc(NCC#Cc2cc3c(N[C@H]4CC[C@@H](N5CCOCC5)CC4)cccc3n2CC(F)(F)F)c(OCC#N)c1] | 2-(5-methanesulfonyl-2-{[3-(4-{[(1S,4S)-4-(morpholin-4-yl)cyclohexyl]amino}-1-(2,2,2-trifluoroethyl)-1H-indol-2-yl)prop-2-yn-1-yl]amino}phenoxy)acetonitrile | 644.2 |
| 187A | 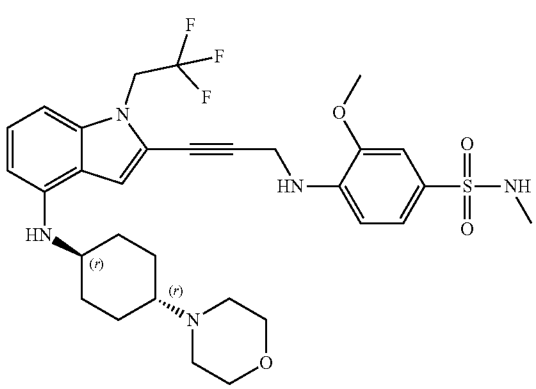 [SMILES: CNS(=O)(=O)c1ccc(NCC#Cc2cc3c(N[C@H]4CC[C@H](N5CCOCC5)CC4)cccc3n2CC(F)(F)F)c(OC)c1] | 3-methoxy-N-methyl-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide | 634.3 |

TABLE 3-continued

| Compound No. | Structure | IUPAC | LC-MS (ES+, m/z) |
|---|---|---|---|
| 188A | 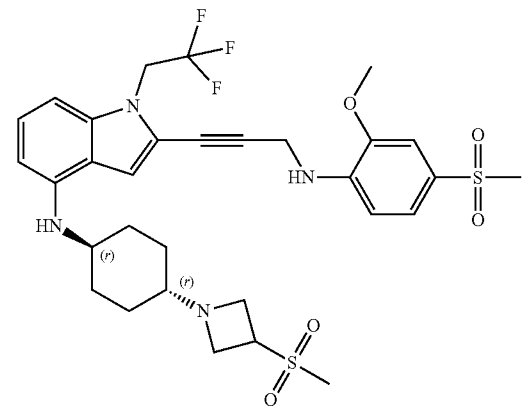 [SMILES: COc1cc(S(C)(=O)=O)ccc1NCC#Cc1cc2c(N[C@H]3CC[C@H](N4CC(S(C)(=O)=O)C4)CC3)cccc2n1CC(F)(F)F] | 2-{3-[(4-methane-sulfonyl-2-methoxy-phenyl)amino]prop-1-yn-1-yl}-N-[(1R,4R)-4-(3-methanesulfonyl-azetidin-1-yl)cyclohexyl]-1-(2,2,2-trifluoroethyl)-1H-indol-4-amine | 667.2 |
| 189A | 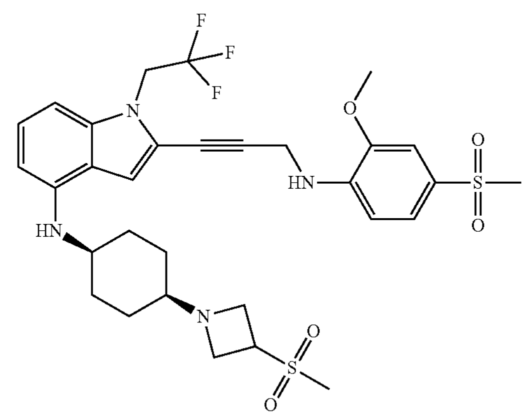 [SMILES: COc1cc(S(C)(=O)=O)ccc1NCC#Cc1cc2c(N[C@H]3CC[C@@H](N4CC(S(C)(=O)=O)C4)CC3)cccc2n1CC(F)(F)F] | 2-(3-((2-methoxy-4-(methylsulfonyl)phenyl)amino)prop-1-yn-1-yl)-N-((1S,4S)-4-(3-(methylsulfonyl)azetidin-1-yl)cyclohexyl)-1-(2,2,2-trifluoroethyl)-1H-indol-4-amine | 667.2 |
| 190A | 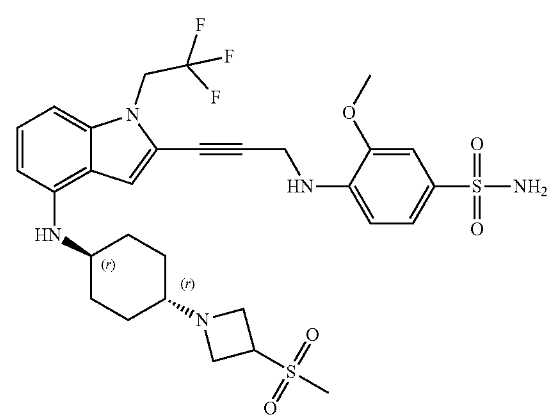 [SMILES: COc1cc(S(N)(=O)=O)ccc1NCC#Cc1cc2c(N[C@H]3CC[C@H](N4CC(S(C)(=O)=O)C4)CC3)cccc2n1CC(F)(F)F] | 3-methoxy-4-{[3-(4-{[(1R,4R)-4-(3-methanesulfonyl-azetidin-1-yl)cyclohexyl]amino}-1-(2,2,2-trifluoroethyl)-1H-indol-2-yl)prop-2-yn-1-yl]amino}benzene-1-sulfonamide | 668.2 |

TABLE 3-continued

| Compound No. | Structure | IUPAC | LC-MS (ES+, m/z) |
|---|---|---|---|
| 191A | 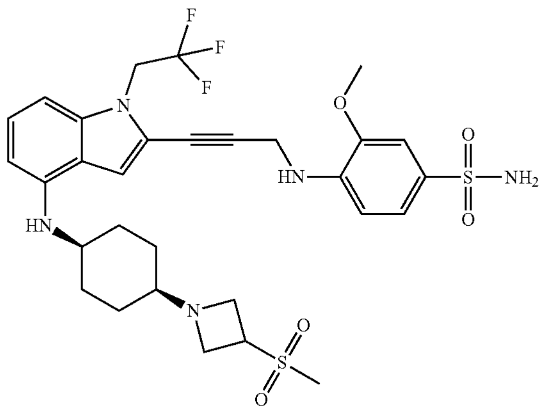 [SMILES: COc1cc(S(N)(=O)=O)ccc1NCC#Cc1cc2c(N[C@H]3CC[C@@H](N4CC(S(C)(=O)=O)C4)CC3)cccc2n1CC(F)(F)F] | 3-methoxy-4-((3-(4-(((1S,4S)-4-(3-(methyl-sulfonyl)azetidin-1-yl)cyclohexyl)amino)-1-(2,2,2-trifluoro-ethyl)-1H-indol-2-yl)prop-2-yn-1-yl)amino)benzenesulfonamide | 668.2 |
| 192A | 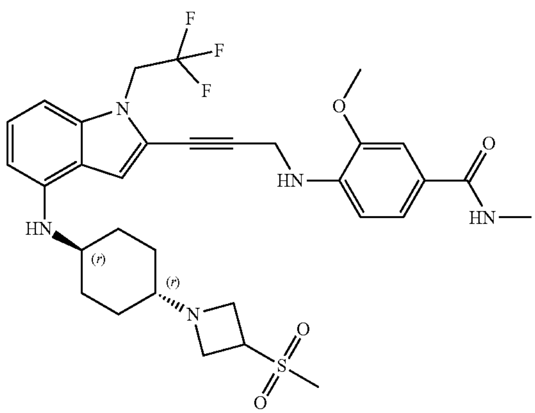 [SMILES: CNC(=O)c1ccc(NCC#Cc2cc3c(N[C@H]4CC[C@H](N5CC(S(C)(=O)=O)C5)CC4)cccc3n2CC(F)(F)F)c(OC)c1] | 3-methoxy-N-methyl-4-{[3-(4-{[(1R,4R)-4-(3-methanesulfonyl-azetidin-1-yl)cyclo-hexyl]amino}-1-(2,2,2-trifluoroethyl)-1H-indol-2-yl)prop-2-yn-1-yl]amino}benzamide | 646.2 |
| 193A | 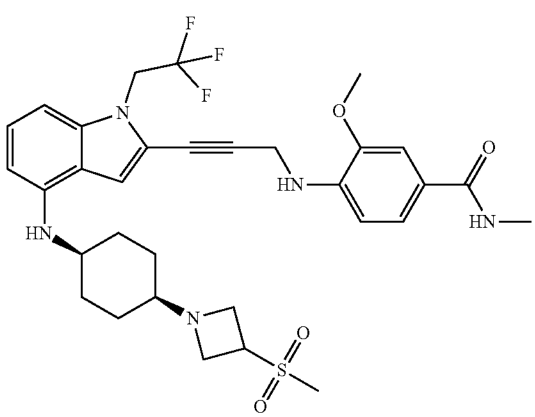 [SMILES: CNC(=O)c1ccc(NCC#Cc2cc3c(N[C@H]4CC[C@@H](N5CC(S(C)(=O)=O)C5)CC4)cccc3n2CC(F)(F)F)c(OC)c1] | 3-methoxy-N-methyl-4-((3-(4-(((1S,4S)-4-(3-(methyl-sulfonyl)azetidin-1-yl)cyclohexyl)amino)-1-(2,2,2-trifluoro-ethyl)-1H-indol-2-yl)prop-2-yn-1-yl)amino)benzamide | 646.2 |

TABLE 3-continued

| Compound No. | Structure | IUPAC | LC-MS (ES+, m/z) |
|---|---|---|---|
| 194A | 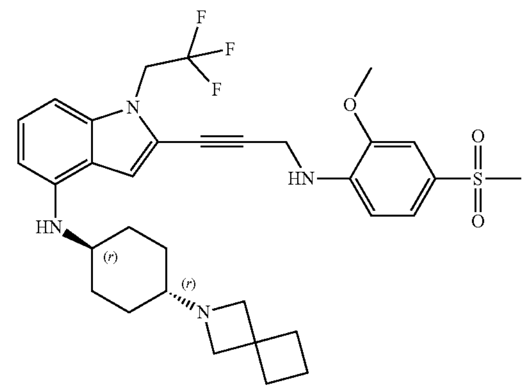 [SMILES: COc1cc(S(C)(=O)=O)ccc1NCC#Cc1cc2c(N[C@H]3CC[C@H](N4CC5(CCC5)C4)CC3)cccc2n1CC(F)(F)F] | 2-{3-[(4-methane-sulfonyl-2-methoxy-phenyl)amino]prop-1-yn-1-yl}-N-[(1R,4R)-4-{2-azaspiro[3.3]heptan-2-yl}cyclohexyl]-1-(2,2,2-trifluoroethyl)-1H-indol-4-amine | 629.2 |
| 195A | 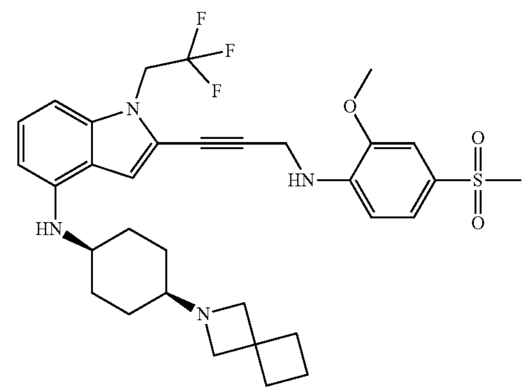 [SMILES: COc1cc(S(C)(=O)=O)ccc1NCC#Cc1cc2c(N[C@H]3CC[C@@H](N4CC5(CCC5)C4)CC3)cccc2n1CC(F)(F)F] | N-((1S,4S)-4-(2-azaspiro[3.3]heptan-2-yl)cyclohexyl)-2-(3-((2-methoxy-4-(methyl-sulfonyl)phenyl)amino)prop-1-yn-1-yl)-1-(2,2,2-trifluoroethyl)-1H-indol-4-amine | 629.2 |
| 196A | 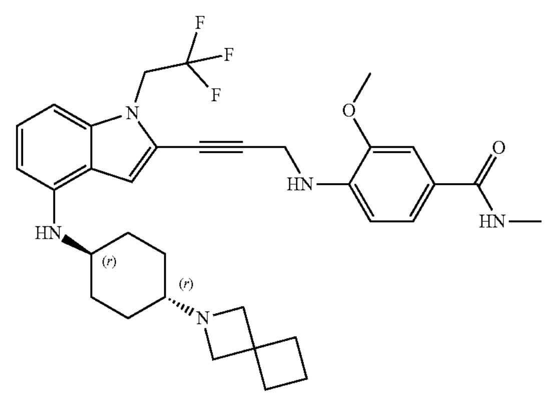 [SMILES: CNC(=O)c1ccc(NCC#Cc2cc3c(N[C@H]4CC[C@H](N5CC6(CCC6)C5)CC4)cccc3n2CC(F)(F)F)c(OC)c1] | 3-methoxy-N-methyl-4-{[3-(4-{[(1R,4R)-4-{2-azaspiro[3.3]heptan-2-yl}cyclohexyl]amino}-1-(2,2,2-trifluoroethyl)-1H-indol-2-yl)prop-2-yn-1-yl]amino}benzamide | 608.3 |
| 197A | 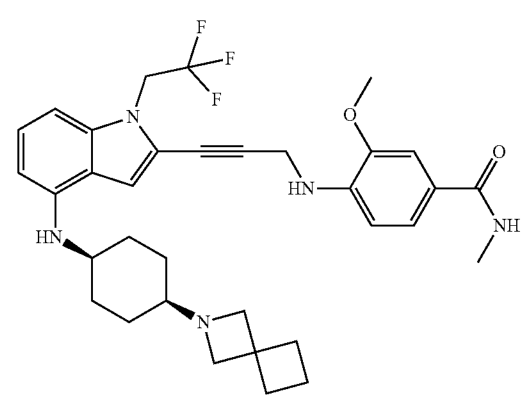 [SMILES: CNC(=O)c1ccc(NCC#Cc2cc3c(N[C@H]4CC[C@@H](N5CC6(CCC6)C5)CC4)cccc3n2CC(F)(F)F)c(OC)c1] | 4-((3-(4-(((1S,4S)-4-(2-azaspiro[3.3]heptan-2-yl)cyclohexyl)amino)-1-(2,2,2-trifluoroethyl)-1H-indol-2-yl)prop-2-yn-1-yl)amino)-3-methoxy-N-methylbenzamide | 608.3 |

TABLE 3-continued

| Compound No. | Structure | IUPAC | LC-MS (ES+, m/z) |
|---|---|---|---|
| 198A | 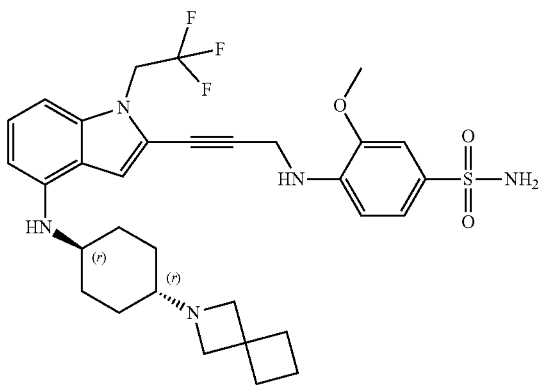 [SMILES: COc1cc(S(N)(=O)=O)ccc1NCC#Cc1cc2c(N[C@H]3CC[C@H](N4CC5(CCC5)C4)CC3)cccc2n1CC(F)(F)F] | 3-methoxy-4-{[3-(4-{[(1R,4R)-4-{2-azaspiro[3.3]heptan-2-yl}cyclohexyl]amino}-1-(2,2,2-trifluoroethyl)-1H-indol-2-yl)prop-2-yn-1-yl]amino}benzene-1-sulfonamide | 630.3 |
| 199A | 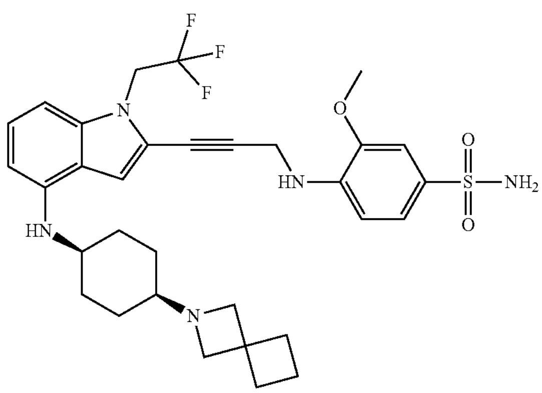 [SMILES: COc1cc(S(N)(=O)=O)ccc1NCC#Cc1cc2c(N[C@H]3CC[C@@H](N4CC5(CCC5)C4)CC3)cccc2n1CC(F)(F)F] | 4-((3-(4-(((1S,4S)-4-(2-azaspiro[3.3]heptan-2-yl)cyclohexyl)amino)-1-(2,2,2-trifluoroethyl)-1H-indol-2-yl)prop-2-yn-1-yl)amino)-3-methoxybenzenesulfonamide | 630.3 |
| 200A | 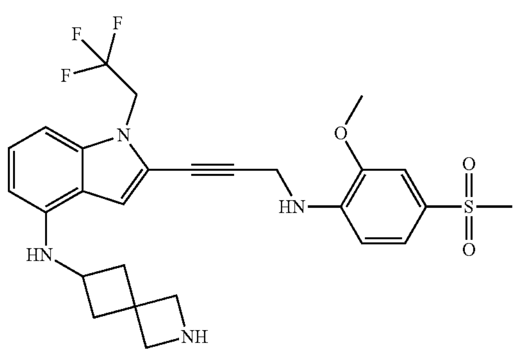 [SMILES: COc1cc(S(C)(=O)=O)ccc1NCC#Cc1cc2c(NC3CC4(CNC4)C3)cccc2n1CC(F)(F)F] | 2-(3-((2-methoxy-4-(methylsulfonyl)phenyl)amino)prop-1-yn-1-yl)-N-(2-azaspiro[3.3]heptan-6-yl)-1-(2,2,2-trifluoroethyl)-1H-indol-4-amine | 547.2 |
| 201A | 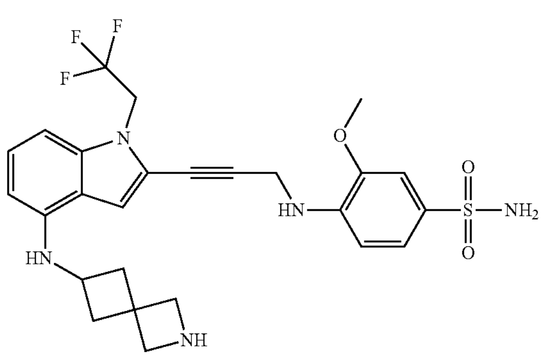 [SMILES: COc1cc(S(N)(=O)=O)ccc1NCC#Cc1cc2c(NC3CC4(CNC4)C3)cccc2n1CC(F)(F)F] | 4-((3-(4-((2-azaspiro[3.3]heptan-6-yl)amino)-1-(2,2,2-trifluoroethyl)-1H-indol-2-yl)prop-2-yn-1-yl)amino)-3-methoxybenzenesulfonamide | 548.2 |

TABLE 3-continued

| Compound No. | Structure | IUPAC | LC-MS (ES+, m/z) |
|---|---|---|---|
| 202A | 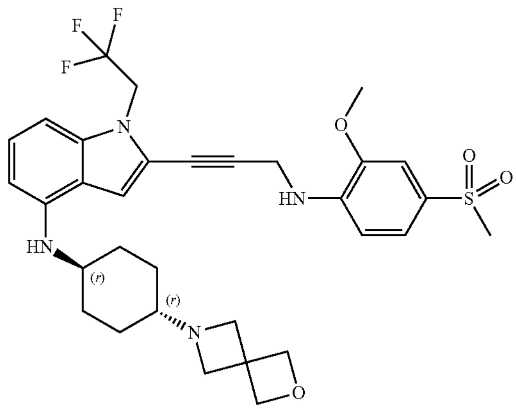 [SMILES: COc1cc(S(C)(=O)=O)ccc1NCC#Cc1cc2c(N[C@H]3CC[C@H](N4CC5(COC5)C4)CC3)cccc2n1CC(F)(F)F] | 2-{3-[(4-methane-sulfonyl-2-methoxy-phenyl)amino]prop-1-yn-1-yl}-N-[(1R,4R)-4-{2-oxa-6-azaspiro[3.3]heptan-6-yl}cyclohexyl]-1-(2,2,2-trifluoro-ethyl)-1H-indol-4-amine | 631.2 |
| 203A | 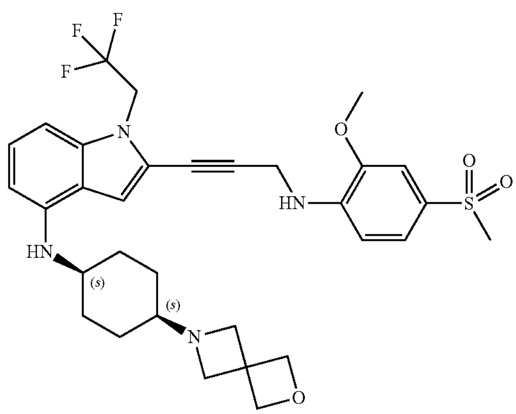 [SMILES: COc1cc(S(C)(=O)=O)ccc1NCC#Cc1cc2c(N[C@H]3CC[C@@H](N4CC5(COC5)C4)CC3)cccc2n1CC(F)(F)F] | 2-{3-[(4-methane-sulfonyl-2-methoxy-phenyl)amino]prop-1-yn-1-yl}-N-[(1S,4S)-4-{2-oxa-6-azaspiro[3.3]heptan-6-yl}cyclo-hexyl]-1-(2,2,2-trifluoro-ethyl)-1H-indol-4-amine | 631.2 |
| 204A | 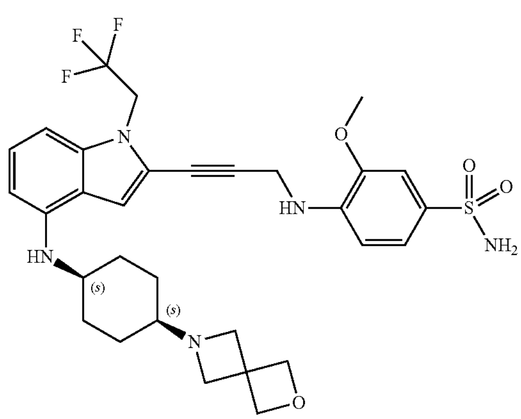 [SMILES: COc1cc(S(N)(=O)=O)ccc1NCC#Cc1cc2c(N[C@H]3CC[C@@H](N4CC5(COC5)C4)CC3)cccc2n1CC(F)(F)F] | 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide | 632.2 |

TABLE 3-continued

| Compound No. | Structure | IUPAC | LC-MS (ES+, m/z) |
|---|---|---|---|
| 205A | 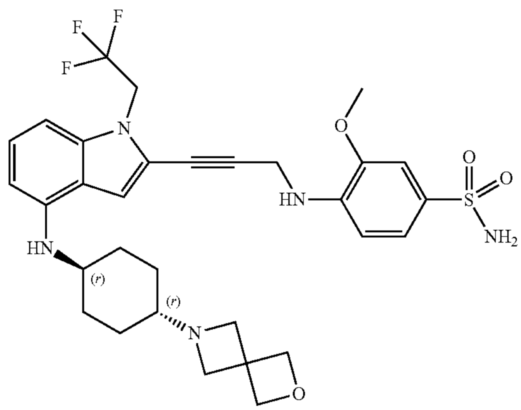 [SMILES: COc1cc(S(N)(=O)=O)ccc1NCC#Cc1cc2c(N[C@H]3CC[C@H](N4CC5(COC5)C4)CC3)cccc2n1CC(F)(F)F] | 3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide | 632.2 |
| 206A | 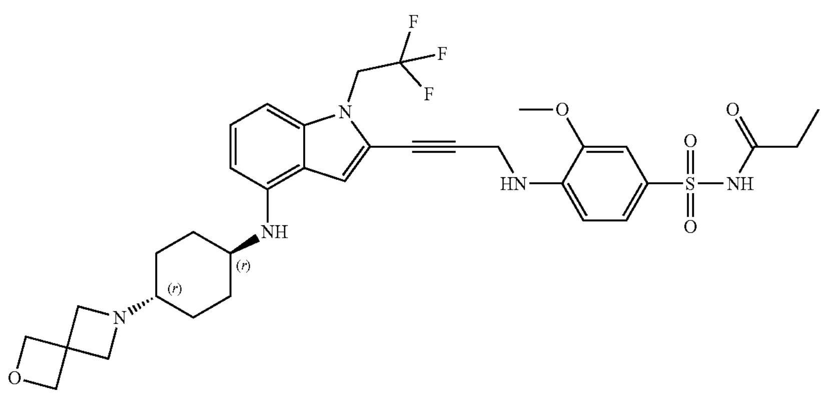 [SMILES: CCC(=O)NS(=O)(=O)c1ccc(NCC#Cc2cc3c(N[C@H]4CC[C@H](N5CC6(COC6)C5)CC4)cccc3n2CC(F)(F)F)c(OC)c1] | N-(3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)propanamide | 688.4 |
| 207A | 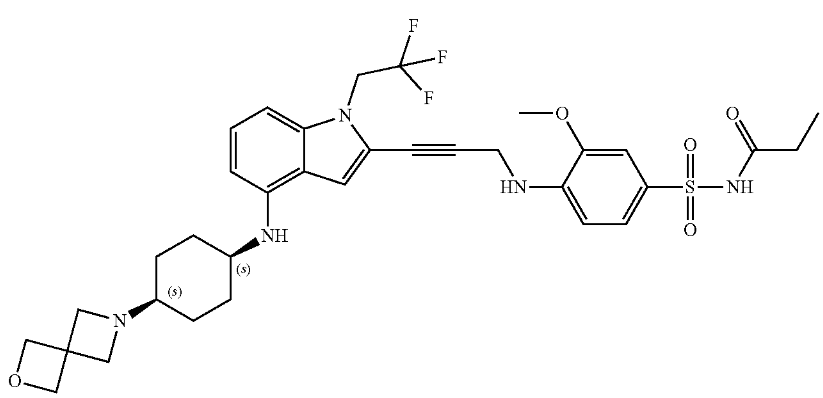 [SMILES: CCC(=O)NS(=O)(=O)c1ccc(NCC#Cc2cc3c(N[C@H]4CC[C@@H](N5CC6(COC6)C5)CC4)cccc3n2CC(F)(F)F)c(OC)c1] | N-(3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)propanamide | 688.4 |

TABLE 3-continued

| Compound No. | Structure | IUPAC | LC-MS (ES+, m/z) |
|---|---|---|---|
| 208A | 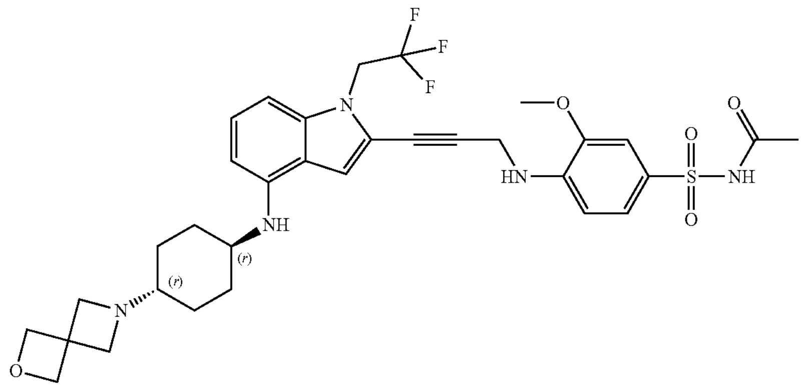 [SMILES: COc1cc(S(=O)(=O)NC(C)=O)ccc1NCC#Cc1cc2c(N[C@H]3CC[C@H](N4CC5(COC5)C4)CC3)cccc2n1CC(F)(F)F] | N-(3-methoxy-4-{[3-(4-{[(1R,4R)-4-{2-oxa-6-azaspiro[3.3]heptan-6-yl}cyclohexyl]amino}-1-(2,2,2-trifluoro-ethyl)-1H-indol-2-yl)prop-2-yn-1-yl]amino}benzene-sulfonyl)acetamide | 674.3 |
| 209A | 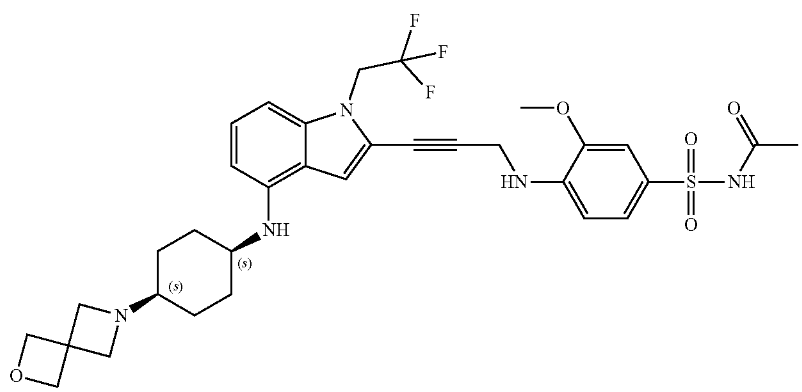 [SMILES: COc1cc(S(=O)(=O)NC(C)=O)ccc1NCC#Cc1cc2c(N[C@H]3CC[C@@H](N4CC5(COC5)C4)CC3)cccc2n1CC(F)(F)F] | N-(3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-sulfonyl)acetamide | 674.3 |
| 210A | 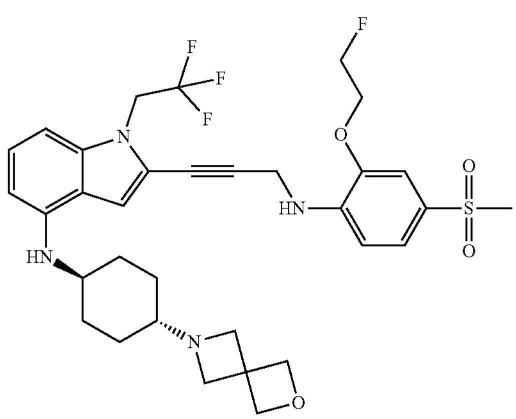 [SMILES: CS(=O)(=O)c1ccc(NCC#Cc2cc3c(N[C@H]4CC[C@H](N5CC6(COC6)C5)CC4)cccc3n2CC(F)(F)F)c(OCCF)c1] | N-((1R,4R)-4-(2-oxa-6-azaspiro[3.3]heptan-6-yl)cyclohexyl)-2-(3-((2-(2-fluoroethoxy)-4-(methylsulfonyl)phenyl)amino)prop-1-yn-1-yl)-1-(2,2,2-trifluoroethyl)-1H-indol-4-amine | 663.2 |

TABLE 3-continued

| Compound No. | Structure | IUPAC | LC-MS (ES+, m/z) |
|---|---|---|---|
| 211A | 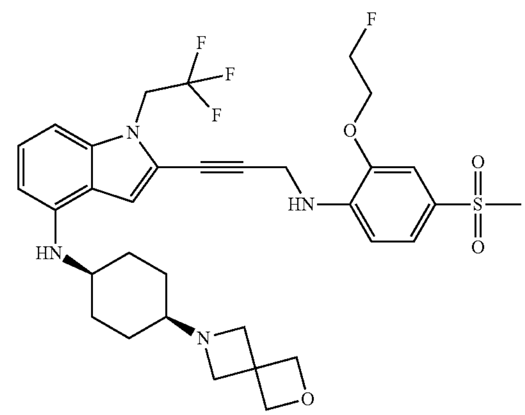 [SMILES: CS(=O)(=O)c1ccc(NCC#Cc2cc3c(N[C@H]4CC[C@@H](N5CC6(COC6)C5)CC4)cccc3n2CC(F)(F)F)c(OCCF)c1] | N-((1S,4S)-4-(2-oxa-6-azaspiro[3.3]heptan-6-yl)cyclohexyl)-2-(3-((2-(2-fluoroethoxy)-4-(methylsulfonyl)phenyl)amino)prop-1-yn-1-yl)-1-(2,2,2-trifluoroethyl)-1H-indol-4-amine | |
| 212A | 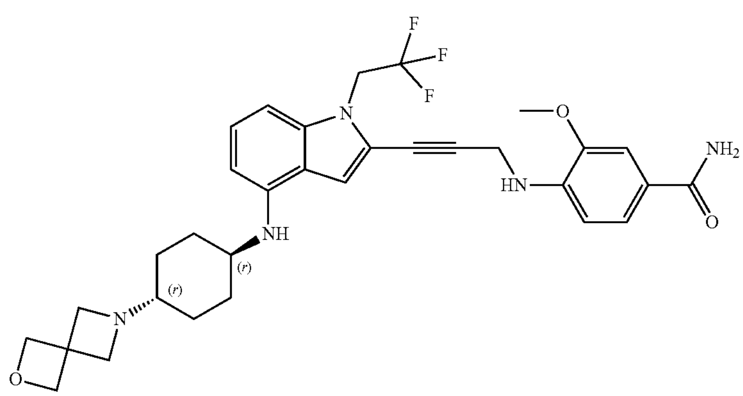 [SMILES: COc1cc(C(N)=O)ccc1NCC#Cc1cc2c(N[C@H]3CC[C@H](N4CC5(COC5)C4)CC3)cccc2n1CC(F)(F)F] | 3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide | 596.1 |
| 213A | 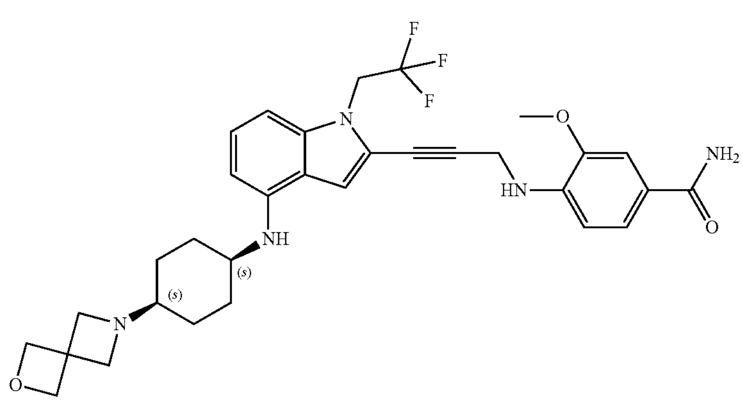 [SMILES: COc1cc(C(N)=O)ccc1NCC#Cc1cc2c(N[C@H]3CC[C@@H](N4CC5(COC5)C4)CC3)cccc2n1CC(F)(F)F] | 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide | 596.1 |

TABLE 3-continued

| Compound No. | Structure | IUPAC | LC-MS (ES+, m/z) |
|---|---|---|---|
| 214A | 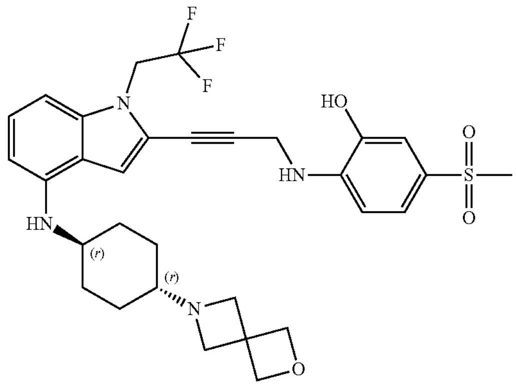 [SMILES: CS(=O)(=O)c1ccc(NCC#Cc2cc3c(N[C@H]4CC[C@H](N5CC6(COC6)C5)CC4)cccc3n2CC(F)(F)F)c(O)c1] | 5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenol | 617.2 |
| 215A | 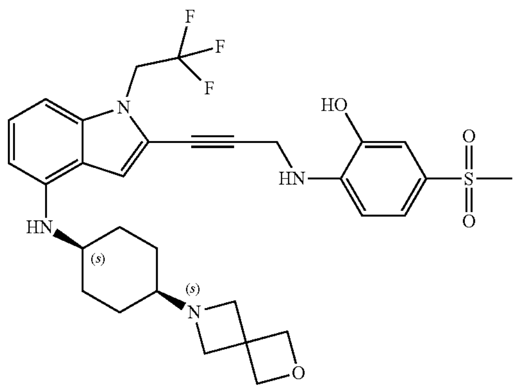 [SMILES: CS(=O)(=O)c1ccc(NCC#Cc2cc3c(N[C@H]4CC[C@@H](N5CC6(COC6)C5)CC4)cccc3n2CC(F)(F)F)c(O)c1] | 5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenol | 617.3 |
| 216A | 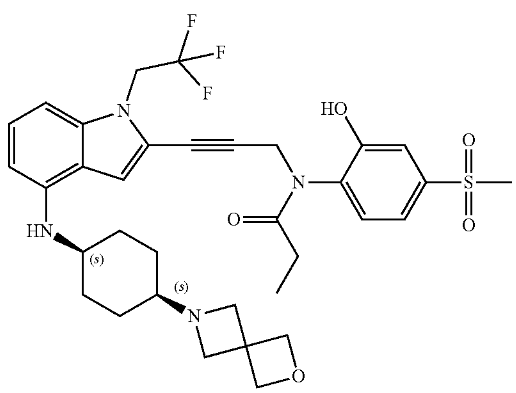 [SMILES: CCC(=O)N(CC#Cc1cc2c(N[C@H]3CC[C@@H](N4CC5(COC5)C4)CC3)cccc2n1CC(F)(F)F)c1ccc(S(C)(=O)=O)cc1O] | N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)propionamide | 673.1 |
| 217A | 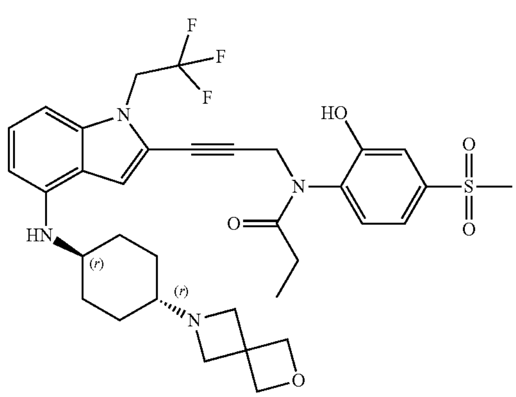 [SMILES: CCC(=O)N(CC#Cc1cc2c(N[C@H]3CC[C@H](N4CC5(COC5)C4)CC3)cccc2n1CC(F)(F)F)c1ccc(S(C)(=O)=O)cc1O] | N-(3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)propionamide | |

TABLE 3-continued

| Compound No. | Structure | IUPAC | LC-MS (ES+, m/z) |
|---|---|---|---|
| 218A | 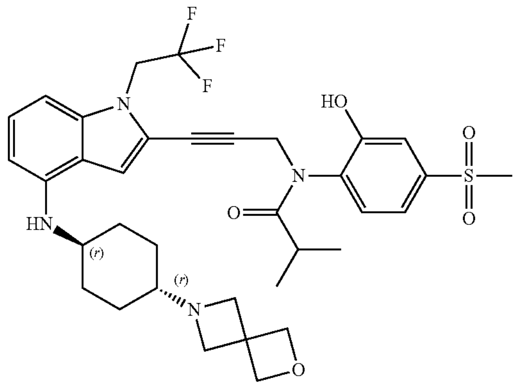 [SMILES: CC(C)C(=O)N(CC#Cc1cc2c(N[C@H]3CC[C@H](N4CC5(COC5)C4)CC3)cccc2n1CC(F)(F)F)c1ccc(S(C)(=O)=O)cc1O] | N-(2-hydroxy-4-methanesulfonylphenyl)-2-methyl-N-[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]propanamide | 687.2 |
| 219A | 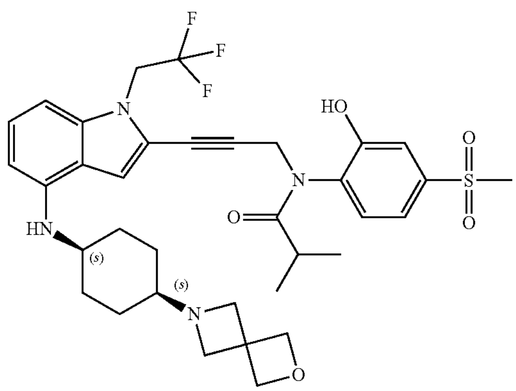 [SMILES: CC(C)C(=O)N(CC#Cc1cc2c(N[C@H]3CC[C@@H](N4CC5(COC5)C4)CC3)cccc2n1CC(F)(F)F)c1ccc(S(C)(=O)=O)cc1O] | N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide | 687.2 |
| 220A | 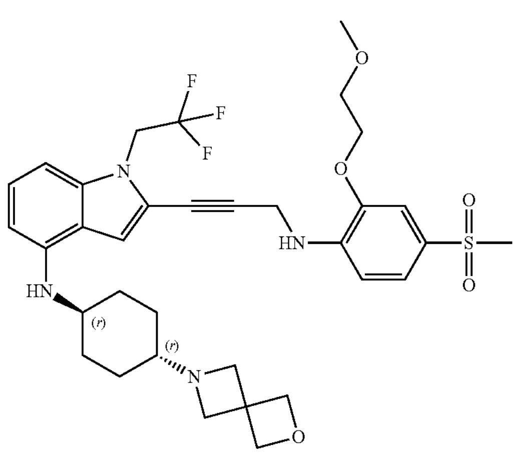 [SMILES: COCCOc1cc(S(C)(=O)=O)ccc1NCC#Cc1cc2c(N[C@H]3CC[C@H](N4CC5(COC5)C4)CC3)cccc2n1CC(F)(F)F] | 2-(3-{[4-methanesulfonyl-2-(2-methoxyethoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine | 675.4 |

TABLE 3-continued

| Compound No. | Structure | IUPAC | LC-MS (ES+, m/z) |
|---|---|---|---|
| 221A | 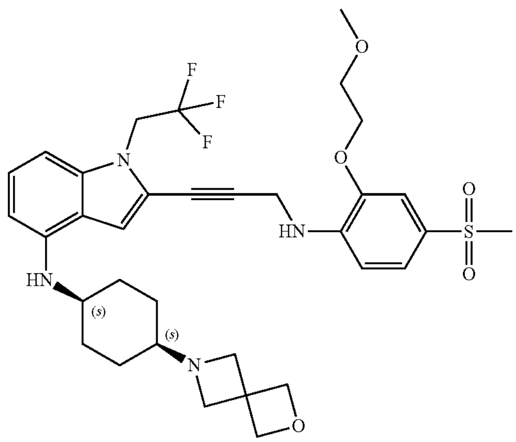 [SMILES: COCCOc1cc(S(C)(=O)=O)ccc1NCC#Cc1cc2c(N[C@H]3CC[C@@H](N4CC5(COC5)C4)CC3)cccc2n1CC(F)(F)F] | 2-(3-{[4-methane-sulfonyl-2-(2-methoxyethoxy)phenyl]amino}prop-1-yn-1-yl)-N-[(1S,4S)-4-{2-oxa-6-azaspiro[3.3]heptan-6-yl}cyclohexyl]-1-(2,2,2-trifluoroethyl)-1H-indol-4-amine | 675.4 |
| 222A | 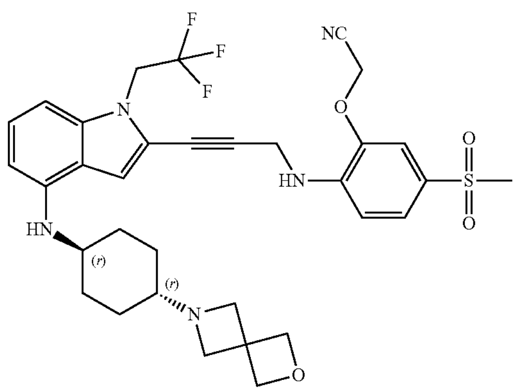 | 2-(5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)acetonitrile | 656.4 |
| 223A | 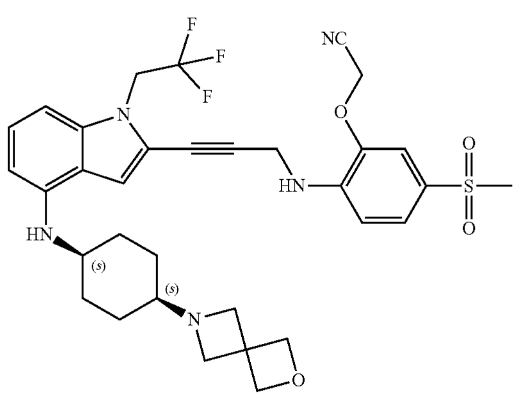 [SMILES: CS(=O)(=O)c1ccc(NCC#Cc2cc3c(N[C@H]4CC[C@@H](N5CC6(COC6)C5)CC4)cccc3n2CC(F)(F)F)c(OCC#N)c1] | 2-(5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)acetonitrile | 656.4 |

TABLE 3-continued

| Compound No. | Structure | IUPAC | LC-MS (ES+, m/z) |
| --- | --- | --- | --- |
| 224A | 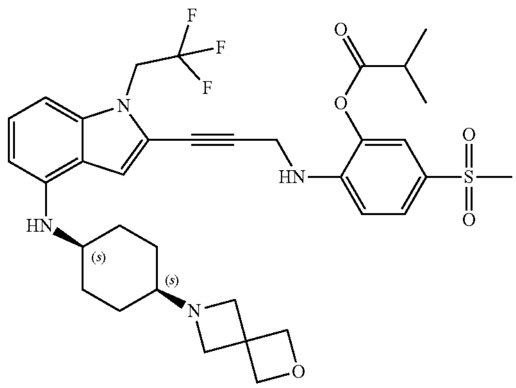 [SMILES: CC(C)C(=O)Oc1cc(S(C)(=O)=O)ccc1NCC#Cc1cc2c(N[C@H]3CC[C@@H](N4CC5(COC5)C4)CC3)cccc2n1CC(F)(F)F] | 5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl 2-methylpropanoate | 687.4 |
| 225A | 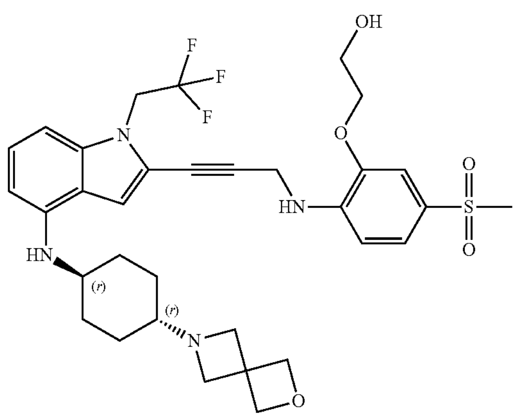 [SMILES: CS(=O)(=O)c1ccc(NCC#Cc2cc3c(N[C@H]4CC[C@H](N5CC6(COC6)C5)CC4)cccc3n2CC(F)(F)F)c(OCCO)c1] | 2-(5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)ethan-1-ol | 661.3 |
| 226A | 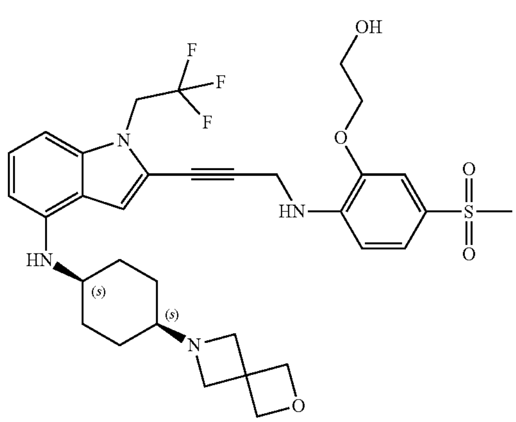 [SMILES: CS(=O)(=O)c1ccc(NCC#Cc2cc3c(N[C@H]4CC[C@@H](N5CC6(COC6)C5)CC4)cccc3n2CC(F)(F)F)c(OCCO)c1] | 2-(5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)ethan-1-ol | 661.1 |

TABLE 3-continued

| Compound No. | Structure | IUPAC | LC-MS (ES+, m/z) |
|---|---|---|---|
| 227A | 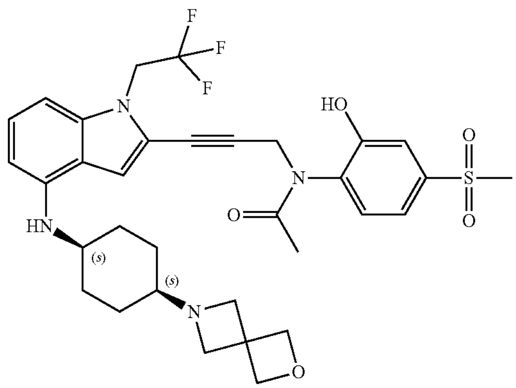 [SMILES: CC(=O)N(CC#Cc1cc2c(N[C@H]3CC[C@@H](N4CC5(COC5)C4)CC3)cccc2n1CC(F)(F)F)c1ccc(S(C)(=O)=O)cc1O] | N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)acetamide | |
| 228A | 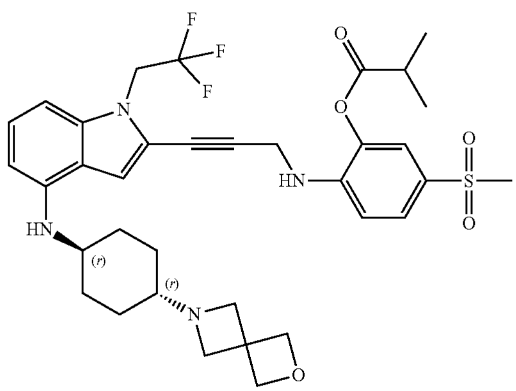 [SMILES: CC(C)C(=O)Oc1cc(S(C)(=O)=O)ccc1NCC#Cc1cc2c(N[C@H]3CC[C@H](N4CC5(COC5)C4)CC3)cccc2n1CC(F)(F)F] | 5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl 2-methylpropanoate | 687.3 |
| 229A | 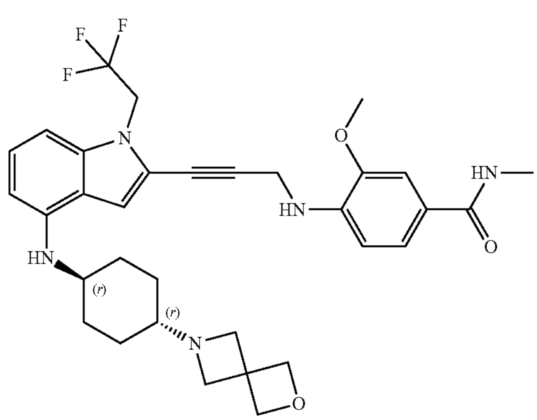 [SMILES: CNC(=O)c1ccc(NCC#Cc2cc3c(N[C@H]4CC[C@H](N5CC6(COC6)C5)CC4)cccc3n2CC(F)(F)F)c(OC)c1] | 3-methoxy-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide | 610.3 |

TABLE 3-continued

| Compound No. | Structure | IUPAC | LC-MS (ES+, m/z) |
|---|---|---|---|
| 230A | 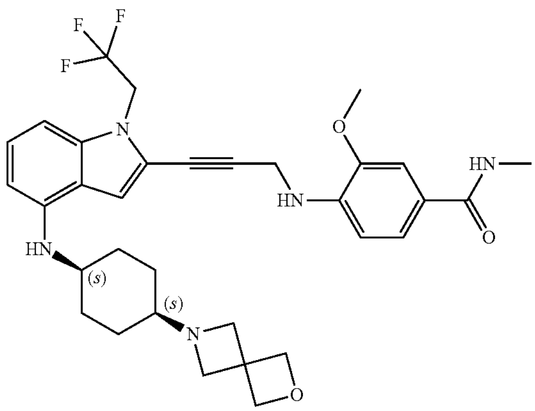 [SMILES: CNC(=O)c1ccc(NCC#Cc2cc3c(N[C@H]4CC[C@@H](N5CC6(COC6)C5)CC4)cccc3n2CC(F)(F)F)c(OC)c1] | 3-methoxy-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide | 610.3 |
| 231A | 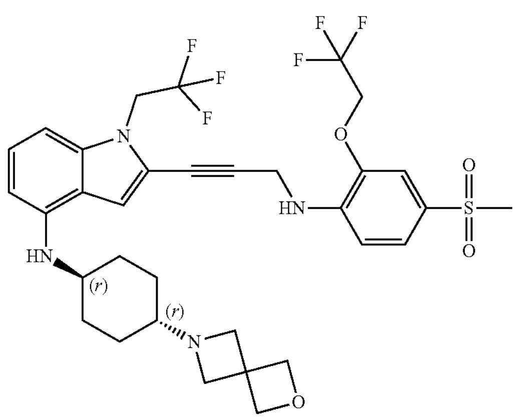 [SMILES: CS(=O)(=O)c1ccc(NCC#Cc2cc3c(N[C@H]4CC[C@H](N5CC6(COC6)C5)CC4)cccc3n2CC(F)(F)F)c(OCC(F)(F)F)c1] | 2-(3-{[4-methanesulfonyl-2-(2,2,2-trifluoroethoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine | 699.3 |
| 232A | 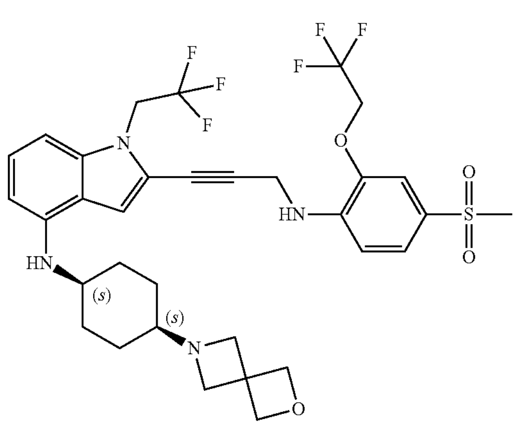 [SMILES: CS(=O)(=O)c1ccc(NCC#Cc2cc3c(N[C@H]4CC[C@@H](N5CC6(COC6)C5)CC4)cccc3n2CC(F)(F)F)c(OCC(F)(F)F)c1] | 2-(3-{[4-methanesulfonyl-2-(2,2,2-trifluoroethoxy)phenyl]amino}prop-1-yn-1-yl)-N-[(1S,4S)-4-{2-oxa-6-azaspiro[3.3]heptan-6-yl}cyclohexyl]-1-(2,2,2-trifluoroethyl)-1H-indol-4-amine | 699.0 |

TABLE 3-continued

| Compound No. | Structure | IUPAC | LC-MS (ES+, m/z) |
|---|---|---|---|
| 233A | 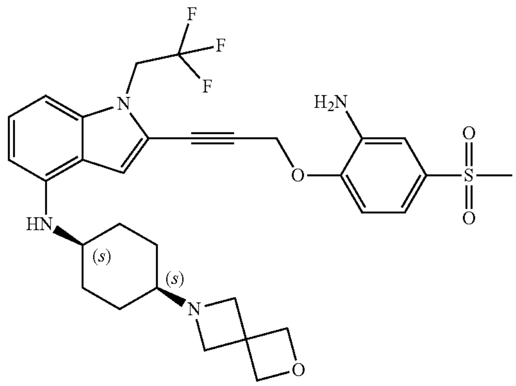 [SMILES: CS(=O)(=O)c1ccc(OCC#Cc2cc3c(N[C@H]4CC[C@@H](N5CC6(COC6)C5)CC4)cccc3n2CC(F)(F)F)c(N)c1] | 2-[3-(2-amino-4-methanesulfonyl-phenoxy)prop-1-yn-1-yl]-N-[(1S,4S)-4-{2-oxa-6-azaspiro[3.3]heptan-6-yl}cyclohexyl]-1-(2,2,2-trifluoroethyl)-1H-indol-4-amine | 617.1 |
| 234A | 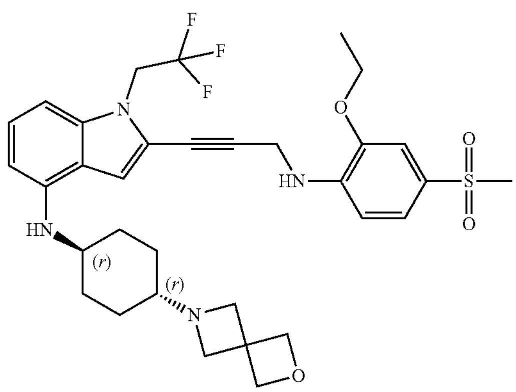 [SMILES: CCOc1cc(S(C)(=O)=O)ccc1NCC#Cc1cc2c(N[C@H]3CC[C@H](N4CC5(COC5)C4)CC3)cccc2n1CC(F)(F)F] | 2-{3-[(2-ethoxy-4-methanesulfonyl-phenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine | 645.2 |
| 235A | 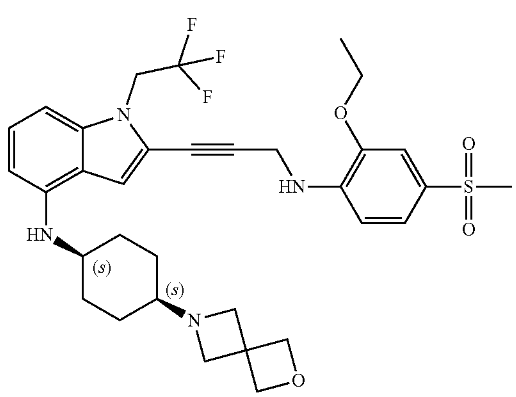 | 2-{3-[(2-ethoxy-4-methanesulfonyl-phenyl)amino]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine | 645.2 |

TABLE 3-continued

| Compound No. | Structure | IUPAC | LC-MS (ES+, m/z) |
|---|---|---|---|
| 236A | 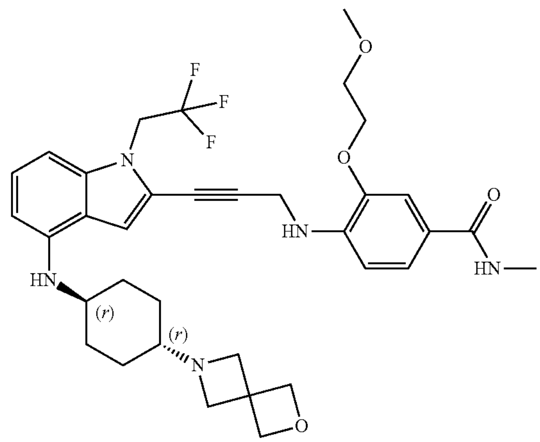 [SMILES: CNC(=O)c1ccc(NCC#Cc2cc3c(N[C@H]4CC[C@H](N5CC6(COC6)C5)CC4)cccc3n2CC(F)(F)F)c(OCCOC)c1] | 3-(2-methoxyethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide | 654.3 |
| 237A | 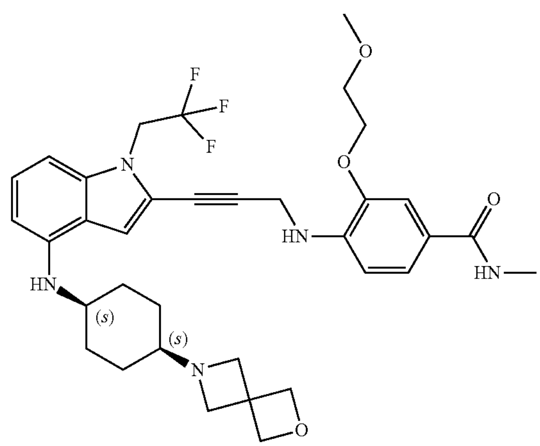 [SMILES: CNC(=O)c1ccc(NCC#Cc2cc3c(N[C@H]4CC[C@@H](N5CC6(COC6)C5)CC4)cccc3n2CC(F)(F)F)c(OCCOC)c1] | 3-(2-methoxyethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide | 654.3 |
| 238A | 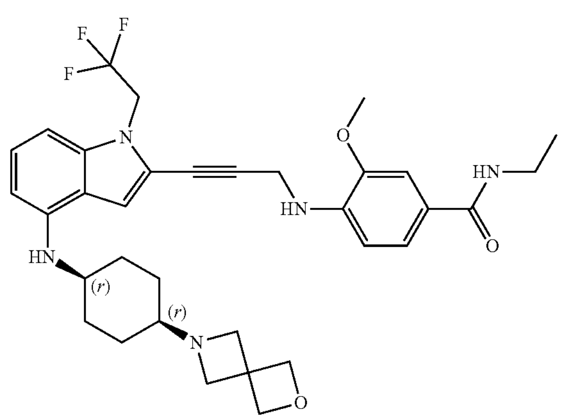 [SMILES: CCNC(=O)c1ccc(NCC#Cc2cc3c(N[C@H]4CC[C@@H](N5CC6(COC6)C5)CC4)cccc3n2CC(F)(F)F)c(OC)c1] | N-ethyl-3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide | 624.3 |

TABLE 3-continued

| Compound No. | Structure | IUPAC | LC-MS (ES+, m/z) |
|---|---|---|---|
| 239A | 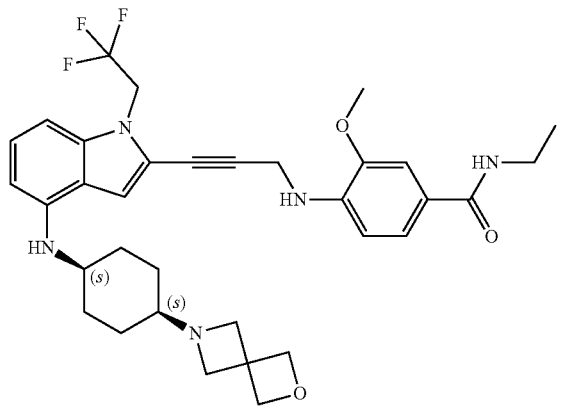 [SMILES: CCNC(=O)c1ccc(NCC#Cc2cc3c(N[C@H]4CC[C@@H](N5CC6(COC6)C5)CC4)cccc3n2CC(F)(F)F)c(OC)c1] | N-ethyl-3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide | 624.3 |
| 240A | 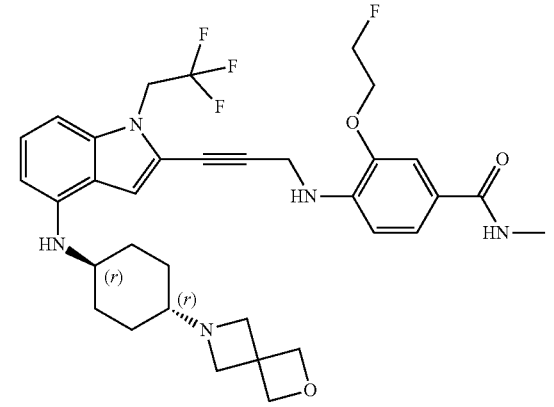 [SMILES: CNC(=O)c1ccc(NCC#Cc2cc3c(N[C@H]4CC[C@H](N5CC6(COC6)C5)CC4)cccc3n2CC(F)(F)F)c(OCCF)c1] | 3-(2-fluoroethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide | 642.3 |
| 241A | 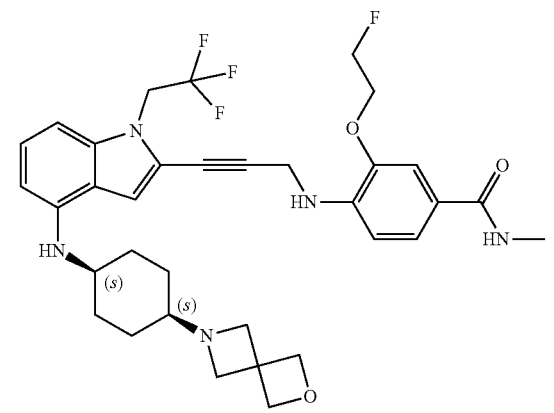 [SMILES: CNC(=O)c1ccc(NCC#Cc2cc3c(N[C@H]4CC[C@@H](N5CC6(COC6)C5)CC4)cccc3n2CC(F)(F)F)c(OCCF)c1] | 3-(2-fluoroethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide | 642.3 |

TABLE 3-continued

| Compound No. | Structure | IUPAC | LC-MS (ES+, m/z) |
|---|---|---|---|
| 242A | 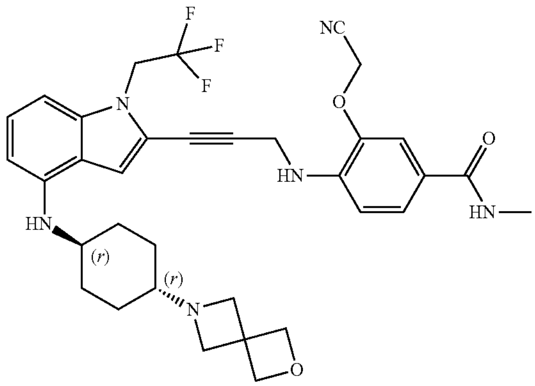 [SMILES: CNC(=O)c1ccc(NCC#Cc2cc3c(N[C@H]4CC[C@H](N5CC6(COC6)C5)CC4)cccc3n2CC(F)(F)F)c(OCC#N)c1] | 3-(cyanomethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide | 635.2 |
| 243A | 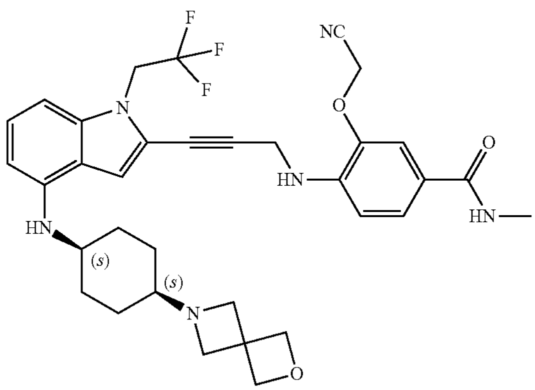 [SMILES: CNC(=O)c1ccc(NCC#Cc2cc3c(N[C@H]4CC[C@@H](N5CC6(COC6)C5)CC4)cccc3n2CC(F)(F)F)c(OCC#N)c1] | 3-(cyanomethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide | 635.3 |
| 244A | 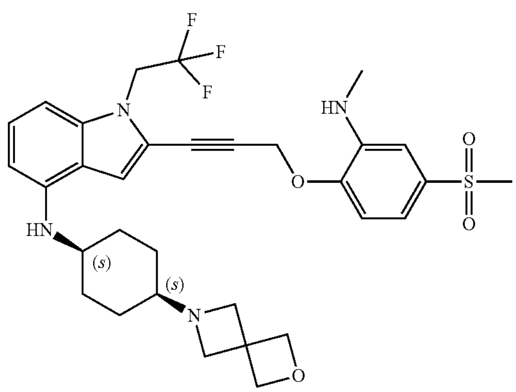 [SMILES: CNc1cc(S(C)(=O)=O)ccc1OCC#Cc1cc2c(N[C@H]3CC[C@@H](N4CC5(COC5)C4)CC3)cccc2n1CC(F)(F)F] | 2-{3-[4-methanesulfonyl-2-(methylamino)phenoxy]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine | 631.3 |
| 245A | 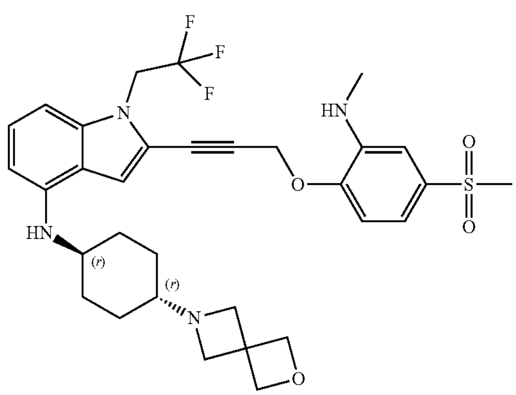 | 2-{3-[4-methanesulfonyl-2-(methylamino)phenoxy]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine | 631.2 |

TABLE 3-continued

| Compound No. | Structure | IUPAC | LC-MS (ES+, m/z) |
|---|---|---|---|
| 246A | 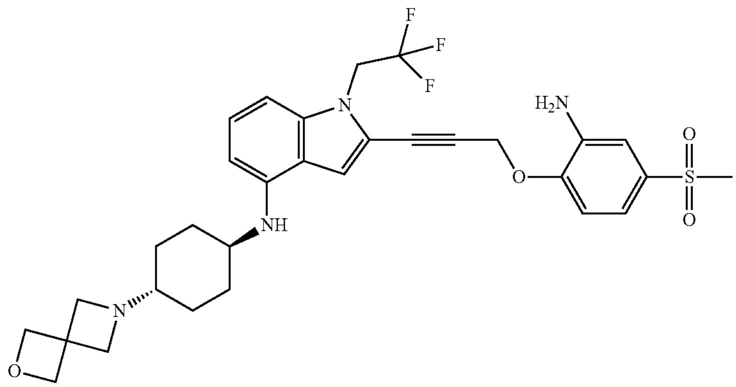 | 2-[3-(2-amino-4-methanesulfonyl-phenoxy)prop-1-yn-1-yl]-N-[(1R,4R)-4-{2-oxa-6-azaspiro[3.3]heptan-6-yl}cyclohexyl]-1-(2,2,2-trifluoroethyl)-1H-indol-4-amine | 617.2 |
| 247A | 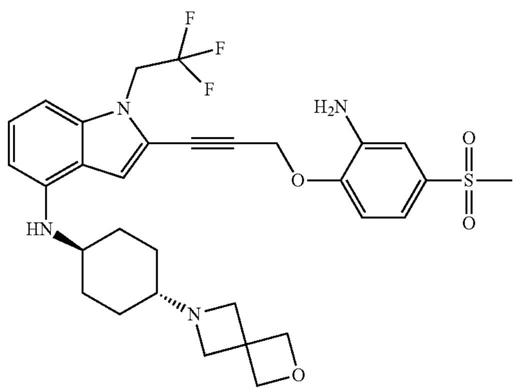 | N-((1R,4R)-4-(2-oxa-6-azaspiro[3.3]heptan-6-yl)cyclohexyl)-2-(3-(2-amino-4-(methyl-sulfonyl)phenoxy)prop-1-yn-1-yl)-1-(2,2,2-trifluoro-ethyl)-1H-indol-4-amine | 617.2 |
| 248A | 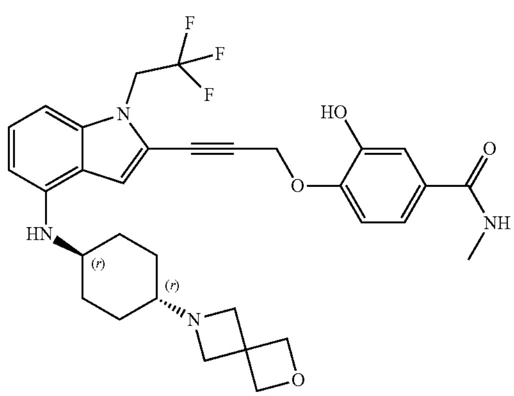 | 3-hydroxy-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide | 596.2 |

TABLE 3-continued

| Compound No. | Structure | IUPAC | LC-MS (ES+, m/z) |
|---|---|---|---|
| 249A | 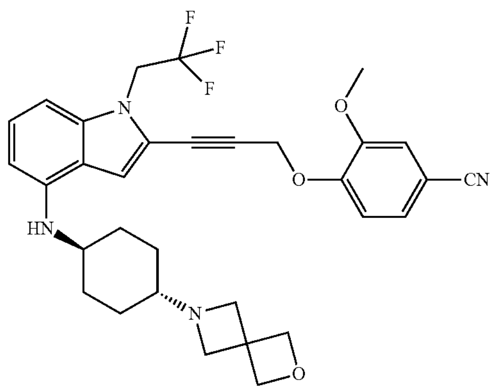 | 3-methoxy-4-[(3-{4-[(4-{2-oxa-6-azaspiro[3.3]heptan-6-yl}cyclohexyl)amino]-1-(2,2,2-trifluoroethyl)-1H-indol-2-yl}prop-2-yn-1-yl)amino]benzonitrile | 578.2 |
| 250A | 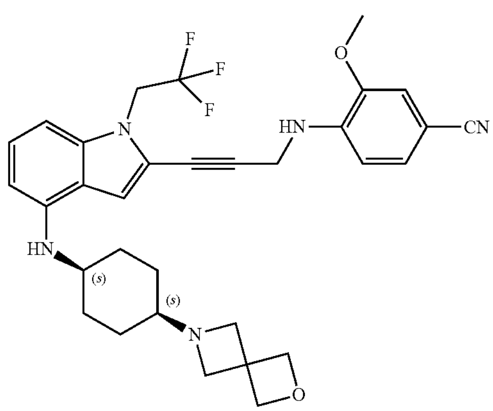 | 3-methoxy-4-{[3-(4-{[(1S,4S)-4-(2-oxa-6-azaspiro[3.3]heptan-6-yl)cyclohexyl]amino}-1-(2,2,2-trifluoroethyl)-1H-indol-2-yl)prop-2-yn-1-yl]amino}benzonitrile | 578.3 |
| 251A | 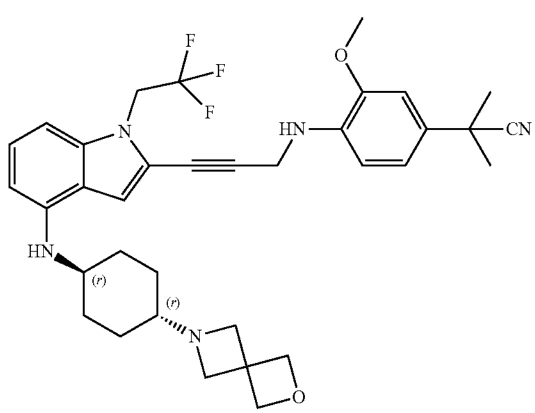 | 2-(3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl)-2-methylpropanenitrile | 620.3 |

TABLE 3-continued

| Compound No. | Structure | IUPAC | LC-MS (ES+, m/z) |
|---|---|---|---|
| 252A | 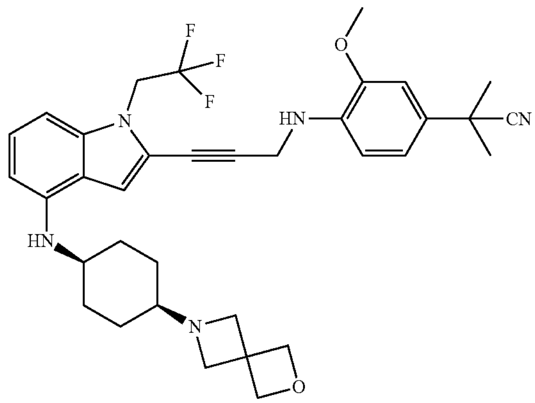 | 2-(4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxyphenyl)-2-methylpropanenitrile | 620.3 |
| 253A | 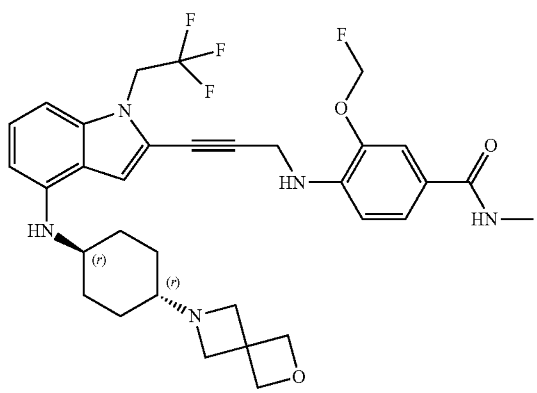 | 3-(fluoromethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide | 628.3 |
| 254A | 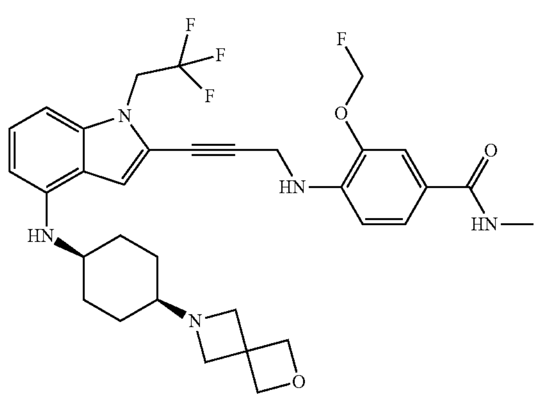 | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-(fluoromethoxy)-N-methylbenzamide | 628.3 |

TABLE 3-continued

| Compound No. | Structure | IUPAC | LC-MS (ES+, m/z) |
|---|---|---|---|
| 255A | 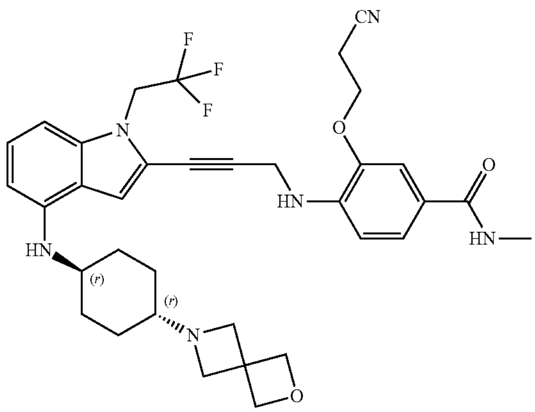 | 3-(2-cyanoethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide | 649.3 |
| 256A | 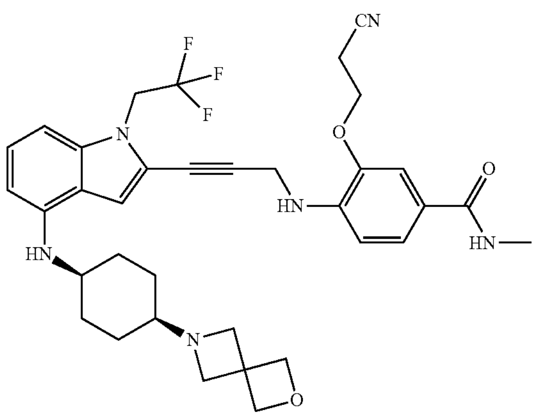 | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-(2-cyanoethoxy)-N-methylbenzamide | 649.3 |
| 257A | 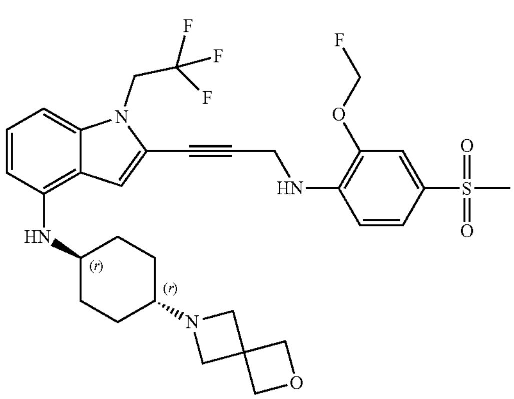 | 2-(3-{[2-(fluoromethoxy)-4-methanesulfonylphenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine | 649.3 |

TABLE 3-continued

| Compound No. | Structure | IUPAC | LC-MS (ES+, m/z) |
|---|---|---|---|
| 258A | 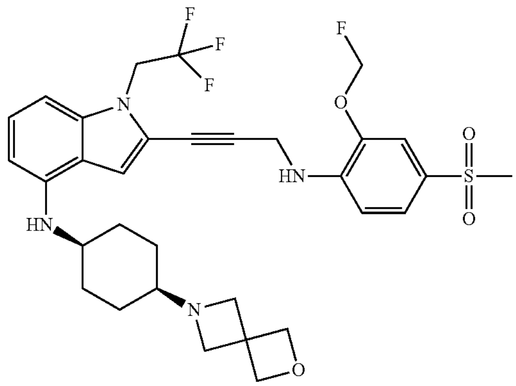 | N-((1S,4S)-4-(2-oxa-6-azaspiro[3.3]heptan-6-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine | 649.3 |
| 259A | 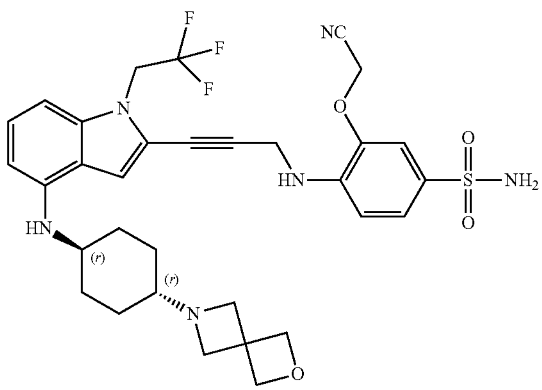 | 3-(cyanomethoxy)-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide | 657.4 |
| 260A | 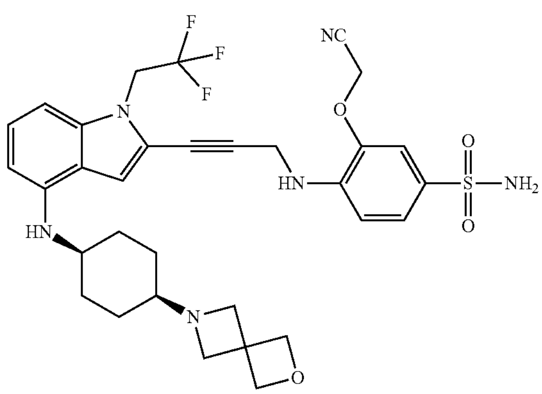 [SMILES: N#CCOc1cc(S(N)(=O)=O)ccc1NCC#Cc1cc2c(N[C@H]3CC[C@@H](N4CC5(COC5)C4)CC3)cccc2n1CC(F)(F)F] | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-(cyanomethoxy)benzenesulfonamide | 657.4 |
| 261A | 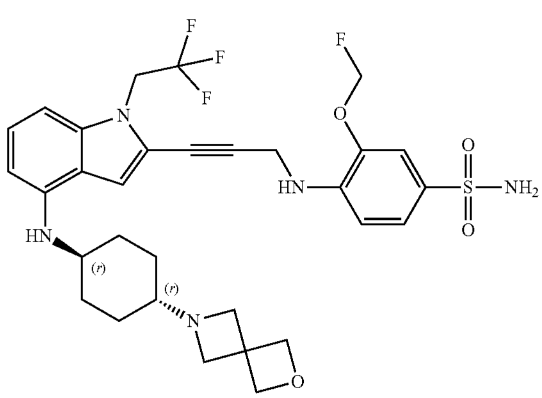 [SMILES: NS(=O)(=O)c1ccc(NCC#Cc2cc3c(N[C@H]4CC[C@H](N5CC6(COC6)C5)CC4)cccc3n2CC(F)(F)F)c(OCF)c1] | 3-(fluoromethoxy)-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide | 650.2 |

TABLE 3-continued

| Compound No. | Structure | IUPAC | LC-MS (ES+, m/z) |
|---|---|---|---|
| 262A | 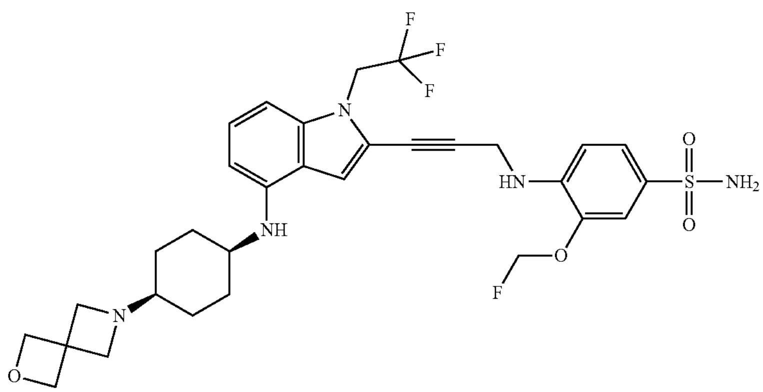 [SMILES: NS(=O)(=O)c1ccc(NCC#Cc2cc3c(N[C@H]4CC[C@@H](N5CC6(COC6)C5)CC4)cccc3n2CC(F)(F)F)c(OCF)c1] | 3-(fluoromethoxy)-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide | 650.2 |
| 263A | 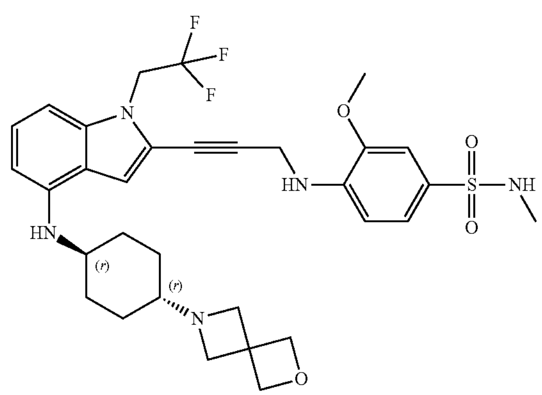 [SMILES: CNS(=O)(=O)c1ccc(NCC#Cc2cc3c(N[C@H]4CC[C@H](N5CC6(COC6)C5)CC4)cccc3n2CC(F)(F)F)c(OC)c1] | 4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N-methylbenzenesulfonamide | 646.2 |
| 264A | 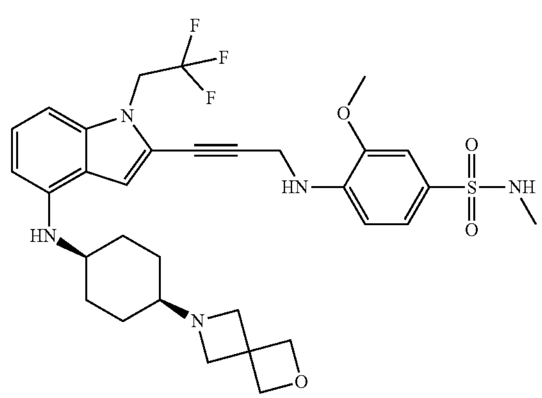 [SMILES: CNS(=O)(=O)c1ccc(NCC#Cc2cc3c(N[C@H]4CC[C@@H](N5CC6(COC6)C5)CC4)cccc3n2CC(F)(F)F)c(OC)c1] | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N-methylbenzenesulfonamide | 646.3 |

TABLE 3-continued

| Compound No. | Structure | IUPAC | LC-MS (ES+, m/z) |
|---|---|---|---|
| 265A | 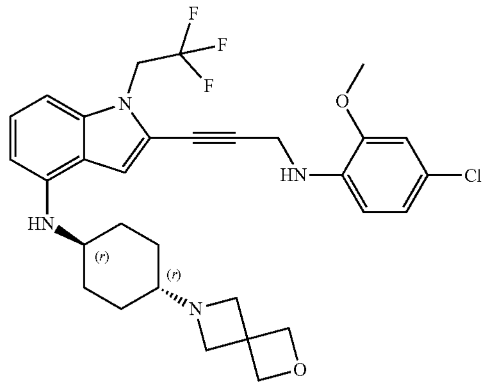 [SMILES: COc1cc(Cl)ccc1NCC#Cc1cc2c(N[C@H]3CC[C@H](N4CC5(COC5)C4)CC3)cccc2n1CC(F)(F)F] | N-((1R,4R)-4-(2-oxa-6-azaspiro[3.3]heptan-6-yl)cyclohexyl)-2-(3-((4-chloro-2-methoxyphenyl)amino)prop-1-yn-1-yl)-1-(2,2,2-trifluoroethyl)-1H-indol-4-amine | 587.2 |
| 266A | 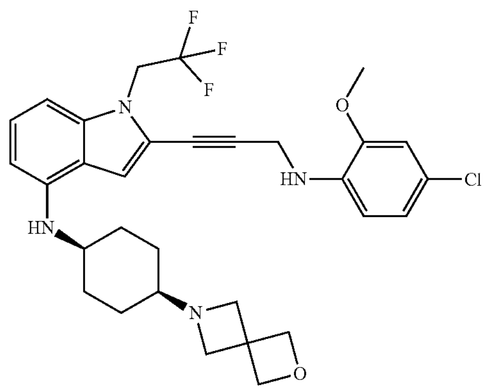 [SMILES: COc1cc(Cl)ccc1NCC#Cc1cc2c(N[C@H]3CC[C@@H](N4CC5(COC5)C4)CC3)cccc2n1CC(F)(F)F] | N-((1S,4S)-4-(2-oxa-6-azaspiro[3.3]heptan-6-yl)cyclohexyl)-2-(3-((4-chloro-2-methoxyphenyl)amino)prop-1-yn-1-yl)-1-(2,2,2-trifluoroethyl)-1H-indol-4-amine | 587.2 |
| 267A | 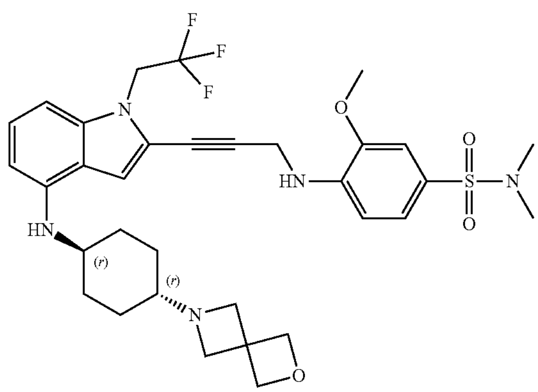 [SMILES: COc1cc(S(=O)(=O)N(C)C)ccc1NCC#Cc1cc2c(N[C@H]3CC[C@H](N4CC5(COC5)C4)CC3)cccc2n1CC(F)(F)F] | 4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N,N-dimethylbenzenesulfonamide | 660.2 |
| 268A | 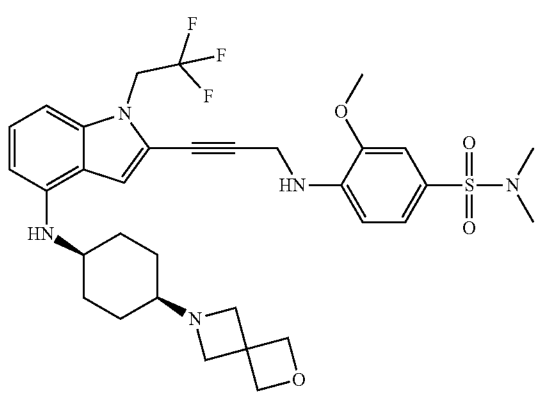 [SMILES: COc1cc(S(=O)(=O)N(C)C)ccc1NCC#Cc1cc2c(N[C@H]3CC[C@@H](N4CC5(COC5)C4)CC3)cccc2n1CC(F)(F)F] | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N,N-dimethylbenzenesulfonamide | 660.2 |

TABLE 3-continued

| Compound No. | Structure | IUPAC | LC-MS (ES+, m/z) |
|---|---|---|---|
| 269A | 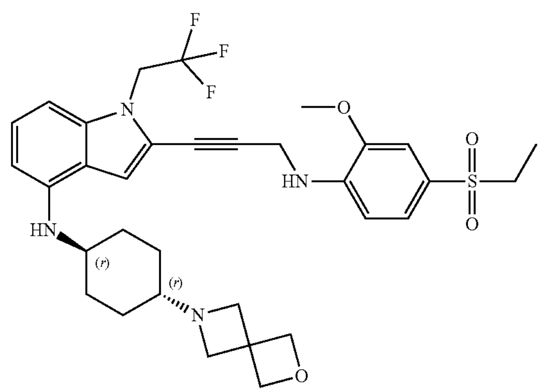 [SMILES: CCS(=O)(=O)c1ccc(NCC#Cc2cc3c(N[C@H]4CC[C@H](N5CC6(COC6)C5)CC4)cccc3n2CC(F)(F)F)c(OC)c1] | N-((1R,4R)-4-(2-oxa-6-azaspiro[3.3]heptan-6-yl)cyclohexyl)-2-(3-((4-(ethylsulfonyl)-2-methoxyphenyl)amino)propl-yn-1-yl)-1-(2,2,2-trifluoroethyl)-1H-indol-4-amine | 645.2 |
| 270A | 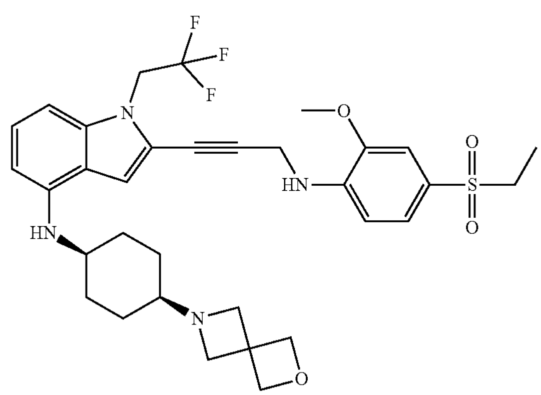 [SMILES: CCS(=O)(=O)c1ccc(NCC#Cc2cc3c(N[C@H]4CC[C@@H](N5CC6(COC6)C5)CC4)cccc3n2CC(F)(F)F)c(OC)c1] | N-((1S,4S)-4-(2-oxa-6-azaspiro[3.3]heptan-6-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine | 645.2 |
| 271A | 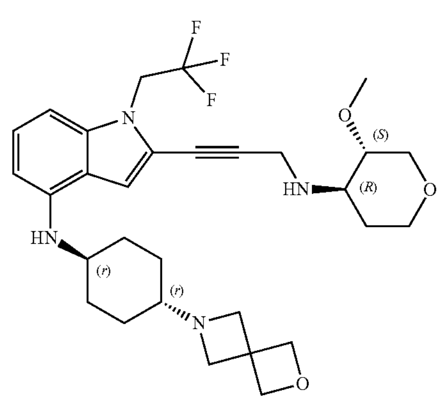 | N-((1R,4R)-4-(2-oxa-6-azaspiro[3.3]heptan-6-yl)cyclohexyl)-2-(3-(((3S,4R)-3-methoxytetrahydro-2H-pyran-4-yl)amino)prop-1-yn-1-yl)-1-(2,2,2-trifluoroethyl)-1H-indol-4-amine | 561.3 |

TABLE 3-continued

| Compound No. | Structure | IUPAC | LC-MS (ES+, m/z) |
| --- | --- | --- | --- |
| 272A | 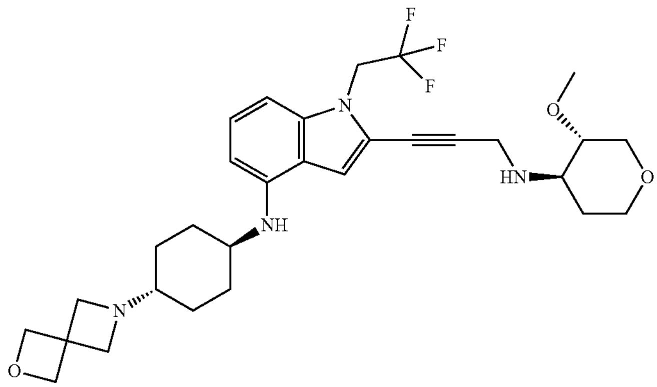 [SMILES: CO[C@@H]1COCC[C@H]1NCC#Cc1cc2c(N[C@H]3CC[C@H](N4CC5(COC5)C4)CC3)cccc2n1CC(F)(F)F] | N-((1S,4S)-4-(2-oxa-6-azaspiro[3.3]heptan-6-yl)cyclohexyl)-2-(3-(((3S,4R)-3-methoxy-tetrahydro-2H-pyran-4-yl)amino)prop-1-yn-1-yl)-1-(2,2,2-trifluoro-ethyl)-1H-indol-4-amine | 561.3 |
| 273A | 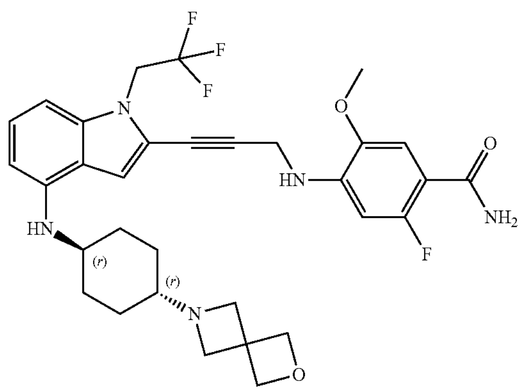 [SMILES: COc1cc(C(N)=O)c(F)cc1NCC#Cc1cc2c(N[C@H]3CC[C@H](N4CC5(COC5)C4)CC3)cccc2n1CC(F)(F)F] | 2-fluoro-5-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide | 614.2 |
| 274A | 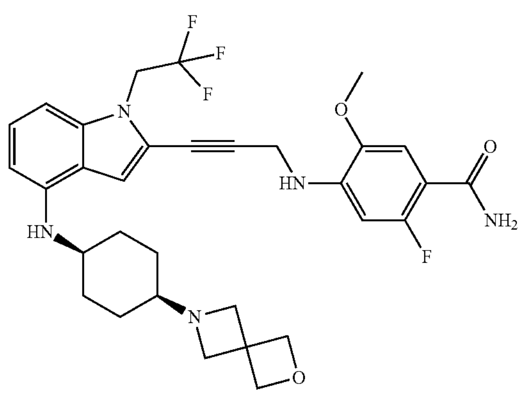 [SMILES: COc1cc(C(N)=O)c(F)cc1NCC#Cc1cc2c(N[C@H]3CC[C@@H](N4CC5(COC5)C4)CC3)cccc2n1CC(F)(F)F] | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxybenzamide | 614.2 |
| 275A | 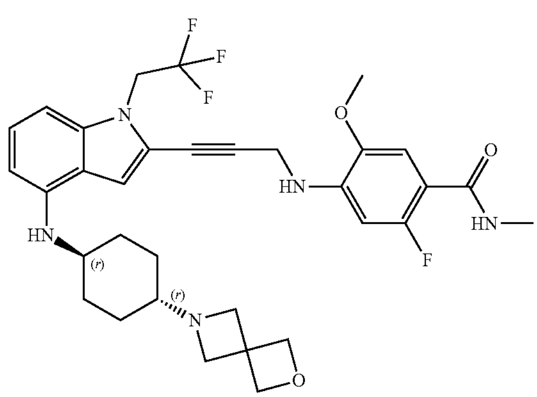 [SMILES: CNC(=O)c1cc(OC)c(NCC#Cc2cc3c(N[C@H]4CC[C@H](N5CC6(COC6)C5)CC4)cccc3n2CC(F)(F)F)cc1F] | 2-fluoro-5-methoxy-N-methyl-4-{[3-(4-{[( R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide | 628.2 |

TABLE 3-continued

| Compound No. | Structure | IUPAC | LC-MS (ES+, m/z) |
|---|---|---|---|
| 276A | 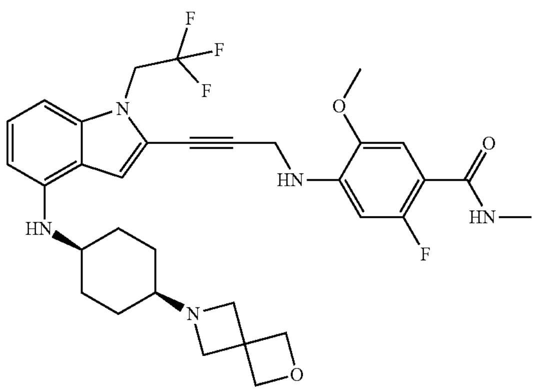 [SMILES: CNC(=O)c1cc(OC)c(NCC#Cc2cc3c(N[C@H]4CC[C@@H](N5CC6(COC6)C5)CC4)cccc3n2CC(F)(F)F)cc1F] | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxy-N-methylbenzamide | 628.2 |
| 277A | 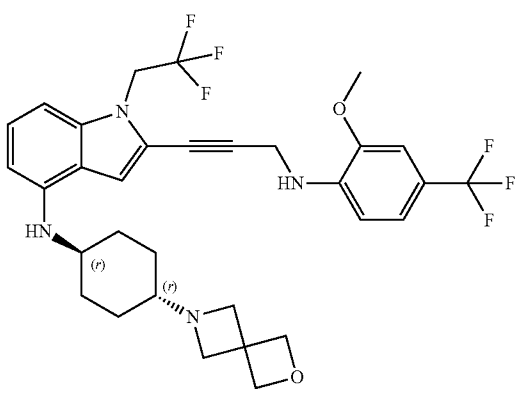 [SMILES: COc1cc(C(F)(F)F)ccc1NCC#Cc1cc2c(N[C@H]3CC[C@H](N4CC5(COC5)C4)CC3)cccc2n1CC(F)(F)F] | 2-(3-{[2-methoxy-4-(trifluoromethyl)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine | 621.2 |
| 278A | 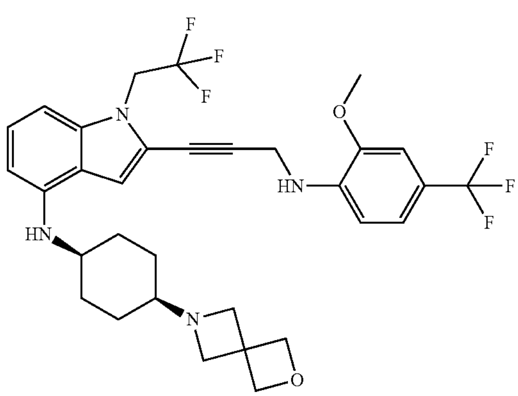 [SMILES: COc1cc(C(F)(F)F)ccc1NCC#Cc1cc2c(N[C@H]3CC[C@@H](N4CC5(COC5)C4)CC3)cccc2n1CC(F)(F)F] | N-((1S,4S)-4-(2-oxa-6-azaspiro[3.3]heptan-6-yl)cyclohexyl)-2-(3-((2-methoxy-4-(trifluoromethyl)phenyl)amino)prop-1-yn-1-yl)-1-(2,2,2-trifluoroethyl)-1H-indol-4-amine | 621.2 |

TABLE 3-continued

| Compound No. | Structure | IUPAC | LC-MS (ES+, m/z) |
|---|---|---|---|
| 279A | 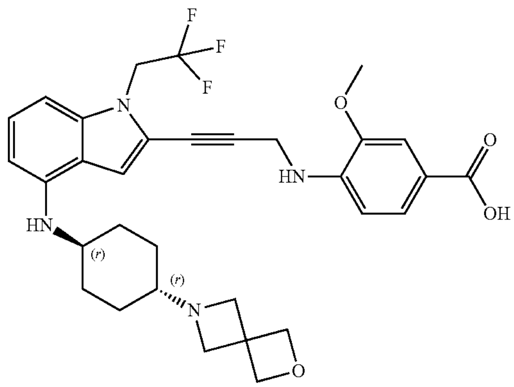 [SMILES: COc1cc(C(=O)O)ccc1NCC#Cc1cc2c(N[C@H]3CC[C@H](N4CC5(COC5)C4)CC3)cccc2n1CC(F)(F)F] | 4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxybenzoic acid | 597.2 |
| 280A | 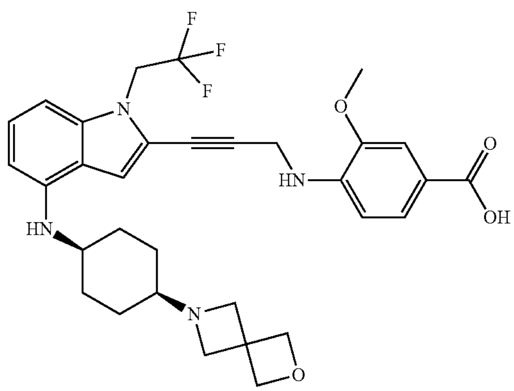 [SMILES: COc1cc(C(=O)O)ccc1NCC#Cc1cc2c(N[C@H]3CC[C@@H](N4CC5(COC5)C4)CC3)cccc2n1CC(F)(F)F] | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxybenzoic acid | 597.2 |
| 281A | 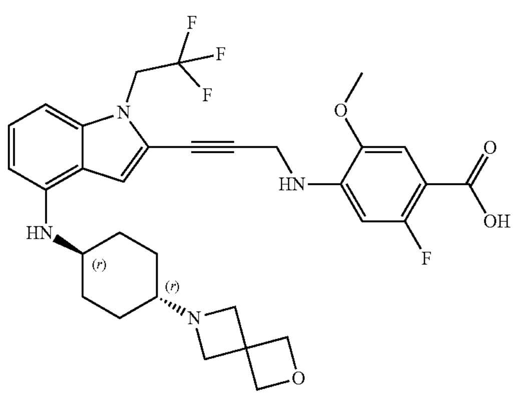 [SMILES: COc1cc(C(=O)O)c(F)cc1NCC#Cc1cc2c(N[C@H]3CC[C@H](N4CC5(COC5)C4)CC3)cccc2n1CC(F)(F)F] | 2-fluoro-5-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzoic acid | 615.2 |
| 282A | 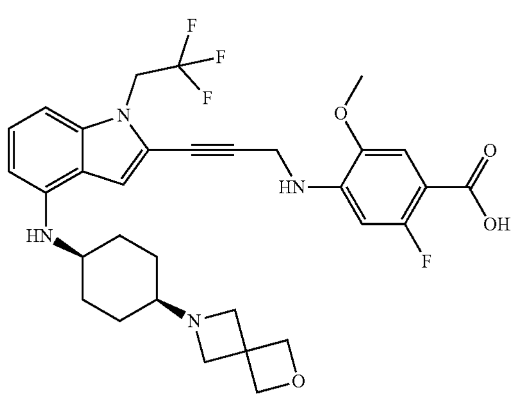 [SMILES: COc1cc(C(=O)O)c(F)cc1NCC#Cc1cc2c(N[C@H]3CC[C@@H](N4CC5(COC5)C4)CC3)cccc2n1CC(F)(F)F] | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxybenzoic acid | 615.2 |

TABLE 3-continued

| Compound No. | Structure | IUPAC | LC-MS (ES+, m/z) |
|---|---|---|---|
| 283A | 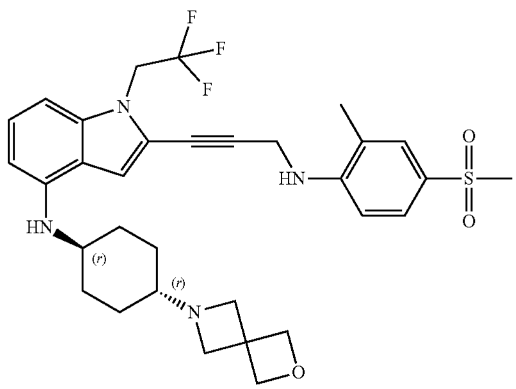 [SMILES: Cc1cc(S(C)(=O)=O)ccc1NCC#Cc1cc2c(N[C@H]3CC[C@H](N4CC5(COC5)C4)CC3)cccc2n1CC(F)(F)F] | 2-{3-[(4-methane-sulfonyl-2-methyl-phenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine | 615.3 |
| 284A | 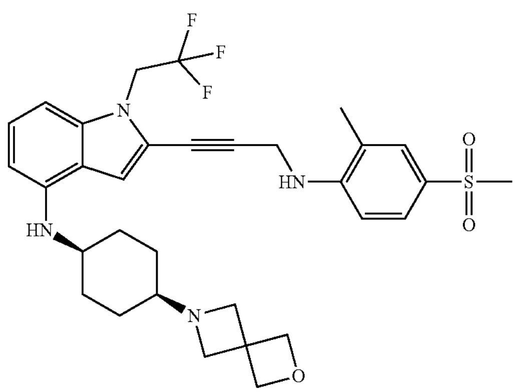 [SMILES: Cc1cc(S(C)(=O)=O)ccc1NCC#Cc1cc2c(N[C@H]3CC[C@@H](N4CC5(COC5)C4)CC3)cccc2n1CC(F)(F)F] | N-((1S,4S)-4-(2-oxa-6-azaspiro[3.3]heptan-6-yl)cyclohexyl)-2-(3-((2-methyl-4-(methyl-sulfonyl)phenyl)amino)prop-1-yn-1-yl)-1-(2,2,2-trifluoroethyl)-1H-indol-4-amine | 615.3 |
| 285A | 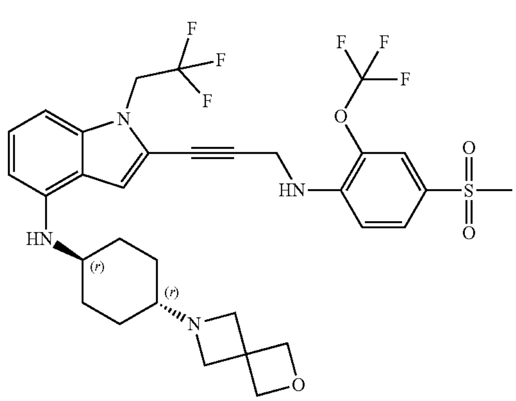 [SMILES: CS(=O)(=O)c1ccc(NCC#Cc2cc3c(N[C@H]4CC[C@H](N5CC6(COC6)C5)CC4)cccc3n2CC(F)(F)F)c(OC(F)(F)F)c1] | 2-(3-{[4-methane-sulfonyl-2-(trifluoro-methoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine | 685.2 |

TABLE 3-continued

| Compound No. | Structure | IUPAC | LC-MS (ES+, m/z) |
|---|---|---|---|
| 286A | 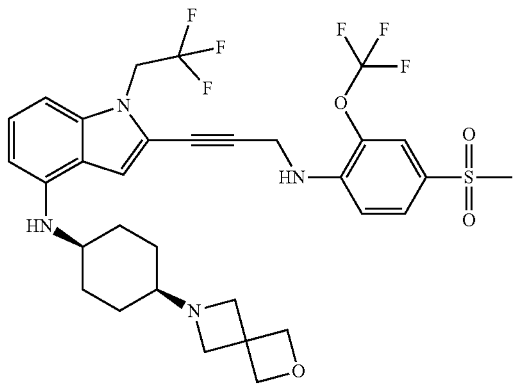 [SMILES: CS(=O)(=O)c1ccc(NCC#Cc2cc3c(N[C@H]4CC[C@@H](N5CC6(COC6)C5)CC4)cccc3n2CC(F)(F)F)c(OC(F)(F)F)c1] | N-((1S,4S)-4-(2-oxa-6-azaspiro[3.3]heptan-6-yl)cyclohexyl)-2-(3-((4-(methylsulfonyl)-2-(trifluoromethoxy)phenyl)amino)prop-1-yn-1-yl)-1-(2,2,2-trifluoroethyl)-1H-indol-4-amine | 685.2 |
| 287A | 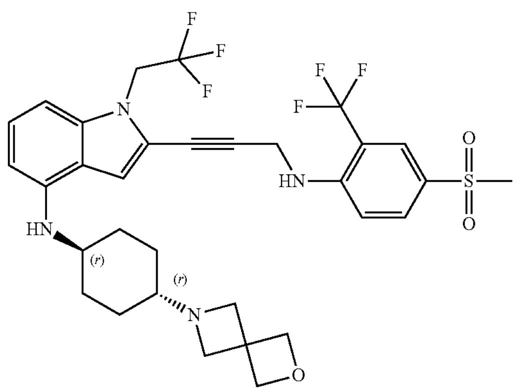 [SMILES: CS(=O)(=O)c1ccc(NCC#Cc2cc3c(N[C@H]4CC[C@H](N5CC6(COC6)C5)CC4)cccc3n2CC(F)(F)F)c(C(F)(F)F)c1] | 2-(3-{[4-methanesulfonyl-2-(trifluoromethyl)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine | 669.2 |
| 288A | 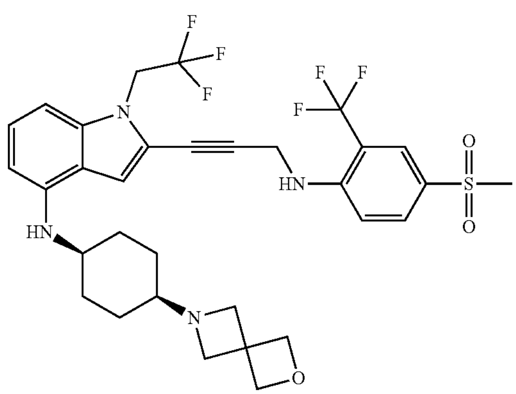 [SMILES: CS(=O)(=O)c1ccc(NCC#Cc2cc3c(N[C@H]4CC[C@@H](N5CC6(COC6)C5)CC4)cccc3n2CC(F)(F)F)c(C(F)(F)F)c1] | N-((1S,4S)-4-(2-oxa-6-azaspiro[3.3]heptan-6-yl)cyclohexyl)-2-(3-((4-(methylsulfonyl)-2-(trifluoromethyl)phenyl)amino)prop-1-yn-1-yl)-1-(2,2,2-trifluoroethyl)-1H-indol-4-amine | 669.2 |
| 289A | 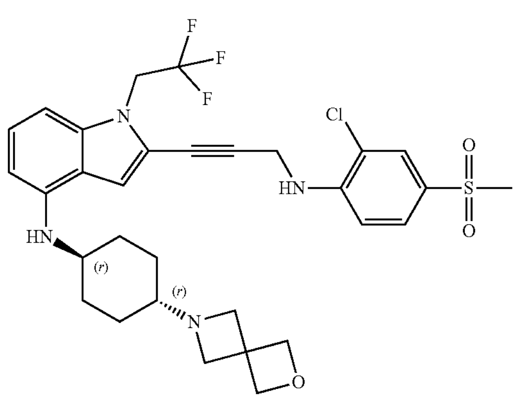 | 2-{3-[(2-chloro-4-methanesulfonyl-phenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine | 635.3 |

TABLE 3-continued

| Compound No. | Structure | IUPAC | LC-MS (ES+, m/z) |
|---|---|---|---|
| 290A | 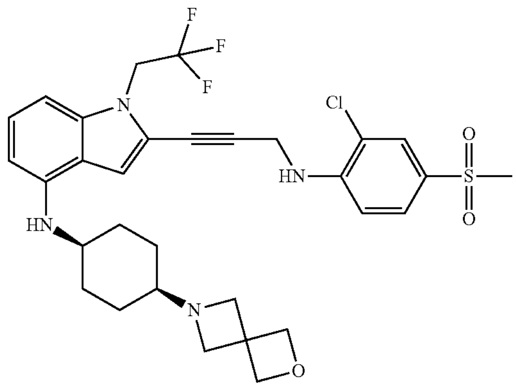 | N-((1S,4S)-4-(2-oxa-6-azaspiro[3.3]heptan-6-yl)cyclohexyl)-2-(3-((2-chloro-4-(methylsulfonyl)phenyl)amino)prop-1-yn-1-yl)-1-(2,2,2-trifluoroethyl)-1H-indol-4-amine | 635.2 |
| 291A | 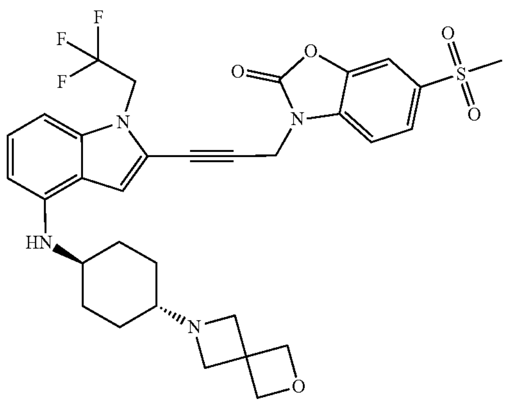 [SMILES: CS(=O)(=O)c1ccc2c(c1)oc(=O)n2CC#Cc1cc2c(N[C@H]3CC[C@H](N4CC5(COC5)C4)CC3)cccc2n1CC(F)(F)F] | 3-(3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)-6-(methylsulfonyl)benzo[d]oxazol-2(3H)-one | 643.2 |
| 292A | 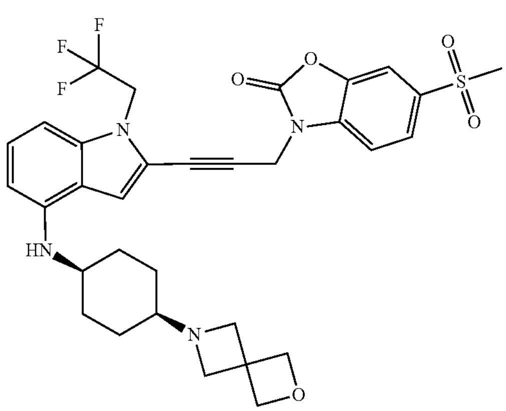 [SMILES: CS(=O)(=O)c1ccc2c(c1)oc(=O)n2CC#Cc1cc2c(N[C@H]3CC[C@@H](N4CC5(COC5)C4)CC3)cccc2n1CC(F)(F)F] | 3-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-6-(methylsulfonyl)benzo[d]oxazol-2(3H)-one | 643.2 |

TABLE 3-continued

| Compound No. | Structure | IUPAC | LC-MS (ES+, m/z) |
|---|---|---|---|
| 293A | 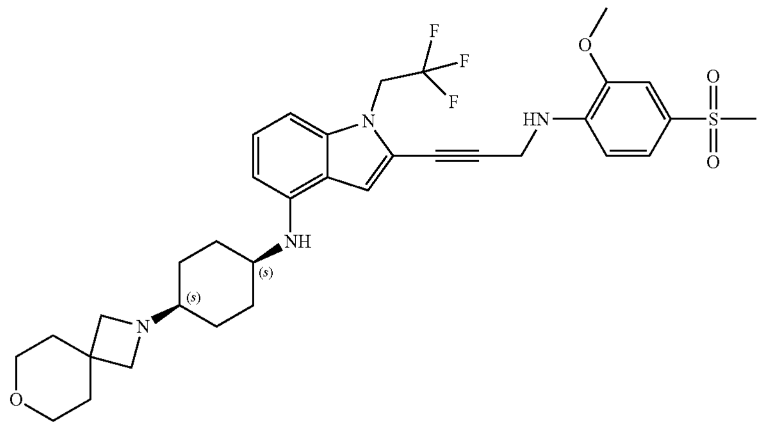 [SMILES: COc1cc(S(C)(=O)=O)ccc1NCC#Cc1cc2c(N[C@H]3CC[C@@H](N4CC5(CCOCC5)C4)CC3)cccc2n1CC(F)(F)F] | 2-{3-[(4-methane-sulfonyl-2-methoxy-phenyl)amino]prop-1-yn-1-yl}-N-[(1S,4S)-4-{7-oxa-2-azaspiro[3.5]nonan-2-yl}cyclo-hexyl]-1-(2,2,2-trifluoro-ethyl)-1H-indol-4-amine | 659.4 |
| 294A | 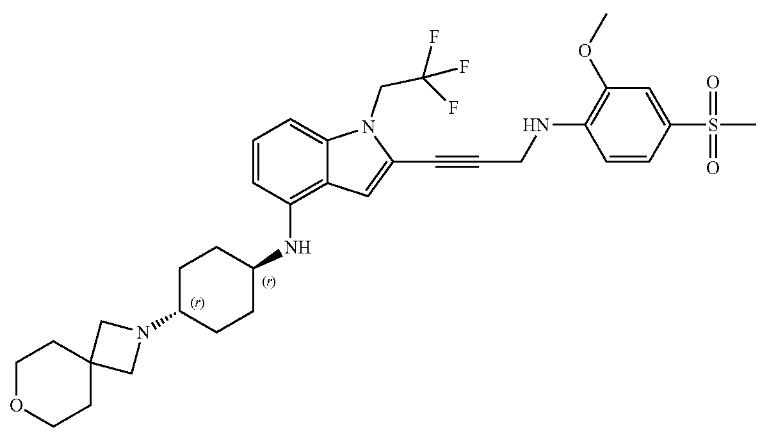 [SMILES: COc1cc(S(C)(=O)=O)ccc1NCC#Cc1cc2c(N[C@H]3CC[C@H](N4CC5(CCOCC5)C4)CC3)cccc2n1CC(F)(F)F] | 2-{3-[(4-methane-sulfonyl-2-methoxy-phenyl)amino]prop-1-yn-1-yl}-N-[(1R,4R)-4-{7-oxa-2-azaspiro[3.5]nonan-2-yl}cyclo-hexyl]-1-(2,2,2-trifluoro-ethyl)-1H-indol-4-amine | 659.3 |
| 295A | 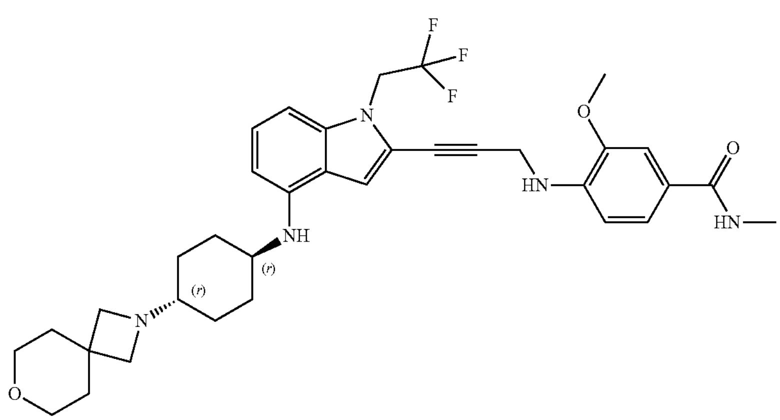 [SMILES: CNC(=O)c1ccc(NCC#Cc2cc3c(N[C@H]4CC[C@H](N5CC6(CCOCC6)C5)CC4)cccc3n2CC(F)(F)F)c(OC)c1] | 3-methoxy-N-methyl-4-{[3-(4-{[(1R,4R)-4-{7-oxa-2-azaspiro[3.5]nonan-2-yl}cyclo-hexyl]amino}-1-(2,2,2-trifluoroethyl)-1H-indol-2-yl)prop-2-yn-1-yl]amino}benzamide | 638.4 |

TABLE 3-continued

| Compound No. | Structure | IUPAC | LC-MS (ES+, m/z) |
|---|---|---|---|
| 296A | 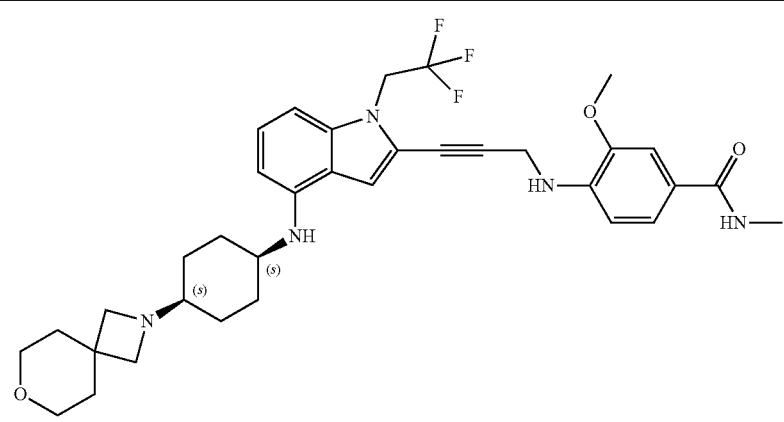 | 3-methoxy-N-methyl-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide | 638.4 |
| 297A | 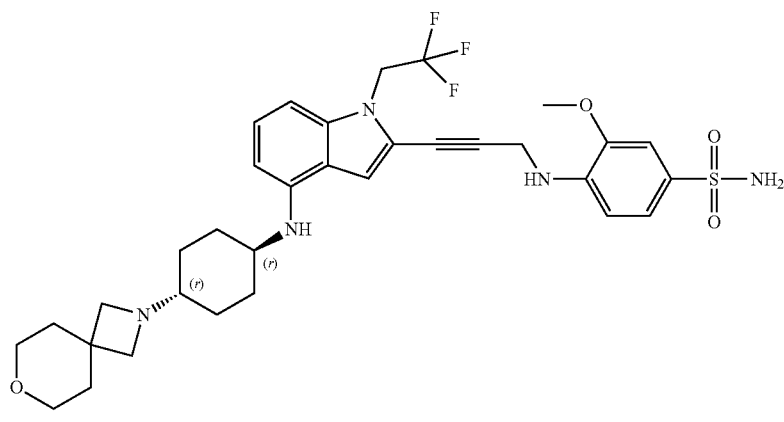 [SMILES: COc1cc(S(N)(=O)=O)ccc1NCC#Cc1cc2c(N[C@H]3CC[C@H](N4CC5(CCOCC5)C4)CC3)cccc2n1CC(F)(F)F] | 3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide | 660.3 |
| 298A | 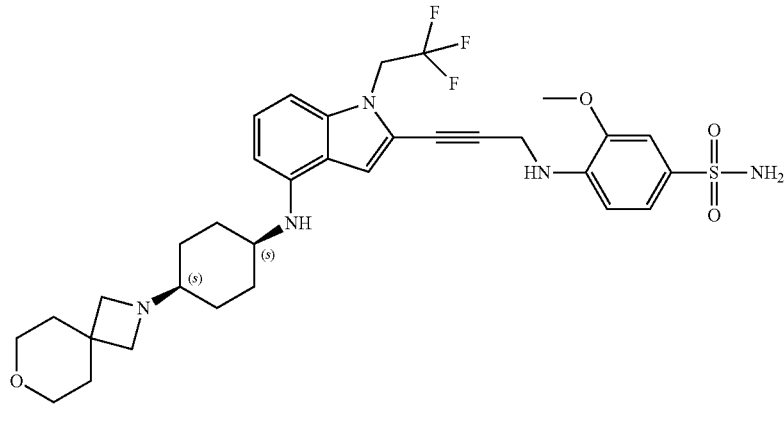 [SMILES: COc1cc(S(N)(=O)=O)ccc1NCC#Cc1cc2c(N[C@H]3CC[C@@H](N4CC5(CCOCC5)C4)CC3)cccc2n1CC(F)(F)F] | 3-methoxy-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide | 660.3 |

TABLE 3-continued

| Compound No. | Structure | IUPAC | LC-MS (ES+, m/z) |
|---|---|---|---|
| 299A | 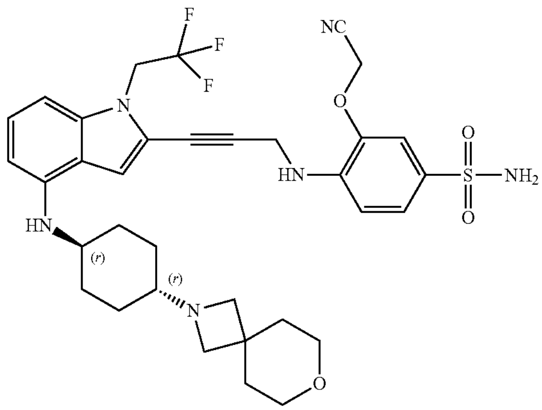 [SMILES: N#CCOc1cc(S(N)(=O)=O)ccc1NCC#Cc1cc2c(N[C@H]3CC[C@H](N4CC5(CCOCC5)C4)CC3)cccc2n1CC(F)(F)F] | 3-(cyanomethoxy)-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide | 685.2 |
| 300A | 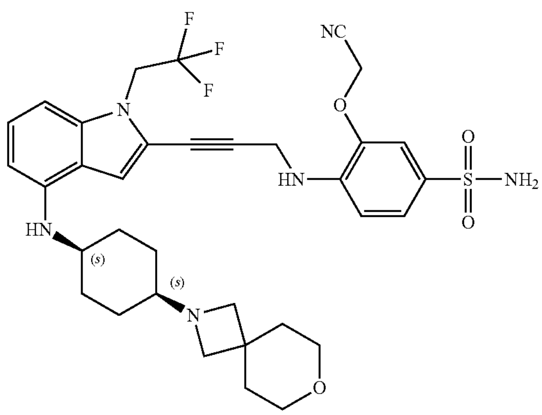 [SMILES: N#CCOc1cc(S(N)(=O)=O)ccc1NCC#Cc1cc2c(N[C@H]3CC[C@@H](N4CC5(CCOCC5)C4)CC3)cccc2n1CC(F)(F)F] | 3-(cyanomethoxy)-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide | 685.2 |
| 301A | 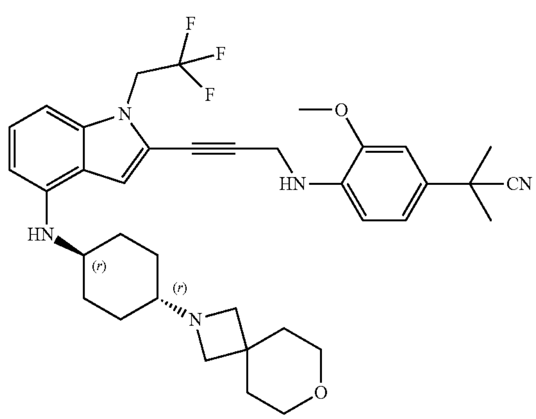 [SMILES: COc1cc(C(C)(C)C#N)ccc1NCC#Cc1cc2c(N[C@H]3CC[C@H](N4CC5(CCOCC5)C4)CC3)cccc2n1CC(F)(F)F] | 2-(3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenyl)-2-methylpropanenitrile | 648.4 |

TABLE 3-continued

| Compound No. | Structure | IUPAC | LC-MS (ES+, m/z) |
|---|---|---|---|
| 302A | 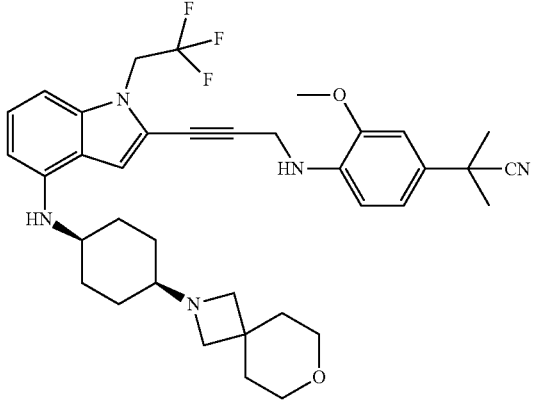 [SMILES: COc1cc(C(C)(C)C#N)ccc1NCC#Cc1cc2c(N[C@H]3CC[C@@H](N4CC5(CCOCC5)C4)CC3)cccc2n1CC(F)(F)F] | 2-(4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)-2-methylpropanenitrile | 648.4 |
| 303A | 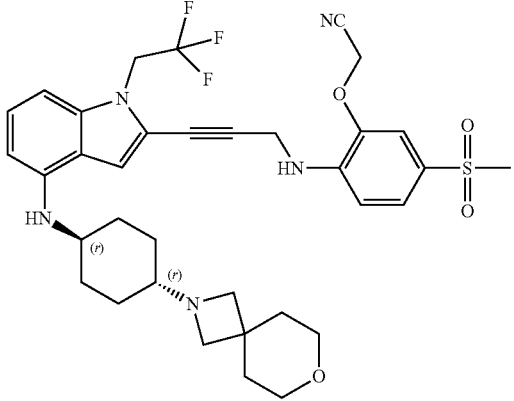 [SMILES: CS(=O)(=O)c1ccc(NCC#Cc2cc3c(N[C@H]4CC[C@H](N5CC6(CCOCC6)C5)CC4)cccc3n2CC(F)(F)F)c(OCC#N)c1] | 2-(5-methanesulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetonitrile | 684.3 |
| 304A | 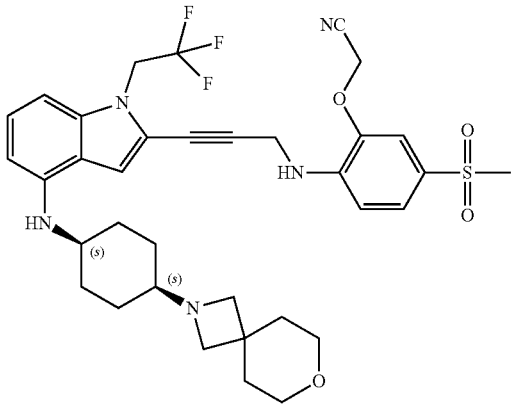 [SMILES: CS(=O)(=O)c1ccc(NCC#Cc2cc3c(N[C@H]4CC[C@@H](N5CC6(CCOCC6)C5)CC4)cccc3n2CC(F)(F)F)c(OCC#N)c1] | 2-(5-methanesulfonyl-2-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetonitrile | 684.3 |

TABLE 3-continued

| Compound No. | Structure | IUPAC | LC-MS (ES+, m/z) |
|---|---|---|---|
| 305A | 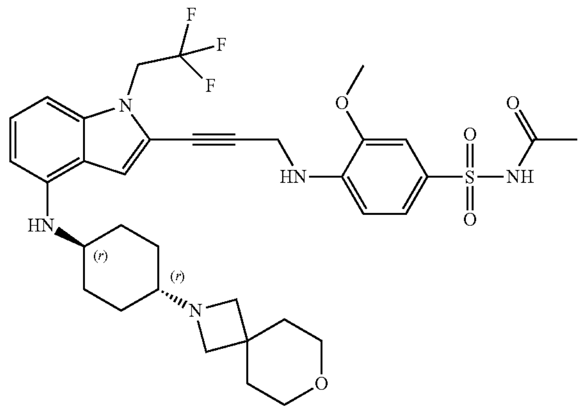 [SMILES: COc1cc(S(=O)(=O)NC(C)=O)ccc1NCC#Cc1cc2c(N[C@H]3CC[C@H](N4CC5(CCOCC5)C4)CC3)cccc2n1CC(F)(F)F] | N-((4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)acetamide | 702.3 |
| 306A | 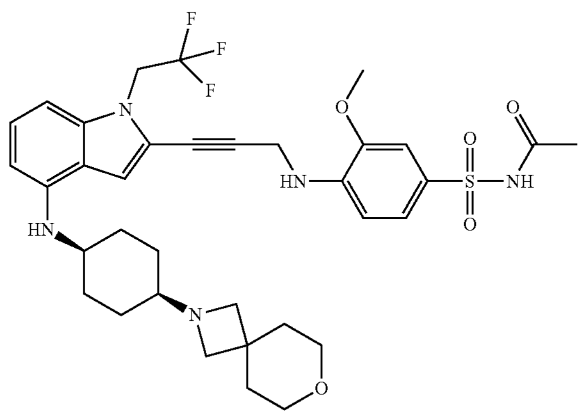 [SMILES: COc1cc(S(=O)(=O)NC(C)=O)ccc1NCC#Cc1cc2c(N[C@H]3CC[C@@H](N4CC5(CCOCC5)C4)CC3)cccc2n1CC(F)(F)F] | N-((4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)acetamide | 702.3 |
| 307A | 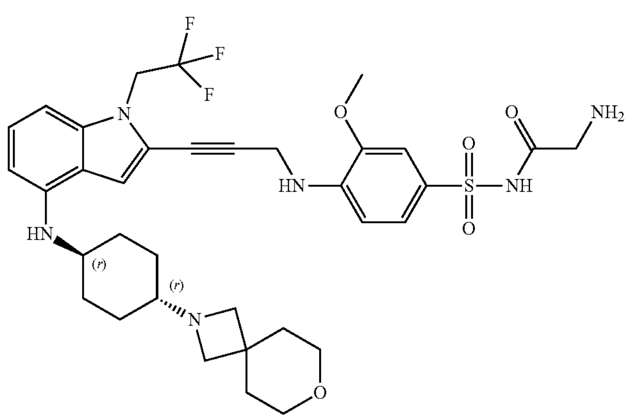 [SMILES: COc1cc(S(=O)(=O)NC(=O)CN)ccc1NCC#Cc1cc2c(N[C@H]3CC[C@H](N4CC5(CCOCC5)C4)CC3)cccc2n1CC(F)(F)F] | N-((4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)-2-aminoacetamide | 717.3 |

TABLE 3-continued

| Compound No. | Structure | IUPAC | LC-MS (ES+, m/z) |
| --- | --- | --- | --- |
| 308A | 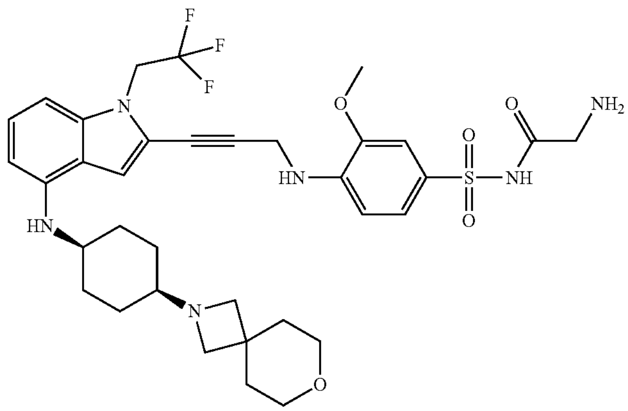 [SMILES: COc1cc(S(=O)(=O)NC(=O)CN)ccc1NCC#Cc1cc2c(N[C@H]3CC[C@@H](N4CC5(CCOCC5)C4)CC3)cccc2n1CC(F)(F)F] | N-((4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)-2-aminoacetamide | 717.3 |
| 309A | 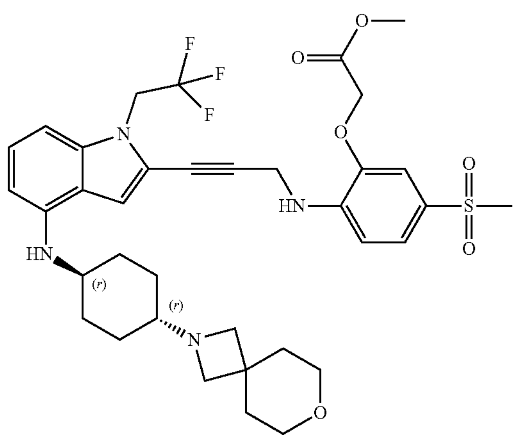 [SMILES: COC(=O)COc1cc(S(C)(=O)=O)ccc1NCC#Cc1cc2c(N[C@H]3CC[C@H](N4CC5(CCOCC5)C4)CC3)cccc2n1CC(F)(F)F] | methyl 2-(5-methane-sulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetate | 717.2 |
| 310A | 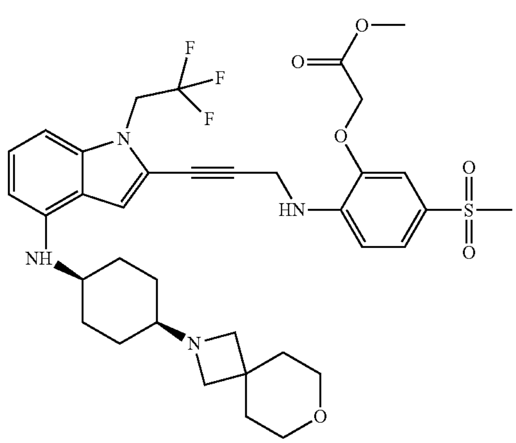 [SMILES: COC(=O)COc1cc(S(C)(=O)=O)ccc1NCC#Cc1cc2c(N[C@H]3CC[C@@H](N4CC5(CCOCC5)C4)CC3)cccc2n1CC(F)(F)F] | methyl 2-(2-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetate | |

TABLE 3-continued

| Compound No. | Structure | IUPAC | LC-MS (ES+, m/z) |
|---|---|---|---|
| 311A | 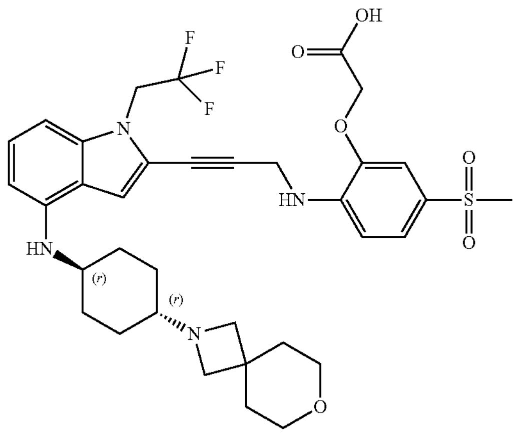 [SMILES: CS(=O)(=O)c1ccc(NCC#Cc2cc3c(N[C@H]4CC[C@H](N5CC6(CCOCC6)C5)CC4)cccc3n2CC(F)(F)F)c(OCC(=O)O)c1] | 2-(5-methanesulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetic acid | 703.2 |
| 312A | 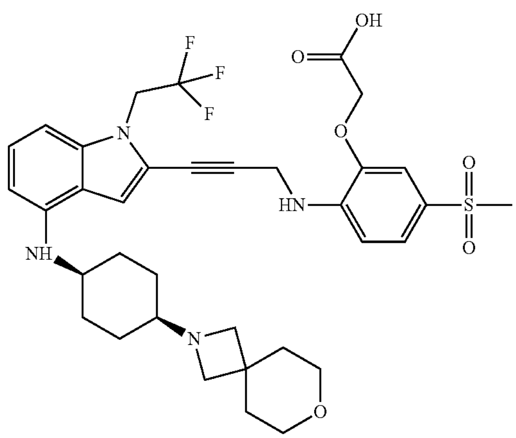 [SMILES: CS(=O)(=O)c1ccc(NCC#Cc2cc3c(N[C@H]4CC[C@@H](N5CC6(CCOCC6)C5)CC4)cccc3n2CC(F)(F)F)c(OCC(=O)O)c1] | 2-(2-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetic acid | |
| 313A | 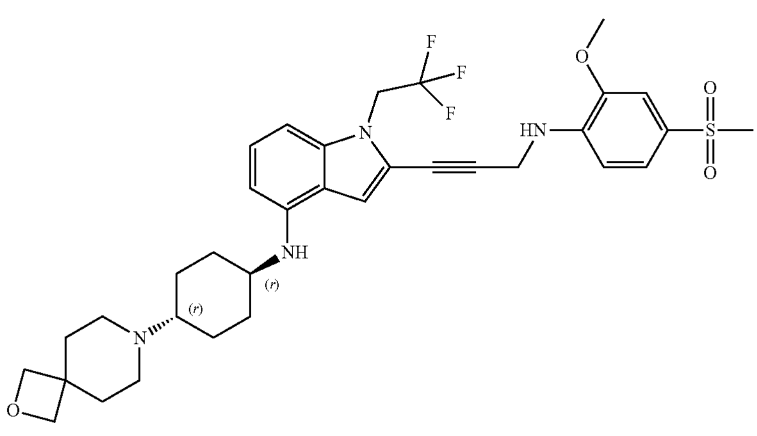 [SMILES: COc1cc(S(C)(=O)=O)ccc1NCC#Cc1cc2c(N[C@H]3CC[C@H](N4CCC5(CC4)COC5)CC3)cccc2n1CC(F)(F)F] | 2-{3-[(4-methanesulfonyl-2-methoxyphenyl)amino]prop-1-yn-1-yl}-N-[(1R,4R)-4-{2-oxa-7-azaspiro[3.5]nonan-7-yl}cyclohexyl]-1-(2,2,2-trifluoroethyl)-1H-indol-4-amine | 659.2 |

TABLE 3-continued

| Compound No. | Structure | IUPAC | LC-MS (ES+, m/z) |
|---|---|---|---|
| 314A | 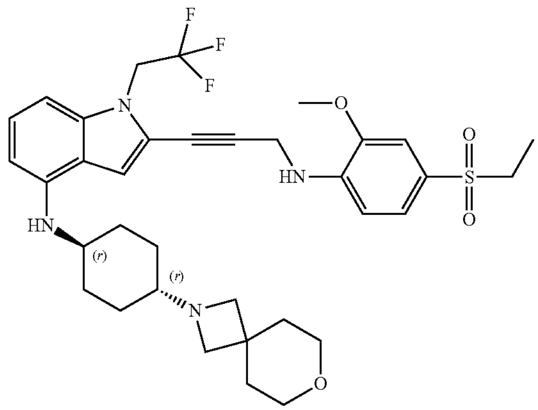 [SMILES: CCS(=O)(=O)c1ccc(NCC#Cc2cc3c(N[C@H]4CC[C@H](N5CC6(CCOCC6)C5)CC4)cccc3n2CC(F)(F)F)c(OC)c1] | 2-(3-{[4-(ethane-sulfonyl)-2-methoxy-phenyl]amino}prop-1-yn-1-yl)-N-[(1R,4R)-4-{7-oxa-2-azaspiro[3.5]nonan-2-yl}cyclohexyl]-1-(2,2,2-trifluoroethyl)-1H-indol-4-amine | 673.4 |
| 315A | 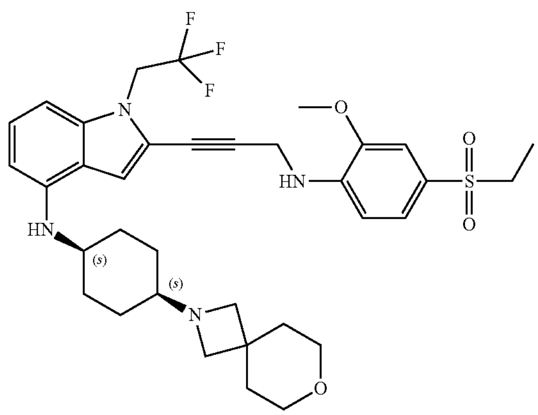 [SMILES: CCS(=O)(=O)c1ccc(NCC#Cc2cc3c(N[C@H]4CC[C@@H](N5CC6(CCOCC6)C5)CC4)cccc3n2CC(F)(F)F)c(OC)c1] | 2-(3-{[4-(ethane-sulfonyl)-2-methoxy-phenyl]amino}prop-1-yn-1-yl)-N-[(1S,4S)-4-{7-oxa-2-azaspiro[3.5]nonan-2-yl}cyclohexyl]-1-(2,2,2-trifluoroethyl)-1H-indol-4-amine | 673.3 |
| 316A | 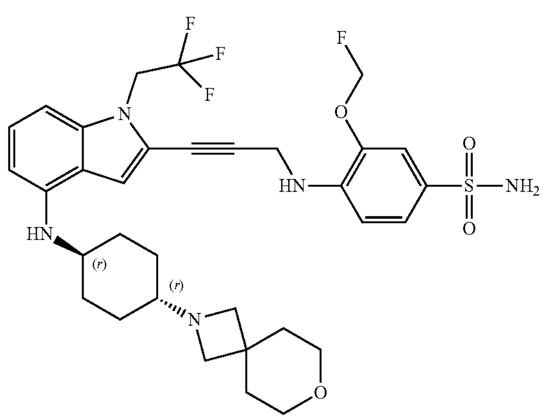 [SMILES: NS(=O)(=O)c1ccc(NCC#Cc2cc3c(N[C@H]4CC[C@H](N5CC6(CCOCC6)C5)CC4)cccc3n2CC(F)(F)F)c(OCF)c1] | 3-(fluoromethoxy)-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide | 678.3 |

TABLE 3-continued

| Compound No. | Structure | IUPAC | LC-MS (ES+, m/z) |
|---|---|---|---|
| 317A | 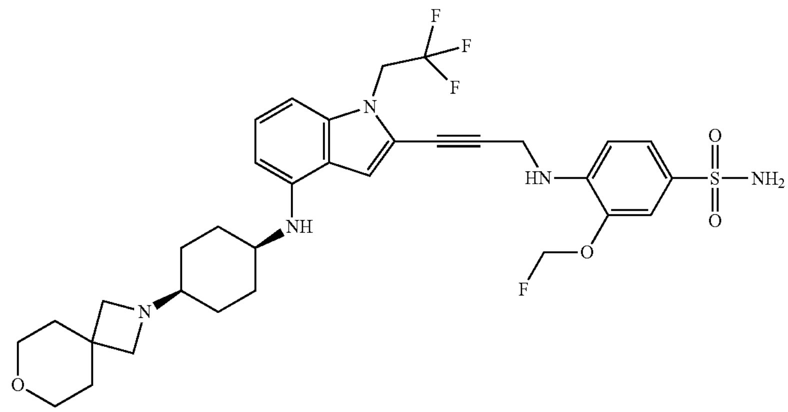 [SMILES: NS(=O)(=O)c1ccc(NCC#Cc2cc3c(N[C@H]4CC[C@@H](N5CC6(CCOCC6)C5)CC4)cccc3n2CC(F)(F)F)c(OCF)c1] | 3-(fluoromethoxy)-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide | 678.2 |
| 318A | 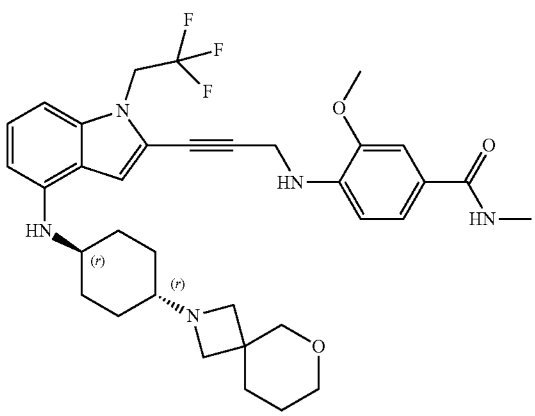 [SMILES: CNC(=O)c1ccc(NCC#Cc2cc3c(N[C@H]4CC[C@H](N5CC6(CCCOC6)C5)CC4)cccc3n2CC(F)(F)F)c(OC)c1] | 3-methoxy-N-methyl-4-{[3-(4-{[(1R,4R)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzamide | 638.3 |
| 319A | 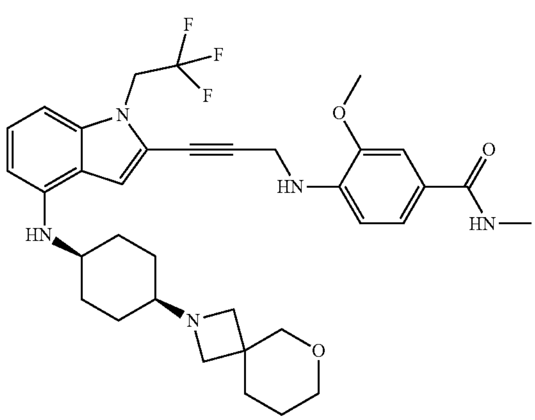 [SMILES: CNC(=O)c1ccc(NCC#Cc2cc3c(N[C@H]4CC[C@@H](N5CC6(CCCOC6)C5)CC4)cccc3n2CC(F)(F)F)c(OC)c1] | 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzamide | 638.3 |

TABLE 3-continued

| Compound No. | Structure | IUPAC | LC-MS (ES+, m/z) |
|---|---|---|---|
| 320A | 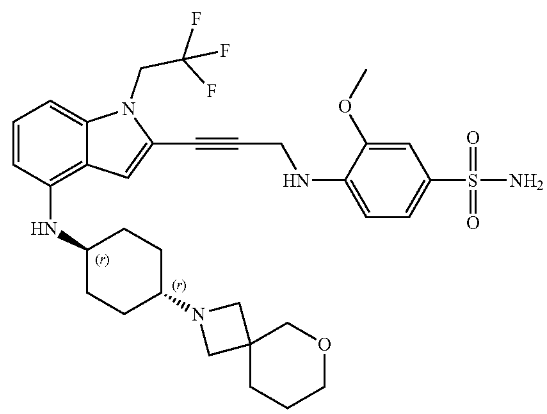 [SMILES: COc1cc(S(N)(=O)=O)ccc1NCC#Cc1cc2c(N[C@H]3CC[C@H](N4CC5(CCCOC5)C4)CC3)cccc2n1CC(F)(F)F] | 3-methoxy-4-{[3-(4-{[(1R,4R)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide | 660.3 |
| 321A | 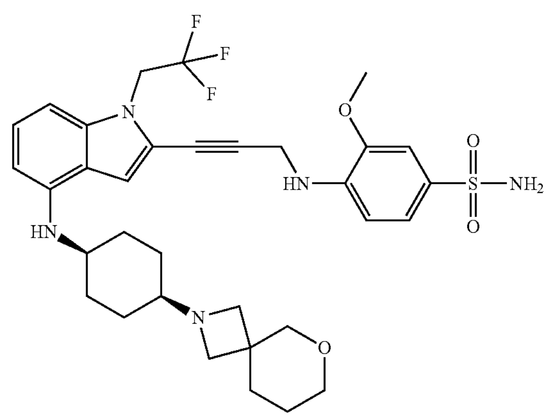 [SMILES: COc1cc(S(N)(=O)=O)ccc1NCC#Cc1cc2c(N[C@H]3CC[C@@H](N4CC5(CCCOC5)C4)CC3)cccc2n1CC(F)(F)F] | 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzene-sulfonamide | 660.3 |
| 322A | 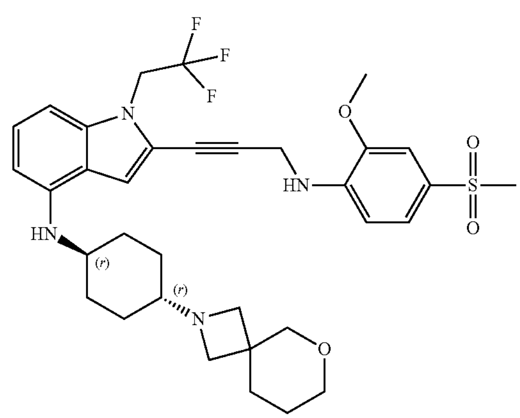 [SMILES: COc1cc(S(C)(=O)=O)ccc1NCC#Cc1cc2c(N[C@H]3CC[C@H](N4CC5(CCCOC5)C4)CC3)cccc2n1CC(F)(F)F] | 2-{3-[(4-methanesulfonyl-2-methoxyphenyl)amino]prop-1-yn-1-yl}-N-[(1R,4R)-4-{6-oxa-2-azaspiro[3.5]nonan-2-yl}cyclohexyl]-1-(2,2,2-trifluoroethyl)-1H-indol-4-amine | 659.2 |

TABLE 3-continued

| Compound No. | Structure | IUPAC | LC-MS (ES+, m/z) |
|---|---|---|---|
| 323A | 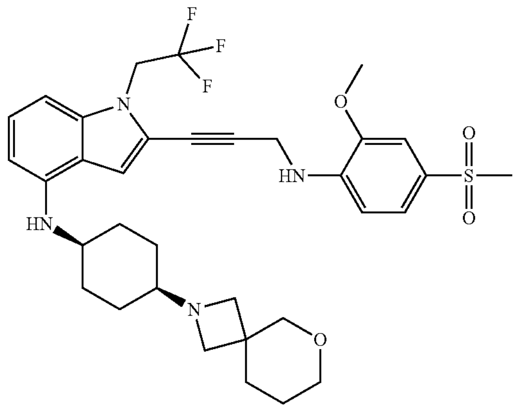 [SMILES: COc1cc(S(C)(=O)=O)ccc1NCC#Cc1cc2c(N[C@H]3CC[C@@H](N4CC5(CCCOC5)C4)CC3)cccc2n1CC(F)(F)F] | N-((1S,4S)-4-(6-oxa-2-azaspiro[3.5]nonan-2-yl)cyclohexyl)-2-(3-((2-methoxy-4-(methylsulfonyl)phenyl)amino)prop-1-yn-1-yl)-1-(2,2,2-trifluoroethyl)-1H-indol-4-amine | 659.2 |
| 324A | 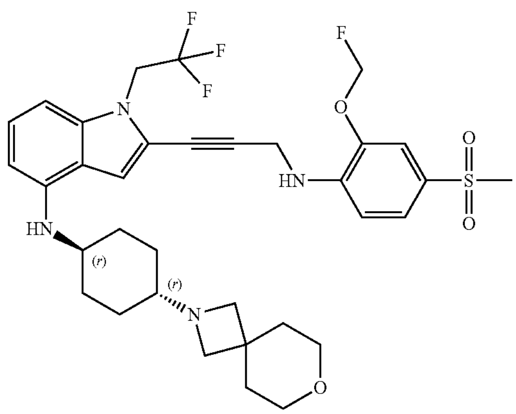 [SMILES: CS(=O)(=O)c1ccc(NCC#Cc2cc3c(N[C@H]4CC[C@H](N5CC6(CCOCC6)C5)CC4)cccc3n2CC(F)(F)F)c(OCF)c1] | N-((1R,4R)-4-(7-oxa-2-azaspiro[3.5]nonan-2-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine | 677.3 |
| 325A | 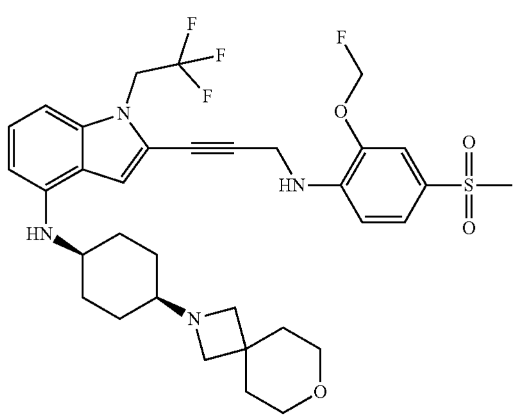 [SMILES: CS(=O)(=O)c1ccc(NCC#Cc2cc3c(N[C@H]4CC[C@@H](N5CC6(CCOCC6)C5)CC4)cccc3n2CC(F)(F)F)c(OCF)c1] | N-((1S,4S)-4-(7-oxa-2-azaspiro[3.5]nonan-2-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine | 677.3 |

TABLE 3-continued

| Compound No. | Structure | IUPAC | LC-MS (ES+, m/z) |
|---|---|---|---|
| 326A | 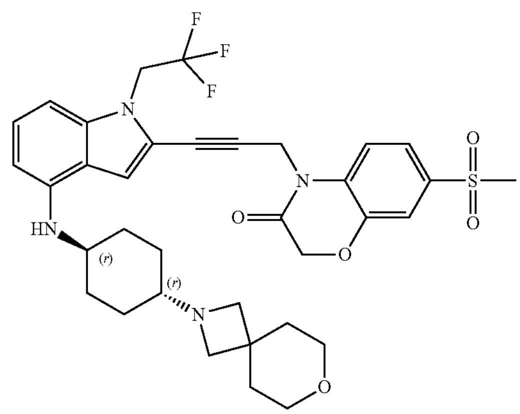 [SMILES: CS(=O)(=O)c1ccc2c(c1)OCC(=O)N2CC#Cc1cc2c(N[C@H]3CC[C@H](N4CC5(CCOCC5)C4)CC3)cccc2n1CC(F)(F)F] | 4-(3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)-7-(methylsulfonyl)-2H-benzo[b][1,4]oxazin-3(4H)-one | 685.3 |
| 327A | 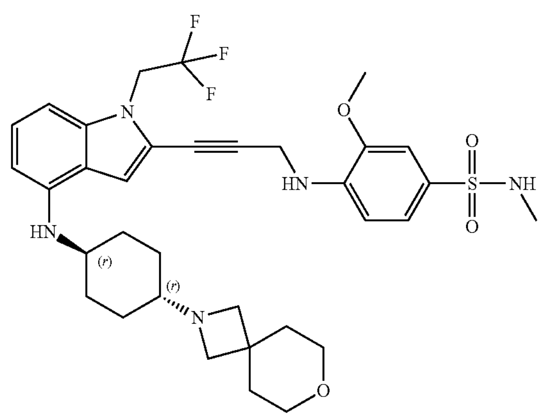 [SMILES: CNS(=O)(=O)c1ccc(NCC#Cc2cc3c(N[C@H]4CC[C@H](N5CC6(CCOCC6)C5)CC4)cccc3n2CC(F)(F)F)c(OC)c1] | 4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzenesulfonamide | 674.3 |
| 328A | 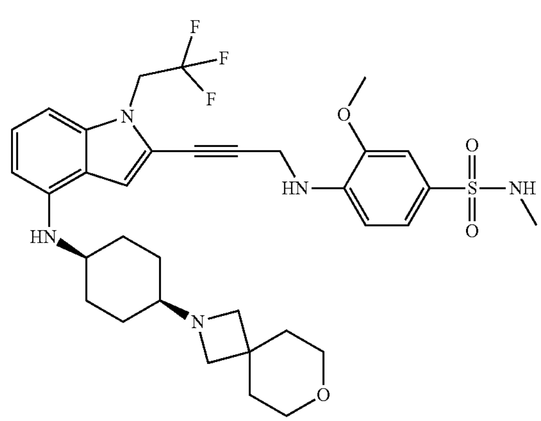 [SMILES: CNS(=O)(=O)c1ccc(NCC#Cc2cc3c(N[C@H]4CC[C@@H](N5CC6(CCOCC6)C5)CC4)cccc3n2CC(F)(F)F)c(OC)c1] | 4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzenesulfonamide | 674.3 |

TABLE 3-continued

| Compound No. | Structure | IUPAC | LC-MS (ES+, m/z) |
|---|---|---|---|
| 329A | 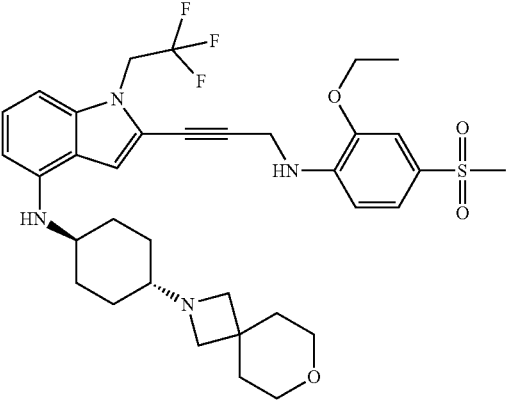 [SMILES: CCOc1cc(S(C)(=O)=O)ccc1NCC#Cc1cc2c(N[C@H]3CC[C@H](N4CC5(CCOCC5)C4)CC3)cccc2n1CC(F)(F)F] | N-((1R,4R)-4-(7-oxa-2-azaspiro[3.5]nonan-2-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine | 673.3 |
| 330A | 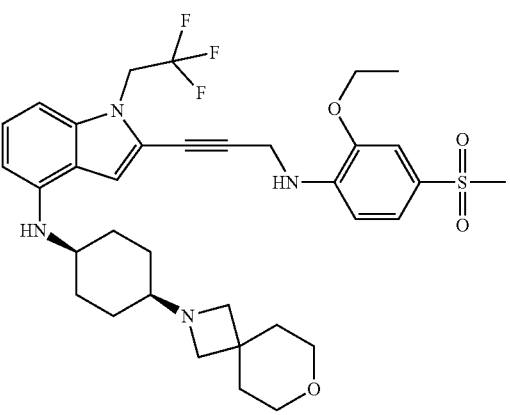 [SMILES: CCOc1cc(S(C)(=O)=O)ccc1NCC#Cc1cc2c(N[C@H]3CC[C@@H](N4CC5(CCOCC5)C4)CC3)cccc2n1CC(F)(F)F] | N-((1S,4S)-4-(7-oxa-2-azaspiro[3.5]nonan-2-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine | 673.3 |
| 331A | 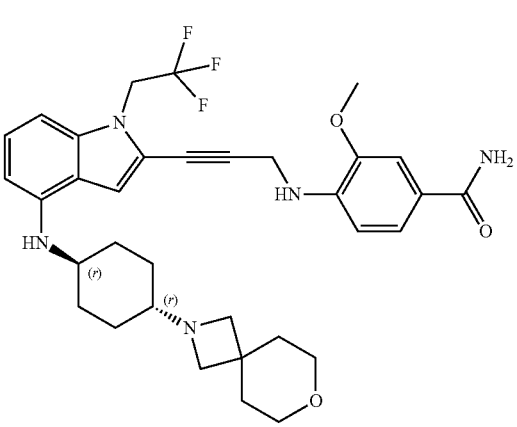 [SMILES: COc1cc(C(N)=O)ccc1NCC#Cc1cc2c(N[C@H]3CC[C@H](N4CC5(CCOCC5)C4)CC3)cccc2n1CC(F)(F)F] | 3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide | 624.3 |

TABLE 3-continued

| Compound No. | Structure | IUPAC | LC-MS (ES+, m/z) |
|---|---|---|---|
| 332A | 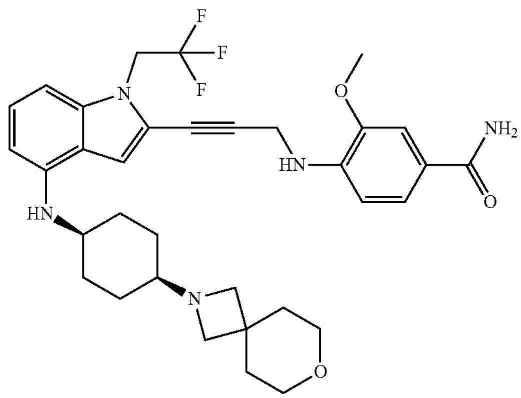 [SMILES: COc1cc(C(N)=O)ccc1NCC#Cc1cc2c(N[C@H]3CC[C@@H](N4CC5(CCOCC5)C4)CC3)cccc2n1CC(F)(F)F] | 4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzamide | 624.3 |
| 333A | 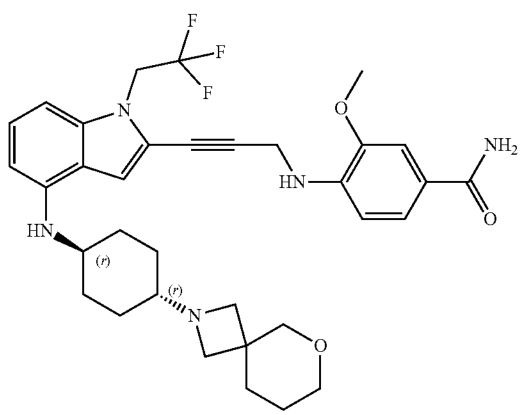 [SMILES: COc1cc(C(N)=O)ccc1NCC#Cc1cc2c(N[C@H]3CC[C@H](N4CC5(CCCOC5)C4)CC3)cccc2n1CC(F)(F)F] | 3-methoxy-4-{[3-(4-{[(1R,4R)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzamide | 624.3 |
| 334A | 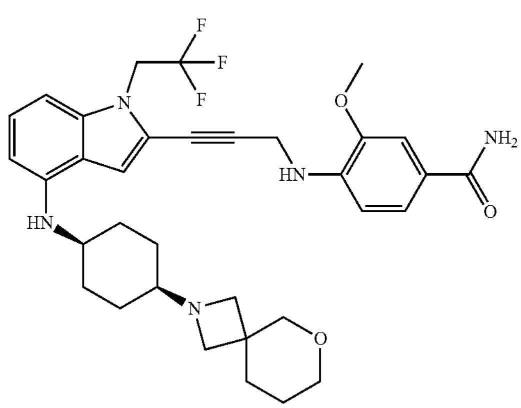 [SMILES: COc1cc(C(N)=O)ccc1NCC#Cc1cc2c(N[C@H]3CC[C@@H](N4CC5(CCCOC5)C4)CC3)cccc2n1CC(F)(F)F] | 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzamide | 624.3 |

TABLE 3-continued

| Compound No. | Structure | IUPAC | LC-MS (ES+, m/z) |
|---|---|---|---|
| 335A | 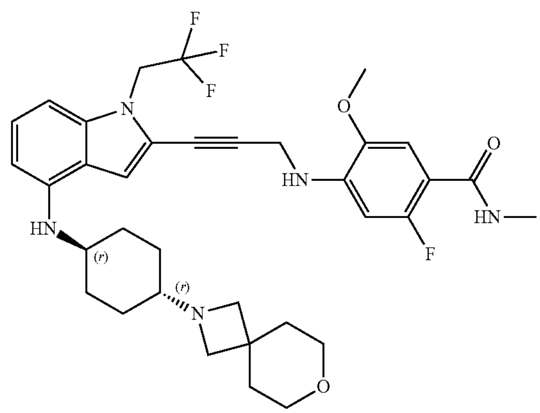 [SMILES: CNC(=O)c1cc(OC)c(NCC#Cc2cc3c(N[C@H]4CC[C@H](N5CC6(CCOCC6)C5)CC4)cccc3n2CC(F)(F)F)cc1F] | 2-fluoro-5-methoxy-N-methyl-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide | 656.3 |
| 336A | 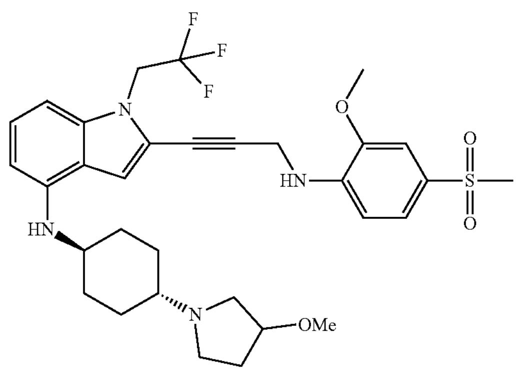 [SMILES: COc1cc(S(C)(=O)=O)ccc1NCC#Cc1cc2c(N[C@H]3CC[C@H](N4CCC(OC)C4)CC3)cccc2n1CC(F)(F)F] | 2-(3-((2-methoxy-4-(methylsulfonyl)phenyl)amino)prop-1-yn-1-yl)-N-((1R,4R)-4-(3-methoxypyrrolidin-1-yl)cyclohexyl)-1-(2,2,2-trifluoroethyl)-1H-indol-4-amine | 633.2 |
| 337A | 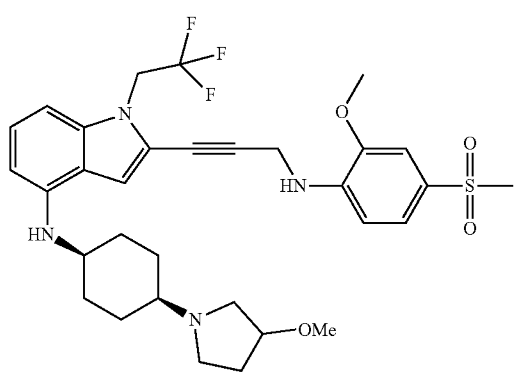 [SMILES: COc1cc(S(C)(=O)=O)ccc1NCC#Cc1cc2c(N[C@H]3CC[C@@H](N4CCC(OC)C4)CC3)cccc2n1CC(F)(F)F] | 2-(3-((2-methoxy-4-(methylsulfonyl)phenyl)amino)prop-1-yn-1-yl)-N-((1S,4S)-4-(3-methoxypyrrolidin-1-yl)cyclohexyl)-1-(2,2,2-trifluoroethyl)-1H-indol-4-amine | 633.2 |
| 338A | 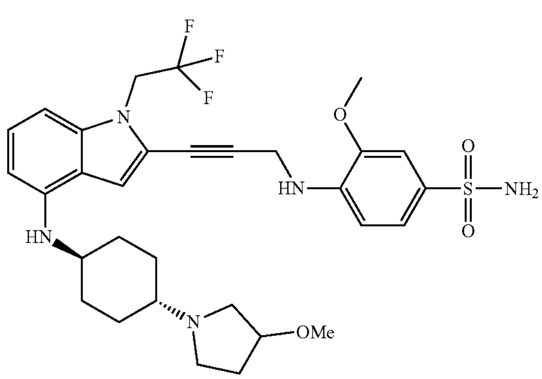 [SMILES: COc1cc(S(N)(=O)=O)ccc1NCC#Cc1cc2c(N[C@H]3CC[C@H](N4CCC(OC)C4)CC3)cccc2n1CC(F)(F)F] | 3-methoxy-4-((3-(4-(((1R,4R)-4-(3-methoxypyrrolidin-1-yl)cyclohexyl)amino)-1-(2,2,2-trifluoroethyl)-1H-indol-2-yl)prop-2-yn-1-yl)amino)benzenesulfonamide | 634.3 |

TABLE 3-continued

| Compound No. | Structure | IUPAC | LC-MS (ES+, m/z) |
|---|---|---|---|
| 339A | 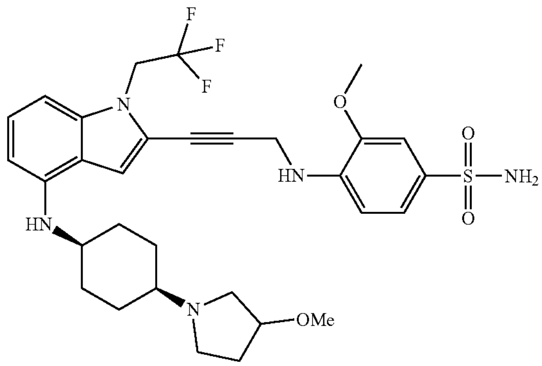 [SMILES: COc1cc(S(N)(=O)=O)ccc1NCC#Cc1cc2c(N[C@H]3CC[C@@H](N4CCC(OC)C4)CC3)cccc2n1CC(F)(F)F] | 3-methoxy-4-((3-(4-(((1S,4S)-4-(3-methoxy-pyrrolidin-1-yl)cyclohexyl)amino)-1-(2,2,2-trifluoroethyl)-1H-indol-2-yl)prop-2-yn-1-yl)amino)benzenesulfonamide | 634.3 |
| 340A | 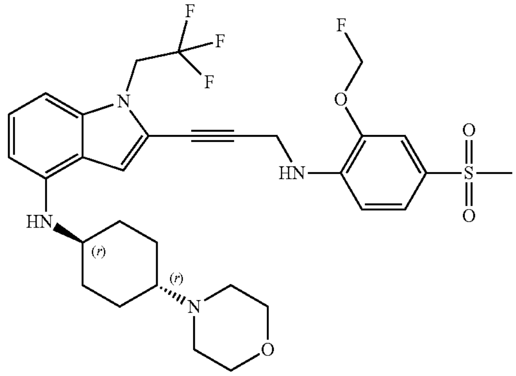 | 2-(3-{[2-(fluoromethoxy)-4-methanesulfonylphenyl]amino}prop-1-yn-1-yl)-N-[(1R,4R)-4-(morpholin-4-yl)cyclohexyl]-1-(2,2,2-trifluoroethyl)-1H-indol-4-amine | 637.2 |
| 341A | 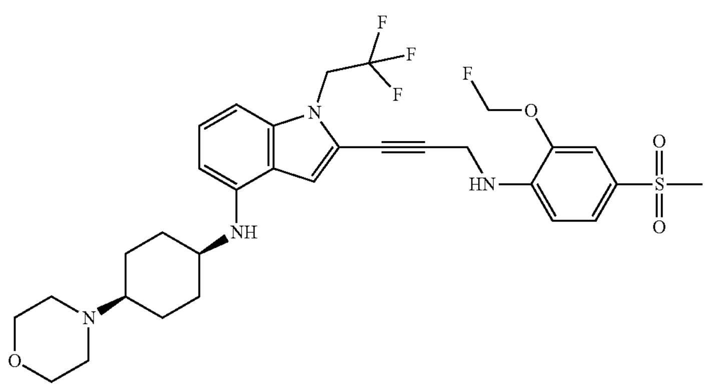 [SMILES: CS(=O)(=O)c1ccc(NCC#Cc2cc3c(N[C@H]4CC[C@@H](N5CCOCC5)CC4)cccc3n2CC(F)(F)F)c(OCF)c1] | 2-(3-{[2-(fluoromethoxy)-4-methanesulfonylphenyl]amino}prop-1-yn-1-yl)-N-[(1S,4S)-4-(morpholin-4-yl)cyclohexyl]-1-(2,2,2-trifluoroethyl)-1H-indol-4-amine | 637.2 |
| 342A | 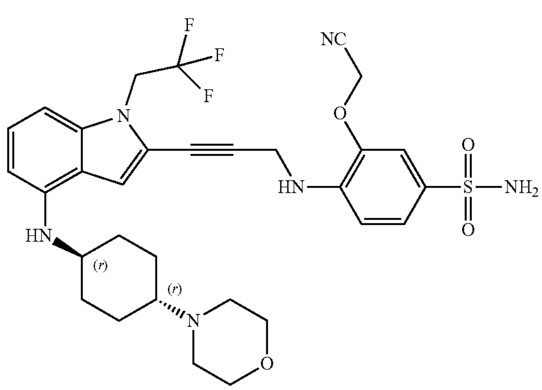 [SMILES: N#CCOc1cc(S(N)(=O)=O)ccc1NCC#Cc1cc2c(N[C@H]3CC[C@H](N4CCOCC4)CC3)cccc2n1CC(F)(F)F] | 3-(cyanomethoxy)-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide | 645.2 |

TABLE 3-continued

| Compound No. | Structure | IUPAC | LC-MS (ES+, m/z) |
|---|---|---|---|
| 343A | 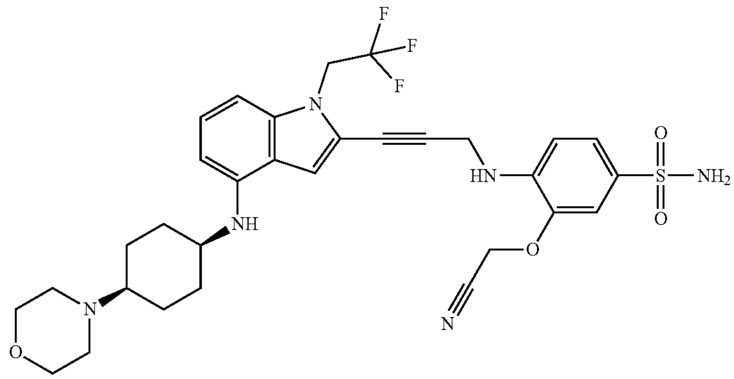 [SMILES: N#CCOc1cc(S(N)(=O)=O)ccc1NCC#Cc1cc2c(N[C@H]3CC[C@@H](N4CCOCC4)CC3)cccc2n1CC(F)(F)F] | 3-(cyanomethoxy)-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzene-1-sulfonamide | 645.2 |
| 344A | 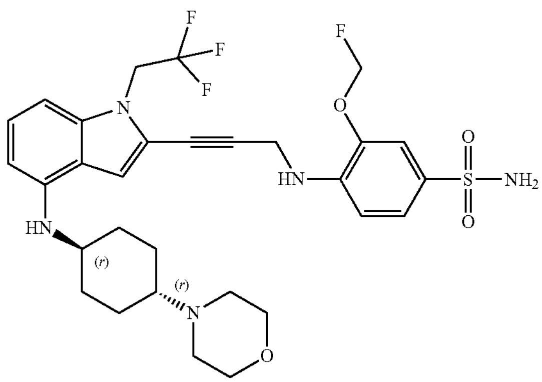 [SMILES: NS(=O)(=O)c1ccc(NCC#Cc2cc3c(N[C@H]4CC[C@H](N5CCOCC5)CC4)cccc3n2CC(F)(F)F)c(OCF)c1] | 3-(fluoromethoxy)-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide | 638.2 |
| 345A | 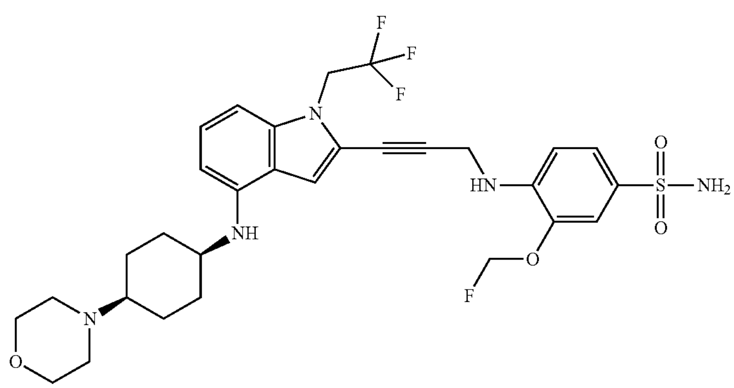 [SMILES: NS(=O)(=O)c1ccc(NCC#Cc2cc3c(N[C@H]4CC[C@@H](N5CCOCC5)CC4)cccc3n2CC(F)(F)F)c(OCF)c1] | 3-(fluoromethoxy)-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzene-1-sulfonamide | 638.2 |
| 346A | 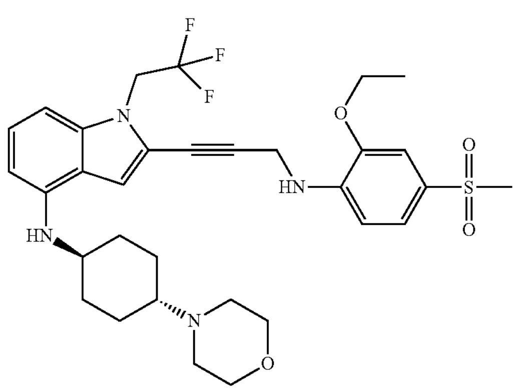 [SMILES: CCOc1cc(S(C)(=O)=O)ccc1NCC#Cc1cc2c(N[C@H]3CC[C@H](N4CCOCC4)CC3)cccc2n1CC(F)(F)F] | 2-(3-((2-ethoxy-4-(methylsulfonyl)phenyl)amino)prop-1-yn-1-yl)-N-((1R,4R)-4-morpholinocyclohexyl)-1-(2,2,2-trifluoroethyl)-1H-indol-4-amine | 633.2 |

TABLE 3-continued

| Compound No. | Structure | IUPAC | LC-MS (ES+, m/z) |
|---|---|---|---|
| 347A | 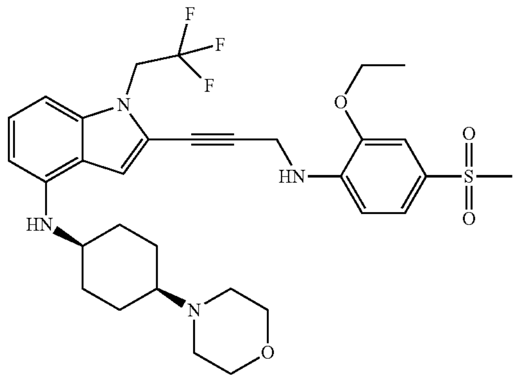 [SMILES: CCOc1cc(S(C)(=O)=O)ccc1NCC#Cc1cc2c(N[C@H]3CC[C@@H](N4CCOCC4)CC3)cccc2n1CC(F)(F)F] | 2-(3-((2-ethoxy-4-(methylsulfonyl)phenyl)amino)prop-1-yn-1-yl)-N-((1S,4S)-4-morpholinocyclohexyl)-1-(2,2,2-trifluoroethyl)-1H-indol-4-amine | 633.2 |
| 348A | 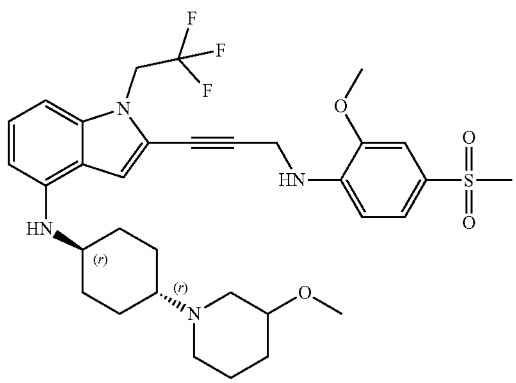 [SMILES: COc1cc(S(C)(=O)=O)ccc1NCC#Cc1cc2c(N[C@H]3CC[C@H](N4CCCC(OC)C4)CC3)cccc2n1CC(F)(F)F] | 2-{3-[(4-methanesulfonyl-2-methoxyphenyl)amino]prop-1-yn-1-yl}-N-[(1R,4R)-4-(3-methoxypiperidin-1-yl)cyclohexyl]-1-(2,2,2-trifluoroethyl)-1H-indol-4-amine | 647.2 |
| 349A | 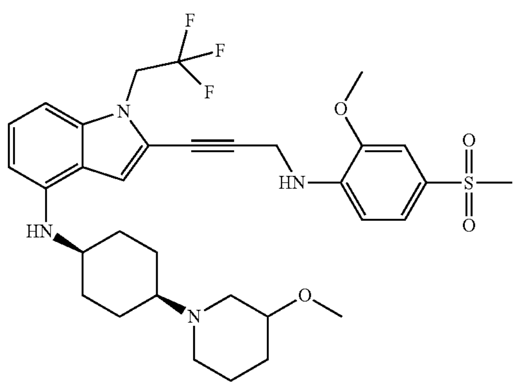 [SMILES: COc1cc(S(C)(=O)=O)ccc1NCC#Cc1cc2c(N[C@H]3CC[C@@H](N4CCCC(OC)C4)CC3)cccc2n1CC(F)(F)F] | 2-(3-((2-methoxy-4-(methylsulfonyl)phenyl)amino)prop-1-yn-1-yl)-N-((1S,4S)-4-(3-methoxypiperidin-1-yl)cyclohexyl)-1-(2,2,2-trifluoroethyl)-1H-indol-4-amine | 647.2 |
| 350A | 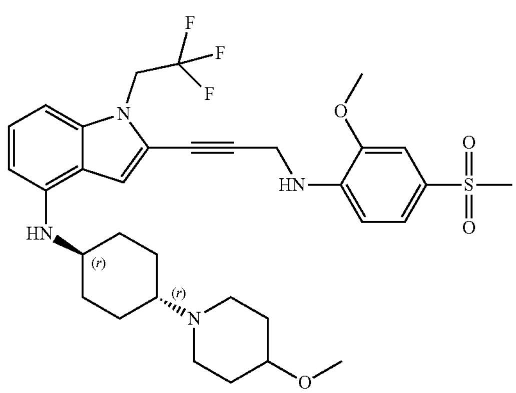 [SMILES: COc1cc(S(C)(=O)=O)ccc1NCC#Cc1cc2c(N[C@H]3CC[C@H](N4CCC(OC)CC4)CC3)cccc2n1CC(F)(F)F] | 2-{3-[(4-methanesulfonyl-2-methoxyphenyl)amino]prop-1-yn-1-yl}-N-[(1R,4R)-4-(4-methoxypiperidin-1-yl)cyclohexyl]-1-(2,2,2-trifluoroethyl)-1H-indol-4-amine | 647.3 |

TABLE 3-continued

| Compound No. | Structure | IUPAC | LC-MS (ES+, m/z) |
|---|---|---|---|
| 351A | 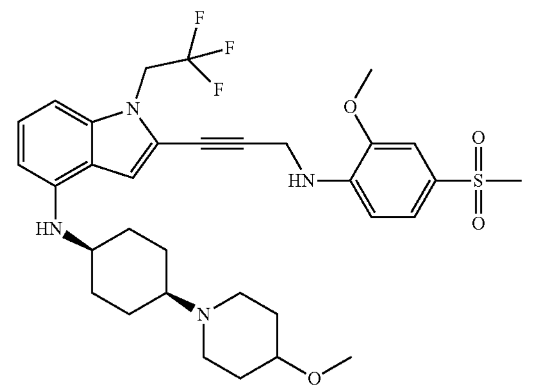 [SMILES: COc1cc(S(C)(=O)=O)ccc1NCC#Cc1cc2c(N[C@H]3CC[C@@H](N4CCC(OC)CC4)CC3)cccc2n1CC(F)(F)F] | 2-(3-((2-methoxy-4-(methylsulfonyl)phenyl)amino)prop-1-yn-1-yl)-N-((1S,4S)-4-(4-methoxypiperidin-1-yl)cyclohexyl)-1-(2,2,2-trifluoroethyl)-1H-indol-4-amine | 647.2 |
| 352A | 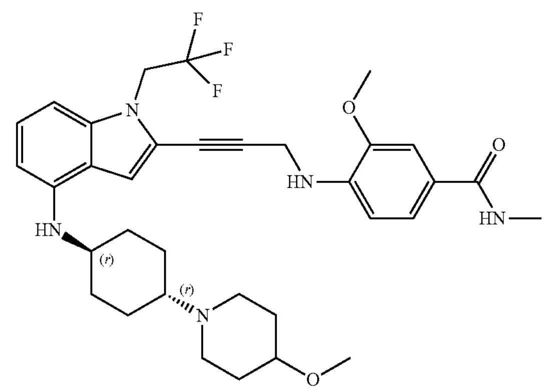 [SMILES: CNC(=O)c1ccc(NCC#Cc2cc3c(N[C@H]4CC[C@H](N5CCC(OC)CC5)CC4)cccc3n2CC(F)(F)F)c(OC)c1] | 3-methoxy-N-methyl-4-{[3-(4-{[(1R,4R)-4-(4-methoxypiperidin-1-yl)cyclohexyl]amino}-1-(2,2,2-trifluoroethyl)-1H-indol-2-yl)prop-2-yn-1-yl]amino}benzamide | 626.3 |
| 353A | 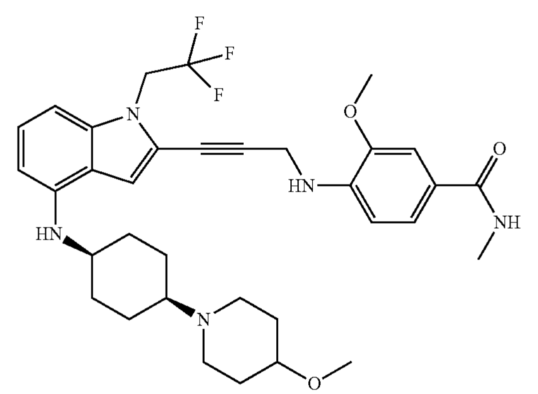 [SMILES: CNC(=O)c1ccc(NCC#Cc2cc3c(N[C@H]4CC[C@@H](N5CCC(OC)CC5)CC4)cccc3n2CC(F)(F)F)c(OC)c1] | 3-methoxy-4-((3-(4-(((1S,4S)-4-(4-methoxypiperidin-1-yl)cyclohexyl)amino)-1-(2,2,2-trifluoroethyl)-1H-indol-2-yl)prop-2-yn-1-yl)amino)-N-methylbenzamide | 626.3 |
| 354A | 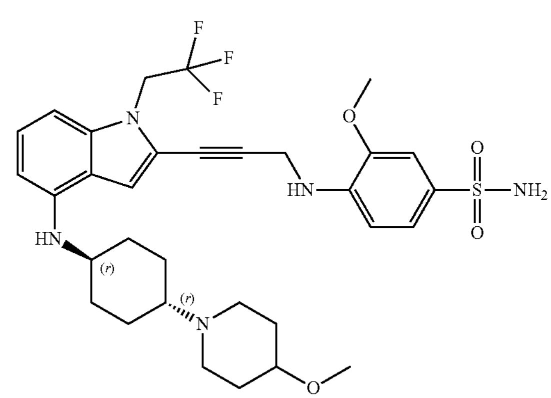 [SMILES: COc1cc(S(N)(=O)=O)ccc1NCC#Cc1cc2c(N[C@H]3CC[C@H](N4CCC(OC)CC4)CC3)cccc2n1CC(F)(F)F] | 3-methoxy-4-{[3-(4-{[(1R,4R)-4-(4-methoxypiperidin-1-yl)cyclohexyl]amino}-1-(2,2,2-trifluoroethyl)-1H-indol-2-yl)prop-2-yn-1-yl]amino}benzene-1-sulfonamide | 648.3 |

TABLE 3-continued

| Compound No. | Structure | IUPAC | LC-MS (ES+, m/z) |
|---|---|---|---|
| 355A | 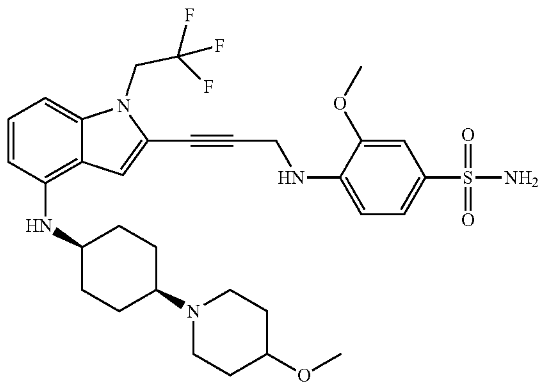 [SMILES: COc1cc(S(N)(=O)=O)ccc1NCC#Cc1cc2c(N[C@H]3CC[C@@H](N4CCC(OC)CC4)CC3)cccc2n1CC(F)(F)F] | 3-methoxy-4-((3-(4-(((1S,4S)-4-(4-methoxypiperidin-1-yl)cyclohexyl)amino)-1-(2,2,2-trifluoroethyl)-1H-indol-2-yl)prop-2-yn-1-yl)amino)benzenesulfonamide | 648.3 |
| 356A | 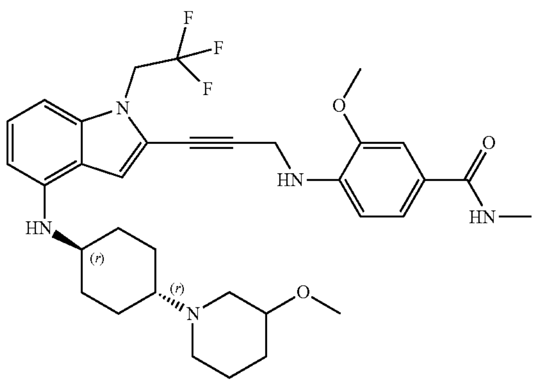 [SMILES: CNC(=O)c1ccc(NCC#Cc2cc3c(N[C@H]4CC[C@H](N5CCCC(OC)C5)CC4)cccc3n2CC(F)(F)F)c(OC)c1] | 3-methoxy-N-methyl-4-{[3-(4-{[(1R,4R)-4-(3-methoxypiperidin-1-yl)cyclohexyl]amino}-1-(2,2,2-trifluoroethyl)-1H-indol-2-yl)prop-2-yn-1-yl]amino}benzamide | 626.3 |
| 357A | 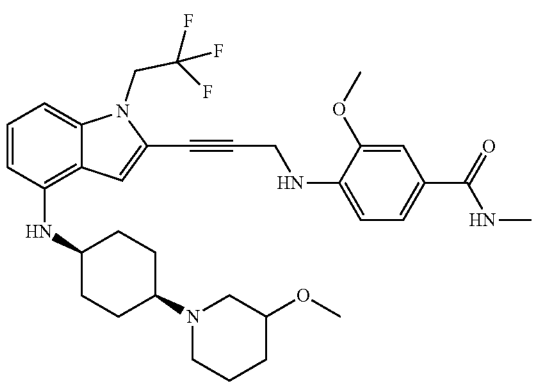 [SMILES: CNC(=O)c1ccc(NCC#Cc2cc3c(N[C@H]4CC[C@@H](N5CCCC(OC)C5)CC4)cccc3n2CC(F)(F)F)c(OC)c1] | 3-methoxy-4-((3-(4-(((1S,4S)-4-(3-methoxypiperidin-1-yl)cyclohexyl)amino)-1-(2,2,2-trifluoroethyl)-1H-indol-2-yl)prop-2-yn-1-yl)amino)-N-methylbenzamide | 626.3 |
| 358A | 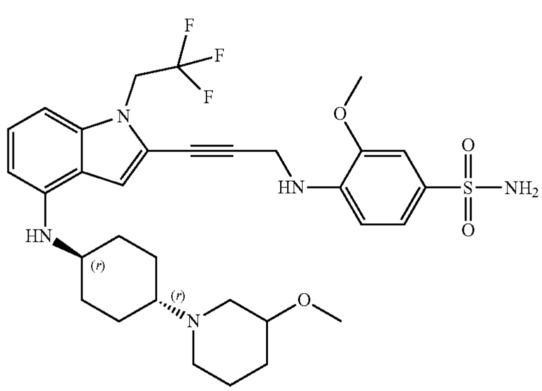 [SMILES: COc1cc(S(N)(=O)=O)ccc1NCC#Cc1cc2c(N[C@H]3CC[C@H](N4CCCC(OC)C4)CC3)cccc2n1CC(F)(F)F] | 3-methoxy-4-{[3-(4-{[(1R,4R)-4-(3-methoxypiperidin-1-yl)cyclohexyl]amino}-1-(2,2,2-trifluoroethyl)-1H-indol-2-yl)prop-2-yn-1-yl]amino}benzene-1-sulfonamide | 648.3 |

TABLE 3-continued

| Compound No. | Structure | IUPAC | LC-MS (ES+, m/z) |
|---|---|---|---|
| 359A | 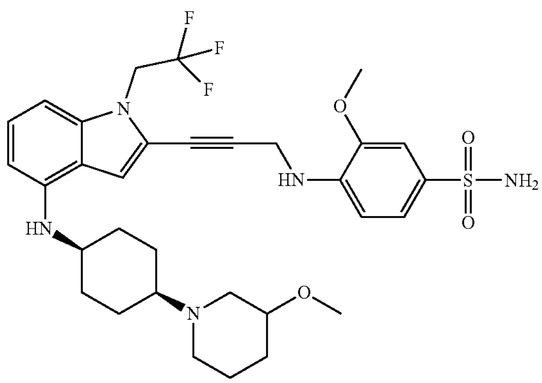 [SMILES: COc1cc(S(N)(=O)=O)ccc1NCC#Cc1cc2c(N[C@H]3CC[C@@H](N4CCCC(OC)C4)CC3)cccc2n1CC(F)(F)F] | 3-methoxy-4-((3-(4-(((1S,4S)-4-(3-methoxypiperidin-1-yl)cyclohexyl)amino)-1-(2,2,2-trifluoroethyl)-1H-indol-2-yl)prop-2-yn-1-yl)amino)benzenesulfonamide | 648.3 |
| 360A | 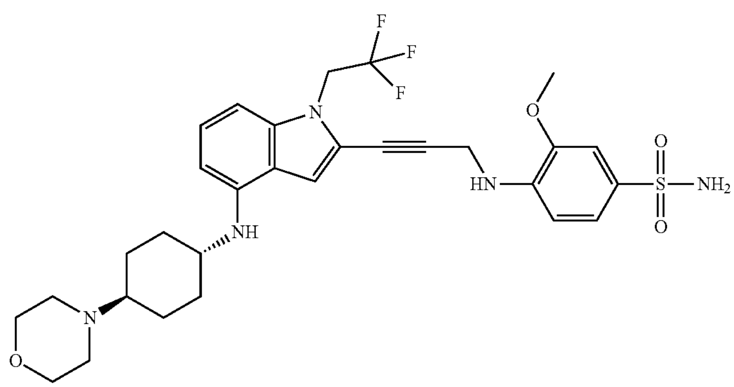 [SMILES: COc1cc(S(N)(=O)=O)ccc1NCC#Cc1cc2c(N[C@H]3CC[C@H](N4CCOCC4)CC3)cccc2n1CC(F)(F)F] | 3-methoxy-4-((3-(4-(((1R,4R)-4-morpholinocyclohexyl)amino)-1-(2,2,2-trifluoroethyl)-1H-indol-2-yl)prop-2-yn-1-yl)amino)benzenesulfonamide | 620.3 |
| 361A | 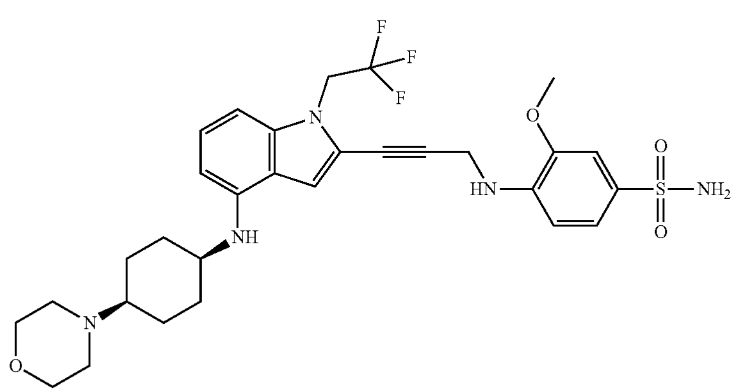 [SMILES: COc1cc(S(N)(=O)=O)ccc1NCC#Cc1cc2c(N[C@H]3CC[C@@H](N4CCOCC4)CC3)cccc2n1CC(F)(F)F] | 3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzenesulfonamide | 620.3 |

TABLE 3-continued

| Compound No. | Structure | IUPAC | LC-MS (ES+, m/z) |
|---|---|---|---|
| 362A | 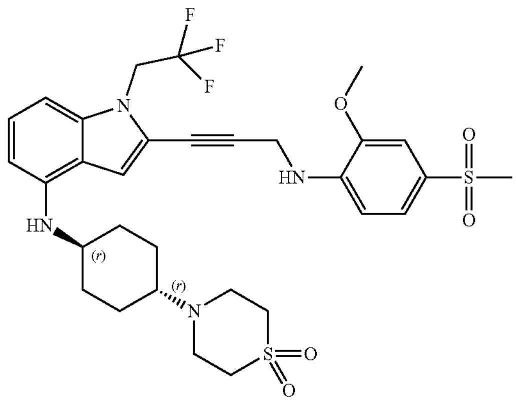 [SMILES: COc1cc(S(C)(=O)=O)ccc1NCC#Cc1cc2c(N[C@H]3CC[C@H](N4CCS(=O)(=O)CC4)CC3)cccc2n1CC(F)(F)F] | 4-[(1R,4R)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1λ⁶-thiomorpholine-1,1-dione | 667.2 |
| 363A | 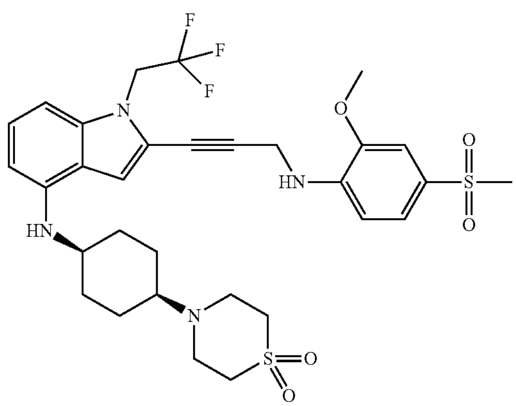 [SMILES: COc1cc(S(C)(=O)=O)ccc1NCC#Cc1cc2c(N[C@H]3CC[C@@H](N4CCS(=O)(=O)CC4)CC3)cccc2n1CC(F)(F)F] | 4-((1S,4S)-4-((2-(3-((2-methoxy-4-(methylsulfonyl)phenyl)amino)prop-1-yn-1-yl)-1-(2,2,2-trifluoroethyl)-1H-indol-4-yl)amino)cyclohexyl)thiomorpholine 1,1-dioxide | 667.2 |
| 364A | 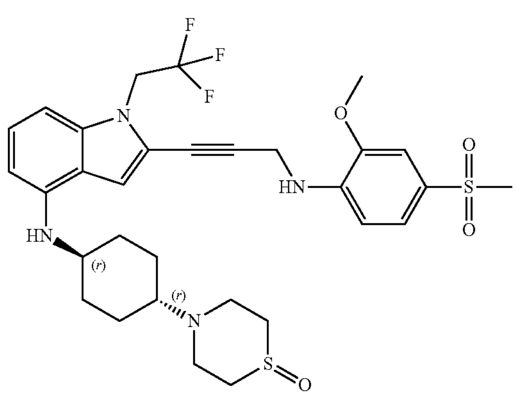 [SMILES: COc1cc(S(C)(=O)=O)ccc1NCC#Cc1cc2c(N[C@H]3CC[C@H](N4CCS(=O)CC4)CC3)cccc2n1CC(F)(F)F] | 4-[(1R,4R)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1λ⁴-thiomorpholin-1-one | 651.2 |

TABLE 3-continued

| Compound No. | Structure | IUPAC | LC-MS (ES+, m/z) |
|---|---|---|---|
| 365A | 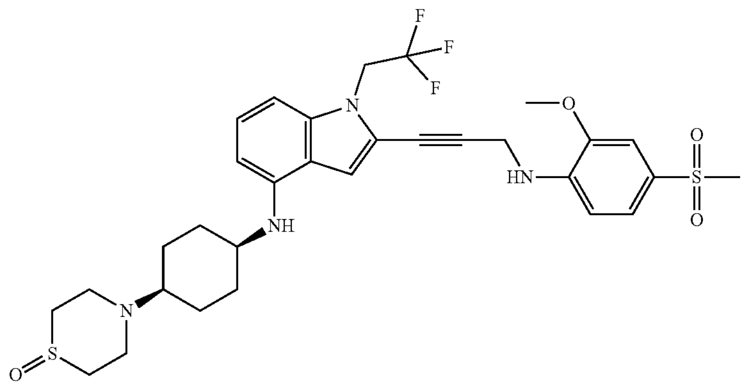 [SMILES: COc1cc(S(C)(=O)=O)ccc1NCC#Cc1cc2c(N[C@H]3CC[C@@H](N4CCS(=O)CC4)CC3)cccc2n1CC(F)(F)F] | 4-[(1S,4S)-4-[(2-{3-[(4-methanesulfonyl-2-methoxyphenyl)amino]prop-1-yn-1-yl}-1-(2,2,2-trifluoroethyl)-1H-indol-4-yl]amino]cyclohexyl]-1λ⁴-thiomorpholin-1-one | 651.2 |
| 366A | 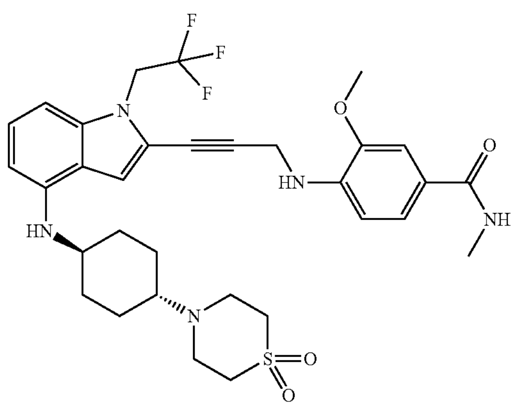 [SMILES: CNC(=O)c1ccc(NCC#Cc2cc3c(N[C@H]4CC[C@H](N5CCS(=O)(=O)CC5)CC4)cccc3n2CC(F)(F)F)c(OC)c1] | 4-((3-(4-(((1R,4R)-4-(1,1-dioxidothiomorpholino)cyclohexyl)amino)-1-(2,2,2-trifluoroethyl)-1H-indol-2-yl)prop-2-yn-1-yl)amino)-3-methoxy-N-methylbenzamide | |
| 367A | 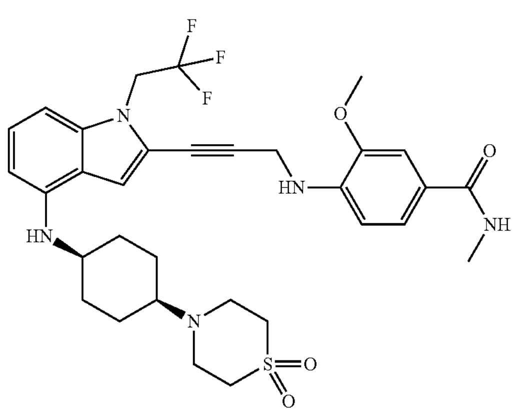 [SMILES: CNC(=O)c1ccc(NCC#Cc2cc3c(N[C@H]4CC[C@@H](N5CCS(=O)(=O)CC5)CC4)cccc3n2CC(F)(F)F)c(OC)c1] | 4-((3-(4-(((1S,4S)-4-(1,1-dioxidothiomorpholino)cyclohexyl)amino)-1-(2,2,2-trifluoroethyl)-1H-indol-2-yl)prop-2-yn-1-yl)amino)-3-methoxy-N-methylbenzamide | 646.2 |

TABLE 3-continued

| Compound No. | Structure | IUPAC | LC-MS (ES+, m/z) |
|---|---|---|---|
| 368A | 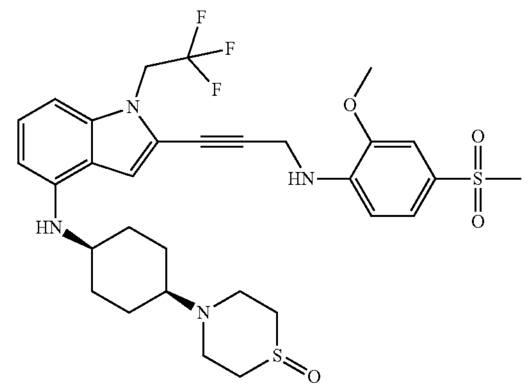 [SMILES: COc1cc(S(C)(=O)=O)ccc1NCC#Cc1cc2c(N[C@H]3CC[C@@H](N4CCS(=O)CC4)CC3)cccc2n1CC(F)(F)F] | 4-((1S,4S)-4-((2-(3-((2-methoxy-4-(methyl-sulfonyl)phenyl)amino)prop-1-yn-1-yl)-1-(2,2,2-trifluoroethyl)-1H-indol-4-yl)amino)cyclohexyl)thiomorpholine 1-oxide | 651.2 |
| 369A | 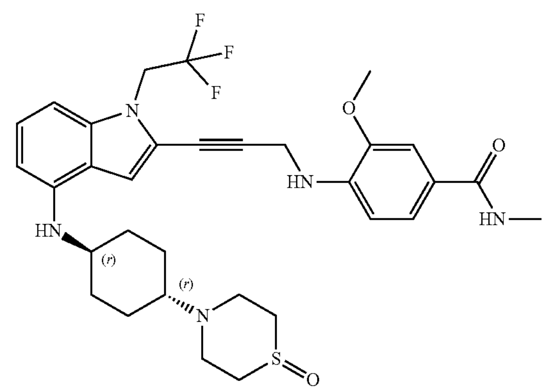 [SMILES: CNC(=O)c1ccc(NCC#Cc2cc3c(N[C@H]4CC[C@H](N5CCS(=O)CC5)CC4)cccc3n2CC(F)(F)F)c(OC)c1] | 3-methoxy-N-methyl-4-{[3-(4-{[(1R,4R)-4-(1-oxo-1λ⁴-thiomorpholin-4-yl)cyclohexyl]amino}-1-(2,2,2-trifluoroethyl)-1H-indol-2-yl)prop-2-yn-1-yl]amino}benzamide | 630.3 |
| 370A | 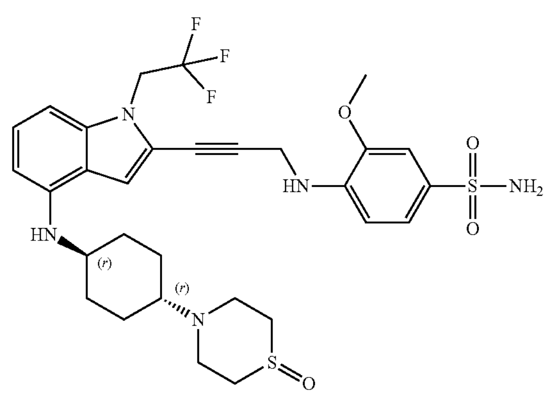 [SMILES: COc1cc(S(N)(=O)=O)ccc1NCC#Cc1cc2c(N[C@H]3CC[C@H](N4CCS(=O)CC4)CC3)cccc2n1CC(F)(F)F] | 3-methoxy-4-{[3-(4-{[(1R,4R)-4-(1-oxo-1λ⁴-thiomorpholin-4-yl)cyclohexyl]amino}-1-(2,2,2-trifluoroethyl)-1H-indol-2-yl)prop-2-yn-1-yl]amino}benzene-1-sulfonamide | 652.2 |
| 371A | 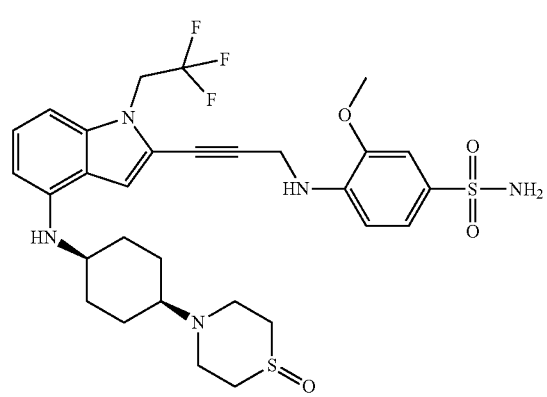 [SMILES: COc1cc(S(N)(=O)=O)ccc1NCC#Cc1cc2c(N[C@H]3CC[C@@H](N4CCS(=O)CC4)CC3)cccc2n1CC(F)(F)F] | 3-methoxy-4-((3-(4-(((1S,4S)-4-(1-oxidothiomorpholino)cyclohexyl)amino)-1-(2,2,2-trifluoroethyl)-1H-indol-2-yl)prop-2-yn-1-yl)amino)benzenesulfonamide | |

TABLE 3-continued

| Compound No. | Structure | IUPAC | LC-MS (ES+, m/z) |
|---|---|---|---|
| 372A | 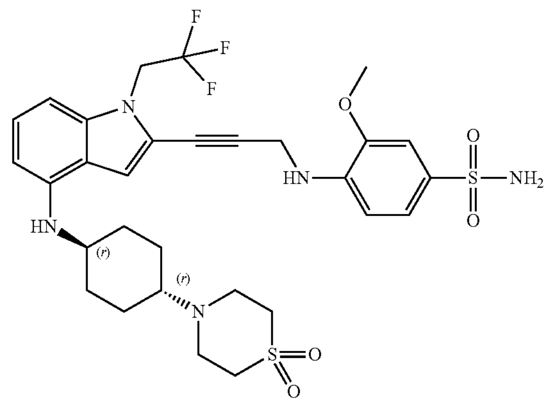 [SMILES: COc1cc(S(N)(=O)=O)ccc1NCC#Cc1cc2c(N[C@H]3CC[C@H](N4CCS(=O)(=O)CC4)CC3)cccc2n1CC(F)(F)F] | 3-methoxy-4-{[3-(4-{[(1R,4R)-4-(1,1-dioxo-1λ⁶-thiomorpholin-4-yl)cyclohexyl]amino}-1-(2,2,2-trifluoroethyl)-1H-indol-2-yl)prop-2-yn-1-yl]amino}benzene-1-sulfonamide | 668.2 |
| 373A | 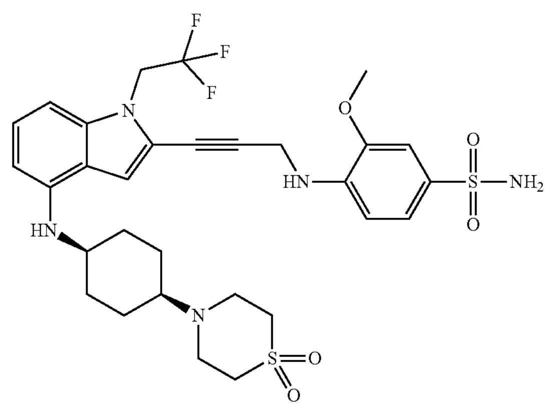 [SMILES: COc1cc(S(N)(=O)=O)ccc1NCC#Cc1cc2c(N[C@H]3CC[C@@H](N4CCS(=O)(=O)CC4)CC3)cccc2n1CC(F)(F)F] | 4-((3-(4-(((1S,4S)-4-(1,1-dioxidothiomorpholino)cyclohexyl)amino)-1-(2,2,2-trifluoroethyl)-1H-indol-2-yl)prop-2-yn-1-yl)amino)-3-methoxybenzenesulfonamide | 668.1 |
| 374A | 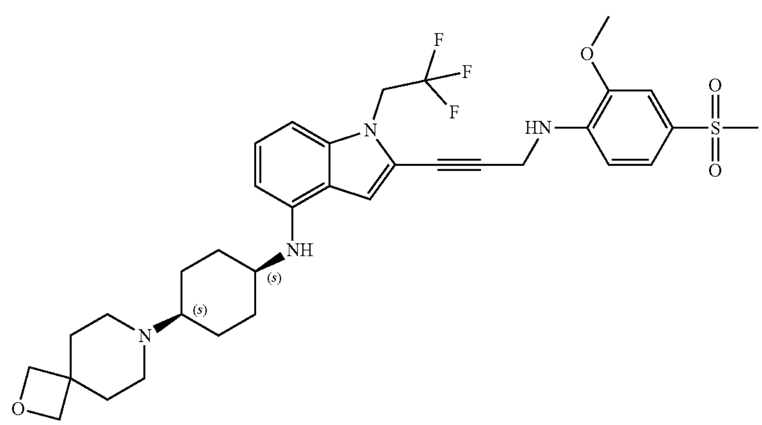 [SMILES: COc1cc(S(C)(=O)=O)ccc1NCC#Cc1cc2c(N[C@H]3CC[C@@H](N4CCC5(CC4)COC5)CC3)cccc2n1CC(F)(F)F] | 2-{3-[(4-methanesulfonyl-2-methoxyphenyl)amino]prop-1-yn-1-yl}-N-[(1S,4S)-4-{2-oxa-7-azaspiro[3.5]nonan-7-yl}cyclohexyl]-1-(2,2,2-trifluoroethyl)-1H-indol-4-amine | 659.3 |

TABLE 3-continued

| Compound No. | Structure | IUPAC | LC-MS (ES+, m/z) |
|---|---|---|---|
| 375A | 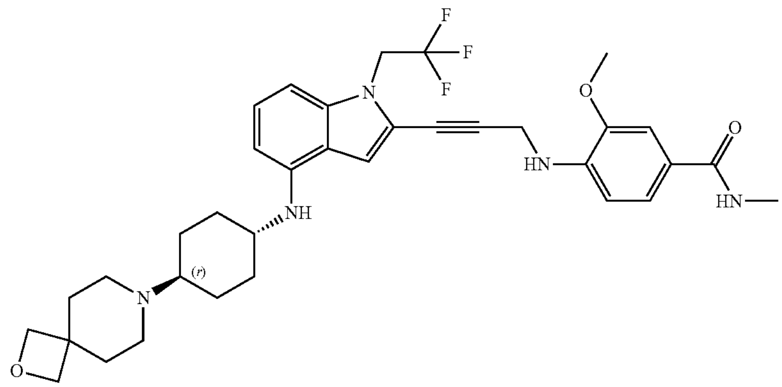 [SMILES: CNC(=O)c1ccc(NCC#Cc2cc3c(N[C@H]4CC[C@H](N5CCC6(CC5)COC6)CC4)cccc3n2CC(F)(F)F)c(OC)c1] | 3-methoxy-N-methyl-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzamide | 638.4 |
| 376A | 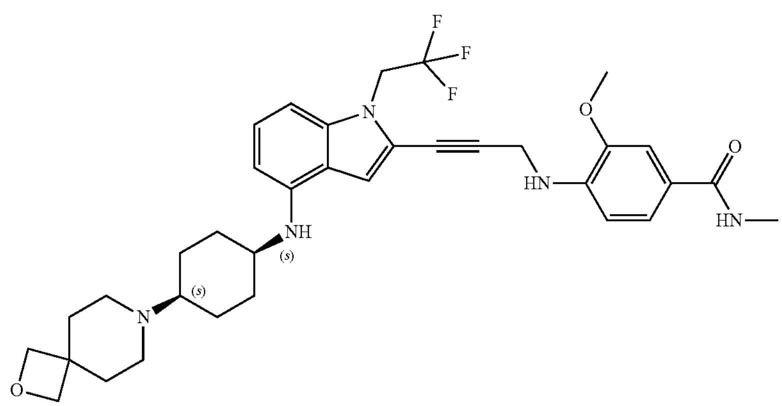 [SMILES: CNC(=O)c1ccc(NCC#Cc2cc3c(N[C@H]4CC[C@@H](N5CCC6(CC5)COC6)CC4)cccc3n2CC(F)(F)F)c(OC)c1] | 3-methoxy-N-methyl-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzamide | 638.3 |
| 377A | 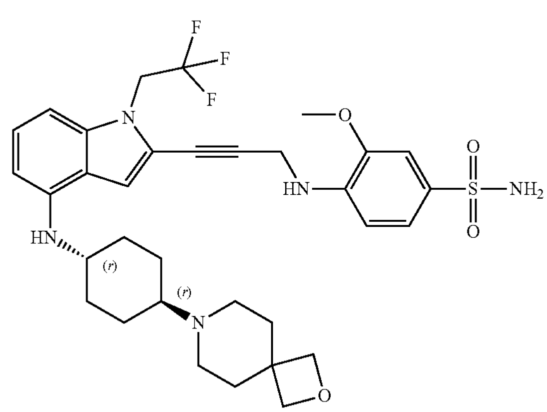 [SMILES: COc1cc(S(N)(=O)=O)ccc1NCC#Cc1cc2c(N[C@H]3CC[C@H](N4CCC5(CC4)COC5)CC3)cccc2n1CC(F)(F)F] | 3-methoxy-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide | 660.2 |

TABLE 3-continued

| Compound No. | Structure | IUPAC | LC-MS (ES+, m/z) |
|---|---|---|---|
| 378A | 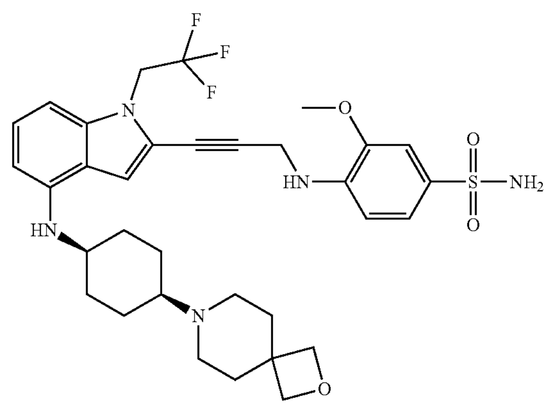 [SMILES: COc1cc(S(N)(=O)=O)ccc1NCC#Cc1cc2c(N[C@H]3CC[C@@H](N4CCC5(CC4)COC5)CC3)cccc2n1CC(F)(F)F] | 4-((3-(4-(((1S,4S)-4-(2-oxa-7-azaspiro[3.5]nonan-7-yl)cyclohexyl)amino)-1-(2,2,2-trifluoroethyl)-1H-indol-2-yl)prop-2-yn-1-yl)amino)-3-methoxybenzenesulfonamide | 660.2 |
| 379A | 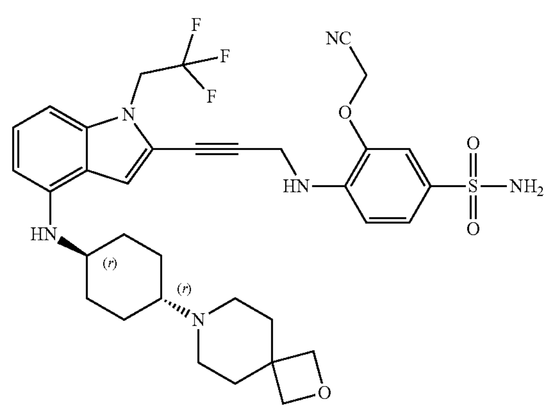 [SMILES: N#CCOc1cc(S(N)(=O)=O)ccc1NCC#Cc1cc2c(N[C@H]3CC[C@H](N4CCC5(CC4)COC5)CC3)cccc2n1CC(F)(F)F] | 3-(cyanomethoxy)-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide | 685.2 |
| 380A | 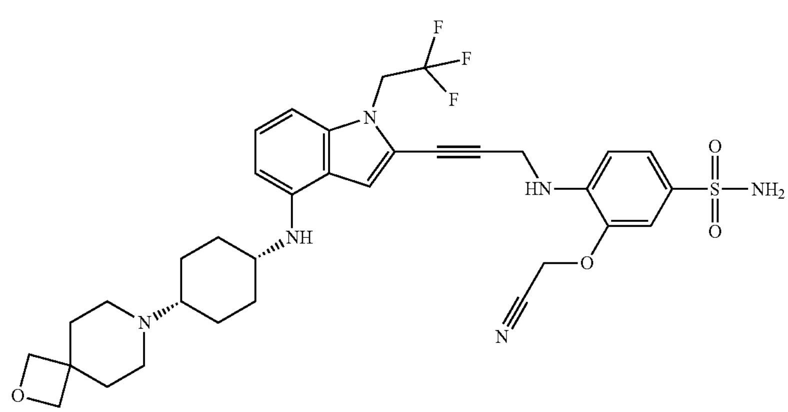 [SMILES: N#CCOc1cc(S(N)(=O)=O)ccc1NCC#Cc1cc2c(N[C@H]3CC[C@@H](N4CCC5(CC4)COC5)CC3)cccc2n1CC(F)(F)F] | 3-(cyanomethoxy)-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide | 685.2 |

TABLE 3-continued

| Compound No. | Structure | IUPAC | LC-MS (ES+, m/z) |
|---|---|---|---|
| 381A | 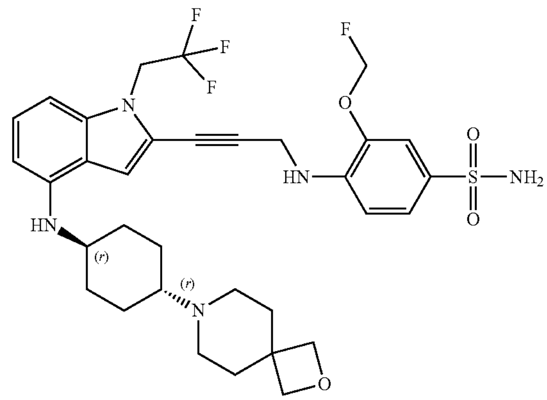 [SMILES: NS(=O)(=O)c1ccc(NCC#Cc2cc3c(N[C@H]4CC[C@H](N5CCC6(CC5)COC6)CC4)cccc3n2CC(F)(F)F)c(OCF)c1] | 3-(fluoromethoxy)-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide | 678.2 |
| 382A | 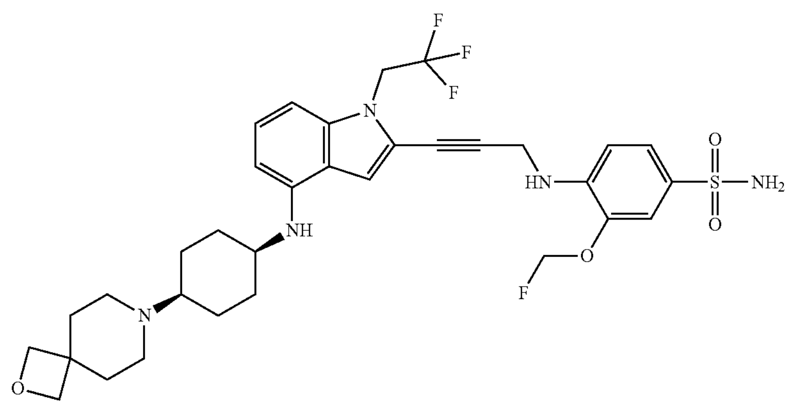 [SMILES: NS(=O)(=O)c1ccc(NCC#Cc2cc3c(N[C@H]4CC[C@@H](N5CCC6(CC5)COC6)CC4)cccc3n2CC(F)(F)F)c(OCF)c1] | 3-(fluoromethoxy)-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide | 678.2 |
| 383A | 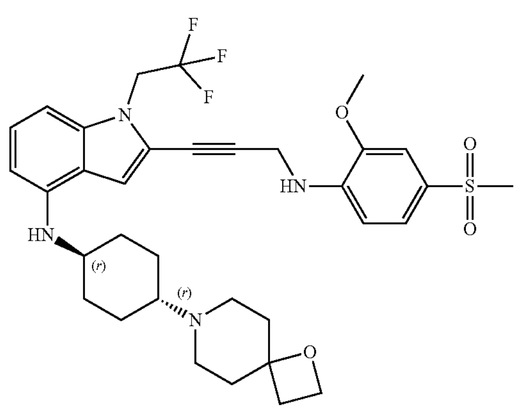 [SMILES: COc1cc(S(C)(=O)=O)ccc1NCC#Cc1cc2c(N[C@H]3CC[C@H](N4CCC5(CCO5)CC4)CC3)cccc2n1CC(F)(F)F] | 2-{3-[(4-methanesulfonyl-2-methoxyphenyl)amino]prop-1-yn-1-yl}-N-[(1R,4R)-4-{1-oxa-7-azaspiro[3.5]nonan-7-yl}cyclohexyl]-1-(2,2,2-trifluoroethyl)-1H-indol-4-amine | 659.3 |

TABLE 3-continued

| Compound No. | Structure | IUPAC | LC-MS (ES+, m/z) |
|---|---|---|---|
| 384A | 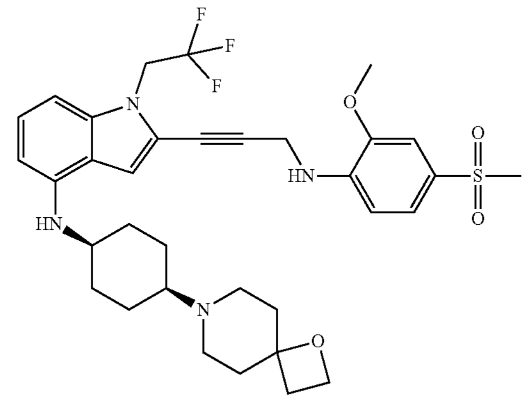 [SMILES: COc1cc(S(C)(=O)=O)ccc1NCC#Cc1cc2c(N[C@H]3CC[C@@H](N4CCC5(CCO5)CC4)CC3)cccc2n1CC(F)(F)F] | N-((1S,4S)-4-(1-oxa-7-azaspiro[3.5]nonan-7-yl)cyclohexyl)-2-(3-((2-methoxy-4-(methylsulfonyl)phenyl)amino)prop-1-yn-1-yl)-1-(2,2,2-trifluoroethyl)-1H-indol-4-amine | 659.3 |
| 385A | 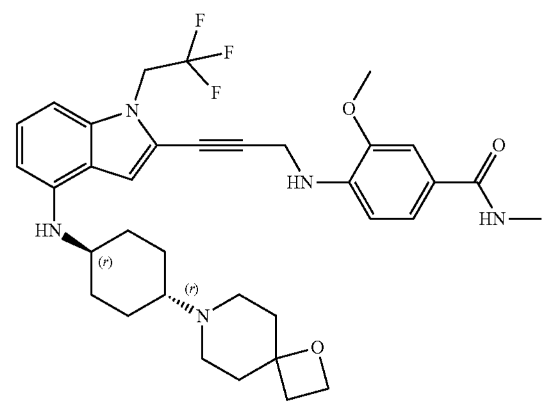 [SMILES: CNC(=O)c1ccc(NCC#Cc2cc3c(N[C@H]4CC[C@H](N5CCC6(CCO6)CC5)CC4)cccc3n2CC(F)(F)F)c(OC)c1] | 3-methoxy-N-methyl-4-{[3-(4-{[(1R,4R)-4-{1-oxa-7-azaspiro[3.5]nonan-7-yl}cyclohexyl]amino}-1-(2,2,2-trifluoroethyl)-1H-indol-2-yl)prop-2-yn-1-yl]amino}benzamide | 638.3 |
| 386A | 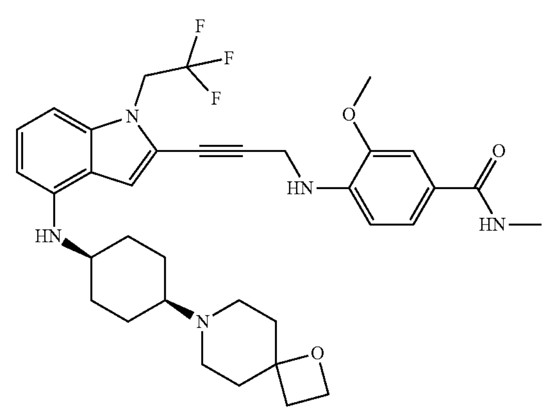 [SMILES: CNC(=O)c1ccc(NCC#Cc2cc3c(N[C@H]4CC[C@@H](N5CCC6(CCO6)CC5)CC4)cccc3n2CC(F)(F)F)c(OC)c1] | 4-((3-(4-(((1S,4S)-4-(1-oxa-7-azaspiro[3.5]nonan-7-yl)cyclohexyl)amino)-1-(2,2,2-trifluoroethyl)-1H-indol-2-yl)prop-2-yn-1-yl)amino)-3-methoxy-N-methylbenzamide | 638.3 |

TABLE 3-continued

| Compound No. | Structure | IUPAC | LC-MS (ES+, m/z) |
|---|---|---|---|
| 387A | 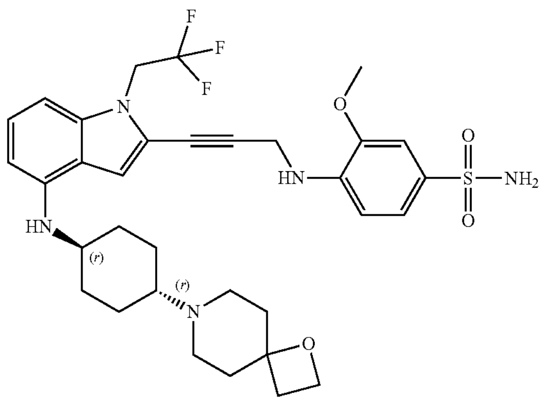 [SMILES: COc1cc(S(N)(=O)=O)ccc1NCC#Cc1cc2c(N[C@H]3CC[C@H](N4CCC5(CCO5)CC4)CC3)cccc2n1CC(F)(F)F] | 3-methoxy-4-{[3-(4-{[(1R,4R)-4-{1-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide | 660.3 |
| 388A | 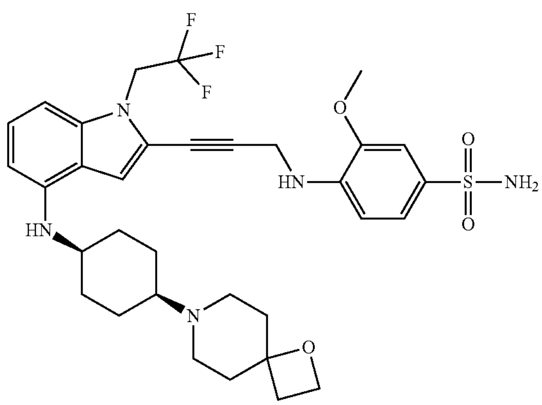 [SMILES: COc1cc(S(N)(=O)=O)ccc1NCC#Cc1cc2c(N[C@H]3CC[C@@H](N4CCC5(CCO5)CC4)CC3)cccc2n1CC(F)(F)F] | 4-((3-(4-(((1S,4S)-4-(1-oxa-7-azaspiro[3.5]nonan-7-yl)cyclohexyl)amino)-1-(2,2,2-trifluoroethyl)-1H-indol-2-yl)prop-2-yn-1-yl)amino)-3-methoxy-benzenesulfonamide | 660.3 |
| 389A | 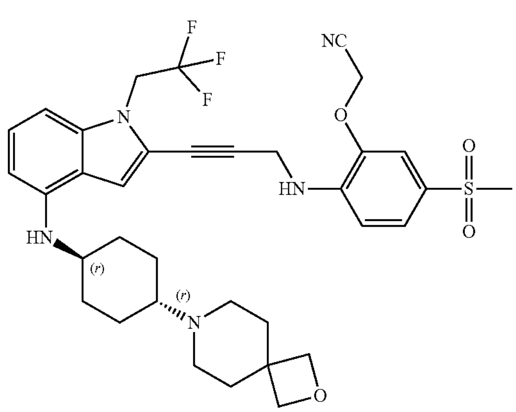 | 2-(5-methanesulfonyl-2-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}phenoxy)acetonitrile | 684.2 |

TABLE 3-continued

| Compound No. | Structure | IUPAC | LC-MS (ES+, m/z) |
|---|---|---|---|
| 390A | 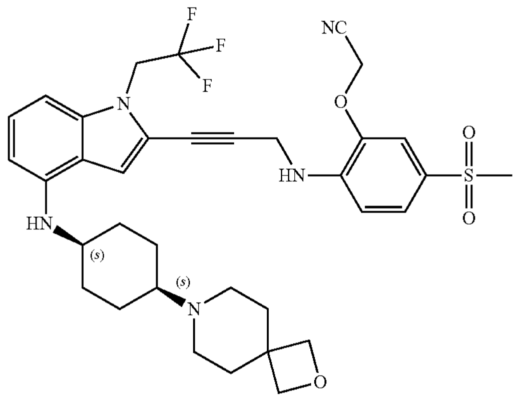 [SMILES: CS(=O)(=O)c1ccc(NCC#Cc2cc3c(N[C@H]4CC[C@@H](N5CCC6(CC5)COC6)CC4)cccc3n2CC(F)(F)F)c(OCC#N)c1] | 2-(5-methanesulfonyl-2-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}phenoxy)acetonitrile | 684.2 |
| 391A | 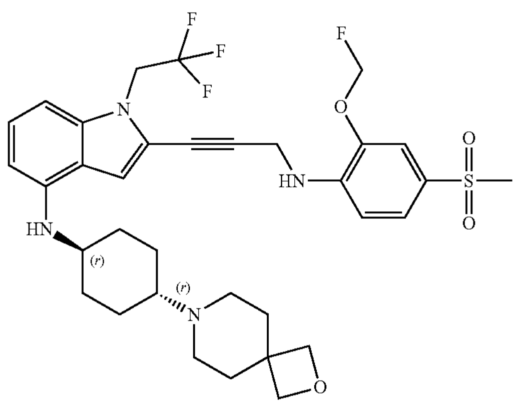 [SMILES: CS(=O)(=O)c1ccc(NCC#Cc2cc3c(N[C@H]4CC[C@H](N5CCC6(CC5)COC6)CC4)cccc3n2CC(F)(F)F)c(OCF)c1] | 2-(3-{[2-(fluoromethoxy)-4-methanesulfonylphenyl]amino}prop-1-yn-1-yl)-N-[(1R,4R)-4-(2-oxa-7-azaspiro[3.5]nonan-7-yl)cyclohexyl]-1-(2,2,2-trifluoroethyl)-1H-indol-4-amine | 677.3 |
| 392A | 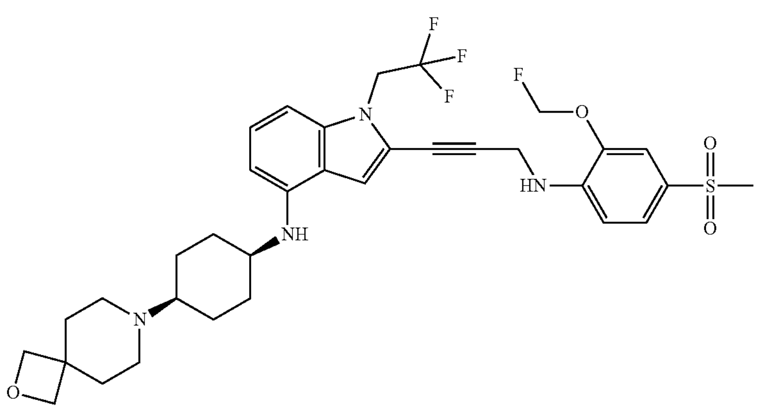 [SMILES: CS(=O)(=O)c1ccc(NCC#Cc2cc3c(N[C@H]4CC[C@@H](N5CCC6(CC5)COC6)CC4)cccc3n2CC(F)(F)F)c(OCF)c1] | 2-(3-{[2-(fluoromethoxy)-4-methanesulfonylphenyl]amino}prop-1-yn-1-yl)-N-[(1S,4S)-4-{2-oxa-7-azaspiro[3.5]nonan-7-yl}cyclohexyl]-1-(2,2,2-trifluoroethyl)-1H-indol-4-amine | 677.3 |

TABLE 3-continued

| Compound No. | Structure | IUPAC | LC-MS (ES+, m/z) |
|---|---|---|---|
| 393A | 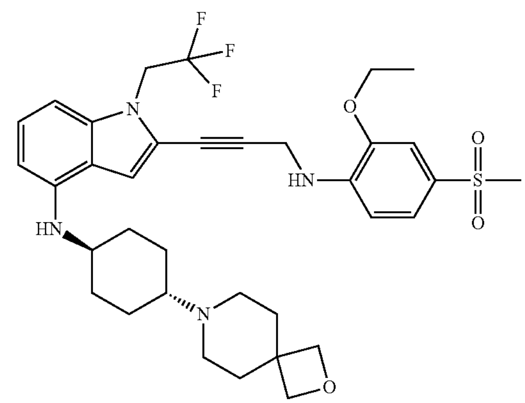 [SMILES: CCOc1cc(S(C)(=O)=O)ccc1NCC#Cc1cc2c(N[C@H]3CC[C@H](N4CCC5(CC4)COC5)CC3)cccc2n1CC(F)(F)F] | N-((1R,4R)-4-(2-oxa-7-azaspiro[3.5]nonan-7-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine | 673.2 |
| 394A | 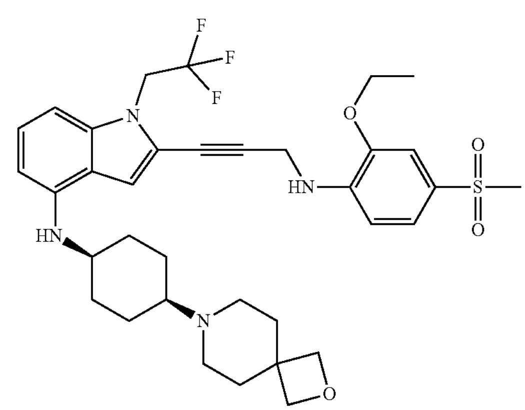 [SMILES: CCOc1cc(S(C)(=O)=O)ccc1NCC#Cc1cc2c(N[C@H]3CC[C@@H](N4CCC5(CC4)COC5)CC3)cccc2n1CC(F)(F)F] | N-((1S,4S)-4-(2-oxa-7-azaspiro[3.5]nonan-7-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine | |
| 395A | 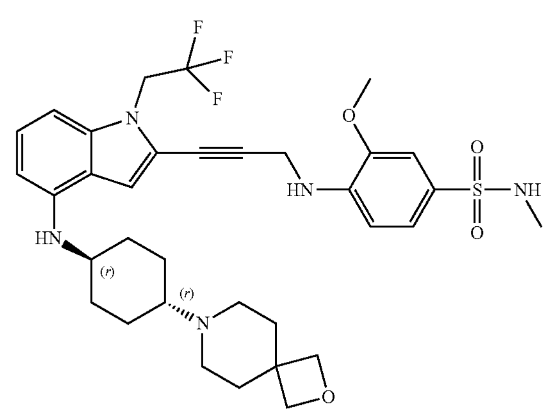 [SMILES: CNS(=O)(=O)c1ccc(NCC#Cc2cc3c(N[C@H]4CC[C@H](N5CCC6(CC5)COC6)CC4)cccc3n2CC(F)(F)F)c(OC)c1] | 3-methoxy-N-methyl-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide | 674.2 |

TABLE 3-continued

| Compound No. | Structure | IUPAC | LC-MS (ES+, m/z) |
|---|---|---|---|
| 396A | 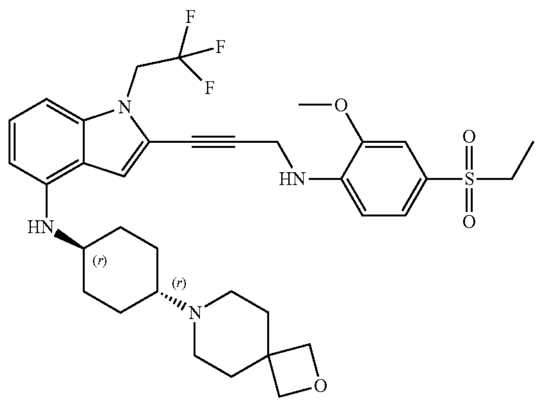 [SMILES: CCS(=O)(=O)c1ccc(NCC#Cc2cc3c(N[C@H]4CC[C@H](N5CCC6(CC5)COC6)CC4)cccc3n2CC(F)(F)F)c(OC)c1] | N-((1R,4R)-4-(2-oxa-7-azaspiro[3.5]nonan-7-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine | 673.2 |
| 397A | 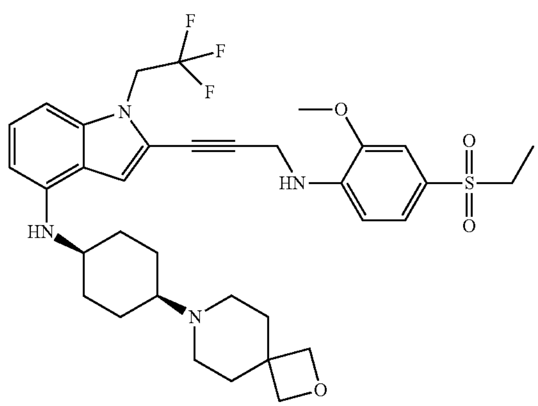 [SMILES: CCS(=O)(=O)c1ccc(NCC#Cc2cc3c(N[C@H]4CC[C@@H](N5CCC6(CC5)COC6)CC4)cccc3n2CC(F)(F)F)c(OC)c1] | N-((1S,4S)-4-(2-oxa-7-azaspiro[3.5]nonan-7-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine | 673.2 |
| 398A | 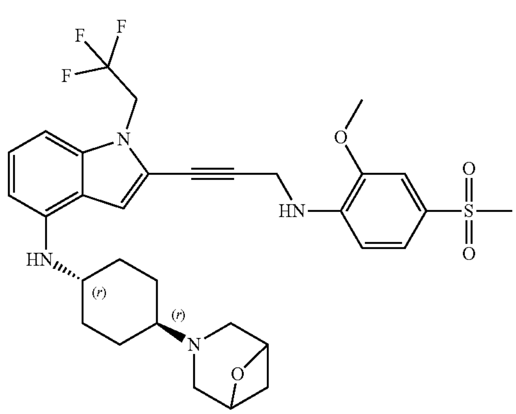 [SMILES: COc1cc(S(C)(=O)=O)ccc1NCC#Cc1cc2c(N[C@H]3CC[C@H](N4CC5CC(C4)O5)CC3)cccc2n1CC(F)(F)F] | 2-{3-[(4-methanesulfonyl-2-methoxyphenyl)amino]prop-1-yn-1-yl}-N-[(1R,4R)-4{6-oxa-3-azabicyclo[3.1.1]heptan-3-yl}cyclohexyl]-1-(2,2,2-trifluoroethyl)-1H-indol-4-amine | 631.2 |

TABLE 3-continued

| Compound No. | Structure | IUPAC | LC-MS (ES⁺, m/z) |
|---|---|---|---|
| 399A | 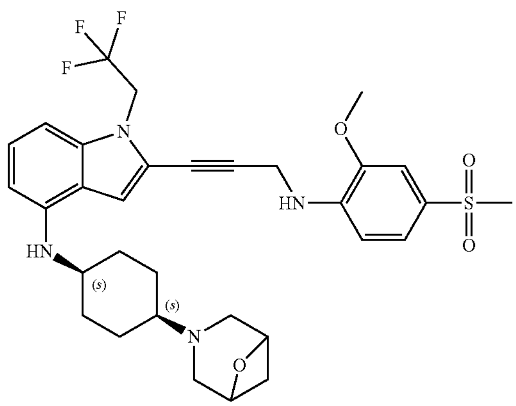 [SMILES: COc1cc(S(C)(=O)=O)ccc1NCC#Cc1cc2c(N[C@H]3CC[C@@H](N4CC5CC(C4)O5)CC3)cccc2n1CC(F)(F)F] | 2-{3-[(4-methanesulfonyl-2-methoxyphenyl)amino]prop-1-yn-1-yl}-N-[(1S,4S)-4-{6-oxa-3-azabicyclo[3.1.1]heptan-3-yl}cyclohexyl]-1-(2,2,2-trifluoroethyl)-1H-indol-4-amine | 631.2 |
| 400A | 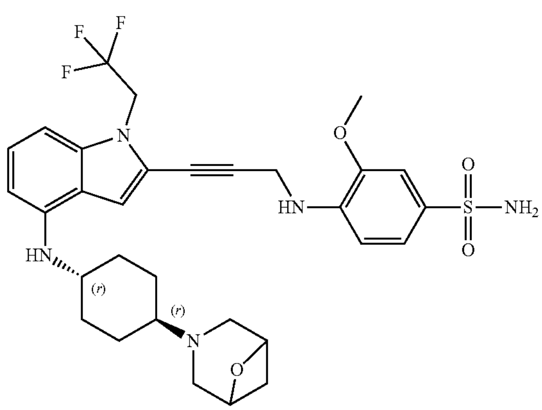 [SMILES: COc1cc(S(N)(=O)=O)ccc1NCC#Cc1cc2c(N[C@H]3CC[C@H](N4CC5CC(C4)O5)CC3)cccc2n1CC(F)(F)F] | 3-methoxy-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzene-1-sulfonamide | 632.2 |
| 401A | 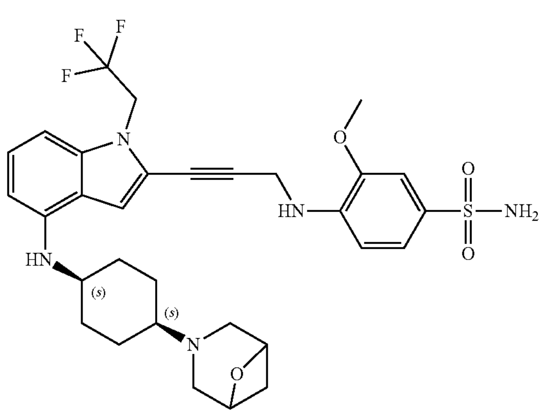 [SMILES: COc1cc(S(N)(=O)=O)ccc1NCC#Cc1cc2c(N[C@H]3CC[C@@H](N4CC5CC(C4)O5)CC3)cccc2n1CC(F)(F)F] | 3-methoxy-4-{[3-(4-{[(1S,4S)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzene-1-sulfonamide | 632.2 |

TABLE 3-continued

| Compound No. | Structure | IUPAC | LC-MS (ES+, m/z) |
|---|---|---|---|
| 402A | 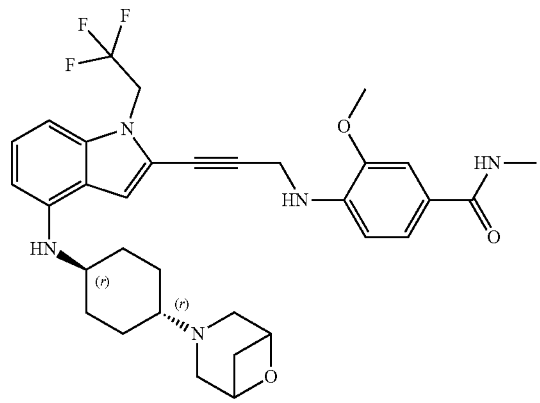 [SMILES: CNC(=O)c1ccc(NCC#Cc2cc3c(N[C@H]4CC[C@H](N5CC6CC(C5)O6)CC4)cccc3n2CC(F)(F)F)c(OC)c1] | 3-methoxy-N-methyl-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzamide | 610.3 |
| 403A | 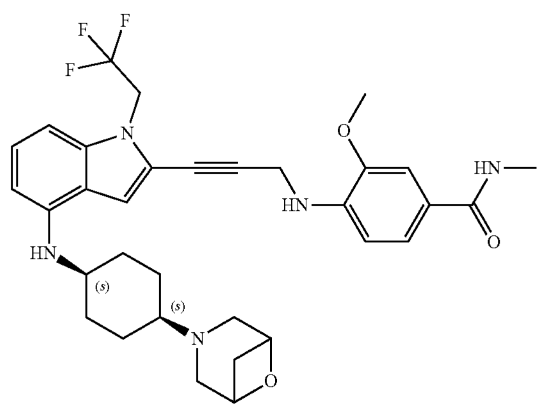 [SMILES: CNC(=O)c1ccc(NCC#Cc2cc3c(N[C@H]4CC[C@@H](N5CC6CC(C5)O6)CC4)cccc3n2CC(F)(F)F)c(OC)c1] | 3-methoxy-N-methyl-4-{[3-(4-{[(1S,4S)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzamide | 610.3 |
| 404A | 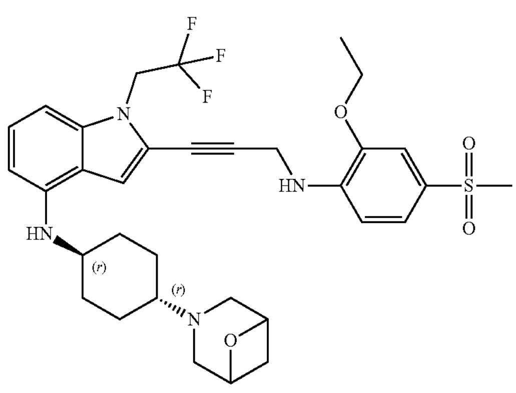 [SMILES: CCOc1cc(S(C)(=O)=O)ccc1NCC#Cc1cc2c(N[C@H]3CC[C@H](N4CC5CC(C4)O5)CC3)cccc2n1CC(F)(F)F] | 2-{3-[(2-ethoxy-4-methanesulfonyl-phenyl)amino]prop-1-yn-1-yl}-N-[(1R,4R)-4-{6-oxa-3-azabicyclo[3.1.1]heptan-3-yl}cyclohexyl]-1-(2,2,2-trifluoroethyl)-1H-indol-4-amine | 645.3 |

TABLE 3-continued

| Compound No. | Structure | IUPAC | LC-MS (ES+, m/z) |
|---|---|---|---|
| 405A | 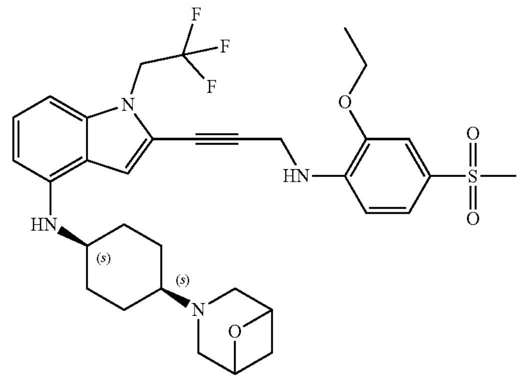 [SMILES: CCOc1cc(S(C)(=O)=O)ccc1NCC#Cc1cc2c(N[C@H]3CC[C@@H](N4CC5CC(C4)O5)CC3)cccc2n1CC(F)(F)F] | 2-{3-[(2-ethoxy-4-methanesulfonyl-phenyl)amino]prop-1-yn-1-yl}-N-[(1S,4S)-4-{6-oxa-3-azabicyclo[3.1.1]heptan-3-yl}cyclohexyl]-1-(2,2,2-trifluoroethyl)-1H-indol-4-amine | 645.3 |
| 406A | 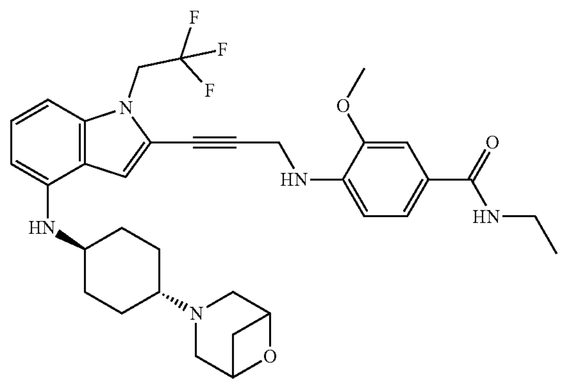 [SMILES: CCNC(=O)c1ccc(NCC#Cc2cc3c(N[C@H]4CC[C@H](N5CC6CC(C5)O6)CC4)cccc3n2CC(F)(F)F)c(OC)c1] | N-ethyl-3-methoxy-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzamide | 624.3 |
| 407A | 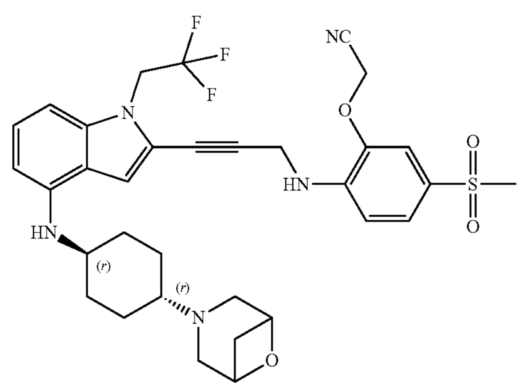 [SMILES: CS(=O)(=O)c1ccc(NCC#Cc2cc3c(N[C@H]4CC[C@H](N5CC6CC(C5)O6)CC4)cccc3n2CC(F)(F)F)c(OCC#N)c1] | 2-(5-methanesulfonyl-2-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}phenoxy)acetonitrile | 656.2 |
| 408A | 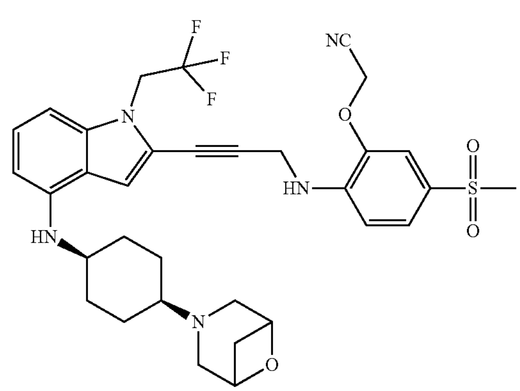 [SMILES: CS(=O)(=O)c1ccc(NCC#Cc2cc3c(N[C@H]4CC[C@@H](N5CC6CC(C5)O6)CC4)cccc3n2CC(F)(F)F)c(OCC#N)c1] | 2-(2-((3-(4-(((1S,4S)-4-(6-oxa-3-azabicyclo[3.1.1]heptan-3-yl)cyclohexyl)amino)-1-(2,2,2-trifluoroethyl)-1H-indol-2-yl)prop-2-yn-1-yl)amino)-5-(methylsulfonyl)phenoxy)acetonitrile | 656.2 |

TABLE 3-continued

| Compound No. | Structure | IUPAC | LC-MS (ES+, m/z) |
|---|---|---|---|
| 409A | 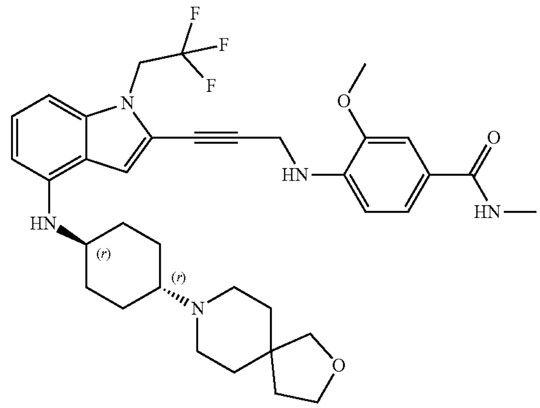 [SMILES: CNC(=O)c1ccc(NCC#Cc2cc3c(N[C@H]4CC[C@H](N5CCC6(CCOC6)CC5)CC4)cccc3n2CC(F)(F)F)c(OC)c1] | 3-methoxy-N-methyl-4-{[3-(4-{[(1R,4R)-4-{2-oxa-8-azaspiro[4.5]decan-8-yl}cyclohexyl]amino}-1-(2,2,2-trifluoroethyl)-1H-indol-2-yl)prop-2-yn-1-yl]amino}benzamide | 652.3 |
| 410A | 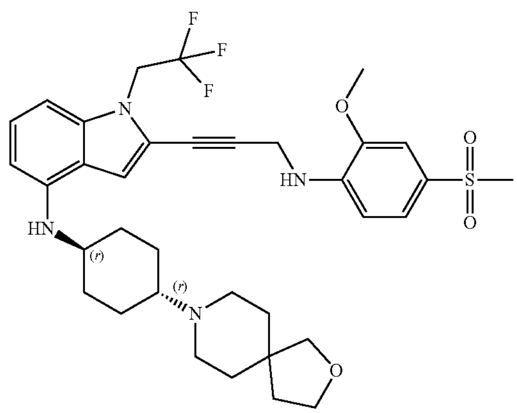 | 2-{3-[(4-methanesulfonyl-2-methoxyphenyl)amino]prop-1-yn-1-yl}-N-[(1R,4R)-4-{2-oxa-8-azaspiro[4.5]decan-8-yl}cyclohexyl]-1-(2,2,2-trifluoroethyl)-1H-indol-4-amine | 673.3 |
| 411A | 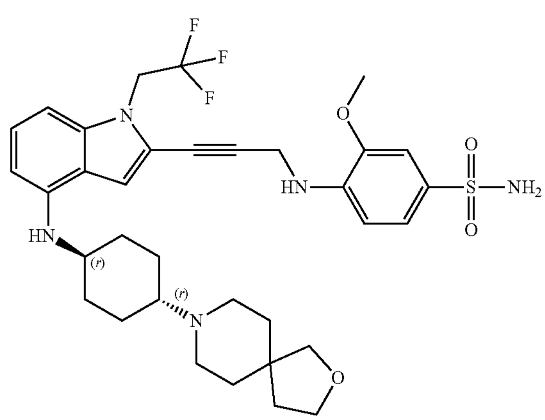 [SMILES: COc1cc(S(N)(=O)=O)ccc1NCC#Cc1cc2c(N[C@H]3CC[C@H](N4CCC5(CCOC5)CC4)CC3)cccc2n1CC(F)(F)F] | 3-methoxy-4-{[3-(4-{[(1R,4R)-4-{2-oxa-8-azaspiro[4.5]decan-8-yl}cyclohexyl]amino}-1-(2,2,2-trifluoroethyl)-1H-indol-2-yl)prop-2-yn-1-yl]amino}benzene-1-sulfonamide | 674.3 |

TABLE 3-continued

| Compound No. | Structure | IUPAC | LC-MS (ES+, m/z) |
|---|---|---|---|
| 412A | 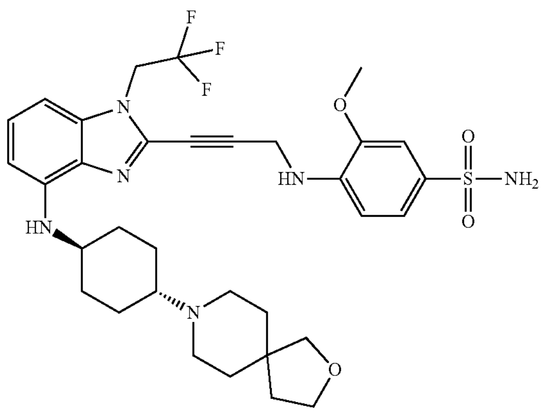 [SMILES: COc1cc(S(N)(=O)=O)ccc1NCC#Cc1nc2c(N[C@H]3CC[C@H](N4CCC5(CCOC5)CC4)CC3)cccc2n1CC(F)(F)F] | 4-((3-(4-(((1R,4R)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxy-benzenesulfonamide | 674.3 |
| 413A | 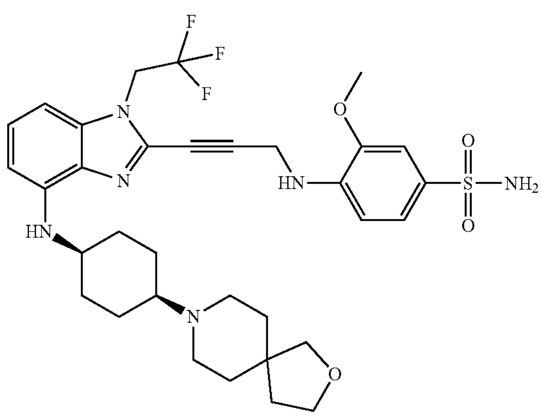 [SMILES: COc1cc(S(N)(=O)=O)ccc1NCC#Cc1nc2c(N[C@H]3CC[C@@H](N4CCC5(CCOC5)CC4)CC3)cccc2n1CC(F)(F)F] | 4-((3-(4-(((1S,4S)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxy-benzenesulfonamide | 674.3 |
| 414A | 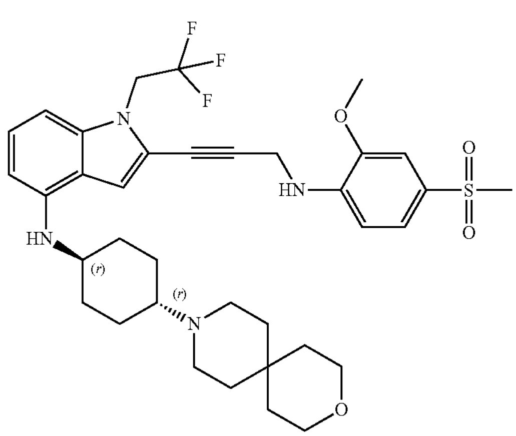 [SMILES: COc1cc(S(C)(=O)=O)ccc1NCC#Cc1cc2c(N[C@H]3CC[C@H](N4CCC5(CCOCC5)CC4)CC3)cccc2n1CC(F)(F)F] | 2-{3-[(4-methane-sulfonyl-2-methoxy-phenyl)amino]prop-1-yn-1-yl}-N-[(1R,4R)-4-{3-oxa-9-azaspiro[5.5]undecan-9-yl}cyclohexyl]-1-(2,2,2-trifluoroethyl)-1H-indol-4-amine | 687.3 |

TABLE 3-continued

| Compound No. | Structure | IUPAC | LC-MS (ES+, m/z) |
|---|---|---|---|
| 415A | 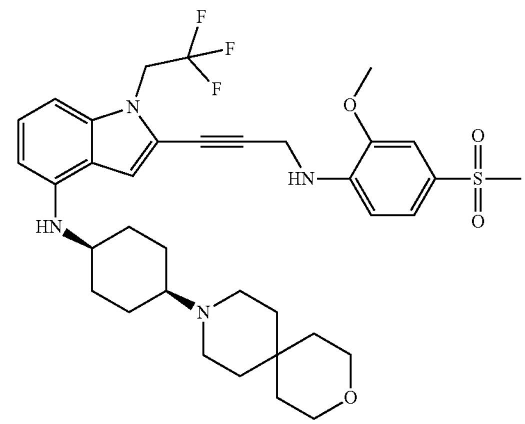 [SMILES: COc1cc(S(C)(=O)=O)ccc1NCC#Cc1cc2c(N[C@H]3CC[C@@H](N4CCC5(CCOCC5)CC4)CC3)cccc2n1CC(F)(F)F] | N-((1S,4S)-4-(3-oxa-9-azaspiro[5.5]undecan-9-yl)cyclohexyl)-2-(3-((2-methoxy-4-(methylsulfonyl)phenyl)amino)prop-1-yn-1-yl)-1-(2,2,2-trifluoroethyl)-1H-indol-4-amine | 687.3 |
| 416A | 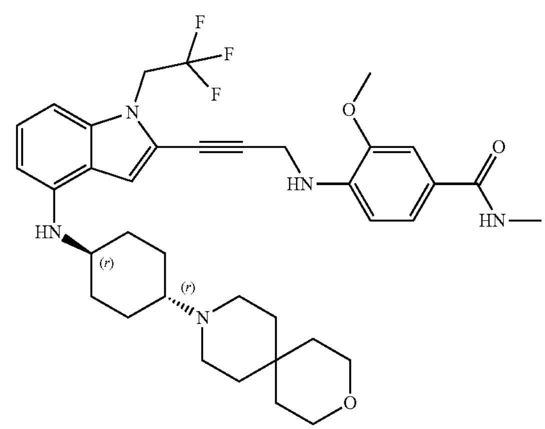 [SMILES: CNC(=O)c1ccc(NCC#Cc2cc3c(N[C@H]4CC[C@H](N5CCC6(CCOCC6)CC5)CC4)cccc3n2CC(F)(F)F)c(OC)c1] | 3-methoxy-N-methyl-4-{[3-(4-{[(1R,4R)-4-{3-oxa-9-azaspiro[5.5]undecan-9-yl}cyclohexyl]amino}-1-(2,2,2-trifluoroethyl)-1H-indol-2-yl)prop-2-yn-1-yl]amino}benzamide | 666.4 |
| 417A | 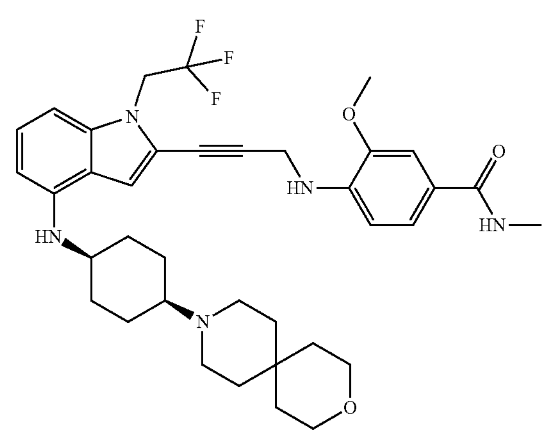 [SMILES: CNC(=O)c1ccc(NCC#Cc2cc3c(N[C@H]4CC[C@@H](N5CCC6(CCOCC6)CC5)CC4)cccc3n2CC(F)(F)F)c(OC)c1] | 4-((3-(4-(((1S,4S)-4-(3-oxa-9-azaspiro[5.5]undecan-9-yl)cyclohexyl)amino)-1-(2,2,2-trifluoroethyl)-1H-indol-2-yl)prop-2-yn-1-yl)amino)-3-methoxy-N-methylbenzamide | 666.3 |

TABLE 3-continued

| Compound No. | Structure | IUPAC | LC-MS (ES+, m/z) |
|---|---|---|---|
| 418A | 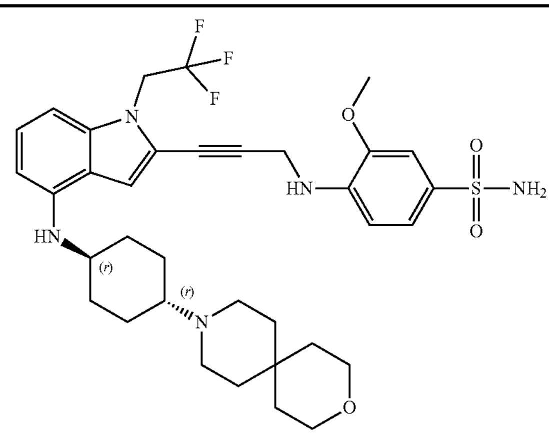 | 3-methoxy-4-{[3-(4-{[(1R,4R)-4-{3-oxa-9-azaspiro[5.5]undecan-9-yl}cyclohexyl]amino}-1-(2,2,2-trifluoroethyl)-1H-indol-2-yl)prop-2-yn-1-yl]amino}benzene-1-sulfonamide | 688.3 |
| 419A | 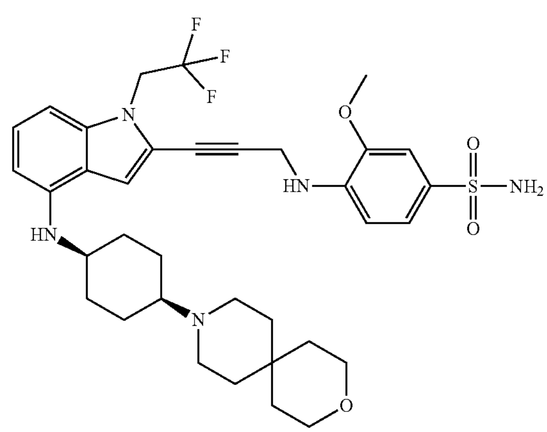 [SMILES: COc1cc(S(N)(=O)=O)ccc1NCC#Cc1cc2c(N[C@H]3CC[C@@H](N4CCC5(CCOCC5)CC4)CC3)cccc2n1CC(F)(F)F] | 4-((3-(4-(((1S,4S)-4-(3-oxa-9-azaspiro[5.5]undecan-9-yl)cyclohexyl)amino)-1-(2,2,2-trifluoroethyl)-1H-indol-2-yl)prop-2-yn-1-yl)amino)-3-methoxybenzene-sulfonamide | 688.3 |
| 420A | 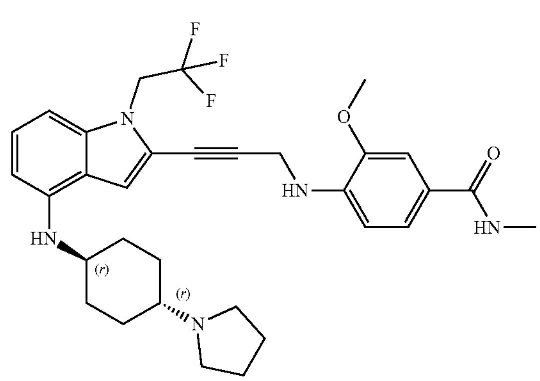 [SMILES: CNC(=O)c1ccc(NCC#Cc2cc3c(N[C@H]4CC[C@H](N5CCCC5)CC4)cccc3n2CC(F)(F)F)c(OC)c1] | 3-methoxy-N-methyl-4-{[3-(4-{[(1R,4R)-4-(pyrrolidin-1-yl)cyclohexyl]amino}-1-(2,2,2-trifluoroethyl)-1H-indol-2-yl)prop-2-yn-1-yl]amino}benzamide | 582.3 |

TABLE 3-continued

| Compound No. | Structure | IUPAC | LC-MS (ES+, m/z) |
|---|---|---|---|
| 421A | 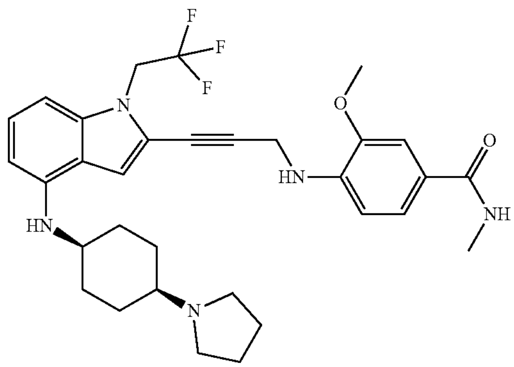 [SMILES: CNC(=O)c1ccc(NCC#Cc2cc3c(N[C@H]4CC[C@@H](N5CCCC5)CC4)cccc3n2CC(F)(F)F)c(OC)c1] | 3-methoxy-N-methyl-4-((3-(4-(((1S,4S)-4-(pyrrolidin-1-yl)cyclohexyl)amino)-1-(2,2,2-trifluoroethyl)-1H-indol-2-yl)prop-2-yn-1-yl)amino)benzamide | 582.3 |
| 422A | 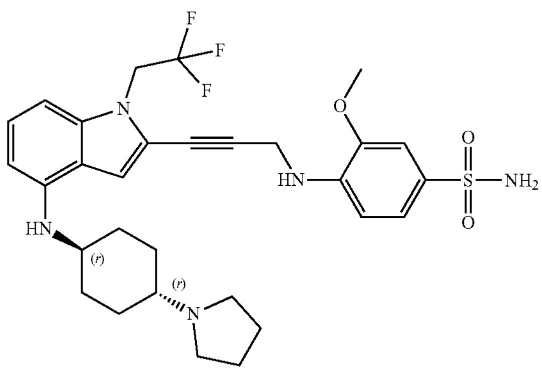 [SMILES: COc1cc(S(N)(=O)=O)ccc1NCC#Cc1cc2c(N[C@H]3CC[C@H](N4CCCC4)CC3)cccc2n1CC(F)(F)F] | 3-methoxy-4-{[3-(4-{[(1R,4R)-4-(pyrrolidin-1-yl)cyclohexyl]amino}-1-(2,2,2-trifluoroethyl)-1H-indol-2-yl)prop-2-yn-1-yl]amino}benzene-1-sulfonamide | 604.3 |
| 423A | 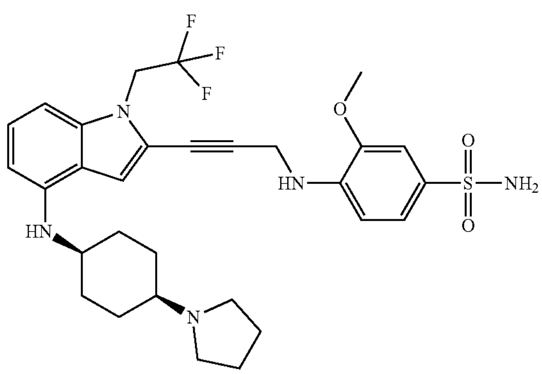 [SMILES: COc1cc(S(N)(=O)=O)ccc1NCC#Cc1cc2c(N[C@H]3CC[C@@H](N4CCCC4)CC3)cccc2n1CC(F)(F)F] | 3-methoxy-4-((3-(4-(((1S,4S)-4-(pyrrolidin-1-yl)cyclohexyl)amino)-1-(2,2,2-trifluoroethyl)-1H-indol-2-yl)prop-2-yn-1-yl)amino)benzene-sulfonamide | 604.2 |
| 424A | 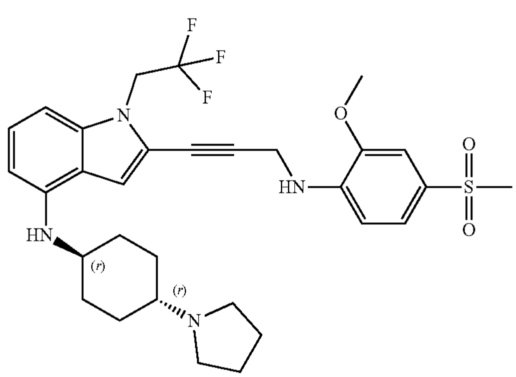 [SMILES: COc1cc(S(C)(=O)=O)ccc1NCC#Cc1cc2c(N[C@H]3CC[C@H](N4CCCC4)CC3)cccc2n1CC(F)(F)F] | 2-{3-[(4-methanesulfonyl-2-methoxyphenyl)amino]prop-1-yn-1-yl}-N-[(1R,4R)-4-(pyrrolidin-1-yl)cyclohexyl]-1-(2,2,2-trifluoroethyl)-1H-indol-4-amine | 603.2 |

TABLE 3-continued

| Compound No. | Structure | IUPAC | LC-MS (ES+, m/z) |
|---|---|---|---|
| 425A | 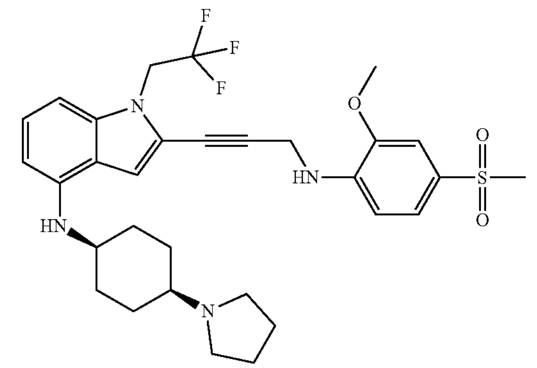 [SMILES: COc1cc(S(C)(=O)=O)ccc1NCC#Cc1cc2c(N[C@H]3CC[C@@H](N4CCCC4)CC3)cccc2n1CC(F)(F)F] | 2-(3-((2-methoxy-4-(methylsulfonyl)phenyl)amino)prop-1-yn-1-yl)-N-((1S,4S)-4-(pyrrolidin-1-yl)cyclohexyl)-1-(2,2,2-trifluoroethyl)-1H-indol-4-amine | 603.2 |
| 426A | 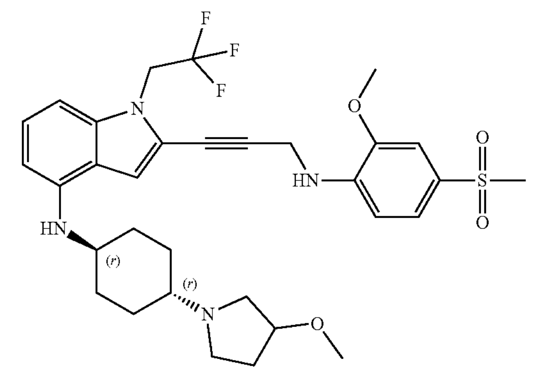 [SMILES: COc1cc(S(C)(=O)=O)ccc1NCC#Cc1cc2c(N[C@H]3CC[C@H](N4CCC(OC)C4)CC3)cccc2n1CC(F)(F)F] | 2-{3-[(4-methanesulfonyl-2-methoxyphenyl)amino]prop-1-yn-1-yl}-N-[(1R,4R)-4-(3-methoxypyrrolidin-1-yl)cyclohexyl]-1-(2,2,2-trifluoroethyl)-1H-indol-4-amine | 633.2 |
| 427A | 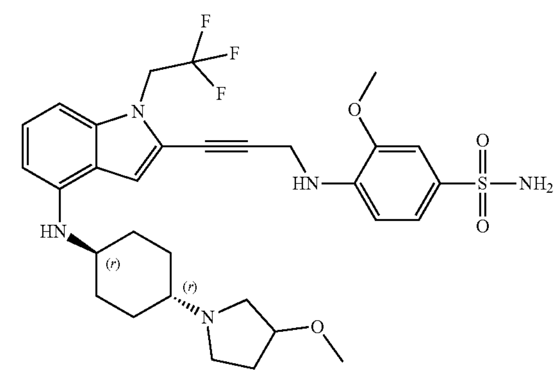 [SMILES: COc1cc(S(N)(=O)=O)ccc1NCC#Cc1cc2c(N[C@H]3CC[C@H](N4CCC(OC)C4)CC3)cccc2n1CC(F)(F)F] | 3-methoxy-4-{[3-(4-{[(1R,4R)-4-(3-methoxypyrrolidin-1-yl)cyclohexyl]amino}-1-(2,2,2-trifluoroethyl)-1H-indol-2-yl)prop-2-yn-1-yl]amino}benzene-1-sulfonamide | 634.3 |
| 428A | 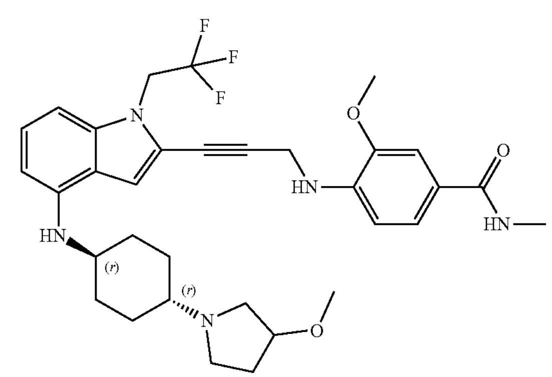 [SMILES: CNC(=O)c1ccc(NCC#Cc2cc3c(N[C@H]4CC[C@H](N5CCC(OC)C5)CC4)cccc3n2CC(F)(F)F)c(OC)c1] | 3-methoxy-N-methyl-4-{[3-(4-{[(1R,4R)-4-(3-methoxypyrrolidin-1-yl)cyclohexyl]amino}-1-(2,2,2-trifluoroethyl)-1H-indol-2-yl)prop-2-yn-1-yl]amino}benzamide | 612.3 |

TABLE 3-continued

| Compound No. | Structure | IUPAC | LC-MS (ES+, m/z) |
|---|---|---|---|
| 429A | 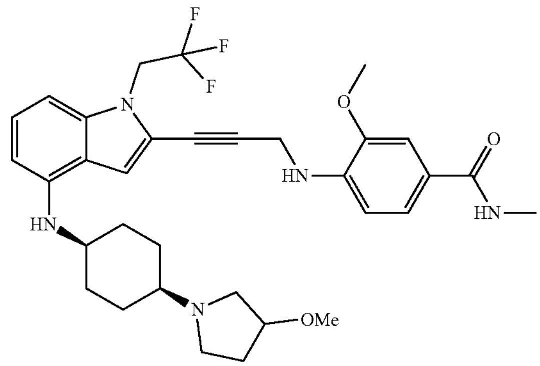 [SMILES: CNC(=O)c1ccc(NCC#Cc2cc3c(N[C@H]4CC[C@@H](N5CCC(OC)C5)CC4)cccc3n2CC(F)(F)F)c(OC)c1] | 3-methoxy-4-((3-(4-(((1S,4S)-4-(3-methoxy-pyrrolidin-1-yl)cyclo-hexyl)amino)-1-(2,2,2-trifluoroethyl)-1H-indol-2-yl)prop-2-yn-1-yl)amino)-N-methylbenzamide | 612.3 |
| 430A | 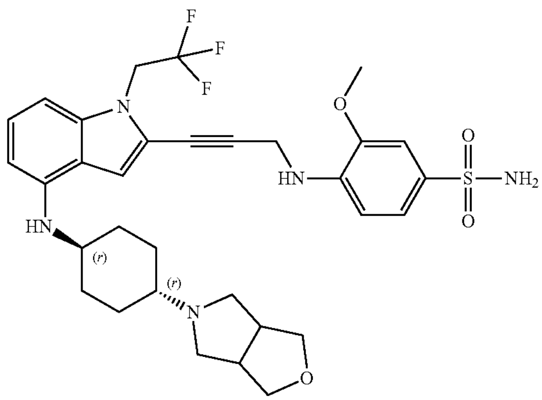 [SMILES: COc1cc(S(N)(=O)=O)ccc1NCC#Cc1cc2c(N[C@H]3CC[C@H](N4CC5COCC5C4)CC3)cccc2n1CC(F)(F)F] | 3-methoxy-4-{[3-(4-{[(1R,4R)-4-{hexahydro-1H-furo[3,4-c]pyrrol-5-yl}cyclohexyl]amino}-1-(2,2,2-trifluoroethyl)-1H-indol-2-yl)prop-2-yn-1-yl]amino}benzene-1-sulfonamide | 646.3 |
| 431A | 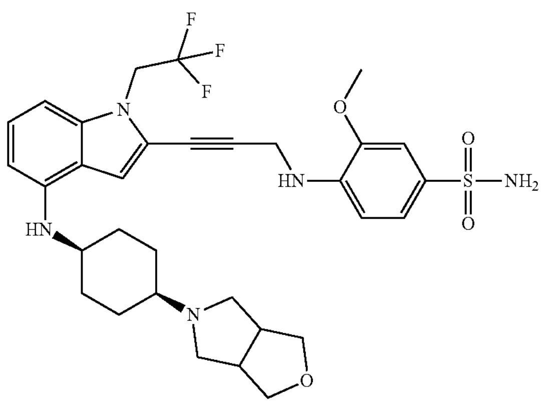 [SMILES: COc1cc(S(N)(=O)=O)ccc1NCC#Cc1cc2c(N[C@H]3CC[C@@H](N4CC5COCC5C4)CC3)cccc2n1CC(F)(F)F] | 3-methoxy-4-((3-(4-(((1S,4S)-4-(tetrahydro-1H-furo[3,4-c]pyrrol-5(3H)-yl)cyclohexyl)amino)-1-(2,2,2-trifluoroethyl)-1H-indol-2-yl)prop-2-yn-1-yl)amino)benzene-sulfonamide | 646.3 |
| 432A | 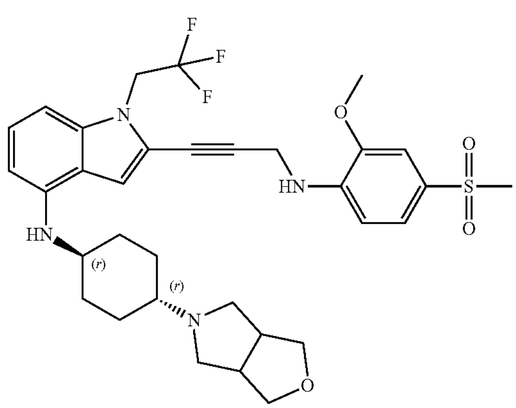 [SMILES: COc1cc(S(C)(=O)=O)ccc1NCC#Cc1cc2c(N[C@H]3CC[C@H](N4CC5COCC5C4)CC3)cccc2n1CC(F)(F)F] | 2-{3-[(4-methane-sulfonyl-2-methoxy-phenyl)amino]prop-1-yn-1-yl}-N-[(1R,4R)-4-{hexahydro-1H-furo[3,4-c]pyrrol-5-yl}cyclohexyl]-1-(2,2,2-trifluoroethyl)-1H-indol-4-amine | 645.2 |

TABLE 3-continued

| Compound No. | Structure | IUPAC | LC-MS (ES+, m/z) |
|---|---|---|---|
| 433A | 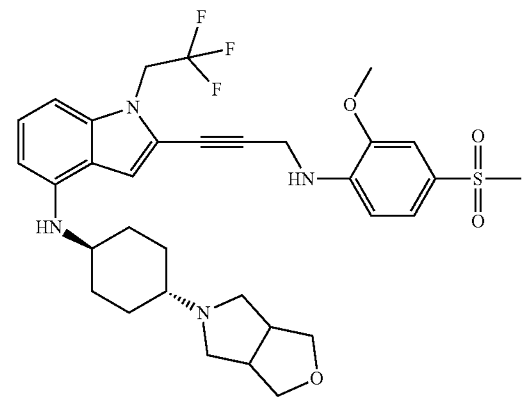 [SMILES: COc1cc(S(C)(=O)=O)ccc1NCC#Cc1cc2c(N[C@H]3CC[C@H](N4CC5COCC5C4)CC3)cccc2n1CC(F)(F)F] | 2-(3-((2-methoxy-4-(methylsulfonyl)phenyl)amino)prop-1-yn-1-yl)-N-((1R,4R)-4-(tetrahydro-1H-furo[3,4-c]pyrrol-5(3H)-yl)cyclohexyl)-1-(2,2,2-trifluoroethyl)-1H-indol-4-amine | 645.2 |
| 434A | 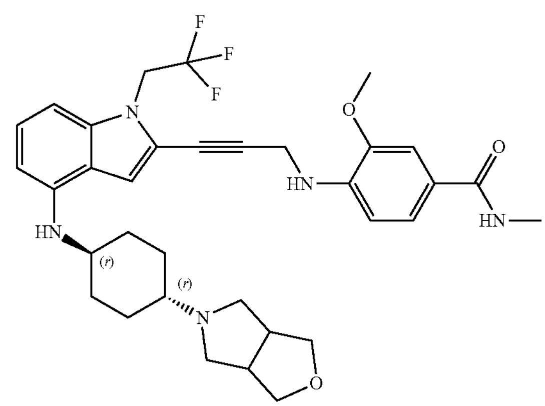 [SMILES: CNC(=O)c1ccc(NCC#Cc2cc3c(N[C@H]4CC[C@H](N5CC6COCC6C5)CC4)cccc3n2CC(F)(F)F)c(OC)c1] | 3-methoxy-N-methyl-4-{[3-(4-{[(1R,4R)-4-{hexahydro-1H-furo[3,4-c]pyrrol-5-yl}cyclohexyl]amino}-1-(2,2,2-trifluoroethyl)-1H-indol-2-yl)prop-2-yn-1-yl]amino}benzamide | 624.3 |
| 435A | 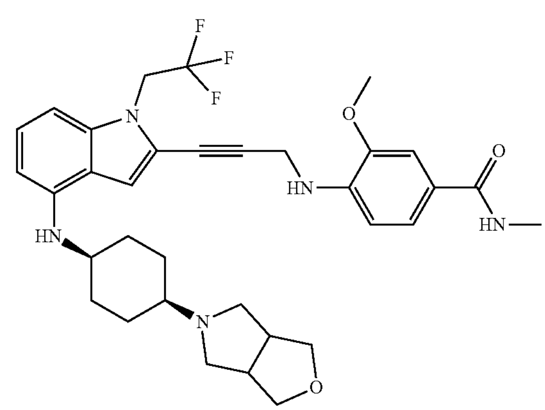 [SMILES: CNC(=O)c1ccc(NCC#Cc2cc3c(N[C@H]4CC[C@@H](N5CC6COCC6C5)CC4)cccc3n2CC(F)(F)F)c(OC)c1] | 3-methoxy-N-methyl-4-((3-(4-(((1S,4S)-4-(tetrahydro-1H-furo[3,4-c]pyrrol-5(3H)-yl)cyclohexyl)amino)-1-(2,2,2-trifluoroethyl)-1H-indol-2-yl)prop-2-yn-1-yl)amino)benzamide | 624.4 |

TABLE 3-continued

| Compound No. | Structure | IUPAC | LC-MS (ES+, m/z) |
|---|---|---|---|
| 436A | 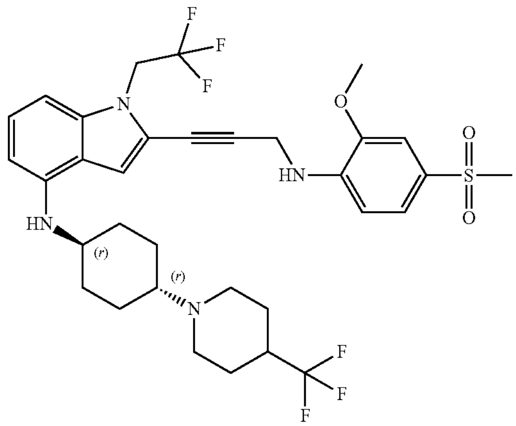 [SMILES: COc1cc(S(C)(=O)=O)ccc1NCC#Cc1cc2c(N[C@H]3CC[C@H](N4CCC(C(F)(F)F)CC4)CC3)cccc2n1CC(F)(F)F] | 2-{3-[(4-methane-sulfonyl-2-methoxy-phenyl)amino]prop-1-yn-1-yl}-N-[(1R,4R)-4-[4-(trifluoromethyl)piperidin-1-yl]cyclohexyl]-1-(2,2,2-trifluoroethyl)-1H-indol-4-amine | 685.2 |
| 437A | 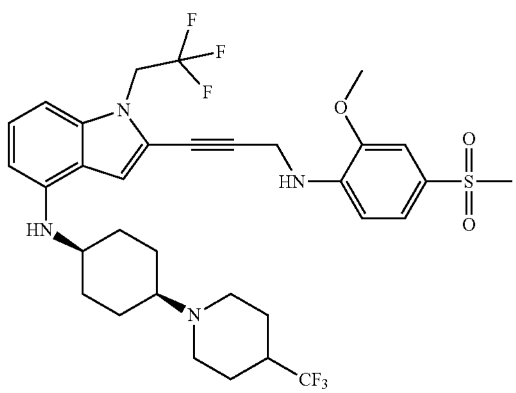 [SMILES: COc1cc(S(C)(=O)=O)ccc1NCC#Cc1cc2c(N[C@H]3CC[C@@H](N4CCC(C(F)(F)F)CC4)CC3)cccc2n1CC(F)(F)F] | 2-(3-((2-methoxy-4-(methylsulfonyl)phenyl)amino)prop-1-yn-1-yl)-1-(2,2,2-trifluoroethyl)-N-((1S,4S)-4-(4-(trifluoromethyl)piperidin-1-yl)cyclohexyl)-1H-indol-4-amine | 685.2 |
| 438A | 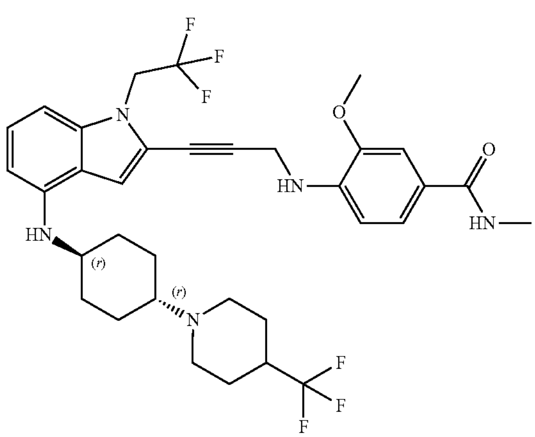 [SMILES: CNC(=O)c1ccc(NCC#Cc2cc3c(N[C@H]4CC[C@H](N5CCC(C(F)(F)F)CC5)CC4)cccc3n2CC(F)(F)F)c(OC)c1] | 3-methoxy-N-methyl-4-{[3-(4-{[(1R,4R)-4-[4-(trifluoromethyl)piperidin-1-yl]cyclohexyl]amino}-1-(2,2,2-trifluoroethyl)-1H-indol-2-yl)prop-2-yn-1-yl]amino}benzamide | 664.3 |

TABLE 3-continued

| Compound No. | Structure | IUPAC | LC-MS (ES+, m/z) |
|---|---|---|---|
| 439A | 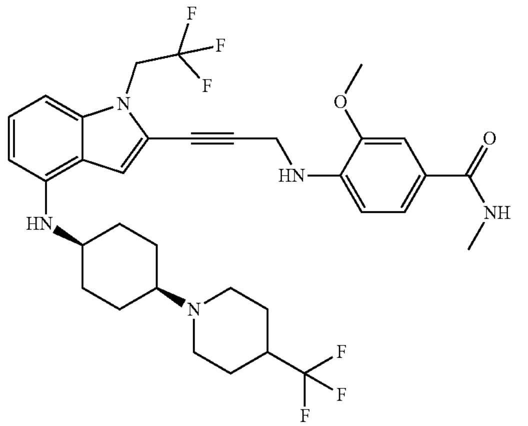 [SMILES: CNC(=O)c1ccc(NCC#Cc2cc3c(N[C@H]4CC[C@@H](N5CCC(C(F)(F)F)CC5)CC4)cccc3n2CC(F)(F)F)c(OC)c1] | 3-methoxy-N-methyl-4-((3-(1-(2,2,2-trifluoroethyl)-4-(((1S,4S)-4-(4-(trifluoromethyl)piperidin-1-yl)cyclohexyl)amino)-1H-indol-2-yl)prop-2-yn-1-yl)amino)benzamide | 664.2 |
| 440A | 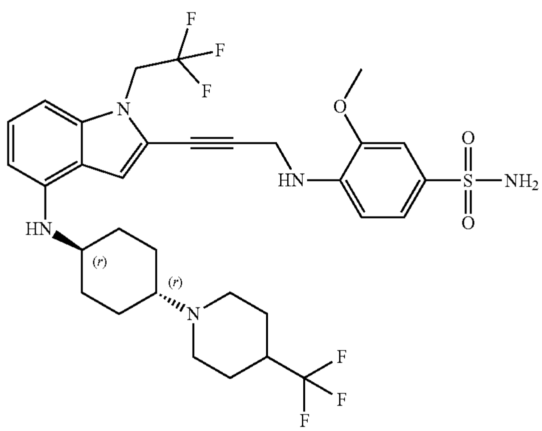 [SMILES: COc1cc(S(N)(=O)=O)ccc1NCC#Cc1cc2c(N[C@H]3CC[C@H](N4CCC(C(F)(F)F)CC4)CC3)cccc2n1CC(F)(F)F] | 3-methoxy-4-{[3-(4-{[(1R,4R)-4-[4-(trifluoromethyl)piperidin-1-yl]cyclohexyl]amino}-1-(2,2,2-trifluoroethyl)-1H-indol-2-yl)prop-2-yn-1-yl]amino}benzene-1-sulfonamide | 686.2 |
| 441A | 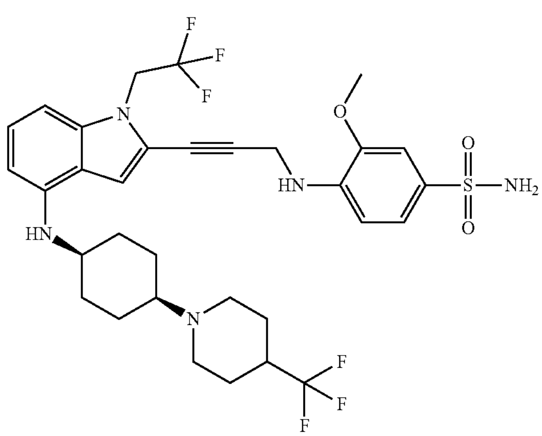 [SMILES: COc1cc(S(N)(=O)=O)ccc1NCC#Cc1cc2c(N[C@H]3CC[C@@H](N4CCC(C(F)(F)F)CC4)CC3)cccc2n1CC(F)(F)F] | 3-methoxy-4-((3-(1-(2,2,2-trifluoroethyl)-4-(((1S,4S)-4-(4-(trifluoromethyl)piperidin-1-yl)cyclohexyl)amino)-1H-indol-2-yl)prop-2-yn-1-yl)amino)benzenesulfonamide | 686.2 |

TABLE 3-continued

| Compound No. | Structure | IUPAC | LC-MS (ES+, m/z) |
|---|---|---|---|
| 442A | 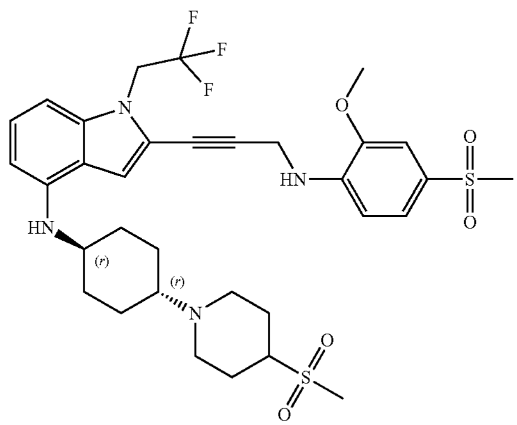 [SMILES: COc1cc(S(C)(=O)=O)ccc1NCC#Cc1cc2c(N[C@H]3CC[C@H](N4CCC(S(C)(=O)=O)CC4)CC3)cccc2n1CC(F)(F)F] | 2-{3-[(4-methane-sulfonyl-2-methoxy-phenyl)amino]prop-1-yn-1-yl}-N-[(1R,4R)-4-(4-methanesulfonylpiperidin-1-yl)cyclohexyl]-1-(2,2,2-trifluoroethyl)-1H-indol-4-amine | 695.2 |
| 443A | 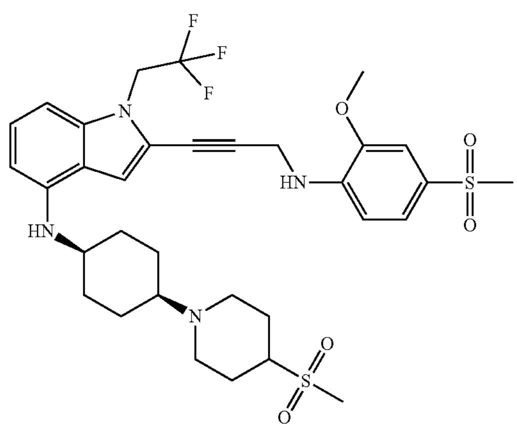 [SMILES: COc1cc(S(C)(=O)=O)ccc1NCC#Cc1cc2c(N[C@H]3CC[C@@H](N4CCC(S(C)(=O)=O)CC4)CC3)cccc2n1CC(F)(F)F] | 2-(3-((2-methoxy-4-(methylsulfonyl)phenyl)amino)prop-1-yn-1-yl)-N-((1S,4S)-4-(4-(methylsulfonyl)piperidin-1-yl)cyclohexyl)-1-(2,2,2-trifluoroethyl)-1H-indol-4-amine | 695.2 |
| 444A | 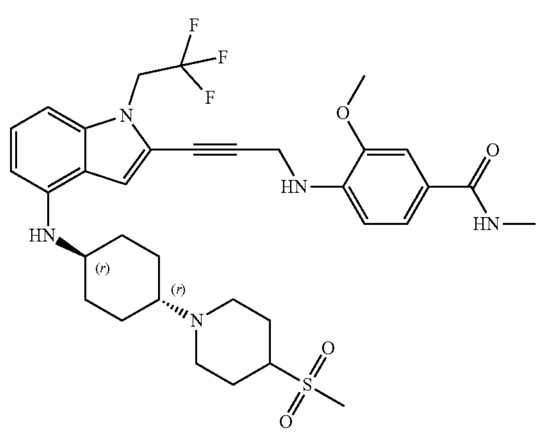 [SMILES: CNC(=O)c1ccc(NCC#Cc2cc3c(N[C@H]4CC[C@H](N5CCC(S(C)(=O)=O)CC5)CC4)cccc3n2CC(F)(F)F)c(OC)c1] | 3-methoxy-N-methyl-4-{[3-(4-{[(1R,4R)-4-(4-methane-sulfonylpiperidin-1-yl)cyclohexyl]amino}-1-(2,2,2-trifluoroethyl)-1H-indol-2-yl)prop-2-yn-1-yl]amino}benzamide | 674.3 |

TABLE 3-continued

| Compound No. | Structure | IUPAC | LC-MS (ES+, m/z) |
|---|---|---|---|
| 445A | 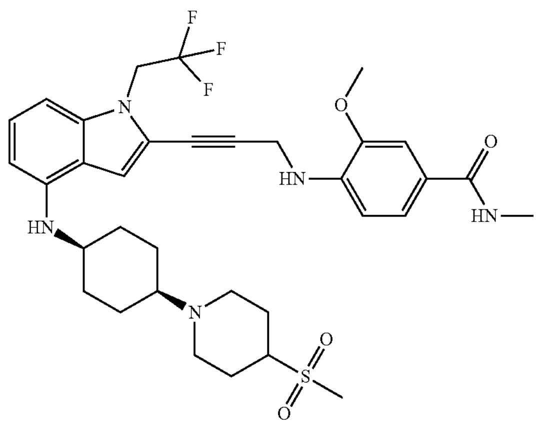 [SMILES: CNC(=O)c1ccc(NCC#Cc2cc3c(N[C@H]4CC[C@@H](N5CCC(S(C)(=O)=O)CC5)CC4)cccc3n2CC(F)(F)F)c(OC)c1] | 3-methoxy-N-methyl-4-((3-(4-(((1S,4S)-4-(4-(methylsulfonyl)piperidin-1-yl)cyclohexyl)amino)-1-(2,2,2-trifluoroethyl)-1H-indol-2-yl)prop-2-yn-1-yl)amino)benzamide | 674.3 |
| 446A | 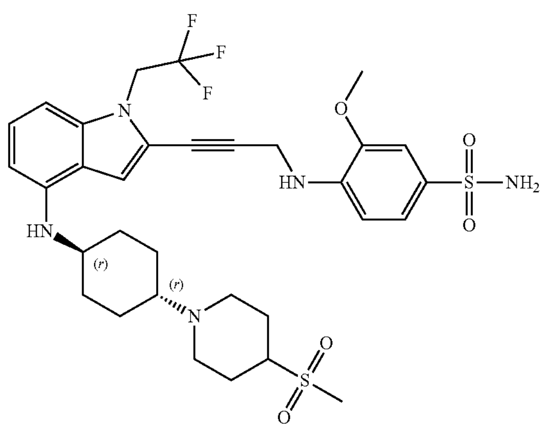 [SMILES: COc1cc(S(N)(=O)=O)ccc1NCC#Cc1cc2c(N[C@H]3CC[C@H](N4CCC(S(C)(=O)=O)CC4)CC3)cccc2n1CC(F)(F)F] | 3-methoxy-4-{[3-(4-{[(1R,4R)-4-(4-methanesulfonyl-piperidin-1-yl)cyclo-hexyl]amino}-1-(2,2,2-trifluoroethyl)-1H-indol-2-yl)prop-2-yn-1-yl]amino}benzene-1-sulfonamide | 696.2 |
| 447A | 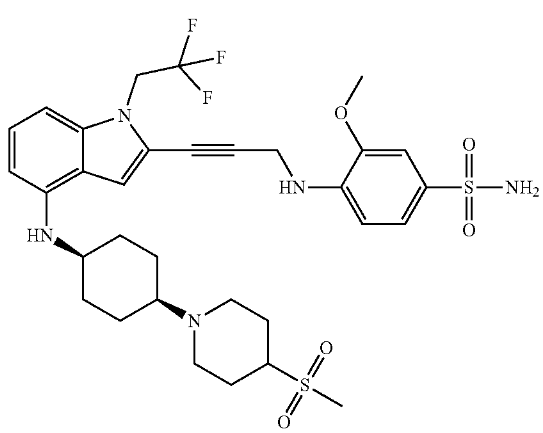 [SMILES: COc1cc(S(N)(=O)=O)ccc1NCC#Cc1cc2c(N[C@H]3CC[C@@H](N4CCC(S(C)(=O)=O)CC4)CC3)cccc2n1CC(F)(F)F] | 3-methoxy-4-((3-(4-(((1S,4S)-4-(4-(methyl-sulfonyl)piperidin-1-yl)cyclohexyl)amino)-1-(2,2,2-trifluoroethyl)-1H-indol-2-yl)prop-2-yn-1-yl)amino)benzenesulfonamide | 696.2 |

TABLE 3-continued

| Compound No. | Structure | IUPAC | LC-MS (ES+, m/z) |
|---|---|---|---|
| 448A | 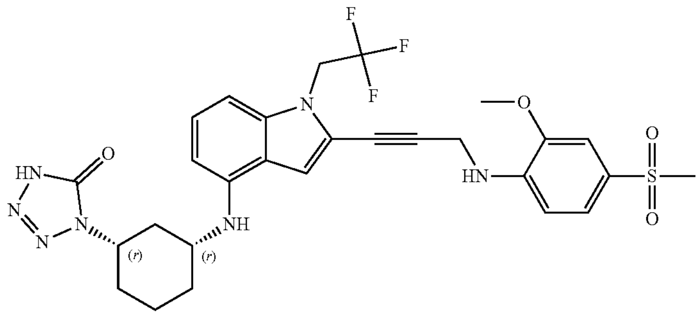 [SMILES: COc1cc(S(C)(=O)=O)ccc1NCC#Cc1cc2c(N[C@@H]3CCC[C@H](n4nn[nH]c4=O)C3)cccc2n1CC(F)(F)F] | 1-[(1S,3R)-3-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-4,5-dihydro-1H-1,2,3,4-tetrazol-5-one | 618.9 |
| 449A | 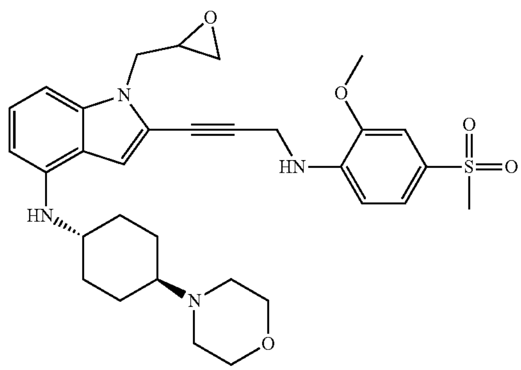 [SMILES: COc1cc(S(C)(=O)=O)ccc1NCC#Cc1cc2c(N[C@H]3CC[C@H](N4CCOCC4)CC3)cccc2n1CC1CO1] | 2-(3-((2-methoxy-4-(methylsulfonyl)phenyl)amino)prop-1-yn-1-yl)-N-((1R,4R)-4-morpholinocyclohexyl)-1-(oxiran-2-ylmethyl)-1H-indol-4-amine | |
| 450A | 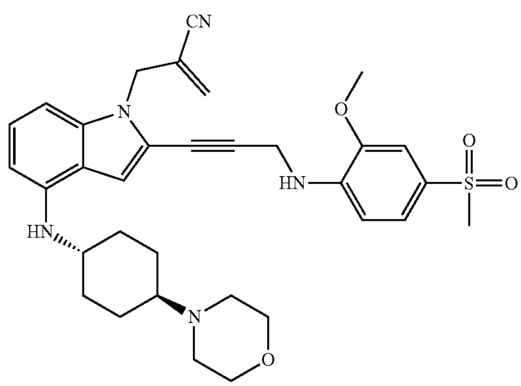 [SMILES: C=C(C#N)Cn1c(C#CCNc2ccc(S(C)(=O)=O)cc2OC)cc2c(N[C@H]3CC[C@H](N4CCOCC4)CC3)cccc21] | 2-((2-(3-((2-methoxy-4-(methylsulfonyl)phenyl)amino)prop-1-yn-1-yl)-4-(((1R,4R)-4-morpholinocyclohexyl)amino)-1H-indol-1-yl)methyl)acrylonitrile | |
| 451A | 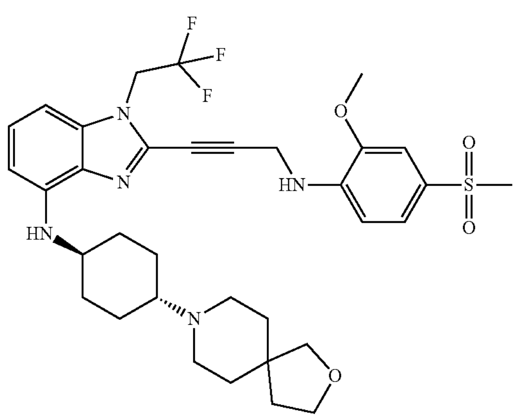 [SMILES: COc1cc(S(C)(=O)=O)ccc1NCC#Cc1nc2c(N[C@H]3CC[C@H](N4CCC5(CCOC5)CC4)CC3)cccc2n1CC(F)(F)F] | N-((1R,4R)-4-(2-oxa-8-azaspiro[4.5]decan-8-yl)cyclohexyl)-2-(3-((2-methoxy-4-(methylsulfonyl)phenyl)amino)prop-1-yn-1-yl)-1-(2,2,2-trifluoroethyl)-1H-benzo[d]imidazol-4-amine | 673.3 |

TABLE 3-continued

| Compound No. | Structure | IUPAC | LC-MS (ES+, m/z) |
|---|---|---|---|
| 452A | 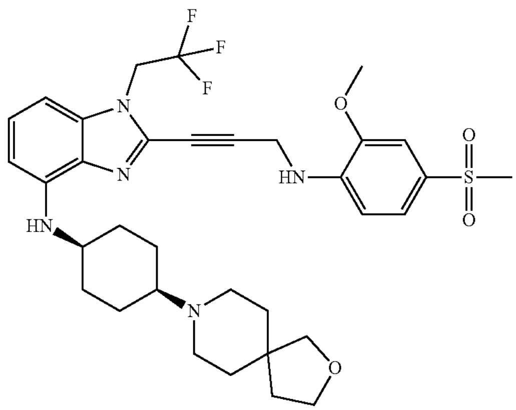 [SMILES: COc1cc(S(C)(=O)=O)ccc1NCC#Cc1nc2c(N[C@H]3CC[C@@H](N4CCC5(CCOC5)CC4)CC3)cccc2n1CC(F)(F)F] | N-((1S,4S)-4-(2-oxa-8-azaspiro[4.5]decan-8-yl)cyclohexyl)-2-(3-((2-methoxy-4-(methylsulfonyl)phenyl)amino)prop-1-yn-1-yl)-1-(2,2,2-trifluoroethyl)-1H-benzo[d]imidazol-4-amine | 673.3 |
| 453A | 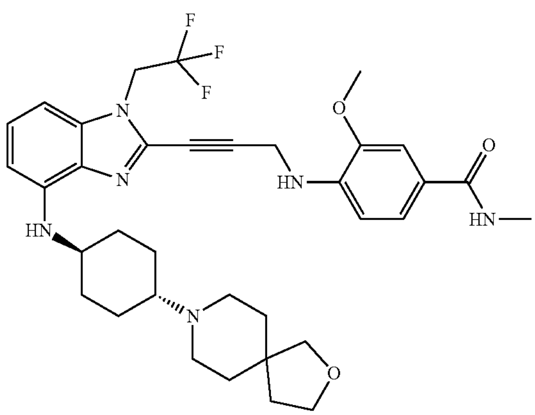 [SMILES: CNC(=O)c1ccc(NCC#Cc2nc3c(N[C@H]4CC[C@H](N5CCC6(CCOC6)CC5)CC4)cccc3n2CC(F)(F)F)c(OC)c1] | 4-((3-(4-(((1R,4R)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxy-N-methylbenzamide | 652.3 |
| 454A | 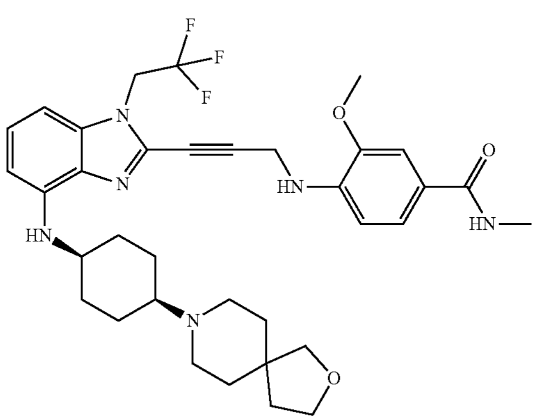 [SMILES: CNC(=O)c1ccc(NCC#Cc2nc3c(N[C@H]4CC[C@@H](N5CCC6(CCOC6)CC5)CC4)cccc3n2CC(F)(F)F)c(OC)c1] | 4-((3-(4-(((1S,4S)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxy-N-methylbenzamide | 652.3 |

D. Compounds with 2-ethynyl-N—(N-heterocyclyl)-1H-indole-4-amine Core

Example D1: Synthesis of 2-(3-((4-methoxypyridin-3-yl)amino)prop-1-yn-1-yl)-N-(1-methylpiperidin-4-yl)-1-(2,2,2-trifluoroethyl)-1H-indol-4-amine (Compound 527A)

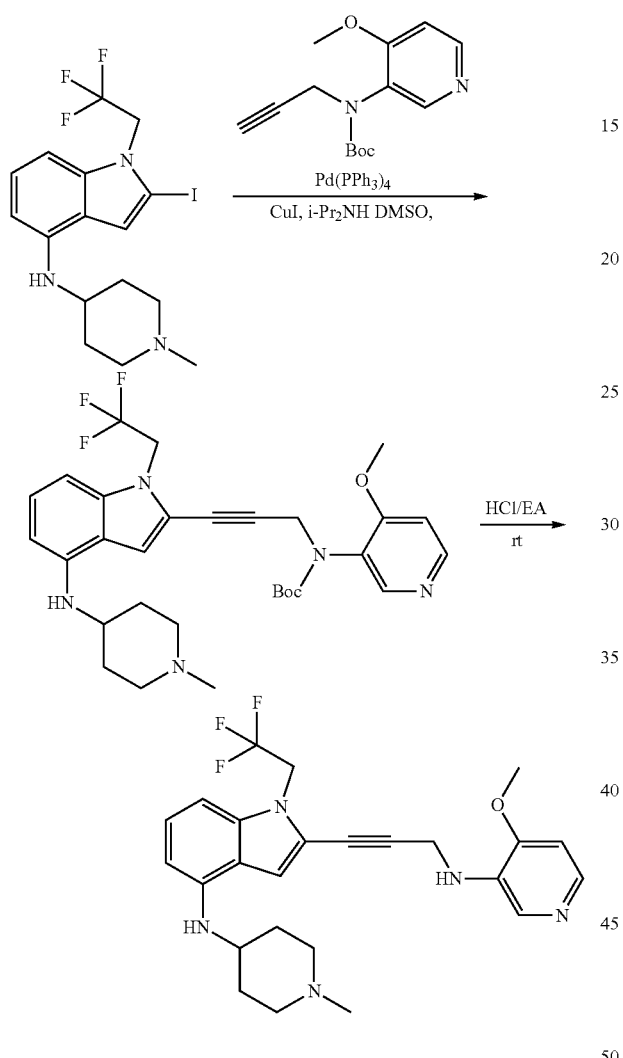

Preparation of tert-butyl (4-methoxypyridin-3-yl)(3-(4-((1-methylpiperidin-4-yl)amino)-1-(2,2,2-trifluoroethyl)-1H-indol-2-yl)prop-2-yn-1-yl)carbamate: To a solution of 2-iodo-N-(1-methyl-4-piperidyl)-1-(2,2,2-trifluoroethyl)indol-4-amine (80 mg, 183 µmol, 1 eq.) in DMSO (3 mL) were added tert-butyl N-(4-methoxy-3-pyridyl)-N-prop-2-ynylcarbamate (96.0 mg, 366 µmol, 2 eq.), CuI (34.9 mg, 183 µmol, 1 eq.), Pd(PPh$_3$)$_4$ (21.1 mg, 18.3 µmol, 0.10 eq.), and N-isopropylpropan-2-amine (1.10 mmol, 154.3 µL, 6 eq.). The mixture was stirred at 40° C. for 2 h. The reaction mixture was partitioned by adding a saturated EDTA solution (20 mL). The mixture was stirred for 2 h, and EtOAc was added to the mixture (20 mL). The organic phase was separated, washed with water (10 mL), dried over anhydrous sodium sulfate, filtered, and concentrated under reduced pressure. The crude residue was purified by prep-TLC to afford tert-butyl N-(4-methoxy-3-pyridyl)-N-[3-[4-[(1-methyl-4-piperidyl)amino]-1-(2,2,2-trifluoroethyl)indol-2-yl]prop-2-ynyl]carbamate (70 mg, 122.5 µmol, 66.9% yield) as a dark yellow solid. MS (ES$^+$, m/z): 572.2.

Preparation of 2-[3-[(4-methoxy-3-pyridyl)amino]prop-1-ynyl]-N-(1-methyl-4-piperidyl)-1-(2,2,2-trifluoroethyl)indol-4-amine: To a solution of tert-butyl N-(4-methoxy-3-pyridyl)-N-[3-[4-[(1-methyl-4-piperidyl)amino]-1-(2,2,2-trifluoroethyl)indol-2-yl]prop-2-ynyl]carbamate (40 mg, 70.0 µmol, 1 eq.) in EtOAc (2 mL) was added HCl/EtOAc (4 M, 4 mL, 1 eq.). The mixture was stirred at 25° C. for 2 h. TLC analysis showed that the starting material was consumed, and one new spot corresponding to the desired product was detected. The reaction mixture was concentrated under reduced pressure and purified by prep-HPLC to afford 2-[3-[(4-methoxy-3-pyridyl)amino]prop-1-ynyl]-N-(1-methyl-4-piperidyl)-1-(2,2,2-trifluoroethyl)indol-4-amine (9.8 mg, 20.6 µmol, 29.5% yield) as a white solid. MS (ES$^+$, m/z): 472.2.

Example D2: Synthesis of 2-{3-[(5-fluoro-4-methanesulfonyl-2-methoxyphenyl)amino]prop-1-yn-1-yl}-N-(1-methylpiperidin-4-yl)-1-(2,2,2-trifluoroethyl)-1H-indol-4-amine (Compound 522A).

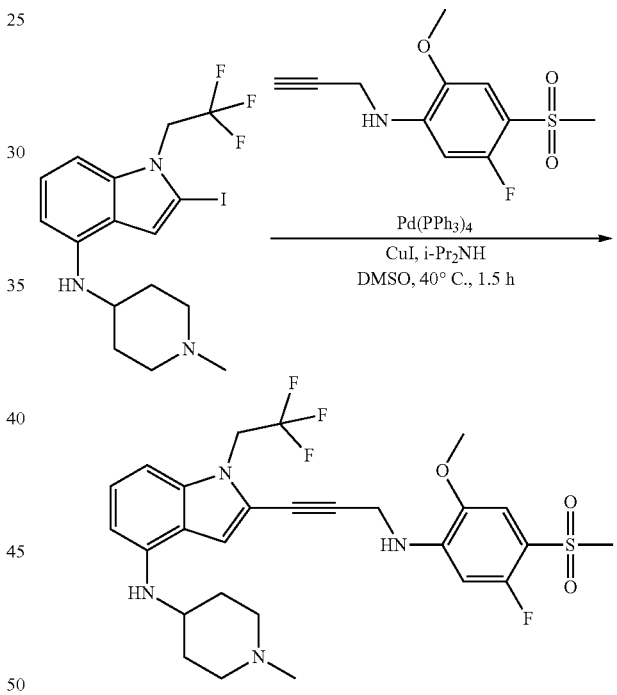

A mixture of 5-fluoro-2-methoxy-4-(methylsulfonyl)-N-(prop-2-yn-1-yl)aniline (90.2 mg, 315.6 µmol, 3 eq.) in DMSO (2 mL) were added i-Pr$_2$NH (1.05 mmol, 150 µL, 10 eq.), CuI (10.0 mg, 52.6 µmol, 0.5 eq.), 2-iodo-N-(1-methylpiperidin-4-yl)-1-(2,2,2-trifluoroethyl)-1H-indol-4-amine (50 mg, 105.2 µmol, 1 eq.), and Pd(PPh$_3$)$_4$ (2.43 mg, 2.10 µmol, 0.02 eq.). The mixture was stirred at 40° C. for 1.5 h under N$_2$. TLC analysis (PE:EtOAc:TEA=100:100:1, R$_f$=0.5) indicated that 50% of the starting material remained, and one major new spot with polarity greater than that of the starting material was detected. The reaction mixture was poured into a saturated EDTA solution (50 mL), and the resulting mixture was stirred at 25° C. for 1 h. The mixture was extracted with EtOAc (90 mL×3). The combined organic layers were washed with brine (90 mL×3), dried over anhydrous sodium sulfate, filtered, and concentrated under reduced pressure. The crude residue was purified by prep-TLC (PE:EtOAc:DCM:MeOH=10:10:10:1, $R_f$=0.5) and prep-HPLC to afford 2-{3-[(5-fluoro-4-methanesulfonyl-2-methoxyphenyl)amino]prop-1-yn-1-yl}-N-(1-methylpiperidin-4-yl)-1-(2,2,2-trifluoroethyl)-1H-indol-4-amine (19.6 mg, 33.5 μmol, 37.1% yield) as a light yellow solid. MS (ES$^+$, m/z): 567.2.

Example D3: Synthesis of Compounds 537A and 538A

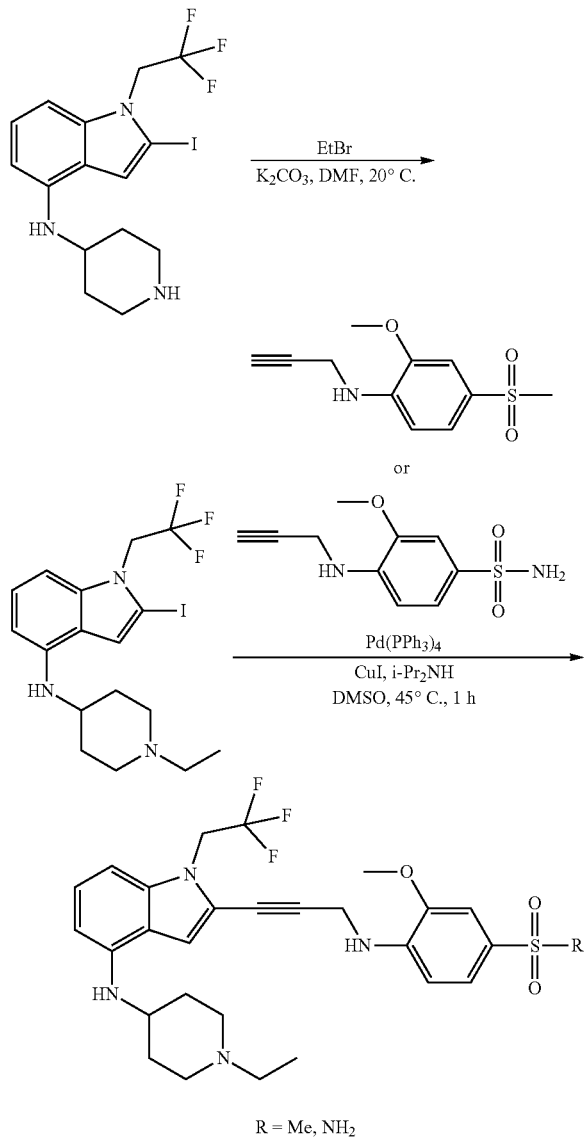

Synthesis of N-(1-ethylpiperidin-4-yl)-2-iodo-1-(2,2,2-trifluoroethyl)-1H-indol-4-amine: To a solution of 2-iodo-N-(piperidin-4-yl)-1-(2,2,2-trifluoroethyl)-1H-indol-4-amine (150 mg, 1 eq.) in DMF (1 mL) was added $K_2CO_3$ (147 mg, 1.06 mmol, 3 eq.). Bromoethane (53 μL, 2 eq.) was then added to the mixture, and the reaction mixture was stirred at 25° C. for 3 h. TLC analysis in MeOH indicated that the starting material was consumed completely, and one new spot had formed. The reaction mixture was diluted with water (40 mL) and extracted with EtOAc (15 mL×3). The combined organic layers were washed with brine (10 mL), dried over anhydrous sodium sulfate, filtered, and concentrated in vacuo to afford crude N-(1-ethylpiperidin-4-yl)-2-iodo-1-(2,2,2-trifluoroethyl)-1H-indol-4-amine (150 mg) as a brown solid.

Representative procedure for Sonogashira coupling reaction: To a mixture of N-(1-ethyl-4-piperidyl)-2-iodo-1-(2,2,2-trifluoroethyl)indol-4-amine (150 mg, 266 μmol, 1 eq) and 2-methoxy-4-methylsulfonyl-N-prop-2-ynyl-aniline (159.1 mg, 531.8 μmol, 2 eq.) in DMSO (3 mL) were added N-isopropylpropan-2-amine (266 μmol, 38 μL, 1 eq.) and Pd(PPh$_3$)$_4$ (6.2 mg, 5.3 μmol, 0.02 eq.) followed by CuI (50.6 mg, 266 μmol, 1 eq.) under $N_2$. The reaction mixture was stirred for 1 h at 45° C. LC-MS analysis showed that the reaction was complete. The mixture was poured into a saturated aqueous EDTA solution (20 mL) and stirred for 1 h. The aqueous phase was extracted with EtOAc (10 mL×3). The combined organic layers were washed with brine (10 mL), dried over anhydrous sodium sulfate, filtered, and concentrated under reduced pressure to give a residue. The residue was purified by prep-TLC (SiO$_2$, PE:EtOAc=1:1) and prep-HPLC to give the desired product (17.8 mg, 30.9 μmol, 11.6% yield). N-(1-ethylpiperidin-4-yl)-2-{3-[(4-methanesulfonyl-2-methoxyphenyl)amino]prop-1-yn-1-yl}-1-(2,2,2-trifluoroethyl)-1H-indol-4-amine, MS (ES$^+$, m/z): 563.2; and 4-[(3-{4-[(1-ethylpiperidin-4-yl)amino]-1-(2,2,2-trifluoroethyl)-1H-indol-2-yl}prop-2-yn-1-yl)amino]-3-methoxybenzene-1-sulfonamide, MS (ES$^+$, m/z): 564.2.

Example D3: Synthesis of 2-{3-[(4-methanesulfonyl-2-methoxyphenyl)amino]prop-1-yn-1-yl}-N-[1-(propan-2-yl)piperidin-4-yl]-1-(2,2,2-trifluoroethyl)-1H-indol-4-amine (Compound 542A)

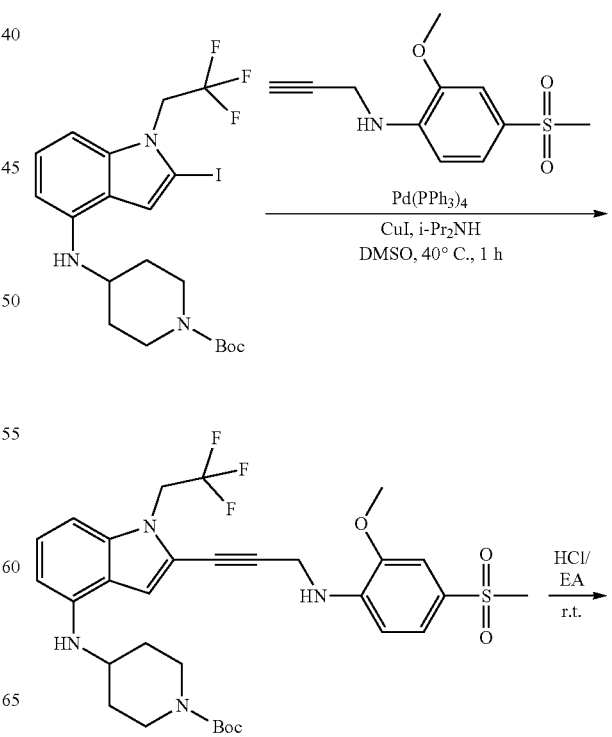

-continued

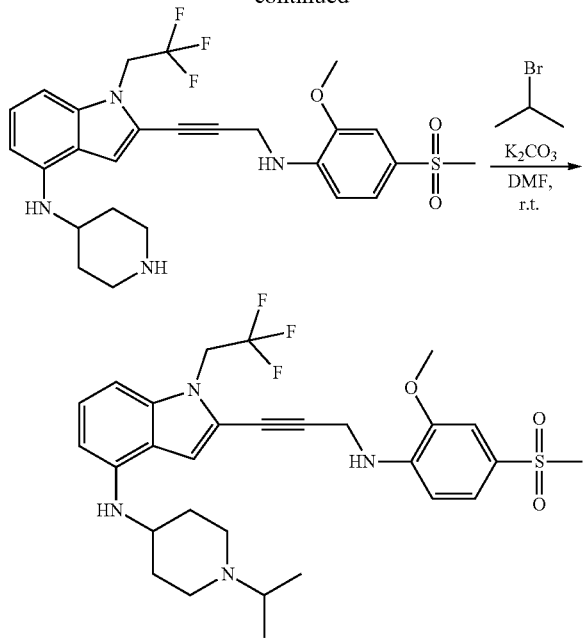

Synthesis of tert-butyl 4-((2-(3-((2-methoxy-4-(methylsulfonyl)phenyl)amino)prop-1-yn-1-yl)-1-(2,2,2-trifluoroethyl)-1H-indol-4-yl)amino)piperidine-1-carboxylate: To a solution of 2-methoxy-4-(methylsulfonyl)-N-(prop-2-yn-1-yl)aniline (1.92 g, 8.03 mmol, 1.2 eq.) in DMSO (70 mL) were added i-Pr$_2$NH (6.77 g, 66.9 mmol, 9.45 mL, 10 eq.), CuI (382.1 mg, 2.01 mmol, 0.3 eq.), tert-butyl 4-((2-iodo-1-(2,2,2-trifluoroethyl)-1H-indol-4-yl)amino)piperidine-1-carboxylate (3.5 g, 6.69 mmol, 1 eq.), and Pd(PPh$_3$)$_4$ (772.8 mg, 669 µmol, 0.1 eq.). The resulting mixture was stirred for 1 h at 40° C. under N$_2$. TLC analysis showed that the reaction was complete. The reaction mixture was diluted with EtOAc (500 mL) and an 2M aqueous EDTA solution (500 mL) and stirred further at 20° C. for 1 h. The mixture was extracted with EtOAc (500 mL×3), washed with brine (500 mL), dried over anhydrous sodium sulfate, and concentrated under reduced pressure to give the crude product. The crude residue was purified by column chromatography (SiO$_2$, PE:EtOAc=4:1 to 1:0) to afford tert-butyl 4-((2-(3-((2-methoxy-4-(methylsulfonyl)phenyl)amino)prop-1-yn-1-yl)-1-(2,2,2-trifluoroethyl)-1H-indol-4-yl)amino)piperidine-1-carboxylate (9 g, 14.18 mmol) as a yellow solid.

Synthesis of 2-(3-((2-methoxy-4-(methylsulfonyl)phenyl)amino)prop-1-yn-1-yl)-N-(piperidin-4-yl)-1-(2,2,2-trifluoroethyl)-1H-indol-4-amine: The solution of tert-butyl 4-((2-(3-((2-methoxy-4-(methylsulfonyl)phenyl)amino)prop-1-yn-1-yl)-1-(2,2,2-trifluoroethyl)-1H-indol-4-yl)amino)piperidine-1-carboxylate (3 g, 4.73 mmol, 1 eq.) in EtOAc (20 mL) was added HCl/EtOAc (4 M, 60 mL, 50.78 eq.). The resulting mixture was stirred for 1 h at 25° C. under N$_2$. TLC analysis showed that the reaction was complete. The reaction was quenched with saturated aqueous NaHCO$_3$ (200 mL), and the mixture was extracted with EtOAc (200 mL×3). The combined organic layers were washed with brine (200 mL×2), dried over anhydrous sodium sulfate, filtered, and concentrated in vacuo. The residue was purified by column chromatography (SiO$_2$, PE:EtOAc=1:1 to 5% TEA in EtOAc) to afford 2-(3-((2-methoxy-4-(methylsulfonyl)phenyl)amino)prop-1-yn-1-yl)-N-(piperidin-4-yl)-1-(2,2,2-trifluoroethyl)-1H-indol-4-amine (6.6 g, 12.1 mmol) as a black-brown solid.

1H NMR (400 MHz, DMSO-d6) δ ppm 7.39 (dd, J=8.38, 1.90 Hz, 1H) 7.26 (d, J=1.96 Hz, 1H) 7.13 (s, 1H) 7.01 (t, J=7.49 Hz, 1H) 6.89 (d, J=8.44 Hz, 1H) 6.72 (d, J=8.31 Hz, 1H) 6.50 (t, J=6.24 Hz, 1H) 6.21 (d, J=7.82 Hz, 1H) 5.69 (d, J=7.95 Hz, 1H) 4.94 (q, J=9.05 Hz, 2H) 4.36 (d, J=6.24 Hz, 2H) 3.88-4.08 (m, 3H) 3.49-3.64 (m, 1H) 3.08-3.27 (m, 5H) 2.81-3.06 (m, 2H) 1.96-2.06 (m, 2H) 1.48-1.64 (m, 2H).

Synthesis of N-(1-isopropylpiperidin-4-yl)-2-(3-((2-methoxy-4-(methylsulfonyl)phenyl)amino)prop-1-yn-1-yl)-1-(2,2,2-trifluoroethyl)-1H-indol-4-amine: To a solution of 2-(3-((2-methoxy-4-(methylsulfonyl)phenyl)amino)prop-1-yn-1-yl)-N-(piperidin-4-yl)-1-(2,2,2-trifluoroethyl)-1H-indol-4-amine (0.25 g, 468 µmol, 1 eq.) in DMF (5 mL) were added 2-bromopropane (1723 mg, 1.40 mmol, 3 eq.) and K$_2$CO$_3$ (193.9 mg, 1.40 mmol, 3 eq.). The resulting mixture was stirred for 6 h at 25° C. under N$_2$. TLC analysis showed 15% of the starting material remained, and 60% of the desired product was detected. The reaction was quenched with water (20 mL), and the mixture was extracted with EtOAc (20 mL×3). The combined organic layers were washed with brine (20 mL×2), dried over anhydrous sodium sulfate, filtered, and concentrated in vacuo. The residue was purified by prep-TLC (SiO$_2$, DCM:MeOH=20:1) and then by prep-HPLC (neutral conditions) to afford 2-{3-[(4-methanesulfonyl-2-methoxyphenyl)amino]prop-1-yn-1-yl}-N-[1-(propan-2-yl)piperidin-4-yl]-1-(2,2,2-trifluoroethyl)-1H-indol-4-amine (0.0545 g, 91.3 µmol, 19.5% yield) as a light yellow solid. MS (ES$^+$, m/z): 577.3.

1H NMR (400 MHz, DMSO-d6) δ ppm 7.39 (dd, J=8.38, 1.90 Hz, 1H) 7.25 (d, J=1.96 Hz, 1H) 7.08 (s, 1H) 6.99 (t, J=8.01 Hz, 1H) 6.89 (d, J=8.44 Hz, 1H) 6.67 (d, J=8.44 Hz, 1H) 6.49 (t, J=6.17 Hz, 1H) 6.15 (d, J=7.82 Hz, 1H) 5.46 (d, J=8.07 Hz, 1H) 4.92 (q, J=9.13 Hz, 2H) 4.35 (d, J=6.11 Hz, 2H) 3.89 (s, 3H) 3.21-3.31 (m, 1H) 3.09 (s, 3H) 2.62-2.83 (m, 2H) 2.53-2.60 (m, 1H) 2.21 (br t, J=10.58 Hz, 2H) 1.93 (br d, J=11.98 Hz, 2H) 1.36-1.48 (m, 2H) 0.97 (d, J=6.60 Hz, 6H).

Example D4: Synthesis of 1-methoxy-3-(4-{[2-(3-{[2-methoxy-4-(trifluoromethyl)phenyl]amino}prop-1-yn-1-yl)-1-(2,2,2-trifluoroethyl)-1H-indol-4-yl]amino}piperidin-1-yl)propan-2-ol (Compound 689A)

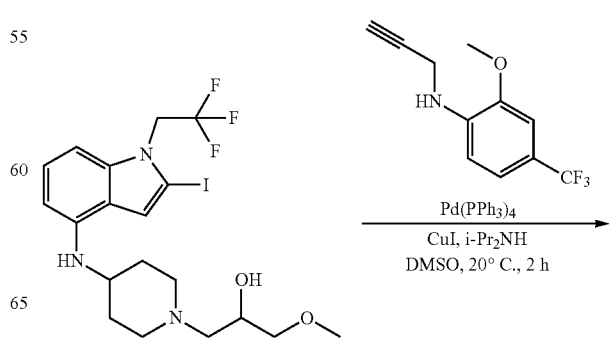

969

-continued

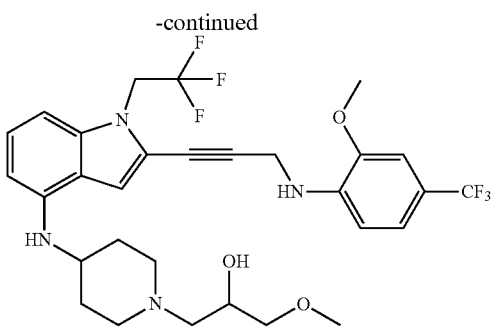

A mixture of 1-[4-[[2-iodo-1-(2,2,2-trifluoroethyl)indol-4-yl]amino]-1-piperidyl]-3-methoxy-propan-2-ol (0.05 g, 97.8 µmol, 1 eq.), 2-methoxy-N-prop-2-ynyl-4-(trifluoromethyl) aniline (44.8 mg, 195.6 µmol, 2 eq.), CuI (9.3 mg, 48.9 µmol, 0.5 eq.), Pd(dppf)Cl$_2$ (7.2 mg, 9.78 µmol, 0.1 eq.), and i-Pr$_2$NH (196 µmol, 27.6 µL, 2 eq.) in DMSO (1 mL) was degassed and purged with N$_2$ three times. The mixture was then stirred at 20° C. for 4 h under a N$_2$ atmosphere. LC-MS and HPLC analysis showed that the starting material was consumed, and the desired product was detected. To the mixture was added an 2M aqueous EDTA solution (15 mL). The resulting mixture was stirred for 1.5 h. The mixture was then extracted with EtOAc (10 mL×8). The organic layer was washed with brine (10 mL), dried over anhydrous sodium sulfate, filtered, and concentrated in vacuo. The crude residue was purified by prep-TLC (SiO$_2$, EtOAc:TEA=50:1) and prep-HPLC to afford 1-methoxy-3-[4-[[2-[3-[2-methoxy-4-(trifluoromethyl)anilino]prop-1-ynyl]-1-(2,2,2-trifluoroethyl)indol-4-yl]amino]-1-piperidyl]propan-2-ol (15.3 mg, 24.5 µmol, 25.1% yield) as a white solid. MS (ES$^+$, m/z): 613.3.

Example D5: Synthesis of 1-{4-[(2-{3-[(5-fluoro-4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol (Compound 677A)

970

-continued

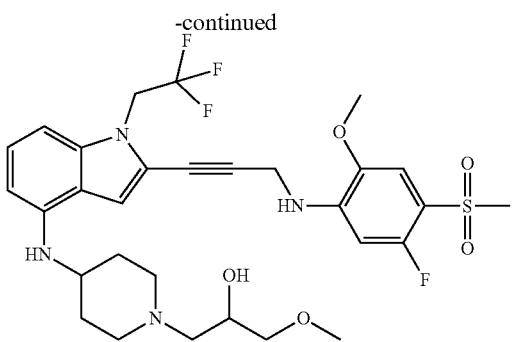

A solution of 5-fluoro-2-methoxy-4-(methylsulfonyl)-N-(prop-2-yn-1-yl)aniline (83.0 mg, 290 µmol, 3 eq.) in DMSO (2 mL) were added i-Pr$_2$NH (968 µmol, 137 µL, 10 eq.), CuI (9.2 mg, 48.4 µmol, 0.5 eq.), 1-(4-((2-iodo-1-(2,2,2-trifluoroethyl)-1H-indol-4-yl)amino)piperidin-1-yl)-3-methoxypropan-2-ol (50 mg, 96.81 µmol, 1 eq.), and Pd(PPh$_3$)$_4$ (2.2 mg, 1.94 µmol, 0.02 eq.). The reaction mixture was stirred at 40° C. for 1.5 h under N$_2$. LC-MS analysis showed that 24% of the starting material remained. Several new peaks were observed, and 36% of the desired product was detected. The reaction mixture was poured into a saturated EDTA solution (120 mL). The mixture was stirred at 25° C. for 1 h. The mixture was extracted with EtOAc (90 mL×3). The combined organic layers were washed with brine (200 mL×3), dried over anhydrous sodium sulfate, filtered, and concentrated under reduced pressure. The crude residue was purified by prep-TLC (PE:EtOAc:TEA=100:100:1, R$_f$=0.45) and prep-HPLC to afford 1-{4-[(2-{3-[(5-fluoro-4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol (27.5 mg, 63.1 µmol) as a light-yellow solid. MS (ES$^{30}$, m/z): 641.2.

Example D6: Synthesis of 3-methoxy-N-methyl-4-({3-[4-({1-[(2-oxo-1,3-dioxolan-4-yl)methyl]piperidin-4-yl}amino)-1-(2,2,2-trifluoroethyl)-1H-indol-2-yl]prop-2-yn-1-yl}amino)benzamide (Compound 762A)

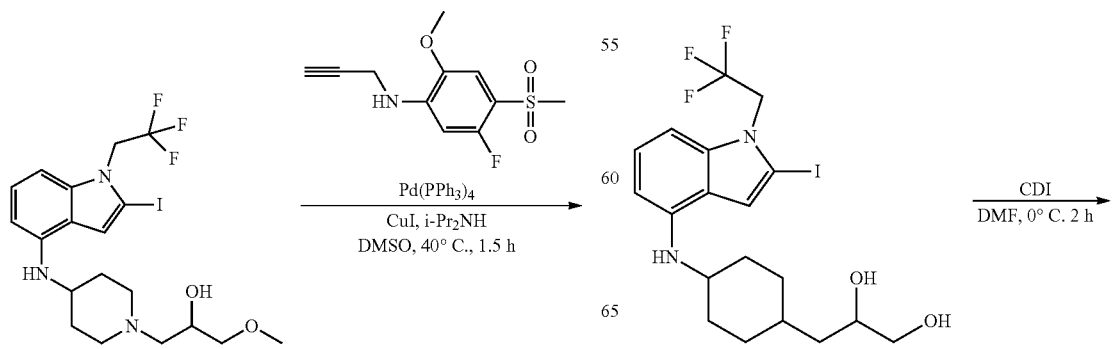

-continued

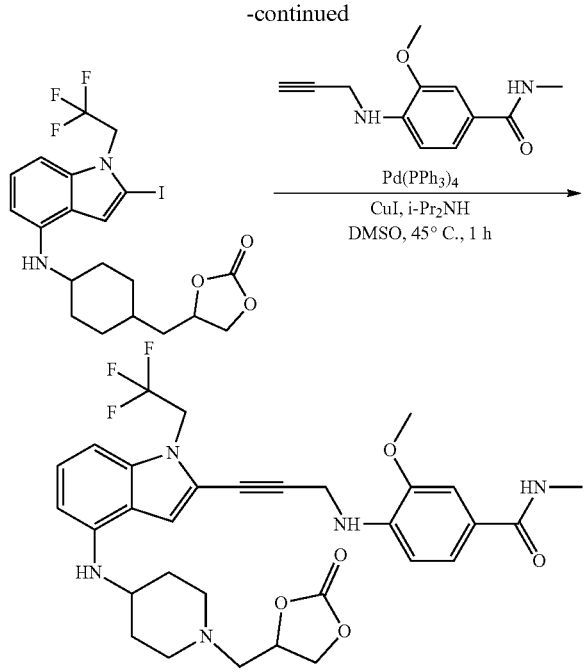

Preparation of 4-((4-((2-iodo-1-(2,2,2-trifluoroethyl)-1H-indol-4-yl)amino)cyclohexyl)methyl)-1,3-dioxolan-2-one: To the solution of 3-(4-((2-iodo-1-(2,2,2-trifluoroethyl)-1H-indol-4-yl)amino)cyclohexyl)propane-1,2-diol (150 mg, 272 μmol, 1 eq) in DMF (3 mL) was added 1,1'-carbonyldiimidazole (CDI) (88.0 mg, 543 μmol, 2 eq.) at 0° C. The mixture was stirred at 0° C. for 2 h. TLC analysis (EtOAc:TEA=20:1, $R_f$=0.43) indicated that the reaction was complete. The reaction mixture was diluted with water (30 mL) and extracted with EtOAc (20 mL×3). The combined organic layers were dried over anhydrous sodium sulfate, filtered, and concentrated under reduced pressure. The crude product was obtained as a light-yellow oil (200 mg, crude) and was used without further purification.

Preparation of 3-methoxy-N-methyl-4-({3-[4-({1-[(2-oxo-1,3-dioxolan-4-yl)methyl]piperidin-4-yl}amino)-1-(2,2,2-trifluoroethyl)-1H-indol-2-yl]prop-2-yn-1-yl}amino)benzamide: To a mixture of 3-methoxy-N-methyl-4-(prop-2-yn-1-ylamino)benzamide (100.1 mg, 458.6 μmol, 2 eq.) and 4-((4-((2-iodo-1-(2,2,2-trifluoroethyl)-1H-indol-4-yl)amino)cyclohexyl)methyl)-1,3-dioxolan-2-one (150 mg, 229 μmol, 1 eq.) in DMSO (3 mL) were added i-Pr$_2$NH (229 μmol, 32.4 μL, 1 eq.), Pd(PPh$_3$)$_4$ (5.3 mg, 4.6 μmol, 0.02 eq.), and CuI (43.7 mg, 229 μmol, 1 eq.) under N$_2$. The resulting mixture was stirred for 1 h at 45° C. TLC analysis (DCM:MeOH=10:1, $R_f$=0.24) indicated that the reaction was complete. The reaction mixture was quenched by adding a saturated aqueous EDTA solution (40 mL) at 25° C. and then extracted with EtOAc (20 mL×3). The combined organic layers were dried over anhydrous sodium sulfate, filtered, and concentrated under reduced pressure to give a residue. The residue was purified by prep-TLC (SiO$_2$, DCM:MeOH=10:1) and prep-HPLC to afford 3-methoxy-N-methyl-4-({3-[4-({1-[(2-oxo-1,3-dioxolan-4-yl)methyl]piperidin-4-yl}amino)-1-(2,2,2-trifluoroethyl)-1H-indol-2-yl]prop-2-yn-1-yl}amino)benzamide (40 mg, 64.4 μmol, 28.1% yield) as a light-yellow solid. MS (ES$^{30}$, m/z): 614.3.

Example D7: Synthesis of Compounds 777A and 778A

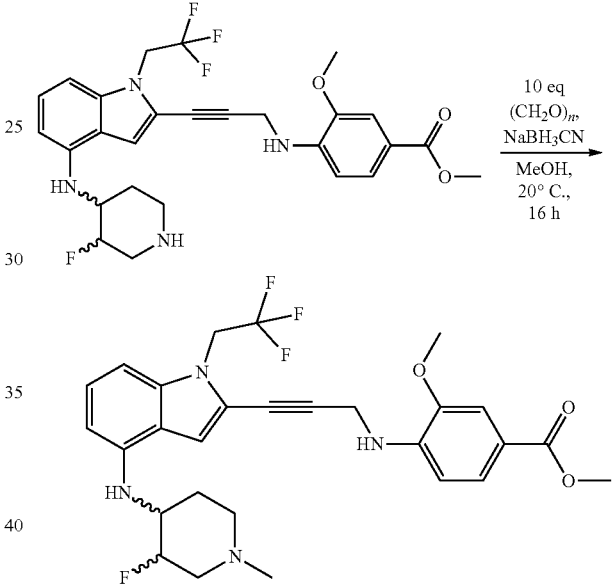

To a solution of methyl 4-((3-(4-((3-fluoropiperidin-4-yl)amino)-1-(2,2,2-trifluoroethyl)-1H-indol-2-yl)prop-2-yn-1-yl)amino)-3-methoxybenzoate (0.6 g, 1.13 mmol, 1 eq.) and paraformaldehyde (67.7 mg, 2.25 mmol, 2 eq.) in MeOH (5 mL) were added NaBH$_3$CN (212.4 mg, 3.38 mmol, 3 eq.) and AcOH (1.13 mmol, 64 μL, 1 eq.). The mixture was stirred at 50° C. for 2 h. TLC analysis ($R_f$=0.65, EtOAc:TEA=10:1) showed that the reaction was complete. The mixture was poured into a saturated aqueous solution of NaHCO$_3$ (80 mL), and the mixture was extracted with EtOAc (80 mL×3). The combined organic layers were washed with brine (30 mL×2), dried over anhydrous sodium sulfate, filtered, and concentrated under reduced pressure. The residue was purified by prep-TLC to afford the desired products.

rac-Methyl 4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzoate, MS (ES$^{30}$, m/z): 547.3; and rac-methyl 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoate, MS (ES$^{30}$, m/z): 547.2.

Example D8: Synthesis of 3-(4-(((3S,4R)-3-fluoro-1-methylpiperidin-4-yl)amino)-1-(2,2,2-trifluoroethyl)-1H-indol-2-yl)prop-2-yn-1-ol (Compound 895A)

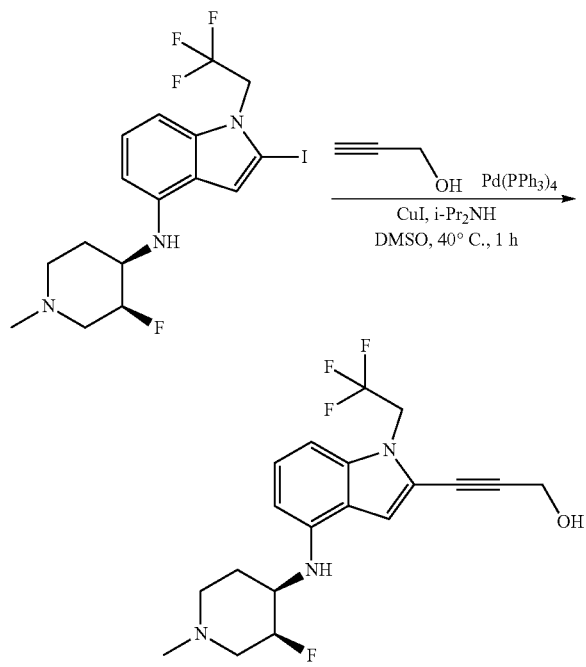

To a solution of prop-2-yn-1-ol (14.8 mg, 263.6 µmol, 1.2 eq.) in DMSO (3 mL) were added i-Pr$_2$NH (2.20 mmol, 189 µL, 10 eq), CuI (8.4 mg, 43.9 µmol, 0.2 eq.), N-((3S,4R)-3-fluoro-1-methylpiperidin-4-yl)-2-iodo-1-(2,2,2-trifluoroethyl)-1H-indol-4-amine ((0.1 g, 220 µmol, 1 eq.)), and Pd(PPh$_3$)$_4$ (12.7 mg, 11.0 µmol, 0.05 eq.). The mixture was heated and stirred at 40° C. for 1 h. TLC analysis indicated that some starting material remained, and one major new spot was detected. The reaction mixture was quenched by adding a saturated aqueous EDTA solution (30 mL), and the mixture was stirred further at 20° C. for 1 h. The mixture was then diluted with water (10 mL) and extracted with EtOAc (20 mL×3). The combined organic layers were washed with brine (15 mL×3), dried over anhydrous sodium sulfate, filtered, and concentrated under reduced pressure. The crude residue was purified by prep-TLC (SiO$_2$, DCM:MeOH=10:1), followed by prep-HPLC to afford 3-(4-(((3S,4R)-3-fluoro-1-methylpiperidin-4-yl)amino)-1-(2,2,2-trifluoroethyl)-1H-indol-2-yl)prop-2-yn-1-ol (0.03 g, 77.9 mol, 35.5% yield). MS (ES$^{30}$, m/z): 384.1.

Example D9: Synthesis of 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonic acid (Compound 931A)

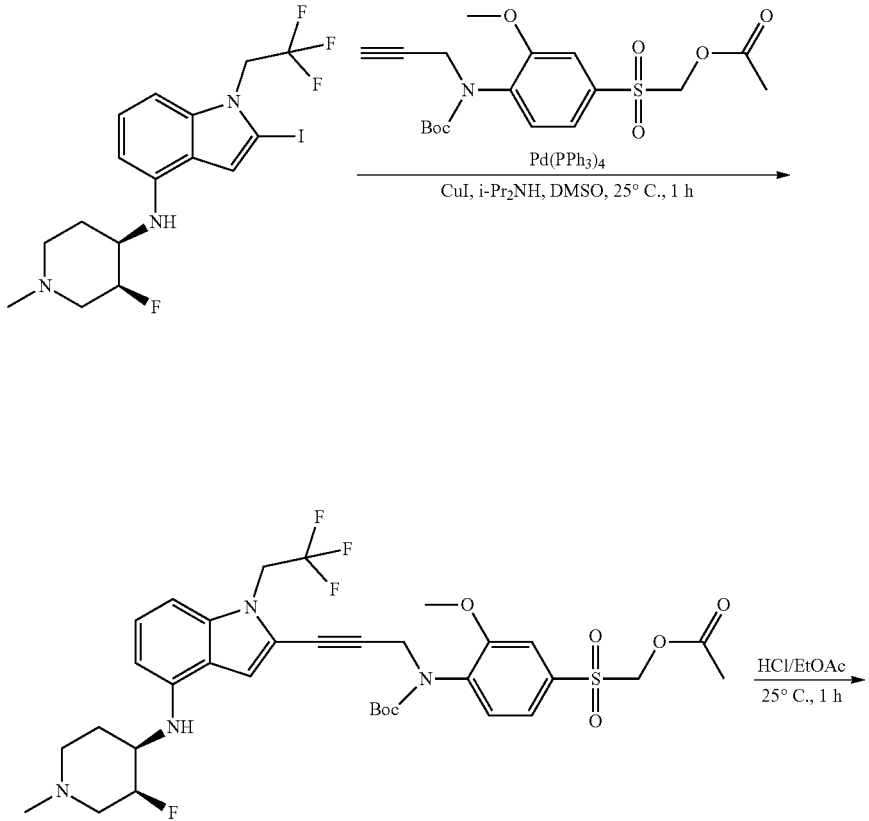

-continued

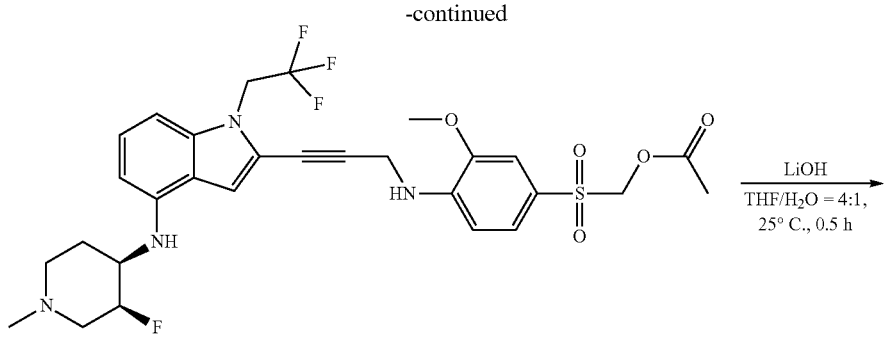

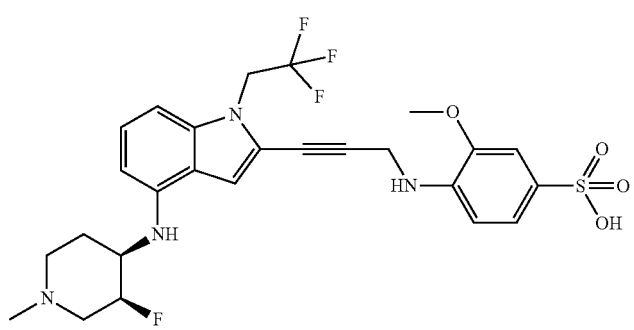

Preparation of ((4-((tert-butoxycarbonyl)(3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxyphenyl)sulfonyl)methyl acetate: To a mixture of ((4-((tert-butoxycarbonyl)(prop-2-yn-1-yl)amino)-3-methoxyphenyl)sulfonyl)mEtOAc (113.5 mg, 285.6 μmol, 1.3 eq.) in DMSO (3 mL), were added i-Pr$_2$NH (2.20 mmol, 310 μL, 10 eq.), CuI (8.8 mg, 43.9 μmol, 0.2 eq.), N-((3S,4R)-3-fluoro-1-methylpiperidin-4-yl)-2-iodo-1-(2,2,2-trifluoroethyl)-1H-indol-4-amine (0.1 g, 220 μmol, 1 eq.), and Pd(PPh$_3$)$_4$ (25.4 mg, 22 μmol, 0.1 eq.). The mixture was stirred at 25° C. for 1 h under N$_2$. TLC analysis showed that the reaction was complete. The reaction mixture was stirred with saturated EDTA solution (100 mL) and EtOAc (50 mL) at 25° C. The mixture was then extracted with EtOAc (50 mL×2), and the organic layer was washed with brine (100 mL×2). The combined organic layers were dried over anhydrous sodium sulfate, filtered, and concentrated under reduced pressure. The crude residue was purified by prep-TLC (SiO$_2$, DCM:MeOH=10:1) to afford ((4-((tert-butoxycarbonyl)(3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxyphenyl)sulfonyl)mEtOAc (0.14 g, 193.2 μmol, 87.9% yield) as a yellow solid.

Preparation of ((4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxyphenyl)sulfonyl)methyl acetate: To a solution of ((4-((tert-butoxycarbonyl)(3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxyphenyl)sulfonyl)methyl acetate (30 mg, 41.4 μmol, 1 eq.) in EtOAc (0.5 mL) was added HCl/EtOAc (4 M, 0.5 mL, 48.32 eq.). The mixture was stirred at 25° C. for 1 h under N$_2$. LC-MS analysis showed that the reaction was complete. The reaction mixture was diluted with saturated NaHCO$_3$ and the pH was adjusted to 8. The resulting mixture was extracted with EtOAc (50 mL×2), and The combined organic layers were washed with water (50 mL×2) and brine (50 mL×2). The organic phase was then dried over anhydrous sodium sulfate, filtered, and concentrated under reduced pressure to afford ((4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxyphenyl)sulfonyl)methyl acetate (40 mg, crude) as a yellow solid. The crude product as used directly in the next step without purification. MS (ES$^{30}$, m/z): 625.2.

Preparation of 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonic acid: To a solution of ((4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxyphenyl)sulfonyl)methyl acetate (30 mg, 48.0 μmol, 1 eq.) in THF (2 mL) and water (0.4 mL) was added LiOH·H$_2$O (6.1 mg, 144 μmol, 3 eq.). The mixture was stirred at 25° C. for 30 min under N$_2$. LC-MS analysis showed that the reaction was complete. The reaction mixture was diluted with saturated NaHCO$_3$, and the pH of the mixture was adjusted to 8. The reaction mixture was then extracted with EtOAc (50 mL×2), and The combined organic layers were washed with water (50 mL×2) and brine (50 mL×2). The organic phase was then dried over anhydrous sodium sulfate, filtered, and concentrated under reduced pressure. The crude residue was purified by prep-HPLC to afford 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonic acid (8.6 mg, 14.6 μmol, 30.4% yield) as a white solid. MS (ES$^{30}$, m/z): 569.2.

Example D10: Synthesis of Compounds 922A and 923A

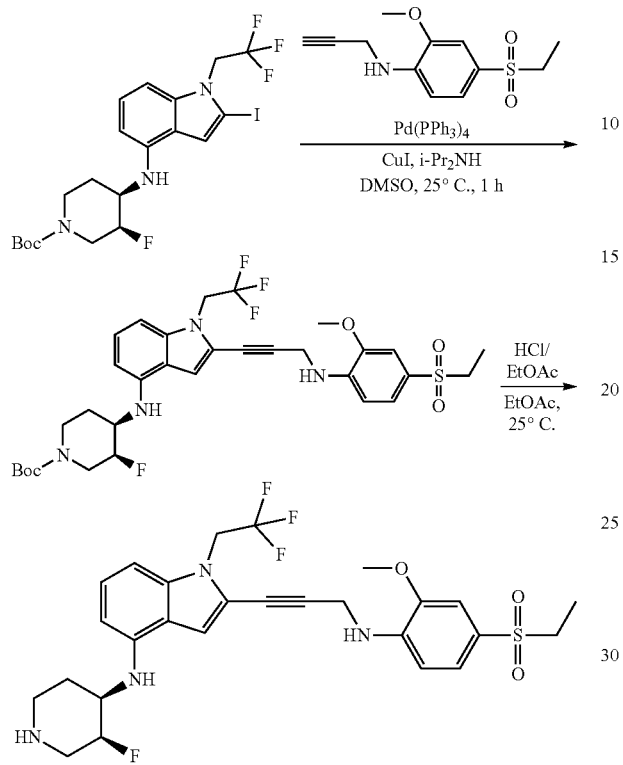

Preparation of tert-butyl (3S,4R)-4-{[2-(3-{[4-(ethanesulfonyl)-2-methoxyphenyl]amino}prop-1-yn-1-yl)-1-(2,2,2-trifluoroethyl)-1H-indol-4-yl]amino}-3-fluoropiperidine-1-carboxylate: To a solution of 4-(ethylsulfonyl)-2-methoxy-N-(prop-2-yn-1-yl)aniline (103 mg, 406 μmol, 1.1 eq.) in DMSO (2 mL) were added i-Pr₂NH (3.69 mmol, 522 μL, 10 eq.), CuI (7.0 mg, 37 μmol, 0.1 eq.), tert-butyl (3S,4R)-3-fluoro-4-((2-iodo-1-(2,2,2-trifluoroethyl)-1H-indol-4-yl)amino)piperidine-1-carboxylate (0.2 g, 369 μmol, 1 eq.), and Pd(PPh₃)₄ (8.5 mg, 7.39 μmol, 0.02 eq.). The solution was degassed and purged with N₂ three times. The mixture was stirred at 25° C. for 1 h. TLC analysis (PE:EtOAc=1:1, $R_f$=0.35) indicated that the starting material was consumed, and one new spot was detected. The reaction mixture was quenched by adding a 2M EDTA solution (20 mL), and the resulting mixture was stirred for 0.5 h. The mixture was extracted with EtOAc (25 mL×3), and The combined organic layers were washed with brine (15 mL), dried over anhydrous sodium sulfate, filtered, and concentrated under reduced pressure. The crude residue was purified by prep-TLC (SiO₂, PE:EtOAc=1:1) to afford tert-butyl (3S,4R)-4-{[2-(3-{[4-(ethanesulfonyl)-2-methoxyphenyl]amino}prop-1-yn-1-yl)-1-(2,2,2-trifluoroethyl)-1H-indol-4-yl]amino}-3-fluoropiperidine-1-carboxylate as a light-yellow solid. 63% yield, MS (ES[30], m/z): 667.3.

Preparation of 2-(3-((4-(ethylsulfonyl)-2-methoxyphenyl)amino)prop-1-yn-1-yl)-N-((3S,4R)-3-fluoropiperidin-4-yl)-1-(2,2,2-trifluoroethyl)-1H-indol-4-amine: A solution of tert-butyl (3S,4R)-4-{[2-(3-{[4-(ethanesulfonyl)-2-methoxyphenyl]amino}prop-1-yn-1-yl)-1-(2,2,2-trifluoroethyl)-1H-indol-4-yl]amino}-3-fluoropiperidine-1-carboxylate (0.1 g, 150 μmol, 1 eq.) in 4M HCl/EtOAc (5 mL) was stirred at 25° C. for 1 h. TLC analysis (PE:EtOAc=0:1, $R_f$=0.12) indicated that the starting material was consumed completely and that one new spot had formed. The reaction mixture was quenched by adding a saturated solution of Na₂CO₃ to adjust the pH of the mixture to 8. The mixture was then extracted with EtOAc (20 mL×3). The combined organic layers were washed with brine (10 mL), dried over anhydrous sodium sulfate, filtered, and concentrated under reduced pressure to afford 2-(3-((4-(ethylsulfonyl)-2-methoxyphenyl)amino)prop-1-yn-1-yl)-N-((3S,4R)-3-fluoropiperidin-4-yl)-1-(2,2,2-trifluoroethyl)-1H-indol-4-amine as a yellow solid. MS (ES[30], m/z): 567.2.

Example D11: Synthesis of Compounds 786A and 787A

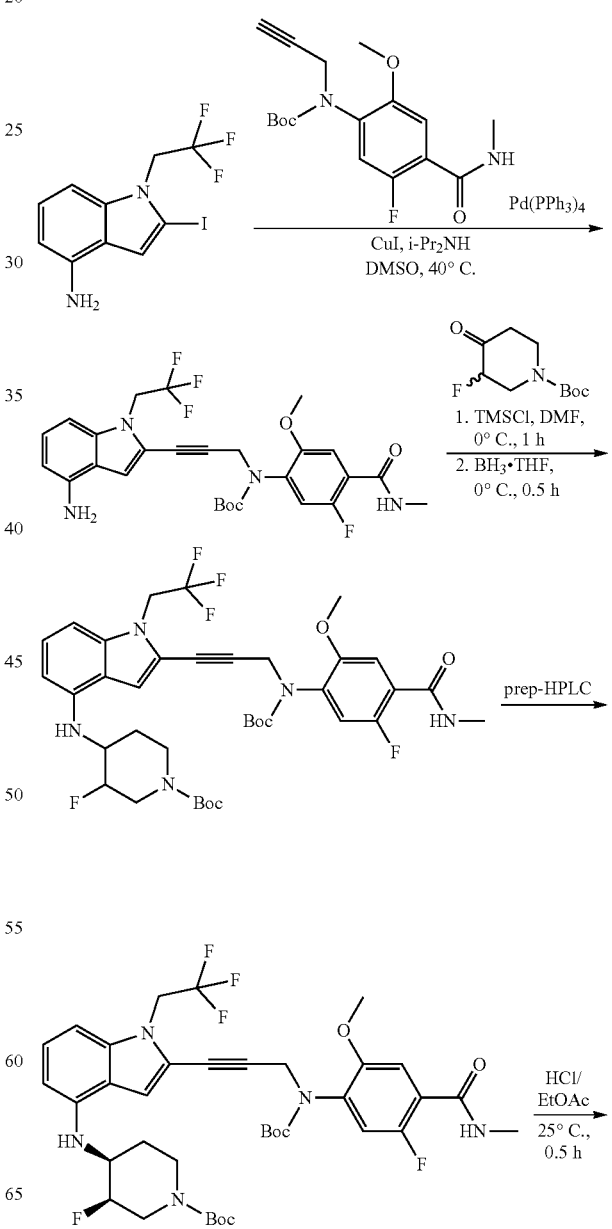

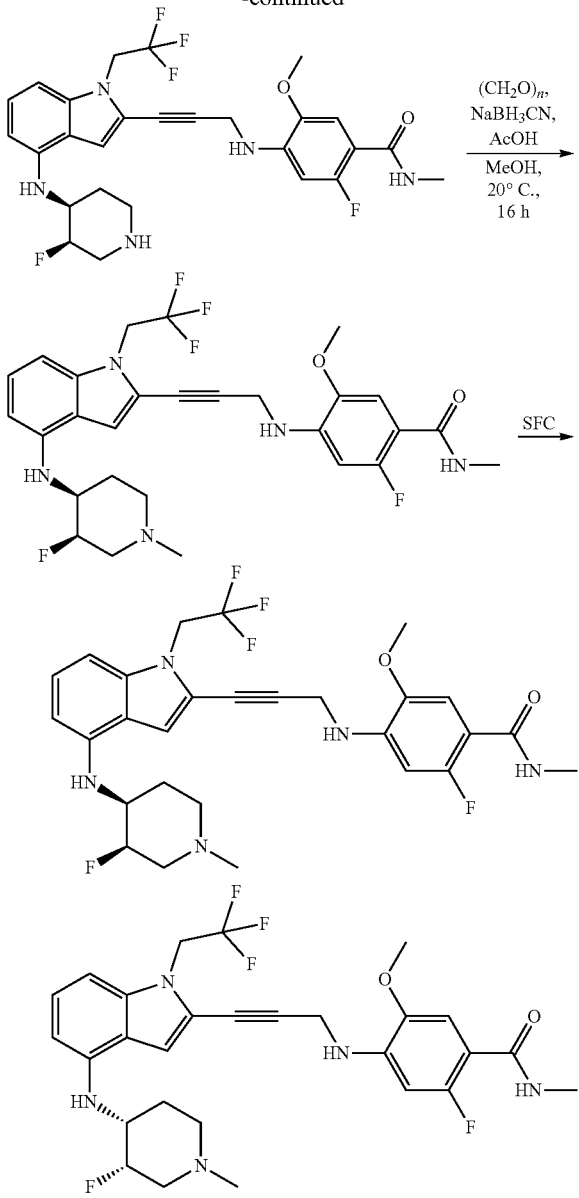

Preparation of tert-butyl (3-(4-amino-1-(2,2,2-trifluoroethyl)-1H-indol-2-yl)prop-2-yn-1-yl)(5-fluoro-2-methoxy-4-(methylcarbamoyl)phenyl)carbamate: To a solution of tert-butyl N-[5-fluoro-2-methoxy-4-(methylcarbamoyl)phenyl]-N-prop-2-ynyl-carbamate (1.38 g, 4.09 mmol, 1.1 eq.) in DMSO (15 mL) were added i-Pr$_2$NH (11.2 mmol, 1.58 mL, 3 eq.), CuI (212.4 mg, 1.12 mmol, 0.3 eq.), 2-iodo-1-(2,2,2-trifluoroethyl)indol-4-amine (1.4 g, 3.72 mmol, 1 eq., HCl salt), and Pd(PPh$_3$)$_4$ (214.8 mg, 186 μmol, 0.05 eq.). The mixture was stirred for 0.5 h at 40° C. under N$_2$. TLC analysis showed that the reaction was complete. The reaction was quenched by adding saturated aqueous EDTA (30 mL), and the mixture was extracted with EtOAc (30 mL×3). The combined organic layers were washed with brine (30 mL×2), dried over anhydrous sodium sulfate, filtered and concentrated in vacuo. The residue was purified by column chromatography (SiO$_2$, PE:EtOAc=4:1 to 1:1) to afford the desired intermediate.

Preparation of tert-butyl (3R,4S)-4-((2-(3-((tert-butoxycarbonyl)(5-fluoro-2-methoxy-4-(methylcarbamoyl)phenyl)amino)prop-1-yn-1-yl)-1-(2,2,2-trifluoroethyl)-1H-indol-4-yl)amino)-3-fluoropiperidine-1-carboxylate: To a mixture of tert-butyl (3-(4-amino-1-(2,2,2-trifluoroethyl)-1H-indol-2-yl)prop-2-yn-1-yl)(5-fluoro-2-methoxy-4-(methylcarbamoyl)phenyl)carbamate (1.5 g, 2.73 mmol, 1 eq.) and tert-butyl 3-fluoro-4-oxo-piperidine-1-carboxylate (2.97 g, 13.7 mmol, 5 eq.) in DMF (30 mL) was added TMSCl (27.4 mmol, 3.47 mL, 10 eq.) at 0° C. The mixture was stirred for 1 h under N$_2$, and BH$_3$·THF (1 M, 5.47 mL, 2 eq.) was added at 0° C. The resulting mixture was stirred for 0.5 h at 0° C. TLC analysis showed that the reaction was complete. The reaction was quenched with water (100 mL), and the mixture was extracted with EtOAc (50 mL×3). The combined organic layers were washed with brine (50 mL×2), dried over anhydrous sodium sulfate, filtered, and concentrated in vacuo to afford the crude product. The crude product was purified by prep-HPLC to afford tert-butyl (3R,4S)-4-((2-(3-((tert-butoxycarbonyl)(5-fluoro-2-methoxy-4-(methylcarbamoyl)phenyl)amino)prop-1-yn-1-yl)-1-(2,2,2-trifluoroethyl)-1H-indol-4-yl)amino)-3-fluoropiperidine-1-carboxylate (0.7 g, 934 μmol, 34.1% yield) as a yellow solid.

Preparation of 2-fluoro-4-((3-(4-(((3R,4S)-3-fluoropiperidin-4-yl)amino)-1-(2,2,2-trifluoroethyl)-1H-indol-2-yl)prop-2-yn-1-yl)amino)-5-methoxy-N-methylbenzamide: A solution of tert-butyl (3R,4S)-4-((2-(3-((tert-butoxycarbonyl)(5-fluoro-2-methoxy-4-(methylcarbamoyl)phenyl)amino)prop-1-yn-1-yl)-1-(2,2,2-trifluoroethyl)-1H-indol-4-yl)amino)-3-fluoropiperidine-1-carboxylate (0.6 g, 800 μmol, 1 eq.) was treated with HCl/EtOAc (4 M, 30 mL, 150 eq.) and stirred for 0.5 h at 25° C. TLC analysis showed that the reaction was complete. The reaction was quenched with a saturated NaHCO$_3$ aqueous solution (50 mL) and extracted with EtOAc (30 mL×3). The combined organic layers were washed with brine (50 mL×2), dried over anhydrous sodium sulfate, filtered, and concentrated in vacuo to afford 2-fluoro-4-((3-(4-(((3R,4S)-3-fluoropiperidin-4-yl)amino)-1-(2,2,2-trifluoroethyl)-1H-indol-2-yl)prop-2-yn-1-yl)amino)-5-methoxy-N-methylbenzamide (0.5 g, crude) as a yellow oil.

Preparation of 2-fluoro-4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-5-methoxy-N-methylbenzamide: To a solution of afford 2-fluoro-4-((3-(4-(((3R,4S)-3-fluoropiperidin-4-yl)amino)-1-(2,2,2-trifluoroethyl)-1H-indol-2-yl)prop-2-yn-1-yl)amino)-5-methoxy-N-methylbenzamide (0.45 g, 819 μmol, 1 eq.) in MeOH (10 mL) were added paraformaldehyde (98.4 mg, 3.28 mmol, 4 eq.), AcOH (2.3 μL, 0.05 eq.), and NaBH$_3$CN (257 mg, 4.09 mmol, 5 eq.). The mixture was heated and stirred for 6 h at 50° C. under N$_2$. TLC analysis showed that the reaction was complete. The reaction was quenched with saturated aqueous NaHCO$_3$ (30 mL) and extracted with EtOAc (30 mL×3). The combined organic layers were washed with brine (30 mL×2), dried over anhydrous sodium sulfate, filtered, and concentrated in vacuo. The residue was purified by prep-HPLC to afford 2-fluoro-4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-5-methoxy-N-methylbenzamide (0.25 g, 444 μmol, 54.2% yield) as a light-yellow solid.

2-fluoro-4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-5-methoxy-N-methylbenzamide was separated by SFC to afford the desired products as white solids.

2-fluoro-4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-5-methoxy-N-methylbenzamide, MS (ES$^{30}$, m/z): 564.3; and 2-fluoro-4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-5-methoxy-N-methylbenzamide, MS (ES[30], m/z): 564.3.

Example D12: Synthesis of Compounds 928A and 941A

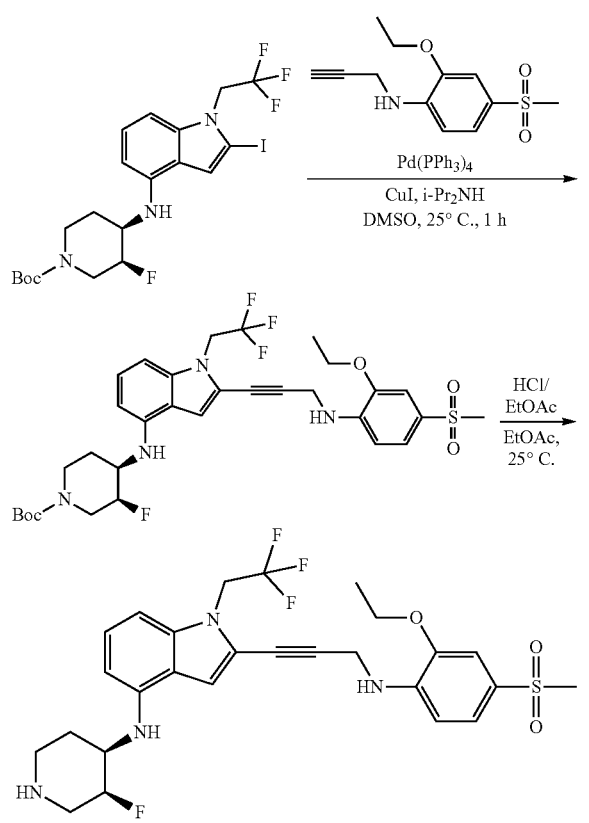

Preparation of tert-butyl (3S,4R)-4-[(2-{3-[(2-ethoxy-4-methanesulfonylphenyl)amino]prop-1-yn-1-yl}-1-(2,2,2-trifluoroethyl)-1H-indol-4-yl)amino]-3-fluoropiperidine-1-carboxylate: To a solution of 2-ethoxy-4-(methylsulfonyl)-N-(prop-2-yn-1-yl)aniline (1.2 eq.) in DMSO (3 mL) were added i-Pr$_2$NH (10 eq.), CuI (0.2 eq.), tert-butyl (3S,4R)-3-fluoro-4-((2-iodo-1-(2,2,2-trifluoroethyl)-1H-indol-4-yl)amino)piperidine-1-carboxylate (0.2 g, 369 μmol, 1 eq.) and Pd(PPh$_3$)$_4$ (0.05 eq.). The mixture was stirred at 40° C. for 1 h under N$_2$. TLC analysis (PE:EtOAc=1:3, R$_f$=0.4) indicated that the starting material was consumed completely, and that one new spot had formed. The reaction mixture was quenched by adding a saturated EDTA solution (30 mL), and the mixture was stirred at 20° C. for 1 h. The mixture was then diluted with water (10 mL) and extracted with EtOAc (40 mL×3). The combined organic layers were washed with brine (30 mL×3), dried over anhydrous sodium sulfate, filtered, and concentrated under reduced pressure to give a residue. The residue was purified by prep-TLC (SiO$_2$, PE:EtOAc=1:1) and prep-HPLC to afford tert-butyl (3S,4R)-4-[(2-{3-[(2-ethoxy-4-methanesulfonylphenyl)amino]prop-1-yn-1-yl}-1-(2,2,2-trifluoroethyl)-1H-indol-4-yl)amino]-3-fluoropiperidine-1-carboxylate as a yellow solid. MS (ES[30], m/z): 611.2 (M−tert-But).

Preparation of 2-{3-[(2-ethoxy-4-methanesulfonylphenyl)amino]prop-1-yn-1-yl}-N-[(3S,4R)-3-fluoropiperidin-4-yl]-1-(2,2,2-trifluoroethyl)-1H-indol-4-amine: A mixture of tert-butyl (3S,4R)-4-[(2-{3-[(2-ethoxy-4-methanesulfonylphenyl)amino]prop-1-yn-1-yl}-1-(2,2,2-trifluoroethyl)-1H-indol-4-yl)amino]-3-fluoropiperidine-1-carboxylate (1 eq.) and HCl/EtOAc (4 M, 2 mL) in EtOAc (1 mL) was stirred at 20° C. for 0.5 h. TLC analysis indicated that the starting material was consumed completely and that one new spot had formed. The reaction mixture was quenched by adding an aqueous saturated Na$_2$CO$_3$ solution to adjust the pH of the mixture to >7. The mixture was then diluted with water (20 mL) and extracted with EtOAc (20 mL×3). The combined organic layers were washed with brine (20 mL×3), dried over anhydrous sodium sulfate, filtered, and concentrated under reduced pressure. The crude residue was purified by prep-HPLC to afford 2-{3-[(2-ethoxy-4-methanesulfonylphenyl)amino]prop-1-yn-1-yl}-N-[(3S,4R)-3-fluoropiperidin-4-yl]-1-(2,2,2-trifluoroethyl)-1H-indol-4-amine as a yellow solid. 51% yield, MS (ES[30], m/z): 567.3.

Example D13: Synthesis of Compounds 460A, 609A, 622A, and 730A

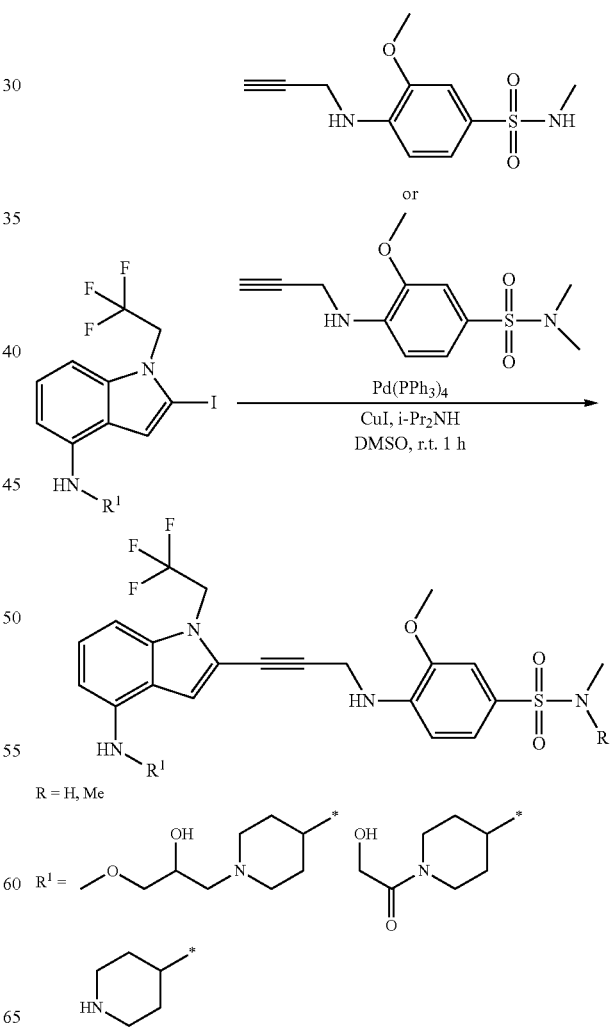

Preparation of desired products: To a mixture of $R^1$-substituted 2-iodo-1-(2,2,2-trifluoroethyl)-1H-indol-4-amine (30 mg, 58.7 µmol, 1 eq.) and 3-methoxy-N,N-dimethyl-4-(prop-2-yn-1-ylamino)benzenesulfonamide or 3-methoxy-N-methyl-4-(prop-2-yn-1-ylamino)benzenesulfonamide (20.4 mg, 64.5 µmol, 1.1 eq.) in DMSO (3 mL) were added CuI (11.2 mg, 59 µmol, 1 eq.), N-isopropylpropan-2-amine (559 µmol, 8.3 µL, 1 eq.) and Pd(PPh$_3$)$_4$ (1.36 mg, 1.17 µmol, 0.02 eq.) under N$_2$. The mixture was stirred for 1 h at 25° C. TLC analysis indicated that the reaction was complete. The reaction mixture was quenched by adding a saturated EDTA solution (60 mL) at 25° C. and stirring the mixture for 1 h. The mixture was then extracted with EtOAc (20 mL×4). The combined organic layers were dried over anhydrous sodium sulfate, filtered, and concentrated under reduced pressure. The residue was purified by prep-TLC to afford the desired products as light-yellow solids.

4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxy-N,N-dimethylbenzene-1-sulfonamide, MS (ES$^{30}$, m/z): 652.4; 4-{[3-(4-{[1-(2-hydroxyacetyl)piperidin-4-yl]amino}-1-(2,2,2-trifluoroethyl)-1H-indol-2-yl)prop-2-yn-1-yl]amino}-3-methoxy-N,N-dimethylbenzene-1-sulfonamide, MS (ES$^{30}$, m/z): 622.4; 3-methoxy-N,N-dimethyl-4-[(3-{4-[(piperidin-4-yl)amino]-1-(2,2,2-trifluoroethyl)-1H-indol-2-yl}prop-2-yn-1-yl)amino]benzene-1-sulfonamide, MS (ES$^{30}$, m/z): 564.3; and 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxy-N-methylbenzene-1-sulfonamide, MS (ES$^{30}$, m/z): 638.2.

Example D14: Synthesis of Compounds 570A and 571A

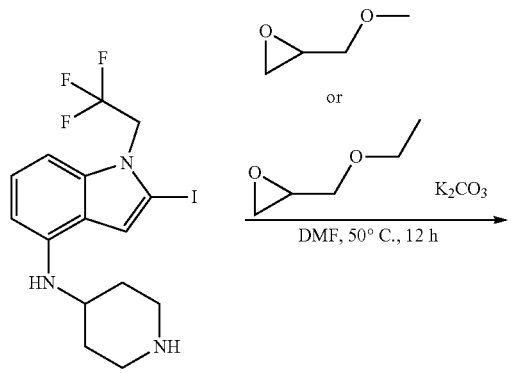

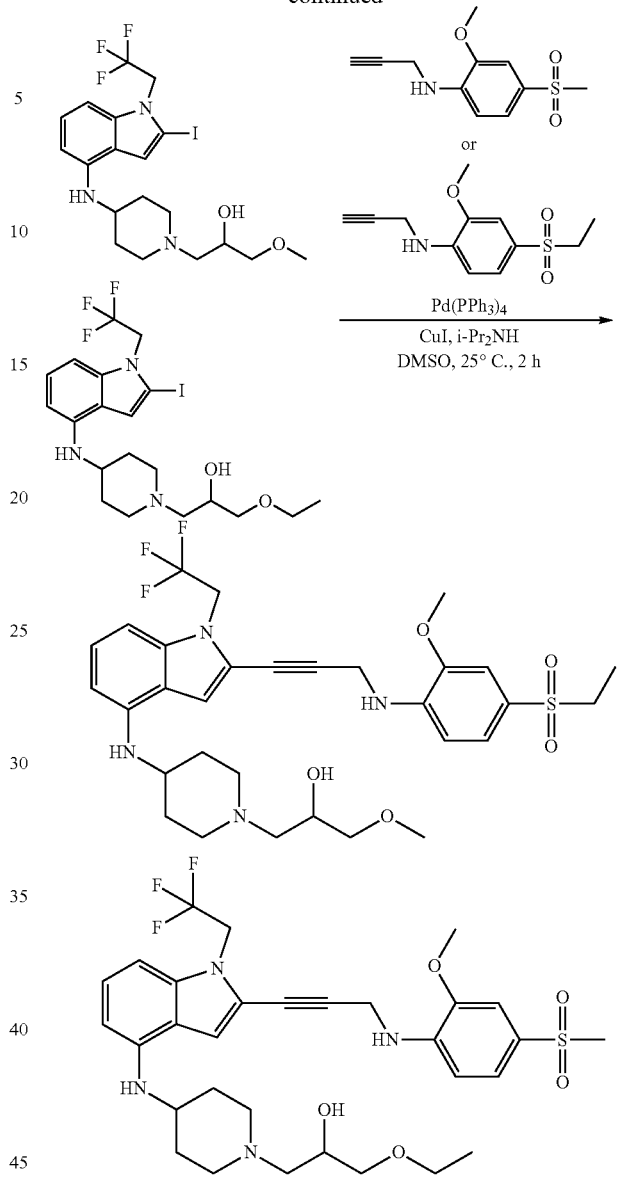

Preparation of 1-(4-((2-iodo-1-(2,2,2-trifluoroethyl)-1H-indol-4-yl)amino)piperidin-1-yl)-3-methoxypropan-2-ol and 1-ethoxy-3-(4-((2-iodo-1-(2,2,2-trifluoroethyl)-1H-indol-4-yl)amino)piperidin-1-yl)propan-2-ol: To a solution of compound 2-iodo-N-(piperidin-4-yl)-1-(2,2,2-trifluoroethyl)-1H-indol-4-amine (10 g, 22.45 mmol, 1 eq.) in DMF (300 mL) were added 2-(methoxymethyl)oxirane or 2-(ethoxy methyl)oxirane (5 eq.) and K$_2$CO$_3$ (3 eq.). The mixture was stirred at 50° C. for 12 h. TLC or LC-MS analysis showed that the starting material was consumed completely. The reaction mixture was diluted by adding water (500 mL) and extracted with EtOAc (200 mL×3). The combined organic layers were washed with brine (40 mL), dried over anhydrous sodium sulfate, filtered, and concentrated. The crude residue was purified by prep-TLC to afford the desired products.

Preparation of 1-(4-((2-(3-((4-(ethylsulfonyl)-2-methoxyphenyl)amino)prop-1-yn-1-yl)-1-(2,2,2-trifluoroethyl)-1H-indol-4-yl)amino)piperidin-1-yl)-3-methoxypropan-2-ol and 1-ethoxy-3-(4-((2-(3-((2-methoxy-4-(methylsulfonyl)

phenyl)amino)prop-1-yn-1-yl)-1-(2,2,2-trifluoroethyl)-1H-indol-4-yl)amino)piperidin-1-yl)propan-2-ol: To a mixture of 2-methoxy-4-(methylsulfonyl)-N-(prop-2-yn-1-yl)aniline or 4-(ethylsulfonyl)-2-methoxy-N-(prop-2-yn-1-yl)aniline (64.6 mg, 178 μmol, 1.2 eq.) in DMSO (3 mL) were added i-Pr$_2$NH (10 eq.), CuI (1 eq.), 1-(4-((2-iodo-1-(2,2,2-trifluoroethyl)-1H-indol-4-yl)amino)piperidin-1-yl)-3-methoxypropan-2-ol or 1-ethoxy-3-(4-((2-iodo-1-(2,2,2-trifluoroethyl)-1H-indol-4-yl)amino)piperidin-1-yl)propan-2-ol (1 eq.), and Pd(PPh$_3$)$_4$ (0.2 eq.) at 25° C. The mixture was stirred at 25° C. for 1 h under N$_2$. LC-MS and TLC analysis showed that the reaction was complete. The reaction mixture was quenched by adding a saturated aqueous EDTA solution (30 mL) at 25° C. and stirring the mixture for 2 h. The reaction mixture was partitioned by adding EtOAc (10 mL). The aqueous phase was extracted with EtOAc (10 mL×3). The organic phase was washed with brine (10 mL×3), dried over anhydrous sodium sulfate, filtered, and concentrated in vacuo. The crude residue was purified by prep-TLC, confirmed by HPLC and LC-MS, then purified by prep-HPLC to give solutions of the desired products, which were isolated by lyophilization.

1-(4-((2-(3-((4-(ethylsulfonyl)-2-methoxyphenyl)amino)prop-1-yn-1-yl)-1-(2,2,2-trifluoroethyl)-1H-indol-4-yl)amino)piperidin-1-yl)-3-methoxypropan-2-ol, MS (ES$^{30}$, m/z): 637.2; 1-ethoxy-3-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)propan-2-ol, MS (ES$^{30}$, m/z): 637.3.

Example D15: Synthesis of Compounds 880A and 884A

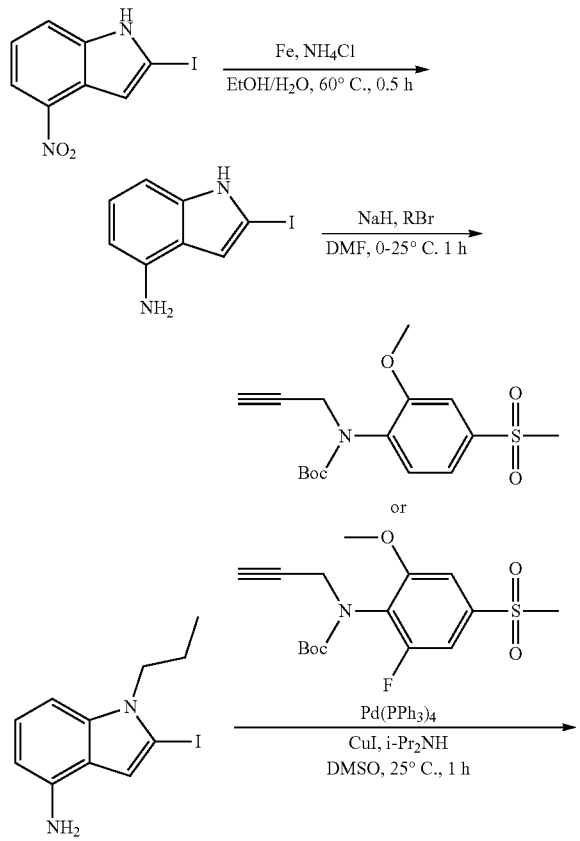

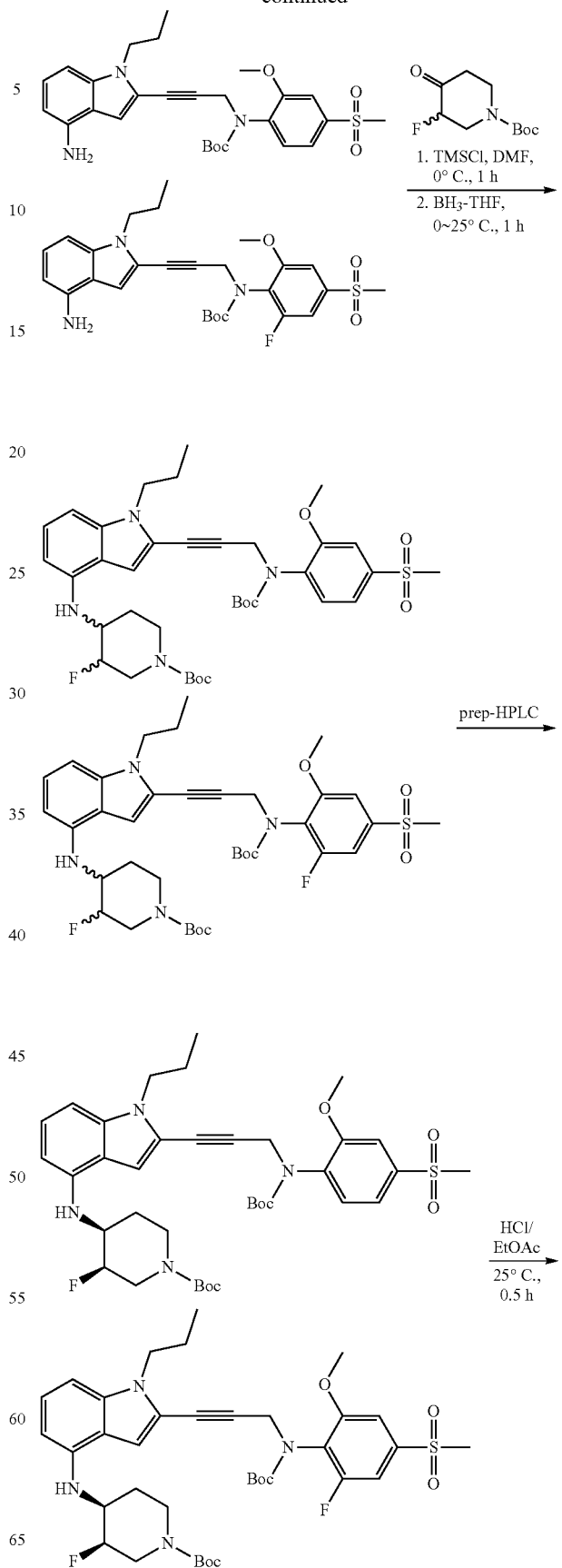

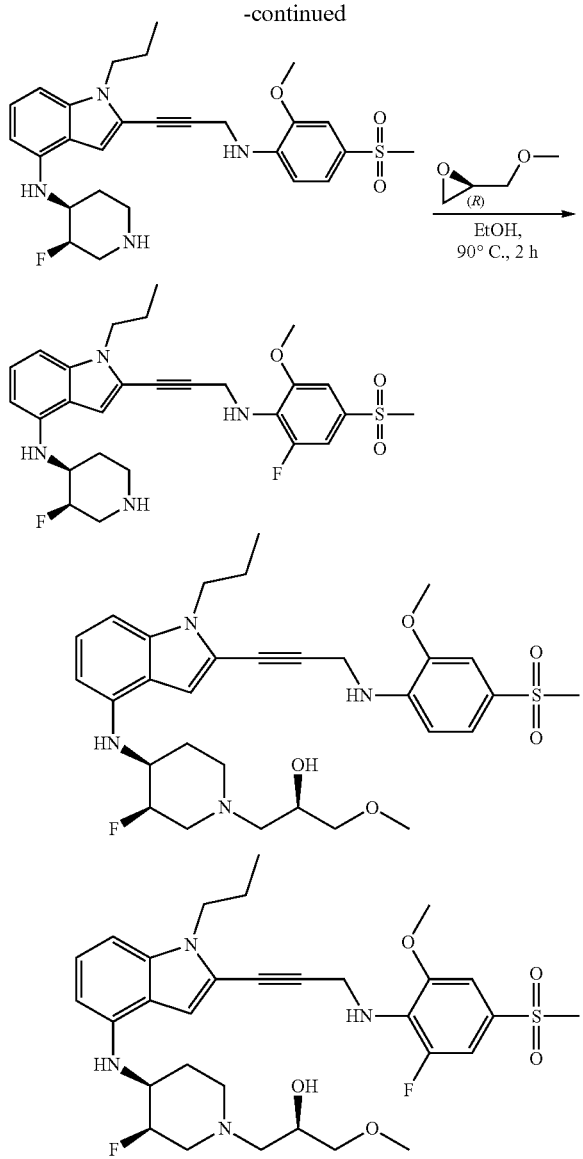

Preparation of 2-iodo-1H-indol-4-amine: To a solution of 2-iodo-4-nitro-1H-indole (4 g, 13.9 mmol, 1 eq.) in EtOH (32 mL) were added a saturated solution of NH₄Cl (8 mL) and Fe (2.33 g, 41.7 mmol, 3 eq.). The mixture was stirred at 60° C. for 0.5 h. TLC analysis showed that the reaction was complete. The reaction mixture was filtered, extracted with EtOAc (100 mL×2), and washed with water (250 mL×2) and brine (250 mL×2). The combined organic layers were dried over anhydrous sodium sulfate, filtered, and concentrated under reduced pressure to give a residue. The residue was purified by column chromatography (SiO₂, PE:EtOAc=10:1 to 8:1) to afford 2-iodo-1H-indol-4-amine (3.2 g, 12.40 mmol, 89.3% yield) as an off-white solid.

Preparation of 2-iodo-1-propyl-1H-indol-4-amine: To a solution of 2-iodo-1H-indol-4-amine (2 g, 7.75 mmol, 1 eq.) in DMF (15 mL) at 0° C. was added NaH (930 mg, 23.3 mmol, 60% in mineral oil, 3 eq.). The reaction mixture was stirred at 0° C. for 0.5 h, and 1-bromopropane (11.6 mmol, 1.06 mL, 1.5 eq.) was added at 25° C. The resulting mixture was stirred at 25° C. for 0.5 h. TLC analysis showed that the reaction was complete. The reaction mixture was quenched with saturated aqueous NH₄Cl (100 mL) at 0° C. The mixture was extracted with EtOAc (100 mL×2) and washed with water (250 mL×2) and brine (250 mL×2). The combined organic layers were dried over anhydrous sodium sulfate, filtered, and concentrated under reduced pressure. The crude residue was purified by column chromatography (SiO₂, PE:EtOAc=30:1 to 10:1) to afford 2-iodo-1-propyl-1H-indol-4-amine (2.1 g, 7 mmol, 90.3% yield) as a brown solid.

Preparation of tert-butyl (3-(4-amino-1-propyl-1H-indol-2-yl)prop-2-yn-1-yl)(2-methoxy-4-(methylsulfonyl)phenyl)carbamate and tert-butyl (3-(4-amino-1-propyl-1H-indol-2-yl)prop-2-yn-1-yl)(2-fluoro-6-methoxy-4-(methylsulfonyl)phenyl)carbamate: To a solution of tert-butyl (2-methoxy-4-(methylsulfonyl)phenyl)(prop-2-yn-1-yl)carbamate (1.53 g, 4.50 mmol, 1.5 eq.) or tert-butyl (2-fluoro-6-methoxy-4-(methylsulfonyl)phenyl)(prop-2-yn-1-yl)carbamate (857.36 mg, 2.40 mmol, 1.2 eq.) in DMSO (8-10 mL) were added i-Pr₂NH (10 eq.), CuI (0.2 eq.), 2-iodo-1-propyl-1H-indol-4-amine (1 eq.), and Pd(PPh₃)₄ (0.1 eq.). The mixture was stirred at 25° C. for 1 h under N₂. TLC analysis showed that the reaction was complete. The reaction mixture was partitioned by adding a saturated EDTA solution (150 mL) and EtOAc (50 mL) at 25° C. The resulting mixture was filtered, extracted with EtOAc (250 mL×2), and washed with water (100 mL×2) and brine (100 mL×2). The combined organic layers were dried over anhydrous sodium sulfate, filtered, and concentrated under reduced pressure. The crude residue was purified by column chromatography (SiO₂, PE:EtOAc=20:1 to 2:1) to afford the desired products as yellow solids. tert-Butyl (3-(4-amino-1-propyl-1H-indol-2-yl)prop-2-yn-1-yl)(2-methoxy-4-(methylsulfonyl)phenyl)carbamate, 78.2% yield; and tert-butyl (3-(4-amino-1-propyl-1H-indol-2-yl)prop-2-yn-1-yl)(2-fluoro-6-methoxy-4-(methylsulfonyl)phenyl)carbamate, 63.3% yield.

Preparation of tert-butyl 4-((2-(3-((tert-butoxycarbonyl)(2-methoxy-4-(methylsulfonyl)phenyl)amino)prop-1-yn-1-yl)-1-propyl-1H-indol-4-yl)amino)-3-fluoropiperidine-1-carboxylate and tert-butyl 4-((2-(3-((tert-butoxycarbonyl)(2-fluoro-6-methoxy-4-(methylsulfonyl)phenyl)amino)prop-1-yn-1-yl)-1-propyl-1H-indol-4-yl)amino)-3-fluoropiperidine-1-carboxylate: To a solution of tert-butyl (3-(4-amino-1-propyl-1H-indol-2-yl)prop-2-yn-1-yl)(2-methoxy-4-(methylsulfonyl)phenyl)carbamate or tert-butyl (3-(4-amino-1-propyl-1H-indol-2-yl)prop-2-yn-1-yl)(2-fluoro-6-methoxy-4-(methylsulfonyl)phenyl)carbamate (1.56 mmol, 1 eq.) in DMF (10 mL) were added tert-butyl 3-fluoro-4-oxopiperidine-1-carboxylate (5 eq.) and TMSCl (10 eq.). The mixture was stirred at 0° C. for 1 h, and BH₃·THF (1 M, 10 eq.) was added. The resulting mixture was stirred at 25° C. for 1 h. LC-MS and TLC analysis showed that the reaction was complete. The reaction mixture was quenched by adding ice water (150 mL) and extracting the mixture with EtOAc (100 mL×2). The combined organic layers were washed with water (250 mL×2) and brine (250 mL×2), dried over anhydrous sodium sulfate, filtered, and concentrated under reduced pressure to afford the desired products.

Preparation of tert-butyl (3R,4S)-4-((2-(3-((tert-butoxycarbonyl)(2-methoxy-4-(methylsulfonyl)phenyl)amino)prop-1-yn-1-yl)-1-propyl-1H-indol-4-yl)amino)-3-fluoropiperidine-1-carboxylate and tert-butyl (3R,4S)-4-((2-(3-((tert-butoxycarbonyl)(2-fluoro-6-methoxy-4-(methylsulfonyl)phenyl)amino)prop-1-yn-1-yl)-1-propyl-1H-indol-4-yl)amino)-3-fluoropiperidine-1-carboxylate: tert-Butyl 4-((2-(3-((tert-butoxycarbonyl)(2-methoxy-4-(methylsulfonyl)phenyl)amino)prop-1-yn-1-yl)-1-propyl-1H-indol-4-yl)

amino)-3-fluoropiperidine-1-carboxylate and tert-butyl 4-((2-(3-((tert-butoxycarbonyl)(2-fluoro-6-methoxy-4-(methylsulfonyl)phenyl)amino)prop-1-yn-1-yl)-1-propyl-1H-indol-4-yl)amino)-3-fluoropiperidine-1-carboxylate were purified by prep-HPLC. The pH of the solutions were adjusted to 8 using a saturated aqueous Na$_2$CO$_3$ solution. Then the aqueous phase was extracted with EtOAc (100 mL×2). The combined organic layers were washed with brine (250 mL×2) dried over anhydrous sodium sulfate, filtered, and concentrated in vacuo to afford the desired products as yellow solids.

tert-Butyl (3R,4S)-4-((2-(3-((tert-butoxycarbonyl)(2-methoxy-4-(methylsulfonyl)phenyl)amino)prop-1-yn-1-yl)-1-propyl-1H-indol-4-yl)amino)-3-fluoropiperidine-1-carboxylate, 33% yield, MS (ES$^{30}$, m/z): 713.3; and tert-butyl (3R,4S)-4-((2-(3-((tert-butoxycarbonyl)(2-fluoro-6-methoxy-4-(methylsulfonyl)phenyl)amino)prop-1-yn-1-yl)-1-propyl-1H-indol-4-yl)amino)-3-fluoropiperidine-1-carboxylate, 21.1% yield, MS (ES$^{30}$, m/z): 731.4.

Preparation of N-((3R,4S)-3-fluoropiperidin-4-yl)-2-(3-((2-methoxy-4-(methylsulfonyl)phenyl)amino)prop-1-yn-1-yl)-1-propyl-1H-indol-4-amine and 2-(3-((2-fluoro-6-methoxy-4-(methylsulfonyl)phenyl)amino)prop-1-yn-1-yl)-N-((3R,4S)-3-fluoropiperidin-4-yl)-1-propyl-1H-indol-4-amine: To a solution of tert-butyl (3R,4S)-4-((2-(3-((tert-butoxycarbonyl)(2-methoxy-4-(methylsulfonyl)phenyl)amino)prop-1-yn-1-yl)-1-propyl-1H-indol-4-yl)amino)-3-fluoropiperidine-1-carboxylate (350.70 μmol 1 eq.) or tert-butyl (3R,4S)-4-((2-(3-((tert-butoxycarbonyl)(2-fluoro-6-methoxy-4-(methylsulfonyl)phenyl)amino)prop-1-yn-1-yl)-1-propyl-1H-indol-4-yl)amino)-3-fluoropiperidine-1-carboxylate (1 eq.) in EtOAc (3 mL) was added HCl/EtOAc (4 M, 3 mL). The mixture was stirred at 25° C. for 0.5 h. TLC analysis showed that the reaction was complete. The reaction mixture was quenched with water (100 mL) and the pH of the mixture was adjusted to 8 using a saturated aqueous Na$_2$CO$_3$ solution. The resulting mixture was extracted with EtOAc (250 mL×2). The combined organic layers were washed with brine (250 mL×2), dried over anhydrous sodium sulfate, filtered, and concentrated in vacuo. The crude residue was purified by prep-TLC (SiO$_2$, DCM:MeOH=10:1) to afford the desired products as yellow solids.

Preparation of (2R)-1-[(3 RS,4 SR)-3-fluoro-4-[(2-{3-[(4-methanesulfonyl-2-methoxyphenyl)amino]prop-1-yn-1-yl}-1-propyl-1H-indol-4-yl)amino]piperidin-1-yl]-3-methoxypropan-2-ol and (2R)-1-[(3 RS,4 SR)-3-fluoro-4-[(2-{3-[(2-fluoro-4-methanesulfonyl-6-methoxyphenyl)amino]prop-1-yn-1-yl}-1-propyl-1H-indol-4-yl)amino]piperidin-1-yl]-3-methoxypropan-2-ol: To a solution of N-((3R,4S)-3-fluoropiperidin-4-yl)-2-(3-((2-methoxy-4-(methylsulfonyl)phenyl)amino)prop-1-yn-1-yl)-1-propyl-1H-indol-4-amine or 2-(3-((2-fluoro-6-methoxy-4-(methylsulfonyl)phenyl)amino)prop-1-yn-1-yl)-N-((3R,4S)-3-fluoropiperidin-4-yl)-1-propyl-1H-indol-4-amine (1 eq.) in EtOH (3 mL) was added (2R)-2-(methoxymethyl)oxirane (6 eq.). The mixture was stirred at 90° C. for 2 h. LC-MS and TLC analysis showed that the reaction was complete. The reaction mixture was quenched with water (50 mL) and extracted with EtOAc (50 mL×2). The combined organic layers were washed with brine (50 mL×2), dried over anhydrous sodium sulfate, filtered, and concentrated under reduced pressure. The crude residue was purified by prep-HPLC to afford the desired products as white solids.

N-((3R,4S)-3-fluoropiperidin-4-yl)-2-(3-((2-methoxy-4-(methylsulfonyl)phenyl)amino)prop-1-yn-1-yl)-1-propyl-1H-indol-4-amine, MS (ES$^{30}$, m/z): 601.2; and 2-(3-((2-fluoro-6-methoxy-4-(methylsulfonyl)phenyl)amino)prop-1-yn-1-yl)-N-((3R,4S)-3-fluoropiperidin-4-yl)-1-propyl-1H-indol-4-amine, MS (ES$^{30}$, m/z): 619.3.

Example D16: Synthesis of (R)-1-((3R,4S)-4-((1-allyl-2-(3-((2-methoxy-4-(methylsulfonyl)phenyl)amino)prop-1-yn-1-yl)-1H-indol-4-yl)amino)-3-fluoropiperidin-1-yl)-3-methoxypropan-2-ol (Compound 881A)

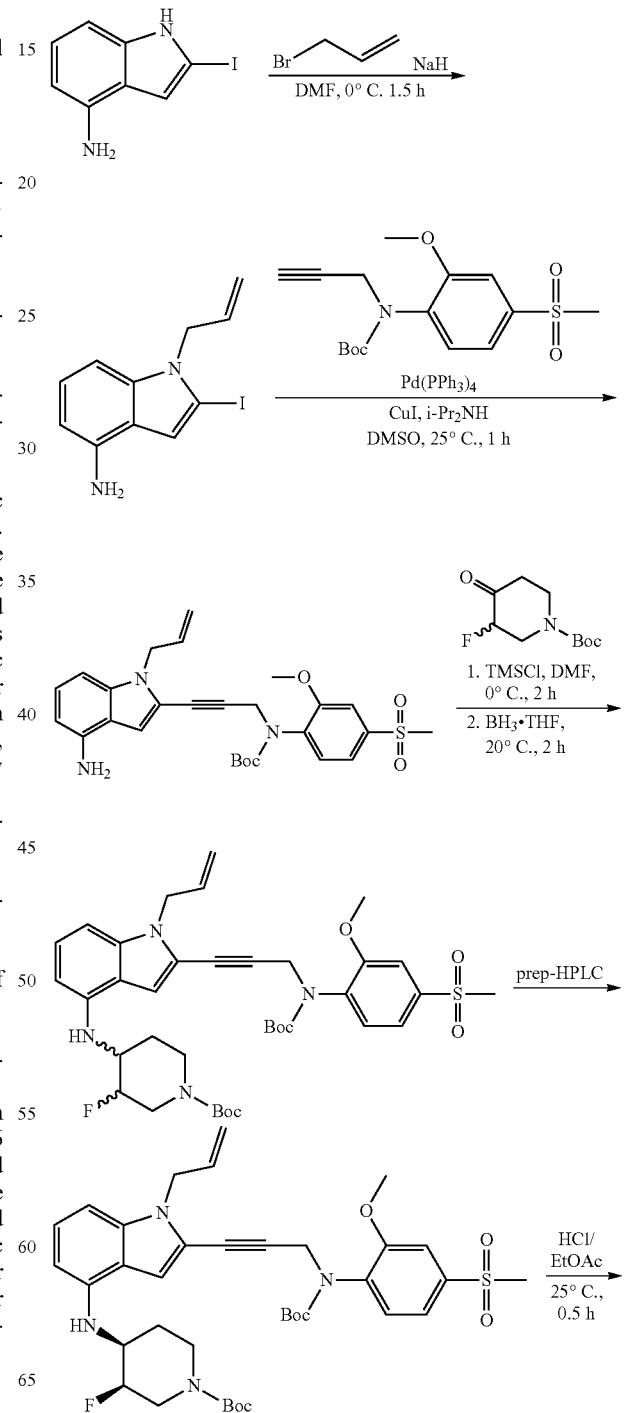

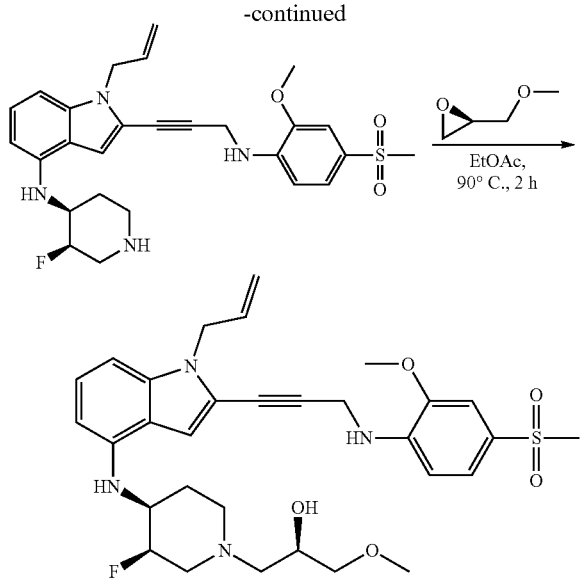

Preparation of 1-allyl-2-iodo-1H-indol-4-amine: To a solution of 2-iodo-1H-indol-4-amine (187.5 mg, 1.55 mmol, 0.5 eq.) in DMF (15 mL) was added NaH (372 mg, 9.30 mmol, 60% in mineral oil, 3 eq.) in one portion at 0° C. under N$_2$. The mixture was stirred at 0° C. for 30 min, and 3-bromoprop-1-ene (3.10 mmol, 18 μL, 1 eq.) was added. The mixture was stirred for 0.5 h at 0° C. TLC analysis showed that 30% of the starting material remained, and two new spots with polarity lower than that of the starting material were detected. An additional portion of 3-Bromoprop-1-ene (1.55 mmol, 0.5 eq.) was added to the reaction, and the resulting mixture was stirred for another 0.5 h at 0° C. TLC analysis showed that 10% of the starting material remained. The reaction was diluted with water (20 mL) and extracted with EtOAc (25 mL×2). The combined organic layers were washed with brine (25 mL×2), dried over anhydrous sodium sulfate, filtered, and concentrated to give a residue. The crude residue was purified by column chromatography (SiO$_2$, PE:EtOAc=6:1 to 4:1) to afford the desired product (530 mg, 1.78 mmol, 57.4% yield) as a brown solid.

Preparation of tert-butyl (3-(1-allyl-4-amino-1H-indol-2-yl)prop-2-yn-1-yl)(2-methoxy-4-(methylsulfonyl)phenyl)carbamate: To a solution of tert-butyl (2-methoxy-4-(methylsulfonyl)phenyl)(prop-2-yn-1-yl)carbamate (724.1 mg, 2.13 mmol, 1.2 eq.) in DMSO (10 mL) were added i-Pr$_2$NH (10.7 mmol, 1.51 mL, 6 eq.) and CuI (338.6 mg, 1.78 mmol, 1 eq.) under N$_2$. Then, 1-allyl-2-iodo-1H-indol-4-amine (530 mg, 1.78 mmol, 1 eq.) and Pd(PPh$_3$)$_4$ (205.4 mg, 178 μmol, 0.1 eq.) were added, and the mixture was stirred at 25° C. for 60 mins. TLC analysis showed that the reaction was complete. The reaction was diluted with water (30 mL) and extracted with EtOAc (30 mL×3). The organic phase was washed with water (30 mL×3) and brine (30 mL×3), dried over anhydrous sodium sulfate, filtered, and concentrated to give a residue. The crude residue was purified by prep-TLC (SiO$_2$, PE:EtOAc=1:1) to afford the desired product (460 mg, 903 μmol, 50.8% yield) as a brown solid.

Preparation of tert-butyl (3R,4S)-4-((1-allyl-2-(3-((tert-butoxycarbonyl)(2-methoxy-4-(methylsulfonyl)phenyl)amino)prop-1-yn-1-yl)-1H-indol-4-yl)amino)-3-fluoropiperidine-1-carboxylate: To a mixture of tert-butyl (3-(1-allyl-4-amino-1H-indol-2-yl)prop-2-yn-1-yl)(2-methoxy-4-(methylsulfonyl)phenyl)carbamate (400 mg, 785 μmol, 1 eq.) and tert-butyl (3R)-3-fluoro-4-oxo-piperidine-1-carboxylate (511.5 mg, 2.35 mmol, 3 eq.) in DMF (10 mL) was added TMSCl (7.85 mmol, 996 μL, 10 eq.) in one portion at 0° C. under N$_2$. The mixture was stirred at 0° C. for 60 min, and BH$_3$·THF (1 M, 7.85 mL, 10 eq.) was added. The mixture was stirred further at 20° C. for 2 h. LC-MS analysis showed that the reaction was complete. The reaction mixture was poured into water (30 mL) water and extracted with EtOAc (30 mL×3). The organic phase was washed with water (30 mL×2) and brine (30 mL×3), dried over anhydrous sodium sulfate, filtered, and concentrated in vacuo to give a residue. The crude residue was purified by prep-HPLC to afford the desired product (150 mg, 211 μmol, 26.9% yield) as a brown solid. MS (ES$^{30}$, m/z): 711.3.

Preparation of 1-allyl-N-((3R,4S)-3-fluoropiperidin-4-yl)-2-(3-((2-methoxy-4-(methylsulfonyl)phenyl)amino)prop-1-yn-1-yl)-1H-indol-4-amine: To a solution of tert-butyl (3R,4S)-4-((1-allyl-2-(3-((tert-butoxycarbonyl)(2-methoxy-4-(methylsulfonyl)phenyl)amino)prop-1-yn-1-yl)-1H-indol-4-yl)amino)-3-fluoropiperidine-1-carboxylate (140 mg, 197 μmol, 1 eq.) in HCl/EtOAc (4 M, 5 mL, 102 eq.) was stirred at 25° C. for 0.5 h. TLC analysis showed that the reaction was complete. The reaction mixture was adjusted to pH=8 by adding a saturated NaHCO$_3$ solution (20 mL), and the organic phase was extracted with EtOAc (25 mL×3). The combined organic layers were washed with brine (25 mL×2), dried over anhydrous sodium sulfate, filtered, and concentrated to give the desired product (90 mg, 176 μmol, 89.5% yield) as a brown gum. MS (ES$^{30}$, m/z): 511.2.

Preparation of (R)-1-((3R,4S)-4-((1-allyl-2-(3-((2-methoxy-4-(methylsulfonyl)phenyl)amino)prop-1-yn-1-yl)-1H-indol-4-yl)amino)-3-fluoropiperidin-1-yl)-3-methoxypropan-2-ol: A mixture of 1-allyl-N-((3R,4S)-3-fluoropiperidin-4-yl)-2-(3-((2-methoxy-4-(methylsulfonyl)phenyl)amino)prop-1-yn-1-yl)-1H-indol-4-amine (50 mg, 97.9 μmol, 1 eq.) and (2R)-2-(methoxymethyl)oxirane (490 μmol, 44 μL, 5 eq.) in EtOH (2 mL) was heated to 90° C. and stirred for 2 h. TLC analysis showed that the reaction was complete. The reaction was diluted with water (20 mL) and extracted with EtOAc (20 mL×2). The combined organic layers were washed with water (20 mL×2) and brine (20 mL×2), dried over anhydrous sodium sulfate, filtered, and concentrated to give a residue. The crude residue was purified by prep-HPLC to afford the desired product (12.1 mg, 20.2 μmol, 20.6% yield) as a white solid. MS (ES$^{30}$, m/z): 599.3.

Example D17: Synthesis of rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-N-(2-hydroxy-3-methoxypropyl)-3-methoxybenzamide (Compound 816A)

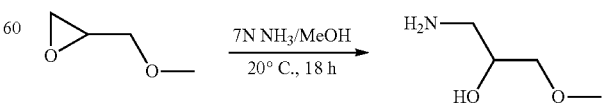

Preparation of 1-amino-3-methoxypropan-2-ol: 2-(Methoxymethyl)oxirane (5.68 mmol, 505 L, 1 eq.) was added to a solution of NH$_3$ (7 M, 811 μL, 1 eq.) in MeOH (20 mL). The solution was stirred at 20° C. for 18 h. The mixture was concentrated, and the crude residue was used directly without purification.

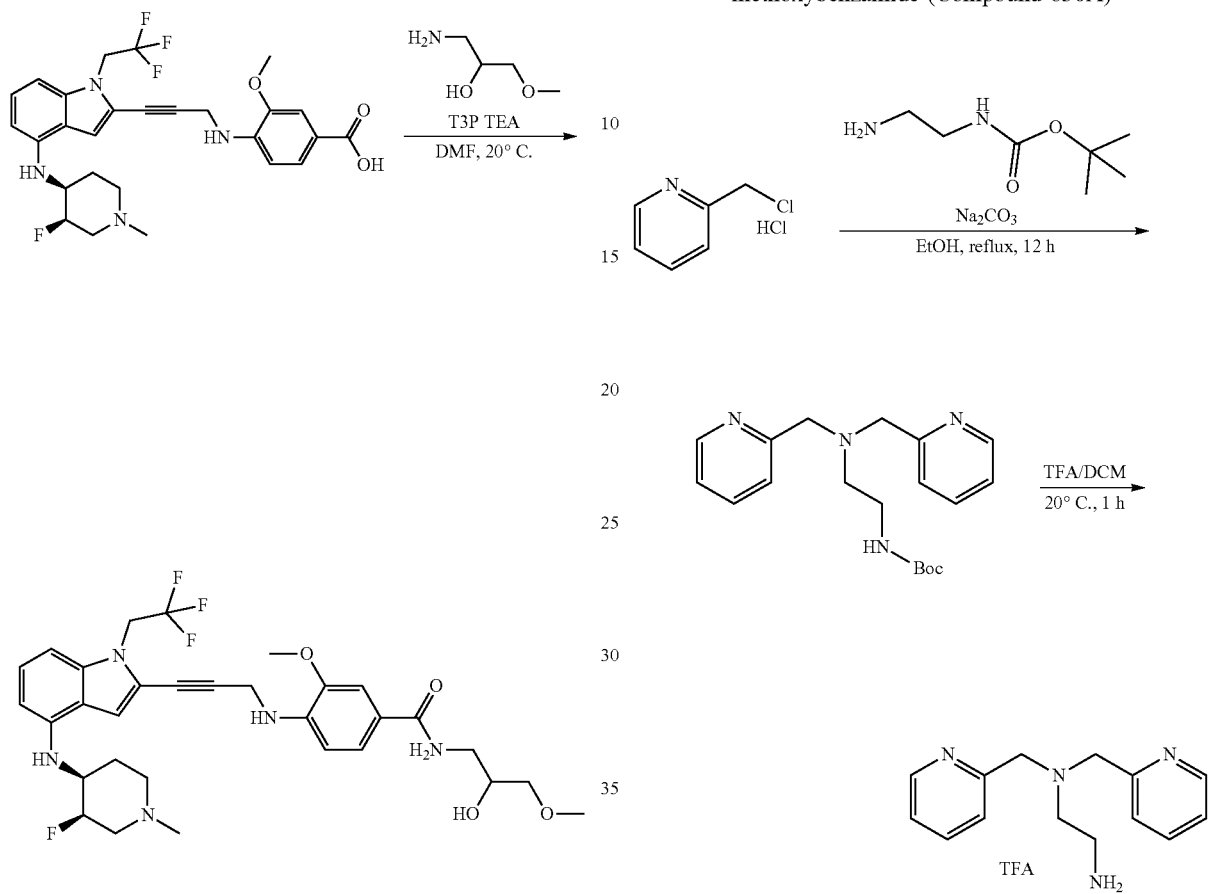

Preparation of rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-N-(2-hydroxy-3-methoxypropyl)-3-methoxybenzamide: To a mixture of 4-[3-[4-[[(3R,4S)-3-fluoro-1-methyl-4-piperidyl]amino]-1-(2,2,2-trifluoroethyl) indol-2-yl]prop-2-ynylamino]-3-methoxybenzoic acid (0.1 g, 178 µmol, 1 eq.), 1-amino-3-methoxypropan-2-ol (37.5 mg, 357 µmol, 2 eq.), and TEA (1.43 mmol, 28.5 µL, 8 eq.) in DMF (3 mL) was added T3P® (357 µmol, 106.1 µL, 2 eq., 50% (wt %) purity in EtOAc) at 0° C. The mixture was stirred at 20° C. for 16 h. TLC analysis (R$_f$=0.5, DCM:MeOH=10:1) showed that half the starting material remained, and some of the desired product was detected. The mixture was extracted with water (10 mL) and EtOAc (15 mL×3). The combined organic layers were washed with brine (5 mL×3), dried over anhydrous sodium sulfate, filtered, and concentrated. The crude residue was purified by prep-HPLC to afford the desired product (0.026 g, 40.1 µmol, 22.5% yield) as a yellow solid. MS (ES$^{30}$, m/z): 620.4.

Example D18: Synthesis of rac-N-(2-{bis[(pyridin-2-yl)methyl]amino}ethyl)-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzamide (Compound 830A)

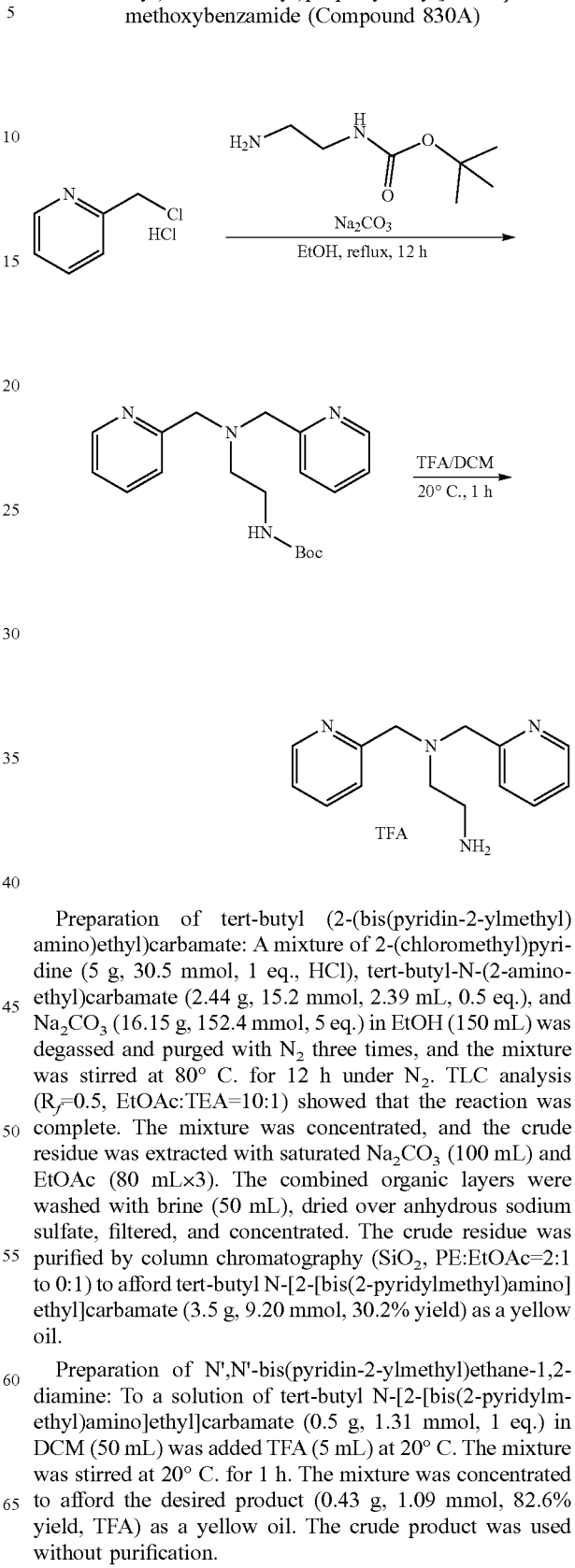

Preparation of tert-butyl (2-(bis(pyridin-2-ylmethyl)amino)ethyl)carbamate: A mixture of 2-(chloromethyl)pyridine (5 g, 30.5 mmol, 1 eq., HCl), tert-butyl-N-(2-aminoethyl)carbamate (2.44 g, 15.2 mmol, 2.39 mL, 0.5 eq.), and Na$_2$CO$_3$ (16.15 g, 152.4 mmol, 5 eq.) in EtOH (150 mL) was degassed and purged with N$_2$ three times, and the mixture was stirred at 80° C. for 12 h under N$_2$. TLC analysis (R$_f$=0.5, EtOAc:TEA=10:1) showed that the reaction was complete. The mixture was concentrated, and the crude residue was extracted with saturated Na$_2$CO$_3$ (100 mL) and EtOAc (80 mL×3). The combined organic layers were washed with brine (50 mL), dried over anhydrous sodium sulfate, filtered, and concentrated. The crude residue was purified by column chromatography (SiO$_2$, PE:EtOAc=2:1 to 0:1) to afford tert-butyl N-[2-[bis(2-pyridylmethyl)amino]ethyl]carbamate (3.5 g, 9.20 mmol, 30.2% yield) as a yellow oil.

Preparation of N',N'-bis(pyridin-2-ylmethyl)ethane-1,2-diamine: To a solution of tert-butyl N-[2-[bis(2-pyridylmethyl)amino]ethyl]carbamate (0.5 g, 1.31 mmol, 1 eq.) in DCM (50 mL) was added TFA (5 mL) at 20° C. The mixture was stirred at 20° C. for 1 h. The mixture was concentrated to afford the desired product (0.43 g, 1.09 mmol, 82.6% yield, TFA) as a yellow oil. The crude product was used without purification.

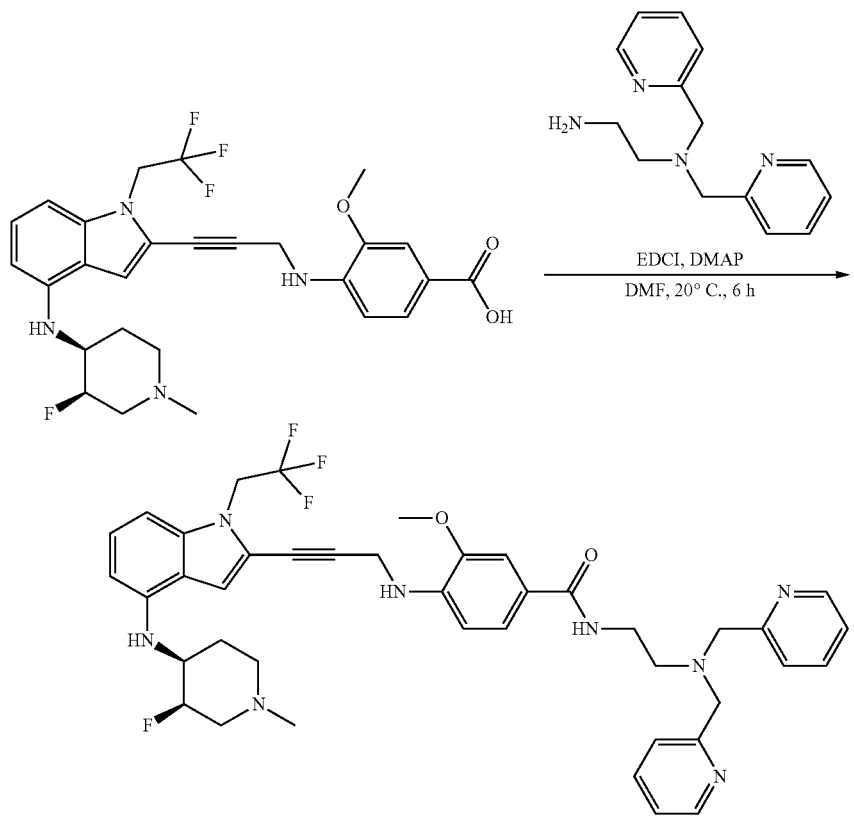

Preparation of rac-N-(2-{bis[(pyridin-2-yl)methyl]amino}ethyl)-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzamide: To a solution of 4-[3-[4-[[(3R,4S)-3-fluoro-1-methyl-4-piperidyl]amino]-1-(2,2,2-trifluoroethyl) indol-2-yl]prop-2-ynylamino]-3-methoxy-benzoic acid (0.1 g, 187.8 µmol, 1 eq.) in DCM (10 mL) were added EDCI (108 mg, 563 µmol, 3 eq.), N',N'-bis(2-pyridylmethyl)ethane-1,2-diamine (54.6 mg, 225.3 µmol, 1.2 eq.), and DMAP (22.9 mg, 187.8 µmol, 1 eq.) at 20° C. The mixture was stirred at 20° C. for 6 h. LC-MS and HPLC analysis showed that the reaction was complete. The mixture was extracted with water (15 mL) and DCM (15 mL×3). The organic layer was washed with brine (10 mL), dried over anhydrous sodium sulfate, filtered, and concentrated. The crude residue was purified by prep-HPLC to afford the desired product (0.031 g, 37.7 µmol, 20.1% yield) as a yellow solid. MS (ES$^{30}$, m/z): 757.4.

Example D19: Synthesis of 4-hydroxy-9-[(2-{3-[(4-methanesulfonyl-2-methoxyphenyl)amino]prop-1-yn-1-yl}-1-(2,2,2-trifluoroethyl)-1H-indol-4-yl)amino]-2-oxa-6λ$^5$-azaspiro[5.5]undecan-6-ylium (Compound 674A)

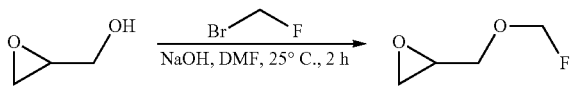

Preparation of 2-((fluoromethoxy)methyl)oxirane: To a solution of oxiran-2-ylmethanol (1 g, 13.50 mmol, 1 eq.) in DMF (10 mL) were added NaOH (539.9 mg, 13.5 mmol, 1 eq.) and bromofluoromethane (1.52 g, 13.5 mmol, 1 eq.) at 25° C. The mixture was stirred at 25° C. for 2 h. TLC analysis (PE:EtOAc=1:1, R$_f$=0.5) showed that the reaction was complete. The reaction was quenched with a saturated NH$_4$Cl solution (20 mL) and extracted with EtOAc (40 mL×3). The combined organic layers were washed with brine (40 mL×3), dried over anhydrous sodium sulfate, filtered, and concentrated to afford the desired product (500 mg, crude) as a light-yellow oil.

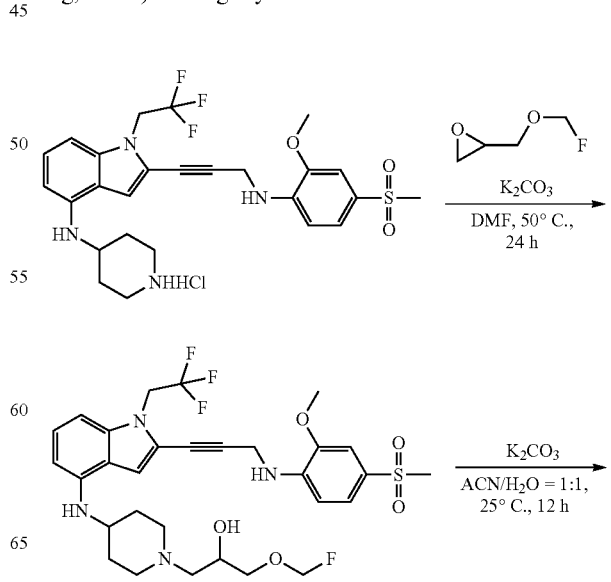

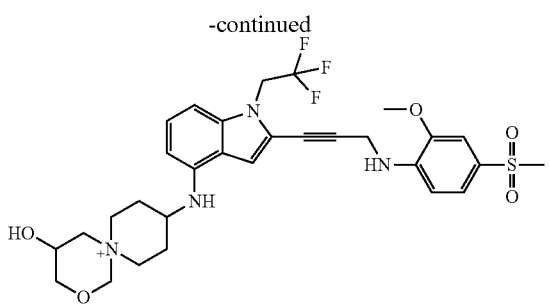

Preparation of 1-(fluoromethoxy)-3-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)propan-2-ol: To a solution of 2-(3-((2-methoxy-4-(methylsulfonyl)phenyl)amino)prop-1-yn-1-yl)-N-(piperidin-4-yl)-1-(2,2,2-trifluoroethyl)-1H-indol-4-amine hydrochloride (200 mg, 350.2 μmol, 1 eq., HCl) in DMF (4 mL) were added 2-((fluoromethoxy)methyl)oxirane (371.6 mg, 3.50 mmol, 10 eq.) and K$_2$CO$_3$ (242.0 mg, 1.75 mmol, 5 eq.) at 25° C. The mixture was heated to 50° C. and stirred further for 12 h. LC-MS analysis showed that 50% of the starting material was converted to the product. The reaction was quenched with saturated solution of NH$_4$Cl (20 mL) and extracted with EtOAc (30 mL×3). The combined organic layers were washed with brine (30 mL×3), dried over anhydrous sodium sulfate, filtered, and concentrated to afford 1-(fluoromethoxy)-3-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)propan-2-ol (300 mg, crude) as a black-brown oil.

Preparation of 4-hydroxy-9-[(2-{3-[(4-methanesulfonyl-2-methoxyphenyl)amino]prop-1-yn-1-yl}-1-(2,2,2-trifluoroethyl)-1H-indol-4-yl)amino]-2-oxa-6λ$^5$-azaspiro[5.5]undecan-6-ylium: To a solution of 1-(fluoromethoxy)-3-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)propan-2-ol (250 mg, 390.2 μmol, 1 eq.) in ACN (3 mL) and water (3 mL) was added K$_2$CO$_3$ (53.9 mg, 390.2 μmol, 1 eq.) in one portion at 25° C. The mixture was stirred at 25° C. for 12 h. LC-MS and HPLC analysis showed that the reaction was complete. The reaction was quenched with water (20 mL) and extracted with EtOAc (30 mL×3). The desired product was found in the aqueous phase, which was concentrated and purified by prep-HPLC to afford the desired product (7.0 mg, 10.5 μmol, 2.7% yield) as a white solid. MS (ES$^{30}$, m/z): 622.2.

Example D20: Synthesis of 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-(2,2,2-trifluoroethoxy)propan-2-ol (Compound 673A)

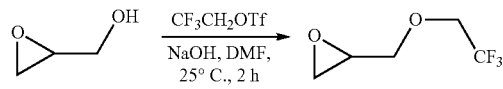

Preparation of 2-((2,2,2-trifluoroethoxy)methyl)oxirane: To a solution of oxiran-2-ylmethanol (1 g, 13.5 mmol, 1 eq.) in DMF (10 mL) were added NaOH (540 mg, 13.5 mmol, 1 eq.) and CF$_3$CH$_2$OTf (3.13 g, 13.5 mmol, 1 eq.) at 25° C. The mixture was stirred at 25° C. for 2 h. TLC analysis (PE:EtOAc=1:1, R$_f$=0.5) showed that the reaction was complete. The reaction was quenched with a saturated NH$_4$Cl solution (20 mL) and extracted with EtOAc (40 mL×3). The combined organic layers were washed with brine (40 mL×3), dried over anhydrous sodium sulfate, filtered, and concentrated to afford 2-((2,2,2-trifluoroethoxy)methyl)oxirane (700 mg, crude) as a light-yellow oil.

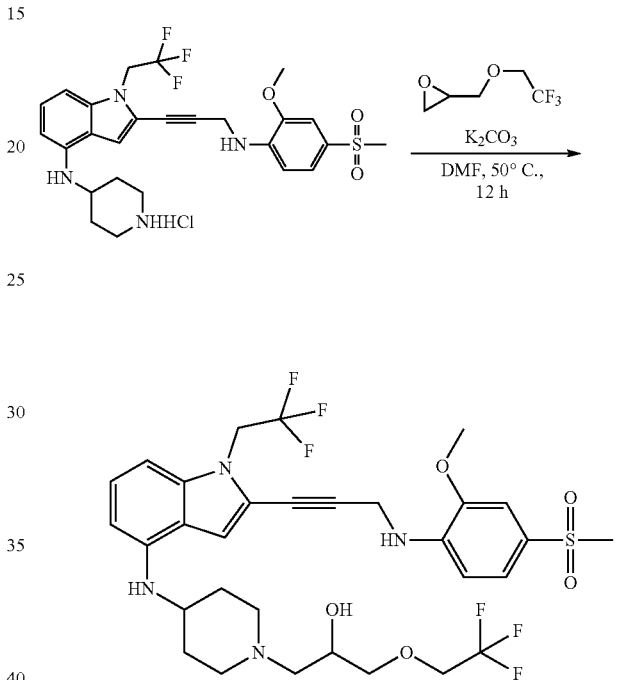

Preparation of 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-(2,2,2-trifluoroethoxy)propan-2-ol: To a solution of 2-(3-((2-methoxy-4-(methylsulfonyl)phenyl)amino)prop-1-yn-1-yl)-N-(piperidin-4-yl)-1-(2,2,2-trifluoroethyl)-1H-indol-4-amine hydrochloride (200 mg, 350.2 μmol, 1 eq., HCl) in DMF (3 mL) were added 2-((2,2,2-trifluoroethoxy)methyl) oxirane (547 mg, 3.50 mmol, 10 eq.) and K$_2$CO$_3$ (242.0 mg, 1.75 mmol, 5 eq.) at 25° C. The mixture was heated to 50° C. and stirred for 12 h. LC-MS analysis showed that the reaction was complete. The reaction was quenched with a saturated NH$_4$Cl solution (20 mL) and extracted with EtOAc (20 mL×3). The combined organic layers were washed with brine (20 mL×3), dried over anhydrous sodium sulfate, filtered, and concentrated. The residue was purified by prep-HPLC to afford the desired product (33.7 mg, 44.7 μmol, 12.8% yield) as a yellow solid. MS (ES$^{30}$, m/z): 691.2.

Example D21: Synthesis of Compounds 519A and 714A
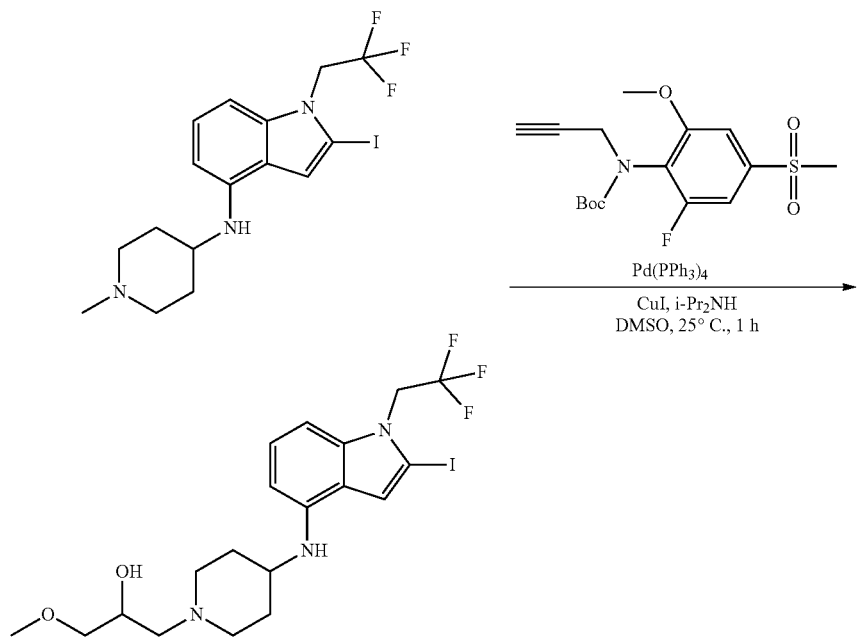 [SMILES: CN1CCC(Nc2cccc3c2cc(I)n3CC(F)(F)F)CC1 ; C#CCN(C(=O)OC(C)(C)C)c1c(F)cc(S(C)(=O)=O)cc1OC ; COCC(O)CN1CCC(Nc2cccc3c2cc(I)n3CC(F)(F)F)CC1 ; "Pd(PPh3)4"]
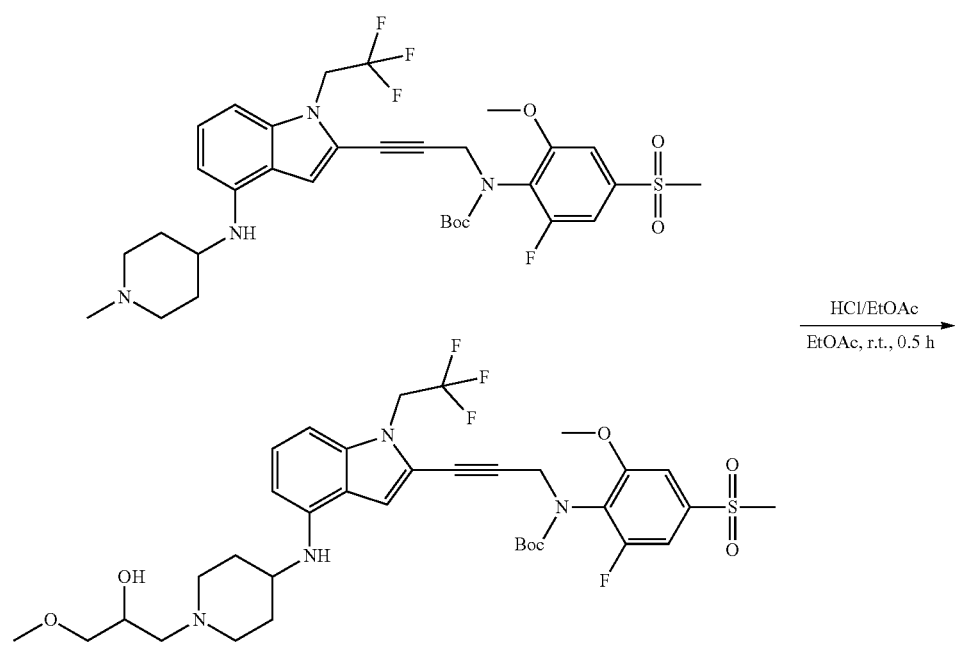

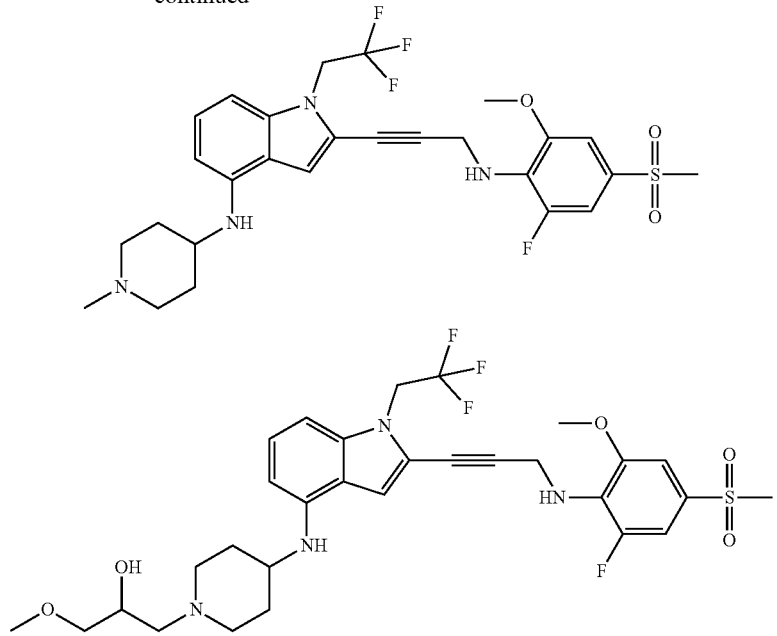

Preparation of tert-butyl (2-fluoro-6-methoxy-4-(methylsulfonyl)phenyl)(3-(4-((1-methylpiperidin-4-yl)amino)-1-(2,2,2-trifluoroethyl)-1H-indol-2-yl)prop-2-yn-1-yl)carbamate and tert-butyl (2-fluoro-6-methoxy-4-(methylsulfonyl)phenyl)(3-(4-((1-(2-hydroxy-3-methoxypropyl)piperidin-4-yl)amino)-1-(2,2,2-trifluoroethyl)-1H-indol-2-yl)prop-2-yn-1-yl)carbamate: To a solution of tert-butyl (2-fluoro-6-methoxy-4-(methylsulfonyl)phenyl)(prop-2-yn-1-yl)carbamate (1.2 eq.) in DMSO (1 mL) were added i-Pr$_2$NH (30 eq.), CuI (2 eq.), 2-iodo-N-(1-methylpiperidin-4-yl)-1-(2,2,2-trifluoroethyl)-1H-indol-4-amine or 1-(4-((2-iodo-1-(2,2,2-trifluoroethyl)-1H-indol-4-yl)amino)piperidin-1-yl)-3-methoxypropan-2-ol (114 μmol, 1 eq.), and Pd(PPh$_3$)$_4$ (0.25 eq.) at 25° C. The mixture was stirred at 25° C. for 1 h under N$_2$. The reaction mixture was poured into saturated EDTA solution (10 mL), and the mixture was stirred at 25° C. for 1 h and extracted with EtOAc. The combined organic layers were washed with brine (20 mL×3) dried over anhydrous sodium sulfate, filtered, and concentrated under reduced pressure. The crude residue was purified by prep-TLC to afford the desired products.

Preparation of 1-{4-[(2-{3-[(2-fluoro-4-methanesulfonyl-6-methoxyphenyl)amino]prop-1-yn-1-yl}-1-(2,2,2-trifluoroethyl)-1H-indol-4-yl)amino]piperidin-1-yl}-3-methoxypropan-2-ol and 2-{3-[(2-fluoro-4-methanesulfonyl-6-methoxyphenyl)amino]prop-1-yn-1-yl}-N-(1-methylpiperidin-4-yl)-1-(2,2,2-trifluoroethyl)-1H-indol-4-amine: A solution of tert-butyl (2-fluoro-6-methoxy-4-(methylsulfonyl)phenyl)(3-(4-((1-methylpiperidin-4-yl)amino)-1-(2,2,2-trifluoroethyl)-1H-indol-2-yl)prop-2-yn-1-yl)carbamate or tert-butyl (2-fluoro-6-methoxy-4-(methylsulfonyl)phenyl)(3-(4-((1-(2-hydroxy-3-methoxypropyl)piperidin-4-yl)amino)-1-(2,2,2-trifluoroethyl)-1H-indol-2-yl)prop-2-yn-1-yl)carbamate (1 eq) in HCl/EtOAc (4 M, 2 mL) was stirred at 25° C. for 0.5 h. A saturated Na$_2$CO$_3$ solution (100 mL) was added to the solution dropwise to adjust the pH of the mixture to >7. The mixture was extracted with EtOAc (30 mL×3). The combined organic layers were washed with brine (30 mL×3), dried over anhydrous sodium sulfate, filtered, and concentrated under reduced pressure to give a residue. The residue was purified by prep-TLC or prep-HPLC to afford the desired products. 1-{4-[(2-{3-[(2-fluoro-4-methanesulfonyl-6-methoxyphenyl)amino]prop-1-yn-1-yl}-1-(2,2,2-trifluoroethyl)-1H-indol-4-yl)amino]piperidin-1-yl}-3-methoxypropan-2-ol, MS (ES$^{30}$, m/z): 641.2; and 2-{3-[(2-fluoro-4-methanesulfonyl-6-methoxyphenyl)amino]prop-1-yn-1-yl}-N-(1-methylpiperidin-4-yl)-1-(2,2,2-trifluoroethyl)-1H-indol-4-amine, MS (ES$^{30}$, m/z): 567.2.

Example D22: Synthesis of 2-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)ethan-1-ol (Compound 693A)

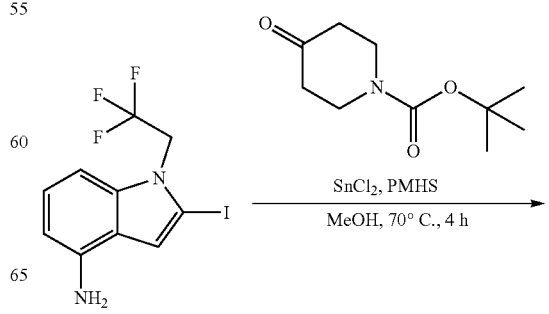

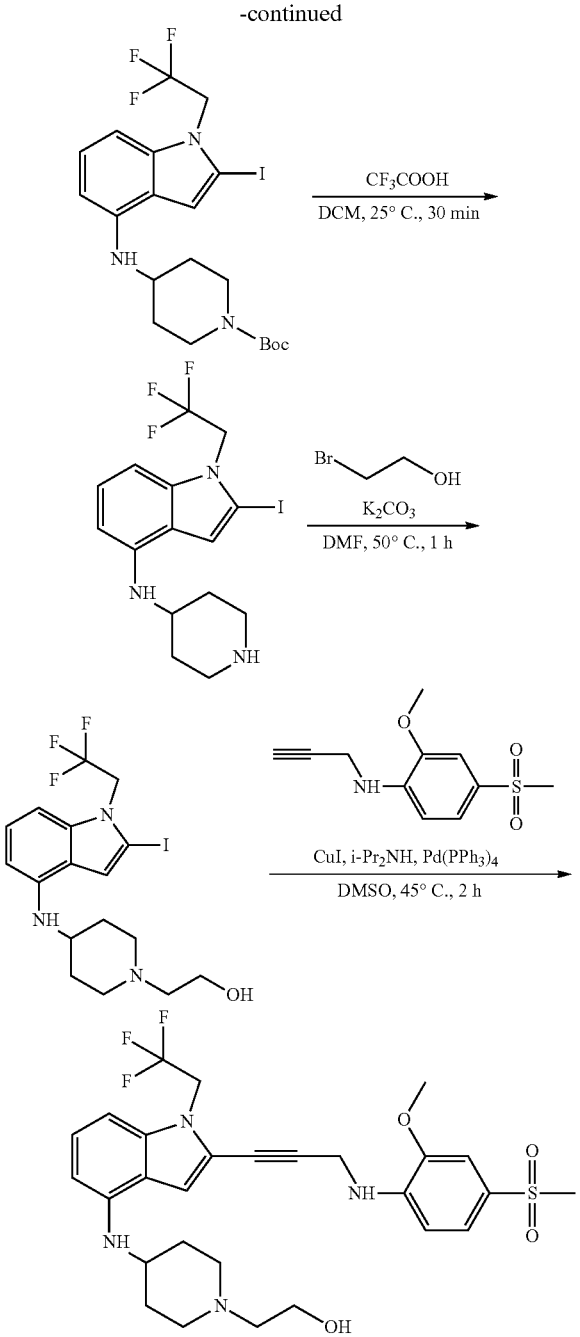

-continued

Preparation of tert-butyl 4-((2-iodo-1-(2,2,2-trifluoroethyl)-1H-indol-4-yl)amino)piperidine-1-carboxylate: To a solution of 2-iodo-1-(2,2,2-trifluoroethyl)indol-4-amine (4 g, 11.8 mmol, 1 eq.) and tert-butyl 4-oxopiperidine-1-carboxylate (11.8 g, 58.8 mmol, 5 eq.) in MeOH (100 mL) were added $SnCl_2 \cdot 2H_2O$ (530.8 mg, 2.35 mmol, 0.20 eq.) and PMHS (CAS [9004-73-3], 3.53 g, 58.81 mmol, 5 eq.). The mixture was stirred at 70° C. for 2 h. LC-MS analysis showed that the starting material was consumed completely, and that one main peak with desired MS data was detected. The reaction mixture was concentrated under reduced pressure. To the crude residue was added PE (700 mL), and the resulting mixture was stirred at 15° C. for 1 h. The mixture was filtered and concentrated to afford tert-butyl 4-((2-iodo-1-(2,2,2-trifluoroethyl)-1H-indol-4-yl)amino)piperidine-1-carboxylate (4.40 g, 7.99 mmol, 67.9% yield) as a gray solid. MS ($ES^{30}$, m/z): 524.1.

Preparation of 2-iodo-N-(piperidin-4-yl)-1-(2,2,2-trifluoroethyl)-1H-indol-4-amine: A solution of tert-butyl 4-((2-iodo-1-(2,2,2-trifluoroethyl)-1H-indol-4-yl)amino)piperidine-1-carboxylate (2.40 g, 4.59 mmol, 1 eq.) in $CF_3COOH$ (4 mL) and DCM (16 mL) was prepared. The reaction mixture was stirred at 25° C. for 30 min. LC-MS analysis showed that the starting material was consumed completely, and that one main peak with desired MS data was detected. The reaction mixture was concentrated under reduced pressure to afford 2-iodo-N-(piperidin-4-yl)-1-(2,2,2-trifluoroethyl)-1H-indol-4-amine (1.70 g, 3.44 mmol, 75.0% yield) as a gray solid. MS ($ES^{30}$, m/z): 424.1.

Preparation of 2-(4-((2-iodo-1-(2,2,2-trifluoroethyl)-1H-indol-4-yl)amino)piperidin-1-yl)ethan-1-ol: To a solution of 2-iodo-N-(piperidin-4-yl)-1-(2,2,2-trifluoroethyl)-1H-indol-4-amine (500 mg, 1.18 mmol, 1 eq.) in DMF (10 mL) were added $K_2CO_3$ (816.4 mg, 5.91 mmol, 5 eq.) and 2-bromoethanol (1.77 mmol, 125.8 µL, 1.50 eq.). The mixture was stirred at 50° C. for 2 h. LC-MS analysis showed that the starting material was consumed completely, and that one main peak with desired MS data was detected. The reaction mixture was partitioned using water (50 mL) and EtOAc (50 mL). The organic phase was separated. The aqueous phase was washed with EtOAc (10 mL×3). The combined organic layers were dried over anhydrous sodium sulfate, filtered, and concentrated under reduced pressure to give a residue. The residue was purified by column chromatography ($SiO_2$, PE:EtOAc=10:1 to 1:1) to afford the desired product (400 mg, 856.0 µmol, 72.6% yield) as a brown solid. MS ($ES^{30}$, m/z): 468.2.

Preparation of 2-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)ethan-1-ol: A solution of 2-methoxy-4-methylsulfonyl-N-prop-2-ynyl-aniline (265.6 mg, 963 µmol, 1.50 eq., HCl) in DMSO (5 mL) was flushed with $N_2$. CuI (122.3 mg, 642 µmol, 1 eq.) and N-isopropylpropan-2-amine (1.93 mmol, 270 µL, 3 eq.) were added to the mixture. 2-(4-((2-iodo-1-(2,2,2-trifluoroethyl)-1H-indol-4-yl)amino)piperidin-1-yl)ethan-1-ol (300 mg, 642 µmol, 1 eq.) was added, the mixture was flushed with $N_2$, and 2-methoxy-4-methylsulfonyl-N-prop-2-ynyl-aniline (265.6 mg, 963 µmol, 1.50 eq., HCl) was added again. The reaction mixture was flushed with $N_2$ again and stirred at 45° C. for 2 h. LC-MS analysis showed that the starting material was consumed completely, and one main peak with desired MS data was detected. The reaction mixture was partitioned using a saturated EDTA solution (20 mL) and EtOAc (20 mL). The organic phase was separated, and the aqueous phase was washed with EtOAc (5 mL×3). The combined organic layers were dried over anhydrous sodium sulfate, filtered, and concentrated under reduced pressure. The crude residue was purified by prep-HPLC to afford the desired product (52.2 mg, 90.2 µmol, 14.1% yield) as a white solid. MS ($ES^{30}$, m/z): 579.2.

Example D23: Synthesis of 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzoic acid (Compound 705A)

Example D24: Synthesis of 2-{3-[(4-methanesulfonyl-2-methoxyphenyl)amino]prop-1-yn-1-yl}-N-[1-(3-methanesulfonylpropyl)piperidin-4-yl]-1-(2,2,2-trifluoroethyl)-1H-indol-4-amine (Compound 706A)

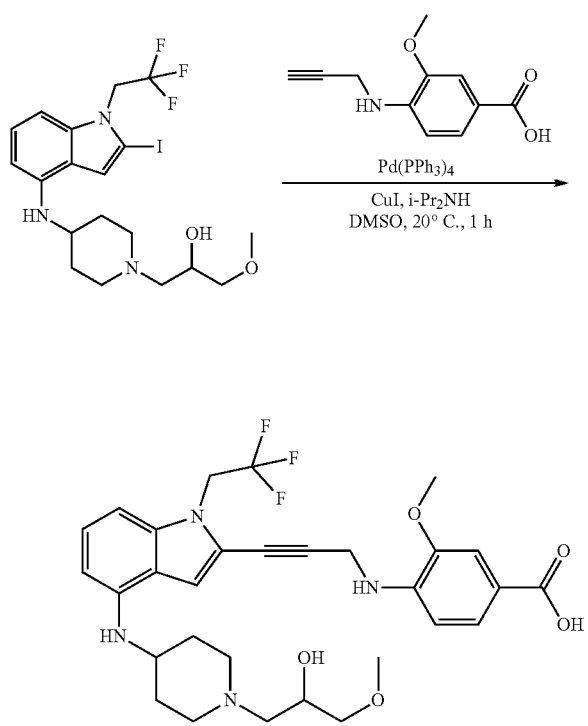

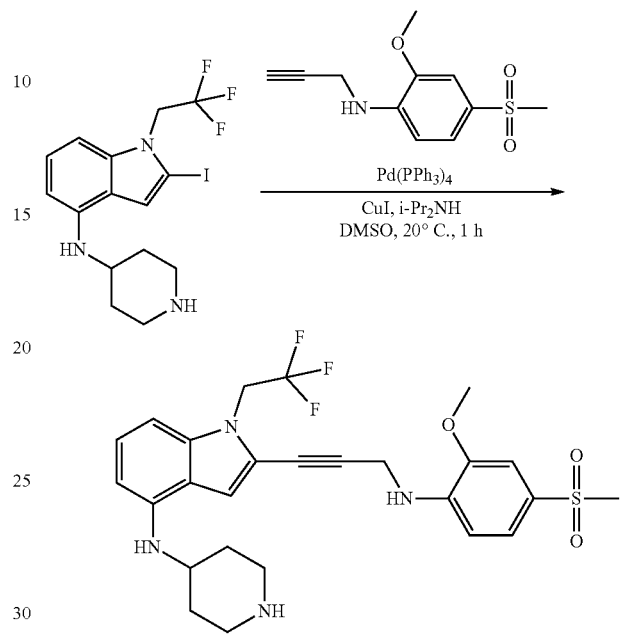

A mixture of 1-(4-((2-iodo-1-(2,2,2-trifluoroethyl)-1H-indol-4-yl)amino)piperidin-1-yl)-3-methoxypropan-2-ol, 3-methoxy-4-(prop-2-ynylamino)benzoic acid (48.16 mg, 234.68 μmol, 1.2 eq.), CuI (37.25 mg, 195.57 μmol, 1 eq.), Pd(PPh₃)₄ (45.20 mg, 39.11 μmol, 0.2 eq.), and i-Pr₂NH (197.90 mg, 1.96 mmol, 276.39 μL, 10 eq.) in DMSO (3 mL) was degassed and purged with N₂ three times. The mixture was stirred at 20° C. for 1 h. under N₂. TLC analysis (EtOAc:TEA=10:1, R$_f$=0.02) indicated that the starting material was consumed completely, and one major new spot was detected. The crude reaction mixture was added to a saturated aqueous EDTA solution and stirred at 20° C. for 1 h. The mixture was extracted with EtOAc (15 mL×3) and The combined organic layers were washed with brine (10 mL×3), dried over anhydrous sodium sulfate, filtered, and concentrated under reduced pressure. The resulting residue was purified by prep-TLC (SiO₂, EtOAc:TEA=15:1) and by prep-HPLC to afford the desired product: 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzoic acid (40 mg, 67.28 μmol, 34.40% yield) as a yellow solid. MS (ES$^{30}$, m/z): 589.3.

Preparation of 2-(3-((2-methoxy-4-(methylsulfonyl)phenyl)amino)prop-1-yn-1-yl)-N-(piperidin-4-yl)-1-(2,2,2-trifluoroethyl)-1H-indol-4-amine: A mixture of 2-iodo-N-(piperidin-4-yl)-1-(2,2,2-trifluoroethyl)-1H-indol-4-amine (0.2 g, 472.57 μmol, 1 eq.), 2-methoxy-4-methylsulfonyl-N-prop-2-ynyl-aniline (135.70 mg, 567.09 μmol, 1.2 eq.), CuI (90 mg, 472.57 μmol, 1 eq.), i-Pr₂NH (478.20 mg, 4.73 mmol, 667.87 μL, 10 eq.), and Pd(PPh₃)₄ (109.22 mg, 94.51 μmol, 0.2 eq.) in DMSO (3 mL) was degassed and purged with N₂ three times. The mixture was stirred at 20° C. for 1 h. under N₂. TLC analysis (EtOAc:TEA=10:1, R$_f$=0.1) indicated that the starting material was consumed completely, and one major new spot was detected. A saturated aqueous EDTA solution was added to the crude reaction mixture, and the resulting mixture was stirred at 20° C. for 1 h. The mixture was extracted with EtOAc (15 mL×3). The combined organic layers were washed with brine (10 mL×3), dried over anhydrous sodium sulfate, filtered, and concentrated under reduced pressure. The crude product 2-(3-((2-methoxy-4-(methylsulfonyl)phenyl)amino)prop-1-yn-1-yl)-N-(piperidin-4-yl)-1-(2,2,2-trifluoroethyl)-1H-indol-4-amine (0.11 g, 185.19 μmol, 39.19% yield) was obtained as a yellow solid and used in the next step without further purification.

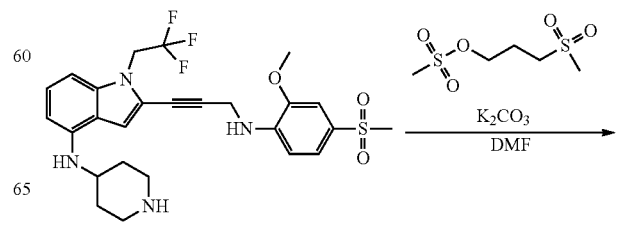

1007

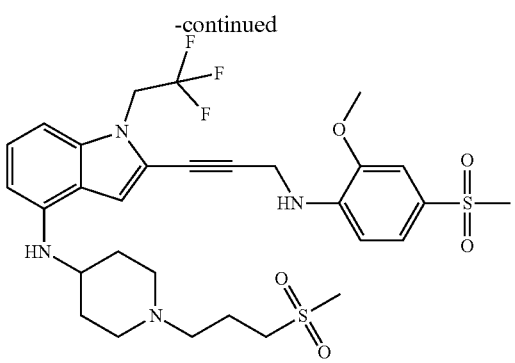

A mixture of 2-(3-((2-methoxy-4-(methylsulfonyl)phenyl)amino)prop-1-yn-1-yl)-N-(piperidin-4-yl)-1-(2,2,2-trifluoroethyl)-1H-indol-4-amine (0.1 g, 187.06 μmol, 1 eq.), 3-methylsulfonylpropyl methanesulfonate (121.37 mg, 561.18 μmol, 3 eq.), and K$_2$CO$_3$ (129.26 mg, 935.29 μmol, 5 eq.) in DMF (3 mL) was stirred at 80° C. for 2 h. under N$_2$. TLC analysis (EtOAc:TEA=10:1, R$_f$=0.25) indicated that one major new spot was detected. The mixture was filtered and concentrated under reduced pressure. The crude residue was purified by prep-HPLC to afford the desired product 2-{3-[(4-methanesulfonyl-2-methoxyphenyl)amino]prop-1-yn-1-yl}-N-[1-(3-methanesulfonylpropyl)piperidin-4-yl]-1-(2,2,2-trifluoroethyl)-1H-indol-4-amine (0.025 g, 37.80 μmol, 20.21% yield) as a yellow solid. MS (ES$^{30}$, m/z): 655.2.

Example D25: Synthesis of Compounds 586A, 587A, 588A, and 589A

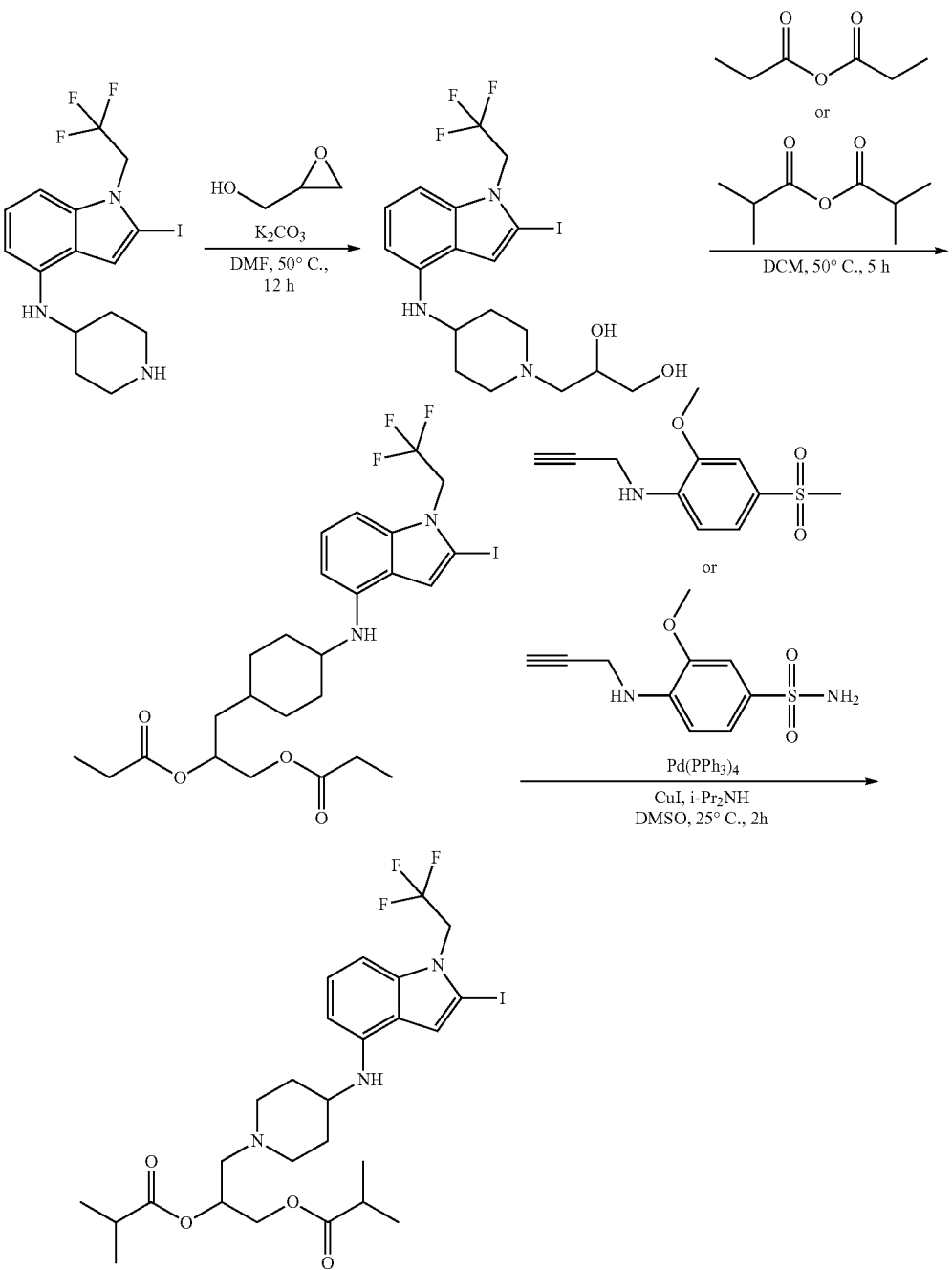

-continued
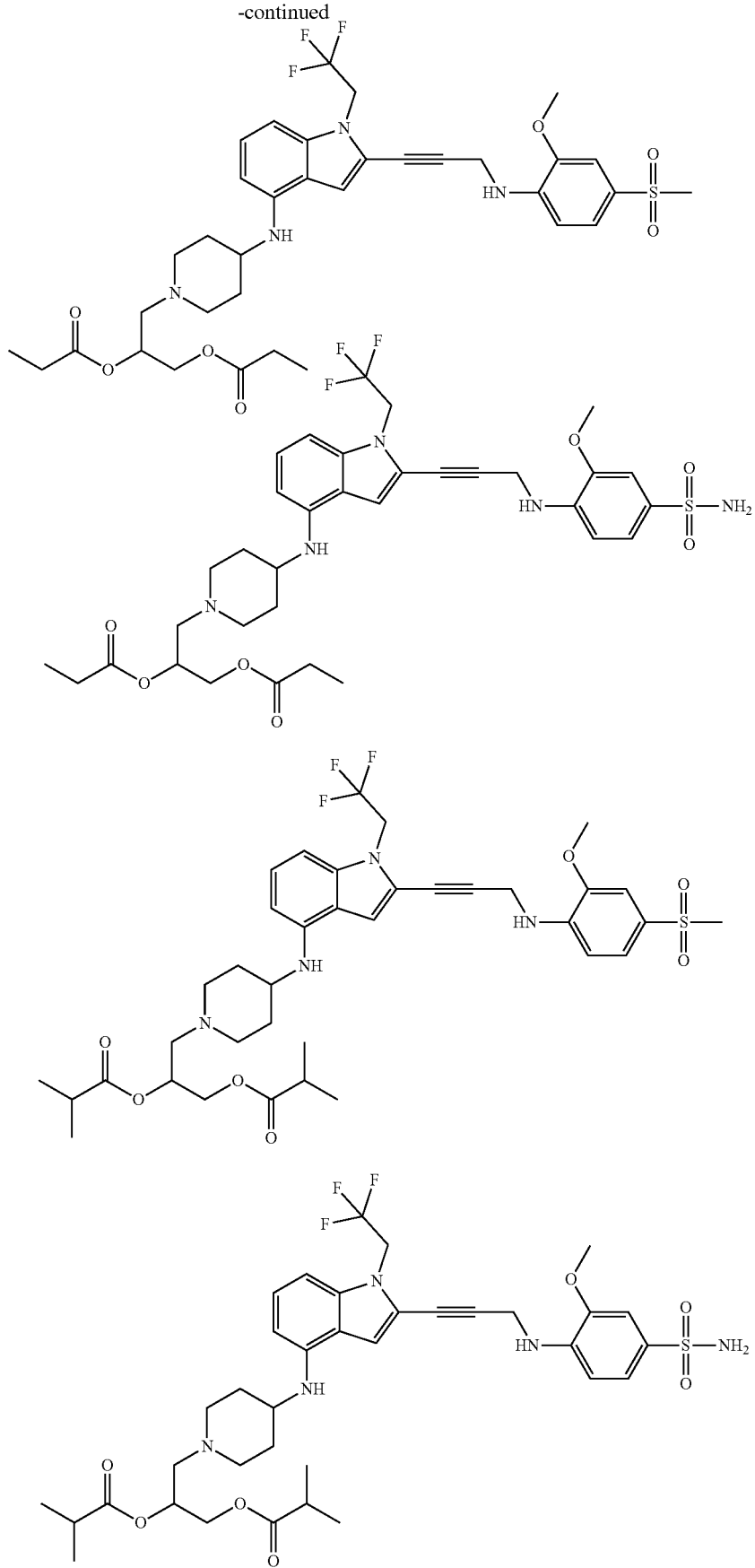

Preparation of 3-(4-((2-iodo-1-(2,2,2-trifluoroethyl)-1H-indol-4-yl)amino)piperidin-1-yl)propane-1,2-diol: To a mixture of 2-iodo-N-(piperidin-4-yl)-1-(2,2,2-trifluoroethyl)-1H-indol-4-amine (2 g, 4.54 mmol, 1 eq.) in DMF (20 mL) were added oxiran-2-ylmethanol (1.68 g, 22.72 mmol, 1.50 mL, 5 eq.) and $K_2CO_3$ (1.88 g, 13.63 mmol, 3 eq.). The mixture was stirred at 50° C. for 5 h. TLC and LC-MS analysis showed that the starting material was consumed completely. The reaction was partitioned by adding water (100 mL) and EtOAc (100 mL). The aqueous phase was extracted with EtOAc (100 mL×3). The combined organic layers were washed with brine (100 mL×3), dried over anhydrous sodium sulfate, filtered, and concentrated to afford the crude product (1.2 g, 2.22 mmol, 48.85% yield) as a black-brown oil. MS ($ES^{30}$, m/z): 497.8.

Preparation of 3-(4-((2-iodo-1-(2,2,2-trifluoroethyl)-1H-indol-4-yl)amino)piperidin-1-yl)propane-1,2-diyl dipropionate and 3-(4-((2-iodo-1-(2,2,2-trifluoroethyl)-1H-indol-4-yl)amino)piperidin-1-yl)propane-1,2-diyl bis(2-methylpropanoate): To a mixture of 3-(4-((2-iodo-1-(2,2,2-trifluoroethyl)-1H-indol-4-yl)amino)piperidin-1-yl) propane-1,2-diol (200 mg, 361.96 μmol, 1 eq.) in DCM (3 mL) was added propionic anhydride (117.76 mg, 904.90 μmol, 116.60 μL, 2.5 eq.) or isobutyric anhydride (143.15 mg, 904.90 μmol, 150.05 μL, 2.5 eq.). The mixture was stirred at 50° C. for 5 h. TLC and LC-MS analysis showed that the starting material was consumed completely. The reaction was partitioned by adding water (100 mL) and EtOAc (20 mL). The aqueous phase was extracted with EtOAc (50 mL×3). The combined organic layers were washed with brine (100 mL×3), dried over anhydrous sodium sulfate, filtered, and concentrated in vacuo. The crude product was purified by prep-TLC (PE:EtOAc=1:1, $R_f$=0.63) to afford the desired products (120 mg, crude) as light-brown oils. 3-(4-((2-iodo-1-(2,2,2-trifluoroethyl)-1H-indol-4-yl)amino)piperidin-1-yl)propane-1,2-diyl dipropionate, MS ($ES^{30}$, m/z): 609.9; 3-(4-((2-iodo-1-(2,2,2-trifluoroethyl)-1H-indol-4-yl)amino)piperidin-1-yl)propane-1,2-diyl bis(2-methylpropanoate), MS ($ES^{30}$, m/z): 638.3.

Preparation of 3-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)propane-1,2-diyl dipropionate: To a solution of 3-(4-((2-iodo-1-(2,2,2-trifluoroethyl)-1H-indol-4-yl)amino)piperidin-1-yl) propane-1,2-diyl dipropionate (60 mg, 98.45 μmol, 1 eq.) in DMSO (2 mL) were added 2-methoxy-4-methylsulfonyl-N-prop-2-ynyl-aniline (31.41 mg, 118.15 μmol, 1.2 eq.), i-$PrNH_2$ (58.20 mg, 984.54 μmol, 84.59 μL, 10 eq.), CuI (18.75 mg, 98.45 μmol, 1 eq.), and $Pd(PPh_3)_4$ (22.75 mg, 19.69 μmol, 0.2 eq.). The mixture was stirred at 25° C. for 2 h under $N_2$. LC-MS and TLC analysis (PE:EtOAc=1:1, $R_f$=0.5) showed that the starting material was consumed completely. The reaction mixture was quenched by addition of a saturated aqueous EDTA solution (20 mL) at 25° C. and stirring for 2 h. The reaction mixture was partitioned between EtOAc and water. The aqueous phase was extracted with EtOAc (5 mL×3) and the organic phase was washed with brine 30 mL (10 mL×3), dried over anhydrous sodium sulfate, filtered, and concentrated in vacuo to give the crude product. The residue was purified by prep-TLC and lyophilized to give the product[3-[4-[[2-[3-(2-methoxy-4-methylsulfonyl-anilino)prop-1-ynyl]-1-(2,2,2-trifluoroethyl)indol-4-yl]amino]-1-piperidyl]-2-propanoyloxy-propyl] propanoate (21.5 mg, 27.92 μmol, 28.36% yield) as a yellow solid. The remaining compounds were synthesized using an analogous method.

1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-(propanoyloxy)propan-2-yl propanoate, (21.5 mg, 28.4% yield) MS ($ES^{30}$, m/z): 721.3; 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}-3-(propanoyloxy)propan-2-yl propanoate, (58.1 mg, 53.8% yield) MS ($ES^{30}$, m/z): 722.2; 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-[(2-methylpropanoyl)oxy]propan-2-yl 2-methylpropanoate, (21.4 mg, 21.7% yield) MS ($ES^{30}$, m/z): 749.3; and 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}-3-[(2-methylpropanoyl)oxy]propan-2-yl 2-methylpropanoate, (23.8 mg, 26.6% yield) MS ($ES^{30}$, m/z): 750.3.

Example D26: Synthesis of Compounds 590A and 591A

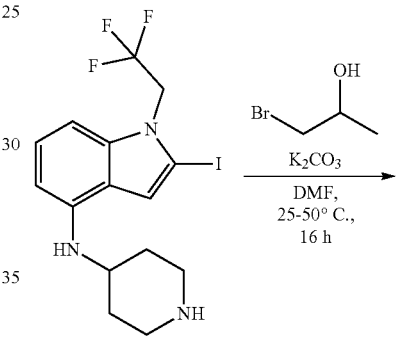

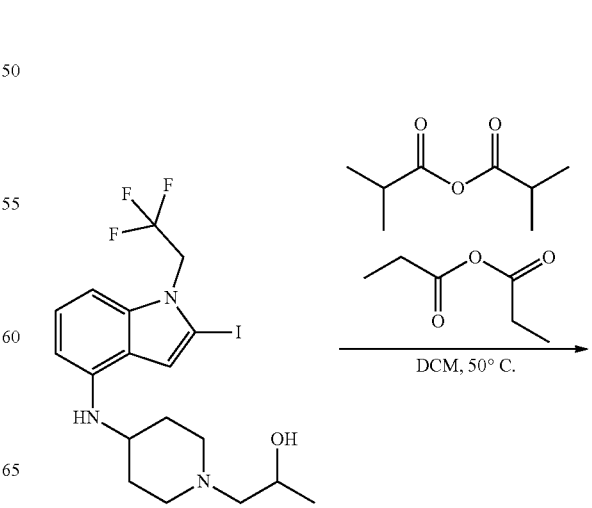

-continued

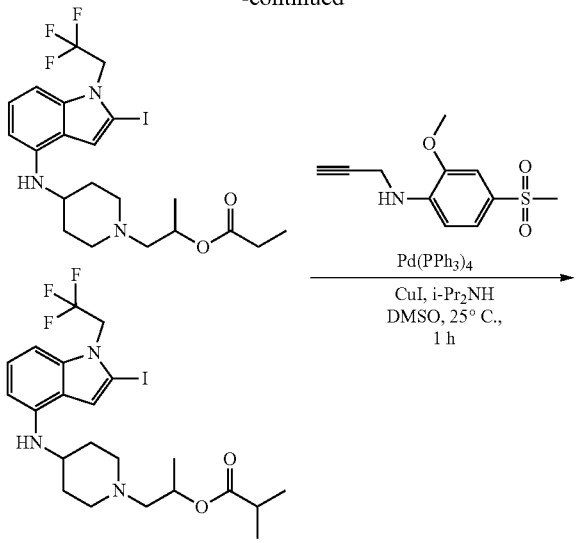

Preparation of 1-(4-((2-iodo-1-(2,2,2-trifluoroethyl)-1H-indol-4-yl)amino)piperidin-1-yl)propan-2-ol: To a mixture of 2-iodo-N-(piperidin-4-yl)-1-(2,2,2-trifluoroethyl)-1H-indol-4-amine (2 g, 4.63 mmol, 1 eq.) in DMF (20 mL) were added 1-bromopropan-2-ol (9.20 g, 46.31 mmol, 10 eq.) and $K_2CO_3$ (3.20 g, 23.16 mmol, 5 eq.) at 25° C. The mixture was stirred at 50° C. for 12 h. TLC and LC-MS analysis showed that the starting material was consumed completely. The reaction was partitioned by adding water (20 mL) and EtOAc (50 mL). The aqueous phase was extracted with EtOAc (50 mL×3). The combined organic layers were washed with brine (50 mL×3), dried over anhydrous sodium sulfate, filtered, and concentrated in vacuo to afford the desired product 1-(4-((2-iodo-1-(2,2,2-trifluoroethyl)-1H-indol-4-yl)amino)piperidin-1-yl)propan-2-ol (3.8 g, crude) as a black-brown oil. MS ($ES^{30}$, m/z): 482.0.

Preparation of 1-(4-((2-iodo-1-(2,2,2-trifluoroethyl)-1H-indol-4-yl)amino)piperidin-1-yl)propan-2-yl isobutyrate: To a solution of 1-[4-[[2-iodo-1-(2,2,2-trifluoroethyl)indol-4-yl]amino]-1-piperidyl]propan-2-ol (0.1 g, 187 µmol, 1 eq.) in DCM (5 mL) was added 2-methylpropanoyl 2-methylpropanoate (118.33 mg, 747.99 µmol, 124.03 µL, 4 eq.), and the reaction mixture was stirred at 50° C. for 10 h. TLC analysis showed that the reaction was completed (EtOAc, $R_f$=0.6). The reaction mixture was quenched by adding water (10 mL) and extracted with EtOAc (15 mL×3). The combined organic layers were washed with brine (50 mL) and water (50 mL), dried over anhydrous sodium sulfate, filtered and concentrated to give the crude product. The crude product was purified by prep-TLC (EtOAc, $R_f$=0.6) to afford [2-[4-[[2-iodo-1-(2,2,2-trifluoroethyl)indol-4-yl]amino]-1-piperidyl]-1-methyl-ethyl]2-methylpropanoate (90 mg, 163.23 µmol, 87.29% yield) as a yellow oil. MS ($ES^{30}$, m/z): 552.0. 1-(4-((2-iodo-1-(2,2,2-trifluoroethyl)-1H-indol-4-yl)amino)piperidin-1-yl)propan-2-yl propionate was prepared followed the procedure described above. 160 mg, 89.57% yield) MS ($ES^{30}$, m/z): 538.2.

Preparation of 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl propanoate and 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl 2-methylpropanoate: To a mixture of 2-methoxy-4-(methylsulfonyl)-N-(prop-2-yn-1-yl)aniline (39.84 mg, 166.49 µmol, 1.2 eq.) in DMSO (2 mL) were added i-Pr$_2$NH (82.01 mg, 1.39 mmol, 119.20 µL, 10 eq.), CuI (26.42 mg, 138.74 µmol, 1 eq.), 1-(4-((2-iodo-1-(2,2,2-trifluoroethyl)-1H-indol-4-yl)amino)piperidin-1-yl)propan-2-yl propionate (90 mg, 138.74 µmol, 1 eq.) or 1-(4-((2-iodo-1-(2,2,2-trifluoroethyl)-1H-indol-4-yl)amino)piperidin-1-yl)propan-2-yl isobutyrate and Pd(PPh$_3$)$_4$ (32.06 mg, 27.75 µmol, 0.2 eq.) at 25° C. The mixture was stirred at 25° C. for 1 h. under N$_2$. LC-MS and TLC analysis showed that the reaction was complete. The reaction mixture was quenched by adding a saturated aqueous EDTA solution (20 mL) at 25° C. and stirred for 2 h. The reaction mixture was partitioned by adding EtOAc (5 mL) and the aqueous phase was extracted with EtOAc (5 mL×3). The organic phase was washed with brine (5 mL×3) dried over anhydrous sodium sulfate, filtered, and concentrated in vacuo to obtain the crude product (100 mg). The crude residue was purified by prep-TLC (DCM:MeOH=20:1, $R_f$=0.5) and prep-HPLC to afford the desired products as light-yellow solids.

1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl propanoate (6.3 mg, 6.98% yield), MS ($ES^{30}$, m/z): 649.3; and 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl 2-methylpropanoate (11.6 mg, 12.11% yield) MS ($ES^{30}$, m/z): 663.3.

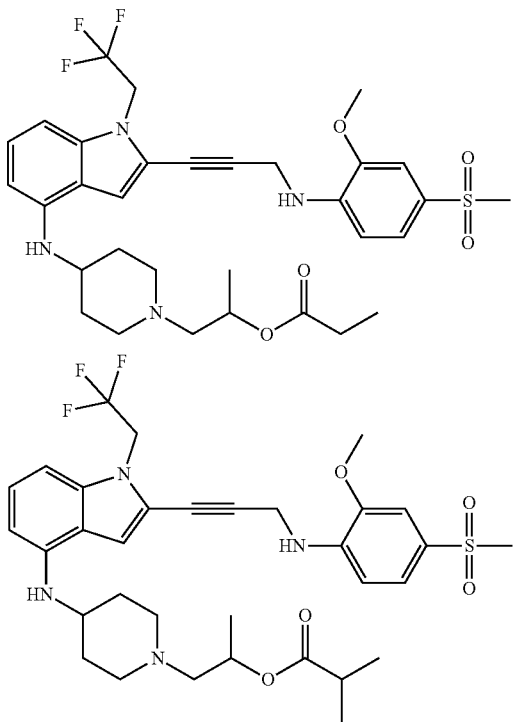

Example D27: Synthesis of 2-hydroxy-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propyl 2-methylpropanoate (Compound 592A)

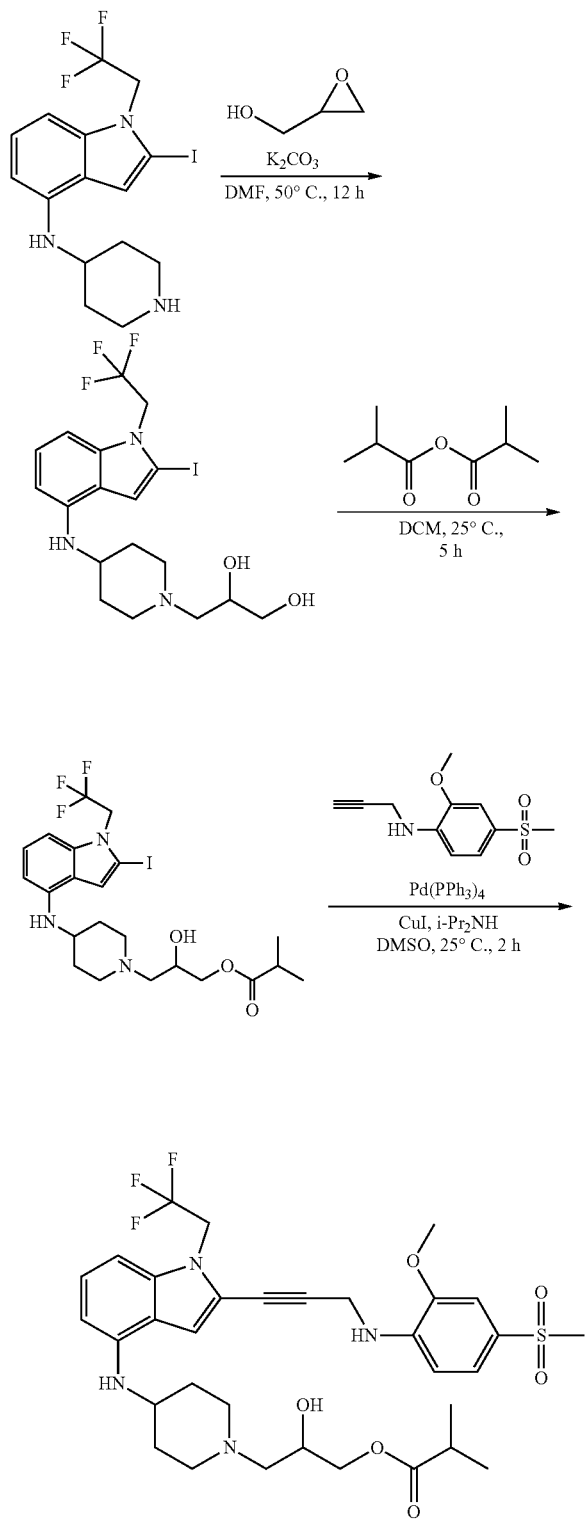

Preparation of 3-(4-((2-iodo-1-(2,2,2-trifluoroethyl)-1H-indol-4-yl)amino)piperidin-1-yl)propane-1,2-diol: To a mixture of 2-iodo-N-(piperidin-4-yl)-1-(2,2,2-trifluoroethyl)-1H-indol-4-amine) (2 g, 4.54 mmol, 1 eq.) in DMF (15 mL) were added oxiran-2-ylmethanol (1.77 g, 22.68 mmol, 1.58 mL, 5 eq.) and K₂CO₃ (1.88 g, 13.61 mmol, 3 eq.) at 25° C. The mixture was stirred at 50° C. for 12 hrs. TLC and LC-MS analysis showed that the starting material was consumed completely. The reaction was partitioned by adding water (20 mL) and EtOAc (10 mL) The aqueous phase was extracted with EtOAc (20 mL×3) The combined organic layers were washed with brine (20 mL×3) dried over anhydrous sodium sulfate, filtered, and dried in vacuo to afford the desired product 3-(4-((2-iodo-1-(2,2,2-trifluoroethyl)-1H-indol-4-yl)amino)piperidin-1-yl)propane-1,2-diol (2.1 g, 83.7% yield) as a black-brown oil.

Preparation of 2-hydroxy-3-[4-[[2-iodo-1-(2,2,2-trifluoroethyl)indol-4-yl]amino]-1-piperidyl]propyl]2-methylpropanoate: To a solution of 3-[4-[[2-iodo-1-(2,2,2-trifluoroethyl)indol-4-yl]amino]-1-piperidyl]propane-1,2-diol (120 mg, 217.18 μmol, 1 eq.) in DCM (3 mL) was added 2-methylpropanoyl 2-methylpropanoate (30.92 mg, 195.46 μmol, 32.41 μL, 0.9 eq.). The mixture was stirred at 25° C. for 5 h. TLC analysis (PE:EtOAc=1:1, $R_f$=0.63) showed that the staring material was consumed completely, and the product was detected. The reaction mixture was partitioned by adding water (100 mL) and EtOAc (10 mL). The aqueous phase was extracted with EtOAc (10 mL×3). The combined organic layers were washed with brine (50 mL×3), dried over anhydrous sodium sulfate, filtered, and concentrated by vacuum to give the crude product. The crude was purified by prep-TLC (PE:EtOAc=1:1, $R_f$=0.63) to give the desired product [2-hydroxy-3-[4-[[2-iodo-1-(2,2,2-trifluoroethyl)indol-4-yl]amino]-1-piperidyl]propyl]2-methylpropanoate (70 mg, crude) as a light brown oil. MS (ES³⁰, m/z): 568.2.

Preparation of 2-hydroxy-3-(4-((2-iodo-1-(2,2,2-trifluoroethyl)-1H-indol-4-yl)amino)piperidin-1-yl)propyl isobutyrate: To a solution of 2-methoxy-4-(methylsulfonyl)-N-(prop-2-yn-1-yl)aniline (39.36 mg, 148.05 μmol, 1.2 eq.) in DMSO (2 mL) were added i-Pr₂NH (72.93 mg, 1.23 mmol, 106 μL, 10 eq.), CuI (23.50 mg, 123.37 μmol, 1 eq.), [2-hydroxy-3-[4-[[2-iodo-1-(2,2,2-trifluoroethyl)indol-4-yl]amino]-1-piperidyl]propyl]2-methylpropanoate (70 mg, 123.37 μmol, 1 eq.), and Pd(PPh₃)₄ (28.51 mg, 24.67 μmol, 0.2 eq.) at 25° C. The mixture was stirred at 25° C. for 1 h under N₂. LC-MS and TLC analysis showed that the reaction was complete. The reaction mixture was quenched by adding a saturated aqueous EDTA solution (20 mL) at 25° C. and stirring the mixture for 2 h. The reaction mixture was partitioned by adding EtOAc (10 mL). The aqueous phase was extracted with EtOAc (5 mL×3). The organic phase was washed with brine (10 mL×3) dried over anhydrous sodium sulfate, filtered, and concentrated in vacuo. The residue was purified by prep-TLC and by prep-HPLC to afford the desired product (9.4 mg, 12.82 μmol, 10.39% yield) as a light-yellow solid. MS (ES³⁰, m/z): 679.3.

Example D28: Synthesis of (4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoyl)-L-glutamic acid (Compound 973A)

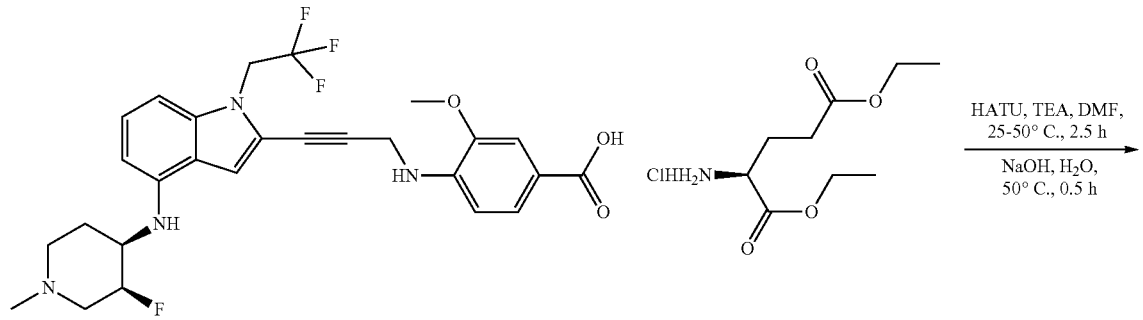

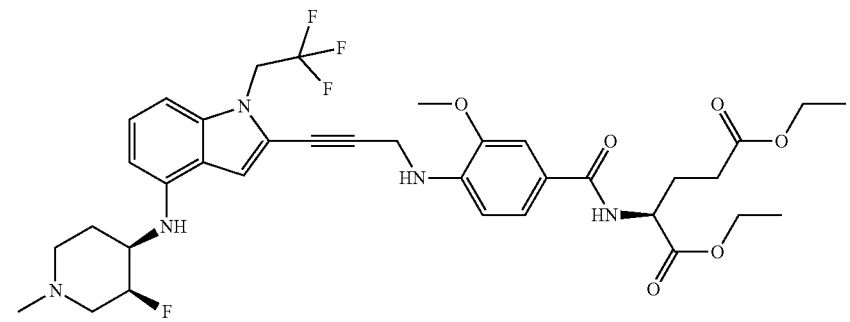

To a solution of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoic acid (0.08 g, 150.23 μmol, 1 eq.) in DMF (2 mL) were added TEA (45.60 mg, 450.68 μmol, 62.73 μL, 3 eq.) and HATU (85.68 mg, 225.34 μmol, 1.5 eq.) at 25° C. The mixture was stirred at 25° C. for 0.5 h. Then diethyl L-glutamate hydrochloride (43.21 mg, 180.27 μmol, 1.2 eq., HCl) was added and the mixture was stirred at 50° C. for 2 h. TLC analysis showed that the starting material was completely consumed. NaOH (12.02 mg, 300.45 μmol, 2 eq.) in water (0.5 mL) was added to the mixture, and the mixture was stirred for 0.5 h at 50° C. LC-MS analysis showed that the reaction was complete. The mixture was purified without workup by prep-HPLC to afford the desired product (4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoyl)-L-glutamic acid (0.033 g, 47.77 μmol, 31.80% yield) as a yellow solid. MS (ES$^{30}$, m/z): 662.3.

Example D29: Synthesis of (4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoyl)-L-glutamine (Compound 974A)

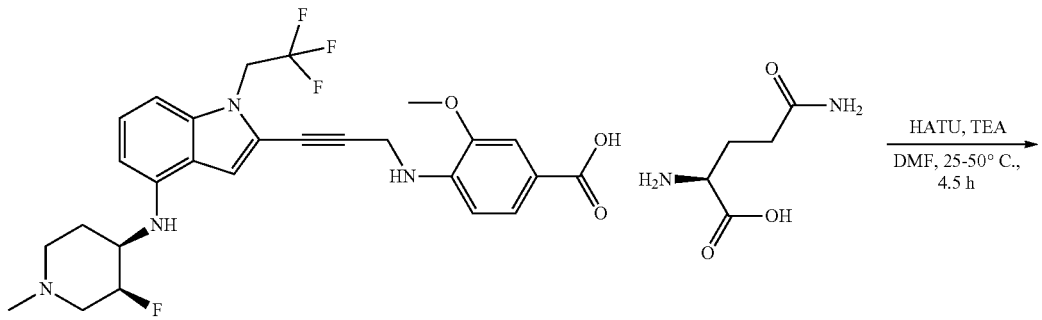

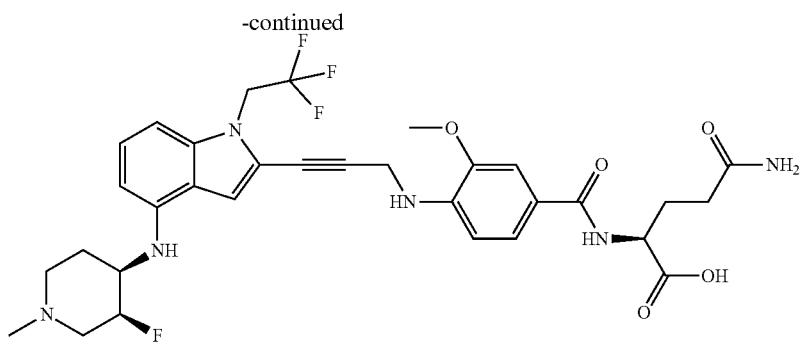

To a solution of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoic acid (0.08 g, 150.23 μmol, 1 eq.) in DMF (3 mL) were added TEA (45.60 mg, 450.68 μmol, 62.73 μL, 3 eq.) and HATU (85.68 mg, 225.34 μmol, 1.5 eq.) at 25° C. The mixture was stirred for 0.5 h. Then, L-glutamine (26.35 mg, 180.27 μmol, 1.2 eq.) was added, and the resulting mixture was stirred at 50° C. for 4 h. LC-MS analysis showed that the starting material was consumed completely. The mixture was purified directly by prep-HPLC to afford the desired product (0.031 g, 46.11 μmol, 30.69% yield) as a white solid. MS (ES$^{30}$, m/z): 661.3.

Example D30: Synthesis of (4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoyl)-L-glutamine (Compound 975A)

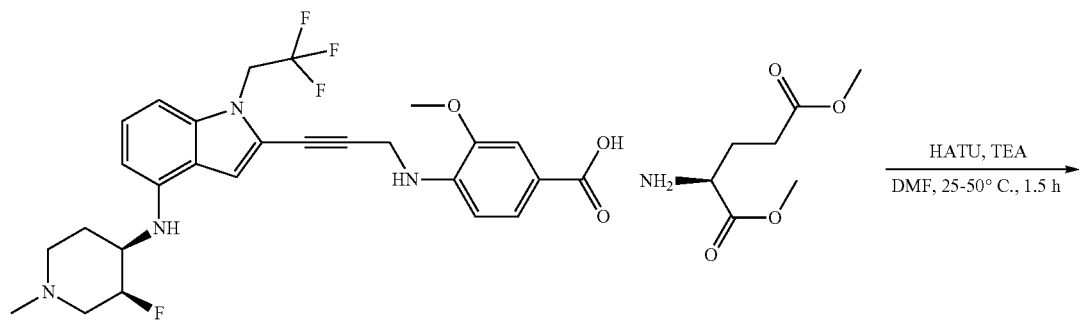

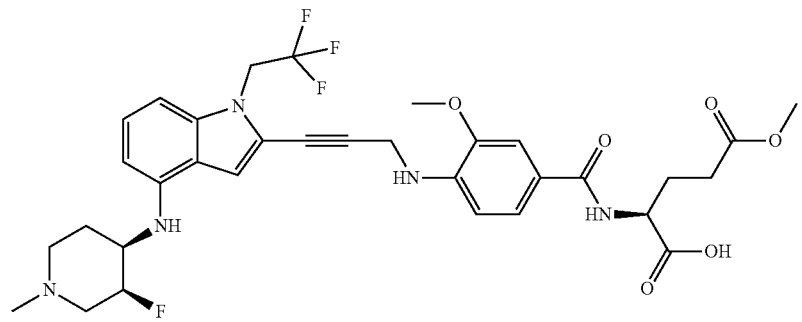

To a solution of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoic acid (100 mg, 187.78 μmol, 1 eq.) in DMF (3 mL) were added TEA (57.01 mg, 563.35 μmol, 78.41 μL, 3 eq.) and HATU (107.10 mg, 281.67 μmol, 1.5 eq.) at 20° C. The mixture was stirred at 25° C. for 0.5 h. Dimethyl L-glutamate (47.69 mg, 225.34 μmol, 1.2 eq., HCl) was added and the resulting mixture was warmed to 50° C. with stirring over 2 h. LC-MS analysis showed that the starting material was consumed completely. The mixture was purified by prep-HPLC to afford the desired product (41 mg, 58.79 μmol, 31.31% yield) as a white solid. MS (ES$^{30}$, m/z): 690.4.

Example D31: Synthesis of Compounds 474A and 475A

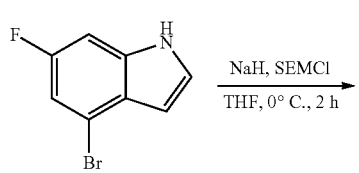

1021
-continued
1022
-continued
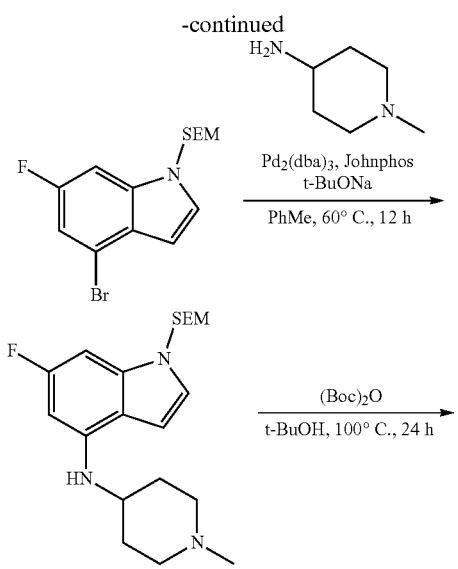
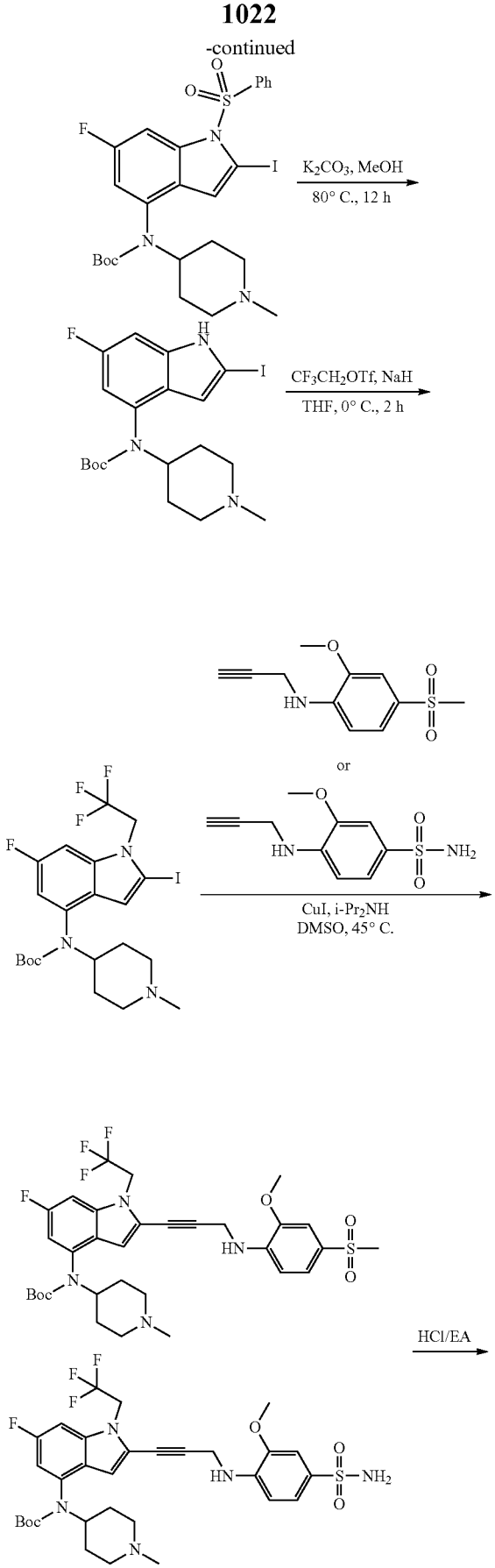

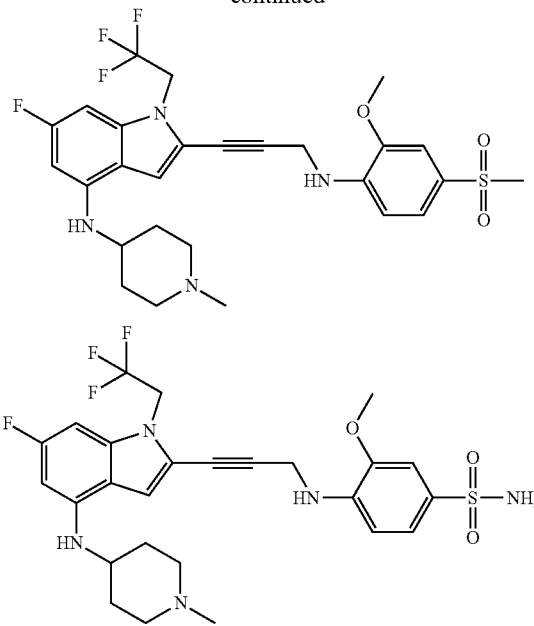

Preparation of 4-bromo-6-fluoro-1-((2-(trimethylsilyl)ethoxy)methyl)-1H-indole: To a mixture of NaH (2.80 g, 70.08 mmol, 60% in mineral oil, 3 eq.) in THF (80 mL) was added into a solution of 4-bromo-6-fluoro-1H-indole (5 g, 23.36 mmol, 1 eq.) in THF ((80 mL) at 0° C. The mixture was stirred for 1 h. then SEMCl (6.62 g, 39.71 mmol, 7.03 mL, 1.7 eq.) was added at 0° C. The mixture was stirred for 1 h at 0° C. LC-MS analysis indicated that the starting material was consumed completely, and that the desired product was detected. The reaction mixture was quenched by adding a saturated aqueous NH$_4$Cl solution (100 mL) and extracted with EtOAc (30 mL×3). The combined organic layers were dried over anhydrous sodium sulfate, filtered, and concentrated under reduced pressure. The crude residue was purified by column chromatography (SiO$_2$, PE:EtOAc=1:0 to 20:1) to afford the desired product (10 g, 29.04 mmol, 62.17% yield) as a light-yellow oil.

Preparation of 6-fluoro-N-(1-methylpiperidin-4-yl)-1-((2-(trimethylsilyl)ethoxy)methyl)-1H-indol-4-amine: To a mixture of 4-bromo-6-fluoro-1-((2-(trimethylsilyl)ethoxy)methyl)-1H-indole (7 g, 20.33 mmol, 1 eq.), 1-methylpiperidin-4-amine (23.22 g, 203.31 mmol, 10 eq.), t-BuONa (2.54 g, 26.43 mmol, 1.3 eq.), and ditert-butyl-(2-phenylphenyl)phosphane (1.21 g, 4.07 mmol, 0.2 eq.) in toluene (10 mL) was added Pd$_2$(dba)$_3$ (2.79 g, 3.05 mmol, 0.15 eq.) at 20° C. The mixture was flushed with N$_2$ and was stirred at 60° C. for 12 h. in a sealed tube. LC-MS analysis indicated that the starting material was consumed. The reaction mixture was quenched by adding a saturated aqueous EDTA solution (200 mL) at 25° C. for 1 h and extracted with EtOAc (20 mL×4). The combined organic layers were dried over anhydrous sodium sulfate, filtered, and concentrated under reduced pressure to give a residue. The residue was purified by column chromatography (SiO$_2$, DCM:MeOH=1:0 to 25:1, R$_f$=0.43) to afford the desired product (4.3 g, 11.39 mmol, 56.01% yield) as a black brown oil. MS (ES$^{3O}$, m/z): 378.1.

Preparation of tert-butyl (6-fluoro-1-((2-(trimethylsilyl)ethoxy)methyl)-1H-indol-4-yl)(1-methylpiperidin-4-yl)carbamate: A solution of 6-fluoro-N-(1-methylpiperidin-4-yl)-1-((2-(trimethylsilyl)ethoxy)methyl)-1H-indol-4-amine (2 g, 5.30 mmol, 1 eq.) in t-BuOH (2 mL) was added into (Boc)$_2$O (34.68 g, 158.91 mmol, 36.51 mL, 30 eq.) at 20° C. The mixture was stirred at 100° C. for 24 h. LC-MS analysis indicated that the starting material was consumed, and that one new major spot was detected. The reaction mixture was concentrated under reduced pressure, and the crude residue was purified by column chromatography (SiO$_2$, DCM:MeOH=1:0 to 20:1, R$_f$=0.43) to afford the desired product (3 g, 4.40 mmol, 41.50% yield) as a black brown solid. MS (ES$^{3O}$, m/z): 478.3.

Preparation of tert-butyl (6-fluoro-1H-indol-4-yl)(1-methylpiperidin-4-yl)carbamate: A solution of tert-butyl (6-fluoro-1-((2-(trimethylsilyl)ethoxy)methyl)-1H-indol-4-yl)(1-methylpiperidin-4-yl)carbamate (1.6 g, 2.34 mmol, 1 eq.) in THF (3 mL) was added into TBAF (1 M, 9.38 mL, 4 eq.) at 20° C. The mixture was stirred for 10 h at 80° C. LC-MS analysis indicated that the starting material was consumed, and one major spot with a mass of the desired product was detected. The reaction mixture was quenched by adding a saturated aqueous EDTA solution (100 mL) at 25° C. and extracted with EtOAc (30 mL×7). The combined organic layers were dried over anhydrous sodium sulfate, filtered, and concentrated under reduced pressure to give a residue. The residue was purified by column chromatography (SiO$_2$, DCM:MeOH=50:1 to 20:1) to afford the desired product (1.8 g, 3.11 mmol, 66.29% yield) as a black brown oil.

Preparation of tert-butyl (6-fluoro-1-(phenylsulfonyl)-1H-indol-4-yl)(1-methylpiperidin-4-yl)carbamate: A mixture of NaH (310.86 mg, 7.77 mmol, 60% in mineral oil, 3 eq.) in THF (5 mL) was added into a solution of tert-butyl (6-fluoro-1H-indol-4-yl)(1-methylpiperidin-4-yl)carbamate (1.5 g, 2.59 mmol, 1 eq.) in THF (5 mL) at 0° C. The mixture was stirred for 1 h. then benzenesulfonyl chloride (915.06 mg, 5.18 mmol, 663.09 µL, 2 eq.) was added at 0° C. The resulting mixture was stirred at 0° C. for 1 h. LC-MS analysis indicated that the starting material was consumed, and one desired product was detected. The reaction mixture was quenched by adding a saturated aqueous NH$_4$Cl solution (100 mL) at 20° C. and extracted with EtOAc (20 mL×4). The combined organic layers were dried over anhydrous sodium sulfate, filtered, and concentrated under reduced pressure to give a residue. The residue was purified by prep-TLC (SiO$_2$, DCM:MeOH=10:1, R$_f$=0.43) to afford the desired product (1.1 g, 1.80 mmol, 34.84% yield) as a black brown oil. MS (ES$^{3O}$, m/z): 488.1.

Preparation of tert-butyl (6-fluoro-2-iodo-1-(phenylsulfonyl)-1H-indol-4-yl)(1-methylpiperidin-4-yl)carbamate: To a solution of tert-butyl (6-fluoro-1-(phenylsulfonyl)-1H-indol-4-yl)(1-methylpiperidin-4-yl)carbamate (300 mg, 492.22 µmol, 1 eq.) in THF (3 mL) at −78° C. was added LDA (2 M, 861.39 µL, 3.5 eq.). The mixture was stirred at −78° C. for 1 h, and a solution of I$_2$ (499.72 mg, 1.97 mmol, 396.60 µL, 4 eq.) in THF (2 mL) was added, and the resulting mixture was stirred for 1 h at −78° C. LC-MS analysis indicated that the starting material was consumed completely. The reaction mixture was quenched by adding a saturated aqueous NH$_4$Cl solution (60 mL) at 20° C. and extracted with EtOAc (20 mL×3). The combined organic layers were dried over anhydrous sodium sulfate, filtered, and concentrated under reduced pressure to give a residue. The crude product was obtained as a black brown oil (1 g, 489.01 µmol, 49.67% yield) and was used in the next step without further purification. MS (ES$^+$, m/z): 613.9.

Preparation of tert-butyl (6-fluoro-2-iodo-1H-indol-4-yl)(1-methylpiperidin-4-yl)carbamate: A mixture of tert-butyl (6-fluoro-2-iodo-1-(phenylsulfonyl)-1H-indol-4-yl)(1- methylpiperidin-4-yl)carbamate (800 mg, 782.42 µmol, 1 eq.) and $K_2CO_3$ (540.68 mg, 3.91 mmol, 5 eq.) in MeOH (3 mL) was stirred at 60° C. for 2 h. LC-MS analysis indicated that the starting material was consumed completely, and one spot for the desired compound was detected. The reaction mixture was quenched by adding water (100 mL) at 20° C. and extracted with EtOAc (30 mL×4). The combined organic layers were dried over anhydrous sodium sulfate, filtered, and concentrated under reduced pressure to give a residue. The residue was purified by prep-TLC ($SiO_2$, DCM: MeOH=8:1, $R_f$=0.43) to afford the desired product (160 mg, 250.15 µmol, 31.97% yield) as a black brown oil. MS ($ES^+$, m/z): 473.9.

Preparation of tert-butyl (6-fluoro-2-iodo-1-(2,2,2-trifluoroethyl)-1H-indol-4-yl)(1-methylpiperidin-4-yl)carbamate: To a mixture of NaH (30.02 mg, 750.44 µmol, 60% in mineral oil, 3 eq.) in THF (2 mL) at 0° C. was added a solution of tert-butyl (6-fluoro-2-iodo-1H-indol-4-yl)(1-methylpiperidin-4-yl)carbamate (0.16 g, 250.15 µmol, 1 eq.) in THF (1 mL). The mixture was stirred for 1 h. at 0° C., and 2,2,2-trifluoroethyl trifluoromethanesulfonate (290.30 mg, 1.25 mmol, 5 eq.) was added and the mixture was stirred at 0° C. for 1 h. LC-MS analysis indicated that the reaction was complete. The reaction mixture was quenched by adding a saturated $NH_4Cl$ solution (15 mL) and was extracted with EtOAc (20 mL×3). The combined organic layers were washed with brine (5 mL), dried over anhydrous sodium sulfate, and concentrated in vacuo. The crude residue (0.16 g, crude) was obtained as a yellow solid and used in the next step without purification. MS ($ES^+$, m/z): 555.8.

Preparation of tert-butyl (6-fluoro-2-(3-((2-methoxy-4-(methylsulfonyl)phenyl)amino)prop-1-yn-1-yl)-1-(2,2,2-trifluoroethyl)-1H-indol-4-yl)(1-methylpiperidin-4-yl)carbamate and tert-butyl (6-fluoro-2-(3-((2-methoxy-4-sulfamoylphenyl)amino)prop-1-yn-1-yl)-1-(2,2,2-trifluoroethyl)-1H-indol-4-yl)(1-methylpiperidin-4-yl)carbamate: To a solution of tert-butyl (6-fluoro-2-iodo-1-(2,2,2-trifluoroethyl)-1H-indol-4-yl)(1-methylpiperidin-4-yl)carbamate (80 mg, 122.45 µmol, 1 eq.) in DMSO (3 mL) were added 2-methoxy-4-(methylsulfonyl)-N-(prop-2-yn-1-yl)aniline (42.26 mg, 160.71 µmol, 1.5 eq.) or 3-methoxy-4-(prop-2-yn-1-ylamino)benzenesulfonamide (73.55 mg, 244.89 µmol, 2 eq.), CuI (25.65 mg, 134.69 µmol, 1.10 eq.), N-isopropylpropan-2-amine (12.39 mg, 122.45 µmol, 17.30 µL, 1 eq.) and $Pd(PPh_3)_4$ (28.30 mg, 24.49 µmol, 0.20 eq.) under $N_2$. The mixture was stirred at 45° C. for 1 h. LC-MS analysis indicated that the starting material was consumed completely, and one new major spot with a mass of the desired product was detected. The reaction mixture was quenched by adding a saturated aqueous EDTA solution (100 mL) at 25° C. The mixture was stirred for 1 h and extracted with EtOAc (50 mL×3). The combined organic layers were dried over anhydrous sodium sulfate, filtered, and concentrated under reduced pressure to give a residue. The residue was purified by prep-TLC to afford the desired product as a black brown solid.

tert-Butyl (6-fluoro-2-(3-((2-methoxy-4-(methylsulfonyl)phenyl)amino)prop-1-yn-1-yl)-1-(2,2,2-trifluoroethyl)-1H-indol-4-yl)(1-methylpiperidin-4-yl)carbamate (25.0 mg, 28% yield), MS ($ES^{30}$, m/z): 667.0; and tert-butyl (6-fluoro-2-(3-((2-methoxy-4-sulfamoylphenyl)amino)prop-1-yn-1-yl)-1-(2,2,2-trifluoroethyl)-1H-indol-4-yl)(1-methylpiperidin-4-yl)carbamate (35.0 mg, 38.5% yield), MS ($ES^{30}$, m/z): 668.0.

Preparation of 4-[(3-{6-fluoro-4-[(1-methylpiperidin-4-yl)amino]-1-(2,2,2-trifluoroethyl)-1H-indol-2-yl}prop-2-yn-1-yl)amino]-3-methoxybenzene-1-sulfonamide and 6-fluoro-2-{3-[(4-methanesulfonyl-2-methoxyphenyl)amino]prop-1-yn-1-yl}-N-(1-methylpiperidin-4-yl)-1-(2,2,2-trifluoroethyl)-1H-indol-4-amine: A solution of tert-butyl (6-fluoro-2-(3-((2-methoxy-4-(methylsulfonyl)phenyl)amino)prop-1-yn-1-yl)-1-(2,2,2-trifluoroethyl)-1H-indol-4-yl)(1-methylpiperidin-4-yl)carbamate (20 mg, 24 µmol, 1 eq.) or tert-butyl (6-fluoro-2-(3-((2-methoxy-4-sulfamoylphenyl)amino)prop-1-yn-1-yl)-1-(2,2,2-trifluoroethyl)-1H-indol-4-yl)(1-methylpiperidin-4-yl)carbamate (35 mg, 47.18 µmol, 1 eq.) in EtOAc (0.5 mL) was added into HCl/EtOAc (4 M, 2 mL, 169.58 eq.) at 20° C. and stirred for 20 min. LC-MS analysis indicated that the starting material was consumed completely, and one main spot with a mass of the desired product was detected. The reaction mixture was concentrated under reduced pressure. The crude residue was purified by prep-HPLC to afford the desire products as light-yellow solids. 4-[(3-{6-fluoro-4-[(1-methylpiperidin-4-yl)amino]-1-(2,2,2-trifluoroethyl)-1H-indol-2-yl}prop-2-yn-1-yl)amino]-3-methoxybenzene-1-sulfonamide (0.6 mg, 3.9% yield), MS ($ES^{30}$, m/z): 567.2; and 6-fluoro-2-{3-[(4-methanesulfonyl-2-methoxyphenyl)amino]prop-1-yn-1-yl}-N-(1-methylpiperidin-4-yl)-1-(2,2,2-trifluoroethyl)-1H-indol-4-amine (3.8 mg, 13.9% yield), MS ($ES^{30}$, m/z): 568.2.

Example D32: Synthesis of 4-[(3-{4-[(1-acetylpiperidin-4-yl)amino]-1-(2,2,2-trifluoroethyl)-1H-indol-2-yl}prop-2-yn-1-yl)amino]-3-methoxybenzene-1-sulfonamide (Compound 749A)

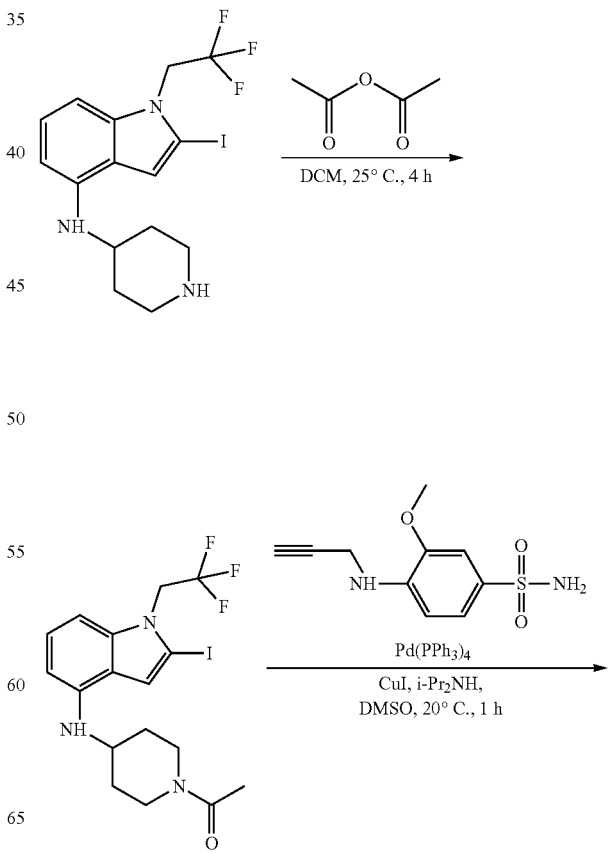

1027

-continued

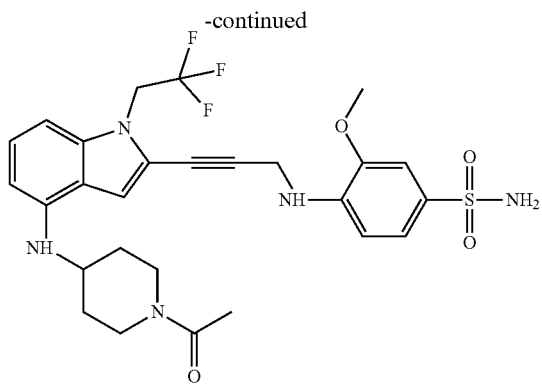

Preparation of 1-(4-((2-iodo-1-(2,2,2-trifluoroethyl)-1H-indol-4-yl)amino)piperidin-1-yl)ethan-1-one: To a mixture of 2-iodo-N-(piperidin-4-yl)-1-(2,2,2-trifluoroethyl)-1H-indol-4-amine (100 mg, 226.84 µmol, 1 eq.) in DCM (3 mL) was added acetic anhydride (20.84 mg, 204.15 µmol, 19.12 L, 0.9 eq.). The mixture was stirred at 25° C. for 4 h. TLC and LC-MS analysis showed that the starting material was consumed completely. The reaction was concentrated to give the crude product as a black brown oil (110.0 mg) and used in the next step without purification. MS (ES$^{30}$, m/z): 466.1.

Preparation of 4-((3-(4-((1-acetylpiperidin-4-yl)amino)-1-(2,2,2-trifluoroethyl)-1H-indol-2-yl)prop-2-yn-1-yl) amino)-3-methoxybenzenesulfonamide: To a solution of 1-(4-((2-iodo-1-(2,2,2-trifluoroethyl)-1H-indol-4-yl)amino) piperidin-1-yl)ethan-1-one (110 mg, 236.43 µmol, 1 eq.) and 3-methoxy-4-(prop-2-yn-1-ylamino)benzenesulfonamide (85.21 mg, 283.72 µmol, 1.2 eq.) in DMSO (3 mL) were added i-Pr$_2$NH (139.76 mg, 2.36 mmol, 203.13 µL, 10 eq.), CuI (45.03 mg, 236.43 µmol, 1 eq.), and Pd(PPh$_3$)$_4$ (54.64 mg, 47.29 µmol, 0.2 eq.) The mixture was stirred at 25° C. for 1 h. LC-MS and TLC analysis showed that the reaction was complete. The reaction mixture was quenched by adding a saturated aqueous EDTA solution (20 mL) at 25° C. and stirring for 2 h. The reaction mixture was partitioned by adding EtOAc (10 mL), and the aqueous phase was extracted with EtOAc (5 mL×3). The organic phase was washed with brine (10 mL×3), dried over anhydrous sodium sulfate, filtered, and concentrated in vacuo. The crude residue was purified by prep-TLC (PE:EtOAc=0:1, R$_f$=0.35), and prep-HPLC to give the desired product 18.3 mg, 12.9% yield, as a light yellow solid. MS (ES$^{30}$, m/z): 578.1.

Example D33: Synthesis of 4-[(3-{4-[(1-acetylpiperidin-4-yl)amino]-1-(2,2,2-trifluoroethyl)-1H-indol-2-yl}prop-2-yn-1-yl)amino]-3-methoxy-N,N-dimethylbenzene-1-sulfonamide (Compound 755A)

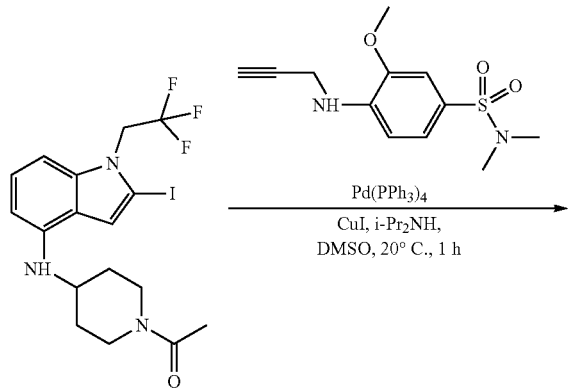

1028

-continued

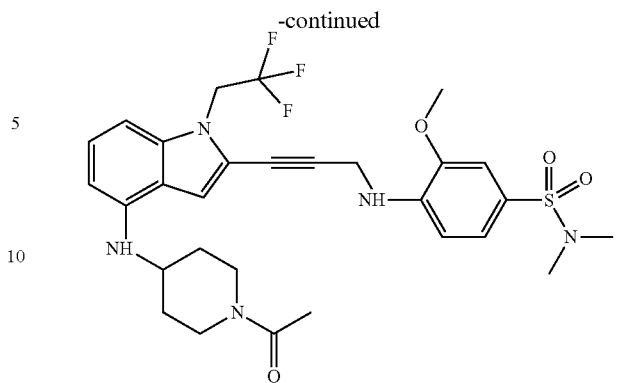

To a mixture of 3-methoxy-N,N-dimethyl-4-(prop-2-yn-1-ylamino)benzenesulfonamide (119.79 mg, 290.17 µmol, 1.5 eq.) in DMSO (1~10 mL) (4 mL) were added i-Pr$_2$NH (195.75 mg, 1.93 mmol, 273.39 µL, 10 eq.), CuI (36.84 mg, 193.44 µmol, 1 eq.), 1-(4-((2-iodo-1-(2,2,2-trifluoroethyl)-1H-indol-4-yl)amino)piperidin-1-yl)ethan-1-one (100 mg, 193.44 µmol, 1 eq.), and Pd(PPh$_3$)$_4$ (44.71 mg, 38.69 µmol, 0.2 eq.) at 20° C. The mixture was stirred at 20° C. for 1 h. EtOAc (10 mL) was added to the mixture, and the resulting mixture was then poured into a saturated EDTA solution (40 mL) and stirred for 15 min. The aqueous phase was extracted with EtOAc (40 mL×2), and the organic layer was poured to a 2N aqueous EDTA solution (40 mL) and stirred further for 1 h. The aqueous phase was extracted with EtOAc (40 mL×3). The combined organic layers were washed with brine (40 mL×3), dried over anhydrous sodium sulfate, mixed with activated carbon, filtered, and concentrated in vacuo. The mixture was purified by prep-HPLC to afford the desired product in 31.6 mg, 26.8% yield. MS (ES$^{30}$, m/z): 606.2.

Example D34: Synthesis of 1-(4-{1[2-(3-{1[2-methoxy-4-(morpholine-4-sulfonyl)phenyl] amino}prop-1-yn-1-yl)-1-(2,2,2-trifluoroethyl)-1H-indol-4-yl]amino}piperidin-1-yl)ethan-1-one (Compound 758A)

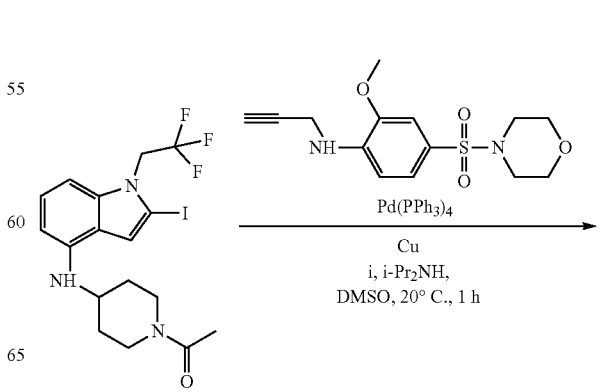

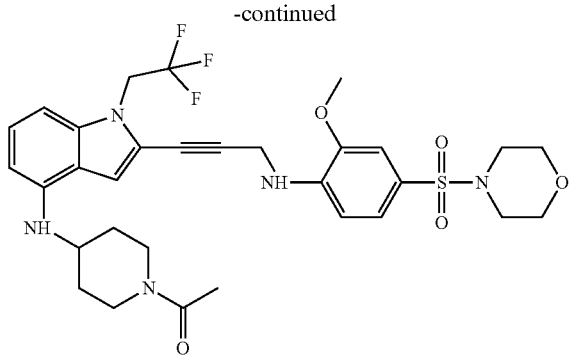

To a solution of 2-methoxy-4-(morpholinosulfonyl)-N-(prop-2-yn-1-yl)aniline (72.77 mg, 232.13 μmol, 1.5 eq.) in DMSO (2 mL) were added i-Pr$_2$NH (156.60 mg, 1.55 mmol, 218.71 μL, 10 eq.), CuI (29.47 mg, 154.76 μmol, 1 eq.), 1-(4-((2-iodo-1-(2,2,2-trifluoroethyl)-1H-indol-4-yl)amino)piperidin-1-yl)ethan-1-one (80 mg, 154.76 μmol, 1 eq.), and Pd(PPh$_3$)$_4$ (35.77 mg, 30.95 μmol, 0.2 eq.) at 20° C. The mixture was stirred at 20° C. for 1 h. LC-MS analysis showed that the reaction was complete. EtOAc (10 mL) was added into the mixture, and the resulting mixture was then poured into a saturated aqueous EDTA solution (40 mL) and stirred for 1 h. The aqueous phase was extracted with EtOAc (40 mL×3). The combined organic layers were washed with brine (40 mL×3), dried over anhydrous sodium sulfate, mixed with activated carbon, filtered, and concentrated in vacuo. The mixture was purified by prep-TLC or column chromatography, then purified by prep-HPLC to afford the desired product (28.04 mg, 30.5% yield), MS (ES$^{30}$, m/z): 648.2.

Example D35: Synthesis of 1-(4-((2-(3-((2-methoxy-4-(methylsulfonyl)phenyl)amino)prop-1-yn-1-yl)-1-(2,2,2-trifluoroethyl)-1H-indol-4-yl)amino)-2-methylpiperidin-1-yl)ethan-1-one (Compound 738A)

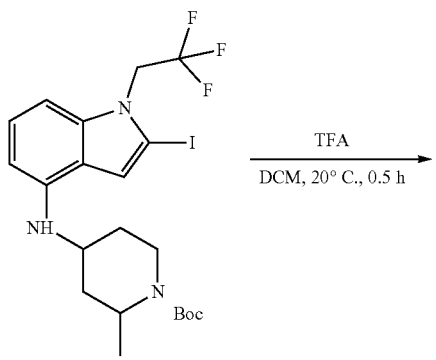

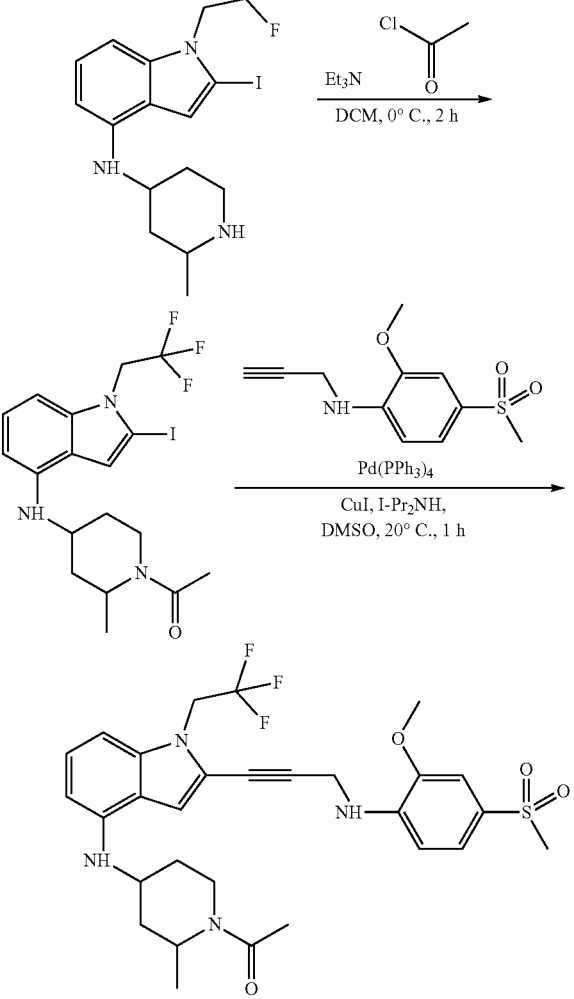

Preparation of 2-iodo-N-(2-methylpiperidin-4-yl)-1-(2,2,2-trifluoroethyl)-1H-indol-4-amine: To a solution of tert-butyl 4-((2-iodo-1-(2,2,2-trifluoroethyl)-1H-indol-4-yl)amino)-2-methylpiperidine-1-carboxylate (320 mg, 595.51 μmol, 1 eq.) in DCM (2 mL) was added TFA (2.04 g, 17.87 mmol, 1.32 mL, 30 eq.). The mixture was stirred at 20° C. for 2 h. TLC analysis (PE:EtOAc=1:1, R$_f$=0.1) showed that the reaction was complete. The reaction mixture was poured into a saturated NaHCO$_3$ solution (20 mL), and the aqueous phase was extracted with EtOAc (10 mL×3). The combined organic layers were washed with brine (20 mL), dried over anhydrous sodium sulfate, filtered, and concentrated in vacuo. The crude residue (370 mg, crude) was obtained as light yellow solid and used in the next step without purification. MS (ES$^{30}$, m/z): 437.9.

Preparation of 1-(4-((2-iodo-1-(2,2,2-trifluoroethyl)-1H-indol-4-yl)amino)-2-methylpiperidin-1-yl)ethan-1-one: A mixture of 2-iodo-N-(2-methylpiperidin-4-yl)-1-(2,2,2-trifluoroethyl)-1H-indol-4-amine and Et$_3$N (256.89 mg, 2.54 mmol, 353.35 μL, 3 eq.) in DCM (4 mL) under N$_2$ at 0° C. was prepared. A solution of acetyl chloride (66.43 mg, 846.22 μmol, 60.39 μL, 1 eq.) in DCM (1 mL) was added dropwise to the mixture. The reaction mixture was stirred at 20° C. for 2 h. LC-MS and TLC analysis (PE:EtOAc=1:1, R$_f$=0.43) showed that the reaction was complete. The mixture was poured into a saturated NaHCO₃ solution (20 mL). The aqueous phase was extracted with EtOAc (20 mL×3). The combined organic layers were washed with brine (40 mL), dried over anhydrous sodium sulfate, filtered, and concentrated in vacuo. The crude residue was purified by prep-TLC (PE:EtOAc=1:1, R$_f$=0.43) to afford the desired product (160 mg, 282.09 μmol, 33.34% yield) as a light yellow solid.

Preparation of 1-(4-((2-(3-((2-methoxy-4-(methylsulfonyl)phenyl)amino)prop-1-yn-1-yl)-1-(2,2,2-trifluoroethyl)-1H-indol-4-yl)amino)-2-methylpiperidin-1-yl)ethan-1-one: To a solution of 2-methoxy-4-(methylsulfonyl)-N-(prop-2-yn-1-yl)aniline (103.02 mg, 370.25 μmol, 1.5 eq.) in DMSO (5 mL) were added i-Pr₂NH (249.77 mg, 2.47 mmol, 348.84 μL, 10 eq.), CuI (47.01 mg, 246.83 μmol, 1 eq.), 1-(4-((2-iodo-1-(2,2,2-trifluoroethyl)-1H-indol-4-yl)amino)-2-methylpiperidin-1-yl)ethan-1-one (140 mg, 246.83 μmol, 1 eq.), and Pd(PPh₃)₄ (57.05 mg, 49.37 μmol, 0.2 eq.) at 20° C. The mixture was stirred at 20° C. for 1 h. EtOAc (10 mL) was added into the mixture, and the resulting mixture was then poured into a 2N aqueous EDTA solution (40 mL) and stirred for 15 min. The aqueous phase was extracted with EtOAc (40 mL×2). The organic layer was poured to a 2N aqueous EDTA solution (40 mL) and stirred for 1 h. The aqueous phase was extracted with EtOAc (40 mL×3). The combined organic layers were washed with brine (40 mL×3), dried over anhydrous sodium sulfate, mixed with activated carbon, filtered, and concentrated in vacuo. The mixture was purified by prep-TLC (PE:EtOAc=0:1, R$_f$=0.42). then purified by prep-HPLC to afford the desired product (14.9 mg, 16.1% yield), MS (ES³⁰, m/z): 591.2.

Example D36: Synthesis of 1-{4-[(2-{3-[(4-methanesulfonyl-2-methoxyphenyl)amino]prop-1-yn-1-yl}-1-(2,2,2-trifluoroethyl)-1H-indol-4-yl)amino]azepan-1-yl}-3-methoxypropan-2-ol (Compound 989A)

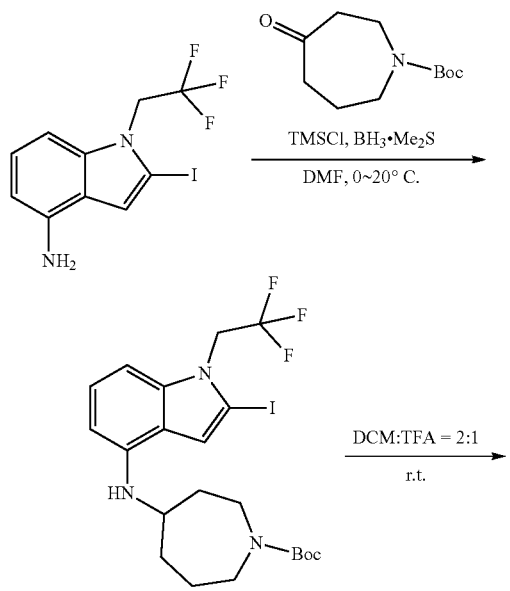

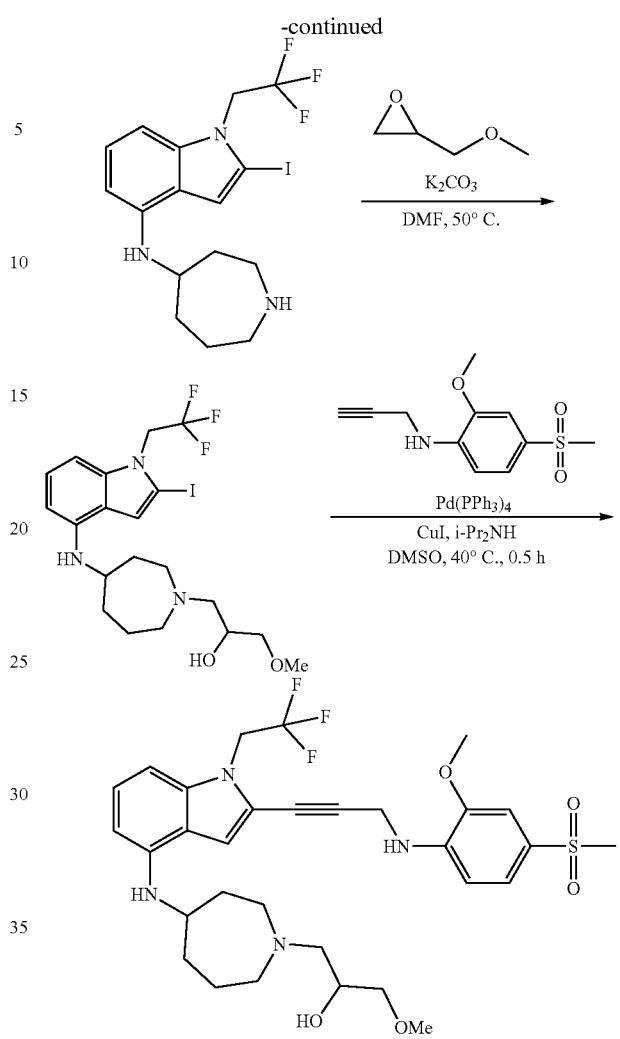

Preparation of tert-butyl 4-((2-iodo-1-(2,2,2-trifluoroethyl)-1H-indol-4-yl)amino)azepane-1-carboxylate: To a solution of 2-iodo-1-(2,2,2-trifluoroethyl)-1H-indol-4-amine (0.5 g, 1.47 mmol, 1 eq.) in DMF (5 mL) were added tert-butyl 4-oxoazepane-1-carboxylate (627.12 mg, 2.94 mmol, 2 eq.) and TMSCl (479.19 mg, 4.41 mmol, 559.80 μL, 3 eq.). The reaction mixture was stirred for 0.5 h. at 20° C. under N₂. BH₃·Me₂S (10 M, 441.07 μL, 3 eq.) was then added dropwise to the reaction mixture at 0° C. and stirring for 0.5 h under N₂. LC-MS analysis showed that the reaction was complete. The reaction was quenched with ice water (20 mL), and the mixture was extracted with EtOAc (20 mL×3). The combined organic layers were washed with brine (20 mL×2), dried over anhydrous sodium sulfate, filtered, and concentrated in vacuo. The crude residue was purified by column chromatography (SiO₂, PE:EtOAc=20:1 to 10:1) to afford tert-butyl 4-((2-iodo-1-(2,2,2-trifluoroethyl)-1H-indol-4-yl)amino)azepane-1-carboxylate (0.69 g, 1.28 mmol, 87.34% yield) as a red oil. MS (ES³⁰, m/z): 538.1.

Preparation of tert-butyl 4-((2-iodo-1-(2,2,2-trifluoroethyl)-1H-indol-4-yl)amino)azepane-1-carboxylate: To a solution of tert-butyl 4-((2-iodo-1-(2,2,2-trifluoroethyl)-1H-indol-4-yl)amino)azepane-1-carboxylate (0.6 g, 1.12 mmol, 1 eq.) in DCM (10 mL) was added TFA (7.70 g, 67.53 mmol, 5 mL, 60.48 eq.). The mixture was stirred for 0.5 h at 20° C. under N₂. LC-MS analysis showed that the reaction was complete. The reaction was quenched with a cold saturated aqueous NaHCO₃ solution (20 mL), and the mixture was extracted with DCM (20 mL×3). The combined organic layers were washed with brine (20 mL×2), dried over anhydrous sodium sulfate, filtered, and concentrated in vacuo to afford tert-butyl 4-((2-iodo-1-(2,2,2-trifluoroethyl)-1H-indol-4-yl)amino)azepane-1-carboxylate (0.55 g, crude) as a red solid. MS (ES³⁰, m/z): 438.2.

Preparation of 1-(4-((2-iodo-1-(2,2,2-trifluoroethyl)-1H-indol-4-yl)amino)azepan-1-yl)-3-methoxypropan-2-ol: To a solution of tert-butyl 4-((2-iodo-1-(2,2,2-trifluoroethyl)-1H-indol-4-yl)amino)azepane-1-carboxylate (0.45 g, 1.03 mmol, 1 eq.) in DMF (10 mL) were added 2-(methoxymethyl)oxirane (453.38 mg, 5.15 mmol, 457.96 µL, 5 eq.) and K₂CO₃ (426.72 mg, 3.09 mmol, 3 eq.). The mixture was stirred for 8 h at 50° C. under N₂. TLC analysis showed 60% of the desired product and 20% of the starting material. The reaction was quenched with water (20 mL) and extracted with EtOAc (20 mL×3). The combined organic layers were washed with brine (20 mL×2), dried over anhydrous sodium sulfate, filtered, and concentrated in vacuo. The crude residue was purified by prep-TLC (SiO₂, DCM:MeOH=10:1) to afford 1-(4-((2-iodo-1-(2,2,2-trifluoroethyl)-1H-indol-4-yl)amino)azepan-1-yl)-3-methoxypropan-2-ol (0.22 g, 418.77 µmol, 40.69% yield) as a yellow oil.

Preparation of 1-{4-[(2-{3-[(4-methanesulfonyl-2-methoxyphenyl)amino]prop-1-yn-1-yl}-1-(2,2,2-trifluoroethyl)-1H-indol-4-yl)amino]azepan-1-yl}-3-methoxypropan-2-ol: To a solution of 2-methoxy-4-methylsulfonyl-N-prop-2-ynyl-aniline (43.73 mg, 182.74 µmol, 1.2 eq.) in DMSO (5 mL) were added i-Pr₂NH (154.09 mg, 1.52 mmol, 215.21 µL, 10 eq.), CuI (8.70 mg, 45.68 µmol, 0.3 eq.), 1-(4-((2-iodo-1-(2,2,2-trifluoroethyl)-1H-indol-4-yl)amino)azepan-1-yl)-3-methoxypropan-2-ol (0.08 g, 152.28 µmol, 1 eq.), and Pd(PPh₃)₄ (8.80 mg, 7.61 µmol, 0.05 eq.). The mixture was stirred for 0.5 h at 40° C. under N₂. LC-MS analysis showed that the reaction was complete. The reaction was diluted with EtOAc (20 mL) and saturated EDTA solution (20 mL) and stirred at 20° C. for 1 h. The mixture was then extracted with EtOAc (20 mL×3) and washed with brine (50 mL), dried over anhydrous sodium sulfate, and concentrated under reduced pressure. The crude residue was purified by prep-HPLC to afford 1-{4-[(2-{3-[(4-methanesulfonyl-2-methoxyphenyl)amino]prop-1-yn-1-yl}-1-(2,2,2-trifluoroethyl)-1H-indol-4-yl)amino]azepan-1-yl}-3-methoxypropan-2-ol (0.0223 g, 32.82 µmol, 21.55% yield) as a yellow solid. MS (ES³⁰, m/z): 637.2.

Example D37: Synthesis of 3-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)propane-1,2-diol (Compound 556A)

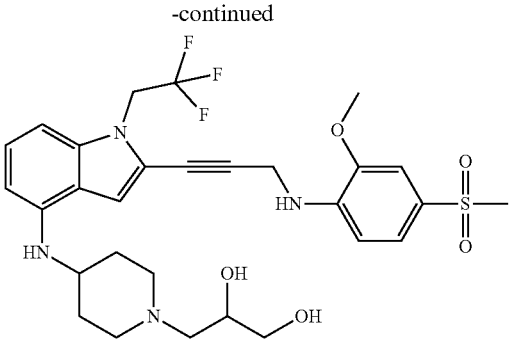

To a solution of 2-(3-((2-methoxy-4-(methylsulfonyl)phenyl)amino)prop-1-yn-1-yl)-N-(piperidin-4-yl)-1-(2,2,2-trifluoroethyl)-1H-indol-4-amine (10.5 g, 19.64 mmol, 1 eq.) in acetonitrile (100 mL) were added K₂CO₃ (5.43 g, 39.28 mmol, 2 eq.) and oxiran-2-ylmethanol (2.91 g, 39.28 mmol, 2.60 mL, 2 eq.; added dropwise) under N₂. The reaction mixture was stirred at 80° C. for 12 h. TLC analysis (PE:EtOAc=0:1) showed that the starting material was consumed completely. The reaction was quenched with aqueous Na₂CO₃ (500 mL) and extracted with DCM (50 mL×2). The combined organic layers were washed with brine (100 mL), dried over anhydrous sodium sulfate, filtered, and concentrated in vacuo. The residue was purified by column chromatography (SiO₂, DCM:MeOH=1000:1 to 20:1) and prep-HPLC to afford the desired product (3.6 g, 5.86 mmol, 29.81% yield) as a yellow solid. MS (ES³⁰, m/z): 609.3.

¹H NMR (400 MHz, DMSO-d₆) δ ppm 7.39-7.36 (dd, 1H), 7.23-7.22 (d, J=1.6 Hz, 1H), 7.05 (s, 1H), 6.99-6.86 (t, J=8.4 Hz, 1H), 6.77-6.47 (d, J=8.4 Hz, 1H), 6.47-6.49 (m, 1H), 6.47-6.34 (t, J=8.4 Hz, 1H), 6.16-6.14 (d, J=8.0 Hz, 1H), 4.92-4.85 (q, J=26.8 Hz, 2H), 4.35-4.34 (d, J=5.2 Hz, 2H), 3.87 (s, 3H), 3.61-3.58 (m, 1H), 3.33-3.30 (m, 3H), 3.01 (s, 3H), 2.85-2.67 (m, 2H), 2.36-2.26 (m, 2H), 2.11-2.10 (m, 2H), 1.91-1.89 (m, 2H) 1.49-1.44 (m, 2H).

Example D38: Synthesis of 3-(2-hydroxy-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propoxy)propane-1,2-diol (Compound 669A)

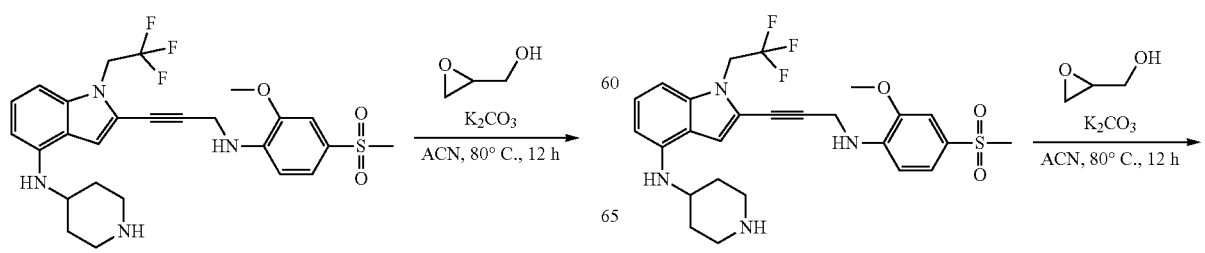

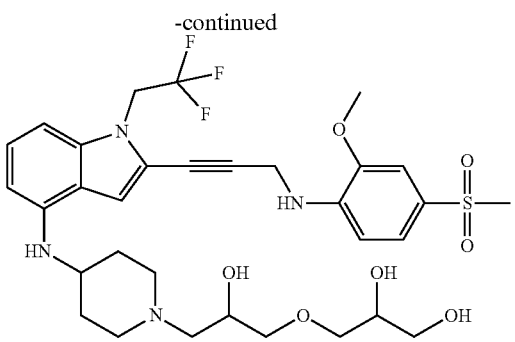

To a solution of 2-[3-(2-methoxy-4-methylsulfonyl-anilino)prop-1-ynyl]-N-(4-piperidyl)-1-(2,2,2-trifluoroethyl)indol-4-amine hydrochloride (0.5 g, 875.5 μmol, 1 eq.) in acetonitrile (20 mL) were added K$_2$CO$_3$ (484.05 mg, 3.50 mmol, 4 eq.) and oxiran-2-ylmethanol (129.72 mg, 1.75 mmol, 115.82 L, 2 eq.) under N$_2$. The reaction mixture was stirred at 80° C. for 16 h. TLC analysis (PE:EtOAc=0:1) showed that the starting material was consumed completely. The reaction was quenched with a saturated aqueous Na$_2$CO$_3$ solution (100 mL) and extracted with DCM (20 mL×2). The combined organic layers were washed with brine (20 mL), dried over anhydrous sodium sulfate, filtered, and concentrated in vacuo. The crude residue was purified by prep-TLC (SiO$_2$, DCM:MeOH=10:1) and prep-HPLC to give the desired product (0.3 g, 443.59 μmol, 50.66% yield) as a yellow solid. MS (ES[30], m/z): 683.2.

$^1$H NMR (400 MHz, DMSO-d$_6$) δ ppm 7.39-7.36 (dd, 1H), 7.23-7.22 (d, J=1.6 Hz, 1H), 7.05 (s, 1H), 6.99-6.86 (t, J=8.4 Hz, 1H), 6.77-6.47 (d, J=8.4 Hz, 1H), 6.47-6.49 (m, 1H), 6.47-6.34 (t, J=8.4 Hz, 1H), 6.16-6.14 (d, J=8.0 Hz, 1H), 4.92-4.85 (q, J=26.8 Hz, 2H), 4.35-4.34 (d, J=5.2 Hz, 2H), 3.87 (s, 3H), 3.61-3.58 (m, 1H), 3.33-3.30 (m, 3H), 3.01 (s, 3H), 2.85-2.67 (m, 2H), 2.36-2.26 (m, 2H), 2.11-2.10 (m, 2H), 1.91-1.89 (m, 2H) 1.49-1.44 (m, 2H).

Example D39: Synthesis of 3-methoxy-4-((3-(4-((1-(2-methoxyethyl)piperidin-4-yl)amino)-1-(2,2,2-trifluoroethyl)-1H-indol-2-yl)prop-2-yn-1-yl)amino)benzenesulfonamide (Compound 614A)

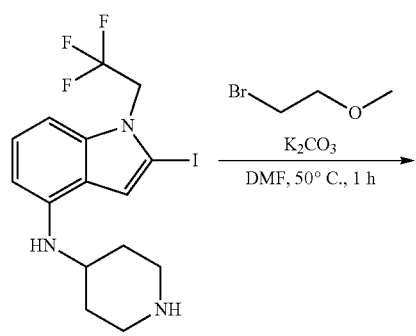

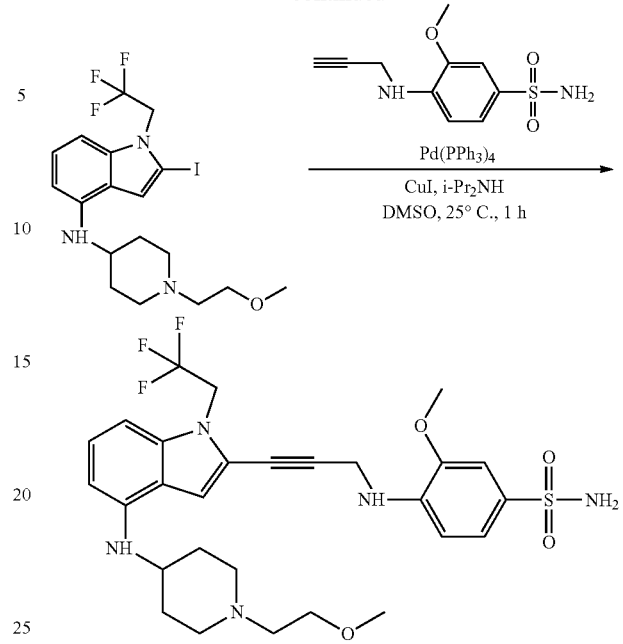

Preparation of 2-iodo-N-(1-(2-methoxyethyl)piperidin-4-yl)-1-(2,2,2-trifluoroethyl)-1H-indol-4-amine: To a solution of 2-iodo-N-(piperidin-4-yl)-1-(2,2,2-trifluoroethyl)-1H-indol-4-amine (100 mg, 222.11 μmol, 1 eq.) in DMF (2 mL) were added K$_2$CO$_3$ (153.48 mg, 1.11 mmol, 5 eq.) and 1-bromo-2-methoxyethane (61.74 mg, 444.22 μmol, 41.72 μL, 2 eq.). The reaction mixture was stirred at 50° C. for 1 h. TLC analysis (DCM:MeOH=10:1, R$_f$=0.43) indicated that the reaction was complete. The reaction mixture was quenched by adding water (40 mL) at 25° C. and extracting the mixture with EtOAc (10 mL×3). The combined organic layers were dried over anhydrous sodium sulfate, filtered, and concentrated under reduced pressure. The crude residue was purified by prep-TLC (SiO$_2$, DCM:MeOH=10:1) to afford the desired product (80 mg, 141.29 μmol, 63.61% yield) as a light-yellow oil. MS (ES[30], m/z): 481.9.

Preparation of 3-methoxy-4-((3-(4-((1-(2-methoxyethyl)piperidin-4-yl)amino)-1-(2,2,2-trifluoroethyl)-1H-indol-2-yl)prop-2-yn-1-yl)amino)benzenesulfonamide: To a mixture of 2-iodo-N-(1-(2-methoxyethyl)piperidin-4-yl)-1-(2,2,2-trifluoroethyl)-1H-indol-4-amine (70 mg, 123.63 μmol, 1 eq.) and 3-methoxy-4-(prop-2-yn-1-ylamino)benzenesulfonamide (41.94 mg, 148.35 μmol, 1.2 eq.) in DMSO (3 mL) were added CuI (23.54 mg, 123.63 μmol, 1 eq.), N-isopropylpropan-2-amine (12.51 mg, 123.63 μmol, 17.47 μL, 1 eq.), and Pd(PPh$_3$)$_4$ (2.86 mg, 2.47 μmol, 0.02 eq.) under N$_2$. The mixture was stirred for 1 h at 25° C. TLC analysis (DCM:MeOH=10:1, R$_f$=0.30) indicated that the reaction was complete. The reaction mixture was quenched by adding a saturated aqueous EDTA solution (60 mL) at 25° C. and stirring the mixture for 1 h. The mixture was then extracted with EtOAc (20 mL×4). The combined organic layers were dried over anhydrous sodium sulfate, filtered, and concentrated under reduced pressure. The crude residue was purified by prep-TLC (SiO$_2$, DCM:MeOH=10:1) and prep-HPLC to afford the desired product (16.1 mg, 25.19 μmol, 20.38% yield) as a light yellow solid. MS (ES[30], m/z): 594.3.

Example D40: Synthesis of Compounds 600A, 608A, and 618A

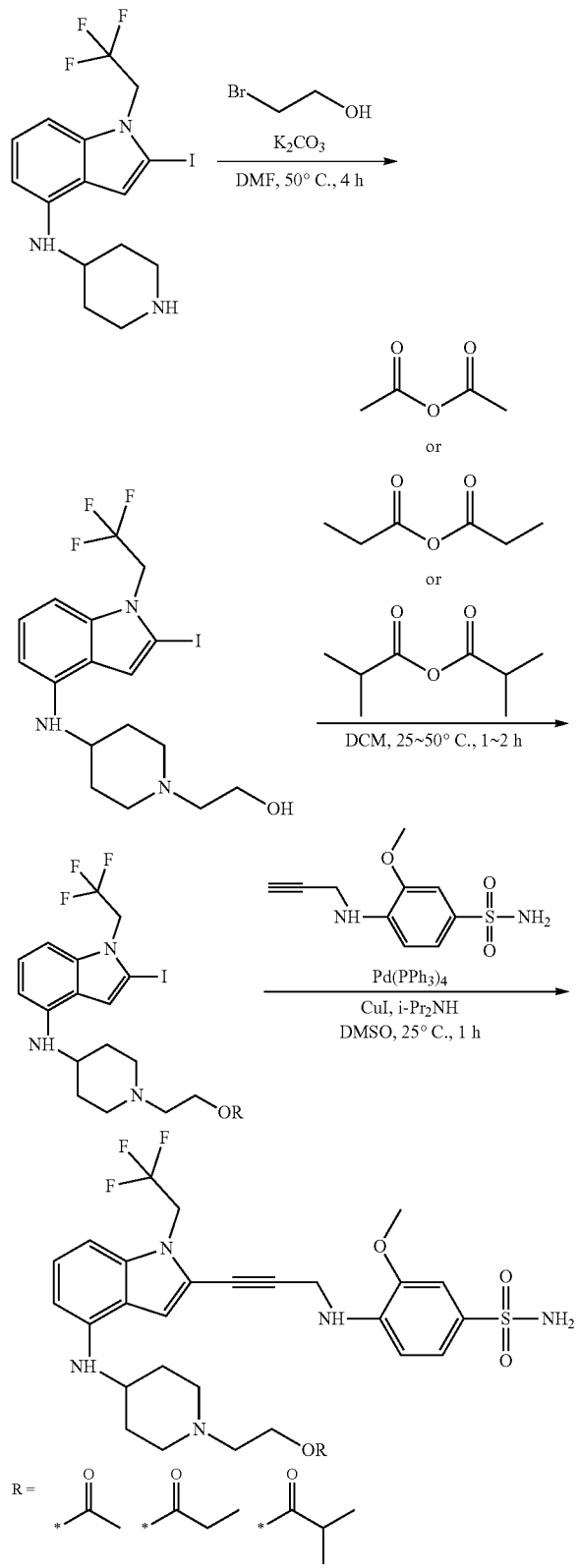

Preparation of 2-(4-((2-iodo-1-(2,2,2-trifluoroethyl)-1H-indol-4-yl)amino)piperidin-1-yl)ethan-1-ol: To a solution of 2-iodo-N-(piperidin-4-yl)-1-(2,2,2-trifluoroethyl)-1H-indol-4-amine (1 g, 2.22 mmol, 1 eq.) in DMF (10 mL) were added into $K_2CO_3$ (460.47 mg, 3.33 mmol, 1.5 eq.) and 2-bromoethan-1-ol (555.12 mg, 4.44 mmol, 315.41 µL, 2 eq.). The reaction mixture was stirred at 50° C. for 4 h. TLC analysis (DCM:MeOH=10:1, $R_f$=0.24) indicated that the reaction was complete. The reaction mixture was quenched by adding water (200 mL) at 25° C. and extracting the mixture with EtOAc (40 mL×3). The combined organic layers were dried over anhydrous sodium sulfate, filtered, and concentrated under reduced pressure. The crude product (1.2 g, crude) was obtained as a black brown oil and used in the next step without further purification. MS ($ES^{30}$, m/z): 468.2.

Preparation of 2-(4-((2-iodo-1-(2,2,2-trifluoroethyl)-1H-indol-4-yl)amino)piperidin-1-yl)EtOAc, 2-(4-((2-iodo-1-(2,2,2-trifluoroethyl)-1H-indol-4-yl)amino)piperidin-1-yl) ethyl propionate, and 2-(4-((2-iodo-1-(2,2,2-trifluoroethyl)-1H-indol-4-yl)amino)piperidin-1-yl)ethyl isobutyrate: To a solution of 2-(4-((2-iodo-1-(2,2,2-trifluoroethyl)-1H-indol-4-yl)amino)piperidin-1-yl)ethan-1-ol (100 mg, 192.61 µmol, 1 eq.) in DCM (3 mL) was added acetic anhydride (13.93 mg, 136.43 µmol, 12.78 µL, 0.5 eq.) or propionic anhydride (23.67 mg, 181.91 µmol, 23.44 µL, 1 eq.) or isobutyric anhydride (152.35 mg, 963.05 µmol, 159.69 µL, 5 eq.) at 50° C. The mixture was stirred at 50° C. for 2 h. TLC analysis (DCM:MeOH=10:1, $R_f$=0.50) indicated that the reaction was complete. The reaction mixture was concentrated under reduced pressure and purified by prep-TLC ($SiO_2$, EtOAc:PE=8:1, $R_f$=0.43) to afford the desired products as light-yellow solids. 2-(4-((2-iodo-1-(2,2,2-trifluoroethyl)-1H-indol-4-yl)amino)piperidin-1-yl)EtOAc (60 mg, 106.03 µmol, 38.9% yield), MS ($ES^{30}$, m/z): 510.1; 2-(4-((2-iodo-1-(2,2,2-trifluoroethyl)-1H-indol-4-yl)amino)piperidin-1-yl)ethyl propionate, (60 mg, 103.19 µmol, 56.72% yield), MS ($ES^{30}$, m/z): 524.1; and 2-(4-((2-iodo-1-(2,2,2-trifluoroethyl)-1H-indol-4-yl)amino)piperidin-1-yl)ethyl isobutyrate, (95 mg, 159.11 µmol, 82.61% yield).

Preparation of 2-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}EtOAc, 2-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}ethyl propanoate, and 2-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}ethyl 2-methylpropanoate: To a solution of 2-(4-((2-iodo-1-(2,2,2-trifluoroethyl)-1H-indol-4-yl)amino)piperidin-1-yl)EtOAc (60 mg, 106.03 µmol, 1 eq.) or 2-(4-((2-iodo-1-(2,2,2-trifluoroethyl)-1H-indol-4-yl)amino)piperidin-1-yl)ethyl propionate (60 mg, 97.45 µmol, 1 eq.); or 2-(4-((2-iodo-1-(2,2,2-trifluoroethyl)-1H-indol-4-yl)amino)piperidin-1-yl)ethyl isobutyrate (95 mg, 159.11 µmol, 1 eq.) and 3-methoxy-4-(prop-2-yn-1-ylamino)benzenesulfonamide (35.97 mg, 127.23 µmol, 1.2 eq.) in DMSO (3 mL) were added CuI (20.19 mg, 106.03 µmol, 1 eq.), N-isopropylpropan-2-amine (10.73 mg, 106.03 µmol, 14.98 µL, 1 eq.), and Pd(PPh$_3$)$_4$ (2.45 mg, 2.12 µmol, 0.02 eq.) under $N_2$. The mixture was stirred for 1 h at 25° C. LC-MS analysis indicated that the reaction was complete. The reaction mixture was quenched by adding a saturated aqueous EDTA solution (60 mL) at 25° C. and stirring the mixture for 1 h. The mixture was then extracted with EtOAc (20 mL×4). The combined organic layers were dried over anhydrous sodium sulfate, filtered, and concentrated under reduced pressure. The residue was purified by prep-TLC ($SiO_2$, DCM:MeOH=10:1, $R_f$=0.30) and prep-HPLC to afford the desired products as light-yellow solids. 2-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}EtOAc (22.9 mg, 36.06 μmol, 34.01% yield) MS (ES³⁰, m/z): 622.3; 2-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}ethyl propanoate (20 mg, 25.17 μmol, 25.83% yield), MS (ES³⁰, m/z): 636.2; and 2-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}ethyl 2-methylpropanoate (20.5 mg, 31.24 μmol, 19.63% yield), MS (ES³⁰, m/z): 650.3.

Example D41: Synthesis of Compounds 534A and 541A

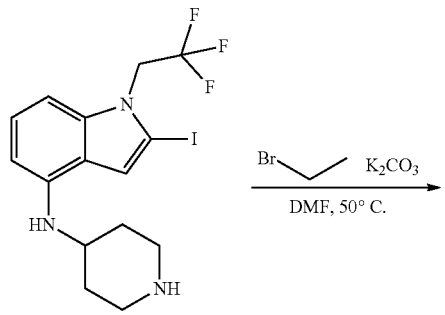

Preparation of N-(1-ethylpiperidin-4-yl)-2-iodo-1-(2,2,2-trifluoroethyl)-1H-indol-4-amine: To a solution of 2-iodo-N-(piperidin-4-yl)-1-(2,2,2-trifluoroethyl)-1H-indol-4-amine (200 mg, 448.95 μmol, 1 eq.) in DMF (8 mL) were added K₂CO₃ (186.14 mg, 1.35 mmol, 3 eq.) and bromoethane (489.19 mg, 4.49 mmol, 335.06 μL, 10 eq.) in one portion under N₂. The mixture was stirred at 40° C. for 60 min. LC-MS analysis showed that the reaction was complete. The reaction was diluted with water (30 mL) and extracted with EtOAc (30 mL×3). The combined organic layers were washed with water (25 mL×2) and brine (25 mL×2), dried over anhydrous sodium sulfate, filtered, and concentrated in vacuo. The crude residue was purified by prep-TLC (SiO₂, DCM:MeOH=10:1, R$_f$=0.29) to afford the desired product (140 mg, 310.24 μmol, 69.10% yield) as a yellow gum. MS (ES³⁰, m/z): 452.2.

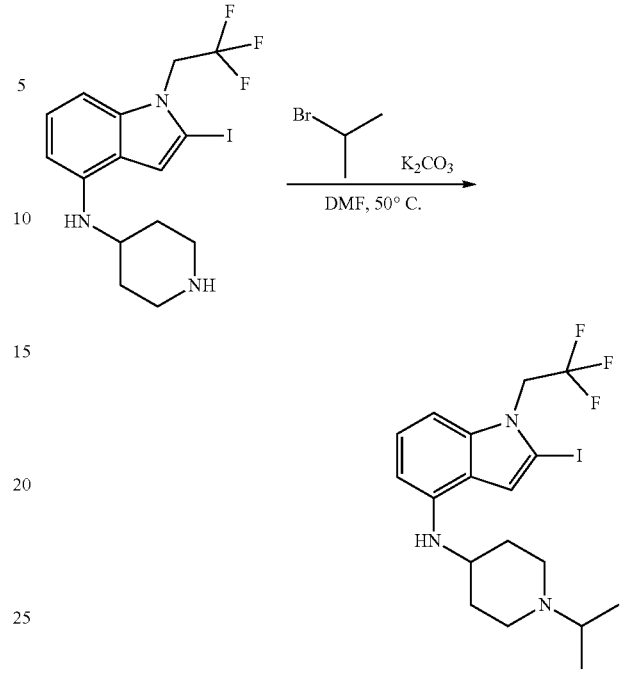

Preparation of 2-iodo-N-(1-isopropylpiperidin-4-yl)-1-(2,2,2-trifluoroethyl)-1H-indol-4-amine: To a solution of 2-iodo-N-(piperidin-4-yl)-1-(2,2,2-trifluoroethyl)-1H-indol-4-amine (200 mg, 448.95 μmol, 1 eq.) in DMF (2 mL) were added K₂CO₃ (186.15 mg, 1.35 mmol, 3 eq.) and 2-bromopropane (552.16 mg, 4.49 mmol, 421.50 μL, 10 eq.) in one portion under N₂. The mixture was stirred at 40° C. for 60 min. LC-MS analysis showed that 15% of the starting material remained, and the desired product was detected. The reaction was diluted with water (30 mL) and extracted with EtOAc (30 mL×3). The combined organic layers were washed with water (25 mL×2) and brine (25 mL×2), dried over anhydrous sodium sulfate, filtered, and concentrated in vacuo. The crude residue was purified by prep-TLC (SiO₂, DCM:MeOH=10:1, R$_f$=0.29) to afford the desired product (130 mg, 279.39 μmol, 62.23% yield) as a yellow solid. MS (ES³⁰, m/z): 466.1.

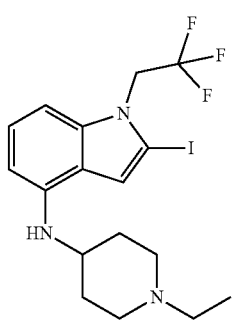

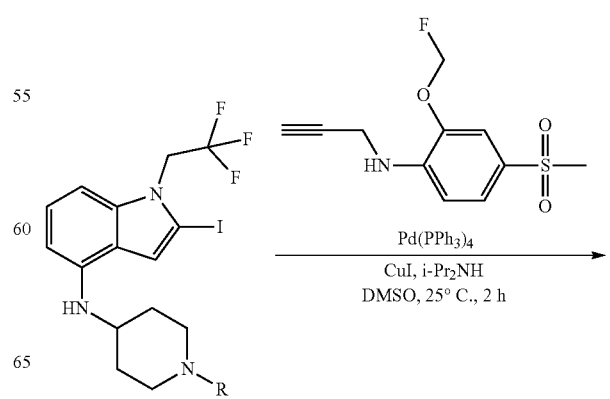

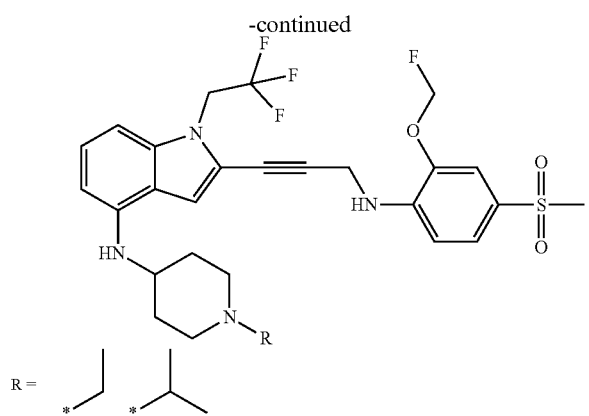

Preparation of N-(1-ethylpiperidin-4-yl)-2-(3-{1[2-(fluoromethoxy)-4-methanesulfonylphenyl]amino}prop-1-yn-1-yl)-1-(2,2,2-trifluoroethyl)-1H-indol-4-amine and 2-(3-{1[2-(fluoromethoxy)-4-methanesulfonylphenyl]amino}prop-1-yn-1-yl)-N-[1-(propan-2-yl)piperidin-4-yl]-1-(2,2,2-trifluoroethyl)-1H-indol-4-amine: To a mixture of N-(1-ethylpiperidin-4-yl)-2-iodo-1-(2,2,2-trifluoroethyl)-1H-indol-4-amine (50 mg, 110.80 μmol, 1 eq.) or 2-iodo-N-(1-isopropylpiperidin-4-yl)-1-(2,2,2-trifluoroethyl)-1H-indol-4-amine (50 mg, 107.46 μmol, 1 eq.) and 2-(fluoromethoxy)-4-(methylsulfonyl)-N-(prop-2-yn-1-yl)aniline (34.21 mg, 132.96 μmol, 1.2 eq.) in DMSO (3 mL) were added N-isopropylpropan-2-amine (112.12 mg, 1.11 mmol, 156.59 μL, 10 eq.), CuI (63.31 mg, 332.40 mol, 3 eq.), and Pd(PPh$_3$)$_4$ (64.02 mg, 55.40 μmol, 0.5 eq.) in one portion under N$_2$. The mixture was stirred at 25° C. for 60 min under N$_2$. LC-MS and TLC analysis showed that the reaction was completed. The reaction mixture was diluted with EtOAc (20 mL), and the resulting mixture was poured into a saturated aqueous EDTA solution (10 mL) and stirred further for 0.5 h. The organic layer was poured into a saturated aqueous EDTA solution (20 mL) and stirred for 1 h, and the aqueous phase was extracted with EtOAc (20 mL×3). The combined organic layers were washed with water (25 mL×3) and brine (15 mL×2), dried over anhydrous sodium sulfate, filtered, and concentrated in vacuo. The crude residue was purified by prep-TLC and prep-HPLC to obtain the desired products as white solids. N-(1-ethylpiperidin-4-yl)-2-(3-{[2-(fluoromethoxy)-4-methanesulfonylphenyl]amino}prop-1-yn-1-yl)-1-(2,2,2-trifluoroethyl)-1H-indol-4-amine (15.4 mg, 25.59 μmol, 23.10% yield), MS (ES$^{3O}$, m/z): 581.3; and 2-(3-{[2-(fluoromethoxy)-4-methanesulfonylphenyl]amino}prop-1-yn-1-yl)-N-[1-(propan-2-yl)piperidin-4-yl]-1-(2,2,2-trifluoroethyl)-1H-indol-4-amine (11.0 mg, 18.04 μmol, 16.78% yield), MS (ES$^{3O}$, m/z): 595.2.

Example D42: Synthesis of N-(1,5-dihydroxypentan-3-yl)-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide (Compound 965A)

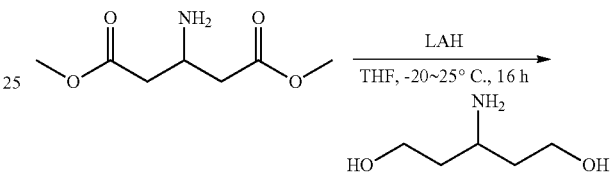

Preparation of 3-aminopentane-1,5-diol: To a solution of dimethyl 3-aminopentanedioate (0.2 g, 1.14 mmol, 1 eq.) in THF (10 mL) was added LiAlH$_4$ (86.66 mg, 2.28 mmol, 2 eq.) at −20° C. The mixture was warmed to 25° C. and stirred for 16 h. Sodium sulfate·10H$_2$O (0.5 g) was slowly added to the mixture, and it was stirred for 0.5 h. The mixture was filtered and concentrated. The residue was dissolved in CH$_3$CN (20 mL) and concentrated to remove water. The crude product (0.12 g, crude) was obtained as a yellow oil and used in the next step without purification.

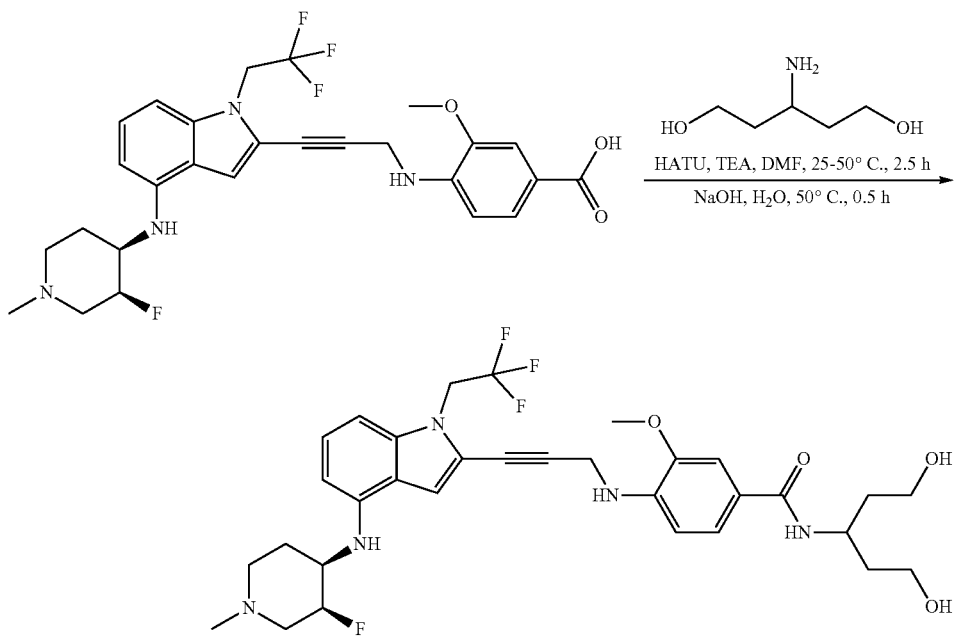

To a solution of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoic acid (0.06 g, 112.67 μmol, 1 eq.) in DMF (2 mL) were added TEA (34.20 mg, 338.01 μmol, 47.05 μL, 3 eq.) and HATU (64.26 mg, 169 μmol, 1.5 eq.). Then, 3-aminopentane-1,5-diol (16.11 mg, 135.20 μmol, 1.2 eq.) was added, and the mixture was warmed to 50° C. and stirred for 1.5 h. The mixture was purified directly using prep-HPLC to afford the desired product (0.033 g, 47.88 μmol, 42.49% yield) as a yellow solid. MS (ES$^{30}$, m/z): 634.3.

Example D43: Synthesis of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-N—((S)-2-hydroxypropyl)-3-methoxybenzamide (Compound 959A)

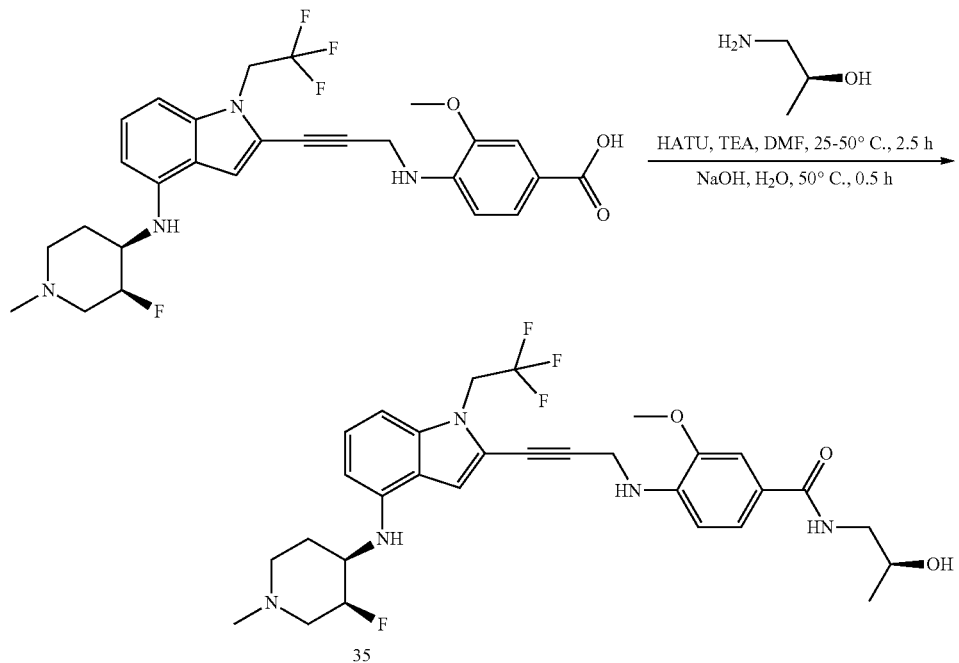

To a solution of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoic acid (0.06 g, 112.67 μmol, 1 eq.) in DMF (1 mL) were added TEA (22.80 mg, 225.34 μmol, 31.36 μL, 2 eq.) and HATU (64.26 mg, 169 μmol, 1.5 eq.) at 25° C. The mixture was stirred for 0.5 h. Then, (S)-1-aminopropan-2-ol (10.16 mg, 135.20 μmol, 10.64 μL, 1.2 eq.) was added, and the mixture was warmed to 50° C. and stirred for 1 h. The reaction mixture was purified directly using prep-HPLC and chiral SFC to afford the desired product (0.030 g, 46.70 μmol, 41.45% yield) as a yellow solid. MS (ES$^{30}$, m/z): 590.2.

Example D44: Synthesis of N-[(2S)-2,3-dihydroxypropyl]-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide (Compound 964A)

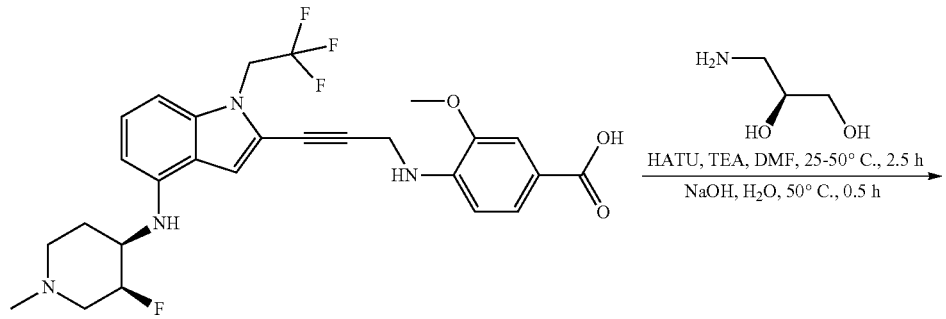

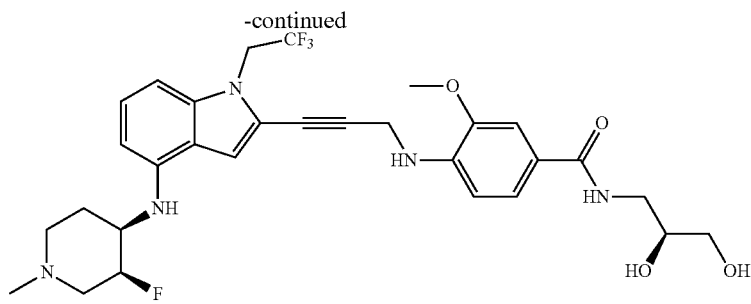

To a solution of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoic acid (0.07 g, 131.45 μmol, 1 eq.) in DMF (2 mL) were added TEA (39.90 mg, 394.34 μmol, 54.89 μL, 3 eq.) and HATU (74.97 mg, 197.17 μmol, 1.5 eq.) at 25° C. The mixture was stirred for 0.5 h. Then, (S)-3-aminopropane-1,2-diol (13.17 mg, 144.59 μmol, 11.16 μL, 1.1 eq.) was added, and the mixture was stirred at 25° C. for 11.5 h. The reaction mixture was purified directly using prep-HPLC to afford the desired product (0.031 g, 50.09 μmol, 38.10% yield) as a yellow solid. MS (ES$^{30}$, m/z): 606.2.

Example D45: Synthesis of Compound 951A, 952A, 953A, 954A, and 955A

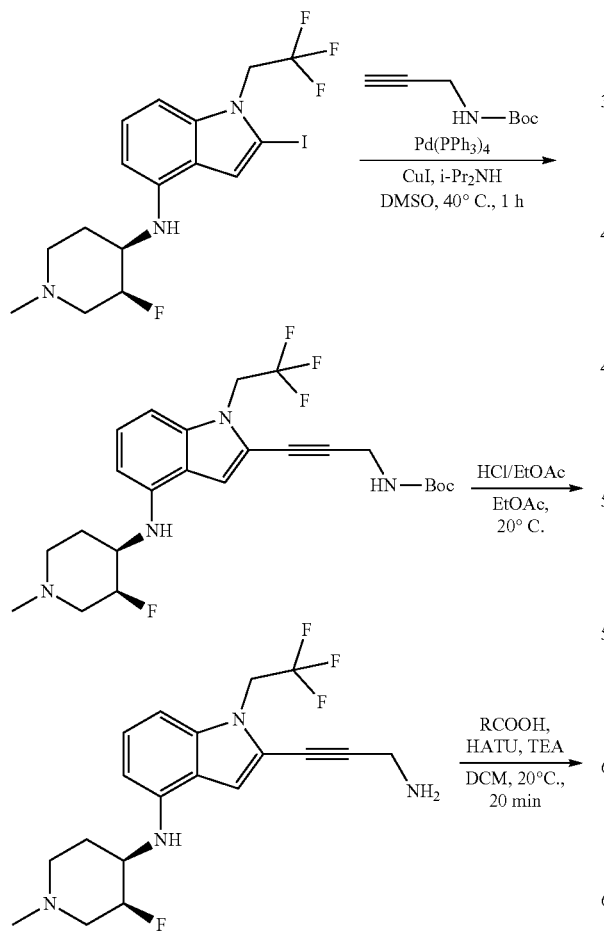

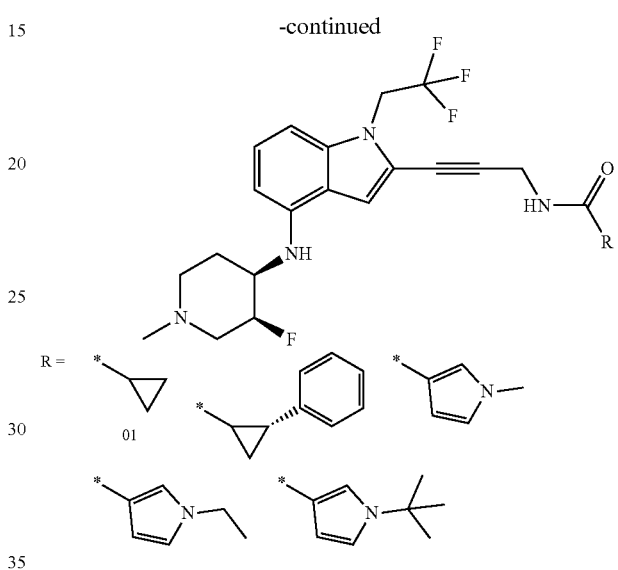

Preparation of tert-butyl (3-(4-(((3S,4R)-3-fluoro-1-methylpiperidin-4-yl)amino)-1-(2,2,2-trifluoroethyl)-1H-indol-2-yl)prop-2-yn-1-yl)carbamate: To a solution of tert-butyl prop-2-yn-1-ylcarbamate (204.55 mg, 1.32 mmol, 1.2 eq.) in DMSO (5 mL) were added i-Pr$_2$NH ((1.11 g, 10.98 mmol, 1.55 mL, 10 eq.), CuI (41.84 mg, 219.67 μmol, 0.2 eq.), N-((3S,4R)-3-fluoro-1-methylpiperidin-4-yl)-2-iodo-1-(2,2,2-trifluoroethyl)-1H-indol-4-amine (0.5 g, 1.10 mmol, 1 eq.), and Pd(PPh$_3$)$_4$ (63.46 mg, 54.92 μmol, 0.05 eq.). The mixture was stirred at 40° C. for 1 h. TLC analysis indicated that the starting material was consumed completely, and one new spot had formed. The reaction mixture was quenched by adding a saturated aqueous EDTA solution (30 mL) solution and stirring the mixture at 20° C. for 1 h. The reaction mixture was diluted with water (10 mL) and extracted with EtOAc (40 mL×3). The combined organic layers were washed with brine (30 mL×3), dried over anhydrous sodium sulfate, filtered, and concentrated under reduced pressure to give a residue. The residue was purified by column chromatography (SiO$_2$, PE:EtOAc=10:1 to 0:1) to afford the desired product as a yellow solid. (0.45 g, 774.07 μmol, 70.48% yield).

Preparation of 2-(3-aminoprop-1-yn-1-yl)-N-((3S,4R)-3-fluoro-1-methylpiperidin-4-yl)-1-(2,2,2-trifluoroethyl)-1H-indol-4-amine: A mixture of tert-butyl (3-(4-(((3S,4R)-3-fluoro-1-methylpiperidin-4-yl)amino)-1-(2,2,2-trifluoroethyl)-1H-indol-2-yl)prop-2-yn-1-yl)carbamate (0.35 g, 725.37 μmol, 1 eq.) and 4M HCl/EtOAc (3 mL) was degassed and purged with N$_2$ three times. The mixture was stirred at 20° C. for 1 h under N$_2$. TLC analysis indicated that the starting material was consumed completely, and that one new spot had formed. The reaction mixture was quenched by adding a saturated aqueous $Na_2CO_3$ solution to adjust the pH of the mixture to >7. The mixture was then diluted with water (10 mL) and extracted with EtOAc (30 mL×3). The combined organic layers were washed with brine (30 mL×3), dried over anhydrous sodium sulfate, filtered, and concentrated under reduced pressure to afford the desired product as a yellow solid (0.25 g, 588.39 µmol, 81.12% yield).

Preparation of desired products: To a mixture of 2-(3-aminoprop-1-yn-1-yl)-N-((3S,4R)-3-fluoro-1-methylpiperidin-4-yl)-1-(2,2,2-trifluoroethyl)-1H-indol-4-amine (0.05 g, 130.75 µmol, 1 eq.) and cyclopropanecarboxylic acid (11.26 mg, 130.75 µmol, 10.33 µL, 1 eq.) in DMF (3 mL) were added TEA (66.15 mg, 653.77 µmol, 91 µL, 5 eq.) and HATU (59.66 mg, 156.90 µmol, 1.2 eq.). The mixture was stirred at 20° C. for 20 min. TLC analysis (DCM:MeOH=10:1, $R_f$=0.5) indicated that the starting material was consumed. The reaction mixture was quenched by adding water (10 mL) and extracting the mixture with EtOAc (10 mL×3). The combined organic layers were washed with brine (10 mL×3), dried over anhydrous sodium sulfate, filtered, and concentrated under reduced pressure to give a residue. The residue was purified by prep-TLC ($SiO_2$, DCM:MeOH=10:1) to afford the desired products as yellow solids.

N-[3-(4-{[(3S,4R)-3-fluoro-1-methylpiperidin-4-yl] amino}-1-(2,2,2-trifluoroethyl)-1H-indol-2-yl)prop-2-yn-1-yl]cyclopropanecarboxamide, (0.018 g, 39.24 µmol, 30% yield), MS ($ES^{30}$, m/z): 451.2; (1R,2R)—N-[3-(4-{[(3S,4R)-3-fluoro-1-methylpiperidin-4-yl]amino}-1-(2,2,2-trifluoroethyl)-1H-indol-2-yl)prop-2-yn-1-yl]-2-phenylcyclopropane-1-carboxamide, (0.026 g, 48.64 µmol, 37% yield), MS ($ES^{30}$, m/z): 527.3; N-[3-(4-{[(3S,4R)-3-fluoro-1-methylpiperidin-4-yl]amino}-1-(2,2,2-trifluoroethyl)-1H-indol-2-yl)prop-2-yn-1-yl]-1-methyl-1H-pyrrole-3-carboxamide, (0.021 g, 42.34 µmol, 32% yield), MS ($ES^{30}$, m/z): 490.2; 1-ethyl-N-[3-(4-{[(3S,4R)-3-fluoro-1-methylpiperidin-4-yl]amino}-1-(2,2,2-trifluoroethyl)-1H-indol-2-yl)prop-2-yn-1-yl]-1H-pyrrole-3-carboxamide, (0.021 g, 40.87 µmol, 31% yield), MS ($ES^{30}$, m/z): 504.2; and 1-tert-butyl-N-[3-(4-{[(3S,4R)-3-fluoro-1-methylpiperidin-4-yl]amino}-1-(2,2,2-trifluoroethyl)-1H-indol-2-yl)prop-2-yn-1-yl]-1H-pyrrole-3-carboxamide, (0.016 g, 29.68 µmol, 23% yield), MS ($ES^{30}$, m/z): 532.3.

Example D46: Synthesis of 2-(3-((4-methoxy-6-(methylsulfonyl)pyridin-3-yl)amino)prop-1-yn-1-yl)-N-(1-methylpiperidin-4-yl)-1-(2,2,2-trifluoroethyl)-1H-indol-4-amine (Compound 476A)

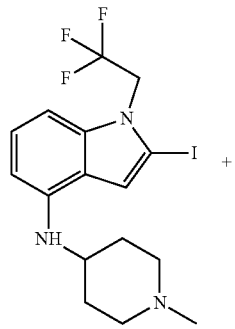

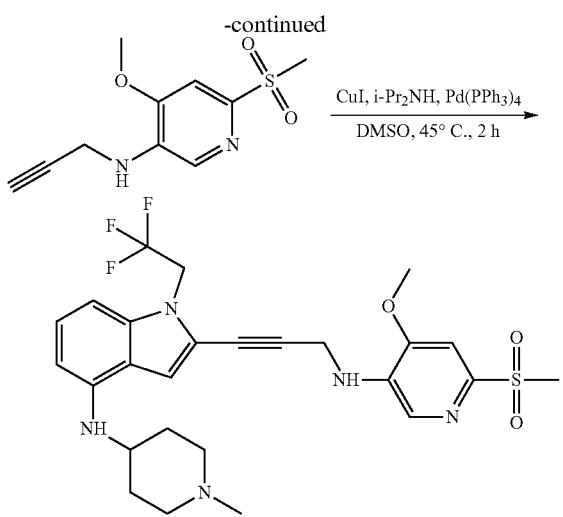

Preparation of 2-(3-((4-methoxy-6-(methylsulfonyl)pyridin-3-yl)amino)prop-1-yn-1-yl)-N-(1-methylpiperidin-4-yl)-1-(2,2,2-trifluoroethyl)-1H-indol-4-amine: A solution of 4-methoxy-6-(methylsulfonyl)-N-(prop-2-yn-1-yl)pyridin-3-amine (50 mg, 180.68 µmol, 1.2 eq., HCl) in DMSO (2 mL) was flushed with $N_2$. To the mixture were added CuI (28.67 mg, 150.56 µmol, 1 eq.), N-isopropylpropan-2-amine (45.71 mg, 451.69 µmol, 63.84 µL, 3 eq.), and 2-iodo-N-(1-methylpiperidin-4-yl)-1-(2,2,2-trifluoroethyl)-1H-indol-4-amine (65.83 mg, 150.56 µmol, 1 eq.), and $Pd(PPh_3)_4$ (13.92 mg, 12.05 µmol, 0.08 eq.) was added. The reaction mixture was flushed again with $N_2$ and stirred at 45° C. for 2 h. LC-MS analysis showed that the starting material was consumed completely, and one main peak with the desired mass was detected. A saturated aqueous EDTA solution (20 mL) was added, and the mixture was stirred at 15° C. for 1 h. Then EtOAc (20 mL) was added. The organic phase was separated, washed with brine (5 mL×3), dried over anhydrous sodium sulfate, filtered, and concentrated under reduced pressure to give a residue. The residue was purified by prep-HPLC to afford the desired product (9.6 mg, 17.47 µmol, 12% yield) as a white solid. MS ($ES^{30}$, m/z): 550.1.

Example D47: Synthesis of Compounds 468A and 554A

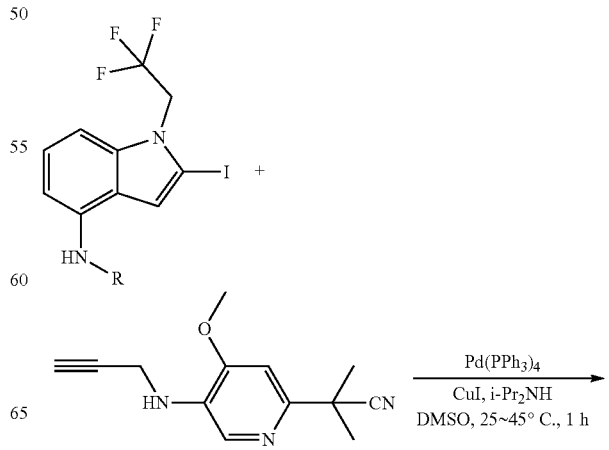

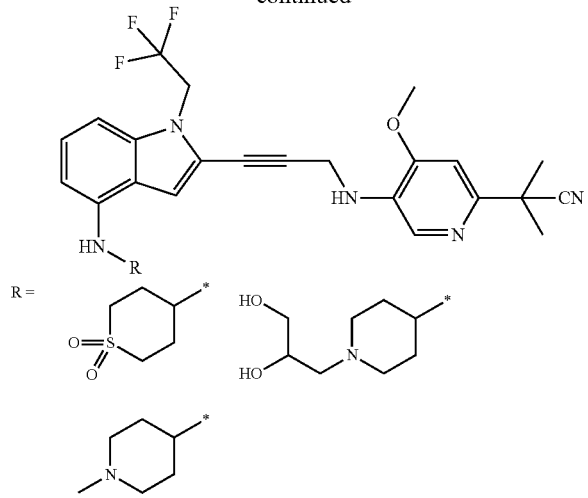

R =

To a solution of 2-[4-methoxy-5-(prop-2-ynylamino)-2-pyridyl]-2-methyl-propanenitrile (44.26 mg, 193.05 μmol, 1.2 eq.) in DMSO (2 mL) were added i-Pr$_2$NH (162.79 mg, 1.61 mmol, 227.35 μL, 10 eq.), CuI (30.64 mg, 160.87 μmol, 1 eq.), 3-[4-[[2-iodo-1-(2,2,2-trifluoroethyl)indol-4-yl]amino]-1-piperidyl]propane-1,2-diol (80 mg, 160.87 μmol, 1 eq.), and Pd(PPh$_3$)$_4$ (37.18 mg, 32.17 μmol, 0.2 eq.) in one portion at 25° C. under N$_2$. The mixture was stirred at 45° C. for 1 h. LC-MS and TLC analysis (EtOAc:MeOH=2:1, R$_f$=0.45) showed that the reaction was complete. EtOAc (10 mL) was poured into the mixture, and the resulting mixture was poured into a saturated aqueous EDTA solution (40 mL) and stirred for 15 min. The aqueous phase was extracted with EtOAc (40 mL×2). The organic layer was poured to a saturated aqueous EDTA solution (40 mL) and stirred for 1 h. The aqueous phase was extracted with EtOAc (40 mL×3). The combined organic layers were washed with brine (40 mL×3), dried over anhydrous sodium sulfate, filtered, and concentrated in vacuo. The residue was purified by prep-TLC (EtOAc:MeOH=2:1, R$_f$=0.45) then purified further by prep-HPLC to afford the desired products.

2-{4-methoxy-5-[(3-{4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile (3.2 mg, 5.68 μmol, 3% yield), MS (ES$^+$, m/z): 539.3; 2-(5-{[3-(4-{[1-(2,3-dihydroxypropyl)piperidin-4-yl]amino}-1-(2,2,2-trifluoroethyl)-1H-indol-2-yl)prop-2-yn-1-yl]amino}-4-methoxypyridin-2-yl)-2-methylpropanenitrile (22.8 mg, 37.17 μmol, 23% yield), MS (ES$^+$, m/z): 599.3; and 2-{5-[(3-{4-[(1,1-dioxo-1λ$^6$-thian-4-yl)amino]-1-(2,2,2-trifluoroethyl)-1H-indol-2-yl}prop-2-yn-1-yl)amino]-4-methoxypyridin-2-yl}-2-methylpropanenitrile (3.5 mg, 6.04 μmol, 4% yield), MS (ES$^+$, m/z): 574.2.

Example D48: Synthesis of Compounds 530A, 692A, 719A, 720A, and 763A

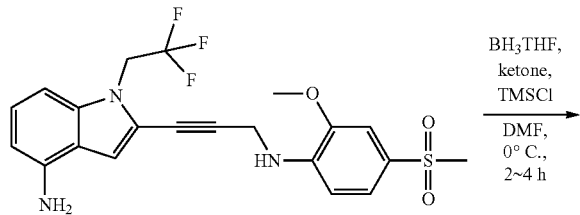

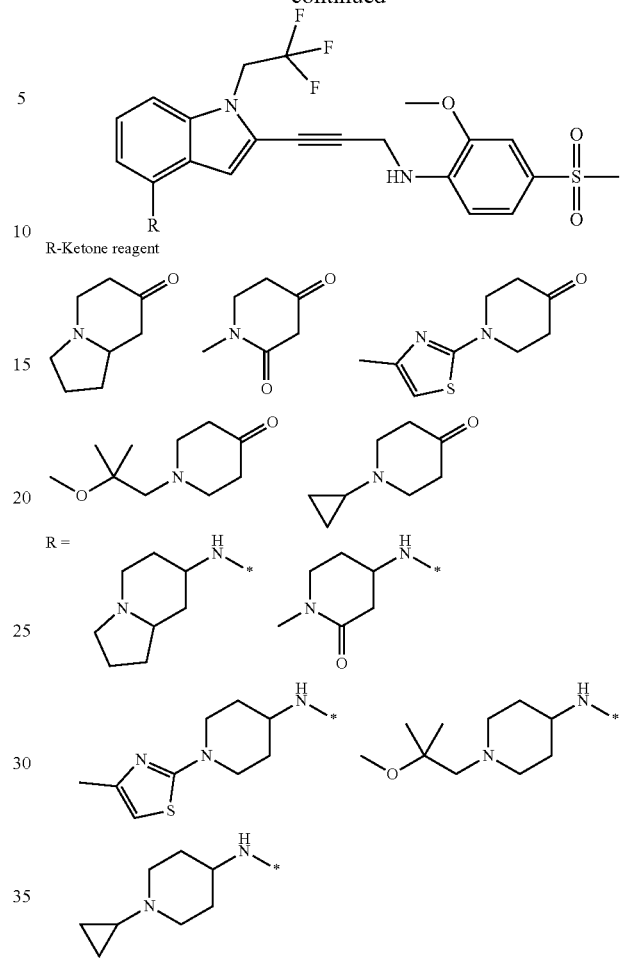

R-Ketone reagent

R =

To a solution of 2-[3-(2-methoxy-4-methylsulfonyl-anilino)prop-1-ynyl]-1-(2,2,2-trifluoroethyl)indol-4-amine (50 mg, 99.68 μmol, 1 eq.) and 1-methylpiperidine-2,4-dione (95.05 mg, 598.06 μmol, 6 eq.) in DMF (3 mL) was added (27.07 mg, 249.19 μmol, 31.63 μL, 2.5 eq.). The mixture was stirred at 0° C. for 2 h. Then, BH$_3$·THF (1 M, 498.38 μL, 5 eq.) was added under N$_2$, and the mixture was stirred at 25° C. for 2 h. LC-MS or TLC analysis indicated that the reaction was complete. The reaction mixture was quenched by adding a saturated aqueous Na$_2$CO$_3$ solution (30 mL). The resulting mixture was then diluted with water (10 mL) and extracted with EtOAc (20 mL×2). The combined organic layers were washed with brine (10 mL), dried over anhydrous sodium sulfate, filtered, and concentrated under reduced pressure. The residue was purified by prep-HPLC to afford the desired products as light yellow solids.

2-{3-[(4-methanesulfonyl-2-methoxyphenyl)amino]prop-1-yn-1-yl}-N-[1-(4-methyl-1,3-thiazol-2-yl)piperidin-4-yl]-1-(2,2,2-trifluoroethyl)-1H-indol-4-amine (30 mg, 45.83 μmol, 21% yield), MS (ES$^{30}$, m/z): 632.2; 2-{3-[(4-methanesulfonyl-2-methoxyphenyl)amino]prop-1-yn-1-yl}-N-[1-(2-methoxy-2-methylpropyl)piperidin-4-yl]-1-(2,2,2-trifluoroethyl)-1H-indol-4-amine (31.7 mg, 50 μmol, 50% yield) MS (ES$^{30}$, m/z): 621.2; 2-(3-((2-methoxy-4-(methylsulfonyl)phenyl)amino)prop-1-yn-1-yl)-N-(octahydroindolizin-7-yl)-1-(2,2,2-trifluoroethyl)-1H-indol-4-amine (10 mg, 17.14 μmol, 39% yield), MS (ES$^{30}$, m/z): 575.2; N-(1-cyclopropylpiperidin-4-yl)-2-{3-[(4-methanesulfonyl-2- methoxyphenyl)amino]prop-1-yn-1-yl}-1-(2,2,2-trifluoro-ethyl)-1H-indol-4-amine, (61 mg, 104.03 μmol, 58% yield), MS (ES³⁰, m/z) 575.2; 4-((2-(3-((2-methoxy-4-(methyl-sulfonyl)phenyl)amino)prop-1-yn-1-yl)-1-(2,2,2-trifluoro-ethyl)-1H-indol-4-yl)amino)-1-methylpiperidin-2-one (23.7 mg, 41.75 μmol, 42% yield), MS (ES³⁰, m/z): 563.2.

Example D49: Synthesis of Compounds 491A, 492A, 496A, 497A, 498A, and 499A

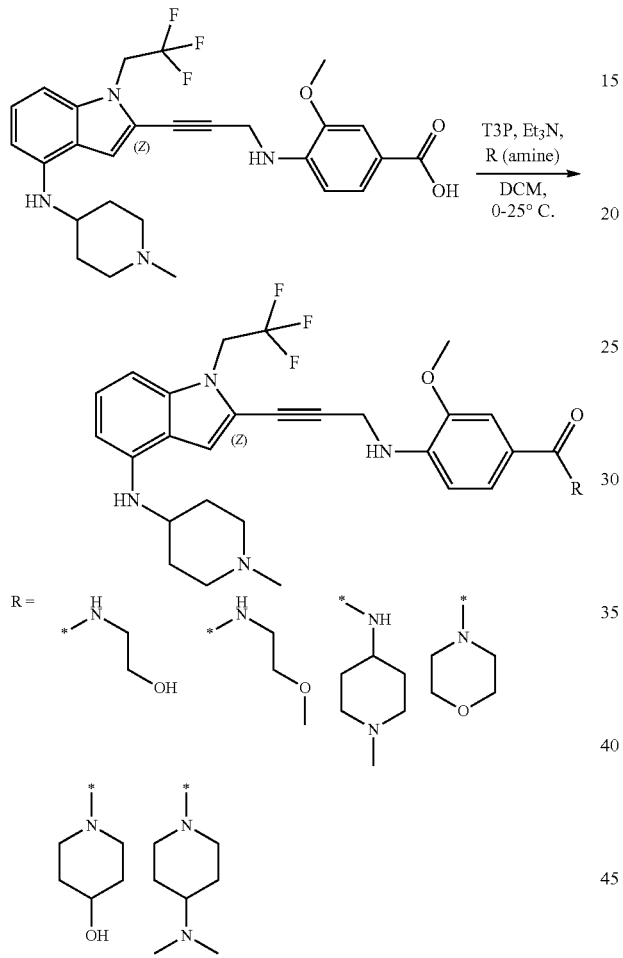

To a solution of 3-methoxy-4-[3-[4-[(1-methyl-4-piperidyl)amino]-1-(2,2,2-trifluoroethyl)indol-2-yl]prop-2-ynylamino]benzoic acid (150 mg, 87.46 μmol, 1 eq.) and 2-aminoethanol (8.01 mg, 131.19 μmol, 7.93 μL, 1.5 eq.) in DCM (5 mL) was added Et₃N (53.10 mg, 524.74 μmol, 73.04 μL, 6 eq.). The mixture was cooled to 0° C., and propylphosphonic anhydride (T3P) (83.48 mg, 131.19 μmol, 78.02 μL, 50% purity, 1.5 eq.) was added. The resulting mixture was stirred at 20° C. for 1~2 h. The reaction mixture was diluted with water (30 mL) and extracted with DCM (10 mL×3). The combined organic layers were washed with brine (10 mL), dried over anhydrous sodium sulfate, filtered and concentrated under reduced pressure to give a residue. The residue was purified by prep-TLC (SiO₂, DCM:MeOH=10:1) and further purified by prep-HPLC to afford the desired products.

N-(2-hydroxyethyl)-3-methoxy-4-[(3-{4-[(1-methylpiperidin-4-yl)amino]-1-(2,2,2-trifluoroethyl)-1H-indol-2-yl}prop-2-yn-1-yl)amino]benzamide (15.1 mg, 26.60 μmol, 30% yield), MS (ES³⁰, m/z): 558.2; 3-methoxy-N-(2-methoxyethyl)-4-[(3-{4-[(1-methylpiperidin-4-yl)amino]-1-(2,2,2-trifluoroethyl)-1H-indol-2-yl}prop-2-yn-1-yl)amino]benzamide (20.2 mg, 35.03 μmol, 40% yield) MS (ES³⁰, m/z): 572.2; 3-methoxy-N-(1-methylpiperidin-4-yl)-4-[(3-{4-[(1-methylpiperidin-4-yl)amino]-1-(2,2,2-trifluoroethyl)-1H-indol-2-yl}prop-2-yn-1-yl)amino]benzamide (14.3 mg, 23.25 μmol, 27% yield), MS (ES³⁰, m/z): 611.3; 2-(3-{[2-methoxy-4-(morpholine-4-carbonyl)phenyl]amino}prop-1-yn-1-yl)-N-(1-methylpiperidin-4-yl)-1-(2,2,2-trifluoroethyl)-1H-indol-4-amine (23.1 mg, 39.14 μmol, 34% yield) MS (ES³⁰, m/z): 584.3; 1-{3-methoxy-4-[(3-{4-[(1-methylpiperidin-4-yl)amino]-1-(2,2,2-trifluoroethyl)-1H-indol-2-yl}prop-2-yn-1-yl)amino]benzoyl}piperidin-4-ol (19.6 mg, 32.37 μmol, 21% yield), MS (ES³⁰, m/z): 598.3; 2-[3-({4-[4-(dimethylamino)piperidine-1-carbonyl]-2-methoxyphenyl}amino)prop-1-yn-1-yl]-N-(1-methylpiperidin-4-yl)-1-(2,2,2-trifluoroethyl)-1H-indol-4-amine (22.1 mg, 34.95 μmol, 30% yield) MS (ES³⁰, m/z): 625.3.

Example D50: Synthesis of 3-methoxy-4-[(3-{4-[(1-methylpiperidin-4-yl)amino]-1-(2,2,2-trifluoro-ethyl)-1H-indol-2-yl}prop-2-yn-1-yl)amino]-N-(oxan-4-yl)benzamide (Compound 500A)

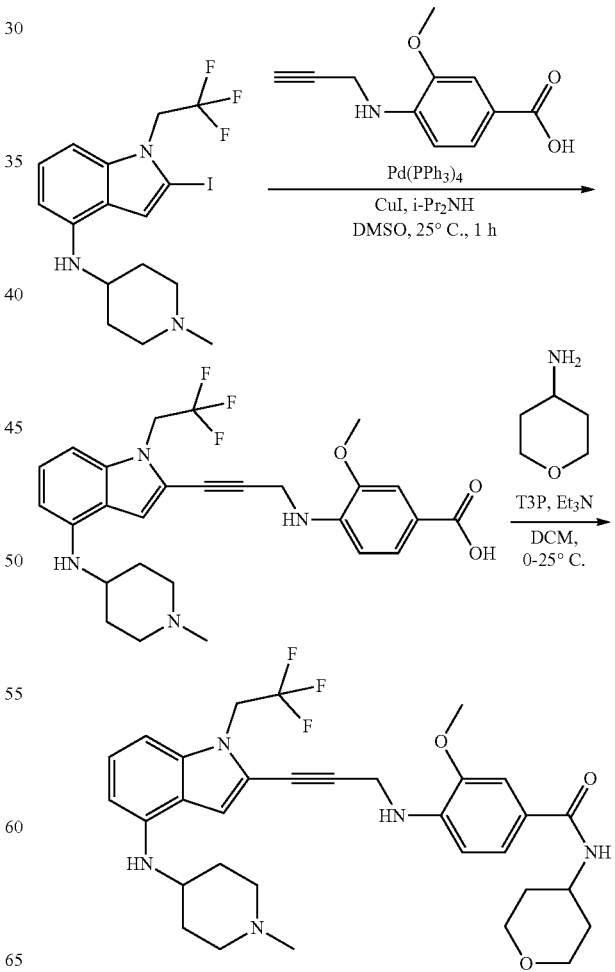

Preparation of 3-methoxy-4-((3-(4-((1-methylpiperidin-4-yl)amino)-1-(2,2,2-trifluoroethyl)-1H-indol-2-yl)prop-2-yn-1-yl)amino)benzoic acid: A mixture of 2-iodo-N-(1-methylpiperidin-4-yl)-1-(2,2,2-trifluoroethyl)-1H-indol-4-amine (1.3 g, 2.97 mmol, 1 eq.), 3-methoxy-4-(prop-2-yn-1-ylamino)benzoic acid (610.13 mg, 2.97 mmol, 1 eq.), N-isopropylpropan-2-amine (601.71 mg, 5.95 mmol, 840.38 μL, 2 eq.), CuI (283.12 mg, 1.49 mmol, 0.5 eq.), and Pd(PPh$_3$)$_4$ (343.57 mg, 297.32 μmol, 0.1 eq.) in DMSO (15 mL) was degassed and purged with N$_2$ three times. The mixture was then stirred at 20° C. for 1 h under N$_2$. TLC analysis (THF:MeOH=5:2, R$_f$=0.1) showed that the reaction was complete. A saturated aqueous EDTA solution (100 mL) was added to the mixture, and the resulting mixture was stirred for 1 h. The mixture was extracted with EtOAc (150 mL×8). The combined organic layers were washed with brine (50 mL×2), and dried over anhydrous sodium sulfate, filtered, and concentrated under reduced pressure. The crude product (2 g, 2.33 mmol, 78% yield) was obtained as a yellow solid and used without purification.

Preparation of 3-methoxy-4-[(3-{4-[(1-methylpiperidin-4-yl)amino]-1-(2,2,2-trifluoroethyl)-1H-indol-2-yl}prop-2-yn-1-yl)amino]-N-(oxan-4-yl)benzamide: To a mixture of 3-methoxy-4-((3-(4-((1-methylpiperidin-4-yl)amino)-1-(2,2,2-trifluoroethyl)-1H-indol-2-yl)prop-2-yn-1-yl)amino) benzoic acid (0.15 g, 291.52 μmol, 1 eq.), tetrahydropyran-4-amine (44.23 mg, 437.29 μmol, 1.5 eq.), and TEA (88.50 mg, 874.57 μmol, 121.73 μL, 3 eq.) in DCM (10 mL) was added T3P® (278.27 mg, 437.29 μmol, 260.07 μL, 50% purity, 1.5 eq.). The mixture was stirred at 20° C. for 1 h under N$_2$. LC-MS analysis detected presence of the desired product. The mixture was diluted with water (15 mL) and was extracted with DCM (20 mL×3). The combined organic layers were washed with brine (10 mL), dried over anhydrous sodium sulfate, filtered, and concentrated under reduced pressure. The crude residue was purified by prep-HPLC to afford the desired product (0.013 g, 20.66 μmol, 7% yield) as a white solid. MS (ES$^{30}$, m/z): 598.3.

Example D51: Synthesis of 2-{3-[(2-methoxy-4-{2-oxa-6-azaspiro[3.3]heptane-6-carbonyl}phenyl)amino]prop-1-yn-1-yl}-N-(1-methylpiperidin-4-yl)-1-(2,2,2-trifluoroethyl)-1H-indol-4-amine (Compound 502A)

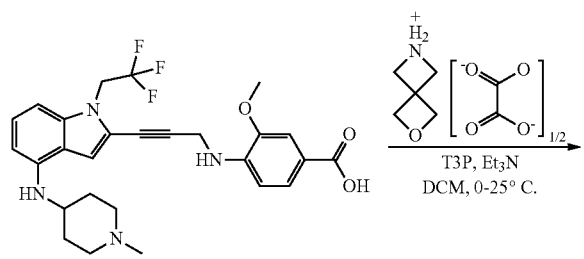

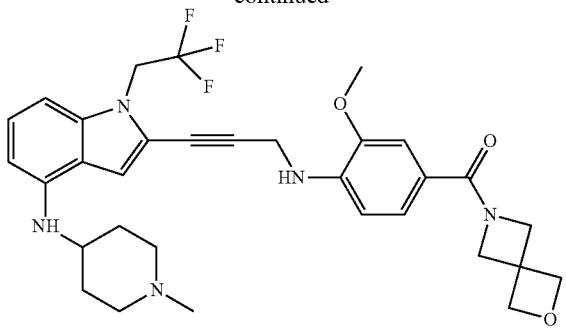

To a mixture of 3-methoxy-4-((3-(4-((1-methylpiperidin-4-yl)amino)-1-(2,2,2-trifluoroethyl)-1H-indol-2-yl)prop-2-yn-1-yl)amino)benzoic acid (0.15 g, 291.52 μmol, 1 eq.), 2-oxa-6-azaspiro[3.3]heptan-6-ium oxalate (82.72 mg, 437.29 μmol, 1.5 eq.), TEA (147.50 mg, 1.46 mmol, 202.88 μL, 5 eq.) in DCM (20 mL) was added T3P® (propanephosphonic acid anhydride) (278.27 mg, 437.29 μmol, 260 μL, 50% purity, 1.5 eq.) dropwise under N$_2$. The mixture was stirred at 20° C. for 1 h under N$_2$. LC-MS and HPLC analysis detected presence of the desired product. The mixture was diluted with water (40 mL) and extracted with DCM (50 mL×3). The combined organic layers were washed with brine (30 mL), dried over anhydrous sodium sulfate, filtered, and concentrated under reduced pressure. The crude residue was purified by prep-HPLC to afford the desired product (0.043 g, 68.58 μmol, 23.52% yield) as a yellow solid. MS (ES$^{30}$, m/z): 596.3.

Example D52: Synthesis of 2-(3-{[2-methoxy-4-(4-methylpiperazine-1-carbonyl)phenyl]amino}prop-1-yn-1-yl)-N-(1-methylpiperidin-4-yl)-1-(2,2,2-trifluoroethyl)-1H-indol-4-amine (Compound 501A)

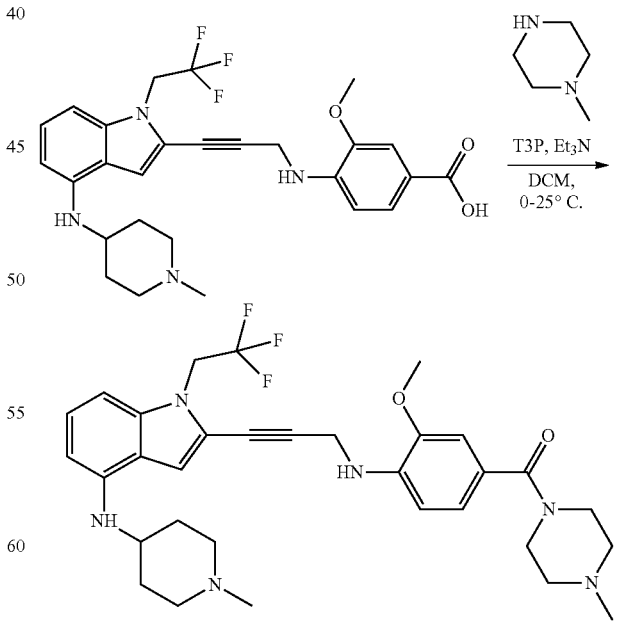

To a mixture of 3-methoxy-4-((3-(4-((1-methylpiperidin-4-yl)amino)-1-(2,2,2-trifluoroethyl)-1H-indol-2-yl)prop-2-yn-1-yl)amino)benzoic acid (0.15 g, 291.52 μmol, 1 eq.), 1-methylpiperazine (44 mg, 437.29 μmol, 48.50 μL, 1.5 eq.), TEA (88.50 mg, 874.57 μmol, 121.73 μL, 3 eq.) in DCM (20 mL) was added T3P® (propanephosphonic acid anhydride) (278.27 mg, 437.29 μmol, 260 μL, 50% purity, 1.5 eq.) dropwise under N$_2$. The mixture was stirred at 20° C. for 1 h under N$_2$. LC-MS and HPLC analysis detected presence of the desired product. The mixture was diluted with water (40 mL) and extracted with DCM (50 mL×3). The combined organic layers were washed with brine (30 mL), dried over anhydrous sodium sulfate, filtered, and concentrated under reduced pressure. The crude residue was purified by prep-HPLC to afford the desired product (0.021 g, 33.43 μmol, 11.47% yield) as a yellow solid. MS (ES$^{30}$, m/z): 597.3.

Example D53: Synthesis of 2-{3-[(2-methoxy-4-{7-oxa-2-azaspiro[3.5]nonane-2-carbonyl}phenyl)amino]prop-1-yn-1-yl}-N-(1-methylpiperidin-4-yl)-1-(2,2,2-trifluoroethyl)-1H-indol-4-amine (Compound 511A)

Example D54: Synthesis of 3-methoxy-4-{1[3-(4-{[1-(oxan-4-yl)piperidin-4-yl]amino}-1-(2,2,2-trifluoroethyl)-1H-indol-2-yl)prop-2-yn-1-yl]amino}benzoic acid (Compound 724A)

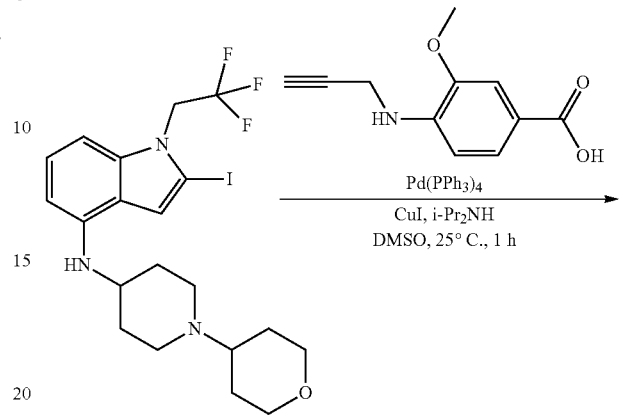

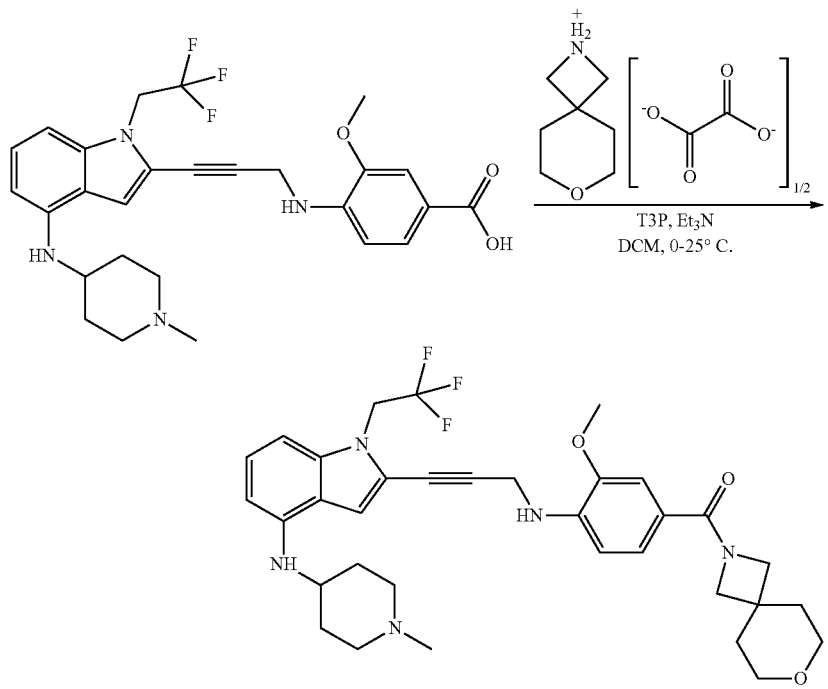

To a mixture of 3-methoxy-4-((3-(4-((1-methylpiperidin-4-yl)amino)-1-(2,2,2-trifluoroethyl)-1H-indol-2-yl)prop-2-yn-1-yl)amino)benzoic acid (0.1 g, 194.35 μmol, 1 eq.), 7-oxa-2-azaspiro[3.5]nonan-2-ium oxalate (80.32 mg, 233.22 μmol, 1.2 eq.), TEA (98.33 mg, 971.75 μmol, 135.26 μL, 5 eq.) in DCM (20 mL) was added T3P® (propanephosphonic acid anhydride) (185.51 mg, 291.52 μmol, 173.38 μL, 50% purity, 1.5 eq.) dropwise under N$_2$. The mixture was stirred at 20° C. for 1 h under N$_2$. LC-MS and HPLC analysis detected presence of the desired product. The mixture was diluted with water (40 mL) and extracted with DCM (50 mL×3). The combined organic layers were washed with brine (30 mL), dried over anhydrous sodium sulfate, filtered, and concentrated under reduced pressure. The crude residue was purified by prep-HPLC to afford the desired product (0.026 g, 38.71 μmol, 19.92% yield) as a yellow solid. MS (ES$^{30}$, m/z): 624.3.

-continued

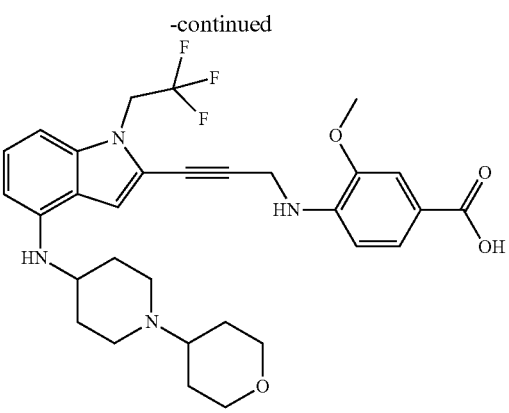

A mixture of 2-iodo-N-(1-(tetrahydro-2H-pyran-4-yl)piperidin-4-yl)-1-(2,2,2-trifluoroethyl)-1H-indol-4-amine (0.1 g, 197.11 µmol, 1 eq.), 3-methoxy-4-(prop-2-yn-1-ylamino)benzoic acid (49 mg, 236.53 µmol, 1.2 eq.) CuI (38 mg, 197.11 µmol, 1 eq.), Pd(PPh$_3$)$_4$ (49.89 mg, 43.17 µmol, 0.2 eq.), and i-Pr$_2$NH (218.42 mg, 2.16 mmol, 305.06 µL, 10 eq.) in DMSO (3 mL) was degassed and purged with N$_2$ three times. The mixture was stirred at 25° C. for 1 h under N$_2$. TLC analysis (EtOAc:TEA=10:1, R$_f$=0.1) indicated that the starting material was consumed, and one new spot was detected. A saturated aqueous EDTA solution (20 mL) was added to the reaction mixture and stirred at 20° C. for 1 h under N$_2$. The reaction mixture was extracted with EtOAc (15 mL×3). The combined organic layers were washed with brine (10 mL×3), dried over anhydrous sodium sulfate, filtered, and concentrated under reduced pressure to give a residue. The residue was purified by prep-TLC (SiO$_2$, EtOAc:TEA=15:1) and prep-HPLC to afford the desired product (0.03 g, 54.77 µmol, 25.38% yield) as a yellow solid. MS (ES$^{30}$, m/z): 585.3.

Example D55: Synthesis of 4-[(3-{4-[(1-cyclopropylpiperidin-4-yl)amino]-1-(2,2,2-trifluoroethyl)-1H-indol-2-yl}prop-2-yn-1-yl)amino]-3-methoxybenzoic acid (Compound 721A)

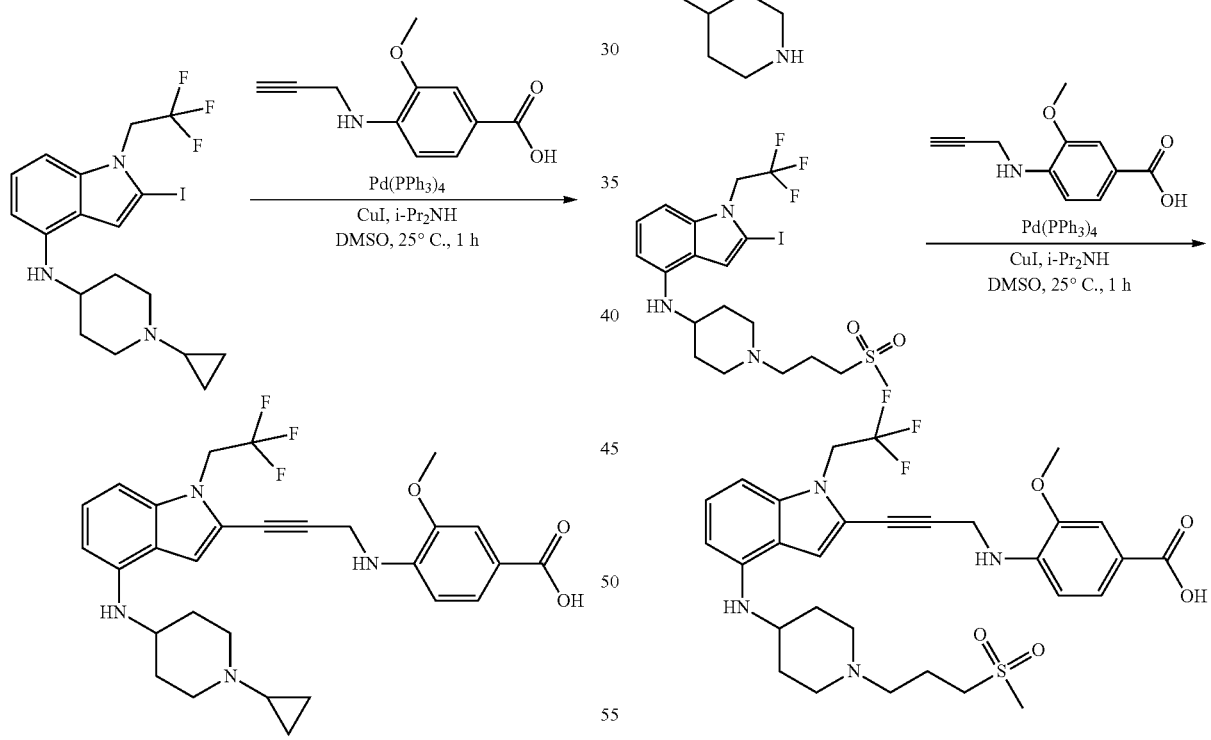

A mixture of 3-methoxy-4-(prop-2-yn-1-ylamino)benzoic acid (53 mg, 259.02 µmol, 1.2 eq.), N-(1-cyclopropylpiperidin-4-yl)-2-iodo-1-(2,2,2-trifluoroethyl)-1H-indol-4-amine (0.1 g, 215.85 µmol, 1 eq.), CuI (37.54 mg, 197.11 µmol, 1 eq.), Pd(PPh$_3$)$_4$ (45.55 mg, 39.42 µmol, 0.2 eq.), and i-Pr$_2$NH (199.46 mg, 1.97 mmol, 278.57 µL, 10 eq.) in DMSO (3 mL) was degassed and purged with N$_2$ three times. The mixture was stirred at 20° C. for 1 h under N$_2$. TLC analysis (EtOAc:TEA=10:1, R$_f$=0.05) indicated that the starting material was consumed, and one new spot was detected. A saturated aqueous EDTA solution (20 mL) was added, and the resulting mixture was stirred at 20° C. for 1 h under N$_2$. The reaction mixture was quenched by adding water (20 mL) and was extracted with EtOAc (15 mL×3). The combined organic layers were washed with brine (10 mL×3), dried over anhydrous sodium sulfate, filtered, and concentrated under reduced pressure to give a residue. The residue was purified by prep-TLC (SiO$_2$, EtOAc:TEA=15:1) and prep-HPLC to give the desired product (0.04 g, 67.53 µmol, 34.26% yield) as a yellow solid. MS (ES$^{30}$, m/z): 541.2.

Example D56: Synthesis of 4-{[3-(4-{[1-(3-methanesulfonylpropyl)piperidin-4-yl]amino}-1-(2,2,2-trifluoroethyl)-1H-indol-2-yl)prop-2-yn-1-yl]amino}-3-methoxybenzoic acid (Compound 707A)

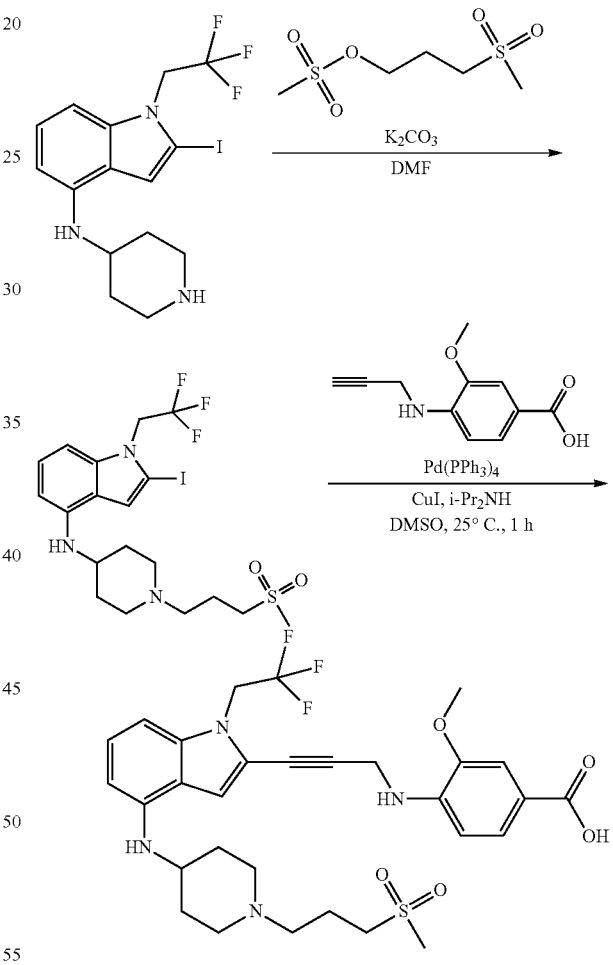

Preparation of 2-iodo-N-(1-(3-(methylsulfonyl)propyl)piperidin-4-yl)-1-(2,2,2-trifluoroethyl)-1H-indol-4-amine: To a solution of 2-iodo-N-(piperidin-4-yl)-1-(2,2,2-trifluoroethyl)-1H-indol-4-amine (0.2 g, 472.57 µmol, 1 eq.) in DMF (3 mL) were added K$_2$CO$_3$ (195.94 mg, 1.42 mmol, 3 eq.) and 3-(methylsulfonyl)propyl methanesulfonate (306.62 mg, 1.42 mmol, 3 eq.). The mixture was stirred at 80° C. for 2 h. TLC analysis (EtOAc:TEA=10:1, R$_f$=0.7) indicated that the starting material was consumed, and one new spot was detected. The reaction mixture was quenched by adding water (20 mL) and was extracted with EtOAc (15 mL×3).

The combined organic layers were washed with brine (10 mL×3), dried over anhydrous sodium sulfate, filtered, and concentrated under reduced pressure to give a residue. The residue was purified by prep-TLC (SiO$_2$, EtOAc=1) to afford the desired product (0.13 g, 191.39 μmol, 40.50% yield) as a yellow oil.

Preparation of 4-{[3-(4-{[1-(3-methanesulfonylpropyl) piperidin-4-yl]amino}-1-(2,2,2-trifluoroethyl)-1H-indol-2-yl)prop-2-yn-1-yl]amino}-3-methoxybenzoic acid: A mixture of 2-iodo-N-(1-(3-(methylsulfonyl)propyl)piperidin-4-yl)-1-(2,2,2-trifluoroethyl)-1H-indol-4-amine (0.1 g, 184.03 μmol, 1 eq.), 3-methoxy-4-(prop-2-yn-1-ylamino)benzoic acid (0.1 g, 184.03 μmol, 1 eq.), CuI (35.05 mg, 184.03 μmol, 1 eq.), Pd(PPh$_3$)$_4$ (42.53 mg, 36.81 μmol, 0.2 eq.), and i-Pr$_2$NH (186.22 mg, 1.84 mmol, 260.09 μL, 10 eq.) in DMSO (3 mL) was degassed and purged with N$_2$ three times. The mixture was stirred at 20° C. for 1 h under N$_2$. TLC analysis (EtOAc:TEA=10:1, R$_f$=0) indicated that the starting material was consumed completely, and one major new spot was detected. The reaction mixture was quenched by adding water (20 mL) and was extracted with EtOAc (15 mL×3). The combined organic layers were washed with brine (10 mL×3), dried over anhydrous sodium sulfate, filtered, and concentrated under reduced pressure to give a residue. The crude residue was purified by prep-HPLC to afford the desired product (0.035 g, 56.39 μmol, 30.64% yield) as a yellow solid. MS (ES$^{30}$, m/z): 621.3.

Example D57: Synthesis of 2-{3-[(4-methanesulfonyl-2-methoxyphenyl)amino]prop-1-yn-1-yl}-3-methyl-N-(1-methylpiperidin-4-yl)-1-(2,2,2-trifluoroethyl)-1H-indol-4-amine (Compound 520A)

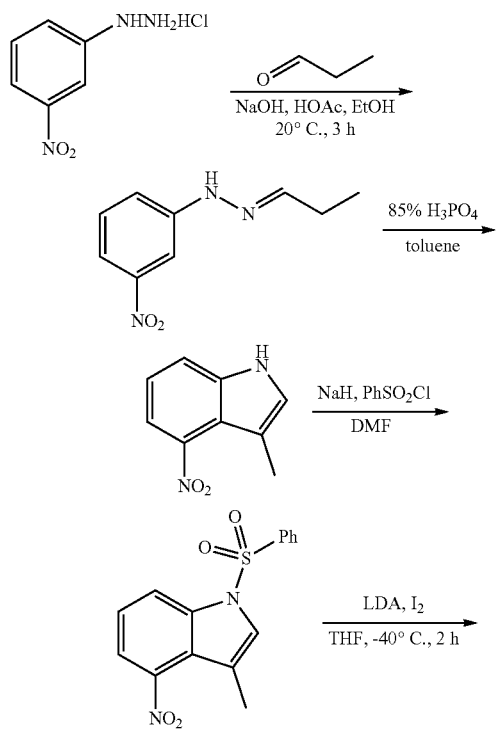

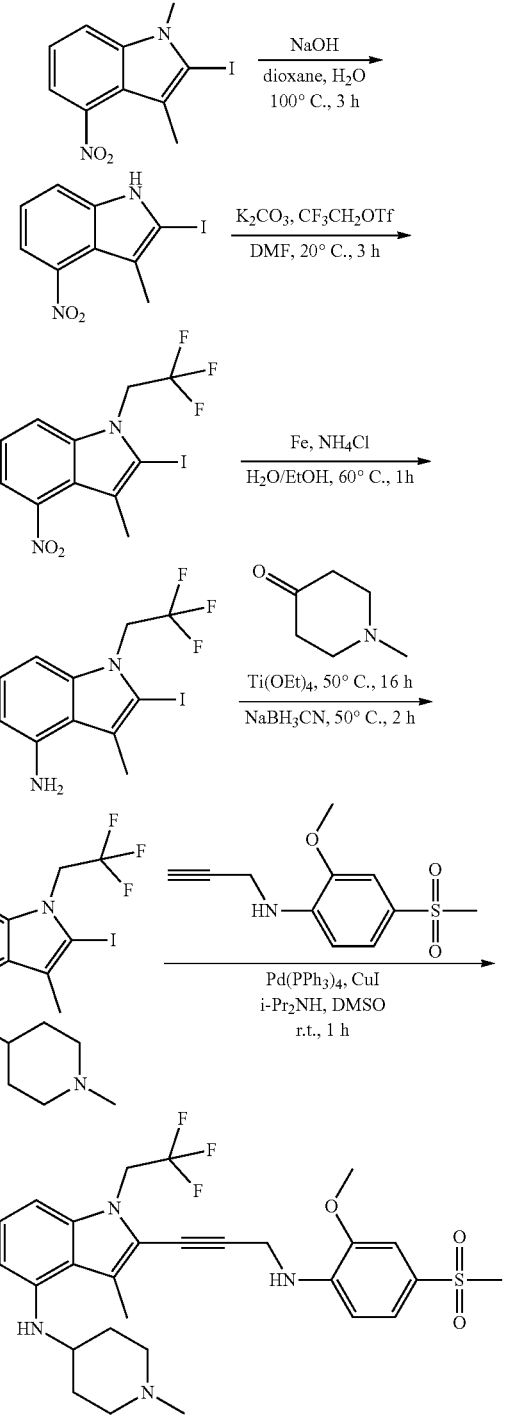

Preparation of (E)-1-(3-nitrophenyl)-2-propylidenehydrazine: An aqueous 2M NaOH solution (90 mL) was added slowly to a stirred suspension of (3-nitrophenyl) hydrazine hydrochloride (13 g, 68.57 mmol, 1 eq.) in EtOH (200 mL) until the pH was 6. AcOH (37 mL) was added to the mixture, followed by propanal (4.78 g, 82.28 mmol, 5.99 mL, 1.2 eq.). The mixture was then stirred for 3 h at 20° C. TLC analysis (R$_f$=0.65, PE:EtOAc=2:1) showed that the starting material was consumed, and one new spot was detected. The mixture was poured into ice-water (800 mL), and the resulting precipitate was isolated via filtration, washed with water, and dried in vacuo. The crude product was obtained (11.5 g, 53.57 mmol, 78.13% yield) as a yellow solid and used without purification.

Preparation of 3-methyl-4-nitro-1H-indole: A mixture of (E)-1-(3-nitrophenyl)-2-propylidenehydrazine (2 g, 10.35 mmol, 1 eq.) and $H_3PO_4$ (15 mL) in toluene (15 mL) was stirred at 100° C. for 2 h. TLC analysis (PE:EtOAc=2:1) showed that the reaction was complete. The mixture was concentrated to remove toluene. Then, 10 N NaOH (5 mL) was added to adjust the pH of the mixture to 8. The mixture was diluted with water (10 mL) and extracted with EtOAc (10 mL×3). The combined organic layers were washed with brine (10 mL×2), dried over anhydrous sodium sulfate, filtered, and concentrated. The residue was purified by prep-HPLC to afford the desired product (6 g) as a yellow solid. MS ($ES^{30}$, m/z): 177.1.

Preparation of 3-methyl-4-nitro-1-(phenylsulfonyl)-1H-indole: To a solution of 3-methyl-4-nitro-1H-indole (5 g, 28.38 mmol, 1 eq.) in DMF (6 mL) and THF (60 mL) was added NaH (1.70 g, 42.57 mmol, 60% in mineral oil, 1.5 eq.) at 0° C. under $N_2$. The mixture was stirred at 0° C. for 0.5 h, and benzenesulfonyl chloride (5.51 g, 31.22 mmol, 4 mL, 1.1 eq.) was added to the reaction mixture at 0° C. The resulting mixture was stirred at 0° C. for 1 h. TLC analysis (PE:EtOAc=2:1, $R_f$=0.6) detected one major new spot. The reaction mixture was poured into a saturated $NH_4Cl$ solution (15 mL), and the aqueous phase was extracted with EtOAc (100 mL×3). The combined organic layers were washed with brine (20 mL×3), dried over anhydrous sodium sulfate, filtered, and concentrated in vacuo to afford the crude product (8.5 g, 24.18 mmol, 85.21% yield) as a yellow solid, which was used without purification.

Preparation of 2-iodo-3-methyl-4-nitro-1-(phenylsulfonyl)-1H-indole: To a solution of 3-methyl-4-nitro-1-(phenylsulfonyl)-1H-indole (5 g, 15.81 mmol, 1 eq.) in THF (150 mL) was added LDA (2 M, 31.61 mL, 4 eq.; slow addition) at −60° C. The mixture was stirred at −40° C. for 0.5 h. Then the mixture was cooled to −60° C., and a solution of $I_2$ (6.02 g, 23.71 mmol, 4.78 mL, 1.5 eq.) in THF (150 mL) was slowly added over 1 h. The mixture was stirred at −60° C. for 4 h. HPLC analysis showed that reaction was complete. Water (300 mL) was slowly added to the reaction, and the mixture was extracted with EtOAc (300 mL×3). The combined organic layers were washed with brine (200 mL), dried over anhydrous sodium sulfate, filtered, and concentrated in vacuo to afford the crude product (6.5 g, crude) as a yellow solid, which was used without purification.

Preparation of 2-iodo-3-methyl-4-nitro-1H-indole: A mixture of 2-iodo-3-methyl-4-nitro-1-(phenylsulfonyl)-1H-indole (6.5 g, 14.70 mmol, 1 eq.) and NaOH (5.88 g, 146.98 mmol, 10 eq.) in dioxane (75 mL) and water (25 mL) was stirred at 100° C. for 3 h under $N_2$. TLC analysis ($R_f$=0.35, PE:EtOAc=4:1) showed that most of the starting material was almost consumed. The mixture was extracted with water (100 mL) and EtOAc (120 mL×3). The organic layer was washed with brine (50 mL), dried over anhydrous sodium sulfate, filtered, and concentrated under reduced pressure. The crude residue was purified by column chromatography ($SiO_2$, PE:EtOAc=80:1 to 50:1) to afford the desired product (2 g, 5.96 mmol, 40.54% yield) as a yellow solid.

Preparation of 2-iodo-3-methyl-4-nitro-1-(2,2,2-trifluoroethyl)-1H-indole: A mixture of 2-iodo-3-methyl-4-nitro-1H-indole (0.4 g, 1.32 mmol, 1 eq.), 2,2,2-trifluoroethyl trifluoromethanesulfonate (922.05 mg, 3.97 mmol, 3 eq.), and $K_2CO_3$ (915.07 mg, 6.62 mmol, 5 eq.) in DMF (5 mL) was stirred at 20° C. for 3 h. under $N_2$ atmosphere. TLC analysis ($R_f$=0.35, PE:EtOAc=4:1) showed that the reaction was complete. The reaction mixture was poured into water (200 mL) and extracted with EtOAc (150 mL×3). The organic layers were washed with brine (30 mL×5), dried over anhydrous sodium sulfate, filtered, and concentrated. The residue was purified by column chromatography ($SiO_2$, PE:EtOAc=40:1 to 30:1) to afford 2-iodo-3-methyl-4-nitro-1-(2,2,2-trifluoroethyl)indole (0.25 g, 650.89 μmol, 49% yield) as a yellow solid.

Preparation of 2-iodo-3-methyl-1-(2,2,2-trifluoroethyl)-1H-indol-4-amine: To a solution of 2-iodo-3-methyl-4-nitro-1-(2,2,2-trifluoroethyl)-1H-indole (1.2 g, 3.12 mmol, 1 eq.) in EtOH (30 mL), $NH_4Cl$ (10 mL), and saturated aqueous solution of $NH_4Cl$ (2.5 mL) was added Fe (872.37 mg, 15.62 mmol, 5 eq.) at 60° C. The mixture was stirred at 60° C. for 1 h. TLC analysis (PE:EtOAc=4:1, $R_f$=0.35) showed that the reaction was complete. The mixture was poured into EtOAc (30 mL) and extracted with water (20 mL) and EtOAc (10 mL×2). The organic layer was washed with brine (15 mL), dried over anhydrous sodium sulfate, filtered, and concentrated. The crude residue was purified by column chromatography ($SiO_2$, PE:EtOAc=20:1 to 5:1) to afford the desired product (0.75 g, 1.91 mmol, 61.01% yield) as a yellow solid.

Preparation of 2-iodo-3-methyl-N-(1-methylpiperidin-4-yl)-1-(2,2,2-trifluoroethyl)-1H-indol-4-amine: To a mixture of 2-iodo-3-methyl-1-(2,2,2-trifluoroethyl)-1H-indol-4-amine (0.05 g, 141.20 μmol, 1 eq.) and 1-methylpiperidin-4-one (39.94 mg, 353 μmol, 41.05 μL, 2.5 eq.) in EtOH (5 mL) was added $Ti(OEt)_4$ (96.63 mg, 423.60 μmol, 87.84 μL, 3 eq.) under $N_2$ at 50° C. The mixture was stirred for 16 h. $NaBH_3CN$ (26.62 mg, 423.60 μmol, 3 eq.) was added into the mixture, and the mixture was stirred further at 50° C. for 3 h under $N_2$. The mixture was poured into a saturated $NaHCO_3$ solution (15 mL) and extracted with EtOAc (25 mL×3). The combined organic layers were filtered through silica, and the filtrate was concentrated. The crude residue was purified by prep-TLC ($SiO_2$, EtOAc:TEA=10:1) to afford the desired product (0.038 g, 75.79 μmol, 53.67% yield) as a brown oil.

Preparation of 2-(3-((2-methoxy-4-(methylsulfonyl)phenyl)amino)prop-1-yn-1-yl)-3-methyl-N-(1-methylpiperidin-4-yl)-1-(2,2,2-trifluoroethyl)-1H-indol-4-amine: A mixture of 2-iodo-3-methyl-N-(1-methylpiperidin-4-yl)-1-(2,2,2-trifluoroethyl)-1H-indol-4-amine (0.038 g, 75.79 μmol, 1 eq.), 2-methoxy-4-(methylsulfonyl)-N-(prop-2-yn-1-yl)aniline (27.20 mg, 113.68 μmol, 1.5 eq.), i-$Pr_2NH$ (76.69 mg, 757.87 μmol, 107.11 μL, 10 eq.), CuI (14.43 mg, 75.79 μmol, 1 eq.), and $Pd(PPh_3)_4$ (17.52 mg, 15.16 μmol, 0.2 eq.) in DMSO (1.5 mL) was degassed and purged with $N_2$ three times. The mixture was stirred at 20° C. for 1 h under $N_2$. TLC analysis ($R_f$=0.25, EtOAc:TEA=10:1) showed that the reaction was complete. A saturated EDTA solution (15 mL) was added to the mixture, and the resulting mixture was stirred for 1 h. The mixture was then extracted with EtOAc (20 mL×3). The combined organic layers were washed with brine (3 mL×5), dried over anhydrous sodium sulfate, filtered, and concentrated. The residue was purified by prep-TLC ($SiO_2$, EtOAc:TEA=10:1, $R_f$=0.25) and prep-HPLC to afford the desired product (0.0205 g, 36.44 μmol, 48.08% yield) as a yellow solid. MS ($ES^{30}$, m/z): 563.3.

Example D58: Synthesis of 1-{4-[(2-{3-[(4-methanesulfonyl-2-methoxyphenyl)amino]prop-1-yn-1-yl}-3-methyl-1-(2,2,2-trifluoroethyl)-1H-indol-4-yl)amino]piperidin-1-yl}-3-methoxypropan-2-ol (Compound 676A)

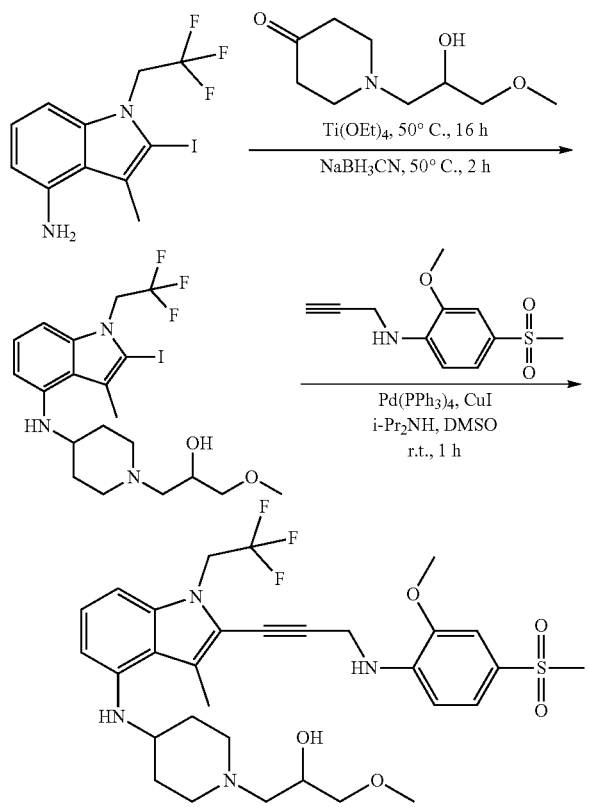

Preparation of 1-(4-((2-iodo-3-methyl-1-(2,2,2-trifluoroethyl)-1H-indol-4-yl)amino)piperidin-1-yl)-3-methoxypropan-2-ol: To a mixture of 2-iodo-3-methyl-1-(2,2,2-trifluoroethyl)-1H-indol-4-amine (0.05 g, 141.20 µmol, 1 eq.) and 1-(2-hydroxy-3-methoxypropyl)piperidin-4-one (66.09 mg, 353 µmol, 2.5 eq.) in EtOH (3 mL) was added $Ti(OEt)_4$ (64.42 mg, 282.40 µmol, 58.56 µL, 2 eq.) under $N_2$ at 50° C. The mixture was stirred for 16 h. $NaBH_3CN$ (26.62 mg, 423.60 µmol, 3 eq.) was added to the mixture, and the mixture was stirred at 50° C. for 3 h under $N_2$. TLC analysis (EtOAc:TEA=10:1, $R_f$=0.3) showed that little starting material remained, and the desired product was detected. The mixture was poured into a saturated aqueous $NaHCO_3$ (15 mL) solution and extracted with EtOAc (30 mL×3). The combined organic layers were filtered through silica, and the filtrate was concentrated. The crude residue was purified by prep-TLC ($SiO_2$, EtOAc:TEA=10:1) to afford the desired product (0.041 g, 70.24 µmol, 49.74% yield) as a brown oil.

Preparation of 1-methoxy-3-(4-((2-(3-((2-methoxy-4-(methylsulfonyl)phenyl)amino)prop-1-yn-1-yl)-3-methyl-1-(2,2,2-trifluoroethyl)-1H-indol-4-yl)amino)piperidin-1-yl)propan-2-ol: A mixture of 1-(4-((2-iodo-3-methyl-1-(2,2,2-trifluoroethyl)-1H-indol-4-yl)amino)piperidin-1-yl)-3-methoxypropan-2-ol (0.041 g, 78.04 µmol, 1 eq.), 2-methoxy-4-(methylsulfonyl)-N-(prop-2-yn-1-yl)aniline (28.01 mg, 117.07 µmol, 1.5 eq.), i-$Pr_2NH$ (78.97 mg, 780.44 µmol, 110.30 µL, 10 eq.), CuI (14.86 mg, 78.04 µmol, 1 eq.), and $Pd(PPh_3)_4$ (18.04 mg, 15.61 µmol, 0.2 eq.) in DMSO (1 mL) was degassed and purged with $N_2$ three times. The mixture was then stirred at 20° C. for 1 h under $N_2$. TLC analysis (EtOAc:TEA=10:1, $R_f$=0.2) showed that the reaction was complete. Saturated aqueous EDTA solution (15 mL) was added to the mixture, and the resulting mixture was stirred for 1 h. The mixture was then extracted with EtOAc (20 mL×3). The combined organic layers were washed with brine (3 mL×5), dried over anhydrous sodium sulfate, filtered, and concentrated. The crude residue was purified by prep-TLC ($SiO_2$, EtOAc:TEA=10:1, $R_f$=0.25) and prep-HPLC to afford the desired product (0.023 g, 35.69 µmol, 45.73% yield) as a yellow solid. MS ($ES^{30}$, m/z): 637.2.

Example D59: Synthesis of Compounds 462A, 583A, 725A, 727A, and 728A

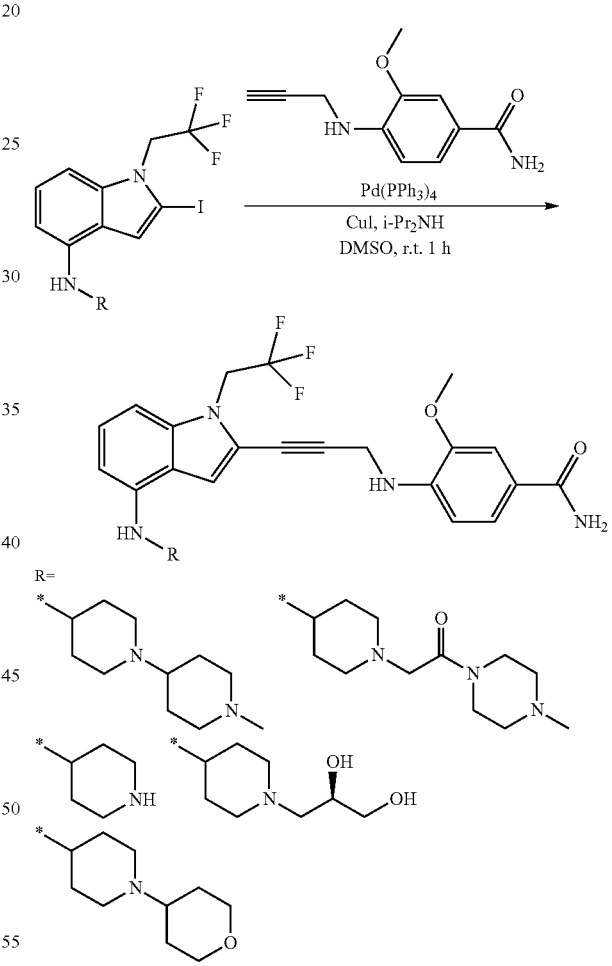

To a solution of 3-methoxy-4-(prop-2-yn-1-ylamino)benzamide (27.89 mg, 129.72 µmol, 1.5 eq.) in DMSO (1 mL) were added i-$Pr_2NH$ (262.52 mg, 2.59 mmol, 364.61 µL, 30 eq.), CuI (32.94 mg, 172.95 µmol, 2 eq.), 2-iodo-N-[1-(1-methyl-4-piperidyl)-4-piperidyl]-1-(2,2,2-trifluoroethyl)indol-4-amine (50 mg, 86.48 µmol, 1 eq.), and $Pd(PPh_3)_4$ (24.98 mg, 21.62 µmol, 0.25 eq.). The mixture was stirred at 20° C. for 1 h under $N_2$. TLC or LC-MS analysis were used to detect completion of the reaction. The reaction mixture was poured into a saturated EDTA solution (20 mL) and the resulting mixture was stirred for 15 min at 20° C. The mixture was extracted with EtOAc (30 mL×3), and the combined organic layers were concentrated under reduced pressure to a volume of 30 mL. The organic solution was poured into a saturated EDTA solution (20 mL) and stirred for 1 h at 20° C. The mixture was extracted with EtOAc (30 mL×3). The combined organic layers were washed with brine, dried over anhydrous sodium sulfate, mixed with active carbon, filtered, and concentrated under reduced pressure to give a residue. The crude residue as purified by prep-TLC and prep-HPLC to afford the desired product.

3-methoxy-4-((3-(4-((1'-methyl-[1,4'-bipiperidin]-4-yl)amino)-1-(2,2,2-trifluoroethyl)-1H-indol-2-yl)prop-2-yn-1-yl)amino)benzamide (11 mg, 16.91 µmol, 20% yield, FA) MS (ES$^{30}$, m/z): 597.3; 3-methoxy-4-((3-(4-((1-(2-(4-methylpiperazin-1-yl)-2-oxoethyl)piperidin-4-yl)amino)-1-(2,2,2-trifluoroethyl)-1H-indol-2-yl)prop-2-yn-1-yl)amino)benzamide (6.90 mg, 8.95 µmol, 10% yield, FA) MS (ES$^{30}$, m/z): 640.3; 3-methoxy-4-((3-(4-(piperidin-4-ylamino)-1-(2,2,2-trifluoroethyl)-1H-indol-2-yl)prop-2-yn-1-yl)amino)benzamide (29 mg, 53.16 µmol, 46% yield, FA) MS (ES$^{30}$, m/z): 500.3; 4-({3-[4-({1-[(2R)-2,3-dihydroxypropyl]piperidin-4-yl}amino)-1-(2,2,2-trifluoroethyl)-1H-indol-2-yl]prop-2-yn-1-yl}amino)-3-methoxybenzamide (95.5 mg, 165.82 µmol, 56% yield) MS (ES$^{30}$, m/z): 574.2; 3-methoxy-4-[3-[4-[(1-tetrahydropyran-4-yl-4-piperidyl)amino]-1-(2,2,2-trifluoroethyl)indol-2-yl]prop-2-ynylamino]benzamide, (8.40 mg, 13.07 µmol, 15.79% yield, FA) MS (ES$^{30}$, m/z): 584.3.

Example D60: Synthesis of Compounds 849A and 850A

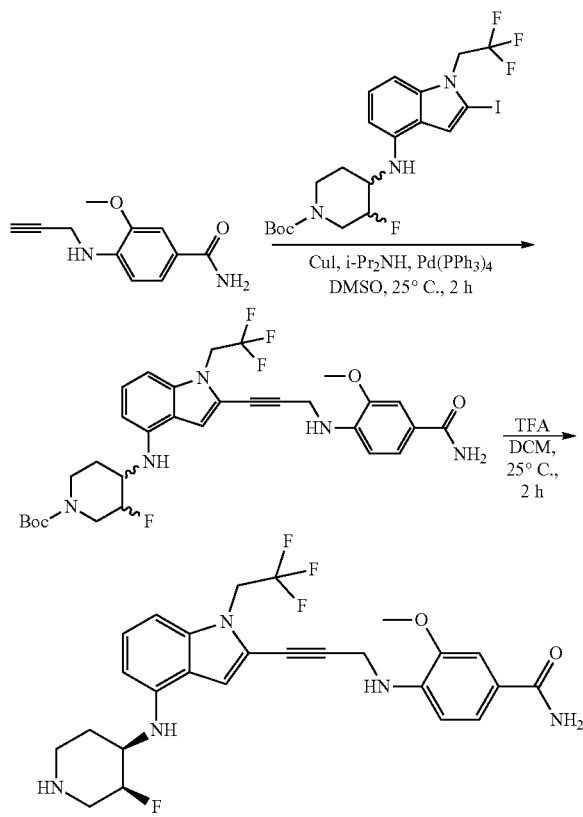

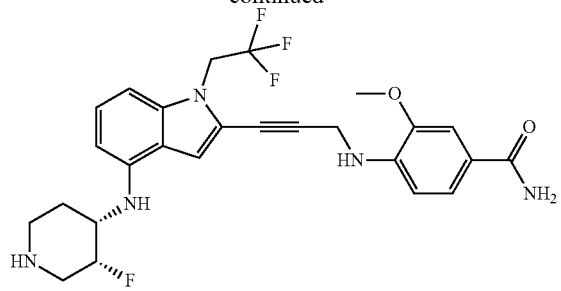

Preparation of tert-butyl 4-((2-(3-((4-carbamoyl-2-methoxyphenyl)amino)prop-1-yn-1-yl)-1-(2,2,2-trifluoroethyl)-1H-indol-4-yl)amino)-3-fluoropiperidine-1-carboxylate: A mixture of tert-butyl 3-fluoro-4-((2-iodo-1-(2,2,2-trifluoroethyl)-1H-indol-4-yl)amino)piperidine-1-carboxylate (100 mg, 184.73 µmol, 1 eq.), 3-methoxy-4-(prop-2-yn-1-ylamino)benzamide (56.59 mg, 277.10 µmol, 1.5 eq.), CuI (35.18 mg, 184.73 µmol, 1 eq.), Pd(PPh$_3$)$_4$ (35.18 mg, 184.73 µmol, 1 eq.) and i-Pr$_2$NH (186.93 mg, 1.85 mmol, 261.08 µL, 10 eq.) in DMSO (25 mL) was degassed and purged with N$_2$ three times. The mixture was stirred at 25° C. for 1 h under N$_2$. TLC and LC-MS analysis showed that the reaction was complete. The reaction mixture was added to a saturated aqueous EDTA solution (30 mL) and stirred for 1 h. The mixture was then extracted with EtOAc (30 mL×3). The combined organic layers were separated, washed with water (30 mL×2) and brine (30 mL×2), dried over anhydrous sodium sulfate, filtered, and concentrated under reduced pressure. The crude residue was purified by prep-TLC (SiO$_2$, DCM:MeOH=20:1) to afford the desired product (63.10% yield) as a light yellow solid. MS (ES$^{30}$, m/z): 618.2.

A solution of tert-butyl 4-((2-(3-((4-carbamoyl-2-methoxyphenyl)amino)prop-1-yn-1-yl)-1-(2,2,2-trifluoroethyl)-1H-indol-4-yl)amino)-3-fluoropiperidine-1-carboxylate (100 mg, 161.91 µmol, 1 eq.) in DCM (2 mL) and TFA (2 mL) was stirred at 25° C. for 1 h. TLC and LC-MS analysis showed that the reaction was complete. The reaction mixture was poured onto ice water (20 mL), and a saturated aqueous Na$_2$CO$_3$ solution was slowly added to the mixture to adjust the pH to 8-9. The mixture was then extracted with DCM (30 mL×3). The combined organic layers were separated, washed with water (30 mL×2) and brine (30 mL×2), dried over anhydrous sodium sulfate, filtered, and concentrated under reduced pressure. The crude residue was purified by prep-HPLC to afford the desired products as light yellow solids.

4-{[3-(4-{[(3S,4R)-3-fluoropiperidin-4-yl]amino}-1-(2,2,2-trifluoroethyl)-1H-indol-2-yl)prop-2-yn-1-yl]amino}-3-methoxybenzamide (28.9 mg, 53.61 µmol, 33% yield), MS (ES$^{30}$, m/z): 518.2; and 4-{[3-(4-{[(3R,4S)-3-fluoropiperidin-4-yl]amino}-1-(2,2,2-trifluoroethyl)-1H-indol-2-yl)prop-2-yn-1-yl]amino}-3-methoxy-N-methylbenzamide (39.9 mg, 77.10 µmol, 60% yield), MS (ES$^{30}$, m/z): 518.2.

Example D61: Synthesis of Compounds 733A and 736A

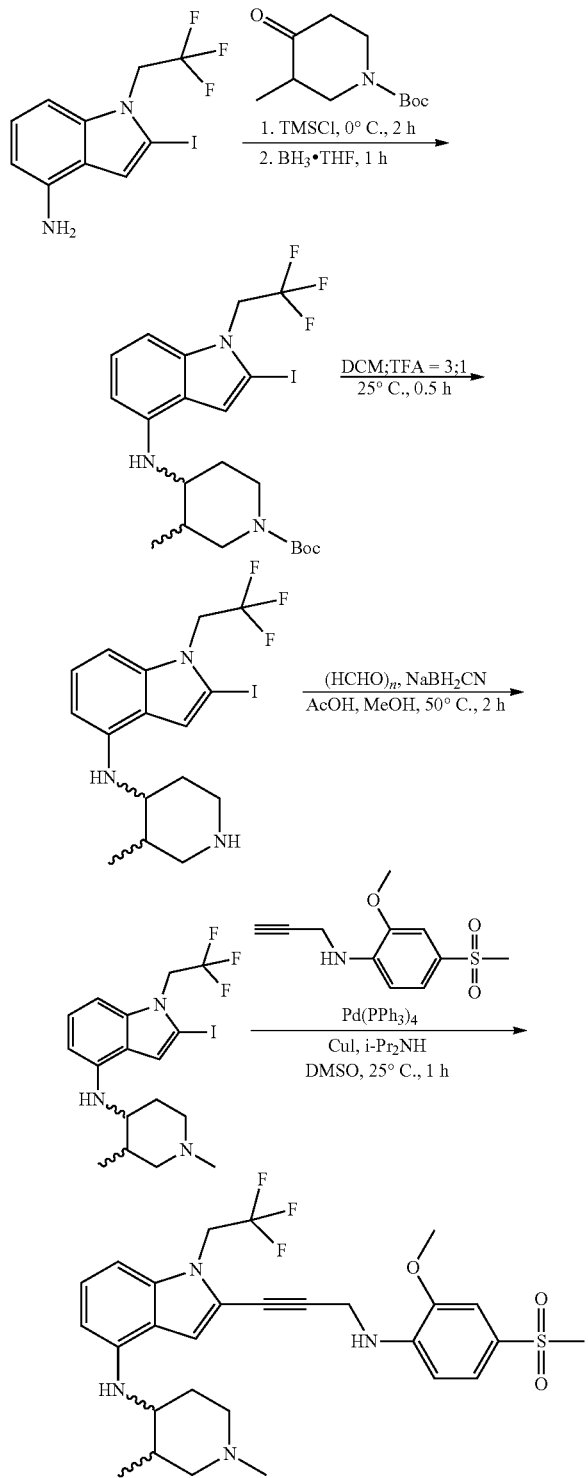

Preparation of tert-butyl 4-((2-iodo-1-(2,2,2-trifluoroethyl)-1H-indol-4-yl)amino)-3-methylpiperidine-1-carboxylate: To a solution of 2-iodo-1-(2,2,2-trifluoroethyl) indol-4-amine (0.5 g, 1.47 mmol, 1 eq.) and tert-butyl 3-methyl-4-oxo-piperidine-1-carboxylate (940.68 mg, 4.41 mmol, 3 eq.) in DMF (5 mL) was added TMSCl (399.32 mg, 3.68 mmol, 466.50 μL, 2.5 eq.) at 0° C. The mixture was stirred at 0° C. for 2 h, then $BH_3$·THF (1 M, 7.35 mL, 5 eq.) was added to the solution under $N_2$ at 0° C. The resulting mixture was stirred further at 25° C. for 1 h. LC-MS analysis showed that the reaction was complete. The reaction mixture was poured into a saturated aqueous $Na_2CO_3$ solution (8 mL) at 0° C. and extracted with EtOAc (10 mL×3). The organic phase was washed with brine (10 mL×3), dried over anhydrous sodium sulfate, filtered, and concentrated under reduced pressure. The crude residue was purified by column chromatography ($SiO_2$, PE:EtOAc=1:0 to 10:1) and prep-HPLC to afford the desired product (0.365 g, 665.67 μmol, 45.28% yield) as a yellow solid.

Preparation of 2-iodo-N-(3-methylpiperidin-4-yl)-1-(2,2,2-trifluoroethyl)-1H-indol-4-amine: To a solution of tert-butyl 4-((2-iodo-1-(2,2,2-trifluoroethyl)-1H-indol-4-yl)amino)-3-methylpiperidine-1-carboxylate (0.1 g, 182.37 μmol, 1 eq.) in DCM (3 mL) was added TFA (1.51 g, 13.24 mmol, 980 μL, 72.58 eq.). The mixture was stirred at 25° C. for 0.5 h. TLC analysis showed that the reaction was complete. A saturated aqueous $Na_2CO_3$ solution was added to the mixture to adjust the pH of the mixture to 9. The mixture was then extracted with EtOAc (20 mL×3). The combined organic layers were washed with brine (20 mL×3), dried over anhydrous sodium sulfate, filtered, and concentrated under reduced pressure. The crude product (0.08 g) was obtained as a yellow solid and used without purification.

Preparation of N-(1,3-dimethylpiperidin-4-yl)-2-iodo-1-(2,2,2-trifluoroethyl)-1H-indol-4-amine: To a mixture of 2-iodo-N-(3-methylpiperidin-4-yl)-1-(2,2,2-trifluoroethyl)-1H-indol-4-amine (0.08 g, 182.97 μmol, 1 eq.) and formaldehyde (54.94 mg, 1.83 mmol, 50.40 μL, 10 eq.) in MeOH (3 mL) was added into AcOH (10.99 ug, 1.83e-1 μmol, 1.05e-2 μL, 0.001 eq.) and stirred at 50° C. for 1 h. Then, $NaBH_3CN$ (57.49 mg, 914.83 μmol, 5 eq.) was added, and the mixture was stirred further at 50° C. for 1 h. TLC analysis showed that the reaction was complete. The reaction mixture was poured into water (10 mL) and extracted with EtOAc (10 mL×3). The organic layer was washed with brine (10 mL×3), dried over anhydrous sodium sulfate, filtered, and concentrated under reduced pressure. The residue was purified by prep-TLC ($SiO_2$, DCM:MeOH=10:1) to afford the desired product (0.07 g, 155.12 μmol, 85% yield) as a yellow solid.

Preparation of N-(1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine: To a mixture of 2-methoxy-4-(methylsulfonyl)-N-(prop-2-yn-1-yl)aniline (44.54 mg, 186.14 μmol, 1.2 eq.) in DMSO (2 mL) were added i-$Pr_2NH$ (156.96 mg, 1.55 mmol, 219.22 μL, 10 eq.), CuI (29.54 mg, 155.12 mol, 1 eq.), N-(1,3-dimethylpiperidin-4-yl)-2-iodo-1-(2,2,2-trifluoroethyl)-1H-indol-4-amine (0.07 g, 155.12 μmol, 1 eq.), and $Pd(PPh_3)_4$ (71.70 mg, 62.05 μmol, 0.4 eq.). The mixture was stirred at 25° C. for 1 h under $N_2$. LC-MS or TLC analysis showed that the reaction was complete. The mixture was poured into a saturated aqueous EDTA solution (15 mL) and stirred for 1 h. The aqueous phase was extracted with EtOAc (10 mL×3). The combined organic layers were washed with brine (10 mL×3), dried over anhydrous sodium sulfate, filtered, and concentrated in vacuo. The residue was purified by pre-TLC ($SiO_2$, DCM:MeOH=10:1) and prep-HPLC to afford the desired products.

N-((3S,4S)-1,3-dimethylpiperidin-4-yl)-2-(3-((2-methoxy-4-(methylsulfonyl)phenyl)amino)prop-1-yn-1-yl)-

1-(2,2,2-trifluoroethyl)-1H-indol-4-amine, 16.6 mg, 14.6% yield, MS (ES[30], m/z): 563.2; and N-((3R,4S)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine, 17.6 mg, 20.1% yield, MS (ES[30], m/z): 563.2.

Example D62: Synthesis of Compounds 701A and 702A

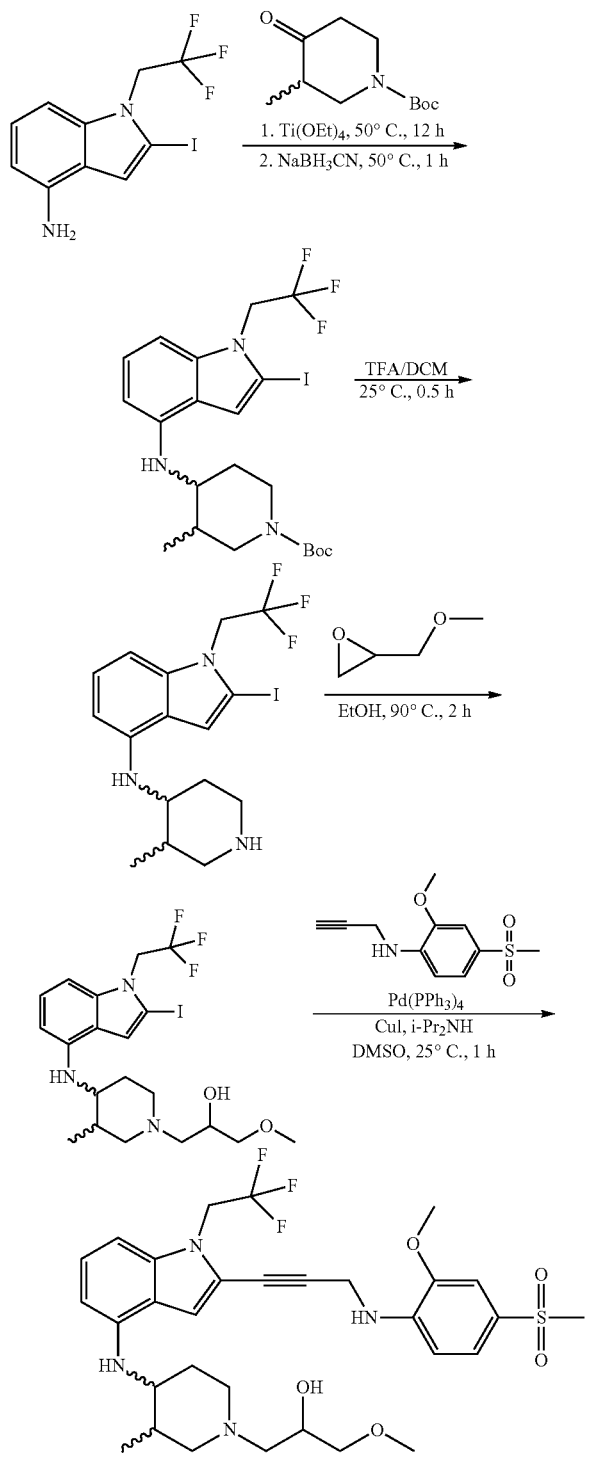

Preparation of tert-butyl 4-((2-iodo-1-(2,2,2-trifluoroethyl)-1H-indol-4-yl)amino)-3-methylpiperidine-1-carboxylate: To a mixture of 2-iodo-1-(2,2,2-trifluoroethyl) indol-4-amine (0.1 g, 294.05 μmol, 1 eq.) and tert-butyl 3-methyl-4-oxo-piperidine-1-carboxylate (940.68 mg, 4.41 mmol, 3 eq.) in EtOH (5 mL) was added Ti(OEt)$_4$ (1.68 g, 7.35 mmol, 1.52 mL, 5 eq.). The mixture was stirred at 50° C. for 12 h, and NaBH$_3$CN (461.96 mg, 7.35 mmol, 5 eq.) was added to the reaction. The mixture was stirred further at 50° C. for 1 h. LC-MS analysis showed that the reaction was complete. The reaction mixture was poured into a saturated aqueous Na$_2$CO$_3$ solution (8 mL) at 0° C., then extracted with EtOAc (10 mL×3). The organic layer was washed with brine (10 mL×3), dried over anhydrous sodium sulfate, filtered, and concentrated under reduced pressure. The residue was purified by column chromatography (SiO$_2$, PE:EtOAc=1:0 to 10:1) and prep-HPLC to afford the desired product (0.262 g, 438.82 μmol, 29.85% yield) as a light yellow solid.

Preparation of 2-iodo-N-(3-methylpiperidin-4-yl)-1-(2,2,2-trifluoroethyl)-1H-indol-4-amine: To a solution of tert-butyl 4-((2-iodo-1-(2,2,2-trifluoroethyl)-1H-indol-4-yl)amino)-3-methylpiperidine-1-carboxylate (0.15 g, 273.56 μmol, 1 eq.) in DCM (3 mL) was added TFA (1.51 g, 13.24 mmol, 980 μL, 48.38 eq.). The mixture was stirred at 25° C. for 0.5 h. TLC analysis showed that the reaction was complete. A saturated aqueous Na$_2$CO$_3$ solution was added to the reaction mixture to adjust the pH of the mixture to 9. The mixture was then extracted with EtOAc (20 mL×3), washed with brine (20 mL×3), dried over anhydrous sodium sulfate, filtered, and concentrated under reduced pressure. The crude product (0.1 g) was obtained as a yellow solid and used without purification. MS (ES[30], m/z): 438.1.

Preparation of 1-(4-((2-iodo-1-(2,2,2-trifluoroethyl)-1H-indol-4-yl)amino)-3-methylpiperidin-1-yl)-3-methoxypropan-2-ol: To a solution of 2-iodo-N-(3-methylpiperidin-4-yl)-1-(2,2,2-trifluoroethyl)-1H-indol-4-(0.1 g, 224.13 μmol, 1 eq.) in EtOH (3 mL) was added 2-(methoxymethyl)oxirane (29.62 mg, 336.20 μmol, 29.92 μL, 1.5 eq.). The reaction mixture was stirred at 90° C. for 2 h. TLC analysis showed that the reaction was complete. The reaction mixture was concentrated under reduced pressure and purified by prep-TLC (SiO$_2$, DCM:MeOH=10:1) to afford the desired product (0.08 g, 152.28 μmol, 68% yield) as a yellow oil.

Preparation of 1-methoxy-3-(4-((2-(3-((2-methoxy-4-(methylsulfonyl)phenyl)amino)prop-1-yn-1-yl)-1-(2,2,2-trifluoroethyl)-1H-indol-4-yl)amino)-3-methylpiperidin-1-yl)propan-2-ol: To a solution of 2-methoxy-4-(methylsulfonyl)-N-(prop-2-yn-1-yl)aniline 2 (43.73 mg, 182.74 μmol, 1.2 eq.) in DMSO (2 mL) were added i-Pr$_2$NH (154.09 mg, 1.52 mmol, 215.21 μL, 10 eq.), CuI (29 mg, 152.28 μmol, 1 eq.), 1-(4-((2-iodo-1-(2,2,2-trifluoroethyl)-1H-indol-4-yl)amino)-3-methylpiperidin-1-yl)-3-methoxypropan-2-ol (0.08 g, 152.28 μmol, 1 eq.), and Pd(PPh$_3$)$_4$ (70.39 mg, 60.91 μmol, 0.4 eq.). The mixture was stirred at 25° C. for 1 h under N$_2$. LC-MS or TLC analysis showed that the reaction was complete. The mixture was poured into a saturated aqueous EDTA solution (15 mL) and stirred for 1 h. The aqueous phase was extracted with EtOAc (10 mL×3). The combined organic layers were washed with brine (10 mL×3), dried over anhydrous sodium sulfate, filtered, and concentrated in vacuo. The residue was purified by prep-TLC (SiO$_2$, DCM:MeOH=10:1) and prep-HPLC to afford the desired products rac-1-[(3R,4R)-4-[(2-{3-[(4-methanesulfonyl-2-methoxyphenyl)amino]prop-1-yn-1-yl}-1-(2,2,2-trifluoroethyl)-1H-indol-4-yl)amino]-3-methylpiperidin-1-yl]-3- methoxypropan-2-ol, 6 mg, 18.5% yield, MS (ES$^{30}$, m/z): 637.3; and rac-1-[(3R,4S)-4-[(2-{3-[(4-methanesulfonyl-2-methoxyphenyl)amino]prop-1-yn-1-yl}-1-(2,2,2-trifluoroethyl)-1H-indol-4-yl)amino]-3-methylpiperidin-1-yl]-3-methoxypropan-2-ol, 20 mg, 48.9% yield, MS (ES$^{30}$, m/z): 637.3.

Example D63: Synthesis of Compounds 675A, 682A, 686A, and 687A

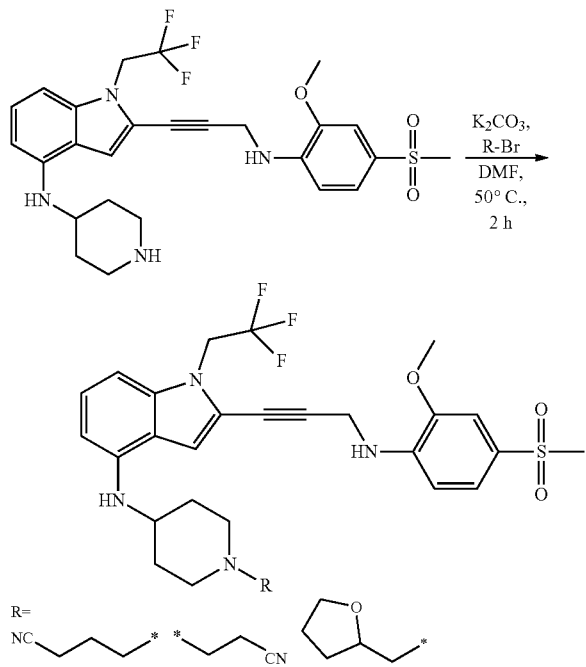

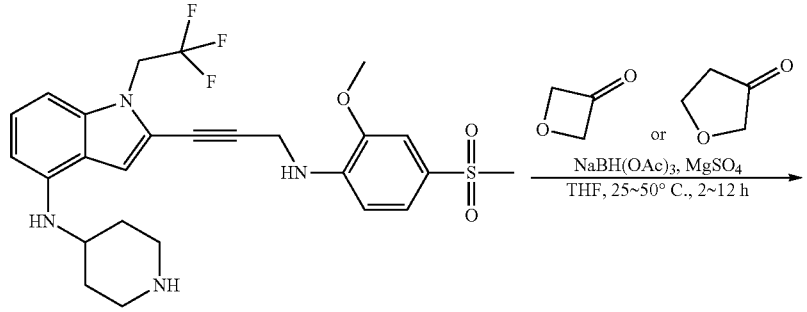

To a solution of 2-(3-((2-methoxy-4-(methylsulfonyl)phenyl)amino)prop-1-yn-1-yl)-N-(piperidin-4-yl)-1-(2,2,2-trifluoroethyl)-1H-indol-4-amine (100 mg, 187.06 μmol, 1 eq.) in DMF (3 mL) were added K$_2$CO$_3$ (51.71 mg, 374.12 μmol, 2 eq.) and 4-bromobutanenitrile (83.05 mg, 561.18 μmol, 40.08 μL, 3 eq.). The mixture was stirred at 50° C. for 2 h. LC-MS or TLC analysis indicated that the reaction was complete. The reaction mixture was quenched by adding water (40 mL) to the reaction mixture at 25° C. and extracting the mixture with EtOAc (10 mL×3). The combined organic layers were washed with brine (20 mL), dried over anhydrous sodium sulfate, filtered, and concentrated under reduced pressure. The crude residue was purified by prep-TLC (SiO$_2$, DCM:MeOH=10:1, R$_f$=0.43) and prep-HPLC to afford the desired products a light yellow solids.

2-{3-[(4-methanesulfonyl-2-methoxyphenyl)amino] prop-1-yn-1-yl}-N-[1-(3-methoxypropyl)piperidin-4-yl]-1-(2,2,2-trifluoroethyl)-1H-indol-4-amine, 15.3 mg, 26.8% yield, MS (ES$^{30}$, m/z): 607.2; 3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propanenitrile, 20.4 mg, 17.0% yield, MS (ES$^{30}$, m/z): 588.2; 4-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)butanenitrile, 24.6 mg, 21.4% yield, MS (ES$^{30}$, m/z): 602.2; and 2-(3-((2-methoxy-4-(methylsulfonyl)phenyl)amino)prop-1-yn-1-yl)-N-(1-((tetrahydrofuran-2-yl)methyl)piperidin-4-yl)-1-(2,2,2-trifluoroethyl)-1H-indol-4-amine, 24.0 mg, 20.4% yield, MS (ES$^{30}$, m/z): 619.2.

Example D64: Synthesis of Compounds 678A and 679A

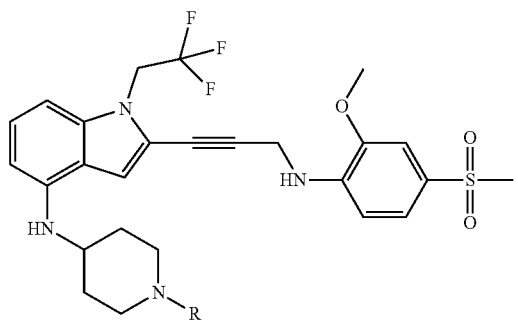

R= 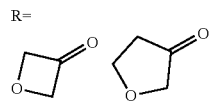

To a mixture of 2-(3-((2-methoxy-4-(methylsulfonyl)phenyl)amino)prop-1-yn-1-yl)-N-(piperidin-4-yl)-1-(2,2,2-trifluoroethyl)-1H-indol-4-amine (100 mg, 187.06 μmol, 1 eq.) and oxetan-3-one (40.44 mg, 561.18 μmol, 3 eq.) or dihydrofuran-3 (2H)-one (48.31 mg, 561.18 μmol, 3 eq.) in THF (3 mL) was added MgSO₄ (112.58 mg, 935.29 μmol, 5 eq.). The reaction mixture was stirred at 40° C. for 2 h, then NaBH(OAc)₃ (198.23 mg, 935.29 μmol, 5 eq.) was added, and the reaction mixture was stirred further for 1 h. TLC analysis (DCM:MeOH=10:1, R$_f$=0.43) indicated that the reaction was complete. The reaction mixture was quenched by adding a saturated aqueous NaHCO₃ solution (40 mL) at 25° C. and extracted with EtOAc (20 mL×3). The combined organic layers were dried over anhydrous sodium sulfate, filtered, and concentrated under reduced pressure. The crude residue was purified by prep-TLC (SiO₂, DCM:MeOH=10:1, R$_f$=0.43) and prep-HPLC to afford the desired products as light yellow solids.

2-{3-[(4-methanesulfonyl-2-methoxyphenyl)amino]prop-1-yn-1-yl}-N-[1-(oxetan-3-yl)piperidin-4-yl]-1-(2,2,2-trifluoroethyl)-1H-indol-4-amine, 13.2 mg, 11.4% yield, MS (ES³⁰, m/z): 591.2; and 2-(3-((2-methoxy-4-(methylsulfonyl)phenyl)amino)prop-1-yn-1-yl)-N-(1-(tetrahydrofuran-3-yl)piperidin-4-yl)-1-(2,2,2-trifluoroethyl)-1H-indol-4-amine, 20.5 mg, 18.0% yield, MS (ES³⁰, m/z): 605.3.

Example D65: Synthesis of 4-((2-(3-((2-methoxy-4-(methylsulfonyl)phenyl)amino)prop-1-yn-1-yl)-1-(2,2,2-trifluoroethyl)-1H-indol-4-yl)amino)-N,N-dimethylpiperidine-1-carboxamide (Compound 754A)

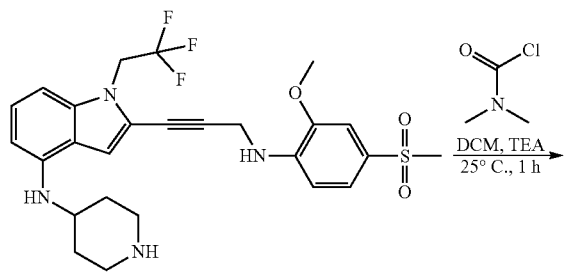

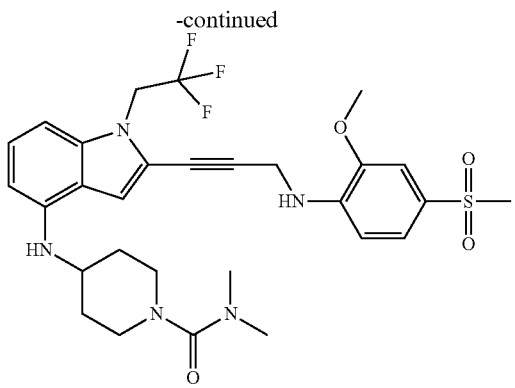

To a solution of 2-(3-((2-methoxy-4-(methylsulfonyl)phenyl)amino)prop-1-yn-1-yl)-N-(piperidin-4-yl)-1-(2,2,2-trifluoroethyl)-1H-indol-4-amine (100 mg, 187.06 μmol, 1 eq.) in DCM (3 mL) were added TEA (37.86 mg, 374.12 μmol, 52.07 μL, 2 eq.) and dimethylcarbamic chloride (40.23 mg, 374.12 μmol, 34.39 μL, 2 eq.). The mixture was stirred at 25° C. for 1 h. LC-MS analysis indicated that the reaction was complete. The reaction mixture was quenched by adding water (40 mL) at 25° C. and extracting the mixture with EtOAc (30 mL×2). The combined organic layers were dried over anhydrous sodium sulfate, filtered, and concentrated under reduced pressure to give a residue. The residue was purified by prep-HPLC to afford the desired product (23.0 mg, 37.97 μmol, 20.30% yield) as a light yellow solid. MS (ES³⁰, m/z): 606.2.

Example D66: Synthesis of 2-(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzenesulfonyl)ethan-1-ol (Compound 939A)

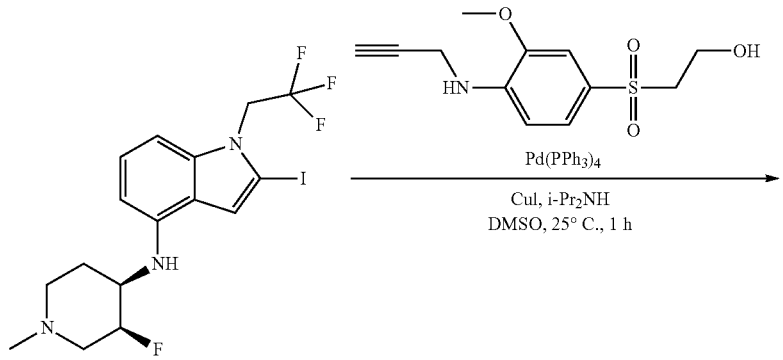

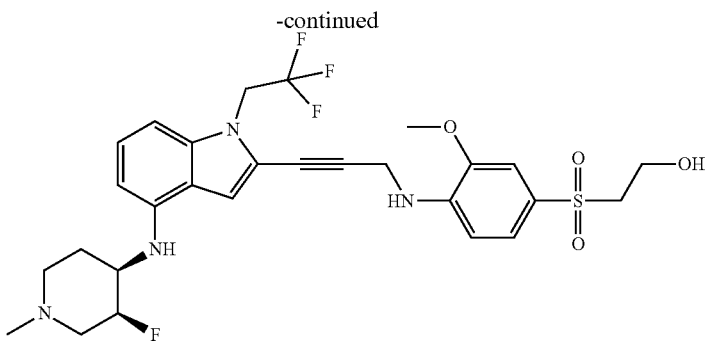

To a solution 2-((3-methoxy-4-(prop-2-yn-1-ylamino)phenyl)sulfonyl)ethan-1-ol (52.06 mg, 193.31 μmol, 1.1 eq.) in DMSO (1 mL) were added i-Pr$_2$NH (266.74 mg, 2.64 mmol, 372.54 μL, 15 eq.), CuI (3.35 mg, 17.57 μmol, 0.1 eq.), N-((3S,4R)-3-fluoro-1-methylpiperidin-4-yl)-2-iodo-1-(2,2,2-trifluoroethyl)-1H-indol-4-amine (0.08 g, 175.73 μmol, 1 eq.), and Pd(PPh$_3$)$_4$ (3.05 mg, 2.64 μmol, 0.015 eq.). The mixture was stirred at 25° C. for 1 h under N$_2$. TLC analysis (DCM:MeOH=10:1, R$_f$=0.4) indicated that 10% of the starting material remained, and one major new spot with polarity greater than that of the starting material was detected. The reaction mixture was quenched by adding a saturated aqueous EDTA solution (120 mL) and stirred for 1 h. The mixture was extracted with EtOAc (40 mL×3). The combined organic layers were washed with brine (40 mL×3), dried over anhydrous sodium sulfate, filtered, and concentrated under reduced pressure. The crude residue was purified by prep-TLC (SiO$_2$, DCM:MeOH=10:1 and reversed-phase HPLC to afford the desired product (28.5 mg, 47.29 μmol, 26.91% yield) as a yellow solid. MS (ES$^{30}$, m/z): 597.2.

1H NMR (400 MHz, DMSO-d6) δ ppm 1.64-1.75 (m, 1H) 1.84-2.00 (m, 1H) 2.11-2.26 (m, 5H) 2.30-2.37 (m, 1H) 2.78-2.86 (m, 1H) 3.01-3.09 (m, 1H) 3.28-3.35 (m, 2H) 3.61-3.65 (m, 2H) 3.81-3.93 (m, 3H) 4.28-4.41 (m, 2H) 4.68-4.79 (m, 1H) 4.82-4.95 (m, 2H) 6.15-6.31 (m, 1H) 6.72 (d, J=8.07 Hz, 1H) 6.88 (d, J=8.44 Hz, 1H) 6.95-7.07 (m, 1H) 7.12-7.23 (m, 2H) 7.27-7.38 (m, 1H) 8.14-8.26 (m, 1H).

Example D67: Synthesis of Compounds 847A and 848A

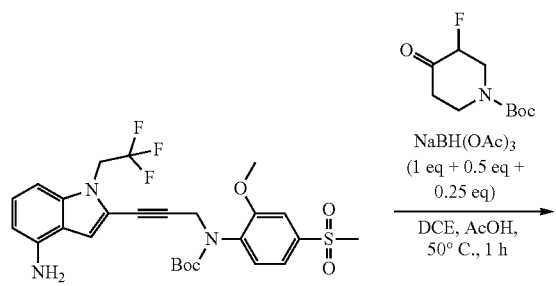

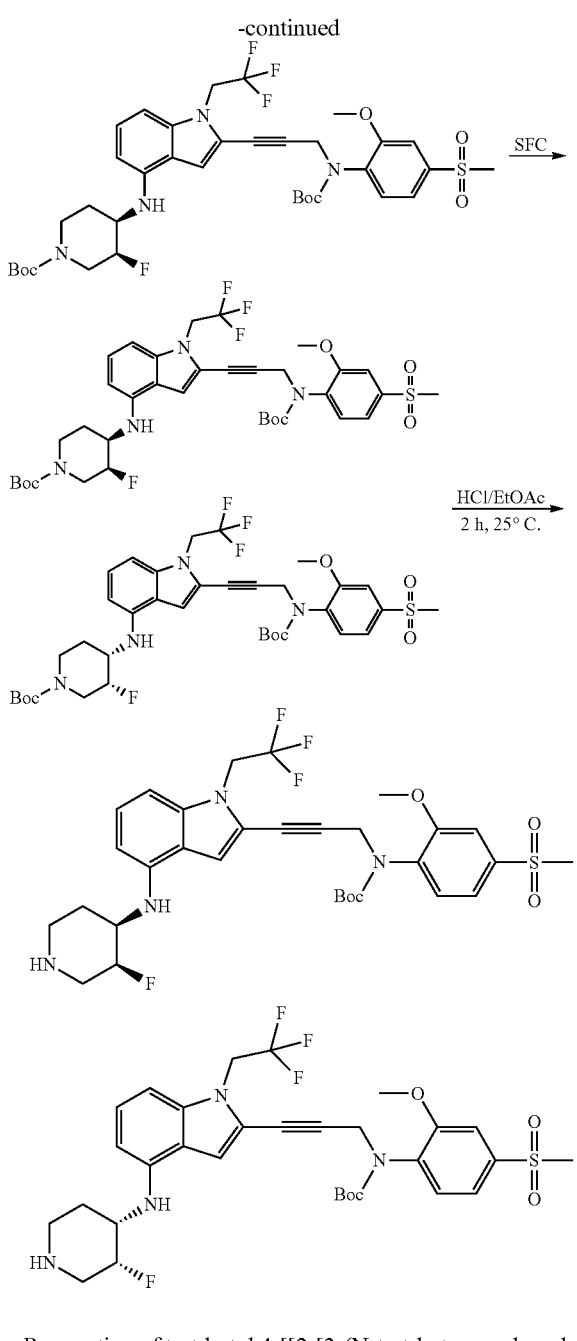

Preparation of tert-butyl 4-[[2-[3-(N-tert-butoxycarbonyl-2-methoxy-4-methylsulfonyl-anilino)prop-1-ynyl]-1-(2,2,2- trifluoroethyl)indol-4-yl]amino]-3-fluoro-piperidine-1-carboxylate: To a solution of tert-butyl N-[3-[4-amino-1-(2,2,2-trifluoroethyl)indol-2-yl]prop-2-ynyl]-N-(2-methoxy-4-methylsulfonyl-phenyl)carbamate (20 g, 36.26 mmol, 1 eq.) in AcOH (160 mL) and DCE (80 mL) was added tert-butyl 3-fluoro-4-oxo-piperidine-1-carboxylate (23.63 g, 108.78 mmol, 3 eq.) at 50° C. The mixture was stirred at 50° C. for 10 min, and NaBH(OAc)$_3$ (7.68 g, 36.26 mmol, 1 eq.) was added into the mixture. After 15 min of stirring, a second batch of NaBH(OAc)$_3$ (3.84 g, 18.13 mmol, 0.5 eq.) was added to the reaction, and three additional batches were added in 15 min intervals (1.92 g, 9.06 mmol, 0.25 eq.; 3.84 g, 18.13 mmol, 0.5 eq.; and 960.61 mg, 4.53 mmol, 0.125 eq.). The mixture was stirred at 50° C. for 25 min. TLC analysis indicated that 3% of the starting material was remained, and one major new spot with polarity lower than that of the starting material was detected. The reaction mixture was quenched by adding water (2000 mL) and diluting the mixture with NaOH (120 g) in water (500 mL) to adjust the pH of the solution to pH>10. The resulting mixture was extracted with EtOAc (500 mL×3). The combined organic layers were washed with brine (500 mL×3), dried over anhydrous sodium sulfate, filtered, and concentrated under reduced pressure to give a residue. The residue was purified by column chromatography (SiO$_2$, PE:EtOAc=5:1 to EtOAc:DCM=2:1). The product was triturated with PE:EtOAc=120 mL:40 mL at 25° C. for 12 h. The residue was then purified by reversed-phase HPLC to give compound tert-butyl 4-[[2-[3-(N-tert-butoxycarbonyl-2-methoxy-4-methylsulfonyl-anilino)prop-1-ynyl]-1-(2,2,2-trifluoroethyl)indol-4-yl]amino]-3-fluoro-piperidine-1-carboxylate (35 g, 45.98 mmol, 63% yield) as a yellow solid.

Preparation of tert-butyl (3S,4R)-4-[[2-[3-(N-tert-butoxycarbonyl-2-methoxy-4-methylsulfonyl-anilino)prop-1-ynyl]-1-(2,2,2-trifluoroethyl)indol-4-yl]amino]-3-fluoro-piperidine-1-carboxylate: tert-butyl 4-[[2-[3-(N-tert-butoxycarbonyl-2-methoxy-4-methylsulfonyl-anilino)prop-1-ynyl]-1-(2,2,2-trifluoroethyl)indol-4-yl]amino]-3-fluoro-piperidine-1-carboxylate (35 g, 46.49 mmol, 1 eq.) was further separated by SFC to afford the desired compounds. Tert-butyl (3S,4R)-4-[[2-[3-(N-tert-butoxycarbonyl-2-methoxy-4-methylsulfonyl-anilino)prop-1-ynyl]-1-(2,2,2-trifluoroethyl)indol-4-yl]amino]-3-fluoro-piperidine-1-carboxylate (16 g, 21.10 mmol, 45% yield) was obtained as a red solid. Tert-butyl (3R,4S)-4-[[2-[3-(N-tert-butoxycarbonyl-2-methoxy-4-methylsulfonyl-anilino)prop-1-ynyl]-1-(2,2,2-trifluoroethyl)indol-4-yl]amino]-3-fluoro-piperidine-1-carboxylate (16 g, 20.36 mmol, 44% yield) was obtained as a yellow solid.

Preparation of N-[(3S,4R)-3-fluoro-4-piperidyl]-2-[3-(2-methoxy-4-methylsulfonyl-anilino)prop-1-ynyl]-1-(2,2,2-trifluoroethyl)indol-4-amine: A mixture of tert-butyl (3S,4R)-4-[[2-[3-(N-tert-butoxycarbonyl-2-methoxy-4-methylsulfonyl-anilino)prop-1-ynyl]-1-(2,2,2-trifluoroethyl)indol-4-yl]amino]-3-fluoro-piperidine-1-carboxylate (15 g, 19.93 mmol, 1 eq.), 4M HCl/EtOAc (373.60 mL, 75 eq.) in EtOAc (75 mL) was stirred at 20° C. for 1 h. under N$_2$. TLC analysis indicated that the starting material was consumed completely, and one new spot was detected. The reaction mixture was filtered to give a solid and dried under reduced pressure. The crude product was triturated with EtOH (150 mL) at 20° C. for 12 h. N-[(3S,4R)-3-fluoro-4-piperidyl]-2-[3-(2-methoxy-4-methylsulfonyl-anilino)prop-1-ynyl]-1-(2,2,2-trifluoroethyl)indol-4-amine was obtained as a yellow solid (10.4 g, 16.29 mmol, 82% yield, 2HCl). MS (ES+, m/z): 553.2.

Example D68: Synthesis of Compounds 834A and 835A

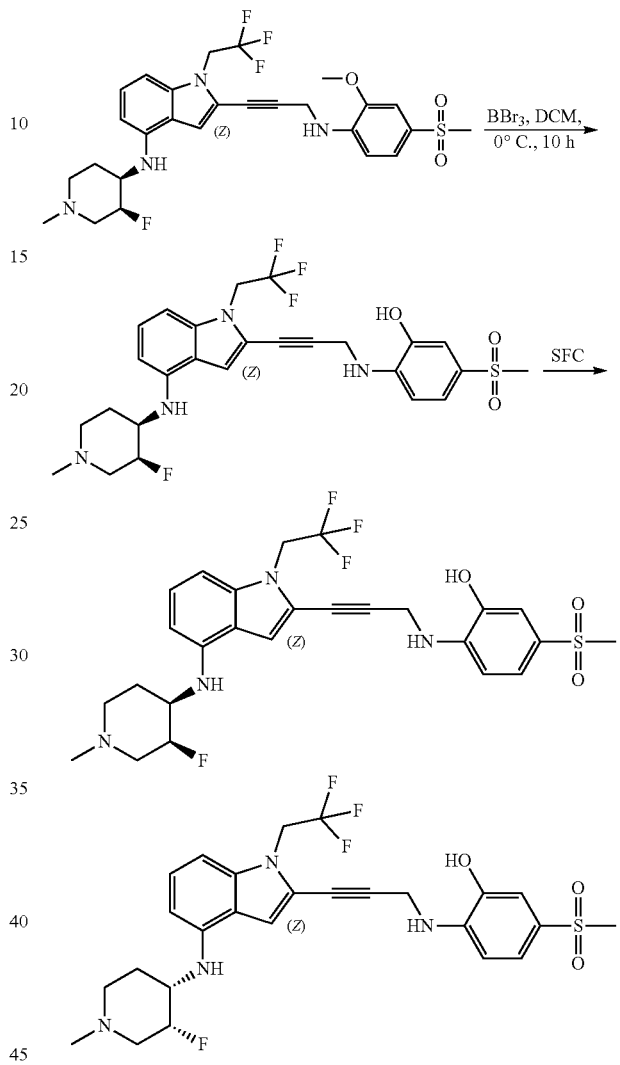

To a solution of N-((3S,4R)-3-fluoro-1-methylpiperidin-4-yl)-2-(3-((2-methoxy-4-(methylsulfonyl)phenyl)amino)prop-1-yn-1-yl)-1-(2,2,2-trifluoroethyl)-1H-indol-4-amine (200 mg, 347.33 µmol, 1 eq.) in DCM (2 mL) was added BBr$_3$ (304.55 mg, 1.22 mmol, 117.13 µL, 3.5 eq.; dropwise addition) at 0° C. The mixture was stirred at 0° C. for 2 h. TLC analysis (DCM:MeOH:TEA=100:5:2, R$_f$=0.4) showed that some of the starting material remained, and one major new spot with polarity greater than that of the starting material was detected. An additional portion of BBr$_3$ (304.55 mg, 1.22 mmol, 117.13 µL, 3.5 eq.) was added to the reaction, and the mixture was stirred at 0° C. for 2 h. TLC analysis indicated that 30% of the starting material remained. A third portion of BBr$_3$ (304.55 mg, 1.22 mmol, 117.13 µL, 3.5 eq.) was added, and the reaction mixture was stirred further at 0° C. for 6 h. TLC analysis indicated that the starting material was consumed completely. A saturated NaHCO$_3$ solution was added into the mixture to adjust the pH of the solution to 8. The mixture extracted with EtOAc (40 mL×3). The combined organic layers were washed with brine (30 mL×3), dried over anhydrous sodium sulfate, filtered, and concentrated under reduced pressure. The residue was purified by prep-TLC (SiO₂, DCM:MeOH: TEA=100:5:2) and SFC to afford 2-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-5-methanesulfonylphenol (40 mg, 70.65 µmol, 20.34% yield) and 2-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-5-methanesulfonylphenol (40 mg, 71.30 µmol, 20.53% yield) as yellow solids. [0709] 2-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-5-methanesulfonylphenol, MS (ES³⁰, m/z): 553.2; and 2-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-5-methanesulfonylphenol, MS (ES³⁰, m/z): 553.2.

Example D69: Synthesis of Compounds 800A and 801A

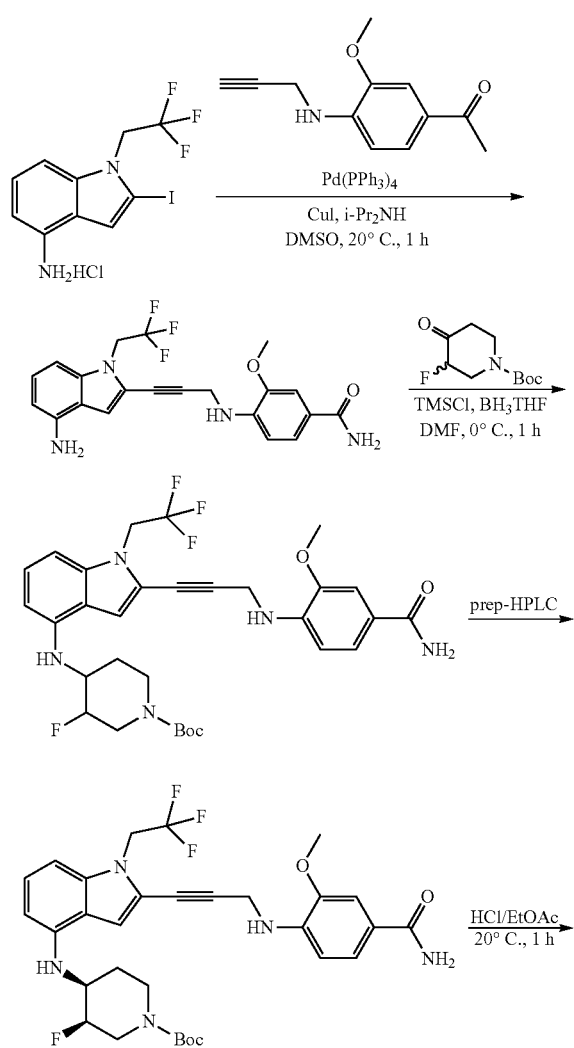

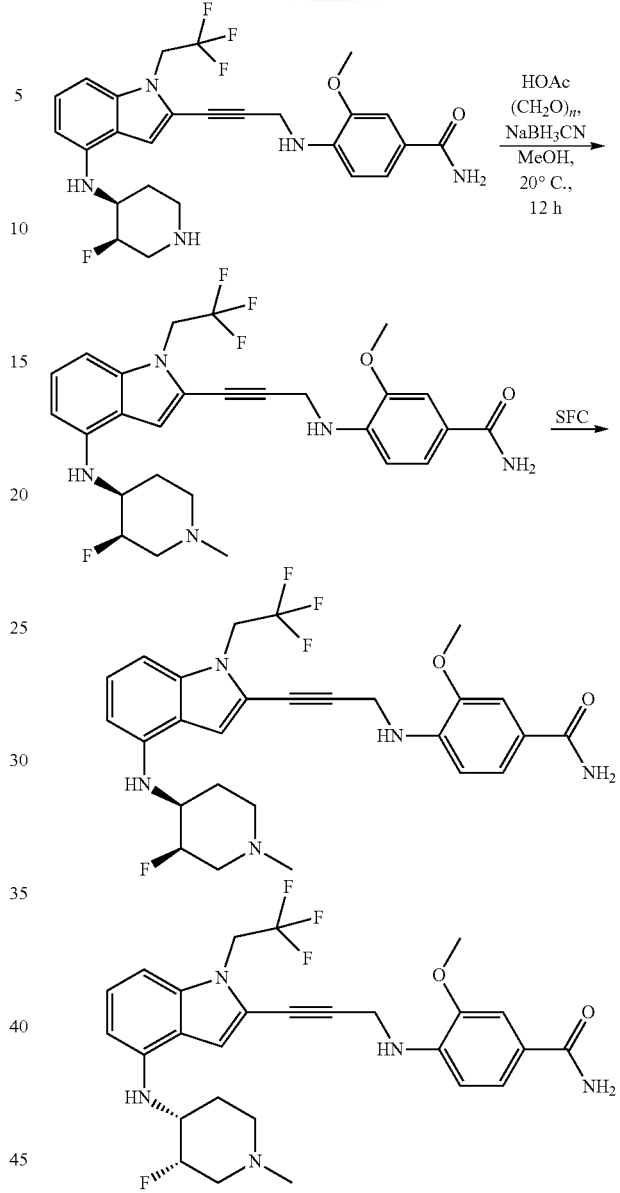

Preparation of 4-((3-(4-amino-1-(2,2,2-trifluoroethyl)-1H-indol-2-yl)prop-2-yn-1-yl)amino)-3-methoxybenzamide: A mixture of 2-iodo-1-(2,2,2-trifluoroethyl)-1H-indol-4-amine hydrochloride (1 g, 2.94 mmol, 1 eq.), 3-methoxy-4-(prop-2-yn-1-ylamino)benzamide (720.62 mg, 3.53 mmol, 1.2 eq.), CuI (672.01 mg, 3.53 mmol, 1.2 eq.), Pd(PPh₃)₄ (679.58 mg, 588.09 µmol, 0.2 eq.), and i-Pr₂NH (2.98 g, 29.40 mmol, 4.16 mL, 10 eq.) in DMSO (10 mL) was degassed and purged with N₂ three times. The mixture was stirred at 20° C. for 1 h under N₂. TLC analysis (PE:EtOAc=5:1, R$_f$=0) showed one major new spot. The reaction mixture was quenched by adding a saturated aqueous EDTA solution (100 mL) and stirring the mixture for 1 h. The mixture was extracted with EtOAc (60 mL×4). The combined organic layers were washed with brine (20 mL×2), filtered, and concentrated under reduced pressure. The residue was purified by column chromatography (SiO₂, PE:EtOAc=1:1 to 0:1) to afford the desired product (1 g, 2.16 mmol, 73.51% yield) as a yellow solid.

Preparation of tert-butyl (3R,4S)-4-((2-(3-((4-carbamoyl-2-methoxyphenyl)amino)prop-1-yn-1-yl)-1-(2,2,2-trifluoroethyl)-1H-indol-4-yl)amino)-3-fluoropiperidine-1-carboxylate: To a mixture of 4-((3-(4-amino-1-(2,2,2-trifluoroethyl)-1H-indol-2-yl)prop-2-yn-1-yl)amino)-3-methoxybenzamide (0.8 g, 1.92 mmol, 1 eq.), tert-butyl 3-fluoro-4-oxopiperidine-1-carboxylate (2.09 g, 9.61 mmol, 5 eq.), TMSCl (532.46 mg, 4.80 mmol, 622.03 µL, 98% purity, 2.5 eq.) in DMF (10 mL) was added BH$_3$·THF (1 M, 5.76 mL, 3 eq.). The mixture was stirred at 0° C. for 1 h under N$_2$. TLC analysis (PE:EtOAc=0:1, R$_f$=0.3) indicated that the starting material remained, and one major new spot was detected. The reaction mixture was quenched by adding water (100 mL) and a saturated Na$_2$CO$_3$ solution (20 mL). The mixture was extracted with EtOAc (40 mL×3). The combined organic layers were washed with brine (20 mL×4), dried over anhydrous sodium sulfate, filtered, and concentrated under reduced pressure. The crude residue was purified by column chromatography (SiO$_2$, PE:EtOAc=3:1 to 0:1) and prep-HPLC to afford the desired product (0.58 g) as a yellow solid.

Preparation of 4-((3-(4-(((3R,4S)-3-fluoropiperidin-4-yl)amino)-1-(2,2,2-trifluoroethyl)-1H-indol-2-yl)prop-2-yn-1-yl)amino)-3-methoxybenzamide: A solution of tert-butyl (3R,4S)-4-((2-(3-((4-carbamoyl-2-methoxyphenyl)amino)prop-1-yn-1-yl)-1-(2,2,2-trifluoroethyl)-1H-indol-4-yl)amino)-3-fluoropiperidine-1-carboxylate (0.58 g, 939.07 µmol, 1 eq.) in HCl/EtOAc (20 mL) was stirred at 20° C. for 1 h under N$_2$. TLC analysis (DCM:MeOH=10:1, R$_f$=0.10) indicated that one major new spot had formed. The reaction mixture was quenched by adding water (15 mL) and a saturated aqueous Na$_2$CO$_3$ solution (15 mL). The mixture was extracted with EtOAc (40 mL×3). The combined organic layers were washed with brine (20 mL×2), filtered, and concentrated under reduced pressure. The crude product (0.4 g, crude) was obtained as a yellow solid and used without purification.

Preparation of 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide and 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzamide: To a mixture of 4-((3-(4-(((3R,4S)-3-fluoropiperidin-4-yl)amino)-1-(2,2,2-trifluoroethyl)-1H-indol-2-yl)prop-2-yn-1-yl)amino)-3-methoxybenzamide (0.3 g, 579.69 µmol, 1 eq.), and (CH$_2$O)$_n$ (174.08 mg, 5.80 mmol, 10 eq.) in MeOH (3 mL) was added AcOH (34.81 mg, 579.69 µmol, 1 eq.). The reaction mixture was stirred at 20° C. for 10 h, NaBH$_3$CN (109.28 mg, 1.74 mmol, 3 eq) was added, and the mixture was stirred further at 20° C. for 2 h under N$_2$. TLC analysis (DCM:MeOH=10:1, R$_f$=0.35) indicated that the starting material remained, and one major new spot was detected. The reaction mixture was quenched by adding a saturated Na$_2$CO$_3$ solution (50 mL) and extracted with EtOAc (40 mL×4). The combined organic layers were washed with brine (20 mL×2), filtered, and concentrated under reduced pressure to give a residue. The residue was purified by prep-TLC (SiO$_2$, DCM:MeOH=10:1) and SFC to afford the desired products as yellow solids.

4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide (0.066 g, 122.55 µmol, 50.11% yield), MS (ES$^{30}$, m/z): 532.2; and 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzamide (0.063 g, 116.39 µmol, 47.59% yield), MS (ES$^{30}$, m/z): 532.2.

Example D70: Synthesis of Compounds 814A and 815A

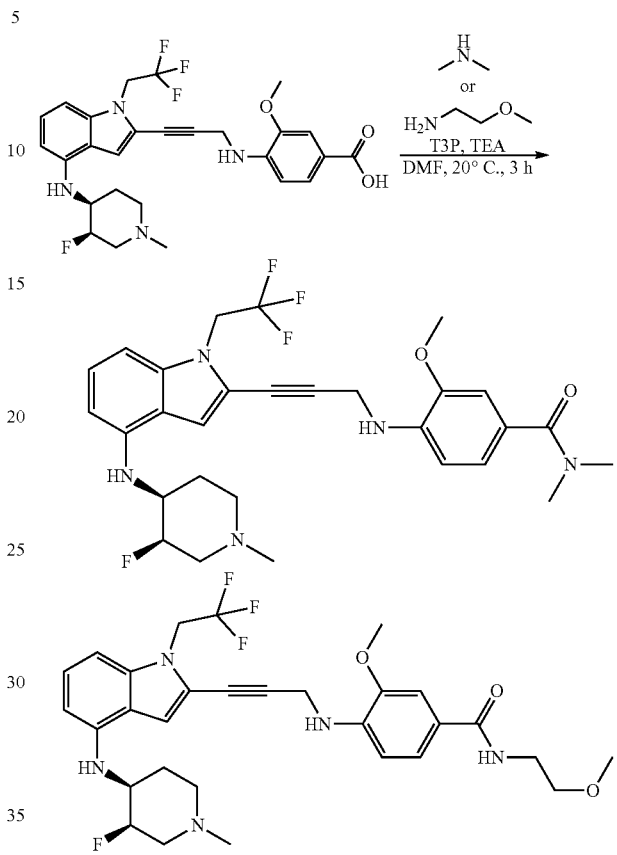

To a mixture of 4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-3-methoxybenzoic acid (0.1 g, 187.78 µmol, 1 eq.), N-methylmethanamine hydrochloride (30.63 mg, 375.57 µmol, 2 eq.) or 2-methoxyethanamine (28.21 mg, 375.57 µmol, 32.65 µL, 2 eq.), TEA (114.01 mg, 1.13 mmol, 156.82 µL, 6 eq.) in DMF (5 mL) was added and T3P® (239 mg, 375.57 µmol, 223.36 µL, 50% purity, 2 eq.). The mixture was stirred at 20° C. for 3 h under N$_2$. TLC analysis (EtOAc:TEA=10:1, R$_f$=0.37) indicated that one major new spot had formed. The reaction mixture was quenched by adding water (20 mL) and extracted with EtOAc (25 mL×4). The combined organic layers were washed with brine (10 mL×3), filtered, and concentrated under reduced pressure to give a residue. The residue was purified by prep-TLC (SiO$_2$, EtOAc:TEA=10:1) and prep-HPLC to afford the desired products as yellow solids.

rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-(2-methoxyethyl)benzamide (0.04 g, 71.12 µmol, 37.87% yield), MS (ES$^{30}$, m/z): 590.4; rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N,N-dimethylbenzamide (0.04 g, 67.37 µmol, 35.87% yield), MS (ES$^{30}$, m/z): 560.3.

Example D71: Synthesis of Compounds 697A and 698A

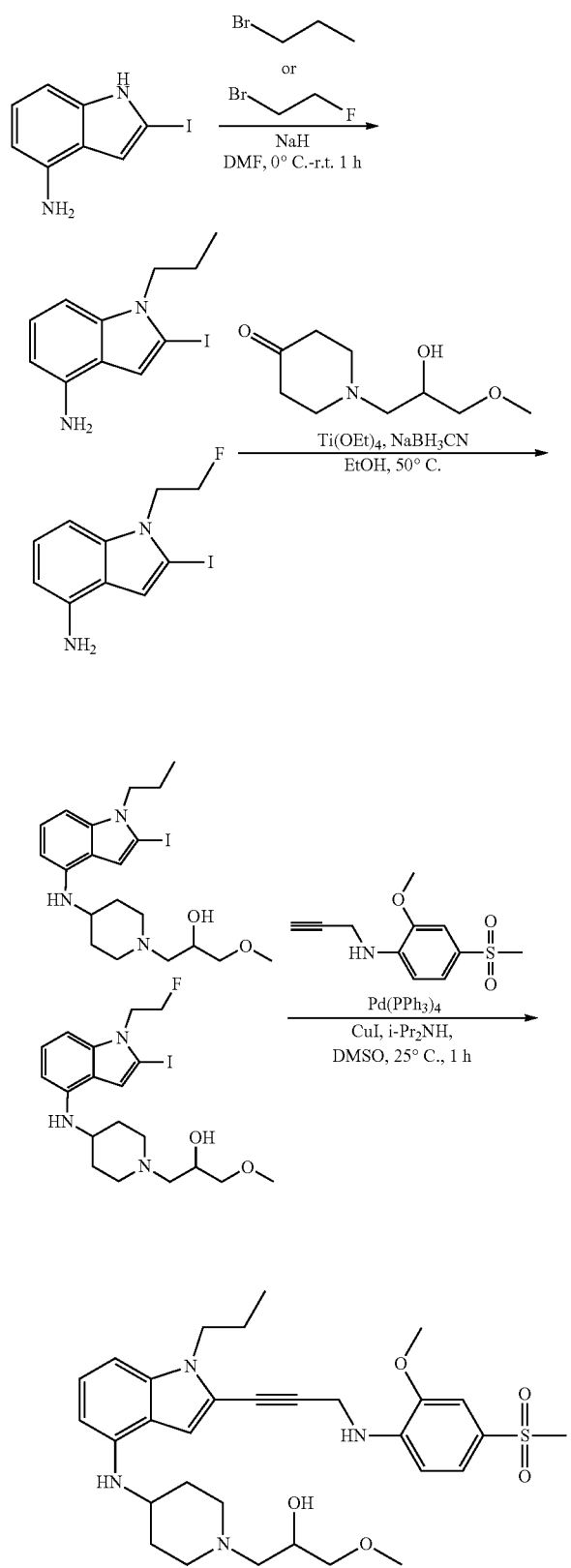

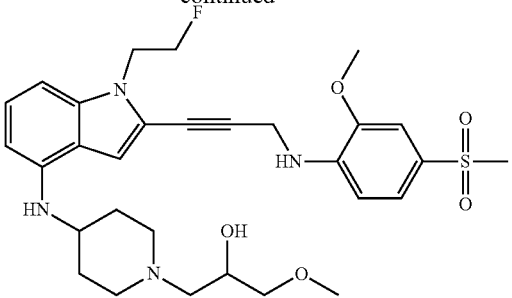

Preparation of 2-iodo-1-propyl-H-indol-4-amine and 1-(2-fluoroethyl)-2-iodo-1H-indol-4-amine: To a solution of 2-iodo-H-indol-4-amine (80 mg, 310.01 μmol, 1 eq.) in DMF (3 mL) was added NaH (37.20 mg, 930.02 μmol, 601 in mineral oil, 3 eq.) at 0° C. The mixture was stirred at 0° C. for 30 min. Then, 1-bromopropane (142.98 mg, 1.16 mmol, 105.91 μL, 1.5 eq.) or 1-bromo-2-fluoroethane (59.04 mg, 465.01 μmol, 1.5 eq.) was added, and the mixture was stirred at 25° C. for 30 min. LC-MS analysis showed that the reaction was complete. The reaction mixture was quenched by adding a saturated aqueous NH₄Cl solution (50 mL) at 0° C. and extracted with EtOAc (50 mL×2). The organic layer was washed with water (100 mL×2) and brine (100 mL×2), dried over anhydrous sodium sulfate, filtered, and concentrated under reduced pressure to give a residue. The residue was (SiO₂, PE:EtOAc=4:1) to afford the desired products.

2-iodo-1-propyl-indol-4-amine (0.17 g, 566.41 μmol, 73% yield) was obtained as a black brown oil. 1-(2-fluoroethyl)-2-iodo-indol-4-amine (70 mg, 230.19 μmol, 74% yield) was obtained as a yellow solid.

Preparation of 1-(4-((2-iodo-1-propyl-1H-indol-4-yl)amino)piperidin-1-yl)-3-methoxypropan-2-ol and 1-(4-((1-(2-fluoroethyl)-2-iodo-1H-indol-4-yl)amino)piperidin-1-yl)-3-methoxypropan-2-ol: To a solution of 2-iodo-1-propyl-11H-indol-4-amine (0.15 g, 499.77 μmol, 1 eq.) and 1-(2-fluoroethyl)-2-iodo-1H-indol-4-amine (60 mg, 197.30 μmol, 1 eq.) in EtOH (3 mL) were added 1-(2-hydroxy-3-methoxypropyl)piperidin-4-one (147.77 mg, 789.21 μmol, 4 eq.) and tetraethoxytitanium (90.01 mg, 394.60 μmol, 81.83 μL, 2 eq.). The mixture was stirred at 50° C. for 1 h, and NaBH₃CN (24.80 mg, 394.60 μmol, 2 eq.) was added. The resulting mixture was stirred further at 50° C. for 1 h. TLC analysis showed that the reaction was complete. The reaction mixture was quenched by adding a saturated aqueous NaHCO₃ solution (100 mL) and extracting the mixture with EtOAc (50 mL×2). The combined organic layers were washed with water (100 mL×2) and brine (100 mL×2), dried over anhydrous sodium sulfate, filtered, and concentrated under reduced pressure. The crude residue was purified by prep-TLC (SiO₂, DCM:MeOH=10:1) to afford the desired product.

1-[4-[(2-iodo-1-propyl-indol-4-yl)amino]-1-piperidyl]-3-methoxy-propan-2-ol (0.18 g, 381.86 μmol, 76% yield) was obtained as a yellow oil. 1-[4-[[1-(2-fluoroethyl)-2-iodo-indol-4-yl]amino]-1-piperidyl]-3-methoxy-propan-2-ol (70 mg, 147.26 μmol, 75% yield) was obtained as a yellow oil.

Preparation of 1-{4-[(2-{3-[(4-methanesulfonyl-2-methoxyphenyl)amino]prop-1-yn-1-yl}-1-propyl-1H-indol-4-yl)amino]piperidin-1-yl}-3-methoxypropan-2-ol and 1-(4-{[1-(2-fluoroethyl)-2-{3-[(4-methanesulfonyl-2-methoxyphenyl)amino]prop-1-yn-1-yl}-1H-indol-4-yl]amino}piperidin-1-yl)-3-methoxypropan-2-ol: To a solution of 2-methoxy-4-(methylsulfonyl)-N-(prop-2-yn-1-yl)aniline (38.07 mg, 159.11 μmol, 1.5 eq.) in DMSO (3 mL) were added i-Pr₂NH (107.34 mg, 1.06 mmol, 149.91 L, 10 eq.), CuI (4.04 mg, 21.21 μmol, 0.2 eq.), 1-(4-((2-iodo-1-propyl-1H-indol-4-yl)amino)piperidin-1-yl)-3-methoxypropan-2-ol (50 mg, 106.07 μmol, 1 eq.) or 1-(4-((1-(2-fluoroethyl)-2-iodo-1H-indol-4-yl)amino)piperidin-1-yl)-3-methoxypropan-2-ol (50 mg, 105.19 μmol, 1 eq.), and Pd(PPh₃)₄ (12.16 mg, 10.52 μmol, 0.1 eq.). The mixture was stirred at 25° C. for 1 h under N₂. TLC analysis showed that the reaction was complete. The reaction mixture was quenched by adding a saturated EDTA solution (50 mL) and EtOAc (25 mL) at 25° C. The aqueous layer was filtered and extracted with EtOAc (50 mL×2). The combined organic layers were washed with water (100 mL×2) and brine (100 mL×2), dried over anhydrous sodium sulfate, filtered, and concentrated under reduced pressure. The crude residue was purified by prep-TLC (SiO₂, DCM:MeOH=10:1) and prep-HPLC to afford the desired product as a white solid.

1-{4-[(2-{3-[(4-methanesulfonyl-2-methoxyphenyl)amino]prop-1-yn-1-yl}-1-propyl-1H-indol-4-yl)amino]piperidin-1-yl}-3-methoxypropan-2-ol, 18.1 mg, 29.3% yield, MS (ES³⁰, m/z): 583.3; and 1-(4-{[1-(2-fluoroethyl)-2-{3-[(4-methanesulfonyl-2-methoxyphenyl)amino]prop-1-yn-1-yl}-1H-indol-4-yl]amino}piperidin-1-yl)-3-methoxypropan-2-ol, 21.5 mg, 34.8% yield, MS (ES³⁰, m/z): 587.2.

Example D72: Synthesis of 1-(4-{[1-(2-chloroethyl)-2-{3-[(4-methanesulfonyl-2-methoxyphenyl)amino]prop-1-yn-1-yl}-1H-indol-4-yl]amino}piperidin-1-yl)-3-methoxypropan-2-ol (Compound 700A)

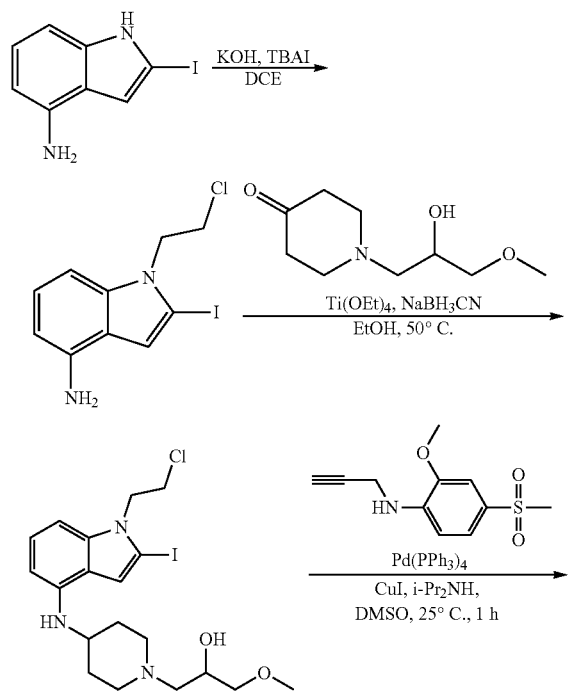

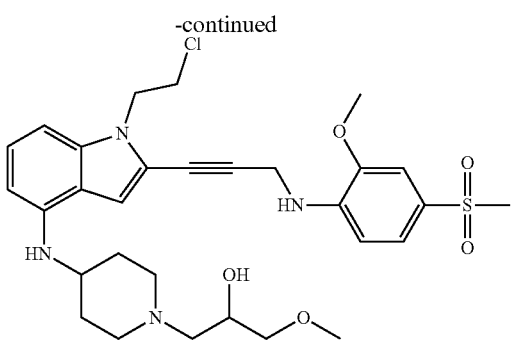

Preparation of 1-(2-chloroethyl)-2-iodo-1H-indol-4-amine: To a solution of 2-iodo-1H-indol-4-amine (0.2 g, 775.02 μmol, 1 eq.) in DCE (4 mL) were added KOH (130.45 mg, 2.33 mmol, 3 eq.) and TBAI (57.25 mg, 155 μmol, 0.2 eq.). The mixture was stirred at 25° C. for 2 h. TLC analysis showed that the reaction was complete. The reaction mixture was diluted with water (100 mL) and extracted with EtOAc (50 mL×2). The combined organic layers were washed with water (100 mL×2) and brine (100 mL×2), dried over anhydrous sodium sulfate, filtered, and concentrated under reduced pressure. The residue was purified by prep-TLC (SiO₂, PE:EtOAc=4:1) to afford the desired product (0.2 g, 623.92 μmol, 80.50% yield) as a brown solid.

Preparation of 1-(4-((1-(2-chloroethyl)-2-iodo-1H-indol-4-yl)amino)piperidin-1-yl)-3-methoxypropan-2-ol: To a solution of 1-(2-chloroethyl)-2-iodo-1H-indol-4-amine (0.18 g, 561.52 μmol, 1 eq.) in EtOH (4 mL) were added 1-(2-hydroxy-3-methoxypropyl)piperidin-4-one (420.55 mg, 2.25 mmol, 4 eq.) and tetraethoxytitanium (256.18 mg, 1.12 mmol, 232.89 μL, 2 eq.). The mixture was stirred at 50° C. for 1 h, then NaBH₃CN (70.57 mg, 1.12 mmol, 2 eq.) was added. The resulting mixture was stirred at 50° C. for 3 h. TLC analysis showed that the reaction was complete. The reaction mixture was quenched by adding a saturated aqueous NaHCO₃ solution (100 mL) and EtOAc (50 mL). The organic layer was filtered under reduced pressure to give liquid phase, which was extracted with EtOAc (50 mL×2). The combined organic layers were washed with water (100 mL×2) and brine (100 mL×2), dried over anhydrous sodium sulfate, filtered, and concentrated under reduced pressure. The residue was purified by prep-TLC (SiO₂, DCM:MeOH=10:1) to afford the desired product (0.22 g, 447.34 μmol, 79.67% yield) as a yellow oil.

Preparation of 1-(4-{[1-(2-chloroethyl)-2-{3-[(4-methanesulfonyl-2-methoxyphenyl)amino]prop-1-yn-1-yl}-1H-indol-4-yl]amino}piperidin-1-yl)-3-methoxypropan-2-ol:
To a solution of 2-methoxy-4-methylsulfonyl-N-prop-2-ynyl-aniline (36.49 mg, 152.50 μmol, 1.5 eq.) in DMSO (3 mL) were added i-Pr₂NH (102.88 mg, 1.02 mmol, 143.69 μL, 10 eq.), CuI (3.87 mg, 20.33 μmol, 0.2 eq.), 1-(4-((1-(2-chloroethyl)-2-iodo-1H-indol-4-yl)amino)piperidin-1-yl)-3-methoxypropan-2-ol (50 mg, 101.67 μmol, 1 eq.), and Pd(PPh₃)₄ (11.75 mg, 10.17 μmol, 0.1 eq.). The mixture was stirred at 25° C. for 1 h under N₂. TLC analysis showed that the reaction was complete. The reaction mixture was stirred by adding a saturated aqueous EDTA solution (50 mL) and EtOAc (25 mL) at 25° C. The aqueous layer was filtered and extracted with EtOAc (50 mL×2). The combined organic layers were washed with water (100 mL×2) and brine (100 mL×2), dried over anhydrous sodium sulfate, filtered, and concentrated under reduced pressure. The crude residue was purified by prep-TLC (SiO$_2$, DCM:MeOH=10:1) and prep-HPLC to afford the desired product (16.1 mg, 26.69 µmol, 26.25% yield) as a white solid. MS (ES$^{30}$, m/z): 603.2.

Example D73: Synthesis of 1-(4-{[1-(2,2-difluoro-ethyl)-2-{3-[(4-methanesulfonyl-2-methoxyphenyl)amino]prop-1-yn-1-yl}-1H-indol-4-yl]amino}piperidin-1-yl)-3-methoxypropan-2-ol (Compound 709A)

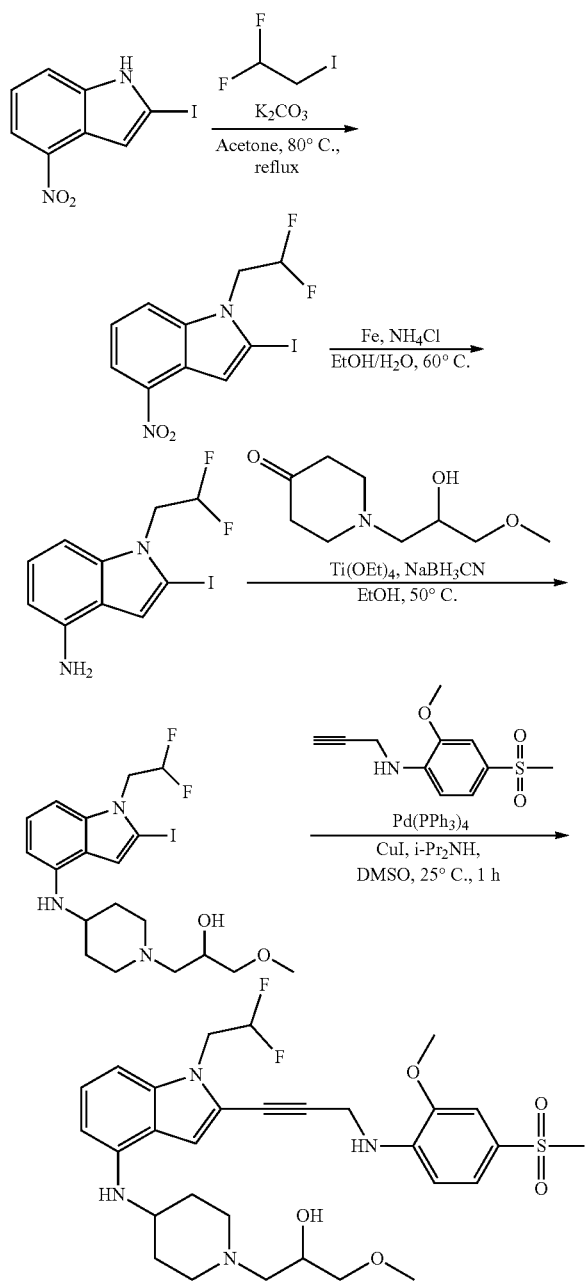

Preparation of 1-(2,2-difluoroethyl)-2-iodo-4-nitro-1H-indole: To a solution of 2-iodo-4-nitro-1H-indole (0.5 g, 1.74 mmol, 1 eq.) in acetone (5 mL) were added 1,1-difluoro-2-iodo-ethane (3.33 g, 17.36 mmol, 9.64 µL, 10 eq.) and K$_2$CO$_3$ (719.74 mg, 5.21 mmol, 3 eq.). The mixture was stirred at 80° C. for 16 h. TLC analysis showed that the reaction was complete. The reaction mixture was diluted with water (100 mL) and extracted with EtOAc (50 mL×2). The combined organic layers were washed with water (100 mL×2) and brine (100 mL×2), dried over anhydrous sodium sulfate, filtered, and concentrated under reduced pressure. The residue was washed by PE to afford the desired product (0.52 g, 1.48 mmol, 85.08% yield) as a yellow solid.

Preparation of 1-(2,2-difluoroethyl)-2-iodo-1H-indol-4-amine: To a solution of 1-(2,2-difluoroethyl)-2-iodo-4-nitro-1H-indole (0.45 g, 1.28 mmol, 1 eq.) in EtOH (4 mL) were added a saturated aqueous solution of NH$_4$Cl (68.37 mg, 1.28 mmol, 1 mL) and Fe (214.13 mg, 3.83 mmol, 3 eq.). The mixture was stirred at 60° C. for 1 h. TLC analysis showed that the reaction was complete. The reaction mixture was filtered and extracted with EtOAc (50 mL×2). The organic layer was washed with water (100 mL×2) and brine (100 mL×2), dried over anhydrous sodium sulfate, filtered, and concentrated under reduced pressure. The residue was purified by prep-TLC (SiO$_2$, PE:EtOAc=4:1) to afford the desired product (0.38 g, 1.18 mmol, 92.31% yield) as a yellow solid.

Preparation of 1-(4-((1-(2,2-difluoroethyl)-2-iodo-1H-indol-4-yl)amino)piperidin-1-yl)-3-methoxypropan-2-ol: To a solution of 1-(2,2-difluoroethyl)-2-iodo-1H-indol-4-amine (0.15 g, 465.71 µmol, 1 eq.) in EtOH (4 mL) were added 1-(2-hydroxy-3-methoxypropyl)piperidin-4-one (348.79 mg, 1.86 mmol, 4 eq.) and tetraethoxytitanium (212.46 mg, 931.41 µmol, 193.15 µL, 2 eq.). The mixture was stirred at 50° C. for 1 h, and NaBH$_3$CN (58.53 mg, 931.41 µmol, 2 eq.) was added to the reaction. The resulting mixture was stirred at 50° C. for 1 h. TLC analysis showed that the reaction was complete. The reaction mixture was quenched by adding a saturated aqueous NaHCO$_3$ solution (100 mL) and EtOAc (50 mL). The mixture was filtered under reduced pressure and extracted with EtOAc (50 mL×2). The combined organic layers were washed with water (100 mL×2) and brine (100 mL×2), dried over anhydrous sodium sulfate, filtered, and concentrated under reduced pressure. The residue was purified by prep-TLC (SiO$_2$, DCM:MeOH=10:1) to give the desired product (0.18 g, 364.87 µmol, 78.35% yield) as a yellow oil.

Preparation of 1-(4-{[1-(2,2-difluoroethyl)-2-{3-[(4-methanesulfonyl-2-methoxyphenyl)amino]prop-1-yn-1-yl}-1H-indol-4-yl]amino}piperidin-1-yl)-3-methoxypropan-2-ol: To a solution of 2-methoxy-4-methylsulfonyl-N-prop-2-ynyl-aniline (36.38 mg, 152.03 µmol, 1.5 eq.) in DMSO (3 mL) were added i-Pr$_2$NH (102.56 mg, 1.01 mmol, 143.24 µL, 10 eq.), CuI (3.86 mg, 20.27 µmol, 0.2 eq.), 1-(4-((1-(2,2-difluoroethyl)-2-iodo-1H-indol-4-yl)amino)piperidin-1-yl)-3-methoxypropan-2-ol (50 mg, 101.35 µmol, 1 eq.), and Pd(PPh$_3$)$_4$ (11.71 mg, 10.14 µmol, 0.1 eq.). The mixture was stirred at 25° C. for 1 h under N$_2$. TLC analysis showed that the reaction was complete. The reaction mixture was quenched by adding a saturated aqueous EDTA solution (50 mL) and EtOAc (25 mL) at 25° C. The mixture was filtered and extracted with EtOAc (50 mL×2). The combined organic layers were washed with water (100 mL×2) and brine (100 mL×2), dried over anhydrous sodium sulfate, filtered, and concentrated under reduced pressure. The crude residue was purified by prep-TLC (SiO$_2$, DCM:MeOH=10:1) and prep-HPLC to give the desired product (23.6 mg, 38.13 µmol, 37.62% yield) as a white solid. MS (ES$^{30}$, m/z): 605.2.

Example D74: Synthesis of 1-{4-[(2-{3-[(4-methanesulfonyl-2-methoxyphenyl)amino]prop-1-yn-1-yl}-1-(3,3,3-trifluoropropyl)-1H-indol-4-yl)amino]piperidin-1-yl}-3-methoxypropan-2-ol (Compound 711A)

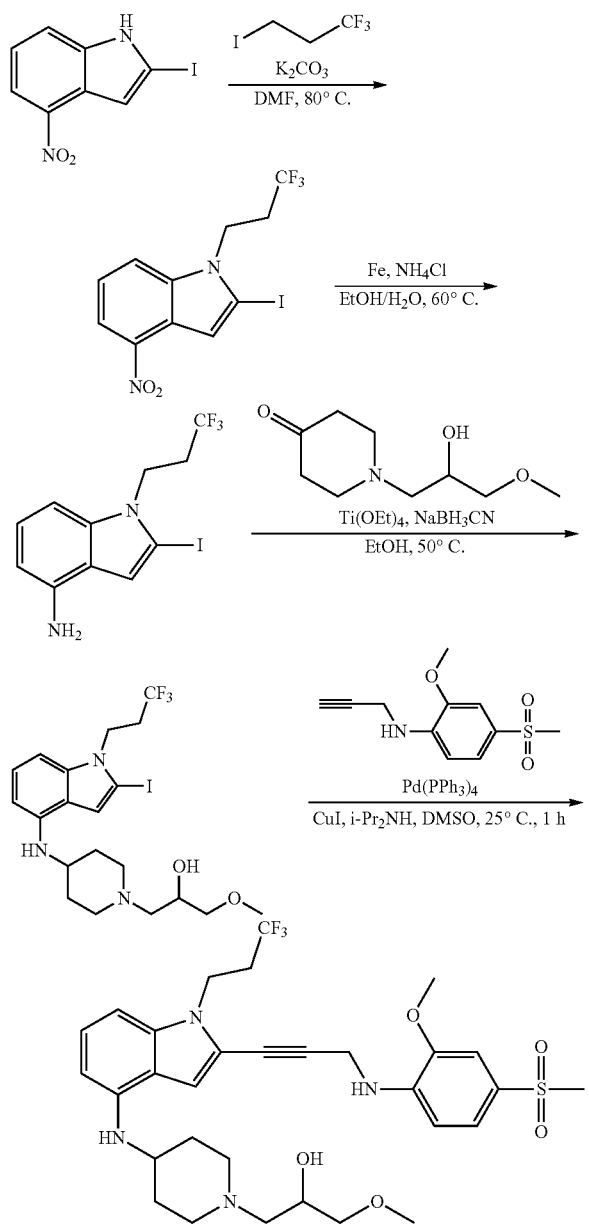

Preparation of 2-iodo-4-nitro-1-(3,3,3-trifluoropropyl)-1H-indole: To a solution of 2-iodo-4-nitro-1H-indole (0.5 g, 1.74 mmol, 1 eq.) in DMF (5 mL) was added 1,1,1-trifluoro-3-iodopropane (3.11 g, 13.89 mmol, 1.63 mL, 8 eq.). Then, $K_2CO_3$ (719.74 mg, 5.21 mmol, 3 eq.) was added, and the mixture was stirred at 80° C. for 5 h. TLC analysis showed that 60% of the starting material remained, and 30% of the desired product was detected. The reaction mixture was diluted with water (150 mL) and extracted with EtOAc (50 mL×2). The combined organic layers were washed with water (100 mL×2) and brine (100 mL×2), dried over anhydrous sodium sulfate, filtered, and concentrated under reduced pressure. The residue was purified by prep-TLC (SiO$_2$, PE:EtOAc=4:1) to afford the desired product (0.15 g, 390.53 μmol, 22.50% yield) as a white solid.

Preparation of 2-iodo-1-(3,3,3-trifluoropropyl)-1H-indol-4-amine: To a solution of 2-iodo-4-nitro-1-(3,3,3-trifluoropropyl)-1H-indole (0.12 g, 312.42 μmol, 1 eq.) in EtOH (2 mL) were added aqueous NH$_4$Cl (4.18 mg in 0.5 mL of water, 78.11 μmol) and Fe (52.35 mg, 937.27 μmol, 3 eq.). The mixture was stirred at 60° C. for 1 h. TLC analysis showed that the reaction was complete. The reaction mixture was filtered and extracted with EtOAc (50 mL×2). The combined organic layers were washed with water (100 mL×2) and brine (100 mL×2), dried over anhydrous sodium sulfate, filtered, and concentrated under reduced pressure. The crude product (0.12 g, crude) was obtained as a white solid and used without purification.

Preparation of 1-(4-((2-iodo-1-(3,3,3-trifluoropropyl)-1H-indol-4-yl)amino)piperidin-1-yl)-3-methoxypropan-2-ol: To a solution of 2-iodo-1-(3,3,3-trifluoropropyl)-1H-indol-4-amine (0.1 g, 282.40 μmol, 1 eq.) in EtOH (2 mL) were added 1-(2-hydroxy-3-methoxy-propyl)piperidin-4-one (211.50 mg, 1.13 mmol, 4 eq.) and tetraethoxytitanium (128.83 mg, 564.80 μmol, 117.12 μL, 2 eq.). The mixture was stirred at 50° C. for 1 h, and NaBH$_3$CN (35.49 mg, 564.80 μmol, 2 eq.) was added. The mixture was stirred at 50° C. for 1 h. TLC analysis showed that the reaction was complete. The reaction mixture was quenched by adding a saturated aqueous NaHCO$_3$ solution (100 mL) and EtOAc (50 mL). The mixture was filtered under reduced pressure to give liquid phase and extracted with EtOAc (50 mL×2). The combined organic layers were washed with water (100 mL×2) and brine (100 mL×2), dried over anhydrous sodium sulfate, filtered, and concentrated under reduced pressure. The residue was purified by prep-TLC (SiO$_2$, DCM:MeOH=10:1) to afford the desired product (0.11 g, 209.39 μmol, 74.15% yield) as a yellow oil.

Preparation of 1-{4-[(2-{3-[(4-methanesulfonyl-2-methoxyphenyl)amino]prop-1-yn-1-yl}-1-(3,3,3-trifluoropropyl)-1H-indol-4-yl)amino]piperidin-1-yl}-3-methoxypropan-2-ol: To a solution of 2-methoxy-4-methylsulfonyl-N-prop-2-ynyl-aniline (34.16 mg, 142.76 μmol, 1.5 eq.) in DMSO (3 mL) were added i-Pr$_2$NH (96.31 mg, 951.76 μmol, 134.51 μL, 10 eq.), CuI (3.63 mg, 19.04 μmol, 0.2 eq.), 1-(4-((2-iodo-1-(3,3,3-trifluoropropyl)-1H-indol-4-yl)amino)piperidin-1-yl)-3-methoxypropan-2-ol (50 mg, 95.18 μmol, 1 eq.), and Pd(PPh$_3$)$_4$ (11 mg, 9.52 μmol, 0.1 eq.). The mixture was stirred at 25° C. for 1 h under N$_2$. TLC analysis showed that the reaction was complete. The reaction mixture was stirred by adding a saturated aqueous EDTA solution (50 mL) and EtOAc (25 mL) at 25° C. The mixture was filtered and extracted with EtOAc (50 mL×2). The combined organic layers were washed with water (100 mL×2) and brine (100 mL×2), dried over anhydrous sodium sulfate, filtered, and concentrated under reduced pressure. The residue was purified by prep-TLC (SiO$_2$, DCM:MeOH=10:1) and prep-HPLC to afford the desired product (19.9 mg, 31.25 μmol, 32.84% yield) as a white solid. MS (ES$^{30}$, m/z): 637.3.

Example D75: Synthesis of 1-(4-{[1-(2,2-difluoro-propyl)-2-{3-[(4-methanesulfonyl-2-methoxyphenyl)amino]prop-1-yn-1-yl}-1H-indol-4-yl]amino}piperidin-1-yl)-3-methoxypropan-2-ol (Compound 712A)

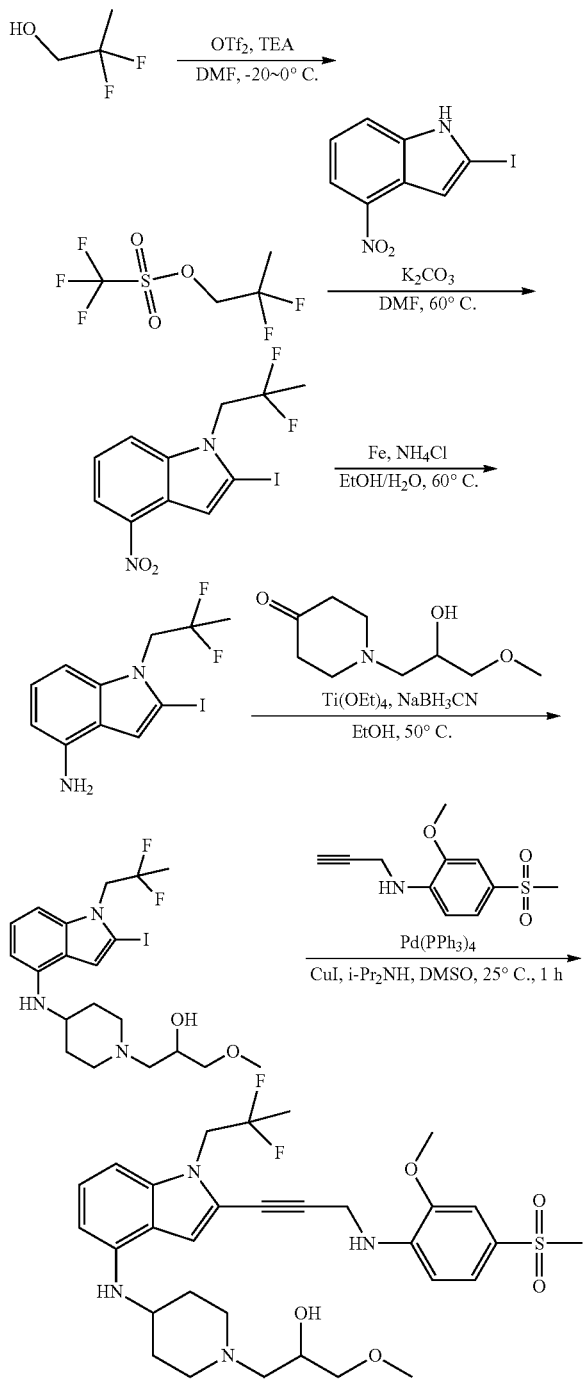

Preparation of 2,2-difluoropropyl trifluoromethanesulfonate: To a solution of 2,2-difluoropropan-1-ol (0.5 g, 5.20 mmol, 1 eq.) in DCM (5 mL) were added TEA (1.05 g, 10.41 mmol, 1.45 mL, 2 eq.) and trifluoromethylsulfonyl trifluoromethanesulfonate (1.91 g, 6.77 mmol, 1.12 mL, 1.3 eq.) dropwise at −20° C. The mixture was stirred at −20° C.~0° C. for 12 h. The reaction mixture was diluted by adding DCM (20 mL), and the resulting mixture was poured into ice water (100 mL) and extracted with DCM (25 mL×2). The combined organic layers were washed with 20% aqueous $Na_2CO_3$ (100 mL×2), water (100 mL×2), and brine (100 mL×2), dried over anhydrous sodium sulfate, filtered, and concentrated under reduced pressure. The crude product (0.6 g, crude) was obtained as a black brown oil and used in the next step without purification.

Preparation of 1-(2,2-difluoropropyl)-2-iodo-4-nitro-1H-indole: To a solution of 2-iodo-4-nitro-1H-indole (0.2 g, 694.34 μmol, 1 eq.) in DMF (3 mL) were added 2,2-difluoropropyl trifluoromethanesulfonate (396.02 mg, 1.74 mmol, 2.5 eq.) and $K_2CO_3$ (287.89 mg, 2.08 mmol, 3 eq.). The mixture was stirred at 80° C. for 2 h. TLC analysis showed that the reaction was complete. The reaction mixture was diluted with water (100 mL) and extracted with EtOAc (50 mL×2). The combined organic layers were washed with water (100 mL×2) and brine (100 mL×2), dried over anhydrous sodium sulfate, filtered, and concentrated under reduced pressure. The residue was purified by prep-TLC ($SiO_2$, PE:EtOAc=4:1) to afford the desired product (0.2 g, 546.30 μmol, 78.68% yield) as a yellow solid.

Preparation of 1-(2,2-difluoropropyl)-2-iodo-1H-indol-4-amine: To a solution of 1-(2,2-difluoropropyl)-2-iodo-4-nitro-1H-indole (0.18 g, 491.67 μmol, 1 eq.) in EtOH (4 mL) were added aqueous $NH_4Cl$ (68.37 mg in 1 mL of water, 1.28 mmol) and Fe (82.38 mg, 1.47 mmol, 3 eq.). The mixture was stirred at 60° C. for 1 h. TLC analysis showed that the reaction was complete. The reaction mixture was filtered and extracted with EtOAc (50 mL×2) and washed with water (100 mL×2) and brine (100 mL×2). The organic layer was dried over anhydrous sodium sulfate, filtered, and concentrated under reduced pressure to give a residue. The crude product (0.18 g, crude) was obtained as a brown solid and used without purification. MS ($ES^{30}$, m/z): 337.0.

Preparation of 1-(4-((1-(2,2-difluoropropyl)-2-iodo-1H-indol-4-yl)amino)piperidin-1-yl)-3-methoxypropan-2-ol: To a mixture of 1-(2,2-difluoropropyl)-2-iodo-1H-indol-4-amine (0.15 g, 357.02 μmol, 1 eq.) in EtOH (3 mL) were added 1-(2-hydroxy-3-methoxy-propyl)piperidin-4-one (267.38 mg, 1.43 mmol, 4 eq.) and tetraethoxytitanium (162.88 mg, 714.03 μmol, 148.07 μL, 2 eq.). The mixture was stirred at 50° C. for 1 h, and $NaBH_3CN$ (44.87 mg, 714.03 μmol, 2 eq.) was added. The resulting mixture was stirred at 50° C. for 1 h. TLC analysis showed that the reaction was complete. The reaction mixture was quenched by adding a saturated aqueous $NaHCO_3$ solution (100 mL) and EtOAc (50 mL). The mixture was filtered and concentrated under reduced pressure. The solution was extracted with EtOAc (50 mL×2). The combined organic layers were washed with water (100 mL×2) and brine (100 mL×2), dried over anhydrous sodium sulfate, filtered, and concentrated under reduced pressure to give a residue. The residue was purified by prep-TLC ($SiO_2$, DCM:MeOH=10:1) to afford the desired product (0.15 g, 295.65 μmol, 82.81% yield) as a brown oil. MS ($ES^{30}$, m/z): 508.2.

Preparation of 1-(4-{[1-(2,2-difluoropropyl)-2-{3-[(4-methanesulfonyl-2-methoxyphenyl)amino]prop-1-yn-1-yl}-1H-indol-4-yl]amino}piperidin-1-yl)-3-methoxypropan-2-ol: To a solution of 2-methoxy-4-methylsulfonyl-N-prop-2-ynyl-aniline (35.37 mg, 147.83 μmol, 1.5 eq.) in DMSO (3 mL) were added i-$Pr_2NH$ (99.72 mg, 985.50 μmol, 139.28 μL, 10 eq.), CuI (3.75 mg, 19.71 mol, 0.2 eq.), 1-(4-((1-(2,2-difluoropropyl)-2-iodo-1H-indol-4-yl)amino)piperidin-1-yl)-3-methoxypropan-2-ol (50 mg, 98.55 μmol, 1 eq.), and Pd(PPh$_3$)$_4$ (11.39 mg, 9.86 μmol, 0.1 eq.). The mixture was stirred at 25° C. for 1 h under N₂. LC-MS analysis showed that the reaction was complete. The reaction mixture was quenched by adding a saturated aqueous EDTA solution (50 mL) and EtOAc (25 mL) at 25° C. The mixture was filtered and extracted with EtOAc (50 mL×2), washed with water (100 mL×2) and brine (100 mL×2). The combined organic layers were dried over anhydrous sodium sulfate, filtered, and concentrated under reduced pressure to give a residue. The residue was purified by prep-TLC (SiO₂, DCM:MeOH=10:1) and prep-HPLC to obtain the desired product (23.3 mg, 37.66 mol, 38.21% yield) as a white solid. MS (ES$^{30}$, m/z): 619.3.

Example D76: Synthesis of Compounds 466A, 467A, 991A, 1035A, and 1051A

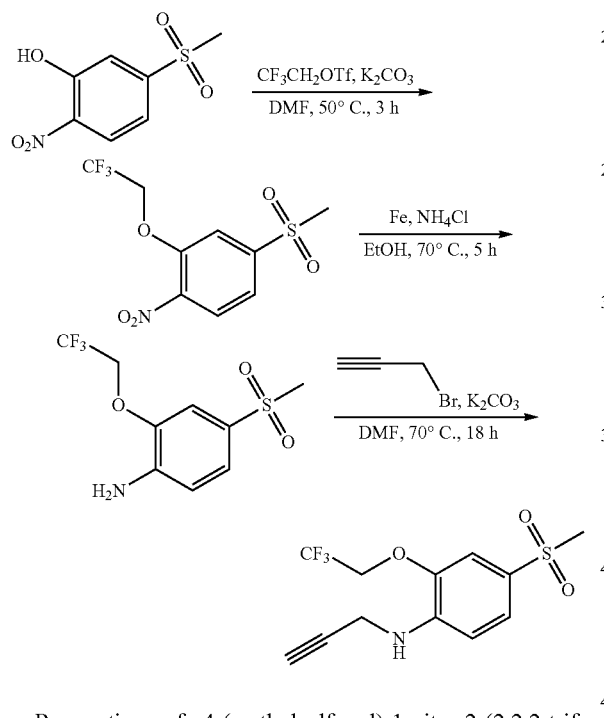

Preparation of 4-(methylsulfonyl)-1-nitro-2-(2,2,2-trifluoroethoxy)benzene: To a solution of 5-(methylsulfonyl)-2-nitrophenol (1.50 g, 6.91 mmol, 1 eq.) in DMF (10 mL) were added K₂CO₃ (2.87 g, 20.73 mmol, 3 eq.) and 2,2,2-trifluoroethyl trifluoromethanesulfonate (2.41 g, 10.37 mmol, 1.50 eq.). The mixture was stirred at 50° C. for 3 h. HPLC analysis showed that the reaction was complete. The residue was poured into water (50 mL), and the aqueous phase was extracted with EtOAc (50 mL×3). The combined organic layers were washed with brine (50 mL×3), dried over anhydrous sodium sulfate, filtered, and concentrated in vacuo to afford the desired product (1.70 g, crude) as a yellow solid.

Preparation of 4-(methylsulfonyl)-2-(2,2,2-trifluoroethoxy)aniline: To a solution of 4-(methylsulfonyl)-1-nitro-2-(2,2,2-trifluoroethoxy)benzene (1.70 g, 5.68 mmol, 1 eq.) in EtOH (20 mL) was added an aqueous NH₄Cl solution (3.04 g in 2 mL of water, 56.81 mmol, 10 eq.). The mixture was heated to 70° C., and Fe (3.17 g, 56.81 mmol, 10 eq.) was added to the mixture. The resulting reaction mixture was stirred further at 70° C. for 2 h. LC-MS and HPLC analysis showed that the starting material remained. An additional portion of Fe (3.17 g, 56.81 mmol, 10 eq.) was added to the reaction, and the mixture was stirred further at 70° C. for 3 h. LC-MS analysis showed that the reaction was complete. The residue was poured into a saturated aqueous NaHCO₃ solution (100 mL), and EtOAc was added (40 mL). The mixture was filtered through a pad of diatomite, and the aqueous phase was extracted with EtOAc (40 mL×3). The combined organic layers were dried over anhydrous sodium sulfate, filtered, and concentrated in vacuo to afford the desired product (1.30 g, crude) as a black brown oil. MS (ES$^{30}$, m/z): 270.1.

Preparation of 4-(methylsulfonyl)-N-(prop-2-yn-1-yl)-2-(2,2,2-trifluoroethoxy)aniline: To a solution of 4-(methylsulfonyl)-2-(2,2,2-trifluoroethoxy)aniline (1.20 g, 4.46 mmol, 1 eq.) in DMF (15 mL) were added 3-bromoprop-1-yne (1.06 g, 8.92 mmol, 768.93 µL, 2 eq.) and K₂CO₃ (1.85 g, 13.38 mmol, 3 eq.). The mixture was heated to 70° C. and stirred for 12 h. TLC analysis showed that 60% of the starting material remained. An additional portion of 3-bromoprop-1-yne (1.06 g, 8.92 mmol, 768.93 µL, 2 eq.) was added to the reaction, and the mixture was stirred at 70° C. for 3 h. TLC analysis showed that 40% of the starting material remained. A third portion of 3-bromoprop-1-yne (1.06 g, 8.92 mmol, 768.93 L, 2 eq.) was added to the reaction, and the mixture was stirred at 70° C. for 3 h. TLC analysis showed that 20% of the starting material remained. The residue was poured into water (50 mL), and the aqueous phase was extracted with EtOAc (40 mL×3). The combined organic layers were washed with brine (50 mL×3), dried over anhydrous sodium sulfate, filtered, and concentrated in vacuo. The crude residue was purified by silica gel chromatography (PE:EtOAc=10:1 to 5:1) to afford the desired product (800 mg, 2.21 mmol, 49.56% yield) as a yellow solid.

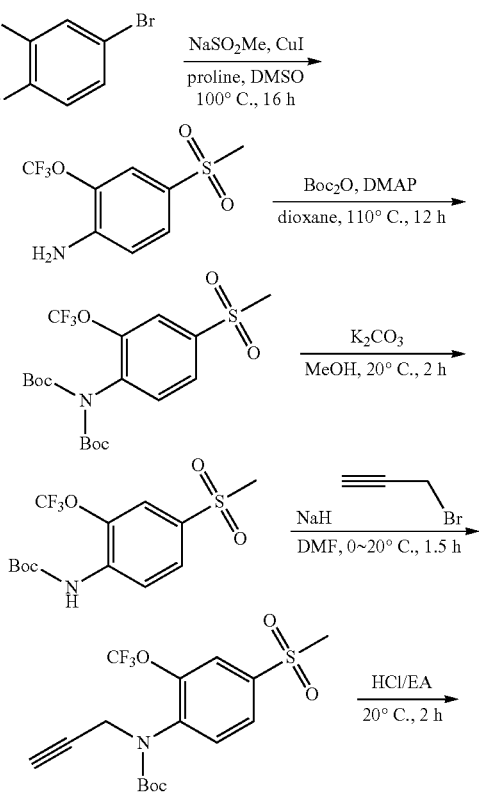

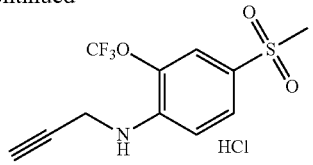

Preparation of 4-(methylsulfonyl)-2-(trifluoromethoxy)aniline: To a mixture of 4-bromo-2-(trifluoromethoxy)aniline (0.5 g, 1.95 mmol, 295.86 µL, 1 eq.) and sodium methyl sulfate (598.13 mg, 5.86 mmol, 3 eq.) in DMSO (8 mL) were added proline (112.42 mg, 976.49 µmol, 0.5 eq.) and CuI (148.78 mg, 781.19 µmol, 0.4 eq.). The reaction mixture was stirred at 100° C. for 16 h. LC-MS and TLC analysis (PE:EtOAc=1:1, R$_f$=0.4) indicated that 50% of the starting material remained, and one major new spot with polarity greater than that of the starting material was detected. The reaction mixture was poured into a saturated aqueous EDTA solution (50 mL) and stirred at 20° C. for 1 h. The mixture was then extracted with EtOAc (50 mL×3). The combined organic layers were washed with brine (50 mL×3), dried over anhydrous sodium sulfate, filtered, and concentrated under reduced pressure. The crude residue was purified by column chromatography (SiO$_2$, PE:EtOAc=10:1 to 1:1) to afford the desired product (0.13 g, 509.38 µmol, 26.08% yield) as a white solid. MS (ES$^{30}$, m/z): 258.2.

Preparation of N,N-di(tert-butoxycarbonyl)-4-(methylsulfonyl)-2-(trifluoromethoxy)aniline: A mixture of 4-(methylsulfonyl)-2-(trifluoromethoxy)aniline (0.08 g, 313.46 µmol, 1 eq.) and di-tert-butyl dicarbonate (136.82 mg, 626.92 µmol, 144.03 µL, 2 eq.) in dioxane (2 mL) was added DMAP (38.30 mg, 313.46 µmol, 1 eq.). The mixture was stirred at 110° C. for 12 h. LC-MS analysis showed that the starting material was consumed completely, and two new main peaks with desired the desired mass was detected. The reaction mixture was poured into water (20 mL) and extracted with EtOAc (20 mL×3). The combined organic layers were washed with brine 30 mL (10 mL×3), dried over anhydrous sodium sulfate, filtered, and concentrated under reduced pressure. The crude residue was purified by prep-TLC (PE:EtOAc=2:1, R$_{f2}$=0.4) to afford the desired product (0.12 g, 233.44 µmol, 93.09% yield) as a white solid.

Preparation of tert-butyl (4-(methylsulfonyl)-2-(trifluoromethoxy)phenyl)carbamate: A mixture of N,N-di(tert-butoxycarbonyl)-4-(methylsulfonyl)-2-(trifluoromethoxy)aniline (120 mg, 231.86 µmol, 4.68 eq.) and K$_2$CO$_3$ (34.23 mg, 247.66 µmol, 5 eq.) in MeOH (5 mL) was stirred at 20° C. for 2 h. TLC analysis (PE:EtOAc=2:1, R$_f$=0.4) indicated that the starting material was consumed completely, and one new spot for the desired product was detected. The reaction mixture was concentrated under reduced pressure to remove solvent. The residue was diluted with water (20 mL) and extracted with EtOAc (20 mL×3). The combined organic layers were washed with brine (20 mL×3), dried over anhydrous sodium sulfate, filtered, and concentrated under reduced pressure to give the crude product (0.075 g, crude) as a yellow solid.

Preparation of tert-butyl (4-(methylsulfonyl)-2-(trifluoromethoxy)phenyl)(prop-2-yn-1-yl)carbamate: To a solution of tert-butyl (4-(methylsulfonyl)-2-(trifluoromethoxy)phenyl)carbamate (0.24 g, 675.43 µmol, 1 eq.) in DMF (8 mL) was added NaH (54.03 mg, 1.35 mmol, 60% in mineral oil, 2 eq.) at 0° C. The mixture was stirred at 0° C. for 0.5 h. A solution of 3-bromoprop-1-yne (120.52 mg, 1.01 mmol, 87.34 µL, 1.5 eq.) in DMF (1 mL) was added dropwise into the reaction mixture, and the mixture was stirred at 0° C. for 0.5 h and at 20° C. for 0.5 h. TLC analysis (PE:EtOAc=2:1, R$_f$=0.3) indicated that the starting material was consumed completely. The reaction mixture was poured into water (10 mL) and extracted with EtOAc (10 mL×3). The combined organic layers were washed with brine (5 mL×3), dried over anhydrous sodium sulfate, filtered, and concentrated under reduced pressure to give a residue. The crude residue was purified by column chromatography (SiO$_2$, PE:EtOAc=10:1 to 2:1) to afford the desired product (0.24 g, 488.08 µmol, 72.26% yield) as a light yellow oil.

Preparation of 4-(methylsulfonyl)-N-(prop-2-yn-1-yl)-2-(trifluoromethoxy)aniline: A mixture of tert-butyl (4-(methylsulfonyl)-2-(trifluoromethoxy)phenyl)(prop-2-yn-1-yl)carbamate (0.05 g, 101.68 µmol, 1 eq.) and HCl/EtOAc (4 M, 2 mL, 78.68 eq.) was stirred at 20° C. for 2 h. HPLC analysis showed that the starting material was consumed completely, and one main peak was detected. The reaction mixture was concentrated under reduced pressure to give the desired product (0.03 g, crude, HCl) as a light yellow solid.

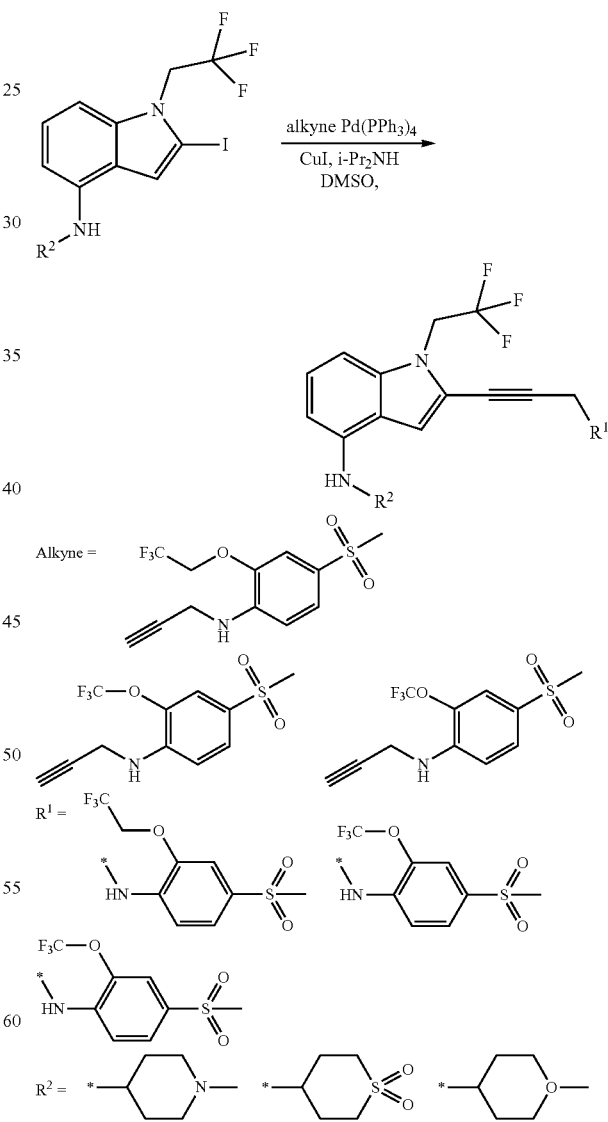

To a mixture of 4-(methylsulfonyl)-N-(prop-2-yn-1-yl)-2-(2,2,2-trifluoroethoxy)aniline (62.08 mg, 171.53 µmol, 1.5 eq.), 4-(methylsulfonyl)-N-(prop-2-yn-1-yl)-2-(trifluoromethoxy)aniline (50.01 mg, 138.16 μmol, 1.5 eq.), or 4-(methylsulfonyl)-N-(prop-2-yn-1-yl)-2-(trifluoromethoxy)aniline (29.93 mg, 90.76 μmol, 0.77 eq., HCl) in DMSO (1~10 mL) were added i-Pr₂NH (115.71 mg, 1.14 mmol, 161.61 L, 10 eq.), CuI (21.78 mg, 114.35 μmol, 1 eq.), 2-iodo-N—R²-1-(2,2,2-trifluoroethyl)-1H-indol-4-amine (50 mg, 114.35 μmol, 1 eq.), and Pd(PPh₃)₄ (26.43 mg, 22.87 μmol, 0.20 eq.) at 20~45° C. The mixture was stirred at 20~45° C. temperature for 1-4 h. TLC or LC-MS analysis was used to detect completion of the reaction. EtOAc (10 mL) was poured into the mixture, and the resulting mixture was poured into a saturated aqueous solution of EDTA (40 mL). The mixture was stirred for 15 min, and the aqueous phase was extracted with EtOAc (40 mL×2). The organic layer was poured into to a saturated aqueous solution of EDTA solution (40 mL) and stirred for 1 h. The aqueous phase was extracted with EtOAc (40 mL×3). The combined organic layers were washed with brine (40 mL×3), dried over anhydrous sodium sulfate, mixed with activated carbon, filtered, and concentrated in vacuo. The mixture was purified by prep-TLC or column chromatography, then purified again once or twice by prep-HPLC to afford the desired products.

N-(1-methylpiperidin-4-yl)-2-(3-((4-(methylsulfonyl)-2-(2,2,2-trifluoroethoxy)phenyl)amino)prop-1-yn-1-yl)-1-(2,2,2-trifluoroethyl)-1H-indol-4-amine, 24.7 mg, 31.7% yield, MS (ES³⁰, m/z): 617.2; 4-((2-(3-((4-(methylsulfonyl)-2-(2,2,2-trifluoroethoxy)phenyl)amino)prop-1-yn-1-yl)-1-(2,2,2-trifluoroethyl)-1H-indol-4-yl)amino)tetrahydro-2H-thiopyran 1,1-dioxide, 8.1 mg, 13.5% yield, MS (ES³⁰, m/z): 652.1; 2-(3-{[4-methanesulfonyl-2-(trifluoromethoxy)phenyl]amino}prop-1-yn-1-yl)-N-(oxan-4-yl)-1-(2,2,2-trifluoroethyl)-1H-indol-4-amine, 18.1 mg, 26.1% yield, MS (ES³⁰, m/z): 590.3; 2-(3-{[4-methanesulfonyl-2-(trifluoromethoxy)phenyl]amino}prop-1-yn-1-yl)-N-(1-methylpiperidin-4-yl)-1-(2,2,2-trifluoroethyl)-1H-indol-4-amine, 38.2 mg, 49.0% yield, MS (ES³⁰, m/z): 603.1; 4-{[2-(3-1{[4-methanesulfonyl-2-(trifluoromethoxy)phenyl]amino}prop-1-yn-1-yl)-1-(2,2,2-trifluoroethyl)-1H-indol-4-yl]amino}-1λ⁶-thiane-1,1-dione and, 16.7 mg, 24.7% yield, MS (ES³⁰, m/z): 638.1.

Example D77: Synthesis of Compounds 680A and 681A

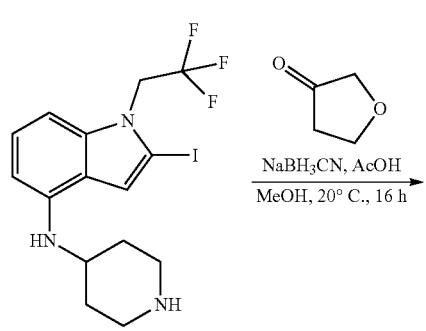

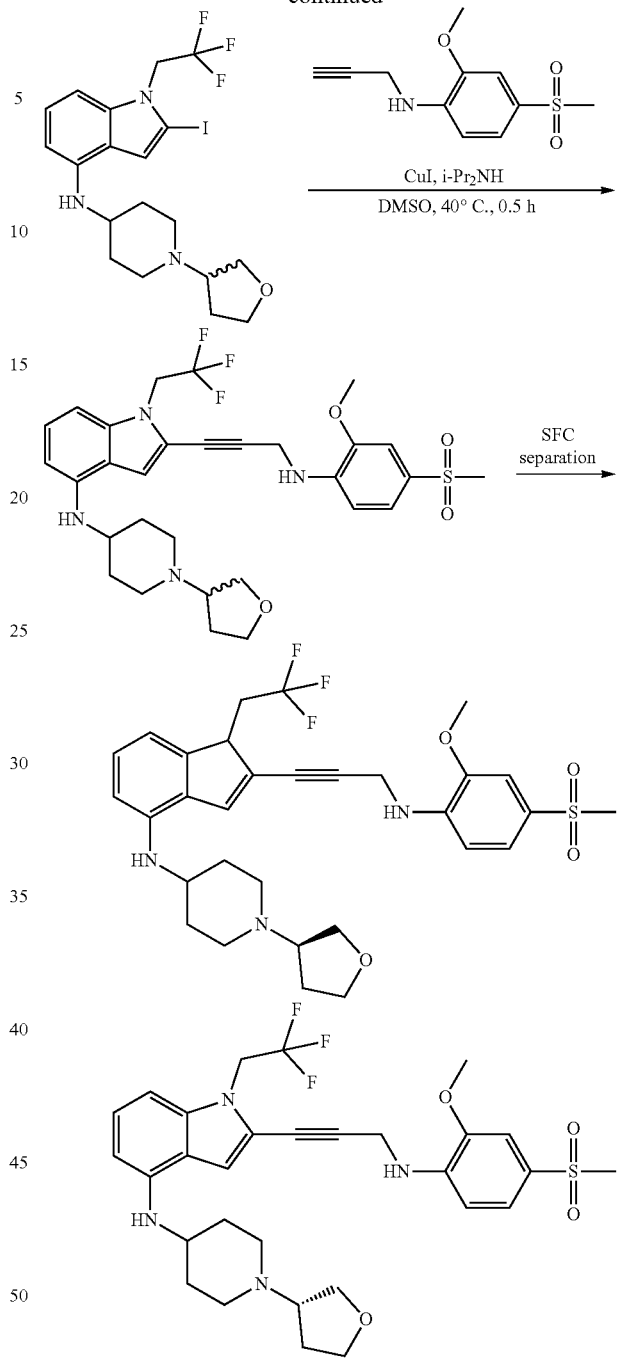

Preparation of 2-iodo-N-(1-(tetrahydrofuran-3-yl)piperidin-4-yl)-1-(2,2,2-trifluoroethyl)-1H-indol-4-amine: To a mixture of 2-iodo-N-(piperidin-4-yl)-1-(2,2,2-trifluoroethyl)-1H-indol-4-amine (10 g, 23.63 mmol, 1 eq.) and tetrahydrofuran-3-one (8.14 g, 94.51 mmol, 4 eq.) in MeOH (100 mL) were added NaBH₃CN (4.45 g, 70.89 mmol, 3 eq.) and AcOH (1.42 g, 23.63 mmol, 1.35 mL, 1 eq.). The mixture was stirred at 20° C. for 16 h. TLC analysis (R_f=0.6, EtOAc:TEA=10:1) showed that most of the starting material was consumed. The mixture was extracted with a saturated NaHCO₃ solution (300 mL) and EtOAc (350 mL×3). The organic layer was washed with brine (300 mL), dried over anhydrous sodium sulfate, filtered, and concentrated. The residue was purified by column chromatography (SiO$_2$, PE:EtOAc=3:1 to 0:1) to afford the desired product (8.3 g, 15.14 mmol, 64.09% yield) as an off-white solid.

Preparation of 2-iodo-N-(piperidin-4-yl)-1-(2,2,2-trifluoroethyl)-1H-indol-4-amine: A mixture of 2-iodo-N-(1-(tetrahydrofuran-3-yl)piperidin-4-yl)-1-(2,2,2-trifluoroethyl)-1H-indol-4-amine (6 g, 12.16 mmol, 1 eq.), 2-methoxy-4-methylsulfonyl-N-prop-2-ynyl-aniline (3.78 g, 15.81 mmol, 1.3 eq.), i-Pr$_2$NH (12.31 g, 121.63 mmol, 17.19 mL, 10 eq.), CuI (1.16 g, 6.08 mmol, 0.5 eq.), and Pd(PPh$_3$)$_4$ (1.41 g, 1.22 mmol, 0.1 eq.) in DMSO (60 mL) was degassed and purged with N$_2$ three times. The mixture was stirred at 20° C. for 1 h under N$_2$. TLC analysis (R$_f$=0.4, EtOAc:TEA=10:1) showed that the reaction was complete. Saturated aqueous EDTA (200 mL) and EtOAc (200 mL) were added to the mixture and stirred for 1 h. Then the mixture was extracted with EtOAc (200 mL×3). The organic layer was washed with brine (150 mL×3), dried over anhydrous sodium sulfate, filtered, and concentrated. The residue was purified by column chromatography (SiO$_2$, PE:EtOAc=3:1 to 0:1) and prep-HPLC. The purified residue was purified further by SFC to obtain the desired products.

(R)-2-(3-((2-methoxy-4-(methylsulfonyl)phenyl)amino)prop-1-yn-1-yl)-N-(1-(tetrahydrofuran-3-yl)piperidin-4-yl)-1-(2,2,2-trifluoroethyl)-1H-indol-4-amine (0.075 g, 124.03 μmol, 1.02% yield), MS (ES$^{3O}$, m/z): 605.3; (S)-2-(3-((2-methoxy-4-(methylsulfonyl)phenyl)amino)prop-1-yn-1-yl)-N-(1-(tetrahydrofuran-3-yl)piperidin-4-yl)-1-(2,2,2-trifluoroethyl)-1H-indol-4-amine (0.085 g, 140.57 μmol, 1.16% yield), MS (ES$^{3O}$, m/z): 605.3.

Example D78: Synthesis of Compounds 878A and 879A

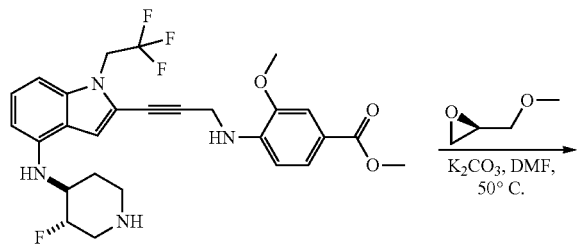

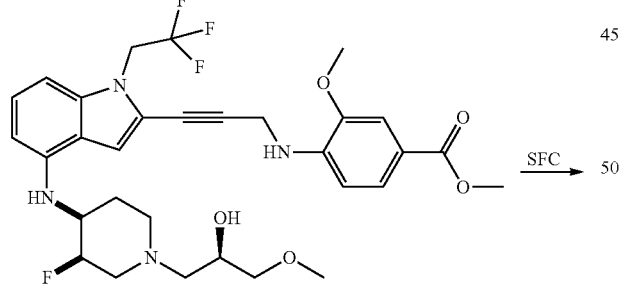

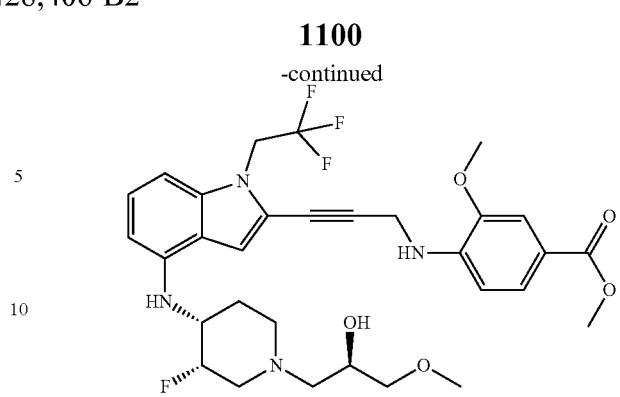

To a mixture of methyl 4-((3-(4-(((3S,4S)-3-fluoropiperidin-4-yl)amino)-1-(2,2,2-trifluoroethyl)-1H-indol-2-yl)prop-2-yn-1-yl)amino)-3-methoxybenzoate (0.15 g, 281.67 μmol, 1 eq.) and (2R)-2-(methoxymethyl)oxirane (124.08 mg, 1.41 mmol, 125.33 μL, 5 eq.) in DMF (5 mL) was added K$_2$CO$_3$ (116.79 mg, 845.02 μmol, 3 eq.). The mixture was stirred at 50° C. for 12 h. TLC analysis (EtOAc:TEA=10:1, R$_f$=0.75) detected one new spot. The reaction mixture was quenched by addition water (10 mL), and then extracted with EtOAc (10 mL×3). The combined organic layers were washed with brine (10 mL×3), dried over anhydrous sodium sulfate, filtered, and concentrated under reduced pressure to give a residue. The residue was purified by prep-HPLC to afford methyl 4-[3-[4-[[(3R,4S)-3-fluoro-1-[(2R)-2-hydroxy-3-methoxy-propyl]-4-piperidyl]amino]-1-(2,2,2-trifluoroethyl)indol-2-yl]prop-2-ynylamino]-3-methoxy-benzoate (0.07 g, 107.15 μmol, 38.04% yield) was obtained as a yellow solid.

The residue was separated by SFC to afford methyl 4-[3-[4-[[(3R,4S)-3-fluoro-1-[(2R)-2-hydroxy-3-methoxy-propyl]-4-piperidyl]amino]-1-(2,2,2-trifluoroethyl)indol-2-yl]prop-2-ynylamino]-3-methoxy-benzoate (0.03 g, 47.76 μmol, 41% yield). MS (ES$^{3O}$, m/z): 621.3. and methyl 4-[3-[4-[[(3S,4R)-3-fluoro-1-[(2R)-2-hydroxy-3-methoxy-propyl]-4-piperidyl]amino]-1-(2,2,2-trifluoroethyl)indol-2-yl]prop-2-ynylamino]-3-methoxy-benzoate (0.03 g, 46.69 μmol, 40% yield). MS (ES$^{3O}$, m/z): 621.4.

Example D79: Synthesis of Compounds 783A and 784A

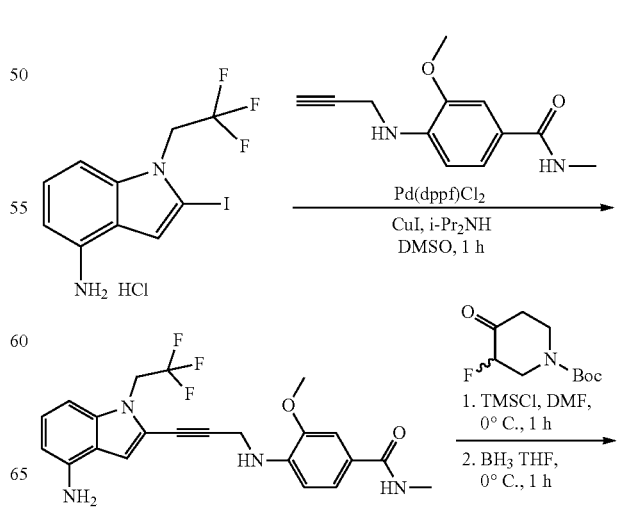

1101

-continued

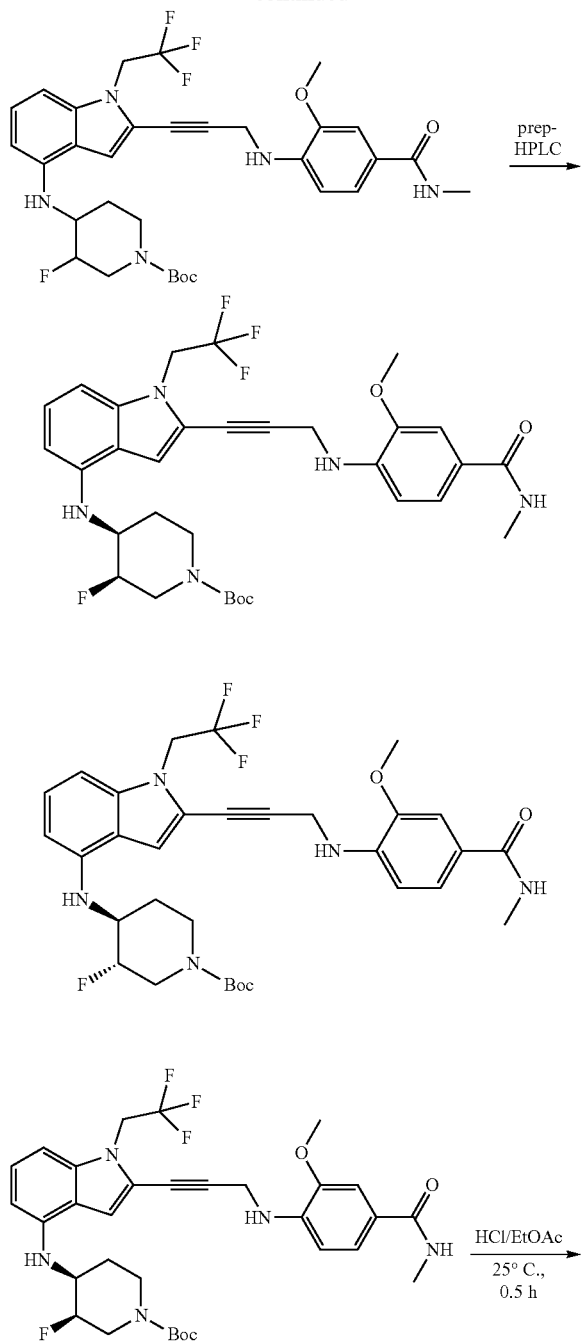

1102

-continued

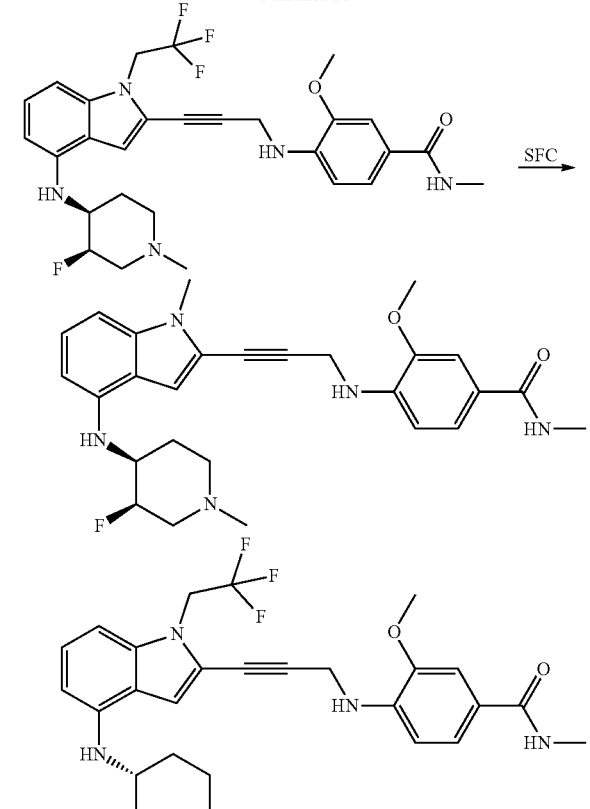

Preparation of 4-((3-(4-amino-1-(2,2,2-trifluoroethyl)-1H-indol-2-yl)prop-2-yn-1-yl)amino)-3-methoxy-N-methylbenzamide: A mixture of 2-iodo-1-(2,2,2-trifluoroethyl)-1H-indol-4-amine hydrochloride (1 g, 2.94 mmol, 1 eq.), 3-methoxy-N-methyl-4-(prop-2-yn-1-ylamino)benzamide (770.11 mg, 3.53 mmol, 1.2 eq.), CuI (560.01 mg, 2.94 mmol, 1 eq.), Pd(PPh$_3$)$_4$ (679.58 mg, 588.09 μmol, 0.2 eq.), and i-Pr$_2$NH (2.98 g, 29.40 mmol, 4.16 mL, 10 eq.) in DMSO (10 mL) was degassed and purged with N$_2$ three times. The mixture was stirred at 20° C. for 1 h under N$_2$. TLC analysis (PE:EtOAc=5:1, R$_f$=0; PE:EtOAc=0:1, R$_f$=0.5) indicated that one major new spot had formed. The reaction mixture was quenched by adding a saturated aqueous EDTA solution (40 mL) with stirring for 1 h. The mixture was diluted with EtOAc (20 mL), and extracted with EtOAc (20 mL×3). The combined organic layers were washed with brine (15 mL×3), dried over anhydrous sodium sulfate, filtered, and concentrated under reduced pressure to give a residue. The crude product was triturated with DCM at 20° C. for 10 min. The residue was purified by column chromatography (SiO$_2$, PE:EtOAc=2:1 to 0:1) to afford the desired product (1.1 g, 2.04 mmol, 69.53% yield) as a yellow solid.

Preparation of tert-butyl (3R,4S)-3-fluoro-4-((2-(3-((2-methoxy-4-(methylcarbamoyl)phenyl)amino)prop-1-yn-1-yl)-1-(2,2,2-trifluoroethyl)-1H-indol-4-yl)amino)piperidine-1-carboxylate: To a mixture of 4-((3-(4-amino-1-(2,2,2-trifluoroethyl)-1H-indol-2-yl)prop-2-yn-1-yl)amino)-3-methoxy-N-methylbenzamide (0.9 g, 2.09 mmol, 1 eq.) and tert-butyl 3-fluoro-4-oxopiperidine-1-carboxylate (2.27 g, 10.45 mmol, 5 eq.) in DMF (10 mL) was added TMSCl (567.92 mg, 5.23 mmol, 663.46 μL, 2.5 eq.) at 0° C. The

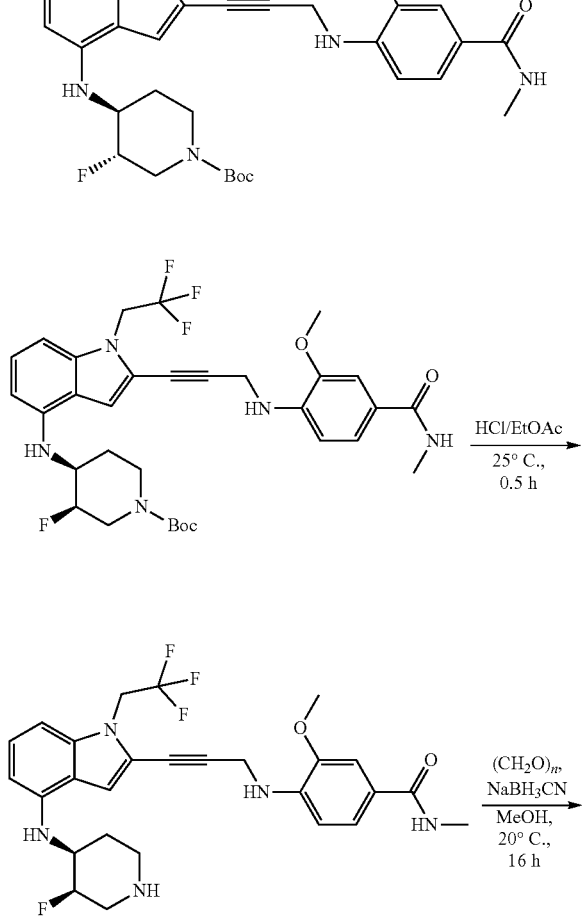

resulting mixture was stirred at 0° C. for 1 h, and BH₃·THF (1 M, 6.27 mL, 3 eq.) was added to the reaction at 0° C. The mixture was stirred further at 0° C. for 1 h. TLC analysis (PE:EtOAc=0:1, $R_f$=0.55) indicated that the starting material remained, and one new spot was detected. The reaction mixture was quenched by adding saturated aqueous Na₂CO₃ (30 mL), diluted with water (30 mL), and extracted with EtOAc (30 mL×3). The combined organic layers were washed with brine (30 mL×3), dried over anhydrous sodium sulfate, filtered, and concentrated under reduced pressure to give a residue. The residue was purified by column chromatography (SiO₂, PE:EtOAc=3:1 to 0:1) and prep-HPLC afford the desired product and tert-butyl (3S,4S)-3-fluoro-4-((2-(3-((2-methoxy-4-(methylcarbamoyl)phenyl)amino) prop-1-yn-1-yl)-1-(2,2,2-trifluoroethyl)-1H-indol-4-yl) amino)piperidine-1-carboxylate a yellow solid.

Preparation of 4-((3-(4-(((3R,4S)-3-fluoropiperidin-4-yl) amino)-1-(2,2,2-trifluoroethyl)-1H-indol-2-yl)prop-2-yn-1-yl)amino)-3-methoxy-N-methylbenzamide: A solution of tert-butyl (3R,4S)-3-fluoro-4-((2-(3-((2-methoxy-4-(methylcarbamoyl)phenyl)amino)prop-1-yn-1-yl)-1-(2,2,2-trifluoroethyl)-1H-indol-4-yl)amino)piperidine-1-carboxylate (0.65 g, 1.03 mmol, 1 eq.) in HCl/EtOAc (20 mL, 4 M) was stirred at 20° C. for 0.5 h under N₂. TLC analysis (DCM: MeOH=10:1, $R_f$=0.1) indicated that the starting material was consumed completely, and one new spot was detected. The reaction mixture was quenched by adding a saturated aqueous solution of NaHCO₃ (30 mL), diluting the mixture with water (30 mL), and extracted the mixture with EtOAc (40 mL×3). The combined organic layers were washed with brine (20 mL×3), dried over anhydrous sodium sulfate, filtered, and concentrated under reduced pressure to give a residue. The crude product (0.5 g, 846.59 μmol, 82.27% yield) was obtained as a yellow solid and used without purification.

Preparation of 4-((3-(4-(((3R,4S)-3-fluoro-1-methylpiperidin-4-yl)amino)-1-(2,2,2-trifluoroethyl)-1H-indol-2-yl) prop-2-yn-1-yl)amino)-3-methoxy-N-methylbenzamide: To a solution of 4-((3-(4-(((3R,4S)-3-fluoropiperidin-4-yl) amino)-1-(2,2,2-trifluoroethyl)-1H-indol-2-yl)prop-2-yn-1-yl)amino)-3-methoxy-N-methylbenzamide (169.49 mg, 5.64 mmol, 10 eq.) and paraformaldehyde (169.49 mg, 5.64 mmol, 10 eq.) in MeOH (3 mL) were added NaBH₃CN (106.40 mg, 1.69 mmol, 3 eq.) and AcOH (33.89 mg, 564.39 μmol, 32.28 μL, 1 eq.). The mixture was degassed and purged with N₂ three times, then was stirred at 20° C. for 12 h under N₂. TLC analysis (DCM:MeOH=10:1, $R_f$=0.6) indicated that the starting material remained, and one major new spot was detected. The reaction mixture was quenched by adding a saturated aqueous solution of Na₂CO₃ (30 mL), diluted with water (30 mL), and extracted with EtOAc (30 mL×3). The combined organic layers were washed with brine (20 mL×3), dried over anhydrous sodium sulfate, filtered, and concentrated under reduced pressure to give a residue. The residue was purified by prep-TLC (SiO₂, DCM: MeOH=10:1) to afford the desired product (0.11 g, 189.53 μmol, 33.58% yield) as a yellow solid.

The residue was separated by SFC to afford 4-[3-[4-[[(3R, 4S)-3-fluoro-1-methyl-4-piperidyl]amino]-1-(2,2,2-trifluoroethyl)indol-2-yl]prop-2-ynylamino]-3-methoxy-N-methyl-benzamide (0.06 g, 107.34 μmol, 45% yield) yellow solid. MS (ES³⁰, m/z): 546.3 and 4-[3-[4-[[(3S,4R)-3-fluoro-1-methyl-4-piperidyl]amino]-1-(2,2,2-trifluoroethyl) indol-2-yl]prop-2-ynylamino]-3-methoxy-N-methyl-benzamide (0.055 g, 98.90 μmol, 42% yield). MS (ES³⁰, m/z): 546.3.

Example D80: Synthesis of 4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-N-isopropyl-3-methoxybenzamide (Compound 807A)

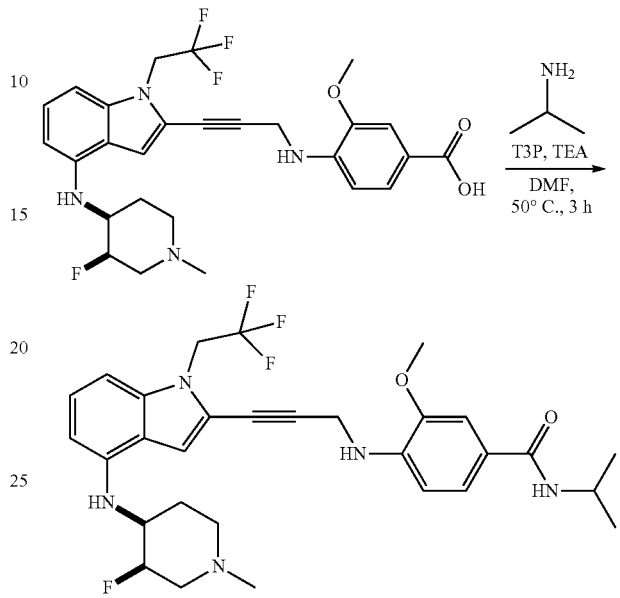

To a mixture of 4-((3-(4-(((3R,4S)-3-fluoro-1-methylpiperidin-4-yl)amino)-1-(2,2,2-trifluoroethyl)-1H-indol-2-yl) prop-2-yn-1-yl)amino)-3-methoxybenzoic acid (0.1 g, 187.78 μmol, 1 eq.), propan-2-amine (22.20 mg, 375.57 μmol, 32.27 μL, 2 eq.), TEA (114.01 mg, 1.13 mmol, 156.82 μL, 6 eq.) in DMF (3 mL) was added T3P® (358.49 mg, 563.35 μmol, 335.04 μL, 50% purity, 3 eq.). The mixture was stirred at 50° C. for 3 h under N₂. TLC analysis (DCM:MeOH=10:1, $R_f$=0.36) indicated that the starting material was consumed, and one major new spot was detected. The reaction mixture was quenched by adding water (30 mL) and extracted with EtOAc (20 mL×3). The combined organic layers were washed with brine (15 mL×3), dried over anhydrous sodium sulfate, filtered and concentrated under reduced pressure to give a residue. The residue was purified by prep-TLC (SiO₂, EtOAc:TEA=10:1) and purified further by prep-HPLC to afford 4-[3-[4-[[(3R, 4S)-3-fluoro-1-methyl-4-piperidyl]amino]-1-(2,2,2-trifluoroethyl)indol-2-yl]prop-2-ynylamino]-N-isopropyl-3-methoxy-benzamide (0.04 g, 68.97 μmol, 37% yield) white solid. MS (ES³⁰, m/z): 574.2.

Example D81: Synthesis of (4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoyl)glycine (Compound 896A)

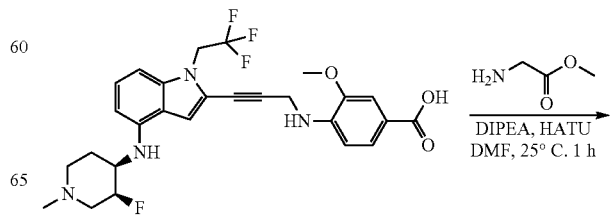

1105

-continued

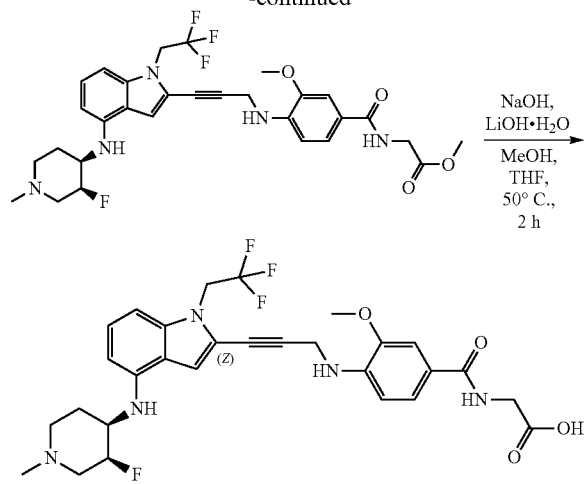

NaOH,
LiOH·H₂O
——————→
MeOH,
THF,
50° C.,
2 h

Preparation of (4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoyl)glycine: To a mixture of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoic acid (0.1 g, mmol, 1 eq.) and methyl 2-aminoacetate hydrochloride (35.71 mg, 220.38 μmol, 1.2 eq., HCl) in DMF (2 mL) were added DIPEA (71.21 mg, 3 eq.) and HATU (104.75 mg, 1.5 eq.) in one portion at 25° C. under N₂. The mixture was stirred at 25° C. for 1 h. TLC analysis (DCM:MeOH=10:1, R$_f$=0.4) showed that the reaction was complete. The residue was poured into water (10 mL), and the aqueous phase was extracted with EtOAc (10 mL×3). The combined organic layers were washed with brine (10 mL×1), dried over anhydrous sodium sulfate, filtered, and concentrated in vacuo. The crude product (0.1 g, crude) was obtained as light yellow solid and used in the next step without purification.

Preparation of methyl (4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoyl)glycinate: To a solution of (4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoyl)glycine (80 mg, 132.54 μmol, 1 eq.) in THF (1 mL), water (1 mL), and MeOH (1 mL) were added NaOH (10.60 mg, 265.07 μmol, 2 eq.) and LiOH·H₂O (11.12 mg, 265.07 mol, 2 eq.). The mixture was stirred at 50° C. for 2 h. TLC analysis (DCM:MeOH=10:1, R$_f$=0.1) showed that the reaction was complete. The residue was poured into water (10 mL), and 1M aqueous HCl was added to the mixture to adjust the pH to 5. The aqueous phase was extracted with EtOAc (10 mL×3). The combined organic layers were washed with brine (10 mL×1), dried over anhydrous sodium sulfate, filtered, and concentrated in vacuo. The residue was purified by prep-HPLC to give the desired product as a light yellow solid (44%). MS (ES³⁰, m/z): 590.2.

1106

Example D82: Synthesis of Compounds 906A, 907A, 917A, and 962A

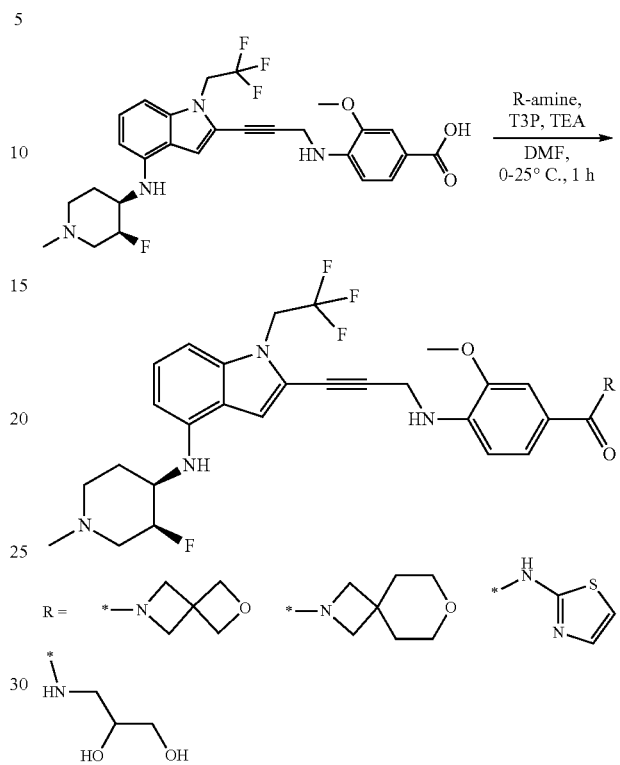

R-amine,
T3P, TEA
——————→
DMF,
0-25° C., 1 h

To a mixture of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoic acid (80 mg, 146.92 μmol, 1 eq.) R-amine (33.35 mg, 176.31 μmol, 1.2 eq.) and TEA (74.34 mg, 734.61 μmol, 102.25 μL, 5 eq.) in DMF (3 mL) was added T3P® (140.24 mg, 220.38 μmol, 131.07 μL, 50% purity, 1.5 eq.) dropwise at 0° C. under N₂. The mixture was stirred at 25° C. for 1 h. TLC analysis indicated that the starting material was consumed completely, and one new spot was detected. The reaction mixture was quenched by adding water (5 mL) and extracted with EtOAc (5 mL×3). The combined organic layers were washed with brine (5 mL×3), dried over anhydrous sodium sulfate, filtered, and concentrated under reduced pressure to give a residue. The residue was purified by prep-HPLC to give the desired products as yellow solids.

N-[(3S,4R)-3-fluoro-1-methylpiperidin-4-yl]-2-{3-[(2-methoxy-4-{2-oxa-6-azaspiro[3.3]heptane-6-carbonyl}phenyl)amino]prop-1-yn-1-yl}-1-(2,2,2-trifluoroethyl)-1H-indol-4-amine, (28.3 mg, 36.9% yield) MS (ES³⁰, m/z): 614.3; N-[(3S,4R)-3-fluoro-1-methylpiperidin-4-yl]-2-{3-[(2-methoxy-4-{7-oxa-2-azaspiro[3.5]nonane-2-carbonyl}phenyl)amino]prop-1-yn-1-yl}-1-(2,2,2-trifluoroethyl)-1H-indol-4-amine, (13.7 mg, 13.9% yield) MS (ES³⁰, m/z): 642.3; N-(2,3-dihydroxypropyl)-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide, (32.7 mg, 36.5% yield) MS (ES³⁰, m/z): 606.3; 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(1,3-thiazol-2-yl)benzamide, (13.7 mg, 14.9% yield) MS (ES³⁰, m/z): 615.2.

Example D83: Synthesis of Compounds 957A, 960A, and 963A

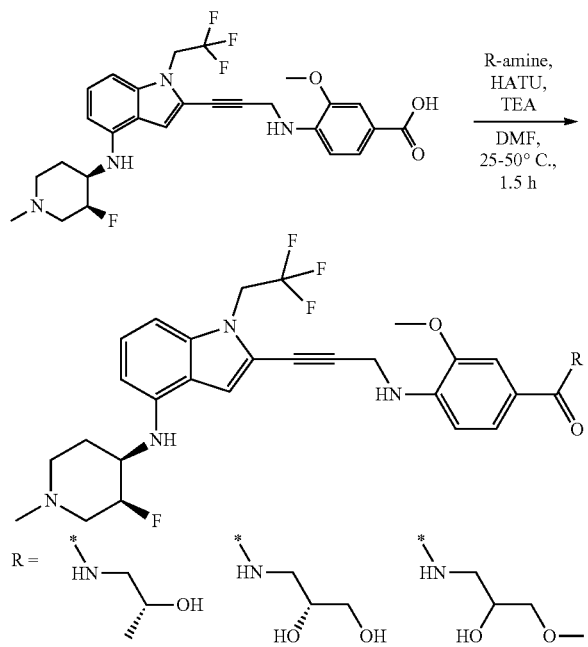

To a solution of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoic acid (70 mg, 130 μmol, 1 eq.) and Amines (19.53 mg, 260 μmol, 20.47 μL, 2 eq.) in DMF (2 mL) were added $Et_3N$ (39.46 mg, 390.01 mol, 54.28 μL, 3 eq.) and HATU (74.15 mg, 195 μmol, 1.5 eq.) in one portion at 25° C. under $N_2$. The mixture was stirred for 0.5 h, and R-amine (2 eq.) was added. The resulting reaction mixture was stirred at 50° C. for 1 h. TLC analysis indicated that the starting material was consumed completely, and one new spot was detected. The reaction mixture was quenched with water (5 mL) and extracted with EtOAc (5 mL×3). The combined organic layers were washed with brine (5 mL×3), dried over anhydrous sodium sulfate, filtered, and concentrated under reduced pressure to give a residue. The residue was purified by prep-HPLC to give the desired products as yellow solids.

4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-N—((R)-2-hydroxypropyl)-3-methoxybenzamide, (28.8 mg, 37.1% yield), MS ($ES^{30}$, m/z): 590.2; N-[(2R)-2,3-dihydroxypropyl]-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide, (32.7 mg, 47.0% yield), MS ($ES^{30}$, m/z): 606.2; 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(2-hydroxy-3-methoxypropyl)-3-methoxybenzamide, (34.3 mg, 49.4% yield). MS ($ES^{30}$, m/z): 620.3.

Example D84: Synthesis of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxy-N-((2R,3R,4R,5S,6R)-2,4,5-trihydroxy-6-(hydroxymethyl)tetrahydro-2H-pyran-3-yl)benzamide (Compound 948A)

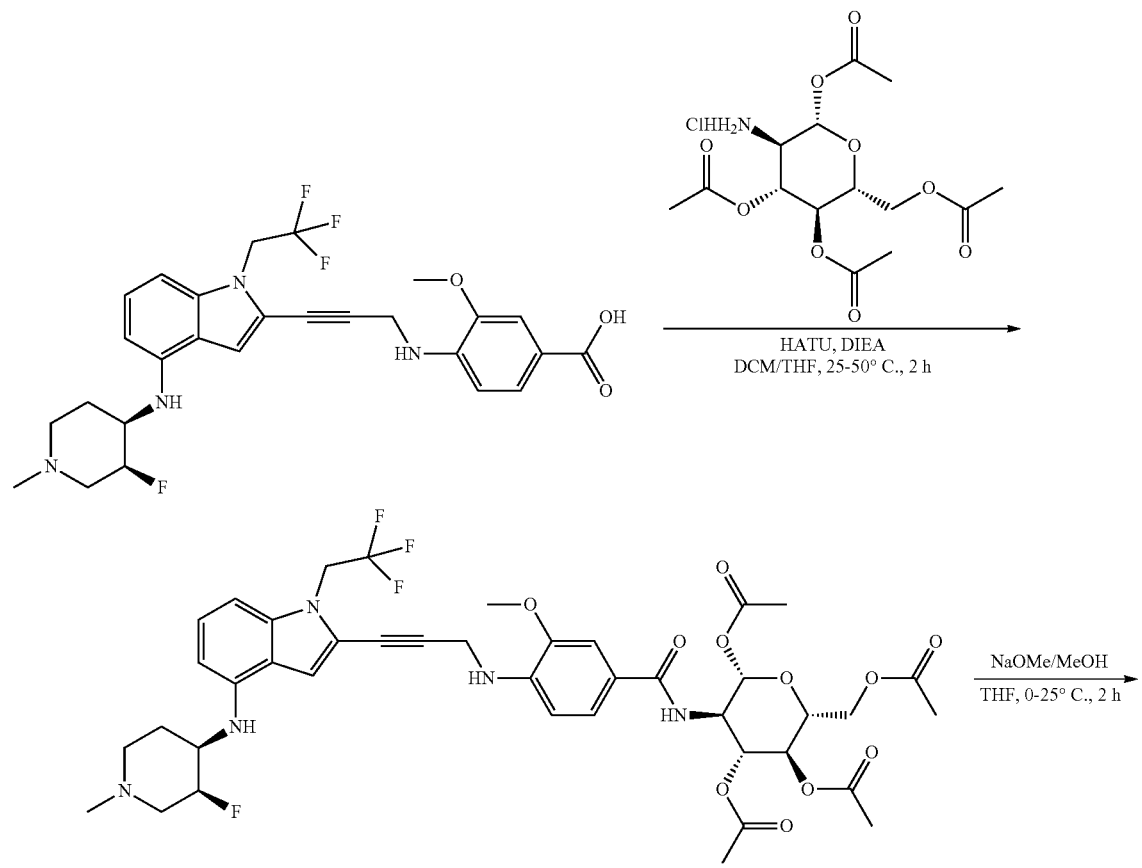

-continued

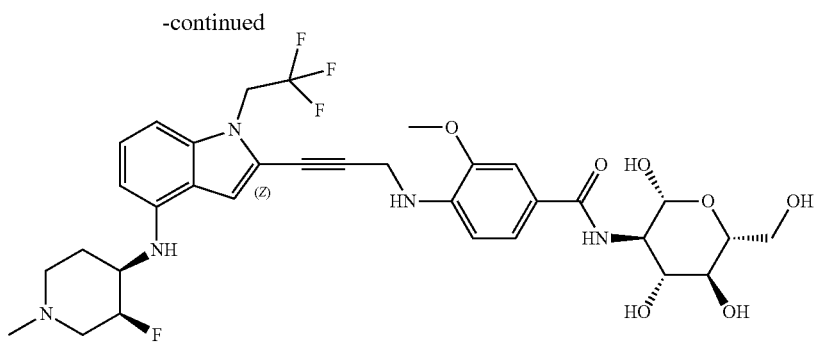

Preparation of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxy-N-((2R,3R,4R,5S,6R)-2,4,5-trihydroxy-6-(hydroxymethyl)tetrahydro-2H-pyran-3-yl)benzamide: To a solution of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoic acid (0.1 g, 183.65 μmol, 1 eq.) in $CH_2Cl_2$ (0.5 mL) and THF (0.5 mL) were added DIPEA (118.68 mg, 918.26 μmol, 159.94 μL, 5 eq.), HATU (139.66 mg, 367.30 μmol, 2 eq.), and [(2R,3S,4R,5R,6S)-3,4,6-triacetoxy-5-aminotetrahydropyran-2-yl]mEtOAc hydrochloride (154.36 mg, 367.30 μmol, 2 eq., HCl) at 25° C. under $N_2$. The mixture was stirred at 50° C. for 2 h. LC-MS analysis showed that the reaction was complete. The residue was poured into water (10 mL), and the aqueous phase was extracted with EtOAc (10 mL×3). The combined organic layers were washed with brine (10 mL×1), dried over anhydrous sodium sulfate, filtered, and concentrated in vacuo. The residue was purified by prep-TLC ($SiO_2$, DCM:MeOH=20:1, $R_f$=0.4) to give the desired product (150 mg, 147.94 μmol, 80.55% yield) as a light yellow solid.

Preparation of (2S,3R,4R,5S,6R)-6-(acetoxymethyl)-3-(4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzamido)tetrahydro-2H-pyran-2,4,5-triyl triacetate: To a solution of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxy-N-((2R,3R,4R,5S,6R)-2,4,5-trihydroxy-6-(hydroxymethyl)tetrahydro-2H-pyran-3-yl)benzamide (140 mg, 138.08 μmol, 1 eq.) in THF (10 mL) and MeOH (30 mL) was added NaOMe (2.98 g, 13.81 mmol, 4 mL, 25% purity, 100 eq.) at 0° C. The mixture was stirred at 25° C. for 2 h. LC-MS analysis showed that the reaction was complete. The reaction mixture was adjusted to pH 5 by adding citric acid (100 mL) dropwise and was then lyophilized. The residue was purified by prep-HPLC to give the desired product (26.9 mg, 37.62 μmol, 1 eq.) as a light yellow solid. MS ($ES^{30}$, m/z): 694.3.

Example D85: Synthesis of Compounds 790A, 791A, 837A, 838A, 841A, 842A, 843A, and 844A

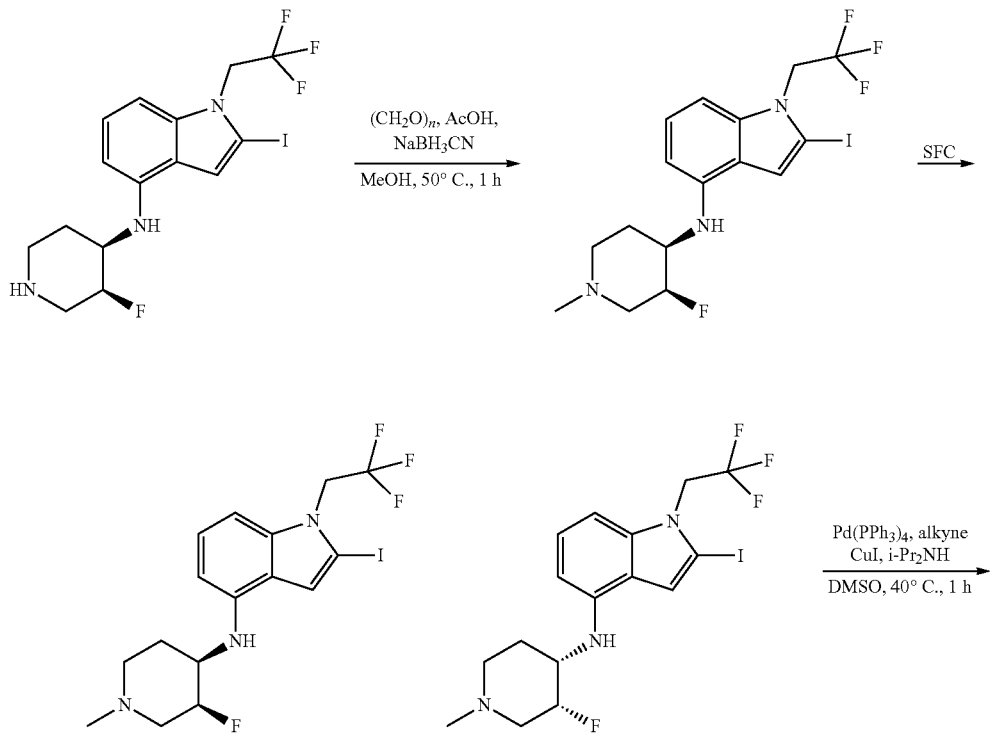

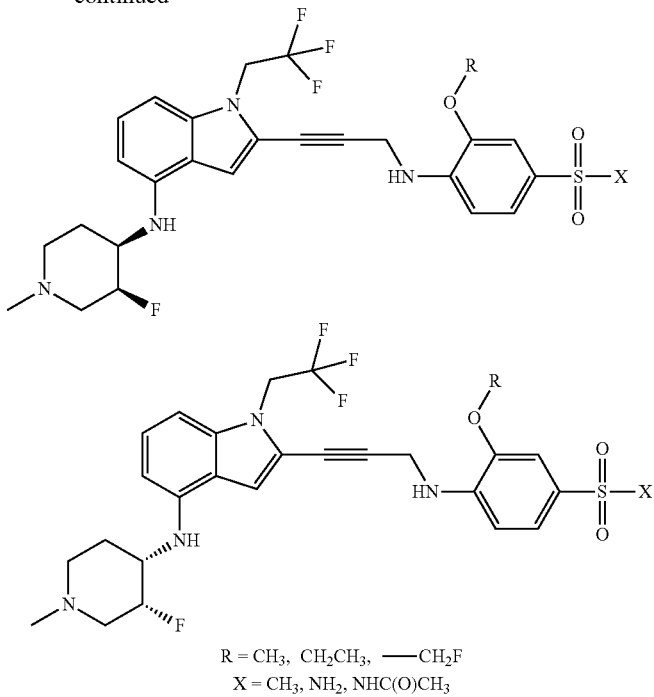

R = CH₃, CH₂CH₃, —CH₂F
X = CH₃, NH₂, NHC(O)CH₃

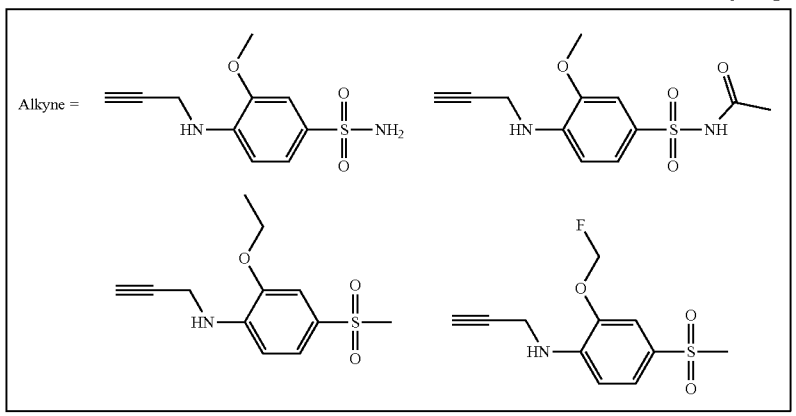

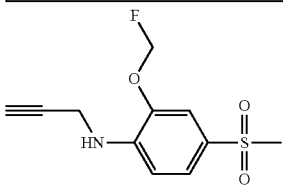

Preparation of N-((3S,4R)-3-fluoro-1-methylpiperidin-4-yl)-2-iodo-1-(2,2,2-trifluoroethyl)-1H-indol-4-amine and N-((3R,4S)-3-fluoro-1-methylpiperidin-4-yl)-2-iodo-1-(2,2,2-trifluoroethyl)-1H-indol-4-amine: To a mixture of N-((3S,4R)-3-fluoropiperidin-4-yl)-2-iodo-1-(2,2,2-trifluoroethyl)-1H-indol-4-amine (4.5 g, 10.20 mmol, 1 eq.) and formaldehyde (1.53 g, 51 mmol, 1.40 mL, 5 eq.) in MeOH (70 mL) was added AcOH (612.49 mg, 10.20 mmol, 583.33 μL, 1 eq.) dropwise at 25° C. Then, NaBH₃CN (1.28 g, 20.40 mmol, 2 eq.) was added to the mixture. The mixture was stirred at 50° C. for 1 h. TLC analysis indicated that the starting material was consumed completely, and one new spot was detected. The mixture was poured into a saturated aqueous solution of Na₂CO₃ (500 mL), and the mixture was stirred at 25° C. for 0.5 h. The mixture was extracted with EtOAc (200 mL×3). The combined organic layers were washed with brine (200 mL×3), dried over anhydrous sodium sulfate, filtered, and concentrated to give the residue. The crude residue was purified by column chromatography (SiO₂, PE:EtOAc=3:1 to 2:1 to EtOAc:MeOH:TEA=10:1:0.1) to give N-((3S,4R)-3-fluoro-1-methylpiperidin-4-yl)-2-iodo-1-(2,2,2-trifluoroethyl)-1H-indol-4-amine as a white solid (3.9 g, 78.9% yield).

N-((3S,4R)-3-fluoro-1-methylpiperidin-4-yl)-2-iodo-1-(2,2,2-trifluoroethyl)-1H-indol-4-amine was separated by SFC to afford the desired products. N-((3S,4R)-3-fluoro-1-methylpiperidin-4-yl)-2-iodo-1-(2,2,2-trifluoroethyl)-1H-indol-4-amine, (1.7 g, 42.9% yield); and N-((3R,4S)-3-fluoro-1-methylpiperidin-4-yl)-2-iodo-1-(2,2,2-trifluoroethyl)-1H-indol-4-amine, (1.8 g, 43.9% yield).

Preparation of final products: To a solution of 3-methoxy-4-(prop-2-yn-1-ylamino)benzenesulfonamide; N-((3-methoxy-4-(prop-2-yn-1-ylamino)phenyl)sulfonyl)acetamide; 2-ethoxy-4-(methylsulfonyl)-N-(prop-2-yn-1-yl)aniline (71.23 mg, 253.06 μmol, 1.2 eq.); or 2-(fluoromethoxy)-4-(methylsulfonyl)-N-(prop-2-yn-1-yl)aniline (67.82 mg, 263.60 μmol, 1.2 eq.) in DMSO (4 mL) were added i-Pr$_2$NH (129.85 mg, 2.20 mmol, 188.73 μL, 10 eq.), CuI (8.37 mg, 43.93 μmol, 0.2 eq.), N-((3S,4R)-3-fluoro-1-methylpiperidin-4-yl)-2-iodo-1-(2,2,2-trifluoroethyl)-1H-indol-4-amine (0.1 g, 219.67 μmol, 1 eq.) or N-((3R,4S)-3-fluoro-1-methylpiperidin-4-yl)-2-iodo-1-(2,2,2-trifluoroethyl)-1H-indol-4-amine (0.1 g, 219.67 μmol, 1 eq.) and Pd(PPh$_3$)$_4$ (12.69 mg, 10.98 μmol, 0.05 eq.). The mixture was stirred at 40° C. for 1 h. TLC analysis indicated that the starting material was consumed completely, and one new spot was detected. The reaction mixture was quenched by adding a saturated aqueous EDTA solution (30 mL) and was stirred at 20° C. for 1 h. The mixture was then diluted with water (20 mL) and extracted with EtOAc (30 mL×3). The combined organic layers were washed with brine (25 mL×3), dried over anhydrous sodium sulfate, filtered, and concentrated under reduced pressure to give a residue. The residue was purified by prep-TLC (SiO$_2$, DCM:MeOH=10:1) and prep-HPLC to afford the desired products. residue was purified by prep-TLC (SiO$_2$, DCM:MeOH=10:1) and prep-HPLC to afford the desired products.

4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonamide, 28 mg, 25% yield, MS (ES$^{30}$, m/z): 568.3; 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonamide, 28.1 mg, 23% yield, MS (ES$^{30}$, m/z): 568.3; N-(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzenesulfonyl)acetamide, 30 mg, 21% yield, MS (ES$^{30}$, m/z): 610.2; N-(4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzenesulfonyl)acetamide, 30 mg, 21% yield, MS (ES$^{30}$, m/z): 610.2; 2-{3-[(2-ethoxy-4-methanesulfonylphenyl)amino]prop-1-yn-1-yl}-N-[(3S,4R)-3-fluoro-1-methylpiperidin-4-yl]-1-(2,2,2-trifluoroethyl)-1H-indol-4-amine, 22 mg, 18% yield, MS (ES$^{30}$, m/z): 581.1; 2-{3-[(2-ethoxy-4-methanesulfonylphenyl)amino]prop-1-yn-1-yl}-N-[(3R,4S)-3-fluoro-1-methylpiperidin-4-yl]-1-(2,2,2-trifluoroethyl)-1H-indol-4-amine, 38 mg, 25% yield, MS (ES$^{30}$, m/z): 581.1; N-[(3S,4R)-3-fluoro-1-methylpiperidin-4-yl]-2-(3-{[2-(fluoromethoxy)-4-methanesulfonylphenyl]amino}prop-1-yn-1-yl)-1-(2,2,2-trifluoroethyl)-1H-indol-4-amine, 35 mg, 27% yield, MS (ES$^{30}$, m/z): 585.3; and N-[(3R,4S)-3-fluoro-1-methylpiperidin-4-yl]-2-(3-{[2-(fluoromethoxy)-4-methanesulfonylphenyl]amino}prop-1-yn-1-yl)-1-(2,2,2-trifluoroethyl)-1H-indol-4-amine, 34.0 mg, MS (ES$^{30}$, m/z): 585.3.

Example D86: Synthesis of Compounds 924A, 933A, 949A, 956A, and 969A

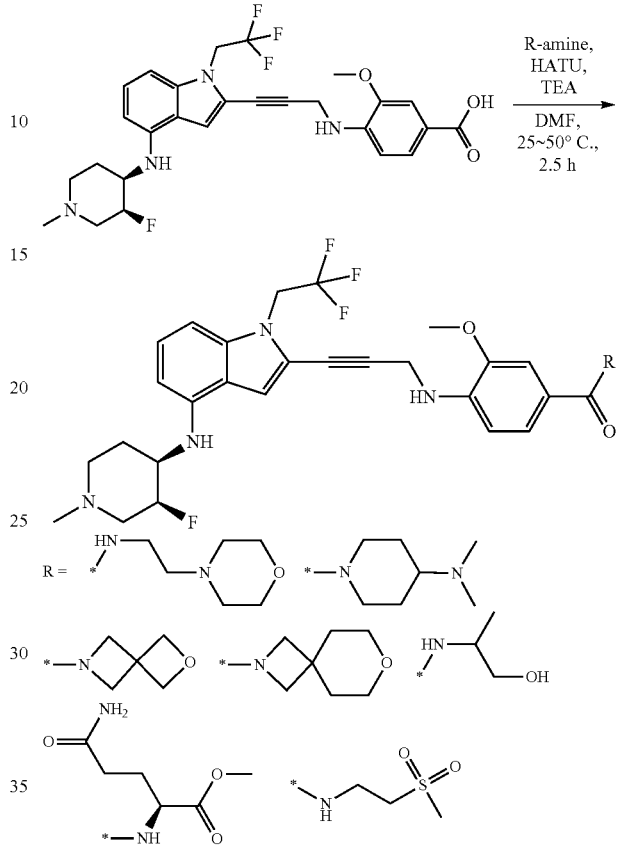

To a solution of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoic acid (0.07 g, 127.50 μmol, 1 eq.) in DMF (2 mL) were added 2-morpholinoethanamine (33.20 mg, 255 μmol, 33.47 μL, 2 eq.), HATU (42.84 mg, 112.67 μmol, 1.2 eq.), and TEA (95.01 mg, 938.92 μmol, 130.69 μL, 10 eq.). The mixture was stirred at 25~50° C. for 2-3 h. TLC analysis (DCM:MeOH=10:1, R$_f$=0.30) indicated that the starting material was consumed completely, and one new spot was detected. The reaction mixture was quenched by adding water (15 mL) and extracted with EtOAc (15 mL×3). The combined organic layers were washed with brine (10 mL×1), dried over anhydrous sodium sulfate, filtered, and concentrated under reduced pressure. The residue was purified by prep-HPLC to afford the desired products as yellow solids.

2-[3-({4-[4-(dimethylamino)piperidine-1-carbonyl]-2-methoxyphenyl}amino)prop-1-yn-1-yl]-N-[(3S,4R)-3-fluoro-1-methylpiperidin-4-yl]-1-(2,2,2-trifluoroethyl)-1H-indol-4-amine, 38.0 mg 44.1% yield, MS (ES$^{30}$, m/z): 643.3; 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-[2-(morpholin-4-yl)ethyl]benzamide, 25.0 mg 41.1% yield, MS (ES$^{30}$, m/z): 645.4; 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-N-(1-hydroxypropan-2-yl)-3-methoxybenzamide, 40.0 mg, MS (ES$^{30}$, m/z): 590.3; methyl (2S)-4-carbamoyl-2-[(4-{[3-

(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]butanoate, 3.0 mg MS (ES³⁰, m/z): 675.3; and 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(2-methanesulfonylethyl)-3-methoxybenzamide, 25.7% yield, MS (ES³⁰, m/z): 638.1. [4-[3-[4-[[(3S,4R)-3-fluoro-1-methyl-4-piperidyl]amino]-1-(2,2,2-trifluoroethyl)indol-2-yl]prop-2-ynylamino]-3-methoxy-phenyl]-(2-oxa-6-azaspiro[3.3]heptan-6-yl)methanone (0.02 g, 32.23 μmol, 79% yield), MS (ES³⁰, m/z): 614.3. Compound [4-[3-[4-[[(3S,4R)-3-fluoro-1-methyl-4-piperidyl]amino]-1-(2,2,2-trifluoroethyl)indol-2-yl]prop-2-ynylamino]-3-methoxy-phenyl]-(7-oxa-2-azaspiro[3.5]nonan-2-yl)methanone (0.025 g, 38.96 μmol, 42% yield) was obtained as a yellow solid. MS (ES³⁰, m/z): 642.3.

Example D87: Synthesis of Compounds 812A and 813A

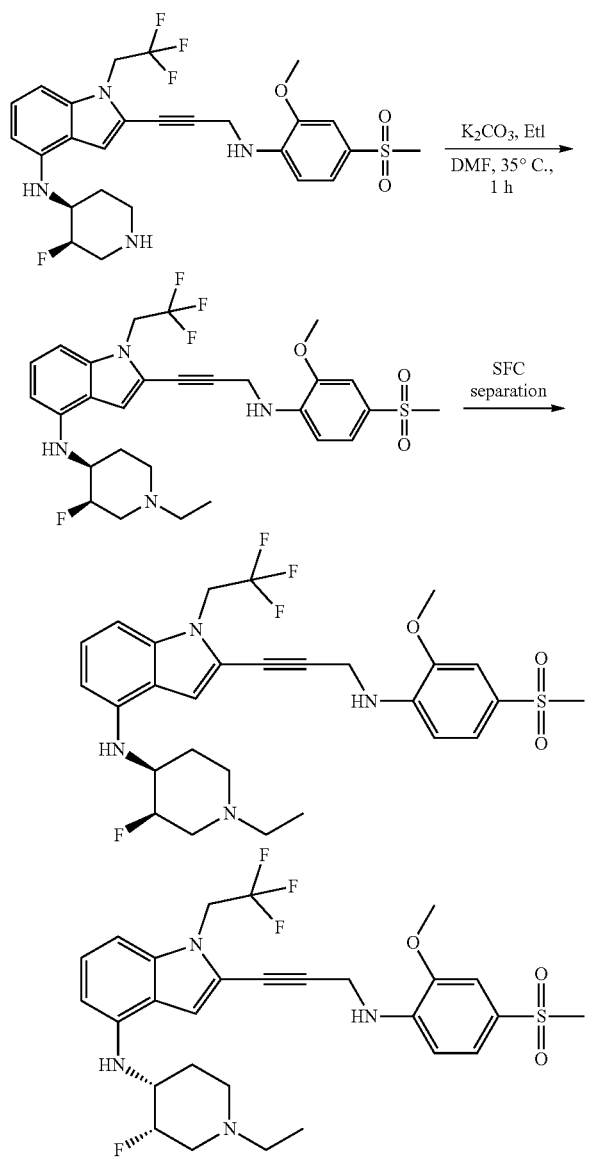

Preparation of N-((3R,4S)-1-ethyl-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine:

To a solution of N-((3R,4S)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine (150 mg, 271.45 μmol, 1 eq.) in DMF (2 mL) was added K₂CO₃ (112.55 mg, 814.36 μmol, 3 eq.) and iodoethane (84.67 mg, 542.90 μmol, 43.42 μL, 2 eq.). The reaction mixture was stirred at 35° C. for 1 h. LC-MS analysis showed that the starting material was consumed completely, and one main peak with desired the desired mass was observed. The reaction mixture was quenched by adding a saturated solution of NaHCO₃ (20 mL) at 25° C. and then extracted with EtOAc (20 mL). The combined organic layers were dried over anhydrous sodium sulfate, filtered, and concentrated in vacuo. The crude residue was purified by prep-TLC (DCM:MeOH=10:1) and prep-HPLC to afford the desired product (100 mg, 172.22 μmol, 63% yield) as a white solid. MS (ES³⁰, m/z): 581.3.

N-((3R,4S)-1-ethyl-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine was purified by SFC to obtain the final desired products as white solids. N-[(3R,4S)-1-ethyl-3-fluoropiperidin-4-yl]-2-{3-[(4-methanesulfonyl-2-methoxyphenyl)amino]prop-1-yn-1-yl}-1-(2,2,2-trifluoroethyl)-1H-indol-4-amine (19 mg, 32.72 μmol, 1 eq.), MS (ES³⁰, m/z): 581.3; and N-[(3S,4R)-1-ethyl-3-fluoropiperidin-4-yl]-2-{3-[(4-methanesulfonyl-2-methoxyphenyl)amino]prop-1-yn-1-yl}-1-(2,2,2-trifluoroethyl)-1H-indol-4-amine, (19 mg, 32.72 μmol, 1 eq.), MS (ES³⁰, m/z): 581.3.

Example D88: Synthesis of 2-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)acetamide (Compound 916A)

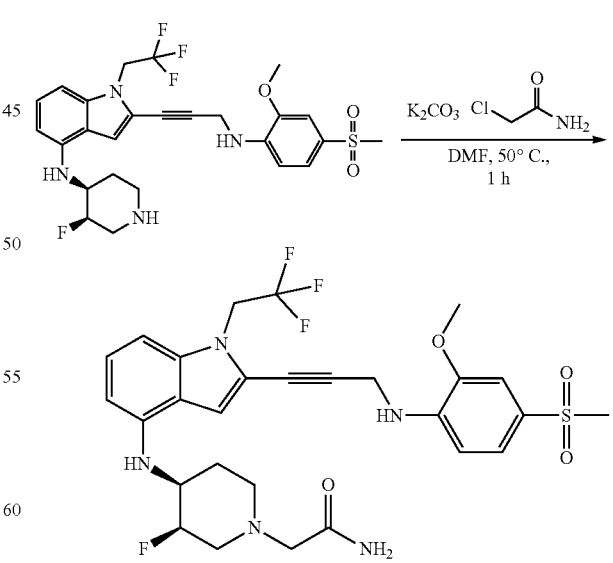

To a solution of N-((3R,4S)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine (150 mg, 271.45 μmol, 1 eq.) in DMF (1 mL) were added K₂CO₃

(112.55 mg, 814.36 µmol, 3 eq.) and 2-chloroacetamide (76.15 mg, 814.36 µmol, 57.90 µL, 3 eq.). The reaction mixture was stirred at 50° C. for 1 h. LC-MS analysis showed that the starting material was consumed completely, and one main peak with the desired mass was observed. The reaction mixture was filtered and concentrated in vacuo and purified by prep-HPLC to obtain the desired product (25 mg, 40.60 µmol) as a white solid. MS (ES$^{30}$, m/z): 610.2.

Example D89: Synthesis of Compounds 808A, 819A, 909A, 910A, 918A, 919A, 924A, and 947A

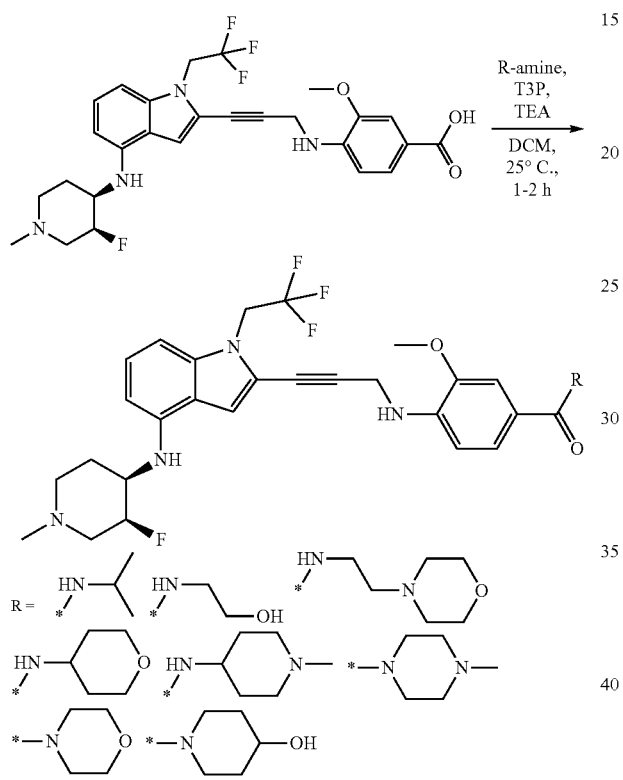

To a mixture of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoic acid (0.07 g, 127.50 µmol, 1 eq.), 1-methylpiperidin-4-amine (29.12 mg, 255.01 µmol, 25.96 µL, 2 eq.), TEA (129.02 mg, 1.28 mmol, 177.47 µL, 10 eq.) in DMF (3 mL) was added T3P® (243.42 mg, 382.51 µmol, 227.49 µL, 50% purity, 3 eq.). The mixture was stirred at 25~50° C. for 2 h under $N_2$. TLC analysis indicated that the starting material was consumed completely, and one new spot was detected. The reaction mixture was quenched by adding water (5 mL) and extracted with EtOAc (5 mL×3). The combined organic layers were washed with brine (5 mL×3), dried over anhydrous sodium sulfate, filtered, and concentrated under reduced pressure to give a residue. The residue was purified by prep-HPLC to afford the desired products as yellow solids.

4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(propan-2-yl)benzamide, 20.0 mg, 18% yield, MS (ES$^{30}$, m/z): 574.4; 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(2-hydroxyethyl)-3-methoxybenzamide, 3.0 mg, 3.8% yield, MS (ES$^{30}$, m/z): 576.3; 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-[2-(morpholin-4-yl)ethyl]benzamide, 25 mg, 12% yield, MS (ES$^{30}$, m/z): 645.4; 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(oxan-4-yl)benzamide, 50 mg, 54% yield, MS (ES$^{30}$, m/z): 616.3; 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(1-methylpiperidin-4-yl)benzamide, 35.0 mg, 42% yield, MS (ES$^{30}$, m/z): 629.3; N-[(3S,4R)-3-fluoro-1-methylpiperidin-4-yl]-2-(3-{[2-methoxy-4-(4-methylpiperazine-1-carbonyl)phenyl]amino}prop-1-yn-1-yl)-1-(2,2,2-trifluoroethyl)-1H-indol-4-amine, 45 mg, 53% yield, MS (ES$^{30}$, m/z): 615.4; N-[(3S,4R)-3-fluoro-1-methylpiperidin-4-yl]-2-(3-{[2-methoxy-4-(morpholine-4-carbonyl)phenyl]amino}prop-1-yn-1-yl)-1-(2,2,2-trifluoroethyl)-1H-indol-4-amine, 45 mg, 56% yield, MS (ES$^{30}$, m/z): 602.3 and 1-(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoyl)piperidin-4-ol, 31 mg, 30% yield, MS (ES$^{30}$, m/z): 616.3.

Example D90: Synthesis of 3-methoxy-4-{[3-(4-{[1-(2-methoxyethyl)piperidin-4-yl]amino}-1-(2,2,2-trifluoroethyl)-1H-indol-2-yl)prop-2-yn-1-yl]amino}-N-methylbenzene-1-sulfonamide (Compound 617A)

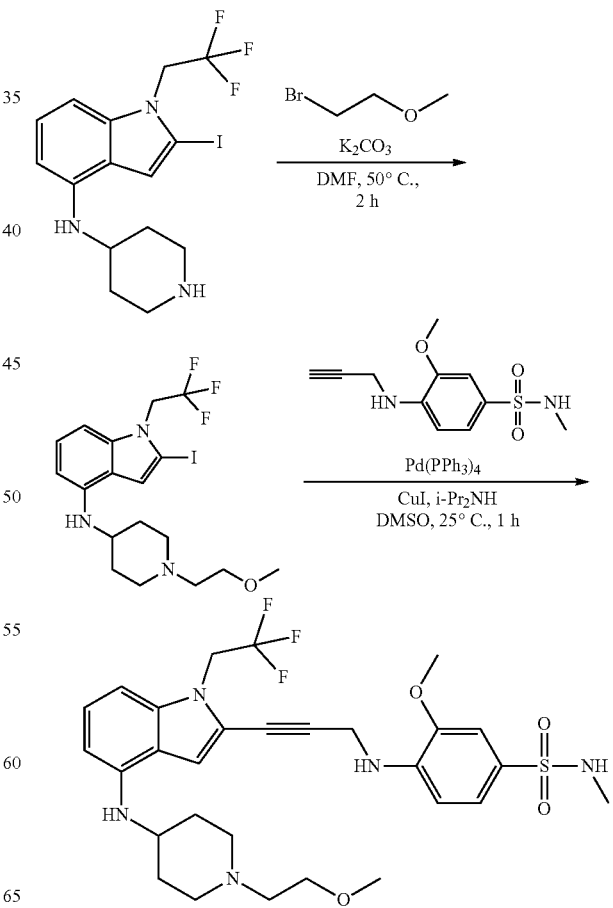

Preparation of 2-iodo-N-(1-(2-methoxyethyl)piperidin-4-yl)-1-(2,2,2-trifluoroethyl)-1H-indol-4-amine: To a solution of 2-iodo-N-(piperidin-4-yl)-1-(2,2,2-trifluoroethyl)-1H-indol-4-amine (100 mg, 222.11 μmol, 1 eq) in DMF (2 mL) were added $K_2CO_3$ (153.48 mg, 1.11 mmol, 5 eq) and 1-bromo-2-methoxyethane (61.74 mg, 444.22 μmol, 41.72 μL, 2 eq). The reaction mixture was stirred at 50° C. for 1 hr. TLC analysis (DCM:MeOH=10:1, $R_f$=0.43) indicated that the reaction was complete. The reaction mixture was quenched by adding water (40 mL) at 25° C. and extracting the mixture with EtOAc (10 mL×3). The combined organic layer was dried over sodium sulfate, filtered, and concentrated under reduced pressure. The crude residue was purified by prep-TLC ($SiO_2$, DCM:MeOH=10:1) to afford the desired product (80 mg, 141.29 μmol, 63.61% yield) as a light-yellow oil. MS ($ES^{30}$, m/z): 481.9.

Preparation of 3-methoxy-4-{[3-(4-{[1-(2-methoxyethyl)piperidin-4-yl]amino}-1-(2,2,2-trifluoroethyl)-1H-indol-2-yl)prop-2-yn-1-yl]amino}-N-methylbenzene-1-sulfonamide: To a solution of 3-methoxy-N-methyl-4-(prop-2-yn-1-ylamino)benzenesulfonamide (31.70 mg, 124.66 μmol, 1.2 eq.) in DMSO (3 mL) were added i-$Pr_2NH$ (105.12 mg, 1.04 mmol, 146.82 μL, 10 eq.), CuI (3.96 mg, 20.78 mol, 0.2 eq.), 2-iodo-N-(1-(2-methoxyethyl)piperidin-4-yl)-1-(2,2,2-trifluoroethyl)-1H-indol-4-amine (50 mg, 103.89 μmol, 1 eq.), and Pd(PPh$_3$)$_4$ (12 mg, 10.39 μmol, 0.1 eq.). The mixture was stirred at 25° C. for 1 h under $N_2$. LC-MS analysis showed that the reaction was complete. The reaction mixture was quenched by adding a saturated aqueous EDTA solution (50 mL) and EtOAc (25 mL) at 25° C. The mixture was extracted with EtOAc (25 mL×2). The combined organic layers were washed with water (100 mL×2) and brine (100 mL×2), dried over anhydrous sodium sulfate, stirred with activated carbon, filtered, and concentrated under reduced pressure. The residue was purified by prep-TLC ($SiO_2$, DCM:MeOH=10:1) and prep-HPLC to afford the desired product (23.4 mg, 38.51 μmol, 37.07% yield) as a white solid. MS ($ES^{30}$, m/z): 608.2.

Example D91: Synthesis of Compounds 845A, 846A, 847A, and 848A

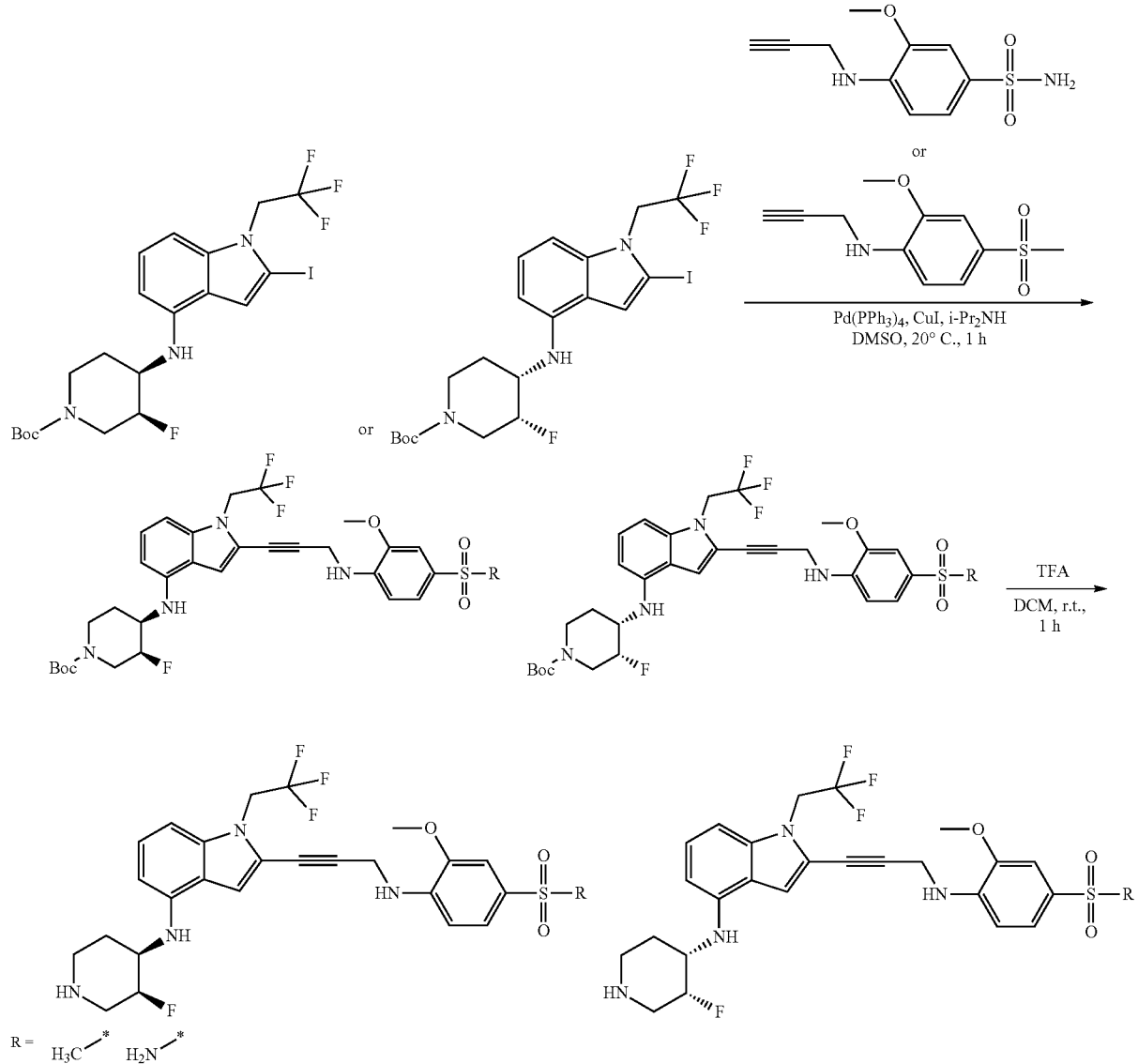

Preparation of tert-butyl (3S,4R)-4-((2-(3-((4-(R-sulfonyl)-2-methoxyphenyl)amino)prop-1-yn-1-yl)-1-(2,2,2-trifluoroethyl)-1H-indol-4-yl)amino)-3-fluoropiperidine-1-carboxylate and tert-butyl (3R,4S)-4-((2-(3-((4-(R-sulfonyl)-2-methoxyphenyl)amino)prop-1-yn-1-yl)-1-(2,2,2-trifluoroethyl)-1H-indol-4-yl)amino)-3-fluoropiperidine-1-carboxylate: To a solution of 3-methoxy-4-(prop-2-yn-1-ylamino)benzenesulfonamide or 2-methoxy-4-(methylsulfonyl)-N-(prop-2-yn-1-yl)aniline (99.46 mg, 415.65 μmol, 1.5 eq.) in DMSO (2 mL) were added i-Pr$_2$NH (280.40 mg, 2.77 mmol, 391.62 L, 10 eq.) and CuI (52.77 mg, 277.10 μmol, 1 eq.) in one portion under N$_2$. Then, tert-butyl (3S,4R)-3-fluoro-4-((2-iodo-1-(2,2,2-trifluoroethyl)-1H-indol-4-yl)amino)piperidine-1-carboxylate (150 mg, 277.10 μmol, 1 eq.) or tert-butyl (3R,4S)-3-fluoro-4-((2-iodo-1-(2,2,2-trifluoroethyl)-1H-indol-4-yl)amino)piperidine-1-carboxylate (150 mg, 277.10 μmol, 1 eq.) and Pd(PPh$_3$)$_4$ (32.02 mg, 27.71 μmol, 0.1 eq.) were added to the mixture. The mixture was purged with N$_2$ three times and stirred at 20° C. for 1 h. LC-MS analysis showed that some starting material remained, and the desired product was detected. EtOAc (20 mL) was poured into the mixture, and the resulting mixture was poured into a saturated aqueous EDTA solution (30 mL) and stirred for 1 h. The aqueous phase was extracted with EtOAc (20 mL×3). The combined organic layers were washed with brine (30 mL×3), dried over anhydrous sodium sulfate, filtered, and concentrated in vacuo to give a residue. The residue was purified by prep-TLC (SiO$_2$, PE:EtOAc=2:1) to afford the desired product (170 mg).

Preparation of final products: To a mixture of tert-butyl (3S,4R)-4-((2-(3-((4-(R-sulfonyl)-2-methoxyphenyl)amino)prop-1-yn-1-yl)-1-(2,2,2-trifluoroethyl)-1H-indol-4-yl)amino)-3-fluoropiperidine-1-carboxylate or tert-butyl (3R,4S)-4-((2-(3-((4-(R-sulfonyl)-2-methoxyphenyl)amino)prop-1-yn-1-yl)-1-(2,2,2-trifluoroethyl)-1H-indol-4-yl)amino)-3-fluoropiperidine-1-carboxylate (100 mg, 153.21 μmol, 1 eq.) in DCM (3 mL) was added TFA (1 mL) in one portion at 20° C. under N$_2$. The mixture was stirred at 20° C. for 60 min. TLC analysis showed that the reaction was complete. The reaction was quenched by adding a saturated aqueous solution of Na$_2$CO$_3$ to adjust the pH of the mixture to 9 and was extracted with EtOAc (15 mL×3). The combined organic layers were washed with brine (15 mL×2), dried over anhydrous sodium sulfate, filtered, and concentrated in vacuo. The residue was purified by prep-HPLC to afford the desired products as white solids.

N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine, 32.7 mg, 38% yield, MS (ES$^{30}$, m/z): 553.2; N-((3R,4S)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine, 39.7 mg, 31% yield, MS (ES$^{30}$, m/z): 553.2; 4-{[3-(4-{[(3S,4R)-3-fluoropiperidin-4-yl]amino}-1-(2,2,2-trifluoroethyl)-1H-indol-2-yl)prop-2-yn-1-yl]amino}-3-methoxybenzene-1-sulfonamide, 36.6 mg, 42% yield, MS (ES$^{30}$, m/z): 554.2; 4-{[3-(4-{[(3R,4S)-3-fluoropiperidin-4-yl]amino}-1-(2,2,2-trifluoroethyl)-1H-indol-2-yl)prop-2-yn-1-yl]amino}-3-methoxybenzene-1-sulfonamide, 37 mg, 29% yield, MS (ES$^{30}$, m/z): 554.2.

Example D92: Synthesis of Compounds 864A, 865A, 866A, and 867A

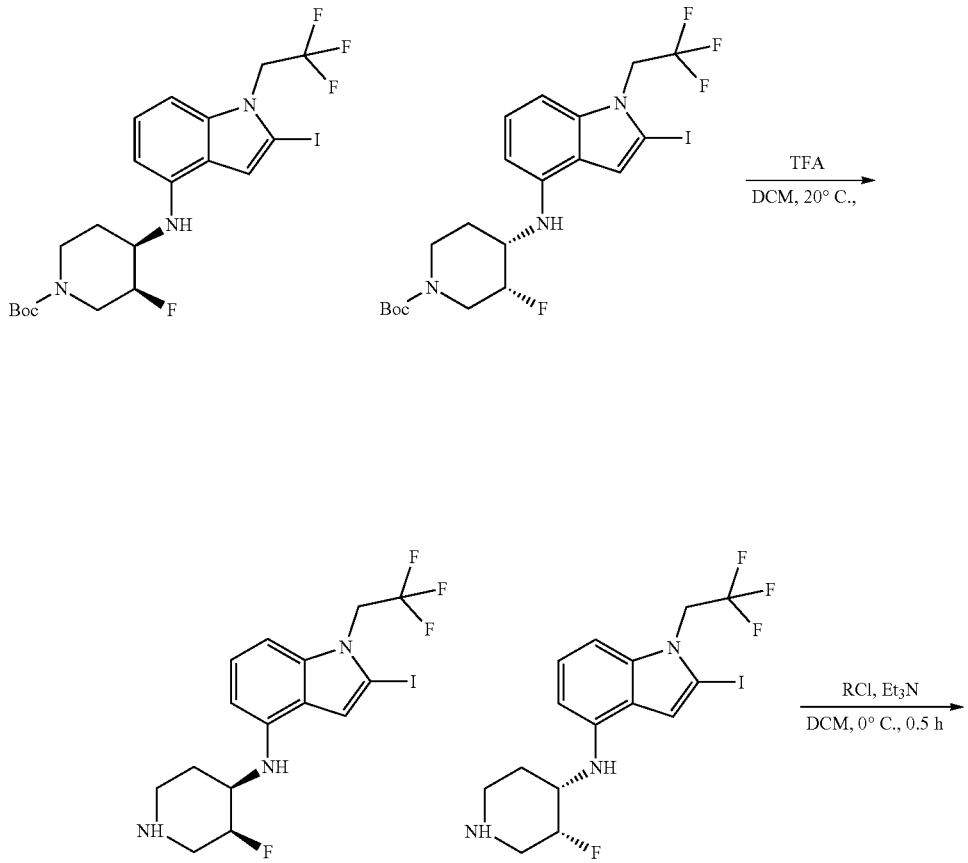

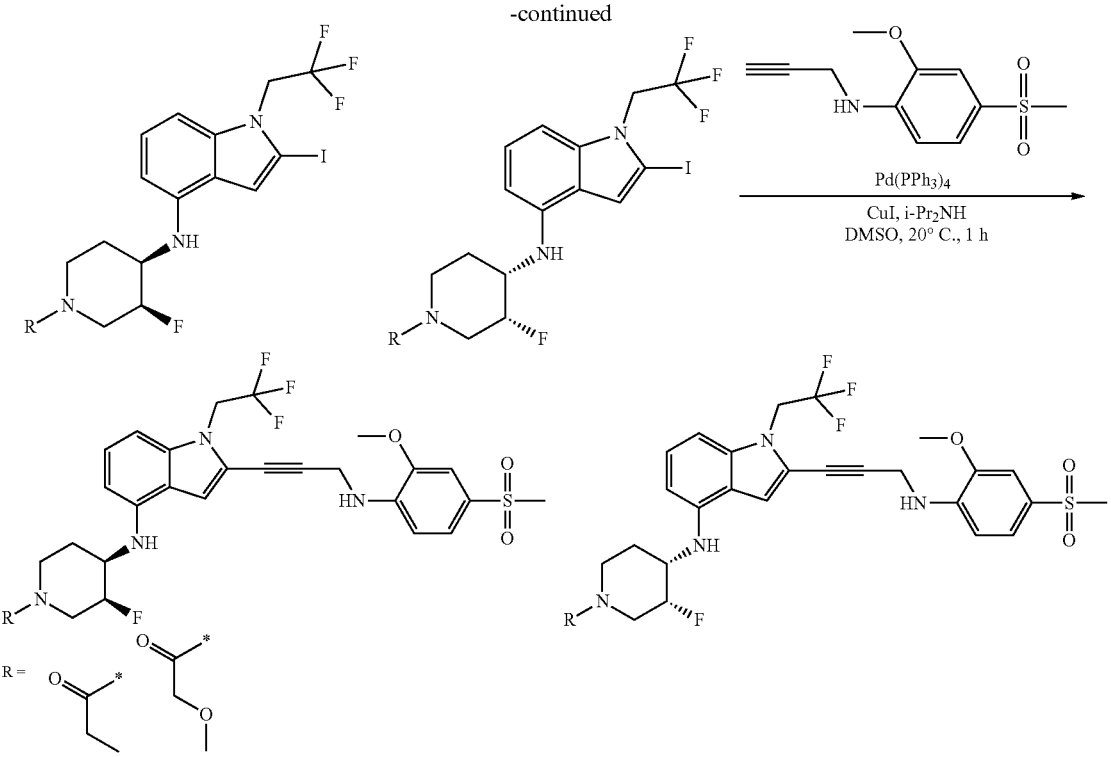

Preparation of N-((3S,4R)-3-fluoropiperidin-4-yl)-2-iodo-1-(2,2,2-trifluoroethyl)-1H-indol-4-amine and N-((3R,4S)-3-fluoropiperidin-4-yl)-2-iodo-1-(2,2,2-trifluoroethyl)-1H-indol-4-amine: To a solution of tert-butyl (3S,4R)-3-fluoro-4-((2-iodo-1-(2,2,2-trifluoroethyl)-1H-indol-4-yl)amino)piperidine-1-carboxylate (1 g, 1.85 mmol, 1 eq.) or tert-butyl (3R,4S)-3-fluoro-4-((2-iodo-1-(2,2,2-trifluoroethyl)-1H-indol-4-yl)amino)piperidine-1-carboxylate (1 g, 1.85 mmol, 1 eq.) in DCM (9 mL) was added TFA (3 mL) in one portion. The mixture was stirred at 20° C. for 1 h. TLC analysis showed that the reaction was complete. The reaction was quenched by adding a saturated aqueous solution of $Na_2CO_3$, adjusting the pH of the mixture to 8, and extracting the mixture with EtOAc (20 mL×3). The organic layer was washed with brine (20 mL×2), dried over anhydrous sodium sulfate, filtered, and concentrated in vacuo to afford the desired products.

Preparation of R-substituted N-((3S,4R)-3-fluoropiperidin-4-yl)-2-iodo-1-(2,2,2-trifluoroethyl)-1H-indol-4-amine and R-substituted N-((3R,4S)-3-fluoropiperidin-4-yl)-2-iodo-1-(2,2,2-trifluoroethyl)-1H-indol-4-amine: To a solution of N-((3S,4R)-3-fluoropiperidin-4-yl)-2-iodo-1-(2,2,2-trifluoroethyl)-1H-indol-4-amine or N-((3R,4S)-3-fluoropiperidin-4-yl)-2-iodo-1-(2,2,2-trifluoroethyl)-1H-indol-4-amine (150 mg, 339.98 µmol, 1 eq.) in DCM (4 mL) were added $Et_3N$ (103.21 mg, 1.02 mmol, 141.96 µL, 3 eq.) and propanoyl chloride (37.75 mg, 407.97 µmol, 37.75 µL, 1.2 eq.) in one portion at 0° C. The reaction mixture was stirred at 0° C. for 0.5 h. TLC analysis showed that the reaction was complete. The reaction was diluted with water (20 mL) and extracted with EtOAc (20 mL×3). The combined organic layers were washed with brine (20 mL×2), dried over anhydrous sodium sulfate, filtered, and concentrated in vacuo. The residue was purified by prep-TLC ($SiO_2$, PE:EtOAc=1:2) to afford the desired product 1-[(3S,4R)-3-fluoro-4-[[2-iodo-1-(2,2,2-trifluoroethyl)indol-4-yl]amino]-1-piperidyl]propan-1-one (140 mg, 281.54 µmol, 82.81% yield).

Preparation of final products: To a solution of 2-methoxy-4-(methylsulfonyl)-N-(prop-2-yn-1-yl)aniline (96.24 mg, 402.20 µmol, 2 eq.) in DMSO (2 mL) were added i-$Pr_2NH$ (203.49 mg, 2.01 mmol, 284.21 µL, 10 eq.) and CuI (38.30 mg, 201.10 µmol, 1 eq.) in one portion under $N_2$. Then R-substituted N-((3S,4R)-3-fluoropiperidin-4-yl)-2-iodo-1-(2,2,2-trifluoroethyl)-1H-indol-4-amine (100 mg, 201.10 µmol, 1 eq.) or R-substituted N-((3R,4S)-3-fluoropiperidin-4-yl)-2-iodo-1-(2,2,2-trifluoroethyl)-1H-indol-4-amine (100 mg, 201.10 µmol, 1 eq.) and $Pd(PPh_3)_4$ (23.24 mg, 20.11 µmol, 0.1 eq.) were added. The mixture was purged with $N_2$ three times, and the reaction mixture was stirred at 20° C. for 1 h. TLC analysis showed that the reaction was complete. EtOAc (20 mL) was poured into the reaction, and the resulting mixture was poured into a saturated aqueous EDTA solution (30 mL) and stirred for 1 h. The aqueous phase was extracted with EtOAc (20 mL×3). The combined organic layers were washed with brine (30 mL×3), dried over anhydrous sodium sulfate, filtered, and concentrated in vacuo. The residue was purified by prep-TLC and prep-HPLC to afford the desired products.

1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]propan-1-one, 36.7 mg, 30% yield, MS ($ES^{30}$, m/z): 609.3; 1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]propan-1-one, 29.3 mg, 24% yield, MS ($ES^{30}$, m/z): 609.3; 1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]-2-methoxyethan-1-one, 26.1 mg, 21% yield, MS ($ES^{30}$, m/z): 625.3; and 1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]-2-methoxyethan-1-one, 20.4 mg, 17% yield, MS (ES$^{30}$, m/z): 625.3.

Example D93: Synthesis of Compounds 732A, 742A, 743A, 744A, 745A, 746A, 747A, 748A, 750A, 751A, 752A, 753A 756A, and 757A

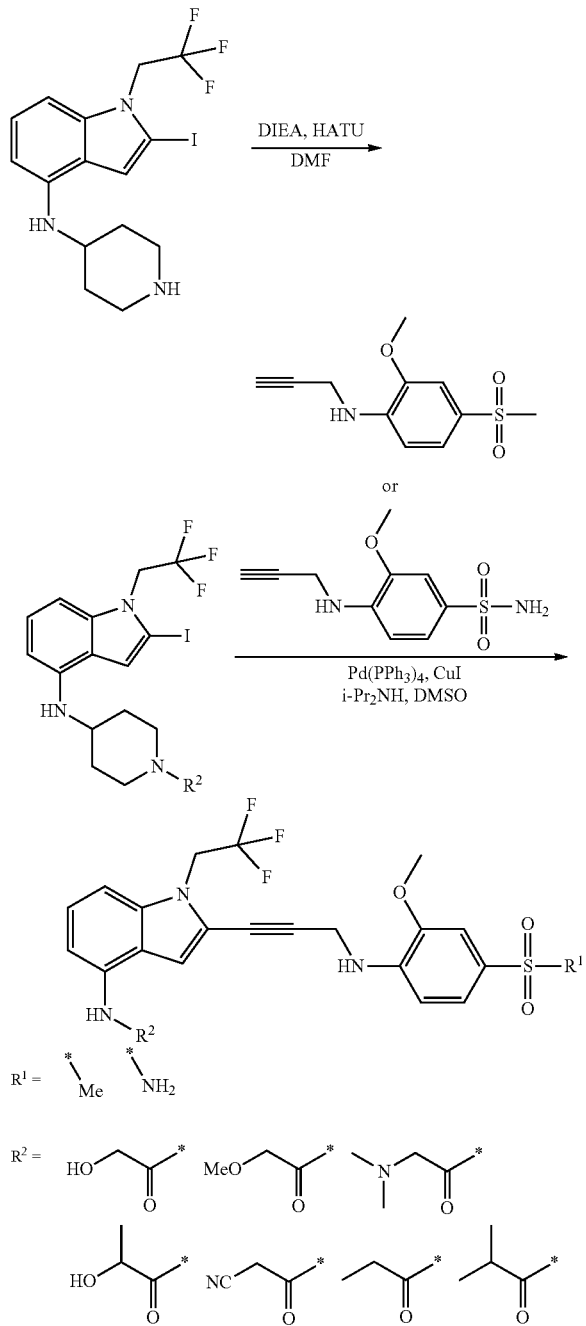

Preparation of 2-iodo-N-(1-(R$^2$-substituted)piperidin-4-yl)-1-(2,2,2-trifluoroethyl)-1H-indol-4-amine: To a solution of 2-iodo-N-(piperidin-4-yl)-1-(2,2,2-trifluoroethyl)-1H-indol-4-amine (100 mg, 226.84 μmol, 1 eq.) in DMF (3 mL) were added 2-methylpropanoic acid (21.98 mg, 249.52 μmol, 23.14 μL, 1.1 eq.), DIEA (58.63 mg, 453.67 μmol, 79.02 μL, 2 eq.), and HATU (129.37 mg, 340.25 μmol, 1.5 eq.). The mixture was stirred at 25° C. for 1 h. TLC and LC-MS analysis showed that the starting material was consumed completely. The reaction was partitioned by adding water (50 mL) and EtOAc (5 mL). The aqueous phase was extracted with EtOAc (30 mL×3). The combined organic layers were washed with brine (50 mL×3), dried over anhydrous sodium sulfate and filtered to give a filter liquor. The filter liquor was dried in vacuo to give the crude product 1-[4-[[2-iodo-1-(2,2,2-trifluoroethyl)indol-4-yl]amino]-1-piperidyl]-2-methyl-propan-1-one (110 mg, crude) as an oil.

Preparation of final products: To a solution of 2-methoxy-4-(methylsulfonyl)-N-(prop-2-yn-1-yl)aniline (46.20 mg, 173.75 μmol, 1.2 eq.) or 3-methoxy-4-(prop-2-yn-1-ylamino)benzenesulfonamide (40.18 mg, 133.79 μmol, 1.2 eq.) in DMSO (2 mL) were added i-Pr$_2$NH (65.90 mg, 1.11 mmol, 95.79 μL, 10 eq.), CuI (21.23 mg, 111.49 μmol, 1 eq.), 2-iodo-N-(1-(R$^2$-substituted)piperidin-4-yl)-1-(2,2,2-trifluoroethyl)-1H-indol-4-amine 1-[4-[[2-iodo-1-(2,2,2-trifluoroethyl)indol-4-yl]amino]-1-piperidyl]-2-methyl-propan-1-one (55 mg, 111.49 μmol, 1 eq.), and Pd(PPh$_3$)$_4$ (25.77 mg, 22.30 μmol, 0.2 eq.) at 25° C. The mixture was stirred for 1 h under N$_2$. LC-MS and TLC analysis showed that the reaction was complete. The reaction mixture was quenched by adding a saturated aqueous EDTA solution (20 mL) at 25° C. and stirred for 2 h. The reaction mixture was partitioned by adding EtOAc (30 mL). The aqueous phase was extracted with EtOAc (30 mL×2) The organic phase was washed with brine (30 mL×2), dried over anhydrous sodium sulfate, filtered, and concentrated in vacuo to give the crude product. The residue was purified by prep-TLC and prep-HPLC to give a solution of the desired product. The solution was lyophilized to give the desired product.

2-hydroxy-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethan-1-one, (9.8 mg, 11.2% yield) MS (ES$^{30}$, m/z): 539.0; 4-{[3-(4-{[1-(2-hydroxyacetyl)piperidin-4-yl]amino}-1-(2,2,2-trifluoroethyl)-1H-indol-2-yl)prop-2-yn-1-yl]amino}-3-methoxybenzene-1-sulfonamide, (11.2 mg, 13.4% yield) MS (ES$^{30}$, m/z): 594.2; 2-methoxy-1-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)ethan-1-one, (13.4 mg, 14.5% yield) (MS (ES$^{30}$, m/z): 607.2; 3-methoxy-4-((3-(4-((1-(2-methoxyacetyl)piperidin-4-yl)amino)-1-(2,2,2-trifluoroethyl)-1H-indol-2-yl)prop-2-yn-1-yl)amino)benzenesulfonamide, (17.1 mg, 19.8% yield) MS (ES$^{30}$, m/z): 607.2; 2-(dimethylamino)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethan-1-one, (14.5 mg, 15.3% yield) (MS (ES$^{30}$, m/z): 620.2; 4-((3-(4-((1-(dimethylglycyl)piperidin-4-yl)amino)-1-(2,2,2-trifluoroethyl)-1H-indol-2-yl)prop-2-yn-1-yl)amino)-3-methoxybenzenesulfonamide, (11.3 mg, 13.7% yield) MS (ES$^{30}$, m/z): 621.2; 2-hydroxy-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-1-one, (9.6 mg, 8.8% yield) MS (ES$^{30}$, m/z): 607.2; 4-{[3-(4-{[1-(2-hydroxypropanoyl)piperidin-4-yl]amino}-1-(2,2,2-trifluoroethyl)-1H-indol-2-yl)prop-2-yn-1-yl]amino}-3-methoxybenzene-1-sulfonamide, (10.7 mg, 10.8% yield) MS (ES$^{30}$, m/z): 608.2; 3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-oxopropanenitrile, (9.8 mg, 8.9% yield) MS (ES³⁰, m/z): 602.2; 4-{[3-(4-{[1-(2-cyanoacetyl)piperidin-4-yl]amino}-1-(2,2,2-trifluoroethyl)-1H-indol-2-yl)prop-2-yn-1-yl]amino}-3-methoxybenzene-1-sulfonamide, (7.5 mg, 5.8% yield) MS (ES³⁰, m/z): 603.2; 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-1-one, (15.3 mg, 21.7% yield) MS (ES³⁰, m/z): 591.2; 3-methoxy-4-[(3-{4-[(1-propanoylpiperidin-4-yl)amino]-1-(2,2,2-trifluoroethyl)-1H-indol-2-yl}prop-2-yn-1-yl)amino]benzene-1-sulfonamide, (11.5 mg, 16.8% yield) MS (ES³⁰, m/z): 592.1; 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-2-methylpropan-1-one, (10.3 mg, 14.3% yield) (MS (ES³⁰, m/z): 605.2; 3-methoxy-4-{[3-(4-{[1-(2-methylpropanoyl)piperidin-4-yl]amino}-1-(2,2,2-trifluoroethyl)-1H-indol-2-yl)prop-2-yn-1-yl]amino}benzene-1-sulfonamide, (13.1 mg, 19.3% yield) MS (ES³⁰, 606.2)

Example D94: Synthesis of Compounds 766A and 767A

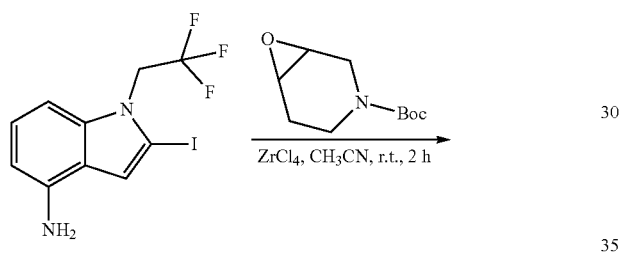

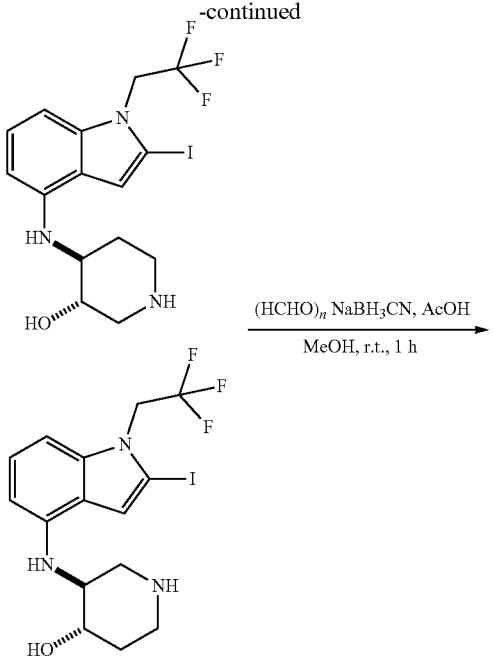

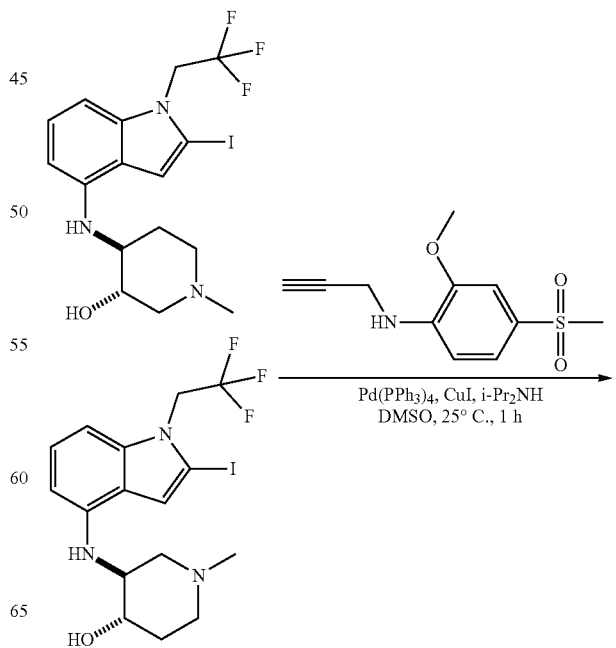

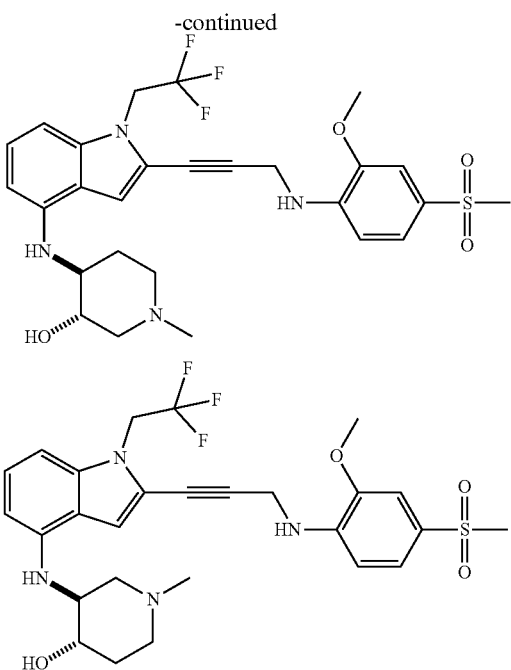

Preparation of tert-butyl (3S,4S)-3-hydroxy-4-((2-iodo-1-(2,2,2-trifluoroethyl)-1H-indol-4-yl)amino)piperidine-1-carboxylate and tert-butyl (3S,4S)-4-hydroxy-3-((2-iodo-1-(2,2,2-trifluoroethyl)-1H-indol-4-yl)amino)piperidine-1-carboxylate: To a mixture of tert-butyl 7-oxa-4-azabicyclo[4.1.0]heptane-4-carboxylate (878.81 mg, 4.41 mmol, 3 eq.) and 2-iodo-1-(2,2,2-trifluoroethyl)indol-4-amine (0.5 g, 1.47 mmol, 1 eq.) in CH$_3$CN (5 mL) was added ZrCl$_4$ (34.26 mg, 147.02 μmol, 12.24 μL, 0.1 eq.). The mixture was stirred at 25° C. for 2 h. TLC and LC-MS analysis showed that the reaction was complete. The reaction was filtered through a pad of diatomaceous earth and concentrated under reduced pressure. The residue was purified by prep-TLC (SiO$_2$, PE:EtOAc=3:1) and by prep-HPLC to afford the desired products as yellow solids.

tert-butyl (3S,4S)-3-hydroxy-4-((2-iodo-1-(2,2,2-trifluoroethyl)-1H-indol-4-yl)amino)piperidine-1-carboxylate (0.14 g, 233.62 μmol, 15.89% yield), MS (ES$^{30}$, m/z): 540.2; and tert-butyl (3S,4S)-4-hydroxy-3-((2-iodo-1-(2,2,2-trifluoroethyl)-1H-indol-4-yl)amino)piperidine-1-carboxylate (0.24 g, 400.50 μmol, 27.24% yield).

Preparation of (3S,4S)-4-((2-iodo-1-(2,2,2-trifluoroethyl)-1H-indol-4-yl)amino)piperidin-3-ol and (3S,4S)-3-((2-iodo-1-(2,2,2-trifluoroethyl)-1H-indol-4-yl)amino)piperidin-4-ol: To a solution of tert-butyl (3S,4S)-3-hydroxy-4-((2-iodo-1-(2,2,2-trifluoroethyl)-1H-indol-4-yl)amino)piperidine-1-carboxylate (0.15 g, 250.31 μmol, 1 eq.) or tert-butyl (3S,4S)-4-hydroxy-3-((2-iodo-1-(2,2,2-trifluoroethyl)-1H-indol-4-yl)amino)piperidine-1-carboxylate (0.15 g, 250.31 μmol, 1 eq.) in DCM (3 mL) was added TFA (1.39 g, 12.16 mmol, 899.98 μL, 48.56 eq.). The mixture was stirred at 25° C. for 0.5~1 h. TLC analysis showed that the reaction was complete. Saturated aqueous solution of Na$_2$CO$_3$ (10 mL) was added to the reaction mixture to adjust the pH of the mixture to 9. The mixture was then extracted with DCM (10 mL×3). The combined organic layers were washed with brine, dried over by anhydrous sodium sulfate, filtered, and concentrated under reduced pressure. The crude product was obtained as a yellow solid and used in the next step without purification.

Preparation of (3S,4S)-4-((2-iodo-1-(2,2,2-trifluoroethyl)-1H-indol-4-yl)amino)-1-methylpiperidin-3-ol and (3S,4S)-3-((2-iodo-1-(2,2,2-trifluoroethyl)-1H-indol-4-yl)amino)-1-methylpiperidin-4-ol: To a mixture of formaldehyde (12.31 mg, 409.82 μmol, 11.29 μL, 2 eq.) and (3S,4S)-4-((2-iodo-1-(2,2,2-trifluoroethyl)-1H-indol-4-yl)amino)piperidin-3-ol or (3S,4S)-3-((2-iodo-1-(2,2,2-trifluoroethyl)-1H-indol-4-yl)amino)piperidin-4-ol (0.09 g, 204.91 μmol, 1 eq.) in MeOH (3 mL) was added AcOH (12.30 mg, 204.91 μmol, 11.72 μL, 1 eq.). The mixture was stirred at 50° C. for 10 min, and NaBH$_3$CN (64.38 mg, 1.02 mmol, 5 eq.) was added. The resulting reaction mixture was stirred further at 50° C. for 1 h. TLC analysis showed that the reaction was complete. The reaction was poured to saturated aqueous solution of Na$_2$CO$_3$ (10 mL) and extracted with DCM (10 mL×3). The residue was purified by prep-TLC (SiO$_2$, DCM:MeOH=10:1) to afford the desired products as yellow solids.

Preparation of final products: To a solution of 2-methoxy-4-methylsulfonyl-N-prop-2-ynyl-aniline (42.76 mg, 178.71 μmol, 1.5 eq.) in DMSO (2 mL) were added N-isopropyl-propan-2-amine (120.56 mg, 1.19 mmol, 168.38 μL, 10 eq.), CuI (22.69 mg, 119.14 μmol, 1 eq.), then (3S,4S)-4-((2-iodo-1-(2,2,2-trifluoroethyl)-1H-indol-4-yl)amino)-1-methylpiperidin-3-ol (0.06 g, 119.14 μmol, 1 eq.) or (3S,4S)-3-((2-iodo-1-(2,2,2-trifluoroethyl)-1H-indol-4-yl)amino)-1-methylpiperidin-4-ol (70 mg, 154.44 mol, 1 eq.), and Pd(PPh$_3$)$_4$ (71.39 mg, 61.78 μmol, 0.4 eq.). The mixture was stirred at 25° C. for 1 h. TLC analysis showed that the reaction was complete. The reaction was diluted with EtOAc (20 mL), poured into saturated aqueous EDTA solution (20 mL) and stirred at 25° C. for 1 h. The resulting mixture was extracted with EtOAc (20 mL×3). The combined organic layers were washed with brine (20 mL×3) dried over anhydrous sodium sulfate, filtered, and concentrated under reduced pressure. The residue was purified by prep-HPLC to afford the desired products as light yellow solids.

rac-(3R,4R)-4-[(2-{3-[(4-methanesulfonyl-2-methoxyphenyl)amino]prop-1-yn-1-yl}-1-(2,2,2-trifluoroethyl)-1H-indol-4-yl)amino]-1-methylpiperidin-3-ol, (41.6 mg, 61.1% yield) MS (ES$^{30}$, m/z): 565.1; and rac-(3R,4S)-3-[(2-{3-[(4-methanesulfonyl-2-methoxyphenyl)amino]prop-1-yn-1-yl}-1-(2,2,2-trifluoroethyl)-1H-indol-4-yl)amino]-1-methylpiperidin-4-ol, (43.3 mg, 49.4% yield) MS (ES$^{30}$, m/z): 565.3.

Example D95: Synthesis of Compounds 523A, 524A, 525A, and 526A

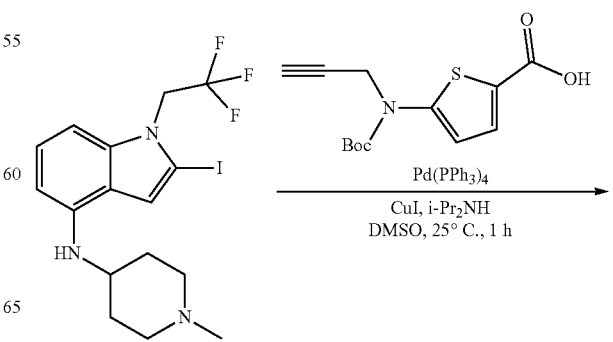

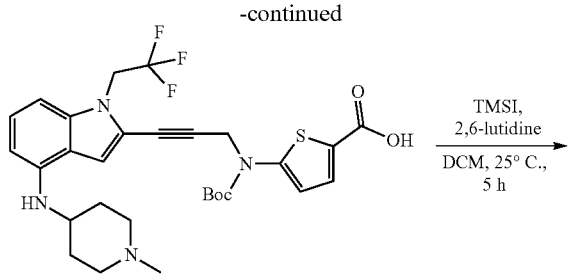

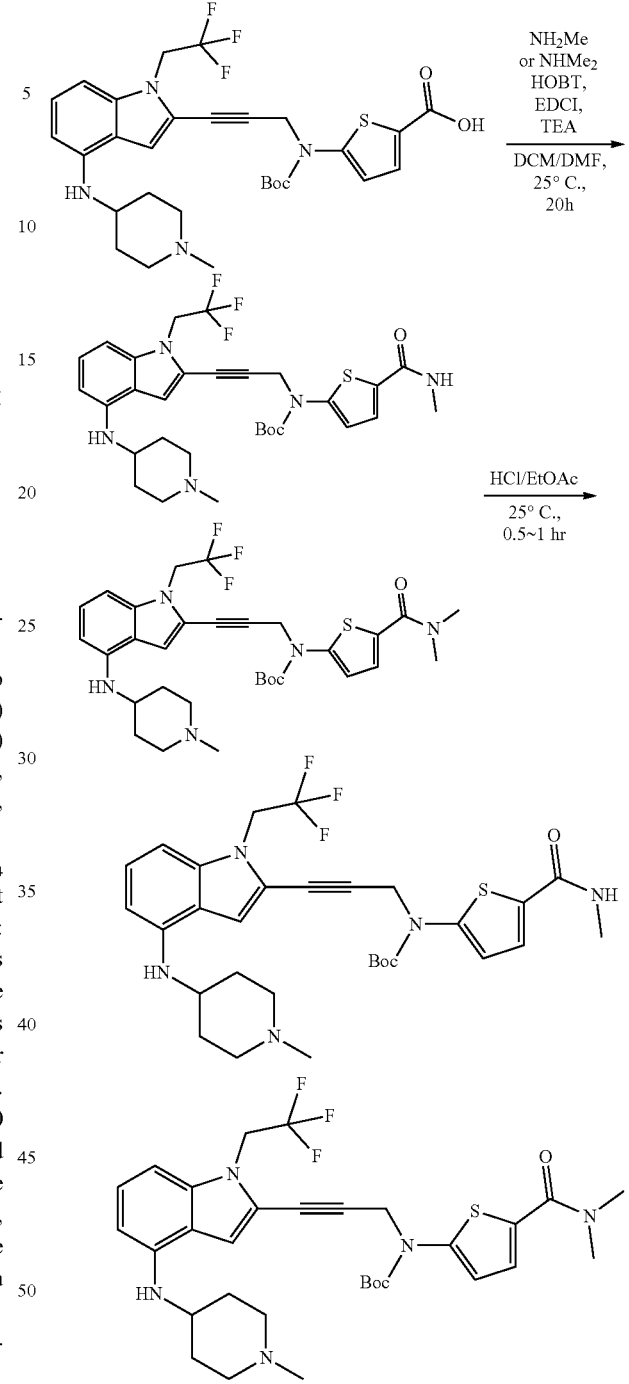

Preparation of 5-((tert-butoxycarbonyl)(3-(4-((1-methylpiperidin-4-yl)amino)-1-(2,2,2-trifluoroethyl)-1H-indol-2-yl)prop-2-yn-1-yl)amino)thiophene-2-carboxylic acid: To a solution of 5-((tert-butoxycarbonyl)(prop-2-yn-1-yl)amino)thiophene-2-carboxylic acid (0.4 g, 1.42 mmol, 1 eq.) in DMSO (2 mL) were added i-Pr$_2$NH (1.44 g, 14.22 mmol, 2.01 mL, 10 eq.), CuI (54.16 mg, 284.37 µmol, 0.2 eq.), 2-iodo-N-(1-methyl-4-piperidyl)-1-(2,2,2-trifluoroethyl)indol-4-amine (621.68 mg, 1.42 mmol, 1 eq.), and Pd(PPh$_3$)$_4$ (82.15 mg, 71.09 µmol, 0.05 eq). The mixture was stirred at 25° C. for 1 h under N$_2$. TLC analysis (DCM:MeOH:TEA=10:1:1, R$_f$=0.2) indicated that the starting material was consumed completely, and one new spot was detected. The reaction mixture was quenched by adding saturated aqueous EDTA solution (20 mL) and stirring the mixture at 20° C. for 1 h. The mixture was then extracted with EtOAc (40 mL×3). The combined organic layers were washed with brine (30 mL×3), dried over anhydrous sodium sulfate, filtered, and concentrated under reduced pressure to give a residue. The residue was purified by column chromatography (SiO$_2$, PE:EtOAc=3:1 to 0:1 to DCM:MeOH=10:1) to afford the desired product (0.71 g, 1.14 mmol, 80.32% yield) as a yellow solid.

Preparation of 5-((3-(4-((1-methylpiperidin-4-yl)amino)-1-(2,2,2-trifluoroethyl)-1H-indol-2-yl)prop-2-yn-1-yl)amino)thiophene-2-carboxylic acid: To a solution of 5-((tert-butoxycarbonyl)(3-(4-((1-methylpiperidin-4-yl)amino)-1-(2,2,2-trifluoroethyl)-1H-indol-2-yl)prop-2-yn-1-yl)amino)thiophene-2-carboxylic acid (0.06 g, 101.58 µmol, 1 eq.) in DCM (2 mL) were added 2,6-lutidine (326.54 mg, 3.05 mmol, 354.94 µL, 30 eq.) and TMSI (609.78 mg, 3.05 mmol, 414.81 µL, 30 eq.). The mixture was stirred at 25° C. for 5 h. LC-MS analysis showed that the starting material was consumed completely, and the desired mass was detected. The reaction mixture was filtered and concentrated under reduced pressure to give a residue. The residue was purified by prep-HPLC to obtain the desired product (0.015 g, 27.34 µmol, 26.91% yield) as a yellow solid. MS (ES$^{30}$, m/z): 489.9.

Preparation of tert-butyl (5-(methylcarbamoyl)thiophen-2-yl)(3-(4-((1-methylpiperidin-4-yl)amino)-1-(2,2,2-trifluoroethyl)-1H-indol-2-yl)prop-2-yn-1-yl)carbamate and N,N-dimethyl-5-((3-(4-((1-methylpiperidin-4-yl)amino)-1-(2,2,2-trifluoroethyl)-1H-indol-2-yl)prop-2-yn-1-yl)amino)thiophene-2-carboxamide: To a solution of 5-((3-(4-((1-methylpiperidin-4-yl)amino)-1-(2,2,2-trifluoroethyl)-1H-indol-2-yl)prop-2-yn-1-yl)amino)thiophene-2-carboxylic acid (0.2 g, 338.61 mol, 1 eq.) and methanamine hydrochloride (45.72 mg, 677.21 µmol, 2 eq.) or N-methylmethanamine hydrochloride (55.22 mg, 677.21 µmol, 2 eq.) in DCM (2 mL) and DMF (2 mL) were added TEA (171.32 mg, 1.69 mmol, 235.65 µL, 5 eq.), HOBt (68.63 mg, 507.91 µmol, 1.5 eq.), and EDCI (97.37 mg, 507.91 µmol, 1.5 eq.). The mixture was stirred at 25° C. for 20 h. HPLC analysis showed that the starting material remained. The reaction was quenched by adding water (30 mL) and extracted with EtOAc (20 mL×3). The combined organic layers were washed with brine (10 mL×2), dried over anhydrous sodium sulfate, filtered, and concentrated under reduced pressure. The residue was purified by prep-HPLC to afford the desired product as a yellow solid.

tert-butyl (5-(methylcarbamoyl)thiophen-2-yl)(3-(4-((1-methylpiperidin-4-yl)amino)-1-(2,2,2-trifluoroethyl)-1H-indol-2-yl)prop-2-yn-1-yl)carbamate (0.08 g, 129.87 µmol, 38.35% yield), MS (ES+, m/z): 604.2; and N,N-dimethyl-5-((3-(4-((1-methylpiperidin-4-yl)amino)-1-(2,2,2-trifluoroethyl)-1H-indol-2-yl)prop-2-yn-1-yl)amino)thiophene-2-carboxamide (0.075 g, 118.99 µmol, 35.14% yield).

Preparation of N-methyl-5-((3-(4-((1-methylpiperidin-4-yl)amino)-1-(2,2,2-trifluoroethyl)-1H-indol-2-yl)prop-2-yn-1-yl)amino)thiophene-2-carboxamide and N,N-dimethyl-5-((3-(4-((1-methylpiperidin-4-yl)amino)-1-(2,2,2-trifluoroethyl)-1H-indol-2-yl)prop-2-yn-1-yl)amino)thiophene-2-carboxamide: A solution of tert-butyl (5-(methylcarbamoyl)thiophen-2-yl)(3-(4-((1-methylpiperidin-4-yl)amino)-1-(2,2,2-trifluoroethyl)-1H-indol-2-yl)prop-2-yn-1-yl)carbamate (0.06 g, 97.40 µmol, 1 eq.) or N,N-dimethyl-5-((3-(4-((1-methylpiperidin-4-yl)amino)-1-(2,2,2-trifluoroethyl)-1H-indol-2-yl)prop-2-yn-1-yl)amino)thiophene-2-carboxamide (0.06 g, 97.13 µmol, 1 eq.) in 4N HCl/EtOAc (5 mL) was stirred at 25° C. for 1 h. LC-MS analysis showed the desired compound. The reaction mixture was filtered and concentrated under reduced pressure to give a residue. The residue was purified by prep-HPLC to obtain the desired product as a yellow solid.

N-methyl-5-((3-(4-((1-methylpiperidin-4-yl)amino)-1-(2,2,2-trifluoroethyl)-1H-indol-2-yl)prop-2-yn-1-yl)amino)thiophene-2-carboxamide (0.035 g, 65.12 µmol, 66.86% yield), MS (ES30, m/z): 504.2; and N,N-dimethyl-5-((3-(4-((1-methylpiperidin-4-yl)amino)-1-(2,2,2-trifluoroethyl)-1H-indol-2-yl)prop-2-yn-1-yl)amino)thiophene-2-carboxamide (0.036 g, 65.31 µmol, 67.24% yield).

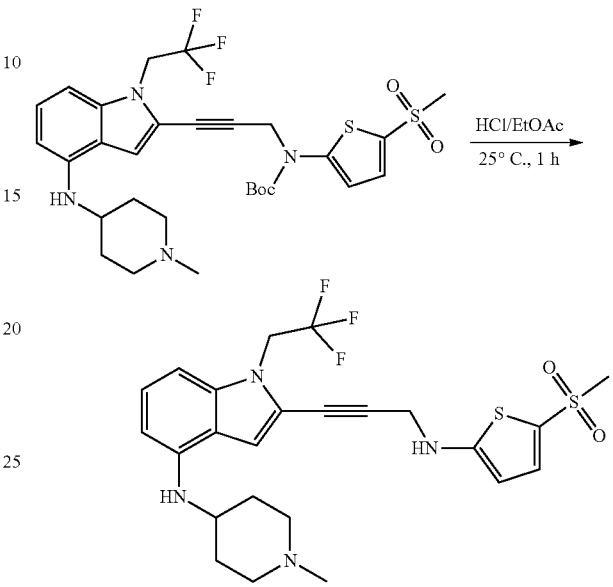

Preparation of N-(1-methylpiperidin-4-yl)-2-(3-((5-(methylsulfonyl)thiophen-2-yl)amino)prop-1-yn-1-yl)-1-(2,2,2-trifluoroethyl)-1H-indol-4-amine: A solution of tert-butyl (3-(4-((1-methylpiperidin-4-yl)amino)-1-(2,2,2-trifluoroethyl)-1H-indol-2-yl)prop-2-yn-1-yl)(5-(methylsulfonyl)thiophen-2-yl)carbamate (0.06 g, 96.04 µmol, 1 eq.) in 4N HCl/EtOAc (3 mL) was stirred at 25° C. for 1 h. HPLC analysis showed that 74.1% of desired compound had formed. The reaction mixture was quenched by adding a saturated solution of Na₂CO₃ (10 mL) to adjust the pH of the mixture to 8 and extracted with EtOAc (10 mL×3). The combined organic layers were washed with brine (10 mL), filtered, and concentrated under reduced pressure. The residue was purified by prep-HPLC to afford the desired product (0.017 g, 30.85 µmol, 32.12% yield) as a yellow solid. MS (ES30, m/z): 525.2.

Example D96: Synthesis of Compounds 839A and 840A

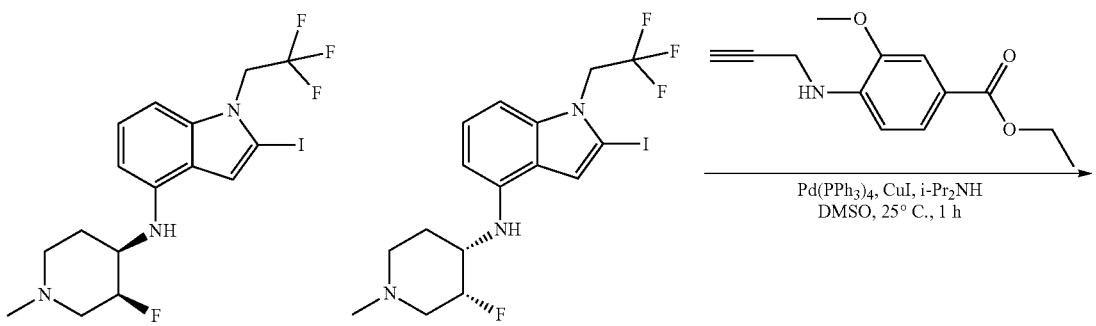

1135 1136

-continued

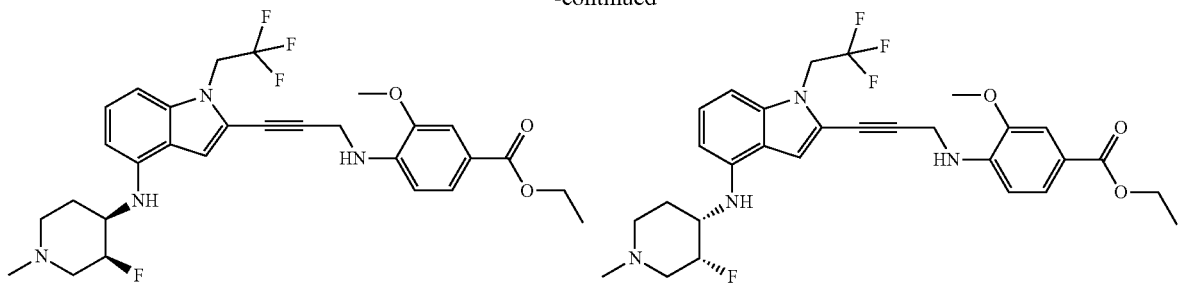

Preparation of ethyl 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoate and ethyl 4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-3-methoxybenzoate: To a solution of ethyl 3-methoxy-4-(prop-2-yn-1-ylamino)benzoate (66.61 mg, 285.57 μmol, 1.3 eq.) in DMSO (3 mL) were added i-Pr$_2$NH (222.28 mg, 2.20 mmol, 310.45 L, 10 eq.), CuI (8.37 mg, 43.93 μmol, 0.2 eq.), N-((3R,4S)-3-fluoro-1-methylpiperidin-4-yl)-2-iodo-1-(2,2,2-trifluoroethyl)-1H-indol-4-amine (100 mg, 219.67 μmol, 1 eq.) or N-((3S,4R)-3-fluoro-1-methylpiperidin-4-yl)-2-iodo-1-(2,2,2-trifluoroethyl)-1H-indol-4-amine (100 mg, 219.67 μmol, 1 eq.), and Pd(PPh$_3$)$_4$ (25.38 mg, 21.97 μmol, 0.1 eq.). The mixture was stirred at 25° C. for 1 h under N$_2$. TLC analysis showed that the reaction was complete. The reaction mixture was quenched by adding a saturated aqueous EDTA solution (100 mL) and EtOAc (50 mL) at 25° C. and extracting the mixture further with EtOAc (50 mL×2). The combined organic layers were washed with brine (100 mL×2), dried over anhydrous sodium sulfate, filtered, and concentrated under reduced pressure to give a residue. The residue was purified by prep-TLC (SiO$_2$, DCM:MeOH=10:1) and prep-HPLC to afford the desired products as white solids.

Ethyl 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoate, 36.1 mg, 29.3% yield, MS (ES$^{30}$, m/z): 561.3; and ethyl 4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-3-methoxybenzoate, 33.2 mg, 27.0% yield, MS (ES$^+$, m/z): 561.3.

Example D97: Synthesis of Compounds 851A, 852A, 857A, and 858A

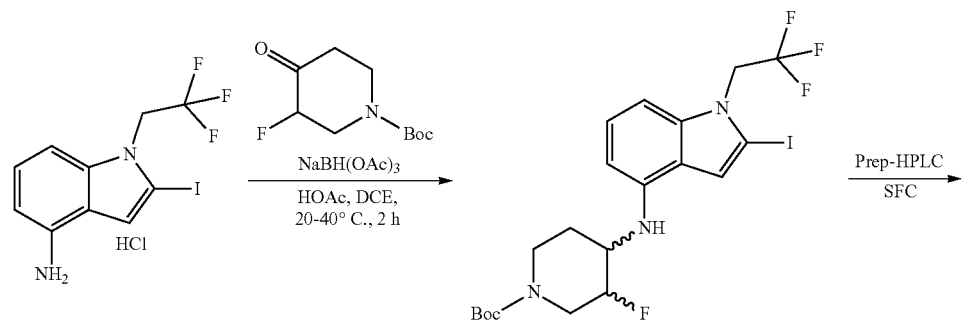

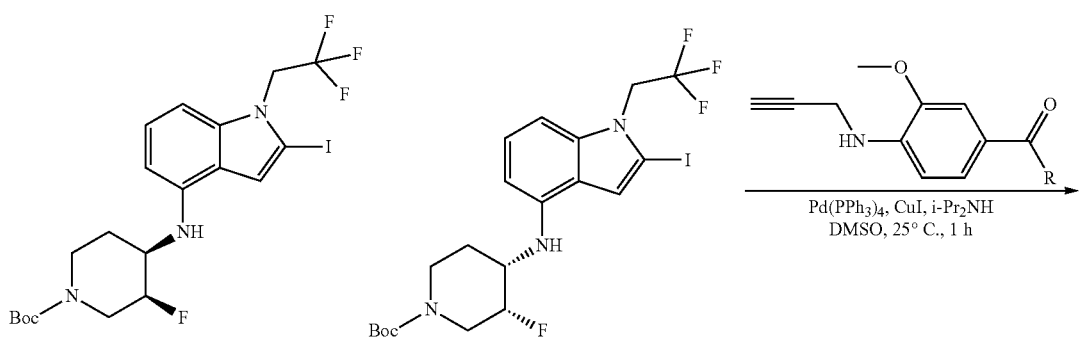

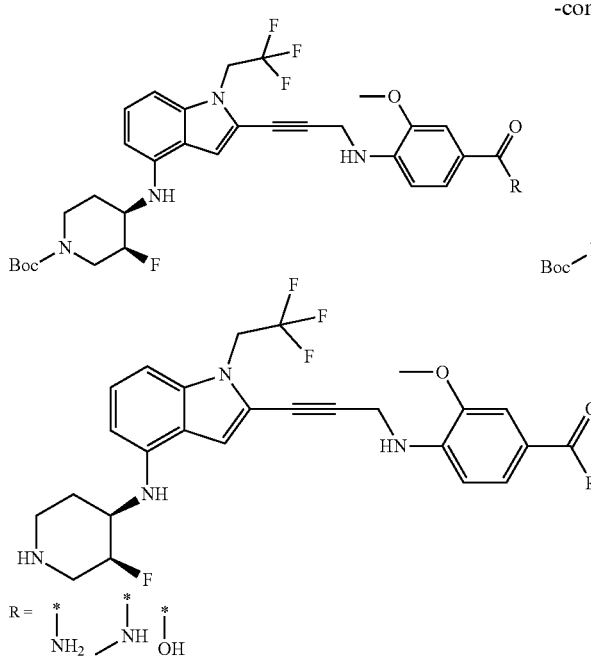
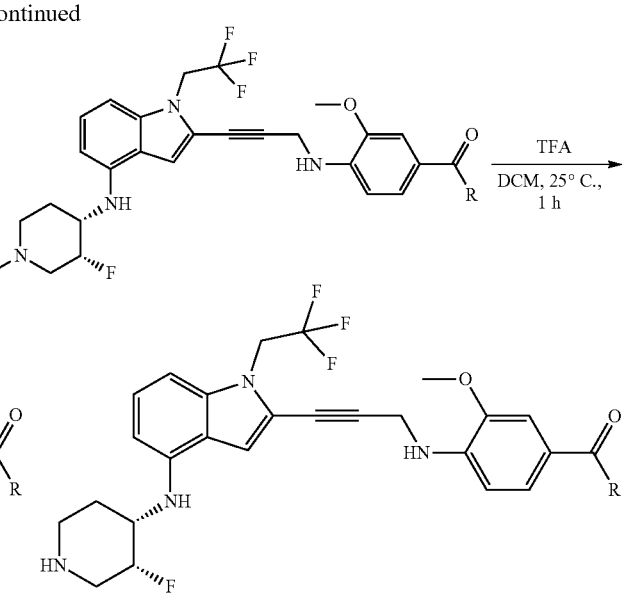

Preparation of tert-butyl 3-fluoro-4-((2-iodo-1-(2,2,2-trifluoroethyl)-1H-indol-4-yl)amino)piperidine-1-carboxylate: To a solution of 2-iodo-1-(2,2,2-trifluoroethyl)-1H-indol-4-amine hydrochloride (60 g, 26.56 mmol, 27.60 mL, 1 eq., HCl) in AcOH (1500 mL) and DCE (500 mL) were added tert-butyl 3-fluoro-4-oxo-piperidine-1-carboxylate (28.85 g, 132.79 mmol, 5 eq.) and NaBH(OAc)$_3$ (14.07 g, 66.39 mmol, 2.5 eq.) at 20° C. The mixture was stirred at 40° C. for 2 h. LC-MS analysis showed that the reaction was complete. The reaction mixture was quenched by adding ice water (2000 mL) at 0° C., adding aqueous 2N NaOH to adjust the pH of the mixture to 8 and extracting the mixture with EtOAc (1000 mL×4). The combined organic layers were washed with brine (1000 mL×2), dried over anhydrous sodium sulfate, filtered, and concentrated under reduced pressure to give a residue. The residue was purified by column chromatography (SiO$_2$, PE:EtOAc=10:1 to 8:1) to obtain the desired product (100 g) as a yellow solid.

Preparation of tert-butyl (3S,4R)-3-fluoro-4-((2-iodo-1-(2,2,2-trifluoroethyl)-1H-indol-4-yl)amino)piperidine-1-carboxylate and tert-butyl (3R,4S)-3-fluoro-4-((2-iodo-1-(2,2,2-trifluoroethyl)-1H-indol-4-yl)amino)piperidine-1-carboxylate: tert-Butyl 3-fluoro-4-((2-iodo-1-(2,2,2-trifluoroethyl)-1H-indol-4-yl)amino)piperidine-1-carboxylate was purified by prep-HPLC and SFC to obtain the desired products as white solids. tert-butyl (3S,4R)-3-fluoro-4-((2-iodo-1-(2,2,2-trifluoroethyl)-1H-indol-4-yl)amino)piperidine-1-carboxylate, 46.8% yield; and tert-butyl (3R,4S)-3-fluoro-4-((2-iodo-1-(2,2,2-trifluoroethyl)-1H-indol-4-yl)amino)piperidine-1-carboxylate, 46.4% yield.

Preparation of tert-butyl (3S,4R)-4-((2-(3-((4-(R-carbonyl)-2-methoxyphenyl)amino)prop-1-yn-1-yl)-1-(2,2,2-trifluoroethyl)-1H-indol-4-yl)amino)-3-fluoropiperidine-1-carboxylate and tert-butyl (3S,4R)-4-((2-(3-((4-(R-carbonyl)-2-methoxyphenyl)amino)prop-1-yn-1-yl)-1-(2,2,2-trifluoroethyl)-1H-indol-4-yl)amino)-3-fluoropiperidine-1-carboxylate: To a solution of R-substituted alkyne (73.92 mg, 360.23 μmol, 1.3 eq.) in DMSO (4 mL) were added i-Pr$_2$NH (280.40 mg, 2.77 mmol, 391.62 μL, 10 eq.), CuI (10.55 mg, 55.42 μmol, 0.2 eq.), tert-butyl (3S,4R)-3-fluoro-4-((2-iodo-1-(2,2,2-trifluoroethyl)-1H-indol-4-yl)amino)piperidine-1-carboxylate or tert-butyl (3R,4S)-3-fluoro-4-((2-iodo-1-(2,2,2-trifluoroethyl)-1H-indol-4-yl)amino) piperidine-1-carboxylate (0.15 g, 277.10 μmol, 1 eq.), and Pd(PPh$_3$)$_4$ (32.02 mg, 27.71 μmol, 0.1 eq.). The mixture was stirred at 25° C. for 1 h under N$_2$. TLC analysis showed that the reaction was complete. The reaction mixture was quenched by adding a saturated aqueous EDTA solution (100 mL) and EtOAc (50 mL) with stirring at 25° C. for 2 h. The mixture was further extracted with EtOAc (50 mL×2). The combined organic layers were washed with brine (100 mL×2), dried over anhydrous sodium sulfate, filtered, and concentrated under reduced pressure. The crude residue was purified by prep-TLC (SiO$_2$, DCM:MeOH=10:1) to afford the desired products as yellow solids.

Preparation of final products: To a mixture of tert-butyl (3S,4R)-4-((2-(3-((4-(R-carbonyl)-2-methoxyphenyl) amino)prop-1-yn-1-yl)-1-(2,2,2-trifluoroethyl)-1H-indol-4-yl)amino)-3-fluoropiperidine-1-carboxylate (100 mg, 161.65 μmol, 1 eq.) or tert-butyl (3S,4R)-4-((2-(3-((4-(R-carbonyl)-2-methoxyphenyl)amino)prop-1-yn-1-yl)-1-(2,2,2-trifluoroethyl)-1H-indol-4-yl)amino)-3-fluoropiperidine-1-carboxylate (100 mg, 161.65 μmol, 1 eq.) in DCM (3 mL) was added TFA (1 mL). The mixture stirred at 25° C. for 1 h under N$_2$. TLC showed that the reaction was completed. The reaction mixture was quenched by adding saturated aqueous sodium carbonate (100 mL) and extracted with EtOAc (50 mL×2). The combined organic layers were washed with brine solution (100 mL×2) in turn. Then dried over anhydrous sodium sulfate, filtered and concentrated under reduced pressure to give a residue. The residue was purified by prep-HPLC to obtain the desired products as white solids.

4-[3-[4-[[(3S,4R)-3-fluoro-4-piperidyl]amino]-1-(2,2,2-trifluoroethyl)indol-2-yl]prop-2-ynylamino]-3-methoxy-benzamide, 28.9 mg, 33.1% yield, MS (ES$^{30}$, m/z): 518.2); 4-[3-[4-[[(3R,4S)-3-fluoro-4-piperidyl]amino]-1-(2,2,2-trifluoroethyl)indol-2-yl]prop-2-ynylamino]-3-methoxy-benzamide 39.9 mg, 59.52% yield, MS (ES³⁰, m/z): 518.2); 4-{[3-(4-{[(3S,4R)-3-fluoropiperidin-4-yl]amino}-1-(2,2,2-trifluoroethyl)-1H-indol-2-yl)prop-2-yn-1-yl]amino}-3-methoxy-N-methylbenzamide, 27.4 mg, 38.0% yield, MS (ES³⁰, m/z): 532.2; 4-{[3-(4-{[(3R,4S)-3-fluoropiperidin-4-yl]amino}-1-(2,2,2-trifluoroethyl)-1H-indol-2-yl)prop-2-yn-1-yl]amino}-3-methoxy-N-methylbenzamide, 30.5 mg, 36.1% yield, MS (ES³⁰, m/z): 532.2; 4-{[3-(4-{[(3S,4R)-3-fluoropiperidin-4-yl]amino}-1-(2,2,2-trifluoroethyl)-1H-indol-2-yl)prop-2-yn-1-yl]amino}-3-methoxybenzoic acid, 32.8 mg, 31% yield, MS (ES³⁰, m/z): 519.2 and 4-{[3-(4-{[(3R,4S)-3-fluoropiperidin-4-yl]amino}-1-(2,2,2-trifluoroethyl)-1H-indol-2-yl)prop-2-yn-1-yl]amino}-3-methoxybenzoic acid, 30.6 mg, 36.1% yield, MS (ES⁺, m/z): 519.2.

Example D98: Synthesis of Compounds 823A and 824A

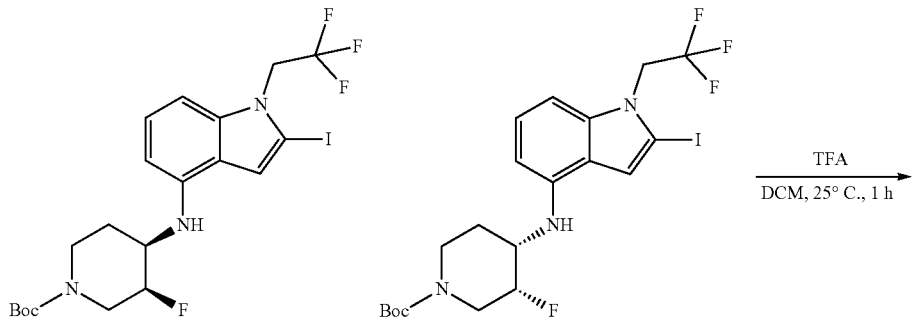

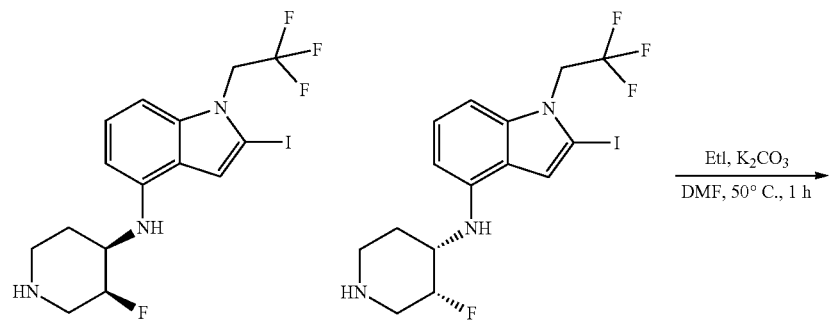

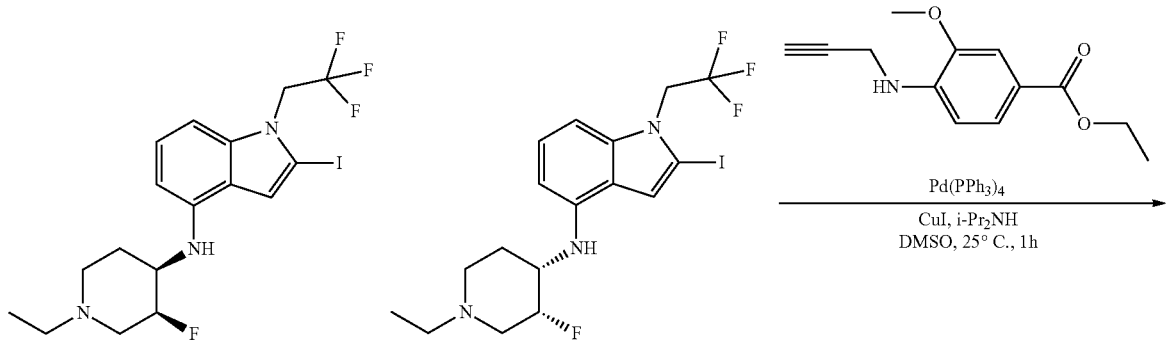

-continued

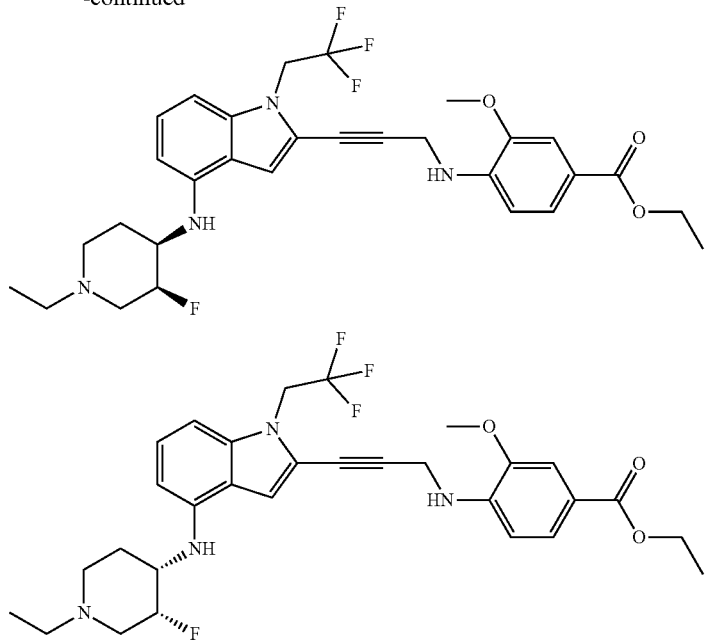

Preparation of N-((3S,4R)-3-fluoropiperidin-4-yl)-2-iodo-1-(2,2,2-trifluoroethyl)-1H-indol-4-amine and N-((3R,4S)-3-fluoropiperidin-4-yl)-2-iodo-1-(2,2,2-trifluoroethyl)-1H-indol-4-amine: To a solution of tert-butyl (3S,4R)-3-fluoro-4-((2-iodo-1-(2,2,2-trifluoroethyl)-1H-indol-4-yl)amino)piperidine-1-carboxylate (0.3 g, 554.20 µmol, 1 eq.) or tert-butyl (3R,4S)-3-fluoro-4-((2-iodo-1-(2,2,2-trifluoroethyl)-1H-indol-4-yl)amino)piperidine-1-carboxylate (0.3 g, 554.20 µmol, 1 eq.) in DCM (3 mL) was added TFA (1 mL). The reaction mixture was stirred at 25° C. for 1 h under $N_2$. LC-MS analysis showed that the reaction was complete. The reaction mixture was quenched by adding a saturated aqueous solution of $Na_2CO_3$ and to adjust the pH of the mixture to 8 and extracted with EtOAc (50 mL×2). The combined organic layers were washed with brine (100 mL×2), dried over anhydrous sodium sulfate, filtered, and concentrated under reduced pressure. The desired products were obtained as yellow solids.

N-((3S,4R)-3-fluoropiperidin-4-yl)-2-iodo-1-(2,2,2-trifluoroethyl)-1H-indol-4-amine, MS ($ES^{30}$, m/z): 442.0; and N-((3R,4S)-3-fluoropiperidin-4-yl)-2-iodo-1-(2,2,2-trifluoroethyl)-1H-indol-4-amine, MS ($ES^{30}$, m/z): 442.0.

Preparation of N-((3S,4R)-1-ethyl-3-fluoropiperidin-4-yl)-2-iodo-1-(2,2,2-trifluoroethyl)-1H-indol-4-amine and N-((3R,4S)-1-ethyl-3-fluoropiperidin-4-yl)-2-iodo-1-(2,2,2-trifluoroethyl)-1H-indol-4-amine: To a solution of N-((3S,4R)-3-fluoropiperidin-4-yl)-2-iodo-1-(2,2,2-trifluoroethyl)-1H-indol-4-amine (0.24 g, 543.97 µmol, 1 eq) or N-((3R,4S)-3-fluoropiperidin-4-yl)-2-iodo-1-(2,2,2-trifluoroethyl)-1H-indol-4-amine (300 mg, 679.96 µmol, 1 eq.) in DMF (3 mL) were added iodoethane (127.26 mg, 815.95 µmol, 65.26 µL, 1.5 eq.) and $K_2CO_3$ (225.54 mg, 1.63 mmol, 3 eq.). The mixture was stirred at 50° C. for 1 h. LC-MS analysis showed that the reaction was complete. The reaction mixture was quenched by adding water (80 mL) and extracted with EtOAc (30 mL×3). The combined organic layers were washed with brine (50 mL×3), dried over anhydrous sodium sulfate, filtered, and concentrated under reduced pressure. The desired products were obtained as yellow solids.

N-((3S,4R)-1-ethyl-3-fluoropiperidin-4-yl)-2-iodo-1-(2,2,2-trifluoroethyl)-1H-indol-4-amine, MS ($ES^{30}$, m/z): 470.0; and N-((3R,4S)-1-ethyl-3-fluoropiperidin-4-yl)-2-iodo-1-(2,2,2-trifluoroethyl)-1H-indol-4-amine, MS ($ES^{30}$, m/z): 470.0.

Preparation of final products: To a solution of ethyl 3-methoxy-4-(prop-2-yn-1-ylamino)benzoate (74.56 mg, 319.65 µmol 1.5 eq.) in DMSO (3 mL) were added i-$Pr_2NH$ (215.64 mg, 2.13 mmol, 301.17 µL, 10 eq.), CuI (8.12 mg, 42.62 µmol 0.2 eq.), N-((3S,4R)-1-ethyl-3-fluoropiperidin-4-yl)-2-iodo-1-(2,2,2-trifluoroethyl)-1H-indol-4-amine (0.1 g, 213.10 µmol, 1 eq) or N-((3R,4S)-1-ethyl-3-fluoropiperidin-4-yl)-2-iodo-1-(2,2,2-trifluoroethyl)-1H-indol-4-amine (0.1 g, 213.10 µmol, 1 eq.), and Pd(PPh$_3$)$_4$ (24.63 mg, 21.31 µmol, 0.1 eq.). The mixture was stirred at 25° C. for 1 h under $N_2$. TLC analysis showed that the reaction was complete. The reaction mixture was quenched by adding a saturated aqueous EDTA solution (100 mL) and extracted with EtOAc (50 mL) at 25° C. The resulting mixture was further extracted with EtOAc (50 mL×2). The combined organic layers were washed with brine (100 mL×2), dried over anhydrous sodium sulfate, filtered, and concentrated under reduced pressure. The residue was purified by prep-TLC and prep-HPLC to obtain the desired products as white solids.

ethyl 4-{1[3-(4-{[(3S,4R)-1-ethyl-3-fluoropiperidin-4-yl]amino}-1-(2,2,2-trifluoroethyl)-1H-indol-2-yl)prop-2-yn-1-yl]amino}-3-methoxybenzoate, 33.4 mg, 27.1% yield, MS ($ES^{30}$, m/z): 575.3; and ethyl 4-{[3-(4-{[(3R,4S)-1-ethyl-3-fluoropiperidin-4-yl]amino}-1-(2,2,2-trifluoroethyl)-1H-indol-2-yl)prop-2-yn-1-yl]amino}-3-methoxybenzoate, 27.9 mg, 22.8% yield, MS ($ES^{30}$, m/z): 575.3.

Example D99: Synthesis of Compounds 796A and 797A

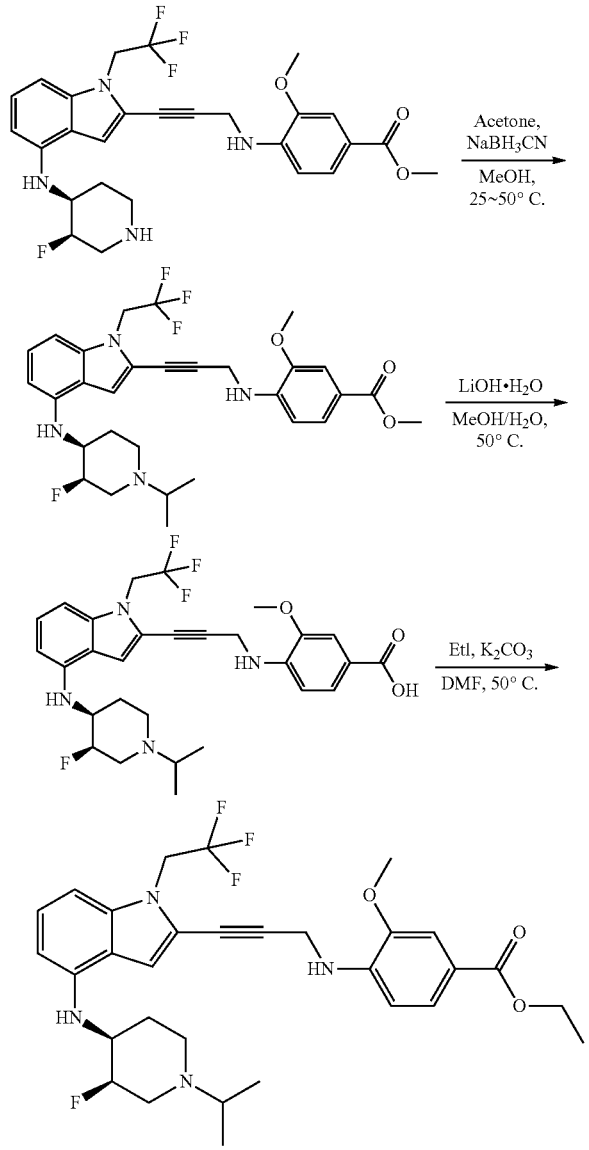

Preparation of methyl 4-((3-(4-(((3R,4S)-3-fluoro-1-isopropylpiperidin-4-yl)amino)-1-(2,2,2-trifluoroethyl)-1H-indol-2-yl)prop-2-yn-1-yl)amino)-3-methoxybenzoate: To a solution of methyl 4-((3-(4-(((3R,4S)-3-fluoropiperidin-4-yl)amino)-1-(2,2,2-trifluoroethyl)-1H-indol-2-yl)prop-2-yn-1-yl)amino)-3-methoxybenzoate (0.3 g, 563.35 µmol, 1 eq.) in MeOH (3 mL) was added acetone (327.19 mg, 5.63 mmol, 414.16 µL, 10 eq.). The mixture was stirred at 25° C. for 1 h, and NaBH$_3$CN (70.80 mg, 1.13 mmol, 2 eq.) was added to the reaction. The resulting reaction mixture was stirred at 25° C. for 1 h and was then stirred further at 50° C. for 12 h. TLC analysis showed that the reaction was complete. The reaction mixture was quenched with water (100 mL) and extracted with EtOAc (50 mL×2). The combined organic layers were washed with brine (100 mL×2), dried over anhydrous sodium sulfate, filtered, and concentrated under reduced pressure. The crude residue was purified by prep-TLC (SiO$_2$, DCM:MeOH=10:1) to afford the desired product (0.3 g, 522.09 µmol, 92.68% yield) as a yellow oil.

Preparation of 4-((3-(4-(((3R,4S)-3-fluoro-1-isopropylpiperidin-4-yl)amino)-1-(2,2,2-trifluoroethyl)-1H-indol-2-yl)prop-2-yn-1-yl)amino)-3-methoxybenzoic acid: To a solution of methyl 4-((3-(4-(((3R,4S)-3-fluoro-1-isopropylpiperidin-4-yl)amino)-1-(2,2,2-trifluoroethyl)-1H-indol-2-yl)prop-2-yn-1-yl)amino)-3-methoxybenzoate (0.25 g, 435.08 µmol, 1 eq.) in MeOH (3 mL) was added LiOH·H$_2$O (365.12 mg, 8.70 mmol, 20 eq.). Then, water (3 mL) was added, and the mixture was stirred at 50° C. for 2 h. TLC analysis showed that the reaction was complete. The reaction mixture was quenched by adding water (100 mL) and extracted with EtOAc (50 mL×2). The combined organic layers were washed with brine (100 mL×2), dried over anhydrous sodium sulfate, filtered, and concentrated under reduced pressure to give a residue. The residue was purified by prep-HPLC to obtain the desired product (22.8 mg, 40.67 µmol, 45.60% yield) as a white solid. MS (ES$^{30}$, m/z): 561.3.

Preparation of ethyl 4-((3-(4-(((3R,4S)-3-fluoro-1-isopropylpiperidin-4-yl)amino)-1-(2,2,2-trifluoroethyl)-1H-indol-2-yl)prop-2-yn-1-yl)amino)-3-methoxybenzoate: To a solution of 4-((3-(4-(((3R,4S)-3-fluoro-1-isopropylpiperidin-4-yl)amino)-1-(2,2,2-trifluoroethyl)-1H-indol-2-yl)prop-2-yn-1-yl)amino)-3-methoxybenzoic acid (60 mg, 107.03 µmol, 1 eq.) in DMF (3 mL) were added iodoethane (50.08 mg, 321.10 µmol, 25.68 µL, 3 eq.) and K$_2$CO$_3$ (44.38 mg, 321.10 µmol, 3 eq.). The mixture was stirred at 50° C. for 1 h. LC-MS analysis showed that the reaction was complete. The reaction mixture was quenched by adding water (100 mL) and extracted with EtOAc (50 mL×2). The combined organic layers were washed with brine (100 mL×2), dried over anhydrous sodium sulfate, filtered, and concentrated under reduced pressure to give a residue. The residue was purified by prep-HPLC to afford the desired product (25.0 mg, 42.47 µmol, 39.68% yield) as a white solid. MS (ES$^{30}$, m/z): 589.3.

Example D100: Synthesis of Compounds 809A, 810A, 821A, and 825A

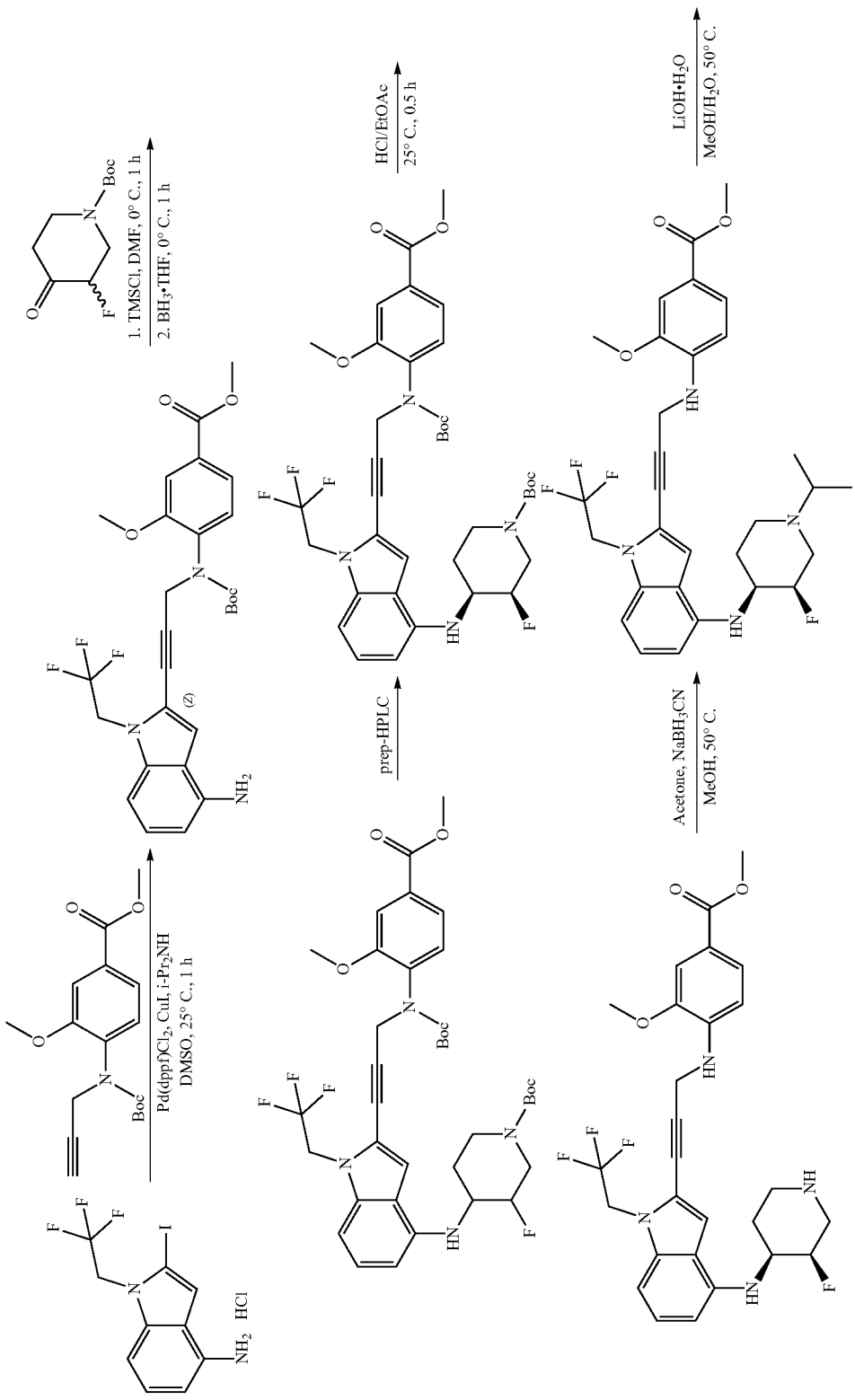

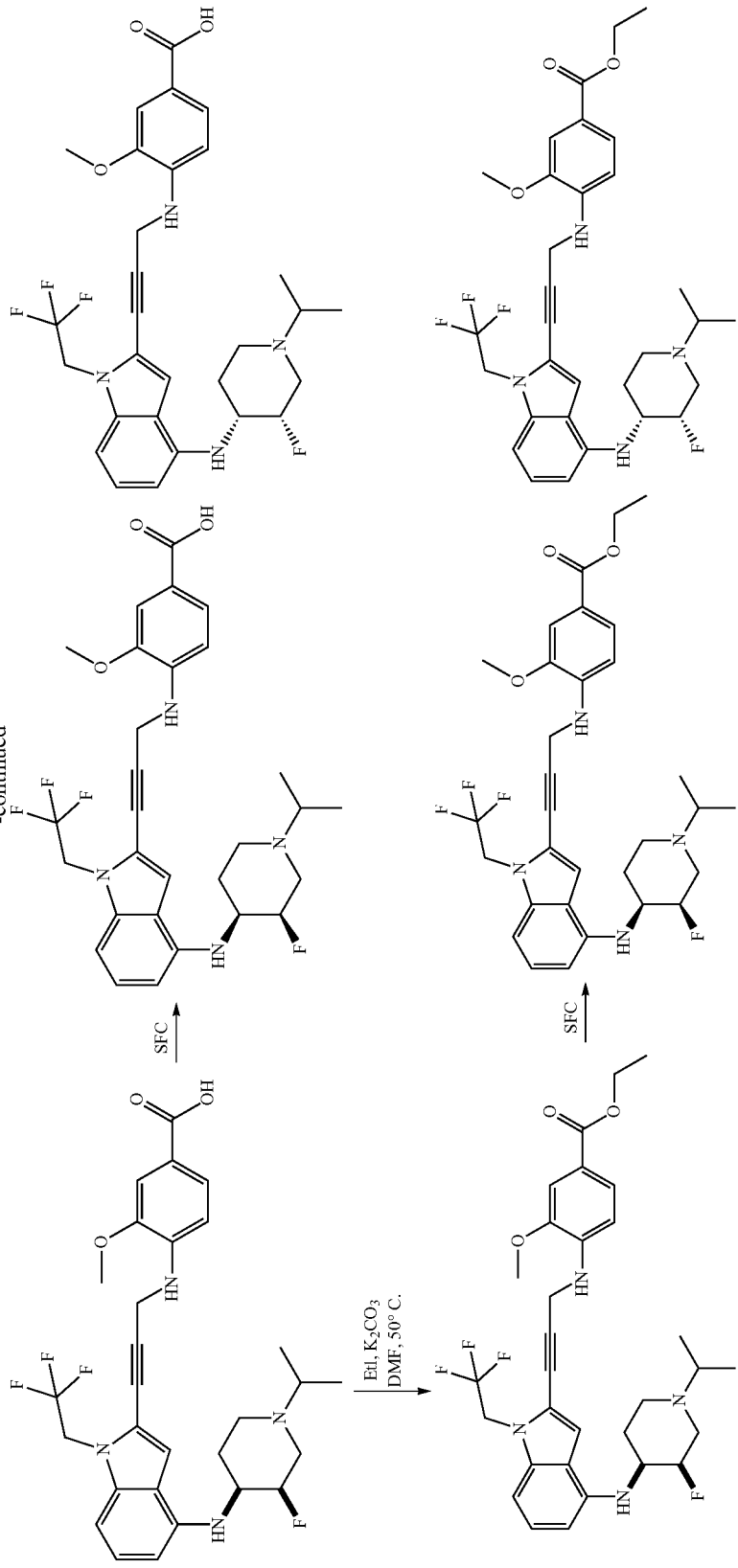

Preparation of methyl 4-((3-(4-amino-1-(2,2,2-trifluoroethyl)-1H-indol-2-yl)prop-2-yn-1-yl)(tert-butoxycarbonyl)amino)-3-methoxybenzoate: To a solution of methyl 4-((tert-butoxycarbonyl)(prop-2-yn-1-yl)amino)-3-methoxybenzoate (1.2 eq.) in DMSO (80 mL) were added i-Pr$_2$NH (10 eq.), CuI (0.2 eq.), 2-iodo-1-(2,2,2-trifluoroethyl)-1H-indol-4-amine hydrochloride (9 g, 1 eq.), and Pd(PPh$_3$)$_4$ (0.05 eq.). The mixture was stirred at 25° C. for 1 h under N$_2$. TLC analysis showed that the reaction was complete. Saturated aqueous EDTA (300 mL) and EtOAc (100 mL) were added to the reaction mixture at 25° C. The resulting mixture was filtered and extracted with EtOAc (150 mL×2). The organic phase was washed with water (500 mL×2) and brine (500 mL×2), dried over anhydrous sodium sulfate, filtered, and concentrated under reduced pressure. The crude residue was purified by column chromatography (SiO$_2$, PE:EtOAc=20:1 to 2:1) to afford the desired product (13.5 g, 25.40 mmol) (86.4% yield) as a black brown oil.

Preparation of tert-butyl 4-((2-(3-((tert-butoxycarbonyl)(2-methoxy-4-(methoxycarbonyl)phenyl)amino)prop-1-yn-1-yl)-1-(2,2,2-trifluoroethyl)-1H-indol-4-yl)amino)-3-fluoropiperidine-1-carboxylate: To a solution of methyl 4-((3-(4-amino-1-(2,2,2-trifluoroethyl)-1H-indol-2-yl)prop-2-yn-1-yl)(tert-butoxycarbonyl)amino)-3-methoxybenzoate (11 g, 1 eq.) in DMF (100 mL) were added tert-butyl 3-fluoro-4-oxopiperidine-1-carboxylate (5 eq.) and TMSCl (2.5 eq.). The mixture was stirred at 0° C. for 1 h, and BH$_3$·THF (1 M, 3 eq.) was added to the mixture. The resulting reaction mixture was stirred at 0° C. for 1 h. LC-MS analysis showed that the reaction was complete. The reaction mixture was quenched by adding ice water (250 mL), and the mixture was extracted with EtOAc (250 mL×2). The combined organic layers were washed with water (500 mL×2) and brine (500 mL×2), dried over anhydrous sodium sulfate, filtered, and concentrated under reduced pressure to afford the desired product (20 g, crude) as a black brown oil. MS (ES$^{30}$, m/z): 755.3.

Preparation of tert-butyl (3R,4S)-4-((2-(3-((tert-butoxycarbonyl)(2-methoxy-4-(methoxycarbonyl)phenyl)amino)prop-1-yn-1-yl)-1-(2,2,2-trifluoroethyl)-1H-indol-4-yl)amino)-3-fluoropiperidine-1-carboxylate: tert-Butyl 4-((2-(3-((tert-butoxycarbonyl)(2-methoxy-4-(methoxycarbonyl)phenyl)amino)prop-1-yn-1-yl)-1-(2,2,2-trifluoroethyl)-1H-indol-4-yl)amino)-3-fluoropiperidine-1-carboxylate was purified by prep-HPLC. The pH of the solution was adjusted to 8 by adding saturated Na$_2$CO$_3$. The solution was concentrated, and the mixture was extracted with EtOAc (250 mL×2). The combined organic layers were washed with brine (500 mL×2), dried over anhydrous sodium sulfate, filtered, and concentrated in vacuo to afford the desired product (10.5 g, 14.33 mmol, 58.33% yield) as a white solid.

Preparation of methyl 4-((3-(4-(((3R,4S)-3-fluoropiperidin-4-yl)amino)-1-(2,2,2-trifluoroethyl)-1H-indol-2-yl)prop-2-yn-1-yl)amino)-3-methoxybenzoate: To a solution of tert-butyl (3R,4S)-4-((2-(3-((tert-butoxycarbonyl)(2-methoxy-4-(methoxycarbonyl)phenyl)amino)prop-1-yn-1-yl)-1-(2,2,2-trifluoroethyl)-1H-indol-4-yl)amino)-3-fluoropiperidine-1-carboxylate (2 g, 2.73 mmol, 1 eq.) in EtOAc (10 mL) was added HCl/EtOAc (4 M, 20 mL, 29.31 eq.). The mixture was stirred at 25° C. for 0.5 h. TLC analysis showed that the reaction was complete. The reaction mixture was quenched by adding water (100 mL), and the pH of the solution was adjusted to 8 by adding saturated Na$_2$CO$_3$. The resulting mixture was extracted with EtOAc (100 mL×2). The combined organic layers were washed with brine (100 mL×2), dried over anhydrous sodium sulfate, filtered, and concentrated in vacuo to obtain the desired product (1.6 g, crude) as a white solid.

Preparation of methyl 4-((3-(4-(((3R,4S)-3-fluoro-1-isopropylpiperidin-4-yl)amino)-1-(2,2,2-trifluoroethyl)-1H-indol-2-yl)prop-2-yn-1-yl)amino)-3-methoxybenzoate: To a solution of methyl 4-((3-(4-(((3R,4S)-3-fluoropiperidin-4-yl)amino)-1-(2,2,2-trifluoroethyl)-1H-indol-2-yl)prop-2-yn-1-yl)amino)-3-methoxybenzoate (0.45 g, 845.02 µmol, 1 eq.) in MeOH (5 mL) was added acetone (490.78 mg, 8.45 mmol, 621.24 µL, 10 eq.). The mixture was stirred at 50° C. for 1 h, and NaBH$_3$CN (106.21 mg, 1.69 mmol, 2 eq.) was added to the reaction. The resulting mixture was stirred at 50° C. for 11 h. TLC analysis showed that the reaction was complete. The reaction mixture was quenched by adding water (100 mL), and the mixture was extracted with EtOAc (50 mL×2). The combined organic layers were washed with brine (100 mL×2), dried over anhydrous sodium sulfate, filtered, and concentrated under reduced pressure. The crude residue was purified by prep-TLC (SiO$_2$, DCM:MeOH=10:1) to obtain the desired product (0.45 g, 783.14 µmol, 92.68% yield) as a yellow oil.

Preparation of 4-((3-(4-(((3R,4S)-3-fluoro-1-isopropylpiperidin-4-yl)amino)-1-(2,2,2-trifluoroethyl)-1H-indol-2-yl)prop-2-yn-1-yl)amino)-3-methoxybenzoic acid: To a solution of methyl 4-((3-(4-(((3R,4S)-3-fluoro-1-isopropylpiperidin-4-yl)amino)-1-(2,2,2-trifluoroethyl)-1H-indol-2-yl)prop-2-yn-1-yl)amino)-3-methoxybenzoate (0.4 g, 696.13 µmol, 1 eq.) in MeOH (3 mL) was added LiOH·H$_2$O (584.19 mg, 13.92 mmol, 20 eq.). Then, water (3 mL) was added to the reaction, and the mixture was stirred at 50° C. for 2 h. TLC analysis showed that the reaction was complete. The reaction mixture was quenched by adding water (100 mL), and the resulting mixture was extracted with EtOAc (50 mL×3). The combined organic layers were washed with brine (100 mL×2), dried over anhydrous sodium sulfate, filtered, and concentrated under reduced pressure to obtain the desired product (0.4 g, crude) as a yellow solid.

4-((3-(4-(((3R,4S)-3-Fluoro-1-isopropylpiperidin-4-yl)amino)-1-(2,2,2-trifluoroethyl)-1H-indol-2-yl)prop-2-yn-1-yl)amino)-3-methoxybenzoic acid was separated by SFC to obtain the desired products. 4-{[3-(4-{[(3S,4R)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoic acid, MS (ES$^{30}$, m/z): 561.2; and 4-{[3-(4-{[(3R,4S)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoic acid, MS (ES$^{30}$, m/z): 561.2.

Preparation of ethyl 4-((3-(4-(((3R,4S)-3-fluoro-1-isopropylpiperidin-4-yl)amino)-1-(2,2,2-trifluoroethyl)-1H-indol-2-yl)prop-2-yn-1-yl)amino)-3-methoxybenzoate: To a solution of 4-((3-(4-(((3R,4S)-3-fluoro-1-isopropylpiperidin-4-yl)amino)-1-(2,2,2-trifluoroethyl)-1H-indol-2-yl)prop-2-yn-1-yl)amino)-3-methoxybenzoic acid (0.15 g, 267.58 µmol, 1 eq.) in DMF (3 mL) were added iodoethane (41.73 mg, 267.58 µmol, 21.40 µL, 1 eq.) and K$_2$CO$_3$ (110.94 mg, 802.74 µmol, 3 eq.). The mixture was stirred at 50° C. for 1 h. TLC analysis showed that the reaction was complete. The reaction mixture was quenched by adding water (100 mL), and the resulting mixture was extracted with EtOAc (50 mL×2). The combined organic layers were washed with brine (100 mL×2), dried over anhydrous sodium sulfate, filtered, and concentrated under reduced pressure to obtain the desired product (0.14 g, crude) as a yellow solid.

Ethyl 4-((3-(4-(((3R,4S)-3-fluoro-1-isopropylpiperidin-4-yl)amino)-1-(2,2,2-trifluoroethyl)-1H-indol-2-yl)prop-2-yn- 1-yl)amino)-3-methoxybenzoate was separated by SFC to obtain the desired products as white solids. Ethyl 4-{[3-(4-{[(3R,4S)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoate, MS (ES³⁰, m/z): 589.2; and ethyl 4-{[3-(4-{[(3S,4R)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoate, MS (ES³⁰, m/z): 589.2.

Example D101: Synthesis of Compounds 822A, 823A, 824A, 828A, 829A, and 958A

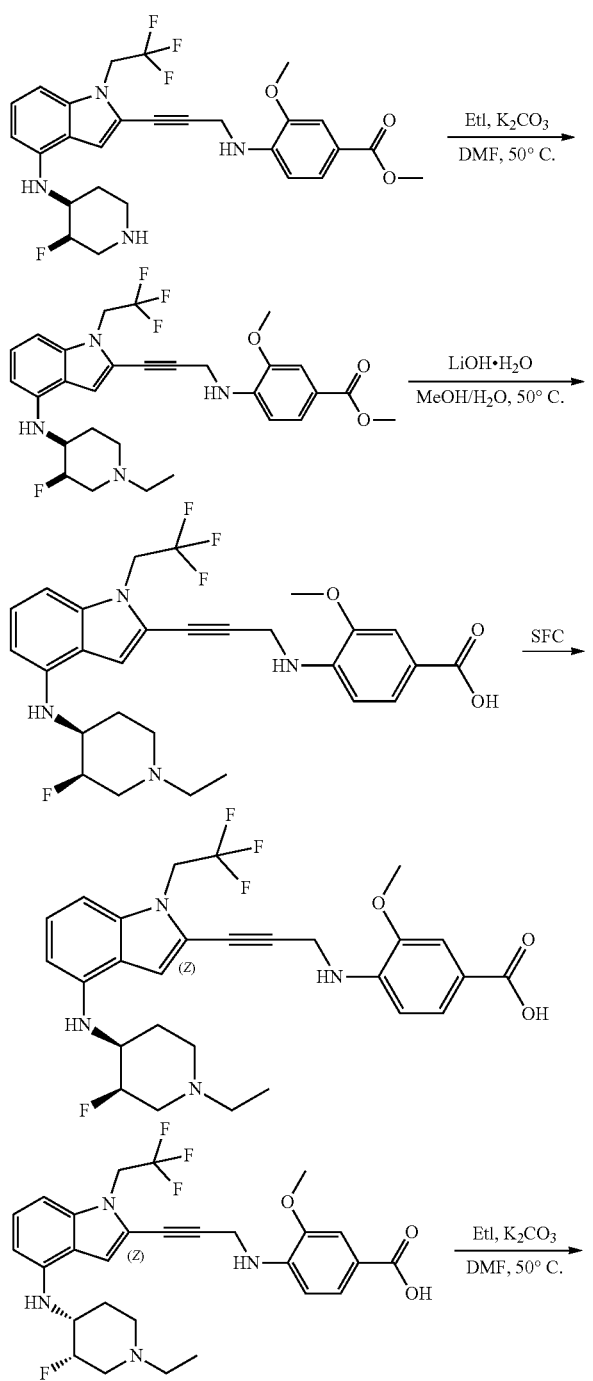

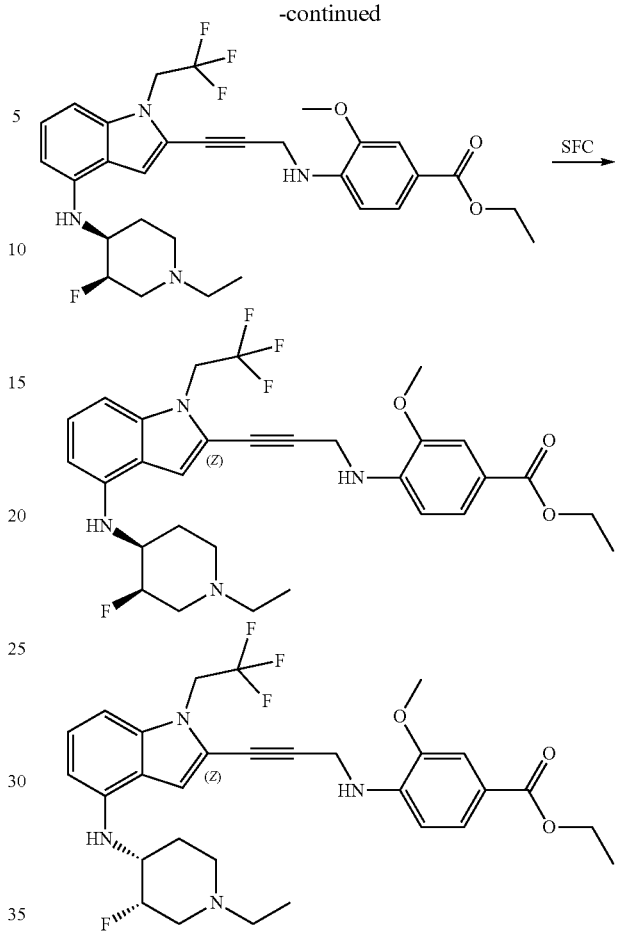

Preparation of methyl 4-((3-(4-(((3R,4S)-1-ethyl-3-fluoropiperidin-4-yl)amino)-1-(2,2,2-trifluoroethyl)-1H-indol-2-yl)prop-2-yn-1-yl)amino)-3-methoxybenzoate: To a solution of methyl 4-((3-(4-(((3R,4S)-3-fluoropiperidin-4-yl)amino)-1-(2,2,2-trifluoroethyl)-1H-indol-2-yl)prop-2-yn-1-yl)amino)-3-methoxybenzoate (0.45 g, 845.02 μmol, 1 eq.) in DMF (5 mL) were added iodoethane (197.69 mg, 1.27 mmol, 101.38 μL, 1.5 eq.) and K₂CO₃ (350.37 mg, 2.54 mmol, 3 eq.). The mixture was stirred at 50° C. for 1 h. TLC analysis showed that the reaction was complete. The reaction mixture was quenched with water (100 mL), and the mixture was extracted with EtOAc (50 mL×2). The combined organic layers were washed with brine (50 mL×2), dried over anhydrous sodium sulfate, filtered, and concentrated under reduced pressure. The crude residue was purified by prep-TLC (SiO₂, DCM:MeOH=10:1) to afford the desired product (0.43 g, 767.06 μmol, 90.77% yield) as a yellow oil.

Preparation of 4-((3-(4-(((3R,4S)-1-ethyl-3-fluoropiperidin-4-yl)amino)-1-(2,2,2-trifluoroethyl)-1H-indol-2-yl)prop-2-yn-1-yl)amino)-3-methoxybenzoic acid: To a solution of methyl 4-((3-(4-(((3R,4S)-1-ethyl-3-fluoropiperidin-4-yl)amino)-1-(2,2,2-trifluoroethyl)-1H-indol-2-yl)prop-2-yn-1-yl)amino)-3-methoxybenzoate (0.38 g, 677.87 μmol, 1 eq.) in MeOH (3 mL) was added LiOH·H₂O (568.92 mg, 13.56 mmol, 20 eq.). Then, water (3 mL) was added to the reaction, and the mixture was stirred at 50° C. for 1 h. TLC analysis showed that the reaction was complete. The reaction mixture was quenched by adding water (100 mL), and the resulting mixture was extracted with EtOAc (50 mL×3).

The combined organic layers were washed with brine (100 mL×2), dried over anhydrous sodium sulfate, filtered, and concentrated under reduced pressure. The residue was purified by prep-HPLC to afford the desired product (20.8 mg, 38.06 μmol) as a white solid. MS (ES$^{30}$, m/z): 574.2.

Preparation of Compounds 828A and 829A: 4-((3-(4-(((3R,4S)-1-Ethyl-3-fluoropiperidin-4-yl)amino)-1-(2,2,2-trifluoroethyl)-1H-indol-2-yl)prop-2-yn-1-yl)amino)-3-methoxybenzoic acid was separated by SFC to obtain the desired products as white solids. 4-{[3-(4-{[(3R,4S)-1-ethyl-3-fluoropiperidin-4-yl]amino}-1-(2,2,2-trifluoro-ethyl)-1H-indol-2-yl)prop-2-yn-1-yl]amino}-3-methoxy-benzoic acid, MS (ES$^{30}$, m/z): 547.3; 4-{[3-(4-{[(3S,4R)-1-ethyl-3-fluoropiperidin-4-yl]amino}-1-(2,2,2-trifluoroethyl)-1H-indol-2-yl)prop-2-yn-1-yl]amino}-3-methoxybenzoic acid, MS (ES$^{30}$, m/z): 547.3.

Preparation of ethyl 4-((3-(4-(((3R,4S)-1-ethyl-3-fluoropiperidin-4-yl)amino)-1-(2,2,2-trifluoroethyl)-1H-indol-2-yl)prop-2-yn-1-yl)amino)-3-methoxybenzoate: To a solution of 4-((3-(4-(((3R,4S)-1-ethyl-3-fluoropiperidin-4-yl)amino)-1-(2,2,2-trifluoroethyl)-1H-indol-2-yl)prop-2-yn-1-yl)amino)-3-methoxybenzoic acid (0.15 g, 274.45 μmol, 1 eq.) in DMF (3 mL) were added iodoethane (64.21 mg, 411.67 μmol, 32.93 μL, 1.5 eq.) and K$_2$CO$_3$ (113.79 mg, 823.34 μmol, 3 eq.). The mixture was stirred at 50° C. for 1 h. LC-MS analysis showed that the reaction was complete. The reaction mixture was quenched by adding water (100 mL), and the mixture was extracted with EtOAc (50 mL×2). The combined organic layers were washed with brine (100 mL×2), dried over anhydrous sodium sulfate, filtered, and concentrated under reduced pressure. The crude residue was purified by prep-HPLC to obtain the desired product (6.0 mg, 10.44 μmol) as a white solid. MS (ES$^{30}$, m/z): 575.2.

Preparation of Compounds 823A and 824A: ethyl 4-((3-(4-(((3R,4S)-1-ethyl-3-fluoropiperidin-4-yl)amino)-1-(2,2,2-trifluoroethyl)-1H-indol-2-yl)prop-2-yn-1-yl)amino)-3-methoxybenzoate was separated by SFC to obtain the desired products as white solids. ethyl 4-{[3-(4-{[(3R,4S)-1-ethyl-3-fluoropiperidin-4-yl]amino}-1-(2,2,2-trifluoroethyl)-1H-indol-2-yl)prop-2-yn-1-yl]amino}-3-methoxy-benzoate, MS (ES$^{30}$, m/z): 575.2; ethyl 4-{[3-(4-{[(3S,4R)-1-ethyl-3-fluoropiperidin-4-yl]amino}-1-(2,2,2-trifluoroethyl)-1H-indol-2-yl)prop-2-yn-1-yl]amino}-3-methoxybenzoate, MS (ES$^{30}$, m/z): 575.2.

Example D102: Synthesis of Compounds 872A and 873A

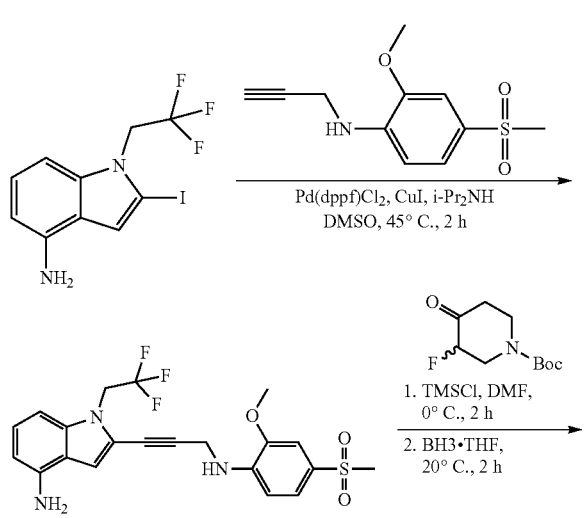

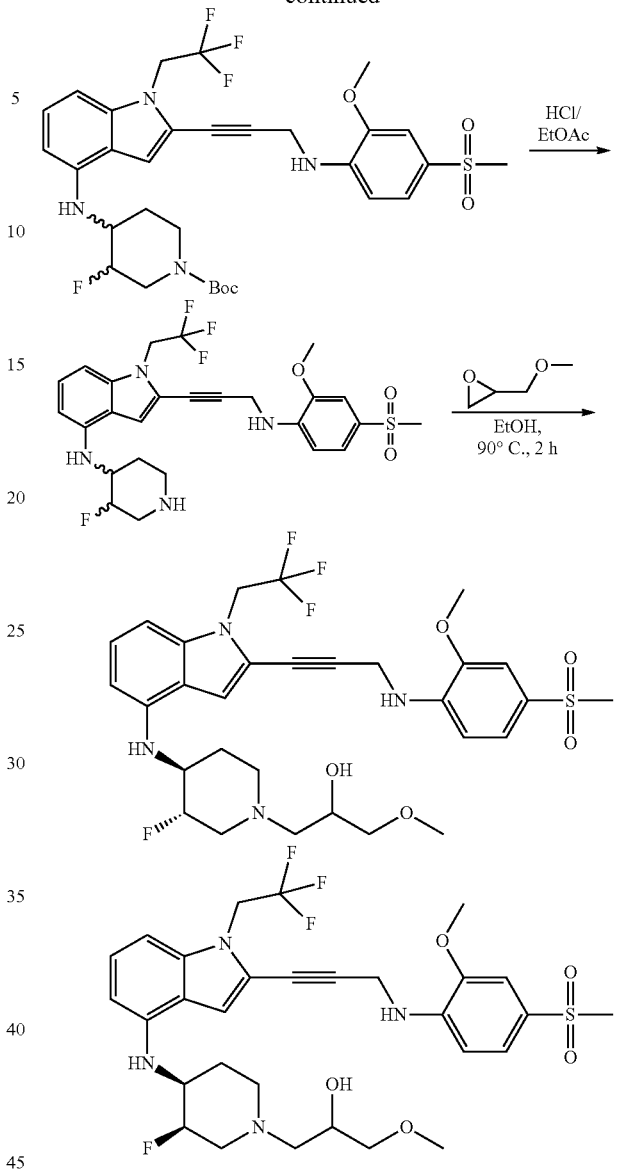

Preparation of 2-(3-((2-methoxy-4-(methylsulfonyl)phenyl)amino)prop-1-yn-1-yl)-1-(2,2,2-trifluoroethyl)-1H-indol-4-amine: To the mixture of 2-iodo-1-(2,2,2-trifluoroethyl)-1H-indol-4-amine (1 g, 2.94 mmol, 1 eq.) and 2-methoxy-4-methylsulfonyl-N-prop-2-ynyl-aniline (1.41 g, 5.88 mmol, 2 eq.) in DMSO (15 mL) were added into N-isopropylpropan-2-amine (2.98 g, 29.40 mmol, 4.16 mL, 10 eq.), Pd(dppf)Cl$_2$ (215.16 mg, 294.05 μmol, 0.1 eq.), and CuI (560.01 mg, 2.94 mmol, 1 eq.) under N$_2$. The mixture was stirred for 2 h at 45° C. LC-MS and TLC analysis (PE:EtOAc=1:1) showed that the reaction was complete. The reaction mixture was quenched by adding saturated aqueous EDTA (100 mL) at 25° C., and the resulting mixture was extracted with EtOAc (50 mL×3). The combined organic layers were dried over anhydrous sodium sulfate, filtered, and concentrated in vacuo. The crude residue was purified by column chromatography (PE:EtOAc=2:1 to 1:1) to afford the desired product (0.8 g, 1.68 mmol, 57.25% yield) as a light yellow solid. MS (ES$^{30}$, m/z): 452.0.

Preparation of tert-butyl 3-fluoro-4-((2-(3-((2-methoxy-4-(methylsulfonyl)phenyl)amino)prop-1-yn-1-yl)-1-(2,2,2- trifluoroethyl)-1H-indol-4-yl)amino)piperidine-1-carboxylate: To a mixture of 2-(3-((2-methoxy-4-(methylsulfonyl)phenyl)amino)prop-1-yn-1-yl)-1-(2,2,2-trifluoroethyl)-1H-indol-4-amine (360.89 mg, 1.66 mmol, 2.5 eq.) and 2-[3-(2-methoxy-4-methylsulfonyl-anilino)prop-1-ynyl]-1-(2,2,2-trifluoroethyl)indol-4-amine (300 mg, 664.51 μmol, 1 eq.) in DMF (6 mL) was added TMSCl (180.48 mg, 1.66 mmol, 210.84 μL, 2.5 eq.). The mixture was stirred at 0° C. for 2 h, and BH$_3$·THF (1 M, 3.32 mL, 5 eq.) was added to the reaction under N$_2$. The mixture was stirred at 20° C. for 2 h. LC-MS analysis showed that the reaction was complete. The reaction mixture was quenched by adding a saturated aqueous Na$_2$CO$_3$ (30 mL) solution, diluted with water (10 mL), and extracted with EtOAc (20 mL×2). The combined organic layers were washed with brine (10 mL), dried over anhydrous sodium sulfate, filtered, and concentrated in vacuo. The crude residue was purified by prep-HPLC to give the desired product (160 mg, 245.14 μmol, 36.89% yield) as a yellow solid. MS (ES$^{30}$, m/z): 653.2.

Preparation of N-(3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine: A solution of tert-butyl 3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidine-1-carboxylate (80 mg, 122.57 μmol, 1 eq.) in HCl/EtOAc (4 M, 8 mL, 261.08 eq.) was stirred at 25° C. for 10 min. LC-MS analysis showed that the reaction was complete. The solution was dried in vacuo to give the crude product. The crude product was neutralized by adding saturated aqueous Na$_2$CO$_3$ (100 mL) and extracted with EtOAc (20 mL). The combined organic layers were washed with brine (100 mL×3), dried over anhydrous sodium sulfate, filtered, and concentrated in vacuo to give the crude product (80 mg, crude) as a light yellow solid. MS (ES$^{30}$, m/z): 553.1.

Preparation of final products: To a solution of N-(3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine (60 mg, 108.58 μmol, 1 eq.) in EtOH (3 mL) was added 2-(methoxymethyl)oxirane (57.40 mg, 651.49 μmol, 57.98 μL, 6 eq.). The mixture was stirred at 90° C. for 2 h under N$_2$. LC-MS analysis showed that the reaction was complete. The reaction mixture was concentrated in vacuo, and the crude residue was purified by prep-HPLC to give the desired products as yellow solids.

1-((3S,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol, 25 mg, 35.0% yield, MS (ES$^{30}$, m/z): 641.2; and 1-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol, 25 mg, 35.0% yield, MS (ES$^{30}$, m/z): 641.2.

Example D103: Synthesis of Compounds 733A and 734A

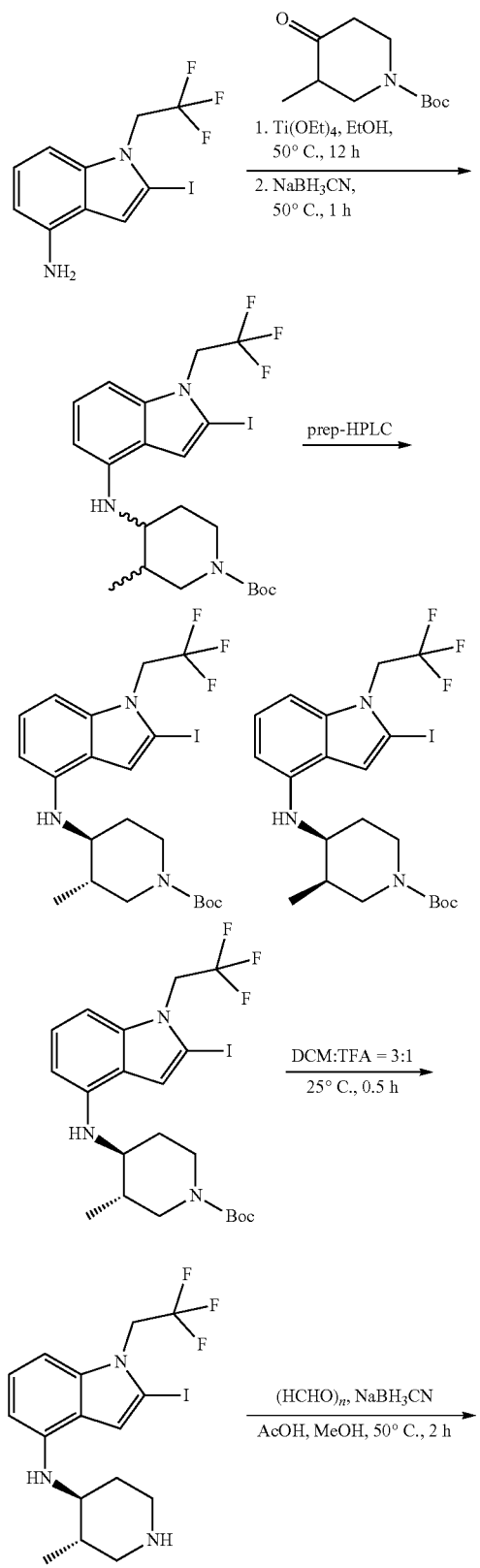

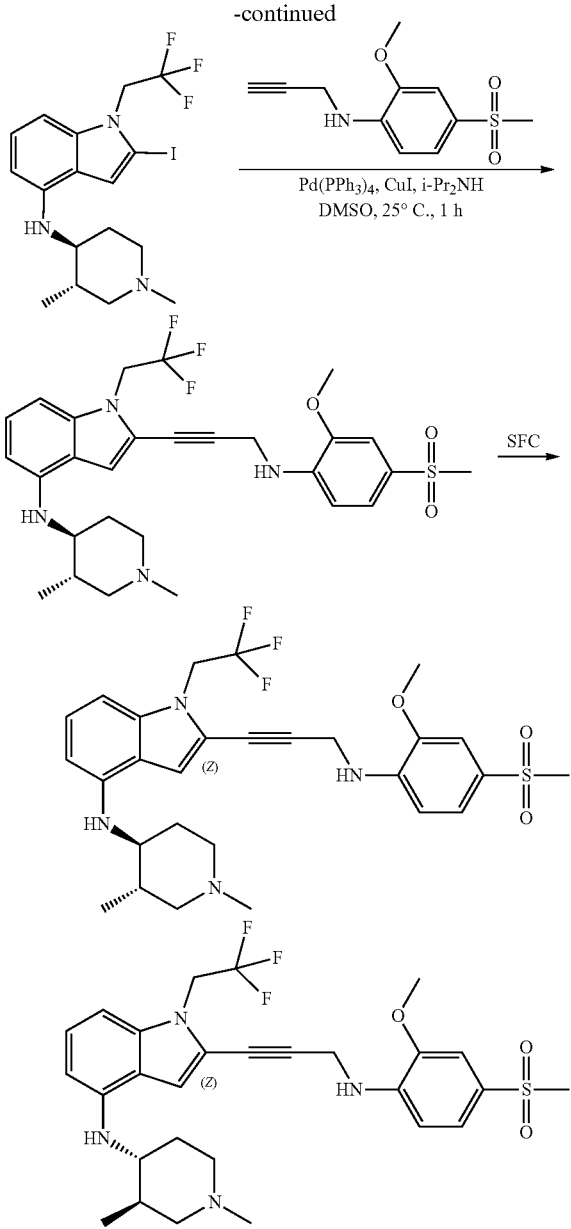

Preparation of tert-butyl (3S,4S)-4-((2-iodo-1-(2,2,2-trifluoroethyl)-1H-indol-4-yl)amino)-3-methylpiperidine-1-carboxylate and tert-butyl (3R,4S)-4-((2-iodo-1-(2,2,2-trifluoroethyl)-1H-indol-4-yl)amino)-3-methylpiperidine-1-carboxylate: To a mixture of 2-iodo-1-(2,2,2-trifluoroethyl) indol-4-amine (2.5 g, 7.35 mmol, 1 eq.) and tert-butyl 3-methyl-4-oxo-piperidine-1-carboxylate (4.70 g, 22.05 mmol, 3 eq.) in EtOH (25 mL) was added Ti(OEt)$_4$ (8.38 g, 36.76 mmol, 7.62 mL, 5 eq.). The mixture was stirred at 50° C. for 12 h, and NaBH$_3$CN (2.31 g, 36.76 mmol, 5 eq.) was added to the reaction mixture. The resulting reaction mixture was stirred at 50° C. for 1 h. LC-MS and TLC analysis showed that the reaction was complete. The reaction was poured saturated aqueous solution of Na$_2$CO$_3$ (8 mL) at 0° C., and the resulting mixture was extracted with EtOAc (40 mL×3). The combined organic layers were washed with brine (40 mL×3), dried over anhydrous sodium sulfate, filtered, and concentrated under reduced pressure. The residue was purified by column chromatography (SiO$_2$, PE:EtOAc=1:0 to 10:1) and prep-HPLC to afford the desired products as grey solids.

Preparation of 2-iodo-N-((3S,4S)-3-methylpiperidin-4-yl)-1-(2,2,2-trifluoroethyl)-1H-indol-4-amine: To a solution of tert-butyl (3S,4S)-4-((2-iodo-1-(2,2,2-trifluoroethyl)-1H-indol-4-yl)amino)-3-methylpiperidine-1-carboxylate (490 mg, 911.87 μmol, 1 eq.) in DCM (6 mL) was added TFA (3.08 g, 27.01 mmol, 2 mL, 29.62 eq.). The mixture was stirred at 25° C. for 0.5 h. TLC analysis showed that the reaction was complete. Saturated aqueous Na$_2$CO$_3$ (20 mL) was added to the mixture to adjust the pH of the mixture to 9, and the resulting mixture was extracted with EtOAc (20 mL×3). The combined organic layers were washed with brine (20 mL×3), dried over anhydrous sodium sulfate, filtered, and concentrated under reduced pressure to obtain the desired product (0.36 g, crude) as a brown solid.

Preparation of N-((3S,4S)-1,3-dimethylpiperidin-4-yl)-2-iodo-1-(2,2,2-trifluoroethyl)-1H-indol-4-amine: To a mixture of 2-iodo-N-((3S,4S)-3-methylpiperidin-4-yl)-1-(2,2,2-trifluoroethyl)-1H-indol-4-amine (0.28 g, 640.38 μmol, 1 eq.) and formaldehyde (38.46 mg, 1.28 mmol, 35.28 μL, 2 eq.) in MeOH (6 mL) was added AcOH (38.46 ug, 0.64 μmol, 3.66e-2 μL, 0.001 eq.). The mixture was then stirred at 50° C. for 1 h, and NaBH$_3$CN (201.21 mg, 3.20 mmol, 5 eq.) was added to the reaction. The reaction mixture was stirred further at 50° C. for 1 h. LC-MS analysis showed that the reaction was complete. The reaction mixture was poured into to water (15 mL), and the resulting mixture was extracted with EtOAc (15 mL×3). The combined organic layers were washed with brine (15 mL×3), dried over anhydrous sodium sulfate, filtered, and concentrated under reduced pressure. The residue was purified by prep-TLC (SiO$_2$, DCM:MeOH=10:1) to afford the desired product (0.24 g, 531.84 μmol, 83.05% yield) as a yellow solid. MS (ES$^{30}$, m/z): 452.1.

Preparation of N-((3S,4S)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine: To a solution of 2-methoxy-4-methylsulfonyl-N-prop-2-ynyl-aniline (127.26 mg, 531.84 μmol, 1.2 eq.) in DMSO (2 mL) were added N-isopropylpropan-2-amine (448.47 mg, 4.43 mmol, 626.36 μL, 10 eq.), CuI (84.41 mg, 443.20 μmol, 1 eq.), N-((3S,4S)-1,3-dimethylpiperidin-4-yl)-2-iodo-1-(2,2-trifluoroethyl)-1H-indol-4-amine (0.2 g, 443.20 μmol, 1 eq.), and Pd(PPh$_3$)$_4$ (204.86 mg, 177.28 μmol, 0.4 eq.). The mixture was stirred at 25° C. for 1 h under N$_2$. TLC analysis showed that the reaction was complete. The reaction was diluted with EtOAc (15 mL), and the resulting mixture was poured into saturated aqueous EDTA (15 mL) and stirred at 25° C. for 1 h. The mixture was extracted with EtOAc (10 mL), and The combined organic layers were washed with brine (10 mL×3), dried over anhydrous sodium sulfate, filtered, and concentrated under reduced pressure. The crude residue was purified by prep-TLC (SiO$_2$, DCM:MeOH=10:1) and prep-HPLC to obtain the desired product (0.1 g, 177.73 μmol, 40.10% yield) as a yellow solid.

Preparation of final products: N-((3S,4S)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine was purified by SFC to obtain the final products. N-((3S,4S)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine (0.0224 g, 39.81 μmol), MS (ES$^{30}$, m/z): 563.2; and N-((3R,4R)-1,3-dimethylpiperidin-4-yl)-2-(3-((2-methoxy-4-(methylsulfonyl)phenyl)

amino)prop-1-yn-1-yl)-1-(2,2,2-trifluoroethyl)-1H-indol-4-amine (0.0222 g, 39.26 μmol), MS (ES³⁰, m/z): 563.3.

Example D104: Synthesis of Compounds 736A and 737A

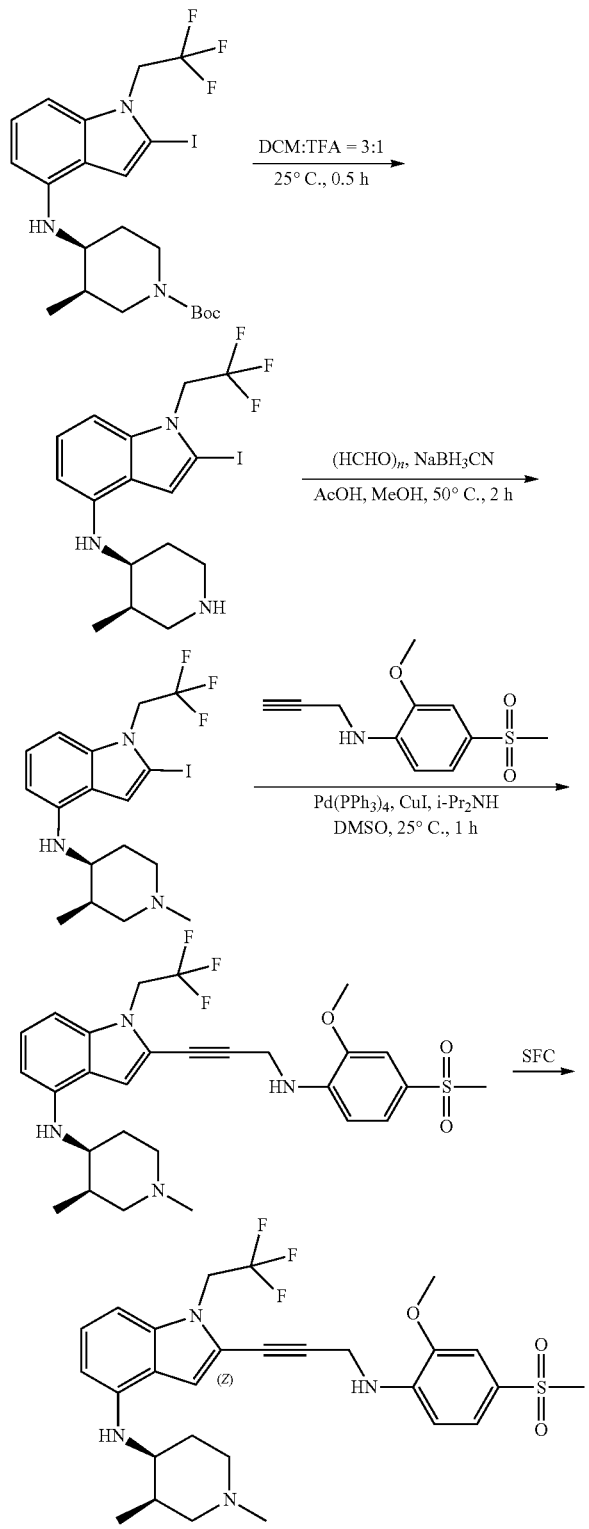

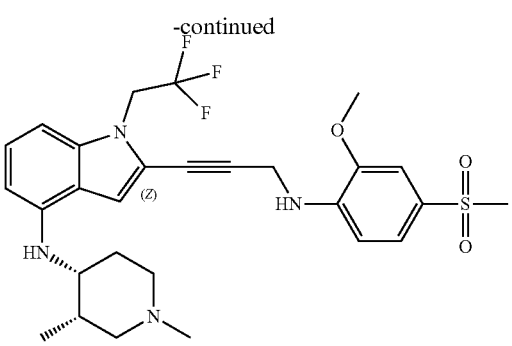

Preparation of 2-iodo-N-((3R,4S)-3-methylpiperidin-4-yl)-1-(2,2,2-trifluoroethyl)-1H-indol-4-amine: To a solution of tert-butyl (3R,4S)-4-[[2-iodo-1-(2,2,2-trifluoroethyl)indol-4-yl]amino]-3-methyl-piperidine-1-carboxylate (0.5 g, 930.48 μmol, 1 eq.) in DCM (3 mL) was added TFA (7.70 g, 67.53 mmol, 5 mL, 72.58 eq.). The mixture was stirred at 25° C. for 0.5 h. TLC analysis showed that the reaction was complete. Saturated aqueous Na₂CO₃ (20 mL) was added to the reaction to adjust the pH of the mixture to 9, and the mixture was extracted with EtOAc (20 mL×3). The combined organic layers were washed with brine (20 mL×3), dried over anhydrous sodium sulfate, filtered, and concentrated under reduced pressure. The crude product (0.4 g, crude) was obtained as a yellow solid and used in the next step without purification.

Preparation of N-((3R,4S)-1,3-dimethylpiperidin-4-yl)-2-iodo-1-(2,2,2-trifluoroethyl)-1H-indol-4-amine: To a mixture of 2-iodo-N-((3R,4S)-3-methylpiperidin-4-yl)-1-(2,2,2-trifluoroethyl)-1H-indol-4-amine (0.35 g, 800.47 μmol, 1 eq.) and formaldehyde (120.17 mg, 4 mmol, 110.25 μL, 5 eq.) in MeOH (3 mL) was added AcOH (48.07 ug, 0.8 μmol, 4.58e-2 μL, 0.001 eq.). The mixture was stirred at 50° C. for 1 h, and NaBH₃CN (251.51 mg, 4 mmol, 5 eq.) was added to the reaction. The reaction mixture was stirred further at 50° C. for 1 h. TLC analysis showed that the reaction was complete. The reaction mixture was poured into water (10 mL) and extracted with EtOAc (10 mL×3). The combined organic layers were washed with brine (10 mL×3), dried over anhydrous sodium sulfate, filtered, and concentrated under reduced pressure. The residue was purified by prep-TLC (SiO₂, DCM:MeOH=10:1) to obtain the desired product (0.13 g, 288.08 μmol, 35.99% yield) as a yellow solid.

Preparation of N-((3R,4S)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine: To a solution of 2-methoxy-4-methylsulfonyl-N-prop-2-ynyl-aniline (63.63 mg, 265.92 μmol, 1.2 eq.) in DMSO (2 mL) were added N-isopropylpropan-2-amine (224.24 mg, 2.22 mmol, 313.18 μL, 10 eq.) and CuI (42.20 mg, 221.60 μmol, 1 eq.), N-((3R,4S)-1,3-dimethylpiperidin-4-yl)-2-iodo-1-(2,2,2-trifluoroethyl)-1H-indol-4-amine (0.1 g, 221.60 μmol, 1 eq.), and Pd(PPh₃)₄ (102.43 mg, 88.64 μmol, 0.4 eq.). The mixture was stirred at 25° C. for 1 h under N₂. TLC analysis showed that the reaction was complete. The reaction mixture was diluted with EtOAc (15 mL), and the resulting mixture was poured into saturated aqueous EDTA solution (15 mL) and stirred further at 25° C. for 1 h. The mixture was extracted with EtOAc (10 mL×3), and The combined organic layers were washed with brine (10 mL×3), dried over anhydrous sodium sulfate, filtered, and concentrated under reduced pressure. The residue was purified by prep- TLC (SiO$_2$, DCM:MeOH=10:1) and prep-HPLC to obtain the desired product (27.80 mg, 49.41 μmol, 22.30% yield) as a white solid.

Preparation of final products: N-((3R,4S)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine was purified by SFC to obtain the desired products as white solids. N-((3R,4S)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine, MS (ES$^{30}$, m/z): 563.2; and N-((3S,4R)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine, MS (ES$^{30}$, m/z): 563.3.

Example D105: Synthesis of Compounds 780A and 781A

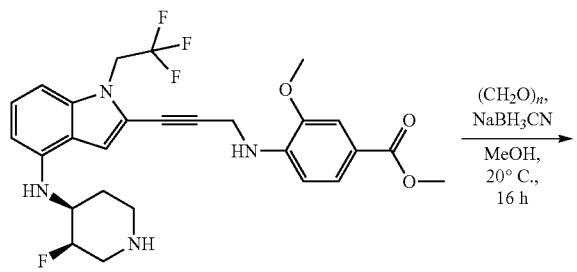

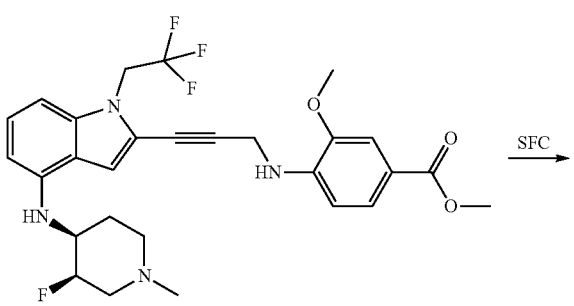

-continued

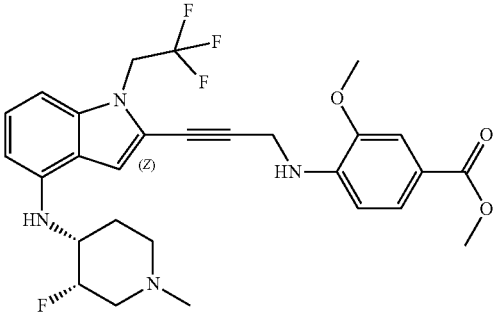

A mixture of methyl 4-((3-(4-(((3R,4S)-3-fluoropiperidin-4-yl)amino)-1-(2,2,2-trifluoroethyl)-1H-indol-2-yl)prop-2-yn-1-yl)amino)-3-methoxybenzoate, NaBH$_3$CN (53.10 mg, 845.02 μmol, 3 eq.), AcOH (16.91 mg, 281.67 μmol, 16.11 μL, 1 eq.). and formaldehyde (84.59 mg, 2.82 mmol, 10 eq.) in MeOH (3 mL) was stirred at 20° C. for 16 h under N$_2$. TLC analysis (EtOAc:TEA=10:1, R$_f$=0.65) indicated that the starting material was consumed completely, and one new spot was detected. The reaction mixture was quenched by adding water (10 mL) and extracted with EtOAc (10 mL×3). The combined organic layers were washed with brine (10 mL×3), dried over anhydrous sodium sulfate, filtered, and concentrated under reduced pressure to give a residue. The residue was purified by prep-HPLC to afford methyl 4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-3-methoxybenzoate (0.07 g, 121.67 μmol, 43.20% yield) as a yellow solid.

Methyl 4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-3-methoxybenzoate was separated by SFC to give the desired final products as yellow solids. 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoic acid (0.03 g, 54.23 μmol, 42.34% yield), MS (ES$^{30}$, m/z): 533.2; and 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoic acid (0.03 g, 54.67 μmol, 42.69% yield), MS (ES$^{30}$, m/z): 533.2.

Example D106: Synthesis of Compounds 832A and 833A

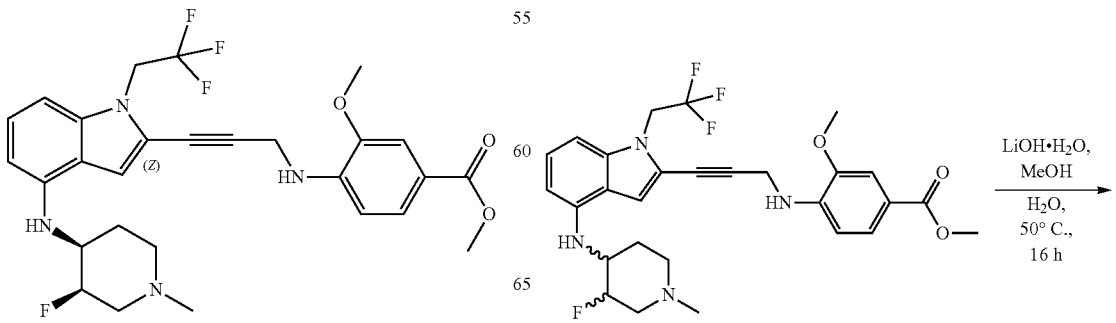

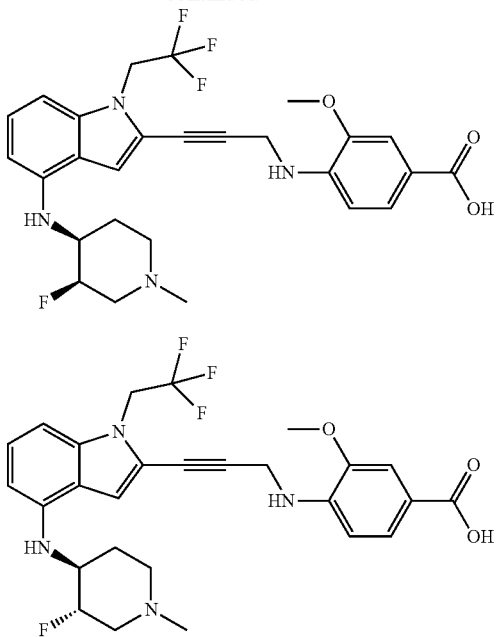

To a solution of methyl 4-((3-(4-((3-fluoro-1-methylpiperidin-4-yl)amino)-1-(2,2,2-trifluoroethyl)-1H-indol-2-yl)prop-2-yn-1-yl)amino)-3-methoxybenzoate(0.18 g, 329.34 μmol, 1 eq) in MeOH (20 mL) was added LiOH·H₂O (20 mL, 10 μmol/L, 10 mL), and the reaction mixture was stirred at 50° C. for 16 h under N₂. TLC analysis (EtOAc:TEA=10:1, R_f=0.01) indicated that the starting material remained, and one major new spot was detected. The reaction mixture was quenched by adding EtOAc (30 mL), and the resulting mixture was further extracted with EtOAc (30 mL×3). The combined organic layers were washed with brine (20 mL×3), dried over anhydrous sodium sulfate, filtered, and concentrated under reduced pressure to give a residue. The crude residue was purified by prep-HPLC to obtain the desired product as a yellow solid (0.1 g, 54.17% yield).

rac-4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-3-methoxybenzoic acid, MS (ES³⁰, m/z): 533.2; and rac-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzoic acid, MS (ES³⁰, m/z): 533.1.

Example D107: Synthesis of Compounds 874A and 875A

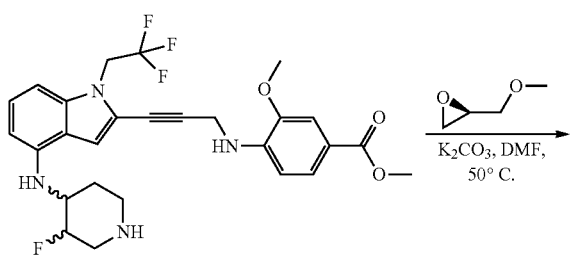

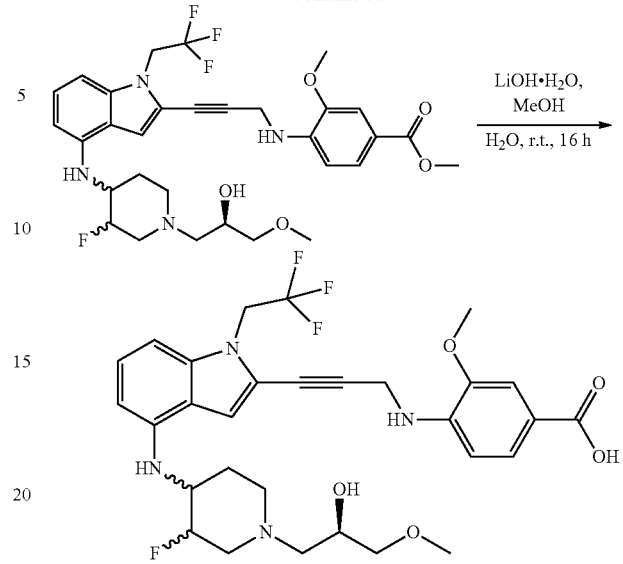

Preparation of methyl 4-((3-(4-((3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoate: To a solution of methyl 4-((3-(4-((3-fluoropiperidin-4-yl)amino)-1-(2,2,2-trifluoroethyl)-1H-indol-2-yl)prop-2-yn-1-yl)amino)-3-methoxybenzoate (0.5 g, 938.92 μmol, 1 eq.) and (2R)-2-(methoxymethyl)oxirane (413.62 mg, 4.69 mmol, 417.79 μL, 5 eq.) in DMF (5 mL) was added K₂CO₃ (389.29 mg, 2.82 mmol, 3 eq.). The mixture was stirred at 50° C. for 12 h. TLC analysis (EtOAc:TEA=10:1, R_f=0.75) detected one major new spot. LC-MS analysis showed that the starting material was consumed completely, and one main peak with the desired m/z or desired mass was detected. The reaction mixture was quenched by adding water (40 mL) and extracted with EtOAc (35 mL×3). The combined organic layers were washed with brine (25 mL×3), dried over anhydrous sodium sulfate, filtered, and concentrated under reduced pressure. The crude residue was purified by column chromatography to afford the desired product (0.35 g, 420.70 μmol, 44.81% yield) as a yellow solid. MS (ES³⁰, m/z): 621.4.

Preparation of 4-((3-(4-((3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid: A mixture of methyl 4-((3-(4-((3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoate (0.1 g, 161.13 μmol, 1 eq.) and LiOH·H₂O (67.61 mg, 1.61 mmol, 10 eq.) in water (0.5 mL) and MeOH (3 mL) was stirred at 50° C. for 12 h under N₂ atmosphere. TLC analysis (EtOAc:TEA=10:1, R_f=0) indicated that the starting material was consumed completely. Several new peaks were shown on LC-MS, and the desired compound was detected. The reaction mixture was quenched by adding EtOAc (30 mL) and extracting the mixture further with EtOAc (30 mL×3). The combined organic layers were washed with brine (20 mL×3), dried over anhydrous sodium sulfate, filtered, and concentrated under reduced pressure. LC-MS and HPLC analysis showed that the reaction was complete. The residue was purified by prep-HPLC to obtain the desired products as blue solids.

4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid, (35 mg) MS (ES³⁰, m/z): 607.2; and 4-((3-(4-(((3S,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid, (35 mg) MS (ES³⁰, m/z): 607.3.

Example D108: Synthesis of Compounds 876A and 877A

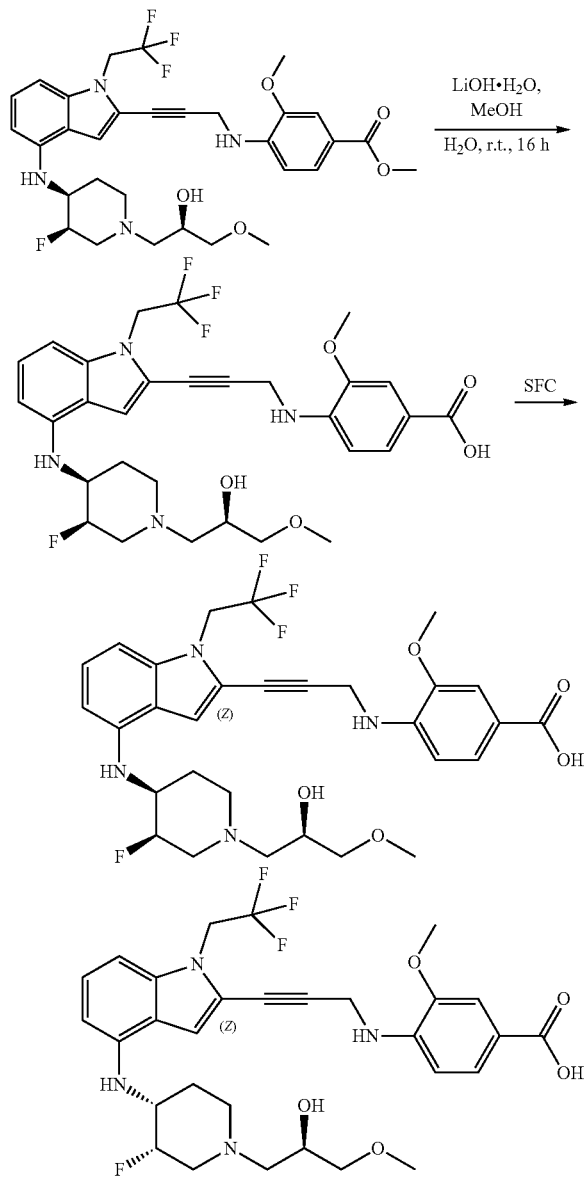

Preparation of 4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid: A solution of methyl 4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoate (0.2 g, 322.25 μmol, 1 eq) and LiOH·H₂O (135.23 mg, 3.22 mmol, 10 eq.) in MeOH (15 mL) and water (3 mL) was stirred at 20° C. for 12 h under N₂. TLC analysis (EtOAc:TEA=10:1, R_f=0) indicated that the starting material was consumed completely. The reaction mixture was quenched by adding EtOAc (30 mL) and extracted with EtOAc (30 mL×3). The combined organic layers were washed with brine (20 mL×3), dried over anhydrous sodium sulfate, filtered, and concentrated under reduced pressure. The residue was purified by prep-TLC (SiO₂, DCM:THF=3:1) to obtain 4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid (0.11 g, 170.46 μmol, 52.90% yield) was obtained as a yellow oil.

Preparation of final products: 4-((3-(4-(((3R,4S)-3-Fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid was separated by SFC to obtain the desired products. 4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid, MS (ES³⁰, m/z): 607.3; and 4-((3-(4-(((3S,4R)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid, MS (ES³⁰, m/z): 607.3.

Example D109: Synthesis of Compounds 940A, 942A, 943A, 945A, 946A, and 947A

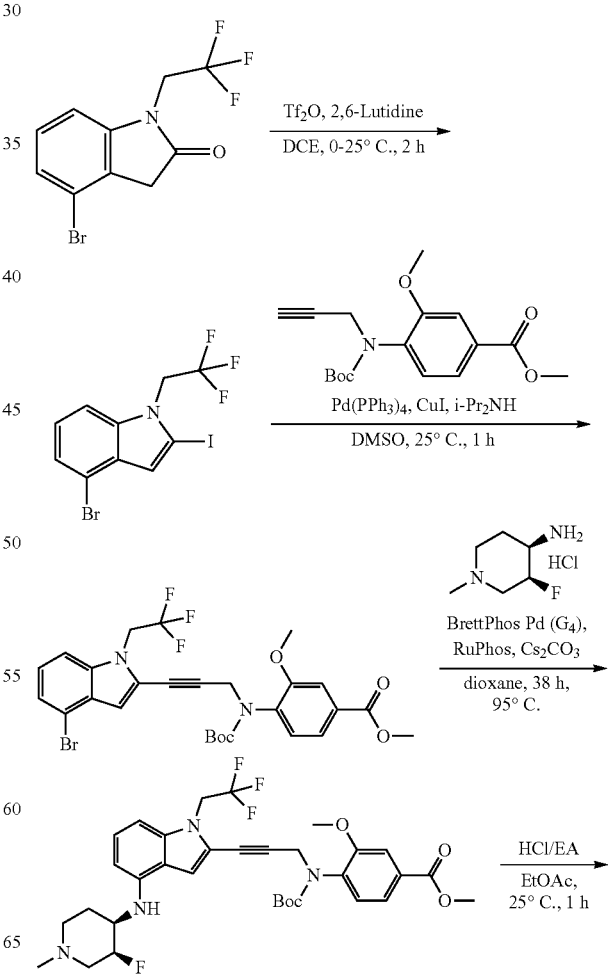

-continued

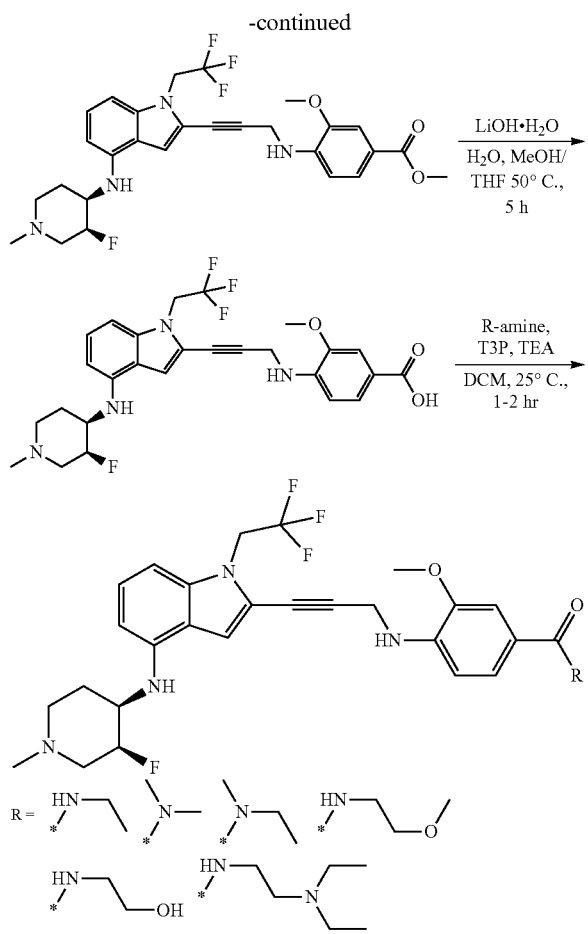

Preparation of 4-bromo-1-(2,2,2-trifluoroethyl)-1H-indol-2-yl trifluoromethanesulfonate: To a solution of 4-bromo-1-(2,2,2-trifluoroethyl)indolin-2-one (10 g, 34.01 mmol, 1 eq.) and 2,6-lutidine (4.37 g, 40.81 mmol, 4.75 mL, 1.2 eq.) in DCM (100 mL) was added trifluoromethylsulfonyl trifluoromethanesulfonate (9.59 g, 34.01 mmol, 5.61 mL, 1 eq.) dropwise at 25° C., and the reaction mixture was stirred at 25° C. for 2 h. TLC analysis showed that the reaction was complete. The reaction mixture was poured into a saturated aqueous solution of $NH_4Cl$ (100 mL). The aqueous phase was extracted with DCM (60 mL×3) and washed with saturated aqueous $NaHCO_3$ (100 mL). The combined organic layers were washed with brine (20 mL), dried over anhydrous sodium sulfate, filtered and concentrated on vacuum. The residue was purified by column chromatography ($SiO_2$, PE:EtOAc=1:0 to 100:1, $R_f$=0.5) to afford [4-bromo-1-(2,2,2-trifluoroethyl)indol-2-yl]trifluoromethanesulfonate (13.0 g, 27.46 mmol, 81% yield) as a yellow solid.

Preparation of methyl 4-((3-(4-bromo-1-(2,2,2-trifluoroethyl)-1H-indol-2-yl)prop-2-yn-1-yl)(tert-butoxycarbonyl)amino)-3-methoxybenzoate: To a solution of methyl 4-((tert-butoxycarbonyl)(prop-2-yn-1-yl)amino)-3-methoxybenzoate (3.20 g, 10.03 mmol, 0.9 eq.) in DMSO (50 mL) were added i-$Pr_2NH$ (11.28 g, 111.47 mmol, 15.75 mL, 10 eq.), CuI (106.15 mg, 557.34 µmol, 0.05 eq.), and 4-bromo-1-(2,2,2-trifluoroethyl)-1H-indol-2-yl trifluoromethanesulfonate (5 g, 11.15 mmol, 1 eq.) at 20° C. Then, $Pd(PPh_3)_4$ (644.04 mg, 557.34 µmol, 0.05 eq.) was added to the reaction, and the mixture was purged with $N_2$ three times. The mixture was then stirred at 25° C. for 1 h. TLC analysis (PE:EtOAc=5:1, $R_f$=0.3) indicated that the starting material was consumed completely, and one new spot was detected. The reaction mixture was quenched by adding saturated aqueous EDTA (500 mL), and the resulting mixture was extracted with EtOAc (200 mL×3). The combined organic layers were washed with brine (200 mL×3), dried over anhydrous sodium sulfate, filtered, and concentrated under reduced pressure. The crude residue was purified by column chromatography ($SiO_2$, PE:EtOAc=15:1 to 8:1) to obtain the desired product (6.2 g, 8.85 mmol, 79.40% yield) as a yellow solid.

$^1$H NMR: (400 MHz, DMSO-d6) δ ppm 1.28-1.41 (m, 9H) 3.86 (s, 3H) 3.88 (s, 3H) 4.48-4.78 (m, 2H) 5.05 (q, J=8.63 Hz, 2H) 6.74-6.78 (m, 1H) 7.18-7.25 (m, 1H) 7.34-7.48 (m, 5H) 7.57-7.64 (m, 3H).

Preparation of methyl 4-((tert-butoxycarbonyl)(3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoate: To a mixture of methyl 4-((3-(4-bromo-1-(2,2,2-trifluoroethyl)-1H-indol-2-yl)prop-2-yn-1-yl)(tert-butoxycarbonyl)amino)-3-methoxybenzoate (5 g, 8.40 mmol, 1 eq.), (3S,4R)-3-fluoro-1-methylpiperidin-4-amine hydrochloride (1.89 g, 9.24 mmol, 1.1 eq., 2HCl), and $Cs_2CO_3$ (10.94 g, 33.59 mmol, 4 eq.) in dioxane (50 mL) were added RuPhos (548.62 mg, 1.18 mmol, 0.14 eq.) and BrettPhos (Pd, $G_4$) (541.12 mg, 587.84 µmol, 0.07 eq.) at 20° C. The resulting mixture was purged with $N_2$ three times and stirred at 95° C. for 38 h. TLC analysis (EtOAc:TEA=10:1, $R_f$=0.3) indicated that 10% of the starting material remained, and one major new spot with polarity greater than that of the starting material was detected. The reaction mixture was quenched by adding saturated aqueous EDTA (500 mL). The mixture was extracted with EtOAc (100 mL×3). The combined organic layers were washed with brine (100 mL×3), dried over anhydrous sodium sulfate, filtered, and concentrated under reduced pressure to give a residue. The crude residue was purified by column chromatography ($SiO_2$, PE:EtOAc=8:1 to 0:1), and the crude product was triturated with MTBE:PE=10 mL: 5 mL at 25° C. for 12 h to afford the desired product (3 g, 4.54 mmol, 54.03% yield) as a yellow solid.

$^1$H NMR: (400 MHz, DMSO-d6) δ ppm 1.22-1.52 (m, 9H) 1.64-1.76 (m, 1H) 1.87-1.99 (m, 1H) 2.08 (brt, J=11.58 Hz, 1H) 2.14-2.30 (m, 4H) 2.77-2.86 (m, 1H) 2.96-3.06 (m, 1H) 3.47-3.66 (m, 1H) 3.83-3.90 (m, 6H) 4.52-4.72 (m, 2H) 4.75 (br s, 1H) 4.80-4.97 (m, 3H) 5.49-5.59 (m, 1H) 6.20-6.29 (m, 1H) 6.69-6.83 (m, 1H) 6.98-7.08 (m, 1H) 7.20 (d, J=2.21 Hz, 1H) 7.38-7.46 (m, 1H) 7.59 (br d, J=3.53 Hz, 2H).

Preparation of methyl 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoate: A solution of methyl 4-((tert-butoxycarbonyl)(3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoate (3 g, 4.50 mmol, 1 eq.) was prepared in HCl/EtOAc (4 M, 90 mL), and the mixture was stirred at 25° C. for 1 h. TLC analysis (EtOAc:TEA=10:1, $R_f$=0.4) indicated that the starting material was consumed completely, and one major new spot with polarity greater than that of the starting material was detected. The mixture was filtered, and the filter cake was diluted with saturated aqueous $Na_2CO_3$ (200 mL) and extracted with EtOAc (80 mL×3). The combined organic layers were washed with brine (50 mL×3), dried over anhydrous sodium sulfate, filtered, and concentrated under reduced pressure to give a residue. The crude product (2.5 g, crude) was obtained as a yellow solid and used in the next step without purification.

Preparation of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoic acid: To a solution of methyl 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoate (2.5 g, 4.57 mmol, 1 eq.), LiOH·H$_2$O (2.88 g, 68.61 mmol, 15 eq.), and NaOH (731.80 mg, 18.30 mmol, 4 eq.) in THF (20 mL), MeOH (20 mL), and water (20 mL) was stirred at 50° C. for 5 h. TLC analysis (EtOAc:MeOH=2:1, $R_f$=0.3) showed that the reaction was complete. The reaction mixture was concentrated to remove MeOH and THF. Water (100 mL) was added to the residue, and 0.5 M HCl was added to adjust the pH of the mixture to pH=5. The mixture with extracted with EtOAc (200 mL×12). The combined organic layers were washed with brine (50 mL×3), dried over anhydrous sodium sulfate, filtered, and concentrated under reduced pressure to give a residue. The crude product was triturated with ACN:MTBA=10 mL: 80 mL at 25° C. for 60 min to obtain the desired product (1.9 g, 3.53 mmol, 77.14% yield) as a yellow solid.

1H NMR: (400 MHz, DMSO-d$_6$) δ ppm 1.88-1.99 (m, 1H) 2.12-2.27 (m, 1H) 2.70-2.82 (m, 3H) 3.12-3.22 (m, 1H) 3.38-3.58 (m, 2H) 3.65-3.78 (m, 1H) 3.80-3.97 (m, 4H) 4.27-4.44 (m, 2H) 4.84-5.00 (m, 2H) 5.02-5.18 (m, 1H) 5.70-5.82 (m, 1H) 6.23-6.35 (m, 2H) 6.75-6.83 (m, 2H) 6.96-7.07 (m, 1H) 7.14-7.23 (m, 1H) 7.29-7.37 (m, 1H) 7.52 (d, J=8.19 Hz, 1H) 10.14-10.47 (m, 1H) 12.08-12.40 (m, 1H).

Preparation of final products: To a mixture of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoic acid (0.07 g, 131.45 μmol, 1 eq.), R-amine (11.85 mg, 262.90 μmol, 17.20 μL, 2 eq.), TEA (66.51 mg, 657.24 μmol, 91.48 μL, 5 eq.) in DCM (3 mL) DMF (3 mL) was added T3P (209.12 mg, 657.24 μmol, 195.44 μL, 5 eq.). The mixture was stirred at 20° C. for 1 h under N$_2$ atmosphere. TLC analysis indicated that the starting material was consumed completely, and one new spot was detected. The reaction mixture was quenched by adding water (5 mL) and extracted with EtOAc (5 mL×3). The combined organic layers were washed with brine (5 mL×3), dried over anhydrous sodium sulfate, filtered, and concentrated under reduced pressure to give a residue. The residue was purified by prep-HPLC to afford the desired products as yellow solids.

N-ethyl-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide, 28.0 mg, 37.7% yield, MS (ES$^{30}$, m/z): 560.2; 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N,N-dimethylbenzamide, 28.0 mg, 38.0% yield, MS (ES$^{30}$, m/z): 560.3; N-ethyl-4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxy-N-methylbenzamide, 38.7% yield, MS (ES$^{30}$, m/z): 588.3; 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(2-methoxyethyl)benzamide, 29.0 mg, 37% yield, MS (ES$^{30}$, m/z): 590.2; 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(2-hydroxyethyl)-3-methoxybenzamide, 30.0 mg, 31.3% yield, MS (ES$^{30}$, m/z): 576.3; and N-[2-(diethylamino)ethyl]-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide, 24.0 mg, 28.7% yield, MS (ES$^{30}$, m/z): 631.4.

Example D110: Synthesis of 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(3-hydroxy-2-methoxypropyl)-3-methoxybenzamide (Compound 966A)

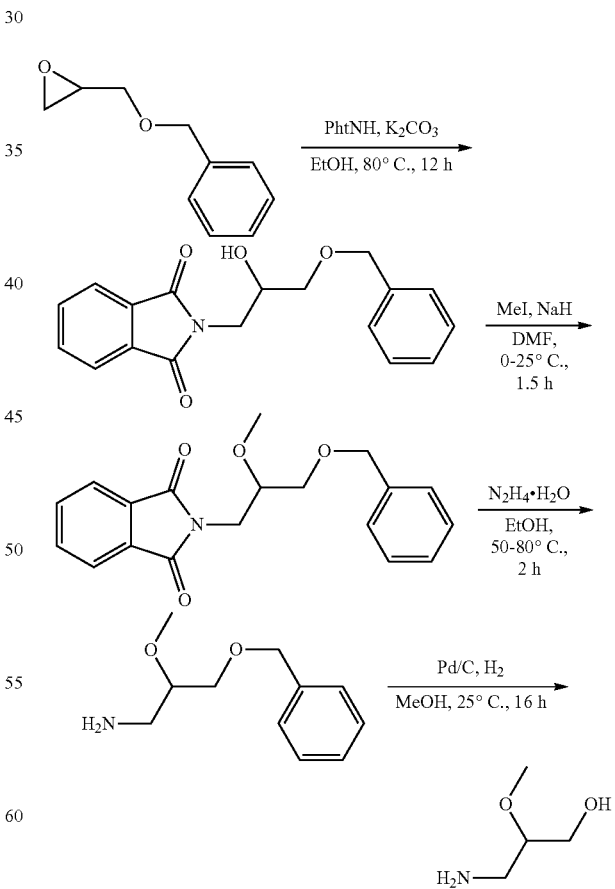

Preparation of 2-(3-(benzyloxy)-2-hydroxypropyl)isoindoline-1,3-dione: To a solution of phthalimide (2 g, 13.59 mmol, 1 eq.) and 2-(benzyloxymethyl)oxirane (2.68 g, 116.31 mmol, 2.48 mL, 1.2 eq.) in EtOH (20 mL) was added K$_2$CO$_3$ (150.30 mg, 1.09 mmol, 0.08 eq.). The mixture was stirred at 80° C. for 12 h. LC-MS and TLC analysis (PE:EtOAc=2:1, R$_f$=0.35) showed that the reaction was complete. The reaction mixture was concentrated in vacuo and purified by column chromatography (SiO$_2$, PE:EtOAc=5:1 to 3:1, R$_f$=0.3) to obtain the desired product (3 g, 9.64 mmol, 70.89% yield) as a light yellow oil. 1H NMR (400 MHz, DMSO-d6) δ=7.87-7.82 (m, 4H), 7.31-7.24 (m, 5H), 5.15 (d, J=4.2 Hz, 1H), 4.47 (s, 2H), 4.01-3.99 (m, 2H), 3.63-3.61 (m, 2H), 3.46-3.41 (m, 2H).

Preparation of 2-(3-(benzyloxy)-2-methoxypropyl)isoindoline-1,3-dione: To a solution of 2-(3-(benzyloxy)-2-hydroxypropyl)isoindoline-1,3-dione (2.5 g, 8.03 mmol, 1 eq.) in DMF (30 mL) was added NaH (481.80 mg, 12.05 mmol, 1.5 eq.) at 0° C. under$_{N2}$. The mixture was stirred for 0.5 h, and MeI (2.28 g, 16.06 mmol, 999.81 μL, 2 eq.) was added dropwise to the reaction. The resulting reaction mixture was stirred at 25° C. for 1 h. TLC analysis (PE:EtOAc=2:1, $_{Rf}$=0.4) showed that the reaction was complete. The reaction mixture was poured into a saturated aqueous solution of NH$_4$Cl (100 mL), and the aqueous phase was extracted with EtOAc (40 mL×3). The combined organic layers were washed with brine (40 mL×1), dried over anhydrous Na$_2$SO$_4$, filtered, and concentrated in vacuo. The residue was purified by column chromatography (SiO$_2$, PE:EtOAc=10:1 to 7:1, R$_f$=0.4) to afford the desired product (1 g, 3.07 mmol, 38.28% yield) as a light yellow oil.

Preparation of 3-(benzyloxy)-2-methoxypropan-1-amine: To a solution of 2-(3-(benzyloxy)-2-methoxypropyl)isoindoline-1,3-dione (1 g, 3.07 mmol, 1 eq.) in EtOH (20 mL) was added N$_2$H$_4$·H$_2$O (314 mg, 6.15 mmol, 304.86 μL, 2 eq.) at 50° C. under N$_2$. The mixture was stirred at 80° C. for 2 h. LC-MS analysis showed that 20% of the starting material remained, and 65% of the desired product was detected. The reaction mixture was concentrated in vacuo and purified by prep-HPLC to obtain the desired product 0.2 g, 1.02 mmol, 33.33% yield as a light yellow oil.

Preparation of 3-amino-2-methoxypropan-1-ol: To a solution of 3-(benzyloxy)-2-methoxypropan-1-amine (0.1 g, 512.14 μmol, 1 eq.) in EtOH (2 mL) was added Pd/C (0.1 g, 93.97 μmol, 10% purity, 1.83e-1 eq.). The mixture was stirred at 40° C. for 8 h and filtered through a pad of silica. The crude residue was purified by prep-HPLC to give the desired product (50 mg) as a colorless oil.

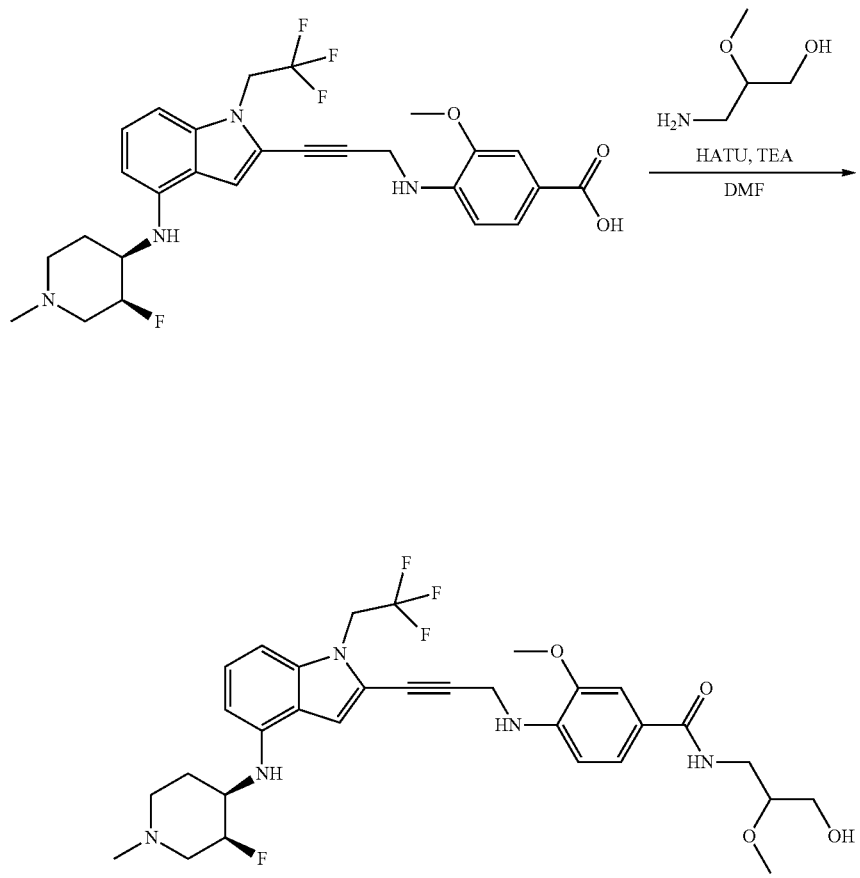

To a solution of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoic acid (0.08 g, 150.23 μmol, 1 eq.) in DMF (5 mL) were added TEA (45.60 mg, 450.68 μmol, 62.73 μL, 3 eq.) and HATU (85.68 mg, 225.34 μmol, 1.5 eq.) at 25° C. The mixture was stirred for 0.5 h, and 3-amino-2-methoxy-propan-1-ol (17.37 mg, 165.25 μmol, 47.85 μL, 1.1 eq.) was added and the mixture. The resulting mixture was stirred at 50° C. for 1 h. LC-MS and HPLC analysis showed that the reaction was complete. The mixture was purified directly using prep-HPLC to obtain the desired product as a yellow solid. 31.0 mg, 28% yield, MS (ES$^{30}$, m/z): 620.3.

Example D111: Synthesis of 1-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]-3-[(2-methylpropanoyl)oxy]propan-2-yl 2-methylpropanoate (Compound 967A)

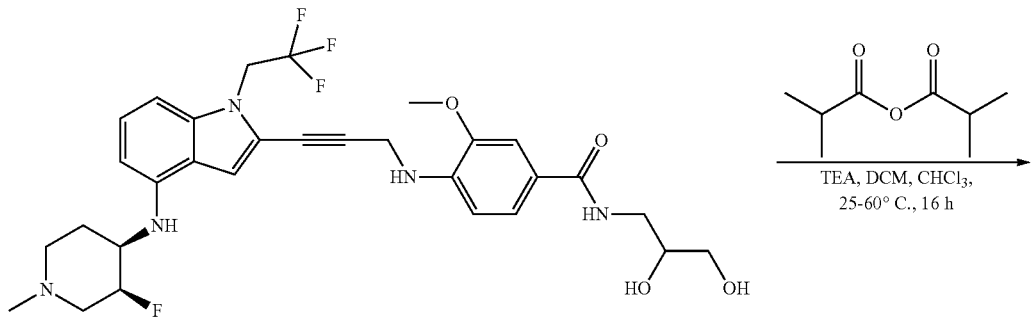

To a solution of N-(2,3-dihydroxypropyl)-4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzamide (80 mg, 132.10 μmol, 1 eq.) in DCM (3 mL) and CHCl₃ (3 mL) were added TEA (40.10 mg, 396.29 μmol, 55.16 L, 3 eq.) and 2-methylpropanoyl 2-methylpropanoate (43.88 mg, 277.40 μmol, 46 μL, 2.1 eq.) at 25° C. The mixture was stirred at 60° C. for 16 h. LC-MS analysis detected the desired product. The mixture was concentrated, and the residue was purified by prep-HPLC to give the desired product as a yellow oil (28.0 mg, 28% yield). MS (ES$^{30}$, m/z): 746.3.

Example D112: Synthesis of 4-{1[3-(4-{1[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-[(2-oxo-1,3-dioxolan-4-yl)methyl]benzamide (Compound 968A)

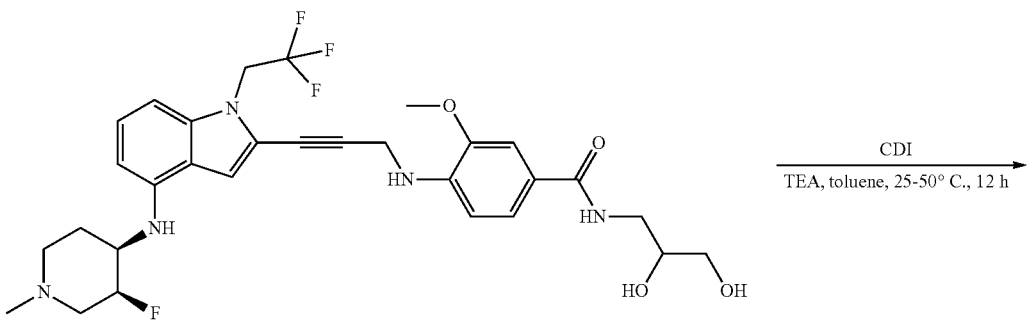

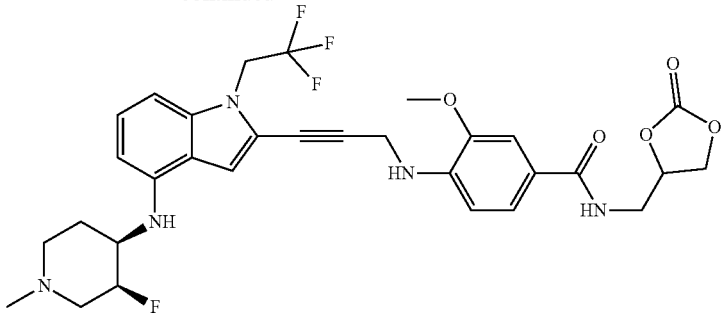

To a solution of N-(2,3-dihydroxypropyl)-4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzamide (0.08 g, 132.10 μmol, 1 eq.) in toluene (5 mL) were added TEA (40.10 mg, 396.29 μmol, 55.16 μL, 3 eq.) and CDI (44.98 mg, 277.40 μmol, 2.1 eq.) at 25° C. The mixture was stirred at 50° C. for 12 h. LC-MS and HPLC analysis showed that the reaction was complete. The mixture was concentrated, and the residue was purified by prep-HPLC to give the desired product as a yellow solid (26.0 mg, 29.9% yield). MS (ES$^{30}$, m/z): 632.2.

Example D113: Preparation of Compound 461A

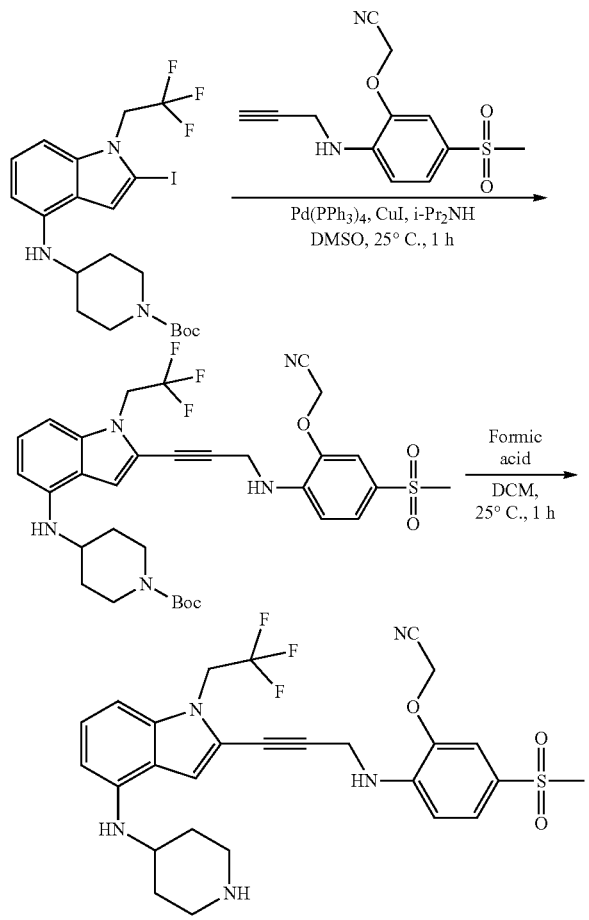

Synthesis of tert-butyl 4-((2-(3-((2-(cyanomethoxy)-4-(methylsulfonyl)phenyl)amino)prop-1-yn-1-yl)-1-(2,2,2-trifluoroethyl)-1H-indol-4-yl)amino)piperidine-1-carboxylate: To a solution of 2-(5-(methylsulfonyl)-2-(prop-2-yn-1-ylamino)phenoxy)acetonitrile (prepared according to EXAMPLE A4) (101.01 mg, 305.73 μmol, 2 eq.) in DMSO (1 mL) were added i-Pr$_2$NH (464.06 mg, 4.59 mmol, 648.13 μL, 30 eq.), CuI (58.23 mg, 305.73 μmol, 2 eq.), tert-butyl 4-((2-iodo-1-(2,2,2-trifluoroethyl)-1H-indol-4-yl)amino)piperidine-1-carboxylate (80 mg, 152.87 μmol, 1 eq.), and Pd(PPh$_3$)$_4$ (44.16 mg, 38.22 μmol, 0.25 eq.). The mixture was stirred at 25° C. for 1 h under N$_2$. TLC analysis (DCM:MeOH=20:1, R$_f$=0.5) indicated that the starting material was consumed completely. The mixture was poured into a saturated aqueous EDTA solution (20 mL), stirred at 25° C. for 1 h, and extracted with EtOAc (20 mL×3). The combined organic layers were washed with brine (20 mL×3), dried over anhydrous sodium sulfate, filtered, and concentrated under reduced pressure. The resulting residue was purified by prep-TLC (DCM:MeOH=20:1, R$_f$=0.5) to afford desired compound tert-butyl 4-((2-(3-((2-(cyanomethoxy)-4-(methylsulfonyl)phenyl)amino)prop-1-yn-1-yl)-1-(2,2,2-trifluoroethyl)-1H-indol-4-yl)amino)piperidine-1-carboxylate (80 mg, 103.07 μmol, 67.43% yield) as a yellow solid.

Synthesis of final product: To a solution of compound tert-butyl 4-((2-(3-((2-(cyanomethoxy)-4-(methylsulfonyl)phenyl)amino)prop-1-yn-1-yl)-1-(2,2,2-trifluoroethyl)-1H-indol-4-yl)amino)piperidine-1-carboxylate (30 mg, 38.65 μmol, 1 eq.) in DCM (1 mL) was added formic acid (732 mg, 15.90 mmol, 600 μL, 411.46 eq.). The mixture was stirred at 25° C. for 1 h, after which time LC-MS analysis indicated that the Boc-protected piperidine was consumed completely. The mixture was concentrated under reduced pressure to give a residue that was purified by prep-HPLC to afford 2-{5-methanesulfonyl-2-[(3-{4-[(piperidin-4-yl)amino]-1-(2,2,2-trifluoroethyl)-1H-indol-2-yl}prop-2-yn-1-yl)amino]phenoxy}acetonitrile (13.2 mg, 20.38 μmol, 52.72% yield) as a yellow solid. MS (ES$^{30}$, m/z): 560.2.

Example D114: Preparation of Compound 715A

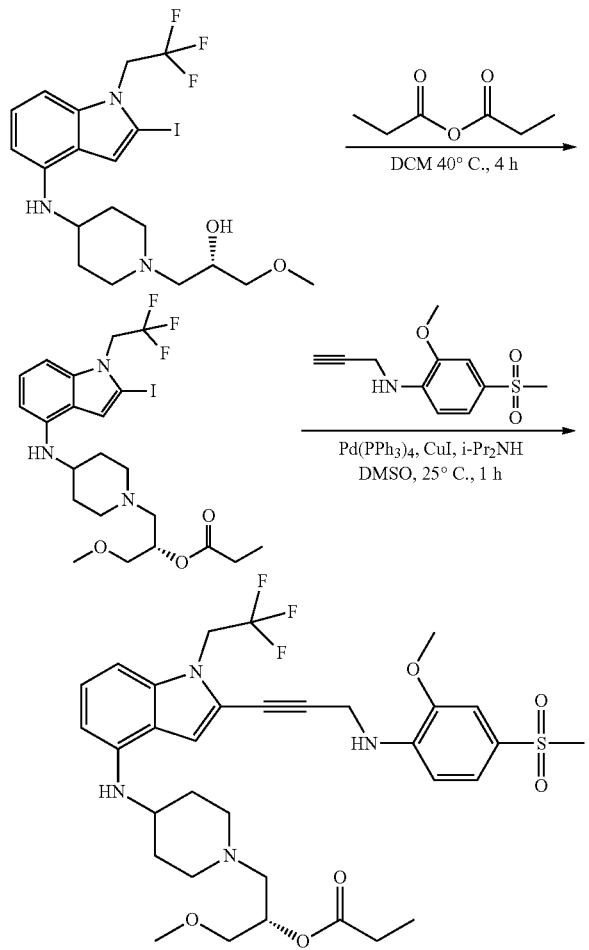

Synthesis of (S)-1-(4-((2-iodo-1-(2,2,2-trifluoroethyl)-1H-indol-4-yl)amino)piperidin-1-yl)-3-methoxypropan-2-yl propionate: To a solution of (S)-1-(4-((2-iodo-1-(2,2,2-trifluoroethyl)-1H-indol-4-yl)amino)piperidin-1-yl)-3-methoxypropan-2-ol (prepared according to the first step of EXAMPLE D142 using (S)-glycidyl methyl ether in place of racemic glycidyl methyl ether) (1.5 g, 2.79 mmol, 1 eq.) in DCM (50 mL) was added propionic anhydride (435.23 mg, 3.34 mmol, 430.92 µL, 1.2 eq.). The mixture was stirred at 45° C. for 4 h. after which time TLC analysis (PE:EtOAc=1:1, $R_f$=0.5) indicated that the reaction was complete. The mixture was concentrated in vacuo, and the residue was purified by column chromatography (SiO$_2$, PE:EtOAc=5:1 to 0:1, $R_f$=0.5) to afford of (S)-1-(4-((2-iodo-1-(2,2,2-trifluoroethyl)-1H-indol-4-yl)amino)piperidin-1-yl)-3-methoxypropan-2-yl propionate (2 g, 3.17 mmol, 56.92% yield) as a light yellow oil. MS (ES$^{30}$, m/z): 568.1.

Synthesis of final product: To a solution of 2-methoxy-4-methylsulfonyl-N-prop-2-ynyl-aniline (830.67 mg, 3.43 mmol, 1.2 eq.) in DMSO (25 mL) was added diisopropylamine (2.89 g, 28.55 mmol, 4.04 mL, 10 eq.) and CuI (108.76 mg, 571.04 µmol, 0.2 eq.), followed by (S)-1-(4-((2-iodo-1-(2,2,2-trifluoroethyl)-1H-indol-4-yl)amino)piperidin-1-yl)-3-methoxypropan-2-yl propionate (1.8 g, 2.86 mmol, 1 eq.) and Pd(PPh$_3$)$_4$ (164.97 mg, 142.76 µmol, 0.05 eq.) under N$_2$. The mixture was stirred at 25° C. for 1 h, after which time TLC analysis (PE:EtOAc=0:1, $R_f$=0.3) indicated that the reaction was complete. The residue was poured into a saturated aqueous EDTA solution (200 mL) and stirred for 1 h, and extracted with EtOAc (100 mL×3). The combined organic layers were washed with brine (100 mL), dried over anhydrous sodium sulfate, filtered, and concentrated in vacuo. The residue was purified by column chromatography (SiO$_2$, PE:EtOAc=1:1 to 0:1, $R_f$=0.3), and then further purified by prep-HPLC to afford the desired product (3.78 g, 5.49 mmol, 93.08% yield) as a light yellow solid.

(2S)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl propanoate; $^1$H NMR (400 MHz, DMSO-d6) δ ppm 1.04 (t, J=7.52 Hz, 3H) 1.33-1.52 (m, 2H) 1.74-1.98 (m, 2H) 2.05-2.20 (m, 2H) 2.26-2.31 (m, 2H) 2.43 (br d, J=5.01 Hz, 3H) 2.59-2.73 (m, 1H) 2.77-2.99 (m, 2H) 3.09 (s, 4H) 3.25 (s, 3H) 3.30 (br s, 1H) 3.44 (d, J=4.65 Hz, 2H) 3.89 (s, 3H) 4.35 (br d, J=6.11 Hz, 2H) 4.92 (q, J=8.97 Hz, 2H) 5.00-5.12 (m, 1H) 5.47 (br d, J=7.95 Hz, 1H) 6.15 (d, J=7.83 Hz, 1H) 6.49 (t, J=6.30 Hz, 1H) 6.67 (br d, J=8.31 Hz, 1H) 6.89 (d, J=8.44 Hz, 1H) 6.94-7.04 (m, 1H) 7.07 (s, 1H) 7.25 (d, J=1.83 Hz, 1H) 7.38 (dd, J=8.31, 1.83 Hz, 1H) 7.35-7.43 (m, 1H). MS (ES$^{30}$, m/z): 679.3.

Example D115: Preparation of Compound 638A

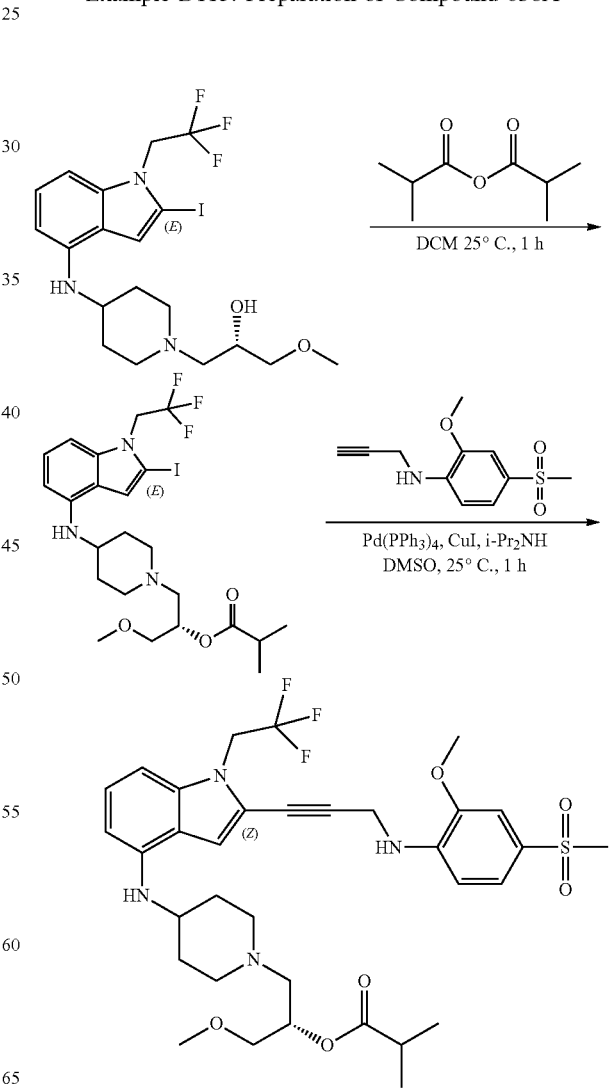

Compound 638A was prepared via a procedure analogous to the synthesis of Compound 715A according to EXAMPLE D114, using isobutyric anhydride in place of propionic anhydride.

(2S)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl 2-methylpropanoate; $^1$H NMR (400 MHz, DMSO-d6) δ ppm 1.09 (dd, J=10.45, 6.91 Hz, 6H) 1.34-1.50 (m, 2H) 1.89 (br s, 2H) 2.01-2.22 (m, 2H) 2.33 (br s, 2H) 2.43 (br s, 2H) 2.76-2.94 (m, 2H) 3.09 (s, 3H) 3.25 (s, 3H) 3.30 (br s, 1H) 3.44 (br d, J=4.65 Hz, 2H) 3.89 (s, 3H) 4.35 (br d, J=5.99 Hz, 2H) 4.92 (q, J=8.56 Hz, 2H) 5.07 (br d, J=5.50 Hz, 1H) 5.47 (br d, J=7.83 Hz, 1H) 6.14 (br d, J=7.83 Hz, 1H) 6.49 (br t, J=6.24 Hz, 1H) 6.67 (br d, J=8.19 Hz, 1H) 6.89 (d, J=8.44 Hz, 1H) 6.99 (br t, J=7.95 Hz, 1H) 7.08 (s, 1H) 7.25 (d, J=1.59 Hz, 1H) 7.38 (br d, J=6.85 Hz, 1H). MS (ES$^{30}$, m/z): 693.4.

Example D116: Preparation of Compound 482A

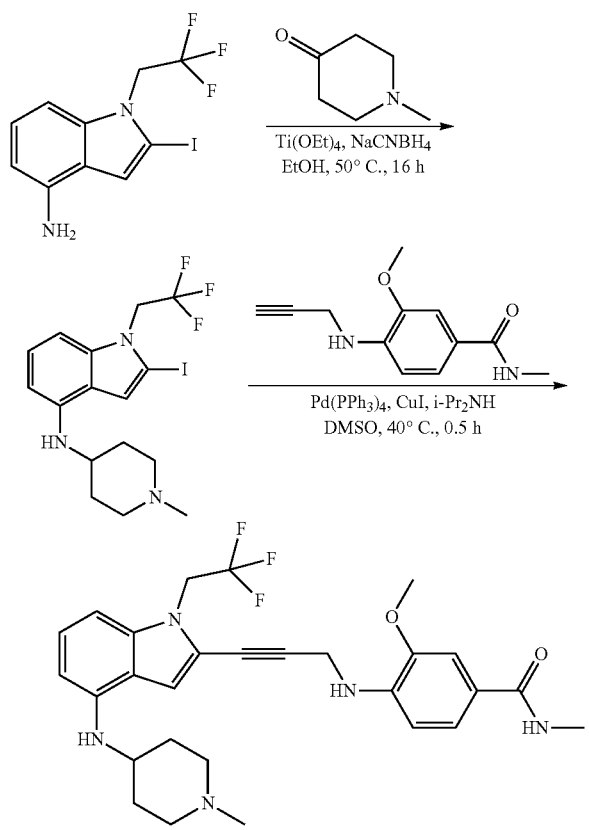

Synthesis of 2-iodo-N-(1-methylpiperidin-4-yl)-1-(2,2,2-trifluoroethyl)-1H-indol-4-amine: To a mixture of 1-methylpiperidin-4-one (8.32 g, 73.51 mmol, 8.55 mL, 5 eq.) and 2-iodo-1-(2,2,2-trifluoroethyl)indol-4-amine (5 g, 14.70 mmol, 1 eq.) in toluene (100 mL) was added Ti(OEt)$_4$ (6.71 g, 29.40 mmol, 6.10 mL, 2 eq.) under N$_2$. The reaction mixture was stirred at 110° C. for 1 h. The reaction mixture was then concentrated, and the resulting residue was dissolved with MeOH (100 mL). Then, NaBH$_4$ (1.11 g, 29.40 mmol, 2 eq.) was added and stirred at 40° C. for 16 h. TLC analysis (PE:EtOAc=0:1, R$_f$=0.0) showed that the starting material was consumed completely. The reaction mixture was filtered, and the filter cake was washed with DCM (200 mL×2). The combined organic layers were washed with brine (200 mL), dried over anhydrous sodium sulfate, filtered and concentrated in vacuo. The residue was purified by column chromatography (SiO$_2$, PE:EtOAc=3:1 to 0:1) to obtained product (6.5 g, 14.12 mmol, 48.03% yield) as light yellow solid.

$^1$H NMR (400 MHz, DMSO-d6) δ ppm 1.17 (t, J=7.09 Hz, 1H) 1.40-1.55 (m, 2H) 1.91 (br d, J=11.13 Hz, 2H) 1.97 (br d, J=1.71 Hz, 1H) 1.99-2.05 (m, 2H) 2.17 (s, 3H) 2.76 (br d, J=11.74 Hz, 2H) 3.25 (br s, 1H) 4.03 (q, J=7.13 Hz, 1H) 4.98 (q, J=8.97 Hz, 2H) 5.40 (d, J=8.07 Hz, 1H) 6.15 (d, J=7.82 Hz, 1H) 6.77 (d, J=8.19 Hz, 1H) 6.90 (t, J=8.01 Hz, 1H) 7.16 (s, 1H).

Synthesis of final product: To a solution of 3-methoxy-N-methyl-4-(prop-2-ynylamino)benzamide (1.11 g, 5.10 mmol, 1.2 eq.) in DMSO (40 mL) was added diisopropylamine (4.30 g, 42.54 mmol, 6.01 mL, 10 eq.) and CuI (162.03 mg, 850.79 μmol, 0.2 eq.) under N$_2$, followed by 2-iodo-N-(1-methylpiperidin-4-yl)-1-(2,2,2-trifluoroethyl)-1H-indol-4-amine (2 g, 4.25 mmol, 1 eq.) and Pd(PPh$_3$)$_4$ (245.78 mg, 212.70 μmol, 0.05 eq.). The mixture was stirred at 45° C. for 1 h, after which time TLC analysis (DCM:MeOH=10:1, R$_f$=0.3) indicated that the reaction was complete. The residue was poured into a saturated aqueous EDTA solution (50 mL) and stirred for 1 h. The aqueous phase was extracted with EtOAc (30 mL×3), and the combined organic layers were washed with brine (40 mL), dried over anhydrous sodium sulfate, filtered, and concentrated in vacuo. The residue was purified by column chromatography (SiO$_2$, PE:EtOAc=2:1 to DCM:MeOH=10:1, R$_f$=0.3) and then further purified by prep-HPLC. The concentrated eluate was then combined with saturated aqueous Na$_2$CO$_3$ (50 mL) to adjust the pH of the solution to 8, stirred for 1 h, and extracted with EtOAc (30 mL×3). The combined organic layers were washed with brine (40 mL), dried over anhydrous sodium sulfate, filtered, and concentrated in vacuo to provide the desired product (3.04 g, 5.67 mmol, 88.16% yield) as a light yellow solid.

3-methoxy-N-methyl-4-[(3-{4-[(1-methylpiperidin-4-yl)amino]-1-(2,2,2-trifluoroethyl)-1H-indol-2-yl}prop-2-yn-1-yl)amino]benzamide: $^1$H NMR (400 MHz, DMSO-d6) δ ppm 1.41-1.56 (m, 2H) 1.92 (br d, J=11.37 Hz, 2H) 2.06 (br d, J=11.00 Hz, 2H) 2.20 (s, 3H) 2.72-2.84 (m, 5H) 3.23-3.29 (m, 1H) 3.84 (s, 3H) 4.31 (brd, J=6.24 Hz, 2H) 4.90 (q, J=9.05 Hz, 2H) 5.48 (d, J=7.95 Hz, 1H) 5.98 (t, J=6.36 Hz, 1H) 6.15 (d, J=7.70 Hz, 1H) 6.67 (d, J=8.07 Hz, 1H) 6.75 (d, J=8.31 Hz, 1H) 6.99 (t, J=7.95 Hz, 1H) 7.06 (s, 1H) 7.35 (d, J=1.59 Hz, 1H) 7.42 (dd, J=8.25, 1.53 Hz, 1H) 8.10 (br d, J=4.52 Hz, 1H). MS (ES$^{30}$, m/z): 528.2.

Example D117: General Procedure for Preparation of Compounds 586A, 587A, 588A, and 589A

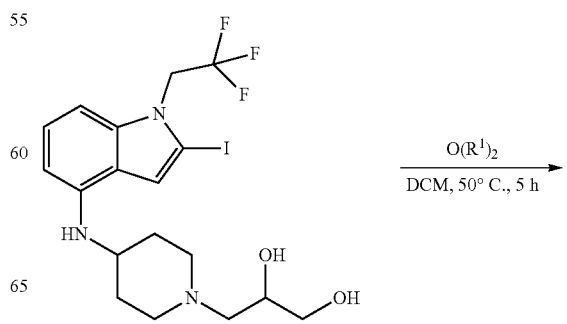

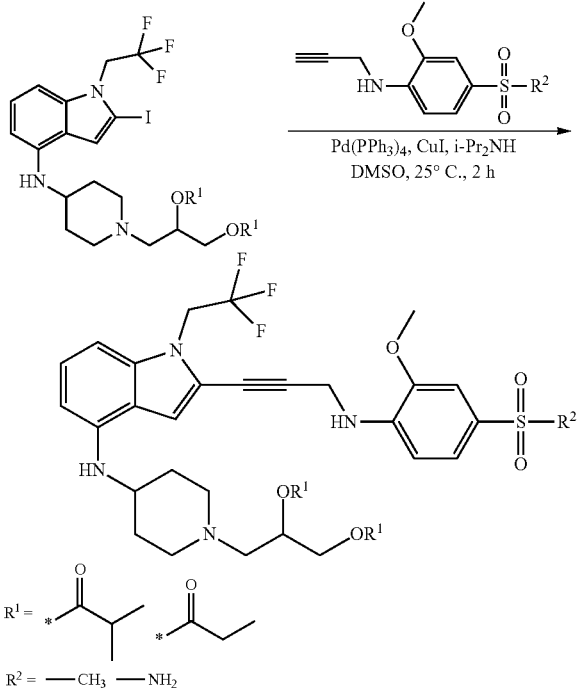

Step 1: To a mixture of 3-(4-((2-iodo-1-(2,2,2-trifluoro-ethyl)-1H-indol-4-yl)amino)piperidin-1-yl)propane-1,2-diol (200 mg, 361.96 μmol, 1 eq.) in DCM (3 mL) was added propanoyl propanoate (117.76 mg, 904.90 μmol, 116.60 μL, 2.5 eq.). The mixture was stirred at −50° C. for ~5 h. TLC and LC-MS analysis indicated that the starting material was consumed completely. The reaction was partitioned between water (100 mL) and EtOAc (10 mL) and then extracted with EtOAc (10 mL×3). The combined organic layers were washed with brine (50 mL×3), dried over anhydrous sodium sulfate, and filtered. The filtrate was concentrated in vacuo to provide the desired compounds 120 mg as light brown oils. MS (ES$^{30}$, m/z): 610.2. The same procedure was repeated to prepare the isobutyryl-protected analogue.

To a mixture of R$^2$-substituted alkyne (31.41 mg, 118.15 μmol, 1.2 eq.) in DMSO (2 mL) were added i-Pr$_2$NH (58.20 mg, 984.54 μmol, 10 eq.), CuI (18.75 mg, 98.45 μmol, 1 eq.), R$^1$-substituted iodoindole (60 mg, 98.45 μmol, 1 eq.), and Pd(PPh$_3$)$_4$ (22.75 mg, 19.69 μmol, 0.2 eq.) at 25° C. The mixture was stirred at 25° C. for 2 h under N$_2$, where after in each case LC-MS and TLC analysis indicated that the reaction was complete. The reaction mixture was quenched by adding a saturated aqueous EDTA solution (20 mL) and stirring the resulting mixture at 25° C. for 2 h. The reaction was partitioned between water (10 mL) and EtOAc (10 mL), and then extracted with EtOAc (20 mL×3). The combined organic layers were washed with brine (10 mL×3) dried over anhydrous sodium sulfate, filtered, and concentrated in vacuo. The residue was purified by prep-TLC, and then further purified by prep-HPLC to give a solution of the desired product. The solution was lyophilized to give the desired compound as a light yellow solid.

1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-(propanoyloxy)propan-2-yl propanoate, (21.5 mg) MS (ES$^{30}$, m/z): 721.3; 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}-3-(propanoyloxy)propan-2-yl propanoate, (12.7 mg) MS (ES$^{30}$, m/z): 722.2; 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-[(2-methylpropanoyl)oxy]propan-2-yl 2-methylpropanoate, (21.4 mg) MS (ES$^{30}$, m/z): 749.3; and 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}-3-[(2-methylpropanoyl)oxy]propan-2-yl 2-methylpropanoate, (23.8 mg) MS (ES$^{30}$, m/z): 750.3.

Example D118: General Procedure for Preparation of Compounds 590A and 591A

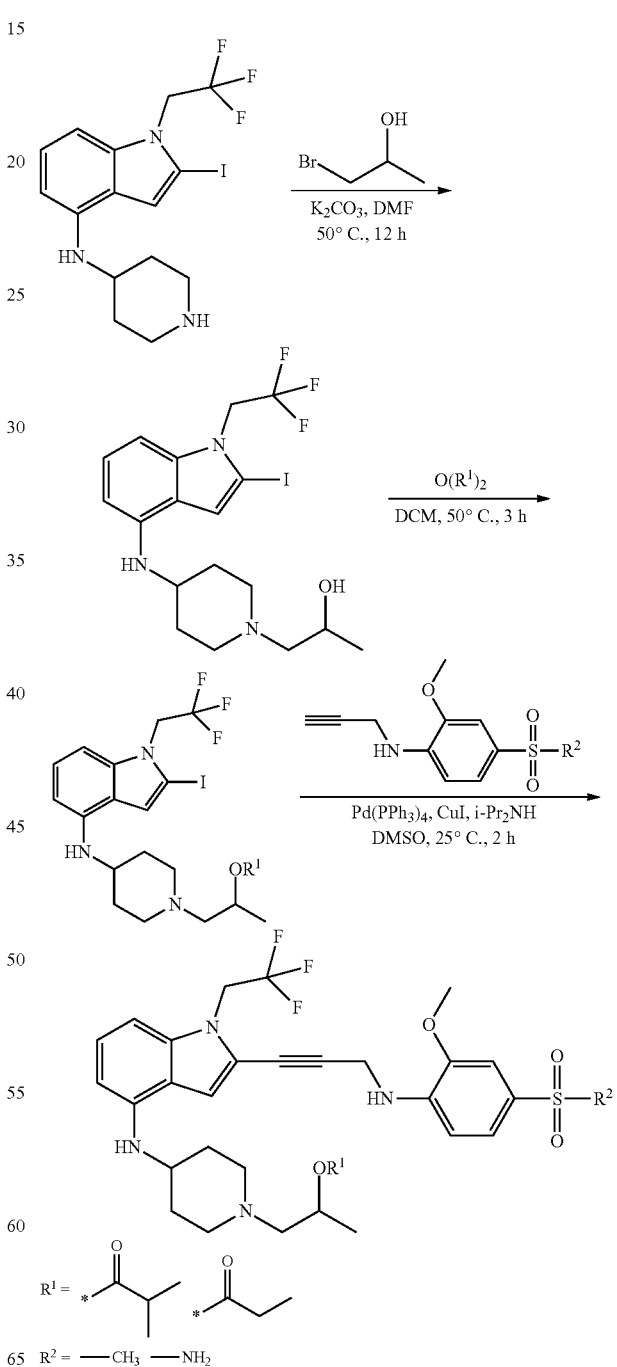

Step 1: To a mixture of 2-iodo-N-(piperidin-4-yl)-1-(2,2,2-trifluoroethyl)-1H-indol-4-amine (2 g, 4.63 mmol, 1 eq.) in DMF (20 mL) was added 1-bromopropan-2-ol (9.20 g, 46.31 mmol, 10 eq.), and $K_2CO_3$ (3.20 g, 23.16 mmol 5 eq.). The mixture was stirred at 50° C. for 12 h, after which time TLC analysis indicated that the starting material was completely consumed. The reaction was partitioned between water (20 mL) and EtOAc (20 mL), and then extracted with EtOAc (50 mL×3). The combined organic layers were washed with brine (50 mL×3), dried over anhydrous sodium sulfate, and filtered. The filtrate was concentrated in vacuo to provide the 1-(4-((2-iodo-1-(2,2,2-trifluoroethyl)-1H-indol-4-yl)amino)piperidin-1-yl)propan-2-ol as a black brown oil (3.8 g).

Step 2: To a mixture of 1-(4-((2-iodo-1-(2,2,2-trifluoroethyl)-1H-indol-4-yl)amino)piperidin-1-yl)propan-2-ol (210 mg, 436.32 µmol, 1 eq.) in DCM (3 mL) was added propanoyl propanoate (62.46 mg, 479.96 µmol, 1.1 eq.). The mixture was stirred at 50° C. for 3 h. TLC and LC-MS analysis indicated that the starting material was consumed completely. The reaction was partitioned between water (15 mL) and EtOAc (10 mL), and then extracted with EtOAc (20 mL×3). The combined organic layers were washed with brine (30 mL), dried over anhydrous sodium sulfate, and filtered. The filtrate was concentrated in vacuo. The crude product was purified by prep-TLC (PE:EtOAc=0:1, $R_f$=0.5) to give the product (140 mg, crude) as a light yellow oil. MS ($ES^{30}$, m/z): 254.9.

Step-Synthesis of final products: To a solution of [2-[4-[[2-iodo-1-(2,2,2-trifluoroethyl)indol-4-yl]amino]-1-piperidyl]-1-methyl-ethyl]propanoate (120 mg, 223.32 µmol, 1 eq.) in DMSO (3 mL) were added 3-methoxy-4-(prop-2-ynylamino)benzenesulfonamide (75.75 mg, 267.98 µmol, 1.2 eq.), i-PrNH$_2$ (132 mg, 2.23 mmol, 191.86 µL, 10 eq.), CuI (42.53 mg, 223.32 µmol, 1 eq.) and Pd(PPh$_3$)$_4$ (51.61 mg, 44.66 µmol, 0.2 eq.). The mixture was flushed with N$_2$ and stirred at 25° C. for 2 hrs. TLC analysis (PE:EtOAc=0:1, $R_f$=0.55) showed that the reaction was complete. The reaction mixture was quenched by adding saturated aqueous EDTA (20 mL) at 25° C. and stirring the resulting mixture for 2 hrs. The mixture was then extracted with EtOAc (10 mL×3). The organic phase was washed with brine (10 mL×3), dried over anhydrous sodium sulfate, filtered, and concentrated in vacuo to give the crude product. The residue was purified by prep-TLC (PE:EtOAc=0:1, $R_f$=0.45), then further purified by prep-HPLC to obtain the final product.

[2-[4-[[2-[3-(2-methoxy-4-sulfamoyl-anilino)prop-1-ynyl]-1-(2,2,2-trifluoroethyl)indol-4-yl]amino]-1-piperidyl]-1-methyl-ethyl]propanoate, 21.9 mg, 14.34% yield, MS ($ES^{30}$, m/z): 650.2; [2-[4-[[2-[3-(2-methoxy-4-methylsulfonyl-anilino)prop-1-ynyl]-1-(2,2,2-trifluoroethyl)indol-4-yl]amino]-1-piperidyl]-1-methyl-ethyl]propanoate, 6.3 mg, 6.98% yield, MS ($ES^{30}$, m/z): 649.3; [2-[4-[[2-[3-(2-methoxy-4-methylsulfonyl-anilino)prop-1-ynyl]-1-(2,2,2-trifluoroethyl)indol-4-yl]amino]-1-piperidyl]-1-methyl-ethyl]2-methylpropanoate, 11.6 mg, 12.11% yield; [2-[4-[[2-[3-(2-methoxy-4-sulfamoyl-anilino)prop-1-ynyl]-1-(2,2,2-trifluoroethyl)indol-4-yl]amino]-1-piperidyl]-1-methyl-ethyl]2-methylpropanoate (20 mg, 10.16% yield. MS ($ES^{30}$, m/z): 663.3.

(rac)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl propanoate, MS ($ES^{30}$): 649.3; and (rac)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl 2-methylpropanoate, MS ($ES^{30}$, m/z): 663.3.

Example D119: General Procedure for Preparation of Compounds 592A and 594A

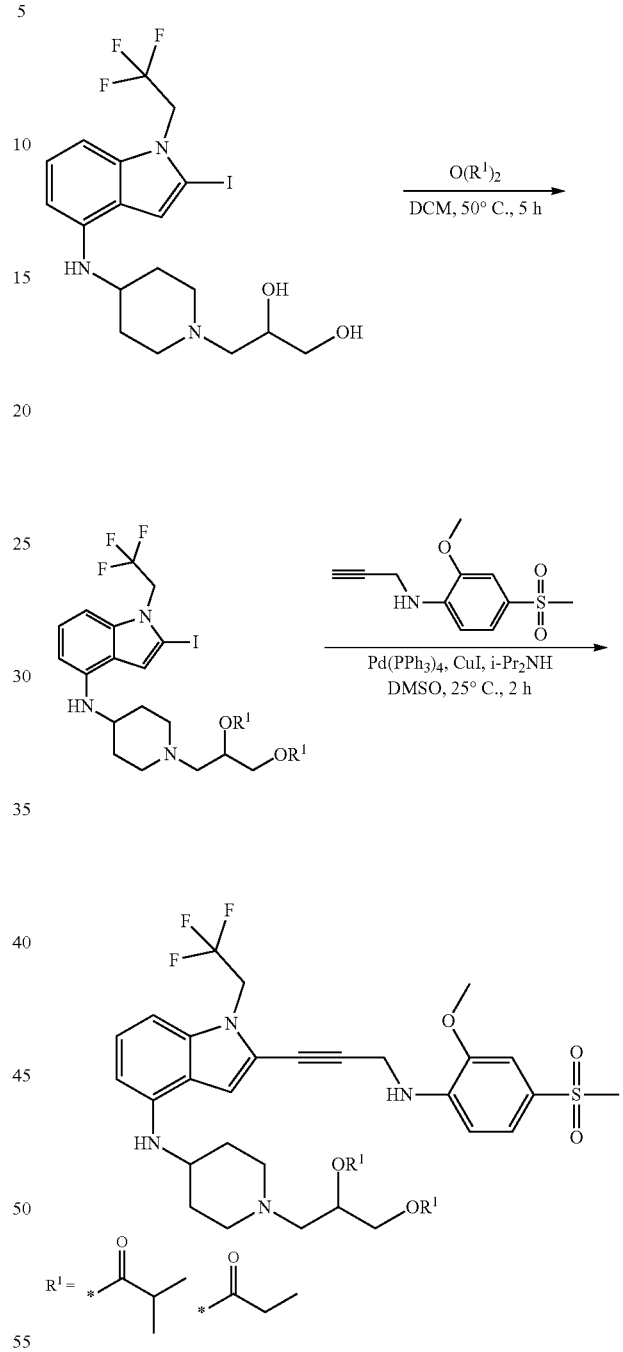

The desired products were prepared according to the procedure specified in EXAMPLE D117 except that 0.9 equivalents of anhydride O(R$^1$)$_2$ were used.

2-hydroxy-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propyl propanoate, MS ($ES^{30}$, m/z): 665.3; and 2-hydroxy-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propyl 2-methylpropanoate, MS ($ES^{30}$, m/z): 679.3.

Example D120: General Procedure for Preparation of Compounds 853A, 854A, 859A, 860A, 862A, and 863A

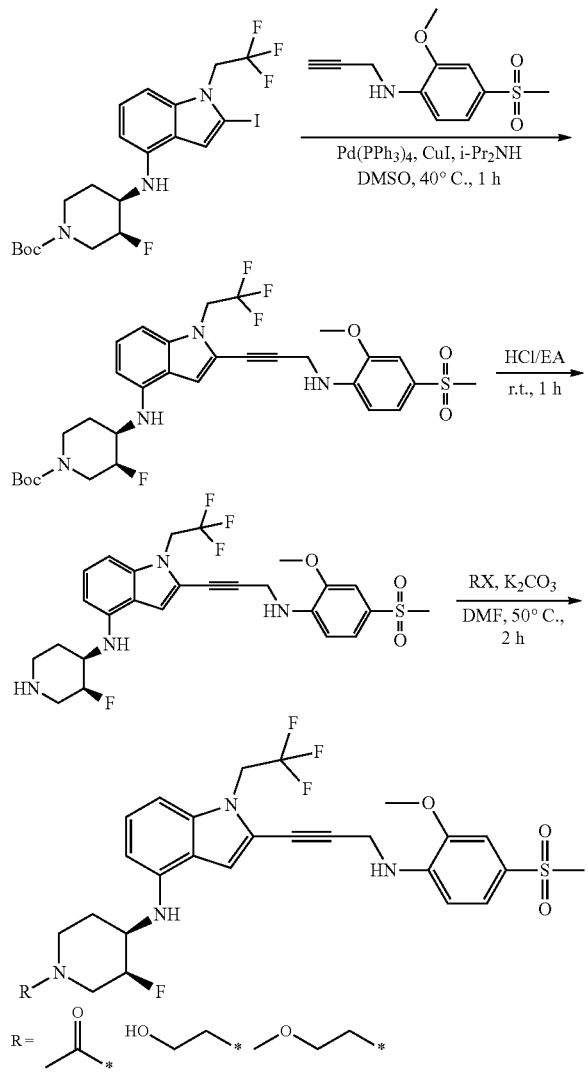

Synthesis of tert-butyl (3S,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidine-1-carboxylate: To a solution of 2-methoxy-4-(methylsulfonyl)-N-(prop-2-yn-1-yl)aniline (1.13 g, 3.33 mmol) in DMSO (15 mL) were added i-Pr$_2$NH (2.80 g, 27.71 mmol, 10 eq.), CuI (105.55 mg, 554.20 μmol, 0.2 eq.), tert-butyl (3S,4R)-3-fluoro-4-((2-iodo-1-(2,2,2-trifluoroethyl)-1H-indol-4-yl)amino)piperidine-1-carboxylate (1.5 g, 2.77 mmol), and Pd(PPh$_3$)$_4$ (160.10 mg, 138.55 μmol, 0.05 eq.). The mixture was stirred at 40° C. for 1 h under N$_2$ atmosphere, after which time TLC (PE:EtOAc=2:1, R$_{f(sm)}$= 0.6, R$_{f(pdt)}$=0.1) indicated that the starting material was completely consumed, and one new spot had formed. The reaction mixture was quenched by adding a saturated aqueous EDTA solution (30 mL), stirring the mixture at 20° C. for 1 h, diluting the mixture with water (10 mL), and extracting the resulting mixture with EtOAc (20 mL×3). The combined organic layers were washed with brine (15 mL×3), dried over anhydrous sodium sulfate, filtered, and concentrated in vacuo. The resulting residue was purified by column chromatography (SiO$_2$, PE:EtOAc=4:1 to 2:1) to provide tert-butyl (3S,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidine-1-carboxylate as a yellow solid (1.8 g). $^1$H NMR (400 MHz, DMSO-d6) δ ppm 1.31-1.43 (18H, m) 1.65-1.74 (1H, m) 1.75-1.86 (1H, m) 2.80-3.05 (1H, m) 3.09-3.28 (4H, m) 3.72-3.87 (1H, m) 3.92 (3H, s) 4.04-4.12 (1H, m) 4.16-4.36 (1H, m) 4.50-4.81 (2H, m) 4.82-4.98 (3H, m) 5.54-5.64 (1H, m) 6.25-6.33 (1H, m) 6.70-6.82 (1H, m) 7.00-7.07 (1H, m) 7.16-7.19 (1H, m) 7.51-7.54 (2H, m) 7.57 (1H, s).

The procedure was repeated using tert-butyl (3R,4S)-3-fluoro-4-((2-iodo-1-(2,2,2-trifluoroethyl)-1H-indol-4-yl)amino)piperidine-1-carboxylate in place of tert-butyl (3S,4R)-3-fluoro-4-((2-iodo-1-(2,2,2-trifluoroethyl)-1H-indol-4-yl)amino)piperidine-1-carboxylate to provide (3R,4S)-4-((2-(3-((tert-butoxycarbonyl)(2-methoxy-4-(methylsulfonyl)phenyl)amino)prop-1-yn-1-yl)-1-(2,2,2-trifluoroethyl)-1H-indol-4-yl)amino)-3-fluoropiperidine-1-carboxylate.

Synthesis of N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine and N-((3R,4S)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine: A solution of tert-butyl (3S,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidine-1-carboxylate (1.8 g, 2.39 mmol, 1 eq.) in HCl/EtOAc (4 M, 36 mL, 60.23 eq.) was stirred at 20° C. for 1 h under N$_2$ atmosphere. TLC analysis (EtOAc:TEA=10:1, R$_{f1}$=0.91, R$_{f2}$=0.1) indicated that the starting material was completely consumed, and one new spot was detected. The reaction mixture was quenched with saturated aqueous Na$_2$CO$_3$ (10 mL) and extracted with EtOAc (10 mL×3). The combined organic layers were washed with brine (10 mL×3), dried over anhydrous sodium sulfate, filtered, and concentrated under reduced pressure to provide N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine as a yellow solid (1.0 g). $^1$H NMR (400 MHz, DMSO-d6) δ ppm 1.61-1.69 (1H, m) 1.75 (1H, qd, J=12.07, 3.56 Hz) 2.56-2.69 (1H, m) 2.72-2.89 (1H, m) 2.95-3.03 (1H, m) 3.05-3.10 (3H, m) 3.12-3.20 (1H, m) 3.60-3.77 (1H, m) 3.87-3.91 (3H, m) 4.32-4.40 (2H, m) 4.65-4.81 (1H, m) 4.86-5.01 (2H, m) 5.48-5.56 (1H, m) 6.19-6.31 (1H, m) 6.45-6.54 (1H, m) 6.69-6.77 (1H, m) 6.84-6.92 (1H, m) 6.94-7.04 (1H, m) 7.17-7.22 (1H, m) 7.23-7.28 (1H, m) 7.37-7.41 (1H, m).

The procedure was repeated using tert-butyl (3R,4S)-4-((2-(3-((tert-butoxycarbonyl)(2-methoxy-4-(methylsulfonyl)phenyl)amino)prop-1-yn-1-yl)-1-(2,2,2-trifluoroethyl)-1H-indol-4-yl)amino)-3-fluoropiperidine-1-carboxylate in place of tert-butyl (3S,4R)-4-((2-(3-((tert-butoxycarbonyl)(2-methoxy-4-(methylsulfonyl)phenyl)amino)prop-1-yn-1-yl)-1-(2,2,2-trifluoroethyl)-1H-indol-4-yl)amino)-3-fluoropiperidine-1-carboxylate to provide N-((3R,4S)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine.

Synthesis of final products: To a solution of N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine (0.05 g, 90.48 μmol, 1 eq.) and acetyl chloride (56.54 mg, 452.42 μmol, 5 eq.), (RX=2-bromoethan-1-ol, or 1-bromo-2-methoxyethane) in DMF (3 mL) was added K$_2$CO$_3$ (37.52 mg, 271.45 µmol, 3 eq. The mixture was stirred at 50° C. for 2 h. TLC analysis (EtOAc:TEA=10:1, R$_f$=0.3) indicated that the starting material was consumed, and one major new spot was detected. The reaction mixture was quenched with water (10 mL), and then extracted with EtOAc (10 mL×3). The combined organic layers were washed with brine (10 mL×3), dried over anhydrous sodium sulfate, filtered, and concentrated under reduced pressure. The residue was purified by prep-HPLC to provide the desired products.

1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one, 27 mg, 27% yield, MS (ES$^{30}$, m/z): 595.2; 2-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-ol, 28 mg, 21% yield, MS (ES$^{30}$, m/z): 597.2; and N-[(3S,4R)-3-fluoro-1-(2-methoxyethyl)piperidin-4-yl]-2-{3-[(4-methanesulfonyl-2-methoxyphenyl)amino]prop-1-yn-1-yl}-1-(2,2,2-trifluoroethyl)-1H-indol-4-amine, 30 mg, 27% yield, MS (ES$^{30}$, m/z): 611.2.

The procedure was repeated using N-((3R,4S)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine in place of N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine.

1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one, (22 mg, 23% yield, MS (ES$^{30}$, m/z): 595.2; 2-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-ol, (26 mg 24% yield, MS (ES$^{30}$, m/z): 597.2; and N-[(3R,4S)-3-fluoro-1-(2-methoxyethyl)piperidin-4-yl]-2-{3-[(4-methanesulfonyl-2-methoxyphenyl)amino]prop-1-yn-1-yl}-1-(2,2,2-trifluoroethyl)-1H-indol-4-amine), (30 mg) 27% yield, MS (ES$^{30}$, m/z): 611.2.

Example D121: Preparation of Compounds 871A and 894A

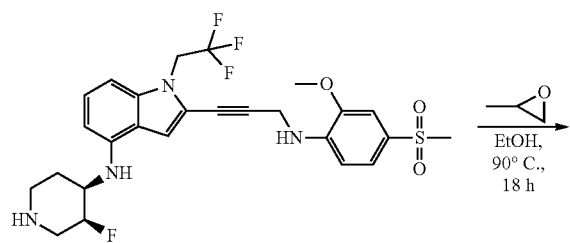

A mixture of N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine (0.1 g, 180.97 mol 1 eq.) and propylene oxide (31.53 mg, 542.90 µmol, 3 eq.) in EtOH (3 mL) was stirred at 90° C. for 18 h. under N$_2$ atmosphere. TLC analysis indicated that one major new spot had formed. The reaction mixture was quenched with water (10 mL) and extracted with EtOAc (20 mL×3). The combined organic layers were washed with brine (15 mL×3), dried over anhydrous sodium sulfate, filtered, and concentrated under reduced pressure. The residue was purified by prep-TLC (SiO$_2$, EtOAc:TEA=10:1) and further purified by prep-HPLC to provide 1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]propan-2-ol, (24 mg, 21.7% yield) MS (ES$^{30}$, m/z): 611.2.

The procedure was repeated using N-((3R,4S)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine in place of N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine to provide 1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]propan-2-ol, MS (ES$^{30}$, m/z): 611.2.

Example D122: Preparation of Compounds 853A and 854A

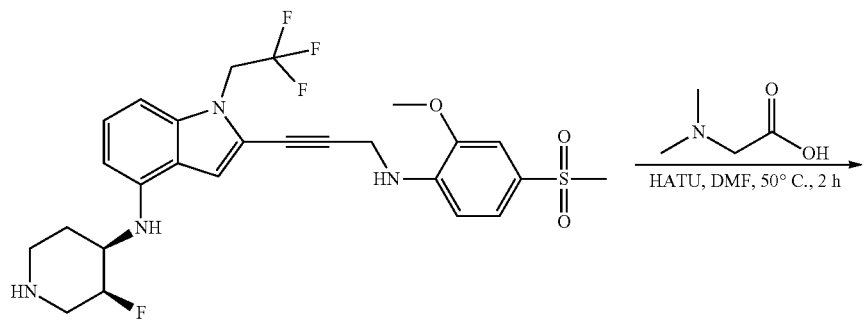

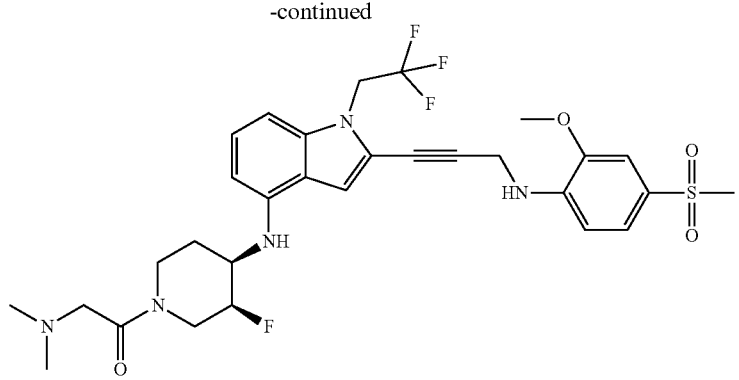

To a solution of N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine (0.05 g, 90.48 µmol and 2-(dimethylamino)acetic acid (18.66 mg, 180.97 µmol, 2 eq.) in DMF (3 mL) were added HATU (68.81 mg, 180.97 µmol, 2 eq.) and TEA (27.47 mg, 271.45 µmol, 37.78 µL, 3 eq.). The mixture was stirred at 50° C. for 2 h. TLC (EtOAc:TEA=10:1, R$_f$=0.35) indicated that the starting material was consumed completely, and one new spot was detected. The reaction mixture was quenched with saturated aqueous solution of Na$_2$CO$_3$ (10 mL), diluted with water (10 mL), and extracted with EtOAc (20 mL×3). The combined organic layers were washed with brine (15 mL×3), dried over anhydrous sodium sulfate, filtered, and concentrated under reduced pressure. The residue was purified by prep-HPLC to provide 2-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-ol, 27 mg, 46.2% yield. MS (ES$^{30}$, m/z): 638.3.

Example D123: Preparation of Compounds 892A and 893A

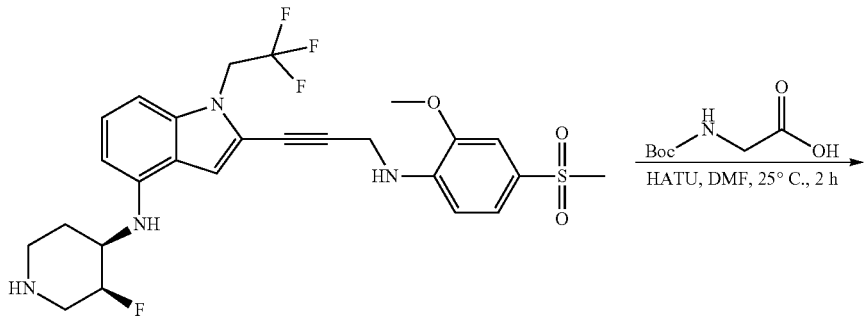

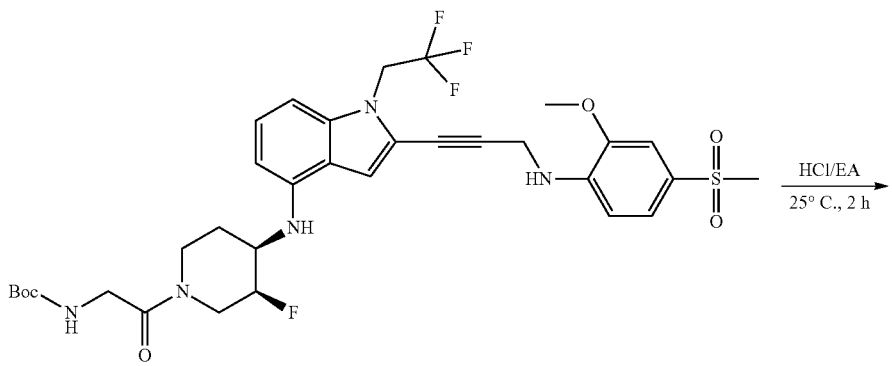

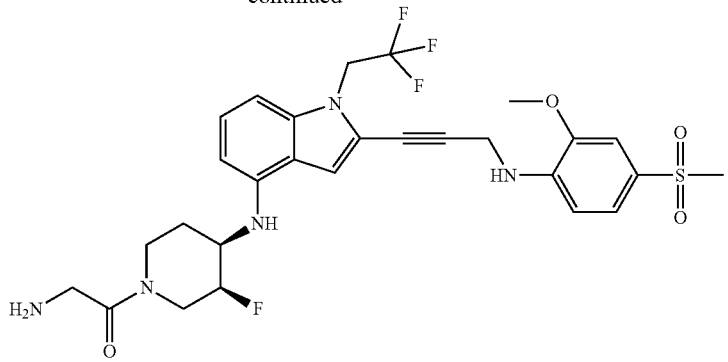

Synthesis of tert-butyl (2-((3S,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-2-oxoethyl)carbamate and tert-butyl (2-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-2-oxoethyl)carbamate: To a solution of N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine (0.1 g, 180.97 μmol, 1 eq.) and 2-(tert-butoxycarbonylamino)acetic acid (63.40 mg, 361.94 μmol, 2 eq.) in DMF (2 mL) was added TEA (91.56 mg, 904.84 μmol, 125.94 μL, 5 eq.) and HATU (206.43 mg, 542.90 μmol, 3 eq.). The mixture was stirred at 25° C. for 2 h under $N_2$ atmosphere, after which time TLC analysis (EtOAc:TEA=10:1, $R_{f1}$=0.1, $R_{f2}$=0.55) indicated that the starting material was completely consumed, and one new spot had formed. The reaction mixture was quenched with water (15 mL) at 25° C. and extracted with EtOAc (15 mL×3). The combined organic layers were washed with brine (10 mL), dried over anhydrous sodium sulfate, filtered, and concentrated under reduced pressure. The residue was purified by prep-TLC ($SiO_2$, EtOAc:TEA=10:1) to provide tert-butyl (2-((3S,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-2-oxoethyl)carbamate (100 mg, 70% yield) as a yellow solid.

The procedure was repeated using N-((3R,4S)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine in place of N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine to provide tert-butyl (2-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-2-oxoethyl)carbamate (68% yield) as a yellow solid.

Synthesis of final products: tert-Butyl (2-((3S,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-2-oxoethyl)carbamate (0.1 g, 140.89 μmol, 1 eq.) was added to HCl/EtOAc (4N, 5 mL). The resulting mixture was stirred at 25° C. for 0.5 h, after which time TLC analysis (EtOAc:TEA=10:1, $R_{f1}$, =0.5, $R_{f1}$=0.25) indicated that the Boc-protected starting material was completely consumed, and one new spot had formed. The reaction mixture was quenched with saturated aqueous $Na_2CO_3$ (10 mL) and extracted with EtOAc (10 mL×3). The combined organic layers were washed with brine (10 mL), filtered, and concentrated under reduced pressure. The residue was purified by prep-HPLC to provide 2-amino-1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one (35 mg, 40.7% yield) as a yellow solid. MS ($ES^{30}$, m/z): 610.2.

The procedure was repeated using tert-butyl (2-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-2-oxoethyl)carbamate in place of tert-butyl (2-((3S,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-2-oxoethyl)carbamate to provide 2-amino-1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one (30 mg, 36% yield) as a yellow solid. MS ($ES^{30}$, m/z): 610.2.

Example D124: Preparation of Compounds 861A and 869A

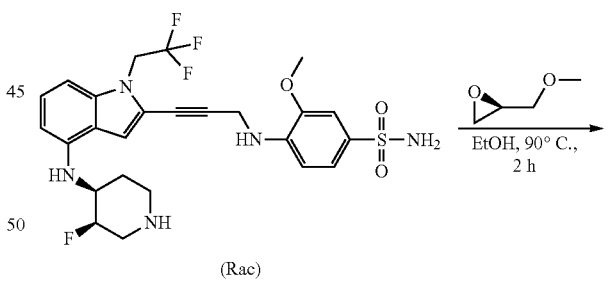

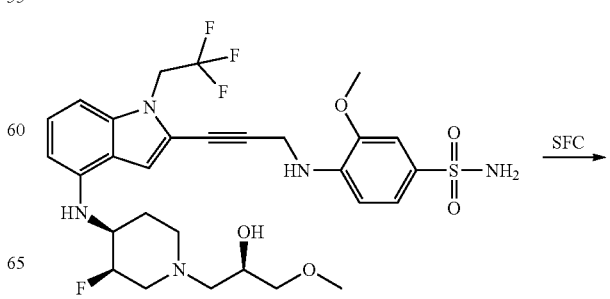

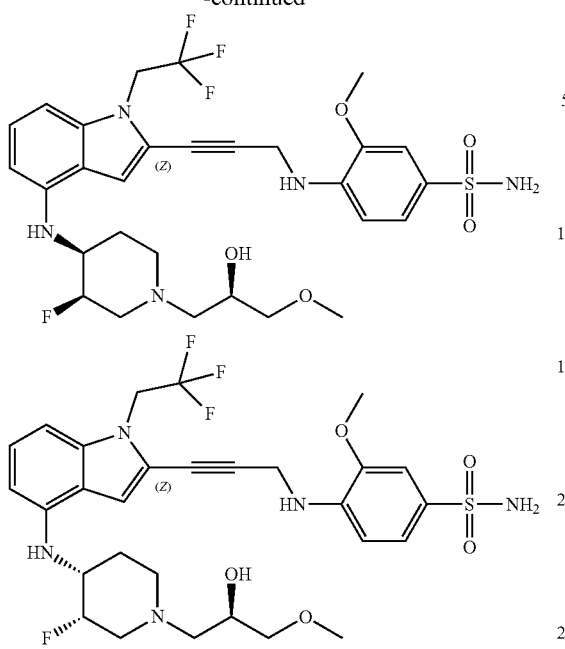

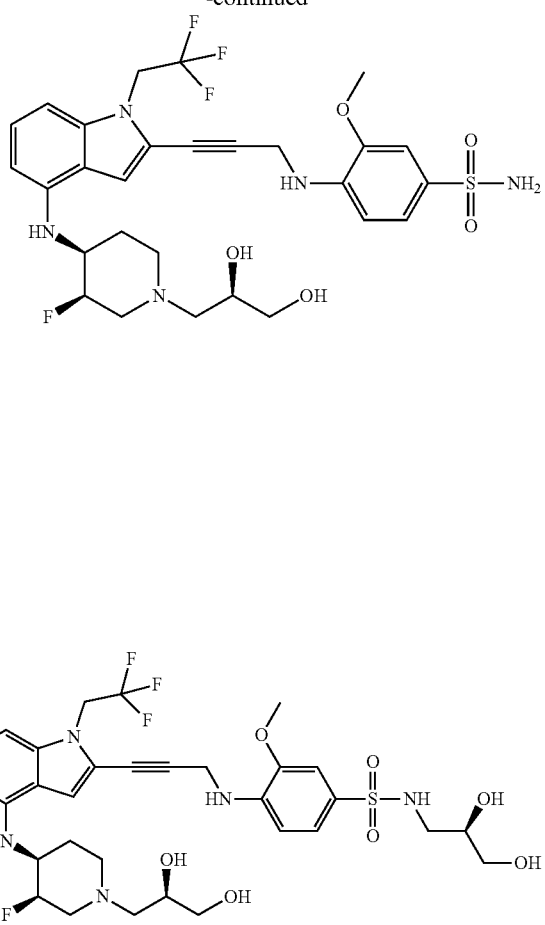

To a solution of (rac)-4-((3-(4-(((3R,4S)-3-fluoropiperidin-4-yl)amino)-1-(2,2,2-trifluoroethyl)-1H-indol-2-yl)prop-2-yn-1-yl)amino)-3-methoxybenzenesulfonamide (150 mg, 270.97 μmol, 1 eq.) in EtOH (2 mL) was added (R)-2-(methoxymethyl)oxirane (143.24 mg, 1.63 mmol, 144.69 μl, 6 eq.). The mixture was stirred at 90° C. for 2 h, after which time TLC analysis (DCM:MeOH=10:1) indicated that the secondary amine starting material was consumed, and one new spot had formed. The reaction mixture was concentrated under reduced pressure. The resulting residue was purified by prep-HPLC, to obtain a mixture of diastereomers (80 mg, 124.67 μmol, 46.01% yield), which was then resolved by chiral SFC to provide the separated diastereomers as light yellow solids.

4-{[3-(4-{[(3R,4S)-3-fluoro-1-[(2R)-2-hydroxy-3-methoxypropyl]piperidin-4-yl]amino}-1-(2,2,2-trifluoroethyl)-1H-indol-2-yl)prop-2-yn-1-yl]amino}-3-methoxybenzene-1-sulfonamide, MS (ES$^{30}$, m/z): 624.3; and 4-{[3-(4-{[(3S,4R)-3-fluoro-1-[(2R)-2-hydroxy-3-methoxypropyl]piperidin-4-yl]amino}-1-(2,2,2-trifluoroethyl)-1H-indol-2-yl)prop-2-yn-1-yl]amino}-3-methoxybenzene-1-sulfonamide, MS (ES$^{30}$, m/z): 624.3.

Example D125: Preparation of Compounds 882A and 883A

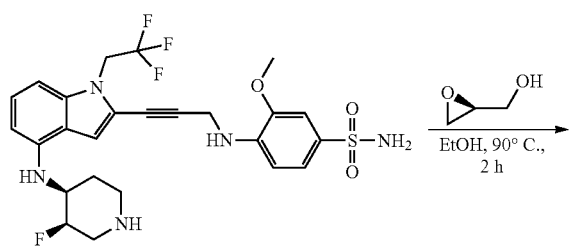

To a solution of (rac)-4-((3-(4-(((3R,4S)-3-fluoropiperidin-4-yl)amino)-1-(2,2,2-trifluoroethyl)-1H-indol-2-yl)prop-2-yn-1-yl)amino)-3-methoxybenzenesulfonamide (300 mg, 541.94 μmol, 1 eq.) in EtOH (7 mL) was added (S)-oxiran-2-ylmethanol (200.73 mg, 2.71 mmol, 179.22 μl, 5 eq.). The mixture was stirred at 90° C. for 2 h, after which time TLC analysis (DCM:MeOH=10:1, Rf=0.43) indicated that the reaction was complete. The reaction mixture was concentrated under reduced pressure to remove solvent, and the residue was purified by prep-TLC (SiO$_2$, DCM:MeOH=10:1). The residue was then further purified by prep-HPLC to afford the diastereomeric mixture (100 mg, 159.32 μmol, 29.40% yield) as a light yellow solid. The byproduct (65 mg, 91.33 μmol), which was also obtained as a light yellow solid, was subjected to resolution by chiral SFC to provide the desired enantiopure products.

4-{[3-(4-{[(3R,4S)-1-[(2R)-2,3-dihydroxypropyl]-3-fluoropiperidin-4-yl]amino}-1-(2,2,2-trifluoroethyl)-1H-indol-2-yl)prop-2-yn-1-yl]amino}-3-methoxybenzene-1-sulfonamide, MS (ES$^{30}$, m/z): 628.3; 4-{[3-(4-{[(3S,4R)-1-[(2R)-2,3-dihydroxypropyl]-3-fluoropiperidin-4-yl]amino}-1-(2,2,2-trifluoroethyl)-1H-indol-2-yl)prop-2-yn-1-yl]amino}-3-methoxybenzene-1-sulfonamide, MS (ES$^{30}$, m/z): 628.3; and N-[(2R)-2,3-dihydroxypropyl]-4-{[3-(4-{[(3RS,4SR)-3-fluoro-1-[(2R)-2-hydroxy-3-methoxypropyl]piperidin-4-yl]amino}-1-(2,2,2-trifluoroethyl)-1H-indol-2-yl)prop-2-yn-1-yl]amino}-3-methoxybenzene-1-sulfonamide, MS (ES$^{30}$, m/z): 702.2 (M-Me).

Example D126: Preparation of Compounds 882A and 883A

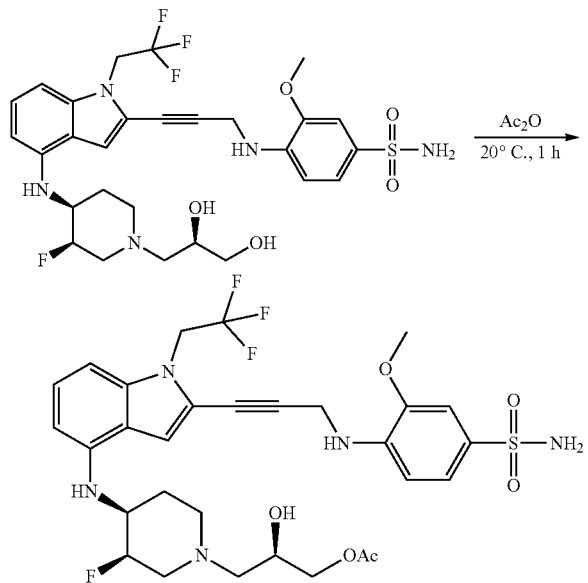

A solution of 4-((3-(4-(((3R,4S)-1-((R)-2,3-dihydroxypropyl)-3-fluoropiperidin-4-yl)amino)-1-(2,2,2-trifluoroethyl)-1H-indol-2-yl)prop-2-yn-1-yl)amino)-3-methoxybenzenesulfonamide (300 mg, 406.28 μmol, 1 eq.) in acetic anhydride (8.34 g, 81.68 mmol, 7.65 mL, 201.04 eq.) was stirred at 20° C. for 1 h, after which time TLC analysis (DCM:MeOH=10:1, $R_f$=0.43) indicated that the reaction was complete. The reaction mixture was concentrated in vacuo, and the residue was purified by prep-TLC (SiO$_2$, DCM:MeOH=10:1, Rf=0.43). Diastereomeric mixture (R)-3-((3R,4S)-3-fluoro-4-((2-(3-((2-methoxy-4-sulfamoylphenyl)amino)prop-1-yn-1-yl)-1-(2,2,2-trifluoroethyl)-1H-indol-4-yl)amino)piperidin-1-yl)propane-1,2-diyl diacetate (100 mg, 136.15 μmol, 33.51% yield) was obtained as a light yellow solid, which was then further purified via chiral SFC to provide 4-{[3-(4-{[(3S,4R)-1-[(2R)-2,3-dihydroxypropyl]-3-fluoropiperidin-4-yl]amino}-1-(2,2,2-trifluoroethyl)-1H-indol-2-yl)prop-2-yn-1-yl]amino}-3-methoxybenzene-1-sulfonamide (25.1 mg, 34.77 μmol) as a light yellow solid (MS (ES$^{30}$, m/z): 628.3), and 4-{[3-(4-{[(3R,4S)-1-[(2R)-2,3-dihydroxypropyl]-3-fluoropiperidin-4-yl]amino}-1-(2,2,2-trifluoroethyl)-1H-indol-2-yl)prop-2-yn-1-yl]amino}-3-methoxybenzene-1-sulfonamide (22.7 mg, 31.16 μmol) as a light yellow solid (MS (ES$^{30}$, m/z): 628.3).

Example D127: Preparation of Compound 891A

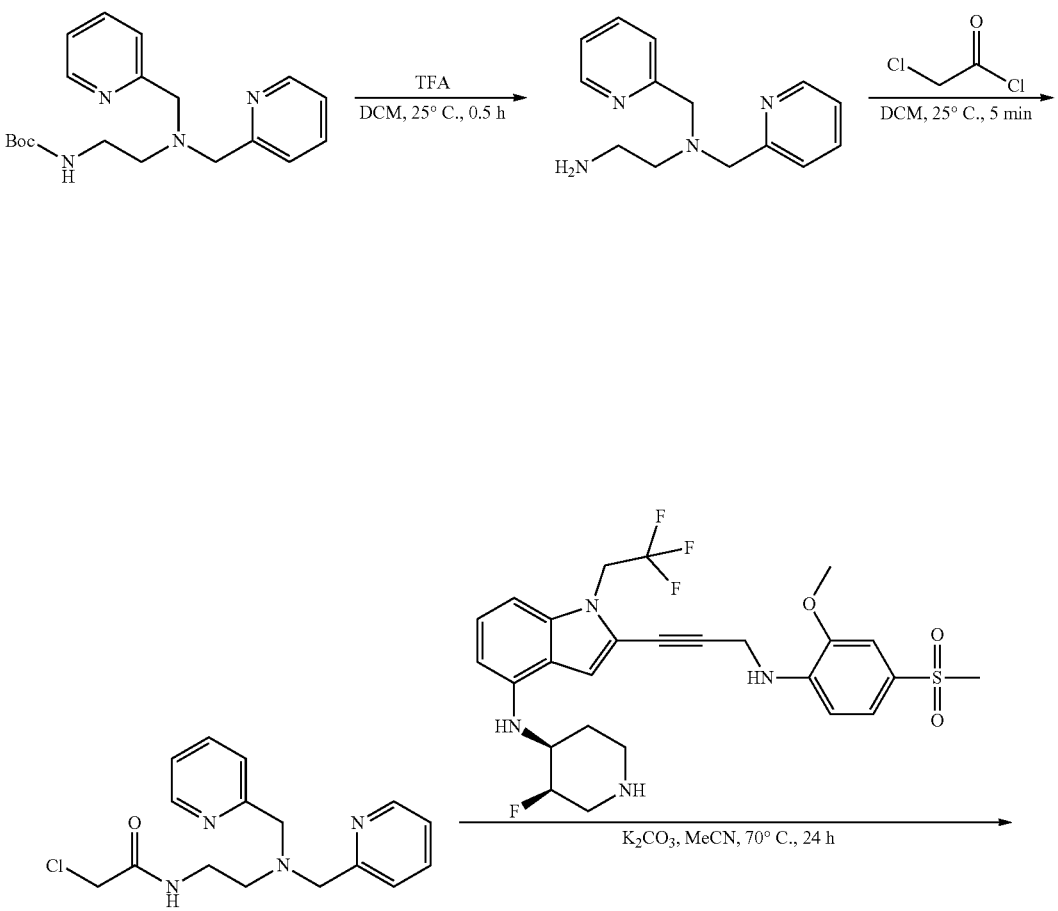

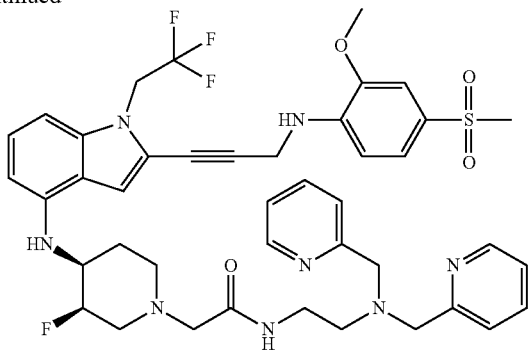

Synthesis of N¹,N¹-bis(pyridin-2-ylmethyl)ethane-1,2-diamine: To a solution of tert-butyl (2-(bis(pyridin-2-ylmethyl)amino)ethyl)carbamate (1.5 g, 4.38 mmol, 1 eq.) in DCM (5 mL) was added TFA (11.55 g, 101.30 mmol, 7.50 mL, 23.12 eq.). The resulting mixture was stirred at 25° C. for 0.5 h, after which time LC-MS analysis indicated that the reaction was complete. The reaction mixture was quenched with saturated solution of $Na_2CO_3$ (100 mL) at 25° C., and then extracted with EtOAc (100 mL×10). The combined organic layers were dried over anhydrous sodium sulfate, filtered, and concentrated under reduced pressure to provide N¹,N¹-bis(pyridin-2-ylmethyl)ethane-1,2-diamine (1.1 g, crude) as a light yellow oil. MS ($ES^{30}$, m/z): 243.1.

Synthesis of N-(2-(bis(pyridin-2-ylmethyl)amino)ethyl)-2-chloroacetamide: To a solution of N¹,N¹-bis(pyridin-2-ylmethyl)ethane-1,2-diamine (500 mg, 2.06 mmol, 1 eq.) in DCM (3 mL) was added chloroacetyl chloride (233.05 mg, 2.06 mmol, 164.12 μl, 1 eq.). The mixture was stirred at 25° C. for 5 min, after which time TLC analysis (DCM: MeOH=10:1, $R_f$=0.24) indicated that the reaction was complete. The reaction mixture was quenched by adding a saturated solution of $Na_2CO_3$ (40 mL) at 25° C. and extracted with DCM (25 mL×4). The combined organic layers were dried over anhydrous sodium sulfate, filtered, and concentrated under reduced pressure to provide N-(2-(bis(pyridin-2-ylmethyl)amino)ethyl)-2-chloroacetamide (550 mg, crude) as a light yellow oil.

Synthesis of final product: To a solution of (rac)-N-((3R,4S)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine (100 mg, 180.97 μmol, 1 eq.) in MeCN (3 mL) was added $K_2CO_3$ (250.12 mg, 1.81 mmol, 10 eq.), followed by then N-(2-(bis(pyridin-2-ylmethyl)amino)ethyl)-2-chloroacetamide (144.23 mg, 361.94 μmol, 2 eq.). The mixture was stirred at 70° C. for 24 h, after which time LC-MS analysis indicated that the reaction was complete. The reaction mixture was filtered and then concentrated under reduced pressure to remove solvent. The residue was purified by prep-HPLC to provide rac-N-(2-{bis[(pyridin-2-yl)methyl]amino}ethyl)-2-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]acetamide (25.8 mg, 30.78 μmol, 17.01% yield) as a light yellow solid.

Example D128: Preparation of Compounds 795A, 802A, 803A

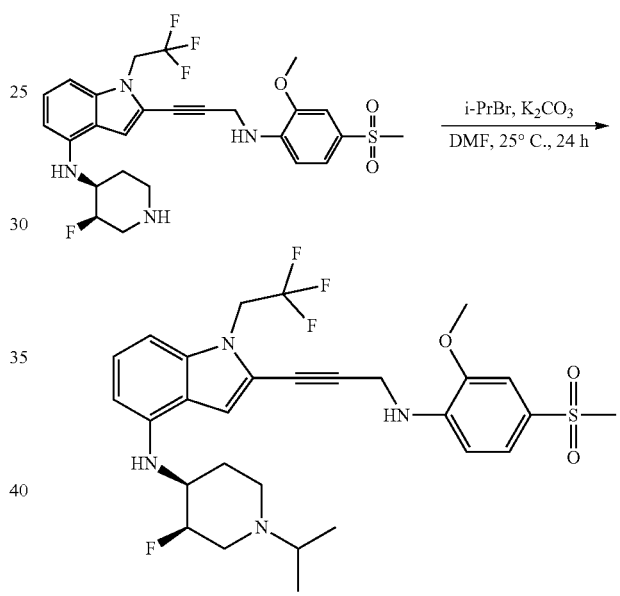

To a solution of (rac)-N-((3R,4S)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine (200 mg, 361.9 μmol, 1 eq.) in DMF (4 mL) was added $K_2CO_3$ (150.1 mg, 1.1 mmol, 3 eq.), followed by 2-bromopropane (445.2 mg, 3.6 mmol, 339.8 μl, 10 eq.). The reaction mixture was stirred at 25° C. for 24 h, after which time TLC analysis indicated that the starting material was consumed completely. The reaction mixture was quenched with water (40 mL), and EtOAc (50 mL) was added. The mixture was extracted with EtOAc (20 mL×3), and the combined organic layers were washed with brine (20 mL×3), dried over anhydrous sodium sulfate, filtered, and concentrated in vacuo. The residue was purified by prep-TLC ($SiO_2$, DCM: MeOH=10:1), dissolved in DCM (5 mL), filtered, and concentrated under reduced pressure. The resulting residue was further purified by prep-HPLC to provide (rac)-N-[(3R,4S)-3-fluoro-1-(propan-2-yl)piperidin-4-yl]-2-{3-[(4-methanesulfonyl-2-methoxyphenyl)amino]prop-1-yn-1-yl}-1-(2,2,2-trifluoroethyl)-1H-indol-4-amine. The constituent enantiomers were then resolved via chiral SFC to provide N-[(3R,4S)-3-fluoro-1-(propan-2-yl)piperidin-4-yl]-2-{3-

[(4-methanesulfonyl-2-methoxyphenyl)amino]prop-1-yn-1-yl}-1-(2,2,2-trifluoroethyl)-1H-indol-4-amine (20.4 mg, 34.27 μmol) was obtained as a light yellow solid (MS (ES³⁰, m/z): 595.3). N-[(3S,4R)-3-fluoro-1-(propan-2-yl)piperidin-4-yl]-2-{3-[(4-methanesulfonyl-2-methoxyphenyl)amino]prop-1-yn-1-yl}-1-(2,2,2-trifluoroethyl)-1H-indol-4-amine (20.8 mg, 34.45 μmol) was obtained as a light yellow solid (MS (ES³⁰, m/z): 595.3).
Example D129: Preparation of Compounds 780A and 792A
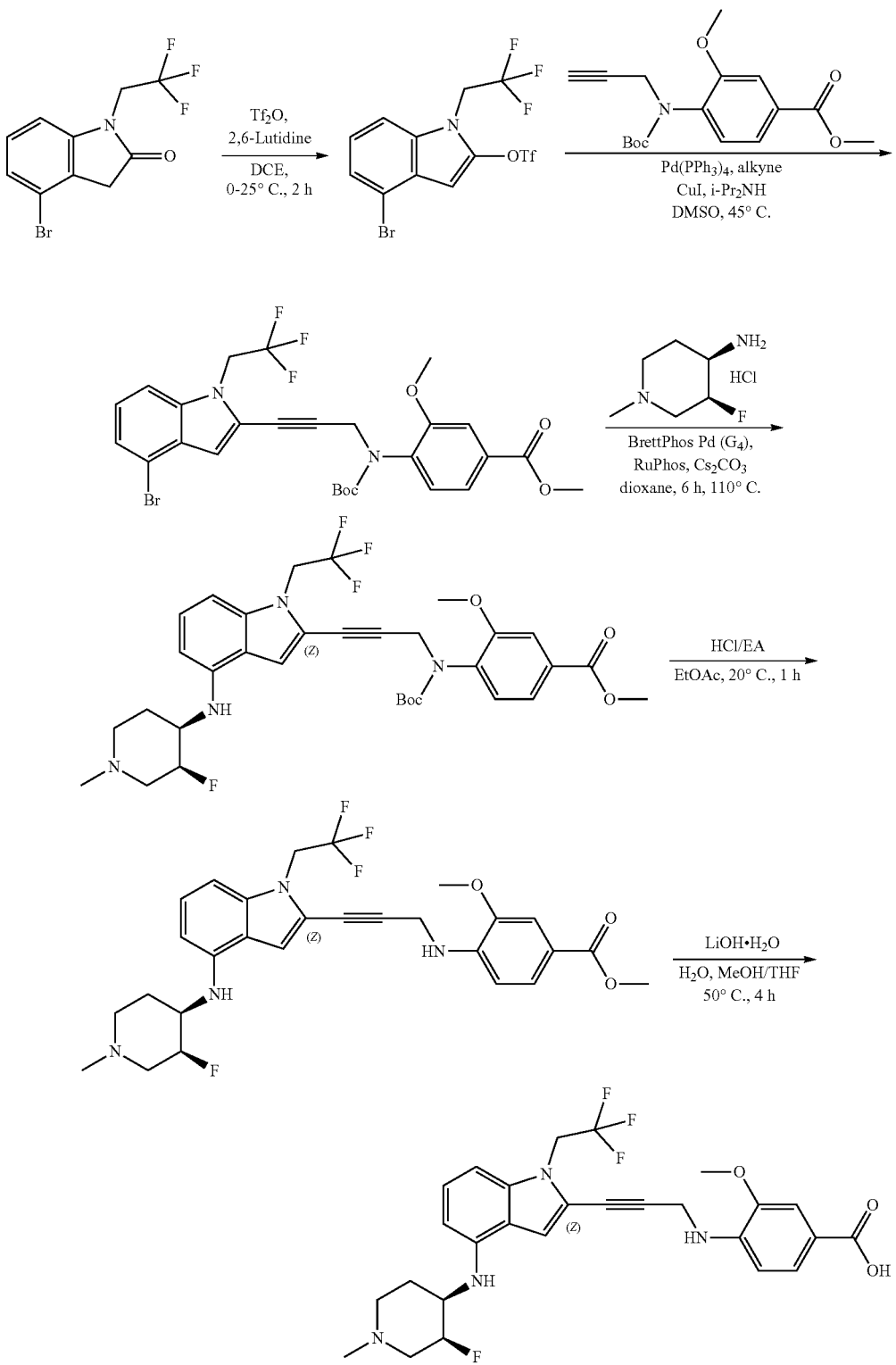

Synthesis of 4-bromo-1-(2,2,2-trifluoroethyl)-1H-indol-2-yl trifluoromethanesulfonate: To a solution of 4-bromo-1-(2,2,2-trifluoroethyl)indolin-2-one (10 g, 34.01 mmol, 1 eq.) and 2,6-lutidine (4.37 g, 40.81 mmol, 4.75 mL, 1.2 eq.) in DCM (100 mL) was added trifluoromethylsulfonyl trifluoromethanesulfonate (9.59 g, 34.01 mmol, 5.61 mL, 1 eq.) dropwise at 25° C. The reaction mixture was stirred at 25° C. for 2 h, after which time TLC analysis (PE:EtOAc=3:1, $R_f$=0.5) indicated that the reaction was complete. The reaction mixture was poured into a saturated aqueous solution of NH$_4$Cl (100 mL) and extracted with DCM (60 mL×3). The remaining aqueous phase added to saturated solution of NaHCO$_3$ (100 mL) and again extracted with DCM (60 mL×3). The combined organic layers were washed with brine (20 mL), dried over anhydrous sodium sulfate, filtered, and concentrated in vacuo. The residue was purified by column chromatography (SiO$_2$, PE:EtOAc=1:0 to 100:1, $R_f$=0.5) to provide [4-bromo-1-(2,2,2-trifluoroethyl)indol-2-yl]trifluoromethanesulfonate (13.0 g, 27.46 mmol, 80.74% yield) as a yellow solid.

Synthesis of methyl 4-((3-(4-bromo-1-(2,2,2-trifluoroethyl)-1H-indol-2-yl)prop-2-yn-1-yl)(tert-butoxycarbonyl)amino)-3-methoxybenzoate: To a solution of methyl 4-((tert-butoxycarbonyl)(prop-2-yn-1-yl)amino)-3-methoxybenzoate (10.72 g, 33.56 mmol, 1.1 eq.) in DMSO (130 mL) was added i-Pr$_2$NH (30.87 g, 305.07 mmol, 43.11 mL, 10 eq.), CuI (290.50 mg, 1.53 mmol, 0.05 eq.) and 4-bromo-1-(2,2,2-trifluoroethyl)-1H-indol-2-yl trifluoromethanesulfonate (13 g, 30.51 mmol, 1 eq.) at 20° C. Pd(PPh$_3$)$_4$ (1.76 g, 1.53 mmol, 0.05 eq.) was then added, and the mixture was purged with N$_2$ three times. The mixture was stirred at 25° C. for 1 h, after which time TLC analysis ($R_f$=0.5, PE:EtOAc=3:1) indicated that the starting material was consumed. EtOAc (200 mL) and a saturated aqueous EDTA solution (300 mL) were added and stirred at 25° C. for 1 h. The mixture was extracted with EtOAc (200 mL×3), and The combined organic layers were washed with brine (50 mL×3) dried over anhydrous sodium sulfate, filtered, and concentrated. The residue was purified by column chromatography (SiO$_2$, PE:EtOAc=15:1 to 8:1), and the solid concentrated eluate was washed with MTBE (45 mL) to provide methyl 4-((3-(4-bromo-1-(2,2,2-trifluoroethyl)-1H-indol-2-yl)prop-2-yn-1-yl)(tert-butoxycarbonyl)amino)-3-methoxybenzoate (14.1 g, 23.45 mmol, 76.87% yield) as a yellow solid.

Synthesis of methyl 4-((tert-butoxycarbonyl)(3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoate: To a mixture of methyl 4-((3-(4-bromo-1-(2,2,2-trifluoroethyl)-1H-indol-2-yl)prop-2-yn-1-yl)(tert-butoxycarbonyl)amino)-3-methoxybenzoate (12 g, 20.15 mmol, 1 eq.), (3S,4R)-3-fluoro-1-methylpiperidin-4-amine dihydrochloride (4.55 g, 22.17 mmol, 1.1 eq.), and Cs$_2$CO$_3$ (26.27 g, 80.62 mmol, 4 eq.) in dioxane (360 mL) was added RuPhos (1.32 g, 2.82 mmol, 0.14 eq.) and BrettPhos (Pd, G$_4$) (1.30 g, 1.41 mmol, 0.07 eq.) at 20° C., then the mixture was purged with N$_2$ three times. The mixture was stirred at 110° C. for 16 h, after which time HPLC indicated that the starting bromoindole was consumed. EtOAc (500 mL) and a saturated EDTA solution (800 mL) were added at 20° C. and stirred for 1 h. The mixture was then extracted with EtOAc (300 mL×3), and The combined organic layers were washed with brine (100 mL×2), dried over anhydrous sodium sulfate, filtered, and concentrated. The residue was purified by column chromatography (SiO$_2$, PE:EtOAc=2:1 to 0:1), and the solid concentrated eluate was washed with MTBE (20 mL) to provide methyl 4-((tert-butoxycarbonyl) (3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoate (10.1 g, 15.13 mmol, 75.09% yield) as a yellow solid.

Synthesis of methyl 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoate: A mixture of methyl 4-((tert-butoxycarbonyl)(3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoate (10.1 g, 15.13 mmol, 1 eq.) in 4N HCl/EtOAc (300 mL) was stirred at 20° C. for 1 h. TLC analysis ($R_f$=0.45, EtOAc:TEA=10:1) indicated that the starting material was completely consumed. The mixture was filtered, and the filtrate was washed with saturated aqueous NaHCO$_3$ (200 mL) and extracted with EtOAc (200 mL×3). The combined organic layers were washed with brine (50 mL), dried over anhydrous sodium sulfate, filtered, and concentrated to provide methyl 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoate (8.0 g, 13.91 mmol, 91.88% yield), as a yellow solid. The residue was used directly in the next step.

Synthesis of 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoic acid: A mixture of compound methyl 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoate (7 g, 12.17 mmol, 1 eq.), LiOH·H$_2$O (10.21 g, 243.34 mmol, 20 eq.) and NaOH (1.95 g, 48.67 mmol, 4 eq.) in THF (70 mL), MeOH (70 mL), and water (70 mL) was stirred at 50° C. for 5 h under N$_2$ atmosphere, after which time TLC analysis ($R_f$=0.3, EtOAc:MeOH=2:1) indicated complete consumption of starting material. The organic solvents were removed in vacuo, and the concentrate was diluted with water (200 mL) and adjusted to pH=5 with 4 N HCl. The resulting precipitate was filtered, and the retentate was washed with water (20 mL×2) and lyophilized to provide a first batch of 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoic acid (4.8 g, 98.083% purity) as a yellow solid. The filtrate was extracted with EtOAc (250 mL×3) and the combined organic layers were washed with brine (50 mL×2), dried over anhydrous sodium sulfate, filtered, and concentrated. The residue was triturated with MTBE (50 mL) to provide a second batch of 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoic acid (2 g) as a yellow solid.

4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoic acid: $^1$H NMR (400 MHz, DMSO-d$_6$) δ=12.21 (br s, 1H), 7.52 (d, J=8.5 Hz, 1H), 7.34 (d, J=1.5 Hz, 1H), 7.18 (s, 1H), 7.02 (t, J=8.0 Hz, 1H), 6.79 (br d, J=8.3 Hz, 1H), 6.76 (br d, J=8.3 Hz, 1H), 6.32-6.22 (m, 2H), 5.61 (br d, J=8.4 Hz, 1H), 5.04-4.84 (m, 3H), 4.34 (br d, J=6.1 Hz, 2H), 3.84 (s, 3H), 3.75-3.60 (m, 1H), 3.42-3.37 (m, 1H), 3.15-2.98 (m, 1H), 2.84-2.53 (m, 2H), 2.47-2.39 (m, 3H), 2.20-1.93 (m, 1H), 1.81 (br d, J=11.9 Hz, 1H). MS (ES$^{30}$, m/z): 533.2.

Example D130: Preparation of Compounds 783A, 804A, and 805A

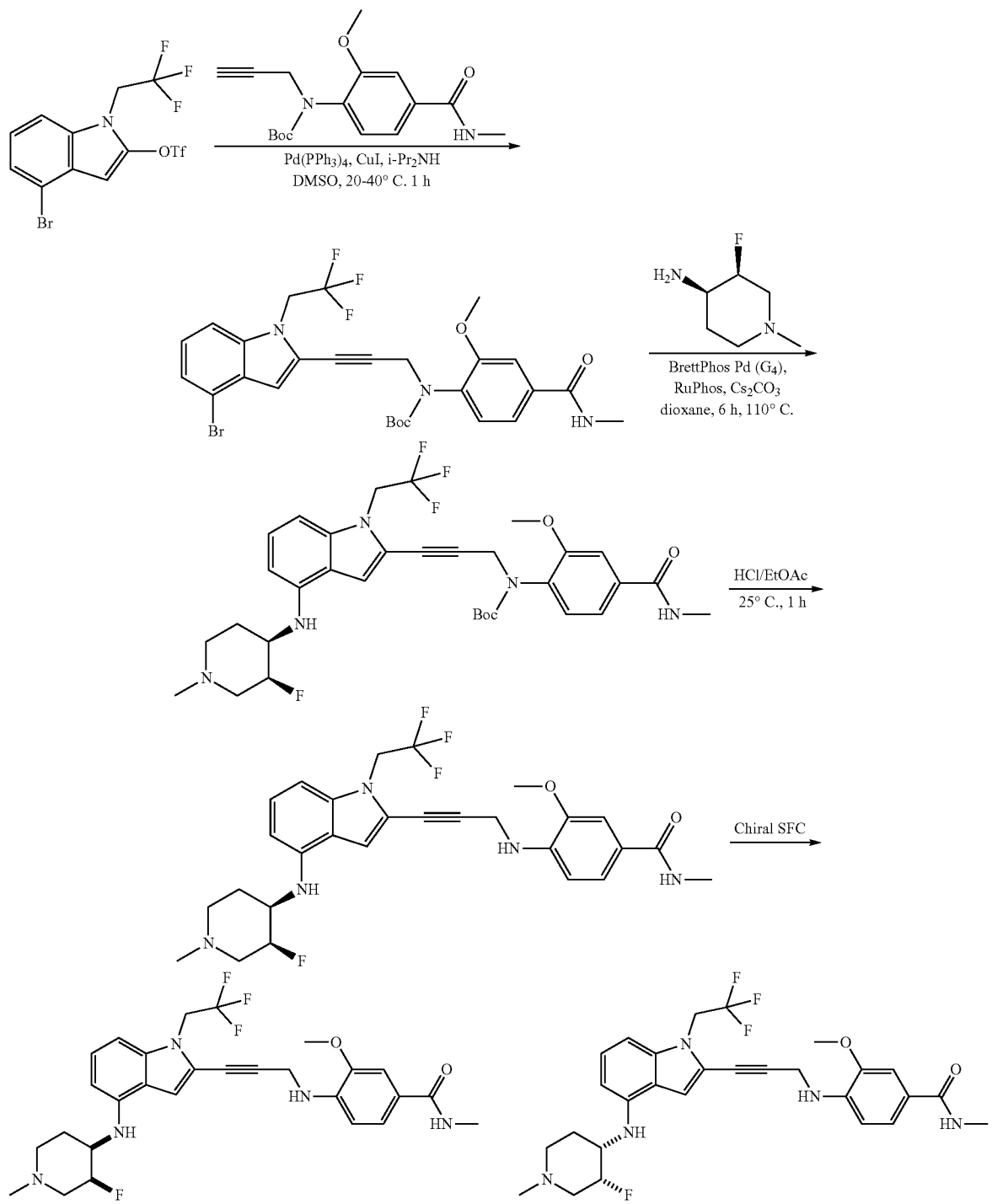

Synthesis of 4-bromo-1-(2,2,2-trifluoroethyl)indoline-2,3-dione: To a mixture of tert-butyl (2-methoxy-4-(methylcarbamoyl)phenyl)(prop-2-yn-1-yl)carbamate (10.68 g, 33.56 mmol, 1.1 eq.) in DMSO (130 mL) was added i-Pr₂NH (30.87 g, 305.07 mmol, 43.11 mL, 10 eq.), CuI (581.01 mg, 3.05 mmol, 0.1 eq.), 4-bromo-1-(2,2,2-trifluoroethyl)-1H-indol-2-yl trifluoromethanesulfonate (13 g, 30.51 mmol, 1 eq.) and Pd(PPh₃)₄ (2.12 g, 1.83 mmol, 0.06 eq.) at 20° C. The mixture was then purged with N₂ three times. The reaction mixture was stirred at 40° C. for 1 h, after which time TLC analysis (R$_f$=0.5, PE:EtOAc=1:1) indicated that the reaction was complete. EtOAc (500 mL) and saturated aqueous EDTA (500 mL), was then added, mixture was stirred at 20° C. for a further 1 h. The mixture was extracted with EtOAc (500 mL×3), and the combined organic layers were dried over anhydrous sodium sulfate, filtered, and concentrated. The residue was purified by column chromatography (SiO$_2$, PE:EtOAc=3:1 to 1:2) to provide 4-bromo-1-(2,2,2-trifluoroethyl)indoline-2,3-dione (13 g, 65% yield) as a yellow solid.

Synthesis of (rac)-tert-butyl (3-(4-(((3S,4R)-3-fluoro-1-methylpiperidin-4-yl)amino)-1-(2,2,2-trifluoroethyl)-1H-indol-2-yl)prop-2-yn-1-yl)(2-methoxy-4-(methylcarbamoyl)phenyl)carbamate: To a mixture of 4-bromo-1-(2,2,2-trifluoroethyl)indoline-2,3-dione (10 g, 16.82 mmol, 1 eq.), (rac)-(3R,4S)-3-fluoro-1-methyl-piperidin-4-amine (3.80 g, 18.51 mmol, 1.1 eq., dihydrochloride salt) in dioxane (300 mL) were added Cs$_2$CO$_3$ (16.44 g, 50.47 mmol, 3 eq.), RuPhos (1.02 g, 2.19 mmol, 0.13 eq), and BrettPhos (Pd, G4) (929.16 mg, 1.01 mmol, 0.06 eq.). The mixture was degassed and purged with N$_2$ three times and then stirred at 110° C. for 6 h. TLC analysis (EtOAc:TEA=10:1, R$_f$=0.35) indicated that the starting material was consumed completely. The reaction mixture was quenched by adding a saturated aqueous EDTA solution (400 mL), and was stirred at 25° C. for 2 h. The mixture was extracted with EtOAc (100 mL×4) and the extracts were treated with 2M HCl solution to adjust the pH of the mixture to 3. Saturated aqueous Na$_2$CO$_3$ was then added to adjust the pH of the mixture to 8, and the mixture was filtered and concentrated under reduced pressure. The residue was purified by column chromatography (SiO$_2$, PE:EtOAc=1:1 to EtOAc:TEA:MeOH=10:1:0.2) to afford (rac)-tert-butyl (3-(4-(((3S,4R)-3-fluoro-1-methylpiperidin-4-yl)amino)-1-(2,2,2-trifluoroethyl)-1H-indol-2-yl)prop-2-yn-1-yl)(2-methoxy-4-(methylcarbamoyl)phenyl)carbamate (9.5 g, 13.24 mmol, 78.71% yield) as a yellow solid.

Synthesis of rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide and chiral resolution of 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide and 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide: A mixture of (rac)-tert-butyl (3-(4-(((3S,4R)-3-fluoro-1-methylpiperidin-4-yl)amino)-1-(2,2,2-trifluoroethyl)-1H-indol-2-yl)prop-2-yn-1-yl)(2-methoxy-4-(methylcarbamoyl)phenyl)carbamate (6.3 g, 9.76 mmol, 1 eq.), in 4N HCl/EtOAc (300 mL) was stirred at 25° C. for 1 h under N$_2$ atmosphere. TLC analysis (EtOAc:TEA=10:1, R$_f$=0.30) indicated that the starting material was consumed completely, and one new spot was observed. The mixture was then treated with saturated aqueous Na$_2$CO$_3$ to adjust the pH of the mixture to 8 and extracted with EtOAc (100 mL×4). The combined organic layers were washed with brine (50 mL×2), dried over anhydrous sodium sulfate, filtered, and concentrated under reduced pressure. The resulting residue was stirred in EtOH (10 mL) at 25° C. for 10 h and then filtered to afford (rac)-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide (4.9 g, 8.53 mmol, 87.45% yield) as a yellow solid.

(Rac)-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide (7.2 g, 13.20 mmol, 1 eq.) was resolved into respective enantiomers via chiral SFC to afford 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide (3.34 g, 6.04 mmol, 45.74% yield) as a yellow solid and 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide (2.34 g, 4.16 mmol, 31.56% yield) as a yellow solid.

4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide: $^1$H NMR (400 MHz, DMSO-d6) δ ppm 1.65-1.72 (m, 1H) 1.87-1.98 (m, 1H) 2.04-2.12 (m, 1H) 2.14-2.29 (m, 4H) 2.72-2.84 (m, 4H) 3.02 (br t, J=10.76 Hz, 1H) 3.47-3.62 (m, 1H) 3.80-3.89 (m, 3H) 4.31 (d, J=6.24 Hz, 2H) 4.72-4.87 (m, 1H) 4.92 (q, J=9.05 Hz, 2H) 5.42-5.55 (m, 1H) 5.94-6.03 (m, 1H) 6.19-6.29 (m, 1H) 6.70-6.79 (m, 2H) 7.00 (t, J=7.95 Hz, 1H) 7.17 (s, 1H) 7.35 (s, 1H) 7.39-7.46 (m, 1H) 8.08-8.13 (m, 1H). MS (ES$^{30}$, m/z): 546.3; 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide, MS (ES$^{30}$, m/z): 546.3.

Example D131: General Procedure for Preparation of Compounds 772 and 773A

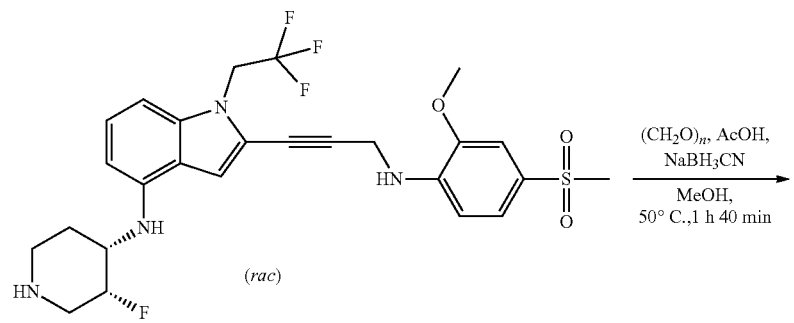

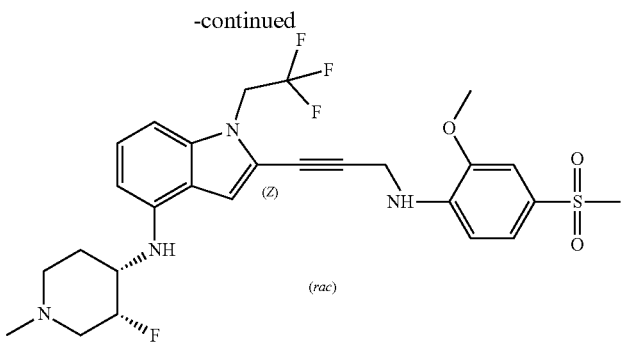

To a solution of (rac)-N-((3R,4S)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine (30 g, 53.48 mmol, 1 eq.) in MeOH (300 mL) were added AcOH (9.31 g, 155 mmol, 8.87 mL, 2.90 eq.), paraformaldehyde (8.03 g), and NaBH₃CN (16.80 g, 267.38 mmol, 5 eq.). The reaction mixture was stirred at 50° C. for 1 h 40 min under N₂, after which time TLC analysis (EtOAc:TEA=10:1, R_f=0.4) indicated that starting material remained, and one major new spot with polarity lower than that of the starting material was detected. Further portions of AcOH (6.21 g, 103.34 mmol, 5.91 mL, 1.93 eq.), paraformaldehyde (1.61 g) and NaBH₃CN (3.36 g, 53.48 mmol, 1 eq.) were then added, and the mixture was stirred at 50° C. for a further 0.5 h. TLC analysis (EtOAc:TEA=10:1, R_f=0.4) indicated that starting material remained. A final portion of paraformaldehyde (802.83 mg) and NaBH₃CN (3.36 g, 53.48 mmol, 1 eq.) were added, and the mixture was stirred at 50° C. for an additional 10 min. TLC analysis (EtOAc:TEA=10:1, R_f=0.4) showed that the starting material was consumed completely. The reaction mixture was poured into a saturated aqueous solution of Na₂CO₃ (4 L) and extracted with EtOAc (1 L×3). The combined organic layers were washed with a saturated aqueous solution of Na₂CO₃ (1 L) and brine (1 L×2), dried over anhydrous sodium sulfate, filtered, and concentrated to ~500 mL. The concentrate was filtered to afford the crude product as the retentate. The retentate was purified by column chromatography (SiO₂, EtOAc) and the enantiomers were separated by chiral SFC to afford the desired pure enantiomers as light yellow solids.

N-[(3S,4R)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine: $^1$H NMR (400 MHz, DMSO-d₆) δ ppm 7.39 (dd, J=8.38, 1.77 Hz, 1H) 7.25 (d, J=1.83 Hz, 1H) 7.18 (s, 1H) 7.01 (t, J=8.01 Hz, 1H) 6.89 (d, J=8.44 Hz, 1H) 6.73 (d, J=8.19 Hz, 1H) 6.48 (t, J=6.17 Hz, 1H) 6.24 (d, J=7.82 Hz, 1H) 5.49 (d, J=8.56 Hz, 1H) 4.93 (q, J=9.17 Hz, 2H) 4.70-4.87 (m, 1H) 4.36 (d, J=6.11 Hz, 2H) 3.89 (s, 3H) 3.47-3.64 (m, 1H) 3.09 (s, 3H) 3.02 (brt, J=10.51 Hz, 1H) 2.79 (br d, J=11.00 Hz, 1H) 2.14-2.30 (m, 4H) 2.02-2.13 (m, 1H) 1.92 (qd, J=12.17, 3.48 Hz, 1H) 1.69 (br d, J=9.78 Hz, 1H). MS (ES³⁰, m/z): 567.2; N-[(3R,4S)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine, MS (ES³⁰, m/z): 567.2.

Example D132: Preparation of Compound 459A

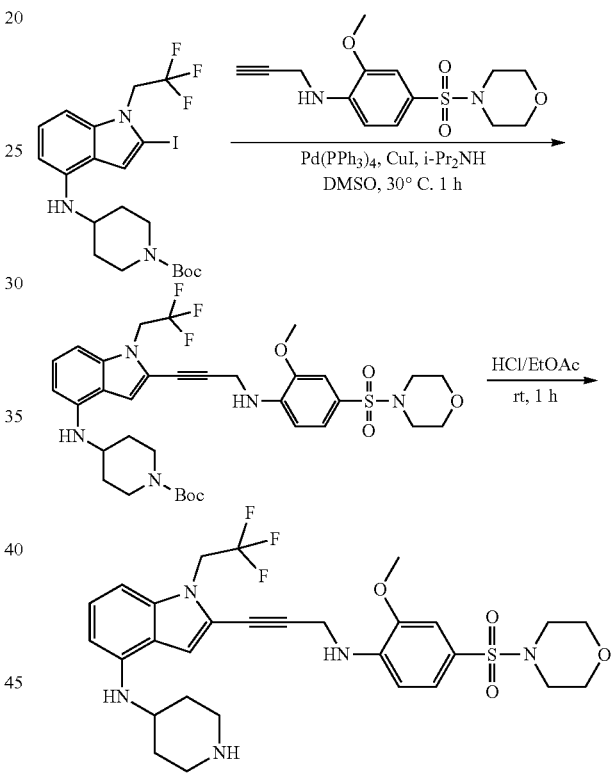

Synthesis of tert-butyl 4-((2-(3-((2-methoxy-4-(morpholinosulfonyl)phenyl)amino)prop-1-yn-1-yl)-1-(2,2,2-trifluoroethyl)-1H-indol-4-yl)amino)piperidine-1-carboxylate: To a mixture 2-methoxy-4-morpholinosulfonyl-N-prop-2-ynyl-aniline (89.05 mg, 283.76 μmol, 1.5 eq.) and tert-butyl 4-((2-iodo-1-(2,2,2-trifluoroethyl)-1H-indol-4-yl)amino)piperidine-1-carboxylate (0.1 g, 189.17 μmol, 1 eq.) (99%) in DMSO (2 mL) were added CuI (36.03 mg, 189.17 μmol, 1 eq.), Pd(PPh₃)₄ (21.86 mg, 18.92 μmol, 0.10 eq.), and diisopropylamine (19.14 mg, 189.17 μmol, 26.74 μL, 1 eq.). The reaction mixture was stirred at 30° C. for 1 h under N₂, after which time LC-MS analysis indicated that the reaction was complete. The reaction was poured into a saturated aqueous EDTA solution (50 mL) and extracted with EtOAc (20 mL×3), and The combined organic layers were washed with saturated aqueous EDTA solution (20 mL) and stirred for 1 h. The organic layer was then washed with brine (50 mL), dried over anhydrous sodium sulfate, and concentrated in vacuo. The crude residue was purified by prep-TLC (PE:EtOAc=1:1, $R_f$=0.32) to provide tert-butyl 4-((2-(3-((2-methoxy-4-(morpholinosulfonyl)phenyl)amino)prop-1-yn-1-yl)-1-(2,2,2-trifluoroethyl)-1H-indol-4-yl)amino)piperidine-1-carboxylate (0.08 g, 90.68 μmol, 47.93% yield) as a yellow solid.

Preparation of final product: To a mixture tert-butyl 4-((2-(3-((2-methoxy-4-(morpholinosulfonyl)phenyl)amino)prop-1-yn-1-yl)-1-(2,2,2-trifluoroethyl)-1H-indol-4-yl)amino)piperidine-1-carboxylate (0.07 g, 79.34 μmol, 1 eq.) was added HCl/EtOAc (4 M, 34.26 mL, 1726.94 eq.). The mixture was stirred at 25° C. for 1 h under $N_2$, after which time LC-MS analysis indicated that the reaction was complete. The mixture was directly concentrated to afford a crude residue that was purified by prep-HPLC to afford 2-(3-{[2-methoxy-4-(morpholine-4-sulfonyl)phenyl]amino}prop-1-yn-1-yl)-N-(piperidin-4-yl)-1-(2,2,2-trifluoroethyl)-1H-indol-4-amine (0.0166 g, 26.89 μmol, 33.89% yield) as a white solid. MS ($ES^{3O}$, m/z): 606.2.

Example D133: General Procedure for Preparation of Compounds 482A and 1003A

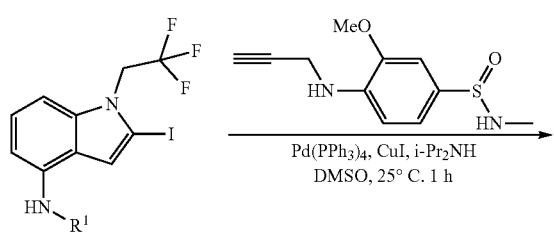

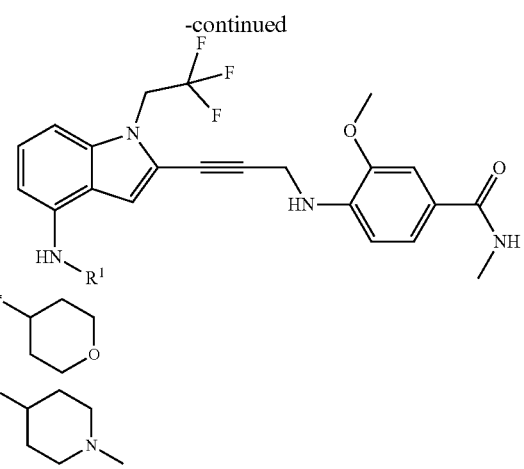

3-Methoxy-N-methyl-4-(prop-2-yn-1-ylamino)benzamide was coupled to the $R^1$-substituted iodoindoles specified above according to the general procedure specified in EXAMPLE D120. In each case, the reactions were deemed complete after stirring for 1 h at 30° C., and the crude compounds were first purified by prep-TLC and further purified by prep-HPLC.

3-methoxy-N-methyl-4-[(3-{4-[(oxan-4-yl)amino]-1-(2,2,2-trifluoroethyl)-1H-indol-2-yl}prop-2-yn-1-yl)amino]benzamide, MS ($ES^{3O}$, m/z): 515.2; and 3-methoxy-N-methyl-4-[(3-{4-[(1-methylpiperidin-4-yl)amino]-1-(2,2,2-trifluoroethyl)-1H-indol-2-yl}prop-2-yn-1-yl)amino]benzamide, MS ($ES^{3O}$, m/z): 528.2.

Example D134: Preparation of methyl 4-((3-(4-(((3S,4R)-3-fluoropiperidin-4-yl)amino)-1-(2,2,2-trifluoroethyl)-1H-indol-2-yl)prop-2-yn-1-yl)amino)-3-methoxybenzoate

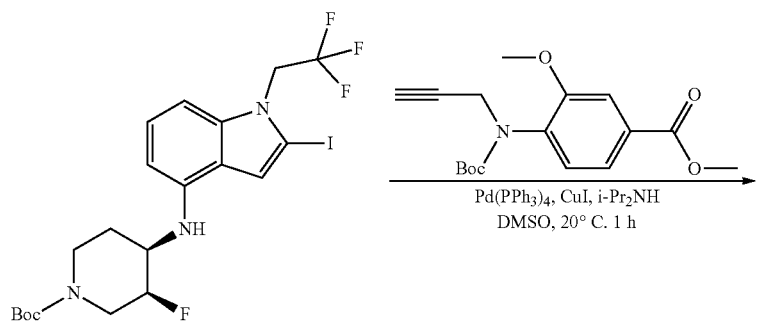

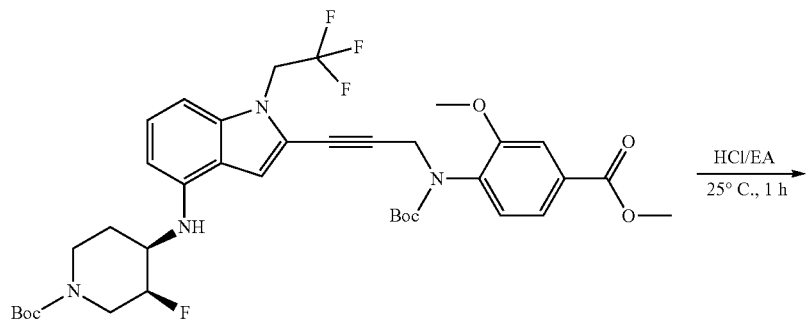

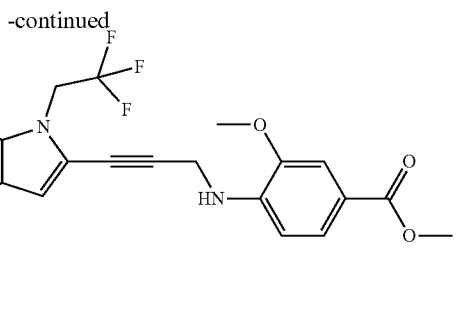

Synthesis of tert-butyl (3S,4R)-4-((2-(3-((tert-butoxycarbonyl)(2-methoxy-4-(methoxycarbonyl)phenyl)amino)prop-1-yn-1-yl)-1-(2,2,2-trifluoroethyl)-1H-indol-4-yl)amino)-3-fluoropiperidine-1-carboxylate and tert-butyl (3R,4S)-4-((2-(3-((tert-butoxycarbonyl)(2-methoxy-4-(methoxycarbonyl)phenyl)amino)prop-1-yn-1-yl)-1-(2,2,2-trifluoroethyl)-1H-indol-4-yl)amino)-3-fluoropiperidine-1-carboxylate: To a solution of methyl 4-((tert-butoxycarbonyl)(prop-2-yn-1-yl)amino)-3-methoxybenzoate (3.54 g, 11.08 mmol, 1.2 eq.) in DMSO (50 mL) were added i-Pr$_2$NH (9.35 g, 92.37 mmol, 13.05 mL, 10 eq.), and CuI (351.83 mg, 1.85 mmol, 0.2 eq.). The mixture was degassed and purged with N$_2$, and tert-butyl (3S,4R)-3-fluoro-4-((2-iodo-1-(2,2,2-trifluoroethyl)-1H-indol-4-yl)amino)piperidine-1-carboxylate (5 g, 9.24 mmol, 1 eq.) and Pd(PPh$_3$)$_4$ (1.07 g, 923.67 µmol, 0.1 eq.) were added. The mixture was stirred at 20° C. for 1 h under N$_2$ atmosphere, after which time TLC analysis (PE:EtOAc=2:1, R$_f$=0.47) indicated that the starting material was completely consumed. The reaction mixture was quenched with a saturated aqueous EDTA solution (250 mL), and extracted with EtOAc (150 mL×3). The combined organic layers were washed with brine (50 mL×2), dried over anhydrous sodium sulfate, filtered, and concentrated under reduced pressure to give a residue. The residue was purified by column chromatography (SiO$_2$, PE:EtOAc=7:1 to 0:1) provide tert-butyl (3S,4R)-4-((2-(3-((tert-butoxycarbonyl)(2-methoxy-4-(methoxycarbonyl)phenyl)amino)prop-1-yn-1-yl)-1-(2,2,2-trifluoroethyl)-1H-indol-4-yl)amino)-3-fluoropiperidine-1-carboxylate as a yellow solid (76% yield). MS (ES$^{30}$, m/z): 733.3.

The procedure was repeated using tert-butyl (3R,4S)-3-fluoro-4-((2-iodo-1-(2,2,2-trifluoroethyl)-1H-indol-4-yl)amino)piperidine-1-carboxylate in place of tert-butyl (3S,4R)-3-fluoro-4-((2-iodo-1-(2,2,2-trifluoroethyl)-1H-indol-4-yl)amino)piperidine-1-carboxylate to provide tert-butyl (3R,4S)-4-((2-(3-((tert-butoxycarbonyl)(2-methoxy-4-(methoxycarbonyl)phenyl)amino)prop-1-yn-1-yl)-1-(2,2,2-trifluoroethyl)-1H-indol-4-yl)amino)-3-fluoropiperidine-1-carboxylate.

Synthesis of methyl 4-((3-(4-(((3S,4R)-3-fluoropiperidin-4-yl)amino)-1-(2,2,2-trifluoroethyl)-1H-indol-2-yl)prop-2-yn-1-yl)amino)-3-methoxybenzoate: A solution of tert-butyl (3S,4R)-4-((2-(3-((tert-butoxycarbonyl)(2-methoxy-4-(methoxycarbonyl)phenyl)amino)prop-1-yn-1-yl)-1-(2,2,2-trifluoroethyl)-1H-indol-4-yl)amino)-3-fluoropiperidine-1-carboxylate (6 g, 7.07 mmol, 1 eq.) dissolved in 4N HCl/EtOAc (30 mL). The mixture was stirred at 25° C. for 1 h, after which time HPLC analysis indicated that the starting material was completely consumed. The reaction mixture was quenched by adding saturated aqueous Na$_2$CO$_3$ (150 mL) until the pH of the mixture was ~9. The mixture was extracted with EtOAc (100 mL×3), and The combined organic layers were washed with brine (30 mL×2), dried over anhydrous sodium sulfate, filtered, and concentrated under reduced pressure to provide crude methyl 4-((3-(4-(((3S,4R)-3-fluoropiperidin-4-yl)amino)-1-(2,2,2-trifluoroethyl)-1H-indol-2-yl)prop-2-yn-1-yl)amino)-3-methoxybenzoate (78% yield) as a yellow solid.

$^1$H NMR: (400 MHz, DMSO-d$_6$) δ ppm 1.59-1.66 (m, 1H) 1.68-1.78 (m, 1H) 2.55-2.61 (m, 1H) 2.69-2.82 (m, 1H) 2.92-3.00 (m, 1H) 3.06-3.14 (m, 1H) 3.31 (br s, 1H) 3.59-3.72 (m, 1H) 3.78 (s, 3H) 3.85 (s, 3H) 4.32-4.37 (m, 2H) 4.62-4.78 (m, 1H) 4.88-4.97 (m, 2H) 5.47-5.55 (m, 1H) 6.22-6.28 (m, 1H) 6.37-6.43 (m, 1H) 6.70-6.75 (m, 1H) 6.79-6.85 (m, 1H) 6.97-7.02 (m, 1H) 7.17-7.21 (m, 1H) 7.32-7.35 (m, 1H) 7.53-7.56 (m, 1H).

The procedure was repeated using tert-butyl (3R,4S)-4-((2-(3-((tert-butoxycarbonyl)(2-methoxy-4-(methoxycarbonyl)phenyl)amino)prop-1-yn-1-yl)-1-(2,2,2-trifluoroethyl)-1H-indol-4-yl)amino)-3-fluoropiperidine-1-carboxylate in place of tert-butyl (3S,4R)-4-((2-(3-((tert-butoxycarbonyl)(2-methoxy-4-(methoxycarbonyl)phenyl)amino)prop-1-yn-1-yl)-1-(2,2,2-trifluoroethyl)-1H-indol-4-yl)amino)-3-fluoropiperidine-1-carboxylate to provide methyl 4-((3-(4-(((3R,4S)-3-fluoropiperidin-4-yl)amino)-1-(2,2,2-trifluoroethyl)-1H-indol-2-yl)prop-2-yn-1-yl)amino)-3-methoxybenzoate.

Example D135: Preparation of Compounds 899A, 903A, 908A, and 912A

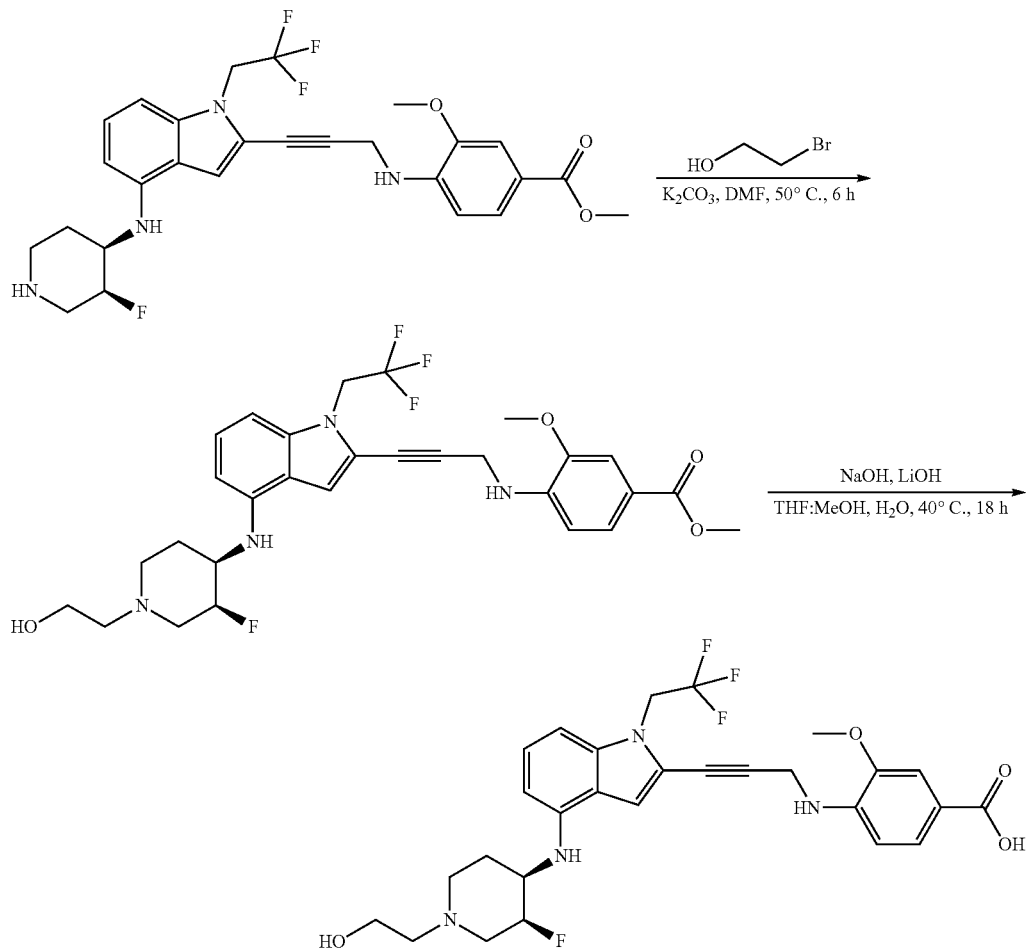

Synthesis of methyl 4-{[3-(4-{[(3S,4R)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoate: To a solution of methyl 4-((3-(4-(((3S,4R)-3-fluoropiperidin-4-yl)amino)-1-(2,2,2-trifluoroethyl)-1H-indol-2-yl)prop-2-yn-1-yl)amino)-3-methoxybenzoate (prepared according to EXAMPLE D134) (300 mg, 450.68 µmol, 1 eq.) in DMF (3 mL) were added $K_2CO_3$ (311.43 mg, 2.25 mmol, 5 eq.) and 2-bromoethanol (225.28 mg, 1.80 mmol, 128 µL, 4 eq.). The mixture was stirred at 50° C. for 6 h, after which time TLC (DCM:MeOH=10:1, $R_f$=0.38) indicated that the starting material was completely consumed, and one new spot had formed. The reaction mixture was quenched with water (20 mL) and extracted with EtOAc (15 mL×3). The combined organic layers were washed with brine (10 mL), dried over anhydrous sodium sulfate, filtered, and concentrated under reduced pressure. The residue was purified by column chromatography ($SiO_2$, PE:EtOAc=3:1 to 0:1) to provide methyl 4-{[3-(4-{[(3S,4R)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoate (49% yield) as a yellow solid. MS ($ES^{30}$, m/z): 577.3.

Synthesis of methyl 4-{[3-(4-{[(3R,4S)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoate: To a solution of methyl 4-((3-(4-(((3R,4S)-3-fluoropiperidin-4-yl)amino)-1-(2,2,2-trifluoroethyl)-1H-indol-2-yl)prop-2-yn-1-yl)amino)-3-methoxybenzoate (1 eq.) in DMF (3 mL) were added $K_2CO_3$ (5 eq.) and 2-bromoethanol (4 eq.). The mixture was stirred at 50° C. for 12 h, after which time TLC analysis indicated that the starting material was completely consumed, and one new spot had formed. The reaction mixture was quenched with water (5 mL) and extracted with EtOAc (5 mL×3). The combined organic layers were washed with brine (5 mL×3), dried over anhydrous sodium sulfate, filtered, and concentrated under reduced pressure. The residue was purified by column chromatography ($SiO_2$, PE:EtOAc=1:1 to 0:1), and further purified by prep-HPLC to afford methyl 4-{[3-(4-{[(3R,4S)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoate (38% yield) as a yellow solid. MS ($ES^{30}$, m/z): 577.2.

Synthesis of 4-{[3-(4-{[(3S,4R)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoic acid and 4-{[3-(4-{[(3R,4S)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoic acid: To a solution of methyl 4-{[3-(4-{[(3S,4R)-3-fluoro-1-(2-hydroxyethyl)piperidin-4-yl]amino}-1-(2,2,2- trifluoroethyl)-1H-indol-2-yl)prop-2-yn-1-yl]amino}-3-methoxybenzoate (0.1 g, 155.57 µmol, 1 eq.) in THF (1 mL), water (1 mL) and MeOH (1 mL) were added NaOH (31.11 mg, 777.86 µmol, 5 eq.) and LiOH·H$_2$O (32.64 mg, 777.86 µmol, 5 eq.). The mixture was stirred at 40° C. for 18 h, after which time TLC analysis (DCM:MeOH=10:1, R$_f$=0.2) indicated that the starting material was completely consumed, and one new spot had formed. 2N HCl (20 mL) was then added to adjust the pH of the mixture to 3, and the mixture was extracted with EtOAc (20 mL×3). The combined organic layers were washed with brine (20 mL), dried over anhydrous sodium sulfate, filtered, and concentrated under reduced pressure. The residue was purified by prep-HPLC to provide 4-{[3-(4-{[(3S,4R)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoic acid (45% yield) as a yellow solid. MS (ES$^{30}$, m/z): 563.2.

The procedure was repeated using methyl 4-{[3-(4-{[(3R,4S)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoate in place of methyl 4-{[3-(4-{[(3S,4R)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoate to provide 4-{[3-(4-{[(3R,4S)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoic acid (27% yield) as a yellow solid. MS (ES$^{30}$, m/z): 563.2.

Example D136: Preparation of Compounds 897A, 898A, 902A, and 904A

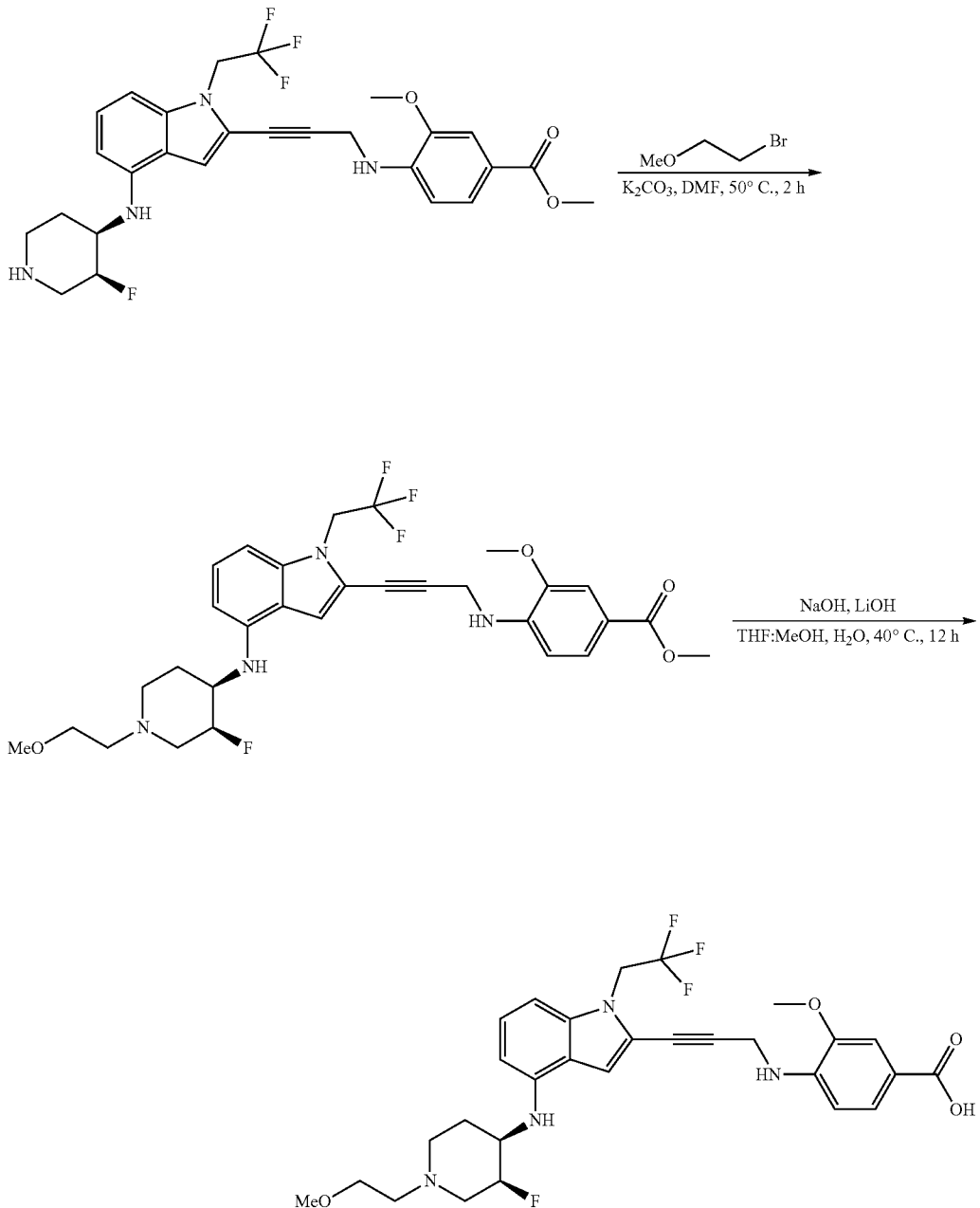

Compounds 897A, 898A, 902A, and 904A were prepared via a procedure analogous to EXAMPLE D135, using 1-bromo-2-methoxy-ethane in place of 2-bromoethanol.

methyl 4-{[3-(4-{[(3S,4R)-3-fluoro-1-(2-methoxyethyl)piperidin-4-yl]amino}-1-(2,2,2-trifluoroethyl)-1H-indol-2-yl)prop-2-yn-1-yl]amino}-3-methoxybenzoate, MS (ES$^{30}$, m/z): 591.3; methyl 4-{[3-(4-{[(3R,4S)-3-fluoro-1-(2-methoxyethyl)piperidin-4-yl]amino}-1-(2,2,2-trifluoroethyl)-1H-indol-2-yl)prop-2-yn-1-yl]amino}-3-methoxybenzoate, MS (ES$^{30}$, m/z): 591.3; 4-{[3-(4-{[(3S,4R)-3-fluoro-1-(2-methoxyethyl)piperidin-4-yl]amino}-1-(2,2,2-trifluoroethyl)-1H-indol-2-yl)prop-2-yn-1-yl]amino}-3-methoxybenzoic acid, MS (ES$^{30}$, m/z): 577.2; and 4-{[3-(4-{[(3R,4S)-3-fluoro-1-(2-methoxyethyl)piperidin-4-yl]amino}-1-(2,2,2-trifluoroethyl)-1H-indol-2-yl)prop-2-yn-1-yl]amino}-3-methoxybenzoic acid, MS (ES$^{30}$, m/z): 577.3.

Example D137: Preparation of Compounds 900A, 905A, 911A, and 921A

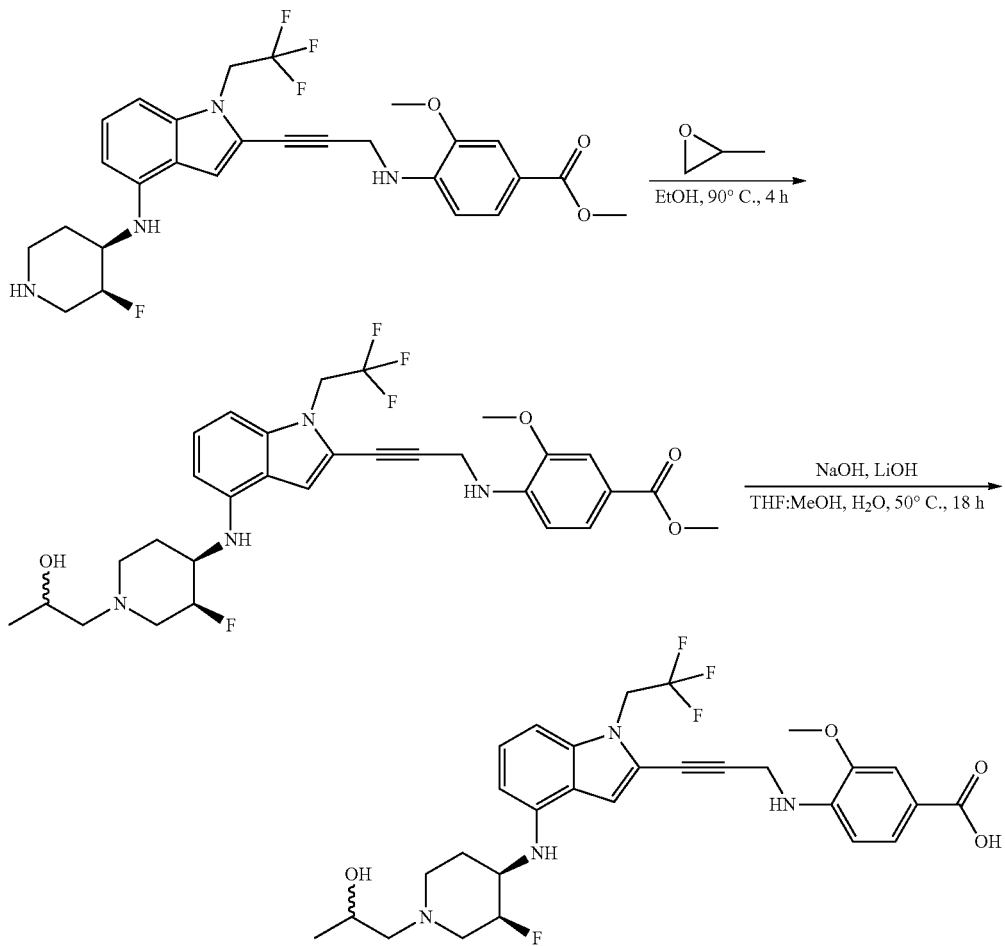

Synthesis of Compounds methyl 4-{[3-(4-{[(3S,4R)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoate and methyl 4-{[3-(4-{[(3R,4S)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoate: A mixture of methyl 4-((3-(4-(((3S,4R)-3-fluoropiperidin-4-yl)amino)-1-(2,2,2-trifluoroethyl)-1H-indol-2-yl)prop-2-yn-1-yl)amino)-3-methoxybenzoate (0.2 g, 375.57 µmol, 1 eq.) and 2-methyloxirane (109.06 mg, 1.88 mmol, 131.72 µL, 5 eq.) in EtOH (3 mL) was stirred at 90° C. for 4 h, after which time TLC analysis (DCM:MeOH=10:1, R$_f$=0.32) indicated that the starting material was completely consumed, and one new spot had formed. The reaction mixture was concentrated under reduced pressure. The residue was purified by prep-TLC (SiO$_2$, DCM:MeOH=10:1) and further purified by prep-HPLC to provide methyl 4-{[3-(4-{[(3S,4R)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoate (180 mg, 43% yield) as a yellow solid. MS (ES$^{30}$, m/z): 591.2.

The procedure was repeated using methyl 4-((3-(4-(((3R,4S)-3-fluoropiperidin-4-yl)amino)-1-(2,2,2-trifluoroethyl)-1H-indol-2-yl)prop-2-yn-1-yl)amino)-3-methoxybenzoate in place of methyl 4-((3-(4-(((3S,4R)-3-fluoropiperidin-4-yl)amino)-1-(2,2,2-trifluoroethyl)-1H-indol-2-yl)prop-2-yn-1-yl)amino)-3-methoxybenzoate to afford methyl 4-{[3-(4-{[(3R,4S)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoate. MS (ES$^+$, m/z): 591.2.

Synthesis of 4-{[3-(4-{[(3S,4R)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoic acid and 4-{[3-(4-{[(3R,4S)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoic acid. To a solution of methyl 4-{[3-(4-{[(3S,4R)-3-fluoro-1-(2- hydroxypropyl)piperidin-4-yl]amino}-1-(2,2,2-trifluoro-ethyl)-1H-indol-2-yl)prop-2-yn-1-yl]amino}-3-methoxybenzoate (0.1 g, 151.71 μmol, 1 eq.) in THF (1 mL), MeOH (1 mL) and water (1 mL) were added NaOH (30.34 mg, 758.54 μmol, 5 eq.) and LiOH·H$_2$O (31.83 mg, 758.54 μmol, 5 eq.). The mixture was stirred at 50° C. for 18 h under N$_2$ atmosphere, after which time TLC analysis (DCM: MeOH=10:1, R$_f$=0.12) indicated that the ester starting material was consumed completely and two new spots had formed. The reaction mixture was quenched by adding 2N HCl (15 mL) to adjust the pH of the mixture to 3 and extracted with EtOAc (15 mL×3). The combined organic layers were washed with brine (10 mL×2), dried over anhydrous sodium sulfate, filtered, and concentrated under reduced pressure. The residue was purified by prep-HPLC to provide 4-{[3-(4-{[(3S,4R)-3-fluoro-1-(2-hydroxypropyl) piperidin-4-yl]amino}-1-(2,2,2-trifluoroethyl)-1H-indol-2-yl)prop-2-yn-1-yl]amino}-3-methoxybenzoic acid (45% yield) as a yellow solid. MS (ES$^{30}$, m/z): 577.3.

The procedure was repeated using methyl 4-{[3-(4-{[(3R,4S)-3-fluoro-1-(2-hydroxypropyl)piperidin-4-yl]amino}-1-(2,2,2-trifluoroethyl)-1H-indol-2-yl)prop-2-yn-1-yl] amino}-3-methoxybenzoate in place of methyl 4-{[3-(4-{[(3S,4R)-3-fluoro-1-(2-hydroxypropyl)piperidin-4-yl] amino}-1-(2,2,2-trifluoroethyl)-1H-indol-2-yl)prop-2-yn-1-yl]amino}-3-methoxybenzoate to afford 4-{[3-(4-{[(3R,4S)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoic acid. MS (ES$^{30}$, m/z): 577.3.

Example D138: Preparation of Compounds 901A, 915A, 925A, and 926A

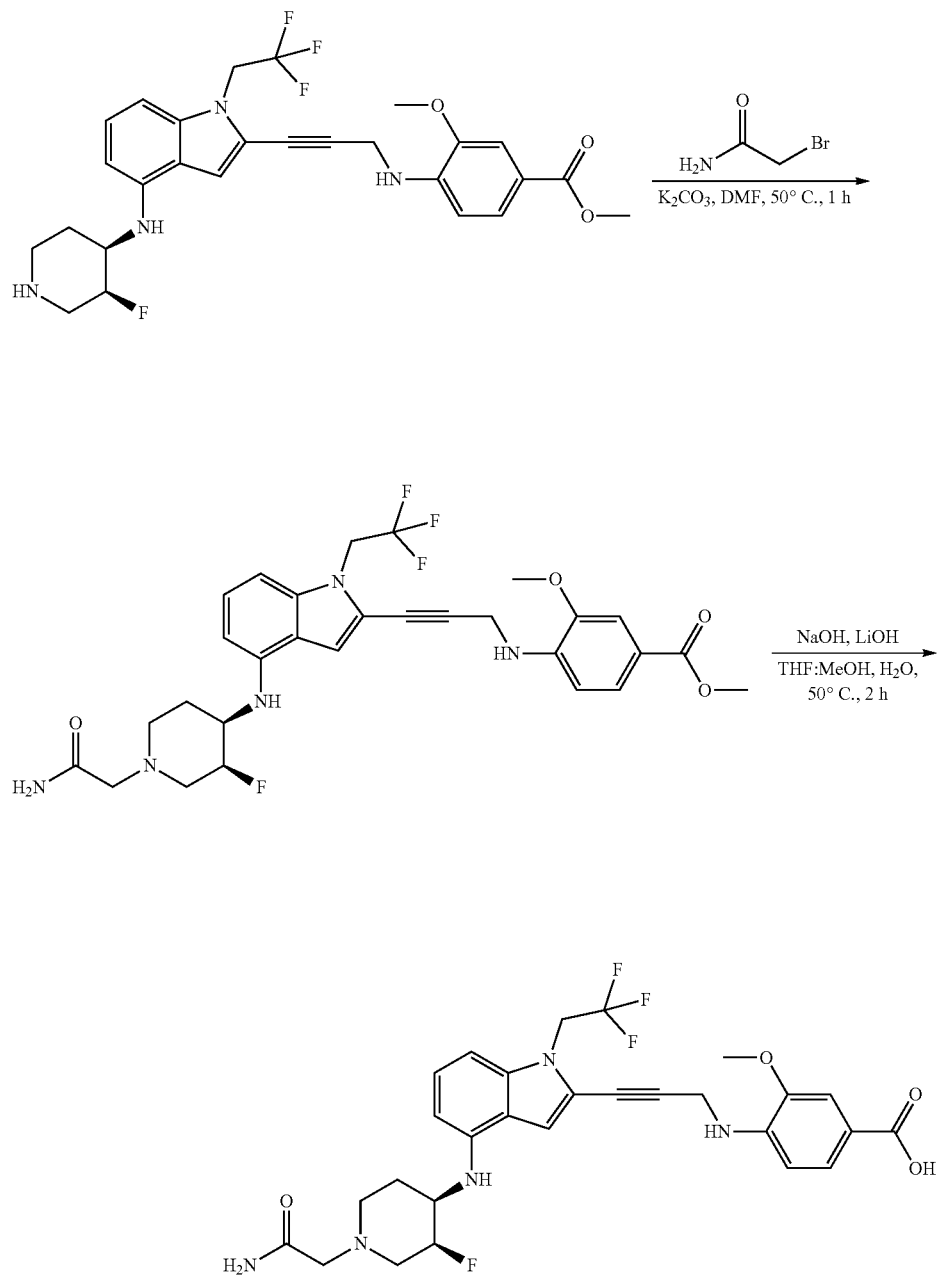

Synthesis of methyl 4-{[3-(4-{[(3S,4R)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoate and methyl 4-{1[3-(4-{[(3R,4S)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoate: To a solution of methyl 4-((3-(4-(((3S,4R)-3-fluoropiperidin-4-yl)amino)-1-(2,2,2-trifluoroethyl)-1H-indol-2-yl)prop-2-yn-1-yl)amino)-3-methoxybenzoate (0.2 g, 375.57 μmol, 1 eq.) in DMF (2 mL) were added 2-bromoacetamide (155.44 mg, 1.13 mmol, 3 eq.) and $K_2CO_3$ (259.53 mg, 1.88 mmol, 5 eq.). The mixture was stirred at 50° C. for 1 h under $N_2$ atmosphere, after which time TLC analysis (DCM:MeOH=10:1, $R_f$=0.46) indicated that the starting material was completely consumed, and one new spot had formed. The reaction mixture was quenched with water (20 mL) and extracted with EtOAc (20 mL×3). The combined organic layers were washed with brine (10 mL), dried over anhydrous sodium sulfate, filtered, and concentrated under reduced pressure. The residue was purified by prep-TLC ($SiO_2$, DCM:MeOH=20:1) to provide methyl 4-{[3-(4-{[(3S,4R)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoate (42% yield) as a yellow oil. MS ($ES^{30}$, m/z): 590.2.

The procedure was repeated using 4-((3-(4-(((3R,4S)-3-fluoropiperidin-4-yl)amino)-1-(2,2,2-trifluoroethyl)-1H-indol-2-yl)prop-2-yn-1-yl)amino)-3-methoxybenzoate in place of methyl 4-((3-(4-(((3S,4R)-3-fluoropiperidin-4-yl)amino)-1-(2,2,2-trifluoroethyl)-1H-indol-2-yl)prop-2-yn-1-yl)amino)-3-methoxybenzoate to afford methyl 4-{[3-(4-{[(3R,4S)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoate. MS ($ES^{30}$, m/z): 590.2.

Synthesis of 4-{[3-(4-{[(3S,4R)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoic acid and 4-{[3-(4-{[(3R,4S)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoic acid: A mixture of methyl 4-{[3-(4-{[(3S,4R)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoate (1 eq.), NaOH (5 eq.), and LiOH (5 eq.) in THF (1 mL), MeOH (1 mL), and water (1 mL) was degassed and purged with $N_2$. The mixture was stirred at 50° C. for 12 h under $N_2$ atmosphere, after which time LC-MS analysis indicated that some starting material remained, and the desired compound was present. The reaction mixture was quenched with water (5 mL) and then extracted with EtOAc (5 mL×3). The combined organic layers were washed with brine (5 mL×3), dried over anhydrous sodium sulfate, filtered, and concentrated under reduced pressure. The residue was purified by prep-HPLC. 4-{[3-(4-{[(3S,4R)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoic acid (12% yield) was obtained as a yellow solid. MS ($ES^{30}$, m/z): 576.2.

The procedure was repeated using methyl 4-{[3-(4-{[(3R,4S)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoate in place of methyl 4-{[3-(4-{[(3S,4R)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoate to provide 4-{[3-(4-{[(3R,4S)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoic acid. MS ($ES^{30}$, m/z): 576.2.

Example D139: Preparation of Compounds 913A, 914A, 920A, 927A, and 934A

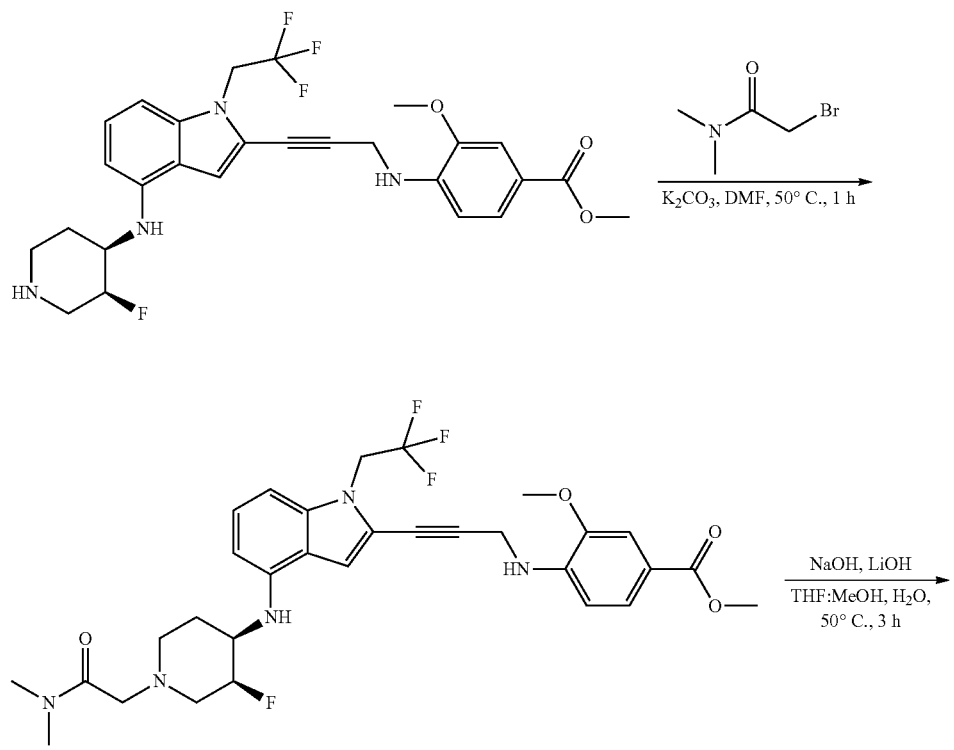

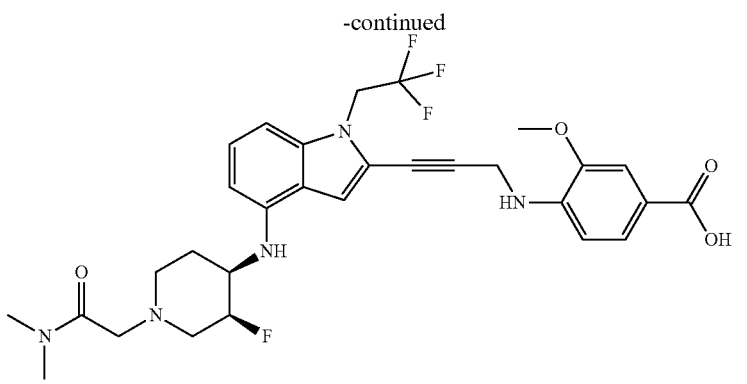

Compounds 913A, 914A, 920A, and 927A were prepared via a procedure analogous to the synthesis of the compounds described in EXAMPLE D138, using 2-bromo-N,N-dimethyl-acetamide in place of 2-bromoacetamide. Compound 934A was obtained as a side-product of the last step. Compounds 913A and 914A were purified via prep-TLC (SiO$_2$, DCM:MeOH=10:1) and prep-HPLC (column: C18 100×30 mm 5 μm; mobile phase: [water (0.2% FA)-ACN]; B %: 25%-55%, 10 min). Compounds 920A, 914A, and 934A were purified via prep-HPLC (column: C18 100×30 mm 5 μm; mobile phase: [water (0.2% FA)-ACN]; B %: 15%-45%, 10 min).

methyl 4-{[3-(4-{[(3S,4R)-1-[(dimethylcarbamoyl)methyl]-3-fluoropiperidin-4-yl]amino}-1-(2,2,2-trifluoroethyl)-1H-indol-2-yl)prop-2-yn-1-yl]amino}-3-methoxybenzoate, MS (ES$^{30}$, m/z): 618.3; methyl 4-{[3-(4-{[(3R,4S)-1-[(dimethylcarbamoyl)methyl]-3-fluoropiperidin-4-yl]amino}-1-(2,2,2-trifluoroethyl)-1H-indol-2-yl)prop-2-yn-1-yl]amino}-3-methoxybenzoate, MS (ES$^{30}$, m/z): 618.3; 4-{[3-(4-{[(3S,4R)-1-[(dimethylcarbamoyl)methyl]-3-fluoropiperidin-4-yl]amino}-1-(2,2,2-trifluoroethyl)-1H-indol-2-yl)prop-2-yn-1-yl]amino}-3-methoxybenzoic acid), MS (ES$^{30}$, m/z): 604.3; 4-{[3-(4-{[(3R,4S)-1-[(dimethylcarbamoyl)methyl]-3-fluoropiperidin-4-yl]amino}-1-(2,2,2-trifluoroethyl)-1H-indol-2-yl)prop-2-yn-1-yl]amino}-3-methoxybenzoic acid, MS (ES$^{30}$, m/z): 604.2; and 4-{[3-(4-{[(3S,4R)-1-(carboxymethyl)-3-fluoropiperidin-4-yl]amino}-1-(2,2,2-trifluoroethyl)-1H-indol-2-yl)prop-2-yn-1-yl]amino}-3-methoxybenzoic acid, MS (ES$^{30}$, m/z): 577.2.

Example D140: Preparation of Compound 487A

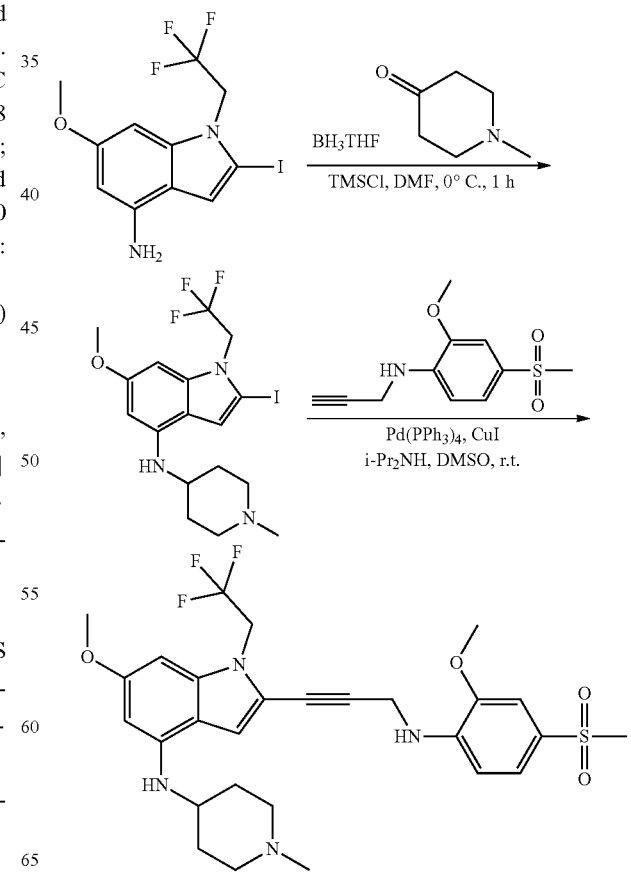

Synthesis of 2-iodo-6-methoxy-N-(1-methylpiperidin-4-yl)-1-(2,2,2-trifluoroethyl)-1H-indol-4-amine: A mixture of 1-methylpiperidin-4-one (30.57 mg, 270.19 µmol, 31.42 µL, 2 eq.), 2-iodo-6-methoxy-1-(2,2,2-trifluoroethyl)indol-4-amine (0.05 g, 135.10 µmol, 1 eq.), and TMSCl (36.69 mg, 337.74 µmol, 42.86 µL, 2.5 eq.) in DMF (2 mL) was degassed and purged with $N_2$, and then $BH_3$·THF (1 M, 337.74 µL, 2.5 eq.) was added. The mixture was stirred at 0° C. for 1 h under $N_2$ atmosphere, after which time TLC analysis (EtOAc:MeOH=20:1, $R_f$=0.24) indicated that the reaction was complete. The reaction mixture was quenched with water (100 mL) at 0° C. and extracted with EtOAc (30 mL×3). The combined organic layers were washed with brine (30 mL), dried over anhydrous sodium sulfate, filtered, and concentrated under reduced pressure. The residue was purified by prep-TLC ($SiO_2$, EtOAc:MeOH=20:1, $R_f$=0.24) to provide 2-iodo-6-methoxy-N-(1-methylpiperidin-4-yl)-1-(2,2,2-trifluoroethyl)-1H-indol-4-amine (0.04 g, 68.48 µmol, 50.69% yield) as a yellow solid.

Synthesis of 2-{3-[(4-methanesulfonyl-2-methoxyphenyl)amino]prop-1-yn-1-yl}-6-methoxy-N-(1-methylpiperidin-4-yl)-1-(2,2,2-trifluoroethyl)-1H-indol-4-amine: To a mixture of 2-methoxy-4-(methylsulfonyl)-N-(prop-2-yn-1-yl)aniline (23.41 mg, 89.03 µmol, 1.3 eq.) and 2-iodo-6-methoxy-N-(1-methylpiperidin-4-yl)-1-(2,2,2-trifluoroethyl)-1H-indol-4-amine (0.04 g, 68.48 µmol, 1 eq.) in DMSO (2 mL) were added CuI (13.04 mg, 68.48 µmol, 1 eq.), followed by $Pd(PPh_3)_4$ (7.91 mg, 6.85 µmol, 0.10 eq.) and diisopropylamine (6.93 mg, 68.48 µmol, 9.68 µL, 1 eq.). The mixture was stirred at 30° C. for 1 h under $N_2$, after which time LC-MS analysis indicated that the reaction was complete. The reaction mixture was quenched with a saturated aqueous solution of EDTA (30 mL) and stirred with EtOAc (10 mL) at 25° C. for 1 h. The resulting mixture was extracted with EtOAc (20 mL×3). The combined organic layers were washed with brine (30 mL), dried over anhydrous sodium sulfate, filtered, and concentrated under reduced pressure. The residue was purified by prep-TLC ($SiO_2$, PE:EtOAc=0:1, $R_f$=0.24) and further purified by prep-HPLC to provide 2-{3-[(4-methanesulfonyl-2-methoxyphenyl)amino]prop-1-yn-1-yl}-6-methoxy-N-(1-methylpiperidin-4-yl)-1-(2,2,2-trifluoroethyl)-1H-indol-4-amine (0.0072 g, 11.12 µmol, 16.24% yield) as a yellow solid. MS ($ES^{30}$, m/z): 579.2.

Example D141: Preparation of Compound 643A

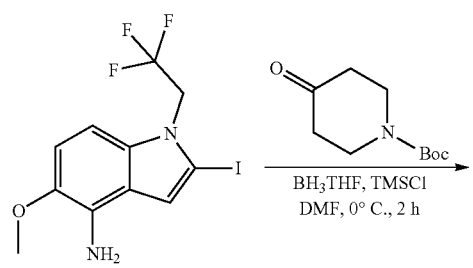

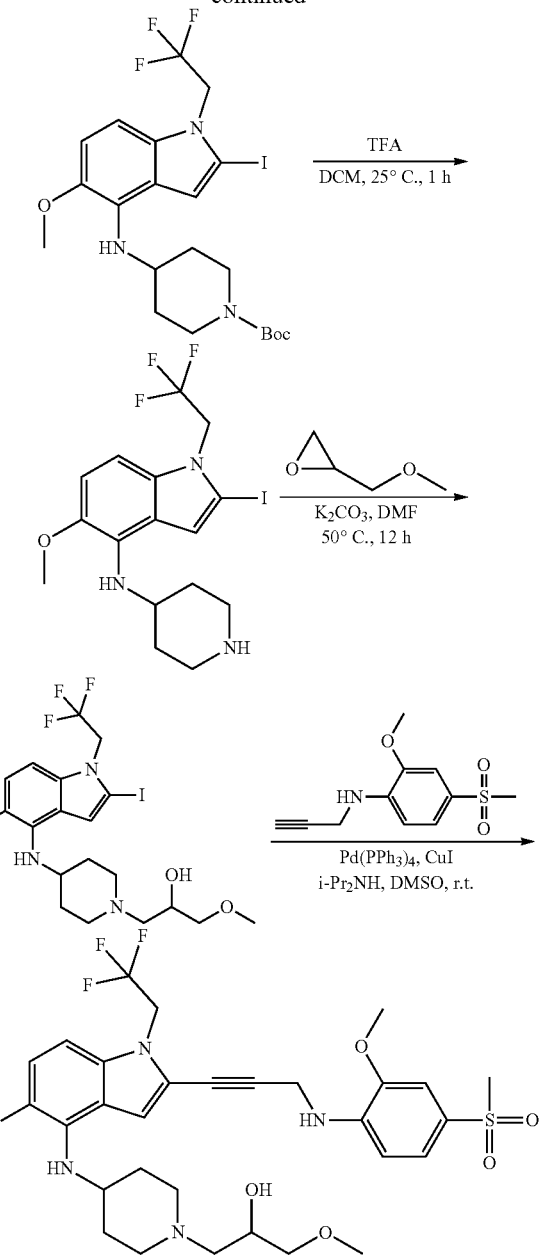

Synthesis of tert-butyl 4-((2-iodo-5-methoxy-1-(2,2,2-trifluoroethyl)-1H-indol-4-yl)amino)piperidine-1-carboxylate: To a mixture of tert-butyl 4-oxopiperidine-1-carboxylate (116.28 mg, 583.61 µmol, 26.80 µL, 3 eq.) and 2-iodo-5-methoxy-1-(2,2,2-trifluoroethyl)-1H-indol-4-amine (0.08 g, 194.54 µmol, 1 eq.) in DMF (2 mL) was added TMSCl (52.84 mg, 486.34 µmol, 61.72 µL, 2.5 eq.). The mixture was then cooled to 0° C., and $BH_3$·THF (1 M, 486.34 µL, 2.5 eq.) was added under $N_2$. The mixture was stirred at 0° C. for 1 h, after which time LC-MS analysis indicated that the reaction was complete. The reaction mixture was quenched with water (100 mL) at 0° C., and then extracted with EtOAc (30 mL×3). The combined organic layers were washed with brine (30 mL), dried over $Na_2SO_4$, filtered, and concentrated under reduced pressure. The residue was purified by prep-TLC ($SiO_2$, PE:EtOAc=1:1, $R_f$=0.43) to provide tert-butyl 4-((2-iodo-5-methoxy-1-(2,2,2-trifluoroethyl)-1H-indol-4- yl)amino)piperidine-1-carboxylate (0.08 g, 115.66 µmol, 59.45% yield) as a yellow oil. MS (ES³⁰, m/z): 554.0.

Synthesis of 2-iodo-5-methoxy-N-(piperidin-4-yl)-1-(2,2,2-trifluoroethyl)-1H-indol-4-amine: To a mixture of tert-butyl 4-((2-iodo-5-methoxy-1-(2,2,2-trifluoroethyl)-1H-indol-4-yl)amino)piperidine-1-carboxylate (0.07 g, 101.20 µmol, 1 eq.) in DCM (0.5 mL) was added TFA (5.39 g, 47.27 mmol, 3.50 mL, 467.10 eq.). The mixture was stirred at 25° C. for 1 h, after which time LC-MS analysis indicated that the reaction was complete. The reaction mixture was quenched with saturated solution of NaHCO₃ (100 mL) at 0° C., diluted with EtOAc (20 mL), and extracted with EtOAc (30 mL×3). The combined organic layers were washed with brine (20 mL), dried over Na₂SO₄, filtered, and concentrated under reduced pressure to provide 2-iodo-5-methoxy-N-(piperidin-4-yl)-1-(2,2,2-trifluoroethyl)-1H-indol-4-amine (0.050 g, 88.25 µmol, 87.21% yield) as a yellow solid, which was directly used in next step. MS (ES³⁰, m/z): 453.8.

Synthesis of 1-(4-((2-iodo-5-methoxy-1-(2,2,2-trifluoroethyl)-1H-indol-4-yl)amino)piperidin-1-yl)-3-methoxypropan-2-ol: A mixture of 2-iodo-5-methoxy-N-(piperidin-4-yl)-1-(2,2,2-trifluoroethyl)-1H-indol-4-amine (0.04 g, 70.60 µmol, 1 eq.), glycidyl methyl ether (31.10 mg, 353.01 µmol, 31.42 µL, 5 eq.), and K₂CO₃ (29.27 mg, 211.81 µmol, 3 eq.) in DMF (1 mL) was stirred at 50° C. for 10 h, after which time LC-MS analysis indicated that a product with the desired mass was present. The reaction mixture was quenched with water (100 mL) at 0° C. and extracted with EtOAc (30 mL×3). The combined organic layers were washed with brine (30 mL), dried over Na₂SO₄, filtered, and concentrated under reduced pressure. The residue was purified by prep-TLC (SiO₂, PE:EtOAc=1:1, R_f=0.43) to provide 1-(4-((2-iodo-5-methoxy-1-(2,2,2-trifluoroethyl)-1H-indol-4-yl)amino)piperidin-1-yl)-3-methoxypropan-2-ol (0.04 g, 59.11 µmol, 83.72% yield) as yellow solid. MS (ES³⁰, m/z): 542.0.

Synthesis of final product: To a of mixture 2-methoxy-4-(methylsulfonyl)-N-(prop-2-yn-1-yl)aniline (17.87 mg, 70.93 µmol, 1.2 eq.) and 1-(4-((2-iodo-5-methoxy-1-(2,2,2-trifluoroethyl)-1H-indol-4-yl)amino)piperidin-1-yl)-3-methoxypropan-2-ol (0.04 g, 59.11 µmol, 1 eq.) in DMSO (2 mL) was added CuI (11.26 mg, 59.11 µmol, 1 eq.), followed by Pd(PPh₃)₄ (6.83 mg, 5.91 µmol, 0.10 eq.) and diisopropylamine (5.98 mg, 59.11 µmol, 8.35 µL, 1 eq.). The mixture was stirred at 30° C. for 1 h under N₂, after which time LC-MS analysis indicated that the reaction was complete. The reaction mixture was quenched with a saturated aqueous solution of EDTA and EtOAc (~10 mL), stirred at 25° C. for 1 h, and extracted with EtOAc (20 mL×3). The combined organic layers were washed with brine (30 mL), dried over anhydrous sodium sulfate, filtered, and concentrated under reduced pressure. The residue was purified by prep-TLC (SiO₂, DCM:MeOH=10:1, R_f=0.24) to provide 1-{4-[(2-{3-[(4-methanesulfonyl-2-methoxyphenyl)amino]prop-1-yn-1-yl}-5-methoxy-1-(2,2,2-trifluoroethyl)-1H-indol-4-yl)amino]piperidin-1-yl}-3-methoxypropan-2-ol (0.0157 g, 23.57 µmol, 39.88% yield) as light yellow solid. MS (ES³⁰, m/z): 653.4.

Example D142: Preparation of Compounds 976A, 977A, 978A, and 979A

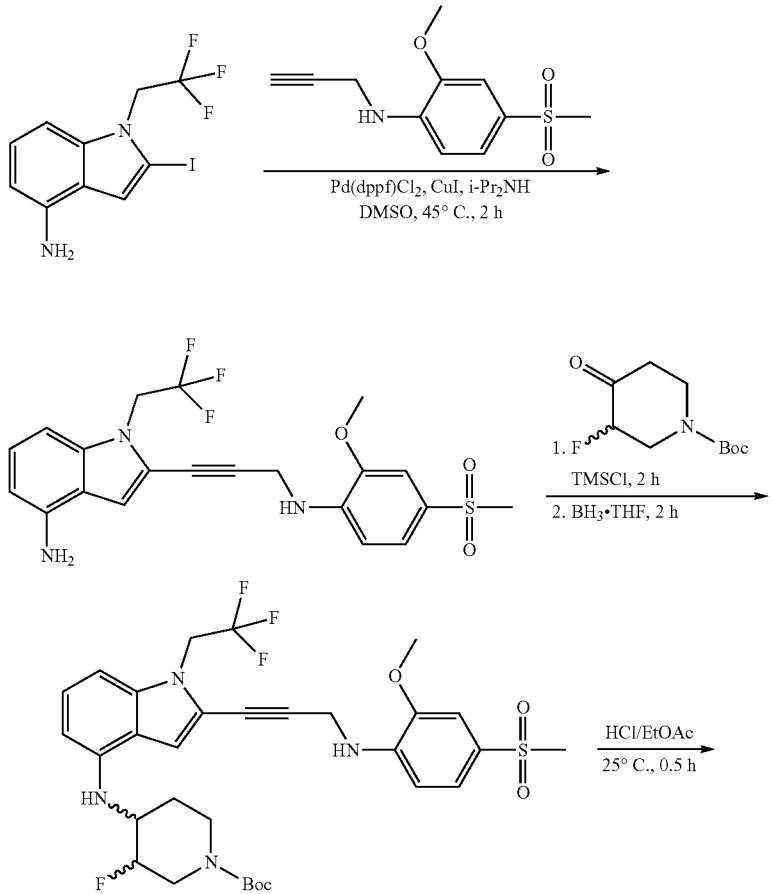

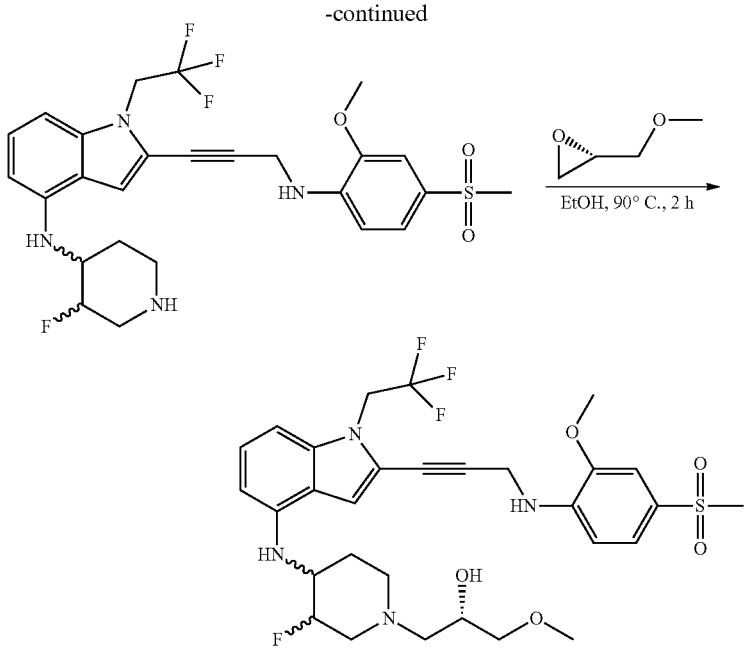

Synthesis of 2-(3-((2-methoxy-4-(methylsulfonyl)phenyl) amino)prop-1-yn-1-yl)-1-(2,2,2-trifluoroethyl)-1H-indol-4-amine: To the mixture of 2-iodo-1-(2,2,2-trifluoroethyl)-1H-indol-4-amine (1 g, 2.94 mmol, 1 eq.) and 2-methoxy-4-methylsulfonyl-N-prop-2-ynyl-aniline (1.41 g, 5.88 mmol, 2 eq.) in DMSO (15 mL) was added diisopropylamine (2.98 g, 29.40 mmol, 4.16 mL, 10 eq.) and Pd(dppf)Cl$_2$ (215.16 mg, 294.05 μmol, 0.1 eq.), followed by CuI (560.01 mg, 2.94 mmol, 1 eq.) under N$_2$. The reaction mixture was stirred for 2 h at 45° C., after which time LC-MS and TLC (PE:EtOAc=1:1) indicated that the reaction was complete. The reaction mixture was quenched by addition of a saturated aqueous solution of EDTA (100 mL) at 25° C., and then extracted with EtOAc (50 mL×3). The combined organic layers were dried over anhydrous sodium sulfate, filtered, and concentrated in vacuo. The resulting residue was purified by column chromatography (PE:EtOAc=2:1 to 1:1) to afford 2-(3-((2-methoxy-4-(methylsulfonyl)phenyl)amino) prop-1-yn-1-yl)-1-(2,2,2-trifluoroethyl)-1H-indol-4-amine (0.8 g, 1.68 mmol, 57.25% yield) as a light yellow solid.

Synthesis of (rac)-tert-butyl (3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidine-1-carboxylate and (rac)-tert-butyl (3S,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino) piperidine-1-carboxylate: To a solution of tert-butyl 3-fluoro-4-oxopiperidine-1-carboxylate (360.89 mg, 1.66 mmol, 2.5 eq.) and 2-[3-(2-methoxy-4-methylsulfonyl-anilino)prop-1-ynyl]-1-(2,2,2-trifluoroethyl)indol-4-amine (300 mg, 664.51 μmol, 1 eq.) in DMF (6 mL) was added TMSCl (180.48 mg, 1.66 mmol, 210.84 μL, 2.5 eq.), and the resulting mixture was stirred at 0° C. for 2 h. BH$_3$·THF (1 M, 3.32 mL, 5 eq.) was then added under N$_2$, and the mixture was stirred for a further 2 h at 20° C., after which time LC-MS analysis indicated that the reaction was complete. The reaction mixture was quenched by adding saturated aqueous Na$_2$CO$_3$ (30 mL), diluted with water (10 mL), and extracted with EtOAc (20 mL×2). The combined organic layers were washed with brine (10 mL), dried over anhydrous sodium sulfate, filtered, and concentrated in vacuo. The crude residue was purified by prep-HPLC to provide (rac)-tert-butyl (3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidine-1-carboxylate (80 mg, 37% yield) and (rac)-tert-butyl (3S,4S)-3-fluoro-4-((2-(3-((2-methoxy-4-(methylsulfonyl)phenyl) amino)prop-1-yn-1-yl)-1-(2,2,2-trifluoroethyl)-1H-indol-4-yl)amino)piperidine-1-carboxylate (80 mg, 37% yield) as yellow solids.

General procedure for synthesis of (rac)-N-((3S,4S)-3-fluoropiperidin-4-yl)-2-(3-((2-methoxy-4-(methylsulfonyl) phenyl)amino)prop-1-yn-1-yl)-1-(2,2,2-trifluoroethyl)-1H-indol-4-amine and (rac)-N-((3S,4R)-3-fluoropiperidin-4-yl)-2-(3-((2-methoxy-4-(methylsulfonyl)phenyl)amino) prop-1-yn-1-yl)-1-(2,2,2-trifluoroethyl)-1H-indol-4-amine: A solution of (rac)-tert-butyl (3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidine-1-carboxylate (80 mg, 122.57 μmol, 1 eq.) or (rac)-tert-butyl (3S,4S)-3-fluoro-4-((2-(3-((2-methoxy-4-(methylsulfonyl) phenyl)amino)prop-1-yn-1-yl)-1-(2,2,2-trifluoroethyl)-1H-indol-4-yl)amino)piperidine-1-carboxylate (80 mg, 122.57 μmol, 1 eq.) in HCl/EtOAc (4 M, 8 mL, 261.08 eq.) was stirred at 25° C. for 10 min, after which time LC-MS analysis indicated that reaction was complete. The solution was concentrated in vacuo. The crude residue was neutralized by adding saturated aqueous Na$_2$CO$_3$ (100 mL), and the resulting mixture was extracted with EtOAc (200 mL). The combined organic layers were washed with brine (100 mL×3), dried over anhydrous sodium sulfate, and filtered to provide crude (rac)-N-((3S,4S)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine or (rac)-N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine as a light yellow solid.

Synthesis of final products: To a solution of (rac)-N-((3S, 4S)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine or (rac)-N-((3S,4R)-3-fluoropiperidin-4-yl)-2-(3-((2-methoxy-4-(methylsulfonyl) phenyl)amino)prop-1-yn-1-yl)-1-(2,2,2-trifluoroethyl)-1H-indol-4-amine (180.97 μmol, 1 eq.) in EtOH (3 mL) was added (S)-glycidyl methyl ether (95.67 mg, 1.09 mmol, 96.63 µL, 6 eq.). The mixture was stirred at 90° C. for 2 h under $N_2$ atmosphere, after which time LC-MS analysis indicated that the reaction was complete. The reaction mixture was concentrated in vacuo and was purified by prep-HPLC to provide the epimeric product as a white solid (55 mg, 85.85 µmol, 47.44% yield), which was then resolved via chiral SFC to provide the desired pure enantiomers.

(S)-1-((3R,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol, MS ($ES^{30}$, m/z): 641.2; (S)-1-((3S,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol, MS ($ES^{30}$, m/z): 641.2; (S)-1-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol, MS ($ES^{30}$, m/z): 641.3; and (S)-1-((3S,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol, MS ($ES^{30}$, m/z): 641.3.

Example D143: Preparation of Compounds 980A and 981A

Compounds 980A and 981A were prepared via a procedure analogous to the synthesis shown in EXAMPLE D142, using racemic glycidyl methyl ether in place of (S)-glycidyl methyl ether.

(rac)-1-((3S,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol, MS ($ES^{30}$, m/z): 641.3; and (rac)-1-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol, MS ($ES^{30}$, m/z): 641.3.

Example D144: General Procedure for Preparation of Compounds 982A, 983A, 984A, and 985A

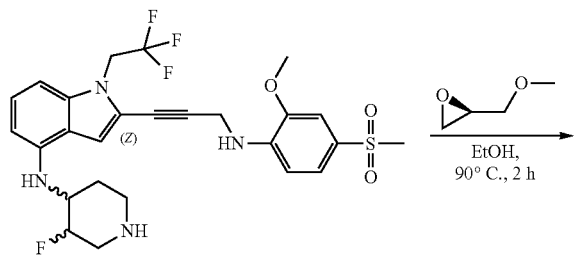

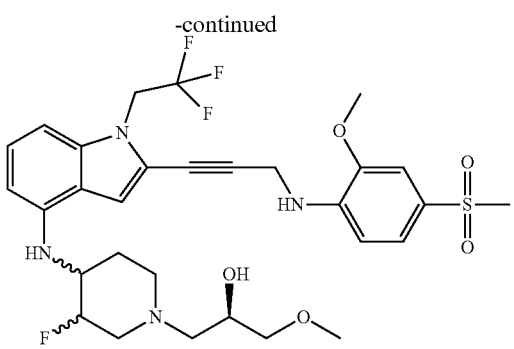

Compounds 982A, 983A, 984A, and 985A were prepared via a procedure analogous to the synthesis shown in EXAMPLE D142, using (R)-glycidyl methyl ether in place of (S)-glycidyl methyl ether.

The epimeric mixture was resolved via chiral SFC to provide the desired pure enantiomers. (R)-1-((3S,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol, MS ($ES^{30}$, m/z): 641.2; (R)-1-((3R,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol, MS ($ES^{30}$, m/z): 641.2; (R)-1-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol, MS ($ES^{30}$, m/z): 641.3; and (R)-1-((3S,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol, MS ($ES^{30}$, m/z): 641.3.

Example D145: Preparation of Compound 987A

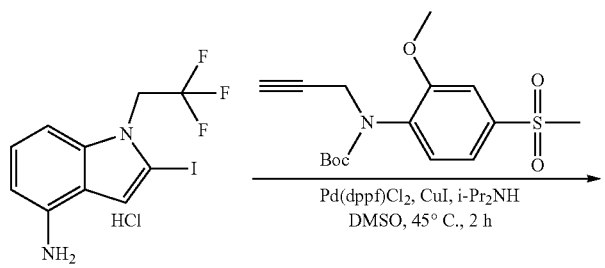

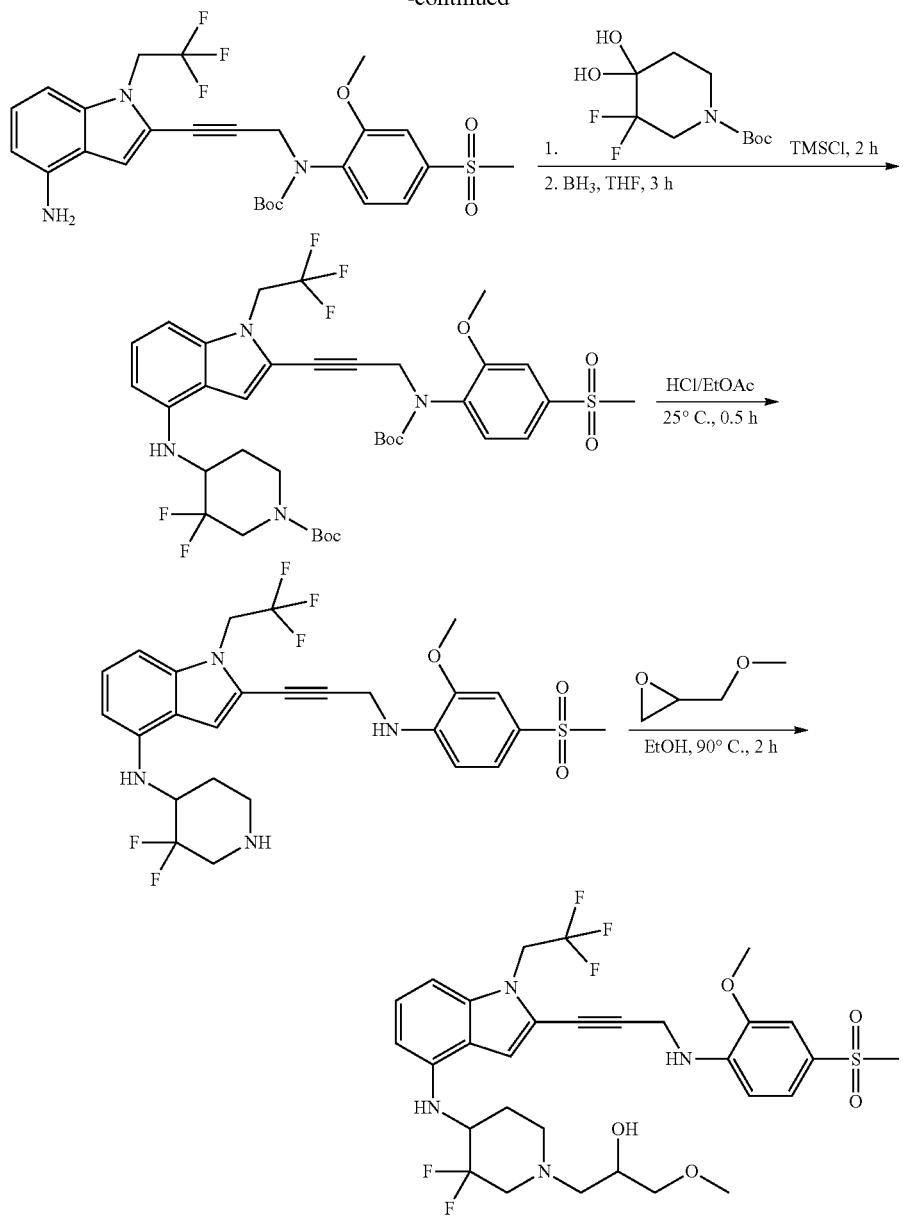

Synthesis of tert-butyl (3-(4-amino-1-(2,2,2-trifluoro-ethyl)-1H-indol-2-yl)prop-2-yn-1-yl)(2-methoxy-4-(methylsulfonyl)phenyl)carbamate: To a mixture of 2-iodo-1-(2,2,2-trifluoroethyl)-1H-indol-4-amine hydrochloride (5 g, 13.28 mmol, 1 eq.) and tert-butyl N-(2-methoxy-4-methylsulfonyl-phenyl)-N-prop-2-ynyl-carbamate (8.11 g, 23.90 mmol, 1.8 eq.) in DMSO (50 mL) were added diisopropylamine (13.44 g, 132.79 mmol, 18.77 mL, 10 eq.) and Pd(dppf)Cl₂ (485.81 mg, 663.93 µmol, 0.05 eq.), followed by CuI (1.26 g, 6.64 mmol, 0.5 eq.) under N₂ atmosphere. The mixture was stirred for 2 h at 45° C., after which time LC-MS and TLC analysis (PE:EtOAc=1:1) indicated that the reaction was complete. The reaction mixture was quenched by adding a saturated aqueous solution of EDTA (150 mL) at 25° C. and extracted with EtOAc (150 mL×3). The combined organic layers were dried over anhydrous sodium sulfate, filtered, and concentrated in vacuo. The residue was purified by column chromatography (SiO₂, PE:EtOAc=3:1 to 1:1) to provide tert-butyl (3-(4-amino-1-(2,2,2-trifluoroethyl)-1H-indol-2-yl)prop-2-yn-1-yl)(2-methoxy-4-(methylsulfonyl)phenyl)carbamate (4.5 g, 8.16 mmol, 61.44% yield) as a red gum.

Synthesis of tert-butyl 4-((2-(3-((tert-butoxycarbonyl)(2-methoxy-4-(methylsulfonyl)phenyl)amino)prop-1-yn-1-yl)-1-(2,2,2-trifluoroethyl)-1H-indol-4-yl)amino)-3,3-difluoropiperidine-1-carboxylate: To a solution of intermediate tert-butyl 3,3-difluoro-4,4-dihydroxypiperidine-1-carboxylate (2.48 g, 9.80 mmol, 4 eq.) and tert-butyl (3-(4-amino-1-(2,2,2-trifluoroethyl)-1H-indol-2-yl)prop-2-yn-1-yl)(2-methoxy-4-(methylsulfonyl)phenyl)carbamate (1.5 g, 2.45 mmol, 1 eq.) in DMF (15 mL) was added TMSCl (798.50 mg, 7.35 mmol, 932.83 µL, 3 eq.). The mixture was stirred at 0° C. for 2 h, then BH₃·THF (1 M, 12.25 mL, 5 eq.) was added under N₂ atmosphere. The mixture was stirred at 25° C. for a further 3 h, after which time TLC analysis indicated a ~2:1 ratio of starting primary amine to product. The reaction mixture was quenched by addition of saturated aqueous Na$_2$CO$_3$ (300 mL), diluted with water (10 mL), and extracted with EtOAc (150 mL×2). The combined organic layers were then washed with brine (10 mL), dried over anhydrous sodium sulfate, filtered, and concentrated under reduced pressure. The residue was purified by column chromatography (PE:EtOAc=3:1 to 2:1) to provide tert-butyl 4-((2-(3-((tert-butoxycarbonyl)(2-methoxy-4-(methylsulfonyl)phenyl)amino)prop-1-yn-1-yl)-1-(2,2,2-trifluoroethyl)-1H-indol-4-yl)amino)-3,3-difluoropiperidine-1-carboxylate (1.5 g, 1.65 mmol, 67.51% yield) as a yellow solid.

Synthesis of N-(3,3-difluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine: A solution of tert-butyl 4-((2-(3-((tert-butoxycarbonyl)(2-methoxy-4-(methylsulfonyl)phenyl)amino)prop-1-yn-1-yl)-1-(2,2,2-trifluoroethyl)-1H-indol-4-yl)amino)-3,3-difluoropiperidine-1-carboxylate (250 mg, 275.69 μmol, 1 eq.) in HCl/EtOAc (4 M, 5 mL, 72.55 eq.) was stirred at 25° C. for 30 min, after which time LC-MS analysis indicated that the reaction was complete. The solution was dried in vacuo to provide a crude residue that was neutralized by the addition of saturated aqueous Na$_2$CO$_3$ (100 mL). The mixture was extracted with EtOAc (200 mL), washed with brine (100 mL×3), dried over anhydrous sodium sulfate, filtered, and concentrated to provide crude N-(3,3-difluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine (130 mg) as a yellow solid.

Synthesis of final product: To a solution of N-(3,3-difluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine (100 mg, 175.26 μmol, 1 eq.) in EtOH (3 mL) was added glycidyl methyl ether (92.65 mg, 1.05 mmol, 93.58 μL, 6 eq.). The mixture was stirred at 90° C. for 2 h under N$_2$ atmosphere, after which time LC-MS analysis indicated that the reaction was complete. The reaction mixture was concentrated in vacuo and purified by prep-HPLC to provide 1-(3,3-difluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol (21.7 mg, 32.85 μmol, 18.74% yield) as a yellow solid. MS (ES$^{30}$, m/z): 659.2.

Example D146: General Procedure for Preparation of Compounds 769A, 770A, 771A, 772A, 773A, and 774A

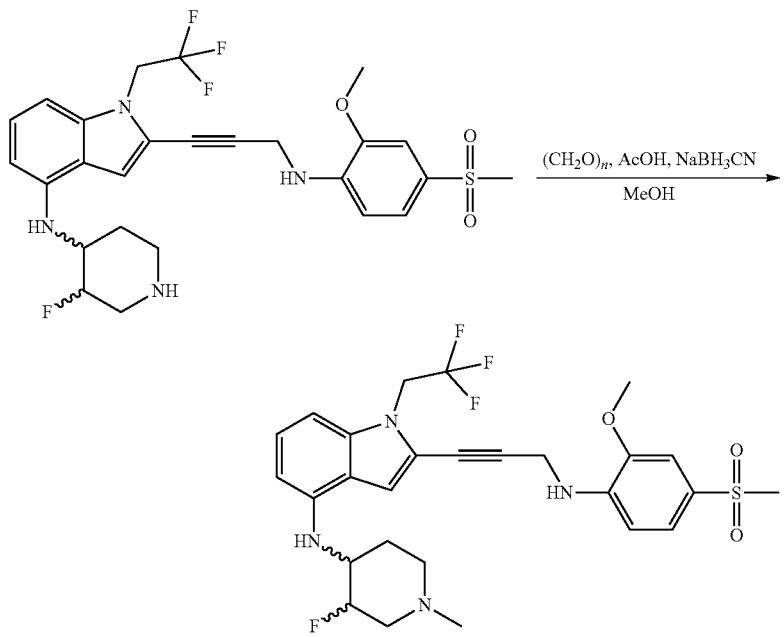

To a solution of (rac)-N-((3S,4S)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine or (rac)-N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine (200 mg, 289.55 μmol, 1 eq.) and (CH$_2$O)n (43.47 mg, 1.45 mmol, 39.88 μL, 5 eq.) in MeOH (3 mL) was added acetic acid (17.39 ug, 0.29 μmol, 0.001 eq.) and NaBH$_3$CN (90.98 mg, 1.45 mmol, 5 eq.). The mixture was stirred at 50° C. for 4 h, then TLC analysis (DCM:MeOH=10:1, R$_f$=0.43) indicated that the reaction was complete. The reaction was quenched by addition of saturated aqueous NaHCO$_3$ (60 mL) and then extracted with EtOAc (20 mL×3). The combined organic layers were dried over anhydrous sodium sulfate, filtered, and concentrated under reduced pressure to provide a residue. The residue was purified by prep-HPLC to provide the desired racemic compounds as light yellow solids. The enantiomers were separated by chiral SFC to obtain the desired products.

(rac)-N-((3R,4R)-3-fluoro-1-methylpiperidin-4-yl)-2-(3-((2-methoxy-4-(methylsulfonyl)phenyl)amino)prop-1-yn-1-yl)-1-(2,2,2-trifluoroethyl)-1H-indol-4-amine, MS (ES$^{30}$, m/z): 567.2; (rac)-N-((3R,4S)-3-fluoro-1-methylpiperidin-4-yl)-2-(3-((2-methoxy-4-(methylsulfonyl)phenyl)amino)prop-1-yn-1-yl)-1-(2,2,2-trifluoroethyl)-1H-indol-4-amine, MS (ES$^{30}$, m/z): 567.2; N-((3R,4R)-3-fluoro-1-methylpiperidin-4-yl)-2-(3-((2-methoxy-4-(methylsulfonyl)phenyl)amino)prop-1-yn-1-yl)-1-(2,2,2-trifluoroethyl)-1H-indol-4- amine, MS (ES³⁰, m/z): 567.2; N-((3R,4S)-3-fluoro-1-methylpiperidin-4-yl)-2-(3-((2-methoxy-4-(methylsulfonyl)phenyl)amino)prop-1-yn-1-yl)-1-(2,2,2-trifluoroethyl)-1H-indol-4-amine, MS (ES³⁰, m/z): 567.2; N-((3S,4S)-3-fluoro-1-methylpiperidin-4-yl)-2-(3-((2-methoxy-4-(methylsulfonyl)phenyl)amino)prop-1-yn-1-yl)-1-(2,2,2-trifluoroethyl)-1H-indol-4-amine, MS (ES³⁰, m/z): 567.2; and N-((3S,4R)-3-fluoro-1-methylpiperidin-4-yl)-2-(3-((2-methoxy-4-(methylsulfonyl)phenyl)amino)prop-1-yn-1-yl)-1-(2,2,2-trifluoroethyl)-1H-indol-4-amine), MS (ES³⁰, m/z): 567.2.

Example D147: General Procedure for Preparation of Compounds 775A, 776A, 790A, and 791A

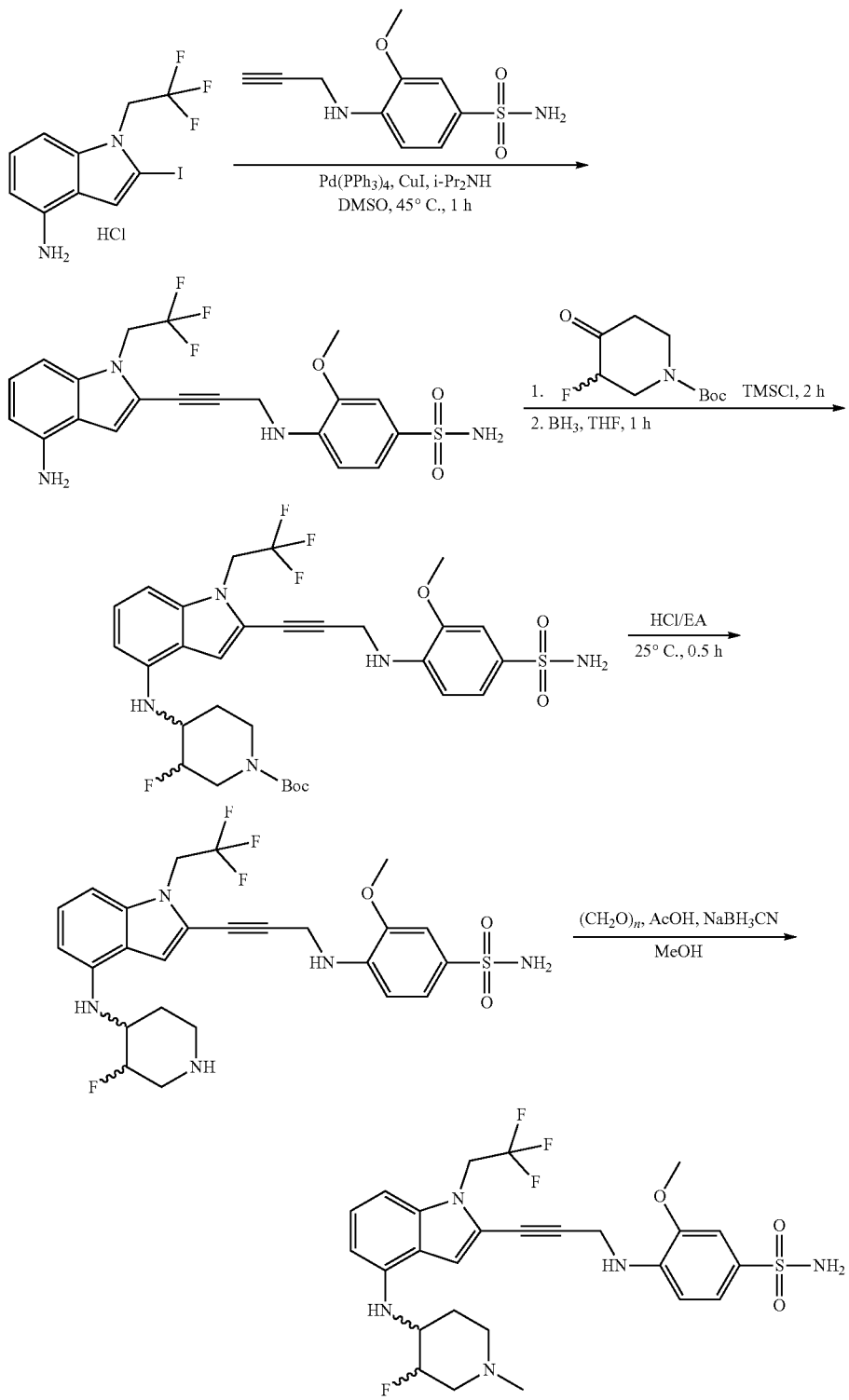

Compounds 775A, 776A, 790A, and 791A were prepared via a procedure analogous to the synthesis of (rac)-N-((3S,4S)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine and (rac)-N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine according to EXAMPLE D141 using 3-methoxy-4-(prop-2-yn-1-ylamino)benzenesulfonamide in place of 2-methoxy-4-(methylsulfonyl)-N-(prop-2-yn-1-yl)aniline and

Example D146

(rac)-4-((3-(4-(((3R,4R)-3-fluoro-1-methylpiperidin-4-yl)amino)-1-(2,2,2-trifluoroethyl)-1H-indol-2-yl)prop-2-yn-1-yl)amino)-3-methoxybenzenesulfonamide, MS (ES$^{30}$, m/z): 568.1; (rac)-4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-3-methoxybenzenesulfonamide, MS (ES$^{30}$, m/z): 568.2; 4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-3-methoxybenzenesulfonamide, MS (ES$^{30}$, m/z): 568.3; and 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzenesulfonamide, MS (ES$^{30}$, m/z): 568.3.

Example D148: General Procedure for Preparation of Compound 986A

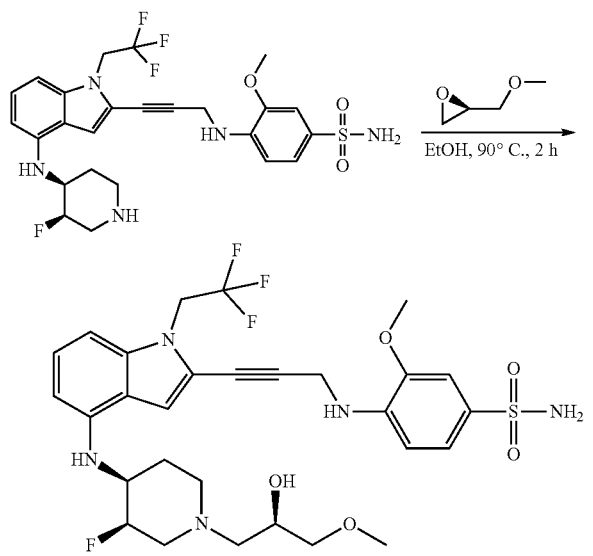

4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzenesulfonamide was prepared via a procedure analogous to EXAMPLE D142, using (R)-glycidyl methyl ether in place of (S)-glycidyl methyl ether and 3-methoxy-4-(prop-2-yn-1-ylamino)benzenesulfonamide in place of 2-methoxy-4-(methylsulfonyl)-N-(prop-2-yn-1-yl)aniline. 4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzenesulfonamide was purified by prep-HPLC and obtained as a white solid.

4-((3-(4-(((3 RS,4 SR)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzenesulfonamide, MS (ES$^{30}$, m/z): 642.3.

Example D149: Preparation of Compounds 549A and 550A

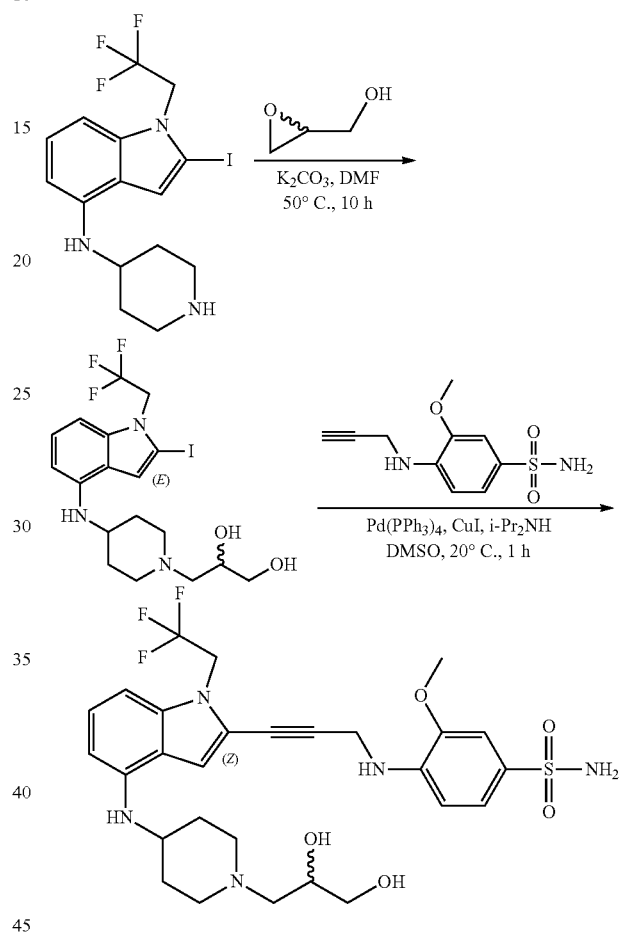

Synthesis of 3-(4-((2-iodo-1-(2,2,2-trifluoroethyl)-1H-indol-4-yl)amino)piperidin-1-yl)propane-1,2-diol: To a solution of 2-iodo-N-(piperidin-4-yl)-1-(2,2,2-trifluoroethyl)-1H-indol-4-amine (0.3 g, 708.86 μmol, 1 eq.) in DMF (3 mL) were added R-glycidol (262.56 mg, 3.54 mmol, 234.43 μL, 5 eq.) and K$_2$CO$_3$ (293.92 mg, 2.13 mmol, 3 eq.). The reaction mixture was stirred at 50° C. for 10 h, quenched with water (10 mL), and extracted with EtOAc (10 mL×3). The combined organic layers were washed with brine (5 mL), dried over anhydrous sodium sulfate and concentrated to provide crude 3-(4-((2-iodo-1-(2,2,2-trifluoroethyl)-1H-indol-4-yl)amino)piperidin-1-yl)propane-1,2-diol (0.3 g) as a yellow oil. The crude product was used to the next step without further purification.

Synthesis of final products: To a solution of 3-methoxy-4-(prop-2-yn-1-ylamino)benzenesulfonamide (116 mg, 1.3 eq.) in DMSO (10 mL) was added CuI (71 mg, 1 eq.) and diisopropylamine (217 mg, 10 eq.). The reaction was degassed with N$_2$, 3-(4-((2-iodo-1-(2,2,2-trifluoroethyl)-1H-indol-4-yl)amino)piperidin-1-yl)propane-1,2-diol (183 mg, 1 eq.) and Pd(PPh$_3$)$_4$ (85 mg, 0.2 eq.) were added, and the reaction mixture was again degassed with N₂. The reaction mixture was stirred at 25° C. for 2 h, after which time LC-MS analysis indicated that the reaction was complete. EtOAc (20 mL) was then added to the reaction mixture, and the mixture was poured into a saturated aqueous solution of EDTA (50 mL) and stirred at 25° C. for 2 h. The aqueous phase was extracted with EtOAc (30 mL×3), and the combined organic layers were washed with brine (40 mL×1), dried over anhydrous sodium sulfate, treated with activated carbon, filtered, and concentrated in vacuo to provide the crude product. The residue was purified by prep-TLC or chromatography on silica-gel (DCM:MeOH=10:1, $R_f$=0.4), then further purified by prep-HPLC provide (rac)-4-({3-[4-({1-[2,3-dihydroxypropyl]piperidin-4-yl}amino)-1-(2,2,2-trifluoroethyl)-1H-indol-2-yl]prop-2-yn-1-yl}amino)-3-methoxybenzene-1-sulfonamide as a yellow solid. MS (ES³⁰, m/z): 610.2. The same procedure was used starting from S-glycidol to obtain the other enantiomer.

Example D150: General Procedure for Preparation of Compounds 580A and 581A

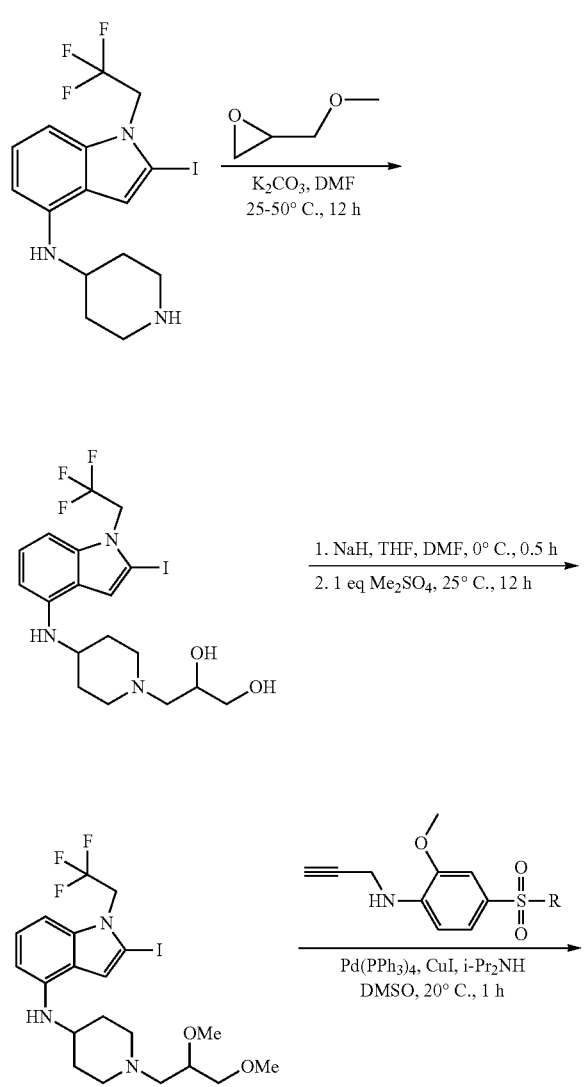

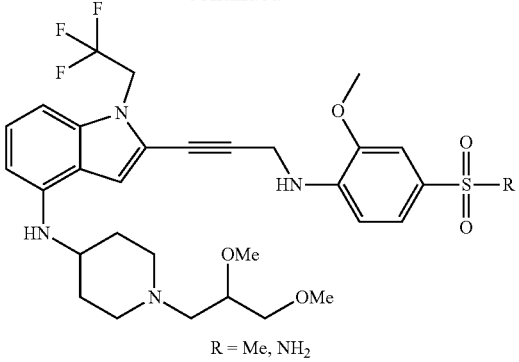

R = Me, NH₂

Synthesis of 1-(4-((2-iodo-1-(2,2,2-trifluoroethyl)-1H-indol-4-yl)amino)piperidin-1-yl)-3-methoxypropan-2-ol: To a mixture of 2-iodo-N-(piperidin-4-yl)-1-(2,2,2-trifluoroethyl)-1H-indol-4-amine (1.5 g, 3.40 mmol, 1 eq.) and glycidyl methyl ether (1.58 g, 17.01 mmol, 1.59 mL, 5 eq., 95% purity) in DMF (30 mL) was added K₂CO₃ (1.41 g, 10.21 mmol, 3 eq.) in one portion at 25° C. under N₂. The mixture was then stirred at 50° C. for 12 h, after which time TLC analysis (EtOAc:MeOH=5:1, $R_f$=0.40) indicated that the reaction was complete. The mixture was cooled to 25° C., poured into water (150 mL), and stirred for 1 min. The aqueous phase was extracted with EtOAc (50 mL×3), and the combined organic layers were washed with brine (50 mL), dried over anhydrous sodium sulfate, filtered, and concentrated in vacuo. The residue was purified by silica gel chromatography (SiO₂, EtOAc/MeOH=1/0, 5/1) to afford 1-(4-((2-iodo-1-(2,2,2-trifluoroethyl)-1H-indol-4-yl)amino)piperidin-1-yl)-3-methoxypropan-2-ol (1.6 g, 2.82 mmol, 82.77% yield) as red oil.

Synthesis of N-(1-(2,3-dimethoxypropyl)piperidin-4-yl)-2-iodo-1-(2,2,2-trifluoroethyl)-1H-indol-4-amine: To a mixture of 1-(4-((2-iodo-1-(2,2,2-trifluoroethyl)-1H-indol-4-yl)amino)piperidin-1-yl)-3-methoxypropan-2-ol (200 mg, 352.03 μmol, 1 eq.) in THF (3 mL) was added NaH (56.32 mg, 1.41 mmol, 60% in mineral oil, 4 eq.) in one portion at 0° C. under N₂. The mixture was stirred at 0° C. for 30 min, and dimethyl sulfate (44.40 mg, 352.03 μmol, 33.39 μL, 1 eq.) was then added in one portion at 0° C. under N₂. The reaction mixture was warmed to 25° C. and stirred for 1 h, after which time TLC analysis (EtOAc:MeOH=5:1, $R_f$=0.72) and LC-MS analysis indicated that the reaction was complete. The mixture was poured into a saturated aqueous NH₄Cl solution (20 mL), stirred for 2 min, and the aqueous phase was extracted with EtOAc (10 mL×3). The combined organic layers were washed with brine (10 mL), dried over anhydrous sodium sulfate, filtered, and concentrated in vacuo. The residue was purified by prep-TLC (EtOAc:MeOH=5:1, $R_f$=0.72) to afford N-(1-(2,3-dimethoxypropyl)piperidin-4-yl)-2-iodo-1-(2,2,2-trifluoroethyl)-1H-indol-4-amine (135 mg, 154.18 μmol, 43.80% yield) as yellow solid.

Synthesis of final products: Compounds 580A and 581A were prepared via a procedure analogous to EXAMPLE C69, using N-(1-(2,3-dimethoxypropyl)piperidin-4-yl)-2-iodo-1-(2,2,2-trifluoroethyl)-1H-indol-4-amine in place of 3-(4-((2-iodo-1-(2,2,2-trifluoroethyl)-1H-indol-4-yl)amino)piperidin-1-yl)propane-1,2-diol.

N-[1-(2,3-dimethoxypropyl)piperidin-4-yl]-2-{3-[(4-methanesulfonyl-2-methoxyphenyl)amino]prop-1-yn-1-yl}-1-(2,2,2-trifluoroethyl)-1H-indol-4-amine, MS (ES³⁰, m/z):

637.3; and 4-{[3-(4-{[1-(2,3-dimethoxypropyl)piperidin-4-yl]amino}-1-(2,2,2-trifluoroethyl)-1H-indol-2-yl)prop-2-yn-1-yl]amino}-3-methoxybenzene-1-sulfonamide, MS (ES30, m/z): 638.2.

Example D151: General Procedure for Preparation of Compounds 569A and 574A

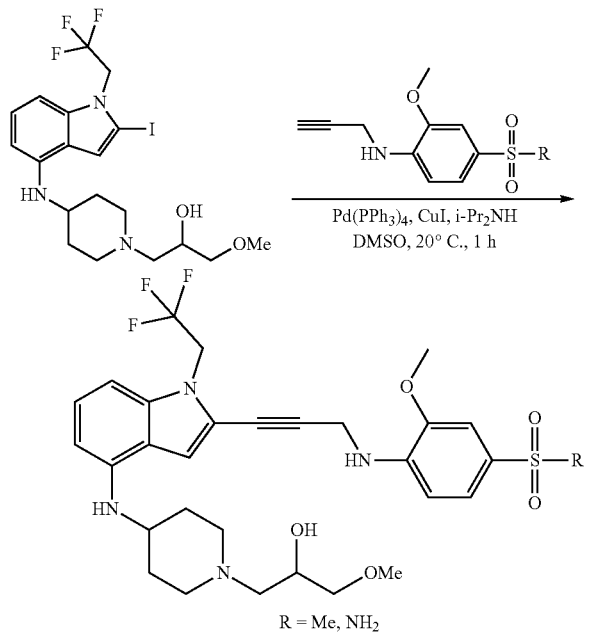

Compounds 569A and 574A were prepared via a procedure analogous to EXAMPLE C69, using 1-(4-((2-iodo-1-(2,2,2-trifluoroethyl)-1H-indol-4-yl)amino)piperidin-1-yl)-3-methoxypropan-2-ol in place of 3-(4-((2-iodo-1-(2,2,2-trifluoroethyl)-1H-indol-4-yl)amino)piperidin-1-yl) propane-1,2-diol.

1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol, MS (ES30, m/z): 623.3; and 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzene-1-sulfonamide, MS (ES30, m/z): 624.2.

Example D152: General Procedure for Preparation of Compounds 573 and 579A

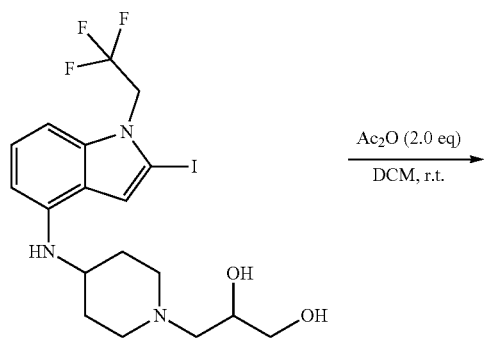

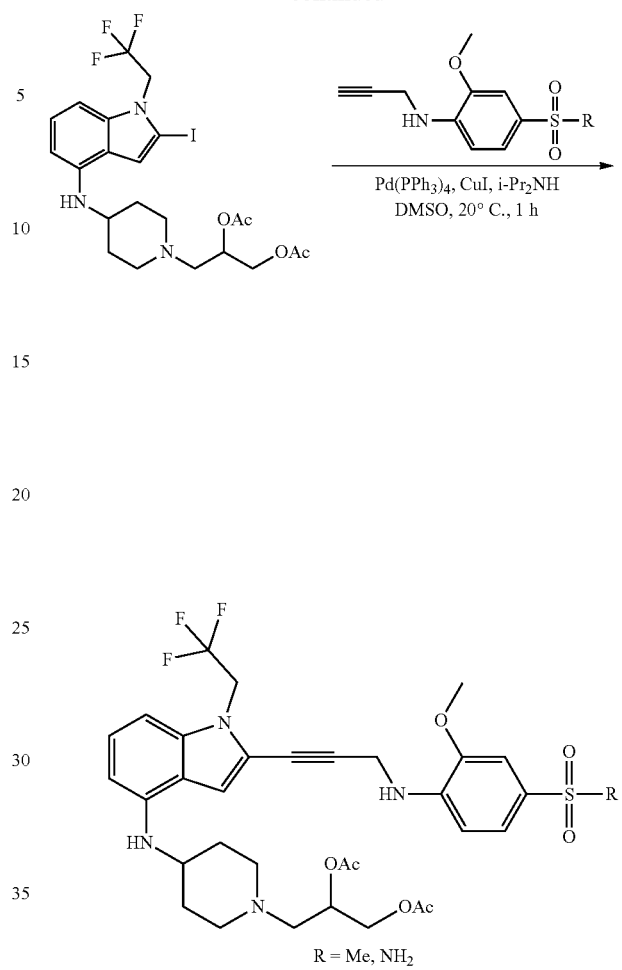

Synthesis of 3-(4-((2-iodo-1-(2,2,2-trifluoroethyl)-1H-indol-4-yl)amino)piperidin-1-yl)propane-1,2-diyl diacetate: To a solution of 3-(4-((2-iodo-1-(2,2,2-trifluoroethyl)-1H-indol-4-yl)amino)piperidin-1-yl)propane-1,2-diol (100 mg, 1 eq.) in DCM (2 mL) was added acetic anhydride (37 mg, 2 eq.), then the mixture was stirred at 25° C. for 4 h, after which time TLC and LC-MS analysis indicated that the starting diol was completely consumed. The solvent was removed by sparging with a stream of N2. The resulting residue was purified by prep-TLC (DCM:MeOH=5:1, Rf=0.80) to afford 3-(4-((2-iodo-1-(2,2,2-trifluoroethyl)-1H-indol-4-yl)amino)piperidin-1-yl)propane-1,2-diyl diacetate as light brown oil.

Synthesis of final products: Compounds 573 and 579A were prepared via a procedure analogous to EXAMPLE C69, using 3-(4-((2-iodo-1-(2,2,2-trifluoroethyl)-1H-indol-4-yl)amino)piperidin-1-yl)propane-1,2-diyl diacetate in place of 3-(4-((2-iodo-1-(2,2,2-trifluoroethyl)-1H-indol-4-yl)amino)piperidin-1-yl)propane-1,2-diol. [0993]1-(acetyloxy)-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl acetate, MS (ES30, m/z): 693.2; and 1-(acetyloxy)-3-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl acetate, MS (ES30, m/z): 694.2.

Example D153: General Procedure for the Preparation of Compounds 566A and 568A

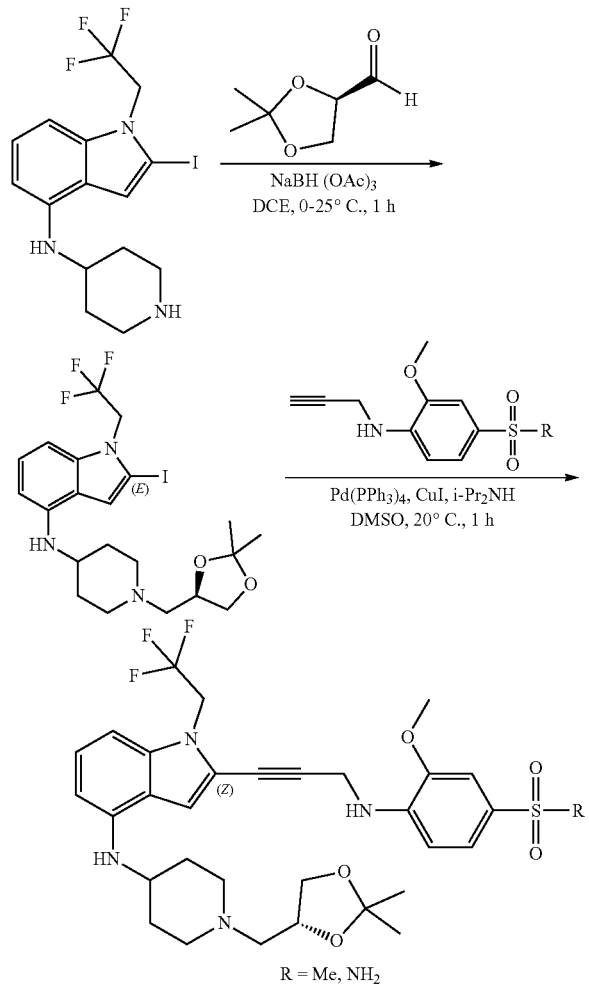

R = Me, NH₂

Synthesis of 3-(4-((2-iodo-1-(2,2,2-trifluoroethyl)-1H-indol-4-yl)amino)piperidin-1-yl)propane-1,2-diyl diacetate: To a solution of 2-iodo-N-(piperidin-4-yl)-1-(2,2,2-trifluoroethyl)-1H-indol-4-amine (300 mg, 1 eq.) and (R)-2,2-dimethyl-1,3-dioxolane-4-carbaldehyde (354 mg, 4 eq.) in 1,2-dichloroethane (20 mL) was added NaBH(OAc)₃ (577 mg, 4 eq.). The mixture was stirred at 22° C. for 1 h, after which time LC-MS and TLC analysis indicated that the reaction was complete. The reaction mixture washed with water (300 mL), and the organic phase was dried over anhydrous sodium sulfate, filtered, and concentrated in vacuo. The residue was purified by prep-TLC (PE:EtOAc=5:1, Rf=0.5) to give (R)—N-(1-((2,2-dimethyl-1,3-dioxolan-4-yl)methyl)piperidin-4-yl)-2-iodo-1-(2,2,2-trifluoroethyl)-1H-indol-4-amine as a yellow oil. (187 mg, 40.9% yield)

Synthesis of final products: Compounds 566A and 568A were prepared via a procedure analogous to EXAMPLE C69 using (R)—N-(1-((2,2-dimethyl-1,3-dioxolan-4-yl)methyl)piperidin-4-yl)-2-iodo-1-(2,2,2-trifluoroethyl)-1H-indol-4-amine in place of 3-(4-((2-iodo-1-(2,2,2-trifluoroethyl)-1H-indol-4-yl)amino)piperidin-1-yl)propane-1,2-diol.

N-(1-{[(4R)-2,2-dimethyl-1,3-dioxolan-4-yl]methyl}piperidin-4-yl)-2-{3-[(4-methanesulfonyl-2-methoxyphenyl)amino]prop-1-yn-1-yl}-1-(2,2,2-trifluoroethyl)-1H-indol-4-amine, MS (ES³⁰, m/z): 649.3; and 4-[(3-{4-[(1-{[(4R)-2,2-dimethyl-1,3-dioxolan-4-yl]methyl}piperidin-4-yl)amino]-1-(2,2,2-trifluoroethyl)-1H-indol-2-yl}prop-2-yn-1-yl)amino]-3-methoxybenzene-1-sulfonamide, MS (ES³⁰, m/z): 650.3.

Example D154: Preparation of Compounds 782A and 783A

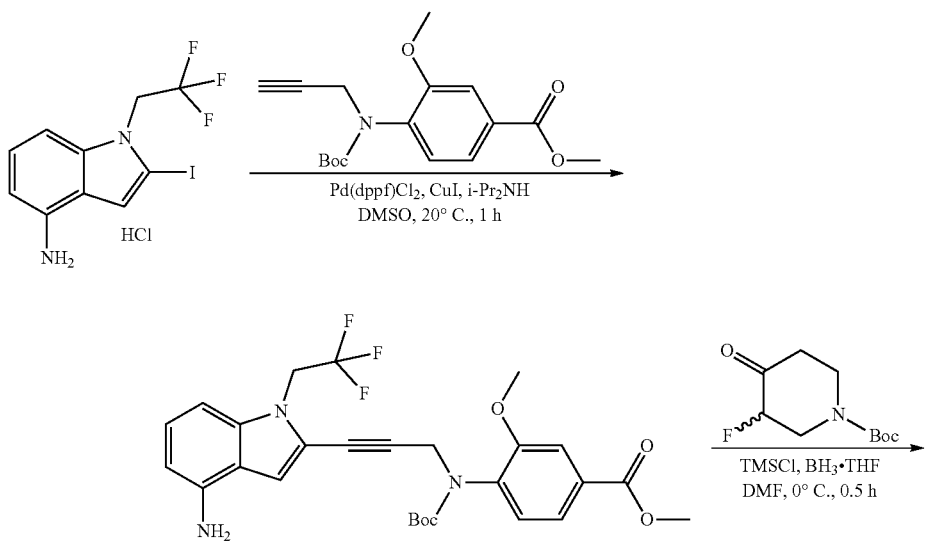

-continued
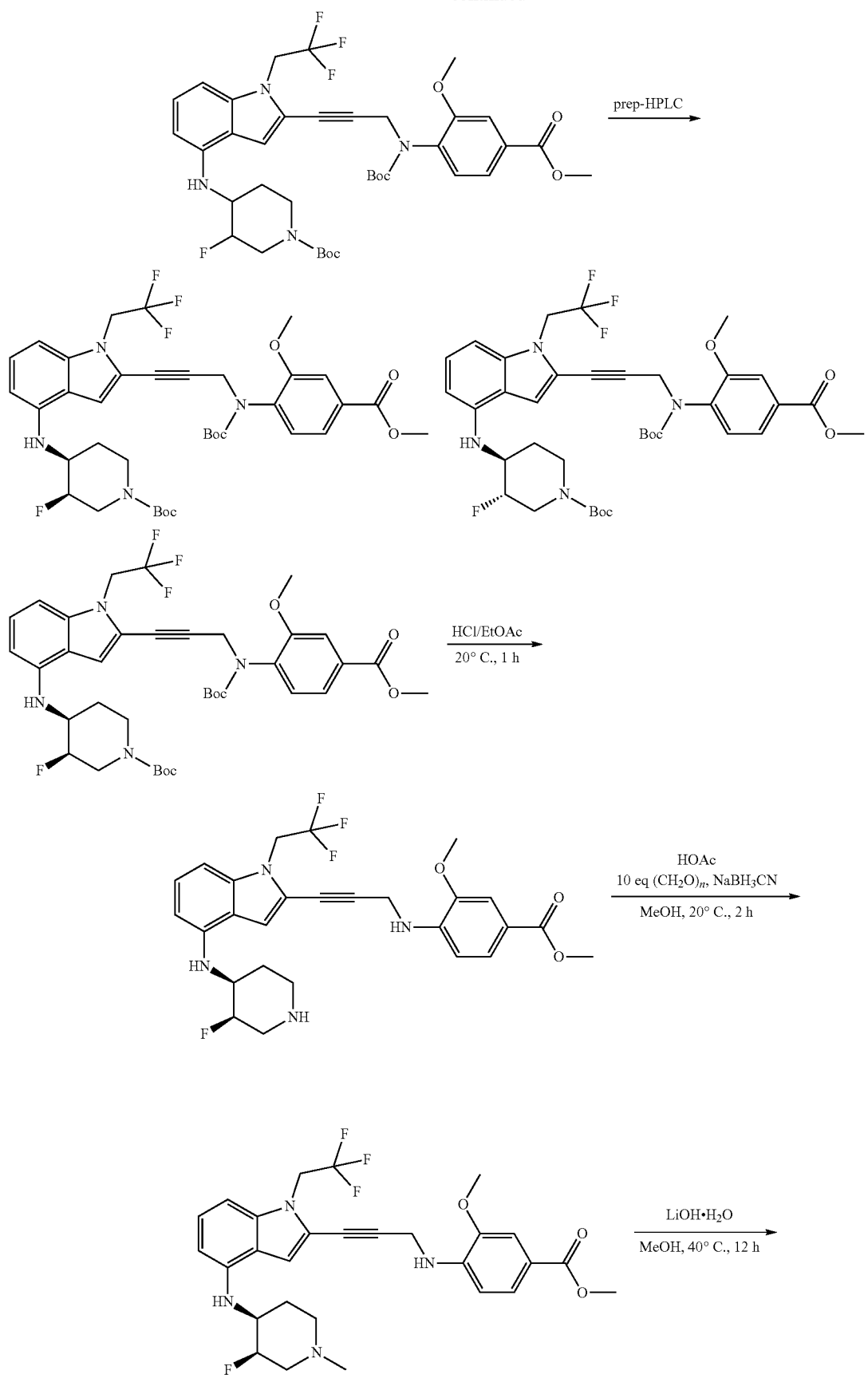

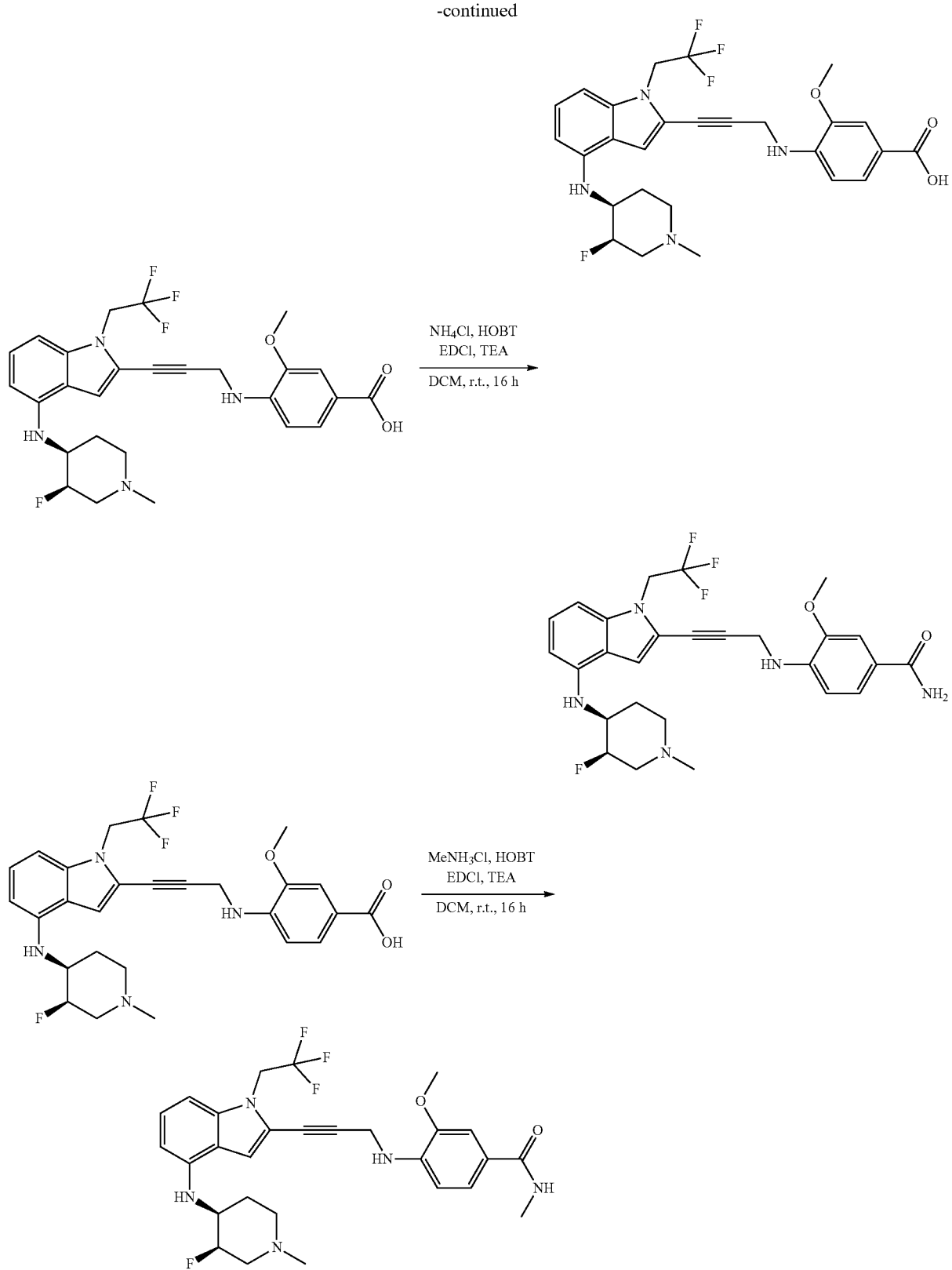
Synthesis of methyl 4-((3-(4-amino-1-(2,2,2-trifluoroethyl)-1H-indol-2-yl)prop-2-yn-1-yl)(tert-butoxycarbonyl)amino)-3-methoxybenzoate: To a solution of methyl 4-((tert-butoxycarbonyl)(prop-2-yn-1-yl)amino)-3-methoxybenzoate (6.9 g, 21.39 mmol, 1.2 eq.) in DMSO (50 mL) were added CuI (1.02 g, 5.35 mmol, 0.3 eq.), diisopropylamine (18.04 g, 178.25 mmol, 25.19 mL, 10 eq.), Pd(PPh$_3$)$_4$ (1.03 g, 891.26 µmol, 0.05 eq.), and 2-iodo-1-(2,2,2-trifluoroethyl)-1H-indol-4-amine hydrochloride (6.06 g, 17.83 mmol, 1 eq.) under N$_2$. The reaction mixture was stirred for 1 h at 20° C., after which time TLC analysis (PE:EtOAc=2:1, R$_f$=0.24) indicated that the reaction was complete. The reaction mixture was quenched with a saturated aqueous solution of EDTA (500 mL) at 25° C., stirred for 1 h, and then extracted with EtOAc (200 mL×3). The combined organic layers were dried over anhydrous sodium sulfate, filtered, and concentrated under reduced pressure. The residue was purified by column chromatography (SiO$_2$, PE:EtOAc=3:1 to 1:2, PE:EtOAc=1:1, R$_f$=0.24) to provide methyl 4-((3-(4-amino-1-(2,2,2-trifluoroethyl)-1H-indol-2-yl)prop-2-yn-1-yl)(tert-butoxycarbonyl)amino)-3-methoxybenzoate (10 g, 13.73 mmol, 77.05% yield) as a brown oil.

Synthesis of (rac)-tert-butyl (3R,4S)-4-((2-(3-((tert-butoxycarbonyl)(2-methoxy-4-(methoxycarbonyl)phenyl)amino)prop-1-yn-1-yl)-1-(2,2,2-trifluoroethyl)-1H-indol-4-yl)amino)-3-fluoropiperidine-1-carboxylate and (rac)-tert-butyl (3S,4S)-4-((2-(3-((tert-butoxycarbonyl)(2-methoxy-4-(methoxycarbonyl)phenyl)amino)prop-1-yn-1-yl)-1-(2,2,2-trifluoroethyl)-1H-indol-4-yl)amino)-3-fluoropiperidine-1-carboxylate: To a solution of tert-butyl 3-fluoro-4-oxopiperidine-1-carboxylate (16 g, 73.65 mmol, 4 eq.) and methyl 4-((3-(4-amino-1-(2,2,2-trifluoroethyl)-1H-indol-2-yl)prop-2-yn-1-yl)(tert-butoxycarbonyl)amino)-3-methoxybenzoate (9.79 g, 18.41 mmol, 1 eq.) in DMF (20 mL) was added TMSCl (6 g, 55.24 mmol, 7.01 mL, 3 eq.). The mixture was stirred at 0° C. for 0.5 h, where after BH$_3$·THF (1 M, 184.13 mL, 10 eq.) was added under N$_2$. The mixture was stirred at 0° C. for an additional 0.5 h, after which time LC-MS analysis indicated that the starting primary amine was completely consumed. The reaction mixture was adjusted to pH-8 with saturated aqueous Na$_2$CO$_3$, diluted with water (50 mL), and extracted with EtOAc 600 mL (150 mL×4). The combined organic layers were washed with brine (100 mL), dried over anhydrous sodium sulfate, filtered, and concentrated under reduced pressure. The residue was purified by prep-HPLC to provide (rac)-tert-butyl (3S,4S)-4-((2-(3-((tert-butoxycarbonyl)(2-methoxy-4-(methoxycarbonyl)phenyl)amino)prop-1-yn-1-yl)-1-(2,2,2-trifluoroethyl)-1H-indol-4-yl)amino)-3-fluoropiperidine-1-carboxylate (5.7 g, 7.78 mmol, 42.25% yield) as a yellow solid. The trans diastereomer was also isolated in 35% yield (4.7 g).

Synthesis of (rac)-methyl 4-((3-(4-(((3R,4S)-3-fluoropiperidin-4-yl)amino)-1-(2,2,2-trifluoroethyl)-1H-indol-2-yl)prop-2-yn-1-yl)amino)-3-methoxybenzoate: To a solution of (rac)-tert-butyl (3S,4S)-4-((2-(3-((tert-butoxycarbonyl)(2-methoxy-4-(methoxycarbonyl)phenyl)amino)prop-1-yn-1-yl)-1-(2,2,2-trifluoroethyl)-1H-indol-4-yl)amino)-3-fluoropiperidine-1-carboxylate (5 g, 6.82 mmol, 1 eq.) was added 4N HCl/EtOAc (34.12 mmol, 20 mL, 5 eq.). The mixture was stirred at 20° C. for 1 h, after which time TLC analysis (DCM:MeOH=10:1) indicated that the protected starting material was completely consumed, and one new spot had appeared. The reaction mixture was adjusted to pH-8 with saturated aqueous Na$_2$CO$_3$, diluted with water (50 mL), and extracted with EtOAc (50 mL×4). The combined organic layers were washed with NaCl (10 mL), dried over anhydrous sodium sulfate, filtered, and concentrated under reduced pressure to provide crude (rac)-methyl 4-((3-(4-(((3R,4S)-3-fluoropiperidin-4-yl)amino)-1-(2,2,2-trifluoroethyl)-1H-indol-2-yl)prop-2-yn-1-yl)amino)-3-methoxybenzoate (4.1 g, crude) as a yellow solid.

Synthesis of (rac)-methyl 4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-3-methoxybenzoate: A mixture of (rac)-methyl 4-((3-(4-(((3R,4S)-3-fluoropiperidin-4-yl)amino)-1-(2,2,2-trifluoroethyl)-1H-indol-2-yl)prop-2-yn-1-yl)amino)-3-methoxybenzoate (0.6 g, 1.13 mmol, 1 eq.), paraformaldehyde (338.30 mg, 11.27 mmol, 310.37 µL, 10 eq.), NaBH$_3$CN (212.41 mg, 3.38 mmol, 3 eq.), and AcOH (67.66 mg, 1.13 mmol, 64.44 µL, 1 eq.) in MeOH (20 mL) was degassed and purged with N$_2$. The mixture was stirred at 20° C. for 2 h under N$_2$ atmosphere, after which time TLC analysis (EtOAc:TEA=10:1, R$_f$=0.65) indicated that one new spot had appeared. The reaction mixture was quenched with saturated aqueous NaHCO$_3$ (30 mL), and then extracted with EtOAc (40 mL×3). The combined organic layers were washed with brine (25 mL×3), dried over anhydrous sodium sulfate, filtered, and concentrated under reduced pressure. The residue was purified by prep-TLC (SiO$_2$, EtOAc:TEA=20:1) to provide (rac)-methyl 4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-3-methoxybenzoate (0.4 g, 658.67 µmol, 58.46% yield) as a yellow solid.

Synthesis of (rac)-4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-3-methoxybenzoic acid: A mixture of (rac)-methyl 4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-3-methoxybenzoate (0.4 g, 731.86 µmol, 1 eq.) in LiOH·H$_2$O (10 mL, 10 M) and MeOH (10 mL) was degassed and purged with N$_2$. The mixture was stirred at 40° C. for 12 h under N$_2$ atmosphere, after which time TLC analysis (EtOAc:TEA=10:1, R$_f$=0) indicated that one new spot had appeared. The reaction mixture was extracted with EtOAc (40 mL×3). The combined organic layers were washed with brine (30 mL×3), dried over anhydrous sodium sulfate, filtered, and concentrated under reduced pressure. The residue was purified by prep-TLC (SiO$_2$, EtOAc:TEA=10:1) to provide (rac)-4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-3-methoxybenzoic acid (0.2 g, 338.01 µmol, 46.19% yield) as a yellow solid.

Synthesis of (rac)-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzamide: A mixture of (rac)-4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-3-methoxybenzoic acid (0.12 g, 225.34 µmol, 1 eq.), NH$_4$Cl (24.11 mg, 450.68 µmol, 2 eq.), HOBt (45.67 mg, 338.01 µmol, 1.5 eq.), EDCI (64.80 mg, 338.01 µmol, 1.5 eq.), and TEA (91.21 mg, 901.36 µmol, 125.46 µL, 4 eq.) in DCM (5 mL) was degassed and purged with N$_2$. The mixture was stirred at 20° C. for 16 h under N$_2$ atmosphere, after which time TLC analysis (EtOAc:TEA=10:1, R$_f$=0.1) indicated that one new major new spot had appeared. The reaction mixture was diluted with EtOAc (15 mL) and extracted with EtOAc (20 mL×3). The combined organic layers were washed with brine (20 mL×3), dried over anhydrous sodium sulfate, filtered, and concentrated under reduced pressure. The residue was purified by prep-HPLC to provide (rac)-4-{[3-(4-{[(3R,4S)-3-fluoro-1-methylpiperidin-4-yl]amino}-1-(2,2,2-trifluoroethyl)-1H- indol-2-yl)prop-2-yn-1-yl]amino}-3-methoxybenzamide as a yellow solid (24.5 mg, 20.5% yield). MS (ES³⁰, m/z): 532.2.

Synthesis of rac-4-{[3-(4-{[(3R,4S)-3-fluoro-1-methylpiperidin-4-yl]amino}-1-(2,2,2-trifluoroethyl)-1H-indol-2-yl) prop-2-yn-1-yl]amino}-3-methoxy-N-methylbenzamide: A mixture of (rac)-4-((3-(4-(((3R,4S)-3-fluoro-1-methylpiperidin-4-yl)amino)-1-(2,2,2-trifluoroethyl)-1H-indol-2-yl) prop-2-yn-1-yl)amino)-3-methoxybenzoic acid (0.12 g, 225.34 μmol, 1 eq.), methylamine hydrochloride (30.43 mg, 450.68 μmol, 2 eq.), HOBt (45.67 mg, 338.01 μmol, 1.5 eq.), EDCI (64.80 mg, 338.01 μmol, 1.5 eq.), and TEA (91.21 mg, 901.36 μmol, 125.46 μL, 4 eq.) in DCM (5 mL) was degassed and purged with N₂. The mixture was stirred at 20° C. for 16 h under N₂ atmosphere, after which time TLC analysis (EtOAc:TEA=10:1, R$_f$=0.2) indicated that one new major spot had formed. The reaction mixture was diluted with EtOAc (15 mL) and extracted with EtOAc (20 mL×3). The combined organic layers were washed with brine (20 mL×3), dried over anhydrous sodium sulfate, filtered, and concentrated under reduced pressure. The residue was purified by prep-TLC (SiO₂, EtOAc:TEA=10:1), and further purified by prep-HPLC to provide (rac)-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide as a yellow solid (22.1 mg, 18.0% yield) MS (ES³⁰, m/z): 546.3.

Example D155: Preparation of Compounds 788A and 789A

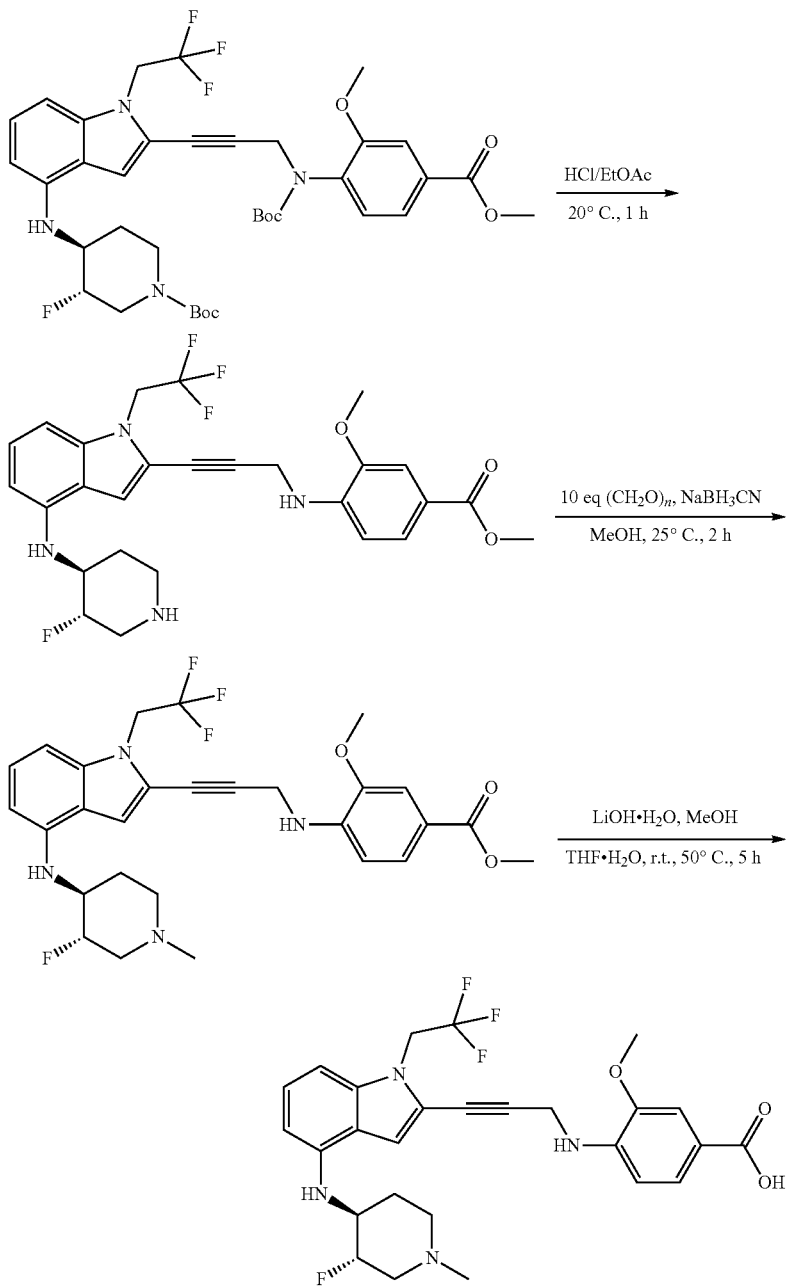

4-{[3-(4-{[(3R,4R)-3-Fluoro-1-methylpiperidin-4-yl]amino}-1-(2,2,2-trifluoroethyl)-1H-indol-2-yl)prop-2-yn-1-yl]amino}-3-methoxybenzoic acid was prepared via an procedure analogous to the synthesis of (rac)-4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-3-methoxybenzoic acid according to steps 3-5 of EXAMPLE D154, using (rac)-methyl 4-((3-(4-(((3S,4S)-3-fluoropiperidin-4-yl)amino)-1-(2,2,2-trifluoroethyl)-1H-indol-2-yl)prop-2-yn-1-yl)amino)-3-methoxybenzoate in place of (rac)-methyl 4-((3-(4-(((3R,4S)-3-fluoropiperidin-4-yl)amino)-1-(2,2,2-trifluoroethyl)-1H-indol-2-yl)prop-2-yn-1-yl)amino)-3-methoxybenzoate. The racemate product was resolved into its constituent enantiomers via chiral SFC.

4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzoic acid (32 mg, 60.09 μmol, 41.05% yield) was obtained as white solid (MS (ES$^{30}$, m/z): 533.1). 4-{[3-(4-{[(3S,4S)-3-fluoro-1-methylpiperidin-4-yl]amino}-1-(2,2,2-trifluoroethyl)-1H-indol-2-yl)prop-2-yn-1-yl]amino}-3-methoxybenzoic acid (26 mg, 48.82 μmol, 33.36% yield) was obtained as a white solid (MS (ES$^{30}$, m/z): 533.1).

Example D156: Synthesis of Compounds 885A, 886A, and 887A

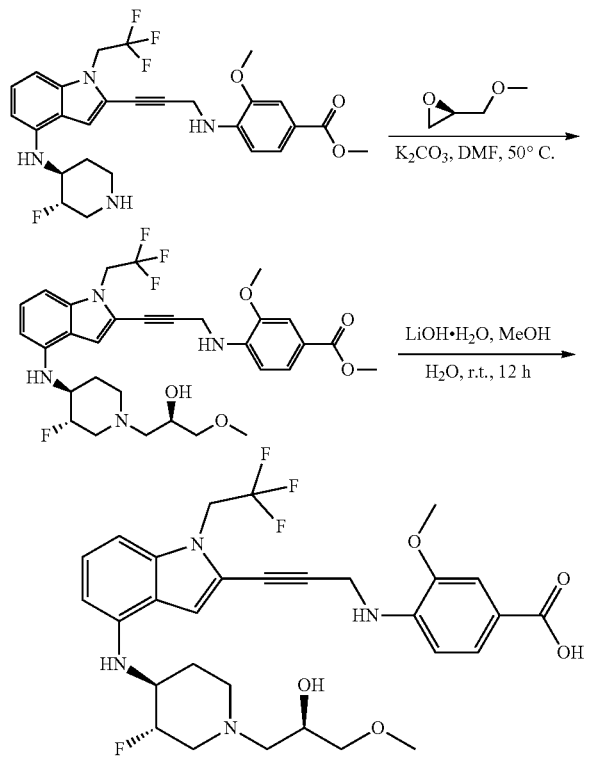

Synthesis of Compound methyl 4-((3-(4-(((3 SR,4 SR)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoate: To a solution of (rac)-methyl 4-((3-(4-(((3S,4S)-3-fluoropiperidin-4-yl)amino)-1-(2,2,2-trifluoroethyl)-1H-indol-2-yl)prop-2-yn-1-yl)amino)-3-methoxybenzoate (500 mg, 938.92 μmol, 1 eq.) and (R)-glycidyl methyl ether (413.62 mg, 4.69 mmol, 417.80 μL, 5 eq.) in DMF (10 mL) was added K$_2$CO$_3$ (389.29 mg, 2.82 mmol, 3 eq.). The mixture was stirred at 50° C. for 12 h, after which time TLC analysis (PE:EtOAc=0:1) indicated that the reaction was complete. The reaction mixture was quenched with water (60 mL) and extracted with EtOAc (20 mL×3). The combined organic layers were washed with brine (30 mL), dried over anhydrous sodium sulfate, filtered, and concentrated under reduced pressure. The residue was purified by prep-TLC (SiO$_2$, PE:EtOAc=0:1) to provide methyl 4-((3-(4-(((3 SR,4 SR)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoate (240 mg, 386.70 μmol, 41.19% yield) as a yellow solid.

Synthesis of final products: To a solution of methyl 4-((3-(4-(((3 SR,4 SR)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoate (200 mg, 322.25 μmol, 1 eq.) in THF (2 mL), water (1 mL), and MeOH (1 mL) was added LiOH-water (135.23 mg, 3.22 mmol, 10 eq.). The mixture was stirred at 50° C. for 12 h, after which time TLC (DCM:MeOH=10:1, R$_f$=0.19) indicated that the reaction was complete. The reaction mixture was quenched with water (60 mL) at 25° C., and then extracted with EtOAc (20 mL×3). The combined organic layers were washed with brine (30 mL), dried over anhydrous sodium sulfate, filtered, and concentrated under reduced pressure. The residue was purified by prep-TLC (SiO$_2$, DCM:MeOH=10:1, R$_f$=0.19), and further purified by prep-HPLC to provide diastereomeric mixture 4-((3-(4-(((3 SR,4 SR)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid (160 mg, 255.85 μmol, 79.39% yield) as a white solid. MS (ES$^{30}$, m/z): 607.3.

The diastereomers were then separated via prep-HPLC to provide 4-((3-(4-(((3S,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid and 4-((3-(4-(((3R,4R)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid.

Example D157: Preparation of Compounds 786A and 793A

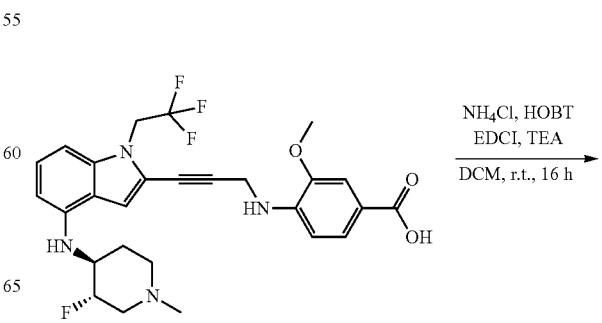

1257

-continued

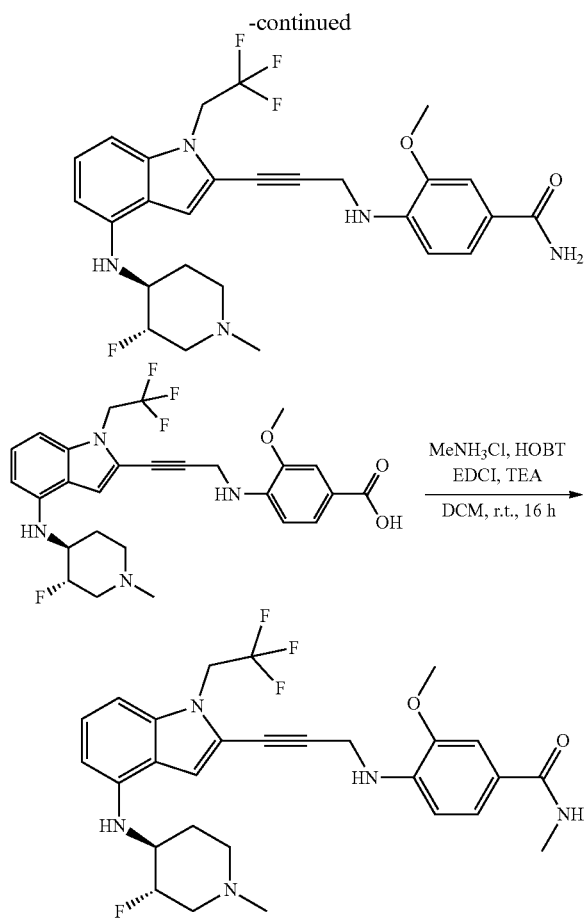

Preparation of rac-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzamide: rac-4-

1258

{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzamide was prepared via a procedure analogous to EXAMPLE D154, using 4-{[3-(4-{[(3S,4S)-3-fluoro-1-methylpiperidin-4-yl]amino}-1-(2,2,2-trifluoroethyl)-1H-indol-2-yl)prop-2-yn-1-yl]amino}-3-methoxybenzoic acid (0.08 g, 150.23 µmol, 1 eq.) in place of (rac)-4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-3-methoxybenzoic acid. The crude residue was purified by prep-HPLC (column: C18 100×30 5 µm; mobile phase: [water (0.225% FA)-ACN]; B %: 1%-30%, 15 min) to provide (rac)-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzamide as a white solid (0.03 g, 56.44 µmol, 37.57% yield). MS (ES$^{30}$, m/z): 532.2.

Synthesis of (rac)-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide: (rac)-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide was prepared via procedure analogous to EXAMPLE D154, using 4-{[3-(4-{[(3S,4S)-3-fluoro-1-methylpiperidin-4-yl]amino}-1-(2,2,2-trifluoroethyl)-1H-indol-2-yl)prop-2-yn-1-yl]amino}-3-methoxybenzoic acid (80 mg, 150.23 µmol, 1 eq.) in place of (rac)-4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-3-methoxybenzoic acid. The crude residue was purified by prep-HPLC (column: C18 100×30 5 µm; mobile phase: [water (0.225% FA)-ACN]; B %: 1%-30%, 15 min) to provide (rac)-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide as a white solid (0.03 g, 54.99 µmol, 36.60% yield). MS (ES$^{30}$, m/z): 546.2.

Example D158: Preparation of Compound 1054A

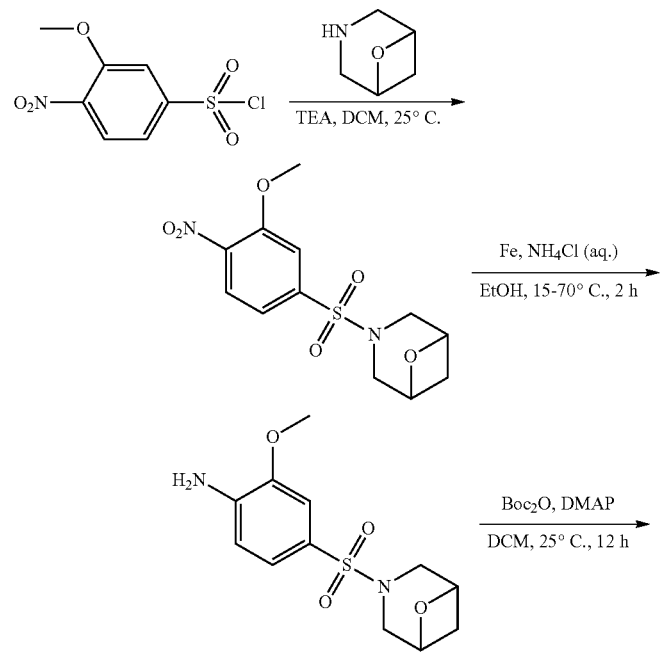

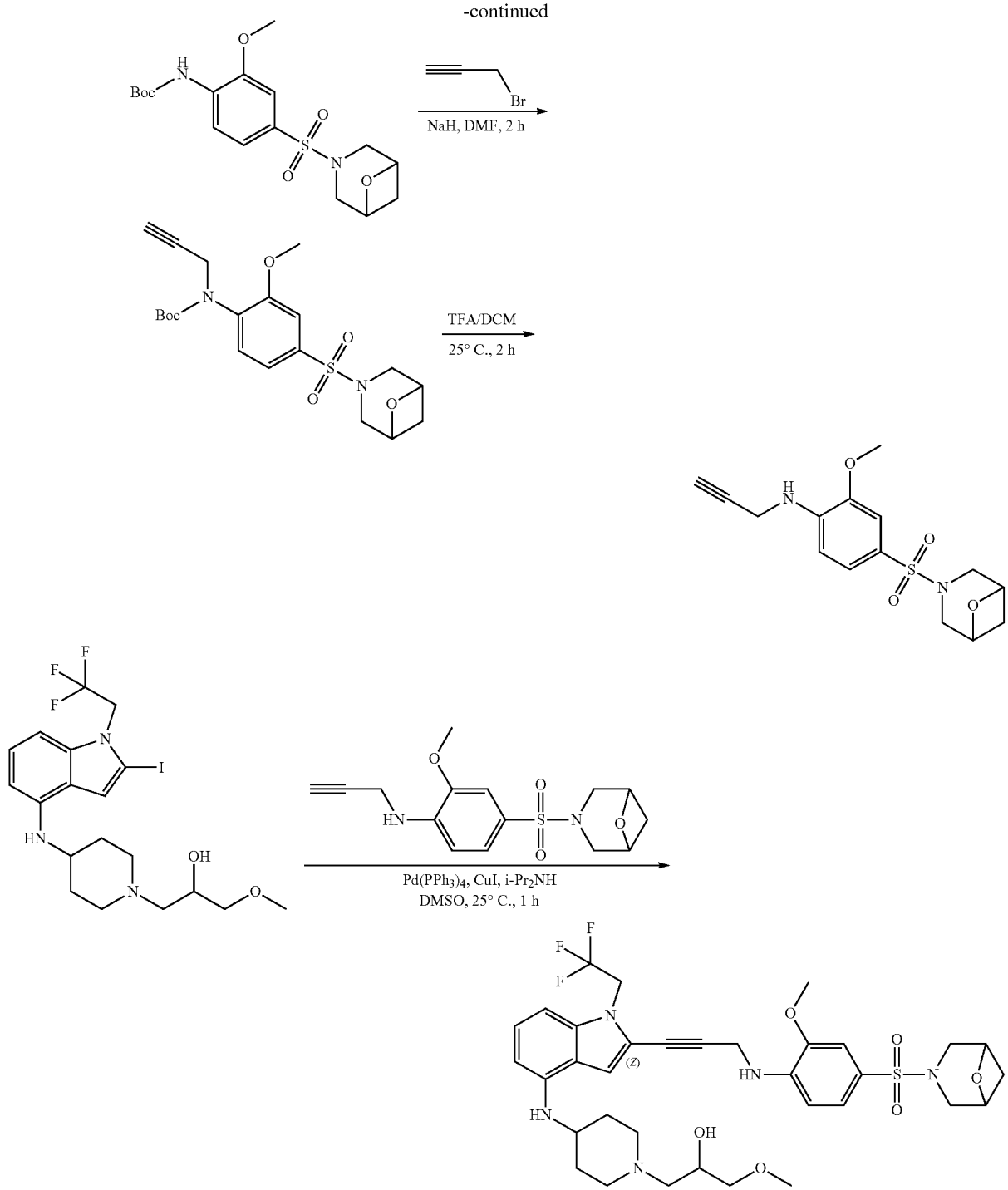

Synthesis of 3-((3-methoxy-4-nitrophenyl)sulfonyl)-6-oxa-3-azabicyclo[3.1.1]heptane: To a solution of 6-oxa-3-azabicyclo[3.1.1]heptane (486.28 mg, 1.79 mmol, 1.1 eq.) in DCM (10 mL) was added TEA (329.73 mg, 3.26 mmol, 453.56 μL, 2 eq.) and 3-methoxy-4-nitrobenzenesulfonyl chloride (410 mg, 1.63 mmol, 1 eq.). The resulting mixture was stirred at 25° C. for 2 h, after which time TLC (PE:EtOAc=3:1, $R_f$=0.19) indicated that the starting sulfonyl chloride was completely consumed, and one new spot was observed. The reaction mixture was poured into water (50 mL) and filtered with diatomite. The aqueous phase was extracted with EtOAc (10 mL×3), and the combined organic layers were dried over anhydrous sodium sulfate, filtered, and concentrated in vacuo. The resulting residue was purified by column chromatography (SiO$_2$, PE:EtOAc=4:1 to 1:1) to afford 3-((3-methoxy-4-nitrophenyl)sulfonyl)-6-oxa-3-azabicyclo[3.1.1]heptane (320 mg, 1.02 mmol, 62.49% yield) as a light yellow solid.

Synthesis of 4-((6-oxa-3-azabicyclo[3.1.1]heptan-3-yl)sulfonyl)-2-methoxyaniline: To a solution of 3-((3-methoxy-4-nitrophenyl)sulfonyl)-6-oxa-3-azabicyclo[3.1.1]heptane (310 mg, 986.28 μmol, 1 eq.) in EtOH (10 mL) and water (2 mL) was added a saturated aqueous NH₄Cl solution (263.79 mg, 4.93 mmol, 172.41 µL, 5 eq.) at 25° C. Fe (275.39 mg, 4.93 mmol, 5 eq.) was then added, and the mixture was stirred at 70° C. for 2 h. TLC analysis (PE:EtOAc=1:1, $R_f$=0.20) indicated that the starting nitro compound was completely consumed, and one new spot was detected. The mixture was concentrated, the resulting residue was extracted with EtOAc (60 mL), and the EtOAc solution was concentrated to afford 4-((6-oxa-3-azabicyclo[3.1.1]heptan-3-yl)sulfonyl)-2-methoxyaniline (260 mg, 914.43 µmol, 92.72% yield) as a black brown solid.

Synthesis of tert-butyl (4-((6-oxa-3-azabicyclo[3.1.1]heptan-3-yl)sulfonyl)-2-methoxyphenyl)carbamate: To a solution of 4-((6-oxa-3-azabicyclo[3.1.1]heptan-3-yl)sulfonyl)-2-methoxyaniline (210 mg, 738.58 µmol, 1 eq.) in DCM (10 mL) were added DMAP (90.23 mg, 738.58 µmol, 1 eq.) and Boc₂O (322.38 mg, 1.48 mmol, 339.35 µL, 2 eq.). The mixture was stirred at 25° C. for 12 h, after which time TLC analysis (PE:EtOAc=0.20, $R_f$=0.20) indicated that the starting primary amine was consumed completely, and one main peak with the desired product mass was detected via LC-MS. The reaction mixture was then poured into water (40 mL) and filtered with diatomite. The aqueous phase was extracted with EtOAc (6 mL×3), and the combined organic layers were dried over anhydrous sodium sulfate, filtered, and concentrated in vacuo. The residue was purified by prep-TLC (PE:EtOAc=5:1, $R_f$=0.20) to afford tert-butyl (4-((6-oxa-3-azabicyclo[3.1.1]heptan-3-yl)sulfonyl)-2-methoxyphenyl)carbamate (130 mg, 338.15 µmol, 45.78% yield) as a yellow oil.

Synthesis of tert-butyl (4-((6-oxa-3-azabicyclo[3.1.1]heptan-3-yl)sulfonyl)-2-methoxyphenyl)(prop-2-yn-1-yl)carbamate: To a solution of tert-butyl (4-((6-oxa-3-azabicyclo[3.1.1]heptan-3-yl)sulfonyl)-2-methoxyphenyl)carbamate (130 mg, 338.15 µmol, 1 eq.) in DMF (4 mL) was added NaH (27.05 mg, 676.30 µmol, 60% w/w, 2 eq.). The mixture was stirred at 0° C. for 30 min, and propargyl bromide was then added (48.27 mg, 405.78 µmol, 34.98 µL, 1.2 eq.). The mixture was stirred at 25° C. for 1.5 h, after which time TLC analysis (PE:EtOAc=5:1, $R_f$=0.26) indicated that the starting secondary amine was consumed completely, and one main peak with the desired product mass was detected via LC-MS. The reaction mixture was poured into water (30 mL) and filtered with diatomite. The aqueous phase was extracted with EtOAc (6 mL×3). The combined organic layers were dried over anhydrous sodium sulfate, filtered, and concentrated in vacuo. The residue was purified by prep-TLC (PE:EtOAc=5:1, $R_f$=0.26) to afford tert-butyl (4-((6-oxa-3-azabicyclo[3.1.1]heptan-3-yl)sulfonyl)-2-methoxyphenyl)(prop-2-yn-1-yl)carbamate (100 mg, 236.69 µmol, 70% yield) as a yellow oil.

Synthesis of 4-((6-oxa-3-azabicyclo[3.1.1]heptan-3-yl)sulfonyl)-2-methoxy-N-(prop-2-yn-1-yl)aniline: To a solution of tert-butyl (4-((6-oxa-3-azabicyclo[3.1.1]heptan-3-yl)sulfonyl)-2-methoxyphenyl)(prop-2-yn-1-yl)carbamate (100 mg, 236.69 µmol, 1 eq.) in DCM (6 mL) was added TFA (2 mL), then the mixture was stirred at 25° C. for 1 h. TLC analysis (PE:EtOAc=1:1, $R_f$=0.22) indicated that the starting Boc-amine was consumed completely. The residue was poured into a saturated aqueous solution of NaHCO₃ (30 mL) and filtered with diatomite. The aqueous phase was extracted with EtOAc (6 mL×3), and the combined organic layers were dried over anhydrous sodium sulfate, filtered, and concentrated in vacuo. The black-brown solid residue containing crude 4-((6-oxa-3-azabicyclo[3.1.1]heptan-3-yl)sulfonyl)-2-methoxy-N-(prop-2-yn-1-yl)aniline (50 mg) was used in next step directly.

Synthesis of final product: To a solution of 4-((6-oxa-3-azabicyclo[3.1.1]heptan-3-yl)sulfonyl)-2-methoxy-N-(prop-2-yn-1-yl)aniline (31.52 mg, 97.79 µmol, 1 eq.) in DMSO (4 mL) were added diisopropylamine (98.95 mg, 977.86 µmol, 138.20 µL, 10 eq.) and CuI (18.62 mg, 97.79 µmol, 1 eq.). The mixture was then degassed with N₂, and 1-(4-((2-iodo-1-(2,2,2-trifluoroethyl)-1H-indol-4-yl)amino)piperidin-1-yl)-3-methoxypropan-2-ol (50 mg, 97.79 µmol, 1 eq.) and Pd(PPh₃)₄ (22.60 mg, 19.56 µmol, 0.2 eq.) were added. The mixture was stirred at 25° C. for 2 h, after which time TLC analysis (PE:EtOAc=1:1, $R_f$=0.21) indicated that ~10% of the iodoindole remained, and one main peak with the desired product mass was detected via LC-MS. The reaction mixture was diluted with EtOAc (5 mL), poured into a saturated EDTA solution (30 mL), and stirred for 1 h. The mixture was then extracted with EtOAc (15 mL×2), and The combined organic layers were washed with brine (10 mL) and concentrated under reduced pressure. The resulting residue was purified by prep-TLC (PE:EtOAc=1:1, $R_f$=0.21) to afford 1-(4-((2-(3-((4-((6-oxa-3-azabicyclo[3.1.1]heptan-3-yl)sulfonyl)-2-methoxyphenyl)amino)prop-1-yn-1-yl)-1-(2,2,2-trifluoroethyl)-1H-indol-4-yl)amino)piperidin-1-yl)-3-methoxypropan-2-ol (4.5 mg, 6.22 µmol, 6.36% yield) as a yellow solid. MS (ES³⁰, m/z): 706.3.

Example D159: Synthesis of 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzene-1-sulfonamide (Compound 574A)

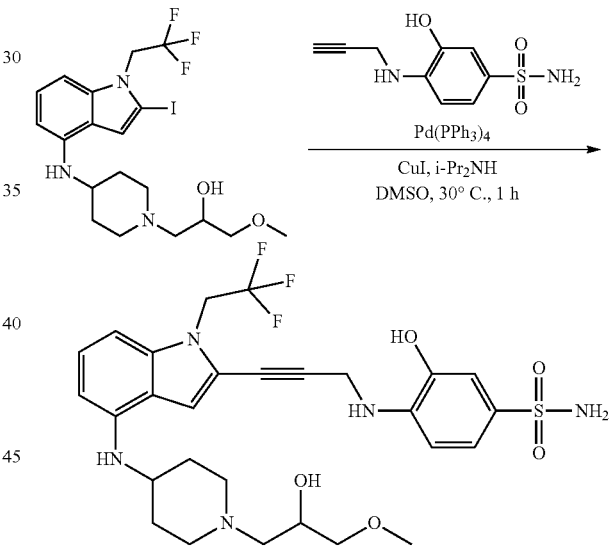

To a mixture 3-hydroxy-4-(prop-2-ynylamino)benzenesulfonamide (41.48 mg, 146.68 µmol, 1.5 eq.) and 1-(4-((2-iodo-1-(2,2,2-trifluoroethyl)-1H-indol-4-yl)amino)piperidin-1-yl)-3-methoxypropan-2-ol (0.05 g, 97.79 µmol, 1 eq.) in DMSO (2 mL) were added CuI (18.62 mg, 97.79 µmol, 1 eq.), Pd(PPh₃)₄ (11.30 mg, 9.78 µmol, 0.10 eq.), and N-isopropylpropan-2-amine (9.89 mg, 97.79 µmol, 13.82 µL, 1 eq.). The mixture was stirred at 30° C. for 1 h under N₂. TLC analysis (PE:EtOAc=0:1, $R_f$=0.23) showed that the reaction was complete. The reaction mixture was quenched by adding a saturated aqueous solution of EDTA (30 mL) and EtOAc (10 mL) and stirring the mixture at 25° C. for 1 h. The aqueous phase was extracted with EtOAc (20 mL×3). The combined organic layers were washed with brine (30 mL), dried over anhydrous sodium sulfate, filtered, and concentrated under reduced pressure to give a residue. The residue was purified by prep-TLC (SiO₂, PE:EtOAc=0:1, $R_f$=0.24) to afford the desired product. MS (ES³⁰, m/z): 624.2.

Example D160: Synthesis of N-(3-(4-((1-(2-hydroxy-3-methoxypropyl)piperidin-4-yl)amino)-1-(2,2,2-trifluoroethyl)-1H-indol-2-yl)prop-2-yn-1-yl)-N-(2-hydroxy-4-(N-propionylsulfamoyl)phenyl)propionamide (Compound 636A)

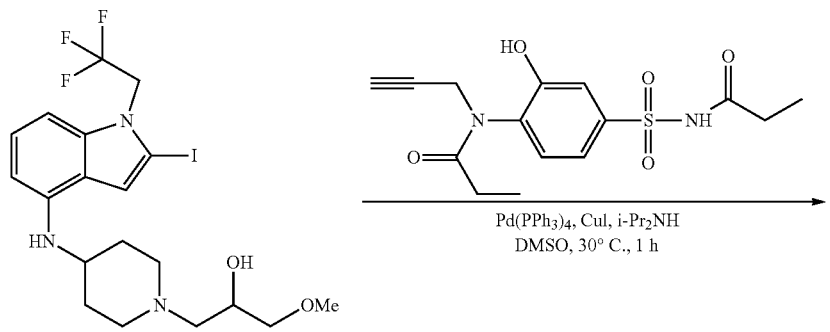

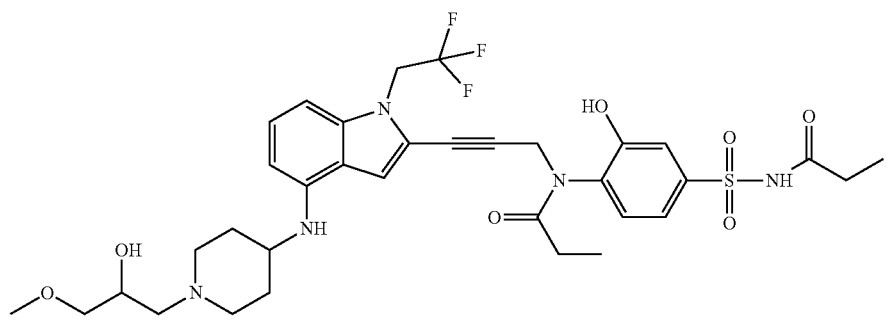

To a mixture N-(2-hydroxy-4-(N-propionylsulfamoyl)phenyl)-N-(prop-2-yn-1-yl)propionamide (57.86 mg, 117.34 μmol, 1.2 eq.) and 1-(4-((2-iodo-1-(2,2,2-trifluoroethyl)-1H-indol-4-yl)amino)piperidin-1-yl)-3-methoxypropan-2-ol (0.05 g, 97.79 μmol, 1 eq.) in DMSO (2 mL) were added CuI (18.62 mg, 97.79 μmol, 1 eq.), Pd(PPh₃)₄ (11.30 mg, 9.78 μmol, 0.10 eq.), and N-isopropylpropan-2-amine (9.89 mg, 97.79 μmol, 13.82 μL, 1 eq.). The mixture was stirred at 30° C. for 1 h under N₂. LC-MS analysis showed that the reaction was complete. The reaction mixture was quenched by adding a saturated aqueous EDTA solution (30 mL) and EtOAc (10 mL) and stirring the mixture at 25° C. for 1 h. The aqueous phase was extracted with EtOAc (20 mL×3). The combined organic layers were washed with brine (30 mL), dried over anhydrous sodium sulfate, filtered, and concentrated under reduced pressure to give a residue. The residue was purified by prep-TLC (SiO₂, PE:EtOAc=0:1, $R_f$=0.24) and prep-HPLC to afford the desired product (12.6 mg, 15.71 μmol, 16.07% yield) as a yellow solid. MS (ES³⁰, m/z): 722.3.

Example D161: General Procedure for Preparation of Compounds 536A, 540A, and 729A

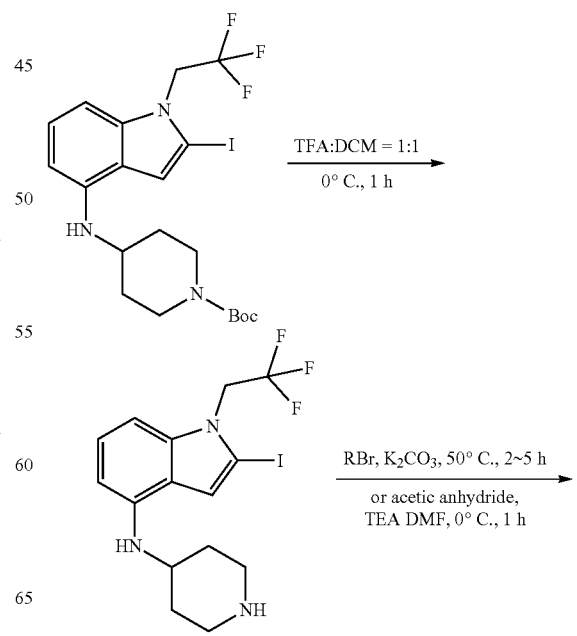

-continued

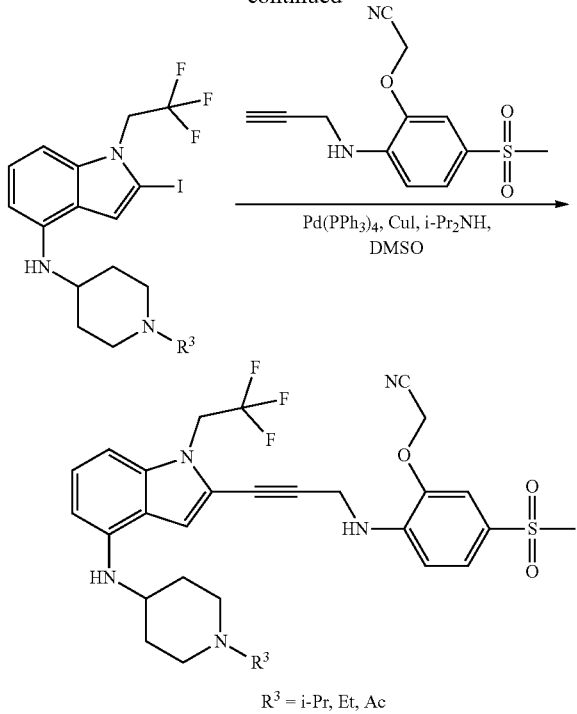

R³ = i-Pr, Et, Ac

Synthesis of 2-iodo-N-(piperidin-4-yl)-1-(2,2,2-trifluoroethyl)-1H-indol-4-amine: To a solution of tert-butyl 4-((2-iodo-1-(2,2,2-trifluoroethyl)-1H-indol-4-yl)amino)piperidine-1-carboxylate (6 g, 10.89 mmol, 1 eq.) in DCM (50 mL) was added TFA (50 mL). The mixture was stirred at 0° C. for 1 h, after which time LC-MS and TLC analysis (PE:EtOAc=5:1, $R_f$=0.1) indicated that reaction was complete. The reaction mixture was concentrated in vacuo, and the residue was poured into water (300 mL) and neutralized by adding saturated aqueous $Na_2CO_3$ (100 mL). The aqueous phase was extracted with EtOAc (200 mL×3). The combined organic layers were washed with brine (100 mL), dried over anhydrous sodium sulfate, filtered, and concentrated in vacuo. The residue was stirred in PE (20 mL) at 25° C. for 1 h and filtered to afford 2-iodo-N-(piperidin-4-yl)-1-(2,2,2-trifluoroethyl)-1H-indol-4-amine (15 g, 31.90 mmol, 97.62% yield) as light yellow solid.

Synthesis of N-(1-ethylpiperidin-4-yl)-2-iodo-1-(2,2,2-trifluoroethyl)-1H-indol-4-amine and 2-iodo-N-(1-isopropylpiperidin-4-yl)-1-(2,2,2-trifluoroethyl)-1H-indol-4-amine: To a mixture of 2-iodo-N-(piperidin-4-yl)-1-(2,2,2-trifluoroethyl)-1H-indol-4-amine (100 mg, 212.66 µmol, 1 eq.) in DMF (2 mL) were added isopropyl bromide or ethyl bromide (45 eq.) and $K_2CO_3$ (146.95 mg, 1.06 mmol, 5 eq.). The resulting mixture was stirred at 50° C. for 2~5 h under $N_2$. The mixture was poured into water (30 mL) and then extracted with EtOAc (30 mL×3). The combined organic layers were washed with brine (30 mL×3), dried over anhydrous sodium sulfate, filtered, and concentrated under reduced pressure to give a residue that was purified by prep-TLC to afford desired compounds N-(1-ethylpiperidin-4-yl)-2-iodo-1-(2,2,2-trifluoroethyl)-1H-indol-4-amine or 2-iodo-N-(1-isopropylpiperidin-4-yl)-1-(2,2,2-trifluoroethyl)-1H-indol-4-amine as yellow solids.

Synthesis of 1-(4-((2-iodo-1-(2,2,2-trifluoroethyl)-1H-indol-4-yl)amino)piperidin-1-yl)ethan-1-one: To a solution of 2-iodo-N-(piperidin-4-yl)-1-(2,2,2-trifluoroethyl)-1H-indol-4-amine (0.2 g, 425.32 µmol, 1 eq.) and TEA (129.11 mg, 1.28 mmol, 177.60 µL, 3 eq.) in DCM (2 mL) was added acetic anhydride (52.10 mg, 510.38 µmol, 47.80 µL, 1.2 eq.). The resulting mixture was stirred 0° C. for 2 h and then poured into water (10 mL). The mixture was extracted with DCM (10 mL×3). The combined organic layers were washed with brine (10 mL×3), dried over anhydrous sodium sulfate, filtered, and concentrated under reduced pressure. The resulting residue was washed with PE (10 mL×3) to afford desired compound 1-(4-((2-iodo-1-(2,2,2-trifluoroethyl)-1H-indol-4-yl)amino)piperidin-1-yl)ethan-1-one (0.15 g, 290.17 µmol, 68.22% yield) as a yellow solid.

Synthesis of final products: To a mixture of 2-(5-(methylsulfonyl)-2-(prop-2-yn-1-ylamino)phenoxy)acetonitrile (prepared according to EXAMPLE A4) (1-2 eq.) in DMSO (2 mL) was added i-$Pr_2NH$ (10~30 eq.). CuI (1~2 eq.), $R^3$-substituted iodoindole (1 eq.), and $Pd(PPh_3)_4$ (0.20~0.50 eq.) were then added to the mixture. The mixture was stirred at 20-40° C. for 1~3 h under $N_2$, and the progress of the reaction was monitored by LC-MS or TLC. The mixture was poured into a saturated EDTA solution (15 mL) and stirred for 1 h. The aqueous phase was extracted with EtOAc (20 mL×3), and the combined organic layers were washed with brine (20 mL×3), dried over anhydrous sodium sulfate, filtered, and concentrated in vacuo. The residue was purified by preparative TLC, preparative HPLC, or preparative TLC followed by preparative HPLC to afford the desired compounds.

2-(5-methanesulfonyl-2-{[3-(4-{[1-(propan-2-yl)piperidin-4-yl]amino}-1-(2,2,2-trifluoroethyl)-1H-indol-2-yl)prop-2-yn-1-yl]amino}phenoxy)acetonitrile, MS ($ES^{30}$, m/z): 602.3; 2-{2-[(3-{4-[(1-ethylpiperidin-4-yl)amino]-1-(2,2,2-trifluoroethyl)-1H-indol-2-yl}prop-2-yn-1-yl)amino]-5-methanesulfonylphenoxy}acetonitrile, MS ($ES^{30}$, m/z): 588.2; and 2-{2-[(3-{4-[(1-acetylpiperidin-4-yl)amino]-1-(2,2,2-trifluoroethyl)-1H-indol-2-yl}prop-2-yn-1-yl)amino]-5-methanesulfonylphenoxy}acetonitrile, MS ($ES^{30}$, m/z): 602.2.

Example D162: Preparation of 1-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)-formamido]-3-methoxypropan-2-yl 2-methylpropanoate

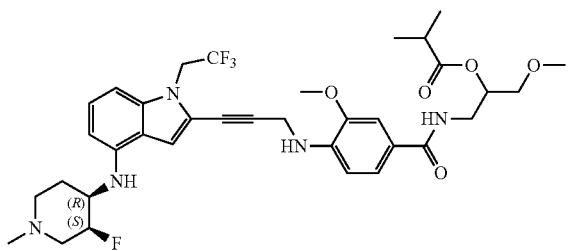

Synthesis of tert-butyl N-[4-[(2-hydroxy-3-methoxy-propyl)carbamoyl]-2-methoxy-phenyl]-N-prop-2-ynyl-carbamate. To a solution of 4-[tert-butoxycarbonyl(prop-2-ynyl)amino]-3-methoxy-benzoic acid (200 mg, 655.04 µmol, 1 eq) in DMF (2 mL) were added 1-amino-3-methoxy-propan-2-ol (103.3 mg, 982.56 µmol, 1.5 eq), HATU (498.1 mg, 1.31 mmol, 2 eq), and TEA (331.4 mg, 3.28 mmol, 456 µL, 5 eq). The mixture was degassed, purged with $N_2$ 3 times, and stirred at 50° C. for 2 h under $N_2$ atmosphere. TLC analysis (PE:EtOAc=1:1, Rf=0.4) indicated that the benzoic acid starting material was consumed. The reaction mixture was diluted with water (30 mL) and extracted with EtOAc (20 mL×3). The combined organic layers were washed with brine (10 mL×3), dried over anhydrous Na$_2$SO$_4$, filtered, and concentrated under reduced pressure to give a crude residue. The residue was purified by prep-TLC (SiO$_2$, PE:EtOAc=1: 1) to give the desired product (170 mg, 66% yield).

Synthesis of [1-[[[4-[tert-butoxycarbonyl(prop-2-ynyl) amino]-3-methoxy-benzoyl]amino]methyl]-2-methoxyethyl]2-methylpropanoate. To a solution of tert-butyl N-[4-[(2-hydroxy-3-methoxy-propyl)carbamoyl]-2-methoxyphenyl]-N-prop-2-ynyl-carbamate (170 mg, 433.18 µmol, 1 eq) in DCM (2 mL) were added TEA (306.8 mg, 3.03 mmol, 422 µL, 7 eq) and 2-methylpropanoyl 2-methylpropanoate (342.6 mg, 2.17 mmol, 359 µL, 5 eq). The mixture was stirred at 25° C. for 4 h under N$_2$ atmosphere. The reaction progress was monitored by TLC analysis (PE:EtOAc=1:1, Rf=0.45). Upon completion of the reaction, the reaction mixture was quenched by addition of water (20 mL) and extracted with DCM (15 mL×3). The combined organic layers were washed with brine (10 mL×2), dried over anhydrous Na$_2$SO$_4$, filtered and concentrated under reduced pressure to give the crude [1-[[[4-[tert-butoxycarbonyl (prop-2-ynyl)amino]-3-methoxy-benzoyl]amino]methyl]-2-methoxy-ethyl]2-methylpropanoate (160 mg), which was used directly in the next reaction without further purification.

Synthesis of [1-(methoxymethyl)-2-[[3-methoxy-4-(prop-2-ynylamino)benzoyl]-amino]ethyl]2-methylpropanoate. A solution of [1-[[[4-[tert-butoxycarbonyl(prop-2-ynyl) amino]-3-methoxy-benzoyl]amino]methyl]-2-methoxyethyl]2-methylpropanoate (160 mg, 345.92 µmol, 1 eq) in TFA (1.5 mL) and DCM (3 mL) was stirred at 25° C. for 15 min. TLC analysis (PE:EtOAc=1:1, Rf=0.25) indicated that 95% of the starting material was consumed, and one major new spot was detected. The reaction mixture was quenched by adding a saturated solution of Na$_2$CO$_3$ to adjust the pH of the solution to 8. The mixture was extracted with DCM (30 mL×3). The combined organic layers were washed with brine (10 mL×2), dried over anhydrous Na$_2$SO$_4$, filtered, and concentrated to dryness under reduced pressure. The crude residue was purified by preparative TLC (SiO$_2$, DCM: MeOH=10:1) to give the desired product (85 mg, 68% yield).

Synthesis of [1-[[[4-[3-[4-[[(3S,4R)-3-fluoro-1-methyl-4-piperidyl]amino]-1-(2,2,2-trifluoroethyl)indol-2-yl]prop-2-ynylamino]-3-methoxy-benzoyl]amino]methyl]-2-methoxy-ethyl]2-methylpropanoate. To a solution of [1-(methoxymethyl)-2-[[3-methoxy-4-(prop-2-ynylamino) benzoyl]amino]ethyl]2-methylpropanoate (79.6 mg, 219.67 µmol, 1 eq) in DMSO (2 mL) were added i-Pr$_2$NH (222.3 mg, 2.20 mmol, 310.45 µL, 10 eq), N-[(3S,4R)-3-fluoro-1-methyl-4-piperidyl]-2-iodo-1-(2,2,2-trifluoroethyl)indol-4-amine (100 mg, 219.67 µmol, 1 eq), CuI (8.4 mg, 43.93 µmol, 0.2 eq), and Pd(PPh$_3$)$_4$ (12.7 mg, 10.98 µmol, 0.05 eq). The reaction mixture was degassed, purged with N$_2$ 3 times, and stirred at 50° C. for 2 h. TLC analysis (DCM: MeOH=10:1, Rf=0.38) indicated that the starting material was consumed completely and one new spot was observed. The reaction mixture was quenched by adding a saturated solution of EDTA (20 mL) and extracted with EtOAc (20 mL×3). The combined organic layers were washed with brine (10 mL×2), dried over anhydrous Na$_2$SO$_4$, filtered, and concentrated under reduced pressure to give a residue. The residue was purified by preparative TLC (SiO$_2$, DCM: MeOH=10:1) and was purified by preparative HPLC (Phe-nomenex Luna C18: 200×40 mm, 10 um; Mobile phase: [water (0.2% FA)/ACN]; B %: 20%-60%, 10 min) to give the product (30 mg, 43% yield). LC-MS (ES$^+$, m/z): 660.1 [(M+H)$^+$].

Example D163: Preparation of 4-{[3-(4-{[(3S,4R)-3-fluoro-1-methylpiperidin-4-yl]amino}-1-(2,2,2-trifluoroethyl)-1H-indol-2-yl)prop-2-yn-1-yl] amino}-N-(1-hydroxypropan-2-yl)-3-methoxybenzamide

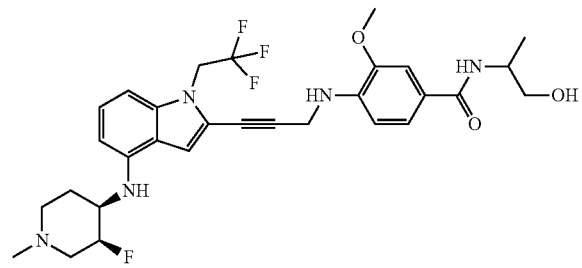 [SMILES: COc1cc(C(=O)NC(C)CO)ccc1NCC#Cc1cc2c(N[C@@H]3CCN(C)C[C@@H]3F)cccc2n1CC(F)(F)F]

To a solution of 4-((3-(4-(((3S,4R)-3-fluoro-1-methylpiperidin-4-yl)amino)-1-(2,2,2-trifluoroethyl)-1H-indol-2-yl) prop-2-yn-1-yl)amino)-3-methoxybenzoic acid (100 mg, 187.78 µmol, 1 eq) and 2-aminopropan-1-ol (16 mg, 206.56 µmol, 16.45 µL, 1.1 eq) in DMF (2 mL) were added HATU (107.1 mg, 281.67 µmol, 1.5 eq) and TEA (57.01 mg, 563.35 µmol, 78.41 µL, 3 eq). The mixture was degassed, purged with N$_2$ 3 times, and stirred at 25° C. for 2 h. LC-MS analysis showed that the starting material was consumed completely. Several new peaks were observed on LC-MS, and 34% of the desired compound was detected. The residue was diluted with water (30 mL) and extracted with EtOAc (30 mL×3). The combined organic layers were washed with brine (20 mL×3), dried over anhydrous Na$_2$SO$_4$, filtered, and concentrated under reduced pressure to give a residue. The crude product was purified by reversed-phase HPLC (column: Phenomenex Luna C18 200×40 mm, 10 um; mobile phase: [water (0.2% FA)-ACN]; B %: 20%-50%, 10 min) to give the desired amide product as a yellow solid (18.6 mg, 17% yield). LC-MS (ES$^+$, m/z): 590.1 [(M+H)$^+$]

Example D164: Preparation of 4-{[3-(4-{[(3S,4R)-3-fluoro-1-methylpiperidin-4-yl]amino}-1-(2,2,2-trifluoroethyl)-1H-indol-2-yl)prop-2-yn-1-yl] amino}-N-(2-hydroxypropyl)-3-methoxybenzamide

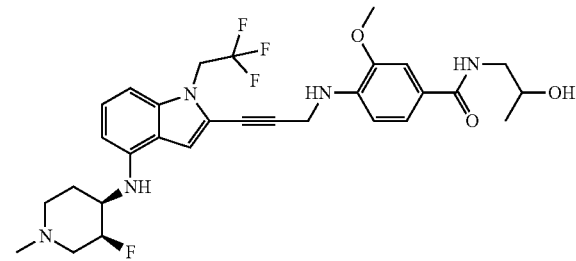 [SMILES: COc1cc(C(=O)NCC(C)O)ccc1NCC#Cc1cc2c(N[C@@H]3CCN(C)C[C@@H]3F)cccc2n1CC(F)(F)F]

To a solution of 4-((3-(4-(((3S,4R)-3-fluoro-1-methylpiperidin-4-yl)amino)-1-(2,2,2-trifluoroethyl)-1H-indol-2-yl) prop-2-yn-1-yl)amino)-3-methoxybenzoic acid (100 mg, 187.78 µmol, 1 eq) and 1-aminopropan-2-ol (15.5 mg, 206.56 µmol, 16.18 µL, 1.1 eq) in DMF (2 mL) were added HATU (107.1 mg, 281.67 µmol, 1.5 eq) and TEA (57.01 mg, 563.34 µmol, 78.41 µL, 3 eq). The mixture was degassed, purged with $N_2$ 3 times, and stirred at 25° C. for 2 h. LC-MS analysis showed that the starting material was consumed completely. Several new peaks were shown on LC-MS, and 35% of the desired compound was detected. The residue was diluted with water (30 mL) and extracted with EtOAc (30 mL×3). The combined organic layers were washed with brine (20 mL×3), dried over anhydrous $Na_2SO_4$, filtered, and concentrated under reduced pressure to give a residue. The crude product was purified by reversed-phase HPLC (column: Phenomenex Luna C18 200×40 mm, 10 um; mobile phase: [water (0.2% FA)-ACN]; B %: 20%-50%, 10 min) to give the desired amide product as a yellow solid (30.8 mg, 27% yield). LC-MS (ES$^+$, m/z): 590.1 [(M+H)$^+$]

Example D165: Preparation of 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-hydroxy-N-methylbenzamide

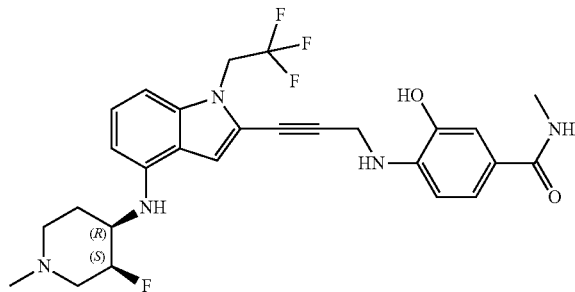

Synthesis of 3-hydroxy-N-methyl-4-(prop-2-ynylamino)benzamide. To a mixture of 3-methoxy-N-methyl-4-(prop-2-ynylamino)benzamide (500 mg, 2.29 mmol, 1 eq) in DCM (10 mL) was added $BBr_3$ (1.43 g, 5.73 mmol, 551.85 µL, 2.5 eq) at −10° C. The mixture was stirred at 0° C. for 1 h. LC-MS analysis showed that 27% of the starting material still remained. Several new peaks were observed on LC-MS, and 57% of the desired compound was detected. The reaction mixture was quenched by addition saturated solution of $Na_2CO_3$ (80 mL) to adjust the pH to 7-8. The mixture was then extracted with DCM:MeOH (100:1, 50 mL×3), filtered and concentrated to dryness under reduced pressure. The crude residue was purified by preparative TLC ($SiO_2$, PE:EtOAc=1:1) to give the product (80 mg, 15% yield). LC-MS (ES$^{30}$, m/z): 205.0 [(M+H)$^+$].

Synthesis of 4-[3-[4-[[(3S,4R)-3-fluoro-1-methyl-4-piperidyl]amino]-1-(2,2,2-trifluoroethyl)indol-2-yl]prop-2-ynylamino]-3-hydroxy-N-methyl-benzamide. To a solution of 3-hydroxy-N-methyl-4-(prop-2-ynylamino)benzamide (27.4 mg, 120.82 µmol, 1.1 eq) in DMSO (1 mL) were added i-Pr$_2$NH (111.1 mg, 1.10 mmol, 155 µL, 10 eq), CuI (2.1 mg, 10.98 µmol, 0.1 eq), and N-[(3S,4R)-3-fluoro-1-methyl-4-piperidyl]-2-iodo-1-(2,2,2-trifluoroethyl)indol-4-amine (50 mg, 109.83 µmol, 1 eq), Pd(PPh$_3$)$_4$ (6.4 mg, 5.49 µmol, 0.05 eq). The mixture was degassed, purged with $N_2$ 3 times, and stirred at 40° C. for 1 h under $N_2$ atmosphere. LC-MS analysis showed that the starting material was consumed completely, and the desired mass was detected. The reaction mixture was quenched by adding a saturated EDTA solution (20 mL) and stirring the mixture for 0.5 h. The mixture was then extracted with EtOAc (10 mL×3). The combined organic layers were washed with brine (10 mL×1), dried over anhydrous $Na_2SO_4$, filtered, and concentrated to dryness under reduced pressure. The crude residue was purified by preparative HPLC (Phenomenex Luna C18 100×30 mm, 5 um; Mobile phase: [water (0.2% FA)-ACN]; B %: 10%-30%, 12 min) to give the desired product (11.8 mg, 20% yield). LC-MS (ES$^+$, m/z): 532.2 [(M+H)$^+$]

Example D166: Preparation of 3-ethoxy-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}benzamide

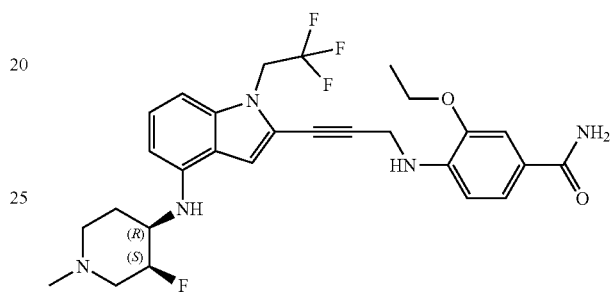

Synthesis of methyl 4-amino-3-ethoxy-benzoate. To a mixture of methyl 4-amino-3-hydroxy-benzoate (200 mg, 1.20 mmol, 1 eq), $K_2CO_3$ (330.7 mg, 2.39 mmol, 2 eq) in DMF (4 mL) was added iodoethane (223.92 mg, 1.44 mmol, 114.83 µL, 1.2 eq). The mixture was stirred at 20° C. for 16 h under $N_2$ atmosphere. TLC analysis (PE:EtOAc=3:1, Rf=0.35) indicated that the starting material was consumed completely, and one new spot was observed. The reaction mixture was quenched by adding water (60 mL) and extracted with EtOAc (35 mL×3). The combined organic layers were washed with brine (10 mL×2), dried over anhydrous $Na_2SO_4$, filtered, and concentrated to dryness under reduced pressure. The crude residue was purified by preparative TLC ($SiO_2$, PE:EtOAc=3:1) to give the desired product (140 mg, 60% yield).

Synthesis of methyl 4-(tert-butoxycarbonylamino)-3-ethoxy-benzoate. A mixture of methyl 4-amino-3-ethoxy-benzoate (140 mg, 717.16 µmol, 1 eq) in Boc$_2$O (782.6 mg, 3.59 mmol, 823.79 µL, 5 eq) was degassed, purged with $N_2$ 3 times, and stirred at 110° C. for 2 h under $N_2$ atmosphere. TLC analysis (PE:EtOAc=3:1, Rf=0.39) indicated that the starting material was consumed completely, and one new spot was observed. The reaction mixture was quenched by adding water (20 mL) and extracted with EtOAc (15 mL×2). The combined organic layers were washed with brine (8 mL), dried over anhydrous $Na_2SO_4$, filtered, and concentrated to dryness under reduced pressure. The crude residue was purified by preparative TLC ($SiO_2$, PE:EtOAc=3:1) to give the desired product (120 mg, 45% yield). LC-MS (ES$^{30}$, m/z): 240.0 [(M−tBu)$^+$]

Synthesis of methyl 4-[tert-butoxycarbonyl(prop-2-ynyl)amino]-3-ethoxy-benzoate. A mixture of methyl 4-(tert-butoxycarbonylamino)-3-ethoxy-benzoate (100 mg, 338.60 µmol, 1 eq), Cs$_2$CO$_3$ (220.7 mg, 677.21 µmol, 2 eq), 3-bromoprop-1-yne (75.5 mg, 507.91 µmol, 54.73 µL, 1.5 eq) in DMF (2 mL) was degassed and purged with $N_2$ 3 times. The mixture was stirred at 25° C. for 3 h under $N_2$ atmosphere. LC-MS analysis showed that the starting material was consumed completely, and the desired mass was detected. The reaction mixture was quenched by adding water (40 mL) and extracted with EtOAc (20 mL×3). The combined organic layers were washed with brine (10 mL), dried over anhydrous Na$_2$SO$_4$, filtered, and concentrated to dryness under reduced pressure to give the crude product (100 mg). The crude product was used in the next step without further purification. LC-MS (ES$^+$, m/z): 278.0 [(M−tBu)$^+$]

Synthesis 4-[tert-butoxycarbonyl(prop-2-ynyl)amino]-3-ethoxy-benzoic acid. A mixture of methyl 4-[tert-butoxycarbonyl(prop-2-ynyl)amino]-3-ethoxy-benzoate (100 mg, 299.96 μmol, 1 eq) and LiOH·H$_2$O (62.9 mg, 1.50 mmol, 5 eq) in MeOH (1.5 mL) and water (0.5 mL) was degassed and purged with N$_2$ 3 times. The mixture was stirred at 25° C. for 2 h under N$_2$ atmosphere. TLC analysis (PE:EtOAc=3:1, Rf=0.3) indicated that the ester starting material was consumed completely, and one new spot was observed. The reaction mixture was concentrated under reduced pressure to remove MeOH and was quenched by adding 1N HCl to adjust the pH of the solution to 3~4, and extracted with EtOAc (20 mL×3). The combined organic layers were washed with brine (20 mL), dried over anhydrous Na$_2$SO$_4$, filtered, and concentrated to dryness under reduced pressure to give crude 4-[tert-butoxycarbonyl(prop-2-ynyl)amino]-3-ethoxy-benzoic acid (80% yield). The crude product was used in the next reaction without further purification.

Synthesis of tert-butyl N-(4-carbamoyl-2-ethoxy-phenyl)-N-prop-2-ynyl-carbamate. A mixture of 4-[tert-butoxycarbonyl(prop-2-ynyl)amino]-3-ethoxy-benzoic acid (80 mg, 250.51 μmol, 1 eq), ammonia·hydrochloride (40.20 mg, 751.52 μmol, 3 eq), HOBt (67.7 mg, 501.02 μmol, 2 eq), EDCI (96.0 mg, 501.02 μmol, 2 eq) and TEA (253.49 mg, 2.51 mmol, 349 μL, 10 eq) in DMF (2 mL) was degassed, purged with N$_2$ 3 times, and stirred at 25° C. for 4 h under N$_2$ atmosphere. LC-MS analysis showed the mass of the desired product. The reaction mixture was quenched by adding water (30 mL) and extracted with EtOAc (15 mL×3). The combined organic layers were washed with brine (10 mL), dried over anhydrous Na$_2$SO$_4$, filtered, and concentrated under reduced pressure to give a residue. The crude residue was purified by preparative TLC (SiO$_2$, PE:EtOAc=1:1) to give the desired product (60 mg, 68% yield). LC-MS (ES$^{30}$, m/z): 263.0 [(M−tBu)$^+$].

Synthesis of tert-butyl N-(4-carbamoyl-2-ethoxy-phenyl)-N-[3-[4-[[(3S,4R)-3-fluoro-1-methyl-4-piperidyl]amino]-1-(2,2,2-trifluoroethyl)indol-2-yl]prop-2-ynyl]carbamate. To a solution of tert-butyl N-(4-carbamoyl-2-ethoxy-phenyl)-N-prop-2-ynyl-carbamate (51.3 mg, 144.98 μmol, 1.1 eq) in DMSO (2 mL) were added i-Pr$_2$NH (134 mg, 1.32 mmol, 186 μL, 10 eq), CuI (2.5 mg, 13.18 μmol, 0.1 eq), N-[(3S,4R)-3-fluoro-1-methyl-4-piperidyl]-2-iodo-1-(2,2,2-trifluoroethyl)indol-4-amine (60 mg, 131.80 μmol, 1 eq), and Pd(PPh$_3$)$_4$ (7.62 mg, 6.59 μmol, 0.05 eq). The reaction mixture was degassed, purged with N$_2$ 3 times, and stirred at 40° C. for 1 h under N$_2$ atmosphere. TLC analysis (EtOAc:MeOH=5:1, Rf=0.30) indicated that the starting material was consumed completely, and one new spot was observed. The reaction was quenched by adding a saturated solution of EDTA (30 mL), stirring the mixture for 0.5 h, and extracted with EtOAc (20 mL×3). The combined organic layers were washed with brine (10 mL), dried over anhydrous Na$_2$SO$_4$, filtered, and concentrated under reduced pressure to give a residue. The crude residue was purified by preparative TLC (SiO$_2$, EtOAc:MeOH=5:1) to give the desired product (75 mg, 82% yield).

Synthesis of 3-ethoxy-4-[3-[4-[[(3S,4R)-3-fluoro-1-methyl-4-piperidyl]amino]-1-(2,2,2-trifluoroethyl)indol-2-yl]prop-2-ynylamino]benzamide. A mixture of tert-butyl N-(4-carbamoyl-2-ethoxy-phenyl)-N-[3-[4-[[(3S,4R)-3-fluoro-1-methyl-4-piperidyl]amino]-1-(2,2,2-trifluoroethyl)indol-2-yl]prop-2-ynyl]carbamate (75 mg, 116.16 μmol, 1 eq), in HCl/EtOAc (3 mL) was stirred at 25° C. for 1 h under N$_2$ atmosphere. TLC analysis (EtOAc:MeOH=5:1, Rf=0.38) indicated that the starting material was consumed completely, and one new spot was observed. The reaction mixture was concentrated under reduced pressure to remove EtOAc and was quenched by adding a saturated solution of Na$_2$CO$_3$ to adjust the pH to 9. The mixture was then extracted with EtOAc (20 mL×2). The combined organic layers were washed with brine (20 mL), dried over anhydrous Na$_2$SO$_4$, filtered, and concentrated under reduced pressure to give a residue. The crude residue was purified by preparative TLC (SiO$_2$, EtOAc:MeOH=5:1). The residue was purified by preparative HPLC (FA condition; column: Welch Xtimate C18 150×2 5 mm, 5 um; Mobile phase: [water (0.2% FA)-ACN]; B %: 20%-40%, 10 min) to give the desired product (25 mg, 39.5% yield). LC-MS (ES$^{30}$, m/z): 546.2 [(M+H)$^+$]

Example D167: Preparation of N-ethyl-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-hydroxybenzamide

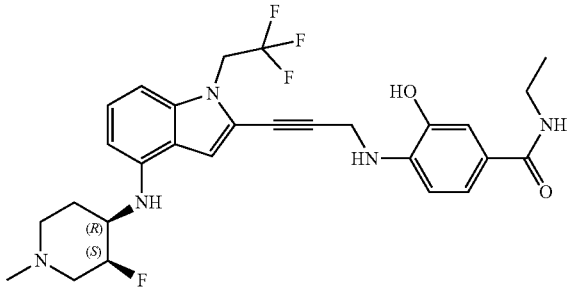

Synthesis of tert-butyl N-[4-(ethylcarbamoyl)-2-methoxy-phenyl]-N-prop-2-ynyl-carbamate. To a solution of 4-[tert-butoxycarbonyl(prop-2-ynyl)amino]-3-methoxy-benzoic acid (1 g, 3.28 mmol, 1 eq) in DMF (10 mL) were added TEA (3.31 g, 32.75 mmol, 4.56 mL, 10 eq), HOBt (885.1 mg, 6.55 mmol, 2 eq), EDCI (1.26 g, 6.55 mmol, 2 eq), and ethanamine (267.1 mg, 3.28 mmol, 387.63 L, 1 eq, HCl). The reaction mixture was degassed, purged with N$_2$ 3 times, and stirred at 30° C. for 2 h under N$_2$ atmosphere. TLC analysis (PE:EtOAc=2:1, Rf=0.41) indicated that the starting material was consumed completely, and one new spot was observed. The reaction mixture was quenched by adding water (100 mL) and extracted with EtOAc (50 mL×2). The combined organic layers were washed with brine (50 mL), dried over anhydrous Na$_2$SO$_4$, filtered, and concentrated under reduced pressure to give a residue. The crude residue was purified by column chromatography (SiO$_2$, PE/EtOAc=0:1 to 3:1) to give the desired product (800 mg, 74% yield).

Synthesis of N-ethyl-3-methoxy-4-(prop-2-ynylamino) benzamide. A mixture of tert-butyl N-[4-(ethylcarbamoyl)-2-methoxy-phenyl]-N-prop-2-ynyl-carbamate (800 mg, 2.41 mmol, 1 eq), in DCM (8 mL) and TFA (4 mL) was degassed and purged with N₂ 3 times, and the mixture was stirred at 25° C. for 0.5 h under N₂ atmosphere. TLC analysis (PE:EtOAc=1:1, Rf=0.4) indicated that the starting material was consumed completely, and one new spot was observed. The reaction mixture was quenched by adding a saturated solution of Na₂CO₃, adjusting the pH of the solution to 7~8, and extracting the mixture with DCM (100 mL×3). The combined organic layers were washed with brine (50 mL), dried over anhydrous Na₂SO₄, filtered, and concentrated under reduced pressure to give a residue. The residue was purified by column chromatography (SiO₂, PE:EtOAc=0:1 to 1:1) to give the desired product (470 mg, 84% yield).

Synthesis of N-ethyl-3-hydroxy-4-(prop-2-ynylamino) benzamide. To a mixture of N-ethyl-3-methoxy-4-(prop-2-ynylamino)benzamide (400 mg, 1.45 mmol, 1 eq) in DCM (10 mL) was added BBr₃ (1.09 g, 4.34 mmol, 418.49 μL, 3 eq) at 0° C. The mixture was stirred at 0° C. for 1.5 h. LC-MS analysis showed that 3.5% of the starting material remained. Several new peaks were shown on LC-MS, and 84% of the desired compound was detected. The reaction mixture was quenched by adding a saturated solution of Na₂CO₃, and 1N HCl was added to the mixture to adjust the pH of the solution to 6. The mixture was then extracted with DCM:MeOH=200:1 (100 mL×2), filtered, and concentrated under reduced pressure to give a residue. The crude product was precipitated using DCM (15 mL), filtered, and concentrated under reduced pressure to give the desired product (180 mg, 53% yield). LC-MS (ES⁺, m/z): 219.1 [(M+H)⁺].

Synthesis of N-ethyl-4-[3-[4-[[(3S,4R)-3-fluoro-1-methyl-4-piperidyl]amino]-1-(2,2,2-trifluoroethyl)indol-2-yl]prop-2-ynylamino]-3-hydroxy-benzamide. To a solution of N-ethyl-3-hydroxy-4-(prop-2-ynylamino)benzamide (41.0 mg, 169.14 μmol, 1.1 eq) in DMSO (1 mL) were added i-Pr₂NH (155.6 mg, 1.54 mmol, 217.32 μL, 10 eq), CuI (2.9 mg, 15.38 μmol, 0.1 eq), N-[(3S,4R)-3-fluoro-1-methyl-4-piperidyl]-2-iodo-1-(2,2,2-trifluoroethyl)indol-4-amine (70 mg, 153.77 μmol, 1 eq), and Pd(PPh₃)₄ (8.9 mg, 7.69 μmol, 0.05 eq). The reaction mixture was degassed and purged with N₂ 3 times, then stirred at 40° C. for 1 h under N₂ atmosphere. TLC analysis (EtOAc:MeOH=4:1, Rf=0.26) indicated that the starting material was consumed completely, and one new spot was observed. The mixture was quenched by adding a saturated solution of EDTA (40 mL), stirring the resulting mixture for 0.5 h, and extracting the mixture with EtOAc (25 mL×2). The combined organic layers were washed with brine (10 mL), dried over anhydrous Na₂SO₄, filtered, and concentrated under reduced pressure to give a residue. The residue was purified by preparative HPLC (Phenomenex Luna C18 200×40 mm, 10 um; mobile phase: [water (0.2% FA)-ACN]; B %: 1%-30%, 8 min) to give the desired product (26 mg, 31% yield). LC-MS (ES⁺, m/z): 546.3 [(M+H)⁺].

Example D168: Preparation of 3-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)-formamido]-2-methoxypropyl 2-methylpropanoate

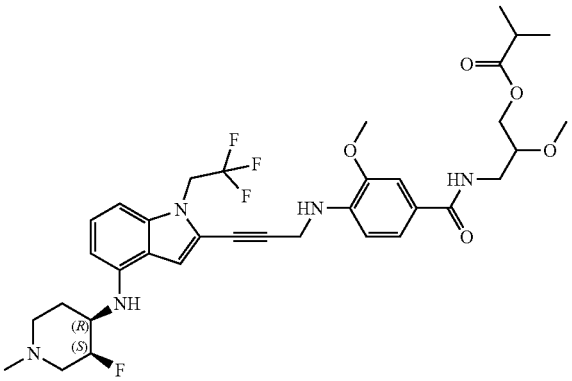

Synthesis of 2-(3-(Benzyloxy)-2-hydroxypropyl)isoindoline-1,3-dione. To a solution of 2-((benzyloxy)methyl)oxirane (2.68 g, 1.2 eq), isoindoline-1,3-dione (2 g, 1 eq) in EtOH (20 mL) was added K₂CO₃ (150.29 mg, 0.08 eq). The mixture was stirred at 80° C. for 12 h. LCMS analysis showed that the starting material was consumed completely, and one main peak with desired mass was observed. The reaction mixture was concentrated under reduced pressure to dryness. The crude residue was purified by column chromatography (SiO₂, PE:EtOAc=20:1 to 2:1). 2-(3-(Benzyloxy)-2-hydroxypropyl)isoindoline-1,3-dione was obtained as a white solid (3.1 g).

Synthesis of 2-(3-(benzyloxy)-2-methoxypropyl)isoindoline-1,3-dione. To a solution of 2-(3-(benzyloxy)-2-hydroxypropyl)-isoindoline-1,3-dione (2 g, 1 eq) and MeI (1.37 g, 1.5 eq) in THF (20 mL) was added NaH (385.40 mg, 60% purity, 1.5 eq) at 0° C., then the mixture was stirred at 25° C. for 16 h. TLC analysis (PE:EtOAc=2:1, R_f=0.6) indicated that the starting material was consumed completely, and one new spot was observed. The reaction mixture was poured into NH₄Cl (150 mL). The aqueous phase was extracted with EtOAc (60 mL×3). The combined organic phase was washed with brine (40 mL), dried with anhydrous Na₂SO₄, filtered, and concentrated in vacuo. The residue was purified by column chromatography (SiO₂, PE:EtOAc=20:1 to 15:1) to give the desired product as a light yellow oil (1.2 g).

Synthesis of 3-(benzyloxy)-2-methoxypropan-1-amine. To a solution of 2-(3-(benzyloxy)-2-methoxypropyl)isoindoline-1,3-dione (1.2 g, 1 eq) in EtOH (12 mL), was added N₂H₄ water (376.80 mg, 98% purity, 2 eq) at 50° C. under N₂, then the mixture was stirred at 80° C. for 2 h. LCMS analysis showed that the starting material was consumed completely, and one main peak with the desired m/z was observed. The reaction mixture was concentrated under reduced pressure to remove the solvent. The crude product was purified by reversed-phase HPLC (column: Xtimate C18 10u 250 mm*80 mm; mobile phase: [water (10 mM NH₄HCO₃)-ACN]; B %: 1%-20%, 27 min). 3-(Benzyloxy)-2-methoxypropan-1-amine was obtained as a clear oil (0.19 g). LCMS (ES³⁰, m/z): 391.2 [(M+1)⁺]

Synthesis of 3-amino-2-methoxypropan-1-ol. To a solution of 3-(benzyloxy)-2-methoxypropan-1-amine (204.71 mg, 1.05 mmol, 1 eq) in MeOH (2 mL) was added Pd/C (10%, 0.15 g) under N₂ atmosphere. The suspension was degassed and purged with H₂ for 3 times. The mixture was stirred under H₂ (50 psi or atm) at 25° C. for 16 h. TLC analysis (DCM:MeOH=10:1, R$_f$=0.2) indicated that the starting material was consumed completely. The reaction mixture was filtered and concentrated under reduced pressure to give a residue. The crude product was used directly in the next step. 3-Amino-2-methoxypropan-1-ol was obtained as a white oil (90 mg, crude). ¹H NMR (400 MHz, Chloroform-d) δ=2.89-2.95 (m, 1H), 2.97-3.05 (m, 1H), 3.28 (br d, J=2.63 Hz, 1H), 3.43-3.46 (m, 3H), 3.69-3.76 (m, 1H), 3.79-3.86 (m, 1H), 7.30 (br s, 1H).

Synthesis of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-N-(3-hydroxy-2-methoxypropyl)-3-methoxybenzamide. To a solution of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoic acid (150 mg, 1 eq) in DMF (2 mL) were added HATU (160.65 mg, 1.5 eq) and TEA (85.51 mg, 3 eq). The mixture was degassed and purged with N₂ for 3 times, and then 3-amino-2-methoxypropan-1-ol (32.58 mg, 1.1 eq) was added dropwise, The mixture was stirred at 25° C. for 1 h. LCMS analysis showed that the starting material was consumed completely, and three main peaks with the desired m/z were observed. The residue was diluted with water (50 mL) and extracted with EtOAc (30 mL×3). The combined organic layers were washed with brine (30 mL×3), dried over anhydrous Na₂SO₄, filtered, and concentrated under reduced pressure to give a residue. The residue was purified by preparative TLC (SiO₂, DCM:MeOH=10:1) to give 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-N-(3-hydroxy-2-methoxypropyl)-3-methoxybenzamide as a yellow solid (100 mg). LCMS (ES³⁰, m/z): 620.3 [(M+1)⁺]

Synthesis of 3-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)-formamido]-2-methoxypropyl 2-methylpropanoate. To a solution of 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-N-(3-hydroxy-2-methoxypropyl)-3-methoxybenzamide (90 mg, 1 eq) in DCM (5 mL) were added 2-methylpropanoyl 2-methylpropanoate (25.3 mg, 1.1 eq) and TEA (44.09 mg, 3 eq), The mixture was stirred at 45° C. for 16 h. TLC analysis (DCM:MeOH=10:1, R$_f$=0.5) indicated that the starting material was consumed completely, and one new spot was observed. The mixture was filtered and concentrated under reduced pressure to give a residue. The residue was purified by preparative TLC (SiO₂, DCM:MeOH=10:1). The residue was purified by preparative TLC (SiO₂, DCM:MeOH=10:1) to give the desired product as a yellow solid (24.2 mg). LCMS (ES⁺, m/z): 690.2 [(M+1)⁺].

Example D169: Preparation of N-ethyl-4-{[3-(4-{[(3S,4R)-3-fluoropiperidin-4-yl]amino}-1-(2,2,2-trifluoroethyl)-1H-indol-2-yl)prop-2-yn-1-yl]amino}-3-methoxybenzamide

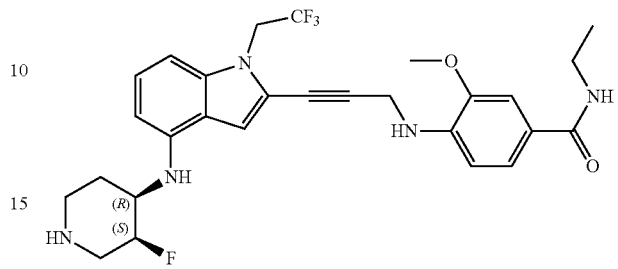

Synthesis of tert-butyl (4-(ethylcarbamoyl)-2-methoxyphenyl)(prop-2-yn-1-yl)carbamate. A mixture of 4-((tert-butoxycarbonyl)(prop-2-yn-1-yl)amino)-3-methoxybenzoic acid (0.4 g, 1.31 mmol, 1 eq) and ethanamine (106.83 mg, 1.31 mmol, 155.05 μL, 1 eq, HCl) in DMF (2 mL) were added HOBt (354.04 mg, 2.62 mmol, 2 eq), EDCI (502.28 mg, 2.62 mmol, 2 eq), and TEA (397.70 mg, 3.93 mmol, 547.04 μL, 3 eq). The mixture was degassed and purged with N₂ 3 times, and then the mixture was stirred at 25° C. for 2 h under N₂ atmosphere. TLC analysis (PE:EtOAc=2:1, R$_f$=0.4) indicated that the starting material was consumed completely, and one new spot was observed. The residue was diluted with water (50 mL) and extracted with EtOAc (30 mL×3). The combined organic layers were washed with brine (20 mL×3), dried over anhydrous Na₂SO₄, filtered, and concentrated under reduced pressure to give a residue. The residue was purified by preparative TLC (SiO₂, PE:EtOAc=2:1) to give tert-butyl (4-(ethylcarbamoyl)-2-methoxyphenyl)(prop-2-yn-1-yl)carbamate as clear oil (400 mg, 83% yield). ¹H NMR (400 MHz, DMSO-d₆) δ=1.10-1.17 (m, 3H), 1.20-1.42 (m, 9H), 3.06-3.14 (m, 1H), 3.31 (br s, 2H), 3.81-3.89 (m, 3H), 3.99-4.63 (m, 2H), 7.20-7.31 (m, 1H), 7.37-7.44 (m, 1H), 7.47-7.53 (m, 1H), 8.44-8.56 (m, 1H).

Synthesis of tert-butyl (3S,4R)-4-((2-(3-((tert-butoxycarbonyl)(4-(ethylcarbamoyl)-2-methoxyphenyl)amino)prop-1-yn-1-yl)-1-(2,2,2-trifluoroethyl)-1H-indol-4-yl)amino)-3-fluoropiperidine-1-carboxylate. To a solution of tert-butyl (4-(ethylcarbamoyl)-2-methoxyphenyl)(prop-2-yn-1-yl)carbamate (55.26 mg, 166.26 μmol, 0.9 eq) in DMSO (2 mL) were added i-PrNH₂ (109.20 mg, 1.85 mmol, 158.72 μL, 10 eq) and CuI (1.76 mg, 9.24 μmol, 0.05 eq). Then, tert-butyl (3S,4R)-3-fluoro-4-((2-iodo-1-(2,2,2-trifluoroethyl)-1H-indol-4-yl)amino)piperidine-1-carboxylate (100 mg, 184.73 μmol, 1 eq) and Pd(PPh₃)₄ (10.67 mg, 9.24 μmol, 0.05 eq) were added, and the resulting mixture was purged with N₂ 3 times. The mixture was stirred at 25° C. for 1 h. TLC analysis (DCM:MeOH=10:1, Rf=0.45) indicated that the starting material was consumed completely, and one new spot was observed. The reaction mixture was quenched by adding a saturated solution of EDTA (100 mL) and extracted with EtOAc (90 mL×3). The combined organic layers were washed with brine (30 mL×3), dried over anhydrous Na₂SO₄, filtered, and concentrated under reduced pressure to give a residue. The crude residue was purified by preparative TLC (SiO₂, DCM:MeOH=10:1) to give the desired product as a yellow solid (70 mg, 50% yield). LC-MS (ES³⁰, m/z): 797.5 [(M+1)⁺]

Synthesis of N-ethyl-4-{[3-(4-{[(3S,4R)-3-fluoropiperidin-4-yl]amino}-1-(2,2,2-trifluoroethyl)-1H-indol-2-yl)prop-2-yn-1-yl]amino}-3-methoxybenzamide. A solution of tert-butyl (3S,4R)-4-((2-(3-((tert-butoxycarbonyl)(4-(ethylcarbamoyl)-2-methoxyphenyl)amino)prop-1-yn-1-yl)-1-(2,2,2-trifluoroethyl)-1H-indol-4-yl)amino)-3-fluoropiperidine-1-carboxylate (70 mg, 93.86 μmol, 1 eq) in HCl/EtOAc (4 M, 2 mL) was stirred at 25° C. for 1 h. TLC analysis (DCM:MeOH=10:1, Rf=0.5) indicated that the starting material was consumed completely, and one new spot was observed. The reaction mixture was diluted with a saturated solution of Na₂CO₃ (50 mL) and extracted with EtOAc (30 mL×3). The combined organic layers were washed with brine (30 mL×3), dried over anhydrous Na₂SO₄, filtered, and concentrated under reduced pressure to give a residue. The residue was purified by preparative TLC (SiO₂, DCM:MeOH=10:1) and then by reversed-phase HPLC (column: Welch Xtimate C18 150×25 mm, 5 um; mobile phase: [water (0.2% FA)-ACN]; B %: 25%-50%, 10 min) to give the desired product as a yellow solid (20.6 mg, 40% yield).

Example D170: Preparation of 4-{[3-(4-{[(3S,4R)-1-ethyl-3-fluoropiperidin-4-yl]amino}-1-(2,2,2-trifluoroethyl)-1H-indol-2-yl)prop-2-yn-1-yl]amino}-3-methoxybenzamide

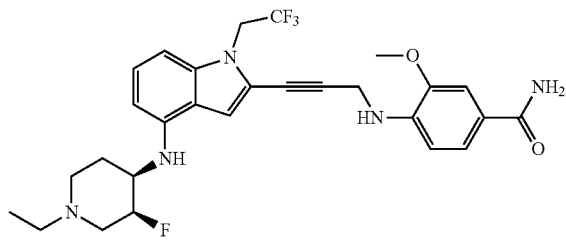 [SMILES: CCN1CC[C@@H](Nc2cccc3c2cc(C#CCNc2ccc(C(N)=O)cc2OC)n3CC(F)(F)F)[C@@H](F)C1]

Synthesis of N-((3S,4R)-1-ethyl-3-fluoropiperidin-4-yl)-2-iodo-1-(2,2,2-trifluoroethyl)-1H-indol-4-amine. To a solution of N-((3S,4R)-3-fluoropiperidin-4-yl)-2-iodo-1-(2,2,2-trifluoroethyl)-1H-indol-4-amine (0.15 g, 339.98 μmol, 1 eq) in DMF (2 mL) were added EtI (79.5 mg, 509.97 μmol, 41 μL, 1.5 eq) and K₂CO₃ (234.9 mg, 1.70 mmol, 5 eq). The mixture was stirred at 25° C. for 2 h under N₂ atmosphere. TLC analysis (PE:EtOAc=2:1, Rf=0.4) indicated that the starting material was consumed completely, and one new spot was observed. The residue was diluted with water (20 mL) and extracted with EtOAc (30 mL×3). The combined organic layers were washed with brine (20 mL×3), dried over anhydrous Na₂SO₄, filtered, and concentrated under reduced pressure to give a residue. The residue was purified by preparative TLC (SiO₂, PE:EtOAc=2:1). N-((3S,4R)-1-ethyl-3-fluoropiperidin-4-yl)-2-iodo-1-(2,2,2-trifluoroethyl)-1H-indol-4-amine was obtained as a yellow solid (120 mg, 68% yield). ¹H NMR (400 MHz, DMSO-d₆) δ=1.00 (t, J=7.09 Hz, 3H) 1.66-1.77 (m, 1H) 1.85-1.96 (m, 1H) 2.05-2.14 (m, 1H) 2.16-2.31 (m, 1H) 2.37 (brd, J=7.09 Hz, 2H) 2.90-2.94 (m, 1H) 3.07-3.17 (m, 1H) 3.51-3.70 (m, 1H) 4.72-4.92 (m, 1H) 4.96-5.05 (m, 2H) 5.35-5.44 (m, 1H) 6.19-6.28 (m, 1H) 6.79-6.86 (m, 1H) 6.88-6.97 (m, 1H) 7.22-7.30 (m, 1H).

Synthesis of tert-butyl (4-carbamoyl-2-methoxyphenyl)(3-(4-(((3S,4R)-1-ethyl-3-fluoropiperidin-4-yl)amino)-1-(2,2,2-trifluoroethyl)-1H-indol-2-yl)prop-2-yn-1-yl)carbamate. To a solution of tert-butyl (4-carbamoyl-2-methoxyphenyl)(prop-2-yn-1-yl)carbamate (58.4 mg, 191.79 μmol, 0.9 eq) in DMSO (2 mL) were added i-PrNH₂ (126 mg, 2.13 mmol, 183 μL, 10 eq), CuI (2.03 mg, 10.66 μmol, 0.05 eq), N-((3S,4R)-1-ethyl-3-fluoropiperidin-4-yl)-2-iodo-1-(2,2,2-trifluoroethyl)-1H-indol-4-amine (100 mg, 213.10 μmol, 1 eq), and Pd(PPh₃)₄ (12.31 mg, 10.66 μmol, 0.05 eq). The mixture was purged with N₂ 3 times then stirred at 25° C. for 1 h. TLC analysis (DCM:MeOH=10:1, Rf=0.5) indicated that the starting material was consumed completely, and one new spot was observed. The reaction mixture was quenched by addition a saturated solution of EDTA (100 mL) and extracted with EtOAc (90 mL×3). The combined organic layers were washed with brine (30 mL×3), dried over anhydrous Na₂SO₄, filtered, and concentrated under reduced pressure to give a residue. The residue was purified by preparative TLC (SiO₂, DCM:MeOH=10:1) to give tert-butyl (4-carbamoyl-2-methoxyphenyl)(3-(4-(((3S,4R)-1-ethyl-3-fluoropiperidin-4-yl)amino)-1-(2,2,2-trifluoroethyl)-1H-indol-2-yl)prop-2-yn-1-yl)carbamate as a yellow solid (100 mg, 69% yield). LC-MS (ES³⁰, m/z): 678.8 [(M+1)⁺].

Synthesis of 4-{[3-(4-{[(3S,4R)-1-ethyl-3-fluoropiperidin-4-yl]amino}-1-(2,2,2-trifluoroethyl)-1H-indol-2-yl)prop-2-yn-1-yl]amino}-3-methoxybenzamide. A solution of tert-butyl (4-carbamoyl-2-methoxyphenyl)(3-(4-(((3S,4R)-1-ethyl-3-fluoropiperidin-4-yl)amino)-1-(2,2,2-trifluoroethyl)-1H-indol-2-yl)prop-2-yn-1-yl)carbamate (100 mg, 154.87 μmol, 1 eq) in HCl/EtOAc (4 M, 2 mL) was stirred at 25° C. for 1 h. TLC analysis (DCM:MeOH=10:1, Rf=0.4) indicated that the starting material was consumed completely, and one new spot was observed. The reaction mixture was diluted with a saturated solution of Na₂CO₃ (50 mL) and extracted with EtOAc (30 mL×3). The combined organic layers were washed with brine (30 mL×3), dried over anhydrous Na₂SO₄, filtered and concentrated under reduced pressure to give a residue. The crude residue was purified by preparative TLC (SiO₂, DCM:MeOH=10:1) then again by preparative TLC (SiO₂, EtOAc:MeOH:TEA=20:1:1) to give 4-{[3-(4-{[(3S,4R)-1-ethyl-3-fluoropiperidin-4-yl]amino}-1-(2,2,2-trifluoroethyl)-1H-indol-2-yl)prop-2-yn-1-yl]amino}-3-methoxybenzamide as a yellow solid (25.2 mg, 30% yield). LC-MS (ES⁺, m/z): 546.2 [(M+1)⁺].

Example D171: Preparation of 5-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-4-methoxy-N,N-dimethylpyridine-2-carboxamide

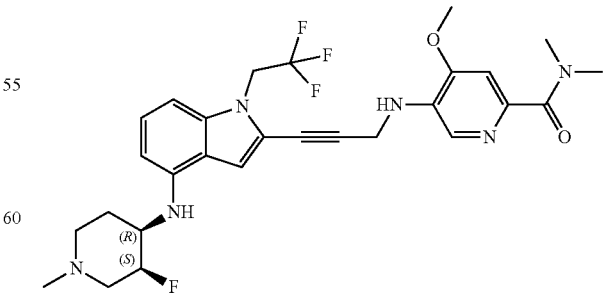

Synthesis of 5-bromo-4-methoxy-pyridine-2-carboxylic acid. A mixture of methyl 5-bromo-4-methoxy-pyridine-2-carboxylate (1 g, 4.06 mmol, 1 eq), LiOH·H₂O (852.7 mg, 20.32 mmol, 5 eq) in THF (8 mL) and water (8 mL) was degassed and purged with $N_2$ 3 times, then stirred at 25° C. for 1 h under $N_2$ atmosphere. TLC analysis (PE:EtOAc=2:1, Rf=0.02) indicated that the starting material was consumed completely, and one new spot was observed. The reaction mixture was quenched by adding 1N HCl to adjust the solution to pH=4 and extracted with EtOAc (30 mL×15). The combined organic layers were washed with brine (20 mL×2), dried over anhydrous $Na_2SO_4$, filtered, and concentrated under reduced pressure to give the crude 5-bromo-4-methoxy-pyridine-2-carboxylic acid (750 mg). LC-MS (ES$^+$, m/z): 231.9 [(M–H)$^+$]. The crude product was used in the next step without further purification.

Synthesis of 5-bromo-4-methoxy-N,N-dimethyl-pyridine-2-carboxamide. A mixture of 5-bromo-4-methoxy-pyridine-2-carboxylic acid (700 mg, 3.02 mmol, 1 eq), N-methylmethanamine (2 M, 1.96 mL, 1.3 eq), HATU (1.38 g, 3.62 mmol, 1.2 eq), and TEA (1.53 g, 15.08 mmol, 2.10 mL, 5 eq) in DMF (10 mL) was degassed and purged with $N_2$ 3 times, and the mixture was stirred at 25° C. for 15 h under $N_2$ atmosphere. TLC analysis (PE:EtOAc=2:1, Rf=0.13) indicated that 10% of the starting material remained, and one major new spot was detected. The reaction mixture was quenched by adding water (100 mL) and extracted with EtOAc (50 mL×5). The combined organic layers were washed with brine (20 mL×2), dried over anhydrous $Na_2SO_4$, filtered, and concentrated under reduced pressure to give a residue. The residue was purified by preparative TLC ($SiO_2$, PE:EtOAc=2:1) to give 5-bromo-4-methoxy-N,N-dimethyl-pyridine-2-carboxamide (500 mg, 64% yield).

Synthesis of tert-butyl N-[6-(dimethylcarbamoyl)-4-methoxy-3-pyridyl]carbamate. To a solution of 5-bromo-4-methoxy-N,N-dimethyl-pyridine-2-carboxamide (300 mg, 1.16 mmol, 1 eq) in dioxane (10 mL) were added $NH_2Boc$ (271 mg, 2.32 mmol, 2 eq), $Cs_2CO_3$ (1.13 g, 3.47 mmol, 3 eq), XPhos (331 mg, 694.71 μmol, 0.6 eq), and $Pd(OAc)_2$ (169 mg, 752.61 μmol, 0.65 eq). The mixture was degassed and purged with $N_2$ 3 times, then stirred at 120° C. for 2 h. TLC analysis (PE:EtOAc=1:1, Rf=20) indicated that the starting material was consumed completely, and new spots were detected. The reaction mixture was quenched by adding water (300 mL) and extracted with EtOAc (50 mL×5). The combined organic layers were washed with brine (30 mL×2), dried over anhydrous $Na_2SO_4$, filtered, and concentrated under reduced pressure to give a residue. The residue was purified by preparative TLC ($SiO_2$, PE:EtOAc=1:1) to give the desired product (200 mg, 59% yield). LC-MS (ES$^{30}$, m/z): 296.1 [(M+H)$^+$].

Synthesis of tert-butyl N-[6-(dimethylcarbamoyl)-4-methoxy-3-pyridyl]-N-prop-2-yny 1-carbamate. To a solution of tert-butyl N-[6-(dimethylcarbamoyl)-4-methoxy-3-pyridyl]carbamate (150 mg, 507.90 μmol, 1 eq) in DMF (3 mL) were added $Cs_2CO_3$ (331 mg, 1.02 mmol, 2 eq) and 3-bromoprop-1-yne (98.18 mg, 660.27 μmol, 71.15 μL, 1.3 eq). The mixture was stirred at 25° C. for 10 h under $N_2$ atmosphere. TLC analysis (PE:EtOAc=0:1, Rf=0.40) indicated that the starting material was consumed completely, and one new spot was detected. The reaction mixture was quenched by adding water (80 mL) and extracted with EtOAc (20 mL×3). The combined organic layers were washed with brine (10 mL×2), dried over anhydrous $Na_2SO_4$, filtered, and concentrated under reduced pressure to give a residue. The crude residue was purified by preparative TLC ($SiO_2$, PE:EtOAc=0:1) to give tert-butyl N-[6-(dimethylcarbamoyl)-4-methoxy-3-pyridyl]-N-prop-2-yny 1-carbamate (115 mg, 68% yield). LC-MS (ES$^+$, m/z): 334.1 [(M+H)$^+$]

Synthesis of tert-butyl N-[6-(dimethylcarbamoyl)-4-methoxy-3-pyridyl]-N-[3-[4-[[(3S,4R)-3-fluoro-1-methyl-4-piperidyl]amino]-1-(2,2,2-trifluoroethyl)indol-2-yl]prop-2-ynyl]carbamate. To a solution of N-[(3S,4R)-3-fluoro-1-methyl-4-piperidyl]-2-iodo-1-(2,2,2-trifluoroethyl)indol-4-amine (130 mg, 285.57 μmol, 1 eq) in DMSO (2 mL) were added i-$Pr_2NH$ (288.97 mg, 2.86 mmol, 403.59 μL, 10 eq), tert-butyl N-[6-(dimethylcarbamoyl)-4-methoxy-3-pyridyl]-N-prop-2-ynyl-carbamate (104.72 mg, 314.13 μmol, 1.1 eq), CuI (10.88 mg, 57.11 μmol, 0.2 eq), and $Pd(PPh_3)_4$ (16.50 mg, 14.28 μmol, 0.05 eq). The mixture was degassed and purged with $N_2$ 3 times then stirred at 50° C. for 1 h under $N_2$ atmosphere. TLC analysis (DCM:MeOH=10:1, Rf=0.50) indicated that the starting material was consumed completely, and new spots were detected. The reaction mixture was quenched by adding a saturated solution of EDTA (150 mL) and stirred for 30 min then extracted with EtOAc (40 mL×3). The combined organic layers were washed with brine (20 mL×2), dried over anhydrous $Na_2SO_4$, filtered, and concentrated under reduced pressure to dryness. The crude residue was purified by preparative TLC ($SiO_2$, DCM:MeOH=10:1) to give tert-butyl N-[6-(dimethylcarbamoyl)-4-methoxy-3-pyridyl]-N-[3-[4-[[(3S,4R)-3-fluoro-1-methyl-4-piperidyl]amino]-1-(2,2,2-trifluoroethyl)indol-2-yl]prop-2-ynyl]carbamate (100 mg, 53% yield). LC-MS (ES$^+$, m/z): 661.3 [(M+H)$^+$].

Synthesis of 5-[3-[4-[[(3S,4R)-3-fluoro-1-methyl-4-piperidyl]amino]-1-(2,2,2-trifluoroet hyl)indol-2-yl]prop-2-ynylamino]-4-methoxy-N,N-dimethyl-pyridine-2-carboxamide. A mixture of tert-butyl N-[6-(dimethylcarbamoyl)-4-methoxy-3-pyridyl]-N-[3-[4-[[(3 S,4R)-3-fluoro-1-methyl-4-piperidyl]amino]-1-(2,2,2-trifluoroethyl)indol-2-yl]prop-2-ynyl]carbamate (100 mg, 151.35 μmol, 1 eq) in EtOAc (10 mL) and 4 M HCl/EtOAc (3 mL) was degassed and purged with $N_2$ 3 times, then stirred at 25° C. for 0.5 h under $N_2$ atmosphere. LC-MS analysis showed that the starting material was consumed completely, and desired mass was detected. The reaction mixture was quenched by adding a saturated solution of $Na_2CO_3$ to adjust the solution to pH 9 and extracted with EtOAc (20 mL×3). The combined organic layers were washed with brine (10 mL×2), dried over anhydrous $Na_2SO_4$, filtered, and concentrated under reduced pressure to dryness. The crude residue was purified by preparative HPLC (Column: Phenomenex Luna C18 200×40 mm, 10 um; Mobile phase: [water (10 mM $NH_4HCO_3$)-ACN]; B %: 20%-50%, 10 min) to give 5-[3-[4-[[(3S,4R)-3-fluoro-1-methyl-4-piperidyl]amino]-1-(2,2, 2-trifluoroet hyl)indol-2-yl]prop-2-ynylamino]-4-methoxy-N,N-dimethyl-pyridine-2-carboxamide (27.5 mg, 32% yield). LC-MS (ES$^+$, m/z): 561.1 [(M+H)$^+$].

Example D172: Preparation of 5-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-4-methoxy-N-methylpyridine-2-carboxamide

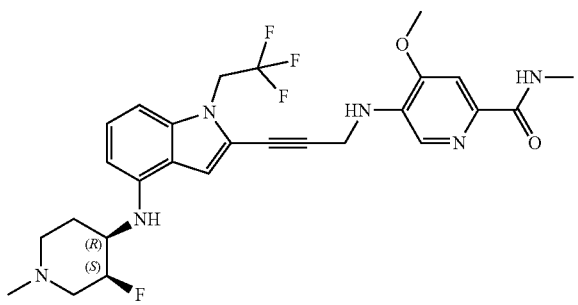

Synthesis of methyl 5-(tert-butoxycarbonylamino)-4-methoxy-pyridine-2-carboxylate. To a solution of methyl 5-bromo-4-methoxy-pyridine-2-carboxylate (300 mg, 1.22 mmol, 1 eq) in dioxane (10 mL) were added $NH_2Boc$ (285.65 mg, 2.44 mmol, 2 eq), $Cs_2CO_3$ (1.19 g, 3.66 mmol, 3 eq), XPhos (348.74 mg, 731.53 μmol, 0.6 eq), and $Pd(OAc)_2$ (177.92 mg, 792.50 μmol, 0.65 eq). The mixture was degassed and purged with $N_2$ 3 times, then stirred at 120° C. for 2 h under $N_2$ atmosphere. TLC analysis (PE:EtOAc=1:1, Rf=0.16) indicated that the starting material was consumed completely, and new spots were detected. The reaction mixture was quenched by adding water (300 mL) and extracted with EtOAc (50 mL×5). The combined organic layers were washed with brine (30 mL×2), dried over anhydrous $Na_2SO_4$, filtered, and concentrated under reduced pressure to give a residue. The residue was purified by preparative TLC ($SiO_2$, PE:EtOAc=1:1) to give methyl 5-(tert-butoxycarbonylamino)-4-methoxy-pyridine-2-carboxylate (160 mg, 47% yield).

Synthesis of methyl 5-[tert-butoxycarbonyl(prop-2-ynyl)amino]-4-methoxy-pyridine-2-carboxylate. A mixture of methyl 5-(tert-butoxycarbonylamino)-4-methoxy-pyridine-2-carboxylate (133.8 mg, 474.04 μmol, 1 eq), $Cs_2CO_3$ (386.1 mg, 1.19 mmol, 2.5 eq), and 3-bromoprop-1-yne (105.7 mg, 711.06 μmol, 76.62 μL, 1.5 eq) in DMF (2 mL) was degassed and purged with $N_2$ 3 times, then stirred at 25° C. for 2 h under $N_2$ atmosphere. TLC analysis (PE:EtOAc=0:1, Rf=0.37) indicated that the starting material was consumed completely, and a new spot was detected. The reaction mixture was quenched by adding water (80 mL) and extracted with EtOAc (20 mL×3). The combined organic layers were washed with brine (10 mL×2), dried over anhydrous $Na_2SO_4$, filtered, and concentrated under reduced pressure to dryness. The residue was purified by preparative TLC ($SiO_2$, PE:EtOAc=0:1) to give methyl 5-[tert-butoxycarbonyl(prop-2-ynyl)amino]-4-methoxy-pyridine-2-carboxylate (125 mg, 82.3% yield).

Synthesis of tert-butyl N-[4-methoxy-6-(methylcarbamoyl)-3-pyridyl]-N-prop-2-ynyl-carbamate. A mixture of methyl 5-[tert-butoxycarbonyl(prop-2-ynyl)amino]-4-methoxy-pyridine-2-carboxylate (105 mg, 327.78 μmol, 1 eq), methanamine (10.2 mg, 327.78 μmol, 1 mL, 1 eq), in THF (1 mL) was degassed and purged with $N_2$ 3 times, then stirred at 25° C. for 5 h under $N_2$ atmosphere. TLC analysis [(PE:EtOAc=1:1) (DCM:MeOH=10:1), Rf=0.45] indicated that the starting material was consumed completely, and one new spot was detected. The reaction mixture was quenched by adding water (50 mL) and extracted with EtOAc (20 mL×3). The combined organic layers were washed with brine (10 mL×2), dried over anhydrous $Na_2SO_4$, filtered, and concentrated under reduced pressure to dryness. The crude product tert-butyl N-[4-methoxy-6-(methylcarbamoyl)-3-pyridyl]-N-prop-2-ynyl-carbamate (95 mg, 91% yield) was used in the next step without further purification. LC-MS ($ES^{30}$, m/z): 320.1 [(M+H)$^+$].

Synthesis of tert-butyl N-[3-[4-[[(3S,4R)-3-fluoro-1-methyl-4-piperidyl]amino]-1-(2,2,2-trifluoroethyl)indol-2-yl]prop-2-ynyl]-N-[4-methoxy-6-(methylcarbamoyl)-3-pyridyl]carbamate. To a solution of N-[(3S,4R)-3-fluoro-1-methyl-4-piperidyl]-2-iodo-1-(2,2,2-trifluoroethyl)indol-4-amine (120 mg, 263.60 μmol, 1 eq) in DMSO (2 mL) were added $i-Pr_2NH$ (266.74 mg, 2.64 mmol, 372.54 μL, 10 eq), tert-butyl N-[4-methoxy-6-(methylcarbamoyl)-3-pyridyl]-N-prop-2-ynyl-carbamate (92.60 mg, 289.96 μmol, 1.1 eq), CuI (10.04 mg, 52.72 μmol, 0.2 eq), and $Pd(PPh_3)_4$ (15.23 mg, 13.18 μmol, 0.05 eq). The mixture was degassed and purged with $N_2$ 3 times, then stirred at 40° C. for 1 h under $N_2$ atmosphere. TLC analysis (DCM:MeOH=10:1, Rf=0.38) indicated that the starting material was consumed completely, and new spots were detected. The reaction mixture was quenched by adding a saturated solution of EDTA (100 mL) and stirring the mixture for 30 min, and extracted with EtOAc (30 mL×3). The combined organic layers were washed with brine (20 mL×2), dried over anhydrous $Na_2SO_4$, filtered, and concentrated under reduced pressure to dryness. The crude residue was purified by preparative TLC ($SiO_2$, DCM:MeOH=10:1) to give tert-butyl N-[3-[4-[[(3S,4R)-3-fluoro-1-methyl-4-piperidyl]amino]-1-(2,2,2-trifluoroethyl)indol-2-yl]prop-2-ynyl]-N-[4-methoxy-6-(methylcarbamoyl)-3-pyridyl]carbamate (100 mg, 59% yield).

Synthesis of 5-[3-[4-[[(3S,4R)-3-fluoro-1-methyl-4-piperidyl]amino]-1-(2,2,2-trifluoroethyl)indol-2-yl]prop-2-ynylamino]-4-methoxy-N-methyl-pyridine-2-carboxamide. A mixture of tert-butyl N-[3-[4-[[(3S,4R)-3-fluoro-1-methyl-4-piperidyl]amino]-1-(2,2,2-trifluoroethyl)indol-2-yl]prop-2-ynyl]-N-[4-methoxy-6-(methylcarbamoyl)-3-pyridyl]carbamate (100 mg, 154.64 μmol, 1 eq) in EtOAc (10 mL) and 4M HCl/EtOAc (3 mL) was degassed and purged with $N_2$ 3 times, then stirred at 25° C. for 1.5 h under $N_2$ atmosphere. LC-MS analysis showed that the desired mass was detected. The reaction mixture was quenched by adding a saturated solution of $Na_2CO_3$ to adjust the solution to pH=9 and extracted with EtOAc (20 mL×4). The combined organic layers were washed with brine (10 mL×2), dried over anhydrous $Na_2SO_4$, filtered, and concentrated under reduced pressure to dryness. The crude residue was purified by preparative HPLC (neutral condition; column: Waters Xbridge Prep OBD C18 150×40 mm, 10 um; mobile phase: [water (10 mM $NH_4HCO_3$)-ACN]; B %: 25%-55%, 8 min) to give 5-[3-[4-[[(3S,4R)-3-fluoro-1-methyl-4-piperidyl]amino]-1-(2,2,2-trifluoroethyl)indol-2-yl]prop-2-ynylamino]-4-methoxy-N-methyl-pyridine-2-carboxamide (30 mg, 36% yield). LC-MS ($ES^+$, m/z): 547.1 [(M+H)$^+$].

Example D173: 1-tert-butyl-N-[3-(4-{[(3S,4R)-3-fluoro-1-methylpiperidin-4-yl]amino}-1-(2,2,2-trifluoroethyl)-1H-indol-2-yl)prop-2-yn-1-yl]-1H-pyrazole-4-carboxamide

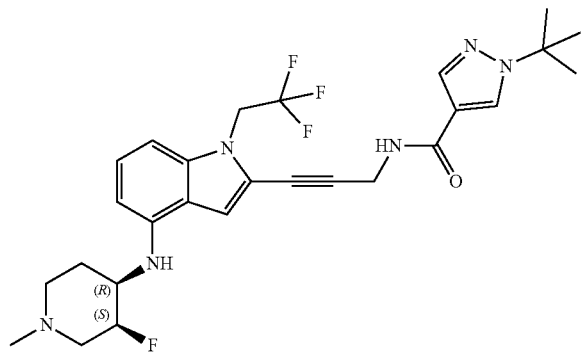

Synthesis of tert-butyl (3-(4-(((3S,4R)-3-fluoro-1-methylpiperidin-4-yl)amino)-1-(2,2,2-trifluoroethyl)-1H-indol-2-yl)prop-2-yn-1-yl)carbamate. To a solution of tert-butyl prop-2-yn-1-ylcarbamate (61.36 mg, 395.40 μmol, 0.9 eq) in DMSO (2 mL) were added i-Pr$_2$NH (444.57 mg, 4.39 mmol, 620.90 μL, 10 eq), CuI (4.18 mg, 21.97 μmol, 0.05 eq), and N-((3S,4R)-3-fluoro-1-methylpiperidin-4-yl)-2-iodo-1-(2,2,2-trifluoroethyl)-1H-indol-4-amine (200 mg, 439.34 μmol, 1 eq) at 20° C., then Pd(PPh$_3$)$_4$ (25.38 mg, 21.97 μmol, 0.05 eq) was added. The mixture was purged with N$_2$ 3 times and stirred at 25° C. for 1 h. TLC analysis (DCM:MeOH=10:1, R$_f$=0.4) indicated that the starting material was consumed completely, and one new spot was detected. The reaction mixture was quenched by adding a saturated solution of EDTA (50 mL) and extracted with EtOAc (40 mL×3). The combined organic layers were washed with brine (30 mL×3), dried over anhydrous Na$_2$SO$_4$, filtered and concentrated under reduced pressure to dryness. The crude residue was purified by preparative TLC (SiO$_2$, DCM:MeOH=10:1) to give tert-butyl (3-(4-(((3S,4R)-3-fluoro-1-methylpiperidin-4-yl)amino)-1-(2,2,2-trifluoroethyl)-1H-indol-2-yl)prop-2-yn-1-yl)carbamate was obtained as a yellow solid (100 mg, 46% yield). $^1$H NMR (400 MHz, DMSO-d$_6$) δ=1.41 (s, 9H), 1.65-1.76 (m, 1H), 1.86-2.01 (m, 1H), 2.04-2.15 (m, 1H), 2.17-2.31 (m, 4H), 2.75-2.88 (m, 1H), 3.04 (brt, J=10.58 Hz, 1H), 3.47-3.73 (m, 1H), 4.03 (d, J=5.62 Hz, 2H), 4.89 (br s, 1H), 4.95-5.12 (m, 2H) 5.48-5.59 (m, 1H) 6.19-6.34 (m, 1H) 6.72-6.84 (m, 1H) 7.03 (t, J=8.01 Hz, 1H) 7.17-7.26 (m, 1H) 7.41 (br s, 1H).

Synthesis of 2-(3-aminoprop-1-yn-1-yl)-N-((3S,4R)-3-fluoro-1-methylpiperidin-4-yl)-1-(2,2,2-trifluoroethyl)-1H-indol-4-amine. To a solution of tert-butyl (3-(4-(((3S,4R)-3-fluoro-1-methylpiperidin-4-yl)amino)-1-(2,2,2-trifluoroethyl)-1H-indol-2-yl)prop-2-yn-1-yl)carbamate (100 mg, 207.25 μmol, 1 eq) in DCM (2.64 g, 31.08 mmol, 2 mL, 149.98 eq) was added TFA (1.54 g, 13.51 mmol, 1 mL, 65.17 eq), and the resulting mixture was stirred at 25° C. for 1 h. TLC analysis (PE:EtOAc=0:1, R$_f$=0.2) indicated that the starting material was consumed completely, and one new spot formed. The reaction mixture was concentrated under nitrogen to remove the solvent. Water (50 mL) was then added, and a saturated solution of Na$_2$CO$_3$ was added to adjust the solution to pH=10. The product was extracted with EtOAc (50 mL×3). The combined organic layers were washed with brine (30 mL×3), dried over anhydrous Na$_2$SO$_4$, filtered, and concentrated under reduced pressure to dryness. The crude residue was purified by reversed-phase HPLC (column: Phenomenex Luna C18 200×40 mm, 10 um; mobile phase: [water (0.2% FA)-ACN]; B %: 1%-40%, 10 min) to give 2-(3-aminoprop-1-yn-1-yl)-N-((3S,4R)-3-fluoro-1-methylpiperidin-4-yl)-1-(2,2,2-trifluoroethyl)-1H-indol-4-amine as a yellow solid (21.6 mg, 27% yield). $^1$H NMR (400 MHz, DMSO-d$_6$) δ=1.67-1.75 (m, 1H), 1.88-2.02 (m, 1H), 2.06-2.14 (m, 1H), 2.16-2.31 (m, 4H), 2.82 (br d, J=11.37 Hz, 1H), 2.99-3.09 (m, 1H), 3.53-3.63 (m, 1H), 3.76 (s, 2H), 4.76-4.90 (m, 1H), 5.02-5.12 (m, 2H), 5.40-5.64 (m, 1H), 6.23-6.31 (m, 1H), 6.74-6.82 (m, 1H), 6.99-7.07 (m, 1H), 7.18-7.25 (m, 1H), 8.24-8.27 (m, 1H).

Synthesis of 1-tert-butyl-N-[3-(4-{[(3S,4R)-3-fluoro-1-methylpiperidin-4-yl]amino}-1-(2,2,2-trifluoroethyl)-1H-indol-2-yl)prop-2-yn-1-yl]-1H-pyrazole-4-carboxamide. To a solution of 1-(tert-butyl)-1H-pyrazole-4-carboxylic acid (48.4 mg, 287.66 μmol, 1.1 eq) in DMF (2 mL) were added HOBt (70.67 mg, 523.02 μmol, 2 eq), EDCI (100.26 mg, 523.02 μmol, 2 eq), TEA (79.39 mg, 784.52 μmol, 109.20 μL, 3 eq), and 2-(3-aminoprop-1-yn-1-yl)-N-((3S,4R)-3-fluoro-1-methylpiperidin-4-yl)-1-(2,2,2-trifluoroethyl)-1H-indol-4-amine (0.1 g, 261.51 μmol, 1 eq). The resulting mixture was stirred at 25° C. for 1 h under N$_2$ atmosphere. TLC analysis (EtOAc:TEA=20:1, R$_f$=0.6) indicated that the starting material was consumed completely, and one new spot was detected. The residue was diluted with water (60 mL) and extracted with EtOAc (30 mL×3). The combined organic layers were washed with brine (20 mL×3), dried over anhydrous Na$_2$SO$_4$, filtered, and concentrated under reduced pressure to give a residue. The crude product was purified by reversed-phase HPLC (column: Phenomenex Luna C18 200×40 mm, 10 um; mobile phase: [water (0.2% FA)-ACN]; B %: 20%-60%, 10 min). 1-tert-butyl-N-[3-(4-{[(3S,4R)-3-fluoro-1-methylpiperidin-4-yl]amino}-1-(2,2,2-trifluoroethyl)-1H-indol-2-yl)prop-2-yn-1-yl]-1H-pyrazole-4-carboxamide was obtained as a yellow solid (30.1 mg, 22% yield). LCMS (ES$^{30}$, m/z): 533.1 [(M+H)$^+$].

Example D174: Preparation of rac-N-[(3R,4S)-4-fluoro-1-methylpiperidin-3-yl]-2-{3-[(4-methanesulfonyl-2-methoxyphenyl)amino]prop-1-yn-1-yl}-1-(2,2,2-trifluoroethyl)-1H-indol-4-amine

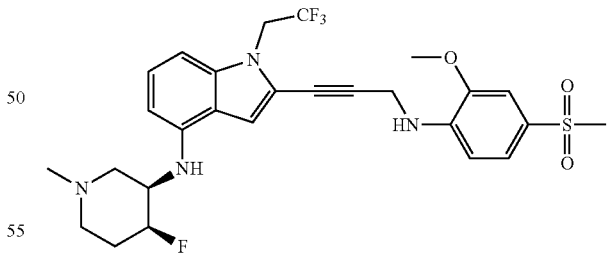

Synthesis of N-[3-[4-bromo-1-(2,2,2-trifluoroethyl)indol-2-yl]prop-2-ynyl]-2-methoxy-4-methylsulfonyl-aniline. A mixture of tert-butyl N-[3-[4-bromo-1-(2,2,2-trifluoroethyl)indol-2-yl]prop-2-ynyl]-N-(2-methoxy-4-methylsulfonyl-phenyl)carbamate (300 mg, 487.44 μmol, 1.1 eq) and HCl/EtOAc (4 M, 5 mL, 45.1 eq) was stirred at 25° C. for 2 h. TLC showed that the reaction was complete. The residue was filtered and concentrated in vacuo to afford the product (200 mg, crude) as a yellow oil, which was used in the next step without purification.

Synthesis of tert-butyl (3R,4S)-4-fluoro-3-[[2-[3-(2-methoxy-4-methylsulfonyl-anilino)prop-1-ynyl]-1-(2,2,2-trifluoroethyl)indol-4-yl]amino]piperidine-1-carboxylate.

To a mixture of N-[3-[4-bromo-1-(2,2,2-trifluoroethyl)indol-2-yl]prop-2-ynyl]-2-methoxy-4-methylsulfonyl-aniline (200 mg, 388.09 µmol, 1.1 eq) and tert-butyl (3R,4S)-3-amino-4-fluoro-piperidine-1-carboxylate (80 mg, 366.52 µmol, 1.0 eq) in THF (7 mL) were added XPhos-Pd-G4 (33.7 mg, 36.65 µmol, 0.1 eq), dicyclohexyl-[2-(2,6-diisopropoxyphenyl)phenyl]phosphane (34.2 mg, 73.30 µmol, 0.2 eq), and $Cs_2CO_3$ (358.3 mg, 1100.00 µmol, 3.0 eq) in one portion at 20° C. under $N_2$. The reaction mixture was then heated to 90° C. and stirred for 2 hours. TLC and LCMS analysis showed that the reaction was completed. The residue was poured into a saturated solution of EDTA (20 mL) and stirred for 120 min. The aqueous phase was extracted with EtOAc (20 mL×3). The combined organic phases were washed with brine (20 mL×3), dried with anhydrous $Na_2SO_4$, filtered, and concentrated to dryness under reduced pressure to give tert-butyl (3R,4S)-4-fluoro-3-[[2-[3-(2-methoxy-4-methylsulfonyl-anilino)prop-1-ynyl]-1-(2,2,2-trifluoroethyl)indol-4-yl]amino]piperidine-1-carboxylate as yellow solid (150 mg, crude). It was used in the next reaction without further purification. LC-MS ($ES^{30}$, m/z): 653.3 [(M+H)$^+$]. 1H NMR (400 MHz, DMSO-d6) δ=7.38 (dd, J=8.40, 2.00 Hz, 1H), 7.25 (d, J=2.00 Hz, 1H), 7.17 (s, 1H), 7.03 (t, J=8.00 Hz, 1H), 6.89 (d, J=8.44 Hz, 1H), 6.79 (d, J=8.20 Hz, 1H), 6.48 (t, J=6.30 Hz, 1H), 6.31 (d, J=7.82 Hz, 1H), 5.53 (d, J=8.44 Hz, 1H), 5.13-4.86 (m, 3H), 4.36 (d, J=6.24 Hz, 2H), 3.89 (s, 3H), 3.76-3.62 (m, 1H), 3.96-3.59 (m, 1H), 3.09 (s, 3H), 2.05-1.96 (m, 1H), 2.17-1.68 (m, 2H), 1.35 (s, 9H).

Synthesis of N-[(3R,4S)-4-fluoro-3-piperidyl]-2-[3-(2-methoxy-4-methylsulfonyl-anilino)prop-1-ynyl]-1-(2,2,2-trifluoroethyl)indol-4-amine. To a mixture of tert-butyl (3R,4S)-4-fluoro-3-[[2-[3-(2-methoxy-4-methylsulfonyl-anilino)prop-1-ynyl]-1-(2,2,2-trifluoroethyl)indol-4-yl]amino]piperidine-1-carboxylate (150 mg, 229.81 µmol, 1.0 eq) was added HCl/EtOAc (4 M, 2.31 mL, 40.2 eq) in one portion at 20° C., and the mixture was stirred for 1 h. TLC and LCMS analysis showed that the reaction was complete. The residue was poured into $NaHCO_3$ (sat.) (10 mL), and the aqueous phase was extracted with EtOAc (20 mL×3). The combined organic phase was washed with brine (20 mL×3), dried over anhydrous $Na_2SO_4$, filtered, and concentrated under reduced pressure to dryness to give the crude product as white solid (70 mg). The crude product was used in the next step without further purification. LC-MS (ES$^+$, m/z): 553.2 [(M+H)$^+$]. 1H NMR (400 MHz, DMSO-d6) δ=7.39 (dd, J=8.38, 1.76 Hz, 1H), 7.25 (d, J=1.76 Hz, 1H), 7.16 (s, 1H), 7.01 (t, J=8.04 Hz, 1H), 6.89 (d, J=8.38 Hz, 1H), 6.75 (d, J=8.16 Hz, 1H), 6.49 (t, J=6.16 Hz, 1H), 6.26 (d, J=7.72 Hz, 1H), 5.44 (d, J=8.82 Hz, 1H), 5.07-4.86 (m, 3H), 4.36 (d, J=6.16 Hz, 2H), 3.89 (s, 3H), 3.78-3.59 (m, 1H), 3.09 (s, 3H), 2.96-2.64 (m, 4H), 1.99-1.67 (m, 2H).

Synthesis of N-[(3R,4S)-4-fluoro-1-methyl-3-piperidyl]-2-[3-(2-methoxy-4-methylsulfonyl-anilino)prop-1-ynyl]-1-(2,2,2-trifluoroethyl)indol-4-amine. To a mixture of N-[(3R,4S)-4-fluoro-3-piperidyl]-2-[3-(2-methoxy-4-methylsulfonyl-anilino)prop-1-ynyl]-1-(2,2,2-trifluoroethyl)indol-4-amine (70 mg, 126.68 µmol, 1.0 eq) and formaldehyde (38 mg, 1270.00 µmol, 0.034 mL, 10.0 eq) in MeOH (3 mL) were added sodium cyanoborohydride (23.88 mg, 380.03 µmol, 3.0 eq) and AcOH (0.76 mg, 12.67 µmol, 0.1 eq) in one portion at 20° C. under $N_2$. The mixture was heated to 50° C. and stirred for 1.5 h. LCMS analysis showed the reaction was completed. The residue was poured into a saturated solution of EDTA (20 mL) and stirred for 120 min. The aqueous phase was extracted with EtOAc (30 mL×3). The combined organic phases were washed with brine (30 mL×3), dried over anhydrous $Na_2SO_4$, filtered, and concentrated in vacuo. The crude product was purified by preparative HPLC (column: Waters Xbridge BEH C18 100× 25 mm, 5 um; mobile phase: [water (10 mM $NH_4HCO_3$)-ACN]; B %: 40%-70%, 10 min) to give N-[(3R,4S)-4-fluoro-1-methyl-3-piperidyl]-2-[3-(2-methoxy-4-methylsulfonyl-anilino)prop-1-ynyl]-1-(2,2,2-trifluoroethyl)indol-4-amine as white solid (23.1 mg, 32% yield). LC-MS ($ES^{30}$, m/z): 567.3 [(M+H)$^+$].

Example D175: N-[(3S,4R)-1-tert-butyl-3-fluoro-4-piperidyl]-2-[3-(2-methoxy-4-methylsulfonyl-anilino)prop-1-ynyl]-1-(2,2,2-trifluoroethyl)indol-4-amine and N-[(3R,4S)-1-tert-butyl-3-fluoro-4-piperidyl]-2-[3-(2-methoxy-4-methylsulfonyl-anilino)prop-1-ynyl]-1-(2,2,2-trifluoroethyl)indol-4-amine

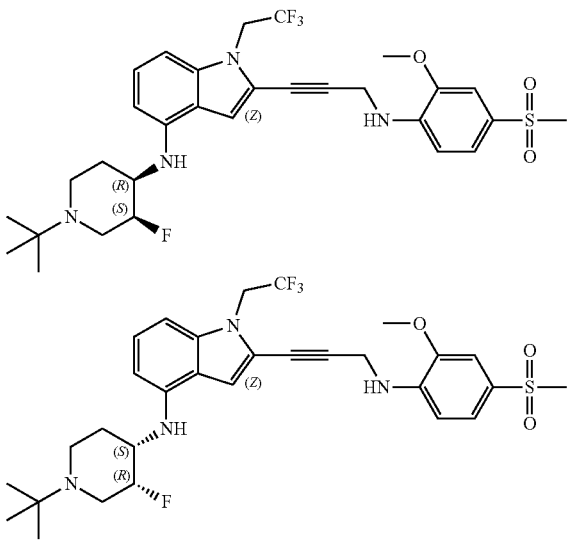

Synthesis of rac-N-(1-tert-butyl-3-fluoro-4-piperidyl)-2-iodo-1-(2,2,2-trifluoroethyl)-indol-4-amine. To a mixture of 2-iodo-1-(2,2,2-trifluoroethyl)indol-4-amine (140 mg, 371.80 µmol, 1.0 eq, HCl) and 1-tert-butyl-3-fluoro-piperidin-4-one (193.22 mg, 1.12 mmol, 3.0 eq) in EtOH (3 mL) was added Ti(OEt)$_4$ (848.1 mg, 3.72 mmol, 771.01 µL, 10.0 eq) in one portion at 50° C. under $N_2$. The reaction mixture was stirred for 14 h, then $NaBH_3CN$ (233.7 mg, 3.72 mmol, 10.0 eq) was added, and the reaction was then heated to 50° C. and stirred for 2 h. TLC and LCMS analysis showed the desired mass. The aqueous phase was extracted with EtOAc (20 mL×3) and water (30 mL). The combined organic phases were washed with brine (20 mL×3), dried over anhydrous $Na_2SO_4$, filtered, and concentrated under reduced pressure. The crude was purified by preparative TLC (SiO$_2$, DCM/MEOH=10:1) to give rac-N-((3S,4R)-1-(tert-butyl)-3-fluoropiperidin-4-yl)-2-iodo-1-(2,2,2-trifluoroethyl)-1H-indol-4-amine (90 mg, 49% yield) as yellow oil and rac-N-((3R,4R)-1-(tert-butyl)-3-fluoropiperidin-4-yl)-2-iodo-1-(2,2,2-trifluoroethyl)-1H-indol-4-amine (45 mg, 24% yield) as yellow oil. LC-MS ($ES^{30}$, m/z): 498.2 [(M+H)$^+$].

Synthesis of N-[(3S,4R)-1-tert-butyl-3-fluoro-4-piperidyl]-2-[3-(2-methoxy-4-methylsulfonyl-anilino)prop-1-ynyl]-1-(2,2,2-trifluoroethyl)indol-4-amine and N-[(3R,4S)-1-tert-butyl-3-fluoro-4-piperidyl]-2-[3-(2-methoxy-4-methylsulfonyl-anilino)prop-1-ynyl]-1-(2,2,2-trifluoroethyl)indol-4-amine. To a mixture of rac-N-((3S,4R)-1-(tert-butyl)-3-fluoropiperidin-4-yl)-2-iodo-1-(2,2,2-trifluoroethyl)-1H-indol-4-amine (90.0 mg, 162.88 μmol, 1.0 eq) and 2-methoxy-4-methylsulfonyl-N-prop-2-ynyl-aniline (77.95 mg, 325.75 μmol, 2.0 eq) in DMSO (2 mL) were added CuI (310.2 ug, 1.63 μmol, 0.1 eq), N-isopropylpropan-2-amine (164.8 mg, 1.63 mmol, 230 μL, 10.0 eq), and Pd(PPh$_3$)$_4$ (9.4 mg, 8.14 μmol, 0.1 eq) in one portion at 25° C. under N$_2$, then the reaction was stirred for 1 h. LCMS analysis showed the desired product. The residue was poured into a saturated solution of EDTA (20 mL), and the biphasic mixture was stirred for 120 min. The layers were separated, and the aqueous phase was extracted with EtOAc (20 mL×3). The combined organic phase was washed with brine (20 mL×3), dried over anhydrous Na$_2$SO$_4$, filtered, and concentrated under reduced pressure to dryness. The crude residue was purified by preparative HPLC (Waters Xbridge Prep OBD C18 150×40 mm, 10 um; mobile phase: [water (10 mM NH$_4$HCO$_3$)-ACN]; B %: 60%-80%, 8 min) to give rac-N-[(3S,4R)-1-tert-butyl-3-fluoro-4-piperidyl]-2-[3-(2-methoxy-4-methylsulfonyl-anilino)prop-1-ynyl]-1-(2,2,2-trifluoroethyl)indol-4-amine as white solid (40 mg, 36% yield). LC-MS (ES$^+$, m/z): 609.2 [(M+H)$^+$].

The enantiomers of rac-N-[(3S,4R)-1-tert-butyl-3-fluoro-4-piperidyl]-2-[3-(2-methoxy-4-methylsulfonyl-anilino)prop-1-ynyl]-1-(2,2,2-trifluoroethyl)indol-4-amine were then separated by chiral SFC (WHELK-01, 0.1% NH$_3$H$_2$O, EtOH) to give: N-[(3S,4R)-1-tert-butyl-3-fluoro-4-piperidyl]-2-[3-(2-methoxy-4-methylsulfonyl-anilino)prop-1-ynyl]-1-(2,2,2-trifluoroethyl)indol-4-amine (pre peak): 13.4 mg, 37% yield. LC-MS (ES$^+$, m/z): 609.3 [(M+H)$^+$]; N-[(3R,4S)-1-tert-butyl-3-fluoro-4-piperidyl]-2-[3-(2-methoxy-4-methylsulfonyl-anilino)prop-1-ynyl]-1-(2,2,2-trifluoroethyl)indol-4-amine (post peak): 15.2 mg, 42% yield. LC-MS (ES$^+$, m/z): 609.3 [(M+H)$^+$].

Example D176: Preparation of 4-[3-[4-[[(3S,4R)-1-tert-butyl-3-fluoro-4-piperidyl]amino]-1-(2,2,2-trifluoroethyl)indol-2-yl]prop-2-ynylamino]-3-methoxy-benzoic acid and 4-[3-[4-[[(3R,4S)-1-tert-butyl-3-fluoro-4-piperidyl]amino]-1-(2,2,2-trifluoroethyl)indol-2-yl]prop-2-ynylamino]-3-methoxy-benzoic acid

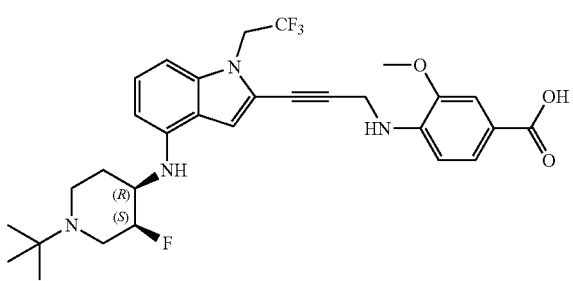

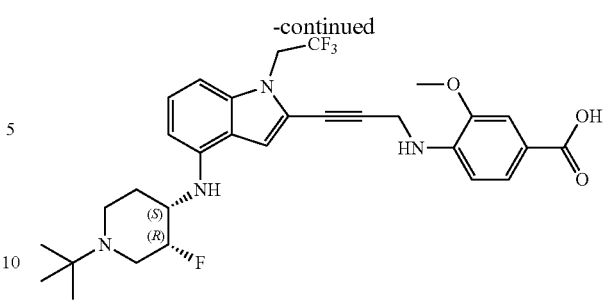

Synthesis of 3-methoxy-4-(prop-2-ynylamino)benzoate. To a mixture of methyl 4-[tert-butoxycarbonyl(prop-2-ynyl)amino]-3-methoxy-benzoate (400 mg, 1.25 mmol, 1.0 eq) in DCM (5 mL) was added TFA (1.54 g, 13.51 mmol, 1 mL, 10.9 eq) in one portion at 25° C. The mixture was stirred for 2 h. LCMS analysis showed that the reaction was completed. A saturated solution of NaHCO$_3$ was added to adjust the solution to pH=8. The aqueous phase was extracted with EtOAc (20 mL×3). The combined organic phases were washed with brine (20 mL×3), dried over anhydrous Na$_2$SO$_4$, filtered, and concentrated under reduced pressure to give the desired product as yellow oil (270 mg, crude). LC-MS (ES$^{30}$, m/z): 220.1 [(M+H)$^+$]

Synthesis of 3-methoxy-4-(prop-2-ynylamino)benzoic acid. To a mixture of crude methyl 3-methoxy-4-(prop-2-ynylamino)benzoate (270 mg, 1.23 mmol, 1.0 eq) in MeOH (2 mL) and water (0.5 mL) was added NaOH (147.8 mg, 3.69 mmol, 3.0 eq) in one portion at 40° C., and the mixture was stirred for 2 h. TLC analysis showed the reaction was complete. 2M HCl was added to adjust the solution to pH=6. The aqueous phase was extracted with EtOAc (20 mL×3). The combined organic phases were washed with brine (20 mL×3), dried over anhydrous Na$_2$SO$_4$, filtered, and concentrated under reduced pressure. The crude product was triturated with EtOAc at 20° C. for 10 min to give 3-methoxy-4-(prop-2-ynylamino)benzoic acid as white solid (200 mg, 974.61 μmol, 79.14% yield).

Synthesis of 4-[3-[4-[[(3S,4R)-1-tert-butyl-3-fluoro-4-piperidyl]amino]-1-(2,2,2-trifluoroethyl)indol-2-yl]prop-2-ynylamino]-3-methoxy-benzoic acid and 4-[3-[4-[[(3R,4S)-1-tert-butyl-3-fluoro-4-piperidyl]amino]-1-(2,2,2-trifluoroethyl)indol-2-yl]prop-2-ynylamino]-3-methoxy-benzoic acid. To a mixture of rac-N-((3S,4R)-1-(tert-butyl)-3-fluoropiperidin-4-yl)-2-iodo-1-(2,2,2-trifluoroethyl)-1H-indol-4-amine (80 mg, 144.78 μmol, 1.0 eq) and 3-methoxy-4-(prop-2-ynylamino)benzoic acid (44.6 mg, 217.17 μmol, 1.5 eq) in DMSO (3 mL) were added CuI (2.76 mg, 14.48 μmol, 0.1 eq), N-isopropylpropan-2-amine (146.5 mg, 1.45 mmol, 204.61 μL, 10.0 eq), and Pd(PPh$_3$)$_4$ (8.4 mg, 7.24 μmol, 0.1 eq) in one portion at 25° C. under N$_2$. The mixture was then stirred for 3 h, and LCMS analysis showed that the reaction was complete. The residue was poured into a saturated solution of EDTA (20 mL) and stirred for 120 min. The layers were separated, and the aqueous phase was extracted with EtOAc (20 mL×3). The combined organic phase was washed with brine (20 mL×3), dried over anhydrous Na$_2$SO$_4$, filtered, and concentrated under reduced pressure. The crude racemic product was first purified by preparative HPLC (Waters Xbridge Prep OBD C18 150×40 mm, 10 um; mobile phase: [water (10 mM NH$_4$HCO$_3$)-ACN]; B %: 60%-80%, 8 min), then the enantiomers were separated by chiral SFC (CHIRALCEL® OJ, MeOH_IPAm) to give: 4-[3-[4-[[(3S,4R)-1-tert-butyl-3-fluoro-4-piperidyl]amino]-1-(2,2,2-trifluoroethyl)indol-2-yl]prop-2- ynylamino]-3-methoxy-benzoic acid (pre peak): 12.9 mg, 16% yield. LC-MS (ES$^{30}$, m/z): 588.3 [(M+H)$^+$]; and 4-[3-[4-[[(3R,4S)-1-tert-butyl-3-fluoro-4-piperidyl]amino]-1-(2,2,2-trifluoroethyl)indol-2-yl]prop-2-ynylamino]-3-methoxy-benzoic acid (post peak): 16.8 mg, 20% yield. LC-MS (ES$^+$, m/z): 588.3 [(M+H)$^+$]

Example D177: Preparation of 4-[3-[4-[[(3S,4R)-1-tert-butyl-3-fluoro-4-piperidyl]amino]-1-(2,2,2-trifluoroethyl)indol-2-yl]-prop-2-ynylamino]-3-methoxy-N-methyl-benzamide and 4-[3-[4-[[(3R,4S)-1-tert-butyl-3-fluoro-4-piperidyl]amino]-1-(2,2,2-trifluoroethyl)indol-2-yl]prop-2-ynylamino]-3-methoxy-N-methyl-benzamide

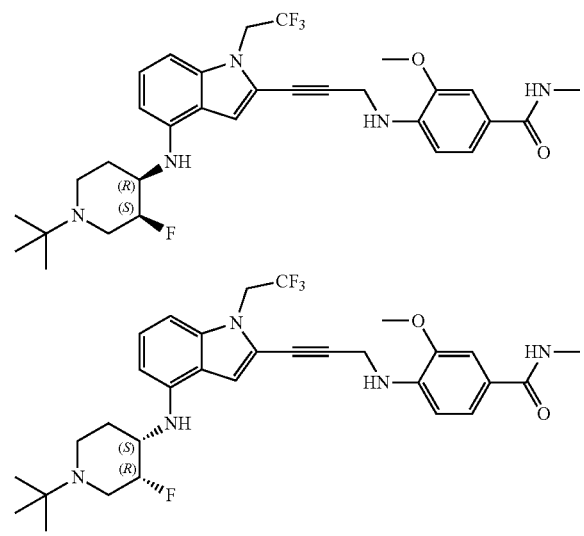

To a mixture of rac-N-((3S,4R)-1-(tert-butyl)-3-fluoropiperidin-4-yl)-2-iodo-1-(2,2,2-trifluoroethyl)-1H-indol-4-amine (160 mg, 289.56 µmol, 1.0 eq) and 3-methoxy-N-methyl-4-(prop-2-ynylamino)benzamide (126.39 mg, 579.12 µmol, 2.0 eq) in DMSO (4 mL) were added CuI (551.5 ug, 2.90 µmol, 0.1 eq), N-isopropylpropan-2-amine (293.0 mg, 2.90 mmol, 409.22 µL, 10.0 eq), and Pd(PPh$_3$)$_4$ (16.7 mg, 14.48 µmol, 0.1 eq) in one portion at 25° C. under N$_2$. The reaction mixture was then stirred for 3 h. LCMS analysis showed the desired product. A saturated solution of EDTA (20 mL) was added, and the mixture was stirred for 2 h. The phases were separated, and the aqueous phase was extracted with EtOAc (20 mL×3). The combined organic phases were washed with brine (20 mL×3), dried over anhydrous Na$_2$SO$_4$, filtered, and concentrated under reduced pressure to dryness. The crude racemic product was first purified by preparative HPLC (Waters Xbridge Prep OBD C18 150×40 mm, 10 um; mobile phase: 10 mM NH$_4$HCO$_3$-MeCN; B %: 60%-80%, 8 min), then the enantiomers were separated by chiral SFC (ChiralPak AD, Isopropyl alcohol_IPAm) to give: 4-[3-[4-[[(3S,4R)-1-tert-butyl-3-fluoro-4-piperidyl]amino]-1-(2,2,2-trifluoroethyl)indol-2-yl]-prop-2-ynylamino]-3-methoxy-N-methyl-benzamide (pre peak): 52.6 mg, 31% yield. LC-MS (ES$^{30}$, m/z): 588.3 [(M+H)$^+$]; 4-[3-[4-[[(3R,4S)-1-tert-butyl-3-fluoro-4-piperidyl]amino]-1-(2,2,2-trifluoroethyl)indol-2-yl]prop-2-ynylamino]-3-methoxy-N-methyl-benzamide (post peak): 33.7 mg, 19.6% yield. LC-MS (ES$^+$, m/z): 588.3 [(M+H)$^+$].

Example D178: Preparation of 4-{[3-(4-{[(3S,4R)-1-ethyl-3-fluoropiperidin-4-yl]amino}-1-(2,2,2-trifluoroethyl)-1H-indol-2-yl)prop-2-yn-1-yl]amino}-3-methoxy-N-methylbenzamide and 4-{[3-(4-{[(3R,4S)-1-ethyl-3-fluoropiperidin-4-yl]amino}-1-(2,2,2-trifluoroethyl)-1H-indol-2-yl)prop-2-yn-1-yl]amino}-3-methoxy-N-methylbenzamide

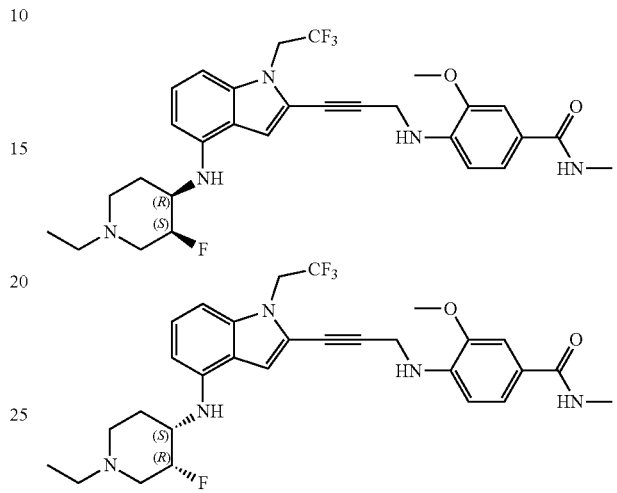

Synthesis of N-[(3S,4R)-1-ethyl-3-fluoro-4-piperidyl]-2-iodo-1-(2,2,2-trifluoroethyl)indol-4-amine. To a solution of N-[(3S,4R)-3-fluoro-4-piperidyl]-2-iodo-1-(2,2,2-trifluoroethyl) indol-4-amine (200 mg, 453.30 µmol, 1.0 eq) in DMF (4 ml) were added K$_2$CO$_3$ (125.3 mg, 906.61 µmol, 2.0 eq) and iodoethane (106.1 mg, 679.96 µmol, 54.38 µL, 1.5 eq). The reaction mixture was stirred at 20° C. for 2 h. LCMS and TLC analysis (SiO$_2$, DCM/MEOH=10:1) showed that the reaction was completed. The reaction was quenched by adding water (20 mL) and extracting the mixture with EtOAc (20 mL×3). The combined organic phases were washed with brine (20 mL×3), dried over anhydrous Na$_2$SO$_4$, filtered, and concentrated in vacuum. The crude was purified by preparative TLC (SiO$_2$, DCM/MEOH=10:1) to give N-[(3S,4R)-1-ethyl-3-fluoro-4-piperidyl]-2-iodo-1-(2,2,2-trifluoroethyl)indol-4-amine as yellow oil (190 mg, 89% yield). LC-MS (ES$^{30}$, m/z): 470.1 [(M+H)$^+$].

Synthesis of 4-[3-[4-[[(3S,4R)-1-ethyl-3-fluoro-4-piperidyl]amino]-1-(2,2,2-trifluoroethyl) indol-2-yl]prop-2-ynylamino]-3-methoxy-N-methyl-benzamide and 4-[3-[4-[[(3R,4S)-1-ethyl-3-fluoro-4-piperidyl]amino]-1-(2,2,2-trifluoroethyl)indol-2-yl]prop-2-ynylamino]-3-methoxy-N-methyl-benzamide. To a mixture of N-[(3S,4R)-1-ethyl-3-fluoro-4-piperidyl]-2-iodo-1-(2,2,2-trifluoroethyl)indol-4-amine (200 mg, 426.21 µmol, 1.0 eq) and 3-methoxy-N-methyl-4-(prop-2-ynylamino)benzamide (102.32 mg, 468.83 µmol, 1.1 eq) in DMSO (5 ml) were added CuI (8.12 mg, 42.62 µmol, 0.1 eq), Pd(PPh$_3$)$_4$ (24.63 mg, 21.31 µmol, 0.05 eq), and N-isopropylpropan-2-amine (431.28 mg, 4.26 mmol, 602.34 µL, 10.0 eq) at 20° C., and the reaction was stirred for 1 h. LCMS analysis showed that the reaction was completed. The residue was poured into a saturated solution of EDTA (20 ml) and stirred for 120 min. The aqueous phase was extracted with EtOAc (30 mL×3). The combined organic phase was washed with brine (30 mL×3), dried over anhydrous Na$_2$SO$_4$, filtered and concentrated in vacuo. The crude residue was purified by prep-HPLC (Phenomenex Luna C18 75×30 mm, 3 um; mobile phase: [water (0.2%

FA)-ACN]; B %: 20%-40%, 10 min) to give the racemic product. The enantiomers were then separated by chiral SFC (DAICEL CHIRALCEL OJ 250×30 mm, 10 um); mobile phase: [0.1% NH$_3$H$_2$O in EtOH]; B %: 45%-45%, 10 min) to give: 4-[3-[4-[[(3S,4R)-1-ethyl-3-fluoro-4-piperidyl]amino]-1-(2,2,2-trifluoroethyl)indol-2-yl]prop-2-ynylamino]-3-methoxy-N-methyl-benzamide (38.6 mg, 16% yield). LC-MS (ES$^+$, m/z): 560.1 [(M+H)]$^+$; and 4-[3-[4-[[(3R,4S)-1-ethyl-3-fluoro-4-piperidyl]amino]-1-(2,2,2-trifluoroethyl) indol-2-yl]prop-2-ynylamino]-3-methoxy-N-methyl-benzamide (27 mg, 110 yield). LC-MS (ES$^+$, m/z): 560.1 [(M+H)$^+$].

TABLE 4 shows compounds with a 2-ethynyl-N-(heterocyclyl)-1H-indole-4-amine core.

TABLE 4

| Compound No. | Structure | IUPAC | LC-MS (ES+, m/z) |
|---|---|---|---|
| 455A | 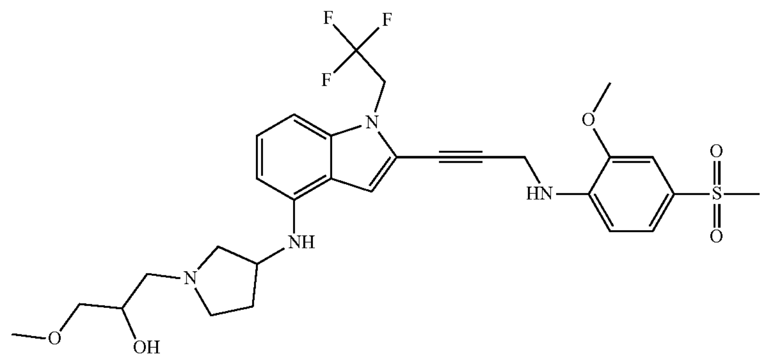 | 1-{3-[(2-{3-[(4-methanesulfonyl-2-methoxyphenyl)amino]prop-1-yn-1-yl}-1-(2,2,2-trifluoroethyl)-1H-indol-4-yl)amino]pyrrolidin-1-yl}-3-methoxypropan-2-ol | 608.9 |
| 456A | 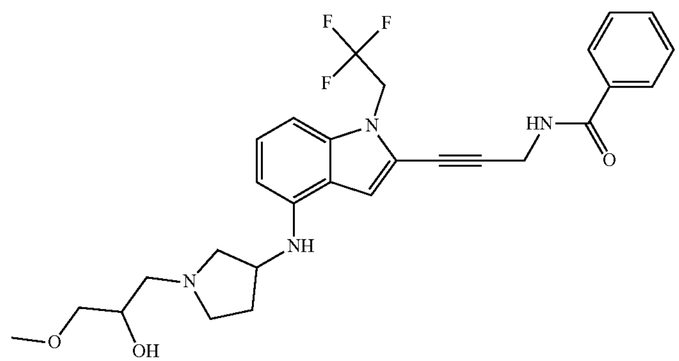 [SMILES: COCC(O)CN1CCC(Nc2cccc3c2cc(C#CCNC(=O)c2ccccc2)n3CC(F)(F)F)C1] | N-[3-(4-{[1-(2-hydroxy-3-methoxypropyl)pyrrolidin-3-yl]amino}-1-(2,2,2-trifluoroethyl)-1H-indol-2-yl)prop-2-yn-1-yl]benzamide | 528.9 |

TABLE 4-continued

| Compound No. | Structure | IUPAC | LC-MS (ES+, m/z) |
|---|---|---|---|
| 457A | 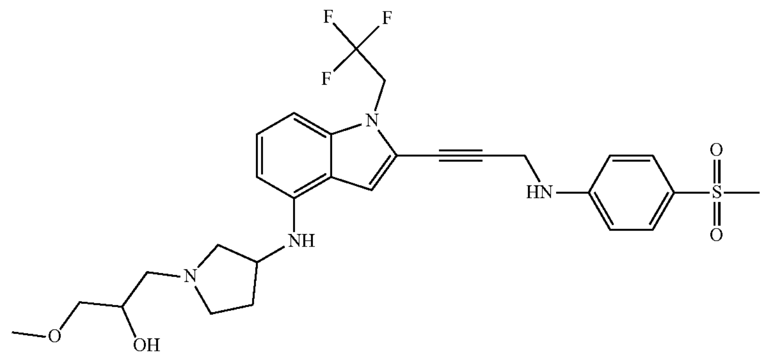 | 1-{3-[(2-{3-[(4-methanesulfonylphenyl)amino]prop-1-yn-1-yl}-1-(2,2,2-trifluoroethyl)-1H-indol-4-yl)amino]pyrrolidin-1-yl}-3-methoxypropan-2-ol | 578.9 |
| 458A | 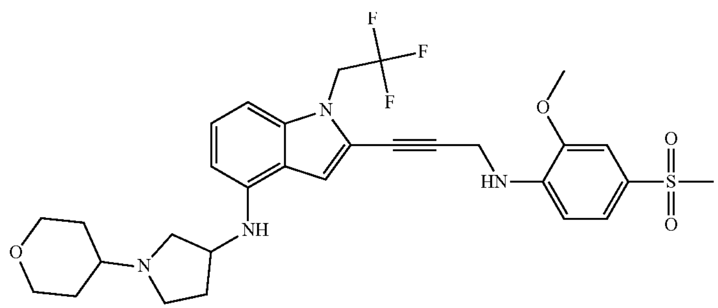 [SMILES: COc1cc(S(C)(=O)=O)ccc1NCC#Cc1cc2c(NC3CCN(C4CCOCC4)C3)cccc2n1CC(F)(F)F] | 2-{3-[(4-methanesulfonyl-2-methoxyphenyl)amino]prop-1-yn-1-yl}-N-[1-(oxan-4-yl)pyrrolidin-3-yl]-1-(2,2,2-trifluoroethyl)-1H-indol-4-amine | 604.9 |
| 459A | 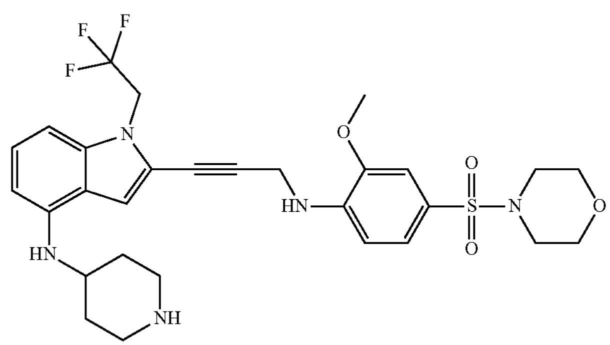 [SMILES: COc1cc(S(=O)(=O)N2CCOCC2)ccc1NCC#Cc1cc2c(NC3CCNCC3)cccc2n1CC(F)(F)F] | 2-(3-{[2-methoxy-4-(morpholine-4-sulfonyl)phenyl]amino}prop-1-yn-1-yl)-N-(piperidin-4-yl)-1-(2,2,2-trifluoroethyl)-1H-indol-4-amine | 606.2 |

TABLE 4-continued

| Compound No. | Structure | IUPAC | LC-MS (ES+, m/z) |
|---|---|---|---|
| 460A | 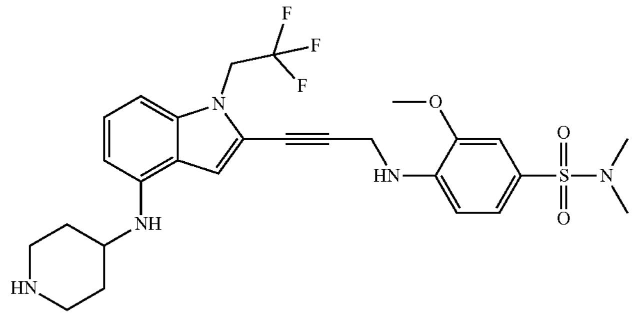 [SMILES: COc1cc(S(=O)(=O)N(C)C)ccc1NCC#Cc1cc2c(NC3CCNCC3)cccc2n1CC(F)(F)F] | 3-methoxy-N,N-dimethyl-4-[(3-{4-[(piperidin-4-yl)amino]-1-(2,2,2-trifluoroethyl)-1H-indol-2-yl}prop-2-yn-1-yl)amino]benzene-1-sulfonamide | 564.3 |
| 461A | 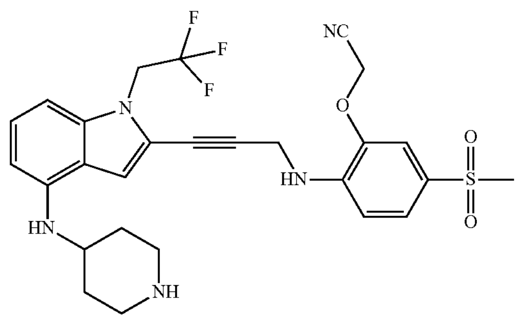 [SMILES: CS(=O)(=O)c1ccc(NCC#Cc2cc3c(NC4CCNCC4)cccc3n2CC(F)(F)F)c(OCC#N)c1] | 2-{5-methanesulfonyl-2-[(3-{4-[(piperidin-4-yl)amino]-1-(2,2,2-trifluoroethyl)-1H-indol-2-yl}prop-2-yn-1-yl)amino]phenoxy}acetonitrile | 560.2 |
| 462A | 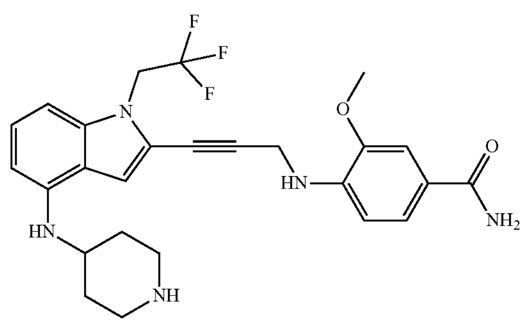 [SMILES: COc1cc(C(N)=O)ccc1NCC#Cc1cc2c(NC3CCNCC3)cccc2n1CC(F)(F)F] | 3-methoxy-4-((3-(4-(piperidin-4-yl)amino)-1-(2,2,2-trifluoroethyl)-1H-indol-2-yl)prop-2-yn-1-yl)amino)benzamide | 500.3 |

TABLE 4-continued

| Compound No. | Structure | IUPAC | LC-MS (ES+, m/z) |
|---|---|---|---|
| 463A | 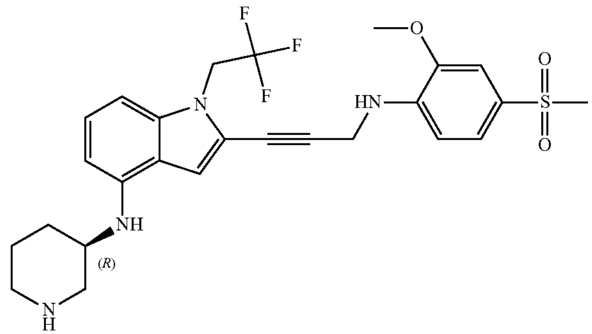 | 2-{3-[(4-methanesulfonyl-2-methoxyphenyl)amino]prop-1-yn-1-yl}-N-[(3R)-piperidin-3-yl]-1-(2,2,2-trifluoroethyl)-1H-indol-4-amine | 534.9 |
| 464A | 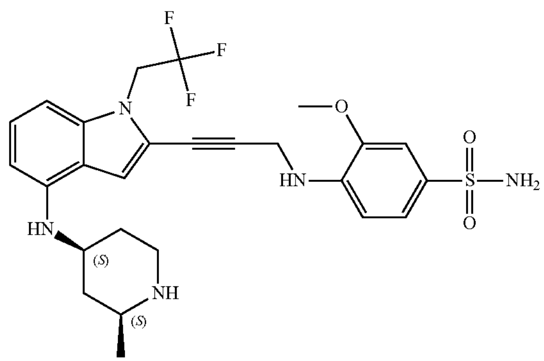 | 3-methoxy-4-{[3-(4-{[(2S,4S)-2-methylpiperidin-4-yl]amino}-1-(2,2,2-trifluoroethyl)-1H-indol-2-yl)prop-2-yn-1-yl]amino}benzene-1-sulfonamide | 550.1 |
| 465A | 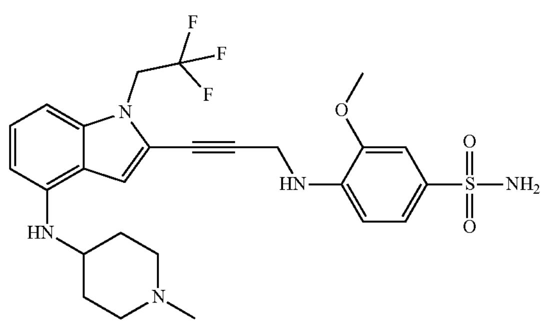 [SMILES: COc1cc(S(N)(=O)=O)ccc1NCC#Cc1cc2c(NC3CCN(C)CC3)cccc2n1CC(F)(F)F] | 3-methoxy-4-((3-(4-((1-methylpiperidin-4-yl)amino)-1-(2,2,2-trifluoroethyl)-1H-indol-2-yl)prop-2-yn-1-yl)amino)benzenesulfonamide | 550.2 |

TABLE 4-continued

| Compound No. | Structure | IUPAC | LC-MS (ES⁺, m/z) |
|---|---|---|---|
| 466A | 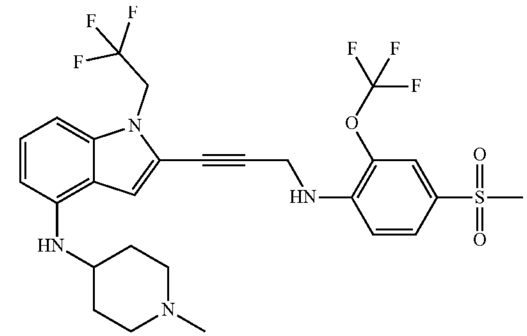 [SMILES: CN1CCC(Nc2cccc3c2cc(C#CCNc2ccc(S(C)(=O)=O)cc2OC(F)(F)F)n3CC(F)(F)F)CC1] | 2-(3-{[4-methanesulfonyl-2-(trifluoromethoxy)phenyl]amino}prop-1-yn-1-yl)-N-(1-methylpiperidin-4-yl)-1-(2,2,2-trifluoroethyl)-1H-indol-4-amine | 603.1 |
| 467A | 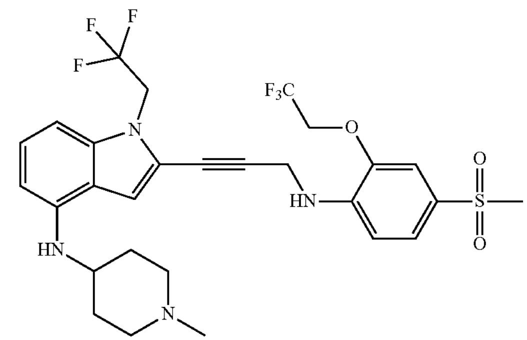 [SMILES: CN1CCC(Nc2cccc3c2cc(C#CCNc2ccc(S(C)(=O)=O)cc2OCC(F)(F)F)n3CC(F)(F)F)CC1] | N-(1-methylpiperidin-4-yl)-2-(3-((4-(methylsulfonyl)-2-(2,2,2-trifluoroethoxy)phenyl)amino)prop-1-yn-1-yl)-1-(2,2,2-trifluoroethyl)-1H-indol-4-amine | 617.2 |
| 468A | 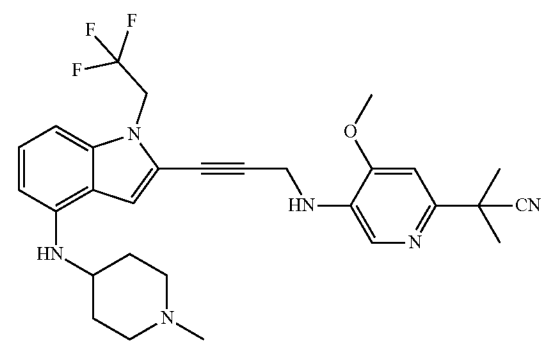 [SMILES: COc1cc(C(C)(C)C#N)ncc1NCC#Cc1cc2c(NC3CCN(C)CC3)cccc2n1CC(F)(F)F] | 2-{4-methoxy-5-[(3-{4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile | 539.3 |

TABLE 4-continued

| Compound No. | Structure | IUPAC | LC-MS (ES+; m/z) |
|---|---|---|---|
| 469A | 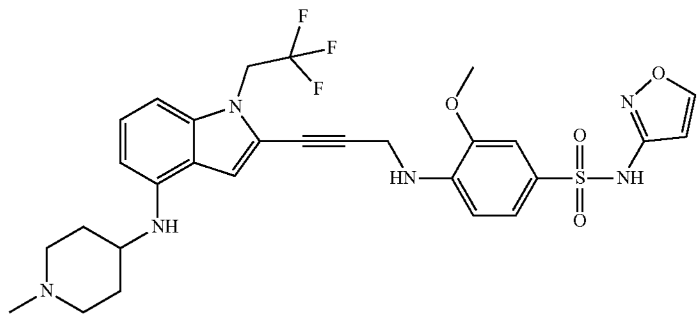 [SMILES: COc1cc(S(=O)(=O)Nc2ccon2)ccc1NCC#Cc1cc2c(NC3CCN(C)CC3)cccc2n1CC(F)(F)F] | 3-methoxy-4-[(3-{4-[(1-methylpiperidin-4-yl)amino]-1-(2,2,2-trifluoroethyl)-1H-indol-2-yl}prop-2-yn-1-yl)amino]-N-(1,2-oxazol-3-yl)benzene-1-sulfonamide | 617.2 |
| 470A | 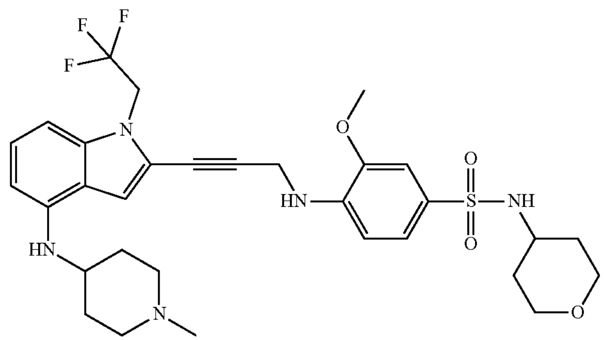 [SMILES: COc1cc(S(=O)(=O)NC2CCOCC2)ccc1NCC#Cc1cc2c(NC3CCN(C)CC3)cccc2n1CC(F)(F)F] | 3-methoxy-4-[(3-{4-[(1-methylpiperidin-4-yl)amino]-1-(2,2,2-trifluoroethyl)-1H-indol-2-yl}prop-2-yn-1-yl)amino]-N-(oxan-4-yl)benzene-1-sulfonamide | 634.2 |
| 471A | 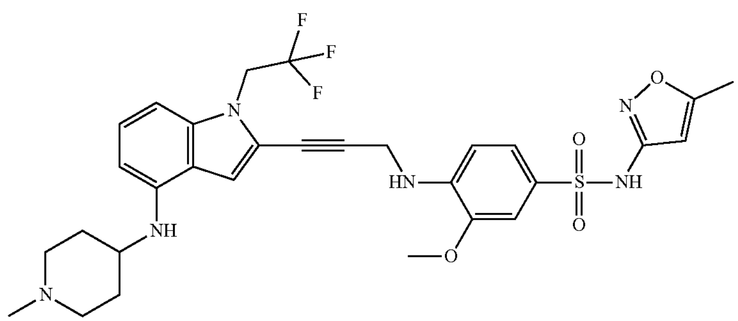 | 3-methoxy-N-(5-methyl-1,2-oxazol-3-yl)-4-[(3-{4-[(1-methylpiperidin-4-yl)amino]-1-(2,2,2-trifluoroethyl)-1H-indol-2-yl}prop-2-yn-1-yl)amino]benzene-1-sulfonamide | 631.2 |

TABLE 4-continued

| Compound No. | Structure | IUPAC | LC-MS (ES+, m/z) |
|---|---|---|---|
| 472A | 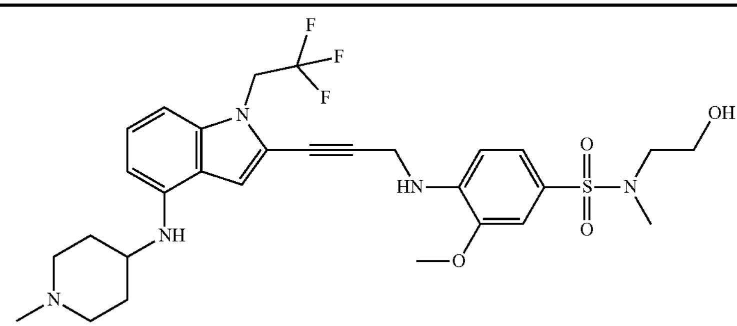 | N-(2-hydroxyethyl)-3-methoxy-4-[(3-{4-[(1-methylpiperidin-4-yl)amino]-1-(2,2,2-trifluoroethyl)-1H-indol-2-yl}prop-2-yn-1-yl)amino]benzene-1-sulfonamide | 608.2 |
| 473A | 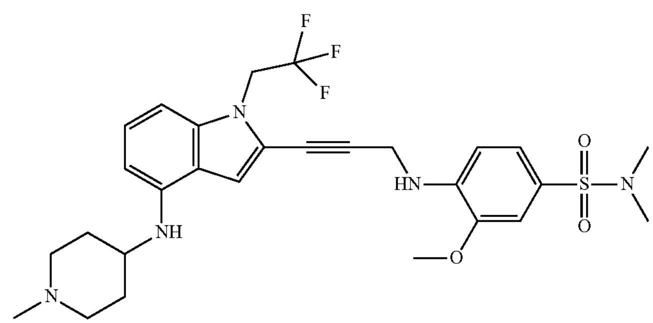 | 3-methoxy-N,N-dimethyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide | 578.2 |
| 474A | 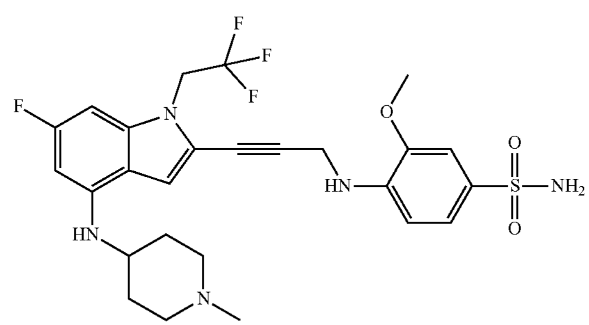 [SMILES: COc1cc(S(N)(=O)=O)ccc1NCC#Cc1cc2c(NC3CCN(C)CC3)cc(F)cc2n1CC(F)(F)F] | 4-[(3-{6-fluoro-4-[(1-methylpiperidin-4-yl)amino]-1-(2,2,2-trifluoroethyl)-1H-indol-2-yl}prop-2-yn-1-yl)amino]-3-methoxybenzene-1-sulfonamide | 568.2 |

TABLE 4-continued

| Compound No. | Structure | IUPAC | LC-MS (ES+, m/z) |
|---|---|---|---|
| 475A | 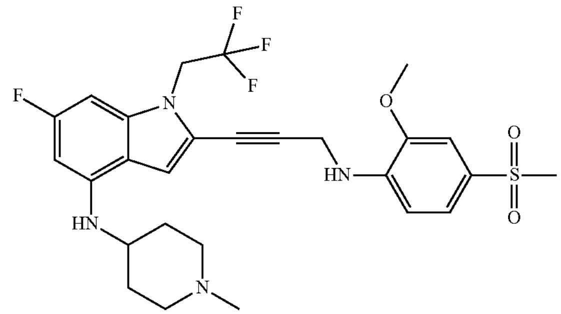 [SMILES: COc1cc(S(C)(=O)=O)ccc1NCC#Cc1cc2c(NC3CCN(C)CC3)cc(F)cc2n1CC(F)(F)F] | 6-fluoro-2-{3-[(4-methanesulfonyl-2-methoxyphenyl)amino]prop-1-yn-1-yl}-N-(1-methylpiperidin-4-yl)-1-(2,2,2-trifluoroethyl)-1H-indol-4-amine | 567.2 |
| 476A | 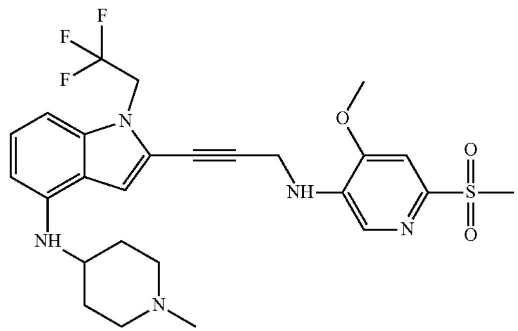 [SMILES: COc1cc(S(C)(=O)=O)ncc1NCC#Cc1cc2c(NC3CCN(C)CC3)cccc2n1CC(F)(F)F] | 2-(3-((4-methoxy-6-(methylsulfonyl)pyridin-3-yl)amino)prop-1-yn-1-yl)-N-(1-methylpiperidin-4-yl)-1-(2,2,2-trifluoroethyl)-1H-indol-4-amine | 550.1 |
| 477A | 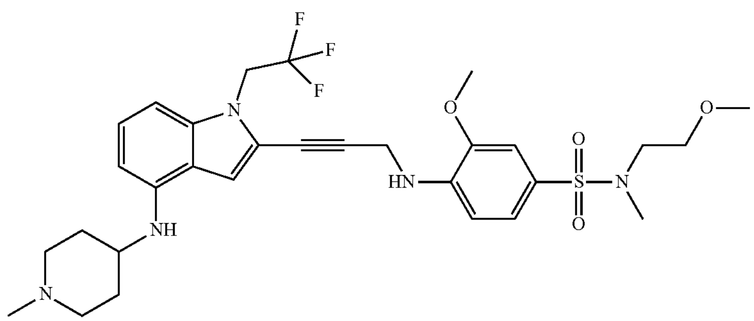 | 3-methoxy-N-(2-methoxyethyl)-N-methyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide | 622.2 |

TABLE 4-continued

| Compound No. | Structure | IUPAC | LC-MS (ES+, m/z) |
|---|---|---|---|
| 478A | 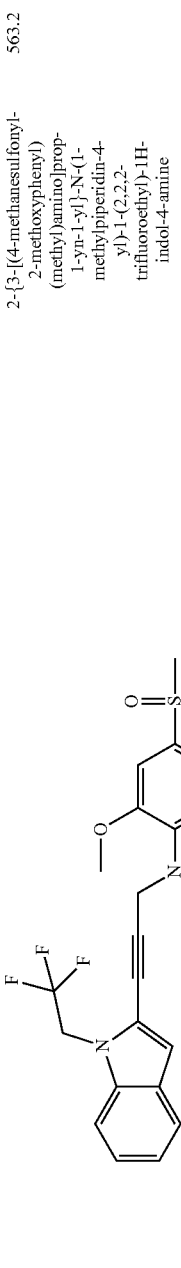 | 2-{3-[(4-methanesulfonyl-2-methoxyphenyl)(methyl)amino]prop-1-yn-1-yl}-N-(1-methylpiperidin-4-yl)-1-(2,2,2-trifluoroethyl)-1H-indol-4-amine | 563.2 |
| 479A | 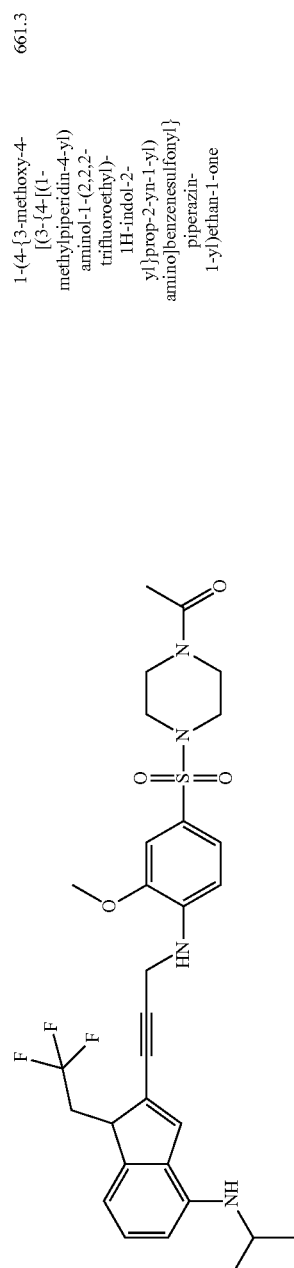 | 1-(4-{3-methoxy-4-[(3-{4-[(1-methylpiperidin-4-yl)aminol-1-(2,2,2-trifluoroethyl)-1H-indol-2-yl}prop-2-yn-1-yl)amino]benzenesulfonyl}piperazin-1-yl)ethan-1-one | 661.3 |
| 480A | 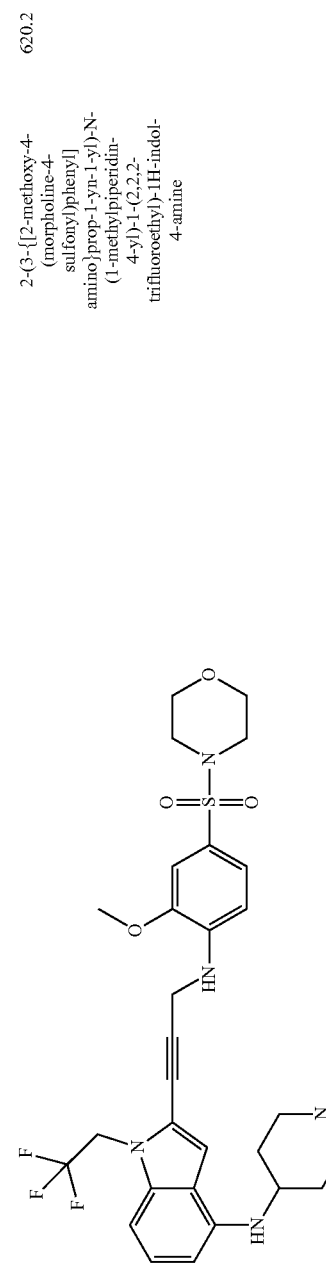 | 2-(3-{[2-methoxy-4-(morpholine-4-sulfonyl)phenyl]amino}prop-1-yn-1-yl)-N-(1-methylpiperidin-4-yl)-1-(2,2,2-trifluoroethyl)-1H-indol-4-amine | 620.2 |

TABLE 4-continued

| Compound No. | Structure | IUPAC | LC-MS (ES+, m/z) |
|---|---|---|---|
| 481A | 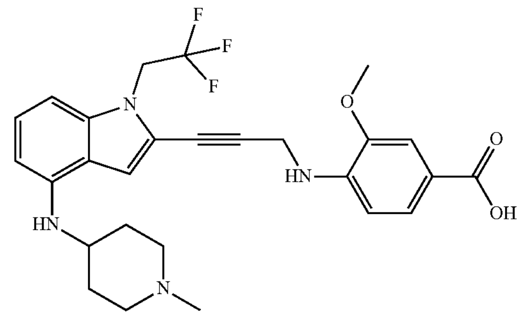 [SMILES: COc1cc(C(=O)O)ccc1NCC#Cc1cc2c(NC3CCN(C)CC3)cccc2n1CC(F)(F)F] | 3-methoxy-4-((3-(4-((1-methylpiperidin-4-yl)amino)-1-(2,2,2-trifluoroethyl)-1H-indol-2-yl)prop-2-yn-1-yl)amino)benzoic acid | 515.1 |
| 482A | 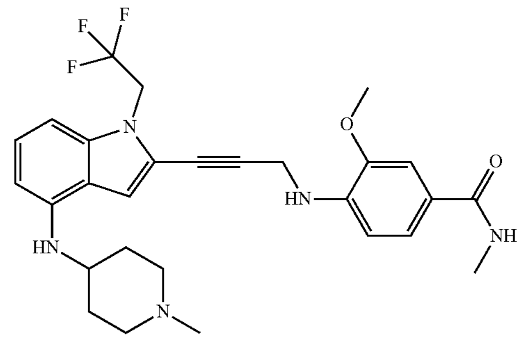 [SMILES: CNC(=O)c1ccc(NCC#Cc2cc3c(NC4CCN(C)CC4)cccc3n2CC(F)(F)F)c(OC)c1] | 3-methoxy-N-methyl-4-[(3-{4-[(1-methylpiperidin-4-yl)amino]-1-(2,2,2-trifluoroethyl)-1H-indol-2-yl}prop-2-yn-1-yl)amino]benzamide | 528.2 |
| 483A | 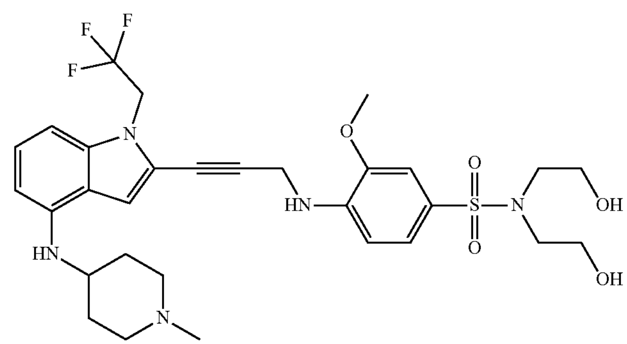 [SMILES: COc1cc(S(=O)(=O)N(CCO)CCO)ccc1NCC#Cc1cc2c(NC3CCN(C)CC3)cccc2n1CC(F)(F)F] | N,N-bis(2-hydroxyethyl)-3-methoxy-4-[(3-{4-[(1-methylpiperidin-4-yl)amino]-1-(2,2,2-trifluoroethyl)-1H-indol-2-yl}prop-2-yn-1-yl)amino]benzene-1-sulfonamide | 638.2 |

TABLE 4-continued

| Compound No. | Structure | IUPAC | LC-MS (ES+, m/z) |
|---|---|---|---|
| 484A | 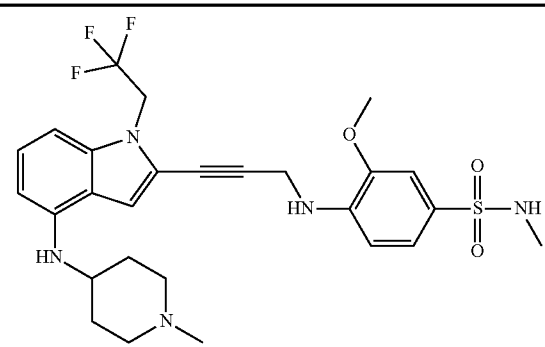 | 3-methoxy-N-methyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide | 564.2 |
| 485A | 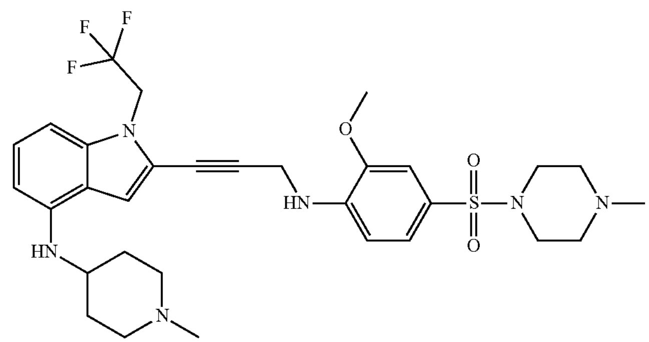 [SMILES: COc1cc(S(=O)(=O)N2CCN(C)CC2)ccc1NCC#Cc1cc2c(NC3CCN(C)CC3)cccc2n1CC(F)(F)F] | 2-[3-({2-methoxy-4-[(4-methylpiperazin-1-yl)sulfonyl]phenyl}amino)prop-1-yn-1-yl]-N-(1-methylpiperidin-4-yl)-1-(2,2,2-trifluoroethyl)-1H-indol-4-amine | 633.3 |
| 486A | 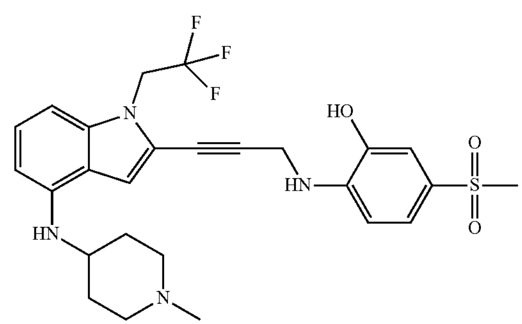 [SMILES: CN1CCC(Nc2cccc3c2cc(C#CCNc2ccc(S(C)(=O)=O)cc2O)n3CC(F)(F)F)CC1] | 5-methanesulfonyl-2-[3-{4-[(1-methylpiperidin-4-yl)amino]-1-(2,2,2-trifluoroethyl)-1H-indol-2-yl}prop-2-yn-1-yl)amino]phenol | 535.2 |

TABLE 4-continued

| Compound No. | Structure | IUPAC | LC-MS (ES+, m/z) |
|---|---|---|---|
| 487A | 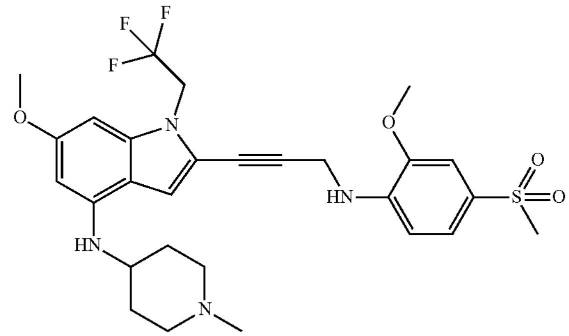 [SMILES: COc1cc(NC2CCN(C)CC2)c2cc(C#CCNc3ccc(S(C)(=O)=O)cc3OC)n(CC(F)(F)F)c2c1] | 2-{3-[(4-methanesulfonyl-2-methoxyphenyl)amino]prop-1-yn-1-yl}-6-methoxy-N-(1-methylpiperidin-4-yl)-1-(2,2,2-trifluoroethyl)-1H-indol-4-amine | 579.2 |
| 488A | 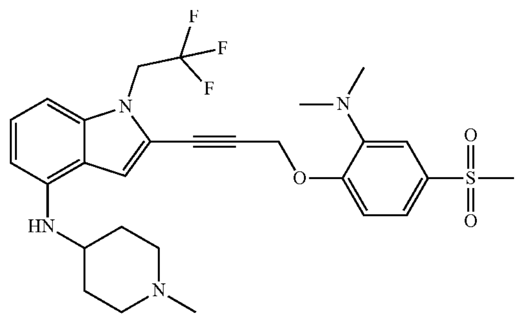 [SMILES: CN1CCC(Nc2cccc3c2cc(C#CCOc2ccc(S(C)(=O)=O)cc2N(C)C)n3CC(F)(F)F)CC1] | 2-{3-[2-(dimethylamino)-4-methanesulfonylphenoxy]prop-1-yn-1-yl}-N-(1-methylpiperidin-4-yl)-1-(2,2,2-trifluoroethyl)-1H-indol-4-amine | 563.2 |
| 489A | 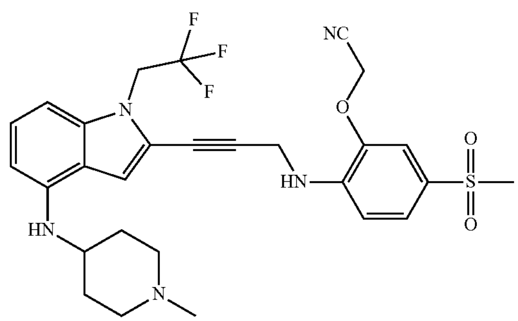 [SMILES: CN1CCC(Nc2cccc3c2cc(C#CCNc2ccc(S(C)(=O)=O)cc2OCC#N)n3CC(F)(F)F)CC1] | 2-{5-methanesulfonyl-2-[(3-{4-[(1-methylpiperidin-4-yl)amino]-1-(2,2,2-trifluoroethyl)-1H-indol-2-yl}prop-2-yn-1-yl)amino]phenoxy}acetonitrile | 574.3 |

TABLE 4-continued

| Compound No. | Structure | IUPAC | LC-MS (ES+, m/z) |
|---|---|---|---|
| 490A | 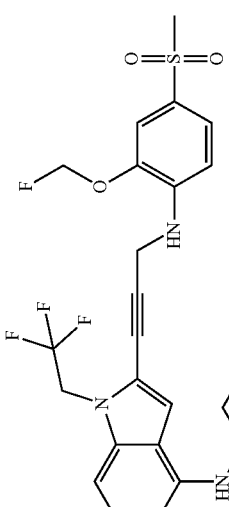 | 2-(3-{[2-(fluoromethoxy)-4-methanesulfonylphenyl]amino}prop-1-yn-1-yl)-N-(1-methylpiperidin-4-yl)-1-(2,2,2-trifluoroethyl)-1H-indol-4-amine | 567.2 |
| 491A | 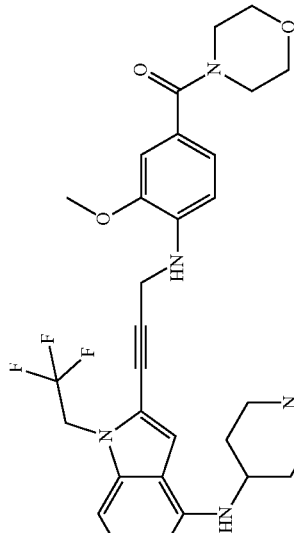 | 2-(3-{[2-methoxy-4-(morpholine-4-carbonyl)phenyl]amino}prop-1-yn-1-yl)-N-(1-methylpiperidin-4-yl)-1-(2,2,2-trifluoroethyl)-1H-indol-4-amine | 584.3 |
| 492A | 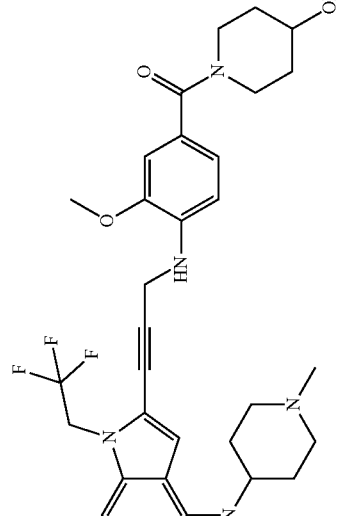 | 1-{3-methoxy-4-[(3-{4-[(1-methylpiperidin-4-yl)amino]-1-(2,2,2-trifluoroethyl)-1H-indol-2-yl}prop-2-yn-1-yl)amino]benzoyl}piperidin-4-ol | 598.3 |

TABLE 4-continued

| Compound No. | Structure | IUPAC | LC-MS (ES+, m/z) |
|---|---|---|---|
| 493A | 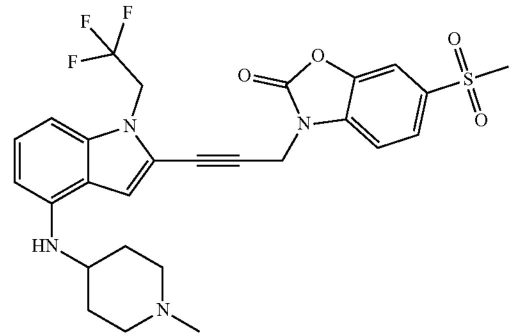 [SMILES: CN1CCC(Nc2cccc3c2cc(C#CCn2c(=O)oc4cc(S(C)(=O)=O)ccc42)n3CC(F)(F)F)CC1] | 3-(3-(4-((1-methylpiperidin-4-yl)amino)-1-(2,2,2-trifluoroethyl)-1H-indol-2-yl)prop-2-yn-1-yl)-6-(methylsulfonyl)benzo[d]oxazol-2(3H)-one | 561.2 |
| 494A | 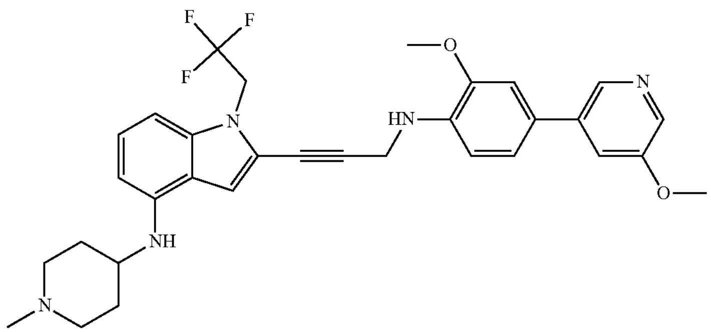 | 2-(3-{[2-methoxy-4-(5-methoxypyridin-3-yl)phenyl]amino}prop-1-yn-1-yl)-N-(1-methylpiperidin-4-yl)-1-(2,2,2-trifluoroethyl)-1H-indol-4-amine | 578.3 |
| 495A | 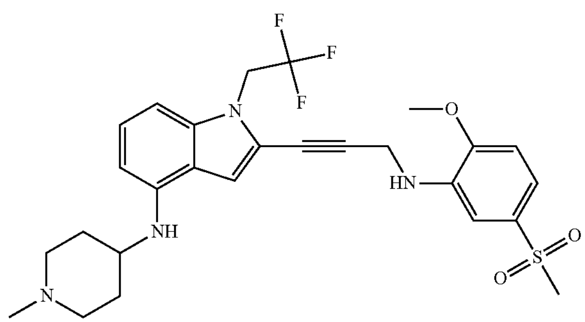 [SMILES: COc1ccc(S(C)(=O)=O)cc1NCC#Cc1cc2c(NC3CCN(C)CC3)cccc2n1CC(F)(F)F] | 2-{3-[(5-methanesulfonyl-2-methoxyphenyl)amino]prop-1-yn-1-yl}-N-(1-methylpiperidin-4-yl)-1-(2,2,2-trifluoroethyl)-1H-indol-4-amine | 549.3 |

TABLE 4-continued

| Compound No. | Structure | IUPAC | LC-MS (ES+, m/z) |
|---|---|---|---|
| 496A | 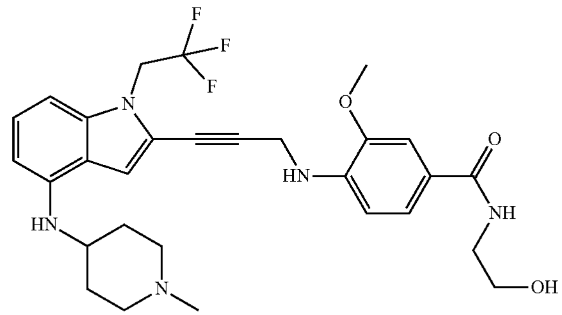 [SMILES: COc1cc(C(=O)NCCO)ccc1NCC#Cc1cc2c(NC3CCN(C)CC3)cccc2n1CC(F)(F)F] | N-(2-hydroxyethyl)-3-methoxy-4-[(3-{4-[(1-methylpiperidin-4-yl)amino]-1-(2,2,2-trifluoroethyl)-1H-indol-2-yl}prop-2-yn-1-yl)amino]benzamide | 558.2 |
| 497A | 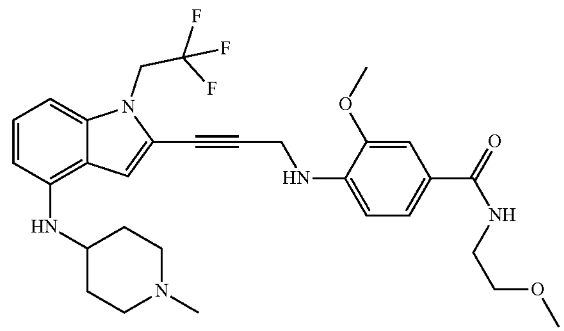 [SMILES: COCCNC(=O)c1ccc(NCC#Cc2cc3c(NC4CCN(C)CC4)cccc3n2CC(F)(F)F)c(OC)c1] | 3-methoxy-N-(2-methoxyethyl)-4-[(3-{4-[(1-methylpiperidin-4-yl)amino]-1-(2,2,2-trifluoroethyl)-1H-indol-2-yl}prop-2-yn-1-yl)amino]benzamide | 572.2 |
| 498A | 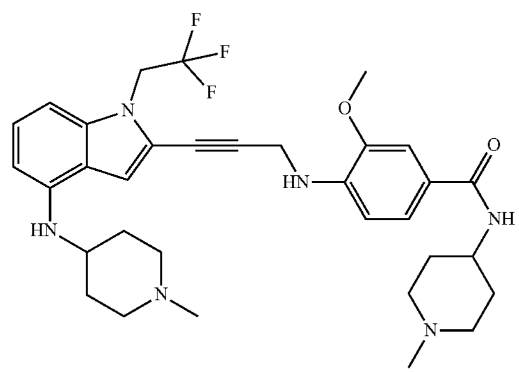 [SMILES: COc1cc(C(=O)NC2CCN(C)CC2)ccc1NCC#Cc1cc2c(NC3CCN(C)CC3)cccc2n1CC(F)(F)F] | 3-methoxy-N-(1-methylpiperidin-4-yl)-4-[(3-{4-[(1-methylpiperidin-4-yl)amino]-1-(2,2,2-trifluoroethyl)-1H-indol-2-yl}prop-2-yn-1-yl)amino]benzamide | 611.3 |

TABLE 4-continued

| Compound No. | Structure | IUPAC | LC-MS (ES+, m/z) |
|---|---|---|---|
| 499A | 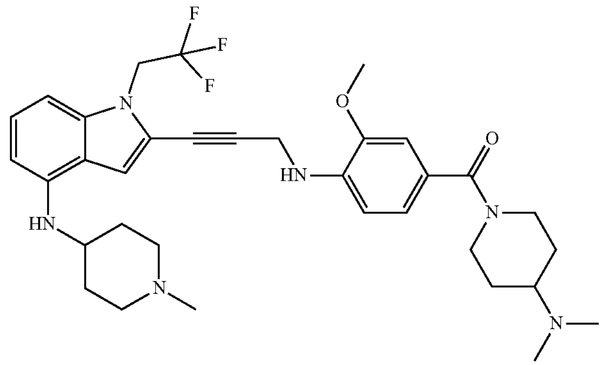 [SMILES: COc1cc(C(=O)N2CCC(N(C)C)CC2)ccc1NCC#Cc1cc2c(NC3CCN(C)CC3)cccc2n1CC(F)(F)F] | 2-[3-({4-[4-(dimethylamino)piperidine-1-carbonyl]-2-methoxyphenyl}amino)prop-1-yn-1-yl]-N-(1-methylpiperidin-4-yl)-1-(2,2,2-trifluoroethyl)-1H-indol-4-amine | 625.3 |
| 500A | 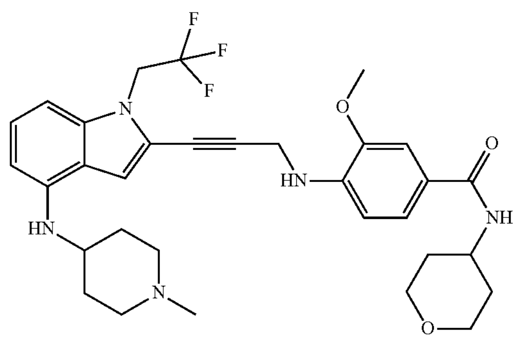 [SMILES: COc1cc(C(=O)NC2CCOCC2)ccc1NCC#Cc1cc2c(NC3CCN(C)CC3)cccc2n1CC(F)(F)F] | 3-methoxy-4-[(3-{4-[(1-methylpiperidin-4-yl)amino]-1-(2,2,2-trifluoroethyl)-1H-indol-2-yl}prop-2-yn-1-yl)amino]-N-(oxan-4-yl)benzamide | 598.3 |

TABLE 4-continued

| Compound No. | Structure | IUPAC | LC-MS (ES+, m/z) |
|---|---|---|---|
| 501A | 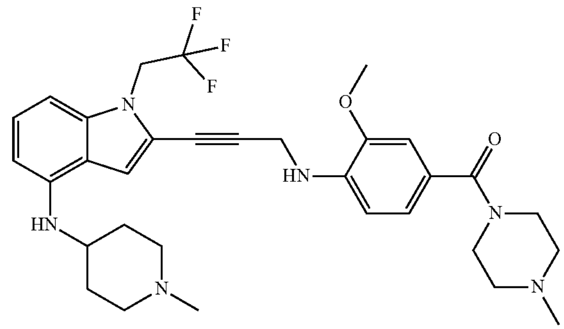 [SMILES: COc1cc(C(=O)N2CCN(C)CC2)ccc1NCC#Cc1cc2c(NC3CCN(C)CC3)cccc2n1CC(F)(F)F] | 2-(3-{[2-methoxy-4-(4-methylpiperazine-1-carbonyl)phenyl]amino}prop-1-yn-1-yl)-N-(1-methylpiperidin-4-yl)-1-(2,2,2-trifluoroethyl)-1H-indol-4-amine | 597.3 |
| 502A | 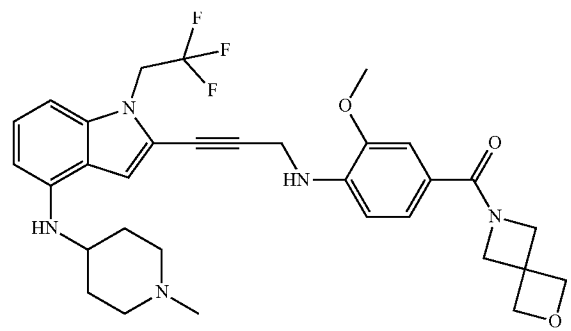 [SMILES: COc1cc(C(=O)N2CC3(COC3)C2)ccc1NCC#Cc1cc2c(NC3CCN(C)CC3)cccc2n1CC(F)(F)F] | 2-{3-[(2-methoxy-4-{2-oxa-6-azaspiro[3.3]heptane-6-carbonyl}phenyl)amino]prop-1-yn-1-yl}-N-(1-methylpiperidin-4-yl)-1-(2,2,2-trifluoroethyl)-1H-indol-4-amine | 596.3 |
| 503A | 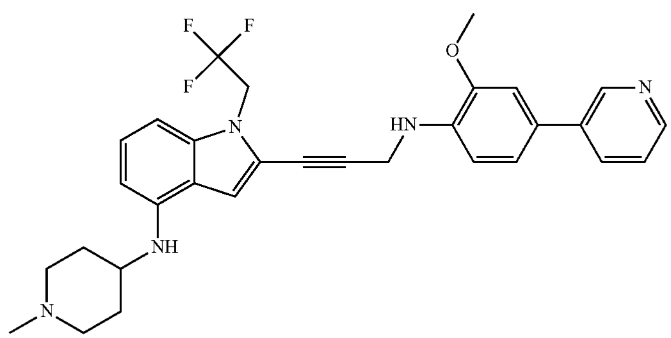 [SMILES: COc1cc(-c2cccnc2)ccc1NCC#Cc1cc2c(NC3CCN(C)CC3)cccc2n1CC(F)(F)F] | 2-(3-{[2-methoxy-4-(pyridin-3-yl)phenyl]amino}prop-1-yn-1-yl)-N-(1-methylpiperidin-4-yl)-1-(2,2,2-trifluoroethyl)-1H-indol-4-amine | 548.3 |

TABLE 4-continued

| Compound No. | Structure | IUPAC | LC-MS (ES+, m/z) |
|---|---|---|---|
| 504A | 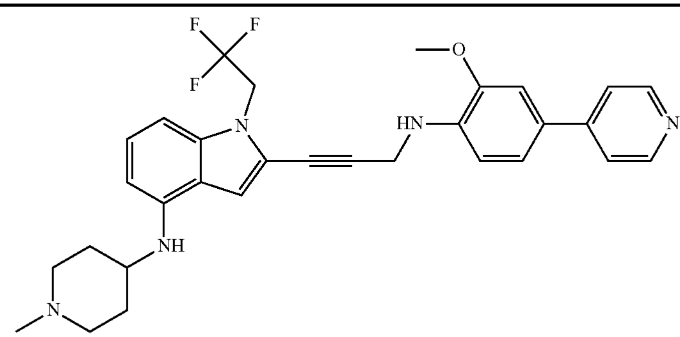 | 2-(3-{[2-methoxy-4-(pyridin-4-yl)phenyl]amino}prop-1-yn-1-yl)-N-(1-methylpiperidin-4-yl)-1-(2,2,2-trifluoroethyl)-1H-indol-4-amine | 548.3 |
| 505A | 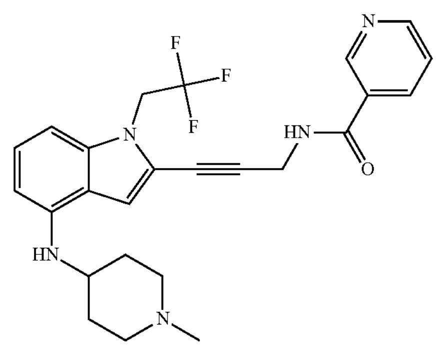 [SMILES: CN1CCC(Nc2cccc3c2cc(C#CCNC(=O)c2cccnc2)n3CC(F)(F)F)CC1] | N-(3-{4-[(1-methylpiperidin-4-yl)amino]-1-(2,2,2-trifluoroethyl)-1H-indol-2-yl}prop-2-yn-1-yl)pyridine-3-carboxamide | 470.2 |
| 506A | 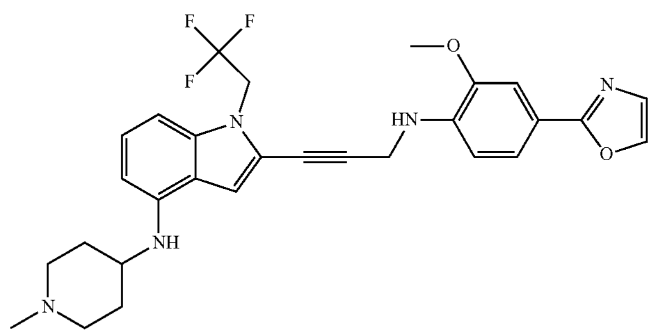 [SMILES: COc1cc(-c2ncco2)ccc1NCC#Cc1cc2c(NC3CCN(C)CC3)cccc2n1CC(F)(F)F] | 2-(3-{[2-methoxy-4-(1,3-oxazol-2-yl)phenyl]amino}prop-1-yn-1-yl)-N-(1-methylpiperidin-4-yl)-1-(2,2,2-trifluoroethyl)-1H-indol-4-amine | 538.3 |

TABLE 4-continued
| Compound No. | Structure | IUPAC | LC-MS (ES+, m/z) |
|---|---|---|---|
| 507A | 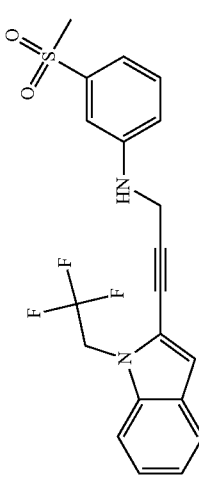 | 2-{3-[(3-methanesulfonylphenyl)amino]prop-1-yn-1-yl}-N-(1-methylpiperidin-4-yl)-1-(2,2,2-trifluoroethyl)-1H-indol-4-amine | 519.2 |
| 508A | 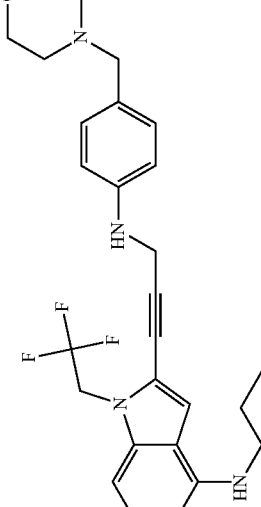 | N-(1-methylpiperidin-4-yl)-2-[3-({4-[(morpholin-4-yl)methyl]phenyl}amino)prop-1-yn-1-yl]-1-(2,2,2-trifluoroethyl)-1H-indol-4-amine | 540.3 |
| 509A | 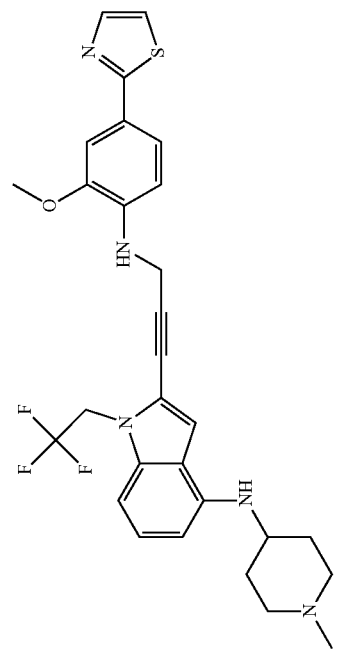 | 2-(3-{[2-methoxy-4-(1,3-thiazol-2-yl)phenyl]amino}prop-1-yn-1-yl)-N-(1-methylpiperidin-4-yl)-1-(2,2,2-trifluoroethyl)-1H-indol-4-amine | 554.2 |

TABLE 4-continued

| Compound No. | Structure | IUPAC | LC-MS (ES+, m/z) |
|---|---|---|---|
| 510A | 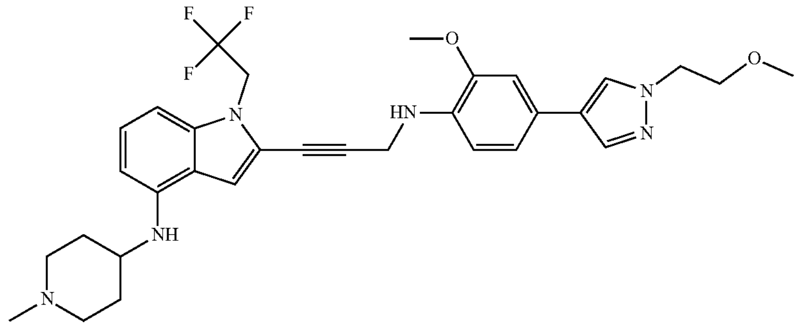 | 2-[3-({2-methoxy-4-[1-(2-methoxyethyl)-1H-pyrazol-4-yl]phenyl}amino)prop-1-yn-1-yl]-N-(1-methylpiperidin-4-yl)-1-(2,2,2-trifluoroethyl)-1H-indol-4-amine | 595.4 |
| 511A | 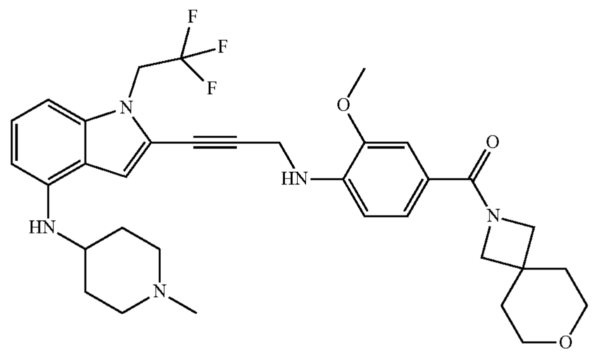 [SMILES: COc1cc(C(=O)N2CC3(CCOCC3)C2)ccc1NCC#Cc1cc2c(NC3CCN(C)CC3)cccc2n1CC(F)(F)F] | 2-{3-[(2-methoxy-4-{7-oxa-2-azaspiro[3.5]nonane-2-carbonyl}phenyl)amino]prop-1-yn-1-yl}-N-(1-methylpiperidin-4-yl)-1-(2,2,2-trifluoroethyl)-1H-indol-4-amine | 624.3 |
| 512A | 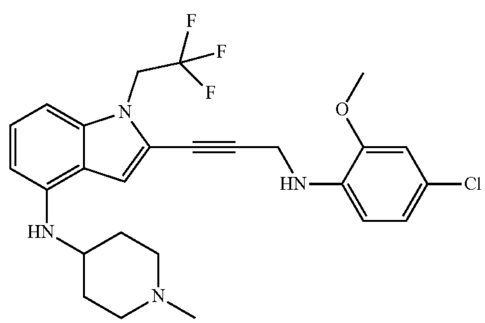 [SMILES: COc1cc(Cl)ccc1NCC#Cc1cc2c(NC3CCN(C)CC3)cccc2n1CC(F)(F)F] | 2-{3-[(4-chloro-2-methoxyphenyl)amino]prop-1-yn-1-yl}-N-(1-methylpiperidin-4-yl)-1-(2,2,2-trifluoroethyl)-1H-indol-4-amine | 505.1 |

TABLE 4-continued

| Compound No. | Structure | IUPAC | LC-MS (ES+, m/z) |
|---|---|---|---|
| 513A | 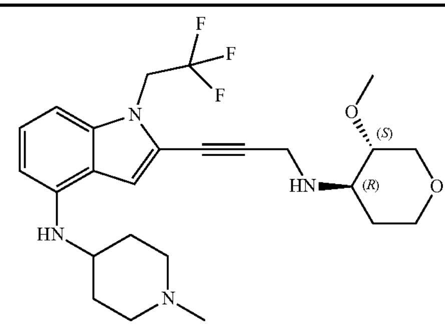 | 2-(3-(((3S,4R)-3-methoxytetrahydro-2H-pyran-4-yl)amino)prop-1-yn-1-yl)-N-(1-methylpiperidin-4-yl)-1-(2,2,2-trifluoroethyl)-1H-indol-4-amine | 479.2 |
| 514A | 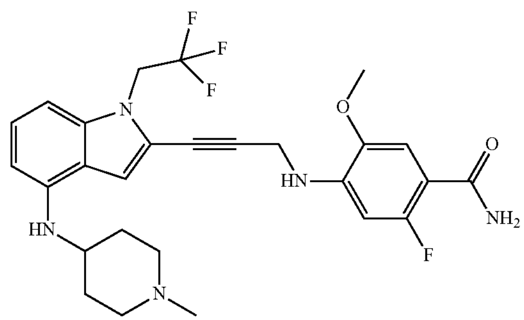 [SMILES: COc1cc(C(N)=O)c(F)cc1NCC#Cc1cc2c(NC3CCN(C)CC3)cccc2n1CC(F)(F)F] | 2-fluoro-5-methoxy-4-[(3-{4-[(1-methylpiperidin-4-yl)amino]-1-(2,2,2-trifluoroethyl)-1H-indol-2-yl}prop-2-yn-1-yl)amino]benzamide | 532.2 |
| 515A | 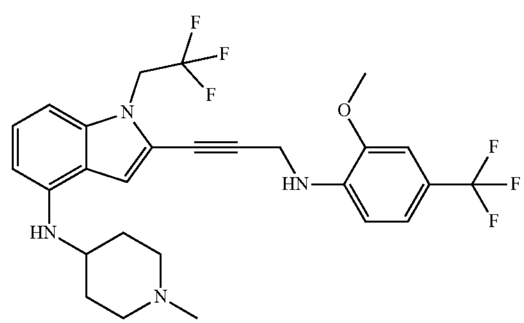 [SMILES: COc1cc(C(F)(F)F)ccc1NCC#Cc1cc2c(NC3CCN(C)CC3)cccc2n1CC(F)(F)F] | 2-(3-{[2-methoxy-4-(trifluoromethyl)phenyl]amino}prop-1-yn-1-yl)-N-(1-methylpiperidin-4-yl)-1-(2,2,2-trifluoroethyl)-1H-indol-4-amine | 539.2 |

TABLE 4-continued

| Compound No. | Structure | IUPAC | LC-MS (ES+, m/z) |
|---|---|---|---|
| 516A | 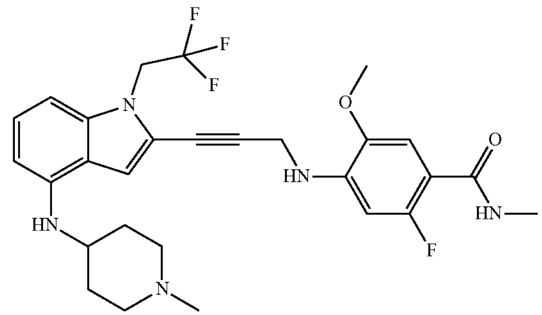 [SMILES: CNC(=O)c1cc(OC)c(NCC#Cc2cc3c(NC4CCN(C)CC4)cccc3n2CC(F)(F)F)cc1F] | 2-fluoro-5-methoxy-N-methyl-4-[(3-{4-[(1-methylpiperidin-4-yl)amino]-1-(2,2,2-trifluoroethyl)-1H-indol-2-yl}prop-2-yn-1-yl)amino]benzamide | 546.2 |
| 517A | 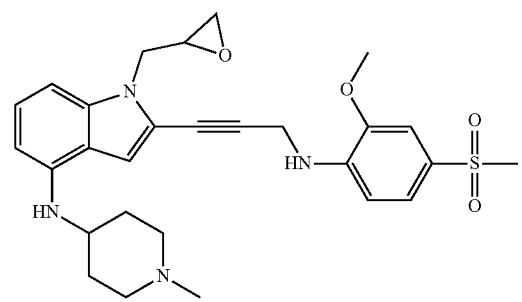 [SMILES: COc1cc(S(C)(=O)=O)ccc1NCC#Cc1cc2c(NC3CCN(C)CC3)cccc2n1CC1CO1] | 2-{3-[(4-methanesulfonyl-2-methoxyphenyl)amino]prop-1-yn-1-yl}-N-(1-methylpiperidin-4-yl)-1-[(oxiran-2-yl)methyl]-1H-indol-4-amine | 523.2 |
| 518A | 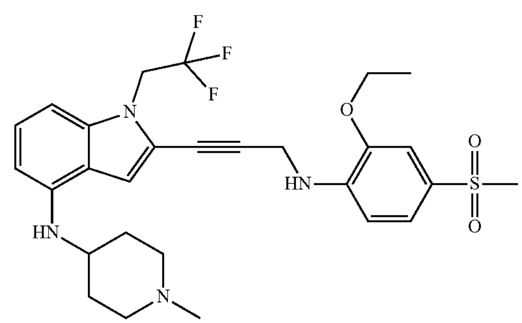 [SMILES: CCOc1cc(S(C)(=O)=O)ccc1NCC#Cc1cc2c(NC3CCN(C)CC3)cccc2n1CC(F)(F)F] | 2-(3-((2-ethoxy-4-(methylsulfonyl)phenyl)amino)prop-1-yn-1-yl)-N-(1-methylpiperidin-4-yl)-1-(2,2,2-trifluoroethyl)-1H-indol-4-amine | 563.2 |

TABLE 4-continued

| Compound No. | Structure | IUPAC | LC-MS (ES+, m/z) |
|---|---|---|---|
| 519A | 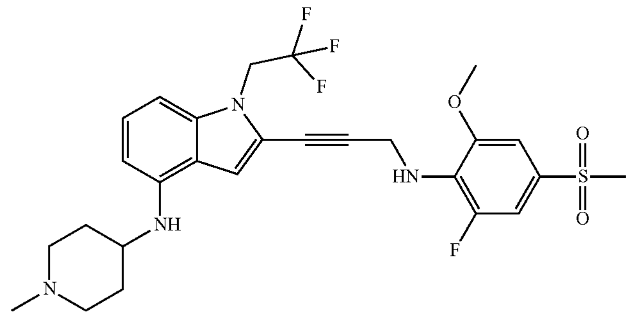 | 2-{3-[(2-fluoro-4-methanesulfonyl-6-methoxyphenyl)amino]prop-1-yn-1-yl]-N-(1-methylpiperidin-4-yl)-1-(2,2,2-trifluoroethyl)-1H-indol-4-amine | 567.2 |
| 520A | 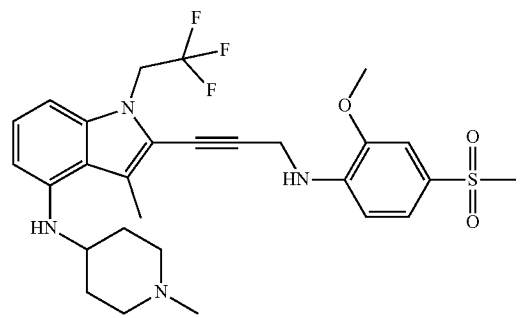 [SMILES: COc1cc(S(C)(=O)=O)ccc1NCC#Cc1c(C)c2c(NC3CCN(C)CC3)cccc2n1CC(F)(F)F] | 2-{3-[(4-methanesulfonyl-2-methoxyphenyl)amino]prop-1-yn-1-yl}-3-methyl-N-(1-methylpiperidin-4-yl)-1-(2,2,2-trifluoroethyl)-1H-indol-4-amine | 563.3 |
| 521A | 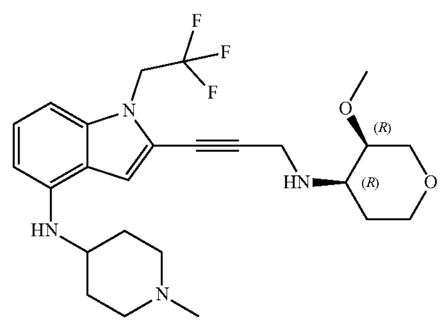 | 2-(3-(((3R,4R)-3-methoxytetrahydro-2H-pyran-4-yl)amino)prop-1-yn-1-yl)-N-(1-methylpiperidin-4-yl)-1-(2,2,2-trifluoroethyl)-1H-indol-4-amine | 497.2 |

TABLE 4-continued

| Compound No. | Structure | IUPAC | LC-MS (ES+, m/z) |
|---|---|---|---|
| 522A | 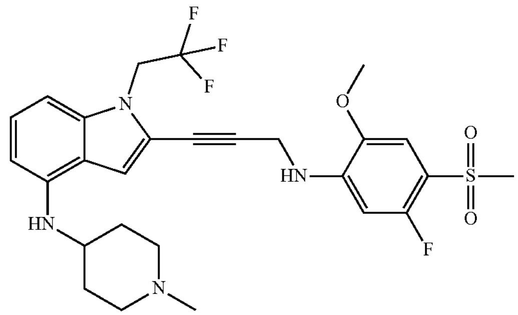 [SMILES: COc1cc(S(C)(=O)=O)c(F)cc1NCC#Cc1cc2c(NC3CCN(C)CC3)cccc2n1CC(F)(F)F] | 2-{3-[(5-fluoro-4-methanesulfonyl-2-methoxyphenyl)amino]prop-1-yn-1-yl}-N-(1-methylpiperidin-4-yl)-1-(2,2,2-trifluoroethyl)-1H-indol-4-amine | 567.2 |
| 523A | 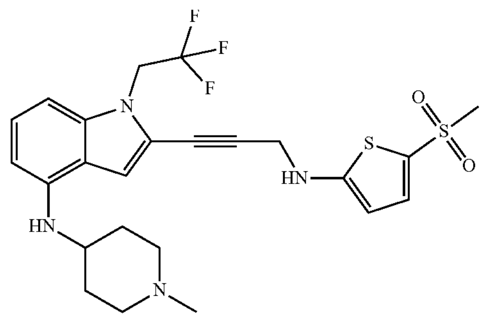 [SMILES: CN1CCC(Nc2cccc3c2cc(C#CCNc2ccc(S(C)(=O)=O)s2)n3CC(F)(F)F)CC1] | 2-{3-[(5-methanesulfonylthiophen-2-yl)amino]prop-1-yn-1-yl}-N-(1-methylpiperidin-4-yl)-1-(2,2,2-trifluoroethyl)-1H-indol-4-amine | 525.2 |
| 524A | 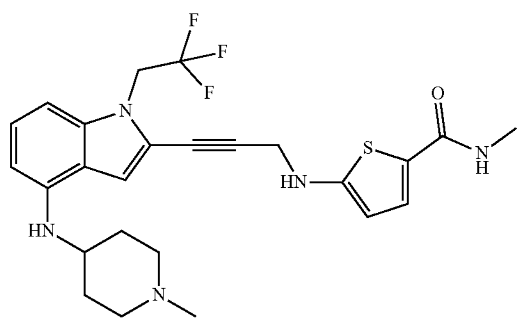 [SMILES: CNC(=O)c1ccc(NCC#Cc2cc3c(NC4CCN(C)CC4)cccc3n2CC(F)(F)F)s1] | N-methyl-5-{3-{4-[(1-methylpiperidin-4-yl)amino]-1-(2,2,2-trifluoroethyl)-1H-indol-2-yl}prop-2-yn-1-yl}aminothiophene-2-carboxamide | 504.2 |

TABLE 4-continued

| Compound No. | Structure | IUPAC | LC-MS (ES+, m/z) |
|---|---|---|---|
| 525A | 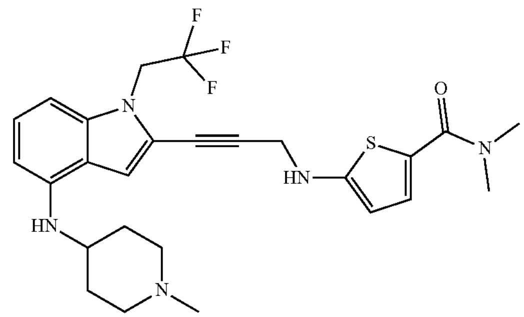 [SMILES: CN1CCC(Nc2cccc3c2cc(C#CCNc2ccc(C(=O)N(C)C)s2)n3CC(F)(F)F)CC1] | N,N-dimethyl-5-[(3-{4-[(1-methylpiperidin-4-yl)amino]-1-(2,2,2-trifluoroethyl)-1H-indol-2-yl}prop-2-yn-1-yl)amino]thiophene-2-carboxamide | 518.2 |
| 526A | 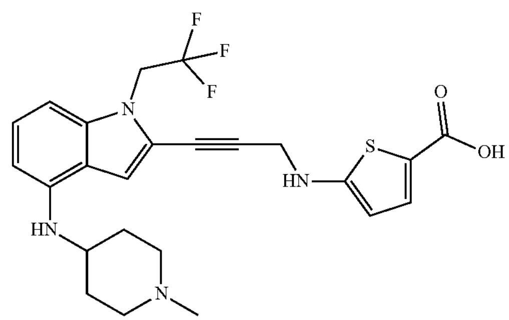 [SMILES: CN1CCC(Nc2cccc3c2cc(C#CCNc2ccc(C(=O)O)s2)n3CC(F)(F)F)CC1] | 5-[(3-{4-[(1-methylpiperidin-4-yl)amino]-1-(2,2,2-trifluoroethyl)-1H-indol-2-yl}prop-2-yn-1-yl)amino]thiophene-2-carboxylic acid | 489.0 |
| 527A | 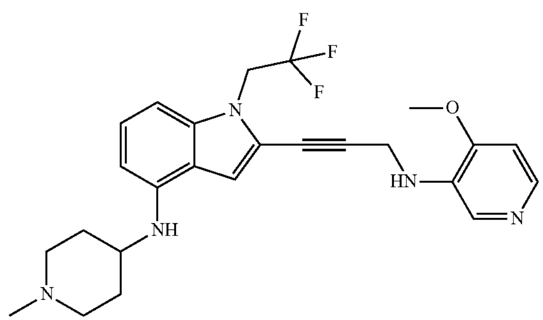 [SMILES: COc1ccncc1NCC#Cc1cc2c(NC3CCN(C)CC3)cccc2n1CC(F)(F)F] | 2-(3-((4-methoxypyridin-3-yl)amino)prop-1-yn-1-yl)-N-(1-methylpiperidin-4-yl)-1-(2,2,2-trifluoroethyl)-1H-indol-4-amine | 472.2 |

TABLE 4-continued

| Compound No. | Structure | IUPAC | LC-MS (ES+, m/z) |
|---|---|---|---|
| 528A | 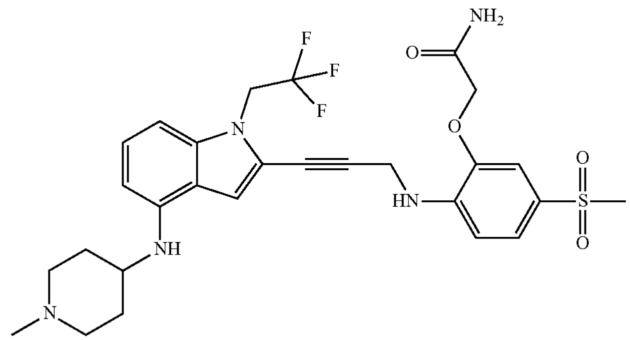 | 2-(2-((3-(4-((1-methylpiperidin-4-yl)amino)-1-(2,2,2-trifluoroethyl)-1H-indol-2-yl)prop-2-yn-1-yl)amino)-5-(methylsulfonyl)phenoxy)acetamide | 592.2 |
| 529A | 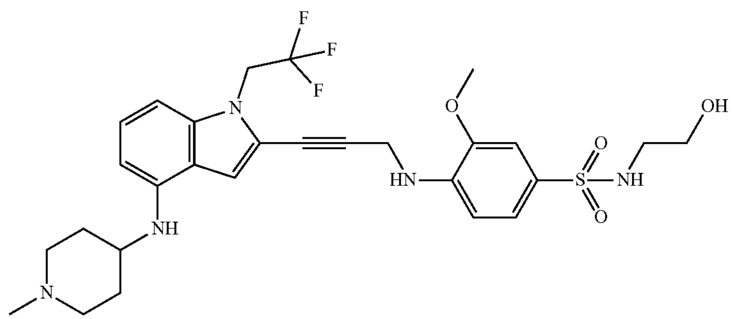 [SMILES: COc1cc(S(=O)(=O)NCCO)ccc1NCC#Cc1cc2c(NC3CCN(C)CC3)cccc2n1CC(F)(F)F] | N-(2-hydroxyethyl)-3-methoxy-4-((3-(4-((1-methylpiperidin-4-yl)amino)-1-(2,2,2-trifluoroethyl)-1H-indol-2-yl)prop-2-yn-1-yl)amino)benzenesulfonamide | 594.2 |
| 530A | 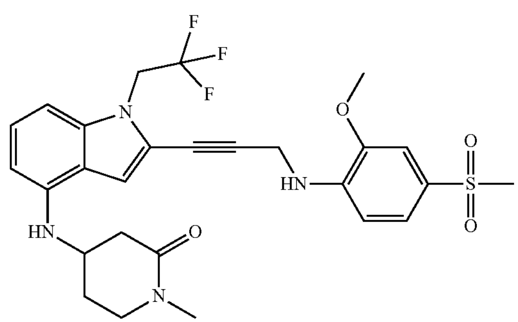 [SMILES: COc1cc(S(C)(=O)=O)ccc1NCC#Cc1cc2c(NC3CCN(C)C(=O)C3)cccc2n1CC(F)(F)F] | 4-((2-(3-((2-methoxy-4-(methylsulfonyl)phenyl)amino)prop-1-yn-1-yl)-1-(2,2,2-trifluoroethyl)-1H-indol-4-yl)amino)-1-methylpiperidin-2-one | 563.2 |

| Compound No. | Structure | IUPAC | LC-MS (ES+, m/z) |
|---|---|---|---|
| 531A | 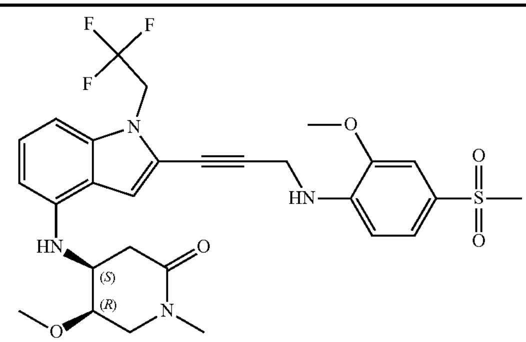 | 2-{3-[(4-methanesulfonyl-2-methoxyphenyl)amino]prop-1-yn-1-yl}-N-[(3R,4S)-3-methoxy-1-methylpiperidin-4-yl]-1-(2,2,2-trifluoroethyl)-1H-indol-4-amine | 578.9 |
| 532A | 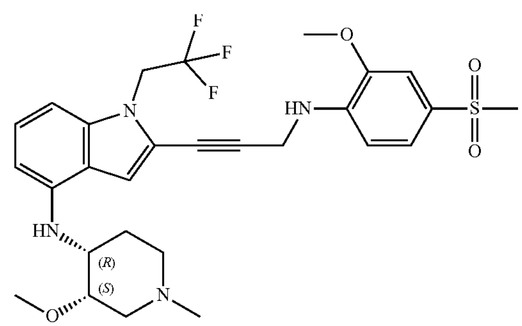 | 2-{3-[(4-methanesulfonyl-2-methoxyphenyl)amino]prop-1-yn-1-yl}-N-[(3S,4R)-3-methoxy-1-methylpiperidin-4-yl]-1-(2,2,2-trifluoroethyl)-1H-indol-4-amine | 578.9 |
| 533A | 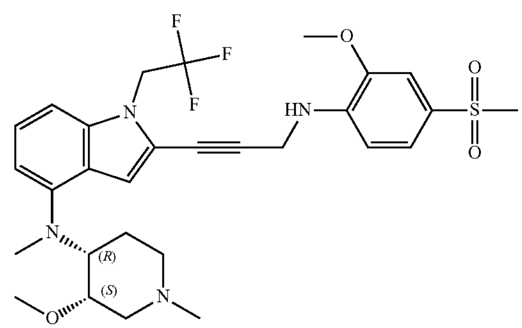 | 2-{3-[(4-methanesulfonyl-2-methoxyphenyl)amino]prop-1-yn-1-yl}-N-[(3S,4R)-3-methoxy-1-methylpiperidin-4-yl]-N-methyl-1-(2,2,2-trifluoroethyl)-1H-indol-4-amine | 636.9 |

| Compound No. | Structure | IUPAC | LC-MS (ES+, m/z) |
|---|---|---|---|
| 534A | 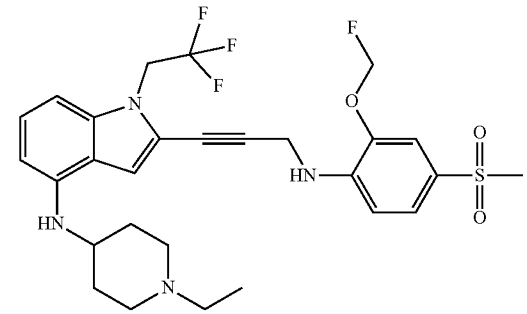 [SMILES: CCN1CCC(Nc2cccc3c2cc(C#CCNc2ccc(S(C)(=O)=O)cc2OCF)n3CC(F)(F)F)CC1] | N-(1-ethylpiperidin-4-yl)-2-(3-{[2-(fluoromethoxy)-4-methanesulfonylphenyl]amino}prop-1-yn-1-yl)-1-(2,2,2-trifluoroethyl)-1H-indol-4-amine | 581.3 |
| 535A | 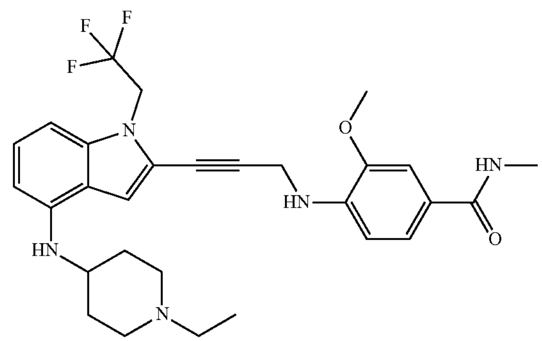 [SMILES: CCN1CCC(Nc2cccc3c2cc(C#CCNc2ccc(C(=O)NC)cc2OC)n3CC(F)(F)F)CC1] | 4-[(3-{4-[(1-ethylpiperidin-4-yl)amino]-1-(2,2,2-trifluoroethyl)-1H-indol-2-yl}prop-2-yn-1-yl)amino]-3-methoxy-N-methylbenzamide | 542.3 |
| 536A | 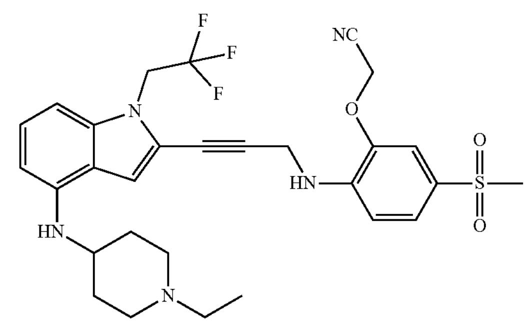 [SMILES: CCN1CCC(Nc2cccc3c2cc(C#CCNc2ccc(S(C)(=O)=O)cc2OCC#N)n3CC(F)(F)F)CC1] | 2-{2-[(3-{4-[(1-ethylpiperidin-4-yl)amino]-1-(2,2,2-trifluoroethyl)-1H-indol-2-yl}prop-2-yn-1-yl)amino]-5-methanesulfonylphenoxy}acetonitrile | 588.2 |

TABLE 4-continued

| Compound No. | Structure | IUPAC | LC-MS (ES+, m/z) |
|---|---|---|---|
| 537A | 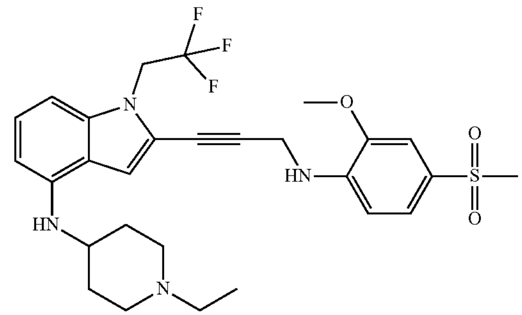 [SMILES: CCN1CCC(Nc2cccc3c2cc(C#CCNc2ccc(S(C)(=O)=O)cc2OC)n3CC(F)(F)F)CC1] | N-(1-ethylpiperidin-4-yl)-2-{3-[(4-methanesulfonyl-2-methoxyphenyl)amino]prop-1-yn-1-yl}-1-(2,2,2-trifluoroethyl)-1H-indol-4-amine | 563.2 |
| 538A | 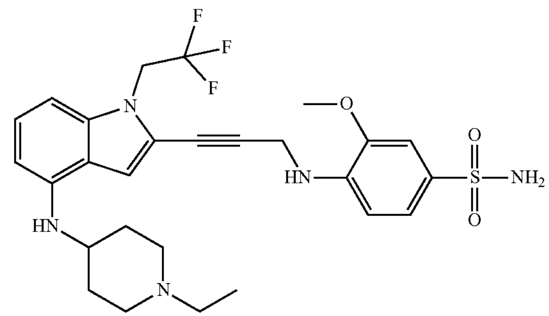 [SMILES: CCN1CCC(Nc2cccc3c2cc(C#CCNc2ccc(S(N)(=O)=O)cc2OC)n3CC(F)(F)F)CC1] | 4-[(3-{4-[(1-ethylpiperidin-4-yl)amino]-1-(2,2,2-trifluoroethyl)-1H-indol-2-yl}prop-2-yn-1-yl)amino]-3-methoxybenzene-1-sulfonamide | 564.2 |
| 539A | 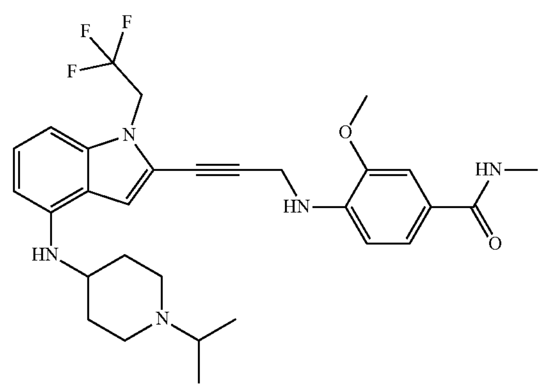 [SMILES: CNC(=O)c1ccc(NCC#Cc2cc3c(NC4CCN(C(C)C)CC4)cccc3n2CC(F)(F)F)c(OC)c1] | 3-methoxy-N-methyl-4-{[3-(4-{[1-(propan-2-yl)piperidin-4-yl]amino}-1-(2,2,2-trifluoroethyl)-1H-indol-2-yl)prop-2-yn-1-yl]amino}benzamide | 556.4 |

TABLE 4-continued

| Compound No. | Structure | IUPAC | LC-MS (ES⁺; m/z) |
|---|---|---|---|
| 540A | 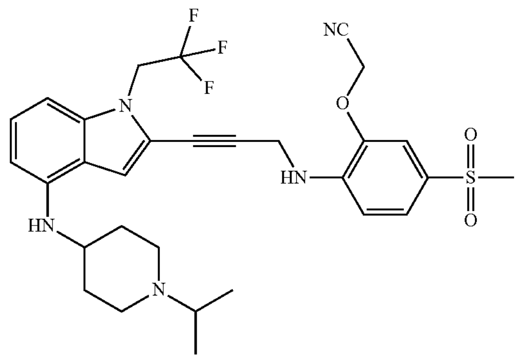 [SMILES: CC(C)N1CCC(Nc2cccc3c2cc(C#CCNc2ccc(S(C)(=O)=O)cc2OCC#N)n3CC(F)(F)F)CC1] | 2-(5-methanesulfonyl-2-{[3-(4-{[1-(propan-2-yl)piperidin-4-yl]amino}-1-(2,2,2-trifluoroethyl)-1H-indol-2-yl)prop-2-yn-1-yl]amino}phenoxy)acetonitrile | 602.3 |
| 541A | 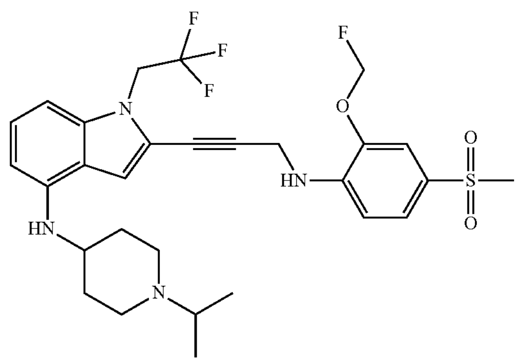 [SMILES: CC(C)N1CCC(Nc2cccc3c2cc(C#CCNc2ccc(S(C)(=O)=O)cc2OCF)n3CC(F)(F)F)CC1] | 2-(3-{[2-(fluoromethoxy)-4-methanesulfonylphenyl]amino}prop-1-yn-1-yl)-N-[1-(propan-2-yl)piperidin-4-yl]-1-(2,2,2-trifluoroethyl)-1H-indol-amine | 595.2 |

TABLE 4-continued
| Compound No. | Structure | IUPAC | LC-MS (ES+, m/z) |
|---|---|---|---|
| 542A | 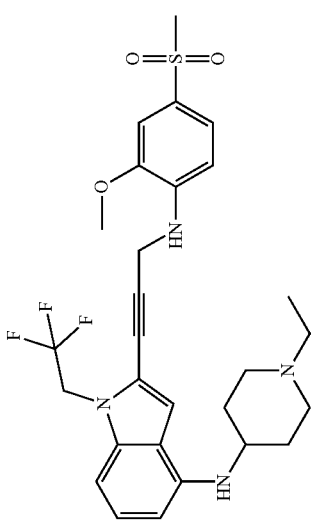 | 2-{3-[(4-methanesulfonyl-2-methoxyphenyl)amino]prop-1-yn-1-yl}-N-[1-(propan-2-yl)piperidin-4-yl]-1-(2,2,2-trifluoroethyl)-1H-indol-4-amine | 577.3 |
| 543A | 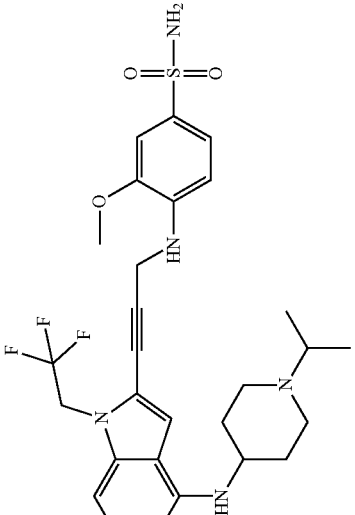 | 3-methoxy-4-{[3-(4-{[1-(propan-2-yl)piperidin-4-yl]amino}-1-(2,2,2-trifluoroethyl)-1H-indol-2-yl)prop-2-yn-1-yl]amino}benzene-1-sulfonamide | 578.2 |

TABLE 4-continued

| Compound No. | Structure | IUPAC | LC-MS (ES+, m/z) |
|---|---|---|---|
| 544A | 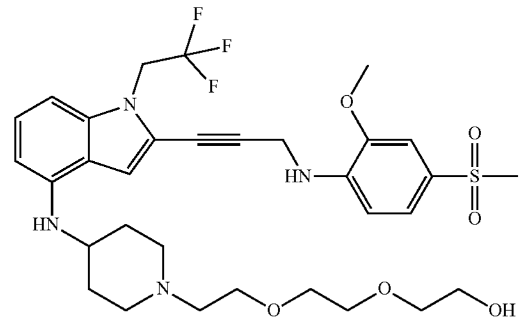 [SMILES: COc1cc(S(C)(=O)=O)ccc1NCC#Cc1cc2c(NC3CCN(CCOCCOCCO)CC3)cccc2n1CC(F)(F)F] | 2-[2-(2-{4-[2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethoxy)ethoxy]ethan-1-ol | 667.2 |
| 545A | 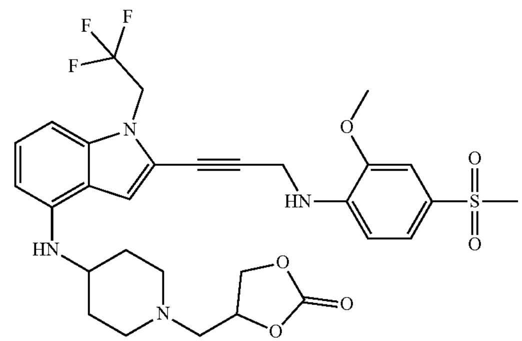 [SMILES: COc1cc(S(C)(=O)=O)ccc1NCC#Cc1cc2c(NC3CCN(CC4COC(=O)O4)CC3)cccc2n1CC(F)(F)F] | 4-({4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}methyl)-1,3-dioxolan-2-one | 635.2 |
| 546A | 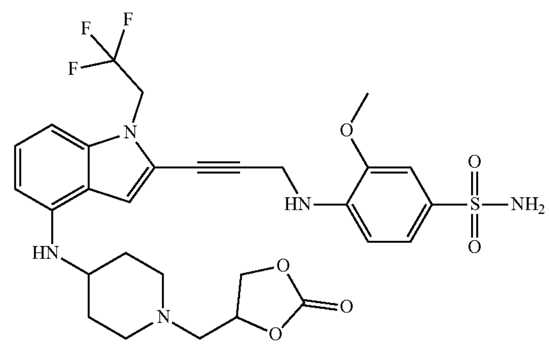 [SMILES: COc1cc(S(N)(=O)=O)ccc1NCC#Cc1cc2c(NC3CCN(CC4COC(=O)O4)CC3)cccc2n1CC(F)(F)F] | 3-methoxy-4-({3-[4-({1-[(2-oxo-1,3-dioxolan-4-yl)methyl]piperidin-4-yl}amino)-1-(2,2,2-trifluoroethyl)-1H-indol-2-yl]prop-2-yn-1-yl}amino)benzene-1-sulfonamide | 636.2 |

TABLE 4-continued

| Compound No. | Structure | IUPAC | LC-MS (ES+, m/z) |
|---|---|---|---|
| 547A | 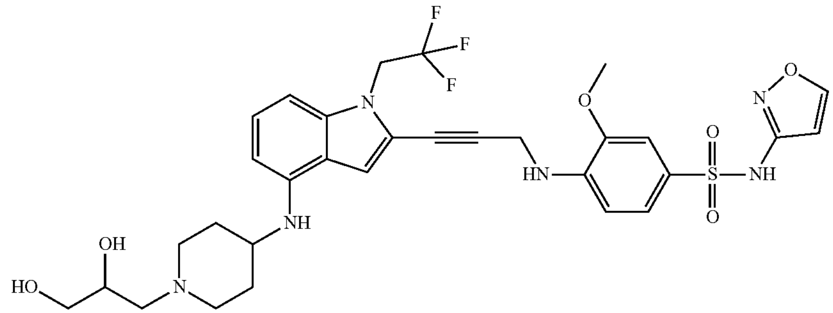 [SMILES: COc1cc(S(=O)(=O)Nc2ccon2)ccc1NCC#Cc1cc2c(NC3CCN(CC(O)CO)CC3)cccc2n1CC(F)(F)F] | 4-{3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-(1,2-oxazol-3-yl)benzene-1-sulfonamide | 677.2 |
| 548A | 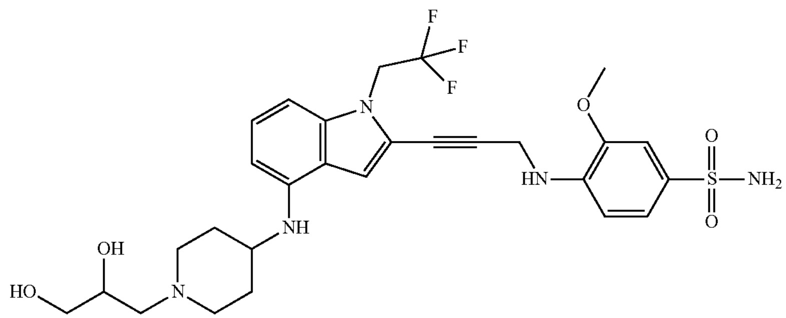 [SMILES: COc1cc(S(N)(=O)=O)ccc1NCC#Cc1cc2c(NC3CCN(CC(O)CO)CC3)cccc2n1CC(F)(F)F] | 4-((3-(4-((1-(2,3-dihydroxypropyl)piperidin-4-yl)amino)-1-(2,2,2-trifluoroethyl)-1H-indol-2-yl)prop-2-yn-1-yl)amino)-3-methoxybenzenesulfonamide | |
| 549A | 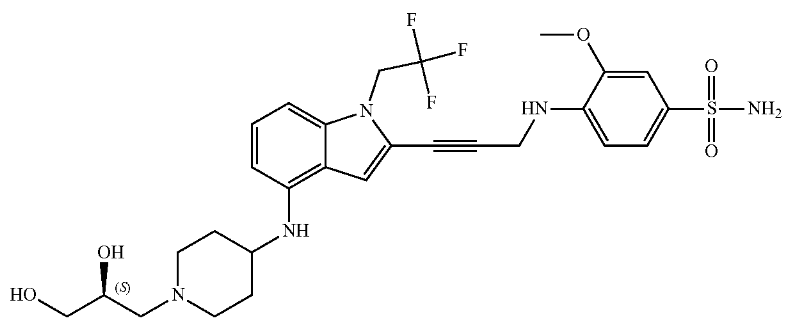 | 4-({3-[4-({1-[(2S)-2,3-dihydroxypropyl]piperidin-4-yl}amino)-1-(2,2,2-trifluoroethyl)-1H-indol-2-yl]prop-2-yn-1-yl}amino)-3-methoxybenzene-1-sulfonamide | 610.1 |

TABLE 4-continued

| Compound No. | Structure | IUPAC | LC-MS (ES+, m/z) |
|---|---|---|---|
| 550A | 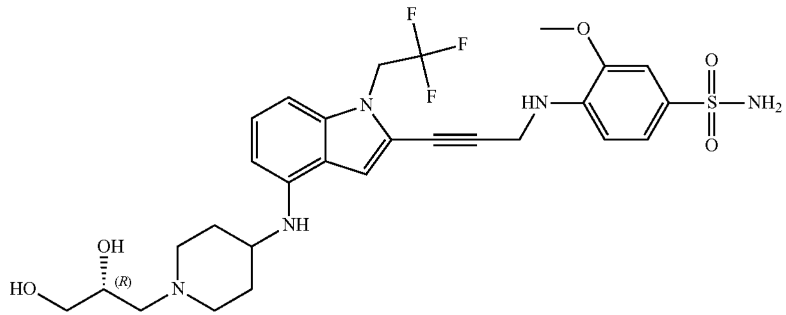 | 4-({3-[4-({1-[(2R)-2,3-dihydroxypropyl]piperidin-4-yl}amino)-1-(2,2,2-trifluoroethyl)-1H-indol-2-yl]prop-2-yn-1-yl}amino)-3-methoxybenzene-1-sulfonamide | 610.2 |
| 551A | 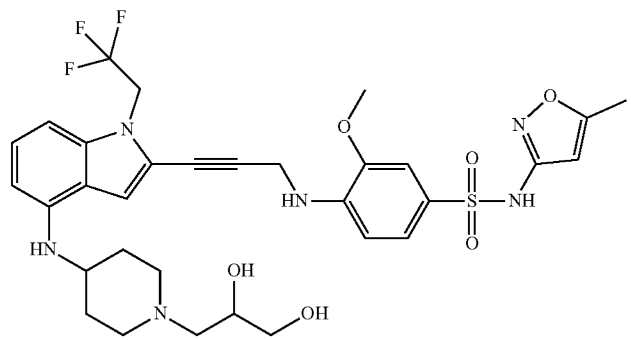 [SMILES: COc1cc(S(=O)(=O)Nc2cc(C)on2)ccc1NCC#Cc1cc2c(NC3CCN(CC(O)CO)CC3)cccc2n1CC(F)(F)F] | 4-[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-(5-methyl-1,2-oxazol-3-yl)benzene-1-sulfonamide | 391.2 |
| 552A | 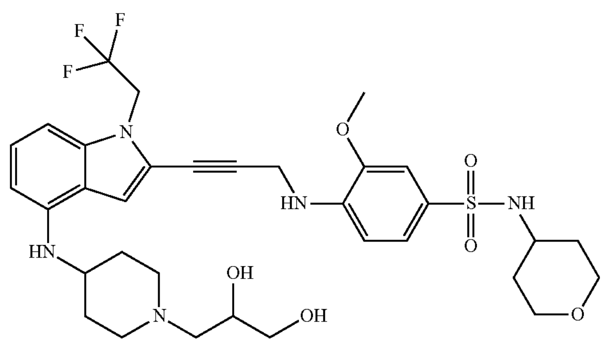 [SMILES: COc1cc(S(=O)(=O)NC2CCOCC2)ccc1NCC#Cc1cc2c(NC3CCN(CC(O)CO)CC3)cccc2n1CC(F)(F)F] | 4-{3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-(oxan-4-yl)benzene-1-sulfonamide | 694.3 |

TABLE 4-continued

| Compound No. | Structure | IUPAC | LC-MS (ES+, m/z) |
|---|---|---|---|
| 553A | 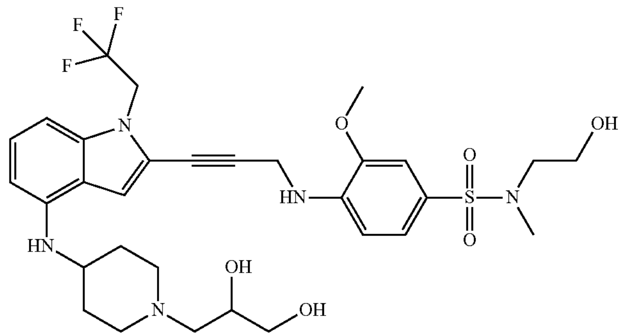 [SMILES: COc1cc(S(=O)(=O)N(C)CCO)ccc1NCC#Cc1cc2c(NC3CCN(CC(O)CO)CC3)cccc2n1CC(F)(F)F] | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-N-(2-hydroxyethyl)-3-methoxy-N-methylbenzene-1-sulfonamide | 668.2 |
| 554A | 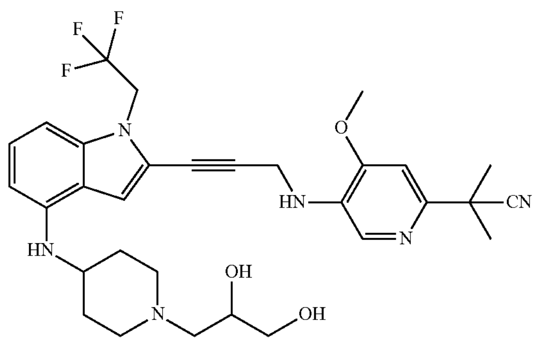 [SMILES: COc1cc(C(C)(C)C#N)ncc1NCC#Cc1cc2c(NC3CCN(CC(O)CO)CC3)cccc2n1CC(F)(F)F] | 2-(5-{[3-(4-{[1-(2,3-dihydroxypropyl)piperidin-4-yl]amino}-1-(2,2,2-trifluoroethyl)-1H-indol-2-yl)prop-2-yn-1-yl]amino}-4-methoxypyridin-2-yl)-2-methylpropanenitrile | 599.3 |

TABLE 4-continued

| Compound No. | Structure | IUPAC | LC-MS (ES+, m/z) |
|---|---|---|---|
| 555A | 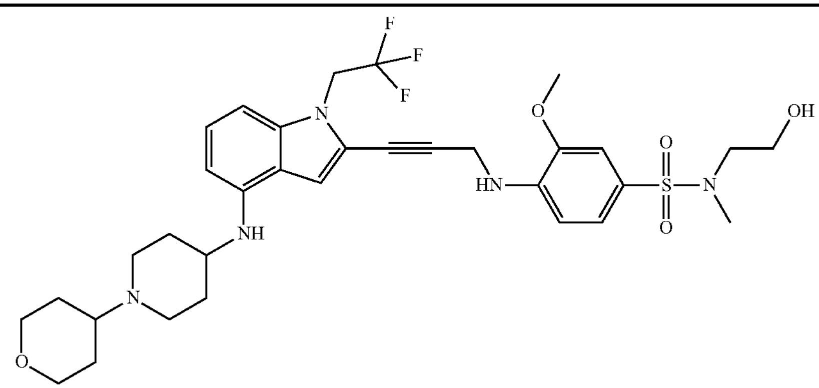 | N-(2-hydroxyethyl)-3-methoxy-N-methyl-4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide | 678.3 |
| 556A | 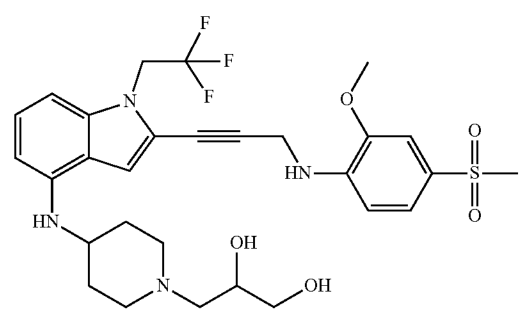 [SMILES: COc1cc(S(C)(=O)=O)ccc1NCC#Cc1cc2c(NC3CCN(CC(O)CO)CC3)cccc2n1CC(F)(F)F] | 3-(4-(2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)propane-1,2-diol | 609.3 |
| 557A | 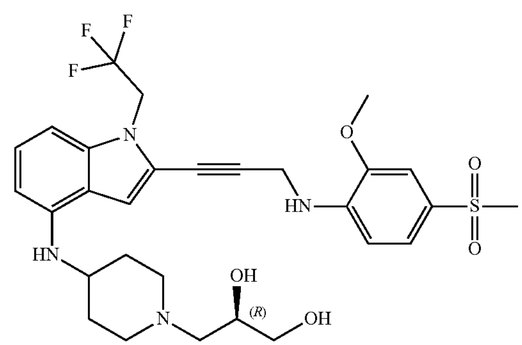 | (2R)-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propane-1,2-diol | 609.2 |

TABLE 4-continued

| Compound No. | Structure | IUPAC | LC-MS (ES+, m/z) |
|---|---|---|---|
| 558A | 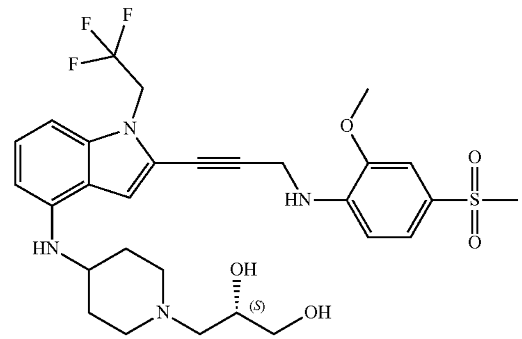 | (2S)-3-{4-[(2-{3-[(4-methanesulfonyl)-2-methoxyphenyl)amino]prop-1-yn-1-yl}-1-(2,2,2-trifluoroethyl)-1H-indol-4-yl)amino]piperidin-1-yl}propane-1,2-diol | 609.2 |
| 559A | 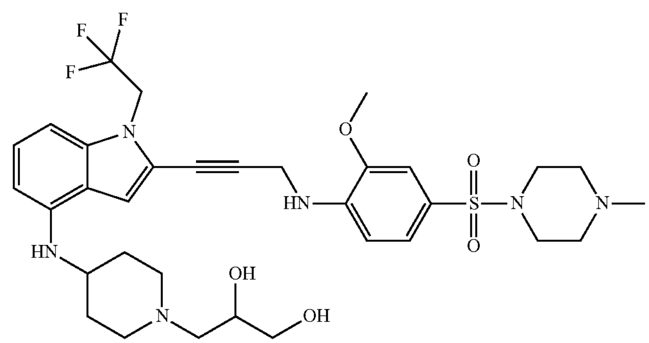 [SMILES: COc1cc(S(=O)(=O)N2CCN(C)CC2)ccc1NCC#Cc1cc2c(NC3CCN(CC(O)CO)CC3)cccc2n1CC(F)(F)F] | 3-[4-({2-[3-({2-methoxy-4-[(4-methylpiperazin-1-yl)sulfonyl]phenyl}amino)prop-1-yn-1-yl]-1-(2,2,2-trifluoroethyl)-1H-indol-4-yl}amino)piperidin-1-yl]propane-1,2-diol | 693.3 |
| 560A | 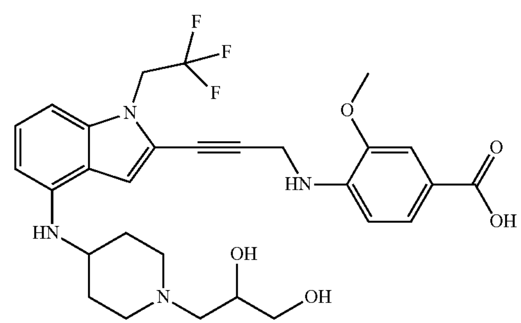 [SMILES: COc1cc(C(=O)O)ccc1NCC#Cc1cc2c(NC3CCN(CC(O)CO)CC3)cccc2n1CC(F)(F)F] | 4-(3-(4-((1-(2,3-dihydroxypropyl)piperidin-4-yl)amino)-1-(2,2,2-trifluoroethyl)-1H-indol-2-yl)prop-2-yn-1-yl)amino)-3-methoxybenzoic acid | 575.2 |

TABLE 4-continued

| Compound No. | Structure | IUPAC | LC-MS (ES+, m/z) |
|---|---|---|---|
| 561A | 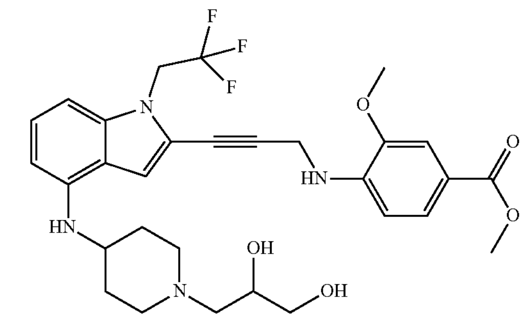 [SMILES: COC(=O)c1ccc(NCC#Cc2cc3c(NC4CCN(CC(O)CO)CC4)cccc3n2CC(F)(F)F)c(OC)c1] | methyl 4-((3-(4-((1-(2,3-dihydroxypropyl)piperidin-4-yl)amino)-1-(2,2,2-trifluoroethyl)-1H-indol-2-yl)prop-2-yn-1-yl)amino)-3-methoxybenzoate | 589.2 |
| 562A | 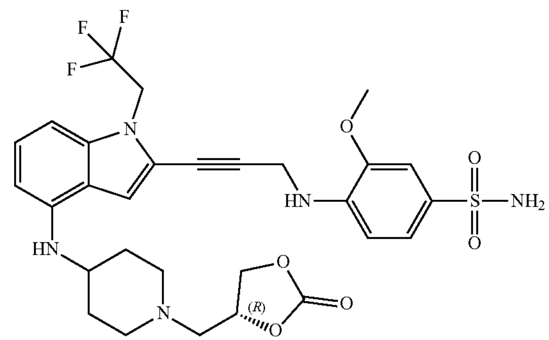 | 3-methoxy-4-[(3-{4-[(1-{[(4R)-2-oxo-1,3-dioxolan-4-yl]methyl}piperidin-4-yl)amino]-1-(2,2,2-trifluoroethyl)-1H-indol-2-yl}prop-2-yn-1-yl)amino]benzene-1-sulfonamide | 636.2 |
| 563A | 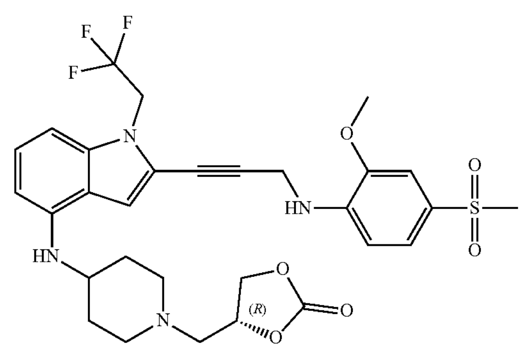 | (4R)-4-({4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}methyl)-1,3-dioxolan-2-one | 635.3 |

TABLE 4-continued

| Compound No. | Structure | IUPAC | LC-MS (ES+, m/z) |
|---|---|---|---|
| 564A | 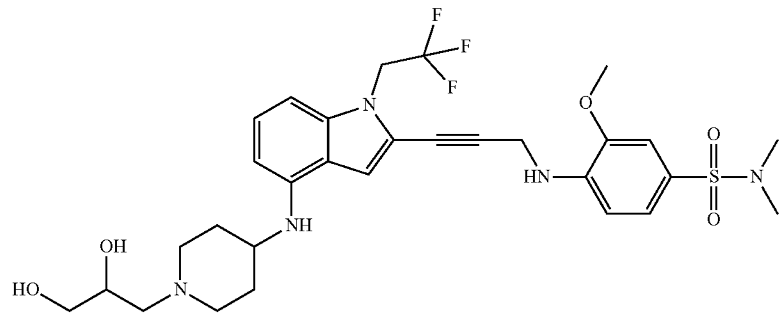 [SMILES: COc1cc(S(=O)(=O)N(C)C)ccc1NCC#Cc1cc2c(NC3CCN(CC(O)CO)CC3)cccc2n1CC(F)(F)F] | 4-[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N,N-dimethylbenzene-1-sulfonamide | 638.3 |
| 565A | 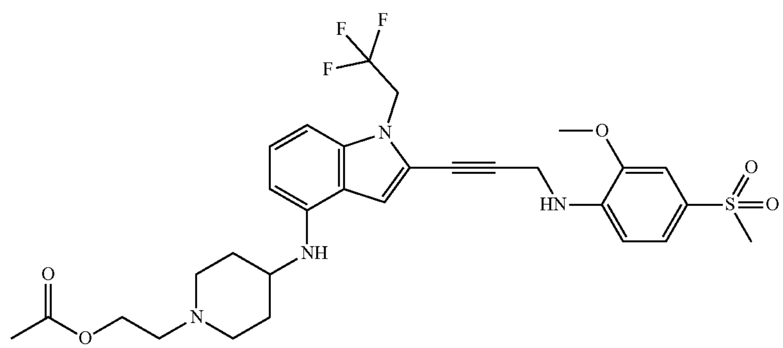 [SMILES: COc1cc(S(C)(=O)=O)ccc1NCC#Cc1cc2c(NC3CCN(CCOC(C)=O)CC3)cccc2n1CC(F)(F)F] | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}EtOAc | 621.3 |
| 566A | 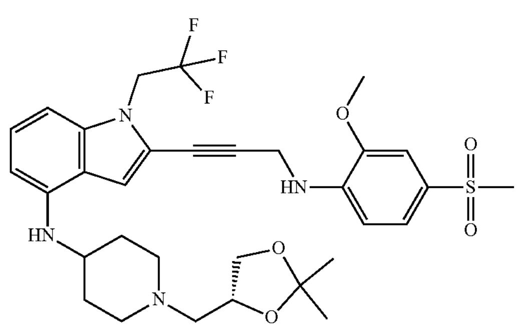 [SMILES: COc1cc(S(C)(=O)=O)ccc1NCC#Cc1cc2c(NC3CCN(C[C@@H]4COC(C)(C)O4)CC3)cccc2n1CC(F)(F)F] | N-(1-{[(4R)-2,2-dimethyl-1,3-dioxolan-4-yl]methyl}piperidin-4-yl)-2-{3-[(4-methanesulfonyl-2-methoxyphenyl)amino]prop-1-yn-1-yl}-1-(2,2,2-trifluoroethyl)-1H-indol-4-amine | 649.3 |

TABLE 4-continued

| Compound No. | Structure | IUPAC | LC-MS (ES+, m/z) |
|---|---|---|---|
| 567A | 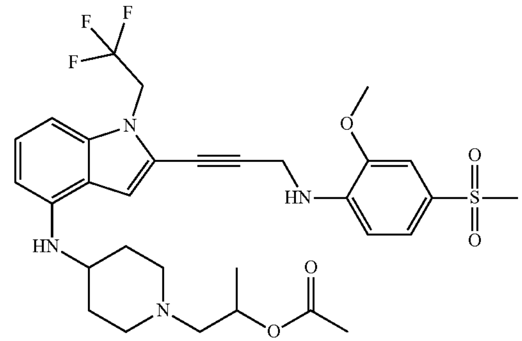 [SMILES: COc1cc(S(C)(=O)=O)ccc1NCC#Cc1cc2c(NC3CCN(CC(C)OC(C)=O)CC3)cccc2n1CC(F)(F)F] | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl acetate | 635.2 |
| 568A | 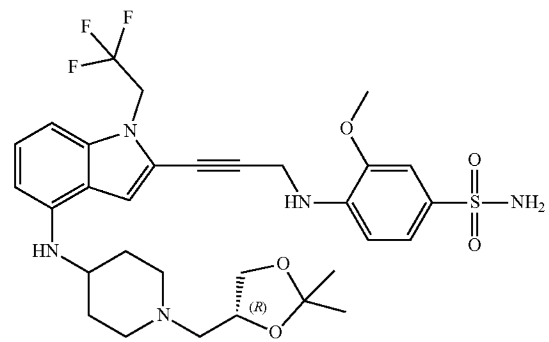 | 4-[(3-{4-[(1-{[(4R)-2,2-dimethyl-1,3-dioxolan-4-yl]methyl}piperidin-4-yl)amino]-1-(2,2,2-trifluoroethyl)-1H-indol-2-yl}prop-2-yn-1-yl)amino]-3-methoxybenzene-1-sulfonamide | 650.3 |
| 569A | 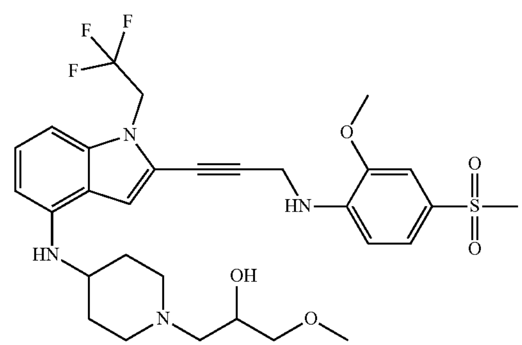 [SMILES: COCC(O)CN1CCC(Nc2cccc3c2cc(C#CCNc2ccc(S(C)(=O)=O)cc2OC)n3CC(F)(F)F)CC1] | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol | 623.3 |

TABLE 4-continued

| Compound No. | Structure | IUPAC | LC-MS (ES+, m/z) |
|---|---|---|---|
| 570A | 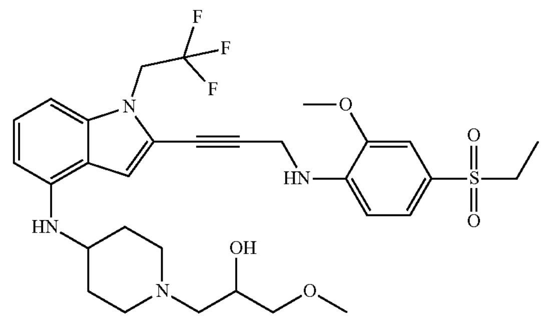 [SMILES: CCS(=O)(=O)c1ccc(NCC#Cc2cc3c(NC4CCN(CC(O)COC)CC4)cccc3n2CC(F)(F)F)c(OC)c1] | 1-(4-((2-(3-((4-(ethylsulfonyl)-2-methoxyphenyl)amino)prop-1-yn-1-yl)-1-(2,2,2-trifluoroethyl)-1H-indol-4-yl)amino)piperidin-1-yl)-3-methoxypropan-2-ol | 637.2 |
| 571A | 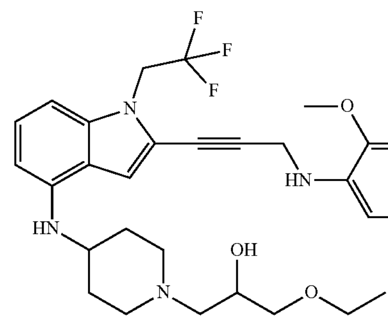 | 1-ethoxy-3-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)propan-2-ol | 637.3 |
| 572A | 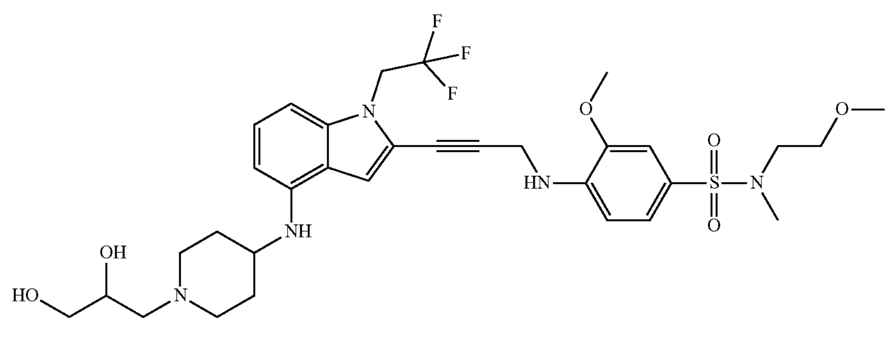 [SMILES: COCCN(C)S(=O)(=O)c1ccc(NCC#Cc2cc3c(NC4CCN(CC(O)CO)CC4)cccc3n2CC(F)(F)F)c(OC)c1] | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-(2-methoxyethyl)-N-methylbenzene-1-sulfonamide | 682.2 |

TABLE 4-continued
| Compound No. | Structure | IUPAC | LC-MS (ES+, m/z) |
|---|---|---|---|
| 573A | 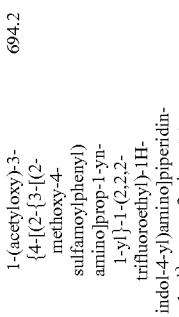 | 1-(acetyloxy)-3-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl acetate | 694.2 |
| 574A | 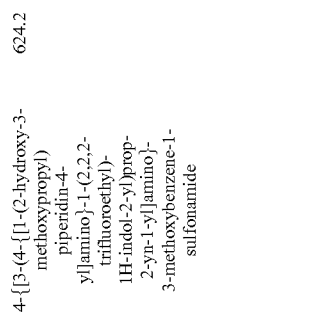 | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzene-1-sulfonamide | 624.2 |

TABLE 4-continued

| Compound No. | Structure | IUPAC | LC-MS (ES+, m/z) |
|---|---|---|---|
| 575A | 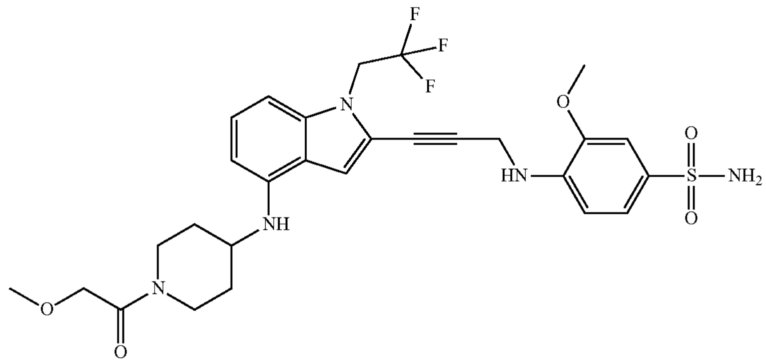 | 3-methoxy-4-[3-(4-{[1-(2-methoxyacetyl)piperidin-4-yl]amino}-1-(2,2,2-trifluoroethyl)-1H-indol-2-yl)prop-2-yn-1-yl]amino}benzene-1-sulfonamide | 608.2 |
| 576A | 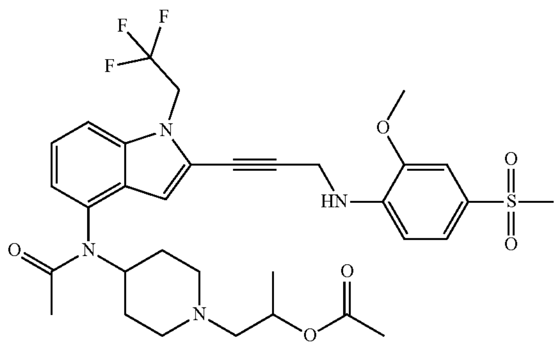 [SMILES: COc1cc(S(C)(=O)=O)ccc1NCC#Cc1cc2c(N(C(C)=O)C3CCN(CC(C)OC(C)=O)CC3)cccc2n1CC(F)(F)F] | 1-(4-(N-(2-(3-((2-methoxy-4-(methylsulfonyl)phenyl)amino)prop-1-yn-1-yl)-1-(2,2,2-trifluoroethyl)-1H-indol-4-yl)acetamido)piperidin-1-yl)propan-2-yl acetate | |
| 577A | 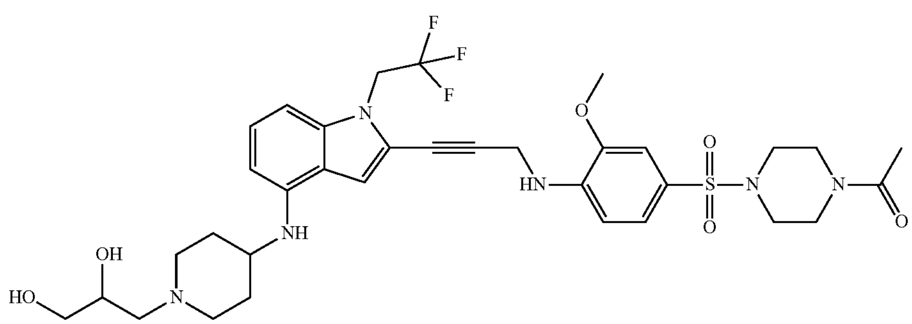 [SMILES: COc1cc(S(=O)(=O)N2CCN(C(C)=O)CC2)ccc1NCC#Cc1cc2c(NC3CCN(CC(O)CO)CC3)cccc2n1CC(F)(F)F] | 1-[4-(4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxybenzenesulfonyl)piperazin-1-yl]ethan-1-one | 721.3 |

| Compound No. | Structure | IUPAC | LC-MS (ES+, m/z) |
|---|---|---|---|
| 578A | 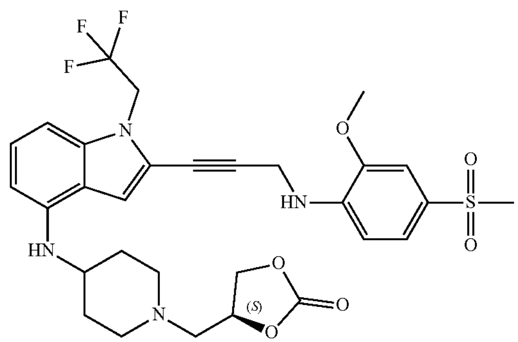 | (4S)-4-({4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}methyl)-1,3-dioxolan-2-one | 635.2 |
| 579A | 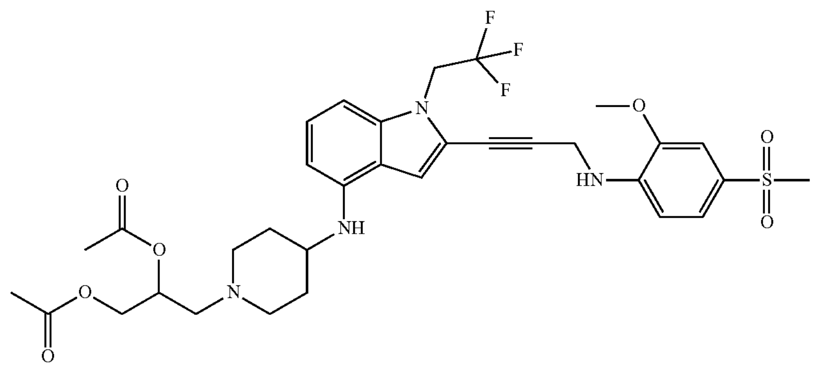 [SMILES: COc1cc(S(C)(=O)=O)ccc1NCC#Cc1cc2c(NC3CCN(CC(COC(C)=O)OC(C)=O)CC3)cccc2n1CC(F)(F)F] | 1-(acetyloxy)-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl acetate | 693.2 |

TABLE 4-continued

| Compound No. | Structure | IUPAC | LC-MS (ES+, m/z) |
|---|---|---|---|
| 580A | 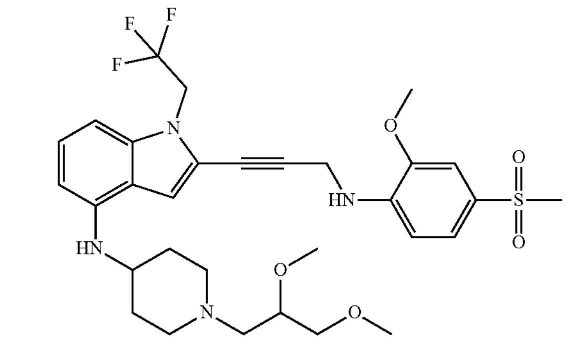 [SMILES: COCC(CN1CCC(Nc2cccc3c2cc(C#CCNc2ccc(S(C)(=O)=O)cc2OC)n3CC(F)(F)F)CC1)OC] | N-[1-(2,3-dimethoxypropyl)piperidin-4-yl]-2-{3-[(4-methanesulfonyl-2-methoxyphenyl)amino]prop-1-yn-1-yl}-1-(2,2,2-trifluoroethyl)-1H-indol-4-amine | 637.3 |
| 581A | 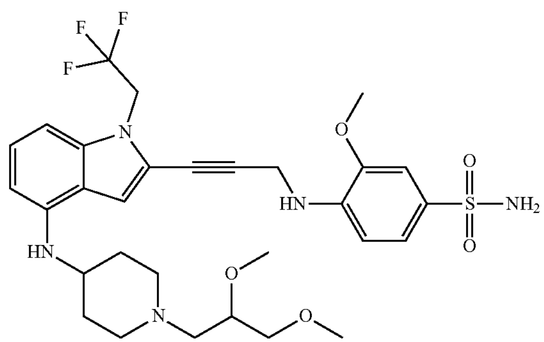 [SMILES: COCC(CN1CCC(Nc2cccc3c2cc(C#CCNc2ccc(S(N)(=O)=O)cc2OC)n3CC(F)(F)F)CC1)OC] | 4-{[3-(4-{[1-(2,3-dimethoxypropyl)piperidin-4-yl]amino}-1-(2,2,2-trifluoroethyl)-1H-indol-2-yl)prop-2-yn-1-yl]amino}-3-methoxybenzene-1-sulfonamide | 638.2 |
| 582A | 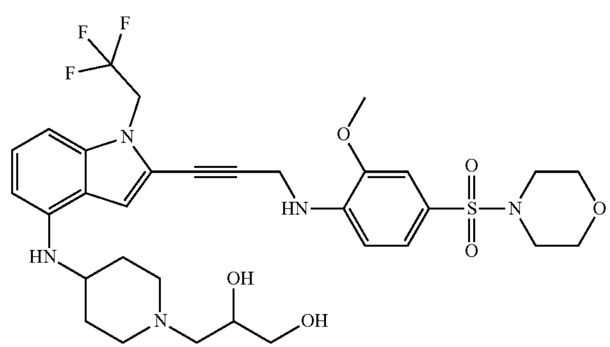 [SMILES: COc1cc(S(=O)(=O)N2CCOCC2)ccc1NCC#Cc1cc2c(NC3CCN(CC(O)CO)CC3)cccc2n1CC(F)(F)F] | 3-(4-{[2-(3-{[2-methoxy-4-(morpholine-4-sulfonyl)phenyl]amino}prop-1-yn-1-yl)-1-(2,2,2-trifluoroethyl)-1H-indol-4-yl]amino}piperidin-1-yl)propane-1,2-diol | 680.2 |

TABLE 4-continued
| Compound No. | Structure | IUPAC | LC-MS (ES+, m/z) |
|---|---|---|---|
| 583A | 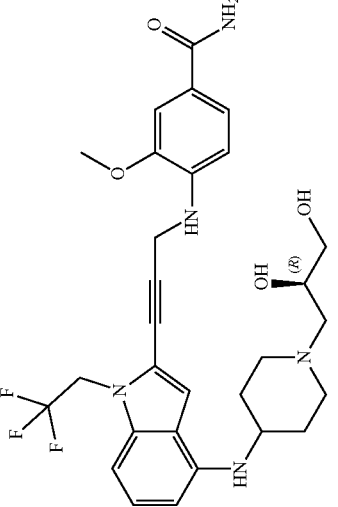 | 4-({3-[4-({1-[(2R)-2,3-dihydroxypropyl]piperidin-4-yl}amino)-1-(2,2,2-trifluoroethyl)-1H-indol-2-yl]prop-2-yn-1-yl}amino)-3-methoxybenzamide | 574.2 |
| 584A | 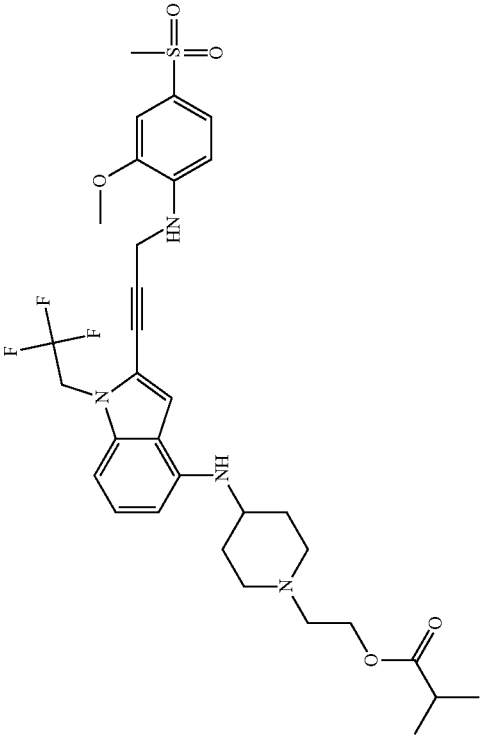 | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl} ethyl 2-methylpropanoate | 649.3 |

TABLE 4-continued
| Compound No. | Structure | IUPAC | LC-MS (ES+, m/z) |
|---|---|---|---|
| 585A | 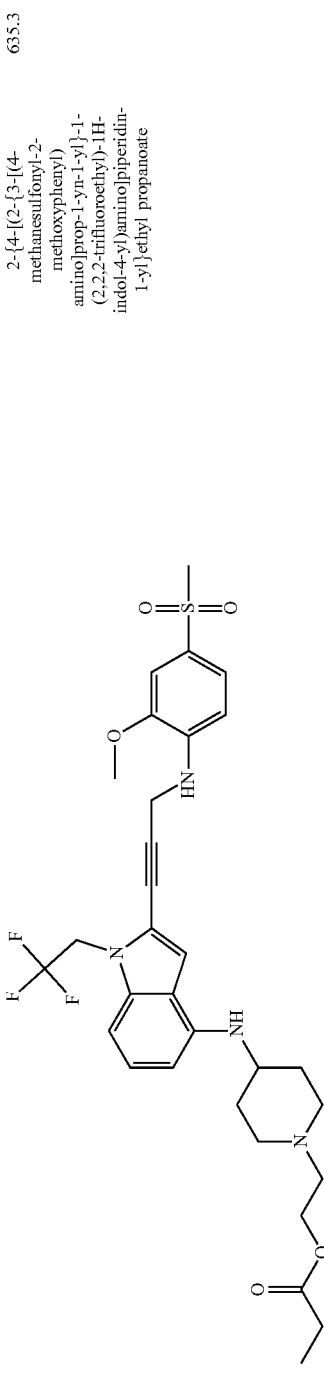 | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethyl propanoate | 635.3 |
| 586A | 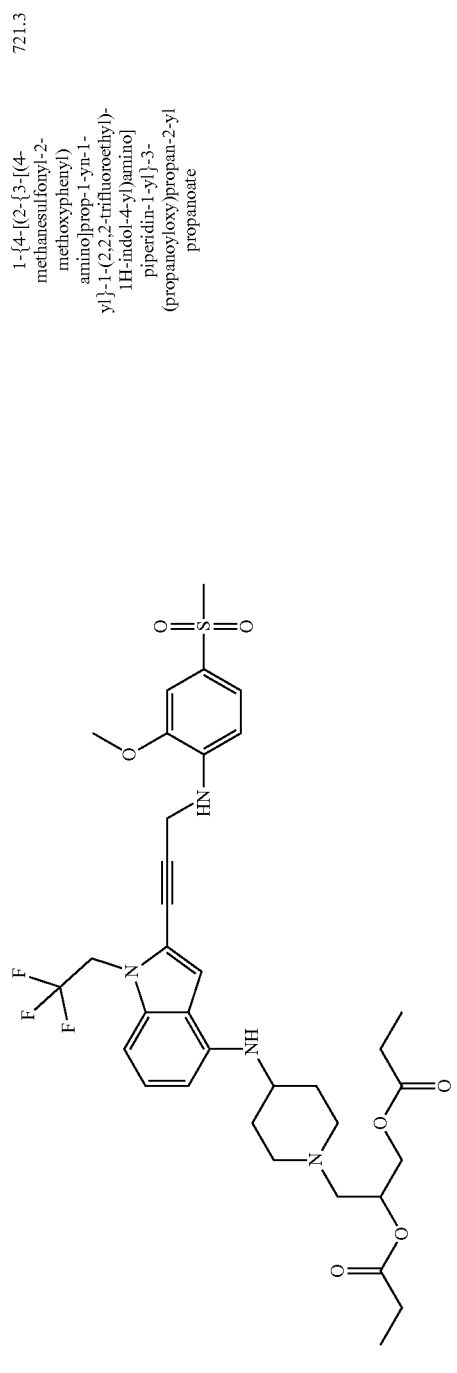 | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-(propanoyloxy)propan-2-yl propanoate | 721.3 |

TABLE 4-continued
| Compound No. | Structure | IUPAC | LC-MS (ES+, m/z) |
|---|---|---|---|
| 587A | 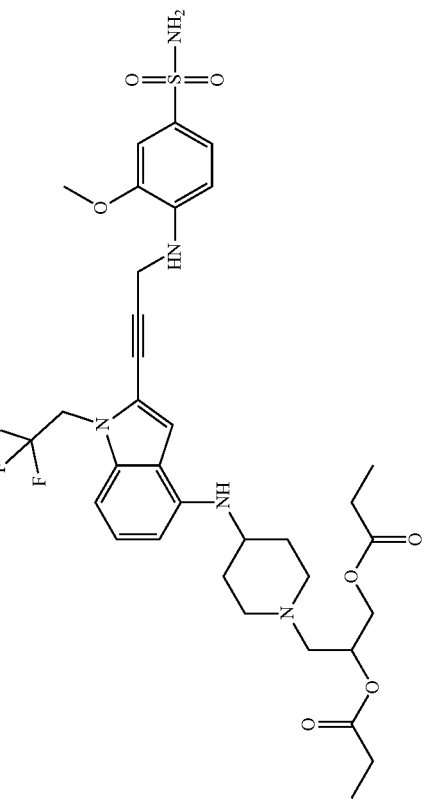 | 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}-3-(propanoyloxy)propan-2-yl propanoate | 722.2 |
| 588A | 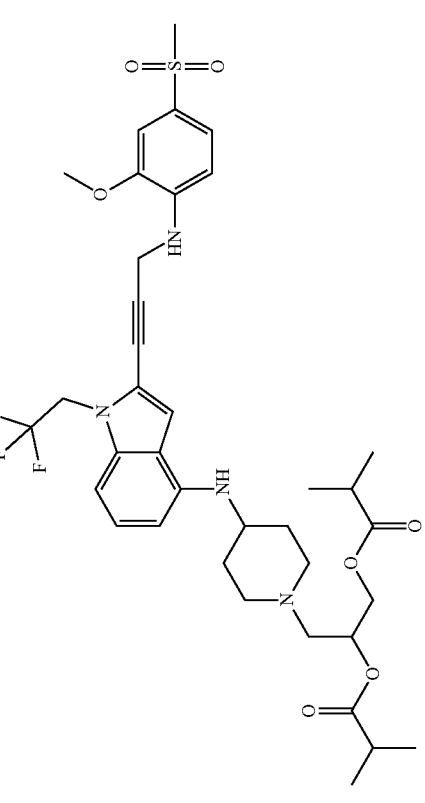 | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-[(2-methylpropanoyl)oxy]propan-2-yl 2-methylpropanoate | 749.3 |

TABLE 4-continued
| Compound No. | Structure | IUPAC | LC-MS (ES+, m/z) |
|---|---|---|---|
| 589A | 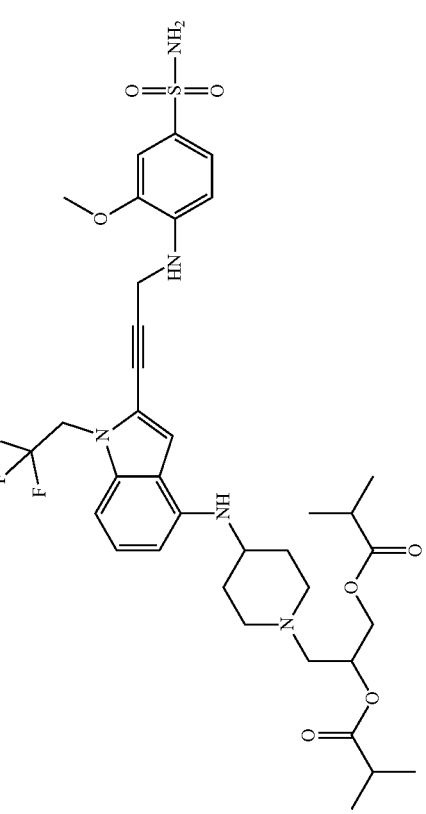 | 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}-3-[(2-methylpropanoyl)oxy]propan-2-yl 2-methylpropanoate | 750.3 |
| 590A | 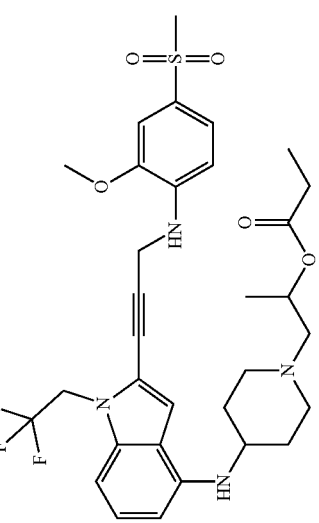 | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl propanoate | 649.3 |

TABLE 4-continued
| Compound No. | Structure | IUPAC | LC-MS (ES+, m/z) |
|---|---|---|---|
| 591A | 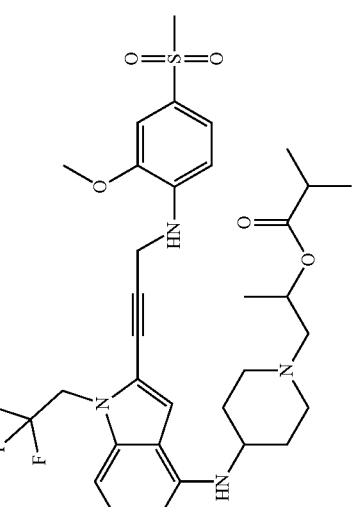 | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl 2-methylpropanoate | 663.3 |
| 592A | 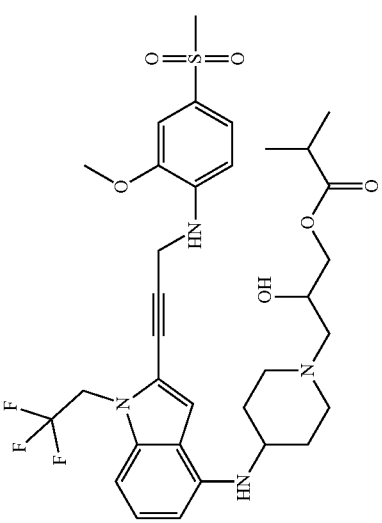 | 2-hydroxy-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propyl 2-methylpropanoate | 679.3 |

TABLE 4-continued

| Compound No. | Structure | IUPAC | LC-MS (ES+, m/z) |
|---|---|---|---|
| 593A | 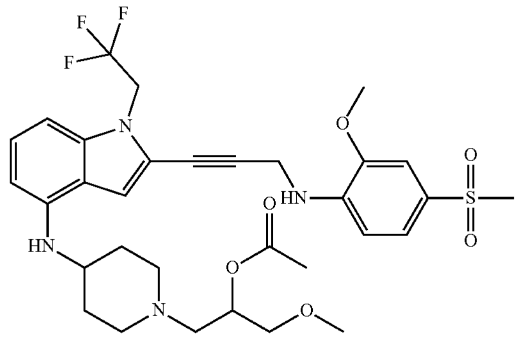 [SMILES: COCC(CN1CCC(Nc2cccc3c2cc(C#CCNc2ccc(S(C)(=O)=O)cc2OC)n3CC(F)(F)F)CC1)OC(C)=O] | 1-{4-[(2-{3-[(4-methanesulfonyl-2-methoxyphenyl)amino]prop-1-yn-1-yl}-1-(2,2,2-trifluoroethyl)-1H-indol-4-yl)aminolpiperidin-1-yl]}-3-methoxypropan-2-yl acetate | 665.3 |
| 594A | 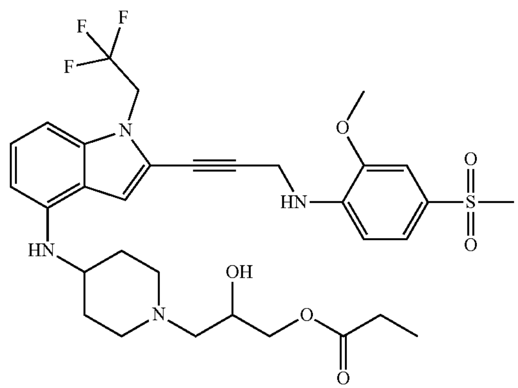 [SMILES: CCC(=O)OCC(O)CN1CCC(Nc2cccc3c2cc(C#CCNc2ccc(S(C)(=O)=O)cc2OC)n3CC(F)(F)F)CC1] | 2-hydroxy-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propyl propanoate | 665.3 |

TABLE 4-continued

| Compound No. | Structure | IUPAC | LC-MS (ES+, m/z) |
|---|---|---|---|
| 595A | 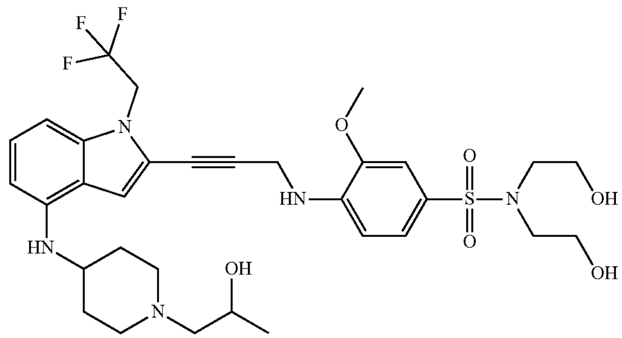 [SMILES: COc1cc(S(=O)(=O)N(CCO)CCO)ccc1NCC#Cc1cc2c(NC3CCN(CC(C)O)CC3)cccc2n1CC(F)(F)F] | N,N-bis(2-hydroxyethyl)-4-{[3-(4-{[1-(2-hydroxypropyl)piperidin-4-yl]amino}-1-(2,2,2-trifluoroethyl)-1H-indol-2-yl)prop-2-yn-1-yl]amino}-3-methoxybenzene-1-sulfonamide | 682.2 |
| 596A | 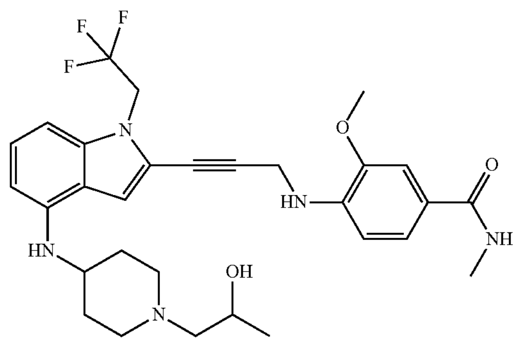 [SMILES: CNC(=O)c1ccc(NCC#Cc2cc3c(NC4CCN(CC(C)O)CC4)cccc3n2CC(F)(F)F)c(OC)c1] | 4-{[3-(4-{[1-(2-hydroxypropyl)piperidin-4-yl]amino}-1-(2,2,2-trifluoroethyl)-1H-indol-2-yl)prop-2-yn-1-yl]amino}-3-methoxy-N-methylbenzamide | 572.3 |
| 597A | 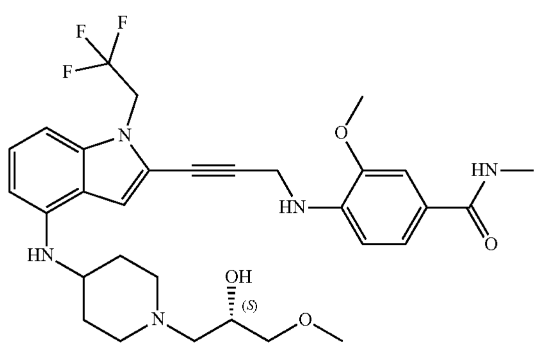 | (S)-4-((3-(4-((1-(2-hydroxy-3-methoxypropyl)piperidin-4-yl)amino)-1-(2,2,2-trifluoroethyl)-1H-indol-2-yl)prop-2-yn-1-yl)amino)-3-methoxy-N-methylbenzamide | 602.3 |

TABLE 4-continued

| Compound No. | Structure | IUPAC | LC-MS (ES+, m/z) |
|---|---|---|---|
| 598A | 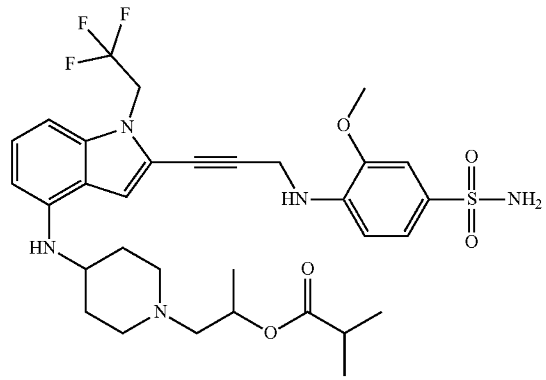 [SMILES: COc1cc(S(N)(=O)=O)ccc1NCC#Cc1cc2c(NC3CCN(CC(C)OC(=O)C(C)C)CC3)cccc2n1CC(F)(F)F] | 1-{4-[(2-{3-[(2-methoxy-4-sulfamoylphenyl)amino]prop-1-yn-1-yl]-1-(2,2,2-trifluoroethyl)-1H-indol-4-yl)amino]piperidin-1-yl}propan-2-yl 2-methylpropanoate | 664.4 |
| 599A | 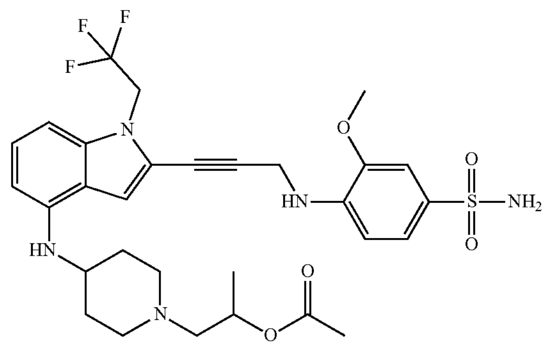 [SMILES: COc1cc(S(N)(=O)=O)ccc1NCC#Cc1cc2c(NC3CCN(CC(C)OC(C)=O)CC3)cccc2n1CC(F)(F)F] | 1-{4-[(2-{3-[(2-methoxy-4-sulfamoylphenyl)amino]prop-1-yn-1-yl]-1-(2,2,2-trifluoroethyl)-1H-indol-4-yl)amino]piperidin-1-yl}propan-2-yl acetate | 636.3 |

TABLE 4-continued
| Compound No. | Structure | IUPAC | LC-MS (ES+, m/z) |
|---|---|---|---|
| 600A | 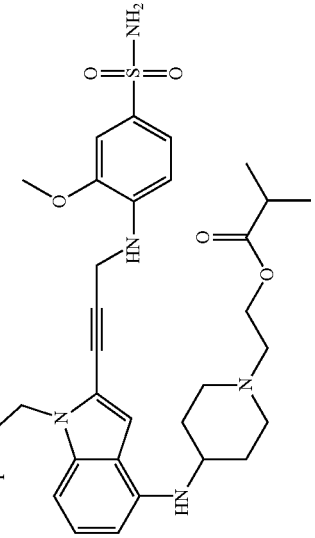 | 2-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}ethyl 2-methylpropanoate | 650.3 |
| 601A | 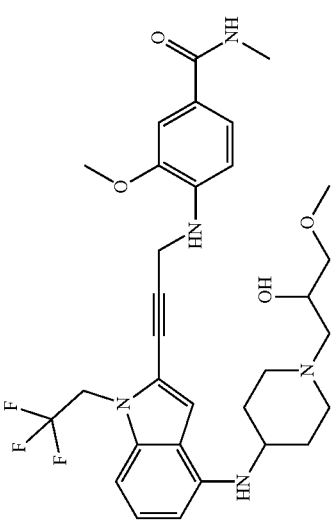 | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxy-N-methylbenzamide | 602.4 |

TABLE 4-continued
| Compound No. | Structure | IUPAC | LC-MS (ES+, m/z) |
|---|---|---|---|
| 602A | 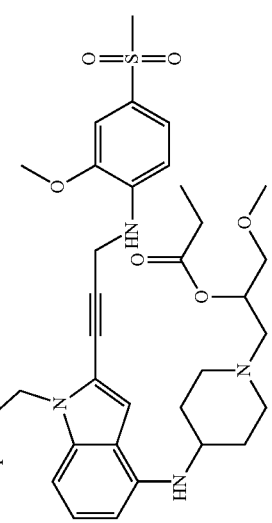 | 1-{4-[(2-{3-[(4-methanesulfonyl-2-methoxyphenyl)amino]prop-1-yn-1-yl]-1-(2,2,2-trifluoroethyl)-1H-indol-4-yl)amino]piperidin-1-yl}-3-methoxypropan-2-yl propanoate | 679.3 |
| 603A | 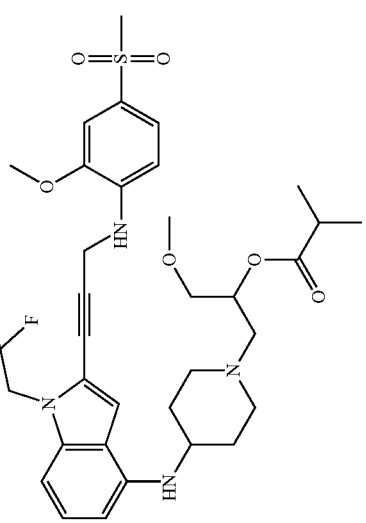 | 1-{4-[(2-{3-[(4-methanesulfonyl-2-methoxyphenyl)amino]prop-1-yn-1-yl]-1-(2,2,2-trifluoroethyl)-1H-indol-4-yl)amino]piperidin-1-yl}-3-methoxypropan-2-yl 2-methylpropanoate | 693.3 |

TABLE 4-continued

| Compound No. | Structure | IUPAC | LC-MS (ES+, m/z) |
|---|---|---|---|
| 604A | 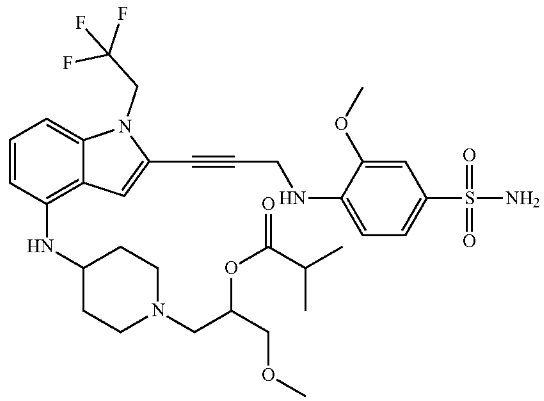 [SMILES: COCC(CN1CCC(Nc2cccc3c2cc(C#CCNc2ccc(S(N)(=O)=O)cc2OC)n3CC(F)(F)F)CC1)OC(=O)C(C)C] | 1-methoxy-3-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl 2-methylpropanoate | 694.3 |
| 605A | 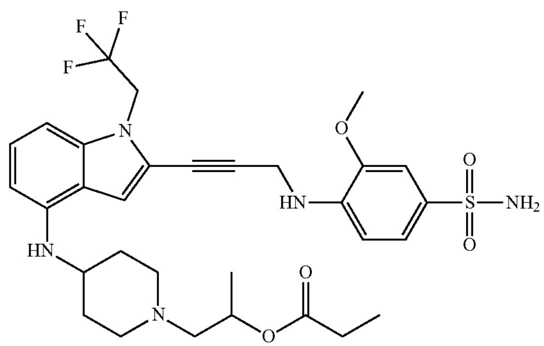 [SMILES: CCC(=O)OC(C)CN1CCC(Nc2cccc3c2cc(C#CCNc2ccc(S(N)(=O)=O)cc2OC)n3CC(F)(F)F)CC1] | 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl propanoate | 650.2 |

TABLE 4-continued

| Compound No. | Structure | IUPAC | LC-MS (ES+, m/z) |
|---|---|---|---|
| 606A | 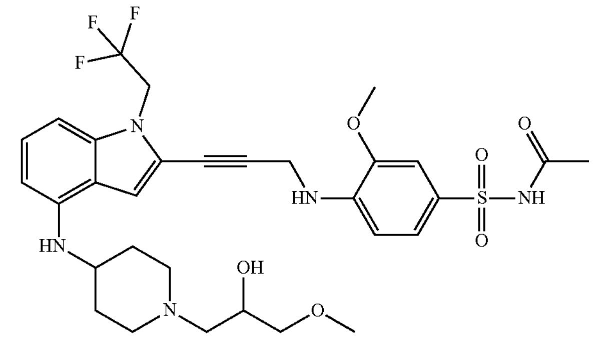 [SMILES: COCC(O)CN1CCC(Nc2cccc3c2cc(C#CCNc2ccc(S(=O)(=O)NC(C)=O)cc2OC)n3CC(F)(F)F)CC1] | N-(4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzenesulfonyl)acetamide | 666.2 |
| 607A | 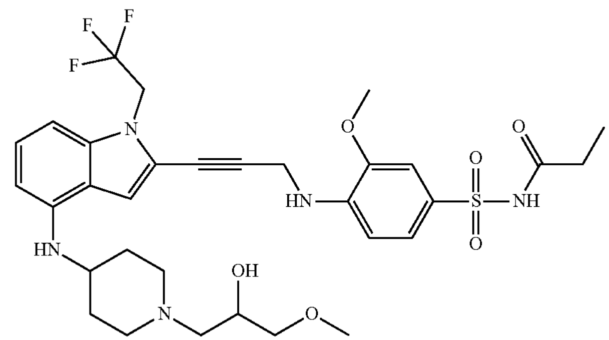 [SMILES: CCC(=O)NS(=O)(=O)c1ccc(NCC#Cc2cc3c(NC4CCN(CC(O)COC)CC4)cccc3n2CC(F)(F)F)c(OC)c1] | N-(4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzenesulfonyl)propanamide | 680.3 |
| 608A | 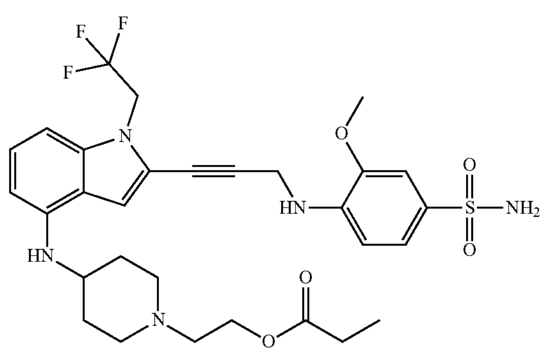 [SMILES: CCC(=O)OCCN1CCC(Nc2cccc3c2cc(C#CCNc2ccc(S(N)(=O)=O)cc2OC)n3CC(F)(F)F)CC1] | 2-(4-{[2-[(3-[(2-methoxy-4-sulfamoylphenyl)amino]prop-1-yn-1-yl]-1-(2,2,2-trifluoroethyl)-1H-indol-4-yl)amino]piperidin-1-yl]ethyl propanoate | 636.2 |

TABLE 4-continued

| Compound No. | Structure | IUPAC | LC-MS (ES⁺, m/z) |
|---|---|---|---|
| 609A | 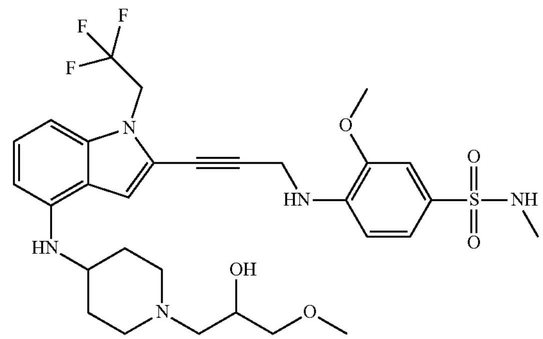 [SMILES: CNS(=O)(=O)c1ccc(NCC#Cc2cc3c(NC4CCN(CC(O)COC)CC4)cccc3n2CC(F)(F)F)c(OC)c1] | 4-{3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxy-N-methylbenzene-1-sulfonamide | 638.2 |
| 610A | 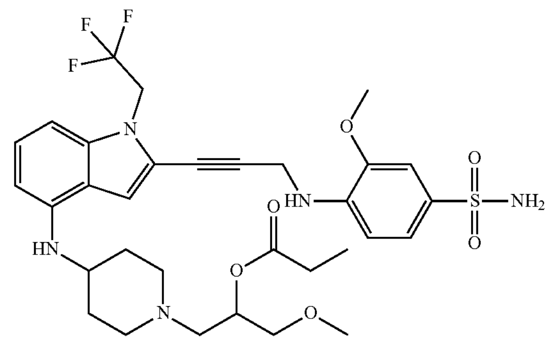 [SMILES: CCC(=O)OC(COC)CN1CCC(Nc2cccc3c2cc(C#CCNc2ccc(S(N)(=O)=O)cc2OC)n3CC(F)(F)F)CC1] | 1-methoxy-3-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl} propan-2-yl propanoate | 680.3 |
| 611A | 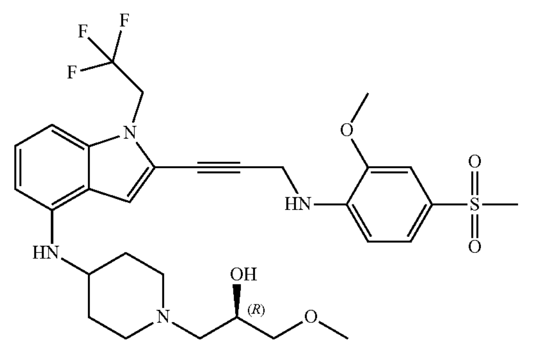 | (2R)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol | 623.3 |

TABLE 4-continued
| Compound No. | Structure | IUPAC | LC-MS (ES+, m/z) |
|---|---|---|---|
| 612A | 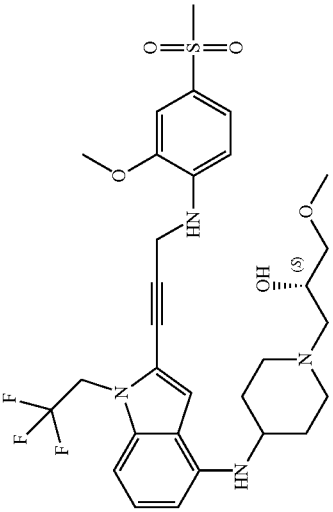 | (2S)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol | 623.4 |
| 613A | 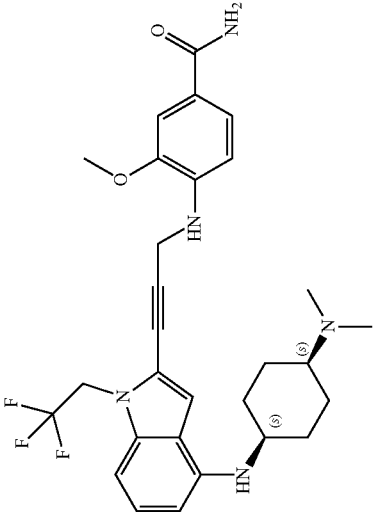 | 3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide | 542.2 |

TABLE 4-continued

| Compound No. | Structure | IUPAC | LC-MS (ES+, m/z) |
|---|---|---|---|
| 614A | 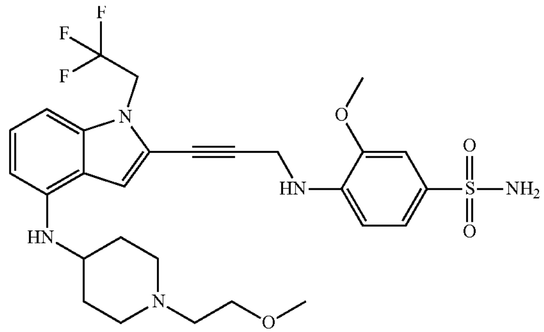 [SMILES: COCCN1CCC(Nc2cccc3c2cc(C#CCNc2ccc(S(N)(=O)=O)cc2OC)n3CC(F)(F)F)CC1] | 3-methoxy-4-((3-(4-((1-(2-methoxyethyl)piperidin-4-yl)amino)-1-(2,2,2-trifluoroethyl)-1H-indol-2-yl)prop-2-yn-1-yl)amino)benzenesulfonamide | |
| 615A | 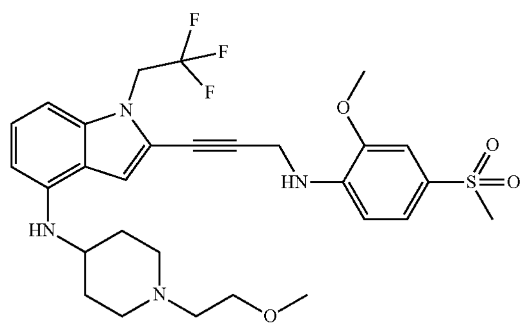 [SMILES: COCCN1CCC(Nc2cccc3c2cc(C#CCNc2ccc(S(C)(=O)=O)cc2OC)n3CC(F)(F)F)CC1] | 2-(3-((2-methoxy-4-(methylsulfonyl)phenyl)amino)prop-1-yn-1-yl)-N-(1-(2-methoxyethyl)piperidin-4-yl)-1-(2,2,2-trifluoroethyl)-1H-indol-4-amine | 593.2 |
| 616A | 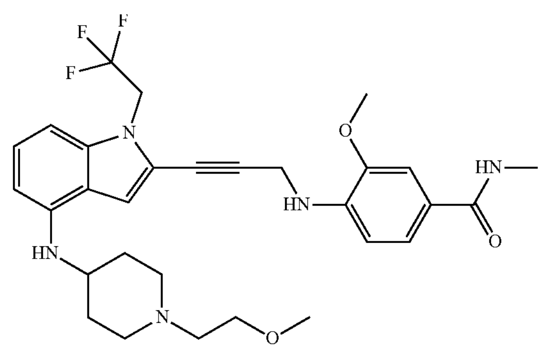 [SMILES: CNC(=O)c1ccc(NCC#Cc2cc3c(NC4CCN(CCOC)CC4)cccc3n2CC(F)(F)F)c(OC)c1] | 3-methoxy-4-{[3-(4-{[1-(2-methoxyethyl)piperidin-4-yl]amino}-1-(2,2,2-trifluoroethyl)-1H-indol-2-yl)prop-2-yn-1-yl]amino}-N-methylbenzamide | 572.3 |

TABLE 4-continued

| Compound No. | Structure | IUPAC | LC-MS (ES+, m/z) |
|---|---|---|---|
| 617A | 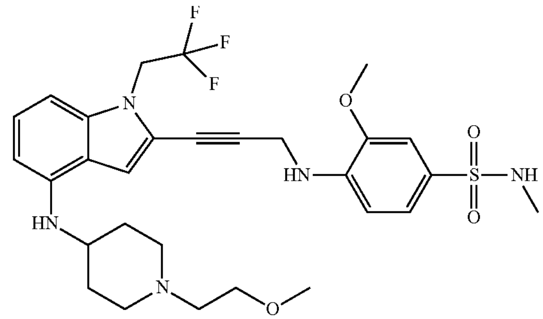 [SMILES: CNS(=O)(=O)c1ccc(NCC#Cc2cc3c(NC4CCN(CCOC)CC4)cccc3n2CC(F)(F)F)c(OC)c1] | 3-methoxy-4-{[3-(4-{[1-(2-methoxyethyl)piperidin-4-yl]amino}-1-(2,2,2-trifluoroethyl)-1H-indol-2-yl)prop-2-yn-1-yl]amino}-N-methylbenzene-1-sulfonamide | 608 |
| 618A | 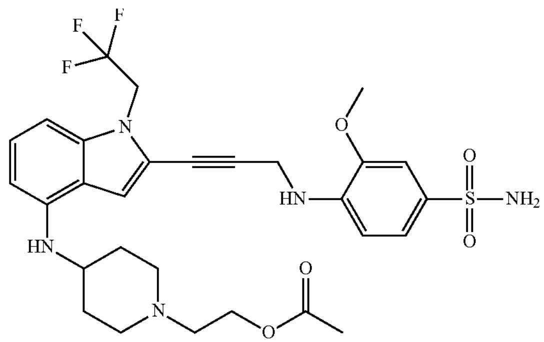 [SMILES: COc1cc(S(N)(=O)=O)ccc1NCC#Cc1cc2c(NC3CCN(CCOC(C)=O)CC3)cccc2n1CC(F)(F)F] | 2-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}EtOAc | 622.3 |
| 619A | 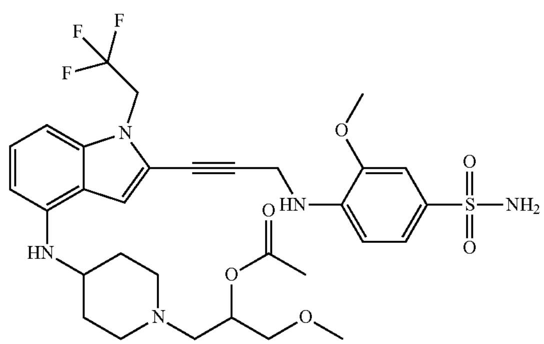 [SMILES: COCC(CN1CCC(Nc2cccc3c2cc(C#CCNc2ccc(S(N)(=O)=O)cc2OC)n3CC(F)(F)F)CC1)OC(C)=O] | 1-methoxy-3-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl acetate | 666.2 |

| Compound No. | Structure | IUPAC | LC-MS (ES⁺, m/z) |
|---|---|---|---|
| 620A | 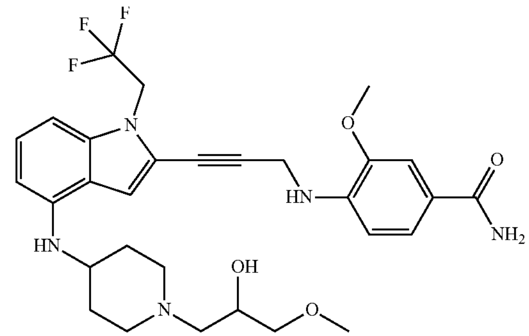 [SMILES: COCC(O)CN1CCC(Nc2cccc3c2cc(C#CCNc2ccc(C(N)=O)cc2OC)n3CC(F)(F)F)CC1] | 4-{3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzamide | 588.3 |
| 621A | 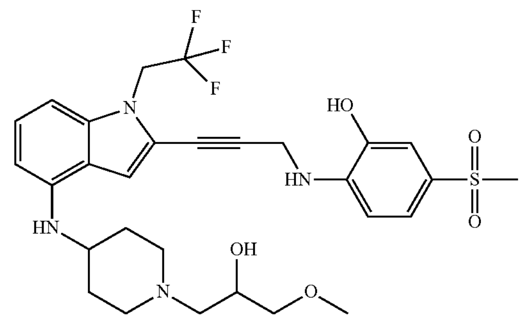 [SMILES: COCC(O)CN1CCC(Nc2cccc3c2cc(C#CCNc2ccc(S(C)(=O)=O)cc2O)n3CC(F)(F)F)CC1] | 2-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-5-methanesulfonylphenol | 609.2 |
| 622A | 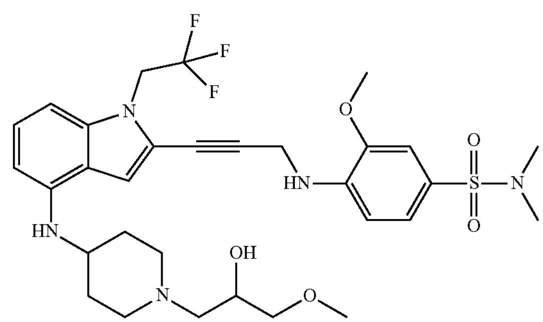 [SMILES: COCC(O)CN1CCC(Nc2cccc3c2cc(C#CCNc2ccc(S(=O)(=O)N(C)C)cc2OC)n3CC(F)(F)F)CC1] | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxy-N,N-dimethylbenzene-1-sulfonamide | 652.4 |

TABLE 4-continued

| Compound No. | Structure | IUPAC | LC-MS (ES+, m/z) |
|---|---|---|---|
| 623A | 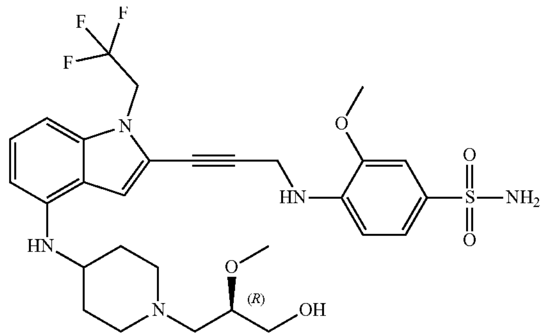 | 4-({3-[4-({1-[(2R)-3-hydroxy-2-methoxypropyl]piperidin-4-yl}amino)-1-(2,2,2-trifluoroethyl)-1H-indol-2-yl]prop-2-yn-1-yl}amino)-3-methoxybenzene-1-sulfonamide | 624.1 |
| 624A | 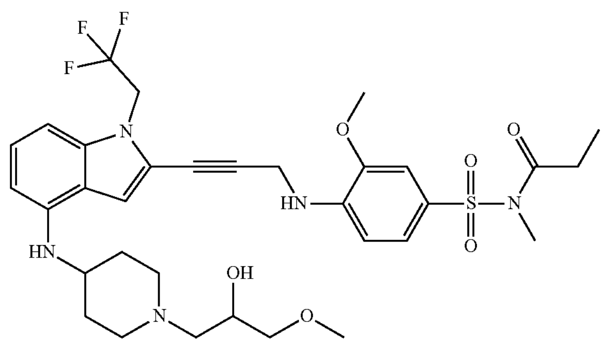 [SMILES: CCC(=O)N(C)S(=O)(=O)c1ccc(NCC#Cc2cc3c(NC4CCN(CC(O)COC)CC4)cccc3n2CC(F)(F)F)c(OC)c1] | N-(4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzenesulfonyl)-N-methylpropanamide | 694.3 |
| 625A | 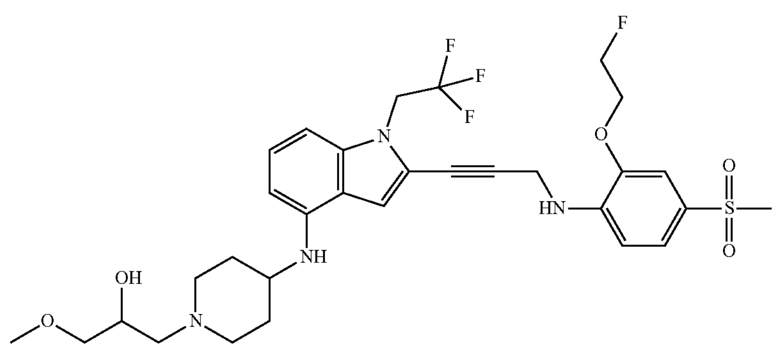 | 1-(4-{3-({[2-(3-{[2-(2-fluoroethoxy)-4-methanesulfonylphenyl]amino}prop-1-yn-1-yl)-1-(2,2,2-trifluoroethyl)-1H-indol-4-yl]amino})piperidin-1-yl)-3-methoxypropan-2-ol | 655.3 |

TABLE 4-continued

| Compound No. | Structure | IUPAC | LC-MS (ES+, m/z) |
|---|---|---|---|
| 626A | 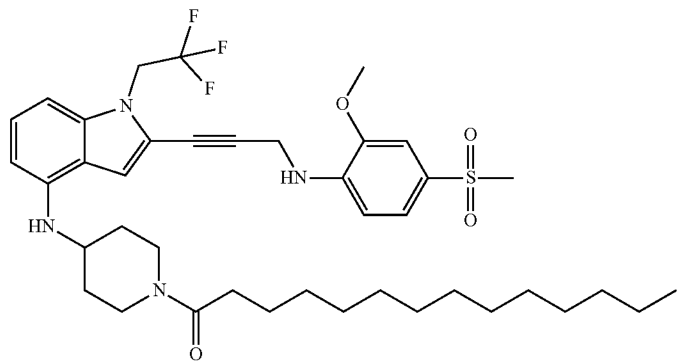 [SMILES: CCCCCCCCCCCCCC(=O)N1CCC(Nc2cccc3c2cc(C#CCNc2ccc(S(C)(=O)=O)cc2OC)n3CC(F)(F)F)CC1] | 1-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)tetradecan-1-one | |
| 627A | 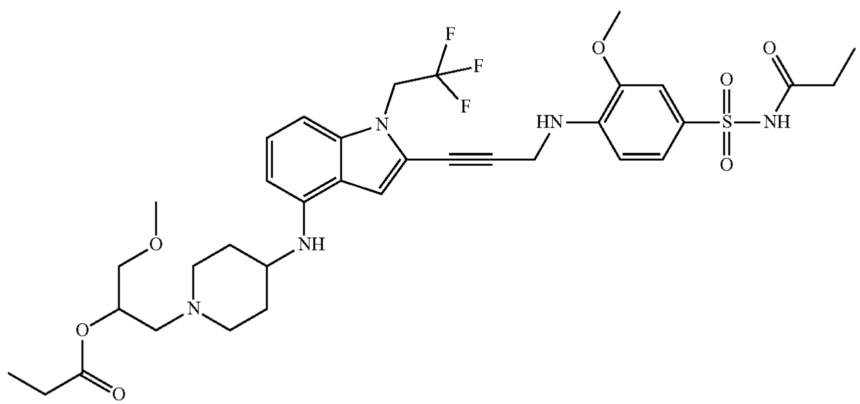 [SMILES: CCC(=O)NS(=O)(=O)c1ccc(NCC#Cc2cc3c(NC4CCN(CC(COC)OC(=O)CC)CC4)cccc3n2CC(F)(F)F)c(OC)c1] | 1-methoxy-3-(4-{[2-(3-{[2-methoxy-4-(propanamidosulfonyl)phenyl]amino}prop-1-yn-1-yl)-1-(2,2,2-trifluoroethyl)-1H-indol-4-yl]amino}piperidin-1-yl)propan-2-yl propanoate | 736.3 |

TABLE 4-continued
| Compound No. | Structure | IUPAC | LC-MS (ES+, m/z) |
|---|---|---|---|
| 628A | 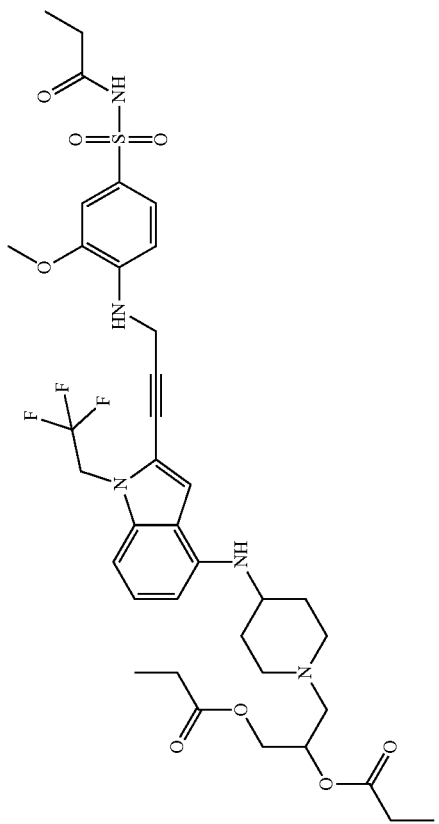 | 1-(4-{[2-(3-{[2-methoxy-4-(propanamidosulfonyl)phenyl]amino}prop-1-yn-1-yl)-1-(2,2,2-trifluoroethyl)-1H-indol-4-yl]amino}piperidin-1-yl)-3-(propanoyloxy)propan-2-yl propanoate | 778.1 |
| 629A | 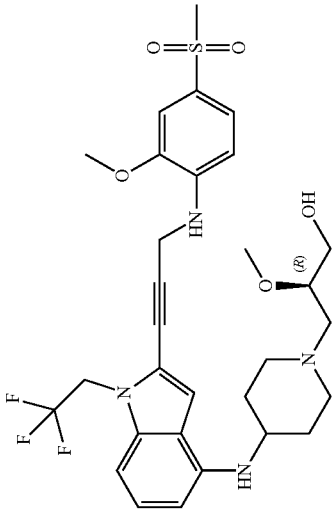 | (2R)-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-2-methoxypropan-1-ol | 623.3 |

TABLE 4-continued

| Compound No. | Structure | IUPAC | LC-MS (ES+, m/z) |
|---|---|---|---|
| 630A | 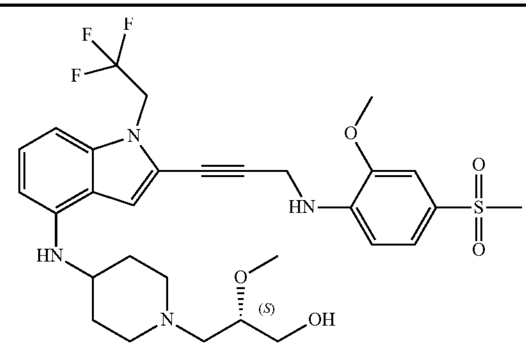 | (2S)-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-2-methoxypropan-1-ol | 623.4 |
| 631A | 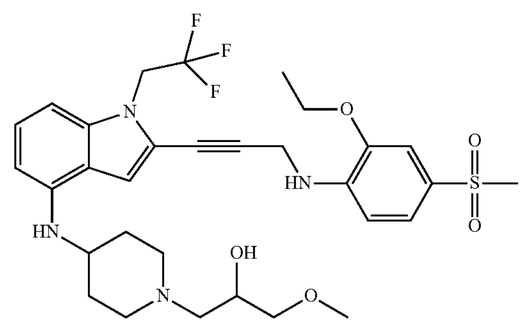 [SMILES: CCOc1cc(S(C)(=O)=O)ccc1NCC#Cc1cc2c(NC3CCN(CC(O)COC)CC3)cccc2n1CC(F)(F)F] | 1-{4-[(2-{3-[(2-ethoxy-4-methanesulfonylphenyl)amino]prop-1-yn-1-yl}-1-(2,2,2-trifluoroethyl)-1H-indol-4-yl)amino]piperidin-1-yl}-3-methoxypropan-2-ol | 637.2 |
| 632A | 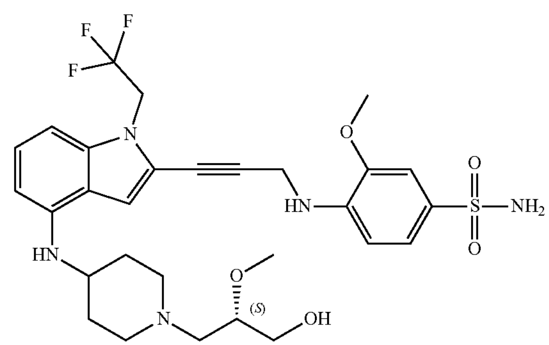 | 4-({3-[4-({1-[(2S)-3-hydroxy-2-methoxypropyl]piperidin-4-yl}amino)-1-(2,2,2-trifluoroethyl)-1H-indol-2-yl]prop-2-yn-1-yl}amino)-3-methoxybenzene-1-sulfonamide | 624.3 |

TABLE 4-continued

| Compound No. | Structure | IUPAC | LC-MS (ES+, m/z) |
|---|---|---|---|
| 633A | 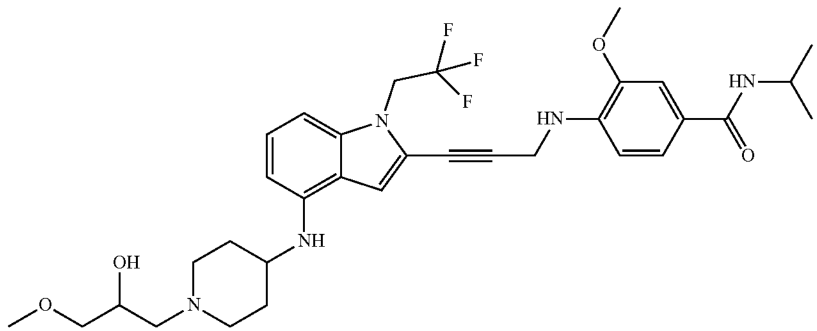 [SMILES: COCC(O)CN1CCC(Nc2cccc3c2cc(C#CCNc2ccc(C(=O)NC(C)C)cc2OC)n3CC(F)(F)F)CC1] | 4-{3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxy-N-(propan-2-yl)benzamide | 630.2 |
| 634A | 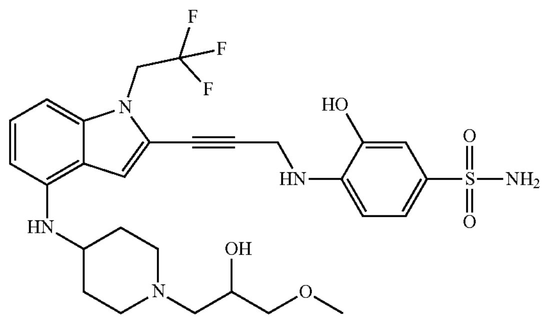 [SMILES: COCC(O)CN1CCC(Nc2cccc3c2cc(C#CCNc2ccc(S(N)(=O)=O)cc2O)n3CC(F)(F)F)CC1] | 3-hydroxy-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}benzene-1-sulfonamide | 610.1 |

TABLE 4-continued

| Compound No. | Structure | IUPAC | LC-MS (ES+, m/z) |
|---|---|---|---|
| 635A | 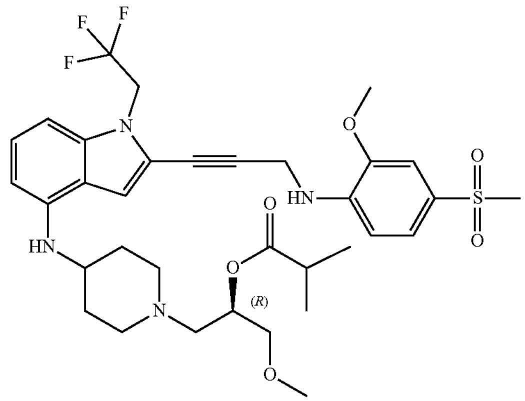 | (2R)-1-{4-[2-{3-[(4-methanesulfonyl-2-methoxyphenyl)amino]prop-1-yn-1-yl}-1-(2,2,2-trifluoroethyl)-1H-indol-4-yl}amino]piperidin-1-yl}-3-methoxypropan-2-yl 2-methylpropanoate | 693.1 |
| 636A | | N-(3-(4-((1-(2-hydroxy-3-methoxypropyl)piperidin-4-yl)amino)-1-(2,2,2-trifluoroethyl)-1H-indol-2-yl)prop-2-yn-1-yl)-N-(2-hydroxy-4-(N-propionylsulfamoyl)phenyl)propion amide | 722.3 |
| 637A | 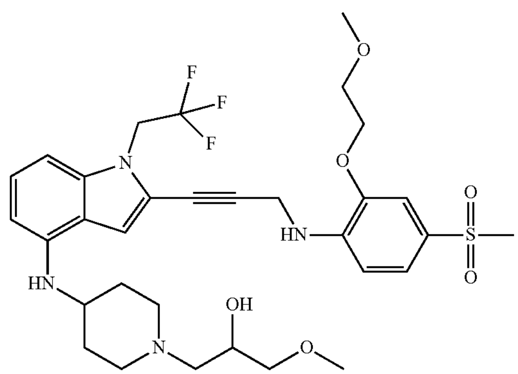 [SMILES: COCCOc1cc(S(C)(=O)=O)ccc1NCC#Cc1cc2c(NC3CCN(CC(O)COC)CC3)cccc2n1CC(F)(F)F] | 1-(4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}piperidin-1-yl)-3-methoxypropan-2-ol | 667.1 |

TABLE 4-continued
| Compound No. | Structure | IUPAC | LC-MS (ES+, m/z) |
|---|---|---|---|
| 638A | 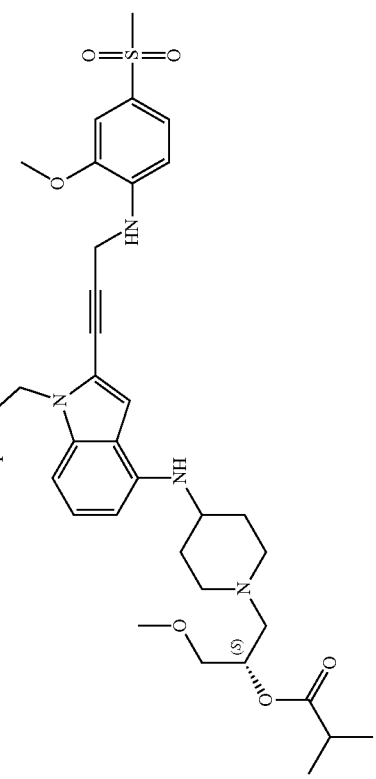 | (2S)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl 2-methylpropanoate | 693.4 |
| 639A | 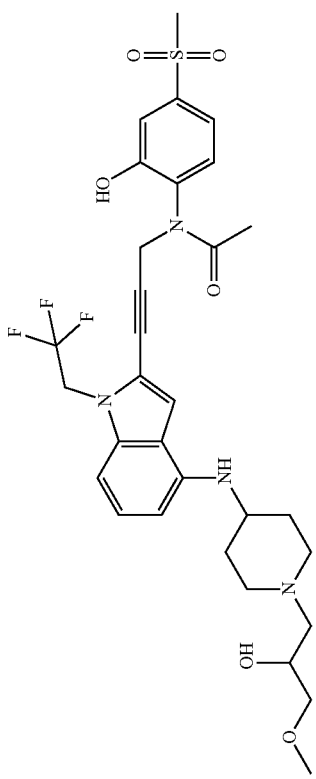 | N-(3-(4-((1-(2-hydroxy-3-methoxypropyl)piperidin-4-yl)amino)-1-(2,2,2-trifluoroethyl)-1H-indol-2-yl)prop-2-yn-1-yl)-N-(2-hydroxy-4-(methylsulfonyl)phenyl)acetamide | |

TABLE 4-continued

| Compound No. | Structure | IUPAC | LC-MS (ES+, m/z) |
|---|---|---|---|
| 640A | 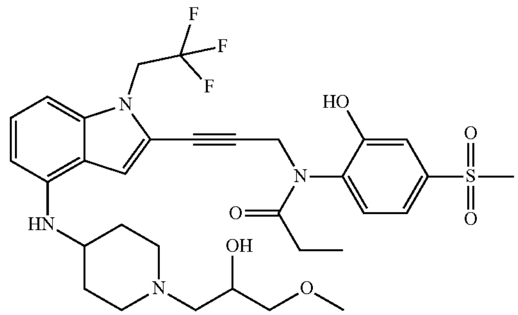 [SMILES: CCC(=O)N(CC#Cc1cc2c(NC3CCN(CC(O)COC)CC3)cccc2n1CC(F)(F)F)c1ccc(S(C)(=O)=O)cc1O] | N-(3-(4-((1-(2-hydroxy-3-methoxypropyl)piperidin-4-yl)amino)-1-(2,2,2-trifluoroethyl)-1H-indol-2-yl)prop-2-yn-1-yl)-N-(2-hydroxy-4-(methylsulfonyl)phenyl)propionamide | 665.3 |
| 641A | 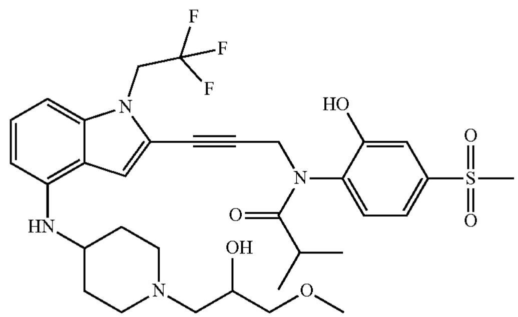 [SMILES: COCC(O)CN1CCC(Nc2cccc3c2cc(C#CCN(C(=O)C(C)C)c2ccc(S(C)(=O)=O)cc2O)n3CC(F)(F)F)CC1] | N-(3-(4-((1-(2-hydroxy-3-methoxypropyl)piperidin-4-yl)amino)-1-(2,2,2-trifluoroethyl)-1H-indol-2-yl)prop-2-yn-1-yl)-N-(2-hydroxy-4-(methylsulfonyl)phenyl)isobutyramide | 679.3 |
| 642A | 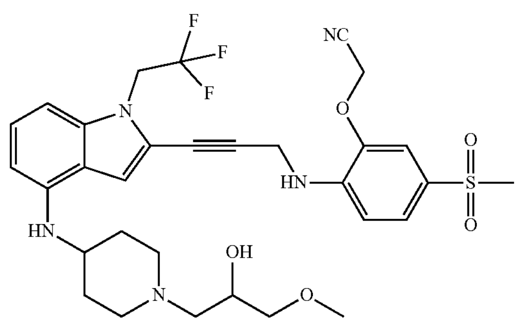 [SMILES: COCC(O)CN1CCC(Nc2cccc3c2cc(C#CCNc2ccc(S(C)(=O)=O)cc2OCC#N)n3CC(F)(F)F)CC1] | 2-(2-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-5-methanesulfonylphenoxy)acetonitrile | 648.3 |

TABLE 4-continued

| Compound No. | Structure | IUPAC | LC-MS (ES+, m/z) |
|---|---|---|---|
| 643A | 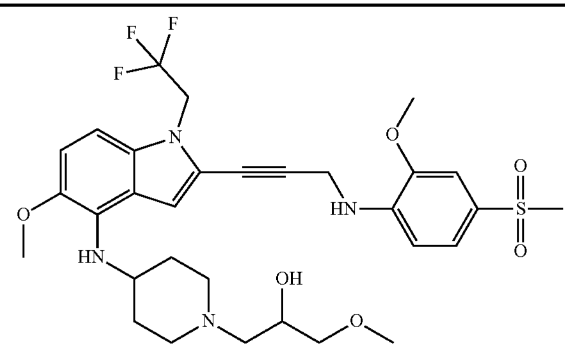 | 1-{4-[(2-{3-[(4-methanesulfonyl-2-methoxyphenyl)amino]prop-1-yn-1-yl}-5-methoxy-1-(2,2,2-trifluoroethyl)-1H-indol-4-yl)amino]piperidin-1-yl}-3-methoxypropan-2-ol | 653.4 |
| 644A | 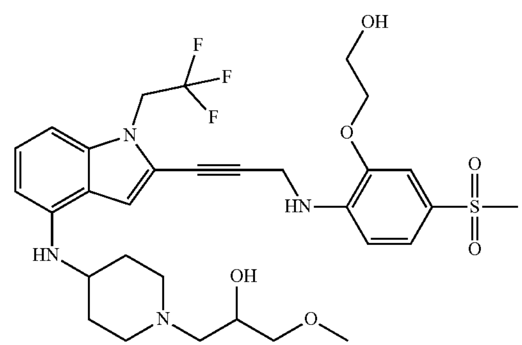 [SMILES: COCC(O)CN1CCC(Nc2cccc3c2cc(C#CCNc2ccc(S(C)(=O)=O)cc2OCCO)n3CC(F)(F)F)CC1] | 1-(4-{[2-(3-{[2-(2-hydroxyethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol | 653.3 |
| 645A | 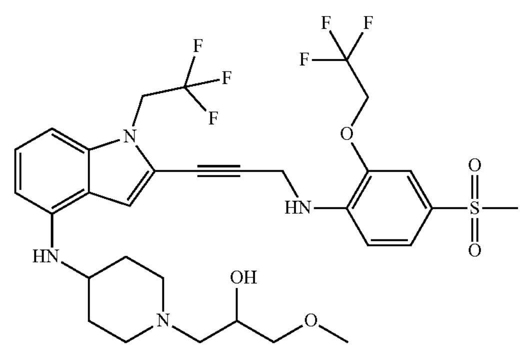 [SMILES: COCC(O)CN1CCC(Nc2cccc3c2cc(C#CCNc2ccc(S(C)(=O)=O)cc2OCC(F)(F)F)n3CC(F)(F)F)CC1] | 1-(4-{[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]amino}piperidin-1-yl)-3-methoxypropan-2-ol | 691.3 |

TABLE 4-continued

| Compound No. | Structure | IUPAC | LC-MS (ES+, m/z) |
|---|---|---|---|
| 646A | 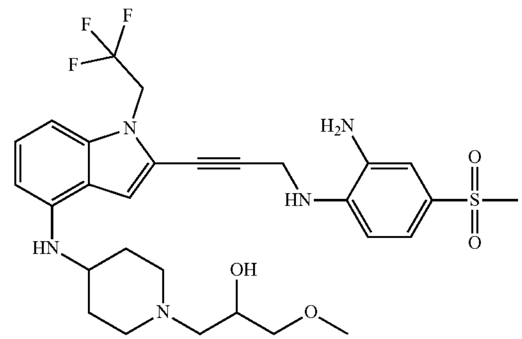 [SMILES: COCC(O)CN1CCC(Nc2cccc3c2cc(C#CCNc2ccc(S(C)(=O)=O)cc2N)n3CC(F)(F)F)CC1] | 1-[4-((2-[3-(2-amino-4-methanesulfonylphenoxy)prop-1-yn-1-yl]-1-(2,2,2-trifluoroethyl)-1H-indol-4-yl}amino)piperidin-1-yl]-3-methoxypropan-2-ol | 609.1 |
| 647A | 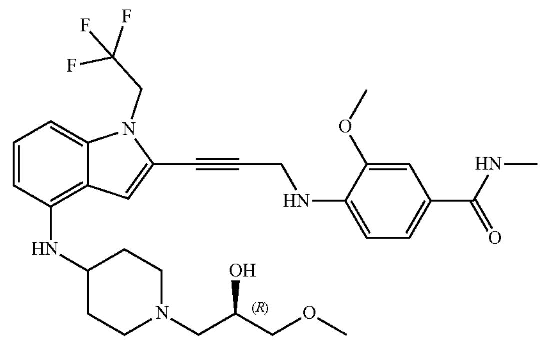 | 4-({3-[4-({1-[(2R)-2-hydroxy-3-methoxypropyl]piperidin-4-yl}amino)-1-(2,2,2-trifluoroethyl)-1H-indol-2-yl]prop-2-yn-1-yl}amino)-3-methoxy-N-methylbenzamide | 602.3 |

TABLE 4-continued

| Compound No. | Structure | IUPAC | LC-MS (ES+, m/z) |
|---|---|---|---|
| 648A | 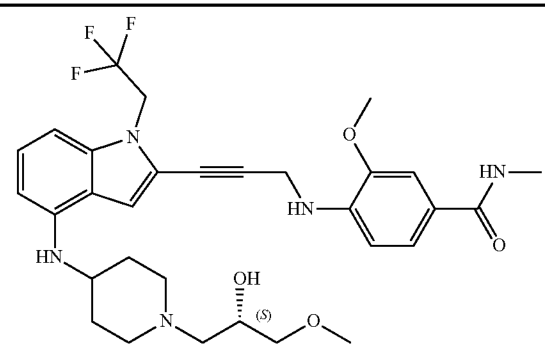 | 4-({3-[4-({1-[(2S)-2-hydroxy-3-methoxypropyl]piperidin-4-yl}amino)-1-(2,2,2-trifluoroethyl)-1H-indol-2-yl]prop-2-yn-1-yl}amino)-3-methoxy-N-methylbenzamide | 602.3 |
| 649A | 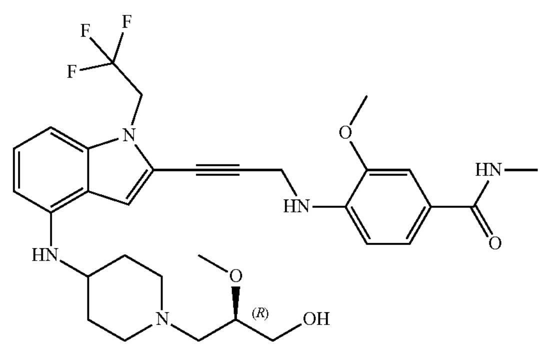 | 4-({3-[4-({1-[(2R)-3-hydroxy-2-methoxypropyl]piperidin-4-yl}amino)-1-(2,2,2-trifluoroethyl)-1H-indol-2-yl]prop-2-yn-1-yl}amino)-3-methoxy-N-methylbenzamide | 602.3 |
| 650A | 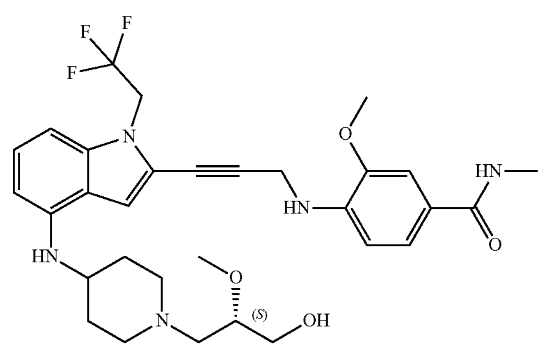 | 4-({3-[4-({1-[(2S)-3-hydroxy-2-methoxypropyl]piperidin-4-yl}amino)-1-(2,2,2-trifluoroethyl)-1H-indol-2-yl]prop-2-yn-1-yl}amino)-3-methoxy-N-methylbenzamide | 602.3 |

TABLE 4-continued
| Compound No. | Structure | IUPAC | LC-MS (ES+, m/z) |
|---|---|---|---|
| 651A | 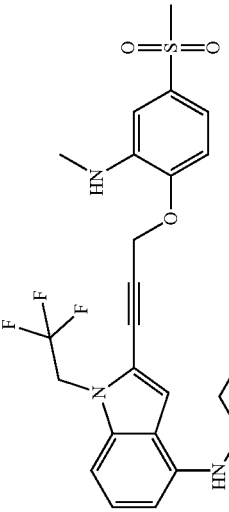 | 1-{4-[(2-{3-[4-methane sulfonyl-2-(methylamino) phenoxy]prop-1-yn-1-yl}-1-(2,2,2-trifluoroethyl)-1H-indol-4-yl)amino] piperidin-1-yl}-3-methoxypropan-2-ol | 623.4 |
| 652A | 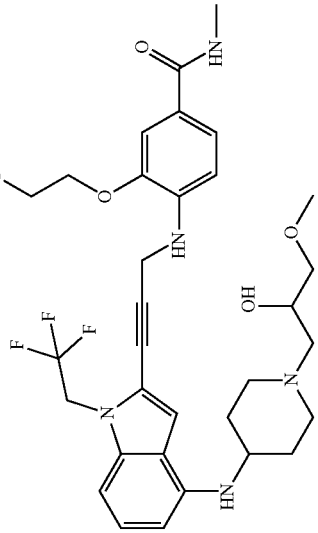 | 3-(2-fluoroethoxy)-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-N-methylbenzamide | 634.3 |

TABLE 4-continued

| Compound No. | Structure | IUPAC | LC-MS (ES+, m/z) |
|---|---|---|---|
| 653A | 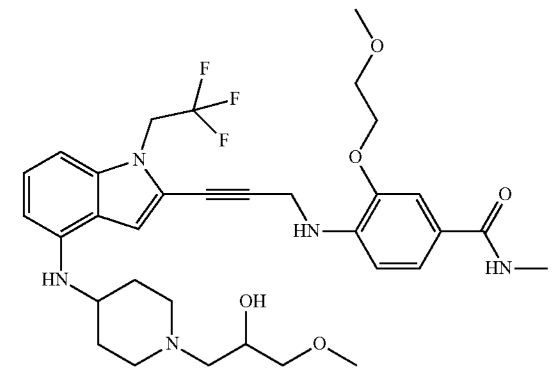 [SMILES: CNC(=O)c1ccc(NCC#Cc2cc3c(NC4CCN(CC(O)COC)CC4)cccc3n2CC(F)(F)F)c(OCCOC)c1] | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-(2-methoxyethoxy)-N-methylbenzamide | 646.3 |
| 654A | 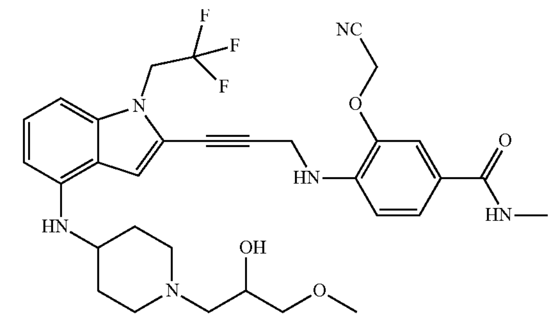 [SMILES: CNC(=O)c1ccc(NCC#Cc2cc3c(NC4CCN(CC(O)COC)CC4)cccc3n2CC(F)(F)F)c(OCC#N)c1] | 3-(cyanomethoxy)-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-N-methylbenzamide | 627.2 |
| 655A | 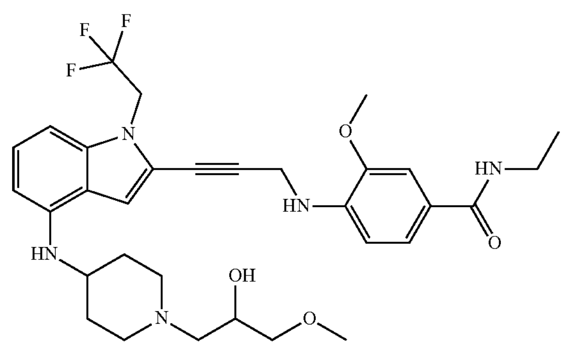 [SMILES: CCNC(=O)c1ccc(NCC#Cc2cc3c(NC4CCN(CC(O)COC)CC4)cccc3n2CC(F)(F)F)c(OC)c1] | N-ethyl-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzamide | 616.3 |

TABLE 4-continued

| Compound No. | Structure | IUPAC | LC-MS (ES+, m/z) |
|---|---|---|---|
| 656A | 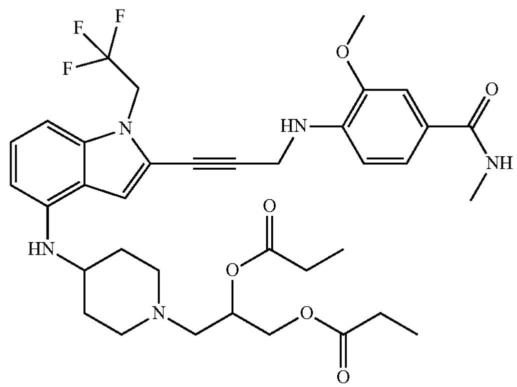 [SMILES: CCC(=O)OCC(CN1CCC(Nc2cccc3c2cc(C#CCNc2ccc(C(=O)NC)cc2OC)n3CC(F)(F)F)CC1)OC(=O)CC] | 1-(4-{[2-(3-{[2-methoxy-4-(methylcarbamoyl)phenyl]amino}prop-1-yn-1-yl)-1-(2,2,2-trifluoroethyl)-1H-indol-4-yl]amino}piperidin-1-yl)-3-(propanoyloxy)propan-2-yl propanoate | 700.3 |
| 657A | 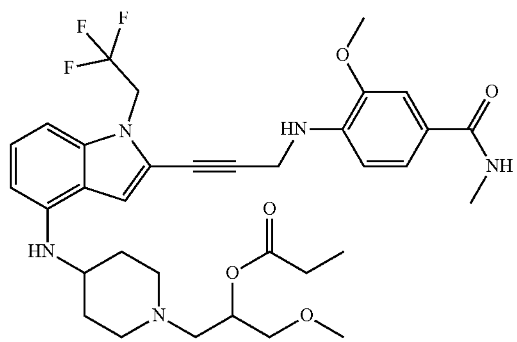 [SMILES: CCC(=O)OC(COC)CN1CCC(Nc2cccc3c2cc(C#CCNc2ccc(C(=O)NC)cc2OC)n3CC(F)(F)F)CC1] | 1-methoxy-3-(4-{[2-(3-{[2-methoxy-4-(methylcarbamoyl)phenyl]amino}prop-1-yn-1-yl)-1-(2,2,2-trifluoroethyl)-1H-indol-4-yl]amino}piperidin-1-yl)propan-2-yl propanoate | 658.3 |

TABLE 4-continued

| Compound No. | Structure | IUPAC | LC-MS (ES+, m/z) |
|---|---|---|---|
| 658A | 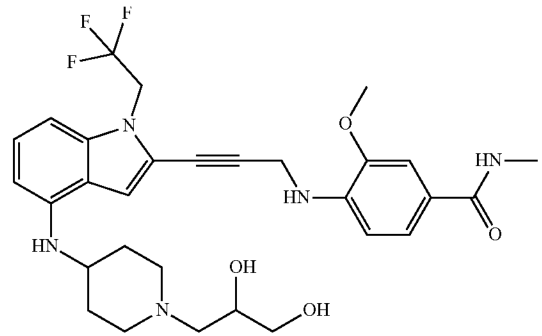 [SMILES: CNC(=O)c1ccc(NCC#Cc2cc3c(NC4CCN(CC(O)CO)CC4)cccc3n2CC(F)(F)F)c(OC)c1] | 4-[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-methylbenzamide | 588.3 |
| 659A | 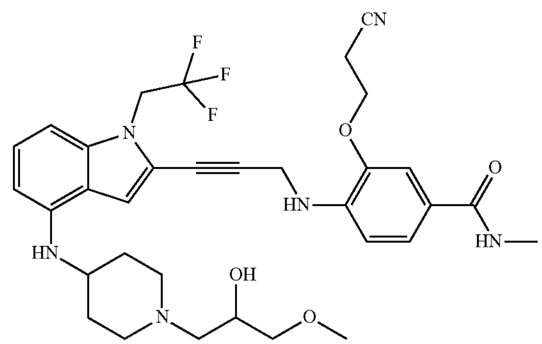 [SMILES: CNC(=O)c1ccc(NCC#Cc2cc3c(NC4CCN(CC(O)COC)CC4)cccc3n2CC(F)(F)F)c(OCCC#N)c1] | 3-(2-cyanoethoxy)-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-N-methylbenzamide | 641.4 |
| 660A | 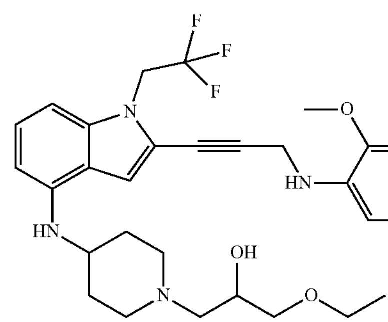 | 1-ethoxy-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-ol | 637.3 |

TABLE 4-continued

| Compound No. | Structure | IUPAC | LC-MS (ES+, m/z) |
|---|---|---|---|
| 661A | 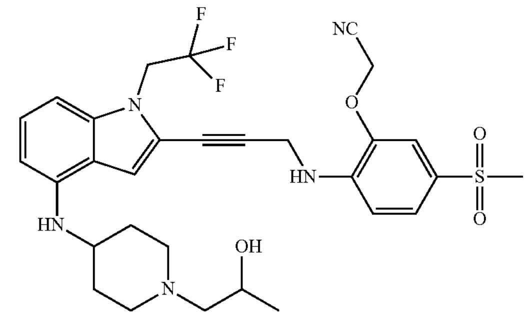 [SMILES: CC(O)CN1CCC(Nc2cccc3c2cc(C#CCNc2ccc(S(C)(=O)=O)cc2OCC#N)n3CC(F)(F)F)CC1] | 2-(2-{[3-(4-{[1-(2-hydroxypropyl)piperidin-4-yl]amino}-1-(2,2,2-trifluoroethyl)-1H-indol-2-yl)prop-2-yn-1-yl]amino}-5-methanesulfonylphenoxy)acetonitrile | 618.12 |
| 662A | 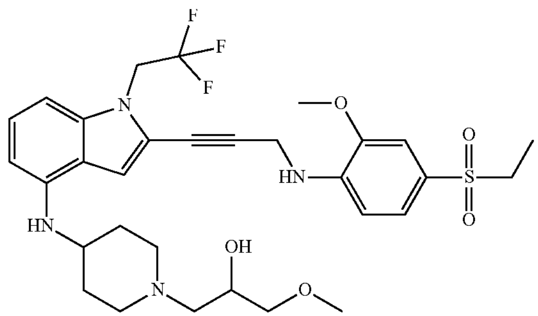 [SMILES: CCS(=O)(=O)c1ccc(NCC#Cc2cc3c(NC4CCN(CC(O)COC)CC4)cccc3n2CC(F)(F)F)c(OC)c1] | 1-(4-{[2-(3-{[4-(ethanesulfonyl)-2-methoxyphenyl]amino}prop-1-yn-1-yl)-1-(2,2,2-trifluoroethyl)-1H-indol-4-yl]amino}piperidin-1-yl)-3-methoxypropan-2-ol | 637.2 |
| 663A | 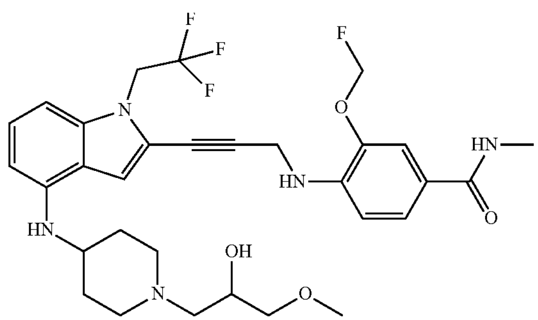 [SMILES: CNC(=O)c1ccc(NCC#Cc2cc3c(NC4CCN(CC(O)COC)CC4)cccc3n2CC(F)(F)F)c(OCF)c1] | 3-(fluoromethoxy)-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-N-methylbenzamide | 620.2 |

TABLE 4-continued

| Compound No. | Structure | IUPAC | LC-MS (ES+, m/z) |
|---|---|---|---|
| 664A | 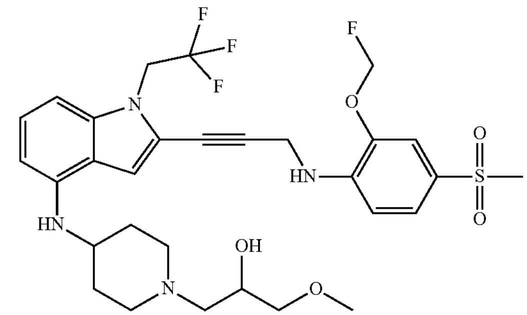 [SMILES: COCC(O)CN1CCC(Nc2cccc3c2cc(C#CCNc2ccc(S(C)(=O)=O)cc2OCF)n3CC(F)(F)F)CC1] | 1-(4-{[2-(3-{[2-(fluoromethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol | 641.6 |
| 665A | 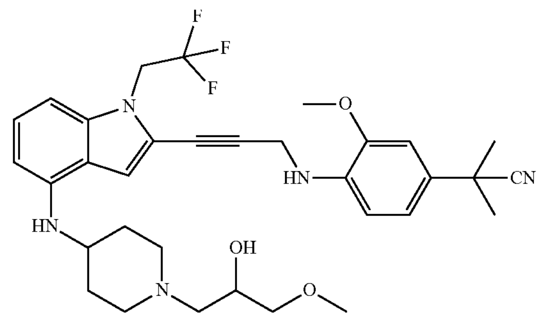 [SMILES: COCC(O)CN1CCC(Nc2cccc3c2cc(C#CCNc2ccc(C(C)(C)C#N)cc2OC)n3CC(F)(F)F)CC1] | 2-(4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxyphenyl)-2-methylpropanenitrile | 612.3 |
| 666A | 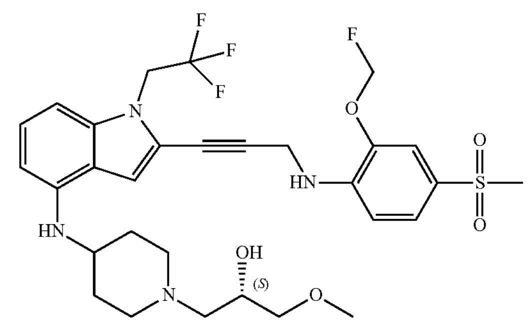 | (2S)-1-(4-{[2-(3-{[2-(fluoromethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol | 641.2 |

TABLE 4-continued

| Compound No. | Structure | IUPAC | LC-MS (ES⁺, m/z) |
|---|---|---|---|
| 667A | 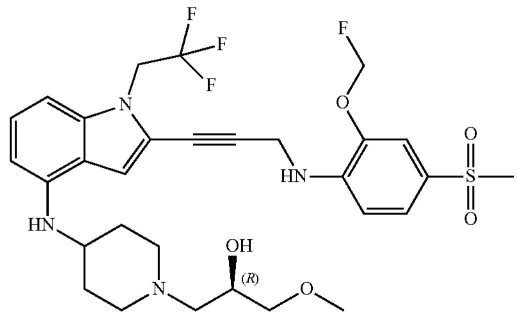 | (2R)-1-(4-{[2-(3-{[2-(fluoromethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol | 641.2 |
| 668A | 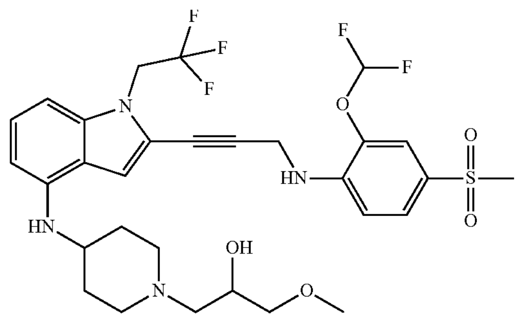 [SMILES: COCC(O)CN1CCC(Nc2cccc3c2cc(C#CCNc2ccc(S(C)(=O)=O)cc2OC(F)F)n3CC(F)(F)F)CC1] | 1-(4-{[2-(3-{[2-(difluoromethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol | 659.2 |
| 669A | 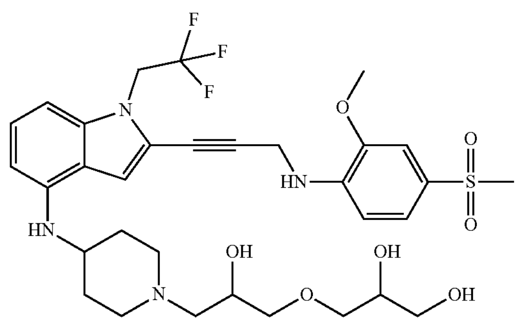 [SMILES: COc1cc(S(C)(=O)=O)ccc1NCC#Cc1cc2c(NC3CCN(CC(O)COCC(O)CO)CC3)cccc2n1CC(F)(F)F] | 3-(2-hydroxy-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propoxy)propane-1,2-diol | 683.2 |

TABLE 4-continued

| Compound No. | Structure | IUPAC | LC-MS (ES+, m/z) |
|---|---|---|---|
| 670A | 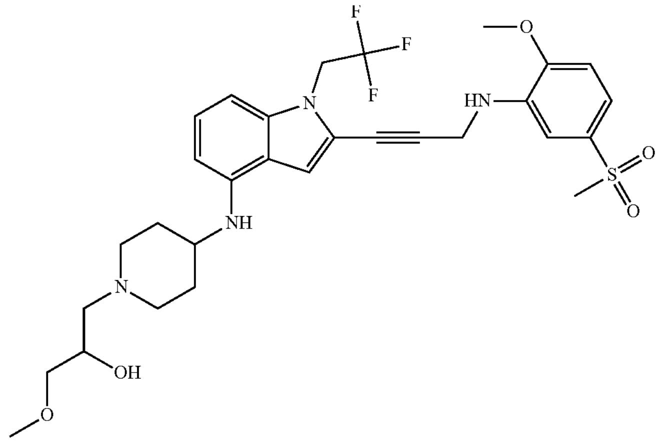 [SMILES: COCC(O)CN1CCC(Nc2cccc3c2cc(C#CCNc2cc(S(C)(=O)=O)ccc2OC)n3CC(F)(F)F)CC1] | 1-{4-[(2-{3-[(5-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol | 623.3 |
| 671A | 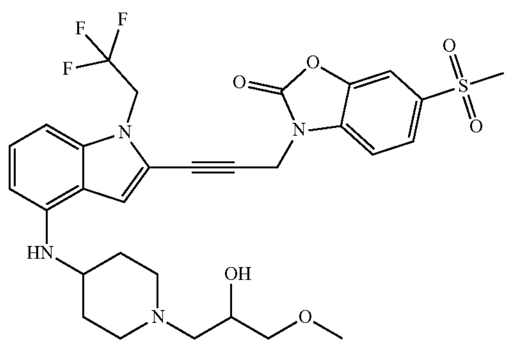 [SMILES: COCC(O)CN1CCC(Nc2cccc3c2cc(C#CCn2c(=O)oc4cc(S(C)(=O)=O)ccc42)n3CC(F)(F)F)CC1] | 3-(3-(4-((1-(2-hydroxy-3-methoxypropyl)piperidin-4-yl)amino)-1-(2,2,2-trifluoroethyl)-1H-indol-2-yl)prop-2-yn-1-yl)-6-(methylsulfonyl)benzo[d]oxazol-2(3H)-one | 635.3 |

TABLE 4-continued
| Compound No. | Structure | IUPAC | LC-MS (ES+, m/z) |
|---|---|---|---|
| 672A | 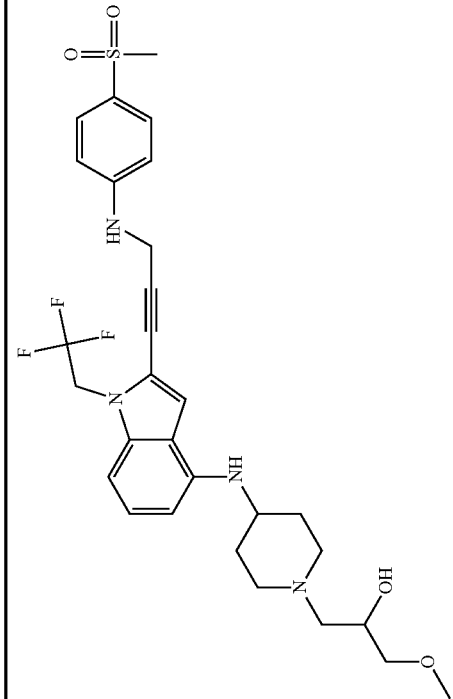 | 1-{4-[(2-{3-[(4-methanesulfonylphenyl)amino]prop-1-yn-1-yl}-1-(2,2,2-trifluoroethyl)-1H-indol-4-yl)amino]piperidin-1-yl}-3-methoxypropan-2-ol | 593.2 |
| 673A | 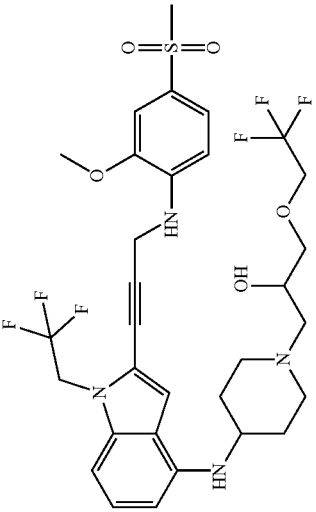 | 1-{4-[2-{3-[(4-methanesulfonyl-2-methoxyphenyl)amino]prop-1-yn-1-yl}-1-(2,2,2-trifluoroethyl)-1H-indol-4-yl)amino]piperidin-1-yl]-3-(2,2,2-trifluoroethoxy)propan-2-ol | 691.2 |

TABLE 4-continued

| Compound No. | Structure | IUPAC | LC-MS (ES⁺, m/z) |
|---|---|---|---|
| 674A | 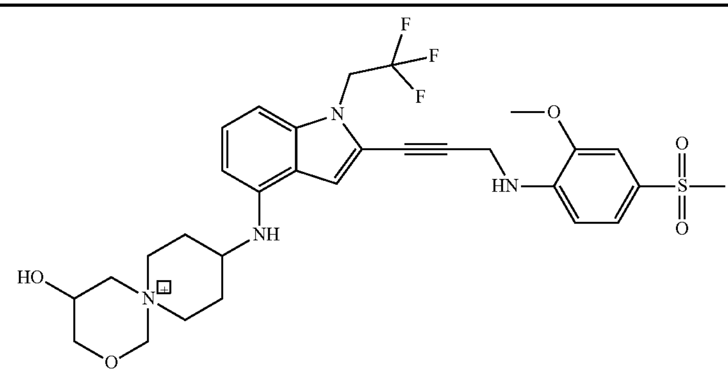 | 4-hydroxy-9-[(2-{3-[(4-methanesulfonyl-2-methoxyphenyl)amino]prop-1-yn-1-yl]-1-(2,2,2-trifluoroethyl)-1H-indol-4-yl)amino]-2-oxa-6λ⁵-azaspiro[5.5]undecan-6-ylium | 622.2 |
| 675A | 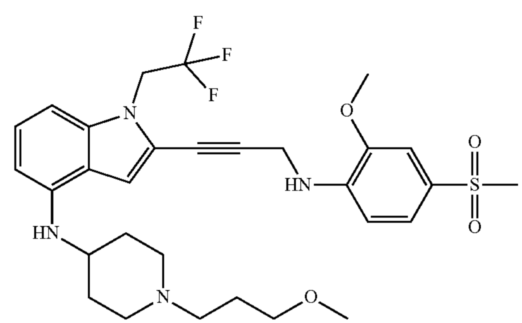 [SMILES: COCCCN1CCC(Nc2cccc3c2cc(C#CCNc2ccc(S(C)(=O)=O)cc2OC)n3CC(F)(F)F)CC1] | 2-{3-[(4-methanesulfonyl-2-methoxyphenyl)amino]prop-1-yn-1-yl}-N-[1-(3-methoxypropyl)piperidin-4-yl]-1-(2,2,2-trifluoroethyl)-1H-indol-4-amine | 607.2 |
| 676A | 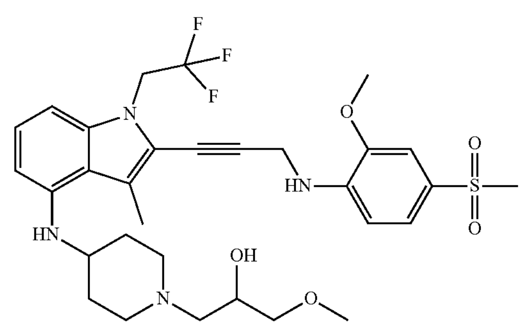 [SMILES: COCC(O)CN1CCC(Nc2cccc3c2c(C)c(C#CCNc2ccc(S(C)(=O)=O)cc2OC)n3CC(F)(F)F)CC1] | 1-{4-[(2-{3-[(4-methanesulfonyl-2-methoxyphenyl)amino]prop-1-yn-1-yl}-3-methyl-1-(2,2,2-trifluoroethyl)-1H-indol-4-yl)amino]piperidin-1-yl}-3-methoxypropan-2-ol | 637.2 |

TABLE 4-continued
| Compound No. | Structure | IUPAC | LC-MS (ES+, m/z) |
|---|---|---|---|
| 677A | 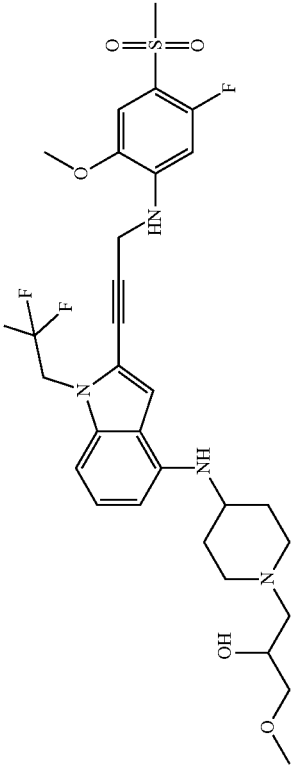 | 1-{4-[(2-{3-[(5-fluoro-4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol | 641.2 |
| 678A | 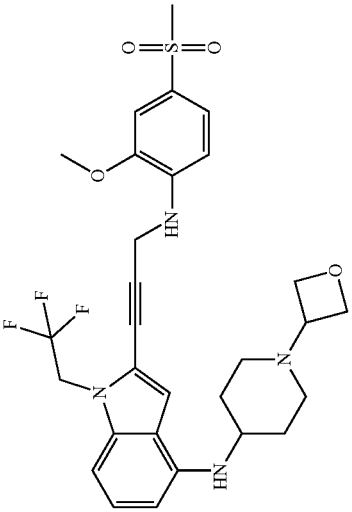 | 2-{3-[(4-methanesulfonyl-2-methoxyphenyl)amino]prop-1-yn-1-yl}-N-[1-(oxetan-3-yl)piperidin-4-yl]-1-(2,2,2-trifluoroethyl)-1H-indol-4-amine | 591.2 |

| Compound No. | Structure | IUPAC | LC-MS (ES+, m/z) |
|---|---|---|---|
| 679A | 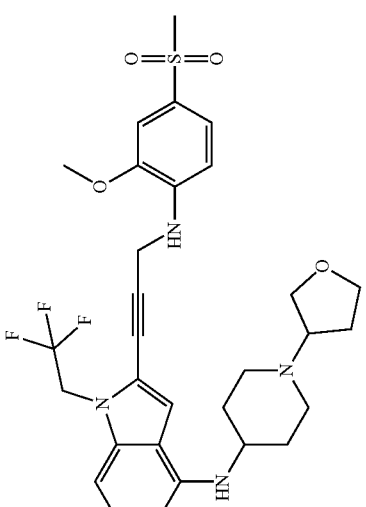 | 2-(3-((2-methoxy-4-(methylsulfonyl)phenyl)amino)prop-1-yn-1-yl)-N-(1-(tetrahydrofuran-3-yl)piperidin-4-yl)-1-(2,2,2-trifluoroethyl)-1H-indol-4-amine | 605.3 |
| 680A | 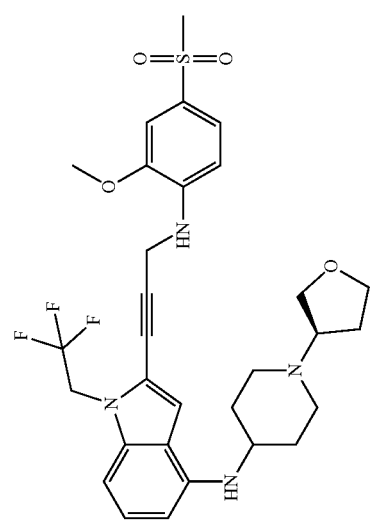 | (R)-2-(3-((2-methoxy-4-(methylsulfonyl)phenyl)amino)prop-1-yn-1-yl)-N-(1-(tetrahydrofuran-3-yl)piperidin-4-yl)-1-(2,2,2-trifluoroethyl)-1H-indol-4-amine | 605.3 |

TABLE 4-continued

| Compound No. | Structure | IUPAC | LC-MS (ES+, m/z) |
|---|---|---|---|
| 681A | 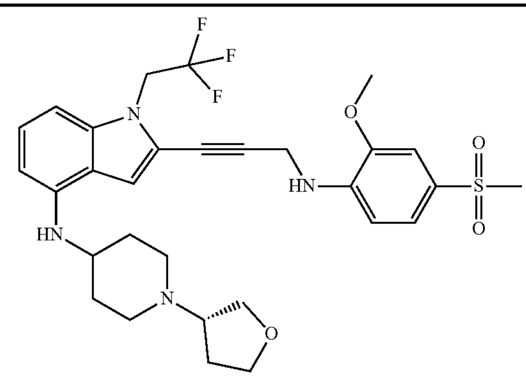 | (S)-2-(3-((2-methoxy-4-(methylsulfonyl)phenyl)amino)prop-1-yn-1-yl)-N-(1-(tetrahydrofuran-3-yl)piperidin-4-yl)-1-(2,2,2-trifluoroethyl)-1H-indol-4-amine | 605.3 |
| 682A | 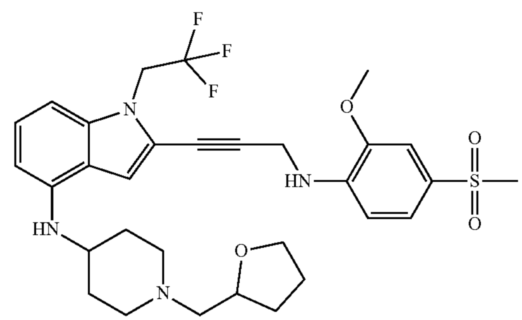 [SMILES: COc1cc(S(C)(=O)=O)ccc1NCC#Cc1cc2c(NC3CCN(CC4CCCO4)CC3)cccc2n1CC(F)(F)F] | 2-(3-((2-methoxy-4-(methylsulfonyl)phenyl)amino)prop-1-yn-1-yl)-N-(1-((tetrahydrofuran-2-yl)methyl)piperidin-4-yl)-1-(2,2,2-trifluoroethyl)-1H-indol-4-amine | 619.2 |
| 683A | 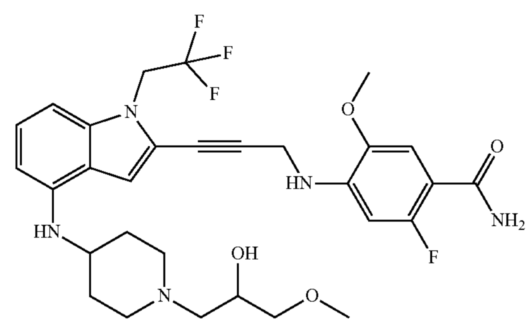 [SMILES: COCC(O)CN1CCC(Nc2cccc3c2cc(C#CCNc2cc(F)c(C(N)=O)cc2OC)n3CC(F)(F)F)CC1] | 2-fluoro-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-5-methoxybenzamide | 606.2 |

| Compound No. | Structure | IUPAC | LC-MS (ES+, m/z) |
|---|---|---|---|
| 684A | 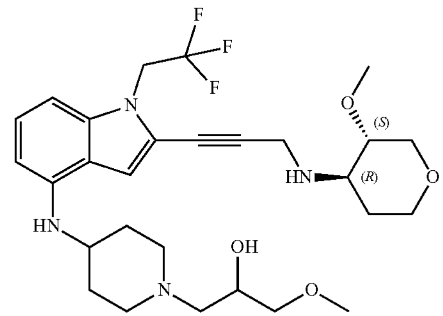 | 1-methoxy-3-(4-((2-(3-(((3S,4R)-3-methoxytetrahydro-2H-pyran-4-yl)amino)prop-1-yn-1-yl)-1-(2,2,2-trifluoroethyl)-1H-indol-4-yl)amino)piperidin-1-yl)propan-2-ol | 553.2 |
| 685A | 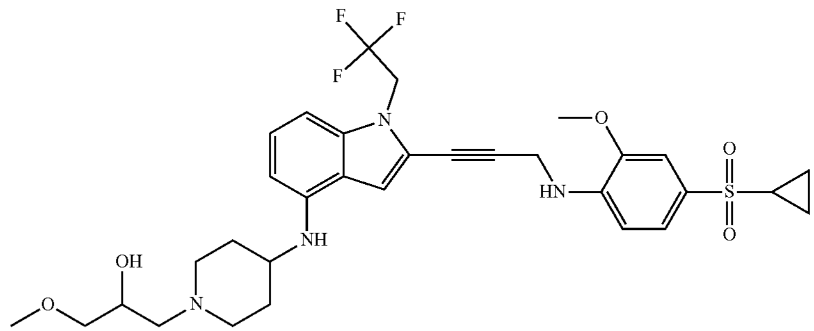 [SMILES: COCC(O)CN1CCC(Nc2cccc3c2cc(C#CCNc2ccc(S(=O)(=O)C4CC4)cc2OC)n3CC(F)(F)F)CC1] | 1-(4-{[2-(3-{[4-(cyclopropanesulfonyl)-2-methoxyphenyl]amino}prop-1-yn-1-yl)-1-(2,2,2-trifluoroethyl)-1H-indol-4-yl]amino}piperidin-1-yl)-3-methoxypropan-2-ol | 649.3 |
| 686A | 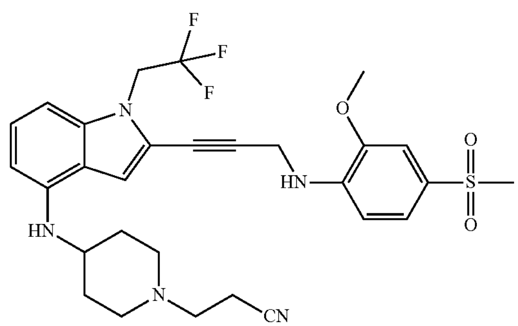 [SMILES: COc1cc(S(C)(=O)=O)ccc1NCC#Cc1cc2c(NC3CCN(CCC#N)CC3)cccc2n1CC(F)(F)F] | 3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propanenitrile | 588.2 |

TABLE 4-continued

| Compound No. | Structure | IUPAC | LC-MS (ES+, m/z) |
|---|---|---|---|
| 687A | 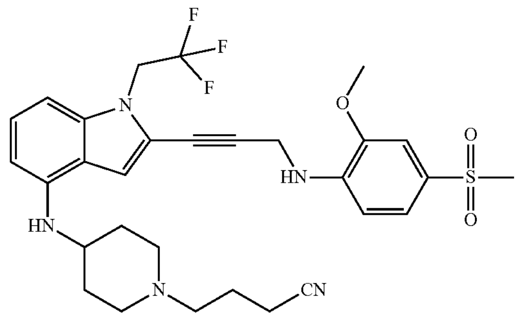 [SMILES: COc1cc(S(C)(=O)=O)ccc1NCC#Cc1cc2c(NC3CCN(CCCC#N)CC3)cccc2n1CC(F)(F)F] | 4-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)butanenitrile | 602.2 |
| 688A | 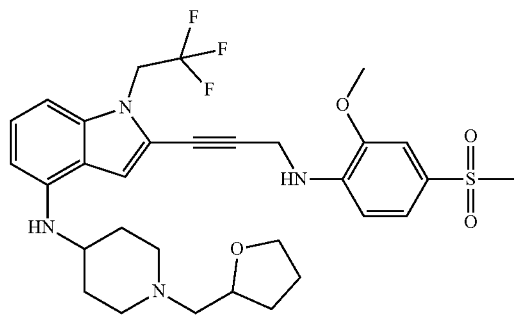 [SMILES: COc1cc(S(C)(=O)=O)ccc1NCC#Cc1cc2c(NC3CCN(CC4CCCO4)CC3)cccc2n1CC(F)(F)F] | 2-{3-[(4-methanesulfonyl-2-methoxyphenyl)amino]prop-1-yn-1-yl}-N-{1-[(oxolan-2-yl)methyl]piperidin-4-yl}-1-(2,2,2-trifluoroethyl)-1H-indol-4-amine | 619.2 |
| 689A | 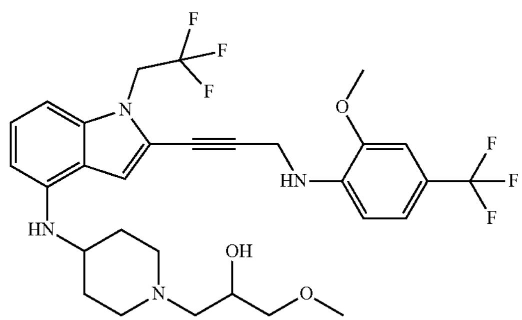 [SMILES: COCC(O)CN1CCC(Nc2cccc3c2cc(C#CCNc2ccc(C(F)(F)F)cc2OC)n3CC(F)(F)F)CC1] | 1-methoxy-3-(4-{[2-(3-{[2-methoxy-4-(trifluoromethyl)phenyl]amino}prop-1-yn-1-yl)-1-(2,2,2-trifluoroethyl)-1H-indol-4-yl]amino}piperidin-1-yl)propan-2-ol | 613.2 |

TABLE 4-continued

| Compound No. | Structure | IUPAC | LC-MS (ES+, m/z) |
|---|---|---|---|
| 690A | 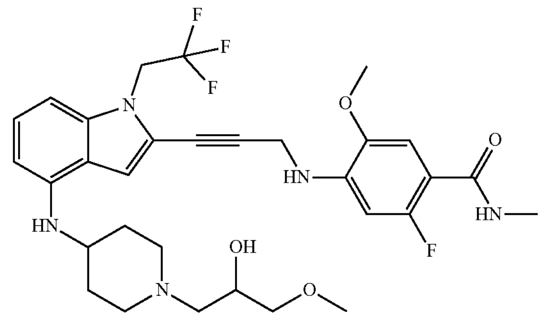 [SMILES: CNC(=O)c1cc(OC)c(NCC#Cc2cc3c(NC4CCN(CC(O)COC)CC4)cccc3n2CC(F)(F)F)cc1F] | 2-fluoro-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-5-methoxy-N-methylbenzamide | 620.3 |
| 691A | | 1-(4-{[2-(3-{[4-(benzenesulfonyl)-2-methoxyphenyl]amino}prop-1-yn-1-yl)-1-(2,2,2-trifluoroethyl)-1H-indol-4-yl]amino}piperidin-1-yl)-3-methoxypropan-2-ol | 685.3 |
| 692A | 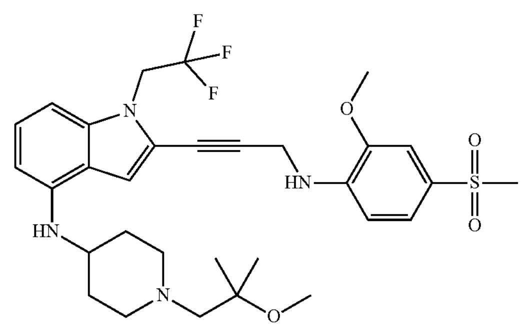 [SMILES: COc1cc(S(C)(=O)=O)ccc1NCC#Cc1cc2c(NC3CCN(CC(C)(C)OC)CC3)cccc2n1CC(F)(F)F] | 2-{3-[(4-methanesulfonyl)-2-methoxyphenyl)amino]prop-1-yn-1-yl}-N-[1-(2-methoxy-2-methylpropyl)piperidin-4-yl]-1-(2,2,2-trifluoroethyl)-1H-indol-4-amine | 621.2 |

| Compound No. | Structure | IUPAC | LC-MS (ES+, m/z) |
|---|---|---|---|
| 693A | 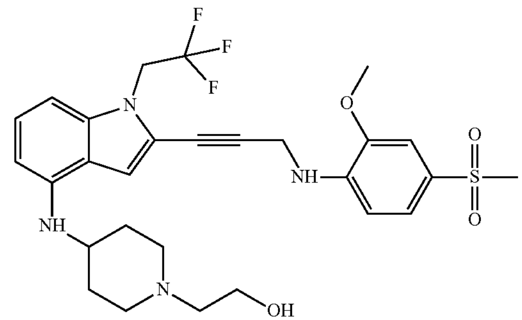 [SMILES: COc1cc(S(C)(=O)=O)ccc1NCC#Cc1cc2c(NC3CCN(CCO)CC3)cccc2n1CC(F)(F)F] | 2-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)ethan-1-ol | 579.2 |
| 694A | 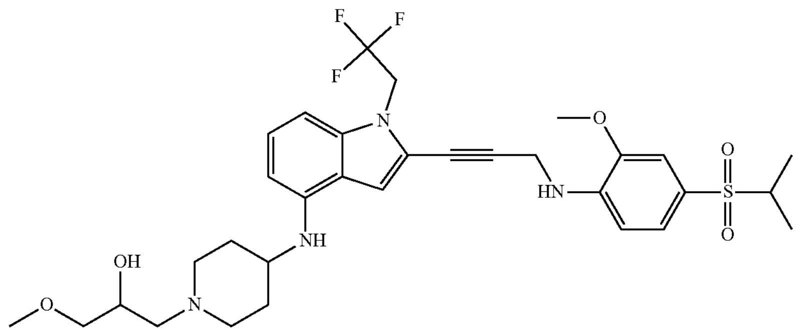 [SMILES: COCC(O)CN1CCC(Nc2cccc3c2cc(C#CCNc2ccc(S(=O)(=O)C(C)C)cc2OC)n3CC(F)(F)F)CC1] | 1-methoxy-3-(4-{[2-(3-{[2-methoxy-4-(propane-2-sulfonyl)phenyl]amino}prop-1-yn-1-yl)-1-(2,2,2-trifluoroethyl)-1H-indol-4-yl]amino}piperidin-1-yl)propan-2-ol | 651.3 |
| 695A | 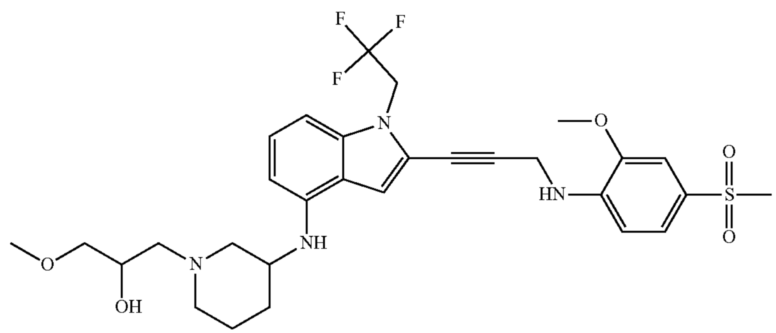 | 1-{3-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol | 622.9 |

TABLE 4-continued

| Compound No. | Structure | IUPAC | LC-MS (ES+, m/z) |
|---|---|---|---|
| 696A | 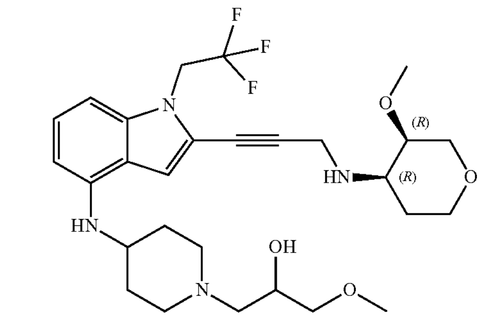 | 1-methoxy-3-(4-((2-(3-(((3R,4R)-3-methoxytetrahydro-2H-pyran-4-yl)amino)prop-1-yn-1-yl)-1-(2,2,2-trifluoroethyl)-1H-indol-4-yl)amino)piperidin-1-yl)propan-2-ol | 553.2 |
| 697A | 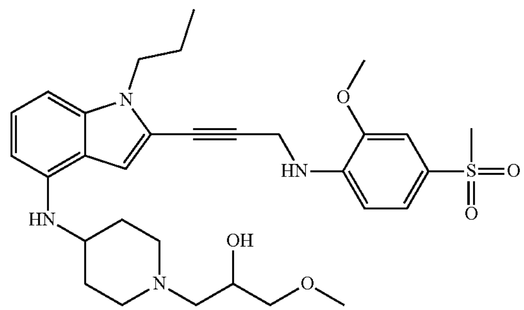 [SMILES: CCCn1c(C#CCNc2ccc(S(C)(=O)=O)cc2OC)cc2c(NC3CCN(CC(O)COC)CC3)cccc21] | 1-{4-[(2-{3-[(4-methanesulfonyl-2-methoxyphenyl)amino]prop-1-yn-1-yl}-1-propyl-1H-indol-4-yl)amino]piperidin-1-yl}-3-methoxypropan-2-ol | 583.3 |
| 698A | 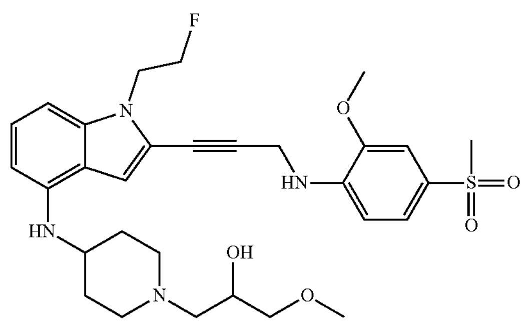 | 1-(4-{[1-(2-fluoroethyl)-2-{3-[(4-methanesulfonyl-2-methoxyphenyl)amino]prop-1-yn-1-yl]-1H-indol-4-yl]amino}piperidin-1-yl)-3-methoxypropan-2-ol | 587.2 |

TABLE 4-continued

| Compound No. | Structure | IUPAC | LC-MS (ES+, m/z) |
|---|---|---|---|
| 699A | 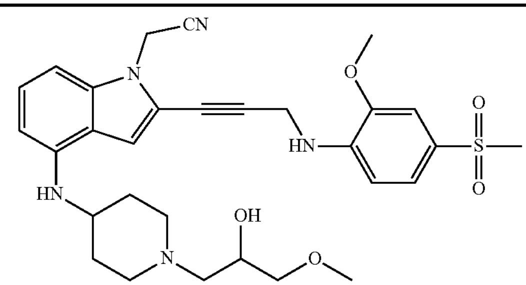 | 2-(4-{[1-(2-hydroxy-3-methoxypropyl)piperidin-4-yl]amino}-2-{3-[(4-methanesulfonyl-2-methoxyphenyl)amino]prop-1-yn-1-yl}-1H-indol-1-yl)acetonitrile | 580.3 |
| 700A | 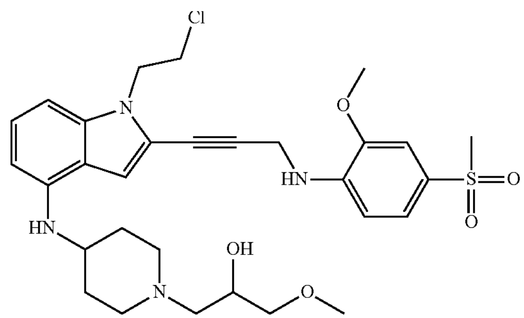 [SMILES: COCC(O)CN1CCC(Nc2cccc3c2cc(C#CCNc2ccc(S(C)(=O)=O)cc2OC)n3CCCl)CC1] | 1-(4-{[1-(2-chloroethyl)-2-{3-[(4-methanesulfonyl-2-methoxyphenyl)amino]prop-1-yn-1-yl]-1H-indol-4-yl]amino}piperidin-1-yl)-3-methoxypropan-2-ol | 603.2 |
| 701A | 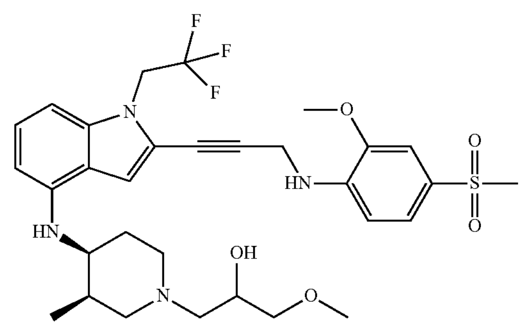 [SMILES: COCC(O)CN1CC[C@H](Nc2cccc3c2cc(C#CCNc2ccc(S(C)(=O)=O)cc2OC)n3CC(F)(F)F)[C@H](C)C1] | rac-1-[(3R,4S)-4-[(2-{3-[(4-methanesulfonyl-2-methoxyphenyl)amino]prop-1-yn-1-yl}-1-(2,2,2-trifluoroethyl)-1H-indol-4-yl)amino]-3-methylpiperidin-1-yl]-3-methoxypropan-2-ol | 637.3 |

TABLE 4-continued

| Compound No. | Structure | IUPAC | LC-MS (ES+, m/z) |
|---|---|---|---|
| 702A | 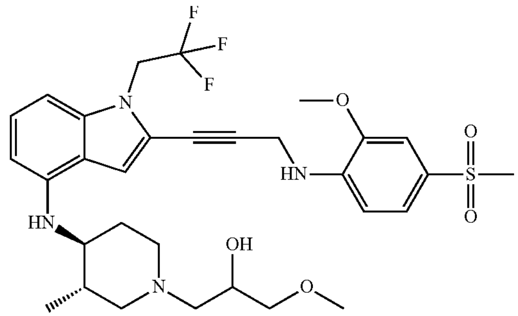 [SMILES: COCC(O)CN1CC[C@H](Nc2cccc3c2cc(C#CCNc2ccc(S(C)(=O)=O)cc2OC)n3CC(F)(F)F)[C@@H](C)C1] | rac-1-[(3R,4R)-4-[(2-{3-[(4-methanesulfonyl-2-methoxyphenyl)amino]prop-1-yn-1-yl]-1-(2,2,2-trifluoroethyl)-1H-indol-4-yl}amino]-3-methylpiperidin-1-yl]-3-methoxypropan-2-ol | 637.3 |
| 703A | 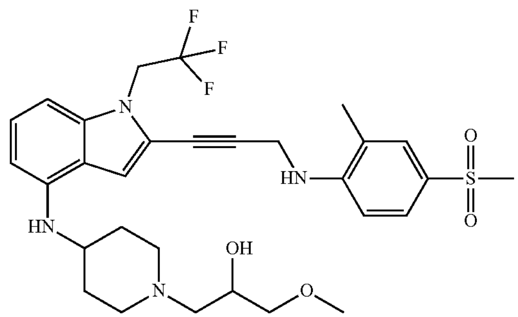 | 1-{4-[(2-{3-[(4-methanesulfonyl-2-methylphenyl)amino]prop-1-yn-1-yl]-1-(2,2,2-trifluoroethyl)-1H-indol-4-yl)amino]piperidin-1-yl}-3-methoxypropan-2-ol | 607.3 |
| 704a | 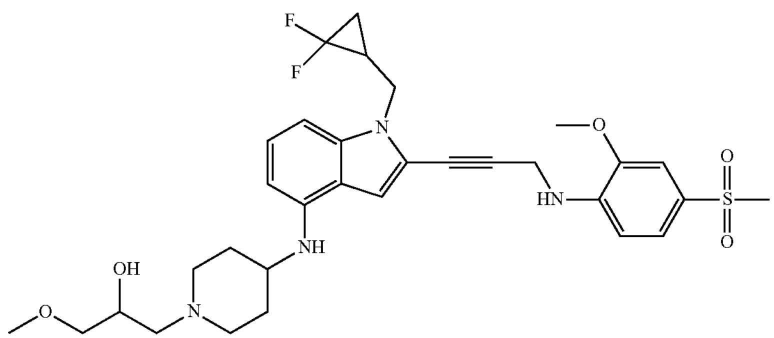 | 1-[4-({1-[(2,2-difluorocyclopropyl)methyl]-2-{3-[(4-methanesulfonyl-2-methoxyphenyl)amino]prop-1-yn-1-yl}-1H-indol-4-yl}amino)piperidin-1-yl]-3-methoxypropan-2-ol | 630.9 |

TABLE 4-continued

| Compound No. | Structure | IUPAC | LC-MS (ES+, m/z) |
|---|---|---|---|
| 705A | 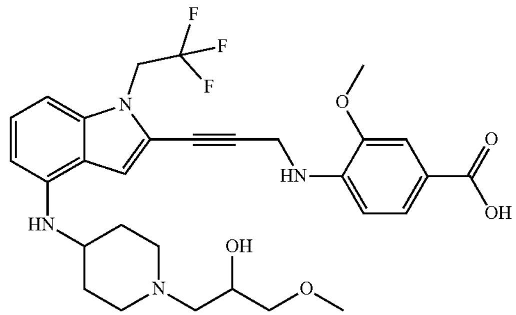 [SMILES: COCC(O)CN1CCC(Nc2cccc3c2cc(C#CCNc2ccc(C(=O)O)cc2OC)n3CC(F)(F)F)CC1] | 4-{3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzoic acid | 589.3 |
| 706A | 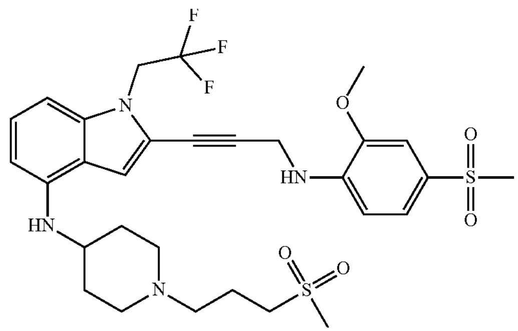 [SMILES: COc1cc(S(C)(=O)=O)ccc1NCC#Cc1cc2c(NC3CCN(CCCS(C)(=O)=O)CC3)cccc2n1CC(F)(F)F] | 2-{3-[(4-methanesulfonyl-2-methoxyphenyl)amino]prop-1-yn-1-yl}-N-{1-(3-methanesulfonylpropyl)piperidin-4-yl]-1-(2,2,2-trifluoroethyl)-1H-indol-4-amine | 655.2 |
| 707A | 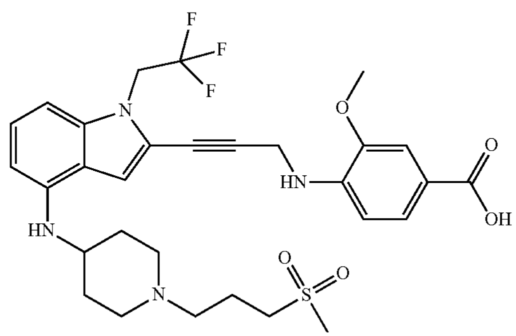 [SMILES: COc1cc(C(=O)O)ccc1NCC#Cc1cc2c(NC3CCN(CCCS(C)(=O)=O)CC3)cccc2n1CC(F)(F)F] | 4-{3-(4-{[1-(3-methanesulfonylpropyl)piperidin-4-yl]amino}-1-(2,2,2-trifluoroethyl)-1H-indol-2-yl)prop-2-yn-1-yl]amino}-3-methoxybenzoic acid | 621.3 |

TABLE 4-continued

| Compound No. | Structure | IUPAC | LC-MS (ES+, m/z) |
|---|---|---|---|
| 708A | 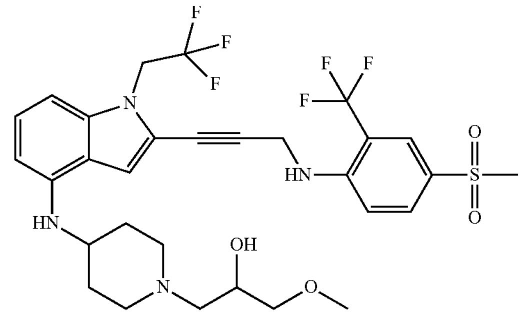 [SMILES: COCC(O)CN1CCC(Nc2cccc3c2cc(C#CCNc2ccc(S(C)(=O)=O)cc2C(F)(F)F)n3CC(F)(F)F)CC1] | 1-(4-{[2-(3-{[4-methanesulfonyl-2-(trifluoromethyl)phenyl]amino}prop-1-yn-1-yl)-1-(2,2,2-trifluoroethyl)-1H-indol-4-yl]amino}piperidin-1-yl)-3-methoxypropan-2-ol | 661.3 |
| 709A | 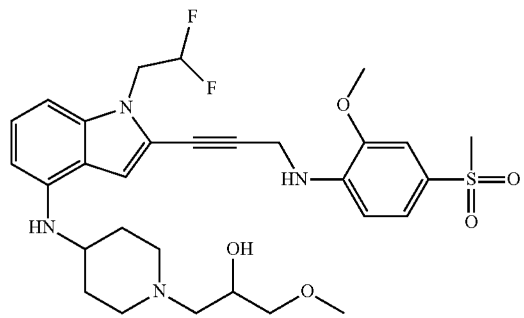 | 1-(4-{[1-(2,2-difluoroethyl)-2-{3-[(4-methanesulfonyl-2-methoxyphenyl)amino]prop-1-yn-1-yl}-1H-indol-4-yl]amino}piperidin-1-yl)-3-methoxypropan-2-ol | 605.2 |
| 710A | 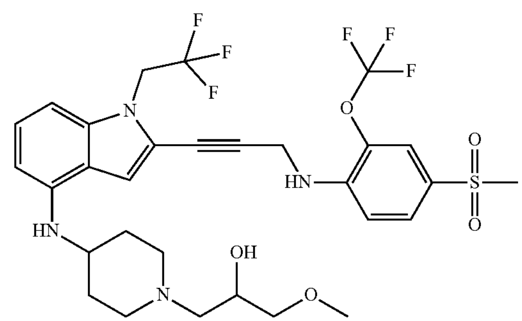 [SMILES: COCC(O)CN1CCC(Nc2cccc3c2cc(C#CCNc2ccc(S(C)(=O)=O)cc2OC(F)(F)F)n3CC(F)(F)F)CC1] | 1-(4-{[2-(3-{[4-methanesulfonyl-2-(trifluoromethoxy)phenyl]amino}prop-1-yn-1-yl)-1-(2,2,2-trifluoroethyl)-1H-indol-4-yl]amino}piperidin-1-yl)-3-methoxypropan-2-ol | 677.1 |

| Compound No. | Structure | IUPAC | LC-MS (ES+, m/z) |
|---|---|---|---|
| 711A | 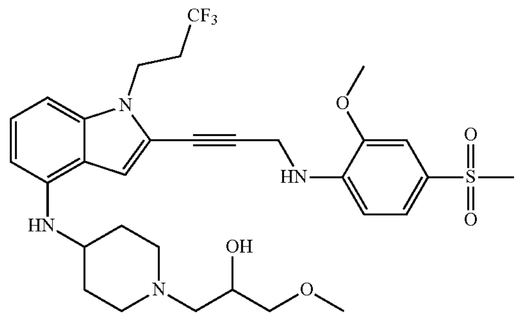 [SMILES: COCC(O)CN1CCC(Nc2cccc3c2cc(C#CCNc2ccc(S(C)(=O)=O)cc2OC)n3CCC(F)(F)F)CC1] | 1-{4-[(2-{3-[(4-methanesulfonyl-2-methoxyphenyl)amino]prop-1-yn-1-yl}-1-(3,3,3-trifluoropropyl)-1H-indol-4-yl)amino]piperidin-1-yl}-3-methoxypropan-2-ol | 637.3 |
| 712A | 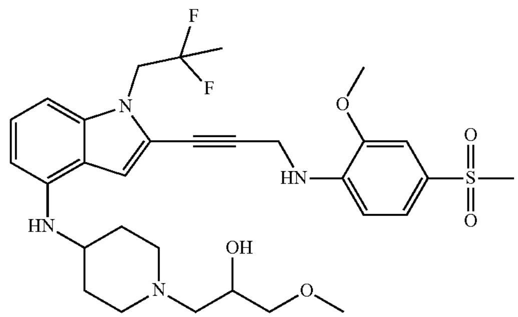 [SMILES: COCC(O)CN1CCC(Nc2cccc3c2cc(C#CCNc2ccc(S(C)(=O)=O)cc2OC)n3CC(C)(F)F)CC1] | 1-(4-{[1-(2,2-difluoropropyl)-2-{3-[(4-methanesulfonyl-2-methoxyphenyl)amino]prop-1-yn-1-yl}-1H-indol-4-yl]amino}piperidin-1-yl)-3-methoxypropan-2-ol | 619.3 |
| 713A | 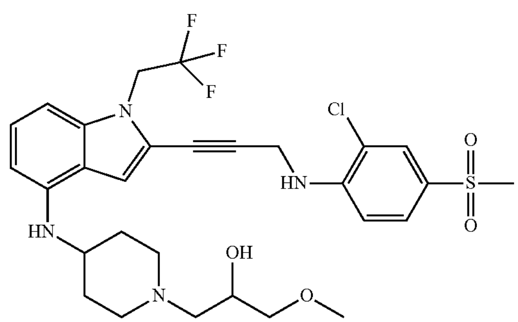 [SMILES: COCC(O)CN1CCC(Nc2cccc3c2cc(C#CCNc2ccc(S(C)(=O)=O)cc2Cl)n3CC(F)(F)F)CC1] | 1-{4-[(2-{3-[(2-chloro-4-methanesulfonylphenyl)amino]prop-1-yn-1-yl}-1-(2,2,2-trifluoroethyl)-1H-indol-4-yl)amino]piperidin-1-yl}-3-methoxypropan-2-ol | 627.4 |

TABLE 4-continued

| Compound No. | Structure | IUPAC | LC-MS (ES+, m/z) |
|---|---|---|---|
| 714A | 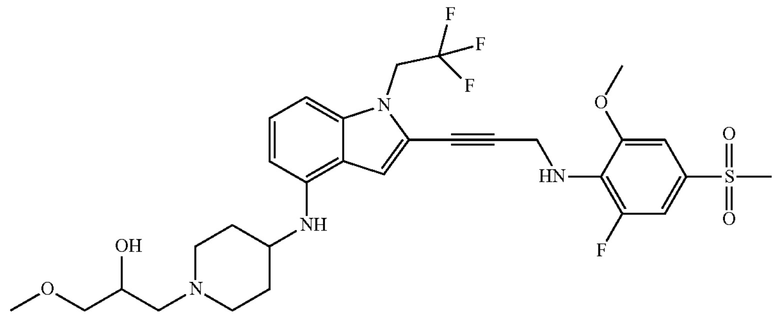 | 1-{4-[(2-{3-[(2-fluoro-4-methanesulfonyl-6-methoxyphenyl)amino]prop-1-yn-1-yl}-1-(2,2,2-trifluoroethyl)-1H-indol-4-yl)amino]piperidin-1-yl}-3-methoxypropan-2-ol | 641.2 |
| 1054A | 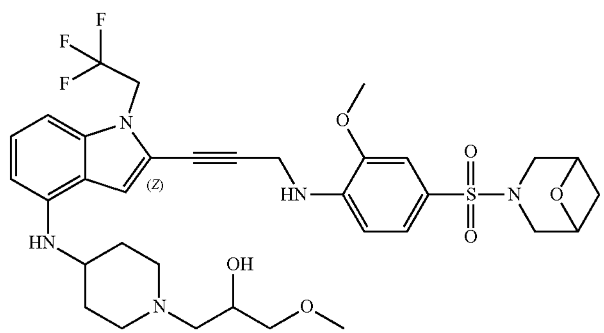 [SMILES: COCC(O)CN1CCC(Nc2cccc3c2cc(C#CCNc2ccc(S(=O)(=O)N4CC5CC(C4)O5)cc2OC)n3CC(F)(F)F)CC1] | 1-(4-((2-(3-((4-((6-oxa-3-azabicyclo[3.1.1]heptan-3-yl)sulfonyl)-2-methoxyphenyl)amino)prop-1-yn-1-yl)-1-(2,2,2-trifluoroethyl)-1H-indol-4-yl)amino)piperidin-1-yl)-3-methoxypropan-2-ol | |
| 715A | 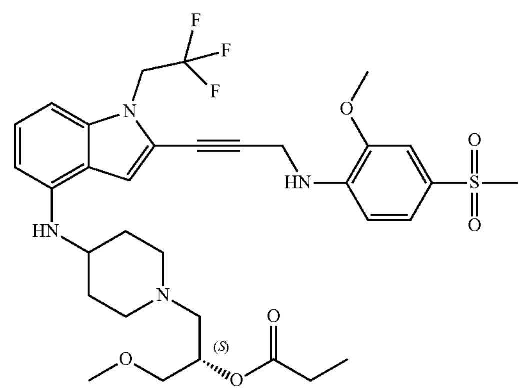 | (2S)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl propanoate | 679.3 |

TABLE 4-continued

| Compound No. | Structure | IUPAC | LC-MS (ES+, m/z) |
|---|---|---|---|
| 716A | 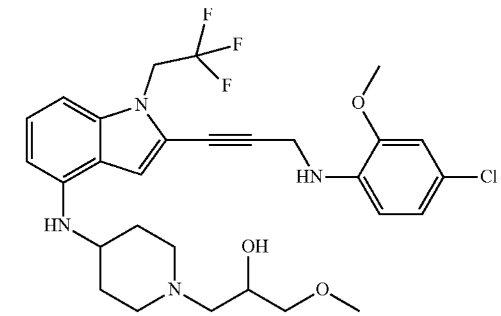 [SMILES: COCC(O)CN1CCC(Nc2cccc3c2cc(C#CCNc2ccc(Cl)cc2OC)n3CC(F)(F)F)CC1] | 1-{4-[(2-{3-[(4-chloro-2-methoxyphenyl)amino]prop-1-yn-1-yl}-1-(2,2,2-trifluoroethyl)-1H-indol-4-yl)amino]piperidin-1-yl}-3-methoxypropan-2-ol | 579.2 |
| 717A | 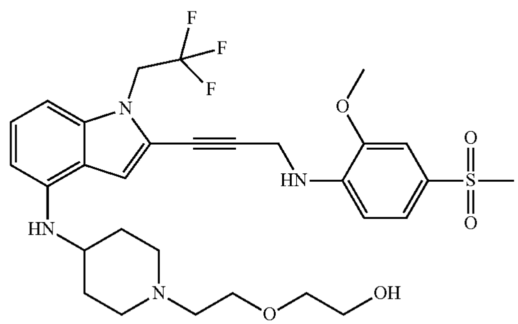 [SMILES: COc1cc(S(C)(=O)=O)ccc1NCC#Cc1cc2c(NC3CCN(CCOCCO)CC3)cccc2n1CC(F)(F)F] | 2-(2-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)ethoxy)ethan-1-ol | 623.2 |

TABLE 4-continued

| Compound No. | Structure | IUPAC | LC-MS (ES+, m/z) |
|---|---|---|---|
| 718A | 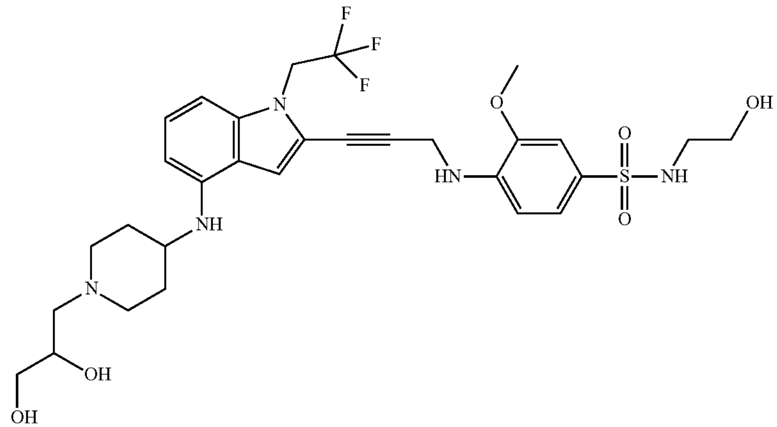 [SMILES: COc1cc(S(=O)(=O)NCCO)ccc1NCC#Cc1cc2c(NC3CCN(CC(O)CO)CC3)cccc2n1CC(F)(F)F] | 4-((3-(4-((1-(2,3-dihydroxypropyl)piperidin-4-yl)amino)-1-(2,2,2-trifluoroethyl)-1H-indol-2-yl)prop-2-yn-1-yl)amino)-N-(2-hydroxyethyl)-3-methoxybenzenesulfonamide | |
| 719A | 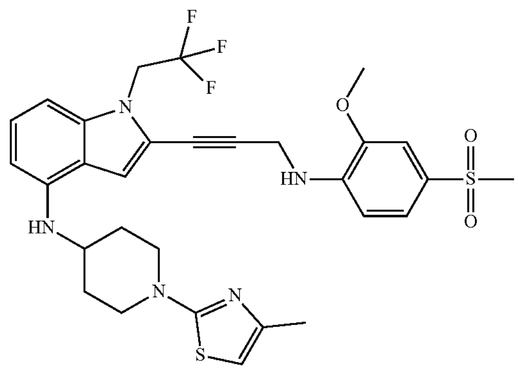 [SMILES: COc1cc(S(C)(=O)=O)ccc1NCC#Cc1cc2c(NC3CCN(c4nc(C)cs4)CC3)cccc2n1CC(F)(F)F] | 2-{3-[((4-methanesulfonyl-2-methoxyphenyl)amino]prop-1-yn-1-yl}-N-[1-(4-methyl-1,3-thiazol-2-yl)piperidin-4-yl]-1-(2,2,2-trifluoroethyl)-1H-indol-4-amine | 632.2 |

TABLE 4-continued
| Compound No. | Structure | IUPAC | LC-MS (ES+, m/z) |
|---|---|---|---|
| 720A | 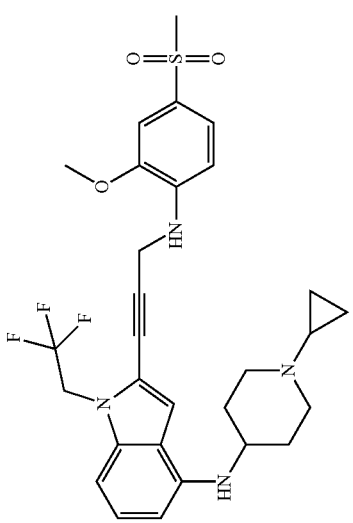 | N-(1-cyclopropylpiperidin-4-yl)-2-{3-[(4-methanesulfonyl-2-methoxyphenyl)amino]prop-1-yn-1-yl}-1-(2,2,2-trifluoroethyl)-1H-indol-4-amine | 575.2 |
| 721A | 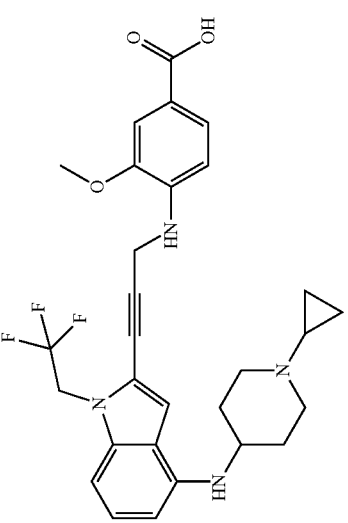 | 4-[(3-{4-[(1-cyclopropylpiperidin-4-yl)amino]-1-(2,2,2-trifluoroethyl)-1H-indol-2-yl}prop-2-yn-1-yl)amino]-3-methoxybenzoic acid | 541.2 |

TABLE 4-continued

| Compound No. | Structure | IUPAC | LC-MS (ES+, m/z) |
|---|---|---|---|
| 722A | 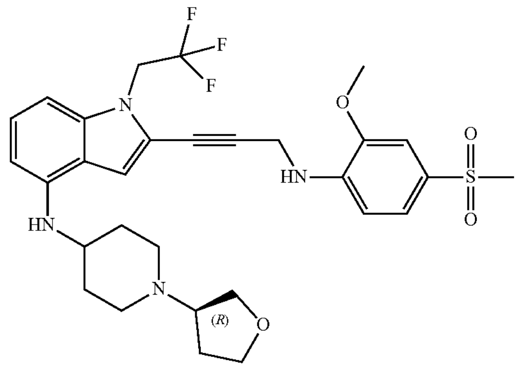 | 2-{3-[(4-methanesulfonyl-2-methoxyphenyl)amino]prop-1-yn-1-yl}-N-{1-[(3R)-oxolan-3-yl]piperidin-4-yl}-1-(2,2,2-trifluoroethyl)-1H-indol-4-amine | 605.2 |
| 723A | 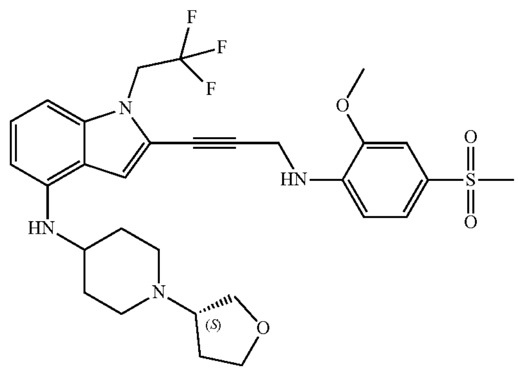 | 2-{3-[(4-methanesulfonyl-2-methoxyphenyl)amino]prop-1-yn-1-yl}-N-{1-[(3S)-oxolan-3-yl]piperidin-4-yl}-1-(2,2,2-trifluoroethyl)-1H-indol-4-amine | 605.3 |

TABLE 4-continued

| Compound No. | Structure | IUPAC | LC-MS (ES+, m/z) |
|---|---|---|---|
| 724A | 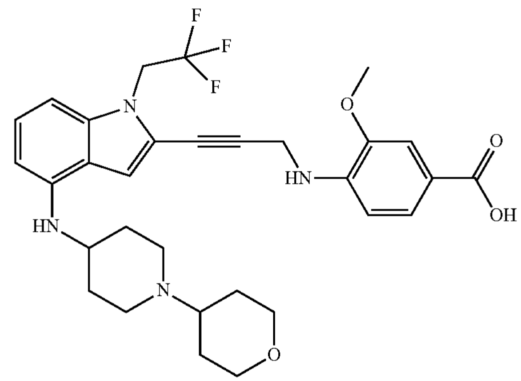 [SMILES: COc1cc(C(=O)O)ccc1NCC#Cc1cc2c(NC3CCN(C4CCOCC4)CC3)cccc2n1CC(F)(F)F] | 3-methoxy-4-{[3-(4-{[1-(oxan-4-yl)piperidin-4-yl]amino}-1-(2,2,2-trifluoroethyl)-1H-indol-2-yl)prop-2-yn-1-yl]amino}benzoic acid | 585.3 |
| 725A | 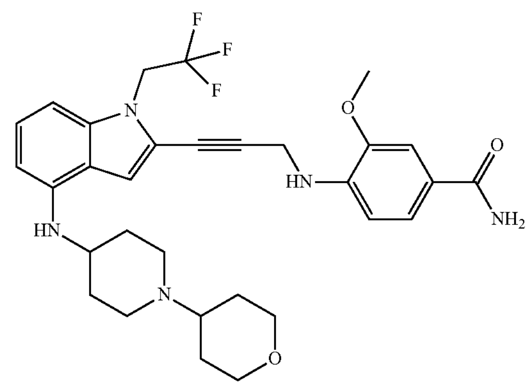 [SMILES: COc1cc(C(N)=O)ccc1NCC#Cc1cc2c(NC3CCN(C4CCOCC4)CC3)cccc2n1CC(F)(F)F] | 3-methoxy-4-((3-(4-((1-(tetrahydro-2H-pyran-4-yl)piperidin-4-yl)amino)-1-(2,2,2-trifluoroethyl)-1H-indol-2-yl)prop-2-yn-1-yl)amino)benzamide | 584.3 |

TABLE 4-continued
| Compound No. | Structure | IUPAC | LC-MS (ES+, m/z) |
|---|---|---|---|
| 726A | 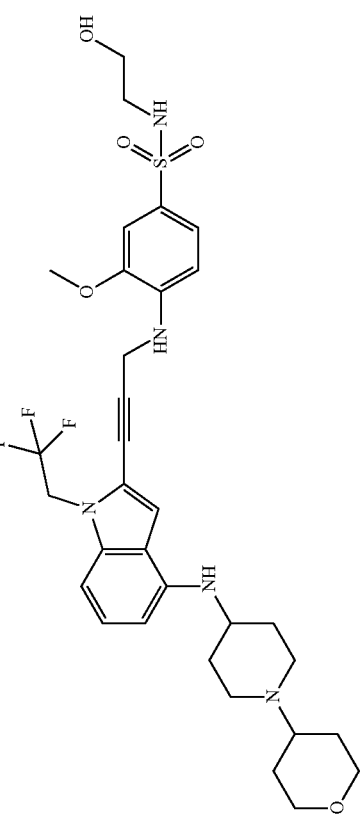 | N-(2-hydroxyethyl)-3-methoxy-4-((3-(4-((1-(tetrahydro-2H-pyran-4-yl)piperidin-4-yl)amino)-1-(2,2,2-trifluoroethyl)-1H-indol-2-yl)prop-2-yn-1-yl)amino)benzenesulfonamide | 664.3 |
| 727A | 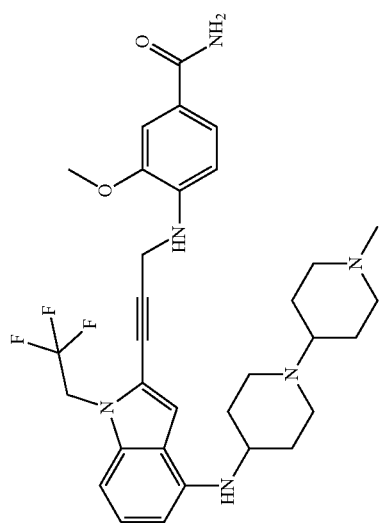 | 3-methoxy-4-((3-(4-((1'-methyl-[1,4'-bipiperidin]-4-yl)amino)-1-(2,2,2-trifluoroethyl)-1H-indol-2-yl)prop-2-yn-1-yl)amino)benzamide | 597.3 |

TABLE 4-continued

| Compound No. | Structure | IUPAC | LC-MS (ES+, m/z) |
|---|---|---|---|
| 728A | 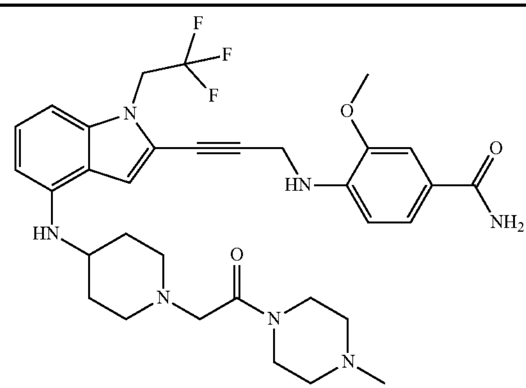 | 3-methoxy-4-((3-(4-((1-(2-(4-methylpiperazin-1-yl)-2-oxoethyl)piperidin-4-yl)amino)-1-(2,2,2-trifluoroethyl)-1H-indol-2-yl)prop-2-yn-1-yl)amino)benzamide | 640.3 |
| 729A | 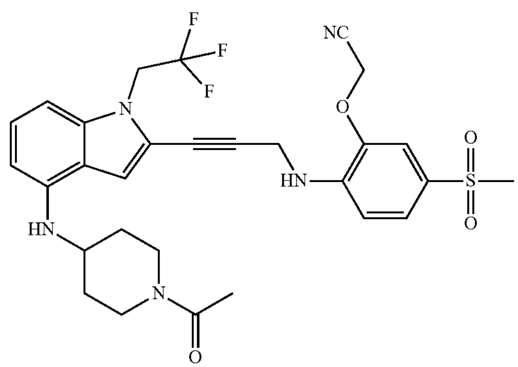 [SMILES: CC(=O)N1CCC(Nc2cccc3c2cc(C#CCNc2ccc(S(C)(=O)=O)cc2OCC#N)n3CC(F)(F)F)CC1] | 2-{2-[(3-{4-[(1-acetylpiperidin-4-yl]amino]-1-(2,2,2-trifluoroethyl)-1H-indol-2-yl]prop-2-yn-1-yl)amino]-5-methanesulfonyl}phenoxy}acetonitrile | 602.2 |

TABLE 4-continued
| Compound No. | Structure | IUPAC | LC-MS (ES+, m/z) |
|---|---|---|---|
| 730A | 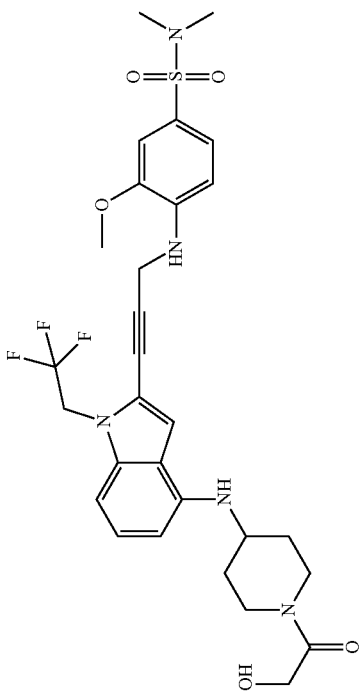 | 4-[3-(4-{[1-(2-hydroxyacetyl)piperidin-4-yl]amino}-1-(2,2,2-trifluoroethyl)-1H-indol-2-yl)prop-2-yn-1-yl]amino)-3-methoxy-N,N-dimethylbenzene-1-sulfonamide | 622.4 |
| 731A | 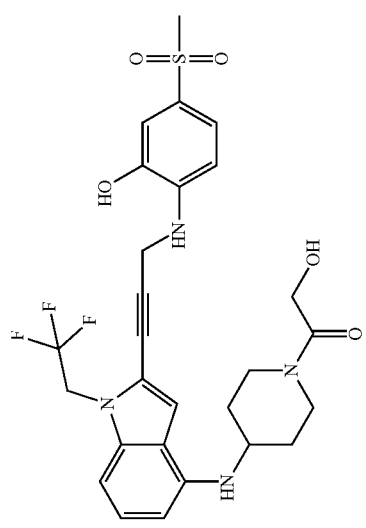 | 2-hydroxy-1-{4-[(2-{3-[(2-hydroxy-4-methanesulfonylphenyl)amino]prop-1-yn-1-yl}-1-(2,2,2-trifluoroethyl)-1H-indol-4-yl)amino]piperidin-1-yl}ethan-1-one | 579.2 |

TABLE 4-continued

| Compound No. | Structure | IUPAC | LC-MS (ES+, m/z) |
|---|---|---|---|
| 732A | 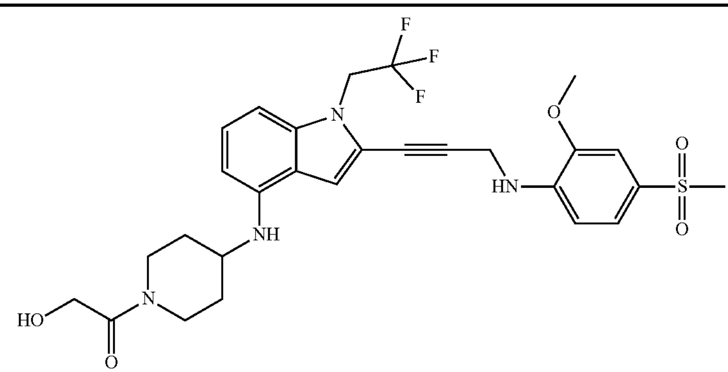 | 2-hydroxy-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethan-1-one | 539.0 |
| 733A | 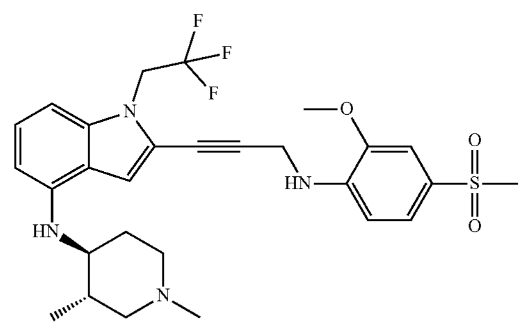 [SMILES: COc1cc(S(C)(=O)=O)ccc1NCC#Cc1cc2c(N[C@H]3CCN(C)C[C@@H]3C)cccc2n1CC(F)(F)F] | N-((3S,4S)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine | 563.2 |
| 734A | 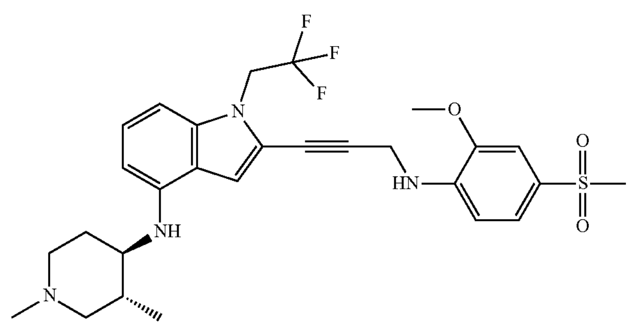 | N-((3R,4R)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine | 563.3 |

TABLE 4-continued

| Compound No. | Structure | IUPAC | LC-MS (ES+, m/z) |
|---|---|---|---|
| 735A | 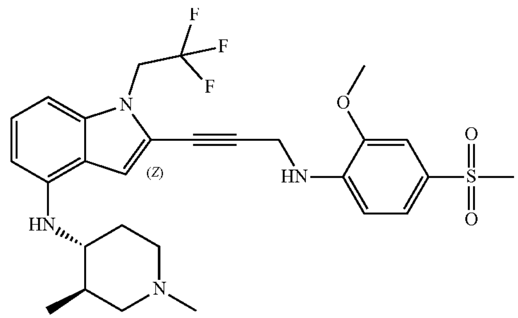 [SMILES: COc1cc(S(C)(=O)=O)ccc1NCC#Cc1cc2c(N[C@@H]3CCN(C)C[C@H]3C)cccc2n1CC(F)(F)F] | N-((3R,4R)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine | 563.3 |
| 736A | 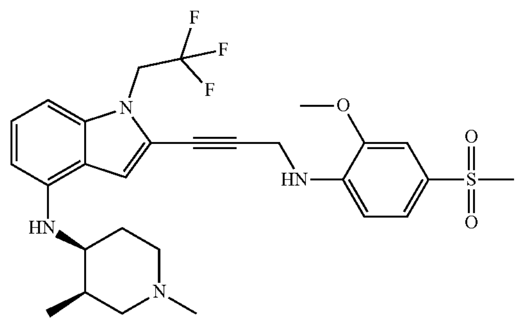 [SMILES: COc1cc(S(C)(=O)=O)ccc1NCC#Cc1cc2c(N[C@H]3CCN(C)C[C@H]3C)cccc2n1CC(F)(F)F] | N-((3R,4S)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine | 563.2 |
| 737A | 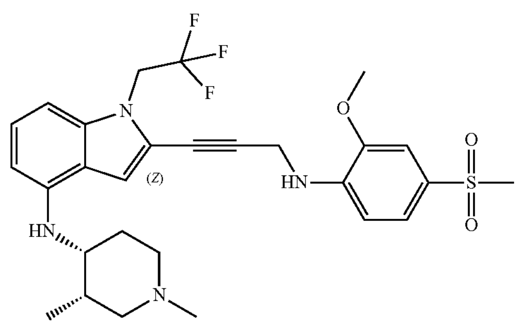 [SMILES: COc1cc(S(C)(=O)=O)ccc1NCC#Cc1cc2c(N[C@@H]3CCN(C)C[C@@H]3C)cccc2n1CC(F)(F)F] | N-((3S,4R)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine | 563.2 |

TABLE 4-continued

| Compound No. | Structure | IUPAC | LC-MS (ES+, m/z) |
|---|---|---|---|
| 738A | 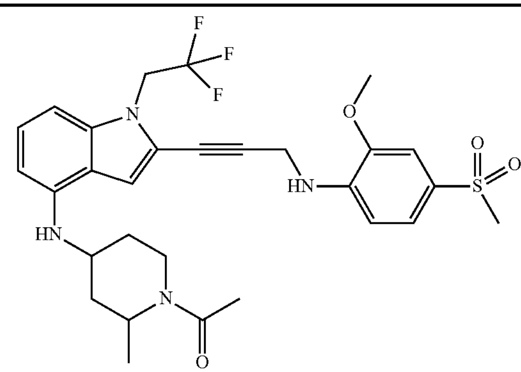 | 1-(4-((2-(3-((2-methoxy-4-(methylsulfonyl)phenyl)amino)prop-1-yn-1-yl)-1-(2,2,2-trifluoroethyl)-1H-indol-4-yl)amino)-2-methylpiperidin-1-yl)ethan-1-one | 591.2 |
| 739A | 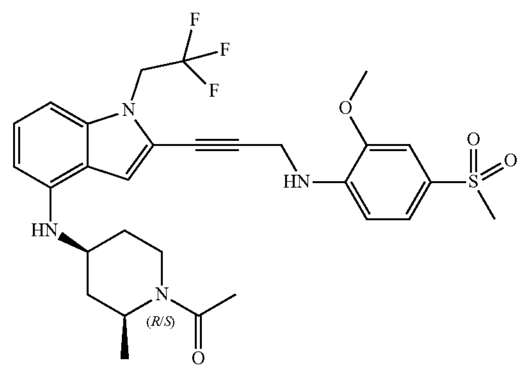 [SMILES: COc1cc(S(C)(=O)=O)ccc1NCC#Cc1cc2c(N[C@H]3CCN(C(C)=O)[C@@H](C)C3)cccc2n1CC(F)(F)F] | 1-{4-[(2-{3-[(4-methanesulfonyl-2-methoxyphenyl)amino]prop-1-yn-1-yl}-1-(2,2,2-trifluoroethyl)-1H-indol-4-yl)amino]-2-methylpiperidin-1-yl}ethan-1-one | 591.2 |

TABLE 4-continued

| Compound No. | Structure | IUPAC | LC-MS (ES+; m/z) |
|---|---|---|---|
| 740A | 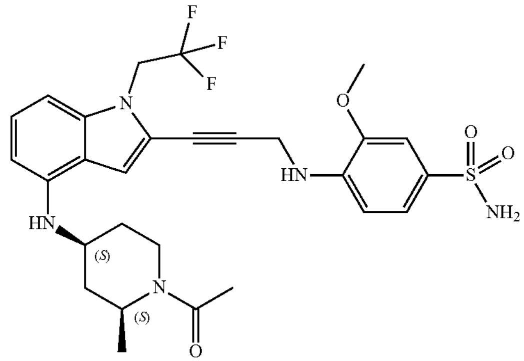 | 4-{[3-(4-{[(2S,4S)-1-acetyl-2-methylpiperidin-4-yl]amino}-1-(2,2,2-trifluoroethyl)-1H-indol-2-yl)prop-2-yn-1-yl]amino}-3-methoxybenzene-1-sulfonamide | 592.2 |
| 741A | 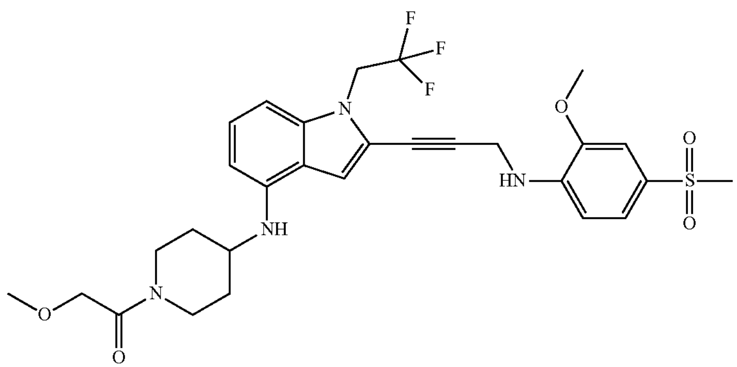 | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-2-methoxyethan-1-one | 607.2 |

TABLE 4-continued
| Compound No. | Structure | IUPAC | LC-MS (ES+, m/z) |
|---|---|---|---|
| 742A | 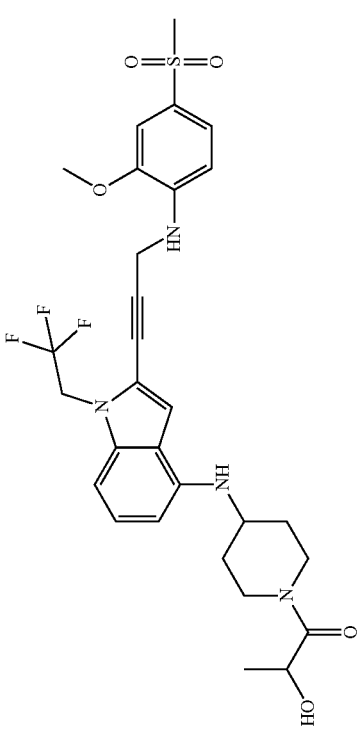 | 2-hydroxy-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-1-one | 607.2 |
| 743A | 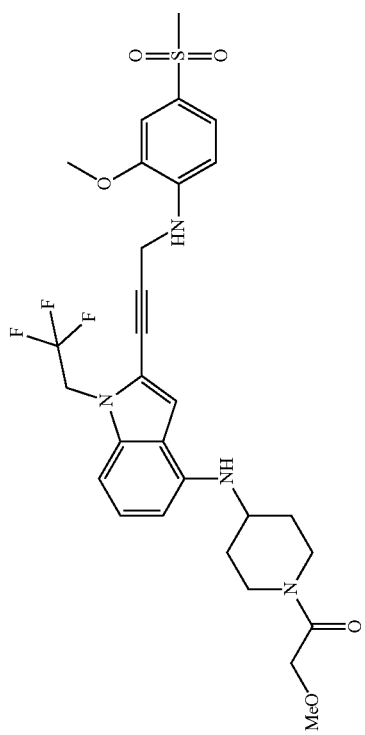 | 2-methoxy-1-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)ethan-1-one | 607.2 |

TABLE 4-continued
| Compound No. | Structure | IUPAC | LC-MS (ES+, m/z) |
|---|---|---|---|
| 744A | 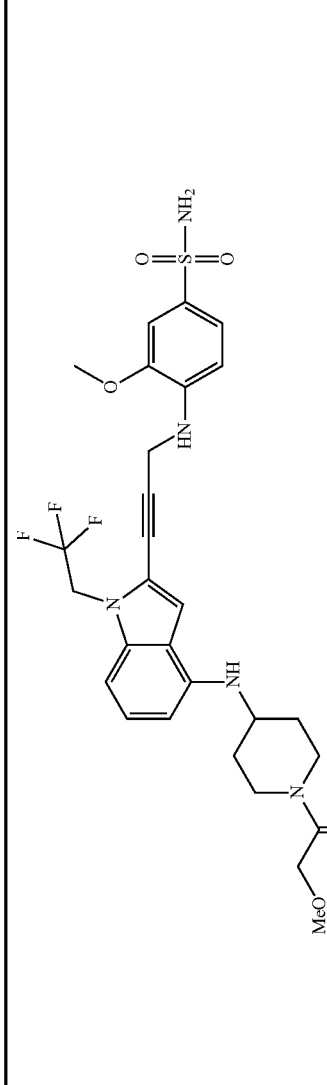 | 3-methoxy-4-((3-(4-((1-(2-methoxyacetyl)piperidin-4-yl)amino)-1-(2,2,2-trifluoroethyl)-1H-indol-2-yl)prop-2-yn-1-yl)amino)benzenesulfonamide | 607.2 |
| 745A | 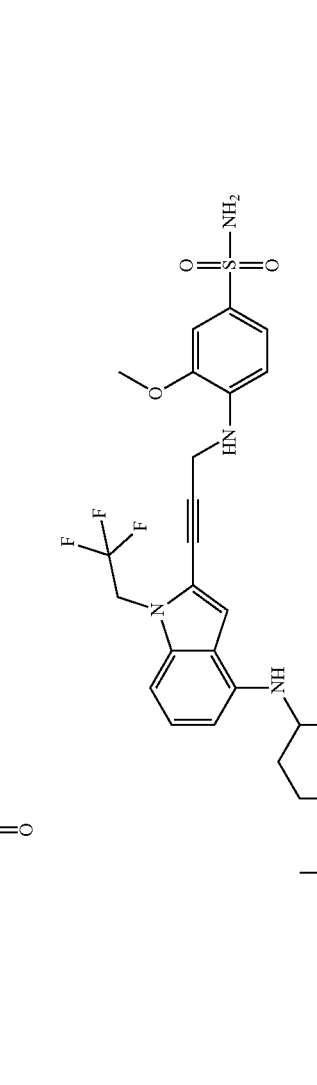 | 4-{[3-(4-{[1-(2-hydroxypropanoyl)piperidin-4-yl]amino}-1-(2,2,2-trifluoroethyl)-1H-indol-2-yl)prop-2-yn-1-yl]amino}-3-methoxybenzene-1-sulfonamide | 608.2 |

TABLE 4-continued

| Compound No. | Structure | IUPAC | LC-MS (ES+, m/z) |
|---|---|---|---|
| 746A | 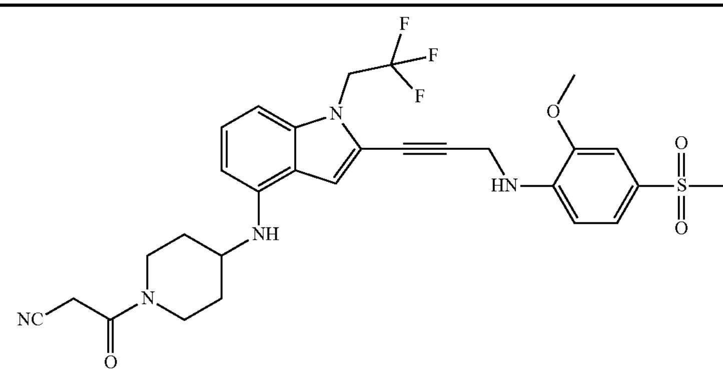 | 3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-oxopropanenitrile | 602.2 |
| 747A | 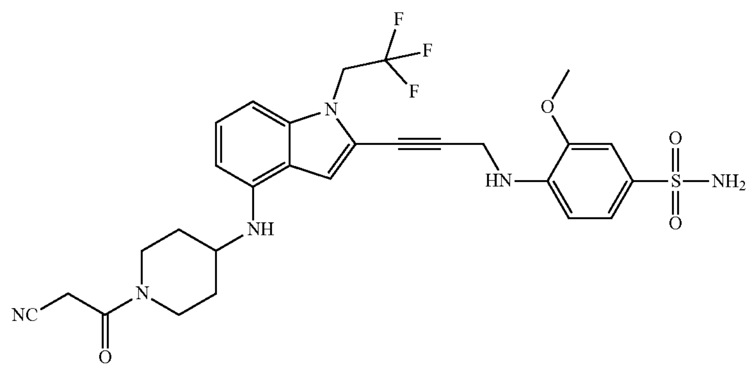 [SMILES: COc1cc(S(N)(=O)=O)ccc1NCC#Cc1cc2c(NC3CCN(C(=O)CC#N)CC3)cccc2n1CC(F)(F)F] | 4-{[3-(4-{[1-(2-cyanoacetyl)piperidin-4-yl]amino}-1-(2,2,2-trifluoroethyl)-1H-indol-2-yl)prop-2-yn-1-yl]amino}-3-methoxybenzene-1-sulfonamide | 603.2 |

TABLE 4-continued

| Compound No. | Structure | IUPAC | LC-MS (ES+, m/z) |
|---|---|---|---|
| 748A | 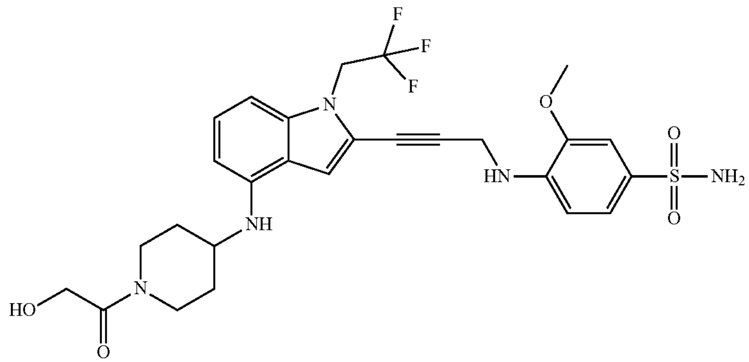 | 4-{[3-(4-{[1-(2-hydroxyacetyl)piperidin-4-yl]amino}-1-(2,2,2-trifluoroethyl)-1H-indol-2-yl)prop-2-yn-1-yl]amino}-3-methoxybenzene-1-sulfonamide | 594.2 |
| 749A | 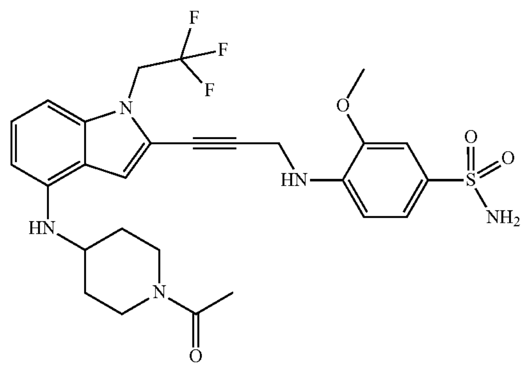 [SMILES: COc1cc(S(N)(=O)=O)ccc1NCC#Cc1cc2c(NC3CCN(C(C)=O)CC3)cccc2n1CC(F)(F)F] | 4-{[3-{4-[(1-acetylpiperidin-4-yl)amino]-1-(2,2,2-trifluoroethyl)-1H-indol-2-yl}prop-2-yn-1-yl]amino}-3-methoxybenzene-1-sulfonamide | 578.1 |

TABLE 4-continued
| Compound No. | Structure | IUPAC | LC-MS (ES+, m/z) |
|---|---|---|---|
| 750A | 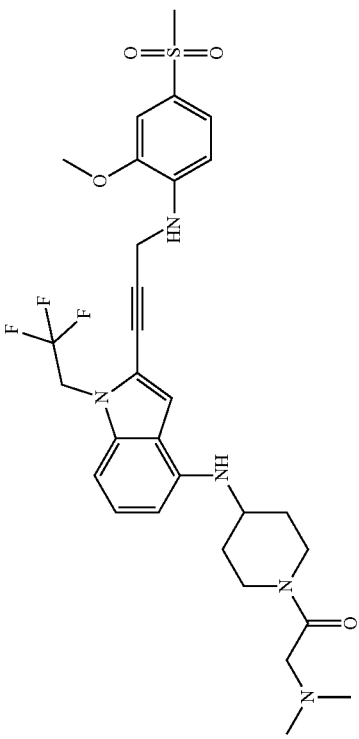 | 2-(dimethylamino)-1-{4-[(2-{3-[(4-methanesulfonyl)-2-methoxyphenyl)amino]prop-1-yn-1-yl}-1-(2,2,2-trifluoroethyl)-1H-indol-4-yl)amino]piperidin-1-yl}ethan-1-one | 620.2 |
| 751A | 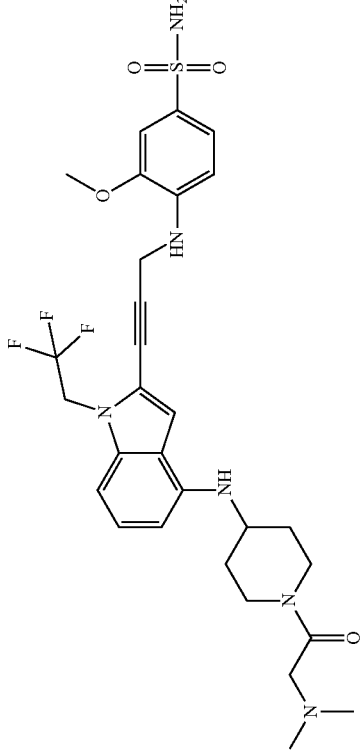 | 4-((3-(4-((1-(dimethylglycyl)piperidin-4-yl)amino)-1-(2,2,2-trifluoroethyl)-1H-indol-2-yl)prop-2-yn-1-yl)amino)-3-methoxybenzenesulfonamide | 621.2 |

TABLE 4-continued

| Compound No. | Structure | IUPAC | LC-MS (ES+, m/z) |
|---|---|---|---|
| 752A | 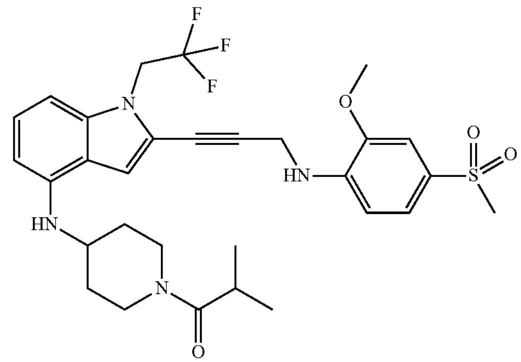 [SMILES: COc1cc(S(C)(=O)=O)ccc1NCC#Cc1cc2c(NC3CCN(C(=O)C(C)C)CC3)cccc2n1CC(F)(F)F] | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-2-methylpropan-1-one | 605.2 |
| 753A | 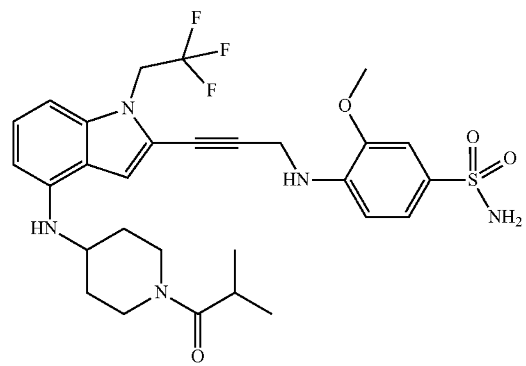 [SMILES: COc1cc(S(N)(=O)=O)ccc1NCC#Cc1cc2c(NC3CCN(C(=O)C(C)C)CC3)cccc2n1CC(F)(F)F] | 3-methoxy-4-{[3-(4-{[1-(2-methylpropanoyl)piperidin-4-yl]amino}-1-(2,2,2-trifluoroethyl)-1H-indol-2-yl)prop-2-yn-1-yl]amino}benzene-1-sulfonamide | 606.2 |

TABLE 4-continued

| Compound No. | Structure | IUPAC | LC-MS (ES+; m/z) |
|---|---|---|---|
| 754A | 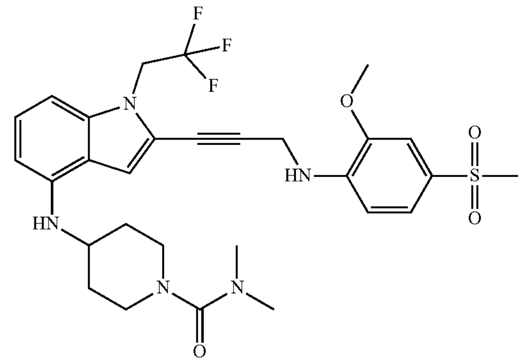 [SMILES: COc1cc(S(C)(=O)=O)ccc1NCC#Cc1cc2c(NC3CCN(C(=O)N(C)C)CC3)cccc2n1CC(F)(F)F] | 4-((2-(3-((2-methoxy-4-(methylsulfonyl)phenyl)amino)prop-1-yn-1-yl)-1-(2,2,2-trifluoroethyl)-1H-indol-4-yl)amino)-N,N-dimethylpiperidine-1-carboxamide | 606.2 |
| 755A | 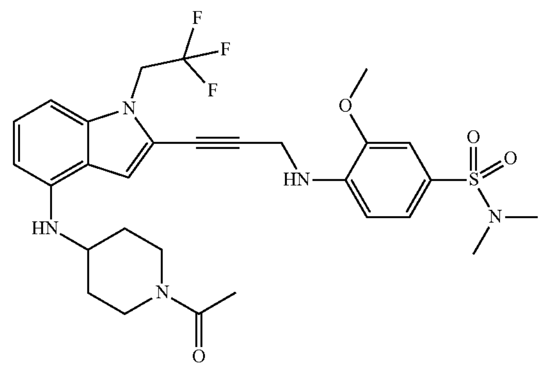 [SMILES: COc1cc(S(=O)(=O)N(C)C)ccc1NCC#Cc1cc2c(NC3CCN(C(C)=O)CC3)cccc2n1CC(F)(F)F] | 4-[(3-{4-[(1-acetylpiperidin-4-yl)amino]-1-(2,2,2-trifluoroethyl)-1H-indol-2-yl}prop-2-yn-1-yl)amino]-3-methoxy-N,N-dimethylbenzene-1-sulfonamide | 606.2 |

TABLE 4-continued

| Compound No. | Structure | IUPAC | LC-MS (ES+, m/z) |
|---|---|---|---|
| 756A | 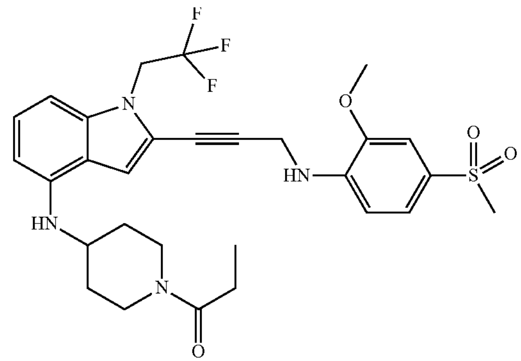 [SMILES: CCC(=O)N1CCC(Nc2cccc3c2cc(C#CCNc2ccc(S(C)(=O)=O)cc2OC)n3CC(F)(F)F)CC1] | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-1-one | 591.2 |
| 757A | 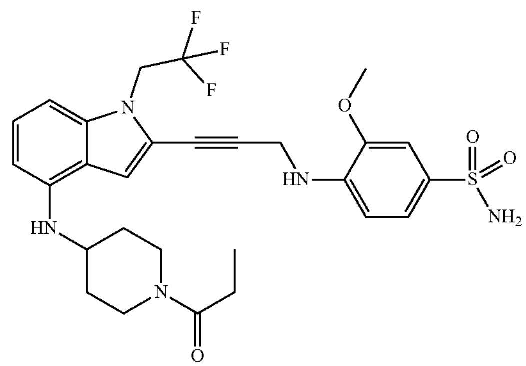 | 3-methoxy-4-[(3-{4-[(1-propanoylpiperidin-4-yl)amino]-1-(2,2,2-trifluoroethyl)-1H-indol-2-yl}prop-2-yn-1-yl)amino]benzene-1-sulfonamide | 592.1 |

TABLE 4-continued

| Compound No. | Structure | IUPAC | LC-MS (ES+, m/z) |
|---|---|---|---|
| 758A | 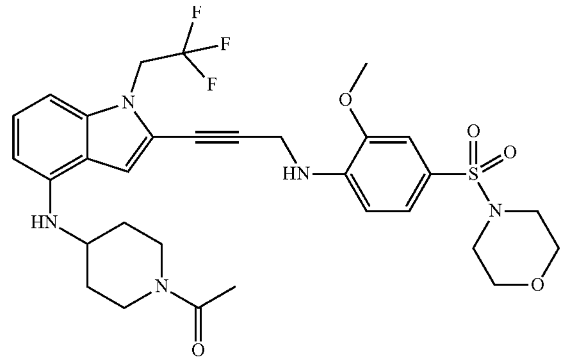 [SMILES: COc1cc(S(=O)(=O)N2CCOCC2)ccc1NCC#Cc1cc2c(NC3CCN(C(C)=O)CC3)cccc2n1CC(F)(F)F] | 1-(4-{[2-(3-{[2-methoxy-4-(morpholine-4-sulfonyl)phenyl]amino}prop-1-yn-1-yl)-1-(2,2,2-trifluoroethyl)-1H-indol-4-yl]amino}piperidin-1-yl)ethan-1-one | 648.2 |
| 759A | 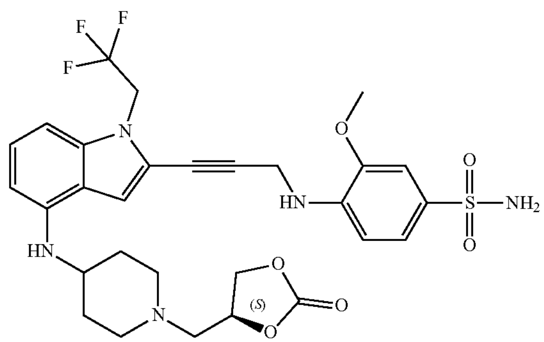 | 3-methoxy-4-[(3-{4-[(1-{[(4S)-2-oxo-1,3-dioxolan-4-yl]methyl}piperidin-4-yl)amino]-1-(2,2,2-trifluoroethyl)-1H-indol-2-yl}prop-2-yn-1-yl)amino]benzene-1-sulfonamide | 636.2 |

TABLE 4-continued
| Compound No. | Structure | IUPAC | LC-MS (ES+, m/z) |
|---|---|---|---|
| 760A | 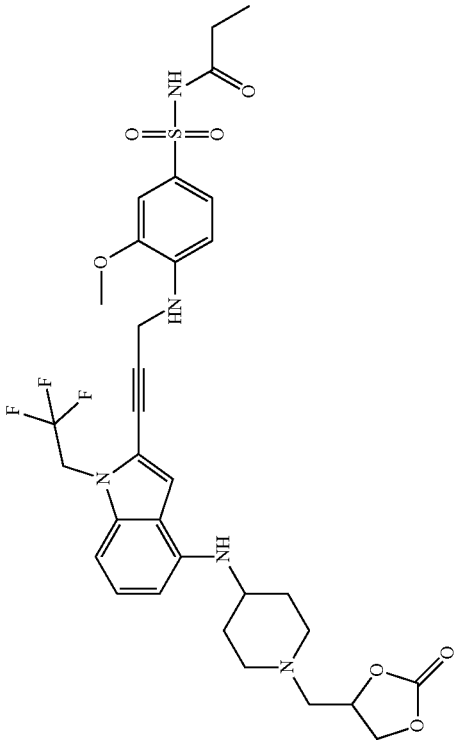 | N-((3-methoxy-4-((3-(4-((1-((2-oxo-1,3-dioxolan-4-yl)methyl)piperidin-4-yl)amino)-1-(2,2,2-trifluoroethyl)-1H-indol-2-yl)prop-2-yn-1-yl)amino)phenyl)sulfonyl)propionamide | |
| 761A | 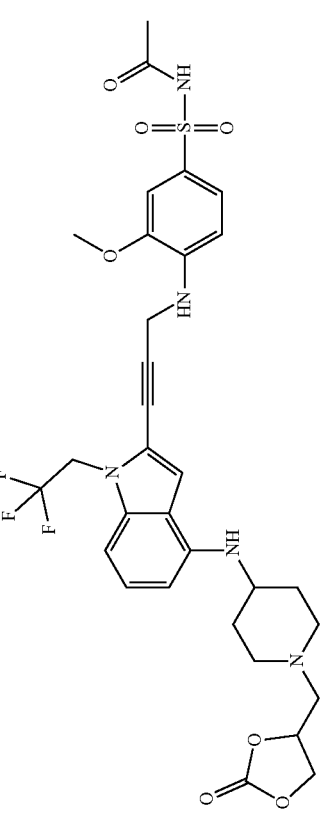 | N-[3-[4-({3-[4-({1-[(2-oxo-1,3-dioxolan-4-yl)methyl]piperidin-4-yl}amino)-1-(2,2,2-trifluoroethyl)-1H-indol-2-yl]prop-2-yn-1-yl}amino)benzenesulfonyl]acetamide | 678.2 |

TABLE 4-continued

| Compound No. | Structure | IUPAC | LC-MS (ES+, m/z) |
|---|---|---|---|
| 762A | 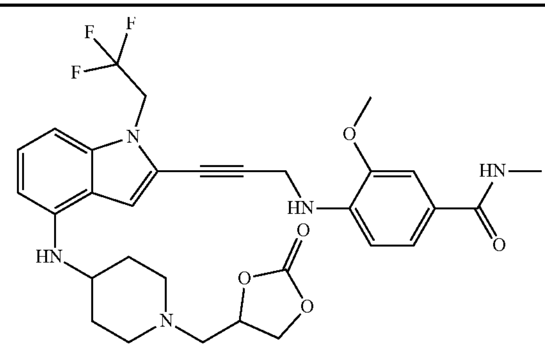 | 3-methoxy-N-methyl-4-({3-[4-({1-[(2-oxo-1,3-dioxolan-4-yl)methyl]piperidin-4-yl}amino)-1-(2,2,2-trifluoroethyl)-1H-indol-2-yl]prop-2-yn-1-yl}amino)benzamide | 614.3 |
| 763A | 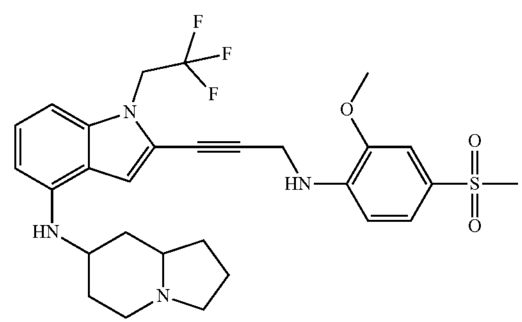 [SMILES: COc1cc(S(C)(=O)=O)ccc1NCC#Cc1cc2c(NC3CCN4CCCC4C3)cccc2n1CC(F)(F)F] | 2-{3-[(2-methoxy-4-(methylsulfonyl)phenyl)amino]prop-1-yn-1-yl}-N-(octahydroindolizin-7-yl)-1-(2,2,2-trifluoroethyl)-1H-indol-4-amine | 575.2 |
| 764A | 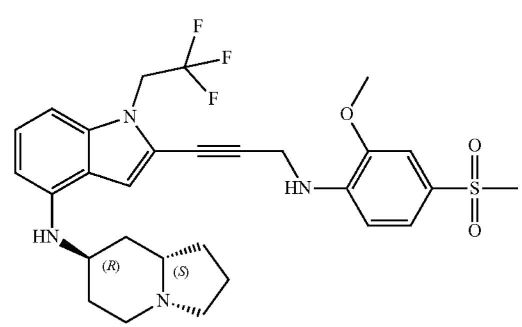 | N-[(7R,8aS)-octahydroindolizin-7-yl]-2-{3-[(4-methanesulfonyl)-2-methoxyphenyl)amino]prop-1-yn-1-yl}-1-(2,2,2-trifluoroethyl)-1H-indol-4-amine | 575.2 |

TABLE 4-continued

| Compound No. | Structure | IUPAC | LC-MS (ES+, m/z) |
|---|---|---|---|
| 765A | 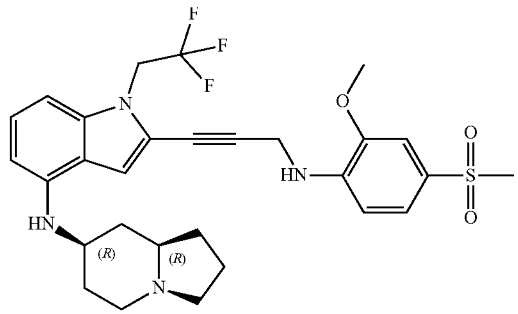 | N-[(7R,8aR)-octahydroindolizin-7-yl]-2-{3-[(4-methanesulfonyl)-2-methoxyphenyl)amino]prop-1-yn-1-yl}-1-(2,2,2-trifluoroethyl)-1H-indol-4-amine | 575.2 |
| 766A | 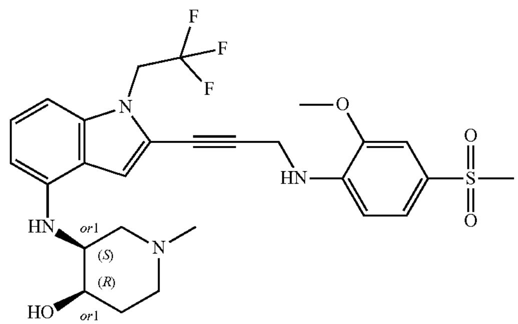 | rac-(3R,4S)-3-[(2-{3-[(4-methanesulfonyl)-2-methoxyphenyl)amino]prop-1-yn-1-yl}-1-(2,2,2-trifluoroethyl)-1H-indol-4-yl)amino]-1-methylpiperidin-4-ol | 565.3 |
| 767A | 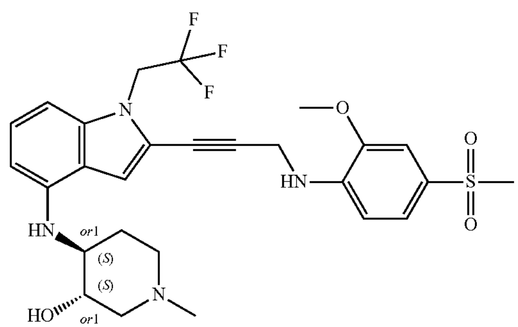 | rac-(3R,4R)-4-[(2-{3-[(4-methanesulfonyl)-2-methoxyphenyl)amino]prop-1-yn-1-yl}-1-(2,2,2-trifluoroethyl)-1H-indol-4-yl)amino]-1-methylpiperidin-3-ol | 565.1 |

TABLE 4-continued

| Compound No. | Structure | IUPAC | LC-MS (ES+; m/z) |
|---|---|---|---|
| 768A | 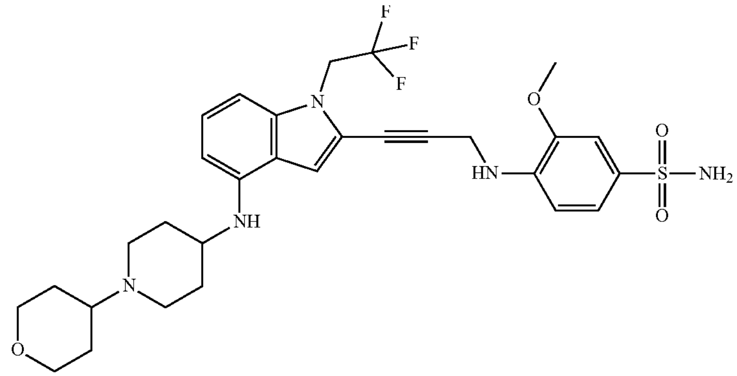 | 3-methoxy-4-((3-(4-(((1-(tetrahydro-2H-pyran-4-yl)piperidin-4-yl)amino)-1-(2,2,2-trifluoroethyl)-1H-indol-2-yl)prop-2-yn-1-yl)amino)benzenesulfonamide | 620.2 |
| 769A | 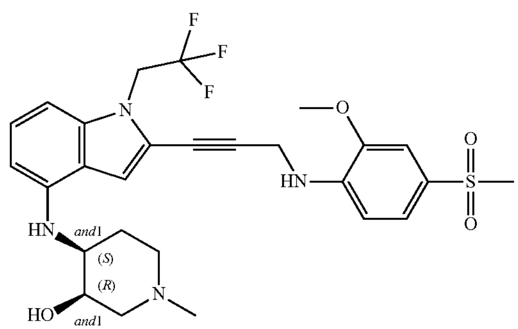 | rac-N-[(3R,4S)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine | 567.2 |
| 770A | 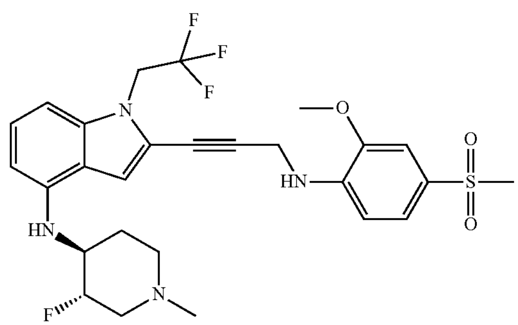 | N-((3S,4S)-3-fluoro-1-methylpiperidin-4-yl)-2-(3-((2-methoxy-4-(methylsulfonyl)phenyl)amino)prop-1-yn-1-yl)-1-(2,2,2-trifluoroethyl)-1H-indol-4-amine | 567.2 |

TABLE 4-continued

| Compound No. | Structure | IUPAC | LC-MS (ES+, m/z) |
|---|---|---|---|
| 771A | 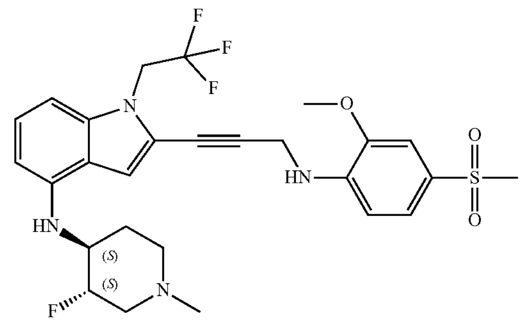 | N-[(3S,4S)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine | 567.2 |
| 772A | 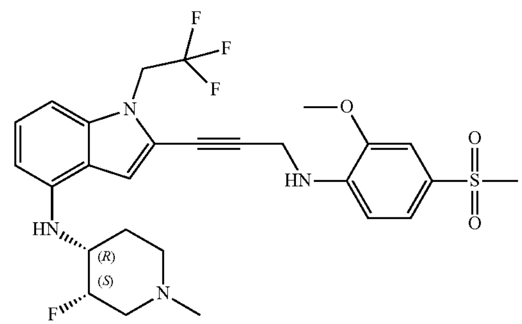 | N-[(3R,4S)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine | 567.2 |
| 773A | 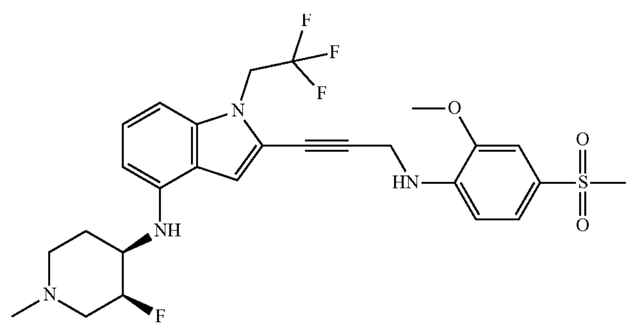 | N-[(3S,4R)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine | 567.2 |

TABLE 4-continued

| Compound No. | Structure | IUPAC | LC-MS (ES+, m/z) |
|---|---|---|---|
| 774A | 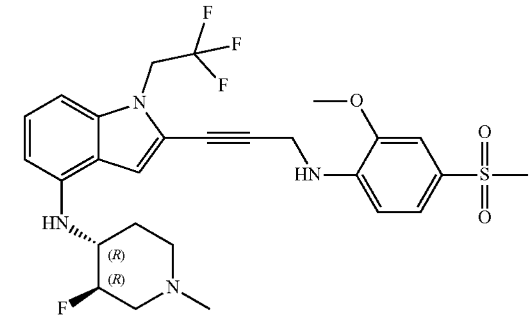 | N-[(3R,4R)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine | 567.2 |
| 775A | 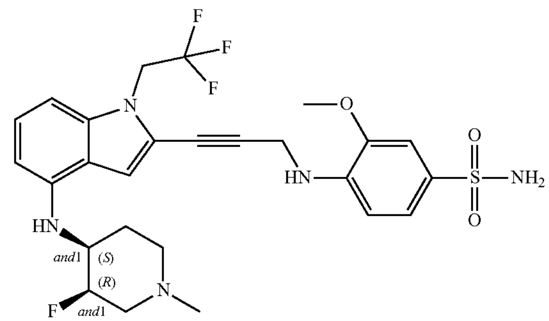 | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonamide | 568.2 |
| 776A | 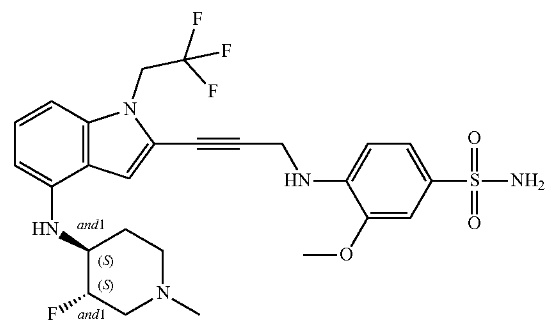 | rac-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonamide | 568.1 |

TABLE 4-continued

| Compound No. | Structure | IUPAC | LC-MS (ES+, m/z) |
|---|---|---|---|
| 777A | 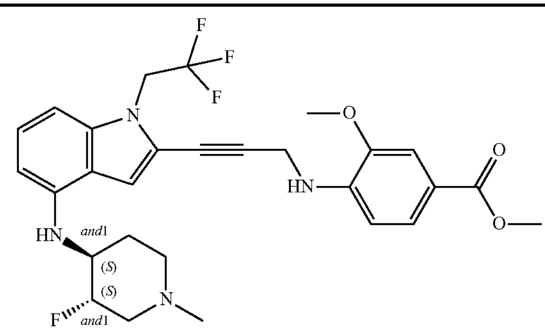 | rac-methyl 4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzoate | 547.3 |
| 778A | 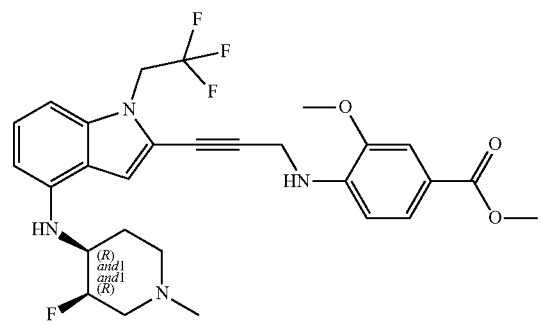 | rac-methyl 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoate | 547.2 |
| 779A | 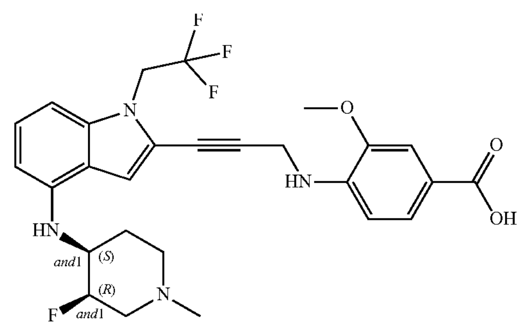 | rac-4-{[3-(4-{[(3R,4S)-3-fluoro-1-methylpiperidin-4-yl]amino}-1-(2,2,2-trifluoroethyl)-1H-indol-2-yl]prop-2-yn-1-yl]amino}-3-methoxybenzoic acid | 533.2 |

TABLE 4-continued

| Compound No. | Structure | IUPAC | LC-MS (ES+, m/z) |
|---|---|---|---|
| 780A | 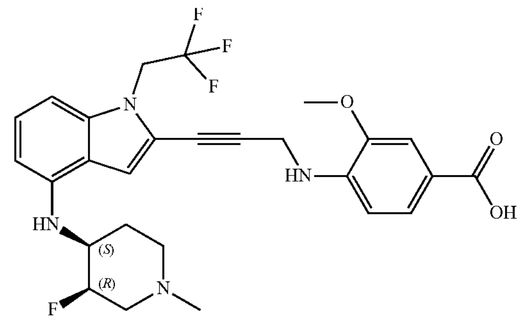 | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoic acid | 533.2 |
| 781A | 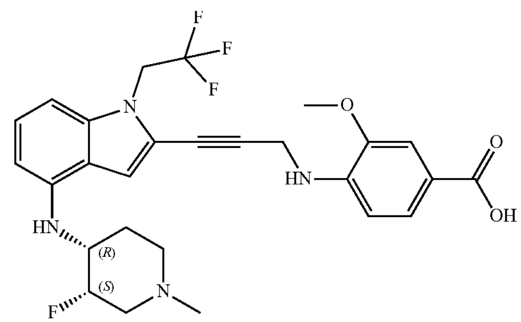 | 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoic acid | 533.2 |
| 782A | 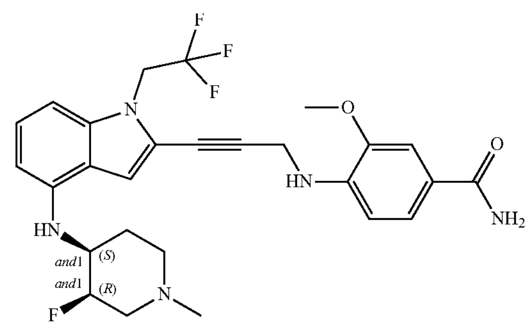 | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzamide | 532.1 |

TABLE 4-continued

| Compound No. | Structure | IUPAC | LC-MS (ES+, m/z) |
|---|---|---|---|
| 783A | 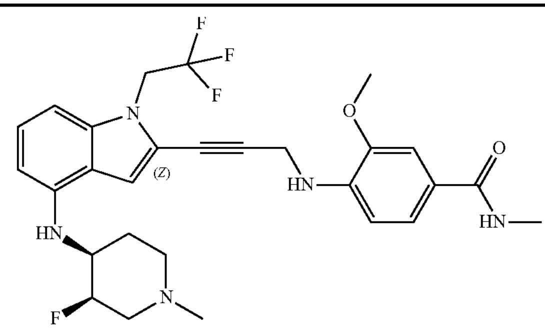 | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide | 546.2 |
| 784A | 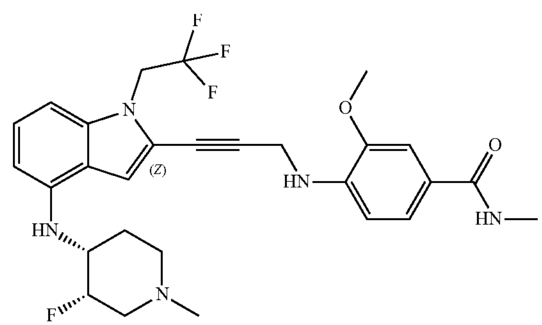 | 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxy-N-methylbenzamide | 546.2 |
| 785A | 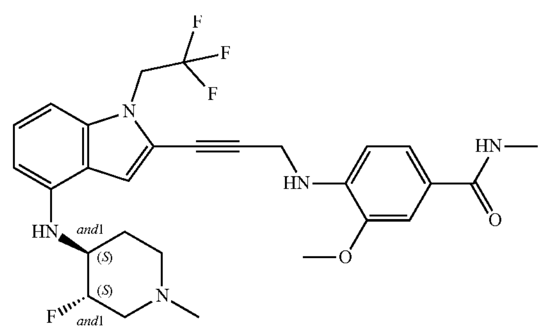 | rac-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide | 546.2 |

TABLE 4-continued

| Compound No. | Structure | IUPAC | LC-MS (ES+, m/z) |
|---|---|---|---|
| 786A | 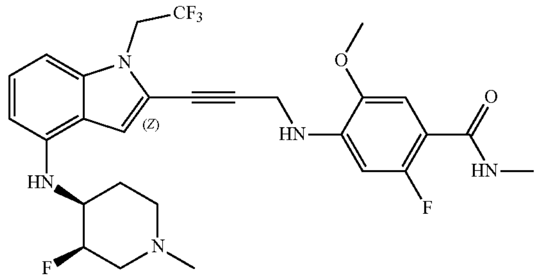 | 2-fluoro-4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-5-methoxy-N-methylbenzamide | 564.3 |
| 787A | 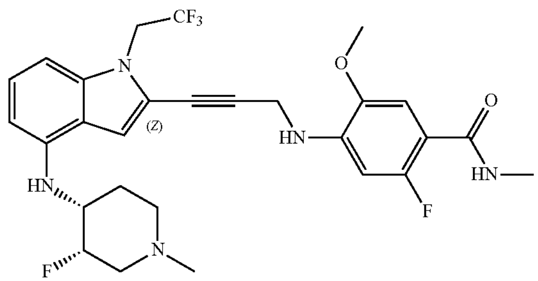 [SMILES: CNC(=O)c1cc(OC)c(NCC#Cc2cc3c(N[C@@H]4CCN(C)C[C@@H]4F)cccc3n2CC(F)(F)F)cc1F] | 2-fluoro-4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-5-methoxy-N-methylbenzamide | 564.3 |
| 788A | 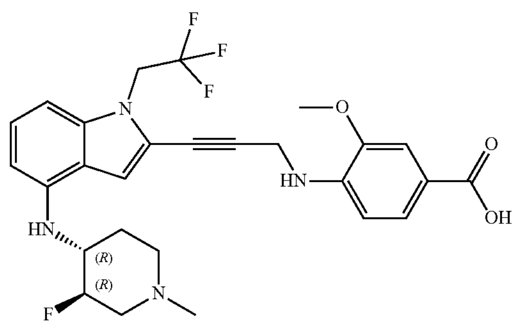 | 4-[[3-(4-{[(3R,4R)-3-fluoro-1-methylpiperidin-4-yl]amino}-1-(2,2,2-trifluoroethyl)-1H-indol-2-yl)prop-2-yn-1-yl]amino]-3-methoxybenzoic acid | 533.1 |

TABLE 4-continued

| Compound No. | Structure | IUPAC | LC-MS (ES+, m/z) |
|---|---|---|---|
| 789A | 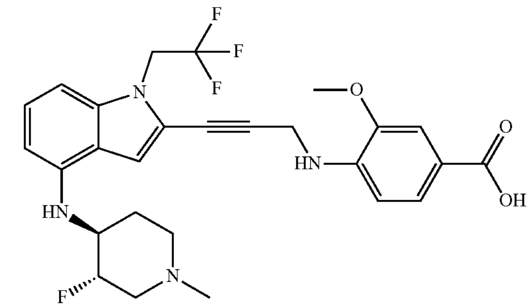 [SMILES: COc1cc(C(=O)O)ccc1NCC#Cc1cc2c(N[C@H]3CCN(C)C[C@@H]3F)cccc2n1CC(F)(F)F] | 4-{[3-(4-{[(3S,4S)-3-fluoro-1-methylpiperidin-4-yl]amino}-1-(2,2,2-trifluoroethyl)-1H-indol-2-yl)prop-2-yn-1-yl]amino}-3-methoxybenzoic acid | 533.1 |
| 790A | 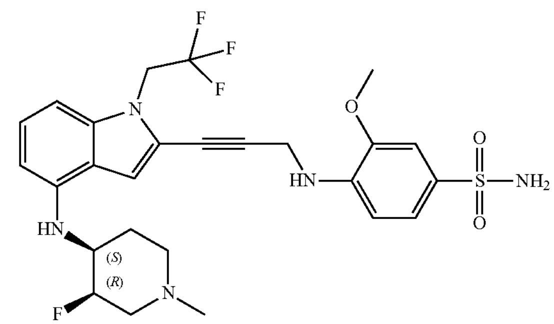 | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonamide | 568.3 |
| 791A | 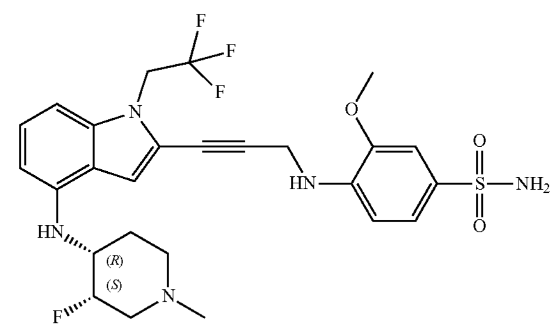 | 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonamide | 568.3 |

TABLE 4-continued

| Compound No. | Structure | IUPAC | LC-MS (ES+, m/z) |
|---|---|---|---|
| 792A | 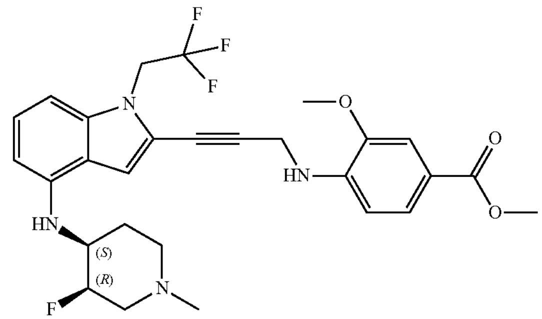 | methyl 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoate | 547.2 |
| 793A | 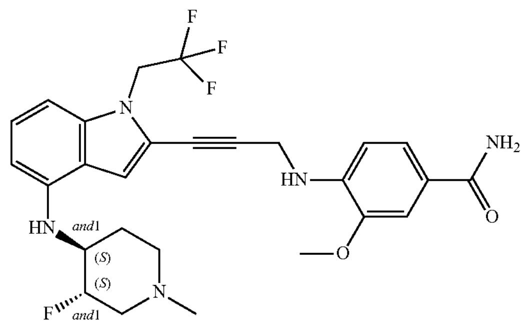 | rac-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzamide | 532.2 |
| 794A | 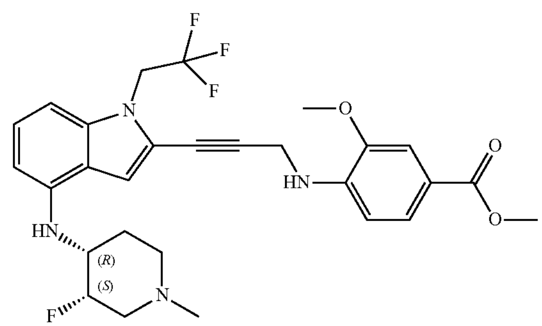 | methyl 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoate | 547.2 |

TABLE 4-continued
| Compound No. | Structure | IUPAC | LC-MS (ES+, m/z) |
|---|---|---|---|
| 795A | 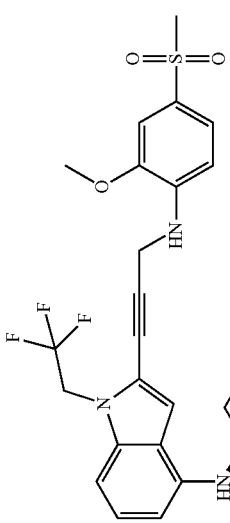 | rac-N-[(3R,4S)-3-fluoro-1-(propan-2-yl)piperidin-4-yl]-2-{3-[(4-methanesulfonyl-2-methoxyphenyl)amino]prop-1-yn-1-yl}-1-(2,2,2-trifluoroethyl)-1H-indol-4-amine | 595.3 |
| 796A | 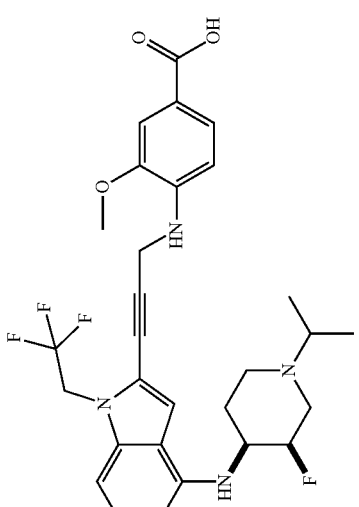 | rac-4-{[3-(4-{[(3R,4S)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoic acid | 561.3 |

TABLE 4-continued
| Compound No. | Structure | IUPAC | LC-MS (ES+, m/z) |
|---|---|---|---|
| 797A | 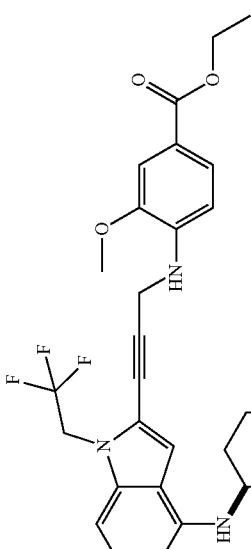 | rac-ethyl 4-{[3-(4-{[(3R,4S)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoate | 589.3 |
| 798A | 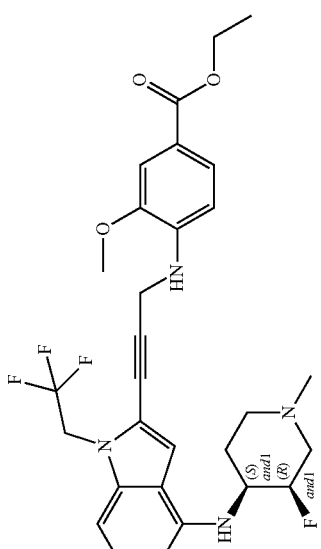 | rac-ethyl 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoate | 561.3 |

TABLE 4-continued

| Compound No. | Structure | IUPAC | LC-MS (ES⁺, m/z) |
|---|---|---|---|
| 799A | 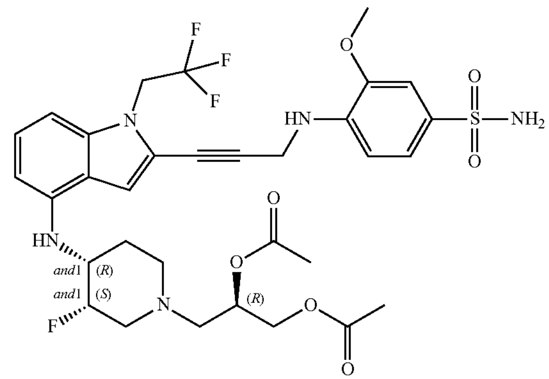 | (2R)-1-(acetyloxy)-3-[(3RS,4SR)-3-fluoro-4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl]propan-2-yl acetate | 712.2 |
| 800A | 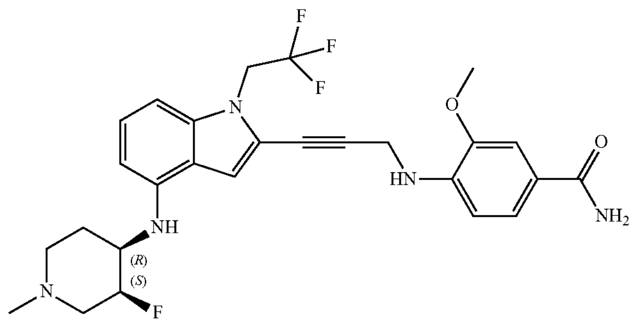 | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide | 532.2 |
| 801A | 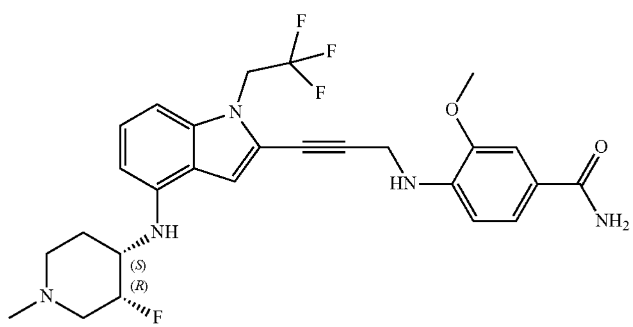 | 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzamide | 532.2 |

TABLE 4-continued

| Compound No. | Structure | IUPAC | LC-MS (ES+, m/z) |
|---|---|---|---|
| 802A | 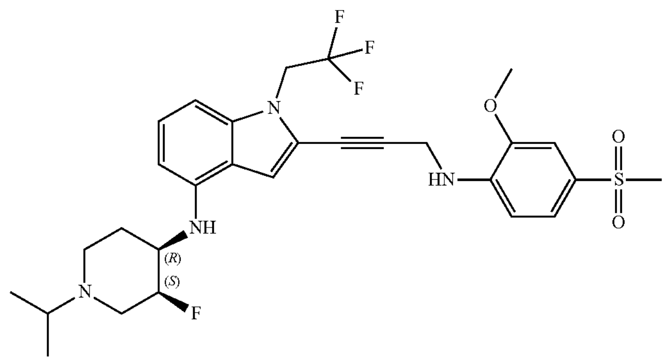 | N-[(3S,4R)-3-fluoro-1-(propan-2-yl)piperidin-4-yl]-2-{3-[(4-methanesulfonyl-2-methoxyphenyl)amino]prop-1-yn-1-yl}-1-(2,2,2-trifluoroethyl)-1H-indol-4-amine | 595.3 |
| 803A | 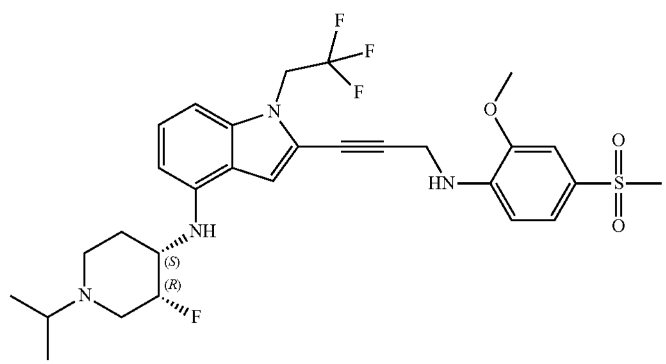 | N-[(3R,4S)-3-fluoro-1-(propan-2-yl)piperidin-4-yl]-2-{3-[(4-methanesulfonyl-2-methoxyphenyl)amino]prop-1-yn-1-yl}-1-(2,2,2-trifluoroethyl)-1H-indol-4-amine | 595.3 |

| Compound No. | Structure | IUPAC | LC-MS (ES+, m/z) |
|---|---|---|---|
| 804A | 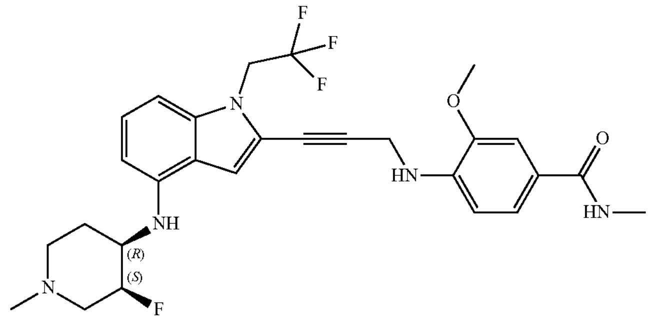 | 4-{3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide | 546.3 |
| 805A | 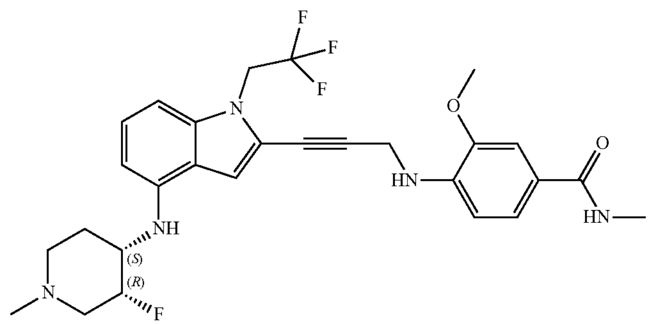 | 4-{3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide | 546.3 |
| 806A | 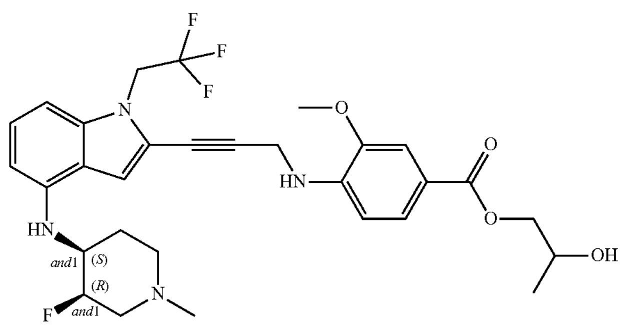 | rac-2-hydroxypropyl 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoate | 591.3 |

TABLE 4-continued

| Compound No. | Structure | IUPAC | LC-MS (ES+, m/z) |
|---|---|---|---|
| 807A | 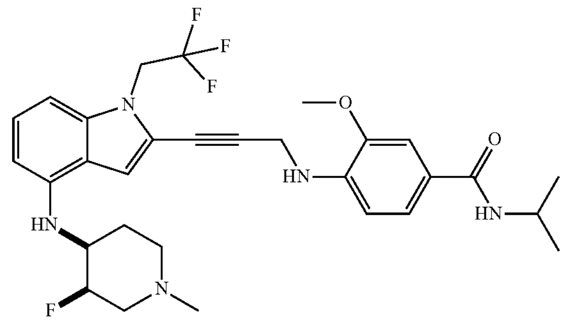 [SMILES: COc1cc(C(=O)NC(C)C)ccc1NCC#Cc1cc2c(N[C@H]3CCN(C)C[C@H]3F)cccc2n1CC(F)(F)F] | 4-({3-(4-(((3R,4S)-3-fluoro-1-methylpiperidin-4-yl)amino)-1-(2,2,2-trifluoroethyl)-1H-indol-2-yl)prop-2-yn-1-yl}amino)-N-isopropyl-3-methoxybenzamide | 574.3 |
| 808A | 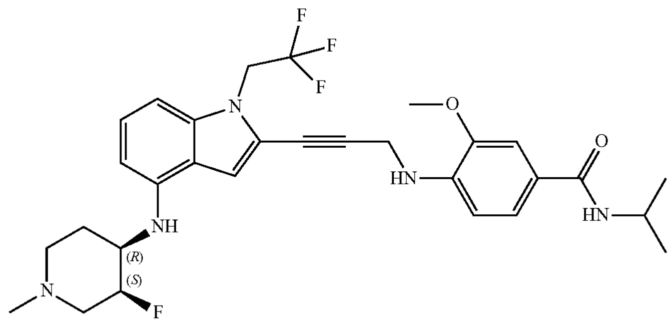 | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(propan-2-yl)benzamide | 574.3 |
| 809A | 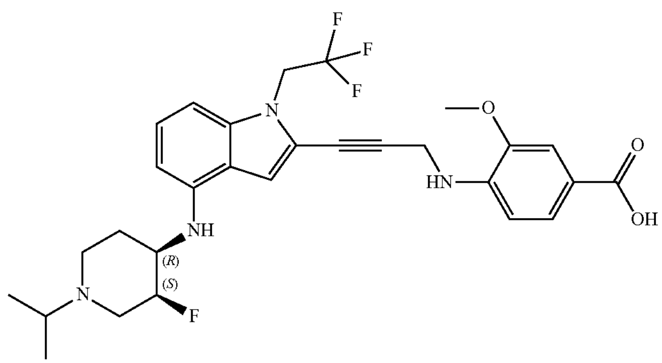 | 4-{[3-(4-{[(3S,4R)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoic acid | 561.2 |

TABLE 4-continued

| Compound No. | Structure | IUPAC | LC-MS (ES+, m/z) |
|---|---|---|---|
| 810A | 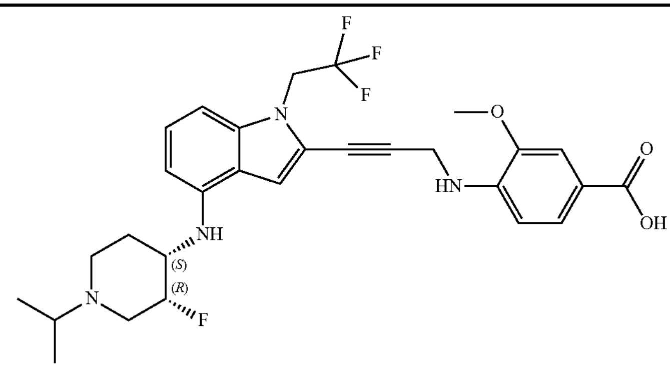 | 4-{[3-(4-{[(3R,4S)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoic acid | 561.2 |
| 811A | 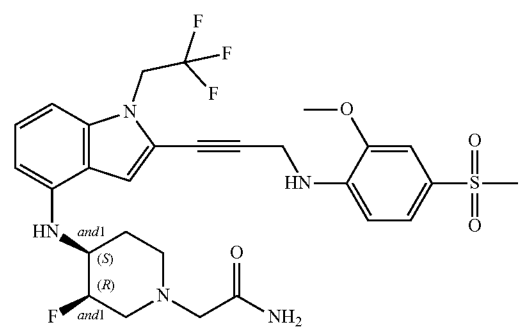 | rac-2-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]acetamide | 610.2 |
| 812A | 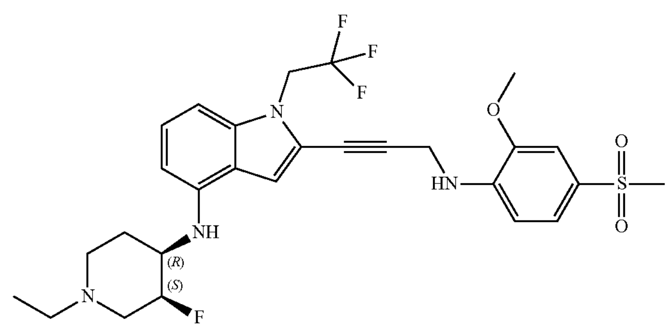 | N-[(3S,4R)-1-ethyl-3-fluoropiperidin-4-yl]-2-{3-[(4-methanesulfonyl-2-methoxyphenyl)amino]prop-1-yn-1-yl}-1-(2,2,2-trifluoroethyl)-1H-indol-4-amine | 581.3 |

TABLE 4-continued

| Compound No. | Structure | IUPAC | LC-MS (ES+, m/z) |
|---|---|---|---|
| 813A | 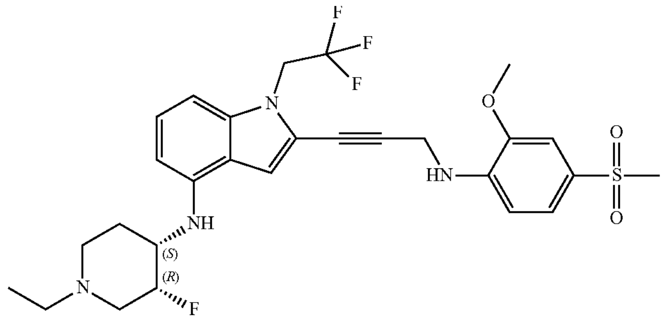 | N-[(3R,4S)-1-ethyl-3-fluoropiperidin-4-yl]-2-{3-[(4-methanesulfonyl-2-methoxyphenyl)amino]prop-1-yn-1-yl}-1-(2,2,2-trifluoroethyl)-1H-indol-4-amine | 581.3 |
| 814A | 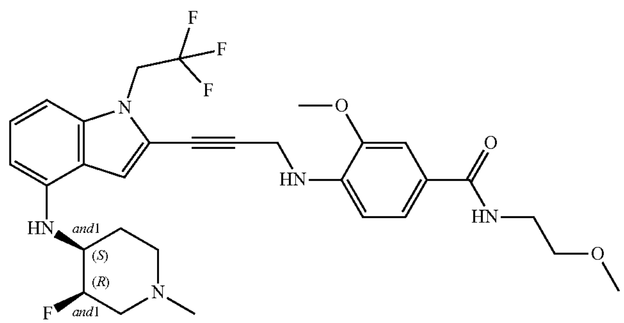 | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-(2-methoxyethyl)benzamide | 590.4 |
| 815A | 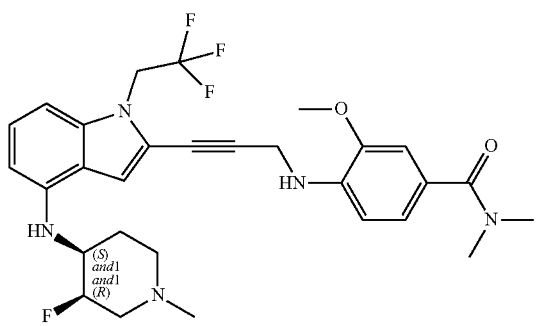 | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N,N-dimethylbenzamide | 560.3 |

TABLE 4-continued

| Compound No. | Structure | IUPAC | LC-MS (ES+, m/z) |
|---|---|---|---|
| 816A | 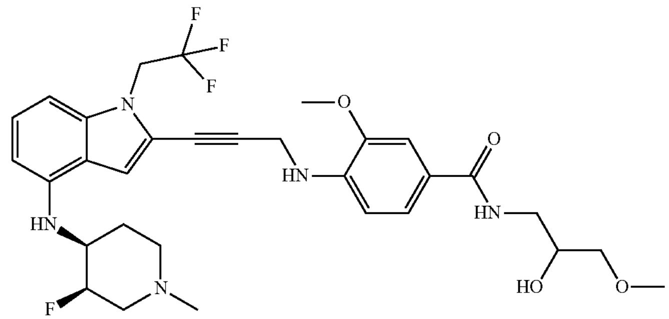 [SMILES: COCC(O)CNC(=O)c1ccc(NCC#Cc2cc3c(N[C@H]4CCN(C)C[C@H]4F)cccc3n2CC(F)(F)F)c(OC)c1] | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-N-(2-hydroxy-3-methoxypropyl)-3-methoxybenzamide | 620.2 |
| 817A | 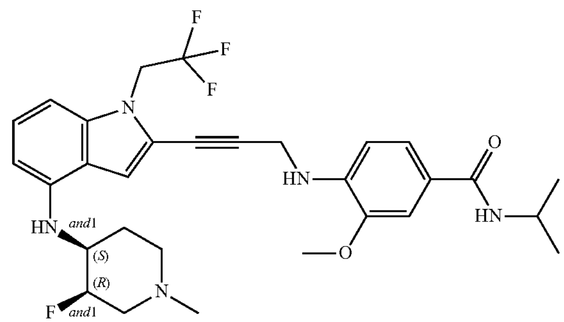 | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-(propan-2-yl)benzamide | 574.3 |
| 818A | 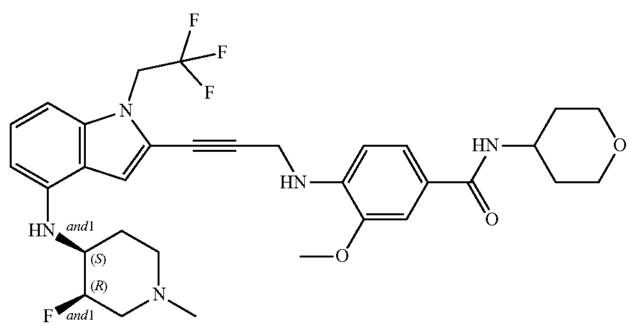 | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-(oxan-4-yl)benzamide | 616.3 |

TABLE 4-continued

| Compound No. | Structure | IUPAC | LC-MS (ES+, m/z) |
|---|---|---|---|
| 819A | 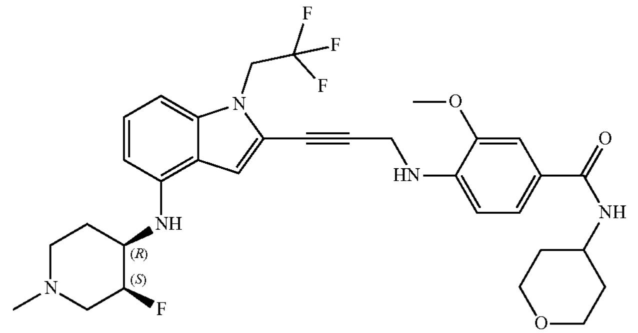 | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(oxan-4-yl)benzamide | 616.3 |
| 820A | 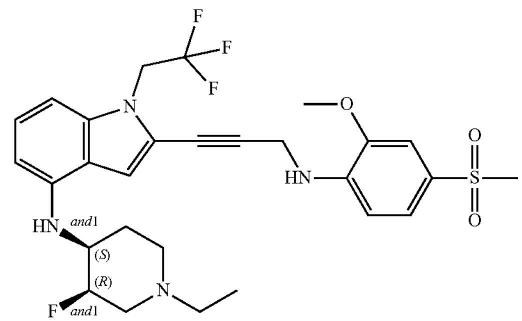 | rac-N-[(3R,4S)-1-ethyl-3-fluoropiperidin-4-yl]-2-{3-[(4-methanesulfonyl-2-methoxyphenyl)amino]prop-1-yn-1-yl}-1-(2,2,2-trifluoroethyl)-1H-indol-4-amine | 581.3 |
| 821A | 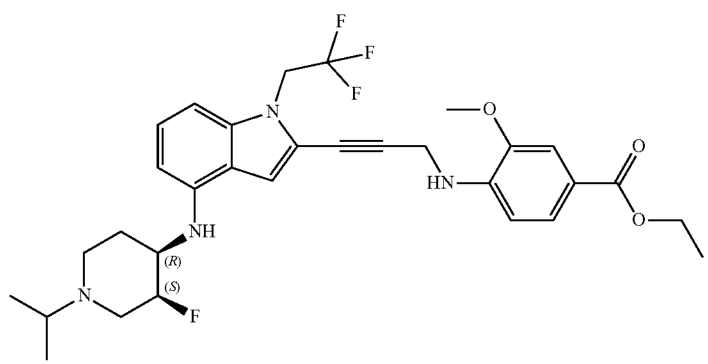 | ethyl 4-{[3-(4-{[(3S,4R)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoate | 589.2 |

TABLE 4-continued

| Compound No. | Structure | IUPAC | LC-MS (ES+, m/z) |
|---|---|---|---|
| 822A | 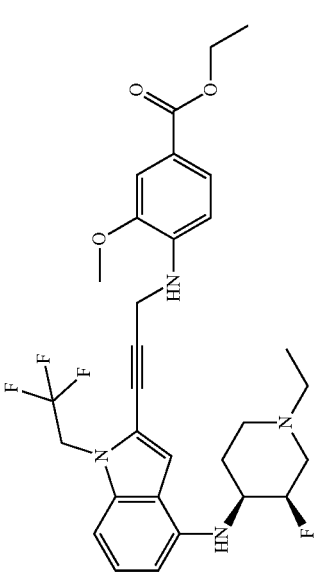 | ethyl 4-(3-(4-(((3R,4S)-1-ethyl-3-fluoropiperidin-4-yl)amino)-1-(2,2,2-trifluoroethyl)-1H-indol-2-yl)prop-2-yn-1-yl)amino)-3-methoxybenzoate | 575.2 |
| 823A | 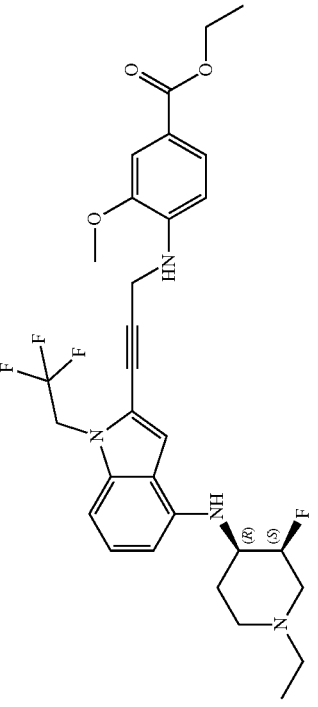 | ethyl 4-{[3-(4-{[(3S,4R)-1-ethyl-3-fluoropiperidin-4-yl]amino}-1-(2,2,2-trifluoroethyl)-1H-indol-2-yl]prop-2-yn-1-yl]amino}-3-methoxybenzoate | 575.2 |
| 824A | 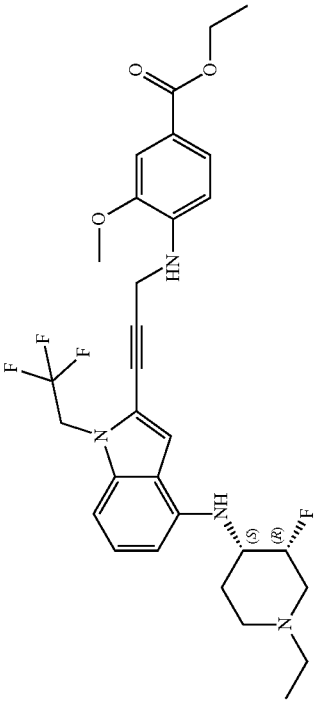 | ethyl 4-{[3-(4-{[(3R,4S)-1-ethyl-3-fluoropiperidin-4-yl]amino}-1-(2,2,2-trifluoroethyl)-1H-indol-2-yl]prop-2-yn-1-yl]amino}-3-methoxybenzoate | 575.2 |

TABLE 4-continued

| Compound No. | Structure | IUPAC | LC-MS (ES+, m/z) |
|---|---|---|---|
| 825A | 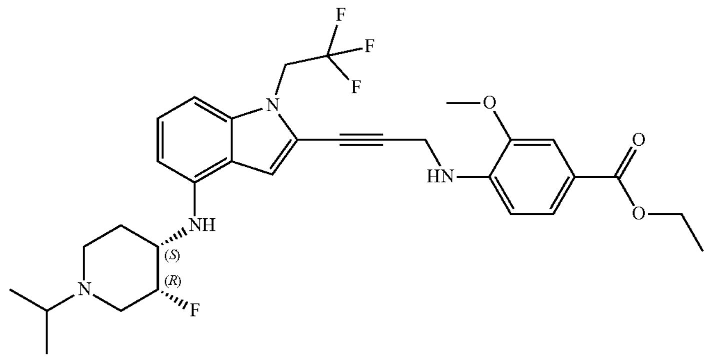 | ethyl 4-{[3-(4-{[(3R,4S)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoate | 589.2 |
| 826A | 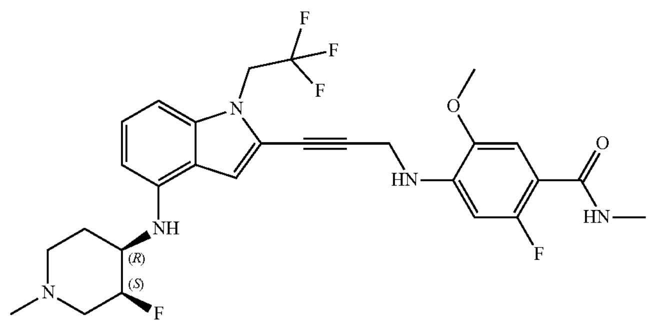 | 2-fluoro-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-5-methoxy-N-methylbenzamide | 564.3 |
| 827A | 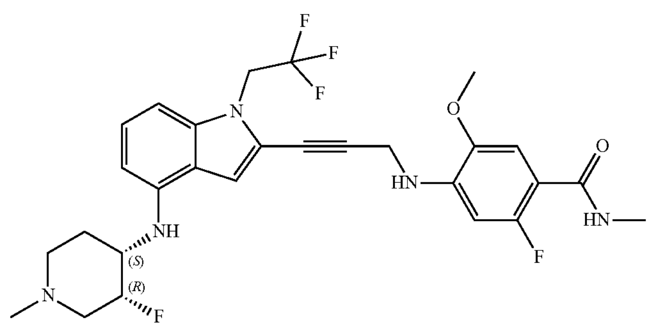 | 2-fluoro-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-5-methoxy-N-methylbenzamide | 564.3 |

TABLE 4-continued

| Compound No. | Structure | IUPAC | LC-MS (ES+, m/z) |
|---|---|---|---|
| 828A | 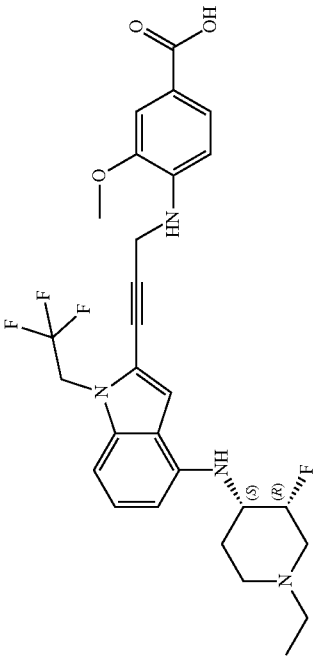 | 4-{[3-(4-{[(3R,4S)-1-ethyl-3-fluoropiperidin-4-yl]amino}-1-(2,2,2-trifluoroethyl)-1H-indol-2-yl)prop-2-yn-1-yl]amino}-3-methoxybenzoic acid | 547.3 |
| 829A | 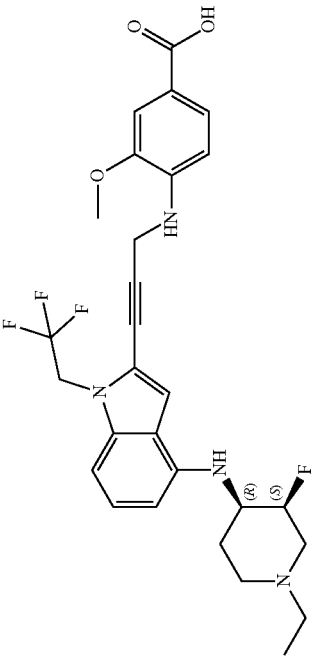 | 4-{[3-(4-{[(3S,4R)-1-ethyl-3-fluoropiperidin-4-yl]amino}-1-(2,2,2-trifluoroethyl)-1H-indol-2-yl)prop-2-yn-1-yl]amino}-3-methoxybenzoic acid | 547.3 |
| 830A | 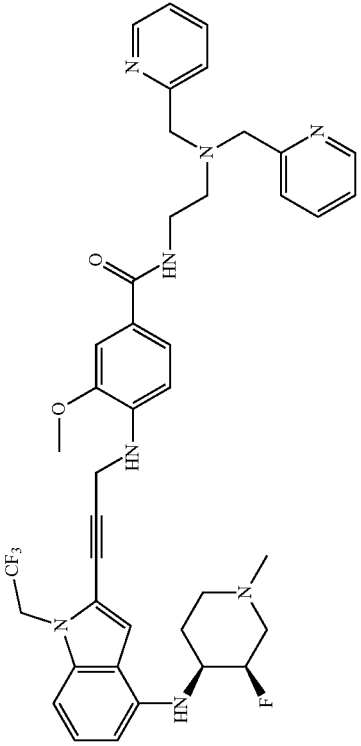 | rac-N-(2-{bis[(pyridin-2-yl)methyl]amino}ethyl)-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzamide | 557.3 |

TABLE 4-continued

| Compound No. | Structure | IUPAC | LC-MS (ES+, m/z) |
|---|---|---|---|
| 831A | 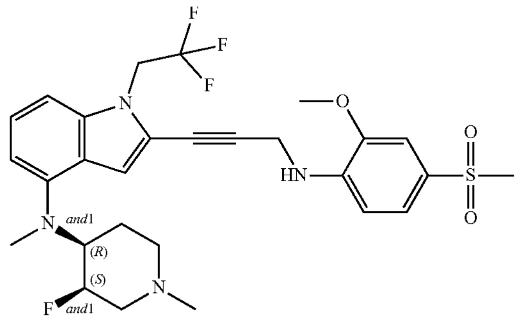 | rac-N-[(3R,4S)-3-fluoro-1-methylpiperidin-4-yl]-2-{3-[(4-methanesulfonyl-2-methoxyphenyl)amino]prop-1-yn-1-yl}-N-methyl-1-(2,2,2-trifluoroethyl)-1H-indol-4-amine | 581.2 |
| 832A | 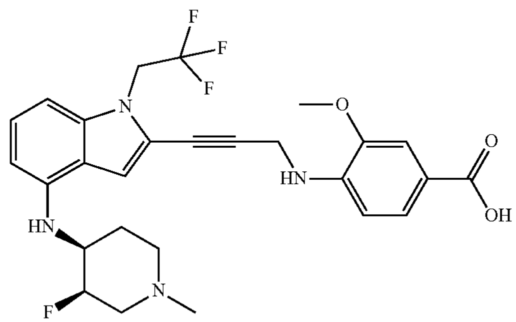 [SMILES: COc1cc(C(=O)O)ccc1NCC#Cc1cc2c(N[C@H]3CCN(C)C[C@H]3F)cccc2n1CC(F)(F)F] | rac-4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-3-methoxybenzoic acid | 533.2 |
| 833A | 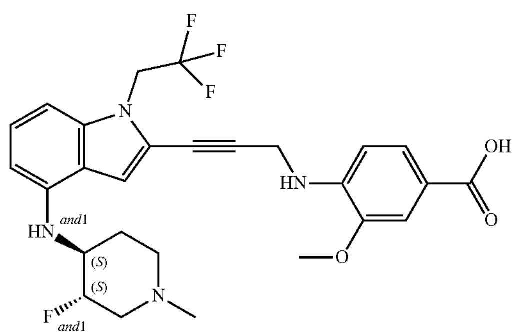 | rac-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzoic acid | 533.1 |

TABLE 4-continued

| Compound No. | Structure | IUPAC | LC-MS (ES+, m/z) |
|---|---|---|---|
| 834A | 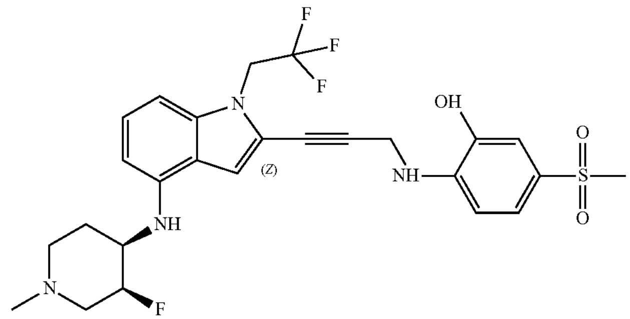 | 2-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-5-methanesulfonylphenol | 553.2 |
| 835A | 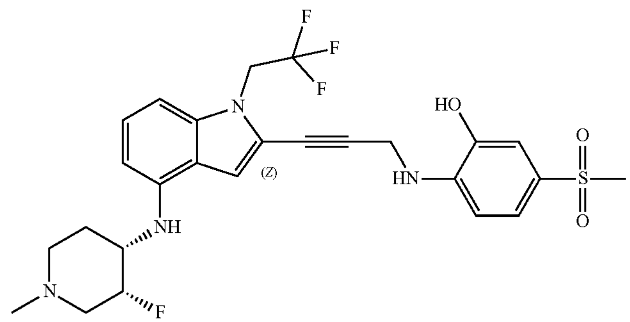 | 2-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-5-methanesulfonylphenol | 553.2 |
| 836A | 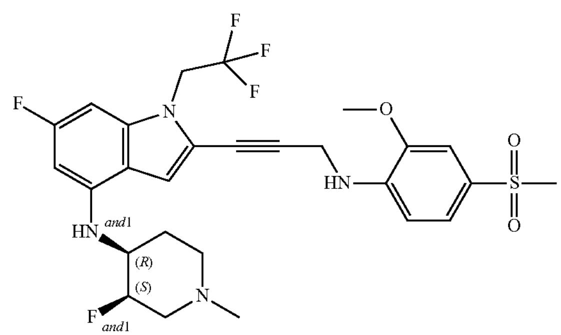 | rac-6-fluoro-N-[(3R,4S)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine | 584.8 |

TABLE 4-continued

| Compound No. | Structure | IUPAC | LC-MS (ES+, m/z) |
|---|---|---|---|
| 837A | 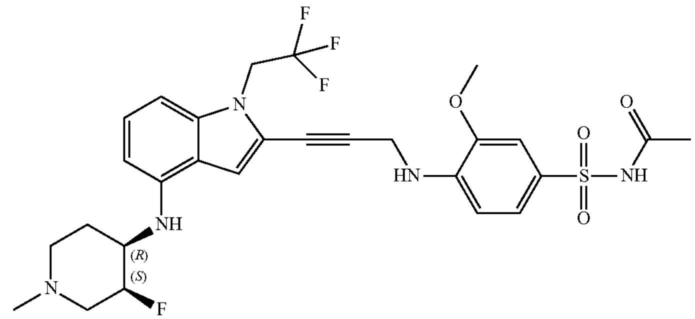 | N-(4-{[3-(4-{[(3S,4R)-3-fluoro-1-methyl]piperidin-4-yl]amino}-1-(2,2,2-trifluoroethyl)-1H-indol-2-yl)prop-2-yn-1-yl]amino}-3-methoxybenzenesulfonyl)acetamide | 610.2 |
| 838A | 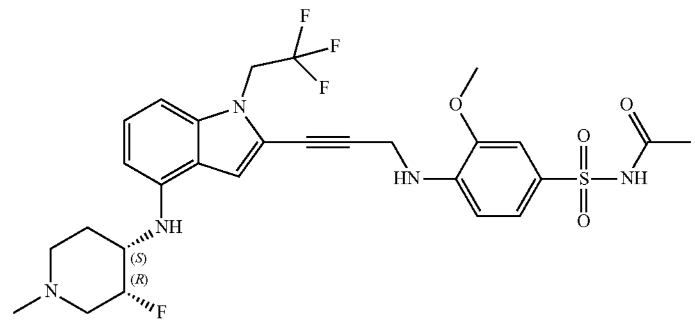 | N-(4-{[3-(4-{[(3R,4S)-3-fluoro-1-methyl]piperidin-4-yl]amino}-1-(2,2,2-trifluoroethyl)-1H-indol-2-yl)prop-2-yn-1-yl]amino}-3-methoxybenzenesulfonyl)acetamide | 610.2 |
| 839A | 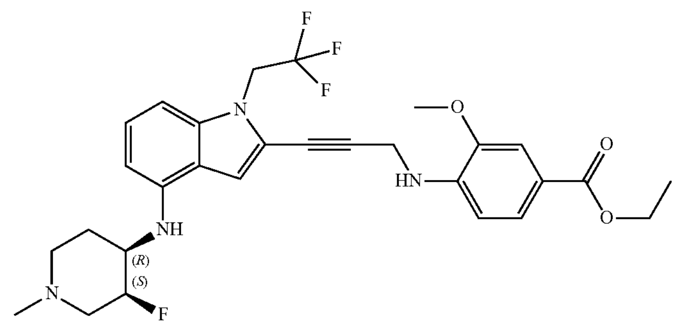 | ethyl 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoate | 561.3 |

TABLE 4-continued

| Compound No. | Structure | IUPAC | LC-MS (ES+, m/z) |
|---|---|---|---|
| 840A | 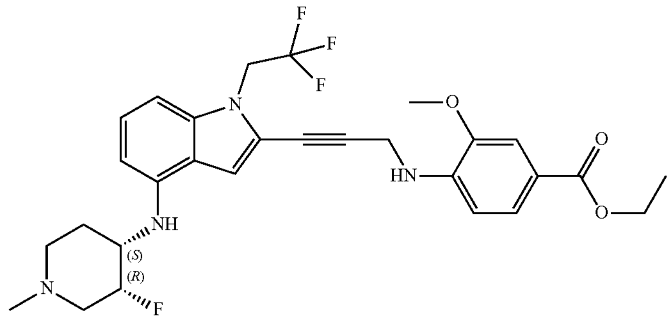 | ethyl 4-[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoate | 561.3 |
| 841A | 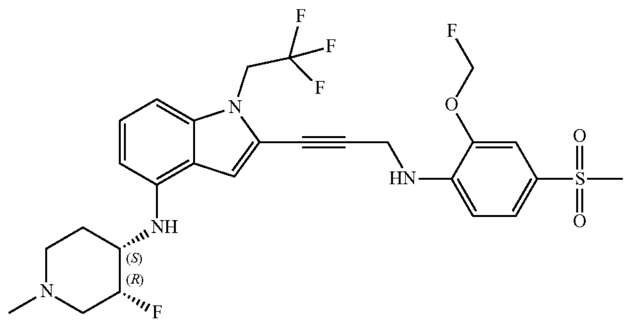 | N-[(3R,4S)-3-fluoro-1-methylpiperidin-4-yl]-2-(3-{[2-(fluoromethoxy)-4-methanesulfonylphenyl]amino}prop-1-yn-1-yl)-1-(2,2,2-trifluoroethyl)-1H-indol-4-amine | 585.3 |
| 842A | 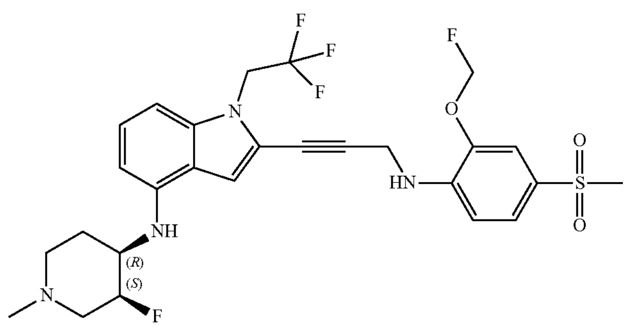 | N-[(3S,4R)-3-fluoro-1-methylpiperidin-4-yl]-2-(3-{[2-(fluoromethoxy)-4-methanesulfonylphenyl]amino}prop-1-yn-1-yl)-1-(2,2,2-trifluoroethyl)-1H-indol-4-amine | 585.3 |

TABLE 4-continued

| Compound No. | Structure | IUPAC | LC-MS (ES+, m/z) |
|---|---|---|---|
| 843A | 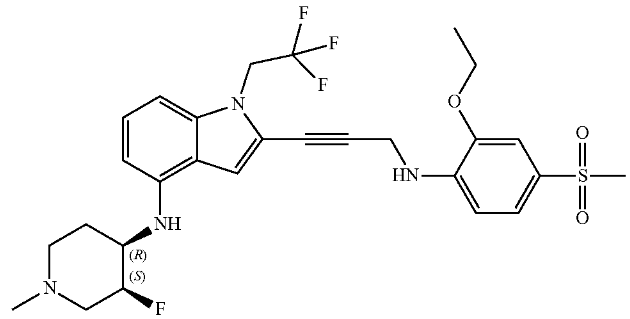 | 2-{3-[(2-ethoxy-4-methanesulfonylphenyl)amino]prop-1-yn-1-yl}-N-[(3S,4R)-3-fluoro-1-methylpiperidin-4-yl]-1-(2,2,2-trifluoroethyl)-1H-indol-4-amine | 581.1 |
| 844A | 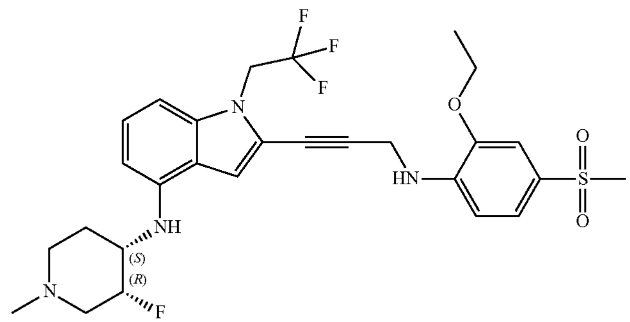 | 2-{3-[(2-ethoxy-4-methanesulfonylphenyl)amino]prop-1-yn-1-yl}-N-[(3R,4S)-3-fluoro-1-methylpiperidin-4-yl]-1-(2,2,2-trifluoroethyl)-1H-indol-4-amine | 581.1 |
| 845A | 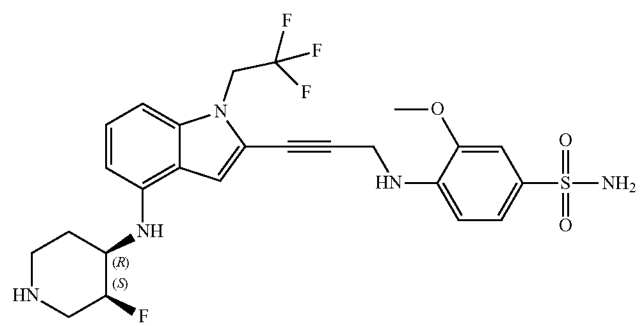 | 4-{[3-(4-{[(3S,4R)-3-fluoropiperidin-4-yl]amino}-1-(2,2,2-trifluoroethyl)-1H-indol-2-yl)prop-2-yn-1-yl]amino}-3-methoxybenzene-1-sulfonamide | 554.2 |

| Compound No. | Structure | IUPAC | LC-MS (ES+, m/z) |
|---|---|---|---|
| 846A | 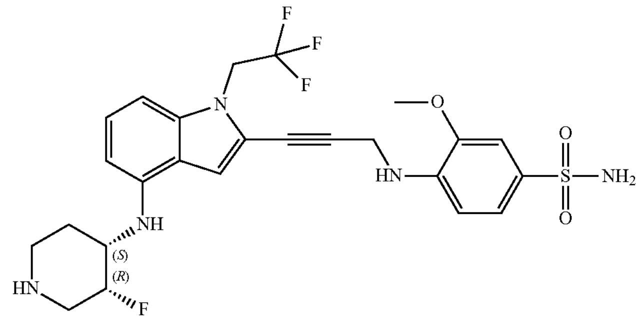 | 4-[3-(4-{[(3R,4S)-3-fluoropiperidin-4-yl]amino}-1-(2,2,2-trifluoroethyl)-1H-indol-2-yl)prop-2-yn-1-yl]amino}-3-methoxybenzene-1-sulfonamide | 554.2 |
| 847A | 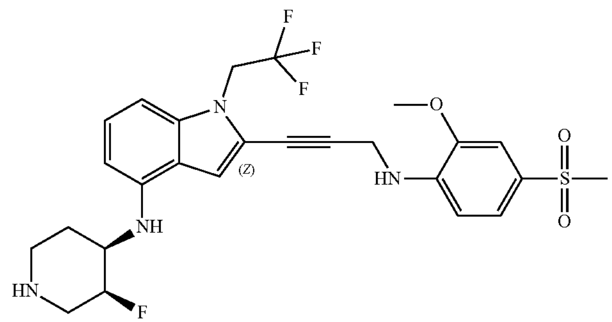 [SMILES: COc1cc(S(C)(=O)=O)ccc1NCC#Cc1cc2c(N[C@@H]3CCNC[C@@H]3F)cccc2n1CC(F)(F)F] | N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine | 553.2 |
| 848A | 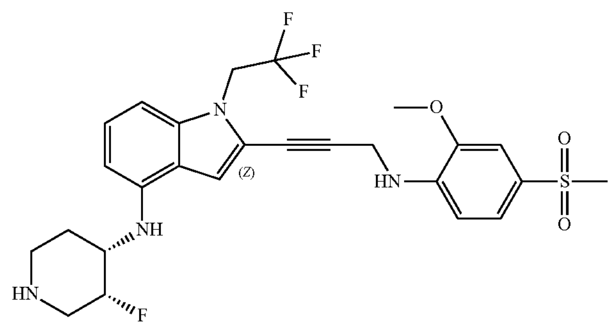 [SMILES: COc1cc(S(C)(=O)=O)ccc1NCC#Cc1cc2c(N[C@H]3CCNC[C@H]3F)cccc2n1CC(F)(F)F] | N-((3R,4S)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine | 553.2 |

TABLE 4-continued

| Compound No. | Structure | IUPAC | LC-MS (ES+, m/z) |
|---|---|---|---|
| 849A | 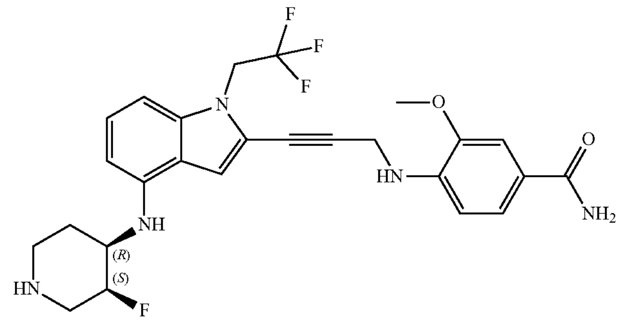 | 4-{3-(4-{[(3S,4R)-3-fluoropiperidin-4-yl]amino}-1-(2,2,2-trifluoroethyl)-1H-indol-2-yl)prop-2-yn-1-yl]amino}-3-methoxybenzamide | 518.2 |
| 850A | 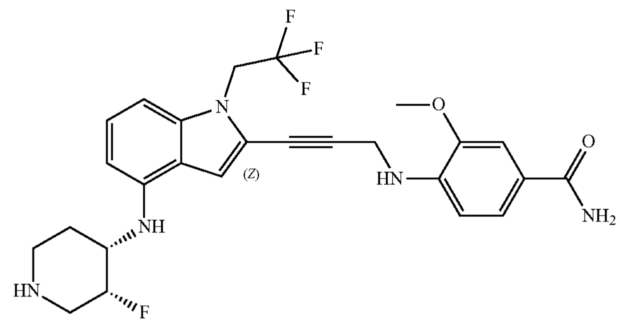 | 4-((3-(4-(((3R,4S)-3-fluoropiperidin-4-yl)amino)-1-(2,2,2-trifluoroethyl)-1H-indol-2-yl)prop-2-yn-1-yl)amino)-3-methoxybenzamide | 518.2 |
| 851A | 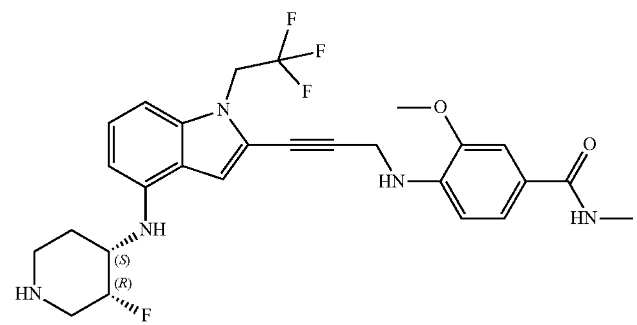 | 4-{3-(4-{[(3R,4S)-3-fluoropiperidin-4-yl]amino}-1-(2,2,2-trifluoroethyl)-1H-indol-2-yl)prop-2-yn-1-yl]amino}-3-methoxy-N-methylbenzamide | 532.2 |

TABLE 4-continued

| Compound No. | Structure | IUPAC | LC-MS (ES+, m/z) |
|---|---|---|---|
| 852A | 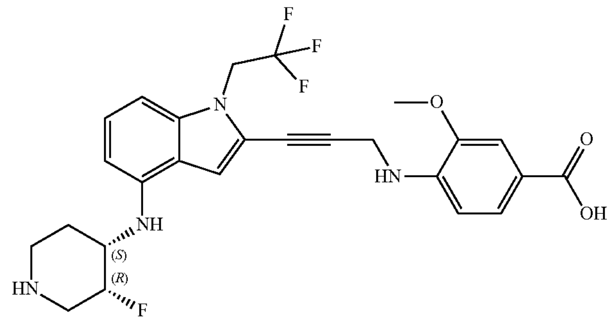 | 4-{[3-(4-{[(3R,4S)-3-fluoropiperidin-4-yl]amino}-1-(2,2,2-trifluoroethyl)-1H-indol-2-yl)prop-2-yn-1-yl]amino}-3-methoxybenzoic acid | 519.2 |
| 853A | 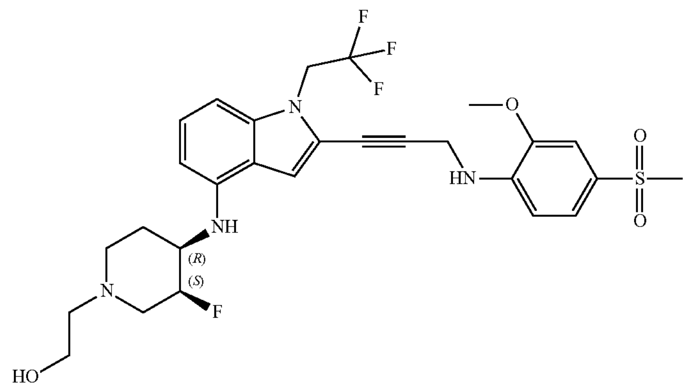 | 2-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-ol | 597.2 |
| 854A | 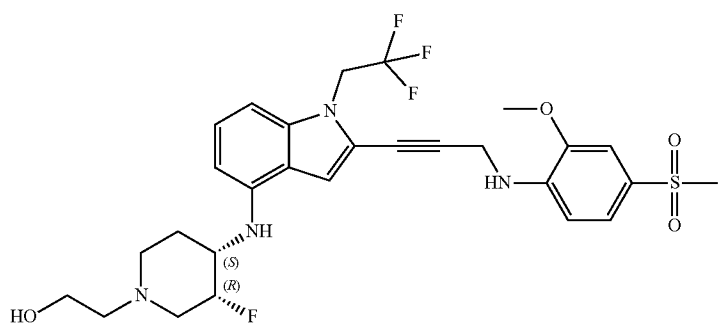 | 2-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-ol | 597.2 |

TABLE 4-continued
| Compound No. | Structure | IUPAC | LC-MS (ES+, m/z) |
|---|---|---|---|
| 855A | 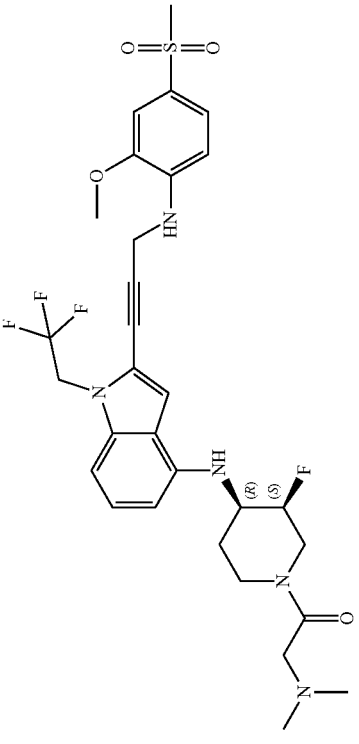 | 2-(dimethylamino)-1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one | 638.3 |
| 856A | 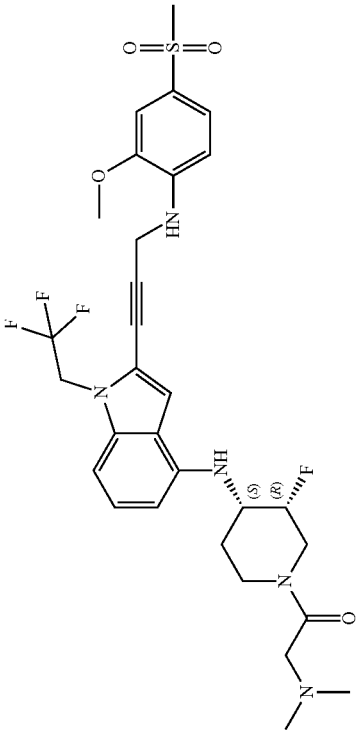 | 2-(dimethylamino)-1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one | 638.3 |

TABLE 4-continued

| Compound No. | Structure | IUPAC | LC-MS (ES+, m/z) |
|---|---|---|---|
| 857A | 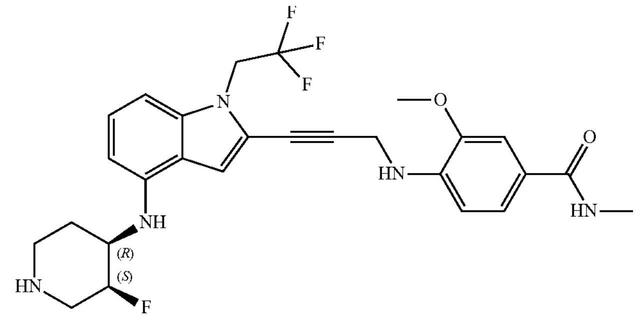 | 4-{3-(4-{[(3S,4R)-3-fluoropiperidin-4-yl]amino}-1-(2,2,2-trifluoroethyl)-1H-indol-2-yl)prop-2-yn-1-yl]amino}-3-methoxy-N-methylbenzamide | 532.2 |
| 858A | 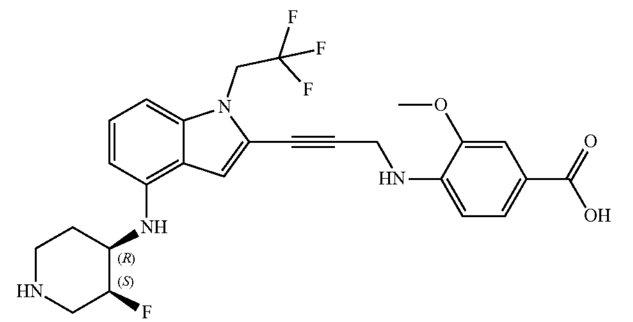 | 4-{3-(4-{[(3S,4R)-3-fluoropiperidin-4-yl]amino}-1-(2,2,2-trifluoroethyl)-1H-indol-2-yl)prop-2-yn-1-yl]amino}-3-methoxybenzoic acid | 519.2 |
| 859A | 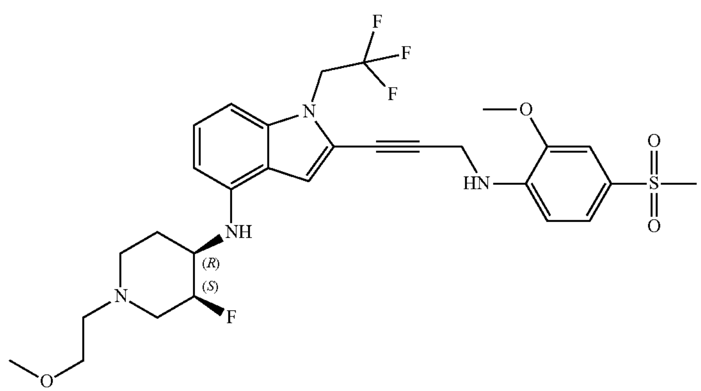 | N-[(3S,4R)-3-fluoro-1-(2-methoxyethyl)piperidin-4-yl]-2-{3-[(4-methanesulfonyl-2-methoxyphenyl)amino]prop-1-yn-1-yl}-1-(2,2,2-trifluoroethyl)-1H-indol-4-amine | 611.2 |

| Compound No. | Structure | IUPAC | LC-MS (ES+, m/z) |
|---|---|---|---|
| 860A | 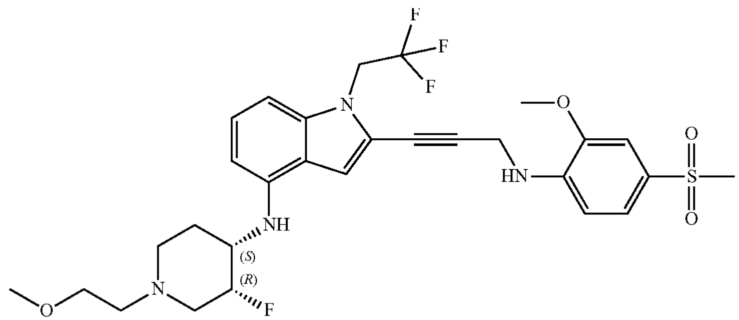 | N-[(3R,4S)-3-fluoro-1-(2-methoxyethyl)piperidin-4-yl]-2-{3-[(4-methanesulfonyl)-2-methoxyphenyl)amino]prop-1-yn-1-yl}-1-(2,2,2-trifluoroethyl)-1H-indol-4-amine | 611.2 |
| 861A | 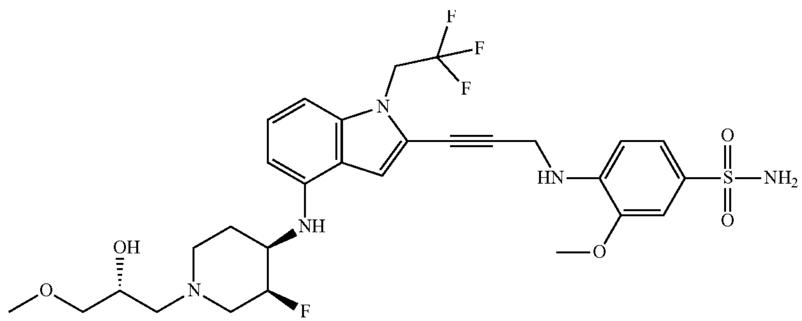 [SMILES: COC[C@H](O)CN1CC[C@@H](Nc2cccc3c2cc(C#CCNc2ccc(S(N)(=O)=O)cc2OC)n3CC(F)(F)F)[C@@H](F)C1] | 4-[{3-(4-{[(3S,4R)-3-fluoro-1-[(2R)-2-hydroxy-3-methoxypropyl]piperidin-4-yl]amino}-1-(2,2,2-trifluoroethyl)-1H-indol-2-yl)prop-2-yn-1-yl]amino]-3-methoxybenzene-1-sulfonamide | 624.3 |
| 862A | 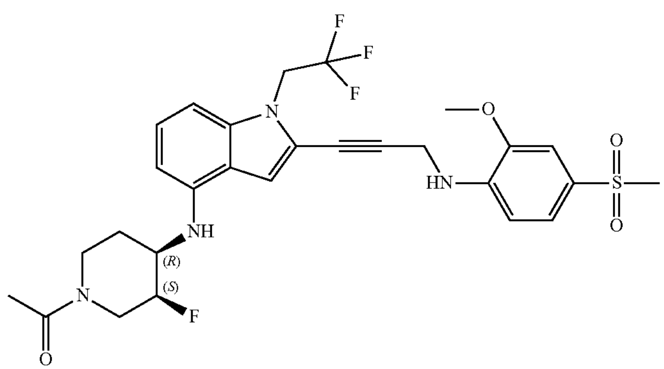 | 1-[(3S,4R)-3-fluoro-4-[(2-{3-[(4-methanesulfonyl)-2-methoxyphenyl)amino]prop-1-yn-1-yl}-1-(2,2,2-trifluoroethyl)-1H-indol-4-yl)amino]piperidin-1-yl]ethan-1-one | 595.2 |

TABLE 4-continued

| Compound No. | Structure | IUPAC | LC-MS (ES+, m/z) |
|---|---|---|---|
| 863A | 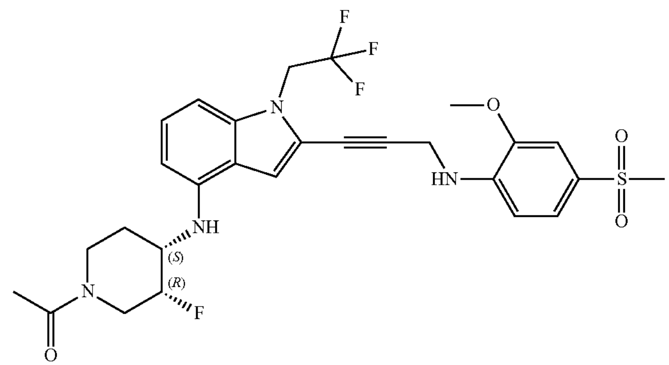 | 1-[(3R,4S)-3-fluoro-4-[(2-{3-[(4-methanesulfonyl-2-methoxyphenyl)amino]prop-1-yn-1-yl]-1-(2,2,2-trifluoroethyl)-1H-indol-4-yl)amino]piperidin-1-yl]ethan-1-one | 595.2 |
| 864A | 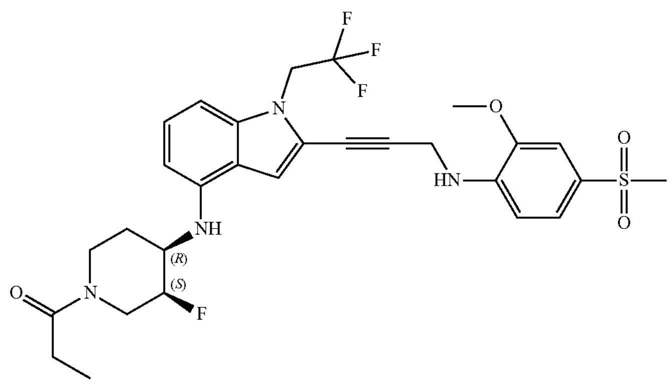 | 1-[(3S,4R)-3-fluoro-4-[(2-{3-[(4-methanesulfonyl-2-methoxyphenyl)amino]prop-1-yn-1-yl]-1-(2,2,2-trifluoroethyl)-1H-indol-4-yl)amino]piperidin-1-yl]propan-1-one | 609.3 |

| Compound No. | Structure | IUPAC | LC-MS (ES+, m/z) |
|---|---|---|---|
| 865A | 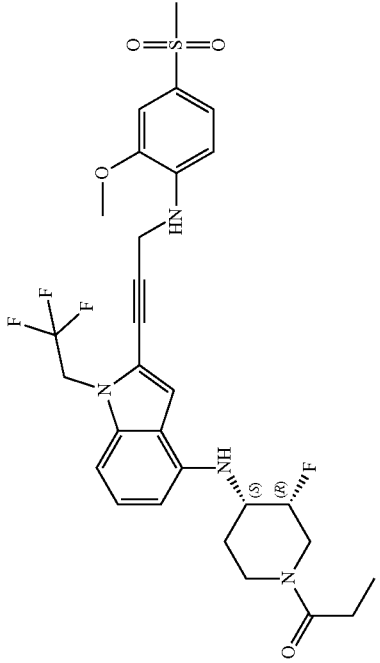 | 1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]propan-1-one | 609.3 |
| 866A | 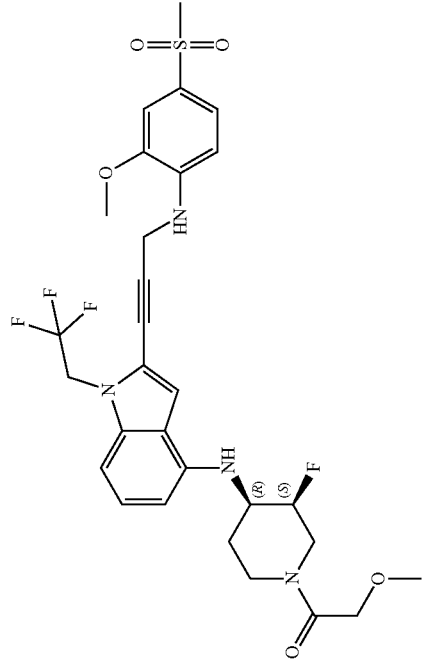 | 1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]-2-methoxyethan-1-one | 625.3 |

TABLE 4-continued
| Compound No. | Structure | IUPAC | LC-MS (ES+, m/z) |
|---|---|---|---|
| 867A | 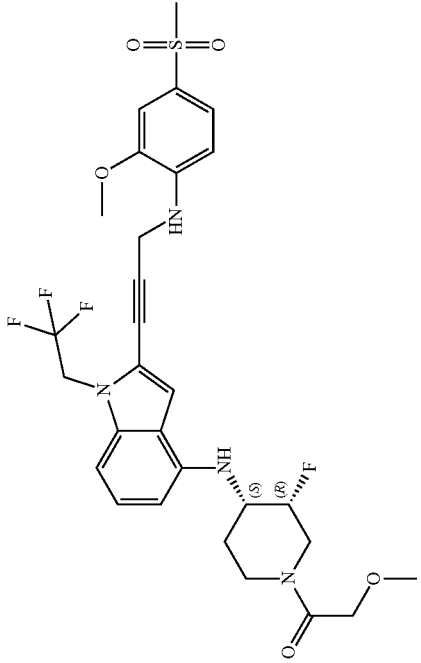 | 1-{[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]-2-methoxyethan-1-one | 625.3 |
| 868A | 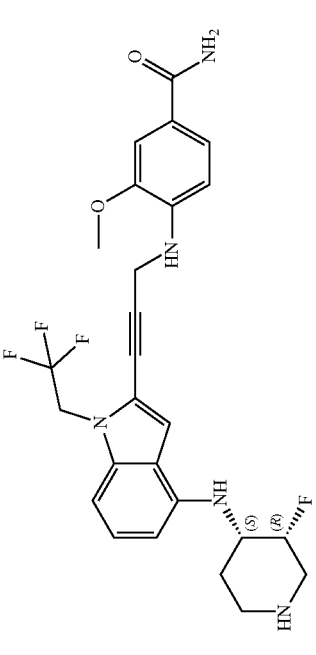 | 4-{[3-(4-{[(3R,4S)-3-fluoropiperidin-4-yl]amino}-1-(2,2,2-trifluoroethyl)-1H-indol-2-yl)prop-2-yn-1-yl]amino}-3-methoxybenzamide | 518.3 |

TABLE 4-continued

| Compound No. | Structure | IUPAC | LC-MS (ES+, m/z) |
|---|---|---|---|
| 869A | 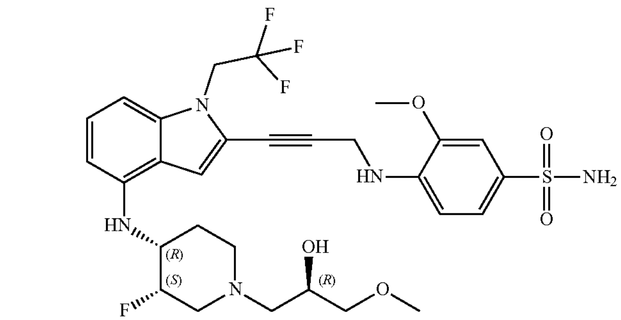 | 4-[3-(4-{[(3R,4S)-3-fluoro-1-[(2R)-2-hydroxy-3-methoxypropyl]piperidin-4-yl]amino}-1-(2,2,2-trifluoroethyl)-1H-indol-2-yl)prop-2-yn-1-yl]amino}-3-methoxybenzene-1-sulfonamide | 642.3 |
| 870A | 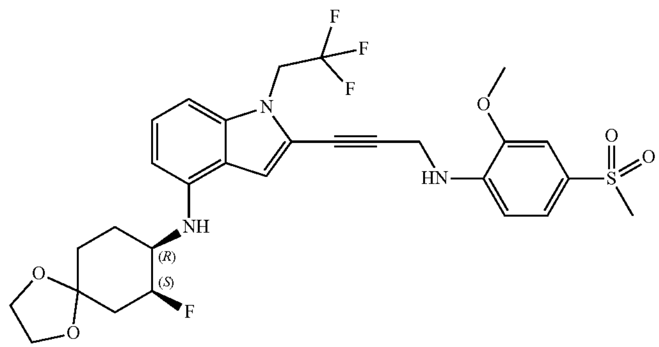 | N-[(7S,8R)-7-fluoro-1,4-dioxaspiro[4.5]decan-8-yl]-2-{3-[(4-methanesulfonyl-2-methoxyphenyl)amino]prop-1-yn-1-yl}-1-(2,2,2-trifluoroethyl)-1H-indol-4-amine | 610.2 |
| 871A | 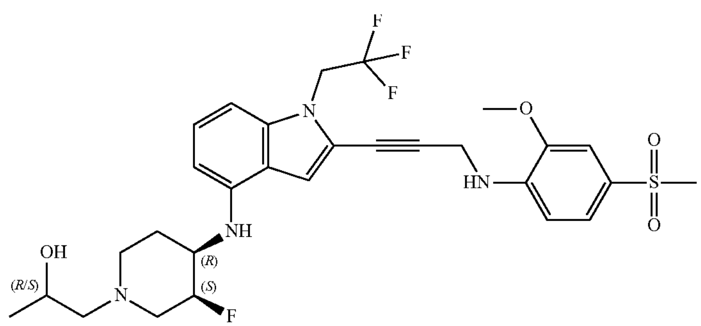 | 1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]propan-2-ol | 611.2 |

TABLE 4-continued

| Compound No. | Structure | IUPAC | LC-MS (ES+, m/z) |
|---|---|---|---|
| 872A | 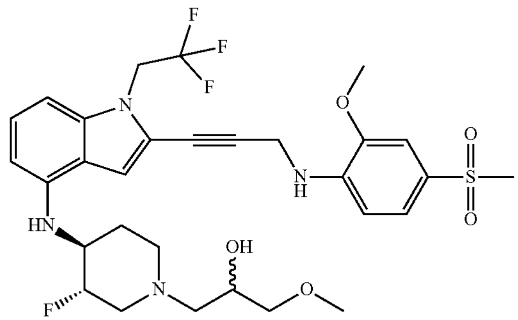 [SMILES: COCC(O)CN1CC[C@H](Nc2cccc3c2cc(C#CCNc2ccc(S(C)(=O)=O)cc2OC)n3CC(F)(F)F)[C@@H](F)C1] | 1-((3S,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol | 641.2 |
| 873A | 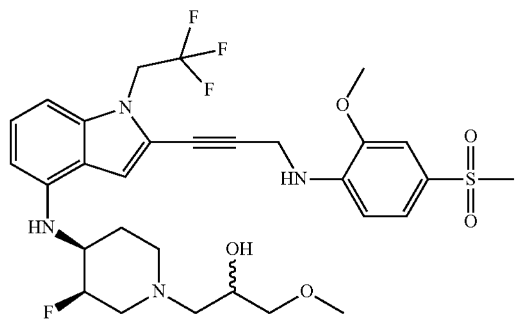 [SMILES: COCC(O)CN1CC[C@H](Nc2cccc3c2cc(C#CCNc2ccc(S(C)(=O)=O)cc2OC)n3CC(F)(F)F)[C@H](F)C1] | 1-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol | 641.2 |
| 874A | 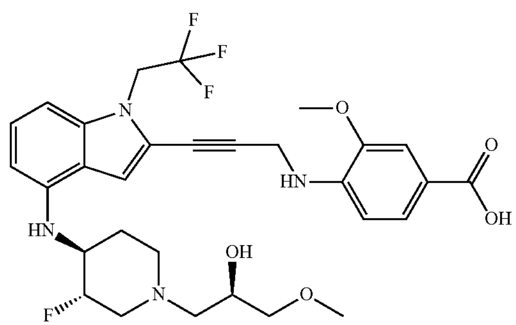 | 4-(3-(4-(((3S,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid | 607.3 |

TABLE 4-continued

| Compound No. | Structure | IUPAC | LC-MS (ES+, m/z) |
|---|---|---|---|
| 875A | 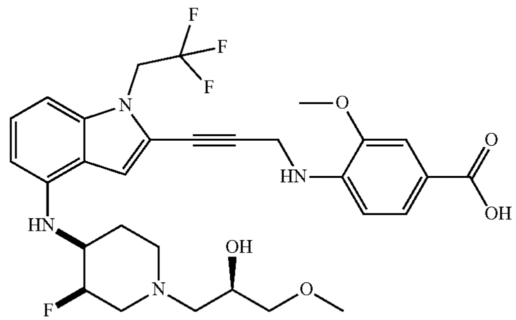 | 4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid | 607.2 |
| 876A | 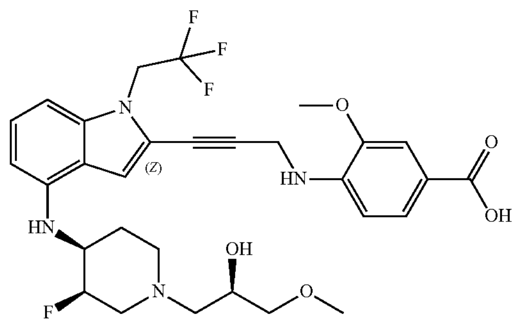 [SMILES: COC[C@H](O)CN1CC[C@H](Nc2cccc3c2cc(C#CCNc2ccc(C(=O)O)cc2OC)n3CC(F)(F)F)[C@H](F)C1] | 4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid | 607.3 |
| 877A | 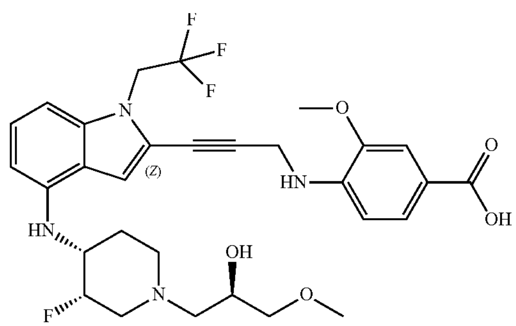 | 4-((3-(4-(((3S,4R)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid | 607.3 |

TABLE 4-continued

| Compound No. | Structure | IUPAC | LC-MS (ES⁺, m/z) |
|---|---|---|---|
| 878A | 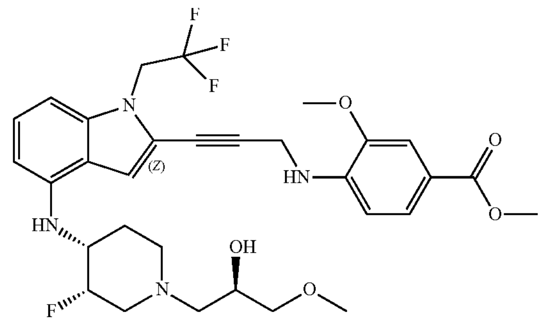 | methyl 4-((3-(4-(((3S,4R)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoate | 621.3 |
| 879A | 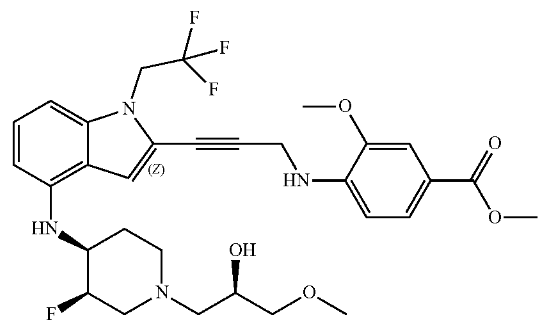 | methyl 4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoate | 621.4 |
| 880A | 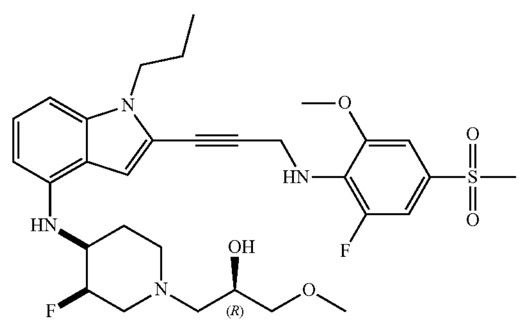 | (R)-1-((3R,4S)-3-fluoro-4-((2-(3-((2-fluoro-6-methoxy-4-(methylsulfonyl)phenyl)amino)prop-1-yn-1-yl)-1-propyl-1H-indol-4-yl)amino)piperidin-1-yl)-3-methoxypropan-2-ol | 619.3 |

| Compound No. | Structure | IUPAC | LC-MS (ES+, m/z) |
|---|---|---|---|
| 881A | 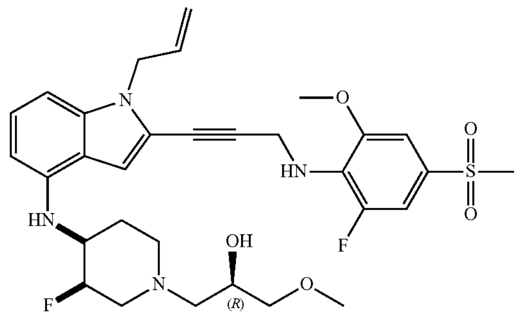 | (R)-1-((3R,4S)-4-((1-allyl-2-(3-((2-fluoro-6-methoxy-4-(methylsulfonyl)phenyl)amino)prop-1-yn-1-yl)-1H-indol-4-yl)amino)-3-fluoropiperidin-1-yl)-3-methoxypropan-2-ol | 599.3 |
| 882A | 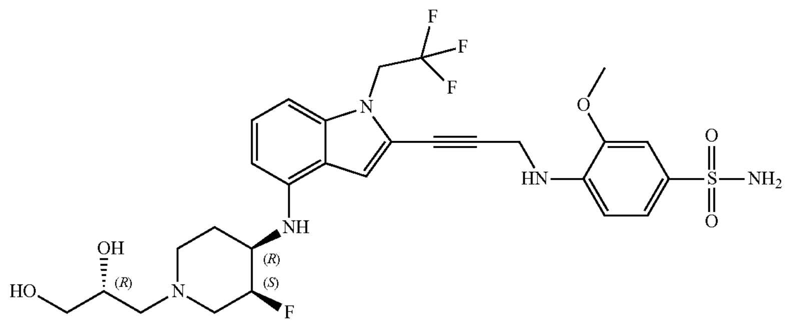 | 4-{[3-(4-{[(3S,4R)-1-[(2R)-2,3-dihydroxypropyl]-3-fluoropiperidin-4-yl]amino}-1-(2,2,2-trifluoroethyl)-1H-indol-2-yl)prop-2-yn-1-yl]amino}-3-methoxybenzene-1-sulfonamide | 628.3 |
| 883A | 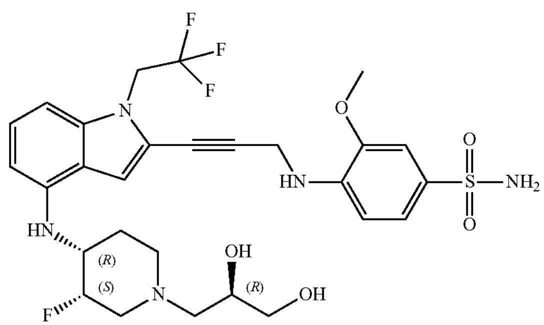 | 4-{[3-(4-{[(3R,4S)-1-[(2R)-2,3-dihydroxypropyl]-3-fluoropiperidin-4-yl]amino}-1-(2,2,2-trifluoroethyl)-1H-indol-2-yl)prop-2-yn-1-yl]amino}-3-methoxybenzene-1-sulfonamide | 628.3 |

TABLE 4-continued

| Compound No. | Structure | IUPAC | LC-MS (ES+, m/z) |
|---|---|---|---|
| 884A | 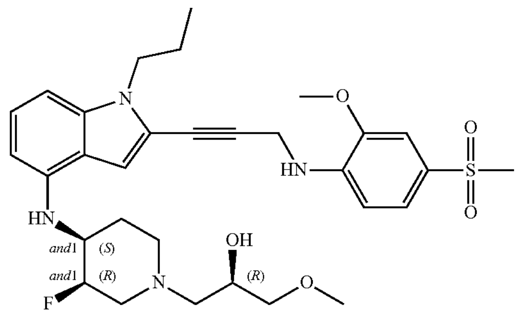 | (2R)-1-[(3RS,4SR)-3-fluoro-4-[(2-{3-[(4-methanesulfonyl-2-methoxyphenyl)amino]prop-1-yn-1-yl}-1-propyl-1H-indol-4-yl)amino]piperidin-1-yl]-3-methoxypropan-2-ol | 601.2 |
| 885A | 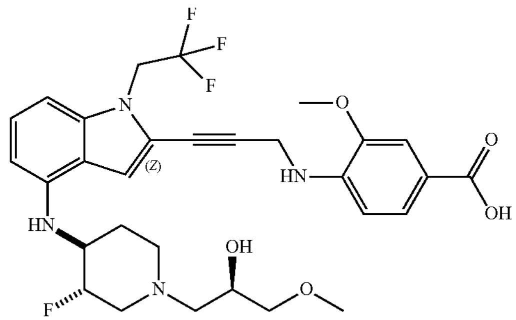 | 4-((3-(4-(((3S,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid | |
| 886A | 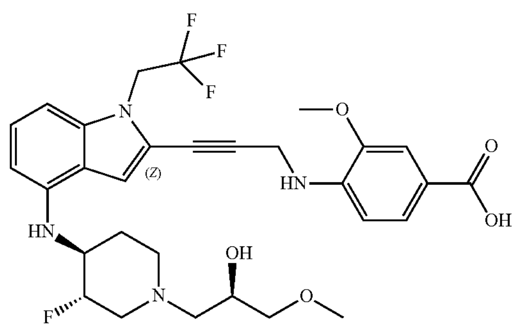 | 4-((3-(4-(((3S,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid | 607.2 |

TABLE 4-continued

| Compound No. | Structure | IUPAC | LC-MS (ES+, m/z) |
|---|---|---|---|
| 887A | 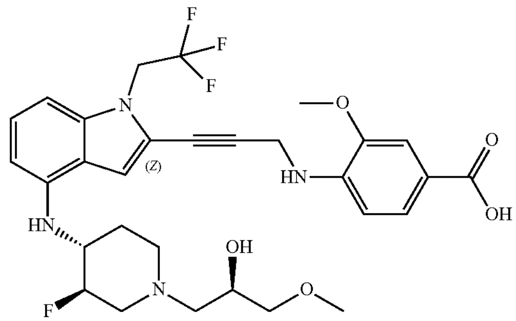 | 4-((3-(4-(((3R,4R)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid | 607.2 |
| 888A | 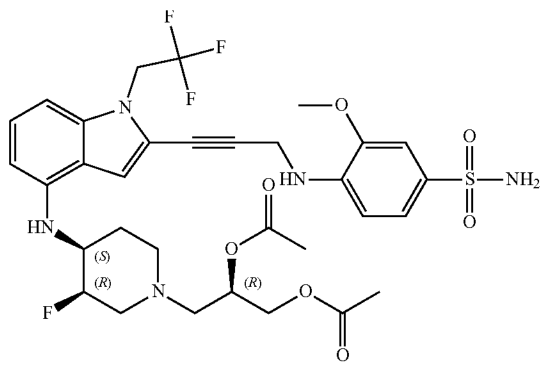 | (2R)-1-(acetyloxy)-3-[(3R,4S)-3-fluoro-4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl]propan-2-yl acetate | 712.2 |
| 889A | 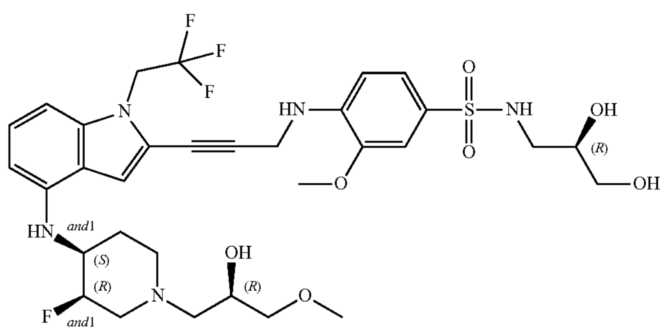 | N-[(2R)-2,3-dihydroxypropyl]-4-{[3-(4-{[(3RS,4SR)-3-fluoro-1-[(2R)-2-hydroxy-3-methoxypropyl]piperidin-4-yl]amino}-1-(2,2,2-trifluoroethyl)-1H-indol-2-yl)prop-2-yn-1-yl]amino}-3-methoxybenzene-1-sulfonamide | 702.2 M-Me |

TABLE 4-continued
| Compound No. | Structure | IUPAC | LC-MS (ES+, m/z) |
|---|---|---|---|
| 890A | 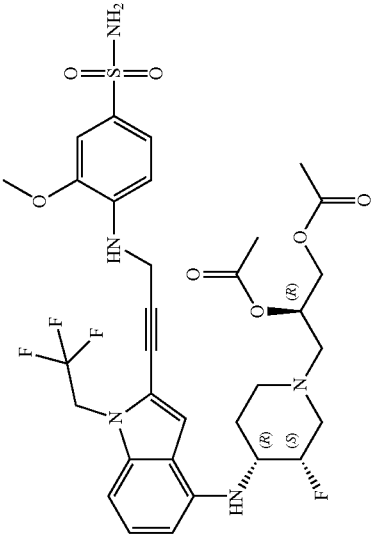 | (2R)-1-(acetyloxy)-3-[(3S,4R)-3-fluoro-4-[(2-{3-[(2-methoxy-4-sulfamoylphenyl)amino]prop-1-yn-1-yl}-1-(2,2,2-trifluoroethyl)-1H-indol-4-yl]amino]piperidin-1-yl] propan-2-yl acetate | 712.3 |
| 891A | 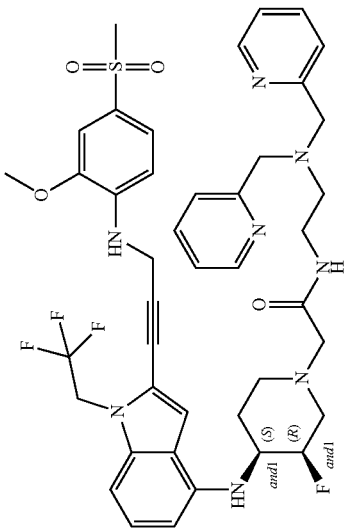 | rac-N-(2-{bis[(pyridin-2-yl)methyl]amino}ethyl)-2-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl]amino]piperidin-1-yl]acetamide | 835.2 |

TABLE 4-continued
| Compound No. | Structure | IUPAC | LC-MS (ES+, m/z) |
|---|---|---|---|
| 892A | 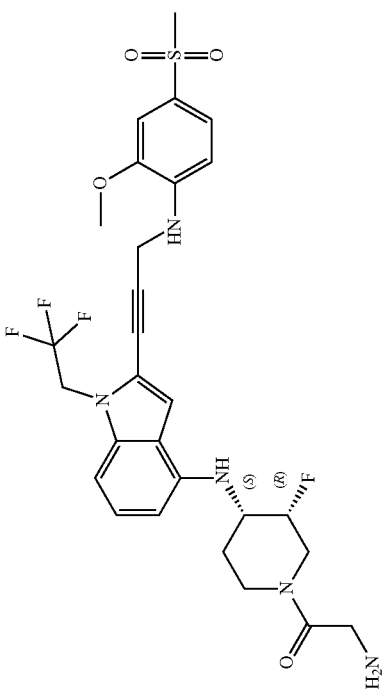 | 2-amino-1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one | 610.2 |
| 893A | 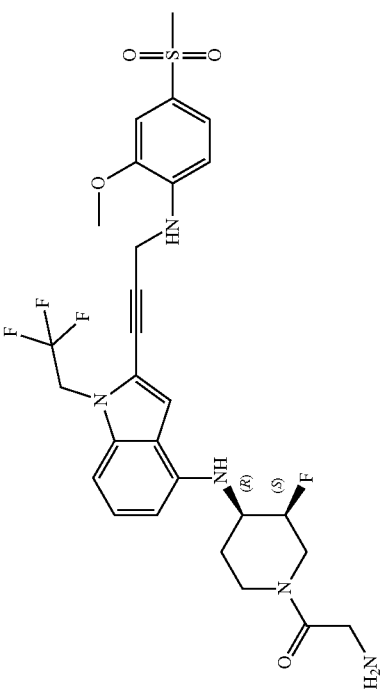 | 2-amino-1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one | 610.2 |

| Compound No. | Structure | IUPAC | LC-MS (ES+, m/z) |
|---|---|---|---|
| 894A | 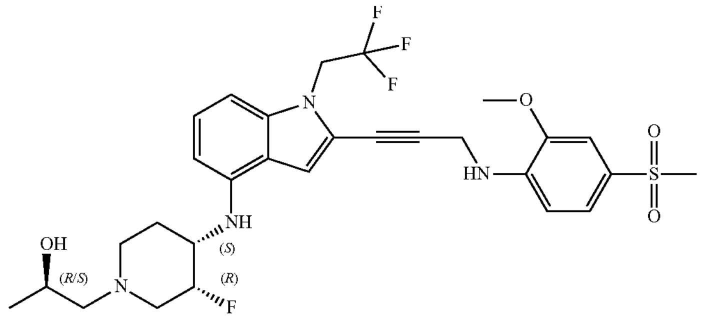 | 1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]propan-2-ol | 611.2 |
| 895A | 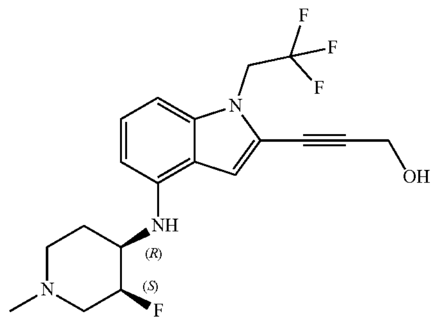 | 3-(4-(((3S,4R)-3-fluoro-1-methylpiperidin-4-yl)amino)-1-(2,2,2-trifluoroethyl)-1H-indol-2-yl)prop-2-yn-1-ol | 384.1 |
| 896A | 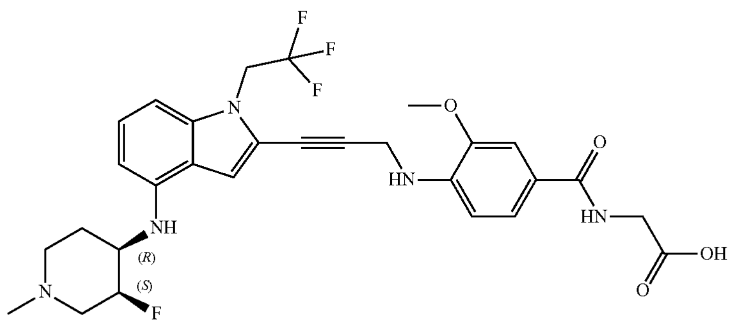 | (4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoyl)glycine | 590.2 |

TABLE 4-continued

| Compound No. | Structure | IUPAC | LC-MS (ES+, m/z) |
|---|---|---|---|
| 897A | 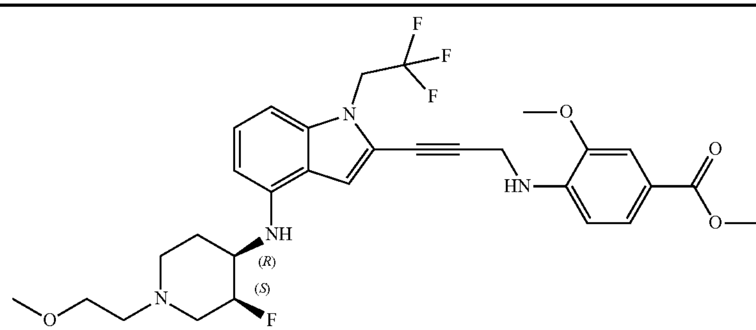 | methyl 4-{[3-(4-{[(3S,4R)-3-fluoro-1-(2-methoxyethyl)piperidin-4-yl]amino}-1-(2,2,2-trifluoroethyl)-1H-indol-2-yl)prop-2-yn-1-yl]amino}-3-methoxybenzoate | 591.3 |
| 898A | 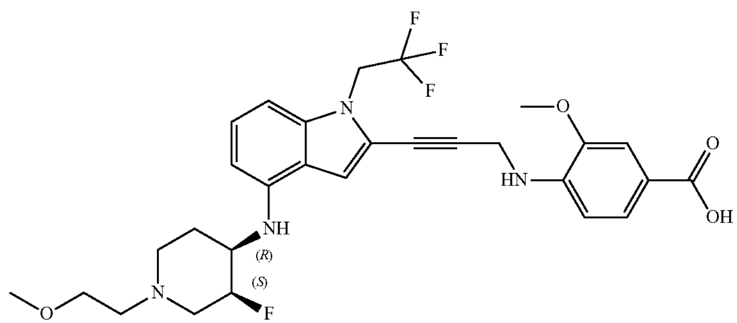 | 4-{[3-(4-{[(3S,4R)-3-fluoro-1-(2-methoxyethyl)piperidin-4-yl]amino}-1-(2,2,2-trifluoroethyl)-1H-indol-2-yl)prop-2-yn-1-yl]amino}-3-methoxybenzoic acid | 577.2 |
| 899A | 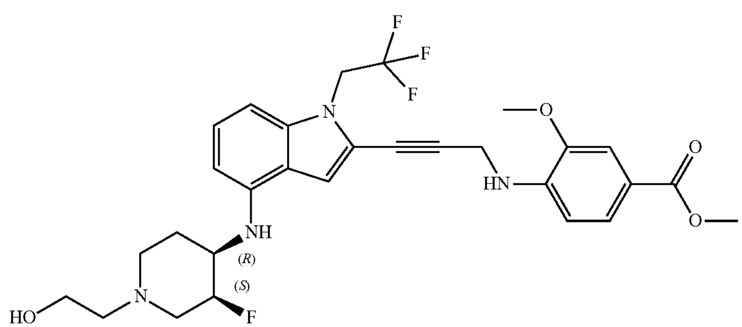 | methyl 4-{[3-(4-{[(3S,4R)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoate | 577.3 |

TABLE 4-continued

| Compound No. | Structure | IUPAC | LC-MS (ES+, m/z) |
|---|---|---|---|
| 900A | 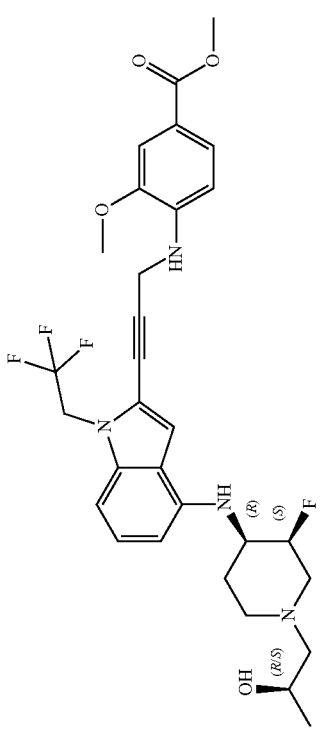 | methyl 4-{[3-(4-{[(3S,4R)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoate | 591.2 |
| 901A | 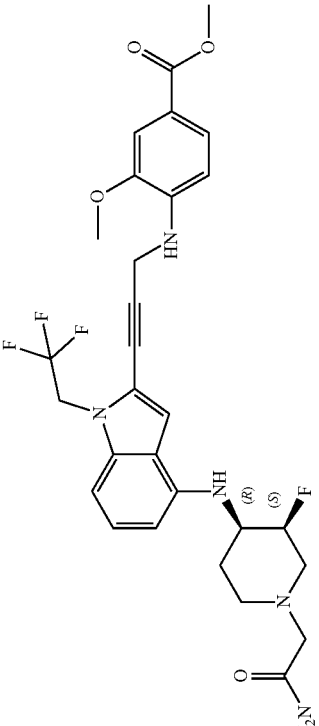 | methyl 4-{[3-(4-{[(3S,4R)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoate | 590.2 |
| 902A | 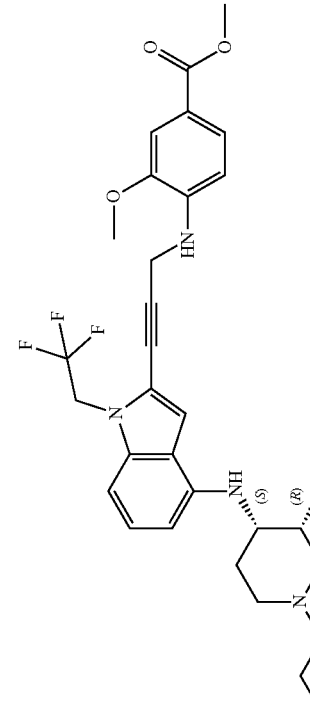 | methyl 4-{[3-(4-{[(3R,4S)-3-fluoro-1-(2-methoxyethyl)piperidin-4-yl]amino}-1-(2,2,2-trifluoroethyl)-1H-indol-2-yl)prop-2-yn-1-yl]amino}-3-methoxybenzoate | 591.3 |

TABLE 4-continued

| Compound No. | Structure | IUPAC | LC-MS (ES+, m/z) |
|---|---|---|---|
| 903A | 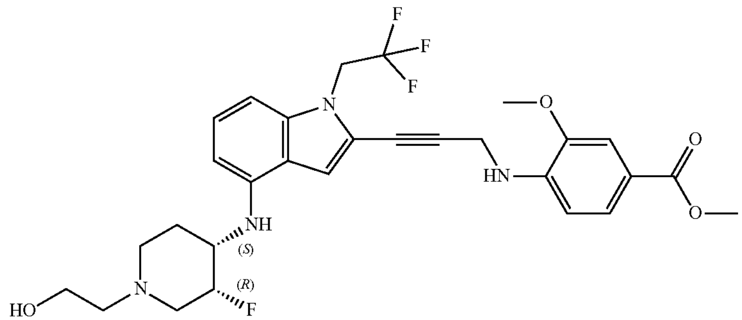 | methyl 4-{[3-(4-{[(3R,4S)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoate | 577.2 |
| 904A | 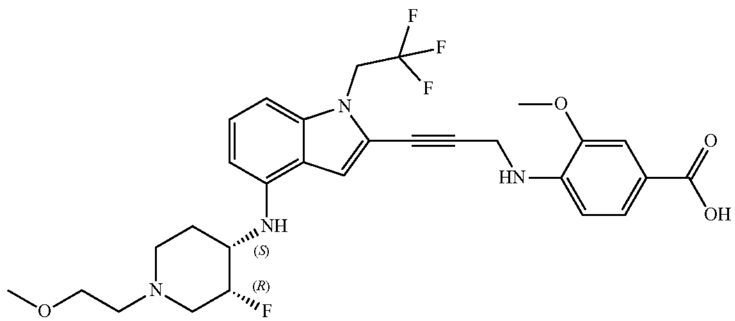 | 4-{[3-(4-{[(3R,4S)-3-fluoro-1-(2-methoxyethyl)piperidin-4-yl]amino}-1-(2,2,2-trifluoroethyl)-1H-indol-2-yl)prop-2-yn-1-yl]amino}-3-methoxybenzoic acid | 577.3 |
| 905A | 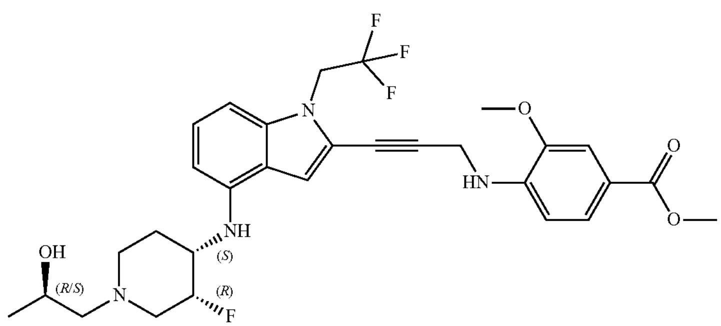 | methyl 4-{[3-(4-{[(3R,4S)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoate | 591.3 |

TABLE 4-continued

| Compound No. | Structure | IUPAC | LC-MS (ES+, m/z) |
|---|---|---|---|
| 906A | 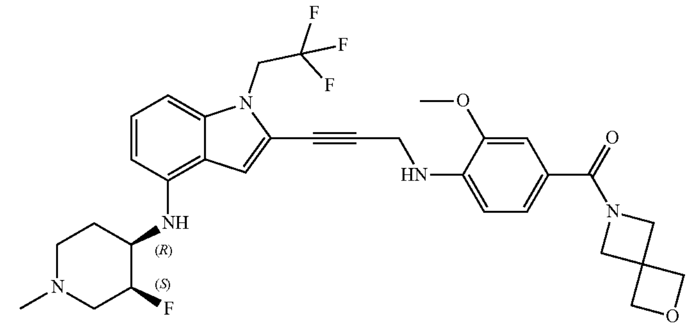 | N-[(3S,4R)-3-fluoro-1-methylpiperidin-4-yl]-2-{3-[(2-methoxy-4-{2-oxa-6-azaspiro[3.3]heptane-6-carbonyl}phenyl)amino]prop-1-yn-1-yl}-1-(2,2,2-trifluoroethyl)-1H-indol-4-amine | 614.3 |
| 907A | 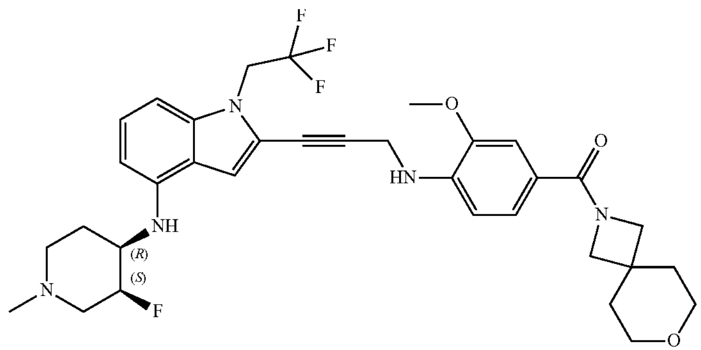 | N-[(3S,4R)-3-fluoro-1-methylpiperidin-4-yl]-2-{3-[(2-methoxy-4-{7-oxa-2-azaspiro[3.5]nonane-2-carbonyl}phenyl)amino]prop-1-yn-1-yl}-1-(2,2,2-trifluoroethyl)-1H-indol-4-amine | 642.3 |
| 908A | 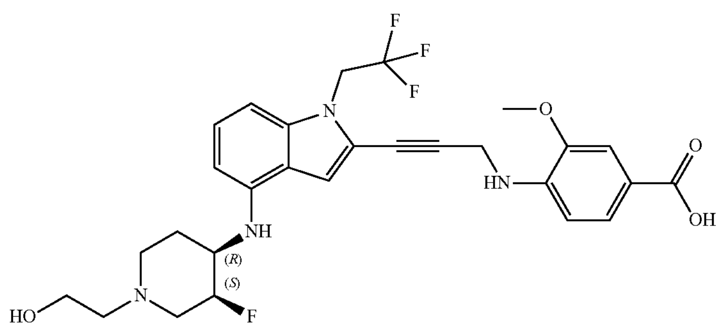 | 4-[{3-(4-{[(3S,4R)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoic acid | 563.2 |

TABLE 4-continued

| Compound No. | Structure | IUPAC | LC-MS (ES+, m/z) |
|---|---|---|---|
| 909A | 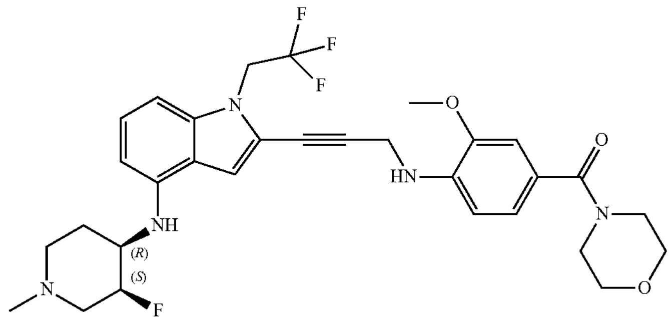 | N-[(3S,4R)-3-fluoro-1-methylpiperidin-4-yl]-2-(3-{[2-methoxy-4-(morpholine-4-carbonyl)phenyl]amino}prop-1-yn-1-yl)-1-(2,2,2-trifluoroethyl)-1H-indol-4-amine | 602.3 |
| 910A | 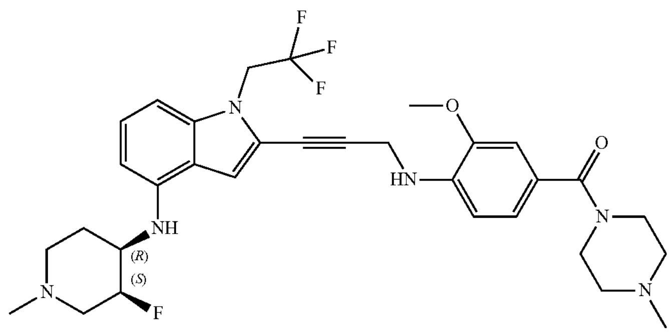 | N-[(3S,4R)-3-fluoro-1-methylpiperidin-4-yl]-2-(3-{[2-methoxy-4-(4-methylpiperazine-1-carbonyl)phenyl]amino}prop-1-yn1-yl)-1-(2,2,2-trifluoroethyl)-1H-indol-4-amine | 615.4 |
| 911A | 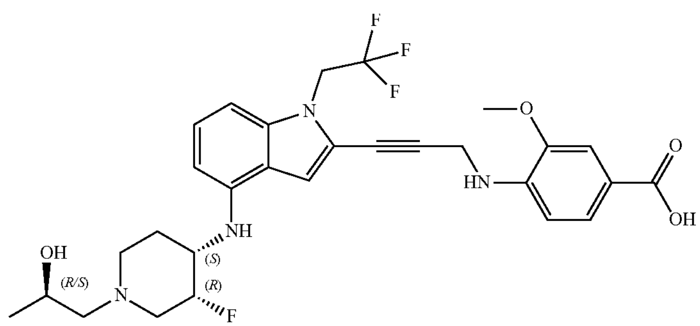 | 4-{[3-(4-{[(3R,4S)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoic acid | 577.3 |

TABLE 4-continued
| Compound No. | Structure | IUPAC | LC-MS (ES+, m/z) |
|---|---|---|---|
| 912A | 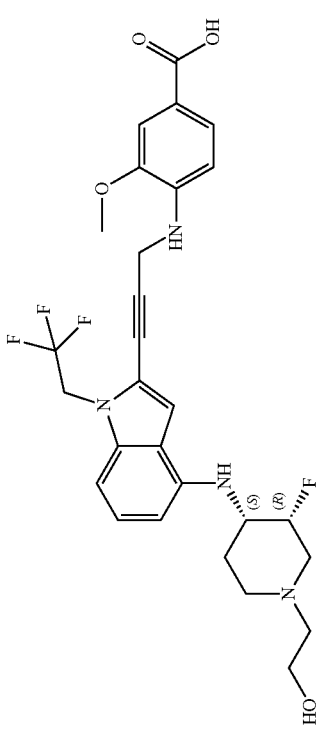 | 4-{[3-(4-{[(3R,4S)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoic acid | 563.2 |
| 913A | 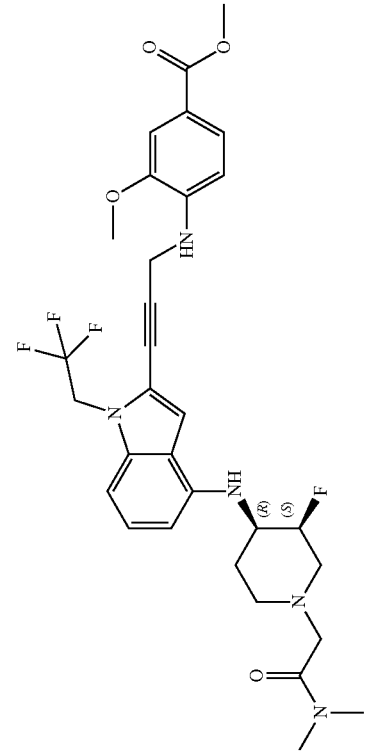 | methyl 4-{[3-(4-{[(3S,4R)-1-[(dimethylcarbamoyl)methyl]-3-fluoropiperidin-4-yl]amino}-1-(2,2,2-trifluoroethyl)-1H-indol-2-yl)prop-2-yn-1-yl]amino}-3-methoxybenzoate | 618.3 |

TABLE 4-continued

| Compound No. | Structure | IUPAC | LC-MS (ES+, m/z) |
|---|---|---|---|
| 914A | 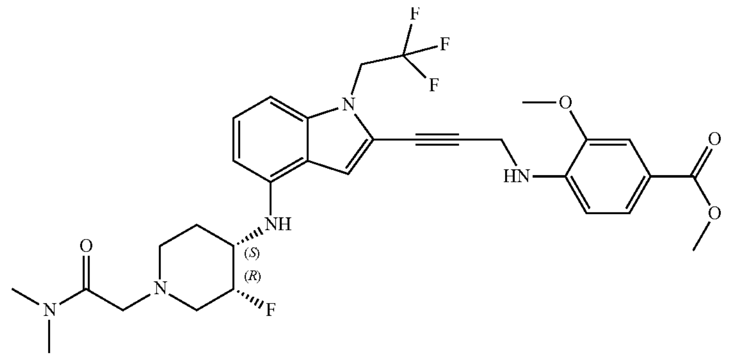 | methyl 4-{[3-(4-{[(3R,4S)-1-[(dimethylcarbamoyl)methyl]-3-fluoropiperidin-4-yl]amino}-1-(2,2,2-trifluoroethyl)-1H-indol-2-yl]prop-2-yn-1-yl]amino}-3-methoxybenzoate | 618.3 |
| 915A | 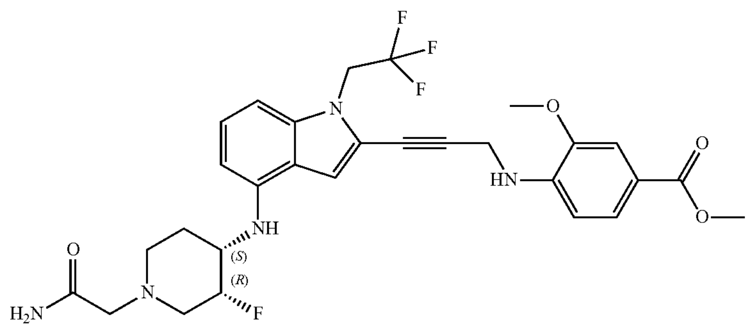 | methyl 4-{[3-(4-{[(3R,4S)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoate | 590.2 |
| 916A | 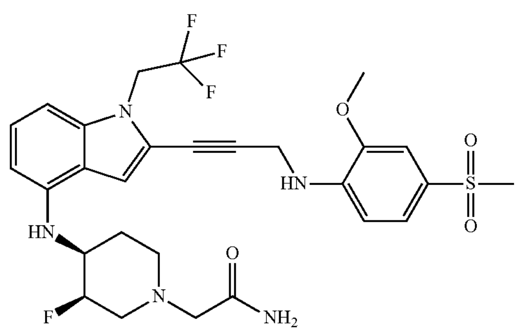 [SMILES: COc1cc(S(C)(=O)=O)ccc1NCC#Cc1cc2c(N[C@H]3CCN(CC(N)=O)C[C@H]3F)cccc2n1CC(F)(F)F] | 2-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)acetamide | 610.2 |

TABLE 4-continued

| Compound No. | Structure | IUPAC | LC-MS (ES+, m/z) |
|---|---|---|---|
| 917A | 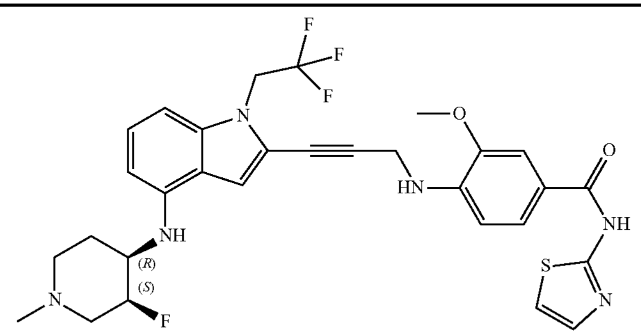 | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(1,3-thiazol-2-yl)benzamide | 615.2 |
| 918A | 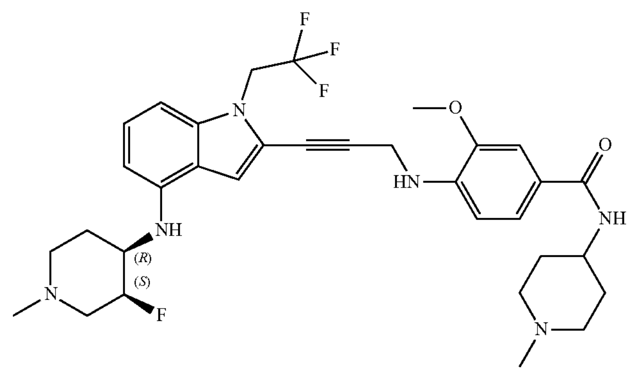 | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(1-methylpiperidin-4-yl)benzamide | 629.3 |
| 919A | 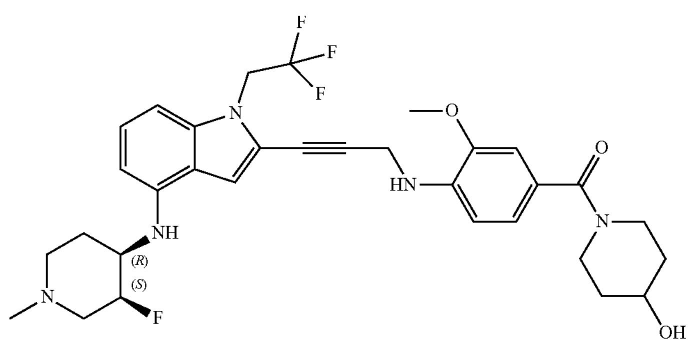 | 1-(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoyl)piperidin-4-ol | 616.3 |

TABLE 4-continued

| Compound No. | Structure | IUPAC | LC-MS (ES+; m/z) |
|---|---|---|---|
| 920A | 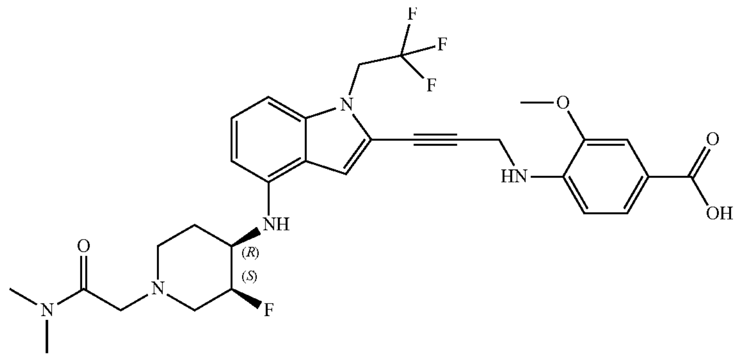 | 4-{[3-(4-{[(3S,4R)-1-[(dimethylcarbamoyl)methyl]-3-fluoropiperidin-4-yl]amino}-1-(2,2,2-trifluoroethyl)-1H-indol-2-yl)prop-2-yn-1-yl]amino}-3-methoxybenzoic acid | 604.3 |
| 921A | 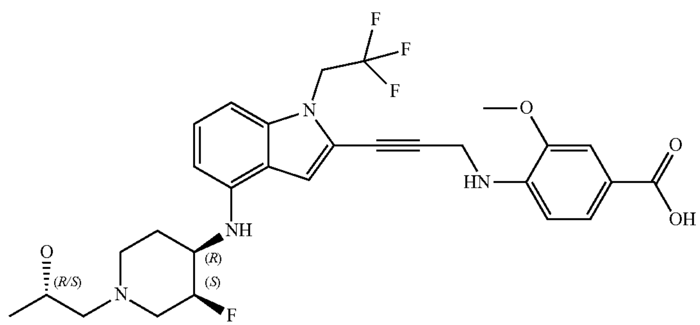 | 4-{[3-(4-{[(3S,4R)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoic acid | 577.3 |

TABLE 4-continued

| Compound No. | Structure | IUPAC | LC-MS (ES+, m/z) |
|---|---|---|---|
| 922A | 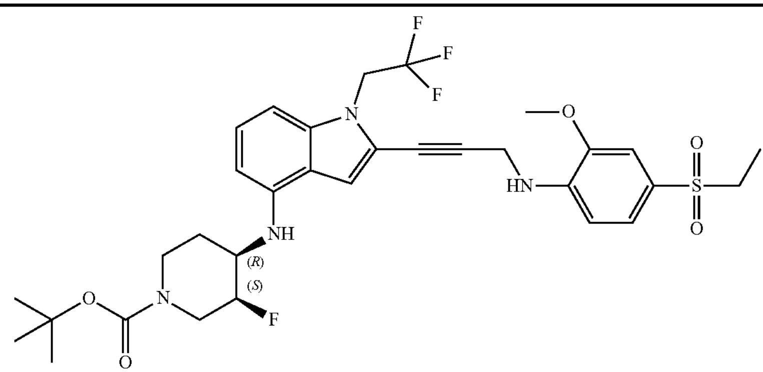 | tert-butyl (3S,4R)-4-{[2-(3-{[4-(ethanesulfonyl)-2-methoxyphenyl]amino}prop-1-yn-1-yl)-1-(2,2,2-trifluoroethyl)-1H-indol-4-yl]amino}-3-fluoropiperidine-1-carboxylate | 667.3 |
| 923A | 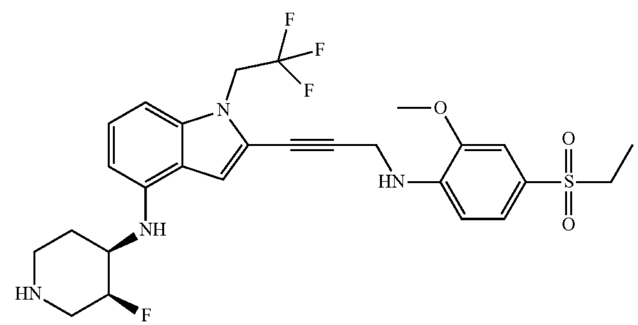 [SMILES: CCS(=O)(=O)c1ccc(NCC#Cc2cc3c(N[C@@H]4CCNC[C@@H]4F)cccc3n2CC(F)(F)F)c(OC)c1] | 2-(3-((4-(ethylsulfonyl)-2-methoxyphenyl)amino)prop-1-yn-1-yl)-N-((3S,4R)-3-fluoropiperidin-4-yl)-1-(2,2,2-trifluoroethyl)-1H-indol-4-amine | 567.2 |
| 924A | 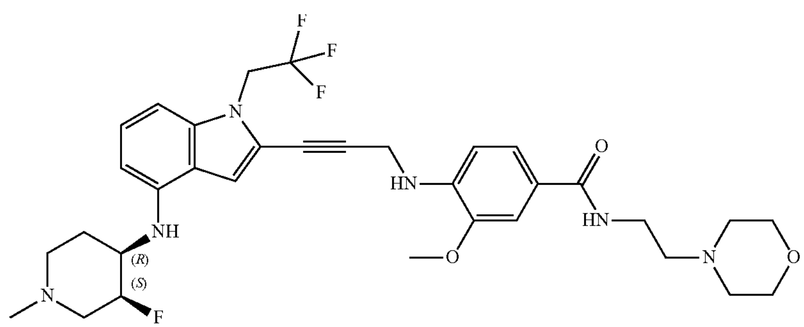 | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-[2-(morpholin-4-yl)ethyl]benzamide | 645.4 |

TABLE 4-continued

| Compound No. | Structure | IUPAC | LC-MS (ES+, m/z) |
|---|---|---|---|
| 925A | 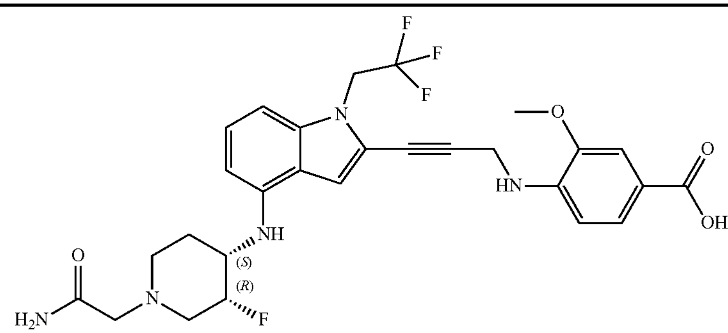 | 4-{[3-(4-{[(3R,4S)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoic acid | 576.3 |
| 926A | 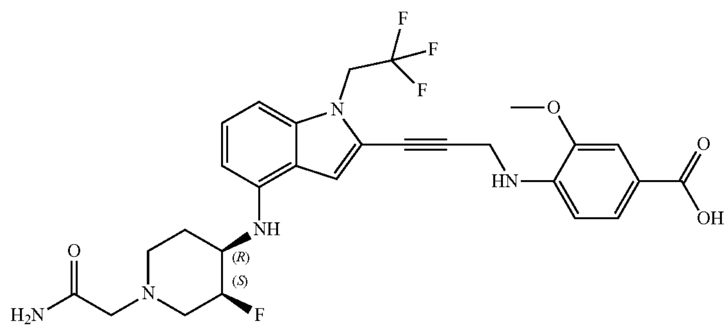 | 4-{[3-(4-{[(3S,4R)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoic acid | 576.2 |
| 927A | 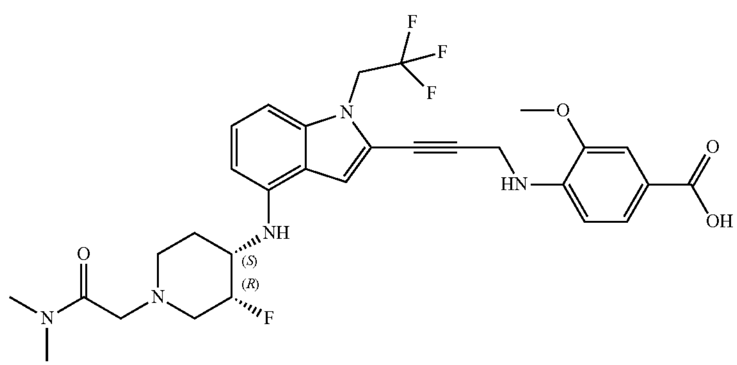 | 4-{[3-(4-{[(3R,4S)-1-[(dimethylcarbamoyl)methyl]-3-fluoropiperidin-4-yl]amino}-1-(2,2,2-trifluoroethyl)-1H-indol-2-yl)prop-2-yn-1-yl]amino}-3-methoxybenzoic acid | 604.2 |

TABLE 4-continued
| Compound No. | Structure | IUPAC | LC-MS (ES+, m/z) |
|---|---|---|---|
| 928A | 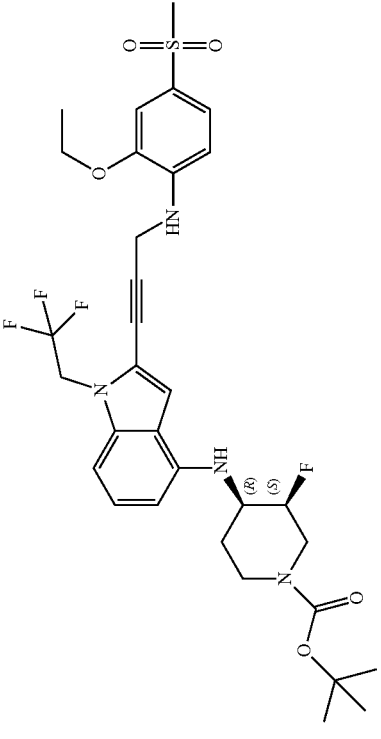 | tert-butyl (3S,4R)-4-[(2-{3-[(2-ethoxy-4-methanesulfonylphenyl)amino]prop-1-yn-1-yl}-1-(2,2,2-trifluoroethyl)-1H-indol-4-yl)amino]-3-fluoropiperidine-1-carboxylate | 611.2 (M-tert-But) |
| 929A | 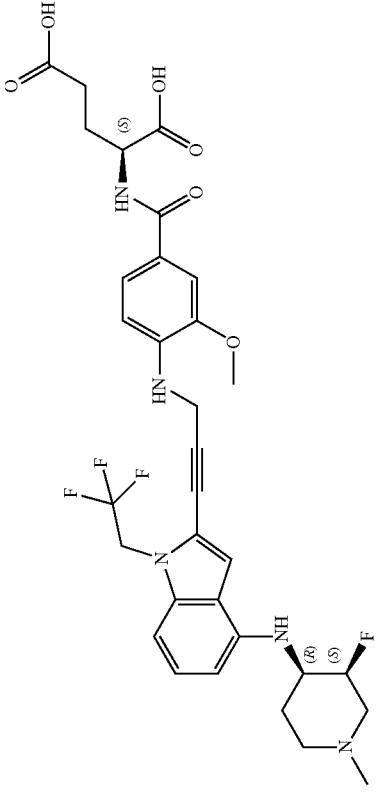 | (2S)-2-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]pentanedioic acid | 662.3 |

TABLE 4-continued

| Compound No. | Structure | IUPAC | LC-MS (ES+, m/z) |
|---|---|---|---|
| 930A | 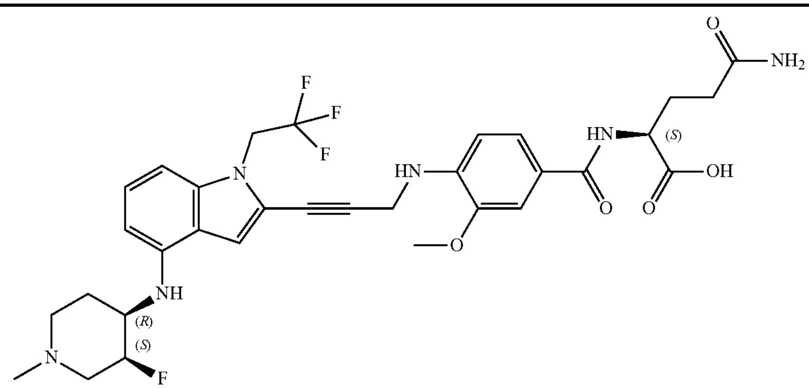 | (2S)-4-carbamoyl-2-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]butanoic acid | 661.3 |
| 931A | 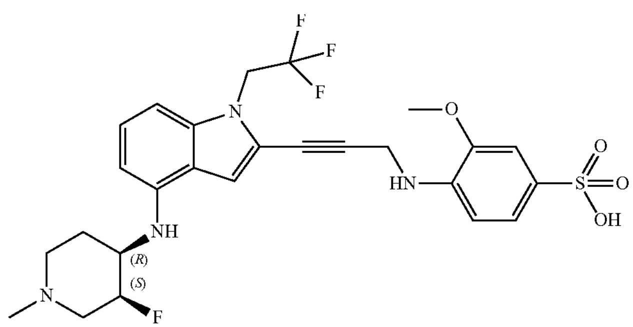 | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonic acid | 569.2 |
| 932A | 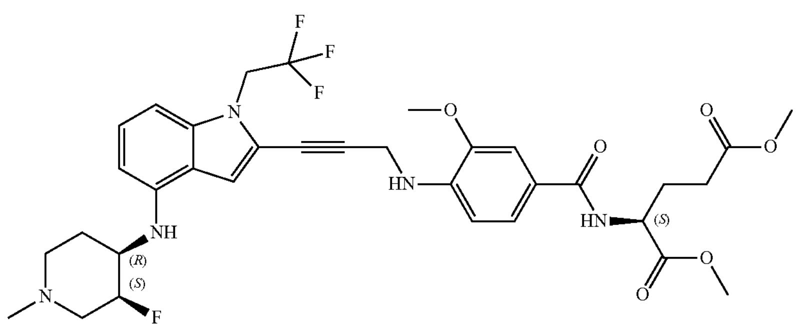 | 1,5-dimethyl (2S)-2-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]pentanedioate | 690.3 |

TABLE 4-continued

| Compound No. | Structure | IUPAC | LC-MS (ES+, m/z) |
|---|---|---|---|
| 933A | 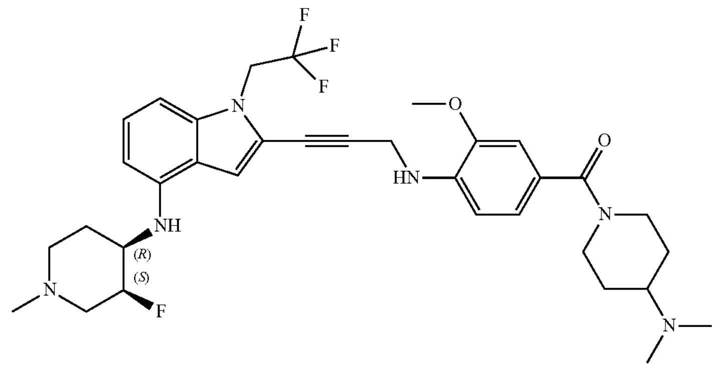 | 2-[3-({4-[4-(dimethylamino)piperidine-1-carbonyl]-2-methoxyphenyl}amino)prop-1-yn-1-yl]-N-[(3S,4R)-3-fluoro-1-methylpiperidin-4-yl]-1-(2,2,2-trifluoroethyl)-1H-indol-4-amine | 643.3 |
| 934A | 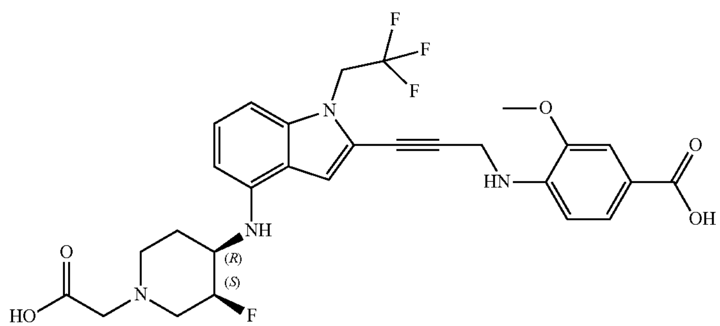 | 4-{[3-(4-{[(3S,4R)-1-(carboxymethyl)-3-fluoropiperidin-4-yl]amino}-1-(2,2,2-trifluoroethyl)-1H-indol-2-yl)prop-2-yn-1-yl]amino}-3-methoxybenzoic acid | 577.2 |

TABLE 4-continued

| Compound No. | Structure | IUPAC | LC-MS (ES+, m/z) |
|---|---|---|---|
| 935A | 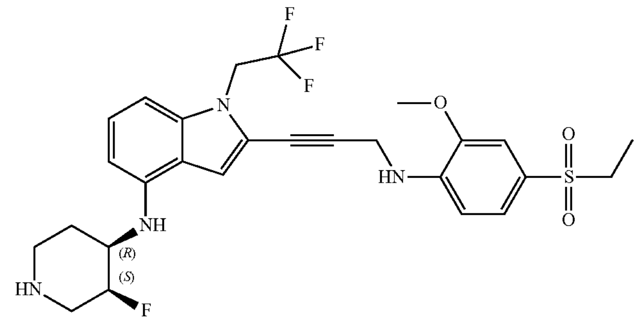 | 2-(3-{[4-(ethanesulfonyl)-2-methoxyphenyl]amino}prop-1-yn-1-yl)-N-[(3S,4R)-3-fluoropiperidin-4-yl]-1-(2,2,2-trifluoroethyl)-1H-indol-4-amine | 567.2 |
| 936A | 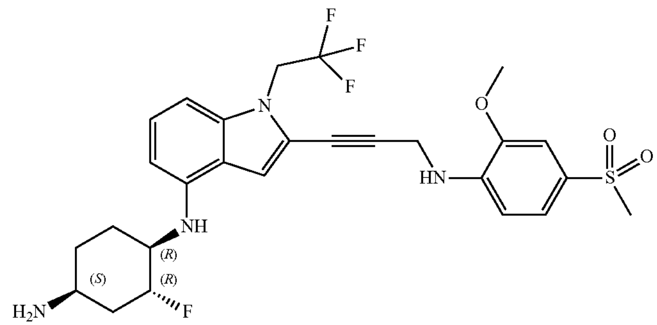 | (1R,2R,4S)-2-fluoro-N¹-(2-{3-[(4-methanesulfonyl-2-methoxyphenyl)amino]prop-1-yn-1-yl}-1-(2,2,2-trifluoroethyl)-1H-indol-4-yl)cyclohexane-1,4-diamine | 567.2 |
| 937A | 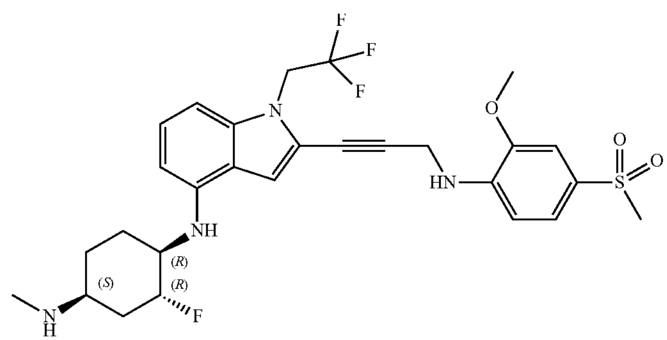 | (1R,2R,4S)-2-fluoro-N¹-(2-{3-[(4-methanesulfonyl-2-methoxyphenyl)amino]prop-1-yn-1-yl}-1-(2,2,2-trifluoroethyl)-1H-indol-4-yl)-N4-methylcyclohexane-1,4-diamine | 581.2 |

TABLE 4-continued

| Compound No. | Structure | IUPAC | LC-MS (ES+, m/z) |
|---|---|---|---|
| 938A | 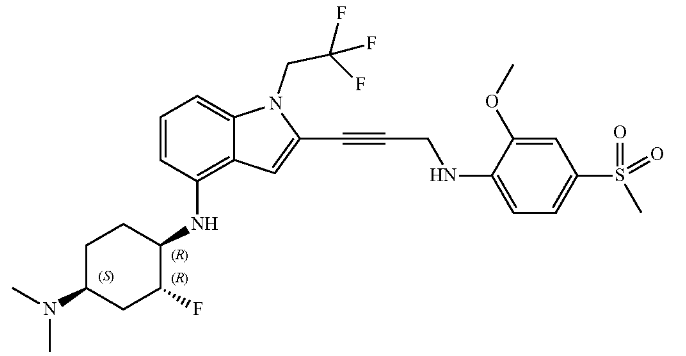 | (1S,3R,4R)-3-fluoro-N4-(2-{3-[(4-methanesulfonyl)-2-methoxyphenyl)amino]prop-1-yn-1-yl}-1-(2,2,2-trifluoroethyl)-1H-indol-4-yl)-N1,N1-dimethylcyclohexane-1,4-diamine | 595.2 |
| 939A | 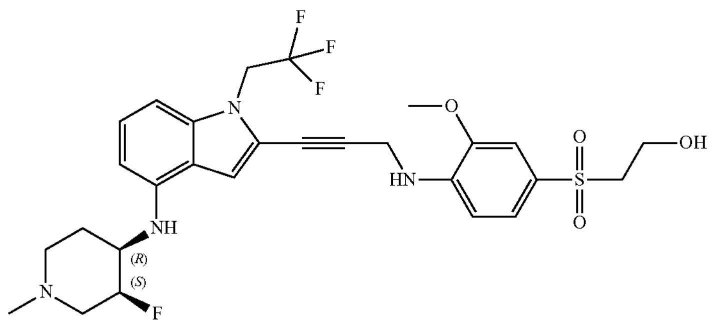 | 2-(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzenesulfonyl)ethan-1-ol | 597.2 |
| 940A | 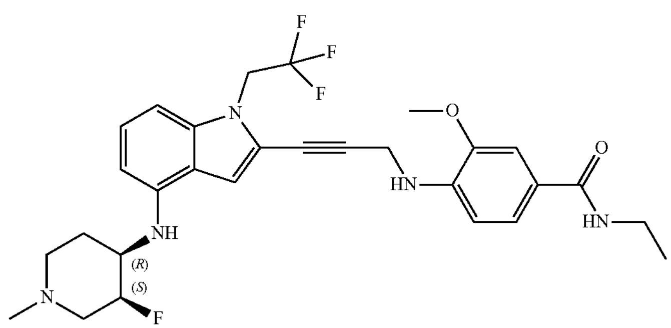 | N-ethyl-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide | 560.2 |

| Compound No. | Structure | IUPAC | LC-MS (ES+, m/z) |
|---|---|---|---|
| 941A | 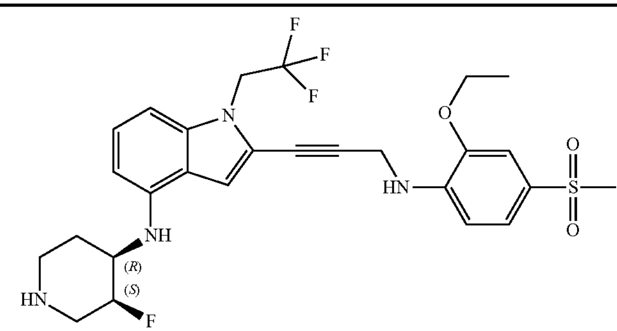 | 2-{3-[(2-ethoxy-4-methanesulfonylphenyl)amino]prop-1-yn-1-yl}-N-[(3S,4R)-3-fluoropiperidin-4-yl]-1-(2,2,2-trifluoroethyl)-1H-indol-4-amine | 567.3 |
| 942A | 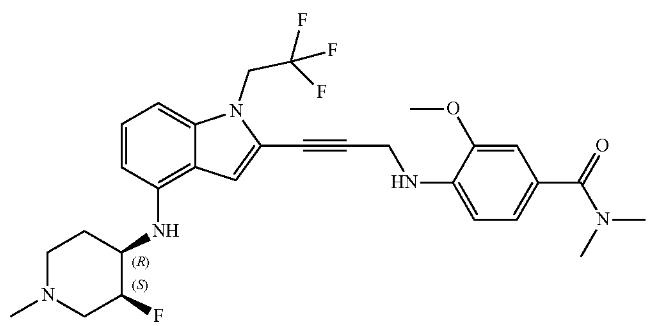 | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N,N-dimethylbenzamide | 560.3 |
| 943A | 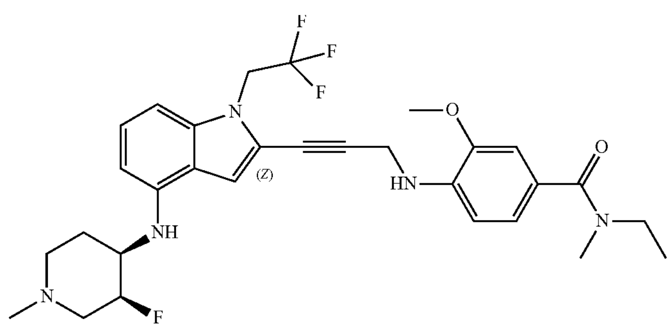 | N-ethyl-4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxy-N-methylbenzamide | 588.3 |

TABLE 4-continued

| Compound No. | Structure | IUPAC | LC-MS (ES+, m/z) |
|---|---|---|---|
| 944A | 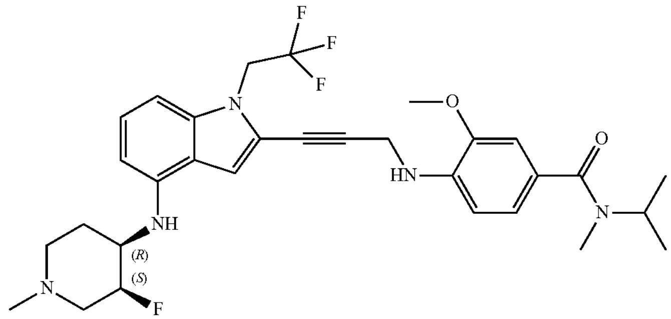 | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-methyl-N-(propan-2-yl)benzamide | 588.3 |
| 945A | 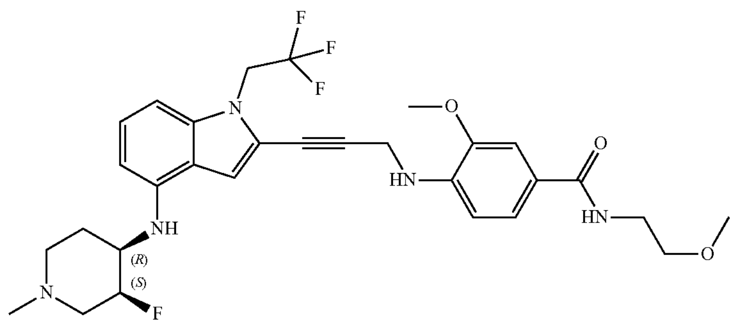 | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(2-methoxyethyl)benzamide | 590.2 |
| 946A | 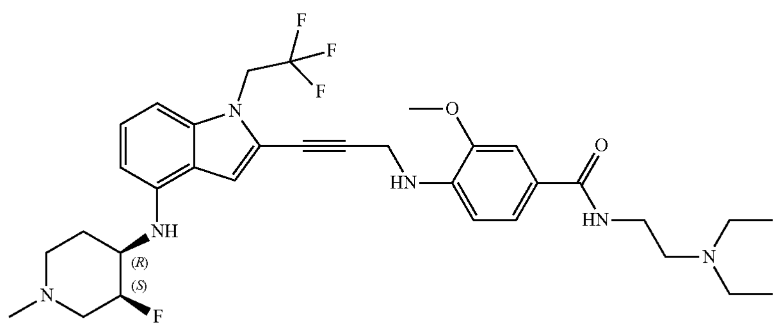 | N-[2-(diethylamino)ethyl]-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide | 631.4 |

TABLE 4-continued

| Compound No. | Structure | IUPAC | LC-MS (ES+, m/z) |
|---|---|---|---|
| 947A | 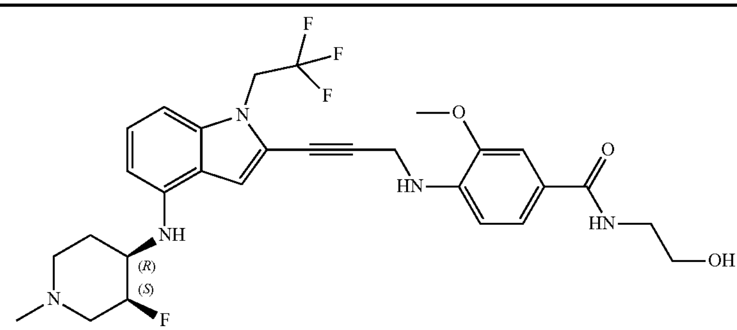 | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(2-hydroxyethyl)-3-methoxybenzamide | 576.3 |
| 948A | 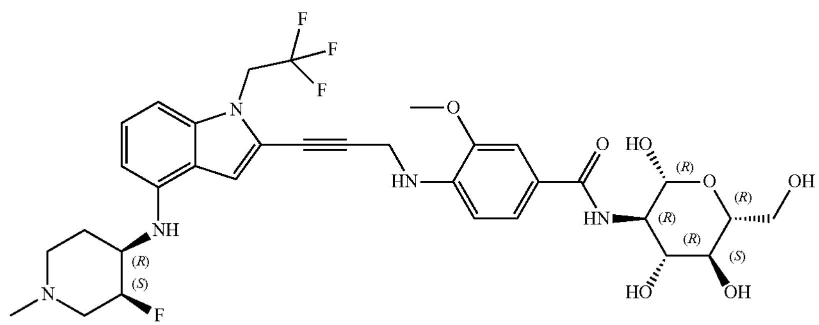 | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-[(2R,3R,4R,5S,6R)-2,4,5-trihydroxy-6-(hydroxymethyl)oxan-3-yl]benzamide | 694.3 |
| 949A | 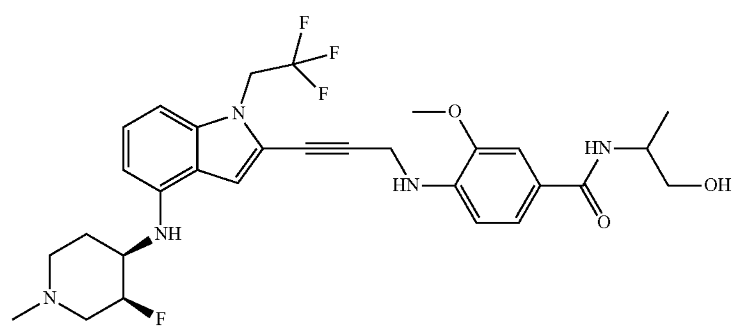 [SMILES: COc1cc(C(=O)NC(C)CO)ccc1NCC#Cc1cc2c(N[C@@H]3CCN(C)C[C@@H]3F)cccc2n1CC(F)(F)F] | 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-N-(1-hydroxypropan-2-yl)-3-methoxybenzamide | 590.3 |

TABLE 4-continued

| Compound No. | Structure | IUPAC | LC-MS (ES+, m/z) |
|---|---|---|---|
| 950A | 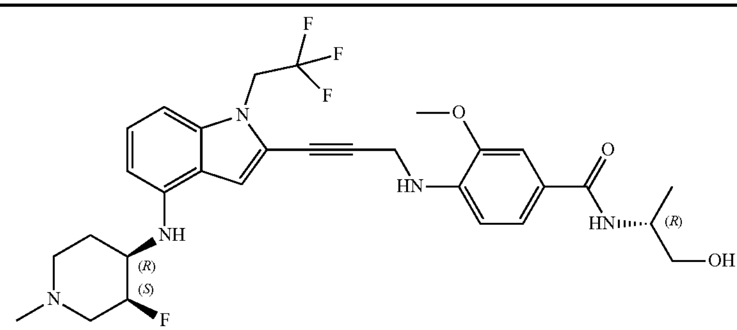 | 4-[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-[(2R)-1-hydroxypropan-2-yl]-3-methoxybenzamide | 590.3 |
| 951A | 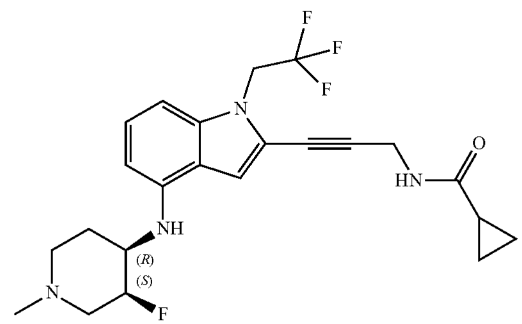 | N-[3-(4-{[(3S,4R)-3-fluoro-1-methylpiperidin-4-yl]amino}-1-(2,2,2-trifluoroethyl)-1H-indol-2-yl)prop-2-yn-1-yl]cyclopropanecarboxamide | 451.2 |
| 952A | 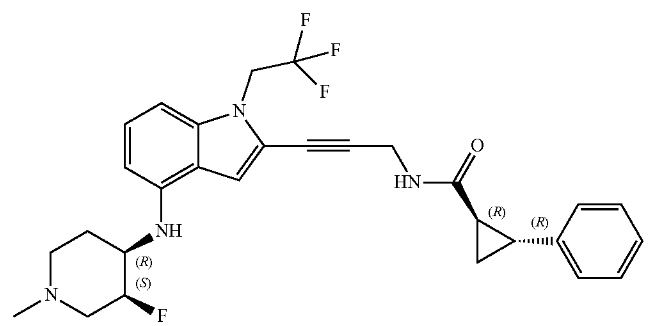 | (1R,2R)-N-[3-(4-{[(3S,4R)-3-fluoro-1-methylpiperidin-4-yl]amino}-1-(2,2,2-trifluoroethyl)-1H-indol-2-yl)prop-2-yn-1-yl]-2-phenylcyclopropane-1-carboxamide | 527.3 |

TABLE 4-continued

| Compound No. | Structure | IUPAC | LC-MS (ES+, m/z) |
|---|---|---|---|
| 953A | 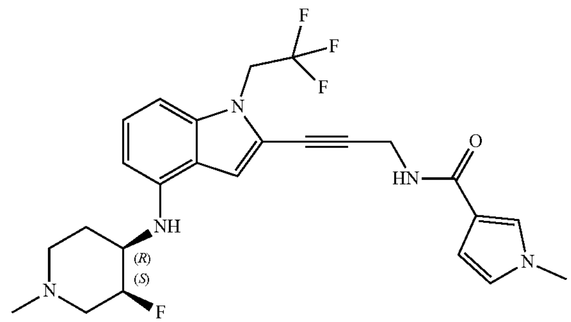 | N-[3-(4-{[(3S,4R)-3-fluoro-1-methylpiperidin-4-yl]amino}-1-(2,2,2-trifluoroethyl)-1H-indol-2-yl)prop-2-yn-1-yl]-1-methyl-1H-pyrrole-3-carboxamide | 490.2 |
| 954A | 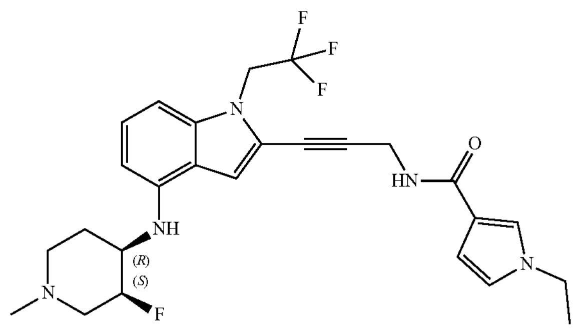 | 1-ethyl-N-[3-(4-{[(3S,4R)-3-fluoro-1-methylpiperidin-4-yl]amino}-1-(2,2,2-trifluoroethyl)-1H-indol-2-yl)prop-2-yn-1-yl]-1H-pyrrole-3-carboxamide | 504.2 |
| 955A | 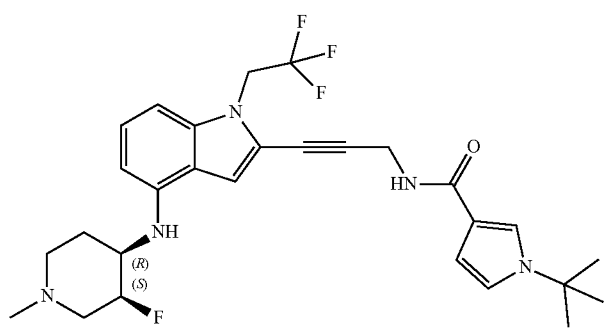 | 1-tert-butyl-N-[3-(4-{[(3S,4R)-3-fluoro-1-methylpiperidin-4-yl]amino}-1-(2,2,2-trifluoroethyl)-1H-indol-2-yl)prop-2-yn-1-yl]-1H-pyrrole-3-carboxamide | 532.3 |

TABLE 4-continued

| Compound No. | Structure | IUPAC | LC-MS (ES+, m/z) |
|---|---|---|---|
| 956A | 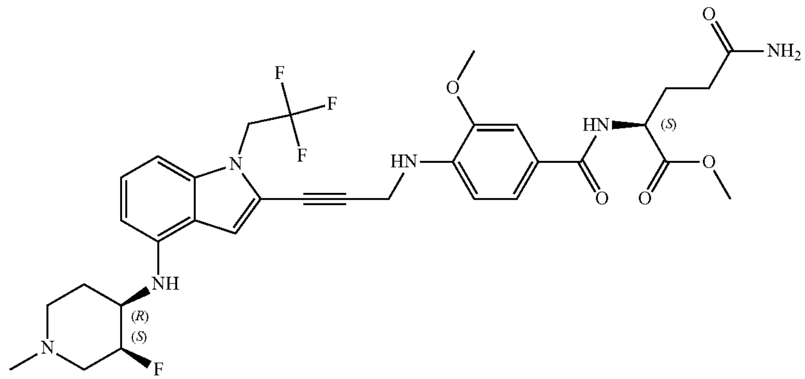 | methyl (2S)-4-carbamoyl-2-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]butanoate | 675.3 |
| 957A | 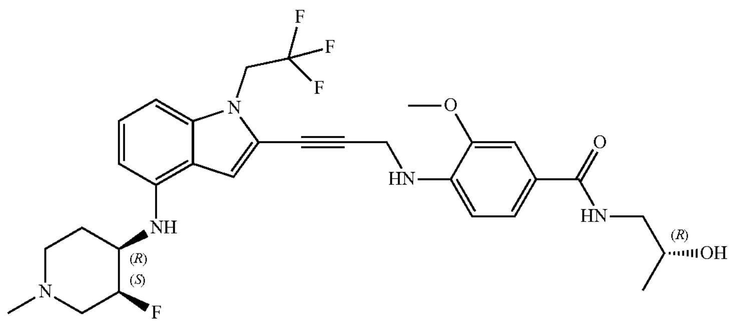 | 4-((3-(4-((3S,4R)-3-fluoro-1-methylpiperidin-4-yl)amino)-1-(2,2,2-trifluoroethyl)-1H-indol-2-yl)prop-2-yn-1-yl)amino)-N-((R)-2-hydroxypropyl)-3-methoxybenzamide | 590.2 |
| 958A | 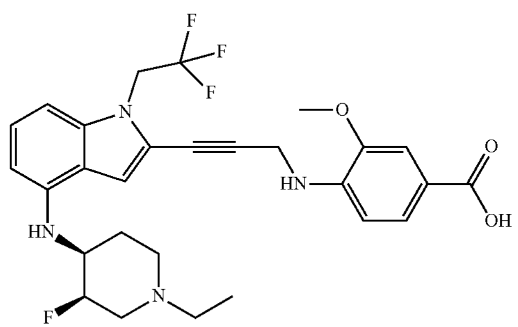 [SMILES: CCN1CC[C@H](Nc2cccc3c2cc(C#CCNc2ccc(C(=O)O)cc2OC)n3CC(F)(F)F)[C@H](F)C1] | rac-4-{[3-(4-{[(3R,4S)-1-ethyl-3-fluoropiperidin-4-yl]amino}-1-(2,2,2-trifluoroethyl)-1H-indol-2-yl)prop-2-yn-1-yl]amino}-3-methoxybenzoic acid | 547.2 |

TABLE 4-continued

| Compound No. | Structure | IUPAC | LC-MS (ES+, m/z) |
|---|---|---|---|
| 959A | 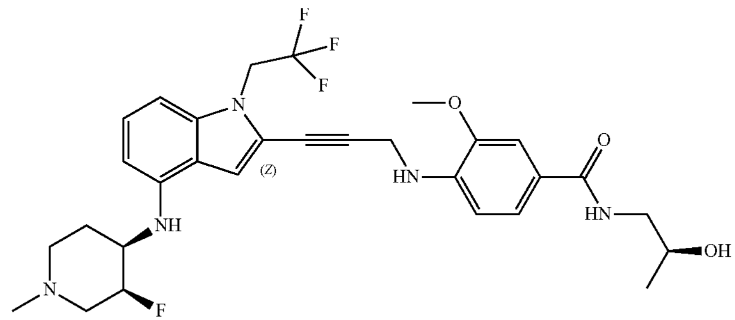 | 4-((3S,4R)-3-fluoro-1-methylpiperidin-4-yl)amino)-1-(2,2,2-trifluoroethyl)-1H-indol-2-yl)prop-2-yn-1-yl)amino)-N-((S)-2-hydroxypropyl)-3-methoxybenzamide | 590.2 |
| 960A | 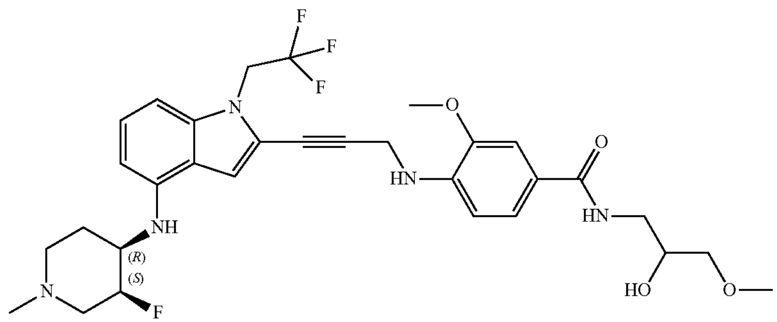 | 4-{[3-(4-{[(3S,4R)-3-fluoro-1-methylpiperidin-4-yl]amino}-1-(2,2,2-trifluoroethyl)-1H-indol-2-yl]prop-2-yn-1-yl]amino}-N-(2-hydroxy-3-methoxypropyl)-3-methoxybenzamide | 620.3 |
| 961A | 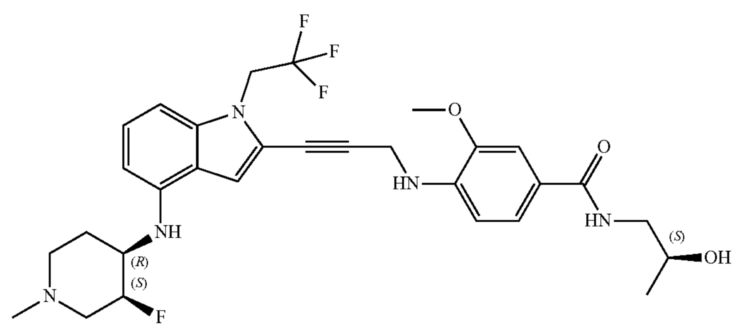 | 4-{[3-(4-{[(3S,4R)-3-fluoro-1-methylpiperidin-4-yl]amino}-1-(2,2,2-trifluoroethyl)-1H-indol-2-yl]prop-2-yn-1-yl]amino}-N-[(2S)-2-hydroxypropyl]-3-methoxybenzamide | 590.3 |

| Compound No. | Structure | IUPAC | LC-MS (ES+, m/z) |
|---|---|---|---|
| 962A | 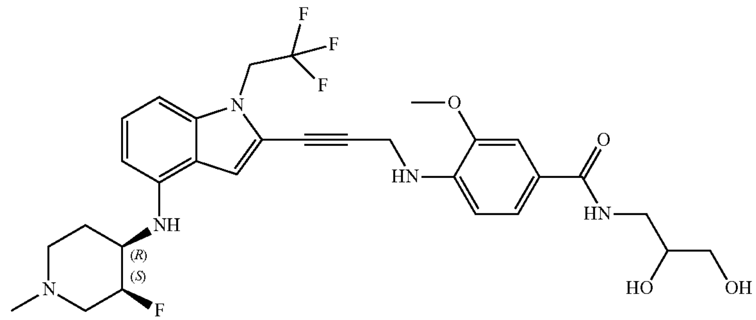 | N-(2,3-dihydroxypropyl)-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide | 606.3 |
| 963A | 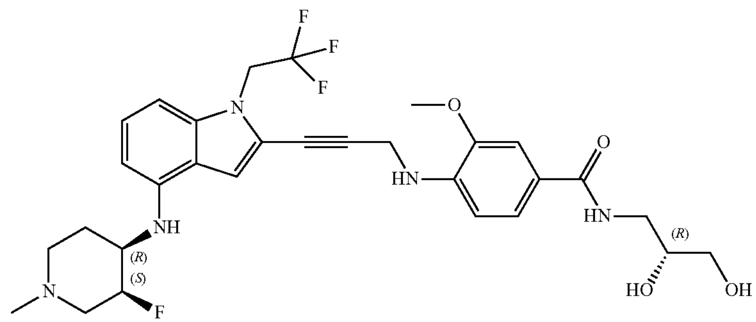 | N-[(2R)-2,3-dihydroxypropyl]-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide | 606.2 |
| 964A | 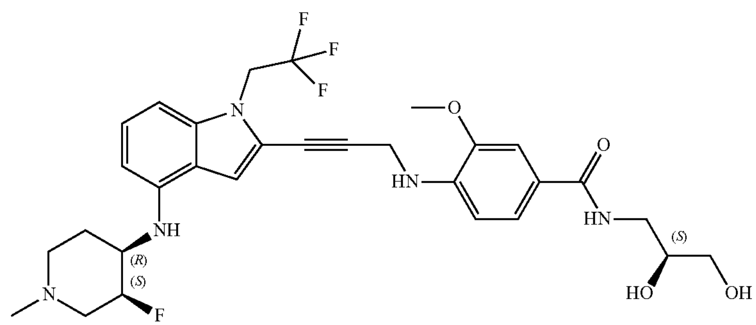 | N-[(2S)-2,3-dihydroxypropyl]-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide | 606.2 |

TABLE 4-continued

| Compound No. | Structure | IUPAC | LC-MS (ES+, m/z) |
|---|---|---|---|
| 965A | 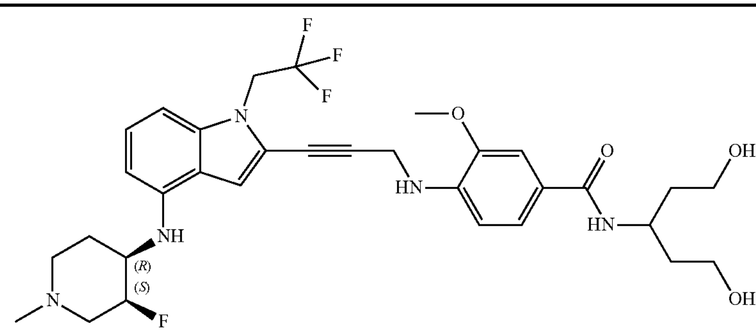 | N-(1,5-dihydroxypentan-3-yl)-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide | 634.3 |
| 966A | 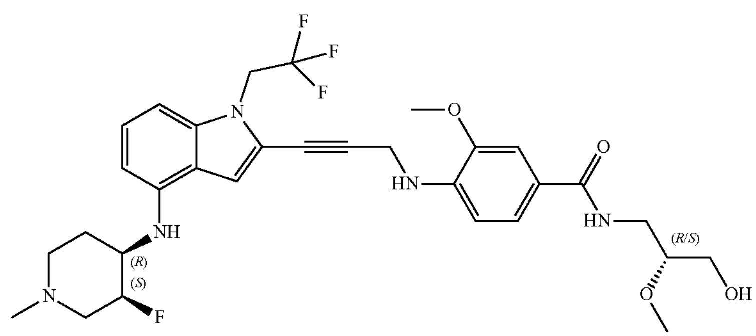 | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(3-hydroxy-2-methoxypropyl)-3-methoxybenzamide | 620.3 |
| 967A | 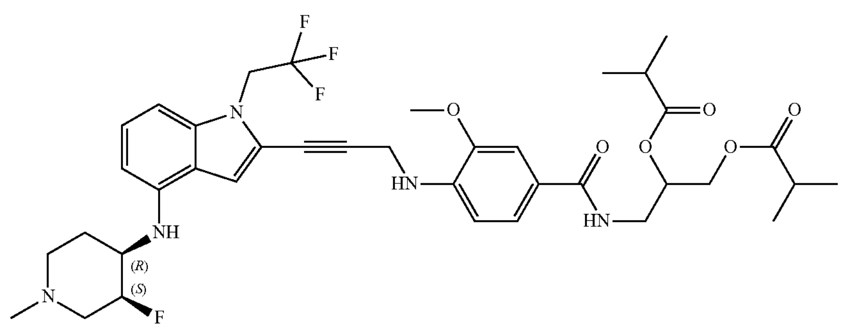 | 1-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]-3-[(2-methylpropanoyl)oxy]propan-2-yl 2-methylpropanoate | 746.3 |

| Compound No. | Structure | IUPAC | LC-MS (ES+, m/z) |
|---|---|---|---|
| 968A | 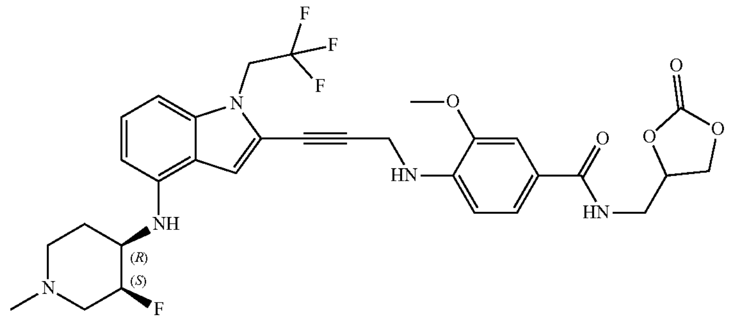 | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-[(2-oxo-1,3-dioxolan-4-yl)methyl]benzamide | 632.2 |
| 969A | 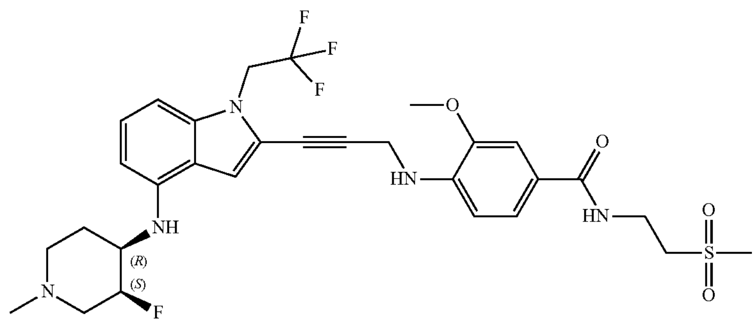 | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(2-methanesulfonylethyl)-3-methoxybenzamide | 638.1 |
| 970A | 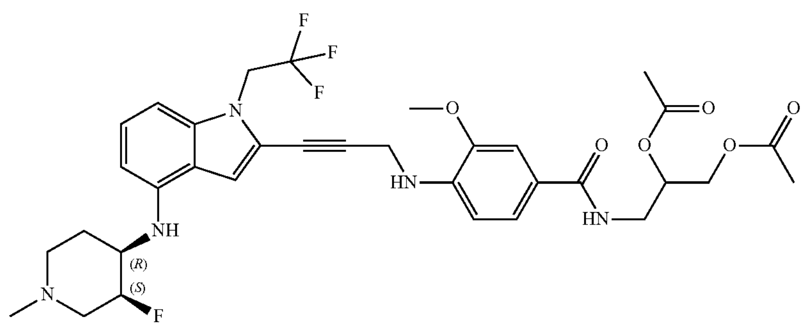 | 1-(acetyloxy)-3-{[4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]propan-2-yl acetate | 690.2 |

TABLE 4-continued

| Compound No. | Structure | IUPAC | LC-MS (ES+, m/z) |
|---|---|---|---|
| 971A | 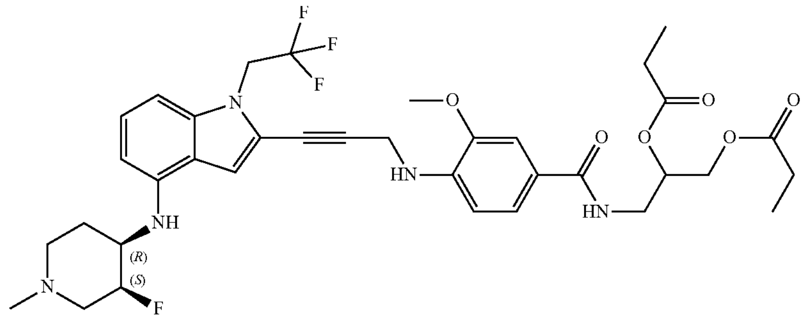 | 1-[(4-{[3-(4-{[(3S,4R)-3-fluoro-1-methylpiperidin-4-yl]amino}-1-(2,2,2-trifluoroethyl)-1H-indol-2-yl]prop-2-yn-1-yl]amino}-3-methoxyphenyl)formamido]-3-(propanoyloxy)propan-2-yl]propanoate | 718.2 |
| 972A | 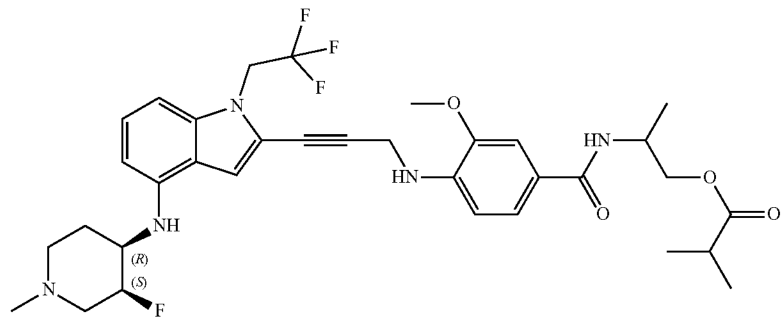 | 2-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]propyl 2-methylpropanoate | 660.1 |
| 973A | 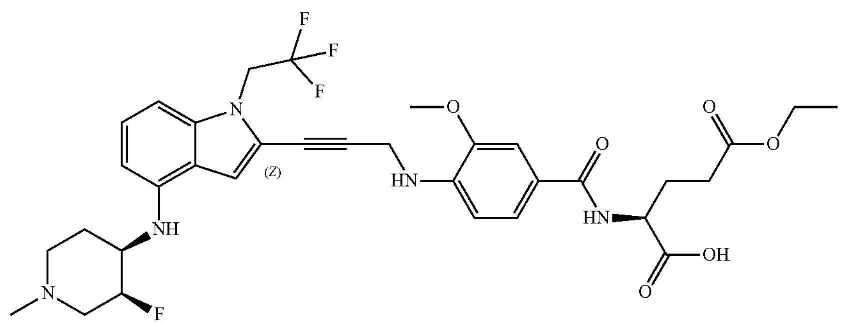 [SMILES: CCOC(=O)CC[C@H](NC(=O)c1ccc(NCC#Cc2cc3c(N[C@@H]4CCN(C)C[C@@H]4F)cccc3n2CC(F)(F)F)c(OC)c1)C(=O)O] | (S)-5-ethoxy-2-(4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzamido)-5-oxopentanoic acid | 649.3 |

TABLE 4-continued

| Compound No. | Structure | IUPAC | LC-MS (ES+, m/z) |
|---|---|---|---|
| 974A | 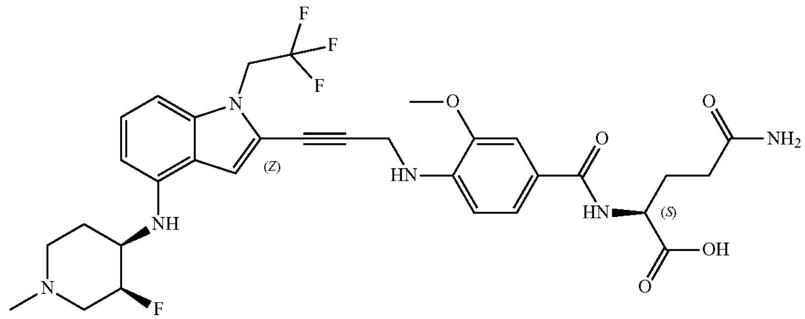 | (4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoyl)-L-glutamine | 661.3 |
| 975A | 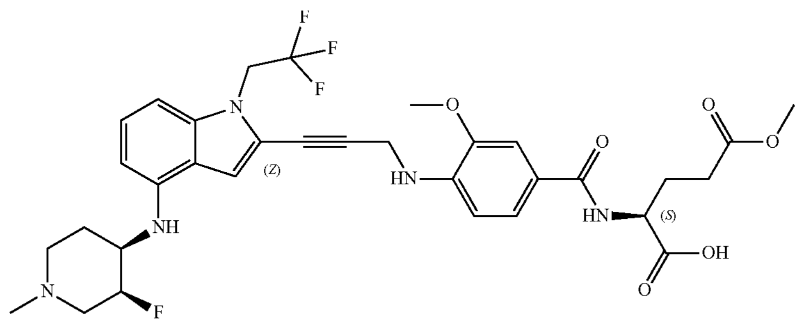 | (S)-2-(4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzamido)-5-methoxy-5-oxopentanoic acid | 694.3 |
| 976A | 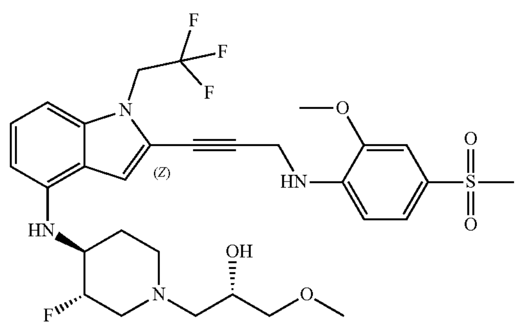 [SMILES: COC[C@@H](O)CN1CC[C@H](Nc2cccc3c2cc(C#CCNc2ccc(S(C)(=O)=O)cc2OC)n3CC(F)(F)F)[C@@H](F)C1] | (S)-1-((3S,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol | 641.2 |

TABLE 4-continued

| Compound No. | Structure | IUPAC | LC-MS (ES+, m/z) |
|---|---|---|---|
| 977A | 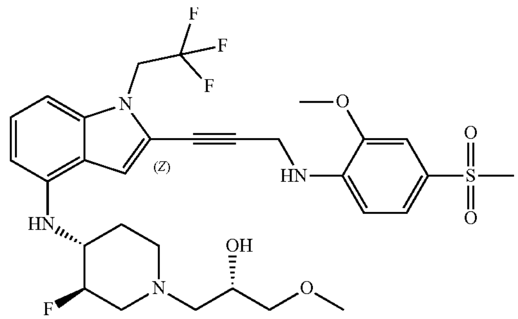 [SMILES: COC[C@@H](O)CN1CC[C@@H](Nc2cccc3c2cc(C#CCNc2ccc(S(C)(=O)=O)cc2OC)n3CC(F)(F)F)[C@H](F)C1] | (S)-1-((3R,4R)-3-fluoro-4-((2-(3-(2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol | 641.2 |
| 978A | 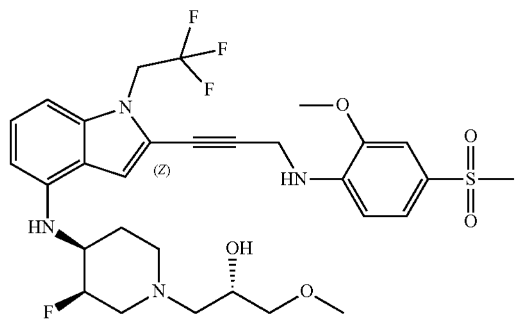 [SMILES: COC[C@@H](O)CN1CC[C@H](Nc2cccc3c2cc(C#CCNc2ccc(S(C)(=O)=O)cc2OC)n3CC(F)(F)F)[C@H](F)C1] | (S)-1-((3R,4S)-3-fluoro-4-((2-(3-(2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol | 641.3 |
| 979A | 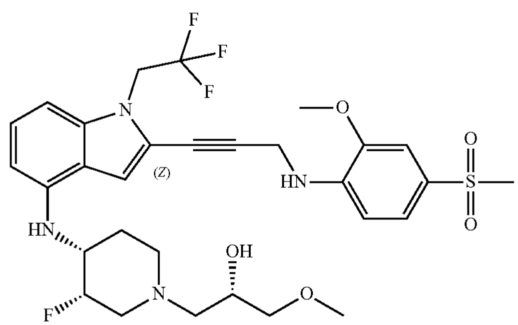 [SMILES: COC[C@@H](O)CN1CC[C@@H](Nc2cccc3c2cc(C#CCNc2ccc(S(C)(=O)=O)cc2OC)n3CC(F)(F)F)[C@@H](F)C1] | (S)-1-((3S,4R)-3-fluoro-4-((2-(3-(2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol | 641.3 |

TABLE 4-continued

| Compound No. | Structure | IUPAC | LC-MS (ES+, m/z) |
|---|---|---|---|
| 980A | 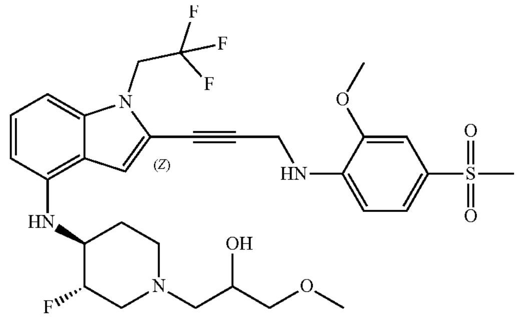 [SMILES: COCC(O)CN1CC[C@H](Nc2cccc3c2cc(C#CCNc2ccc(S(C)(=O)=O)cc2OC)n3CC(F)(F)F)[C@@H](F)C1] | 1-((3S,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol | 641.3 |
| 981A | 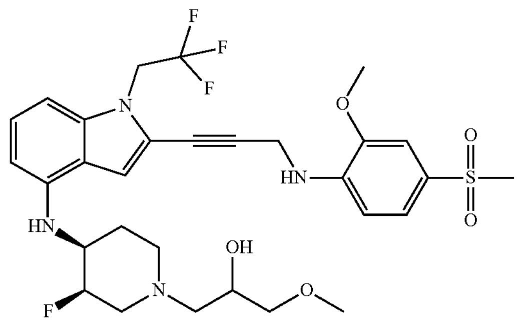 [SMILES: COCC(O)CN1CC[C@H](Nc2cccc3c2cc(C#CCNc2ccc(S(C)(=O)=O)cc2OC)n3CC(F)(F)F)[C@H](F)C1] | 1-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol | 641.3 |
| 982A | 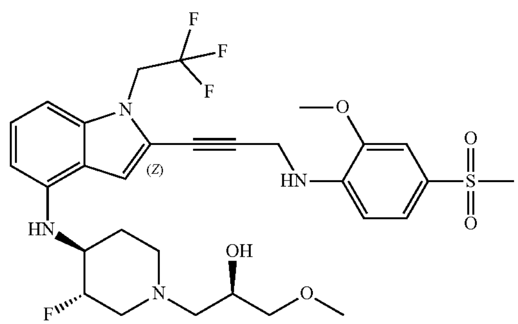 [SMILES: COC[C@H](O)CN1CC[C@H](Nc2cccc3c2cc(C#CCNc2ccc(S(C)(=O)=O)cc2OC)n3CC(F)(F)F)[C@@H](F)C1] | (R)-1-((3S,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol | 641.2 |

TABLE 4-continued

| Compound No. | Structure | IUPAC | LC-MS (ES+, m/z) |
|---|---|---|---|
| 983A | 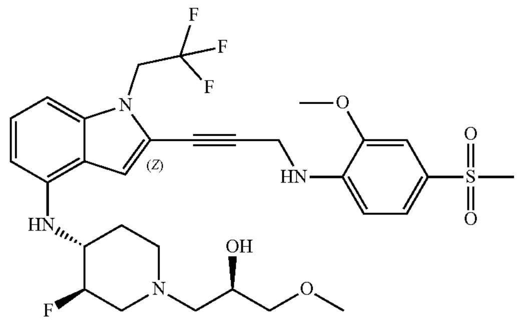 [SMILES: COC[C@H](O)CN1CC[C@@H](Nc2cccc3c2cc(C#CCNc2ccc(S(C)(=O)=O)cc2OC)n3CC(F)(F)F)[C@H](F)C1] | (R)-1-((3R,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol | 641.2 |
| 984A | 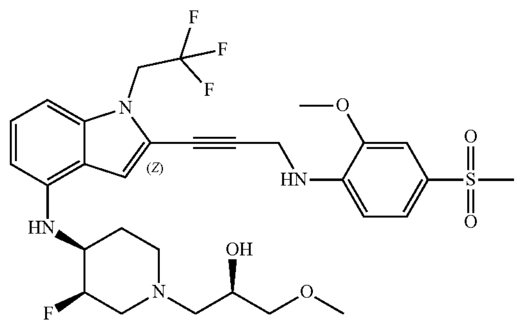 [SMILES: COC[C@H](O)CN1CC[C@H](Nc2cccc3c2cc(C#CCNc2ccc(S(C)(=O)=O)cc2OC)n3CC(F)(F)F)[C@H](F)C1] | (R)-1-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol | 641.3 |
| 985A | 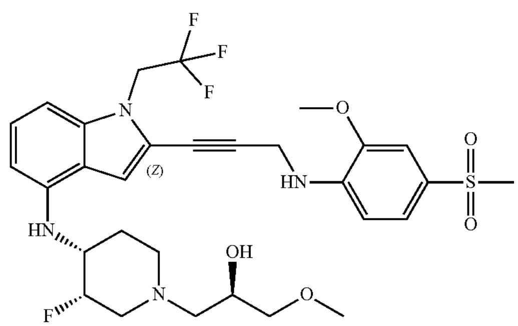 [SMILES: COC[C@H](O)CN1CC[C@@H](Nc2cccc3c2cc(C#CCNc2ccc(S(C)(=O)=O)cc2OC)n3CC(F)(F)F)[C@@H](F)C1] | (R)-1-((3S,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol | 641.3 |

TABLE 4-continued

| Compound No. | Structure | IUPAC | LC-MS (ES+, m/z) |
|---|---|---|---|
| 986A | 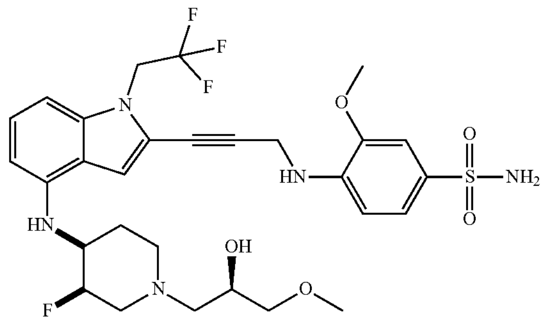 [SMILES: COC[C@H](O)CN1CC[C@H](Nc2cccc3c2cc(C#CCNc2ccc(S(N)(=O)=O)cc2OC)n3CC(F)(F)F)[C@H](F)C1] | 4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzenesulfonamide | 642.3 |
| 987A | 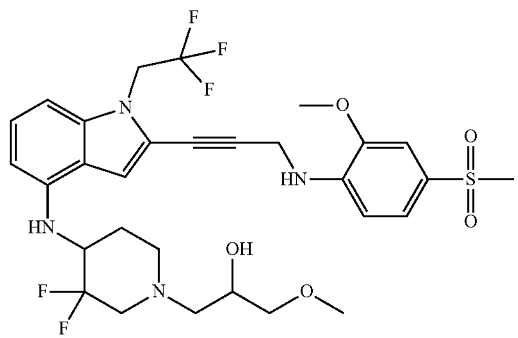 [SMILES: COCC(O)CN1CCC(Nc2cccc3c2cc(C#CCNc2ccc(S(C)(=O)=O)cc2OC)n3CC(F)(F)F)C(F)(F)C1] | 1-(3,3-difluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol | 659.2 |
| 988A | 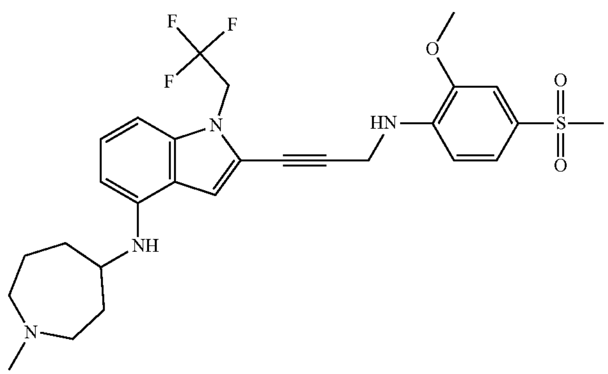 | 2-{3-[(4-methanesulfonyl-2-methoxyphenyl)amino]prop-1-yn-1-yl}-N-(1-methylazepan-4-yl)-1-(2,2,2-trifluoroethyl)-1H-indol-4-amine | 563.2 |

TABLE 4-continued

| Compound No. | Structure | IUPAC | LC-MS (ES+, m/z) |
|---|---|---|---|
| 989A | 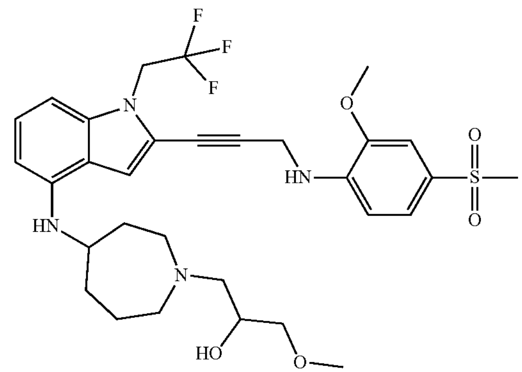 [SMILES: COCC(O)CN1CCCC(Nc2cccc3c2cc(C#CCNc2ccc(S(C)(=O)=O)cc2OC)n3CC(F)(F)F)CC1] | 1-{4-[(2-{3-[(4-methanesulfonyl-2-methoxyphenyl)amino]prop-1-yn-1-yl}-1-(2,2,2-trifluoroethyl)-1H-indol-4-yl)amino]azepan-1-yl}-3-methoxypropan-2-ol | 637.2 |
| 990A | 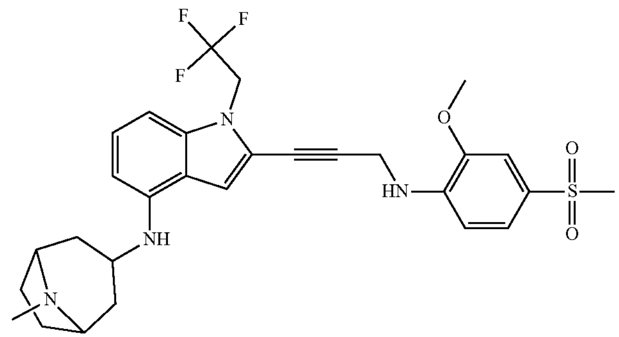 | 2-{3-[(4-methanesulfonyl-2-methoxyphenyl)amino]prop-1-yn-1-yl}-N-{8-methyl-8-azabicyclo[3.2.1]octan-3-yl}-1-(2,2,2-trifluoroethyl)-1H-indol-4-amine | 575.2 |

TABLE 4-continued

| Compound No. | Structure | IUPAC | LC-MS (ES+, m/z) |
|---|---|---|---|
| 1055A | 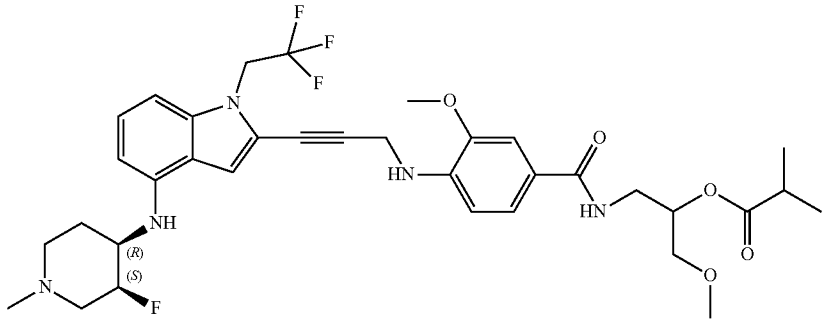 | 1-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]-3-methoxypropan-2-yl 2-methylpropanoate | 690.2 |
| 1056A | 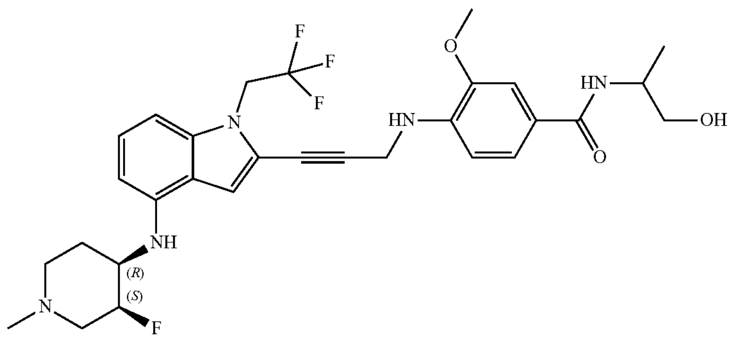 | 4-[(3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(1-hydroxypropan-2-yl)-3-methoxybenzamide | 590.1 |
| 1057A | 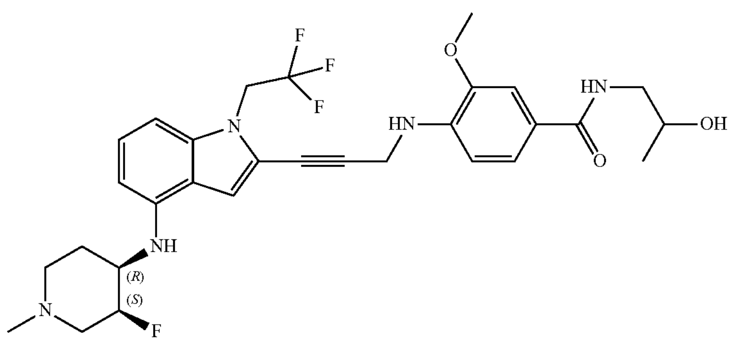 | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(2-hydroxypropyl)-3-methoxybenzamide | 590.1 |

TABLE 4-continued

| Compound No. | Structure | IUPAC | LC-MS (ES+, m/z) |
|---|---|---|---|
| 1058A | 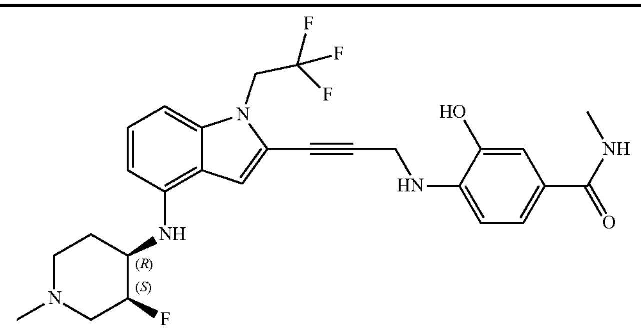 | 4-{[3-(4-{[(3S,4R)-3-fluoro-1-methylpiperidin-4-yl]amino}-1-(2,2,2-trifluoroethyl)-1H-indol-2-yl]prop-2-yn-1-yl]amino}-3-hydroxy-N-methylbenzamide | 532.2 |
| 1059A | 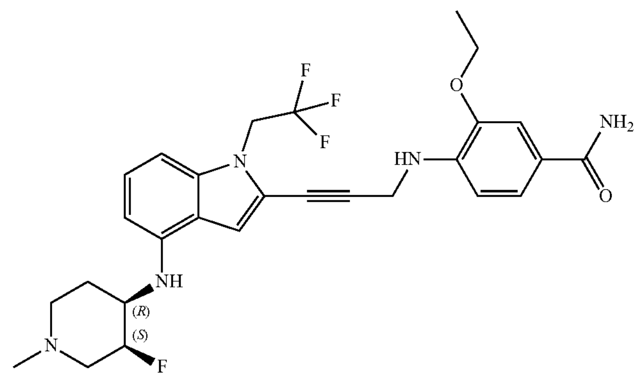 | 3-ethoxy-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}benzamide | 546.2 |
| 1060A | 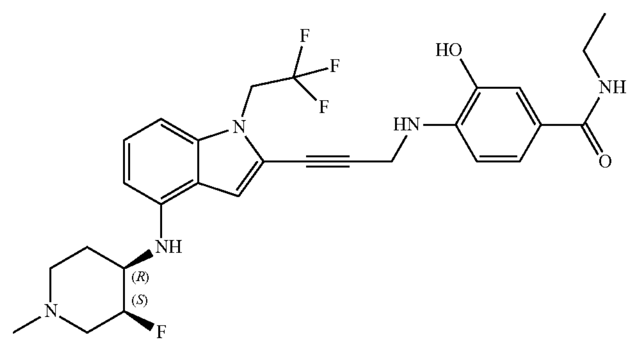 | N-ethyl-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-hydroxybenzamide | 546.3 |

TABLE 4-continued
| Compound No. | Structure | IUPAC | LC-MS (ES+, m/z) |
|---|---|---|---|
| 1061A | 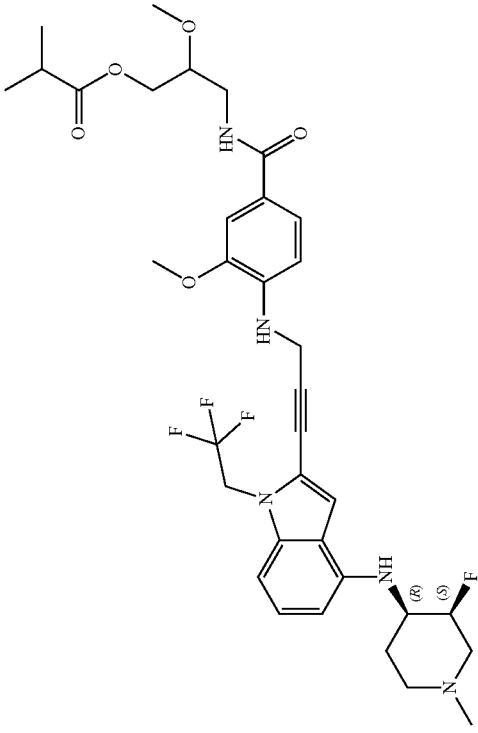 | 3-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]-2-methoxypropyl 2-methylpropanoate | 690.2 |
| 1062A | 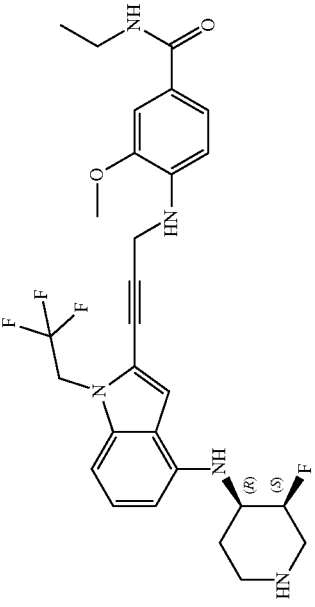 | N-ethyl-4-{[3-(4-{[(3S,4R)-3-fluoropiperidin-4-yl]amino}-1-(2,2,2-trifluoroethyl)-1H-indol-2-yl)prop-2-yn-1-yl]amino}-3-methoxybenzamide | 546.2 |

TABLE 4-continued

| Compound No. | Structure | IUPAC | LC-MS (ES+, m/z) |
|---|---|---|---|
| 1063A | 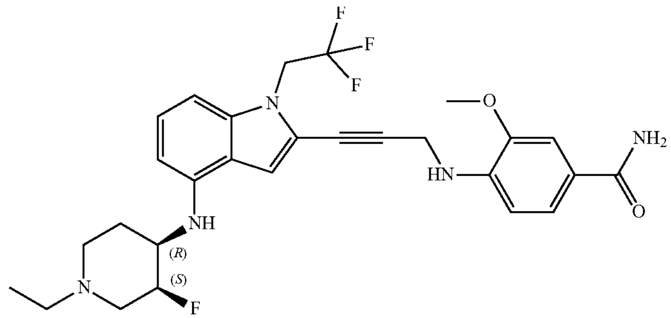 | 4-{[3-(4-{[(3S,4R)-1-ethyl-3-fluoropiperidin-4-yl]amino}-1-(2,2,2-trifluoroethyl)-1H-indol-2-yl)prop-2-yn-1-yl]amino}-3-methoxybenzamide | 546.2 |
| 1064A | 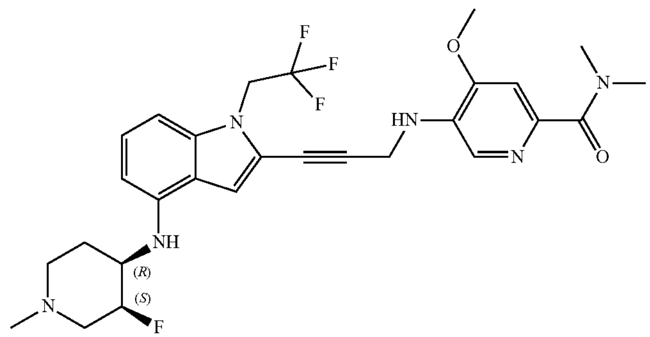 | 5-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-4-methoxy-N,N-dimethylpyridine-2-carboxamide | 561.1 |
| 1065A | 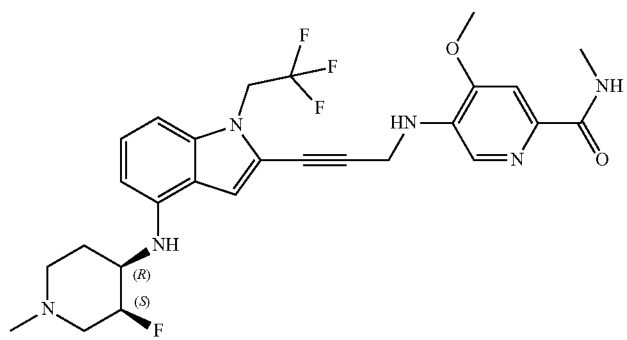 | 5-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-4-methoxy-N-methylpyridine-2-carboxamide | 547.1 |

TABLE 4-continued

| Compound No. | Structure | IUPAC | LC-MS (ES+, m/z) |
|---|---|---|---|
| 1066A | 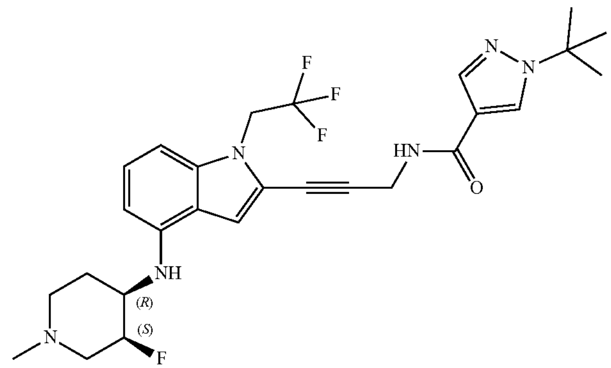 | 1-tert-butyl-N-[3-(4-{[(3S,4R)-3-fluoro-1-methylpiperidin-4-yl]amino}-1-(2,2,2-trifluoroethyl)-1H-indol-2-yl)prop-2-yn-1-yl]-1H-pyrazole-4-carboxamide | 533.1 |
| 1067A | 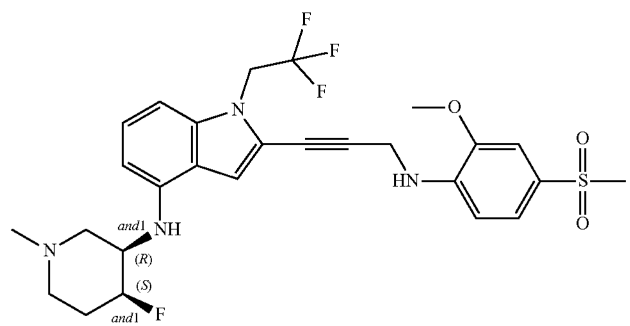 | rac-N-[(3R,4S)-4-fluoro-1-methylpiperidin-3-yl]-2-{3-[(4-methanesulfonyl)-2-methoxyphenyl)amino]prop-1-yn-1-yl}-1-(2,2,2-trifluoroethyl)-1H-indol-4-amine | 567.2 |
| 1068A | 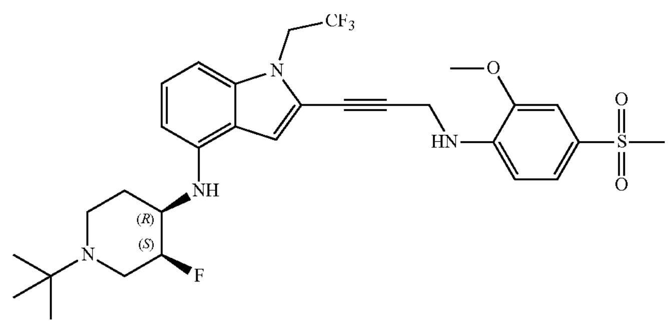 | N-((3S,4R)-1-(tert-butyl)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine | 609.2 |

TABLE 4-continued
| Compound No. | Structure | IUPAC | LC-MS (ES+, m/z) |
|---|---|---|---|
| 1069A | 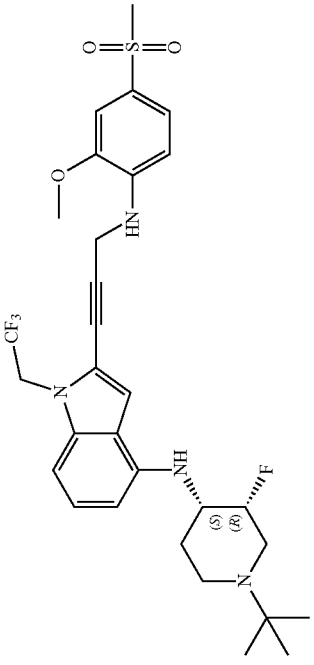 | N-[(3R,4S)-1-tert-butyl-3-fluoropiperidin-4-yl]-2-{3-[(4-methanesulfonyl)-2-methoxyphenyl)amino]prop-1-yn-1-yl}-1-(2,2,2-trifluoroethyl)-1H-indol-4-amine | 609.3 |
| 1070A | 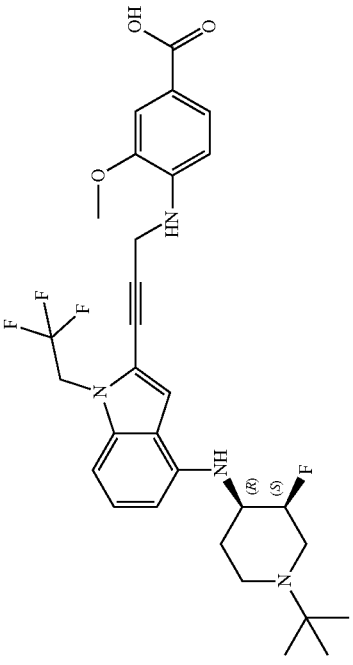 | 4-{[3-(4-{[(3S,4R)-1-tert-butyl-3-fluoropiperidin-4-yl]amino}-1-(2,2,2-trifluoroethyl)-1H-indol-2-yl)prop-2-yn-1-yl]amino}-3-methoxybenzoic acid | 575.3 |

TABLE 4-continued
| Compound No. | Structure | IUPAC | LC-MS (ES+, m/z) |
|---|---|---|---|
| 1071A | 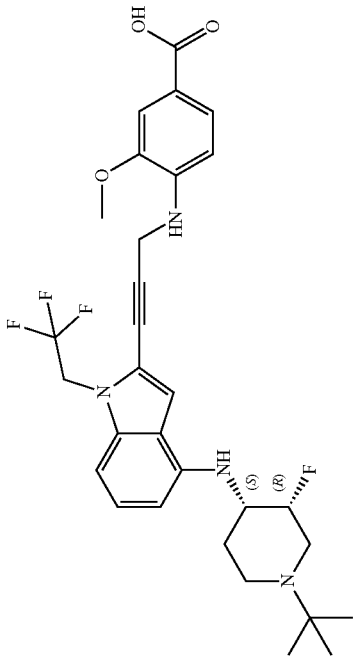 | 4-{[3-(4-{[(3R,4S)-1-tert-butyl-3-fluoropiperidin-4-yl]amino}-1-(2,2,2-trifluoroethyl)-1H-indol-2-yl)prop-2-yn-1-yl]amino}-3-methoxybenzoic acid | 575.3 |
| 1072A | 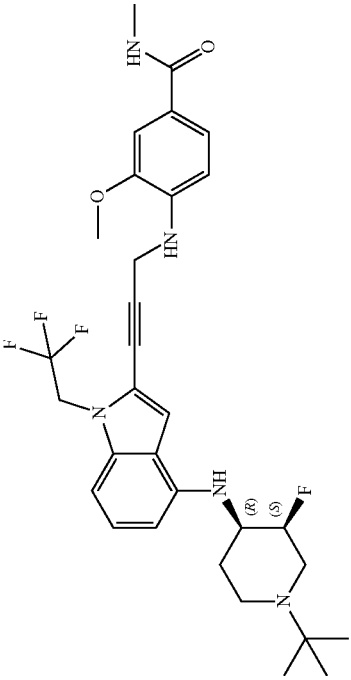 | 4-{[3-(4-{[(3S,4R)-1-tert-butyl-3-fluoropiperidin-4-yl]amino}-1-(2,2,2-trifluoroethyl)-1H-indol-2-yl)prop-2-yn-1-yl]amino}-3-methoxy-N-methylbenzamide | 588.3 |

TABLE 4-continued

| Compound No. | Structure | IUPAC | LC-MS (ES+, m/z) |
|---|---|---|---|
| 1073A | 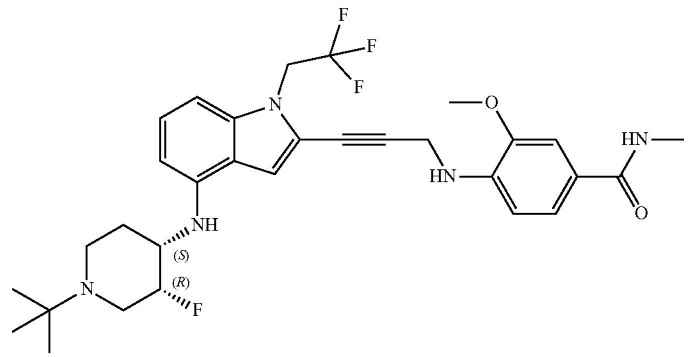 | 4-{[3-(4-{[(3R,4S)-1-tert-butyl-3-fluoropiperidin-4-yl]amino}-1-(2,2,2-trifluoroethyl)-1H-indol-2-yl)prop-2-yn-1-yl]amino}-3-methoxy-N-methylbenzamide | 588.3 |
| 1074A | 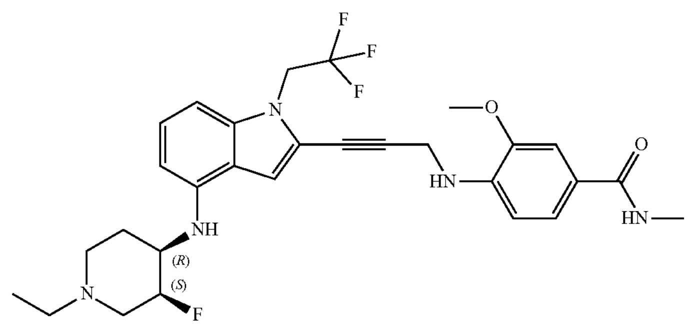 | 4-{[3-(4-{[(3S,4R)-1-ethyl-3-fluoropiperidin-4-yl]amino}-1-(2,2,2-trifluoroethyl)-1H-indol-2-yl)prop-2-yn-1-yl]amino}-3-methoxy-N-methylbenzamide | 560.1 |
| 1075A | 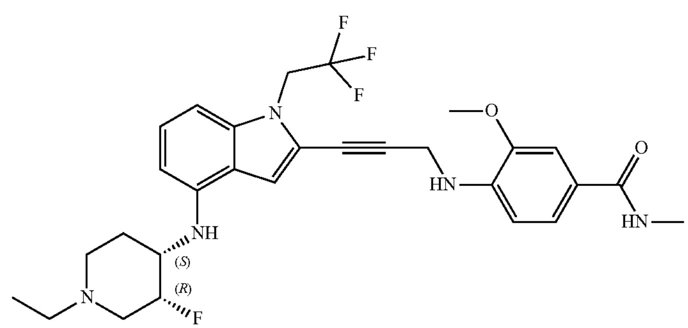 | 4-{[3-(4-{[(3R,4S)-1-ethyl-3-fluoropiperidin-4-yl]amino}-1-(2,2,2-trifluoroethyl)-1H-indol-2-yl)prop-2-yn-1-yl]amino}-3-methoxy-N-methylbenzamide | 560.1 |

E. Compounds with 2-ethynyl-N-(tetrahydropyran-4-yl)-1H-indole-4-amine core

Example E1: Synthesis of Compounds 1023A and 1024A

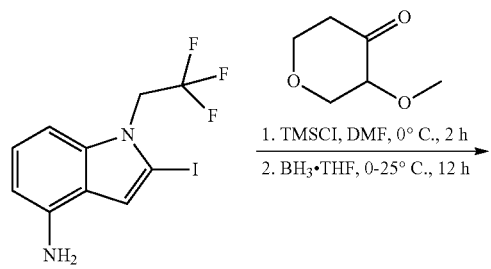

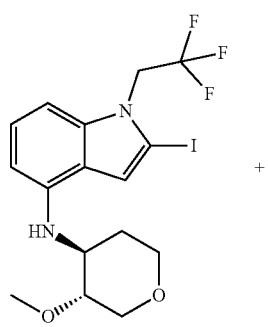

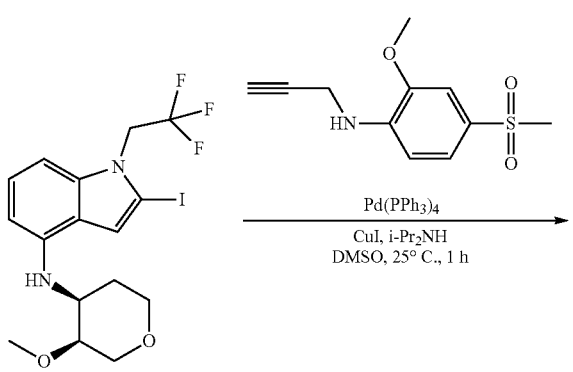

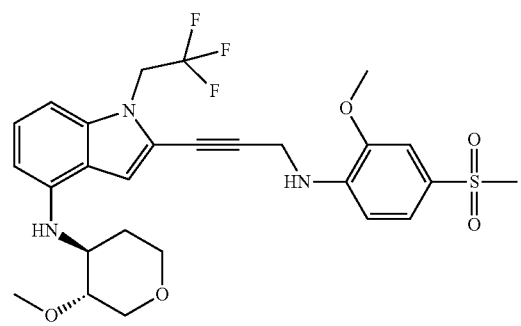

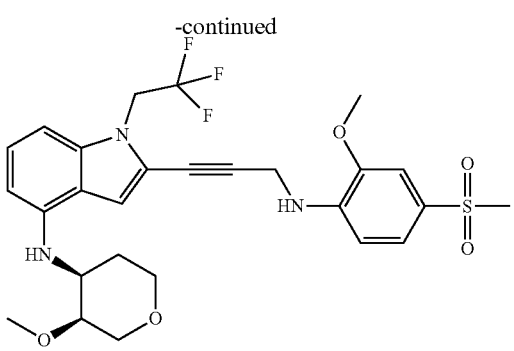

Preparation of 2-iodo-N-((3R,4S)-3-methoxytetrahydro-2H-pyran-4-yl)-1-(2,2,2-trifluoroethyl)-1H-indol-4-amine and 2-iodo-N-((3S,4S)-3-methoxytetrahydro-2H-pyran-4-yl)-1-(2,2,2-trifluoroethyl)-1H-indol-4-amine: To a solution of 2-iodo-1-(2,2,2-trifluoroethyl)indol-4-amine (0.5 g, 1.47 mmol, 1 eq.) and 3-methoxytetrahydropyran-4-one (765.35 mg, 5.88 mmol, 4 eq.) in DMF (5 mL) was added TMSCl (399.32 mg, 3.68 mmol, 466.50 µL, 2.5 eq.) at 0° C. The reaction mixture was stirred at 0° C. for 2 h, then BH$_3$·THF (1M, 7.35 mL, 5 eq.) was added to the mixture under N$_2$ at 0° C. The resulting mixture was stirred at 25° C. for 1 h. LC-MS analysis showed that the reaction was complete. The reaction was poured into a saturated aqueous solution of NH$_4$Cl (15 mL) and extracted with EtOAc (15 mL×3). The combined organic layers were washed with brine (15 mL×3), dried over anhydrous sodium sulfate, filtered, and concentrated under reduced pressure. The residue was purified by prep-TLC (SiO$_2$, PE:EtOAc=2:1) and prep-HPLC to afford the desired racemic products as light-yellow solids. 2-Iodo-N-[(3R,4R)-3-methoxytetrahydropyran-4-yl]-1-(2,2,2-trifluoroethyl)indol-4-amine (0.04 g, 79.26 µmol, 5.39% yield), MS (ES$^{30}$, m/z): 455.1; 2-iodo-N-[(3S,4R)-3-methoxytetrahydropyran-4-yl]-1-(2,2,2-trifluoroethyl)indol-4-amine (0.03 g, 59.44 µmol, 4.04% yield), MS (ES$^{30}$, m/z): 455.1.

Preparation of final products: To a solution of 2-methoxy-4-(methylsulfonyl)-N-(prop-2-yn-1-yl)aniline (1.2 eq., HCl) in DMSO were added N-isopropylpropan-2-amine (10 eq.), CuI (1 eq.), 2-iodo-N-[(3R,4R)-3-methoxytetrahydropyran-4-yl]-1-(2,2,2-trifluoroethyl)indol-4-amine or 2-iodo-N-[(3S,4R)-3-methoxytetrahydropyran-4-yl]-1-(2,2,2-trifluoroethyl)indol-4-amine (1 eq.), and Pd(PPh$_3$)$_4$ (0.4 eq.). The reaction mixture was stirred at 25° C. for 1 h. LC-MS analysis showed that the reaction was complete. The reaction was diluted with EtOAc (15 mL), and the resulting mixture was poured into saturated aqueous EDTA (15 mL) and stirred at 25° C. for 1 h. The mixture was extracted with EtOAc (10 mL×3). The combined organic layers were washed with brine (10 mL×3), dried over anhydrous sodium sulfate, filtered, and concentrated under reduced pressure. The residue was purified by prep-TLC (SiO$_2$, DCM:MeOH=10:1) and prep-HPLC to afford the desired products as light-yellow solids.

2-(3-((2-methoxy-4-(methylsulfonyl)phenyl)amino)prop-1-yn-1-yl)-N-((3R,4S)-3-methoxytetrahydro-2H-pyran-4-yl)-1-(2,2,2-trifluoroethyl)-1H-indol-4-amine, MS (ES$^{30}$, m/z): 566.2; and 2-(3-((2-methoxy-4-(methylsulfonyl)phenyl)amino)prop-1-yn-1-yl)-N-((3S,4S)-3-methoxytetrahydro-2H-pyran-4-yl)-1-(2,2,2-trifluoroethyl)-1H-indol-4-amine, MS (ES$^{30}$, m/z): 566.2.

Example E2: Synthesis of Compounds 1025A and 1026A

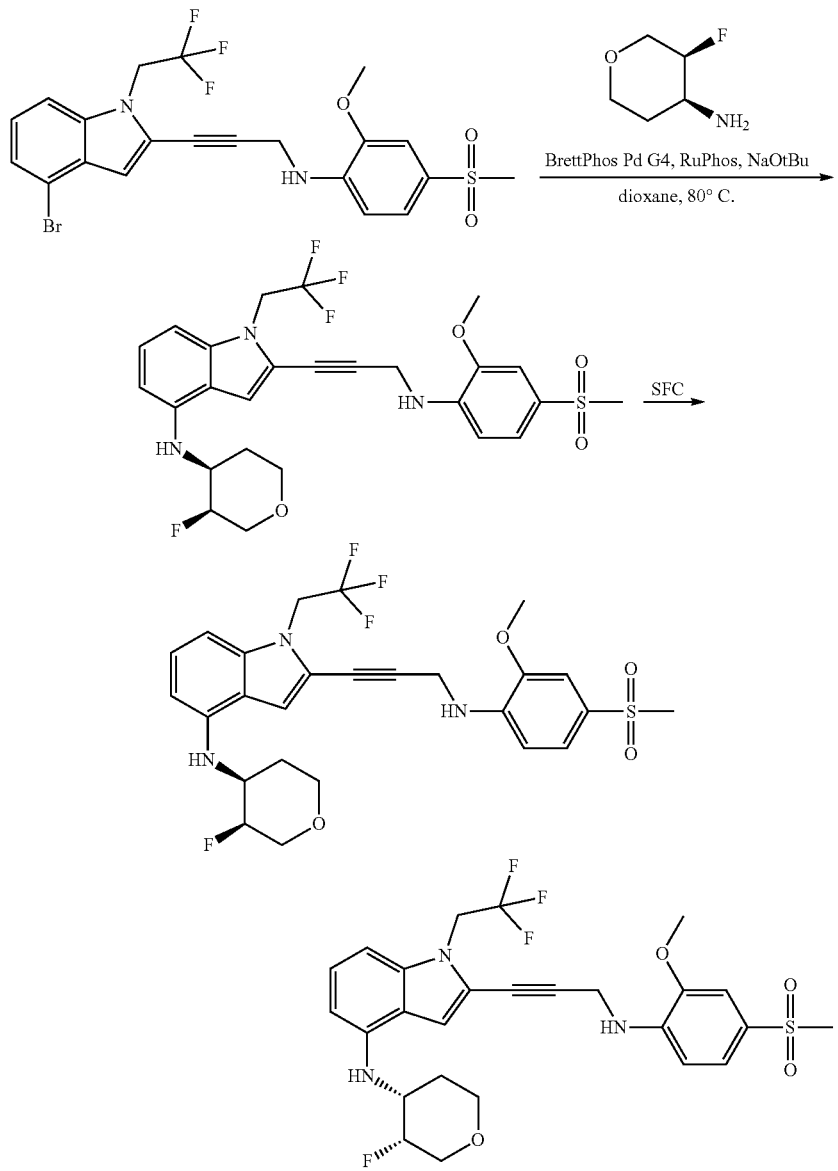

Preparation of N-((3S,4S)-3-fluorotetrahydro-2H-pyran-4-yl)-2-(3-((2-methoxy-4-(methylsulfonyl)phenyl)amino)prop-1-yn-1-yl)-1-(2,2,2-trifluoroethyl)-1H-indol-4-amine:
To a mixture of N-(3-(4-bromo-1-(2,2,2-trifluoroethyl)-1H-indol-2-yl)prop-2-yn-1-yl)-2-methoxy-4-(methylsulfonyl)aniline (50 mg, 97.02 μmol, 1 eq.) and (3S,4S)-3-fluorotetrahydropyran-4-amine (30.19 mg, 194.05 μmol, 2 eq., HCl) in dioxane (6.25 mL) were added NaOtBu (35.43 mg, 368.69 μmol, 3.8 eq.) and RuPhos (14.49 mg, 31.05 μmol, 0.32 eq.). The reaction mixture was stirred at 80° C. for 40 mins. TLC analysis showed no reaction. NaOtBu (35.43 mg, 368.69 μmol, 3.8 eq.) and BrettphosPdG4 (89.31 mg, 97.02 μmol, 1 eq.) were added to the reaction, and the mixture was stirred at 80° C. for another 40 mins. TLC analysis showed that very little starting material remained, and one new major spot for the desired product was detected. EtOAc (20 mL) was poured into the mixture, and the resulting mixture was then poured into a saturated solution of EDTA (30 mL) and stirred for 1 h. The aqueous phase was extracted with EtOAc (20 mL×3). The combined organic layers were washed with brine (30 mL×3), dried over anhydrous sodium sulfate, treated with activated carbon to remove color, filtered, and concentrated in vacuo. The crude residue was purified by prep-TLC (SiO$_2$, PE:EtOAc=1:1) and prep-HPLC to obtain the desired product (105 mg, 189.68 μmol, 32.58% yield) as a yellow solid. MS (ES$^{30}$, m/z): 554.2.

Preparation of N-[(3S,4S)-3-fluorooxan-4-yl]-2-{3-[(4-methanesulfonyl-2-methoxyphenyl)amino]prop-1-yn-1-yl}-1-(2,2,2-trifluoroethyl)-1H-indol-4-amine and N-[(3R,4R)-3-fluorooxan-4-yl]-2-{3-[(4-methanesulfonyl-2-methoxyphenyl)amino]prop-1-yn-1-yl}-1-(2,2,2-trifluoroethyl)-1H-indol-4-amine: The residue from the previous step was purified by prep-SFC to obtain the desired products as white solids.

N-[(3S,4S)-3-fluorooxan-4-yl]-2-{3-[(4-methanesulfo-nyl-2-methoxyphenyl)amino]prop-1-yn-1-yl}-1-(2,2,2-trifluoroethyl)-1H-indol-4-amine (15.4 mg, 27.76 μmol, 14.64% yield), MS (ES$^{30}$, m/z): 554.2; and N-[(3R,4R)-3-fluorooxan-4-yl]-2-{3-[(4-methanesulfonyl-2-methoxyphenyl)amino]prop-1-yn-1-yl}-1-(2,2,2-trifluoroethyl)-1H-indol-4-amine (21.2 mg, 38.30 μmol, 20.19% yield), MS (ES$^{30}$, m/z): 554.2.

Example E3: Synthesis of 3-methoxy-4-((3-(4-((tetrahydro-2H-pyran-4-yl)amino)-1-(2,2,2-trifluoroethyl)-1H-indol-2-yl)prop-2-yn-1-yl)amino)benzamide (Compound 1006A)

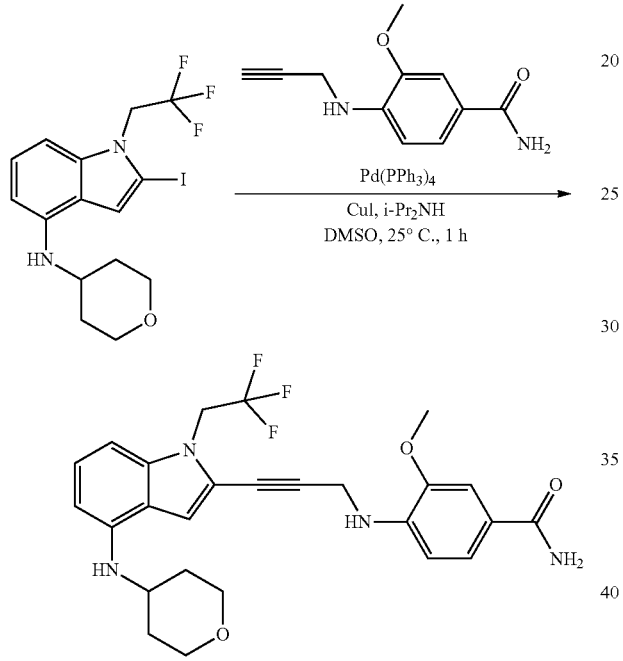

To a solution of 3-methoxy-4-(prop-2-yn-1-ylamino)benzamide (1.1 g, 4.85 mmol, 1.44 eq.) in DMSO (15 mL) were added i-Pr$_2$NH (3.40 g, 33.59 mmol, 4.75 mL, 10 eq.), CuI (639.77 mg, 3.36 mmol, 1 eq.), 2-iodo-N-(tetrahydro-2H-pyran-4-yl)-1-(2,2,2-trifluoroethyl)-1H-indol-4-amine (1.5 g, 3.36 mmol, 1 eq.), and Pd(PPh$_3$)$_4$ (776.37 mg, 671.85 μmol, 0.2 eq.) in one portion at 25° C. under N$_2$. The mixture was stirred at 25° C. for 1 h. TLC analysis (PE:EtOAc=0:1, R$_f$=0.36) showed that the reaction was complete. EtOAc (30 mL) was poured into the mixture, and the resulting mixture was poured into a saturated aqueous solution of EDTA (100 mL) and stirred for 15 min. The aqueous phase was extracted with EtOAc (50 mL×2). The organic layer was poured into a saturated aqueous EDTA solution (100 mL) and stirred for 1 h. The aqueous phase was extracted with EtOAc (50 mL×3). The combined organic layers were washed with brine (50 mL×3), dried over anhydrous sodium sulfate, treated with activated carbon, filtered, and concentrated in vacuo. The crude residue was purified by silica gel chromatography (SiO$_2$, PE:EtOAc=1:0 to 0:1) and prep-HPLC to afford the desired product as a yellow solid. MS (ES$^{30}$, m/z): 501.1.

Example E4: Synthesis of Compounds 997A and 998A

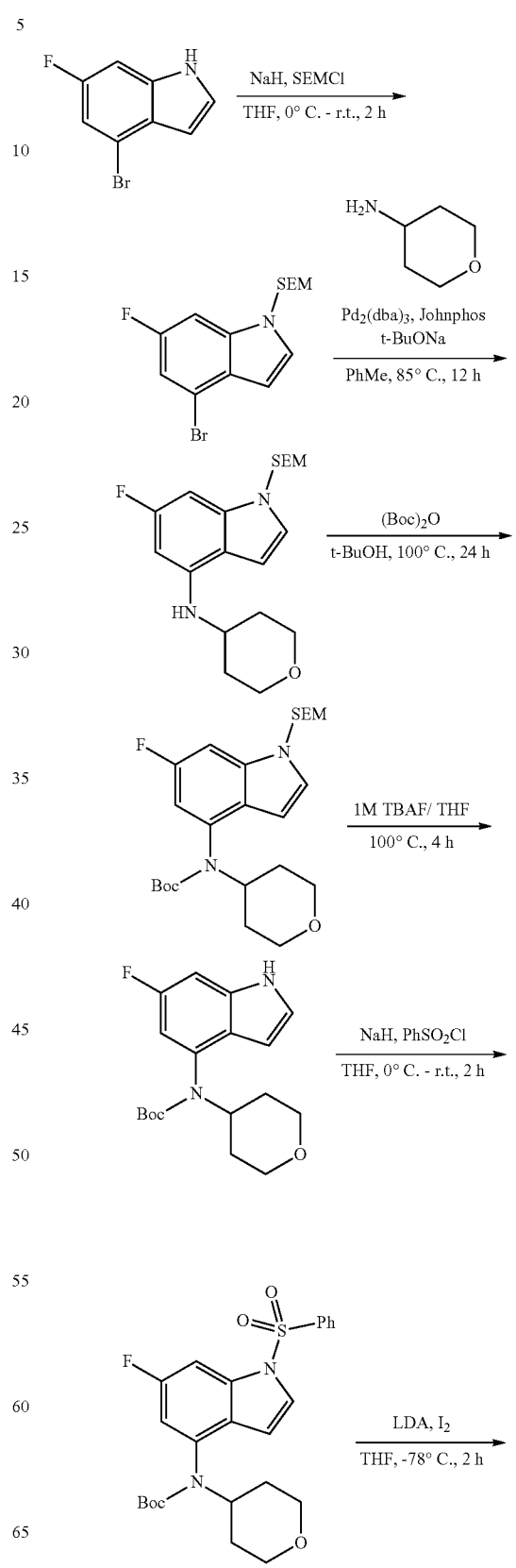

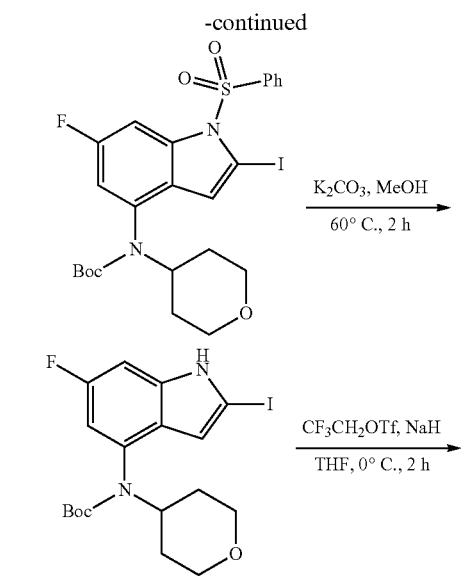

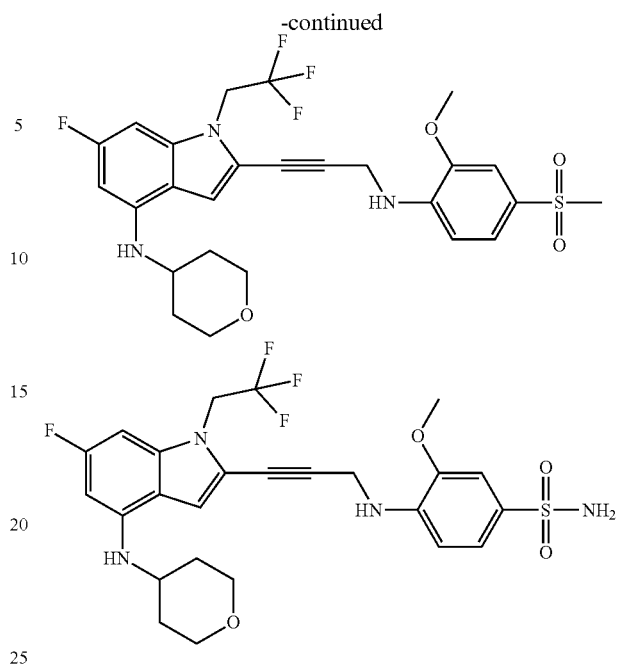

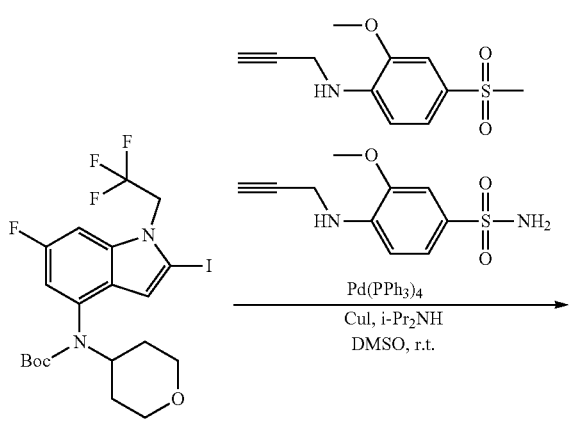

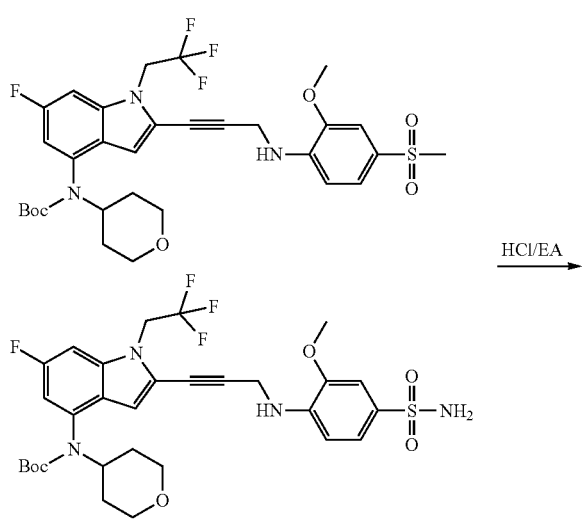

Preparation of 4-bromo-6-fluoro-1-((2-(trimethylsilyl)ethoxy)methyl)-1H-indole: To a mixture of NaH (2.80 g, 70.08 mmol, 60% in mineral oil, 3 eq.) in THF (5 mL) at 0° C. was added a solution of 2-(chloromethoxy)ethyl-trimethyl-silane (5.84 g, 35.04 mmol, 6.20 mL, 1.5 eq.) in THF (5 mL). The mixture was stirred at 0° C. for 1 h, and 4-bromo-6-fluoro-1H-indole (5 g, 23.36 mmol, 1 eq.) was added to the reaction. The resulting reaction mixture was stirred at 0° C. for 1 h. TLC analysis (PE:EtOAc=5:1, $R_f$=0.43) showed that the reaction was complete. The reaction mixture was quenched by adding saturated aqueous NH$_4$Cl (50 mL) and extracting the mixture with EtOAc (200 mL×3). The organic layer was washed with brine (500 mL), dried over anhydrous sodium sulfate, filtered, and concentrated under reduced pressure. The crude product was purified using column chromatography (SiO$_2$, PE:EtOAc=5:1, $R_f$=0.43) to give the desired product (14 g, 32.12 mmol, 68.76% yield) as a yellow oil. MS (ES$^{30}$, m/z): 346.0.

Preparation of 6-fluoro-N-(tetrahydro-2H-pyran-4-yl)-1-((2-(trimethylsilyl)ethoxy)methyl)-1H-indol-4-amine: To a solution of tetrahydro-2H-pyran-4-amine (4.87 g, 48.19 mmol, 3 eq.) in toluene (10 mL) were added 4-bromo-6-fluoro-1-((2-(trimethylsilyl)ethoxy)methyl)-1H-indole (7 g, 16.06 mmol, 1 eq.), Pd$_2$(dba)$_3$ (2.94 g, 3.21 mmol, 0.20 eq.), NaOtBu (2.01 g, 20.88 mmol, 1.30 eq.), and ditert-butyl-(2-phenylphenyl)phosphine (958.57 mg, 3.21 mmol, 0.20 eq.) at 20° C. The mixture was stirred at 85° C. for 12 h in a sealed tube. LC-MS analysis showed that the starting material was converted to one main product. The reaction mixture was poured into a saturated aqueous solution of EDTA (150 mL) and extracted with EtOAc (200 mL×3). The combined organic layers were stirred with saturated EDTA solution (200 mL) for 1 h. The organic layer was washed with brine (100 mL), dried over anhydrous sodium sulfate, filtered, and concentrated under reduced pressure. The crude product was purified by column chromatography (SiO$_2$, PE:EtOAc=5:1, $R_f$=0.43) to give the desired product (5.5 g, 9.51 mmol, 59.18% yield) as a yellow oil. MS (ES$^{30}$, m/z): 365.0.

Preparation of tert-butyl (6-fluoro-1-((2-(trimethylsilyl)ethoxy)methyl)-1H-indol-4-yl)(tetrahydro-2H-pyran-4-yl)

carbamate: To a solution of 6-fluoro-N-(tetrahydro-2H-pyran-4-yl)-1-((2-(trimethylsilyl)ethoxy)methyl)-1H-indol-4-amine (5.5 g, 9.51 mmol, 1 eq.) in t-BuOH (30 mL) was added Boc$_2$O (20.75 g, 95.05 mmol, 21.84 mL, 10 eq.) at 20° C. The mixture was stirred at 100° C. for 20 h. LC-MS and HPLC analysis showed that 50% of the product had formed. The reaction mixture was added to water (500 mL) and extracted with EtOAc (200 mL×3). The organic layer was washed with brine (500 mL), dried over anhydrous sodium sulfate, filtered, and concentrated in vacuo. The crude product was purified by column chromatography (SiO$_2$, PE:EtOAc=5:1, R$_f$=0.43) to afford the desired product (0.8 g, 1.21 mmol, 12.68% yield) as a yellow oil. MS (ES$^{30}$, m/z): 469.5.

Preparation of tert-butyl (6-fluoro-1H-indol-4-yl)(tetrahydro-2H-pyran-4-yl)carbamate: To a solution of tert-butyl (6-fluoro-1-((2-(trimethylsilyl)ethoxy)methyl)-1H-indol-4-yl)(tetrahydro-2H-pyran-4-yl)carbamate (1.5 g, 2.10 mmol, 1 eq.) in THF (5 mL) was added TBAF (1 M, 20.98 mL, 10 eq.) at 20° C. The mixture was stirred at 100° C. for 4 h. HPLC analysis showed that the reaction was complete. The reaction mixture was quenched with saturated aqueous solution of NaHCO$_3$ (50 mL) and extracted with EtOAc (100 mL×3). The organic layer was washed with brine (50 mL), dried over anhydrous sodium sulfate, filtered, and concentrated under reduced pressure. The crude product was purified by column chromatography (SiO$_2$, PE:EtOAc=4:1) to afford the desired product (0.42 g, 879.23 μmol, 41.90% yield) as a yellow solid.

Preparation of tert-butyl (6-fluoro-1-(phenylsulfonyl)-1H-indol-4-yl)(tetrahydro-2H-pyran-4-yl)carbamate: To a mixture of NaH (100.48 mg, 2.51 mmol, 60% in mineral oil, 3 eq.) in THF (2 mL) at 0° C. was added a solution of tert-butyl (6-fluoro-1H-indol-4-yl)(tetrahydro-2H-pyran-4-yl)carbamate (0.4 g, 837.36 μmol, 1 eq.) in THF (2 mL). The mixture was stirred at 0° C. for 1 h, and benzenesulfonyl chloride (221.84 mg, 1.26 mmol, 160.76 μL, 1.5 eq.) was added to the reaction. The mixture was stirred further at 0° C. for 1 h. LC-MS analysis showed that the reaction was complete. The reaction was quenched with saturated aqueous solution of NH$_4$Cl (50 mL) and extracted with EtOAc (10 mL×3). The organic layer was washed with brine (5 mL), dried over anhydrous sodium sulfate, filtered, and concentrated under reduced pressure. The crude product was purified by column chromatography (SiO$_2$, PE:EtOAc=2:1) to give the desired product (0.3 g, 606.90 μmol, 72.48% yield) as a yellow solid.

Preparation of tert-butyl (6-fluoro-2-iodo-1-(phenylsulfonyl)-1H-indol-4-yl)(tetrahydro-2H-pyran-4-yl)carbamate: To a solution of tert-butyl (6-fluoro-1-(phenylsulfonyl)-1H-indol-4-yl)(tetrahydro-2H-pyran-4-yl)carbamate (0.11 g, 213.26 μmol, 1 eq.) in THF (3 mL) at −78° C. was added LDA (2 M, 373.20 μL, 3.5 eq.). The mixture was stirred at −78° C. for 1 h, and a solution of I$_2$ (216.51 mg, 853.03 μmol, 171.83 μL, 4 eq.) in THF (2 mL) was added to the reaction. The mixture was stirred further at −78° C. for 1 h. LC-MS analysis showed that the reaction was complete. The reaction mixture was quenched by adding saturated aqueous NH$_4$Cl and extracted the mixture with EtOAc (20 mL×3). The organic layer was washed with brine (5 mL), dried over anhydrous sodium sulfate, filtered, and concentrated in vacuo. The crude product was purified by prep-TLC (PE: EtOAc=1:1) to give the desired product (0.25 g, 416.36 μmol, 65.08% yield) as a yellow solid.

Preparation of tert-butyl (6-fluoro-2-iodo-1H-indol-4-yl)(tetrahydro-2H-pyran-4-yl)carbamate: To a solution of tert-butyl (6-fluoro-2-iodo-1-(phenylsulfonyl)-1H-indol-4-yl)(tetrahydro-2H-pyran-4-yl)carbamate (0.12 g, 199.85 μmol, 1 eq.) in MeOH (3 mL) was added K$_2$CO$_3$ (110.49 mg, 799.41 μmol, 4 eq.). The mixture was stirred at 60° C. for 2 h. HPLC analysis showed that the reaction was complete. The reaction mixture was added to water (50 mL) and extracted with EtOAc (20 mL×3). The organic layer was washed with brine (50 mL), dried over anhydrous sodium sulfate, filtered, and concentrated to give the crude product (0.16 g, crude) as a yellow solid.

Preparation of tert-butyl (6-fluoro-2-iodo-1-(2,2,2-trifluoroethyl)-1H-indol-4-yl)(tetrahydro-2H-pyran-4-yl)carbamate: To a mixture of NaH (28.68 mg, 716.95 μmol, 60% in mineral oil, 3 eq.) in THF (2 mL) at 0° C. was added a solution of tert-butyl (6-fluoro-2-iodo-1H-indol-4-yl)(tetrahydro-2H-pyran-4-yl)carbamate (0.11 g, 238.98 μmol, 1 eq.) in THF (1 mL). The mixture was stirred at 0° C. for 1 h, and 2,2,2-trifluoroethyl trifluoromethanesulfonate (277.34 mg, 1.19 mmol, 5 eq.) was added to the reaction. The resulting reaction mixture was stirred further at 0° C. for 1 h. LC-MS analysis showed that the reaction was complete. The reaction mixture was quenched by adding saturated aqueous NH$_4$Cl (15 mL) and extracting the mixture with EtOAc (20 mL×3). The organic layer was washed with brine (5 mL), dried over anhydrous sodium sulfate, filtered, and concentrated under reduced pressure to afford the crude product (0.11 g, crude) as a yellow solid.

Preparation of tert-butyl (6-fluoro-2-(3-((2-methoxy-4-(methylsulfonyl)phenyl)amino)prop-1-yn-1-yl)-1-(2,2,2-trifluoroethyl)-1H-indol-4-yl)(tetrahydro-2H-pyran-4-yl)carbamate and tert-butyl (6-fluoro-2-(3-((2-methoxy-4-sulfamoylphenyl)amino)prop-1-yn-1-yl)-1-(2,2,2-trifluoroethyl)-1H-indol-4-yl)(tetrahydro-2H-pyran-4-yl)carbamate: To a mixture 2-methoxy-4-(methylsulfonyl)-N-(prop-2-yn-1-yl)aniline or 3-methoxy-4-(prop-2-yn-1-ylamino)benzenesulfonamide (2 eq.) and tert-butyl (6-fluoro-2-iodo-1-(2,2,2-trifluoroethyl)-1H-indol-4-yl)(tetrahydro-2H-pyran-4-yl)carbamate (0.07 g, 129.08 μmol, 1 eq.) in DMSO (5 mL) were added CuI (1 eq.), Pd(PPh$_3$)$_4$ (0.10 eq.), and N-isopropylpropan-2-amine (1 eq.). The mixture was stirred at 25° C. for 1 h. LC-MS analysis showed that the reaction was complete. The reaction mixture was poured into water (50 mL) and extracted with EtOAc (20 mL×3). The combined organic layers were washed with saturated aqueous EDTA (20 mL) by stirring the mixture for 1 h. The organic layer was washed with brine (50 mL), dried over anhydrous sodium sulfate, filtered, and concentrated under reduced pressure. The crude product was purified by prep-TLC to give the desired products as yellow solids.

Preparation of 6-fluoro-2-{3-[(4-methanesulfonyl-2-methoxyphenyl)amino]prop-1-yn-1-yl}-N-(oxan-4-yl)-1-(2,2,2-trifluoroethyl)-1H-indol-4-amine and 4-[(3-{6-fluoro-4-[(oxan-4-yl)amino]-1-(2,2,2-trifluoroethyl)-1H-indol-2-yl}prop-2-yn-1-yl)amino]-3-methoxybenzene-1-sulfonamide: A mixture of tert-butyl (6-fluoro-2-(3-((2-methoxy-4-(methylsulfonyl)phenyl)amino)prop-1-yn-1-yl)-1-(2,2,2-trifluoroethyl)-1H-indol-4-yl)(tetrahydro-2H-pyran-4-yl)carbamate or tert-butyl (6-fluoro-2-(3-((2-methoxy-4-sulfamoylphenyl)amino)prop-1-yn-1-yl)-1-(2,2,2-trifluoroethyl)-1H-indol-4-yl)(tetrahydro-2H-pyran-4-yl)carbamate (50 mg, 1 eq.) in 4N HCl/EtOAc (4 mL, 254 eq.) was stirred at 25° C. for 1 h. LC-MS analysis showed that the reaction was complete. The reaction was concentrated to give the crude products.

6-fluoro-2-{3-[(4-methanesulfonyl-2-methoxyphenyl)amino]prop-1-yn-1-yl}-N-(oxan-4-yl)-1-(2,2,2-trifluoroethyl)-1H-indol-4-amine, MS (ES$^{30}$, m/z): 554.1; and 4-[(3-{6-fluoro-4-[(oxan-4-yl)amino]-1-(2,2,2-trifluoroethyl)-

1H-indol-2-yl}prop-2-yn-1-yl)amino]-3-methoxybenzene-1-sulfonamide, MS (E S*, m/z): 555.1.

Example E5: Synthesis of Compounds 1016A, 1017A, 1018A, 1019A, 1020A, 1021A, 1027A, 1028A, 1029A, 1030A, 1031A, and 1032A

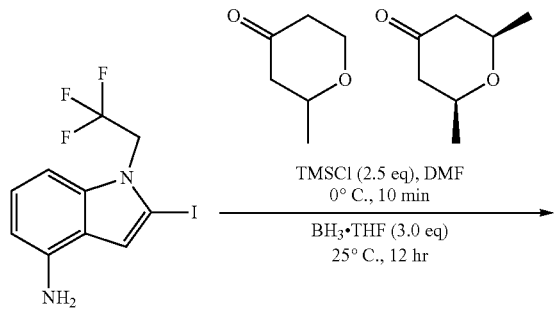

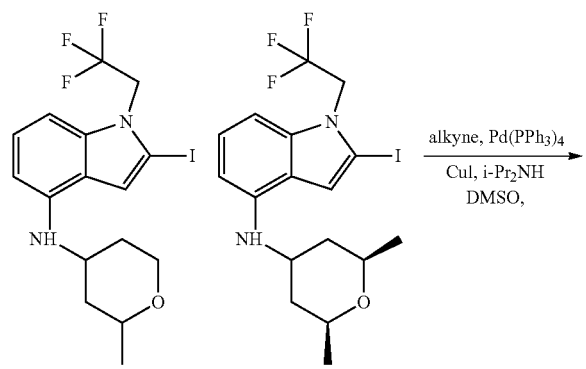

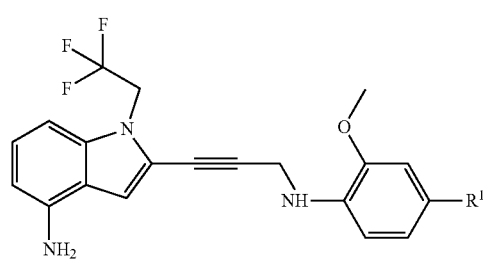

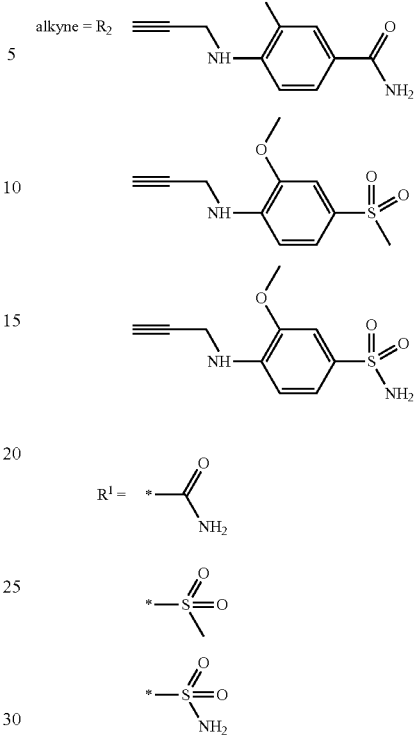

Preparation of 2-iodo-N-(2-methyltetrahydro-2H-pyran-4-yl)-1-(2,2,2-trifluoroethyl)-1H-indol-4-amine and N-((2R,6S)-2,6-dimethyltetrahydro-2H-pyran-4-yl)-2-iodo-1-(2,2,2-trifluoroethyl)-1H-indol-4-amine: To a mixture of 2-iodo-1-(2,2,2-trifluoroethyl)-1H-indol-4-amine (500 mg, 1 eq.) and 2-methyltetrahydro-4H-pyran-4-one (500 mg, 1 eq.) or (2R,6S)-2,6-dimethyltetrahydro-4H-pyran-4-one (376 mg, 2 eq.) in DMF (10 mL) was added TMSCl (399 mg, 2.5 eq.). The mixture was stirred at 0° C. for 1 h, and BH₃·THF (379 mg, 3 eq., 1 M) was added to the reaction under N₂. The mixture was stirred at 0° C. for 12 h. TLC (PE:EtOAc=5:1, Rf=0.50) indicated the reaction was completed. The reaction mixture was poured into water (150 mL), then extracted with EtOAc (80 mL×3). The combined organic layers was washed with saturated brine (80 mL), filtered and concentrated under reduced pressure to afford the desired compound.

Preparation of final products: To a solution of alkyne (1.2 eq.) in DMSO (5 mL) were added CuI (1 eq.) and i-Pr₂NH (10 eq.). The solution was degassed with N₂ three times, and 2-iodo-N-(2-methyltetrahydro-2H-pyran-4-yl)-1-(2,2,2-trifluoroethyl)-1H-indol-4-amine or N-((2R,6S)-2,6-dimethyltetrahydro-2H-pyran-4-yl)-2-iodo-1-(2,2,2-trifluoroethyl)-1H-indol-4-amine (1 eq.) and Pd(PPh₃)₄ (0.2 eq.) were added to the solution. The reaction mixture was stirred at 25° C. for 2 h. TLC analysis showed that the starting material was consumed completely, and one main peak with the desired mass was detected. The reaction mixture was diluted with EtOAc (5 mL), and the resulting mixture was poured into saturated aqueous EDTA (30 mL) and stirred for 1 h. The mixture was then extracted with EtOAc (15 mL×2). The combined organic layers were washed with brine (10 mL) and concentrated under reduced pressure. The crude residue was purified by prep-TLC to afford the desired products.

3-methoxy-4-{[3-(4-{[(2S,4R)-2-methyloxan-4-yl]
amino}-1-(2,2,2-trifluoroethyl)-1H-indol-2-yl)prop-2-yn-1-
yl]amino}benzamide, MS (ES³⁰, m/z): 515.2; 3-methoxy-
4-{[3-(4-{[(2S,4S)-2-methyloxan-4-yl]amino}-1-(2,2,2-
trifluoroethyl)-1H-indol-2-yl)prop-2-yn-1-yl]amino}ben-
zamide, MS (ES³⁰, m/z): 515.2; 3-methoxy-4-{[3-(4-{[(2S,
4R)-2-methyloxan-4-yl]amino}-1-(2,2,2-trifluoroethyl)-
1H-indol-2-yl)prop-2-yn-1-yl]amino}benzene-1-sulfona-
mide, MS (ES³⁰, m/z): 551.2; 3-methoxy-4-{[3-(4-{[(2S,
4S)-2-methyloxan-4-yl]amino}-1-(2,2,2-trifluoroethyl)-1H-
indol-2-yl)prop-2-yn-1-yl]amino}benzene-1-sulfonamide,
MS (ES³⁰, m/z): 551.2; 3-methoxy-4-{[3-(4-{[(2R,4S,6S)-
2,6-dimethyloxan-4-yl]amino}-1-(2,2,2-trifluoroethyl)-1H-
indol-2-yl)prop-2-yn-1-yl]amino}benzamide, MS (ES³⁰,
m/z): 529.2; 3-methoxy-4-{[3-(4-{[(2R,4R,6S)-2,6-dimeth-
yloxan-4-yl]amino}-1-(2,2,2-trifluoroethyl)-1H-indol-2-yl)
prop-2-yn-1-yl]amino}benzamide, MS (ES³⁰, m/z): 529.2;
2-{3-[(4-methanesulfonyl-2-methoxyphenyl)amino]prop-1-
yn-1-yl}-N-[(2R,4S,6S)-2,6-dimethyloxan-4-yl]-1-(2,2,2-
trifluoroethyl)-1H-indol-4-amine, MS (ES³⁰, m/z): 564.2;
2-{3-[(4-methanesulfonyl-2-methoxyphenyl)amino]prop-1-
yn-1-yl}-N-[(2R,4R,6S)-2,6-dimethyloxan-4-yl]-1-(2,2,2-
trifluoroethyl)-1H-indol-4-amine, MS (ES³⁰, m/z): 564.2;
3-methoxy-4-{[3-(4-{[(2R,4S,6S)-2,6-dimethyloxan-4-yl]
amino}-1-(2,2,2-trifluoroethyl)-1H-indol-2-yl)prop-2-yn-1-
yl]amino}benzene-1-sulfonamide, MS (ES³⁰, m/z): 565.2;
and 3-methoxy-4-{[3-(4-{[(2R,4R,6S)-2,6-dimethyloxan-4-
yl]amino}-1-(2,2,2-trifluoroethyl)-1H-indol-2-yl)prop-2-
yn-1-yl]amino}benzene-1-sulfonamide, MS (ES³⁰, m/z):
565.2; 2-{3-[(4-methanesulfonyl-2-methoxyphenyl)amino]
prop-1-yn-1-yl}-N-[(2S,4S)-2-methyloxan-4-yl]-1-(2,2,2-
trifluoroethyl)-1H-indol-4-amine, MS (ES³⁰, m/z): 550.2;
2-{3-[(4-methanesulfonyl-2-methoxyphenyl)amino]prop-1-
yn-1-yl}-N-[(2S,4R)-2-methyloxan-4-yl]-1-(2,2,2-trifluoro-
ethyl)-1H-indol-4-amine, MS (ES³⁰, m/z): 550.2.

Example E6: General Procedure for Preparation of
Compounds 1010A and 1012A

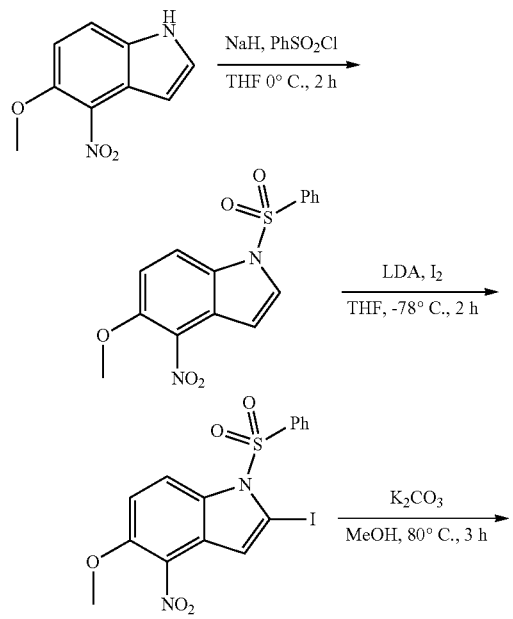

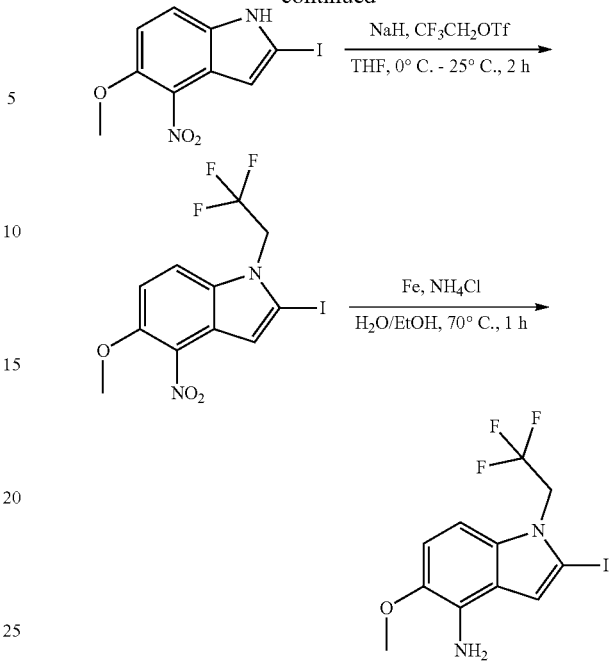

Synthesis of 5-methoxy-4-nitro-1-(phenylsulfonyl)-1H-
indole: In each of two separate, identical batches, a solution
of 5-methoxy-4-nitro-1H-indole (2 g, 10.41 mmol, 1 eq.) in
THF (1 mL) was added to a mixture of NaH (1.25 g, 31.22
mmol, 60% in mineral oil, 3 eq.) and THF (3 mL) at 0° C.
The mixture was stirred for 1 h at 0° C., and then added
benzenesulfonyl chloride (2.76 g, 15.61 mmol, 2 mL, 1.5
eq.) was added. The mixture was stirred for an additional 1
h at 0° C., after which time TLC (PE:EtOAc=4:1, $R_f$=0.43)
indicated that the reaction was complete. The batches were
combined, and the resulting mixture was quenched by
addition of saturated aqueous NH₄Cl (20 mL) at 0° C., and
then diluted with EtOAc (20 mL) and extracted with EtOAc
(20 mL×3). The combined organic layers were washed with
brine (20 mL), dried over sodium sulfate, filtered, and
concentrated under reduced pressure. The crude residue was
washed with PE (20 mL) to provide 5-methoxy-4-nitro-1-
(phenylsulfonyl)-1H-indole (7 g, 16.85 mmol, 80.96%
yield) as a yellow solid, which was used directly in the next
step without further purification.

Synthesis of 2-iodo-5-methoxy-4-nitro-1-(phenylsulfo-
nyl)-1H-indole: To each of two separate, identical batches
containing a mixture of 5-methoxy-4-nitro-1-(phenylsulfo-
nyl)-1H-indole (0.5 g, 1.20 mmol, 1 eq.) in THF (30 mL) at
-78° C. was added lithium diisopropylamide (2 M, 2.41 mL,
4 eq.). The mixture was stirred 1 h at -78° C. under N₂. I₂
(1.22 g, 4.81 mmol, 969.81 µL, 4 eq.) in THF (13 mL) was
then added, and the mixture was stirred for an additional 1
h at -78° C. under N₂. The batches were then combined, and
the resulting mixture was poured into saturated aqueous
NH₄Cl solution (25 mL) and stirred for 5 min, and then
extracted with EtOAc (25 mL×3). The combined organic
layers were washed with brine (20 mL×3), dried over
anhydrous sodium sulfate, filtered, and concentrated in
vacuo. The residue was purified by prep-TLC (SiO₂, PE:E-
tOAc=4:1) to provide 2-iodo-5-methoxy-4-nitro-1-(phe-
nylsulfonyl)-1H-indole (0.7 g, 763.81 µmol, 31.73% yield)
as a yellow solid.

Synthesis of 2-iodo-5-methoxy-4-nitro-1H-indole: A mixture of 2-iodo-5-methoxy-4-nitro-1-(phenylsulfonyl)-1H-indole (0.7 g, 763.81 µmol, 1 eq.) and K$_2$CO$_3$ (316.69 mg, 2.29 mmol, 3 eq.) in MeOH (5 mL) was stirred at 70° C. for 2 h, after which time LC-MS analysis indicated that the reaction was complete. The residue was poured into water (25 mL), stirred for 5 min, and then extracted with EtOAc (25 mL×3). The combined organic layers were washed with brine (20 mL×3), dried over anhydrous sodium sulfate, filtered, and concentrated in vacuo. The residue was purified by column chromatography (SiO$_2$, PE:EtOAc=4:1, R$_f$=0.31) to provide 2-iodo-5-methoxy-4-nitro-1H-indole (0.1 g, 251.52 µmol, 32.93% yield) as a yellow solid.

Synthesis of 2-iodo-5-methoxy-4-nitro-1-(2,2,2-trifluoroethyl)-1H-indole: To a mixture of NaH (30.18 mg, 754.56 µmol, 60% in mineral oil, 3 eq.) in THF (2 mL) at 0° C. was added 2-iodo-5-methoxy-4-nitro-1H-indole (0.1 g, 251.52 µmol, 1 eq.) in THF (2 mL). The mixture was stirred for 1 h at 0° C., and 2,2,2-trifluoroethyl trifluoromethanesulfonate (291.89 mg, 1.26 mmol, 5 eq.) was added. The mixture was stirred at 0° C. for an additional 1 h, after which time TLC analysis (PE:EtOAc=1:1, R$_f$=0.43) indicated that the reaction was complete. The reaction mixture was then quenched by adding saturated aqueous NH$_4$Cl (20 mL) at 0° C., diluted with EtOAc (20 mL), and extracted with EtOAc (20 mL×3). The combined organic layers were washed with brine (20 mL), dried over anhydrous sodium sulfate, filtered, and concentrated under reduced pressure to provide 2-iodo-5-methoxy-4-nitro-1-(2,2,2-trifluoroethyl)-1H-indole (0.1 g, crude) as a yellow solid. The crude residue was used directly in the next step.

Synthesis of 2-iodo-5-methoxy-1-(2,2,2-trifluoroethyl)-1H-indol-4-amine: To a mixture of 2-iodo-5-methoxy-4-nitro-1-(2,2,2-trifluoroethyl)-1H-indole (0.1 g, 249.94 µmol, 1 eq.) in EtOH (5 mL) and water (1 mL) was added saturated aqueous NH$_4$Cl (66.85 mg, 1.25 mmol, 43.69 µL, 5 eq.). The mixture was heated to 70° C., and Fe (69.79 mg, 1.25 mmol, 5 eq.) was added. The mixture stirred at 70° C. for 1 h, after which time LC-MS analysis indicated that the reaction was complete. water (20 mL) was added, and then the mixture was extracted with EtOAc (20 mL×3). The combined organic layers were washed with brine (20 mL), dried over anhydrous sodium sulfate, filtered, and concentrated under reduced pressure. The residue was purified by prep-TLC (SiO$_2$, PE:EtOAc=1:1 R$_f$=0.43) to provide 2-iodo-5-methoxy-1-(2,2,2-trifluoroethyl)-1H-indol-4-amine (0.035 g, 80.38 µmol, 32.16% yield) as a yellow solid.

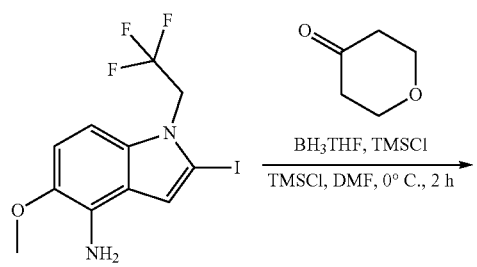

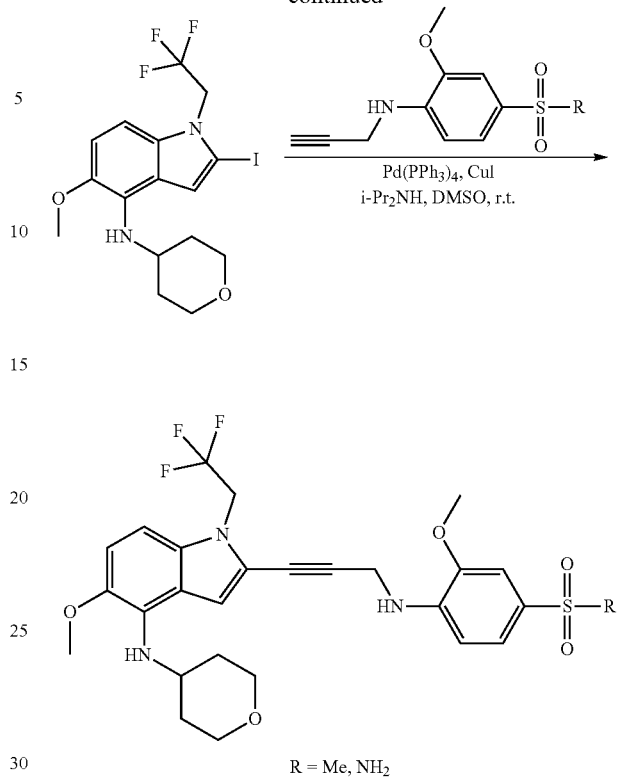

R = Me, NH$_2$

Synthesis of 2-iodo-5-methoxy-N-(tetrahydro-2H-pyran-4-yl)-1-(2,2,2-trifluoroethyl)-1H-indol-4-amine: To a mixture of tetrahydropyran-4-one (24.14 mg, 241.15 µmol, 22.15 µL, 3 eq.) and 2-iodo-5-methoxy-1-(2,2,2-trifluoroethyl)-1H-indol-4-amine (0.035 g, 80.38 µmol, 1 eq.) in DMF (2 mL) was added TMSCl (21.83 mg, 200.95 µmol, 25.50 µL, 2.5 eq.). The mixture was cooled to 0° C., and BH$_3$·THF (1 M, 200.95 µL, 2.5 eq.) was then added under N$_2$. The mixture was stirred at 0° C. for 1 h, after which time LC-MS analysis indicated that the reaction was complete. The reaction mixture was quenched by adding water (100 mL) at 0° C. and then extracted with EtOAc (30 mL×3). The combined organic layers were washed with brine (30 mL), dried over anhydrous sodium sulfate, filtered, and concentrated under reduced pressure. The residue was purified by prep-TLC (SiO$_2$, PE:EtOAc=1:1, R$_f$=0.28) to provide 2-iodo-5-methoxy-N-(tetrahydro-2H-pyran-4-yl)-1-(2,2,2-trifluoroethyl)-1H-indol-4-amine (0.03 g, 56.14 µmol, 69.84% yield) as a yellow solid.

Preparation of final products: 2-iodo-5-methoxy-N-(tetrahydro-2H-pyran-4-yl)-1-(2,2,2-trifluoroethyl)-1H-indol-4-amine was coupled to the R-substituted alkynes specified above according to the general procedure specified in EXAMPLE C51. In each case, the reactions were deemed complete after stirring for 1 h at 30° C., and the crude compounds were first purified by prep-TLC and further purified by prep-HPLC.

3-methoxy-4-[(3-{5-methoxy-4-[(oxan-4-yl)amino]-1-(2,2,2-trifluoroethyl)-1H-indol-2-yl}prop-2-yn-1-yl)amino]benzene-1-sulfonamide, MS (ES$^{30}$, m/z): 567.3; and 2-{3-[(4-methanesulfonyl-2-methoxyphenyl)amino]prop-1-yn-1-yl}-5-methoxy-N-(oxan-4-yl)-1-(2,2,2-trifluoroethyl)-1H-indol-4-amine, MS (ES$^{30}$, m/z): 566.2.

Example E7: Preparation of Compound 1013A

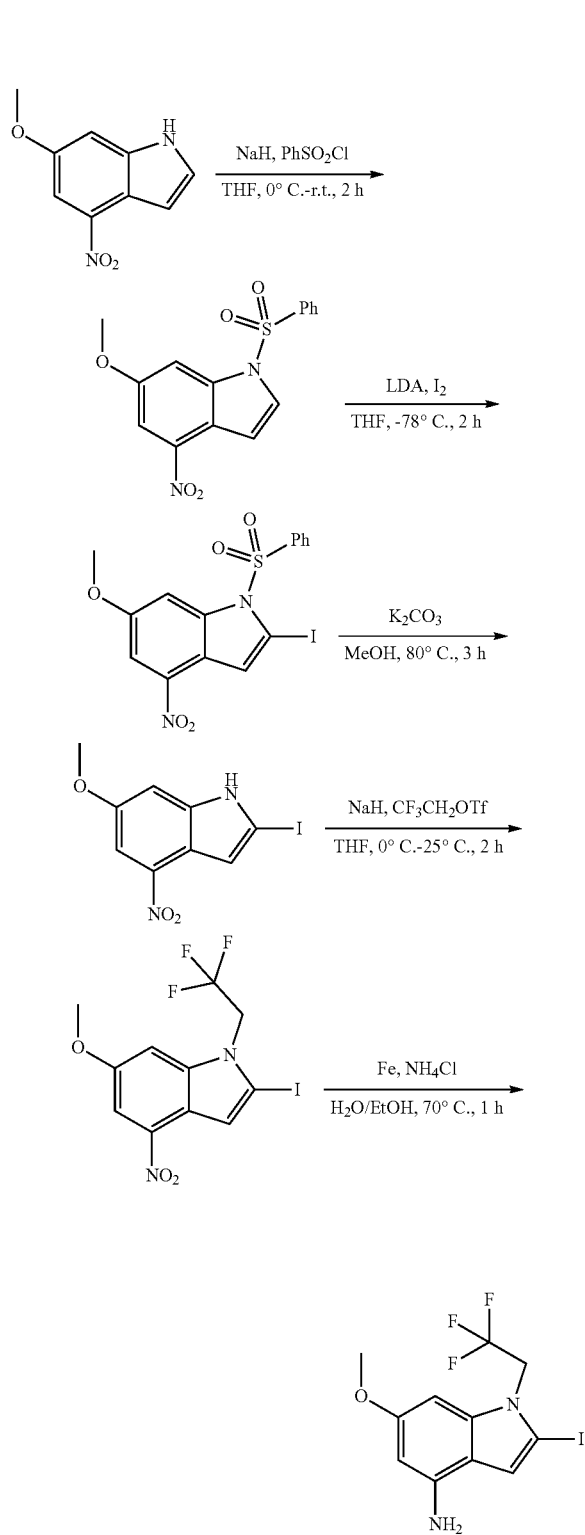

2-iodo-6-methoxy-1-(2,2,2-trifluoroethyl)-1H-indol-4-amine was prepared via an analogous procedure to the synthesis of 2-iodo-5-methoxy-1-(2,2,2-trifluoroethyl)-1H-indol-4-amine according to EXAMPLE E6, using 6-methoxy-4-nitro-1H-indole in place of 5-methoxy-4-nitro-1H-indole.

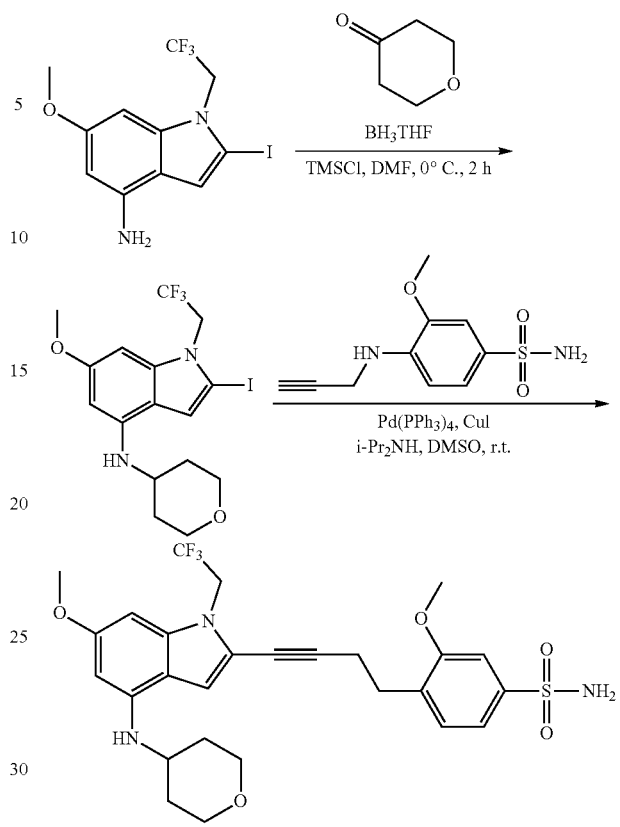

Synthesis of 2-iodo-6-methoxy-N-(tetrahydro-2H-pyran-4-yl)-1-(2,2,2-trifluoroethyl)-1H-indol-4-amine: To a mixture of tetrahydropyran-4-one (27.59 mg, 275.59 μmol, 25.31 μL, 3 eq.) and 2-iodo-6-methoxy-1-(2,2,2-trifluoroethyl)indol-4-amine (0.04 g, 91.86 μmol, 1 eq.) in DMF (2 mL) was added TMSCl (24.95 mg, 229.66 μmol, 29.15 μL, 2.5 eq.). The mixture was cooled to 0° C., and BH$_3$·THF (1 M, 229.66 μL, 2.5 eq.) was then added under N$_2$. The mixture was stirred at 0° C. for 1 h, after which time LC-MS analysis indicated that the reaction was complete. The reaction mixture was quenched by adding water (100 mL) at 0° C., and then extracted with EtOAc (30 mL×3). The combined organic layers were washed with brine (30 mL), dried over anhydrous sodium sulfate, filtered, and concentrated under reduced pressure. The residue was purified by prep-TLC (SiO$_2$, PE:EtOAc=4:1, R$_f$=0.44) to provide 2-iodo-6-methoxy-N-(tetrahydro-2H-pyran-4-yl)-1-(2,2,2-trifluoroethyl)-1H-indol-4-amine (0.035 g, 61.64 μmol, 67.10% yield) as a yellow solid.

Preparation of final product: To a mixture of 3-methoxy-4-(prop-2-yn-1-ylamino)benzenesulfonamide (24.45 mg, 91.58 μmol, 1.3 eq.) and 2-iodo-6-methoxy-N-(tetrahydro-2H-pyran-4-yl)-1-(2,2,2-trifluoroethyl)-1H-indol-4-amine (0.04 g, 70.45 μmol, 1 eq.) in DMSO (2 mL) was added CuI (13.42 mg, 70.45 μmol, 1 eq.), followed by Pd(PPh$_3$)$_4$ (8.14 mg, 7.04 μmol, 0.10 eq.) and diisopropylamine (7.13 mg, 70.45 μmol, 9.96 μL, 1 eq.). The mixture was stirred at 30° C. for 1 h under N$_2$, after which time TLC analysis (PE:EtOAc=1:1, R$_f$=0.23) indicated that the reaction was complete. The reaction mixture was quenched by adding a saturated aqueous solution of EDTA (30 mL) and EtOAc (10 mL), stirred at 25° C. for 1 h, and extracted with EtOAc (20 mL×3). The combined organic layers were washed with brine (30 mL), dried over anhydrous sodium sulfate, filtered, and concentrated under reduced pressure. The residue was purified by prep-TLC (SiO₂, PE:EtOAc=0:1, R$_f$=0.24), then further purified by prep-HPLC to provide 3-methoxy-4-[(3-{6-methoxy-4-[(oxan-4-yl)amino]-1-(2,2,2-trifluoroethyl)-1H-indol-2-yl}prop-2-yn-1-yl)amino]benzene-1-sulfonamide (0.0155 g, 26.59 μmol, 37.74% yield) as white solid. MS (ES⁺, m/z): 567.0.

TABLE 5 shows compounds with a 2-ethynyl-N-(tetrahydropyran-4-yl)-1H-indole-4-amine core.

TABLE 5

| Compound No. | Structure | IUPAC | LC-MS (ES⁺, m/z) |
|---|---|---|---|
| 991A | 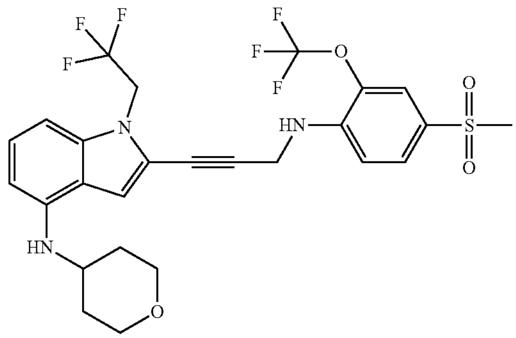 [SMILES: CS(=O)(=O)c1ccc(NCC#Cc2cc3c(NC4CCOCC4)cccc3n2CC(F)(F)F)c(OC(F)(F)F)c1] | 2-(3-{[4-methanesulfonyl-2-(trifluoromethoxy)phenyl]amino}prop-1-yn-1-yl)-N-(oxan-4-yl)-1-(2,2,2-trifluoroethyl)-1H-indol-4-amine | 590.3 |
| 992A | 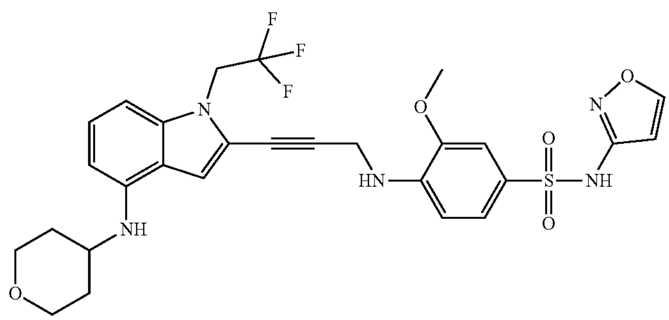 [SMILES: COc1cc(S(=O)(=O)Nc2ccon2)ccc1NCC#Cc1cc2c(NC3CCOCC3)cccc2n1CC(F)(F)F] | 3-methoxy-4-[(3-{4-[(oxan-4-yl)amino]-1-(2,2,2-trifluoroethyl)-1H-indol-2-yl}prop-2-yn-1-yl)amino]-N-(1,2-oxazol-3-yl)benzene-1-sulfonamide | 604.2 |
| 993A | 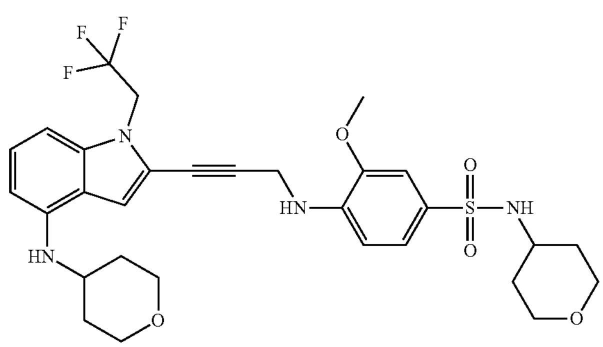 [SMILES: COc1cc(S(=O)(=O)NC2CCOCC2)ccc1NCC#Cc1cc2c(NC3CCOCC3)cccc2n1CC(F)(F)F] | 3-methoxy-N-(oxan-4-yl)-4-[(3-{4-[(oxan-4-yl)amino]-1-(2,2,2-trifluoroethyl)-1H-indol-2-yl}prop-2-yn-1-yl)amino]benzene-1-sulfonamide | 621.3 |
| 994A | 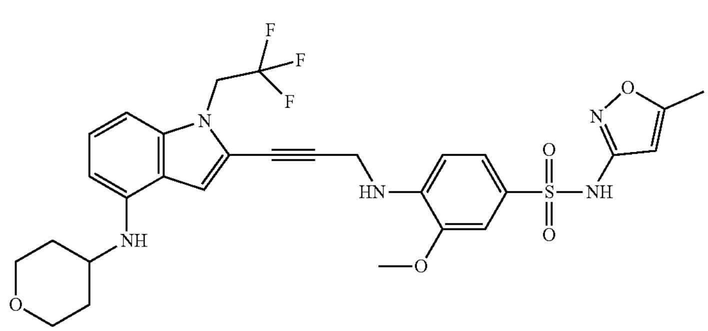 [SMILES: COc1cc(S(=O)(=O)Nc2cc(C)on2)ccc1NCC#Cc1cc2c(NC3CCOCC3)cccc2n1CC(F)(F)F] | 3-methoxy-N-(5-methyl-1,2-oxazol-3-yl)-4-[(3-{4-[(oxan-4-yl)amino]-1-(2,2,2-trifluoroethyl)-1H-indol-2-yl}prop-2-yn-1-yl)amino]benzene-1-sulfonamide | 618.2 |

TABLE 5-continued

| Compound No. | Structure | IUPAC | LC-MS (ES+, m/z) |
|---|---|---|---|
| 995A | 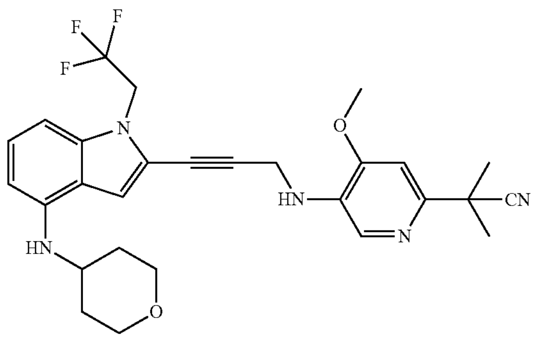 [SMILES: COc1cc(C(C)(C)C#N)ncc1NCC#Cc1cc2c(NC3CCOCC3)cccc2n1CC(F)(F)F] | 2-{4-methoxy-5-[(3-{4-[(oxan-4-yl)amino]-1-(2,2,2-trifluoroethyl)-1H-indol-2-yl}prop-2-yn-1-yl)amino]pyridin-2-yl}-2-methylpropanenitrile | 526.2 |
| 996A | 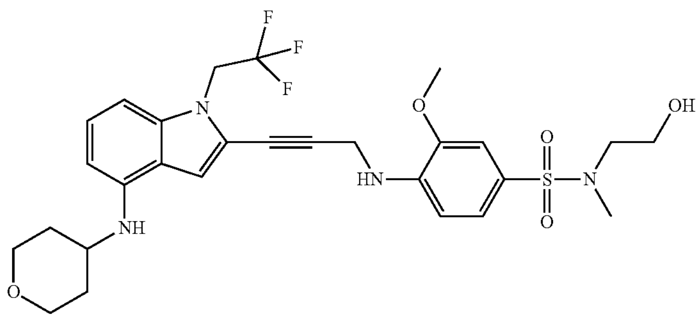 [SMILES: COc1cc(S(=O)(=O)N(C)CCO)ccc1NCC#Cc1cc2c(NC3CCOCC3)cccc2n1CC(F)(F)F] | N-(2-hydroxyethyl)-3-methoxy-N-methyl-4-[(3-{4-[(oxan-4-yl)amino]-1-(2,2,2-trifluoroethyl)-1H-indol-2-yl}prop-2-yn-1-yl)amino]benzene-1-sulfonamide | 595.2 |
| 997A | 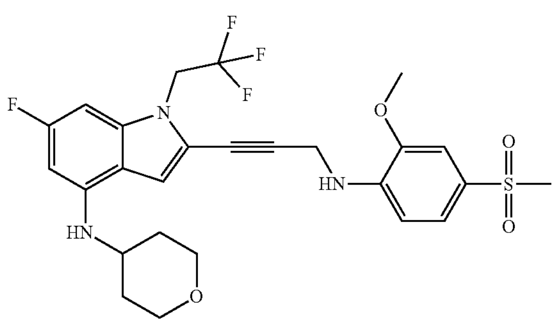 [SMILES: COc1cc(S(C)(=O)=O)ccc1NCC#Cc1cc2c(NC3CCOCC3)cc(F)cc2n1CC(F)(F)F] | 6-fluoro-2-{3-[(4-methanesulfonyl-2-methoxyphenyl)amino]prop-1-yn-1-yl}-N-(oxan-4-yl)-1-(2,2,2-trifluoroethyl)-1H-indol-4-amine | 554.1 |
| 998A | 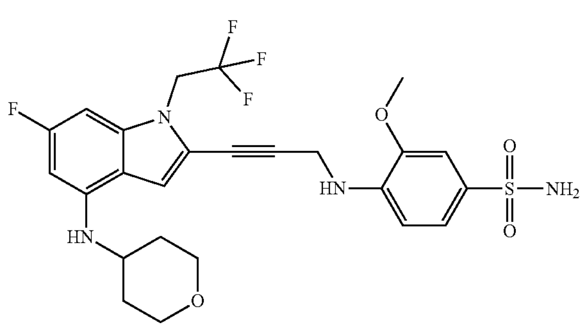 [SMILES: COc1cc(S(N)(=O)=O)ccc1NCC#Cc1cc2c(NC3CCOCC3)cc(F)cc2n1CC(F)(F)F] | 4-[(3-{6-fluoro-4-[(oxan-4-yl)amino]-1-(2,2,2-trifluoroethyl)-1H-indol-2-yl}prop-2-yn-1-yl)amino]-3-methoxybenzene-1-sulfonamide | 555.1 |

TABLE 5-continued

| Compound No. | Structure | IUPAC | LC-MS (ES+, m/z) |
|---|---|---|---|
| 999A | 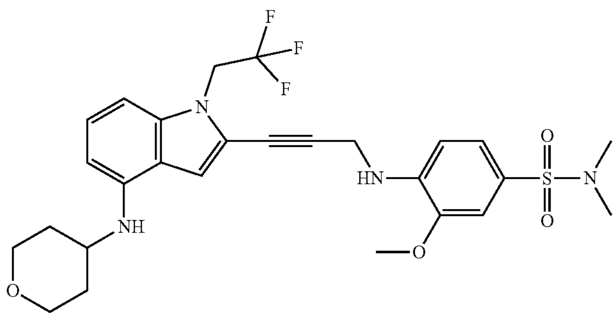 [SMILES: COc1cc(S(=O)(=O)N(C)C)ccc1NCC#Cc1cc2c(NC3CCOCC3)cccc2n1CC(F)(F)F] | 3-methoxy-N,N-dimethyl-4-[(3-{4-[(oxan-4-yl)amino]-1-(2,2,2-trifluoroethyl)-1H-indol-2-yl}prop-2-yn-1-yl)amino]benzene-1-sulfonamide | 565.2 |
| 1000A | 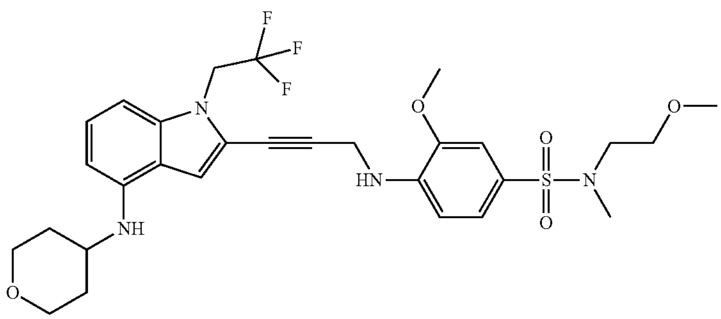 [SMILES: COCCN(C)S(=O)(=O)c1ccc(NCC#Cc2cc3c(NC4CCOCC4)cccc3n2CC(F)(F)F)c(OC)c1] | 3-methoxy-N-(2-methoxyethyl)-N-methyl-4-[(3-{4-[(oxan-4-yl)amino]-1-(2,2,2-trifluoroethyl)-1H-indol-2-yl}prop-2-yn-1-yl)amino]benzene-1-sulfonamide | 609.2 |
| 1001A | 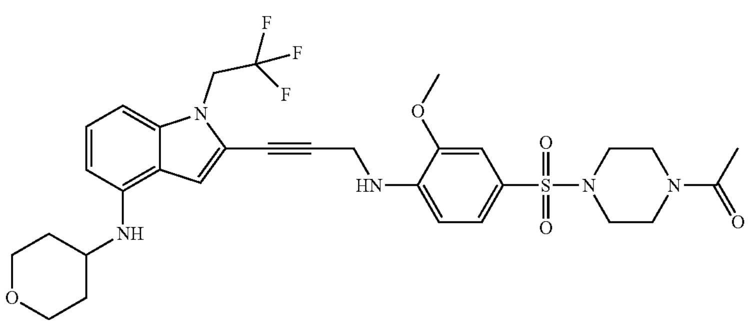 [SMILES: COc1cc(S(=O)(=O)N2CCN(C(C)=O)CC2)ccc1NCC#Cc1cc2c(NC3CCOCC3)cccc2n1CC(F)(F)F] | 1-(4-{3-methoxy-4-[(3-{4-[(oxan-4-yl)amino]-1-(2,2,2-trifluoroethyl)-1H-indol-2-yl}prop-2-yn-1-yl)amino]benzenesulfonyl}piperazin-1-yl)ethan-1-one | 648.2 |
| 1002A | 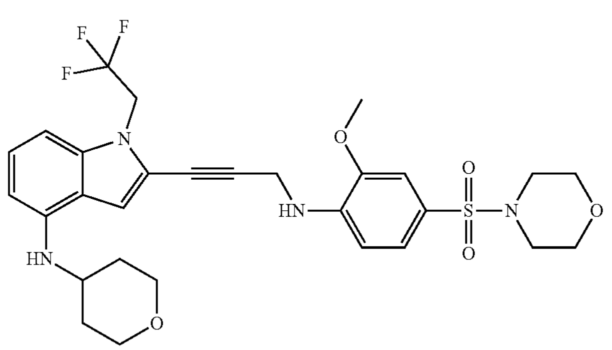 [SMILES: COc1cc(S(=O)(=O)N2CCOCC2)ccc1NCC#Cc1cc2c(NC3CCOCC3)cccc2n1CC(F)(F)F] | 2-(3-{[2-methoxy-4-(morpholine-4-sulfonyl)phenyl]amino}prop-1-yn-1-yl)-N-(oxan-4-yl)-1-(2,2,2-trifluoroethyl)-1H-indol-4-amine | 607.2 |

TABLE 5-continued

| Compound No. | Structure | IUPAC | LC-MS (ES+, m/z) |
|---|---|---|---|
| 1003A | 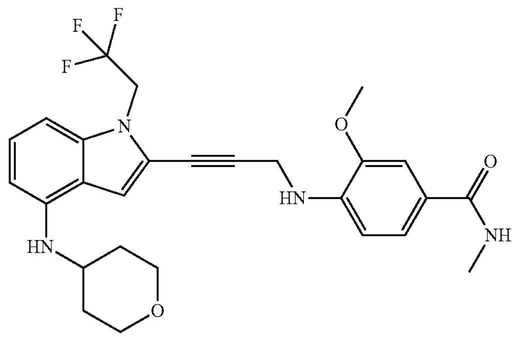 [SMILES: CNC(=O)c1ccc(NCC#Cc2cc3c(NC4CCOCC4)cccc3n2CC(F)(F)F)c(OC)c1] | 3-methoxy-N-methyl-4-[(3-{4-[(oxan-4-yl)amino]-1-(2,2,2-trifluoroethyl)-1H-indol-2-yl}prop-2-yn-1-yl)amino]benzamide | 515.2 |
| 1004A | 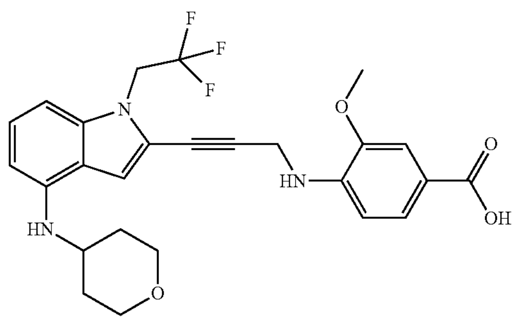 [SMILES: COc1cc(C(=O)O)ccc1NCC#Cc1cc2c(NC3CCOCC3)cccc2n1CC(F)(F)F] | 3-methoxy-4-((3-(4-((tetrahydro-2H-pyran-4-yl)amino)-1-(2,2,2-trifluoroethyl)-1H-indol-2-yl)prop-2-yn-1-yl)amino)benzoic acid | 502.2 |
| 1005A | 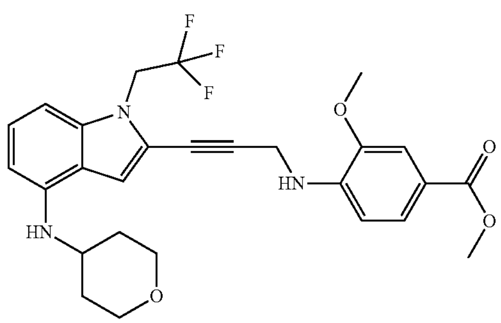 [SMILES: COC(=O)c1ccc(NCC#Cc2cc3c(NC4CCOCC4)cccc3n2CC(F)(F)F)c(OC)c1] | methyl 3-methoxy-4-((3-(4-((tetrahydro-2H-pyran-4-yl)amino)-1-(2,2,2-trifluoroethyl)-1H-indol-2-yl)prop-2-yn-1-yl)amino)benzoate | 516.2 |
| 1006A | 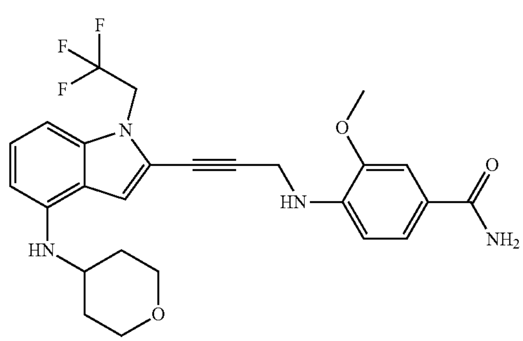 [SMILES: COc1cc(C(N)=O)ccc1NCC#Cc1cc2c(NC3CCOCC3)cccc2n1CC(F)(F)F] | 3-methoxy-4-((3-(4-((tetrahydro-2H-pyran-4-yl)amino)-1-(2,2,2-trifluoroethyl)-1H-indol-2-yl)prop-2-yn-1-yl)amino)benzamide | 501.1 |

TABLE 5-continued

| Compound No. | Structure | IUPAC | LC-MS (ES+, m/z) |
|---|---|---|---|
| 1007A | 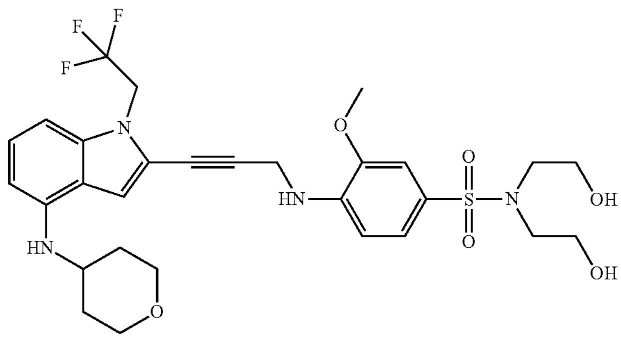 [SMILES: COc1cc(S(=O)(=O)N(CCO)CCO)ccc1NCC#Cc1cc2c(NC3CCOCC3)cccc2n1CC(F)(F)F] | N,N-bis(2-hydroxyethyl)-3-methoxy-4-[(3-{4-[(oxan-4-yl)amino]-1-(2,2,2-trifluoroethyl)-1H-indol-2-yl}prop-2-yn-1-yl)amino]benzene-1-sulfonamide | 625.2 |
| 1008A | 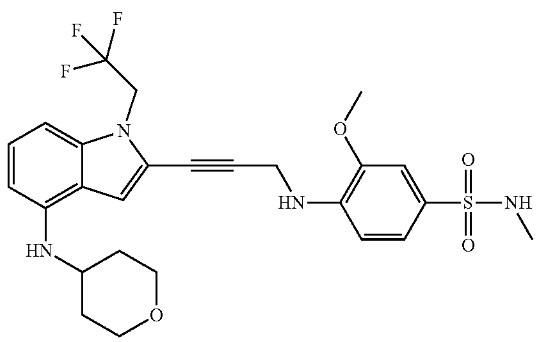 [SMILES: CNS(=O)(=O)c1ccc(NCC#Cc2cc3c(NC4CCOCC4)cccc3n2CC(F)(F)F)c(OC)c1] | 3-methoxy-N-methyl-4-[(3-{4-[(oxan-4-yl)amino]-1-(2,2,2-trifluoroethyl)-1H-indol-2-yl}prop-2-yn-1-yl)amino]benzene-1-sulfonamide | 551.2 |
| 1009A | 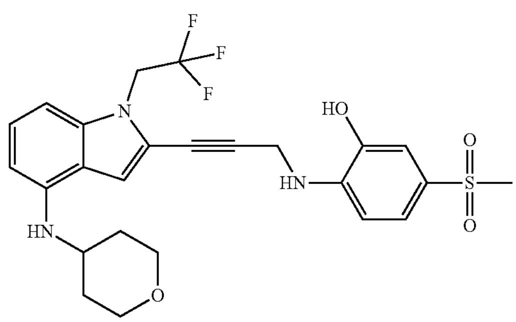 | 5-methanesulfonyl-2-[(3-{4-[(oxan-4-yl)amino]-1-(2,2,2-trifluoroethyl)-1H-indol-2-yl}prop-2-yn-1-yl)amino]phenol | 522.1 |
| 1010A | 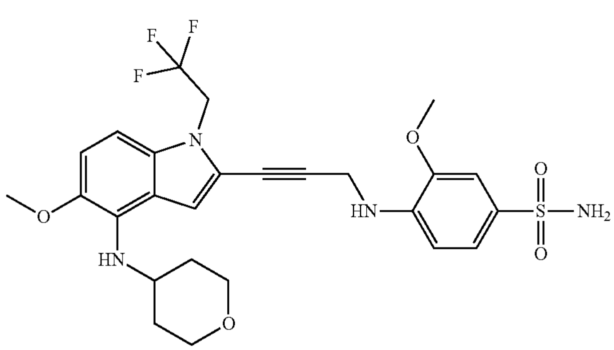 [SMILES: COc1cc(S(N)(=O)=O)ccc1NCC#Cc1cc2c(NC3CCOCC3)c(OC)ccc2n1CC(F)(F)F] | 3-methoxy-4-[(3-{5-methoxy-4-[(oxan-4-yl)amino]-1-(2,2,2-trifluoroethyl)-1H-indol-2-yl}prop-2-yn-1-yl)amino]benzene-1-sulfonamide | 567.3 |

TABLE 5-continued

| Compound No. | Structure | IUPAC | LC-MS (ES+, m/z) |
|---|---|---|---|
| 1011A | 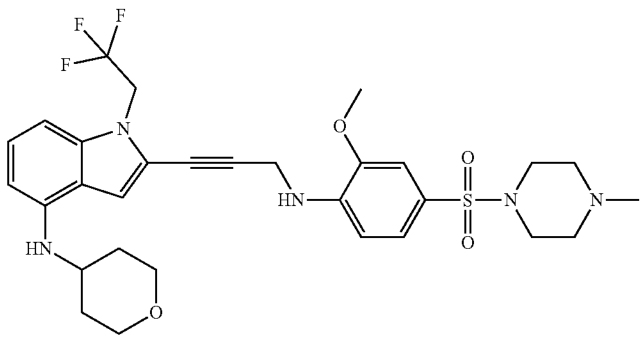 [SMILES: COc1cc(S(=O)(=O)N2CCN(C)CC2)ccc1NCC#Cc1cc2c(NC3CCOCC3)cccc2n1CC(F)(F)F] | 2-[3-({2-methoxy-4-[(4-methylpiperazin-1-yl)sulfonyl]phenyl}amino)prop-1-yn-1-yl]-N-(oxan-4-yl)-1-(2,2,2-trifluoroethyl)-1H-indol-4-amine | 620.4 |
| 1012A | 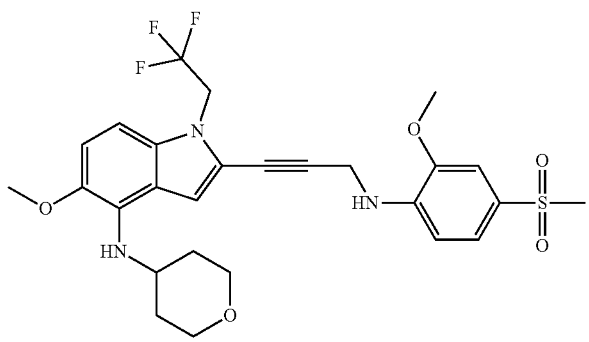 | 2-{3-[(4-methanesulfonyl-2-methoxyphenyl)amino]prop-1-yn-1-yl}-5-methoxy-N-(oxan-4-yl)-1-(2,2,2-trifluoroethyl)-1H-indol-4-amine | 566.2 |
| 1013A | 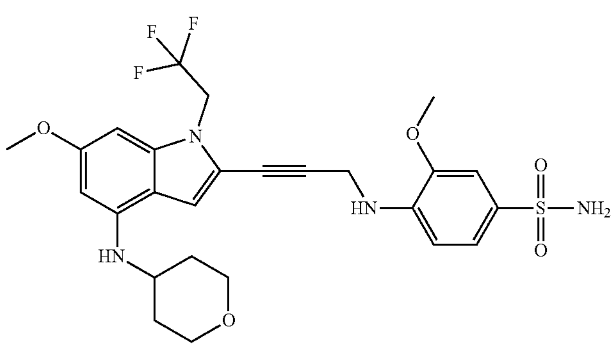 [SMILES: COc1cc(NC2CCOCC2)c2cc(C#CCNc3ccc(S(N)(=O)=O)cc3OC)n(CC(F)(F)F)c2c1] | 3-methoxy-4-[(3-{6-methoxy-4-[(oxan-4-yl)amino]-1-(2,2,2-trifluoroethyl)-1H-indol-2-yl}prop-2-yn-1-yl)amino]benzene-1-sulfonamide | 567.0 |
| 1014A | 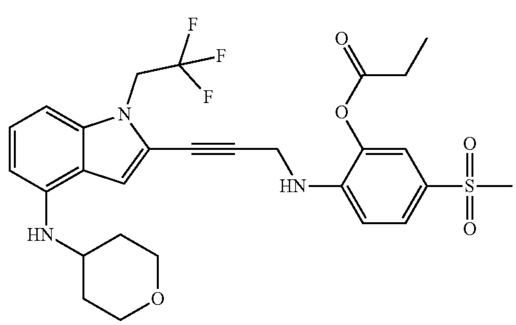 [SMILES: CCC(=O)Oc1cc(S(C)(=O)=O)ccc1NCC#Cc1cc2c(NC3CCOCC3)cccc2n1CC(F)(F)F] | 5-methanesulfonyl-2-[(3-{4-[(oxan-4-yl)amino]-1-(2,2,2-trifluoroethyl)-1H-indol-2-yl}prop-2-yn-1-yl)amino]phenyl propanoate | 578.2 |

TABLE 5-continued

| Compound No. | Structure | IUPAC | LC-MS (ES+, m/z) |
|---|---|---|---|
| 1015A | 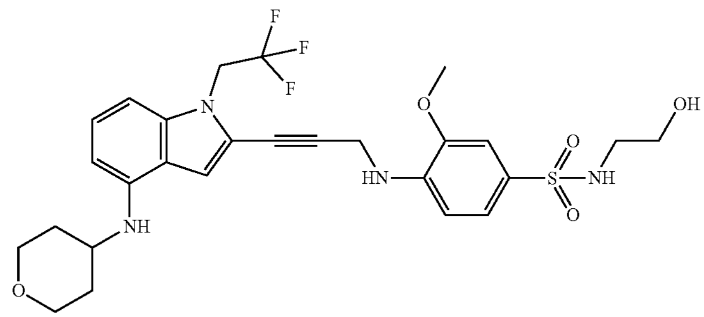 [SMILES: COc1cc(S(=O)(=O)NCCO)ccc1NCC#Cc1cc2c(NC3CCOCC3)cccc2n1CC(F)(F)F] | N-(2-hydroxyethyl)-3-methoxy-4-((3-(4-((tetrahydro-2H-pyran-4-yl)amino)-1-(2,2,2-trifluoroethyl)-1H-indol-2-yl)prop-2-yn-1-yl)amino)benzenesulfonamide | 581.2 |
| 1016A | 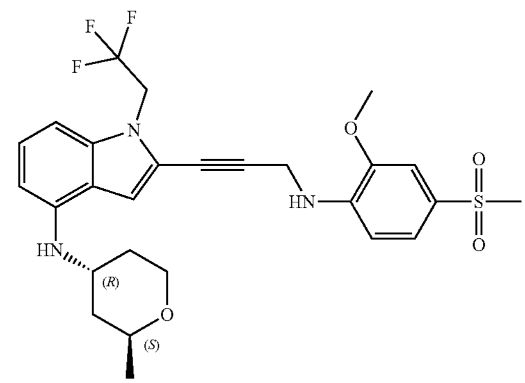 | 2-{3-[(4-methanesulfonyl-2-methoxyphenyl)amino]prop-1-yn-1-yl}-N-[(2S,4R)-2-methyloxan-4-yl]-1-(2,2,2-trifluoroethyl)-1H-indol-4-amine | 550.2 |
| 1017A | 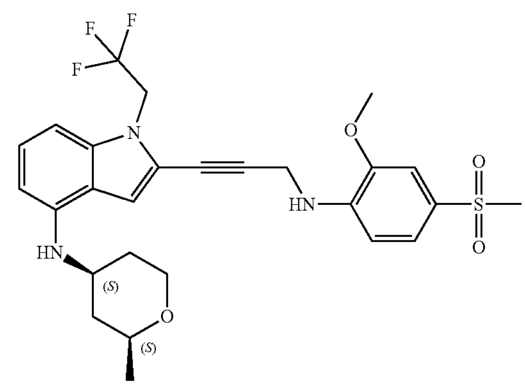 | 2-{3-[(4-methanesulfonyl-2-methoxyphenyl)amino]prop-1-yn-1-yl}-N-[(2S,4S)-2-methyloxan-4-yl]-1-(2,2,2-trifluoroethyl)-1H-indol-4-amine | 550.2 |
| 1018A | 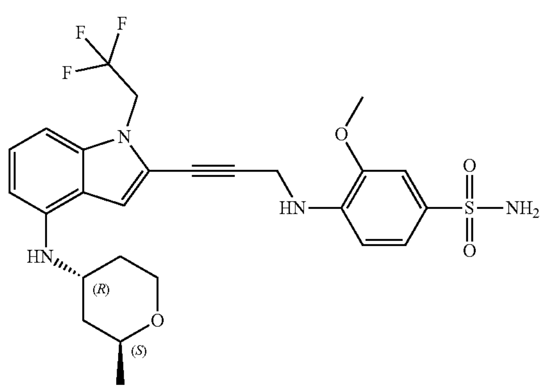 | 3-methoxy-4-{[3-(4-{[(2S,4R)-2-methyloxan-4-yl]amino}-1-(2,2,2-trifluoroethyl)-1H-indol-2-yl)prop-2-yn-1-yl]amino}benzene-1-sulfonamide | 551.2 |

TABLE 5-continued

| Compound No. | Structure | IUPAC | LC-MS (ES+, m/z) |
|---|---|---|---|
| 1019A | 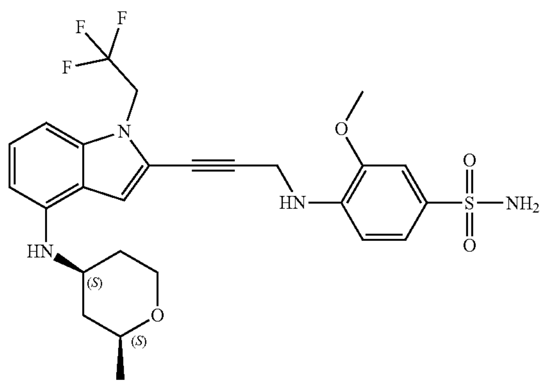 | 3-methoxy-4-{[3-(4-{[(2S,4S)-2-methyloxan-4-yl]amino}-1-(2,2,2-trifluoroethyl)-1H-indol-2-yl)prop-2-yn-1-yl]amino}benzene-1-sulfonamide | 551.2 |
| 1020A | 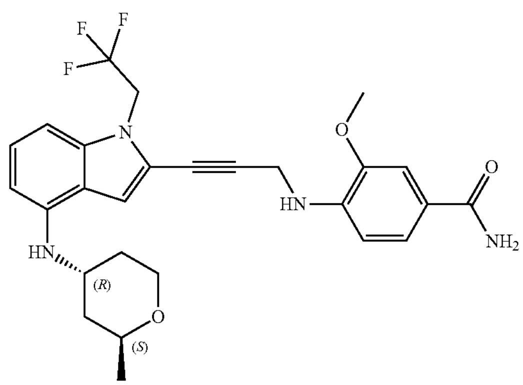 | 3-methoxy-4-{[3-(4-{[(2S,4R)-2-methyloxan-4-yl]amino}-1-(2,2,2-trifluoroethyl)-1H-indol-2-yl)prop-2-yn-1-yl]amino}benzamide | 515.2 |
| 1021A | 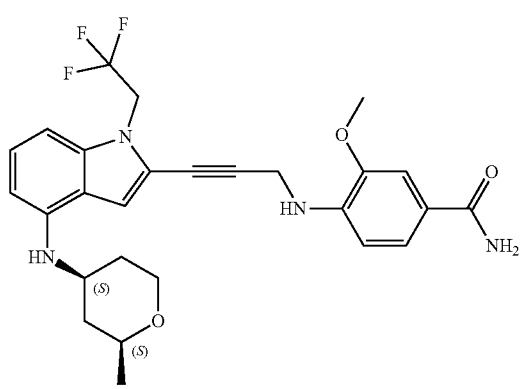 | 3-methoxy-4-{[3-(4-{[(2S,4S)-2-methyloxan-4-yl]amino}-1-(2,2,2-trifluoroethyl)-1H-indol-2-yl)prop-2-yn-1-yl]amino}benzamide | 515.2 |
| 1022A | 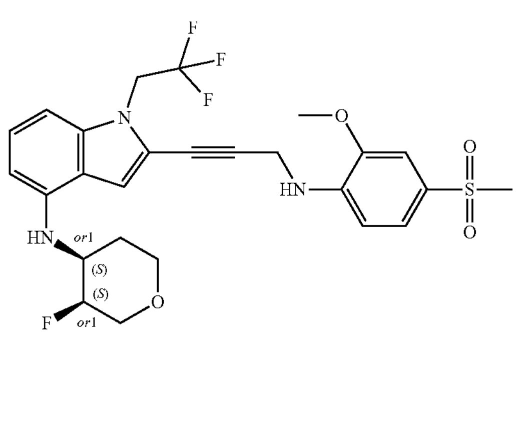 | rac-N-[(3R,4R)-3-fluorooxan-4-yl]-2-{3-[(4-methanesulfonyl-2-methoxyphenyl)amino]prop-1-yn-1-yl}-1-(2,2,2-trifluoroethyl)-1H-indol-4-amine | 553.9 |

TABLE 5-continued

| Compound No. | Structure | IUPAC | LC-MS (ES+, m/z) |
|---|---|---|---|
| 1023A | 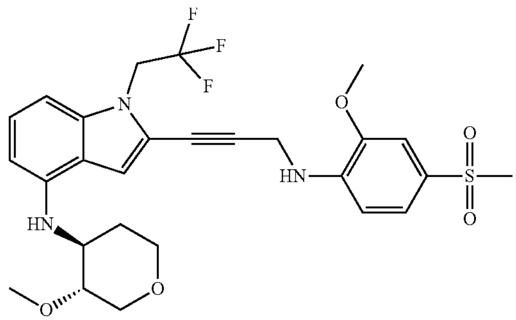 [SMILES: COc1cc(S(C)(=O)=O)ccc1NCC#Cc1cc2c(N[C@H]3CCOC[C@@H]3OC)cccc2n1CC(F)(F)F] | 2-(3-((2-methoxy-4-(methylsulfonyl)phenyl)amino)prop-1-yn-1-yl)-N-((3R,4S)-3-methoxytetrahydro-2H-pyran-4-yl)-1-(2,2,2-trifluoroethyl)-1H-indol-4-amine | 566.2 |
| 1024A | 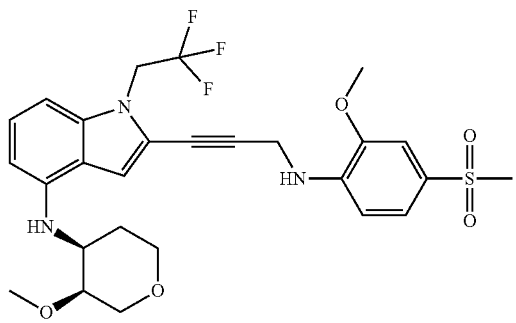 | 2-(3-((2-methoxy-4-(methylsulfonyl)phenyl)amino)prop-1-yn-1-yl)-N-((3S,4S)-3-methoxytetrahydro-2H-pyran-4-yl)-1-(2,2,2-trifluoroethyl)-1H-indol-4-amine | 566.2 |
| 1025A | 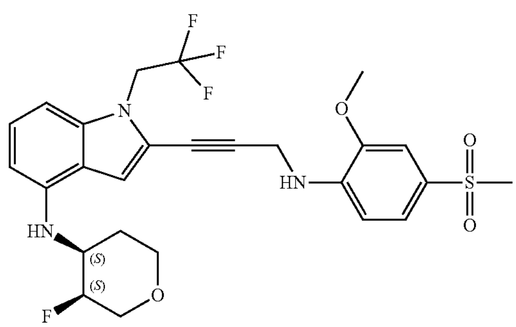 | N-[(3S,4S)-3-fluorooxan-4-yl]-2-{3-[(4-methanesulfonyl-2-methoxyphenyl)amino]prop-1-yn-1-yl}-1-(2,2,2-trifluoroethyl)-1H-indol-4-amine | 554.2 |
| 1026A | 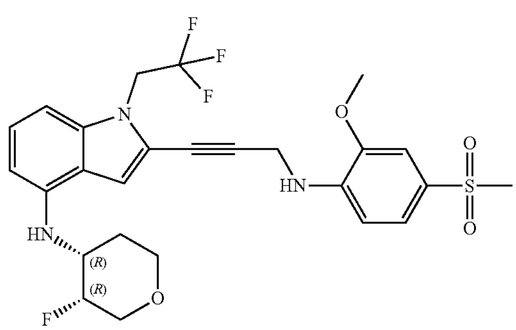 | N-[(3R,4R)-3-fluorooxan-4-yl]-2-{3-[(4-methanesulfonyl-2-methoxyphenyl)amino]prop-1-yn-1-yl}-1-(2,2,2-trifluoroethyl)-1H-indol-4-amine | 554.2 |

TABLE 5-continued

| Compound No. | Structure | IUPAC | LC-MS (ES+, m/z) |
|---|---|---|---|
| 1027A | 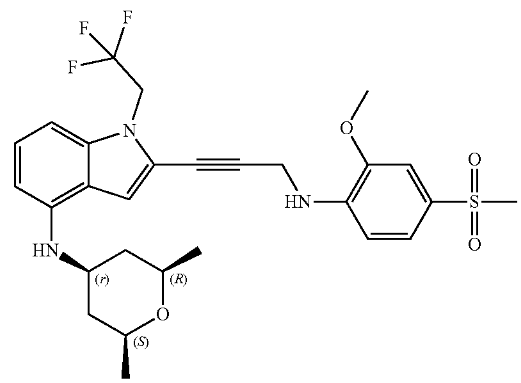 | 2-{3-[(4-methanesulfonyl-2-methoxyphenyl)amino]prop-1-yn-1-yl}-N-[(2R,4R,6S)-2,6-dimethyloxan-4-yl]-1-(2,2,2-trifluoroethyl)-1H-indol-4-amine | 564.2 |
| 1028A | 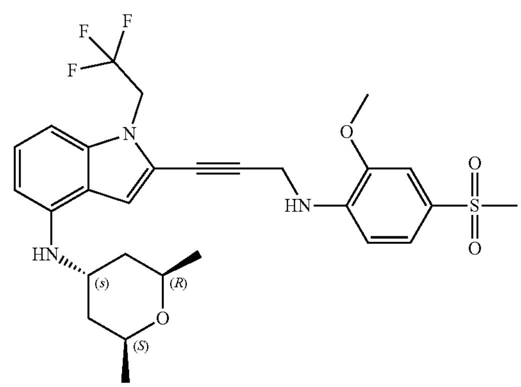 | 2-{3-[(4-methanesulfonyl-2-methoxyphenyl)amino]prop-1-yn-1-yl}-N-[(2R,4S,6S)-2,6-dimethyloxan-4-yl]-1-(2,2,2-trifluoroethyl)-1H-indol-4-amine | 564.2 |
| 1029A | 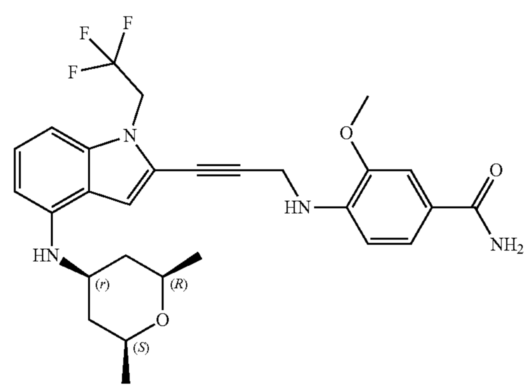 | 3-methoxy-4-{[3-(4-{[(2R,4R,6S)-2,6-dimethyloxan-4-yl]amino}-1-(2,2,2-trifluoroethyl)-1H-indol-2-yl)prop-2-yn-1-yl]amino}benzamide | 529.2 |
| 1030A | 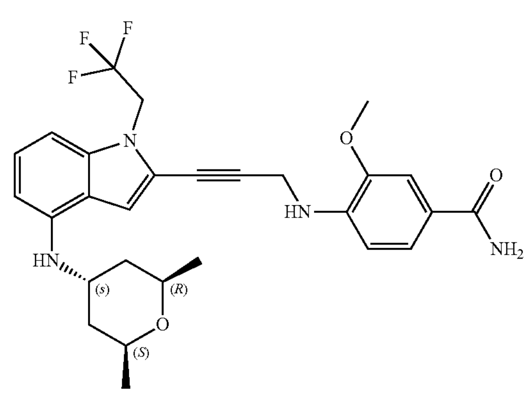 | 3-methoxy-4-{[3-(4-{[(2R,4S,6S)-2,6-dimethyloxan-4-yl]amino}-1-(2,2,2-trifluoroethyl)-1H-indol-2-yl)prop-2-yn-1-yl]amino}benzamide | 529.2 |

TABLE 5-continued

| Compound No. | Structure | IUPAC | LC-MS (ES+, m/z) |
|---|---|---|---|
| 1031A | 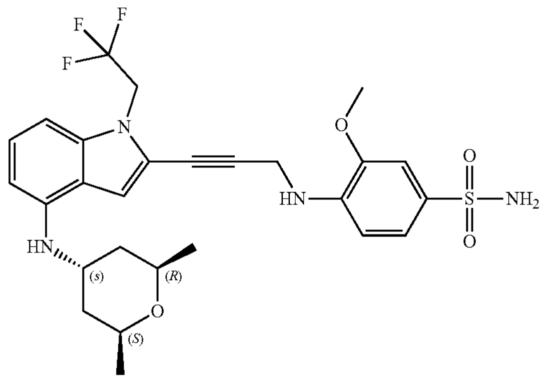 | 3-methoxy-4-{[3-(4-{[(2R,4S,6S)-2,6-dimethyloxan-4-yl]amino}-1-(2,2,2-trifluoroethyl)-1H-indol-2-yl)prop-2-yn-1-yl]amino}benzene-1-sulfonamide | 565.2 |
| 1032A | 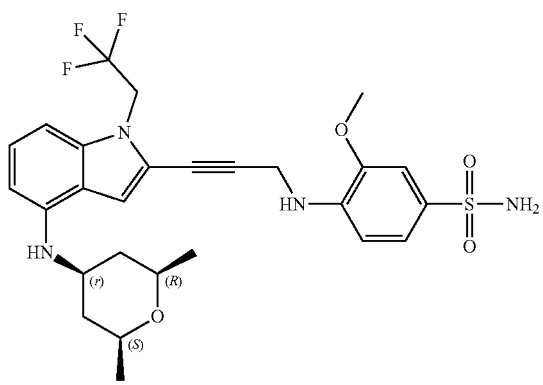 | 3-methoxy-4-{[3-(4-{[(2R,4R,6S)-2,6-dimethyloxan-4-yl]amino}-1-(2,2,2-trifluoroethyl)-1H-indol-2-yl)prop-2-yn-1-yl]amino}benzene-1-sulfonamide | 565.2 |

F. Compounds with 4-((2-ethynyl-1H-indol-4-yl)amino)tetrahydro-2H-thiopyran 1,1-dioxide core Example F1: Synthesis of 4-((2-(3-((4-methoxypyridin-3-yl)amino)prop-1-yn-1-yl)-1-(2,2,2-trifluoroethyl)-1H-indol-4-yl)amino)tetrahydro-2H-thiopyran 1,1-dioxide (Compound 1033A)

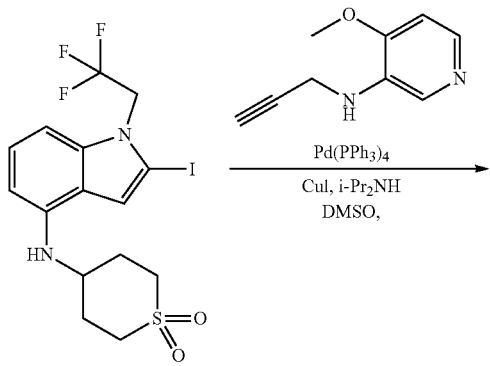

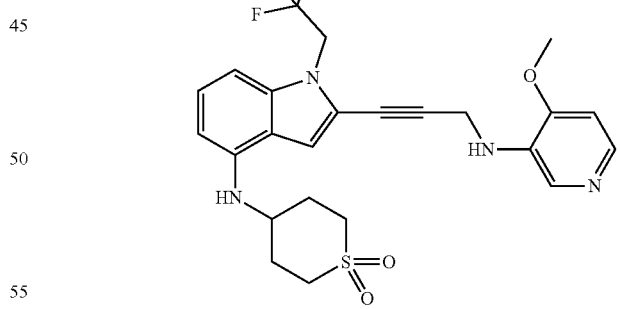

-continued

4-Methoxy-N-prop-2-ynyl-pyridin-3-amine was prepared using the method described in EXAMPLE D1.

To a solution of N-(1,1-dioxothian-4-yl)-2-iodo-1-(2,2,2-trifluoroethyl)indol-4-amine (70 mg, 148.22 µmol, 1 eq.) in DMSO (3 mL) were added 4-methoxy-N-prop-2-ynyl-pyridin-3-amine (36.06 mg, 222.34 µmol, 1.50 eq.), CuI (28.23 mg, 148.22 µmol, 1 eq.), Pd(PPh₃)₄ (17.13 mg, 14.82 µmol, 0.10 eq.), and N-isopropylpropan-2-amine (89.99 mg, 889.34 µmol, 124.99 µL, 6 eq.). The mixture was stirred at 40° C. for 2 h. The reaction mixture was quenched with saturated aqueous EDTA (20 mL) and stirred for 2 h. Then, EtOAc (20 mL) was added to the mixture. The organic phase was separated, washed with water (10 mL), dried over anhydrous sodium sulfate, filtered, and concentrated under reduced pressure. The crude residue was purified by prep-HPLC to afford N-(1,1-dioxothian-4-yl)-2-[3-[(4-methoxy-3-pyridyl)amino]prop-1-ynyl]-1-(2,2,2-trifluoroethyl)indol-4-amine (5 mg, 9.87 μmol, 6.66% yield) as a white solid. MS (ES$^{30}$, m/z): 507.1.

Example F2: Synthesis of 4-((2-(3-((4-methoxy-6-(methylsulfonyl)pyridin-3-yl)amino)prop-1-yn-1-yl)-1-(2,2,2-trifluoroethyl)-1H-indol-4-yl)amino)tetrahydro-2H-thiopyran 1,1-dioxide (Compound 1050A)

HCl) in DMSO (2 mL) was flushed with $N_2$. CuI (20.16 mg, 105.87 μmol, 1 eq.) and N-isopropyl amine (32.14 mg, 317.62 μmol, 44.89 μL, 3 eq.) were added to the mixture. 4-((2-iodo-1-(2,2,2-trifluoroethyl)-1H-indol-4-yl)amino)tetrahydro-2H-thiopyran 1,1-dioxide (50 mg, 105.87 μmol, 1 eq.) and Pd(PPh$_3$)$_4$ (9.79 mg, 8.47 μmol, 0.08 eq.) were added, and the resulting mixture was flushed again with $N_2$. The resulting reaction mixture was stirred at 45° C. for 2 h. LC-MS analysis showed that the starting material was consumed completely, and one main peak with the desired mass was detected. Saturated aqueous EDTA (20 mL) was added, and the mixture was stirred at 15° C. for 1 h. The reaction mixture was partitioned by adding saturated aqueous EDTA (20 mL) and EtOAc (20 mL). The organic phase was separated, washed with brine (5 mL×3), dried over

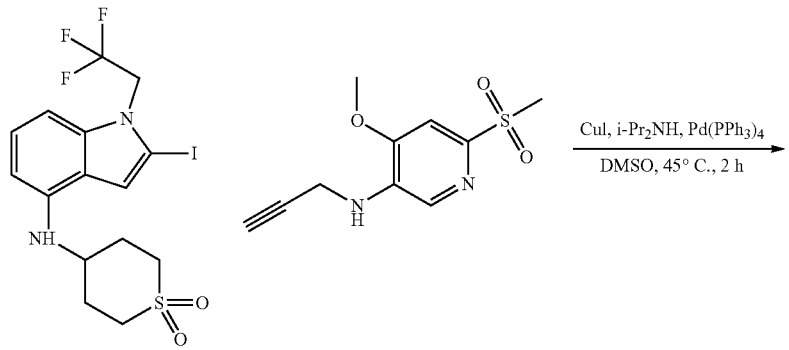

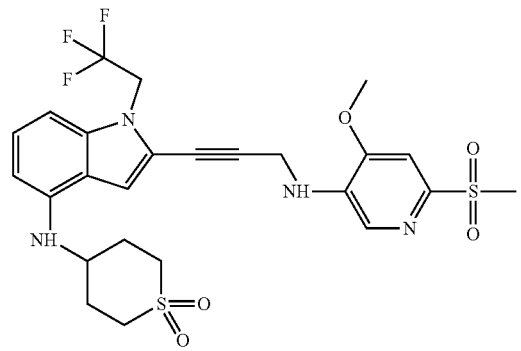

4-Methoxy-6-(methylsulfonyl)-N-(prop-2-yn-1-yl)pyridin-3-amine was prepared using the method described in EXAMPLE D47.

A solution of 4-methoxy-6-(methylsulfonyl)-N-(prop-2-yn-1-yl)pyridin-3-amine (35.16 mg, 127.05 μmol, 1.2 eq., anhydrous sodium sulfate, filtered, and concentrated under reduced pressure to give a residue. The residue was purified by prep-HPLC to afford the desired product (7.8 mg, 13.34 μmol, 12.60% yield) as a white solid. MS (ES$^{30}$, m/z): 585.0.

Example F3: Procedure for Preparation of Compound 1047A

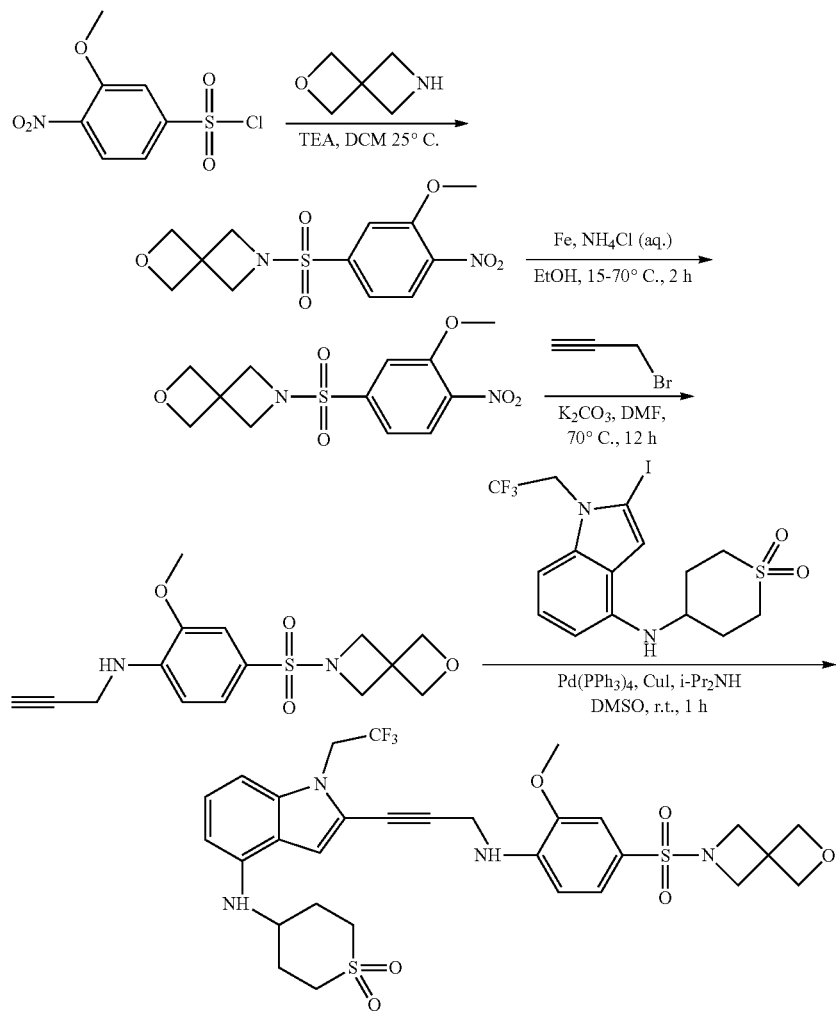

Synthesis of 6-((3-methoxy-4-nitrophenyl)sulfonyl)-2-oxa-6-azaspiro[3.3]heptane: To a solution of 2-oxa-6-azaspiro[3.3]heptane (451.03 mg, 2.38 mmol, 1.2 eq.) in DCM (5 mL) was TEA (402.12 mg, 3.97 mmol, 553.12 µL, 2 eq.), followed by 3-methoxy-4-nitrobenzenesulfonyl chloride (500 mg, 1.99 mmol, 1 eq.) at 0° C. The temperature was slowly increased to 25° C. and stirred for 16 h, after which time TLC analysis (PE:EtOAc=2:1, $R_f$=0.43) indicated that the starting sulfonyl chloride was consumed. The reaction mixture was quenched by adding water (40 mL) at 25° C., and then extracted with EtOAc (40 mL×3). The combined organic layers were dried over anhydrous sodium sulfate, filtered, and concentrated under reduced pressure. The resulting residue was purified by column chromatography (SiO$_2$, PE:EtOAc=5:1 to 1:1) to afford 6-((3-methoxy-4-nitrophenyl)sulfonyl)-2-oxa-6-azaspiro[3.3]heptane (550 mg, 1.57 mmol, 39.63% yield) as a yellow solid.

Synthesis of 4-((2-oxa-6-azaspiro[3.3]heptan-6-yl)sulfonyl)-2-methoxyaniline: A solution of 6-((3-methoxy-4-nitrophenyl)sulfonyl)-2-oxa-6-azaspiro[3.3]heptane (550 mg, 1.57 mmol, 1 eq.) and NH$_4$Cl (421.21 mg, 7.87 mmol, 275.30 µL, 5 eq.) in EtOH (10 mL) and water (2 mL) was added into Fe (879.48 mg, 15.75 mmol, 10 eq.) at 70° C. and stirred for 2 h, after which time LC-MS analysis indicated that the starting nitro compound was consumed, and one main peak with the desired product mass was detected. The mixture was filtered, diluted with water (100 mL), and extracted with EtOAc (30 mL×3). The combined organic layers were dried over anhydrous sodium sulfate, filtered, and concentrated under reduced pressure. The brown solid residue containing 4-((2-oxa-6-azaspiro[3.3]heptan-6-yl)sulfonyl)-2-methoxyaniline (450 mg, 1.35 mmol, 85.42% yield) was used into the next step without further purification.

Synthesis of 4-((2-oxa-6-azaspiro[3.3]heptan-6-yl)sulfonyl)-2-methoxy-N-(prop-2-yn-1-yl)aniline: To a solution of propargyl bromide (355.63 mg, 2.99 mmol, 257.70 µL, 20 eq.) in DMF (2 mL) was added 4-((2-oxa-6-azaspiro[3.3]heptan-6-yl)sulfonyl)-2-methoxyaniline (50 mg, 149.47 µmol, 1 eq.) and K$_2$CO$_3$ (41.32 mg, 298.95 µmol, 2 eq.). The mixture was stirred at 70° C. for 12 h. LC-MS analysis indicated that 80% of the starting primary amine was consumed, and one main peak with the desired product mass was detected. The reaction mixture was quenched by adding water (40 mL) at 25° C., and then extracted with EtOAc (10 mL×3). The combined organic layers were dried over anhydrous sodium sulfate, filtered, and concentrated under reduced pressure. The resulting residue was purified by prep-TLC (SiO$_2$, PE:EtOAc=1:1, R$_f$=0.32) to provide 4-((2-oxa-6-azaspiro[3.3]heptan-6-yl)sulfonyl)-2-methoxy-N-(prop-2-yn-1-yl)aniline (40 mg, 111.67 µmol, 74.71% yield) as a light yellow solid.

Preparation of final product: To a solution of 4-((2-iodo-1-(2,2,2-trifluoroethyl)-1H-indol-4-yl)amino)tetrahydro-2H-thiopyran 1,1-dioxide (50 mg, 105.87 µmol, 1 eq.) and 4-((2-oxa-6-azaspiro[3.3]heptan-6-yl)sulfonyl)-2-methoxy-N-(prop-2-yn-1-yl)aniline (40 mg, 111.67 µmol, 1.05 eq.) in DMSO (3 mL) was added CuI (20.16 mg, 105.87 µmol, 1 eq.) and diisopropylamine (10.71 mg, 105.87 µmol, 14.96 µL, 1 eq.), followed by Pd(PPh$_3$)$_4$ (2.45 mg, 2.12 µmol, 0.02 eq.) under N$_2$. The reaction mixture was then stirred for 1 h at 25° C., after which time LC-MS analysis indicated that the starting iodoindole was completely consumed, and one main peak with the desired product mass was detected. The reaction mixture was quenched by adding saturated aqueous EDTA (60 mL), stirring the mixture at 25° C. for 1 h, and then extracting the mixture with EtOAc (20 mL×4). The combined organic layers were dried over anhydrous sodium sulfate, filtered, and concentrated under reduced pressure. The resulting residue was purified by prep-TLC (SiO$_2$, EtOAc:MeOH=2:1, R$_f$=0.30), and further purified by prep-HPLC to afford 4-((2-(3-((4-((2-oxa-6-azaspiro[3.3]heptan-6-yl)sulfonyl)-2-methoxyphenyl)amino)prop-1-yn-1-yl)-1-(2,2,2-trifluoroethyl)-1H-indol-4-yl)amino)tetrahydro-2H-thiopyran 1,1-dioxide (8.8 mg, 13.20 µmol, 12.47% yield) as a light yellow solid. MS (ES$^+$, m/z): 667.1.

TABLE 6 shows compounds with a 4-((2-ethynyl-H-indol-4-yl)amino)tetrahydro-2H-thiopyran 1,1-dioxide core.

TABLE 6

| Compound No. | Structure | IUPAC | LC-MS (ES$^+$, m/z) |
| --- | --- | --- | --- |
| 1033A | 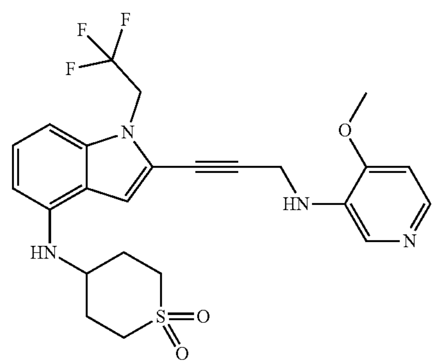 [SMILES: COc1ccncc1NCC#Cc1cc2c(NC3CCS(=O)(=O)CC3)cccc2n1CC(F)(F)F] | 4-((2-(3-((4-methoxypyridin-3-yl)amino)prop-1-yn-1-yl)-1-(2,2,2-trifluoroethyl)-1H-indol-4-yl)amino)tetrahydro-2H-thiopyran 1,1-dioxide | 507.1 |
| 1034A | 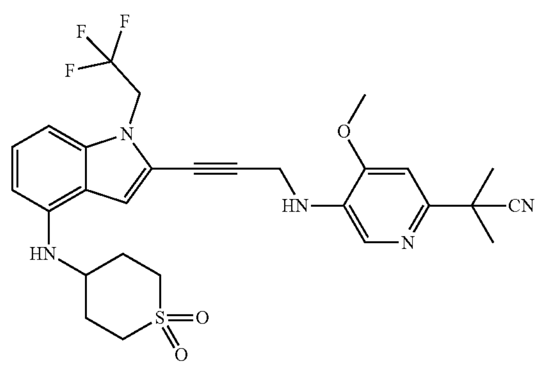 [SMILES: COc1cc(C(C)(C)C#N)ncc1NCC#Cc1cc2c(NC3CCS(=O)(=O)CC3)cccc2n1CC(F)(F)F] | 2-{5-[(3-{4-[(1,1-dioxo-1λ$^6$-thian-4-yl)amino]-1-(2,2,2-trifluoroethyl)-1H-indol-2-yl}prop-2-yn-1-yl)amino]-4-methoxypyridin-2-yl}-2-methylpropanenitrile | 574.2 |
| 1035A | 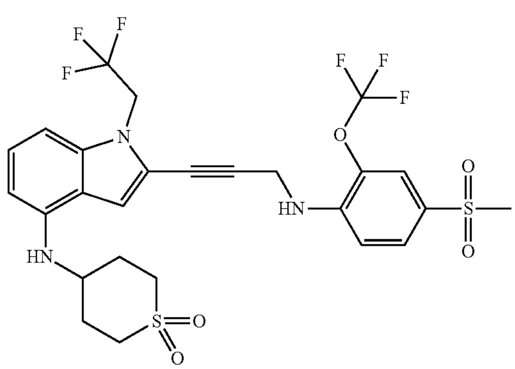 [SMILES: CS(=O)(=O)c1ccc(NCC#Cc2cc3c(NC4CCS(=O)(=O)CC4)cccc3n2CC(F)(F)F)c(OC(F)(F)F)c1] | 4-{[2-(3-{[4-methanesulfonyl-2-(trifluoromethoxy)phenyl]amino}prop-1-yn-1-yl)-1-(2,2,2-trifluoroethyl)-1H-indol-4-yl]amino}-1λ$^6$-thiane-1,1-dione | 638.1 |

TABLE 6-continued

| Compound No. | Structure | IUPAC | LC-MS (ES+, m/z) |
|---|---|---|---|
| 1036A | 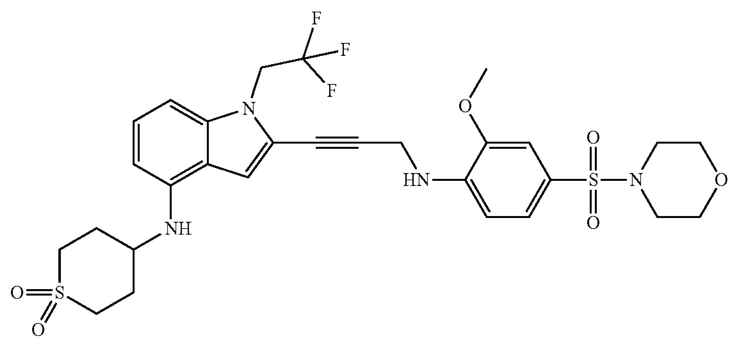 [SMILES: COc1cc(S(=O)(=O)N2CCOCC2)ccc1NCC#Cc1cc2c(NC3CCS(=O)(=O)CC3)cccc2n1CC(F)(F)F] | 4-{[2-(3-{[2-methoxy-4-(morpholine-4-sulfonyl)phenyl]amino}prop-1-yn-1-yl)-1-(2,2,2-trifluoroethyl)-1H-indol-4-yl]amino}-1λ⁶-thiane-1,1-dione | 655.3 |
| 1037A | 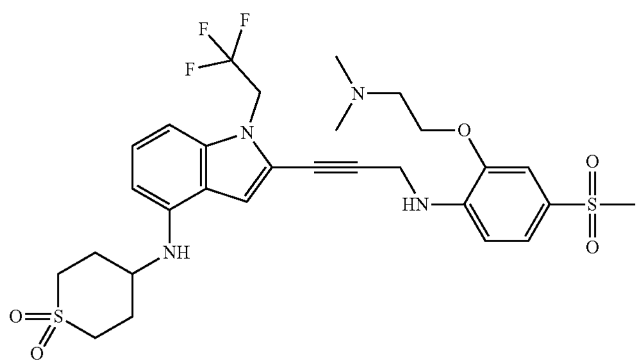 [SMILES: CN(C)CCOc1cc(S(C)(=O)=O)ccc1NCC#Cc1cc2c(NC3CCS(=O)(=O)CC3)cccc2n1CC(F)(F)F] | 4-({2-[3-({2-[2-(dimethylamino)ethoxy]-4-methanesulfonylphenyl}amino)prop-1-yn-1-yl]-1-(2,2,2-trifluoroethyl)-1H-indol-4-yl}amino)-1λ⁶-thiane-1,1-dione | 641.2 |
| 1038A | 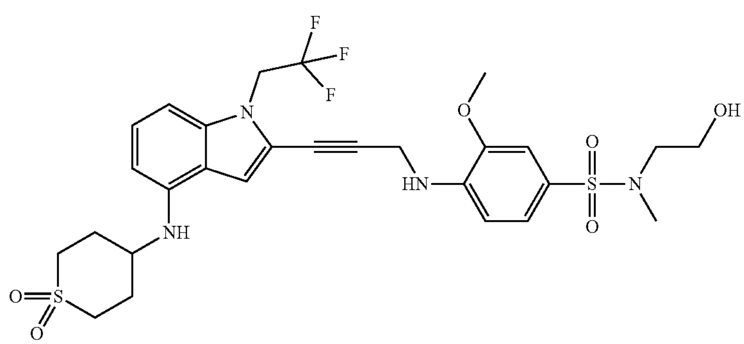 [SMILES: COc1cc(S(=O)(=O)N(C)CCO)ccc1NCC#Cc1cc2c(NC3CCS(=O)(=O)CC3)cccc2n1CC(F)(F)F] | 4-[3-{4-[(1,1-dioxo-1λ⁶-thian-4-yl)amino]-1-(2,2,2-trifluoroethyl)-1H-indol-2-yl}prop-2-yn-1-yl)amino]-N-(2-hydroxyethyl)-3-methoxy-N-methylbenzene-1-sulfonamide | 643.1 |
| 1039A | 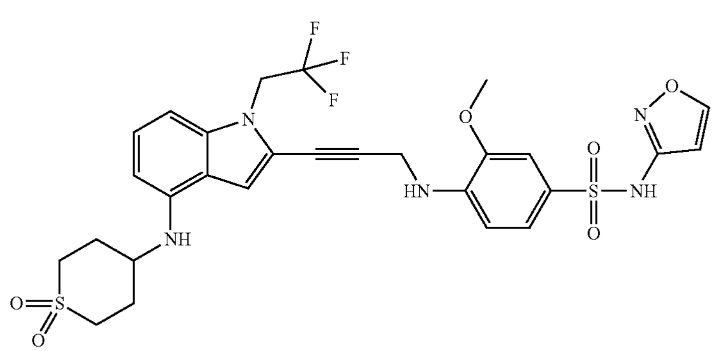 [SMILES: COc1cc(S(=O)(=O)Nc2ccon2)ccc1NCC#Cc1cc2c(NC3CCS(=O)(=O)CC3)cccc2n1CC(F)(F)F] | 4-[(3-{4-[(1,1-dioxo-1λ⁶-thian-4-yl)amino]-1-(2,2,2-trifluoroethyl)-1H-indol-2-yl}prop-2-yn-1-yl)amino]-3-methoxy-N-(1,2-oxazol-3-yl)benzene-1-sulfonamide | 652.1 |

TABLE 6-continued

| Compound No. | Structure | IUPAC | LC-MS (ES+, m/z) |
|---|---|---|---|
| 1040A | 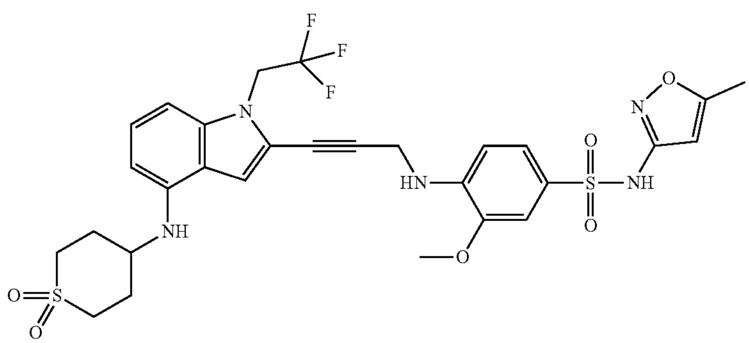 [SMILES: COc1cc(S(=O)(=O)Nc2cc(C)on2)ccc1NCC#Cc1cc2c(NC3CCS(=O)(=O)CC3)cccc2n1CC(F)(F)F] | 4-[(3-{4-[(1,1-dioxo-1λ⁶-thian-4-yl)amino]-1-(2,2,2-trifluoroethyl)-1H-indol-2-yl}prop-2-yn-1-yl)amino]-3-methoxy-N-(5-methyl-1,2-oxazol-3-yl)benzene-1-sulfonamide | 666.2 |
| 1041A | 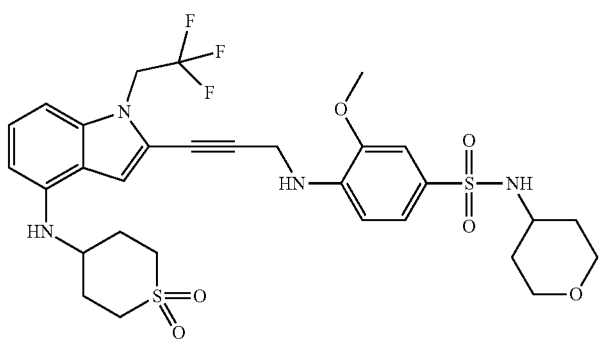 [SMILES: COc1cc(S(=O)(=O)NC2CCOCC2)ccc1NCC#Cc1cc2c(NC3CCS(=O)(=O)CC3)cccc2n1CC(F)(F)F] | 4-[(3-{4-[(1,1-dioxo-1λ⁶-thian-4-yl)amino]-1-(2,2,2-trifluoroethyl)-1H-indol-2-yl}prop-2-yn-1-yl)amino]-3-methoxy-N-(oxan-4-yl)benzene-1-sulfonamide | 669.1 |
| 1042A | 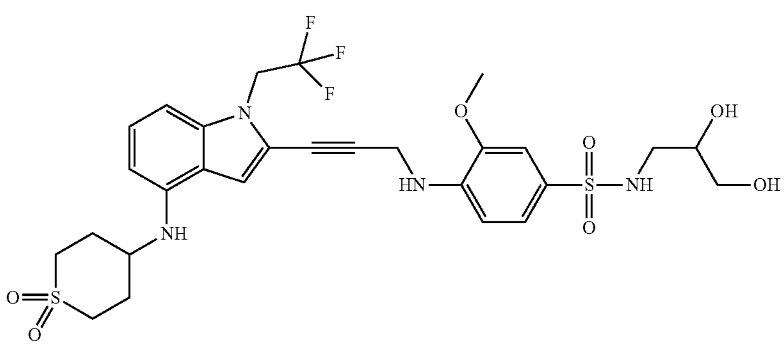 [SMILES: COc1cc(S(=O)(=O)NCC(O)CO)ccc1NCC#Cc1cc2c(NC3CCS(=O)(=O)CC3)cccc2n1CC(F)(F)F] | N-(2,3-dihydroxypropyl)-4-[(3-{4-[(1,1-dioxo-1λ⁶-thian-4-yl)amino]-1-(2,2,2-trifluoroethyl)-1H-indol-2-yl}prop-2-yn-1-yl)amino]-3-methoxybenzene-1-sulfonamide | 659.1 |
| 1043A | 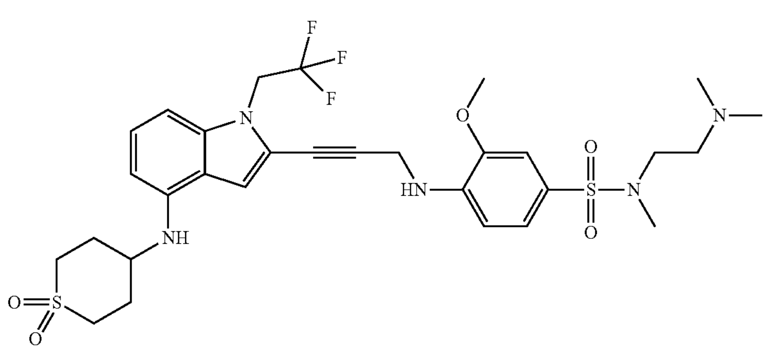 [SMILES: COc1cc(S(=O)(=O)N(C)CCN(C)C)ccc1NCC#Cc1cc2c(NC3CCS(=O)(=O)CC3)cccc2n1CC(F)(F)F] | N-[2-(dimethylamino)ethyl]-4-[(3-{4-[(1,1-dioxo-1λ⁶-thian-4-yl)amino]-1-(2,2,2-trifluoroethyl)-1H-indol-2-yl}prop-2-yn-1-yl)amino]-3-methoxy-N-methylbenzene-1-sulfonamide | 670.2 |

TABLE 6-continued

| Compound No. | Structure | IUPAC | LC-MS (ES+, m/z) |
|---|---|---|---|
| 1044A | 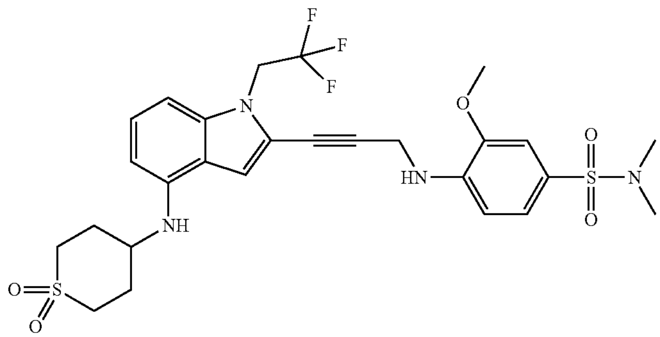 [SMILES: COc1cc(S(=O)(=O)N(C)C)ccc1NCC#Cc1cc2c(NC3CCS(=O)(=O)CC3)cccc2n1CC(F)(F)F] | 4-[(3-{4-[(1,1-dioxo-1λ6-thian-4-yl)amino]-1-(2,2,2-trifluoroethyl)-1H-indol-2-yl}prop-2-yn-1-yl)amino]-3-methoxy-N,N-dimethylbenzene-1-sulfonamide | 613.1 |
| 1045A | 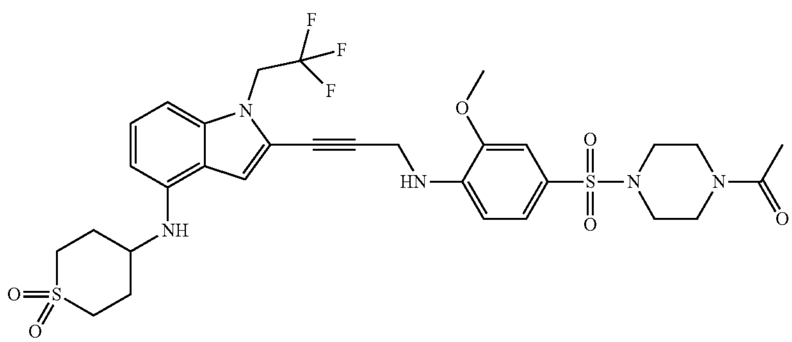 [SMILES: COc1cc(S(=O)(=O)N2CCN(C(C)=O)CC2)ccc1NCC#Cc1cc2c(NC3CCS(=O)(=O)CC3)cccc2n1CC(F)(F)F] | 4-({2-[3-({4-[(4-acetylpiperazin-1-yl)sulfonyl]-2-methoxyphenyl}amino)prop-1-yn-1-yl]-1-(2,2,2-trifluoroethyl)-1H-indol-4-yl}amino)-1λ6-thiane-1,1-dione | 696.2 |
| 1046A | 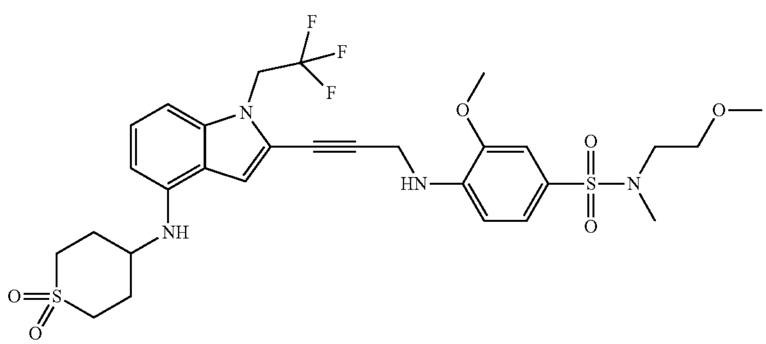 [SMILES: COCCN(C)S(=O)(=O)c1ccc(NCC#Cc2cc3c(NC4CCS(=O)(=O)CC4)cccc3n2CC(F)(F)F)c(OC)c1] | 4-[(3-{4-[(1,1-dioxo-1λ6-thian-4-yl)amino]-1-(2,2,2-trifluoroethyl)-1H-indol-2-yl}prop-2-yn-1-yl)amino]-3-methoxy-N-(2-methoxyethyl)-N-methylbenzene-1-sulfonamide | 657.2 |
| 1047A | 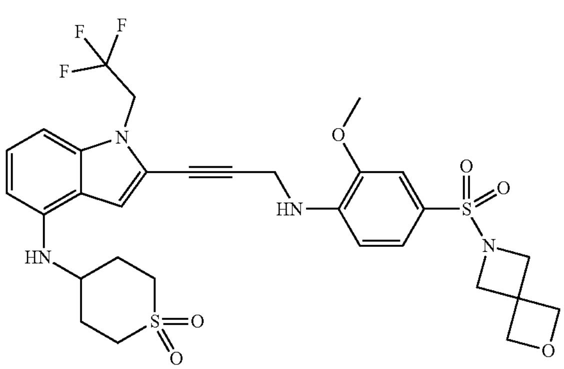 [SMILES: COc1cc(S(=O)(=O)N2CC3(COC3)C2)ccc1NCC#Cc1cc2c(NC3CCS(=O)(=O)CC3)cccc2n1CC(F)(F)F] | 4-[(2-{3-[(2-methoxy-4-{2-oxa-6-azaspiro[3.3]heptane-6-sulfonyl}phenyl)amino]prop-1-yn-1-yl}-1-(2,2,2-trifluoroethyl)-1H-indol-4-yl)amino]-1λ6-thiane-1,1-dione | 667.1 |

TABLE 6-continued

| Compound No. | Structure | IUPAC | LC-MS (ES+, m/z) |
|---|---|---|---|
| 1048A | 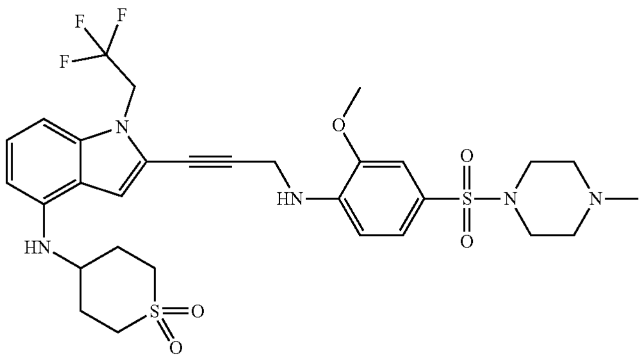 [SMILES: COc1cc(S(=O)(=O)N2CCN(C)CC2)ccc1NCC#Cc1cc2c(NC3CCS(=O)(=O)CC3)cccc2n1CC(F)(F)F] | 4-({2-[3-({2-methoxy-4-[(4-methylpiperazin-1-yl)sulfonyl]phenyl}amino)prop-1-yn-1-yl]-1-(2,2,2-trifluoroethyl)-1H-indol-4-yl}amino)-1λ⁶-thiane-1,1-dione | 668.2 |
| 1049A | 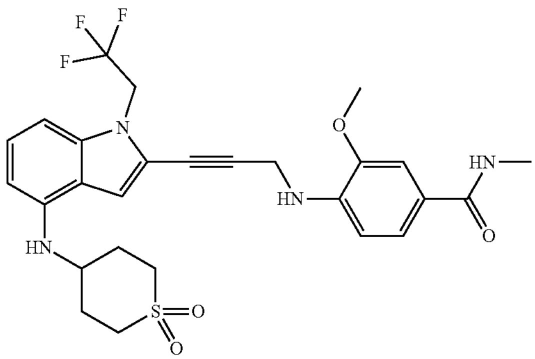 [SMILES: CNC(=O)c1ccc(NCC#Cc2cc3c(NC4CCS(=O)(=O)CC4)cccc3n2CC(F)(F)F)c(OC)c1] | 4-[(3-{4-[(1,1-dioxo-1λ⁶-thian-4-yl)amino]-1-(2,2,2-trifluoroethyl)-1H-indol-2-yl}prop-2-yn-1-yl)amino]-3-methoxy-N-methylbenzamide | 563.2 |
| 1050A | 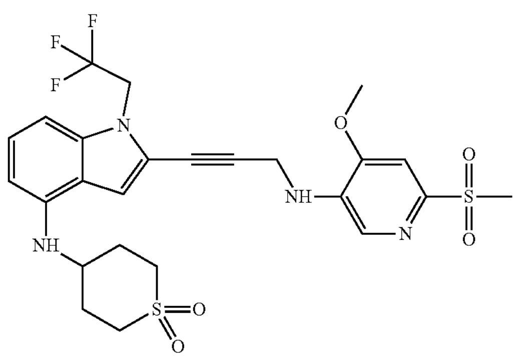 [SMILES: COc1cc(S(C)(=O)=O)ncc1NCC#Cc1cc2c(NC3CCS(=O)(=O)CC3)cccc2n1CC(F)(F)F] | 4-((2-(3-((4-methoxy-6-(methylsulfonyl)pyridin-3-yl)amino)prop-1-yn-1-yl)-1-(2,2,2-trifluoroethyl)-1H-indol-4-yl)amino)tetrahydro-2H-thiopyran 1,1-dioxide | |
| 1051A | 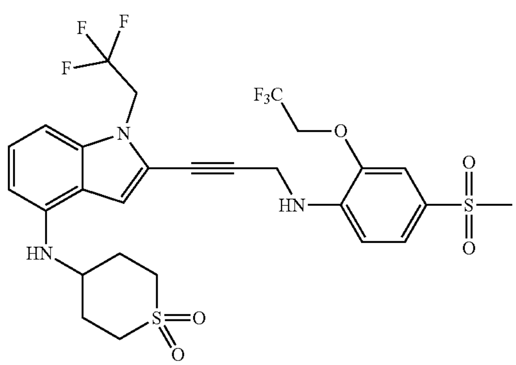 [SMILES: CS(=O)(=O)c1ccc(NCC#Cc2cc3c(NC4CCS(=O)(=O)CC4)cccc3n2CC(F)(F)F)c(OCC(F)(F)F)c1] | 4-((2-(3-((4-(methylsulfonyl)-2-(2,2,2-trifluoroethoxy)phenyl)amino)prop-1-yn-1-yl)-1-(2,2,2-trifluoroethyl)-1H-indol-4-yl)amino)tetrahydro-2H-thiopyran 1,1-dioxide | 652.1 |

TABLE 6-continued

| Compound No. | Structure | IUPAC | LC-MS (ES+, m/z) |
|---|---|---|---|
| 1052A | 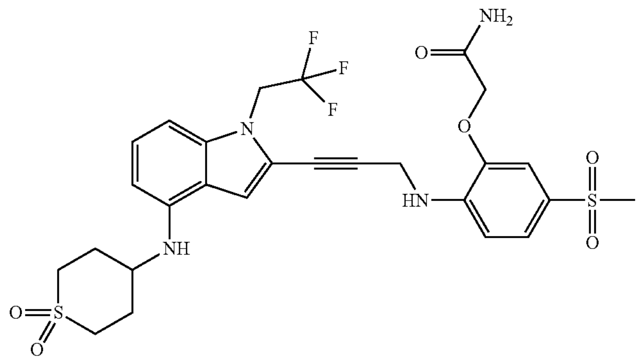 [SMILES: CS(=O)(=O)c1ccc(NCC#Cc2cc3c(NC4CCS(=O)(=O)CC4)cccc3n2CC(F)(F)F)c(OCC(N)=O)c1] | 2-(2-((3-(4-((1,1-dioxidotetrahydro-2H-thiopyran-4-yl)amino)-1-(2,2,2-trifluoroethyl)-1H-indol-2-yl)prop-2-yn-1-yl)amino)-5-(methylsulfonyl)phenoxy)acetamide | 627.2 |
| 1053A | 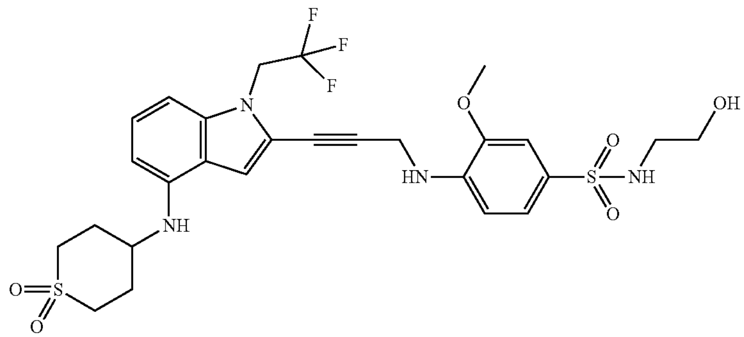 [SMILES: COc1cc(S(=O)(=O)NCCO)ccc1NCC#Cc1cc2c(NC3CCS(=O)(=O)CC3)cccc2n1CC(F)(F)F] | 2-(2-((3-(4-((1,1-dioxidotetrahydro-2H-thiopyran-4-yl)amino)-1-(2,2,2-trifluoroethyl)-1H-indol-2-yl)prop-2-yn-1-yl)amino)-5-(methylsulfonyl)phenoxy)acetamide | 629.2 |

Example G: In Vitro DNA Binding Activity Assay

The ability of a compound of the invention to stabilize p53 Y220C and increase the DNA binding activity of p53 Y220C was measured by a homogeneous time-resolved fluorescence (HTRF) assay. Recombinant His-tagged p53 Y220C used in the HTRF assay was expressed in the bacterium E. coli. The recombinant protein was a truncation mutant containing only amino acids 94-312 of p53, which encompassed the DNA binding domain (DBD) of p53 (SEQ ID NO.: 1). The His-tagged p53 Y220C was tested for DNA binding ability with a consensus sequence of DNA (DNA duplex with a sequence of 5'-ATTAGGCATGTCTAGG-CATGTCTAGG-3'; SEQ ID NO.: 2). SEQ ID NO.: 2 was then conjugated with a biotin label and used in the activity assay.

The binding of the recombinant His-tagged p53 Y220C protein and the biotin-labeled consensus DNA was measured using fluorescence resonance energy transfer (FRET). For the FRET assay, the binding between the p53 mutant and the DNA sequence was measured by detecting the fluorescence of the interaction between an anti-His antibody conjugated to allophycocyanin (APC) and streptavidin conjugated to europium to detect the biotin-labeled DNA.

The test compounds were prepared as 4.5 mM stock solutions in dimethyl sulfoxide (DMSO). The compounds of the disclosure were used to test the stabilization of p53 Y220C and increase in DNA binding activity of p53 Y220C. The stock solutions were then serially diluted 3-fold in DMSO, and 1.2 µL of the diluted solutions was added to each well of a 384-well polypropylene black plate. 30 µL of a 181 nM solution of the recombinant His-tagged p53 Y220C protein and 12.1 nM of APC conjugated anti-His tag antibody in ice-cold Assay Buffer 1 (50 mM Tris-HCl, pH 7.4; 75 mM KCl; 0.75 mM DTT; and 0.2 mg/mL bovine serum albumin (BSA) was added to each well containing the test compounds.

As a background control, 30 µL of Assay Buffer 1 containing 12.1 nM of APC anti-His antibody was also added into a second set of serially-diluted compound plates. The test and control samples were spun at 1200 rpm for 1 minute and incubated at room temperature for 15 minutes. The samples were then further incubated at either 27° C. or 29° C. for 60 min. Five microliters of 311 nM biotin labeled consensus DNA (SEQ ID NO.: 2) and 13.03 nM europium-conjugated streptavidin in Assay Buffer 2 (50 mM Tris-HCl, pH 7.4; 75 mM KCl; and 0.2 mg/mL BSA) were added to each well for both the test and control plates. The plates were spun at 1200 rpm for 1 minute and incubated at room temperature for 20 minutes. The assay signals were monitored by reading excitation at 340 nm, and emission fluorescence at 615 nm and 665 nm on a plate reader.

Normalized time-resolved fluorescence resonance energy transfer (TR-FRET) assay signal ($R_n$) was calculated by the formula:

$$R_n = [(A - B_a - CD)/(D - B_d)](D_c - B_d)$$

where A was the fluorescence intensity of the sample at 665 nm;

D was the fluorescence intensity of the sample at 615 nm;

$B_a$ and $B_d$ were plate background readings at 665 nm and 615 nm, respectively; and $D_c$ was the fluorescence intensity of 1.8 nM Eu-SA in the assay buffer at 615 nm.

The cross talk factor (C) was determined by the following formula:

$$C=(A_c-B_a)/(D_c-B_d)$$

where $A_c$ was the fluorescence intensity of 1.8 nM Eu-labeled anti-FLAG antibody in the assay buffer at 665 nm.

The percentage of activation of protein DNA binding in the presence of a compound of the invention compared to the absence of the compound was denoted by a $SC_{150}$ value, which indicated the concentration of the compound required to increase the DNA binding activity by 50%. The $SC_{150}$ values were calculated using either Prism™ or Activity-Base™.

TABLE 7

| Compound Number | $SC_{150}$ (μM) |
| --- | --- |
| 1A | +++ |
| 2A | ++ |
| 3A | ++++ |
| 4A | + |
| 5A | ++++ |
| 6A | ++++ |
| 7A | ++++ |
| 8A | ++++ |
| 9A | ++++ |
| 10A | ++++ |
| 11A | ++++ |
| 12A | + |
| 13A | ++++ |
| 14A | ++++ |
| 15A | ++++ |
| 16A | ++++ |
| 17A | ++++ |
| 18A | + |
| 19A | + |
| 20A | + |
| 21A | + |
| 22A | + |
| 23A | + |
| 24A | + |
| 25A | + |
| 26A | + |
| 27A | + |
| 28A | ++ |
| 29A | + |
| 30A | + |
| 31A | + |
| 32A | + |
| 33A | + |
| 34A | + |
| 35A | + |
| 36A | +++ |
| 37A | + |
| 39A | + |
| 41A | + |
| 43A | + |
| 44A | + |
| 45A | + |
| 48A | + |
| 49A | + |
| 50A | + |
| 51A | + |
| 54A | + |
| 55A | + |
| 56A | + |
| 57A | + |
| 58A | + |
| 61A | + |
| 62A | + |
| 63A | + |
| 64A | + |
| 65A | + |
| 66A | + |
| 67A | + |
| 68A | + |
| 69A | + |
| 70A | + |
| 71A | + |
| 72A | + |
| 73A | + |
| 74A | + |
| 75A | ++ |
| 76A | + |
| 77A | ++++ |
| 78A | +++ |
| 79A | + |
| 80A | + |
| 81A | + |
| 82A | + |
| 83A | + |
| 84A | ++ |
| 85A | + |
| 86A | + |
| 87A | + |
| 88A | + |
| 89A | + |
| 92A | + |
| 93A | + |
| 94A | +++ |
| 95A | + |
| 96A | ++ |
| 97A | + |
| 98A | + |
| 99A | + |
| 100A | + |
| 101A | + |
| 102A | + |
| 103A | + |
| 104A | + |
| 105A | + |
| 106A | + |
| 107A | + |
| 108A | ++ |
| 109A | + |
| 110A | + |
| 111A | ++++ |
| 112A | +++ |
| 113A | + |
| 114A | + |
| 115A | ++ |
| 117A | + |
| 119A | + |
| 120A | + |
| 121A | + |
| 123A | + |
| 125A | ++++ |
| 127A | + |
| 130A | + |
| 132A | + |
| 134A | + |
| 136A | + |
| 138A | +++ |
| 139A | + |
| 140A | + |
| 142A | + |
| 144A | + |
| 146A | + |
| 148A | + |
| 149A | + |
| 150A | + |
| 151A | + |
| 152A | + |
| 153A | + |
| 155A | + |
| 157A | + |
| 160A | + |
| 162A | + |
| 164A | + |
| 165A | + |
| 166A | + |
| 168A | + |
| 170A | + |
| 171A | + |
| 172A | + |
| 173A | + |

TABLE 7-continued

| Compound Number/SC$_{150}$ (μM) | |
|---|---|
| 174A | + |
| 175A | ++ |
| 176A | + |
| 177A | + |
| 178A | + |
| 179A | ++ |
| 180A | + |
| 183A | + |
| 185A | + |
| 186A | + |
| 187A | + |
| 188A | + |
| 190A | + |
| 192A | + |
| 194A | + |
| 196A | + |
| 198A | + |
| 202A | + |
| 203A | + |
| 204A | + |
| 205A | + |
| 206A | + |
| 207A | + |
| 208A | + |
| 209A | + |
| 210A | + |
| 212A | + |
| 213A | + |
| 214A | + |
| 215A | + |
| 218A | ++++ |
| 220A | + |
| 221A | + |
| 222A | + |
| 223A | + |
| 224A | + |
| 225A | + |
| 226A | + |
| 228A | + |
| 229A | + |
| 230A | + |
| 231A | + |
| 232A | + |
| 233A | ++ |
| 234A | + |
| 235A | + |
| 236A | + |
| 237A | + |
| 238A | + |
| 239A | + |
| 240A | + |
| 241A | + |
| 242A | + |
| 243A | + |
| 244A | ++ |
| 245A | + |
| 248A | + |
| 249A | + |
| 250A | + |
| 251A | + |
| 253A | + |
| 255A | + |
| 257A | + |
| 259A | + |
| 261A | + |
| 263A | + |
| 265A | + |
| 267A | + |
| 269A | + |
| 273A | + |
| 275A | + |
| 277A | ++ |
| 279A | + |
| 281A | + |
| 283A | + |
| 285A | + |
| 287A | + |
| 289A | + |
| 293A | + |
| 294A | + |
| 295A | + |
| 296A | + |
| 297A | + |
| 298A | + |
| 299A | + |
| 300A | + |
| 301A | + |
| 303A | + |
| 304A | + |
| 305A | + |
| 307A | + |
| 309A | + |
| 311A | ++ |
| 313A | + |
| 314A | + |
| 315A | + |
| 316A | + |
| 318A | + |
| 320A | + |
| 322A | + |
| 324A | + |
| 327A | + |
| 329A | + |
| 331A | + |
| 333A | + |
| 335A | + |
| 340A | + |
| 342A | + |
| 344A | + |
| 346A | + |
| 348A | + |
| 350A | + |
| 352A | + |
| 354A | + |
| 356A | + |
| 358A | + |
| 362A | + |
| 364A | + |
| 369A | + |
| 370A | + |
| 372A | + |
| 374A | + |
| 375A | + |
| 376A | + |
| 377A | + |
| 379A | + |
| 381A | + |
| 383A | + |
| 385A | + |
| 387A | + |
| 389A | + |
| 390A | + |
| 391A | + |
| 393A | + |
| 395A | + |
| 398A | + |
| 399A | + |
| 400A | + |
| 401A | ++ |
| 402A | + |
| 403A | ++ |
| 404A | + |
| 405A | + |
| 406A | + |
| 407A | + |
| 409A | + |
| 410A | + |
| 411A | + |
| 414A | + |
| 416A | + |
| 418A | + |
| 420A | + |
| 422A | + |
| 424A | + |
| 426A | + |
| 427A | + |

TABLE 7-continued

| Compound Number | SC$_{150}$ (µM) |
|---|---|
| 428A | + |
| 430A | + |
| 432A | + |
| 434A | + |
| 436A | + |
| 438A | + |
| 440A | + |
| 442A | + |
| 444A | + |
| 446A | + |
| 448A | ++ |
| 455A | + |
| 456A | ++++ |
| 457A | ++ |
| 458A | + |
| 459A | + |
| 460A | + |
| 461A | + |
| 463A | + |
| 464A | + |
| 466A | + |
| 468A | + |
| 469A | + |
| 470A | + |
| 471A | + |
| 472A | + |
| 473A | + |
| 474A | + |
| 475A | +++ |
| 477A | + |
| 478A | ++++ |
| 479A | + |
| 480A | + |
| 482A | + |
| 483A | + |
| 484A | + |
| 485A | + |
| 486A | + |
| 487A | ++ |
| 488A | +++ |
| 489A | + |
| 490A | + |
| 491A | + |
| 492A | + |
| 494A | + |
| 495A | +++ |
| 496A | + |
| 497A | + |
| 498A | + |
| 499A | + |
| 500A | + |
| 501A | + |
| 502A | + |
| 503A | ++ |
| 504A | + |
| 505A | +++ |
| 506A | + |
| 507A | ++ |
| 508A | + |
| 509A | + |
| 510A | + |
| 511A | + |
| 512A | ++ |
| 514A | + |
| 515A | ++ |
| 516A | + |
| 517A | +++ |
| 519A | ++++ |
| 520A | +++ |
| 522A | + |
| 523A | + |
| 524A | + |
| 525A | + |
| 526A | ++ |
| 531A | ++ |
| 532A | ++ |
| 533A | ++ |
| 534A | + |
| 535A | + |
| 536A | + |
| 537A | + |
| 538A | + |
| 539A | + |
| 540A | + |
| 541A | + |
| 542A | + |
| 543A | + |
| 544A | + |
| 545A | + |
| 546A | + |
| 547A | + |
| 549A | + |
| 550A | + |
| 551A | + |
| 552A | + |
| 553A | + |
| 554A | + |
| 555A | + |
| 557A | + |
| 558A | + |
| 559A | + |
| 562A | + |
| 563A | + |
| 564A | + |
| 565A | + |
| 566A | + |
| 567A | + |
| 568A | + |
| 569A | + |
| 572A | + |
| 573A | + |
| 574A | + |
| 575A | + |
| 577A | + |
| 578A | + |
| 579A | + |
| 580A | + |
| 581A | + |
| 582A | + |
| 583A | + |
| 584A | + |
| 585A | + |
| 586A | + |
| 587A | + |
| 588A | +++ |
| 589A | ++ |
| 590A | + |
| 591A | + |
| 592A | + |
| 593A | + |
| 594A | + |
| 595A | + |
| 596A | + |
| 598A | + |
| 599A | + |
| 600A | + |
| 601A | + |
| 602A | + |
| 603A | + |
| 604A | + |
| 605A | + |
| 606A | + |
| 607A | + |
| 608A | + |
| 609A | + |
| 610A | + |
| 611A | + |
| 612A | + |
| 613A | + |
| 616A | + |
| 617A | + |
| 618A | + |
| 619A | + |
| 620A | + |
| 621A | + |
| 622A | + |

TABLE 7-continued

| Compound Number | SC$_{150}$ (μM) |
|---|---|
| 623A | + |
| 624A | + |
| 625A | + |
| 627A | + |
| 628A | + |
| 629A | + |
| 630A | + |
| 631A | + |
| 632A | + |
| 633A | + |
| 634A | + |
| 635A | + |
| 637A | + |
| 638A | + |
| 642A | + |
| 643A | +++ |
| 644A | + |
| 645A | + |
| 646A | + |
| 647A | + |
| 648A | + |
| 649A | + |
| 650A | + |
| 651A | + |
| 652A | + |
| 653A | + |
| 654A | + |
| 655A | + |
| 656A | + |
| 657A | + |
| 658A | + |
| 659A | + |
| 660A | + |
| 661A | + |
| 662A | + |
| 663A | + |
| 664A | + |
| 665A | + |
| 666A | + |
| 667A | + |
| 668A | + |
| 669A | + |
| 670A | ++++ |
| 672A | + |
| 673A | + |
| 674A | + |
| 675A | + |
| 676A | +++ |
| 677A | + |
| 678A | + |
| 683A | + |
| 685A | + |
| 686A | + |
| 688A | + |
| 689A | +++ |
| 690A | + |
| 691A | + |
| 692A | + |
| 694A | + |
| 695A | + |
| 697A | + |
| 698A | + |
| 699A | + |
| 700A | + |
| 701A | + |
| 702A | + |
| 703a | + |
| 704a | ++ |
| 705A | + |
| 706A | + |
| 707A | + |
| 708A | ++ |
| 709A | + |
| 710A | + |
| 711A | ++ |
| 712A | ++ |
| 713A | + |
| 714A | ++++ |
| 715A | + |
| 716A | ++ |
| 719A | +++ |
| 720A | + |
| 721A | + |
| 722A | + |
| 723A | + |
| 724A | + |
| 729A | + |
| 730A | + |
| 731A | + |
| 732A | + |
| 739A | + |
| 740A | + |
| 741A | + |
| 742A | + |
| 745A | + |
| 746A | + |
| 747A | + |
| 748A | + |
| 749A | + |
| 750A | + |
| 751A | + |
| 752A | + |
| 753A | + |
| 755A | + |
| 756A | + |
| 757A | + |
| 758A | + |
| 759A | + |
| 761A | + |
| 762A | + |
| 764A | + |
| 765A | + |
| 766A | + |
| 767A | + |
| 769A | + |
| 771A | + |
| 772A | + |
| 773A | + |
| 774A | + |
| 775A | + |
| 776A | + |
| 777A | + |
| 778A | + |
| 779A | + |
| 780A | + |
| 781A | + |
| 782A | + |
| 783A | + |
| 785A | + |
| 788A | + |
| 789A | ++ |
| 790A | + |
| 791A | + |
| 792A | + |
| 793A | + |
| 794A | + |
| 795A | + |
| 796A | + |
| 797A | + |
| 798A | + |
| 799A | + |
| 800A | + |
| 801A | + |
| 802A | + |
| 803A | + |
| 804A | + |
| 805A | + |
| 806A | + |
| 808A | + |
| 809A | + |
| 810A | + |
| 811A | + |
| 812A | + |
| 813A | + |
| 814A | + |
| 815A | + |

TABLE 7-continued

| Compound Number | SC$_{150}$ (μM) |
|---|---|
| 816A | + |
| 817A | + |
| 818A | + |
| 819A | + |
| 820A | + |
| 821A | + |
| 823A | + |
| 824A | + |
| 825A | + |
| 826A | + |
| 827A | + |
| 828A | + |
| 829A | + |
| 830A | + |
| 831A | + |
| 833A | ++ |
| 834A | + |
| 835A | + |
| 836A | + |
| 837A | + |
| 838A | + |
| 839A | + |
| 840A | + |
| 841A | + |
| 842A | + |
| 843A | + |
| 844A | + |
| 845A | + |
| 846A | + |
| 848A | + |
| 849A | + |
| 851A | + |
| 852A | + |
| 853A | + |
| 854A | + |
| 855A | + |
| 856A | + |
| 857A | + |
| 858A | + |
| 859A | + |
| 860A | + |
| 862A | + |
| 863A | + |
| 864A | + |
| 865A | + |
| 866A | + |
| 867A | + |
| 868A | + |
| 869A | + |
| 870A | + |
| 871A | + |
| 878A | + |
| 879A | + |
| 880A | ++++ |
| 882A | + |
| 883A | + |
| 884A | + |
| 888A | + |
| 889A | + |
| 890A | + |
| 891A | + |
| 892A | + |
| 893A | + |
| 894A | + |
| 895A | +++ |
| 896A | + |
| 897A | + |
| 898A | + |
| 899A | + |
| 900A | + |
| 901A | + |
| 902A | + |
| 903A | + |
| 904A | + |
| 905A | + |
| 906A | + |
| 907A | + |
| 908A | + |
| 909A | + |
| 910A | + |
| 911A | + |
| 912A | + |
| 913A | + |
| 914A | + |
| 915A | + |
| 917A | + |
| 918A | + |
| 919A | + |
| 920A | + |
| 921A | + |
| 922A | ++ |
| 924A | + |
| 925A | + |
| 926A | + |
| 927A | + |
| 928A | ++++ |
| 929A | + |
| 930A | + |
| 931A | + |
| 932A | + |
| 933A | + |
| 934A | + |
| 935A | + |
| 936A | + |
| 937A | + |
| 938A | + |
| 939A | + |
| 940A | + |
| 941A | + |
| 942A | + |
| 944A | + |
| 945A | + |
| 946A | + |
| 947A | + |
| 948A | + |
| 950A | + |
| 951A | + |
| 952A | + |
| 953A | + |
| 954A | + |
| 955A | + |
| 956A | + |
| 957A | + |
| 958A | + |
| 960A | + |
| 961A | + |
| 962A | + |
| 963A | + |
| 964A | + |
| 965A | + |
| 966A | + |
| 967A | + |
| 968A | + |
| 969A | + |
| 970A | + |
| 971A | + |
| 972A | + |
| 988A | + |
| 989A | + |
| 990A | + |
| 991A | + |
| 992A | + |
| 993A | + |
| 994A | + |
| 995A | + |
| 996A | + |
| 997A | + |
| 998A | + |
| 999A | + |
| 1000A | + |
| 1001A | + |
| 1002A | + |
| 1003A | + |
| 1007A | + |
| 1008A | + |
| 1009A | + |

TABLE 7-continued

| Compound Number/SC$_{150}$ (µM) | |
|---|---|
| 1010A | ++++ |
| 1011A | + |
| 1012A | ++++ |
| 1013A | +++ |
| 1014A | + |
| 1016A | + |
| 1017A | + |
| 1018A | + |
| 1019A | + |
| 1020A | + |
| 1021A | + |
| 1022A | + |
| 1023A | ++ |
| 1024A | + |
| 1025A | + |
| 1026A | + |
| 1027A | ++ |
| 1028A | +++ |
| 1029A | +++ |
| 1030A | ++ |
| 1031A | + |
| 1032A | ++ |
| 1034A | + |
| 1035A | + |
| 1036A | + |
| 1037A | ++ |
| 1038A | + |
| 1039A | + |
| 1040A | + |
| 1041A | + |
| 1042A | + |
| 1043A | + |
| 1044A | + |
| 1045A | + |
| 1046A | + |
| 1047A | + |
| 1048A | + |
| 1049A | + |
| 1055A | + |
| 1056A | + |
| 1057A | + |
| 1058A | + |
| 1059A | + |
| 1060A | + |
| 1061A | + |
| 1062A | + |
| 1063A | + |
| 1064A | + |
| 1065A | + |
| 1066A | + |
| 1067A | + |
| 1068A | + |
| 1069A | + |
| 1070A | + |
| 1071A | + |
| 1072A | + |
| 1073A | + |
| 1074A | + |
| 1075A | + |

+ = 0 µM ≤ SC$_{150}$ < 0.05 µM
++ = 0.05 µM ≤ SC$_{150}$ < 0.1 µM
+++ = 0.1 µM ≤ SC$_{150}$ < 0.2 µM
++++ = 0.2 µM ≤ SC$_{150}$ < 1 µM

EMBODIMENTS

The following non-limiting embodiments provide illustrative examples of the invention, but do not limit the scope of the invention.

Embodiment 1. A compound of the formula:

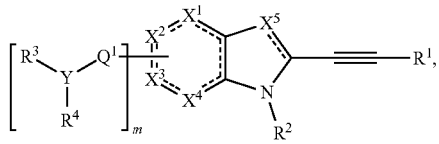

wherein:
each ═══ is independently a single bond or a double bond;
$X^1$ is $CR^5$, $CR^5R^6$, N, $NR^5$, O, S, C═O, C═S, or a carbon atom connected to $Q^1$;
$X^2$ is $CR^7$, $CR^7R^8$, N, $NR^7$, O, S, C═O, C═S, or a carbon atom connected to $Q^1$;
$X^3$ is $CR^9$, $CR^9R^{10}$, N, $NR^9$, O, S, C═O, C═S, or a carbon atom connected to $Q^1$;
$X^4$ is $CR^{11}$, $CR^{11}R^{12}$, N, $NR^{11}$, O, S, C═O, C═S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
$Q^1$ is C═O, C═S, C═$CR^{14}R^{15}$, C═$NR^{14}$, alkylene, alkenylene, or alkynylene, each of which is independently substituted or unsubstituted, or a bond;
m is 1, 2, 3, or 4;
Y is N, O, or absent;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, C═O, C═S, —CN, —Si$R^{16}R^{17}R^{18}$, alkyl, alkenyl, alkynyl, aryl, heteroaryl, or heterocyclyl, each of which is independently substituted or unsubstituted, or hydrogen;
each $R^3$ and $R^4$ is independently, —C(O)$R^{19}$, —C(O)O$R^{19}$, —C(O)N$R^{19}R^{20}$, —SO$R^{19}$, —SO$_2R^{19}$, alkyl, alkylene, alkenyl, alkenylene, alkynyl, aryl, heteroaryl, or heterocyclyl, each of which is independently substituted or unsubstituted, or hydrogen, or $R^3$ and $R^4$ together with the Y atom to which $R^3$ and $R^4$ are bound form a ring, wherein the ring is substituted or unsubstituted, or $R^3$ is absent;
each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen,
or a pharmaceutically-acceptable salt thereof, wherein the compound is not a compound of Table 1.

Embodiment 2. A compound of the formula:

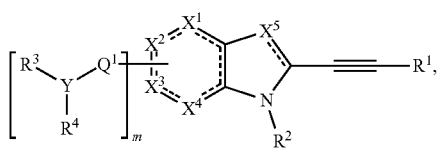

wherein:
- each ====== is independently a single bond or a double bond;
- $X^1$ is $CR^5$, $CR^5R^6$, N, $NR^5$, O, S, C=O, C=S, or a carbon atom connected to $Q^1$;
- $X^2$ is $CR^7$, $CR^7R^8$, N, $NR^7$, O, S, C=O, C=S, or a carbon atom connected to $Q^1$;
- $X^3$ is $CR^9$, $CR^9R^{10}$, N, $NR^9$, O, S, C=O, C=S, or a carbon atom connected to $Q^1$;
- $X^4$ is $CR^{11}$, $CR^{11}R^{12}$, N, $NR^{11}$, O, S, C=O, C=S, or a carbon atom connected to $Q^1$;
- $X^5$ is $CR^{13}$, N, or $NR^{13}$;
- wherein at least one of $X^1$, $X^2$, $X^3$, and $X^4$ is a carbon atom connected to $Q^1$;
- $Q^1$ is C=O, C=S, C=$CR^{14}R^{15}$, C=$NR^{14}$, alkylene, alkenylene, or alkynylene, each of which is independently substituted or unsubstituted, or a bond;
- m is 1, 2, 3, or 4;
- Y is N, O, or absent;
- $R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, C=O, C=S, —CN, —Si$R^{16}R^{17}R^{18}$, alkyl, alkenyl, alkynyl, aryl, heteroaryl, or heterocyclyl, each of which is independently substituted or unsubstituted, or hydrogen;
- each $R^3$ and $R^4$ is independently, —C(O)$R^{19}$, —C(O)O$R^{19}$, —C(O)N$R^{19}R^{20}$, —SO$R^{19}$, —SO$_2R^{19}$, alkyl, alkylene, alkenyl, alkenylene, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent, wherein at least one of $R^3$ and $R^4$ is alkyl, alkylene, alkenyl, alkenylene, alkynyl, aryl, heteroaryl, or heterocyclyl, each of which is substituted at least with halo-;
- each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
- each $R^{19}$ and $R^{20}$ is C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
- each $R^{21}$ and $R^{22}$ is independently alkyl, alkenyl, alkynyl, aryl, heteroaryl, or heterocyclyl, each of which is independently substituted or unsubstituted, or hydrogen; and
- each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

Embodiment 3. The compound of embodiment 1 or 2, wherein $X^1$ is a carbon atom connected to $Q^1$.

Embodiment 4. The compound of embodiment 1 or 2, wherein $X^2$ is a carbon atom connected to $Q^1$.

Embodiment 5. The compound of any one of embodiments 1-4, wherein $Q^1$ is a bond.

Embodiment 6. The compound of any one of embodiments 1-5, wherein Y is N or O.

Embodiment 7. The compound of any one of embodiments 1-6, wherein Y is N.

Embodiment 8. The compound of any one of embodiments 1-7, wherein m is 1.

Embodiment 9. The compound of any one of embodiments 1-7, wherein m is 2.

Embodiment 10. The compound of any one of embodiments 1-3 and 5-8, wherein the compound is of the formula:

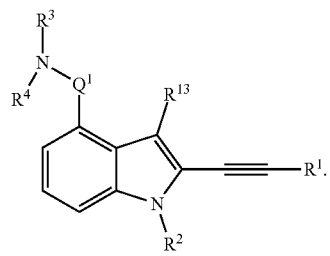

Embodiment 11. The compound of any one of embodiments 1-3, 5-8, and 10, wherein the compound has the formula:

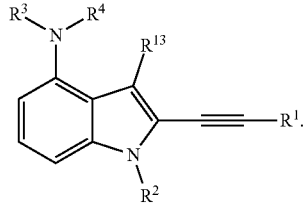

Embodiment 12. The compound of any one of embodiments 1, 2, and 4-8, wherein the compound is of the formula:

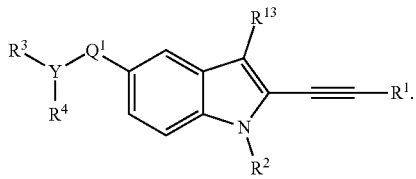

Embodiment 13. The compound of any one of embodiments 1, 2, 4-8, and 12, wherein the compound has the formula:

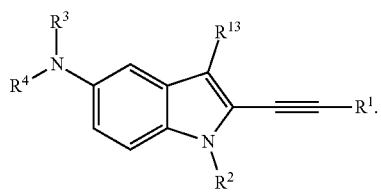

Embodiment 14. The compound of any one of embodiments 1-13, wherein $R^1$ is alkyl, alkenyl, —C(O)$R^{16}$, —C(O)O$R^{16}$, or —C(O)N$R^{16}R^{17}$.

Embodiment 15. The compound of any one of embodiments 1-14, wherein $R^1$ is substituted alkyl.

Embodiment 16. The compound of any one of embodiments 1-15, wherein $R^1$ is alkyl substituted with N$R^{16}R^{17}$.

Embodiment 17. The compound of any one of embodiments 1-8, 10, 11, and 14-16, wherein the compound is of the formula:

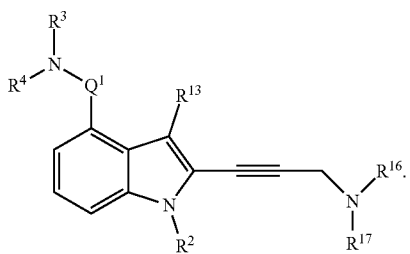

Embodiment 18. The compound of any one of embodiments 1-8, 10, 11, and 14-17, wherein the compound has the formula:

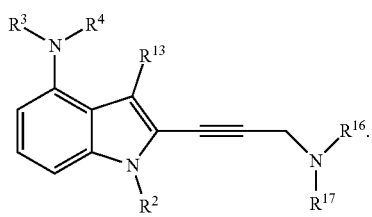

Embodiment 19. The compound of any one of embodiments 1-8 and 12-16, wherein the compound is of the formula:

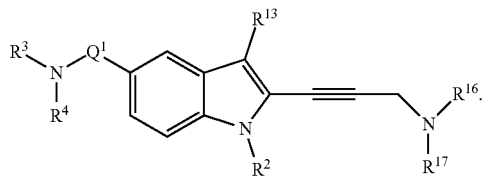

Embodiment 20. The compound of any one of embodiments 1-8, 12-16, and 19, wherein the compound has the formula:

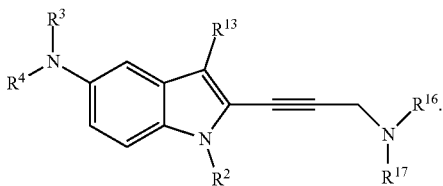

Embodiment 21. The compound of any one of embodiments 1-20, wherein each $R^{16}$ and $R^{17}$ is independently alkyl, alkenyl, aryl, heteroaryl, heterocyclyl, each of which is independently substituted or unsubstituted, or hydrogen.

Embodiment 22. The compound of any one of embodiments 1-21, wherein $R^{16}$ is hydrogen or alkyl.

Embodiment 23. The compound of any one of embodiments 1-22, wherein $R^{17}$ is aryl, heteroaryl, or heterocyclyl, each of which is independently substituted or unsubstituted.

Embodiment 24. The compound of any one of embodiments 1-23, wherein $R^{17}$ is substituted aryl.

Embodiment 25. The compound of any one of embodiments 1-24, wherein $R^{17}$ is substituted phenyl.

Embodiment 26. The compound of any one of embodiments 1-25, wherein $R^{17}$ is phenyl substituted with a sulfoxide group, carboxyl group, amide group, amino group, alkyl, alkoxy, hydroxy, halo, cyano, or heterocyclyl, each of which is independently substituted or unsubstituted.

Embodiment 27. The compound of any one of embodiments 1-26, wherein $R^{17}$ is phenyl substituted with methoxy.

Embodiment 28. The compound of any one of embodiments 1-26, wherein $R^{17}$ is phenyl substituted with a substituted sulfoxide group.

Embodiment 29. The compound of any one of embodiments 1-26, wherein $R^{17}$ is phenyl substituted with a carboxyl group.

Embodiment 30. The compound of any one of embodiments 1-26, wherein $R^{17}$ is phenyl substituted with a substituted amide group.

Embodiment 31. The compound of any one of embodiments 1-30, wherein $R^2$ is hydrogen or substituted or unsubstituted alkyl.

Embodiment 32. The compound of any one of embodiments 1-31, wherein $R^2$ is substituted $C_1$-$C_5$-alkyl.

Embodiment 33. The compound of any one of embodiments 1-32, wherein $R^2$ is trifluoroethyl.

Embodiment 34. The compound of any one of embodiments 1-32, wherein $R^2$ is cycloalkyl.

Embodiment 35. The compound of any one of embodiments 1-34, wherein $R^{13}$ is alkyl, alkenyl, hydrogen, or halogen.

Embodiment 36. The compound of any one of embodiments 1-35, wherein $R^{13}$ is hydrogen.

Embodiment 37. The compound of any one of embodiments 1-3, 4-8, 10, 11, 14-18, 21-33, 35, and 36, wherein the compound has the formula:

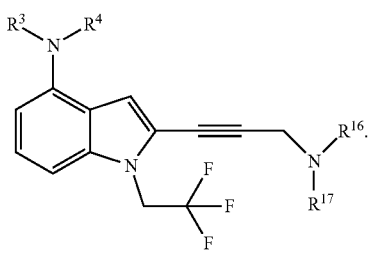

Embodiment 38. The compound of any one of embodiments 1, 2, 4-8, 12-16, 19-33, 35, and 36, wherein the compound has the formula:

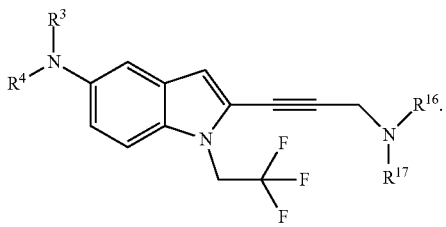

Embodiment 39. The compound of any one of embodiments 1-38, wherein at least one of $R^3$ and $R^4$ is aryl, heteroaryl, or heterocyclyl, each of which is substituted at least with halo-.

Embodiment 40. The compound of any one of embodiments 1-39, wherein $R^3$ is H, and $R^4$ is aryl, heteroaryl, or heterocyclyl, each of which is substituted at least with halo-.

Embodiment 41. The compound of any one of embodiments 1-40, wherein $R^3$ is H, and $R^4$ is aryl substituted at least with fluoro-.

Embodiment 42. The compound of any one of embodiments 1-40, wherein $R^3$ is H, and $R^4$ is heteroaryl substituted at least with fluoro-.

Embodiment 43. The compound of any one of embodiments 1-42, wherein $R^3$ is H, and $R^4$ is heterocyclyl substituted at least with fluoro-.

Embodiment 44. The compound of any one of embodiments 1-43, wherein at least one of R and $R^4$ is aryl, heteroaryl, or heterocyclyl, each of which is substituted at least with chloro-.

Embodiment 45. The compound of any one of embodiments 1-44, wherein $R^3$ is H, and $R^4$ is heterocyclyl substituted at least with chloro-.

Embodiment 46. The compound of any one of embodiments 1-45, wherein $R^4$ is substituted piperidinyl.

Embodiment 47. The compound of any one of embodiments 1-47, wherein $R^4$ is piperidinyl substituted at least with alkyl, carboxy, heterocyclyl, or an amide group, each of which is substituted or unsubstituted.

Embodiment 48. The compound of any one of embodiments 1-47, wherein $R^4$ is unsubstituted or substituted methyl piperidinyl.

Embodiment 49. The compound of any one of embodiments 1-48, wherein $R^4$ is 3-fluoro-1-methylpiperidinyl.

Embodiment 50. The compound of any one of embodiments 1-47, wherein $R^4$ is piperidinyl substituted with a substituted or unsubstituted methoxypropanol.

Embodiment 51. The compound of any one of embodiments 1-47 and 50, wherein $R^4$ is 3-fluoro-1-(2-hydroxy-3-methoxypropyl)piperidinyl.

Embodiment 52. The compound of any one of embodiments 1-45, wherein $R^4$ is unsubstituted or substituted tetrahydropyranyl.

Embodiment 53. The compound of any one of embodiments 1-45 and 52, wherein $R^4$ is unsubstituted tetrahydropyranyl.

Embodiment 54. The compound of any one of embodiments 1-45 and 52, wherein $R^4$ is tetrahydropyranyl substituted with alkyl.

Embodiment 55. The compound of any one of embodiments 1-45, 52, and 54, wherein $R^4$ is tetrahydrothiopyran-1,1-dioxide.

Embodiment 56. The compound of any one of embodiments 1-3, 5-8, 10, 11, 14-18, 21-28, 31-33, and 35-37, wherein the compound is:

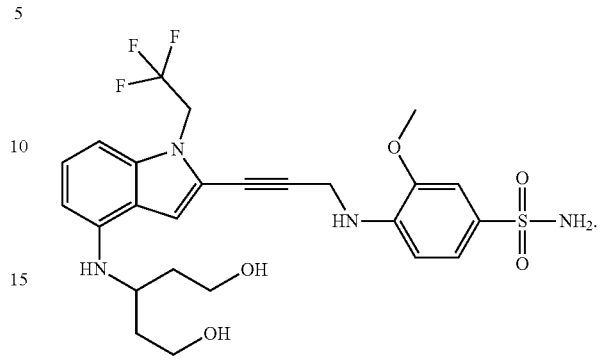

Embodiment 57. The compound of any one of embodiments 1-3, 5-8, 10, 11, 14-18, 21-28, 31-33, and 35-37, wherein the compound is:

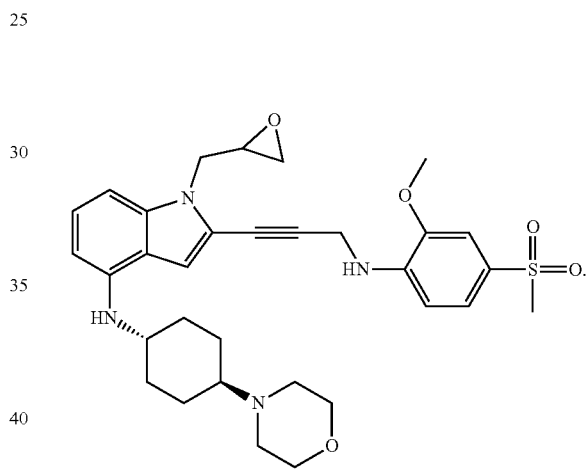

Embodiment 58. The compound of any one of embodiments 1-3, 5-8, 10, 11, 14-18, 21-28, 31-33, and 35-37, wherein the compound is:

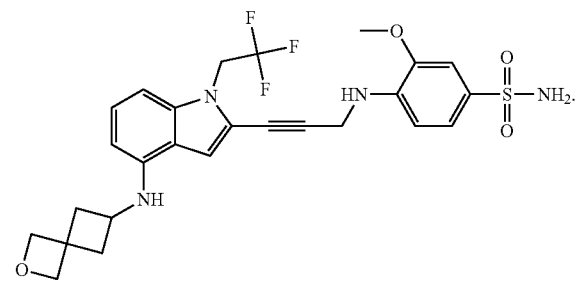 [SMILES: COc1cc(S(N)(=O)=O)ccc1NCC#Cc1cc2c(NC3CC4(COC4)C3)cccc2n1CC(F)(F)F]

Embodiment 59. The compound of any one of embodiments 1-3, 5-8, 10, 11, 14-18, 21-28, 31-33, 35-37, and 39-49, wherein the compound is:

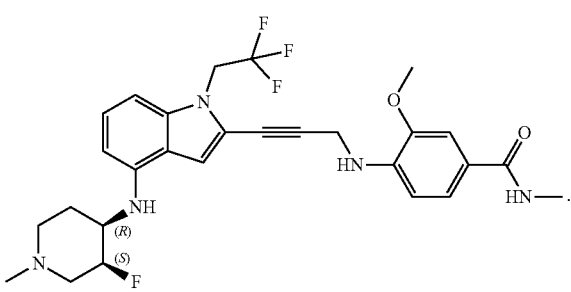

Embodiment 60. The compound of any one of embodiments 1-3, 5-8, 10, 11, 14-18, 21-28, 31-33, 35-37, and 39-49, wherein the compound is:

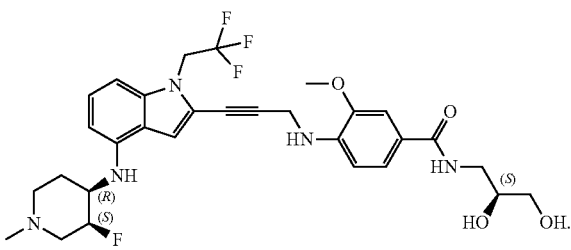

Embodiment 61. The compound of any one of embodiments 1-3, 5-8, 10, 11, 14-18, 21-28, 31-33, and 35-37, wherein the compound is:

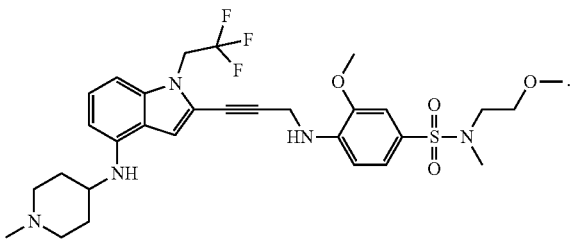

Embodiment 62. The compound of any one of embodiments 1-3, 5-8, 10, 11, 14-18, 21-28, 31-33, and 35-37, wherein the compound is:

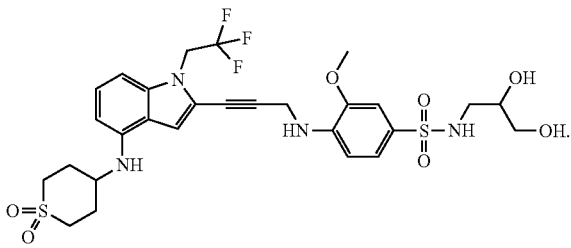 [SMILES: COc1cc(S(=O)(=O)NCC(O)CO)ccc1NCC#Cc1cc2c(NC3CCS(=O)(=O)CC3)cccc2n1CC(F)(F)F]

Embodiment 63. The compound of any one of embodiments 1-3, 5-8, 10, 11, 14-18, 21-28, 31-33, and 35-37, wherein the compound is:

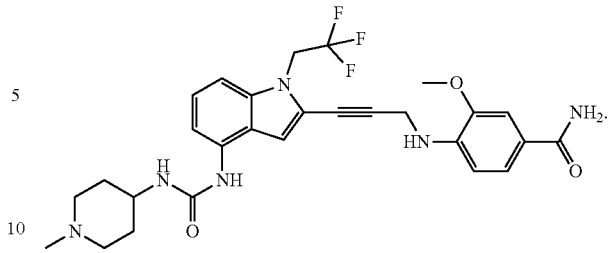

Embodiment 64. The compound of any one of embodiments 1-3, 5-8, 10, 11, 14-18, 21-28, 31-33, 35-37, and 39-49, wherein the compound is:

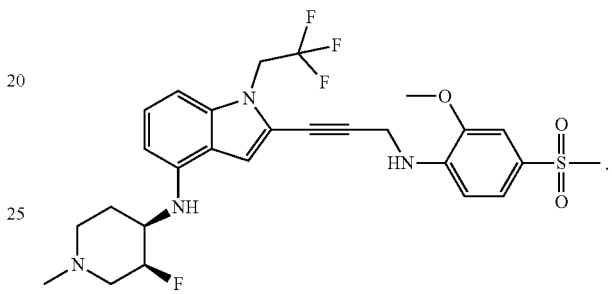

Embodiment 65. A compound comprising: a heterocyclyl group comprising a halogen substituent, wherein the compound binds a mutant p53 protein and increases wild-type p53 activity of the mutant p53 protein.

Embodiment 66. The compound of embodiment 65, wherein the compound further comprises an indole group attached to the heterocyclyl group.

Embodiment 67. The compound of embodiment 66, wherein the indole group has a 1,1,1-trifluoroethyl substituent at a 1-position of the indole group.

Embodiment 68. The compound of any one of embodiments 65-67, wherein the indole group has a propargyl substituent at a 2-position of the indole group.

Embodiment 69. The compound of embodiment 68, wherein the propargyl substituent is attached to the indole group via an sp carbon atom of the propargyl substituent.

Embodiment 70. The compound of embodiment 68 or 69, wherein the propargyl substituent is attached to a nitrogen atom of an aniline group via a methylene group of the propargyl substituent.

Embodiment 71. The compound of any one of embodiments 66-70, wherein the indole group comprises an amino substituent at a 4-position of the indole group.

Embodiment 72. The compound of embodiment 71, wherein the amino substituent is attached to the heterocyclyl group.

Embodiment 73. The compound of any one of embodiments 65-72, wherein the heterocyclyl group is a piperidine group.

Embodiment 74. The compound of any one of embodiments 65-73, wherein the halogenated substituent comprises a fluoro group.

Embodiment 75. The compound of any one of embodiments 65-73, wherein the halogenated substituent comprises a chloro group.

Embodiment 76. The compound of any one of embodiments 65-75, wherein the heterocyclyl group further comprises at least one substituent group.

Embodiment 77. The compound of any one of embodiments 65-76, wherein the heterocyclyl group comprises an alkyl group.

Embodiment 78. The compound of any one of embodiments 65-77, wherein the heterocyclyl group comprises a methyl group.

Embodiment 79. The compound of any one of embodiments 65-78, wherein the heterocyclyl group is a methylpiperidine group.

Embodiment 80. The compound of any one of embodiments 65-79, wherein the heterocyclyl group is 1-methylpiperidinyl.

Embodiment 81. The compound of any one of embodiments 65-80, wherein the heterocyclyl group is 1-methylpiperidin-4-yl.

Embodiment 82. The compound of any one of embodiments 65-81, wherein the heterocyclyl group is 3-fluoro-1-methylpiperidin-4-yl.

Embodiment 83. The compound of embodiment 70, wherein, the aniline group is substituted with a hydroxyl group, sulfhydryl group, halogens, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group.

Embodiment 84. The compound of embodiment 70 or 83, wherein the aniline group is substituted with an alkoxy group.

Embodiment 85. The compound of any one of embodiments 70, 83, or 84, wherein the aniline group is substituted with a sulfonamide group.

Embodiment 86. The compound of any one of embodiments 70 or 83-85, wherein the aniline group is substituted with an amide.

Embodiment 87. The compound of any one of embodiments 65-86, wherein the compound is of the formula

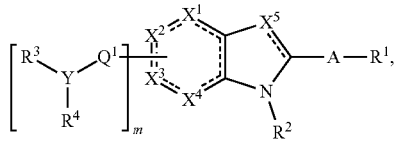

wherein:
each ------- is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
A is a linking group;
$Q^1$ is C=O, C=S, C=$CR^{14}R^{15}$, C=$NR^{14}$, alkylene, alkenylene, or alkynylene, each of which is independently substituted or unsubstituted, or a bond;
m is 1, 2, 3, or 4;
Y is N, O, or absent;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;
each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent; wherein at least one of $R^3$ and $R^4$ is alkyl, alkylene, alkenyl, alkenylene, alkynyl, alkynylene, aryl, heteroaryl, or heterocyclyl, each of which is substituted with at least halo;
each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is independently —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen,
or a pharmaceutically-acceptable salt thereof.

Embodiment 88. The compound of any one of embodiments 65-87, wherein the compound is of the formula:

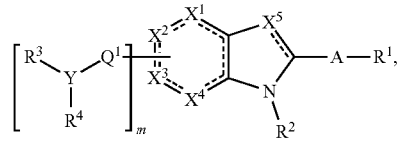

wherein:
each ------- is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
A is a linking group;

$Q^1$ is C=O, C=S, C=CR$^{14}$R$^{15}$, C=NR$^{14}$, alkylene, alkenylene, or alkynylene, each of which is independently substituted or unsubstituted, or a bond;

m is 1, 2, 3, or 4;

Y is N, O, or absent;

R$^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, heterocyclyl, or halo, each of which is independently substituted or unsubstituted, or hydrogen;

each R$^3$ and R$^4$ is independently —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted, or hydrogen, or R$^3$ and R$^4$ together with the nitrogen atom to which R$^3$ and R$^4$ are bound form a ring, wherein the ring is substituted or unsubstituted, or R$^3$ is absent;

each R$^2$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, and R$^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

each R$^{19}$ and R$^{20}$ is independently —C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;

each R$^{21}$ and R$^{22}$ is independently alkyl, alkenyl, alkynyl, aryl, heteroaryl, or heterocyclyl, each of which is independently substituted or unsubstituted, or hydrogen; and each R$^{23}$ and R$^{24}$ is independently alkyl, alkenyl, alkynyl, aryl, heteroaryl, or heterocyclyl, each of which is independently substituted or unsubstituted, or hydrogen, or a pharmaceutically-acceptable salt thereof, wherein the compound is not a compound of Table 1.

Embodiment 89. The compound of any one of embodiments 65-88, wherein the compound is of the formula:

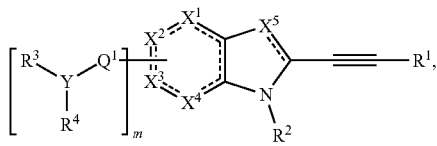

wherein:
each ------- is independently a single bond or a double bond;

$X^1$ is CR$^5$, CR$^5$R$^6$, N, NR$^5$, O, S, C=O, C=S, or a carbon atom connected to $Q^1$;

$X^2$ is CR$^7$, CR$^7$R$^8$, N, NR$^7$, O, S, C=O, C=S, or a carbon atom connected to $Q^1$;

$X^3$ is CR$^9$, CR$^9$R$^{10}$, N, NR$^9$, O, S, C=O, C=S, or a carbon atom connected to $Q^1$;

$X^4$ is CR$^{11}$, CR$^{11}$R$^{12}$, N, NR$^{11}$, O, S, C=O, C=S, or a carbon atom connected to $Q^1$;

$X^5$ is CR$^{13}$, N, or NR$^{13}$;

wherein at least one of $X^1$, $X^2$, $X^3$, and $X^4$ is a carbon atom connected to $Q^1$;

$Q^1$ is C=O, C=S, C=CR$^{14}$R$^{15}$, C=NR$^{14}$, alkylene, alkenylene, or alkynylene, each of which is independently substituted or unsubstituted, or a bond;

m is 1, 2, 3, or 4;

Y is N, O, or absent;

R$^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, C=O, C=S, —CN, —SiR$^{16}$R$^{17}$R$^{18}$, alkyl, alkenyl, alkynyl, aryl, heteroaryl, or heterocyclyl, each of which is independently substituted or unsubstituted, or hydrogen;

each R$^3$ and R$^4$ is independently, —C(O)R$^{19}$, —C(O)OR$^{19}$, —C(O)NR$^{19}$R$^{20}$, —SOR$^{19}$, —SO$_2$R$^{19}$, alkyl, alkylene, alkenyl, alkenylene, alkynyl, aryl, heteroaryl, or heterocyclyl, each of which is independently substituted or unsubstituted, or hydrogen, or R$^3$ and R$^4$ together with the Y atom to which R$^3$ and R$^4$ are bound form a ring, wherein the ring is substituted or unsubstituted, or R$^3$ is absent;

each R$^2$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, and R$^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

each R$^{19}$ and R$^{20}$ is C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;

each R$^{21}$ and R$^{22}$ is independently alkyl, alkenyl, alkynyl, aryl, heteroaryl, or heterocyclyl, each of which is independently substituted or unsubstituted, or hydrogen; and each R$^{23}$ and R$^{24}$ is independently alkyl, alkenyl, alkynyl, aryl, heteroaryl, or heterocyclyl, each of which is independently substituted or unsubstituted, or hydrogen, or a pharmaceutically-acceptable salt thereof, wherein the compound is not a compound of Table 1.

Embodiment 90. The compound of any one of embodiments 65-89, wherein the compound is of the formula:

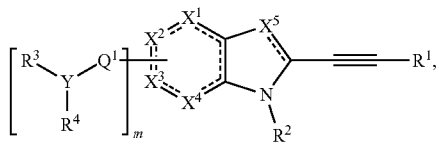

wherein:
each ------- is independently a single bond or a double bond;

$X^1$ is CR$^5$, CR$^5$R$^6$, N, NR$^5$, 0, S, C=O, C=S, or a carbon atom connected to $Q^1$;

$X^2$ is CR$^7$, CR$^7$R$^8$, N, NR$^7$, O, S, C=O, C=S, or a carbon atom connected to $Q^1$;

$X^3$ is CR$^9$, CR$^9$R$^{10}$, N, NR$^9$, O, S, C=O, C=S, or a carbon atom connected to $Q^1$;

$X^4$ is CR$^{11}$, CR$^{11}$R$^{12}$, N, NR$^{11}$, O, S, C=O, C=S, or a carbon atom connected to $Q^1$;

$X^5$ is CR$^{13}$, N, or NR$^{13}$;

wherein at least one of $X^1$, $X^2$, $X^3$, and $X^4$ is a carbon atom connected to $Q^1$;

$Q^1$ is C=O, C=S, C=CR$^{14}$R$^{15}$, C=NR$^{14}$, alkylene, alkenylene, or alkynylene, each of which is independently substituted or unsubstituted, or a bond;

m is 1, 2, 3, or 4;

Y is N, O, or absent;

R$^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, C=O, C=S, —CN, —SiR$^{16}$R$^{17}$R$^{18}$, alkyl, alkenyl, alkynyl, aryl, heteroaryl, or heterocyclyl, each of which is independently substituted or unsubstituted, or hydrogen;

each R$^3$ and R$^4$ is independently, —C(O)R$^{19}$, —C(O)OR$^{19}$, —C(O)NR$^{19}$R$^{20}$, —SOR$^{19}$, —SO$_2$R$^{19}$, alkyl, alkylene, alkenyl, alkenylene, alkynyl, aryl, heteroaryl, or heterocyclyl, each of which is independently substituted or unsubstituted, or hydrogen, or R$^3$ and R$^4$ together with the nitrogen atom to which R$^3$ and R$^4$ are bound form a ring, wherein the ring is substituted or unsubstituted, or R$^3$ is absent, wherein at least one of R$^3$ and R$^4$ is alkyl, alkylene, alkenyl, alkenylene, alkynyl, aryl, heteroaryl, or heterocyclyl, each of which is substituted at least with halo-;

each R$^2$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, and R$^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

each R$^{19}$ and R$^{20}$ is C(O)R$^{23}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;

each R$^{21}$ and R$^{22}$ is independently alkyl, alkenyl, alkynyl, aryl, heteroaryl, or heterocyclyl, each of which is independently substituted or unsubstituted, or hydrogen; and each R$^{23}$ and R$^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

Embodiment 91. The compound of embodiments 87 or 88, wherein A is alkylene, alkenylene, or alkynylene, each of which is substituted or unsubstituted.

Embodiment 92. The compound of any one of embodiments 87, 88, or 91, wherein A is alkylene.

Embodiment 93. The compound of any one of embodiments 87, 88, or 91, wherein A is alkenylene.

Embodiment 94. The compound of any one of embodiments 87, 99, or 91, wherein A is alkynylene.

Embodiment 95. The compound of any one of embodiments 87-90, wherein $Q^1$ is a bond.

Embodiment 96. The compound of any one of embodiments 87-90, wherein m is 1.

Embodiment 97. The compound of any one of embodiments 87-90, wherein m is 2.

Embodiment 98. The compound of any one of embodiments 87-90, wherein Y is N or O.

Embodiment 99. The compound of any one of embodiments 87-98, Y is N.

Embodiment 100. The compound of any one of embodiments 87-99, wherein R$^1$ is alkyl, alkenyl, —C(O)R$^{16}$, —C(O)OR$^{16}$, or —C(O)NR$^{16}$R$^{17}$.

Embodiment 101. The compound of any one of embodiments 87-100, wherein R$^1$ is substituted alkyl.

Embodiment 102. The compound of any one of embodiments 87-101, wherein R$^1$ is alkyl substituted with NR$^{16}$R$^{17}$.

Embodiment 103. The compound of any one of embodiments 87-102, wherein each R$^{16}$ and R$^{17}$ is independently alkyl, alkenyl, aryl, heteroaryl, heterocyclyl, each of which is independently substituted or unsubstituted, or hydrogen.

Embodiment 104. The compound of any one of embodiments 87-103, wherein R$^{16}$ is hydrogen or alkyl.

Embodiment 105. The compound of any one of embodiments 87-104, wherein R$^{17}$ is aryl, heteroaryl, or heterocyclyl, each of which is independently substituted or unsubstituted.

Embodiment 106. The compound of any one of embodiments 87-105, wherein R$^{17}$ is substituted aryl.

Embodiment 107. The compound of any one of embodiments 87-106, wherein R$^{17}$ is substituted phenyl.

Embodiment 108. The compound of any one of embodiments 87-107, wherein R$^{17}$ is phenyl substituted with a sulfoxide group, carboxyl group, amide group, amino group, alkyl, alkoxy, hydroxy, halo, cyano, or heterocyclyl, each of which is independently substituted or unsubstituted.

Embodiment 109. The compound of any one of embodiments 87-108, wherein R$^{17}$ is phenyl substituted with methoxy.

Embodiment 110. The compound of any one of embodiments 87-108, wherein R$^{17}$ is phenyl substituted with a substituted sulfoxide group.

Embodiment 111. The compound of any one of embodiments 87-108, wherein R$^{17}$ is phenyl substituted with a carboxyl group.

Embodiment 112. The compound of any one of embodiments 87-108, wherein R$^{17}$ is phenyl substituted with a substituted amide group.

Embodiment 113. The compound of any one of embodiments 87-112, wherein R$^2$ is hydrogen or substituted or unsubstituted alkyl.

Embodiment 114. The compound of any one of embodiments 87-113, wherein R$^2$ is substituted alkyl.

Embodiment 115. The compound of any one of embodiments 87-114, wherein R$^2$ is trifluoroethyl.

Embodiment 116. The compound of any one of embodiments 87-114, wherein R$^2$ is substituted or unsubstituted cycloalkyl.

Embodiment 117. The compound of any one of embodiments 87-116, wherein R$^{13}$ is substituted or unsubstituted alkyl or alkenyl; hydrogen, or halogen.

Embodiment 118. The compound of any one of embodiments 87-117, wherein R$^{13}$ is hydrogen.

Embodiment 119. The compound of any one of embodiments 87-118, wherein at least one of R$^3$ and R$^4$ is aryl, heteroaryl, or heterocyclyl, each of which is substituted at least with halo-.

Embodiment 120. The compound of any one of embodiments 87-119, wherein R$^3$ is H, and R$^4$ is aryl, heteroaryl, or heterocyclyl, each of which is substituted at least with halo-.

Embodiment 121. The compound of any one of embodiments 87-120, wherein R$^4$ is aryl substituted at least with fluoro-.

Embodiment 122. The compound of any one of embodiments 87-120, wherein R$^4$ is heteroaryl substituted at least with fluoro-.

Embodiment 123. The compound of any one of embodiments 87-120, wherein R$^4$ is heterocyclyl substituted at least with fluoro-.

Embodiment 124. The compound of any one of embodiments 87-120 or 123, wherein R$^4$ is substituted piperidinyl.

Embodiment 125. The compound of any one of embodiments 87-120, 123, or 124, wherein $R^4$ is piperidinyl substituted at least with alkyl, carboxy, heterocyclyl, or an amide group, each of which is substituted or unsubstituted.

Embodiment 126. The compound of any one of embodiments 87-120 or 123-125, wherein $R^4$ is unsubstituted or substituted methyl piperidinyl.

Embodiment 127. The compound of any one of embodiments 87-120 or 123-126, wherein $R^4$ is 3-fluoro-1-methylpiperidinyl.

Embodiment 128. The compound of any one of embodiments 87-120 or 123-125, wherein $R^4$ is piperidinyl substituted with a substituted or unsubstituted methoxypropanol.

Embodiment 129. The compound of any one of embodiments 87-120 123-125, or 128, wherein $R^4$ is 3-fluoro-1-(2-hydroxy-3-methoxypropyl)piperidinyl.

Embodiment 130. The compound of any one of embodiments 87-120, wherein $R^4$ is unsubstituted or substituted tetrahydropyranyl.

Embodiment 131. The compound of any one of embodiments 87-120 or 130, wherein $R^4$ is tetrahydropyranyl substituted with alkyl.

Embodiment 132. The compound of any one of embodiments 87-120, 130, or 131, wherein $R^4$ is tetrahydrothiopyran-1,1-dioxide.

Embodiment 133. The compound of any one of embodiments 65-132, wherein the compound binds the mutant p53 protein and reconforms the mutant p53 protein to wild type conformation p53.

Embodiment 134. The compound of any one of embodiments 65-133, wherein the compound has oral bioavailability that is at least about 50% greater than that of an analogous compound that lacks the halo substituent on the heterocyclyl group.

Embodiment 135. A method of treating a cancer, the method comprising administering to a subject in need thereof a compound of Formula (I):

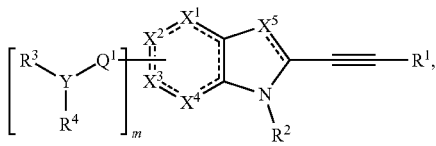

wherein:
each ------- is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
$Q^1$ is C=O, C=S, C=$CR^{14}R^{15}$, C=$NR^{14}$, alkylene, alkenylene, or alkynylene, each of which is independently substituted or unsubstituted, or a bond;
m is 1, 2, 3, or 4;
Y is N, O, or absent;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, C=O, C=S, —CN, —Si$R^{16}R^{17}R^{18}$, alkyl, alkenyl, alkynyl, aryl, heteroaryl, or heterocyclyl, each of which is independently substituted or unsubstituted, or hydrogen;

each $R^3$ and $R^4$ is independently, —C(O)$R^{19}$, —C(O)O$R^{19}$, —C(O)N$R^{19}R^{20}$, —SO$R^{19}$, —SO$_2R^{19}$, alkyl, alkylene, alkenyl, alkenylene, alkynyl, aryl, heteroaryl, or heterocyclyl, each of which is independently substituted or unsubstituted, or hydrogen, or $R^3$ and $R^4$ together with the Y atom to which $R^3$ and $R^4$ are bound form a ring, wherein the ring is substituted or unsubstituted, or $R^3$ is absent;

each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically acceptable salt thereof;
wherein the compound has an $SC_{150}$ value for p53 Y220C of less than 1 M as measured by a homogeneous time-resolved fluorescence (HTRF) assay.

Embodiment 136. The method of embodiment 135, wherein the cancer has one p53 mutation.

Embodiment 137. The method of embodiment 135 or 136, wherein the one p53 mutation is Y220C.

Embodiment 138. The method of embodiment 135, wherein the cancer has two p53 mutations.

Embodiment 139. The method of embodiment 138, wherein one of the two p53 mutations is Y220C.

Embodiment 140. The method of embodiment 138 or 139, wherein one of the two p53 mutations is a mutation to R306.

Embodiment 141. The method of embodiment 138 or 139, wherein one of the two p53 mutations is a mutation to A74.

Embodiment 142. The method of embodiment 138, wherein one of the two p53 mutations is a mutation to M237.

Embodiment 143. The method of any one of embodiments 135-142, wherein the compound has an $SC_{150}$ value of less than 0.2 µM.

Embodiment 144. The method of any one of embodiments 135-143, wherein the compound has an $SC_{150}$ value of less than 0.1 µM.

Embodiment 145. The method of any one of embodiments 135-144, wherein the compound has an $SC_{150}$ value of less than 0.05 µM.

Embodiment 146. A compound of the formula:

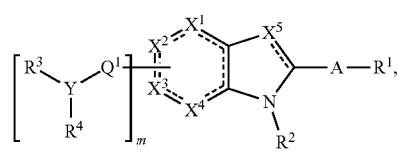

wherein:
each ------- is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
A is a linking group;
$Q^1$ is C=O, C=S, C=$CR^{14}R^{15}$, C=$NR^{14}$, alkylene, alkenylene, or alkynylene, each of which is independently substituted or unsubstituted, or a bond;
m is 1, 2, 3, or 4;
Y is N, O, or absent;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;
each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent; wherein at least one of $R^3$ and $R^4$ is alkyl, alkylene, alkenyl, alkenylene, alkynyl, alkynylene, aryl, heteroaryl, or heterocyclyl, each of which is substituted with at least halo;
each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is independently —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen,
or a pharmaceutically-acceptable salt thereof.

Embodiment 147. A compound of the formula:

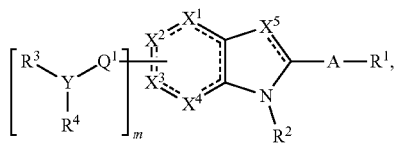

wherein:
each ------- is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
A is a linking group;
$Q^1$ is C=O, C=S, C=$CR^{14}R^{15}$, C=$NR^{14}$, alkylene, alkenylene, or alkynylene, each of which is independently substituted or unsubstituted, or a bond;
m is 1, 2, 3, or 4;
Y is N, O, or absent;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;
each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is independently —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen,
or a pharmaceutically-acceptable salt thereof, wherein the compound is not a compound of Table 1.

Embodiment 148. The compound of embodiment 146 or 147, wherein $X^1$ is a carbon atom connected to $Q^1$.
Embodiment 149. The compound of embodiment 146 or 147, wherein $X^2$ is a carbon atom connected to $Q^1$.
Embodiment 150. The compound of any one of embodiments 146-149, wherein $Q^1$ is a bond.
Embodiment 151. The compound of any one of embodiments 146-150, wherein Y is N or O.
Embodiment 152. The compound of any one of embodiments 146-151, wherein Y is N.

Embodiment 153. The compound of any one of embodiments 146-152, wherein m is 1.

Embodiment 154. The compound of any one of embodiments 146-152, wherein m is 2.

Embodiment 155. The compound of any one of embodiments 146-154, wherein A is alkylene, alkenylene, or alkynylene, each of which is substituted or unsubstituted.

Embodiment 156. The compound of any one of embodiments 146-155, wherein A is alkylene.

Embodiment 157. The compound of any one of embodiments 146-155, wherein A is alkenylene.

Embodiment 158. The compound of any one of embodiments 146-155, wherein A is alkynylene.

Embodiment 159. The compound of any one of embodiments 146-154, wherein A is an aryl group that is substituted or unsubstituted.

Embodiment 160. The compound of any one of embodiments 146-154, wherein A is a heteroaryl group that is substituted or unsubstituted.

Embodiment 161. The compound of any one of embodiments 146-154, wherein A is heterocyclyl group that is substituted or unsubstituted.

Embodiment 162. The compound of any one of embodiments 146-148, 150-153, 155, or 158, wherein the compound is of the formula:

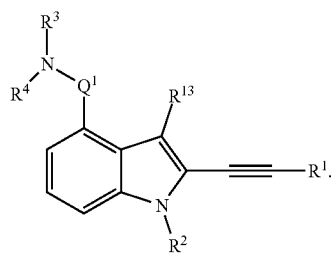

Embodiment 163. The compound of any one of embodiments 146-148, 141, 151-153, 155, or 158, wherein the compound is of the formula:

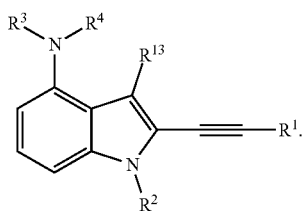

Embodiment 164. The compound of any one of embodiments 146, 147, 149-153, 155, or 158, wherein the compound has the formula:

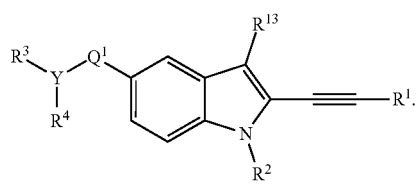

Embodiment 165. The compound of any one of embodiments 146, 147, 151-153, 155, or 158, wherein the compound has the formula:

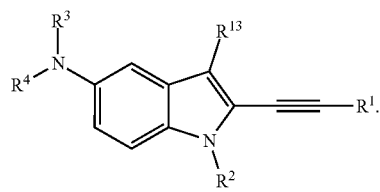

Embodiment 166. The compound of any one of embodiments 146-165, wherein $R^1$ is alkyl, alkenyl, —C(O)$R^{16}$, —C(O)O$R^{16}$, or —C(O)N$R^{16}R^{17}$.

Embodiment 167. The compound of any one of embodiments 146-166, wherein $R^1$ is substituted alkyl.

Embodiment 168. The compound of any one of embodiments 146-167, wherein $R^1$ is alkyl substituted with N$R^{16}R^{17}$.

Embodiment 169. The compound of any one of embodiments 146-148, 150-153, 155, 158, or 166-168, wherein the compound is of the formula:

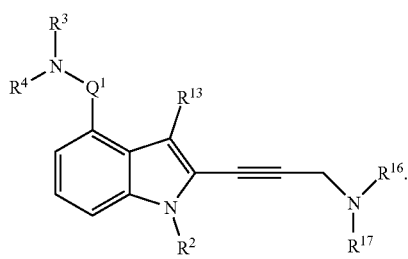

Embodiment 170. The compound of any one of embodiments 146-148, 141, 151-153, 155, 158, or 166-168, wherein the compound is of the formula:

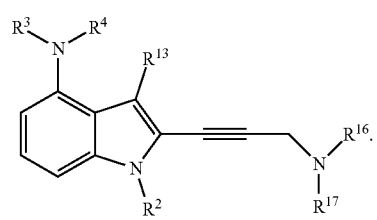

Embodiment 171. The compound of any one of embodiments 146, 147, 149-153, 155, 158, or 166-168, wherein the compound is of the formula:

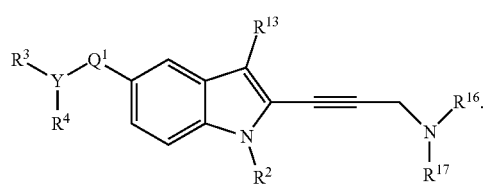

Embodiment 172. The compound of any one of embodiments 146, 147, 151-153, 155, 158, or 166-168, wherein the compound is of the formula:

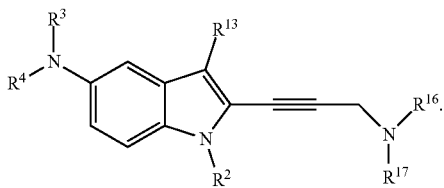

Embodiment 173. The compound of any one of embodiments 146-172, wherein each $R^{16}$ and $R^{17}$ is independently alkyl, alkenyl, aryl, heteroaryl, heterocyclyl, each of which is independently substituted or unsubstituted, or hydrogen.

Embodiment 174. The compound of any one of embodiments 146-173, wherein $R^{16}$ is hydrogen or alkyl.

Embodiment 175. The compound of any one of embodiments 146-174, wherein $R^{17}$ is aryl, heteroaryl, or heterocyclyl, each of which is independently substituted or unsubstituted.

Embodiment 176. The compound of any one of embodiments 146-175, wherein $R^{17}$ is substituted aryl.

Embodiment 177. The compound of any one of embodiments 146-176, wherein $R^{17}$ is substituted phenyl.

Embodiment 178. The compound of any one of embodiments 146-177, wherein $R^{17}$ is phenyl substituted with a sulfoxide group, carboxyl group, amide group, amino group, alkyl, alkoxy, hydroxy, halo, cyano, or heterocyclyl, each of which is independently substituted or unsubstituted.

Embodiment 179. The compound of any one of embodiments 146-178, wherein $R^{17}$ is phenyl substituted with methoxy.

Embodiment 180. The compound of any one of embodiments 146-179, wherein $R^{17}$ is phenyl substituted with a substituted sulfoxide group.

Embodiment 181. The compound of any one of embodiments 146-179, wherein $R^{17}$ is phenyl substituted with a carboxyl group.

Embodiment 182. The compound of any one of embodiments 146-179, wherein $R^{17}$ is phenyl substituted with a substituted amide group.

Embodiment 183. The compound of any one of embodiments 146-182, wherein $R^2$ is hydrogen or substituted or unsubstituted alkyl.

Embodiment 184. The compound of any one of embodiments 146-183, wherein $R^2$ is substituted alkyl.

Embodiment 185. The compound of any one of embodiments 146-184, wherein $R^2$ is trifluoroethyl.

Embodiment 186. The compound of any one of embodiments 146-184, wherein $R^2$ is substituted or unsubstituted cycloalkyl.

Embodiment 187. The compound of any one of embodiments 146-186, wherein $R^{13}$ is substituted or unsubstituted alkyl or alkenyl; hydrogen, or halogen.

Embodiment 188. The compound of any one of embodiments 146-187, wherein $R^{13}$ is hydrogen.

Embodiment 189. The compound of any one of embodiments 146-148, 141, 151-153, 155, 158, 166-168, 173-185, 187, or 188, wherein the compound has the formula:

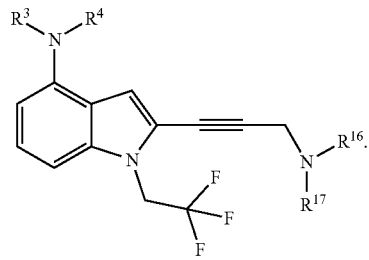

Embodiment 190. The compound of any one of embodiments 146, 147, 151-153, 155, 158, 166-168, 173-185, 187, or 188, wherein the compound has the formula:

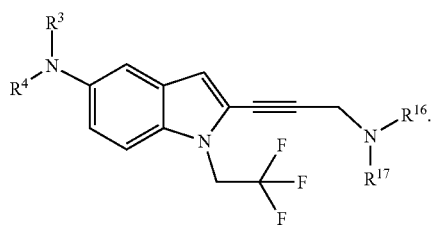

Embodiment 191. The compound of any one of embodiments 146-190, wherein at least one of $R^3$ and $R^4$ is aryl, heteroaryl, or heterocyclyl, each of which is substituted at least with halo-.

Embodiment 192. The compound of any one of embodiments 146-191, wherein $R^3$ is H, and $R^4$ is aryl, heteroaryl, or heterocyclyl, each of which is substituted at least with halo-.

Embodiment 193. The compound of any one of embodiments 146-192, wherein $R^4$ is aryl substituted at least with fluoro-.

Embodiment 194. The compound of any one of embodiments 146-192, wherein $R^4$ is heteroaryl substituted at least with fluoro-.

Embodiment 195. The compound of any one of embodiments 146-192, wherein $R^4$ is heterocyclyl substituted at least with fluoro-.

Embodiment 196. The compound of any one of embodiments 146-191, wherein at least one of $R^3$ and $R^4$ is aryl, heteroaryl, or heterocyclyl, each of which is substituted at least with chloro-.

Embodiment 197. The compound of any one of embodiments 146-191 or 196, wherein $R^3$ is H, and $R^4$ is heterocyclyl substituted at least with chloro-.

Embodiment 198. The compound of any one of embodiments 146-191 or 197, wherein $R^4$ is substituted piperidinyl.

Embodiment 199. The compound of any one of embodiments 146-191, 197, or 198, wherein $R^4$ is piperidinyl substituted at least with alkyl, carboxy, heterocyclyl, or an amide group, each of which is substituted or unsubstituted.

Embodiment 200. The compound of any one of embodiments 146-191 or 197-199, wherein $R^4$ is unsubstituted or substituted methyl piperidinyl.

Embodiment 201. The compound of any one of embodiments 146-191 or 197-200, wherein $R^4$ is 3-fluoro-1-methylpiperidinyl.

Embodiment 202. The compound of any one of embodiments 146-191 or 197-199, wherein $R^4$ is piperidinyl substituted with a substituted or unsubstituted methoxypropanol.

Embodiment 203. The compound of any one of embodiments 146-192, 195, or 202, wherein R⁴ is 3-fluoro-1-(2-hydroxy-3-methoxypropyl)piperidinyl.

Embodiment 204. The compound of any one of embodiments 146-192, 195, 197, wherein R⁴ is unsubstituted or substituted tetrahydropyranyl.

Embodiment 205. The compound of any one of embodiments 146-192, 195, 197, or 204, wherein R⁴ is unsubstituted tetrahydropyranyl.

Embodiment 206. The compound of any one of embodiments 146-192, 195, 197, or 204, wherein R⁴ is tetrahydropyranyl substituted with alkyl.

Embodiment 207. The compound of any one of embodiments 146-192, 195, 197, 204, or 206, wherein R⁴ is tetrahydrothiopyran-1,1-dioxide.

Embodiment 208. The compound of any one of embodiments 147, 148, 150-153, 155, 158, 166-168, 173-180, 183-185, 187, 188, or 189, wherein the compound is:

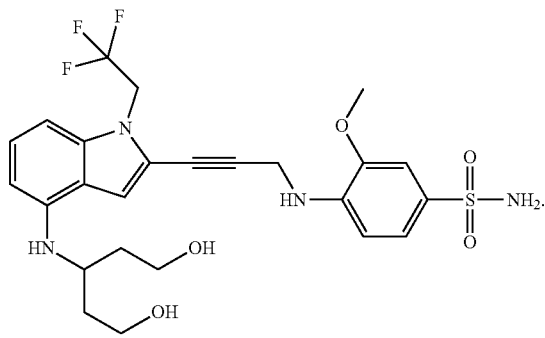 [SMILES: COc1cc(S(N)(=O)=O)ccc1NCC#Cc1cc2c(NC(CCO)CCO)cccc2n1CC(F)(F)F]

Embodiment 209. The compound of any one of embodiments 147, 148, 150-153, 155, 158, 166-168, 173-180, 183-185, 187, 188, or 189, wherein the compound is:

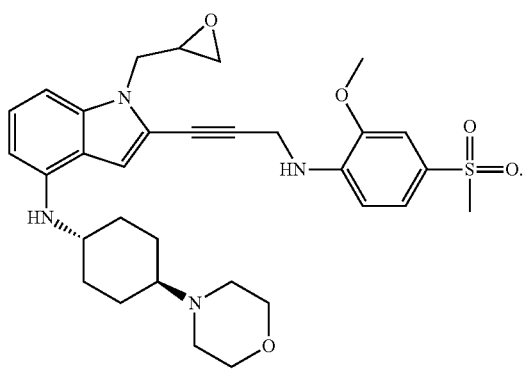 [SMILES: COc1cc(S(C)(=O)=O)ccc1NCC#Cc1cc2c(N[C@H]3CC[C@H](N4CCOCC4)CC3)cccc2n1CC1CO1]

Embodiment 210. The compound of any one of embodiments 147, 148, 150-153, 155, 158, 166-168, 173-180, 183-185, 187, 188, or 189, wherein the compound is:

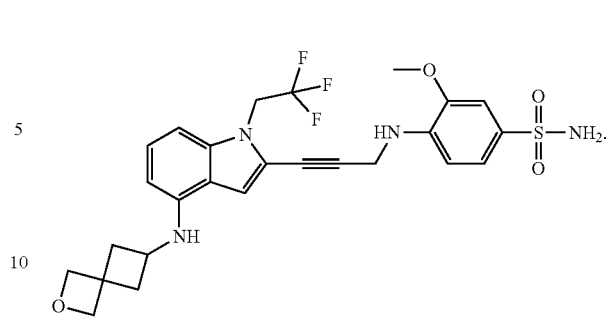

Embodiment 211. The compound of any one of embodiments 146-148, 150-153, 155, 158, 166-168, 173-180, 183-185, 187, 188, or 189, wherein the compound is:

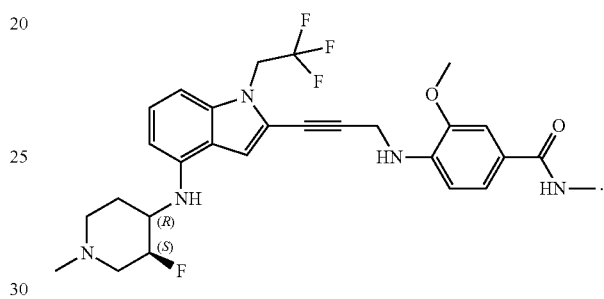

Embodiment 212. The compound of any one of embodiments 146-148, 150-153, 155, 158, 166-168, 173-180, 183-185, 187, 188, or 189, wherein the compound is:

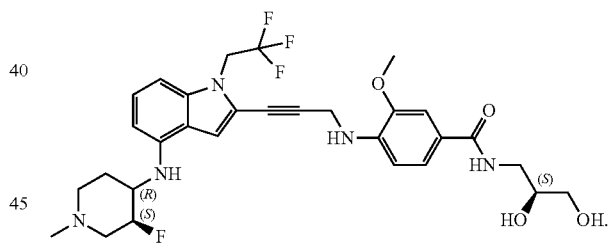

Embodiment 213. The compound of any one of embodiments 147, 148, 150-153, 155, 158, 166-168, 173-180, 183-185, 187, 188, or 189, wherein the compound is:

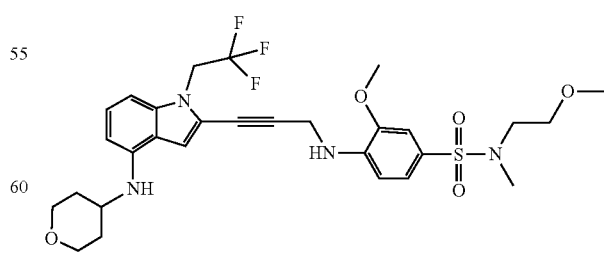

Embodiment 214. The compound of any one of embodiments 147, 148, 150-153, 155, 158, 166-168, 173-180, 183-185, 187, 188, or 189, wherein the compound is:

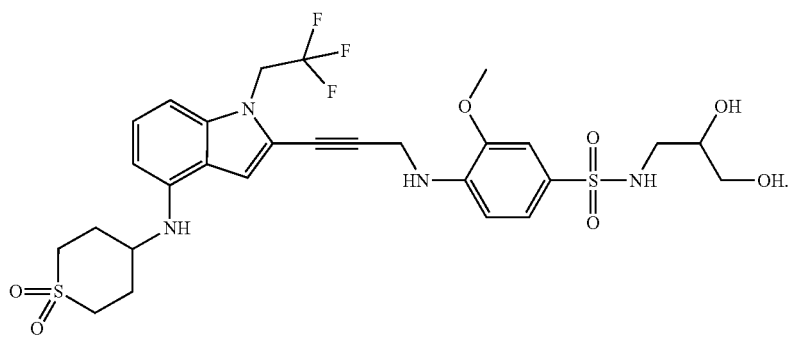 [SMILES: COc1cc(S(=O)(=O)NCC(O)CO)ccc1NCC#Cc1cc2c(NC3CCS(=O)(=O)CC3)cccc2n1CC(F)(F)F]

Embodiment 215. The compound of any one of embodiments 147, 148, 150-153, 155, 158, 166-168, 173-180, 183-185, 187, 188, or 189, wherein the compound is:

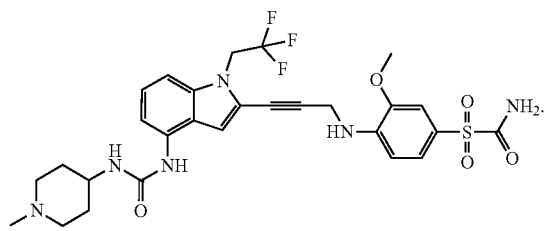 [SMILES: COc1cc(S(=O)(=O)C(N)=O)ccc1NCC#Cc1cc2c(NC(=O)NC3CCN(C)CC3)cccc2n1CC(F)(F)F]

Embodiment 216. The compound of any one of embodiments 146-148, 150-153, 155, 158, 166-168, 173-180, 183-185, 187, 188, or 189, wherein the compound is:

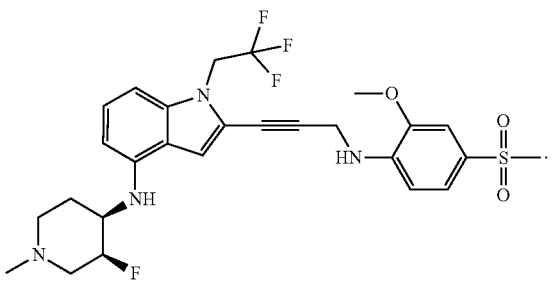

Embodiment 217. A method of inducing apoptosis in a cell, the method comprising contacting the cell with a therapeutically-effective amount of a compound that binds a p53 mutant, wherein the compound is a compound of any one of embodiments 1-216.

Embodiment 218. The method of embodiment 217, wherein the compound increases the ability of the p53 mutant to bind DNA.

Embodiment 219. The method of embodiment 217 or 218, wherein the cell expresses the p53.

Embodiment 220. The method of any one of embodiments 217-219, wherein the p53 mutant has a mutation at amino acid 220.

Embodiment 221. The method of any one of embodiments 217-220, wherein the p53 mutant is p53 Y220C.

Embodiment 222. The method of any one of embodiments 217-221, wherein the compound induces a conformational change in the p53 mutant.

Embodiment 223. The method of any one of embodiments 217-222, wherein the compound selectively binds the p53 mutant as compared to a wild type p53.

Embodiment 224. The method of any one of embodiments 217-223, wherein the therapeutically-effective amount is from about 50 mg to about 3000 mg.

Embodiment 225. The method of any one of embodiments 217-224, wherein the compound increases a stability of a biologically-active conformation of the p53 mutant relative to a stability of the biologically-active conformation of the p53 mutant in an absence of the compound.

Embodiment 226. A method of treating a cancer, the method comprising administering to a subject in need thereof a therapeutically-effective amount of a compound of any one of embodiments 1-216.

Embodiment 227. The method of embodiment 226, wherein the cancer is ovarian cancer.

Embodiment 228. The method of embodiment 226, wherein the cancer is breast cancer.

Embodiment 229. The method of embodiment 226, wherein the cancer is lung cancer.

Embodiment 230. The method of any one of embodiments 226-229, wherein the therapeutically-effective amount is from about 20 mg to about 2000 mg.

Embodiment 231. The method of any one of embodiments 74-78, wherein the administration is oral.

Embodiment 232. The method of any one of embodiments 74-78, wherein the administration is intravenous.

Embodiment 233. The method of any one of embodiments 74-78, wherein the administration is subcutaneous.

Embodiment 234. The method of any one of embodiments 74-78, wherein the administration is topical.

Embodiment 235. The method of any one of embodiments 74-82, wherein the subject is human.

Embodiment 236. The method of any one of embodiments 74-83, wherein the compound increases a stability of a biologically-active conformation of the p53 mutant relative to a stability of the biologically-active conformation of the p53 mutant in an absence of the compound.

What is claimed is:

1. A method of treating a cancer, the method comprising administering to a subject in need thereof a therapeutically-effective amount of a compound, wherein the cancer expresses a p53 mutant, wherein the p53 mutant is p53 Y220C, wherein the compound is of the formula:

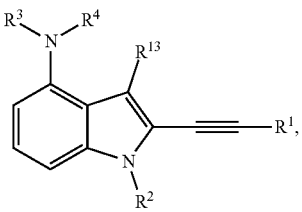

wherein:
$R^1$ is alkyl substituted with $NR^{16}R^{17}$,
$R^2$ is substituted alkyl;
each of $R^3$ and $R^{13}$ is hydrogen;
$R^4$ is aryl, heteroaryl, or heterocyclyl, each of which is substituted with at least halo;
$R^{16}$ and $R^{17}$ are each independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen; and
each $R^{21}$ and $R^{22}$ is independently alkyl, alkenyl, alkynyl, aryl, heteroaryl, or heterocyclyl, each of which is independently substituted or unsubstituted, or hydrogen
or a pharmaceutically-acceptable salt thereof.

2. The method of claim 1, wherein each $R^{16}$ and $R^{17}$ is independently alkyl, alkenyl, aryl, heteroaryl, heterocyclyl, each of which is independently substituted or unsubstituted, or hydrogen.

3. The method of claim 2, wherein $R^{16}$ is hydrogen or alkyl.

4. The method of claim 2, wherein $R^{17}$ is aryl, heteroaryl, or heterocyclyl, each of which is independently substituted or unsubstituted.

5. The method of claim 4, wherein $R^{17}$ is substituted aryl.

6. The method of claim 5, wherein $R^{17}$ is phenyl substituted with a sulfoxide group, sulfone group, carboxyl group, amide group, amino group, alkyl, alkoxy, hydroxy, or heterocyclyl, each of which is independently substituted or unsubstituted.

7. The method of claim 5, wherein $R^{17}$ is phenyl substituted with an amide group.

8. The method of claim 1, wherein $R^4$ is heterocyclyl substituted at least with halo-.

9. The method of claim 8, wherein $R^4$ is heterocyclyl substituted at least with fluoro-.

10. The method of claim 8, wherein $R^4$ is piperidinyl substituted at least with halo-.

11. The method of claim 1, wherein the compound is:

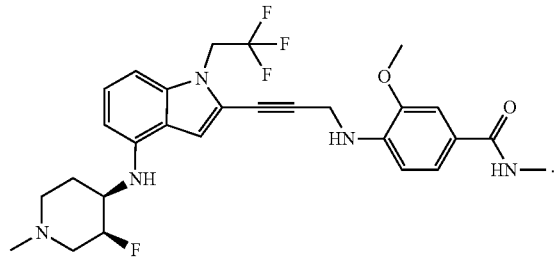

12. The method of claim 1, wherein the compound is:

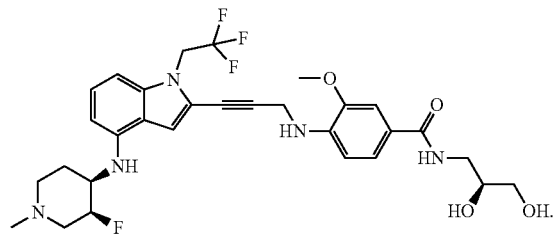 [SMILES: COc1cc(C(=O)NC[C@H](O)CO)ccc1NCC#Cc1cc2c(N[C@@H]3CCN(C)C[C@@H]3F)cccc2n1CC(F)(F)F]

13. The method of claim 1, wherein the compound is:

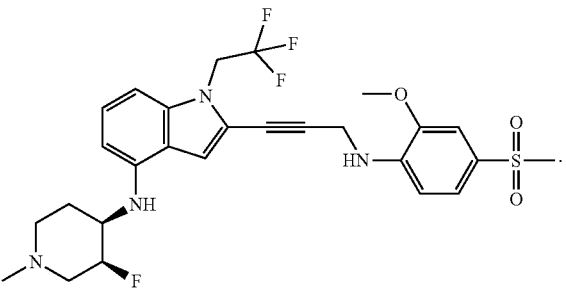

14. The method of claim 1, wherein the cancer is ovarian cancer.

15. The method of claim 1, wherein the cancer is breast cancer.

16. The method of claim 1, wherein the cancer is lung cancer.

17. The method of claim 1, wherein the therapeutically-effective amount is from about 50 mg to about 3000 mg.

18. The method of claim 1, wherein the administration is oral.

19. The method of claim 1, wherein the administration is intravenous.

20. The method of claim 1, wherein the subject is human.

* * * * *